(12) United States Patent
Clark

(10) Patent No.: US 11,905,295 B2
(45) Date of Patent: Feb. 20, 2024

(54) SOLID FORMS OF TABERNANTHALOG MONOFUMARATE SALT FOR TREATING NEUROLOGICAL DISORDERS AND/OR PSYCHIATRIC DISORDERS

(71) Applicant: Terran Biosciences Inc., New York, NY (US)

(72) Inventor: Samuel Clark, New York, NY (US)

(73) Assignee: Terran Biosciences Inc., New York, NY (US)

( * ) Notice: Subject to any disclaimer, the term of this patent is extended or adjusted under 35 U.S.C. 154(b) by 0 days.

(21) Appl. No.: 18/176,462

(22) Filed: Feb. 28, 2023

(65) Prior Publication Data

US 2023/0279017 A1    Sep. 7, 2023

Related U.S. Application Data

(63) Continuation of application No. 18/056,717, filed on Nov. 17, 2022.

(60) Provisional application No. 63/319,734, filed on Mar. 14, 2022, provisional application No. 63/316,998, filed on Mar. 5, 2022, provisional application No. 63/310,981, filed on Feb. 16, 2022, provisional application No. 63/280,514, filed on Nov. 17, 2021, provisional application No. 63/280,519, filed on Nov. 17, 2021.

(51) Int. Cl.
  *A61K 31/551* (2006.01)
  *C07D 487/14* (2006.01)
  *C07D 487/04* (2006.01)

(52) U.S. Cl.
  CPC ........ *C07D 487/04* (2013.01); *C07B 2200/13* (2013.01)

(58) Field of Classification Search
  CPC ............................ A61K 31/551; C07D 487/14
  USPC .......................................... 514/217; 540/586
  See application file for complete search history.

(56) References Cited

U.S. PATENT DOCUMENTS

| | | | |
|---|---|---|---|
| 3,652,588 | A | 3/1972 | Hester, Jr. |
| 3,676,558 | A | 7/1972 | Hester, Jr. |
| 3,839,357 | A | 10/1974 | Hester, Jr. |
| 11,414,423 | B1 | 8/2022 | Olson et al. |
| 2023/0159544 | A1 | 5/2023 | Duncton et al. |
| 2023/0257385 | A1 | 8/2023 | Duncton et al. |

FOREIGN PATENT DOCUMENTS

| | | | | |
|---|---|---|---|---|
| CA | 834205 | A | 2/1970 | |
| DE | 1695943 | A1 | 5/1971 | |
| FR | 1524495 | A | 5/1968 | |
| FR | 6699 | M | 2/1969 | |
| GB | 1062840 | A | 3/1967 | |
| GB | 1180615 | A | 2/1970 | |
| JP | 2017031088 | A | 2/2017 | |
| NL | 6515701 | A | 6/1966 | |
| WO | WO-0105793 | A1 | 1/2001 | |
| WO | WO-0224700 | A2 | 3/2002 | |
| WO | WO-0224701 | A2 | 3/2002 | |
| WO | WO-2020176599 | A1 | 9/2020 | |
| WO | WO-2021252691 | A1 | 12/2021 | |
| WO | WO-2021252692 | A1 | 12/2021 | |
| WO | WO-2022081631 | A1 | 4/2022 | |
| WO | WO-2023077125 | A2 | 5/2023 | |
| WO | WO 2023092045 | | * 5/2023 | ........... C07D 487/04 |
| WO | WO-2023092045 | A1 | 5/2023 | |

OTHER PUBLICATIONS

Jordan, V. C. Nature Reviews: Drug Discovery, 2, 2003, 205.*
Hackam, et al. JAMA, 296(14), 2006, 1731-1732.*
Al-Muhammed et al. "In-vivo studies on dexamethasone sodium phosphate liposomes", Journal of microencapsulation, (1996);13(3):293-305.
Berge et al. "Pharmaceutical salts", Journal of pharmaceutical sciences, (1977); 66(1):1-19.
Byrn et al. "Pharmaceutical solids: a strategic approach to regulatory considerations", Pharmaceutical Research, (1995); 12:945-954.
Cameron et al. "A non-hallucinogenic psychedelic analogue with therapeutic potential", Nature; (2021), 589(7842):474-479.
Chonn et al. "Recent advances in liposomal drug-delivery systems", Current Opinion in Biotechnology, (1995); 6(6):698-708.
Diker, K., et al., "Practical Syntheses of Hexahydroazepino [4,5-b]-and Hexahydroazocino [4,5-b] Indoles", Tetrahedron Letters, (1995), 36(20):3511-3512.
Dong et al. "Psychedelic-inspired drug discovery using an engineered biosensor", Cell, (2021); 184(10):2779-2792.
Efange, S.M.N., et al., "Modified Ibogaine Fragments: Synthesis and Preliminary Pharmacological Characterization of 3-ethyl-5-phenyl-1,2,3,4,5,6-Hexahydroazepino [4,5-b] benzothiophenes", Journal of Medicinal Chemistry, (1998) 41, 4486-4491.
Eyles JE, et al. "Oral delivery and fate of poly (lactic acid) microsphere-encapsulated interferon in rats", Journal of pharmacy and pharmacology, (1997); 49(7):669-774.
File History of PCT/US2022/078990, filed on Oct. 31, 2022, 182 pages.

(Continued)

*Primary Examiner* — Douglas M Willis
(74) *Attorney, Agent, or Firm* — COOLEY LLP; Ivor R. Elrifi; Chen Chen

(57) ABSTRACT

Disclosed herein are salt and solid forms of tabernanthalog. Disclosed solid forms may be a polymorph of tabernanthalog fumarate, and/or may have improved properties, such as improved physical, chemical and/or pharmacokinetic properties. Disclosed salts include pharmaceutically acceptable salts of tabernanthalog. Disclosed solid forms include free base and salt forms of tabernanthalog, including amorphous and crystalline forms of tabernanthalog, such as tabernanthalog free base or a salt thereof. Also disclosed are methods for making the salts and solid forms and methods for administering the same. The salt and solid forms of tabernanthalog and salts thereof are useful for treating neurological disease and/or a psychiatric disorder in a subject.

28 Claims, 487 Drawing Sheets
(309 of 487 Drawing Sheet(s) Filed in Color)

(56) References Cited

OTHER PUBLICATIONS

File History of PCT/US2022/080091, filed on Nov. 17, 2022, 1205 pages.
Gao, Z.H., et al., "Controlled release of a contraceptive steroids from biodegradable and injectable gel formulations: in vitro evaluation," Pharm Res., (1995);12(6):857-863.
Haleblian et al. "Pharmaceutical applications of polymorphism", Journal of Pharmaceutical Sciences, (1969); 58(8):911-929.
Harley-Mason, J., et al."Hydroxytryptamines. Part III. Synthesis of an azepindole derivative by molecular rearrangement", Journal of the Chemical Society (Resumed), (1955); 374-376.
Hester, J.B., et al., "Azepinoindoles. I. Hexahydroazepino [4, 5-b] indoles", Journal of Medicinal Chemistry, (1968); 11(1):101-106.
Ly et al. "Psychedelics promote structural and functional neural plasticity", Cell Reports, (2018); 23(11):3170-3182.
Minto et al. "Pharmacokinetics and pharmacodynamics of nandrolone esters in oil vehicle: effects of ester, injection site and injection volume", Journal of pharmacology and experimental therapeutics, (1997); 281(1):93-102.
Ostro MJ, et al. "Use of liposomes as injectable-drug delivery systems", American Journal of Hospital Pharmacy, (1989), 46:1576-1587.
Panduranga RK. "Recent developments of collagen-based materials for medical applications and drug delivery systems", Journal of Biomaterials Science, Polymer Edition, (1995); 7(7):623-645.
Rohatagi, S., et al., "Pharmacokinetic and pharmacodynamic evaluation of triamcinolone acetonide after intravenous, oral, and inhaled administration", The Journal of Clinical Pharmacology, (1995); 35(12):1187-1193.
Tjwa, M.K.T., "Budesonide inhaled via Turbuhaler: a more effective treatment for asthma than beclomethasone dipropionate via Rotahaler", Annals of Allergy, Asthma & Immunology: official publication of the American College of Allergy, Asthma, & Immunology, (1995); 75(2):107-111.
Database STN, CAS Registry No. 15918-87-3 "Azepino[4,5-b]indole, 1,2,3,4,5,6-hexahydro-8-methoxy-" (CA Index Name), Chemical Abstracts Service, American Chemical Society entered Nov. 16, 1984; retrieved Jun. 23, 2023; 3 pages.
Zetler, G., et al., "Refractory Period and Strophanthin Actions, as Influenced by Four Indole Alkaloids and Two Synthetic Azepinoindoles," Pharmacology, (1972), 8(54):235-243.

* cited by examiner

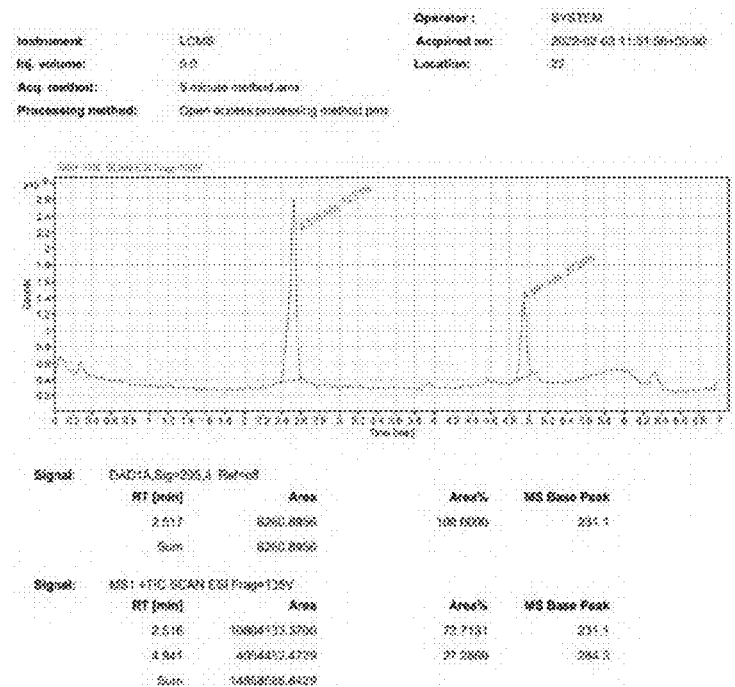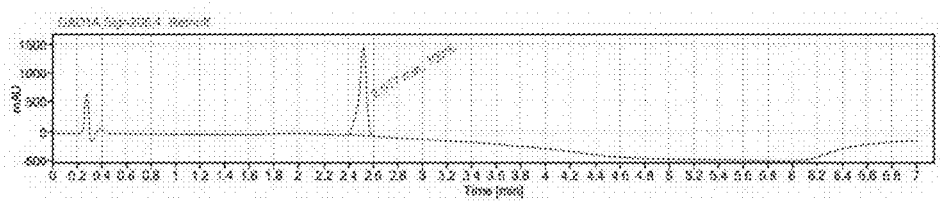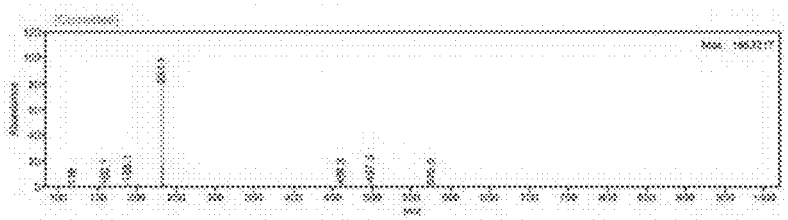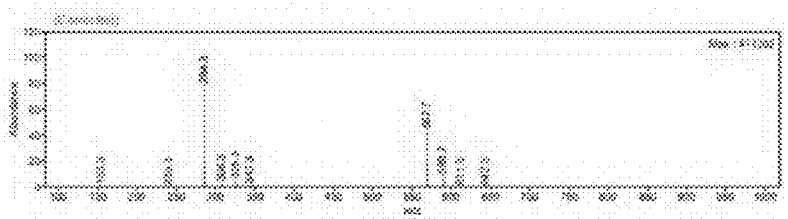
FIG. 92

| | |
|---|---|
| Compound | 11-M2 (Experiment Reference 11-Sample Reference M2) |
| Formula | $C_{18}H_{22}N_2O_5$ |
| $D_{calc.}$/ g cm$^{-3}$ | 1.318 |
| $m$/mm$^{-1}$ | 0.801 |
| Formula Weight | 346.37 |
| Color | colorless |
| Shape | block-shaped |
| Size/mm$^3$ | 0.13×0.05×0.03 |
| $T$/K | 300(2) |
| Crystal System | monoclinic |
| Space Group | $P2_1/c$ |
| $a$/Å | 7.43280(10) |
| $b$/Å | 8.59740(10) |
| $c$/Å | 27.5143(3) |
| $a$/° | 90 |
| $b$/° | 96.6990(10) |
| $g$/° | 90 |
| $V$/Å$^3$ | 1746.24(4) |
| $Z$ | 4 |
| $Z'$ | 1 |
| Wavelength/Å | 1.54184 |
| Radiation type | Cu K$_\alpha$ |
| $Q_{min}$/° | 3.235 |
| $Q_{max}$/° | 76.907 |
| Measured Refl's. | 32845 |
| Indep't Refl's | 3622 |
| Refl's I≥2 $s$(I) | 3220 |
| $R_{int}$ | 0.0333 |
| Parameters | 237 |
| Restraints | 1 |
| Largest Peak | 0.188 |
| Deepest Hole | -0.173 |
| GooF | 1.033 |
| $wR_2$ (all data) | 0.1071 |
| $wR_2$ | 0.1036 |
| $R_1$ (all data) | 0.0462 |
| $R_1$ | 0.0409 |

Structure Quality Indicators

Reflections: 0.79 · 55.1 · 3.33% · 100

Refinement: -0.001 · 0.2 · -0.2 · 1.033

FIG. 285

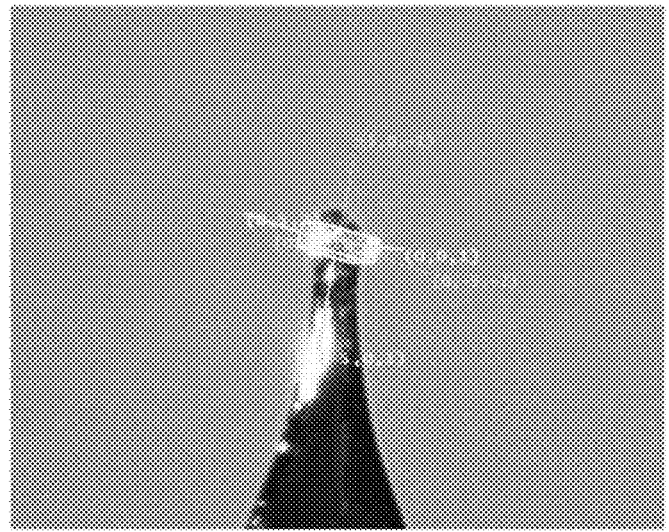

| Compound | 11-Q2 (Experiment Reference 11- Sample Reference Q2) |
|---|---|
| Formula | $C_{8.12}H_{10.5}NO_{1.62}$ |
| $D_{calc.}$/ g cm$^{-3}$ | 1.192 |
| $m$/mm$^{-1}$ | 0.680 |
| Formula Weight | 148.17 |
| Color | yellow |
| Shape | rod-shaped |
| Size/mm$^3$ | 0.10×0.03×0.01 |
| $T$/K | 300(2) |
| Crystal System | monoclinic |
| Space Group | $C2/c$ |
| $a$/Å | 21.7386(8) |
| $b$/Å | 9.7033(5) |
| $c$/Å | 15.8640(8) |
| $a$/° | 90 |
| $b$/° | 99.182(4) |
| $g$/° | 90 |
| $V$/Å$^3$ | 3303.4(3) |
| Z | 16 |
| Z' | 2 |
| Wavelength/Å | 1.54184 |
| Radiation type | Cu K$_a$ |
| $Q_{min}$/° | 4.120 |
| $Q_{max}$/° | 77.152 |
| Measured Refl's. | 11278 |
| Indep't Refl's | 3227 |
| Refl's I≥2 $s$(I) | 2190 |
| $R_{int}$ | 0.0472 |
| Parameters | 218 |
| Restraints | 5 |
| Largest Peak | 0.610 |
| Deepest Hole | -0.305 |
| GooF | 1.043 |
| $wR_2$ (all data) | 0.2751 |
| $wR_2$ | 0.2468 |
| $R_1$ (all data) | 0.1137 |
| $R_1$ | 0.0857 |

Structure Quality Indicators

Reflections:

Refinement:

FIG. 286

| T/K | 300(2) |
|---|---|
| Crystal System | monoclinic |
| Space Group | P2$_1$/c |
| a/Å | 7.43280(10) |
| b/Å | 8.59740(10) |
| c/Å | 27.5143(3) |
| a/° | 90 |
| b/° | 96.6990(10) |
| g/° | 90 |
| V/Å$^3$ | 1746.24(4) |

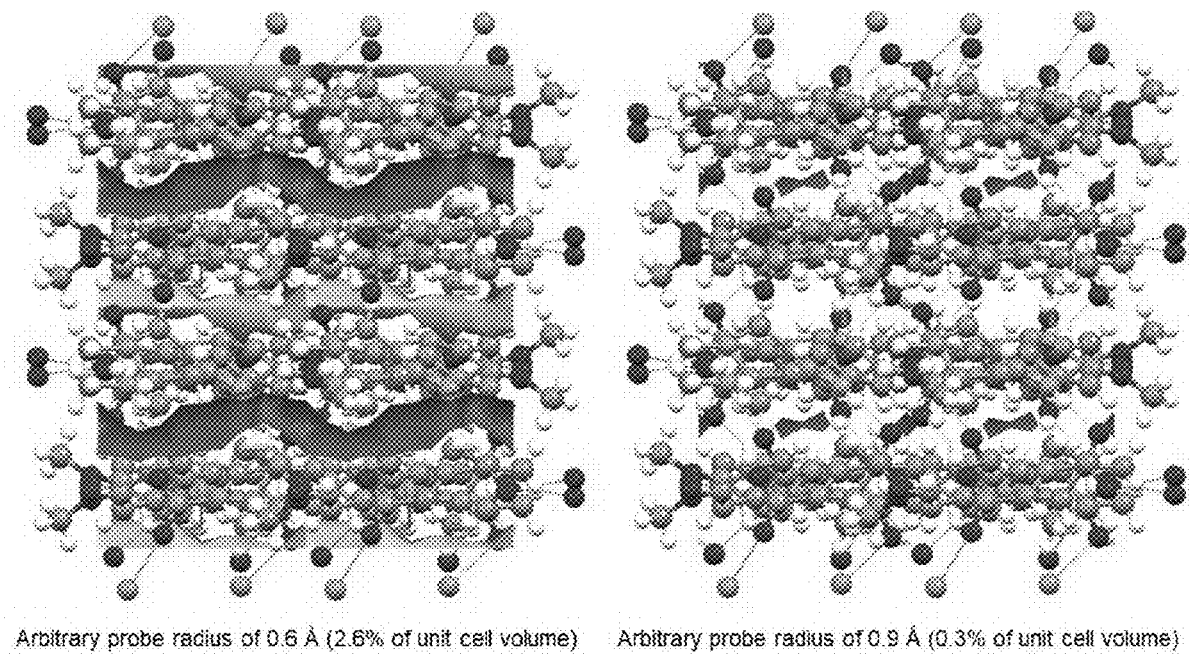
Arbitrary probe radius of 0.6 Å (2.6% of unit cell volume)   Arbitrary probe radius of 0.9 Å (0.3% of unit cell volume)
FIG. 290
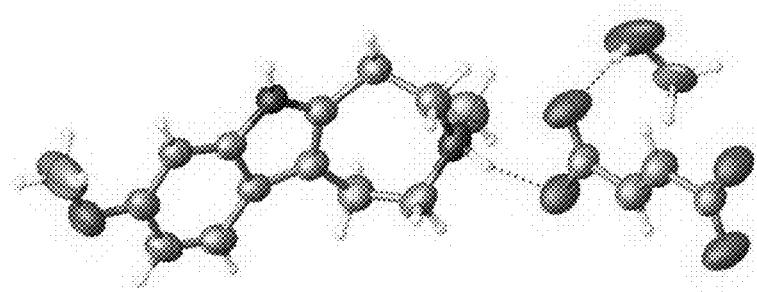
FIG. 291
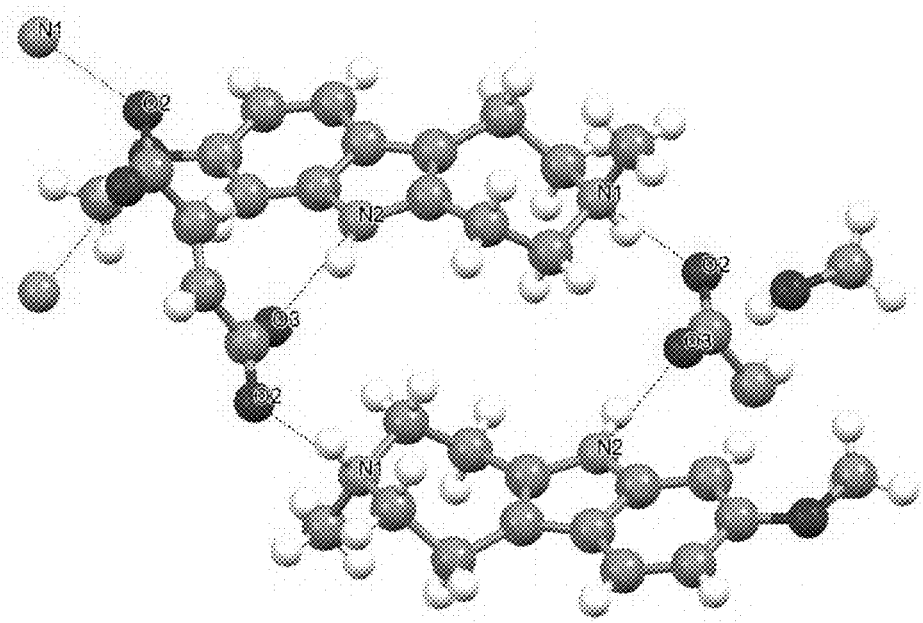

| T/K | 300(2) |
|---|---|
| Crystal System | monoclinic |
| Space Group | C2/c |
| a/Å | 21.7386(8) |
| b/Å | 9.7033(5) |
| c/Å | 15.8640(8) |
| a/° | 90 |
| b/° | 99.182(4) |
| g/° | 90 |
| V/Å$^3$ | 3303.4(3) |

FIG. 292

Arbitrary probe radius of 0.4 Å (10% of unit cell volume)

Stoichiometry: 1 to 1 API to fumarate
Solvents: 2-MeTHF n.d.

Stoichiometry: 1 to 1 API to fumarate
Solvents: MeCN: 0.1% w/w

Stoichiometry: 1 to 1 API to fumarate
Solvents: EtOAc: 3.2% w/w

Stoichiometry: Co-resonated
Solvents: MeCN 0.2% w/w

Stoichiometry: 1 to 1 API to fumarate
Solvents: toluene: 4.6% w/w

Stoichiometry: 1 to 1 API to fumarate
Solvents: MeOH: 0.2% w/w

Stoichiometry: 1 to 1 API to fumarate

Solvents: Nitromethane: 0.2% w/w

Stoichiometry: 1 to 1 API to fumarate

Solvents: n.d.

Stoichiometry: 1 to 1 API to fumarate

Solvents: MeOH: 0.7% w/w, MeCN: 0.3% w/w

Stoichiometry: 1 to 1 API to fumarate
Solvents: isopropyl acetate: 10.0% w/w

Stoichiometry: 1 to 1 API to fumarate
Solvents: butanol: 6.3% w/w

Stoichiometry: 2 to 1 API to fumarate
Solvents: Ethanol 4.9% w/w, MeCN 0.2% w/w Stoichiometry: 2 to 1 API to fumarate
Solvents: Acetone: 0.2% w/w
Acetonitrile: 0.3% w/w
Methanol: 2.4% w/w

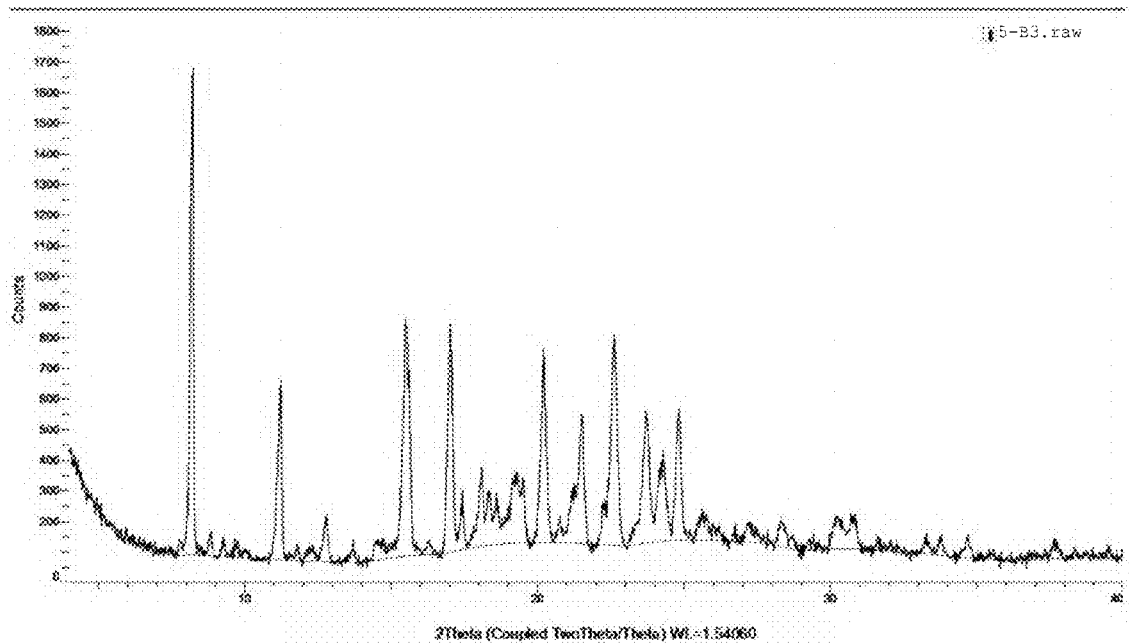
FIG. 377F
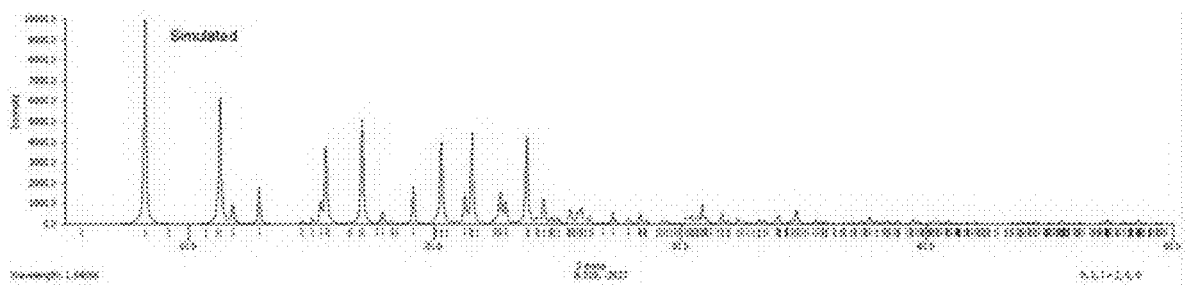

Stoichiometry: 2 to 1 API to fumarate
Solvents: Isopropanol: 0.9% w/w

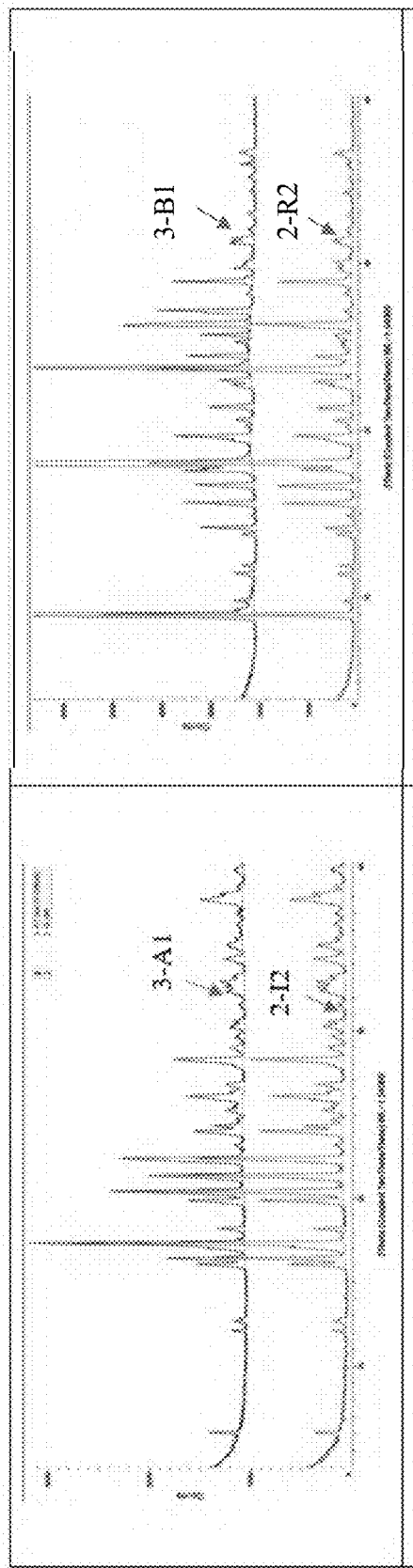
FIG. 405
FIG. 406
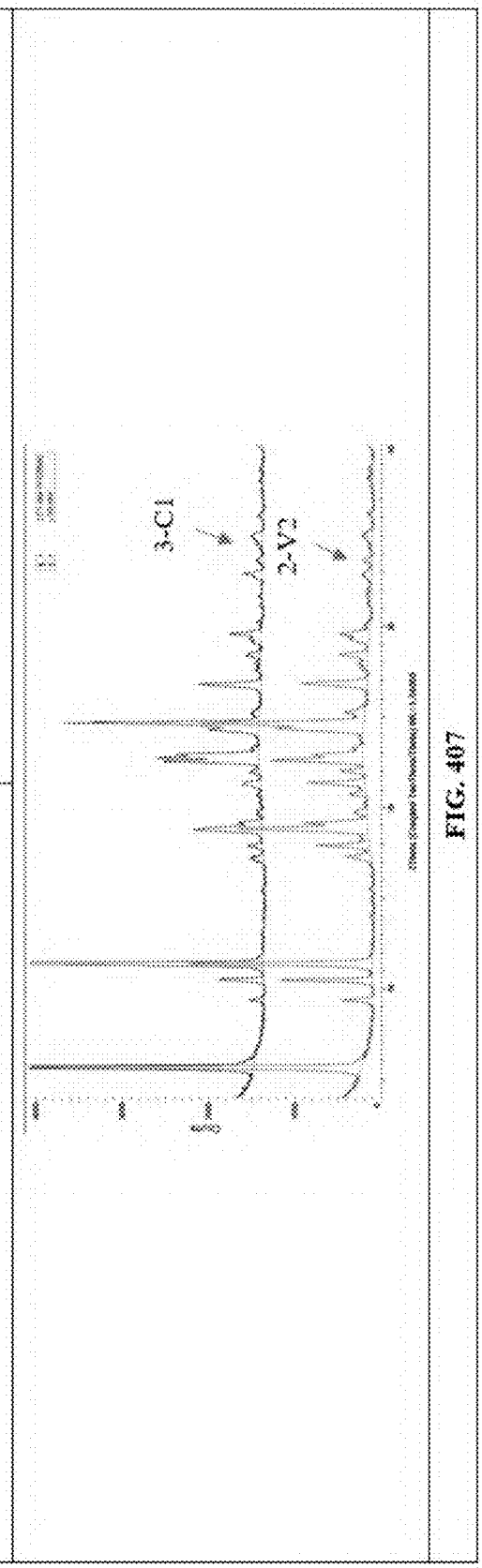
FIG. 407

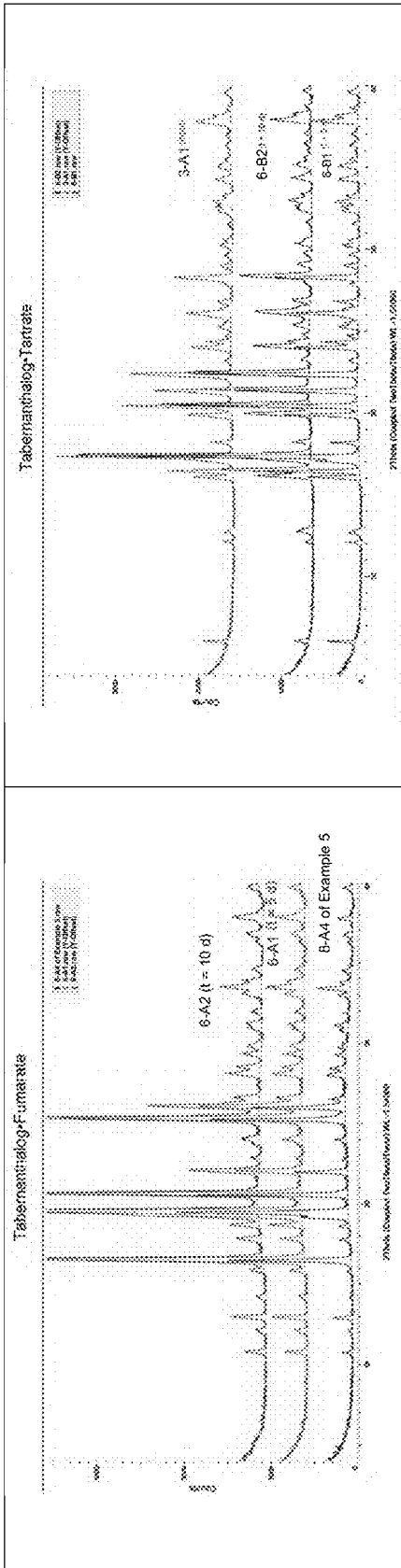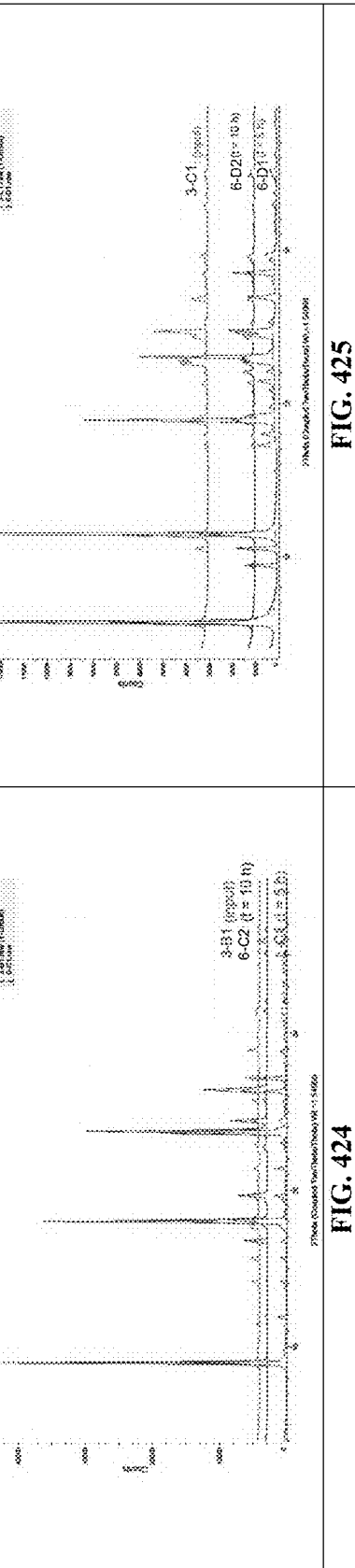
FIG. 422
FIG. 423
FIG. 424
FIG. 425

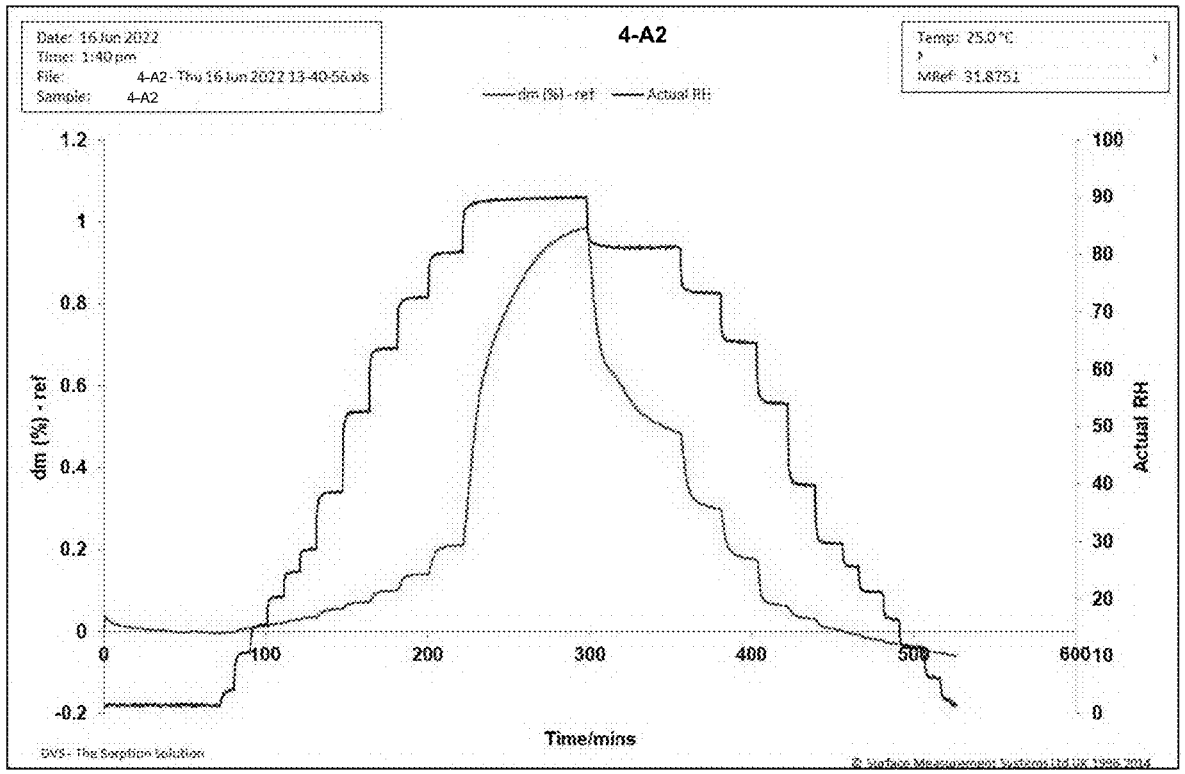
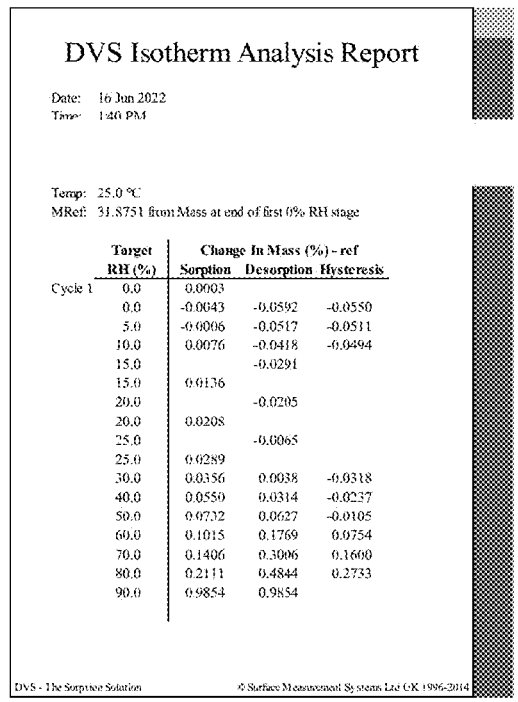
FIG. 455

DVS Isotherm Analysis Report

Date: 13 Jun 2022
Time: 10:55 AM
File:
Meth:
Sample:
Temp: 25.0 °C
MRef: 21.7087 from Mass at end of first 0% RH stage

|  | Target RH (%) | Change In Mass (%) - ref | | |
|---|---|---|---|---|
|  |  | Sorption | Desorption | Hysteresis |
| Cycle 1 | 0.0 | -0.0002 |  |  |
|  | 0.0 | -0.0014 | -0.0367 | -0.0353 |
|  | 5.0 | 0.0014 | -0.0341 | -0.0355 |
|  | 10.0 | 0.0018 | -0.0321 | -0.0339 |
|  | 15.0 |  | -0.0316 |  |
|  | 15.0 | -0.0018 |  |  |
|  | 20.0 |  | -0.0287 |  |
|  | 20.0 | -0.0026 |  |  |
|  | 25.0 |  | -0.0279 |  |
|  | 25.0 | -0.0022 |  |  |
|  | 30.0 | 0.0016 | -0.0233 | -0.0249 |
|  | 40.0 | 0.0021 | -0.0182 | -0.0204 |
|  | 50.0 | 0.0056 | -0.0138 | -0.0194 |
|  | 60.0 | 0.0092 | -0.0011 | -0.0103 |
|  | 70.0 | 0.0088 | 0.0337 | 0.0249 |
|  | 80.0 | 0.0461 | 0.0629 | 0.0169 |
|  | 90.0 | 0.1184 | 0.1184 |  |

1.0 PLM

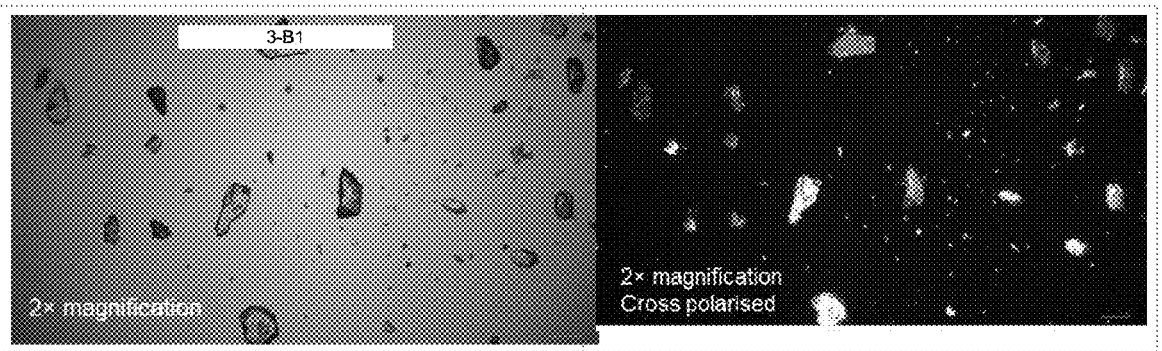
FIG. 647 | FIG. 648
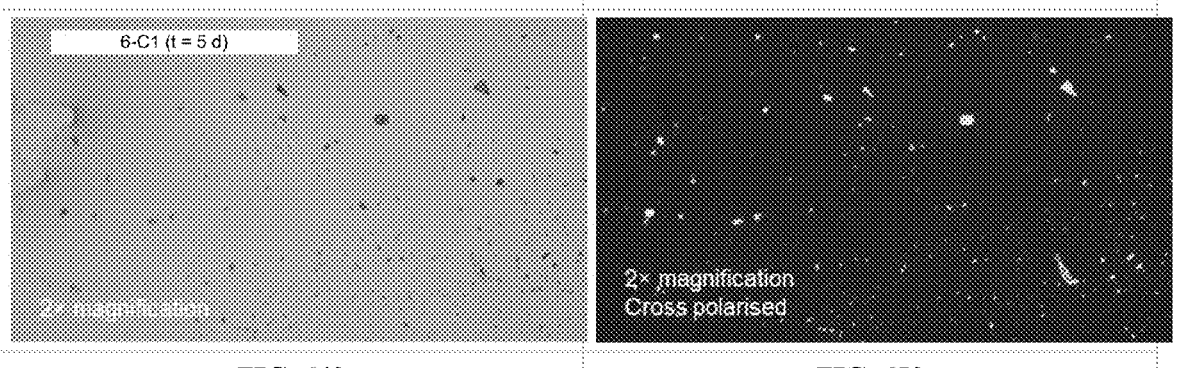
FIG. 649 | FIG. 650
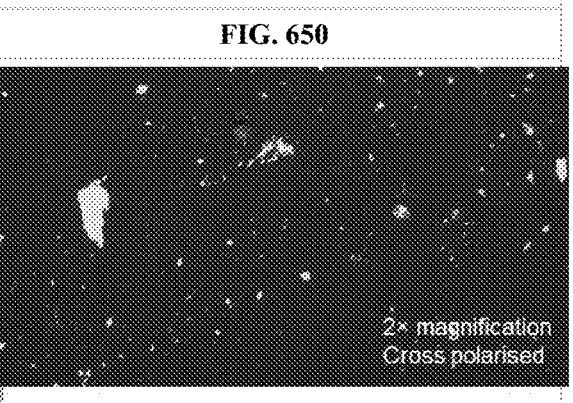
FIG. 651 | FIG. 652

Tabernanthalog Sorbate

MW: 342.44
Formula: $C_{20}H_{26}N_2O_3$

| Experimental reference | Experiment input reference | Picture at t = 5 days | Picture at t = 10 days |
|---|---|---|---|
| Experiment 10-Sample A1, Experiment 10-Sample A2 (open vial) | Experiment 1-Sample A2 (Form A) | | |
| Experiment 10-Sample B1, Experiment 10-Sample B2 (double bagged vial) | | | |

| T/K | 100(2) |
|---|---|
| Crystal System | monoclinic |
| Space Group | P21/c |
| a/Å | 9.3410(3) |
| b/Å | 6.4173(2) |
| c/Å | 30.5108(12) |
| a/° | 90 |
| b/° | 95.374(3) |
| g/° | 90 |
| V/Å³ | 1820.90(11) |
| Z | 1 |
| Z' | 4 |

| T/K | 100(2) |
|---|---|
| Crystal System | monoclinic |
| Space Group | P2$_1$/c |
| a/Å | 16.07470(10) |
| b/Å | 12.14150(10) |
| c/Å | 10.85080(10) |
| a/° | 90 |
| b/° | 109.2390(10) |
| g/° | 90 |
| V/Å$^3$ | 1999.49(3) |
| Z | 4 |
| Z' | 1 |

Residual ethanol: 0.1% w/w
1 to 1 ratio of API to sorbic acid.

Residual ethanol: 0.1% w/w
1 to 1 ratio of API to sorbic acid.

1 to 1 ratio of API to sorbic acid.

Residual ethanol: 0.3% w/w
1 to 1 ratio of API to sorbic acid.

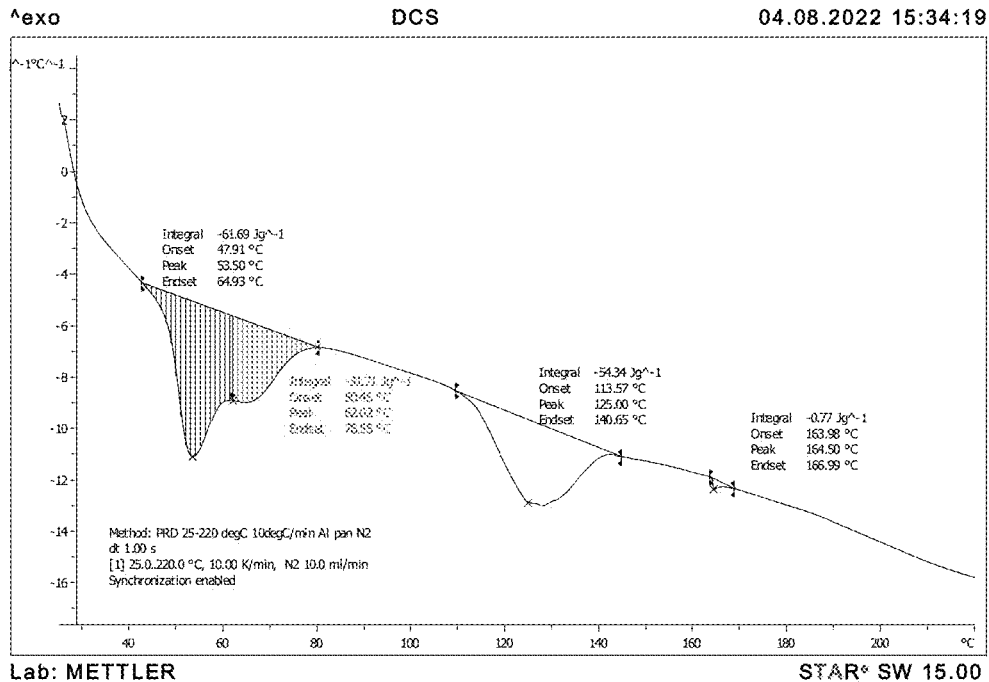
FIG. 762
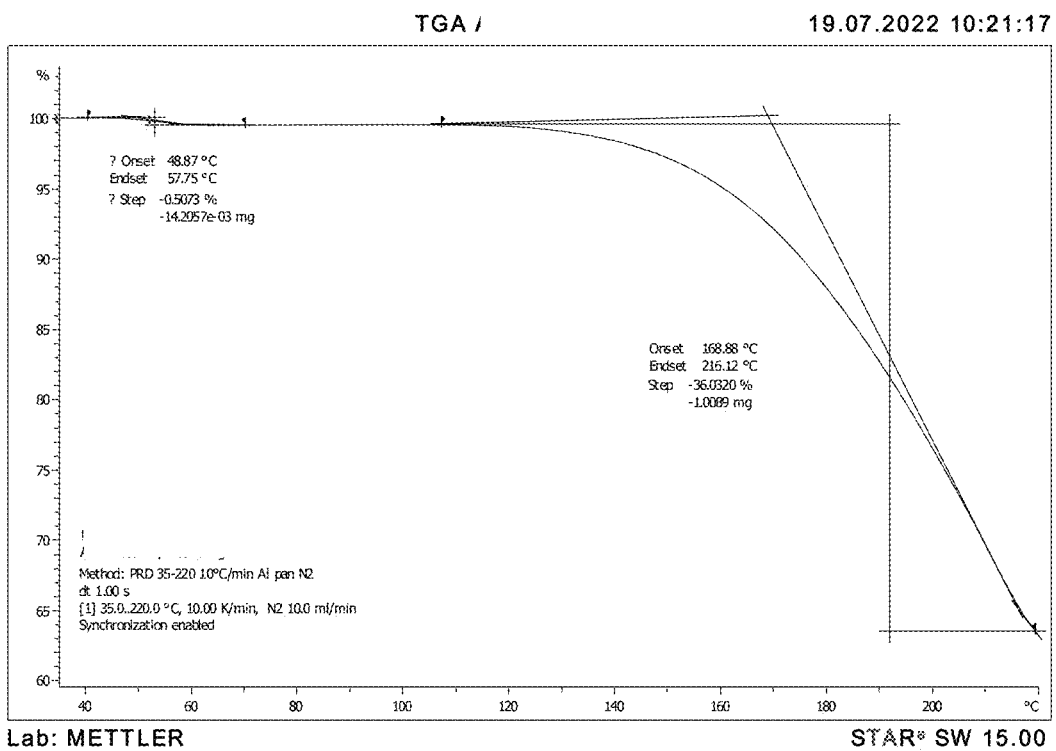

Residual ethyl formate: 0.9% w/w
1 to 1 ratio of API to sorbic acid.

| | |
|---|---|
| Compound | Experiment 11-Sample A1 |
| Formula | $C_{20}H_{26}N_2O_3$ |
| $D_{calc}$/ g cm$^{-3}$ | 1.249 |
| $m$/mm$^{-1}$ | 0.675 |
| Formula Weight | 342.43 |
| Colour | colourless |
| Shape | block-shaped |
| Size/mm$^3$ | 0.24×0.07×0.03 |
| T/K | 100(2) |
| Crystal System | monoclinic |
| Space Group | $P2_1/c$ |
| a/Å | 9.3410(3) |
| b/Å | 6.4173(2) |
| c/Å | 30.5108(12) |
| a/° | 90 |
| b/° | 95.374(3) |
| g/° | 90 |
| V/Å$^3$ | 1820.90(11) |
| Z | 4 |
| Z' | 1 |
| Wavelength/Å | 1.54184 |
| Radiation type | Cu K$_\alpha$ |
| $Q_{min}$/° | 4.755 |
| $Q_{max}$/° | 76.705 |
| Measured Refl's. | 13832 |
| Indep't Refl's | 3694 |
| Refl's I≥2 s(I) | 3203 |
| $R_{int}$ | 0.0462 |
| Parameters | 300 |
| Restraints | 568 |
| Largest Peak | 0.359 |
| Deepest Hole | -0.311 |
| GooF | 1.094 |
| $wR_2$ (all data) | 0.2098 |
| $wR_2$ | 0.2030 |
| $R_1$ (all data) | 0.0931 |
| $R_1$ | 0.0826 |

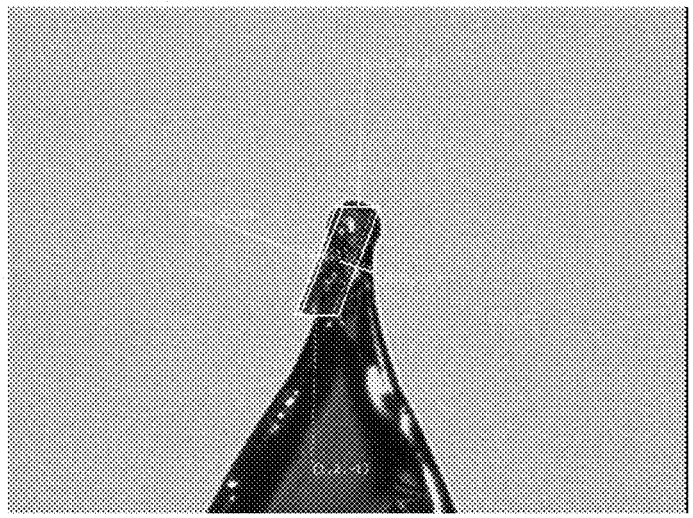

Notes: The sorbate moiety is disordered. The occupancy of the two components has been freely refined to approximately 0.67 and 0.33.

Structure Quality Indicators

Reflections: 0.79 | 24.9 | | 99.2

Refinement: 0.000 | 0.4 | -0.3 | 1.094

FIG. 810

| Compound | Experiment 12-Sample A2 |
|---|---|
| Formula | $C_{20}H_{28}N_2O_4$ |
| $D_{calc}$ / g cm$^{-3}$ | 1.197 |
| $m$/mm$^{-1}$ | 0.676 |
| Formula Weight | 360.44 |
| Colour | colourless |
| Shape | block-shaped |
| Size/mm$^3$ | 0.22×0.16×0.02 |
| $T$/K | 100(2) |
| Crystal System | monoclinic |
| Space Group | $P2_1/c$ |
| $a$/Å | 16.07470(10) |
| $b$/Å | 12.14150(10) |
| $c$/Å | 10.85080(10) |
| $a$/° | 90 |
| $b$/° | 109.2390(10) |
| $g$/° | 90 |
| $V$/Å$^3$ | 1999.49(3) |
| $Z$ | 4 |
| $Z'$ | 1 |
| Wavelength/Å | 1.54184 |
| Radiation type | Cu K$_\alpha$ |
| $Q_{min}$/° | 2.912 |
| $Q_{max}$/° | 70.074 |
| Measured Refl's. | 51305 |
| Indep't Refl's | 3786 |
| Refl's I≥2 $s$(I) | 3542 |
| $R_{int}$ | 0.0483 |
| Parameters | 250 |
| Restraints | 0 |
| Largest Peak | 0.233 |
| Deepest Hole | -0.188 |
| GooF | 1.039 |
| $wR_2$ (all data) | 0.0874 |
| $wR_2$ | 0.0861 |
| $R_1$ (all data) | 0.0369 |
| $R_1$ | 0.0347 |

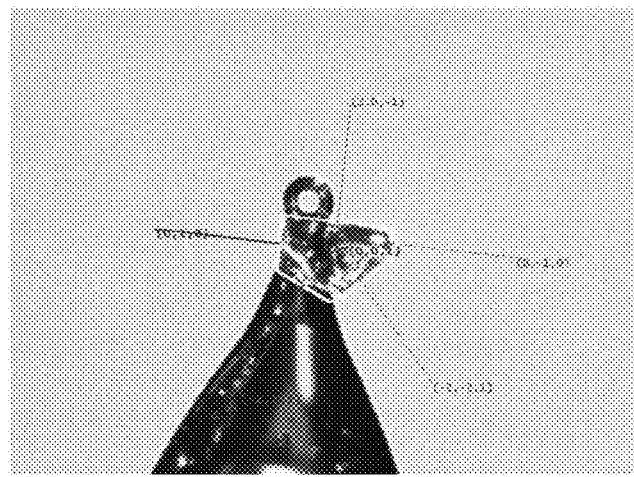

Structure Quality Indicators

Reflections:  0.82  72.5  100

Refinement:  0.000  0.2  -0.2  1.039

FIG. 811

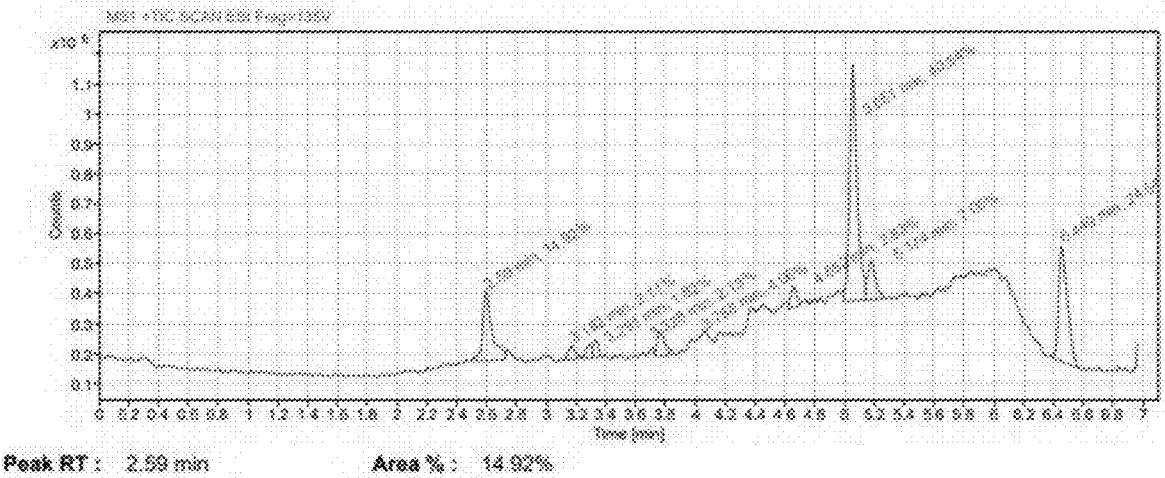
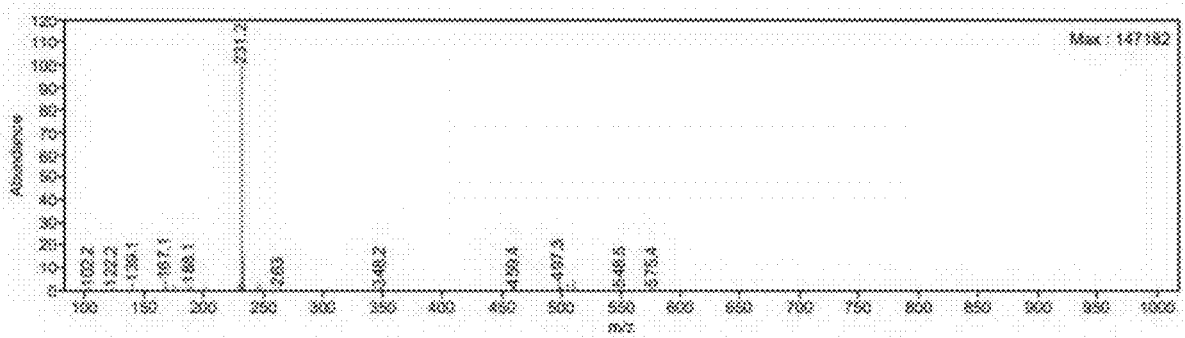
FIG. 816

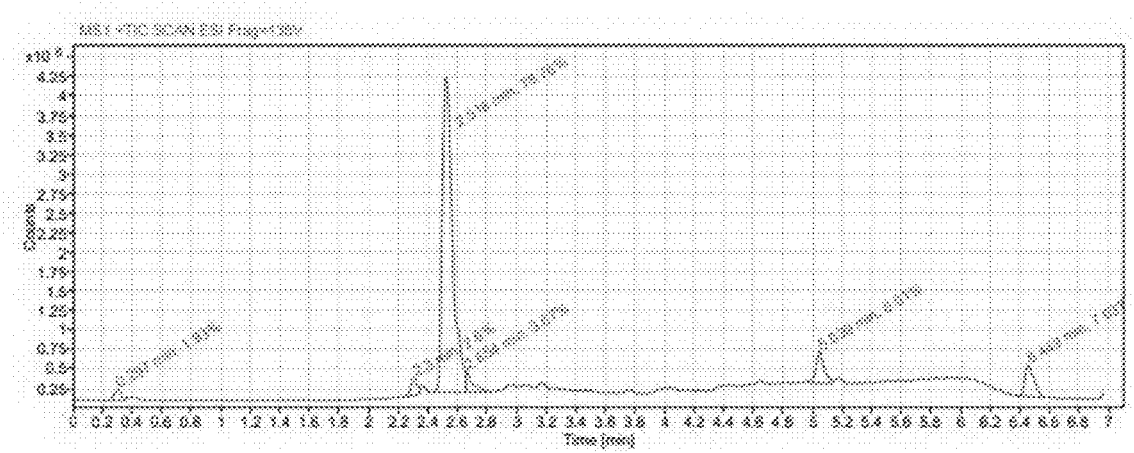
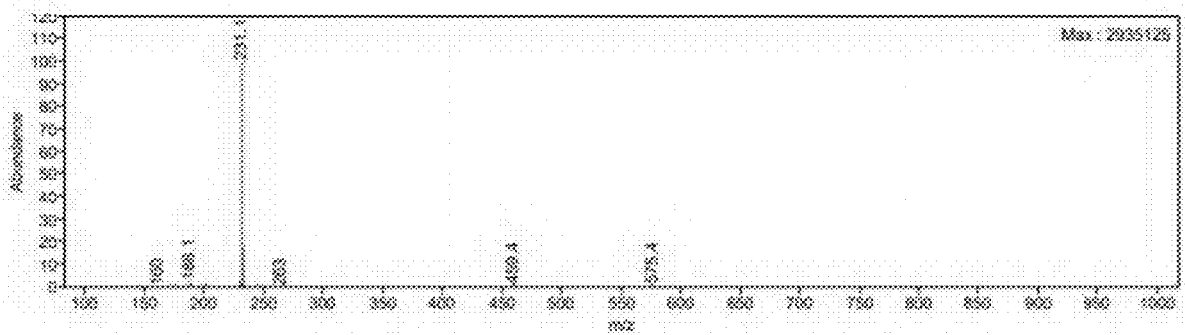
FIG. 825

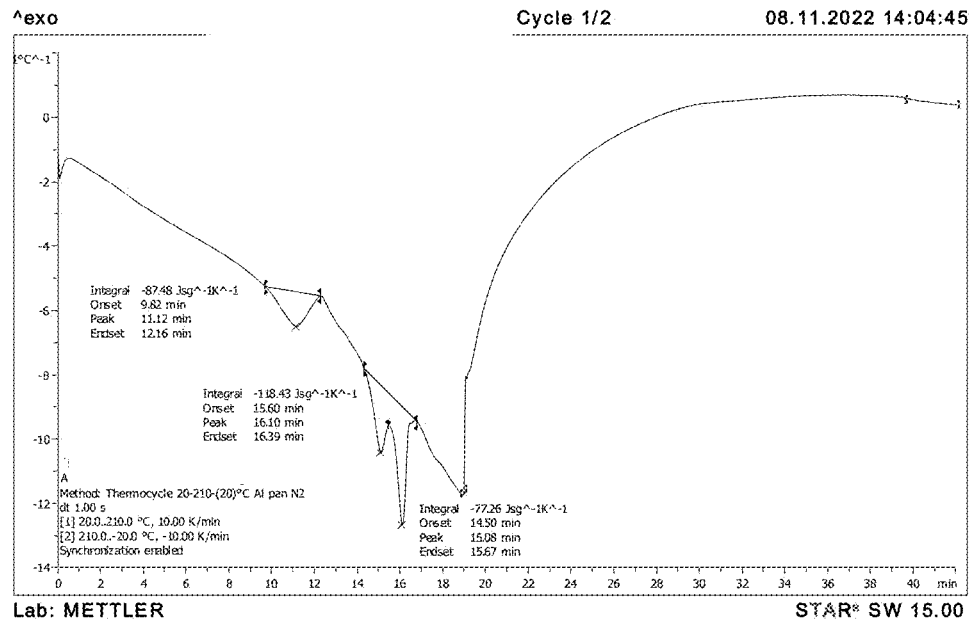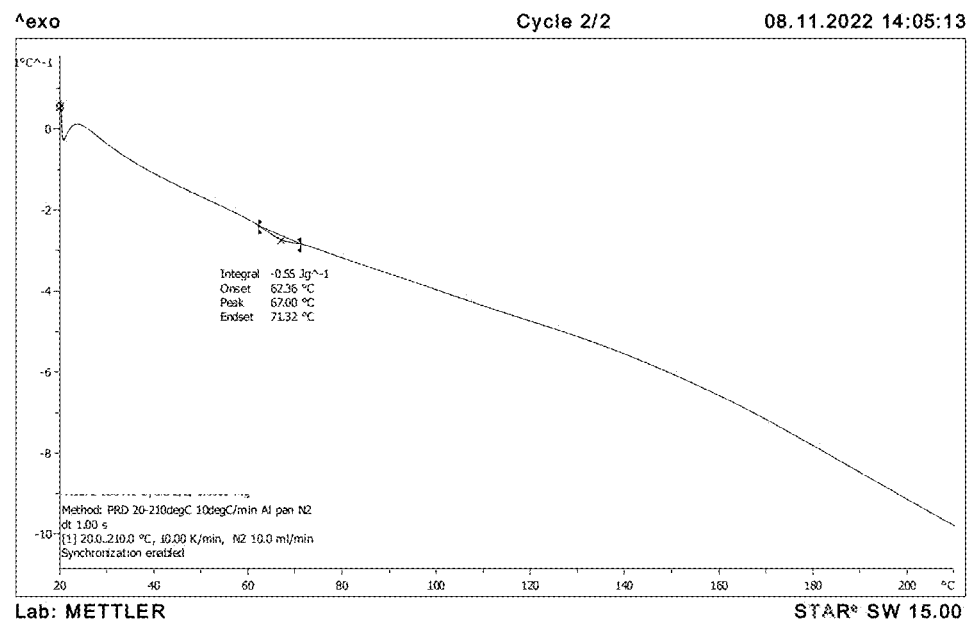
FIG. 852

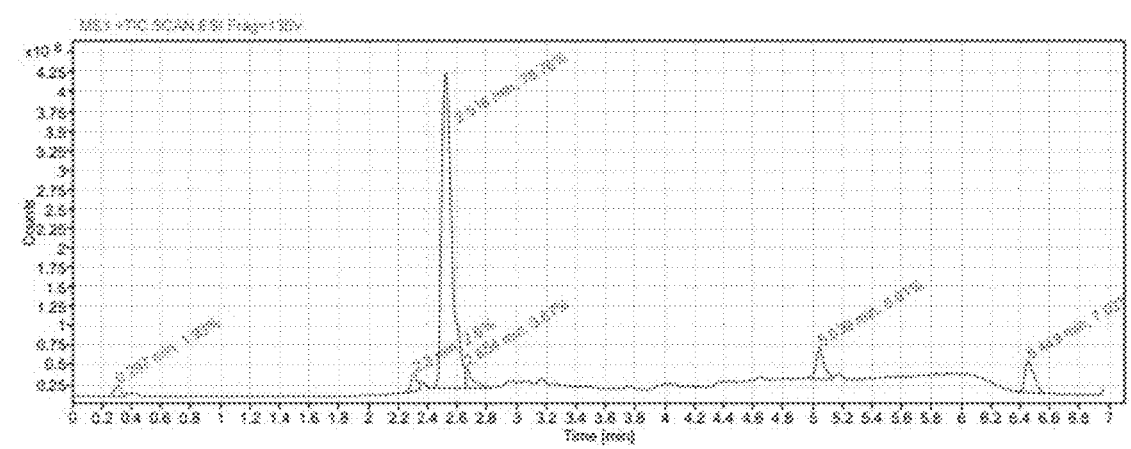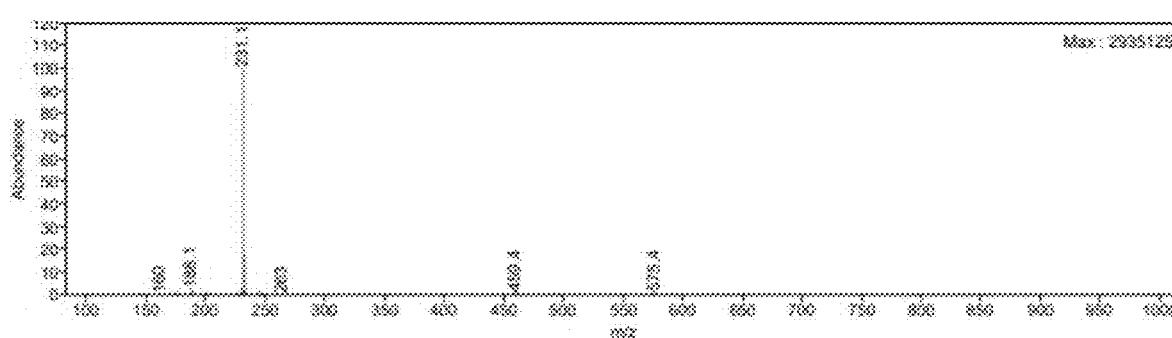
FIG. 857

Tabernanthalog*Native

Tabernanthalog*Native

SOLID FORMS OF TABERNANTHALOG MONOFUMARATE SALT FOR TREATING NEUROLOGICAL DISORDERS AND/OR PSYCHIATRIC DISORDERS

CROSS-REFERENCES TO RELATED APPLICATIONS

This application is a continuation of U.S. patent application Ser. No. 18/056,717 filed on Nov. 17, 2022 which claims priority to, and the benefit of, U.S. Provisional Application No. 63/280,514 filed on Nov. 17, 2021, U.S. Provisional Application No. 63/280,519 filed on Nov. 17, 2021, U.S. Provisional Application No. 63/310,981 filed on Feb. 16, 2022, U.S. Provisional Application No. 63/316,998 filed on Mar. 5, 2022, and U.S. Provisional Application No. 63/319,734 filed on Mar. 14, 2022, which are incorporated herein by reference in their entirety to the full extent permitted by law.

FIELD OF THE INVENTION

The present disclosure relates to salt and solid forms of 8-methoxy-3-methyl-1,2,3,4,5,6-hexahydroazepino[4,5-b]indole (commonly known as tabernanthalog), processes for their preparation and their use in the manufacture of a medicament for treating patients. The disclosure is also directed to pharmaceutical compositions containing at least one salt or solid form of tabernanthalog and to the therapeutic and/or prophylactic use of such salt and solid forms and compositions.

SUMMARY

The present disclosure is directed to salt and solid forms of tabernanthalog. It is also directed to the crystalline (such as solvates, non-solvates, polymorphs, salts, and a cocrystals) or amorphous (such as solvates, non-solvates, salts, and amorphized co-crystals) forms of the salt and solid forms of tabernanthalog.

Also disclosed are methods for making the salt and solid forms of tabernanthalog, as well as methods for using the same. In some embodiments, the solid form of tabernanthalog is a polymorph of the free base form of tabernanthalog. In other embodiments, the form of tabernanthalog is a salt form, such as a pharmaceutically acceptable salt. In salt embodiments of tabernanthalog, the salt may be provided in a solid form. Such solid forms of salts can be amorphous or crystalline. The solid form of tabernanthalog or a salt thereof may be a crystalline solid. In some embodiments, the crystalline solid may be substantially a single form, such as a polymorph form. In other embodiments, the solid form of tabernanthalog may be a solvate, such as a hydrate.

In some embodiments, the disclosed salt and solid forms of tabernanthalog have at least one desired property, or at least one particularly improved property compared to other forms of tabernanthalog, such as tabernanthalog free base, or compared to an amorphous form of tabernanthalog. In other embodiments, the at least one desired property, or the at least one particularly improved property of the salt and solid forms of tabernanthalog disclosed herein may comprise a physical property, a chemical property, a pharmacokinetic property, or a combination thereof. In yet other embodiments, the at least one desired property, or the at least one particularly improved property comprises a melting point, a glass transition temperature, flowability, thermal stability, mechanical stability, shelf life, stability against polymorphic transition, a hygroscopic property, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof.

Also disclosed herein are pharmaceutical compositions comprising a salt or a solid form of tabernanthalog, and further optionally comprising at least one pharmaceutically acceptable excipient.

A method for administering the salt or solid form of tabernanthalog is also disclosed herein. In some embodiments, the method comprises administering to a subject an effective amount of a salt or solid form of tabernanthalog, or a pharmaceutical composition thereof. In some embodiments, the subject is suffering from a neurological disease or a psychiatric disorder, or both, such as a neurodegenerative disorder. The neurological disorder or psychiatric disorder, or both, may comprise depression, addiction, anxiety, or a post-traumatic stress disorder. The neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

In some embodiments, administering the salt or solid form of tabernanthalog, or a pharmaceutical composition thereof comprises oral, intravenous, parenteral, or topical administration. In certain embodiments, oral administration is used. In other embodiments, the salt or solid form of tabernanthalog, or a pharmaceutical composition is administration by injection, inhalation, intraocular, intravaginal, intrarectal or transdermal routes.

In some embodiments, the tabernanthalog fumarate salt is crystalline polymorphic salt of tabernanthalog with Pattern #1, Pattern #2a, Pattern #2b, Pattern #2c, Pattern #2d, Pattern #3, Pattern #4a, Pattern #4b, Pattern #5, Pattern #6a, Pattern #6b, Pattern #7, Pattern #8, Pattern #9, Pattern #10, Pattern #11, Pattern #12, Pattern #13, Pattern #14, Pattern #15, Pattern #16, Pattern #17, Pattern #18, Pattern #19, Pattern #°2θ, Pattern #21, Pattern #22, or a mixture thereof.

In some embodiments, the tabernanthalog monofumarate salt is crystalline polymorphic Pattern #1 characterized by two or more, or three XRPD signals selected from the group consisting of 25.5 °2θ, 16.3 °2θ, and 19.3 °2θ (±0.2 °2θ; ±0.1 °2θ; or 0.0 °2θ; Cu Kα1 radiation).

In some embodiments, the tabernanthalog monofumarate salt is crystalline polymorphic Pattern #1 characterized by XRPD signals at 25.5 °2θ, 16.3 °2θ, and 19.3 °2θ (±0.2 °2θ; ±0.1 °2θ; or 0.0 °2θ; Cu Kα1 radiation).

In some embodiments, the tabernanthalog monofumarate salt is crystalline polymorphic Pattern #1 characterized by two or more, or three XRPD signals as shown in Table 155.

In some embodiments, the tabernanthalog monofumarate salt is crystalline polymorphic Pattern #1 characterized by two or more, or three XRPD signals selected from the group consisting of 25.5 °2θ, 16.3 °2θ, and 19.3 °2θ (±0.2 °2θ; ±0.1 °2θ; or 0.0 °2θ; Cu Kα1 radiation).

In some embodiments, the tabernanthalog monofumarate salt is crystalline polymorphic Pattern #1 characterized by XRPD signals at 25.5 °2θ, 16.3 °2θ, and 19.3 °2θ (±0.2 °2θ; ±0.1 °2θ; or 0.0 °2θ; Cu Kα1 radiation).

In some embodiments, the tabernanthalog monofumarate salt is crystalline polymorphic Pattern #1 characterized by two or more, or three XRPD signals as shown in Table 156.

In some embodiments, the tabernanthalog fumarate salt has an $^1$H NMR spectra as provided in FIGS. 295 and 296.

In some embodiments, the tabernanthalog fumarate salt has a TGA profile as provided in FIG. 299.

In some embodiments, the TGA profile of the tabernanthalog fumarate salt shows a first TG event (−2.1% w/w).

In some embodiments, the tabernanthalog fumarate salt has a DSC profile as provided in FIG. 300.

In some embodiments, the DSC profile of the tabernanthalog fumarate salt exhibits a bimodal transition corresponding to the melting of two different crystal forms.

In some embodiments, the tabernanthalog fumarate salt has a DVS profile as provided in FIG. 301.

In some embodiments, the tabernanthalog monofumarate salt is crystalline polymorphic Pattern #1 characterized by two or more, or three XRPD signals selected from the group consisting of 25.5 °2θ, 16.3 °2θ, 19.3 °2θ, 16.7 °2θ, 5.1 °2θ, 10.2 °2θ, 27.2 °2θ, 18.1 °2θ, 9 °2θ, and 26.8 °2θ(±0.2 °2θ; ±0.1 °2θ; or 0.0 °2θ; Cu Kα1 radiation).

In some embodiments, the tabernanthalog monofumarate salt is crystalline polymorphic Pattern #1 characterized by XRPD signals at 25.5 °2θ, 16.3 °2θ, 19.3 °2θ, 16.7 °2θ, 5.1 °2θ, 10.2 °2θ, 27.2 °2θ, 18.1 °2θ, 9 °2θ, and 26.8 °2θ (±0.2 °2θ; ±0.1 °2θ; or 0.0 °2θ; Cu Kα1 radiation).

In some embodiments, the tabernanthalog monofumarate salt is crystalline polymorphic Pattern #1 characterized by two or more, or three XRPD signals as shown in Table 157.

In some embodiments, the tabernanthalog monofumarate salt is crystalline polymorphic Pattern #2a characterized by XRPD signals at 25.6 °2θ, 16.4 °2θ, 17.1 °2θ, 23 °2θ, 9.1 °2θ, 27.3 °2θ, 15.7 °2θ, 26.8 °2θ, 18.1 °2θ, 20.7 °2θ, 12.3 °2θ, 25 °2θ, 22.8 °2θ, 21 °2θ, 14.2 °2θ, 24.7 °2θ, 17.4 °2θ, 18.8 °2θ, and 22.3 °2θ (±0.2 °2θ; ±0.1 °2θ; or 0.0 °2θ; Cu Kα1 radiation).

In some embodiments, the tabernanthalog monofumarate salt is crystalline polymorphic Pattern #2a characterized by two or more, or three XRPD signals selected from the group consisting of 25.6 °2θ, 16.4 °2θ, and 17.1 °2θ (±0.2 °2θ; ±0.1 °2θ; or 0.0 °2θ; Cu Kα1 radiation).

In some embodiments, the tabernanthalog monofumarate salt is crystalline polymorphic Pattern #2a characterized by XRPD signals at 25.6 °2θ, 16.4 °2θ, and 17.1 °2θ (±0.2 °2θ; ±0.1 °2θ; or 0.0 °2θ; Cu Kα1 radiation).

In some embodiments, the tabernanthalog monofumarate salt is crystalline polymorphic Pattern #2a characterized by two or more, or three XRPD signals as shown in Table 158.

In some embodiments, the tabernanthalog monofumarate salt is crystalline polymorphic Pattern #2a characterized by an $^1$H NMR spectrum as depicted in FIG. 313.

In some embodiments, the tabernanthalog monofumarate salt is crystalline polymorphic Pattern #2a characterized by an XRPD profile as depicted in FIG. 3.

In some embodiments, the tabernanthalog monofumarate salt is crystalline polymorphic Pattern #2a characterized by a TGA profile as depicted in FIG. 315.

In some embodiments, the tabernanthalog monofumarate salt is crystalline polymorphic Pattern #2a characterized by a DSC profile as depicted in FIG. 316.

In some embodiments, the tabernanthalog monofumarate salt is crystalline polymorphic Pattern #2b characterized by two or more, or three XRPD signals selected from the group consisting of 25.5 °2θ, 16.3 °2θ, 24.6 °2θ, 18.1 °2θ, 9.0 °2θ, 25.1 °2θ, 15.8 °2θ, 26.8 °2θ, 15.5 °2θ, and 17.0 °2θ, (±0.2 °2θ; ±0.1 °2θ; or ±0.0 °2θ; Cu Kα1 radiation).

In some embodiments, the tabernanthalog monofumarate salt is crystalline polymorphic Pattern #2b characterized by XRPD signals at 25.5 °2θ, 16.3 °2θ, 24.6 °2θ, 18.1 °2θ, 9.0 °2θ, 25.1 °2θ, 15.8 °2θ, 26.8 °2θ, 15.5 °2θ, and 17.0 °2θ (±0.2 °2θ; ±0.1 °2θ; or ±0.0 °2θ; Cu Kα1 radiation).

In some embodiments, the tabernanthalog monofumarate salt is crystalline polymorphic Pattern #2b characterized by two or more, or three XRPD signals as shown in Table 159.

In some embodiments, the tabernanthalog monofumarate salt is crystalline polymorphic Pattern #2c characterized by two or more, or three XRPD signals selected from the group consisting of 25.5 °2θ, 16.3 °2θ, 19.3 °2θ, 16.7 °2θ, 22.3 °2θ, 27.2 °2θ, 9 °2θ, 18.1 °2θ, 26.8 °2θ, and 17.7 °2θ (±0.2 °2θ; ±0.1 °2θ; or ±0.0 °2θ; Cu Kα1 radiation).

In some embodiments, the tabernanthalog monofumarate salt is crystalline polymorphic Pattern #2c characterized by XRPD signals at 25.5 °2θ, 16.3 °2θ, 19.3 °2θ, 16.7 °2θ, 22.3 °2θ, 27.2 °2θ, 9 °2θ, 18.1 °2θ, 26.8 °2θ, and 17.7 °2θ (±0.2 °2θ; ±0.1 °2θ; or ±0.0 °2θ; Cu Kα1 radiation).

In some embodiments, the tabernanthalog monofumarate salt is crystalline polymorphic Pattern #2c characterized by two or more, or three XRPD signals as shown in Table 160.

In some embodiments, the tabernanthalog monofumarate salt is crystalline polymorphic Pattern #2d characterized by two or more, or three XRPD signals selected from the group consisting of 25.6 °2θ, 16.3 °2θ, 16.2 °2θ, 25.2 °2θ, 9.1 °2θ, 22.1 °2θ, 26 °2θ, 26.8 °2θ, 18.1 °2θ, and 19.9 °2θ (±0.2 °2θ; ±0.1 °2θ; or ±0.0 °2θ; Cu Kα1 radiation).

In some embodiments, the tabernanthalog monofumarate salt is crystalline polymorphic Pattern #2d characterized by XRPD signals at 25.6 °2θ, 16.3 °2θ, 16.2 °2θ, 25.2 °2θ, 9.1 °2θ, 22.1 °2θ, 26 °2θ, 26.8 °2θ, 18.1 °2θ, and 19.9 °2θ (±0.2 °2θ; ±0.1 °2θ; or 0.0 °2θ; Cu Kα1 radiation).

In some embodiments, the tabernanthalog monofumarate salt is crystalline polymorphic Pattern #2d characterized by two or more, or three XRPD signals as shown in Table 161.

In some embodiments, the tabernanthalog monofumarate salt is crystalline polymorphic Pattern #3 characterized by two or more, or three XRPD signals selected from the group consisting of 25.5 °2θ, 16.3 °2θ, 16.6 °2θ, 20.1 °2θ, 26.0 °2θ, 22.2 °2θ, 26.8 °2θ, 16.8 °2θ, 18.8 °2θ, and 9.0 °2θ (±0.2 °2θ; ±0.1 °2θ; or 0.0 °2θ; Cu Kα1 radiation).

In some embodiments, the tabernanthalog monofumarate salt is crystalline polymorphic Pattern #3 characterized by XRPD signals at 25.5 °2θ, 16.3 °2θ, 16.6 °2θ, 20.1 °2θ, 26.0 °2θ, 22.2 °2θ, 26.8 °2θ, 16.8 °2θ, 18.8 °2θ, and 9.0 °2θ (±0.2 °2θ; ±0.1 °2θ; or ±0.0 °2θ; Cu Kα1 radiation).

In some embodiments, the tabernanthalog monofumarate salt is crystalline polymorphic Pattern #3 characterized by two or more, or three XRPD signals as shown in Table 162.

In some embodiments, the tabernanthalog monofumarate salt is crystalline polymorphic Pattern #4a characterized by two or more, or three XRPD signals selected from the group consisting of 25.5 °2θ, 16.3 °2θ, 8.2 °2θ, 11.3 °2θ, 9.0 °2θ, 23.8 °2θ, 19.3 °2θ, 17.1 °2θ, 19.4 °2θ, and 26.8 °2θ (±0.2 °2θ; ±0.1 °2θ; or 0.0 °2θ; Cu Kα1 radiation).

In some embodiments, the tabernanthalog monofumarate salt is crystalline polymorphic Pattern #4a characterized by XRPD signals at 25.5 °2θ, 16.3 °2θ, 8.2 °2θ, 11.3 °2θ, 9.0 °2θ, 23.8 °2θ, 19.3 °2θ, 17.1 °2θ, 19.4 °2θ, and 26.8 °2θ (±0.2 °2θ; ±0.1 °2θ; or 0.0 °2θ; Cu Kα1 radiation).

In some embodiments, the tabernanthalog monofumarate salt is crystalline polymorphic Pattern #4a characterized by two or more, or three XRPD signals as shown in Table 163.

In some embodiments, the tabernanthalog monofumarate salt is crystalline polymorphic Pattern #4b characterized by two or more, or three XRPD signals selected from the group consisting of 25.6 °2θ, 16.3 °2θ, 8.2 °2θ, 9.1 °2θ, 17.2 °2θ, 18.1 °2θ, 26.8 °2θ, 15.7 °2θ, 27.3 °2θ, and 21.5 °2θ (±0.2 °2θ; ±0.1 °2θ; or 0.0 °2θ; Cu Kα1 radiation).

In some embodiments, the tabernanthalog monofumarate salt is crystalline polymorphic Pattern #4b characterized by XRPD signals at 25.6 °2θ, 16.3 °2θ, 8.2 °2θ, 9.1 °2θ, 17.2 °2θ, 18.1 °2θ, 26.8 °2θ, 15.7 °2θ, 27.3 °2θ, and 21.5 °2θ (±0.2 °2θ; ±0.1 °2θ; or 0.0 °2θ; Cu Kα1 radiation).

In some embodiments, the tabernanthalog monofumarate salt is crystalline polymorphic Pattern #4b characterized by two or more, or three XRPD signals as shown in Table 164.

In some embodiments, the tabernanthalog hemifumarate salt is crystalline polymorphic Pattern #5 characterized by two or more, or three XRPD signals selected from the group consisting of 8.2 °2θ, 16.9 °2θ, 21.4 °2θ, 23.6 °2θ, 20.0 °2θ, 11.1 °2θ, 15.4 °2θ, 25.5 °2θ, 22.5 °2θ, and 23.9 °2θ (±0.2 °2θ; ±0.1 °2θ; or 0.0 °2θ; Cu Kα1 radiation).

In some embodiments, the tabernanthalog hemifumarate salt is crystalline polymorphic Pattern #5 characterized by XRPD signals at 8.2 °2θ, 16.9 °2θ, 21.4 °2θ, 23.6 °2θ, 20.0 °2θ, 11.1 °2θ, 15.4 °2θ, 25.5 °2θ, 22.5 °2θ, and 23.9 °2θ (±0.2 °2θ; ±0.1 °2θ; or 0.0 °2θ; Cu Kα1 radiation).

In some embodiments, the tabernanthalog hemifumarate salt is crystalline polymorphic Pattern #5 characterized by two or more, or three XRPD signals as shown in Table 181B.

In some embodiments, the tabernanthalog monofumarate salt is crystalline polymorphic Pattern #6a characterized by two or more, or three XRPD signals selected from the group consisting of 19.6 °2θ, 16.6 °2θ, 20.7 °2θ, 25.4 °2θ, 19.3 °2θ, 26.2 °2θ, 22.1 °2θ, and 33.6 °2θ (±0.2 °2θ; ±0.1 °2θ; or ±0.0 °2θ; Cu Kα1 radiation).

In some embodiments, the tabernanthalog monofumarate salt is crystalline polymorphic Pattern #6a characterized by two or more, or three XRPD signals selected from the group consisting of 19.6 °2θ, 16.6 °2θ, 20.7 °2θ, 25.4 °2θ, 19.3 °2θ, and 26.2 °2θ (±0.2 °2θ; ±0.1 °2θ; or ±0.0 °2θ; Cu Kα1 radiation).

In some embodiments, the tabernanthalog monofumarate salt is crystalline polymorphic Pattern #6a characterized by two or more, or three XRPD signals selected from the group consisting of 19.6 °2θ, 16.6 °2θ, 20.7 °2θ, 25.4 °2θ, 19.3 °2θ, and 26.2 °2θ (±0.2 °2θ; ±0.1 °2θ; or ±0.0 °2θ; Cu Kα1 radiation).

In some embodiments, the tabernanthalog monofumarate salt is crystalline polymorphic Pattern #6a characterized by two or more, or three XRPD signals selected from the group consisting of 19.6 °2θ, 16.6 °2θ, and 20.7 °2θ (±0.2 °2θ; ±0.1 °2θ; or 0.0 °2θ; Cu Kα1 radiation).

In some embodiments, the tabernanthalog monofumarate salt is crystalline polymorphic Pattern #6a characterized by XRPD signals at 19.6 °2θ, 16.6 °2θ, 20.7 °2θ, 25.4 °2θ, 19.3 °2θ, 26.2 °2θ, 22.1 °2θ, 33.6 °2θ, and 13 °2θ (±0.2 °2θ; ±0.1 °2θ; or ±0.0 °2θ; Cu Kα1 radiation).

In some embodiments, the tabernanthalog monofumarate salt is crystalline polymorphic Pattern #6a characterized by XRPD signals at 19.6 °2θ, 16.6 °2θ, and 20.7 °2θ (±0.2 °2θ; ±0.1 °2θ; or 0.0 °2θ; Cu Kα1 radiation).

In some embodiments, the tabernanthalog monofumarate salt is crystalline polymorphic Pattern #6a characterized by two or more, or three XRPD signals as shown in Table 166.

In some embodiments, the tabernanthalog monofumarate salt is crystalline polymorphic Pattern #6a characterized by an ¹H NMR spectrum as depicts in FIG. 344.

In some embodiments, the tabernanthalog monofumarate salt is crystalline polymorphic Pattern #6a characterized by an XRPD profile as depicts in FIG. 13.

In some embodiments, the tabernanthalog monofumarate salt is crystalline polymorphic Pattern #6a characterized by TGA profile as depicted in FIG. 347.

In some embodiments, the tabernanthalog monofumarate salt is crystalline polymorphic Pattern #6a characterized by a DSC profile as depicted in FIG. 348.

In some embodiments, the tabernanthalog monofumarate salt is crystalline polymorphic Pattern #6b characterized by two or more, or three XRPD signals selected from the group consisting of 19.4 °2θ, 16.5 °2θ, 20.5 °2θ, 25.3 °2θ, 26 °2θ, 22 °2θ, 12.9 °2θ, 8.2 °2θ, 33.4 °2θ, and 37.7 °2θ (±0.2 °2θ; ±0.1 °2θ; or 0.0 °2θ; Cu Kα1 radiation).

In some embodiments, the tabernanthalog monofumarate salt is crystalline polymorphic Pattern #6b characterized by XRPD signals at 19.4 °2θ, 16.5 °2θ, 20.5 °2θ, 25.3 °2θ, 26 °2θ, 22 °2θ, 12.9 °2θ, 8.2 °2θ, 33.4 °2θ, and 37.7 °2θ (±0.2 °2θ; ±0.1 °2θ; or ±0.0 °2θ; Cu Kα1 radiation).

In some embodiments, the tabernanthalog monofumarate salt is crystalline polymorphic Pattern #6b characterized by two or more, or three XRPD signals as shown in Table 167.

In some embodiments, the tabernanthalog monofumarate salt is crystalline polymorphic Pattern #7 characterized by two or more, or three XRPD signals selected from the group consisting of 16.4 °2θ, 25.6 °2θ, 15.9 °2θ, 7.2 °2θ, 24.9 °2θ, 19.4 °2θ, 9.1 °2θ, 21.3 °2θ, 19.8 °2θ, and 16.8 °2θ (±0.2 °2θ; ±0.1 °2θ; or 0.0 °2θ; Cu Kα1 radiation).

In some embodiments, the tabernanthalog monofumarate salt is crystalline polymorphic Pattern #7 characterized by XRPD signals at 16.4 °2θ, 25.6 °2θ, 15.9 °2θ, 7.2 °2θ, 24.9 °2θ, 19.4 °2θ, 9.1 °2θ, 21.3020, 19.8 °2θ, and 16.8 °2θ (±0.2 °2θ; ±0.1 °2θ; or ±0.0 °2θ; Cu Kα1 radiation).

In some embodiments, the tabernanthalog monofumarate salt is crystalline polymorphic Pattern #7 characterized by two or more, or three XRPD signals as shown in Table 168.

In some embodiments, the tabernanthalog monofumarate salt is crystalline polymorphic Pattern #8 characterized by two or more, or three XRPD signals selected from the group consisting of 25.5 °2θ, 16.3 °2θ, 15.8 °2θ, 24.2 °2θ, 20.5 °2θ, 24.8 °2θ, 18 °2θ, 19 °2θ, 7.6 °2θ, and 9 °2θ (±0.2 °2θ; ±0.1 °2θ; or 0.0 °2θ; Cu Kα1 radiation).

In some embodiments, the tabernanthalog monofumarate salt is crystalline polymorphic Pattern #8 characterized by XRPD signals at 25.5 °2θ, 16.3 °2θ, 15.8 °2θ, 24.2 °2θ, 20.5 °2θ, 24.8 °2θ, 18 °2θ, 19 °2θ, 7.6 °2θ, and 9 °2θ (±0.2 °2θ; ±0.1 °2θ; or ±0.0 °2θ; Cu Kα1 radiation).

In some embodiments, the tabernanthalog monofumarate salt is crystalline polymorphic Pattern #8 characterized by two or more, or three XRPD signals as shown in Table 169.

In some embodiments, the tabernanthalog monofumarate salt is crystalline polymorphic Pattern #9 characterized by two or more, or three XRPD signals selected from the group consisting of 15.9 °2θ, 25.6 °2θ, 24.7 °2θ, 16.4 °2θ, 19.5 °2θ, 21.9 °2θ, 17.1 °2θ, 8 °2θ, 9.2 °2θ, and 20.8 °2θ (±0.2 °2θ; ±0.1 °2θ; or 0.0 °2θ; Cu Kα1 radiation).

In some embodiments, the tabernanthalog monofumarate salt is crystalline polymorphic Pattern #9 characterized by XRPD signals at 15.9 °2θ, 25.6 °2θ, 24.7 °2θ, 16.4 °2θ, 19.5 °2θ, 21.9 °2θ, 17.1 °2θ, 8 °2θ, 9.2 °2θ, and 20.8 °2θ (±0.2 °2θ; ±0.1 °2θ; or ±0.0 °2θ; Cu Kα1 radiation).

In some embodiments, the tabernanthalog monofumarate salt is crystalline polymorphic Pattern #9 characterized by two or more, or three XRPD signals as shown in Table 170.

In some embodiments, the tabernanthalog monofumaratefmonoumarate salt is crystalline polymorphic Pattern #10 characterized by two or more, or three XRPD signals selected from the group consisting of 25.5 °2θ, 16.9 °2θ, 16.3 °2θ, 21.3 °2θ, 23.5 °2θ, 8.2 °2θ, 10.8 °2θ, 23.4 °2θ, 9.1 °2θ, and 19.8 °2θ (±0.2 °2θ; ±0.1 °2θ; or 0.0 °2θ; Cu Kα1 radiation).

In some embodiments, the tabernanthalog monofumarate salt is crystalline polymorphic Pattern #10 characterized by XRPD signals at 25.5 °2θ, 16.9 °2θ, 16.3 °2θ, 21.3 °2θ, 23.5

°2θ, 8.2 °2θ, 10.8 °2θ, 23.4 °2θ, 9.1 °2θ, and 19.8 °2θ (±0.2 °2θ; ±0.1 °2θ; or ±0.0 °2θ; Cu Kα1 radiation).

In some embodiments, the tabernanthalog monofumarate salt is crystalline polymorphic Pattern #10 characterized by two or more, or three XRPD signals as shown in Table 171.

In some embodiments, the tabernanthalog monofumarate salt is crystalline polymorphic Pattern #11 characterized by two or more, or three XRPD signals selected from the group consisting of 16.1 °2θ, 25.7 °2θ, 16.4 °2θ, 21.6 °2θ, 20.4 °2θ, 7.5 °2θ, 9.2 °2θ, 23.9 °2θ, 20.9 °2θ, and 17.4 °2θ (±0.2 °2θ; ±0.1 °2θ; or 0.0 °2θ; Cu Kα1 radiation).

In some embodiments, the tabernanthalog monofumarate salt is crystalline polymorphic Pattern #11 characterized by XRPD signals at 16.1 °2θ, 25.7 °2θ, 16.4 °2θ, 21.6 °2θ, 20.4 °2θ, 7.5 °2θ, 9.2 °2θ, 23.9 °2θ, 20.9 °2θ, and 17.4 °2θ (±0.2 °2θ; ±0.1 °2θ; or ±0.0 °2θ; Cu Kα1 radiation).

In some embodiments, the tabernanthalog monofumarate salt is crystalline polymorphic Pattern #11 characterized by two or more, or three XRPD signals as shown in Table 172.

In some embodiments, the tabernanthalog monofumarate salt is crystalline polymorphic Pattern #12 characterized by two or more, or three XRPD signals selected from the group consisting of 16.3 °2θ, 25.6 °2θ, 21.6 °2θ, 20.3 °2θ, 8.3 °2θ, 9.1 °2θ, 18.2 °2θ, 23 °2θ, 10.8 °2θ, and 14.3 °2θ(±0.2 °2θ; ±0.1 °2θ; or 0.0 °2θ; Cu Kα1 radiation).

In some embodiments, the tabernanthalog monofumarate salt is crystalline polymorphic Pattern #12 characterized by XRPD signals at 16.3 °2θ, 25.6 °2θ, 21.6 °2θ, 20.3 °2θ, 8.3 °2θ, 9.1 °2θ, 18.2 °2θ, 23 °2θ, 10.8 °2θ, and 14.3 °2θ (±0.2 °2θ; ±0.1 °2θ; or ±0.0 °2θ; Cu Kα1 radiation).

In some embodiments, the tabernanthalog monofumarate salt is crystalline polymorphic Pattern #12 characterized by two or more, or three XRPD signals as shown in Table 173.

In some embodiments, the tabernanthalog monofumarate salt is crystalline polymorphic Pattern #13 characterized by two or more, or three XRPD signals selected from the group consisting of 25.6 °2θ, 16 °2θ, 16.4 °2θ, 25.0 °2θ, 19.7 °2θ, 17.5 °2θ, 8.1 °2θ, 21.9 °2θ, 9.1 °2θ, and 10.5 °2θ(±0.2 °2θ; ±0.1 °2θ; or 0.0 °2θ; Cu Kα1 radiation).

In some embodiments, the tabernanthalog monofumarate salt is crystalline polymorphic Pattern #13 characterized by XRPD signals at 25.6 °2θ, 16 °2θ, 16.4 °2θ, 25.0 °2θ, 19.7 °2θ, 17.5 °2θ, 8.1 °2θ, 21.9 °2θ, 9.1 °2θ, and 10.5 °2θ (±0.2 °2θ; ±0.1 °2θ; or 0.0 °2θ; Cu Kα1 radiation).

In some embodiments, the tabernanthalog monofumarate salt is crystalline polymorphic Pattern #13 characterized by two or more, or three XRPD signals as shown in Table 174.

In some embodiments, the tabernanthalog hemifumarate salt is crystalline polymorphic Pattern #14 characterized by two or more, or three XRPD signals selected from the group consisting of 8.2 °2θ, 15.5 °2θ, and 17 °2θ (±0.2 °2θ; ±0.1 °2θ; or 0.0 °2θ; Cu Kα1 radiation).

In some embodiments, the tabernanthalog hemifumarate salt is crystalline polymorphic Pattern #14 characterized by XRPD signals at 8.2 °2θ, 15.5 °2θ, and 17 °2θ (±0.2 °2θ; ±0.1 °2θ; or ±0.0 °2θ; Cu Kα1 radiation).

In some embodiments, the tabernanthalog hemifumarate salt is crystalline polymorphic Pattern #14 characterized by two or more, or three XRPD signals as shown in Table 181D.

In some embodiments, the tabernanthalog hemifumarate salt is crystalline polymorphic Pattern #14 characterized by an $^1$H NMR spectrum as depicted in FIG. 377E.

In some embodiments, the tabernanthalog hemifumarate salt is crystalline polymorphic Pattern #14 characterized by an XRPD profile as depicted in FIG. 377F.

In some embodiments, the tabernanthalog hemifumarate salt is crystalline polymorphic Pattern #14 characterized by a TGA profile as depicted in FIG. 377I.

In some embodiments, the tabernanthalog hemifumarate salt is crystalline polymorphic Pattern #14 characterized by a DSC profile as depicted in FIG. 377J.

In some embodiments, the tabernanthalog monofumarate salt is crystalline polymorphic Pattern #15 characterized by two or more, or three XRPD signals selected from the group consisting of 16.2 °2θ, 17 °2θ, 25.5 °2θ, 23.3 °2θ, 21 °2θ, 16.9 °2θ, 19.9 °2θ, 24.4 °2θ, 8.4 °2θ, and 25.1 °2θ(±0.2 °2θ; ±0.1 °2θ; or 0.0 °2θ; Cu Kα1 radiation).

In some embodiments, the tabernanthalog monofumarate salt is crystalline polymorphic Pattern #15 characterized by XRPD signals at 16.2 °2θ, 17 °2θ, 25.5 °2θ, 23.3 °2θ, 21 °2θ, 16.9 °2θ, 19.9 °2θ, 24.4 °2θ, 8.4 °2θ, and 25.1 °2θ (±0.2 °2θ; ±0.1 °2θ; or ±0.0 °2θ; Cu Kα1 radiation).

In some embodiments, the tabernanthalog monofumarate salt is crystalline polymorphic Pattern #15 characterized by two or more, or three XRPD signals as shown in Table 176.

In some embodiments, the tabernanthalog monofumarate salt is crystalline polymorphic Pattern #16 characterized by two or more, or three XRPD signals selected from the group consisting of 25.6 °2θ, 16.4 °2θ, 17 °2θ, 24.4 °2θ, 19.3 °2θ, 9.1 °2θ, 16.8 °2θ, 9.6 °2θ, 18.1 °2θ, and 22.4 °2θ(±0.2 °2θ; ±0.1 °2θ; or 0.0 °2θ; Cu Kα1 radiation).

In some embodiments, the tabernanthalog monofumarate salt is crystalline polymorphic Pattern #16 characterized by XRPD signals at 25.6 °2θ, 16.4 °2θ, 17 °2θ, 24.4 °2θ, 19.3 °2θ, 9.1 °2θ, 16.8 °2θ, 9.6 °2θ, 18.1 °2θ, and 22.4 °2θ (±0.2 °2θ; ±0.1 °2θ; or ±0.0 °2θ; Cu Kα1 radiation).

In some embodiments, the tabernanthalog monofumarate salt is crystalline polymorphic Pattern #16 characterized by two or more, or three XRPD signals as shown in Table 177.

In some embodiments, the tabernanthalog monofumarate salt is crystalline polymorphic Pattern #17 characterized by two or more, or three XRPD signals selected from the group consisting of 25.6 °2θ, 16.4 °2θ, 16.6 °2θ, 23.6 °2θ, 21.7 °2θ, 19.6 °2θ, 26.9 °2θ, 9.1 °2θ, 22.4 °2θ, and 23.2 °2θ (±0.2 °2θ; ±0.1 °2θ; or ±0.0 °2θ; Cu Kα1 radiation).

In some embodiments, the tabernanthalog monofumarate salt is crystalline polymorphic Pattern #17 characterized by XRPD signals at 25.6 °2θ, 16.4 °2θ, 16.6 °2θ, 23.6 °2θ, 21.7 °2θ, 19.6 °2θ, 26.9 °2θ, 9.1 °2θ, 22.4 °2θ, and 23.2 °2θ (±0.2 °2θ; ±0.1 °2θ; or ±0.0 °2θ; Cu Kα1 radiation).

In some embodiments, the tabernanthalog monofumarate salt is crystalline polymorphic Pattern #17 characterized by two or more, or three XRPD signals as shown in Table 178.

In some embodiments, the tabernanthalog monofumarate salt is crystalline polymorphic Pattern #18 characterized by two or more, or three XRPD signals selected from the group consisting of 25.6 °2θ, 16 °2θ, 18 °2θ, 16.3 °2θ, 21.4 °2θ, 26.8 °2θ, 23 °2θ, 25.9 °2θ, 15.5 °2θ, and 11 °2θ (±0.2 °2θ; ±0.1 °2θ; or 0.0 °2θ; Cu Kα1 radiation).

In some embodiments, the tabernanthalog monofumarate salt is crystalline polymorphic Pattern #18 characterized by XRPD signals at 25.6 °2θ, 16 °2θ, 18 °2θ, 16.3 °2θ, 21.4 °2θ, 26.8 °2θ, 23 °2θ, 25.9 °2θ, 15.5 °2θ, and 11 °2θ (±0.2 °2θ; ±0.1 °2θ; or ±0.0 °2θ; Cu Kα1 radiation).

In some embodiments, the tabernanthalog monofumarate salt is crystalline polymorphic Pattern #18 characterized by two or more, or three XRPD signals as shown in Table 179.

In some embodiments, the tabernanthalog monofumarate salt is crystalline polymorphic Pattern #19 characterized by two or more, or three XRPD signals selected from the group consisting of 25.6 °2θ, 25.5 °2θ, 16.4 °2θ, 20.5 °2θ, 16.3

°2θ, 26.7 °2θ, 22.8 °2θ, 19.5 °2θ, 19.4 °2θ, and 17.0 °2θ (±0.2 °2θ; ±0.1 °2θ; or 0.0 °2θ; Cu Kα1 radiation).

In some embodiments, the tabernanthalog monofumarate salt is crystalline polymorphic Pattern #19 characterized by XRPD signals at 25.6 °2θ, 25.5 °2θ, 16.4 °2θ, 20.5 °2θ, 16.3 °2θ, 26.7 °2θ, 22.8 °2θ, 19.5 °2θ, 19.4 °2θ, and 17.0 °2θ (±0.2 °2θ; ±0.1 °2θ; or ±0.0 °2θ; Cu Kα1 radiation).

In some embodiments, the tabernanthalog monofumarate salt is crystalline polymorphic Pattern #19 characterized by two or more, or three XRPD signals as shown in Table 180.

In some embodiments, the tabernanthalog monofumarate salt is crystalline polymorphic Pattern #20 characterized by two or more, or three XRPD signals selected from the group consisting of 6.1 °2θ, 25.5 °2θ, 16.3 °2θ, 19.0 °2θ, 18.2 °2θ, 15.9 °2θ, and 16.7 °2θ (±0.2 °2θ; ±0.1 °2θ; or ±0.0 °2θ; Cu Kα1 radiation).

In some embodiments, the tabernanthalog monofumarate salt is crystalline polymorphic Pattern #20 characterized by XRPD signals at 6.1 °2θ, 25.5 °2θ, 16.3 °2θ, 19.0 °2θ, 18.2 °2θ, 15.9 °2θ, and 16.7 °2θ (±0.2 °2θ; ±0.1 °2θ; or 0.0 °2θ; Cu Kα1 radiation).

In some embodiments, the tabernanthalog monofumarate salt is crystalline polymorphic Pattern #20 characterized by two or more, or three XRPD signals as shown in Table 181.

In some embodiments, the tabernanthalog hemifumarate salt is crystalline polymorphic Pattern #21 characterized by two or more, or three XRPD signals selected from the group consisting of 19.2 °2θ, 16.7 °2θ, 25.4 °2θ, 22.2 °2θ, 27.2 °2θ, 18.1 °2θ, 17.7 °2θ, 21.2 °2θ, 26.1 °2θ, and 6.7 °2θ (±0.2 °2θ; ±0.1 °2θ; or 0.0 °2θ; Cu Kα1 radiation).

In some embodiments, the tabernanthalog hemifumarate salt is crystalline polymorphic Pattern #21 characterized by XRPD signals at 19.2 °2θ, 16.7 °2θ, 25.4 °2θ, 22.2 °2θ, 27.2 °2θ, 18.1 °2θ, 17.7 °2θ, 21.2 °2θ, 26.1 °2θ, and 6.7 °2θ (±0.2 °2θ; ±0.1 °2θ; or ±0.0 °2θ; Cu Kα1 radiation).

In some embodiments, the tabernanthalog hemifumarate salt is crystalline polymorphic Pattern #21 characterized by two or more, or three XRPD signals as shown in Table 182.

In some embodiments, the tabernanthalog hemifumarate salt is crystalline polymorphic Pattern #22 characterized by two or more, or three XRPD signals selected from the group consisting of 18.9 °2θ, 19.3 °2θ, 16.7 °2θ, 27.3 °2θ, 18.2 °2θ, 25.5 °2θ, 6.7 °2θ, 17.7 °2θ, 20.2 °2θ, and 22.3 °2θ (±0.2 °2θ; ±0.1 °2θ; or 0.0 °2θ; Cu Kα1 radiation).

In some embodiments, the tabernanthalog hemifumarate salt is crystalline polymorphic Pattern #22 characterized by XRPD signals at 18.9 °2θ, 19.3 °2θ, 16.7 °2θ, 27.3 °2θ, 18.2 °2θ, 25.5 °2θ, 6.7 °2θ, 17.7 °2θ, 20.2 °2θ, and 22.3 °2θ (±0.2 °2θ; ±0.1 °2θ; or ±0.0 °2θ; Cu Kα1 radiation).

In some embodiments, the tabernanthalog hemifumarate salt is crystalline polymorphic Pattern #22 characterized by two or more, or three XRPD signals as shown in Table 183.

In some embodiments, the tabernanthalog monofumarate salt has Pattern #6a (Form A) has a crystal data as shown in FIG. 285 when collected using Single Crystal XRD.

In some embodiments, Form A of the tabernanthalog monofumarate salt is obtained from suspension equilibration of the tabernanthalog fumarate salt in water (5 vol) at 90° C., and the product is isolated by filtration and dried under sustained nitrogen flux (<1 bar) over 20 h at 20° C.

In some embodiments, Form A of the tabernanthalog monofumarate salt is obtained from suspension equilibration of the tabernanthalog fumarate salt in water (5 vol) at 20° C., and the product is isolated by filtration and dried under sustained nitrogen flux (<1 bar) over 20 h at 20° C.

In some embodiments, Form B of the tabernanthalog monofumarate salt is obtained from suspension equilibration of the tabernanthalog fumarate salt in acetonitrile (5 vol) at 40° C., and the product is isolated by centrifugation and oven-dried under vacuum over 20 h at 40° C.

In some embodiments, the tabernanthalog hemifumarate salt has Pattern #14 (Form I) has a crystal data as shown in FIG. 286 when collected using single Crystal XRD.

In some embodiments, Form I of the tabernanthalog hemifumarate salt is obtained from dissolution of Tabernanthalog (native); TBG Native and fumaric acid (0.5 equiv) in methanol (20 vol).

In some embodiments, the tabernanthalog fumarate salt Form A (unary fumarate, Pattern #6a), is prepared from water (anhydrous form, generated via suspension equilibration in water at 20° C.).

In some embodiments, in the presence of Form A, Form B slowly evolves into Form A under competitive suspension equilibration conditions.

In some embodiments, metastable forms obtained via suspension equilibration and wet pellets, readily undergo conversion into Form A during drying.

In some embodiments, Form A exhibits greatest relative stability amongst other forms of the tabernanthalog fumarate salt.

In some embodiments, the hemi-fumarate salt of the tabernanthalog fumarate salt is prepared and re-proportionated into the fumarate salt during an ageing cycle.

In some embodiments, stability assessment of the supplied material (Pattern #1) at 40° C./75% RH executed over a 4-to-5-week period shows no evidence for hydrate formation, chemical degradation or disproportionation of the API.

In some embodiments, the tabernanthalog salt is a tabernanthalog sorbate salt, a tabernanthalog tartrate salt, a tabernanthalog maleate salt, or a tabernanthalog benzoate salt.

In some embodiments, the tabernanthalog salt has at least one of the following characteristics: (a) a unique powder diffraction pattern by XRPD, (b) a flat baseline leading to single melt event by DSC, (c) a flat baseline up to the melt by TGA, (d) a significantly reduced impurity burden and absence of trace solvents by $^1$H NMR, and (e) an optically crystalline and reasonably equant morphology under cross-polarized filter.

In yet other embodiments, the tabernanthalog salt is at least about 95% pure as measured by HPLC.

In other embodiments, the tabernanthalog salt is at least about 95% pure as measured by UV chromatographic method.

In some embodiments, Form A of the tabernanthalog sorbate salt is obtained from heat-up/cool-down crystallization of tabernanthalog (native) with sorbic acid in ethanol (5.0 vol) at 85° C.

The product was isolated by centrifugation and was oven-dried under reduced pressure over 20 h at 40° C.

In yet other embodiments, Form A of the tabernanthalog sorbate salt is obtained heat-up/cool-down crystallization of tabernanthalog (native) with sorbic acid in ethanol (3.0 vol) and the salt is isolated by filtration and dried under sustained nitrogen flux (<1 bar) over 20 h at 20° C.

In one embodiment, Form A of the tabernanthalog sorbate salt is a unary sorbate with 24.7% w/w th., sorbic acid (i.e., 1.0 mol of API to 1.0 mol sorbic acid).

In one embodiment, Form A of the tabernanthalog sorbate salt is crystalline characterized by two or more, or three XRPD signals selected from the group consisting of 5.7 °2θ, 11.4 °2θ, 24.7 °2θ, 18.8 °2θ, 10.5 °2θ, 22.6 °2θ, 24.4 °2θ, 26.9 °2θ, 19.1 °2θ, and 21.4 °2θ (±0.2 °2θ; ±0.1 °2θ; or ±0.0 °2θ; Cu Kα1 radiation).

In one embodiment, Form A of the tabernanthalog sorbate salt is crystalline characterized by two or more, or three XRPD signals selected from the group consisting of 5.7 °2θ, 11.4 °2θ, and 24.7020 (±0.2 °2θ; ±0.1 °2θ; or 0.0 °2θ; Cu Kα1 radiation).

In one embodiment, Form A of the tabernanthalog sorbate salt is crystalline characterized by XRPD signals at 5.7 °2θ, 11.4 °2θ, 24.7 °2θ, 18.8 °2θ, 10.5 °2θ, 22.6 °2θ, 24.4 °2θ, 26.9 °2θ, 19.1 °2θ, and 21.4020 (±0.2 °2θ; ±0.1 °2θ; or 0.0 °2θ; Cu Kα1 radiation).

In one embodiment, Form A of the tabernanthalog sorbate salt is crystalline characterized by XRPD signals at 5.7 °2θ, 11.4 °2θ, and 24.7 °2θ (±0.2 °2θ; ±0.1 °2θ; or ±0.0 °2θ; Cu Kα1 radiation).

In some embodiments, Form A of the tabernanthalog sorbate salt is crystalline characterized two or more, or three XRPD signals as shown in Table 216.

In some embodiments, Form A of the tabernanthalog sorbate salt is crystalline characterized two or more, or three XRPD signals as shown in FIG. 384.

In some embodiments, Form A of the tabernanthalog sorbate salt exhibits an $^1$H NMR spectrum as depicted in FIG. 451, FIG. 561, or FIG. 562.

In some embodiments, Form A of the tabernanthalog sorbate salt exhibits a DSC profile as depicted in FIG. 453.

In some embodiments, Form A of the tabernanthalog sorbate salt exhibits a TGA profile as depicted in FIG. 454.

In some embodiments, Form A of the tabernanthalog sorbate salt exhibits a DVS profile as depicted in FIG. 455 or FIG. 456.

In some embodiments, Form A of the tabernanthalog sorbate salt exhibits an XRPD pattern as depicted in FIG. 384.

In some embodiments, Form A of the tabernanthalog sorbate salt exhibits an XRPD pattern post DVS as depicted in FIG. 458.

In some embodiments, Form A of the tabernanthalog sorbate salt exhibits an HPLC spectrum as depicted in FIG. 460 or FIG. 566.

In some embodiments, Form A of the tabernanthalog sorbate salt exhibits at least one property as listed in Table 192.

In some embodiments, the tabernanthalog sorbate salt is crystalline polymorphic (Form A) and characterized by XRPD signals at 5.7 °2θ, 11.4 °2θ, and 22.8 °2θ (±0.2 °2θ; ±0.1 °2θ; or 0.0 °2θ; Cu Kα1 radiation).

In some embodiments, the tabernanthalog sorbate salt is crystalline polymorphic (Form A) and characterized by two or more, or three XRPD signals selected from the group consisting of 5.7 °2θ, 11.4 °2θ, and 22.8 °2θ (±0.2 °2θ; ±0.1 °2θ; or 0.0 °2θ; Cu Kα1 radiation).

In some embodiments, the tabernanthalog sorbate salt is crystalline polymorphic (Form A) and characterized by XRPD signals at 5.7 °2θ, 11.4 °2θ, 22.6 °2θ and 24.7 °2θ (±0.2 °2θ; ±0.1 °2θ; or 0.0 °2θ; Cu Kα1 radiation).

In some embodiments, the tabernanthalog sorbate salt is crystalline polymorphic (Form A) and characterized by two or more, or three XRPD signals selected from the group consisting of 5.7 °2θ, 11.4 °2θ, 22.6 °2θ and 24.7 °2θ (±0.2 °2θ; ±0.1 °2θ; or 0.0 °2θ; Cu Kα1 radiation).

In some embodiments, the tabernanthalog sorbate salt (Form A) has a crystal data when collected using Single Crystal XRD as follows: $C_{20}H_{26}N_2O_3$, $M_r$=342.43, monoclinic, $P2_1/c$ (No. 14), a=9.3410(3) Å, b=6.4173(2) Å, c=30.5108(12) Å, b=95.374(3), a=g=90°, V=1820.90(11) Å$^3$, T=100(2) K, Z=4, Z'=1, m(Cu K$_a$)=0.675 mm$^{-1}$, 13832 reflections measured, 3694 unique ($R_{int}$=0.0462) which were used in all calculations. The final wR$_2$ was 0.2098 (all data) and R$_1$ was 0.0826 (I≥2 s(I)).

In some embodiments, the tabernanthalog sorbate salt is crystalline polymorphic (Form B; Pattern #1) and characterized by XRPD signals at 7.5 °2θ, and 15.1 °2θ (±0.2 °2θ; ±0.1 °2θ; or 0.0 °2θ; Cu Kα1 radiation).

In some embodiments, the tabernanthalog sorbate salt is crystalline polymorphic (Form C; Pattern #2) and characterized by XRPD signals at 5.7 °2θ, and 11.5 °2θ (±0.2 °2θ; ±0.1 °2θ; or ±0.0 °2θ; Cu Kα1 radiation).

In some embodiments, the tabernanthalog sorbate salt is crystalline polymorphic (Form C; Pattern #2) and characterized by XRPD signals at 5.7 °2θ, 22.4 °2θ, 11.5 °2θ, 16.7 °2θ, 17.3 °2θ, 18.5 °2θ, 18.7 °2θ, 17.8 °2θ, 11.2 °2θ, 20.1 °2θ, 13.9 °2θ, and 29.7 °2θ (±0.2 °2θ; ±0.1 °2θ; or ±0.0 °2θ; Cu Kα1 radiation).

In some embodiments, the tabernanthalog sorbate salt is crystalline polymorphic (Form C; Pattern #2) and characterized by two or more, or three XRPD signals selected from the group consisting of 5.7 °2θ, 22.4 °2θ, 11.5 °2θ, 16.7 °2θ, 17.3 °2θ, 18.5 °2θ, 18.7 °2θ, 17.8 °2θ, 11.2 °2θ, 20.1 °2θ, 13.9 °2θ, and 29.7 °2θ (±0.2 °2θ; ±0.1 °2θ; or ±0.0 °2θ; Cu Kα1 radiation).

In some embodiments, the tabernanthalog sorbate salt·$H_2O$ (hydrate) has a crystal data when collected using Single Crystal XRD as follows: $C_{20}H_{28}N_2O_4$, $M_r$=360.44, monoclinic, $P2_1/c$ (No. 14), a=16.07470(10) Å, b=12.14150(10) Å, c=10.85080(10) Å, b=109.2390(10)°, a=g=90°, V=1999.49(3) Å$^3$, T=100(2) K, Z=4, Z'=1, m(Cu K$_a$)=0.676 mm$^{-1}$, 51305 reflections measured, 3786 unique ($R_{int}$=0.0483) which were used in all calculations. The final wR$_2$ was 0.0874 (all data) and R$_1$ was 0.0347 (I≥2 s(I)).

In one embodiment, the tabernanthalog sorbate salt is characterized by one of the following properties: (1) show minimal reduction in CP (from 99.76% area to 99.70% area), (2) is highly soluble in the SIF buffers (apart from FaSSGF), (3) exhibits higher crystallographic quality than the tabernanthalog fumarate salt, (4) has better solvent and impurity rejection on scale-up.

The foregoing and other objects, features, and advantages of the invention will become more apparent from the following detailed description, which proceeds with reference to the accompanying figures.

BRIEF DESCRIPTION OF THE DRAWINGS

The accompanying drawings, which are included to provide a further understanding of the present disclosure, are incorporated in and constitute a part of this specification, illustrate aspects of the present disclosure and, together with the detailed description, serve to explain the principles of the present disclosure. The patent or application file contains at least one drawing executed in color. Copies of this patent or patent application publication with color drawing(s) will be provided by the Office upon request and payment of the necessary fee.

FIG. 92 depicts the LC-MS report of 5-O1 (Experiment Reference 5-Sample Reference O1).

FIG. 116 depicts the XRPD profile of 6-N2 (Experiment Reference 6-Sample Reference N2) (Pattern #1).

FIG. 117 depicts the XRPD profile of 6-O1 (Experiment Reference 6-Sample Reference O1) (Pattern #1).

FIG. 118 depicts the XRPD profile of 6-P2 (Experiment Reference 6-Sample Reference P2) (Pattern #4a).

FIG. 119 depicts the XRPD profile of 6-Q2 (Experiment Reference 6-Sample Reference Q2) (Pattern #2b).

FIG. 120 depicts the XRPD profile of 6-R1 (Experiment Reference 6-Sample Reference R1) (Pattern #3).

FIG. 121 depicts the XRPD profile of 6-S1 (Experiment Reference 6-Sample Reference S1) (Pattern #6a).

FIG. 122 depicts the XRPD profile of 7-A2 (Experiment Reference 7-Sample Reference A2) (Pattern #19).

FIG. 123 depicts the XRPD profile of 7-B1 (Experiment Reference 7-Sample Reference B1) (Pattern #2a).

FIG. 124 depicts the XRPD profile of 7-C1 (Experiment Reference 7-Sample Reference C1) (Pattern #1).

FIG. 125 depicts the XRPD profile of 7-C2 (Experiment Reference 7-Sample Reference C2) (Pattern #1).

FIG. 126 depicts the XRPD profile of 7-D1 (Experiment Reference 7-Sample Reference D1) (Pattern #3).

FIG. 127 depicts the XRPD profile of 7-D2 (Experiment Reference 7-Sample Reference D2) (Pattern #1).

Figure 128:
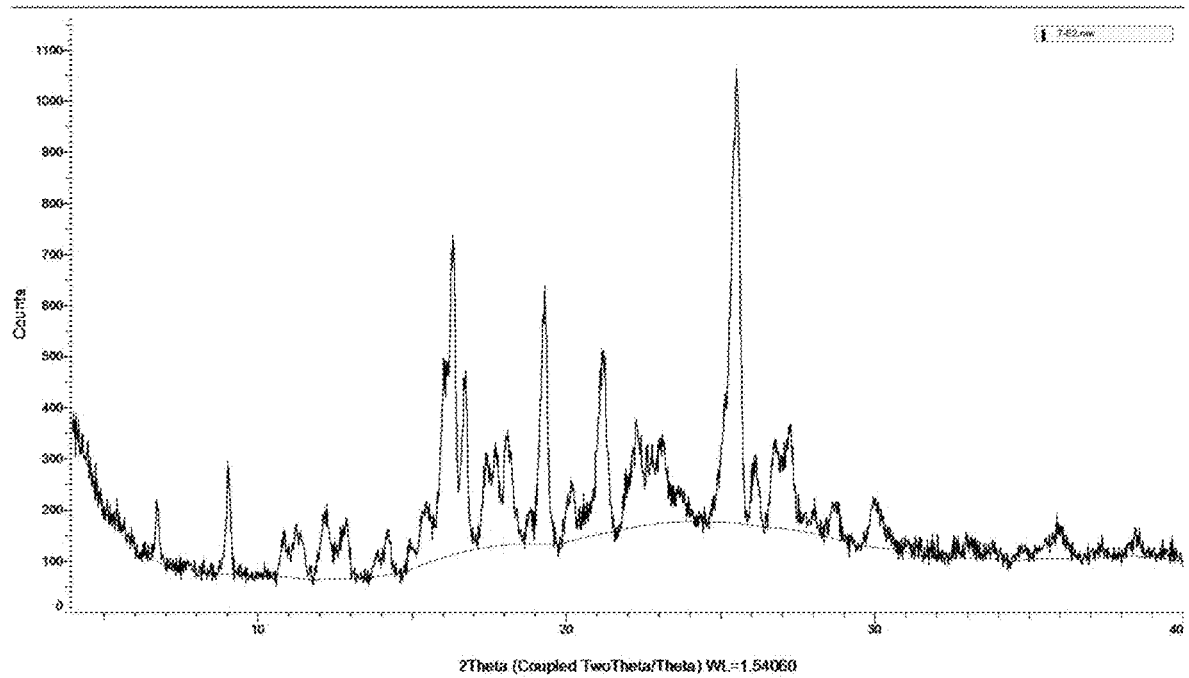

FIG. 128 depicts the XRPD profile of 7-E2 (Experiment Reference 7-Sample Reference E2) (Pattern #1).

Figures 129, 130:
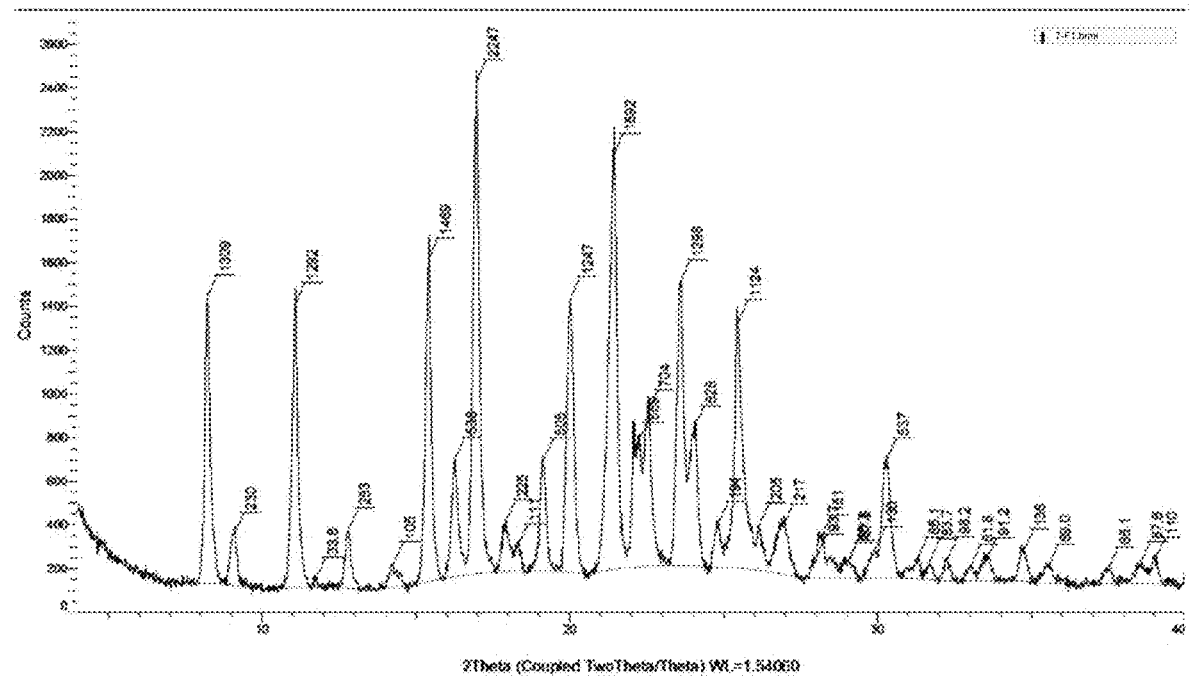

FIG. 129 depicts the XRPD profile of 7-F1 (Experiment Reference 7-Sample Reference F1) (Pattern #5).

FIG. 130 depicts the XRPD profile of 7-G1 (Experiment Reference 7-Sample Reference G1) (Pattern #9).

Figure 131:
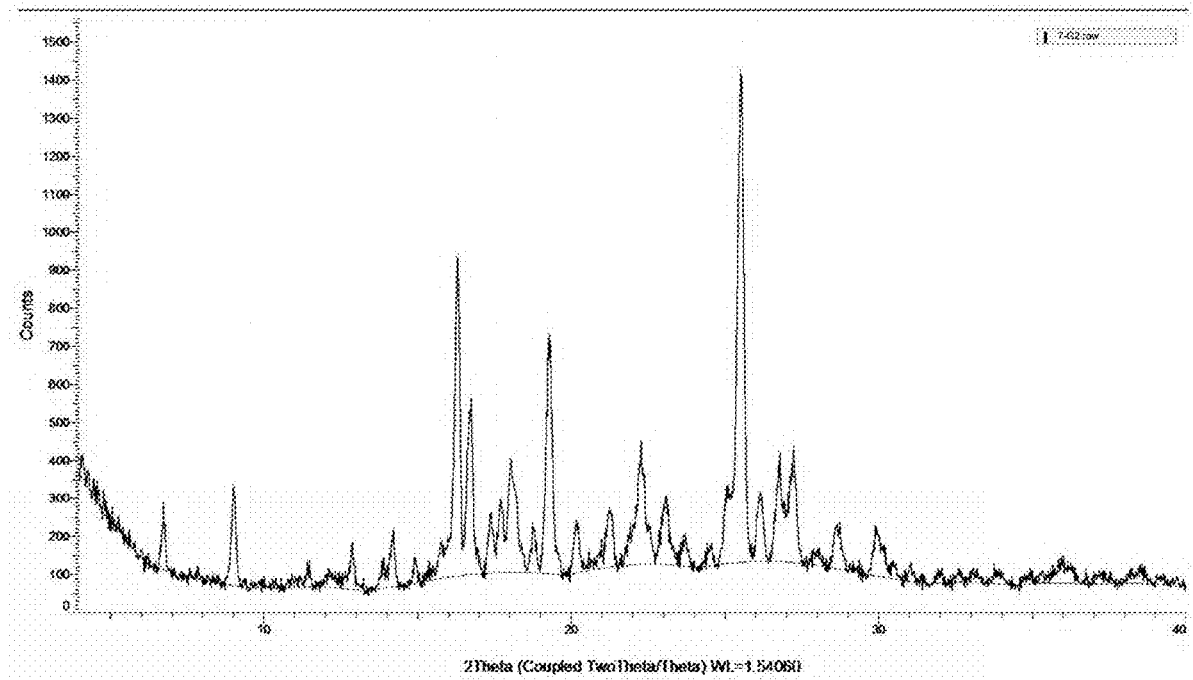

FIG. 131 depicts the XRPD profile of 7-G2 (Experiment Reference 7-Sample Reference G2) (Pattern #1).

Figure 132:
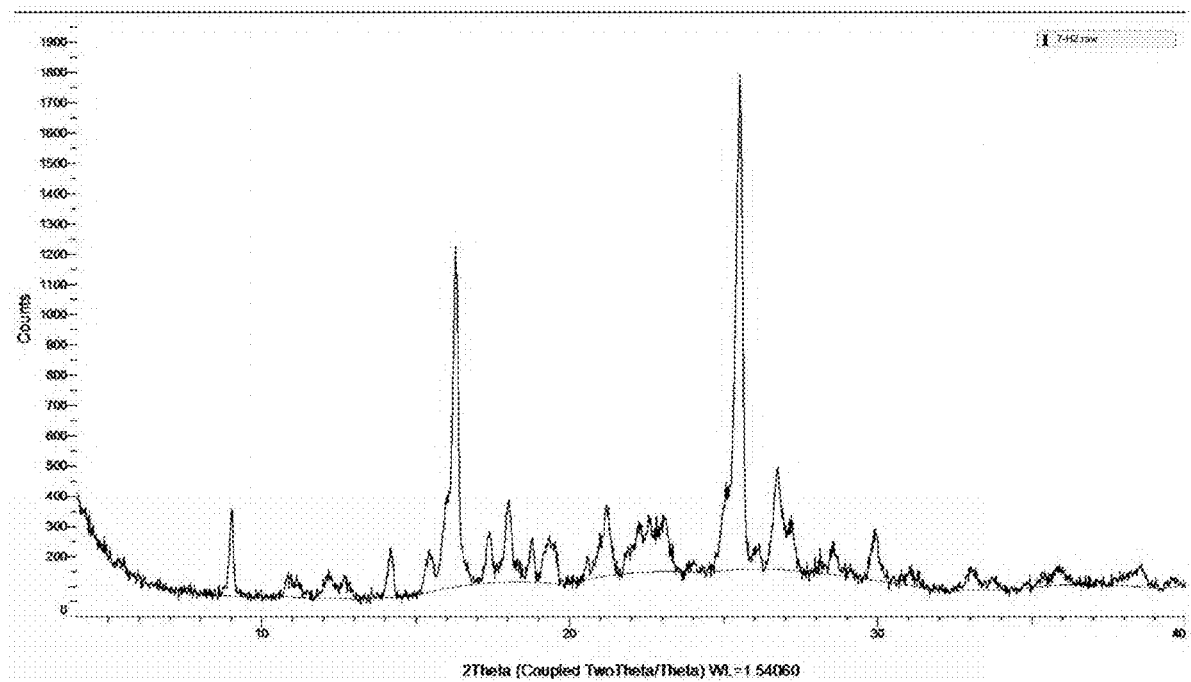

FIG. 132 depicts the XRPD profile of 7-H2 (Experiment Reference 7-Sample Reference H2) (Pattern #2b).

Figure 133:
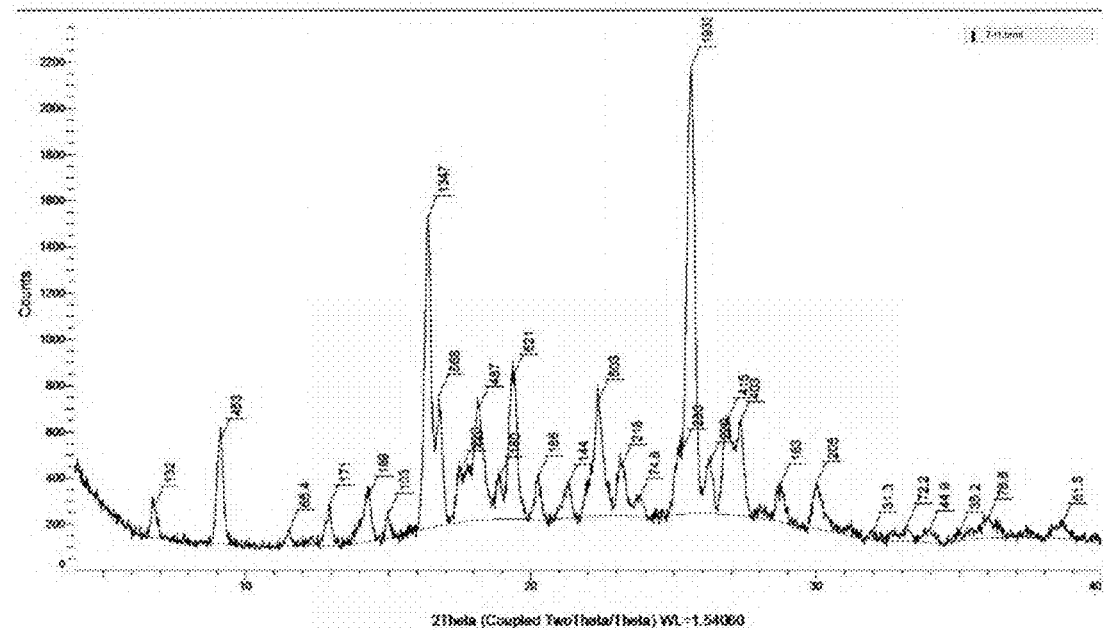

FIG. 133 depicts the XRPD profile of 7-I1 (Experiment Reference 7-Sample Reference I1) (Pattern #1).

Figure 134:
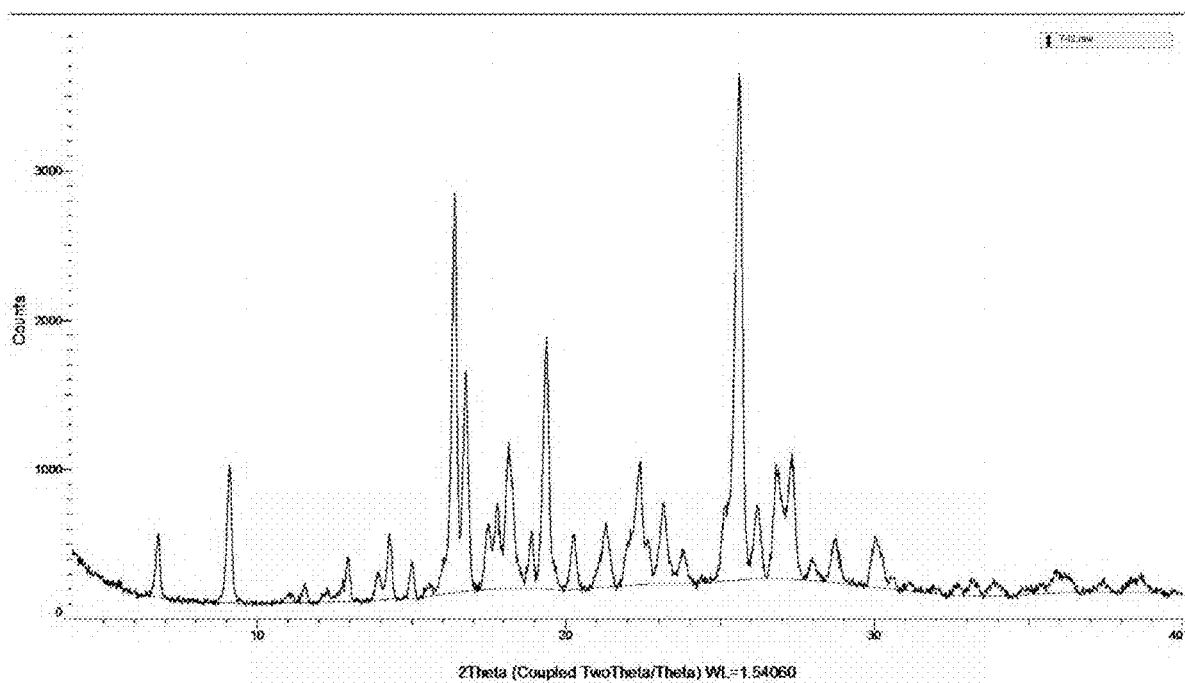

FIG. 134 depicts the XRPD profile of 7-I2 (Experiment Reference 7-Sample Reference I2) (Pattern #1).

Figure 135:
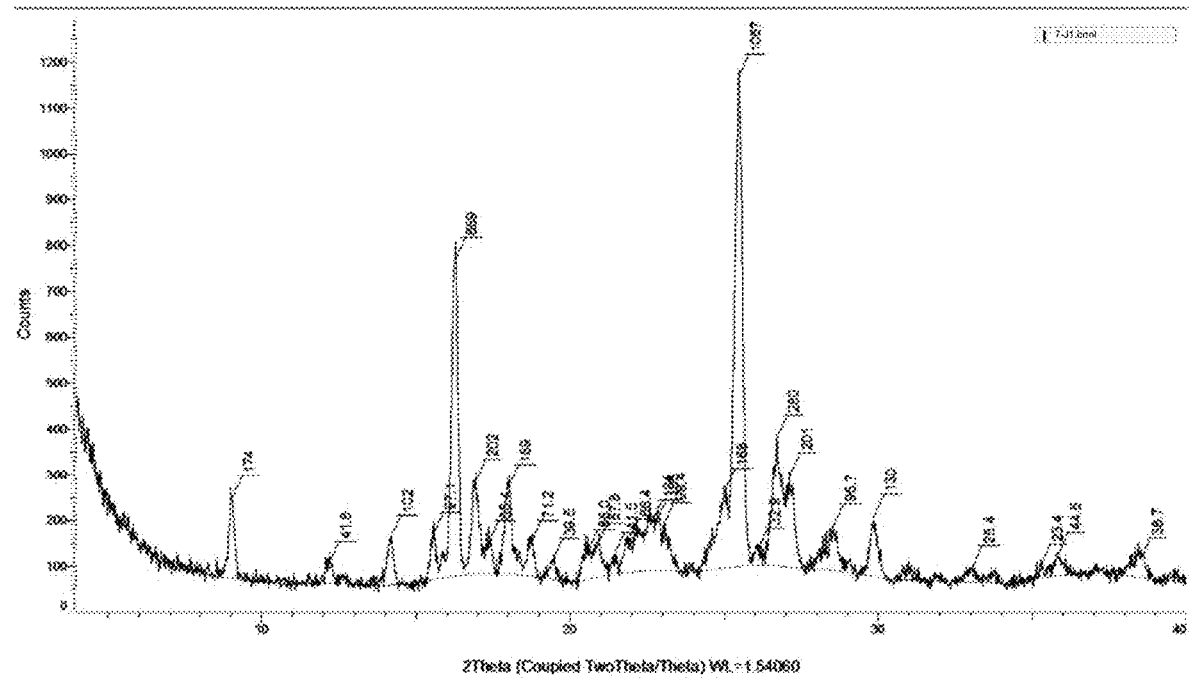

FIG. 135 depicts the XRPD profile of 7-J1 (Experiment Reference 7-Sample Reference J1) (Pattern #2a).

Figure 136:
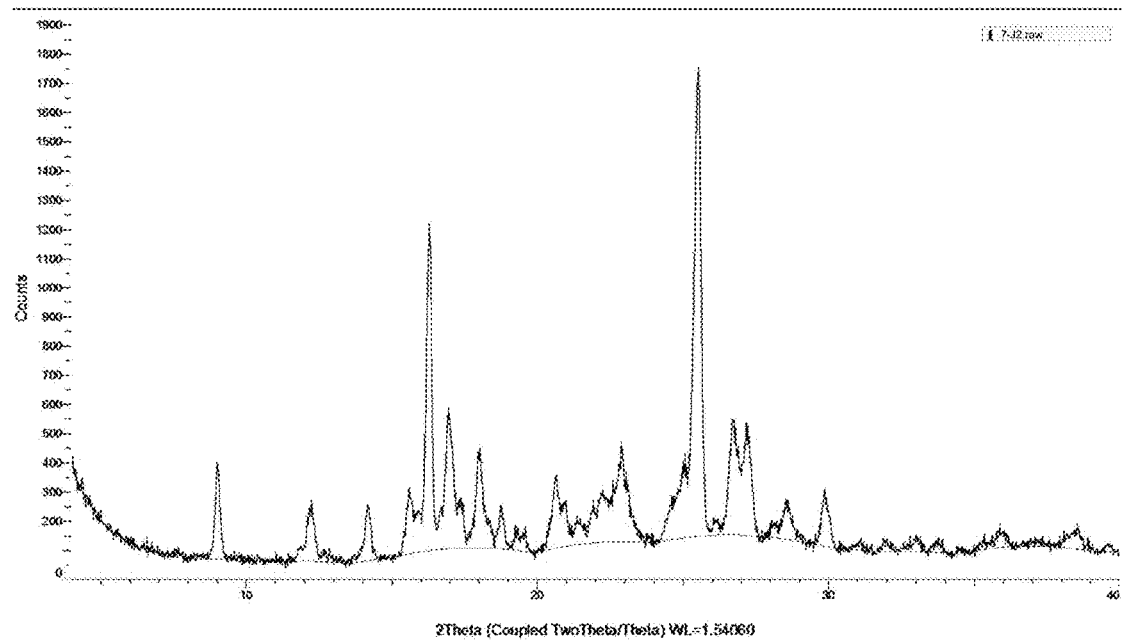

FIG. 136 depicts the XRPD profile of 7-J2 (Experiment Reference 7-Sample Reference J2) (Pattern #2a).

Figure 137:
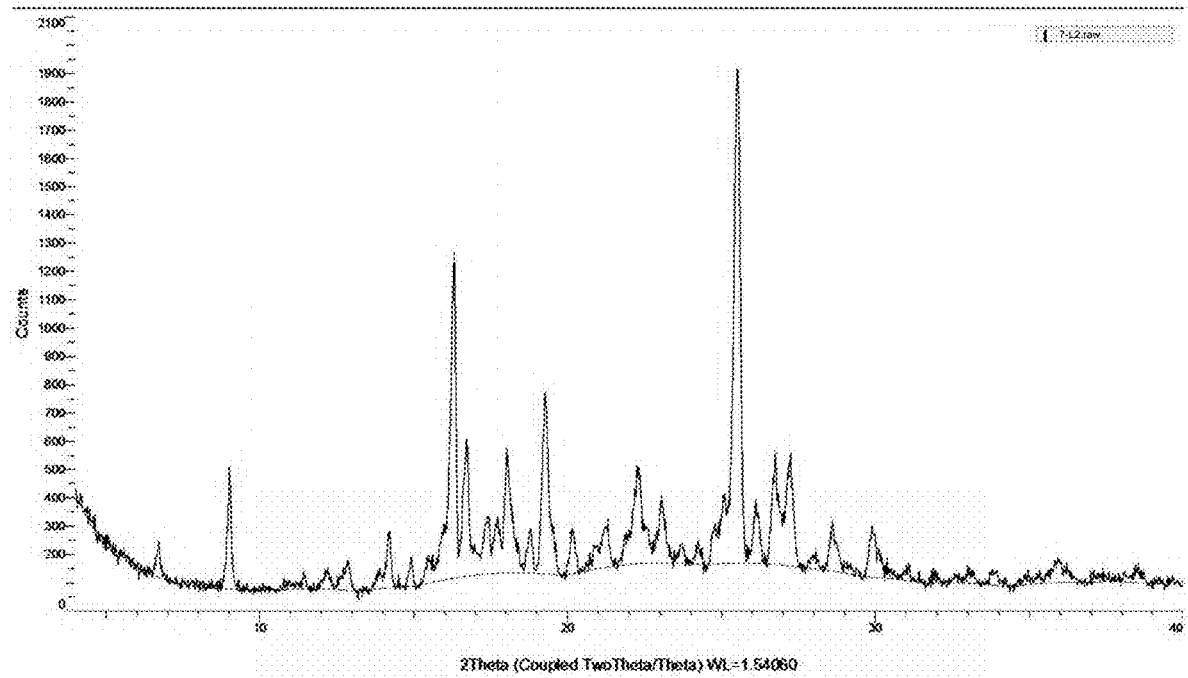

FIG. 137 depicts the XRPD profile of 7-L2 (Experiment Reference 7-Sample Reference L2) (Pattern #1).

Figure 138:
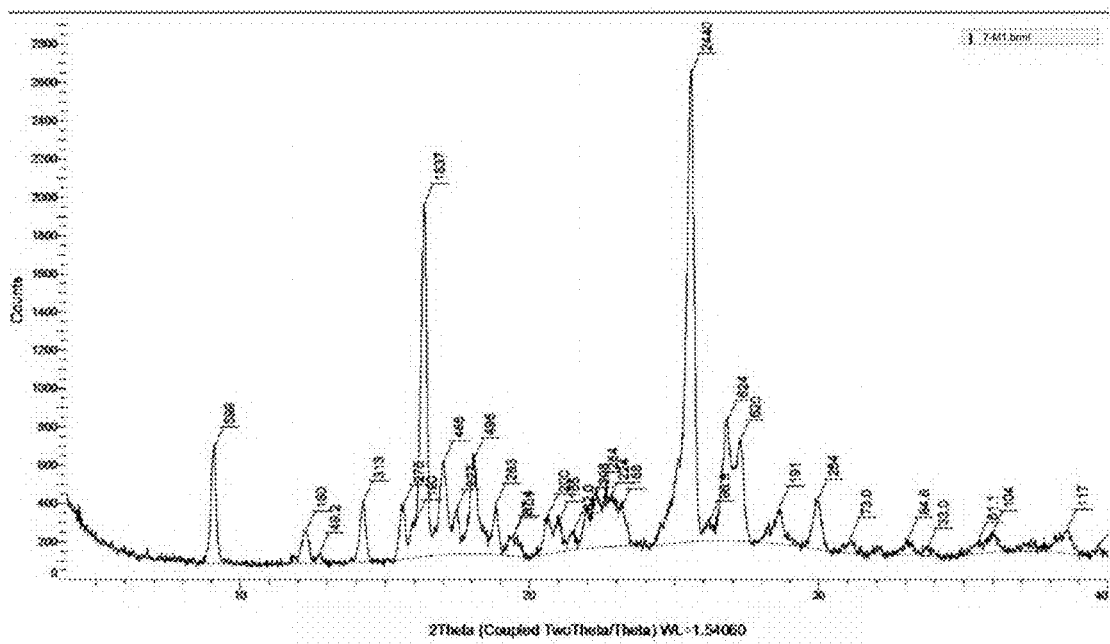

FIG. 138 depicts the XRPD profile of 7-M1 (Experiment Reference 7-Sample Reference M1) (Pattern #2a).

Figure 139:
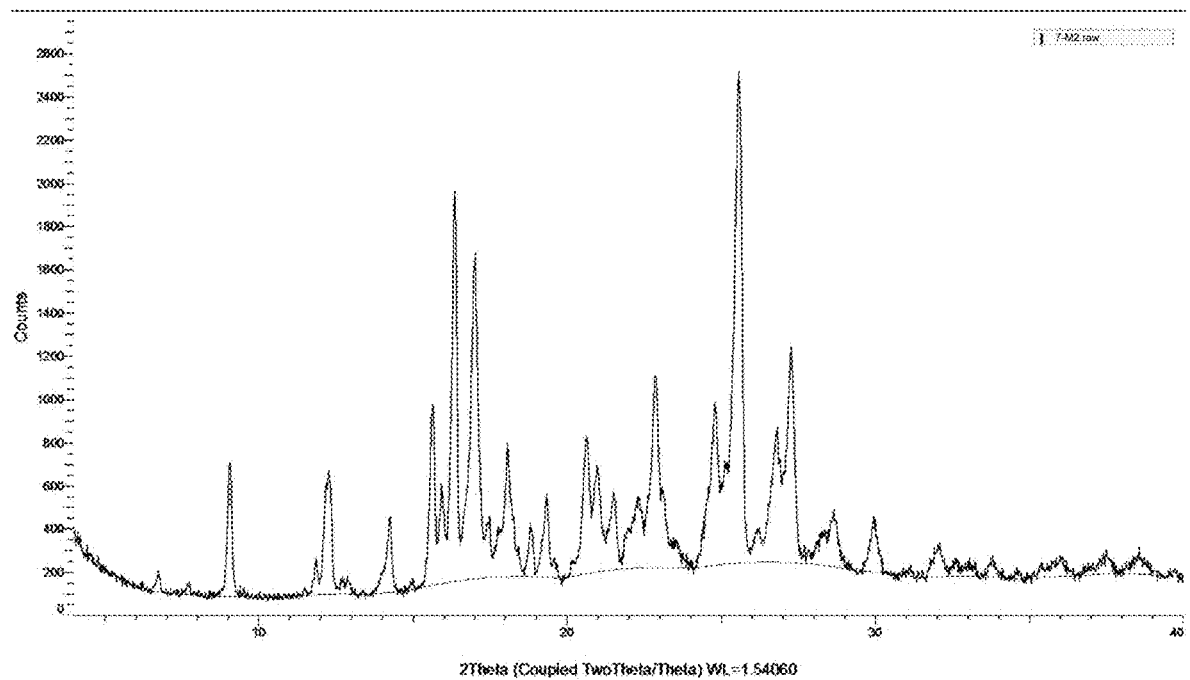

FIG. 139 depicts the XRPD profile of 7-M2 (Experiment Reference 7-Sample Reference M2) (Pattern #2a).

Figure 140:
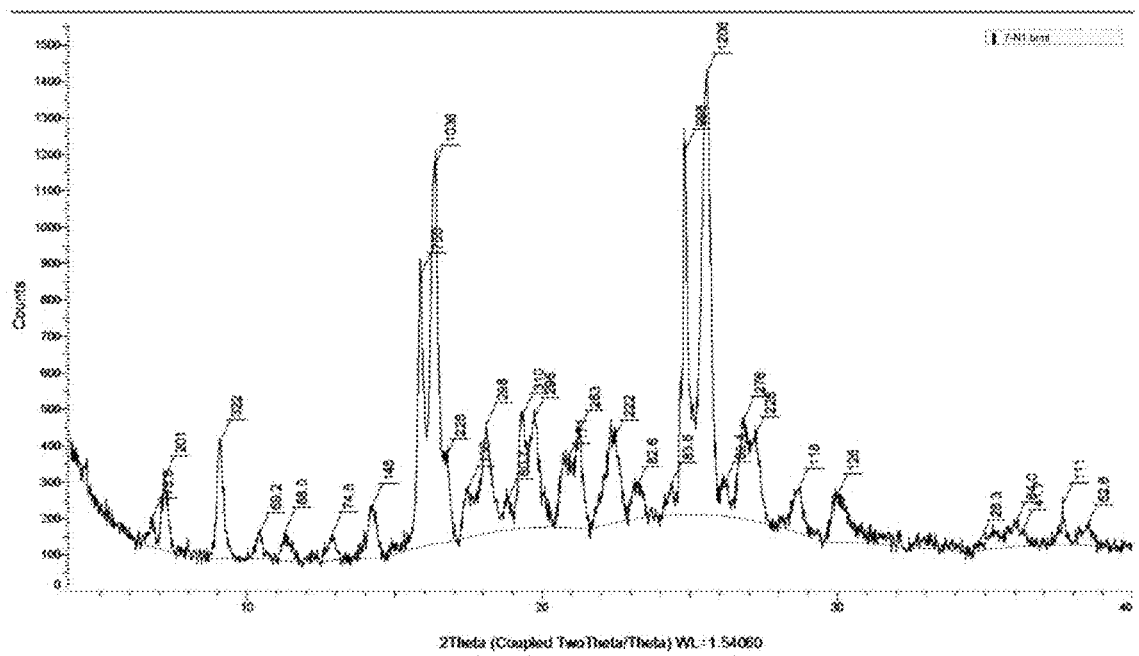

FIG. 140 depicts the XRPD profile of 7-N1 (Experiment Reference 7-Sample Reference N1) (Pattern #7).

Figure 141:
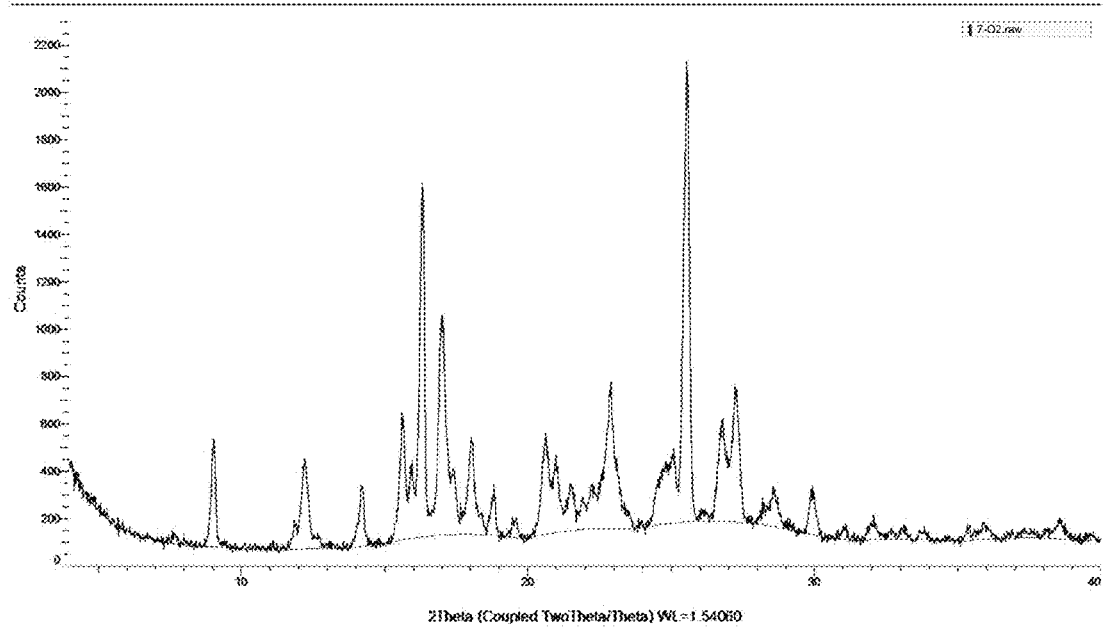

FIG. 141 depicts the XRPD profile of 7-O2 (Experiment Reference 7-Sample Reference O2) (Pattern #2a).

Figure 142:
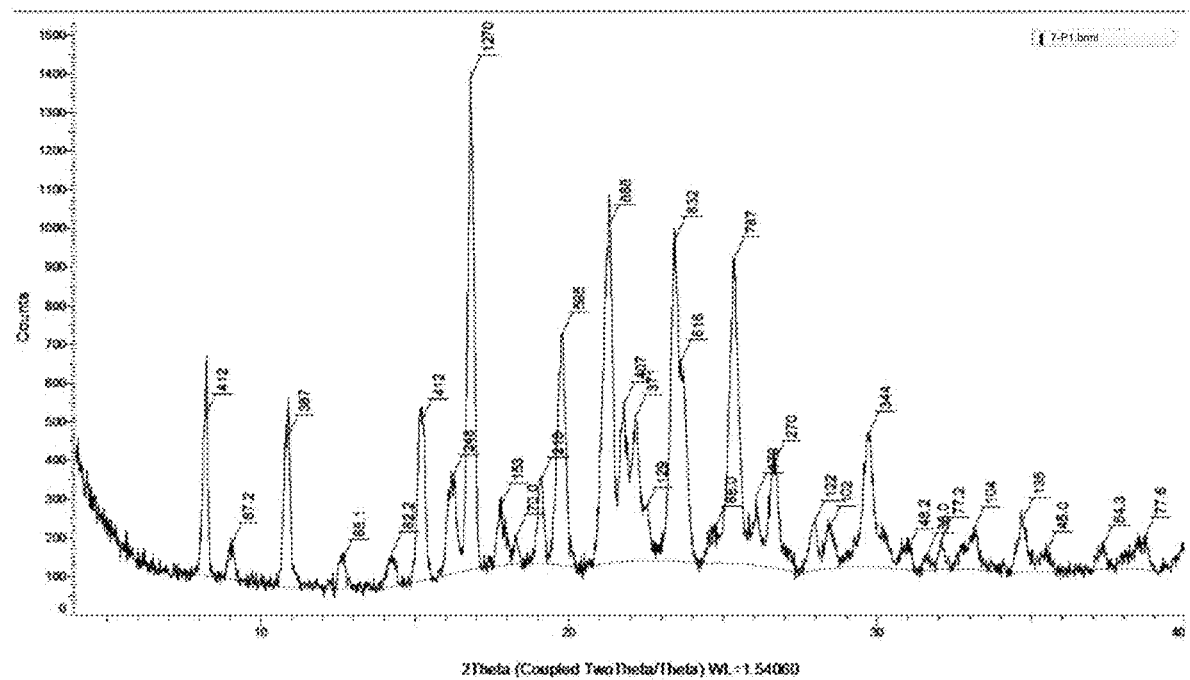

FIG. 142 depicts the XRPD profile of 7-P1 (Experiment Reference 7-Sample Reference P1) (Pattern #10).

Figure 143:
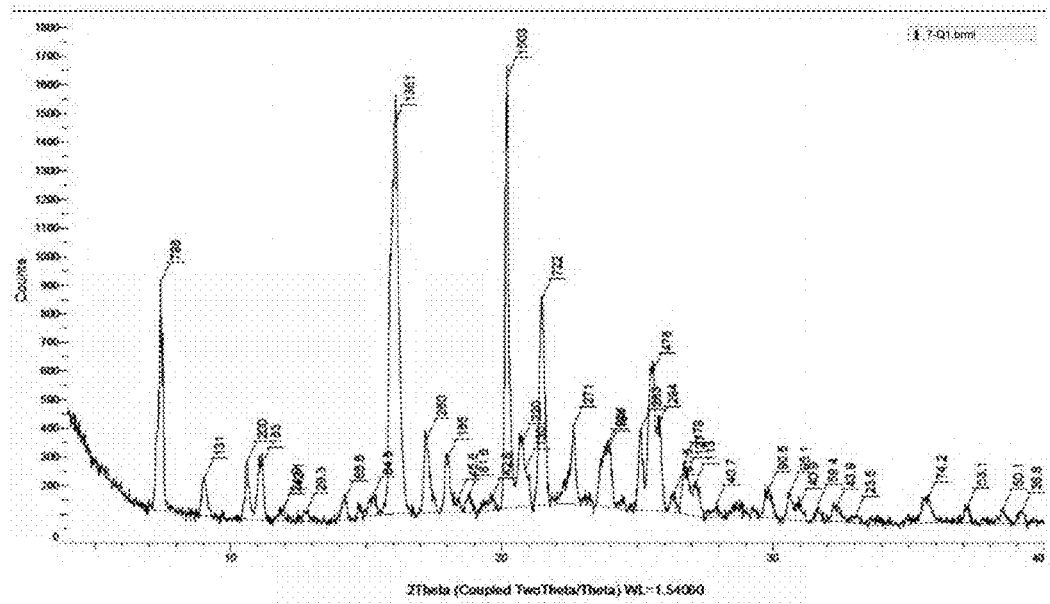

FIG. 143 depicts the XRPD profile of 7-Q1 (Experiment Reference 7-Sample Reference Q1) (Pattern #11).

Figure 144:
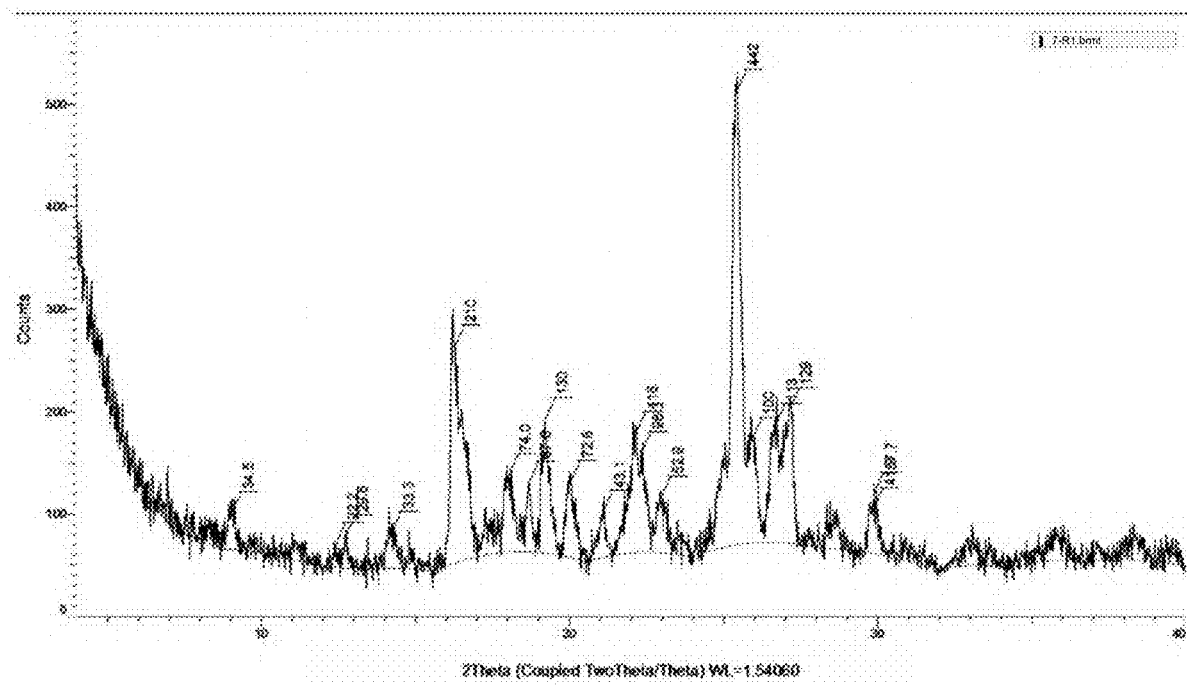

FIG. 144 depicts the XRPD profile of 7-R1 (Experiment Reference 7-Sample Reference R1) (Pattern #i).

Figure 145:
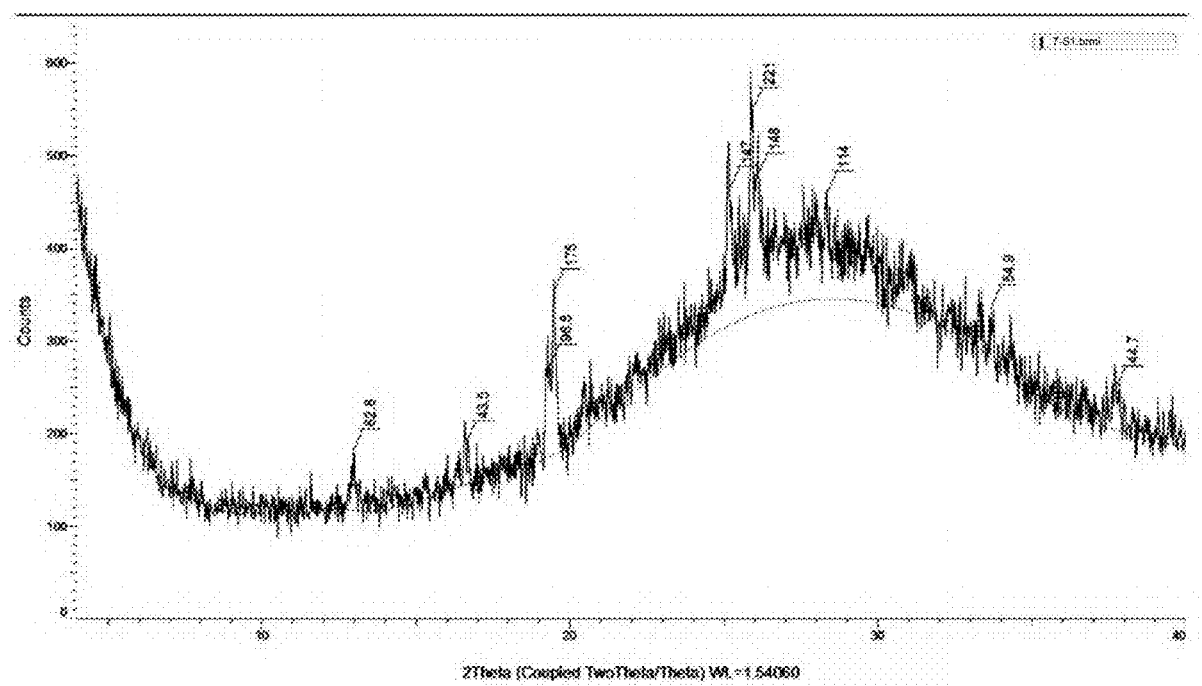

FIG. 145 depicts the XRPD profile of 7-S1 (Experiment Reference 7-Sample Reference S1) (Pattern #8, amorphized).

Figure 146:
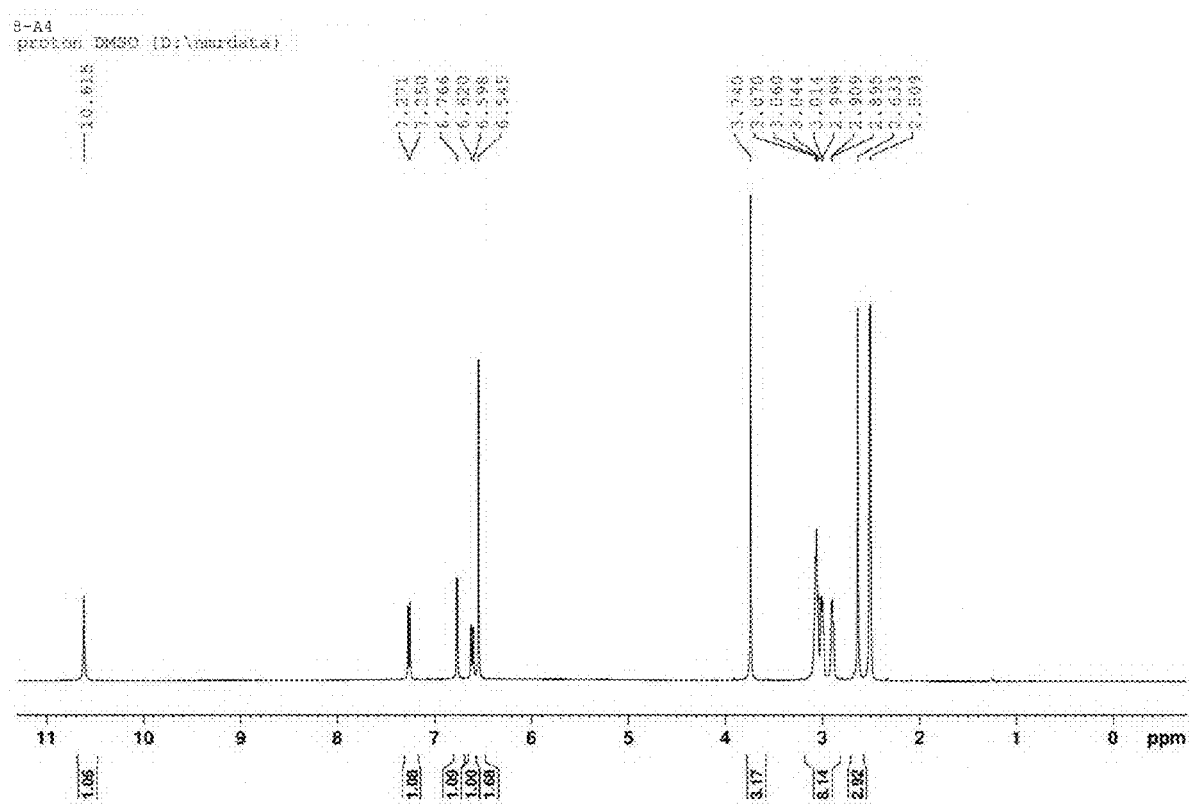

FIG. 146 depicts the $^1$H NMR spectrum of 8-A4 (Experiment Reference 8-Sample Reference A4), analysis was acquired in DMSO-d6 and calibrated to the non-deuterated solvent residual at 2.50 ppm API to Fumaric acid, 1.0 to 1.0.

Figure 147:
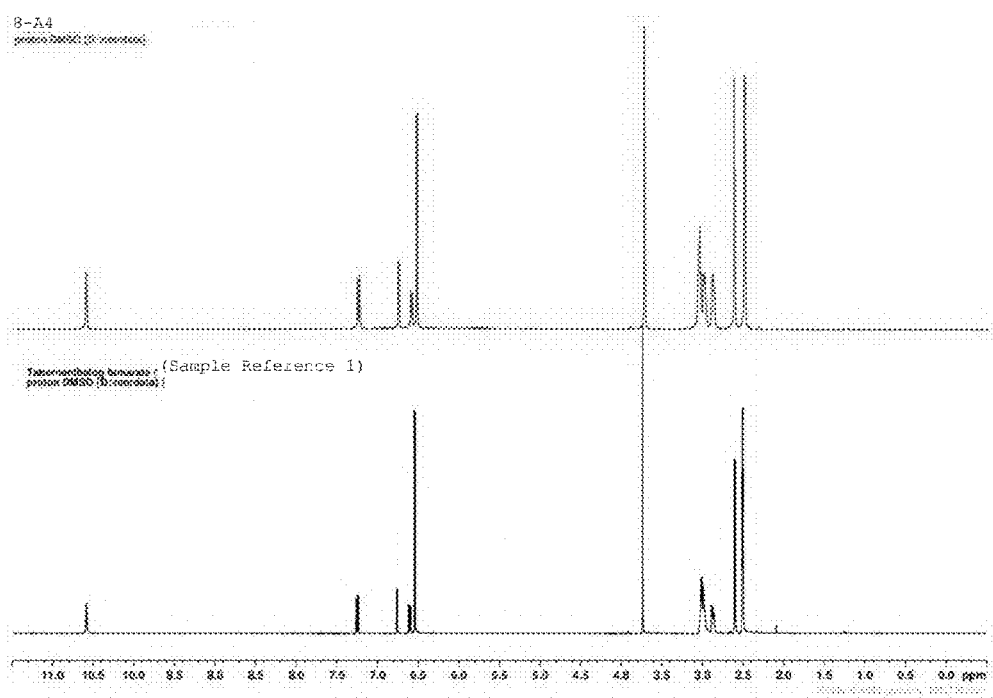

FIG. 147 depicts the $^1$H NMR spectra overlay of 8-A4 (Experiment Reference 8-Sample Reference A4) and input (Sample Reference 1).

Figure 148:
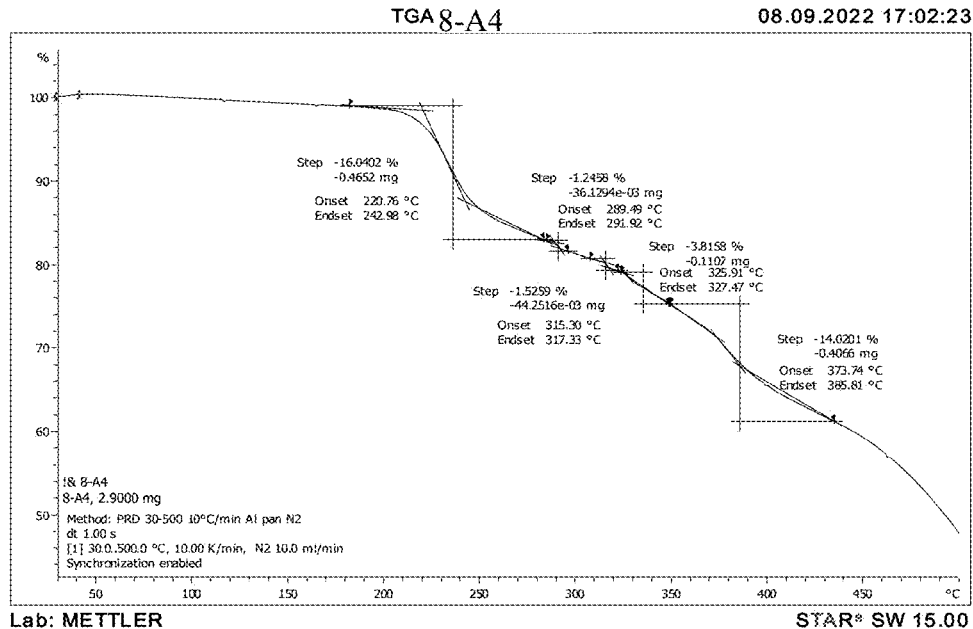

FIG. 148 depicts the TGA profile of 8-A4 (Experiment Reference 8-Sample Reference A4), analysis was acquired at a ramp rate of +10° C./minute.

Figure 149:
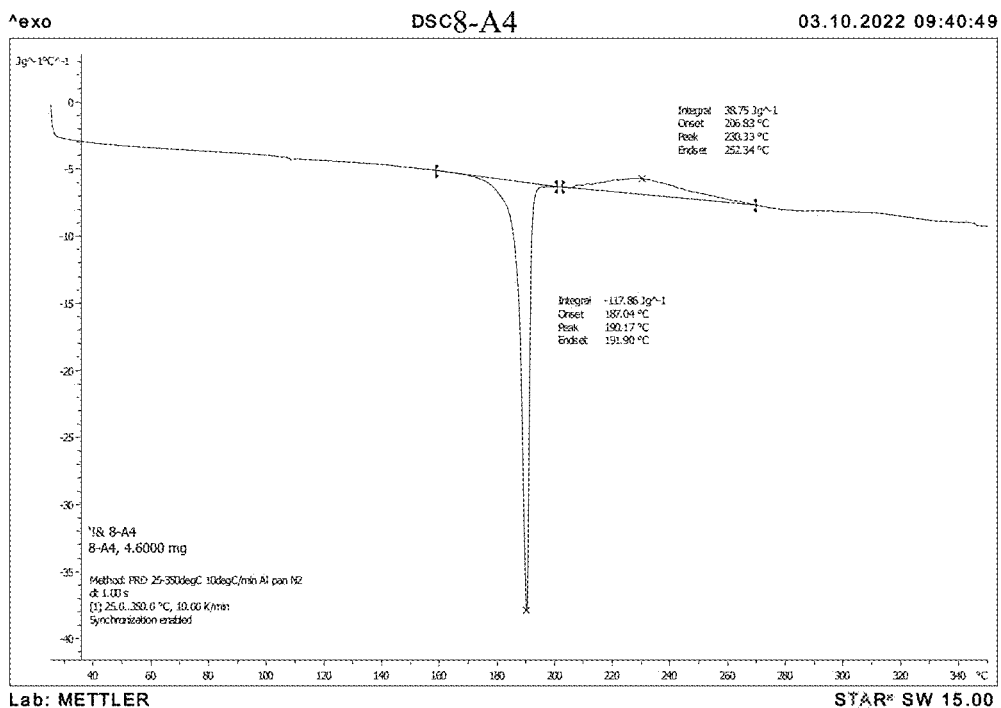

FIG. 149 depicts the DSC profile of 8-A4 (Experiment Reference 8-Sample Reference A4), analysis was acquired at a ramp rate of +10° C./minute.

Figure 150:
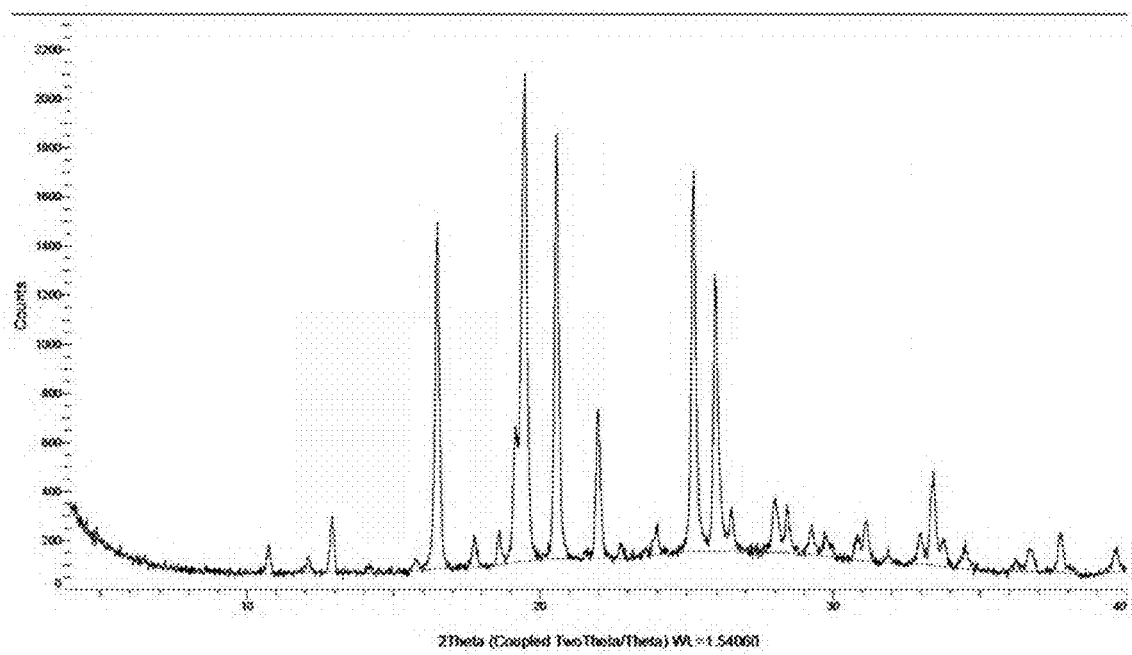

FIG. 150 depicts the XRPD profile of 8-A4 (Experiment Reference 8-Sample Reference A4) (Form A, Pattern #6a).

Figure 151:
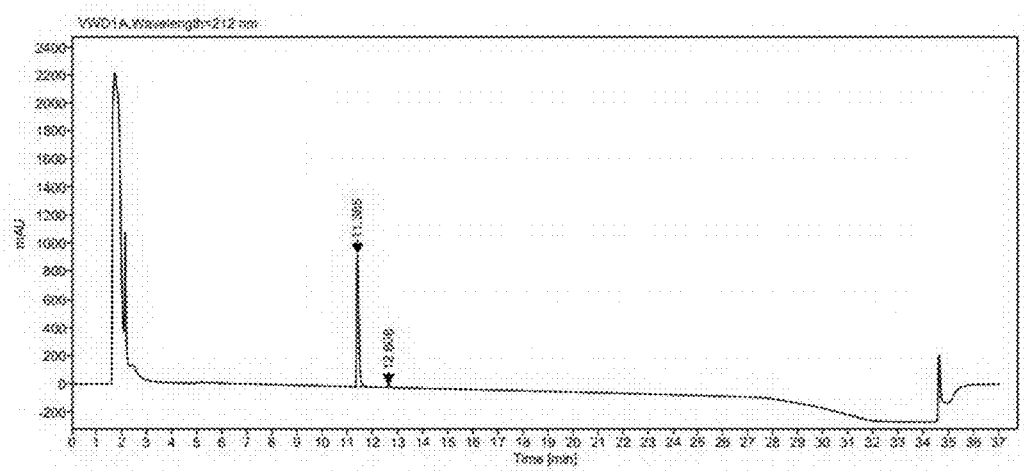

FIG. 151 depicts the HPLC profile of 8-A4 (Experiment Reference 8-Sample Reference A4) (Form A, Pattern #6a). The peak at ca. 2 min correspond to DMSO, as it was used as the sample diluent.

Figure 152:
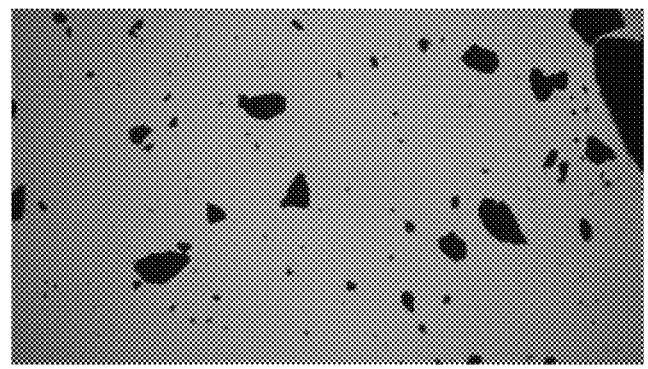

FIG. 152 depicts the PLM of 8-A4 (Experiment Reference 8-Sample Reference A4) normal polarized (magnification×2).

Figure 153:
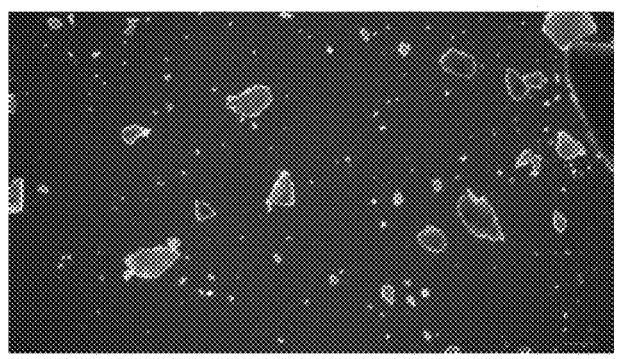

FIG. 153 depicts the PLM of 8-A4 (Experiment Reference 8-Sample Reference A4) cross polarized (magnification×2).

Figure 154:
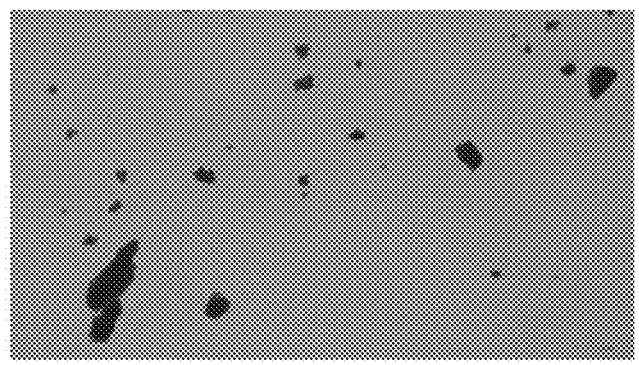

FIG. 154 depicts the PLM of 8-A4 (Experiment Reference 8-Sample Reference A4) normal polarized (magnification×5).

Figure 155:
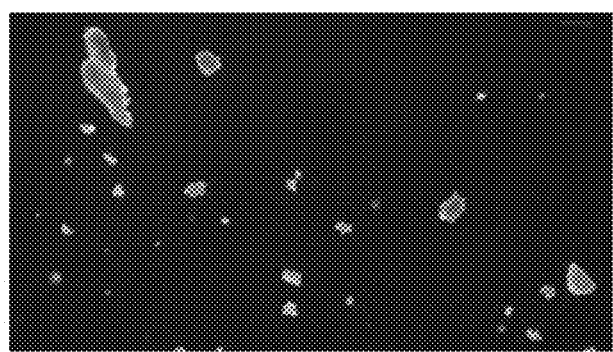

FIG. 155 depicts the PLM of 8-A4 (Experiment Reference 8-Sample Reference A4) normal polarized (magnification×5).

Figure 156:
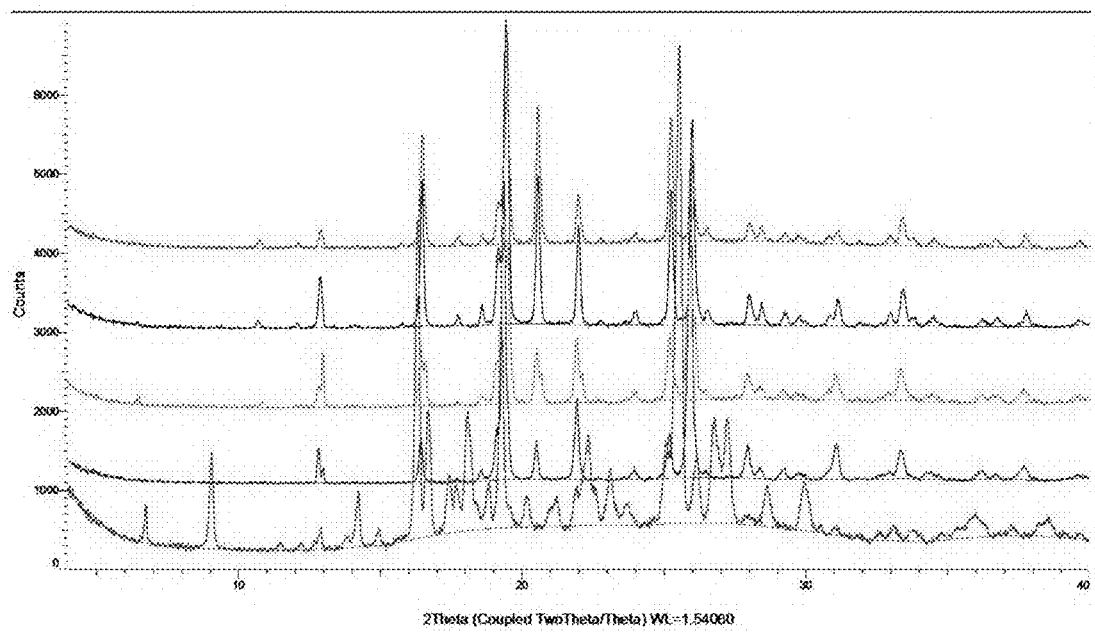

FIG. 156 depicts the monitoring the conversion of the tabernanthalog monofumarate salt (Sample Reference 1) in water at 20° C. by XRPD analysis. Overlay of, from bottom to top, the tabernanthalog monofumarate salt (Pattern #1, Sample Reference 1), 8-A1 (t=24 h), 8-A2 (t=48 h), 8-A3 (t=4 d) and 8-A4 (t=10 d) wherein 8-A1=(Experiment Reference 8-Sample Reference A1); 8-A2=(Experiment Reference 8-Sample Reference A2); 8-A3=(Experiment Reference 8-Sample Reference A3); and 8-A4=(Experiment Reference 8-Sample Reference A4).

Figure 157:
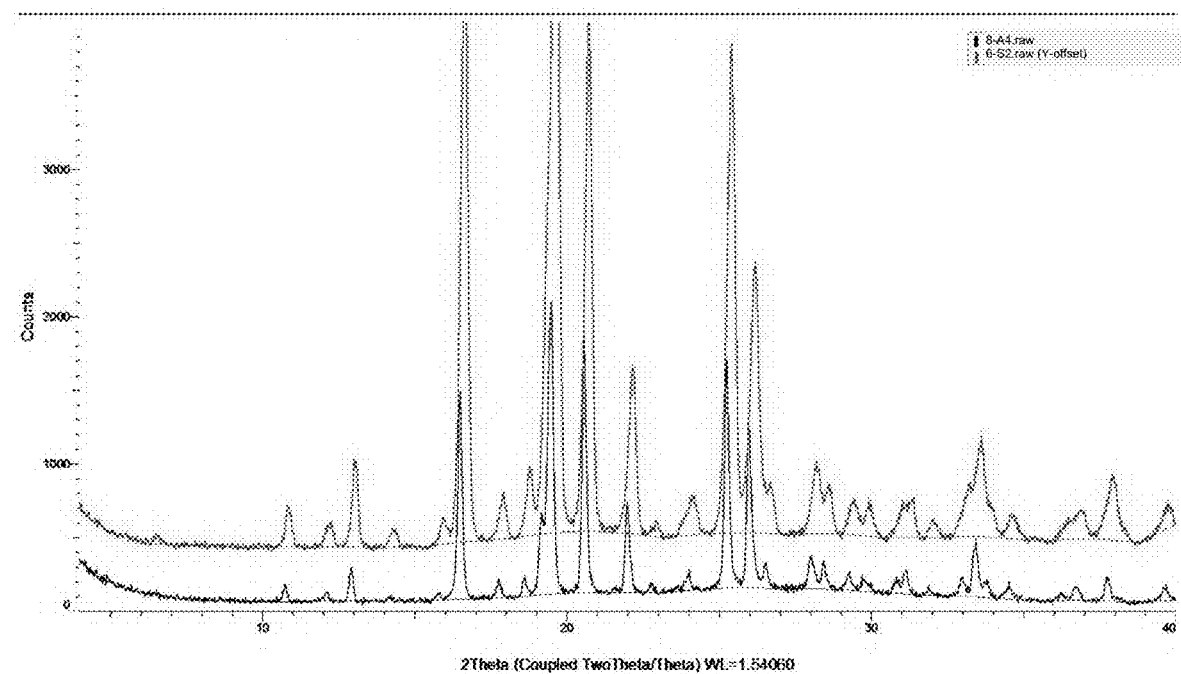

FIG. 157 depicts the XRPD diffractogram overlay of 8-A4 (Experiment Reference 8-Sample Reference A4) and 6-S2 (Experiment Reference 6-Sample Reference S2).

Figure 158:
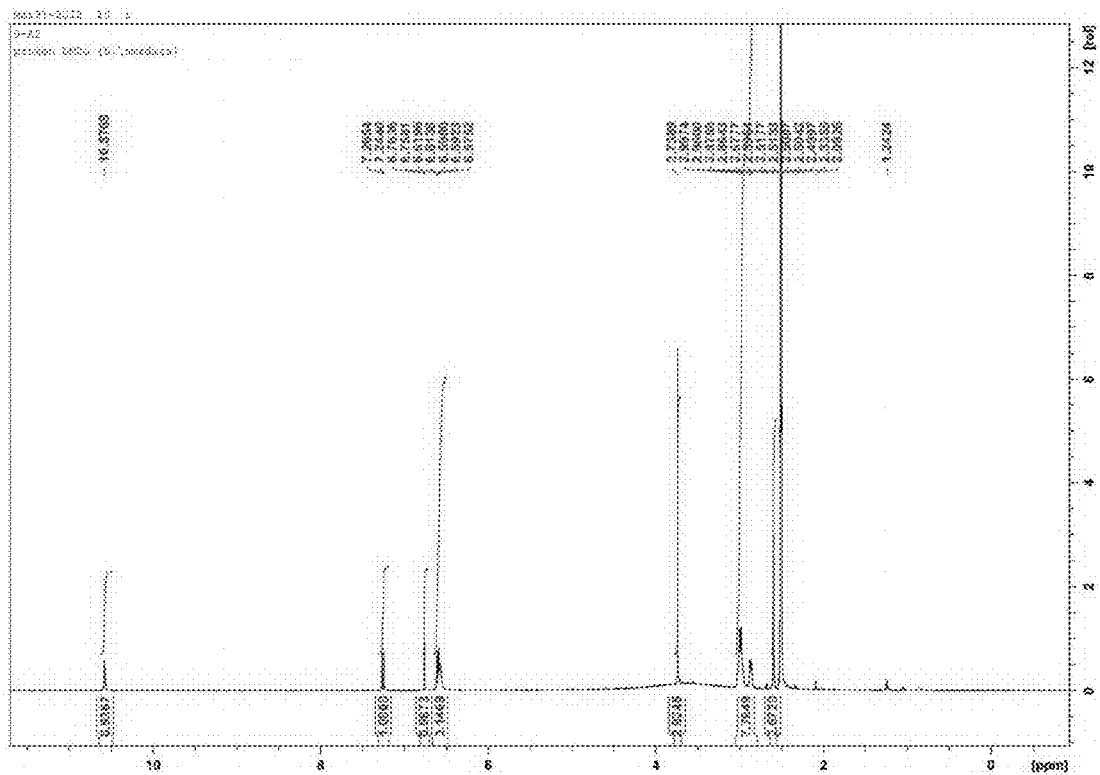

FIG. 158 depicts the $^1$H NMR spectrum of 9-A2 (Experiment Reference 9-Sample Reference A2) that was acquired in DMSO-d$_6$ and calibrated to the non-deuterated solvent residual at 2.50 ppm.

Figure 159:
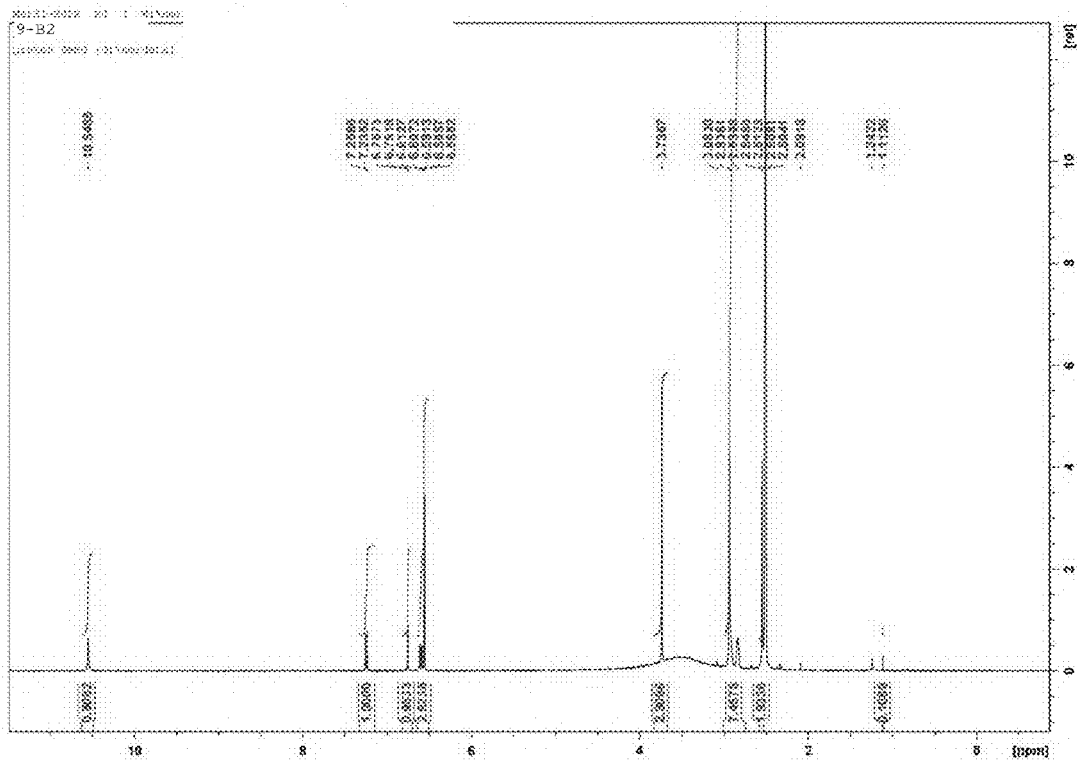

FIG. 159 depicts the $^1$H NMR spectrum of 9-B2 (Experiment Reference 9-Sample Reference B2), analysis was acquired in DMSO-d6 and calibrated to the non-deuterated solvent residual at 2.50 ppm. Residual tBME 0.3% w/w.

Figure 160:
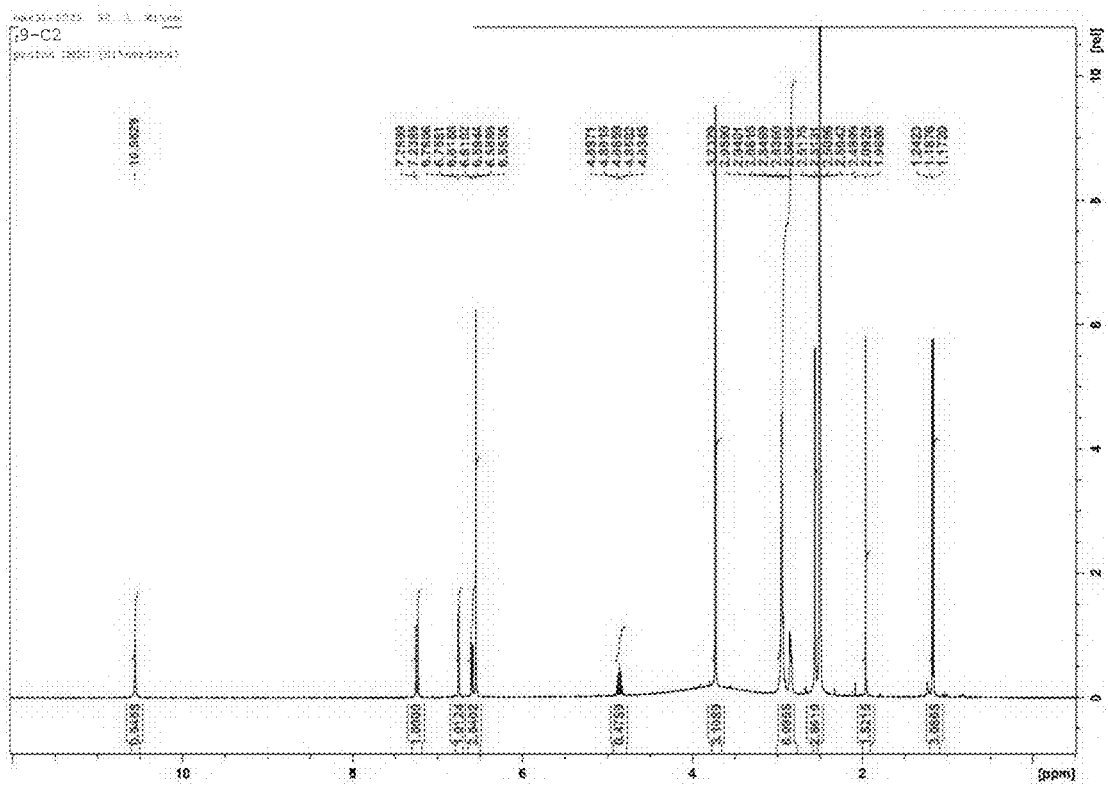

FIG. 160 depicts the $^1$H NMR spectrum of 9-C2 (Experiment Reference 9-Sample Reference C2), analysis was acquired in DMSO-d$_6$ and calibrated to the non-deuterated solvent residual at 2.50 ppm. Residual IPAC 13.2% w/w (ca. th. solvate 22.8% w/w).

Figure 161:
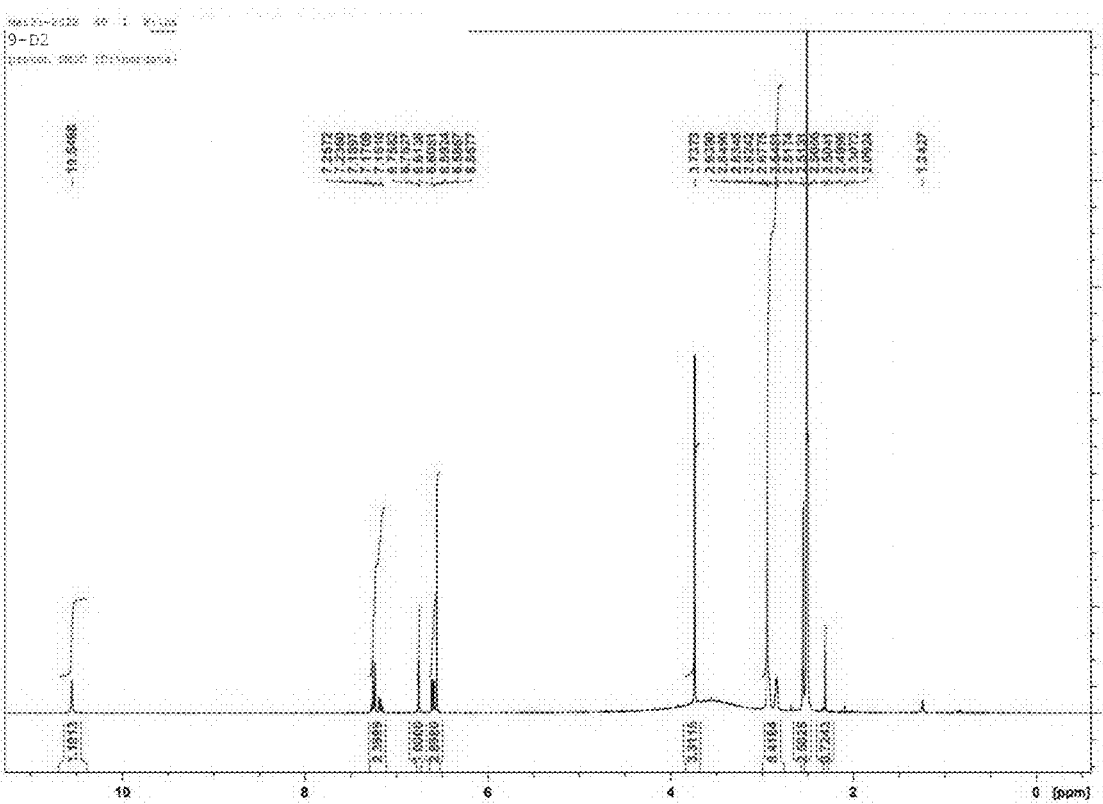

FIG. 161 depicts the $^1$H NMR spectrum of 9-D2 (Experiment Reference 9-Sample Reference D2), analysis was acquired in DMSO-d$_6$ and calibrated to the non-deuterated solvent residual at 2.50 ppm. Residual toluene 6.0% w/w (ca. th. solvate 21.0% w/w).

Figure 162:
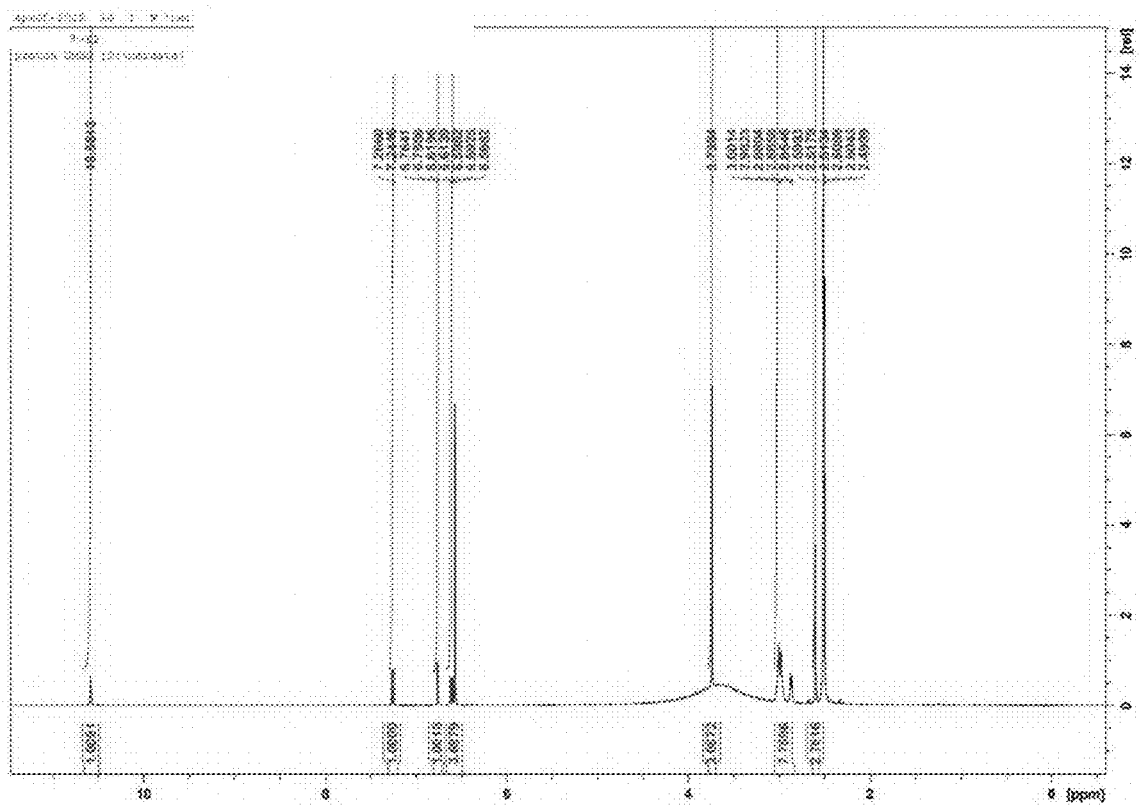

FIG. 162 depicts the $^1$H NMR spectrum of 9-E2 (Experiment Reference 9-Sample Reference E2), analysis was acquired in DMSO-d6 and calibrated to the non-deuterated solvent residual at 2.50 ppm.

Figure 163:
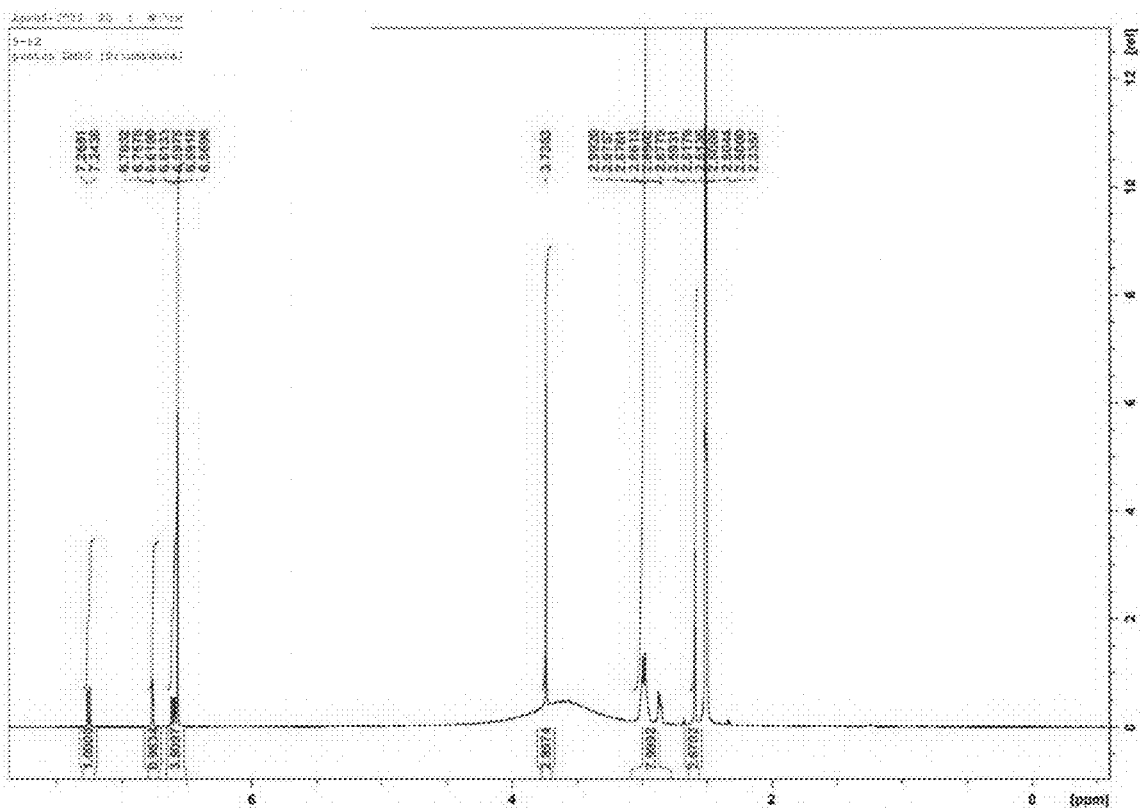

FIG. 163 depicts the $^1$H NMR spectrum of 9-F2 (Experiment Reference 9-Sample Reference F2), analysis was acquired in DMSO-d$_6$ and calibrated to the non-deuterated solvent residual at 2.50 ppm.

Figure 164:
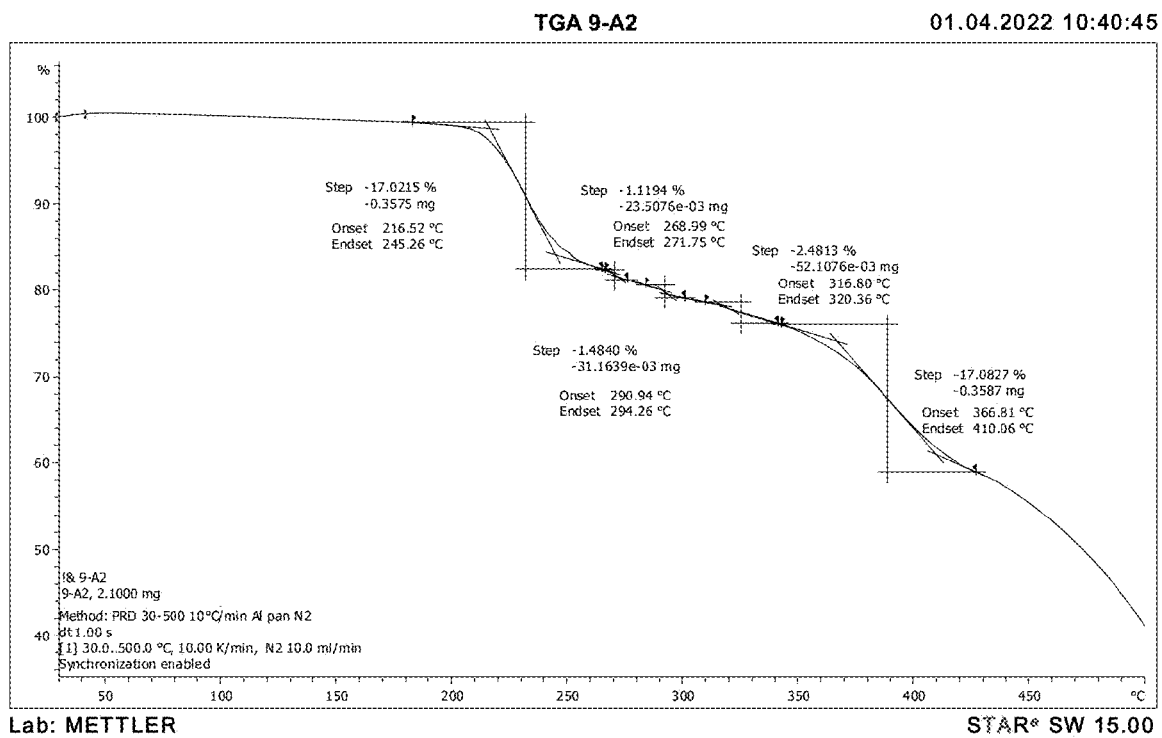

FIG. 164 depicts the TGA profile of 9-A2 (Experiment Reference 9-Sample Reference A2), analysis was acquired at a ramp rate of +10° C./minute.

Figure 165:
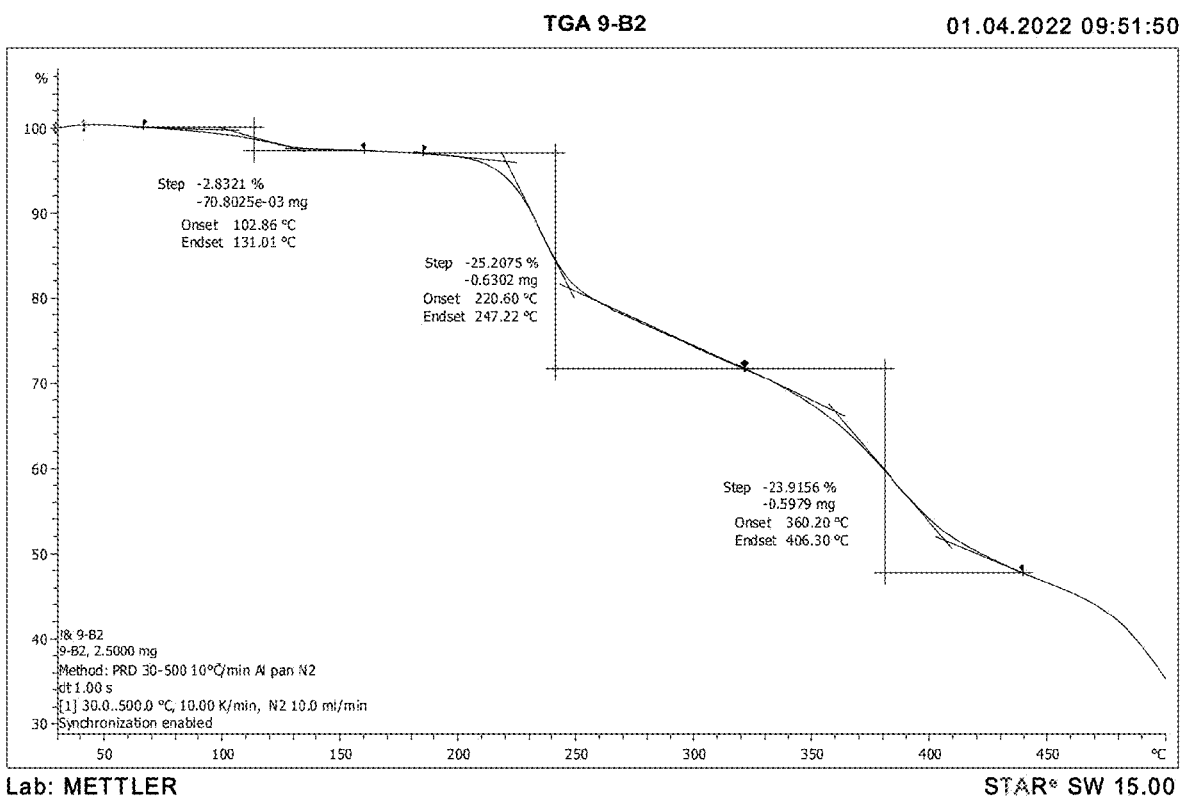

FIG. 165 depicts the TGA profile of 9-B2 (Experiment Reference 9-Sample Reference B2), analysis was acquired at a ramp rate of +10° C./minute.

Figure 166:
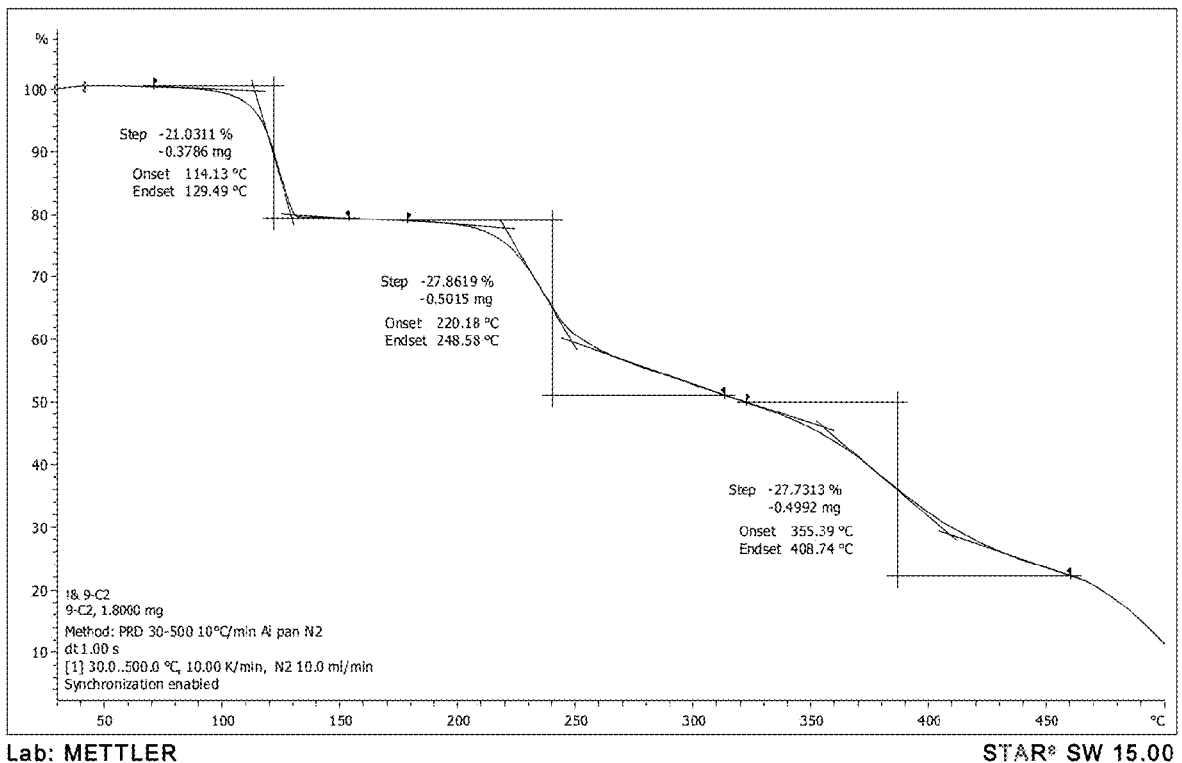

FIG. 166 depicts the TGA profile of 9-C2 (Experiment Reference 9-Sample Reference C2), analysis was acquired at a ramp rate of +10° C./minute.

Figure 167:
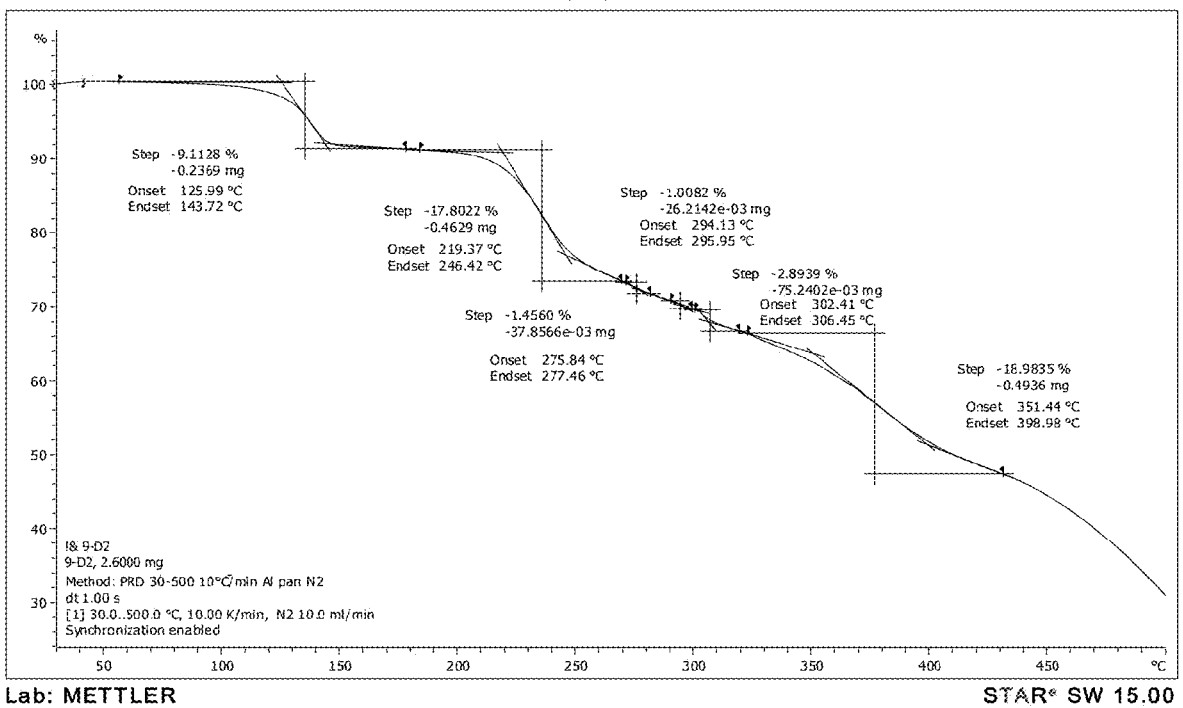

FIG. 167 depicts the TGA profile of 9-D2 (Experiment Reference 9-Sample Reference D2), analysis was acquired at a ramp rate of +10° C./minute.

Figure 168:
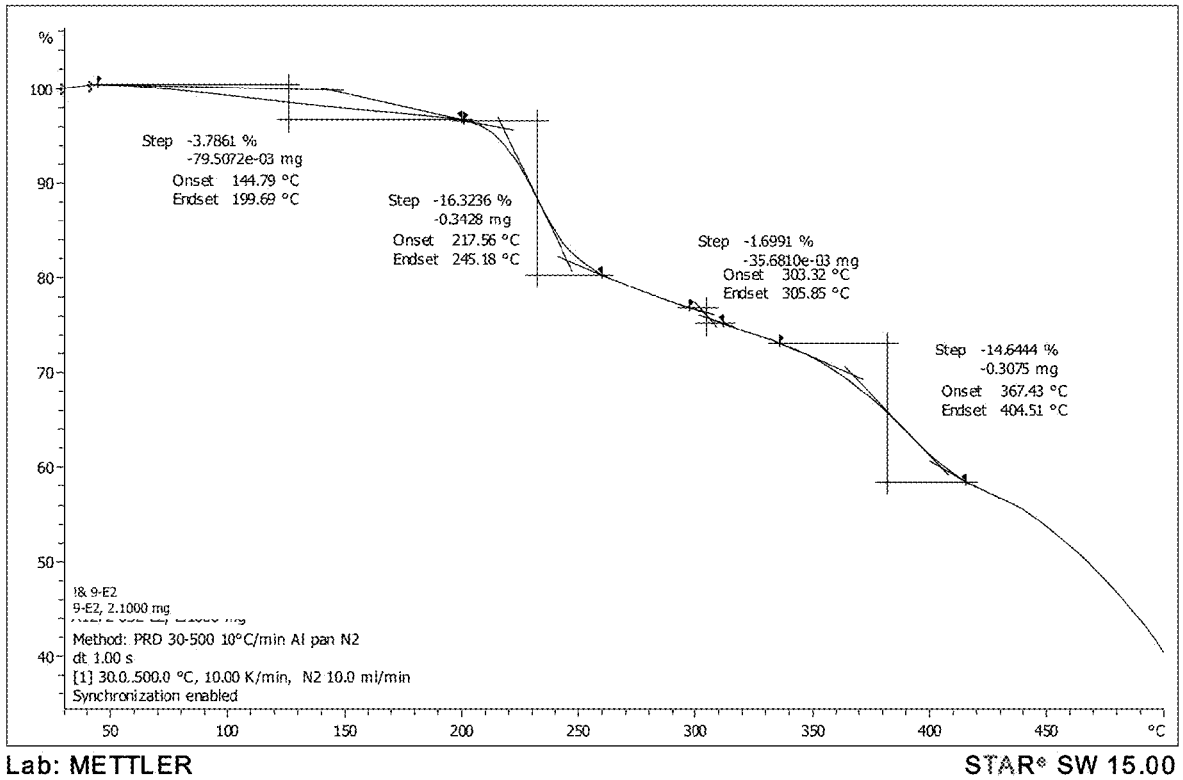

FIG. 168 depicts the TGA profile of 9-E2 (Experiment Reference 9-Sample Reference E2), analysis was acquired at a ramp rate of +10° C./minute.

Figure 169:
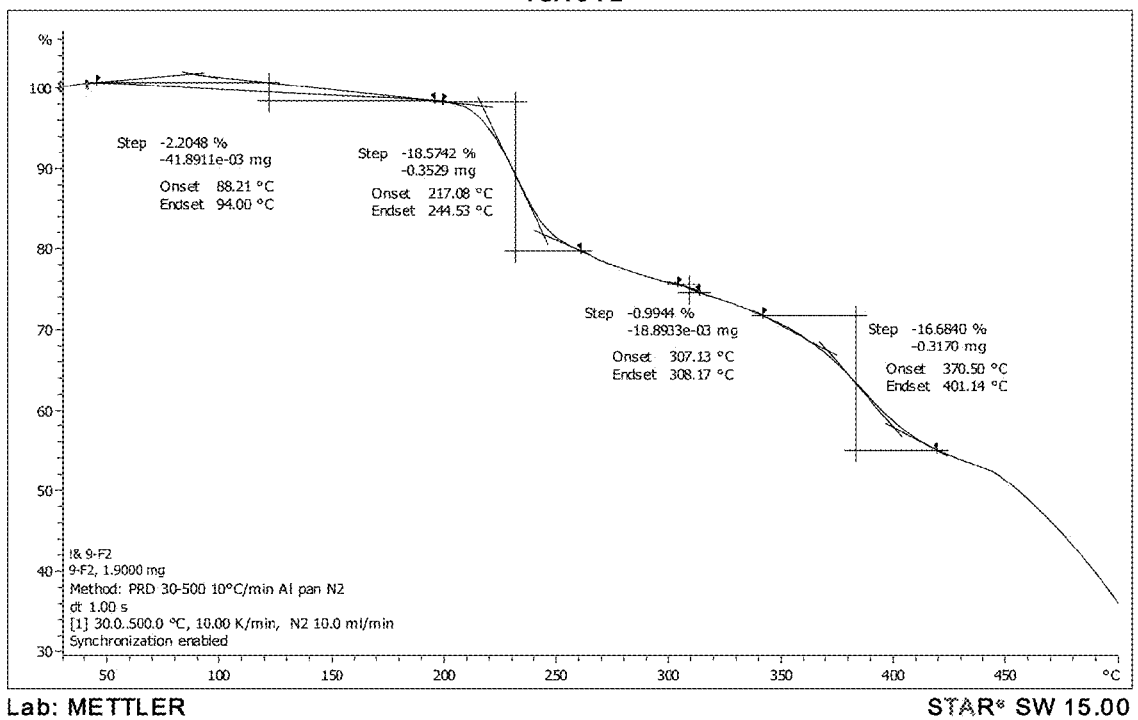

FIG. 169 depicts the TGA profile of 9-F2 (Experiment Reference 9-Sample Reference F2), analysis was acquired at a ramp rate of +10° C./minute.

Figure 170:
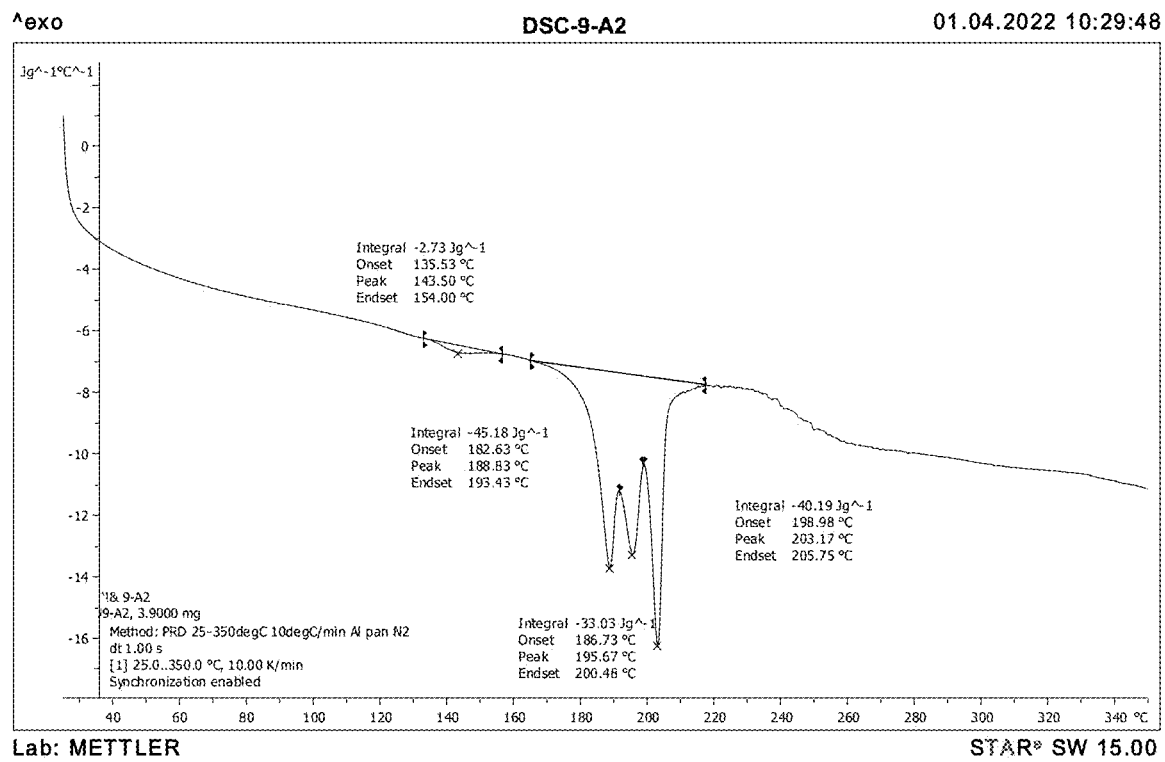

FIG. 170 depicts the DSC profile of 9-A2 (Experiment Reference 9-Sample Reference A2), analysis was acquired at a ramp rate of +10° C./minute. Higher melt event >200° C., was observed.

Figure 171:
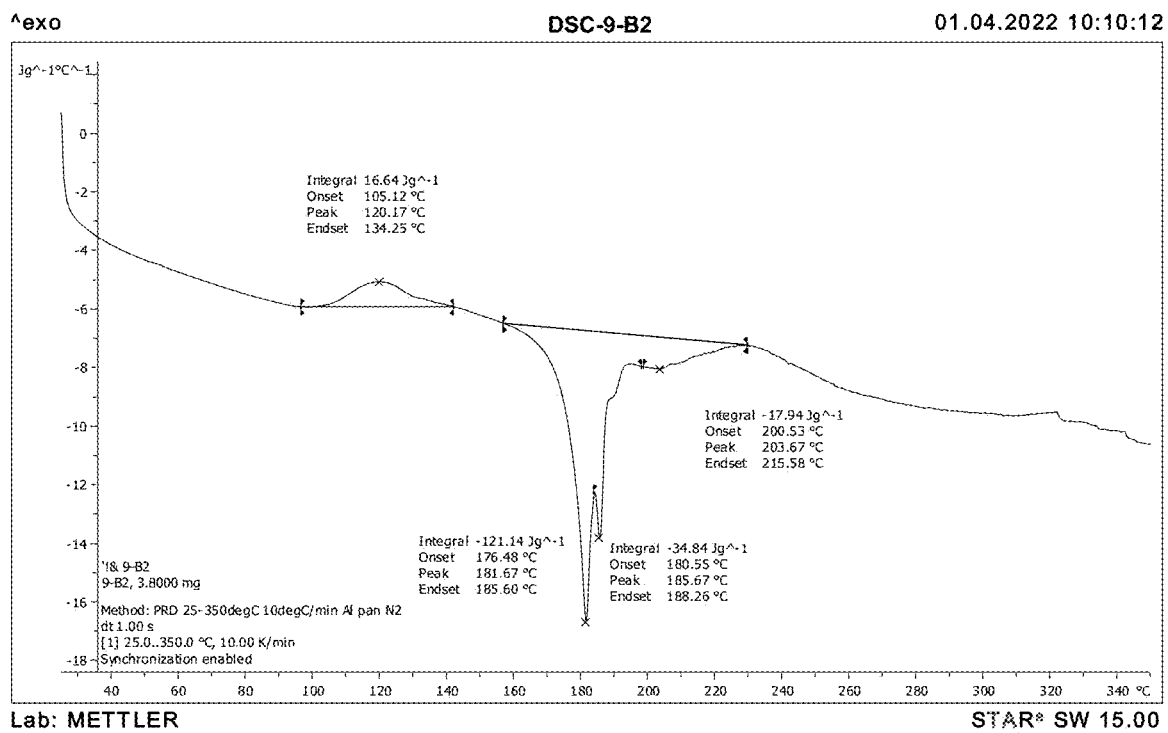

FIG. 171 depicts the DSC profile of 9-B2 (Experiment Reference 9-Sample Reference B2), analysis was acquired at a ramp rate of +10° C./minute.

Figure 172:
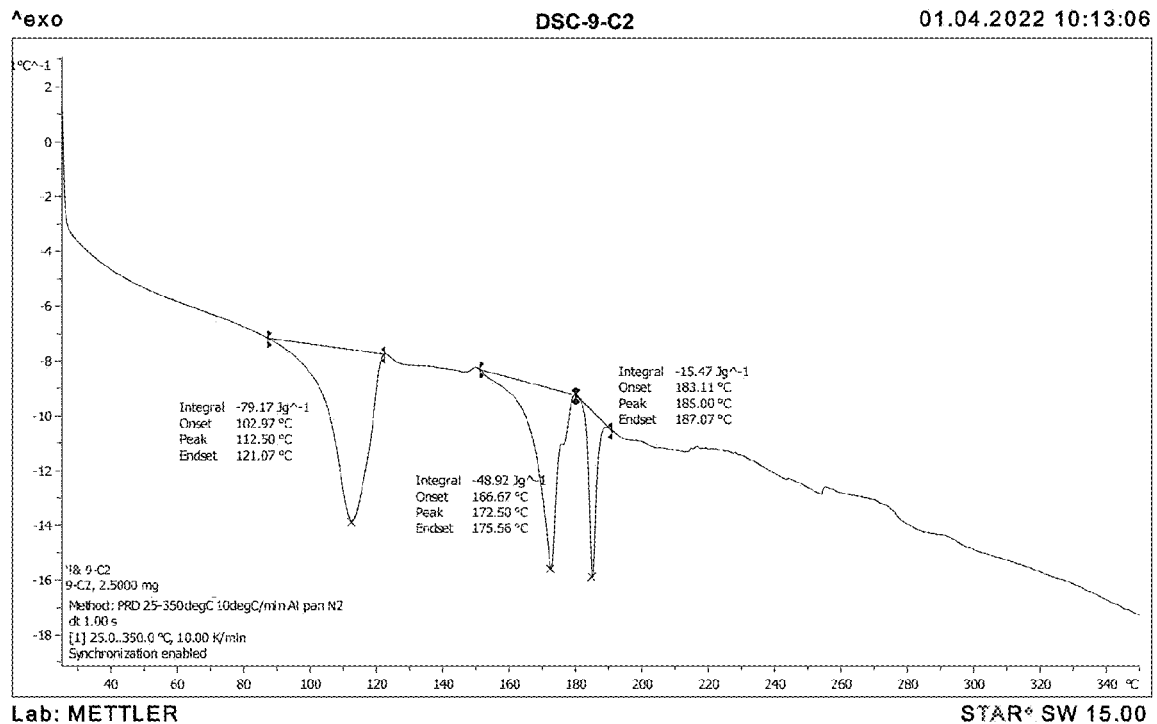

FIG. 172 depicts the DSC profile of 9-C2 (Experiment Reference 9-Sample Reference C2), analysis was acquired at a ramp rate of +10° C./minute.

Figure 173:
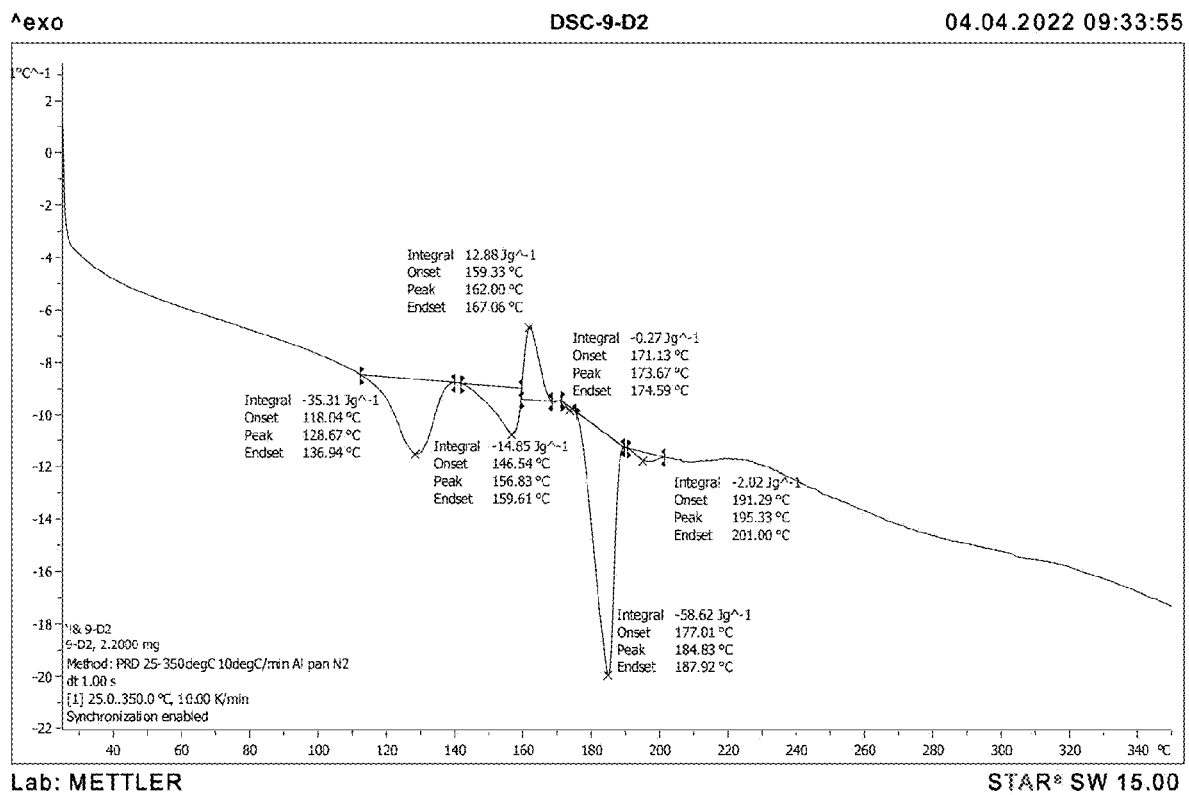

FIG. 173 depicts the DSC profile of 9-D2 (Experiment Reference 9-Sample Reference D2), analysis was acquired at a ramp rate of +10° C./minute.

Figure 174:
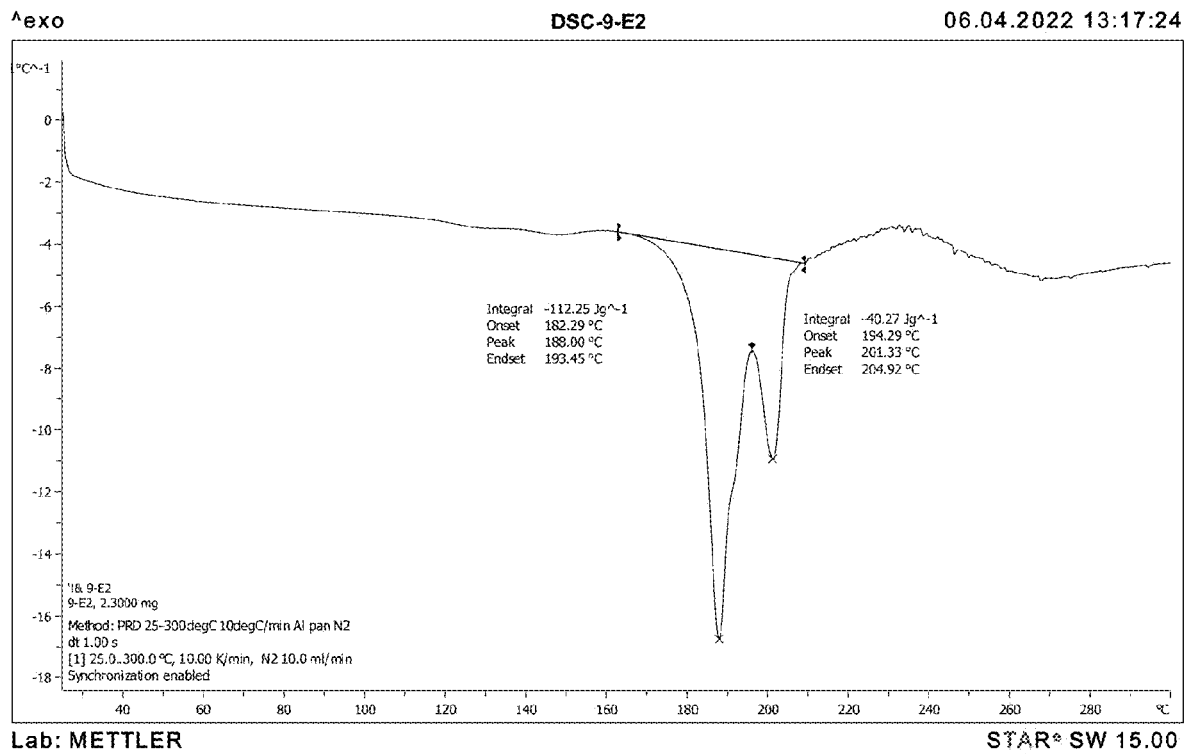

FIG. 174 depicts the DSC profile of 9-E2 (Experiment Reference 9-Sample Reference E2), analysis was acquired at a ramp rate of +10° C./minute.

Figure 175:
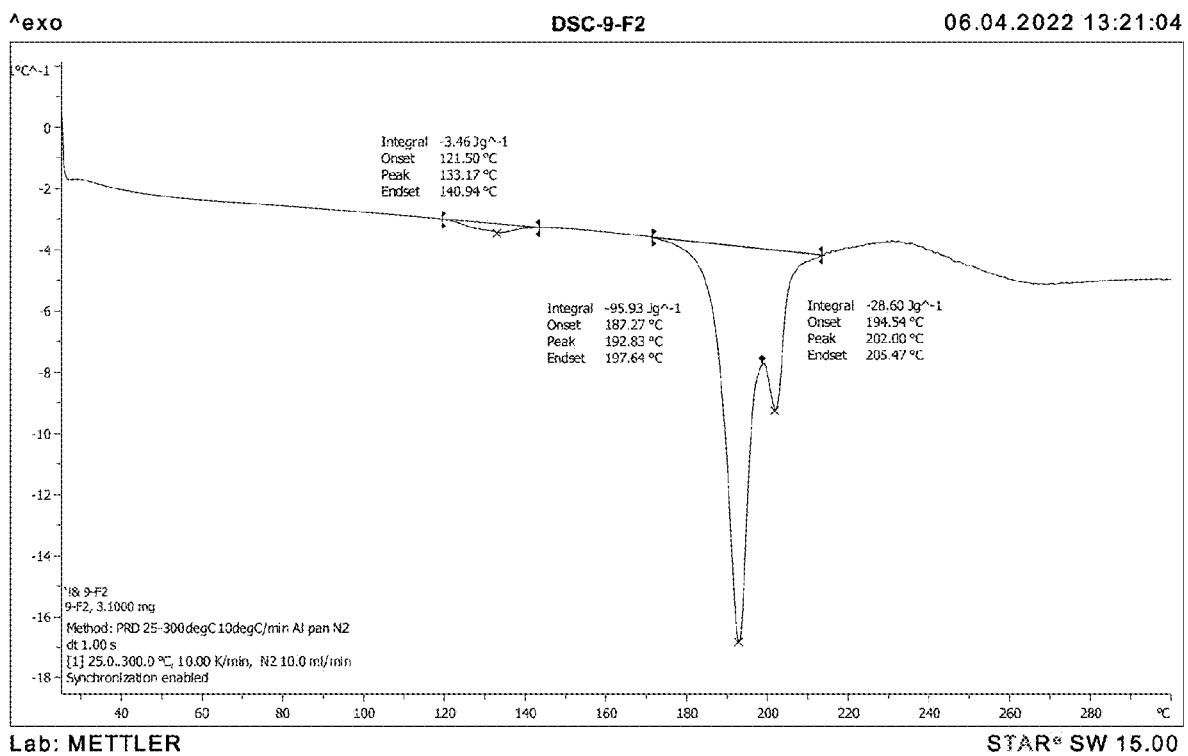

FIG. 175 depicts the DSC profile of 9-F2 (Experiment Reference 9-Sample Reference F2), analysis was acquired at a ramp rate of +10° C./minute.

Figure 176:
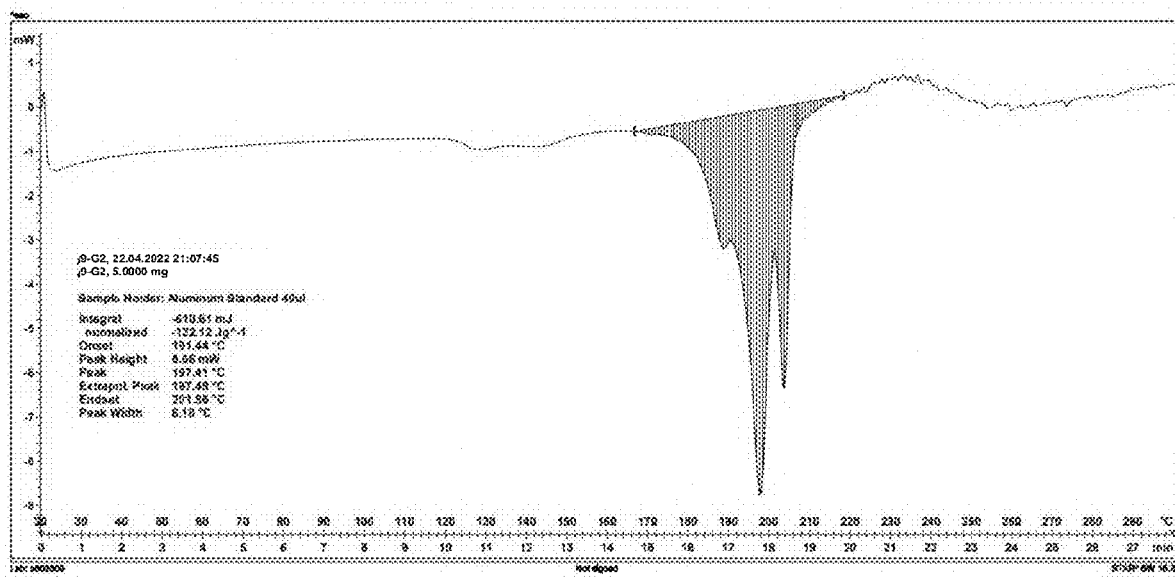

FIG. 176 depicts the DSC profile of 9-G2 (Experiment Reference 9-Sample Reference G2), analysis was acquired at a ramp rate of +10° C./minute.

Figure 177:
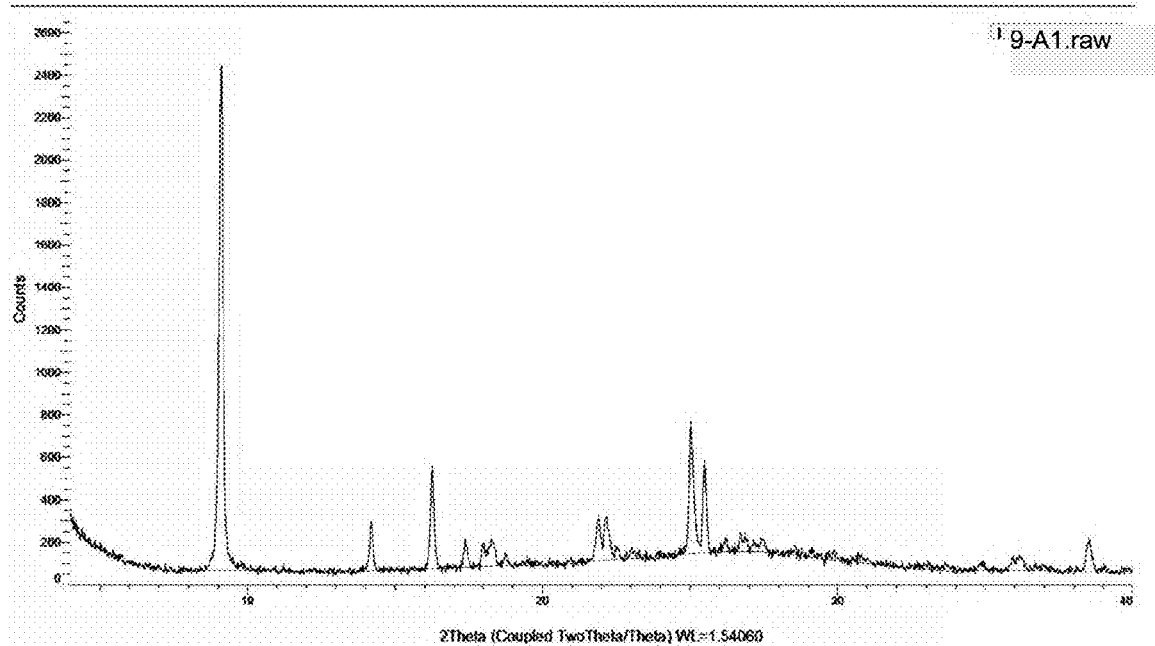

FIG. 177 depicts the XRPD profile of 9-A1 (Experiment Reference 9-Sample Reference A1) (Incoherent).

Figure 178:
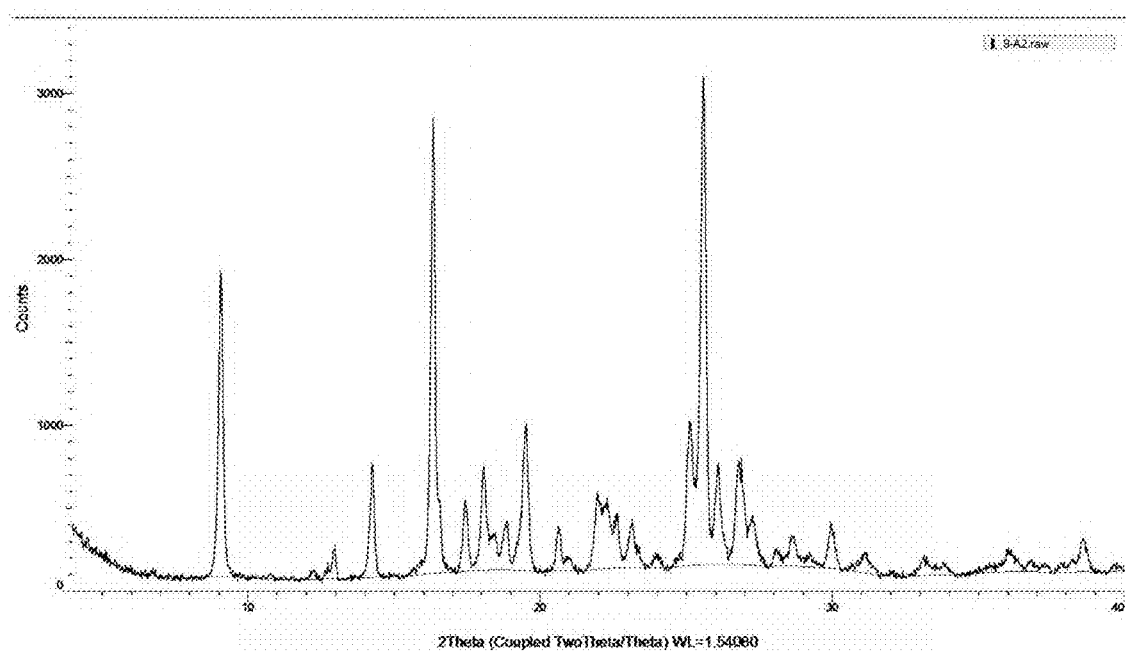

FIG. 178 depicts the XRPD profile of 9-A2 (Experiment Reference 9-Sample Reference A2) (Pattern #2c).

Figure 179:
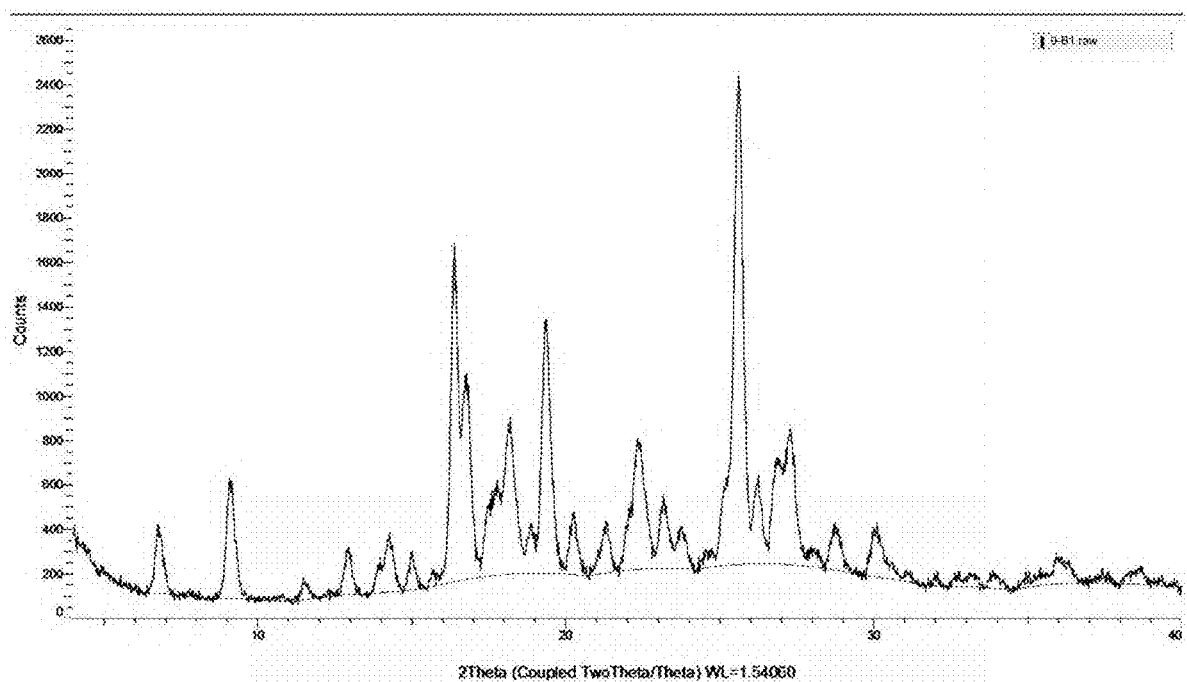

FIG. 179 depicts the XRPD profile of 9-B1 (Experiment Reference 9-Sample Reference B1) (Pattern #1).

Figure 180:
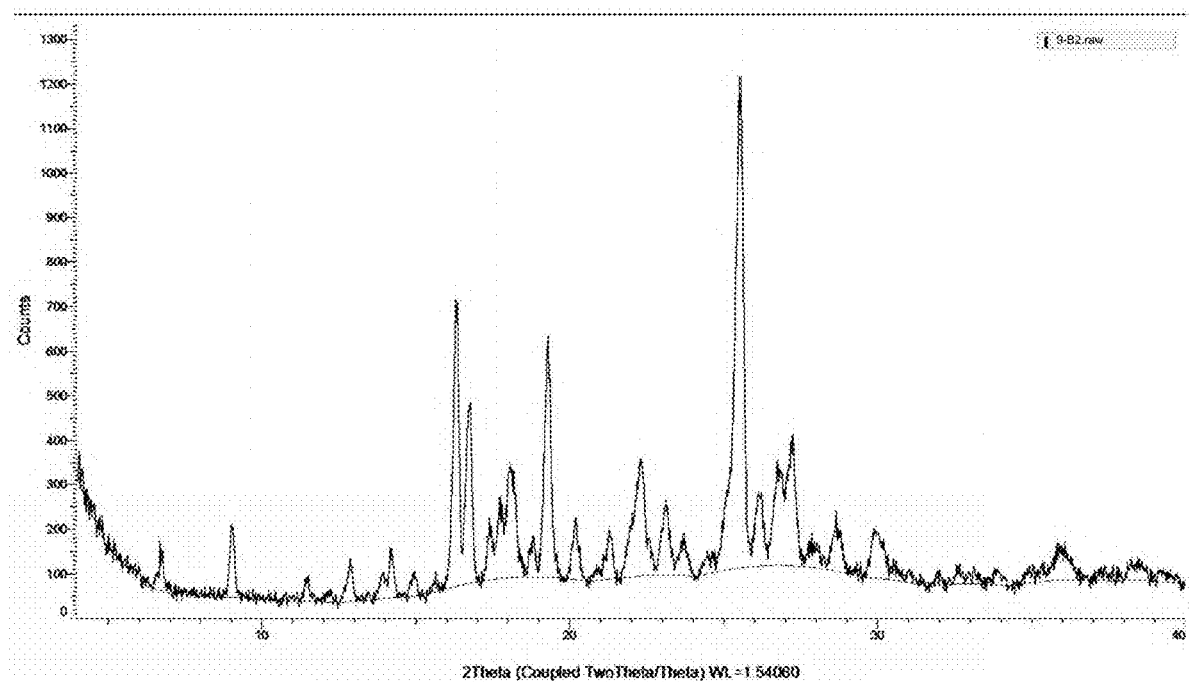

FIG. 180 depicts the XRPD profile of 9-B2 (Experiment Reference 9-Sample Reference B2) (Pattern #1).

Figure 181:
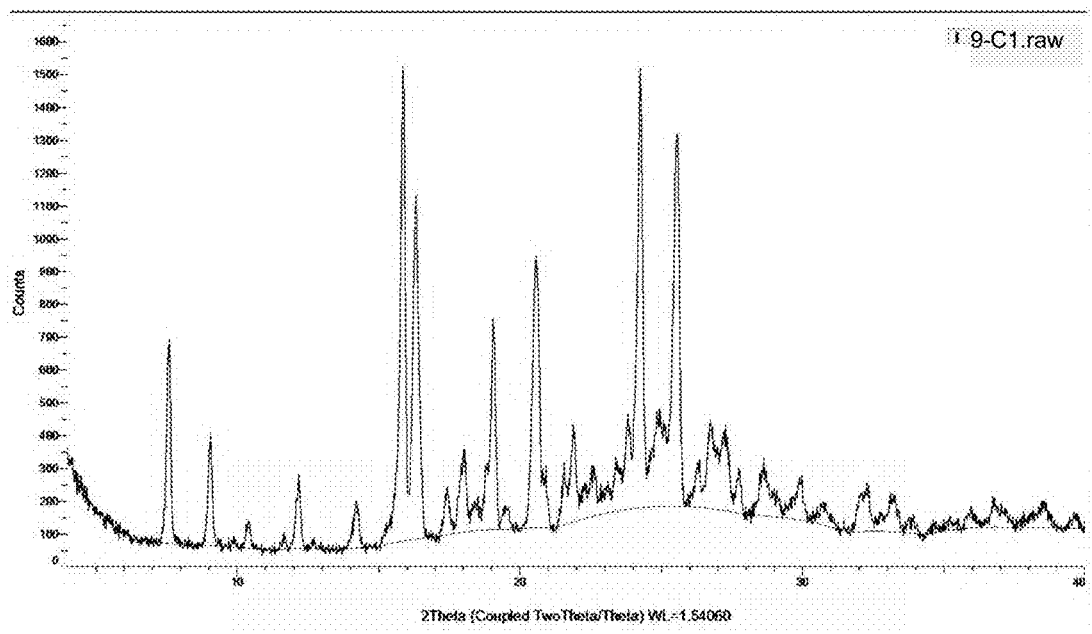

FIG. 181 depicts the XRPD profile of 9-C1 (Experiment Reference 9-Sample Reference C1) (Pattern #8).

Figure 182:
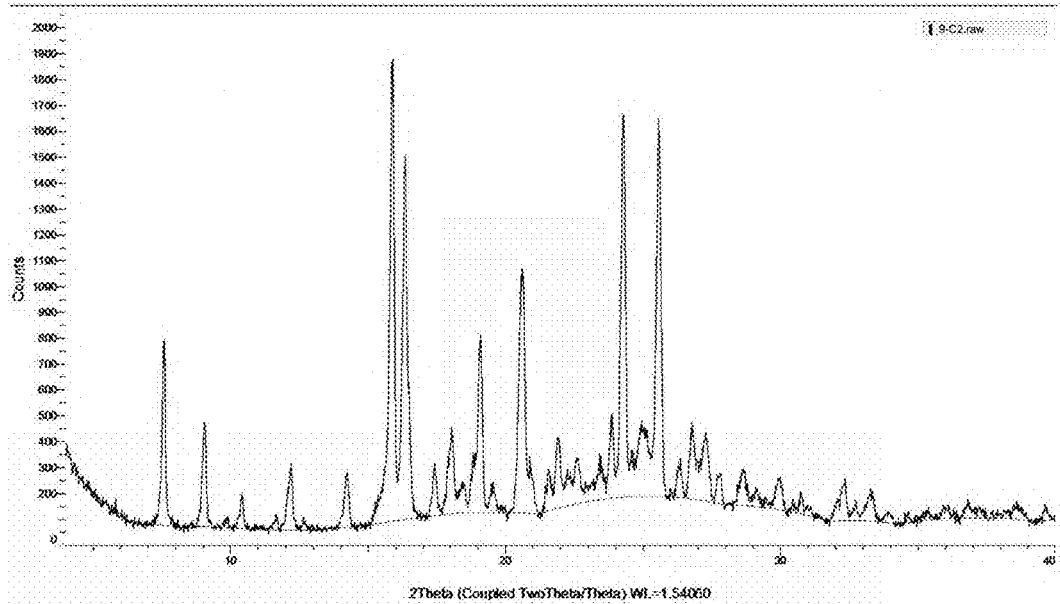

FIG. 182 depicts the XRPD profile of 9-C2 (Experiment Reference 9-Sample Reference C2) (Pattern #8).

Figure 183:
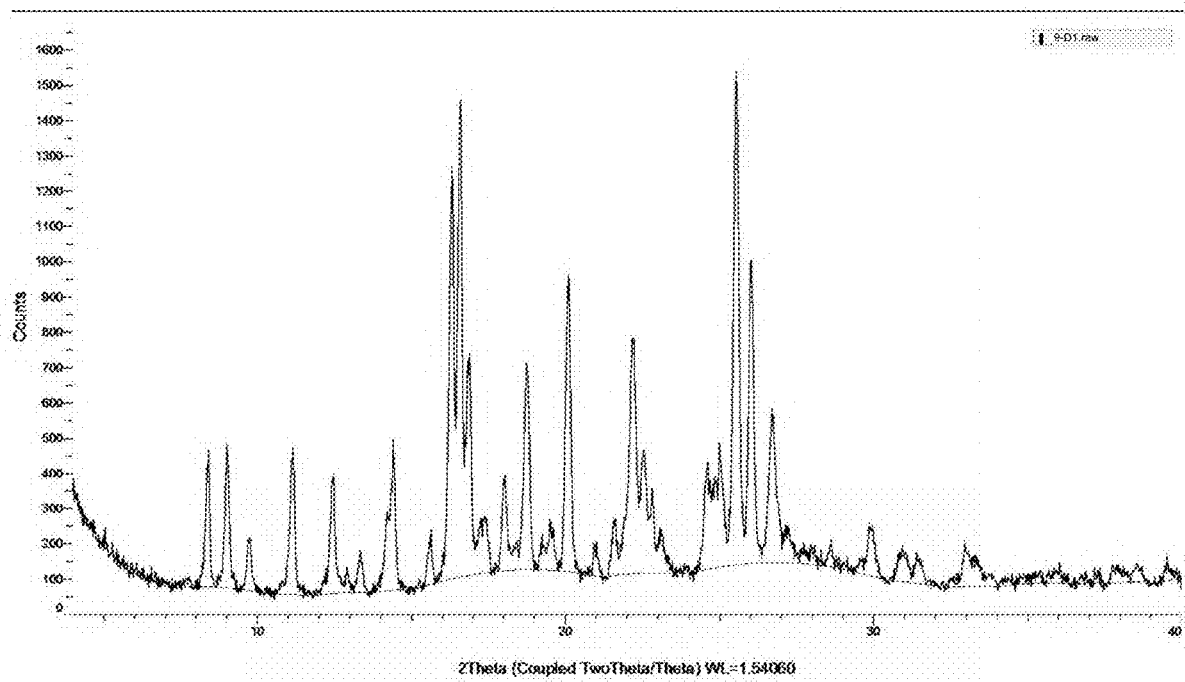

FIG. 183 depicts the XRPD profile of 9-D1 (Experiment Reference 9-Sample Reference D1) (Pattern #3).

Figure 184:
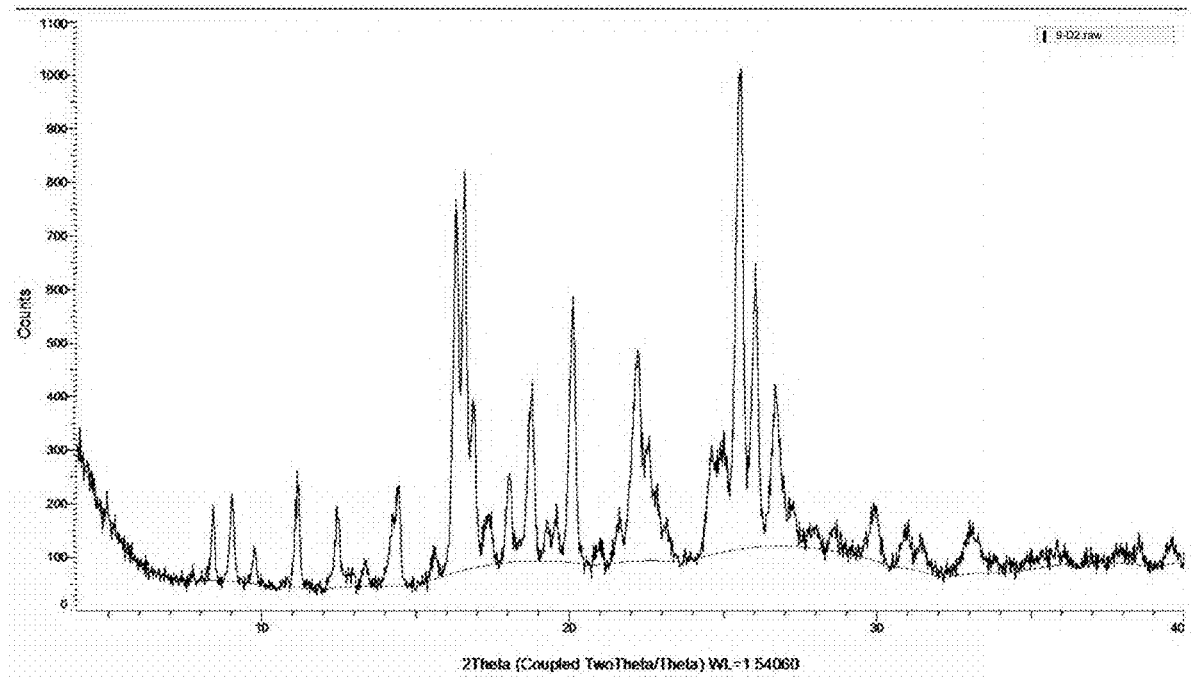

FIG. 184 depicts the XRPD profile of 9-D2 (Experiment Reference 9-Sample Reference D2) (Pattern #3).

Figure 185:
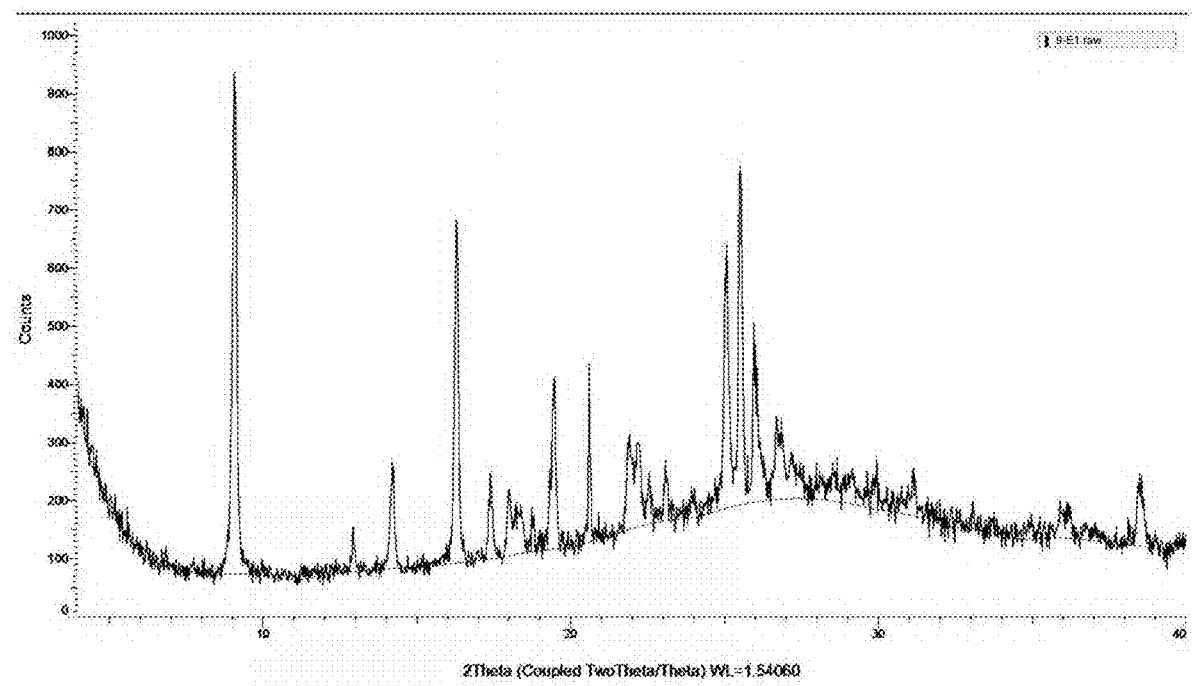

FIG. 185 depicts the XRPD profile of 9-E1 (Experiment Reference 9-Sample Reference E1) (Pattern #2c).

Figure 186:
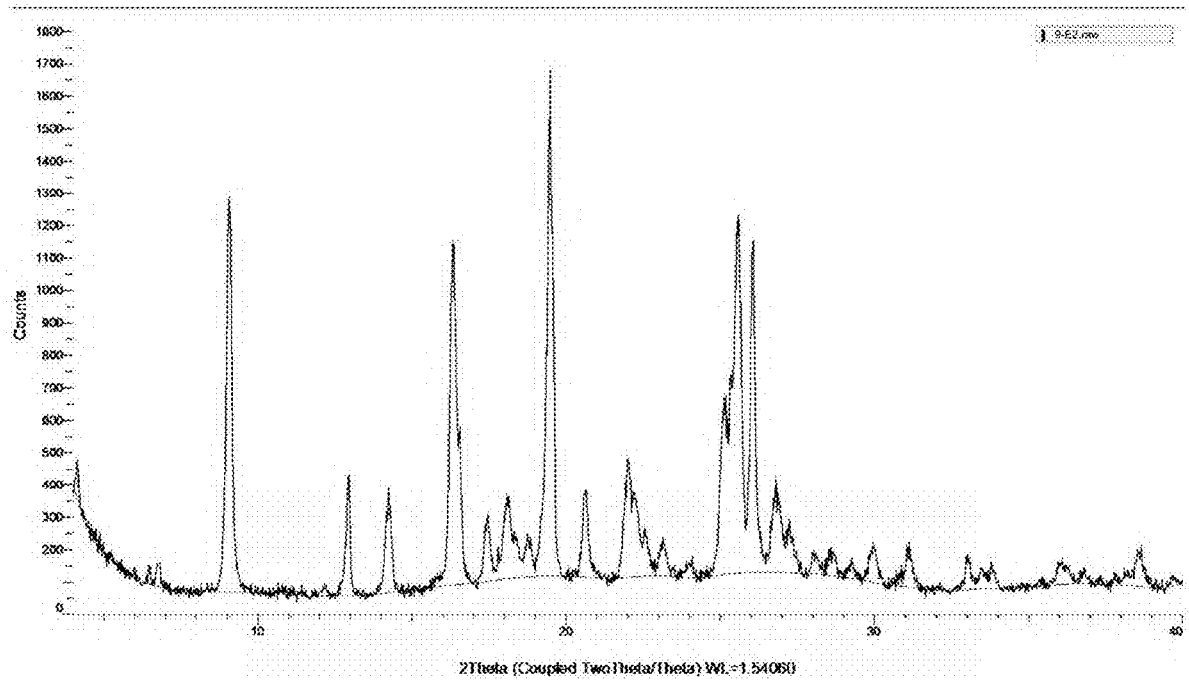

FIG. 186 depicts the XRPD profile of 9-E2 (Experiment Reference 9-Sample Reference E2) (Pattern #2c).

Figure 187:
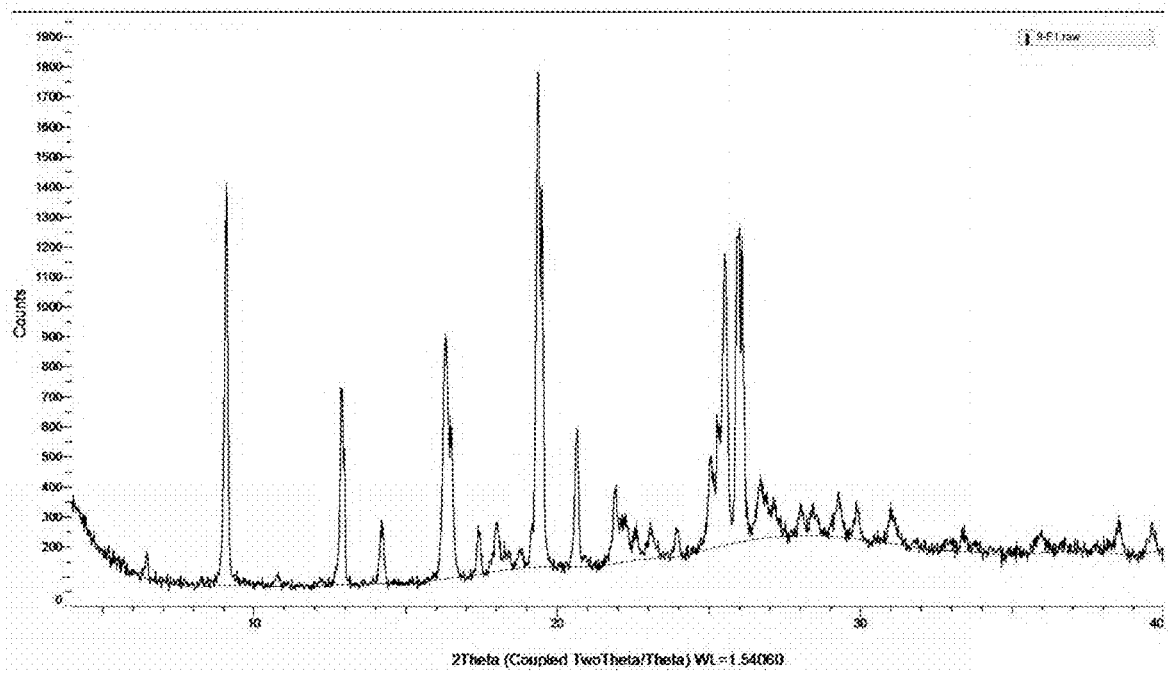

FIG. 187 depicts the XRPD profile of 9-F1 (Experiment Reference 9-Sample Reference F1) (Pattern #2c).

Figure 188:
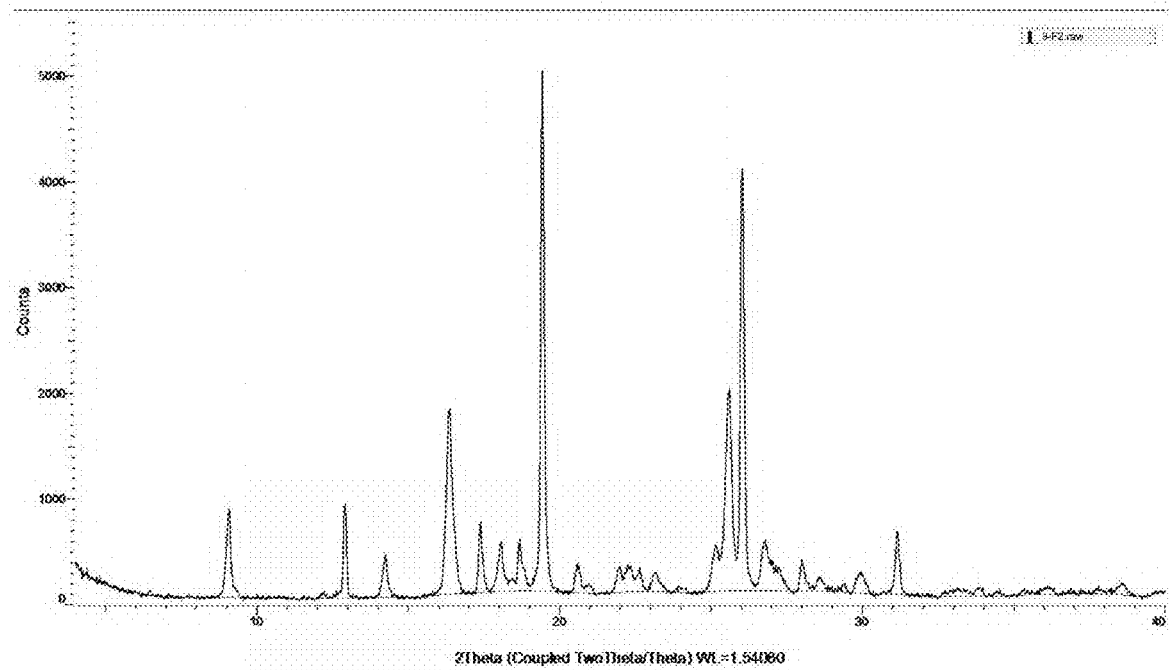

FIG. 188 depicts the XRPD profile of 9-F2 (Experiment Reference 9-Sample Reference F2) (Pattern #2c).

Figure 189:
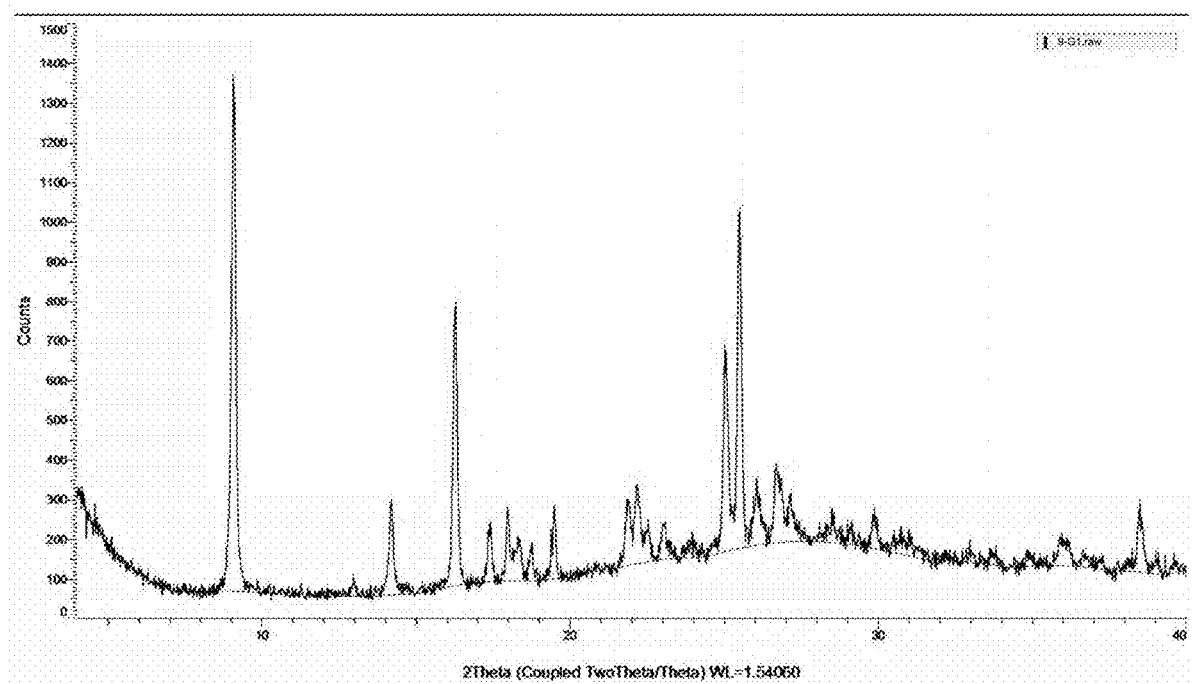

FIG. 189 depicts the XRPD profile of 9-G1 (Experiment Reference 9-Sample Reference G1) (Pattern #2c).

Figure 190:
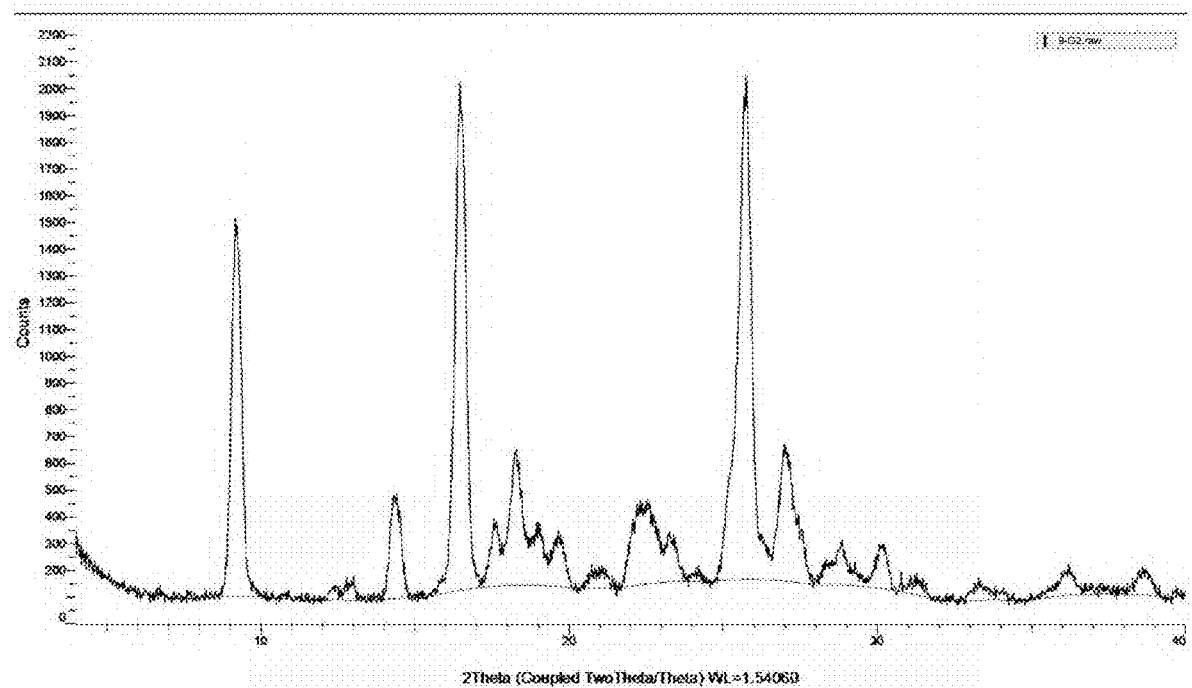

FIG. 190 depicts the XRPD profile of 9-G2 (Experiment Reference 9-Sample Reference G2) (Pattern #2c).

Figure 191:
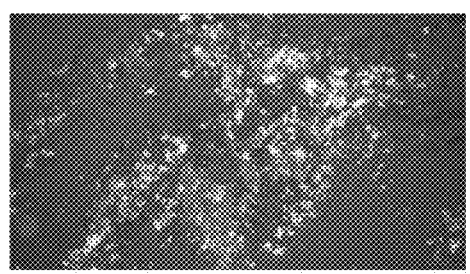

FIG. 191 depicts the 9-E2 (Experiment Reference 9-Sample Reference E2) cross polarized (magnification×2).

Figure 192:
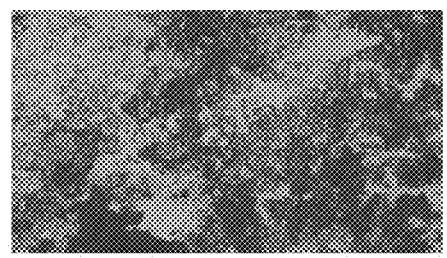

FIG. 192 depicts the 9-E2 (Experiment Reference 9-Sample Reference E2) normal polarized (magnification×5).

Figure 193:
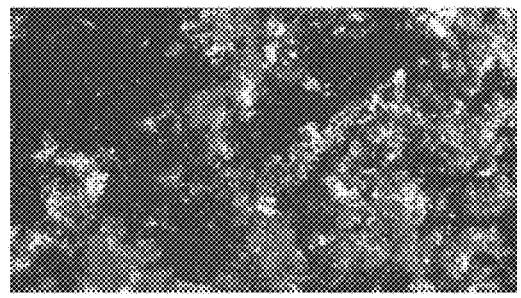

FIG. 193 depicts the 9-E2 (Experiment Reference 9-Sample Reference E2) cross polarized (magnification×5).

Figure 194:

FIG. 194 depicts the 9-E2 (Experiment Reference 9-Sample Reference E2) normal polarized (magnification×25).

Figure 195:
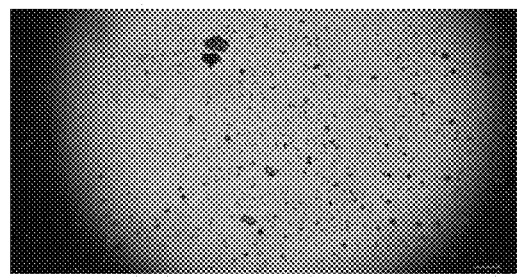

FIG. 195 depicts the 9-F2 (Experiment Reference 9-Sample Reference F2) normal polarized (magnification×2).

Figure 196:

FIG. 196 depicts the 9-F2 (Experiment Reference 9-Sample Reference F2) normal polarized (magnification×5).

Figure 197:
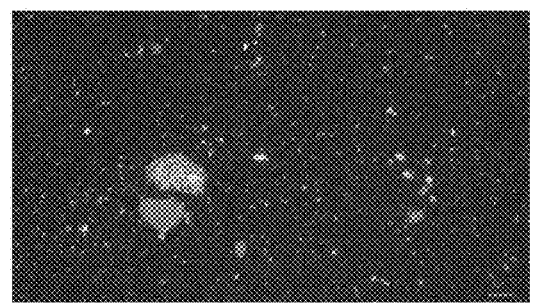

FIG. 197 depicts the 9-F2 (Experiment Reference 9-Sample Reference F2) cross polarized (magnification×5).

Figure 198:
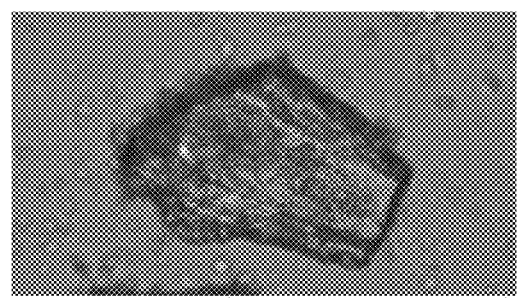

FIG. 198 depicts the 9-F2 (Experiment Reference 9-Sample Reference F2) normal polarized (magnification×25).

Figure 199:
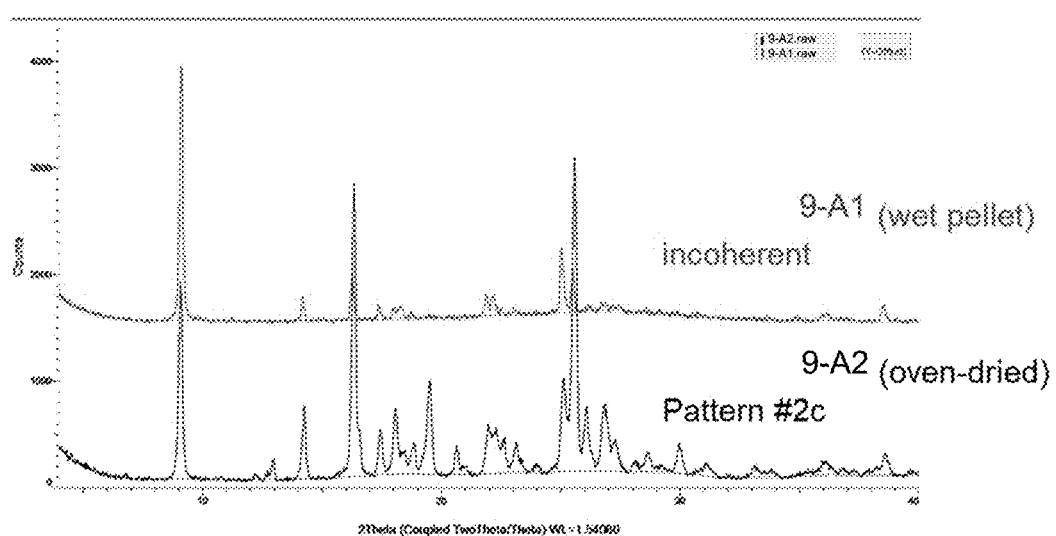

FIG. 199 depicts the XRPD diffractogram overlay of 9-A1 (Experiment Reference 9-Sample Reference A1) and 9-A2 (Experiment Reference 9-Sample Reference A2) (water).

Figure 200:
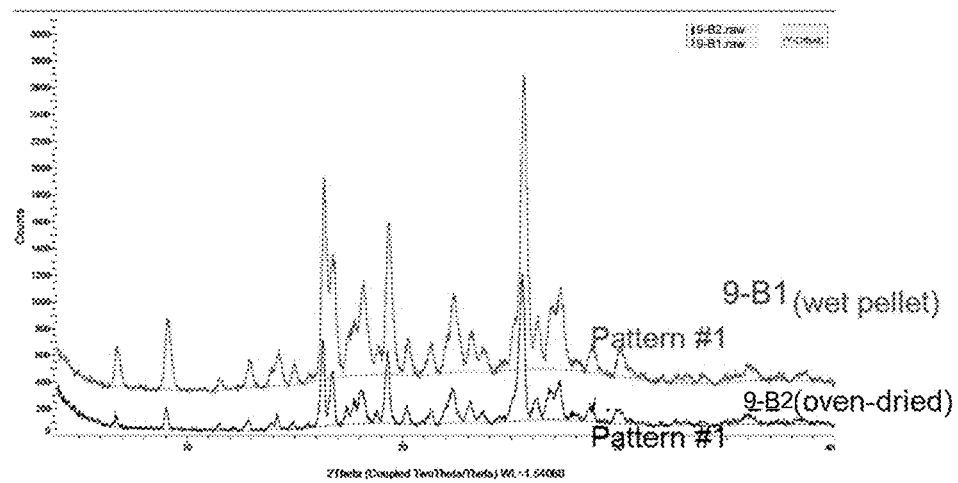

FIG. 200 depicts the XRPD diffractogram overlay of 9-B1 (Experiment Reference 9-Sample Reference B1) and 9-B2 (Experiment Reference 9-Sample Reference B2) (tBME).

Figure 201:
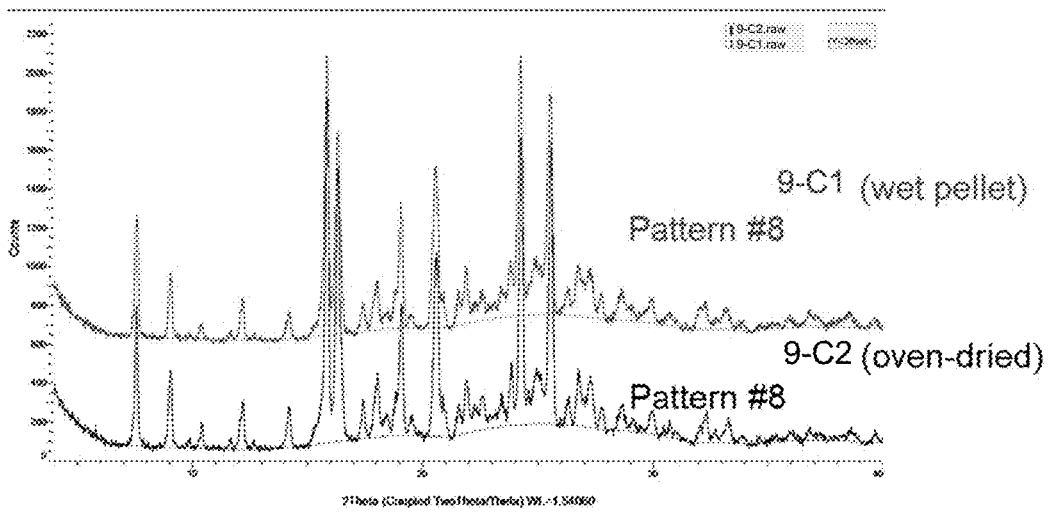

FIG. 201 depicts the XRPD diffractogram overlay of 9-C1 (Experiment Reference 9-Sample Reference C1) and 9-C2 (Experiment Reference 9-Sample Reference C2) (iPAC).

Figure 202:
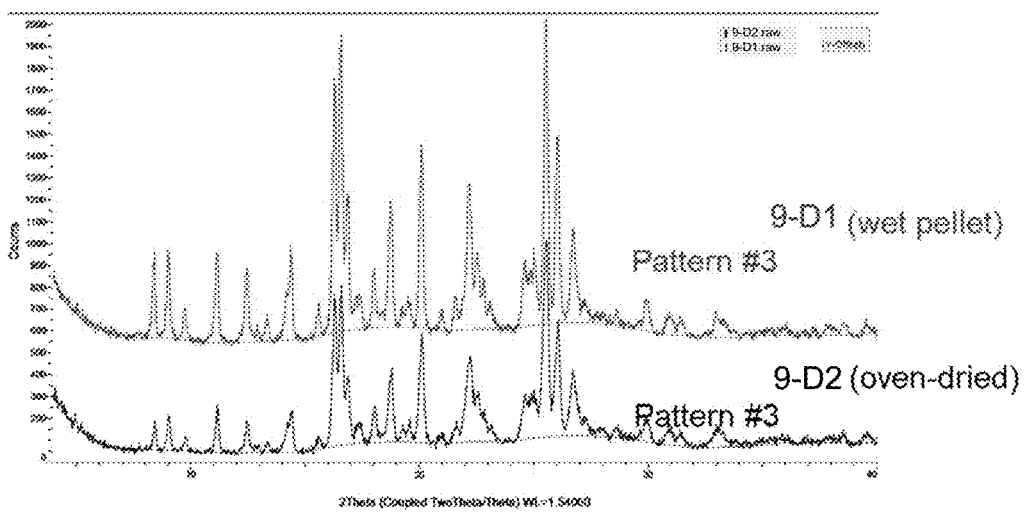

FIG. 202 depicts the XRPD diffractogram overlay of 9-D1 (Experiment Reference 9-Sample Reference D1) and 9-D2 (Experiment Reference 9-Sample Reference D2) (toluene).

Figure 203:
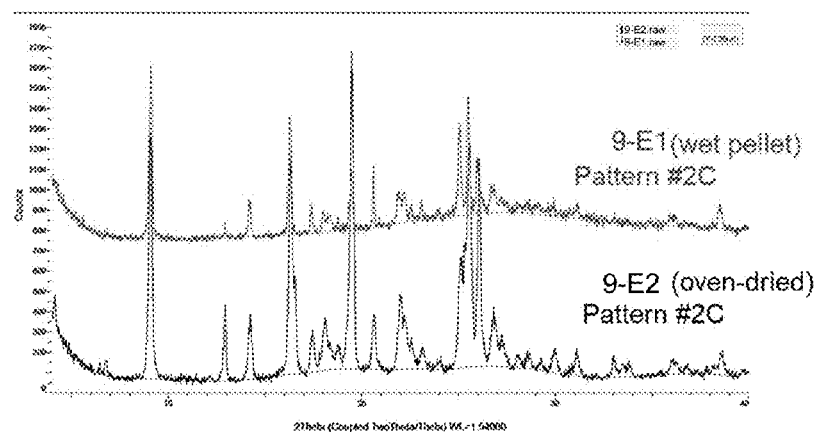

FIG. 203 depicts the XRPD diffractogram overlay of 9-E1 (Experiment Reference 9-Sample Reference E1) and 9-E2 (Experiment Reference 9-Sample Reference E2) (water).

Figure 204:
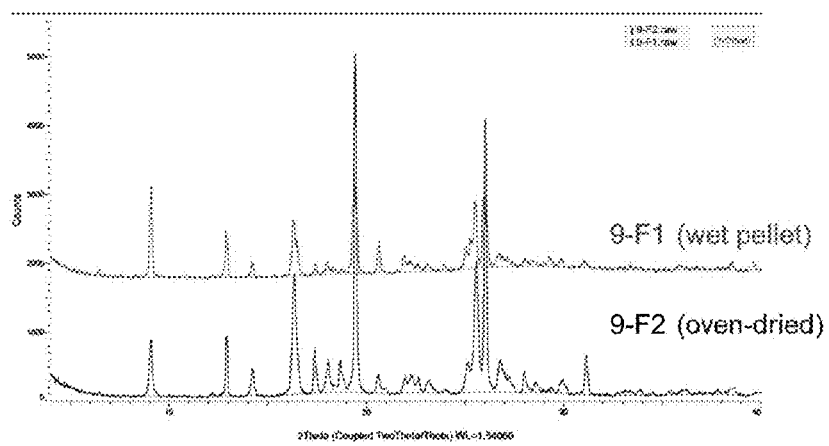

FIG. 204 depicts the XRPD diffractogram overlay of 9-F1 (Experiment Reference 9-Sample Reference F1) and 9-F2 (Experiment Reference 9-Sample Reference F2) (water).

Figure 205:
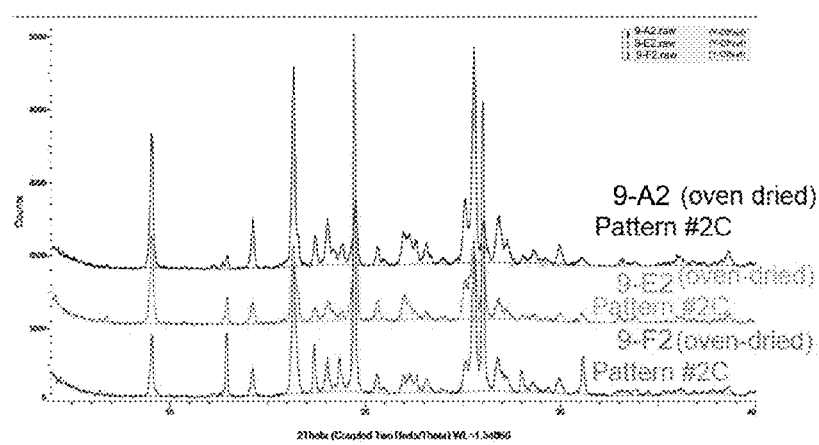

FIG. 205 depicts the XRPD diffractogram overlay of 9-A2 (Experiment Reference 9-Sample Reference A2), 9-E2 (Experiment Reference 9-Sample Reference E2) and 9-F2 (Experiment Reference 9-Sample Reference F2).

Figure 206:
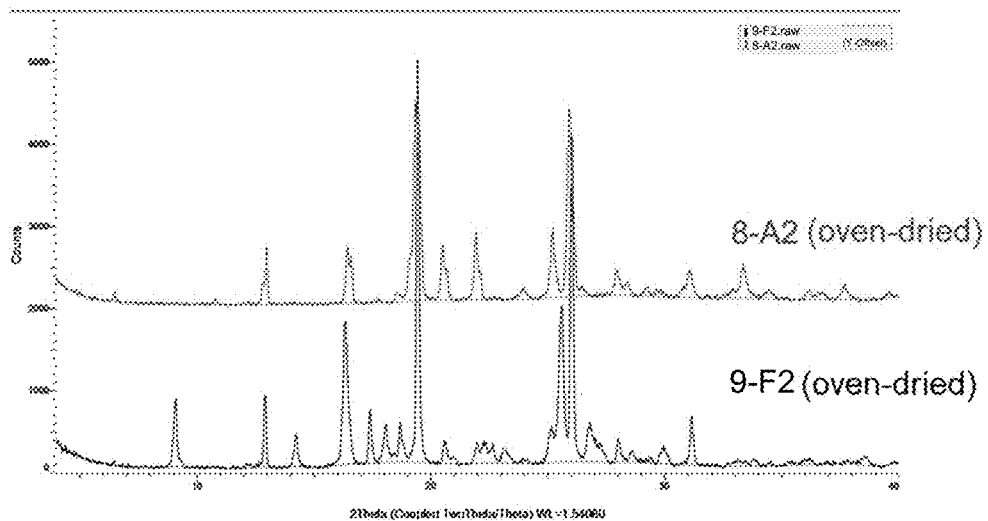

FIG. 206 depicts the XRPD diffractogram overlay of 8-A2 (Experiment Reference 8-Sample Reference A2) (input) and 9-F2 (Experiment Reference 9-Sample Reference F2).

Figure 207:
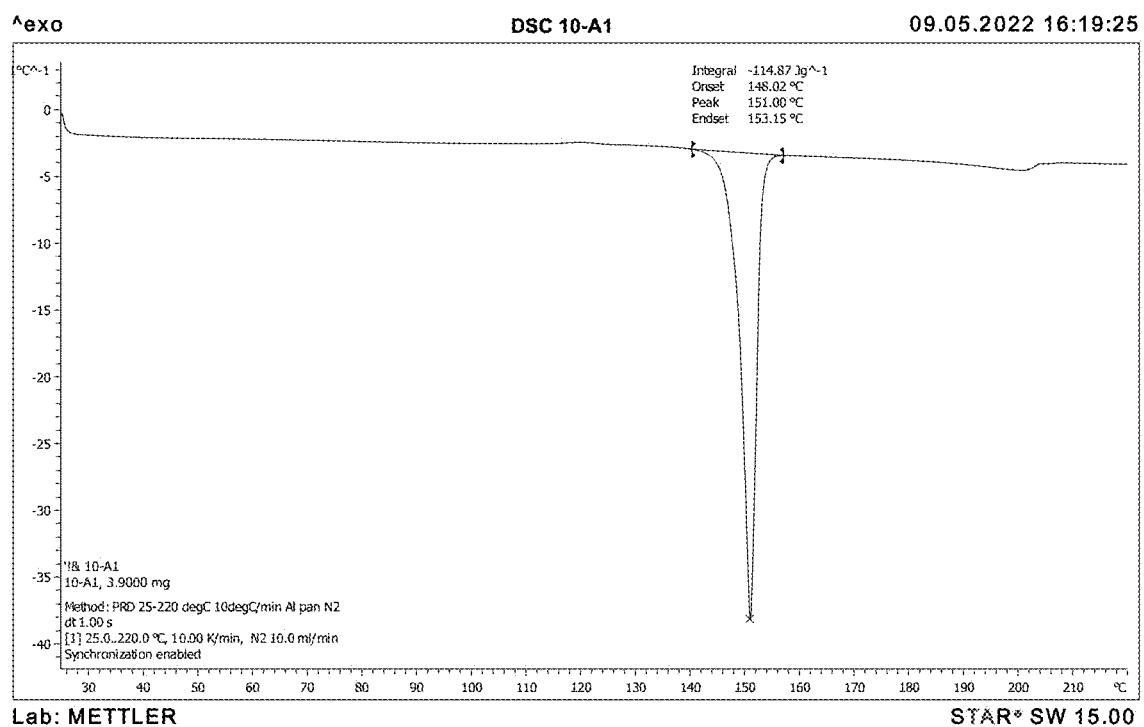

FIG. 207 depicts the DSC profile of 10-A1 (Experiment Reference 10-Sample Reference A1), analysis was acquired at a ramp rate of +10° C./minute.

Figure 208:
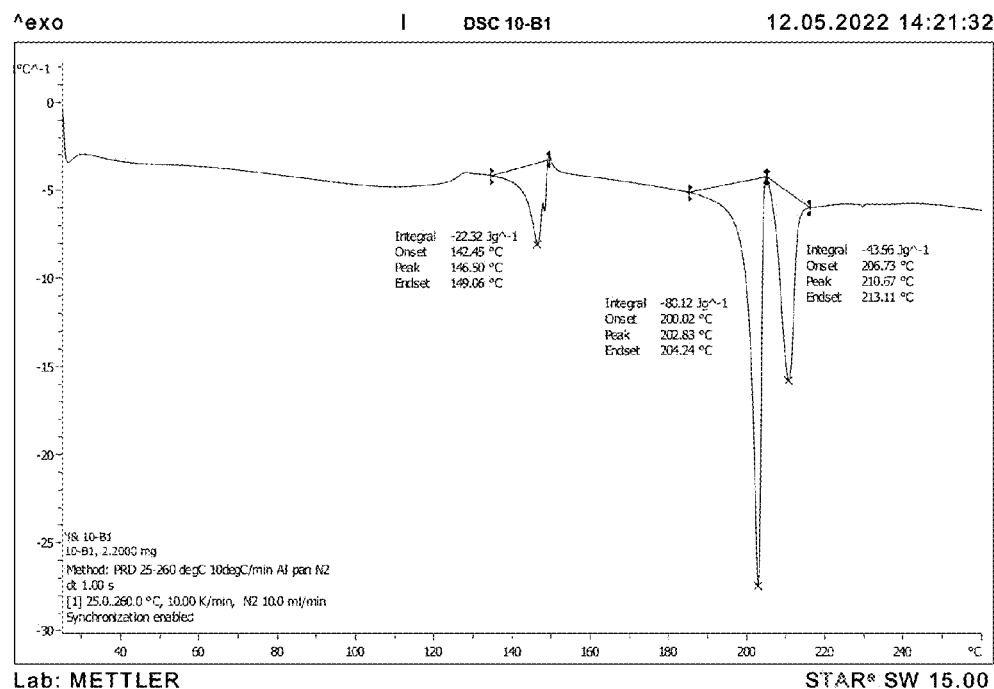

FIG. 208 depicts the DSC profile of 10-B1 (Experiment Reference 10-Sample Reference B1), analysis was acquired at a ramp rate of +10° C./minute.

Figure 209:
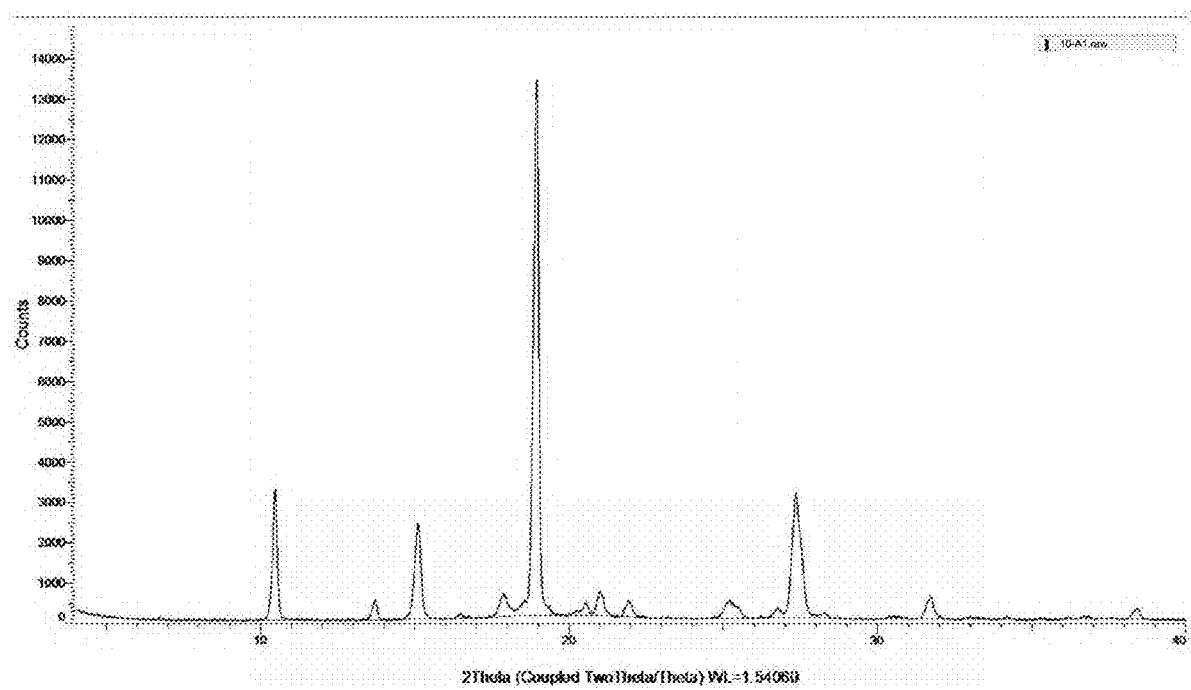

FIG. 209 depicts the XRPD profile of 10-A1 (Experiment Reference 10-Sample Reference A1) (Pattern #22).

Figure 210:
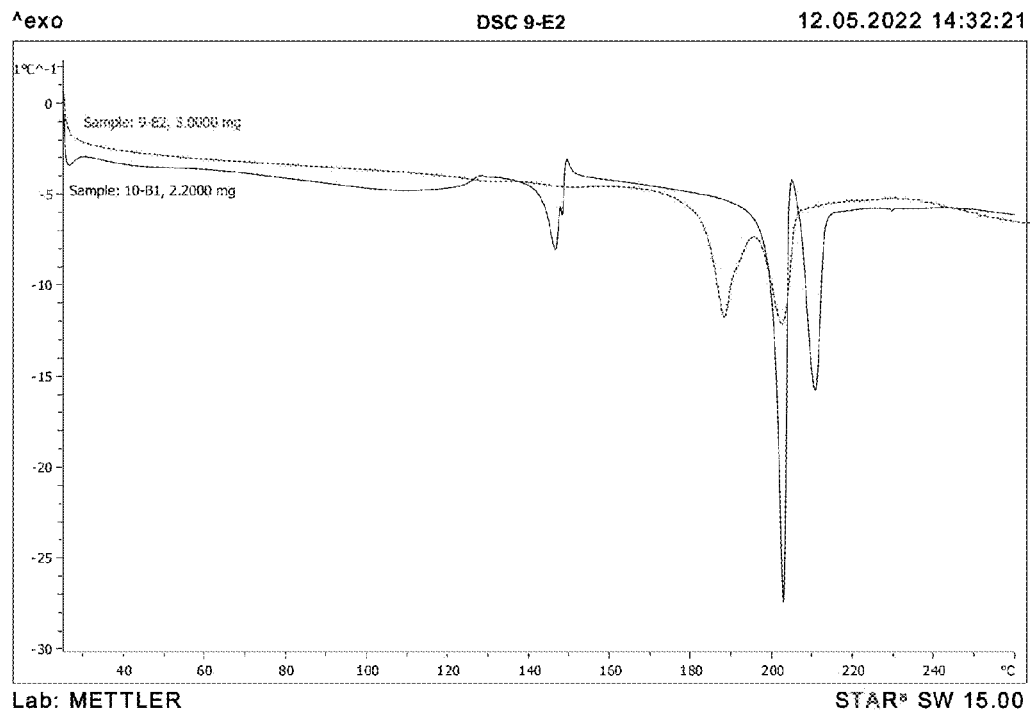

FIG. 210 depicts the DSC thermogram overlay of 9-E2 (Experiment Reference 9-Sample Reference E2) (red) and 10-B1 (Experiment Reference 10-Sample Reference B1) (black).

Figure 211:
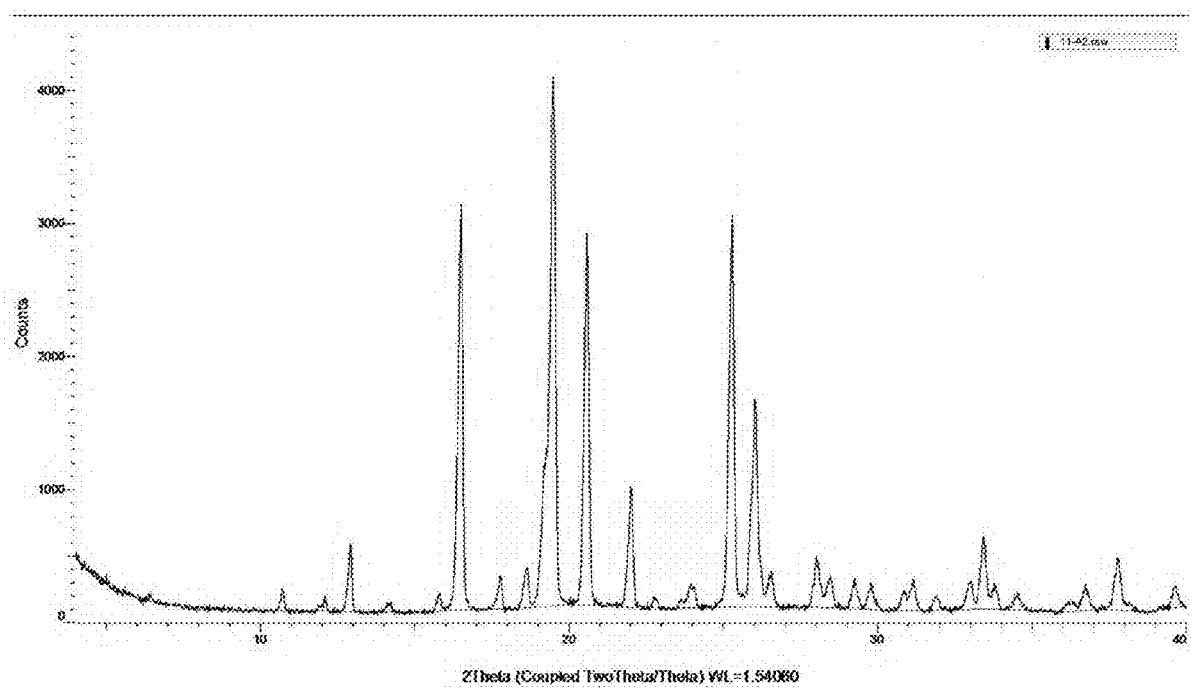

FIG. 211 depicts the XRPD profile of 11-A2 (Experiment Reference 11-Sample Reference A2) (Pattern #6a).

Figure 212:
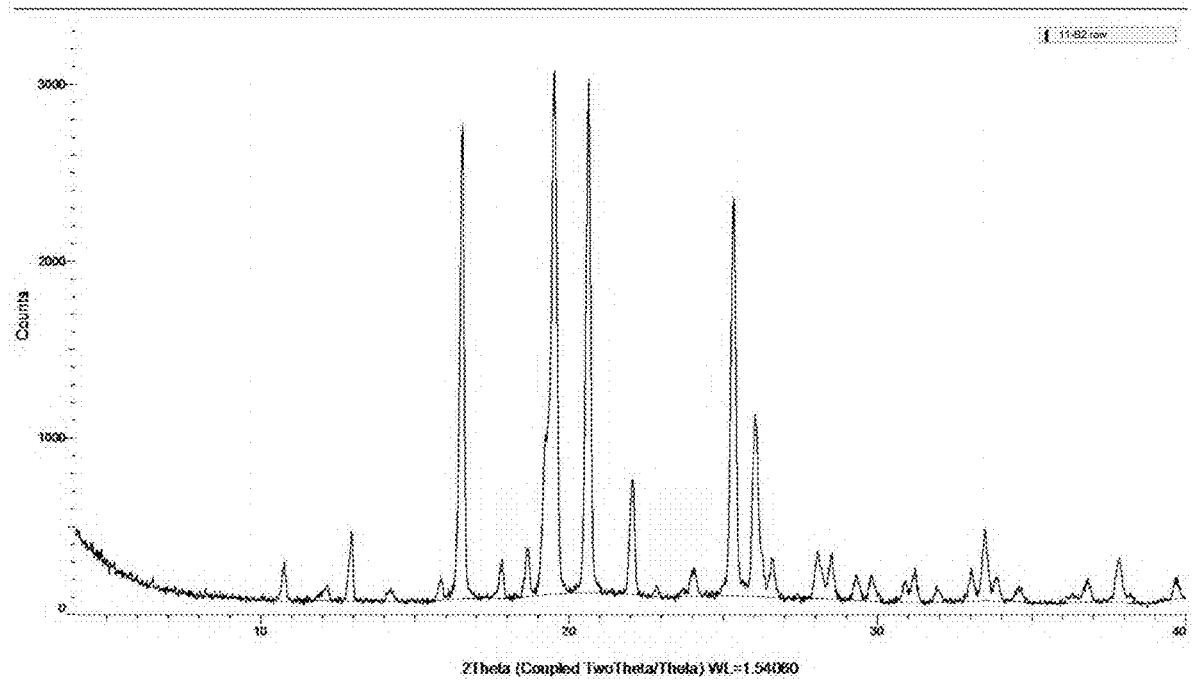

FIG. 212 depicts the XRPD profile of 11-B2 (Experiment Reference 11-Sample Reference B2) (Pattern #6a).

Figure 213:
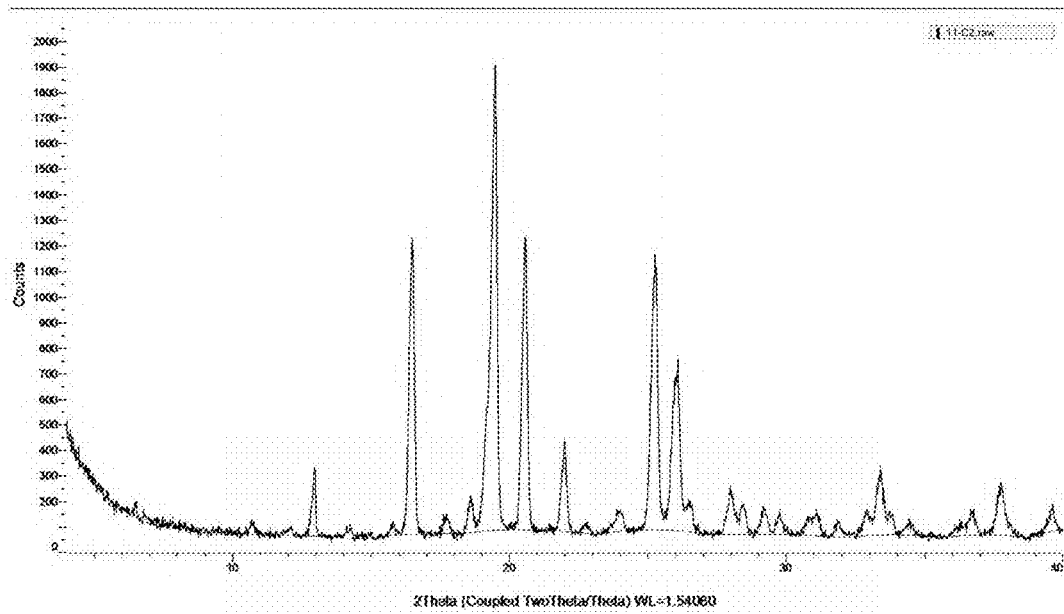

FIG. 213 depicts the XRPD profile of 11-C2 (Experiment Reference 11-Sample Reference C2) (Pattern #6a).

Figure 214:
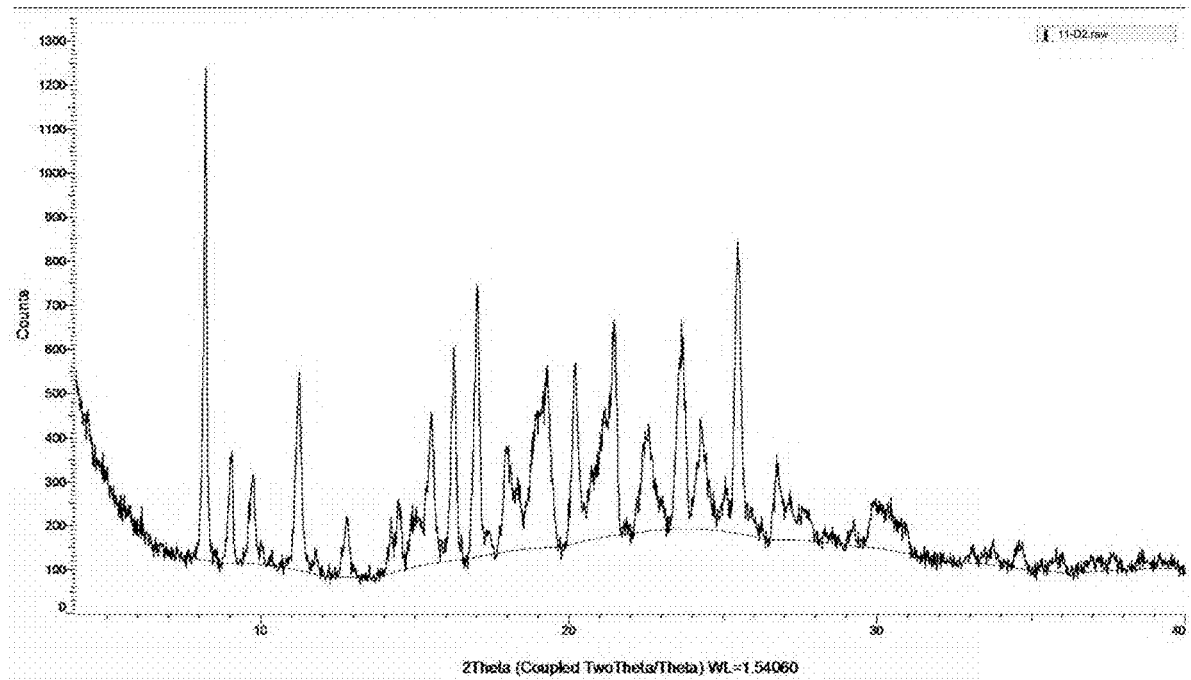

FIG. 214 depicts the XRPD profile of 11-D2 (Experiment Reference 11-Sample Reference D2) (Pattern #5).

Figure 215:
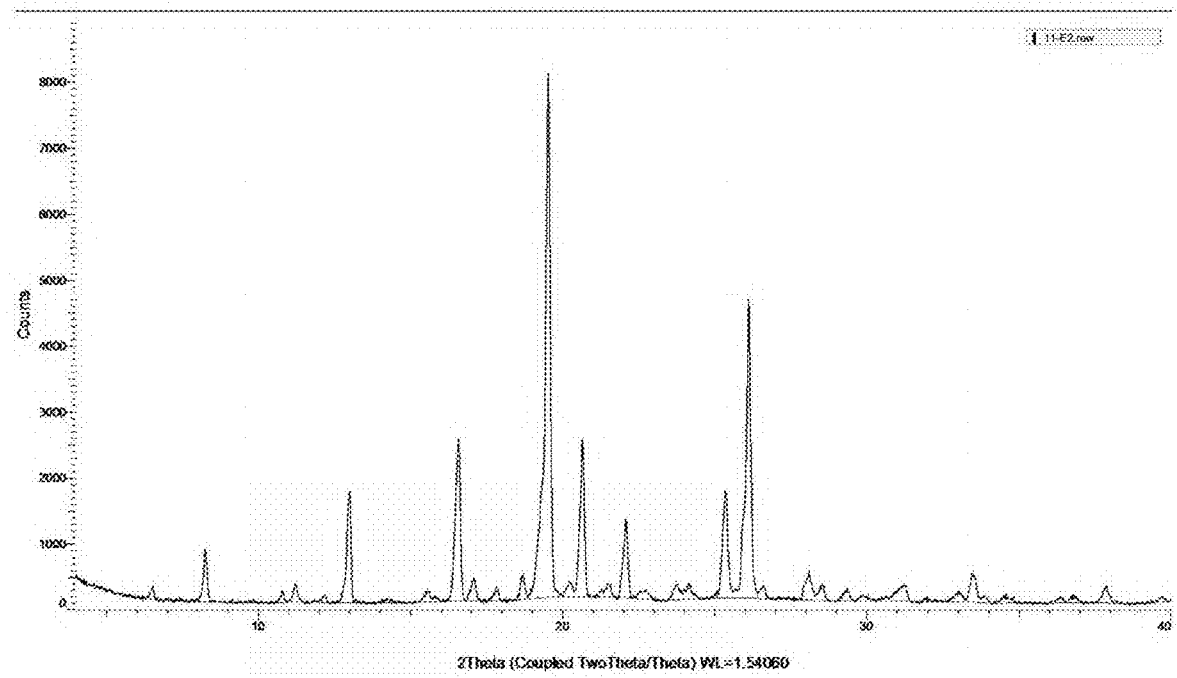

FIG. 215 depicts the XRPD profile of 11-E2 (Experiment Reference 11-Sample Reference E2) (Pattern #6b).

Figure 216:
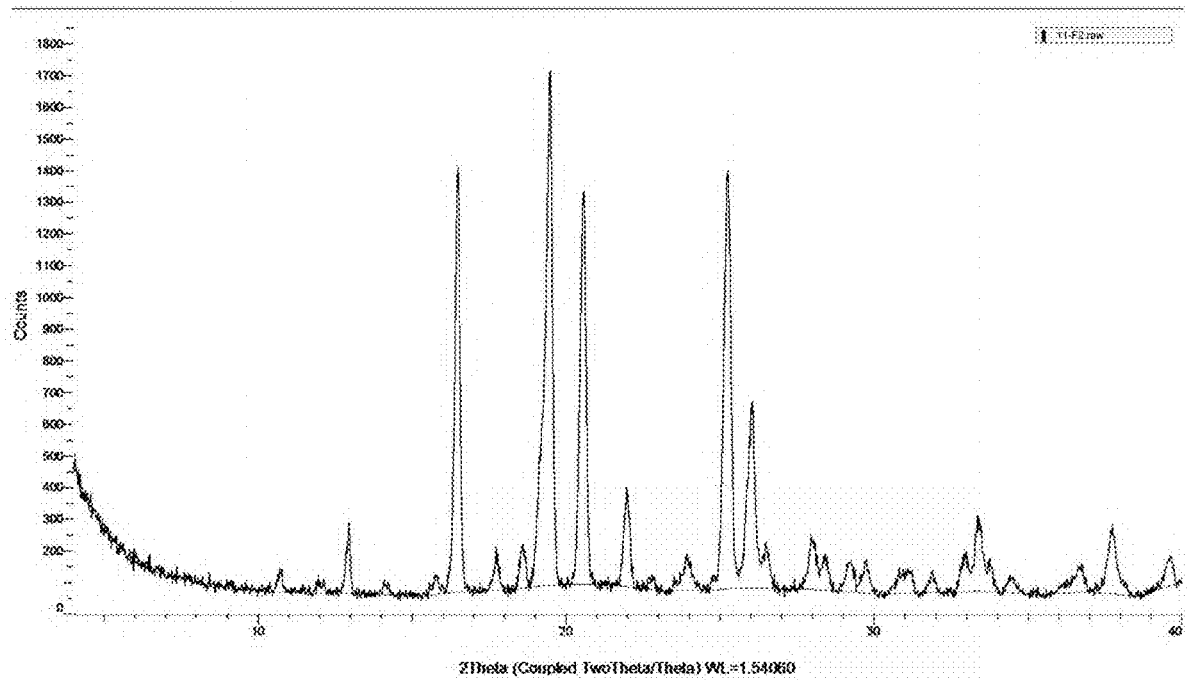

FIG. 216 depicts the XRPD profile of 11-F2 (Experiment Reference 11-Sample Reference F2) (Pattern #6a).

Figure 217:
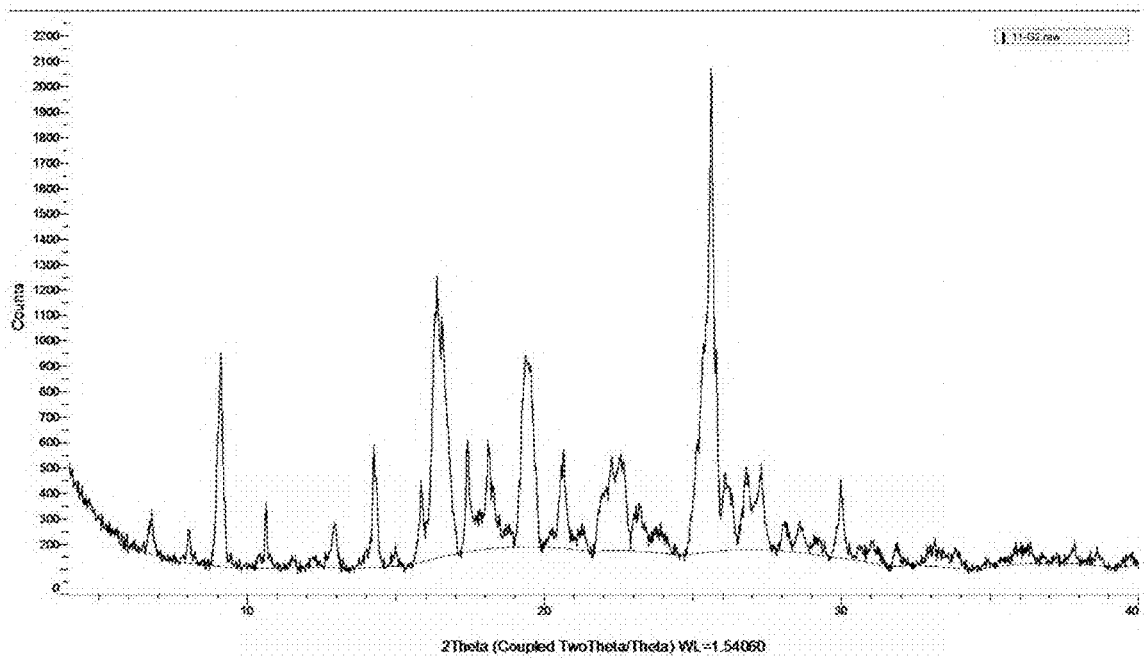

FIG. 217 depicts the XRPD profile of 11-G2 (Experiment Reference 11-Sample Reference G2) (Pattern #1).

Figure 218:
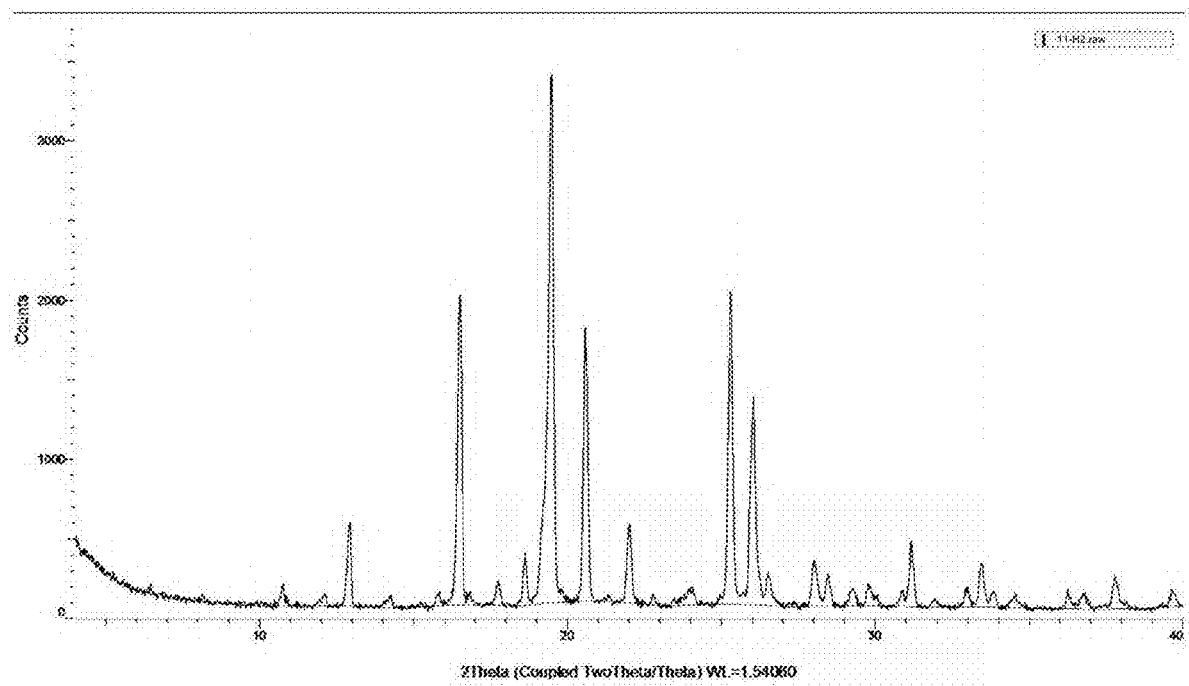

FIG. 218 depicts the XRPD profile of 11-H2 (Experiment Reference 11-Sample Reference H2) (Pattern #6a).

Figure 219:
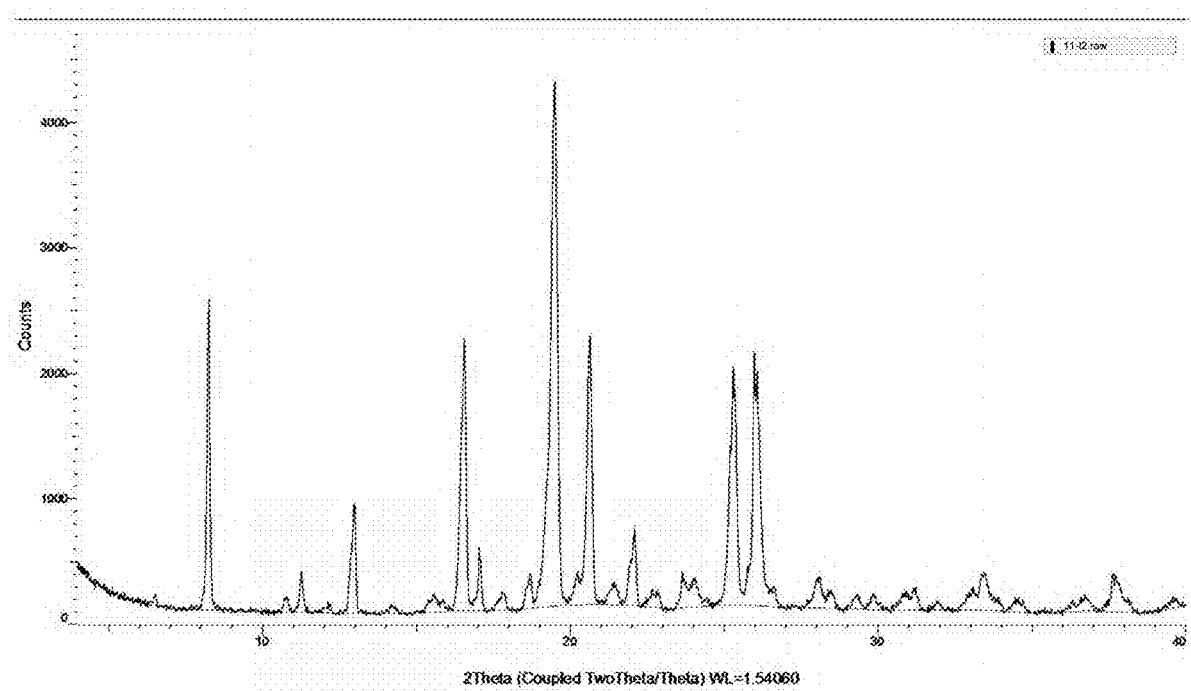

FIG. 219 depicts the XRPD profile of 11-I2 (Experiment Reference 11-Sample Reference I2) (Pattern #6b).

Figure 220:
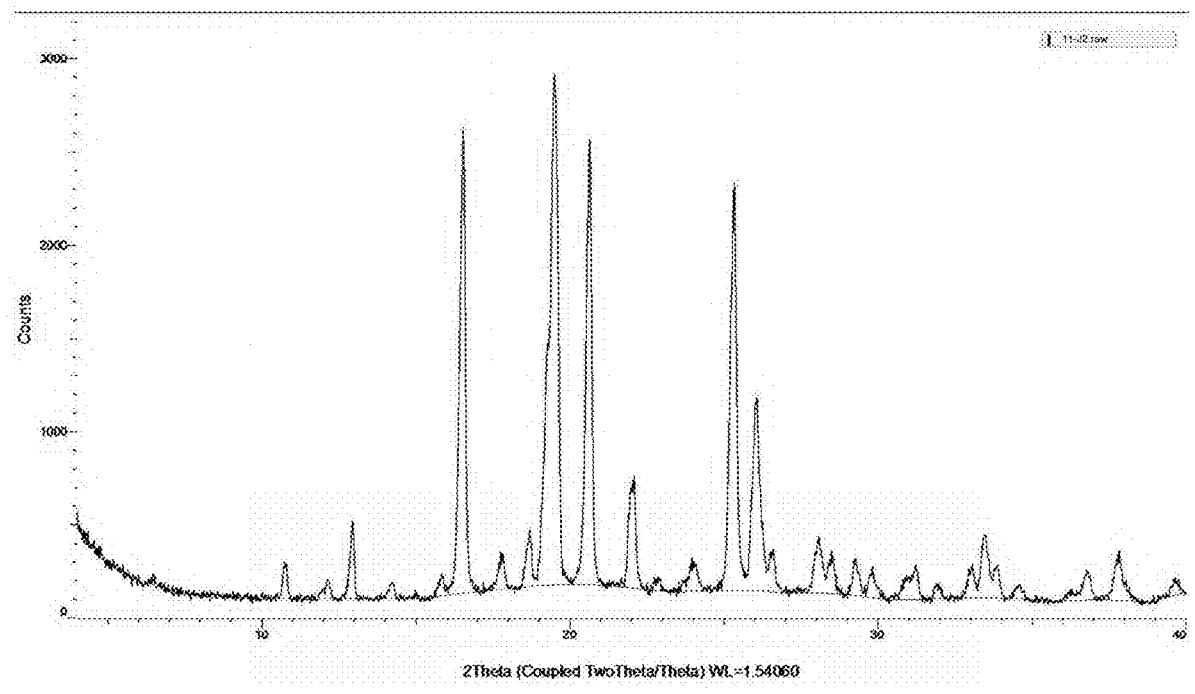

FIG. 220 depicts the XRPD profile of 11-J2 (Experiment Reference 11-Sample Reference J2) (Pattern #6a).

Figure 221:
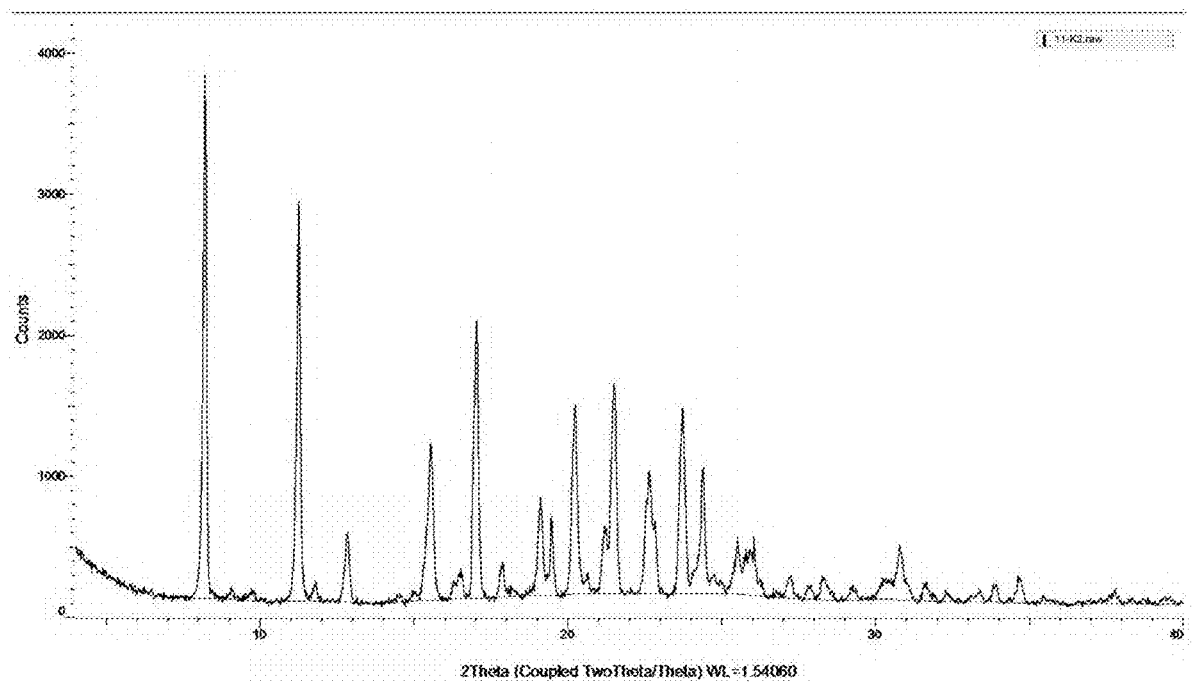

FIG. 221 depicts the XRPD profile of 11-K2 (Experiment Reference 11-Sample Reference K2) (Pattern #5).

Figure 222:
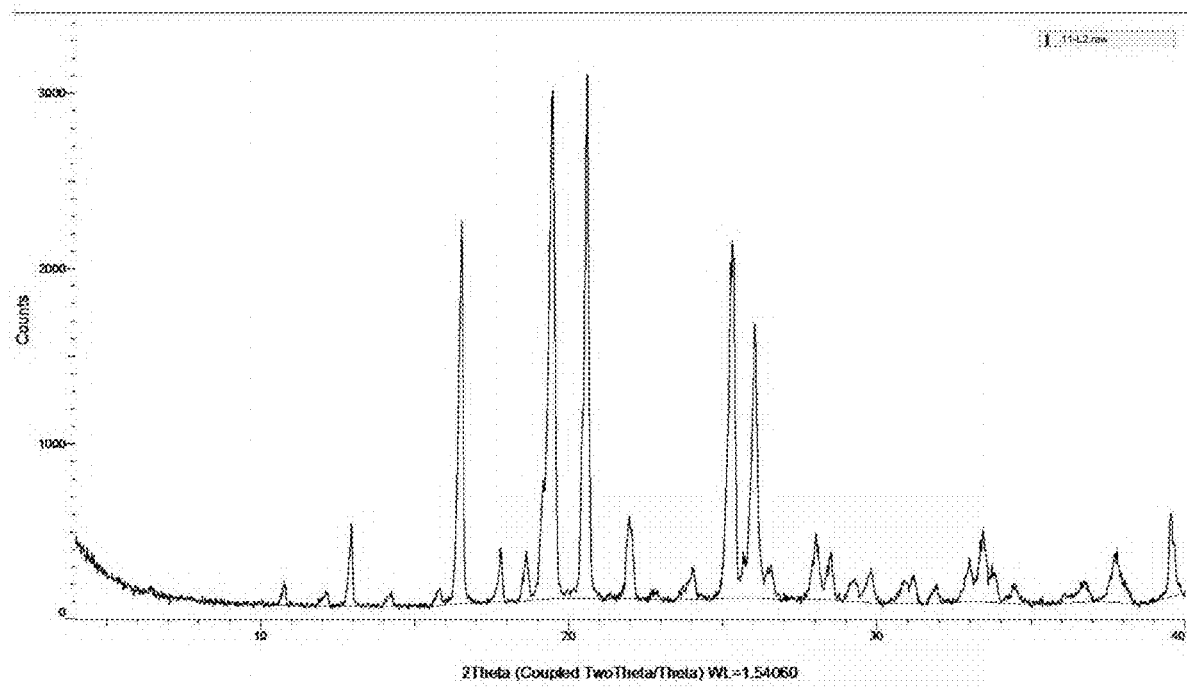

FIG. 222 depicts the XRPD profile of 11-L2 (Experiment Reference 11-Sample Reference L2) (Pattern #6a).

Figure 223:
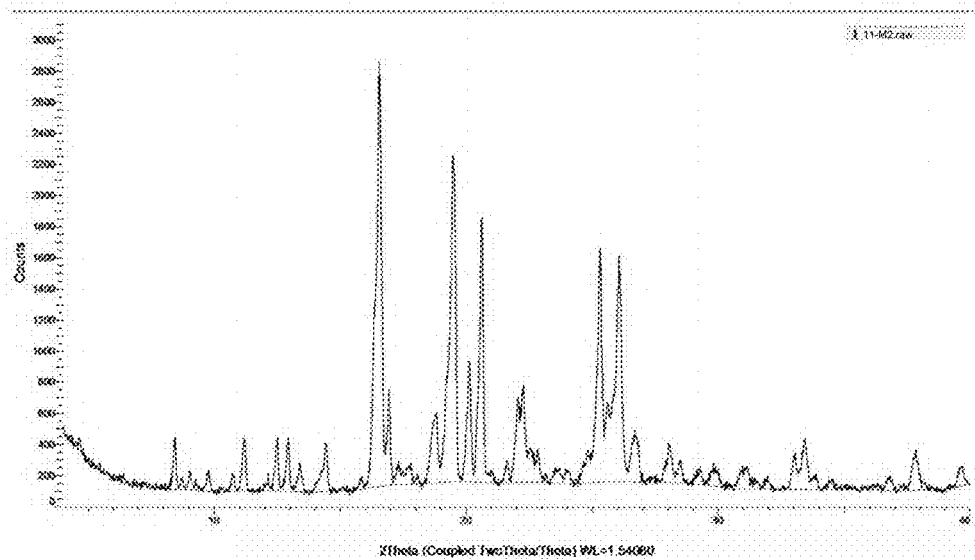

FIG. 223 depicts the XRPD profile of 11-M2 (Experiment Reference 11-Sample Reference M2) (Pattern #6a).

Figure 224:
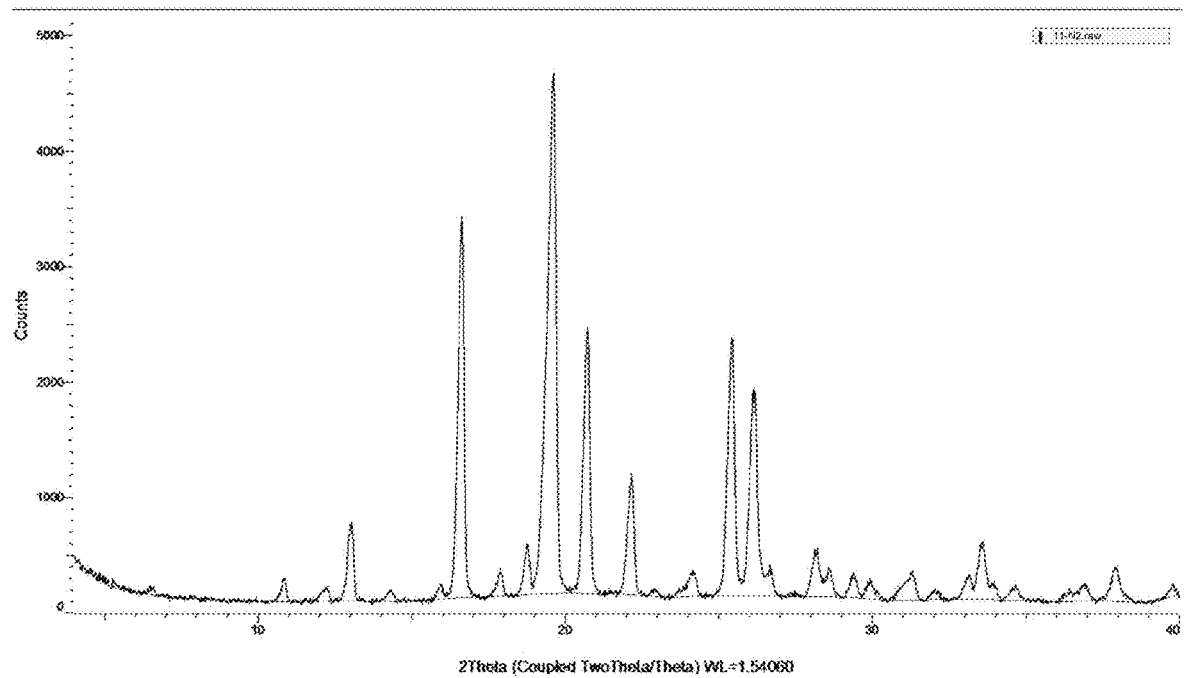

FIG. 224 depicts the XRPD profile of 11-N2 (Experiment Reference 11-Sample Reference N2) (Pattern #6a).

Figure 225:
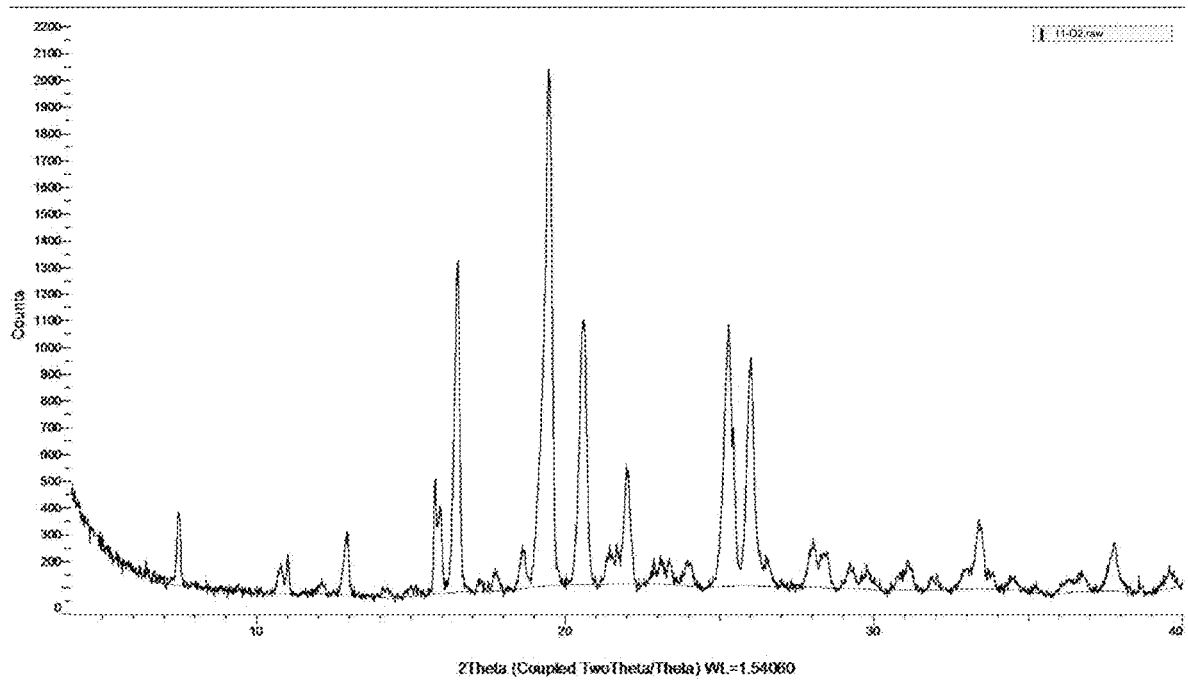

FIG. 225 depicts the XRPD profile of 11-O2 (Experiment Reference 11-Sample Reference O2) (Pattern #6a).

Figure 226:
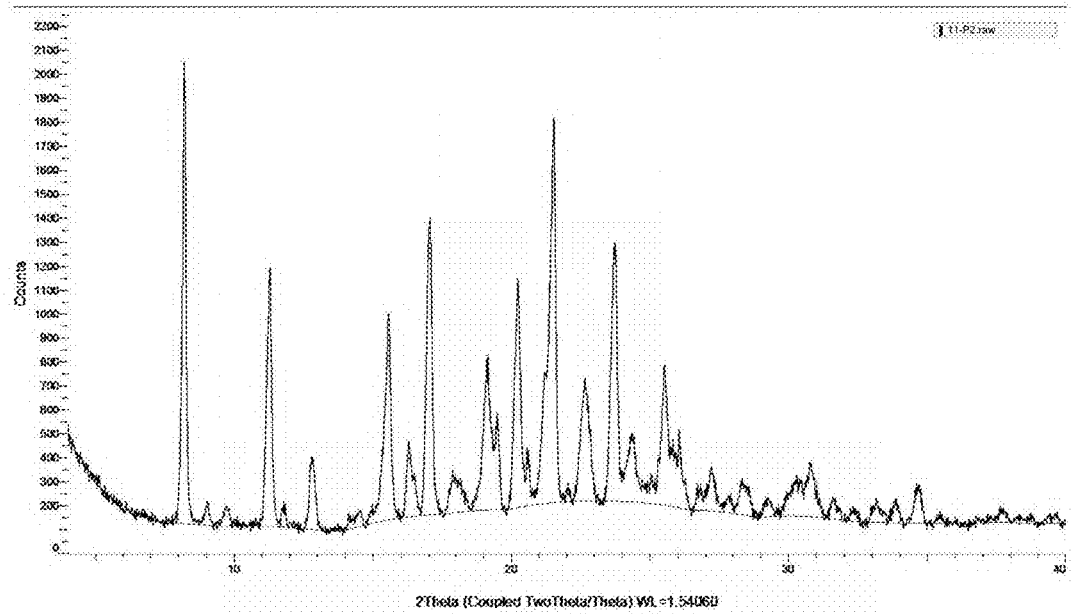

FIG. 226 depicts the XRPD profile of 11-P2 (Experiment Reference 11-Sample Reference P2) (Pattern #5).

Figure 227:
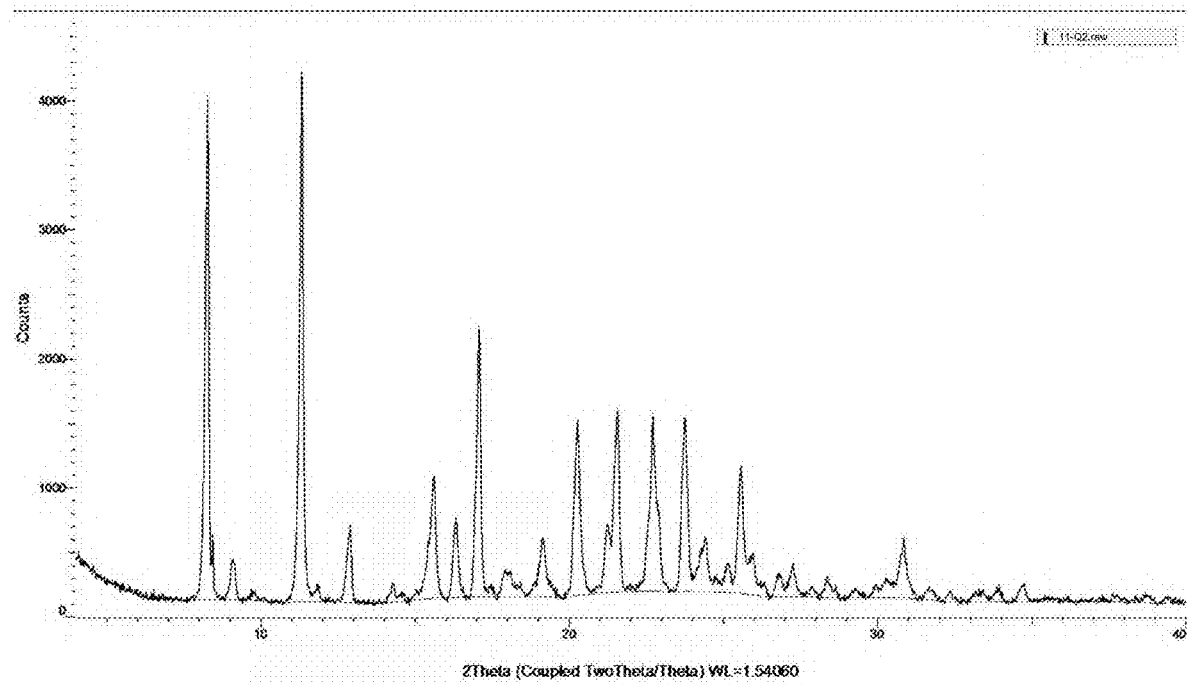

FIG. 227 depicts the XRPD profile of 11-Q2 (Experiment Reference 11-Sample Reference Q2) (Pattern #14).

Figure 228:
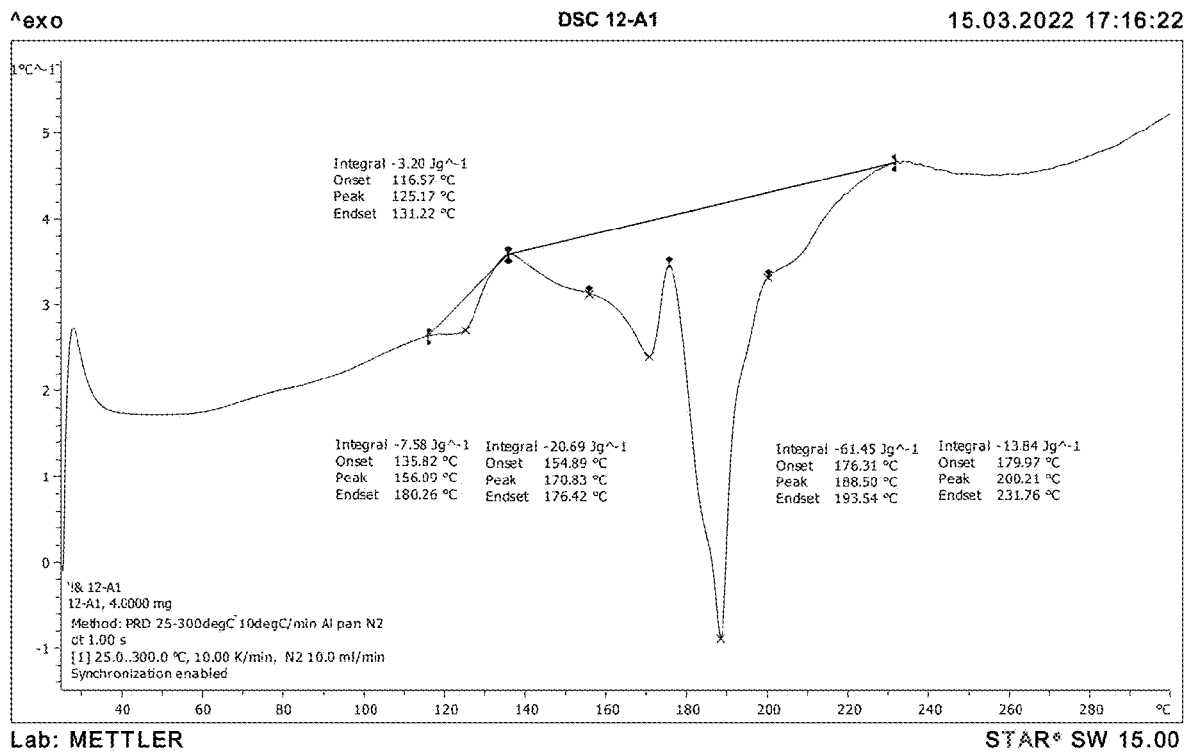

FIG. 228 depicts the DSC profile of 12-A1 (Experiment Reference 12-Sample Reference A1), analysis was acquired at a ramp rate of +10° C./minute.

Figure 229:
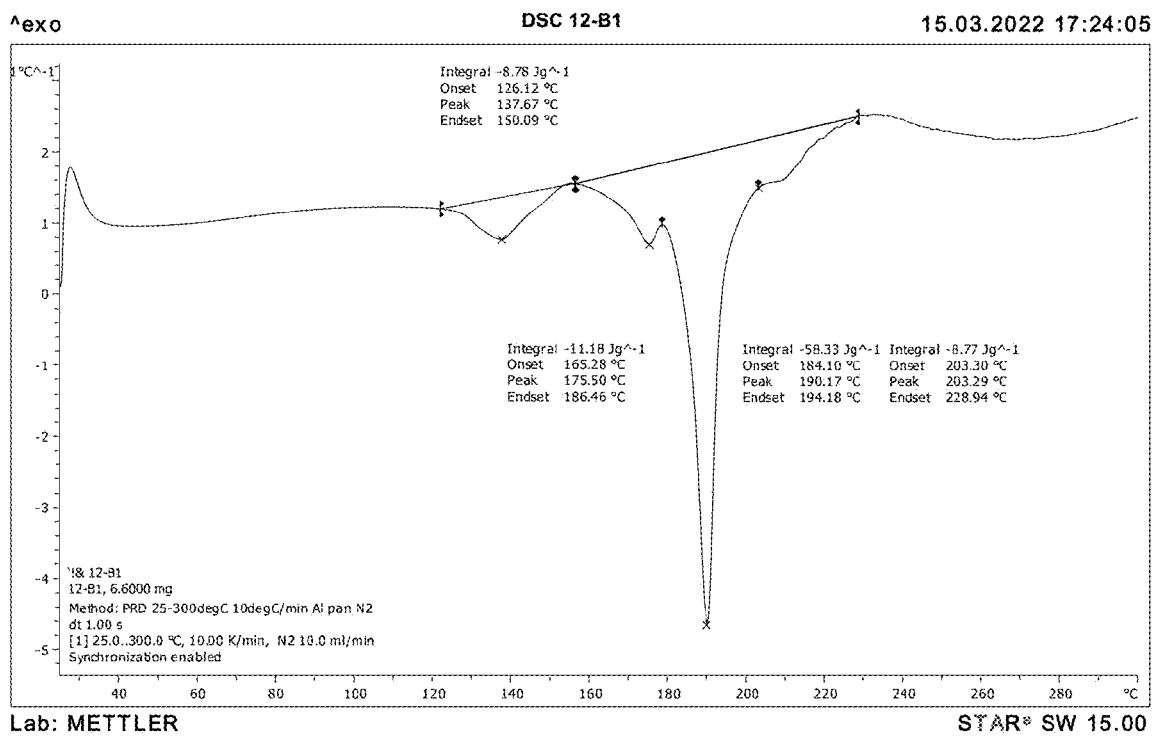

FIG. 229 depicts the DSC profile of 12-B1 (Experiment Reference 12-Sample Reference B1), analysis was acquired at a ramp rate of +10° C./minute.

Figure 230:
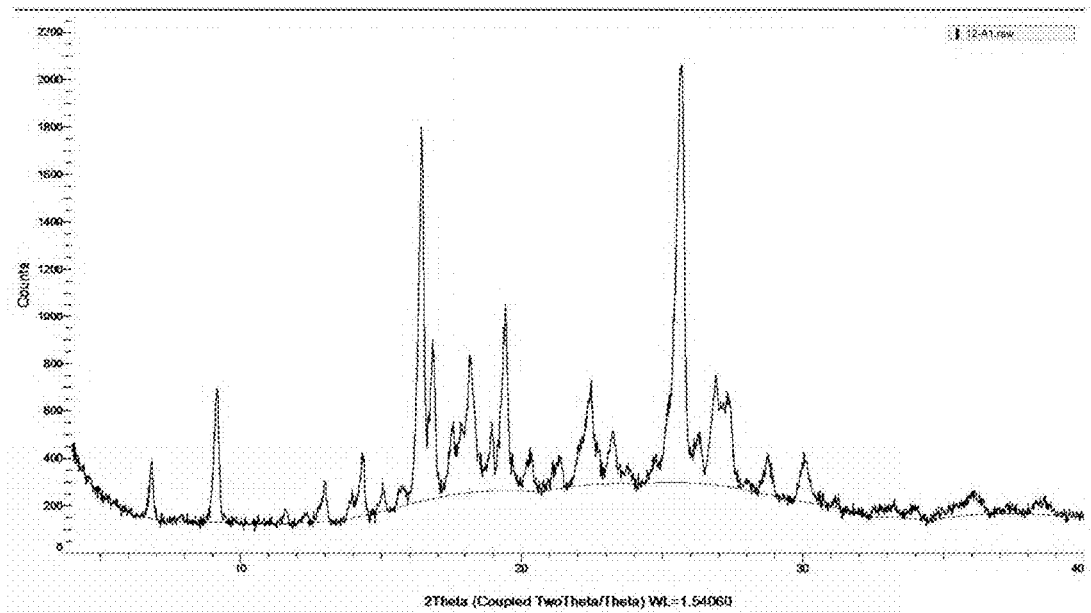

FIG. 230 depicts the XRPD profile of 12-A1 (Experiment Reference 12-Sample Reference A1) (slow conversion to Pattern #6a).

Figure 231:
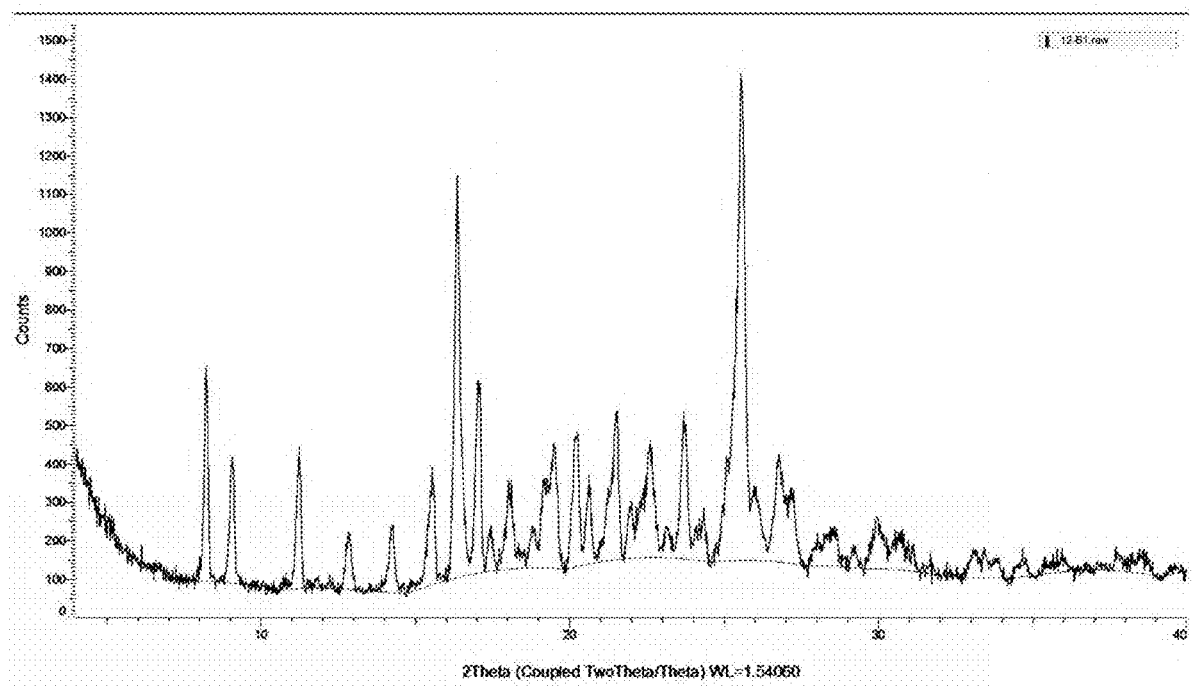

FIG. 231 depicts the XRPD profile of 12-B1 (Experiment Reference 12-Sample Reference B1) (slow conversion to Pattern #6a).

Figure 232:
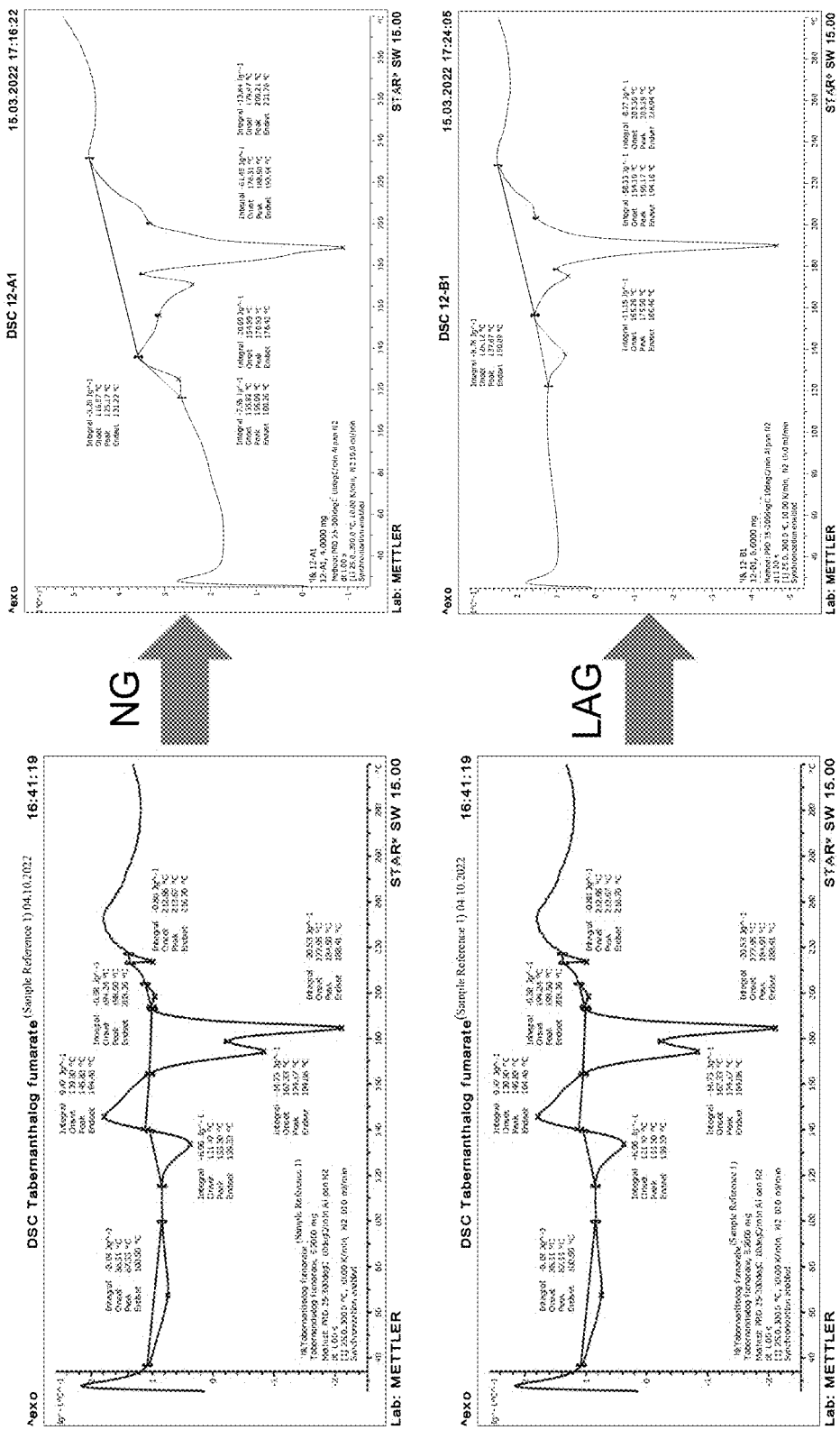

FIG. 232 depicts the DSC thermograms under neat grinding (NG, 12-A1 (Experiment Reference 12-Sample Reference A1)) and under liquid assisted grinding conditions (LAG, 12-B1 (Experiment Reference 12-Sample Reference B1)). Tabernanthalog monofumarate (left, top and bottom, Pattern #1) 12-A1 (top right, NG, Pattern #6a), 12-B1 (bottom right, LAG, Pattern #6a).

Figure 233:
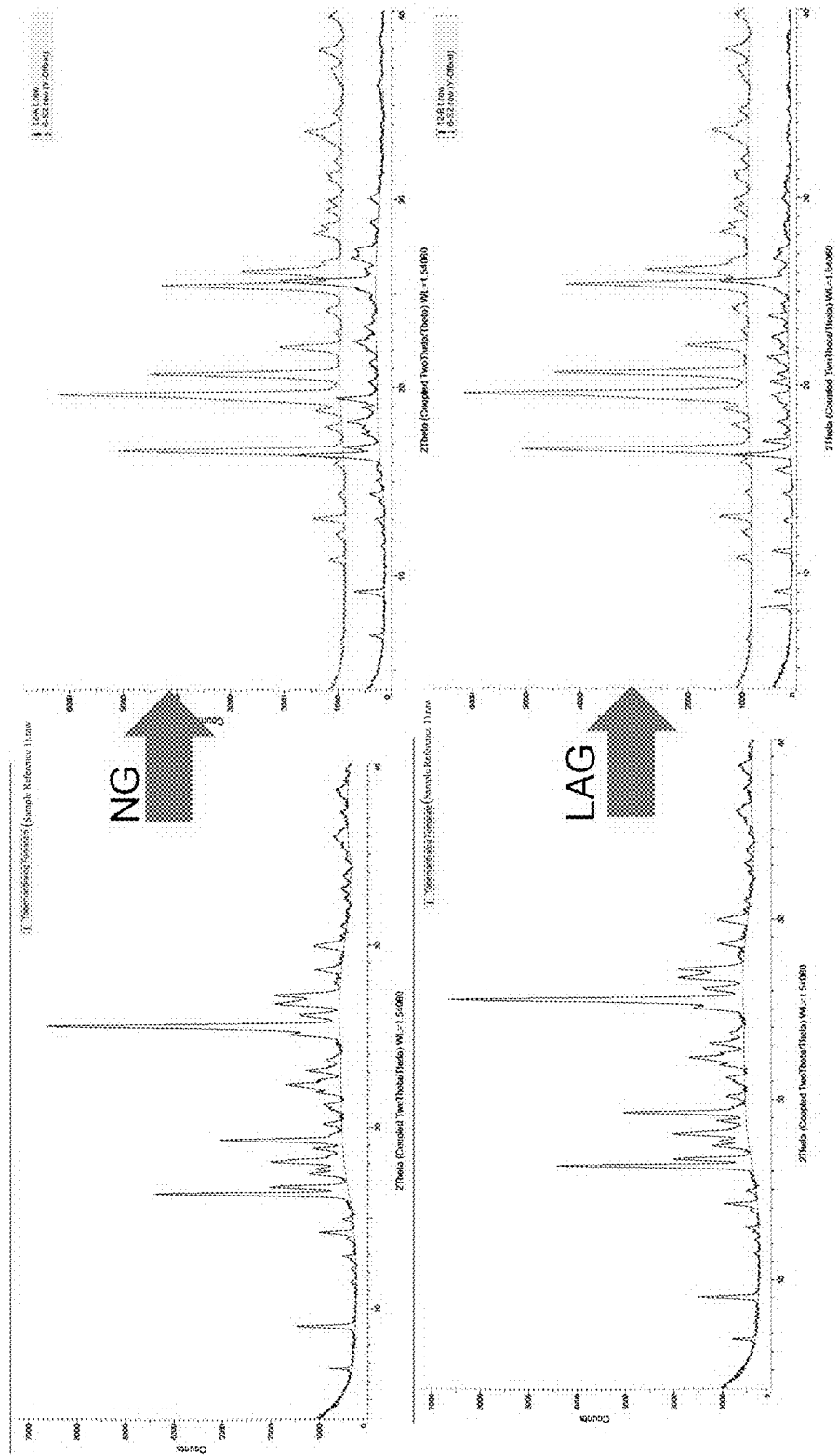

FIG. 233 depicts the XRPD diffractograms under neat grinding (NG, 12-A1 (Experiment Reference 12-Sample Reference A1), Pattern #6a, top right) and under liquid assisted grinding conditions (LAG, 12-B1 (Experiment Reference 12-Sample Reference B1), Pattern #6a, bottom, right). Input material (tabernanthalog monofumarate (left, top and bottom, Pattern #1).

Figure 234:
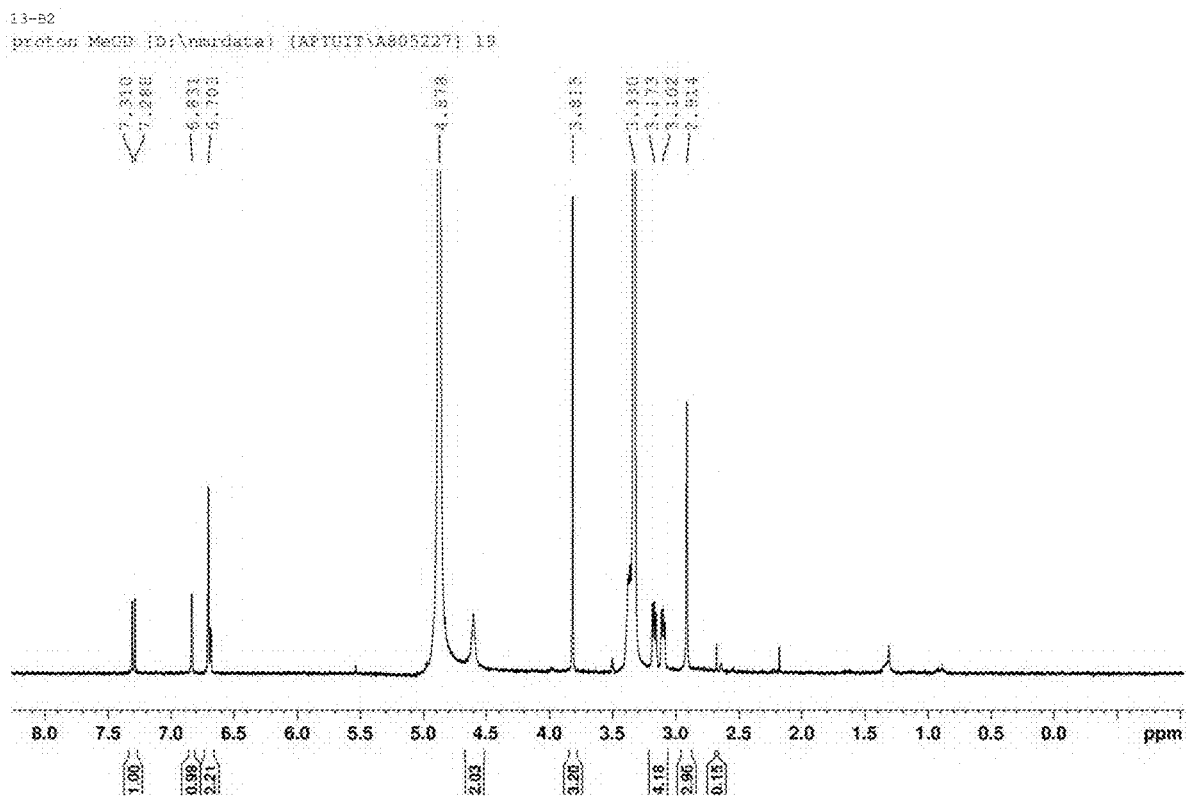

FIG. 234 depicts the $^1$H NMR spectrum of 13-B2 (Experiment Reference 13-Sample Reference B2), analysis was acquired in MeOD-d$_4$ and calibrated to the non-deuterated solvent residual at 3.31 ppm. Residual DMSO 1.1% w/w (ca. th. solvate 18.4% w/w).

Figure 235:
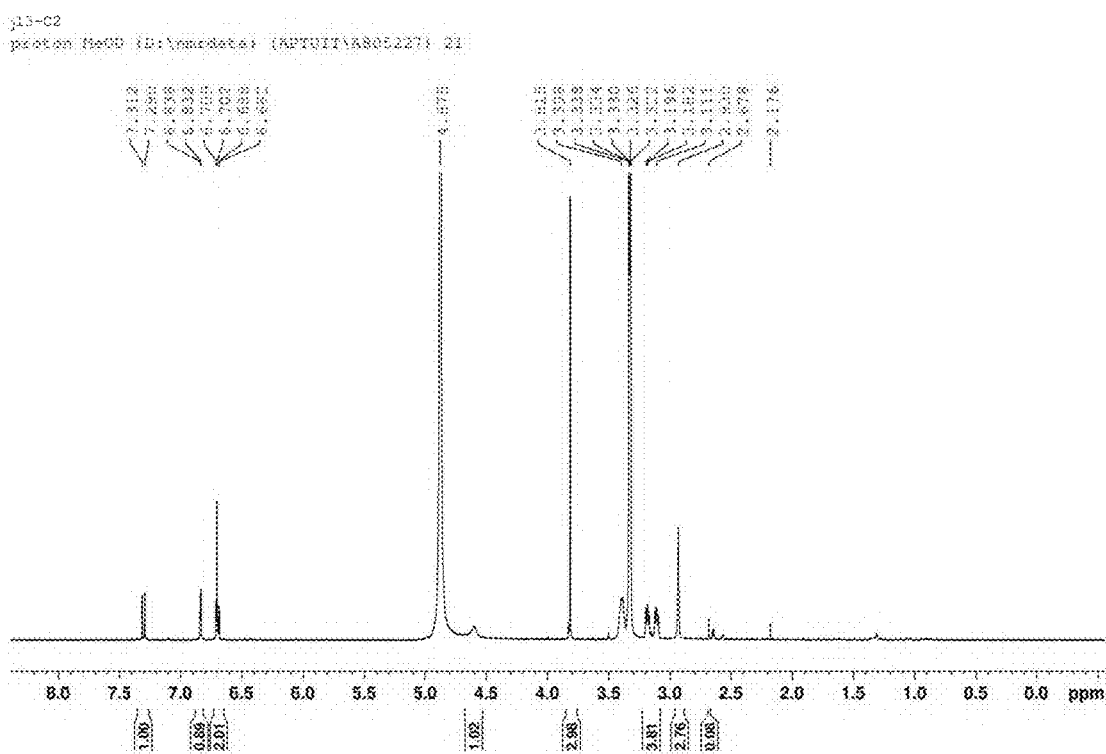

FIG. 235 depicts the $^1$H NMR spectrum of 13-C2 (Experiment Reference 13-Sample Reference C2), analysis was acquired in MeOD-d4 and calibrated to the non-deuterated solvent residual at 3.31 ppm. Residual DMSO 0.6% w/w (ca. th. solvate 18.4% w/w).

Figure 236:
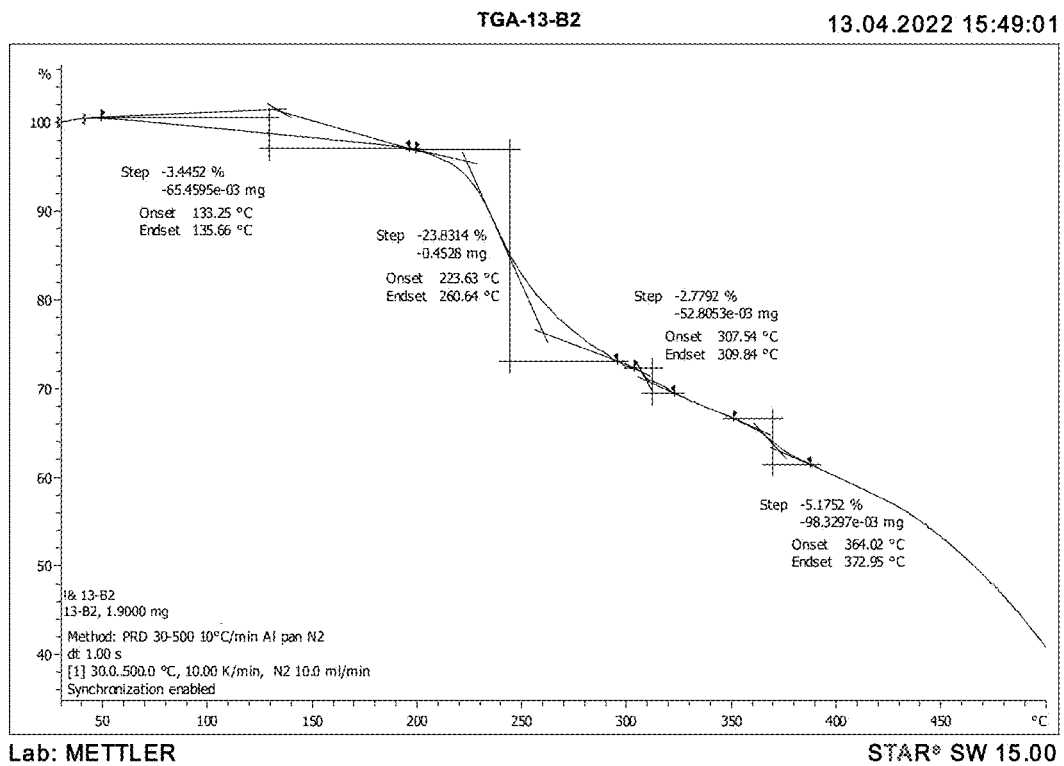

FIG. 236 depicts the TGA profile of 13-B2 (Experiment Reference 13-Sample Reference B2), analysis was acquired at a ramp rate of +10° C./minute.

Figure 237:
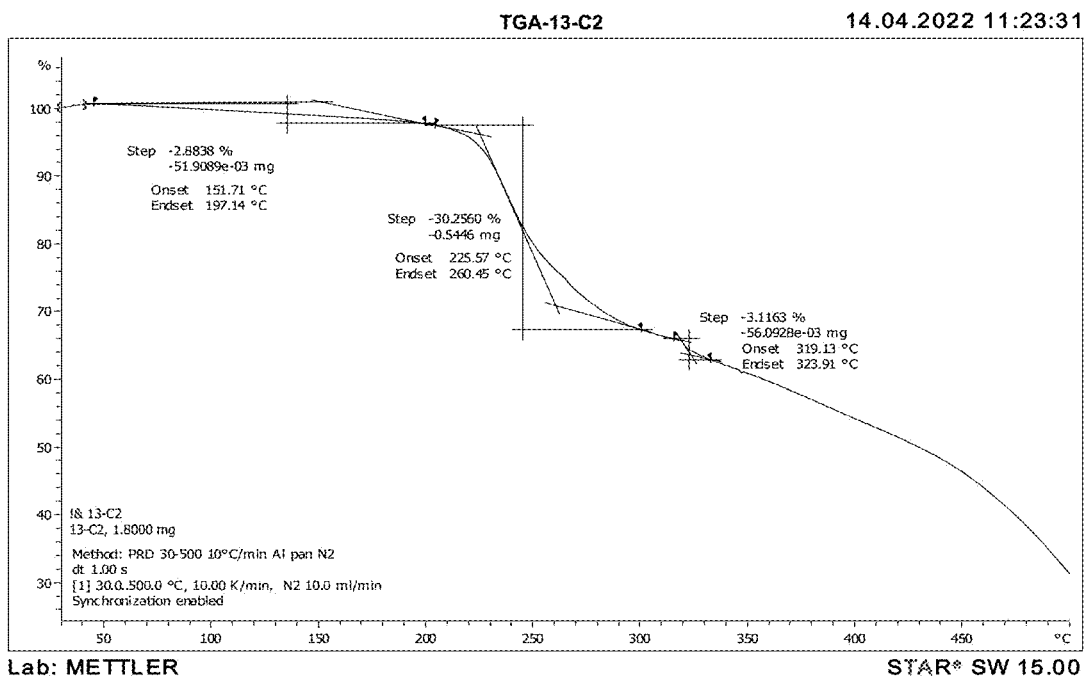

FIG. 237 depicts the TGA profile of 13-C2 (Experiment Reference 13-Sample Reference C2), analysis was acquired at a ramp rate of +10° C./minute.

Figure 238:
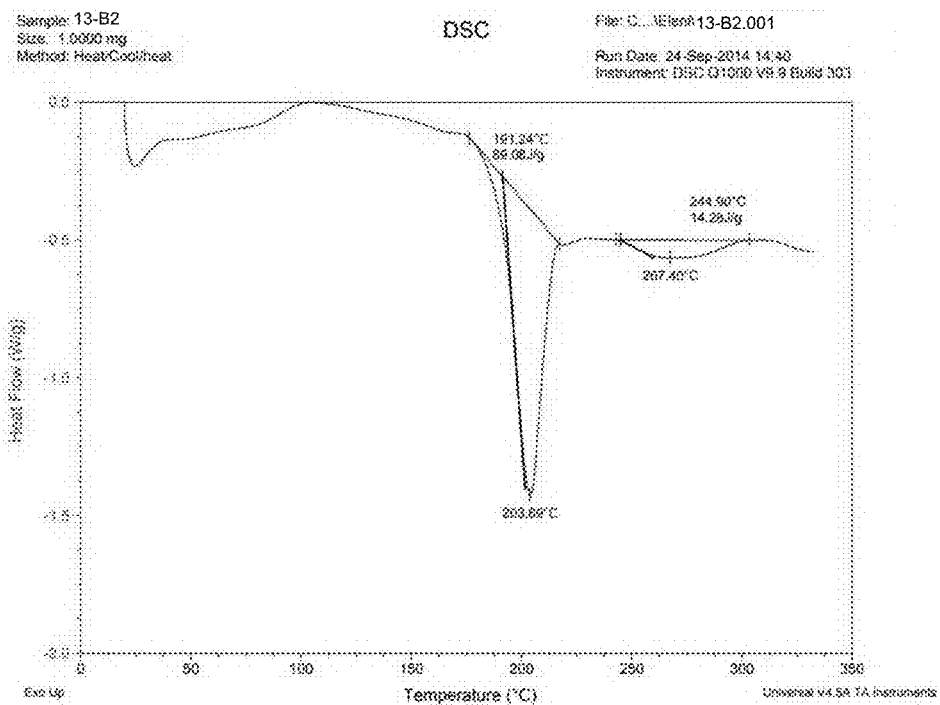

FIG. 238 depicts the DSC profile of 13-B2 (Experiment Reference 13-Sample Reference B2).

Figure 239:
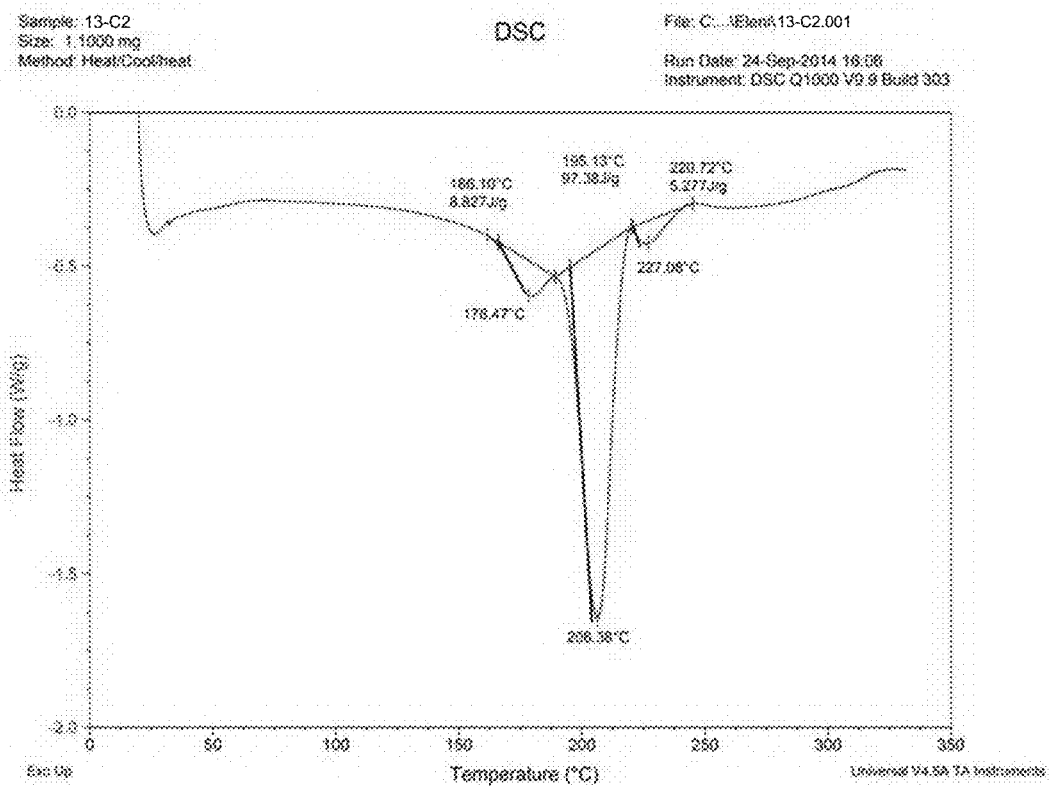

FIG. 239 depicts the DSC profile of 13-C2 (Experiment Reference 13-Sample Reference C2).

Figure 240:
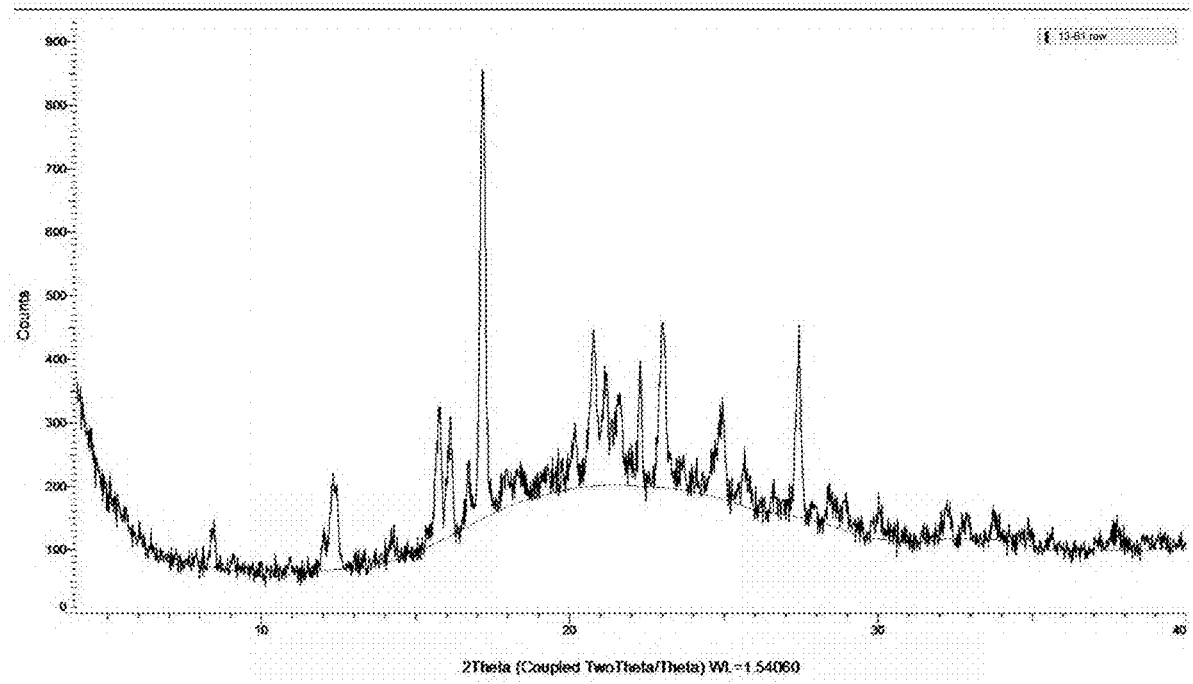

FIG. 240 depicts the XRPD profile of 13-B1 (Experiment Reference 13-Sample Reference B1) (wet sample, Pattern #24).

Figure 241:
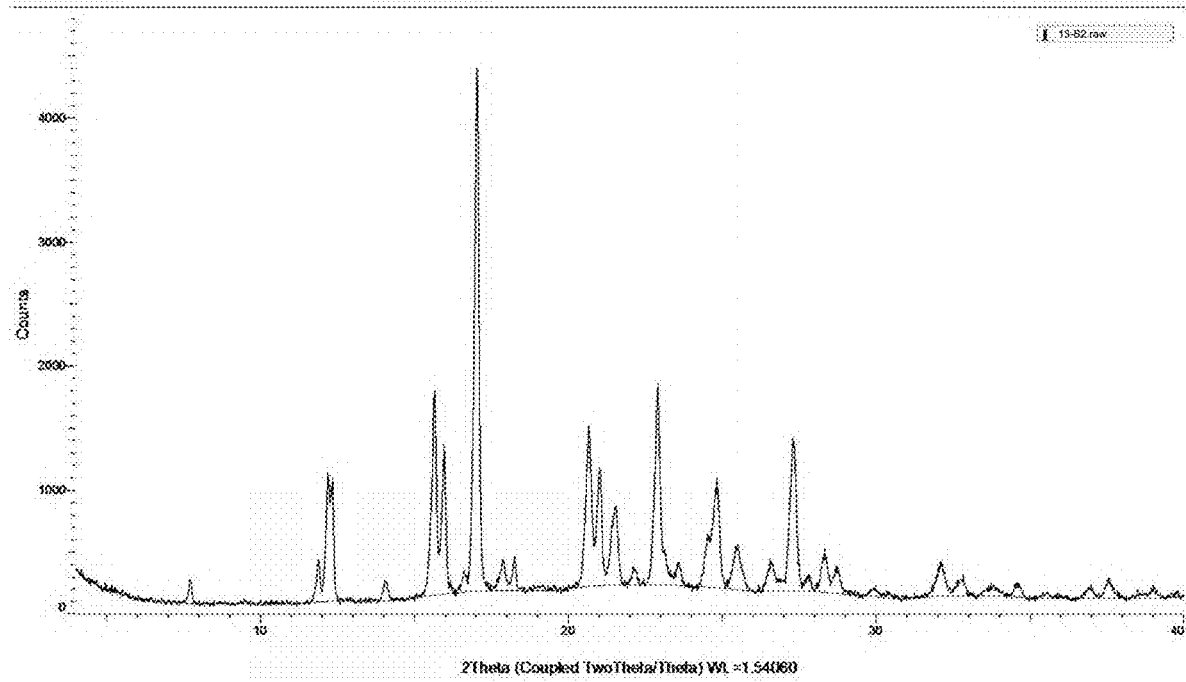

FIG. 241 depicts the XRPD profile of 13-B2 (Experiment Reference 13-Sample Reference B2) (oven dried, Pattern #24).

Figure 242:
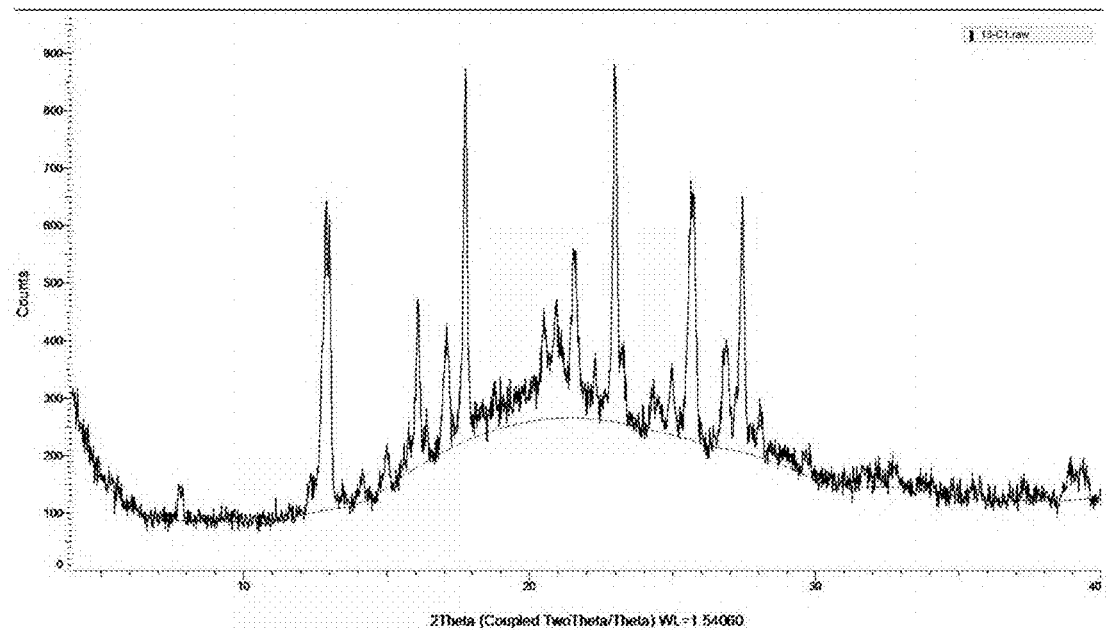

FIG. 242 depicts the XRPD profile of 13-C1 (Experiment Reference 13-Sample Reference C1) (wet sample, Pattern #23).

Figure 243:
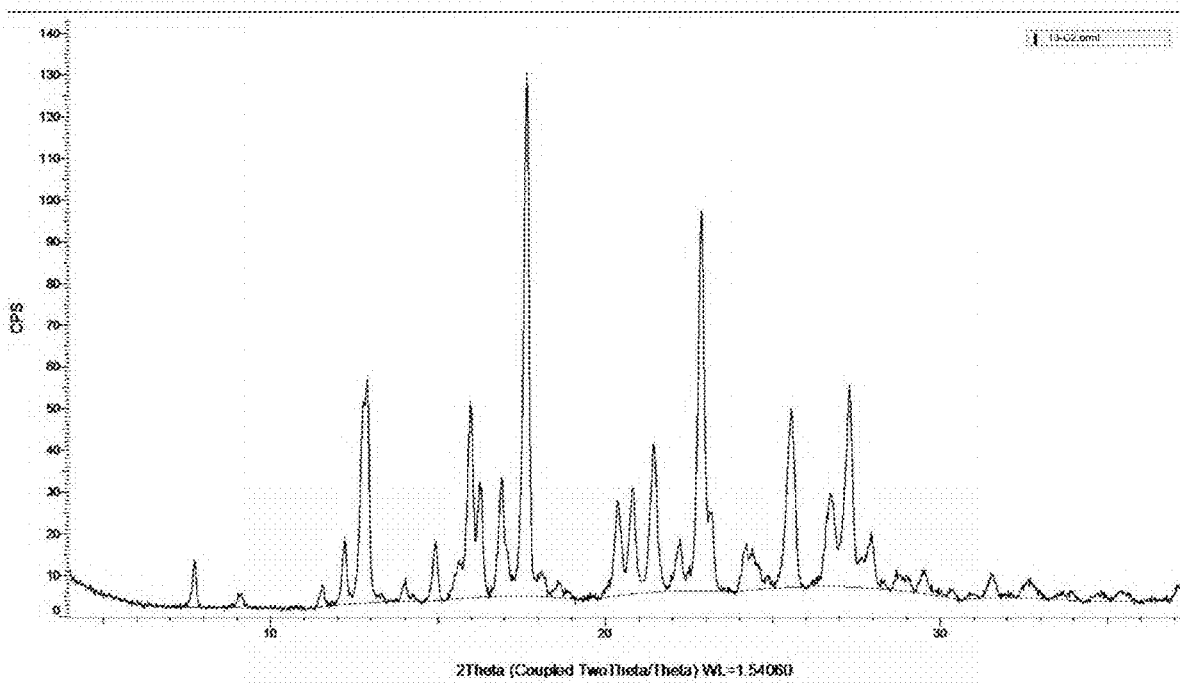

FIG. 243 depicts the XRPD profile of 13-C2 (Experiment Reference 13-Sample Reference C2) (oven dried, Pattern #23).

Figure 244:
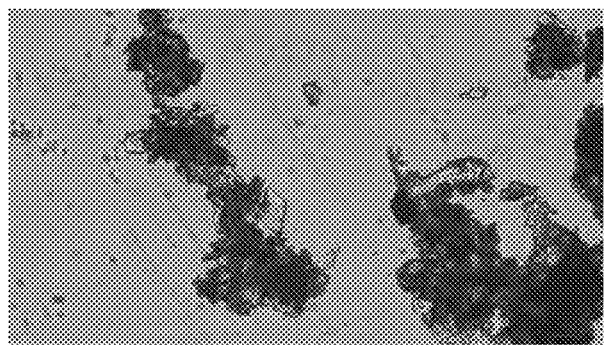

FIG. 244 depicts the 13-B2 (Experiment Reference 13-Sample Reference B2) normal polarized (magnification× 5).

Figure 245:
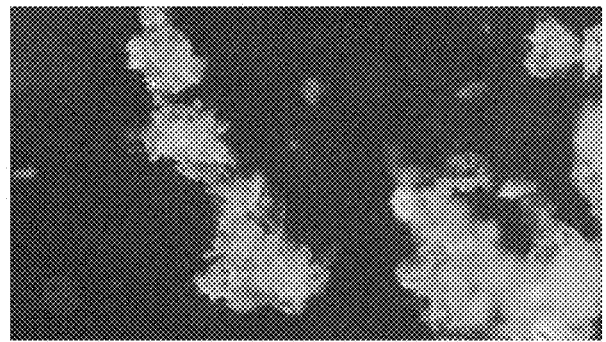

FIG. 245 depicts the 13-B2 (Experiment Reference 13-Sample Reference B2) cross polarized (magnification× 5).

Figure 246:
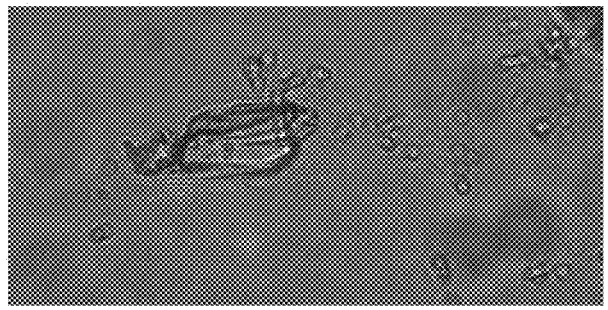

FIG. 246 depicts the 13-B2 (Experiment Reference 13-Sample Reference B2) normal polarized (magnification× 25).

Figure 247:
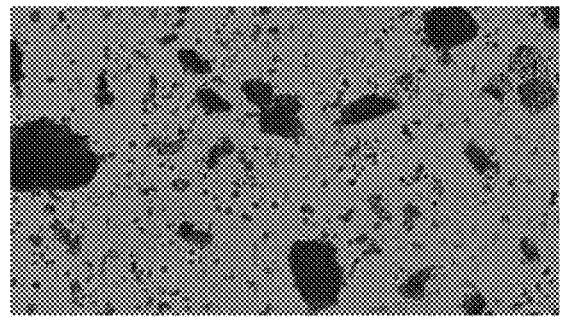

FIG. 247 depicts the 13-C2 (Experiment Reference 13-Sample Reference C2) normal polarized (magnification× 5).

Figure 248:
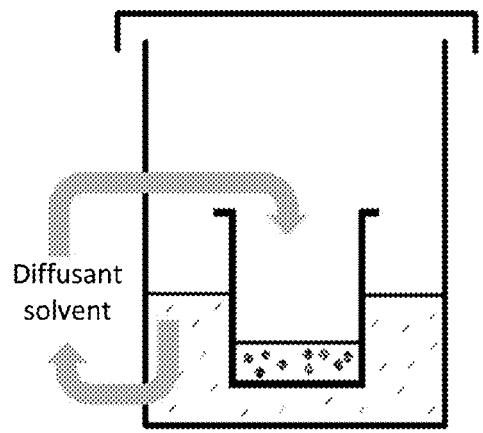

FIG. 248 depicts the illustration of vapor diffusion experiment apparatus set-up.

Figure 249:
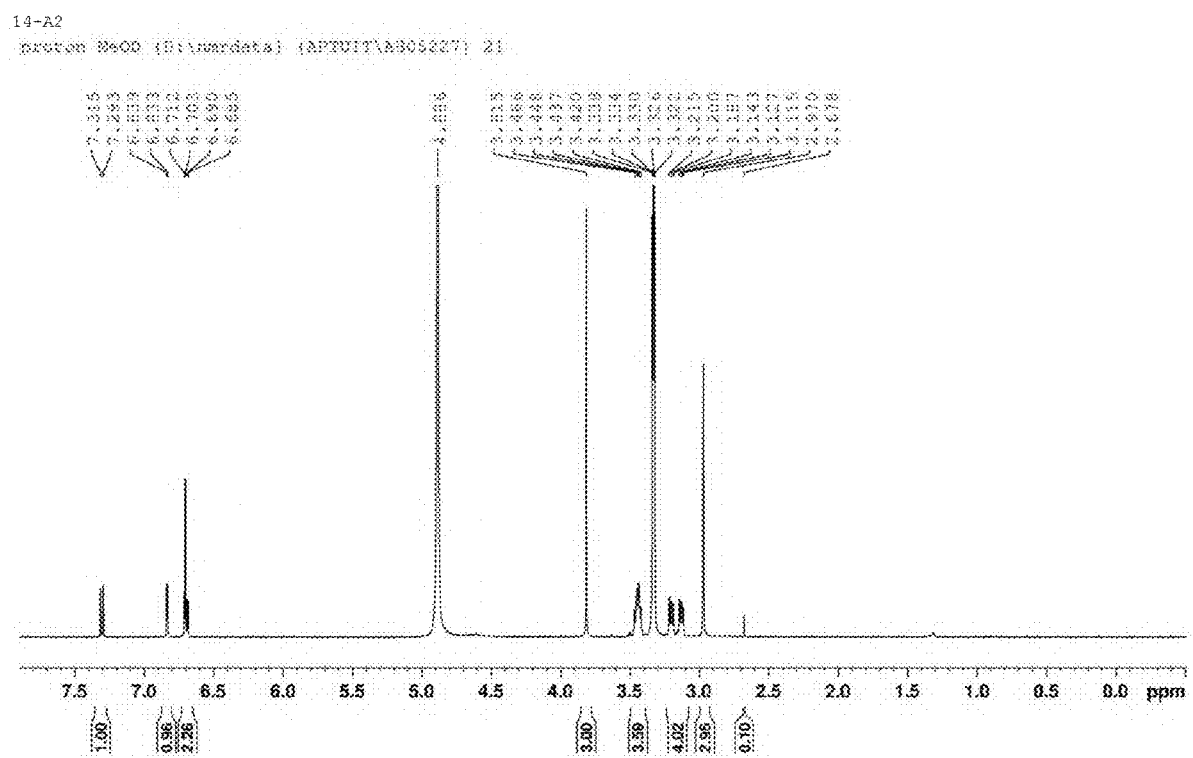

FIG. 249 depicts the $^1$H NMR spectrum of 14-A2 (Experiment Reference 14-Sample Reference A2), analysis was acquired in MeOD-d$_4$ and calibrated to the non-deuterated solvent residual at 3.31 ppm. Residual DMSO 0.8% w/w (ca. th. solvate 18.4% w/w).

Figure 250:
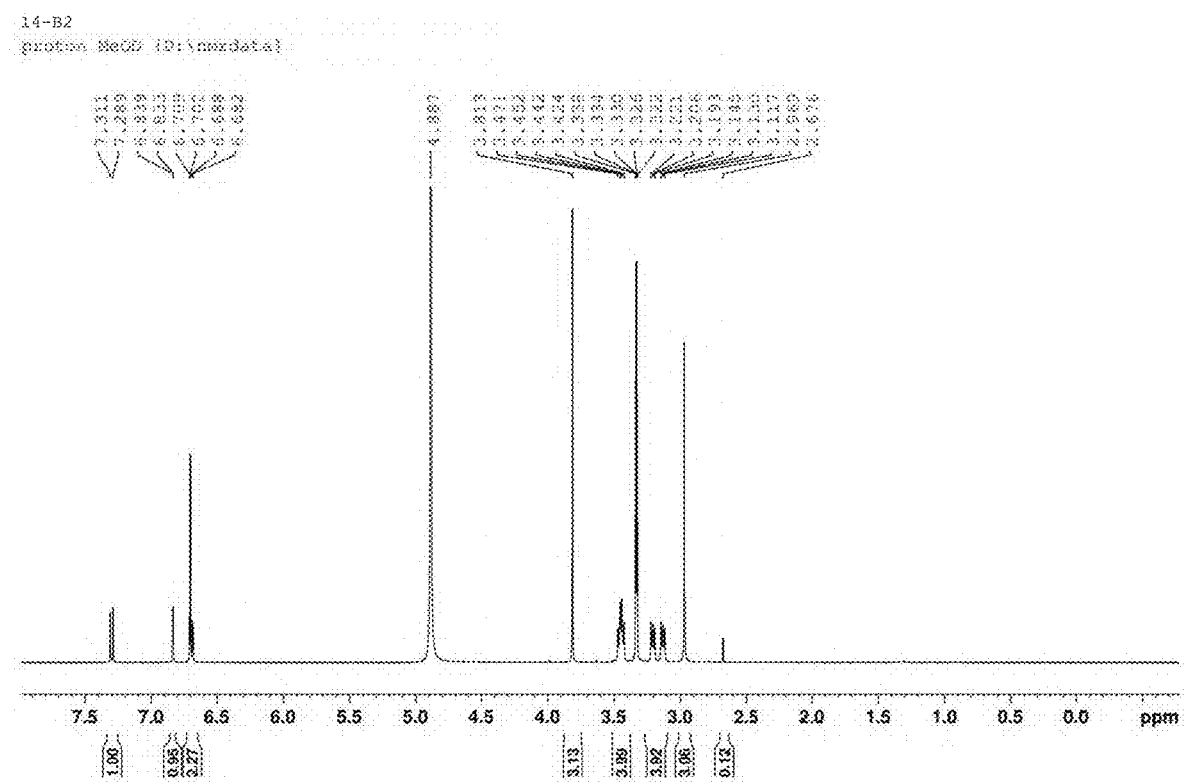

FIG. 250 depicts the $^1$H NMR spectrum of 14-B2 (Experiment Reference 14-Sample Reference B2), analysis was acquired in MeOD-d$_4$ and calibrated to the non-deuterated solvent residual at 3.31 ppm. Residual DMSO 0.9% w/w (ca. th. solvate 18.4% w/w).

Figure 251:
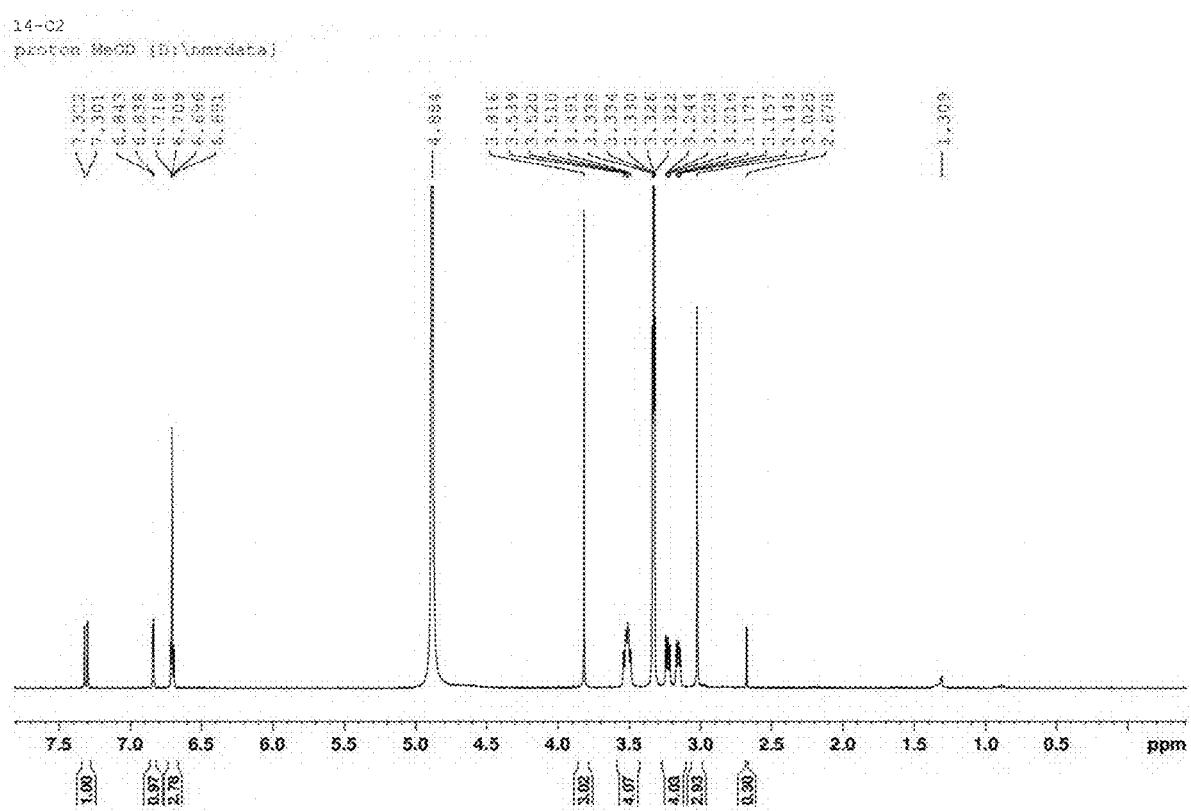

FIG. 251 depicts the $^1$H NMR spectrum of 14-C2 (Experiment Reference 14-Sample Reference C2), analysis was acquired in MeOD-d$_4$ and calibrated to the non-deuterated solvent residual at 3.31 ppm. Residual DMSO 0.9% w/w (ca. th. solvate 18.4% w/w).

Figure 252:
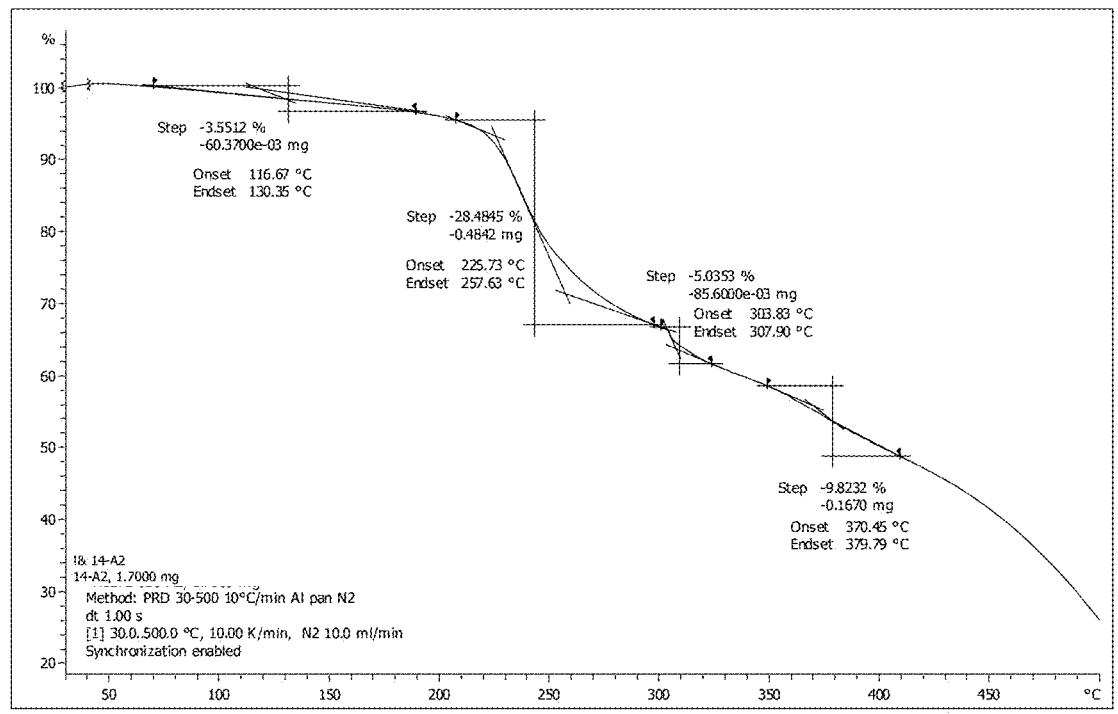

FIG. 252 depicts the TGA profile of 14-A2 (Experiment Reference 14-Sample Reference A2), analysis was acquired at a ramp rate of +10° C./minute.

Figure 253:
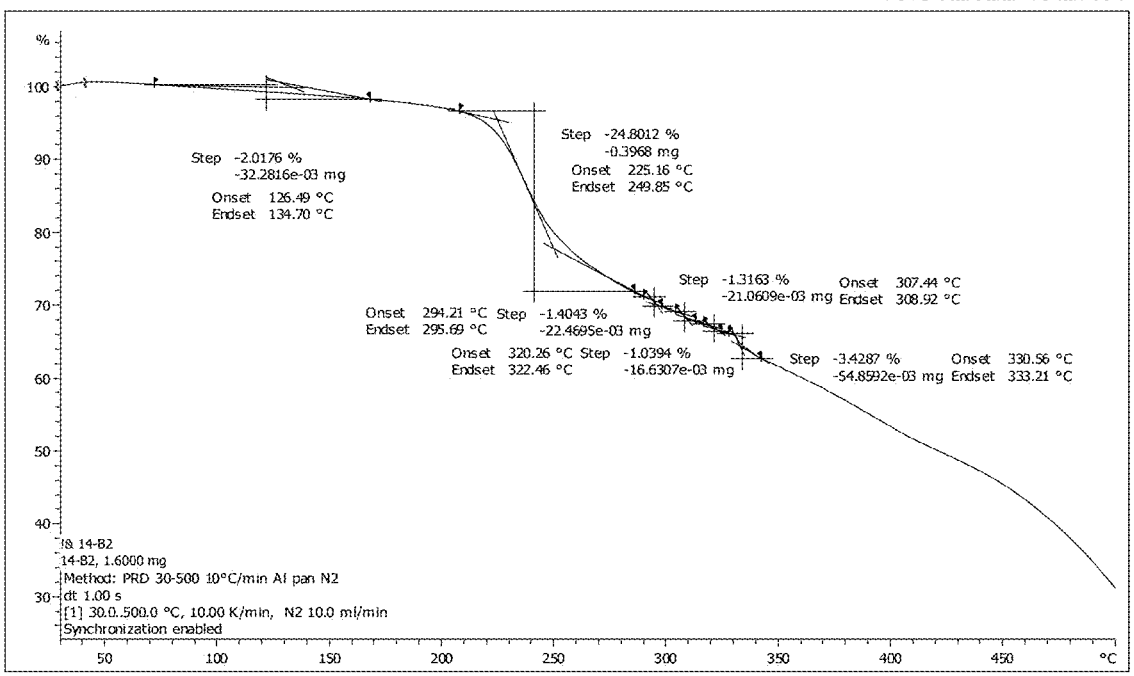

FIG. 253 depicts the TGA profile of 14-B2 (Experiment Reference 14-Sample Reference B2), analysis was acquired at a ramp rate of +10° C./minute.

Figure 254:
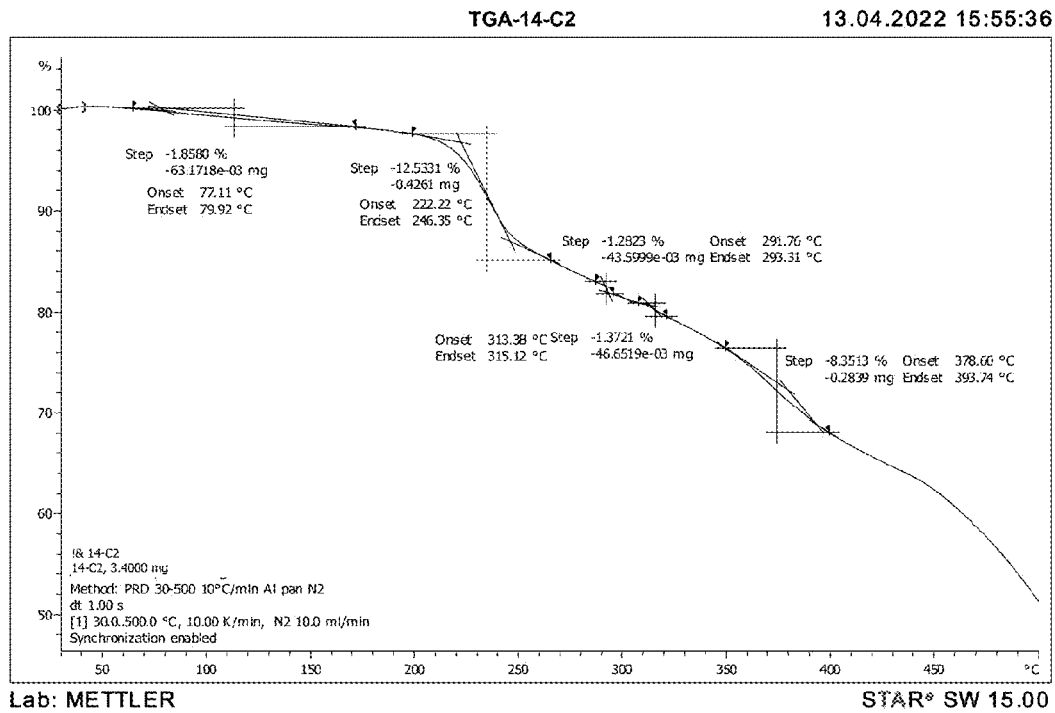

FIG. 254 depicts the TGA profile of 14-C2 (Experiment Reference 14-Sample Reference C2), analysis was acquired at a ramp rate of +10° C./minute.

Figure 255:
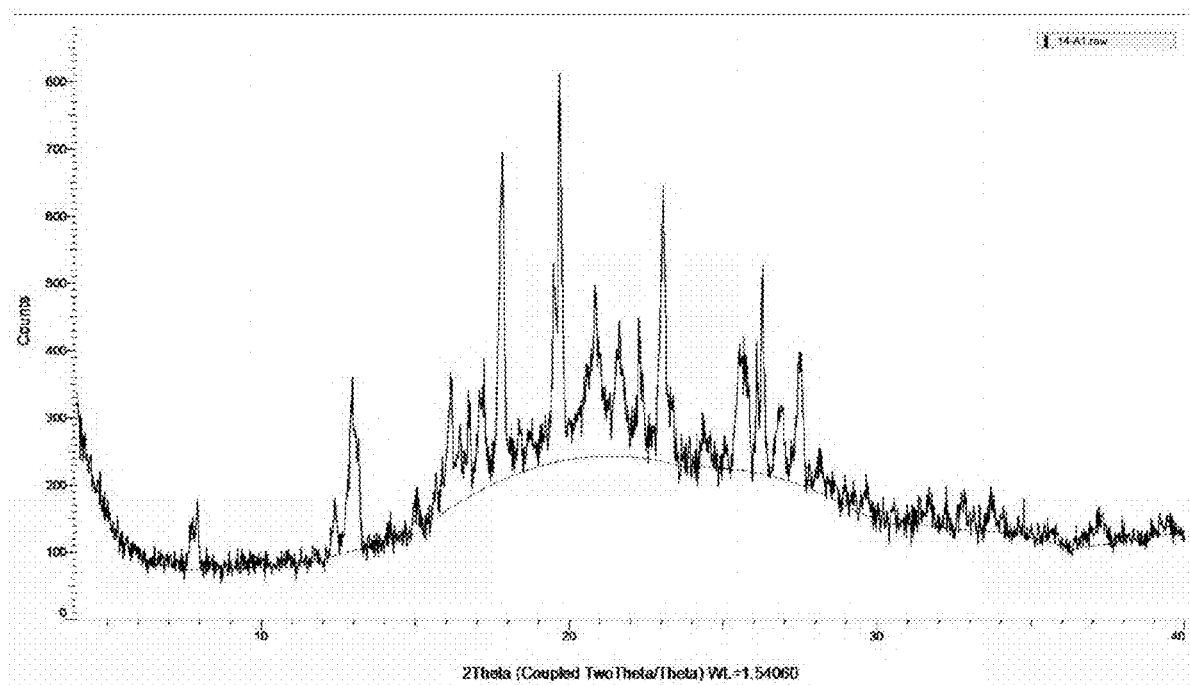

FIG. 255 depicts the XRPD profile of 14-A1 (Experiment Reference 14-Sample Reference A1) (wet sample, disordered Pattern #23).

Figure 256:
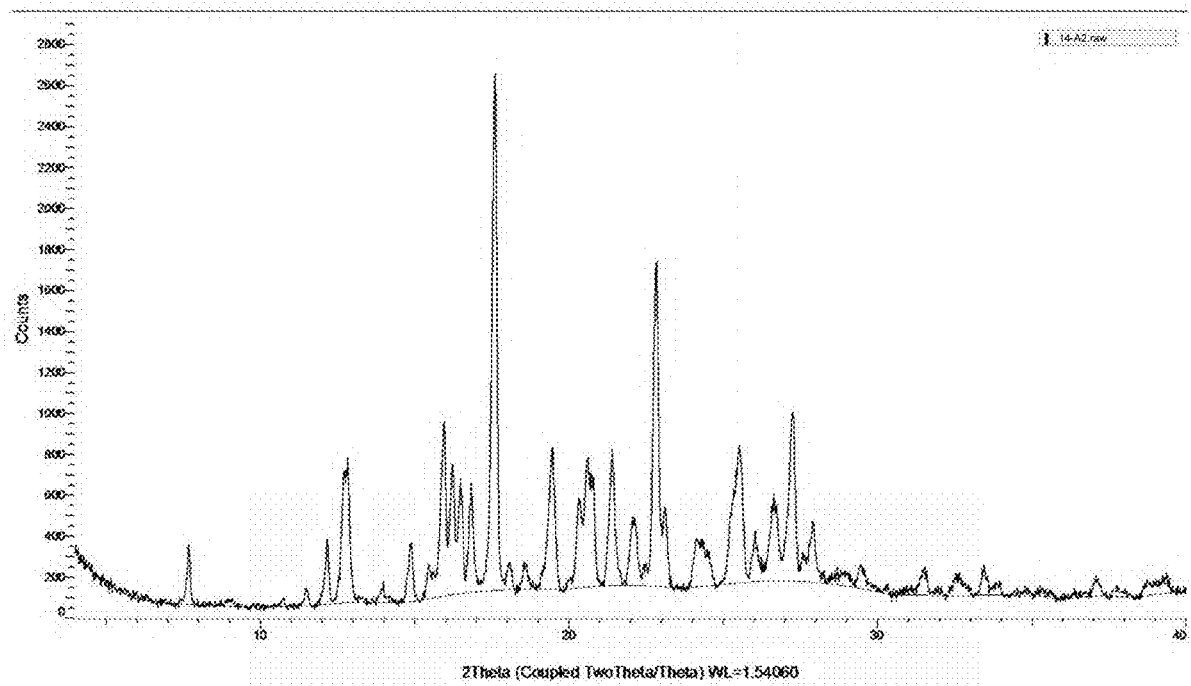

FIG. 256 depicts the XRPD profile of 14-A2 (Experiment Reference 14-Sample Reference A2) (oven dried sample, Pattern #23).

Figure 257:
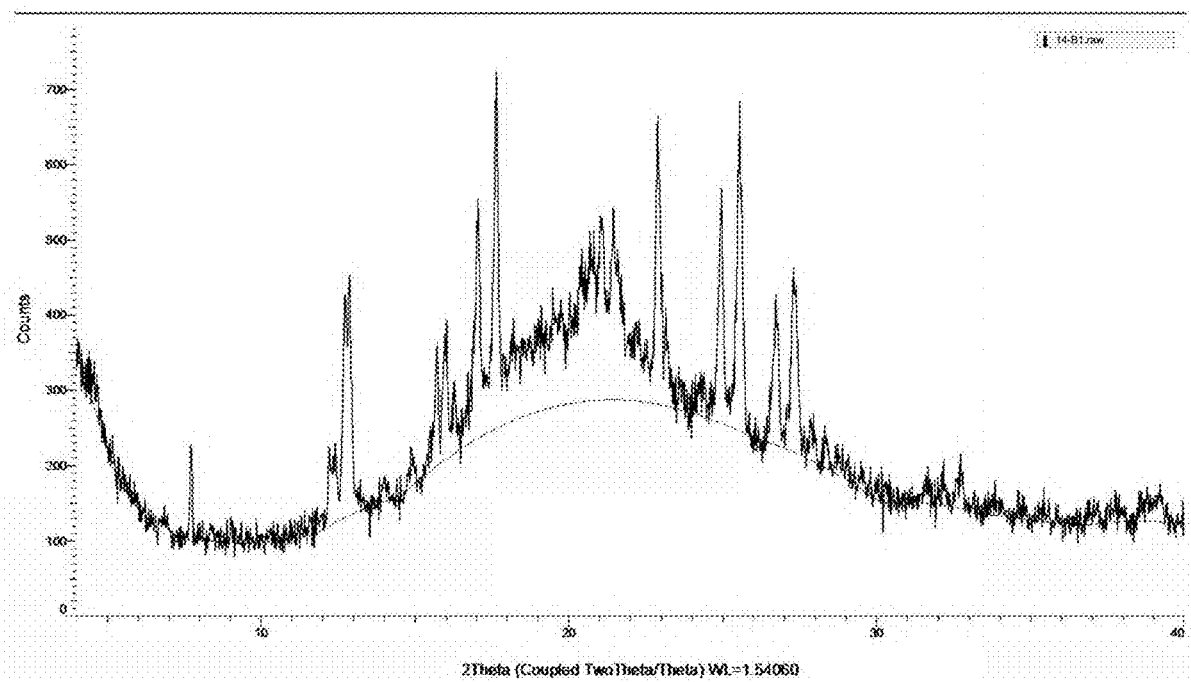

FIG. 257 depicts the XRPD profile of 14-B1 (Experiment Reference 14-Sample Reference B1) (wet sample, disordered Pattern #23).

Figure 258:
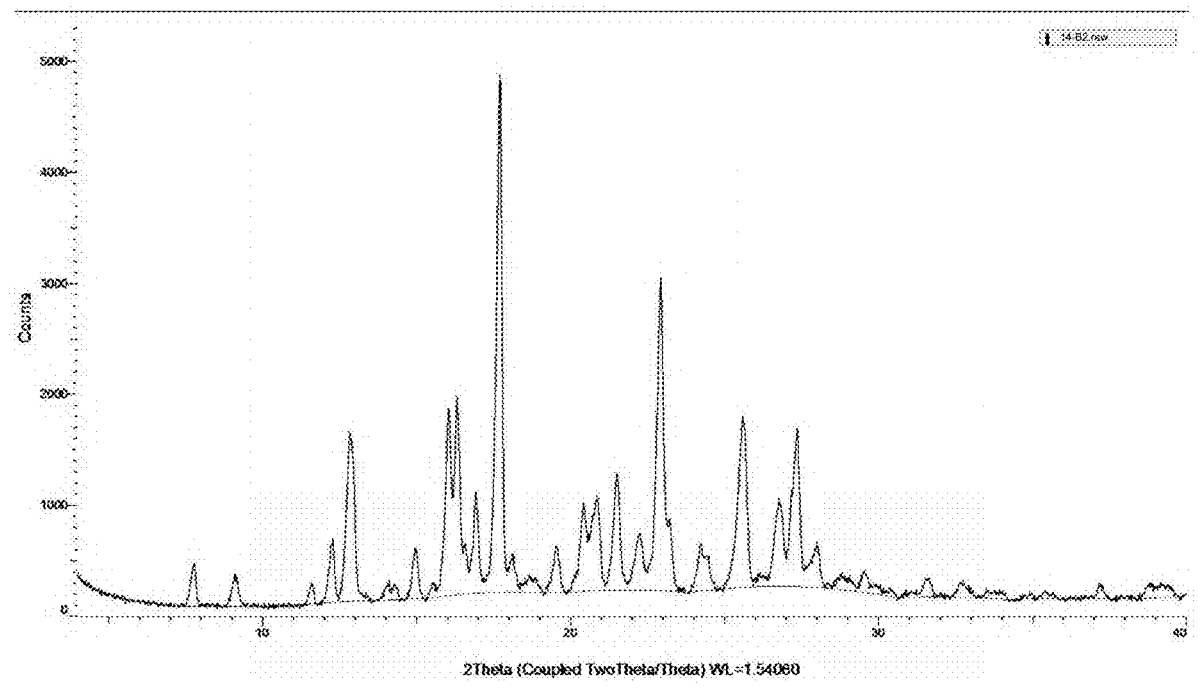

FIG. 258 depicts the XRPD profile of 14-B2 (Experiment Reference 14-Sample Reference B2) (oven dried sample, Pattern #23).

Figure 259:
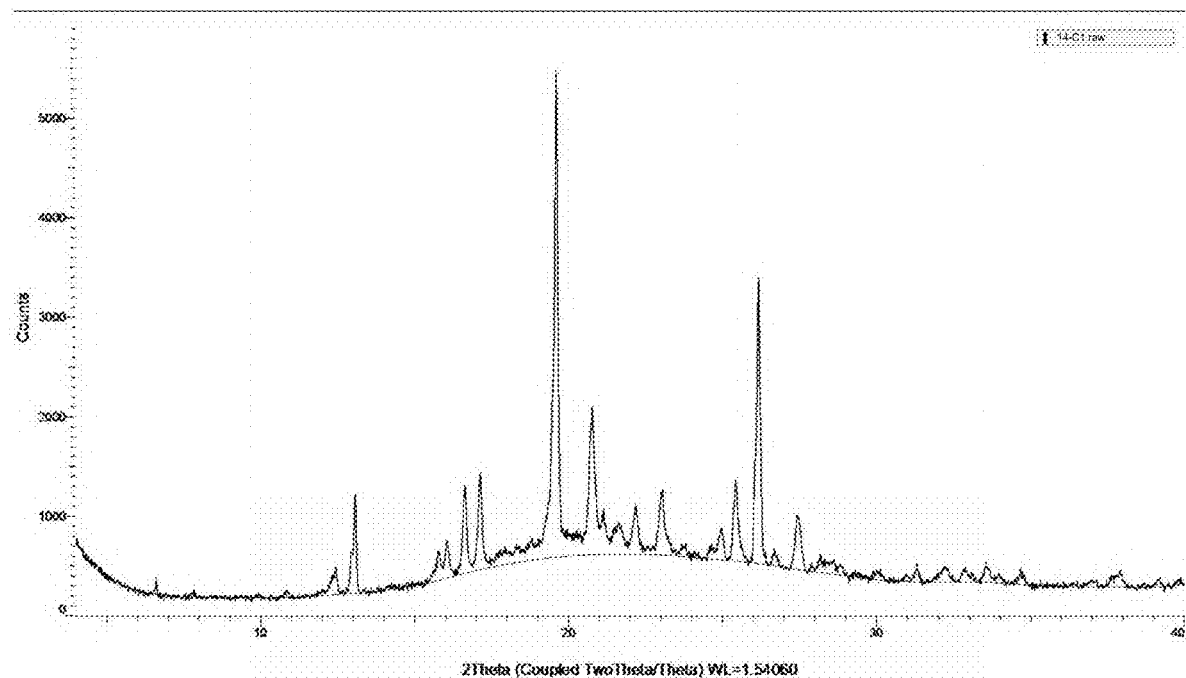

FIG. 259 depicts the XRPD profile of 14-C1 (Experiment Reference 14-Sample Reference C1) (wet sample, high background Pattern #6a).

Figure 260:
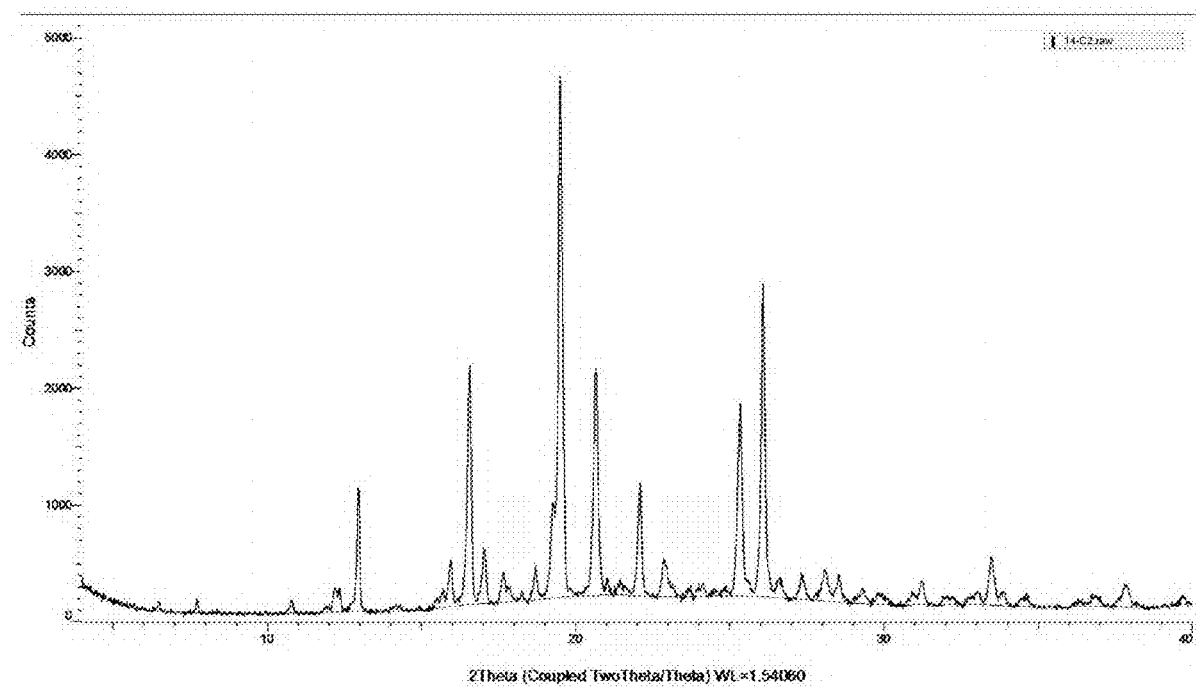

FIG. 260 depicts the XRPD profile of 14-C2 (Experiment Reference 14-Sample Reference C2) (oven dried sample, Pattern #6a).

Figure 261:

FIG. 261 depicts the 14-A (Experiment Reference 14-Sample Reference A) showed a solid in the bottom of the vial after 6 days.

Figure 262:
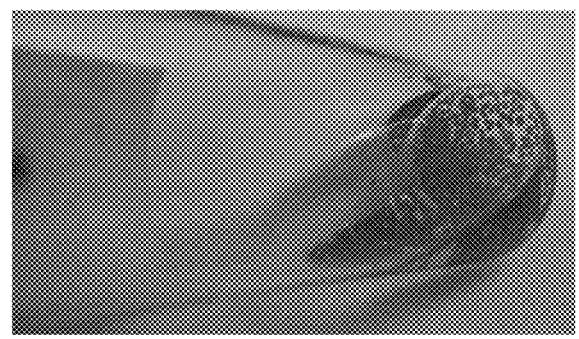

FIG. 262 depicts the 14-B (Experiment Reference 14-Sample Reference B) showed lots of small solid pellets in the bottom of the vial after 6 days.

Figure 263:
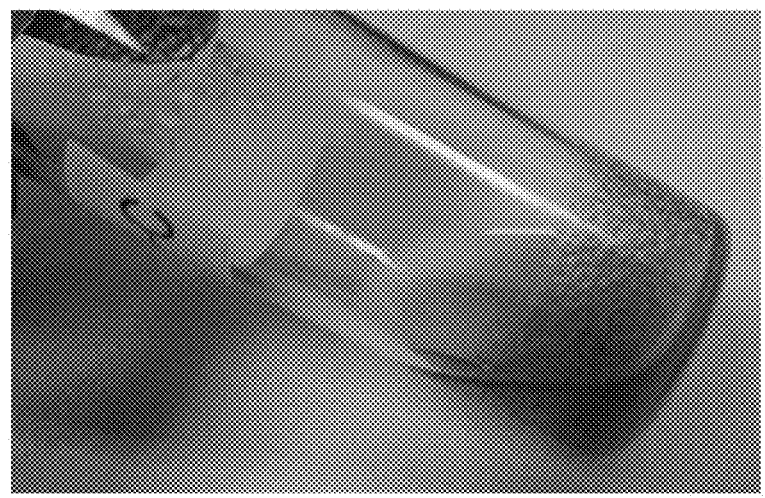

FIG. 263 depicts the 14-C (Experiment Reference 14-Sample Reference C) showed a wet powder in the bottom of the vial after 6 days.

Figure 264:
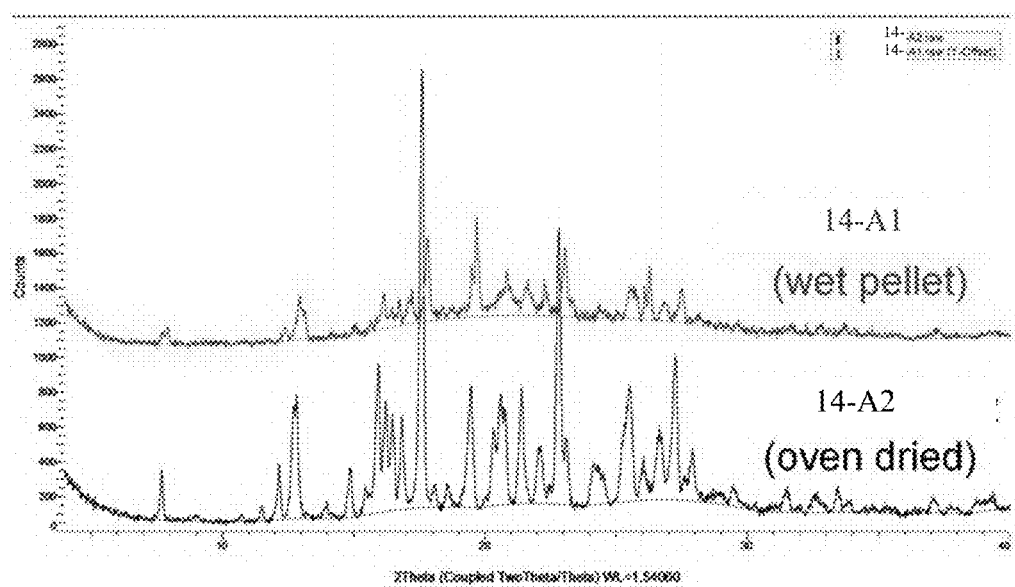

FIG. 264 depicts the XRPD diffractogram overlay of 14-A1 (Experiment Reference 14-Sample Reference A1) (disordered Pattern #23) and 14-A2 (Experiment Reference 14-Sample Reference A2) (Pattern #23).

Figure 265:
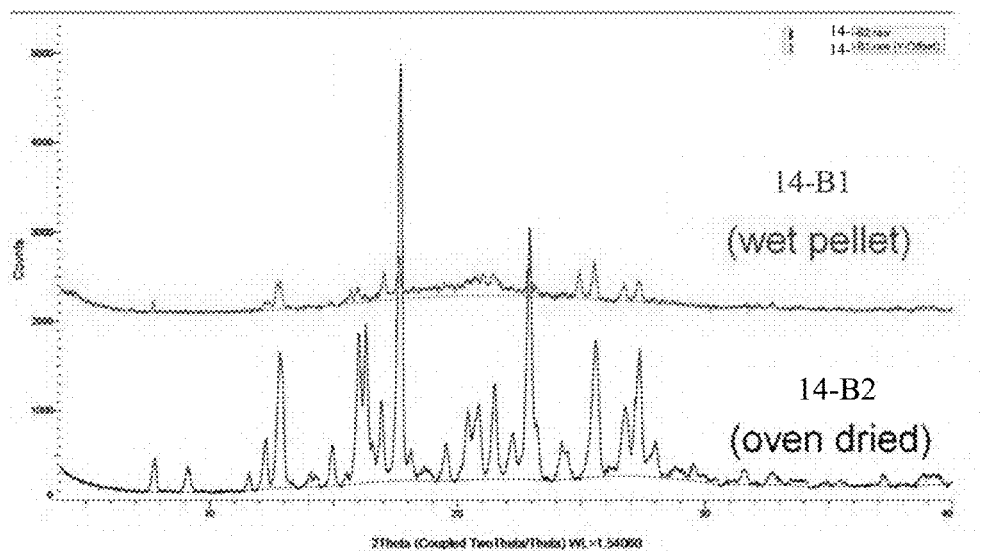

FIG. 265 depicts the XRPD diffractogram overlay of 14-B1 (Experiment Reference 14-Sample Reference B1) (disordered Pattern #23) and 14-B2 (Experiment Reference 14-Sample Reference B2) (Pattern #23).

Figure 266:
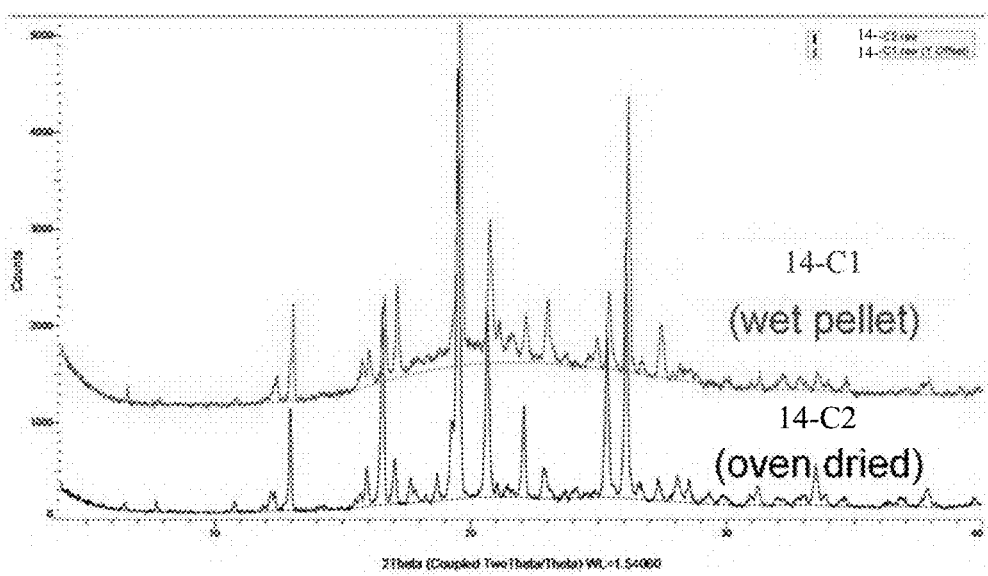

FIG. 266 depicts the XRPD diffractogram overlay of 14-C1 (Experiment Reference 14-Sample Reference C1) (high background Pattern #6a) and 14-C2 (Experiment Reference 14-Sample Reference C2) (Pattern #6a).

Figure 267:
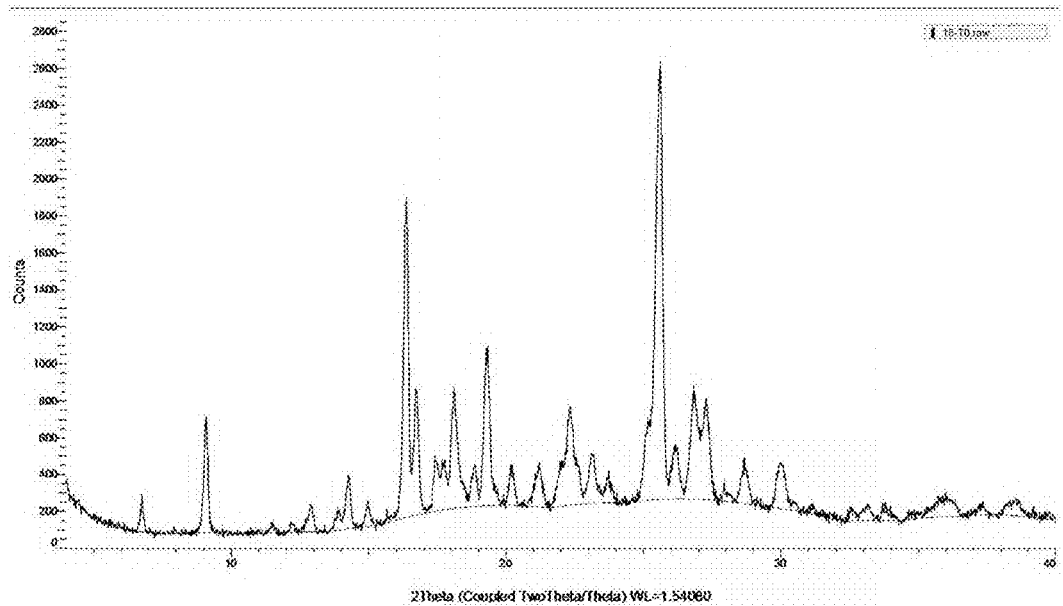

FIG. 267 depicts the XRPD profile of 15-TO (Experiment Reference 15-Sample Reference TO) (Pattern #1, Sample Reference 1).

Figure 268:
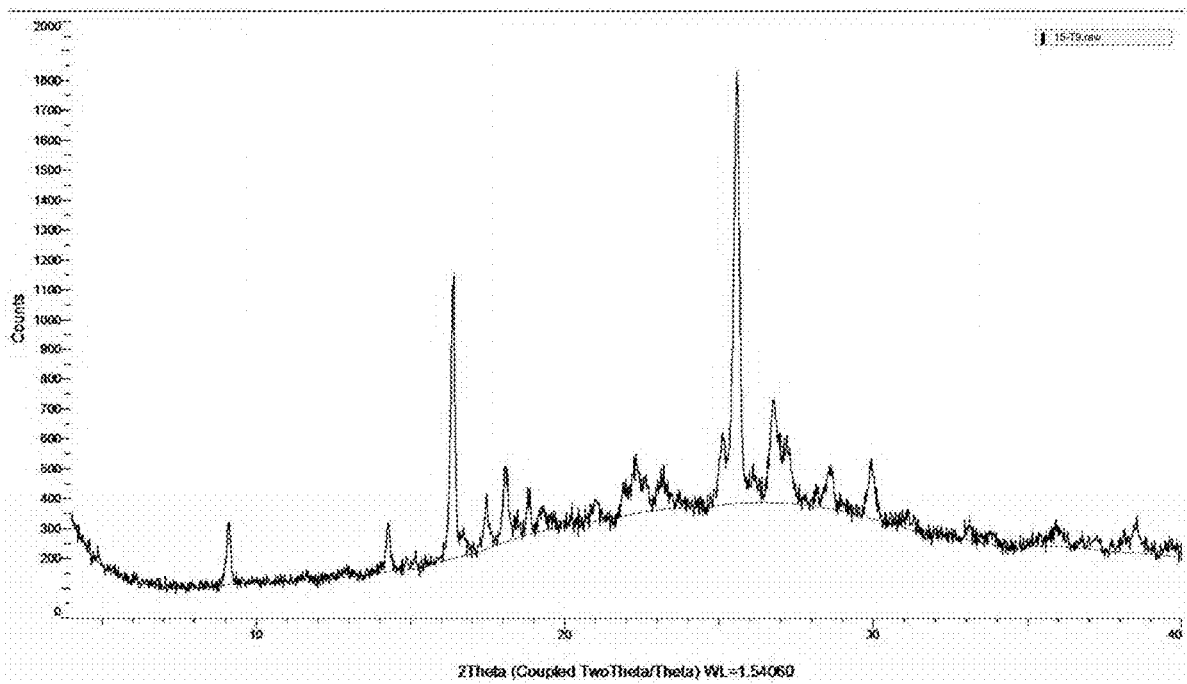

FIG. 268 depicts the XRPD profile of 15-T9 (Experiment Reference 15-Sample Reference T9) (amorphousised Pattern #1).

Figure 269:
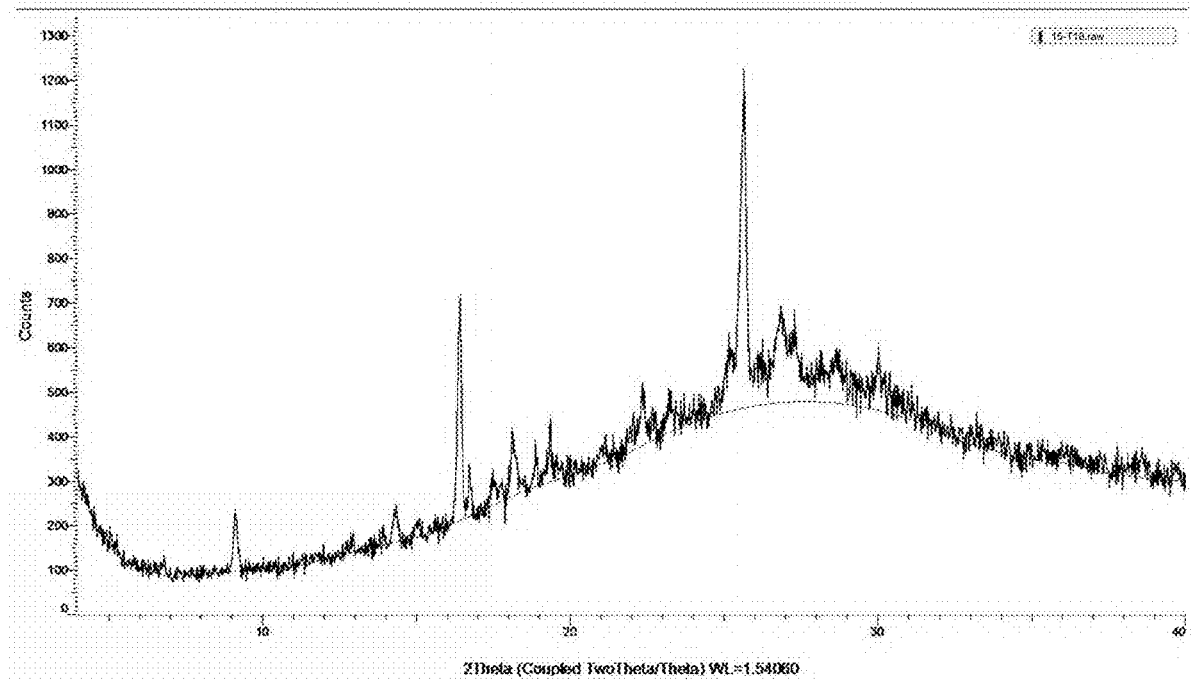

FIG. 269 depicts the XRPD profile of 15-T18 (Experiment Reference 15-Sample Reference T18) (amorphousised Pattern #1).

Figure 270:
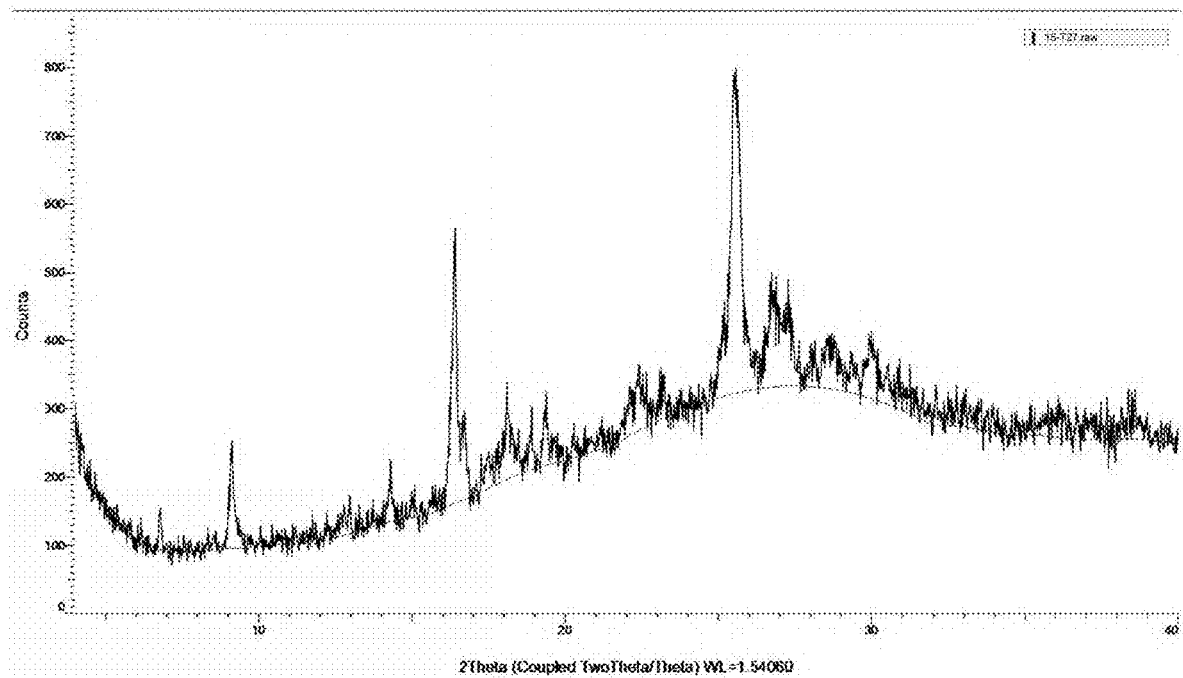

FIG. 270 depicts the XRPD profile of 15-T27 (Experiment Reference 15-Sample Reference T27) (amorphousised Pattern #1).

Figure 271:
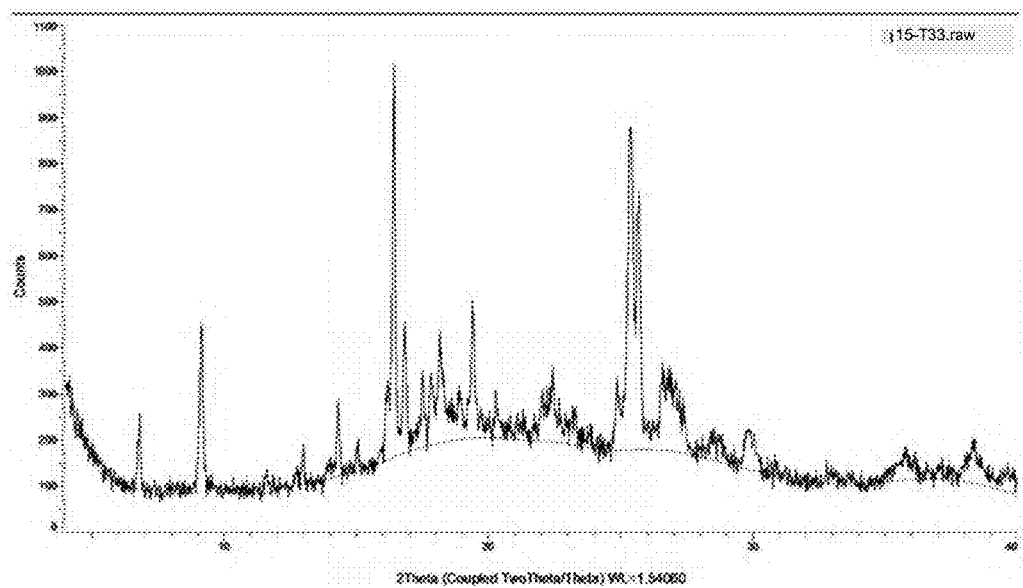

FIG. 271 depicts the XRPD profile of 15-T33 (Experiment Reference 15-Sample Reference T33) (amorphousised Pattern #1).

Figure 272:
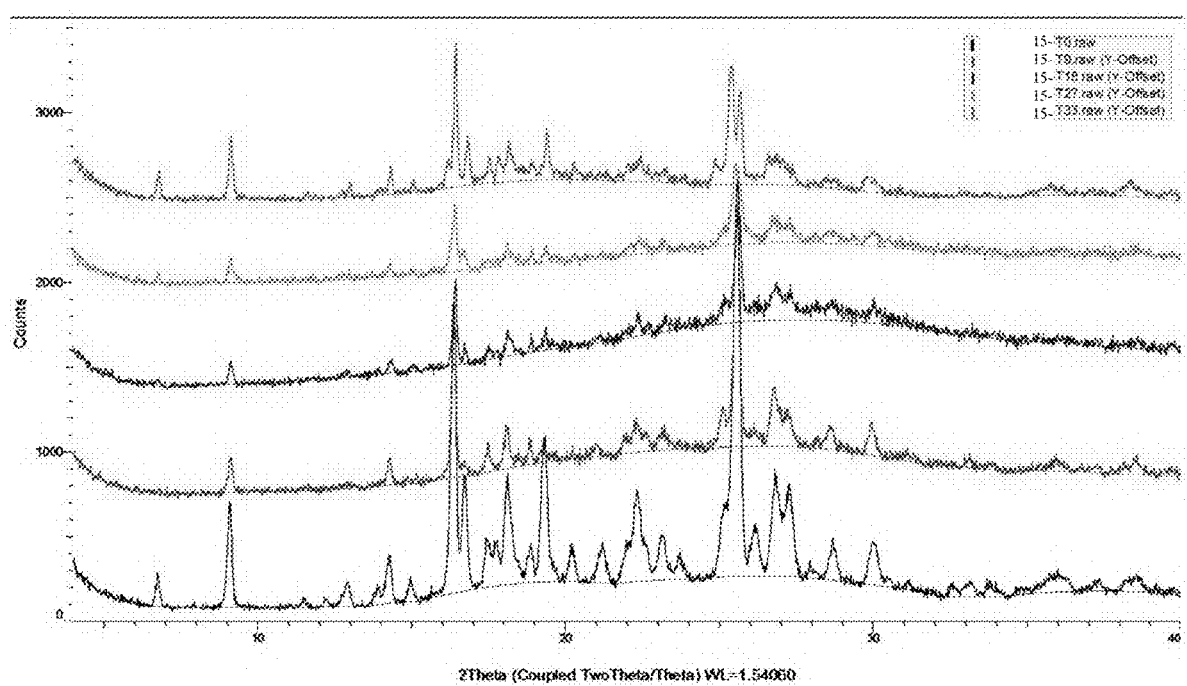

FIG. 272 depicts the XRPD diffractogram overlay of the various time points of, from bottom to top, Experiment Reference 15 (T=0 (Sample Reference 1), T=9 min, T=18 min, T=27 min, T=33 h), wherein 15-TO (Experiment Reference 15-Sample Reference TO); 15-T9 (Experiment Reference 15-Sample Reference T9); 15-T18 (Experiment Reference 15-Sample Reference T18); 15-T27 (Experiment Reference 15-Sample Reference T27) and 15-T33 (Experiment Reference 15-Sample Reference T33).

Figure 273:
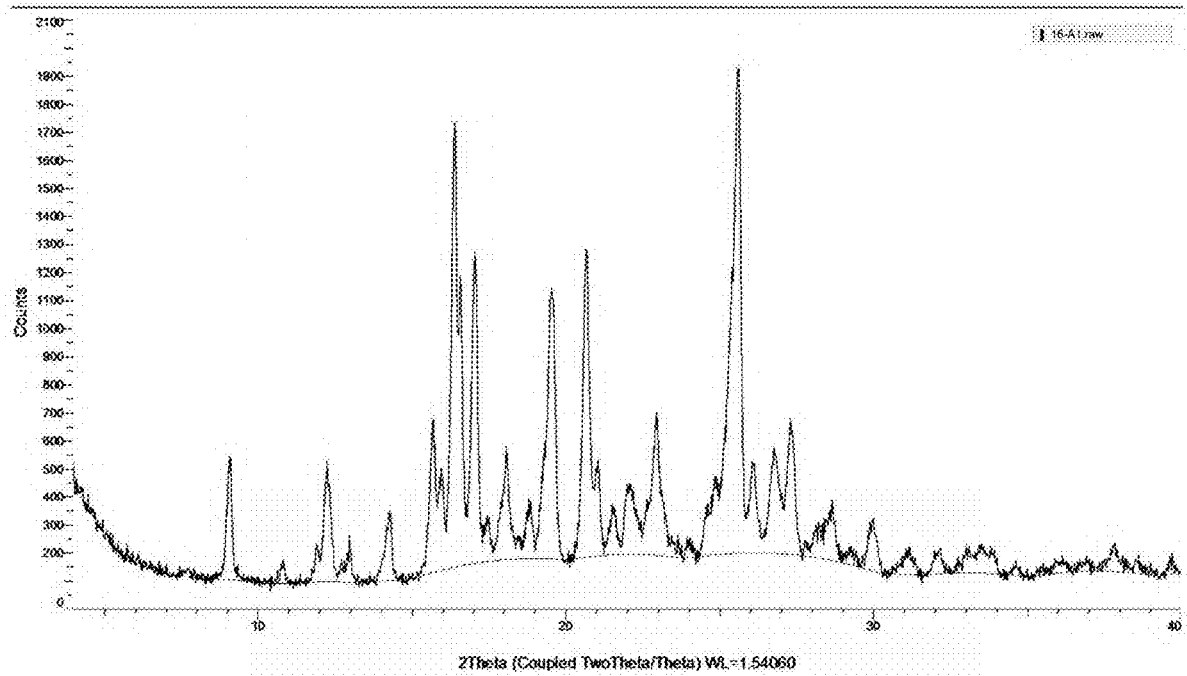

FIG. 273 depicts the XRPD profile of 16-A1 (wet sample, t=24 h) (Experiment Reference 16-Sample Reference A1).

Figure 274:
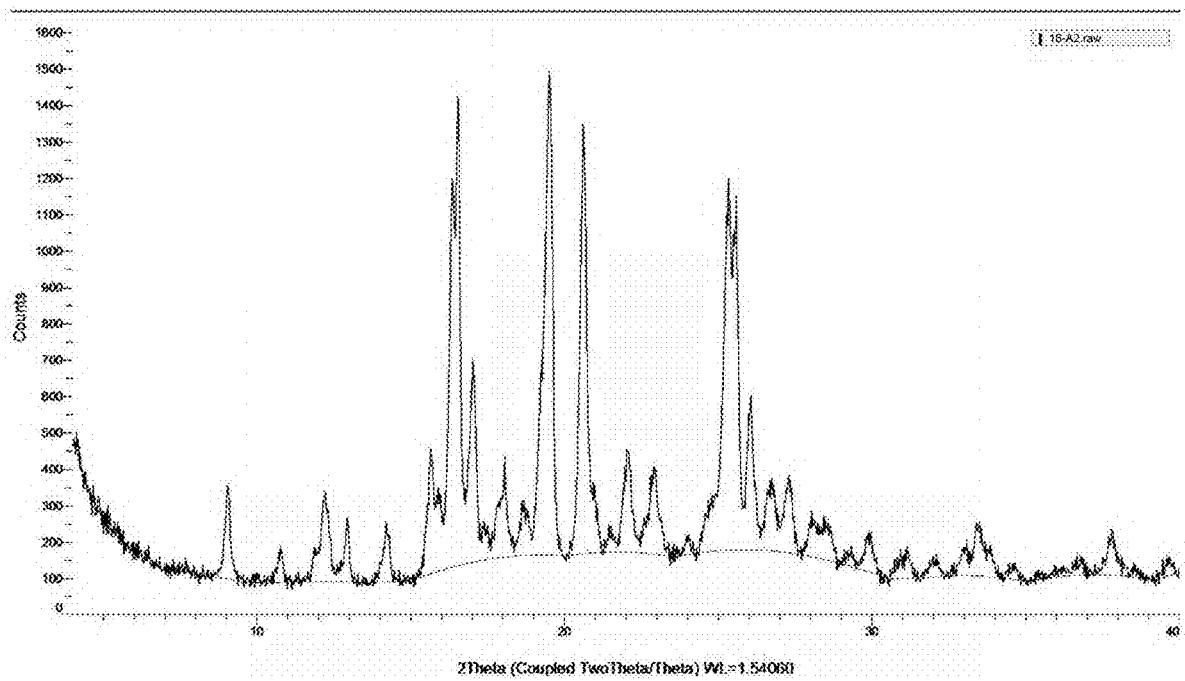

FIG. 274 depicts the XRPD profile of 16-A2 (wet sample, t=48 h) (Experiment Reference 16-Sample Reference A2).

Figure 275:
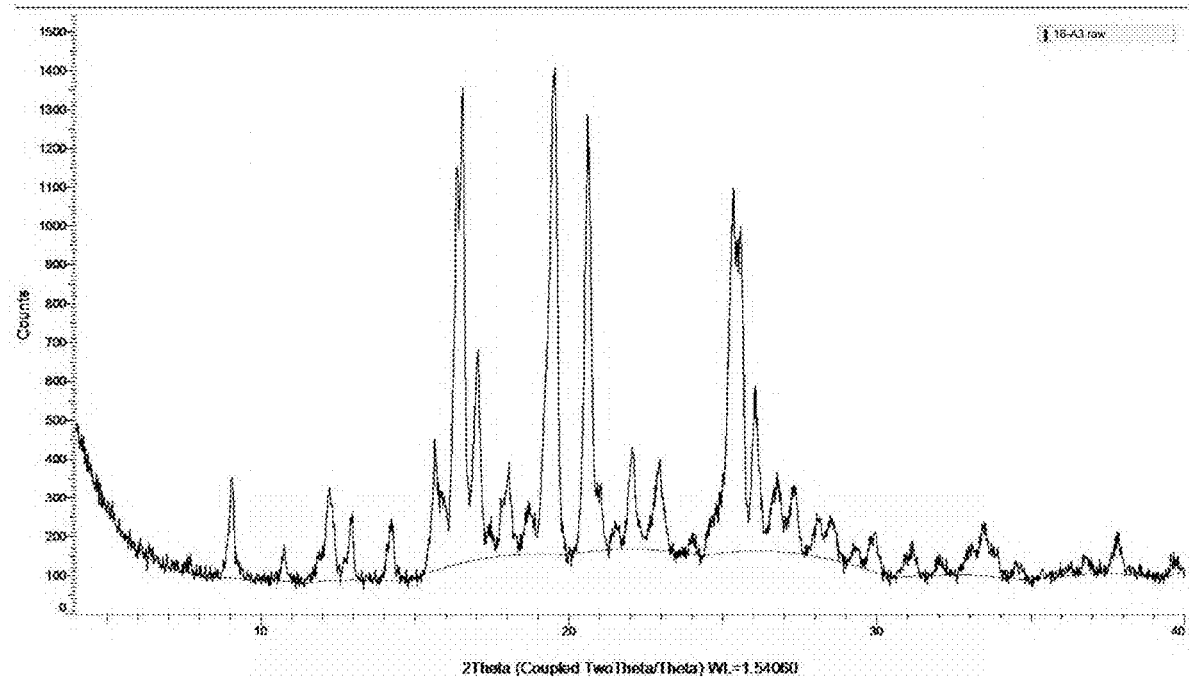

FIG. 275 depicts the XRPD profile of 16-A3 (wet sample, t=108 h) (Experiment Reference 16-Sample Reference A3).

Figure 276:
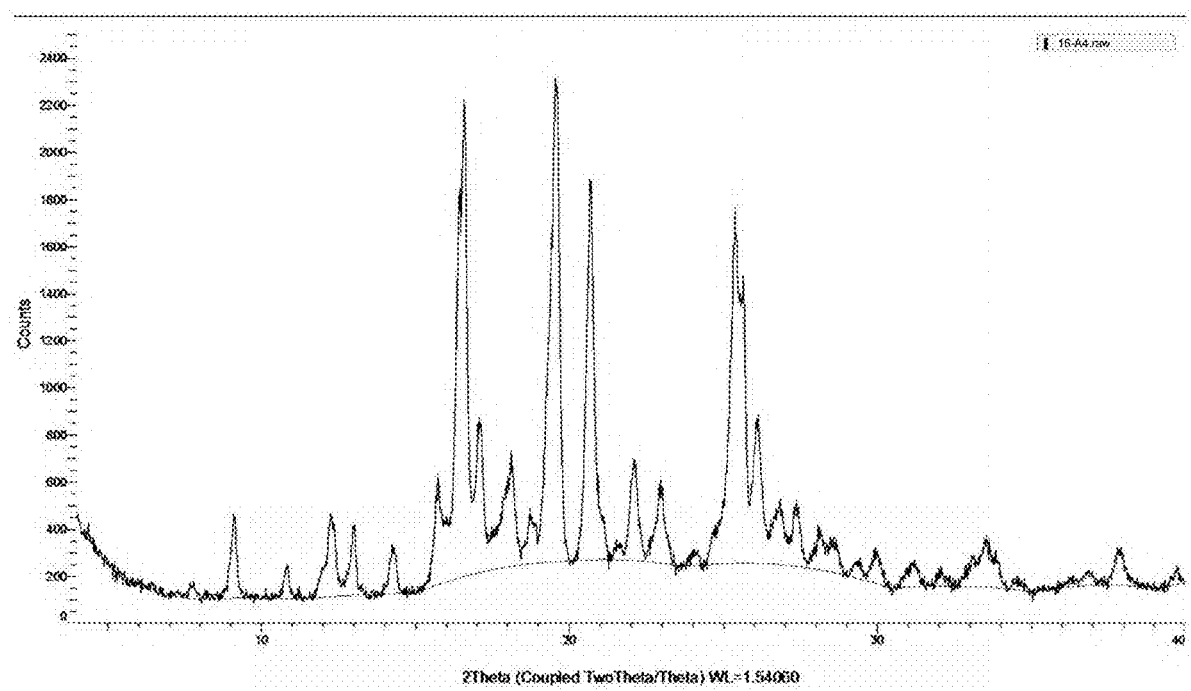

FIG. 276 depicts the XRPD profile of 16-A4 (wet sample, t=192 h) (Experiment Reference 16-Sample Reference A4).

Figure 277:
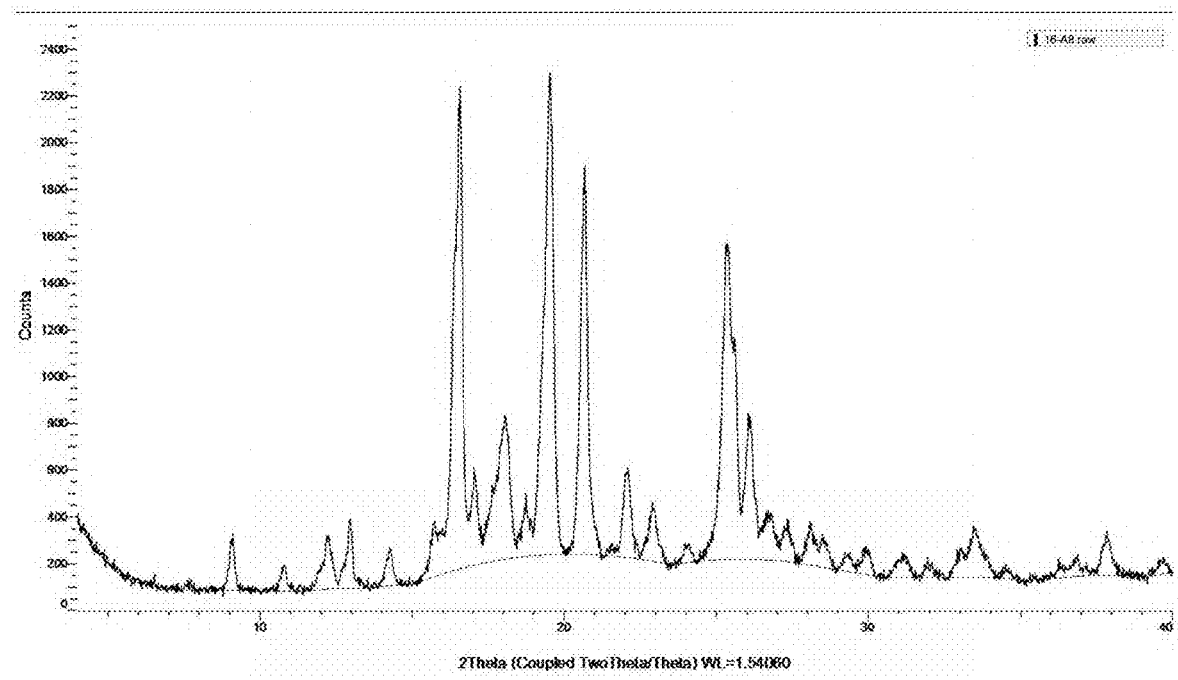

FIG. 277 depicts the XRPD profile of 16-A8 (wet sample, t=4 weeks) (Experiment Reference 16-Sample Reference A8).

Figure 278:
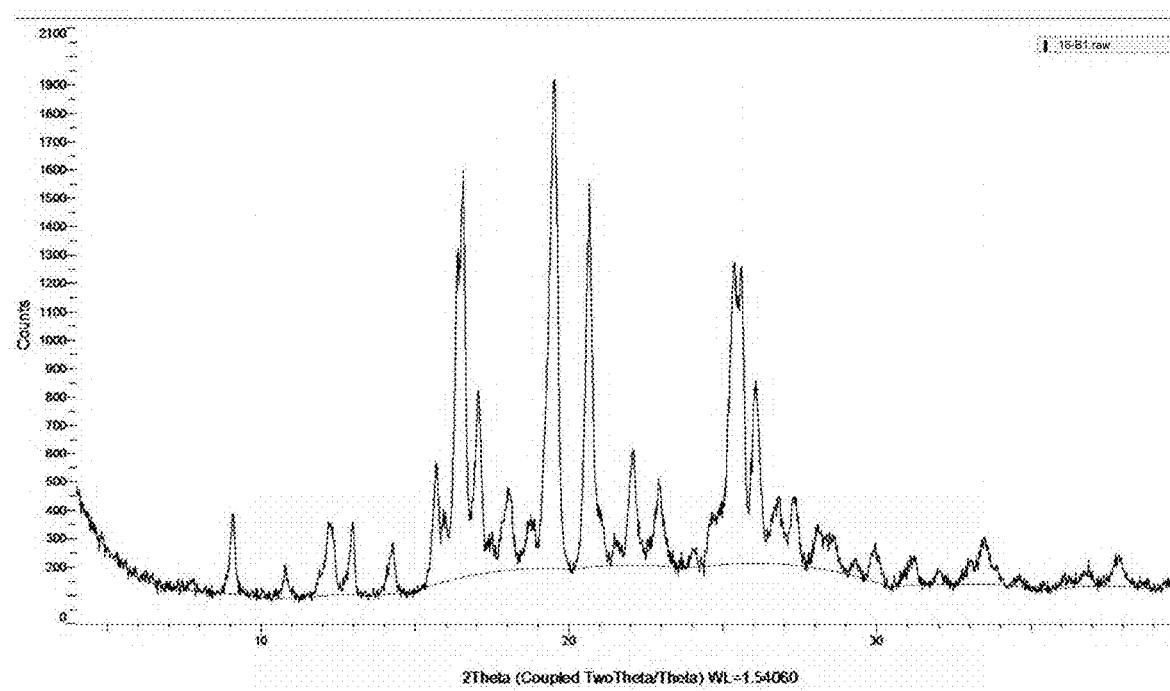

FIG. 278 depicts the XRPD profile of 16-B1 (wet sample, t=24 h) (Experiment Reference 16-Sample Reference B1).

Figure 279:
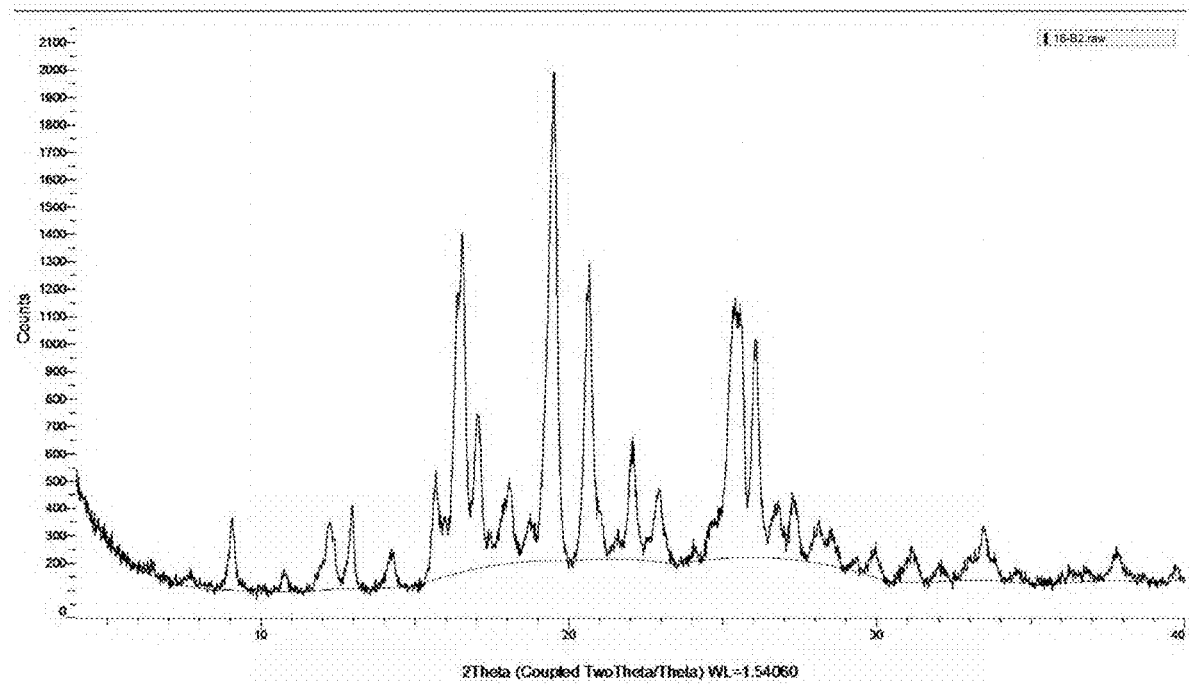

FIG. 279 depicts the XRPD profile of 16-B2 (wet sample, t=48 h) (Experiment Reference 16-Sample Reference B2).

Figure 280:
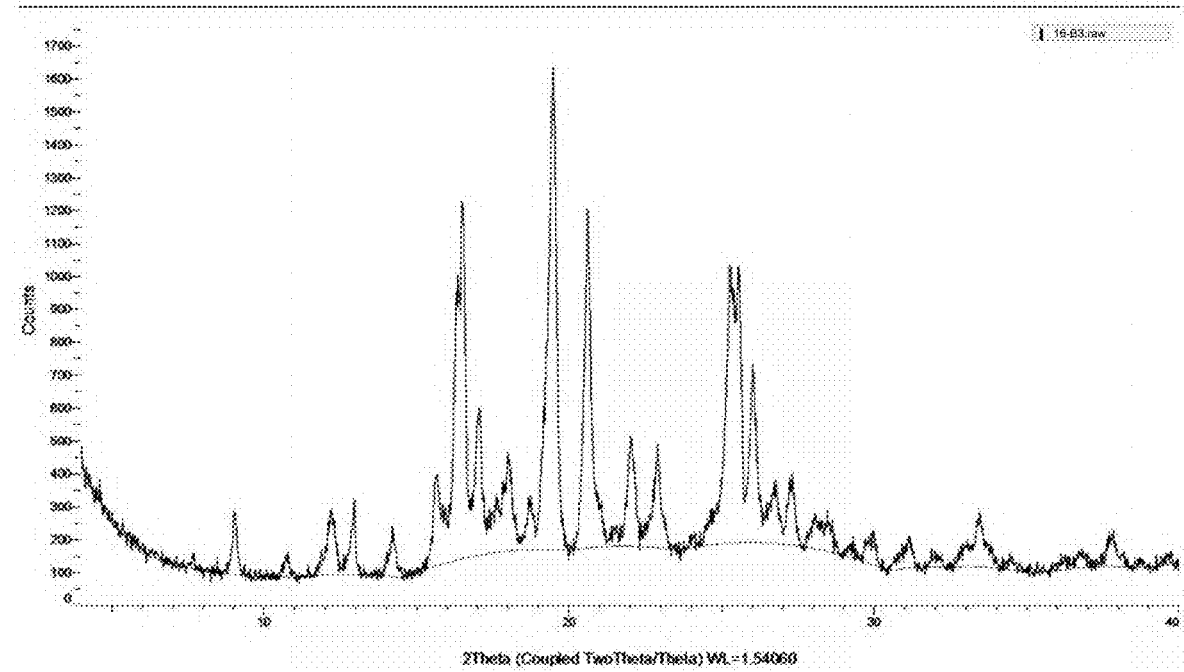

FIG. 280 depicts the XRPD profile of 16-B3 (wet sample, t=108 h) (Experiment Reference 16-Sample Reference B3).

Figure 281:
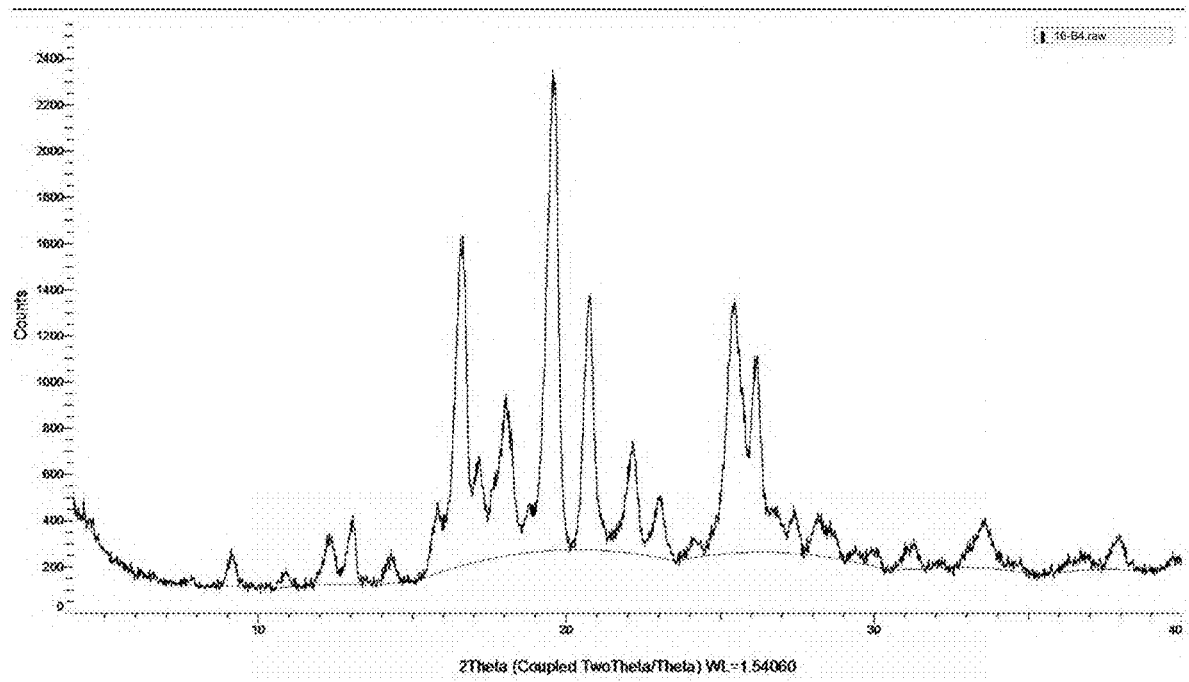

FIG. 281 depicts the XRPD profile of 16-B4 (wet sample, t=192 h). (Experiment Reference 16-Sample Reference B4).

Figure 282:
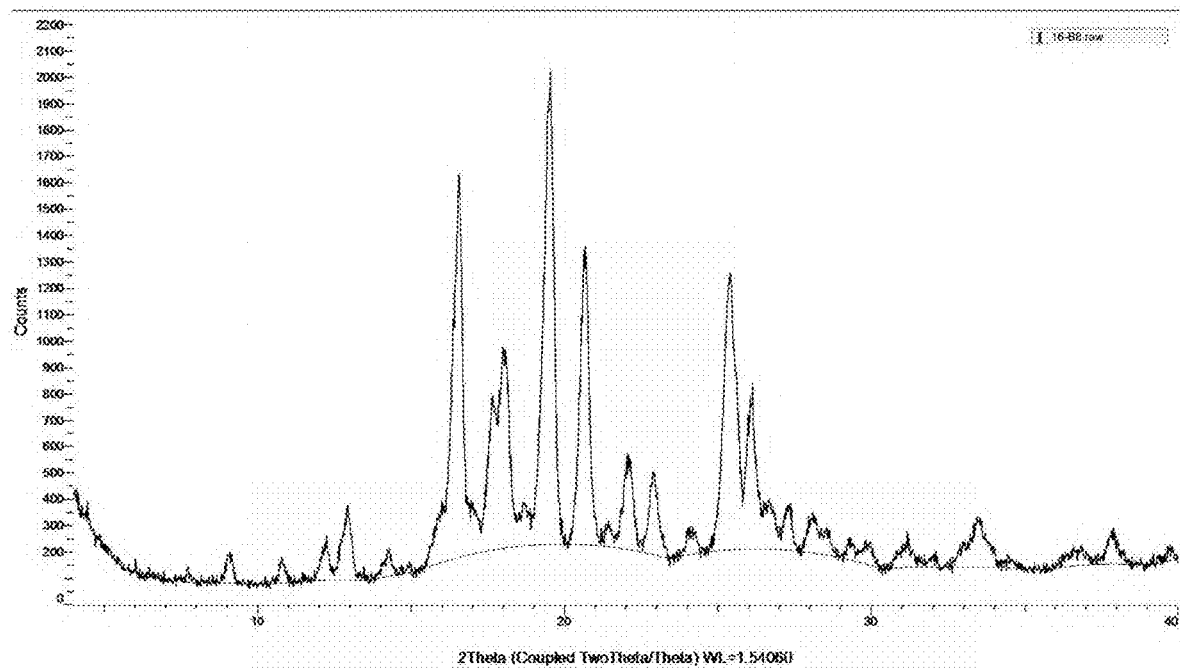

FIG. 282 depicts the XRPD profile of 16-B8 (wet sample, t=4 weeks) (Experiment Reference 16-Sample Reference B8).

Figure 283:
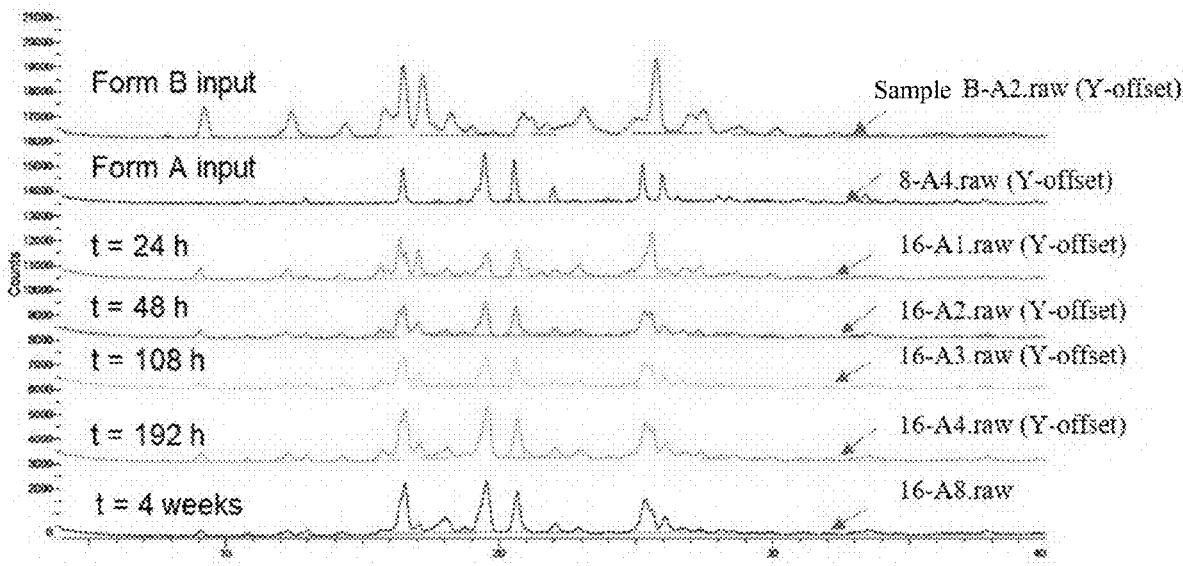

FIG. 283 depicts the timepoints of the suspension equilibration in tBME at 20° C. XRPD diffractogram overlay of, from top to bottom, Sample B-A2 (Form B, Pattern #2a), 8-A4 (Form A, Pattern #6a), 16-A1 (t=24 h, 16-A2 (t=48 h), 16-A3 (t=108 h), 16-A4 (t=192 h) 16-A8 (t=4 weeks).

Figure 284:
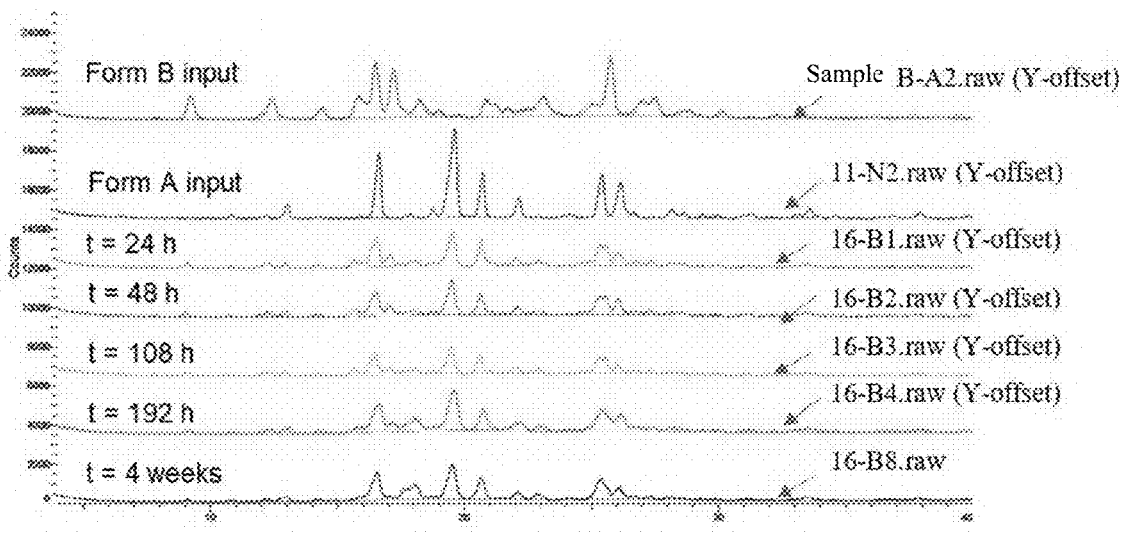

FIG. 284 depicts the timepoints of the suspension equilibration in tBME at 40° C. XRPD diffractogram overlay of, from top to bottom, Sample B-A2 (Form B, Pattern #2a), 8-A4 (Form A, Pattern #6a), 16-B1 (t=24 h, 16-B2 (t=48 h), 16-B3 (t=108 h), 16-B4 (t=192 h) 16-B8 (t=4 weeks).

FIG. 285 depicts the crystal data for 11-M2 (Experiment Reference 11-Sample Reference M2).

FIG. 286 depicts the crystal data for 11-Q2 (Experiment Reference 11-Sample Reference Q2).

Figure 287:
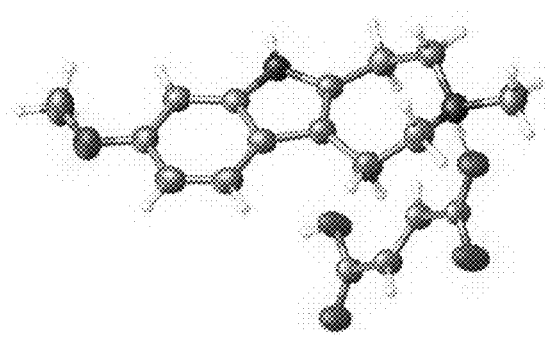

FIG. 287 depicts the crystal structure of the tabernanthalog monofumarate salt (Pattern #6a, Form A).

Figure 288:
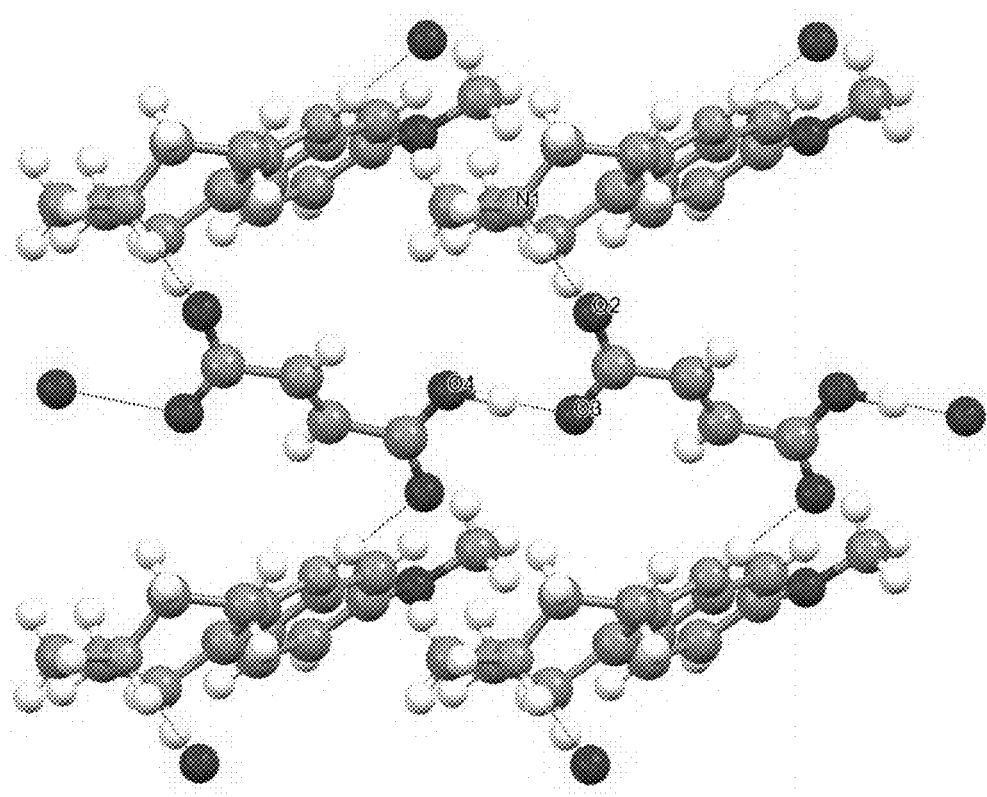

FIG. 288 depicts the hydrogen bonding network of the tabernanthalog monofumarate salt (Pattern #6a, Form A).

Figure 289:
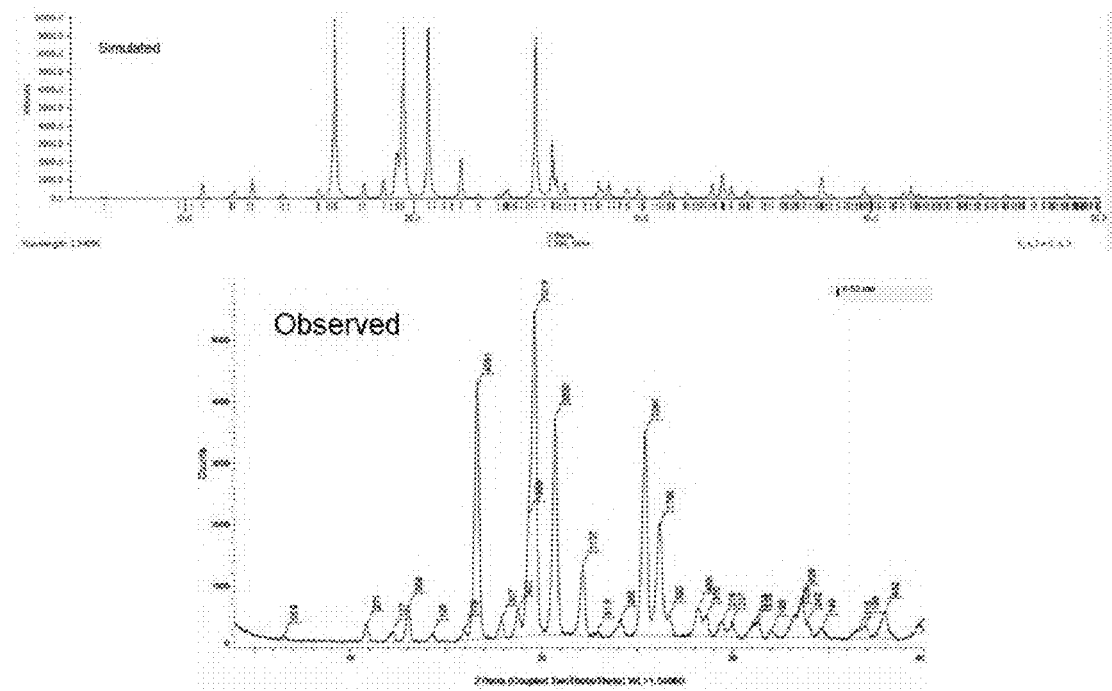

FIG. 289 depicts the comparison of simulated powder pattern 11-M2 (Experiment Reference 11-Sample Reference M2, top) and experimentally obtained powder diffraction pattern for 6-S2 (Experiment Reference 6-Sample Reference S2) (Form A, Pattern #6a, reference, bottom).

Figure 289A:
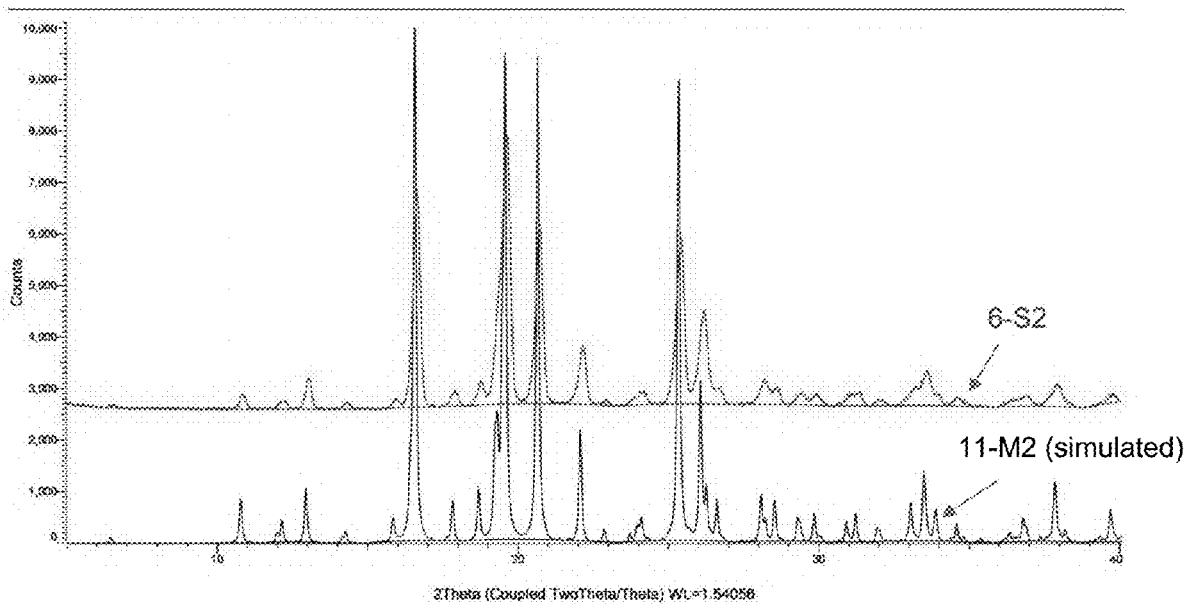

FIG. 289A depicts the XRPD diffractogram overlay of simulated powder diffraction pattern (bottom, 11-M2 (Experiment Reference 11-Sample Reference M2), Form A) and 6-S2 ((Experiment Reference 6-Sample Reference S2), top, Form A reference).

FIG. 290 depicts the SCXRD (11-M2 (Experiment Reference 11-Sample Reference M2)), structural void analyses.

FIG. 291 depicts the crystal structure of tabernanthalog hemifumarate (Pattern #14, Form I).

FIG. 292 depicts the hydrogen bonding network of tabernanthalog hemifumarate (Pattern #14, Form I).

Figure 293:
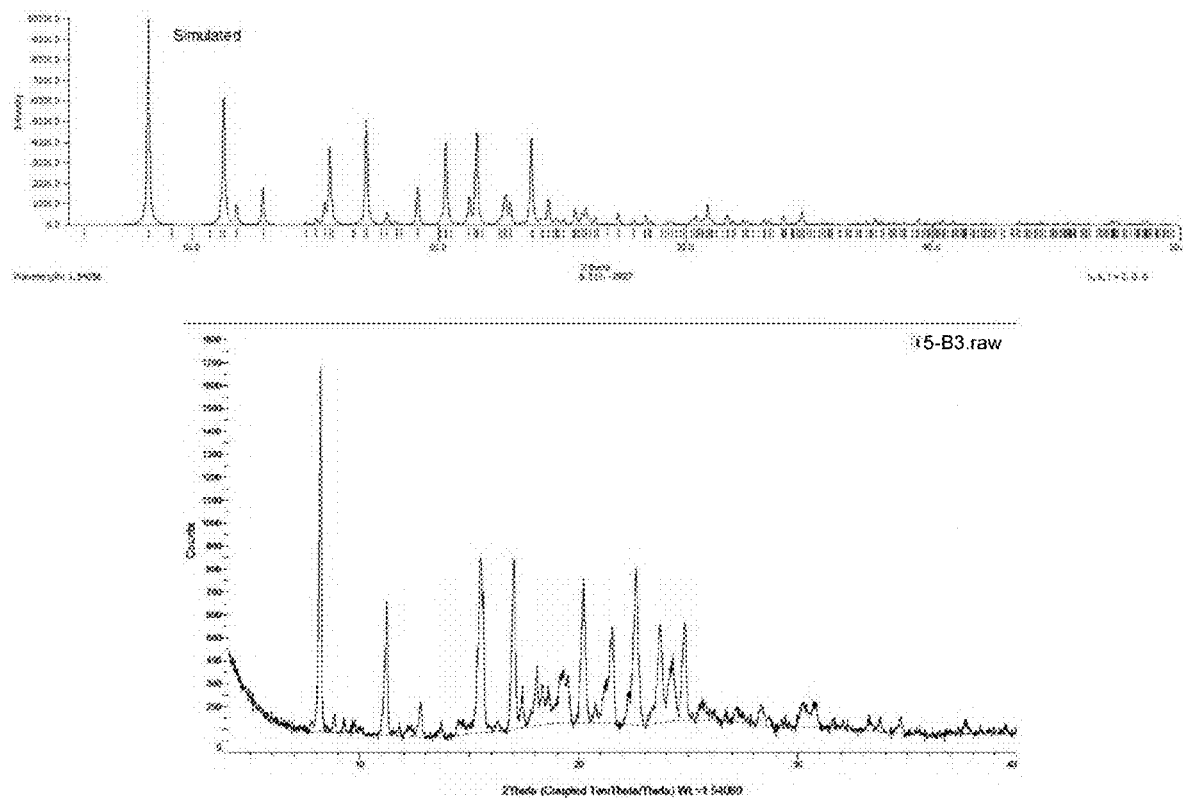

FIG. 293 depicts the comparison of simulated powder pattern 11-Q2 (Experiment Reference 11-Sample Reference Q2) and experimentally obtained powder diffraction pattern for 5-B3 (Experiment Reference 5-Sample Reference B3).

Figure 293A:
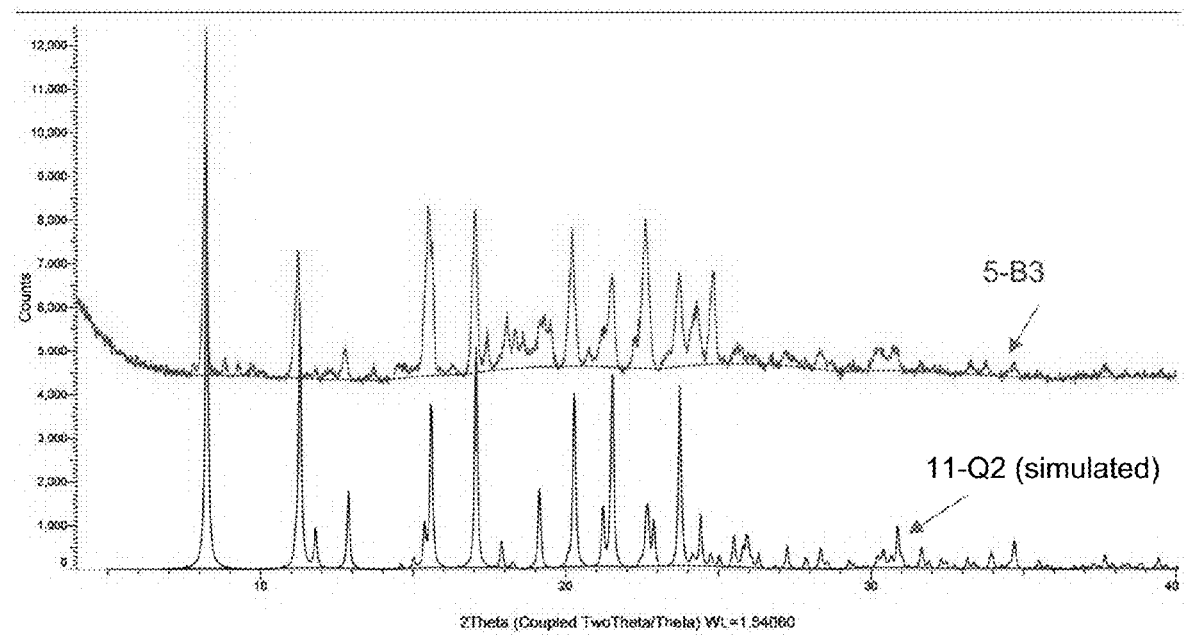

FIG. 293A depicts the XRPD diffractogram overlay of simulated powder diffraction pattern 11-Q2 (Experiment Reference 11-Sample Reference Q2), bottom, Form I) and 5-B3 ((Experiment Reference 5-Sample Reference B3), top, Form I reference).

Figure 294:
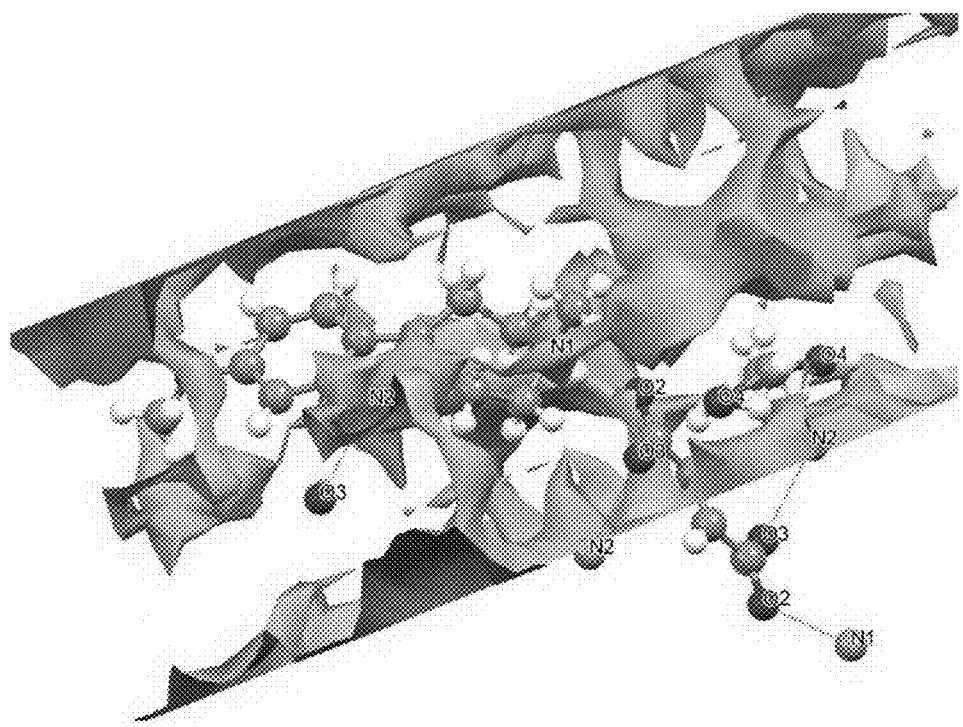

FIG. 294 depicts the SCXRD (11-Q2 (Experiment Reference 11-Sample Reference Q2)), structural void analyses.

Figure 295:
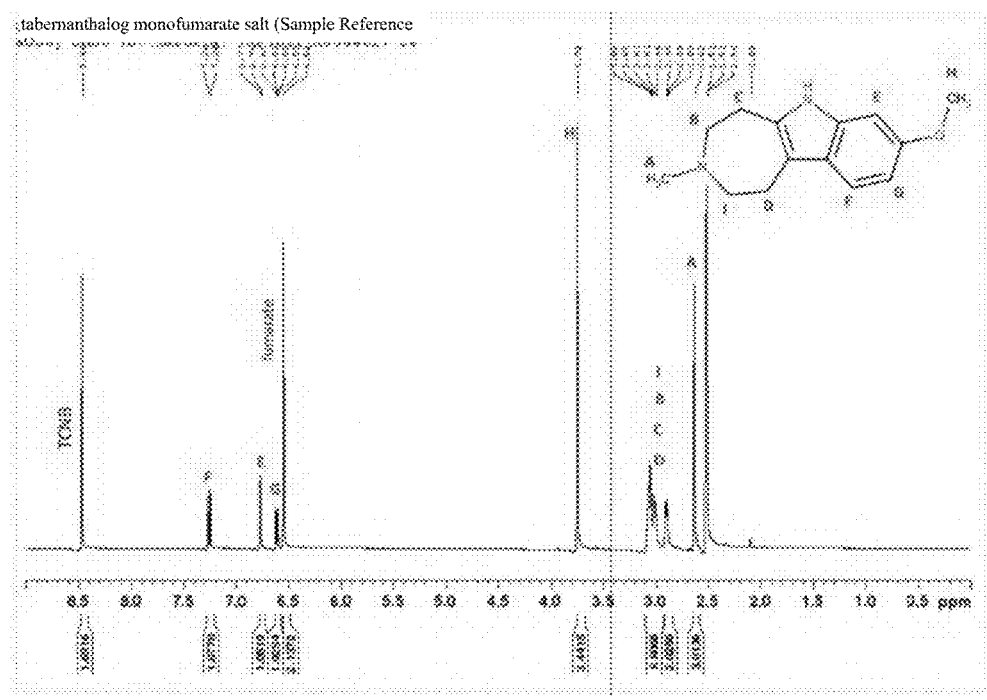

FIG. 295 depicts the Q NMR assay (vs TCNB) of the tabernanthalog monofumarate salt (Sample Reference 1, Pattern #1, 93.13% w/w), spectrum was acquired in DMSO-$d_6$ and calibrated to the non-deuterated solvent residual at 2.50 ppm. API to Fumaric acid, 1.0 to 1.0.

Figure 296:
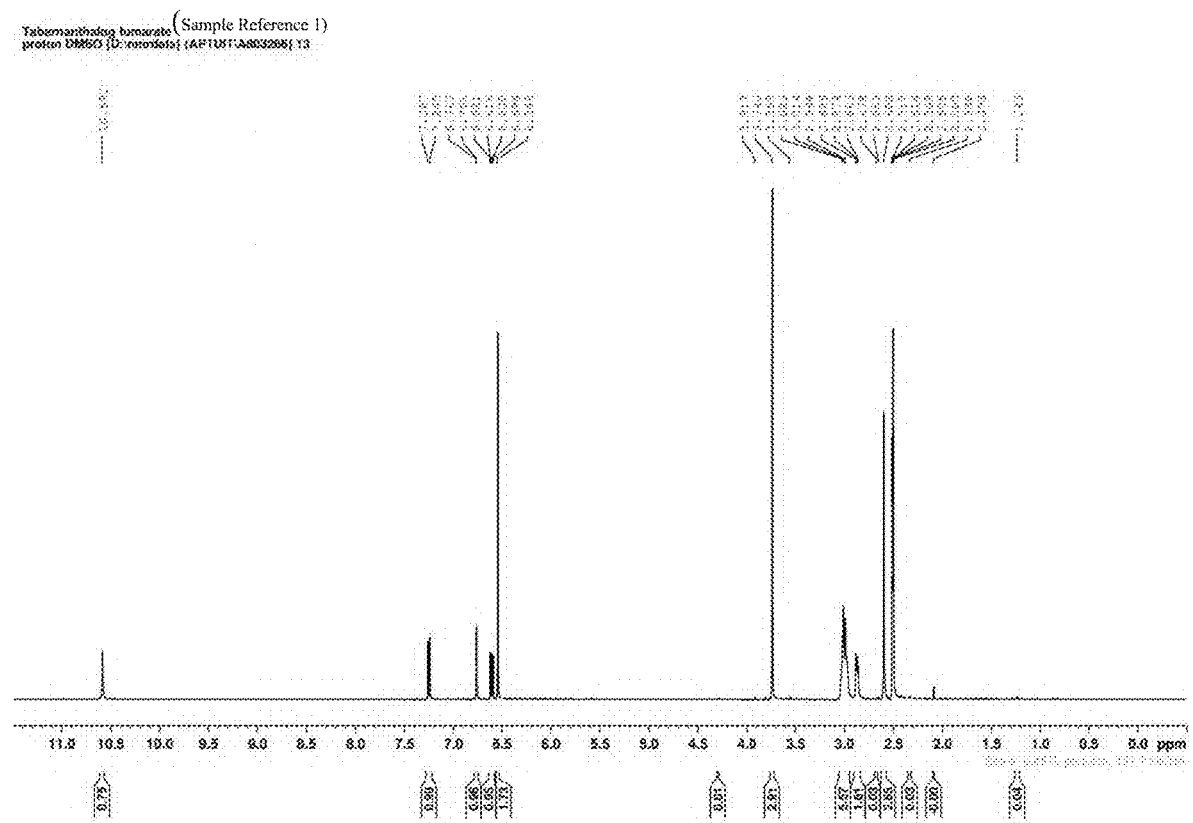

FIG. 296 depicts the $^1$H NMR of the tabernanthalog monofumarate salt (Sample Reference 1, Pattern #1), spectrum was acquired in DMSO-$d_e$ and calibrated to the non-deuterated solvent residual at 2.50 ppm. Acetonitrile content calculated 0.2% w/w.

Figure 297:
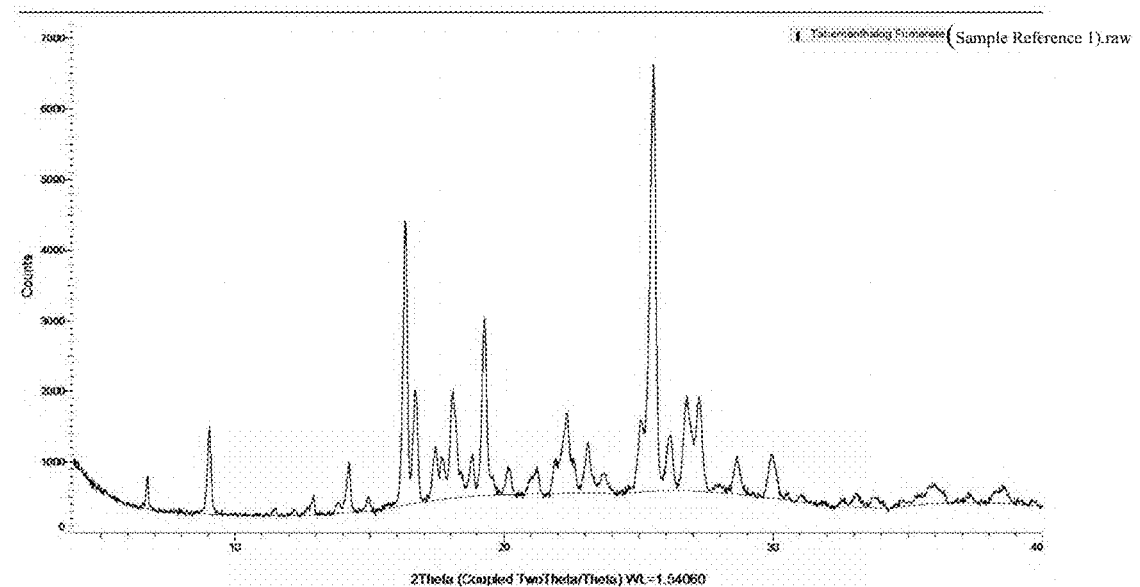

FIG. 297 depicts the XRPD profile of the tabernanthalog monofumarate salt (Sample Reference 1, Pattern #1).

Figure 298:
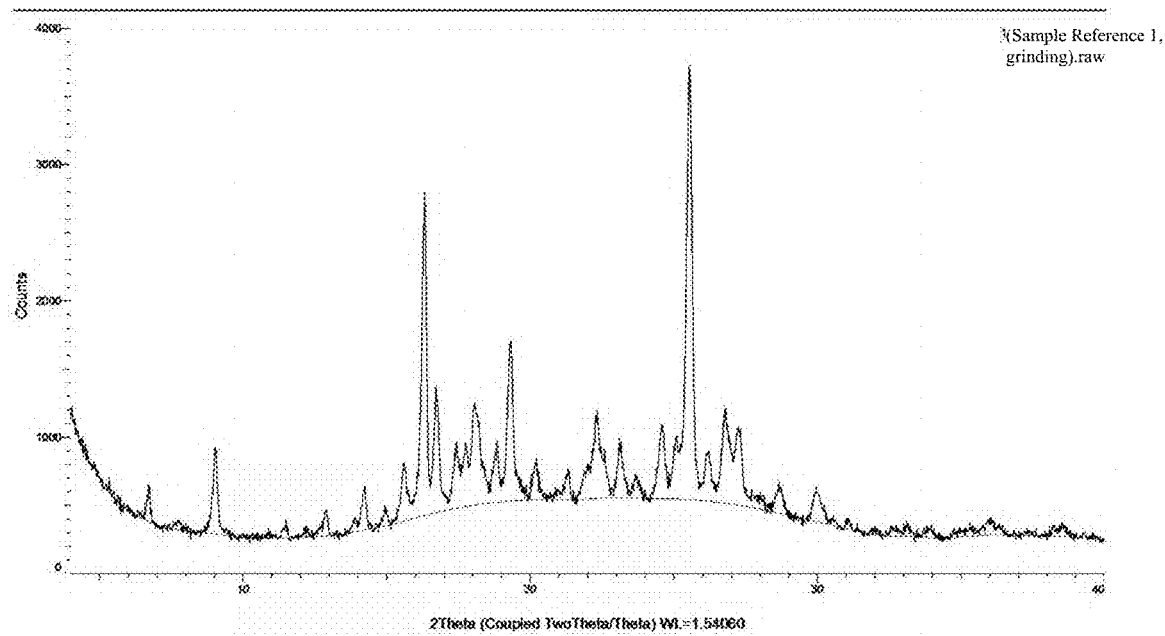

FIG. 298 depicts the XRPD profile of the tabernanthalog monofumarate salt ground (Sample Reference 1, Pattern #1).

Figure 299:
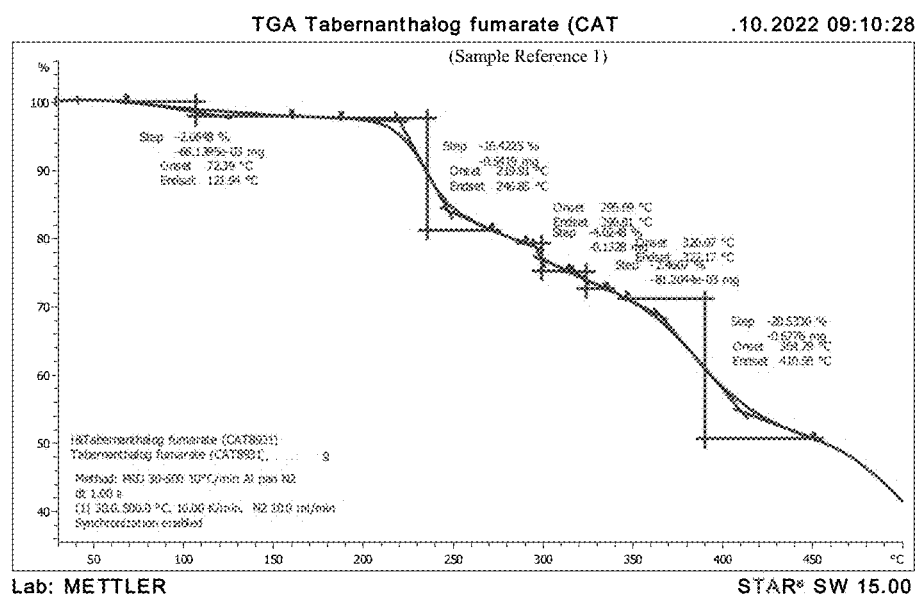

FIG. 299 depicts the TGA profile of the tabernanthalog monofumarate salt (Sample Reference 1, Pattern #1, not ground), analysis was acquired at a ramp rate of +10° C./minute. The first TG event (−2.1% w/w) was consistent with the release of volatiles, potentially water and solvent (water −2.6% w/w+acetonitrile −0.2% w/w). Significant weight loss was observed at higher temperature (>200° C.), attributed to chemical degradation and ablation of the sample.

Figure 300:
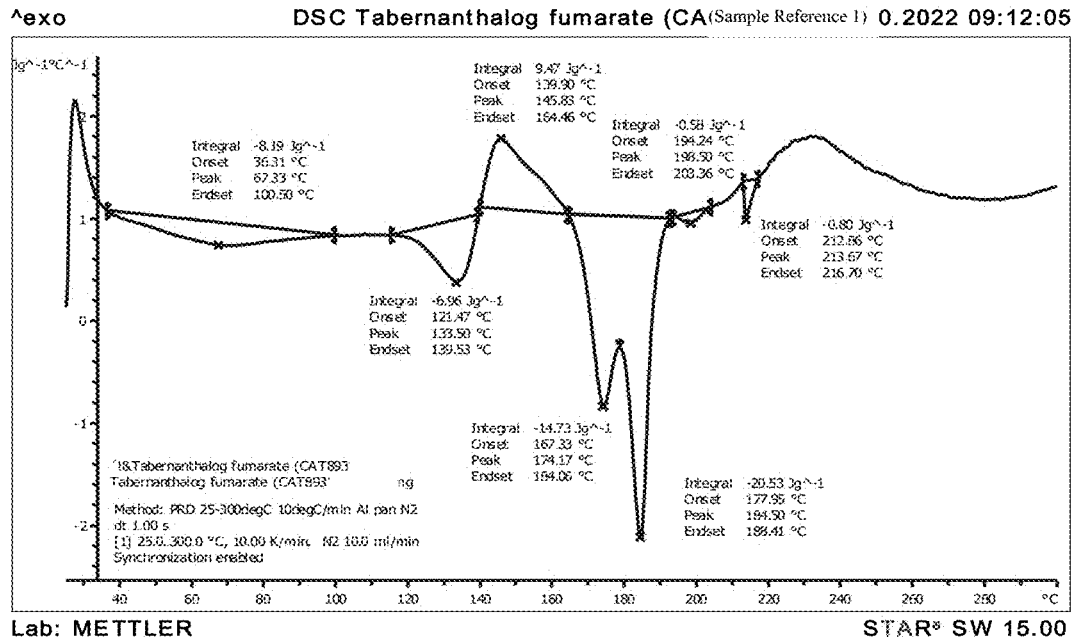

FIG. 300 depicts the DSC of the tabernanthalog monofumarate salt (Pattern #1, Sample Reference 1, not ground), analysis was acquired at a ramp rate of +10° C./minute.

Figure 301:
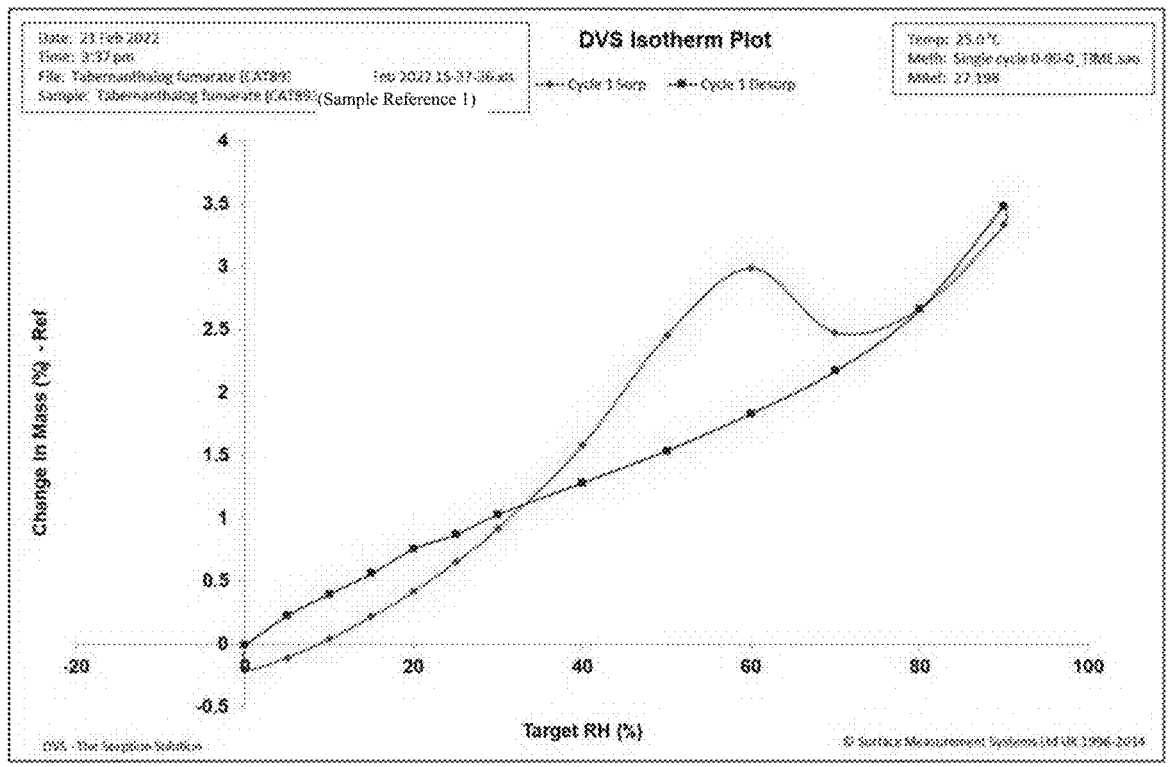

FIG. 301 depicts the DVS profiles of the tabernanthalog monofumarate salt (Pattern #1, Sample Reference 1, not ground).

Figure 302:
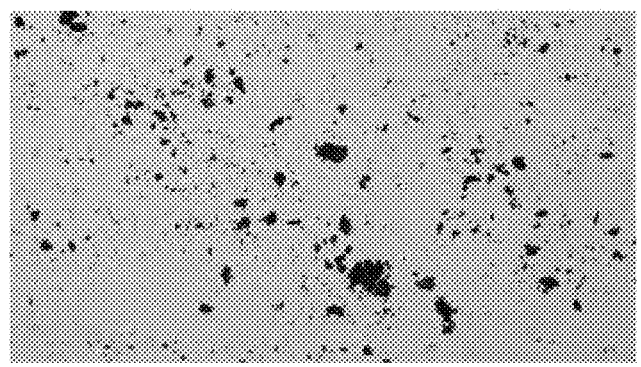

FIG. 302: depicts the PLM of the tabernanthalog monofumarate salt (Pattern #1, Sample Reference 1, not ground), normal polarized (magnification×2).

Figure 303:
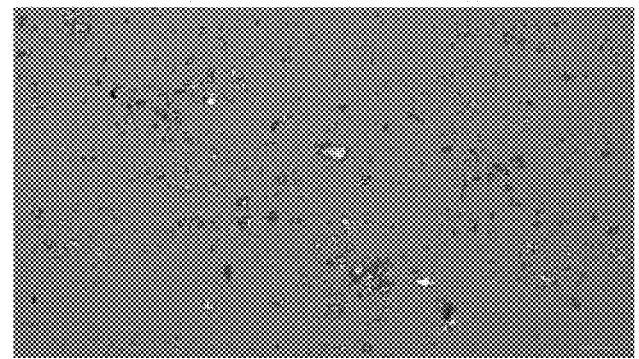

FIG. 303 depicts the PLM of the tabernanthalog monofumarate salt (Pattern #1, Sample Reference 1, not ground), cross polarized (magnification×5).

Figure 304:
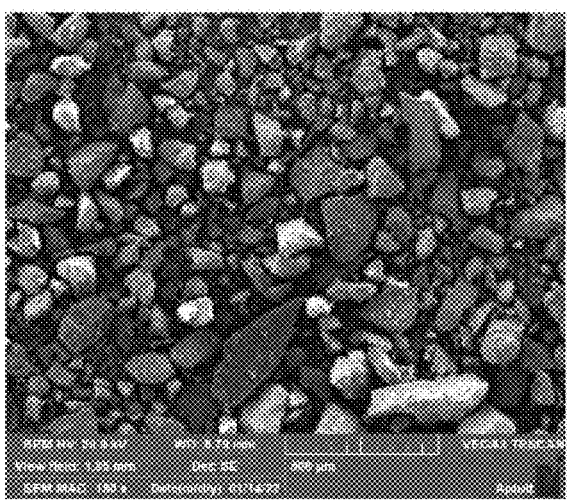

FIG. 304 depicts the SEM surface topography of the tabernanthalog monofumarate salt (Pattern #1, Sample Reference 1, not ground), resolution at 150×.

Figure 305:
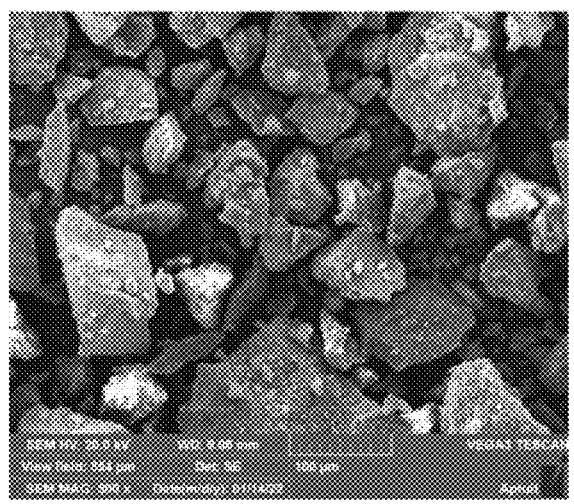

FIG. 305 depicts the SEM surface topography of the tabernanthalog monofumarate salt (Pattern #1, Sample Reference 1, not ground), resolution at 500×.

Figure 306:
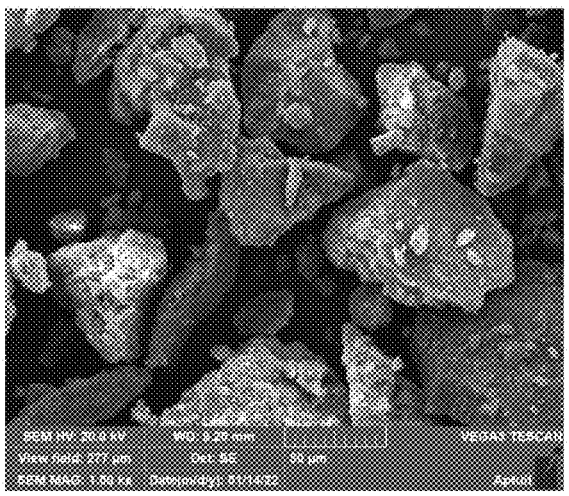

FIG. 306 depicts the SEM surface topography of the tabernanthalog monofumarate salt (Pattern #1, Sample Reference 1, not ground), resolution at 1000×.

Figure 307:
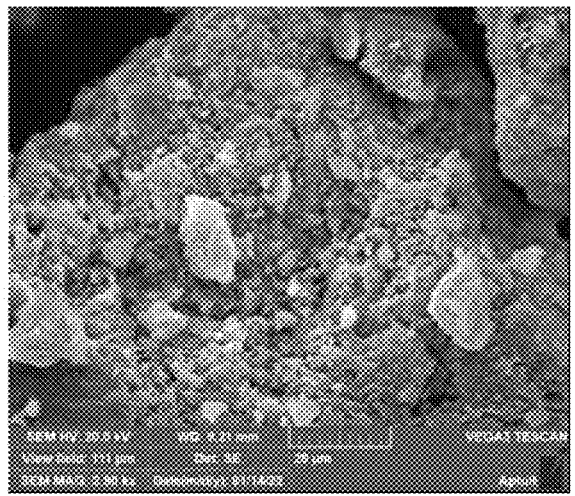

FIG. 307 depicts the SEM surface topography of the tabernanthalog monofumarate salt (Pattern #1, Sample Reference 1, not ground), resolution at 2500×.

Figure 308:
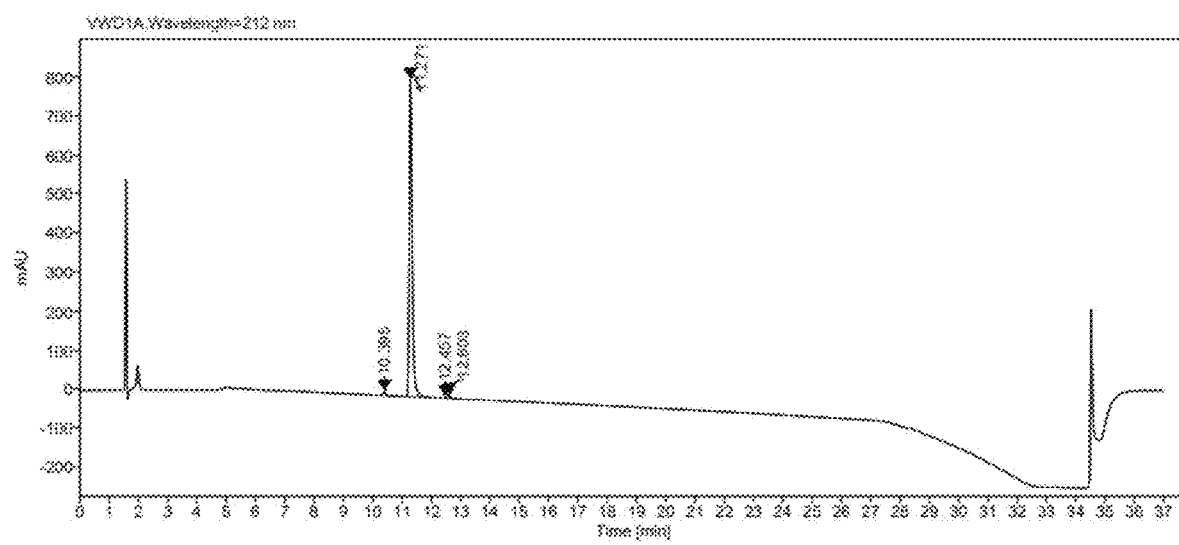

FIG. 308 depicts the HPLC profile of the tabernanthalog monofumarate salt (Pattern #1, Sample Reference 1, not ground).

Figure 309:
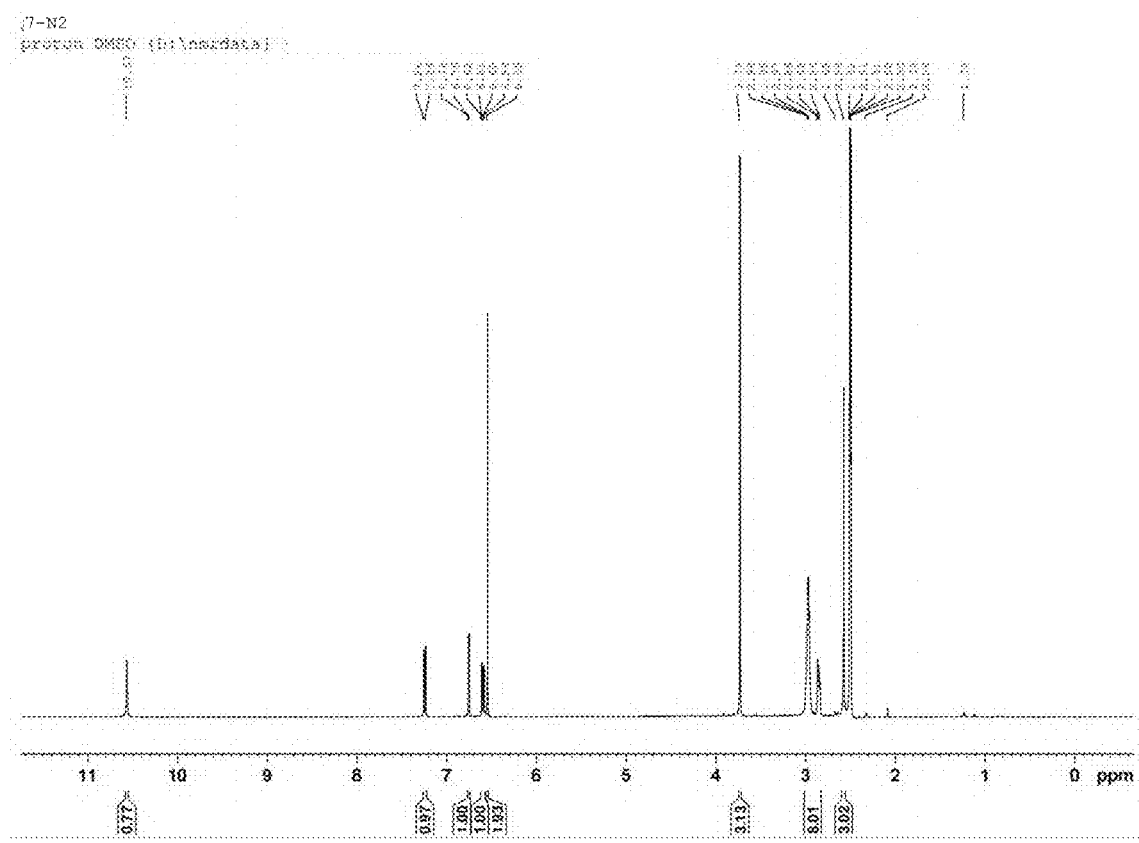

FIG. 309 depicts the $^1$H NMR spectrum of 7-N2 (Experiment Reference 7-Sample Reference N2) (suspended in 2-MeTHF), analysis was acquired in DMSO-d6 and calibrated to the non-deuterated solvent residual at 2.50 ppm API to Fumaric acid, 1.0 to 1.0. 2-MeTHF n.d.

Figure 311:
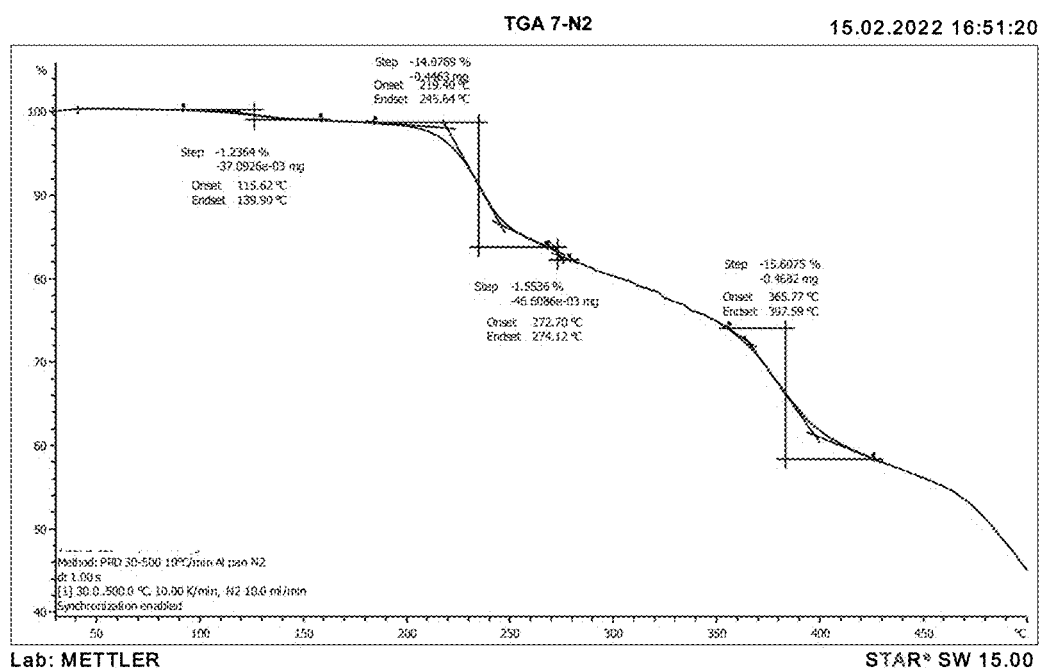

FIG. 311 depicts the TGA profile of 7-N2 (Experiment Reference 7-Sample Reference N2), analysis was acquired at a ramp rate of +10° C./minute.

Figure 312:
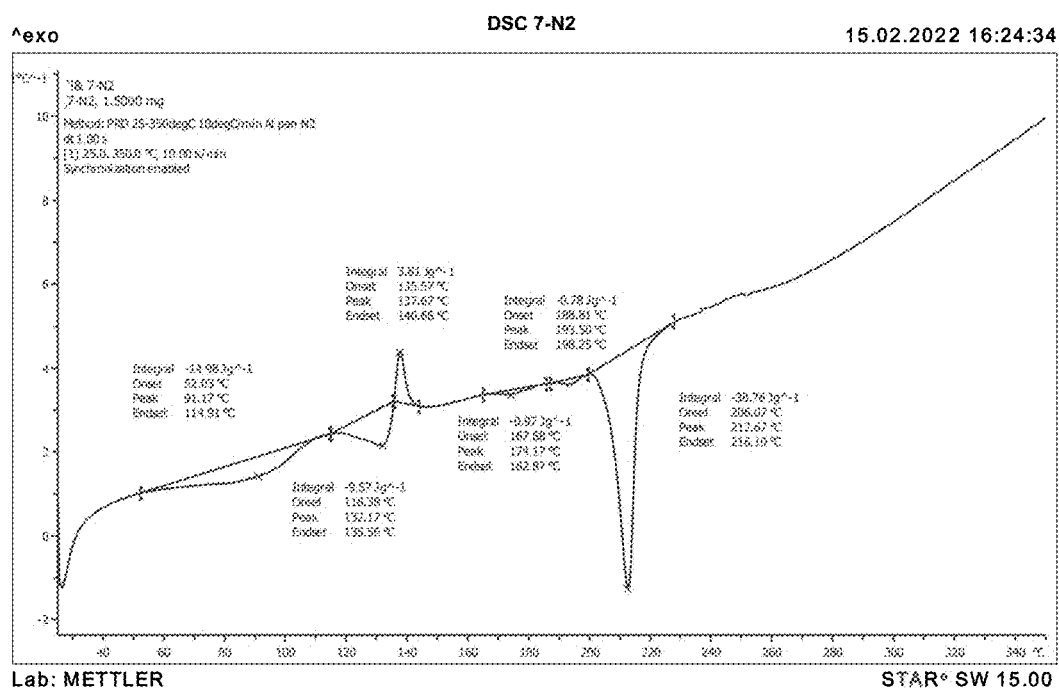

FIG. 312 depicts the DSC profile of 7-N2 (Experiment Reference 7-Sample Reference N2), analysis was acquired at a ramp rate of +10° C./minute.

Figure 313:
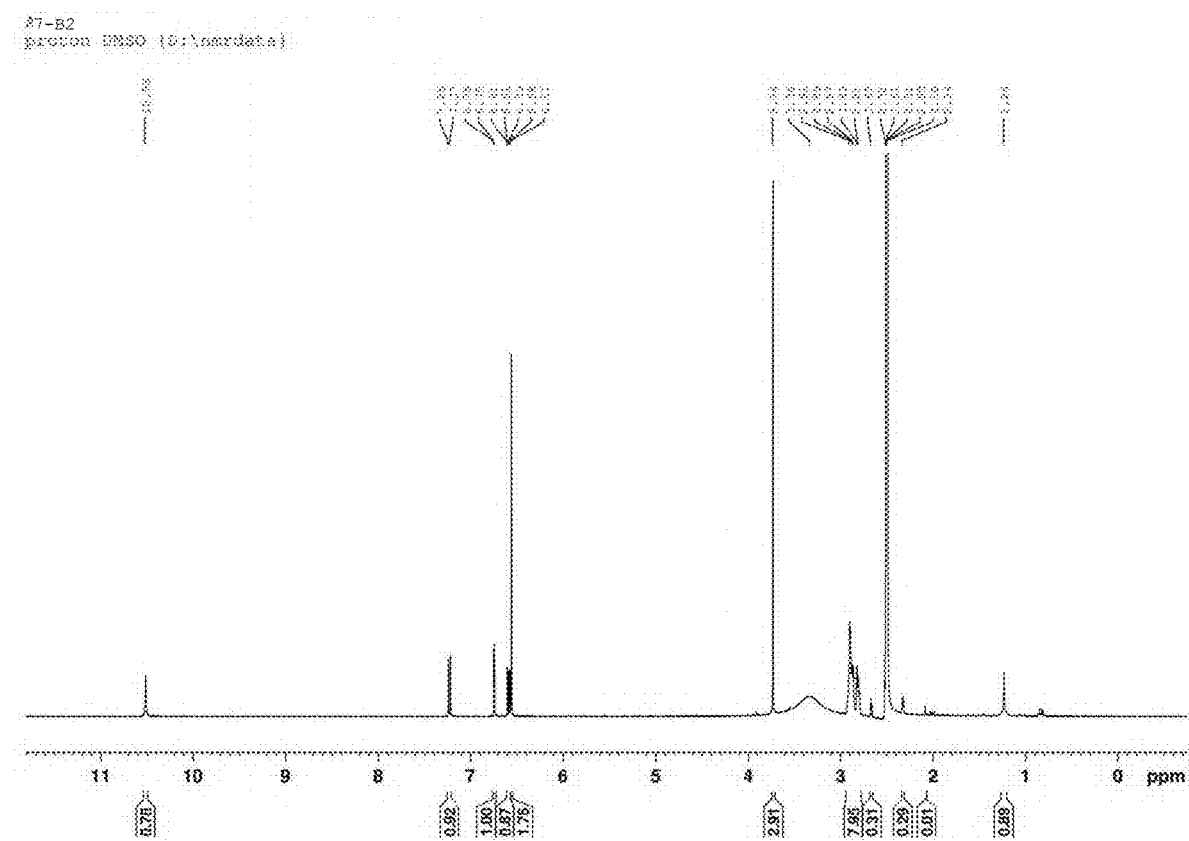

FIG. 313 depicts the $^1$H NMR spectrum of 7-B2 (Experiment Reference 7-Sample Reference B2) (suspended in MeCN), analysis was acquired in DMSO-d6 and calibrated to the non-deuterated solvent residual at 2.50 ppm. API to Fumaric acid, 1.0 to 1.0, 0.03% w/w MeCN content.

Figure 315:
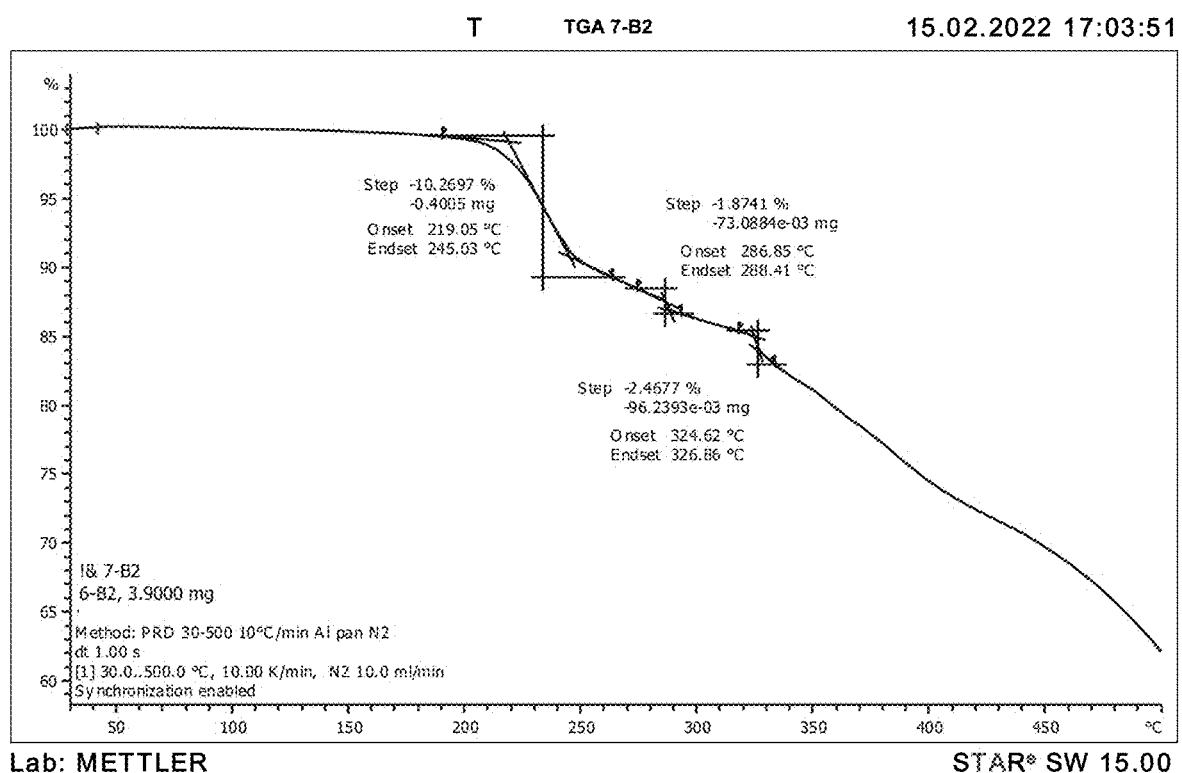

FIG. 315 depicts the TGA profile of 7-B2 (Experiment Reference 7-Sample Reference B2), analysis was acquired at a ramp rate of +10° C./minute.

Figure 316:
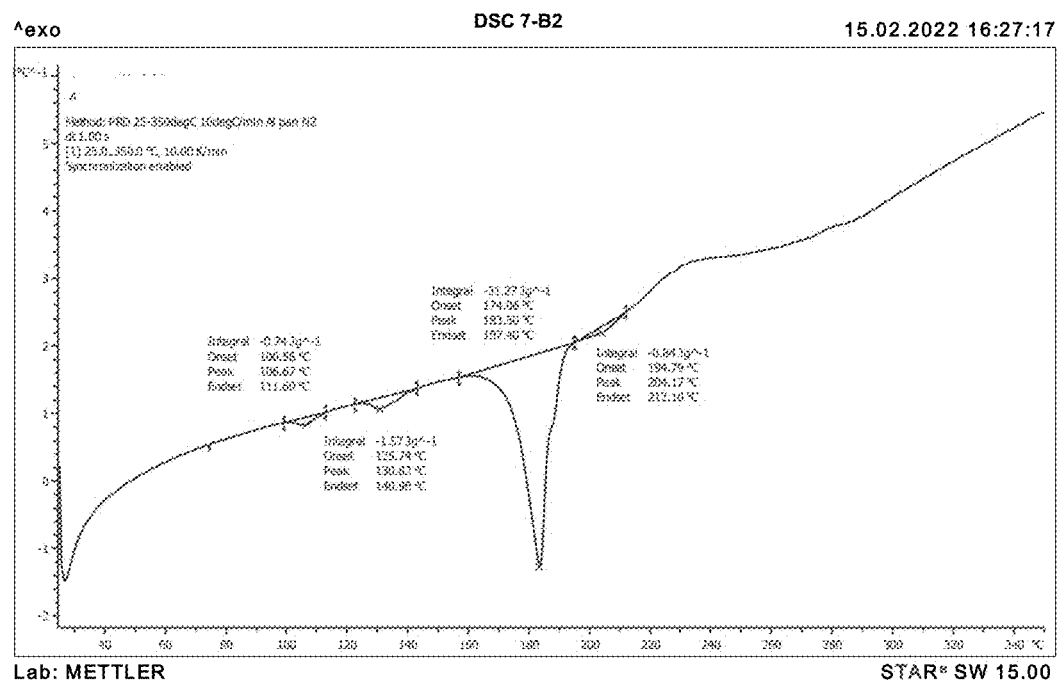

FIG. 316 depicts the DSC profile of 7-B2 (Experiment Reference 7-Sample Reference B2), analysis was acquired at a ramp rate of +10° C./minute.

Figure 317:
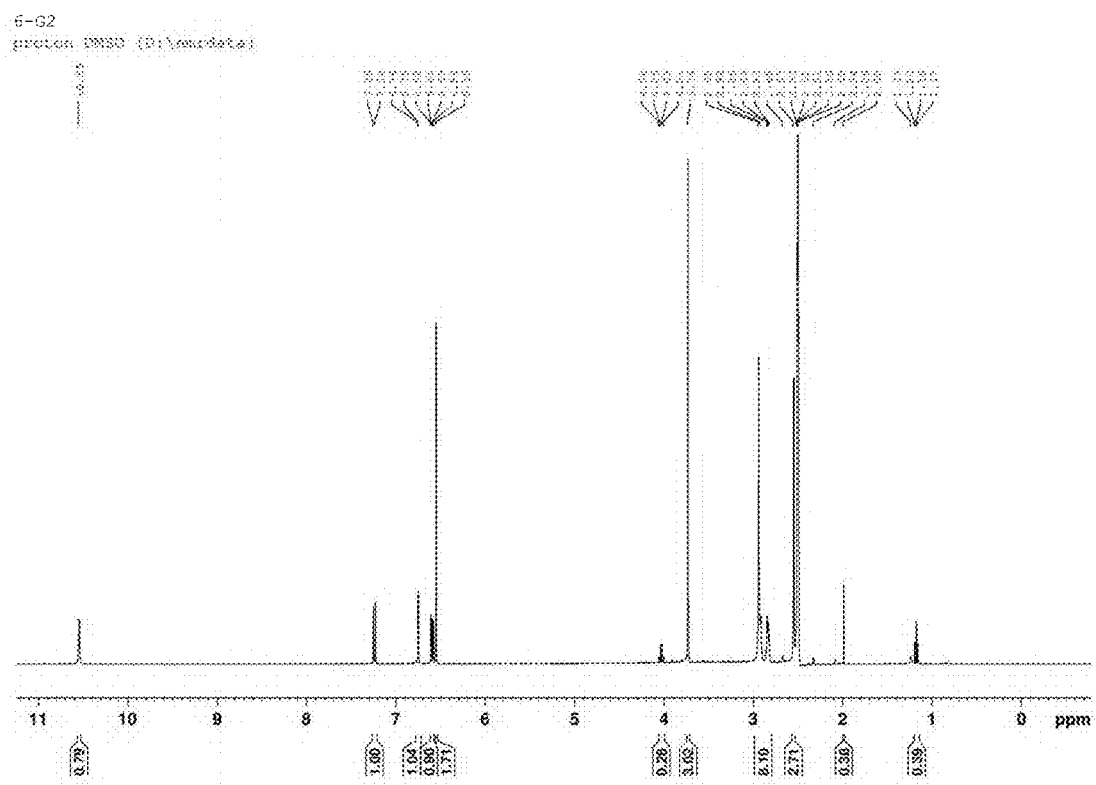

FIG. 317 depicts the $^1$H NMR spectrum of 6-G2 (Experiment Reference 6-Sample Reference G2) (suspended in ethyl acetate), analysis was acquired in DMSO-d6 and calibrated to the non-deuterated solvent residual at 2.50 ppm API to Fumaric acid, 1.0 to 1.0. Residual ethyl acetate (3.2% w/w).

Figure 319:
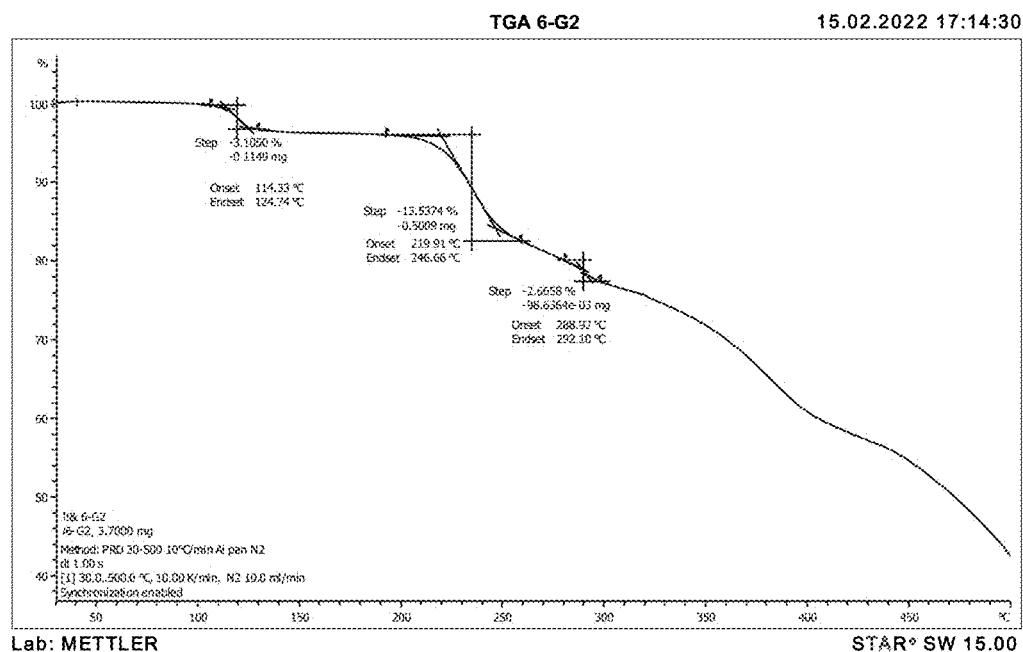

FIG. 319 depicts the TGA profile of 6-G2 (Experiment Reference 6-Sample Reference G2), analysis was acquired at a ramp rate of +10° C./minute.

Figure 320:
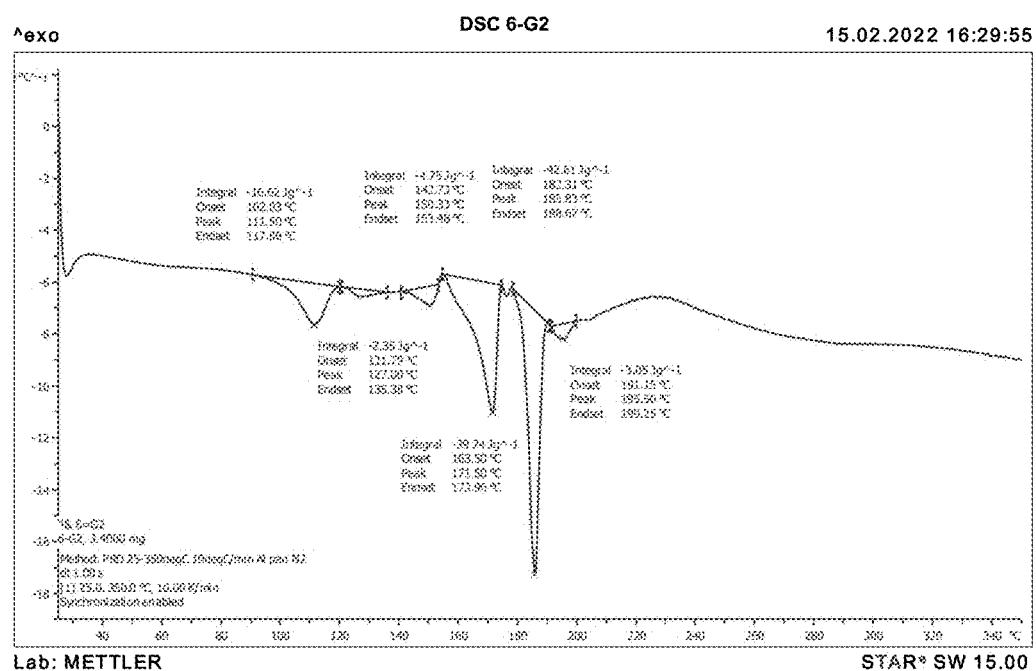

FIG. 320 depicts the DSC profile of 6-G2 (Experiment Reference 6-Sample Reference G2), analysis was acquired at a ramp rate of +10° C./minute.

Figure 321:
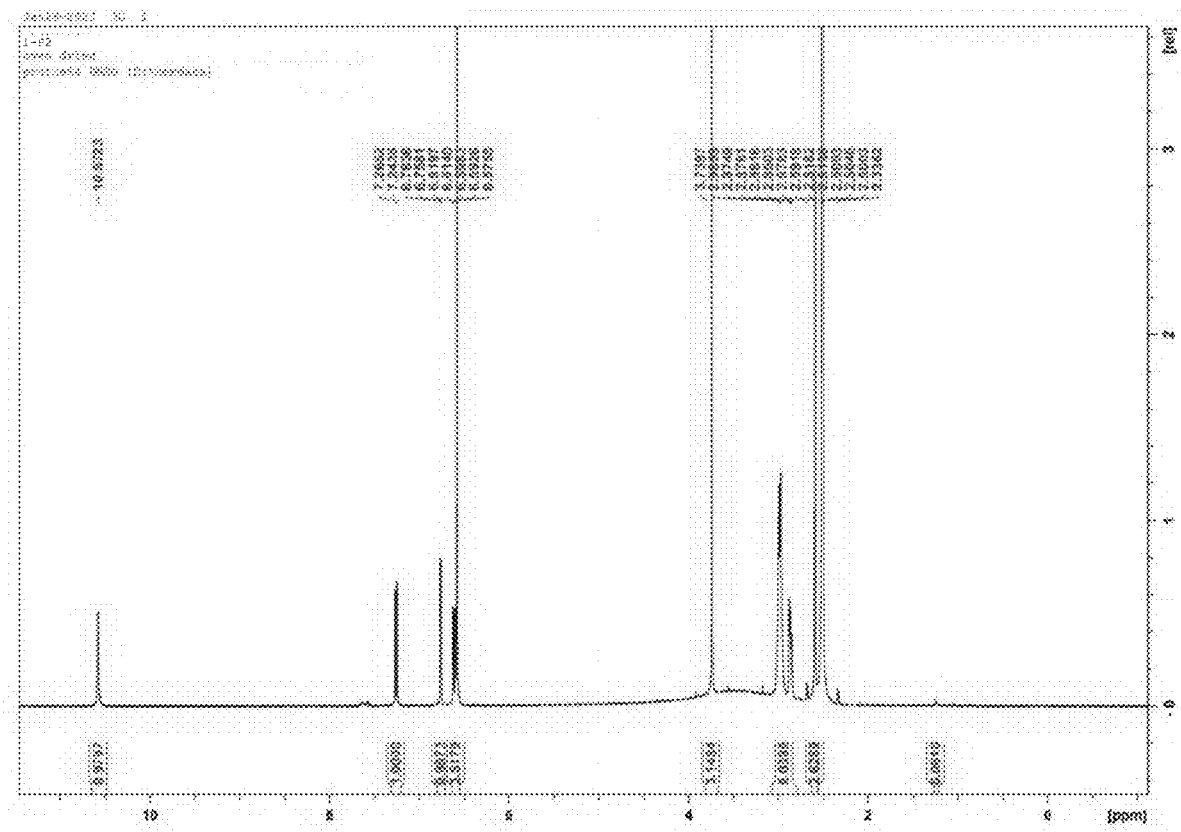

FIG. 321 depicts the $^1$H NMR spectrum of 1-P2 (Experiment Reference 1-Sample Reference P2) (crystallized from water, oven dried), analysis was acquired in DMSO-d6 and calibrated to the non-deuterated solvent residual at 2.50 ppm API to Fumaric acid, 1.0 to 1.0. Residual acetonitrile (0.2% w/w).

Figure 322:
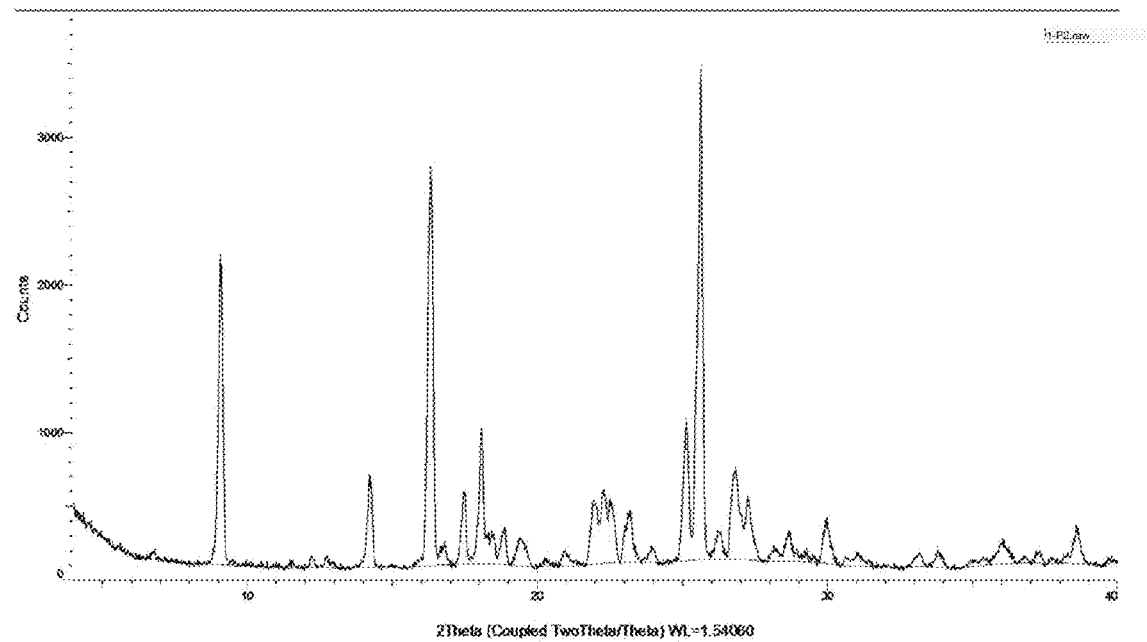

FIG. 322 depicts the XRPD profile of 1-P2 (Experiment Reference 1-Sample Reference P2).

Figure 323:
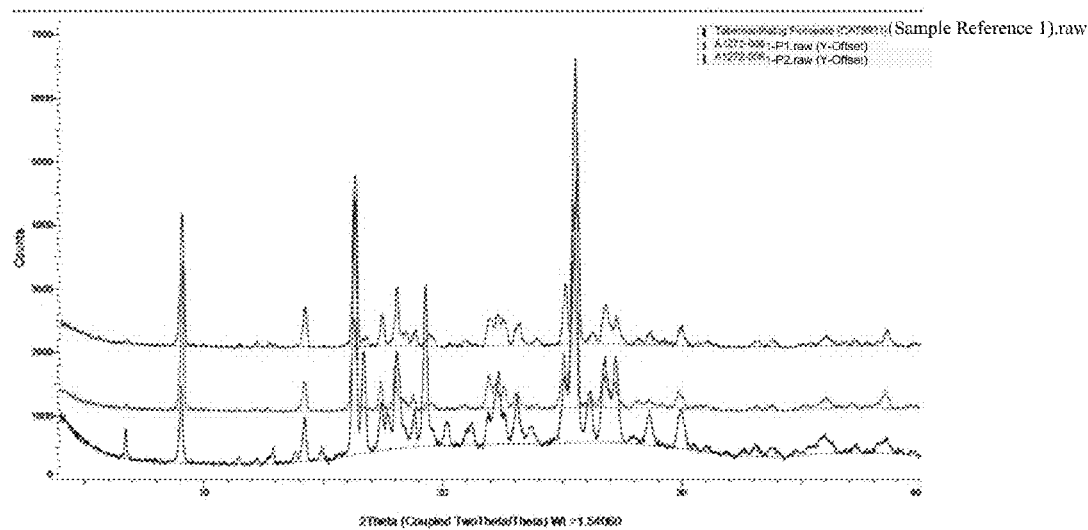

FIG. 323 depicts the XRPD overlay of, from bottom to top, the tabernanthalog fumarate salt (Sample Reference 1), 1-P1 (Experiment Reference 1-Sample Reference P1) (wet pellet) and 1-P2 (Experiment Reference 1-Sample Reference P2) (oven dried) [Key differences: 16.7°, 19.3°2θ; approx. isostructural].

Figure 324:
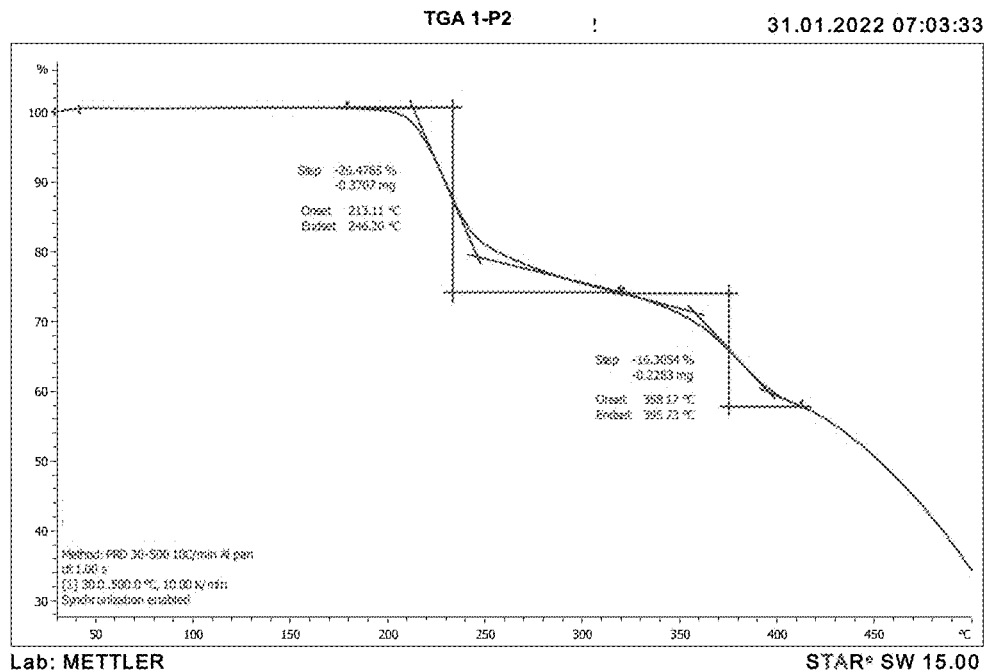

FIG. 324 depicts the TGA profile of 1-P2 (Experiment Reference 1-Sample Reference P2), analysis was acquired at a ramp rate of +10° C./minute (Approximately flat baseline, preceding melt, likely to be anhydrous form).

Figure 325:
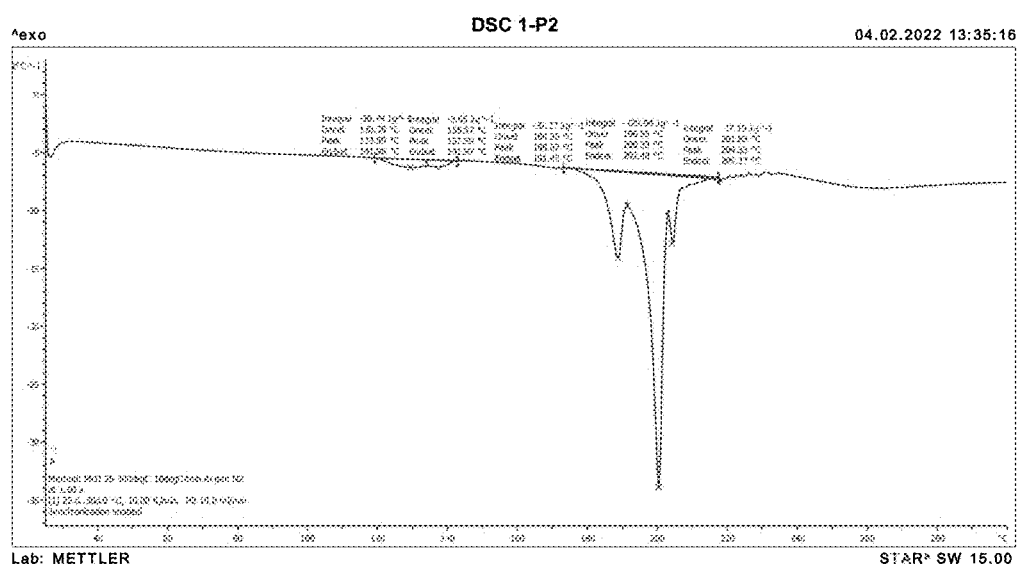

FIG. 325 depicts the DSC profile of 1-P2 (Experiment Reference 1-Sample Reference P2), analysis was acquired at a ramp rate of +10° C./minute.

Figure 326:
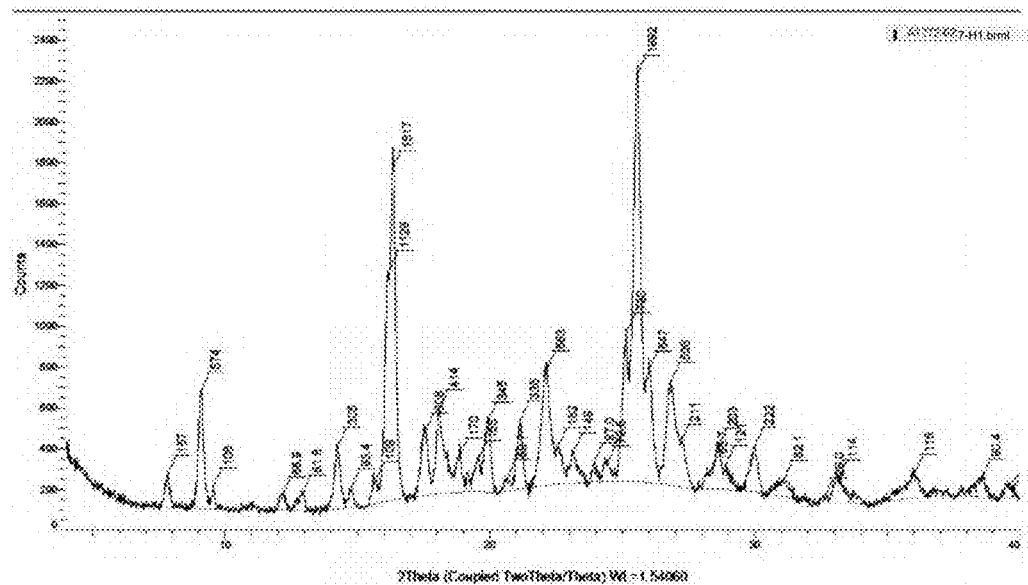

FIG. 326 depicts the XRPD profile of 7-H1 (Experiment Reference 7-Sample Reference H1).

Figure 327:
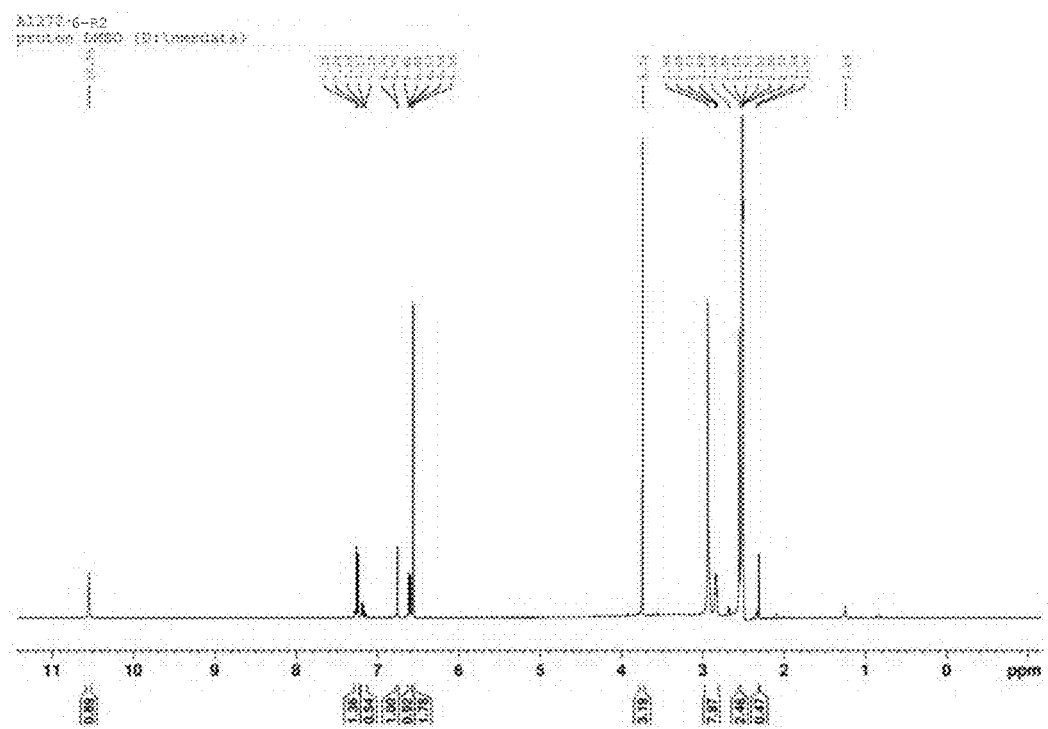

FIG. 327 depicts the $^1$H NMR spectrum of 6-R2 (Experiment Reference 6-Sample Reference R2) (suspended in toluene), analysis was acquired in DMSO-d6 and calibrated to the non-deuterated solvent residual at 2.50 ppm API to Fumaric acid, 1.0 to 1.0. Residual toluene (4.6% w/w).

Figure 329:
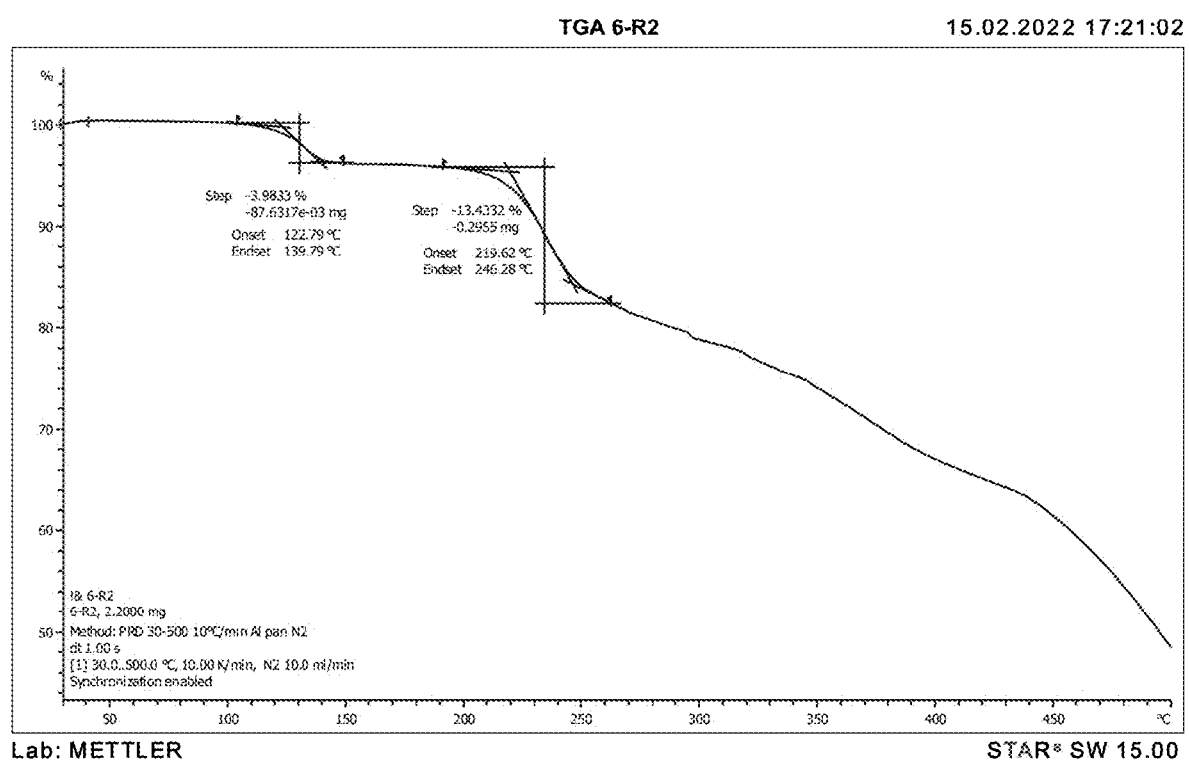

FIG. 329 depicts the TGA profile of 6-R2 (Experiment Reference 6-Sample Reference R2), analysis was acquired at a ramp rate of +10° C./minute.

Figure 330:
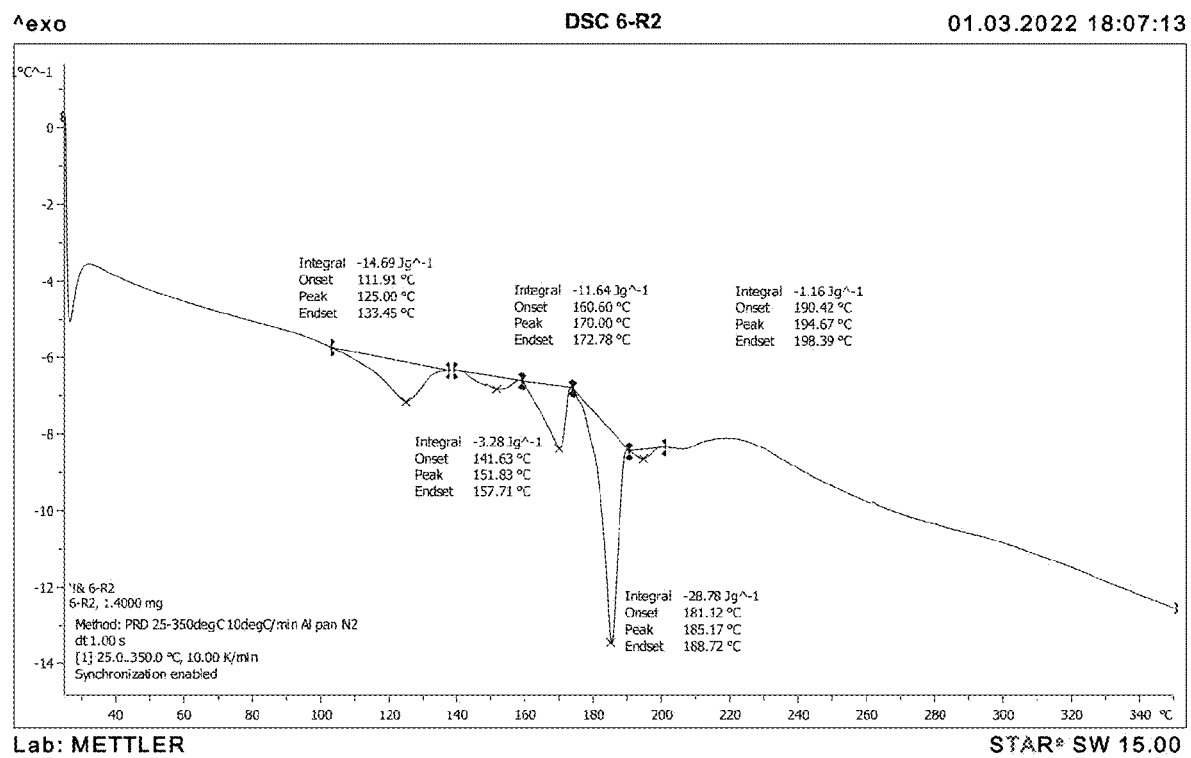

FIG. 330 depicts the DSC profile of 6-R2 (Experiment Reference 6-Sample Reference R2), analysis was acquired at a ramp rate of +10° C./minute.

Figure 331:
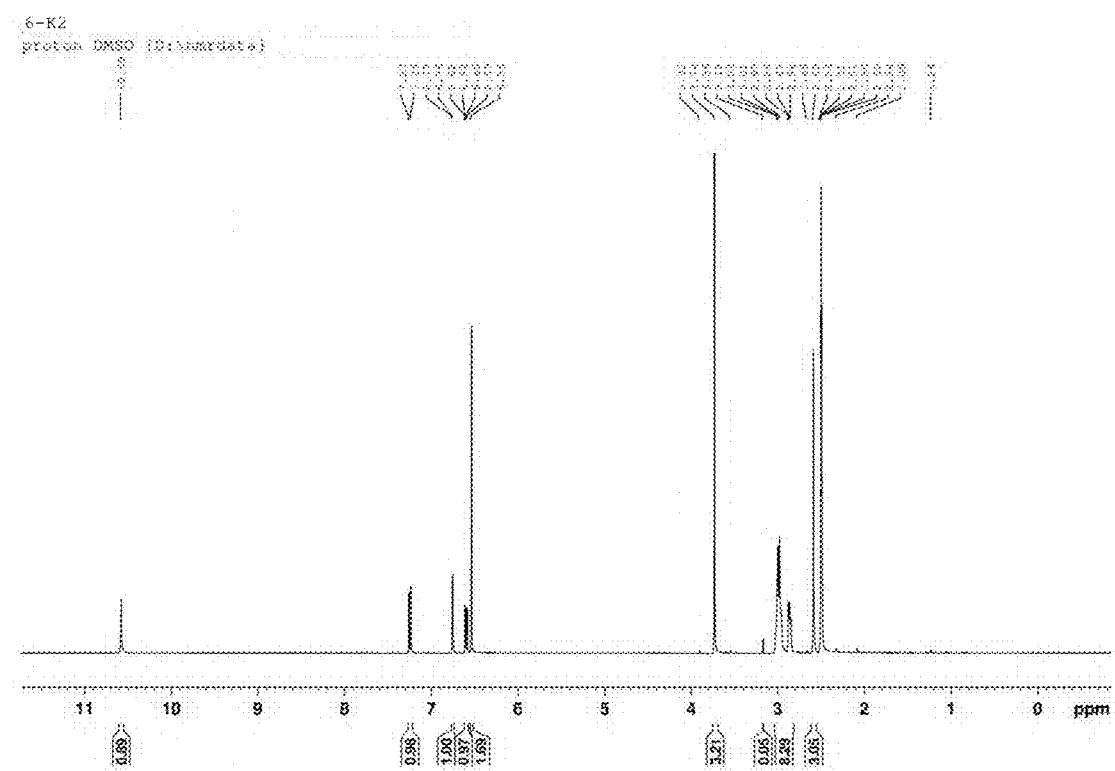

FIG. 331 depicts the $^1$H NMR spectrum of 6-K2 (Experiment Reference 6-Sample Reference K2) (suspended in methanol), analysis was acquired in DMSO-d6 and calibrated to the non-deuterated solvent residual at 2.50 ppm API to Fumaric acid, 1.0 to 1.0. Residual methanol (0.2% w/w).

Figure 333:
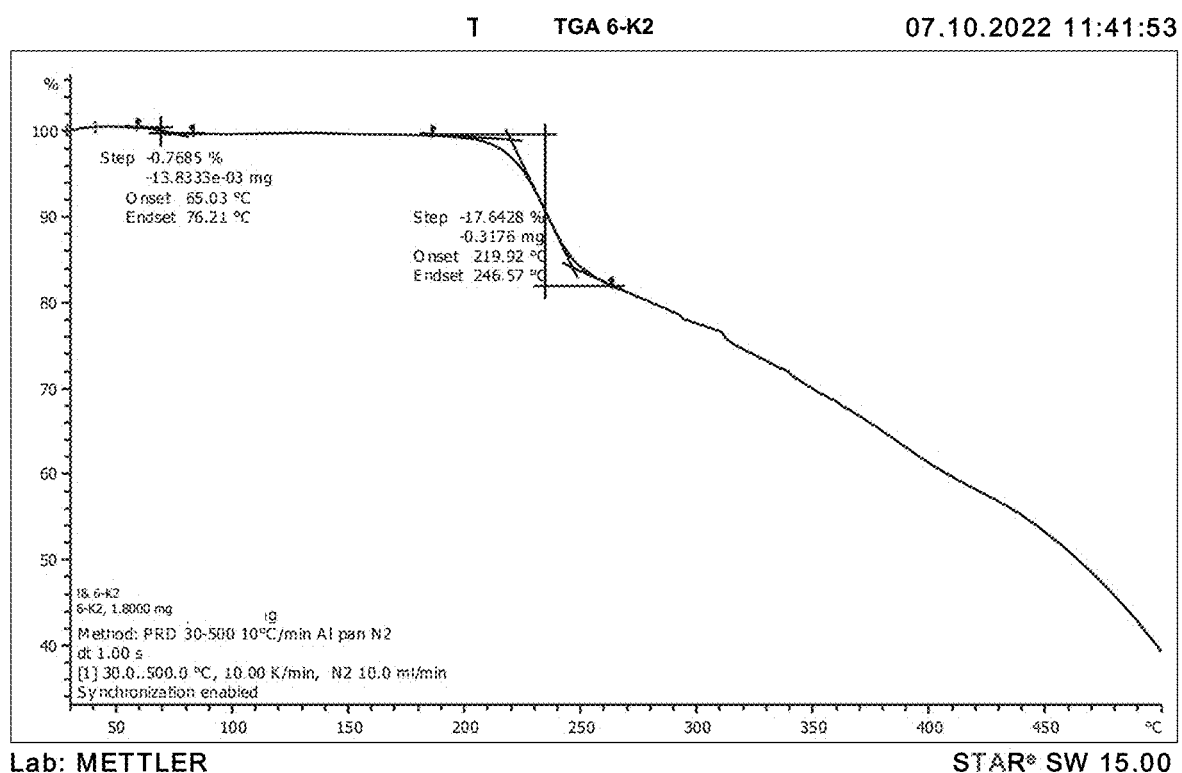

FIG. 333 depicts the TGA profiles of 6-K2 (Experiment Reference 6-Sample Reference K2), analysis was acquired at a ramp rate of +10° C./minute.

Figure 334:
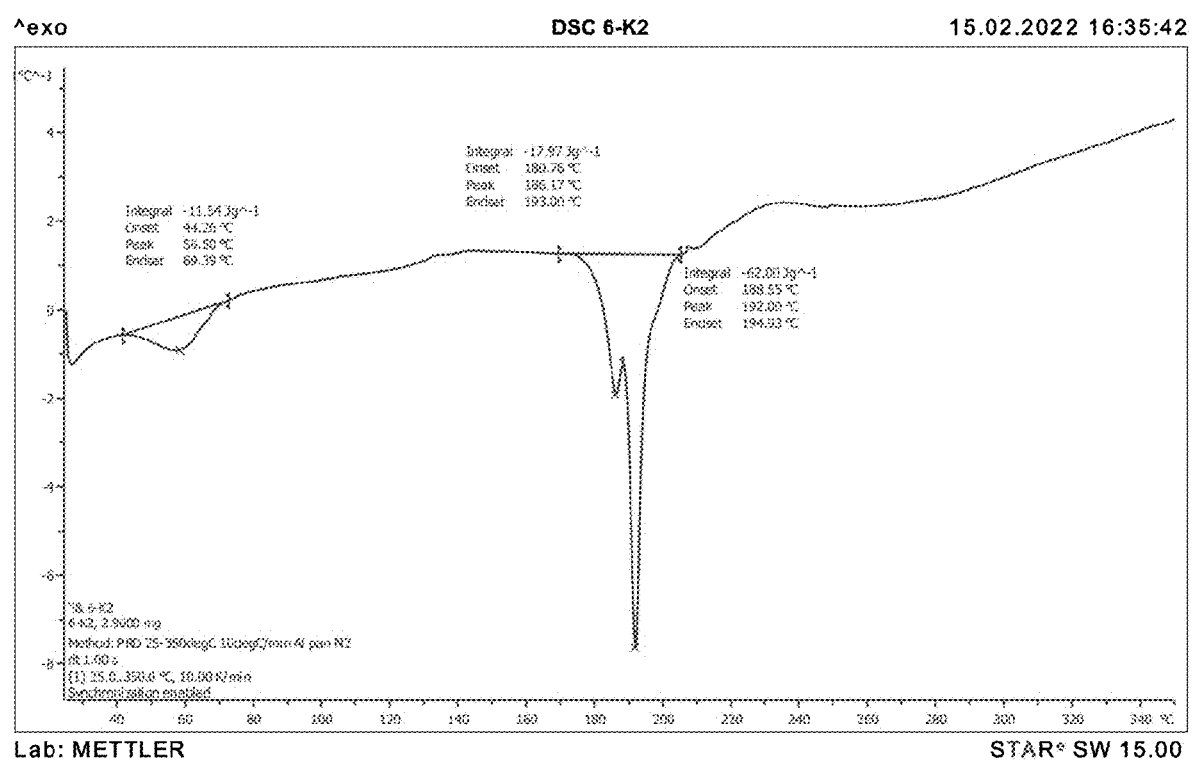

FIG. 334 depicts the DSC profile of 6-K2 (Experiment Reference 6-Sample Reference K2), analysis was acquired at a ramp rate of +10° C./minute.

Figure 335:
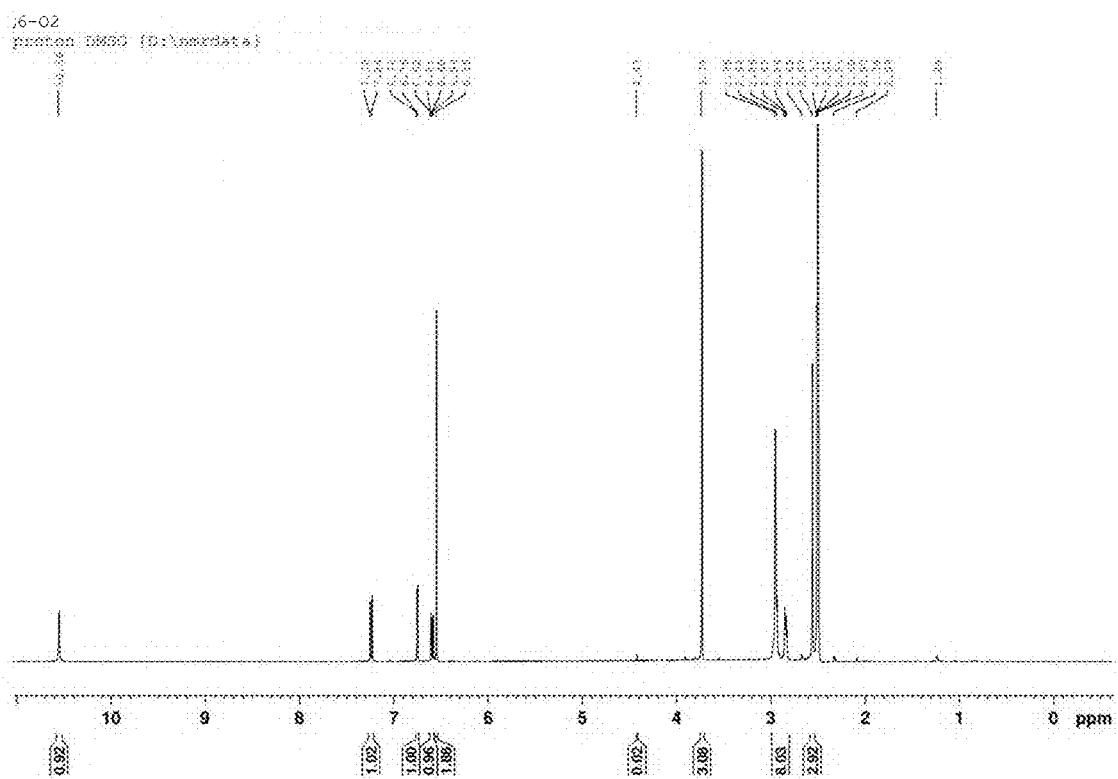

FIG. 335 depicts the $^1$H NMR spectrum of 6-O2 (Experiment Reference 6-Sample Reference O2) (suspended in nitromethane), analysis was acquired in DMSO-d6 and calibrated to the non-deuterated solvent residual at 2.50 ppm. API to Fumaric acid, 1.0 to 1.0. Residual nitromethane (0.2% w/w).

Figure 337:
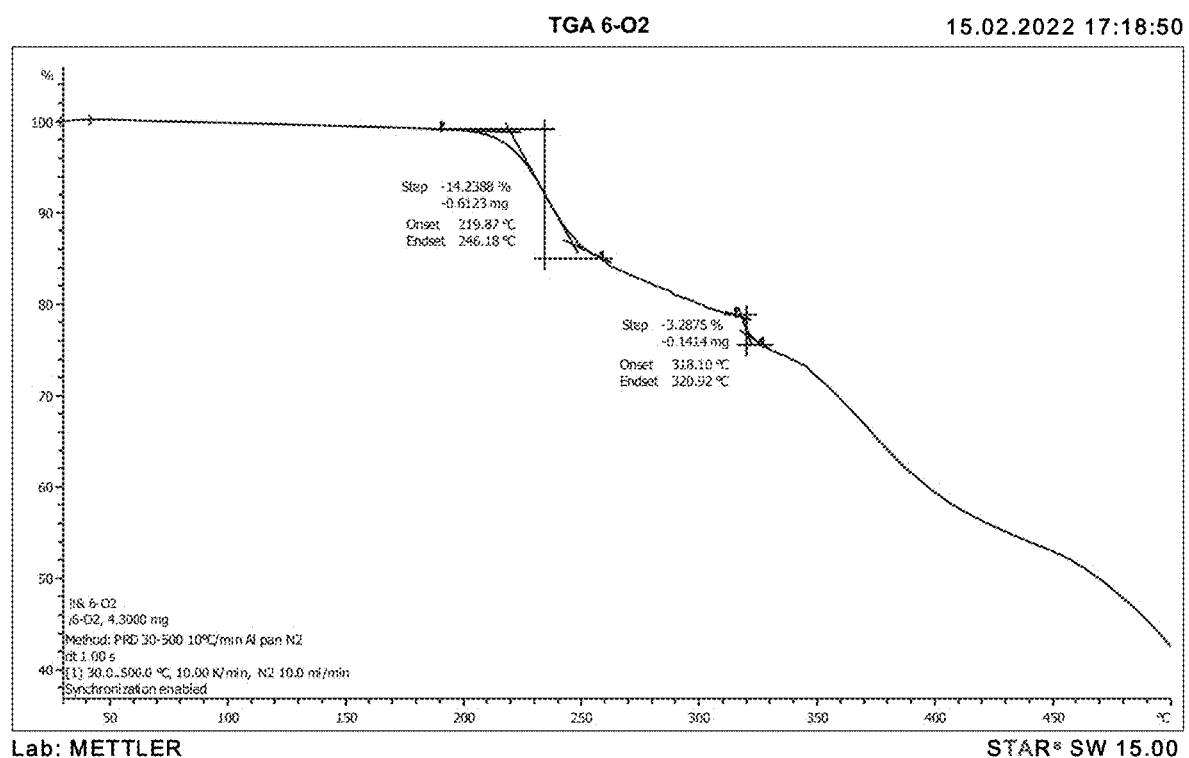

FIG. 337 depicts the TGA profile of 6-O2 (Experiment Reference 6-Sample Reference O2), analysis was acquired at a ramp rate of +10° C./minute.

Figure 338:
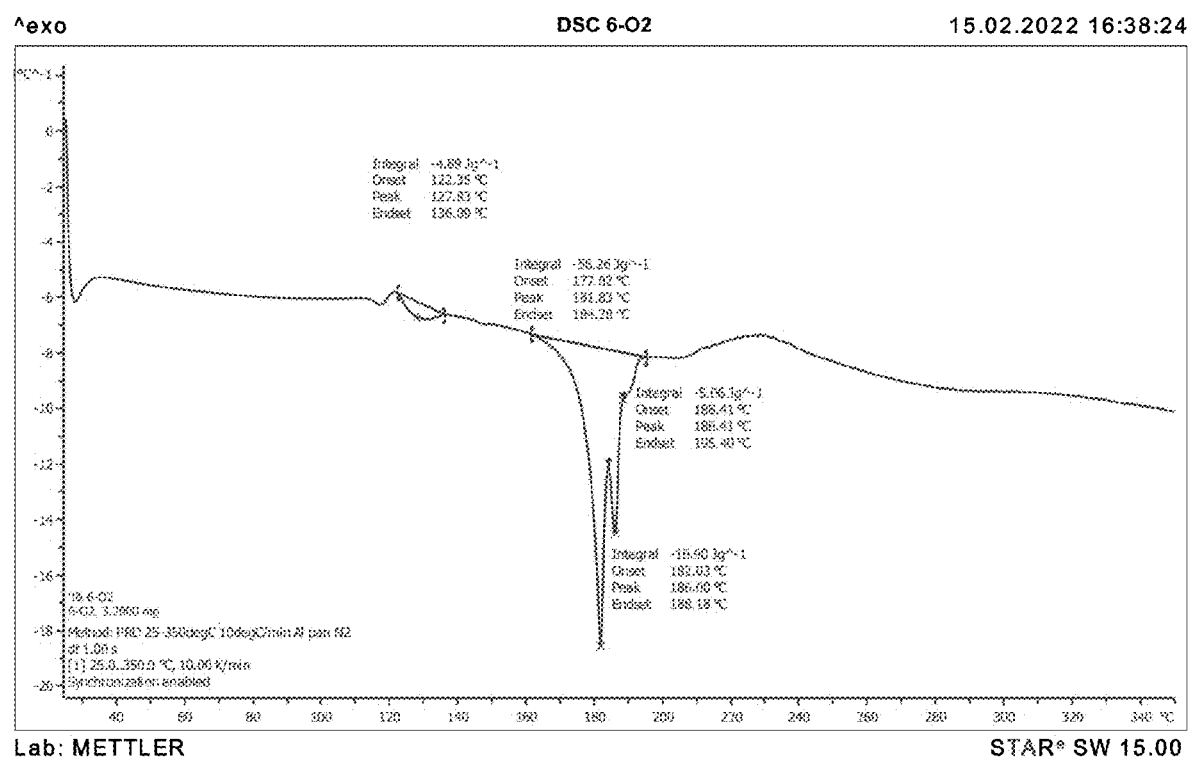

FIG. 338 depicts the DSC profile of 6-O2 (Experiment Reference 6-Sample Reference O2), analysis was acquired at a ramp rate of +10° C./minute.

Figure 344:
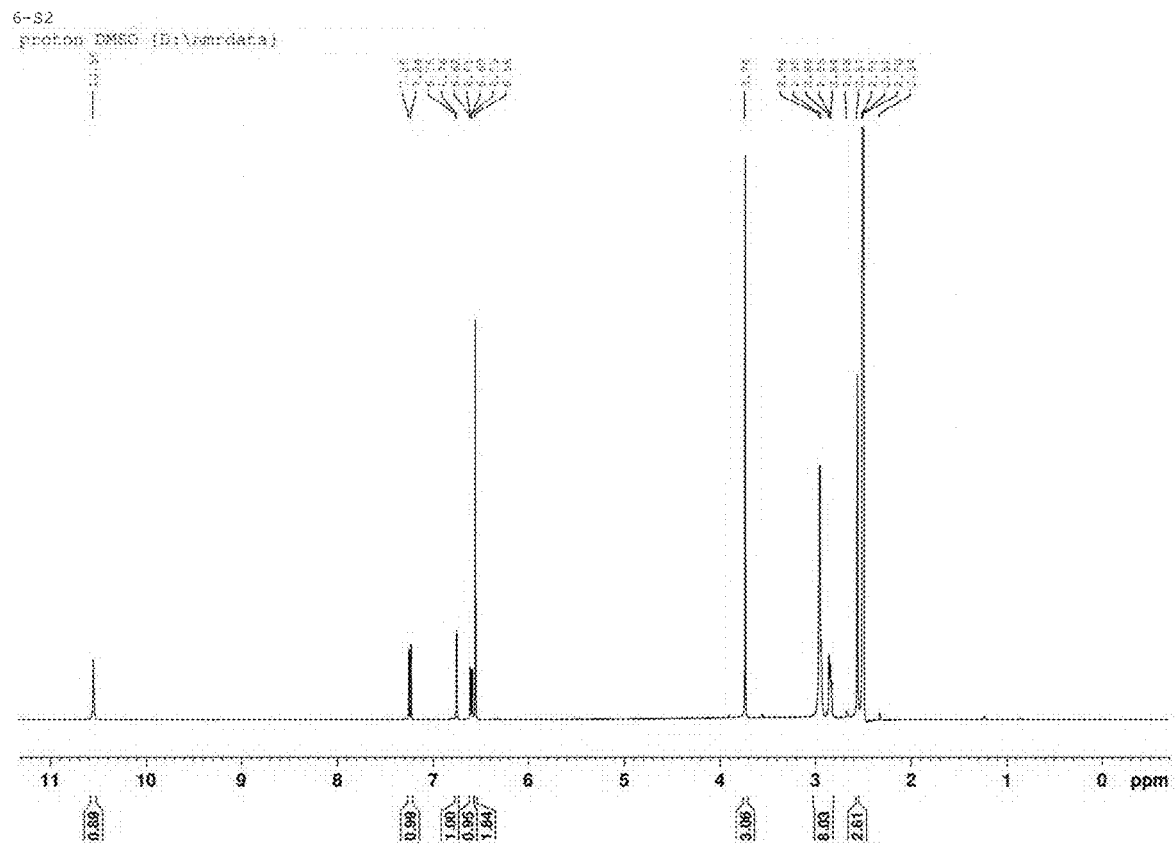

FIG. 344 depicts the $^1$H NMR spectrum of 6-S2 (Experiment Reference 6-Sample Reference S2) (suspended in water), analysis was acquired in DMSO-d6 and calibrated to the non-deuterated solvent residual at 2.50 ppm API to Fumaric acid, 1.0 to 1.0, and was anhydrous and solvent free. Small decrease in the impurity burden was observed in aryl and aliphatic regions, post crystallization.

Figure 345:
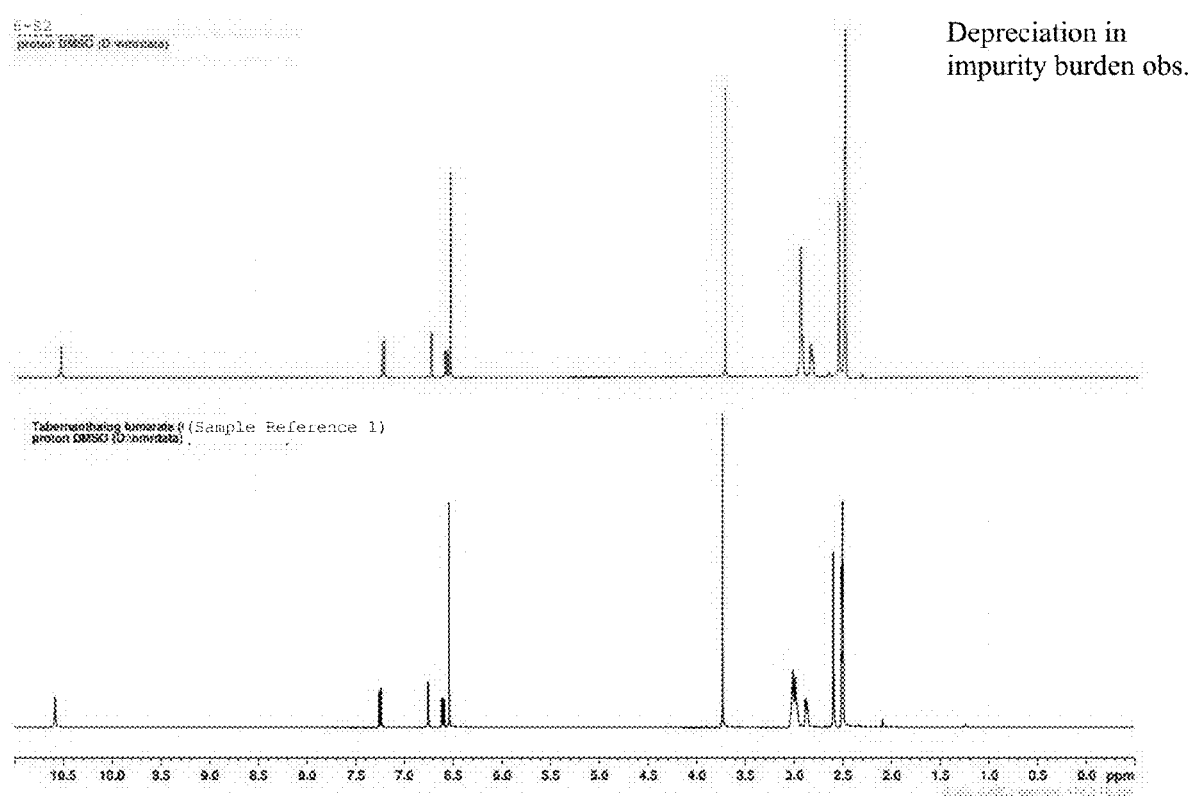

FIG. 345 depicts the $^1$H NMR spectra overlay of 6-S2 (Experiment Reference 6-Sample Reference S2) (suspended in water, top) and supplied tabernanthalog monofumarate salt (Sample Reference 1, bottom), analysis was acquired in DMSO-d6 and calibrated to the non-deuterated solvent residual at 2.50 ppm.

Figure 346A:
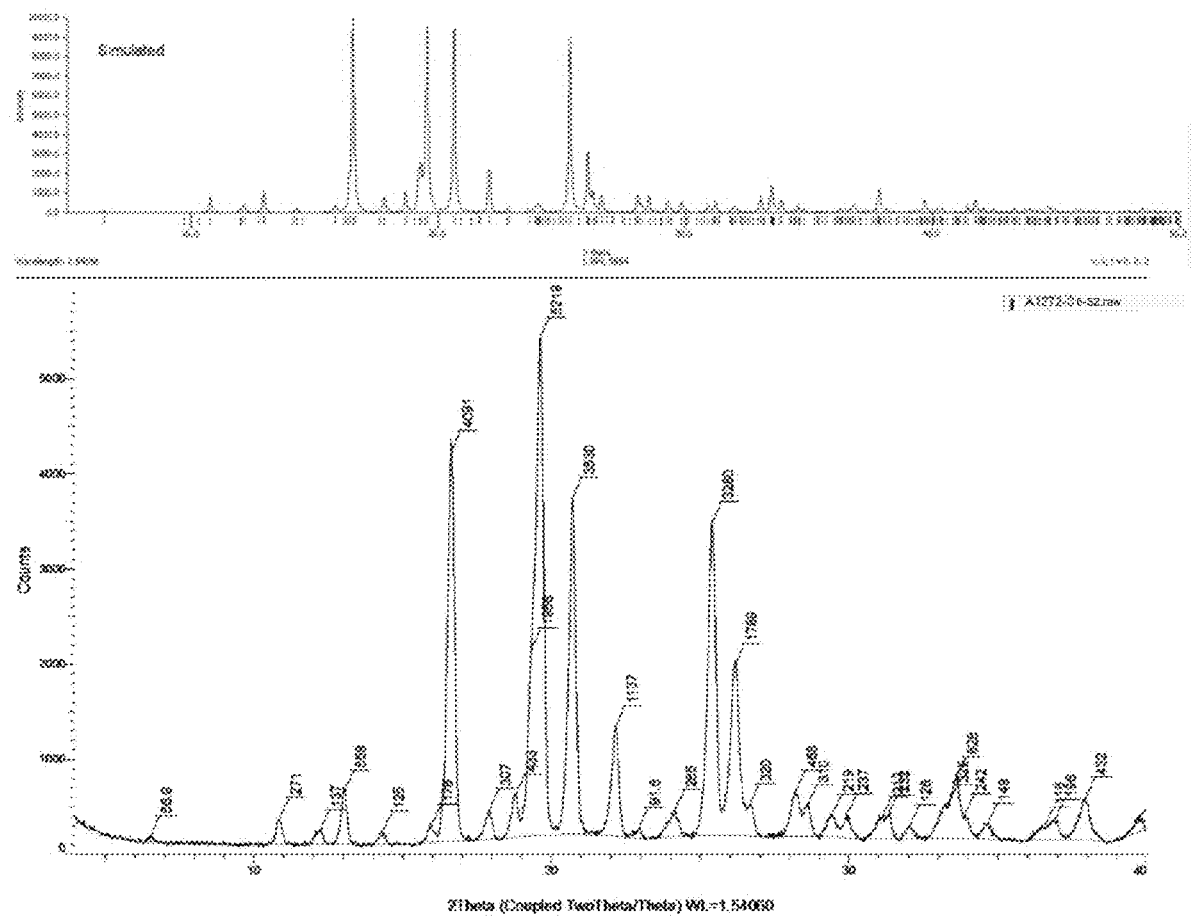

FIG. 346(A) depicts the overlay of XRPD profiles of a calculated powder pattern for tabernanthalog monofumarate, Pattern #6a, Form A (top) and 6-S2 (bottom).

Figure 346B:
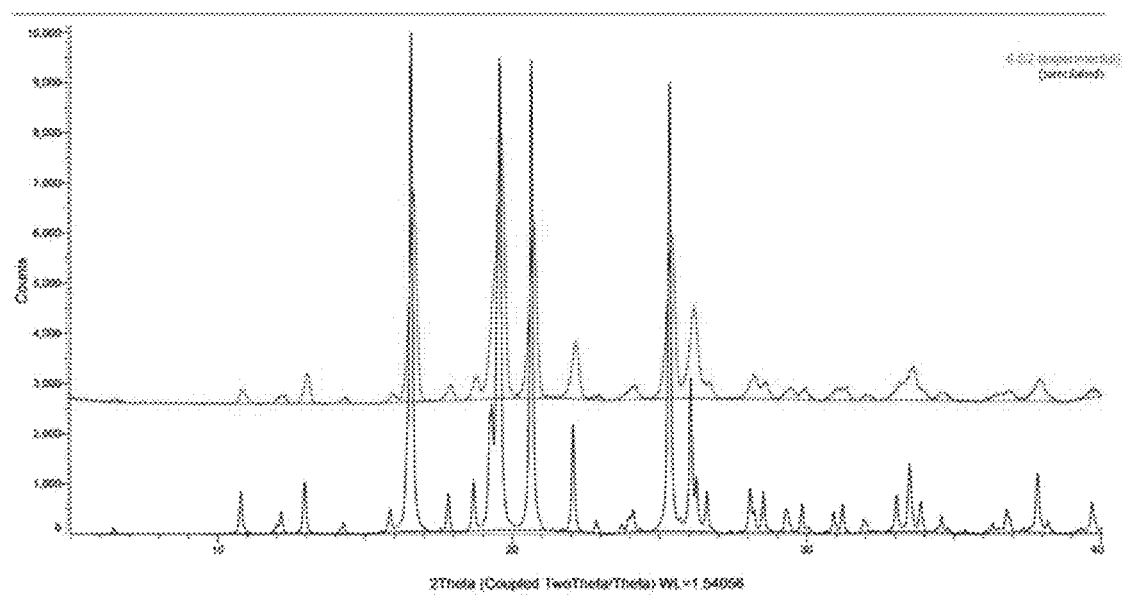

FIG. 346(B) depicts the overlay of experimental and simulated patterns of tabernanthalog monofumarate (Pattern #6a, Form A).

Figure 347:
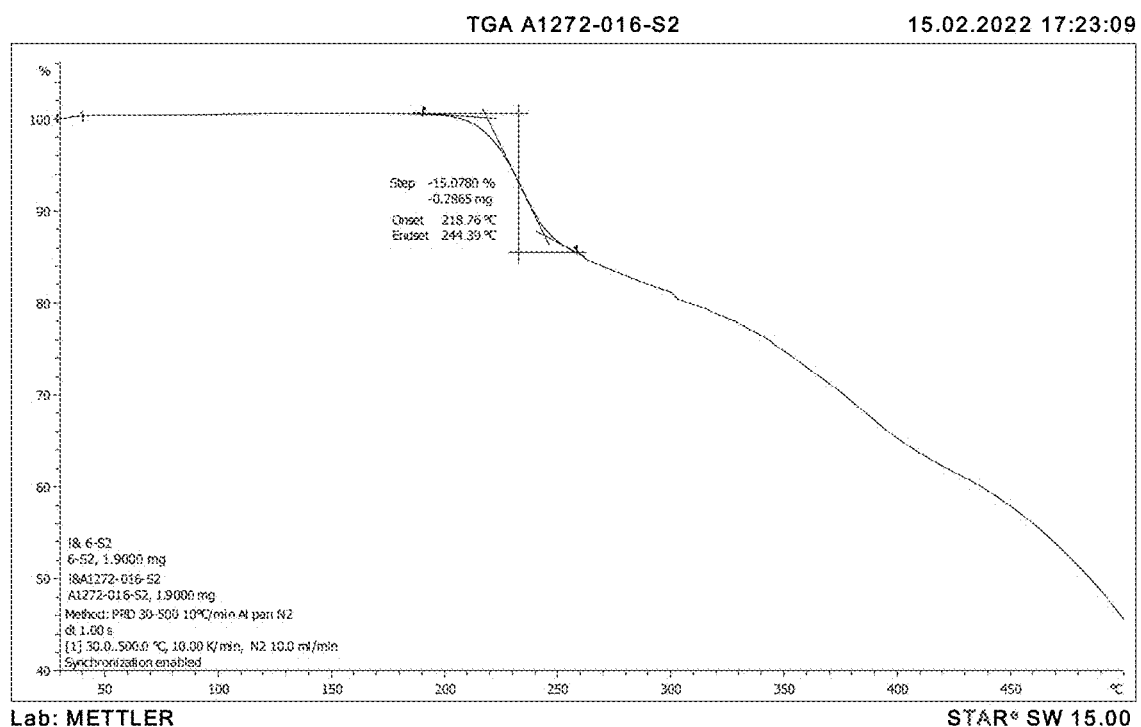

FIG. 347 depicts the TGA profile of 6-S2 (Experiment Reference 6-Sample Reference S2), analysis was acquired at a ramp rate of +10° C./minute.

Figure 348:
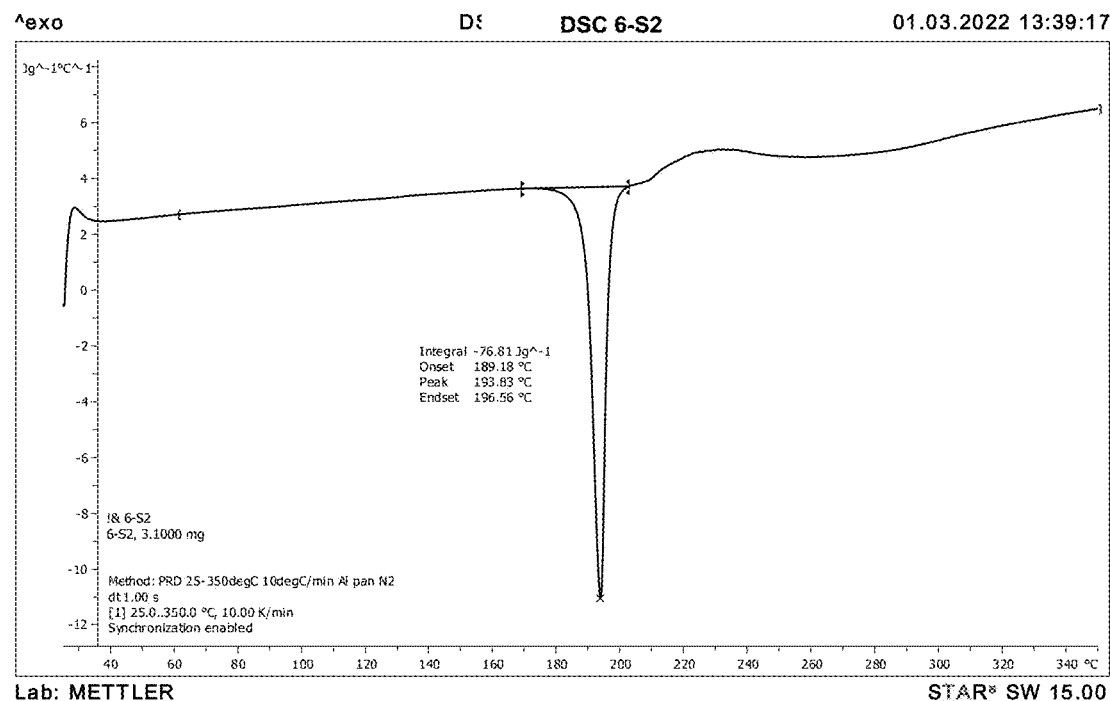

FIG. 348 depicts the DSC profile of 6-S2 (Experiment Reference 6-Sample Reference S2), analysis was acquired at a ramp rate of +10° C./minute.

Figure 349:
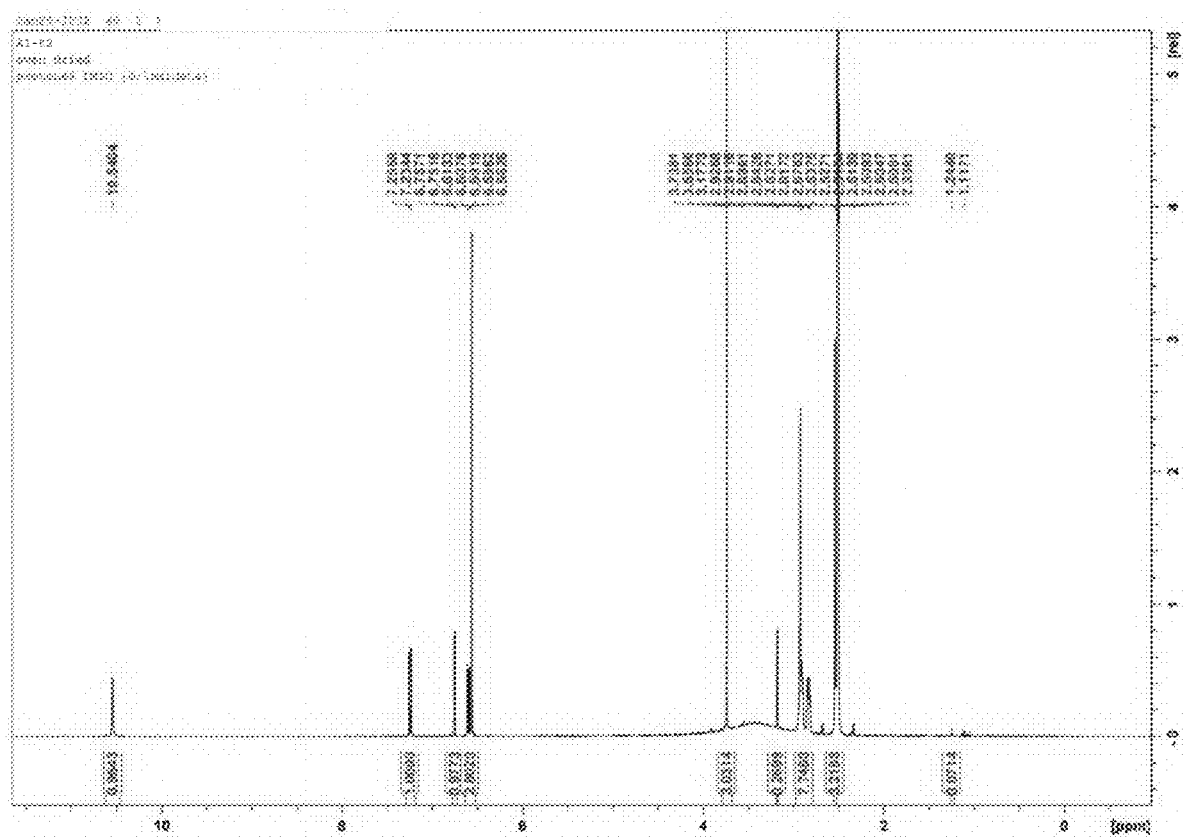

FIG. 349 depicts the $^1$H NMR spectrum of 1-K2 (Experiment Reference 1-Sample Reference K2) (crystallized from methanol), analysis was acquired in DMSO-d6 and calibrated to the non-deuterated solvent residual at 2.50 ppm API to Fumaric acid, 1.0 to 1.0. Specimen contained 0.7% w/w methanol, (th. solvate calc., 8.5% w/w). Residual acetonitrile (0.3% w/w).

Figure 350:
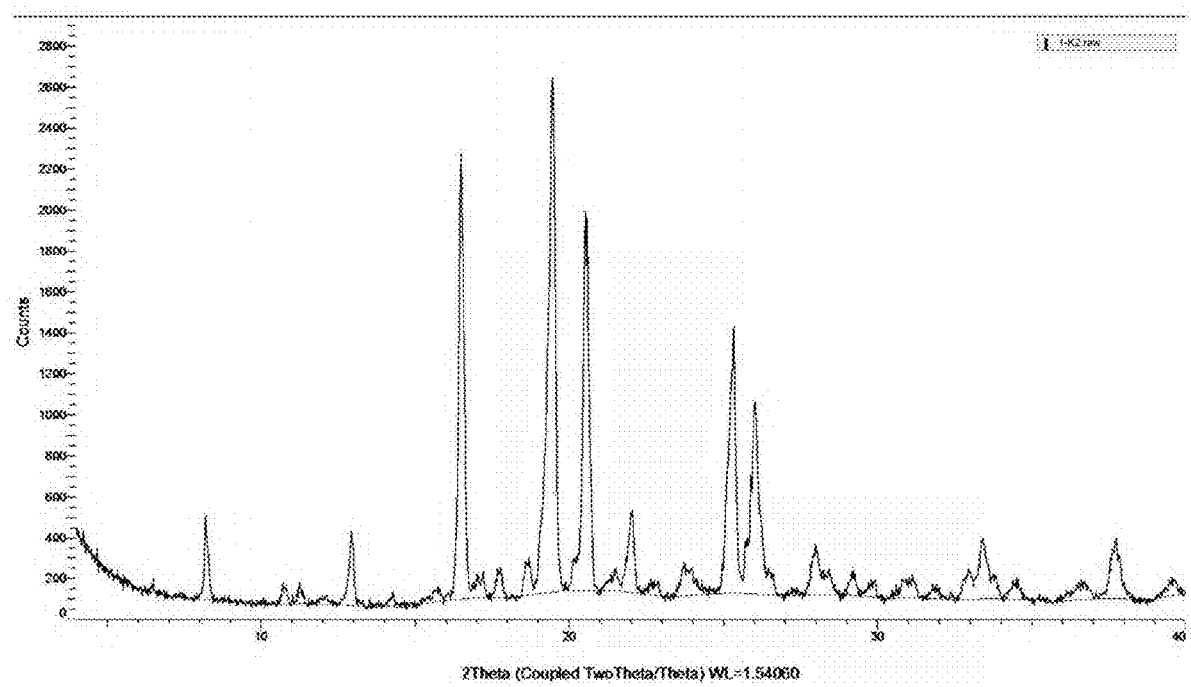

FIG. 350 depicts the XRPD profile of 1-K2 (Experiment Reference 1-Sample Reference K2) (oven dried) [Form A (Isostructural+reflections 8.2°, 11.4° 2θ].

Figure 351:
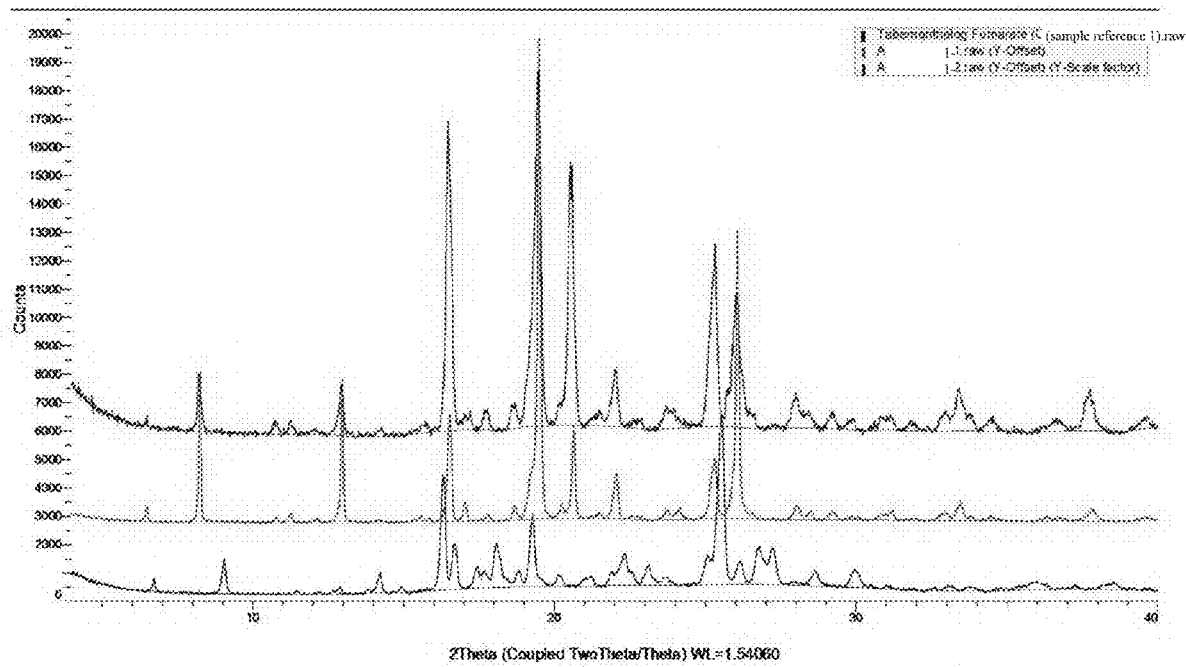

FIG. 351 depicts the XRPD overlay of, from bottom to top, the tabernanthalog monofumarate salt (Sample Reference 1), 1-K1 (Experiment Reference 1-Sample Reference K1) (wet pellet) and 1-K2 (Experiment Reference 1-Sample Reference K2) (oven dried). Key differences. 8.2°, 13.0°, 16.6°, 19.5°, 20.7°, 25.3°, 26.0° 2θ.

Figure 352:
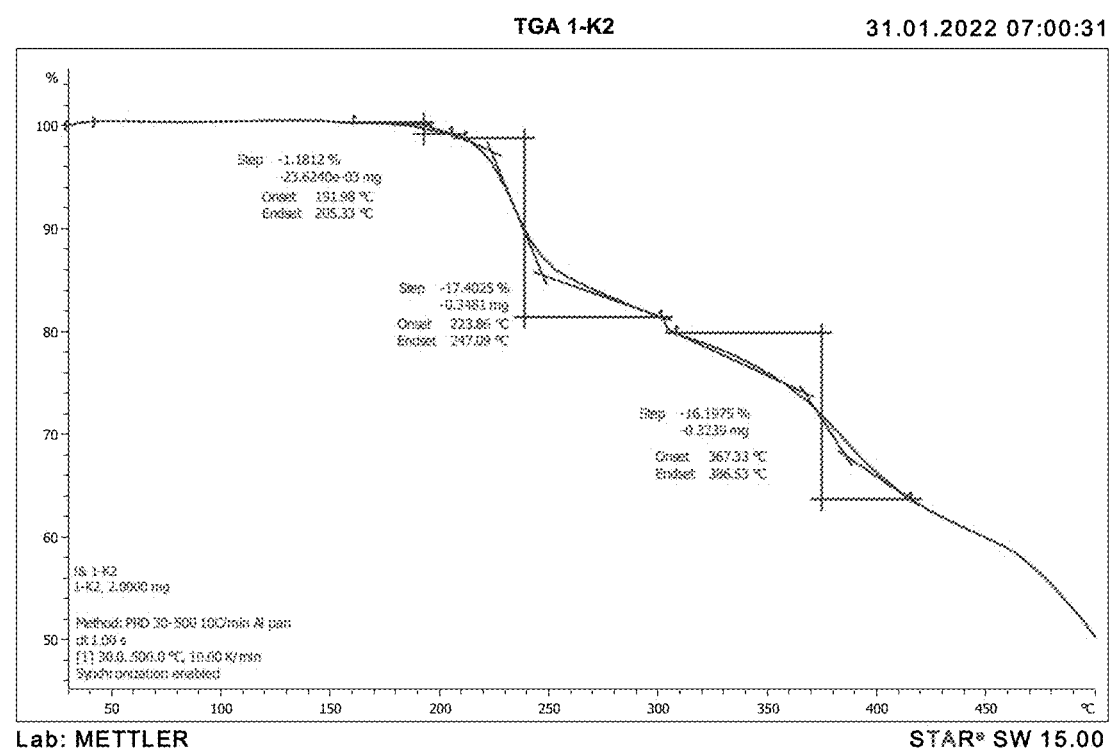

FIG. 352 depicts the TGA profile of 1-K2 (Experiment Reference 1-Sample Reference K2), analysis was acquired at a ramp rate of +10° C./minute (Flat baseline (anhydrous)).

Figure 353:
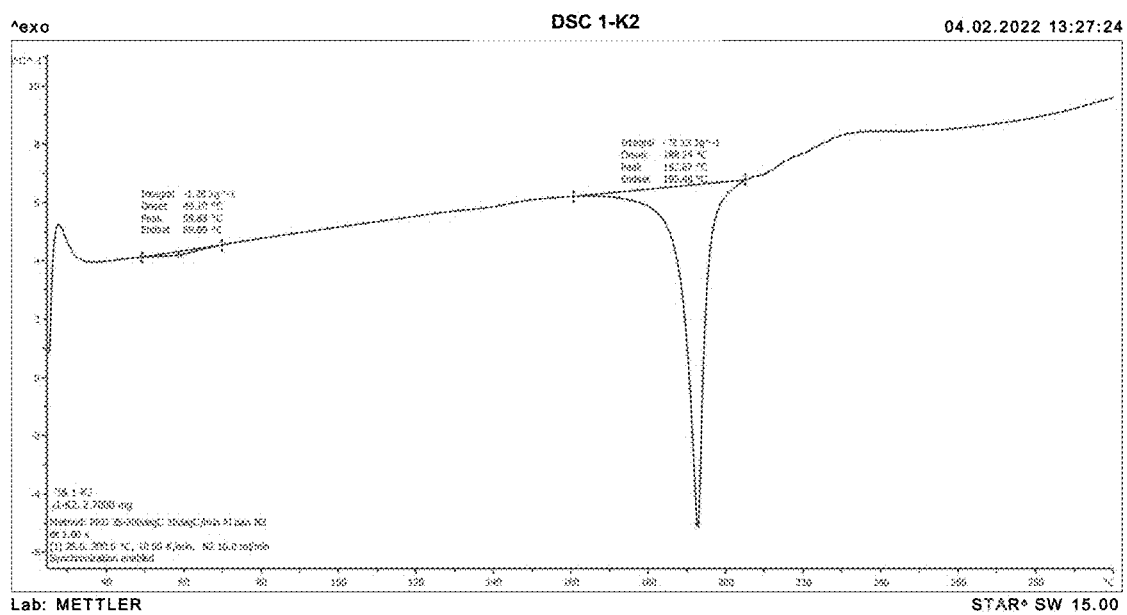

FIG. 353 depicts the DSC profile of 1-K2 (Experiment Reference 1-Sample Reference K2), analysis was acquired at a ramp rate of +10° C./minute.

Figure 354:
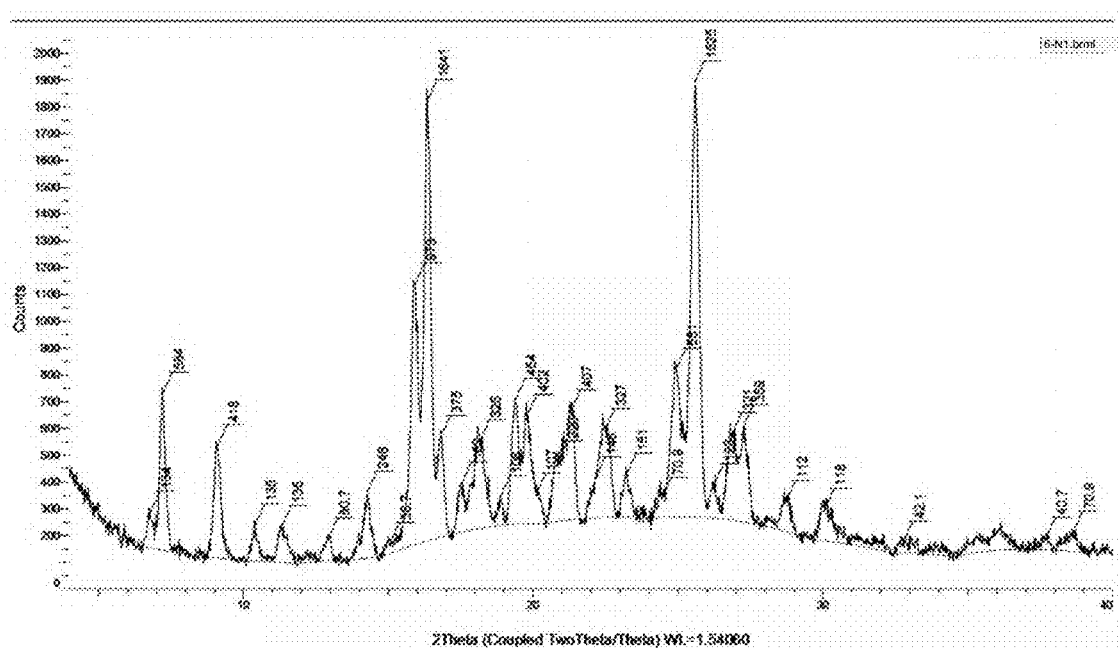

FIG. 354 depicts the XRPD profile of 6-N1 (Experiment Reference 6-Sample Reference N1) (wet pellet). 6-N1 converted to Pattern #1 upon oven-drying (6-N2) (Experiment Reference 6-Sample Reference N2).

Figure 355:
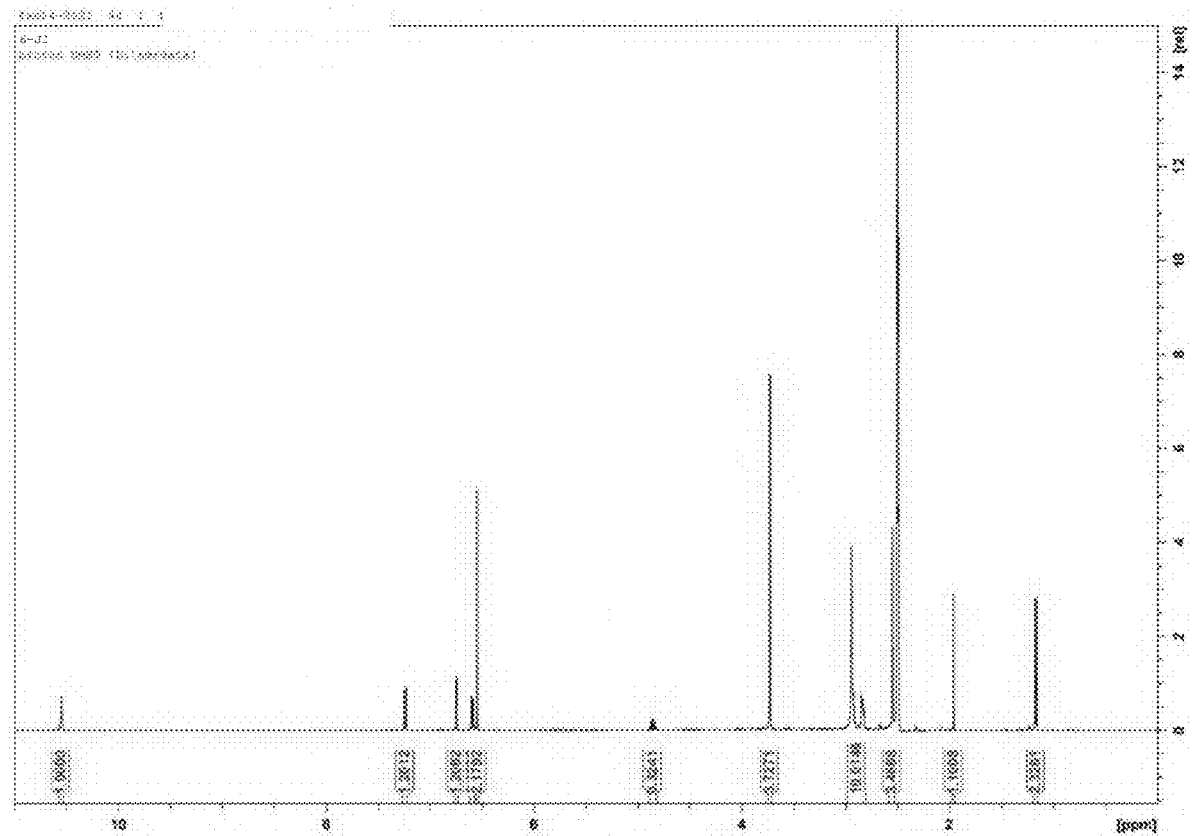

FIG. 355 depicts the $^1$H NMR spectrum of (6-J2) (Experiment Reference 6-Sample Reference J2) (suspended in isopropyl acetate), analysis was acquired in DMSO-d6 and calibrated to the non-deuterated solvent residual at 2.50 ppm API to Fumaric acid, 1.0 to 1.0. Residual isopropyl acetate 10.0% w/w. (th. solvate calc., 22.8% w/w).

Figure 357:
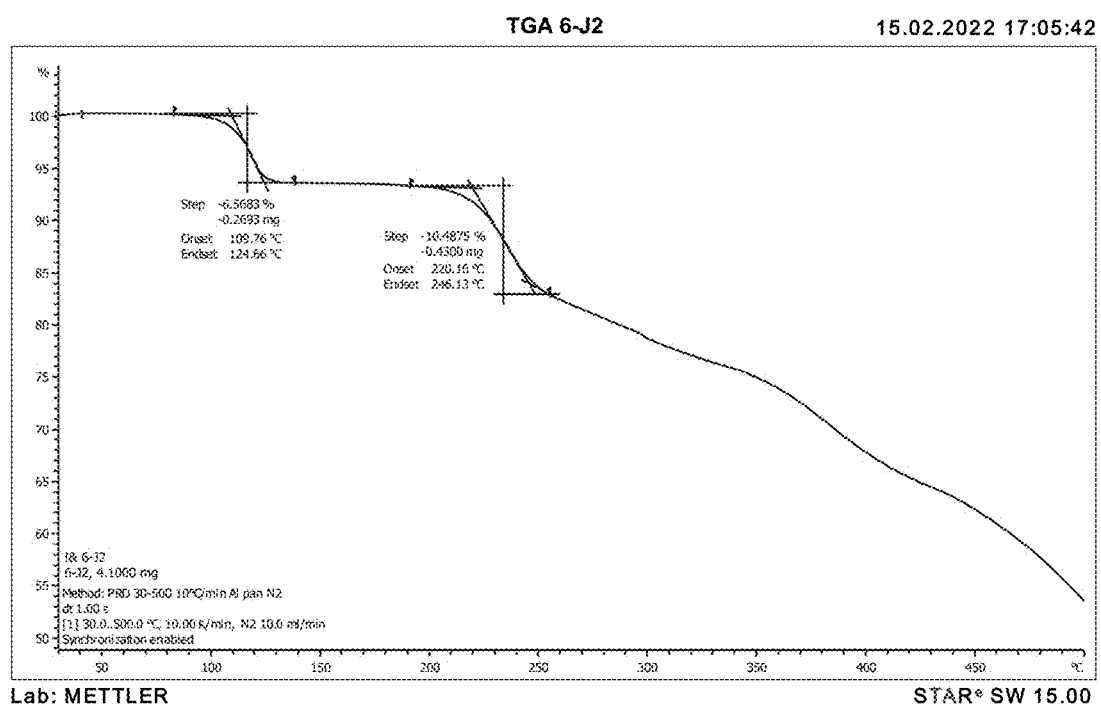

FIG. 357 depicts the TGA profiles of 6-J2 (Experiment Reference 6-Sample Reference J2), analysis was acquired at a ramp rate of +10° C./minute.

Figure 358:
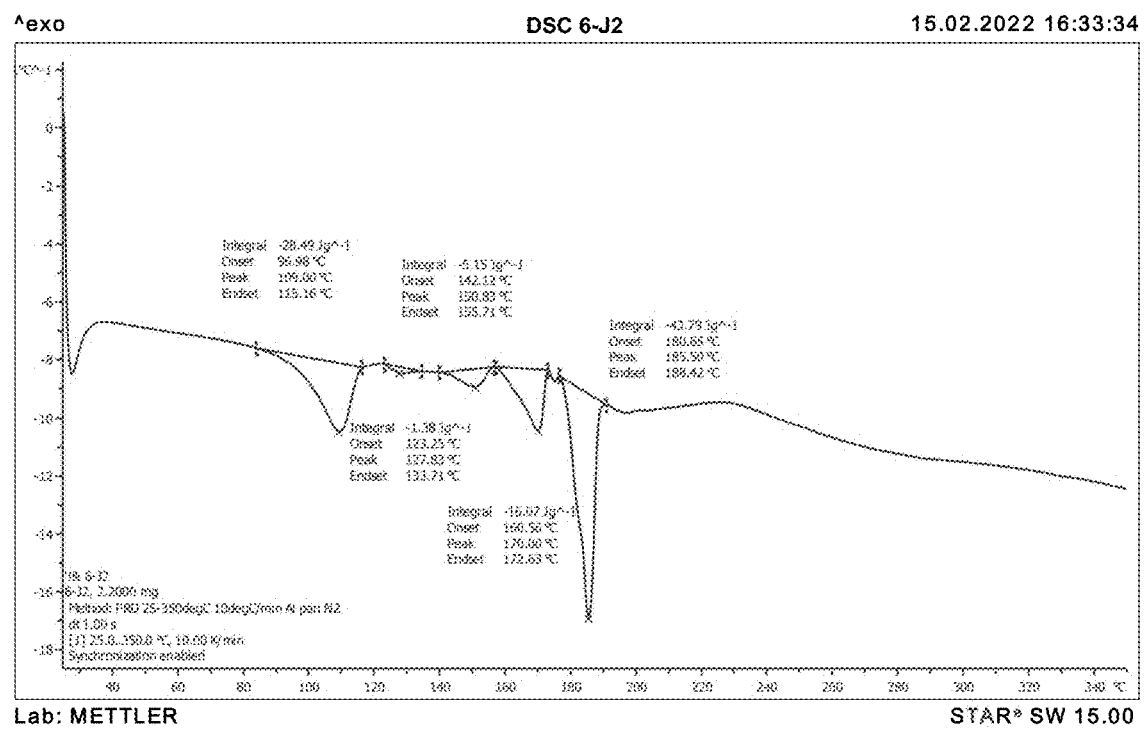

FIG. 358 depicts the DSC profile of 6-J2 (Experiment Reference 6-Sample Reference J2), analysis was acquired at a ramp rate of +10° C./minute.

Figure 359:
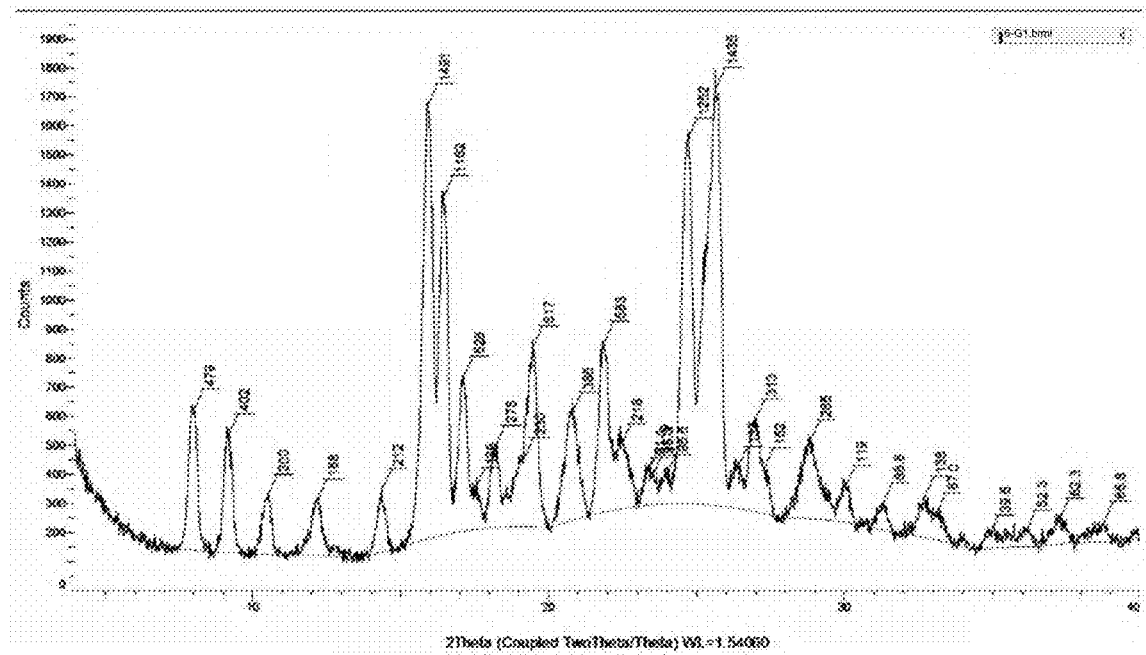
Figure 360:
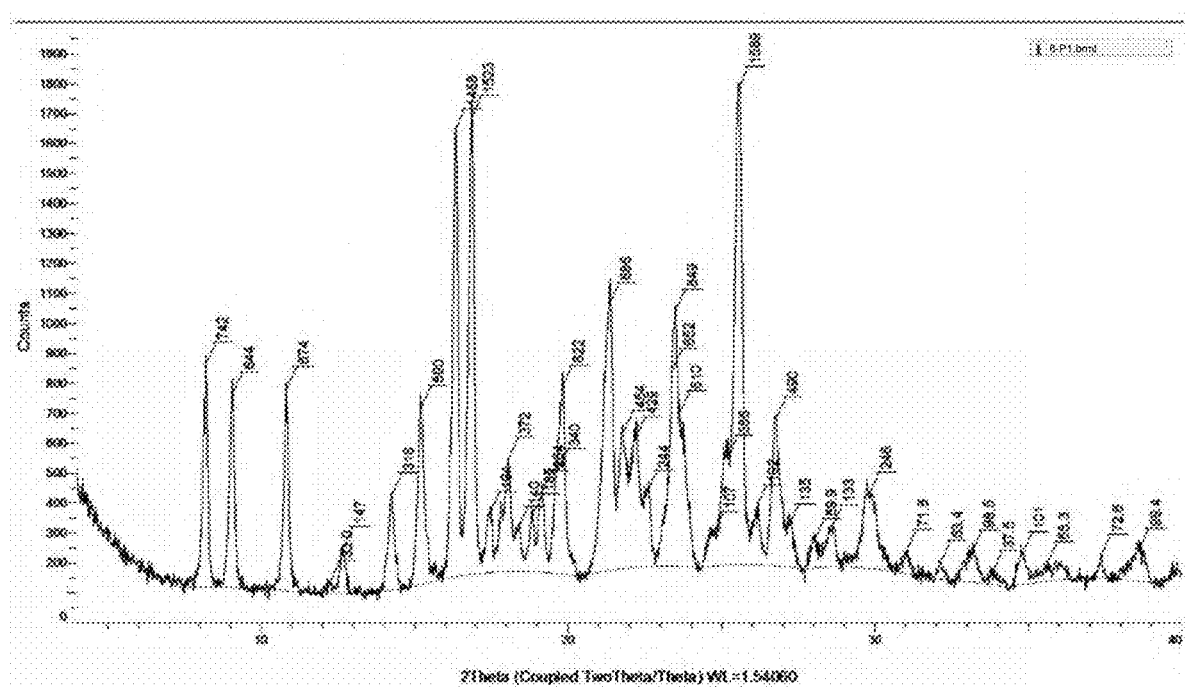

FIG. 359 depicts the XRPD profile of 6-G1 (Experiment Reference 6-Sample Reference G1) (oven dried). 6-G1 converted to Pattern #2b upon oven-drying (7-G2) (Experiment Reference 7-Sample Reference G2), FIG. 360 depicts the XRPD profile of 6-P1 (Experiment Reference 6-Sample Reference P1).

Figure 361:
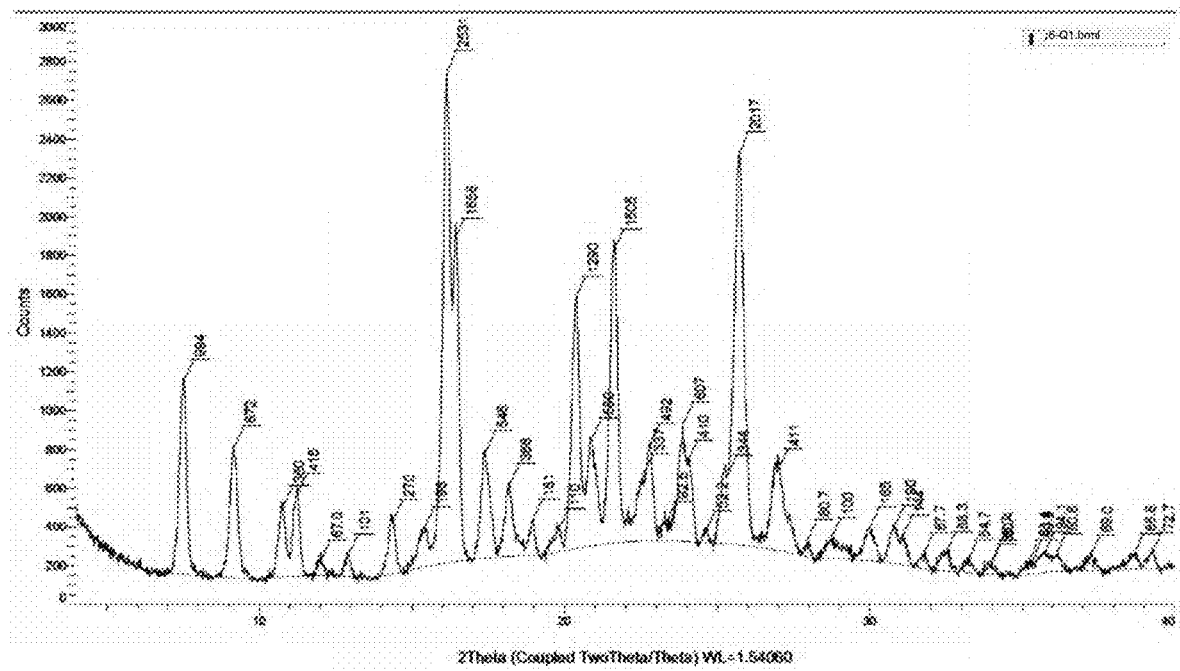

FIG. 361 depicts the XRPD profile of 6-Q1 (Experiment Reference 6-Sample Reference Q1).

Figure 362:
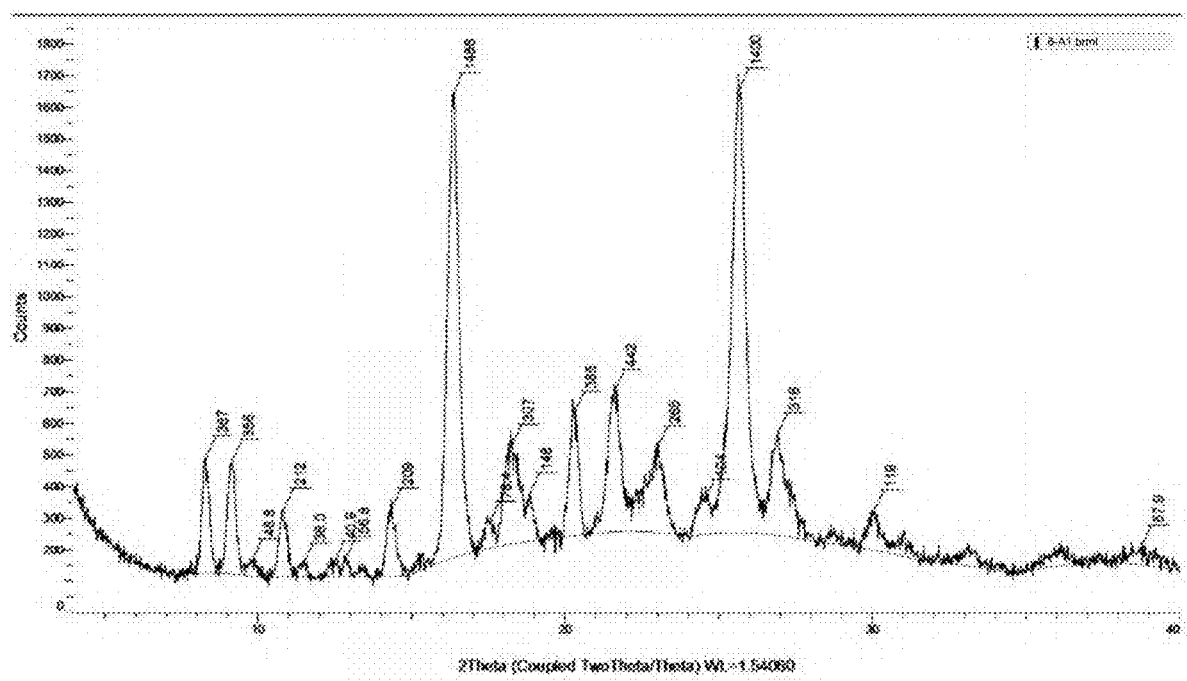

FIG. 362 depicts the XRPD profile of (6-A1) (Experiment Reference 6-Sample Reference A1). 6-A1 converted to Pattern #2b upon oven-drying (6-A2) (Experiment Reference 6-Sample Reference A2).

Figure 363:
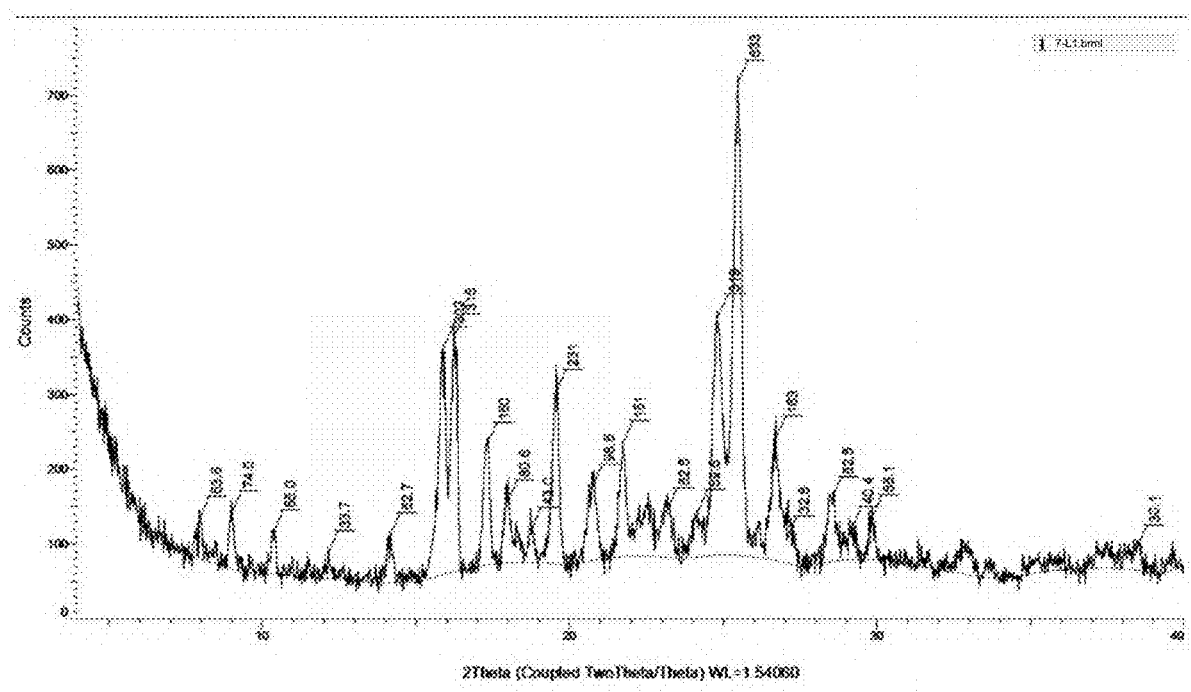

FIG. 363 depicts the XRPD profile of 7-L1 (Experiment Reference 7-Sample Reference L1).

Figure 368:
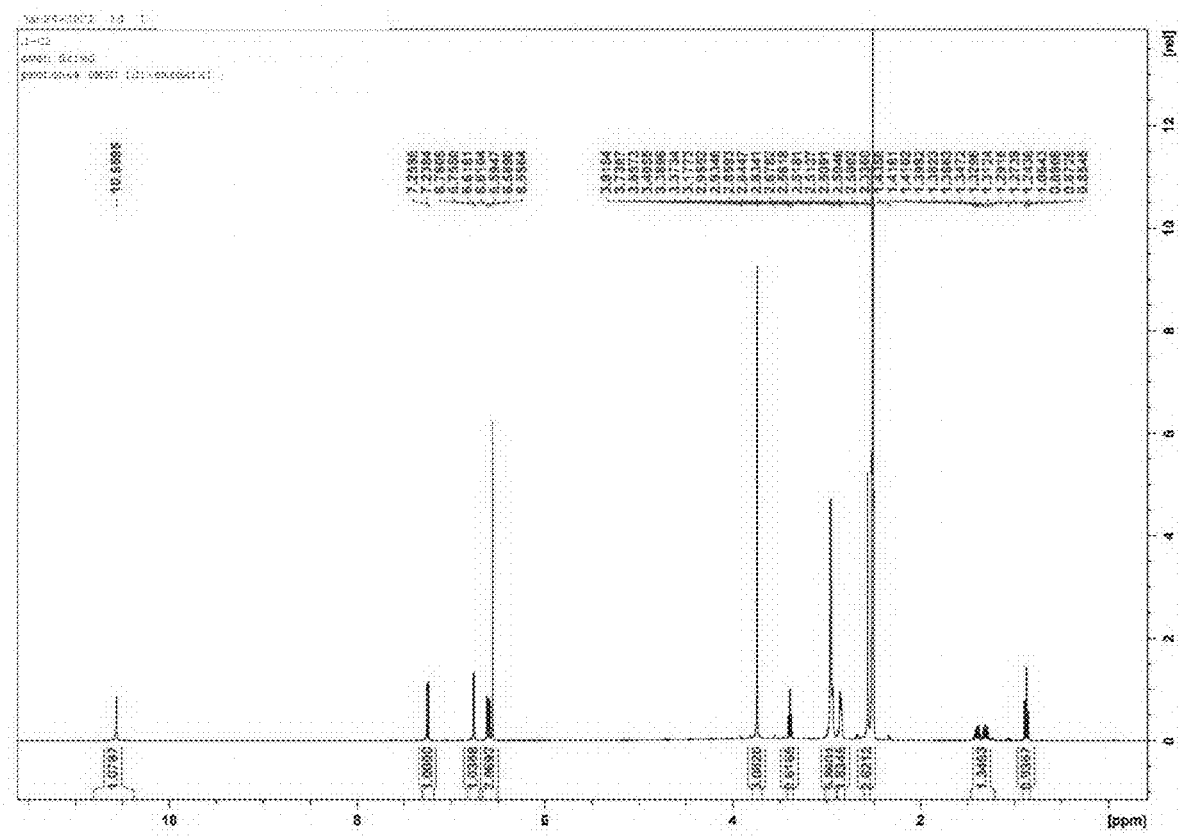

FIG. 368 depicts the $^1$H NMR spectrum of (1-C2) (Experiment Reference 1-Sample Reference C2) (crystallised from butanol), analysis was acquired in DMSO-d6 and calibrated to the non-deuterated solvent residual at 2.50 ppm API to Fumaric acid, 1.0 to 1.0. Specimen contained 6.3% w/w butanol, (th. solvate calc., 13.7% w/w). Acetonitrile could not be quantified due to co-resonant signal.

Figure 370:
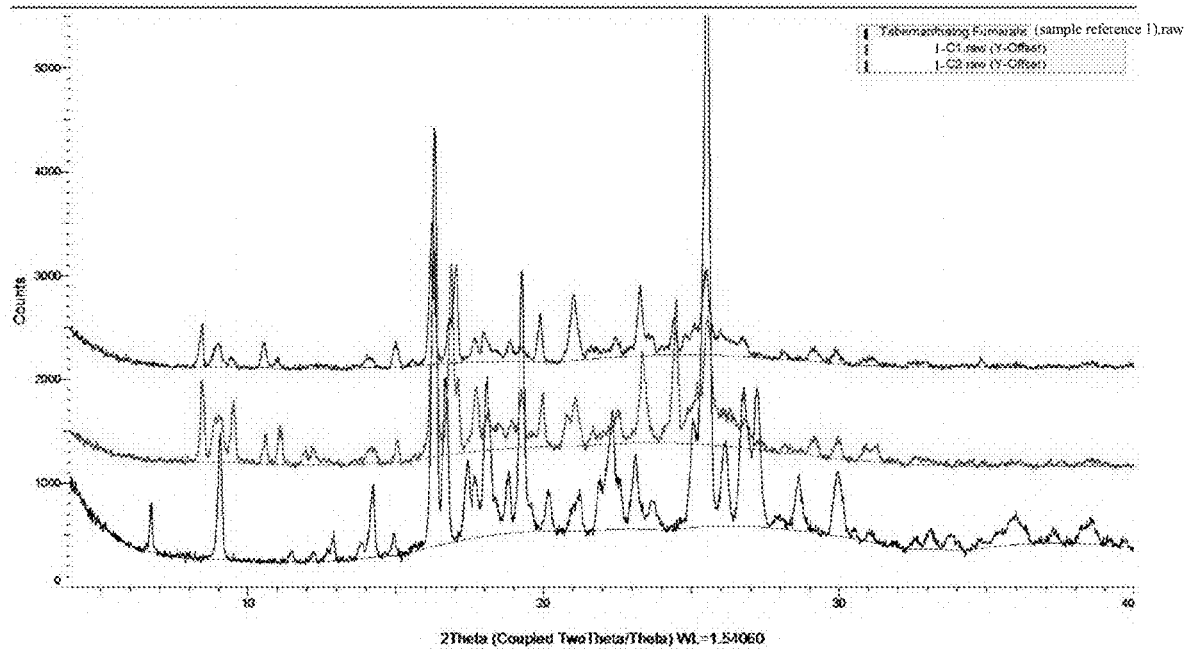

FIG. 370 depicts the XRPD overlay of, form bottom to top, the tabernanthalog monofumarate salt (Pattern #1, Sample Reference 1), 1-C1 (Experiment Reference 1-Sample Reference C1) (wet pellet) and (1-C2) (Experiment Reference 1-Sample Reference C2) (oven dried). Key differences: 8.4°, 9.4°, 10.7°, 11.1°, 16.90, 23.4°, 24.5° 2θ.

Figure 371:
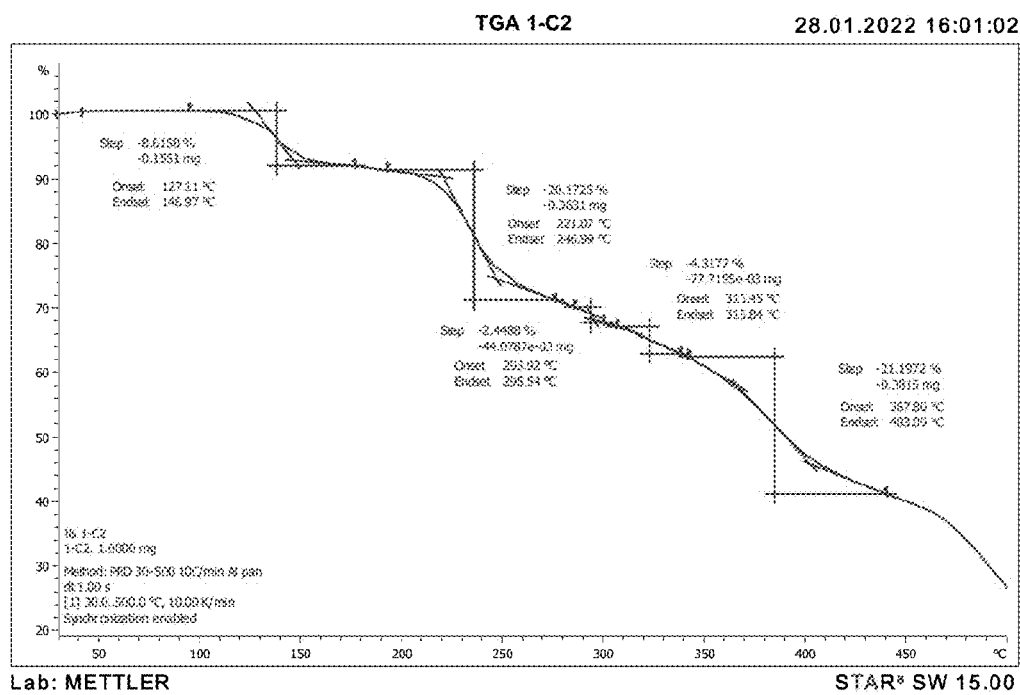

FIG. 371 depicts the TGA profiles of 1-C2 (Experiment Reference 1-Sample Reference C2), analysis was acquired at a ramp rate of +10° C./minute. Weight loss transition (−8.6% w/w) attributed in part to butanol release. Probable butanol, hemi-solvate.

Figure 372:
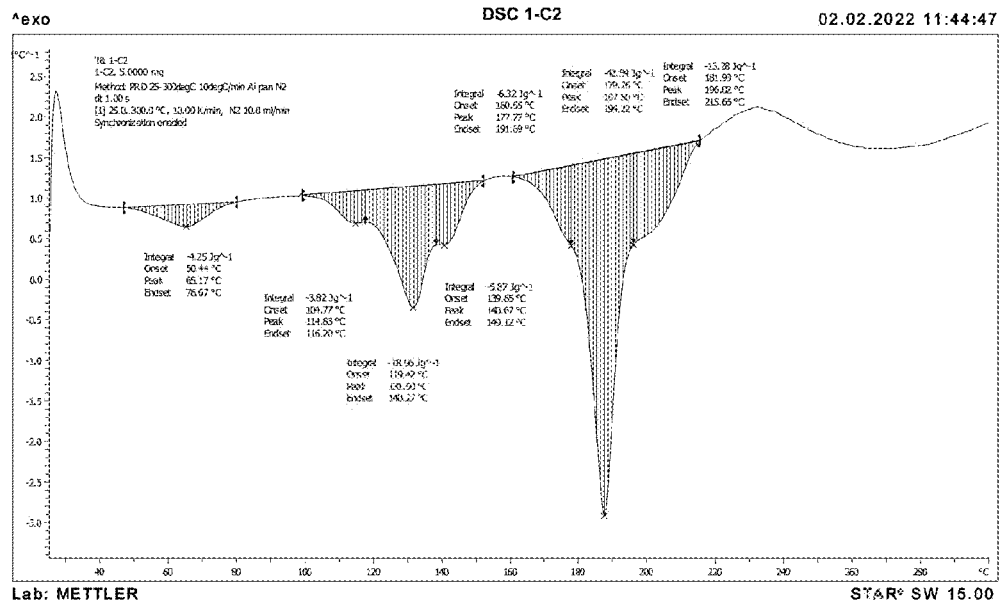

FIG. 372 depicts the DSC of 1-C2 (Experiment Reference 1-Sample Reference C2), analysis was acquired at a ramp rate of +10° C./minute.

Figure 373:
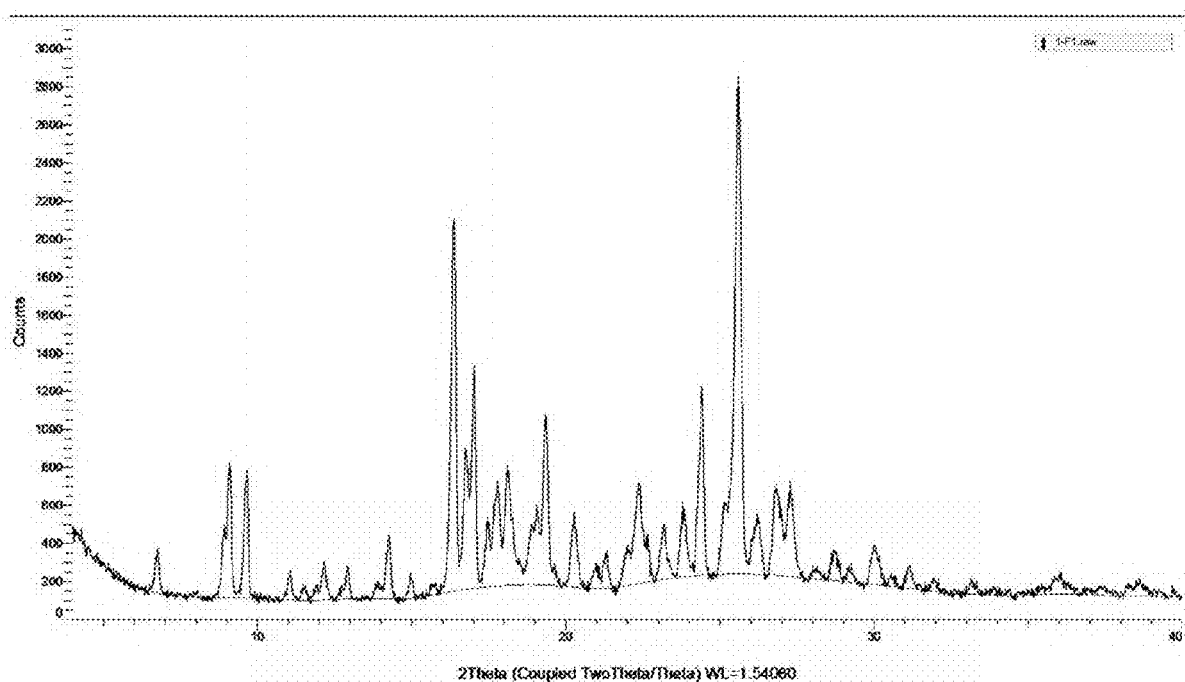

FIG. 373 depicts the XRPD profile of 1-F1 (Experiment Reference 1-Sample Reference F1).

Figures 374, 375:
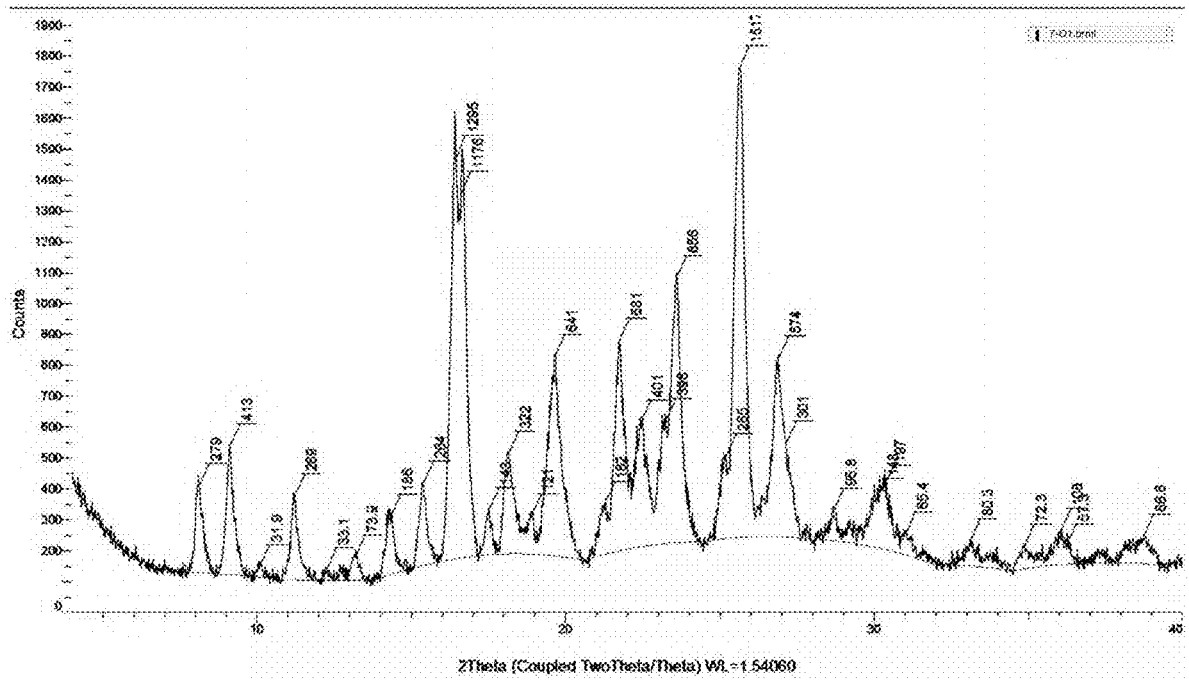

FIG. 374 depicts the XRPD profile of 7-O1 (Experiment Reference 7-Sample Reference O1).

FIG. 375 depicts the XRPD profile of tabernanthalog DSC XRPD 150C (Sample Reference 1), cold cryst., 150° C.

Figure 376:
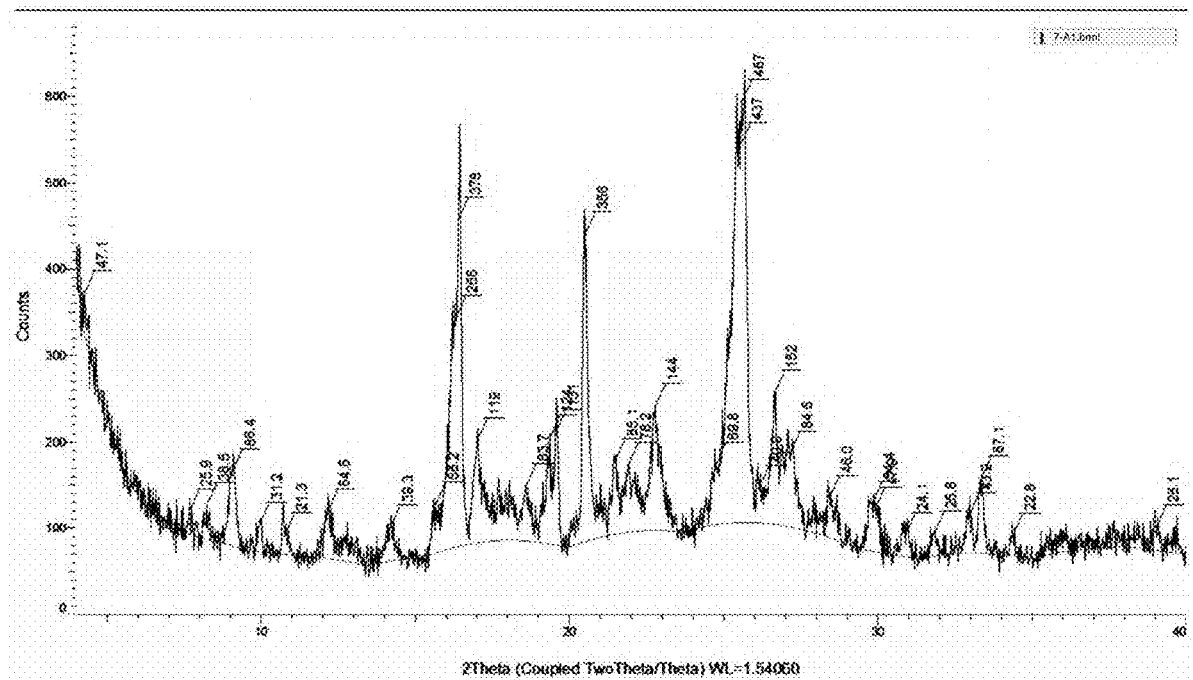
Figure 377:
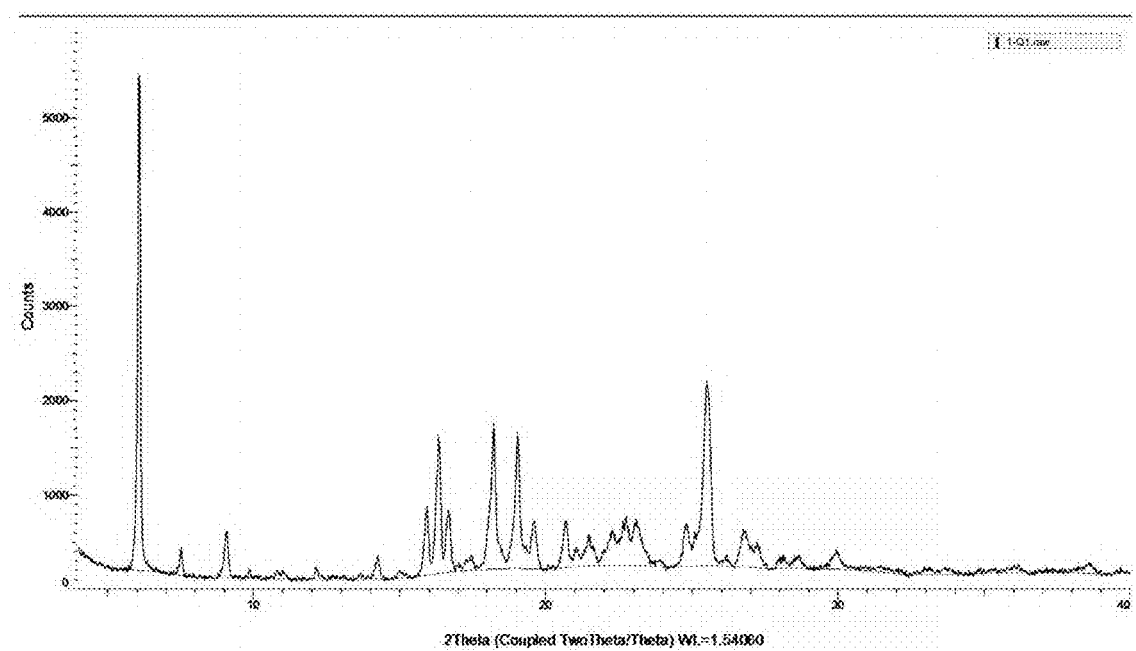

FIG. 376 depicts the XRPD profile of 7-A1 (Experiment Reference 7-Sample Reference A1); High disorder. 7-A1 remained as Pattern #19 upon oven-drying (7-A2) (Experiment Reference 7-Sample Reference A2) FIG. 377 depicts the XRPD profile of 1-Q1.

Figure 377A:
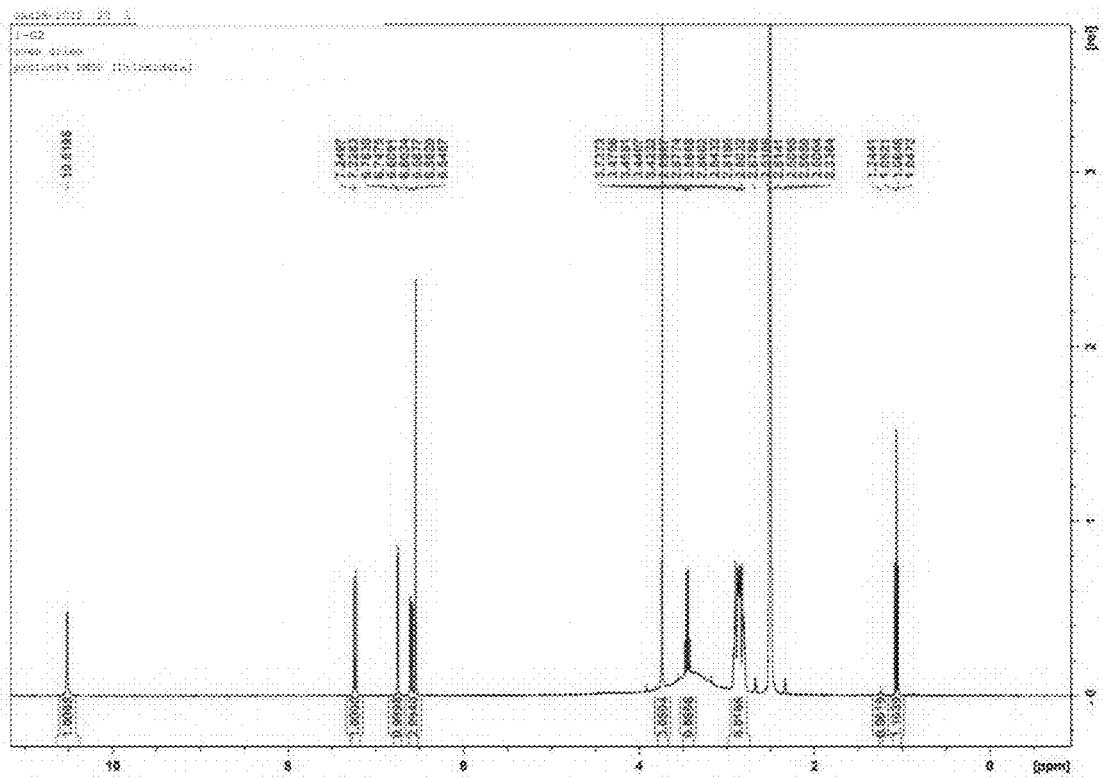

FIG. 377A depicts the $^1$H NMR spectrum of 1-G2 (Experiment Reference 1-Sample Reference G2) (crystallized from ethanol), analysis was acquired in DMSO-d$_6$ and calibrated to the non-deuterated solvent residual at 2.50 ppm. API to Fumaric acid, 2.0 to 1.0. Specimen contained 4.9% w/w ethanol, (th. solvate calc., 11.7% w/w). Residual acetonitrile (0.2% w/w).

Figure 377B:
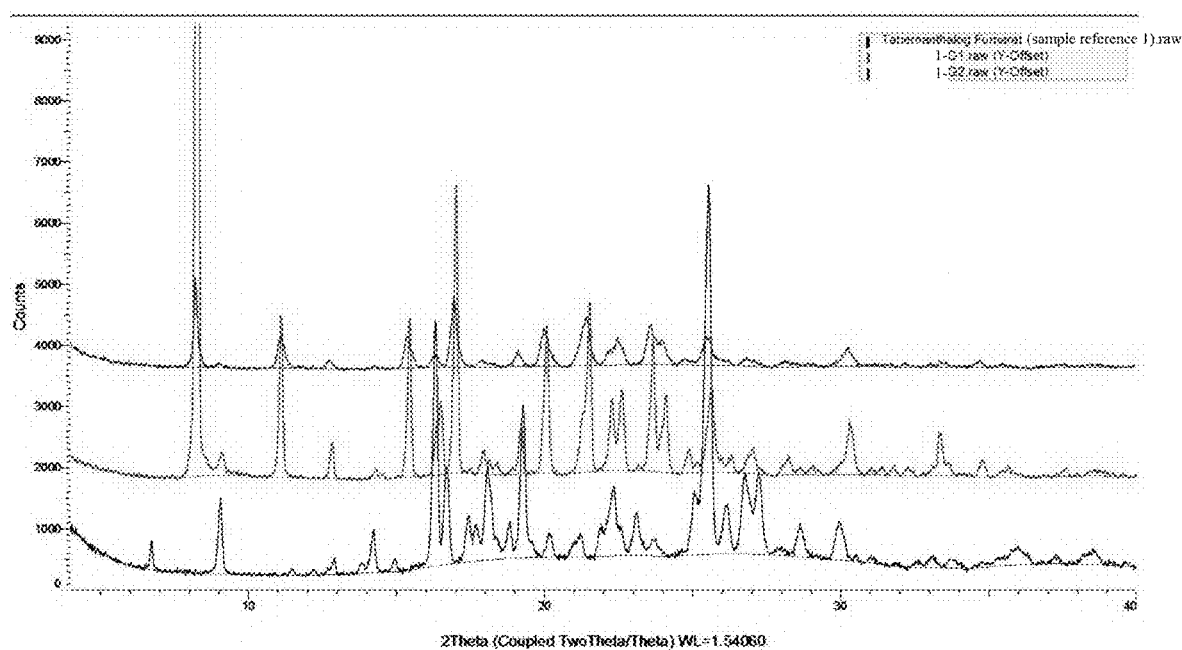

FIG. 377B depicts the XRPD overlay of, from bottom to top, the tabernanthalog monofumarate salt (Pattern #1, Sample Reference 1), 1-G1 (Experiment Reference 1-Sample Reference G1) (wet pellet) and 1-G2 (Experiment Reference 1-Sample Reference G2) (oven dried). Key differences. 8.20, 11.10, 15.5°, 17.00, 21.6° 2θ.

Figure 377C:
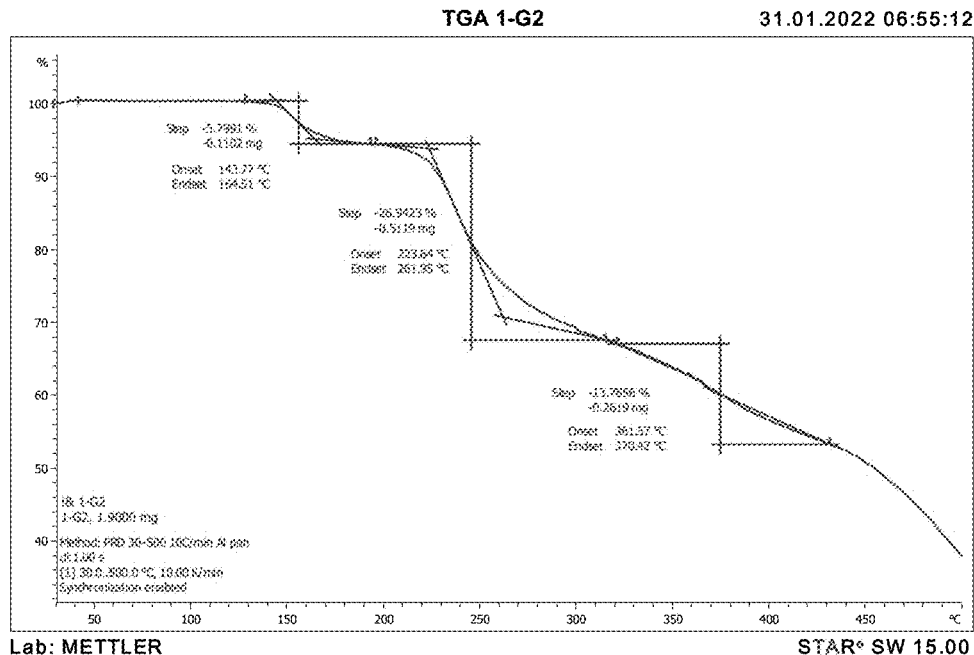

FIG. 377C depicts the TGA profile of 1-G2 (Experiment Reference 1-Sample Reference G2), analysis was acquired at a ramp rate of +10° C./minute. Weight loss transition (−5.8% w/w) attributed to ethanol release. Probable ethanol, hemi-solvate.

Figure 377D:
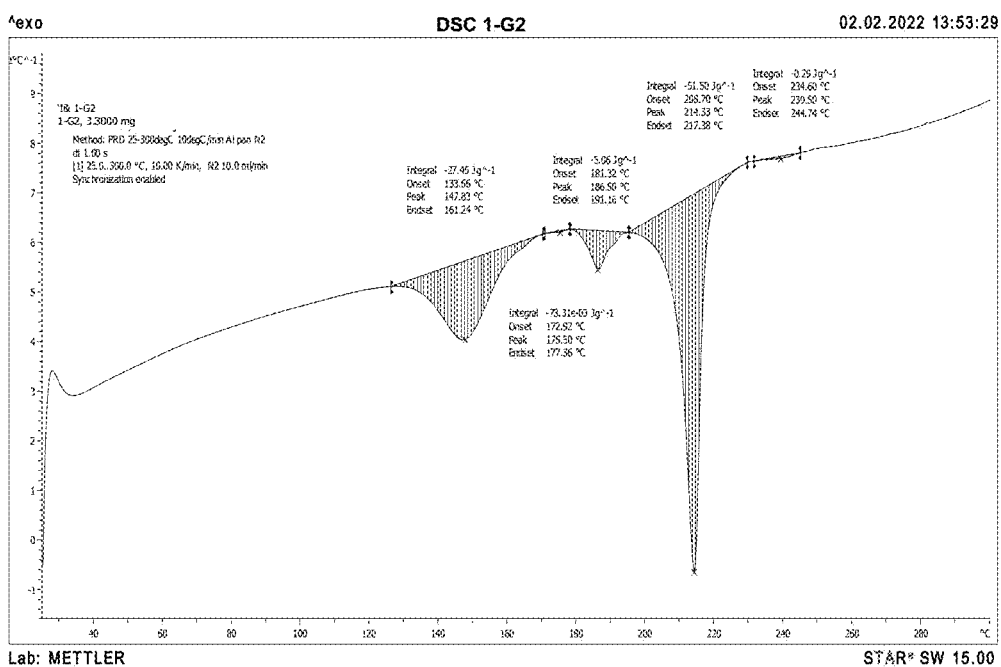

FIG. 377D depicts the DSC profile of 1-G2 (Experiment Reference 1-Sample Reference G2), analysis was acquired at a ramp rate of +10° C./minute.

Figure 377E:
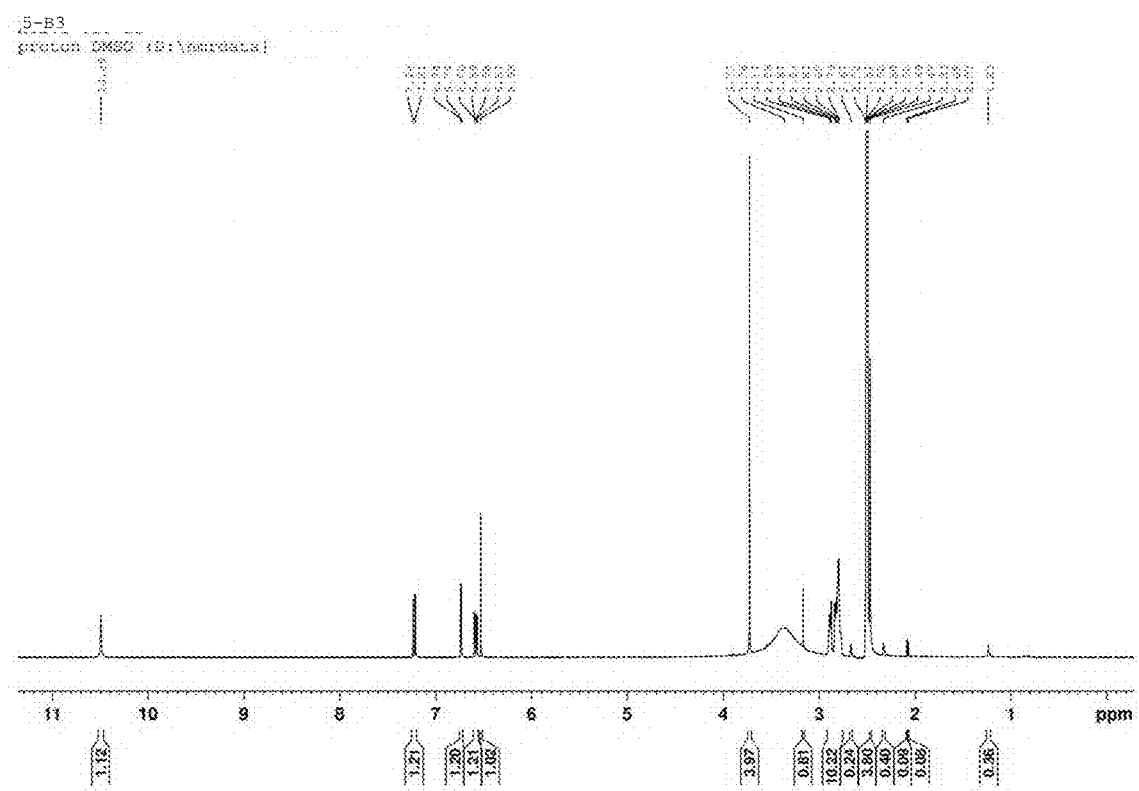

FIG. 377E depicts the $^1$H NMR spectrum of (5-B3) (Experiment Reference 5-Sample Reference B3), analysis was acquired in DMSO-d$_6$ and calibrated to the non-deuterated solvent residual at 2.50 ppm. API to Fumaric acid, 2.0 to 1.0. 0.2% w/w acetone, 0.3% w/w acetonitrile, and 2.4% w/w methanol content.

FIG. 377F depicts the XRPD profile of (5-B3) (Experiment Reference 5-Sample Reference B3).

Figure 377G:
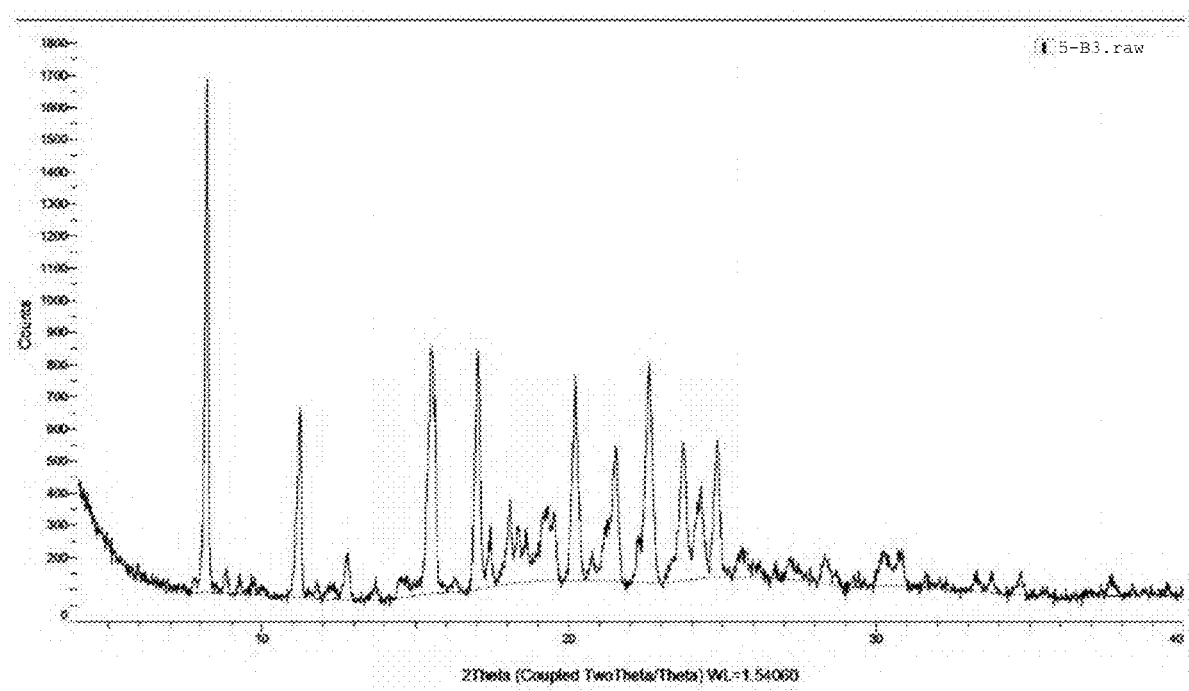

FIG. 377G depicts the XRPD profiles of a simulated powder pattern for tabernanthalog hemifumarate, Pattern #14, Form I (11-Q2 ((Experiment Reference 11-Sample Reference Q2), top) and 5-B3 (Experiment Reference 5-Sample Reference B3) (bottom).

Figure 377H:
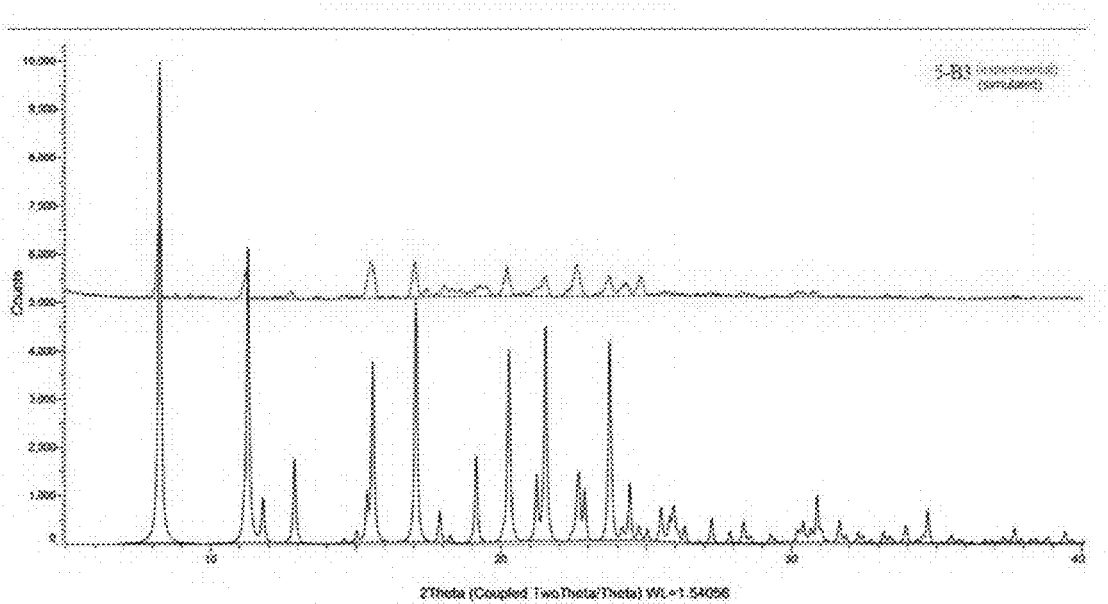

FIG. 377H depicts the overlay of experimental and simulated patterns of tabernanthalog hemifumarate (Pattern #14, Form I).

Figure 377I:
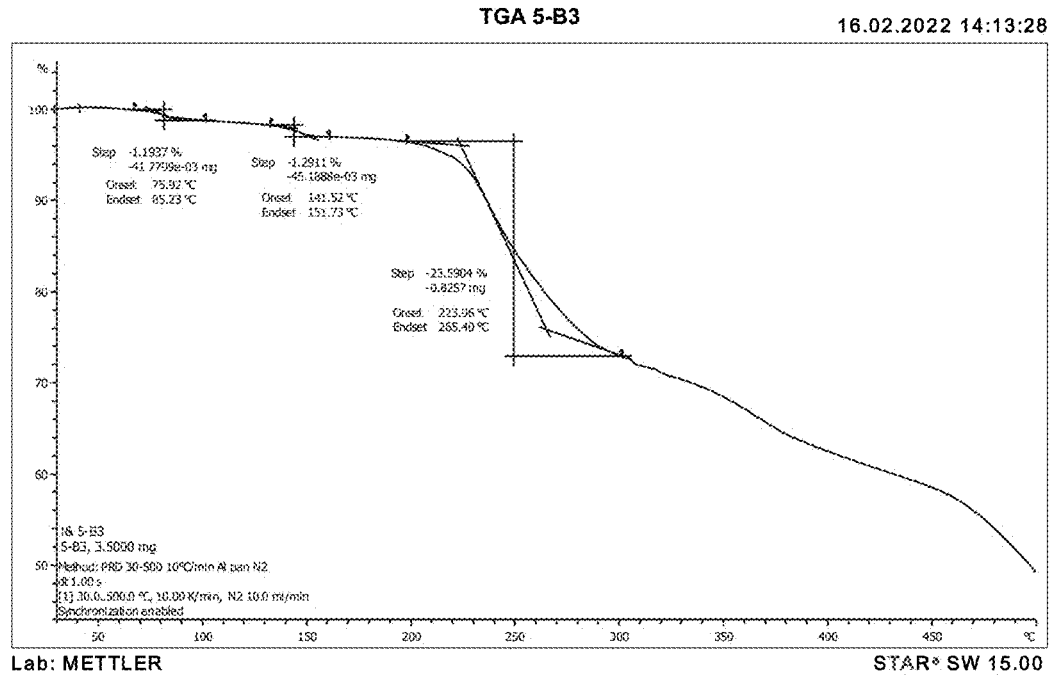

FIG. 377I depicts the TGA profile of (5-B3) (Experiment Reference 5-Sample Reference B3), analysis was acquired at a ramp rate of +10° C./minute.

Figure 377J:
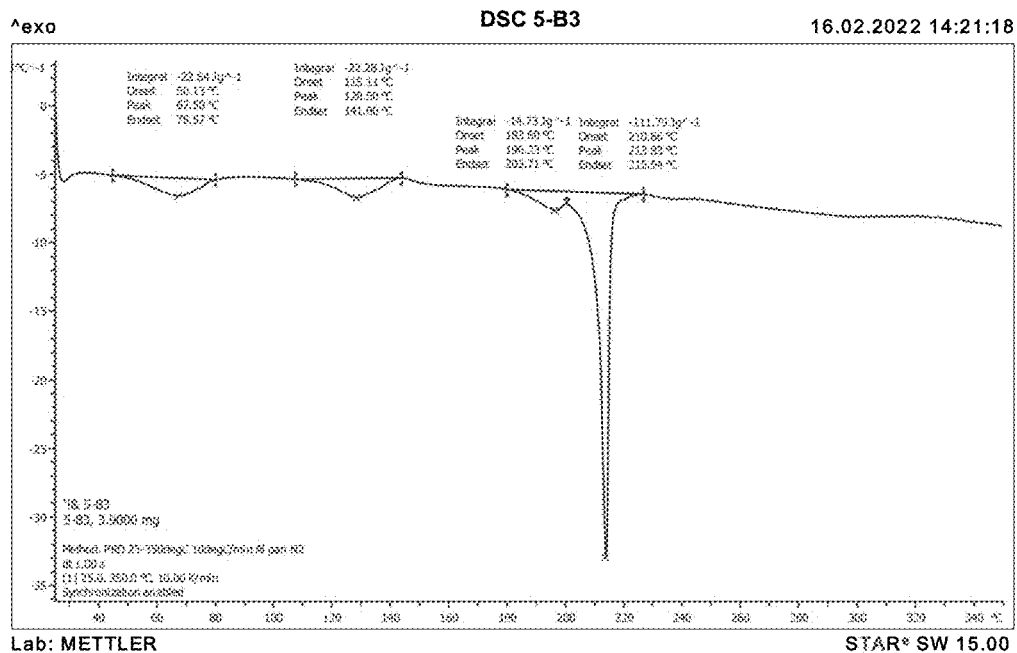

FIG. 377J depicts the DSC profile of (5-B3) (Experiment Reference 5-Sample Reference B3), analysis was acquired at a ramp rate of +10° C./minute.

Figure 378:
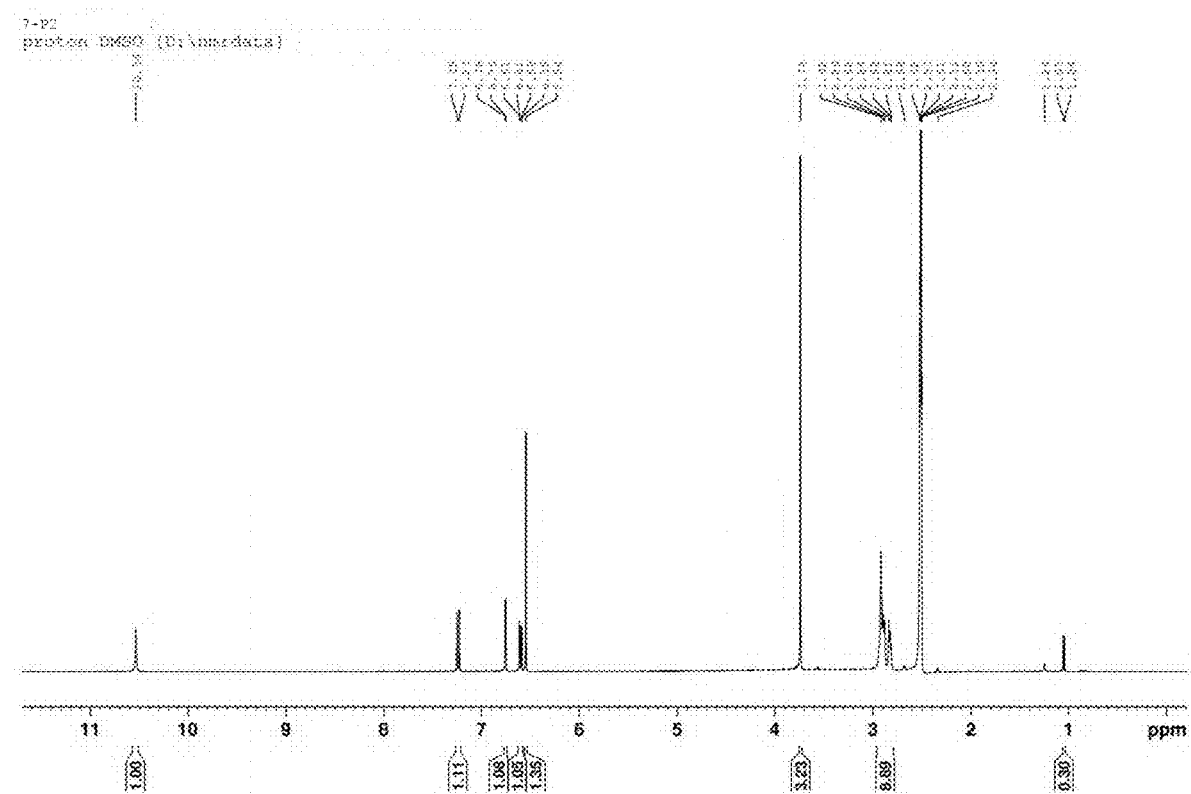

FIG. 378 depicts the $^1$H NMR spectrum of 7-P2 (Experiment Reference 7-Sample Reference P2) (suspended in isopropanol), analysis was acquired in DMSO-d6 and calibrated to the non-deuterated solvent residual at 2.50 ppm API to Fumaric acid, 2.0 to 1.0. Residual isopropanol 0.9% w/w.

Figure 380:
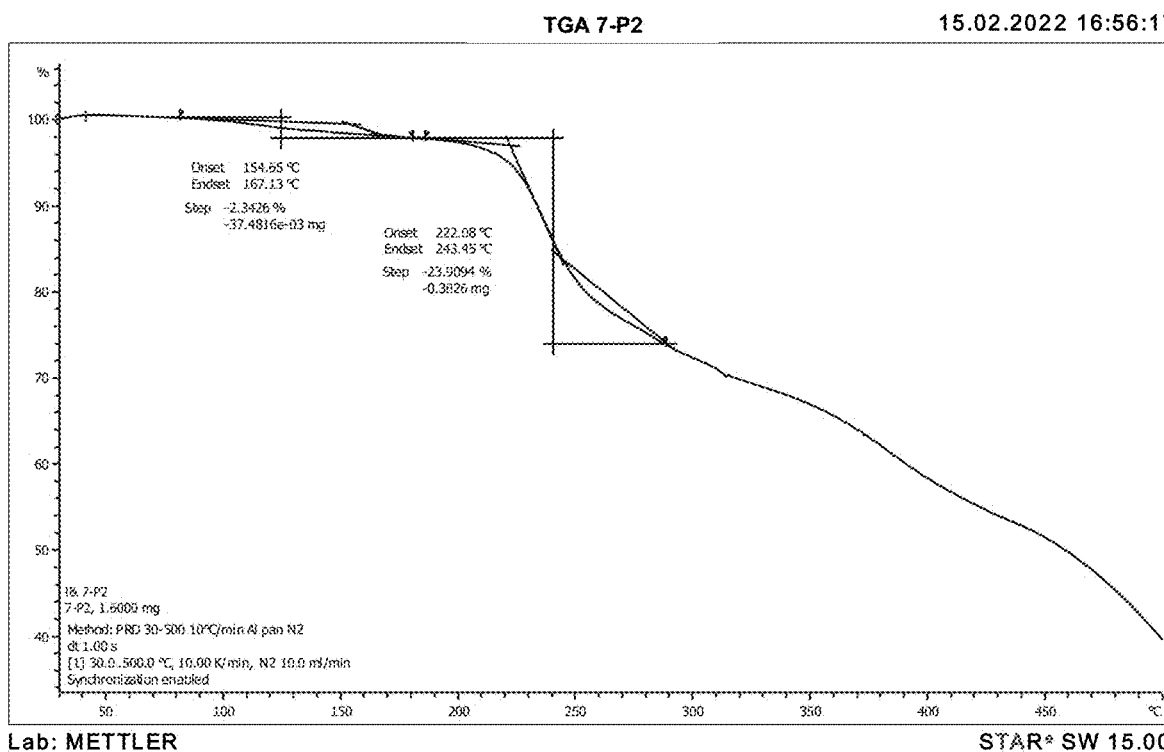

FIG. 380 depicts the TGA profile of 7-P2 (Experiment Reference 7-Sample Reference P2), analysis was acquired at a ramp rate of +10° C./minute.

Figure 381:
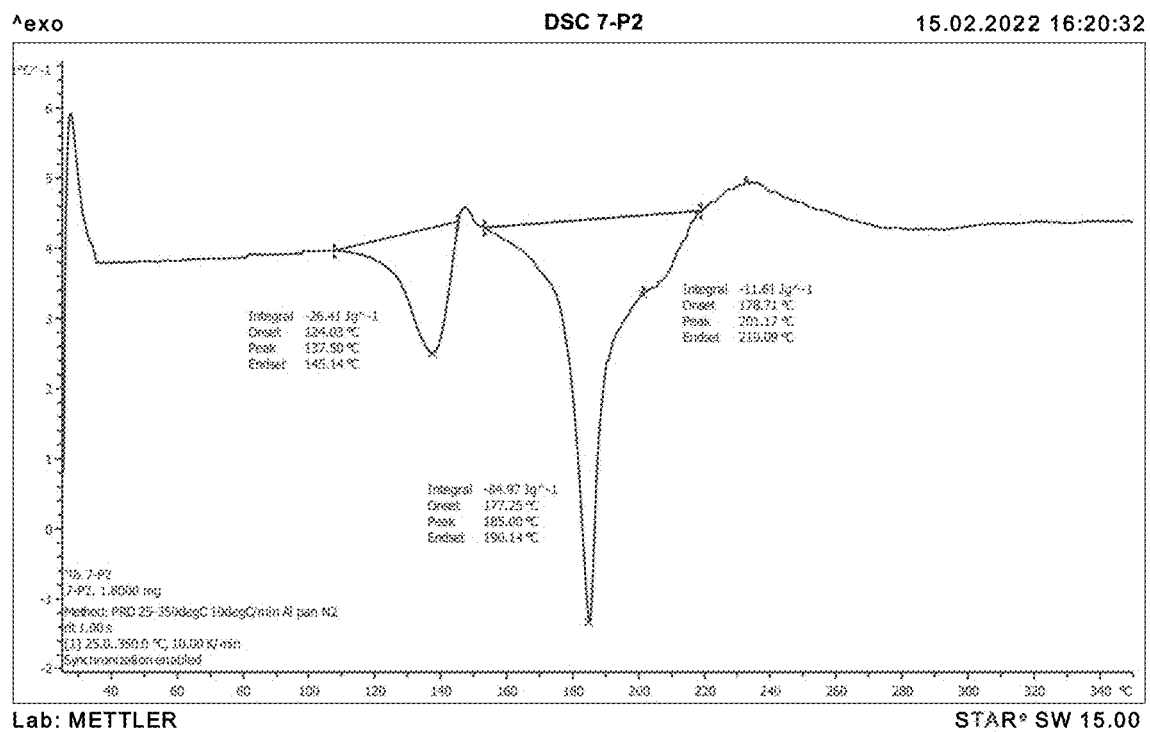

FIG. 381 depicts the DSC of 7-P2 (Experiment Reference 7-Sample Reference P2), analysis was acquired at a ramp rate of +10° C./minute.

Figure 382:
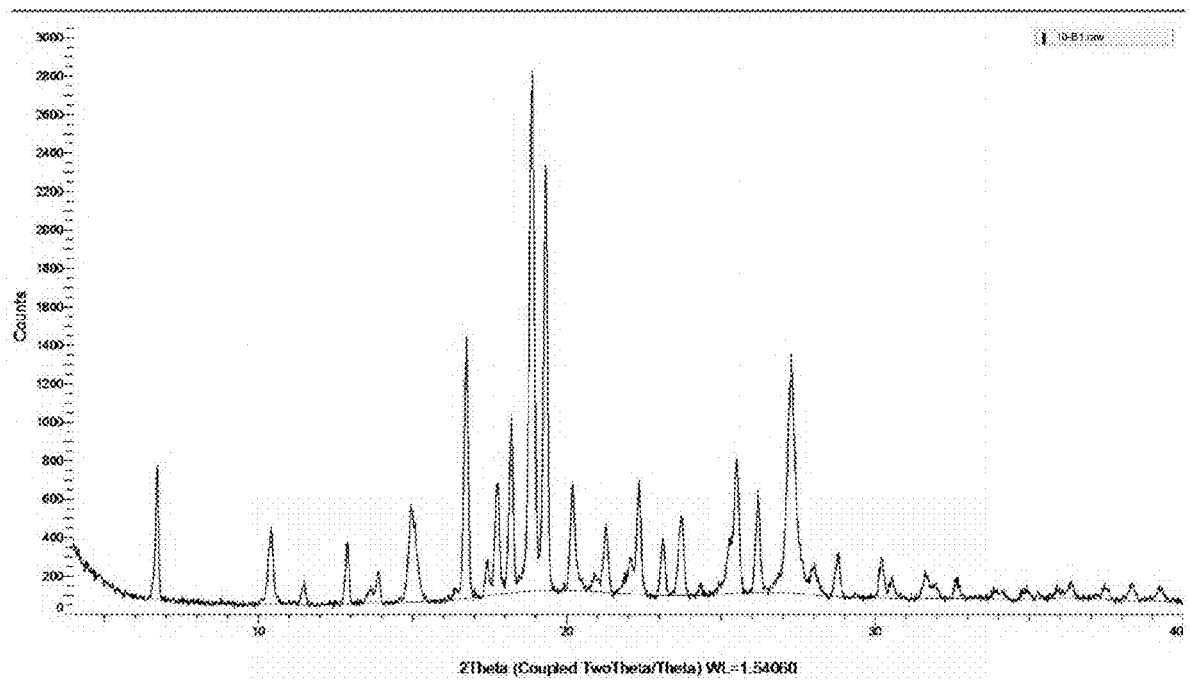

FIG. 382 depicts the XRPD profile of 10-B1 (Experiment Reference 10-Sample Reference B1).

Figure 383:
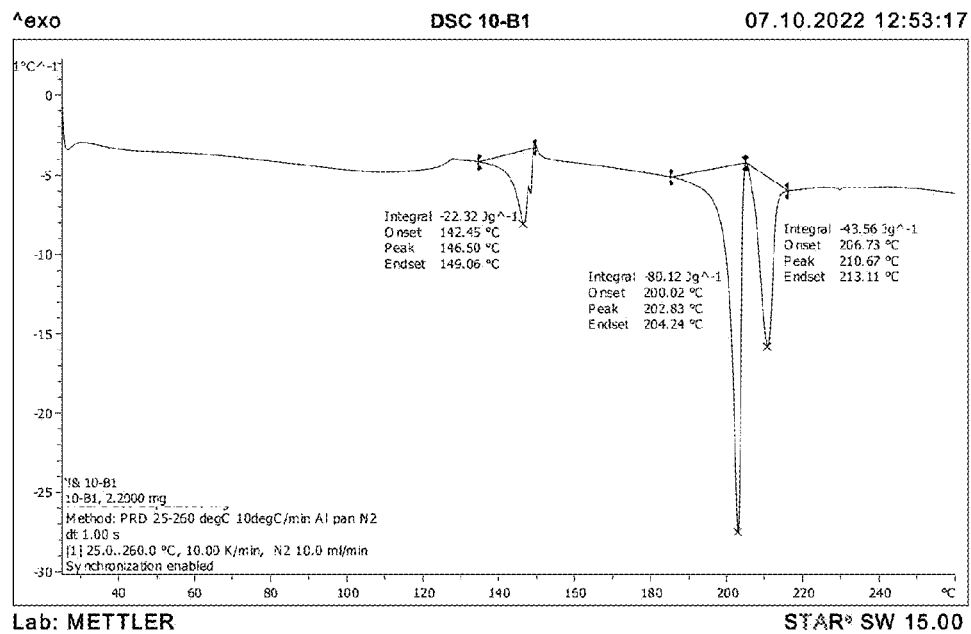

FIG. 383 depicts the DSC of 10-B1 (Experiment Reference 10-Sample Reference B1), analysis was acquired at a ramp rate of +10° C./minute.

Figure 384:
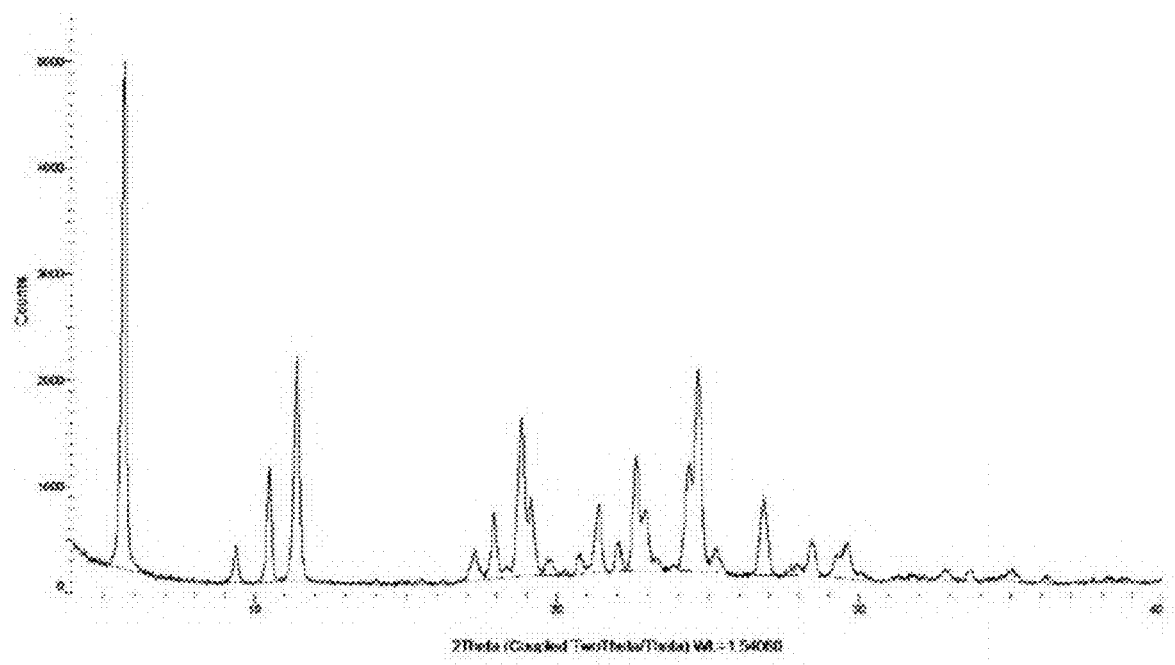

FIG. 384 depicts an XRPD diffractogram of the tabernanthalog sorbate salt. The XRPD signals observed in this diffractogram are characterized in Table 216.

Figure 385:
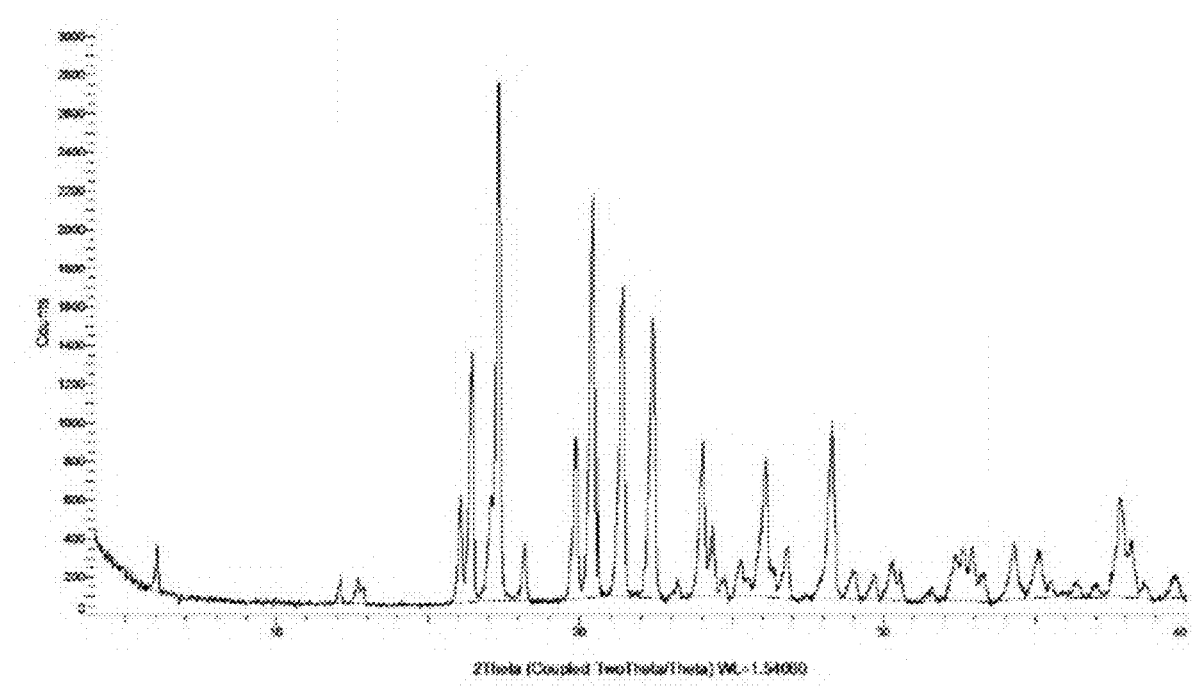

FIG. 385 depicts an XRPD diffractogram of the tabernanthalog tartrate salt. The XRPD signals observed in this diffractogram are characterized in Table 217.

Figure 386:
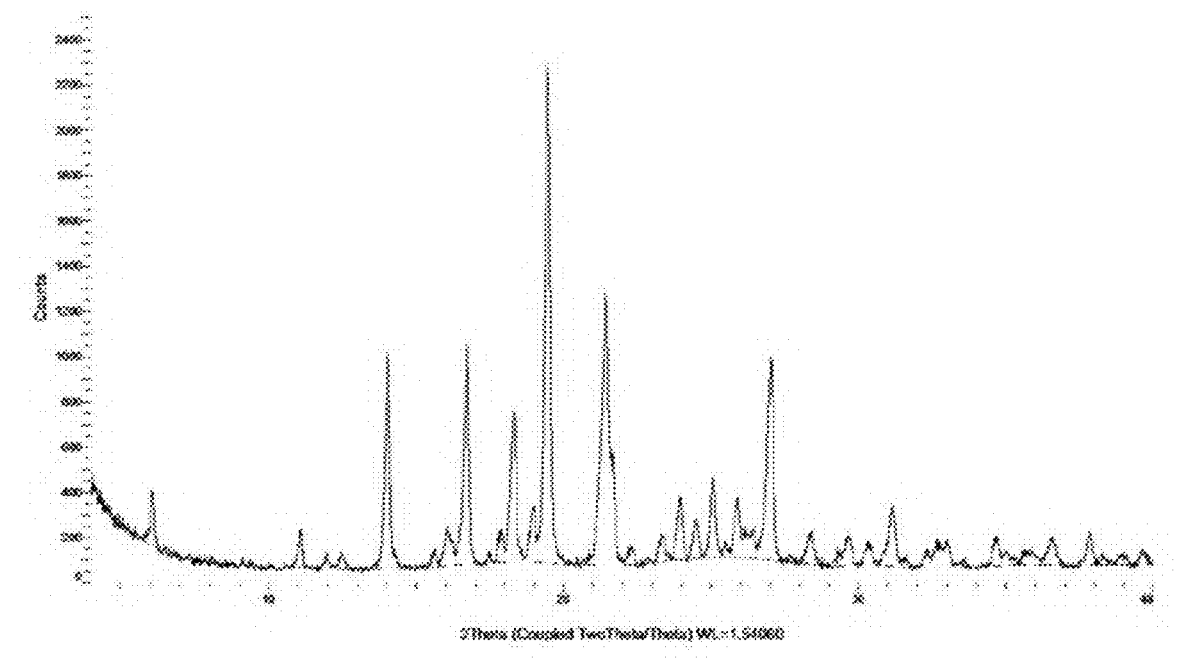

FIG. 386 depicts an XRPD diffractogram of the tabernanthalog malate salt. The XRPD signals observed in this diffractogram are characterized in Table 219.

Figure 387:
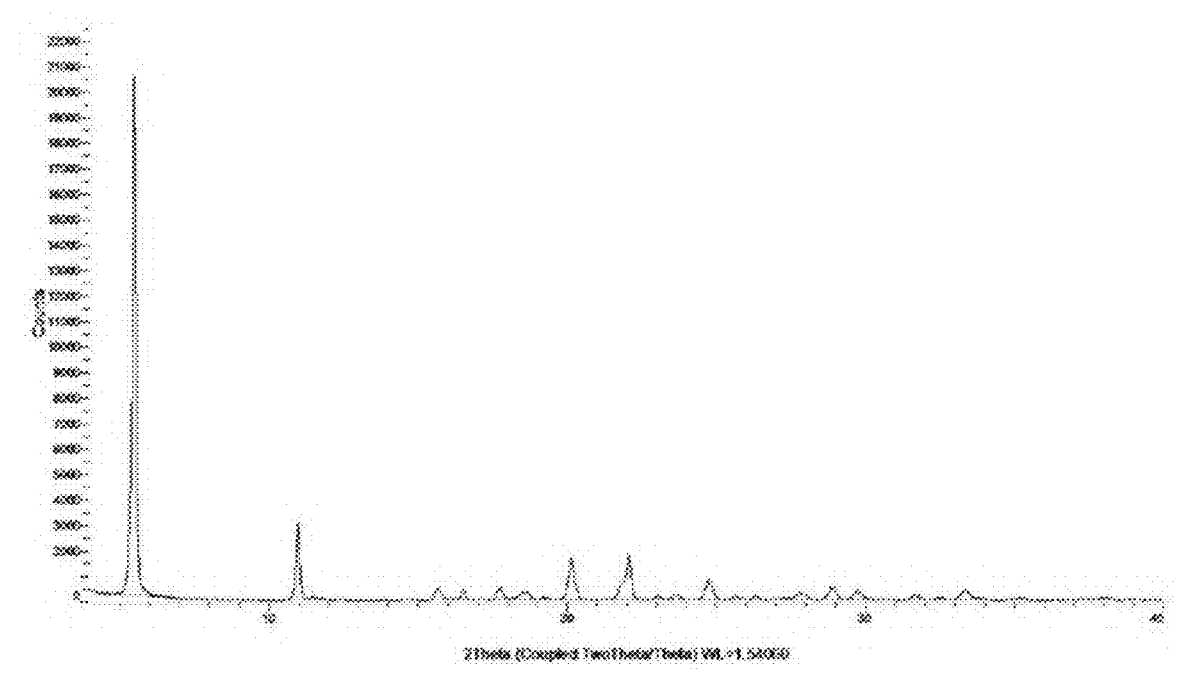

FIG. 387 depicts an XRPD diffractogram of the tabernanthalog tosylate salt. The XRPD signals observed in this diffractogram are characterized in Table 220.

Figure 388:
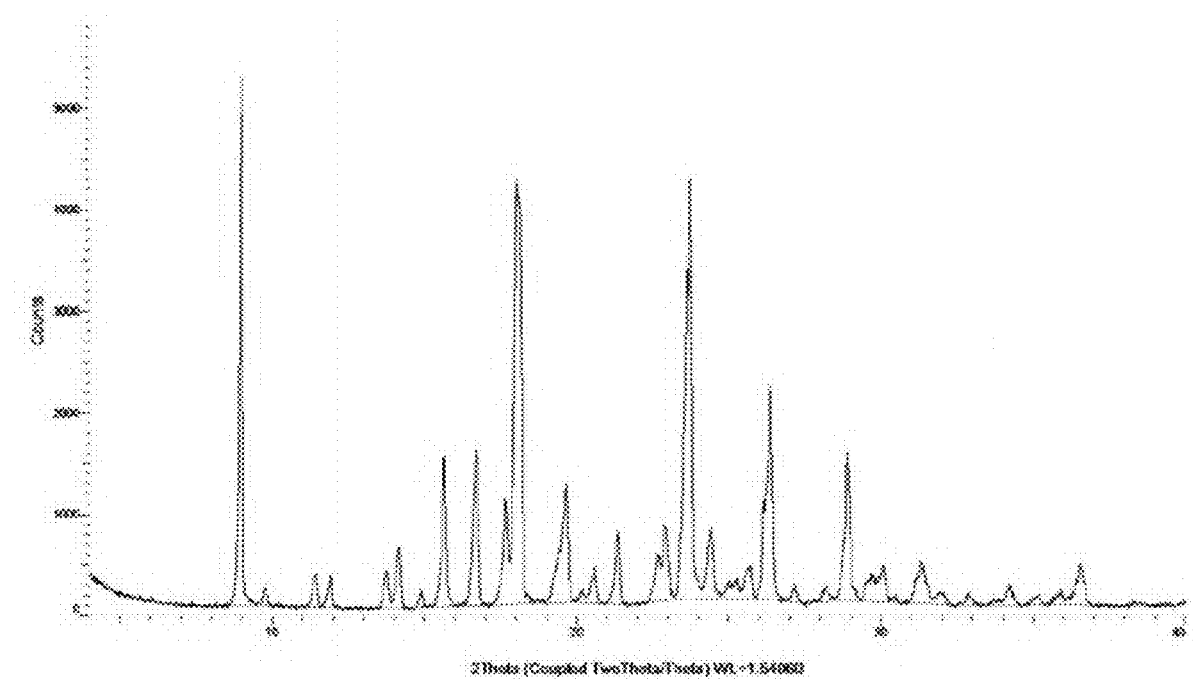

FIG. 388 depicts an XRPD diffractogram of the tabernanthalog benzoate salt. The XRPD signals observed in this diffractogram are characterized in Table 218.

Figure 389:
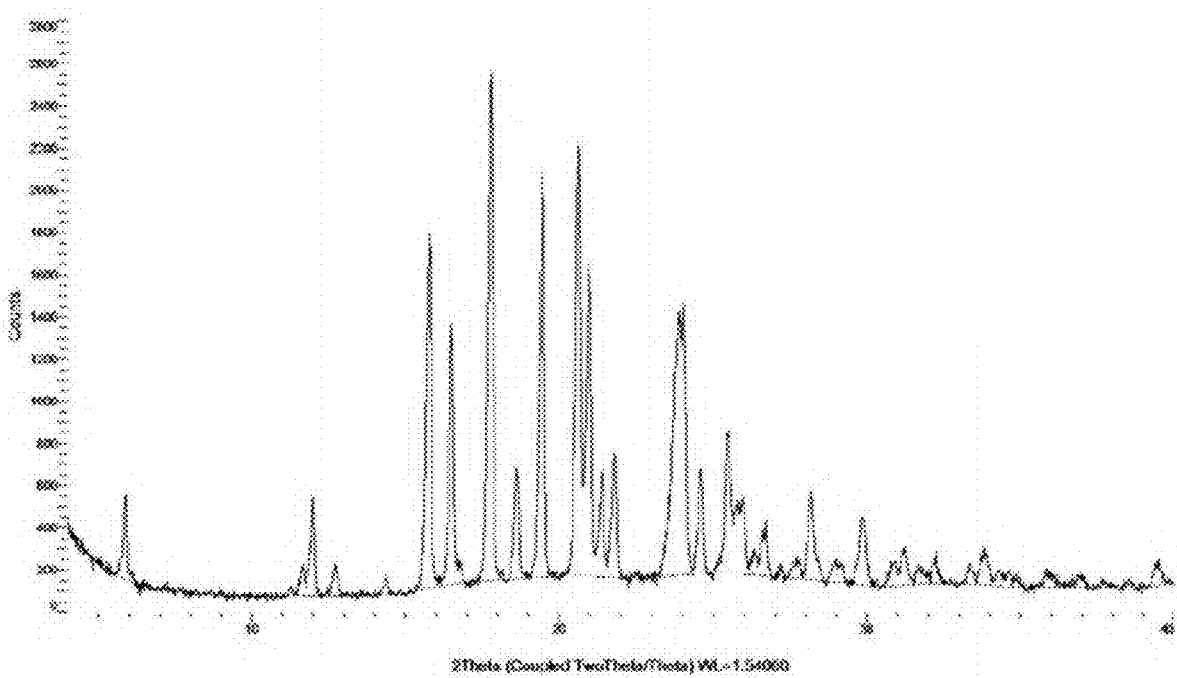

FIG. 389 depicts an XRPD diffractogram of the tabernanthalog adipate salt. The XRPD signals observed in this diffractogram are characterized in Table 221.

Figure 390:
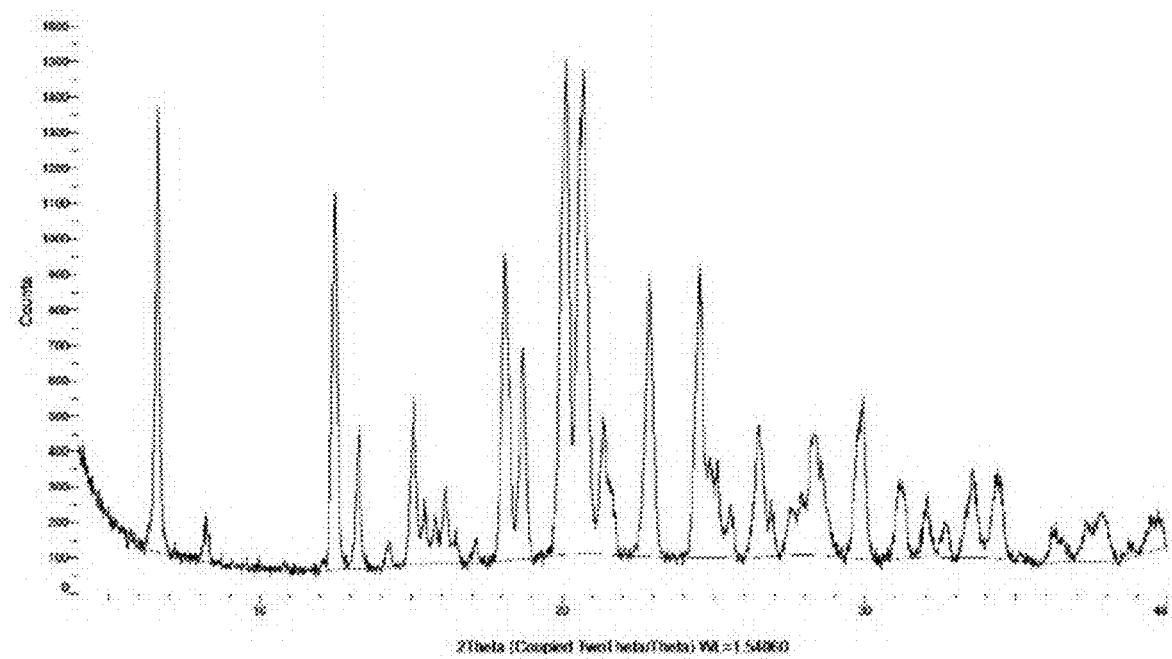

FIG. 390 depicts an XRPD diffractogram of the tabernanthalog glucoronate salt. The XRPD signals observed in this diffractogram are characterized in Table 222.

Figure 391:
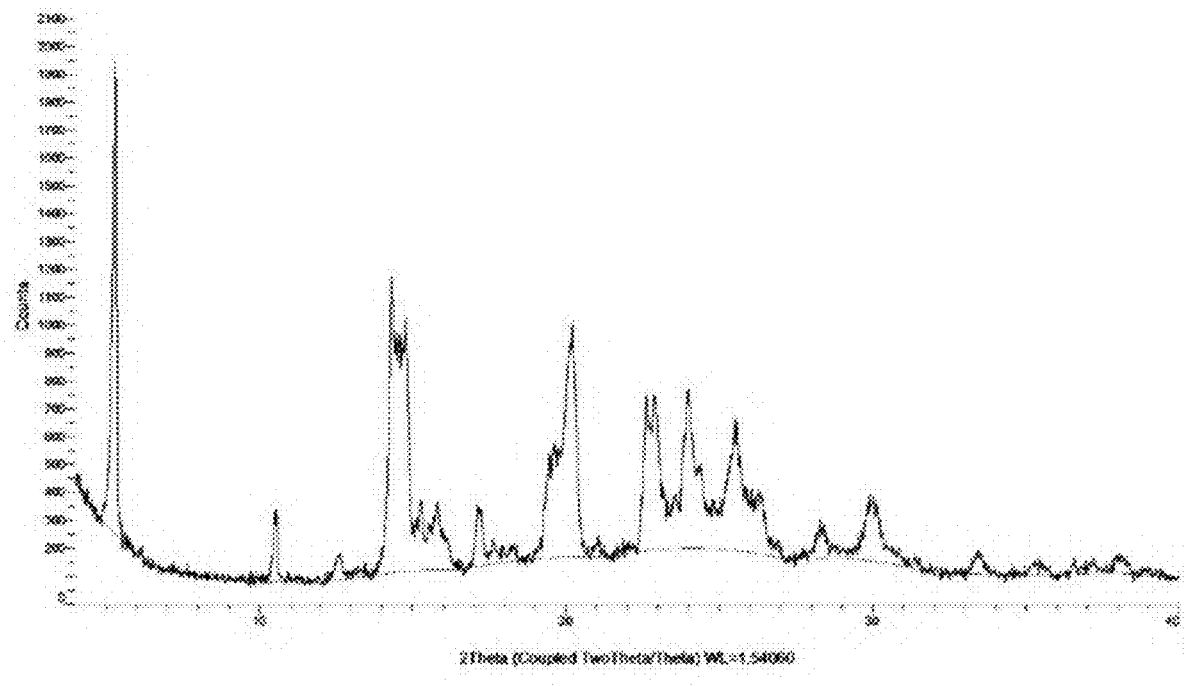

FIG. 391 depicts an XRPD diffractogram of the tabernanthalog phosphate salt. The XRPD signals observed in this diffractogram are characterized in Table 223.

Figure 392:
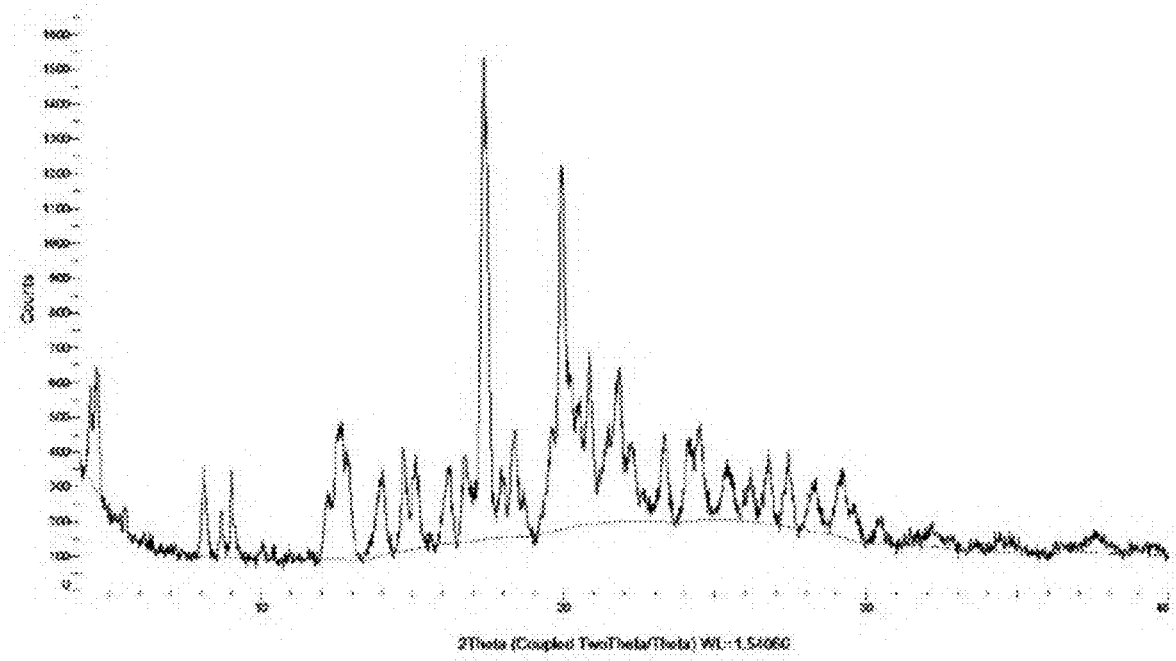

FIG. 392 depicts an XRPD diffractogram of the tabernanthalog edisylate salt. The XRPD signals observed in this diffractogram are characterized in Table 224.

Figure 393:
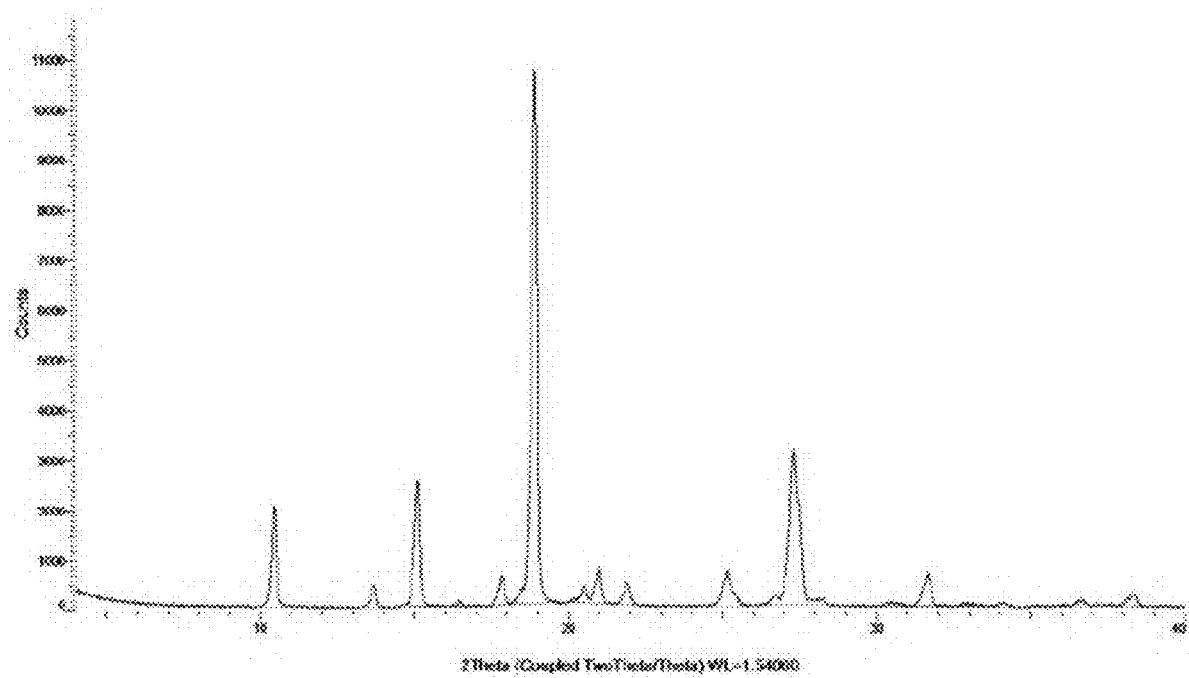

FIG. 393 depicts an XRPD diffractogram of tabernanthalog. The XRPD signals observed in this diffractogram are characterized in Table 215.

Figure 394:
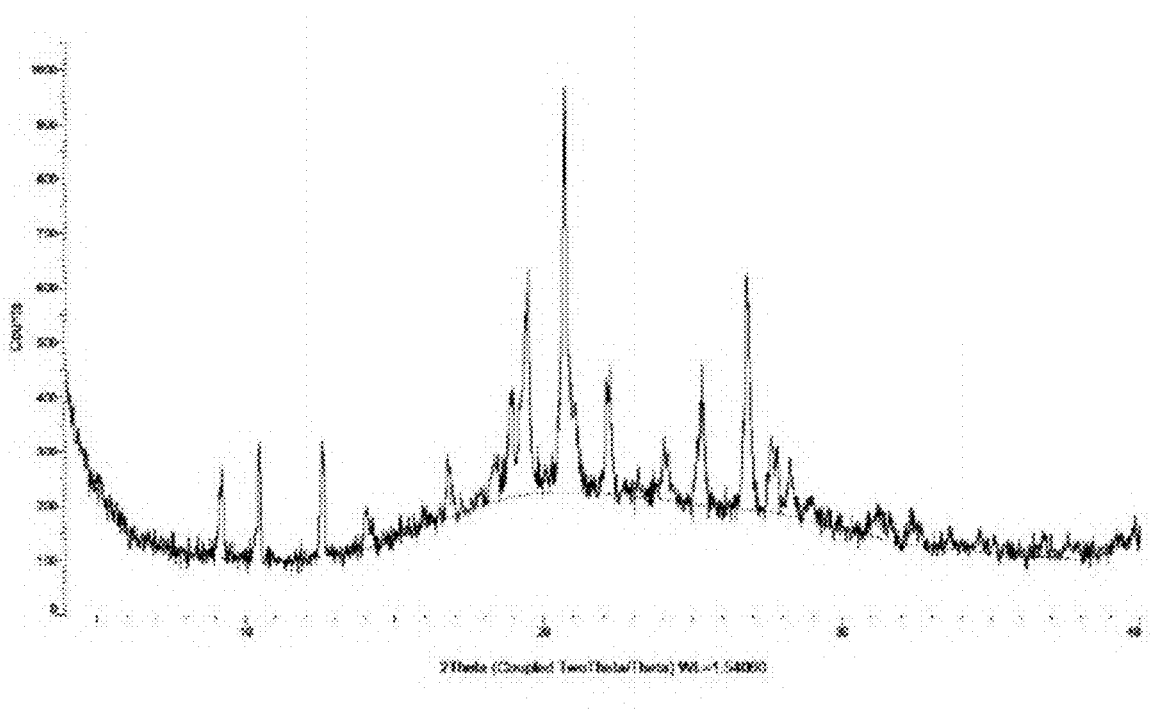

FIG. 394 depicts an XRPD diffractogram of the tabernanthalog maleate salt. The XRPD signals observed in this diffractogram are characterized in Table 225.

Figure 395:
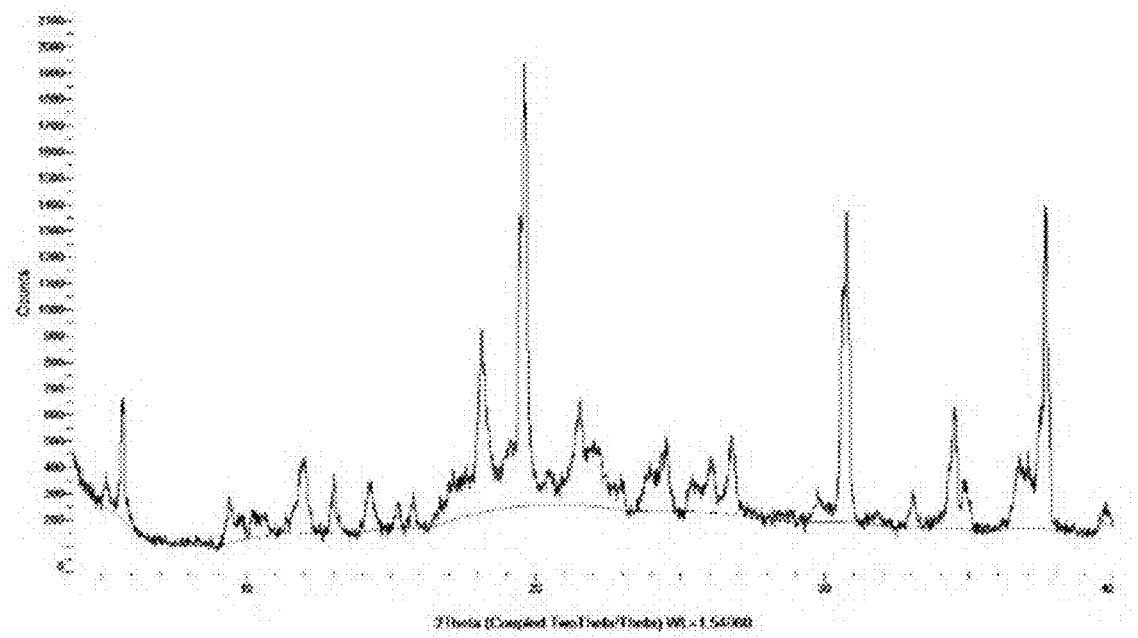

FIG. 395 depicts an XRPD diffractogram of the tabernanthalog galactarate salt. The XRPD signals observed in this diffractogram are characterized in Table 226.

Figure 396:
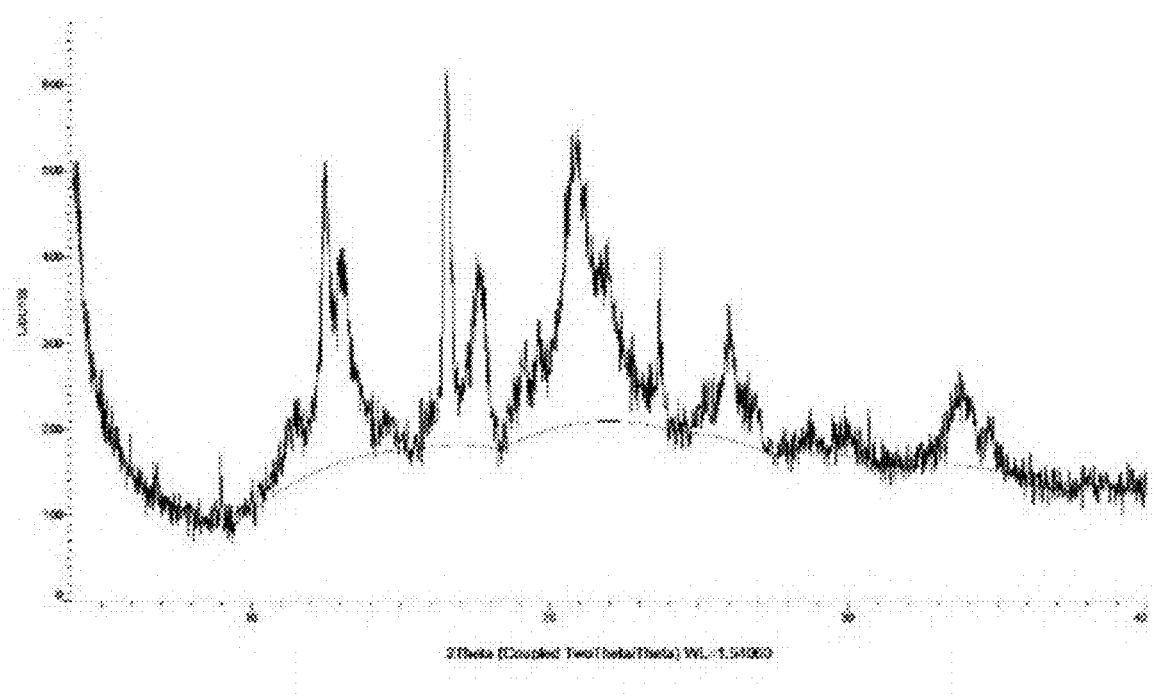

FIG. 396 depicts an XRPD diffractogram of the tabernanthalog citrate salt. The XRPD signals observed in this diffractogram are characterized in Table 227.

Figure 397:
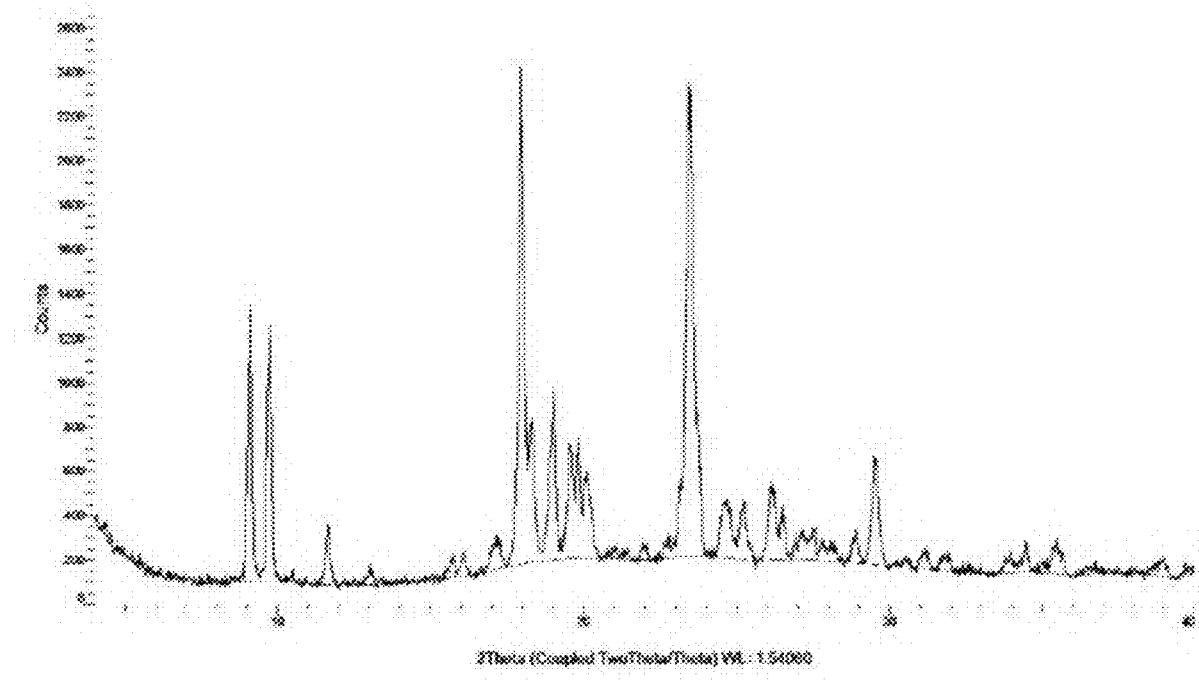

FIG. 397 depicts an XRPD diffractogram of the tabernanthalog glycolate salt. The XRPD signals observed in this diffractogram are characterized in Table 228.

Figure 398:
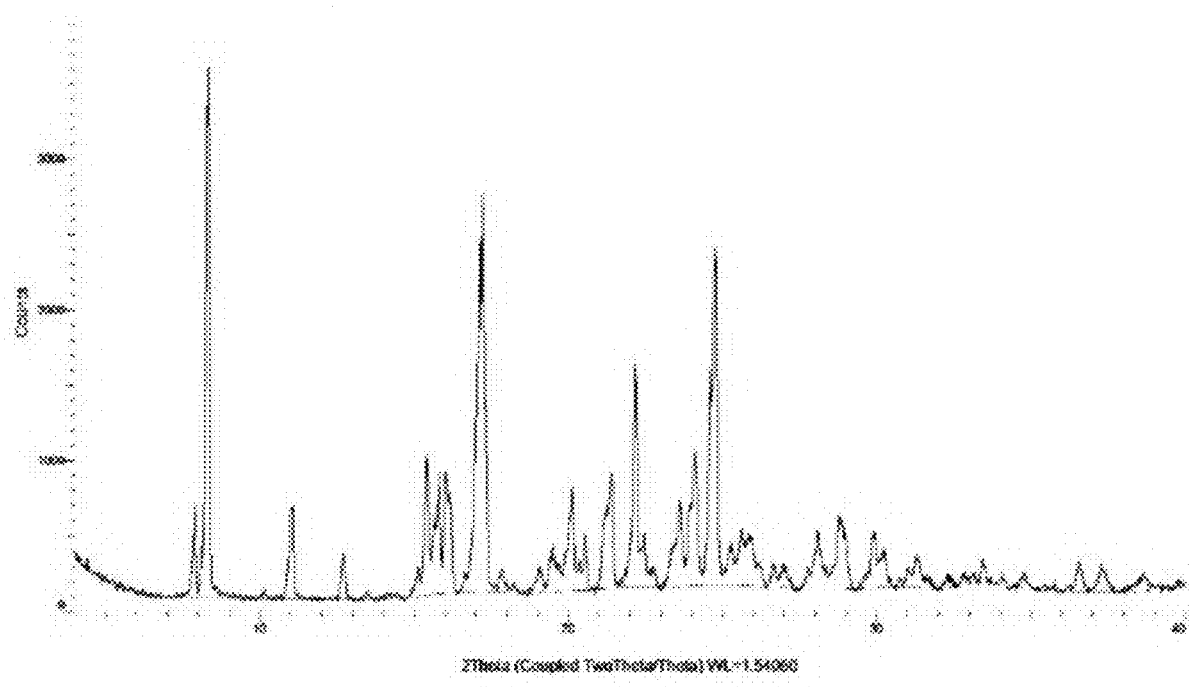

FIG. 398 depicts an XRPD diffractogram of the tabernanthalog succinate salt. The XRPD signals observed in this diffractogram are characterized in Table 229.

Figure 399:
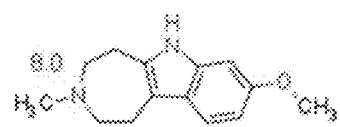

FIG. 399 depicts the calculated (c) $pK_a$ of tabernanthalog.

Figure 400:
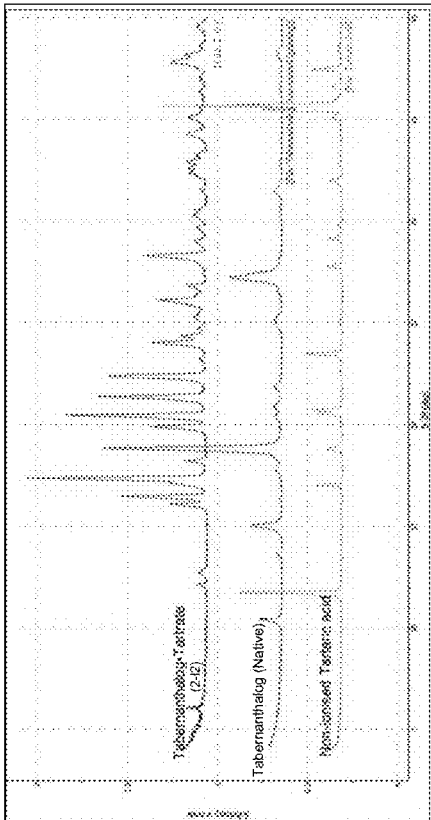

FIG. 400 depicts the XRPD powder diffraction pattern of the tabernanthalog sorbate salt compared to that of non-ionized tabernanthalog and sorbic acid.

Figure 401:
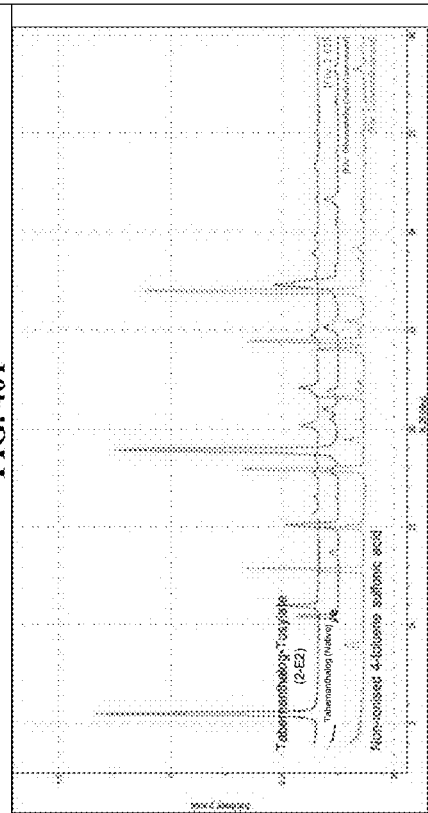

FIG. 401 depicts the XRPD powder diffraction pattern of the tabernanthalog tartrate salt compared to that of non-ionized tabernanthalog and L-tartaric acid.

Figure 402:
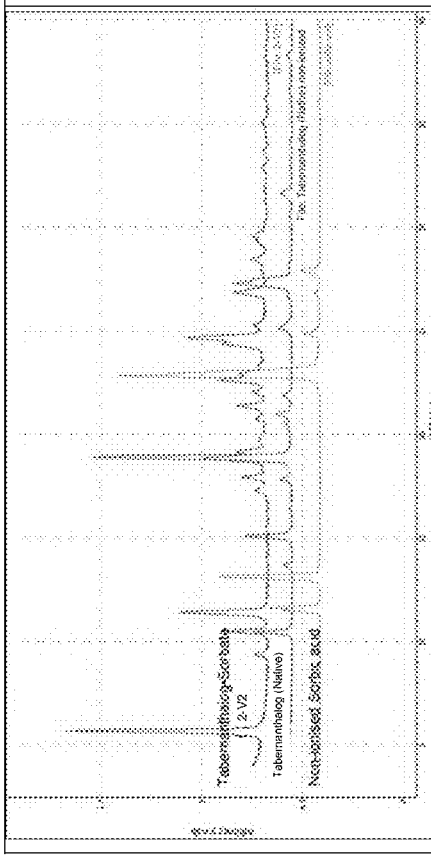

FIG. 402 depicts the XRPD powder diffraction pattern of the tabernanthalog malate salt compared to that of non-ionized Tabernanthalog and malic acid.

Figure 403:
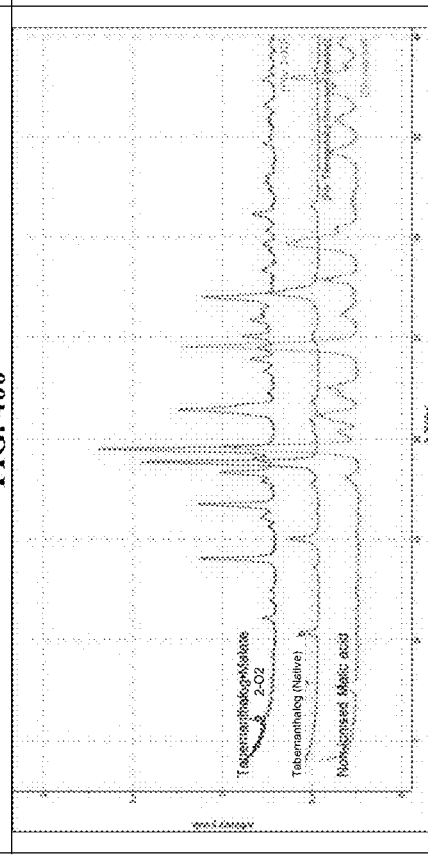

FIG. 403 depicts the XRPD powder diffraction pattern of the tabernanthalog tosylate salt compared to that of non-ionized Tabernanthalog and p-toluene sulfonic acid.

Figure 404:
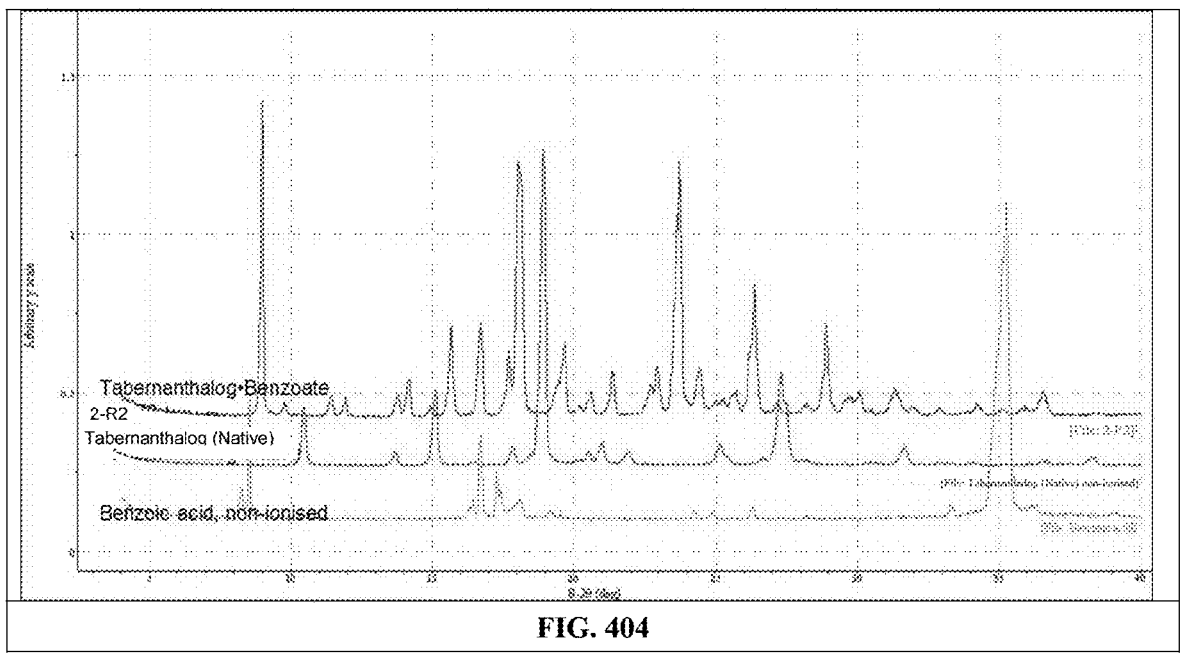

FIG. 404 depicts the XRPD powder diffraction pattern of the tabernanthalog benzoate salt (2-R2; (Experiment Reference 2-Sample Reference R2)) compared to that of non-ionized tabernanthalog (native) and benzoic acid.

FIG. 405 depicts the XRPD diffractogram overlay of the tabernanthalog tartrate salt, 3-A1 (Experiment Reference 3-Sample Reference A1, top) and 2-I2 (Experiment Reference 2-Sample Reference I2, bottom).

FIG. 406 depicts the XRPD diffractogram overlay of the tabernanthalog benzoate salt, 3-B1 (Experiment Reference 3-Sample Reference B1, top) and 2-R2 (Experiment Reference 2-Sample Reference R2, bottom).

FIG. 407 depicts the XRPD diffractogram overlay of the tabernanthalog sorbate salt, 3-C1 (Experiment Reference 3-Sample Reference C1, top) and 2-V2 (Experiment Reference 2-Sample Reference V2, bottom).

Figure 408:
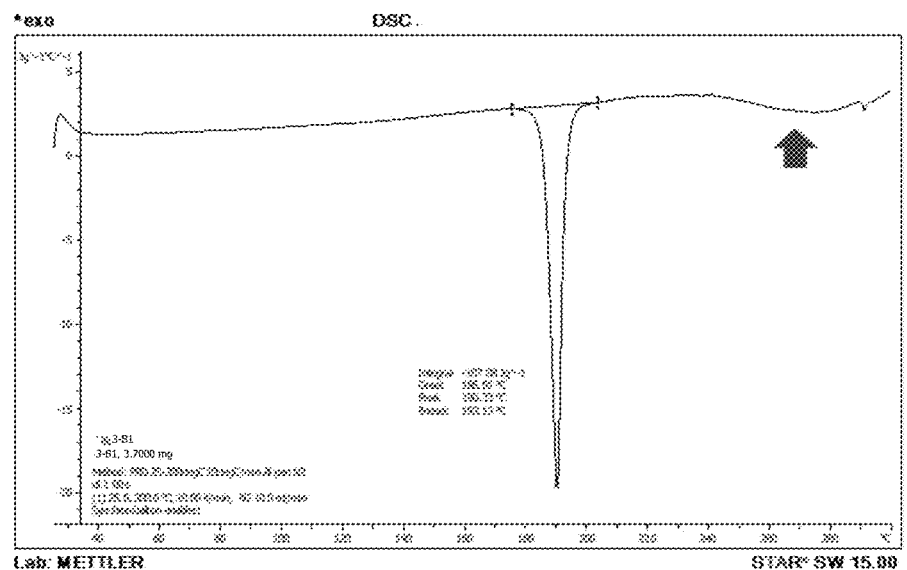

FIG. 408 depicts the DSC thermogram of 3-B1 (Experiment Reference 3-Sample Reference B1).

Figure 409:
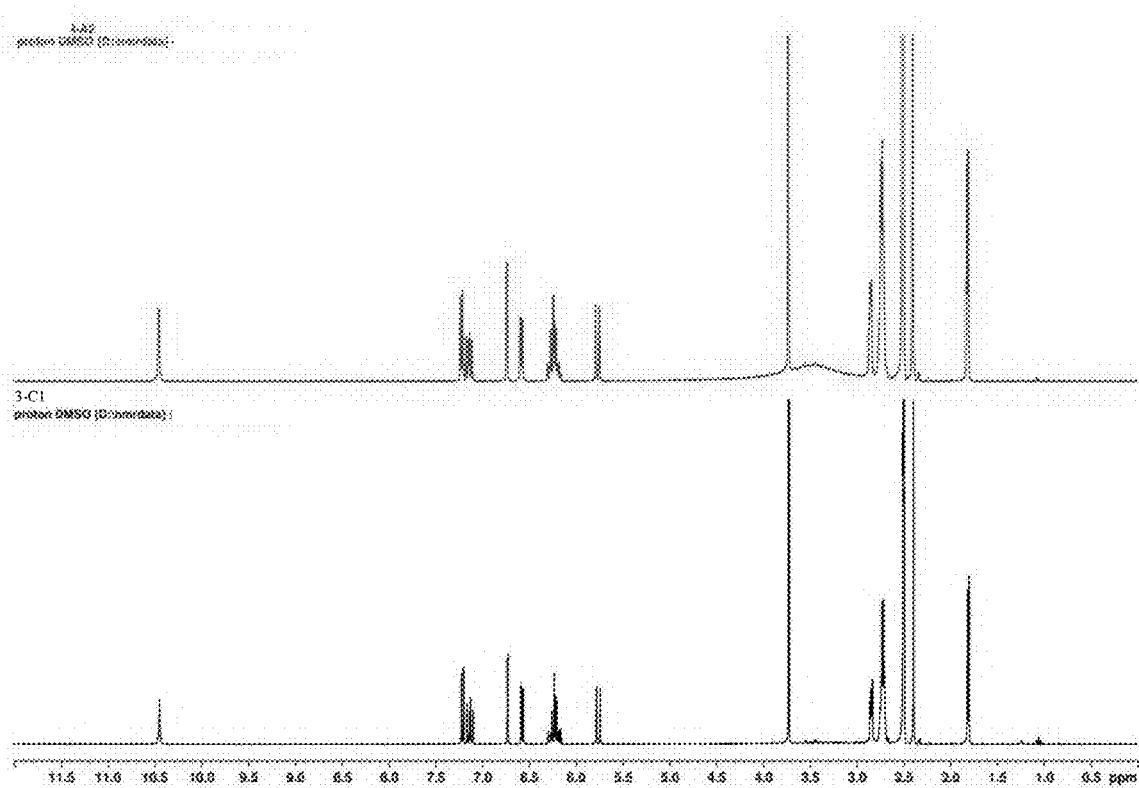
Figure 410:
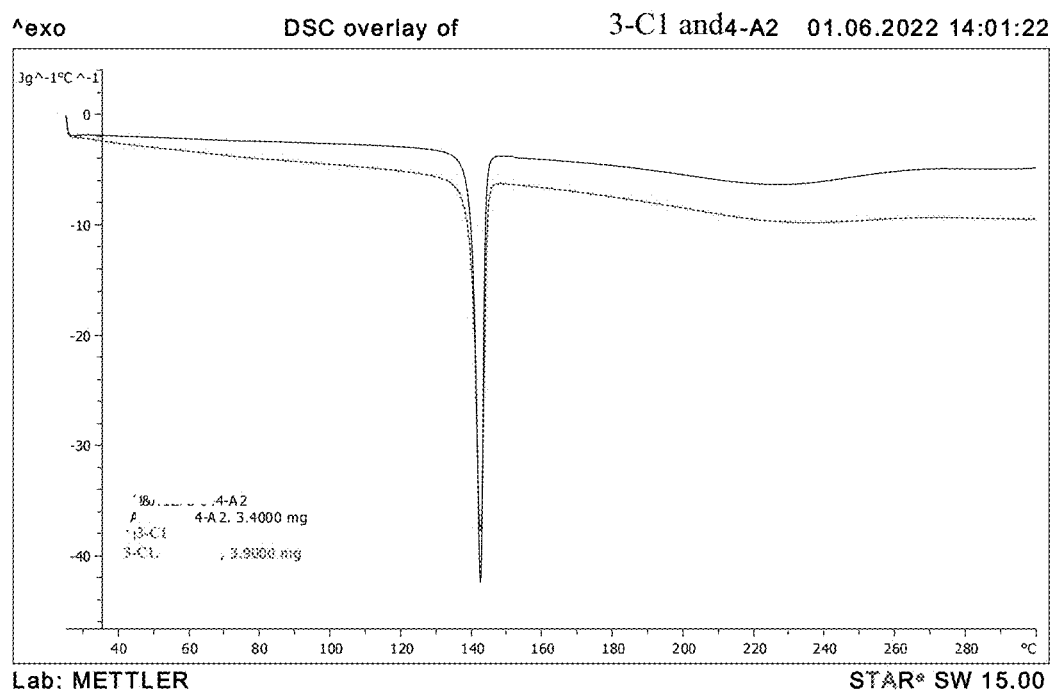

FIG. 409 depicts the 1H NMR spectrum overlay of the tabernanthalog sorbate salt (4-A2; Experiment Reference 4-Sample Reference A2) (top; concordant with reference) and 3-C1 (Experiment Reference 3-Sample Reference C1) (bottom) FIG. 410 depicts the DSC thermogram overlay of the tabernanthalog sorbate salt (4-A2; Experiment Reference 4-Sample Reference A2) and 3-C1 (Experiment Reference 3-Sample Reference C1).

Figure 411:
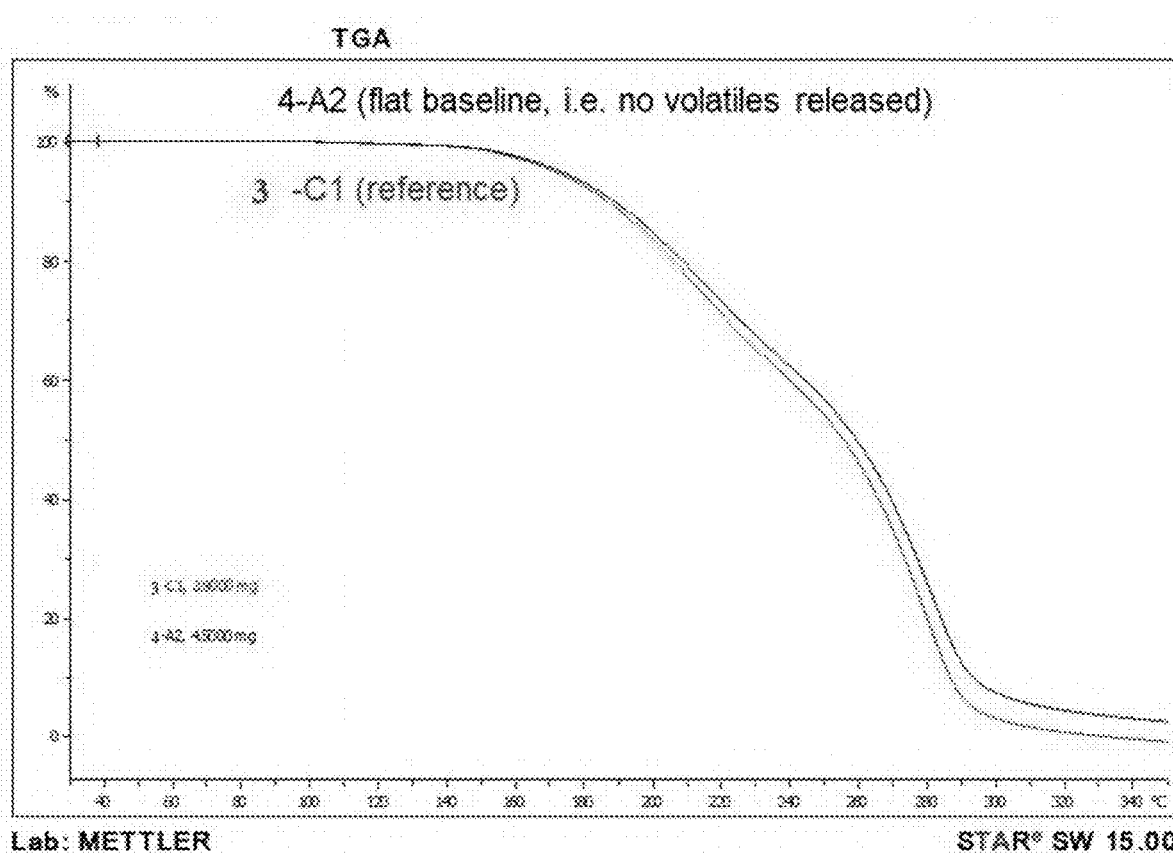

FIG. 411 depicts the TGA thermogram overlay of the tabernanthalog sorbate salt (4-A2; Experiment Reference 4-Sample Reference A2) and 3-C1 (Experiment Reference 3-Sample Reference C1).

Figure 412:
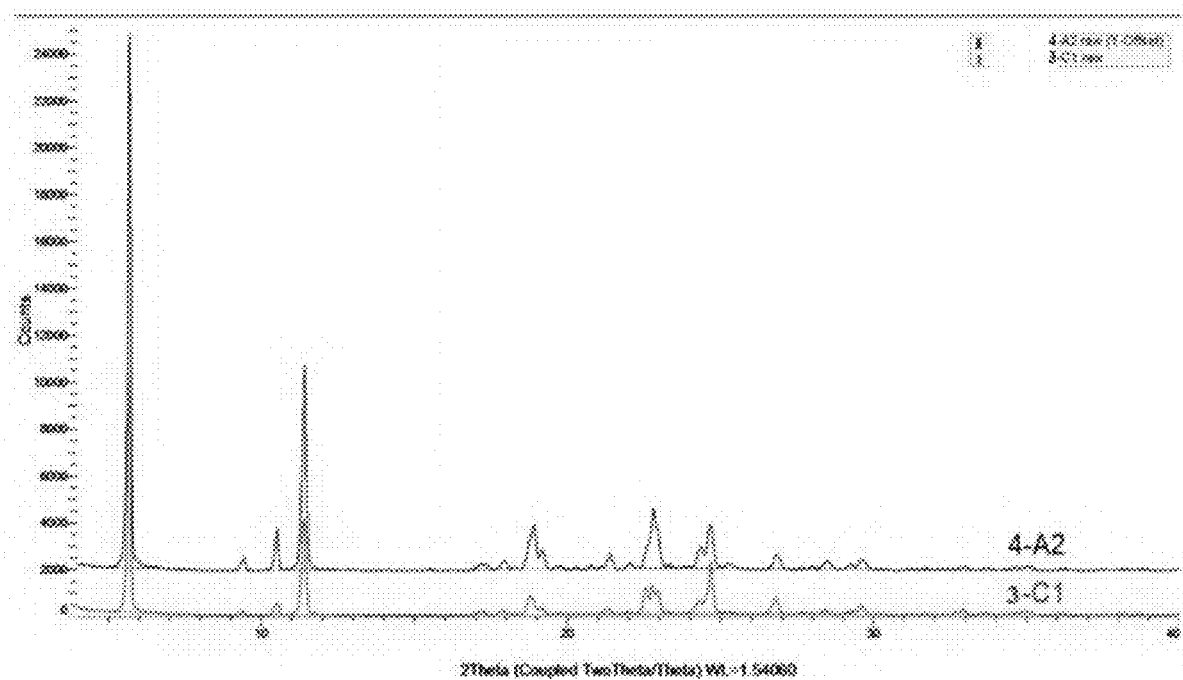

FIG. 412 depicts the XRPD diffractogram overlay of the tabernanthalog sorbate salt (4-A2; Experiment Reference 4-Sample Reference A2; congruent with the reference pattern) with 3-C1 (Experiment Reference 3-Sample Reference C1).

Figure 413:
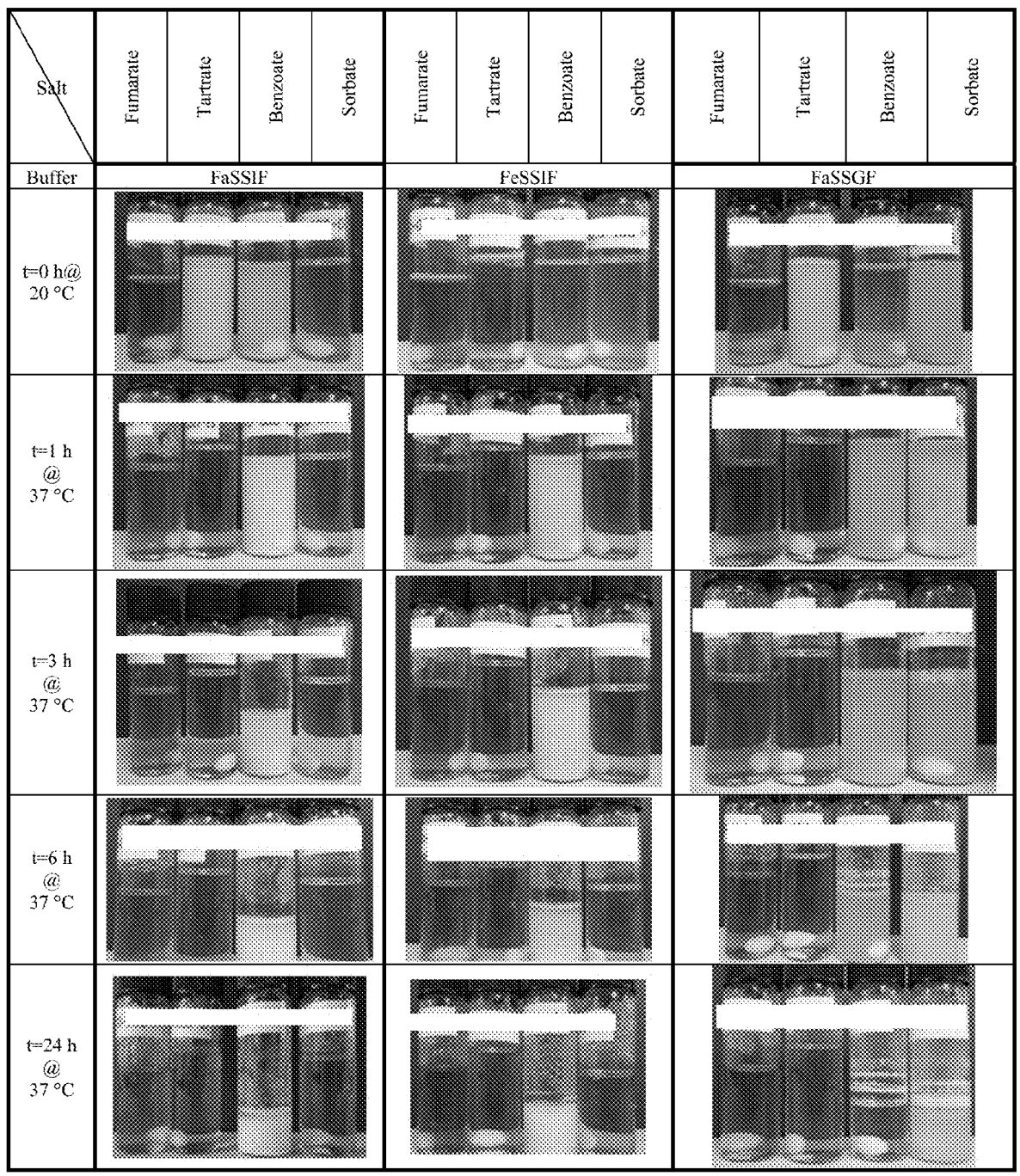

FIG. 413 depicts the photographs of the SIF buffer solubility panel, recorded at timepoints t=0, 1 h, 3 h, 6 h and 24 h; all dissolved except the tabernanthalog benzoate salt (5-C (Experiment Reference 5-Sample Reference C), 5-G (Experiment Reference 5-Sample Reference G), and 5-K (Experiment Reference 5-Sample Reference K)) in all SIF buffers. The tabernanthalog sorbate salt (5-L; Experiment Reference 5-Sample Reference L) remained suspended only in FaSSGF.

Figure 414:
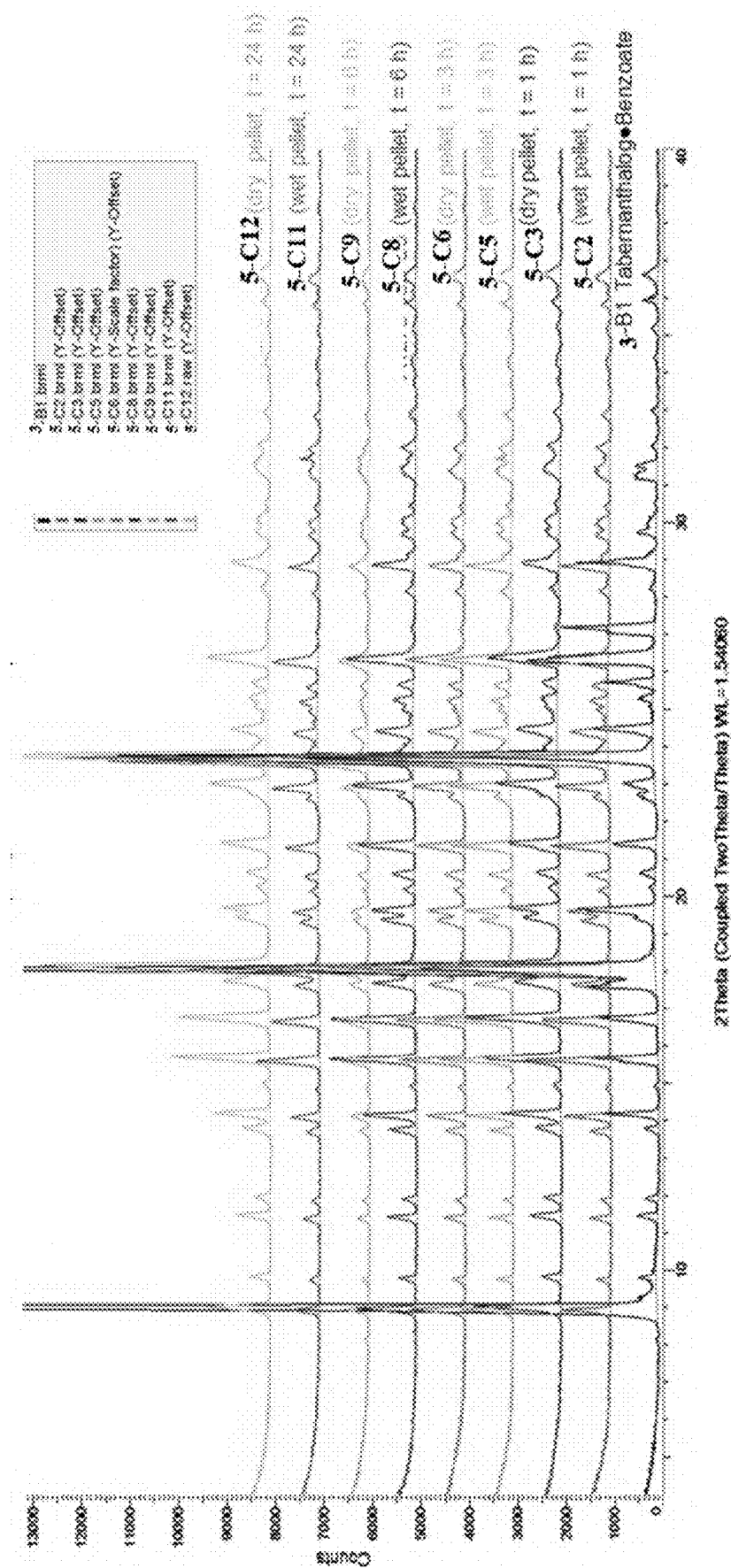

FIG. 414 depicts the XRPD diffractogram overlay of the tabernanthalog benzoate salt (input batch 3-B1 (Experiment Reference 3-Sample Reference B1)) and the various time point analyses from FaSSIF (5-C (Experiment Reference 5-Sample Reference C), wet and dry pellets).

Figure 415:
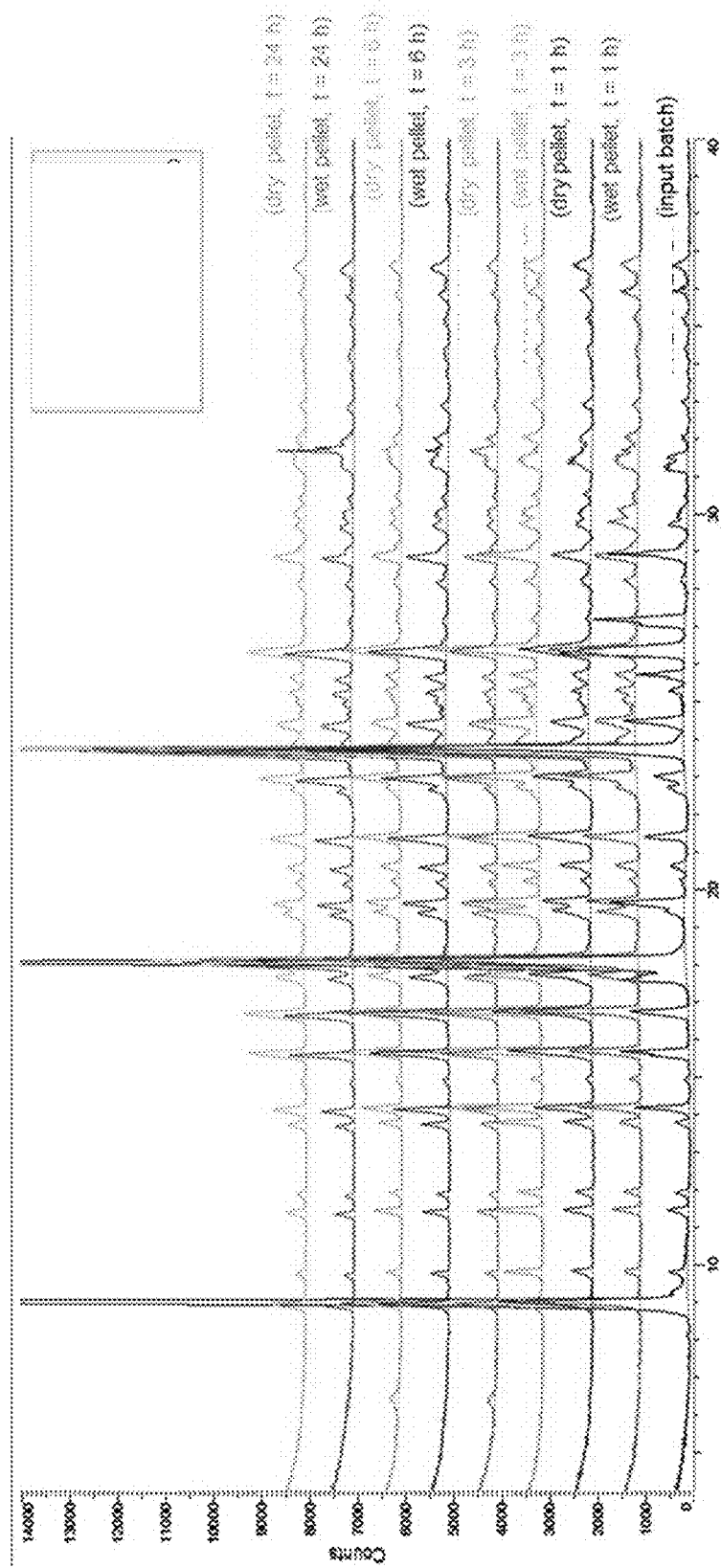

FIG. 415 depicts the XRPD diffractogram overlay of the tabernanthalog benzoate salt (input batch 3-B1: Experiment Reference 3-Sample Reference B1) and the various time point analyses from FeSSIF (5-G (Experiment Reference 5-Sample Reference G), wet and dry pellets).

Figure 416:
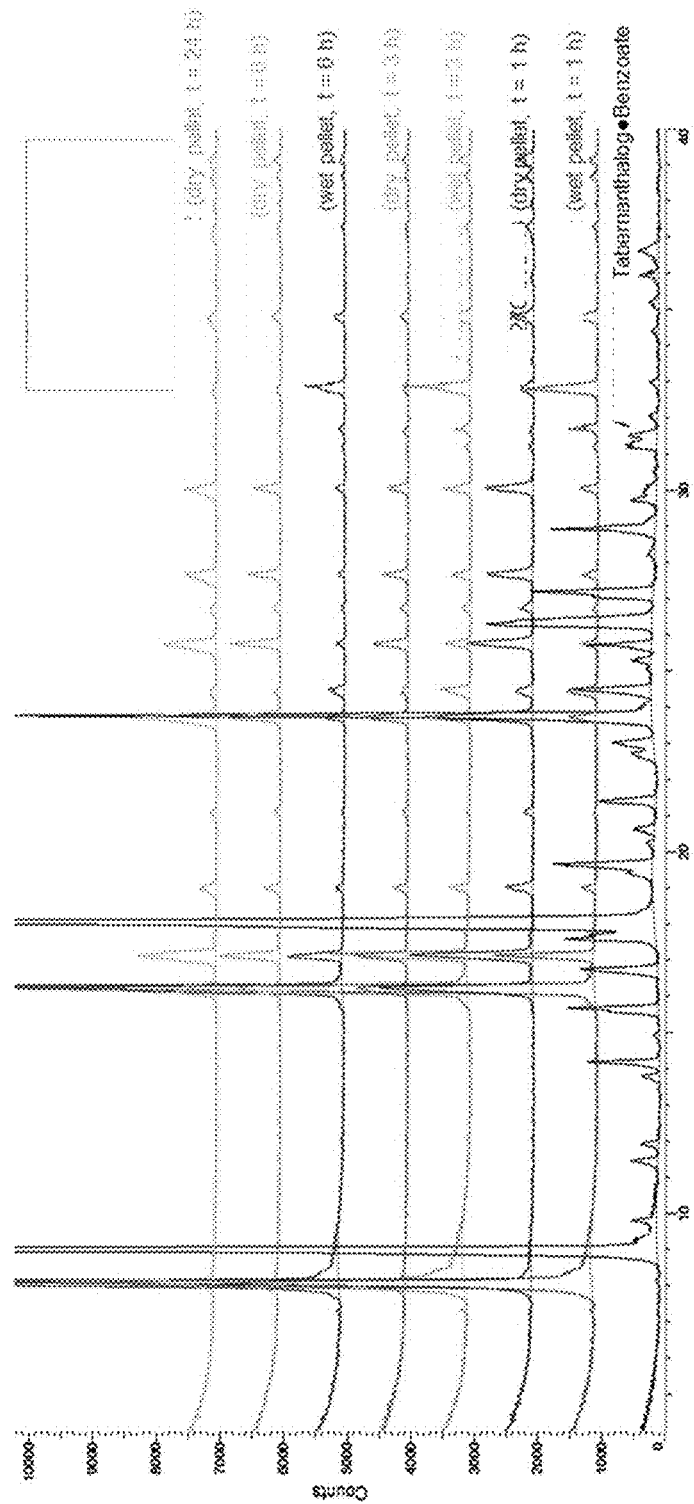

FIG. 416 depicts the XRPD diffractogram overlay of the tabernanthalog benzoate salt (input batch 3-B1; Experiment Reference 3-Sample Reference B1) and the various time point analyses from FaSSGF (wet and dry pellets). For 5-K11 (Experiment Reference 5-Sample Reference K11) (wet pellet, t=24 h), there was insufficient material for analysis.

Figure 417:
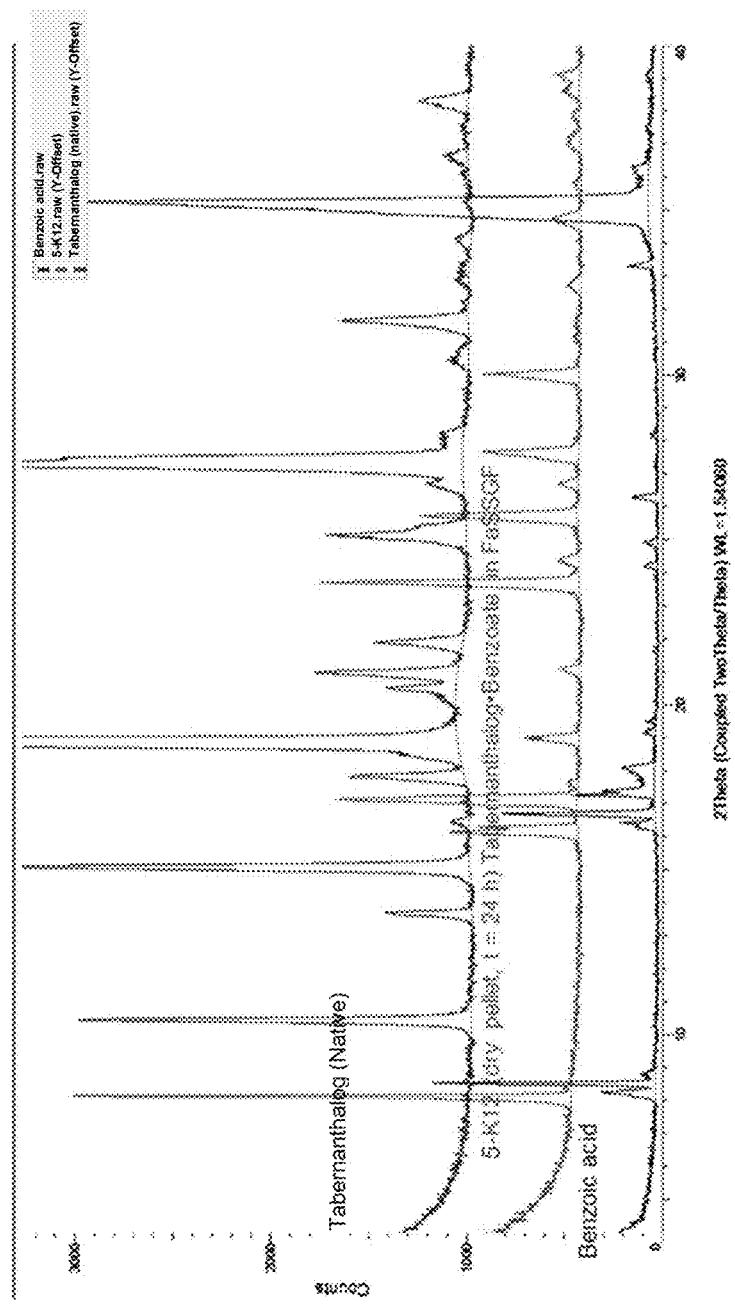

FIG. 417 depicts the XRPD diffractogram overlay of 5-K12 (Experiment Reference 5-Sample Reference K12) (dry pellet, t=24 h, middle) with tabernanthalog (native) (top) and benzoic acid (bottom).

Figure 418:
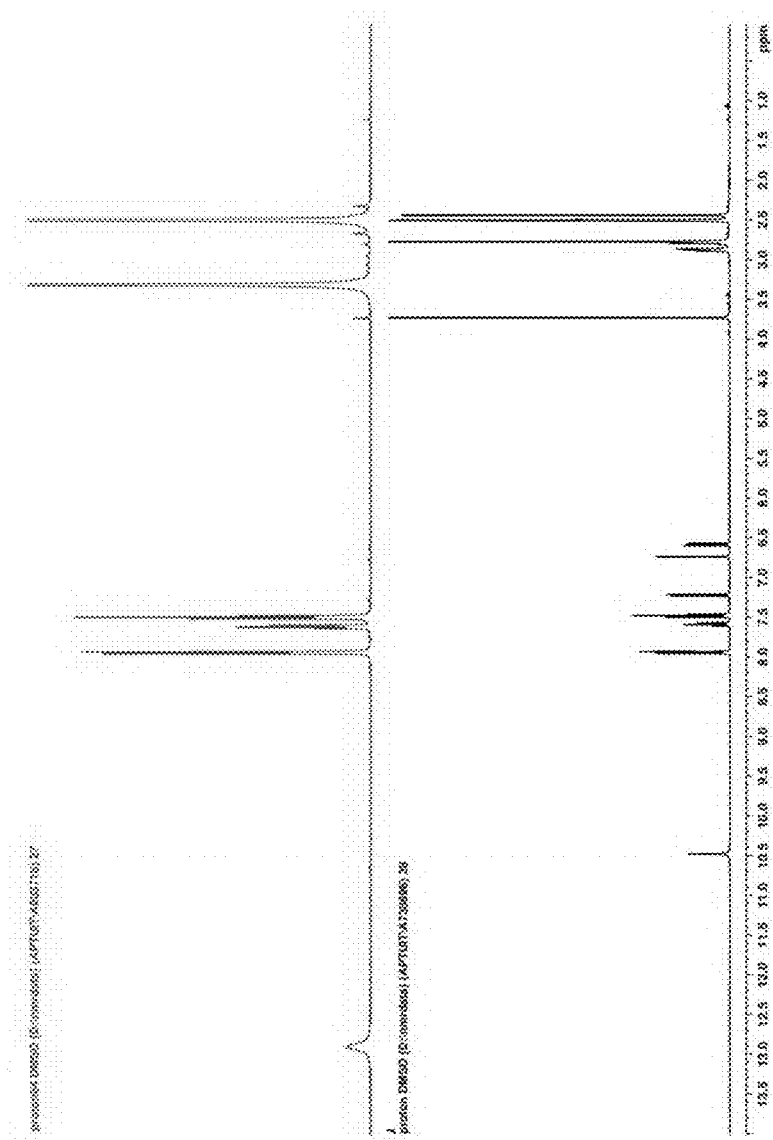

FIG. 418 depicts the $^1$H NMR overlay of 5-K12 (Experiment Reference 5-Sample Reference K12) (dry pellet, t=24 h, top) and 3-B1 (Experiment Reference 3-Sample Reference B1) (Tabernanthalog (native), input, bottom). In the $^1$H NMR analysis, API peaks are absent from 5-K12.

Figure 419:
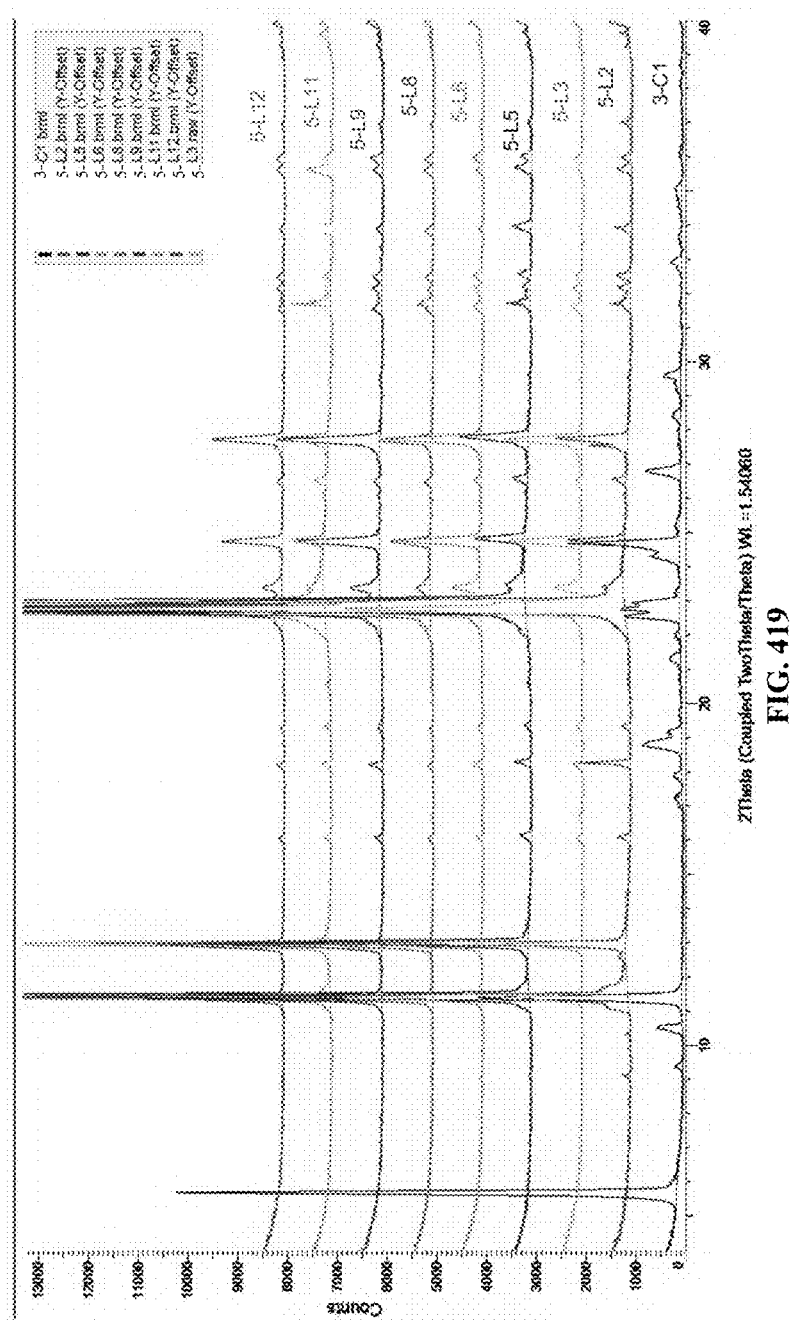

FIG. 419 depicts the XRPD diffractogram overlay of, from bottom to top, the tabernanthalog sorbate salt (input batch 3-C1; Experiment Reference 3-Sample Reference C1) and the various time point analyses from FaSSGF 5-L2 (wet pellet, t=1 h), 5-L3 (dry pellet, t=1 h) 5-L5 (wet pellet, t=3 h), 5-L6 (dry pellet, t=3 h), 5-L8 (wet pellet, t=6 h), 5-L9 (dry pellet, t=6 h), 5-L11 (wet pellet, t=24 h), 5-L12 (dry pellet, t=24 h), wherein 5-L2 is (Experiment Reference 5-Sample Reference L2); 5-L3 is (Experiment Reference 5-Sample Reference L3); 5-L5 is (Experiment Reference 5-Sample Reference L5); 5-L6 is (Experiment Reference 5-Sample Reference L6); 5-L8 is (Experiment Reference 5-Sample Reference L8); 5-L9 is (Experiment Reference 5-Sample Reference L9); 5-L11 is (Experiment Reference 5-Sample Reference L11); and 5-L12 is (Experiment Reference 5-Sample Reference L12).

Figure 420:
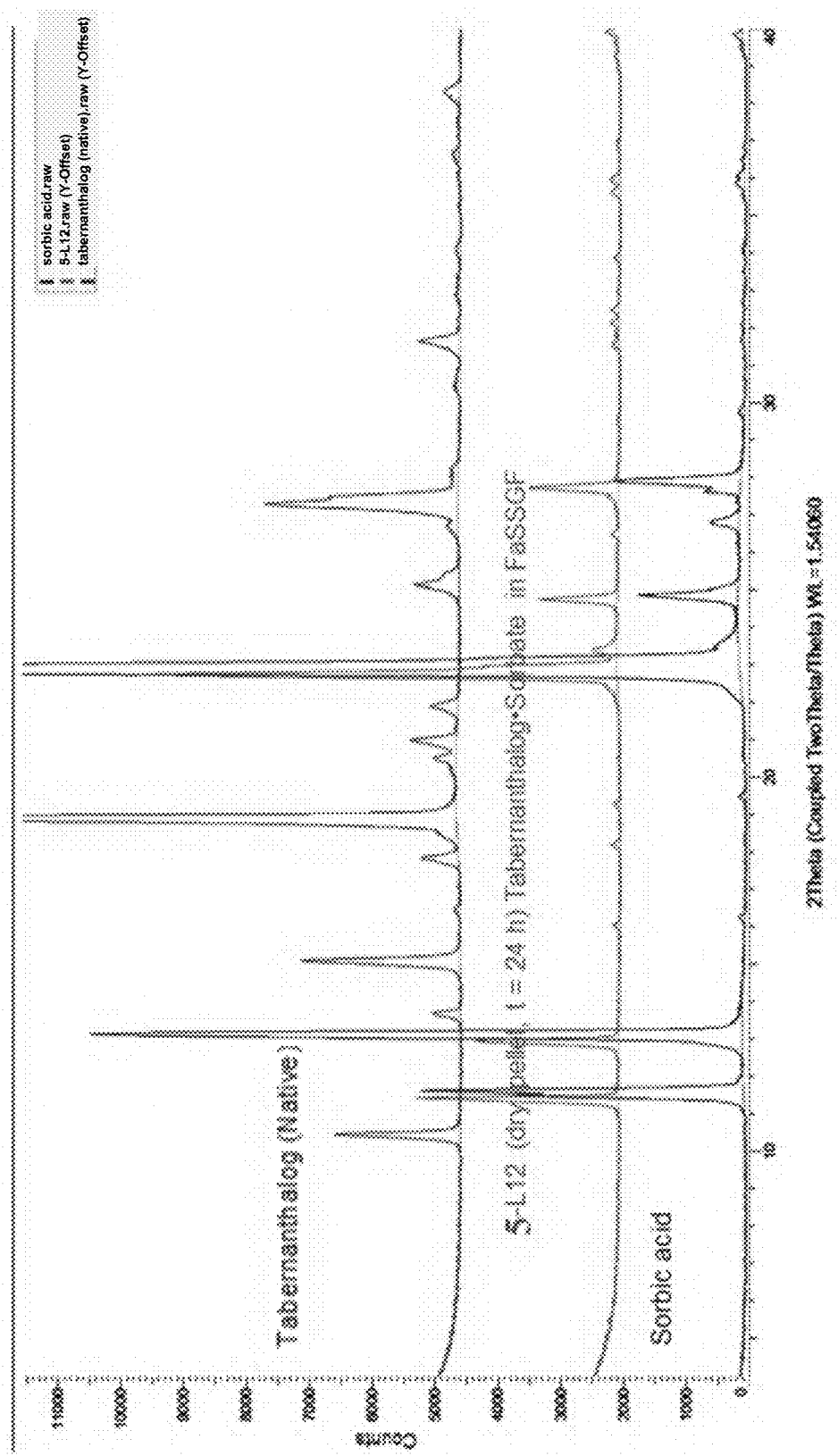

FIG. 420 depicts the XRPD diffractogram overlay of 5-L12 (Experiment Reference 5-Sample Reference L12) (dry pellet, t=24 h, middle) with tabernanthalog (native) (top) and sorbic acid (bottom).

Figure 421:
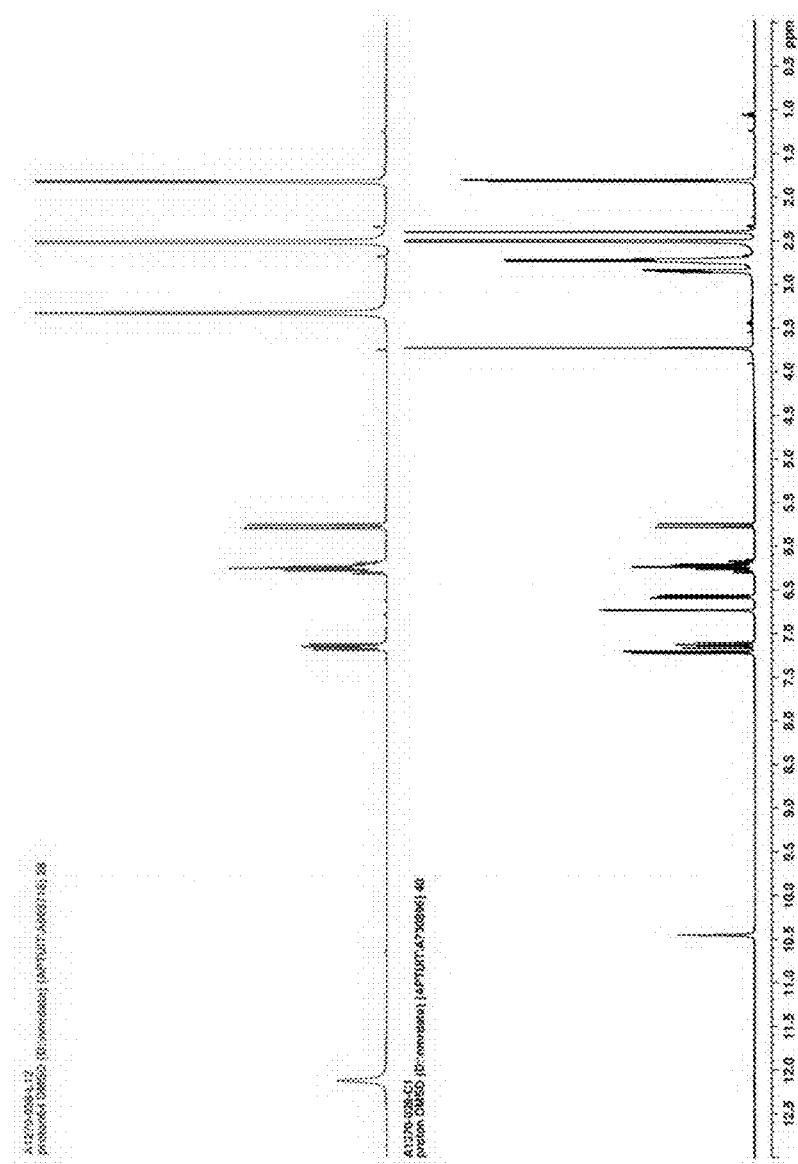

FIG. 421 depicts the $^1$H NMR overlay of 5-L12 (Experiment Reference 5-Sample Reference L12) (dry pellet, t=24 h, top) and 3-C1 (Experiment Reference 3-Sample Reference C1, tabernanthalog sorbate salt, input, bottom). The API peaks are absent from 5-L12.

FIG. 422 depicts the XRPD diffractogram overlay of, from bottom to top, 8-A4 of Example 5 (Experiment Reference 8-Sample Reference A4) of Example 5) (input, bottom), 6-A1 (Experiment Reference 6-Sample Reference A1) (t=5 d, middle) and 6-A2 (Experiment Reference 6-Sample Reference A2) (t=10 d, top).

FIG. 423 depicts the XRPD diffractogram overlay of 3-A1 (Experiment Reference 3-Sample Reference A1) (input, top), 6-B1 (Experiment Reference 6-Sample Reference B1) (t=5 d, bottom) and 6-B2 (Experiment Reference 6-Sample Reference B2) (t=10 d, middle).

FIG. 424 depicts the XRPD diffractogram overlay of 3-B1 (Experiment Reference 3-Sample Reference B1) (input, top), 6-C1 (Experiment Reference 6-Sample Reference C1) (t=5 d, bottom) and 6-C2 (Experiment Reference 6-Sample Reference C2) (t=10 d, middle).

FIG. 425 depicts the XRPD diffractogram overlay of 3-C1 (Experiment Reference 3-Sample Reference C1) (input, top), 6-D1 (Experiment Reference 6-Sample Reference D1) (t=5 d, bottom) and 6-D2 (Experiment Reference 6-Sample Reference D2) (t=10 d, middle).

Figures 426, 427, 428, 429:
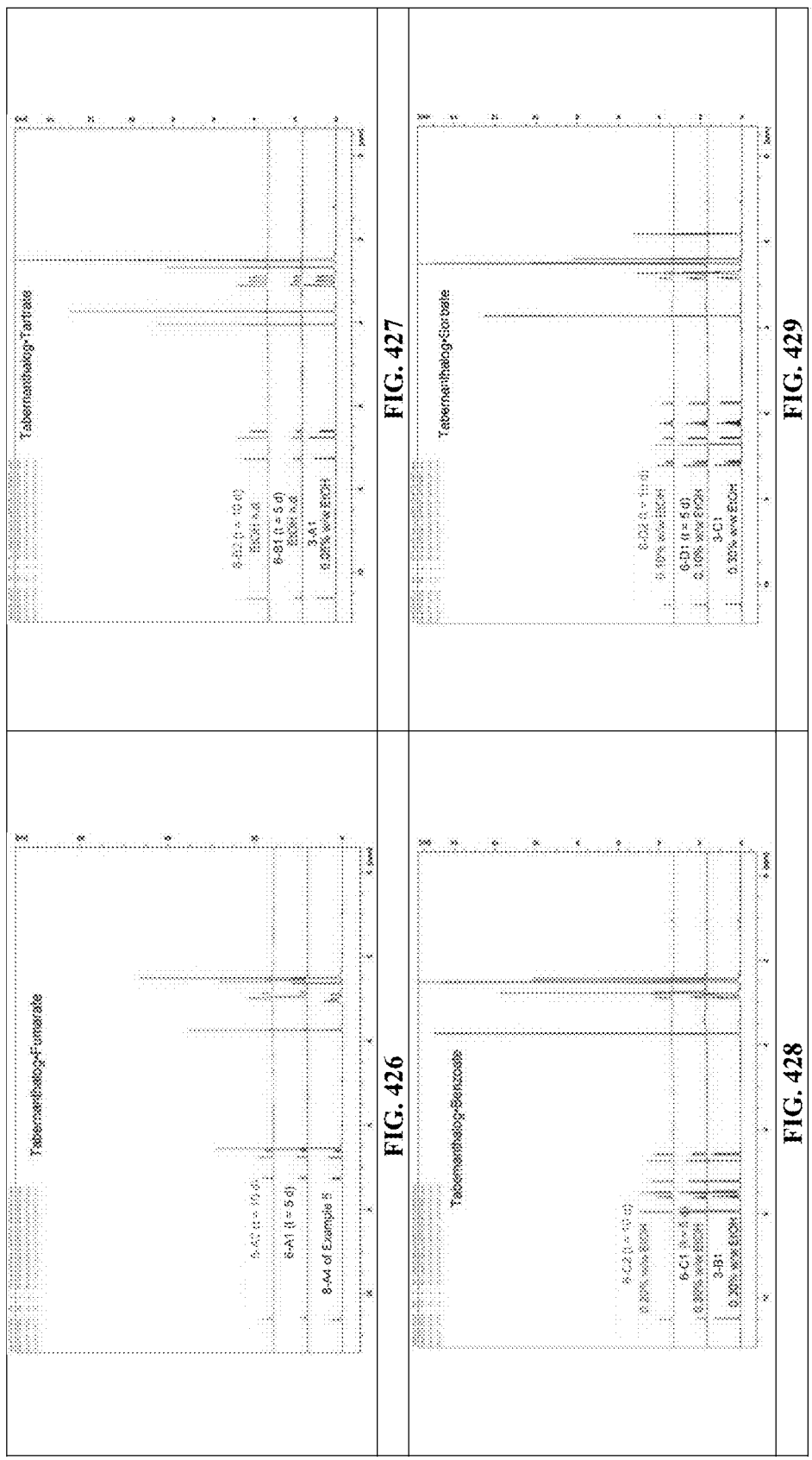

FIG. 426 depicts the $^1$H NMR spectrum overlay of [8-A4 (Experiment Reference 8-Sample Reference A4) of Example 5)] (input, bottom), 6-A1 (Experiment Reference 6-Sample Reference A1) (t=5 d, middle) and 6-A2 (Experiment Reference 6-Sample Reference A2) (t=10 d, top).

FIG. 427 depicts the $^1$H NMR spectrum overlay of 3-A1 (Experiment Reference 3-Sample Reference A1) (input, bottom), 6-B1 (Experiment Reference 6-Sample Reference B1) (t=5 d, middle) and 6-B2 (Experiment Reference 6-Sample Reference B2) (t=10 d, top).

FIG. 428 depicts the $^1$H NMR spectrum overlay of 3-B1 (Experiment Reference 3-Sample Reference B1) (input, bottom), 6-C1 (Experiment Reference 6-Sample Reference C1) (t=5 d, middle) and 6-C2 (Experiment Reference 6-Sample Reference C2) (t=10 d, top).

FIG. 429 depicts the $^1$H NMR spectrum overlay of 3-C1 (Experiment Reference 3-Sample Reference C1) (input, bottom), 6-D1 (Experiment Reference 6-Sample Reference D1) (t=5 d, middle) and 6-D2 (Experiment Reference 6-Sample Reference D2) (t=10 d, top).

Figure 430:
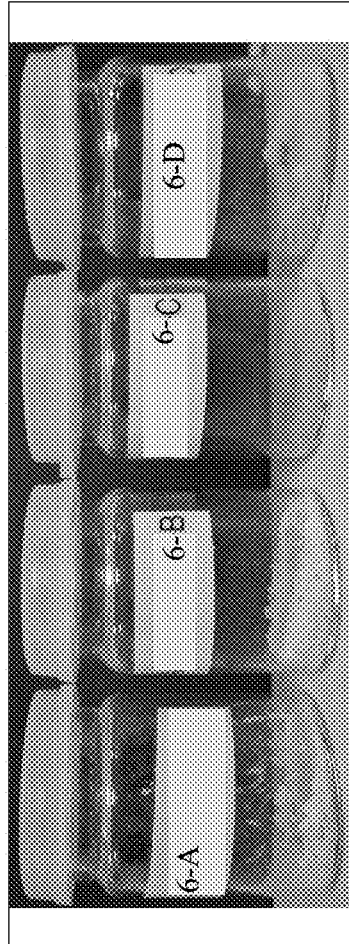

FIG. 430 depicts the photograph of 6-A (Experiment Reference 6-Sample Reference A, fumarate), 6-B (Experiment Reference 6-Sample Reference B, tartrate), 6-C (Experiment Reference 6-Sample Reference C, benzoate), and 6-D (Experiment Reference 6-Sample Reference D, sorbate) at t=0. [Note pictured loosely capped; stability panel commenced open capped.] Salt identities: A=Fumarate, B=Tartrate, C=Benzoate, D=Sorbate.

Figure 431:
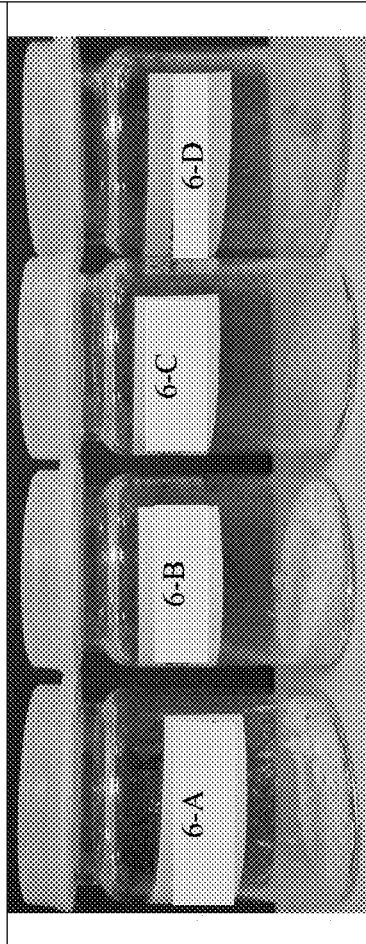

FIG. 431 depicts the photograph of 6-A (Experiment Reference 6-Sample Reference A, fumarate), 6-B (Experiment Reference 6-Sample Reference B, tartrate), 6-C (Experiment Reference 6-Sample Reference C, benzoate), and 6-D (Experiment Reference 6-Sample Reference D, sorbate) at t=5 d. Salt identities: A=Fumarate, B=Tartrate, C=Benzoate, D=Sorbate.

Figure 432:
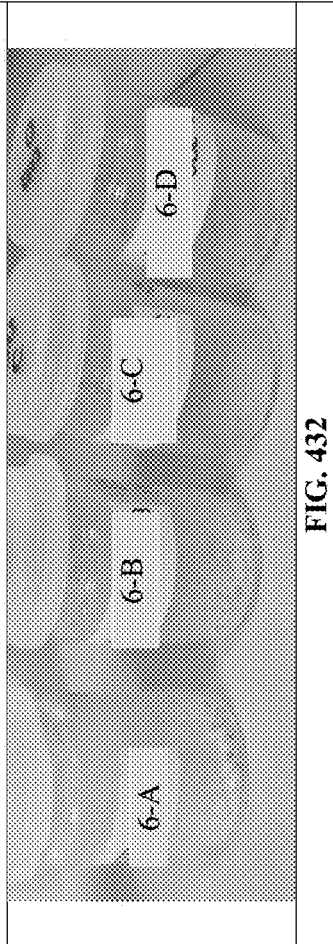

FIG. 432 depicts the photographs of 6-A (Experiment Reference 6-Sample Reference A, fumarate), 6-B (Experiment Reference 6-Sample Reference B, tartrate), 6-C (Experiment Reference 6-Sample Reference C, benzoate), and 6-D (Experiment Reference 6-Sample Reference D, sorbate) at t=10 d. Salt identities: A=Fumarate, B=Tartrate, C=Benzoate, D=Sorbate.

Figures 433, 434:
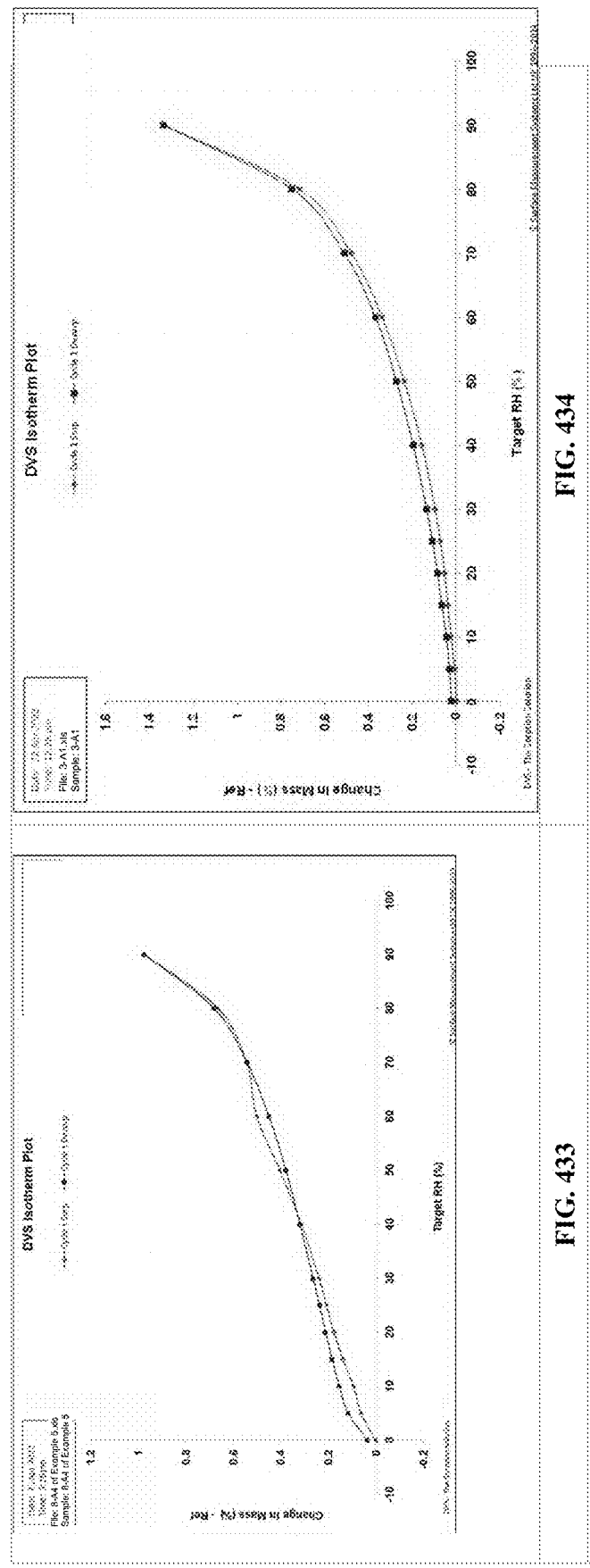

FIG. 433 depicts the DVS Sorption isotherms of the tabernanthalog monofumarate salt [Pattern #6a, Form A, 8-A4 (Experiment Reference 8-Sample Reference A4) of Example 5)].

FIG. 434 depicts the DVS Desorption isotherms of the tabernanthalog tartrate salt (3-A1 (Experiment Reference 3-Sample Reference A1)).

Figures 435, 436:
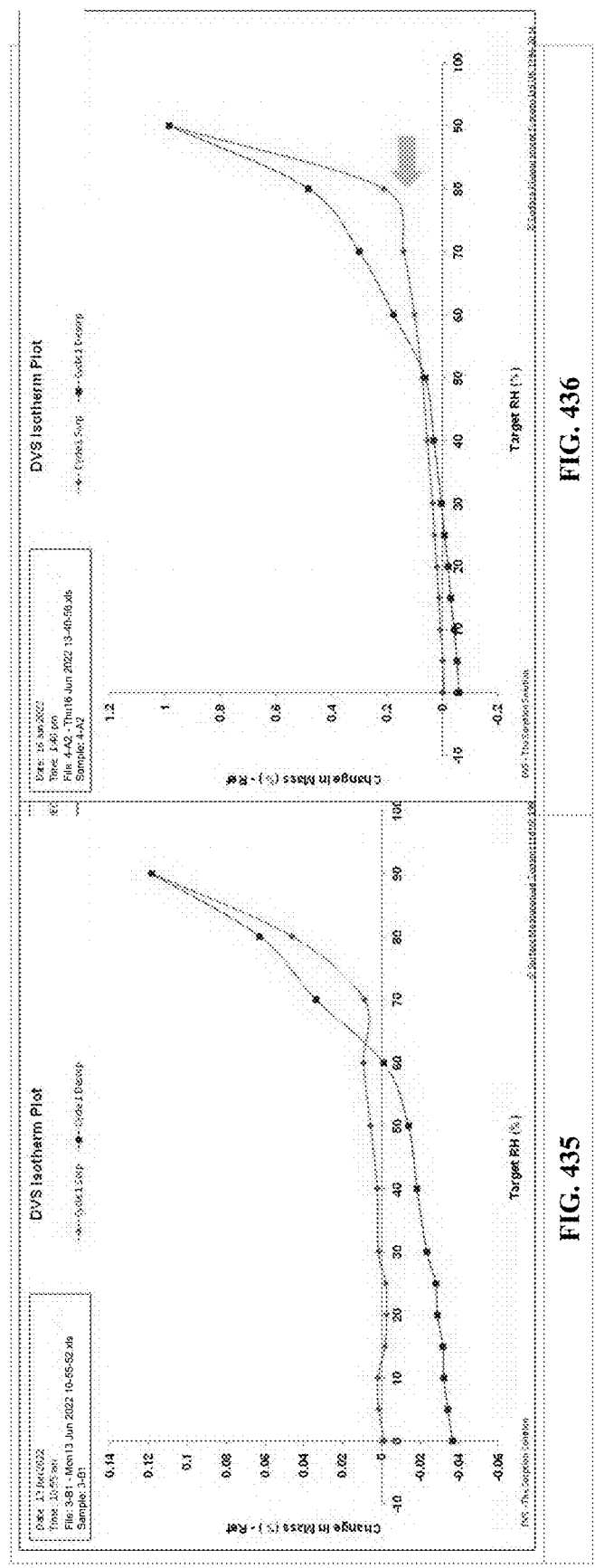

FIG. 435 depicts the DVS Sorption isotherms of the tabernanthalog benzoate salt (3-B1 (Experiment Reference 3-Sample Reference B1)).

FIG. 436 depicts the DVS Desorption isotherms of the tabernanthalog sorbate salt (4-A2 (Experiment Reference 4-Sample Reference A2)).

Figure 437:
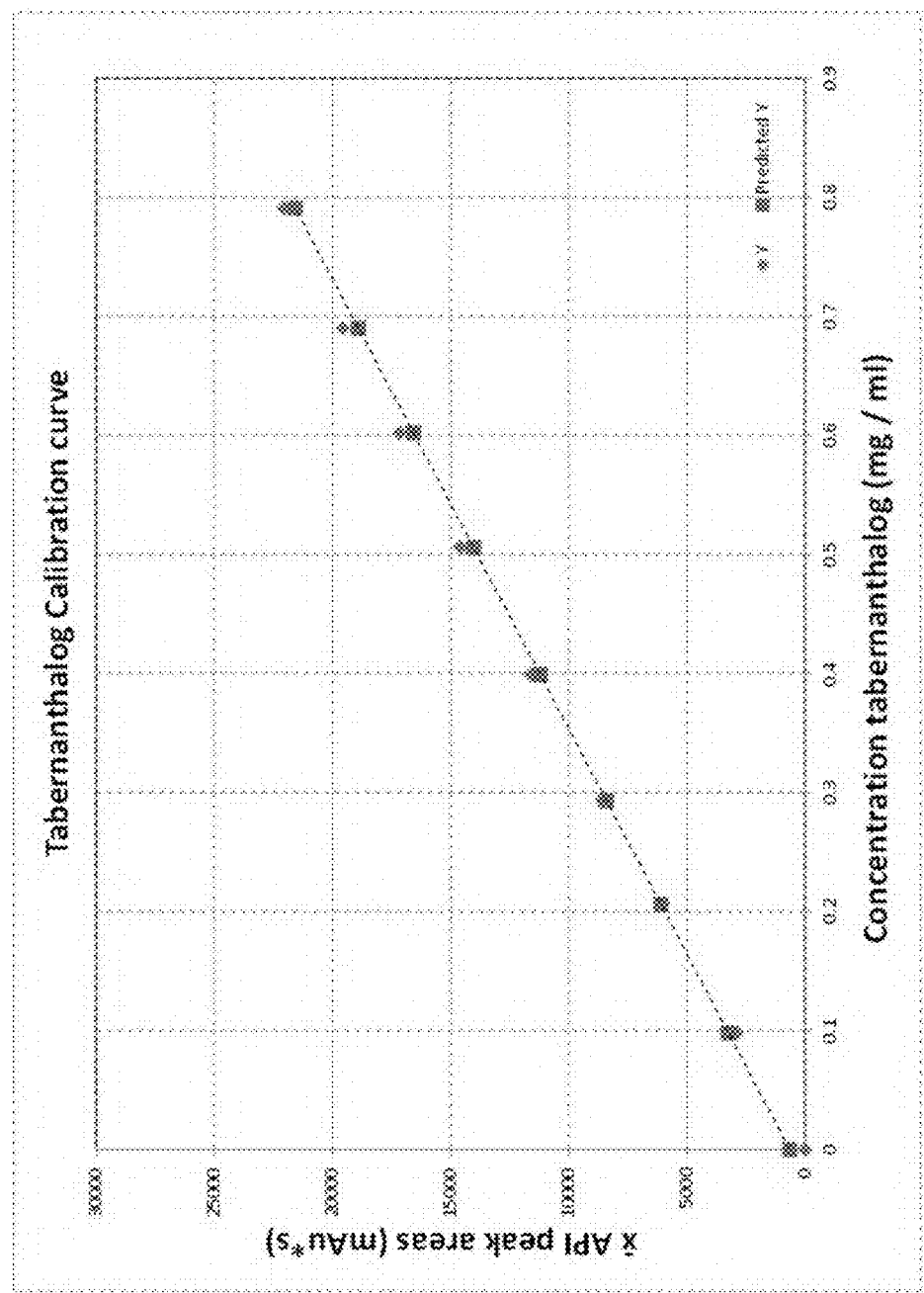

FIG. 437 depicts the calibration curve of tabernanthalog.

Figure 438:
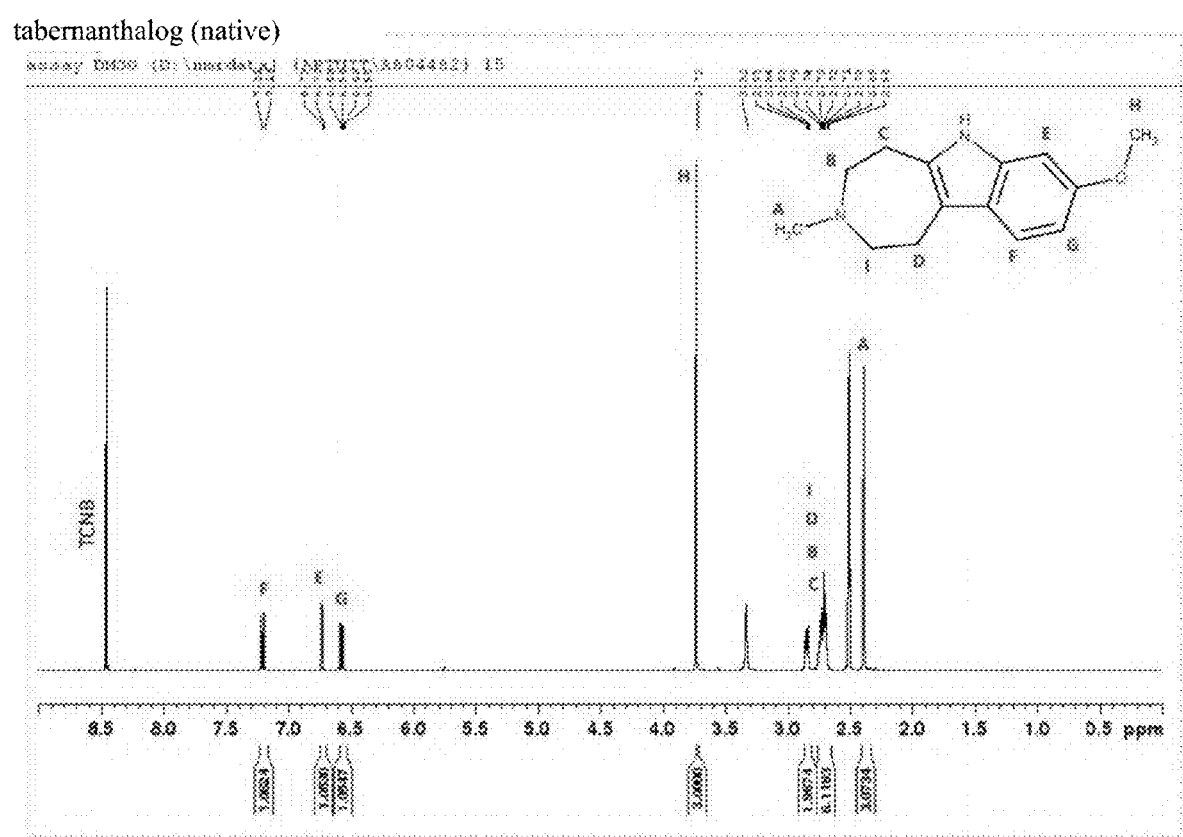

FIG. 438 depicts the Q $^1$H NMR of tabernanthalog (native), analysis was acquired in DMSO-d6 and calibrated to the non-deuterated solvent residual at 2.50 ppm. Q $^1$H NMR assay (vs TCNB) showed 99.0% w/w. DCM content 0.2% w/w. KF titre determined water content 0.2% w/w (ca. 25 mg sample analyzed).

Figure 439:
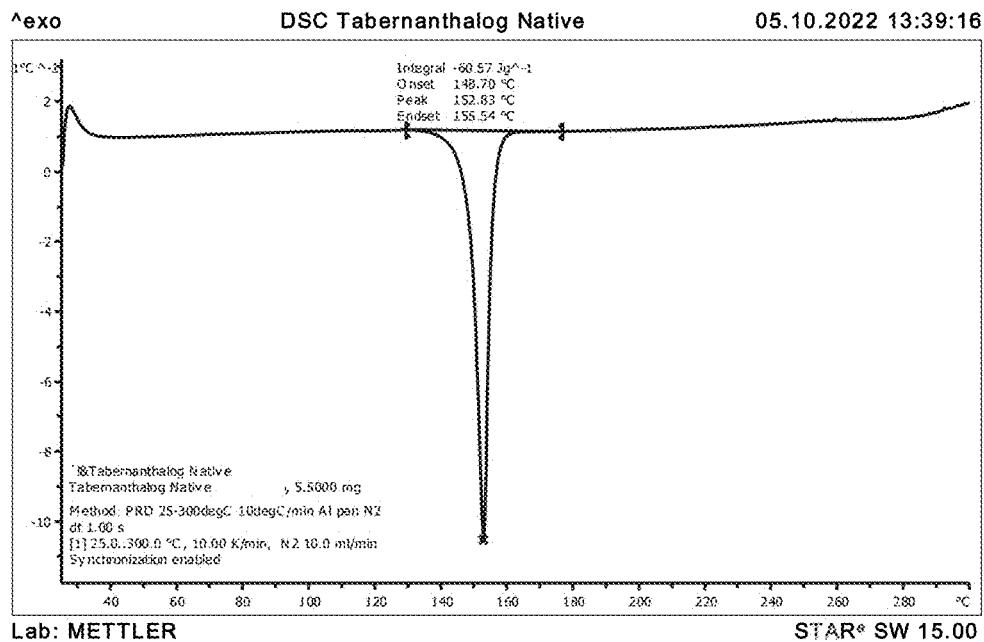

FIG. 439 depicts the DSC profile of tabernanthalog (native), analysis was acquired at a ramp rate of +10° C./minute. Consistent with single sharp melt event 149° C. (−60.6 Jg$^{-1}$); non-ablative, cf. The tabernanthalog fumarate salt. The change in $c_p$ at the beginning of each thermal segment was attributed to the weight differential between the reference and sample pans.

Figure 440:
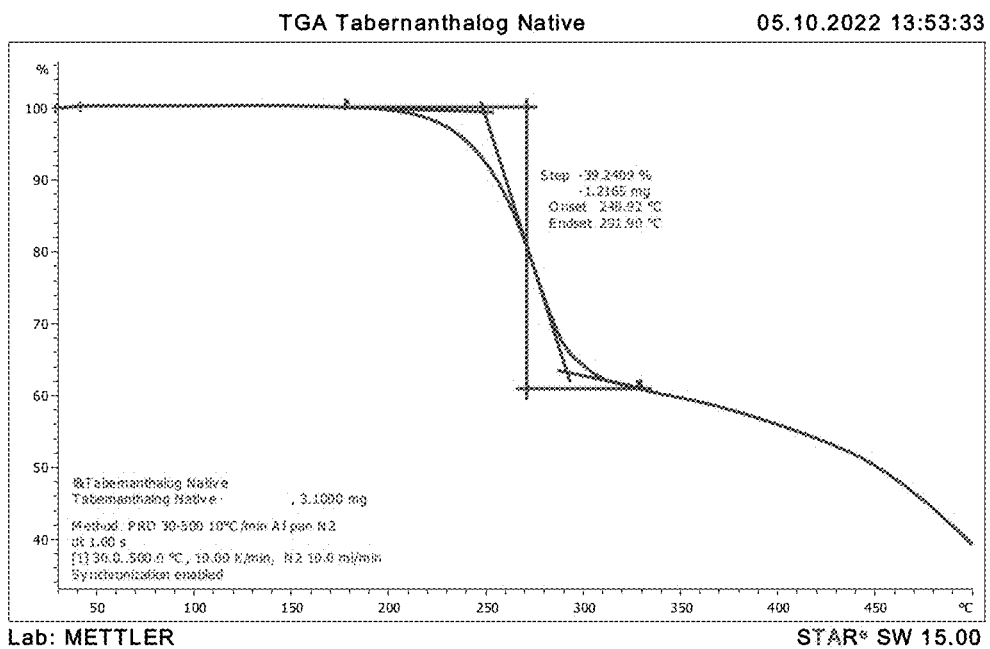

FIG. 440 depicts the TGA profile of tabernanthalog (native), analysis was acquired at a ramp rate of +10° C./minute. Flat baseline was observed <200° C. Significant weight loss was observed at higher temperature (>200° C.), attributed to chemical degradation and ablation of the sample.

Figure 442:
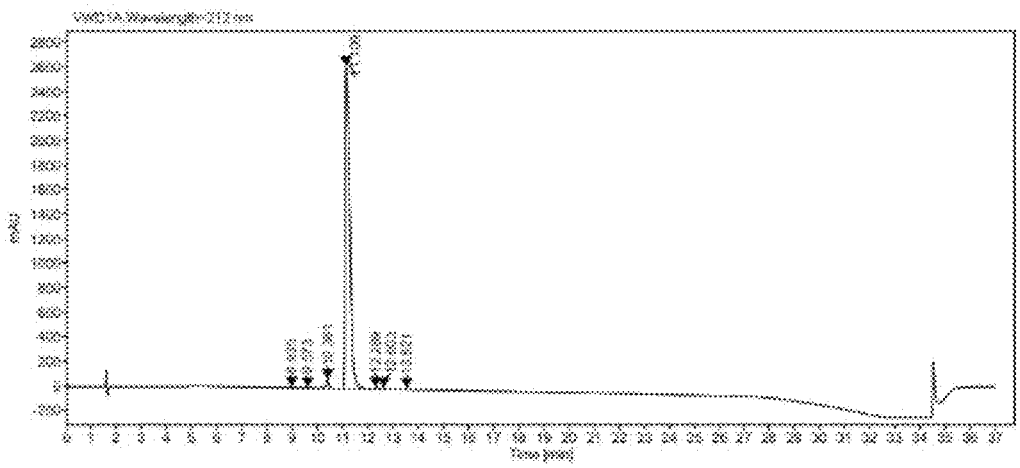

FIG. 442 depicts the HPLC of tabernanthalog (native).

Figure 443:
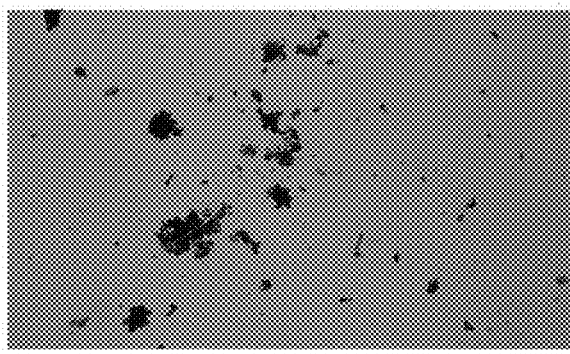

FIG. 443 depicts the PLM of tabernanthalog (native)×2 mag, NP.

Figure 444:
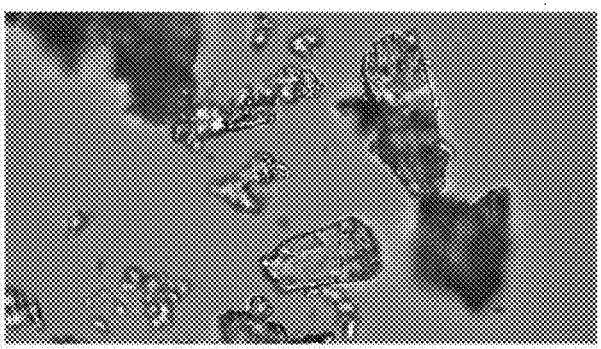

FIG. 444 depicts the PLM of tabernanthalog (native)×20 mag, NP (Non-homogeneous optically crystalline specimen).

Figure 445:
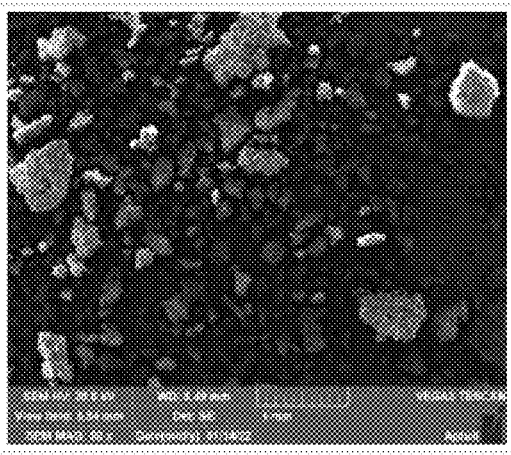

FIG. 445 depicts the SEM of tabernanthalog (native), resolution at 150×(wide field).

Figure 446:
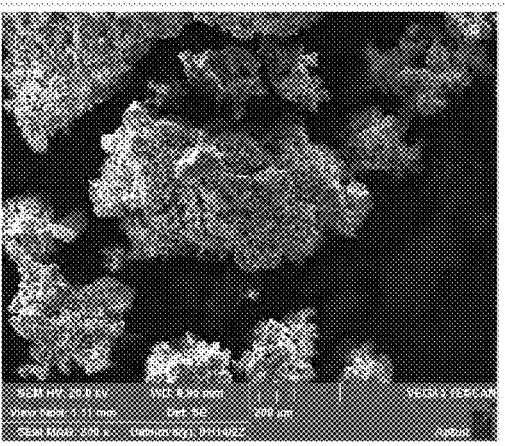

FIG. 446 depicts the SEM of tabernanthalog (native), resolution at 250×(wide field).

Figure 447:
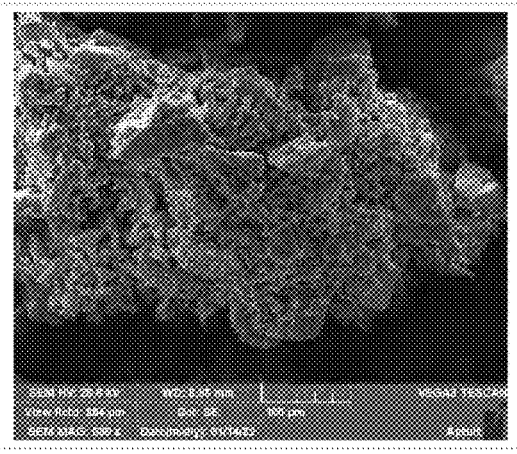

FIG. 447 depicts the SEM of tabernanthalog (native), resolution at 500×(wide field).

Figure 448:
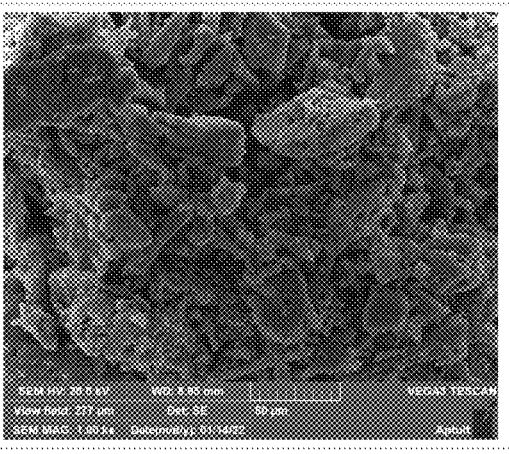

FIG. 448 depicts the SEM of tabernanthalog (native), resolution at 1000×(wide field).

Figures 449, 450:
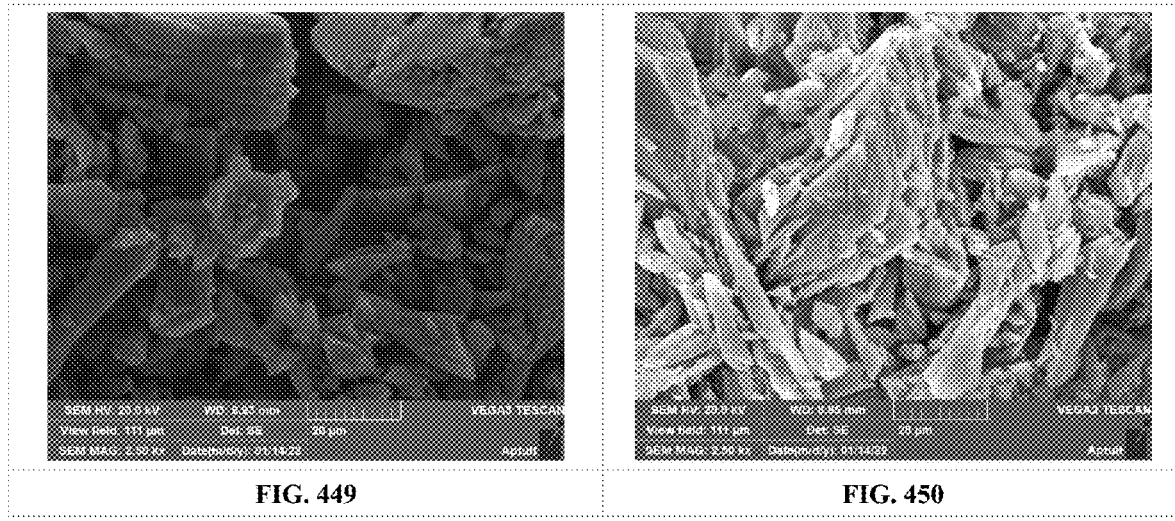

FIG. 449 depicts the SEM of tabernanthalog (native), resolution at 2500×(wide field).

FIG. 450 depicts the SEM of tabernanthalog (native), resolution at 2500×(different aspect).

Figure 451:
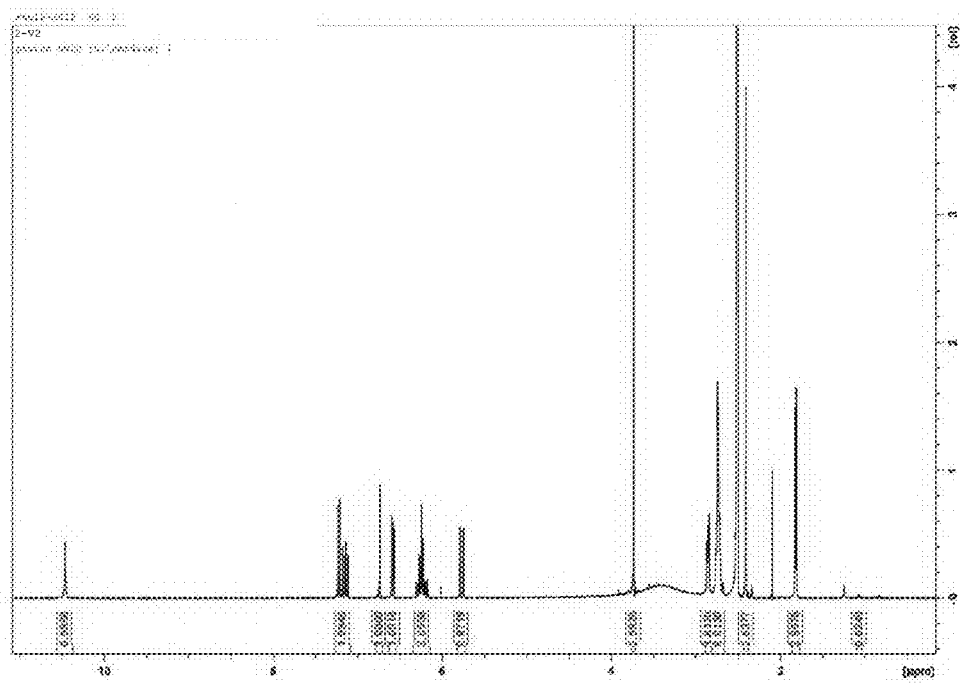

FIG. 451 depicts the $^1$H NMR of 2-V2 (Experiment Reference 2-Sample Reference V2), acquired in DMSO-d6 and calibrated to the non-deuterated solvent residual at 2.50 ppm. 1.0 mol of API to 1.0 mol sorbic acid. Ethanol content 0.1% w/w.

Figure 452:
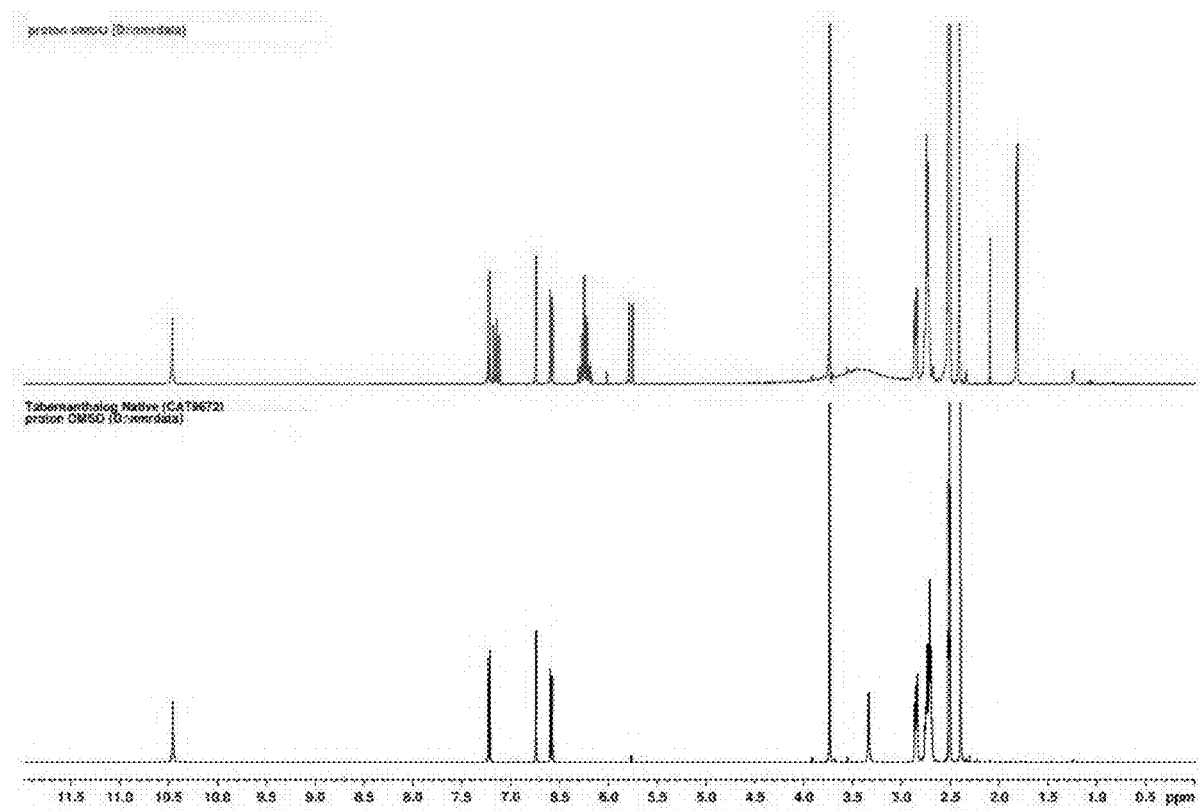

FIG. 452 depicts the $^1$H NMR of tabernanthalog sorbate salt 2-V2 (Experiment Reference 2-Sample Reference V2) (top spectrum), overlaid with Tabernanthalog (native) (bottom spectrum).

Figure 453:
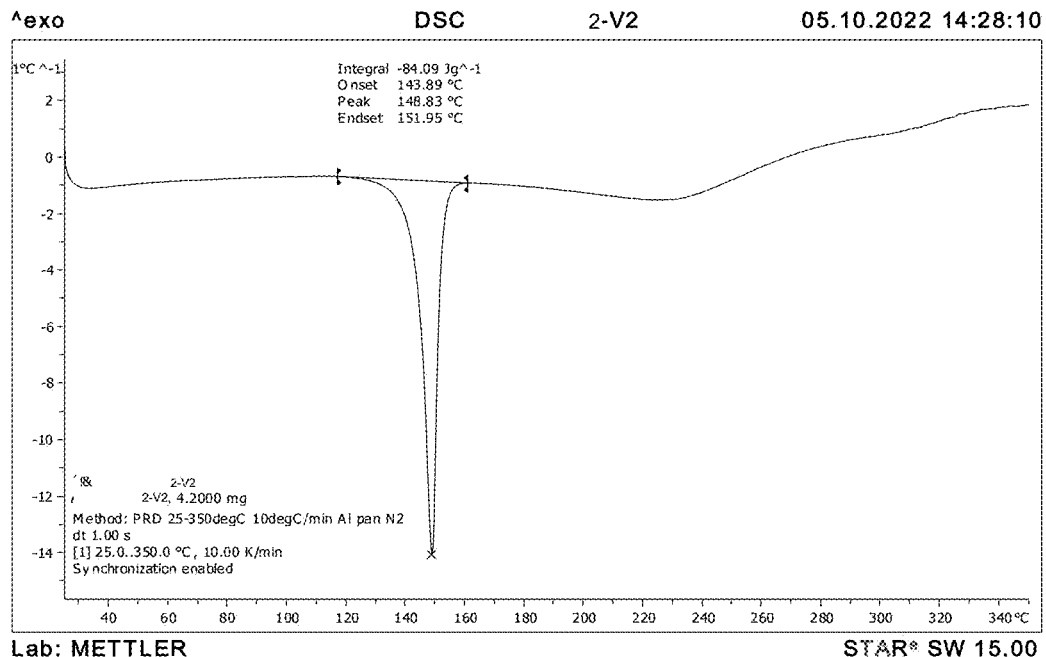

FIG. 453 depicts the DSC profile of tabernanthalog sorbate salt; 2-V2 (Experiment Reference 2-Sample Reference V2), analysis was acquired at a ramp rate of +10° C./minute.

Figure 454:
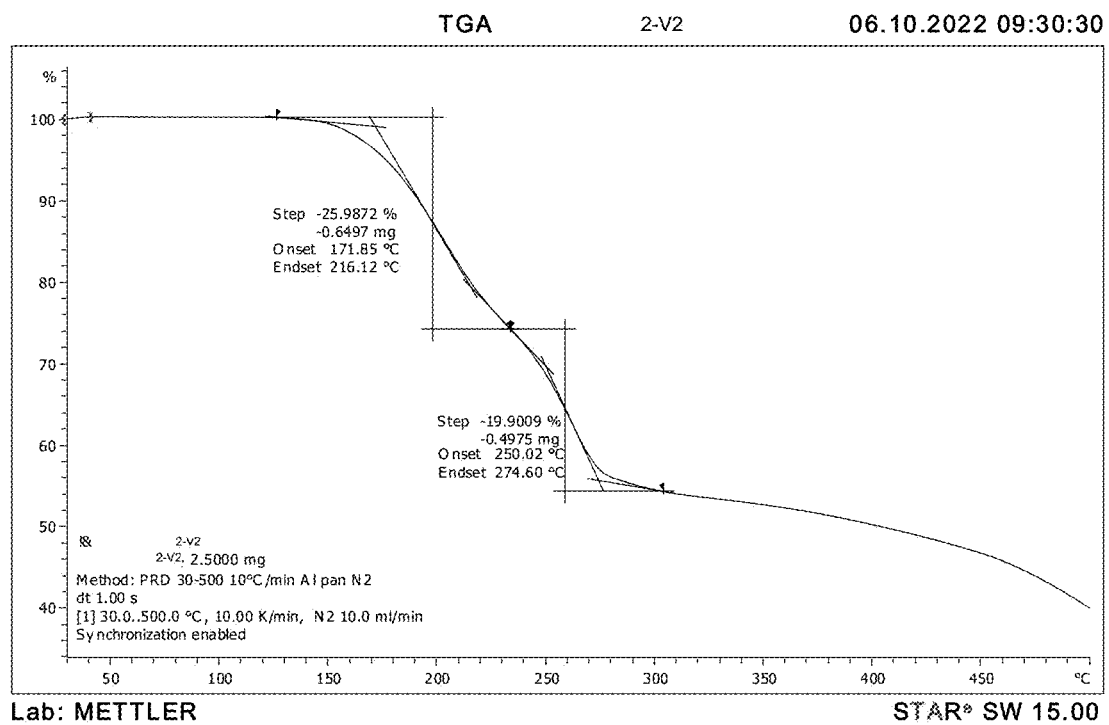

FIG. 454 depicts the TGA of tabernanthalog sorbate salt, 2-V2 (Experiment Reference 2-Sample Reference V2), analysis was acquired at a ramp rate of +10° C./minute.

FIG. 455 depicts the DVS of tabernanthalog sorbate salt, 4-A2 (Experiment Reference 4-Sample Reference A2), kinetic plot and isotherm analysis report.

Figure 456:
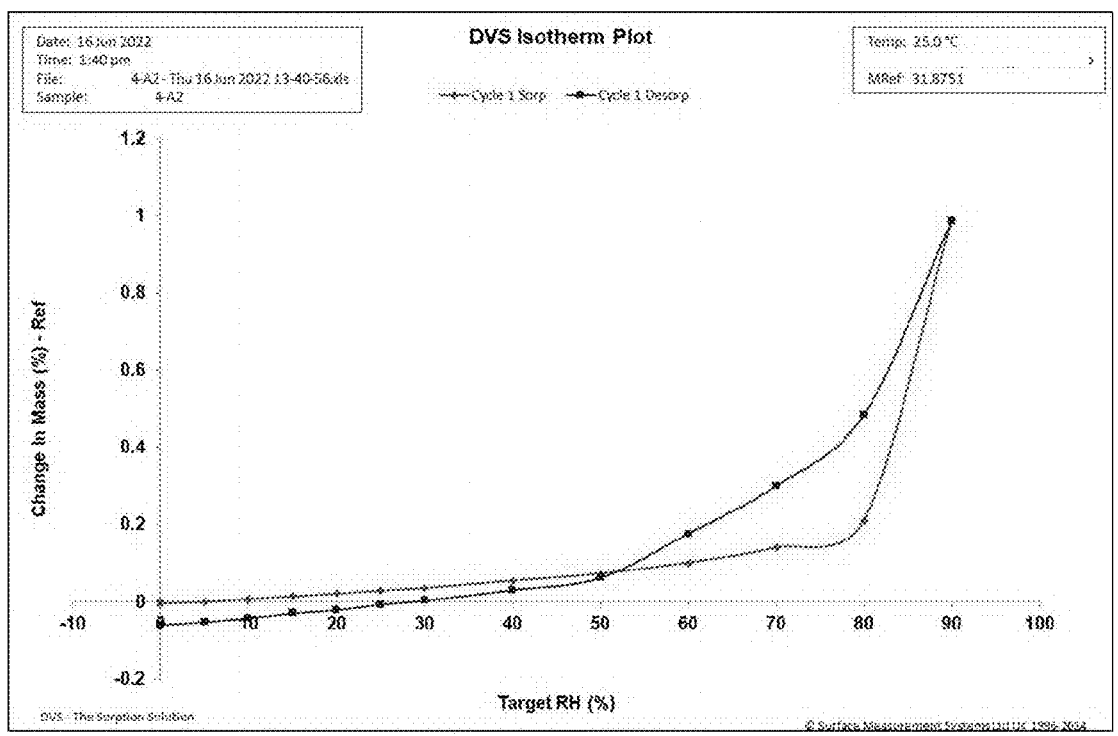

FIG. 456 depicts the DVS of tabernanthalog sorbate salt; 4-A2 (Experiment Reference 4-Sample Reference A2), isothermal plot.

Figure 458:
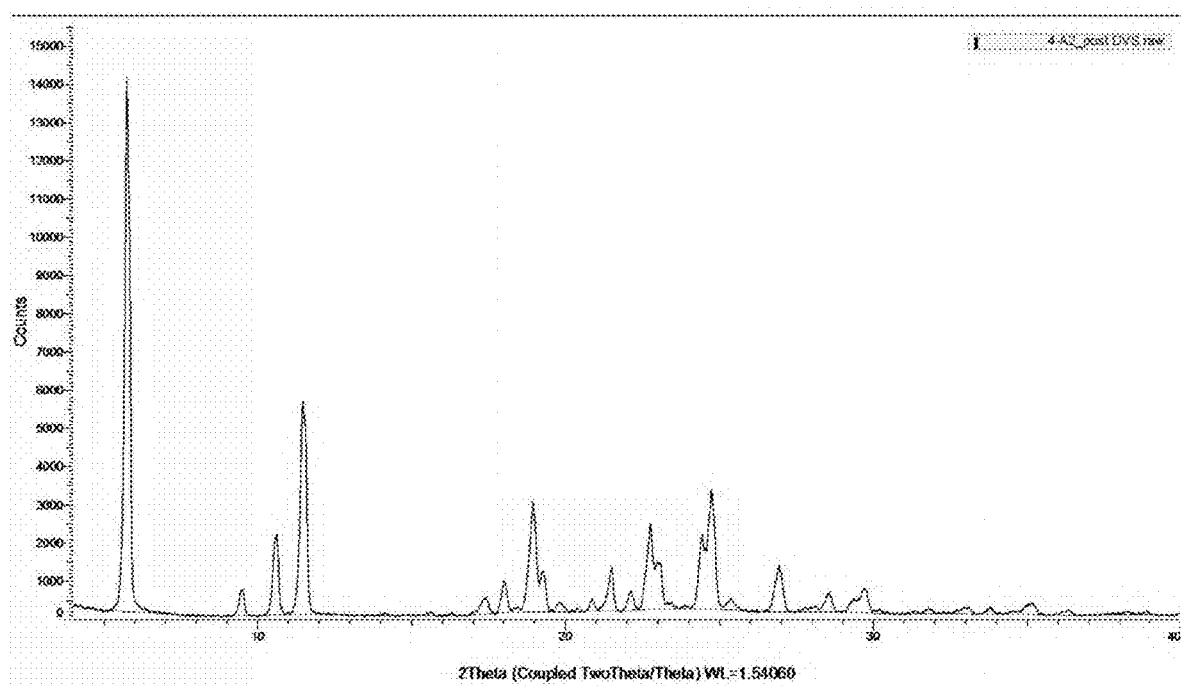

FIG. 458 depicts the XRPD of tabernanthalog sorbate salt; 4-A2 (Experiment Reference 4-Sample Reference A2) post DVS.

Figure 459:
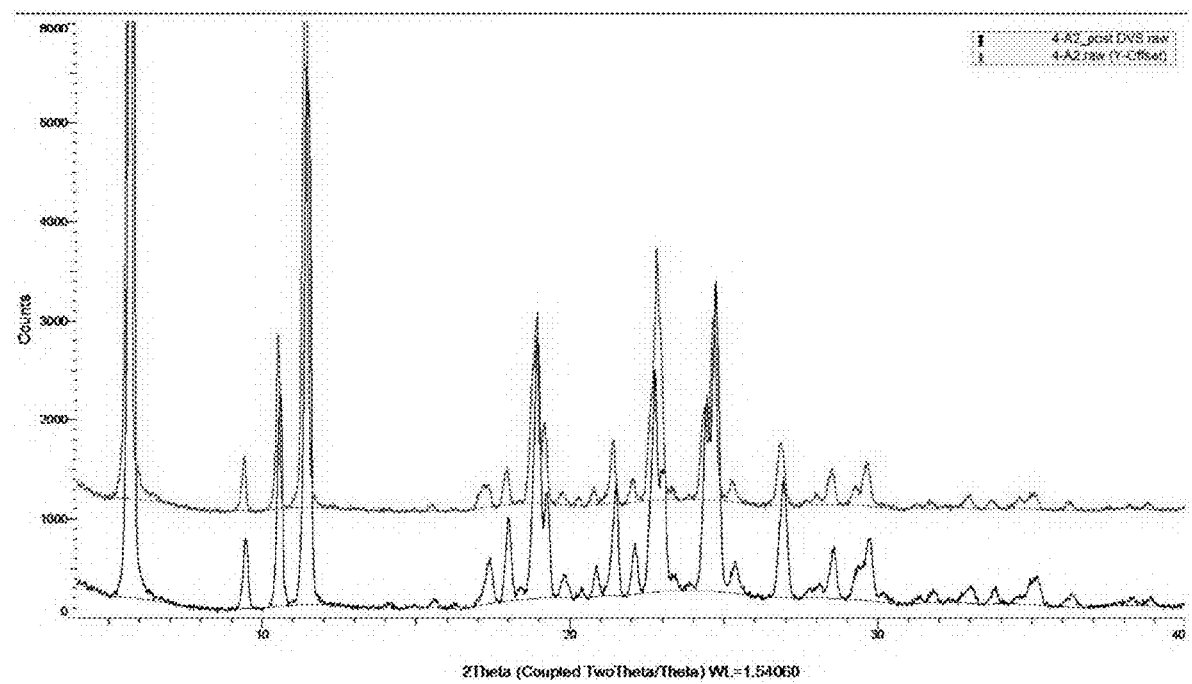

FIG. 459 depicts the XRPD of tabernanthalog sorbate salt; 4-A2 (Experiment Reference 4-Sample Reference A2) (post DVS 0 to 90% RH, bottom diffractogram), compared with the input sample tabernanthalog sorbate salt; 4-A2 (top diffractogram).

Figure 460:
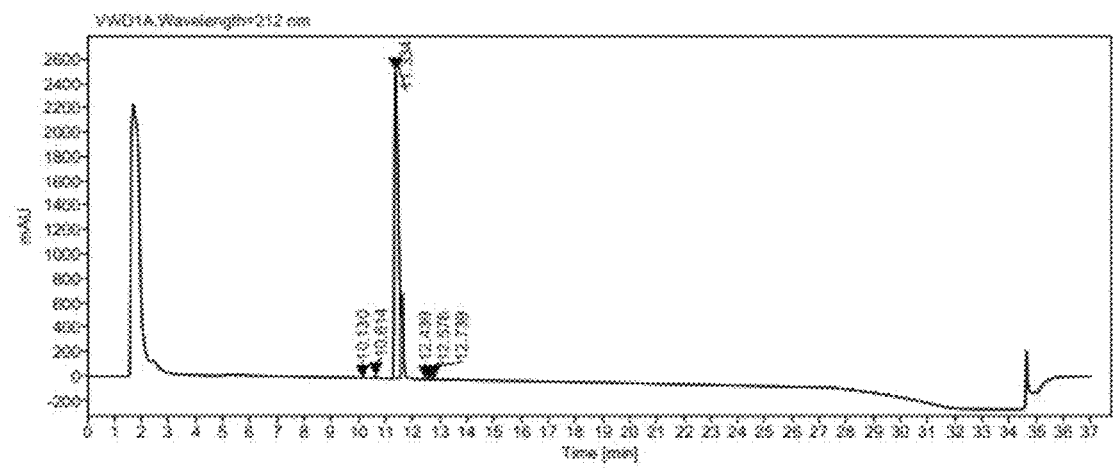

FIG. 460 depicts the HPLC of tabernanthalog sorbate salt; 3-C1 (Experiment Reference 3-Sample Reference C1).

Figure 461:
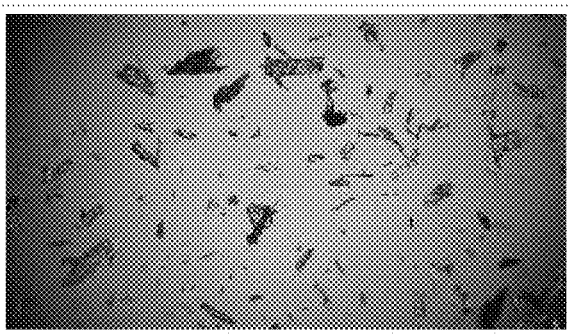

FIG. 461 depicts the PLM of tabernanthalog sorbate salt; 3-C1 (Experiment Reference 3-Sample Reference C1)×2 mag, NP.

Figure 462:
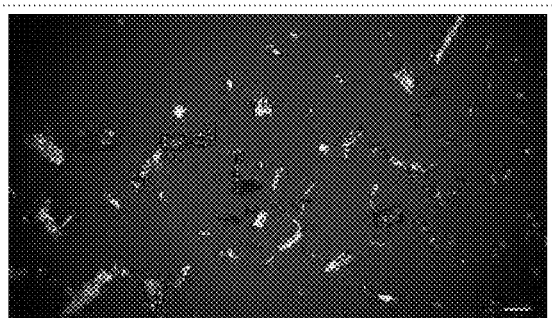

FIG. 462 depicts the PLM of tabernanthalog sorbate salt; 3-C1 (Experiment Reference 3-Sample Reference C1)×2 mag, CP.

Figure 463:
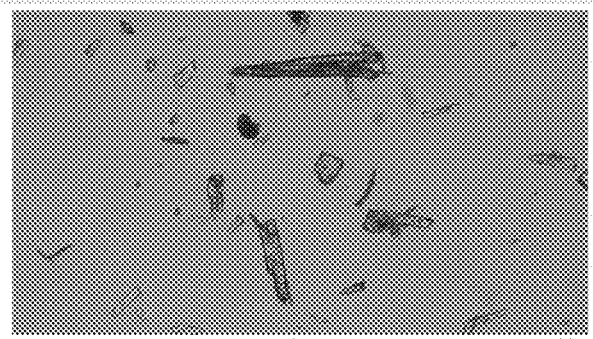

FIG. 463 depicts the PLM of tabernanthalog sorbate salt; 3-C1 (Experiment Reference 3-Sample Reference C1)×5 mag, NP.

Figure 464:
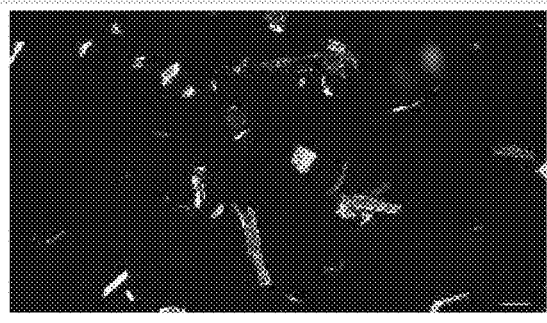

FIG. 464 depicts the PLM of tabernanthalog sorbate salt; 3-C1 (Experiment Reference 3-Sample Reference C1)×5 mag, CP.

Figure 465:
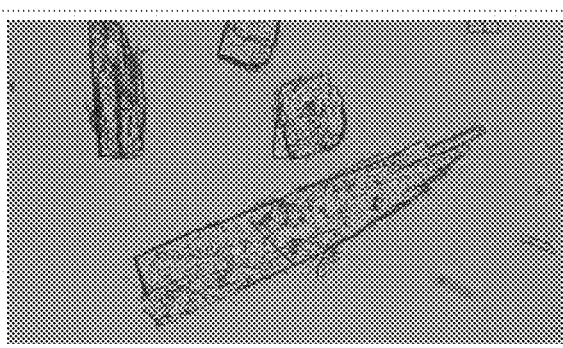

FIG. 465 depicts the PLM of tabernanthalog sorbate salt; 3-C1 (Experiment Reference 3-Sample Reference C1)×20 mag, NP.

Figure 466:
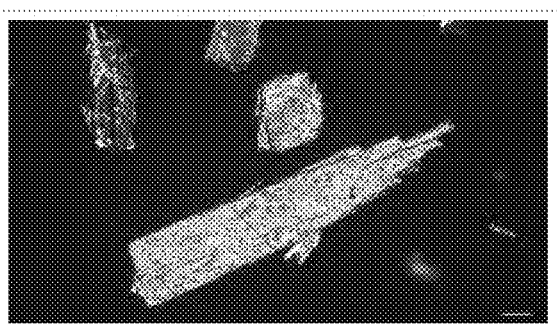

FIG. 466 depicts the PLM of tabernanthalog sorbate salt: 3-C1 (Experiment Reference 3-Sample Reference C1)×20 mag, CP.

Figure 467:
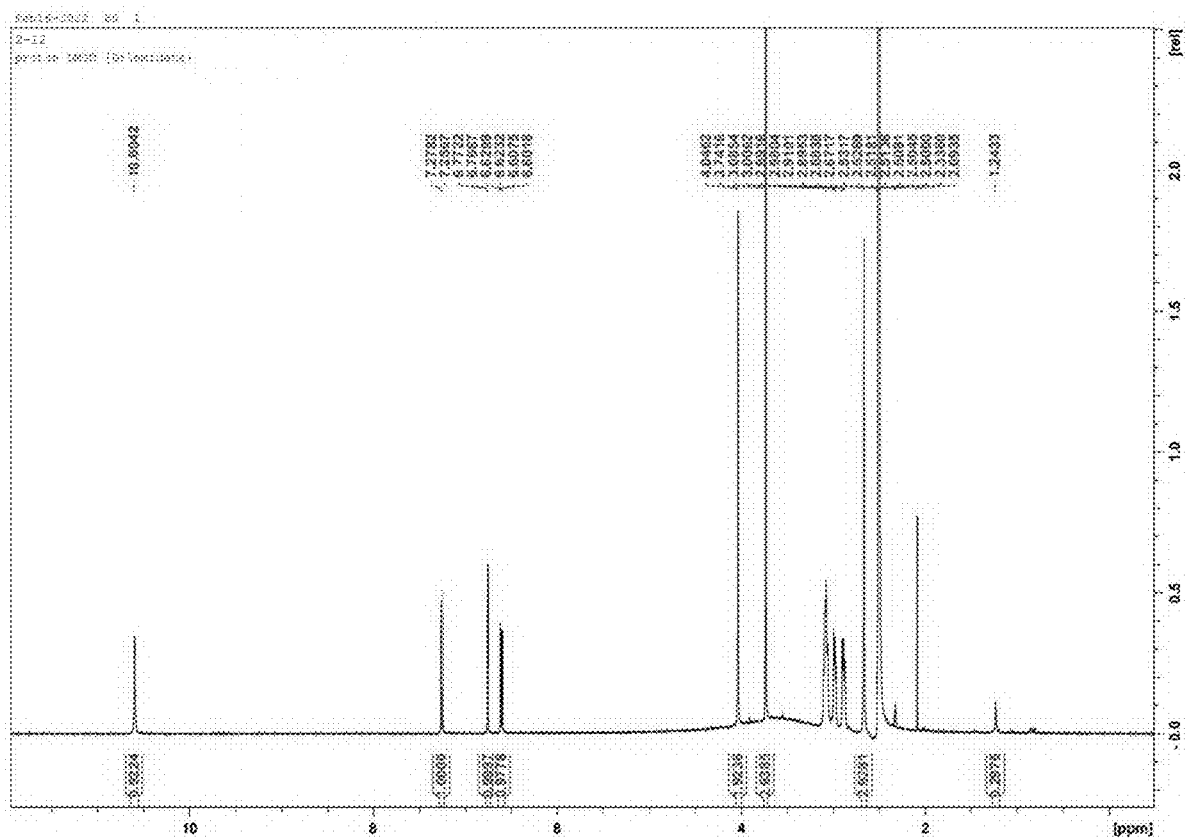

FIG. 467 depicts the $^1$H NMR of tabernanthalog tartrate salt; 2-I2 (Experiment Reference 2-Sample Reference I2), analysis was acquired in DMSO-d6 and calibrated to the non-deuterated solvent residual at 2.50 ppm. 1.0 mol of API to 1.0 mol L-tartaric acid. Ethanol content 0.1% w/w.

Figure 468:
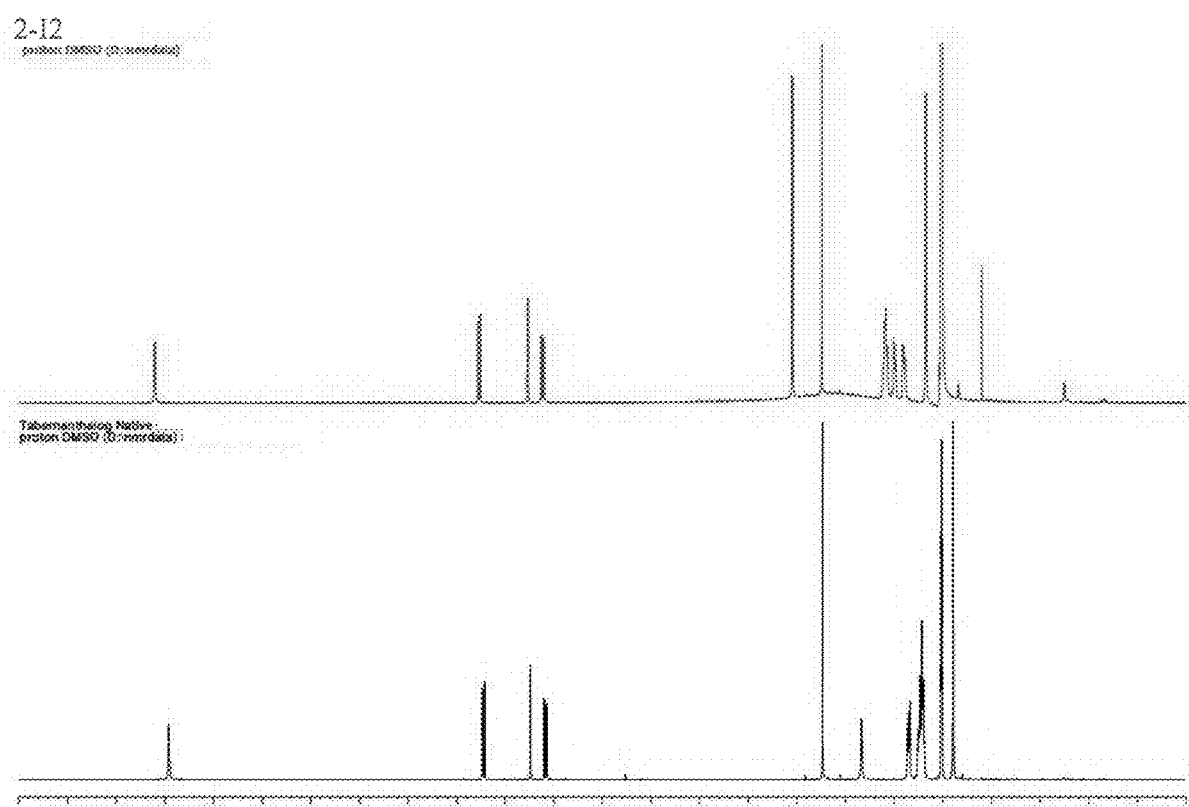

FIG. 468 depicts the $^1$H NMR of tabernanthalog tartrate salt; 2-I2 (Experiment Reference 2-Sample Reference I2) (top spectrum), overlaid with Tabernanthalog (native) (bottom spectrum).

Figure 469:
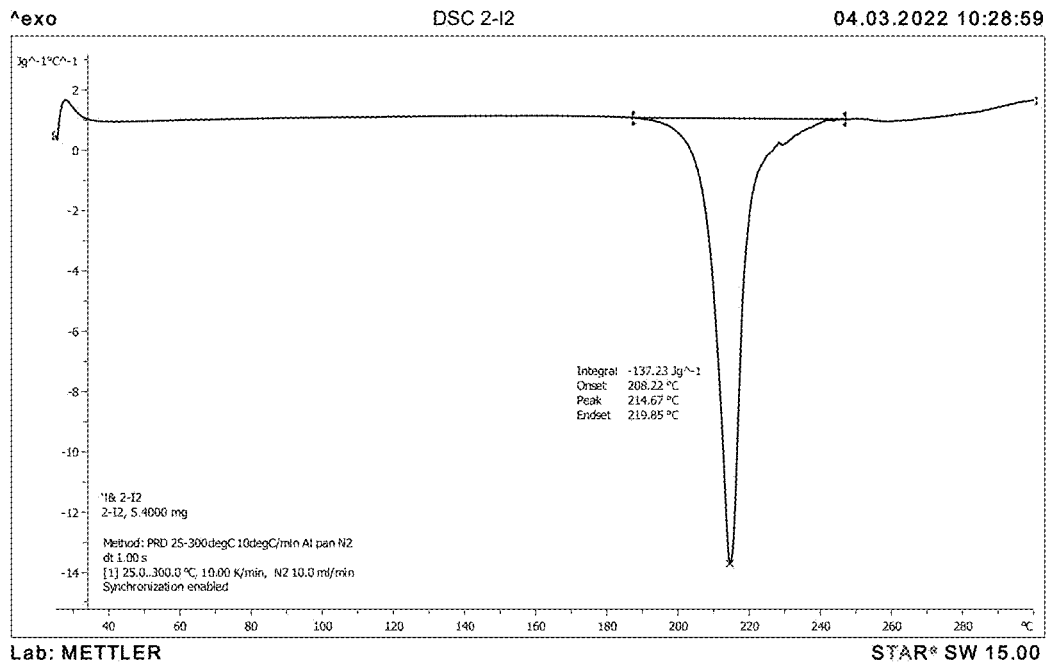

FIG. 469 depicts the DSC profile of tabernanthalog tartrate salt; 2-I2 (Experiment Reference 2-Sample Reference I2), analysis was acquired at a ramp rate of +10° C./minute.

Figure 470:
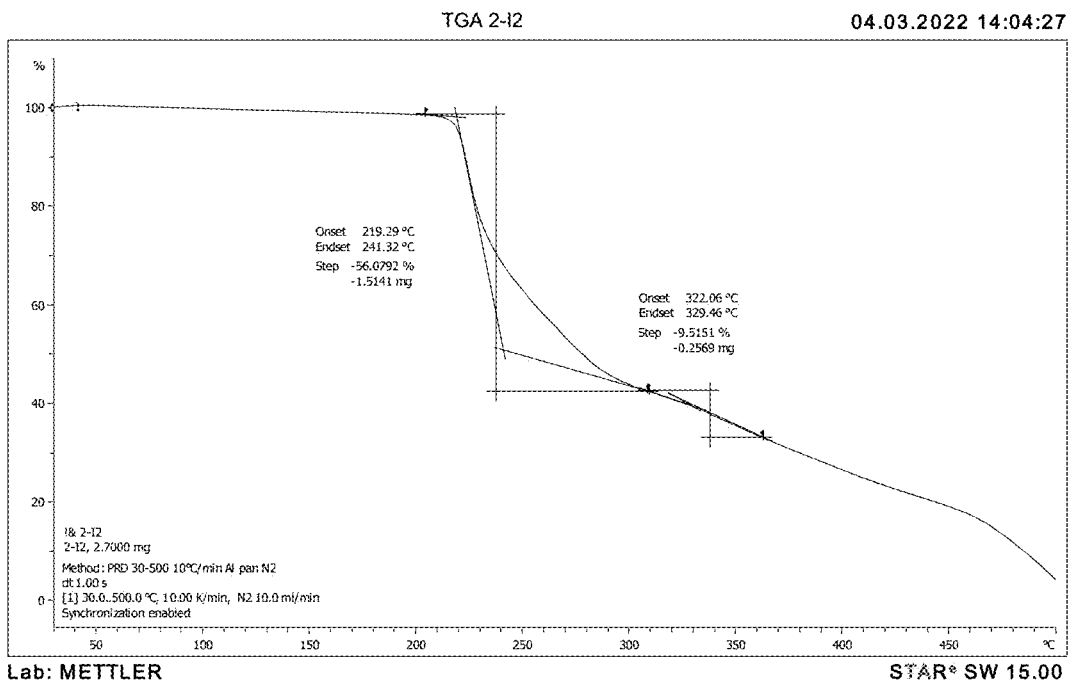

FIG. 470 depicts the TGA of tabernanthalog tartrate salt; 2-I2 (Experiment Reference 2-Sample Reference I2), analysis was acquired at a ramp rate of +10° C./minute.

Figure 471:
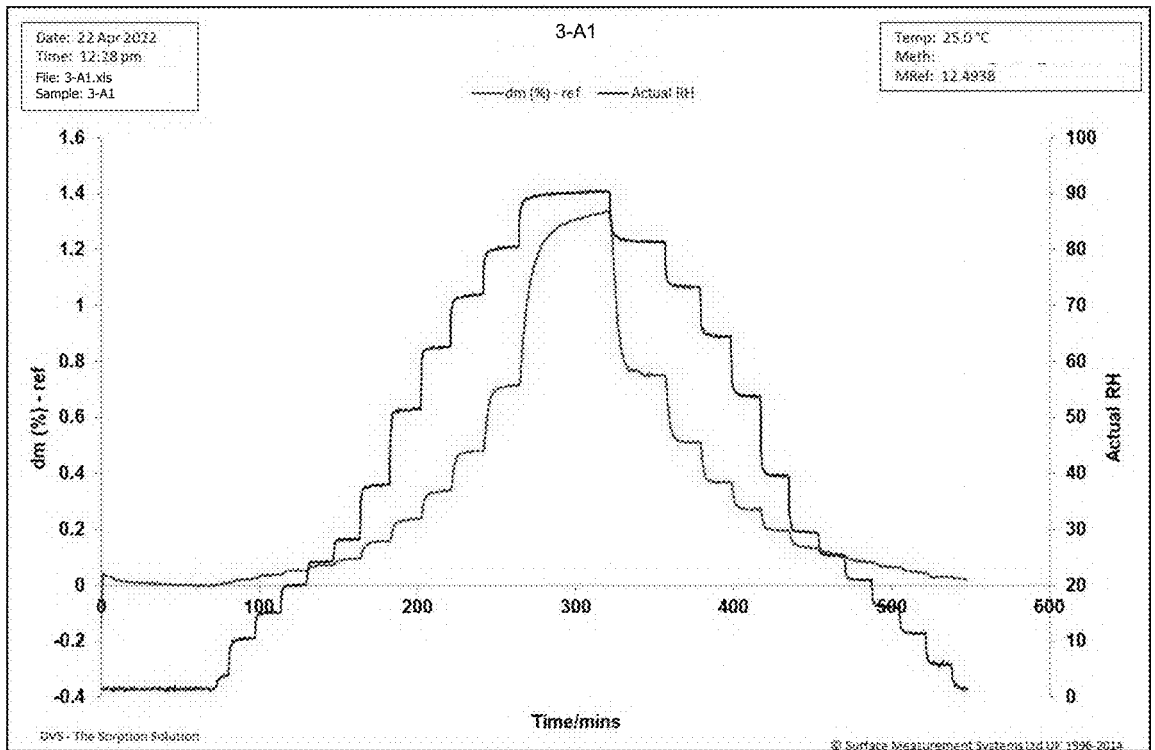

FIG. 471 depicts the DVS of tabernanthalog tartrate salt; 3-A1 (Experiment Reference 3-Sample Reference A1), kinetic plot and isotherm analysis report.

Figure 472:
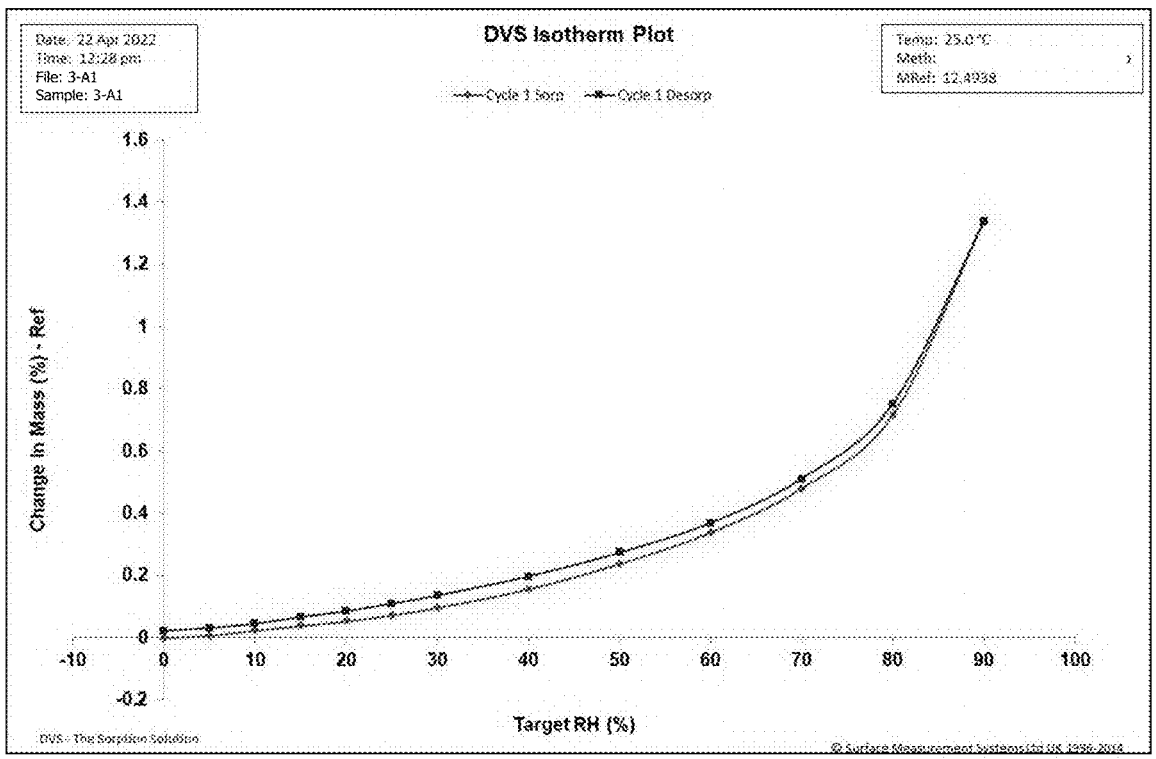
Figure 474:
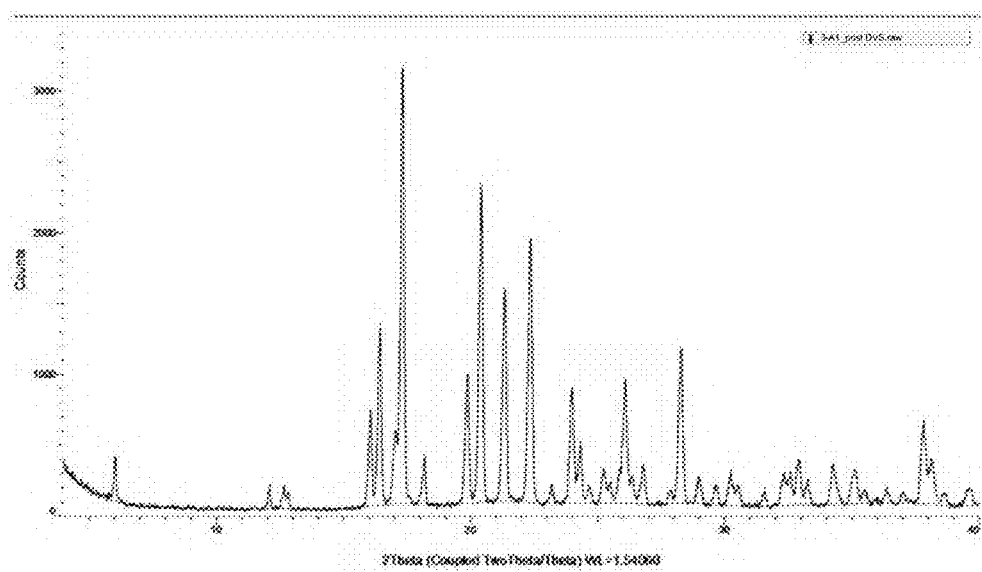

FIG. 472 depicts the DVS of tabernanthalog tartrate salt; 3-A1 (Experiment Reference 3-Sample Reference A1), isothermal plot FIG. 474 depicts the XRPD of tabernanthalog tartrate salt; 3-A1 (Experiment Reference 3-Sample Reference A1) post DVS.

Figure 475:
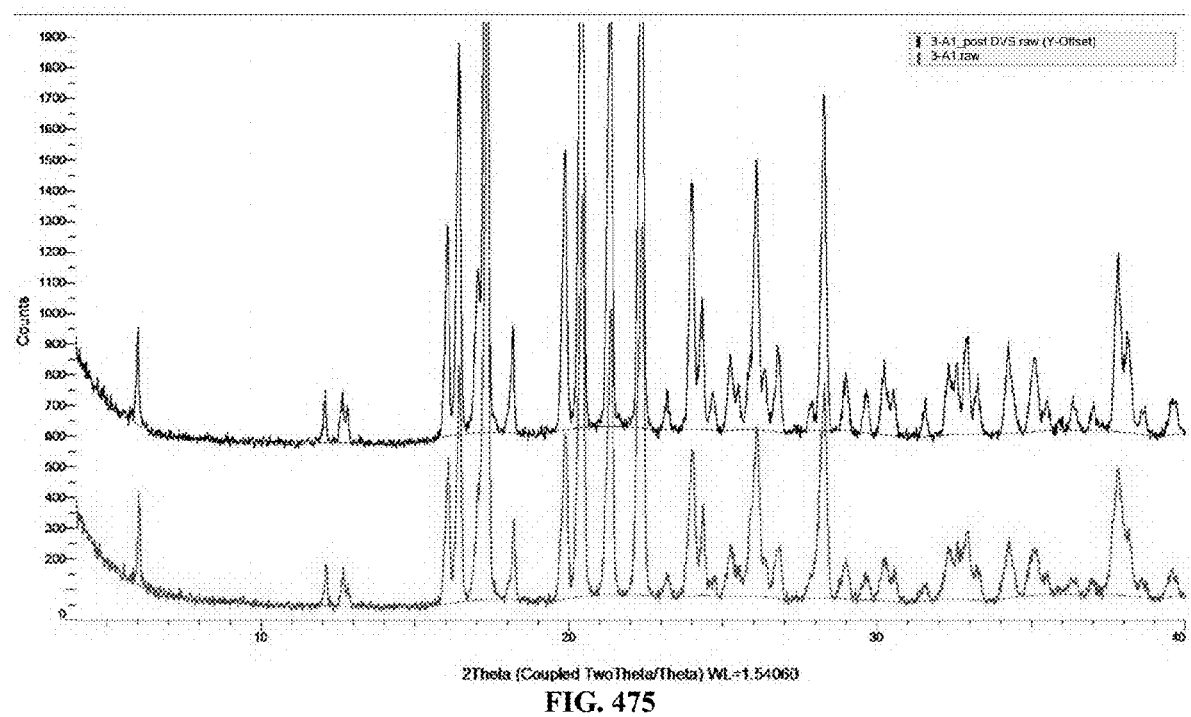

FIG. 475 depicts the XRPD of tabernanthalog tartrate salt; 3-A1 (Experiment Reference 3-Sample Reference A1) post DVS 0 to 90% RH, top diffractogram), compared with the input sample of tabernanthalog tartrate salt; 3-A1 (bottom diffractogram).

Figure 476:
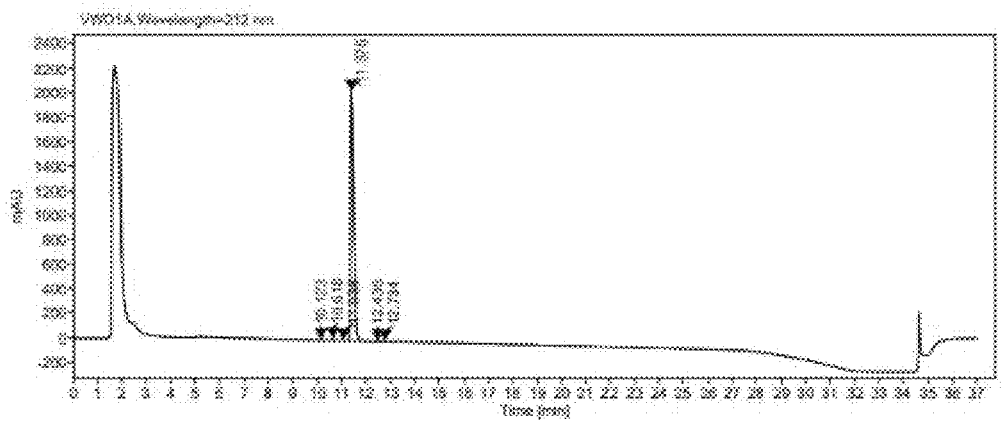

FIG. 476 depicts the HPLC of tabernanthalog tartrate salt; 3-A1 (Experiment Reference 3-Sample Reference A1).

Figure 477:
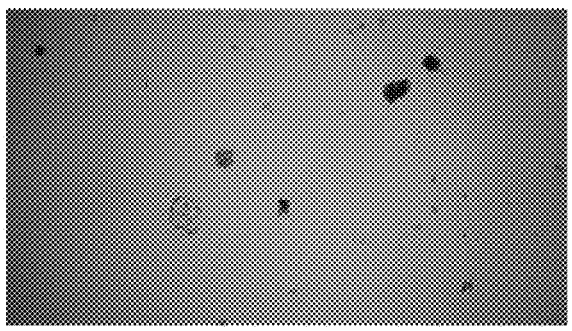

FIG. 477 depicts the PLM of tabernanthalog tartrate salt; 3-A1 (Experiment Reference 3-Sample Reference A1)×2 mag, NP.

Figure 478:
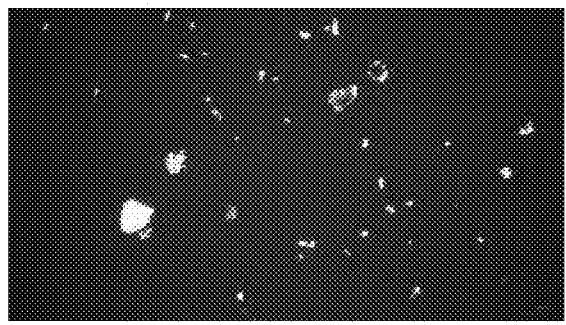

FIG. 478 depicts the PLM of tabernanthalog tartrate salt; 3-A1 (Experiment Reference 3-Sample Reference A1)×2 mag, CP.

Figure 479:
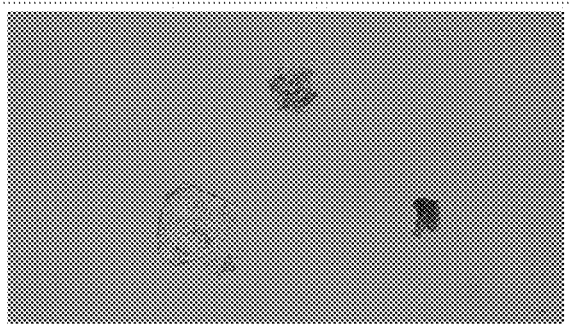

FIG. 479 depicts the PLM of tabernanthalog tartrate salt; 3-A1 (Experiment Reference 3-Sample Reference A1)×5 mag, NP.

Figure 480:
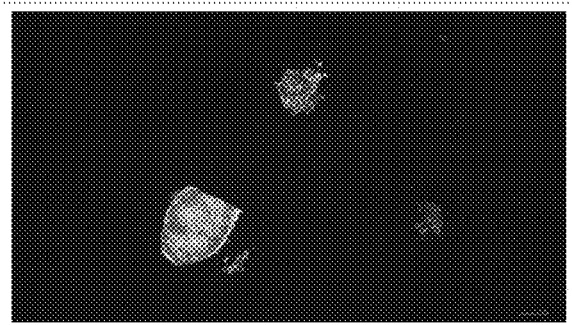

FIG. 480 depicts the PLM of tabernanthalog tartrate salt; 3-A1 (Experiment Reference 3-Sample Reference A1)×5 mag, CP.

Figure 481:
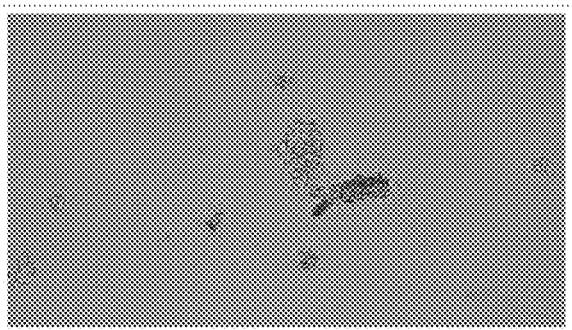

FIG. 481 depicts the PLM of tabernanthalog tartrate salt; 3-A1 (Experiment Reference 3-Sample Reference A1)×5 mag, NP.

Figure 482:
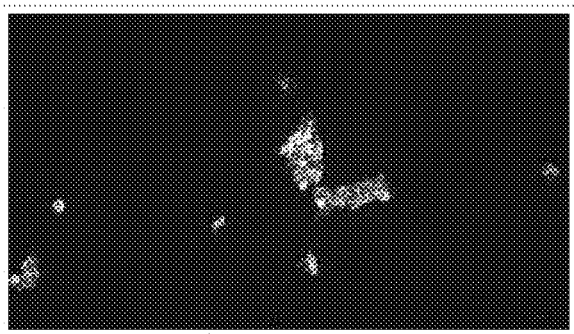

FIG. 482 depicts the PLM of tabernanthalog tartrate salt; 3-A1 (Experiment Reference 3-Sample Reference A1)×5 mag, CP.

Figure 483:
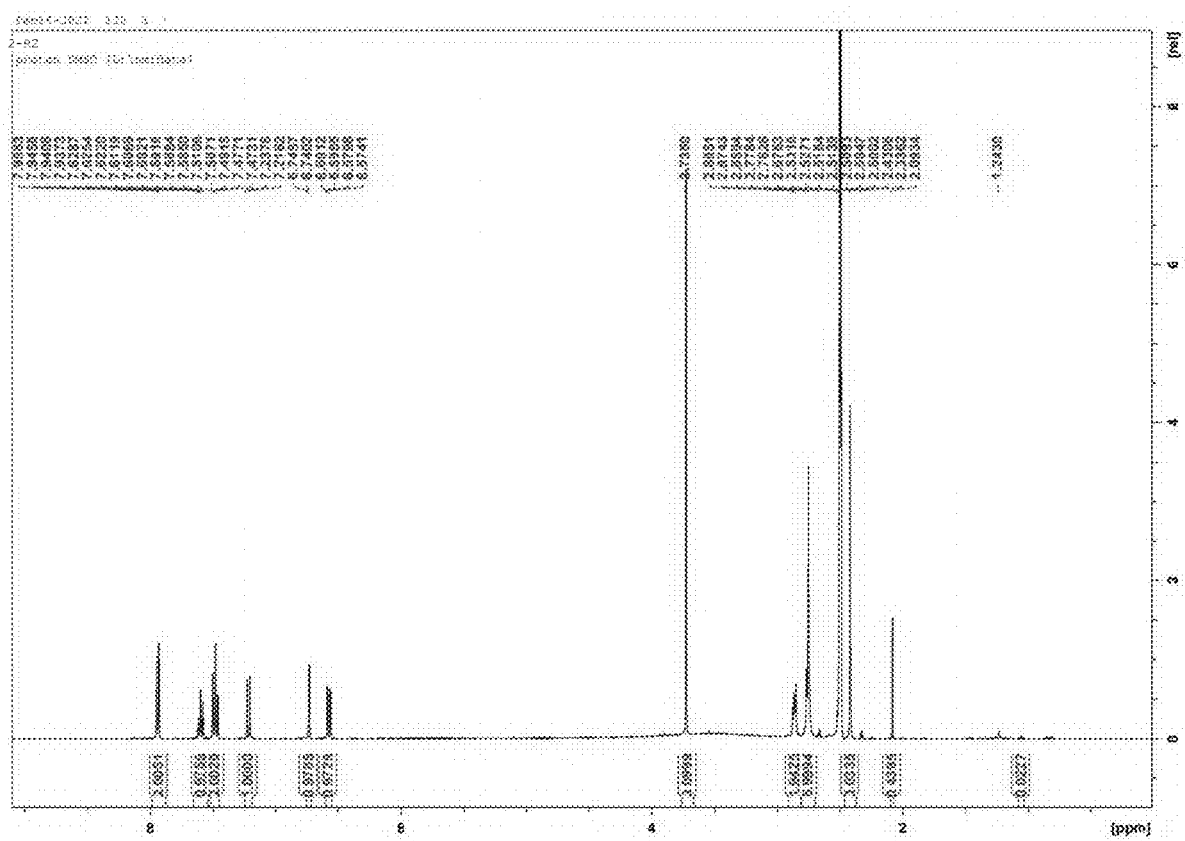

FIG. 483 depicts the $^1$H NMR of tabernanthalog benzoate salt; 2-R2 (Experiment Reference 2-Sample Reference R2), acquired in DMSO-d6 and calibrated to the non-deuterated solvent residual at 2.50 ppm. 1.0 mol of API to 1.0 mol of benzoic acid. Ethanol content 0.1% w/w.

Figure 484:
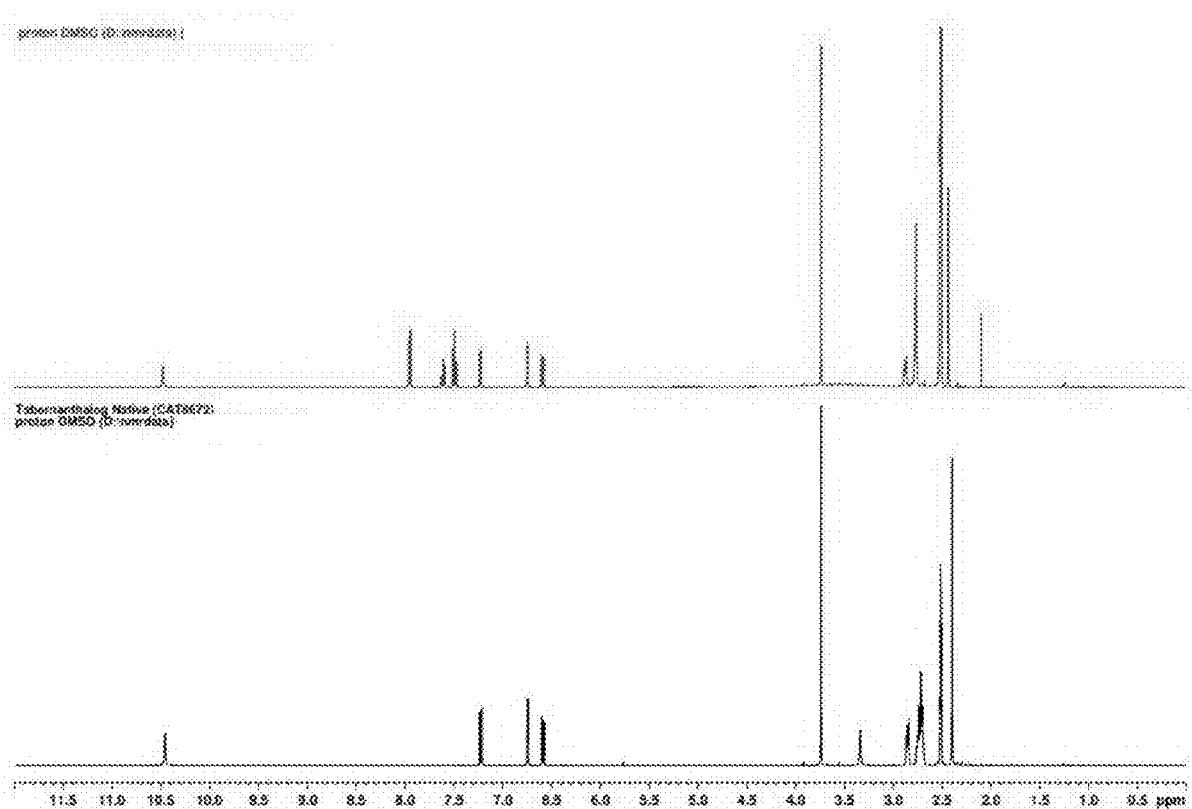

FIG. 484 depicts the $^1$H NMR of tabernanthalog benzoate salt; 2-R2 (Experiment Reference 2-Sample Reference R2) (top spectrum), overlaid with Tabernanthalog (native) (bottom spectrum). Depreciation in impurity burden is observed.

Figure 485:
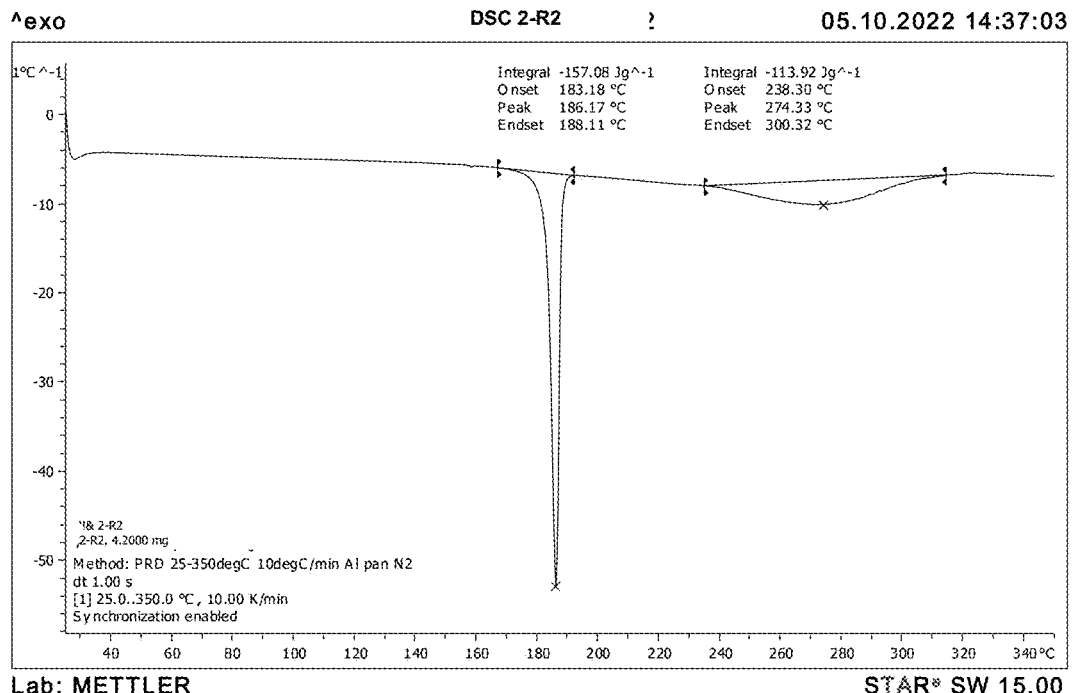

FIG. 485 depicts the DSC profile of tabernanthalog benzoate salt; 2-R2 (Experiment Reference 2-Sample Reference R2), analysis was acquired at a ramp rate of +10° C./minute.

Figure 486:
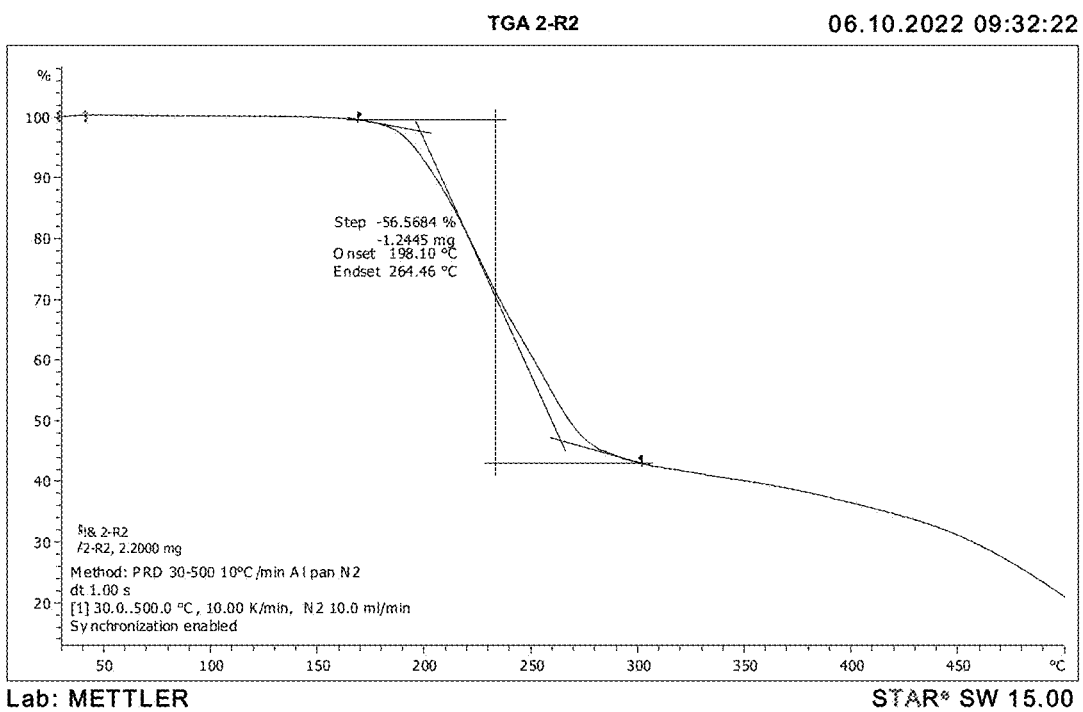

FIG. 486 depicts the TGA of tabernanthalog benzoate salt; 2-R2 (Experiment Reference 2-Sample Reference R2), analysis was acquired at a ramp rate of +10° C./minute.

Figure 486A:
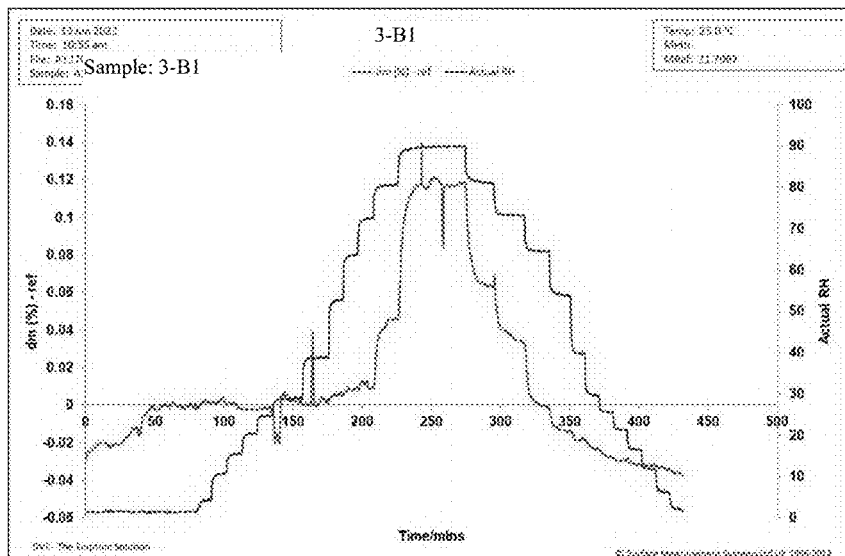

FIG. 486(A) depicts the DVS of tabernanthalog benzoate salt; 3-B1 (Experiment Reference 3-Sample Reference B1), kinetic plot and isotherm analysis report.

Figure 486B:
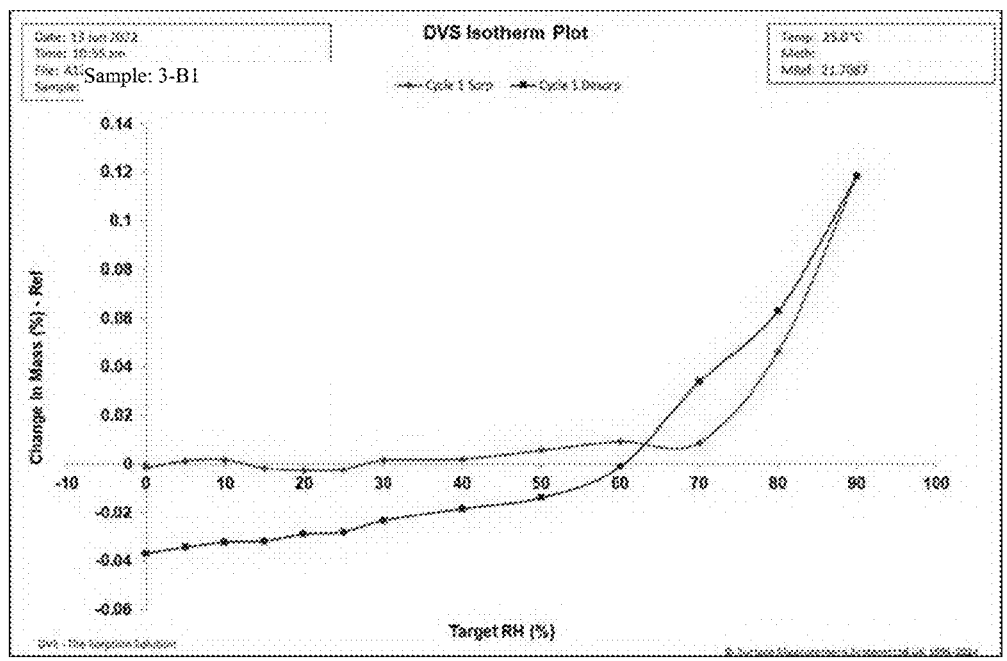

FIG. 486B) depicts the DVS of tabernanthalog benzoate salt; 3-B1 (Experiment Reference 3-Sample Reference B1), isothermal plot.

Figure 486C:
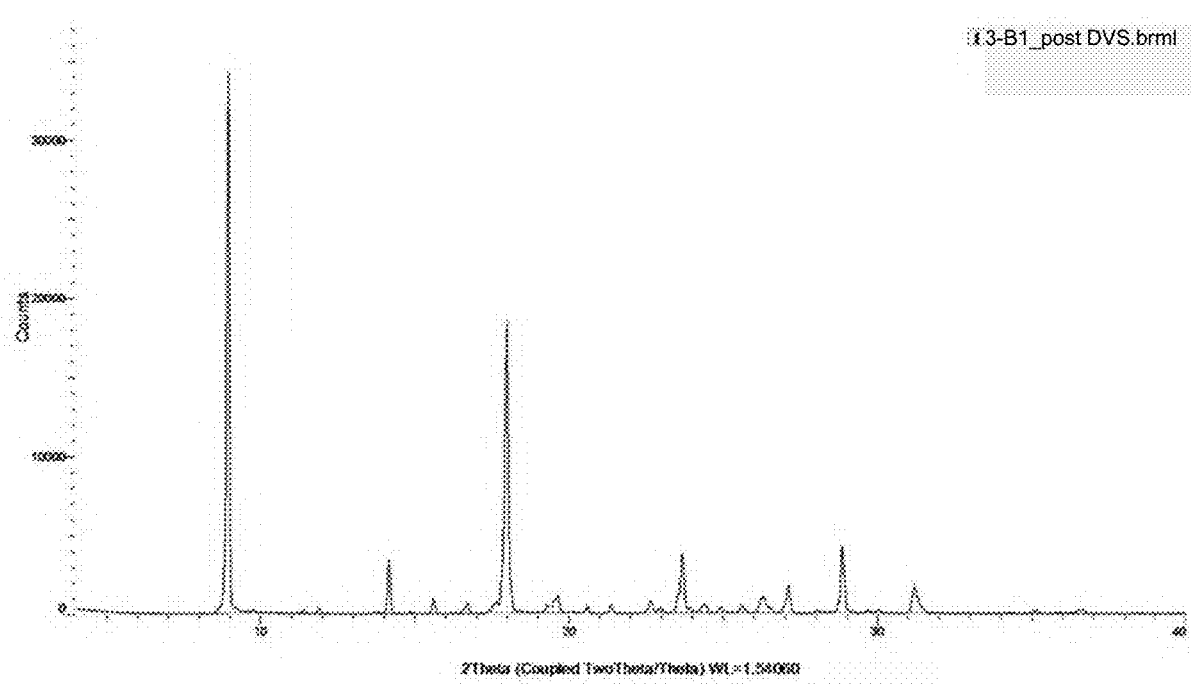

FIG. 486(C) depicts the XRPD of tabernanthalog benzoate salt; 3-B1 (Experiment Reference 3-Sample Reference B1) post DVS.

Figure 486D:
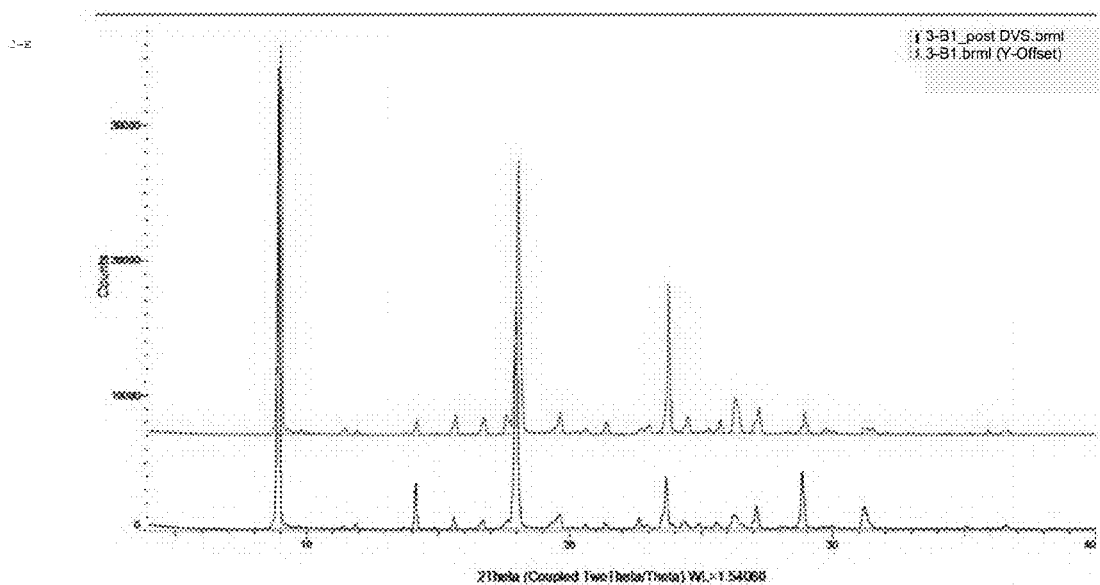

FIG. 486(D) depicts the XRPD of tabernanthalog benzoate salt; 3-B1 (Experiment Reference 3-Sample Reference B1) (post DVS 0 to 90% RH, bottom diffractogram), compared with the input sample of tabernanthalog benzoate salt; 3-B1 (top diffractogram).

Figure 486E:
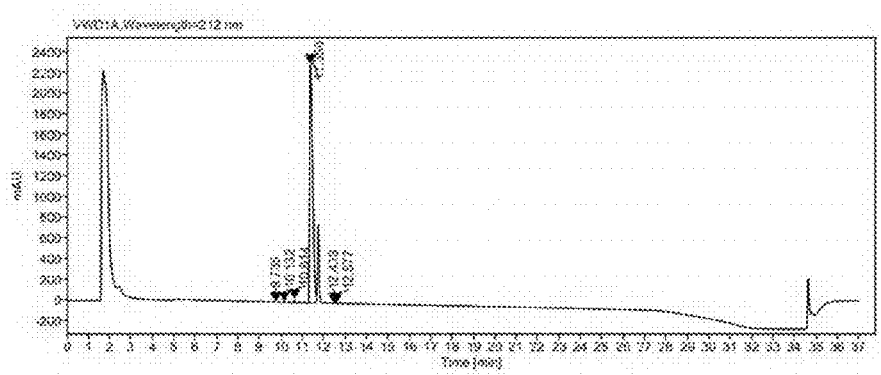

FIG. 486(E) depicts the HPLC of tabernanthalog benzoate salt; 3-B1 (Experiment Reference 3-Sample Reference B1).

Figure 486F:
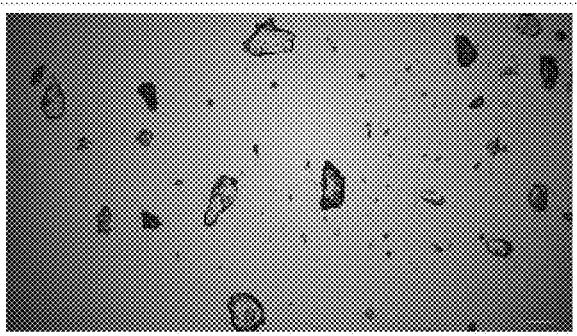

FIG. 486(F) depicts the PLM of tabernanthalog benzoate salt; 3-B1 (Experiment Reference 3-Sample Reference B1)×2 mag, NP.

Figure 486G:
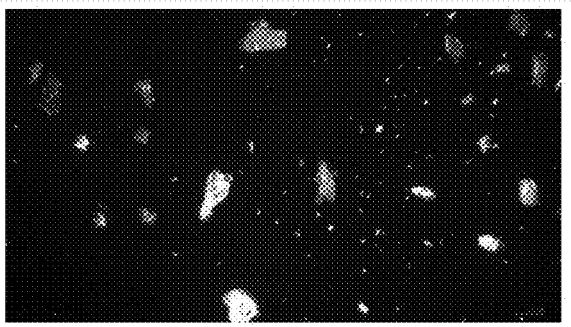

FIG. 486(G) depicts the PLM of tabernanthalog benzoate salt; 3-B1 (Experiment Reference 3-Sample Reference B1)×2 mag, CP.

Figure 486H:
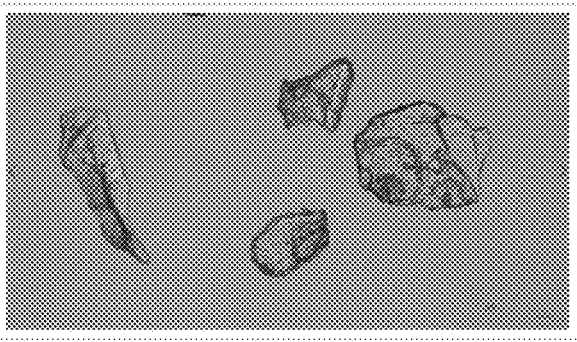

FIG. 486(H) depicts the PLM of tabernanthalog benzoate salt; 3-B1 (Experiment Reference 3-Sample Reference B1)×5 mag, NP.

Figure 486I:
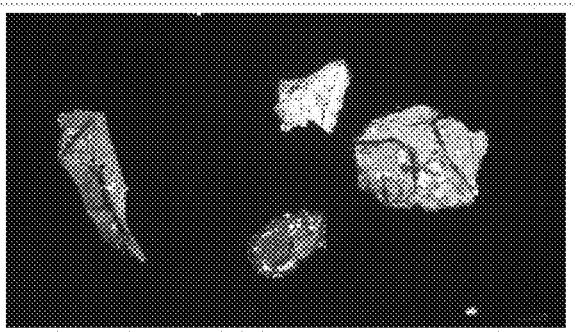

FIG. 486(I) depicts the PLM of tabernanthalog benzoate salt; 3-B1 (Experiment Reference 3-Sample Reference B1)×5 mag, CP.

Figure 486J:
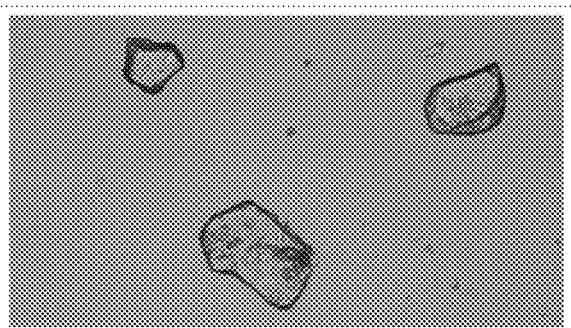

FIG. 486(J) depicts the PLM of tabernanthalog benzoate salt; 3-B1 (Experiment Reference 3-Sample Reference B1)×5 mag, NP.

Figure 486K:
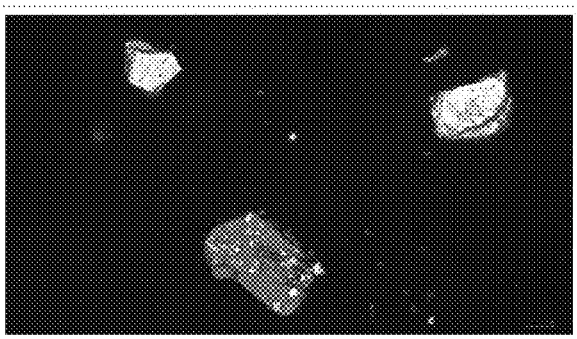
Figure 488:
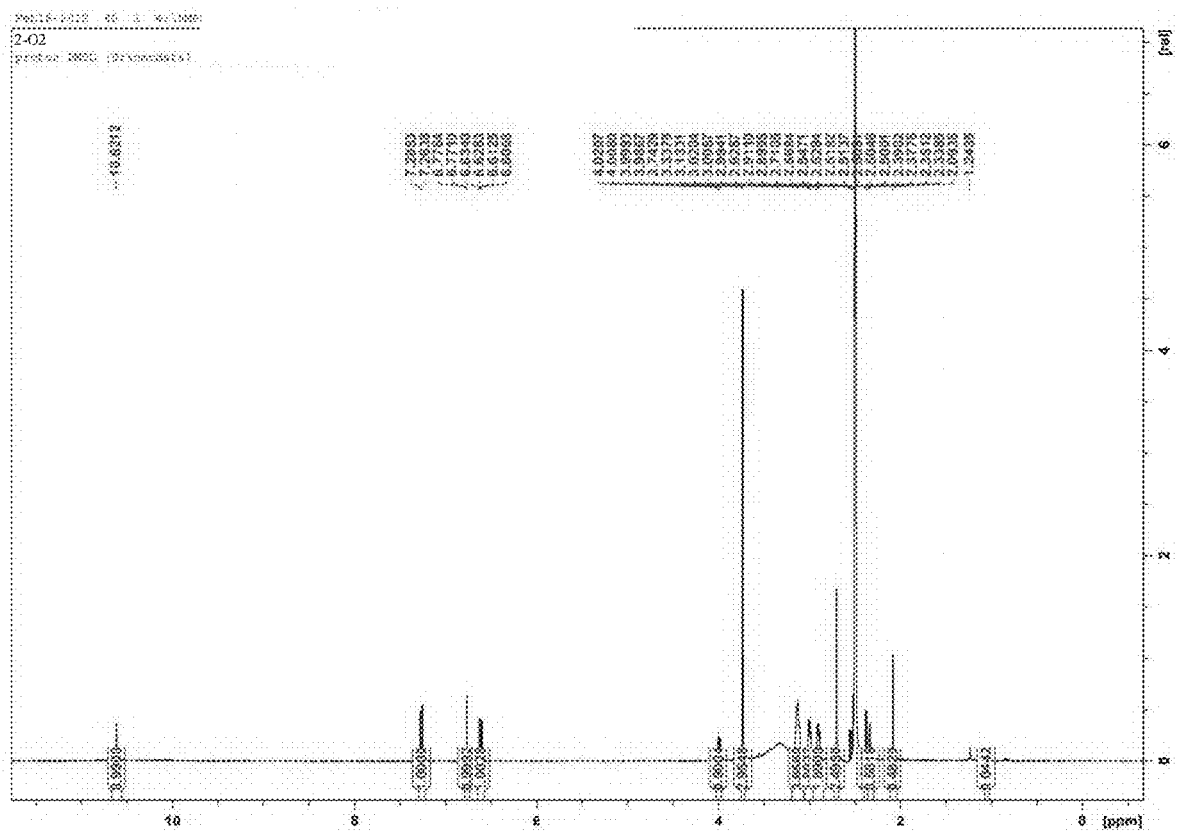

FIG. 486(K) depicts the PLM of tabernanthalog benzoate salt; 3-B1 (Experiment Reference 3-Sample Reference B1)×5 mag, CP. FIG. 488 depicts the $^1$H NMR of tabernanthalog malate salt; 2-O2 (Experiment Reference 2-Sample Reference O2), acquired in DMSO-d6 and calibrated to the non-deuterated solvent residual at 2.50 ppm. 1.0 mol of API to 1.0 mol L-malic acid. Ethanol content 0.2% w/w.

FIG. 488 depicts the =H NMR of tabernanthalog malate salt; 2-O2 (Experiment Reference 2-Sample Reference O2), acquired in DMSO-d6 and calibrated to the non-deuterated solvent residual at 2.50 ppm. 1.0 mol of API to 1.0 mol L-malic acid. Ethanol content 0.2% w/w.

Figure 489:
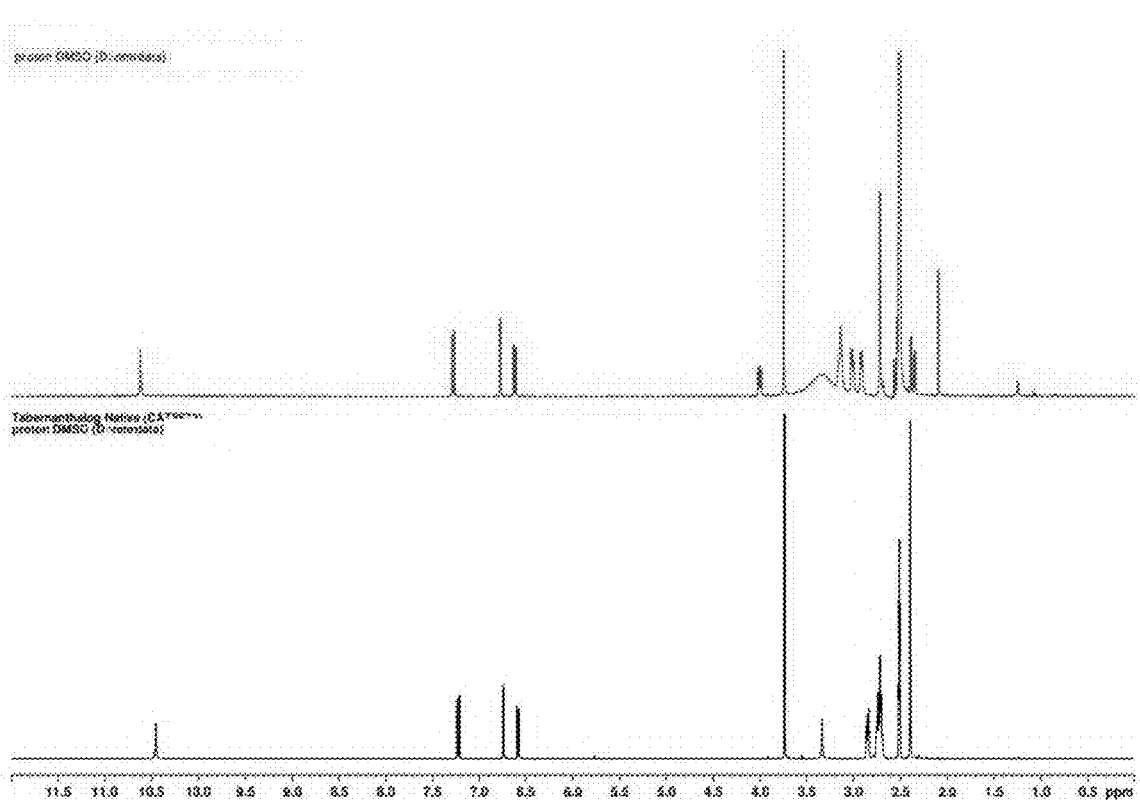

FIG. 489 depicts the $^1$H NMR of tabernanthalog malate salt; 2-O2 (Experiment Reference 2-Sample Reference O2) (top spectrum), overlaid with Tabernanthalog (native) (bottom spectrum). The comparison shows a slight appreciation in impurity burden compared to the free base.

Figure 490:
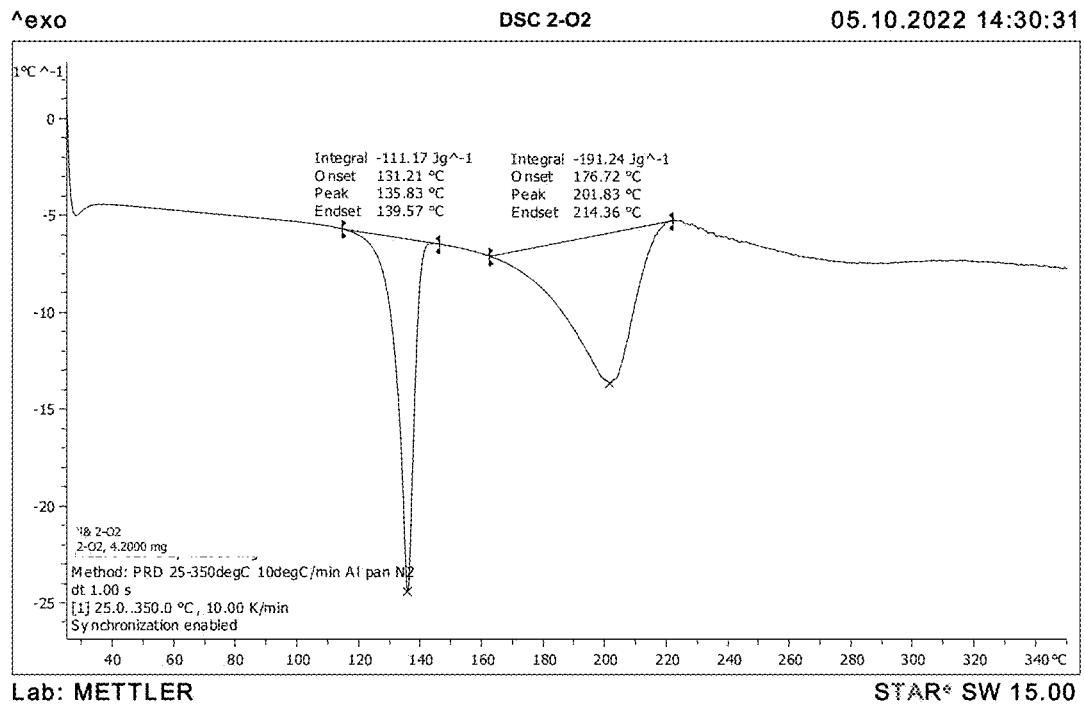

FIG. 490 depicts the DSC profile of tabernanthalog malate salt; 2-O2 (Experiment Reference 2-Sample Reference O2), analysis was acquired at a ramp rate of +10° C./minute.

Figure 491:
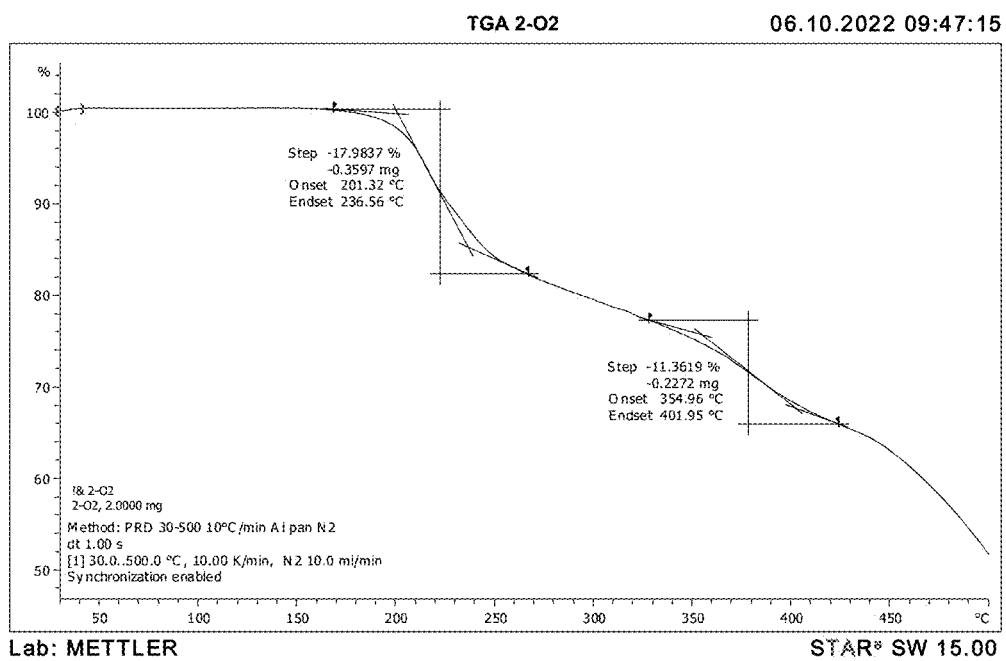

FIG. 491 depicts the TGA of tabernanthalog malate salt; 2-O2 (Experiment Reference 2-Sample Reference O2), analysis was acquired at a ramp rate of +10° C./minute.

Figure 492:
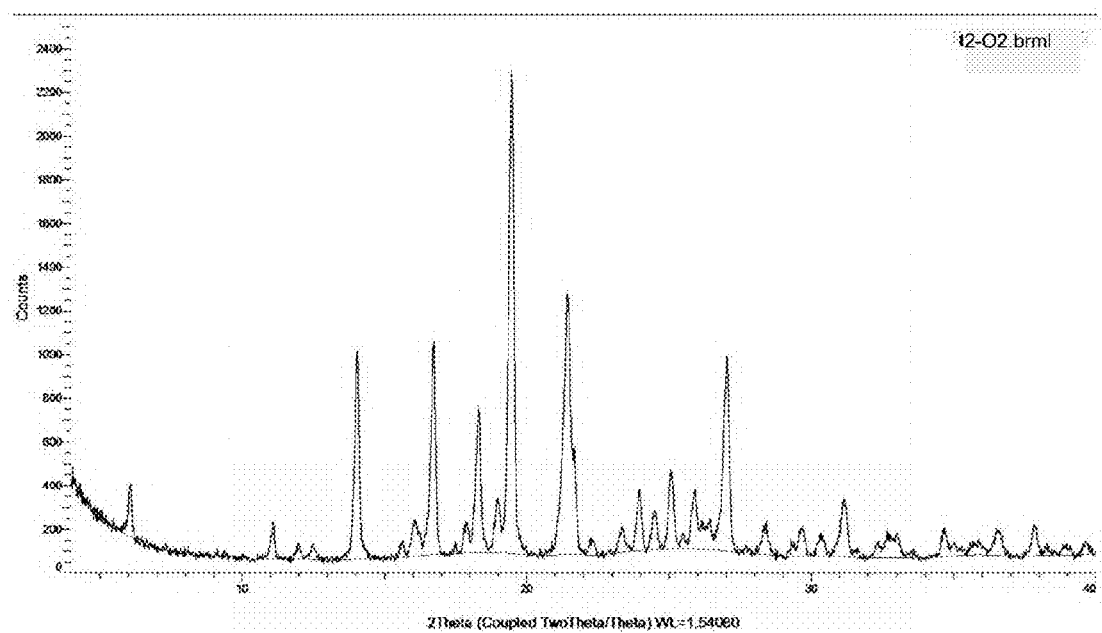

FIG. 492 depicts the XRPD of tabernanthalog malate salt; 2-O2 (Experiment Reference 2-Sample Reference O2).

Figure 493:
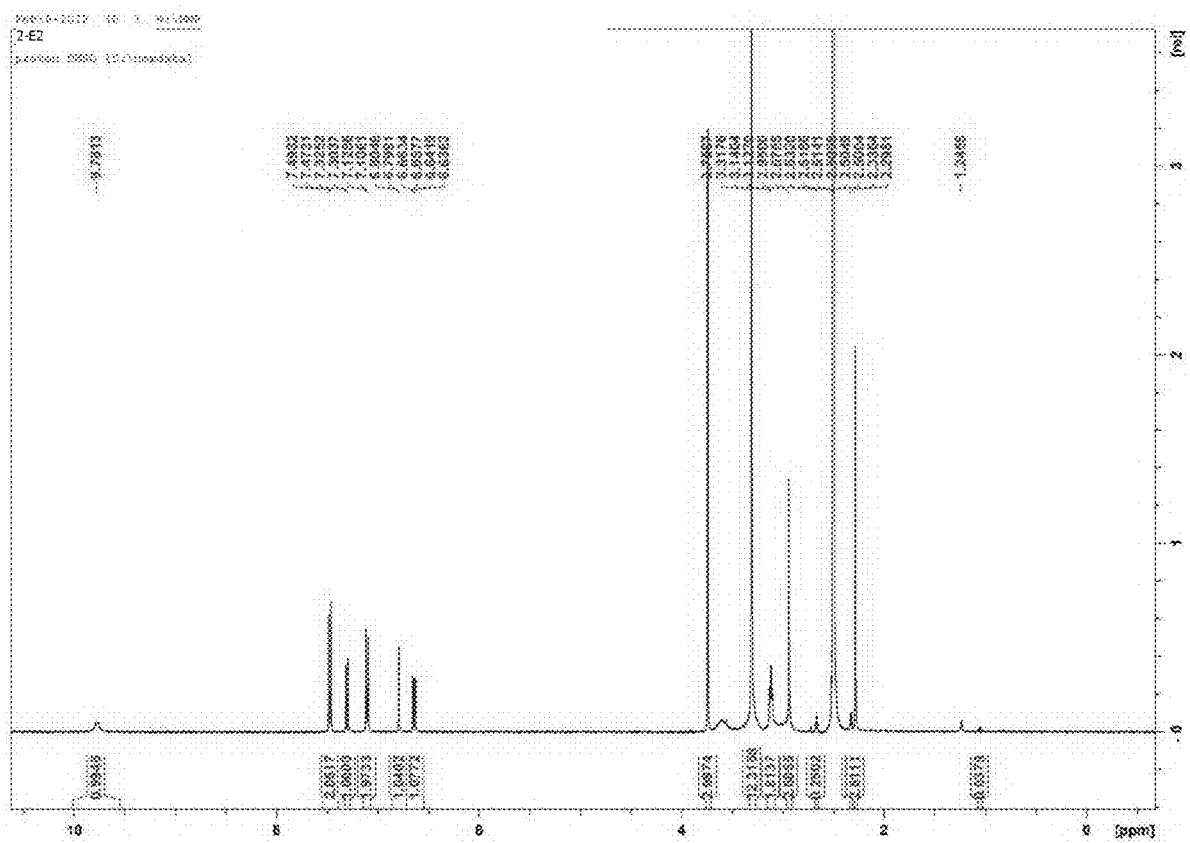

FIG. 493 depicts the $^1$H NMR of tabernanthalog tosylate salt; 2-E2 (Experiment Reference 2-Sample Reference E2), analysis was acquired in DMSO-d6 and calibrated to the non-deuterated solvent residual at 2.50 ppm. 1.0 mol of API to 1.0 mol of p-toluenesulfonic acid. Ethanol content 0.1% w/w.

Figure 494:
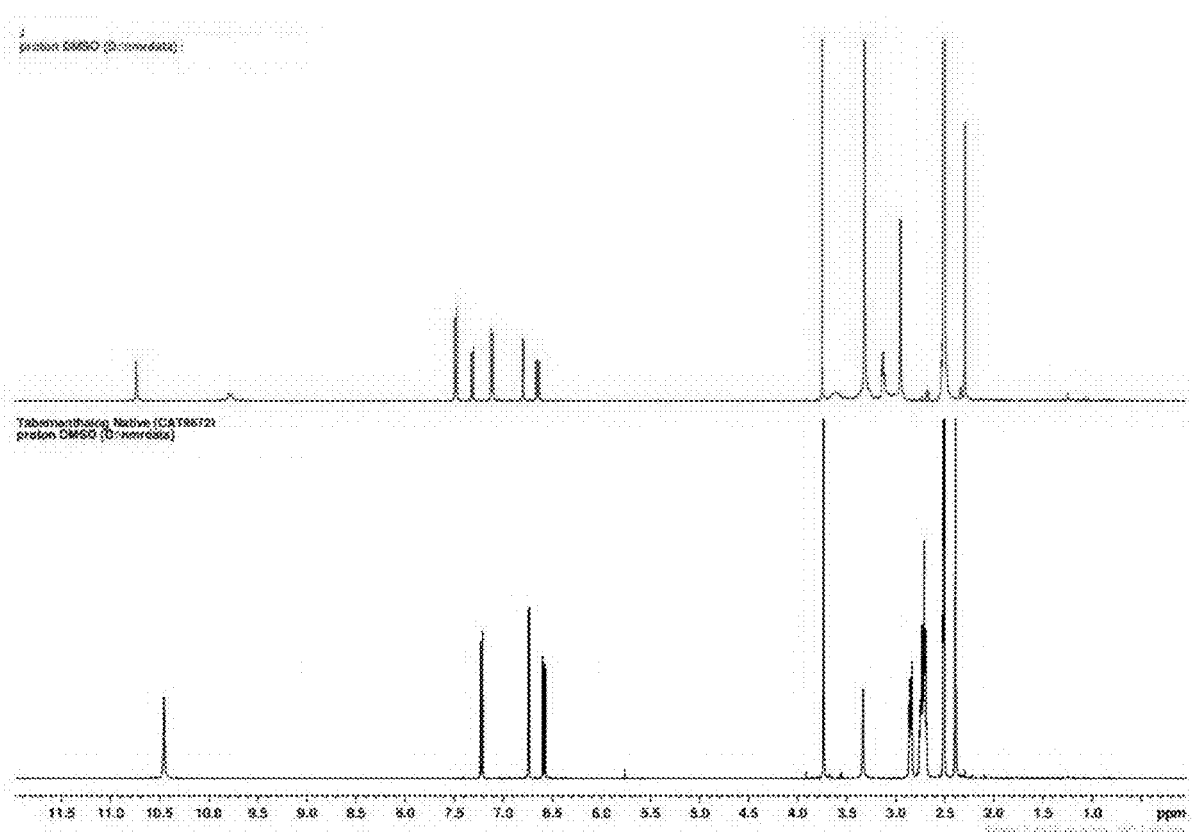

FIG. 494 depicts the $^1$H NMR of tabernanthalog tosylate salt; 2-E2 (Experiment Reference 2-Sample Reference E2) (top spectrum), overlaid with Tabernanthalog (native) (bottom spectrum). Slight appreciation in impurity burden compared to the free base is shown.

Figure 495:
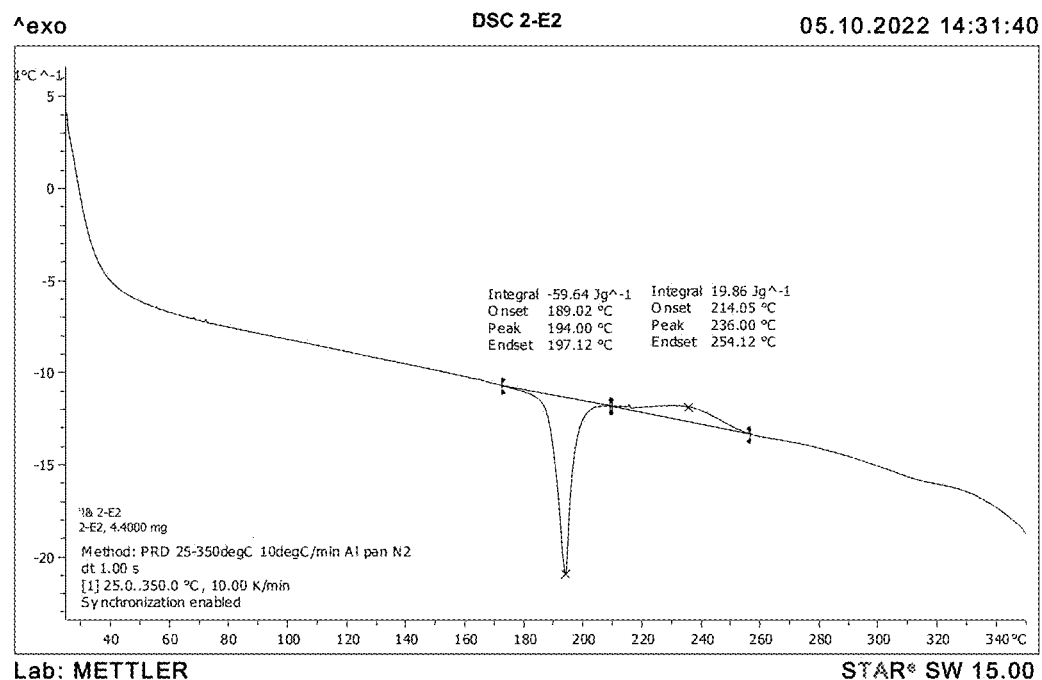

FIG. 495 depicts the DSC profile of tabernanthalog tosylate salt; 2-E2 (Experiment Reference 2-Sample Reference E2), analysis was acquired at a ramp rate of +10° C./minute.

Figure 496:
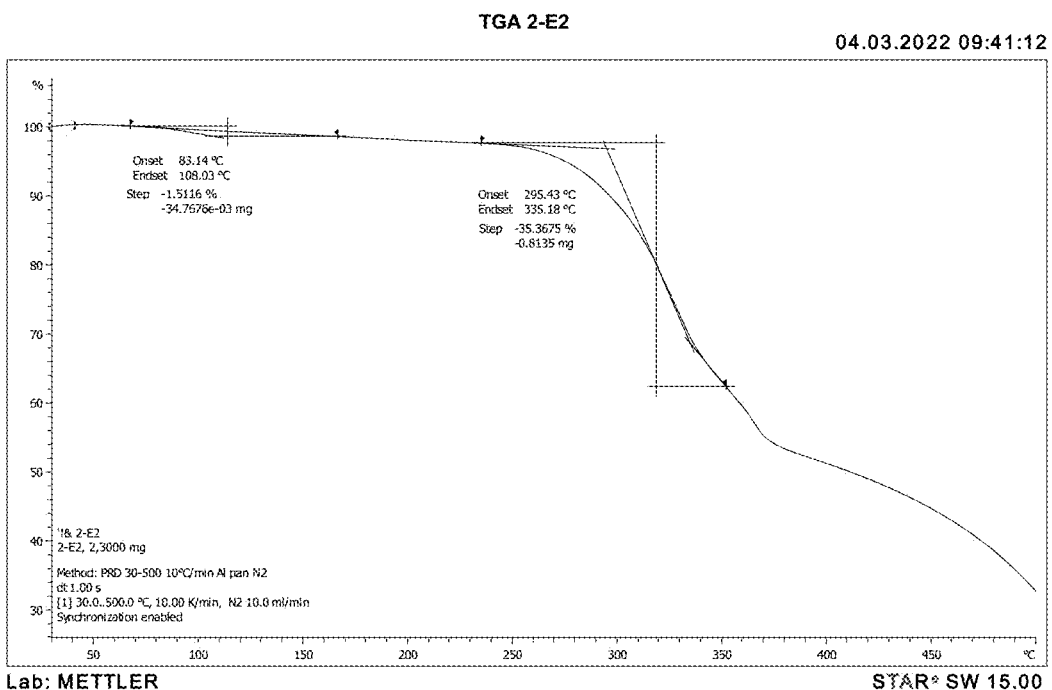

FIG. 496 depicts the TGA of tabernanthalog tosylate salt; 2-E2 (Experiment Reference 2-Sample Reference E2), analysis was acquired at a ramp rate of +10° C./minute. Small −Δwt., not solvent, attributed to water from hydrated p-toluenesulfonic acid.

Figure 496A:
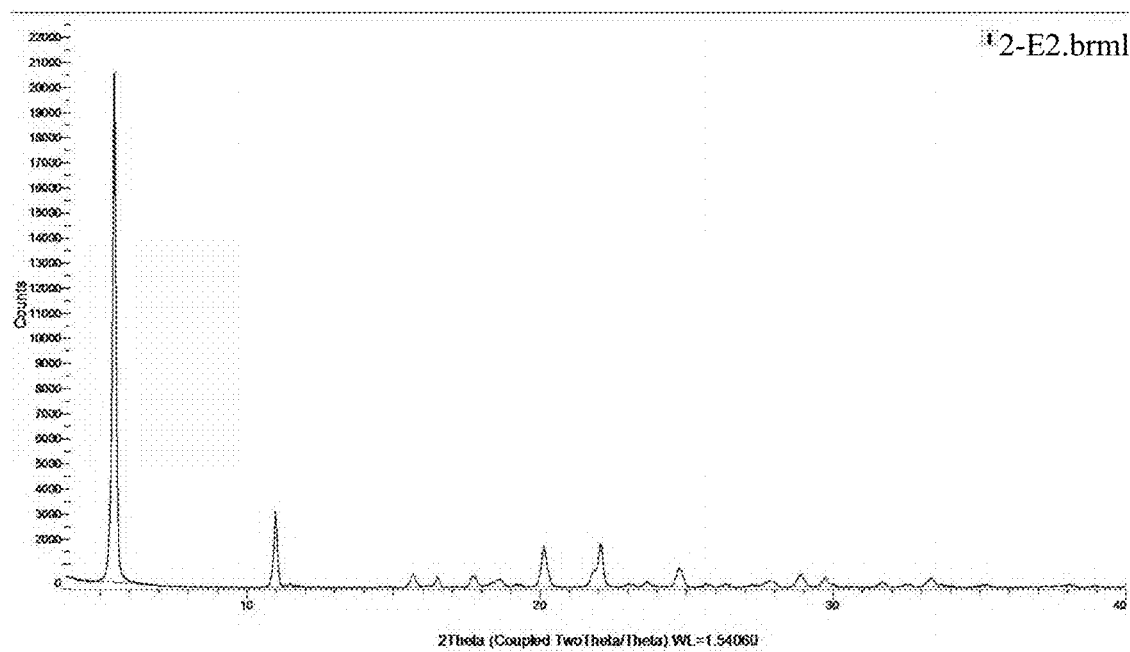

FIG. 496A depicts the XRPD of tabernanthalog tosylate salt (2-E2; Experiment Reference 2-Sample Reference E2). Highly crystalline, low angle reflection dominated, probably due to particle effects. Diffraction pattern should improve with increased powder averaging.

Figure 509:
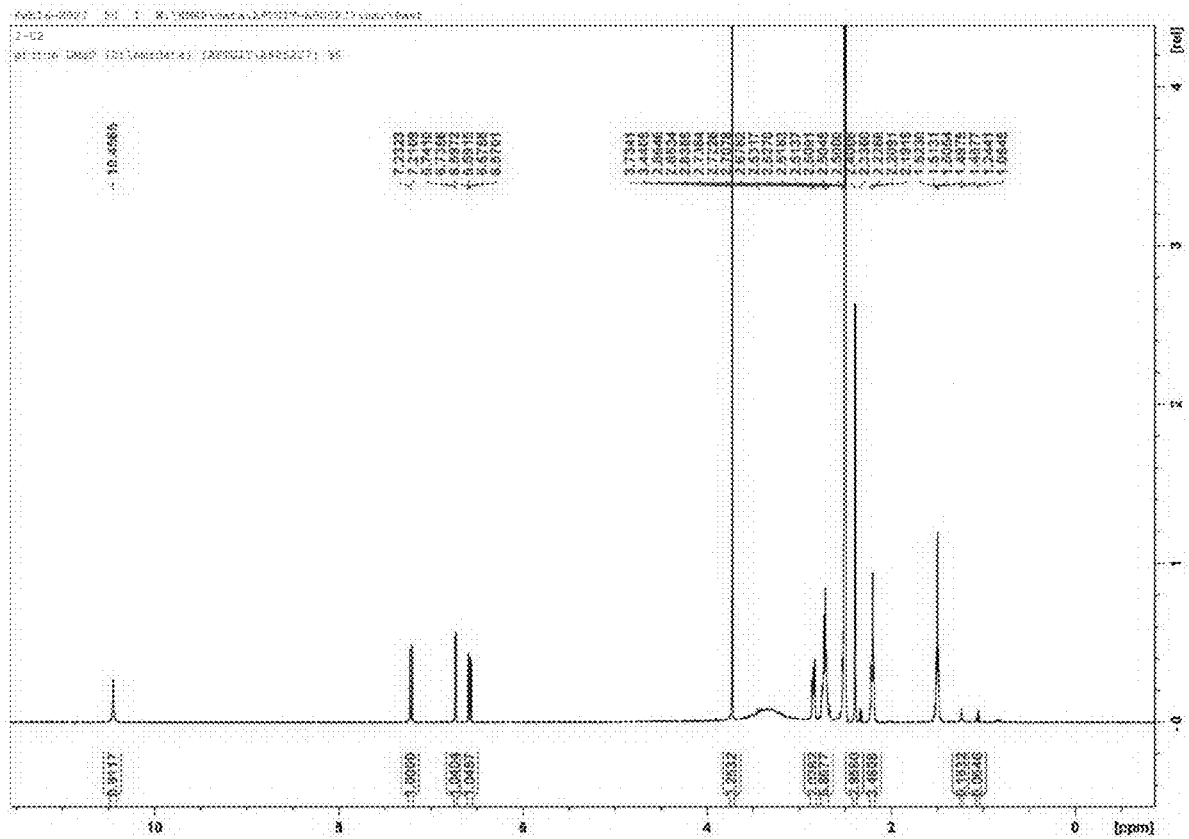

FIG. 509 depicts the $^1$H NMR of tabernanthalog adipate salt, 2-U2 (Experiment Reference 2-Sample Reference U2), analysis was acquired in DMSO-d6 and calibrated to the non-deuterated solvent residual at 2.50 ppm. 1.0 mol of API to 1.0 mol of adipic acid. Ethanol content 0.3% w/w.

Figure 510:
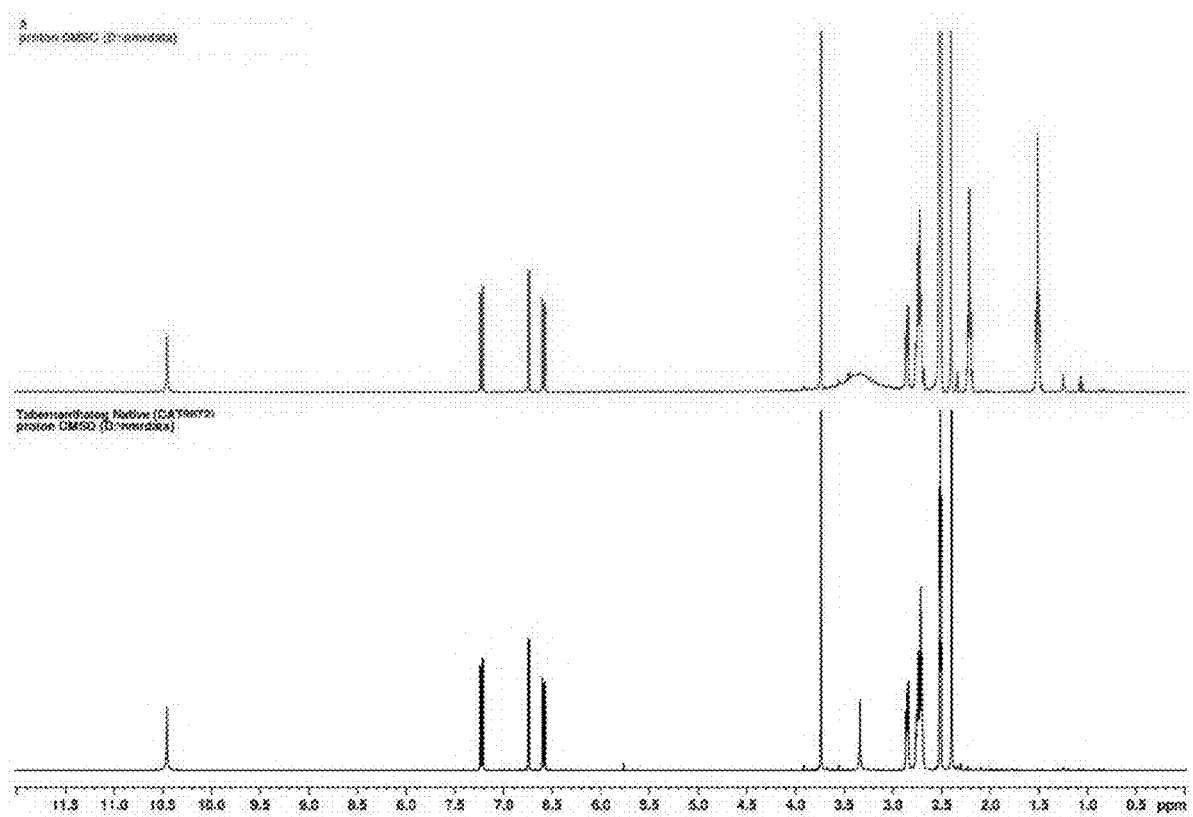

FIG. 510 depicts the $^1$H NMR of tabernanthalog adipate salt; 2-U2 (Experiment Reference 2-Sample Reference U2) (top spectrum), overlaid with Tabernanthalog (native) (bottom spectrum).

Figure 511:
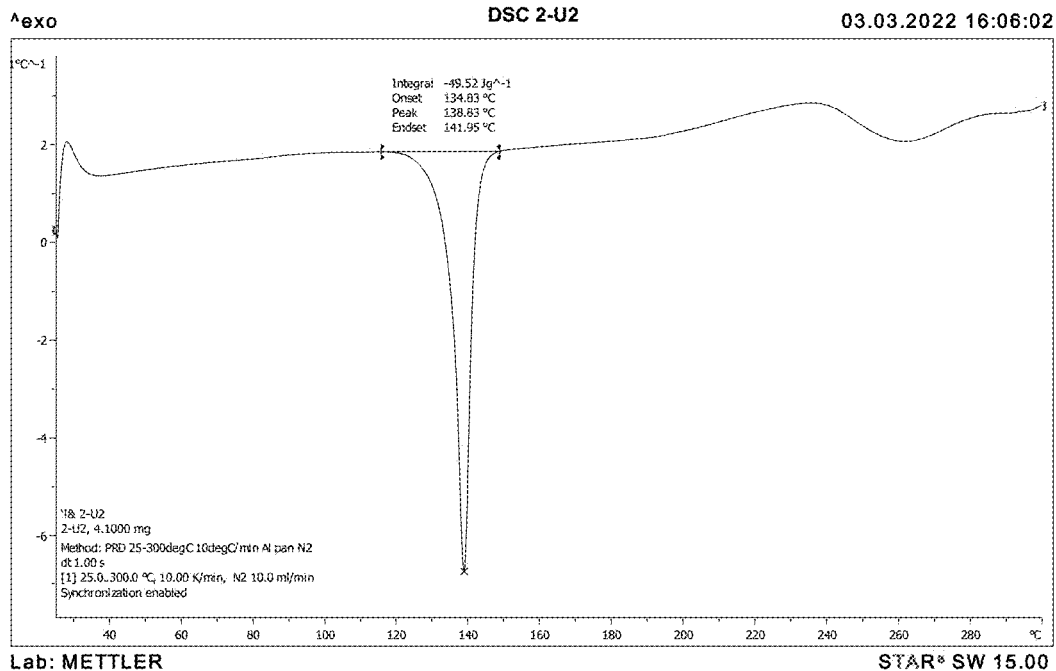

FIG. 511 depicts the DSC profile of tabernanthalog adipate salt; 2-U2 (Experiment Reference 2-Sample Reference U2), analysis was acquired at a ramp rate of +10° C./minute.

Figure 512:
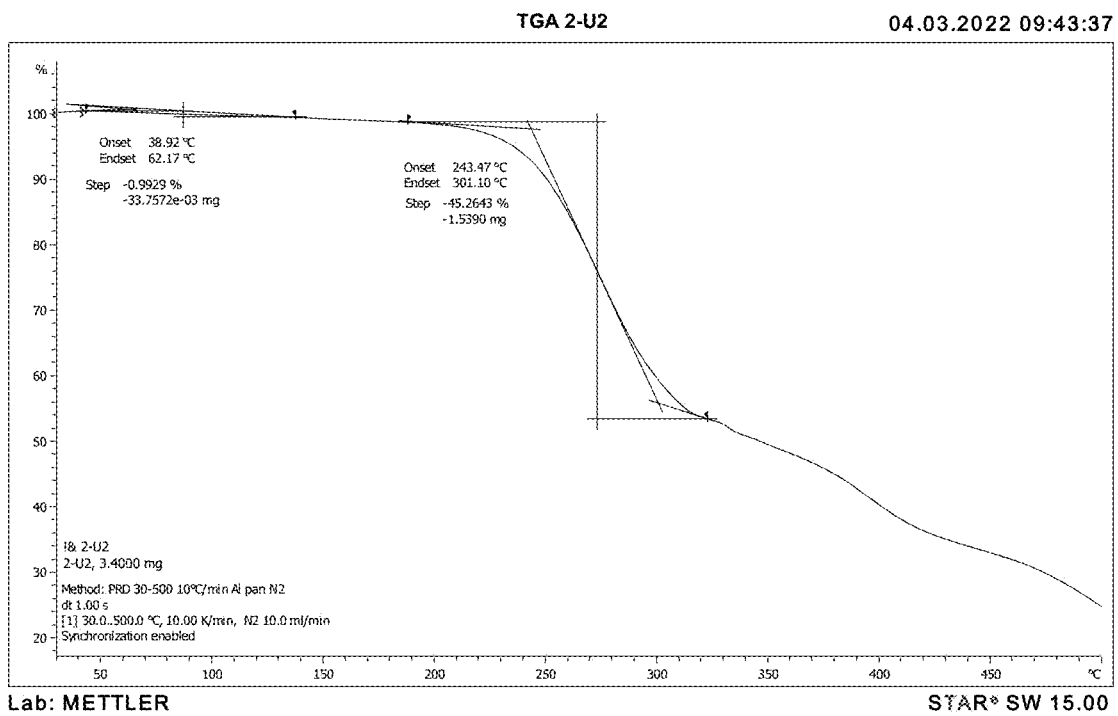

FIG. 512 depicts the TGA of tabernanthalog adipate salt; 2-U2 (Experiment Reference 2-Sample Reference U2), analysis was acquired at a ramp rate of +10° C./minute.

Figure 514:
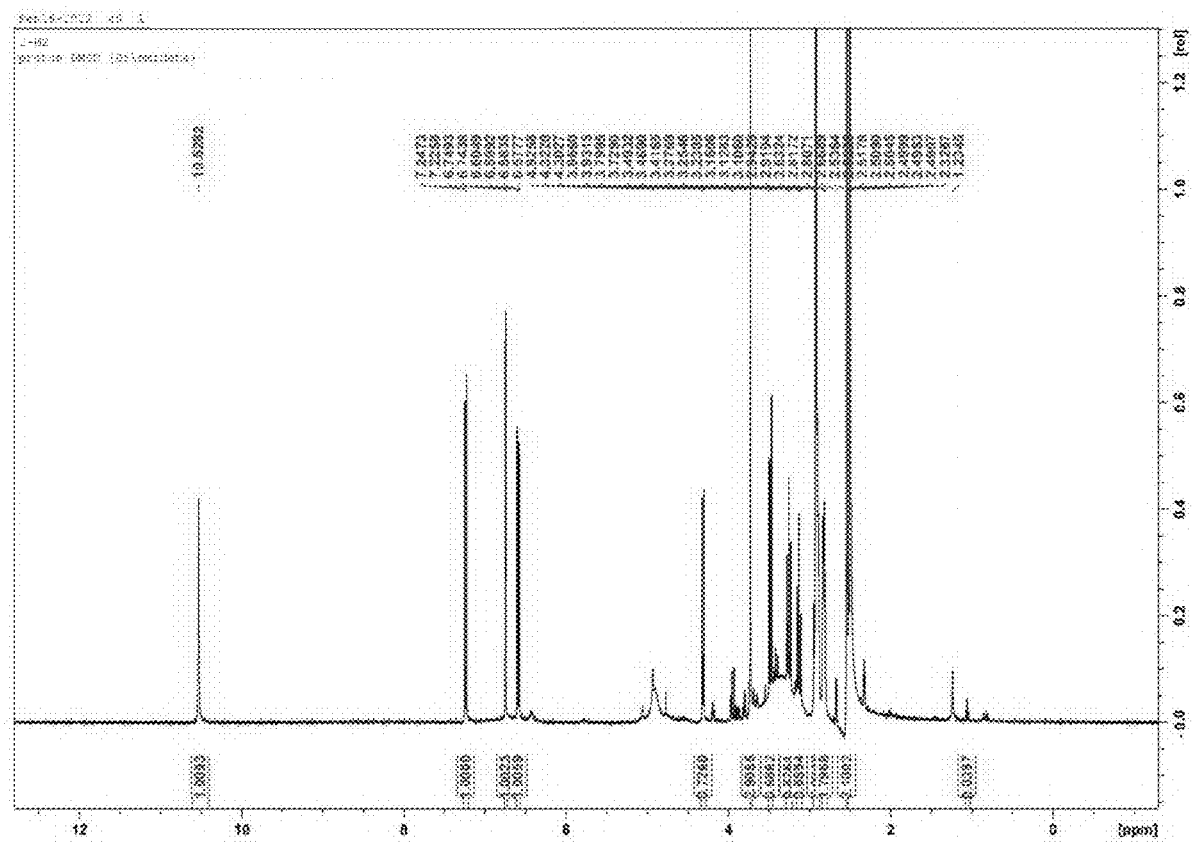

FIG. 514 depicts the $^1$H NMR of tabernanthalog glucuronate salt; 2-M2 (Experiment Reference 2-Sample Reference M2), analysis was acquired in DMSO-d6 and calibrated to the non-deuterated solvent residual at 2.50 ppm. 1.0 mol of API to 0.7 mol of D-glucuronic acid (counterion stoichiometry<unity+appreciation in impurity burden). Ethanol content 0.2% w/w.

Figure 515:
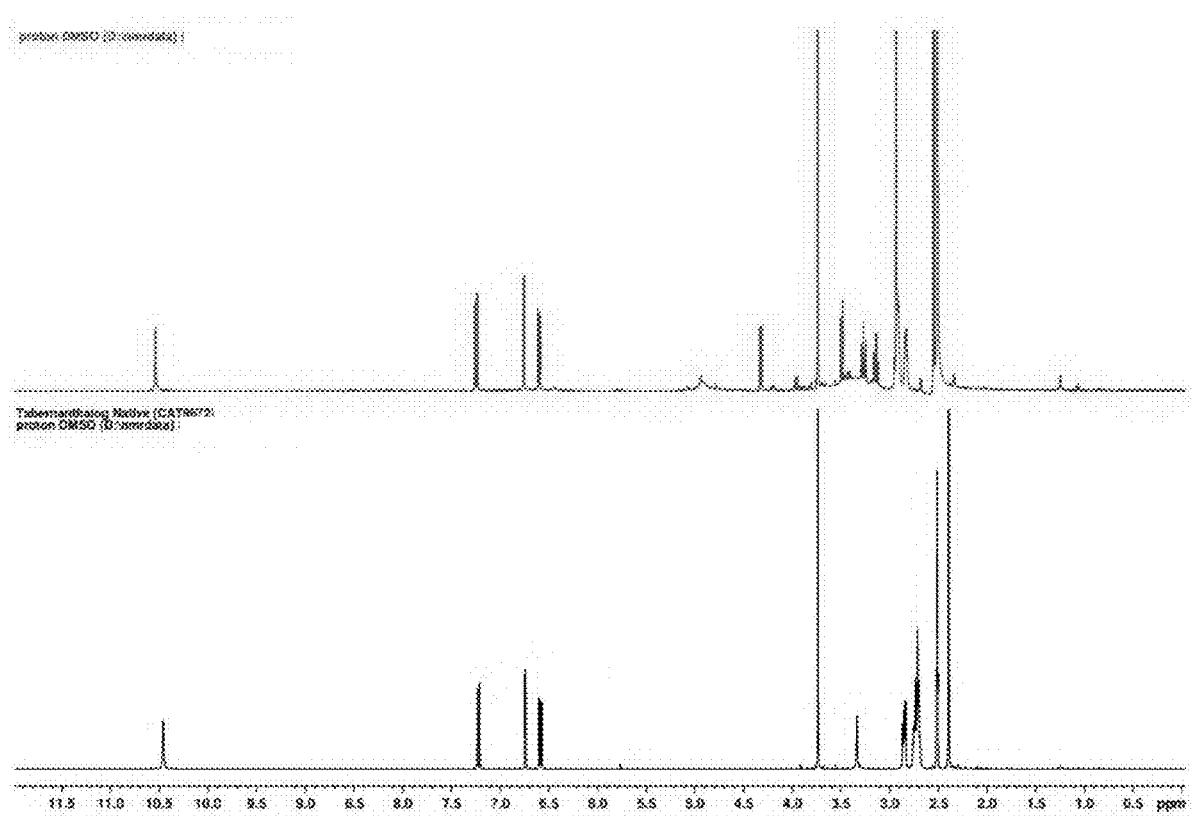

FIG. 515 depicts the $^1$H NMR of tabernanthalog glucuronate salt; 2-M2 (Experiment Reference 2-Sample Reference M2) (top spectrum), overlaid with tabernanthalog (native) (bottom spectrum).

Figure 516:
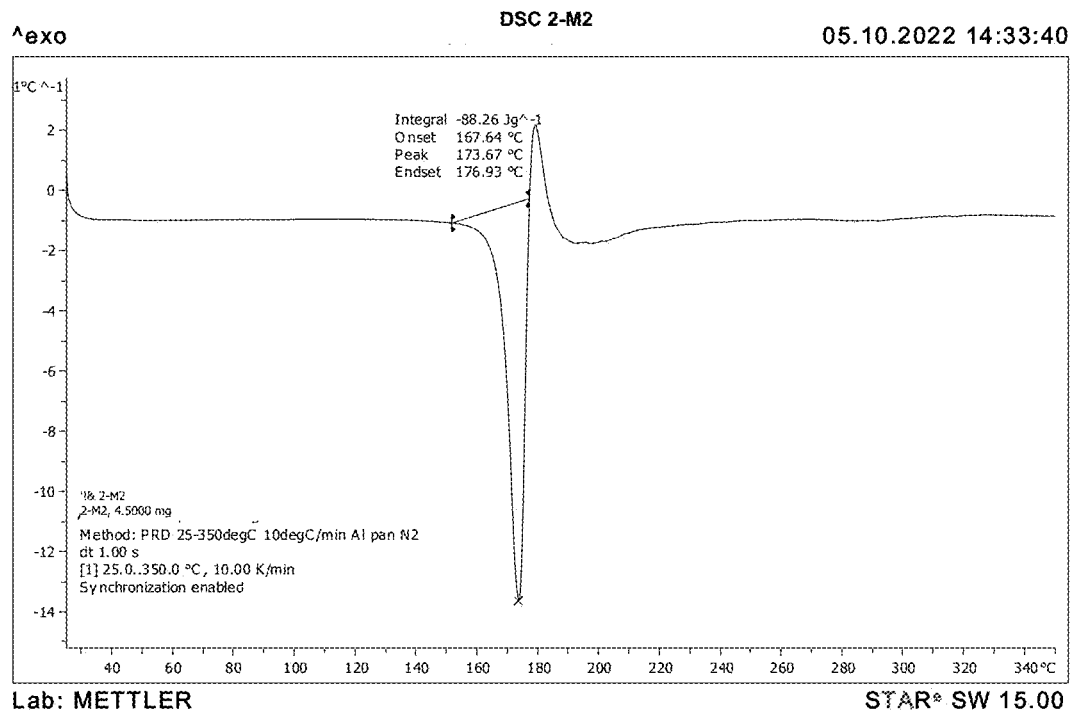

FIG. 516 depicts the DSC profile of tabernanthalog glucuronate salt; 2-M2 (Experiment Reference 2-Sample Reference M2), analysis was acquired at a ramp rate of +10° C./minute.

Figure 517:
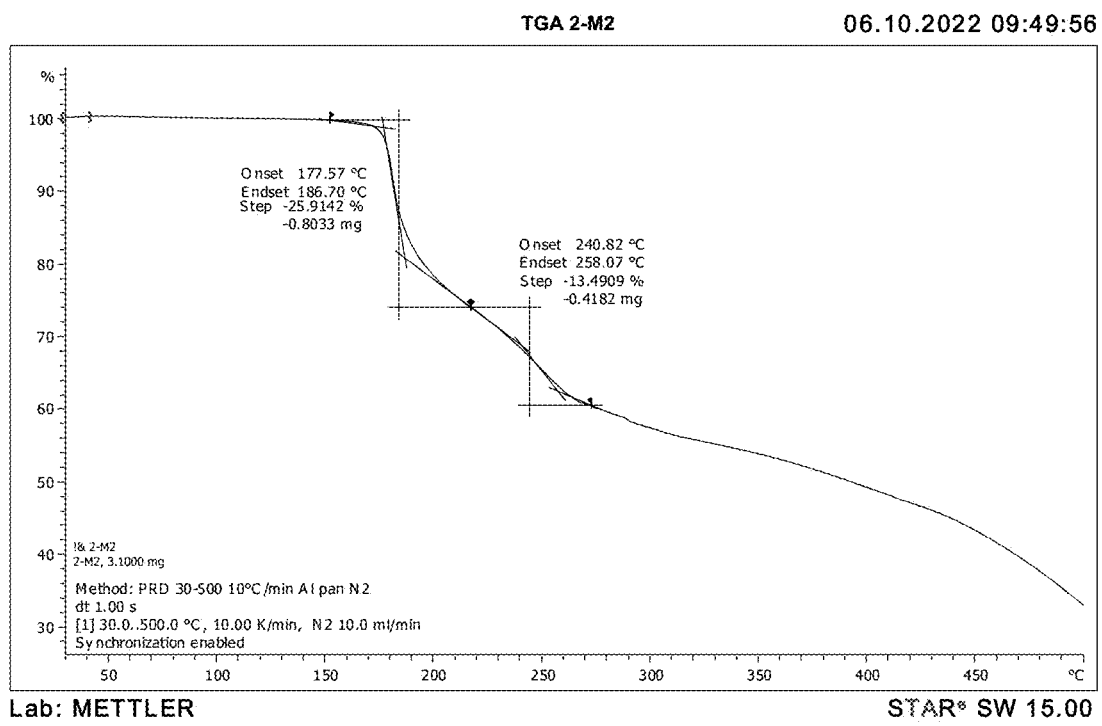

FIG. 517 depicts the TGA of tabernanthalog glucuronate salt; 2-M2 (Experiment Reference 2-Sample Reference M2), analysis was acquired at a ramp rate of +10° C./minute.

Figure 519:
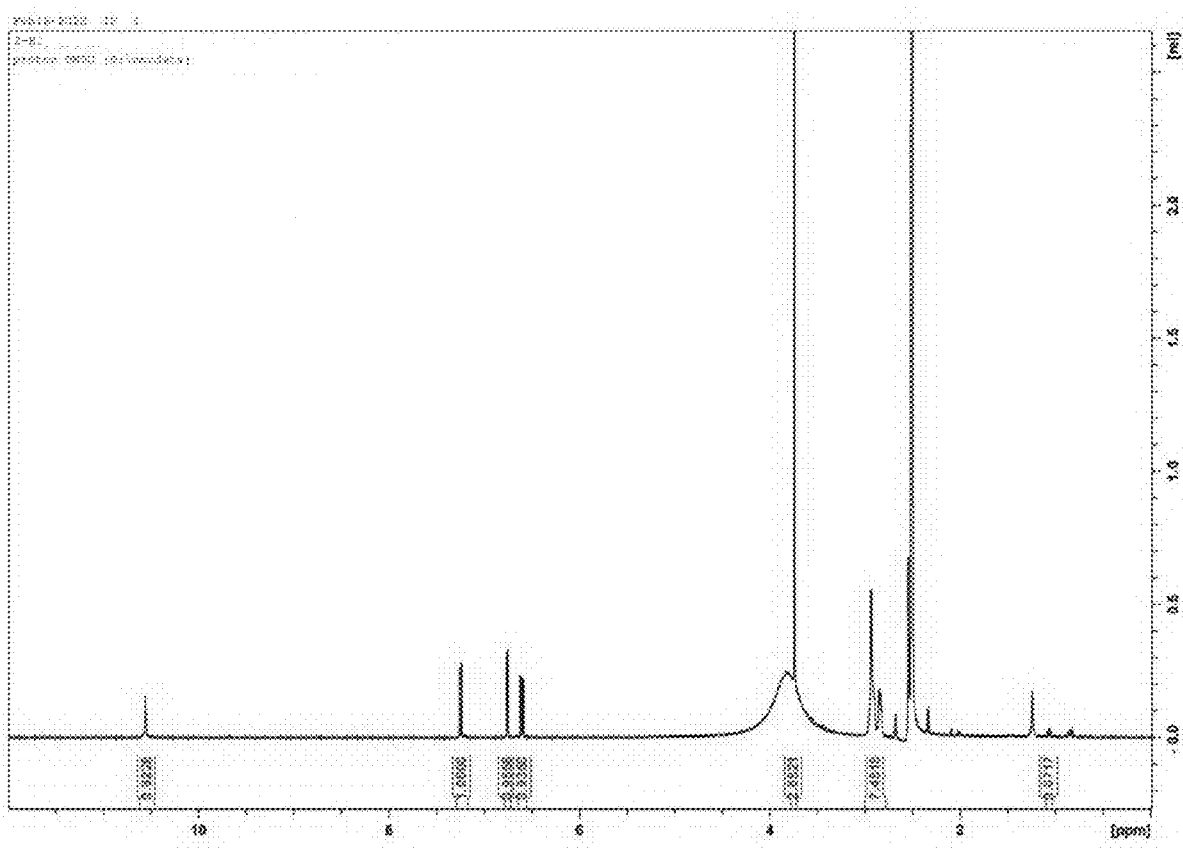

FIG. 519 depicts the $^1$H NMR of tabernanthalog phosphate salt; 2-H2 (Experiment Reference 2-Sample Reference H2), acquired in DMSO-d6 and calibrated to the non-deuterated solvent residual at 2.50 ppm. 1.0 mol of API to 0.7 mol of phosphoric acid. Ethanol content 0.3% w/w. Counterion stoichiometry<unity+appreciation in impurity burden.

Figure 520:
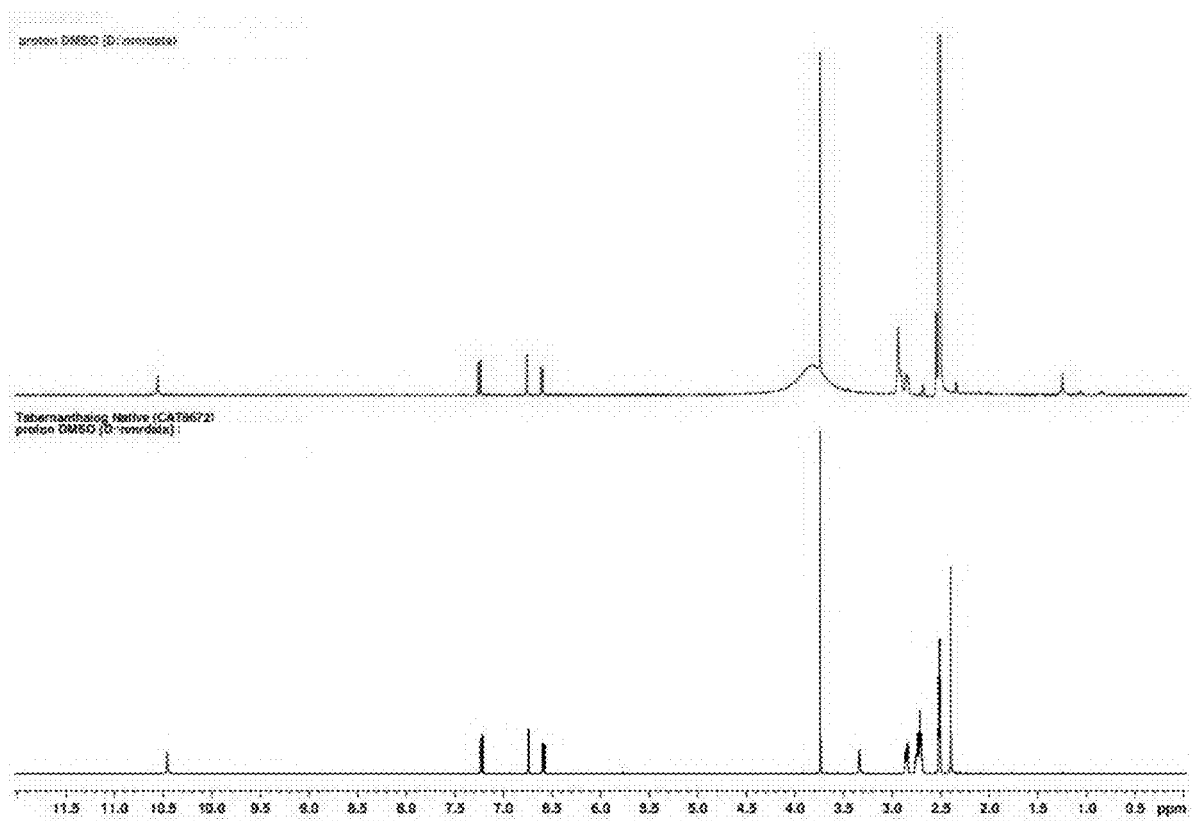

FIG. 520 depicts the $^1$H NMR of tabernanthalog phosphate salt; 2-H2 (Experiment Reference 2-Sample Reference H2) (top spectrum), overlaid with Tabernanthalog (native) (bottom spectrum).

Figure 521:
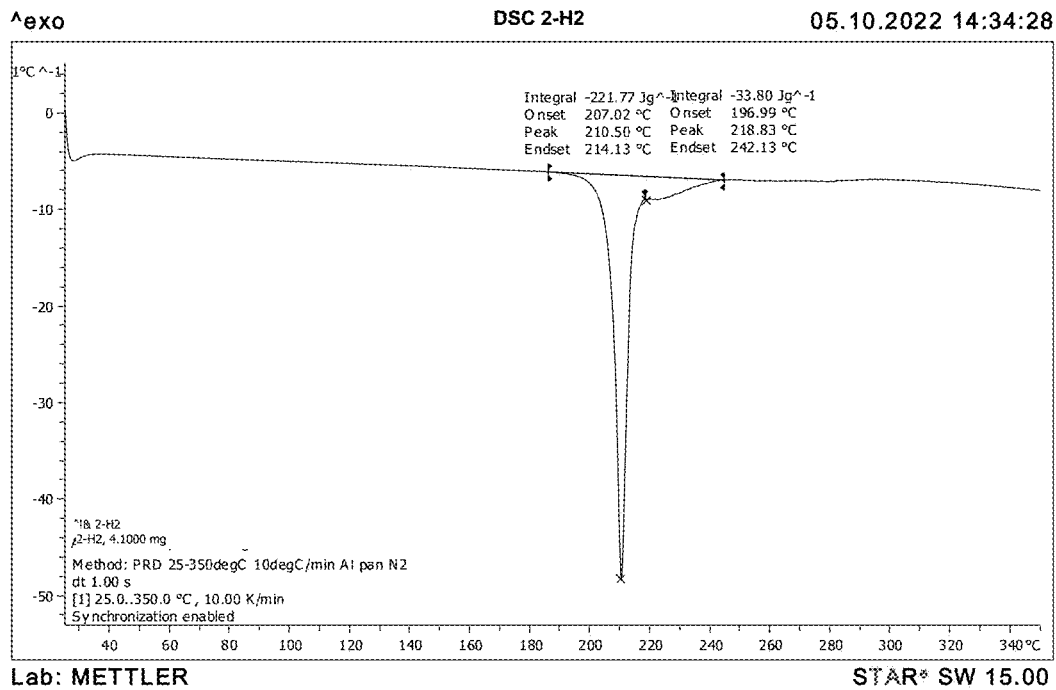

FIG. 521 depicts the DSC profile of tabernanthalog phosphate salt; 2-H2 (Experiment Reference 2-Sample Reference H2), analysis was acquired at a ramp rate of +10° C./minute.

Figure 522:
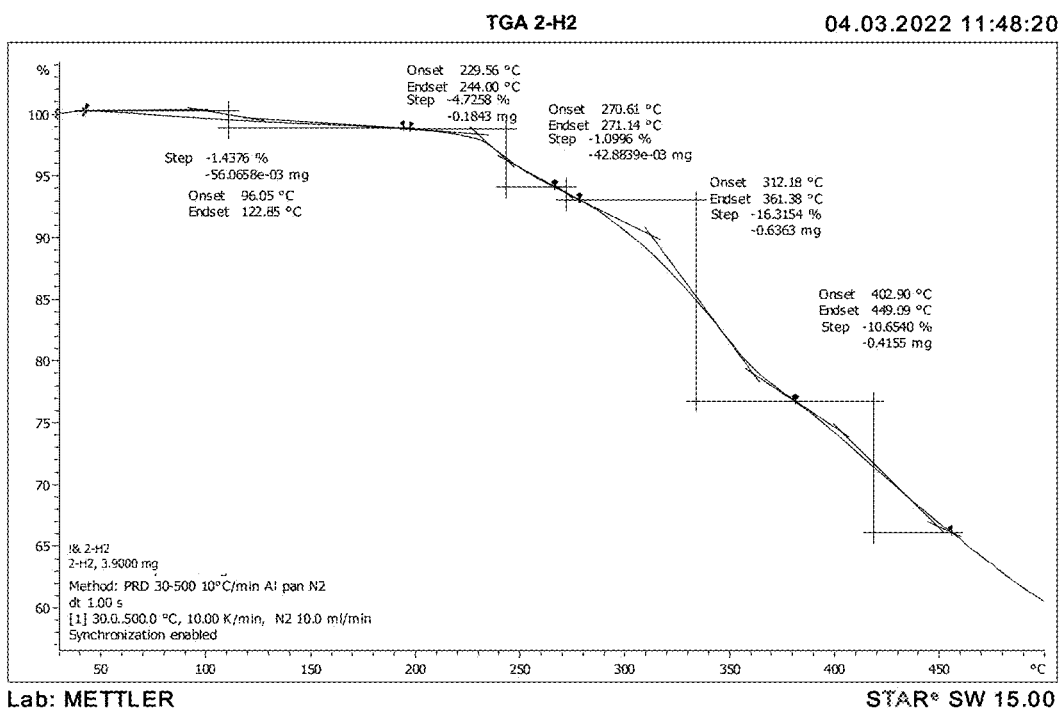

FIG. 522 depicts the TGA of tabernanthalog phosphate salt; 2-H2 (Experiment Reference 2-Sample Reference H2), analysis was acquired at a ramp rate of +10° C./minute.

Figure 524:
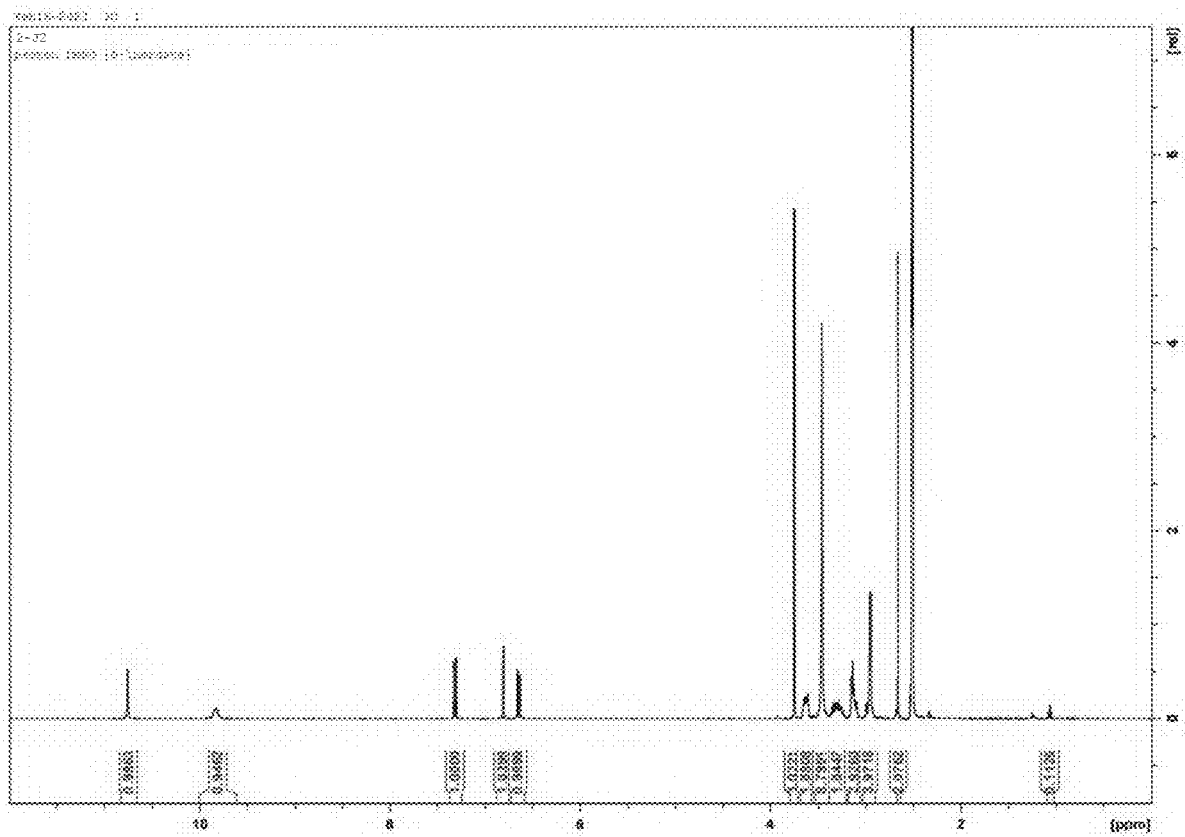

FIG. 524 depicts the $^1$H NMR of tabernanthalog edisylate salt; 2-J2 (Experiment Reference 2-Sample Reference J2), analysis was acquired in DMSO-d6 and calibrated to the non-deuterated solvent residual at 2.50 ppm. 1.0 mol of API to 1.0 mol of ethane-1,2-disulfonic acid. Ethanol content 0.4% w/w.

Figure 525:
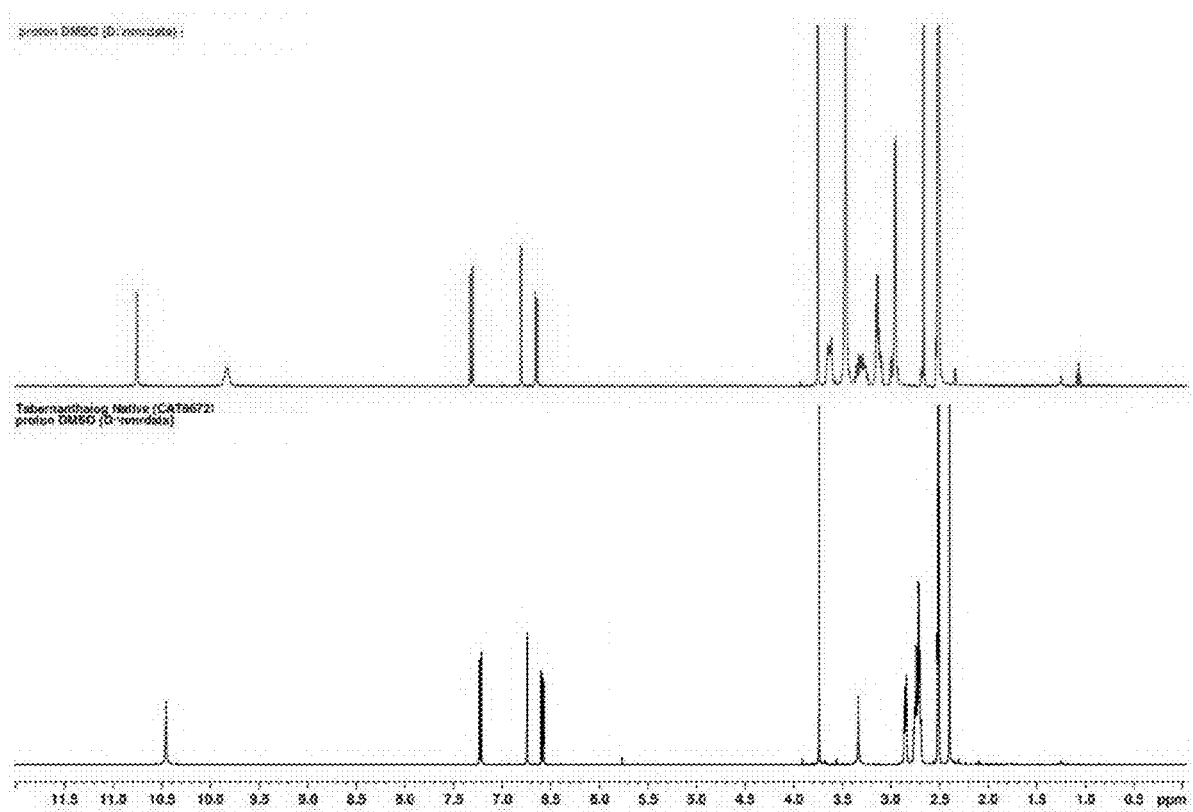

FIG. 525 depicts the $^1$H NMR of tabernanthalog edisylate salt; 2-J2 (Experiment Reference 2-Sample Reference J2) (top spectrum; small decrease in the impurity burden was observed in aryl and aliphatic regions), overlaid with Tabernanthalog (native) (bottom spectrum).

Figure 526:
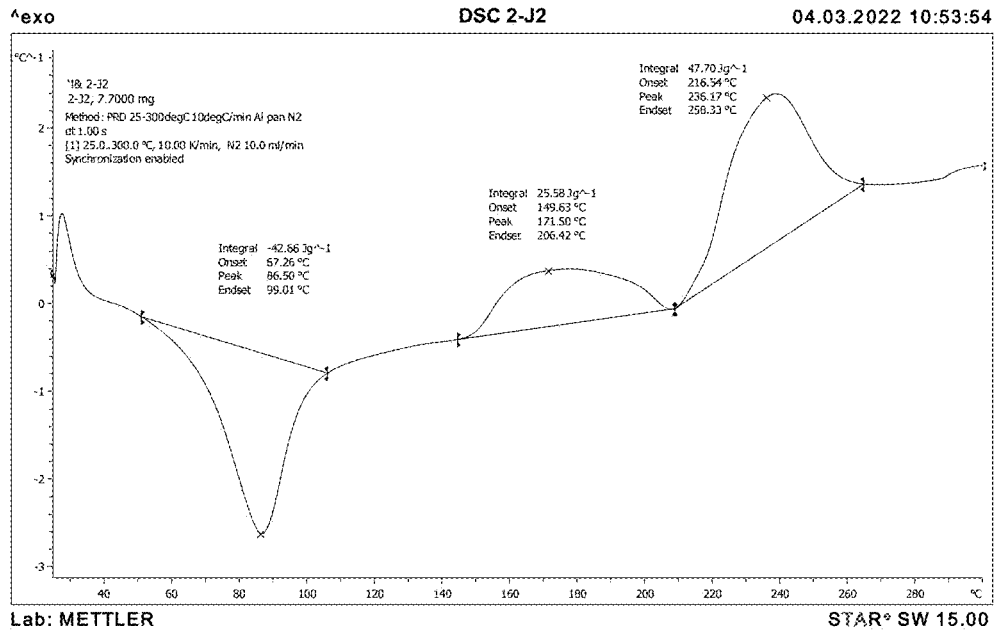

FIG. 526 depicts the DSC profile of tabernanthalog edisylate salt; 2-J2 (Experiment Reference 2-Sample Reference J2), analysis was acquired at a ramp rate of +10° C./minute.

Figure 527:
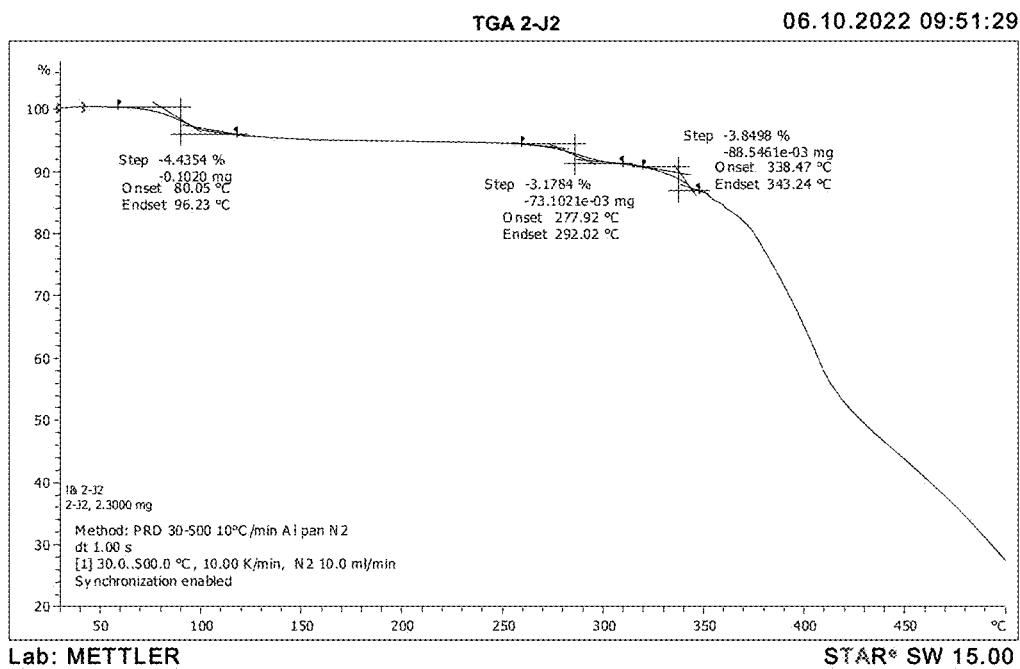

FIG. 527 depicts the TGA of tabernanthalog edisylate salt; 2-J2 (Experiment Reference 2-Sample Reference J2), analysis was acquired at a ramp rate of +10° C./minute. −Δ wt., attributed to water release, originating from hydrated counter ion (EDSA·2H$_2$O).

Figure 529:
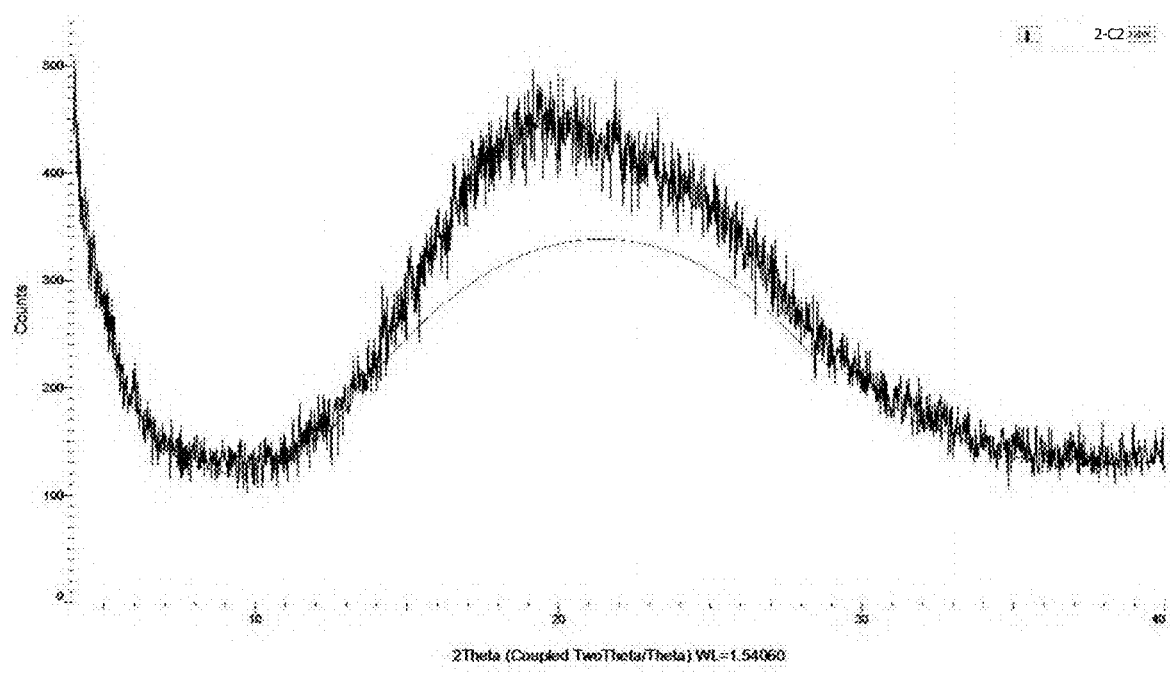

FIG. 529 depicts the XRPD of the tabernanthalog sulfate salt, 2-C2 (Experiment Reference 2-Sample Reference C2) (amorphous).

Figure 535:
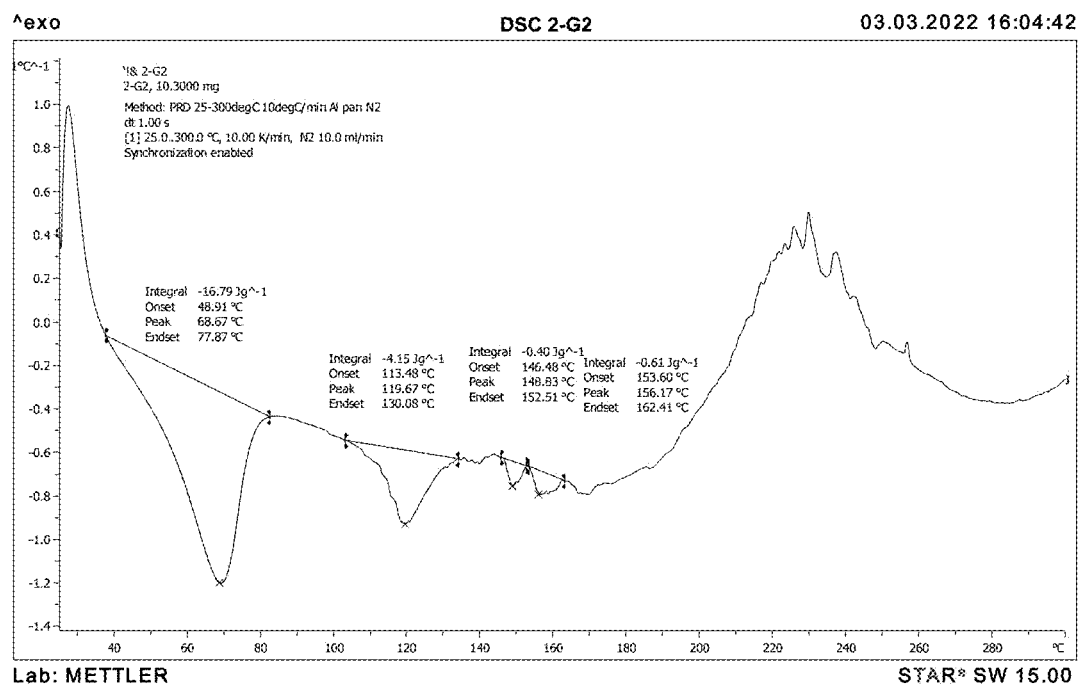

FIG. 535 depicts the DSC profile of 2-G2 (Experiment Reference 2-Sample Reference G2; the tabernanthalog maleate salt), analysis was acquired at a ramp rate of +10° C./minute.

Figure 536:
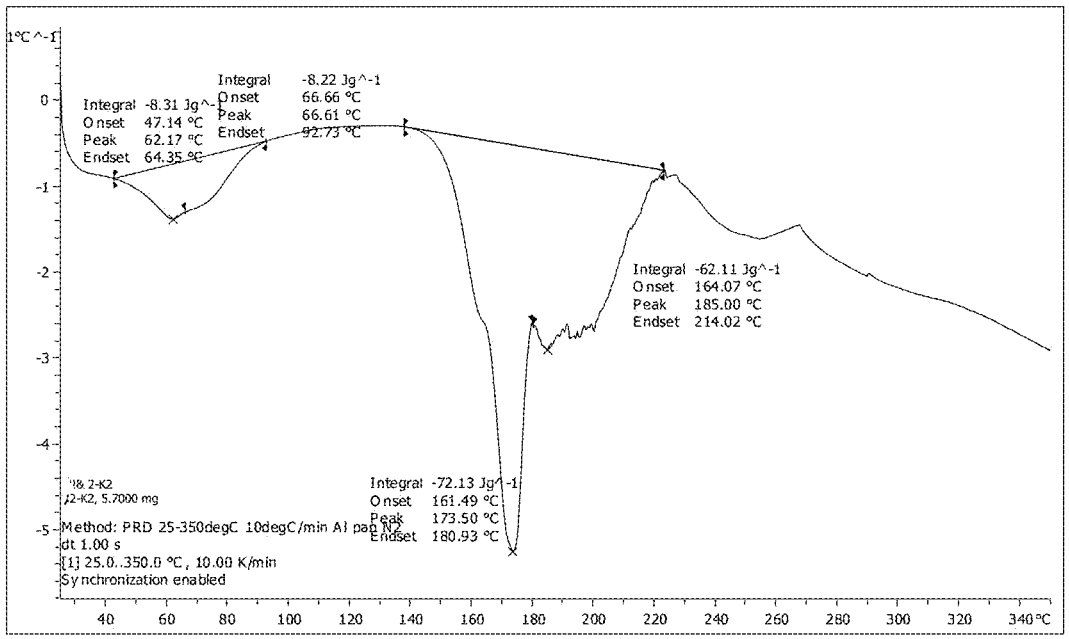

FIG. 536 depicts the DSC profile of 2-K2 (Experiment Reference 2-Sample Reference K2; the tabernanthalog galactarate salt), analysis was acquired at a ramp rate of +10° C./minute.

Figure 537:
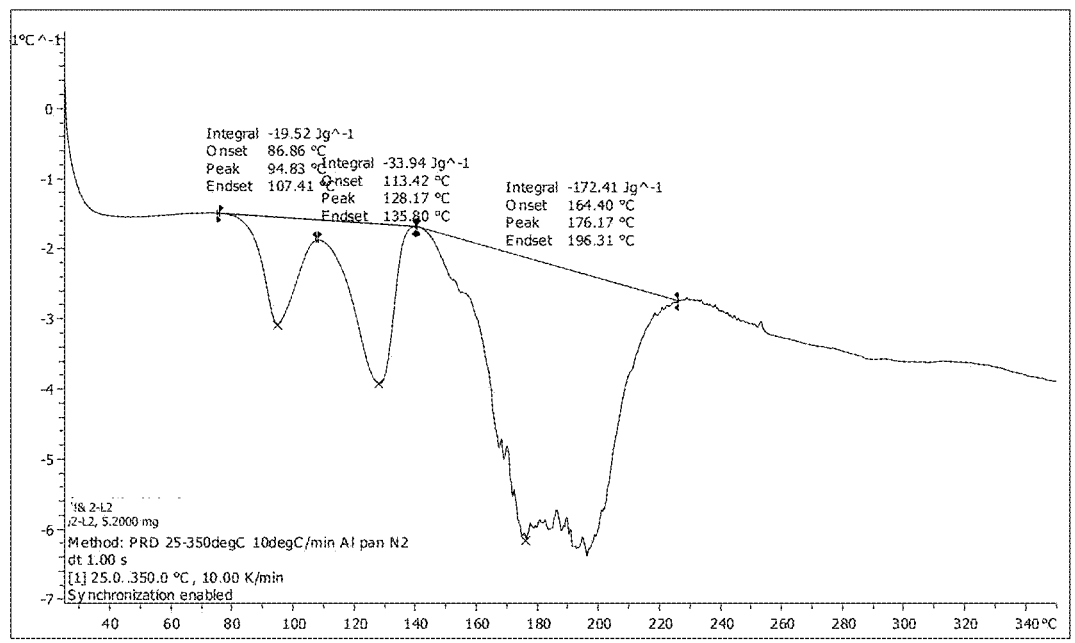

FIG. 537 depicts the DSC profile of 2-L2 (Experiment Reference 2-Sample Reference L2; the tabernanthalog citrate salt), analysis was acquired at a ramp rate of +10° C./minute.

Figure 538:
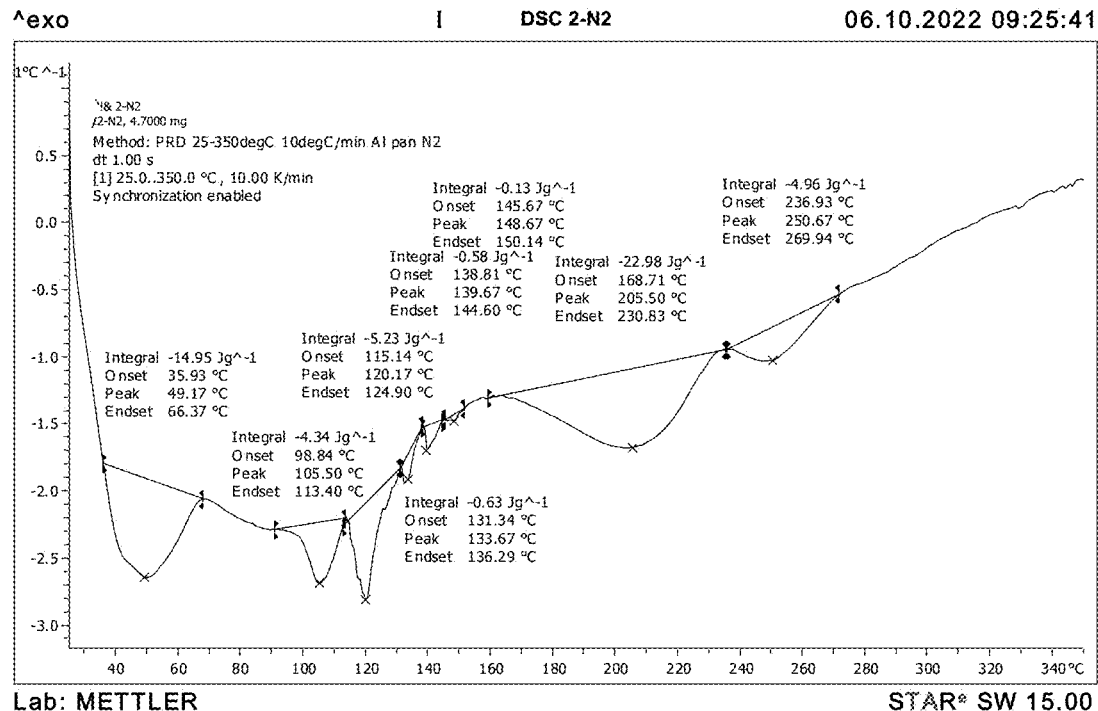

FIG. 538 depicts the DSC profile of 2-N2 (Experiment Reference 2-Sample Reference N2; the tabernanthalog glycolate salt), analysis was acquired at a ramp rate of +10° C./minute.

Figure 539:
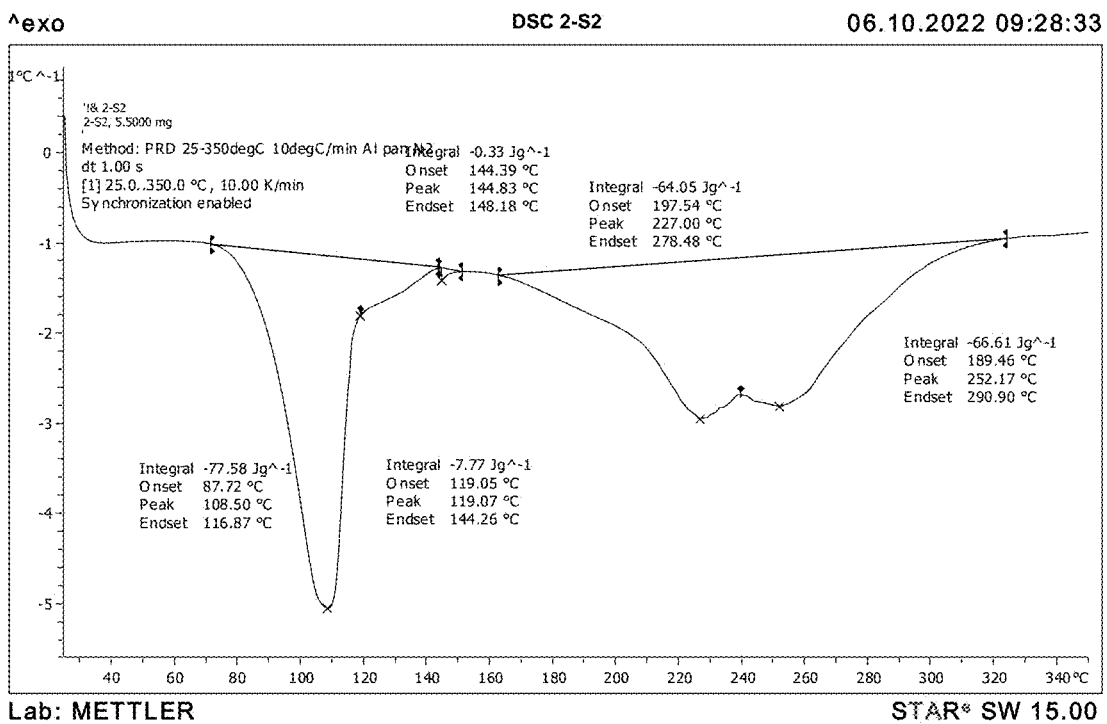

FIG. 539 depicts the DSC profile of 2-S2 (Experiment Reference 2-Sample Reference S2; the tabernanthalog succinate salt), analysis was acquired at a ramp rate of +10° C./minute.

Figure 540:
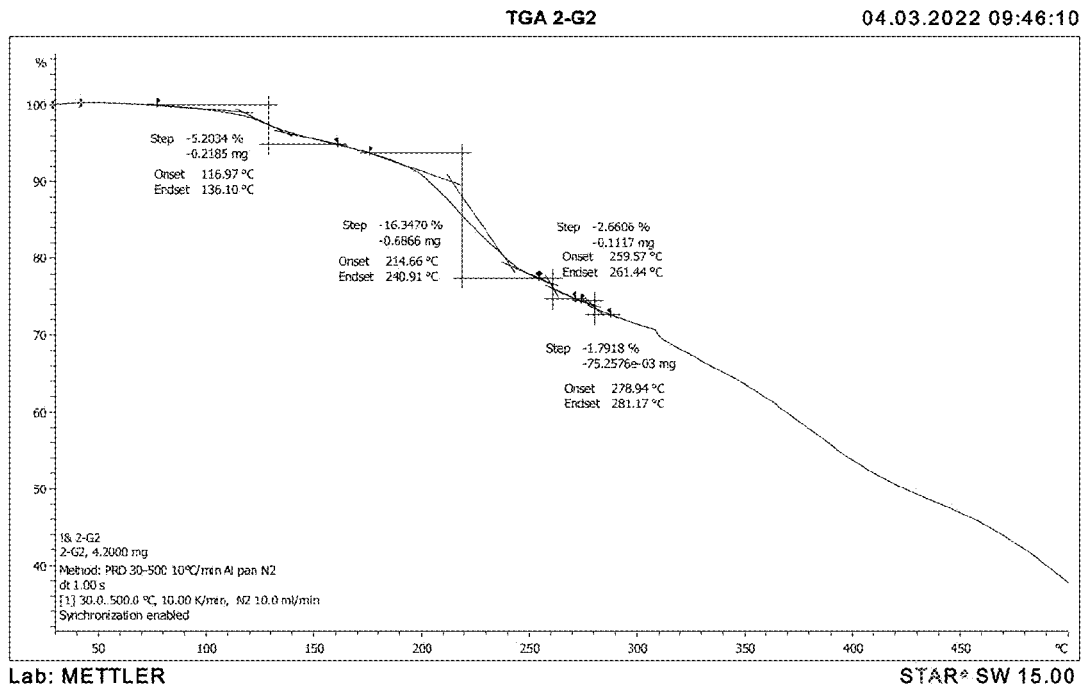

FIG. 540 depicts the TGA of the tabernanthalog maleate salt (2-G2; Experiment Reference 2-Sample Reference G2), analysis was acquired at a ramp rate of +10° C./minute.

Figure 541:
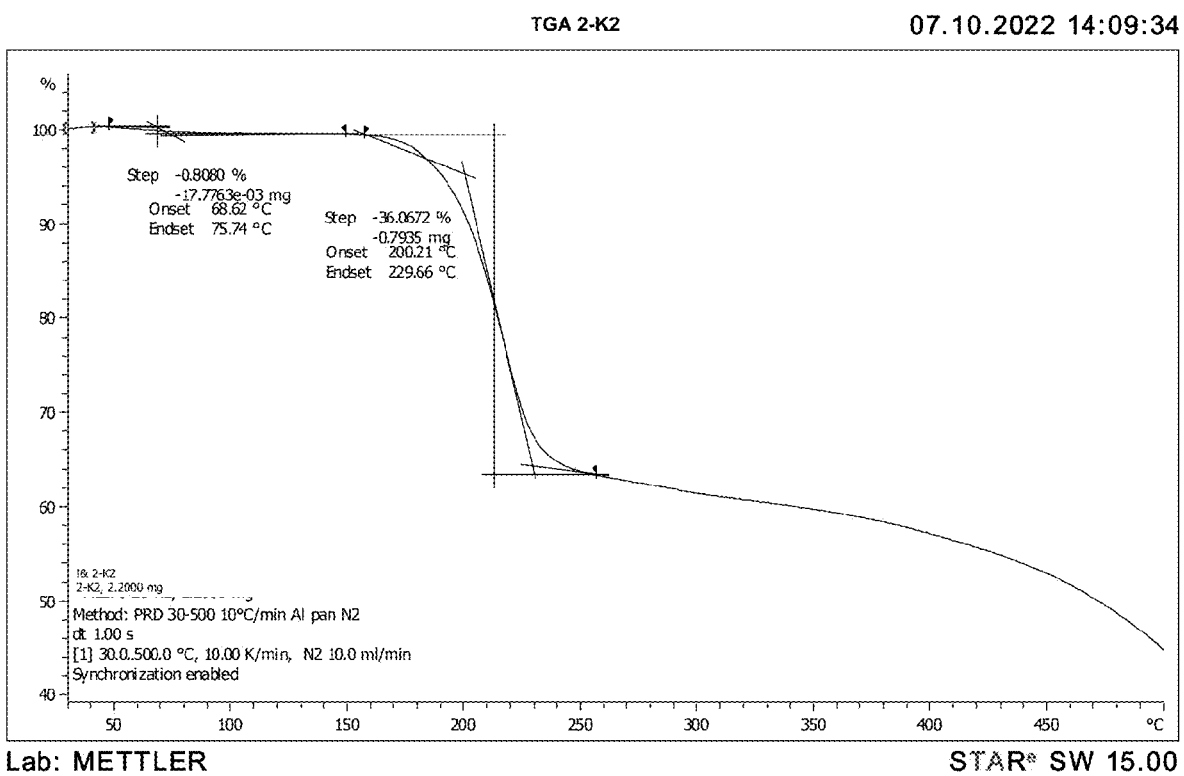

FIG. 541 depicts the TGA of the tabernanthalog galactarate salt (2-K2; Experiment Reference 2-Sample Reference K2)), analysis was acquired at a ramp rate of +10° C./minute.

Figure 542:
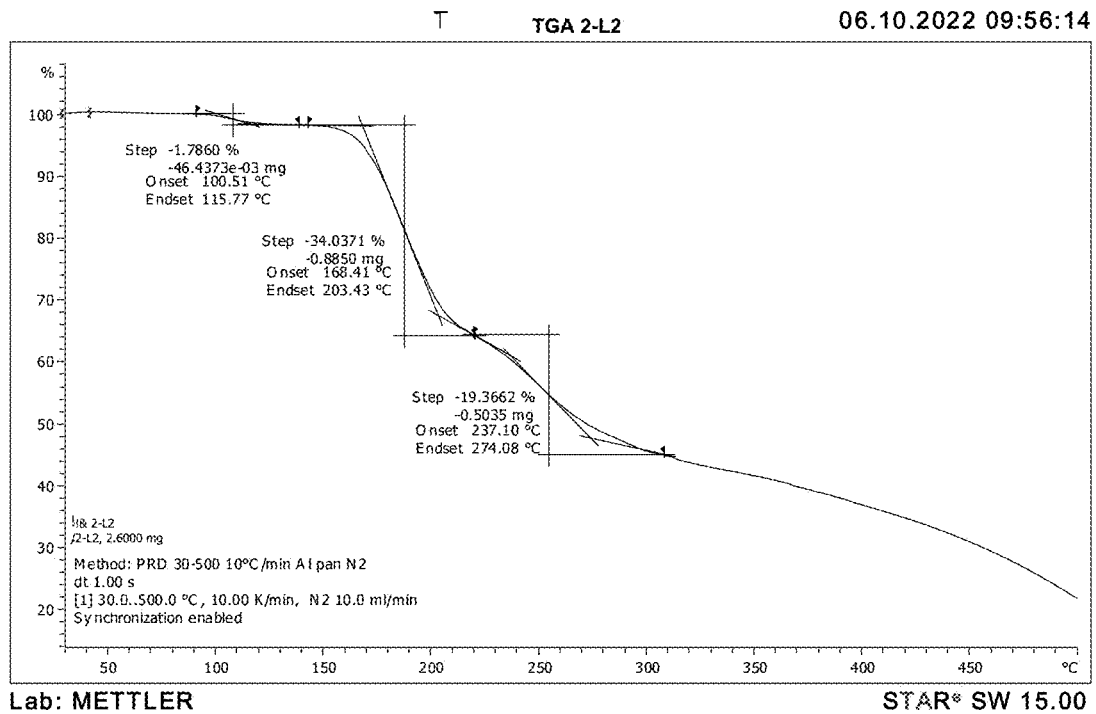

FIG. 542 depicts the TGA of the tabernanthalog citrate salt (2-L2; Experiment Reference 2-Sample Reference L2), analysis was acquired at a ramp rate of +10° C./minute.

Figure 543:
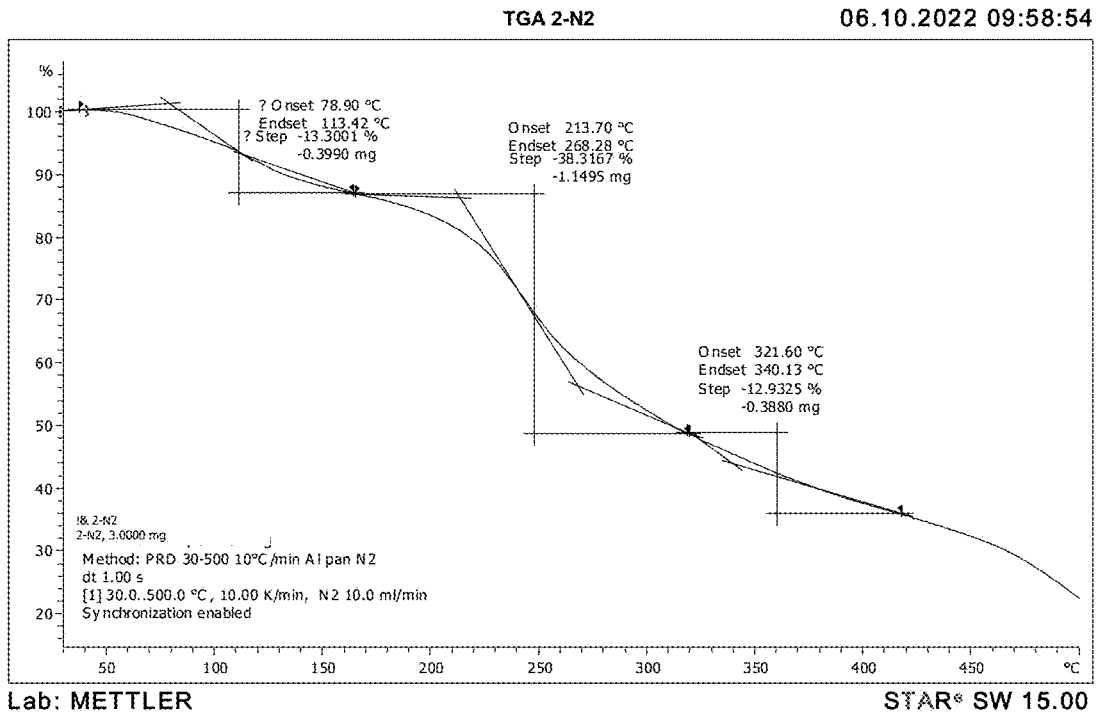

FIG. 543 depicts the TGA of the tabernanthalog glycolate salt (2-N2; Experiment Reference 2-Sample Reference N2), analysis was acquired at a ramp rate of +10° C./minute.

Figure 544:
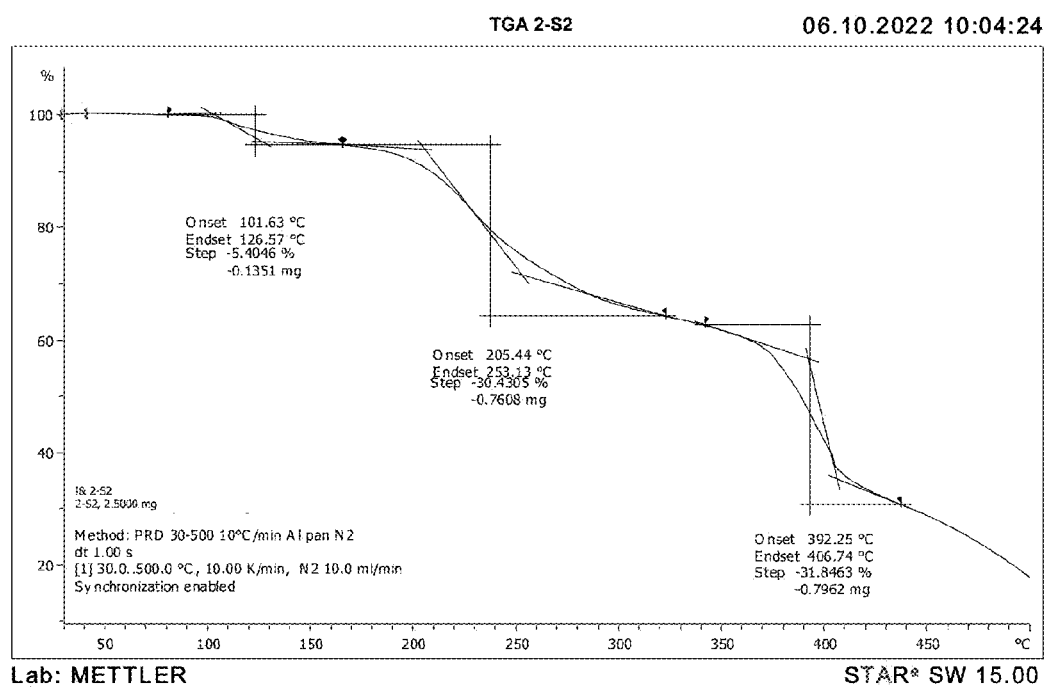

FIG. 544 depicts the TGA of the tabernanthalog succinate salt (2-S2; Experiment Reference 2-Sample Reference S2), analysis was acquired at a ramp rate of +10° C./minute.

Figure 545:
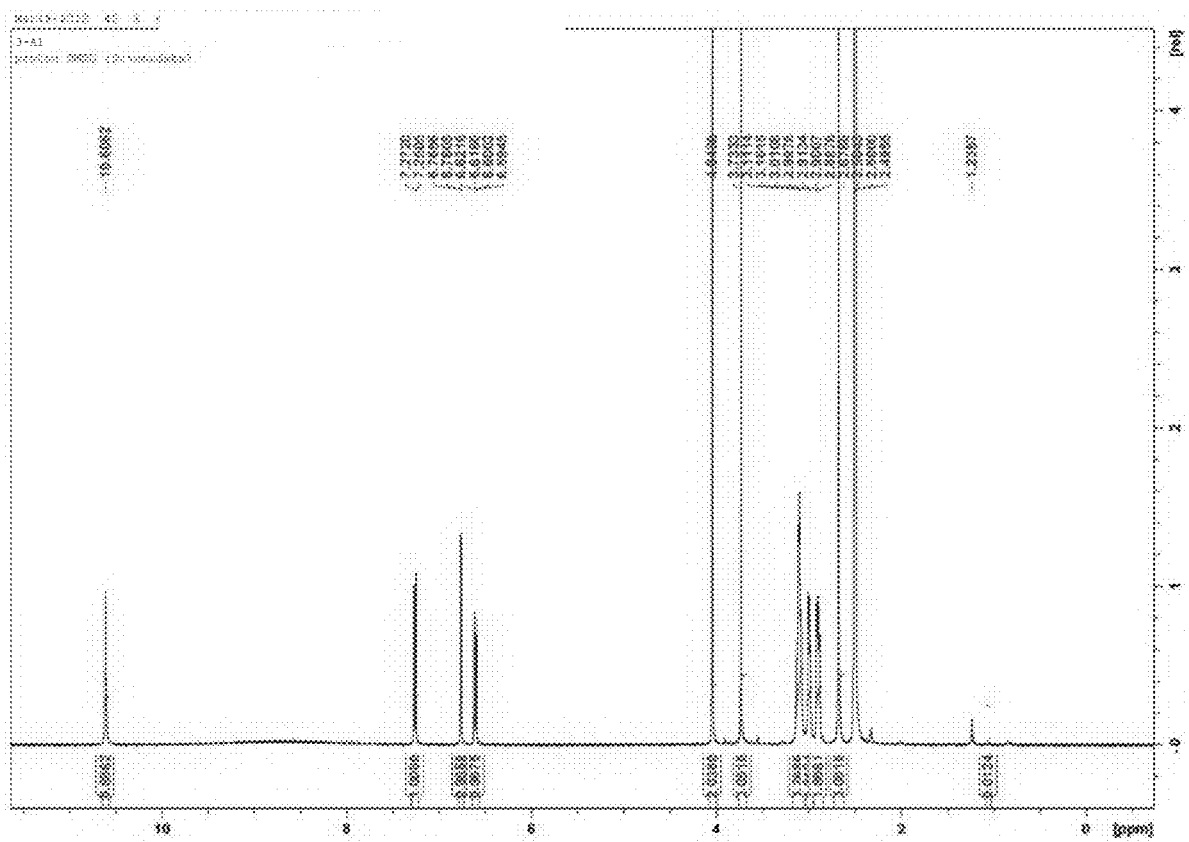

FIG. 545 depicts the $^1$H NMR of 3-A1 (Experiment Reference 3-Sample Reference A1) (The tabernanthalog tartrate salt), analysis was acquired in DMSO-d6 and calibrated to the non-deuterated solvent residual at 2.50 ppm. 1.0 mol of API to 1.0 mol of L-tartaric acid. Ethanol content 0.05% w/w.

Figure 546:
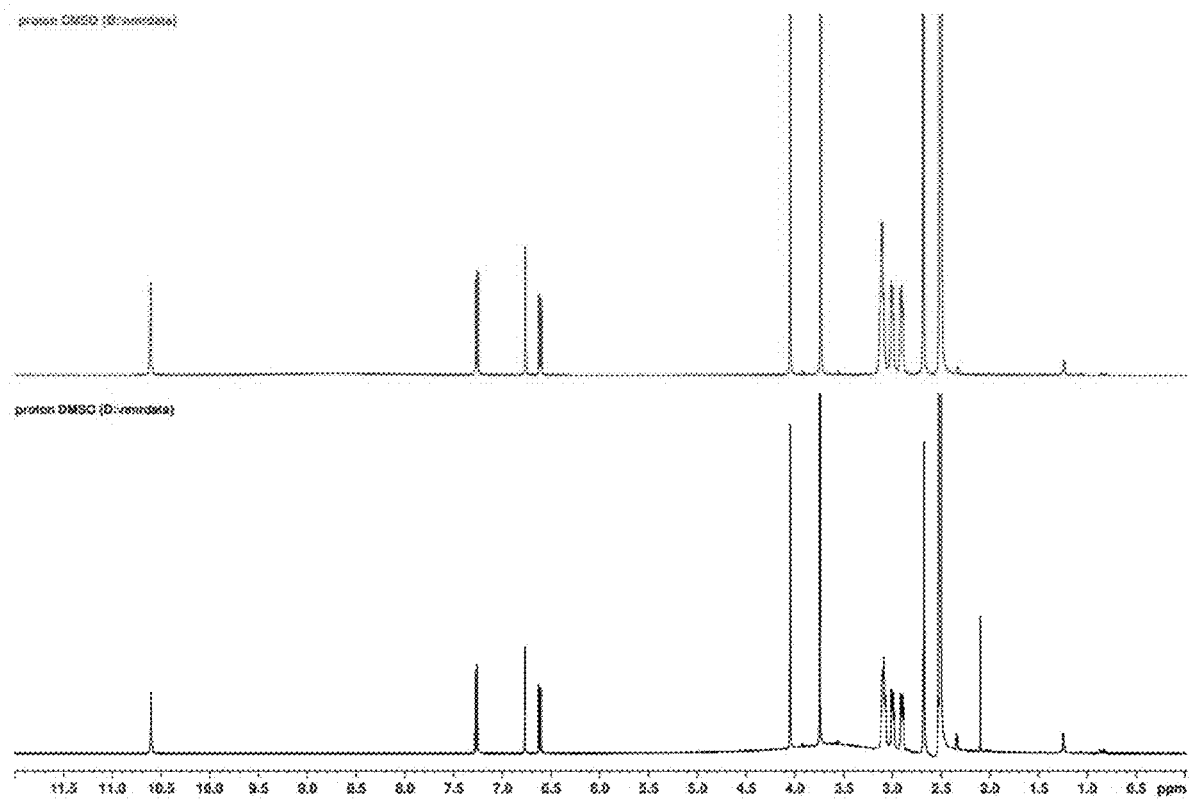

FIG. 546 depicts the $^1$H NMR of tabernanthalog tartrate salt; 3-A1 (Experiment Reference 3-Sample Reference A1) (top spectrum), overlaid with tabernanthalog tartrate salt; 2-I2 (Experiment Reference 2-Sample Reference I2) (bottom spectrum).

Figure 547:
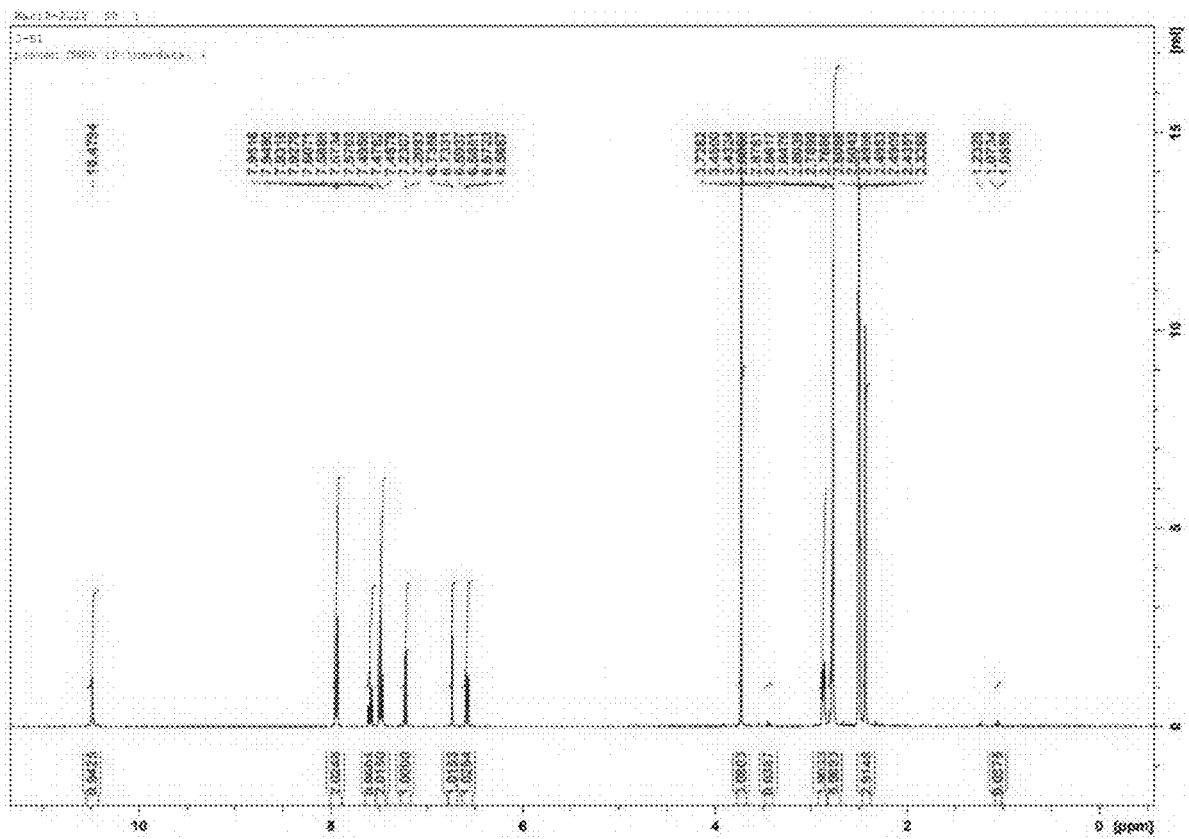

FIG. 547 depicts the $^1$H NMR of 3-B1 (Experiment Reference 3-Sample Reference B1) (The tabernanthalog benzoate salt), analysis was acquired in DMSO-d6 and calibrated to the non-deuterated solvent residual at 2.50 ppm. 1.0 mol of API to 1.0 mol of benzoic acid. Ethanol content 0.3% w/w.

Figure 548:
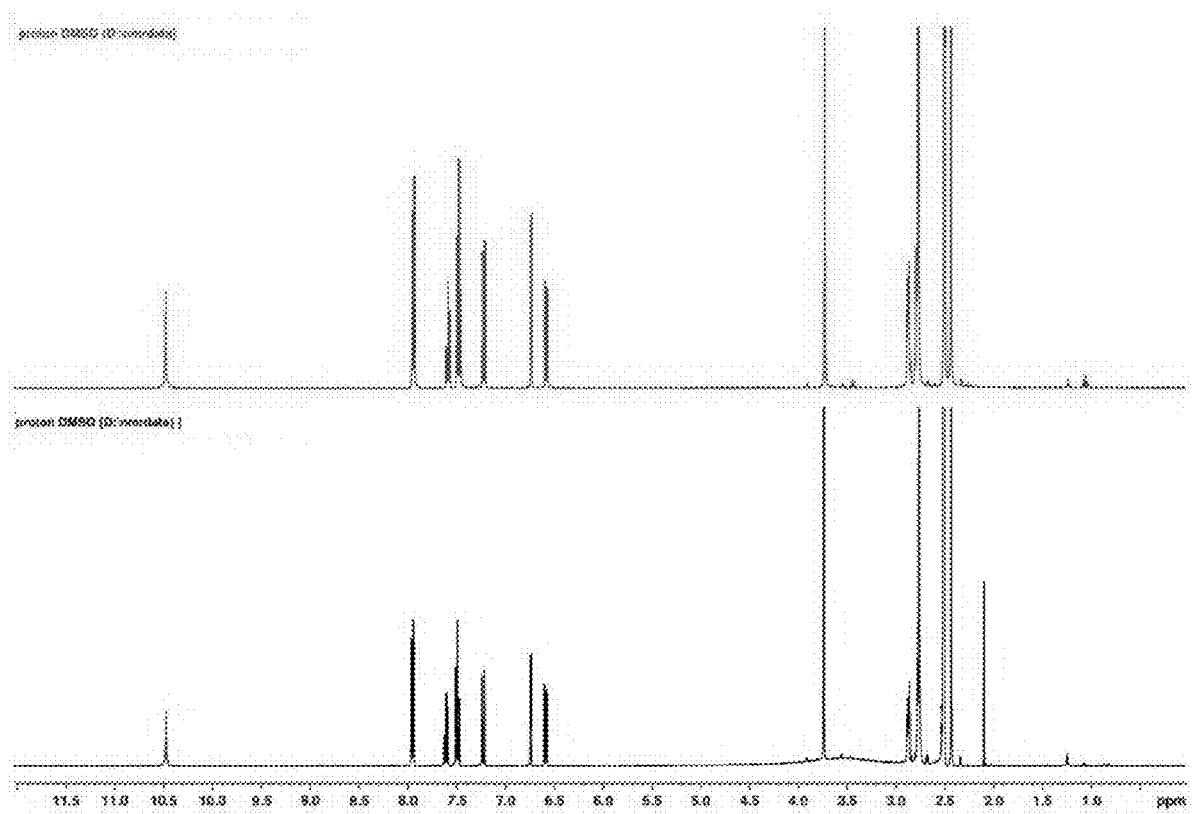

FIG. 548 depicts the $^1$H NMR of tabernanthalog benzoate salt; 3-B1 (Experiment Reference 3-Sample Reference B1) (top spectrum), overlaid with tabernanthalog benzoate salt; 2-R2 (Experiment Reference 2-Sample Reference R2) (bottom spectrum).

Figure 549:
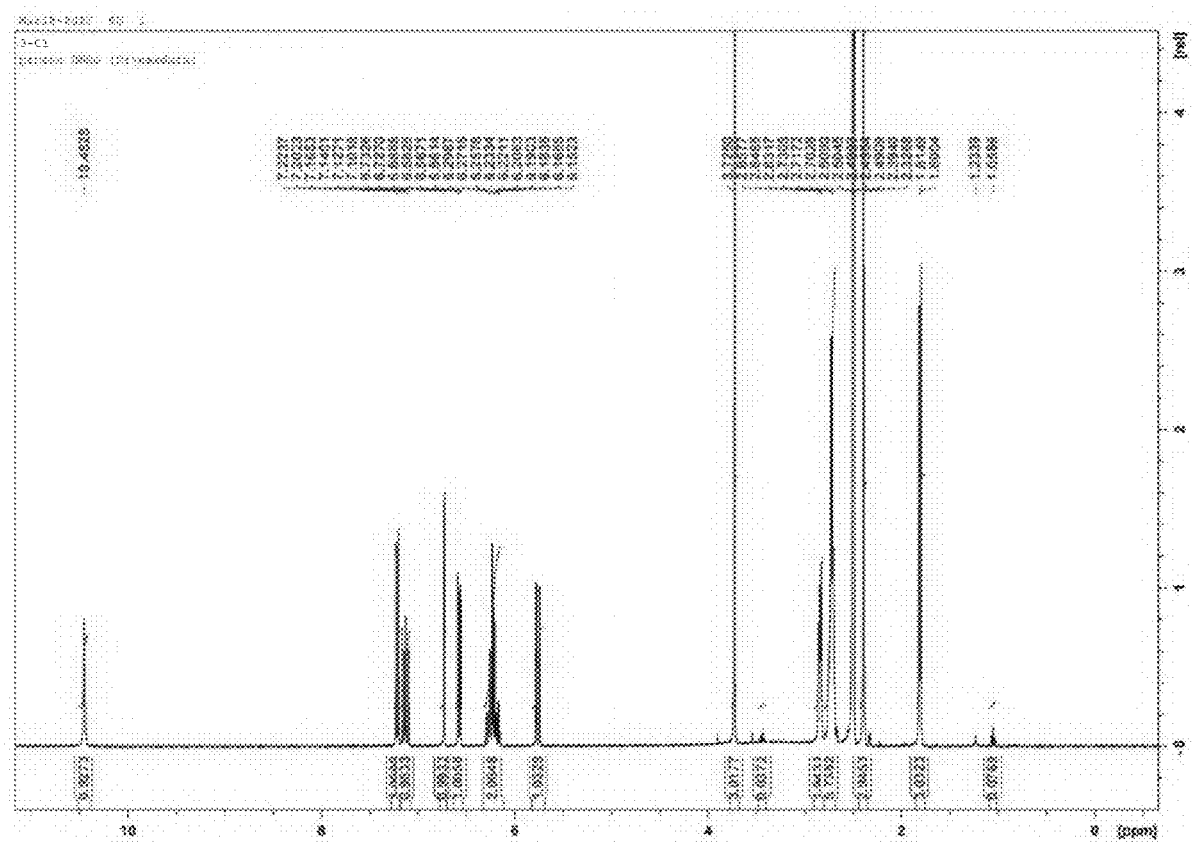

FIG. 549 depicts the $^1$H NMR of 3-C1 (Experiment Reference 3-Sample Reference C1; the tabernanthalog sorbate salt), analysis was acquired in DMSO-d6 and calibrated to the non-deuterated solvent residual at 2.50 ppm. 1.0 mol of API to 1.0 mol of sorbic acid. Ethanol content 0.3% w/w.

Figure 550:
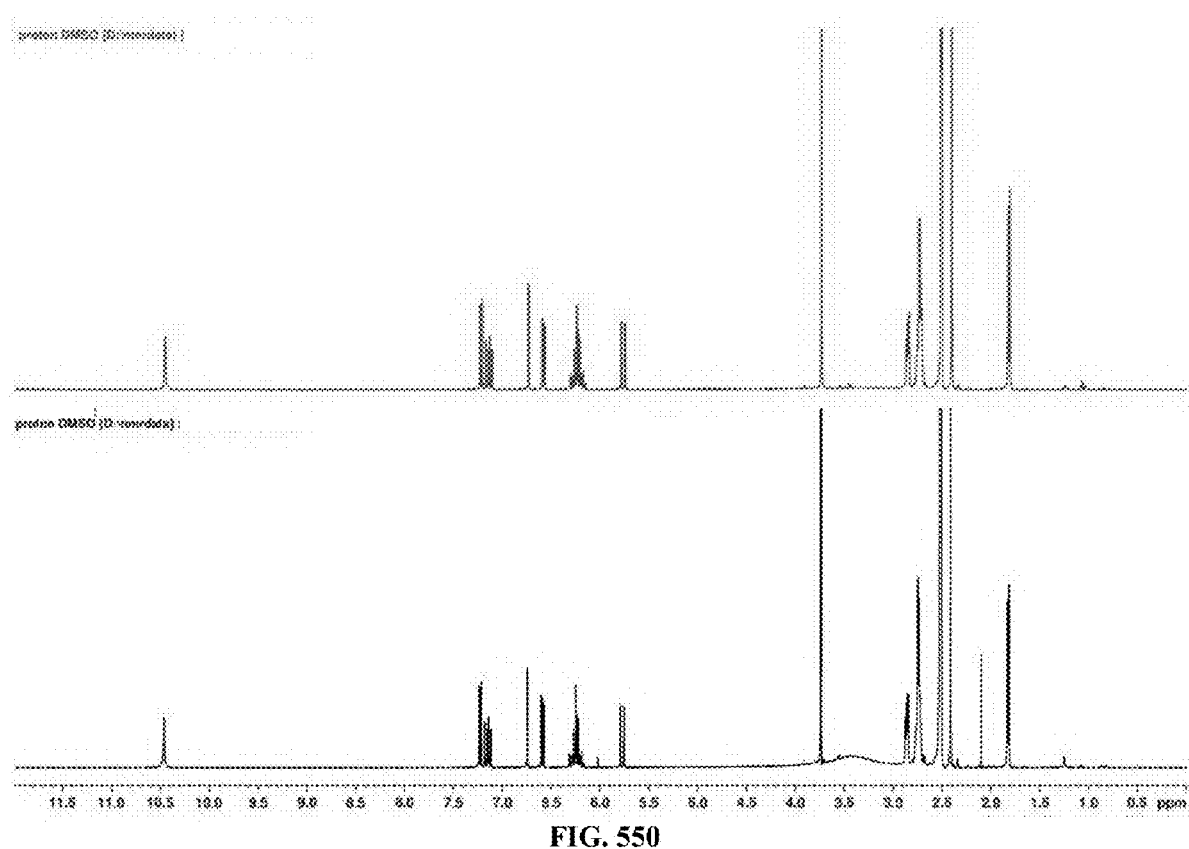

FIG. 550 depicts the $^1$H NMR of tabernanthalog sorbate salt; 3-C1 (Experiment Reference 3-Sample Reference C1; top spectrum), overlaid with tabernanthalog sorbate salt; 2-V2 (Experiment Reference 2-Sample Reference V2; bottom spectrum).

Figure 551:
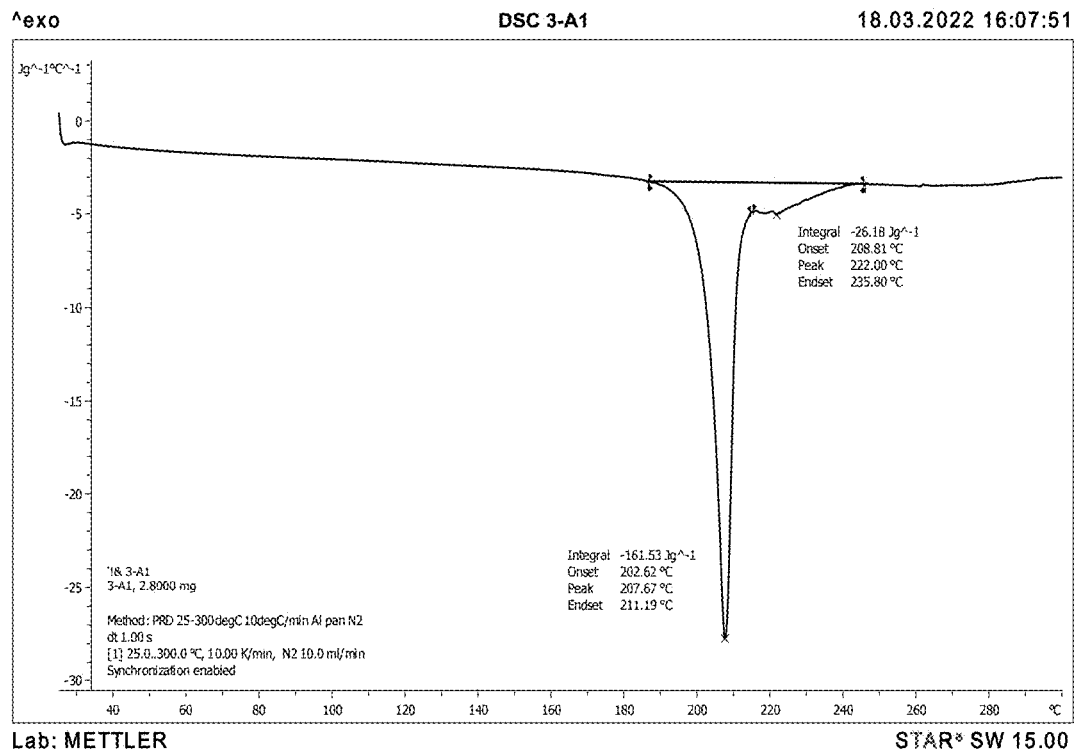

FIG. 551 depicts the DSC profile of 3-A1 (Experiment Reference 3-Sample Reference A1; the tabernanthalog tartrate salt), analysis was acquired at a ramp rate of +10° C./minute.

Figure 552:
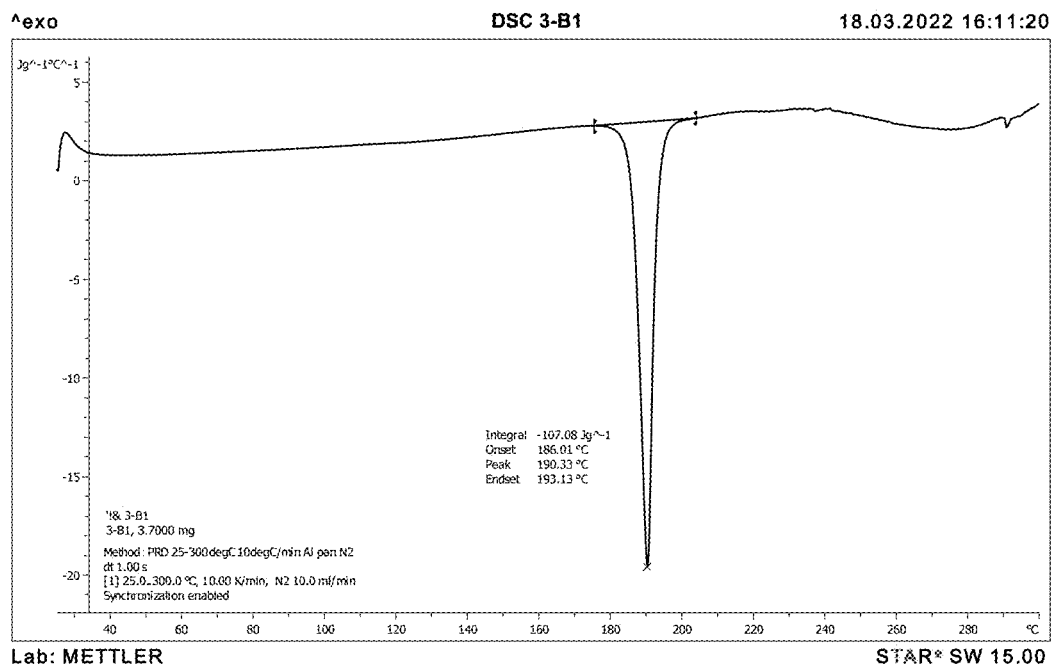

FIG. 552 depicts the DSC profile of 3-B1 (Experiment Reference 3-Sample Reference B1; the tabernanthalog benzoate salt), analysis was acquired at a ramp rate of +10° C./minute.

Figure 553:
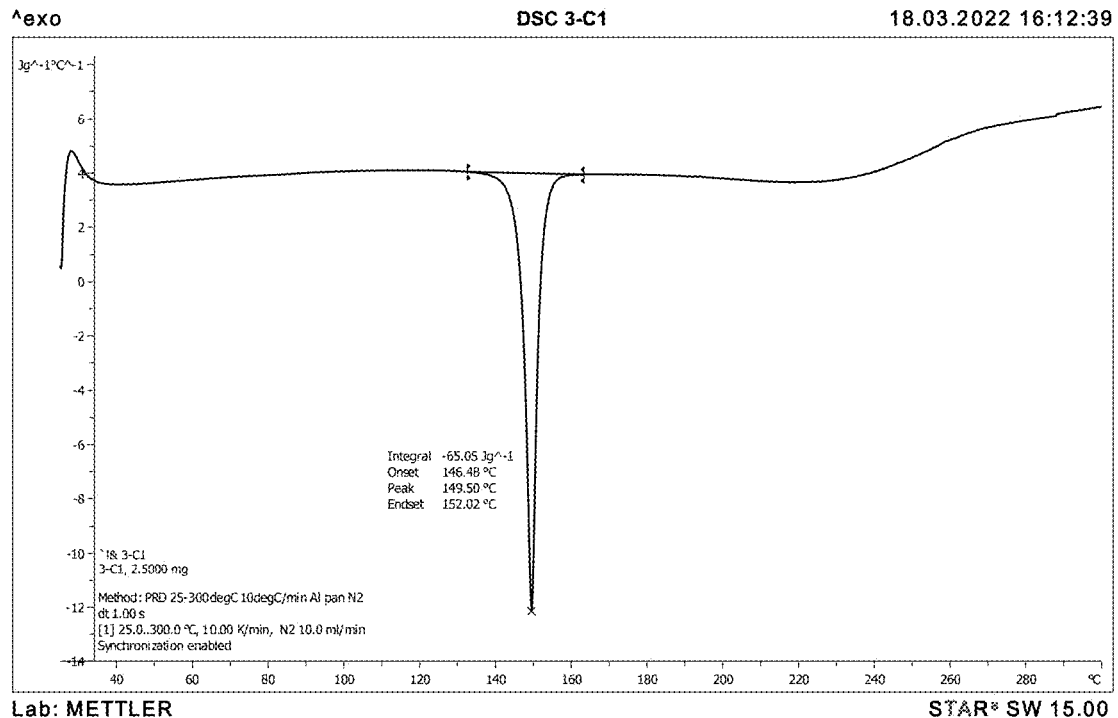

FIG. 553 depicts the DSC profile of 3-C1 (Experiment Reference 3-Sample Reference C1; the tabernanthalog benzoate salt), analysis was acquired at a ramp rate of +10° C./minute.

Figure 554:
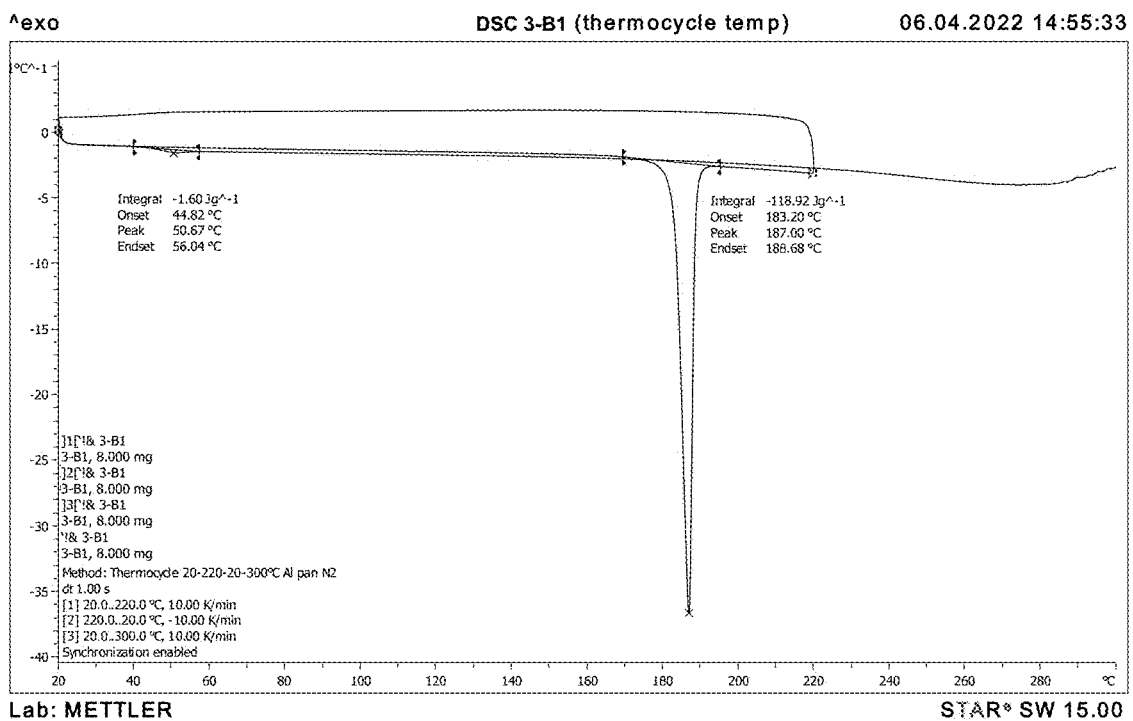

FIG. 554 depicts the DSC profile of 3-B1 (Experiment Reference 3-Sample Reference B1; the tabernanthalog benzoate salt), analysis was acquired at a ramp rate of +10° C./minute from 20° C. to 220° C., 220° C. to 20° C., and 20° C. to 300° C.

Figure 555:
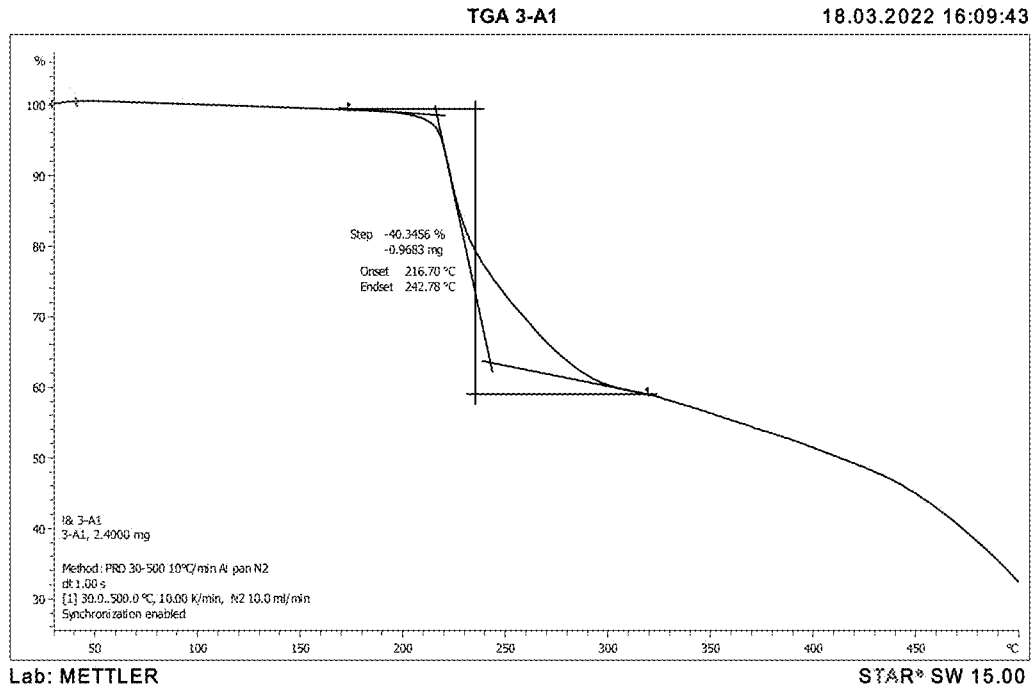

FIG. 555 depicts the TGA of 3-A1 (Experiment Reference 3-Sample Reference A1; the tabernanthalog tartrate salt), analysis was acquired at a ramp rate of +10° C./minute.

Figure 556:
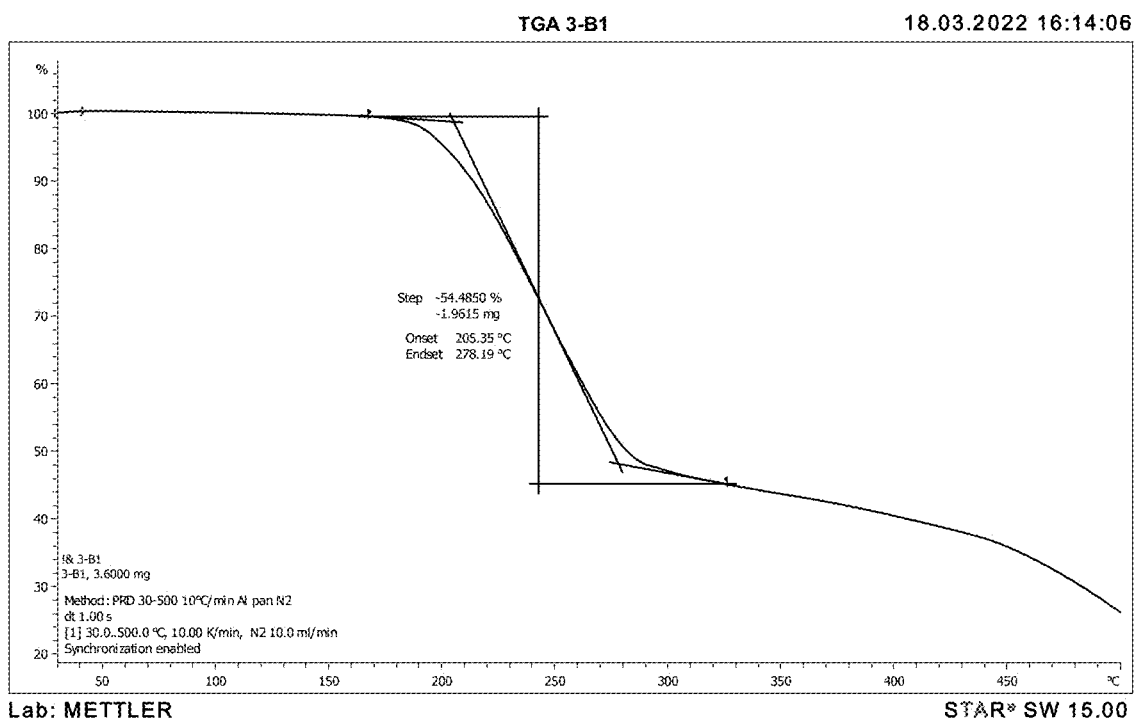

FIG. 556 depicts the TGA of 3-B1 (Experiment Reference 3-Sample Reference B1; the tabernanthalog benzoate salt), analysis was acquired at a ramp rate of +10° C./minute.

Figure 557:
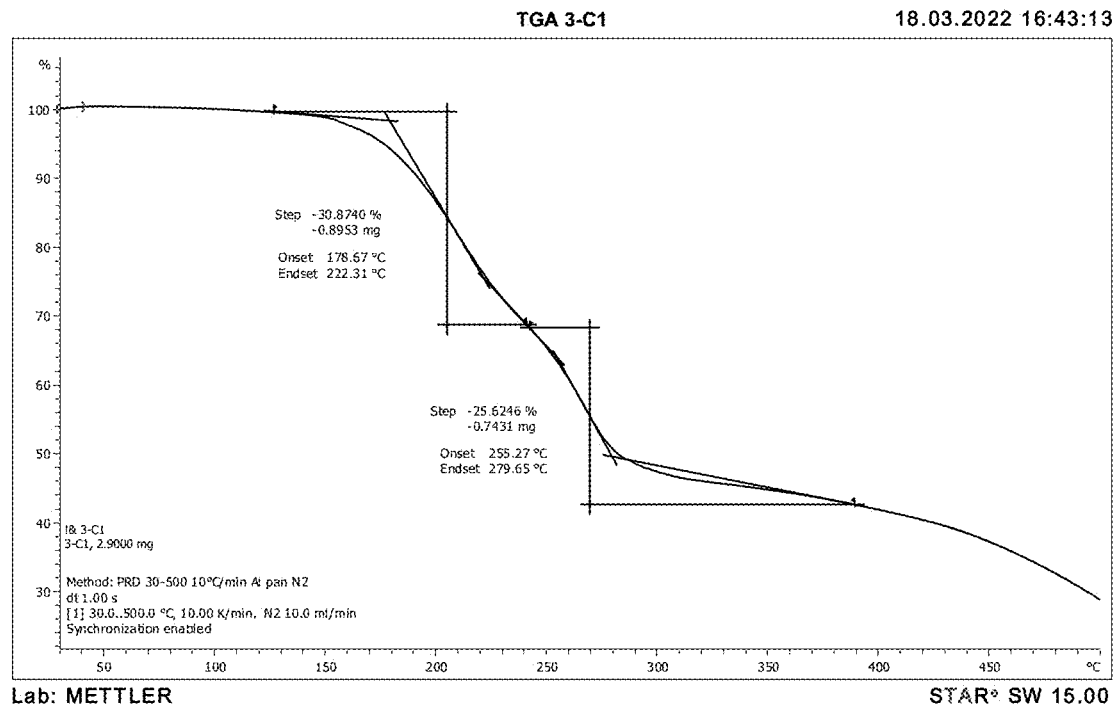

FIG. 557 depicts the TGA of 3-C1 (Experiment Reference 3-Sample Reference C1; the tabernanthalog sorbate salt), analysis was acquired at a ramp rate of +10° C./minute.

Figure 558:
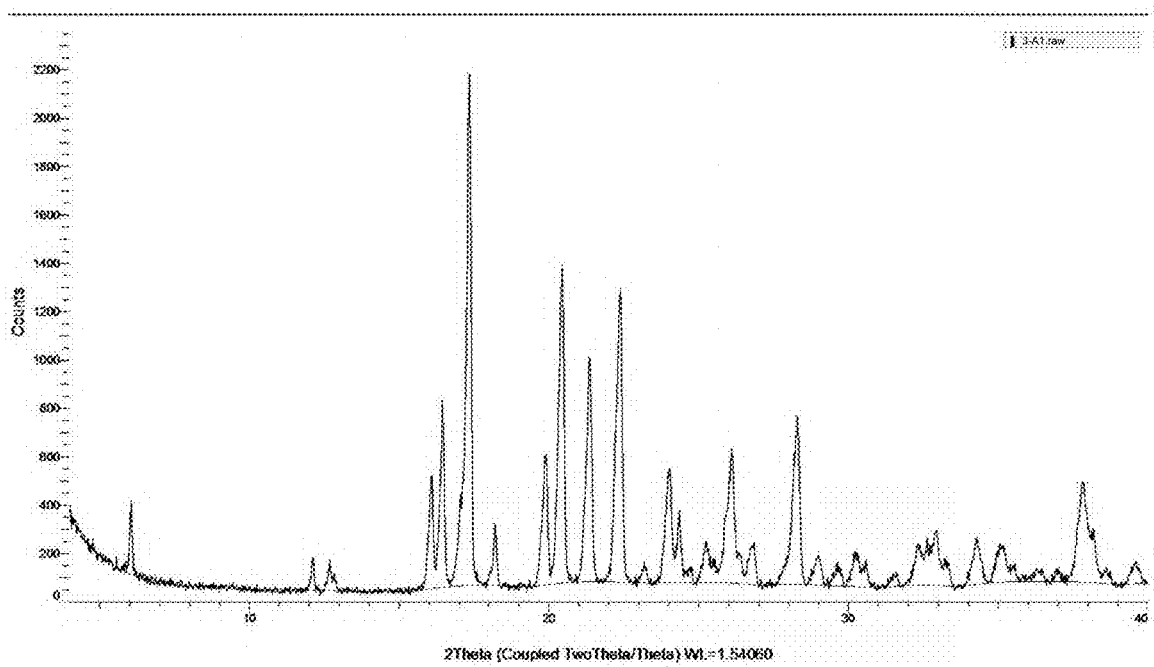

FIG. 558 depicts the XRPD 3-A1 (Experiment Reference 3-Sample Reference A1; the tabernanthalog tartrate salt).

Figure 559:
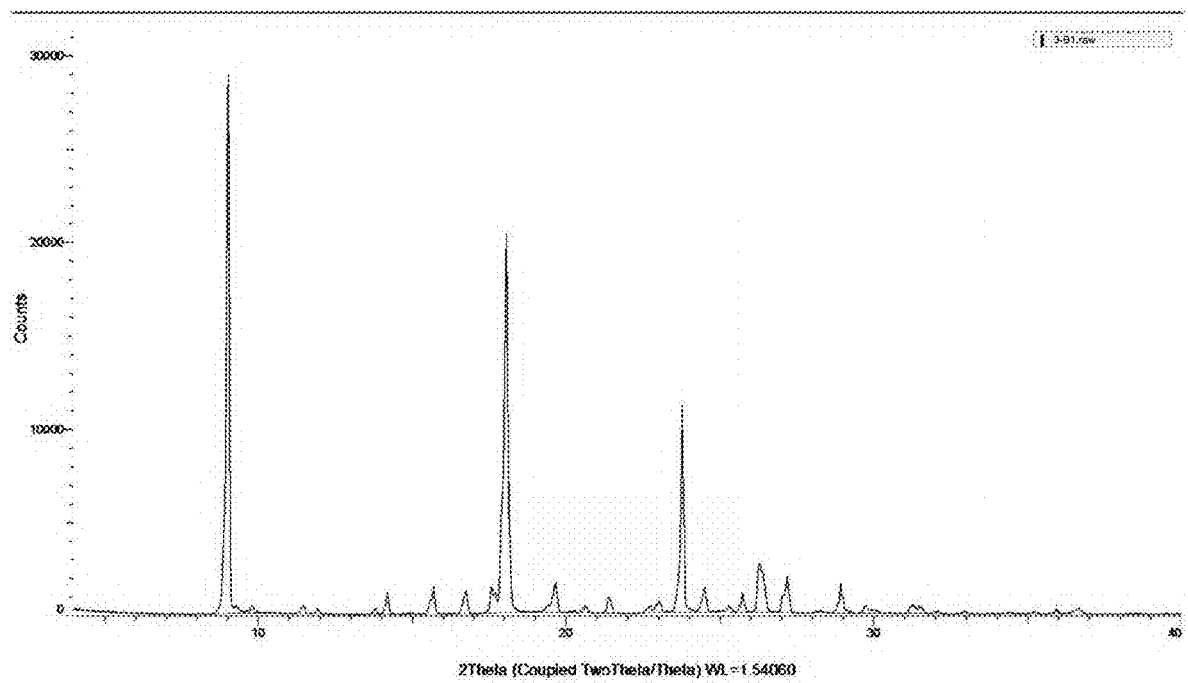

FIG. 559 depicts the XRPD 3-B1 (Experiment Reference 3-Sample Reference B1; the tabernanthalog benzoate salt).

Figure 560:
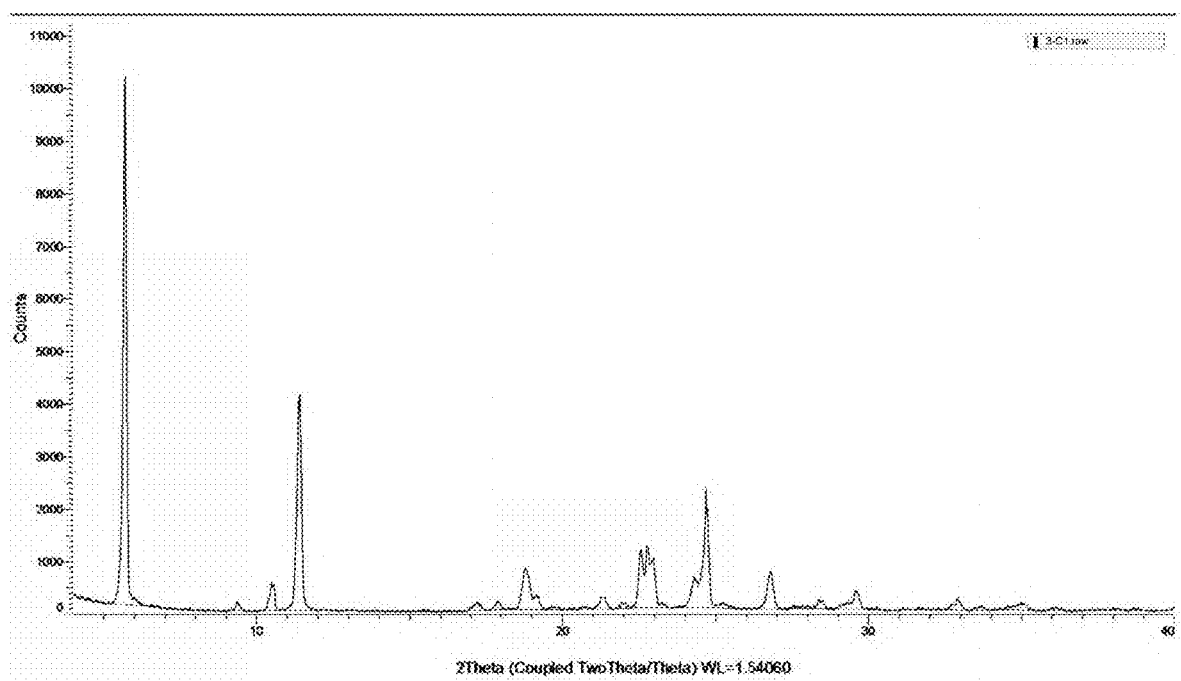

FIG. 560 depicts the XRPD 3-C1 (Experiment Reference 3-Sample Reference C1; the tabernanthalog sorbate salt).

Figure 561:
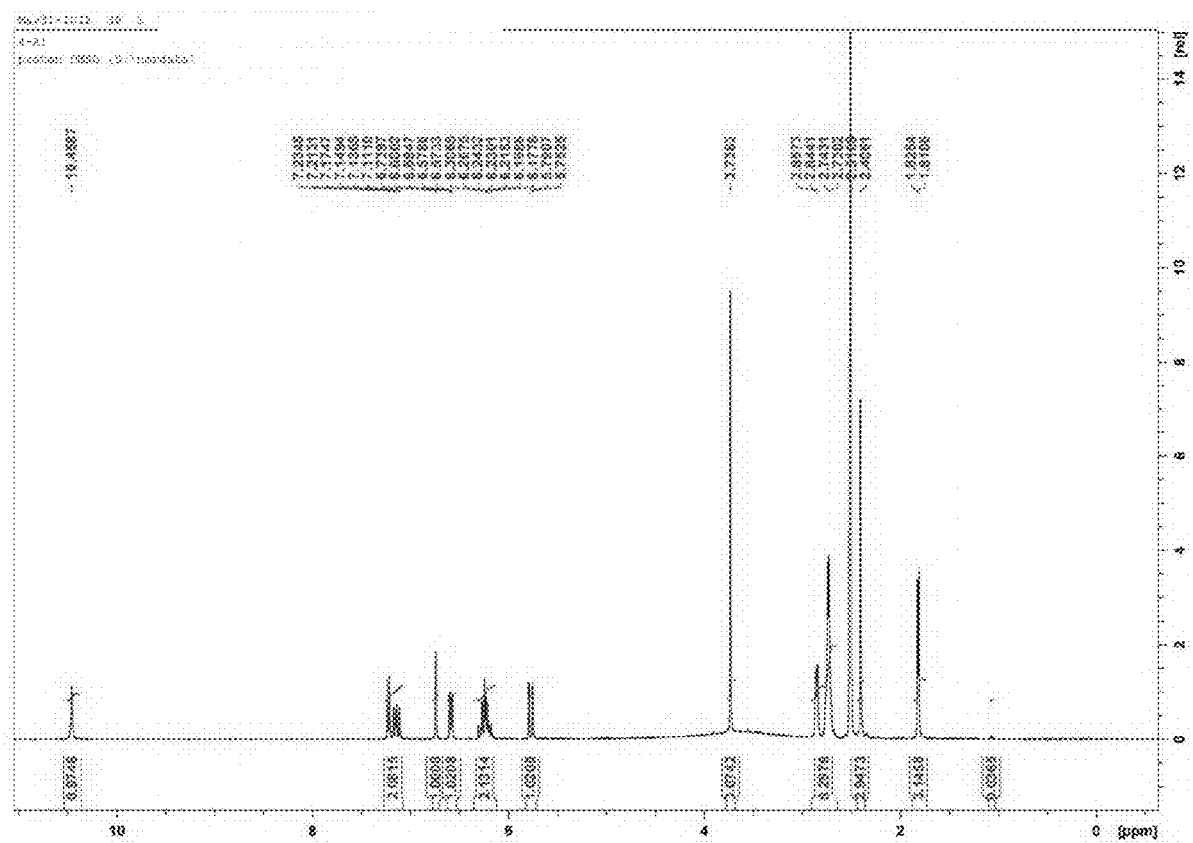

FIG. 561 depicts the $^1$H NMR of tabernanthalog sorbate salt: 4-A1 (Experiment Reference 4-Sample Reference A1), analysis was acquired in DMSO-d6 and calibrated to the non-deuterated solvent residual at 2.50 ppm. 1.0 mol of API to 1.0 mol of sorbic acid. Ethanol content 0.2% w/w.

Figure 562:
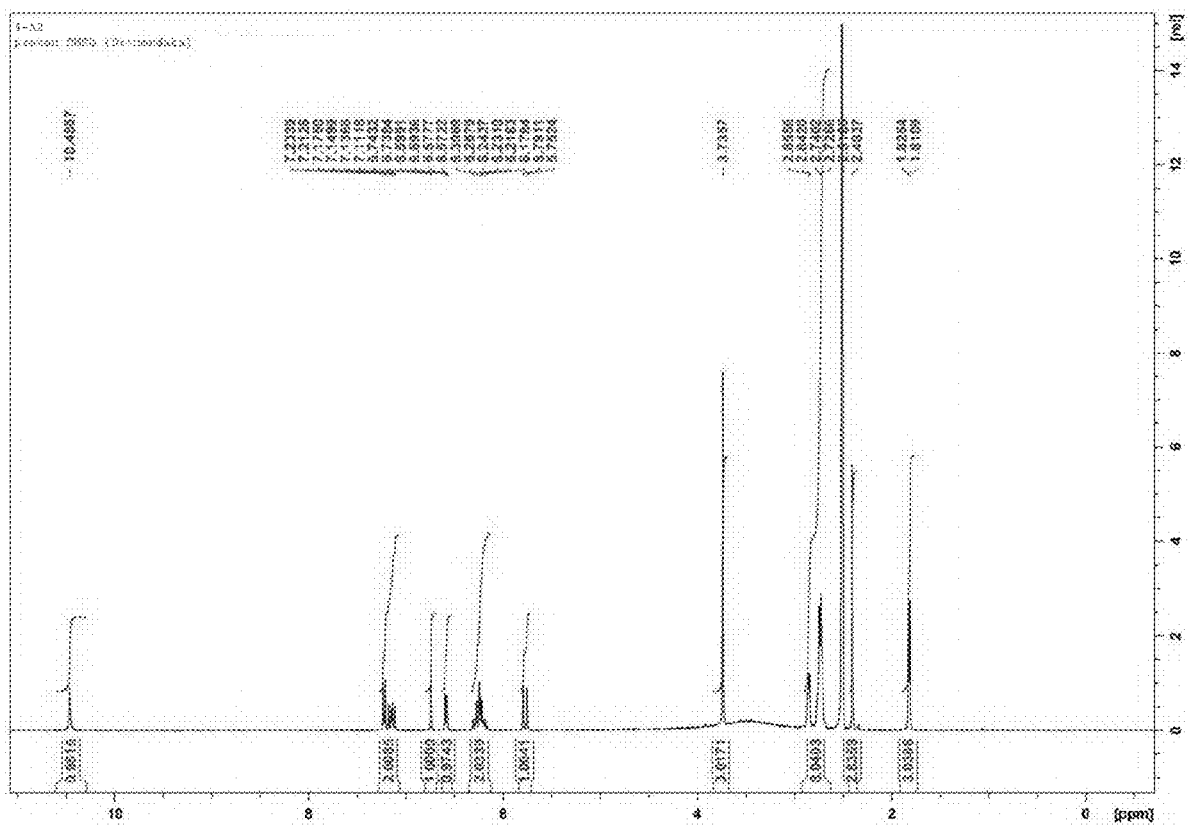

FIG. 562 depicts the $^1$H NMR of tabernanthalog sorbate salt; 4-A2 (Experiment Reference 4-Sample Reference A2), acquired in DMSO-d6 and calibrated to the non-deuterated solvent residual at 2.50 ppm. 1.0 mol of API to 1.0 mol of sorbic acid. Ethanol content 0.1% w/w.

Figure 563:
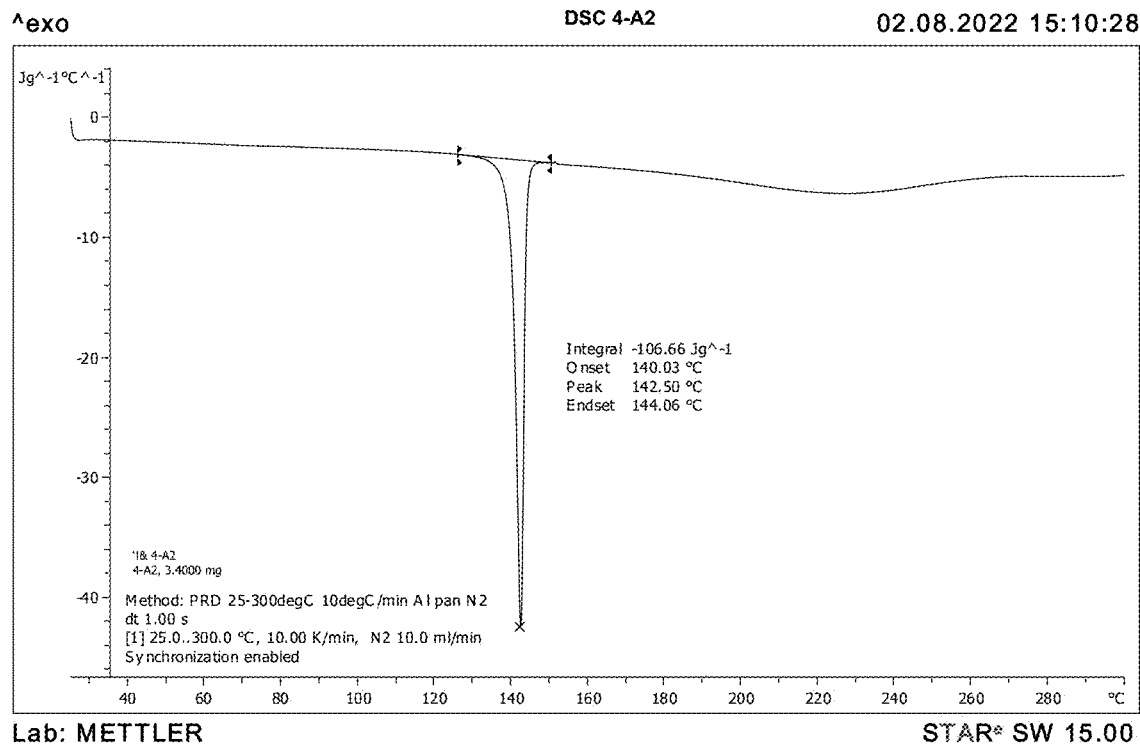

FIG. 563 depicts the DSC profile of 4-A2 (Experiment Reference 4-Sample Reference A2), analysis was acquired at a ramp rate of +10° C./minute.

Figure 564:
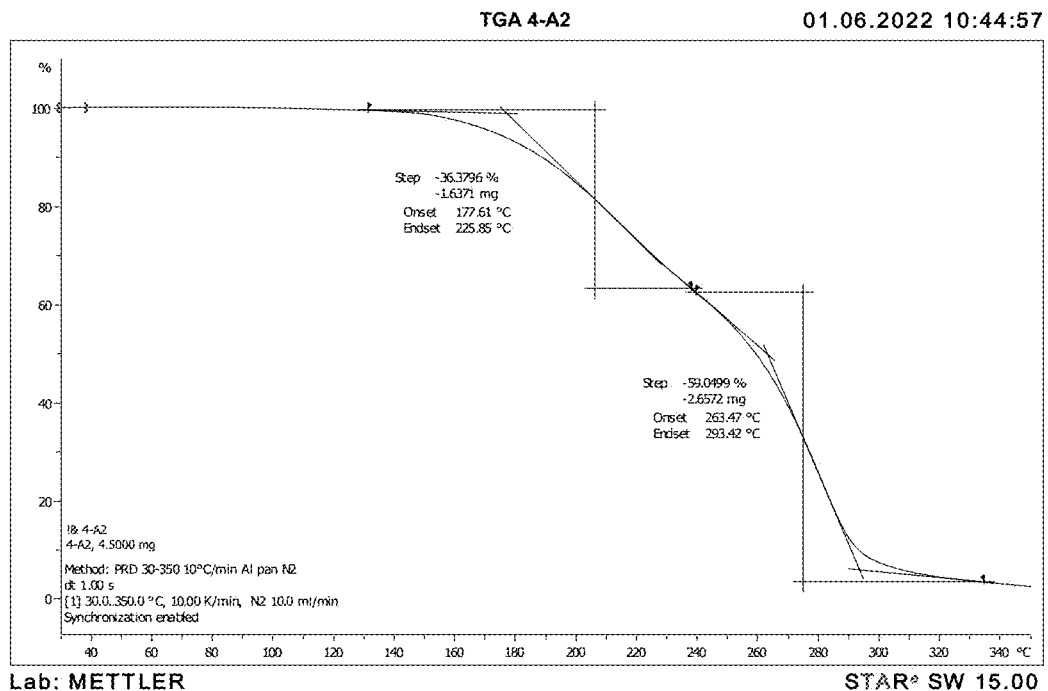

FIG. 564 depicts the TGA of 4-A2 (Experiment Reference 4-Sample Reference A2), analysis was acquired at a ramp rate of +10° C./minute.

Figure 565:
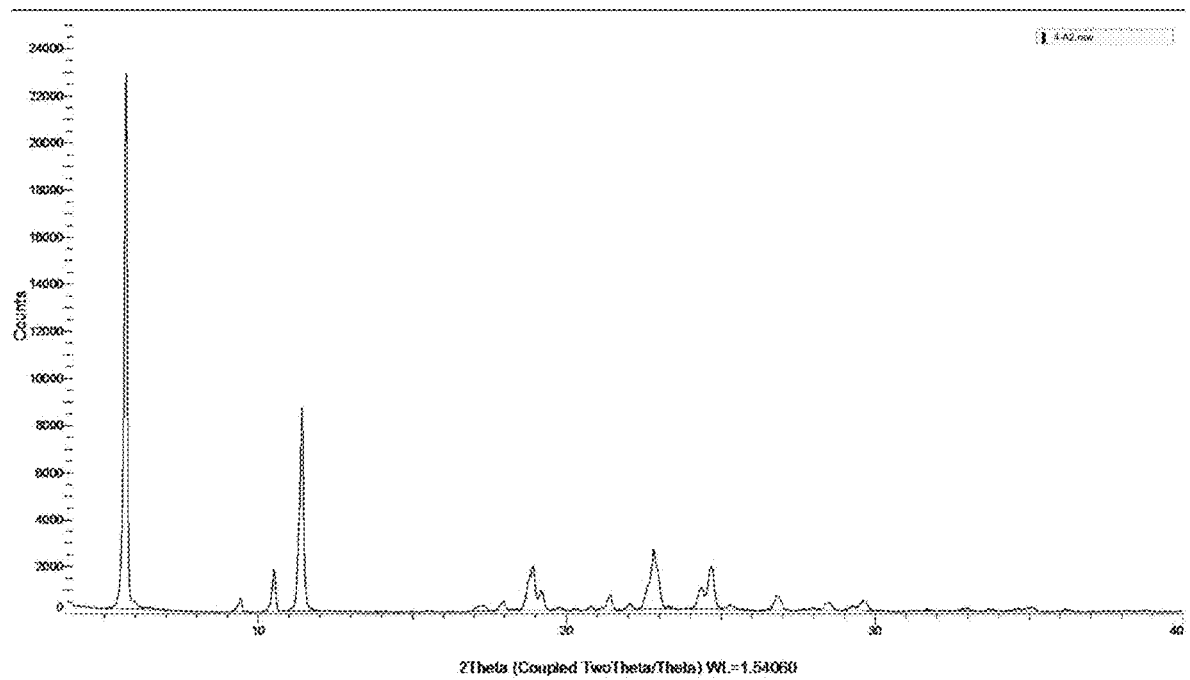

FIG. 565 depicts the XRPD 4-A2 (Experiment Reference 4-Sample Reference A2; the tabernanthalog sorbate salt).

Figure 566:
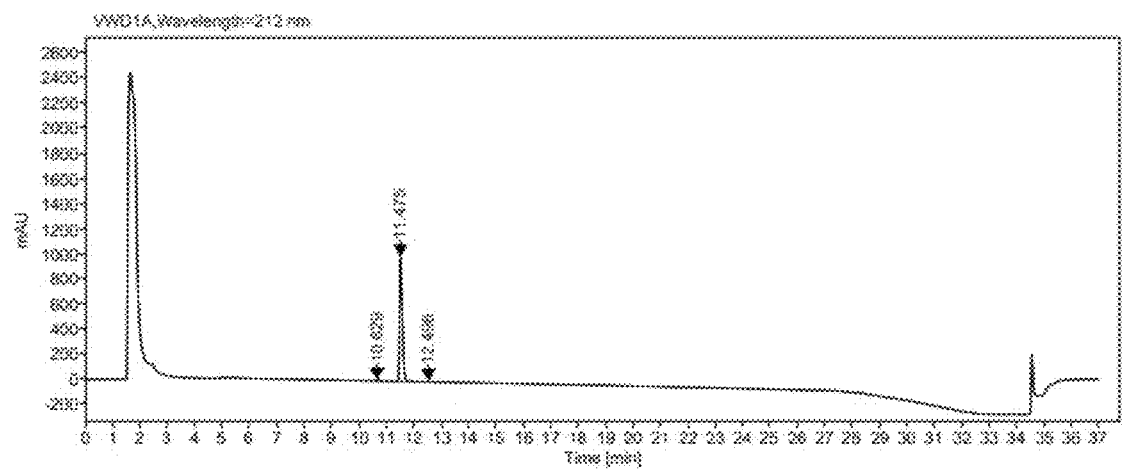

FIG. 566 depicts the HPLC of tabernanthalog sorbate salt; 4-A2 (Experiment Reference 4-Sample Reference A2).

Figure 567:
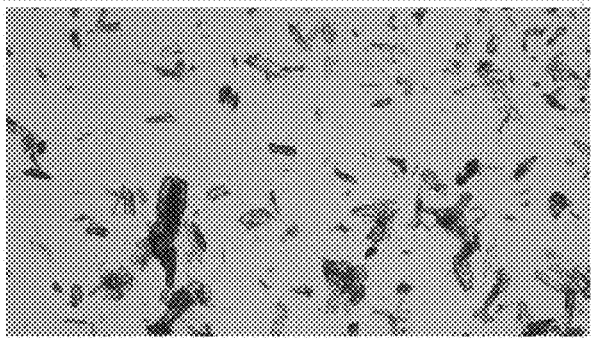

FIG. 567 depicts the PLM of tabernanthalog sorbate salt; 4-A2 (Experiment Reference 4-Sample Reference A2)×2 mag, NP.

Figure 568:
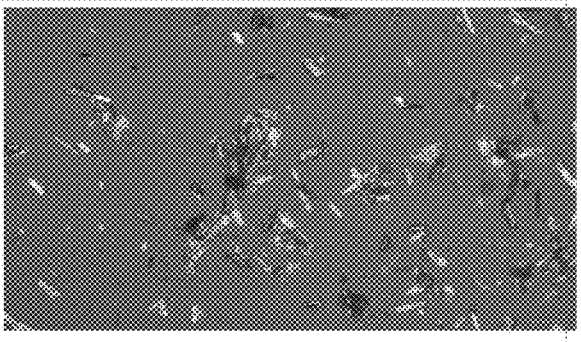

FIG. 568 depicts the PLM of tabernanthalog sorbate salt: 4-A2 (Experiment Reference 4-Sample Reference A2)×2 mag, CP.

Figure 569:
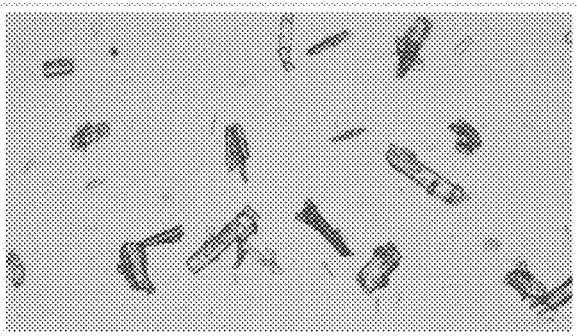

FIG. 569 depicts the PLM of tabernanthalog sorbate salt; 4-A2 (Experiment Reference 4-Sample Reference A2)×5 mag, NP.

Figure 570:
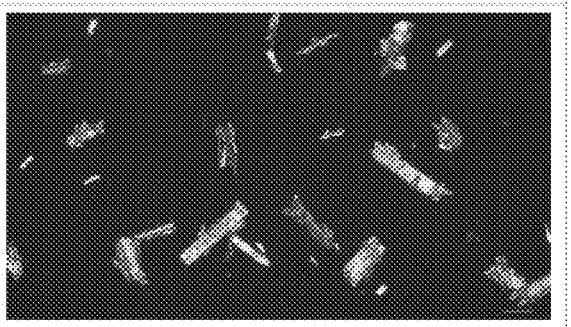

FIG. 570 depicts the PLM of tabernanthalog sorbate salt; 4-A2 (Experiment Reference 4-Sample Reference A2)×5 mag, CP.

Figure 571:
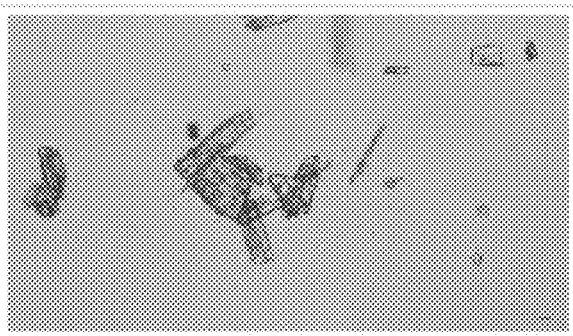

FIG. 571 depicts the PLM of tabernanthalog sorbate salt; 4-A2 (Experiment Reference 4-Sample Reference A2)×5 mag, NP.

Figure 572:
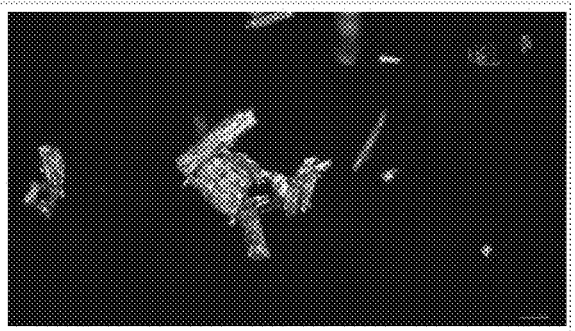

FIG. 572 depicts the PLM of tabernanthalog sorbate salt; 4-A2 (Experiment Reference 4-Sample Reference A2)×5 mag, CP.

Figure 573:
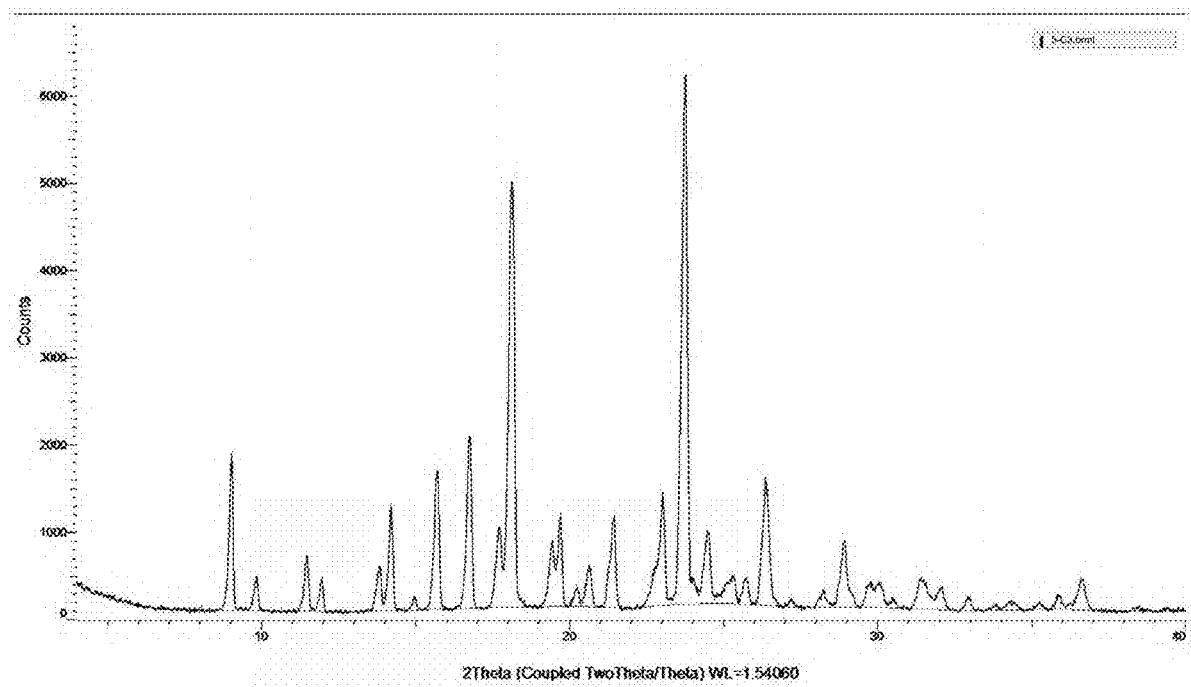

FIG. 573 depicts the XRPD profile of 5-C3 (Experiment Reference 5-Sample Reference C3; the tabernanthalog benzoate salt in FaSSIF, t=1 h, dry pellet).

Figure 574:
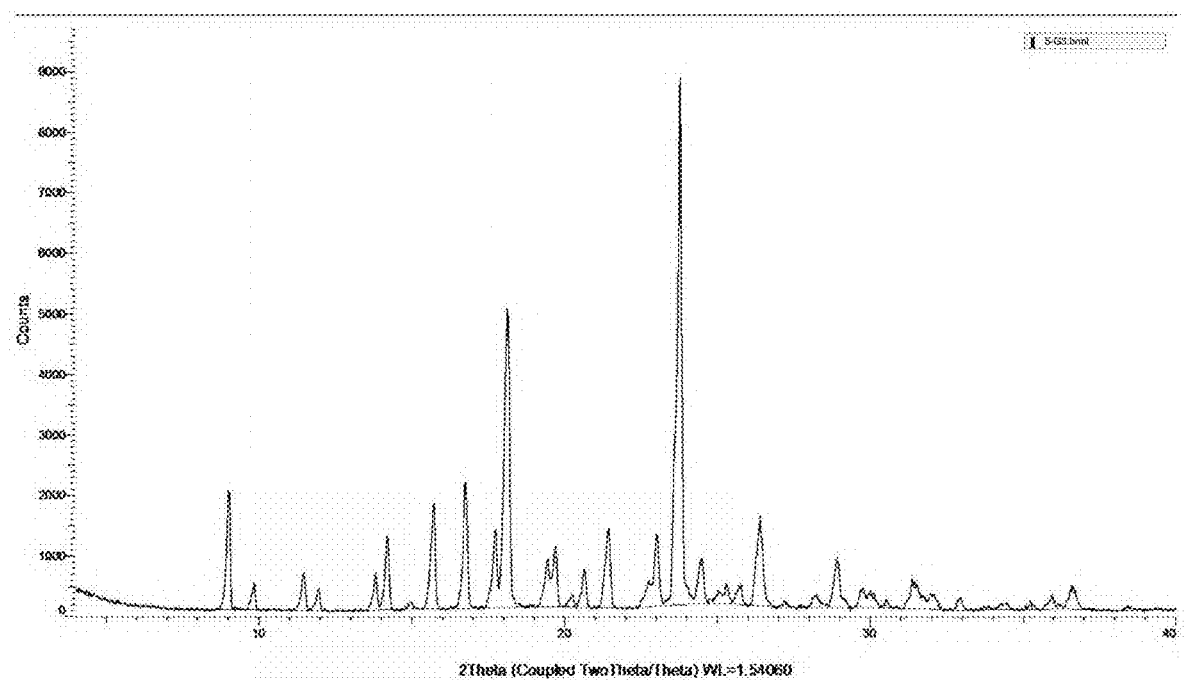

FIG. 574 depicts the XRPD profile of 5-G3 (Experiment Reference 5-Sample Reference G3; the tabernanthalog benzoate salt in FeSSIF, t=1 h, dry pellet).

Figure 575:
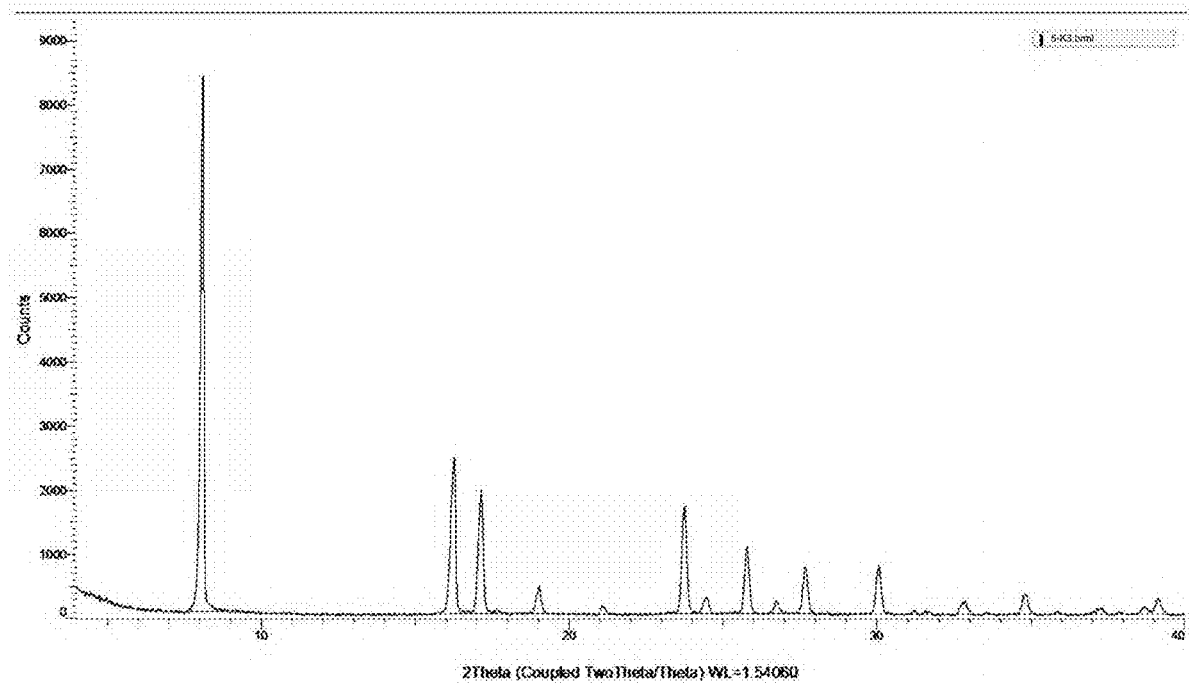

FIG. 575 depicts the XRPD 5-K3 (Experiment Reference 5-Sample Reference K3; the tabernanthalog benzoate salt in FaSSGF, t=1 h, dry pellet).

Figure 576:
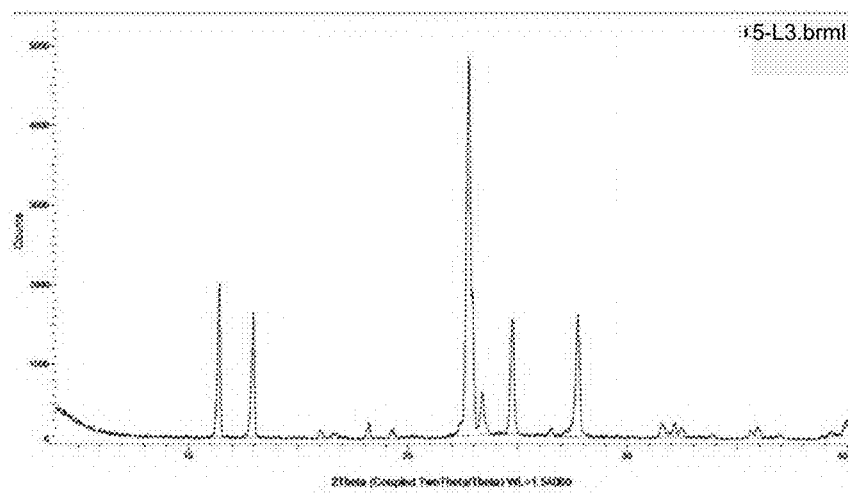

FIG. 576 depicts the XRPD 5-L3 (Experiment Reference 5-Sample Reference L3; the tabernanthalog sorbate salt in FaSSGF, t=1 h, dry pellet).

Figure 577:
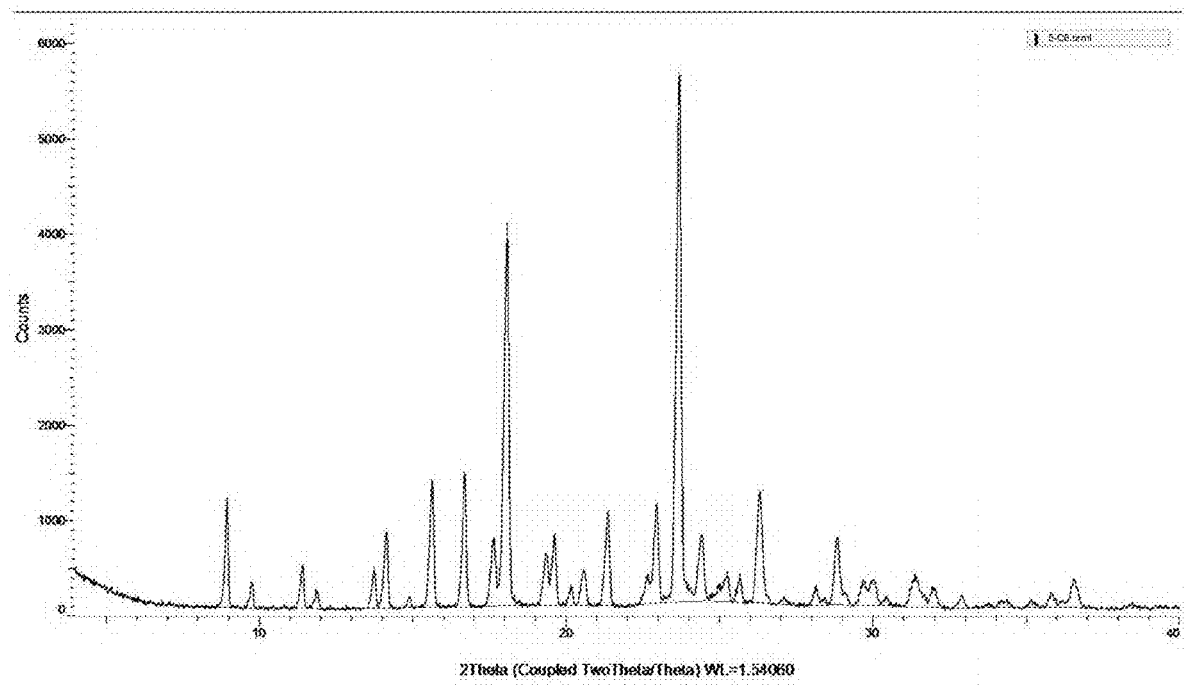

FIG. 577 depicts the XRPD 5-C6 (Experiment Reference 5-Sample Reference C6; the tabernanthalog benzoate salt in FaSSIF, t=3 h, dry pellet).

Figure 578:
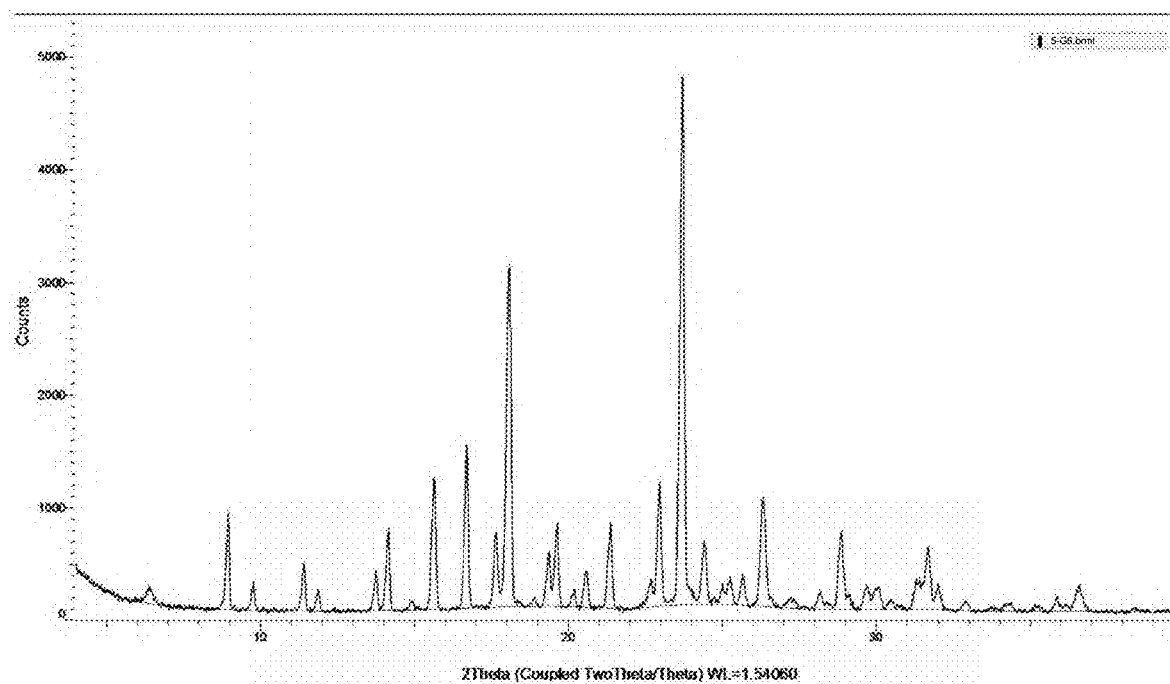

FIG. 578 depicts the XRPD 5-G6 (Experiment Reference 5-Sample Reference G6; the tabernanthalog benzoate salt in FeSSIF, t=3 h, dry pellet).

Figure 579:
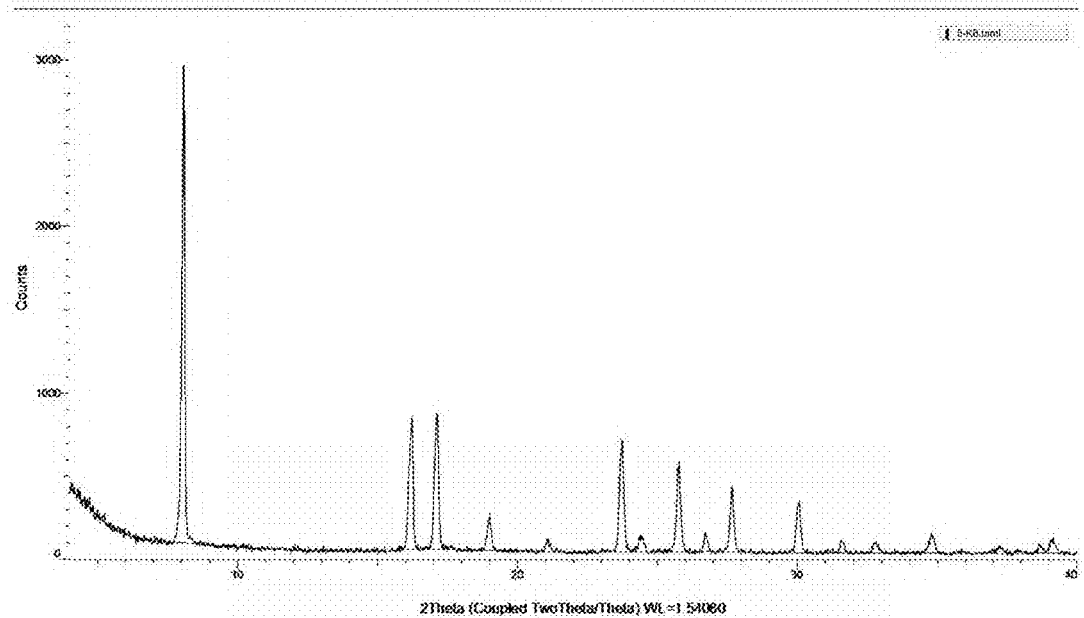

FIG. 579 depicts the XRPD 5-K6 (Experiment Reference 5-Sample Reference K6; the tabernanthalog benzoate salt in FaSSGF, t=3 h, dry pellet).

Figure 580:
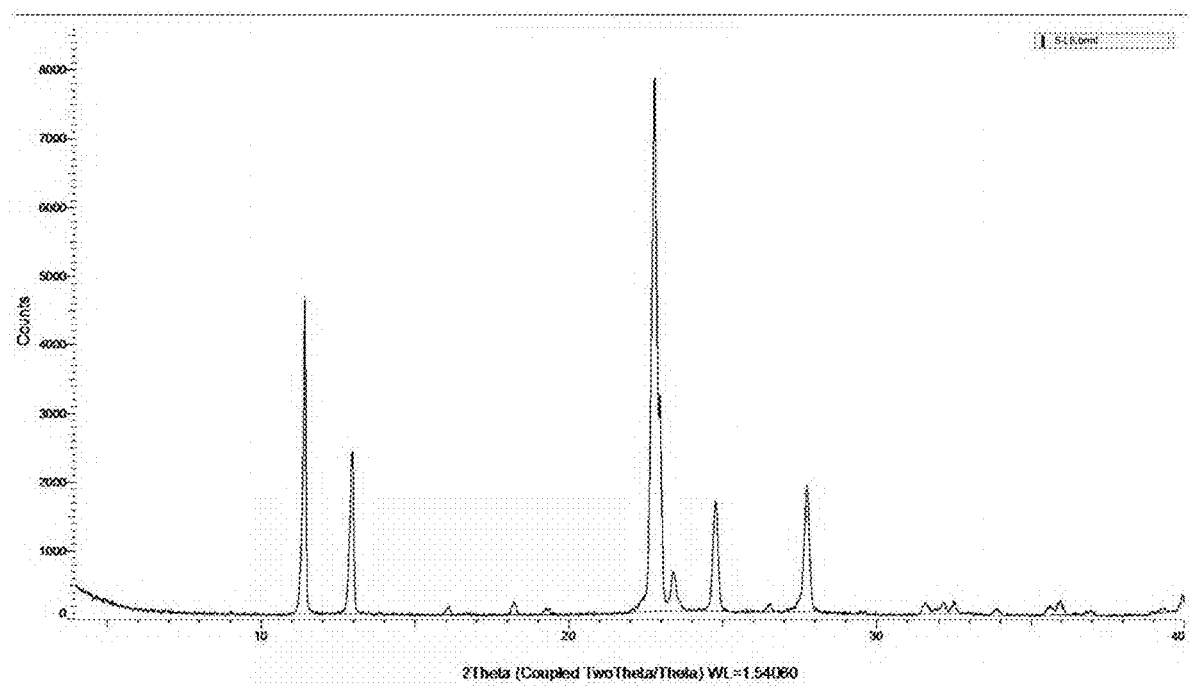

FIG. 580 depicts the XRPD 5-L6 (Experiment Reference 5-Sample Reference L6; the tabernanthalog sorbate salt in FaSSGF, t=3 h, dry pellet).

Figure 581:
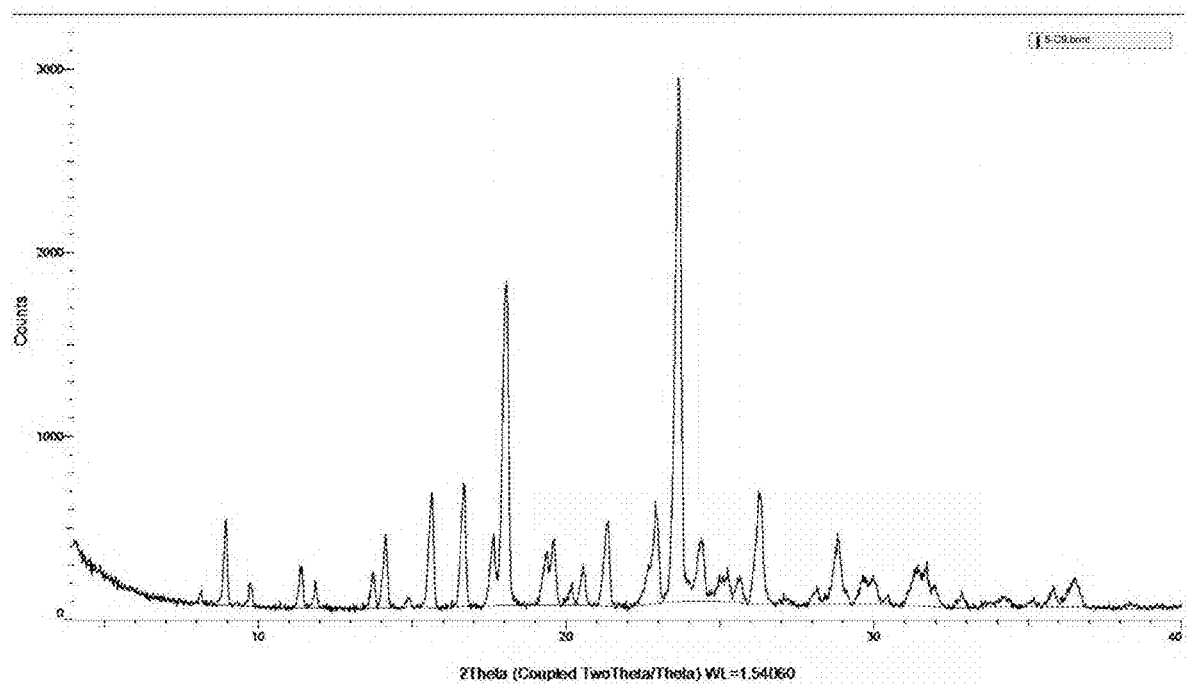

FIG. 581 depicts the XRPD 5-C9 (Experiment Reference 5-Sample Reference C9; the tabernanthalog benzoate salt in FaSSIF, t=6 h, dry pellet).

Figure 582:
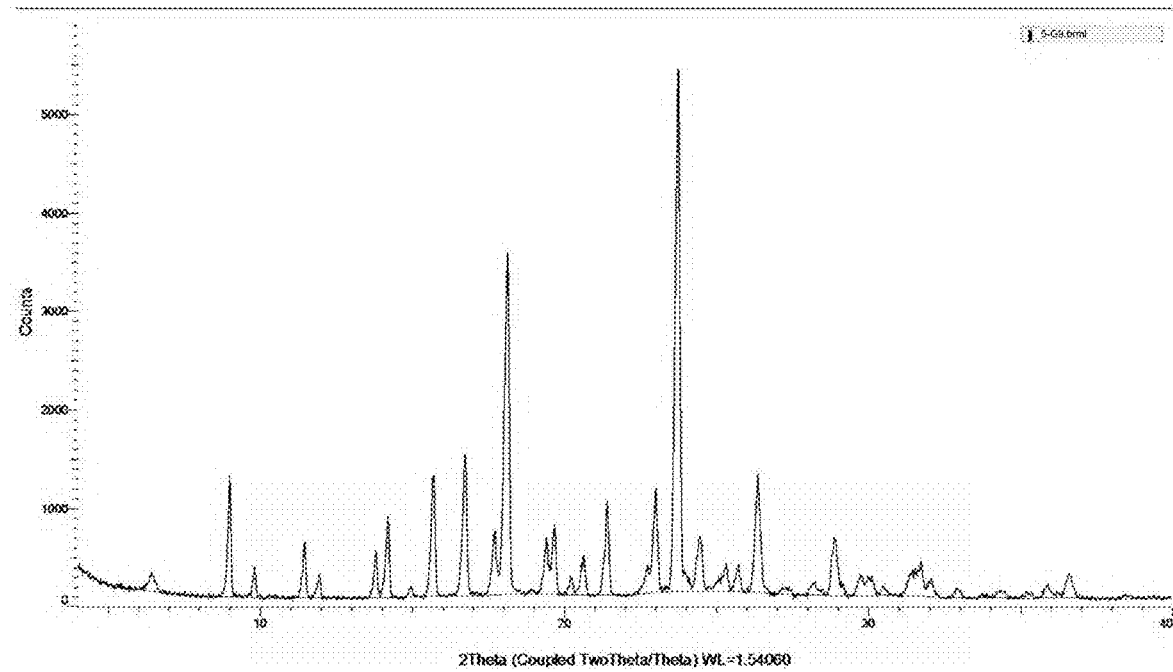

FIG. 582 depicts the XRPD 5-G9 (Experiment Reference 5-Sample Reference G9; the tabernanthalog benzoate salt in FeSSIF, t=6 h, dry pellet).

Figure 583:
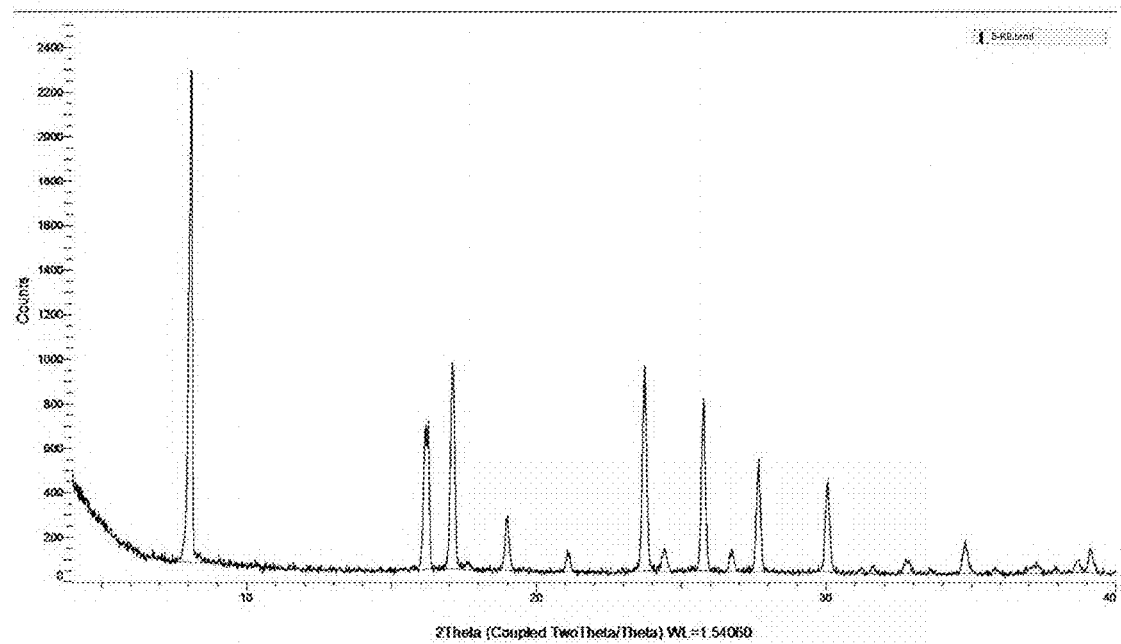

FIG. 583 depicts the XRPD 5-K9 (Experiment Reference 5-Sample Reference K9; the tabernanthalog benzoate salt in FaSSGF, t=6 h, dry pellet).

Figure 584:
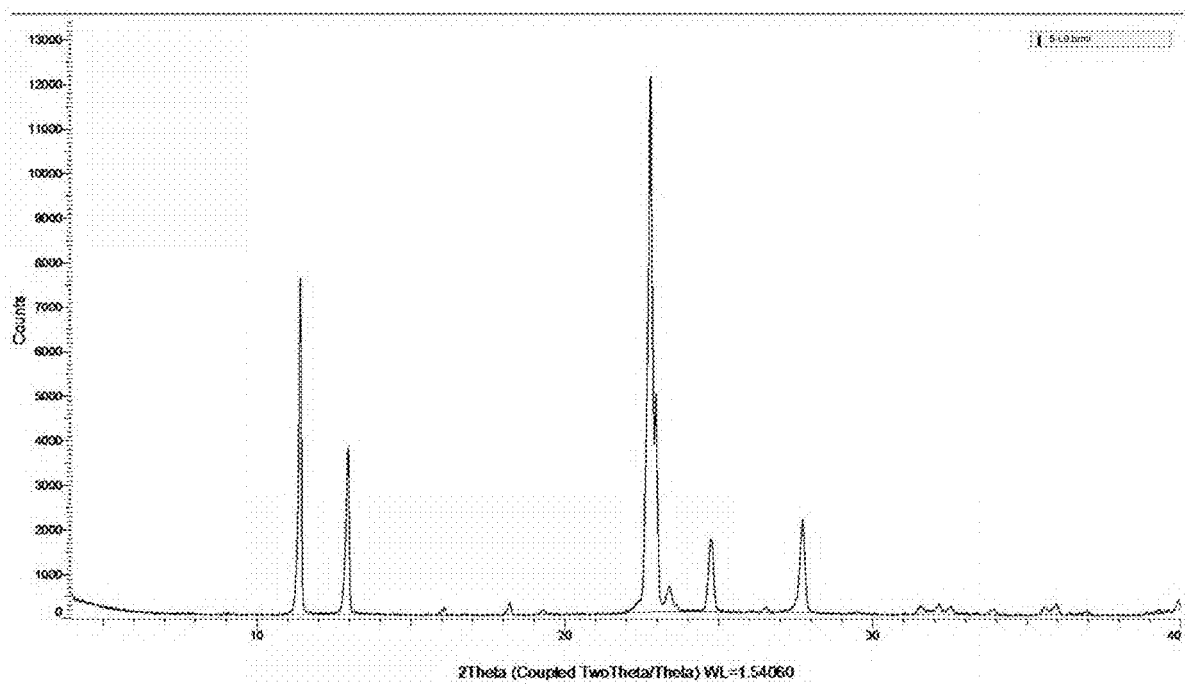

FIG. 584 depicts the XRPD 5-L9 (Experiment Reference 5-Sample Reference L9; the tabernanthalog sorbate salt in FaSSGF, t=6 h, dry pellet).

Figure 585:
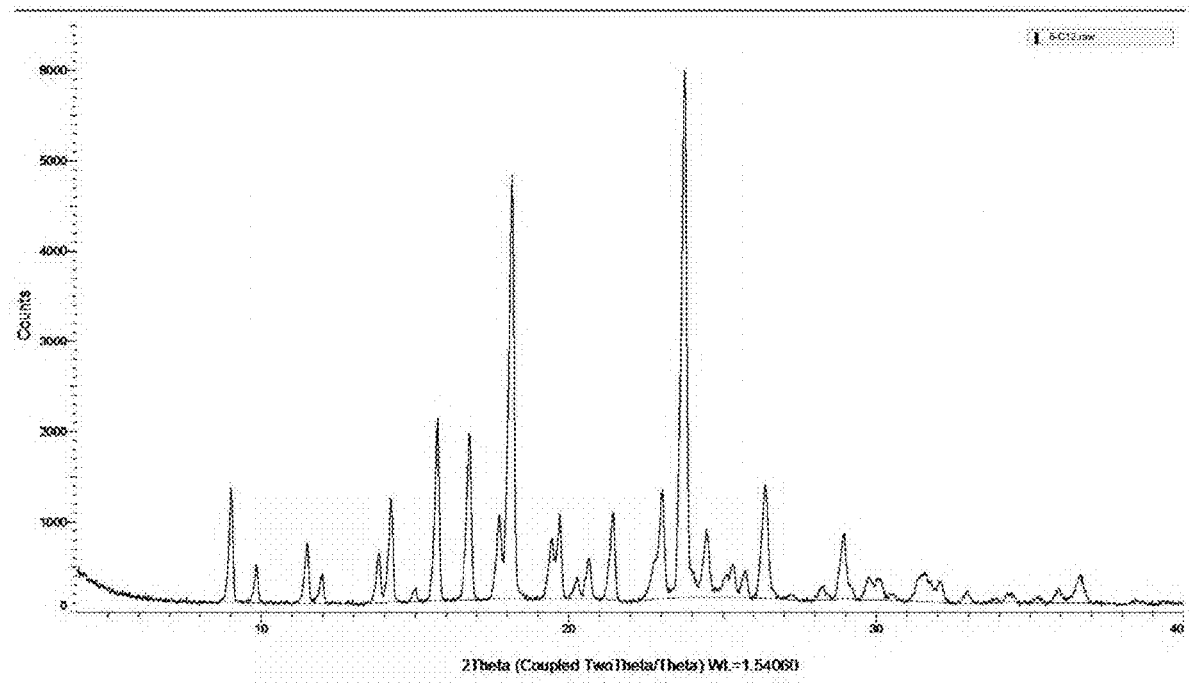

FIG. 585 depicts the XRPD 5-C12 (Experiment Reference 5-Sample Reference C12; the tabernanthalog benzoate salt in FaSSIF, t=24 h, dry pellet).

Figure 586:
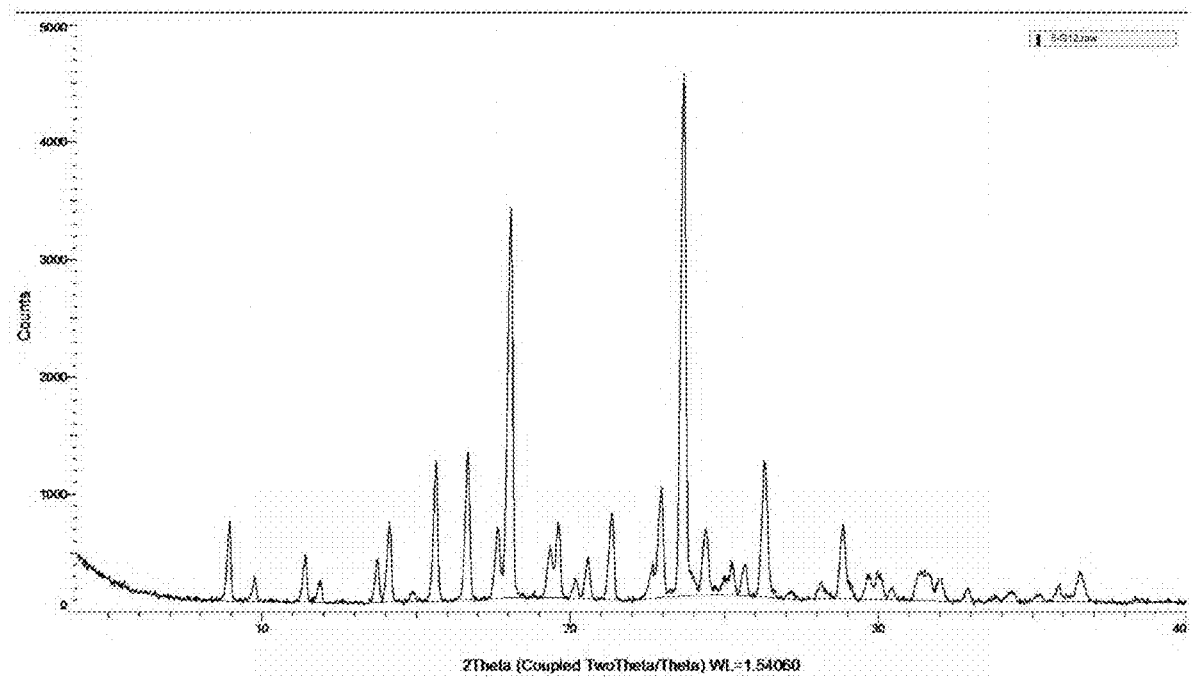

FIG. 586 depicts the XRPD 5-G12 (Experiment Reference 5-Sample Reference G12; the tabernanthalog benzoate salt in FeSSIF, t=24 h, dry pellet).

Figure 587:
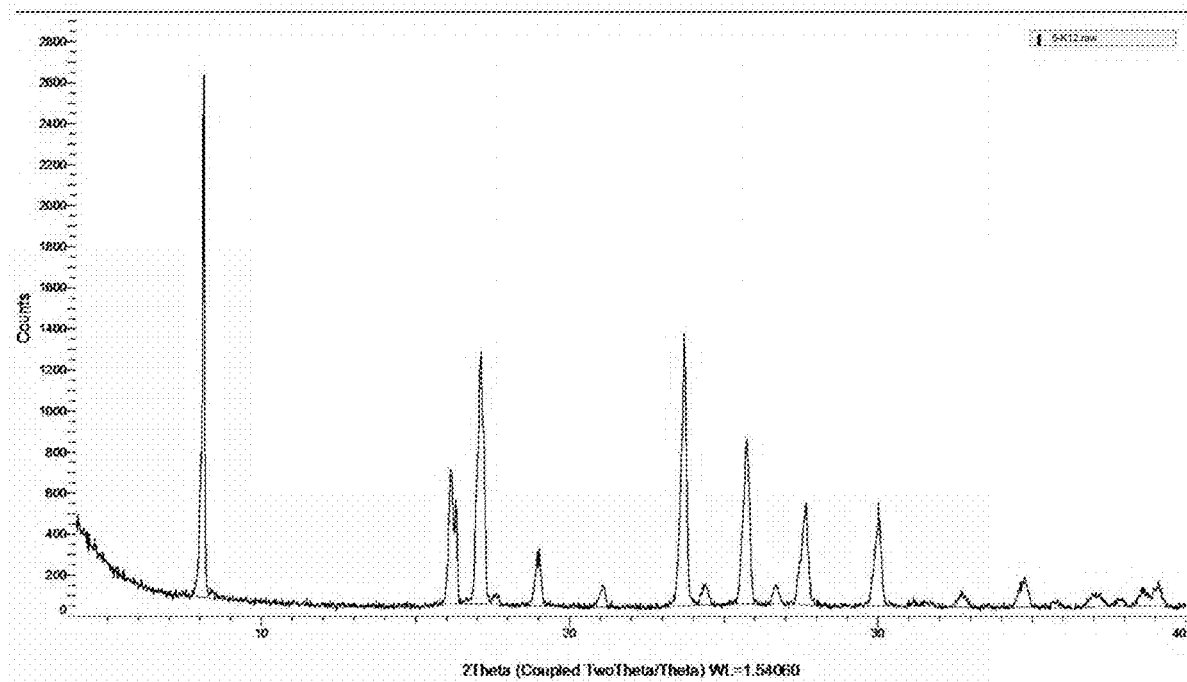

FIG. 587 depicts the XRPD 5-K12 (Experiment Reference 5-Sample Reference K12; the tabernanthalog benzoate salt in FaSSGF, t=24 h, dry pellet).

Figure 588:
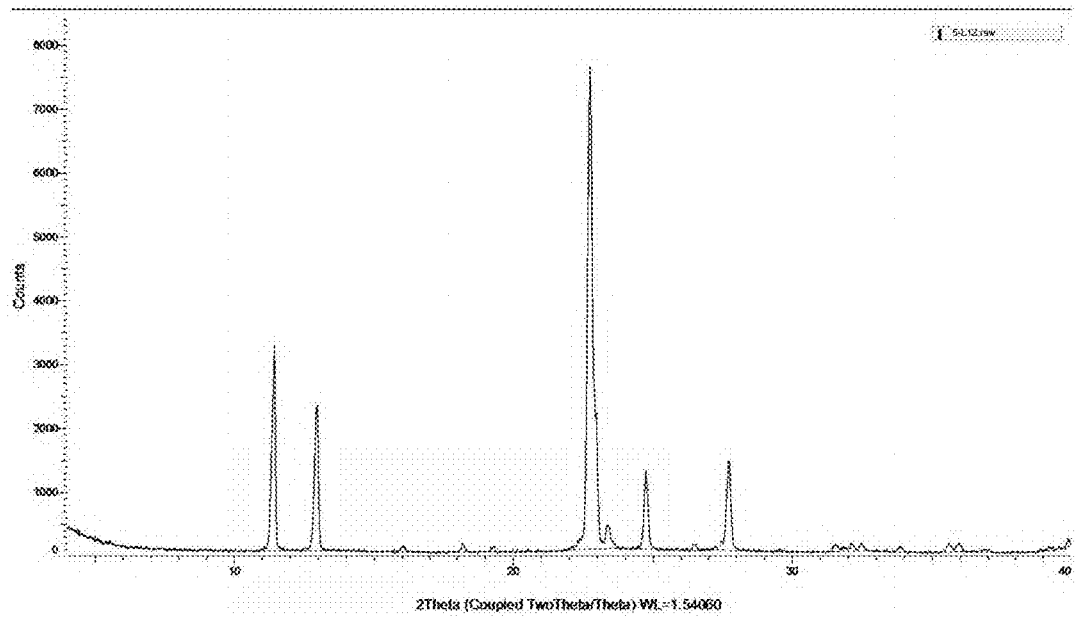

FIG. 588 depicts the XRPD 5-L12 (Experiment Reference 5-Sample Reference L12; the tabernanthalog sorbate salt in FaSSGF, t=24 h, dry pellet).

Figure 589:
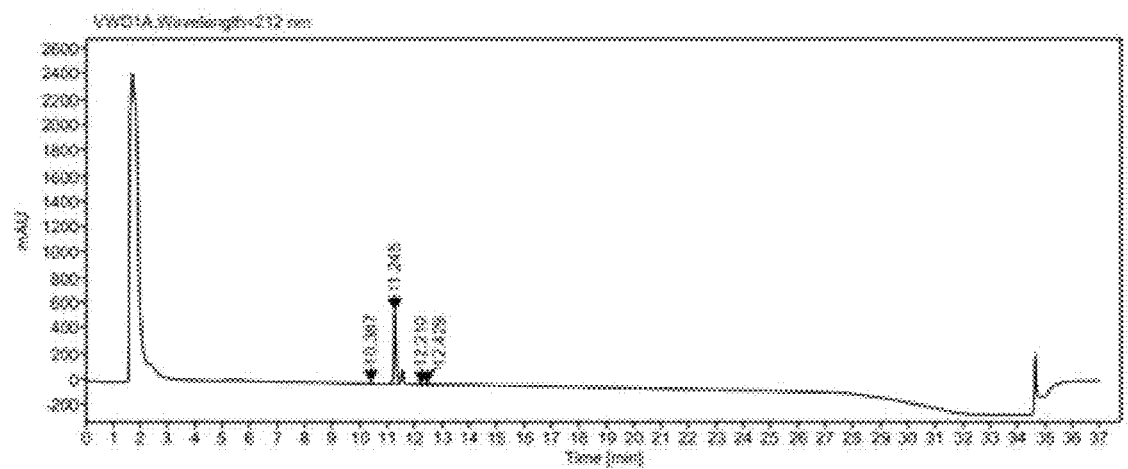

FIG. 589 depicts the HPLC of 5-C1 (Experiment Reference 5-Sample Reference C1; the tabernanthalog benzoate salt in FaSSIF, t=1 h, 50× dilution).

Figure 590:
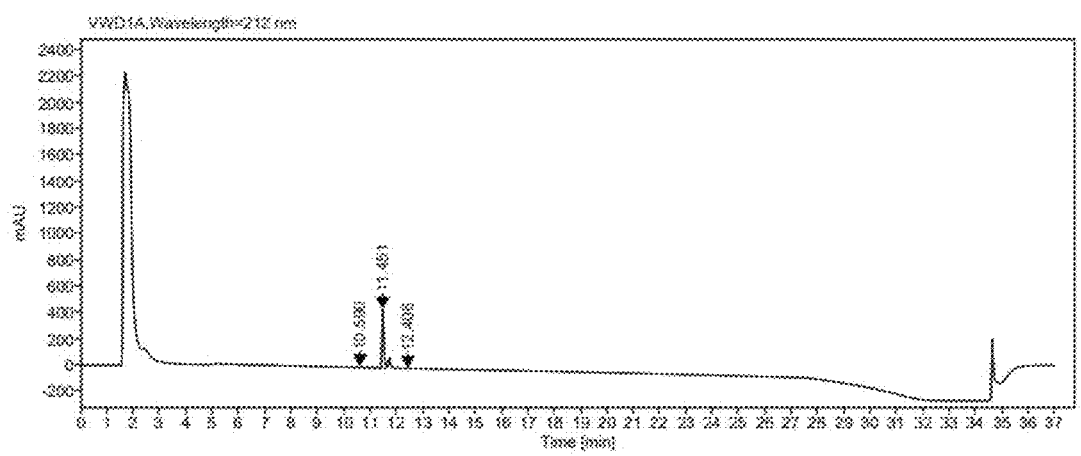

FIG. 590 depicts the HPLC of 5-C4 (Experiment Reference 5-Sample Reference C4; the tabernanthalog benzoate salt in FaSSIF, t=3 h, 50× dilution).

Figure 591:
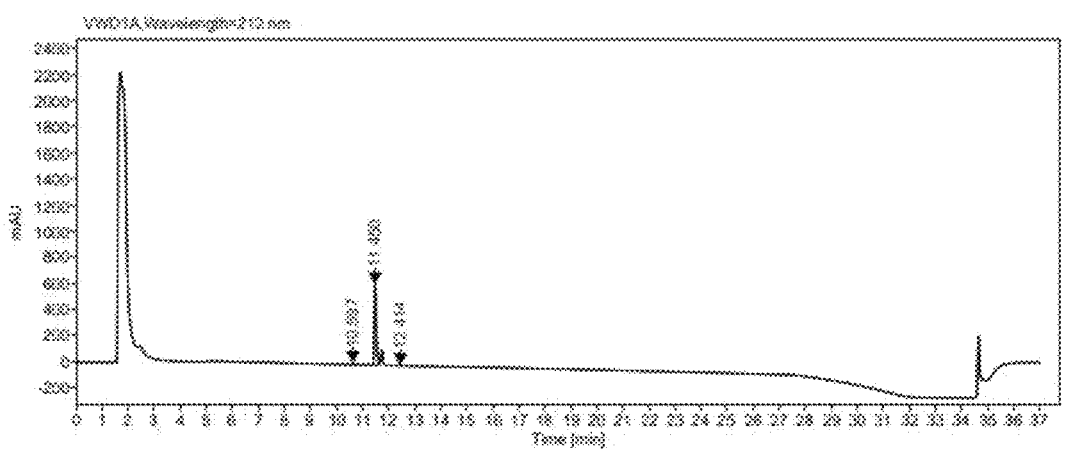

FIG. 591 depicts the HPLC of 5-C7 (Experiment Reference 5-Sample Reference C7; the tabernanthalog benzoate salt in FaSSIF, t=6 h, 50× dilution).

Figure 592:
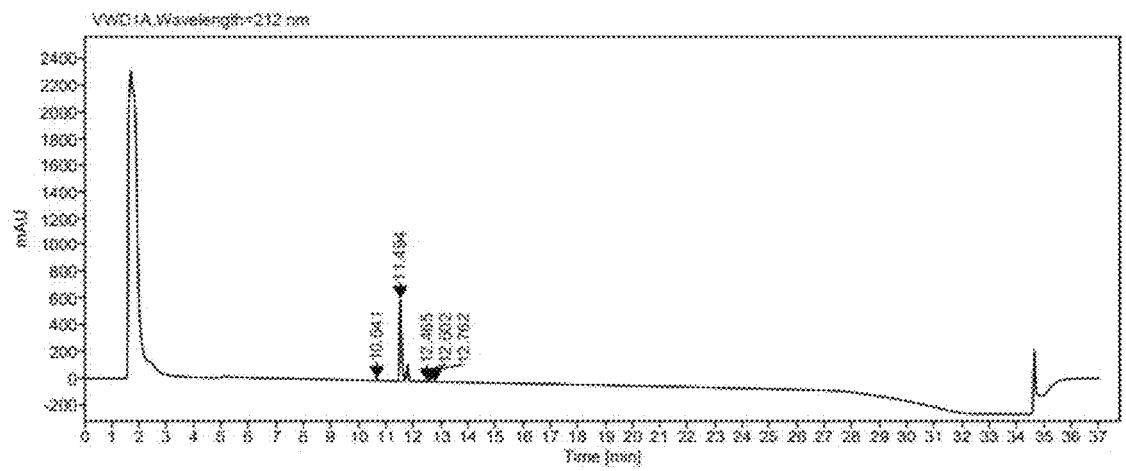

FIG. 592 depicts the HPLC of 5-C10 (Experiment Reference 5-Sample Reference C10; the tabernanthalog benzoate salt in FaSSIF, t=24 h, 50× dilution).

Figure 593:
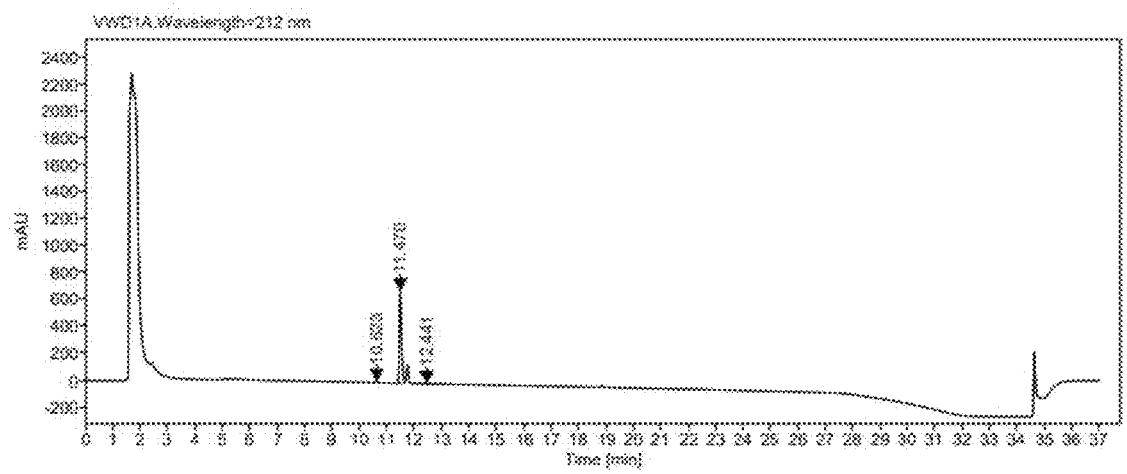

FIG. 593 depicts the HPLC of 5-G1 (Experiment Reference 5-Sample Reference G1; the tabernanthalog benzoate salt in FeSSIF, t=1 h, 50× dilution).

Figure 594:
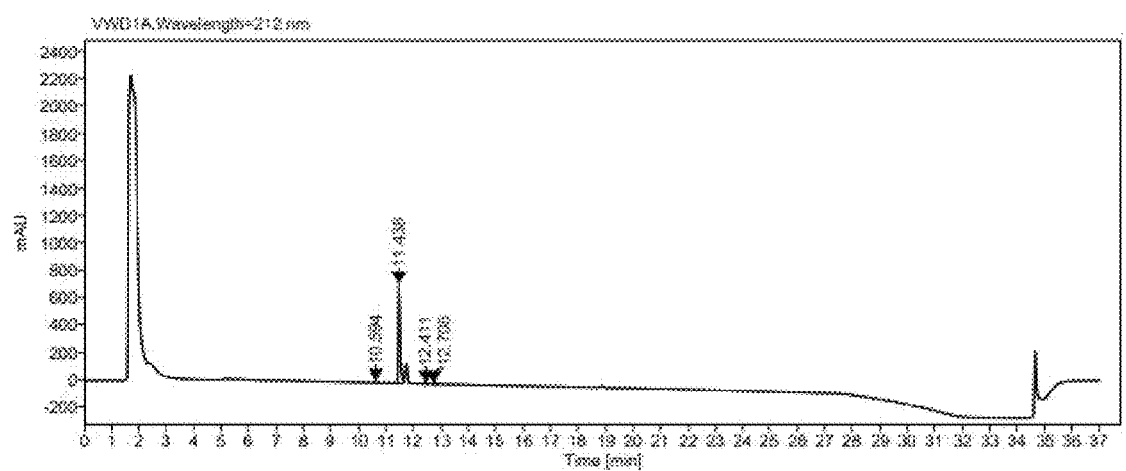

FIG. 594 depicts the HPLC of 5-G4 (Experiment Reference 5-Sample Reference G4; the tabernanthalog benzoate salt in FeSSIF, t=3 h, 50× dilution).

Figure 595:
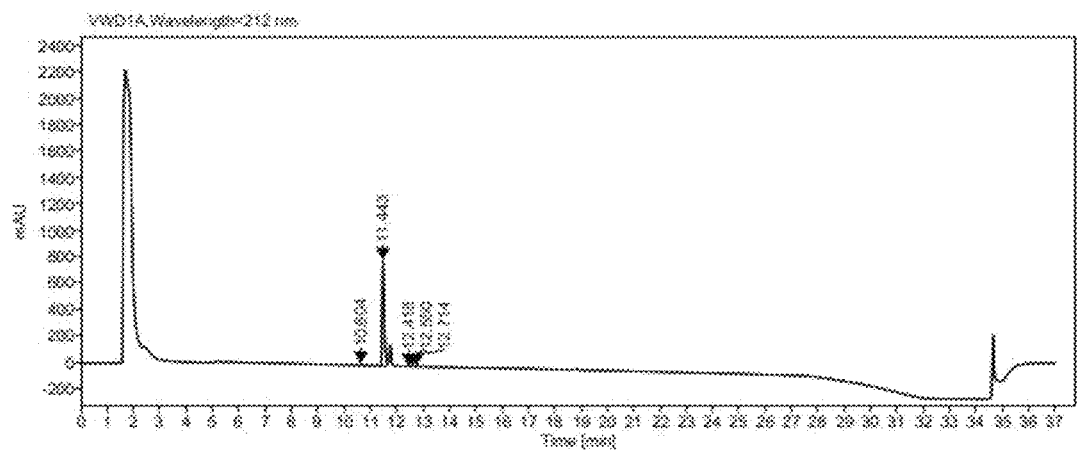

FIG. 595 depicts the HPLC of 5-G7 (Experiment Reference 5-Sample Reference G7; the tabernanthalog benzoate salt in FeSSIF, t=6 h, 50× dilution).

Figure 596:
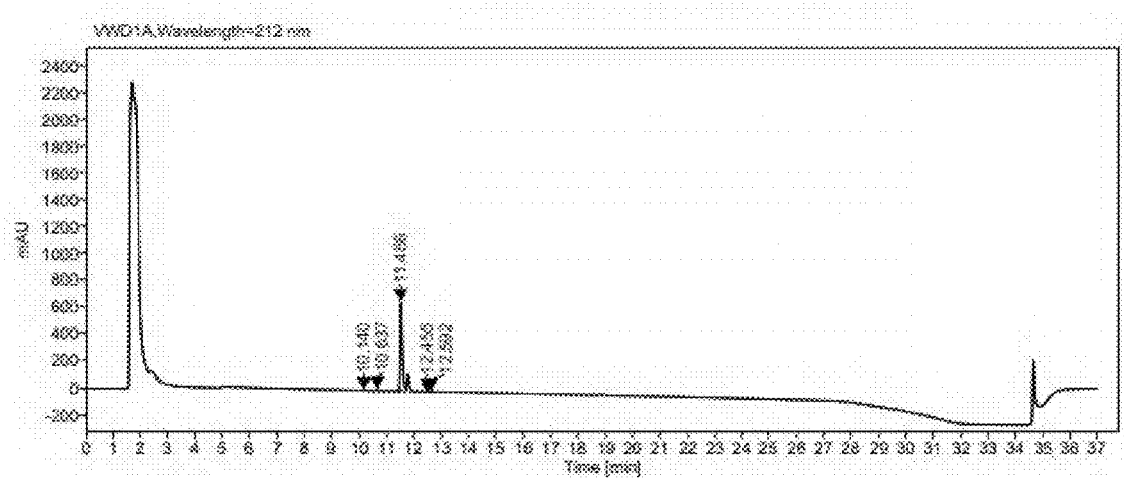

FIG. 596 depicts the HPLC of 5-G10 (Experiment Reference 5-Sample Reference G10; the tabernanthalog benzoate salt in FeSSIF, t=24 h, 50× dilution).

Figure 597:
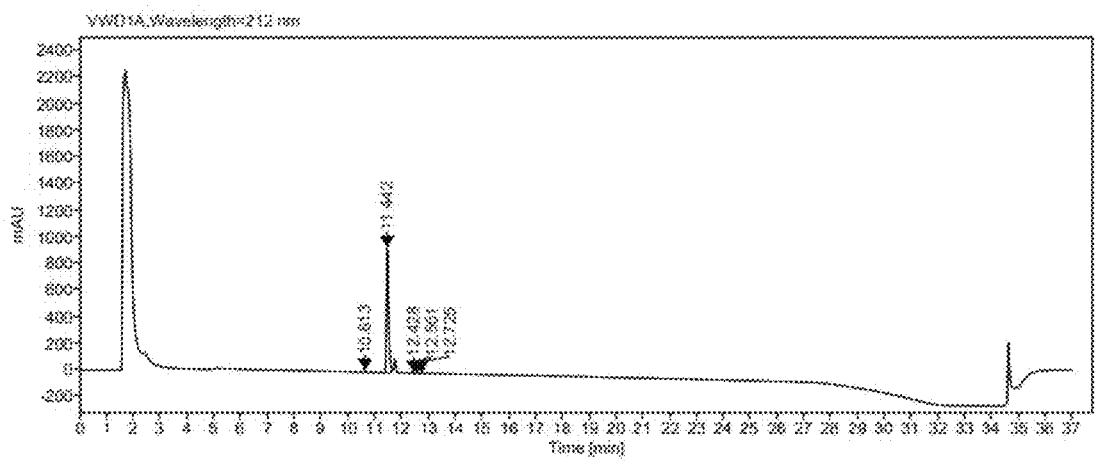

FIG. 597 depicts the HPLC of 5-K1 (Experiment Reference 5-Sample Reference K1; the tabernanthalog benzoate salt in FaSSGF, t=1 h, 100× dilution).

Figure 598:
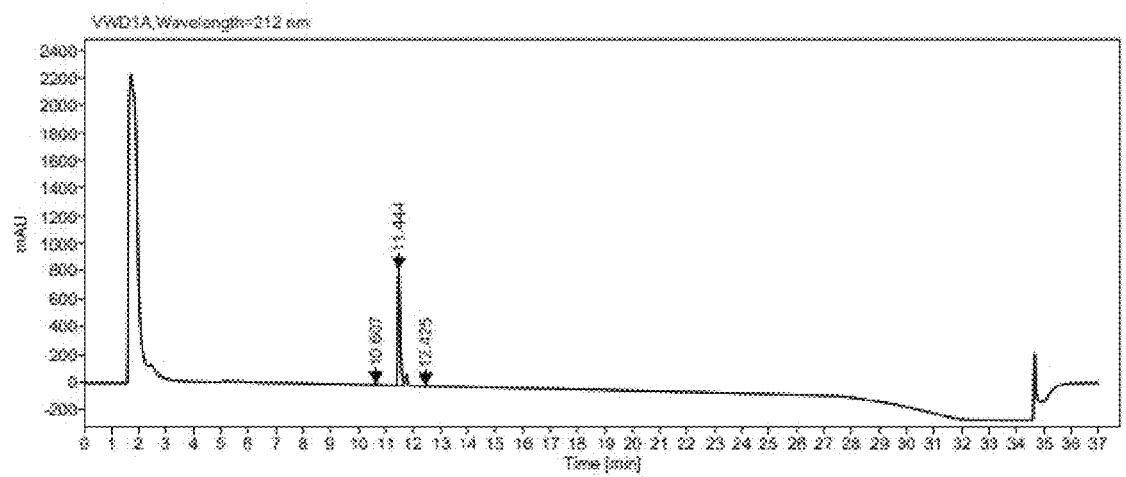

FIG. 598 depicts the HPLC of 5-K4 (Experiment Reference 5-Sample Reference K4; the tabernanthalog benzoate salt in FaSSGF, t=3 h, 100× dilution).

Figure 599:
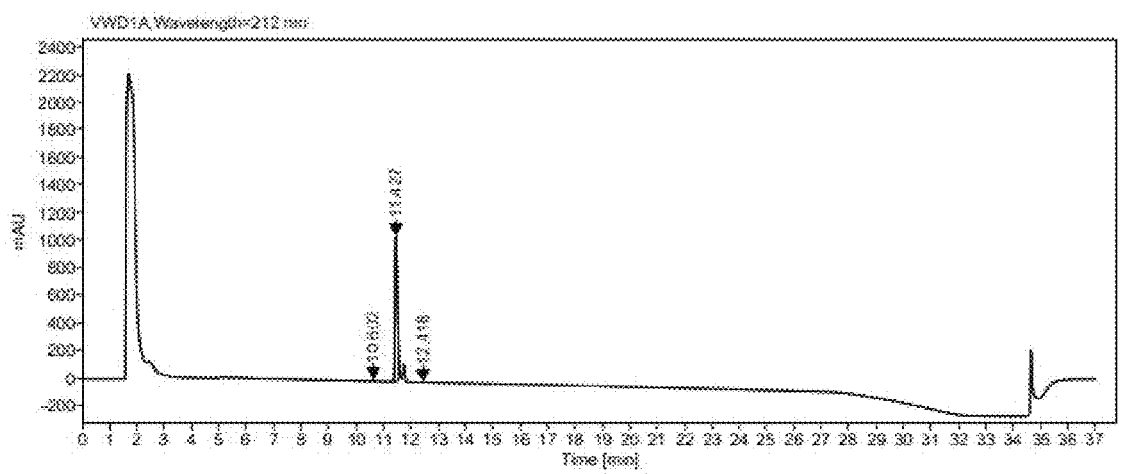

FIG. 599 depicts the HPLC of 5-K7 (Experiment Reference 5-Sample Reference K7; the tabernanthalog benzoate salt in FaSSGF, t=6 h, 100× dilution).

Figure 600:
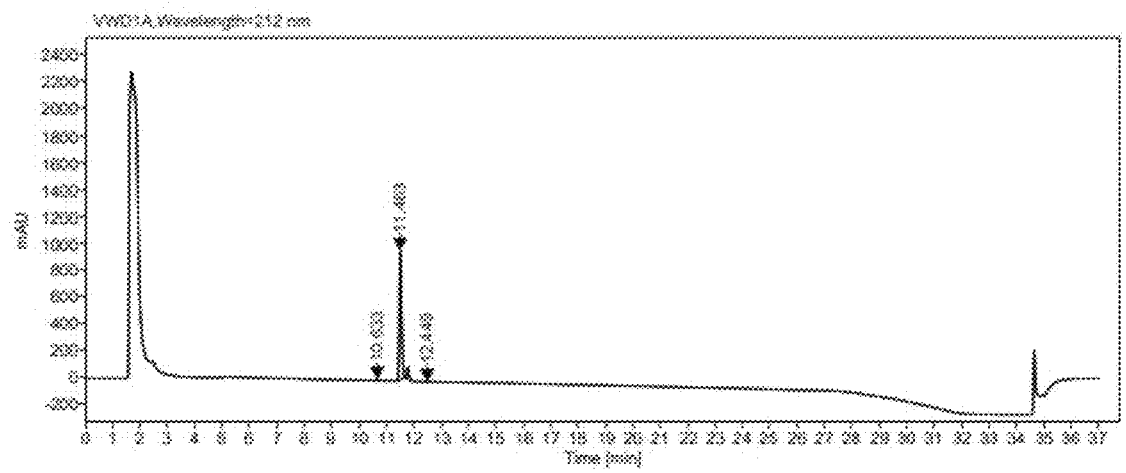

FIG. 600 depicts the HPLC of 5-K10 (Experiment Reference 5-Sample Reference K10; the tabernanthalog benzoate salt in FaSSGF, t=24 h, 100× dilution).

Figure 601:
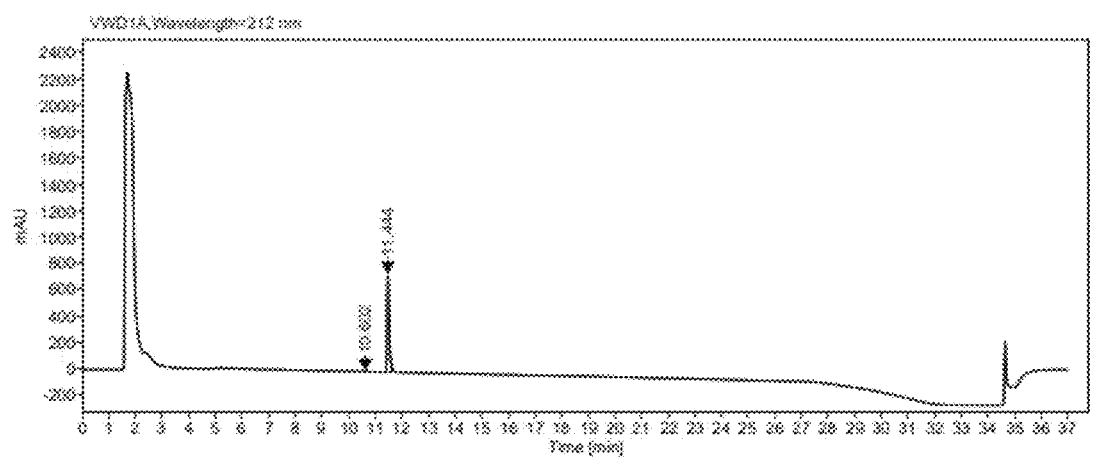

FIG. 601 depicts the HPLC of 5-L1 (Experiment Reference 5-Sample Reference L1; the tabernanthalog sorbate salt in FaSSGF, t=1 h, 100× dilution).

Figure 602:
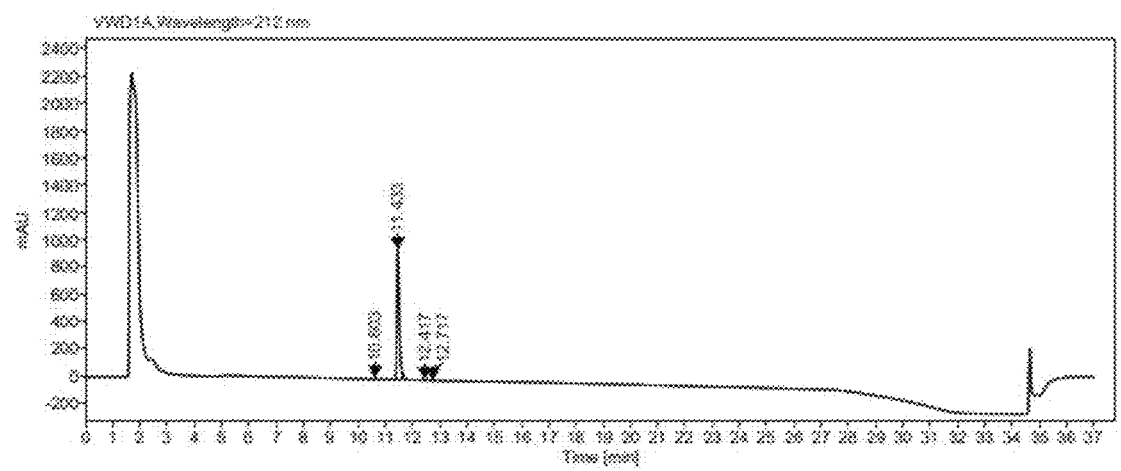

FIG. 602 depicts the HPLC of 5-L4 (Experiment Reference 5-Sample Reference L4; the tabernanthalog sorbate salt in FaSSGF, t=3 h, 100× dilution).

Figure 603:
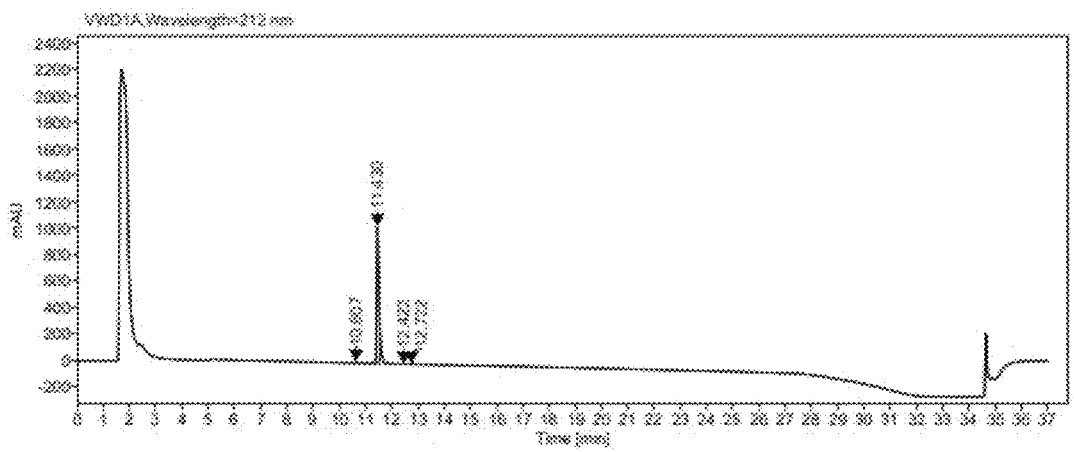

FIG. 603 depicts the HPLC of 5-L7 (Experiment Reference 5-Sample Reference L7; the tabernanthalog sorbate salt in FaSSGF, t=6 h, 100× dilution).

Figure 604:
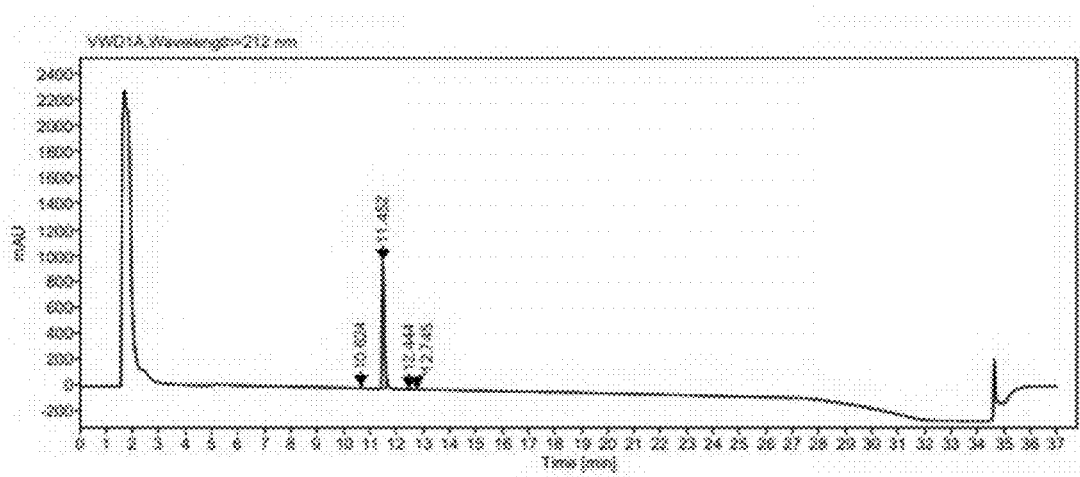

FIG. 604 depicts the HPLC of 5-L10 (Experiment Reference 5-Sample Reference L10; the tabernanthalog sorbate salt in FaSSGF, t=24 h, 100× dilution).

Figure 605:
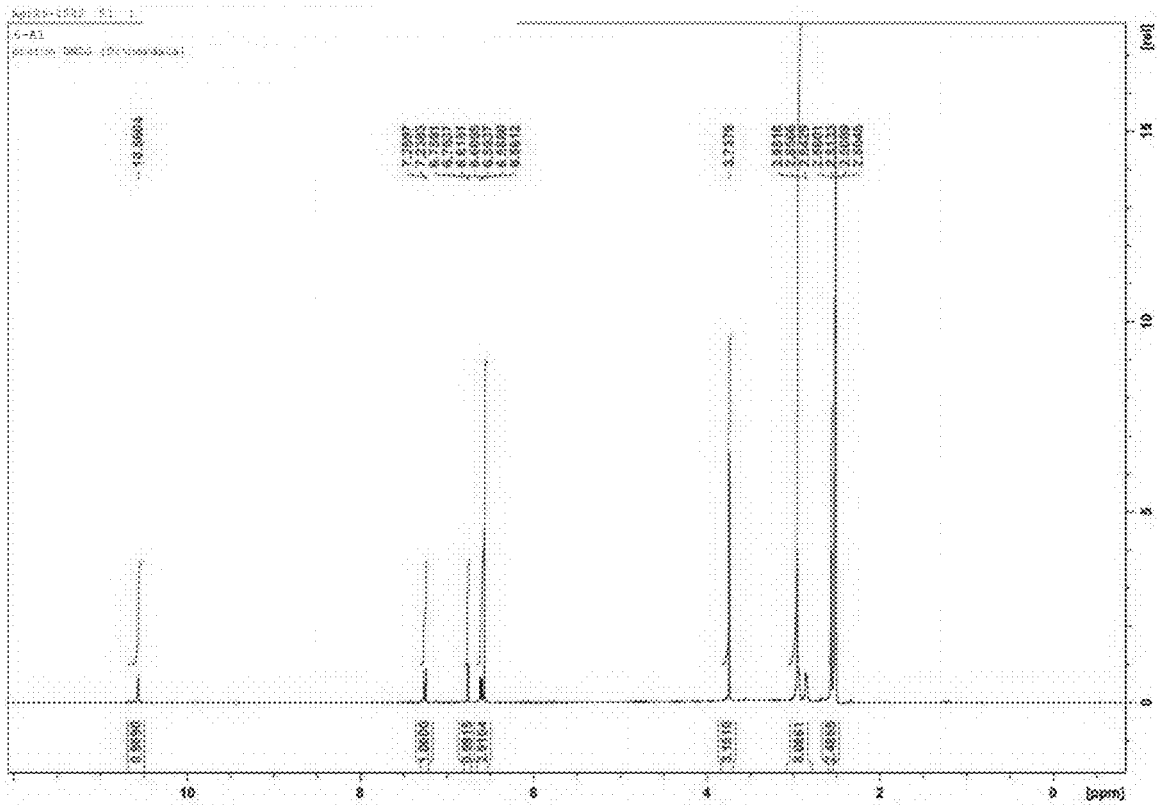

FIG. 605 depicts the $^1$H NMR of tabernanthalog monofumarate salt; 6-A1 (Experiment Reference 6-Sample Reference A1) (t=5 d), analysis was acquired in DMSO-d6 and calibrated to the non-deuterated solvent residual at 2.50 ppm. 1.0 mol of API to 1.0 mol of fumaric acid.

Figure 606:
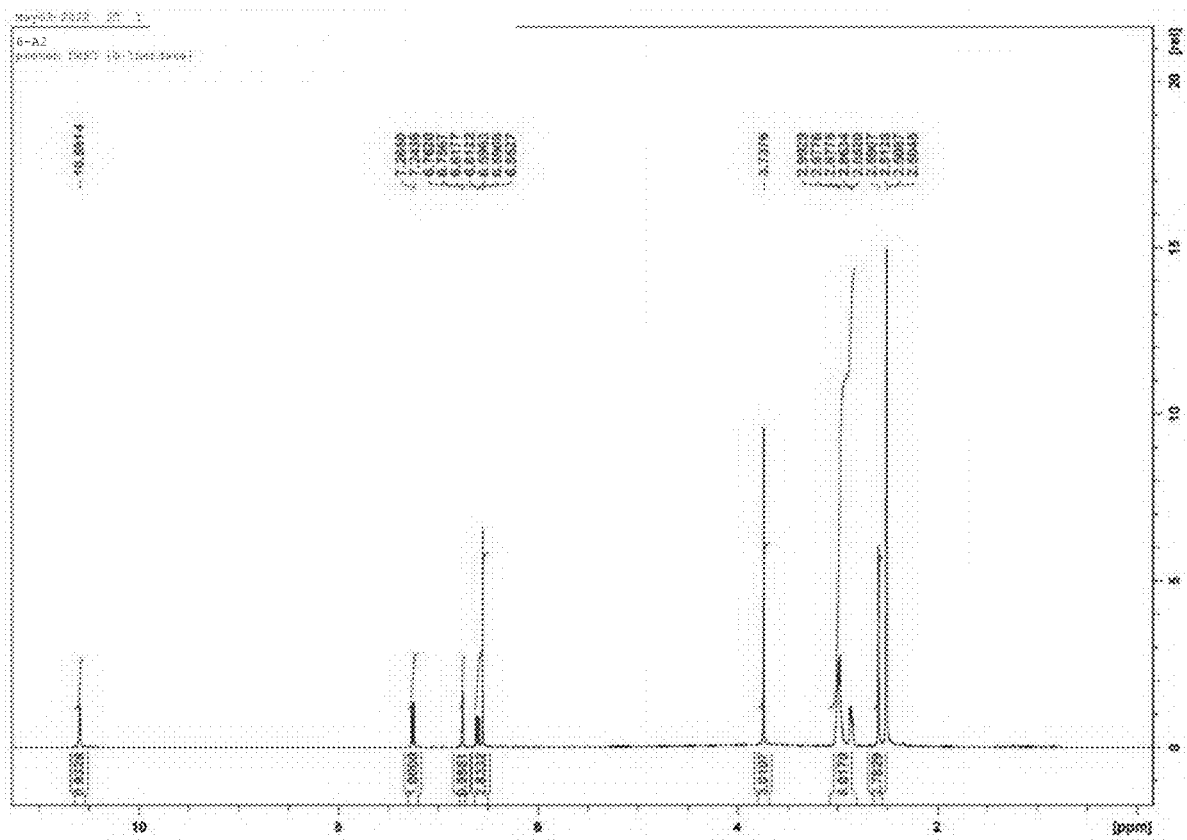

FIG. 606 depicts the $^1$H NMR of tabernanthalog monofumarate salt; 6-A2 (Experiment Reference 6-Sample Reference A2) (t=10 d), acquired in DMSO-d6 and calibrated to the non-deuterated solvent residual at 2.50 ppm. 1.0 mol of API to 1.0 mol of fumaric acid.

Figure 607:
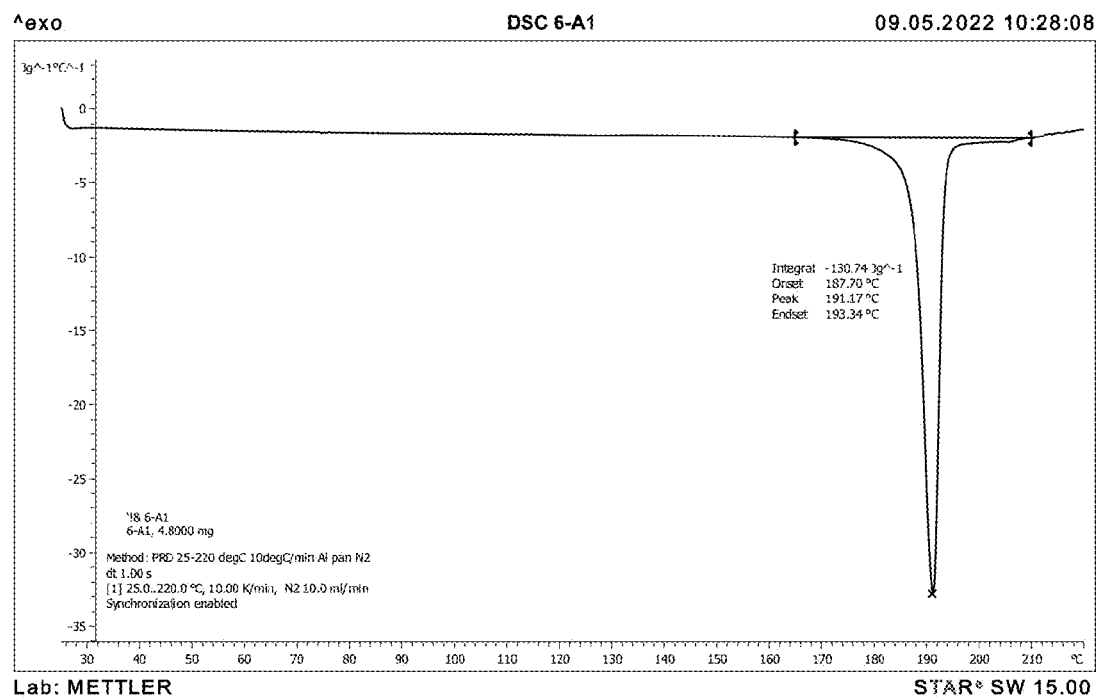

FIG. 607 depicts the DSC profile of tabernanthalog monofumarate salt; 6-A1 (Experiment Reference 6-Sample Reference A1) (t=5 d), analysis was acquired at a ramp rate of +10° C./minute.

Figure 608:
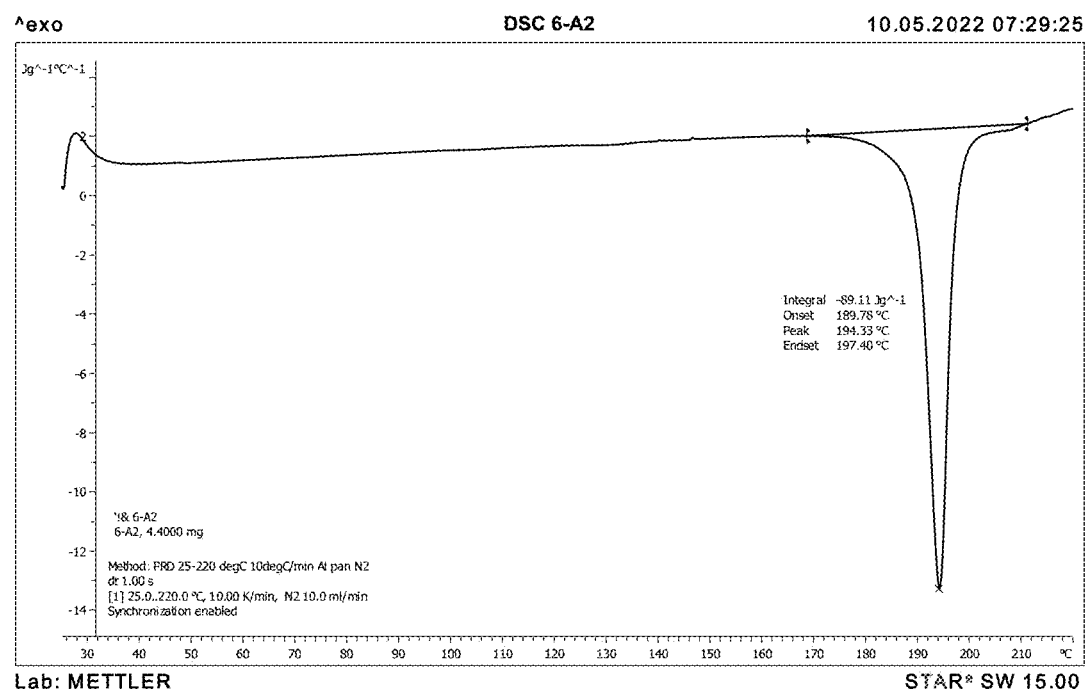

FIG. 608 depicts the DSC profile of tabernanthalog monofumarate salt; 6-A2 (Experiment Reference 6-Sample Reference A2) (t=10 d), analysis was acquired at a ramp rate of +10° C./minute.

Figure 609:
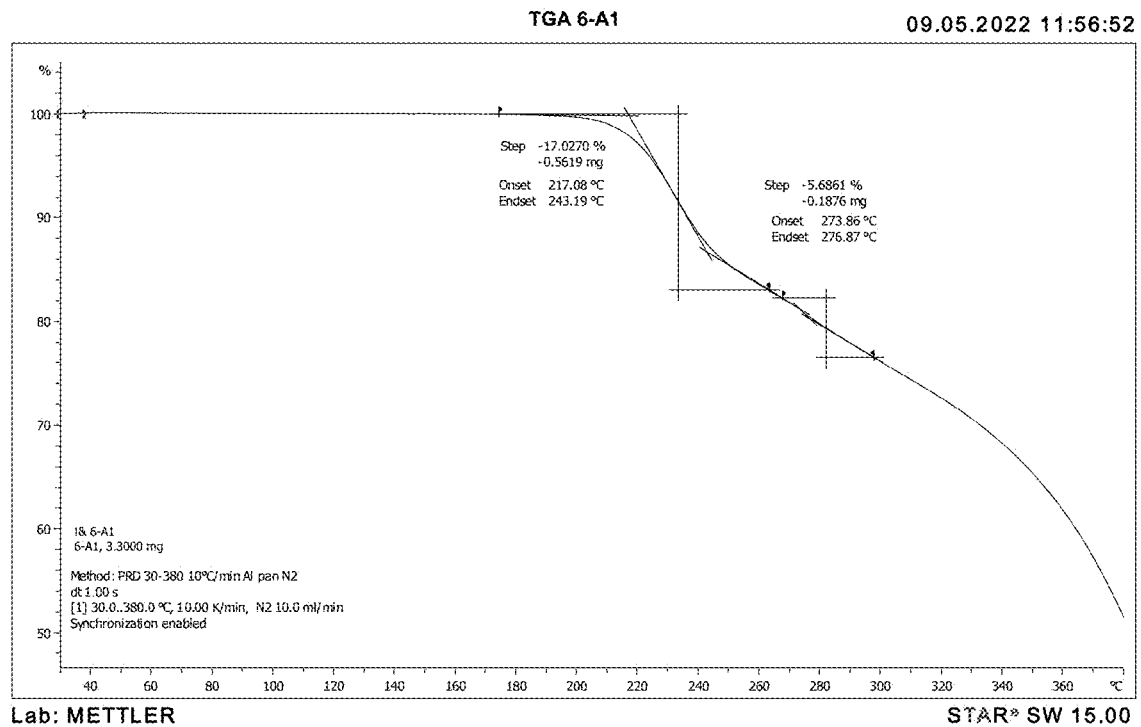

FIG. 609 depicts the TGA of tabernanthalog monofumarate salt; 6-A1 (Experiment Reference 6-Sample Reference A1) (t=5 d), analysis was acquired at a ramp rate of +10° C./minute.

Figure 610:
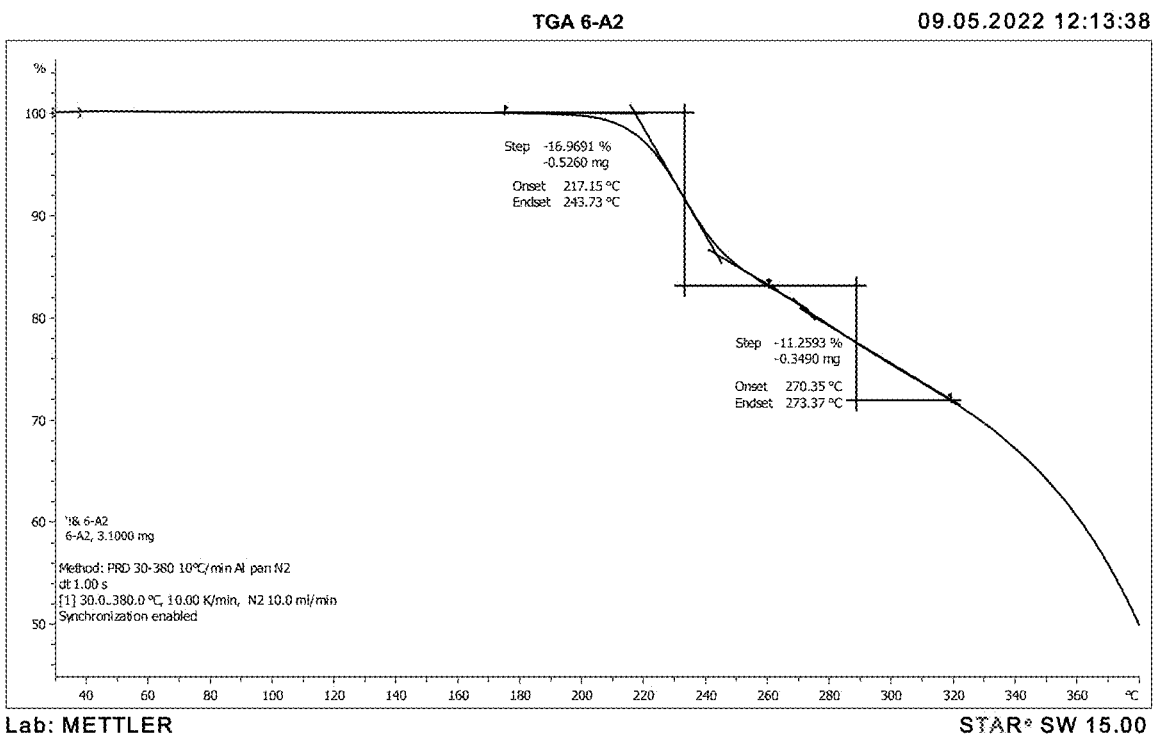

FIG. 610 depicts the TGA of tabernanthalog monofumarate salt; 6-A2 (Experiment Reference 6-Sample Reference A2) (t=10 d), analysis was acquired at a ramp rate of +10° C./minute.

Figure 611:
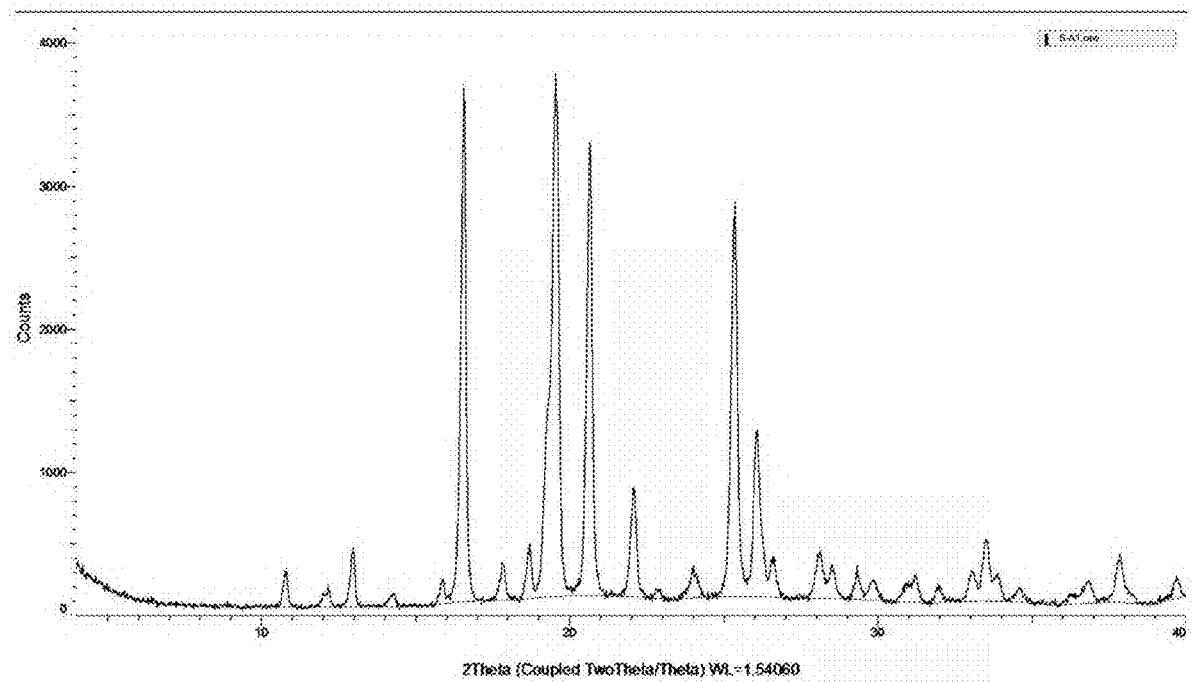

FIG. 611 depicts the XRPD of tabernanthalog monofumarate salt; 6-A1 (Experiment Reference 6-Sample Reference A1) (t=5 d).

Figure 612:
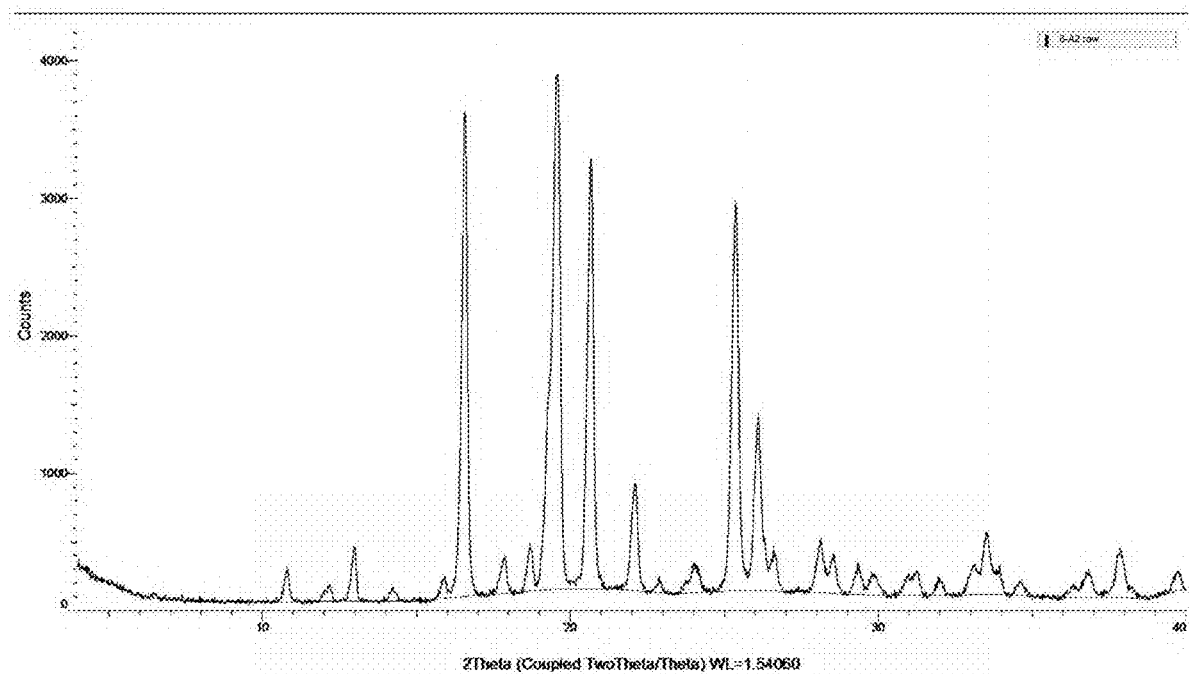

FIG. 612 depicts the XRPD of tabernanthalog monofumarate salt; 6-A2 (Experiment Reference 6-Sample Reference A2) (t=10 d).

Figure 613:
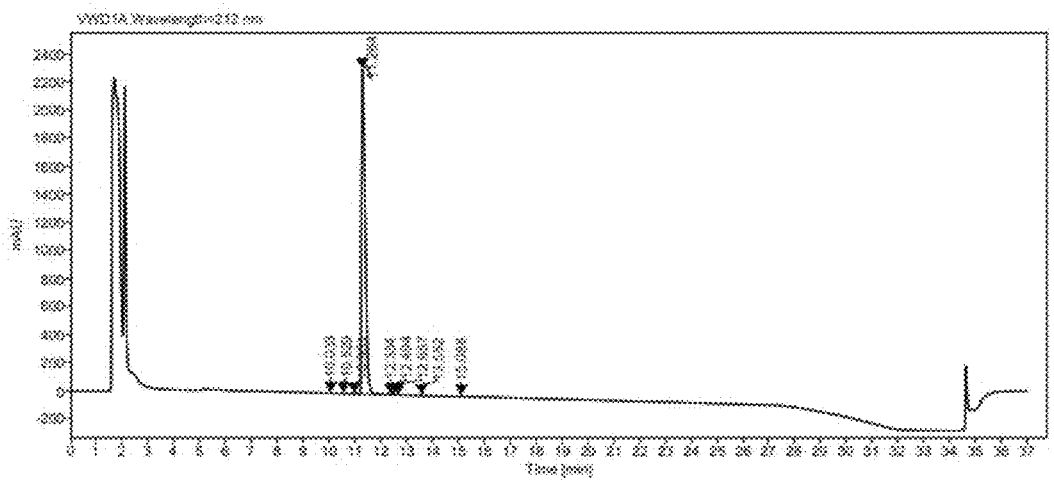

FIG. 613 depicts the HPLC of tabernanthalog monofumarate salt; 6-A1 (Experiment Reference 6-Sample Reference A1) (t=5 d).

Figure 614:
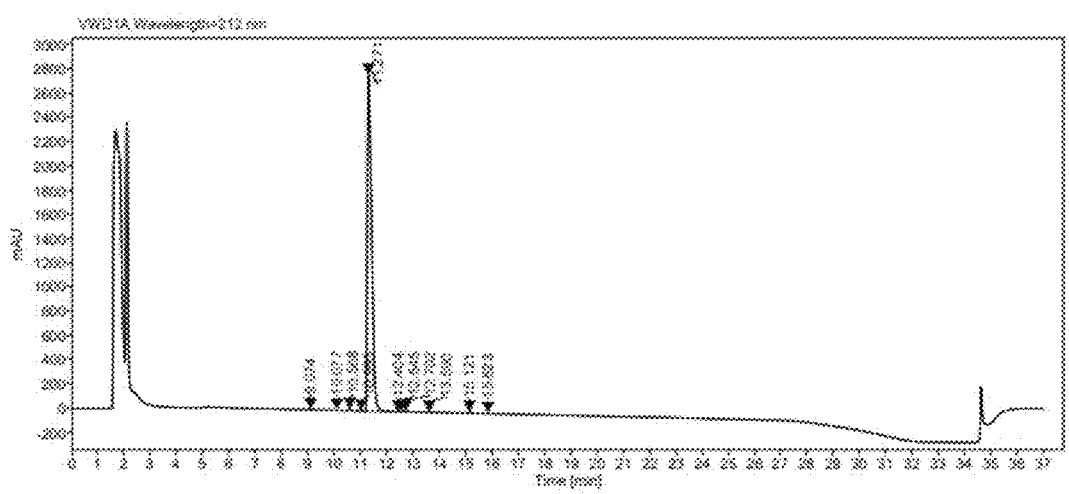

FIG. 614 depicts the HPLC of tabernanthalog monofumarate salt; 6-A2 (Experiment Reference 6-Sample Reference A2) (t=10 d).

Figure 615:
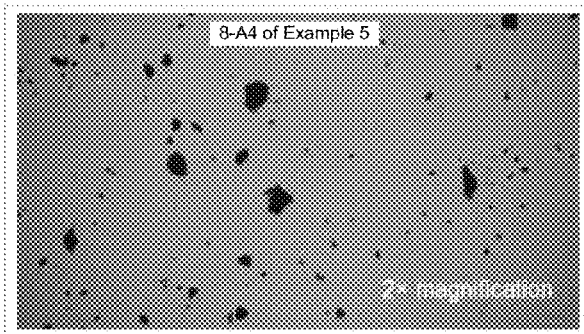

FIG. 615 depicts the PLM of tabernanthalog monofumarate salt, 8-A4 of Example 5 (Experiment Reference 8-Sample Reference A4 of Example 5) (input)×2 mag, NP.

Figure 616:
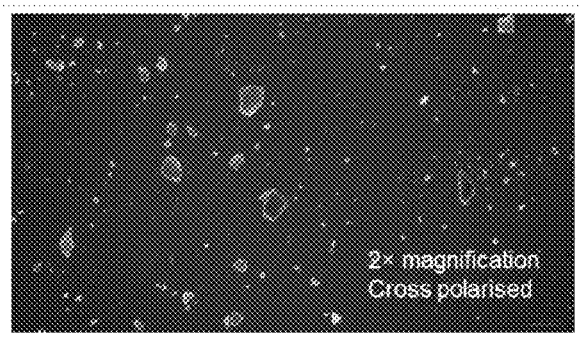

FIG. 616 depicts the PLM of tabernanthalog monofumarate salt; 8-A4 of Example 5 (Experiment Reference 8-Sample Reference A4 of Example 5) (input)×2 mag, CP.

Figure 617:
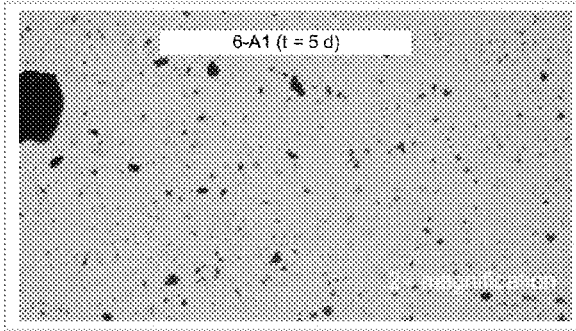

FIG. 617 depicts the PLM of tabernanthalog monofumarate salt; 6-A1 (Experiment Reference 6-Sample Reference A1) (t=5 d)×5 mag, NP.

Figure 618:
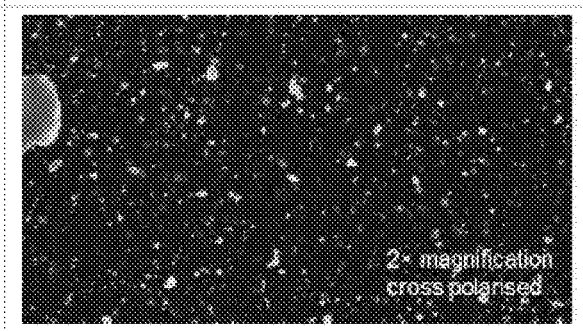

FIG. 618 depicts the PLM of tabernanthalog monofumarate salt; 6-A1 (Experiment Reference 6-Sample Reference A1) (t=5 d)×5 mag, CP.

Figure 619:
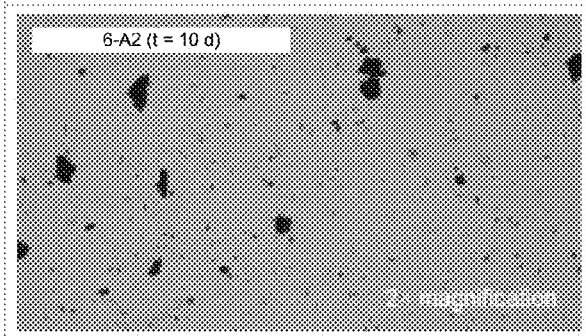

FIG. 619 depicts the PLM of tabernanthalog monofumarate salt; 6-A2 (Experiment Reference 6-Sample Reference A2) (t=10 d)×5 mag, NP.

Figure 620:
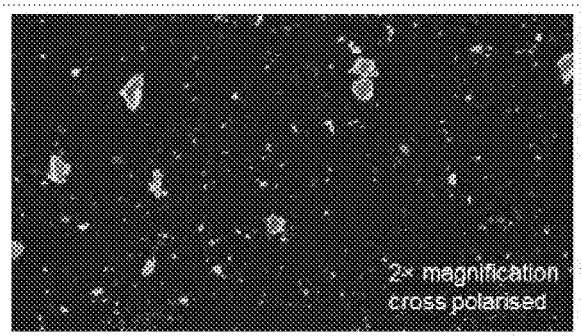

FIG. 620 depicts the PLM of tabernanthalog monofumarate salt, 6-A2 (Experiment Reference 6-Sample Reference A2) (t=10 d)×5 mag, CP.

Figure 621:
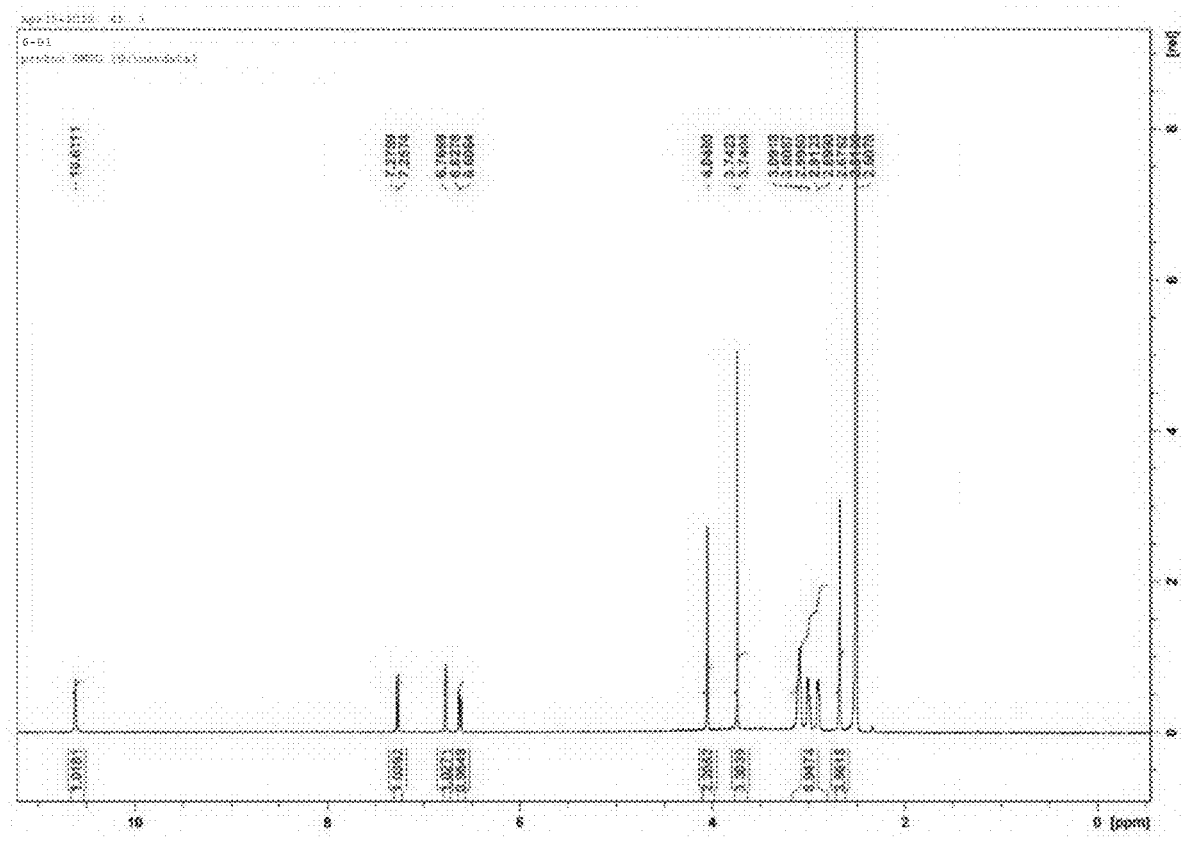

FIG. 621 depicts the $^1$H NMR of tabernanthalog tartrate salt; 6-B1 (Experiment Reference 6-Sample Reference B1) (t=5 d), analysis was acquired in DMSO-d6 and calibrated to the non-deuterated solvent residual at 2.50 ppm. 1.0 mol of API to 1.0 mol of L-tartaric acid, 1.0 to 1.0. Ethanol not detected.

Figure 622:
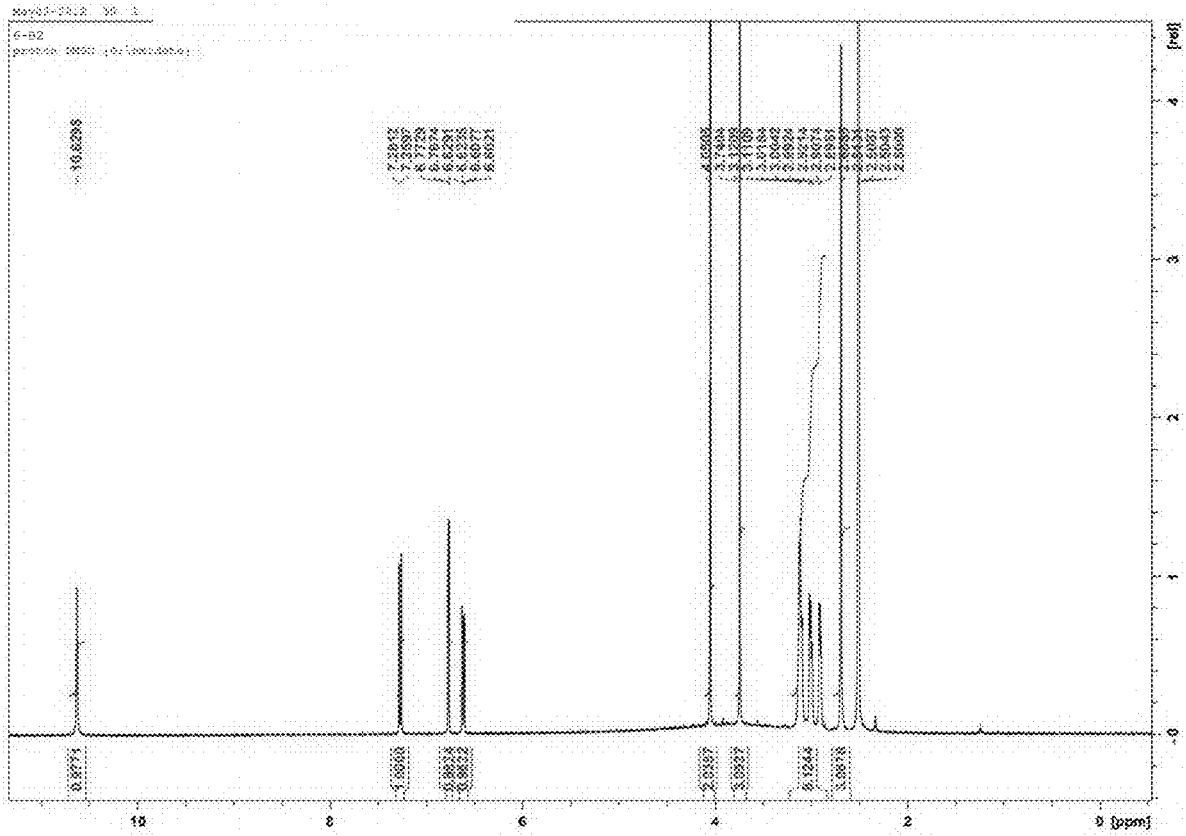

FIG. 622 depicts the $^1$H NMR of tabernanthalog tartrate salt; 6-B2 (Experiment Reference 6-Sample Reference B2) (t=10 d), acquired in DMSO-d6 and calibrated to the non-deuterated solvent residual at 2.50 ppm. 1.0 mol of API to 1.0 mol of L-tartaric acid.

Figure 623:
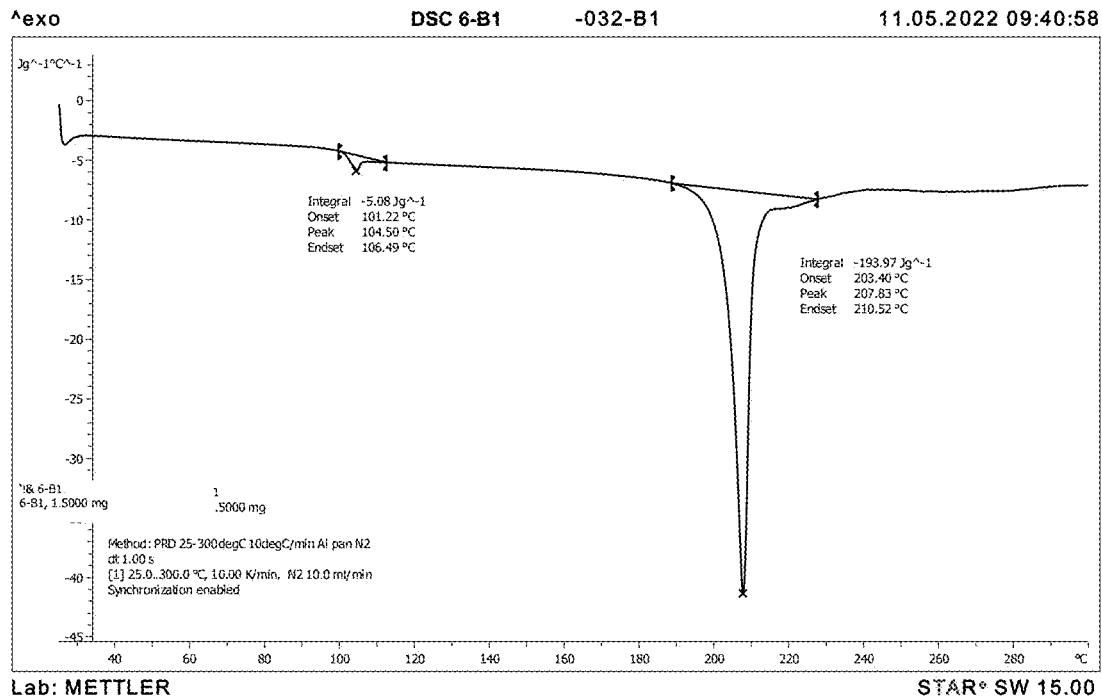

FIG. 623 depicts the DSC profile of tabernanthalog tartrate salt; 6-B1 (Experiment Reference 6-Sample Reference B1) (t=5 d), analysis was acquired at a ramp rate of +10° C./minute.

Figure 624:
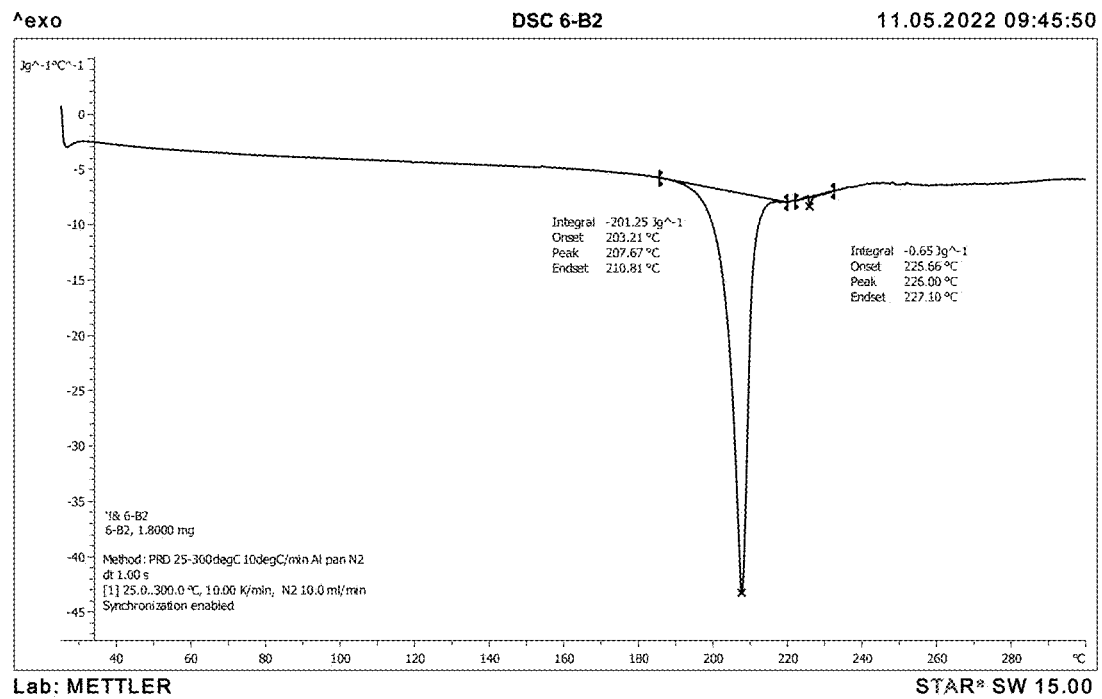

FIG. 624 depicts the DSC profile of tabernanthalog tartrate salt; 6-B2 (Experiment Reference 6-Sample Reference B2) (t=10 d), analysis was acquired at a ramp rate of +10° C./minute.

Figure 625:
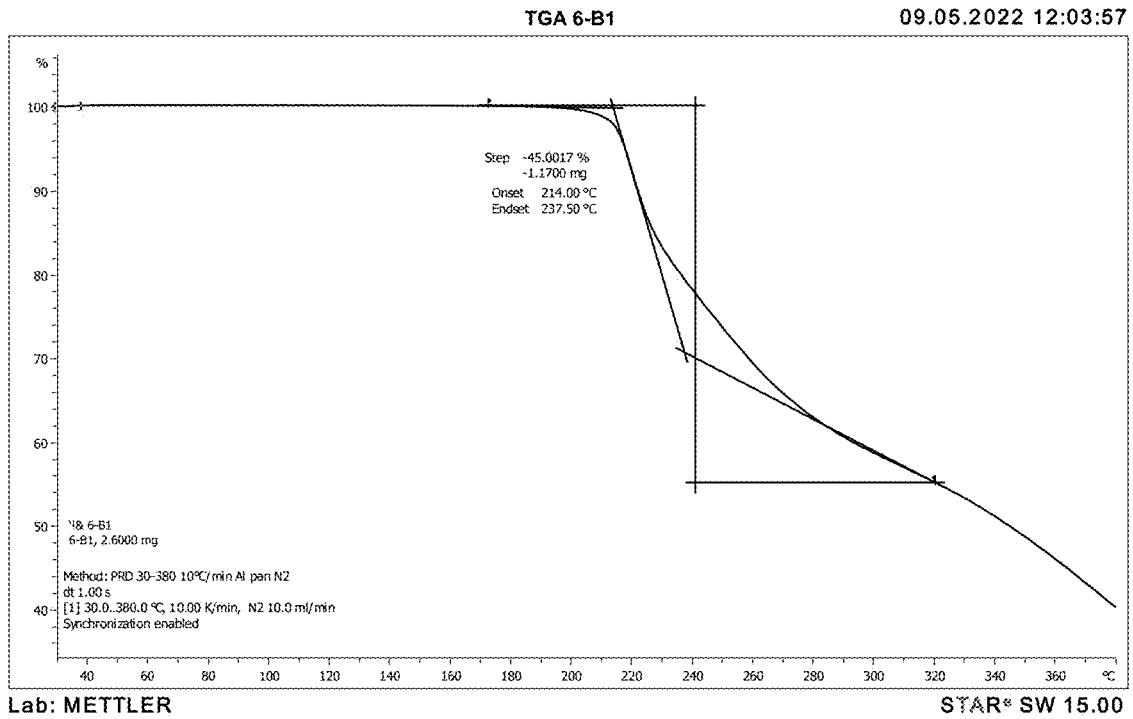

FIG. 625 depicts the TGA of tabernanthalog tartrate salt; 6-B1 (Experiment Reference 6-Sample Reference B1) (t=5 d), analysis was acquired at a ramp rate of +10° C./minute.

Figure 626:
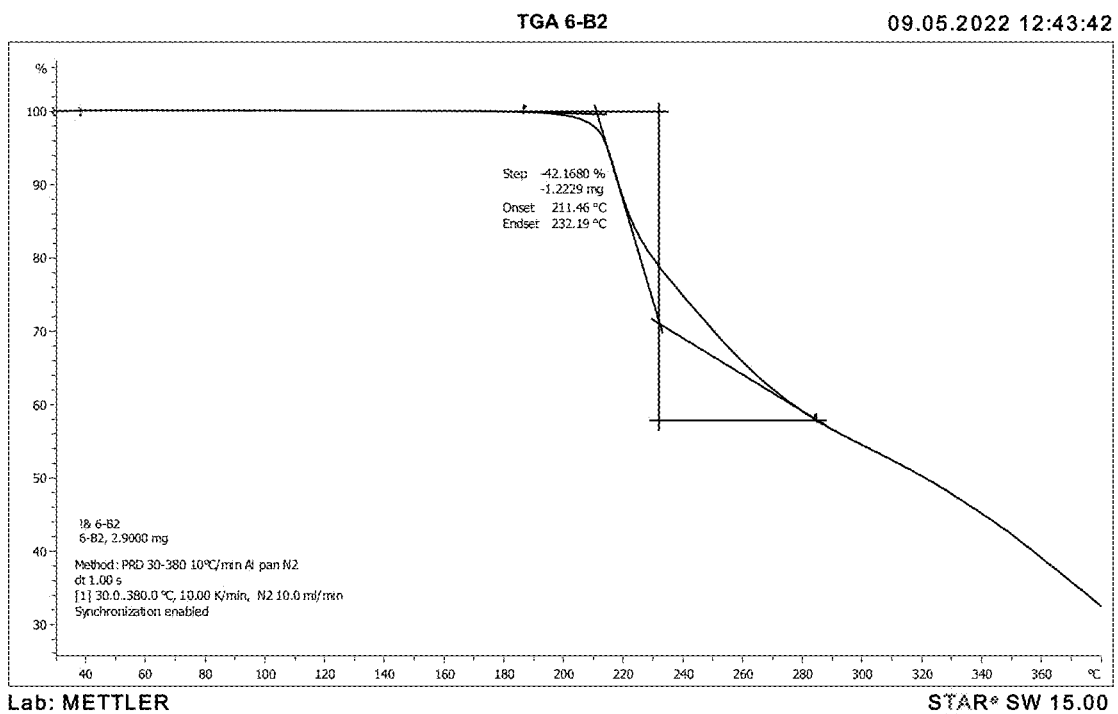

FIG. 626 depicts the TGA of tabernanthalog tartrate salt; 6-B2 (Experiment Reference 6-Sample Reference B2) (t=10 d), analysis was acquired at a ramp rate of +10° C./minute.

Figure 627:
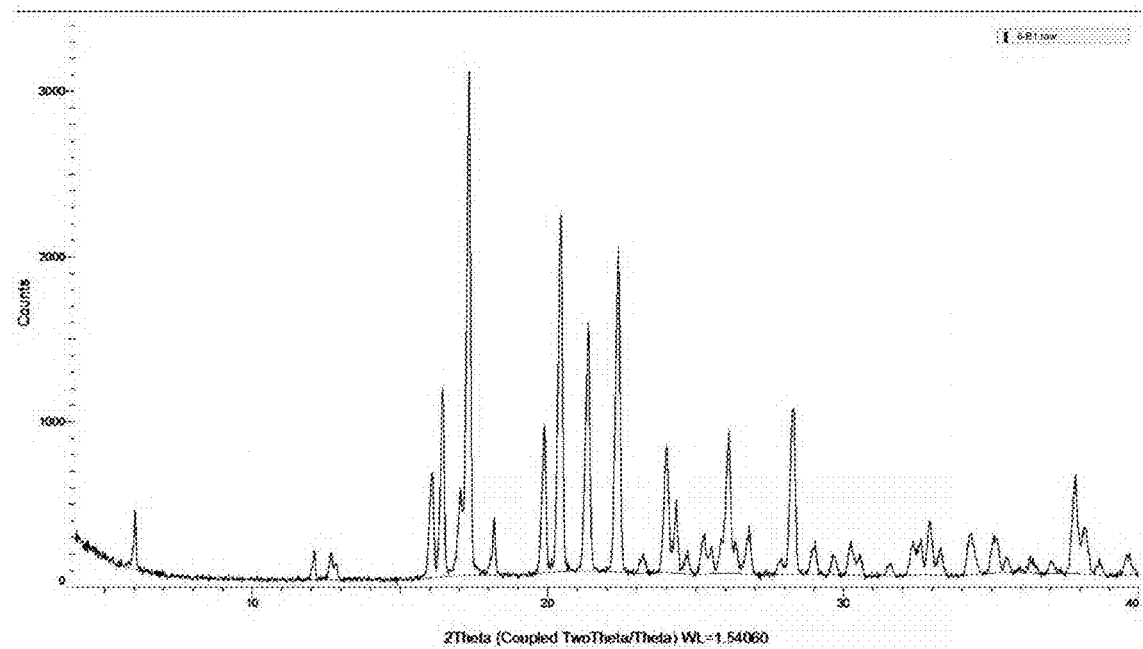

FIG. 627 depicts the XRPD of tabernanthalog tartrate salt; 6-B1 (Experiment Reference 6-Sample Reference B1) (t=5 d).

Figure 628:
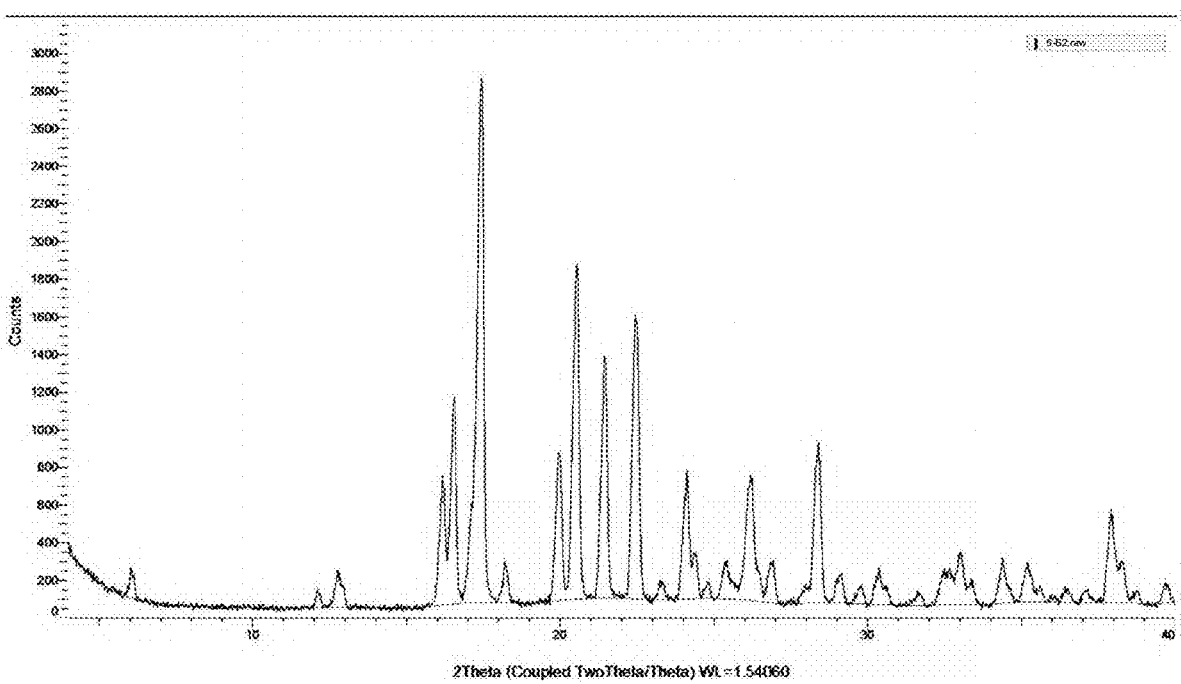

FIG. 628 depicts the XRPD of tabernanthalog tartrate salt; 6-B2 (Experiment Reference 6-Sample Reference B2) (t=10 d).

Figure 629:
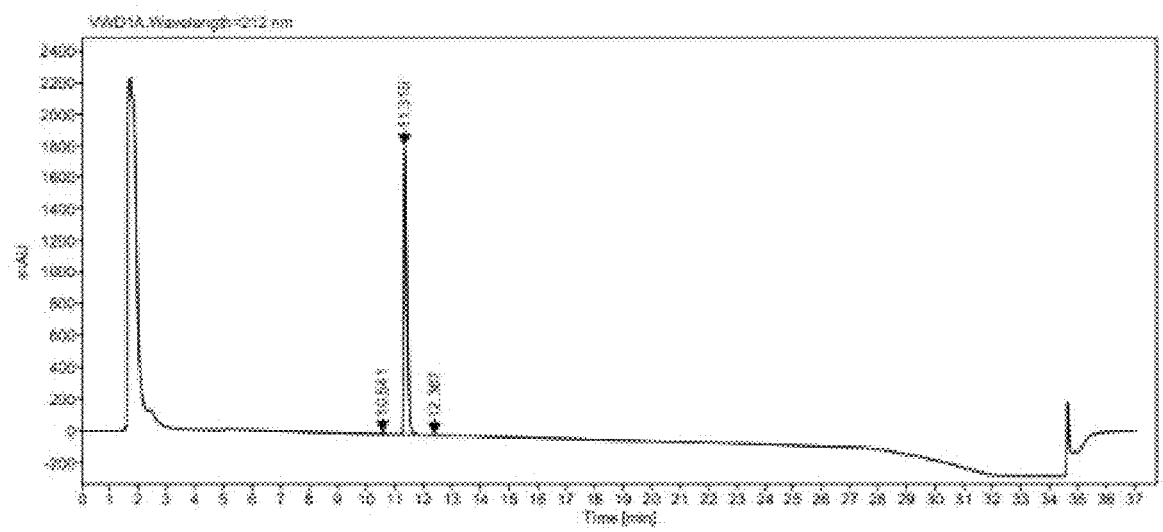

FIG. 629 depicts the HPLC of tabernanthalog tartrate salt; 6-B1 (Experiment Reference 6-Sample Reference B1) (t=5 d).

Figure 630:
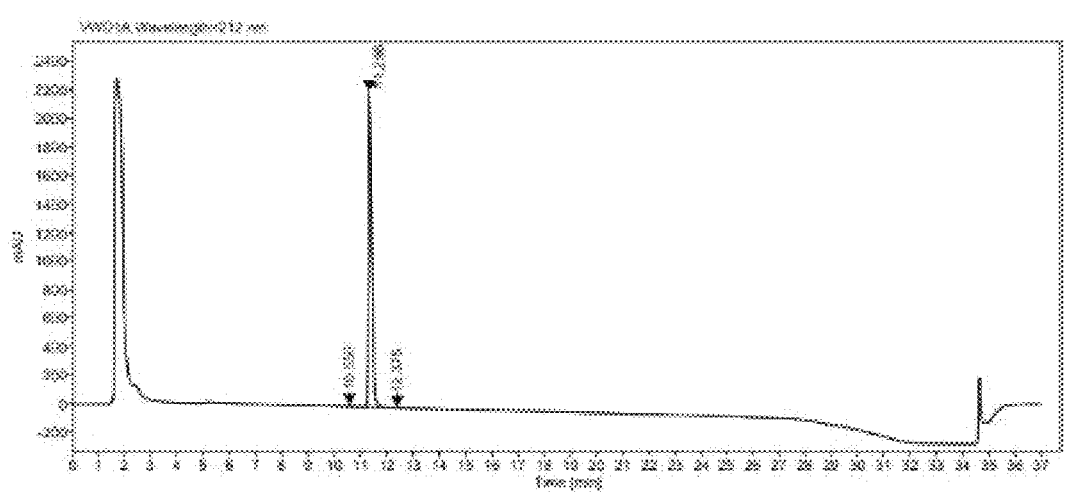

FIG. 630 depicts the HPLC of tabernanthalog tartrate salt, 6-B2 (Experiment Reference 6-Sample Reference B2) (t=10 d).

Figure 631:
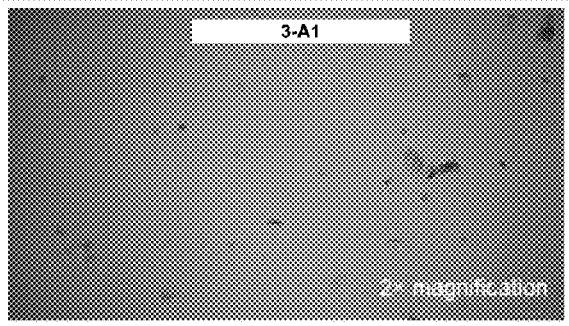

FIG. 631 depicts the PLM of tabernanthalog tartrate salt; 3-A1 (Experiment Reference 3-Sample Reference A1) (input)×2 mag, NP.

Figure 632:
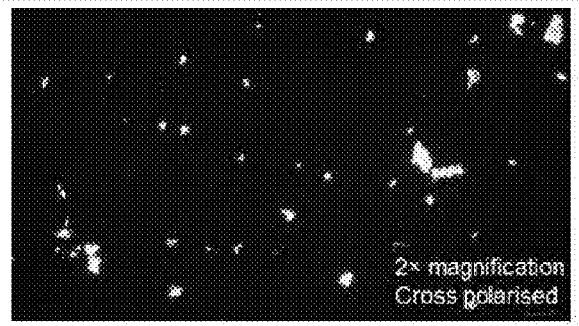

FIG. 632 depicts the PLM of tabernanthalog tartrate salt; 3-A1 (Experiment Reference 3-Sample Reference A1) (input)×2 mag, CP.

Figure 633:
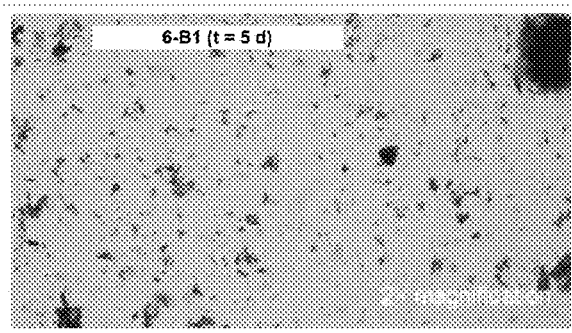

FIG. 633 depicts the PLM of tabernanthalog tartrate salt; 6-B1 (Experiment Reference 6-Sample Reference B1) (t=5 d)×5 mag, NP.

Figure 634:
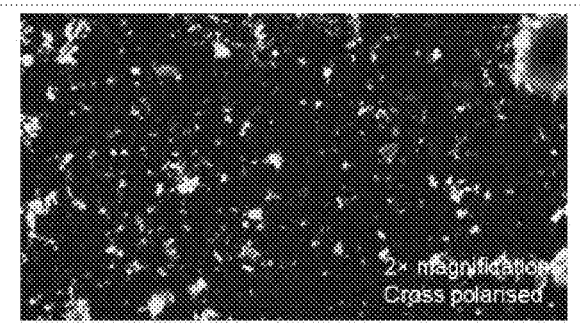

FIG. 634 depicts the PLM of tabernanthalog tartrate salt; 6-B1 (Experiment Reference 6-Sample Reference B1) (t=5 d)×5 mag, CP.

Figure 635:
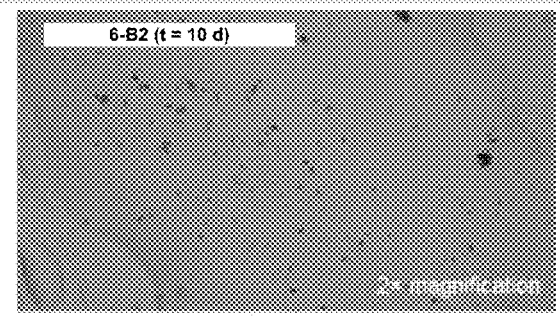

FIG. 635 depicts the PLM of tabernanthalog tartrate salt; 6-B2 (Experiment Reference 6-Sample Reference B2) (t=10 d)×5 mag, NP.

Figure 636:
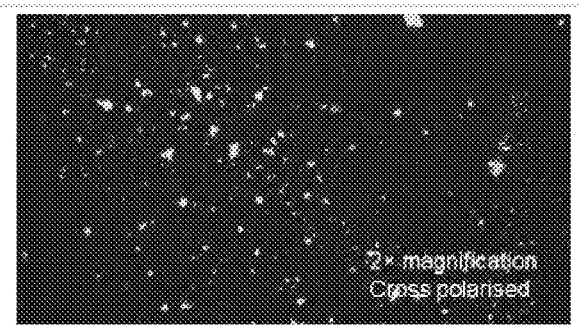

FIG. 636 depicts the PLM of tabernanthalog tartrate salt; 6-B2 (Experiment Reference 6-Sample Reference B2) (t=10 d)×5 mag, CP.

Figure 637:
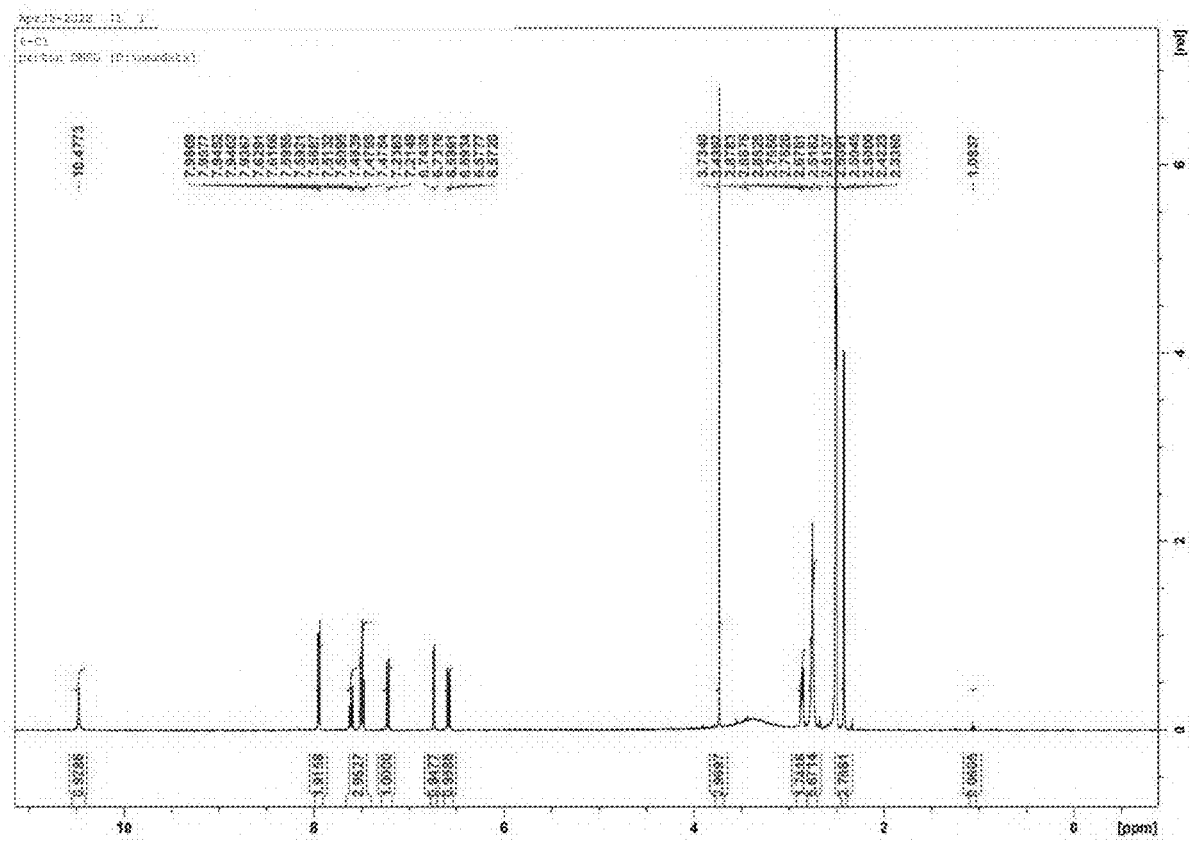

FIG. 637 depicts the $^1$H NMR of tabernanthalog benzoate salt; 6-C1 (Experiment Reference 6-Sample Reference C1) (t=5 d), analysis was acquired in DMSO-d6 and calibrated to the non-deuterated solvent residual at 2.50 ppm. 1.0 mol of API to 1.0 mol of benzoic acid. Ethanol content 0.3% w/w.

Figure 638:
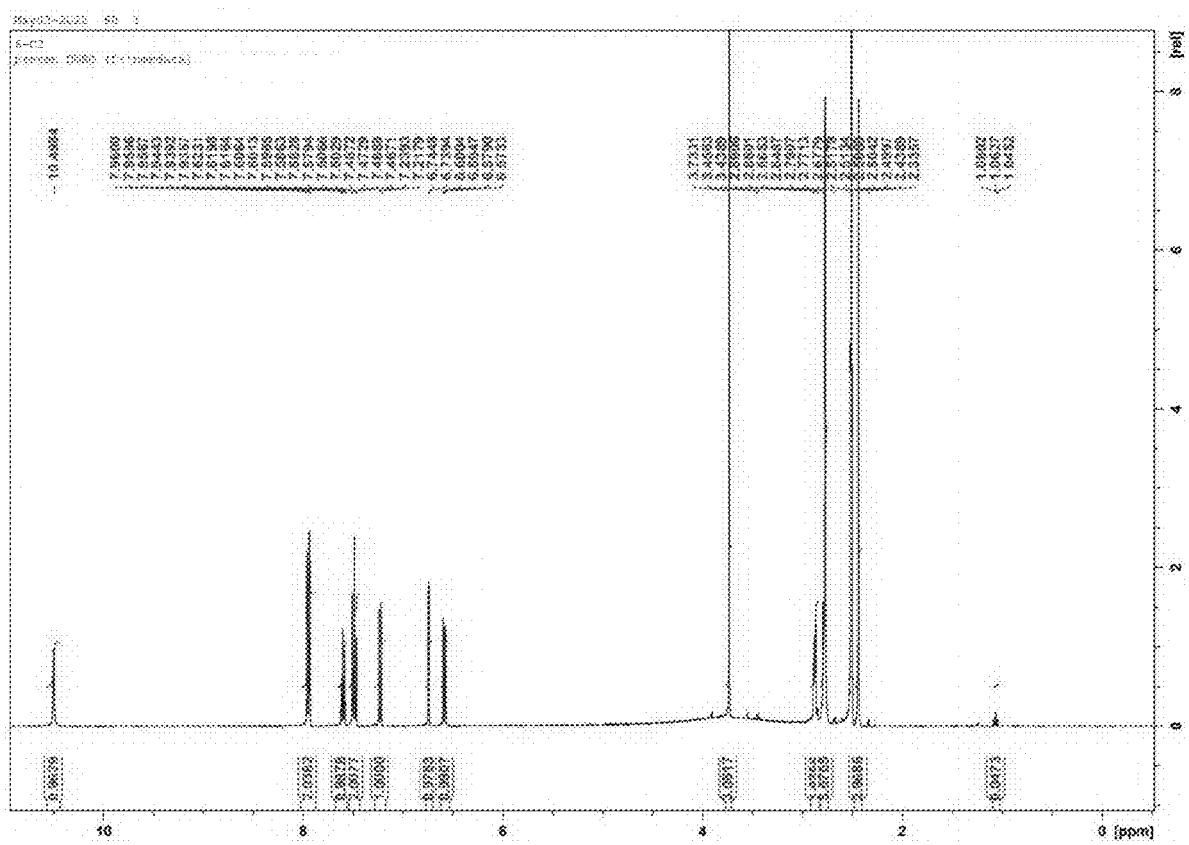

FIG. 638 depicts the $^1$H NMR of tabernanthalog benzoate salt; 6-C2 (Experiment Reference 6-Sample Reference C2) (t=10 d), analysis was acquired in DMSO-d6 and calibrated to the non-deuterated solvent residual at 2.50 ppm. 1.0 mol of API to 1.0 mol of benzoic acid. Ethanol content 0.2% w/w.

Figure 639:
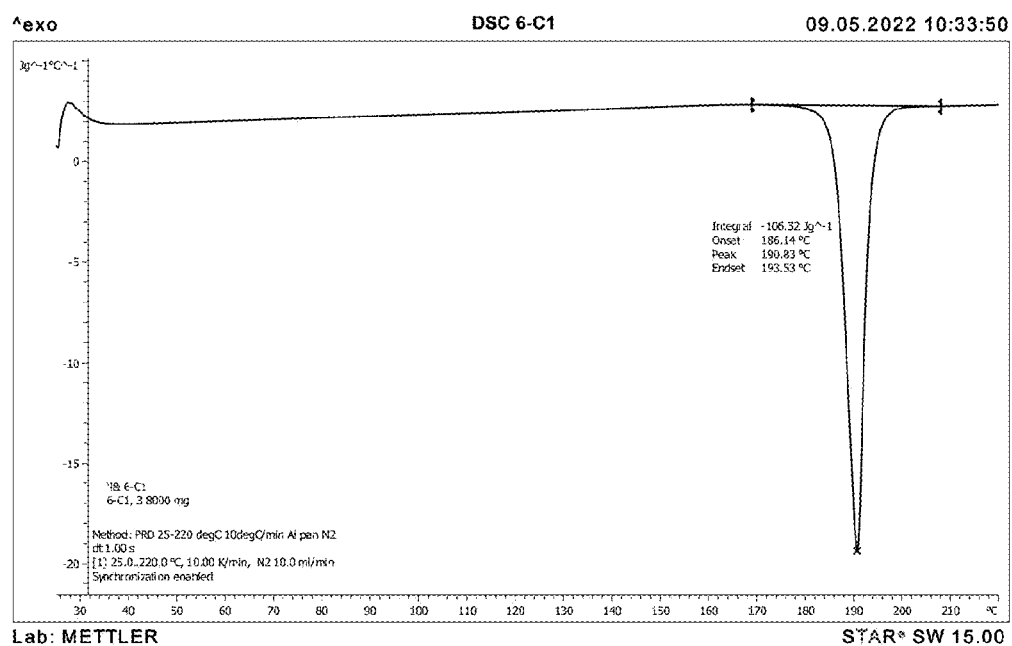

FIG. 639 depicts the DSC profile of tabernanthalog benzoate salt; 6-C1 (Experiment Reference 6-Sample Reference C1) (t=5 d), analysis was acquired at a ramp rate of +10° C./minute.

Figure 640:
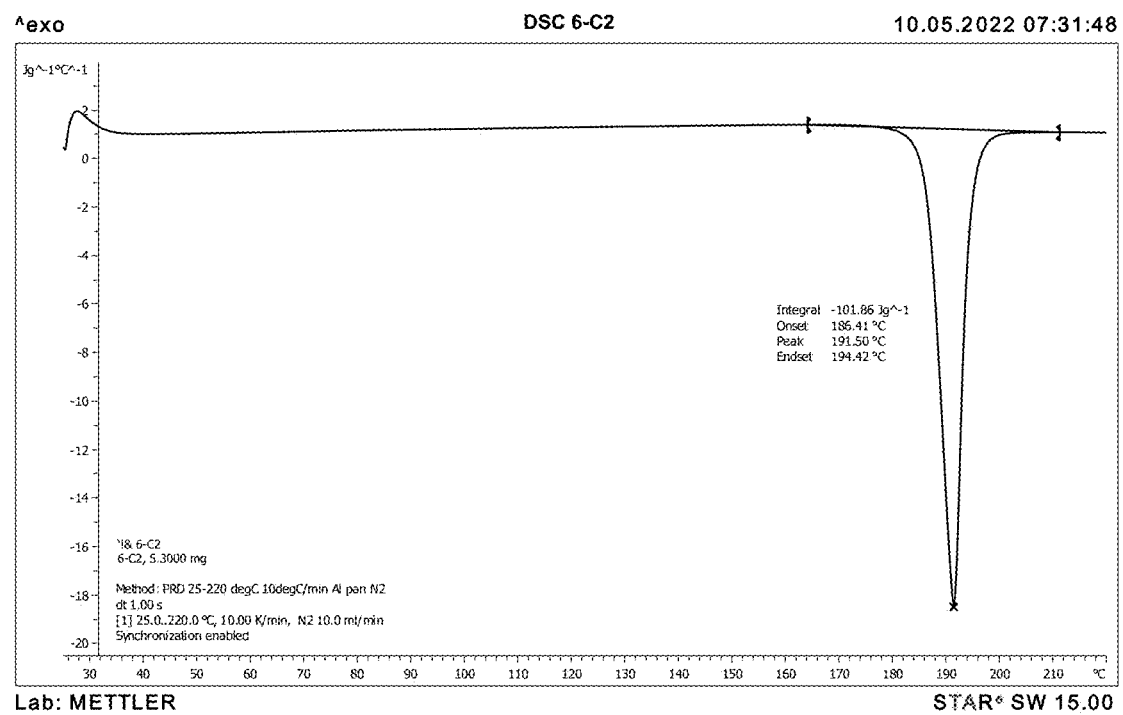

FIG. 640 depicts the DSC profile of tabernanthalog benzoate salt; 6-C2 (Experiment Reference 6-Sample Reference C2) (t=10 d), analysis was acquired at a ramp rate of +10° C./minute.

Figure 641:
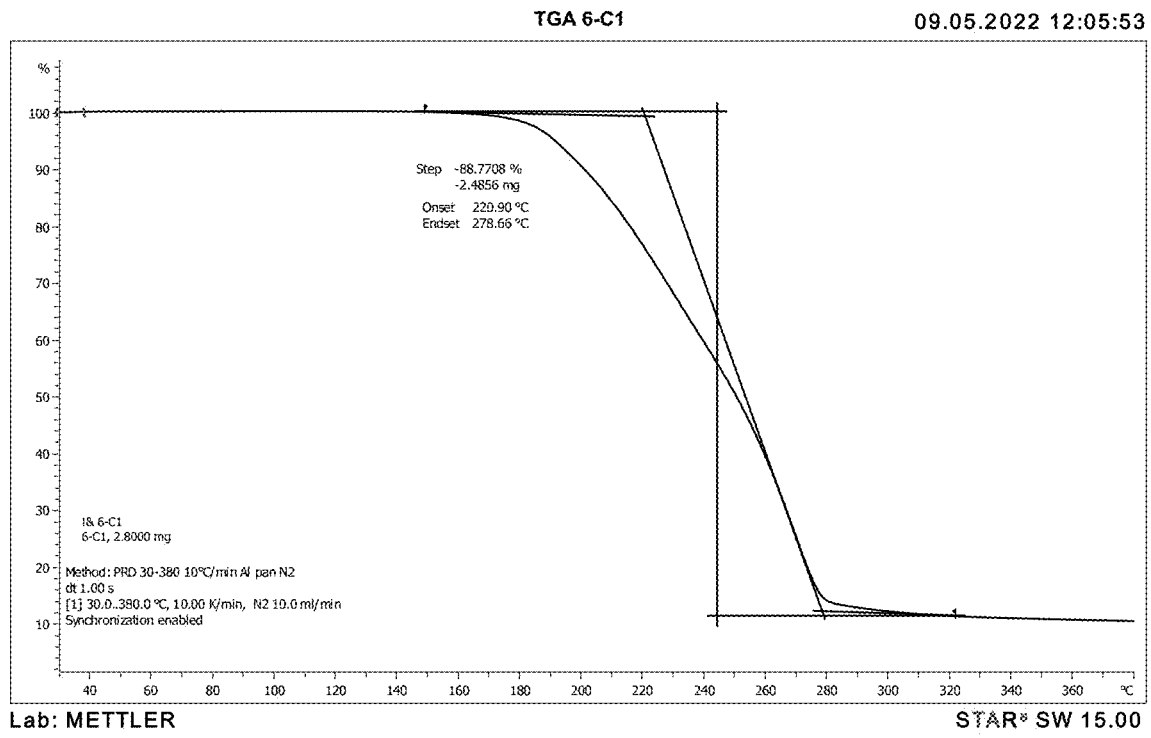

FIG. 641 depicts the TGA of tabernanthalog benzoate salt; 6-C1 (Experiment Reference 6-Sample Reference C1) (t=5 d), analysis was acquired at a ramp rate of +10° C./minute.

Figure 642:
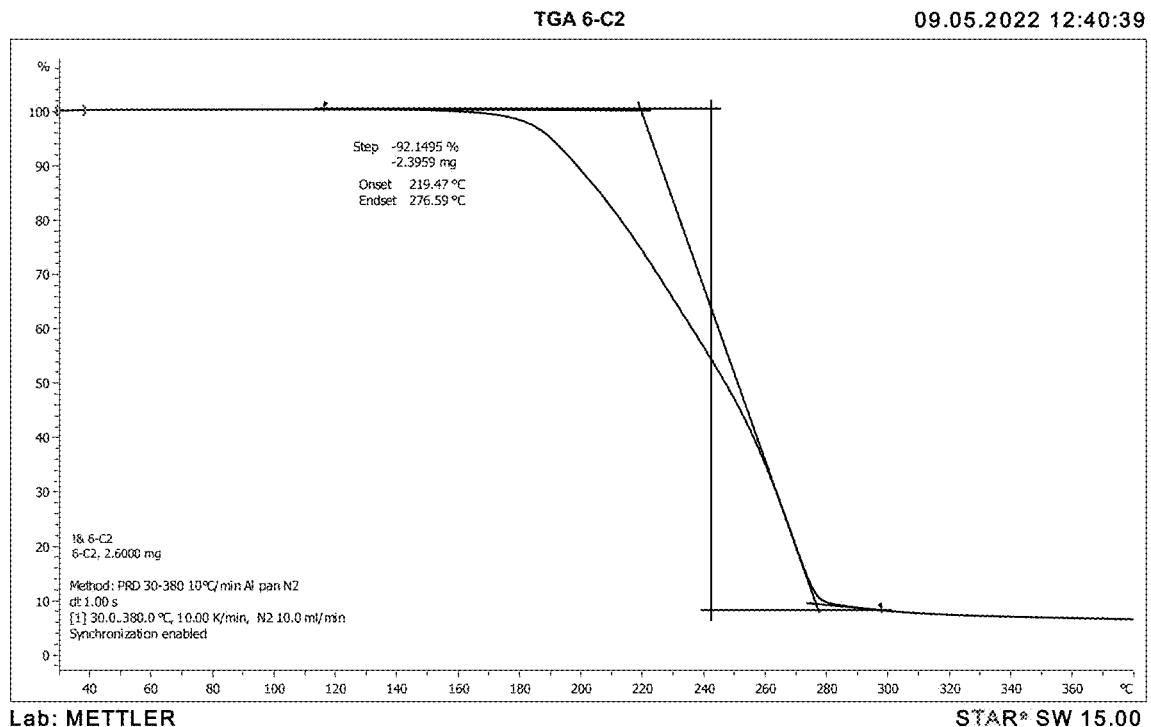

FIG. 642 depicts the TGA of tabernanthalog benzoate salt; 6-C2 (Experiment Reference 6-Sample Reference C2) (t=10 d), analysis was acquired at a ramp rate of +10° C./minute.

Figure 643:
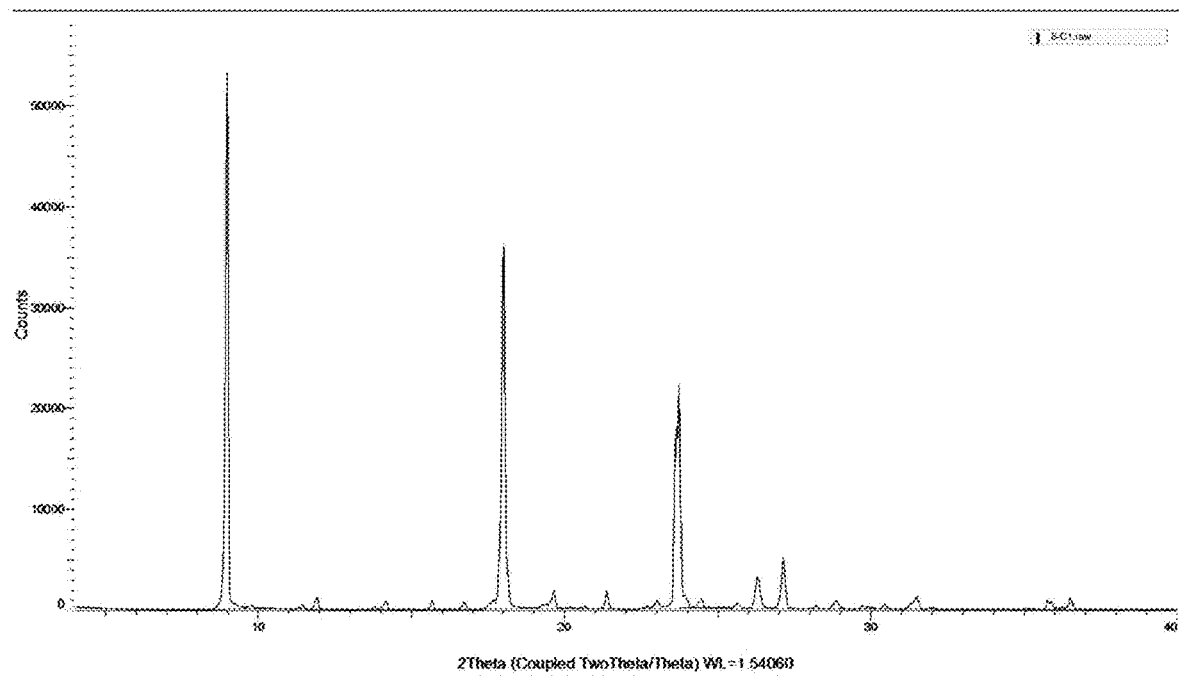

FIG. 643 depicts the XRPD of tabernanthalog benzoate salt; 6-C1 (Experiment Reference 6-Sample Reference C1) (t=5 d).

Figure 644:
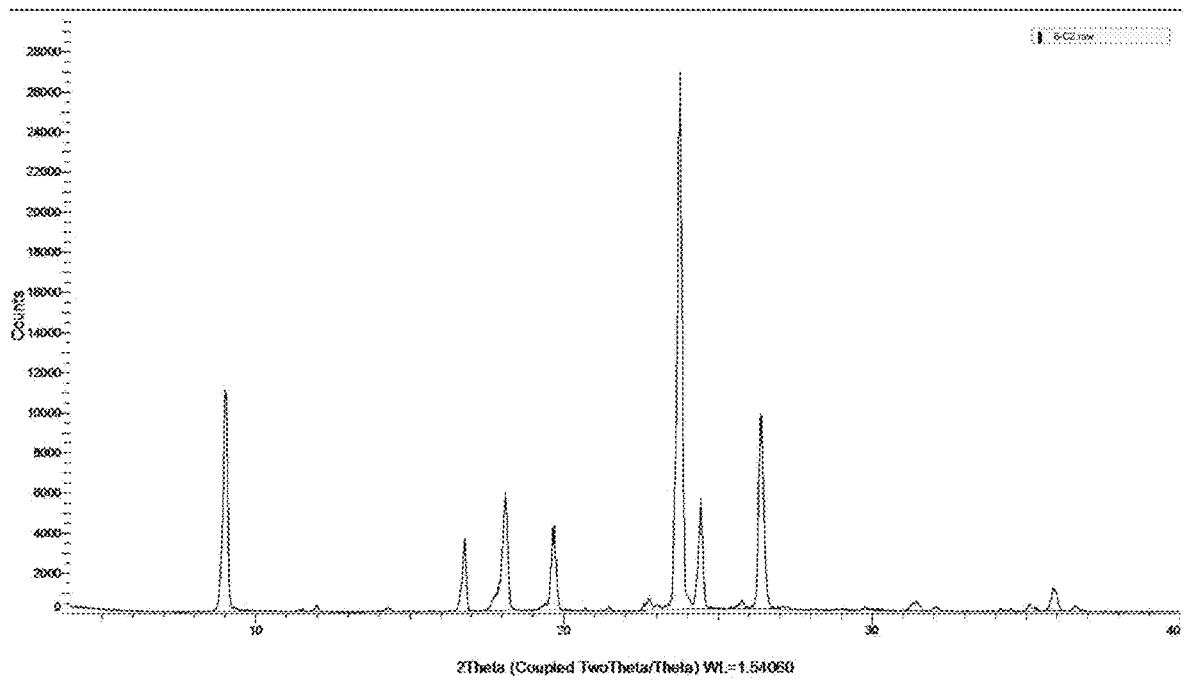

FIG. 644 depicts the XRPD of tabernanthalog benzoate salt; 6-C2 (Experiment Reference 6-Sample Reference C2) (t=10 d).

Figure 645:
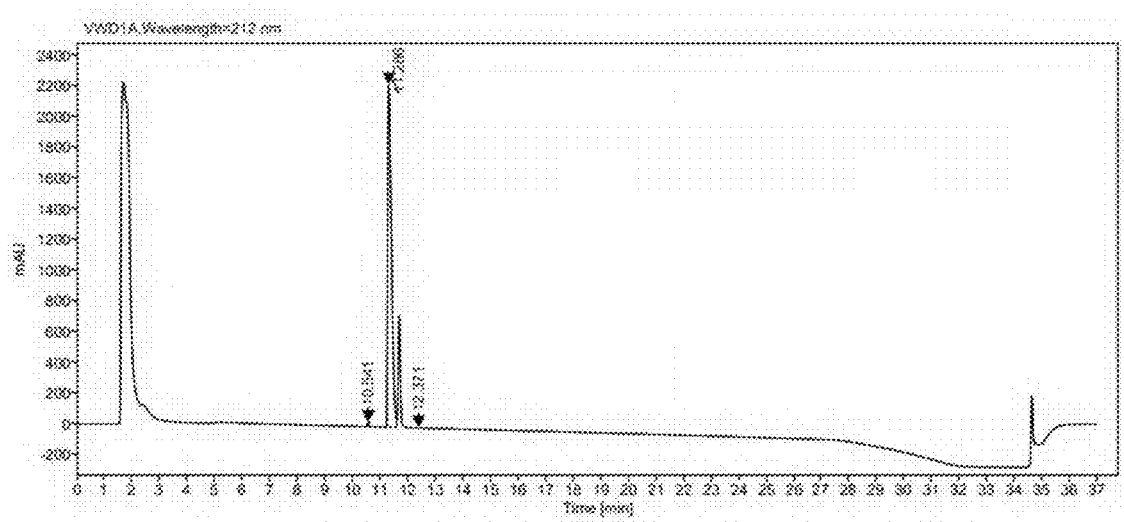

FIG. 645 depicts the HPLC of tabernanthalog benzoate salt; 6-C1 (Experiment Reference 6-Sample Reference C1) (t=5 d).

Figure 646:
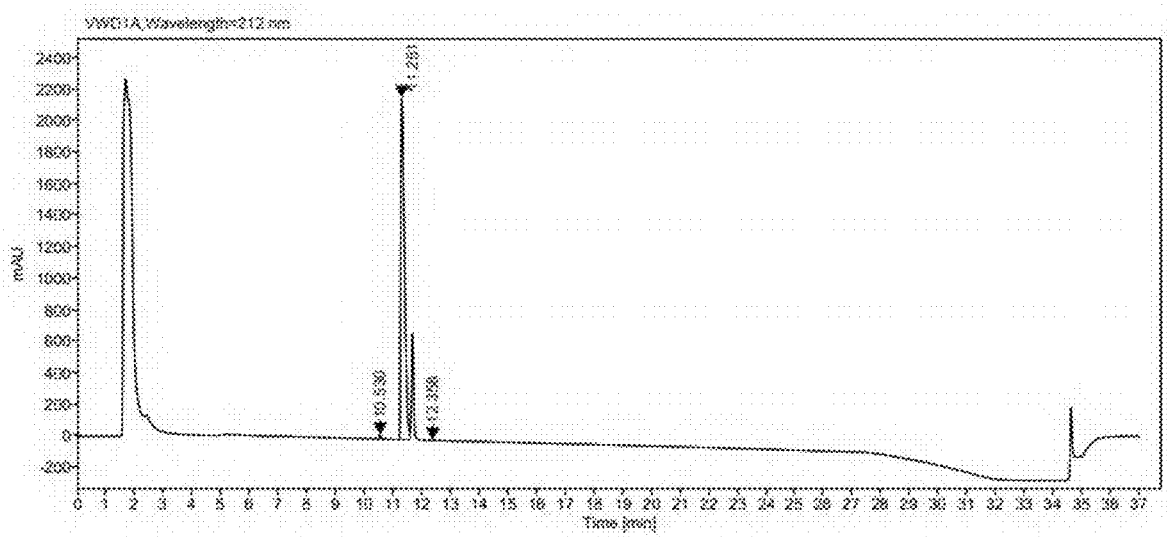

FIG. 646 depicts the HPLC of tabernanthalog benzoate salt; 6-C2 (Experiment Reference 6-Sample Reference C2) (t=10 d).

FIG. 647 depicts the PLM of tabernanthalog benzoate salt; 3-B1 (Experiment Reference 3-Sample Reference B1) (input)×2 mag, NP.

FIG. 648 depicts the PLM of tabernanthalog benzoate salt, 3-B1 (Experiment Reference 3-Sample Reference B1) (input)×2 mag, CP.

FIG. 649 depicts the PLM of tabernanthalog benzoate salt; 6-C1 (Experiment Reference 6-Sample Reference C1) (t=5 d)×2 mag, NP.

FIG. 650 depicts the PLM of tabernanthalog benzoate salt; 6-C1 (Experiment Reference 6-Sample Reference C1) (t=5 d)×2 mag, CP.

FIG. 651 depicts the PLM of tabernanthalog benzoate salt; 6-C2 (Experiment Reference 6-Sample Reference C2) (t=10 d)×2 mag, NP.

FIG. 652 depicts the PLM of tabernanthalog benzoate salt; 6-C2 (Experiment Reference 6-Sample Reference C2) (t=10 d)×2 mag, CP.

Figure 653:
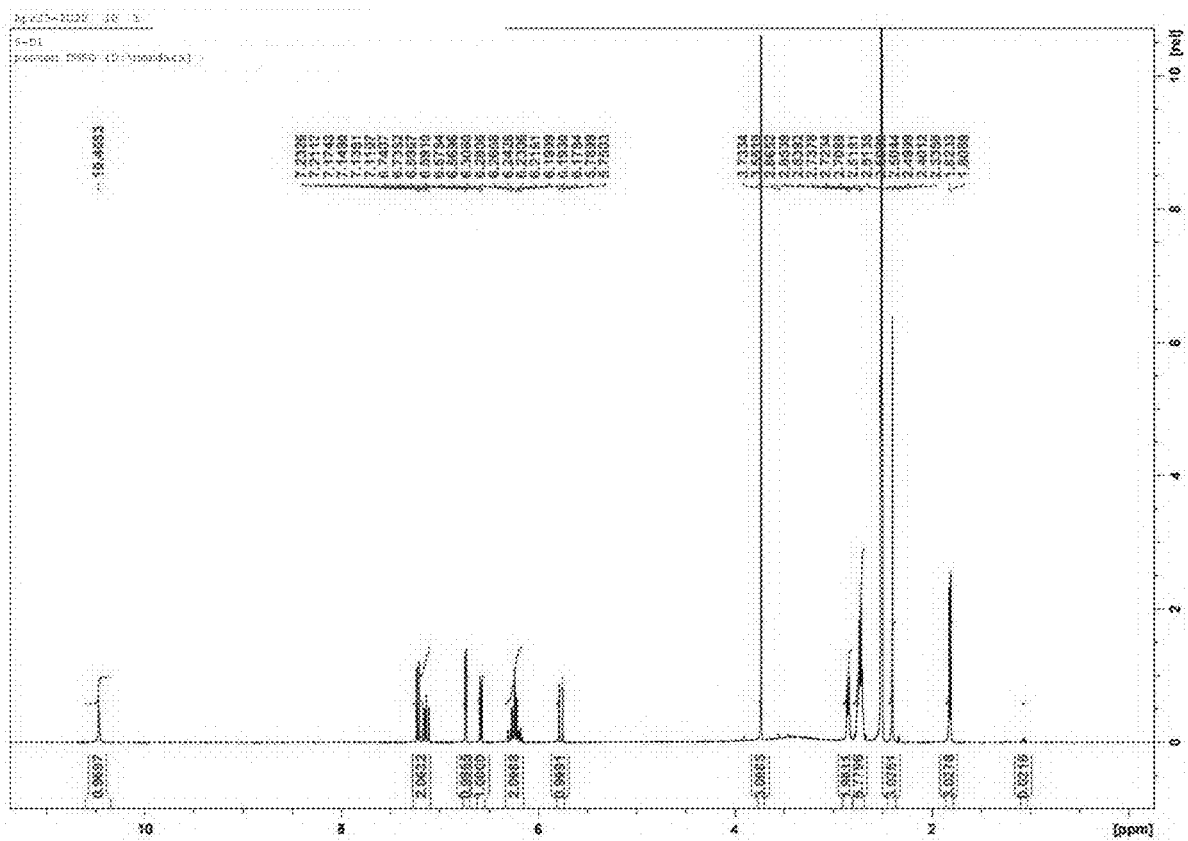

FIG. 653 depicts the $^1$H NMR of tabernanthalog sorbate salt; 6-D1 (Experiment Reference 6-Sample Reference D1) (t=5 d), analysis was acquired in DMSO-d6 and calibrated to the non-deuterated solvent residual at 2.50 ppm. 1.0 mol of API to 1.0 mol of sorbic acid. Ethanol content 0.1% w/w.

Figure 654:
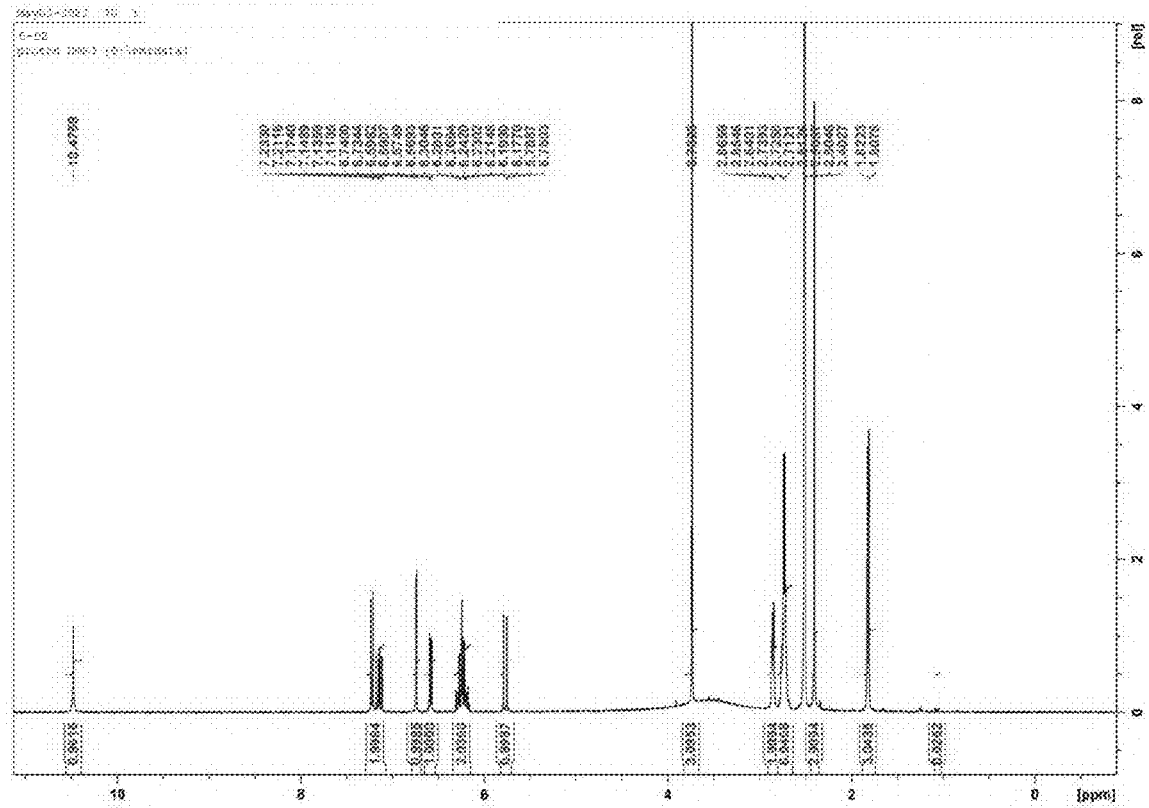

FIG. 654 depicts the $^1$H NMR of tabernanthalog sorbate salt; 6-D2 (Experiment Reference 6-Sample Reference D2) (t=10 d), analysis was acquired in DMSO-d6 and calibrated to the non-deuterated solvent residual at 2.50 ppm. 1.0 mol of API to 1.0 mol of sorbic acid. Ethanol content 0.1% w/w.

Figure 655:
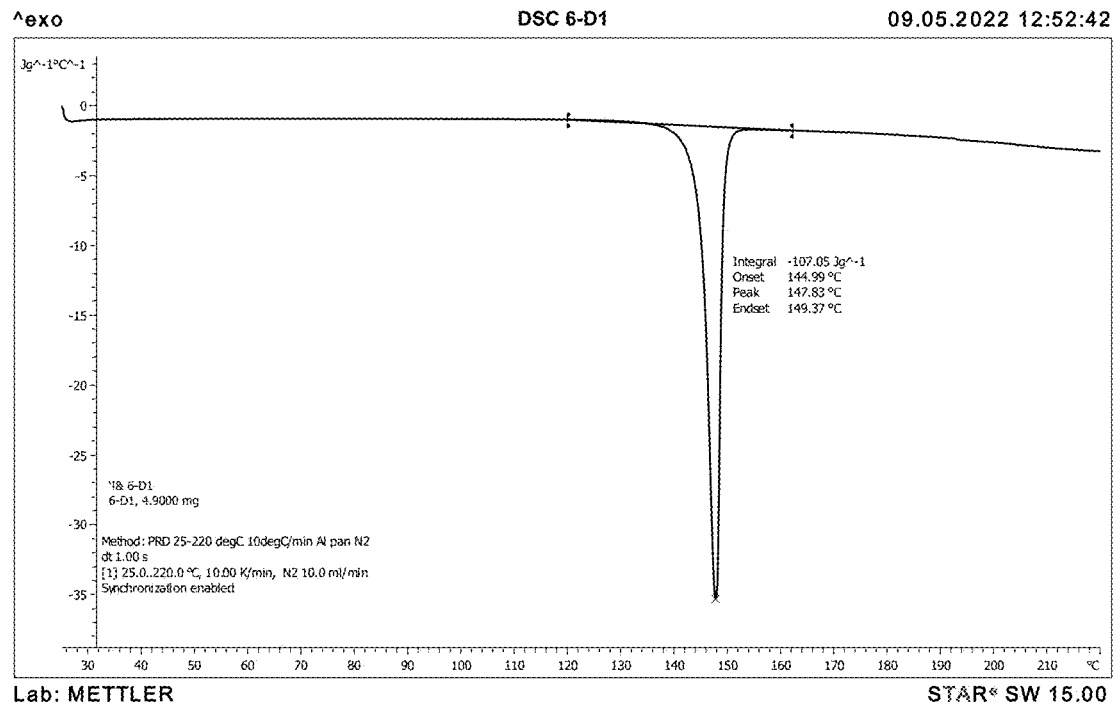

FIG. 655 depicts the DSC profile of tabernanthalog sorbate salt; 6-D1 (Experiment Reference 6-Sample Reference D1) (t=5 d), analysis was acquired at a ramp rate of +10° C./minute.

Figure 656:
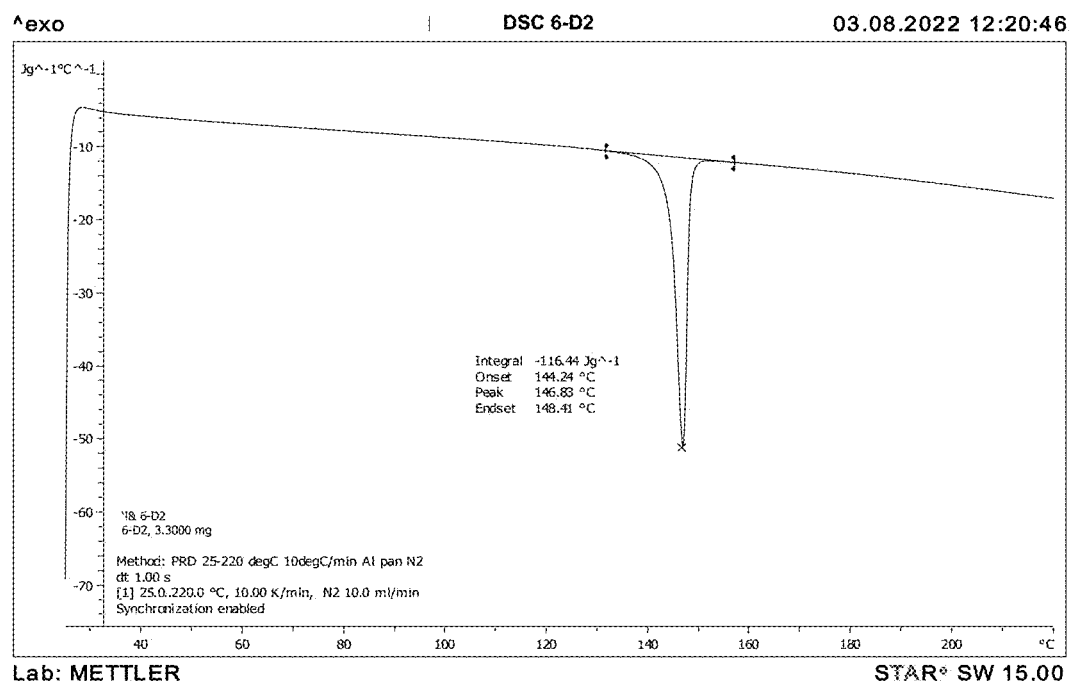

FIG. 656 depicts the DSC profile of tabernanthalog sorbate salt; 6-D2 (Experiment Reference 6-Sample Reference D2) (t=10 d), analysis was acquired at a ramp rate of +10° C./minute.

Figure 657:
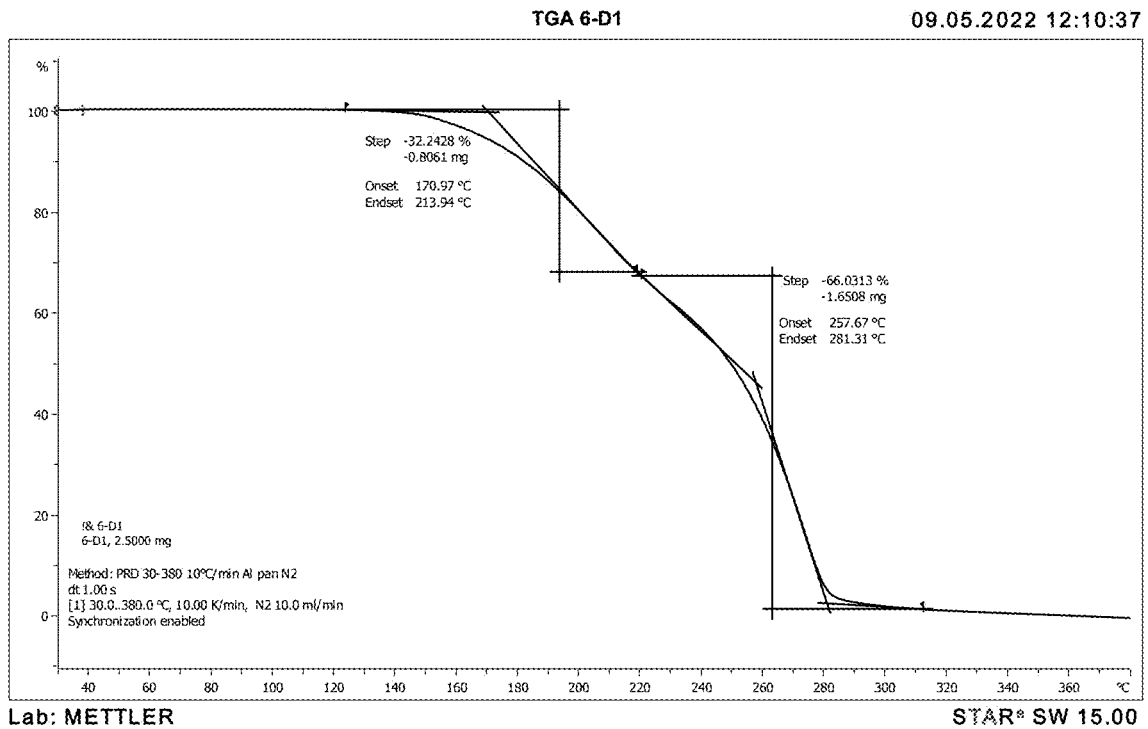

FIG. 657 depicts the TGA of tabernanthalog sorbate salt; 6-D1 (Experiment Reference 6-Sample Reference D1) (t=5 d), analysis was acquired at a ramp rate of +10° C./minute.

Figure 658:
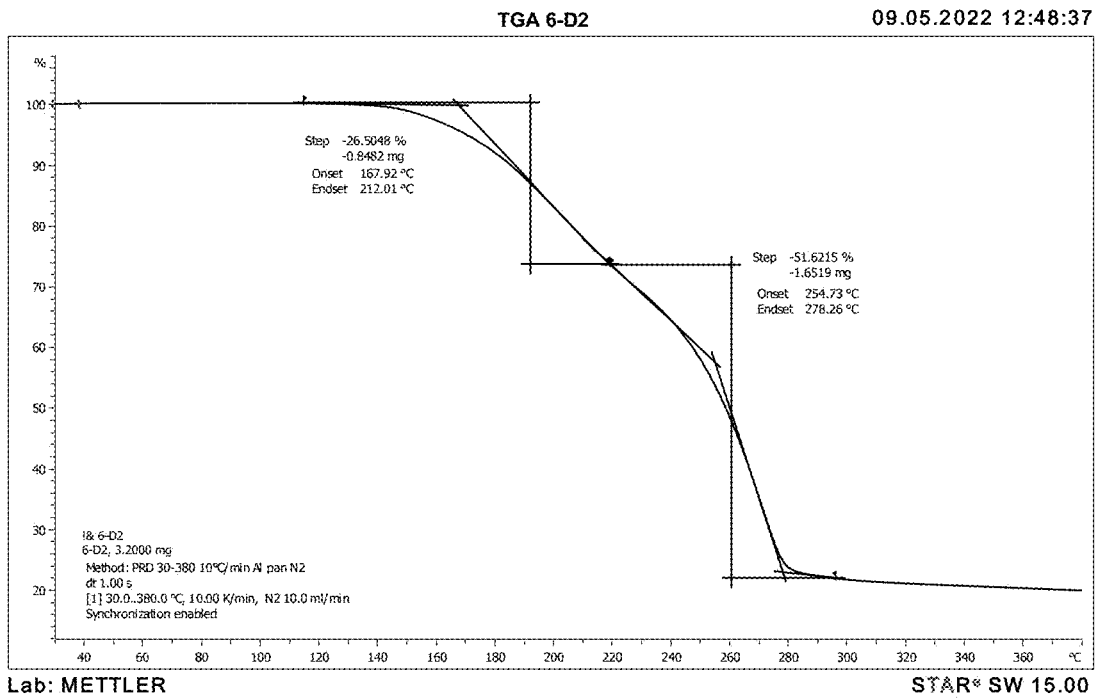

FIG. 658 depicts the TGA of tabernanthalog sorbate salt; 6-D2 (Experiment Reference 6-Sample Reference D2) (t=10 d), analysis was acquired at a ramp rate of +10° C./minute.

Figure 659:
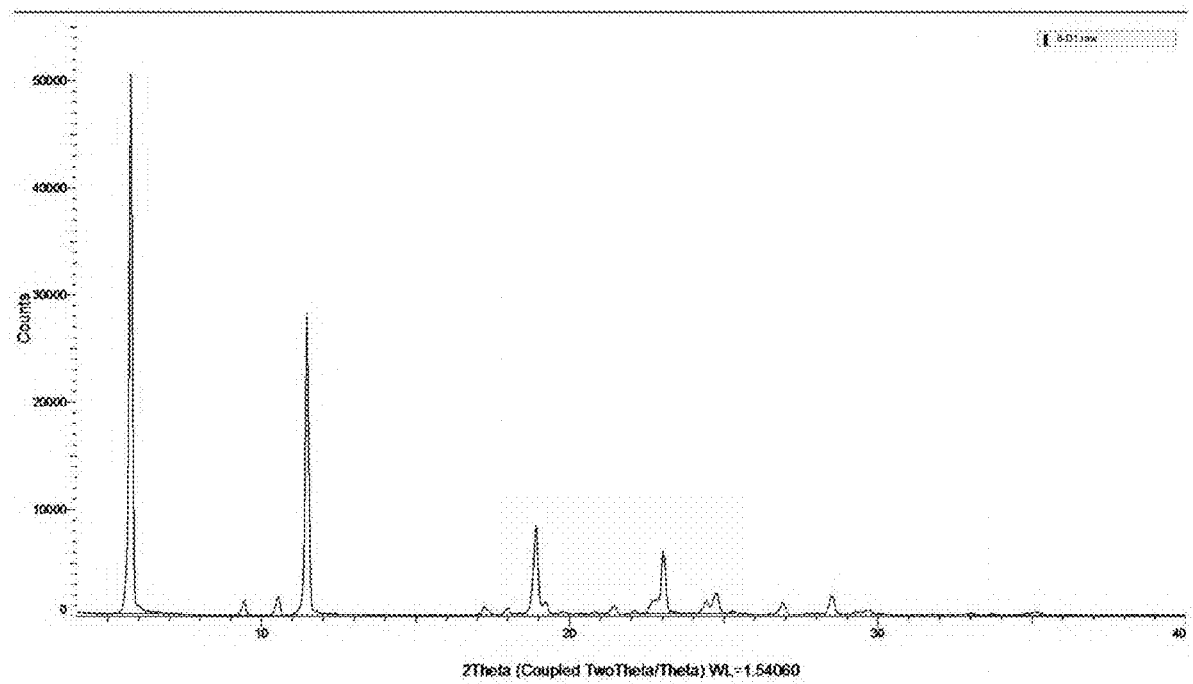

FIG. 659 depicts the XRPD of tabernanthalog sorbate salt; 6-D1 (Experiment Reference 6-Sample Reference D1) (t=5 d).

Figure 660:
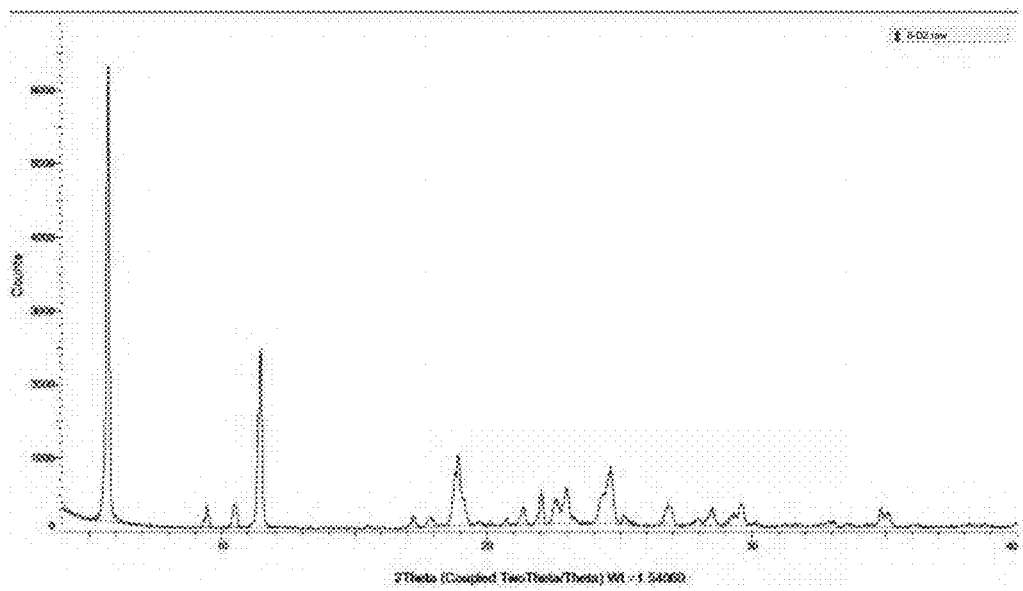

FIG. 660 depicts the XRPD of tabernanthalog sorbate salt; 6-D2 (Experiment Reference 6-Sample Reference D2) (t=10 d).

Figure 661:
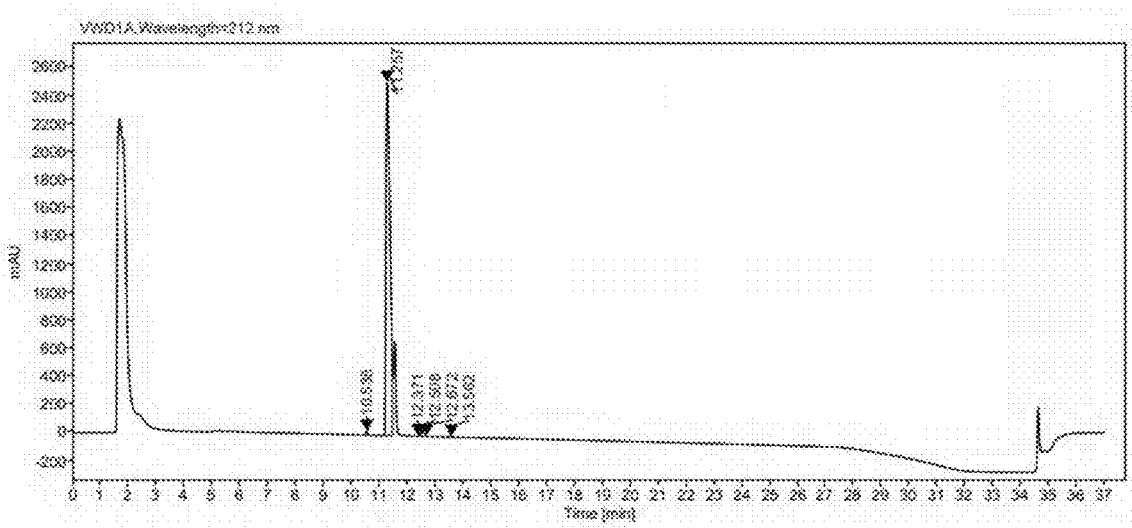

FIG. 661 depicts the HPLC of tabernanthalog sorbate salt; 6-D1 (Experiment Reference 6-Sample Reference D1) (t=5 d).

Figure 662:
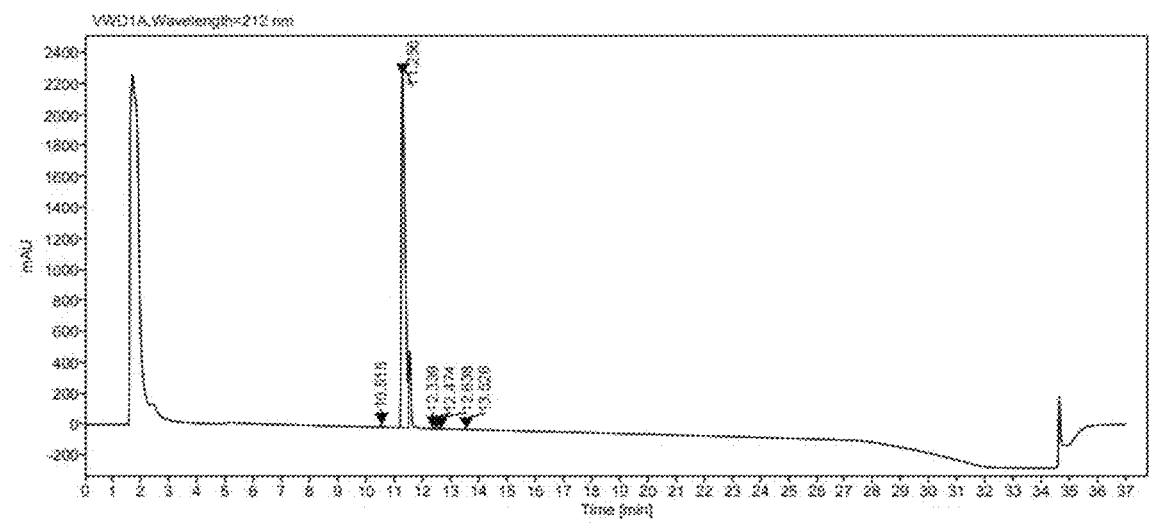

FIG. 662 depicts the HPLC of tabernanthalog sorbate salt; 6-D2 (Experiment Reference 6-Sample Reference D2) (t=10 d).

Figure 663:
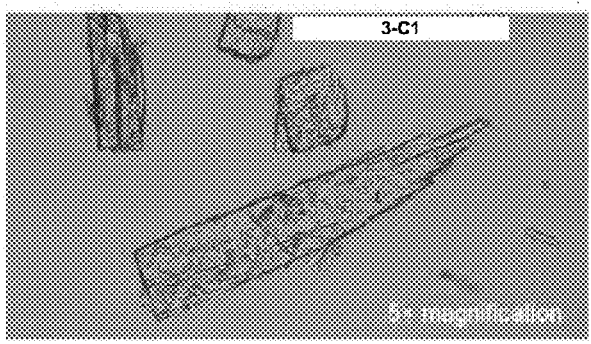

FIG. 663 depicts the PLM of tabernanthalog sorbate salt. 3-C1 (Experiment Reference 3-Sample Reference C1) (input)×5 mag, NP.

Figure 664:
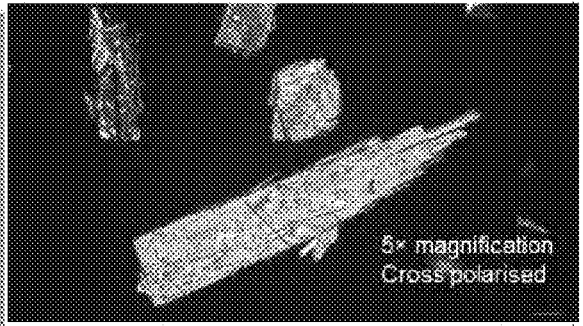

FIG. 664 depicts the PLM of tabernanthalog sorbate salt; 3-C1 (Experiment Reference 3-Sample Reference C1) (input)×5 mag, CP.

Figure 665:
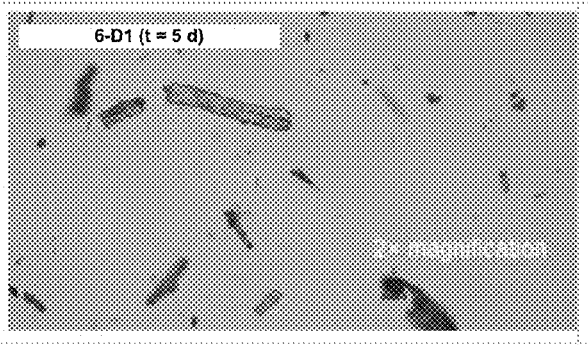

FIG. 665 depicts the PLM of tabernanthalog sorbate salt; 6-D1 (Experiment Reference 6-Sample Reference D1) (t=5 d)×2 mag, NP.

Figure 666:
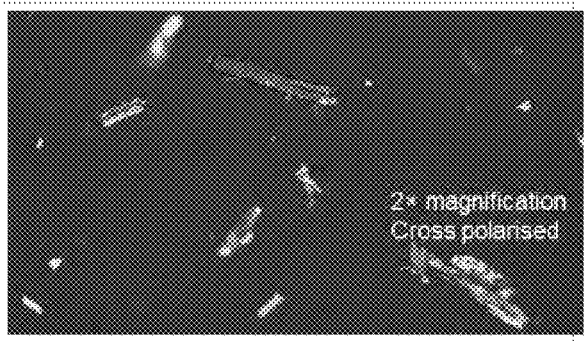

FIG. 666 depicts the PLM of tabernanthalog sorbate salt; 6-D1 (Experiment Reference 6-Sample Reference D1) (t=5 d)×2 mag, CP.

Figure 667:
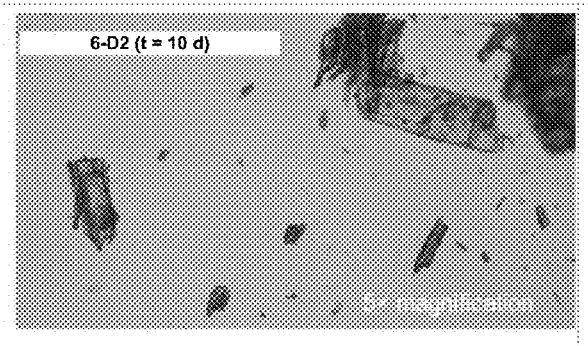

FIG. 667 depicts the PLM of tabernanthalog sorbate salt; 6-D2 (Experiment Reference 6-Sample Reference D2) (t=10 d)×5 mag, NP.

Figure 668:
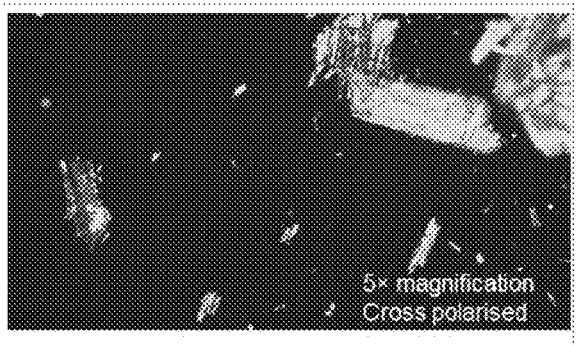

FIG. 668 depicts the PLM of tabernanthalog sorbate salt, 6-D2 (Experiment Reference 6-Sample Reference D2) (t=10 d)×5 mag, CP.

Figure 669:
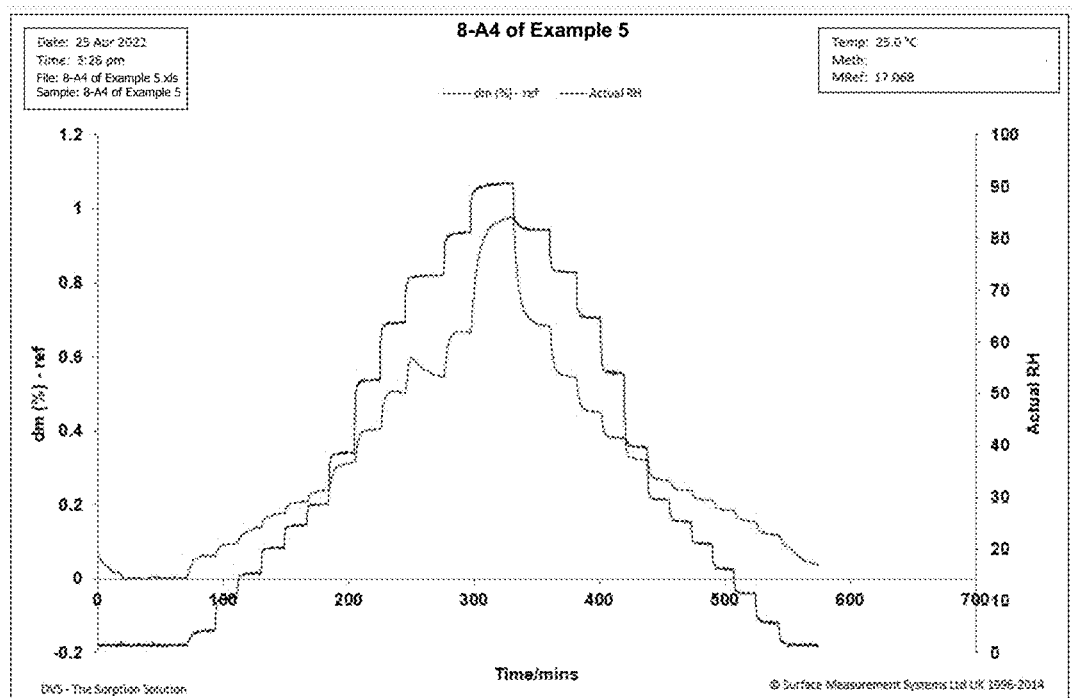

FIG. 669 depicts the DVS of tabernanthalog monofumarate salt; 8-A4 of Example 5 ((Experiment Reference 8-Sample Reference A4 of Example 5), kinetic plot and isotherm analysis report.

Figure 670:

FIG. 670 depicts the DVS of tabernanthalog monofumarate salt; 8-A4 of Example 5 ((Experiment Reference 8-Sample Reference A4 of Example 5), isothermal plot.

Figure 671:
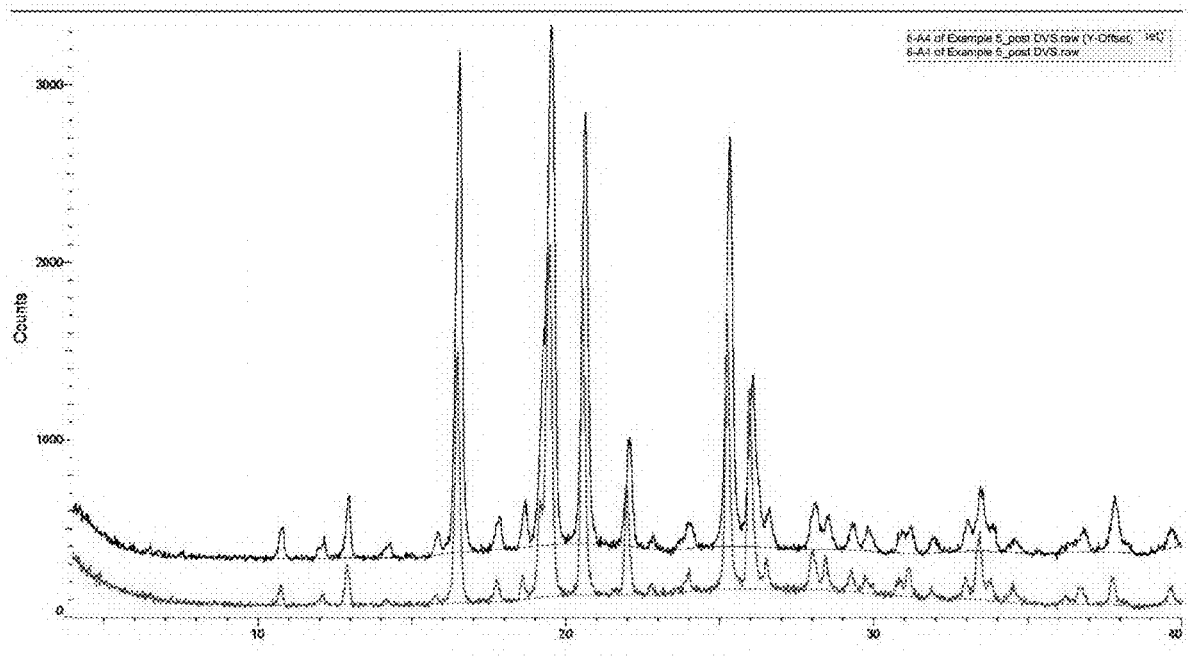

FIG. 671 depicts the XRPD of tabernanthalog monofumarate salt; 8-A4 of Example 5 (Experiment Reference 8-Sample Reference A4 of Example 5) (post DVS 0 to 90% RH, top diffractogram), compared with the input sample tabernanthalog monofumarate salt; 8-A4 of Example 5 (bottom diffractogram).

Figure 672:
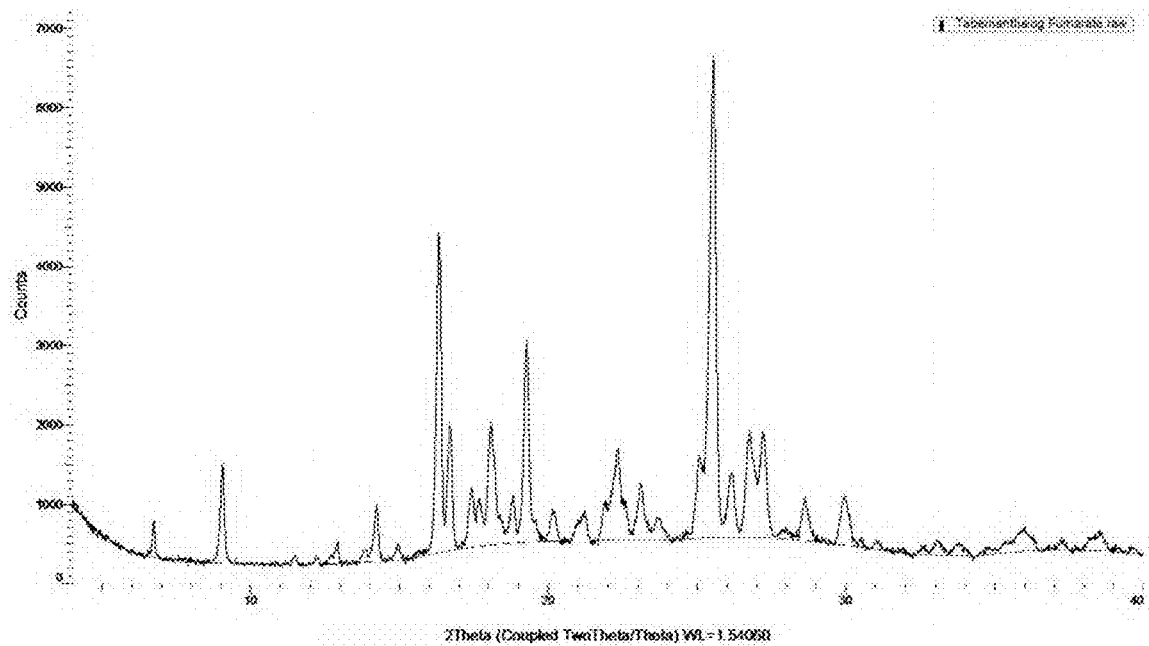

FIG. 672 depicts the XRPD of the as-received fumarate material (ref. batch: Sample Reference 1). It was characterized as Pattern #1.

Figure 673:
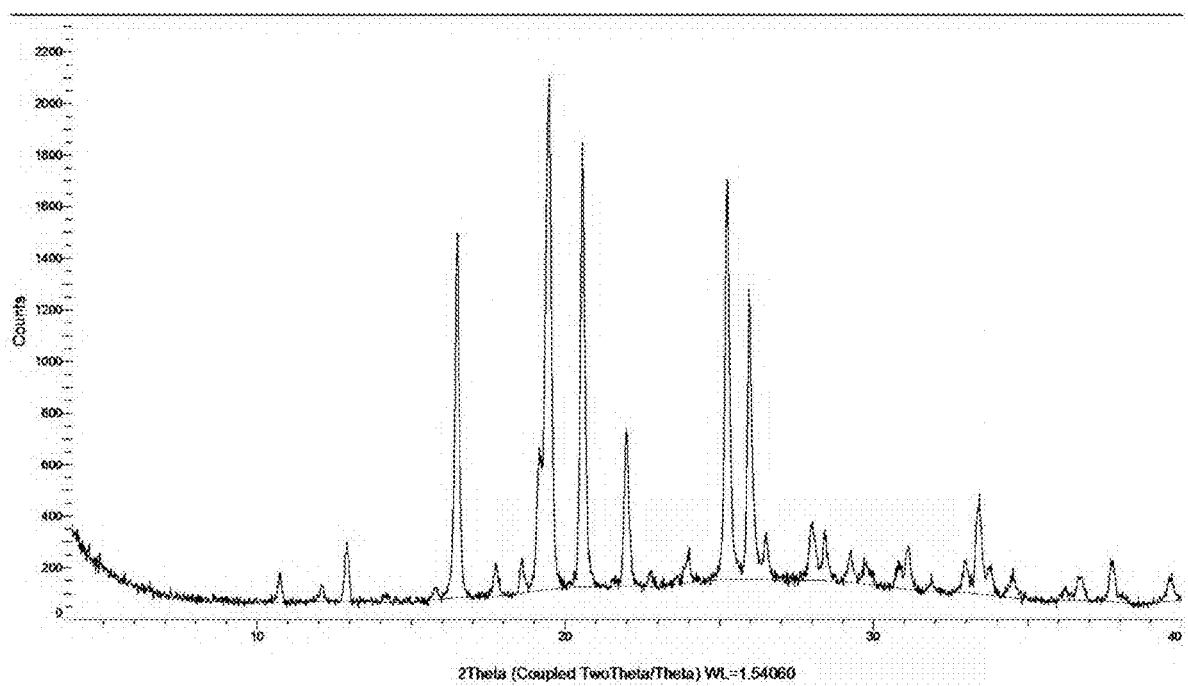

FIG. 673 depicts the XRPD profile of Pattern #6a, Form A.

Figure 674:
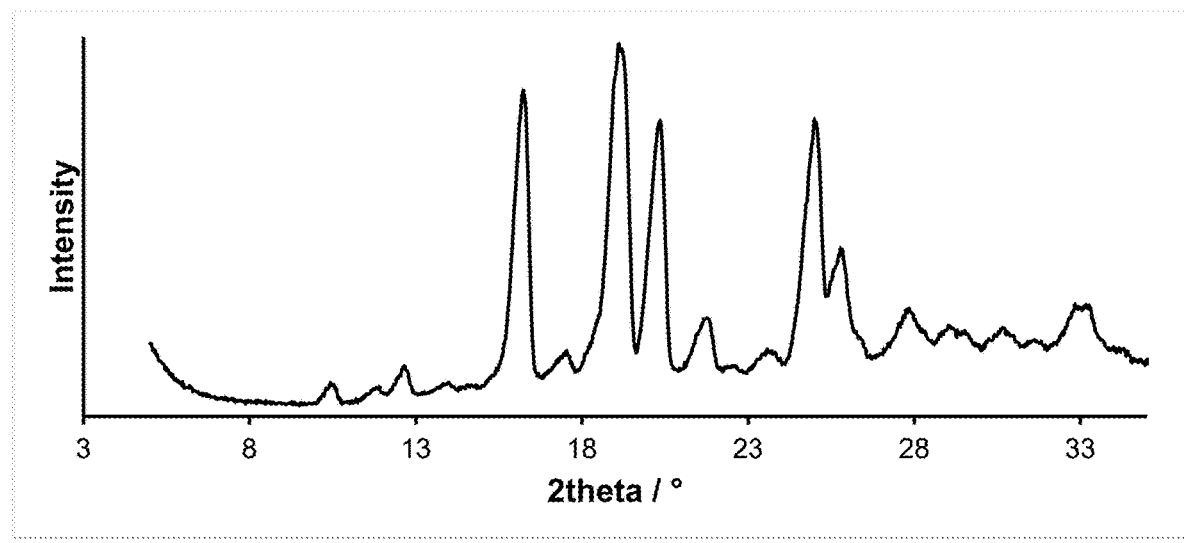

FIG. 674 depicts the XRPD of the tabernanthalog fumarate sample prepared.

Figure 675:
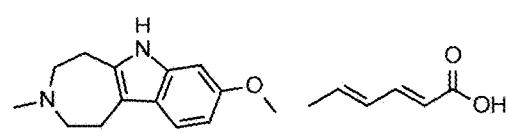

FIG. 675 depicts the tabernanthalog sorbate salt.

Figure 676:
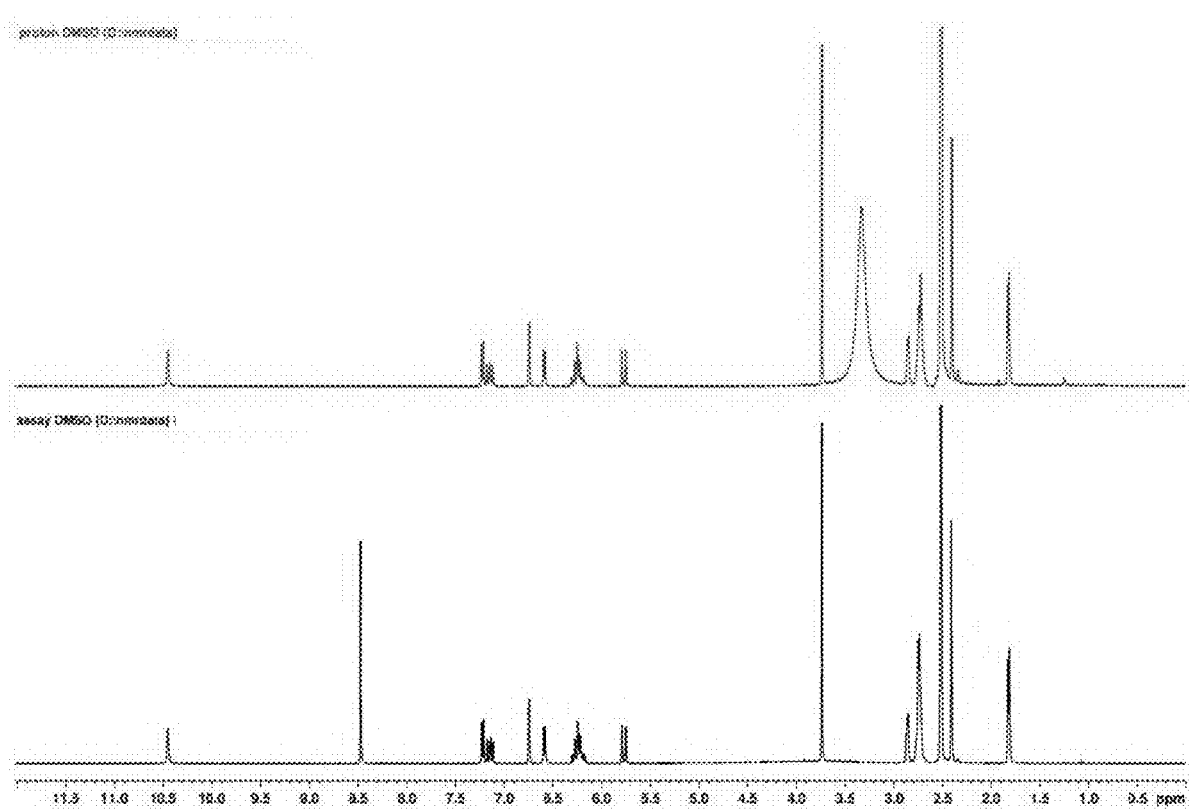

FIG. 676 depicts the overlaid of $^1$H NMR spectra of Experiment 2-Sample M2 (MEK n.d., top) and Experiment 1-Sample A2 (Form A, assay, bottom). DMSO-d$_6$ used as deuterated solvent.

TCNB used in Experiment 1-Sample A2 as internal standard.

Figure 677:
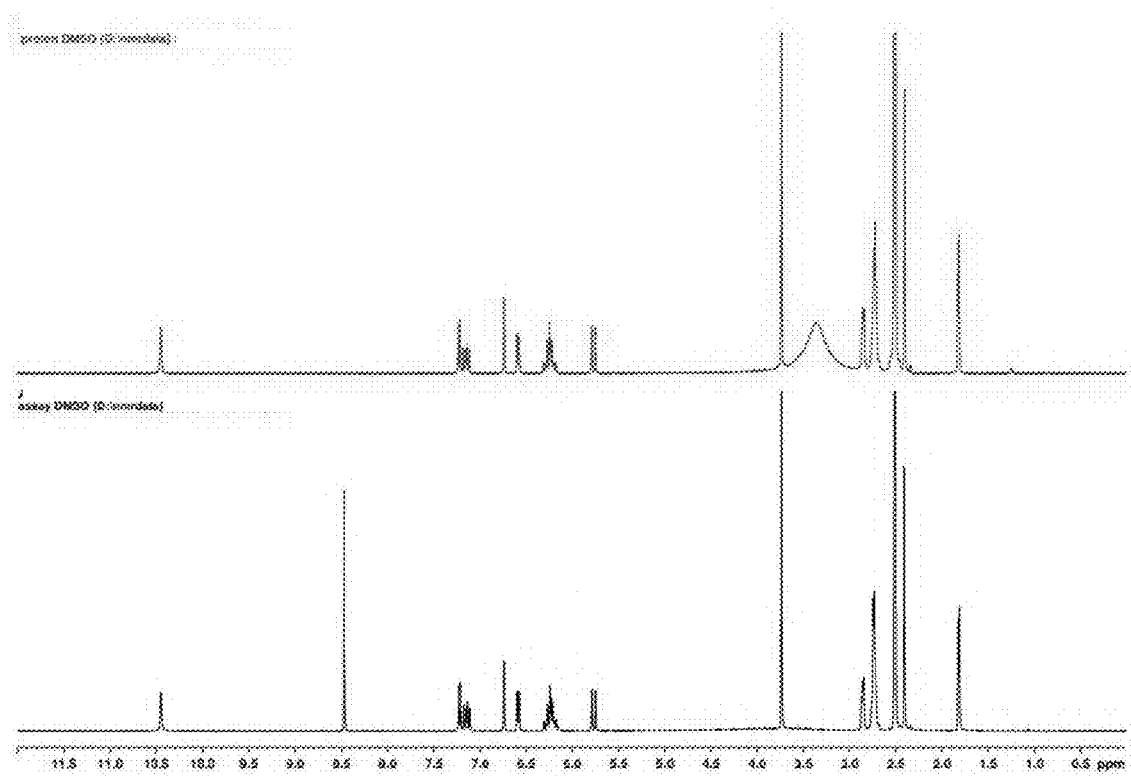

FIG. 677 depicts the overlaid of $^1$H NMR spectra of Experiment 2-Sample O2 (nitromethane n.d., top) and Experiment 1-Sample A2 (Form A, assay, bottom). DMSO-d$_6$ used as deuterated solvent. TCNB used in Experiment 1-Sample A2 as internal standard.

Figure 678:
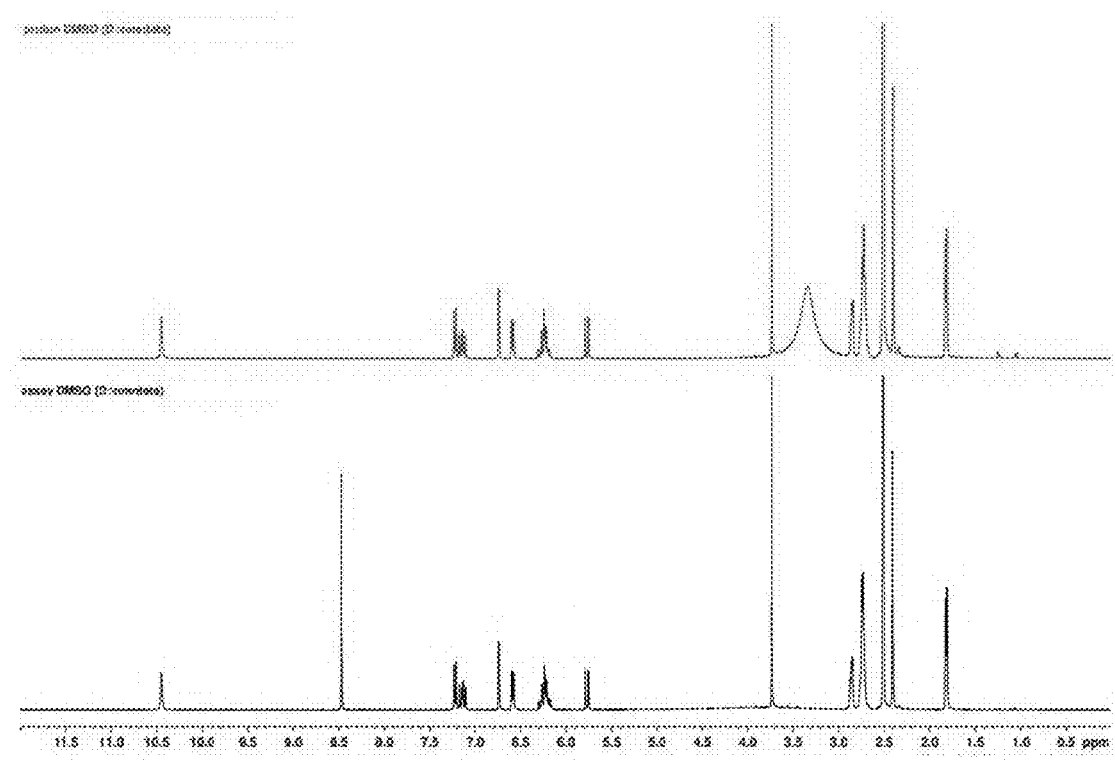

FIG. 678 depicts the overlaid $^1$H NMR spectra of Experiment 2-Sample S2 (from water, insufficient material for KF analysis, top) and Experiment 1-Sample A2 (Form A, assay, bottom). DMSO-d$_6$ used as deuterated solvent. TCNB used in Experiment 1-Sample A2 as internal standard.

Figure 679:
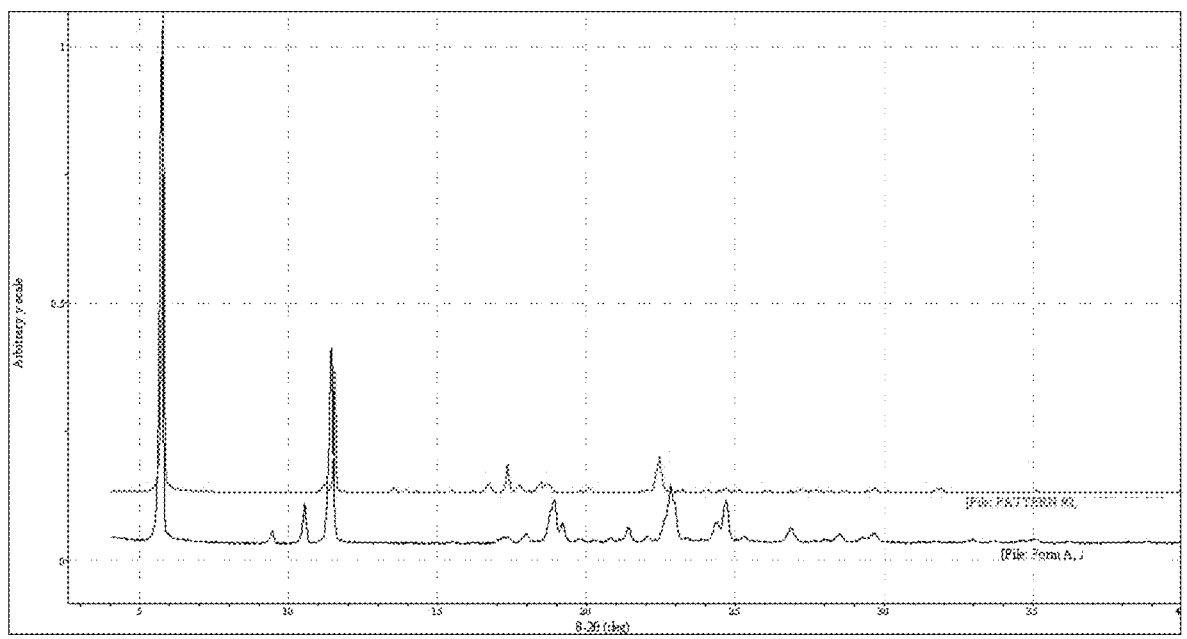

FIG. 679 depicts the overlaid of XRPD profiles of Experiment 3-Sample R1 (pattern #2, top) and Experiment 1-Sample A2 (Form A, bottom)

Figure 680:
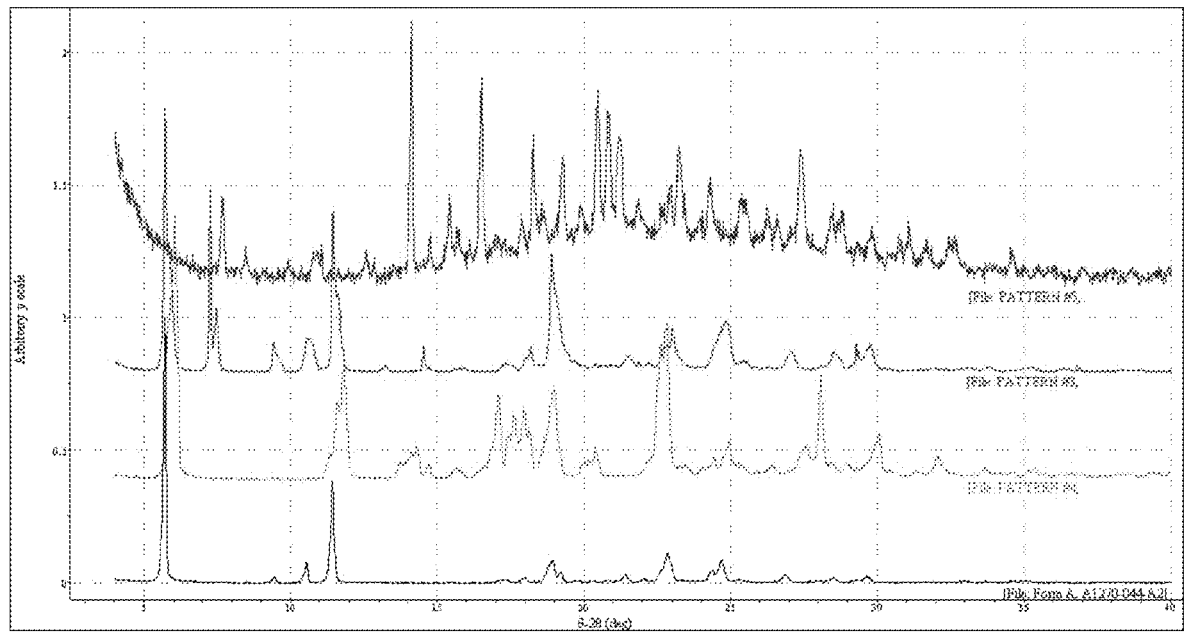

FIG. 680 depicts the overlaid of XRPD profiles of, from top to bottom, Experiment 4-Sample E1 (pattern #5), Experiment 4-Sample H i (pattern #3), Experiment 4-Sample R1 (pattern #4) and Experiment 1-Sample A2 (Form A).

Figure 681:
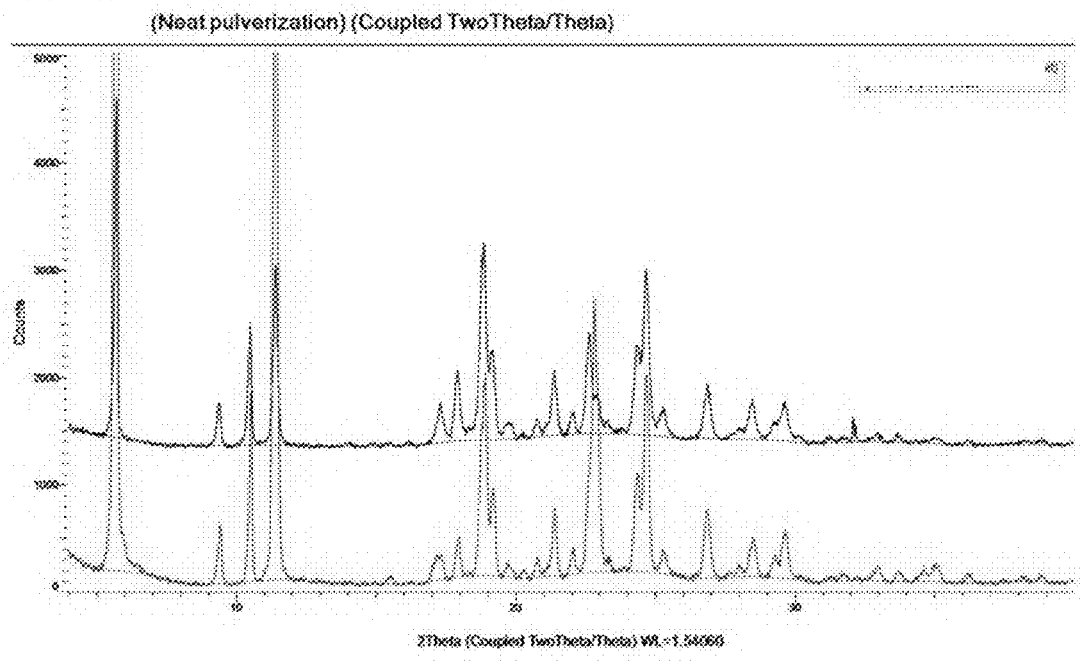

FIG. 681 depicts the overlaid of XRPD profiles of Experiment 7-Sample A (neat, top) and Experiment 1-Sample A2 (Form A, bottom).

Figure 682:
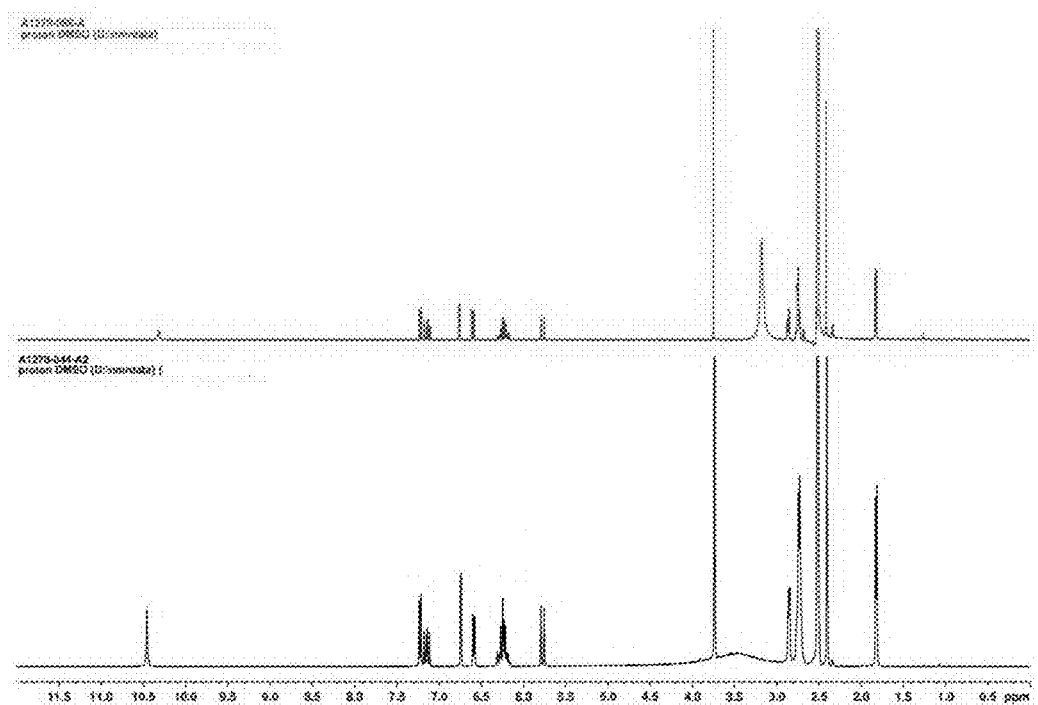

FIG. 682 depicts the overlaid of $^1$H NMR spectra of Experiment 7-Sample A (top) and Experiment 1-Sample A2 (Form A, bottom). DMSO-d$_6$ used as deuterated solvent.

Figure 683:
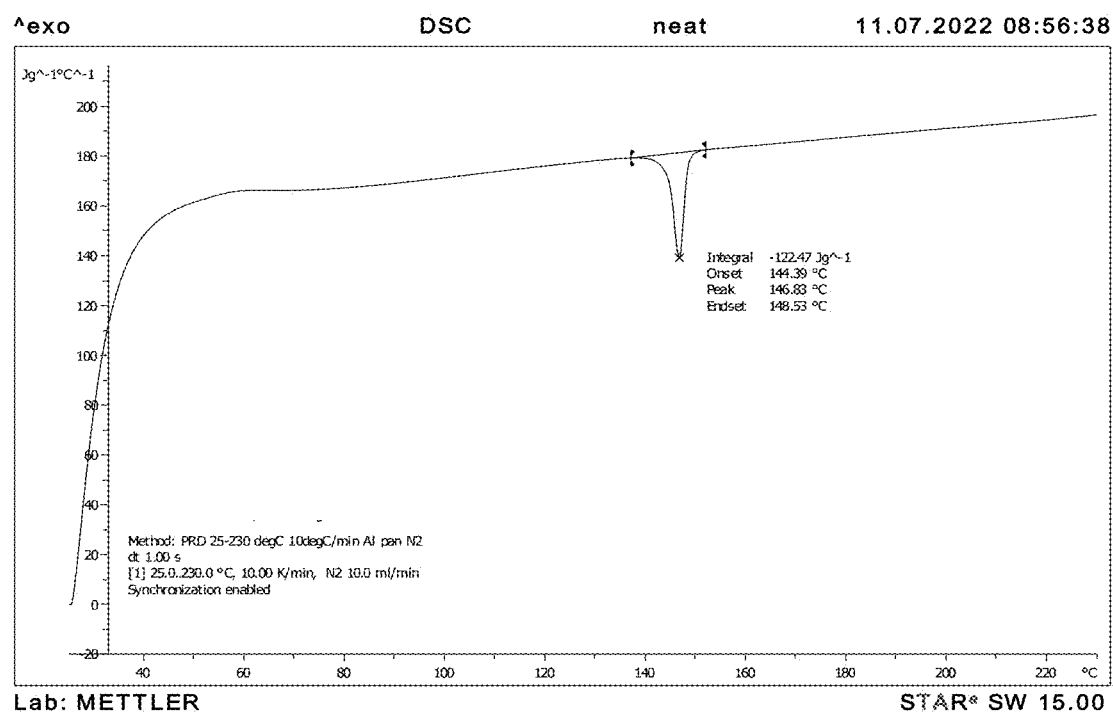

FIG. 683 depicts the DSC profile of Experiment 7-Sample A neat.

Figure 684:
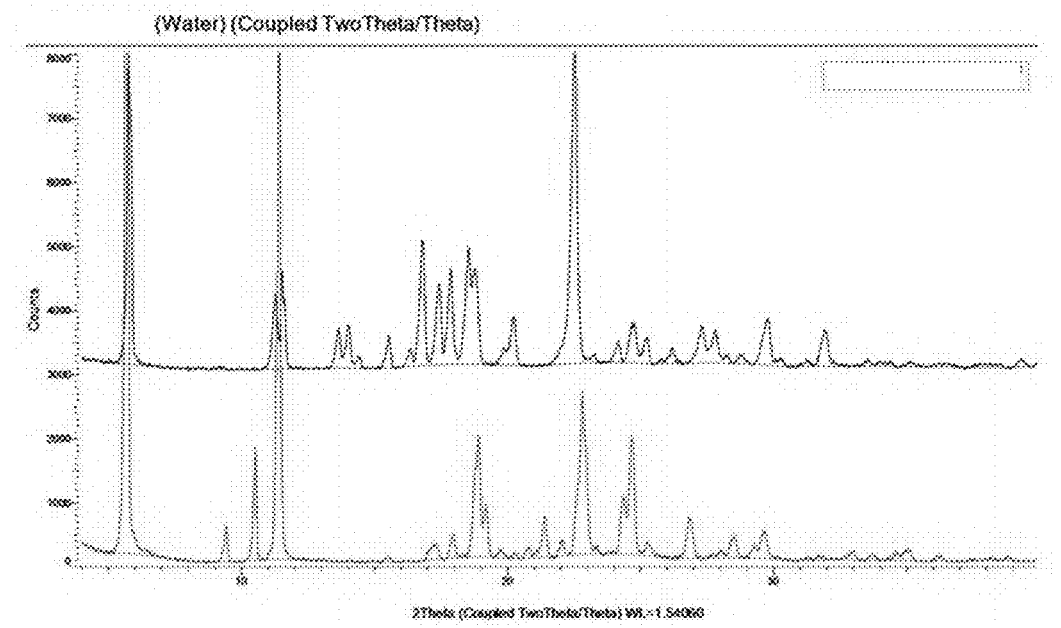

FIG. 684 depicts the overlaid of XRPD profiles of Experiment 7-Sample B (water, top) and Experiment 1-Sample A2 (Form A, bottom).

Figure 685:
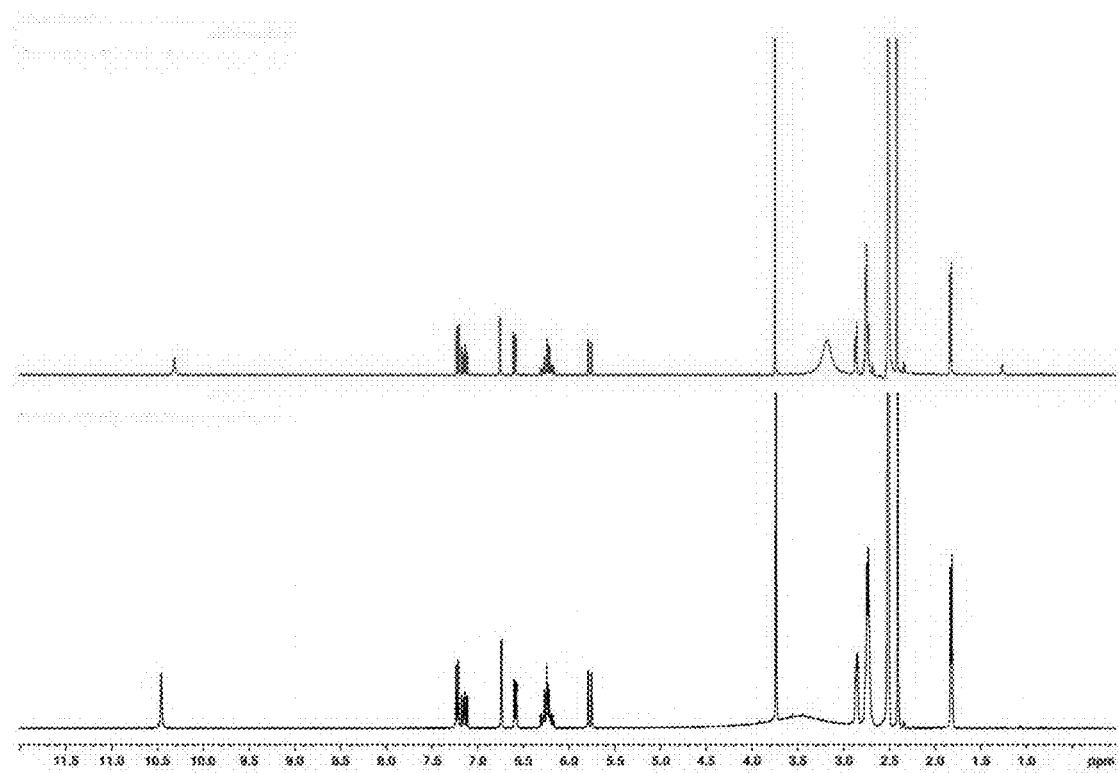

FIG. 685 depicts the overlaid of $^1$H NMR spectra of Experiment 7-Sample B (top) and Experiment 1-Sample A2 (Form A, bottom). DMSO-d$_6$ used as deuterated solvent.

Figure 686:
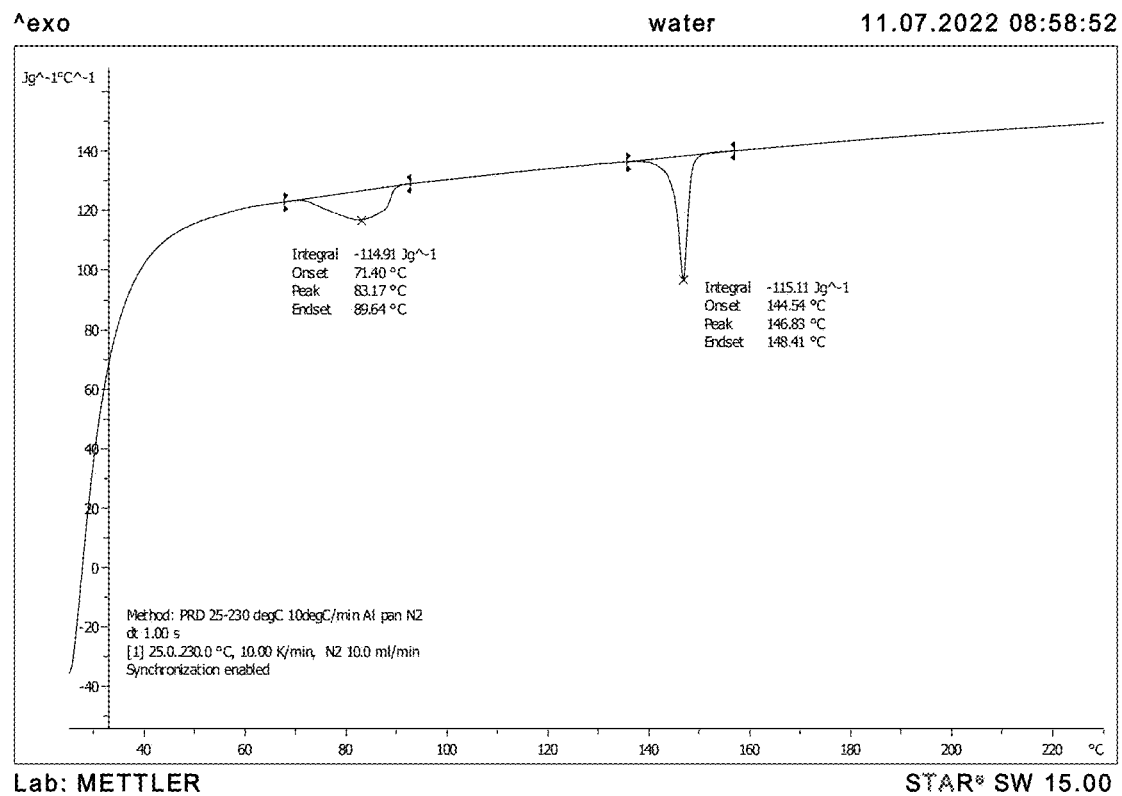

FIG. 686 depicts the DSC profile of Experiment 7-Sample B water.

Figure 687:
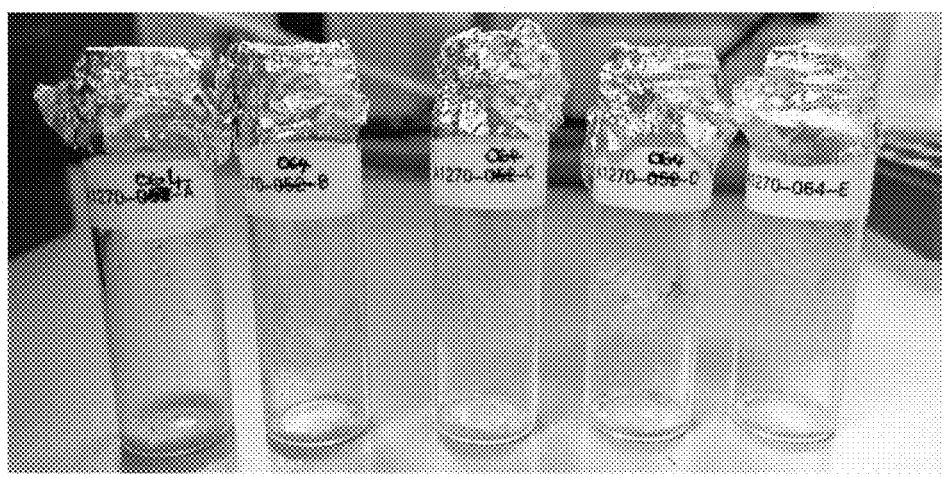

FIG. 687 depicts the samples after 7 days. From left to right: Experiment 6-Sample A, B, C, D and E.

Figure 688:
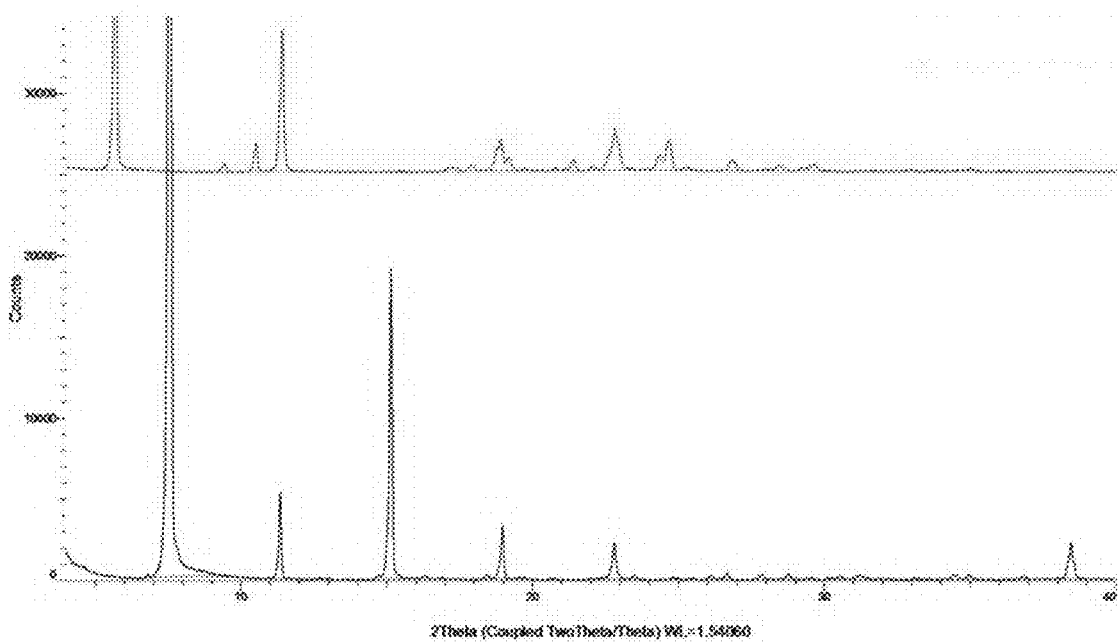

FIG. 688 depicts the overlaid of XRPD profiles of Tabernanthalog Sorbate at t=0: Experiment 6-Sample A1 (via evaporation from water and consistent with pattern #1, Form B, bottom) and Experiment 1-Sample A2 (Form A, top).

Figure 689:
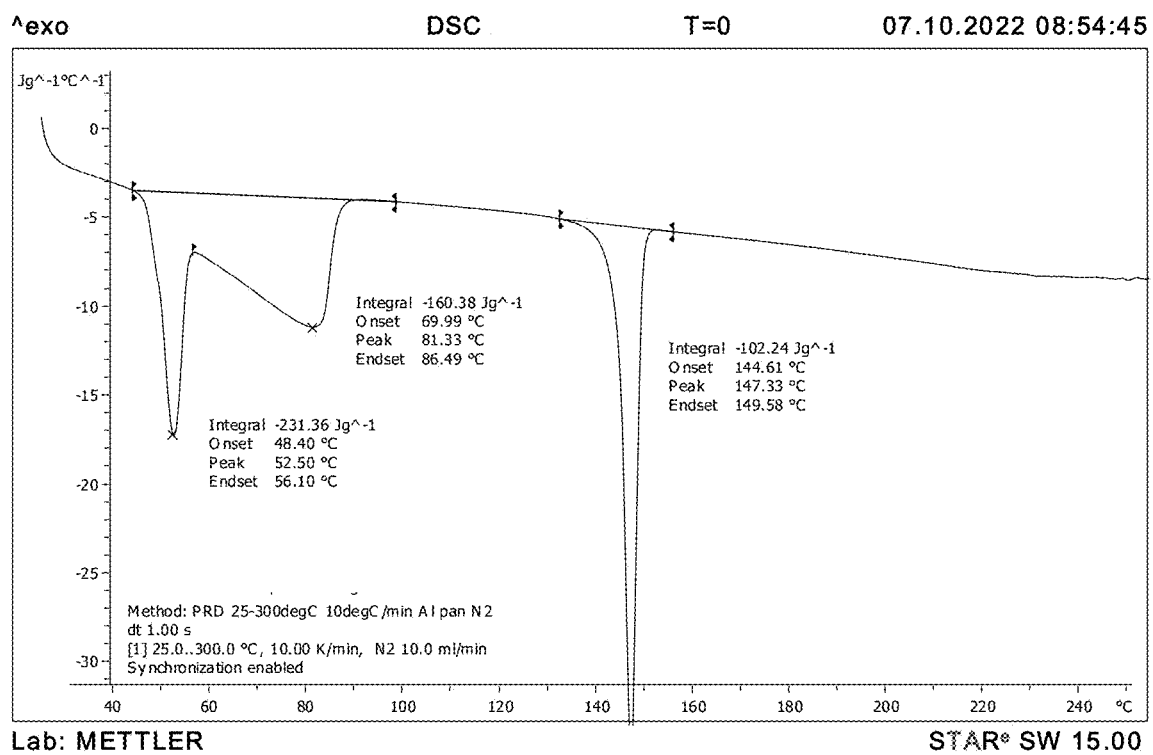

FIG. 689 depicts the DSC profile of Experiment 6-Sample A1 T=0. De-hydration behaviour more consistent with channel or pocket hydration; no transition was evident into Form A.

Figure 690:
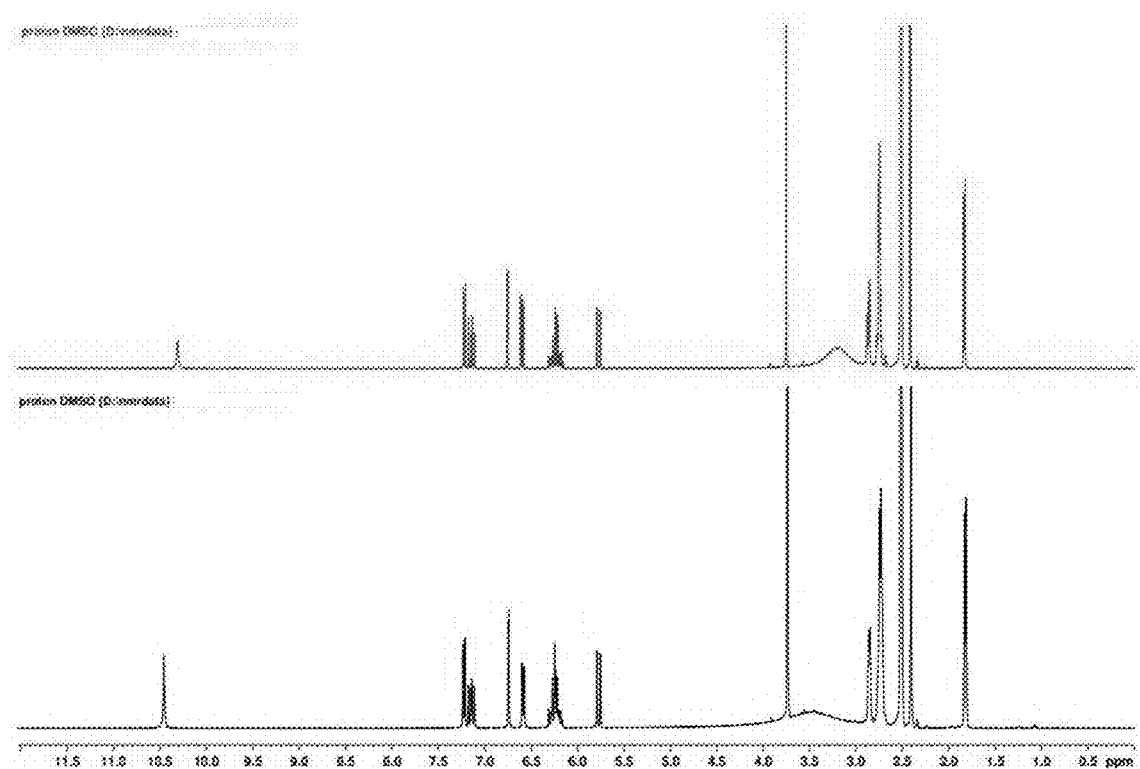

FIG. 690 depicts the overlay of $^1$H NMR spectra of Tabernanthalog Sorbate at t=0: Experiment 6-Sample A1 (via evaporation from water and consistent with pattern #1, Form B, bottom) and Experiment 1-Sample A2 (Form A, top). DMSO-d$_6$ used as deuterated solvent.

Figure 691:
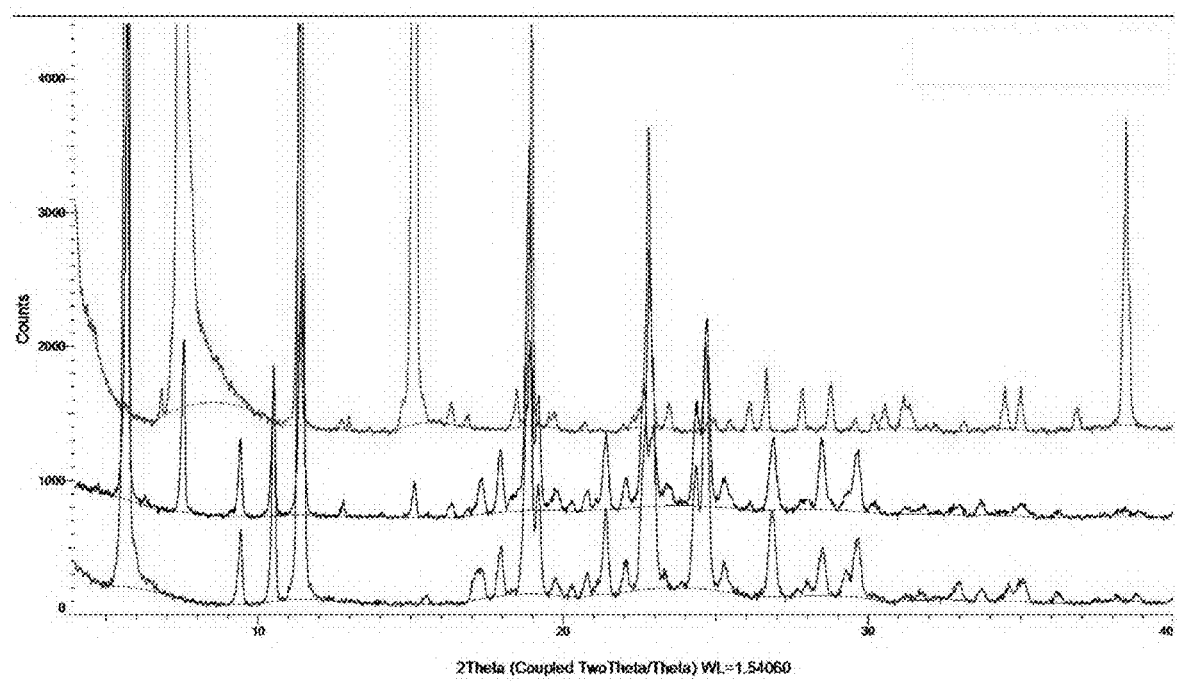

FIG. 691 depicts the overlay of XRPD profiles of Tabernanthalog Sorbate at t=8 days: Experiment 6-Sample A1 (t=8 d) (t=8 days, Pattern changed, appeared to be reverting into Form A; middle) and Experiment 6-Sample A1 (t=0, Pattern #1, Form B, top) and Tabernanthalog sorbate salt (Experiment 1-Sample A2, Form A, reference standard, bottom).

Figure 692:
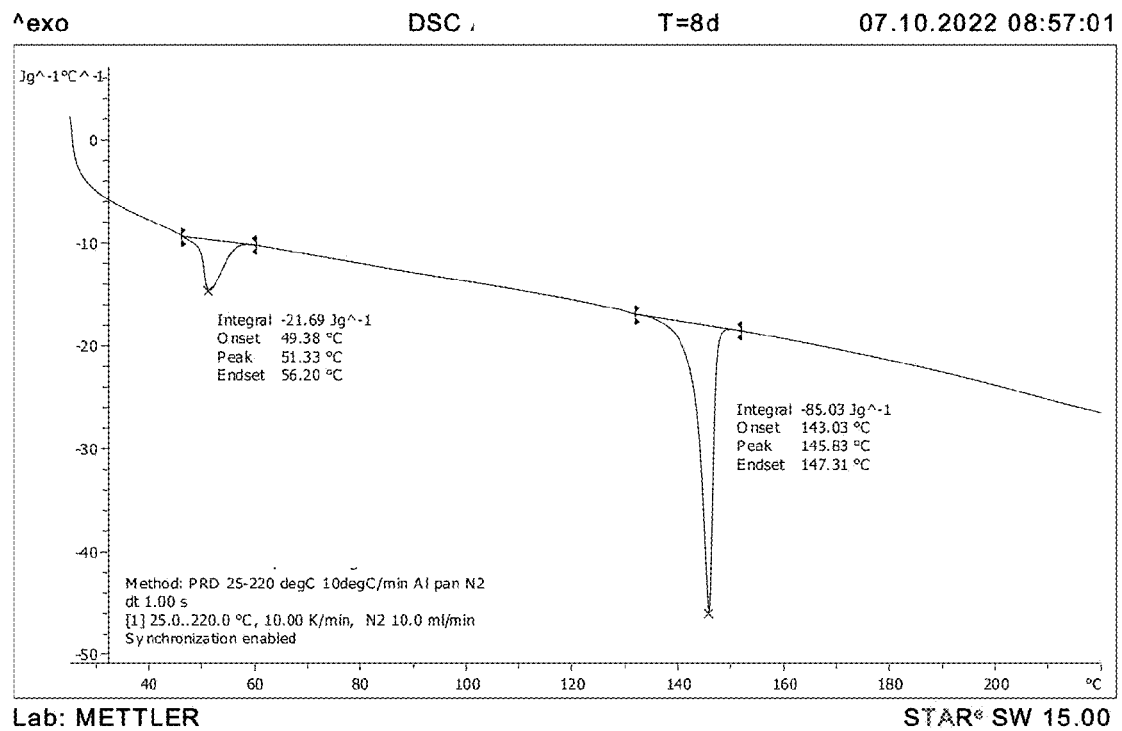

FIG. 692 depicts the DSC profile of Experiment 6-Sample A1 T=8d at t=8 days. De-hydration enthalpy converted to single mode present at T=8 days and enthalpy reduced.

Figure 693:
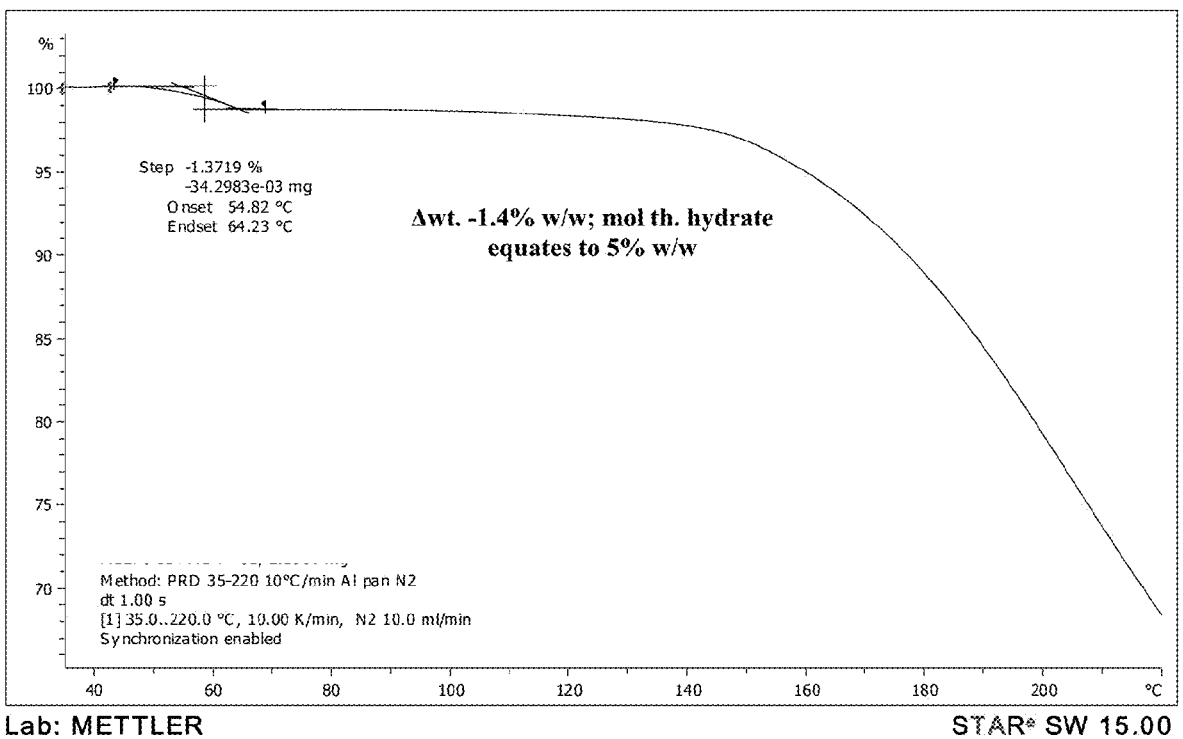

FIG. 693 depicts the TGA profile of Experiment 6-Sample A1 T=8d at t=8 days.

Figure 694:
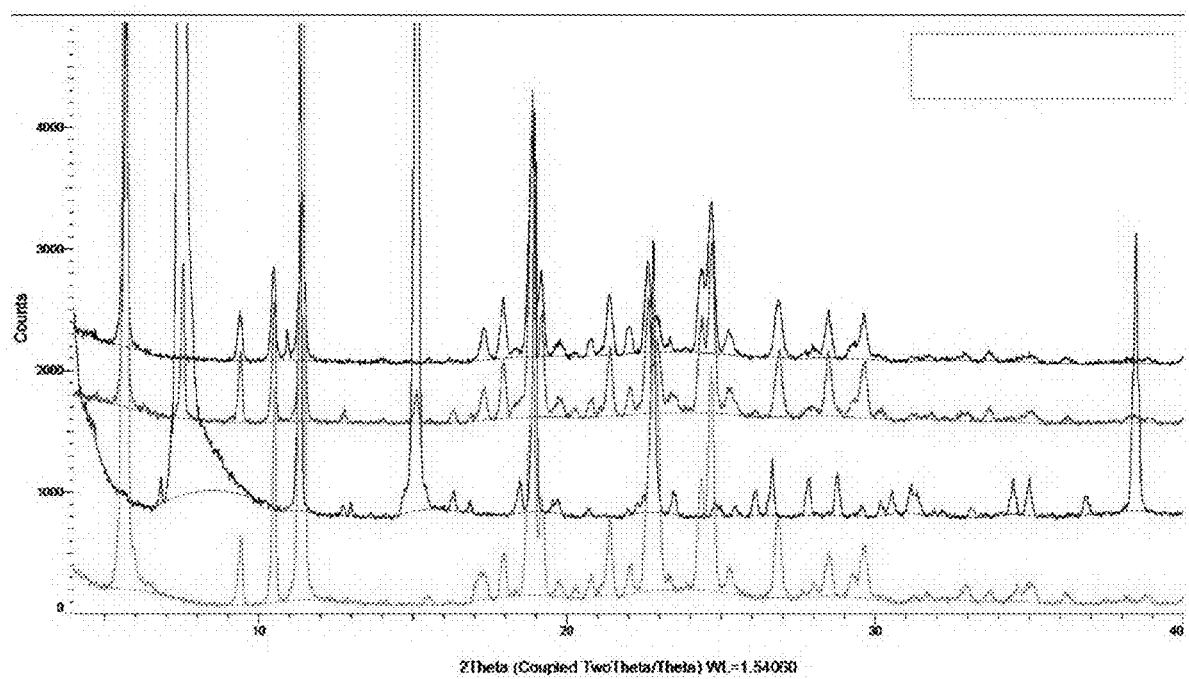

FIG. 694 depicts the overlay of, from bottom to top, XRPD profiles of Tabernanthalog Sorbate: Experiment 1-Sample A2 (Form A), Experiment 6-Sample A1 (t=0, Pattern #1, Form B), Experiment 6-Sample A1 (t=8d) (t=8 days, Pattern changed, appeared to be reverting into Form A) and Experiment 6-Sample A1 after DSC (DSC up to 80° C., congruent with Form A).

Figure 695:
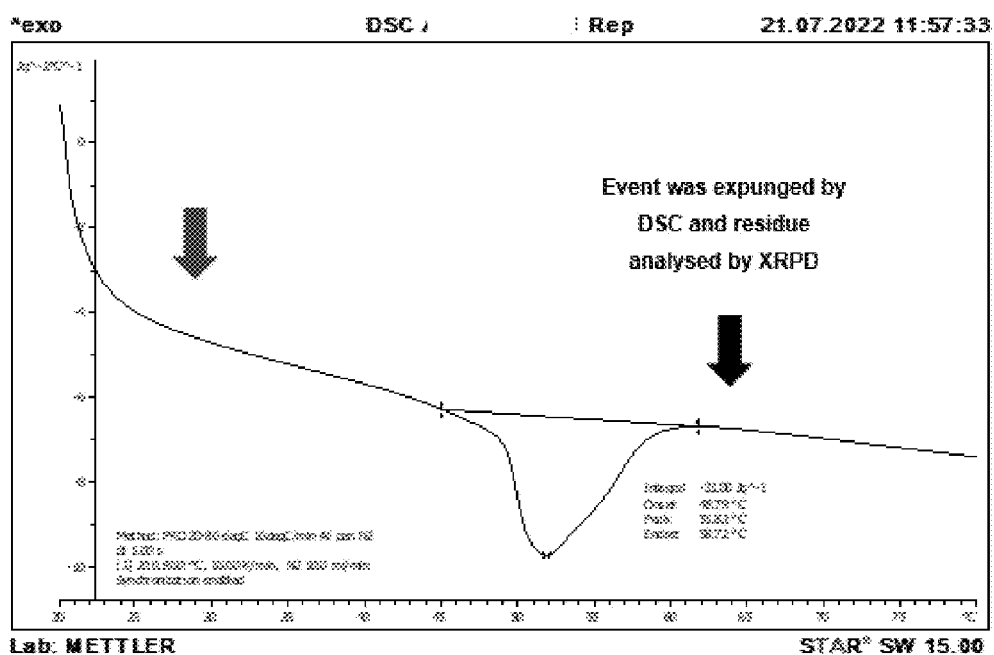

FIG. 695 depicts the DSC profile of Experiment 6-Sample A1 Rep.

Figure 696:
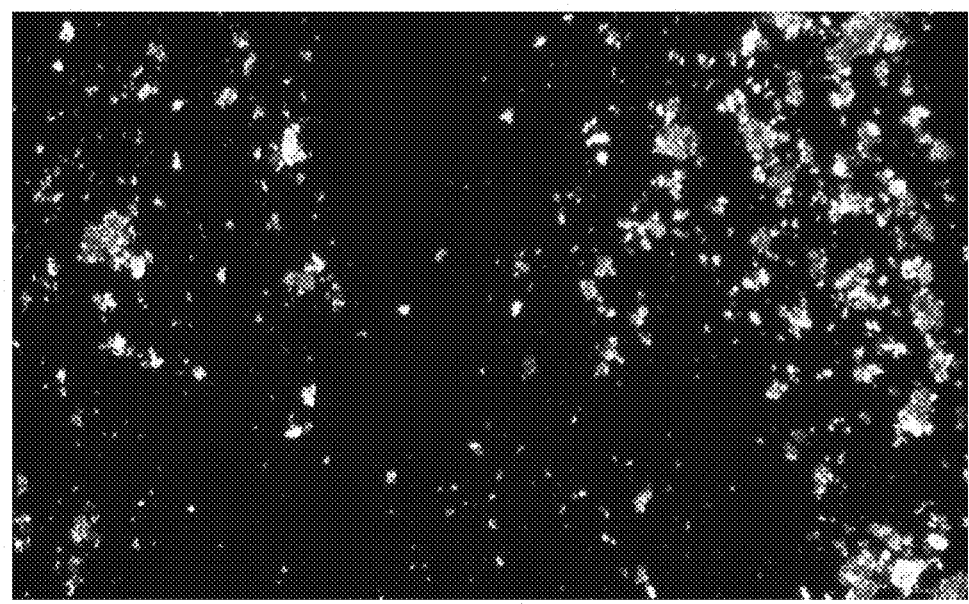

FIG. 696 depicts the PLM of Experiment 6-Sample A1 (normal polarisation, ×2 magnification.).

Figure 697:
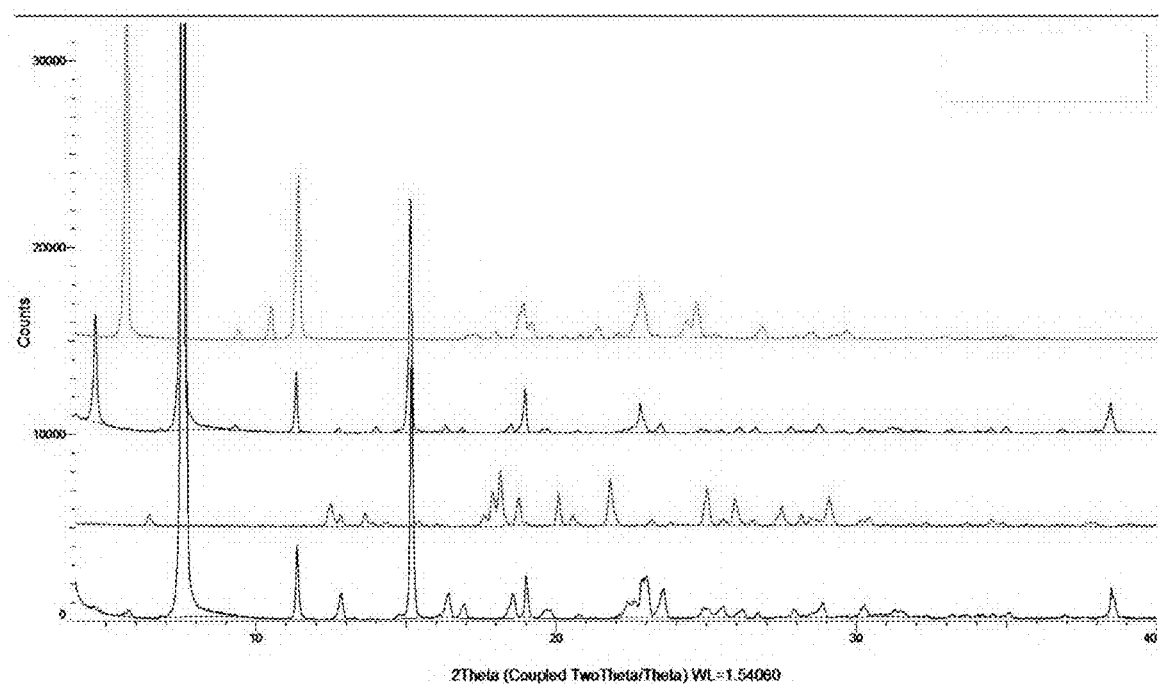

FIG. 697 depicts the overlay of, from top to bottom, $^1$H NMR spectra of Tabernanthalog Sorbate samples: Experiment 1-Sample A2 (Form A), Experiment 8-Sample A1 (wet pellet, Pattern #1, Form B), Experiment 8-Sample A2 (dried under $N_2$ purge, different from Pattern #1, Form B and Form A) and Experiment 5-Sample Q1 (Pattern #1, Form B crystallised from water).

Figures 698, 698A:
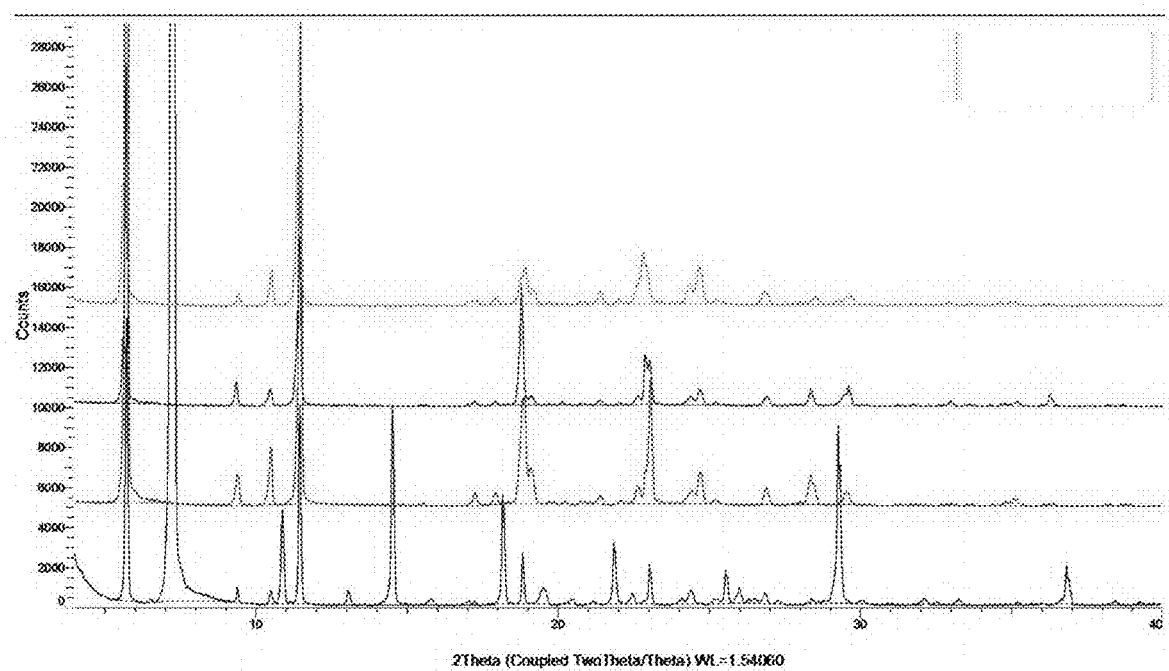

FIG. 698 depicts the overlay of, from top to bottom, $^1$H NMR spectra of Tabernanthalog Sorbate samples: Experiment 1-Sample A2 (Form A), Experiment 8-Sample B1 (wet pellet, Form A), Experiment 8-Sample B2 (dried under $N_2$ purge, Form A) and Experiment 5-Sample G1 (Pattern '#6, crystallised from EtOAc/heptane).

FIG. 698A depicts the summary of results.

Figure 699:
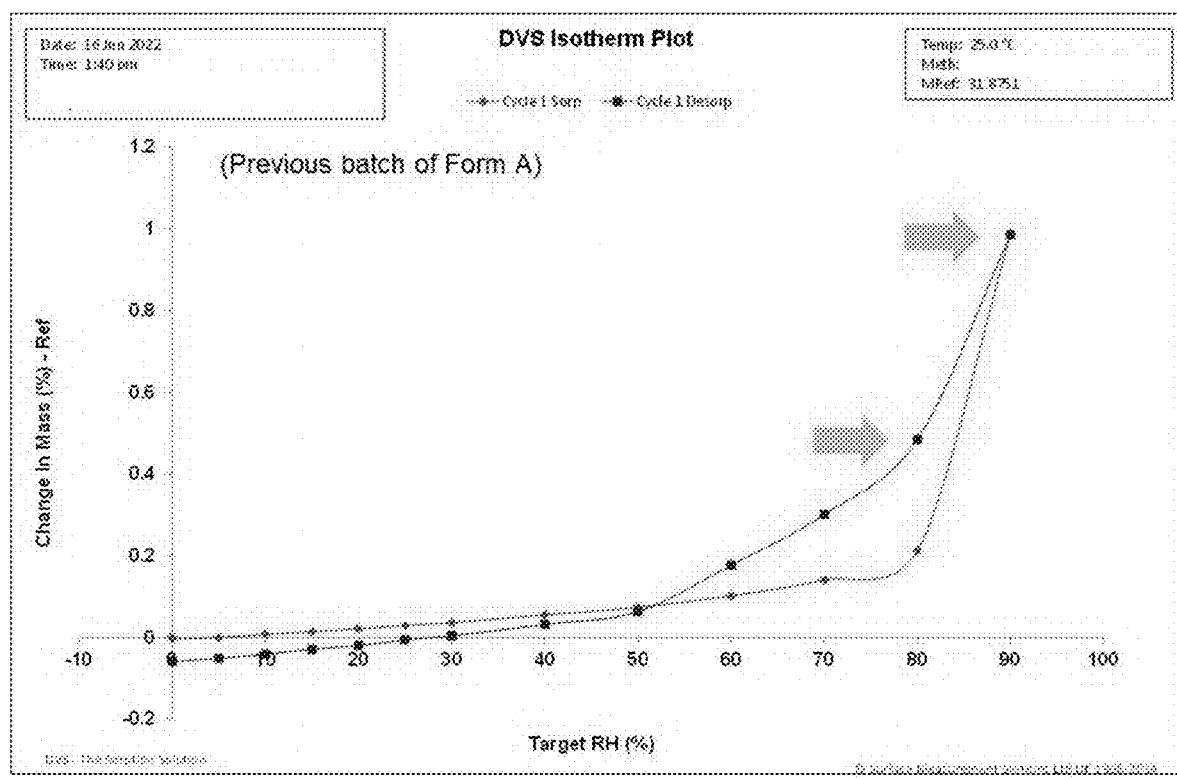

FIG. 699 depicts the DVS data of Experiment 1-Sample A2.

Figure 700:
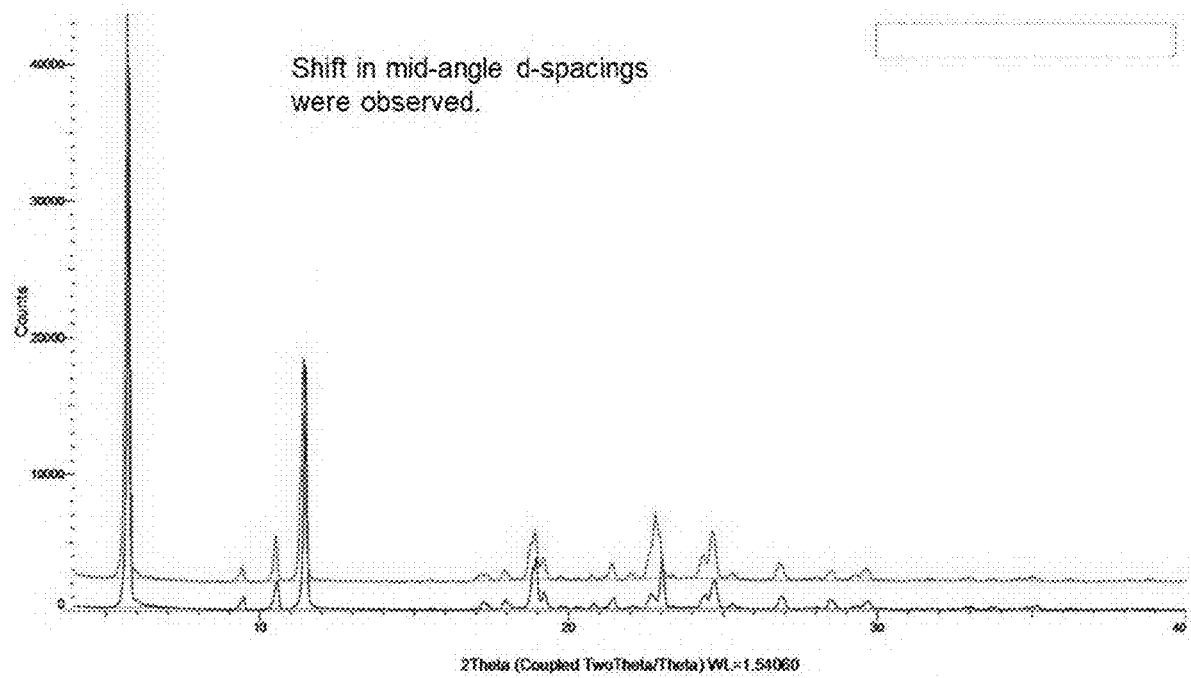

FIG. 700 depicts the overlay of XRPD profiles of Experiment 11-Sample A1 Post DVS (bottom) and Experiment 1-Sample A2 (top).

Figure 701:
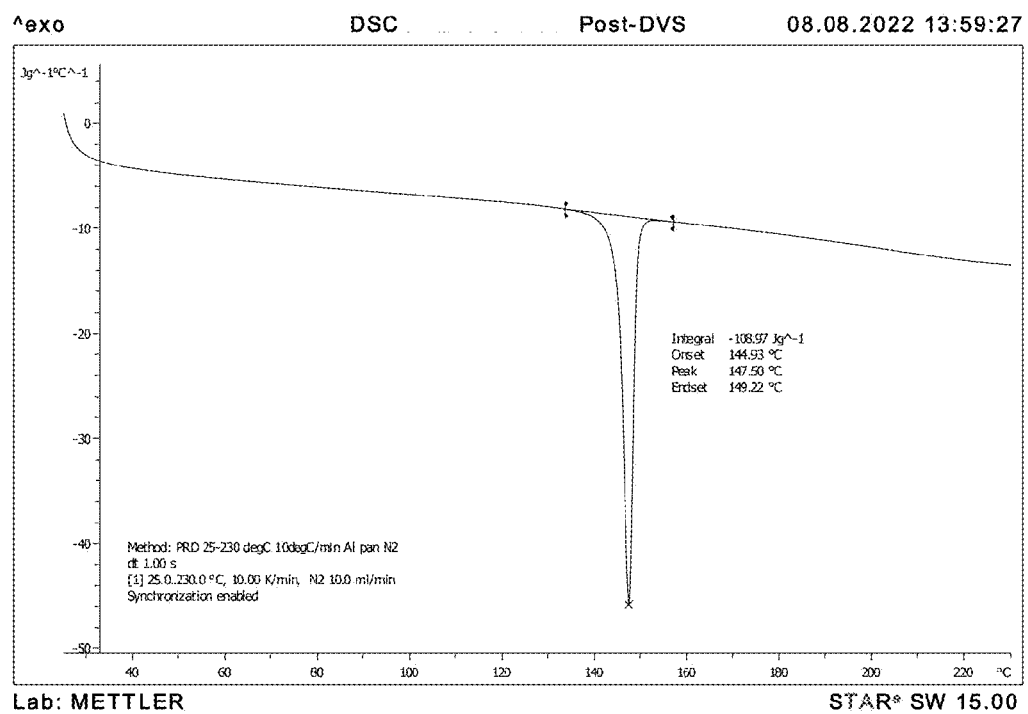

FIG. 701 depicts the DSC profile of Experiment 11-Sample A1 post DVS, m.p. of specimen at 80% RH was consistent with Form A.

Figure 702:
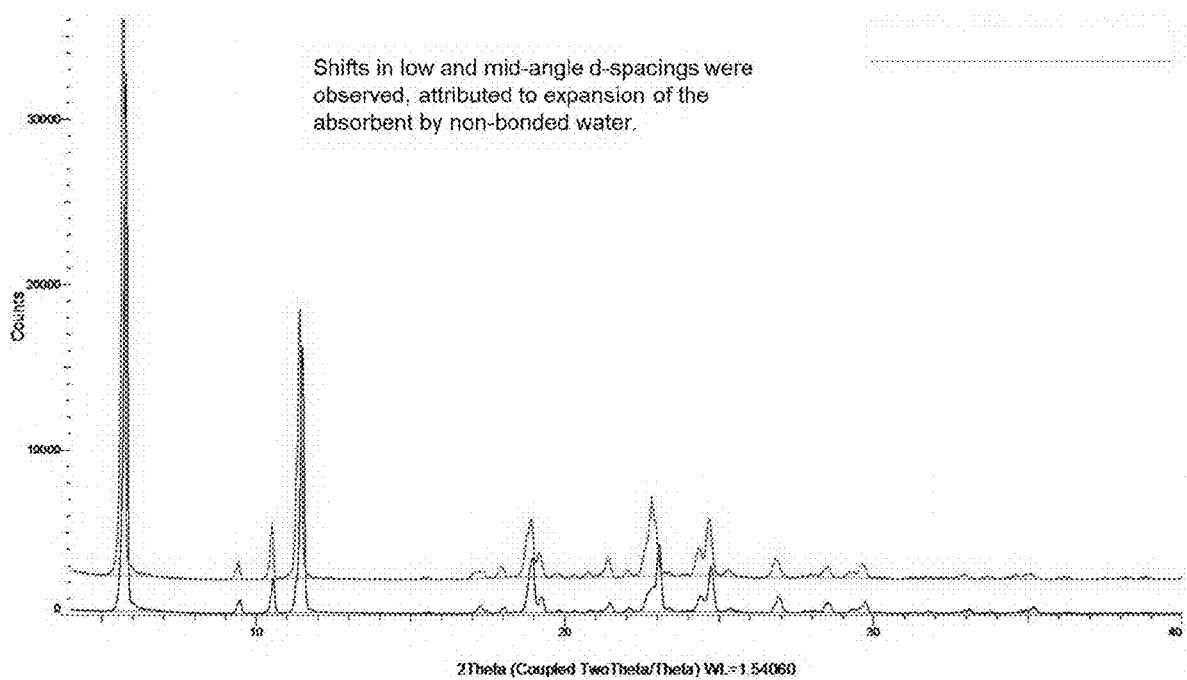

FIG. 702 depicts the overlay of XRPD profiles of Experiment 11-Sample A1 post DVS (0 to 90 RH, bottom) and Experiment 1-Sample A2 (top).

Figure 703:
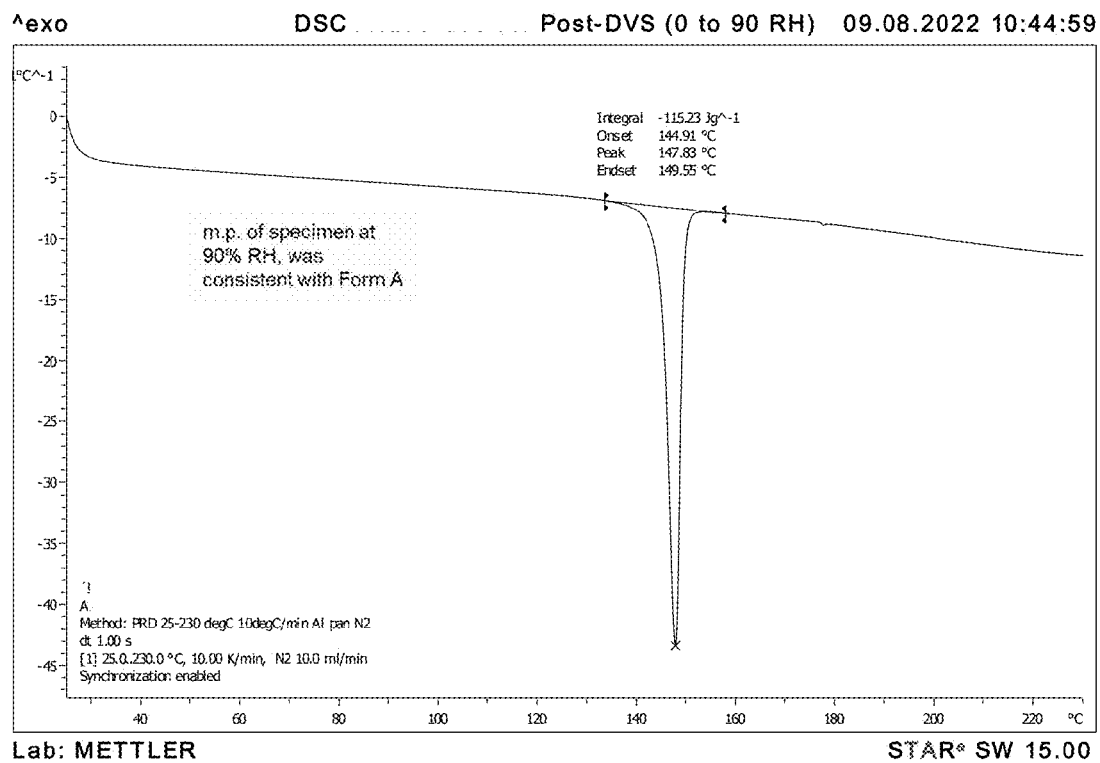

FIG. 703 depicts the DSC profile of Experiment 11-Sample A1 post DVS (0% to 90% RH).

Figure 704:
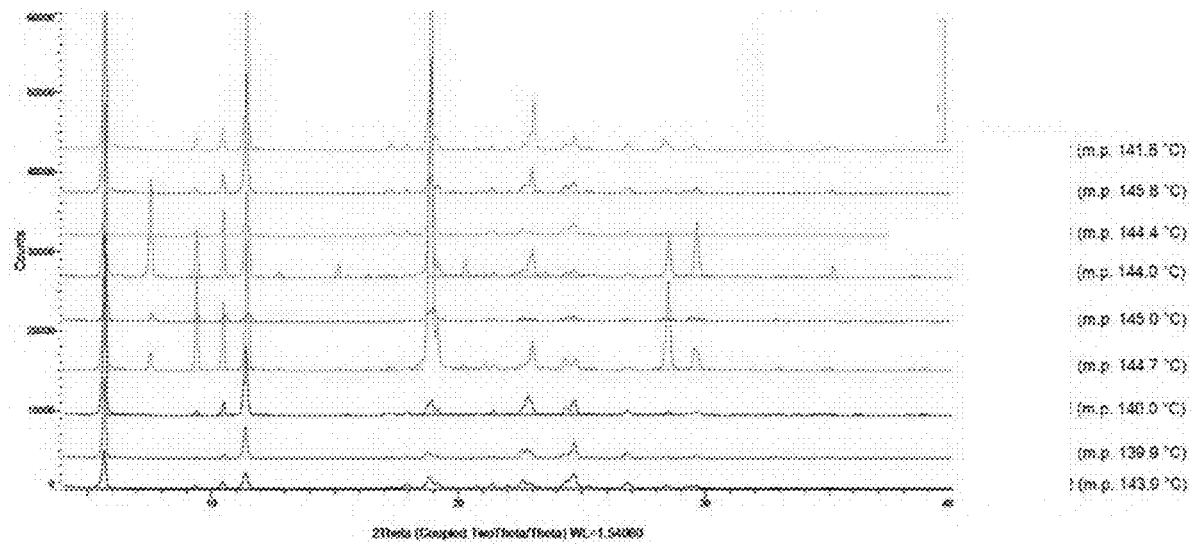

FIG. 704 depicts the overlay of XRPD profiles of the various batches that resemble Form A.

Figure 705:
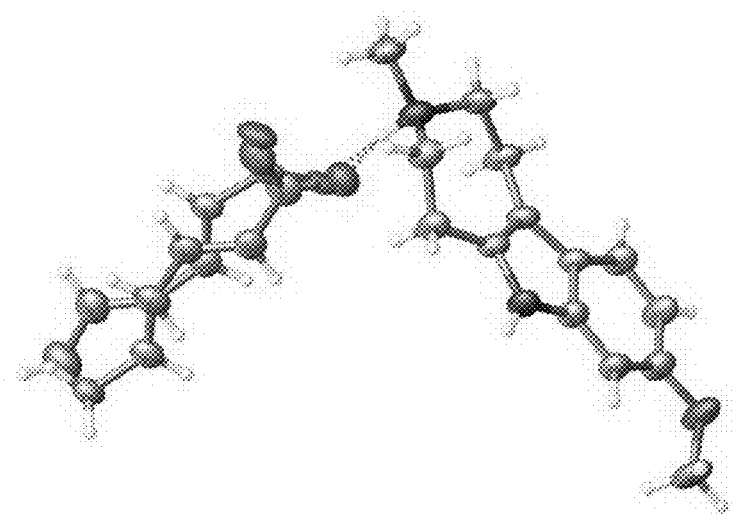

FIG. 705 depicts the asymmetric unit of Experiment 11-Sample A1 (Form A) at 100K with thermal ellipsoids drawn at 50% probability. Both disorder components shown.

Figure 706:
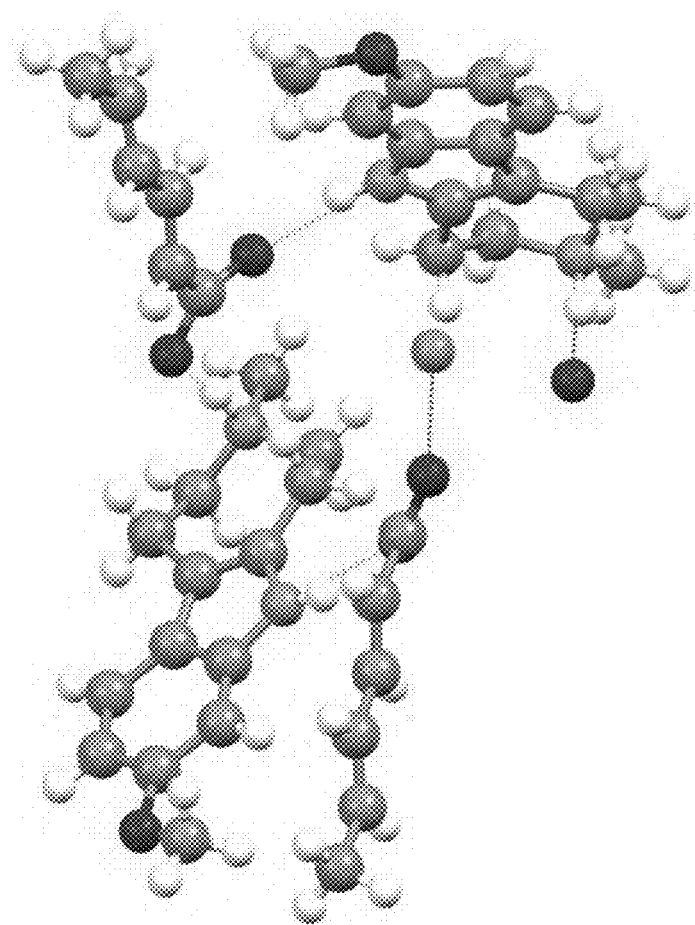

FIG. 706 depicts the hydrogen bonding network of Tabernanthalog sorbate salt (Experiment 11-Sample A1, Form A).

Figure 707:
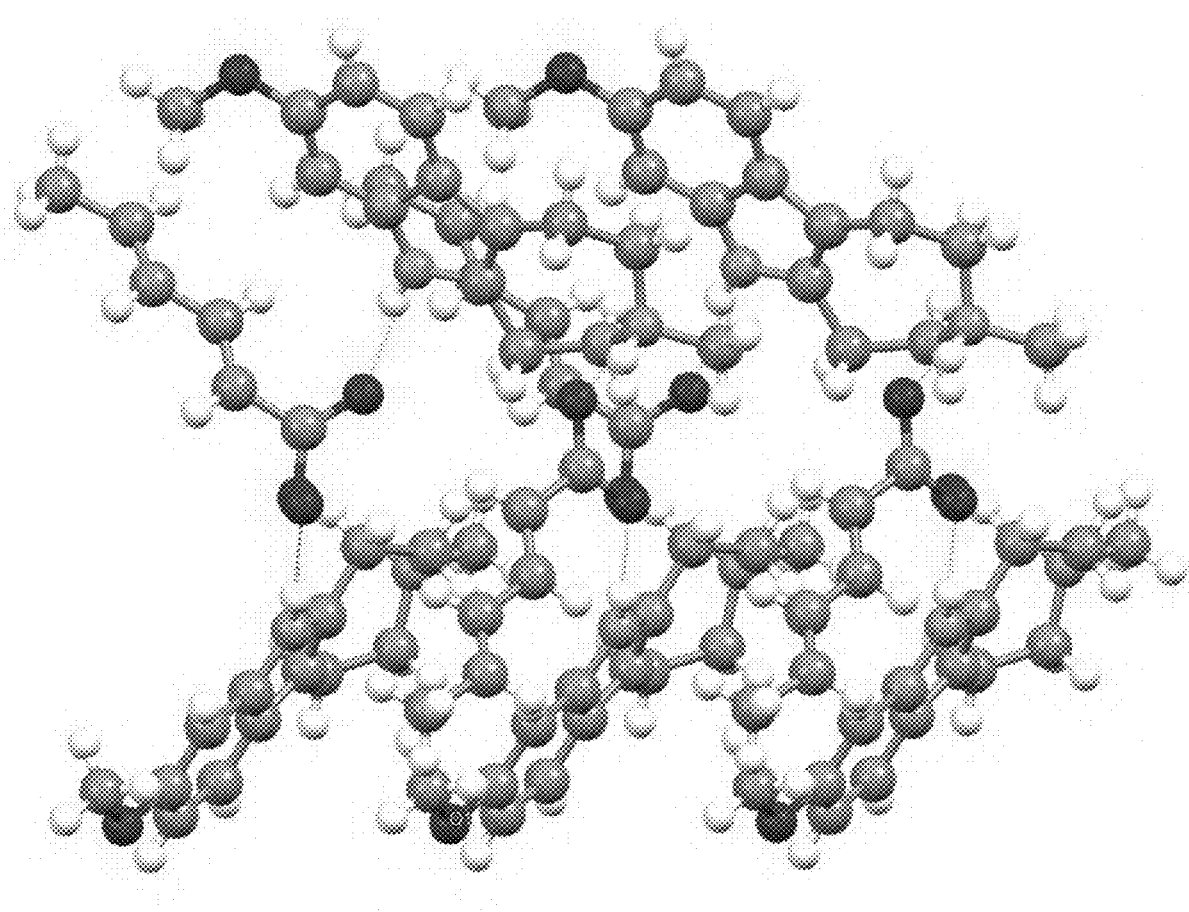

FIG. 707 depicts the hydrogen bonding network of Tabernanthalog sorbate salt (Experiment 11-Sample A1, Form A).

Figure 708:
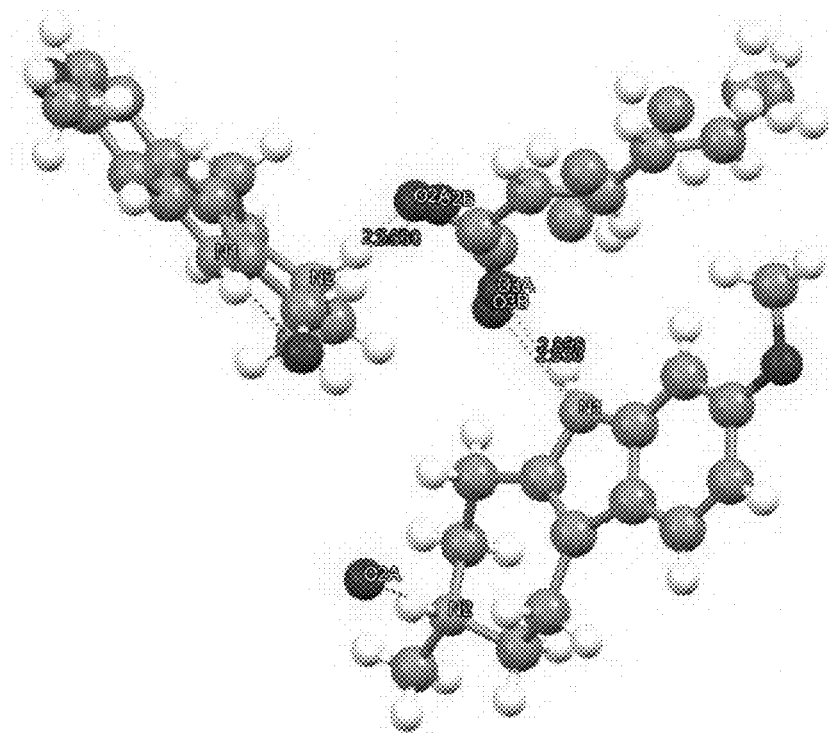

FIG. 708 depicts the calculated hydrogen bond lengths of Tabernanthalog sorbate salt (Experiment 11-Sample A1, Form A).

Figure 709:
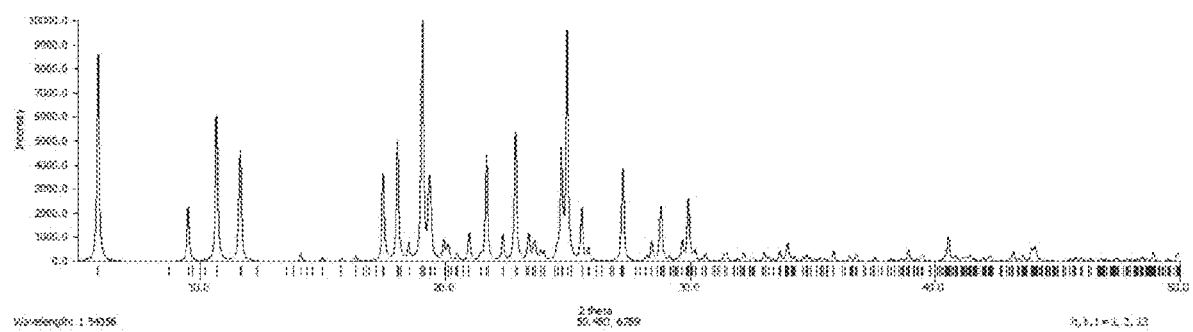

FIG. 709 depicts the simulated powder diffraction pattern of Tabernanthalog sorbate salt (Experiment 11-Sample A1, Form A).

Figure 710:
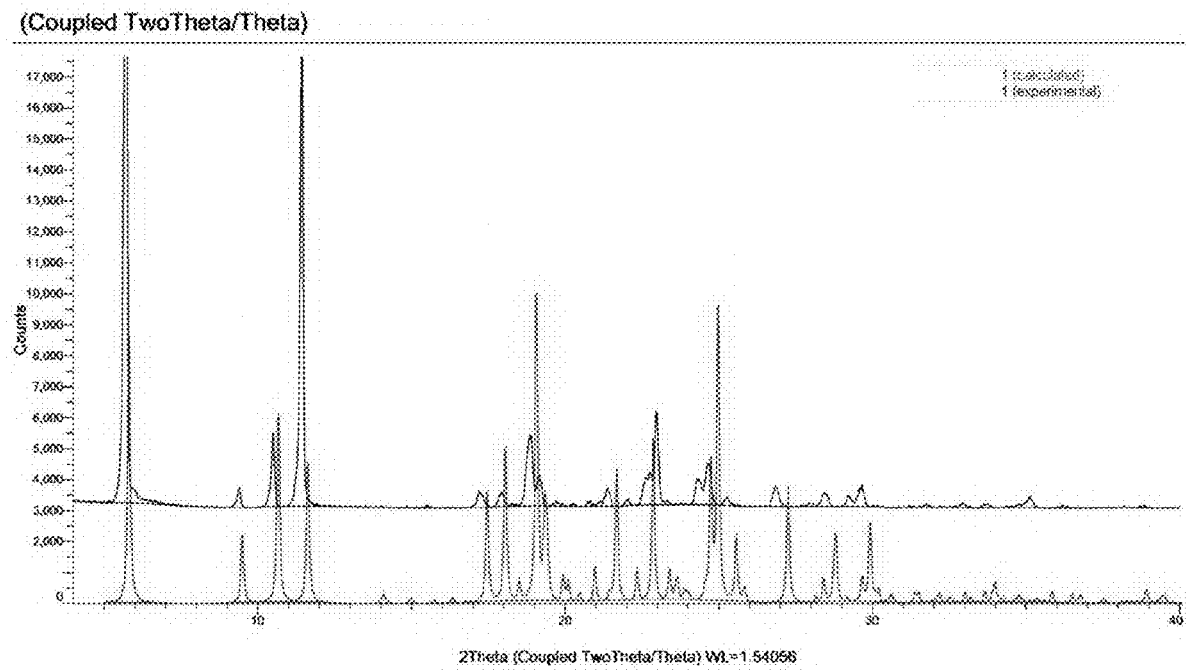

FIG. 710 depicts the XRPD diffractogram overlay of simulated powder diffraction pattern of Tabernanthalog sorbate salt (bottom, Experiment 11-Sample A1, Form A) and Experiment 11-Sample A1 (top, Form A, experimental).

Figure 711:
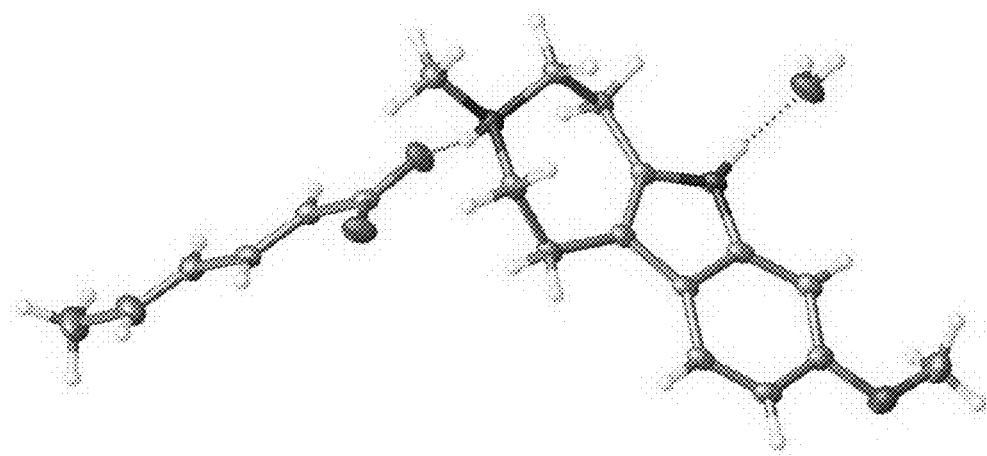

FIG. 711 depicts the asymmetric unit of Tabernanthalog sorbate salt·$H_2O$ (Experiment 12-Sample A2) at 100K with thermal ellipsoids drawn at 50% probability. Both disorder components shown.

Figure 712:
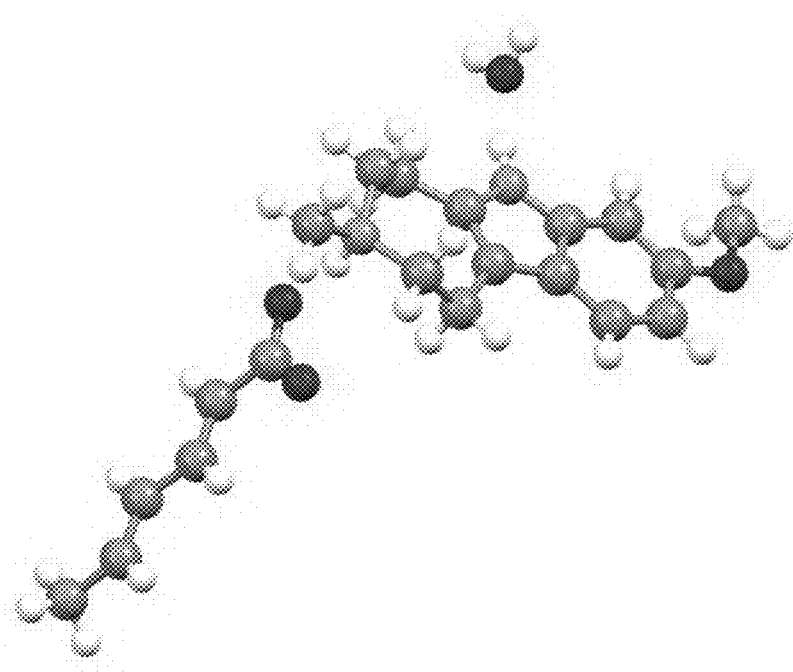

FIG. 712 depicts the asymmetric unit of Tabernanthalog sorbate salt-$H_2O$ (Experiment 12-Sample A2) at 100K with thermal ellipsoids drawn at 50% probability. Both disorder components shown.

Figure 713:
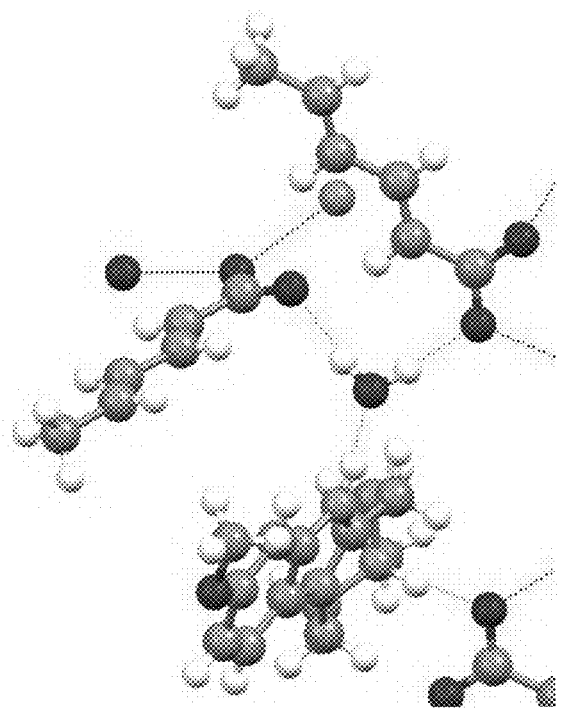

FIG. 713 depicts the hydrogen bonding network of Tabernanthalog sorbate salt·$H_2O$ (Experiment 12-Sample A2).

Figure 714:
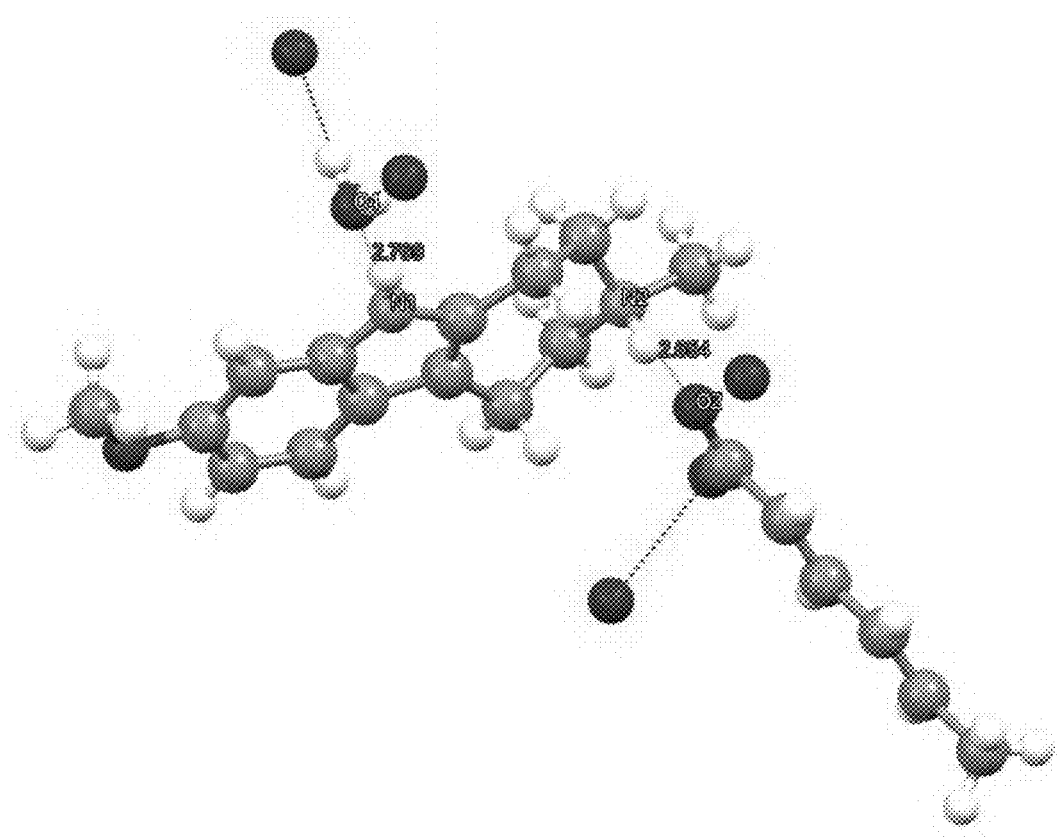

FIG. 714 depicts the calculated hydrogen bond lengths of Tabernanthalog sorbate salt·$H_2O$ (Experiment 12-Sample A2).

Figure 715:
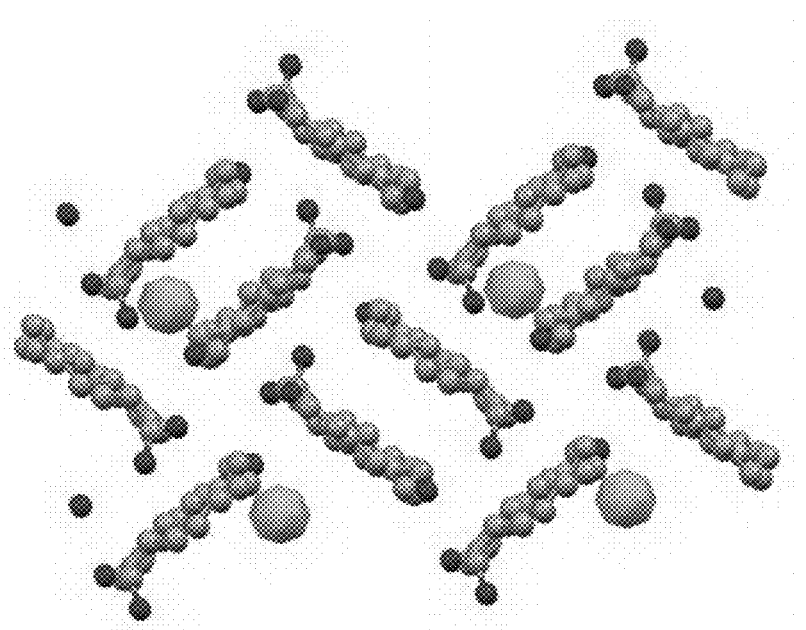

FIG. 715 depicts the void space analysis of Tabernanthalog sorbate salt·$H_2O$ (Experiment 12-Sample A2).

Figure 716:
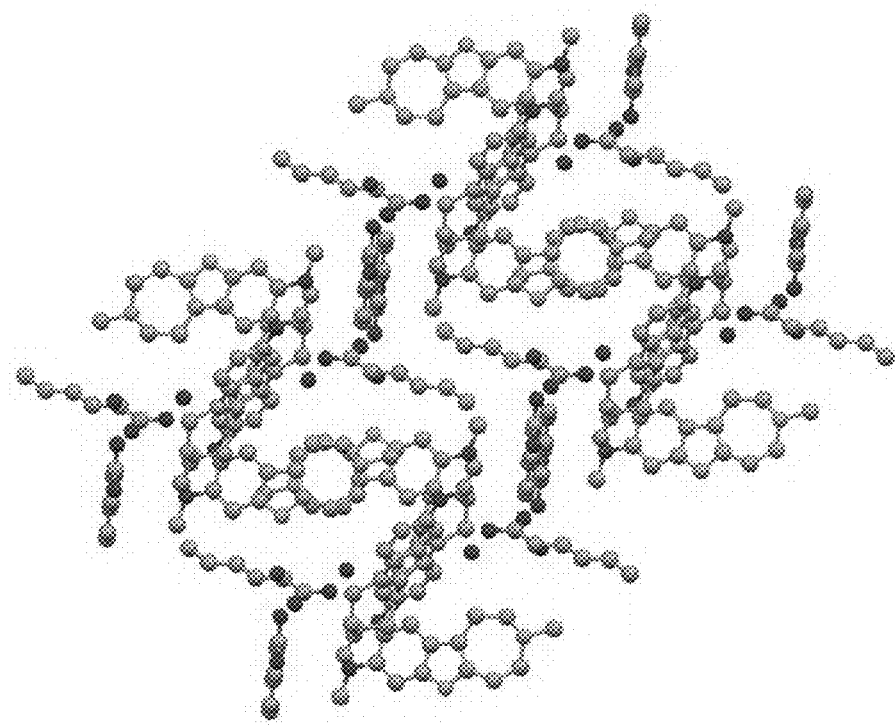

FIG. 716 depicts the packing of Tabernanthalog sorbate salt·$H_2O$ (Experiment 12-Sample A2).

Figure 717:
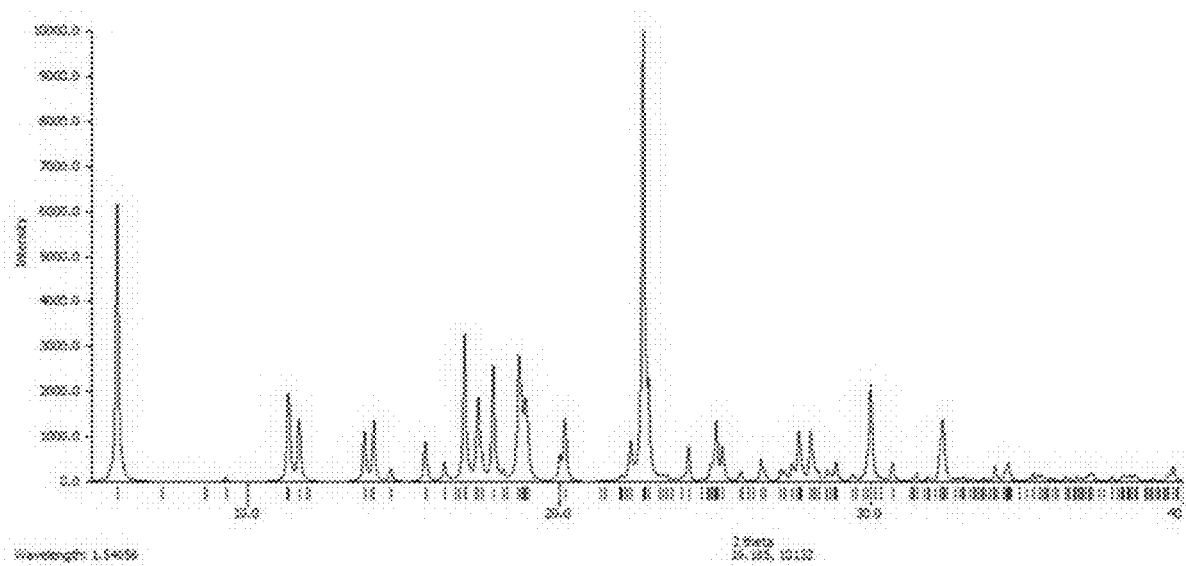

FIG. 717 depicts the simulated powder diffraction pattern of Tabernanthalog sorbate salt·$H_2O$ (Experiment 12-Sample A2).

Figure 718:
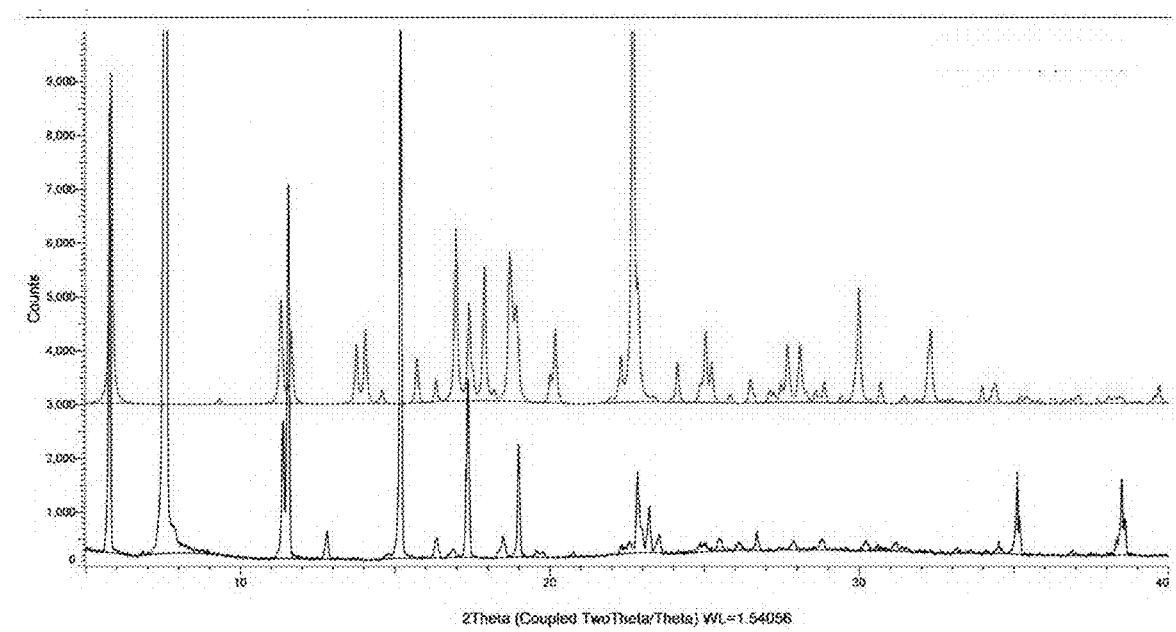

FIG. 718 depicts the XRPD diffractogram overlay of simulated powder diffraction pattern of Tabernanthalog sorbate salt·$H_2O$ (top, Experiment 12-Sample A2, hydrate) and Experiment 12-Sample A2 (bottom, experimental).

Figure 719:
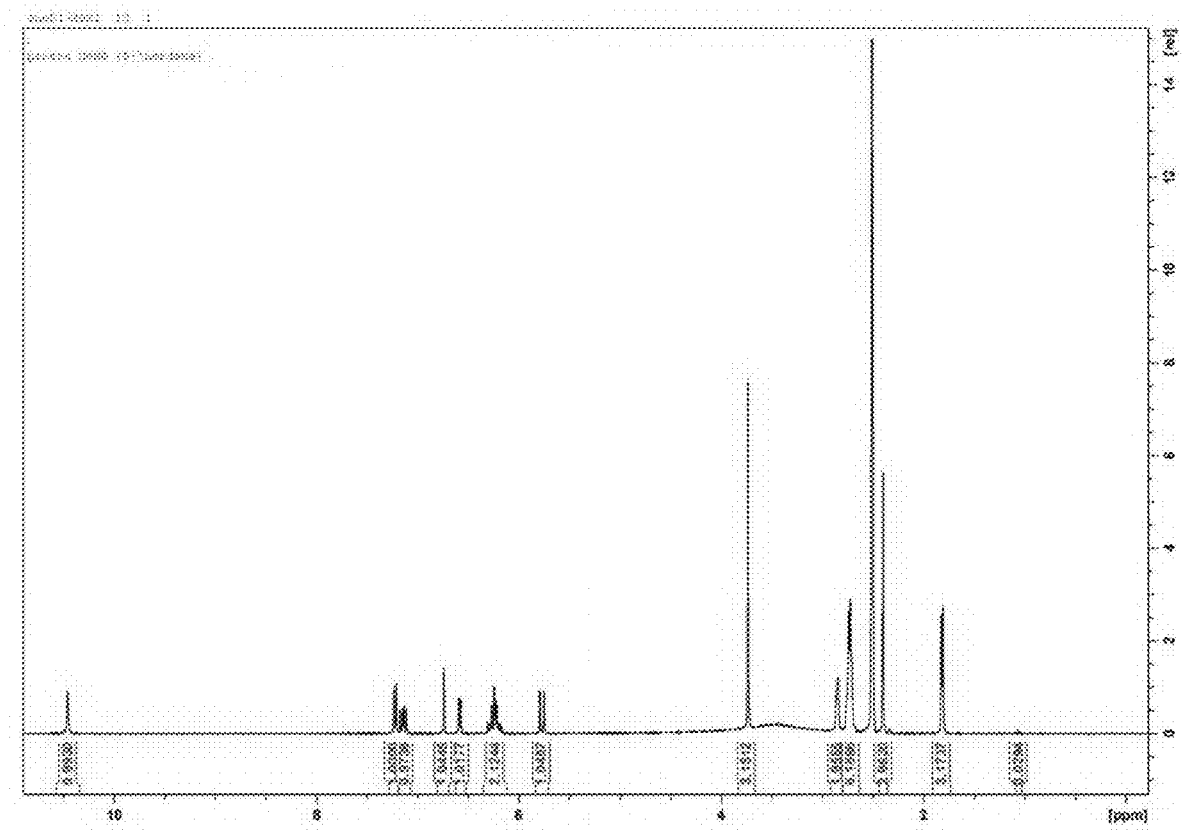

FIG. 719 depicts the $^1$H NMR spectrum of Experiment 1-Sample A2 in DMSO-$d_6$ used as deuterated solvent.

Figure 720:
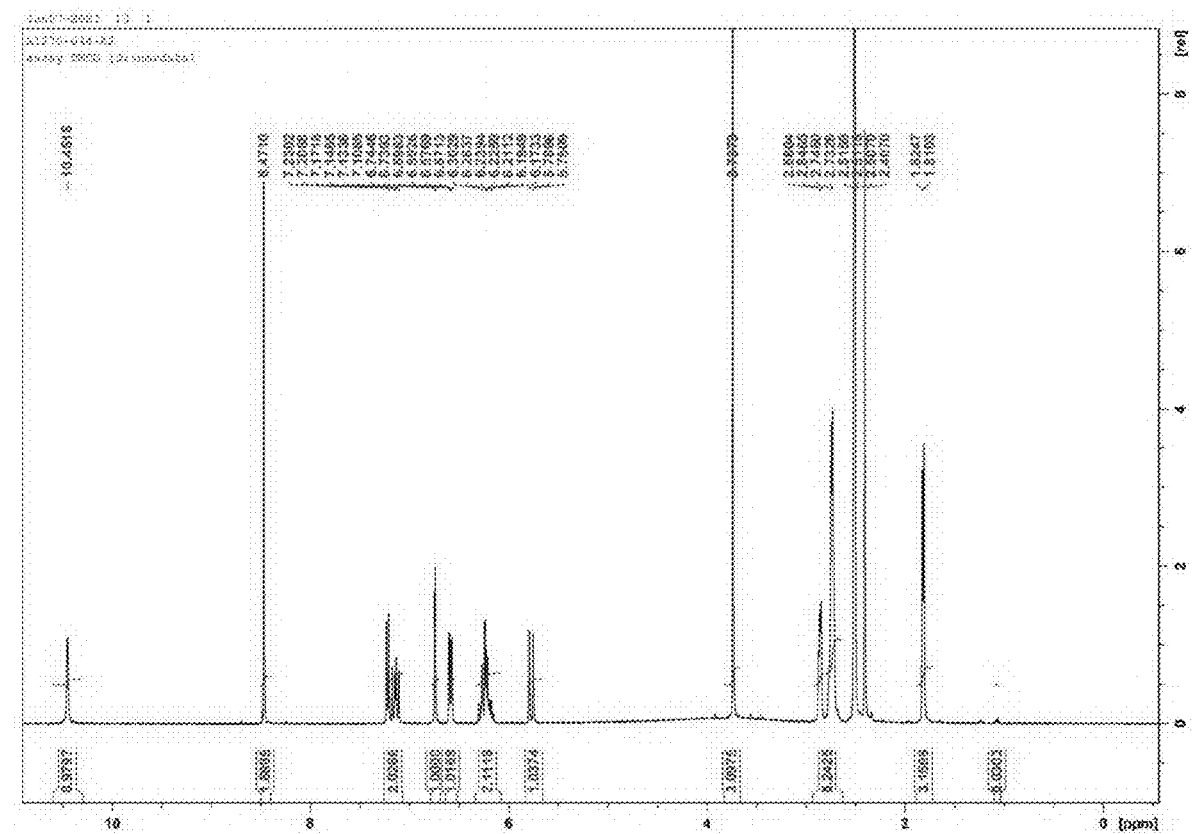

FIG. 720 depicts the Q NMR assay of Experiment 1-Sample A2 in DMSO-$d_6$ used as deuterated solvent. 99.9% w/w assay.

Figure 721:
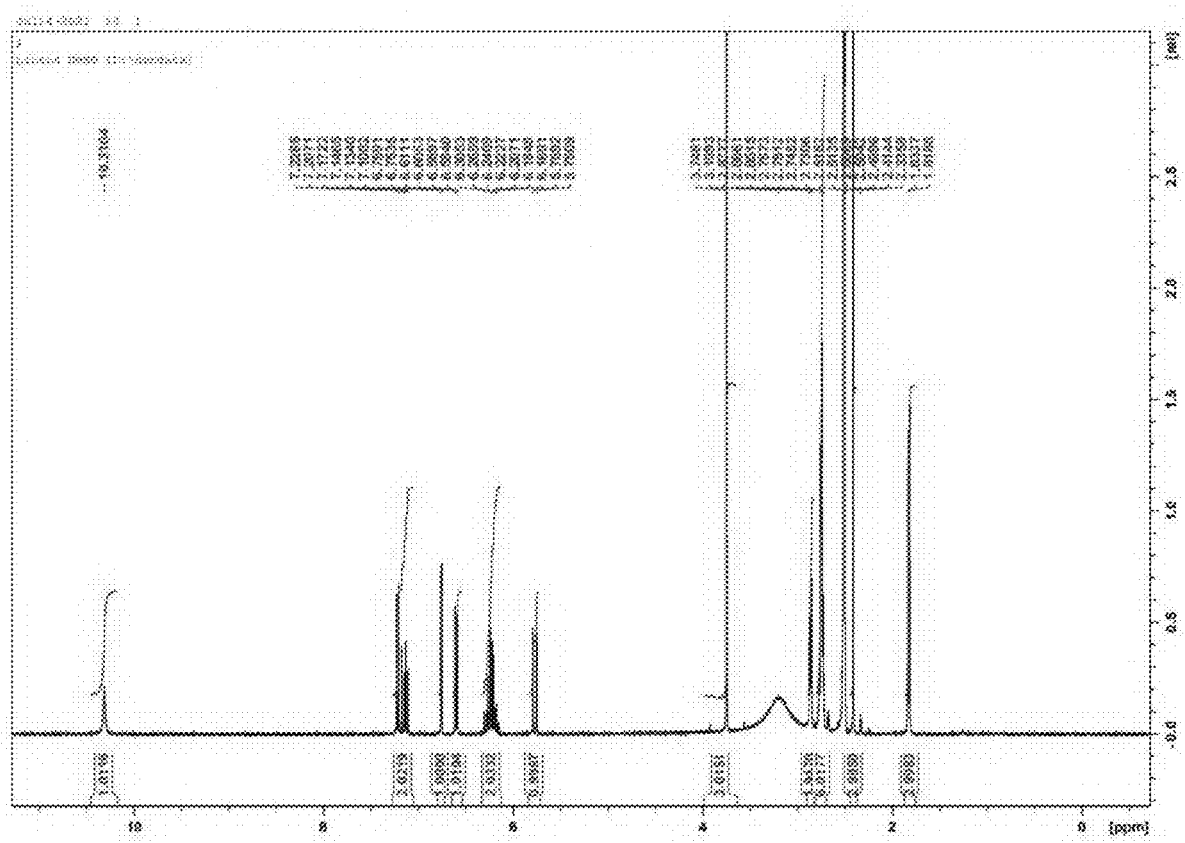

FIG. 721 depicts the $^1$H NMR spectrum of Experiment 6-Sample A1. DMSO-$d_6$ used as deuterated solvent.

Figure 722:
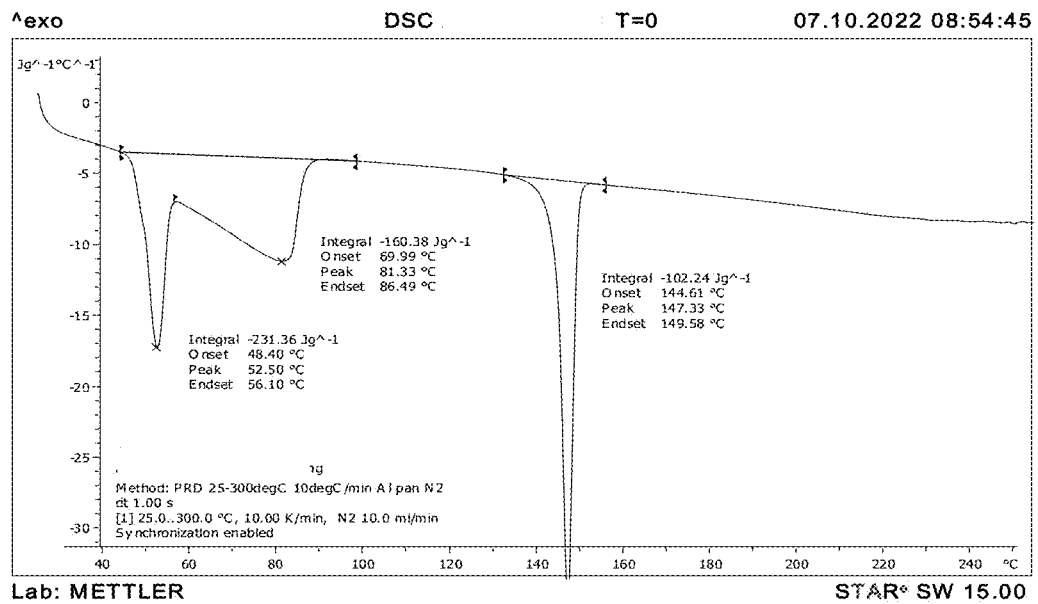

FIG. 722 depicts the DSC profile of Experiment 6-Sample A1, t=0.

Figure 723:
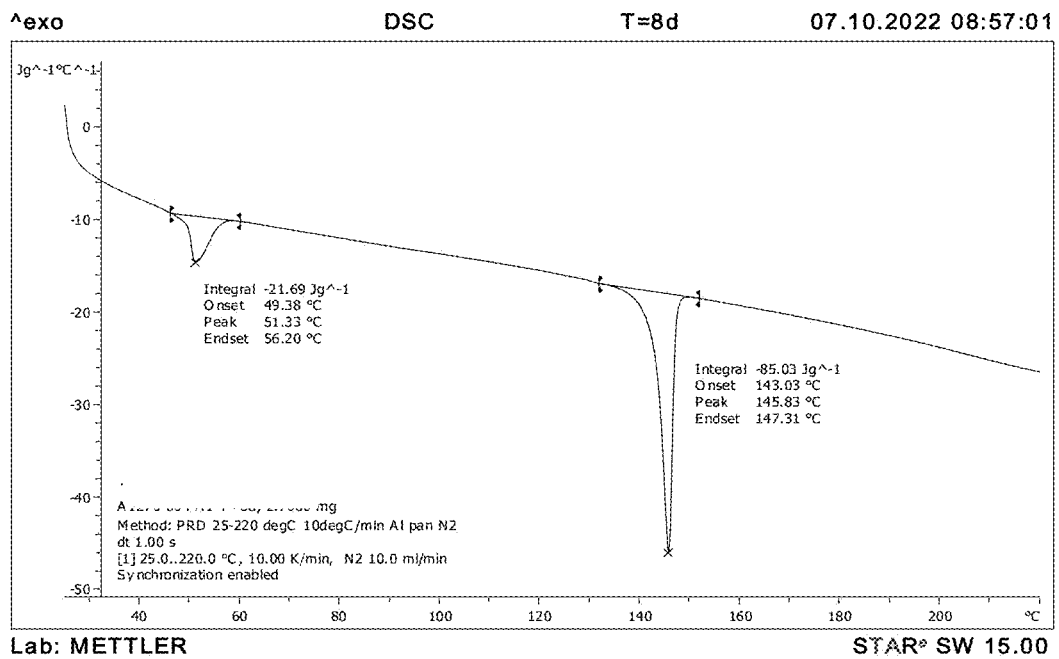

FIG. 723 depicts the DSC profile of Experiment 6-Sample A1, t=8 days.

Figure 724:
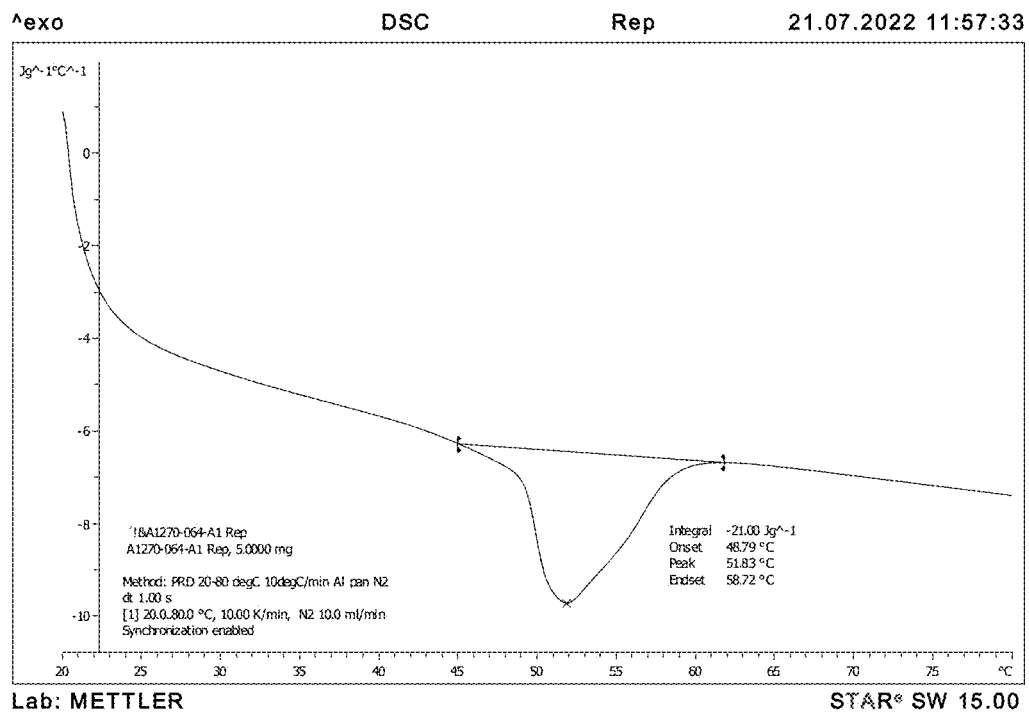

FIG. 724 depicts the DSC profile of Experiment 6-Sample A1 Rep from 20 to 80° C.

Figure 725:
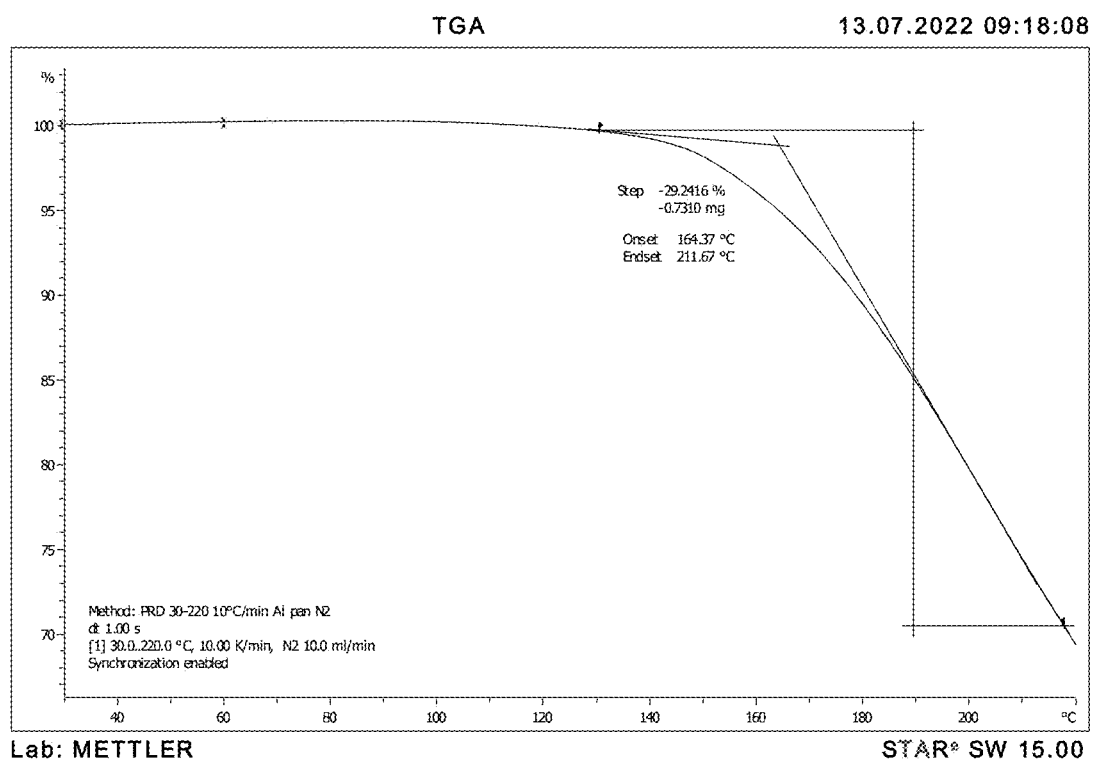

FIG. 725 depicts the TGA profile of Experiment 6-Sample A1 t=0 days.

Figure 726:
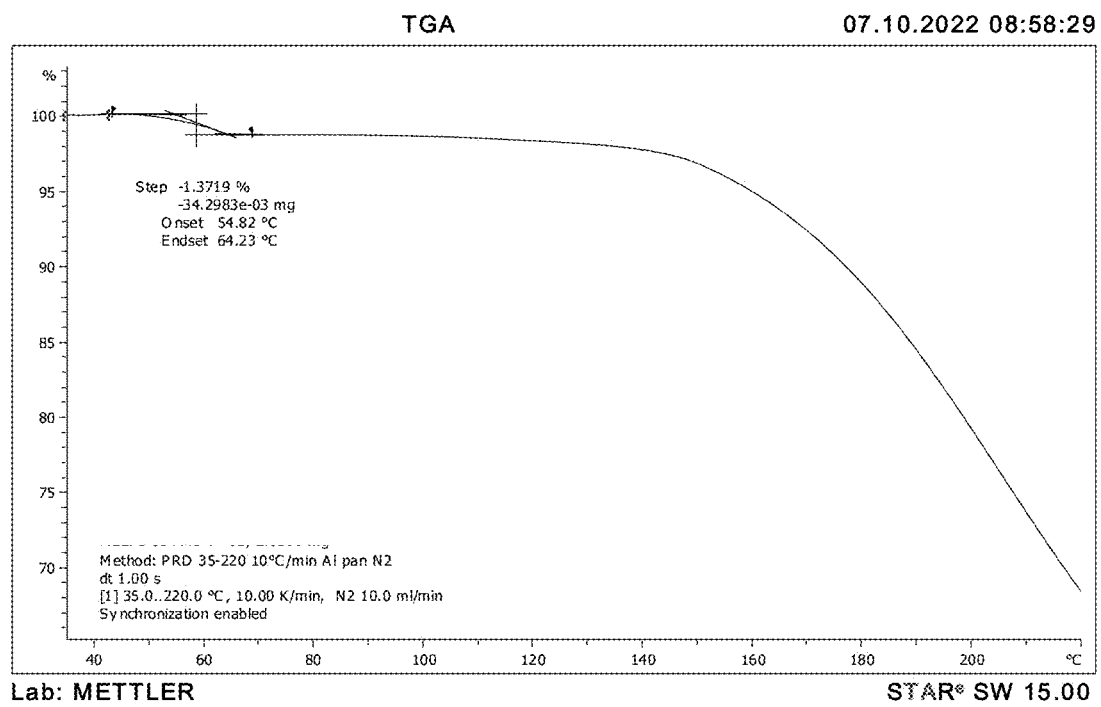

FIG. 726 depicts the TGA profile of Experiment 6-Sample A1 t=8 days.

Figure 727:
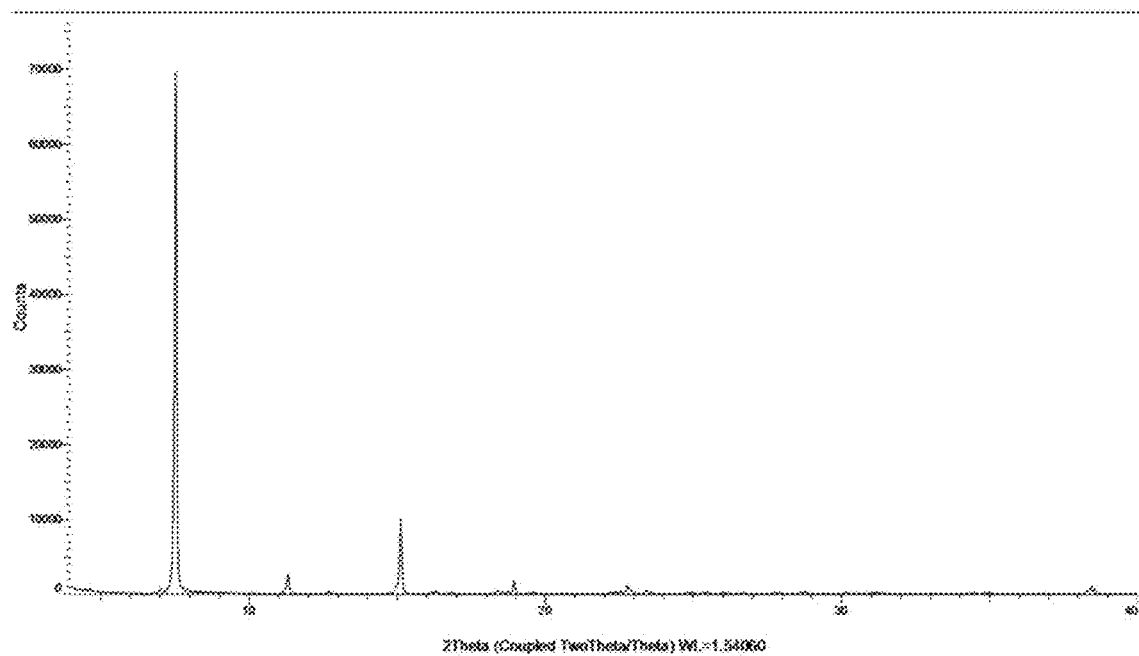

FIG. 727 depicts the XRPD profile of Experiment 2-Sample S1.

Figure 728:
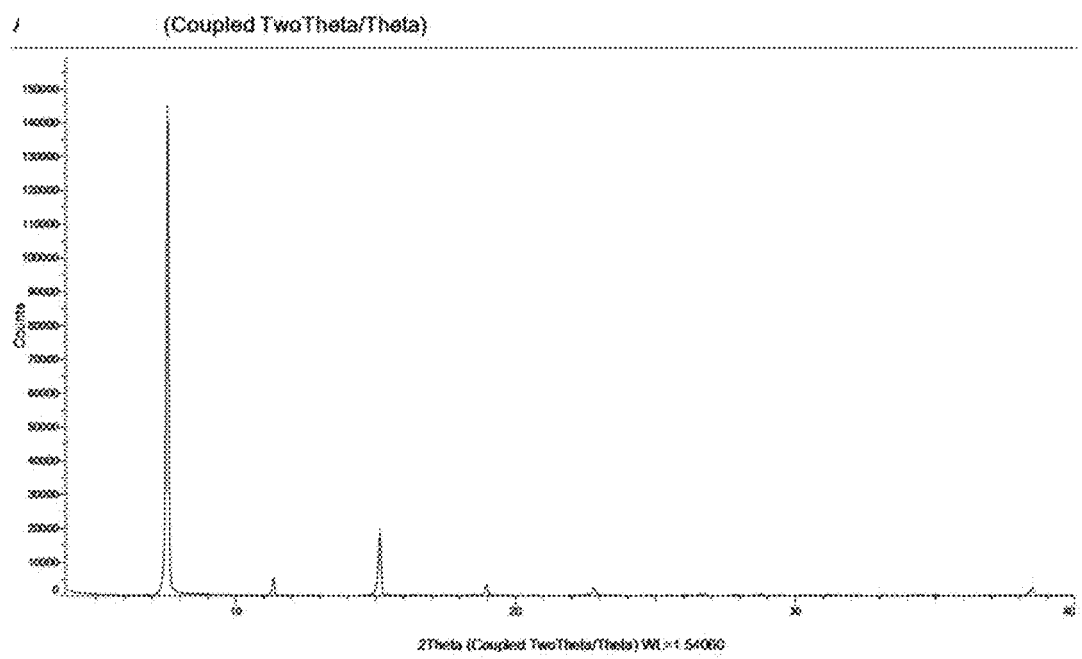

FIG. 728 depicts the XRPD profile of Experiment 6-Sample A1.

Figure 728A:
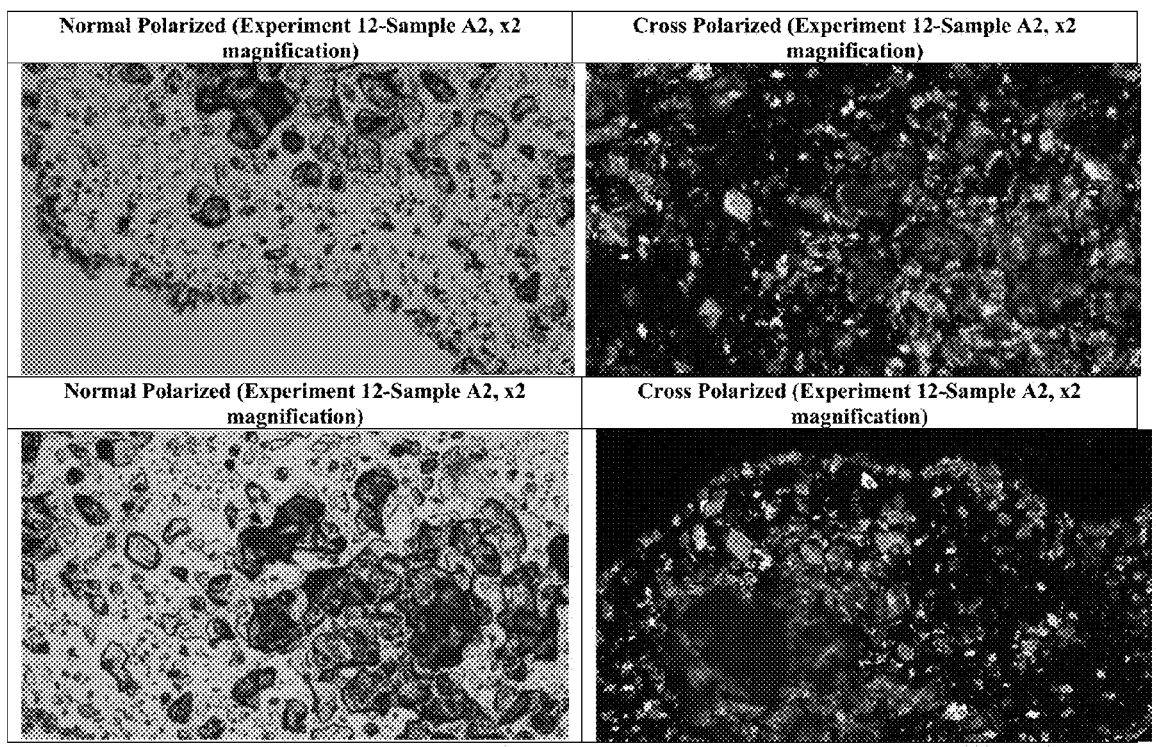

FIG. 728A depicts the PLM of Experiment 12-Sample A2.

Figure 729:
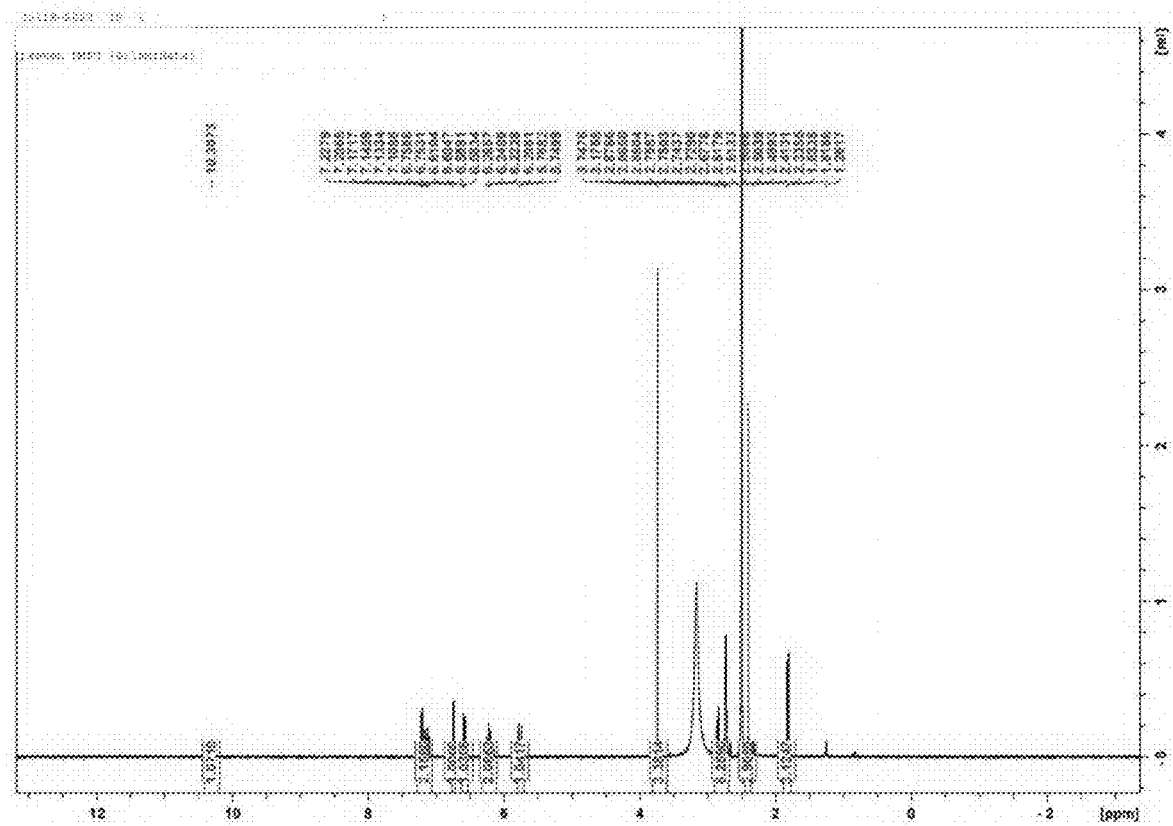

FIG. 729 depicts the $^1$H NMR spectrum of Experiment 10-Sample A2.

Figure 730:
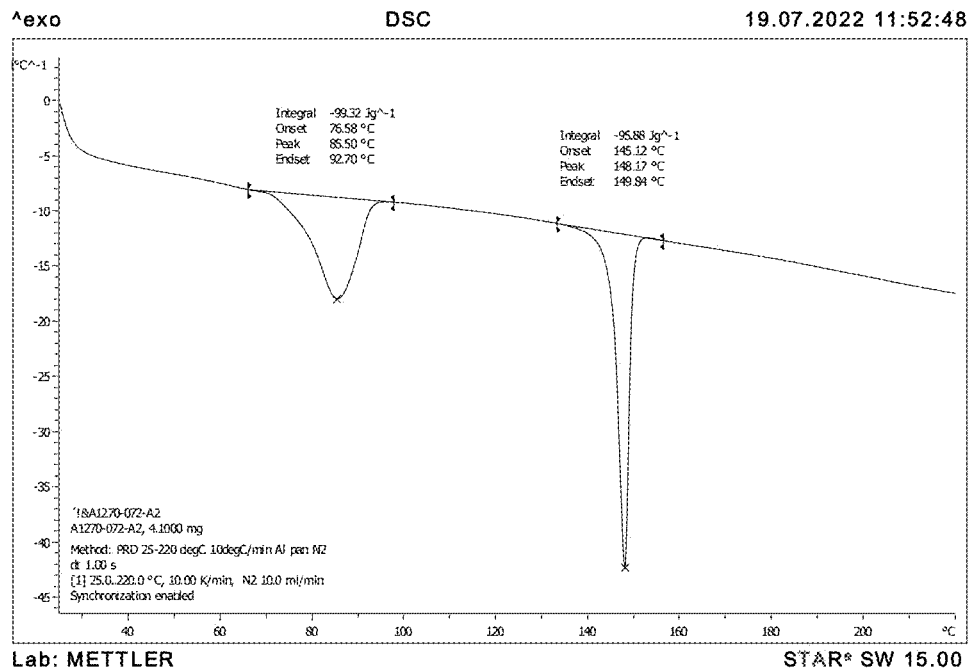

FIG. 730 depicts the DSC profile of Experiment 10-Sample A2.

Figure 731:
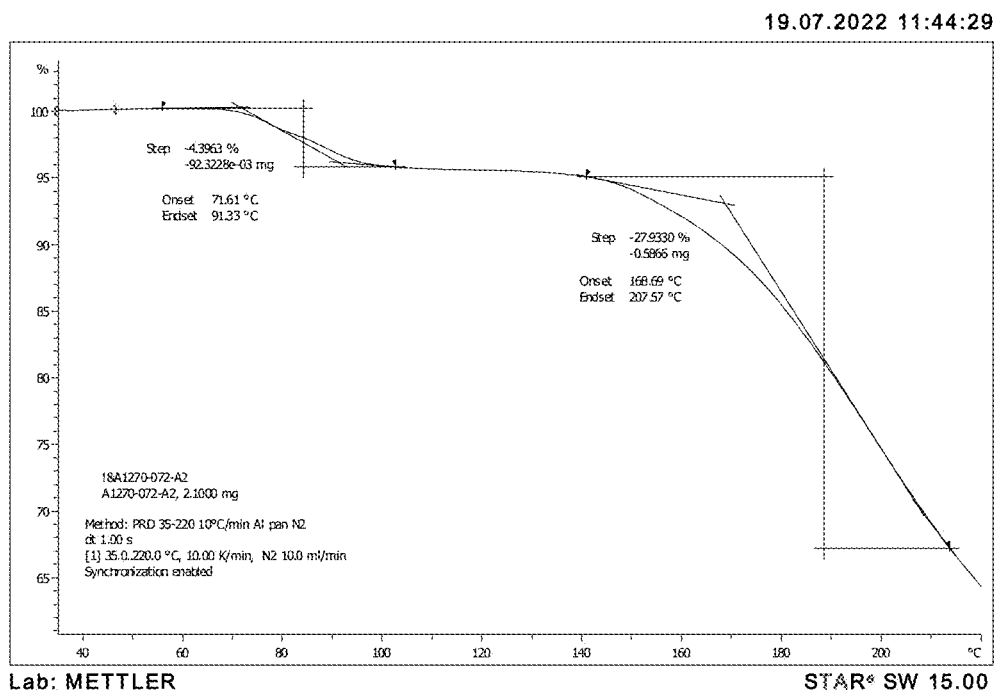

FIG. 731 depicts the TGA profile of Experiment 10-Sample A2.

Figure 732:
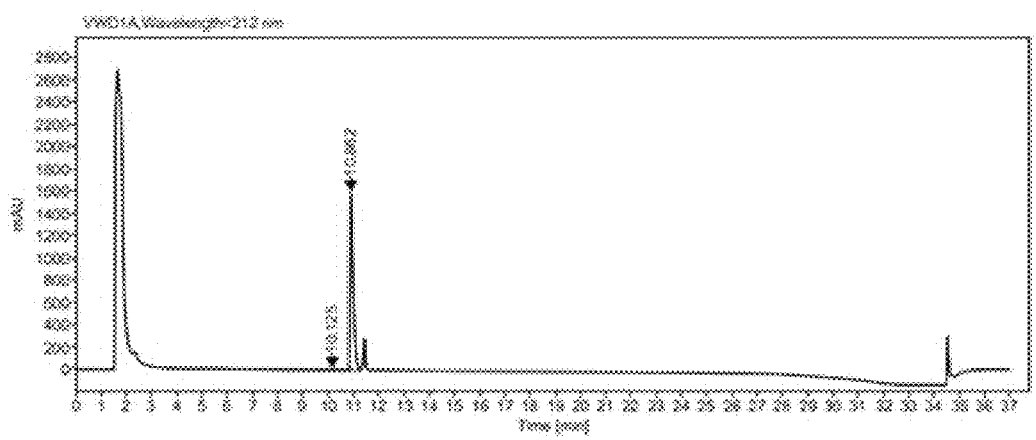

FIG. 732 depicts the HPLC profile of Experiment 10-Sample A2.

Figure 733:
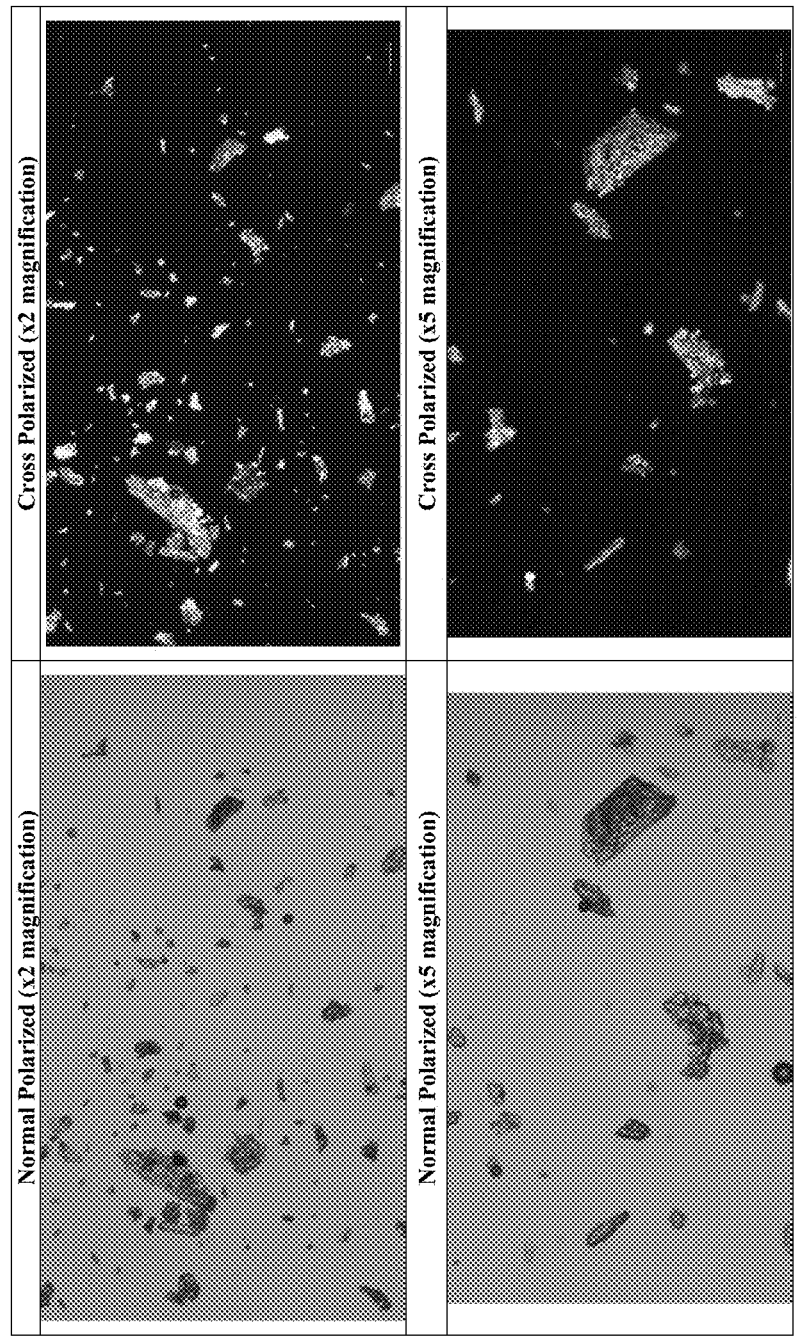

FIG. 733 depicts the PLM of Experiment 10-Sample A2.

Figure 734:
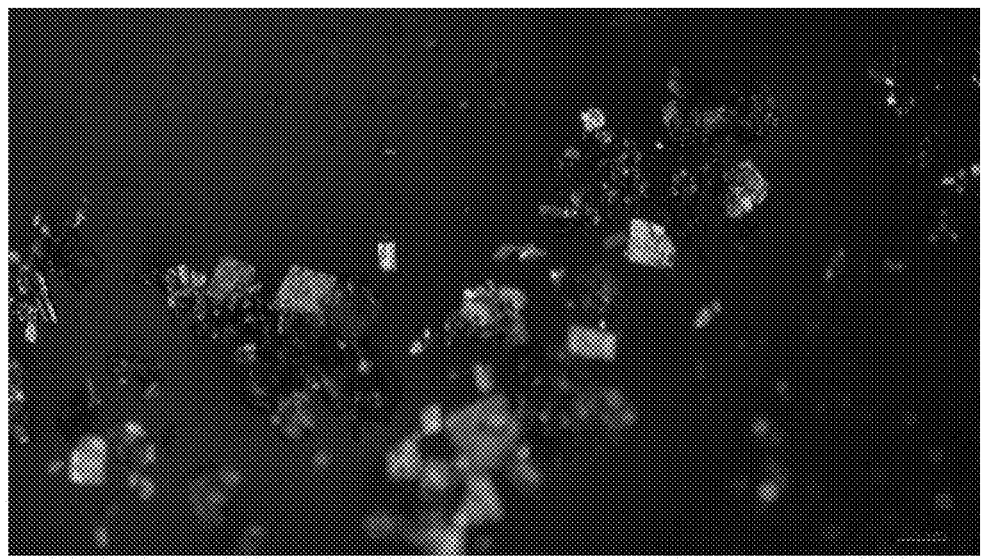

FIG. 734 depicts the PLM of Experiment 3-Sample R1 (cross-polarised).

Figure 735:
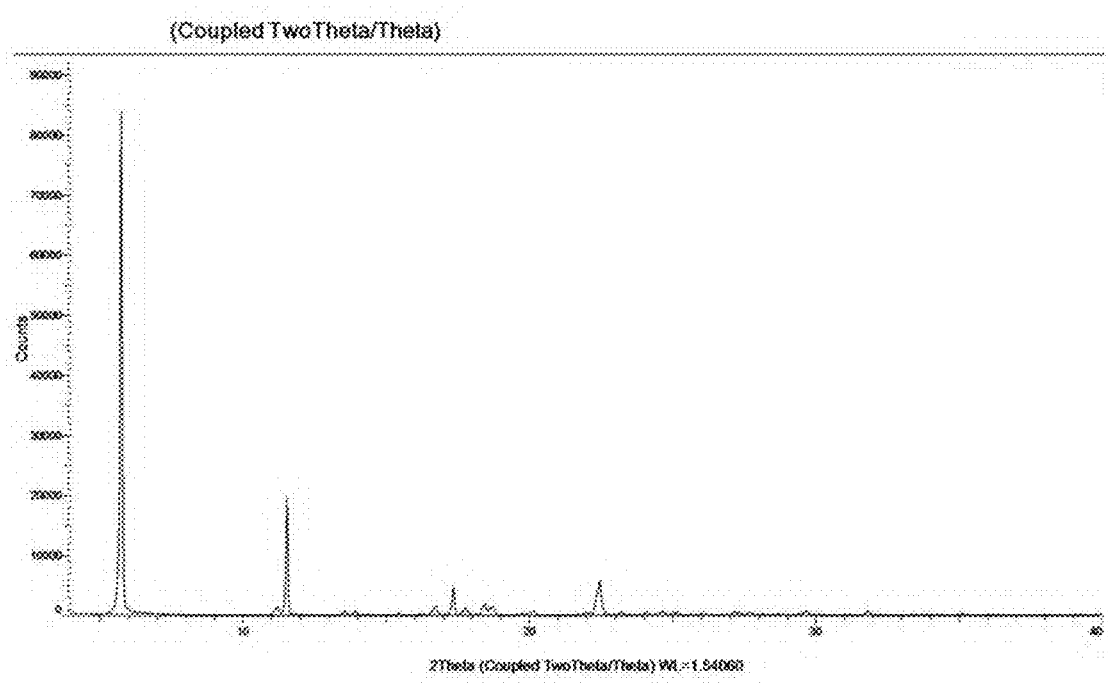

FIG. 735 depicts the XRPD profile of Experiment 3-Sample R1.

Figure 736:
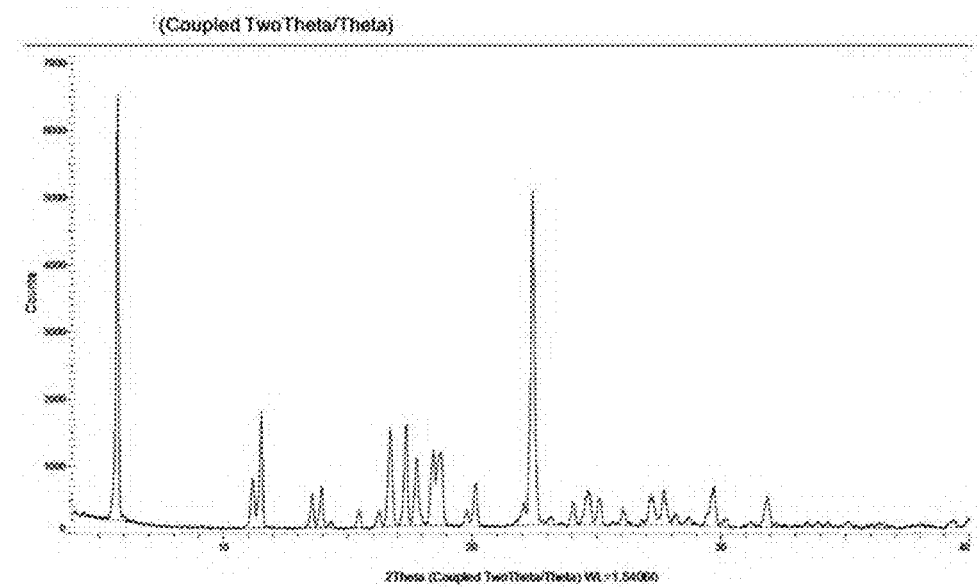

FIG. 736 depicts the XRPD profile of Experiment 10-Sample A2.

Figure 737:
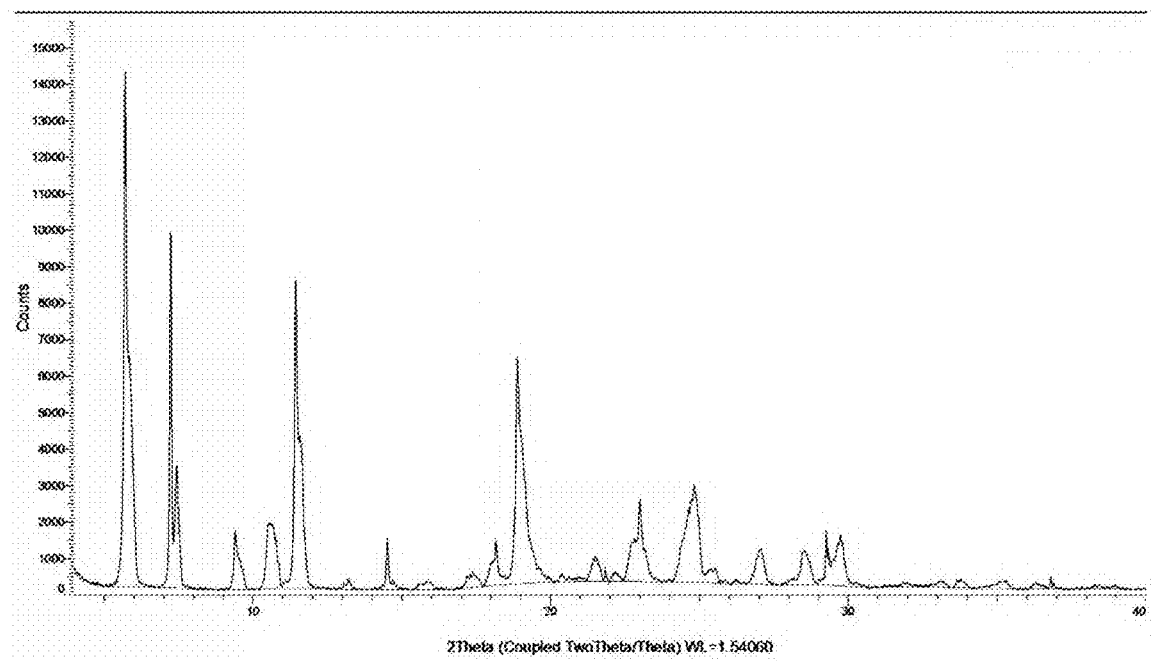

FIG. 737 depicts the XRPD profile of Experiment 4-Sample H1.

Figure 738:
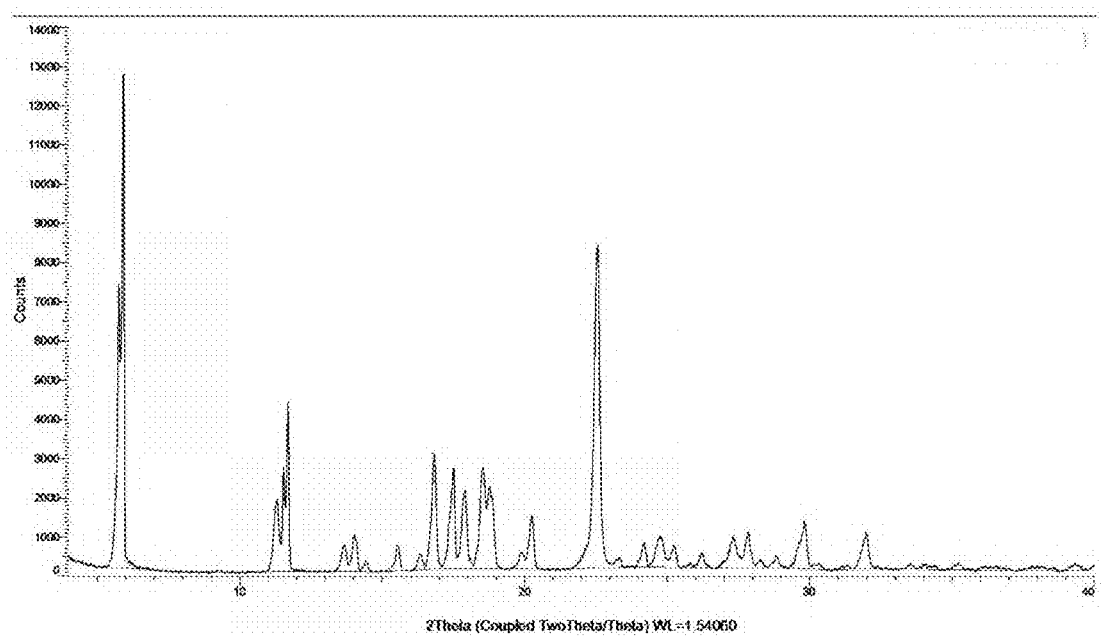

FIG. 738 depicts the XRPD profile of Experiment 5-Sample R1.

Figure 739:
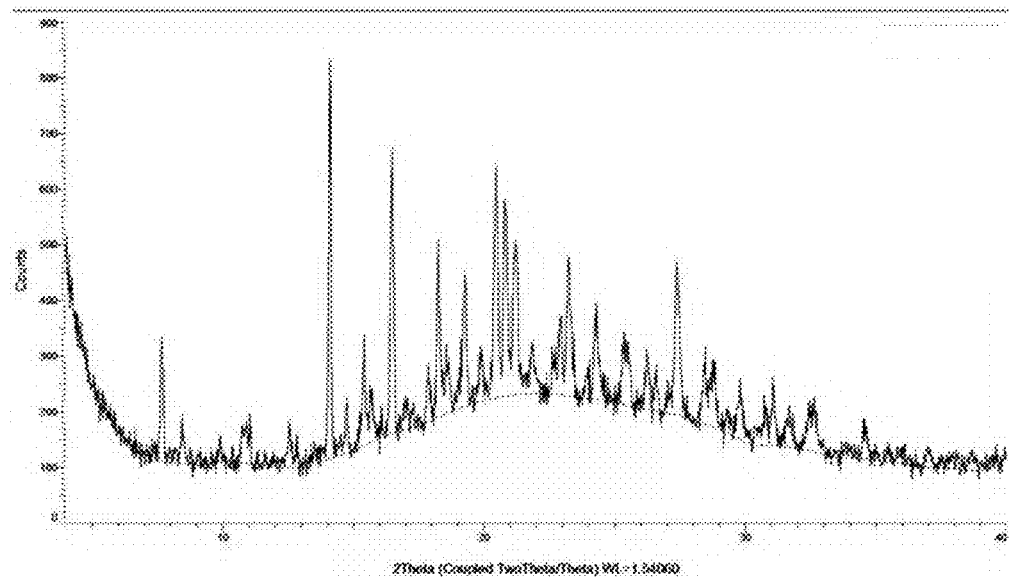

FIG. 739 depicts the XRPD profile of Experiment 4-Sample E1.

Figure 740:
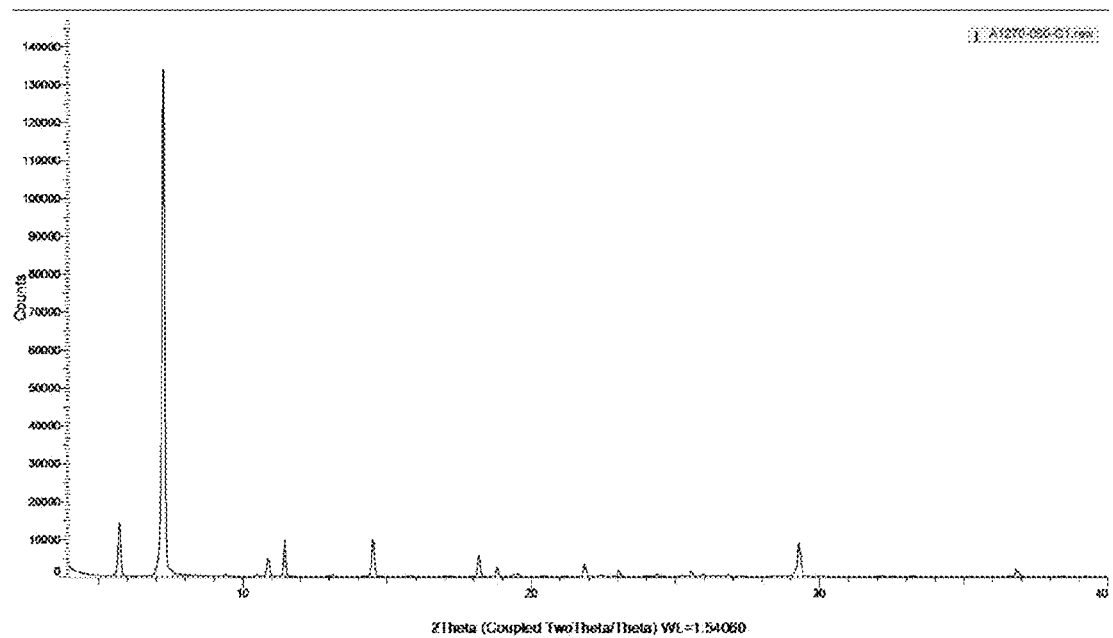

FIG. 740 depicts the XRPD profile of Experiment 5-Sample G1.

Figure 741:
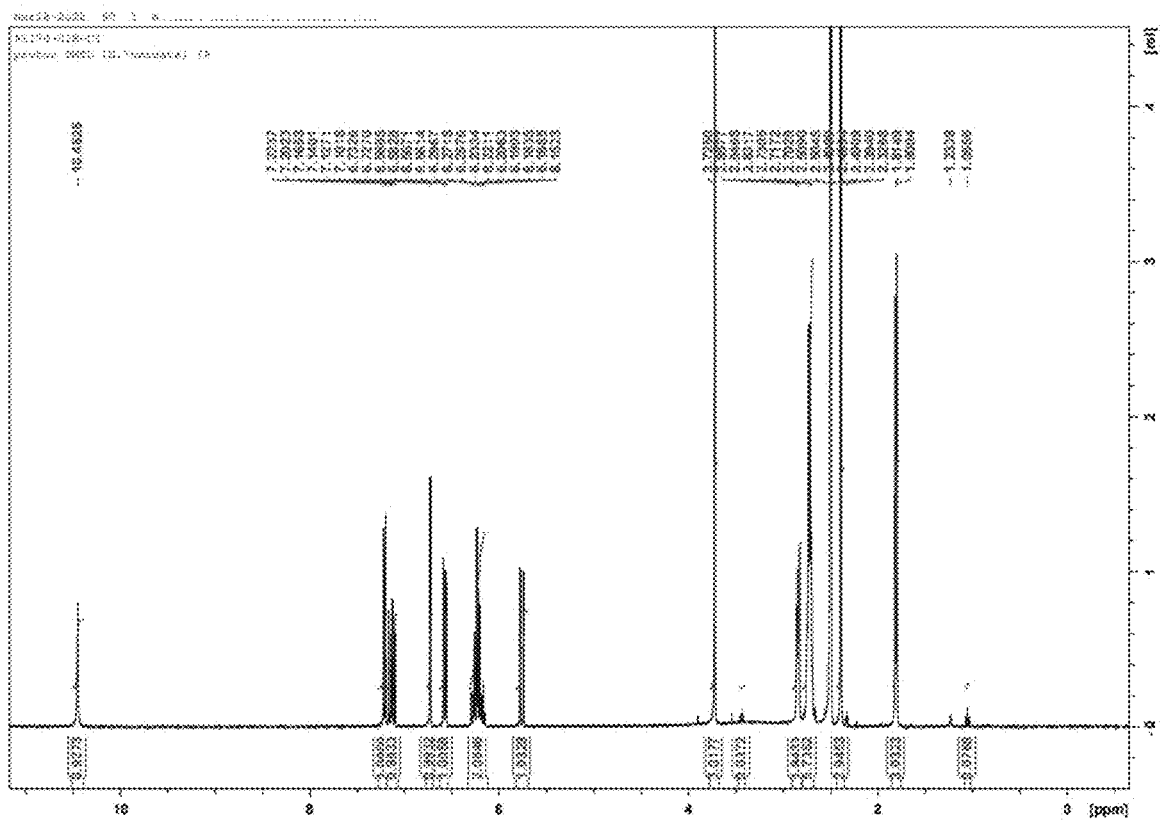

FIG. 741 depicts the $^1$H NMR spectrum of Experiment 13-Sample CL DMSO-$d_6$ used as deuterated solvent.

Figure 742:
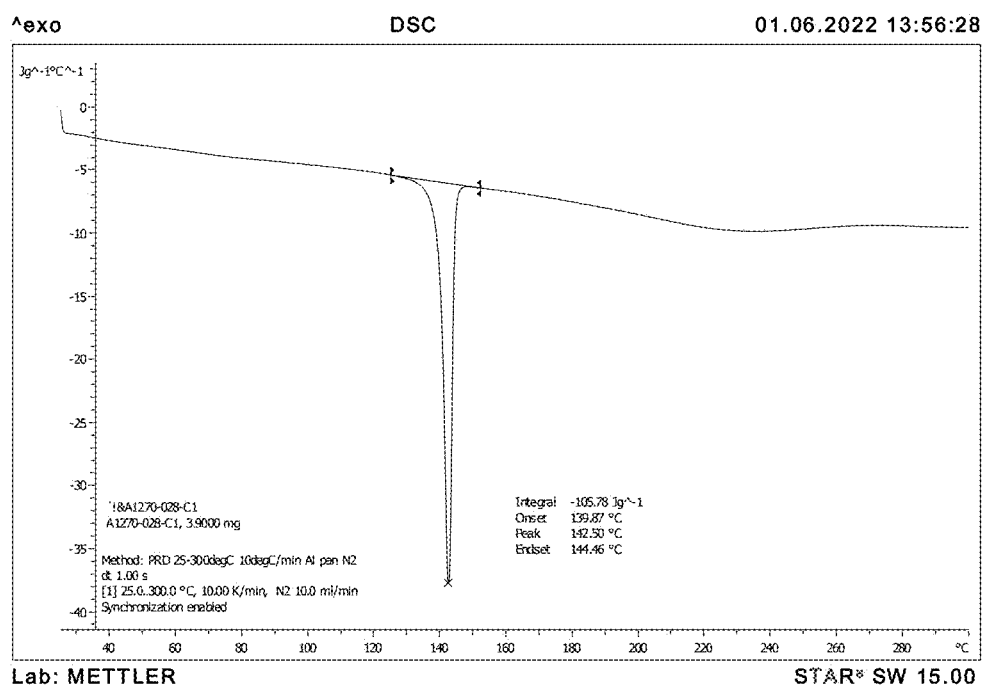

FIG. 742 depicts the DSC profile of Experiment 13-Sample CL.

Figure 743:
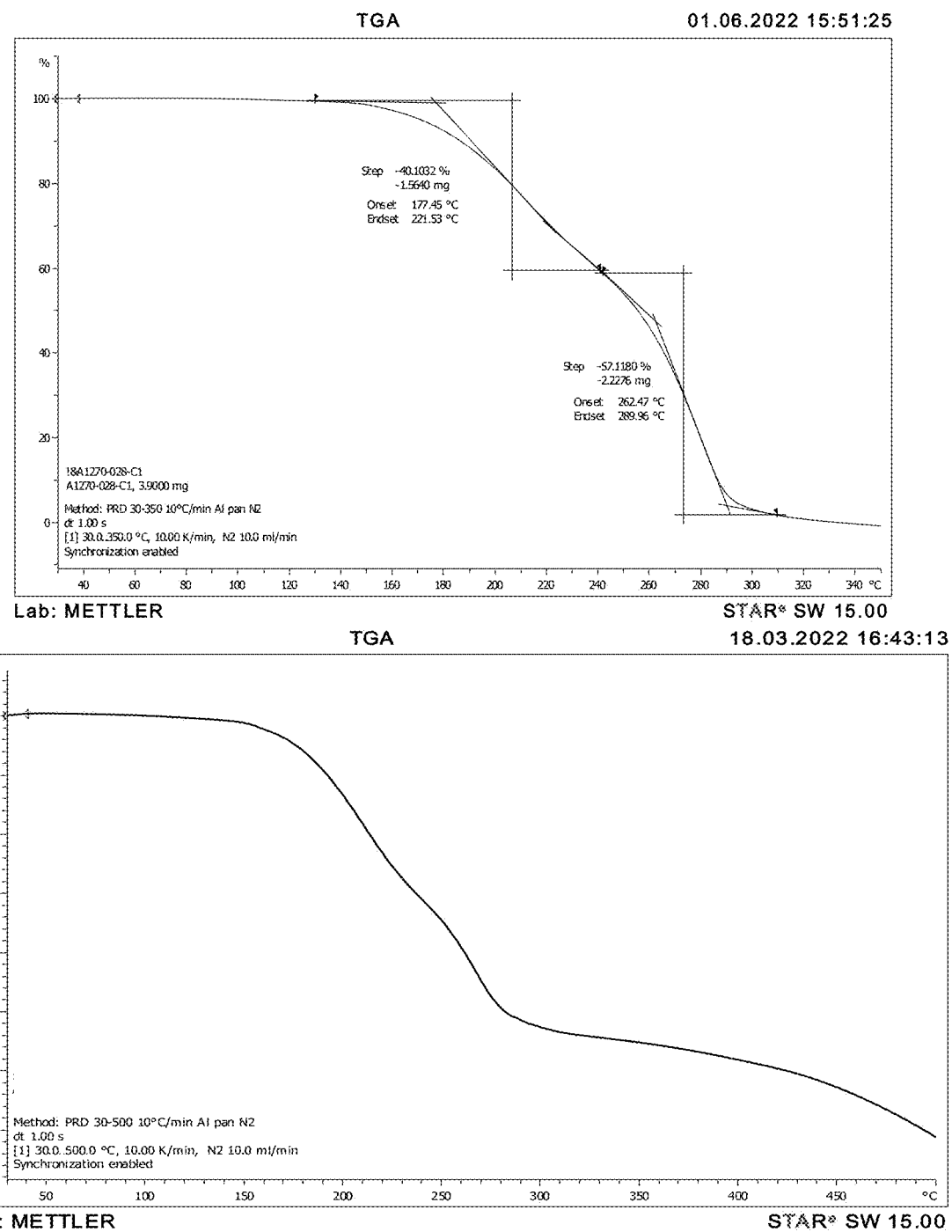

FIG. 743 depicts the TGA profile of Experiment 13-Sample C1.

Figure 744:
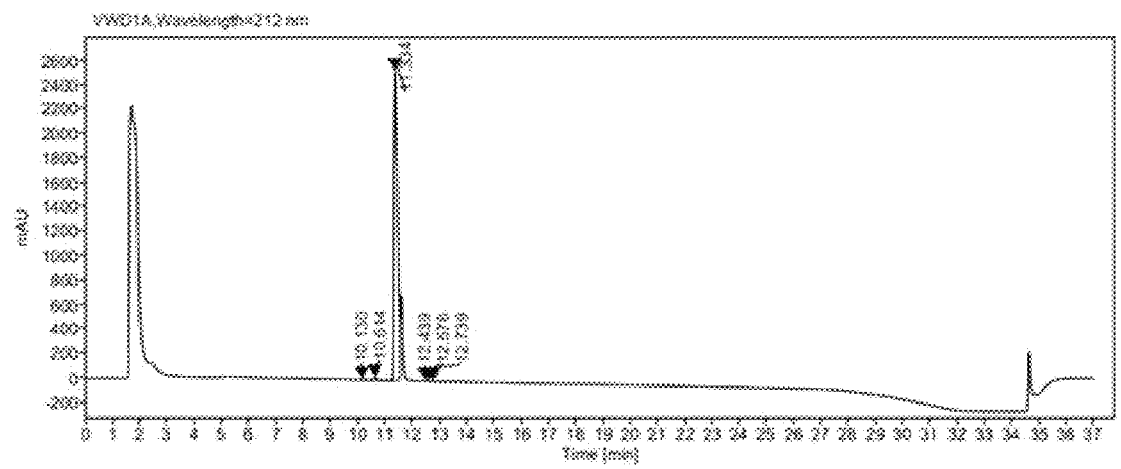

FIG. 744 depicts the HPLC profile of Experiment 13-Sample C1.

Figure 755:
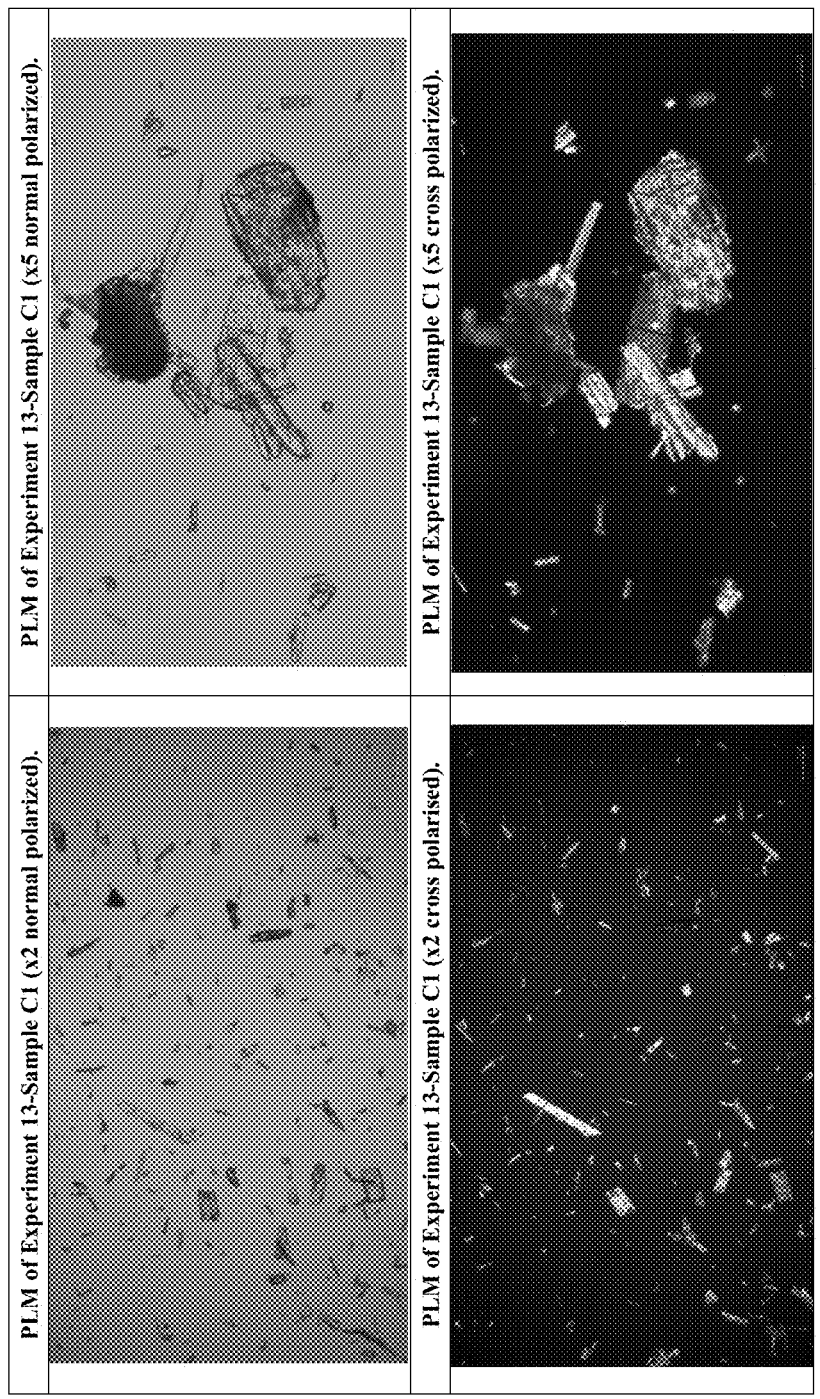

FIG. 755 depicts the polarized light microscopy of Experiment 13-Sample C1.

Figure 756:
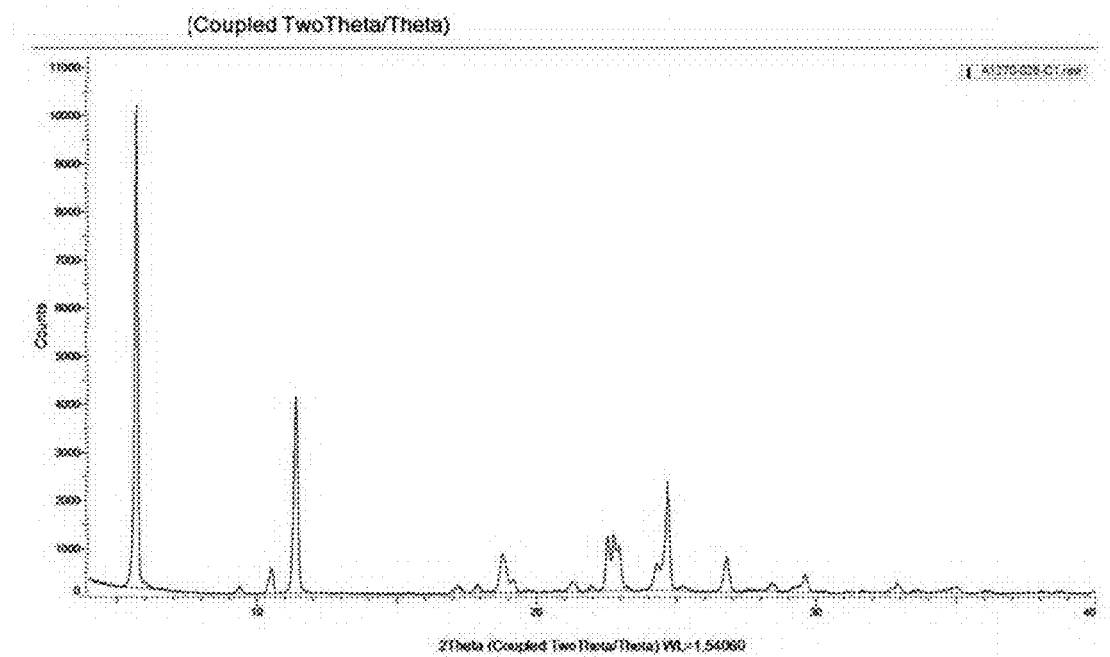

FIG. 756 depicts the XRPD profile of Experiment 13-Sample C1.

Figure 757:
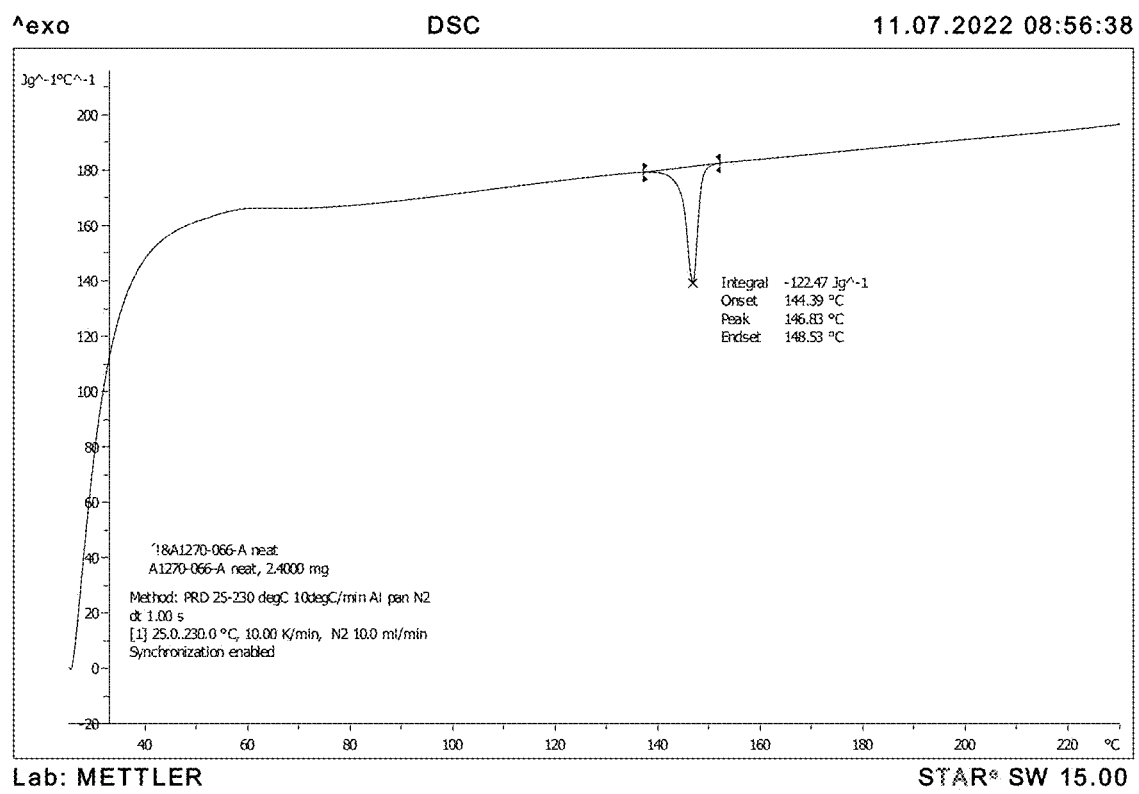

FIG. 757 depicts the DSC profile of Experiment 7-Sample A Neat.

Figure 758:
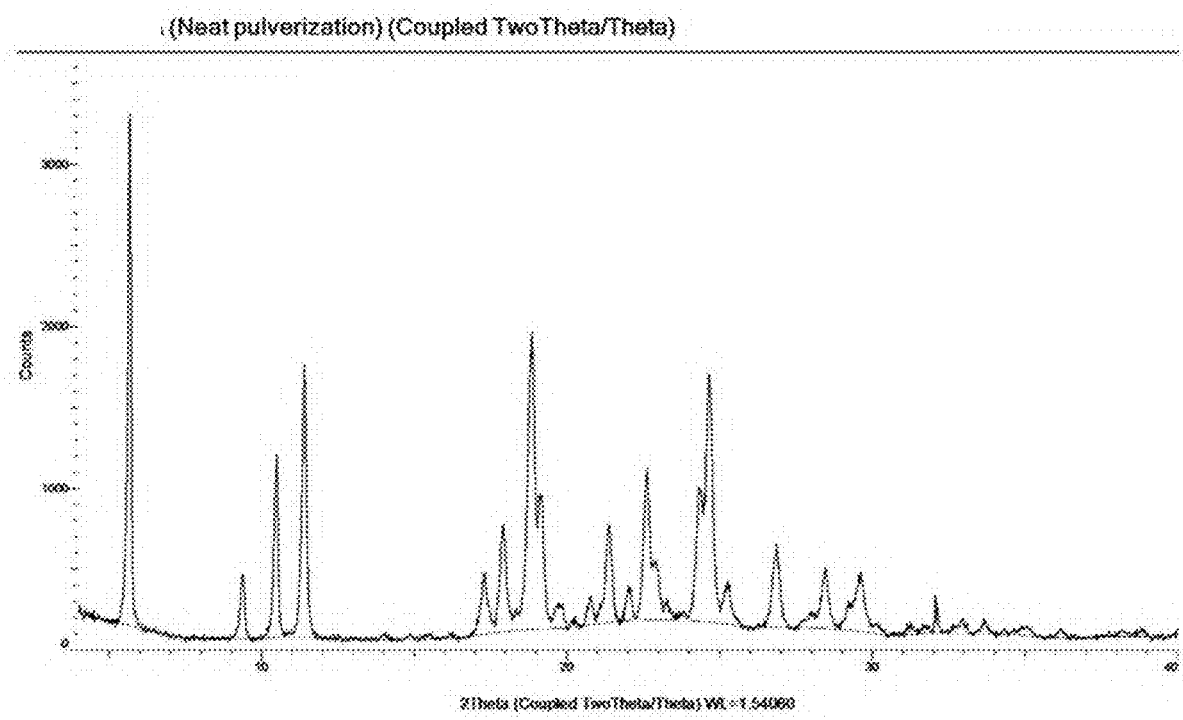

FIG. 758 depicts the XRPD profile of Experiment 7-Sample A Neat pulverization.

Figure 759:
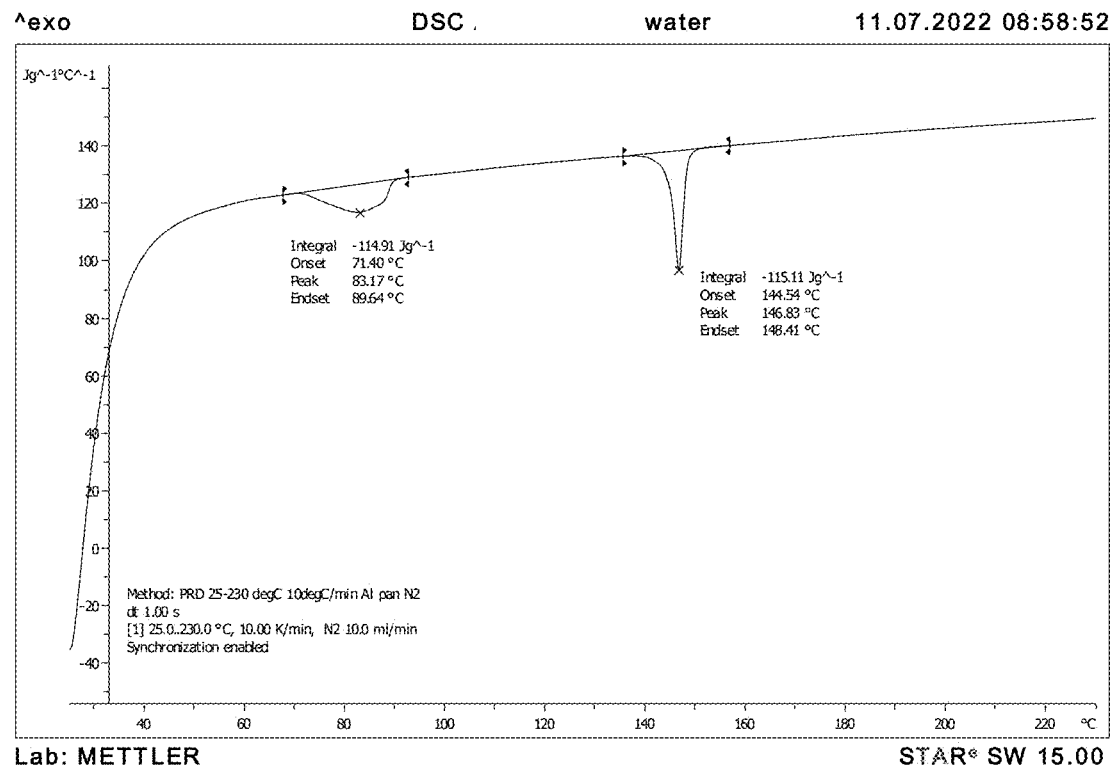

FIG. 759 depicts the DSC profile of Experiment 7-Sample B water.

Figure 760:
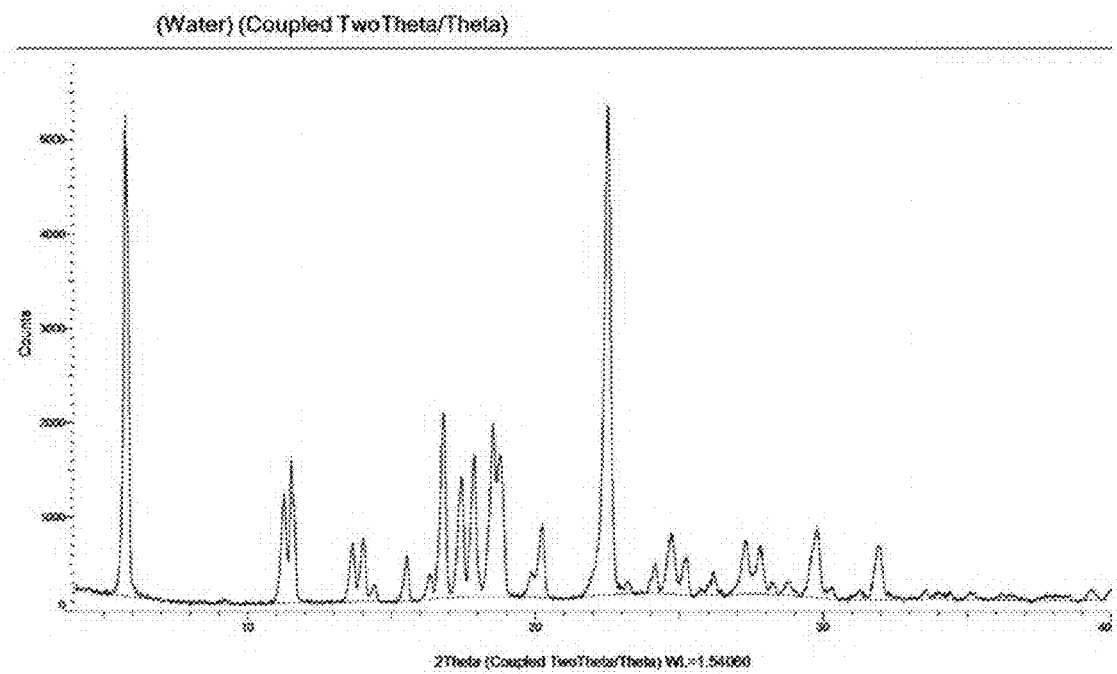

FIG. 760 depicts the XRPD profile of Experiment 7-Sample B water.

Figure 761:
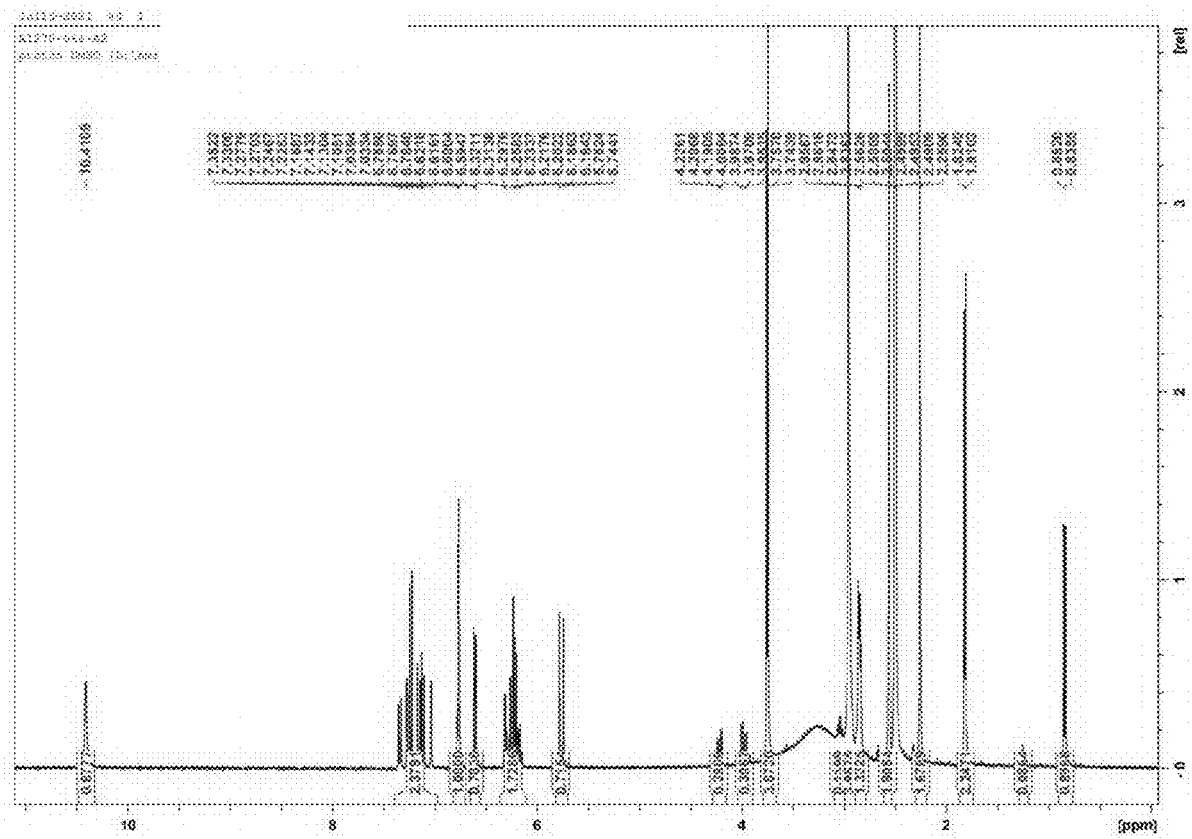

FIG. 761 depicts the $^1$H NMR spectrum of Experiment 8-Sample A2. DMSO-$d_6$ used as deuterated solvent. The chemical composition appears different chemical composition and is attributed to reaction with ethyl formate. Solvent exchange had occurred during oven-drying.

FIG. 762 depicts the DSC profile of Experiment 8-Sample A2.

Figure 763:
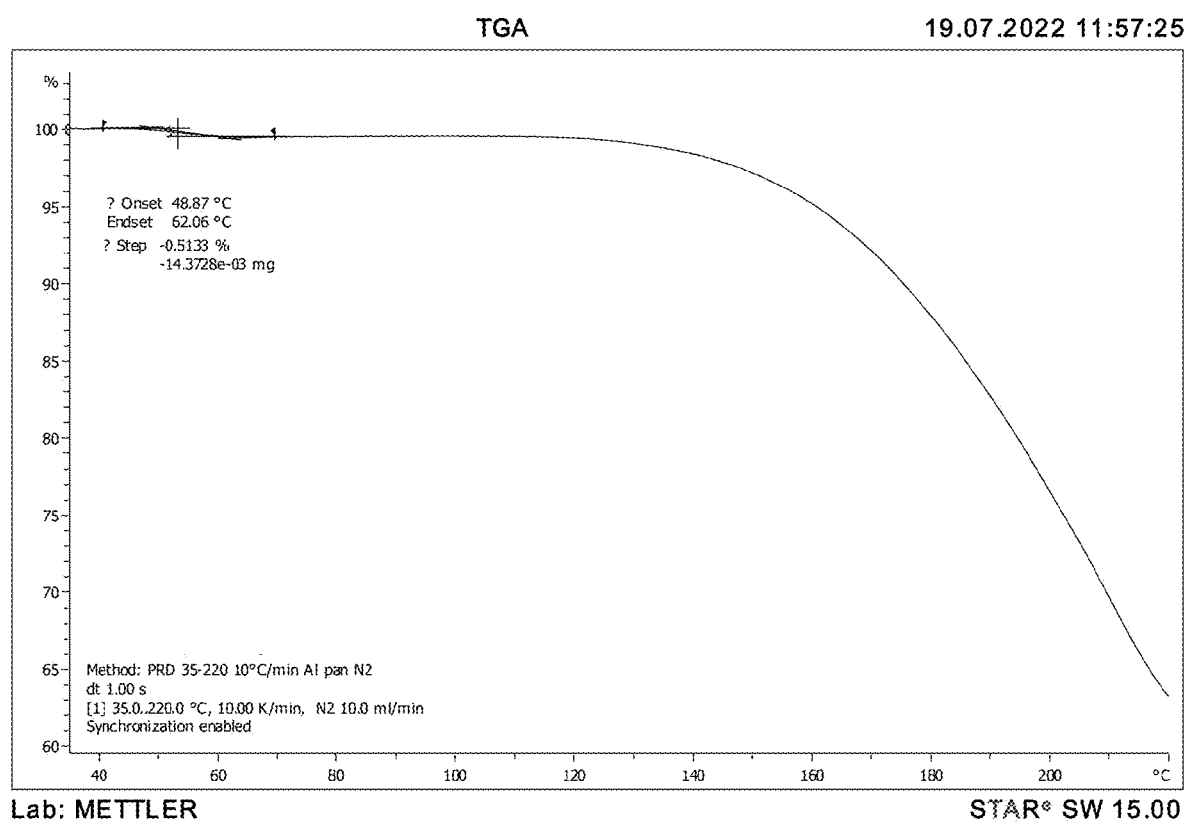

FIG. 763 depicts the TGA profile of Experiment 8-Sample A2.

Figure 764:
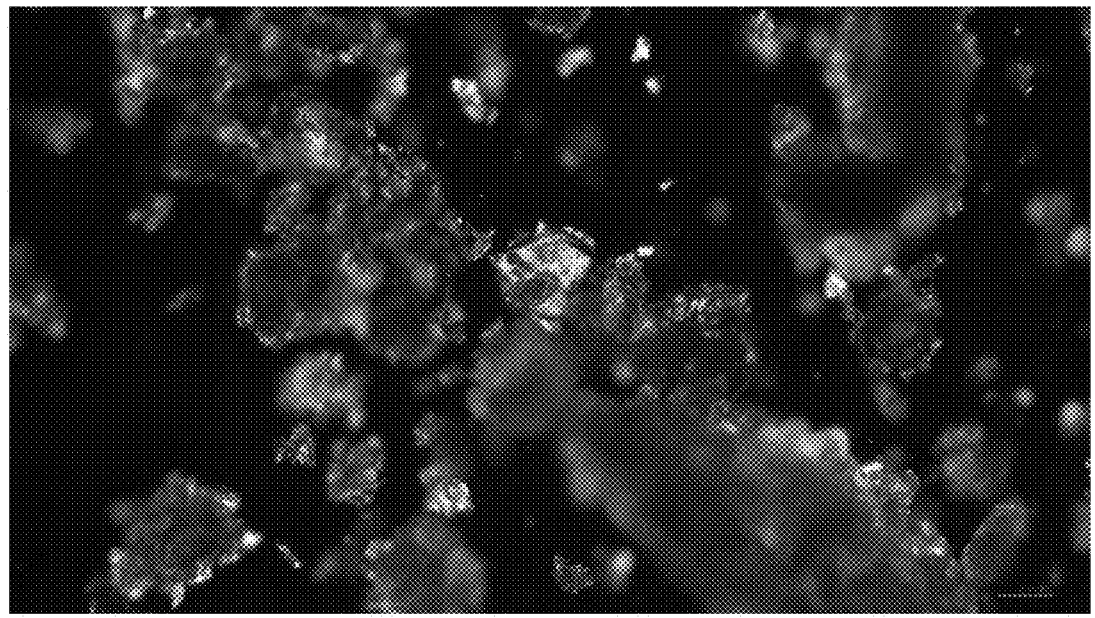

FIG. 764 depicts the PLM of Experiment 8-Sample A2.

Figure 765:
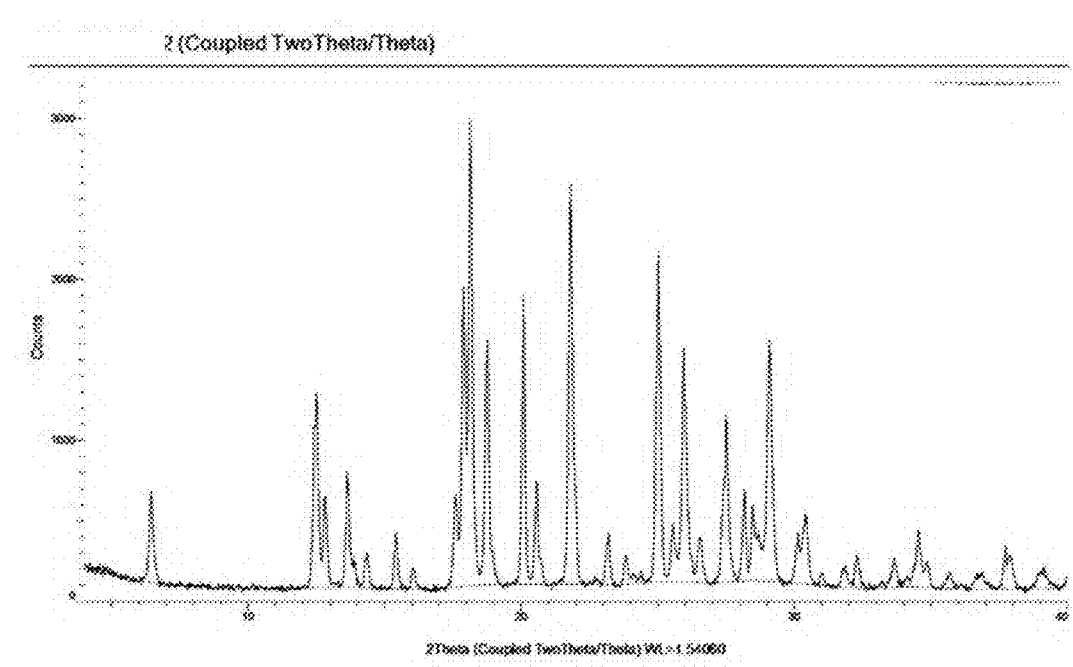

FIG. 765 depicts the XRPD profile of Experiment 8-Sample A2.

Figure 766:
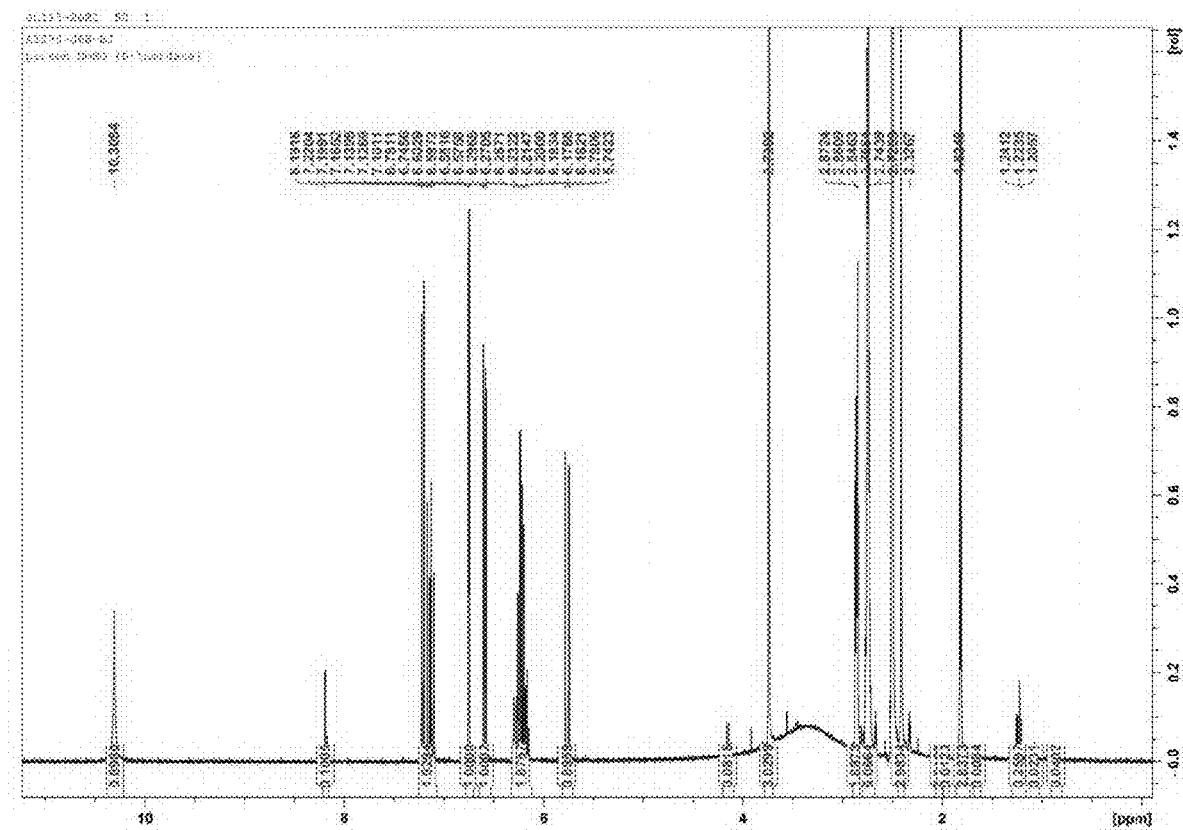

FIG. 766 depicts the $^1$H NMR spectrum of Experiment 8-Sample B2. DMSO-$d_6$ used as deuterated solvent.

Figure 767:
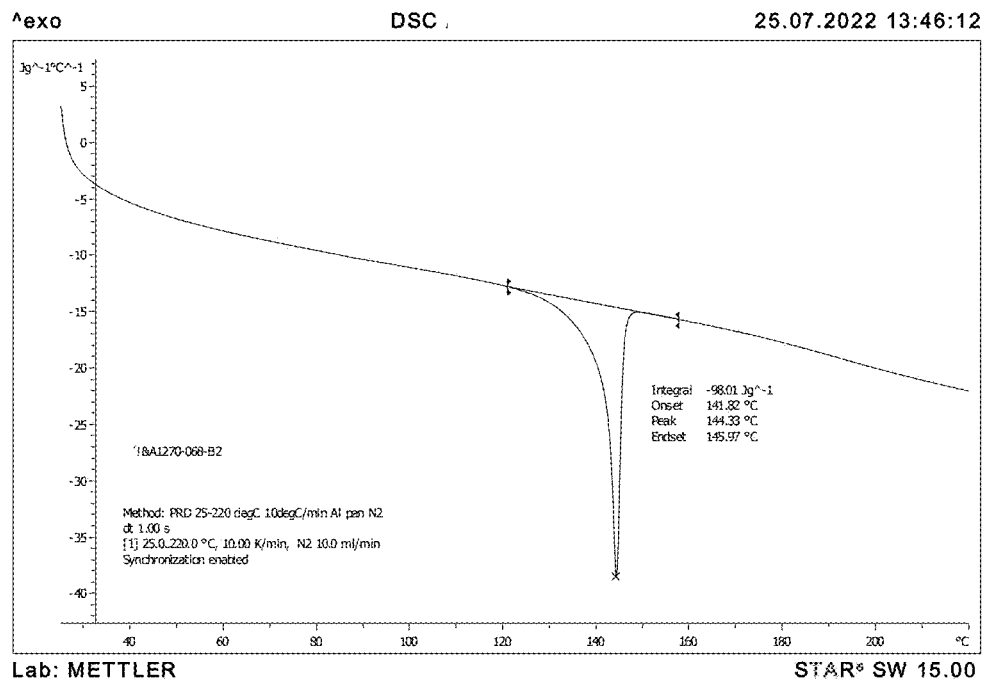

FIG. 767 depicts the DSC profile of Experiment 8-Sample B2.

Figure 768:
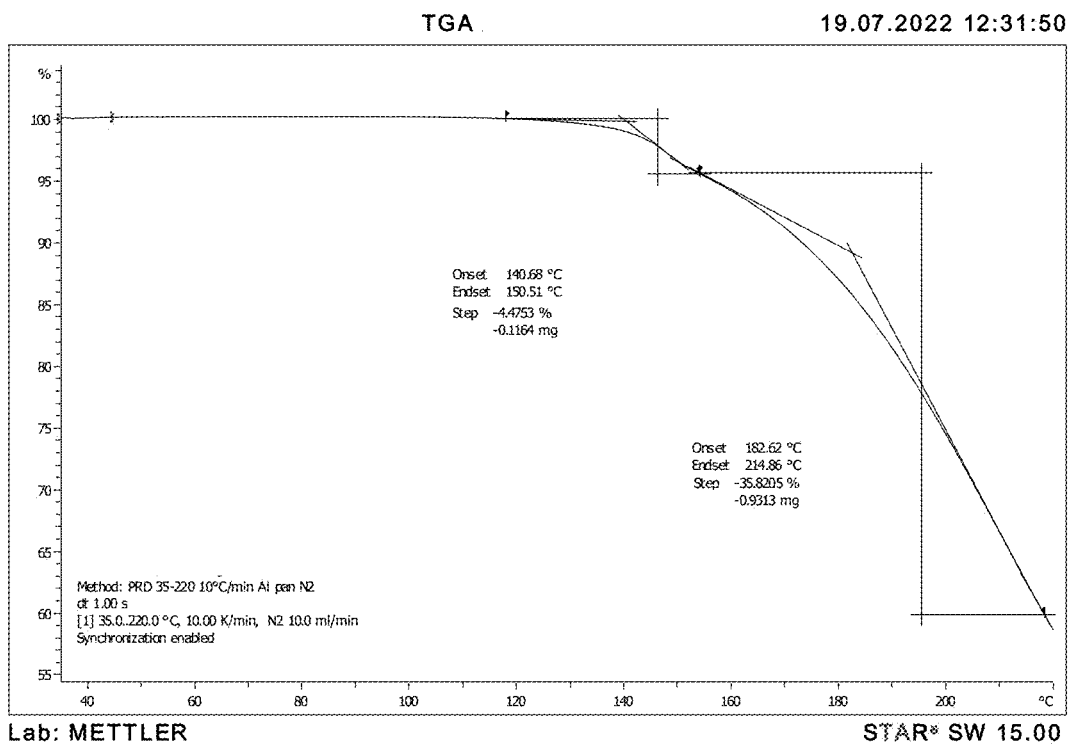

FIG. 768 depicts the TGA profile of Experiment 8-Sample B2.

Figure 769:
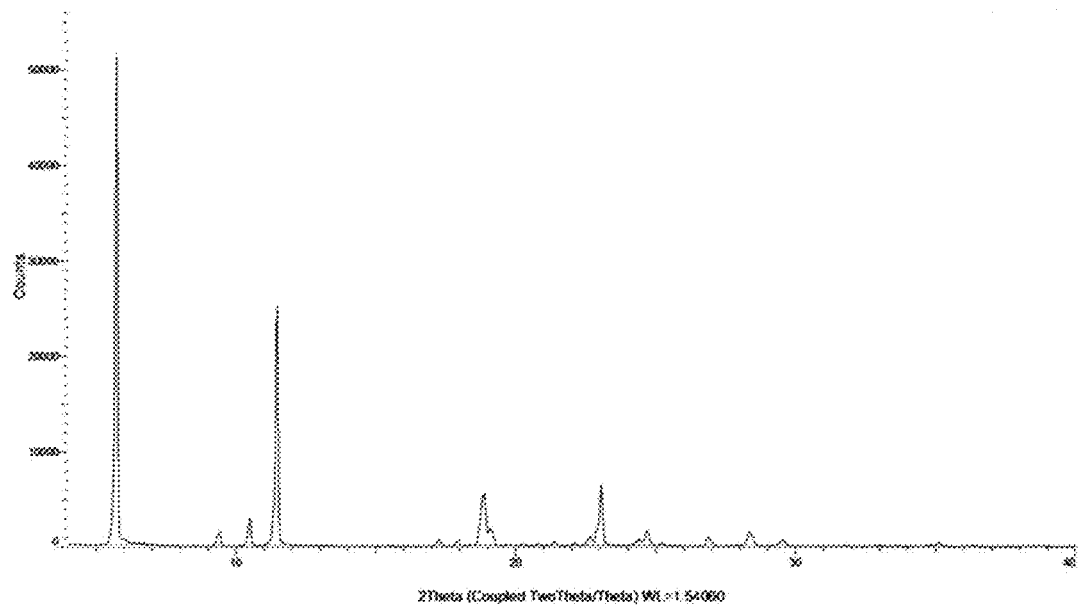

FIG. 769 depicts the XRPD profile of Experiment 8-Sample B2.

Figure 770:
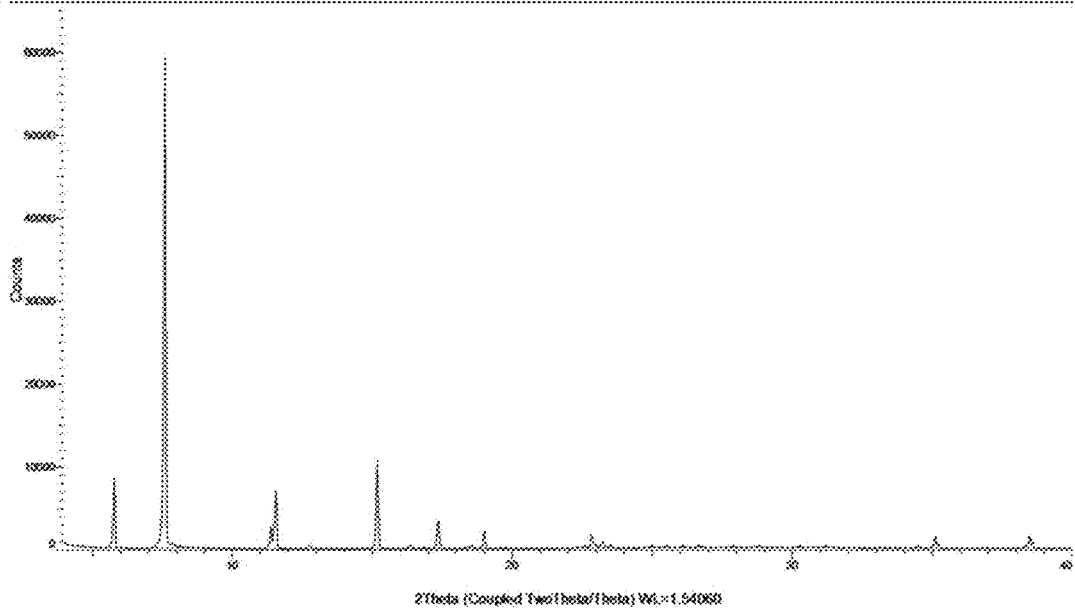

FIG. 770 depicts the XRPD profile of Experiment 12-Sample A2.

Figure 771:
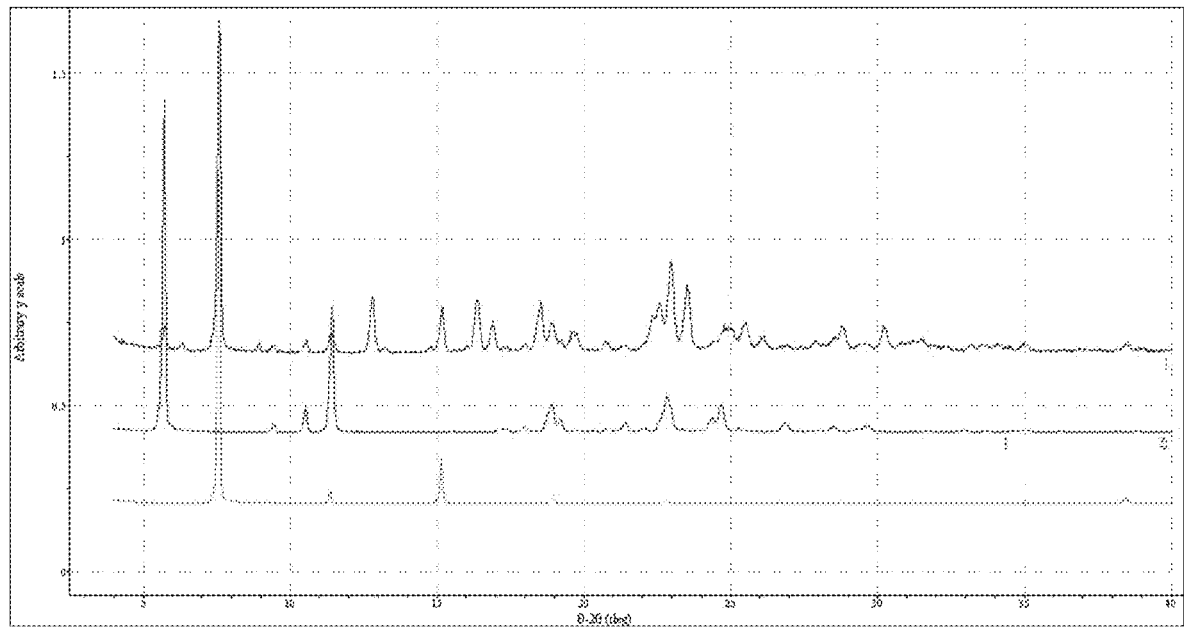

FIG. 771 depicts the Overlaid of XRPD profiles of Tabernanthalog sorbate salt samples: Experiment 6-Sample B1 (via evaporation from methanol/acetone consistent with Pattern #1>Form A>unk, top), Experiment 6-Sample A1 (via evaporation from water, Pattern #1, Form B, bottom) and Experiment 1-Sample A2 (Form A, middle).

Figure 772:
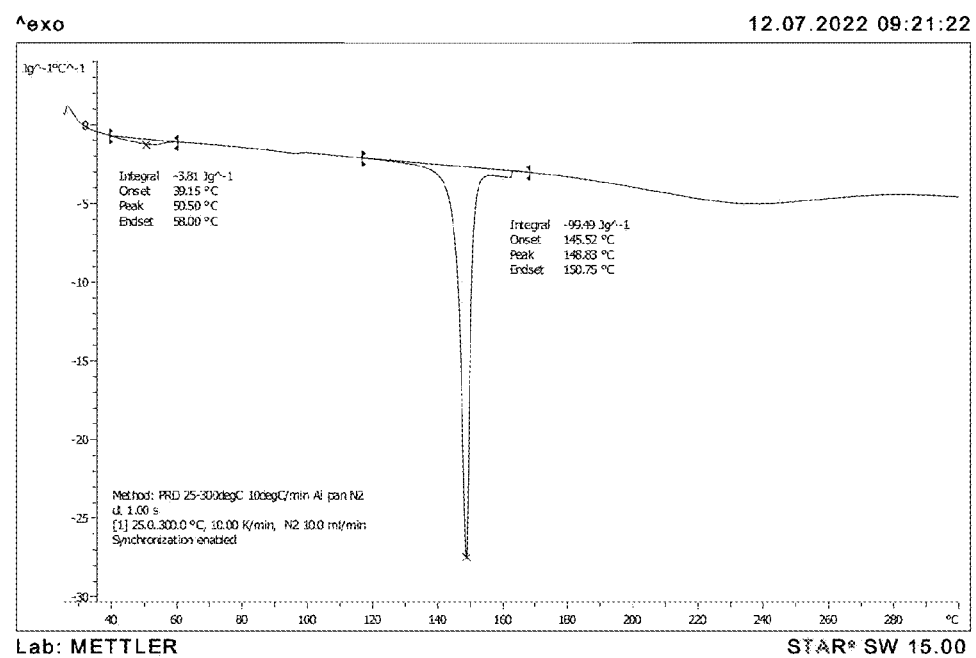

FIG. 772 depicts the DSC profile of Experiment 6-Sample B1. Predominantly Form A.

Figure 773:
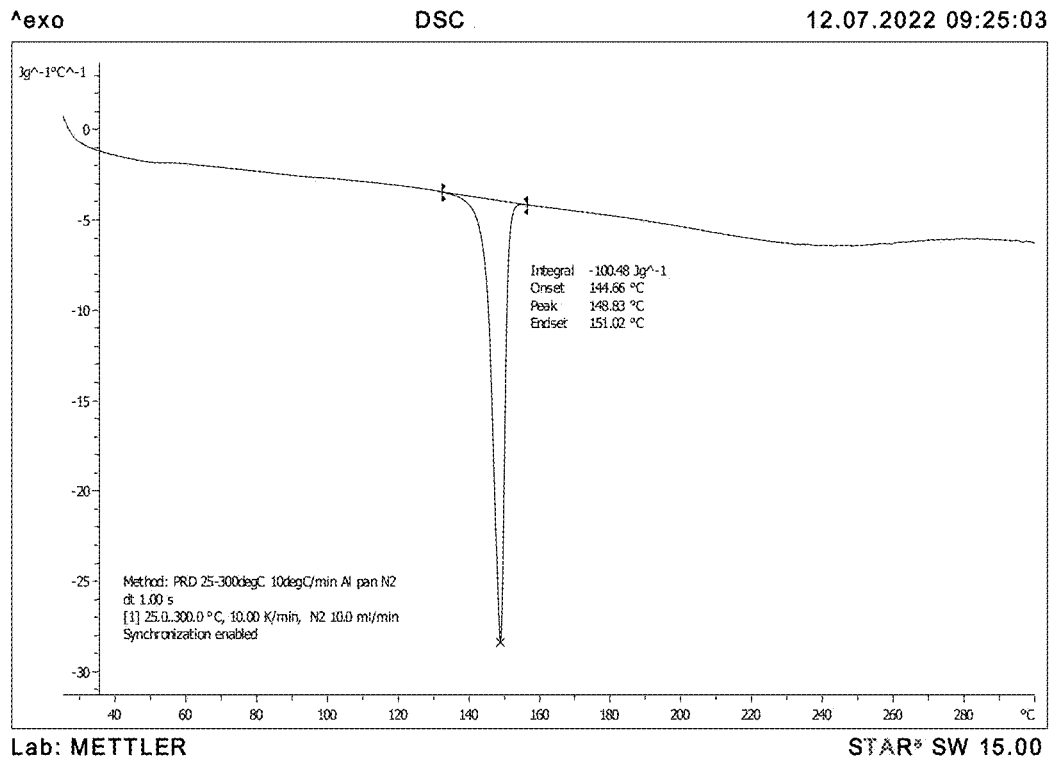

FIG. 773 depicts the DSC profile of Experiment 6-Sample C1 (Methanol/acetonitrile) Form A.

Figure 774:
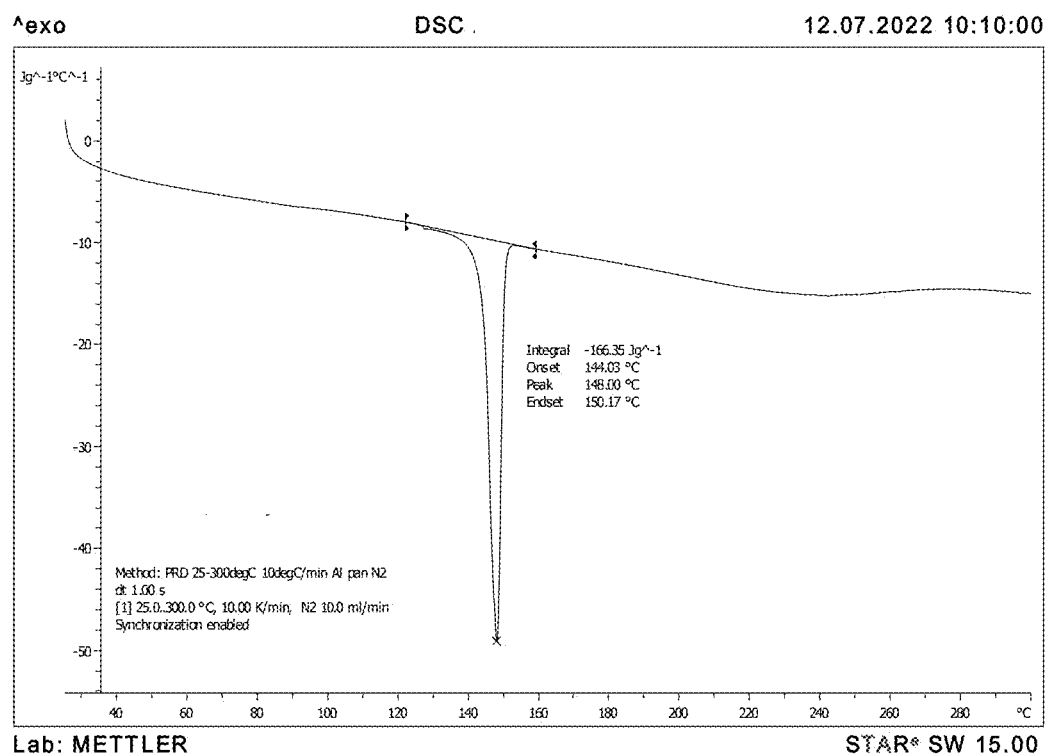

FIG. 774 depicts the DSC profile of Experiment 6-Sample D1 (Methanol/THF) Form A.

Figure 775:
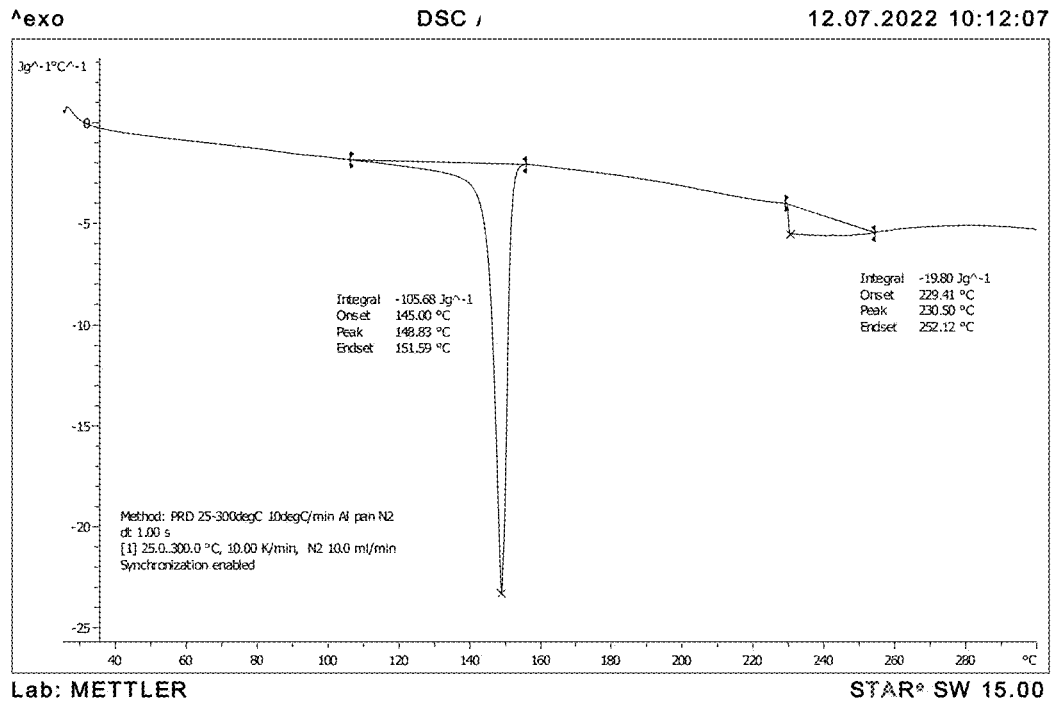

FIG. 775 depicts the DSC profile of Experiment 6-Sample E1 (Methanol/DCM) Form A.

Figure 776:
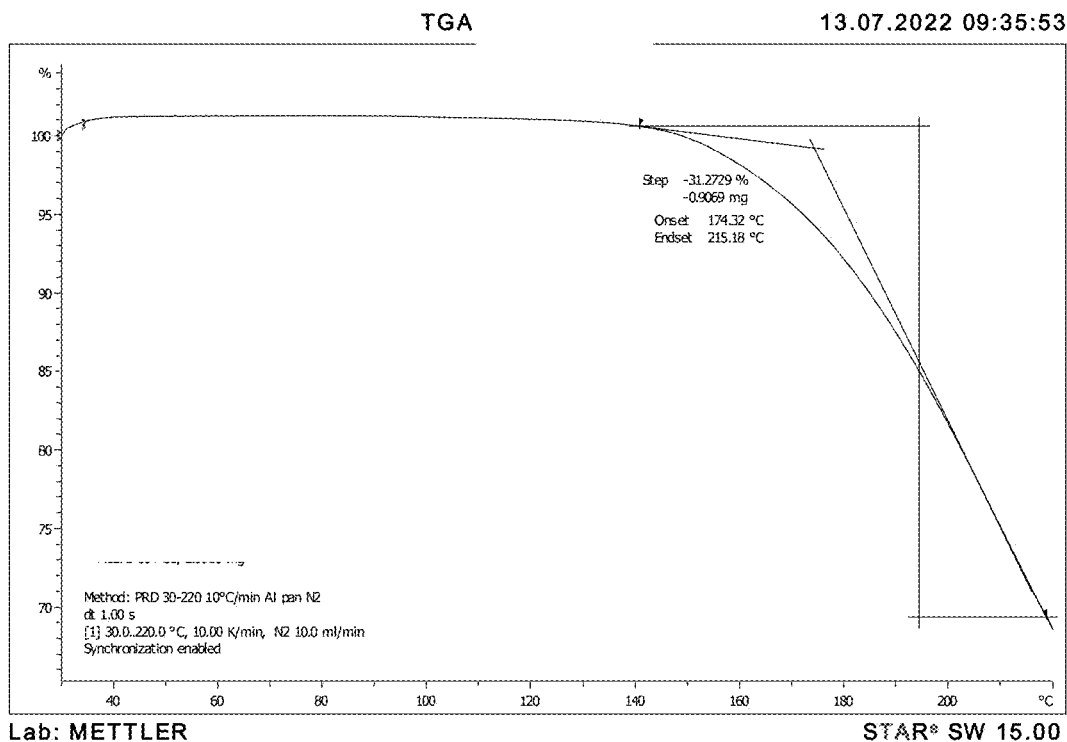

FIG. 776 depicts the TGA profile of Experiment 6-Sample C1 (Methanol/acetonitrile) Form A.

Figure 777:
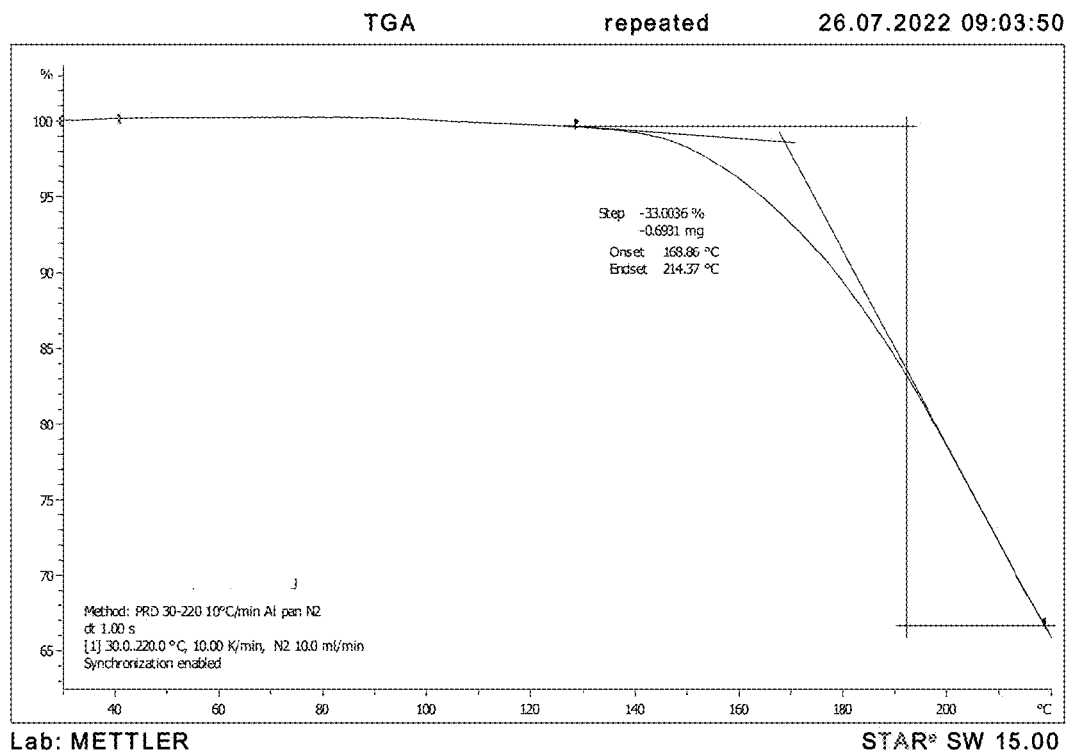

FIG. 777 depicts the TGA profile of Experiment 6-Sample C1 repeated (Methanol/acetonitrile) Form A. Repeated, positive pressure event gave TGA>unity.

Figure 778:
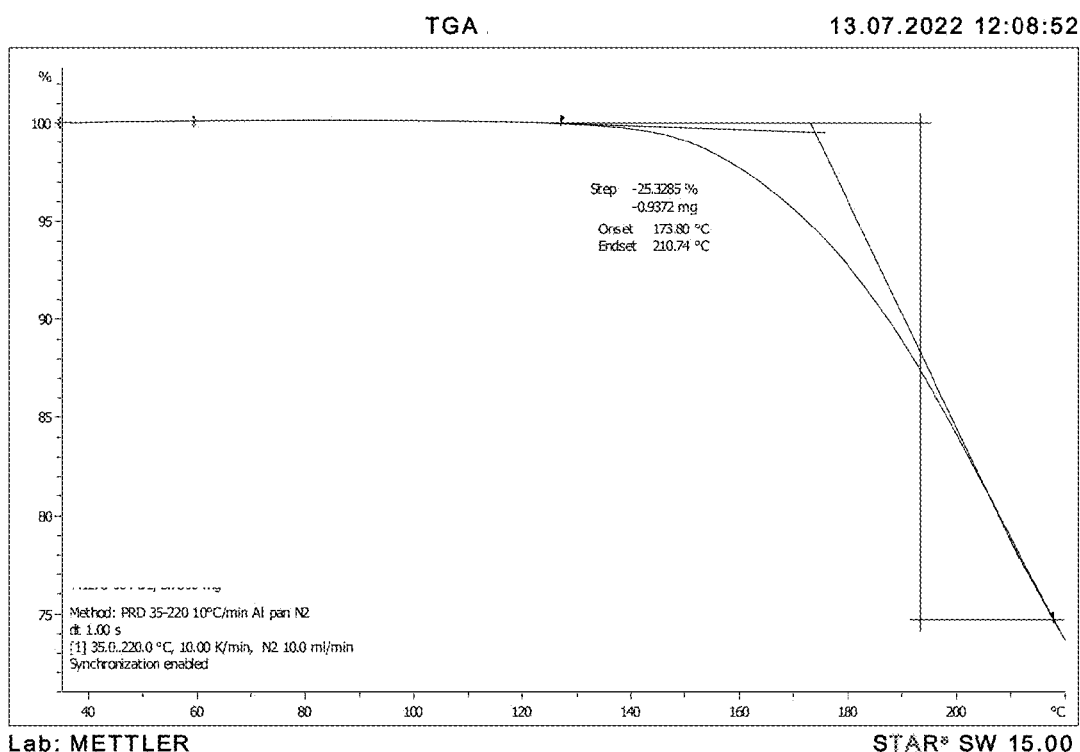

FIG. 778 depicts the TGA profile of Experiment 6-Sample D1 (Methanol/THF) Form A.

Figure 779:
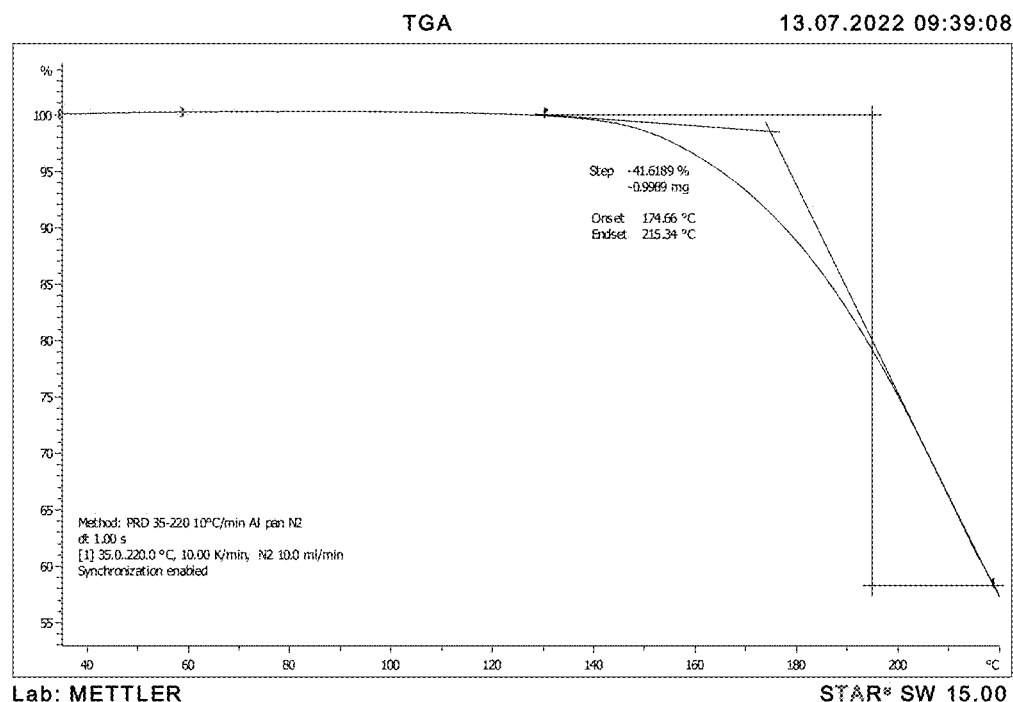

FIG. 779 depicts the TGA profile of Experiment 6-Sample E1 (Methanol/DCM) Form A.

Figure 780:
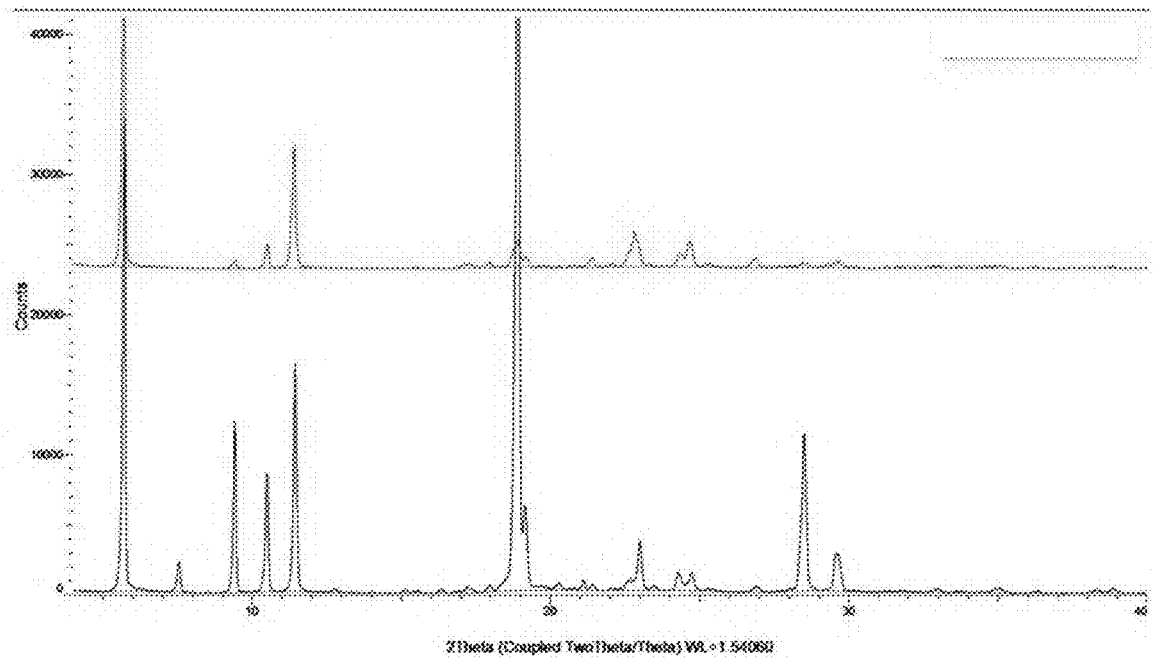

FIG. 780 depicts the overlay of XRPD profiles of Experiment 1-Sample A2 (form A, top) and Experiment 6-Sample C1 (methanol/acetonitrile, bottom).

Figure 781:
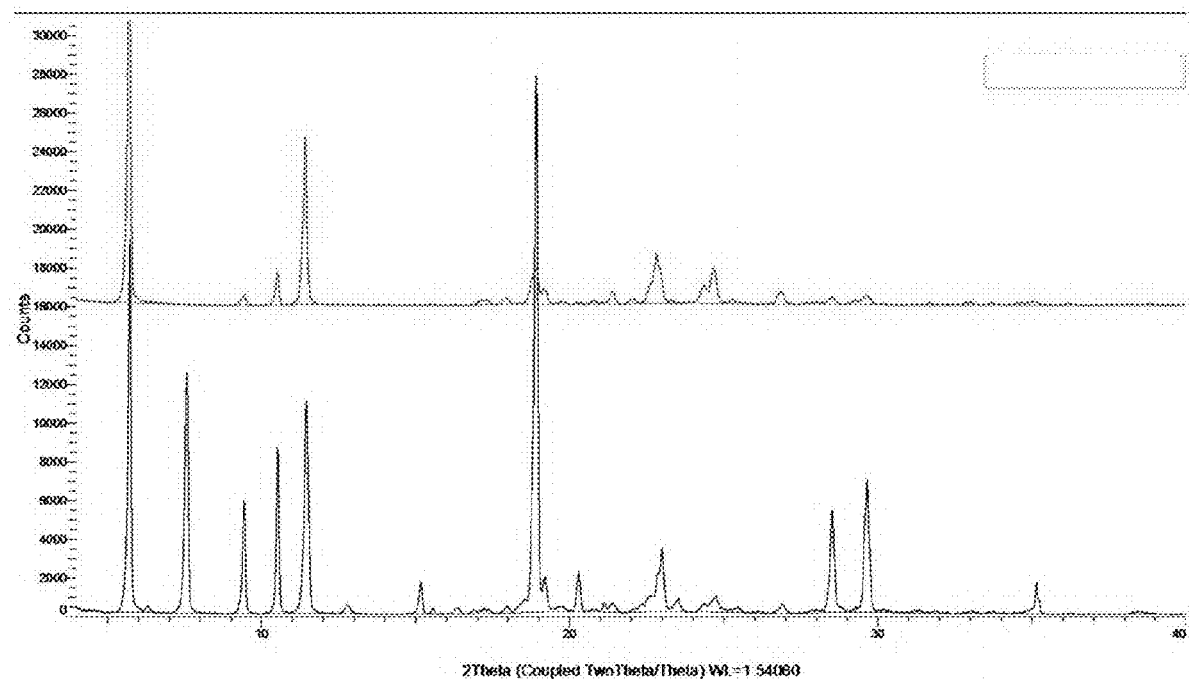

FIG. 781 depicts the overlay of XRPD profiles of Experiment 1-Sample A2 (form A, top) and Experiment 6-Sample D1 (methanol/THF, bottom).

Figure 782:
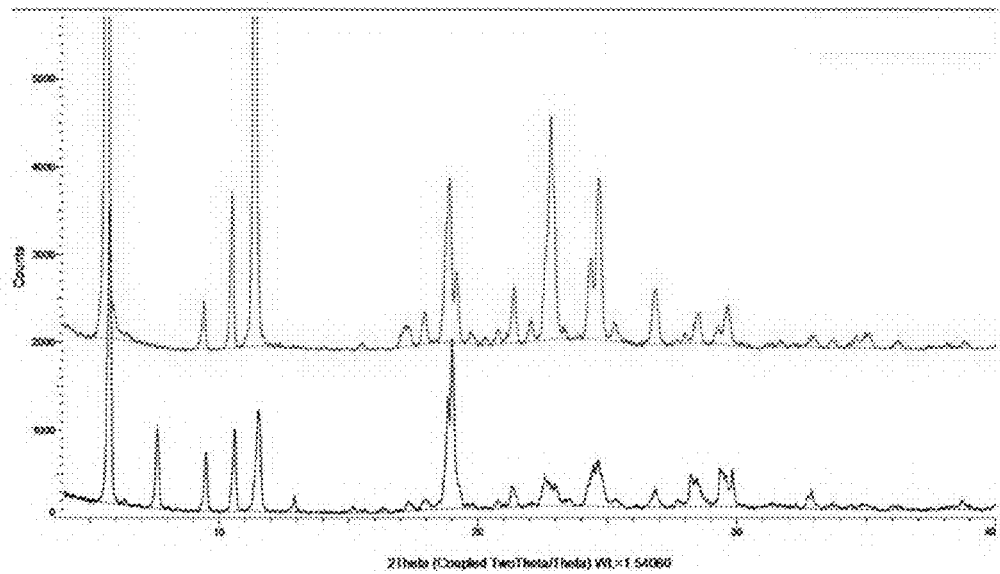

FIG. 782 depicts the overlay of XRPD profiles of Experiment 1-Sample A2 (form A, top) and Experiment 6-Sample E1 (methanol/DCM, bottom).

Figure 783:
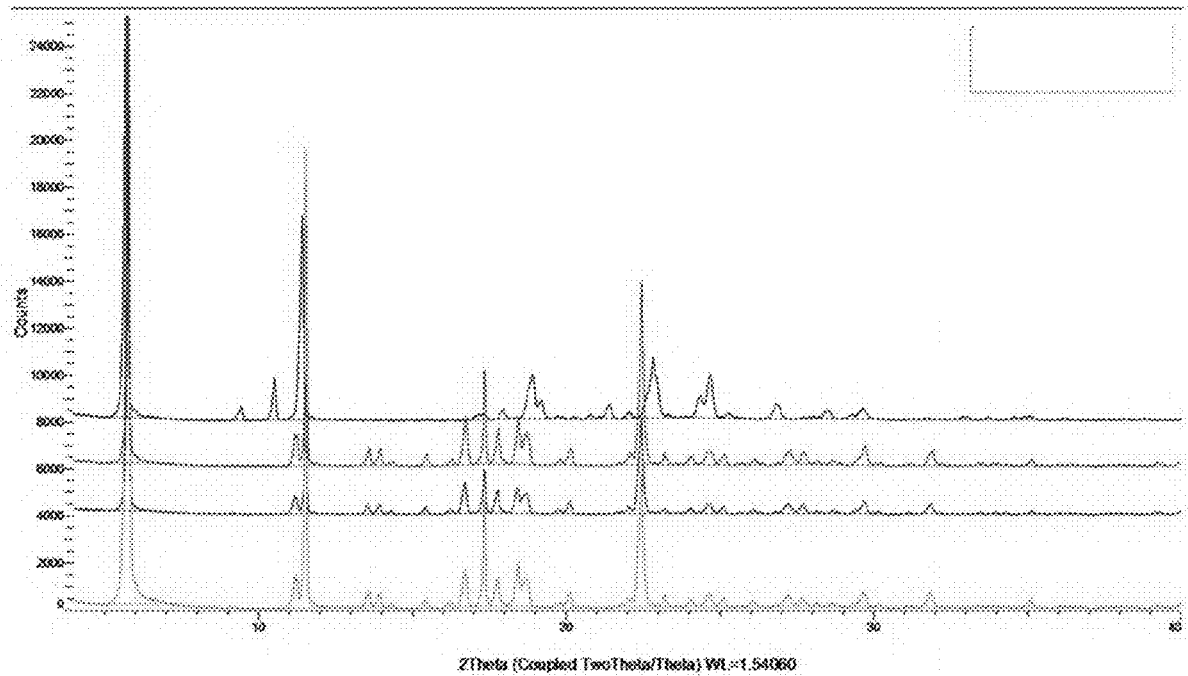

FIG. 783 depicts the overlay of, from top to bottom, XRPD of Experiment 1-Sample A2 (Form A), Experiment 9-Sample A1 (wet pellet, Pattern #2), Experiment 9-Sample A2 (dried under N2 purge, Pattern #2) and Experiment 3-Sample R1 (wet pellet, Pattern #2).

Figure 784:
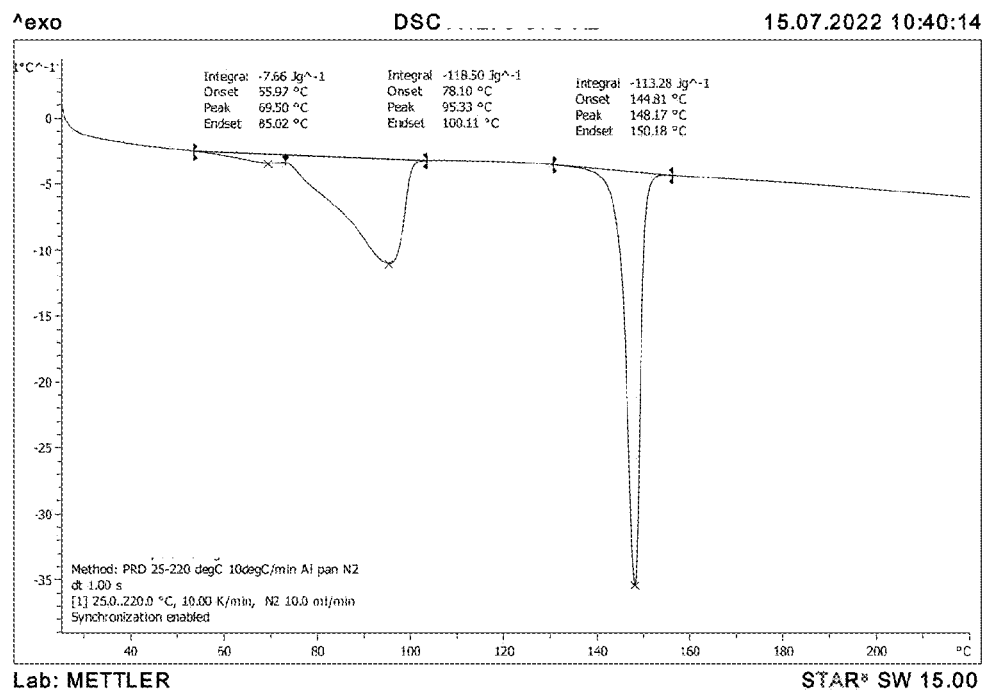

FIG. 784 depicts the DSC profile of Experiment 9-Sample A2 (t=0).

Figure 785:
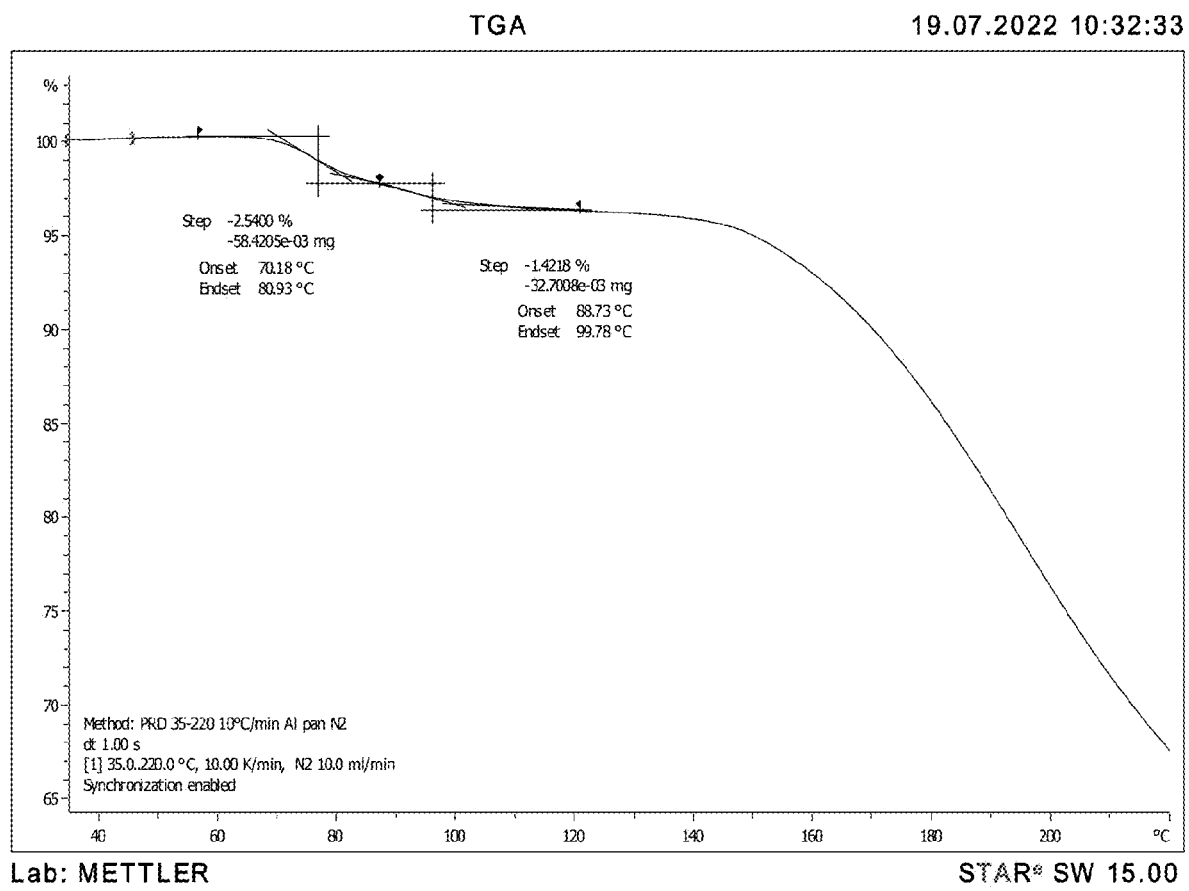

FIG. 785 depicts the DSC profile of Experiment 9-Sample A2 (t=4 days).

Figure 786:
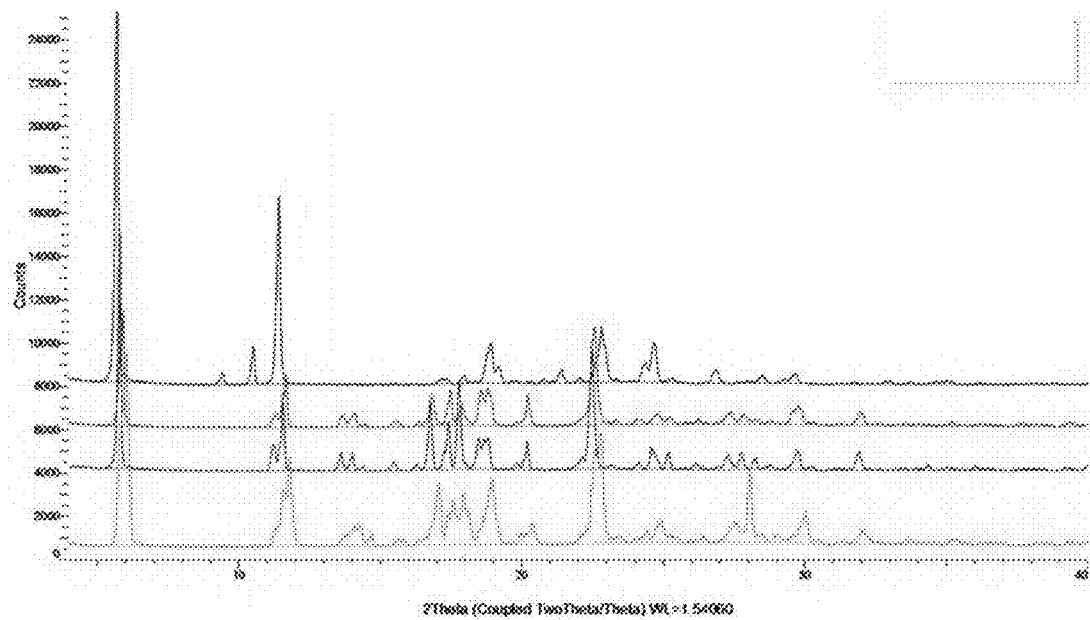

FIG. 786 depicts the overlay of, from top to bottom, XRPD of Experiment 1-Sample A2 (Form A), Experiment 9-Sample B1 (wet pellet, Pattern #2), Experiment 9-Sample B2 (dried under N2 purge, Pattern #2) and Experiment 4-Sample R1 (wet pellet, Pattern #4).

Figure 787:
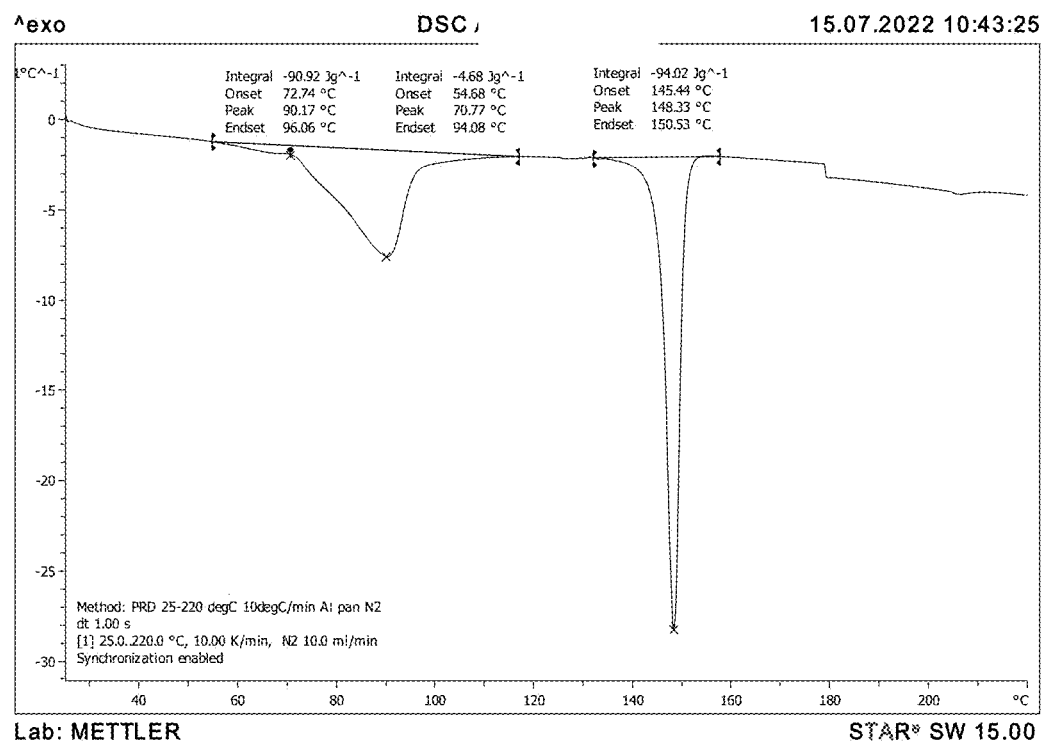

FIG. 787 depicts the DSC profile of Experiment 9-Sample B2.

Figure 788:
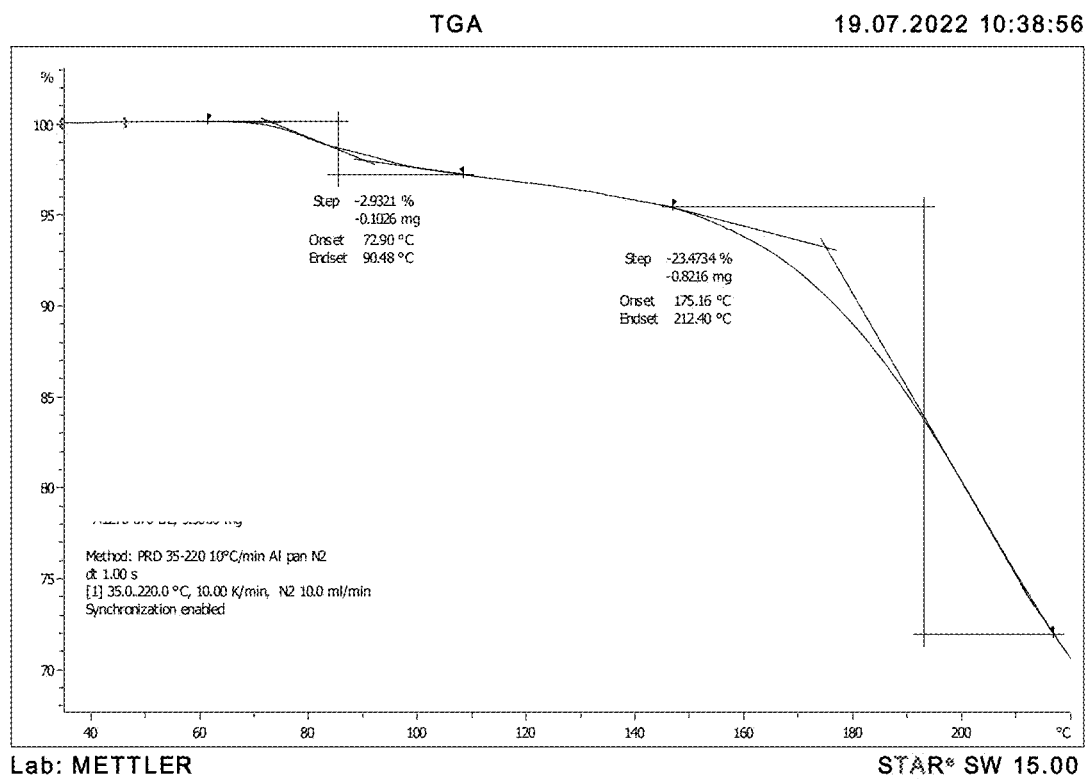

FIG. 788 depicts the TGA profile of Experiment 9-Sample B2 (T=0).

Figure 789:
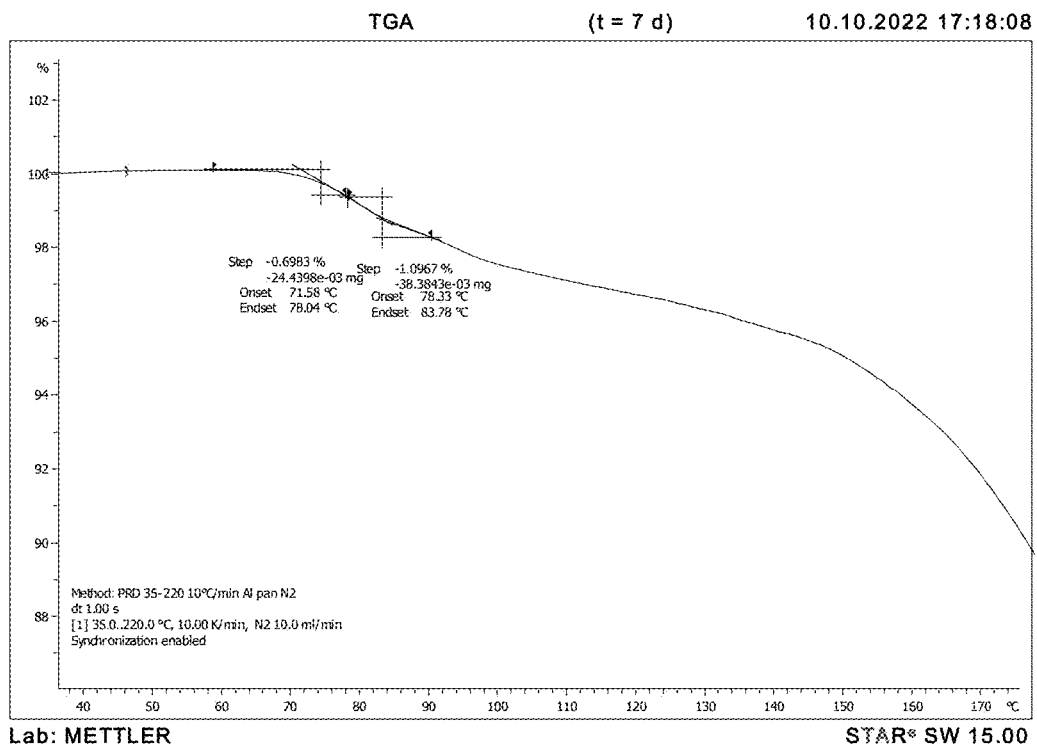

FIG. 789 depicts the TGA profile of Experiment 9-Sample B2 (t=7 days).

Figure 790:
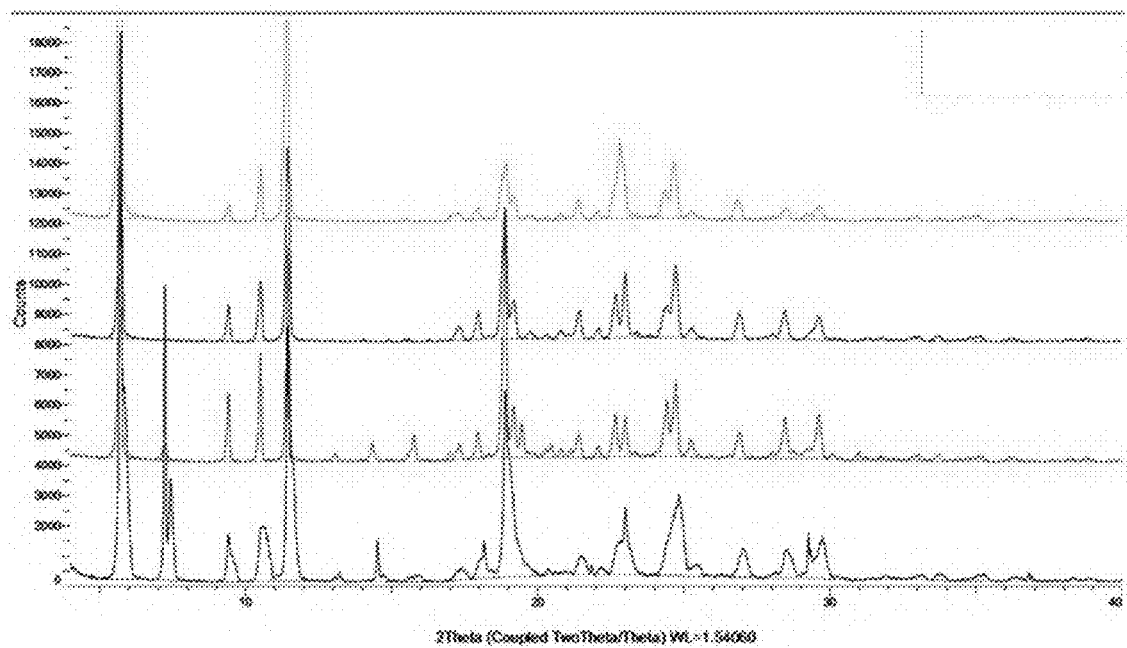

FIG. 790 depicts the overlay of XRPD of, from top to bottom, Experiment 1-Sample A2 (Form A), Experiment 9-Sample C1 (wet pellet, Form A), Experiment 9-Sample C2 (dried under N2 purge, Form A) and Experiment 4-Sample H1 (wet pellet, Pattern #3).

Figure 791:
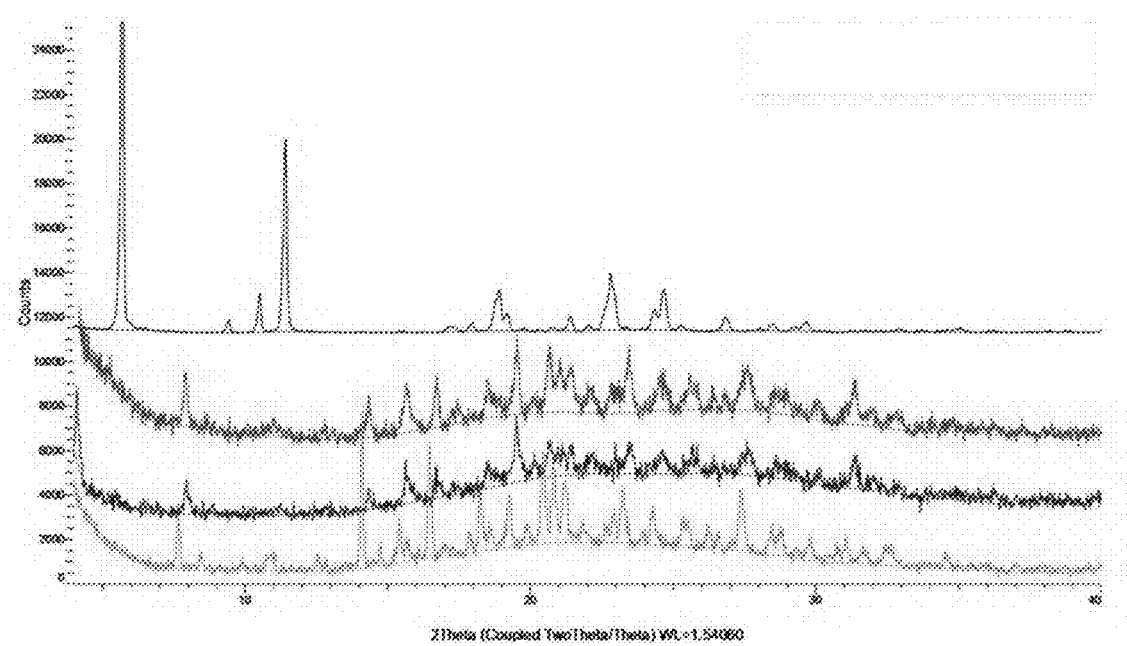

FIG. 791 depicts the overlay of, from top to bottom, XRPD of Experiment 1-Sample A2 (Form A), Experiment 9-Sample D1 (wet pellet, Pattern #5), Experiment 9-Sample D2 (dried under N2 purge, Pattern #5) and Experiment 4-Sample E1 (wet pellet, Pattern #5).

Figure 792:
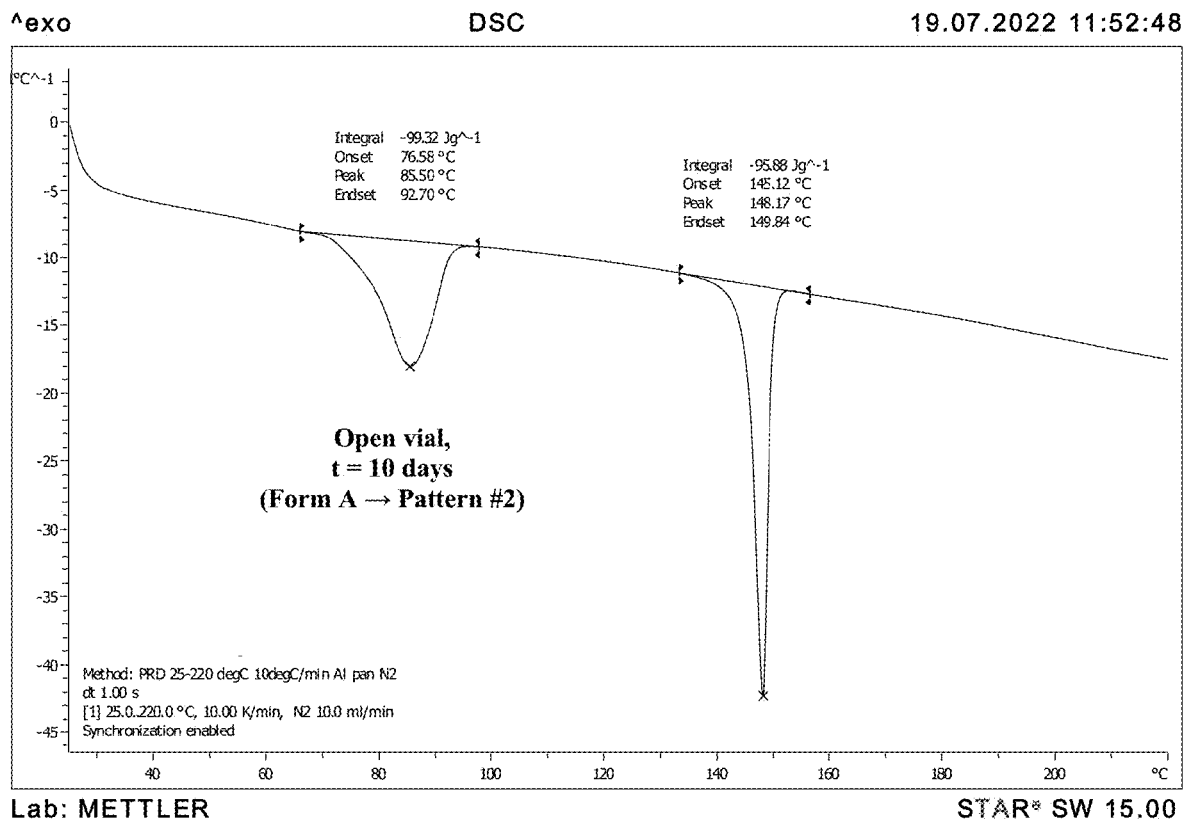

FIG. 792 depicts the DSC profile of Experiment 10-Sample A2.

Figure 793:
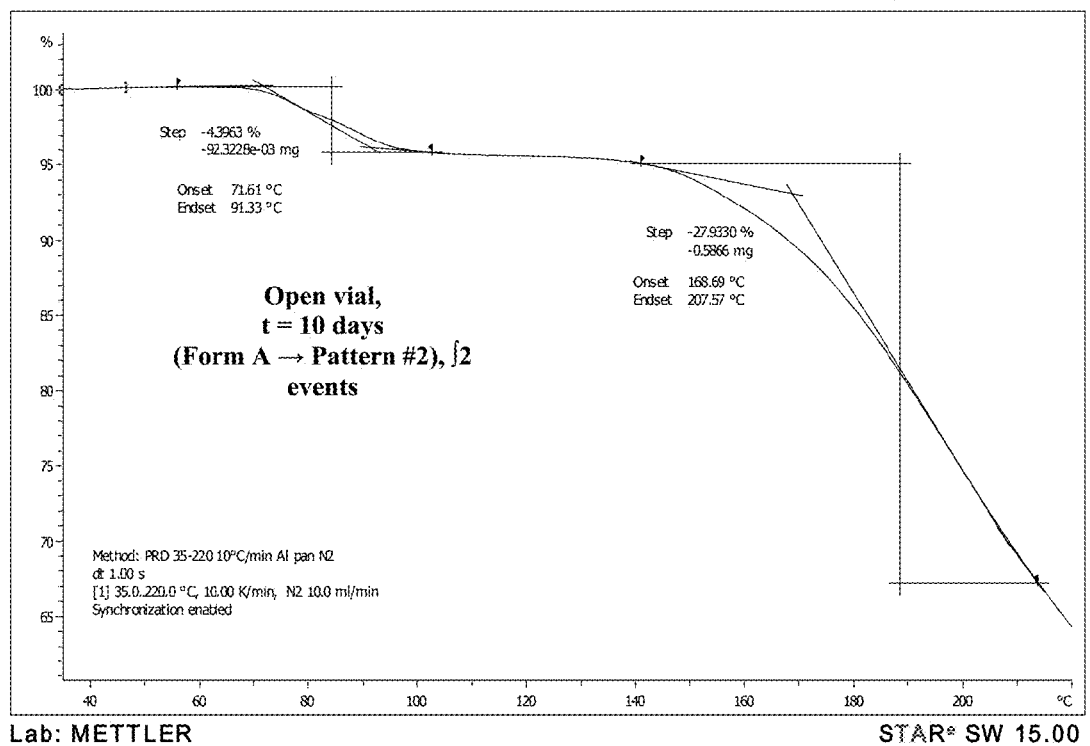

FIG. 793 depicts the TGA profile of Experiment 10-Sample A2 (t=10 days).

Figure 794:
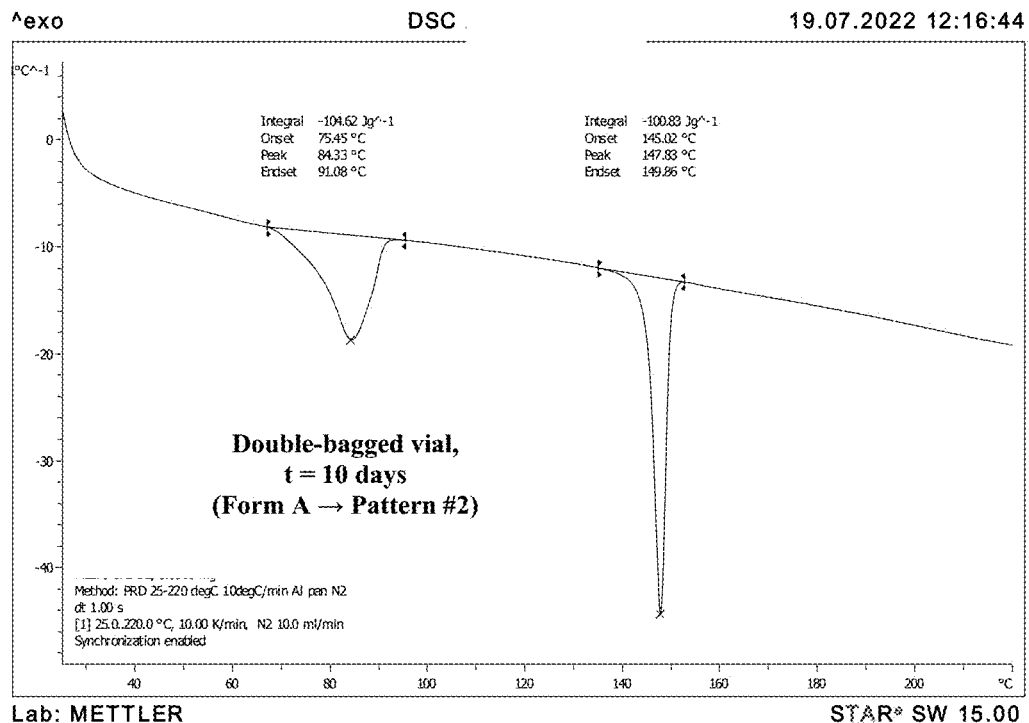

FIG. 794 depicts the DSC profile of Experiment 10-Sample B2 (t=10 days).

Figure 795:
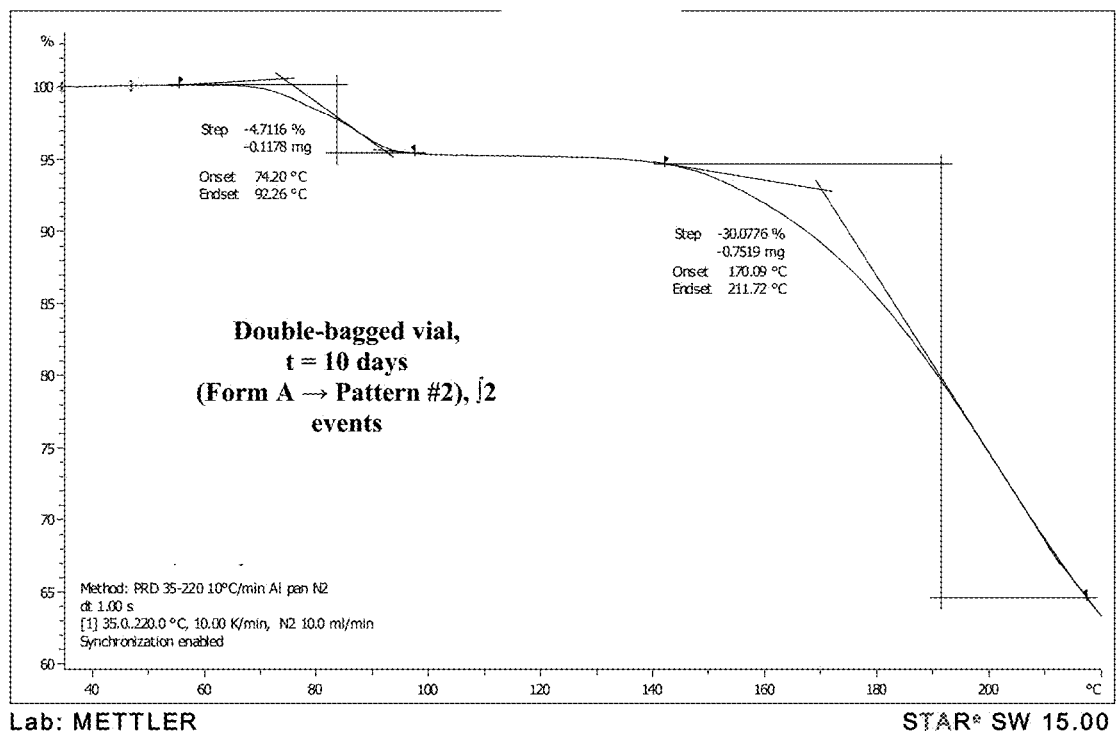

FIG. 795 depicts the TGA profile of Experiment 10-Sample B2 (t=10 days).

Figure 796:
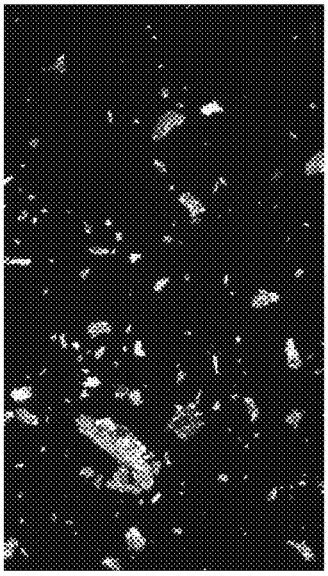

FIG. 796 depicts the PLM of Experiment 10-Sample A2 and B2 (t=10 days).

Figure 797:
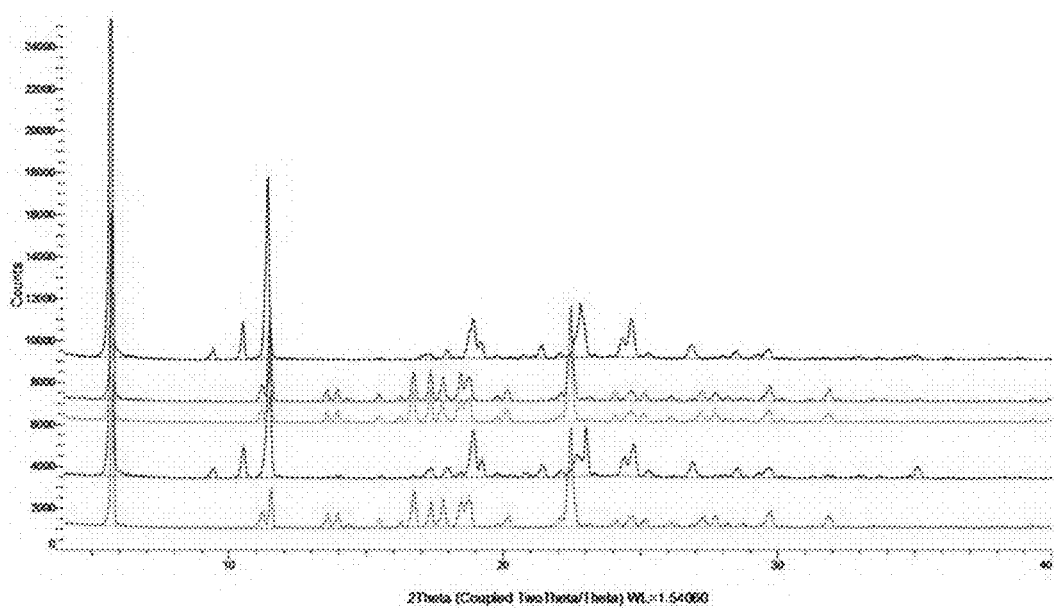

FIG. 797 depicts the overlay of, from top to bottom, XRPD of Experiment 1-Sample A2 (Form A), Experiment 10-Sample A1 (5 days, open vial Pattern #2), Experiment 10-Sample A2 (10 days, open vial, Pattern #2), Experiment 10-Sample B1 (5 days, double-bagged vial, Form A) and Experiment 10-Sample B2 (10 days, double-bagged vial, Pattern #2).

Figure 798:
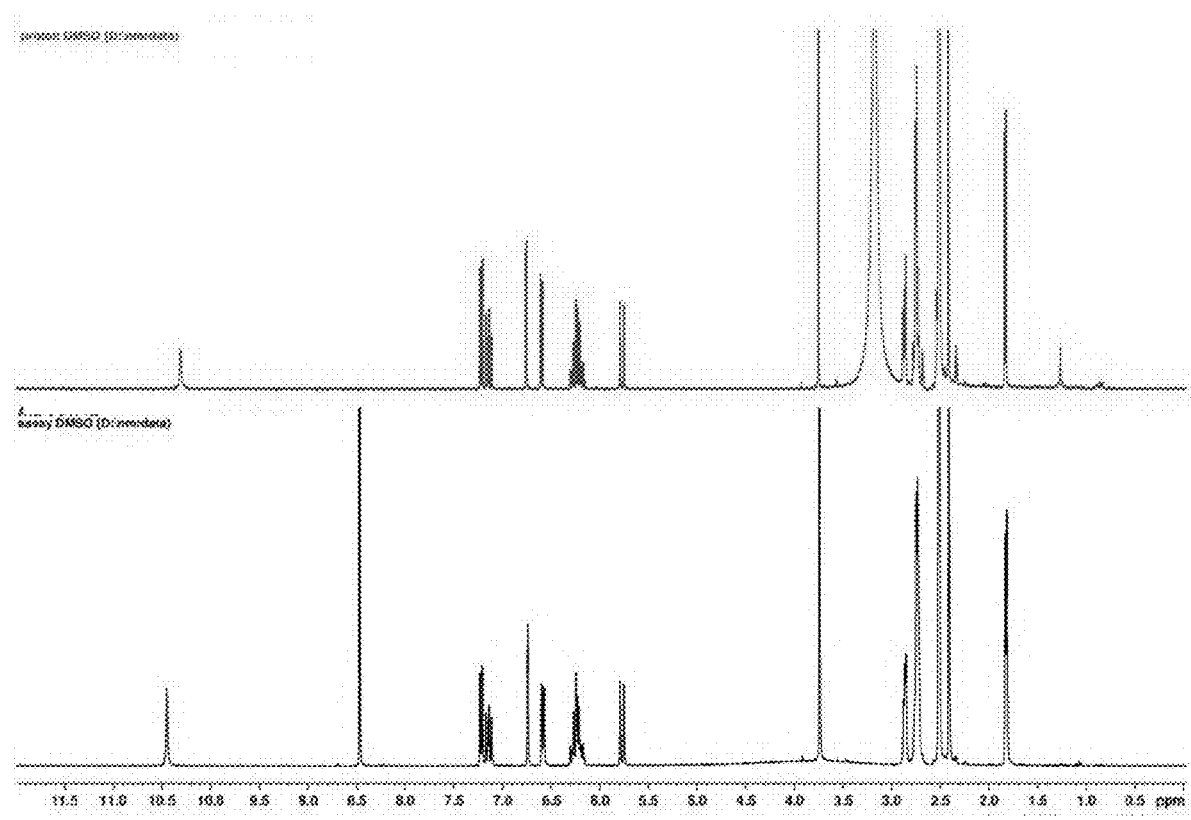

FIG. 798 depicts the overlay of $^1$H NMR spectra of Experiment 10-Sample A2 (t=10 days, open vial, top) and Experiment 1-Sample A2 (Q NMR assay, bottom). DMSO-$d_6$ used as deuterated solvent and TCNB used as internal standard in Experiment 1-Sample A2.

Figure 799:
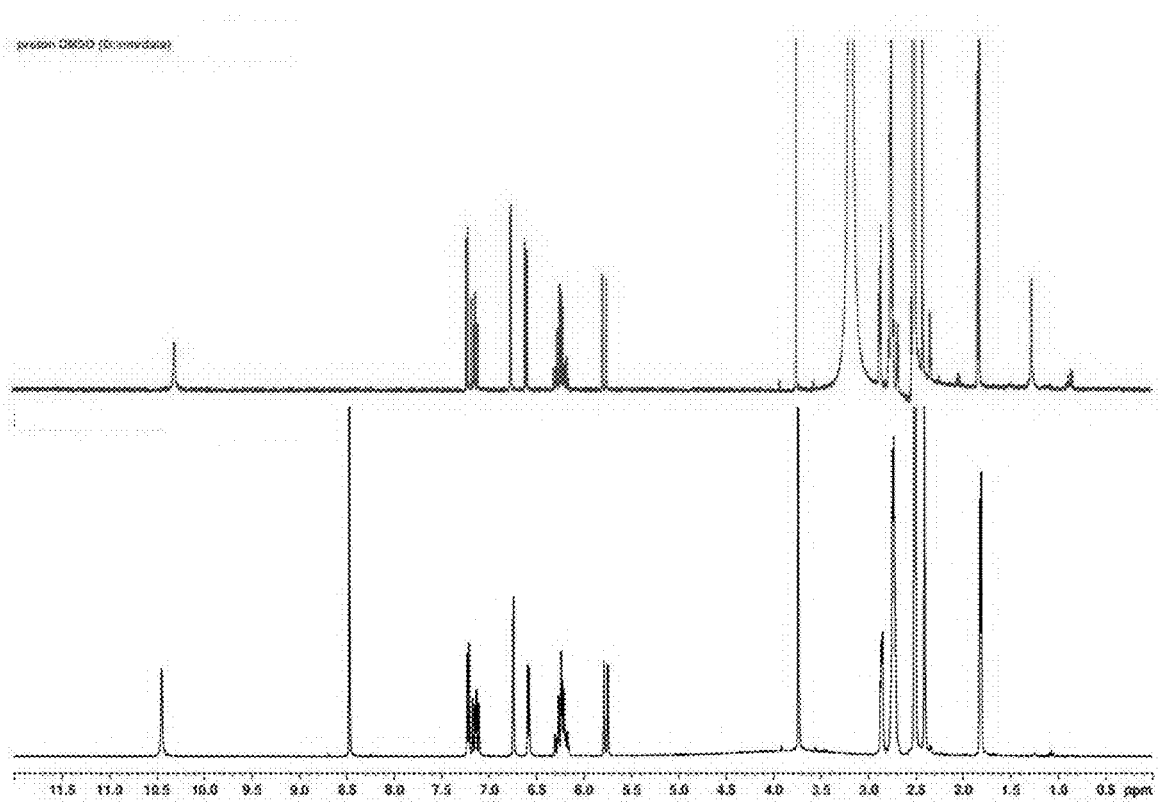

FIG. 799 depicts the overlay of $^1$H NMR spectra of Experiment 10-Sample B2 (t=10 days, double-bagged vial, top) and Experiment 1-Sample A2 (Q NMR assay, bottom). DMSO-$d_6$ used as deuterated solvent and TCNB used as internal standard in Experiment 1-Sample A2.

Figure 800:
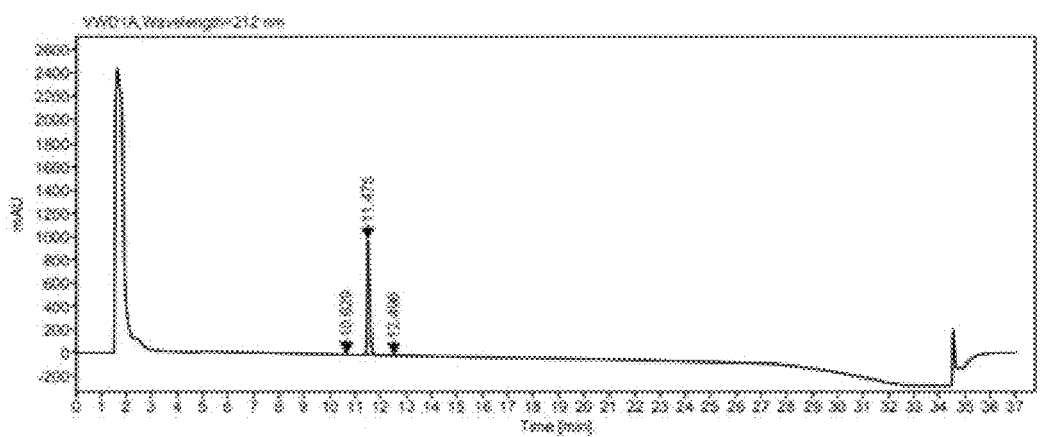

FIG. 800 depicts the HPLC profile of Experiment 1-Sample A2 input.

Figure 801:
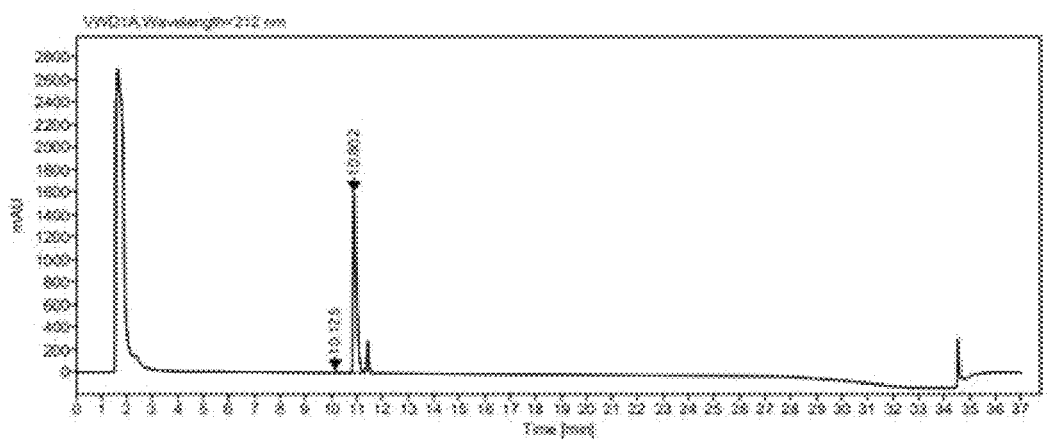

FIG. 801 depicts the HPLC profile of Experiment 10-Sample A2 t=10 days, open vial.

Figure 802:
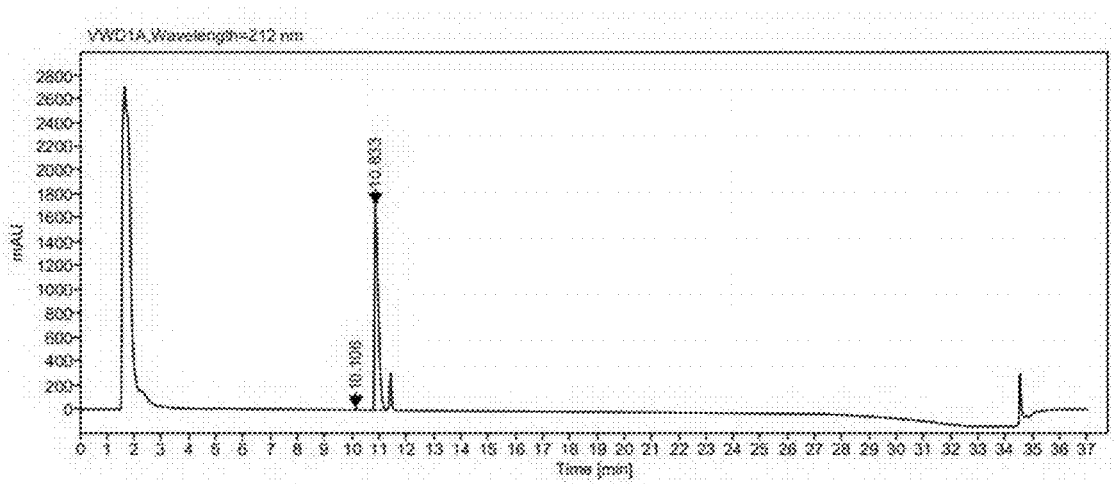

FIG. 802 depicts the HPLC profile of Experiment 10-Sample B2 t=10 days, open vial.

Figure 803:
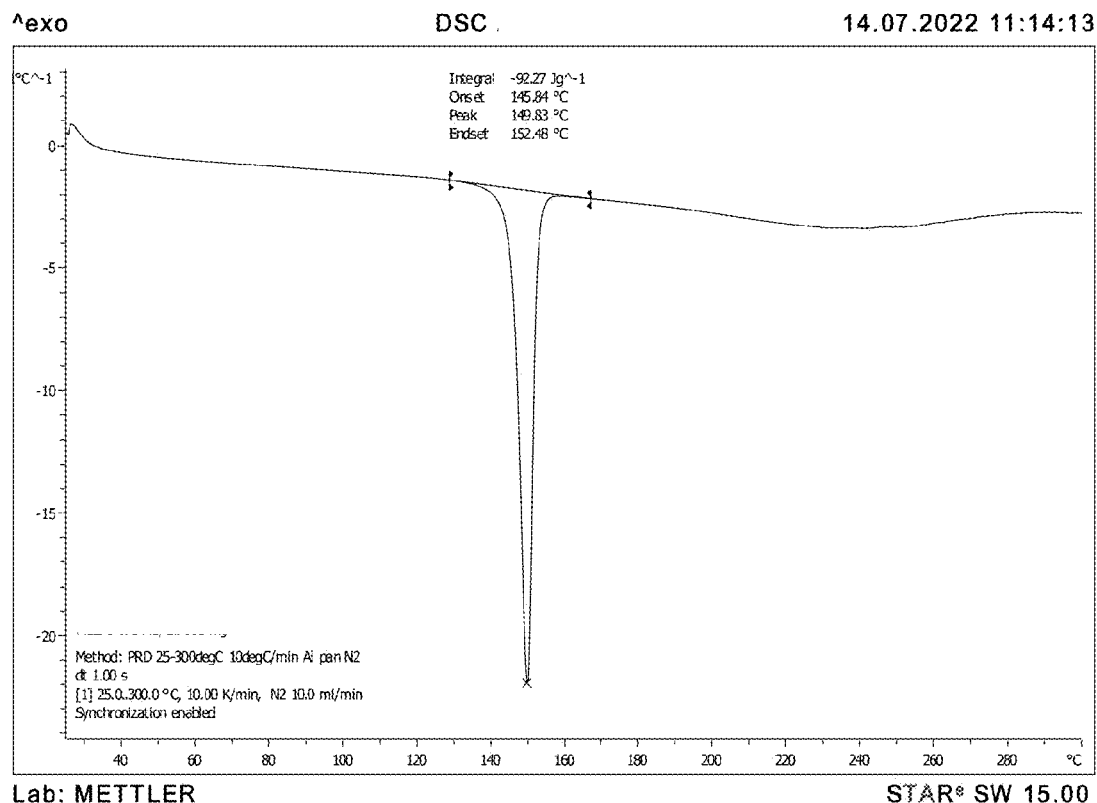

FIG. 803 depicts the DSC profile of A127-076-A1.

Figure 804:
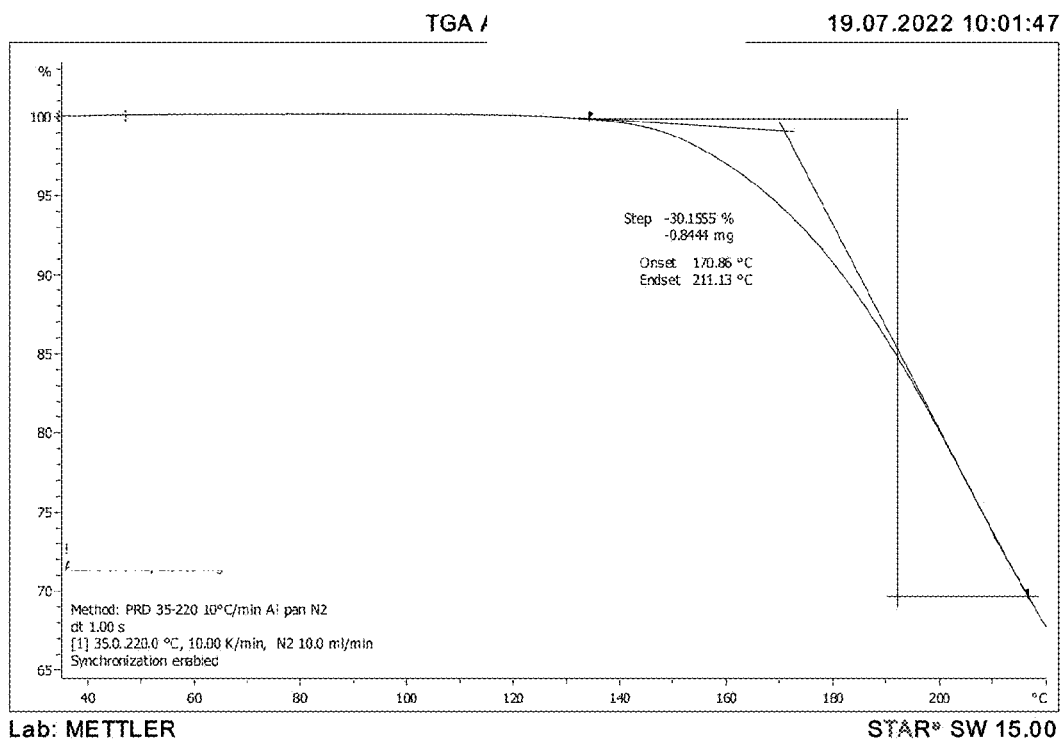

FIG. 804 depicts the TGA profile of A127-076-A1.

Figure 805:
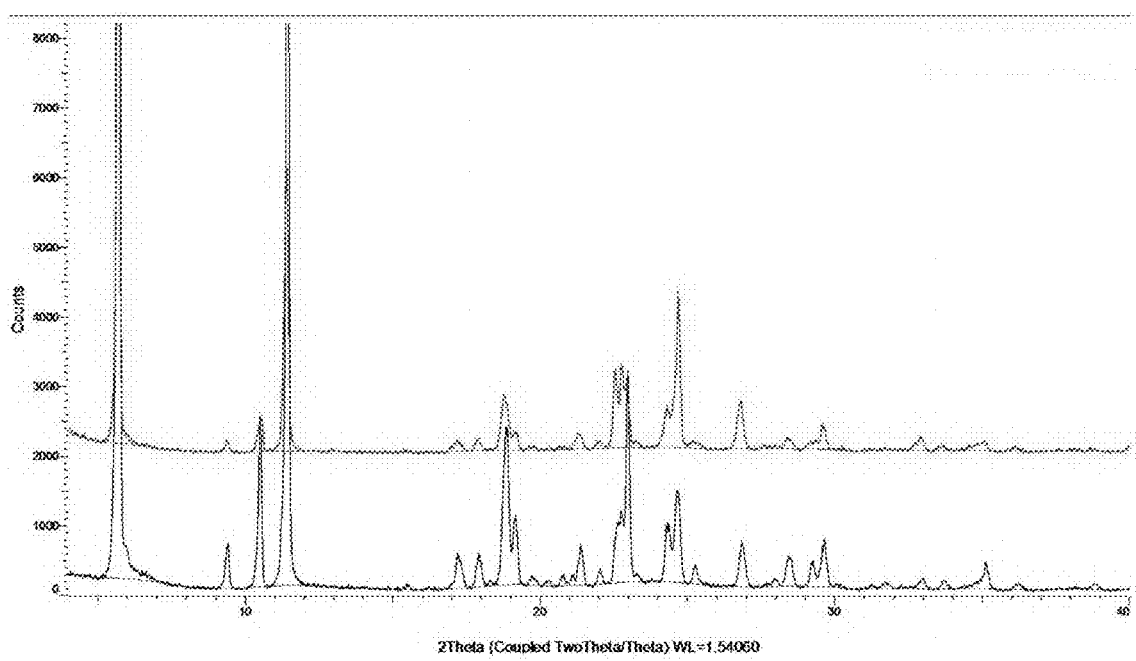

FIG. 805 depicts the overlay of XRPD profiles of Experiment 13-Sample C1 (initial 1 g batch, top) and Experiment 11-Sample A1 (re-prep, bottom).

Figure 806:
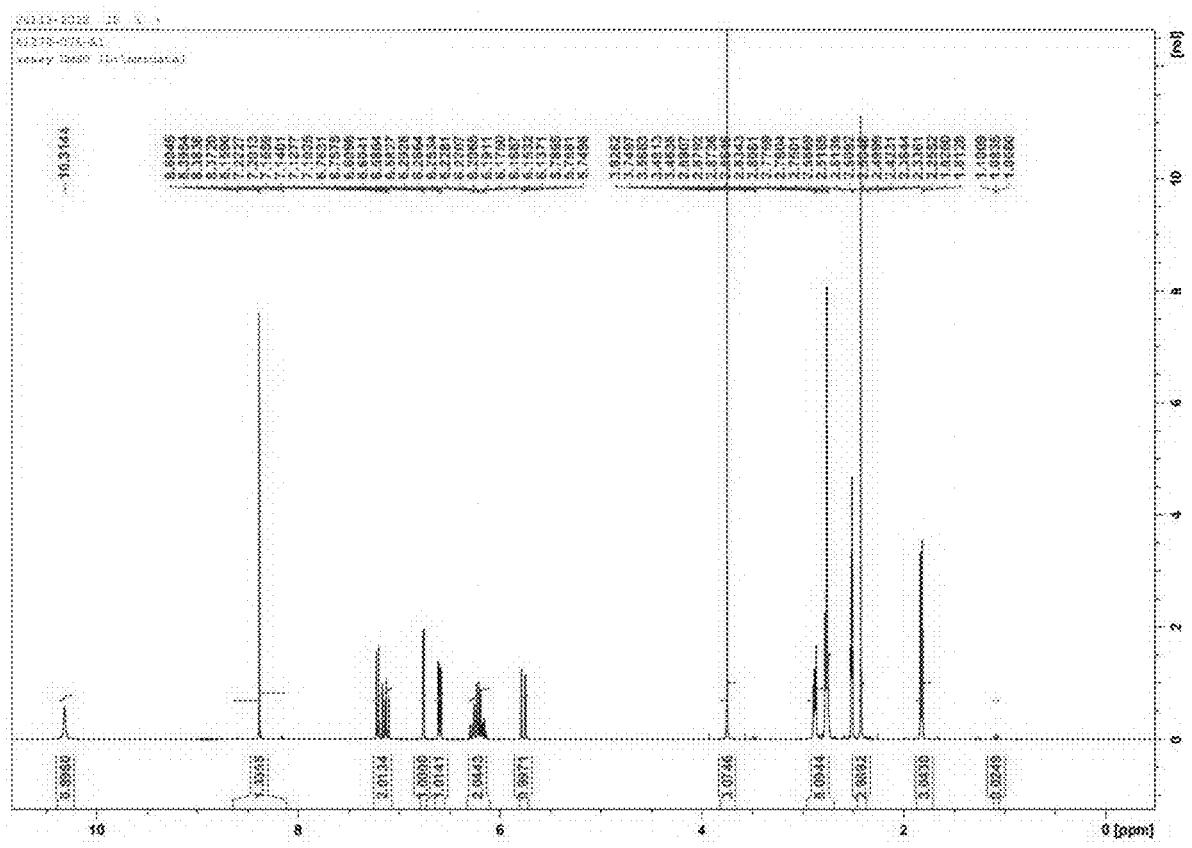

FIG. 806 depicts the $^1$H NMR spectrum of Experiment 11-Sample AL. DMSO-$d_6$ used as deuterated solvent and TCNB used as internal standard. 99.5% w/w assay. 0.1% w/w ethanol content 1 to 1 ratio of API to sorbic acid.

Figure 807:
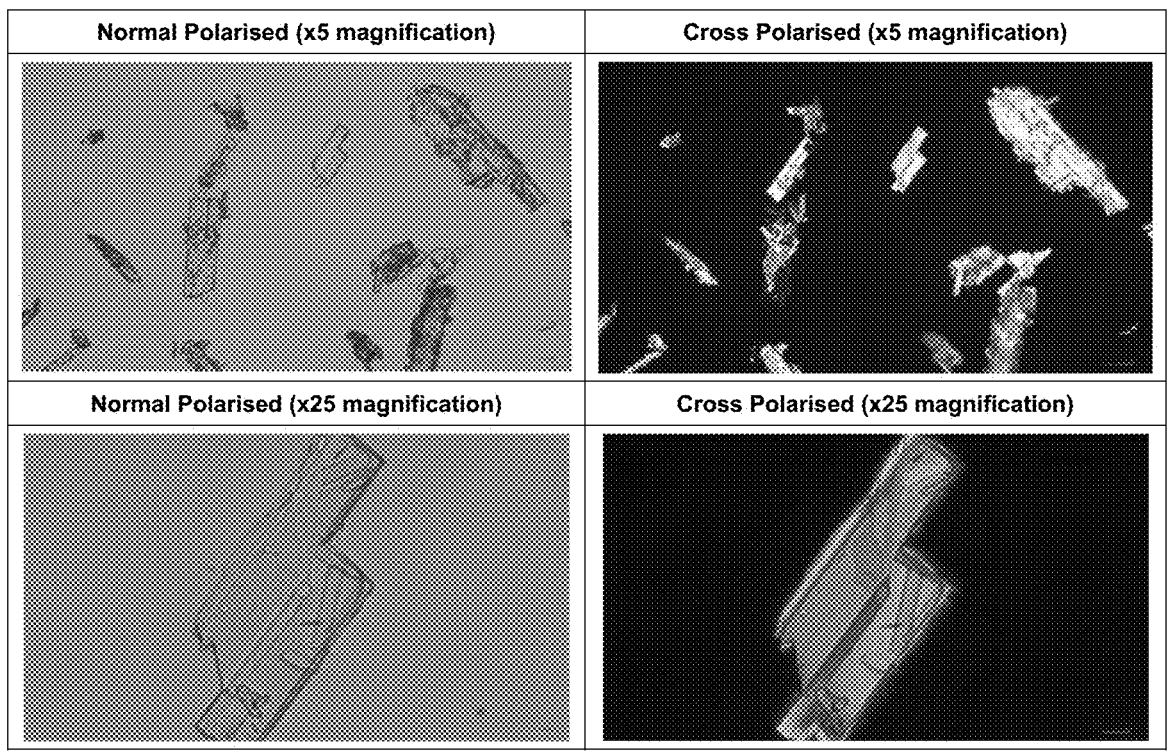

FIG. 807 depicts the PLM of Experiment 11-Sample-A1.

Figure 808:
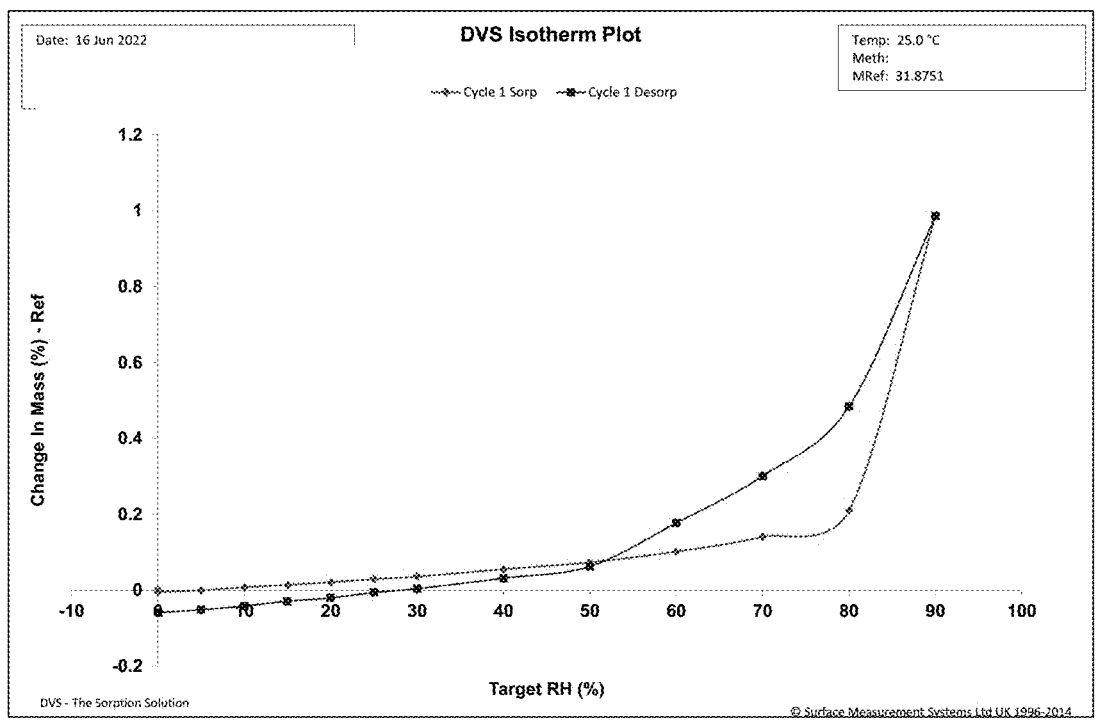

FIG. 808 depicts the DVS isotherm plot of Experiment 1-Sample A2.

Figure 809:
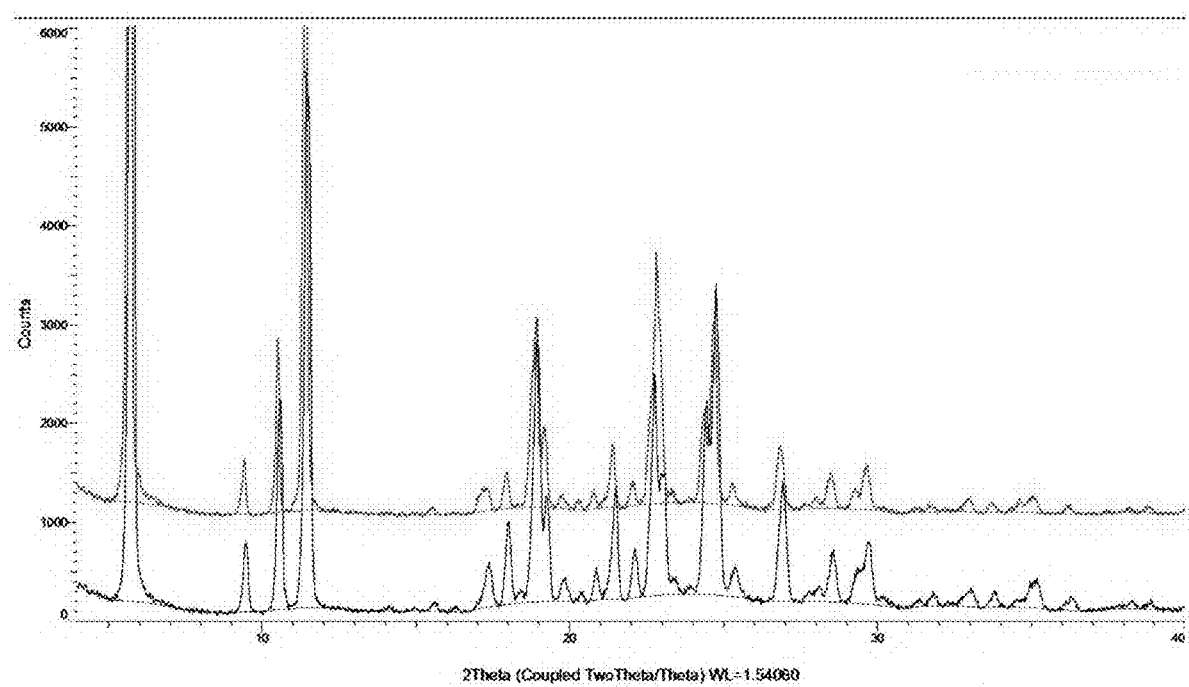

FIG. 809 depicts the overlay of XRPD profiles of Experiment 1-Sample A2 (form A, top) and Experiment 1-Sample A2_post-DVS (form A, bottom).

FIG. 810 depicts the SC-XRPD Characterization of Tabernanthalog Sorbate Form A.

FIG. 811 depicts the SC-XRPD Characterization of Tabernanthalog Sorbate Hydrate.

Figure 812:
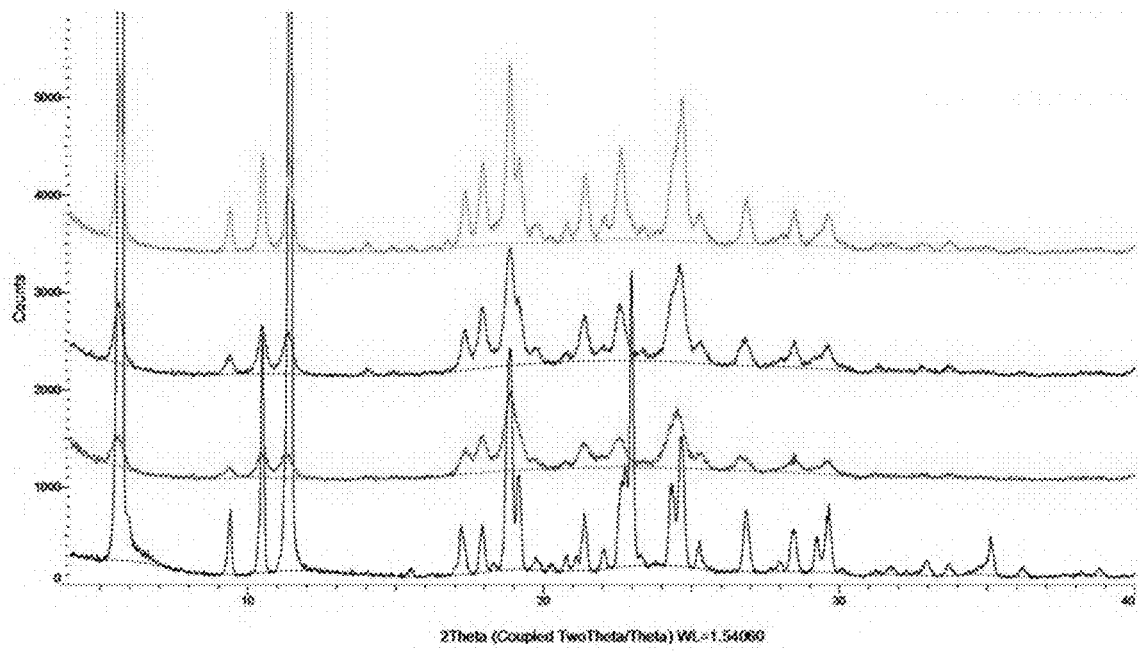

FIG. 812 depicts the overlay of, from bottom to top, XRPD profiles of Tabernanthalog·Sorbate, Input, Form A, Experiment 6-Sample A1 (30 Hz, 2 h), Experiment 6-Sample A2 (30 Hz, 5.5 h), and Experiment 6-Sample A3 (30 Hz, 1 h, Tetradecafluorohexane).

Figure 813:
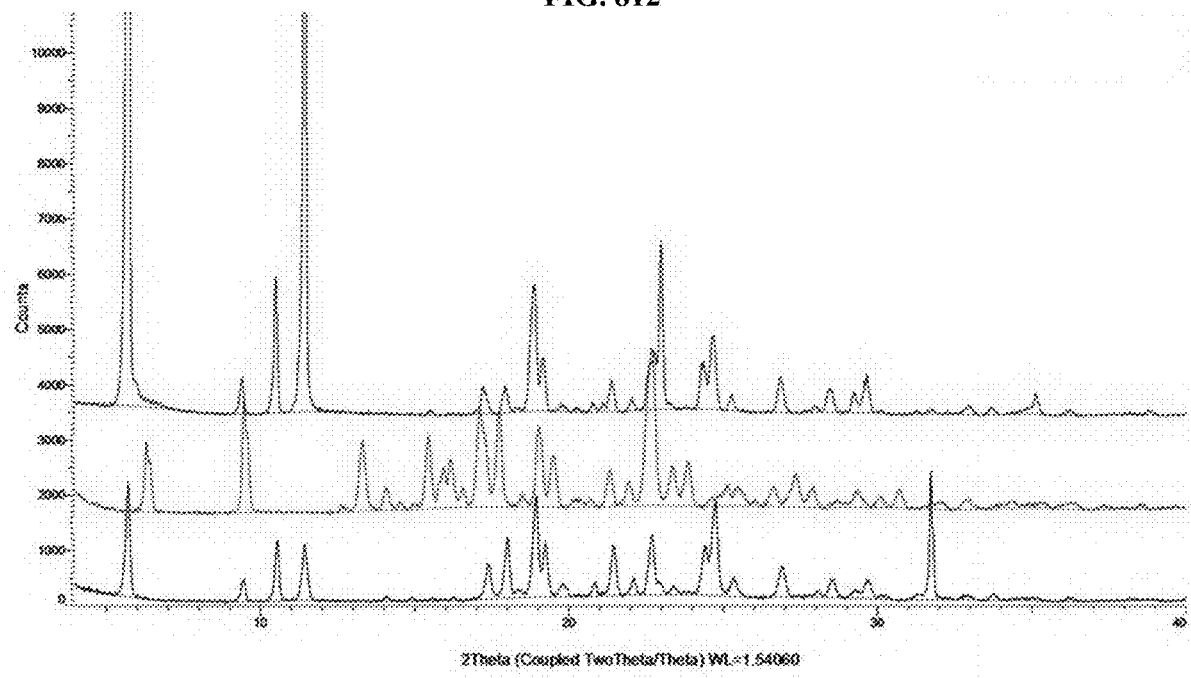

FIG. 813 depicts the overlay of XRPD profiles of, from bottom to top, Experiment 3-Sample C2 (Tabernanthalog·Sorbate, Form A), Experiment 3-Sample C1 (Tabernanthalog·Sorbate, Input, Pattern #7) and A1270-076-A1 (Tabernanthalog·Sorbate, Form A).

Figure 814:
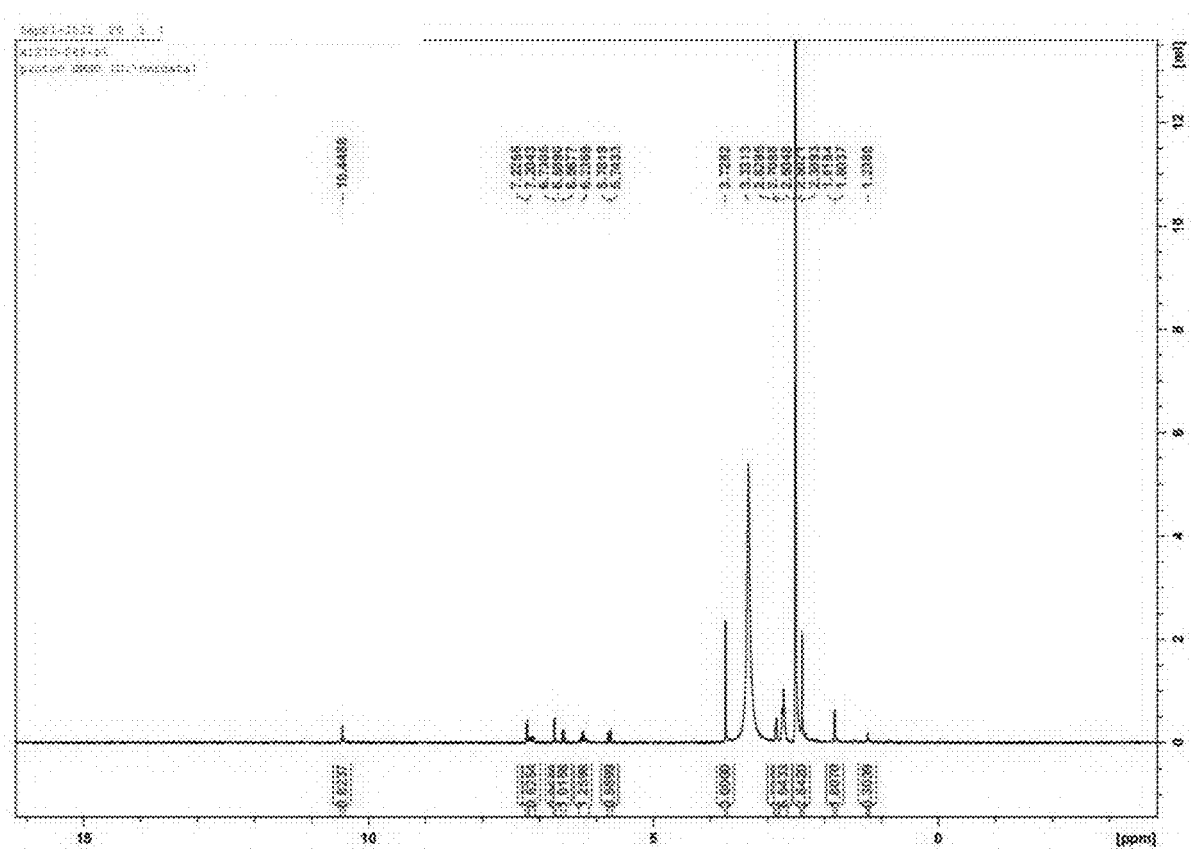

FIG. 814 depicts the $^1$H NMR spectrum of Experiment 1-Sample D1 (Tabernanthalog·Sorbate, Amorphous) in deuterated DMSO-$d_6$ and calibrated to the non-deuterated solvent residual of 2.50 ppm.

Figure 815:
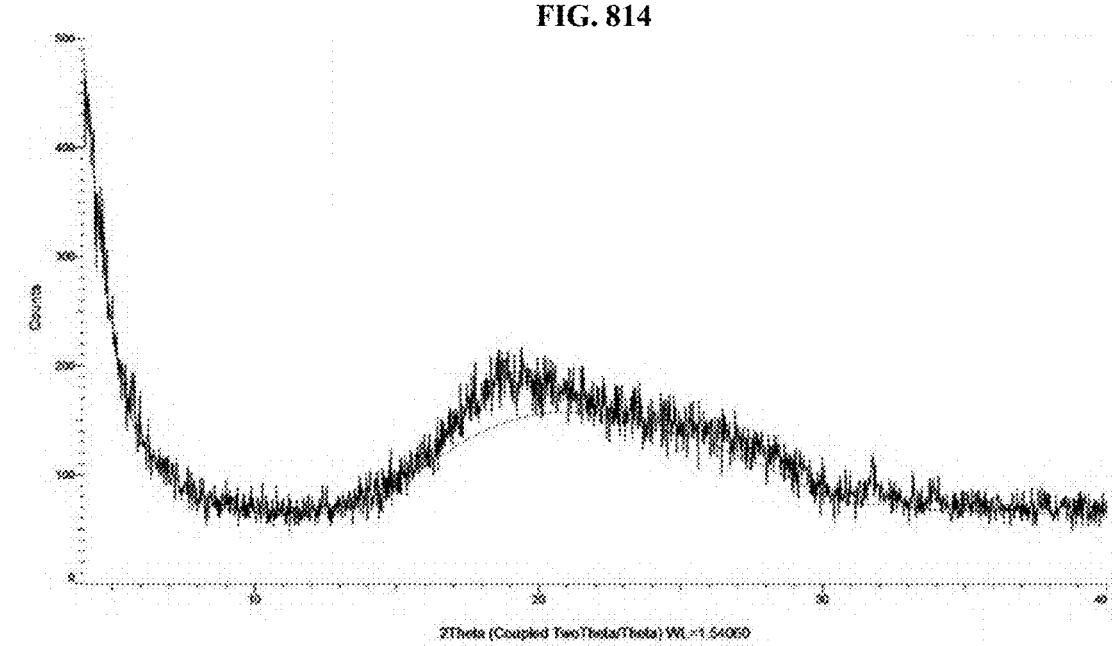

FIG. 815 depicts the XRPD profile of Experiment 1-Sample D1 (Tabernanthalog·Sorbate, amorphous).

FIG. 816 depicts the LC-MS profile of Experiment 1-Sample E1 (Tabernanthalog·Sorbate, Amorphous), Spectra (top) M/Z (bottom).

Figure 817:
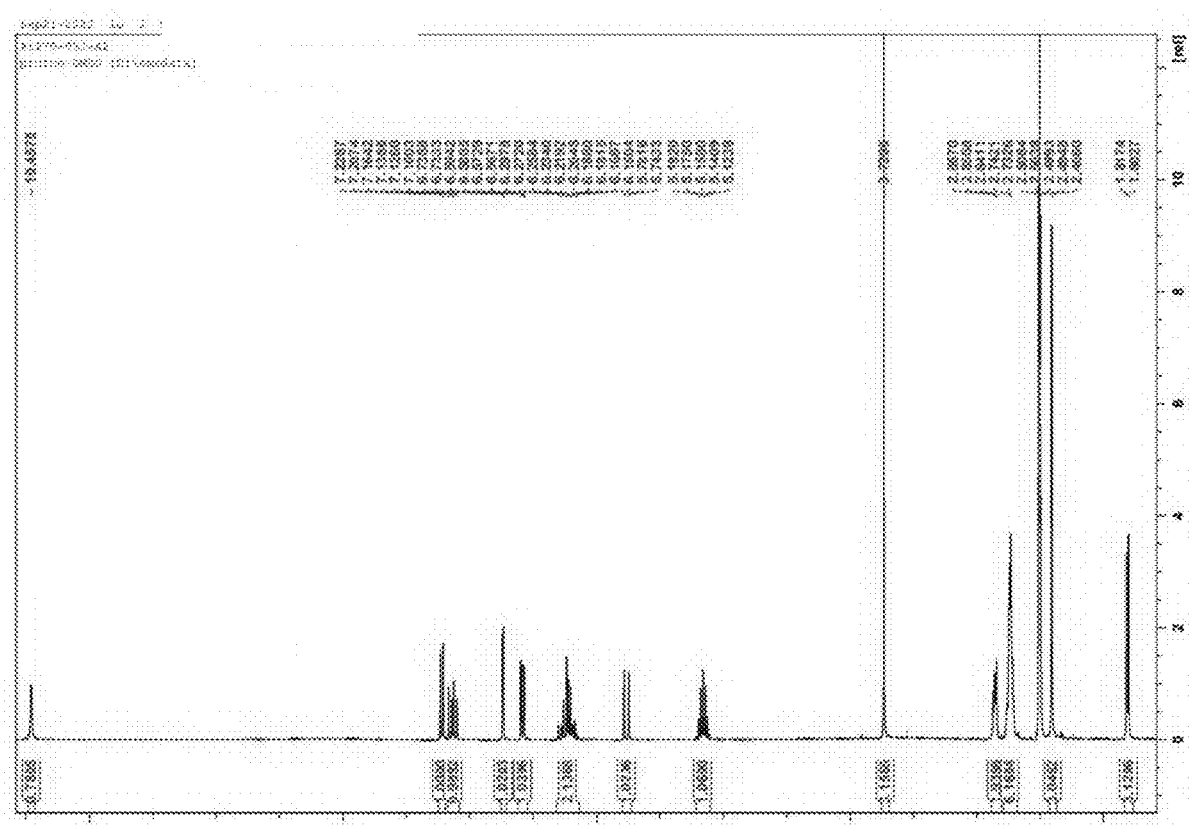

FIG. 817 depicts the $^1$H NMR spectrum of Experiment 3-Sample A2 (Tabernanthalog·Sorbate·HemiHFIPA, Pattern #7) in deuterated DMSO-$d_6$, calibrated to the non-deuterated solvent residual.

Figure 818:
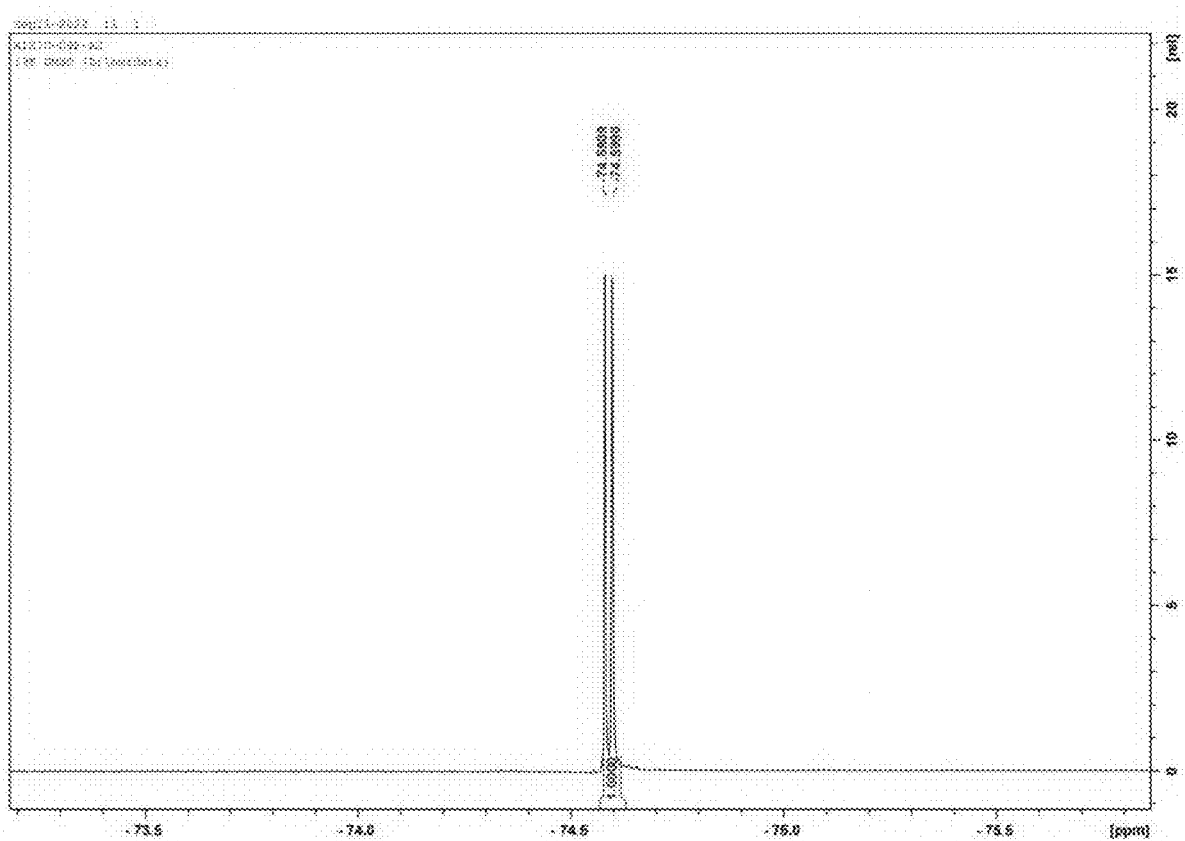

FIG. 818 depicts the $^{19}$F NMR spectrum of Experiment 3-Sample A2 (Tabernanthalog·Sorbate·HemiHFIPA, Pattern #7) in deuterated DMSO-$d_6$.

Figure 819:
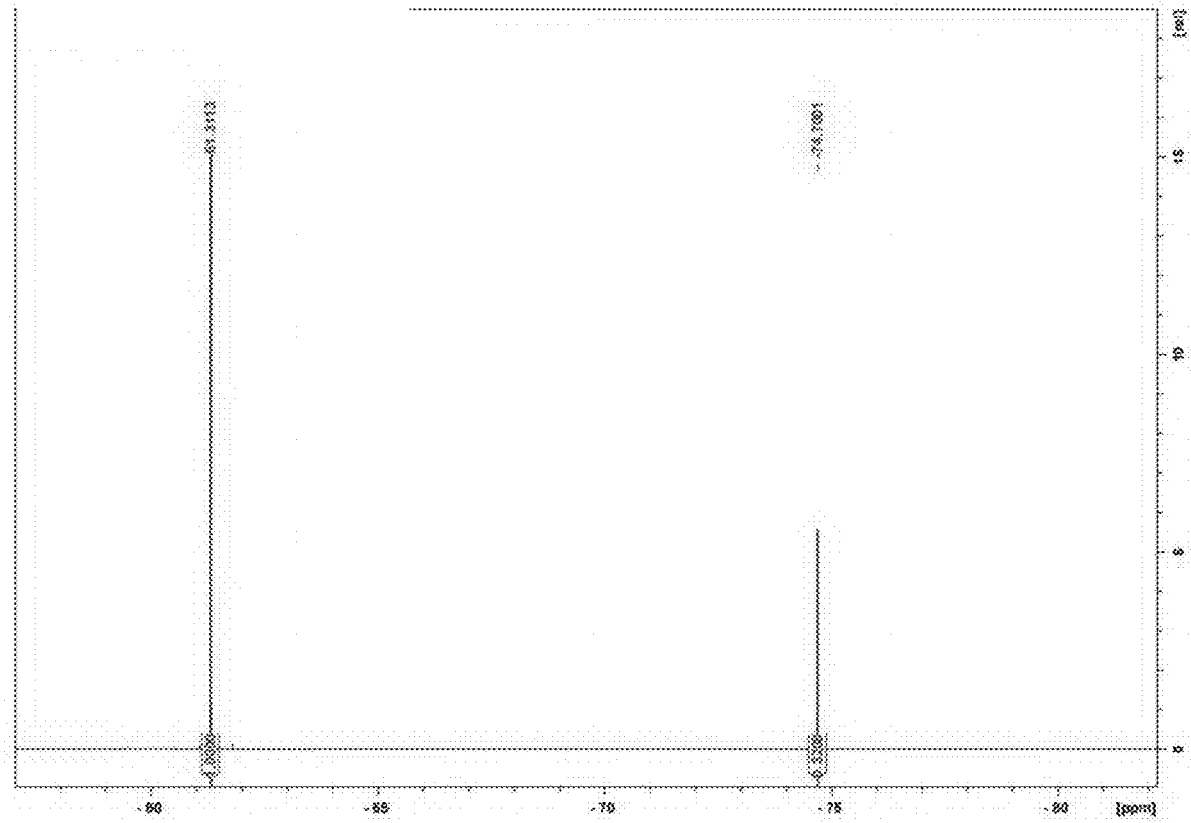

FIG. 819 depicts the $^{19}$F NMR spectrum of Experiment 3-Sample A2 (Tabernanthalog·Sorbate·HemiHFIPA, Pattern #7) versus internal standard α,α,α-trifluorotoluene in deuterated DMSO-$d_6$.

Figure 820:
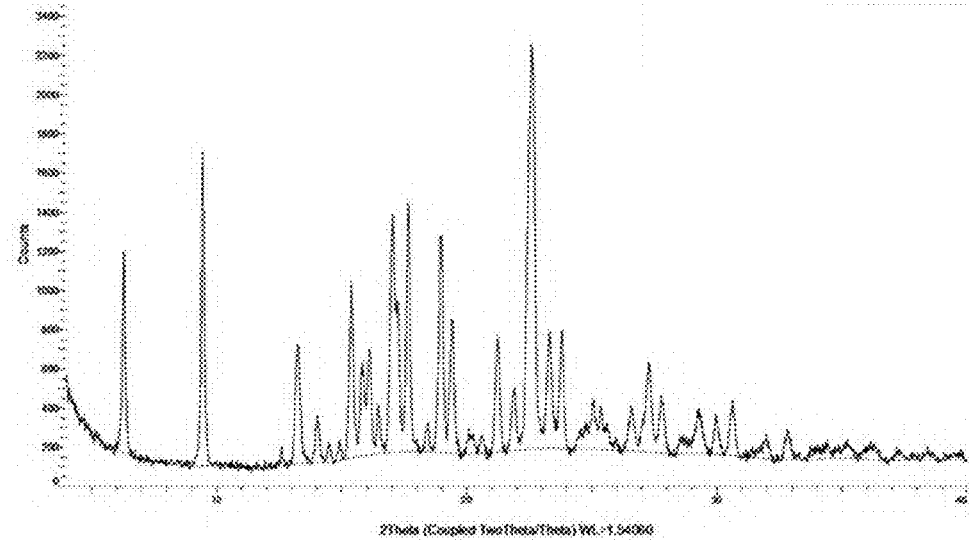

FIG. 820 depicts the XRPD profile of Experiment 3-Sample A2 (Tabernanthalog·Sorbate·HemiHFIPA, Pattern #7).

Figure 821:
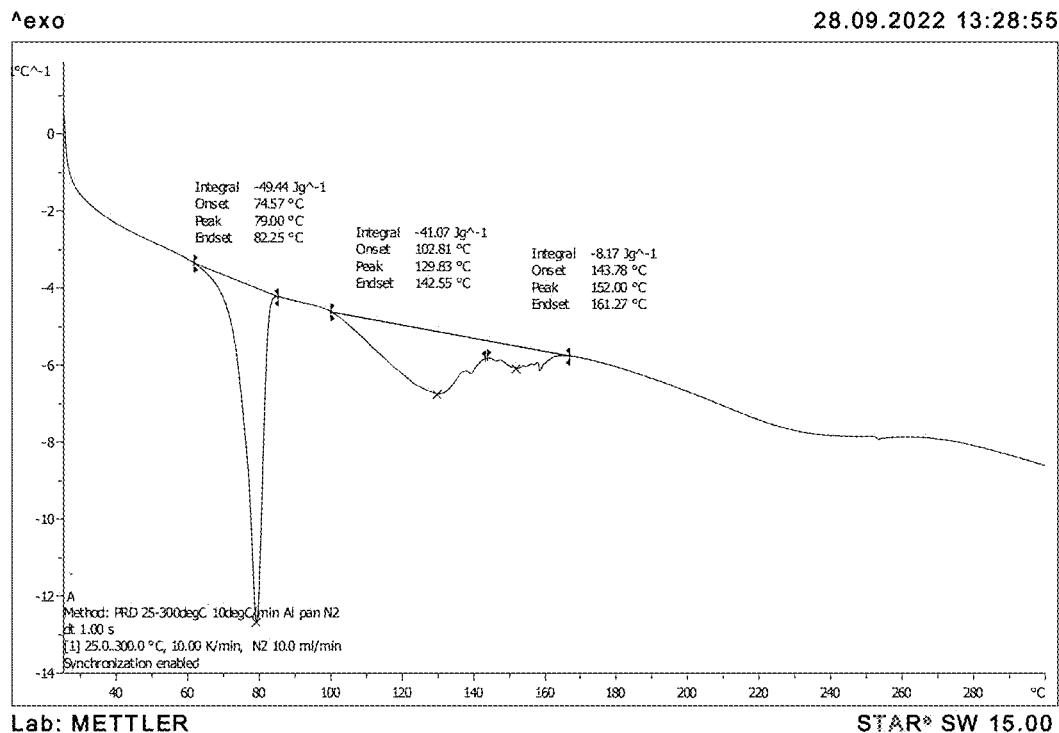

FIG. 821 depicts the DSC profile of Experiment 3-Sample A2 (Tabernanthalog·Sorbate·HemiHFIPA, Pattern #7).

Figure 822:
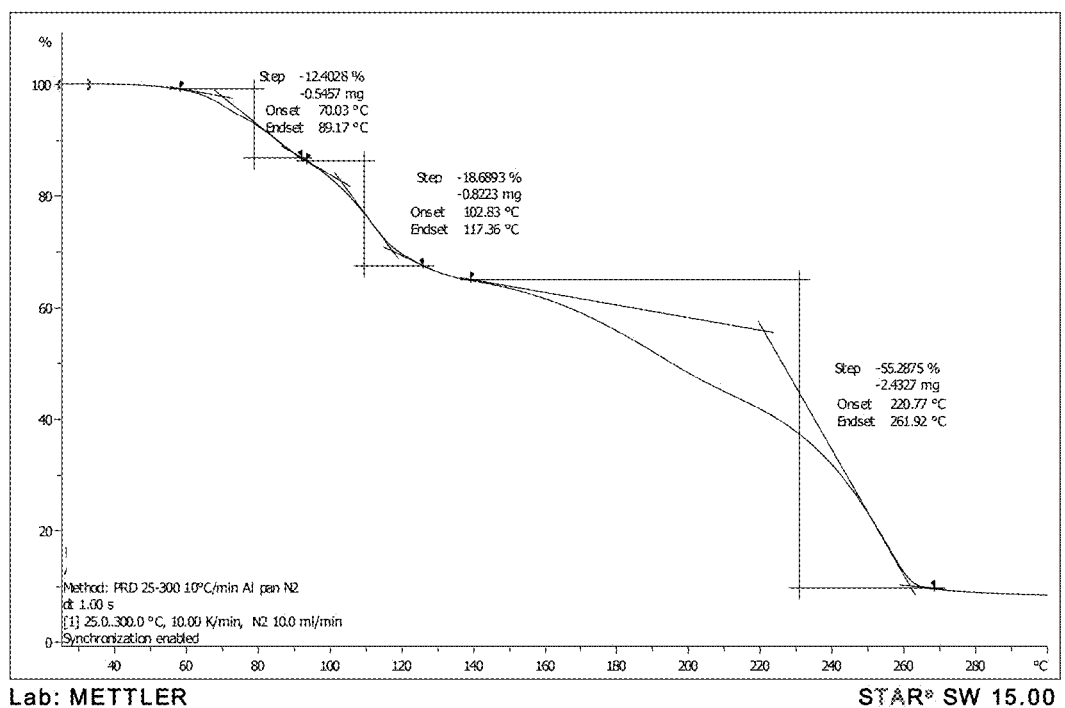

FIG. 822 depicts TGA profile of Experiment 3-Sample A2 (Tabernanthalog·Sorbate·HemiHFIPA, Pattern #7).

Figure 823:
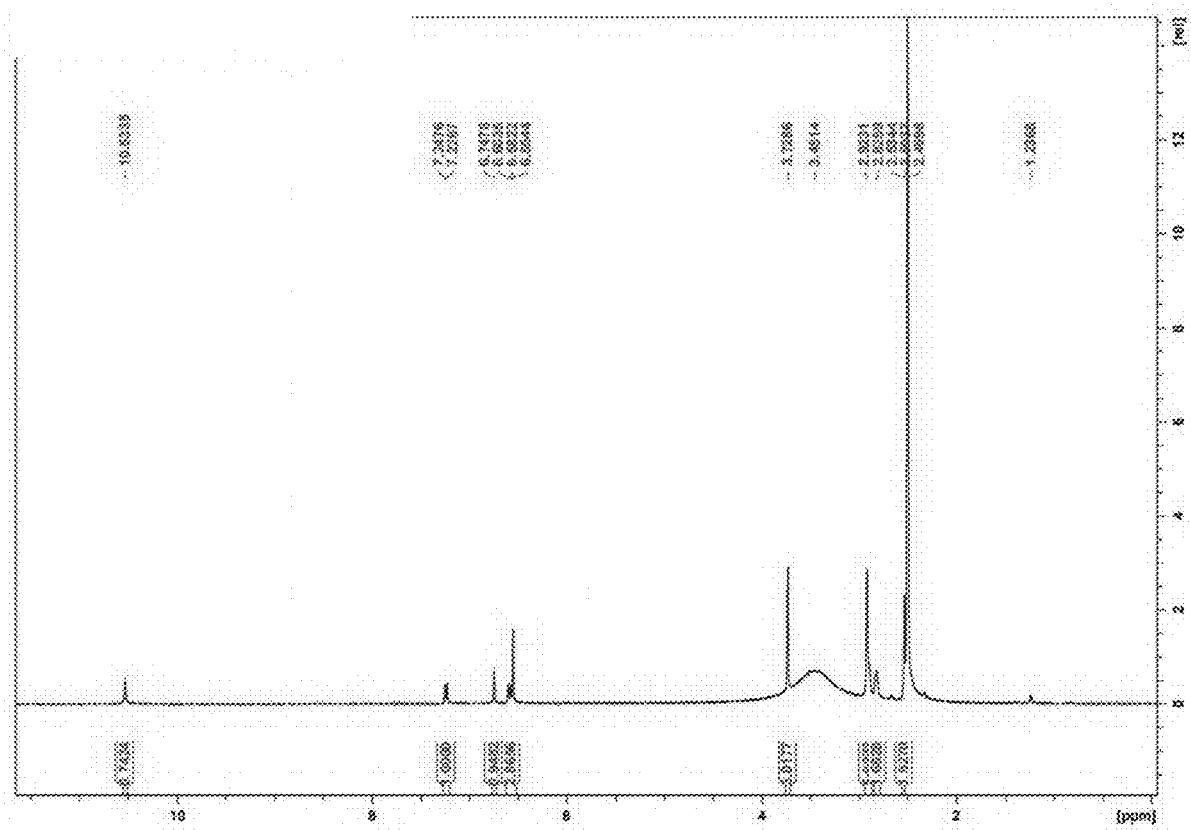

FIG. 823 depicts the $^1$H NMR spectrum of Experiment 2-Sample D1 (Tabernanthalog·Monofumarate, Amorphous) in deuterated DMSO-$d_6$.

Figure 824:
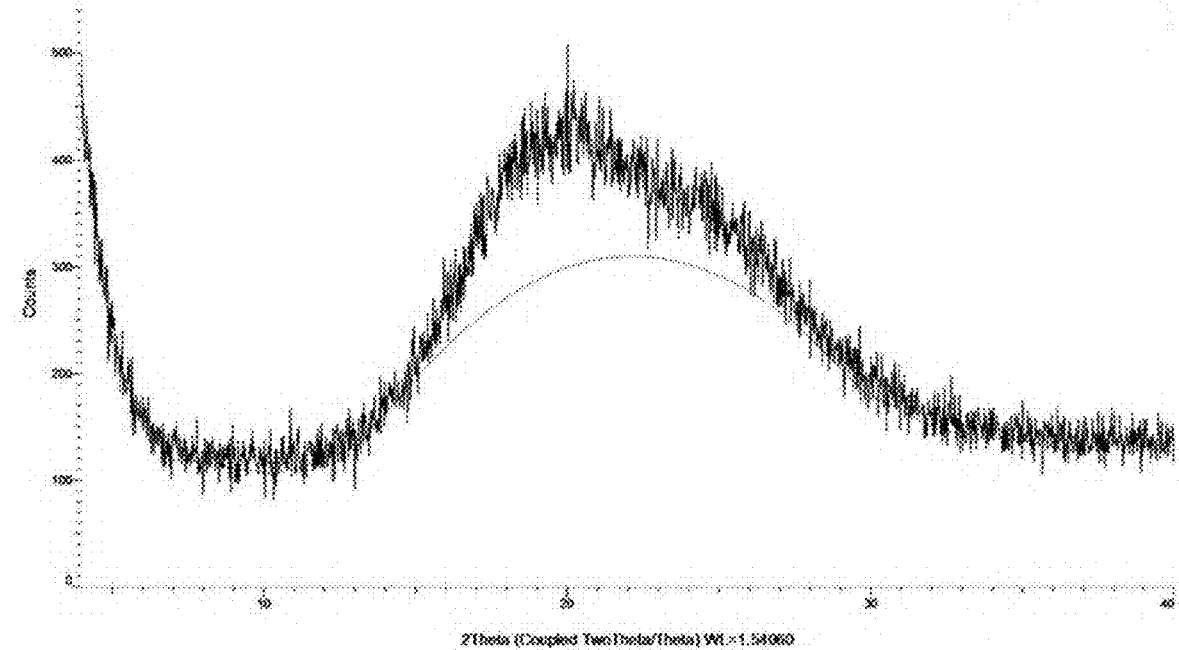

FIG. 824 depicts the XRPD profile of Experiment 2-Sample D1 (Tabernanthalog·Monofumarate).

FIG. 825 depicts the LC-MS profile of Experiment 2-Sample E1 (Tabernanthalog·Monofumarate, Amorphous), Spectra (top) M/Z (bottom).

Figure 826:
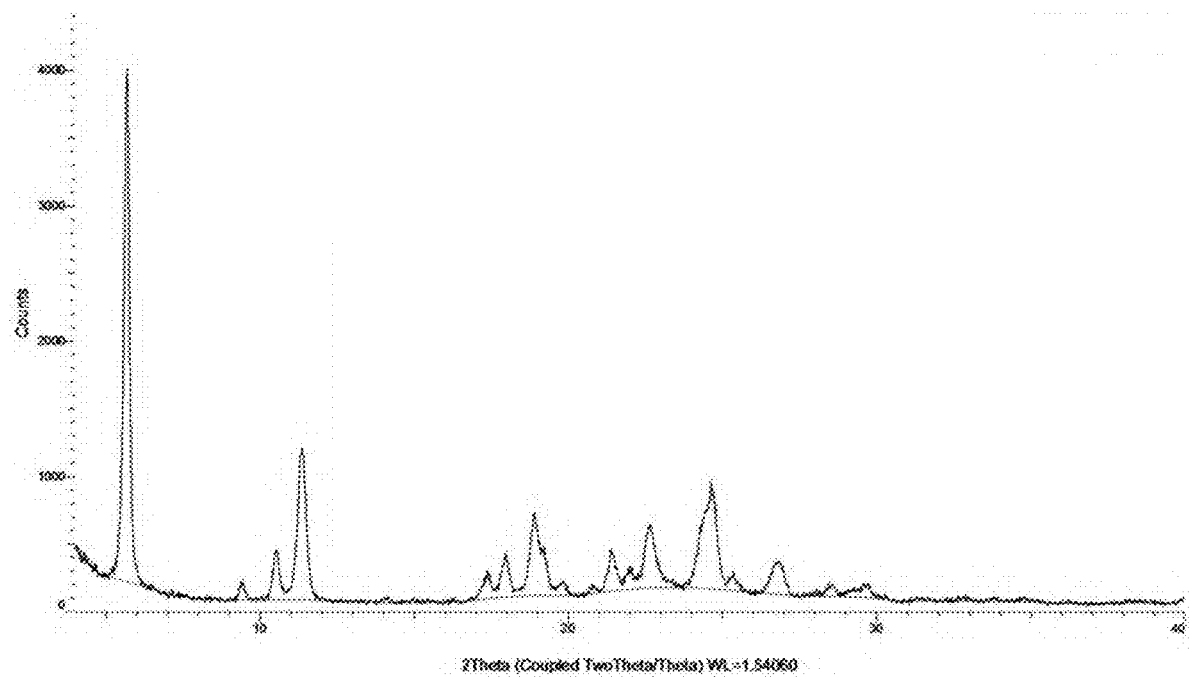

FIG. 826 depicts the XRPD profile of Experiment 4-Sample A1 (Tabernanthalog·Sorbate, Form A).

Figure 827:
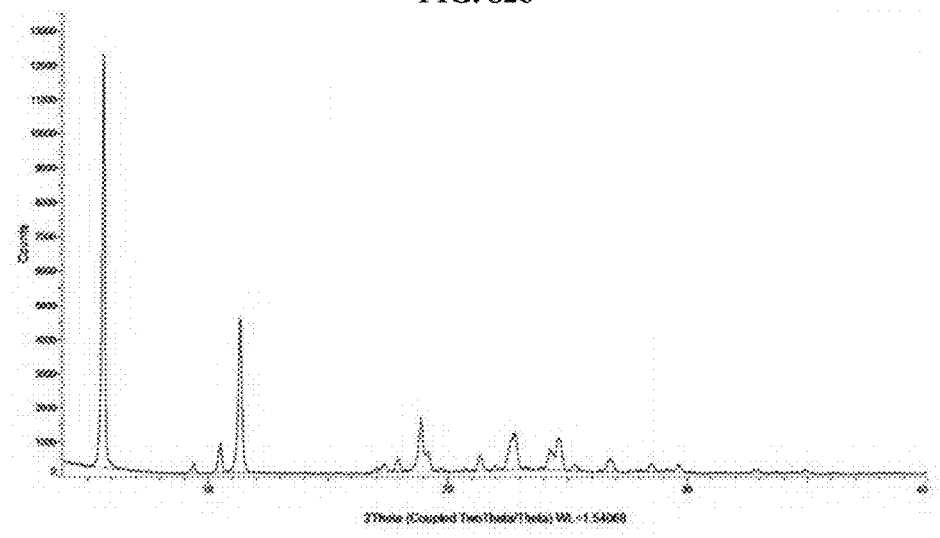

FIG. 827 depicts the XRPD profile of Experiment 4-Sample A2 (Tabernanthalog·Sorbate, Form A).

Figure 828:
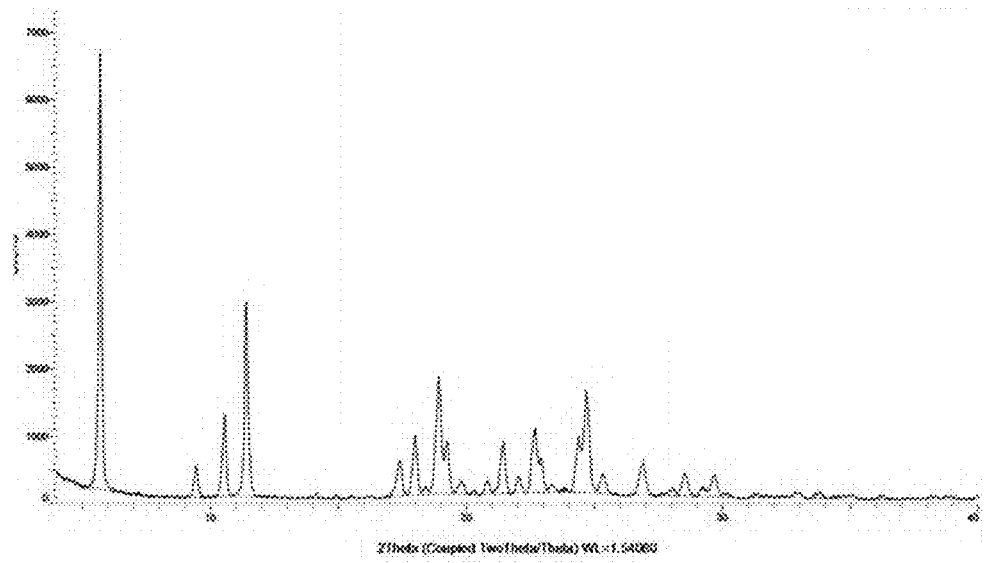

FIG. 828 depicts the XRPD profile of Experiment 4-Sample A3 (Tabernanthalog·Sorbate, Form A).

Figure 829:
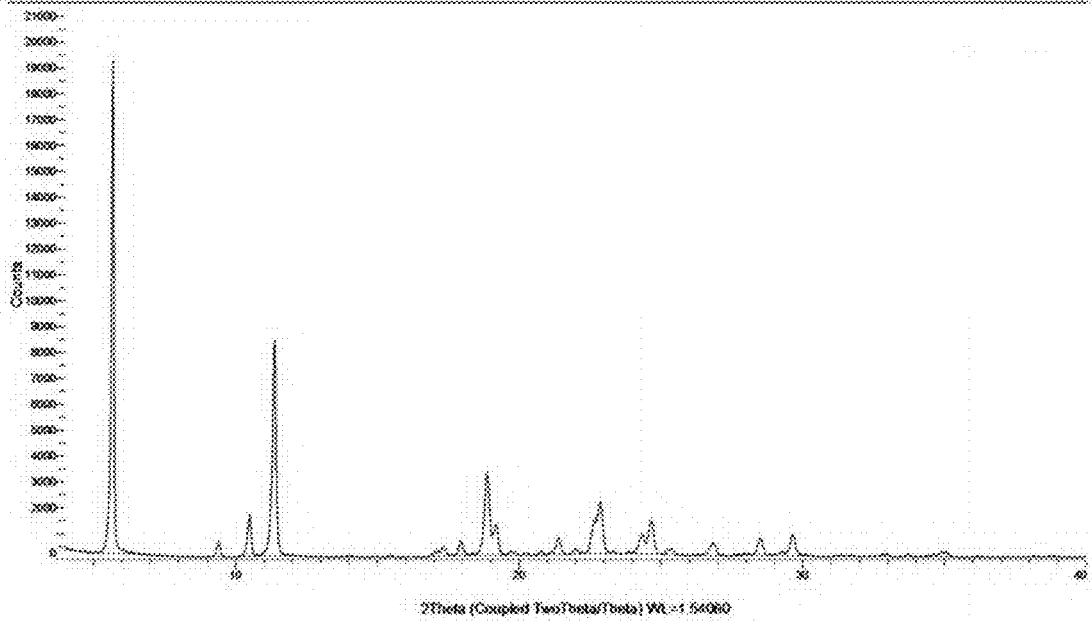

FIG. 829 depicts the XRPD profile of Experiment 4-Sample A4 (Tabernanthalog·Sorbate, Form A).

Figure 830:
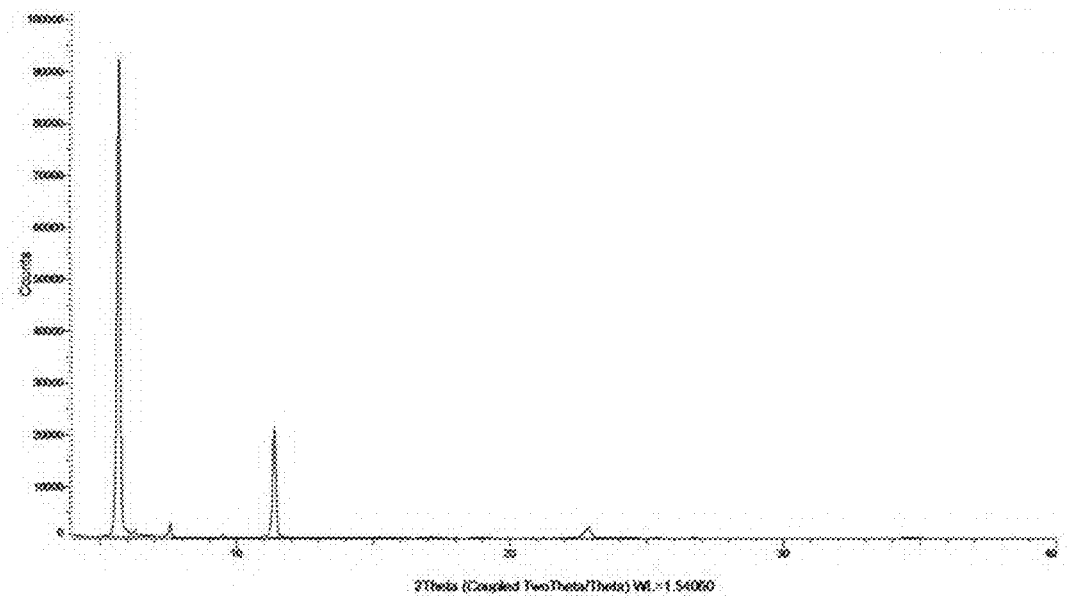

FIG. 830 depicts the XRPD profile of Experiment 4-Sample B1 (Tabernanthalog·Sorbate·HemiHFIPA, Pattern #7).

Figure 831:
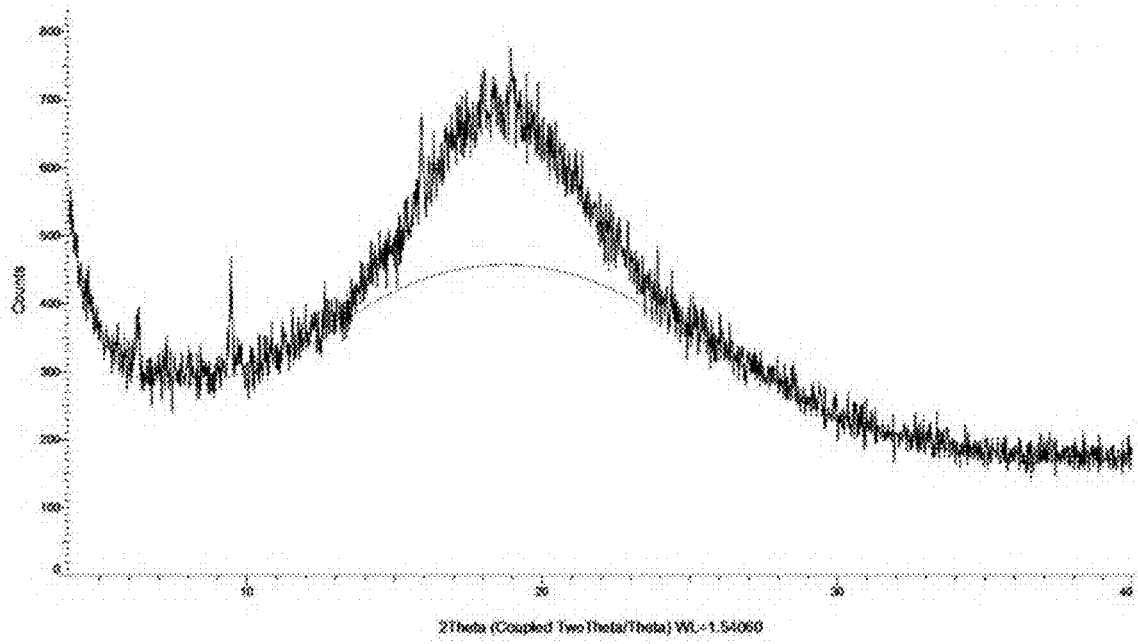

FIG. 831 depicts the XRPD profile of Experiment 4-Sample B2 (Tabernanthalog·Sorbate).

Figure 832:
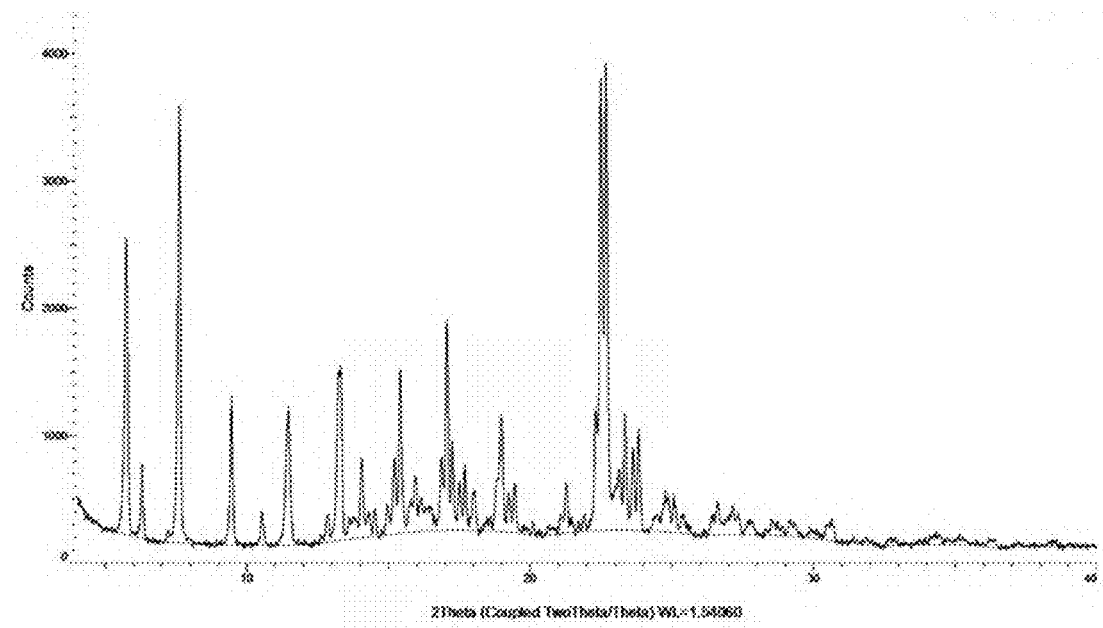

FIG. 832 depicts the XRPD profile of Experiment 4-Sample B3 (Tabernanthalog·Sorbate, Pattern #7).

Figure 833:
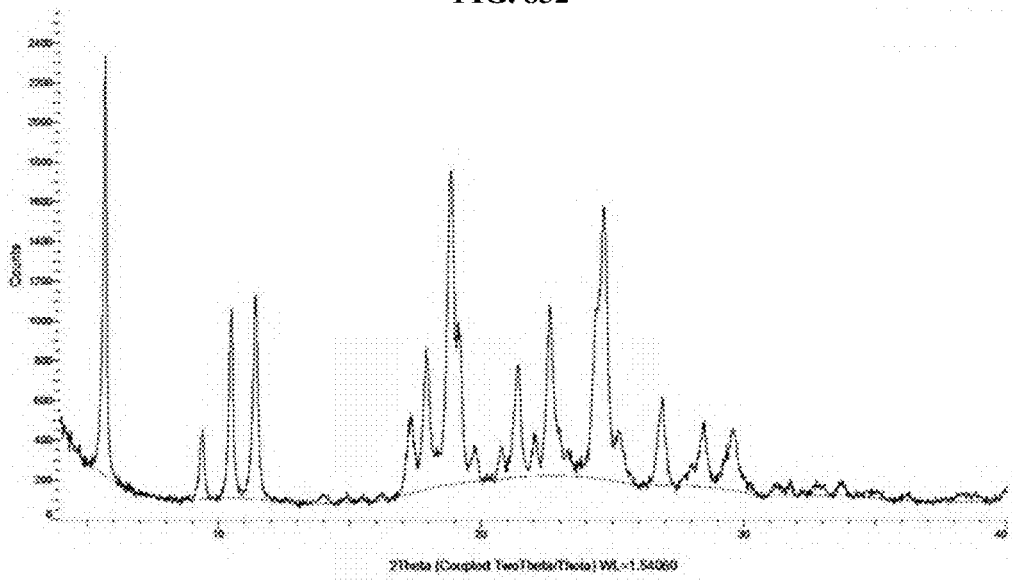

FIG. 833 depicts the XRPD profile of Experiment 4-Sample C1 (Tabernanthalog·Sorbate, Form A).

Figure 834:
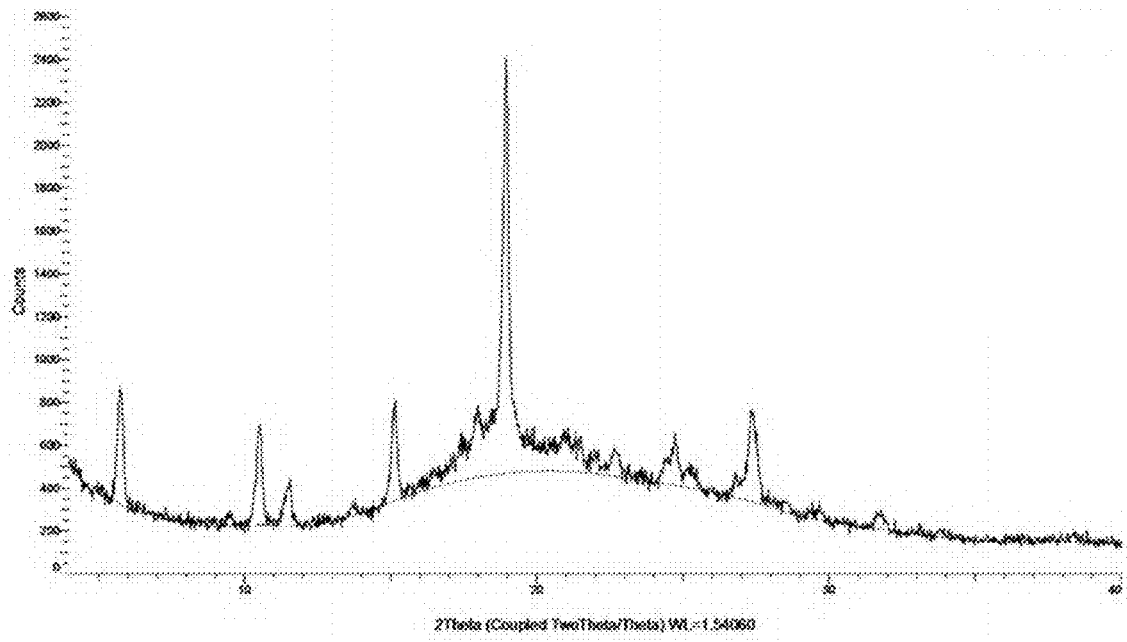

FIG. 834 depicts the XRPD profile of Experiment 4-Sample D1 (Tabernanthalog·Sorbate, Form A).

Figure 835:
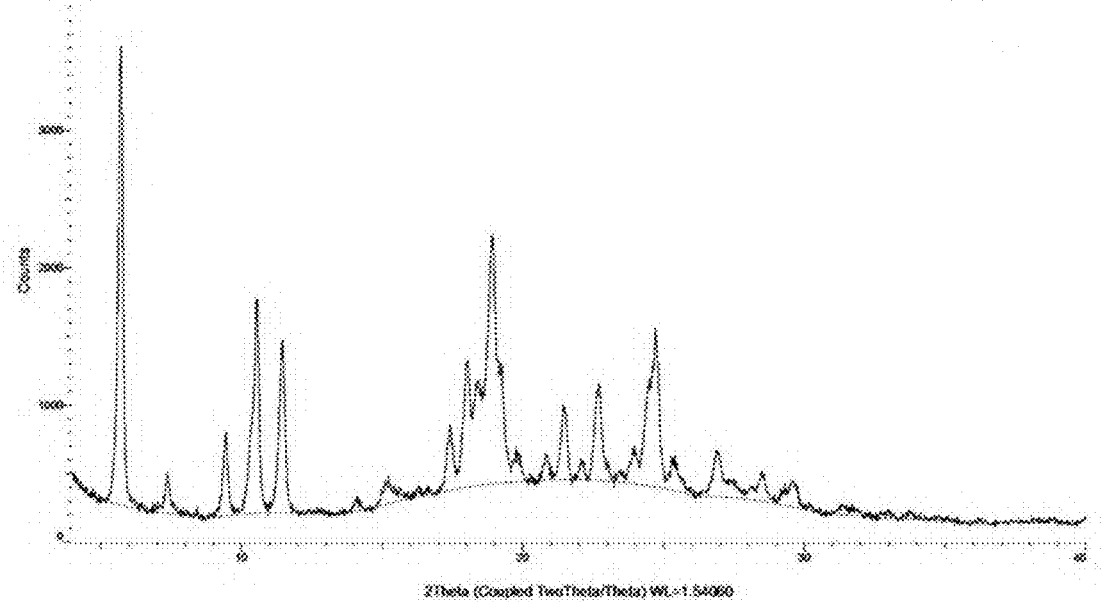

FIG. 835 depicts the XRPD profile of Experiment 4-Sample D2 (Tabernanthalog·Sorbate, Form A).

Figure 836:
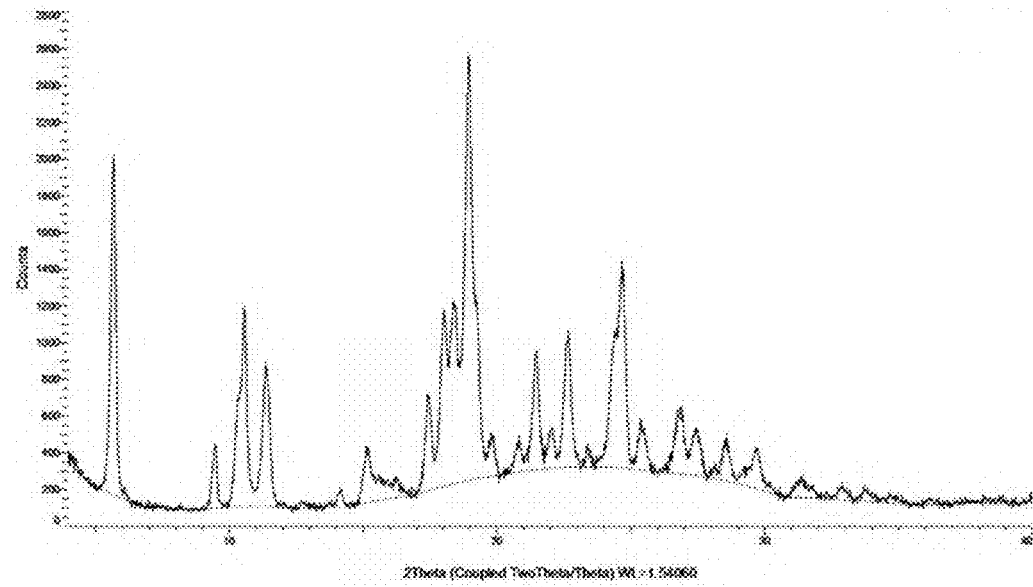

FIG. 836 depicts the XRPD profile of Experiment 4-Sample E1 (Tabernanthalog·Sorbate, Form A).

Figure 837:
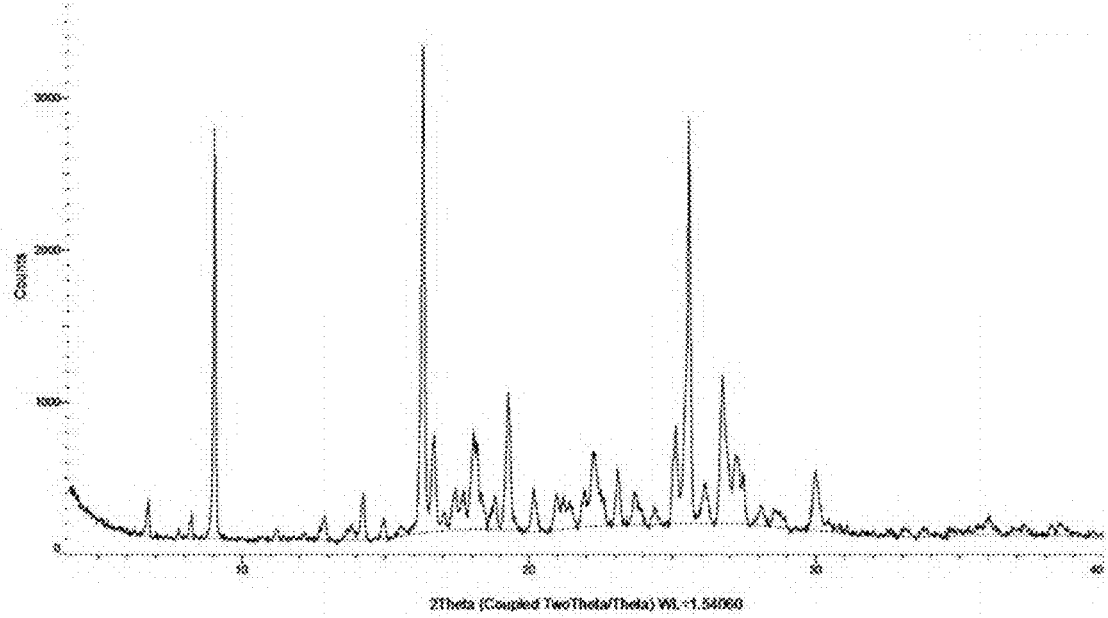

FIG. 837 depicts the XRPD profile of Experiment 5-Sample A1 (Tabernanthalog·Monofumarate, Pattern #1).

Figure 838:
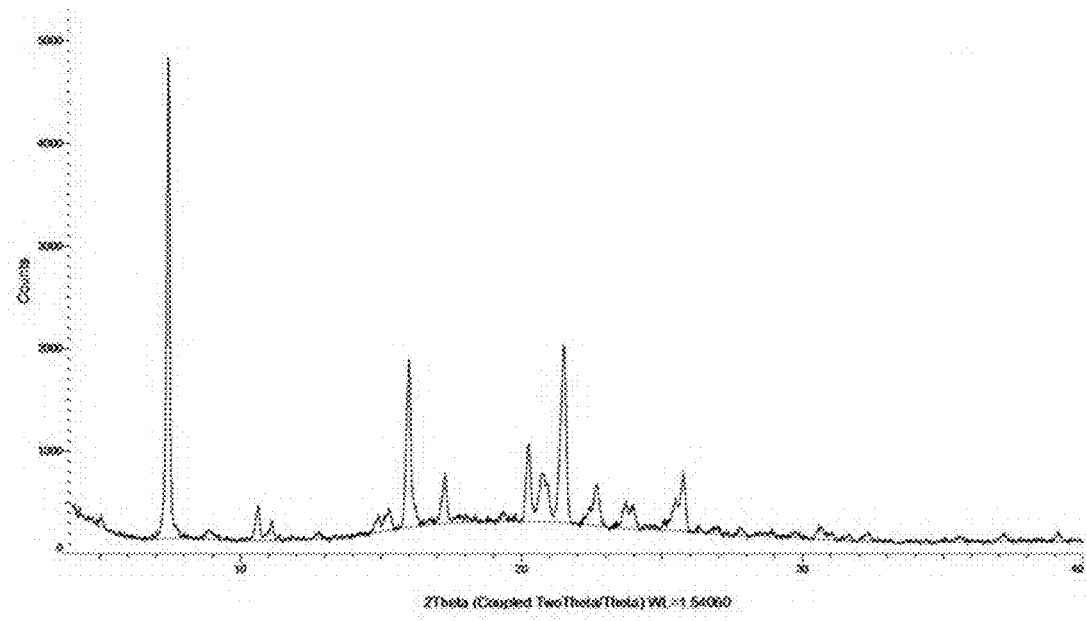

FIG. 838 depicts the XRPD profile of Experiment 5-Sample A2 (Tabernanthalog·Monofumarate, Pattern #11).

Figure 839:
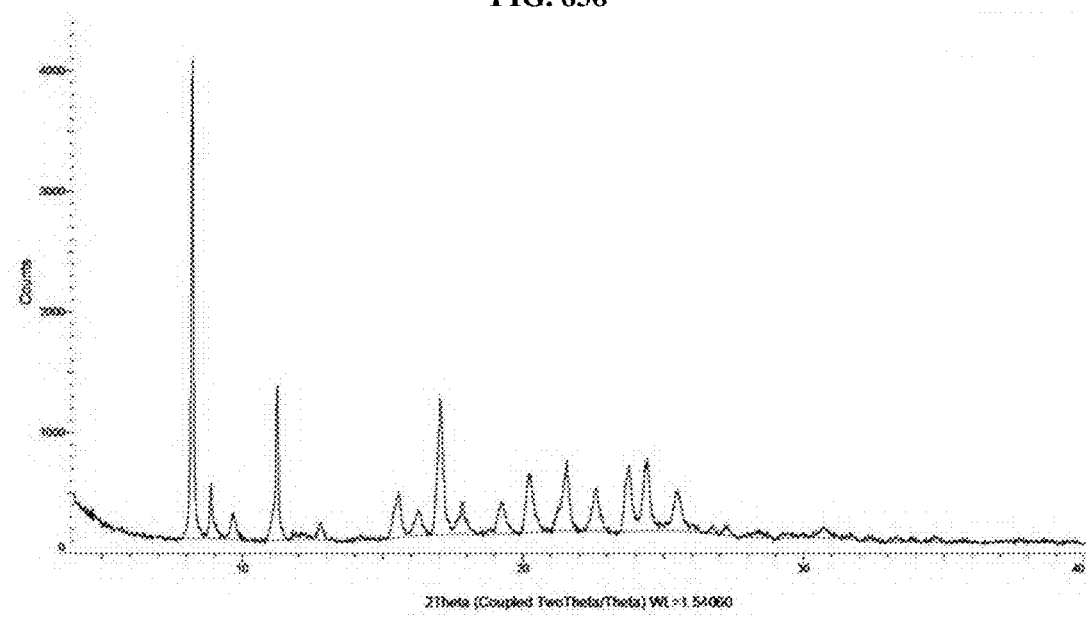

FIG. 839 depicts the XRPD profile of Experiment 5-Sample A3 (Tabernanthalog·Monofumarate, Pattern #3).

Figure 840:
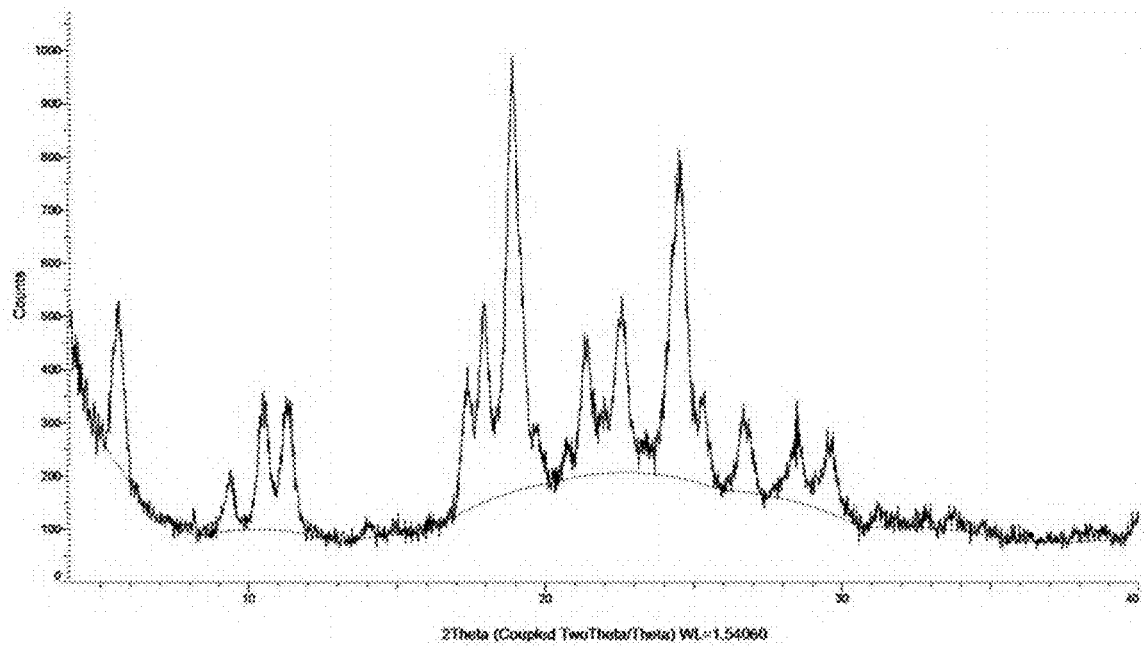

FIG. 840 depicts the XRPD profile of Experiment 6-Sample A1 (Tabernanthalog·Sorbate, Form A).

Figure 841:
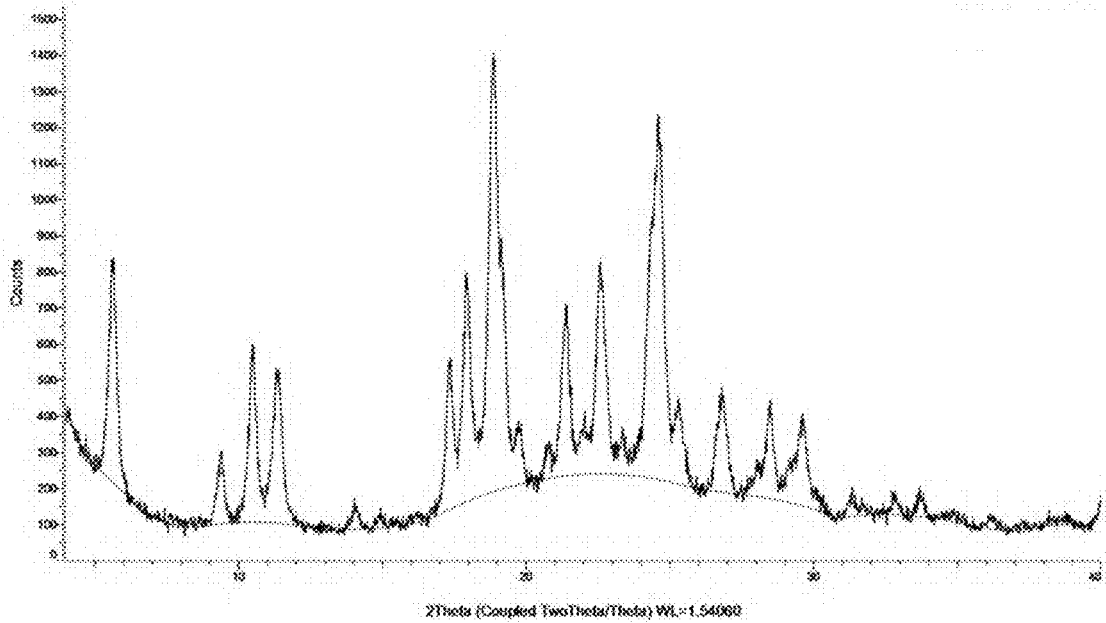

FIG. 841 depicts the XRPD profile of Experiment 6-Sample A2 (Tabernanthalog·Sorbate, Form A).

Figure 842:
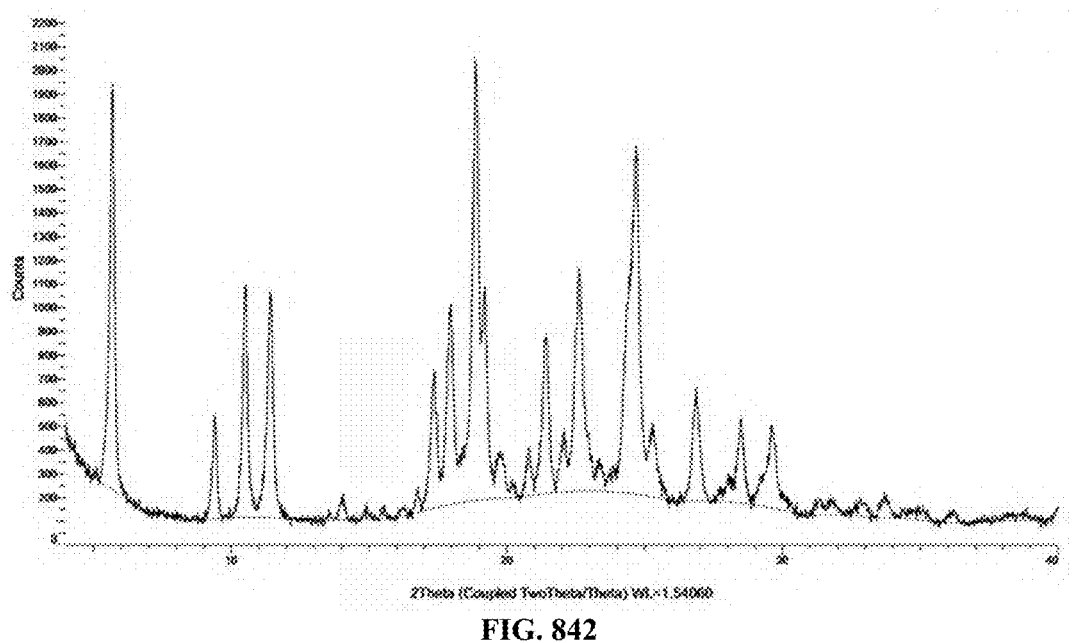

FIG. 842 depicts the XRPD profile of Experiment 6-Sample A3 (Tabernanthalog·Sorbate, Form A).

Figure 843:
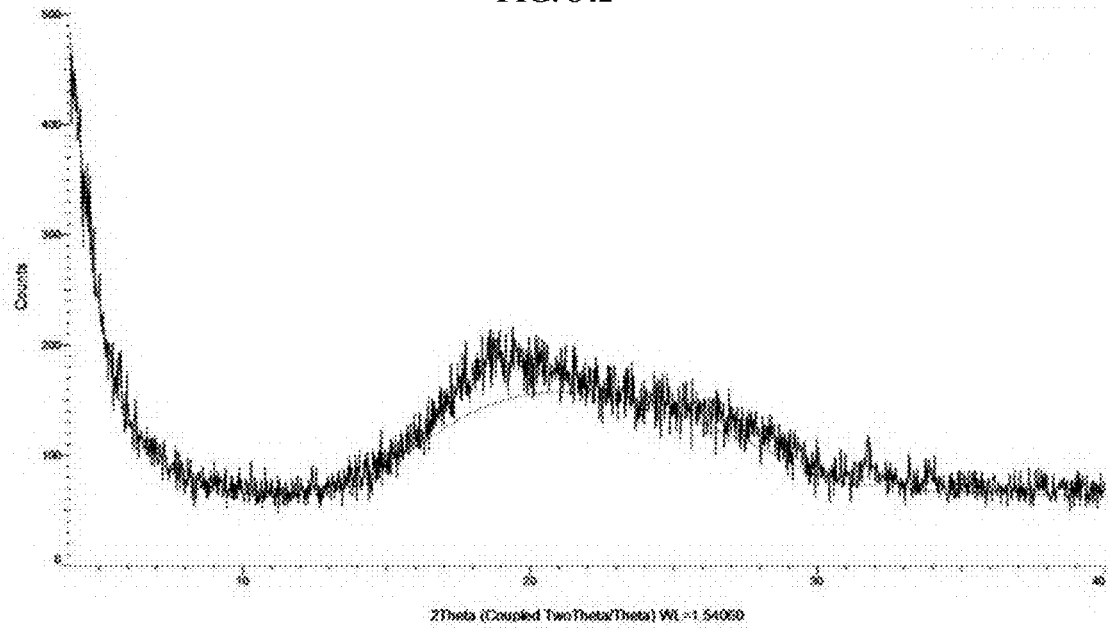

FIG. 843 depicts the XRPD profile of Experiment 1-Sample D1 (Tabernanthalog·Sorbate, amorphous).

Figure 844:
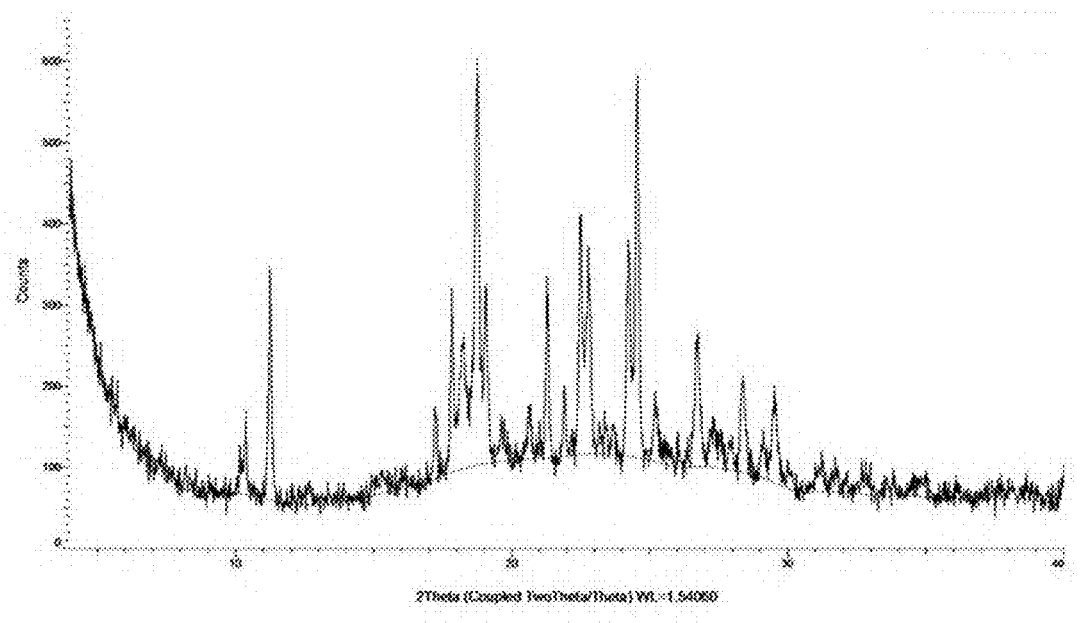

FIG. 844 depicts the XRPD profile of Experiment 1-Sample D2 (Tabernanthalog·Sorbate, Form A). Experiment 1-Sample D1 left standing overnight in ambient conditions to yield crystalline material (Experiment 1-Sample D2).

Figure 845:
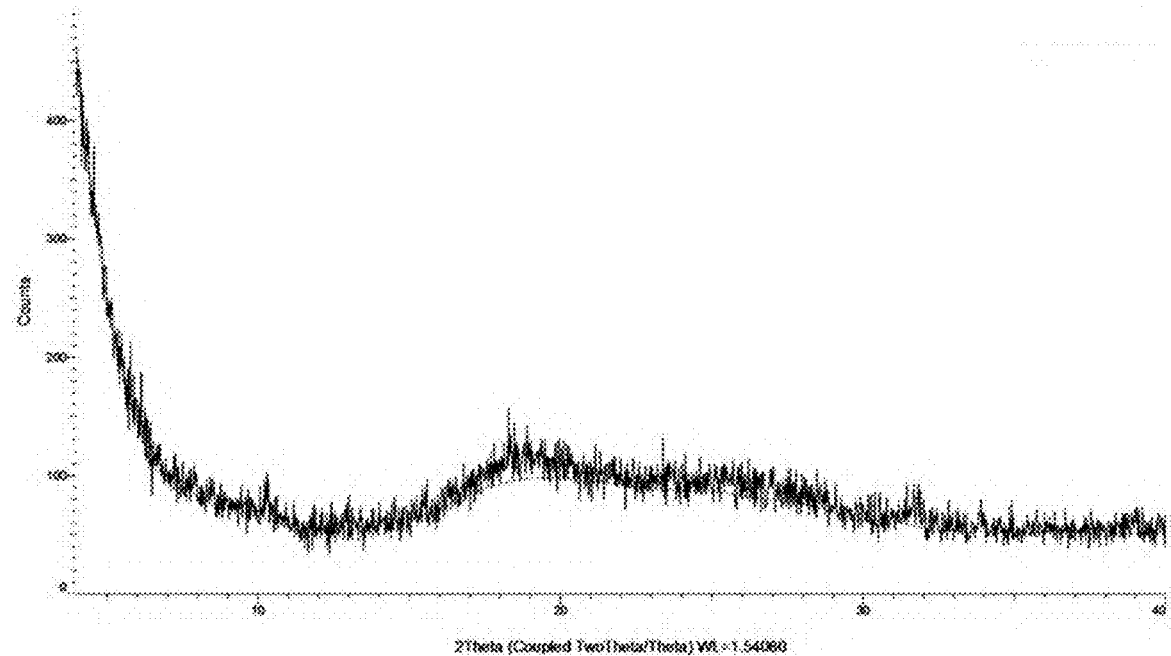

FIG. 845 depicts the XRPD profile of Experiment 1-Sample E1 (Tabernanthalog·Sorbate, amorphous).

Figure 846:
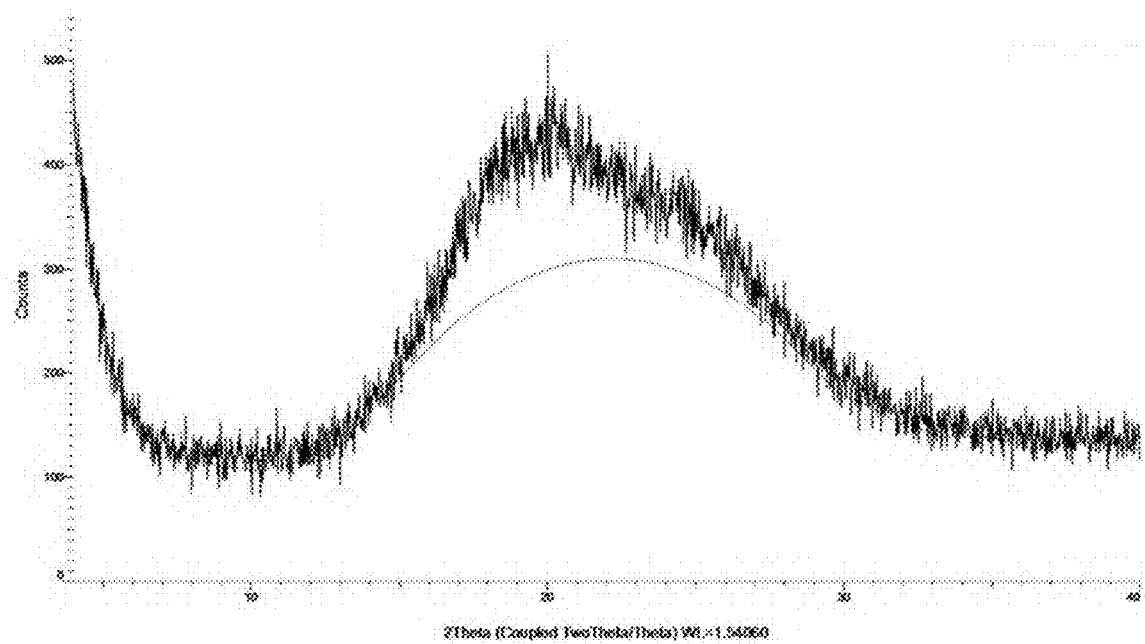

FIG. 846 depicts the XRPD profile of Experiment 2-Sample D1 (Tabernanthalog·Monofumarate, amorphous).

Figure 847:
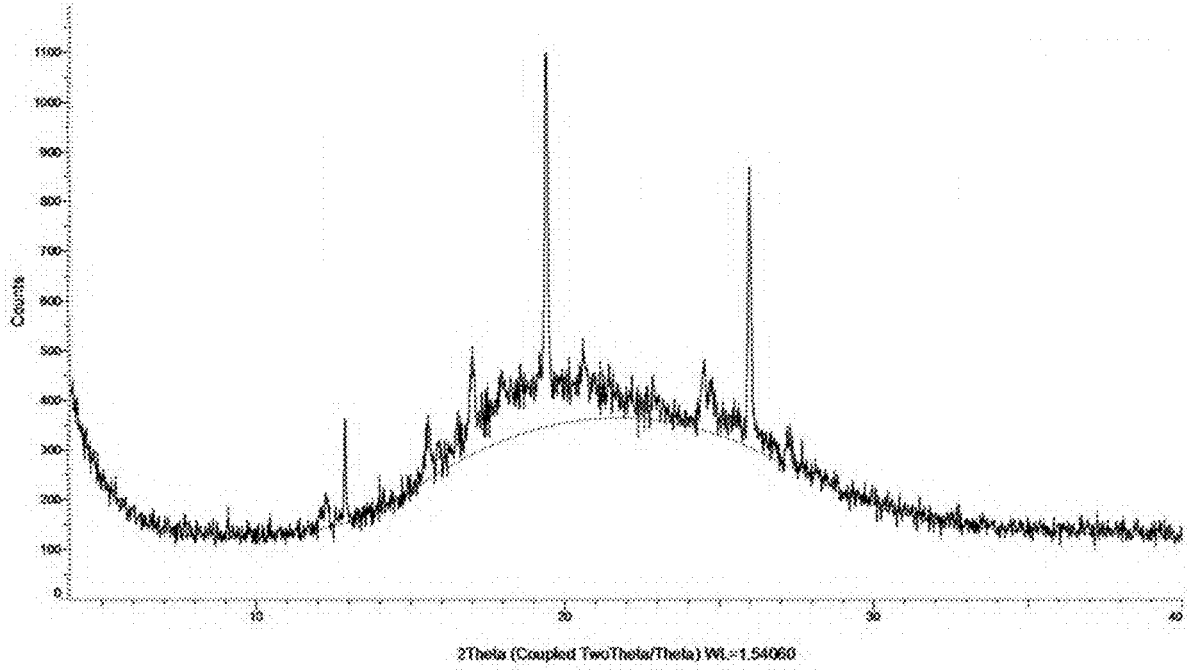

FIG. 847 depicts the XRPD profile of Experiment 2-Sample E1 (Tabernanthalog·Monofumarate).

Figure 848:
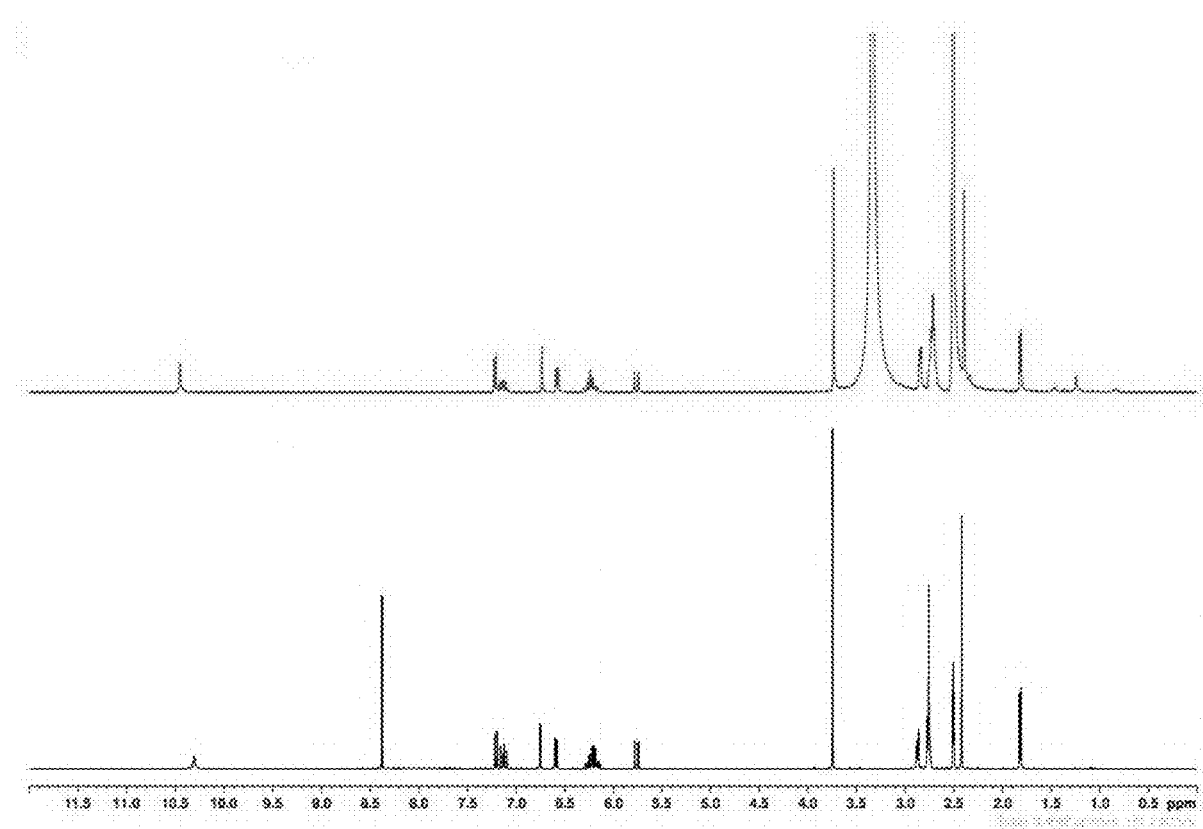

FIG. 848 depicts an overlay of $^1$H NMR spectra of Experiment 1-Sample D1 (Tabernanthalog·Sorbate, Amorphous, DMSO-$d_6$ upper spectrum, top) and A1270-076-A1 (Tabernanthalog·Sorbate, Form A, DMSO-$d_6$, Internal standard: TCNB, lower spectrum, bottom).

Figure 849:
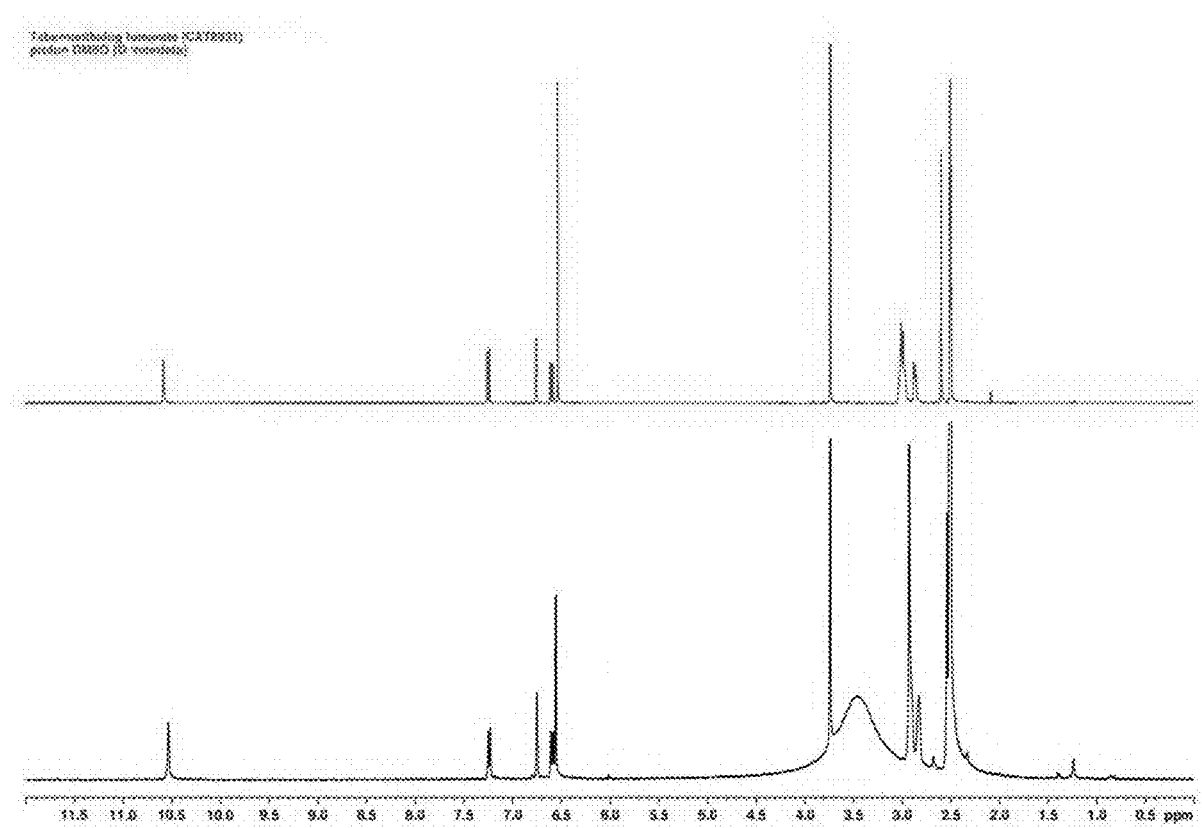

FIG. 849 depicts an overlay of $^1$H NMR spectra of Experiment 2-Sample D1 (Tabernanthalog·Monofumarate, amorphous, DMSO-$d_6$, lower spectrum, bottom and Tabernanthalog·Monofumarate (Tabernanthalog·Monofumarate, Pattern #1, DMSO-$d_6$ top).

Figure 850:
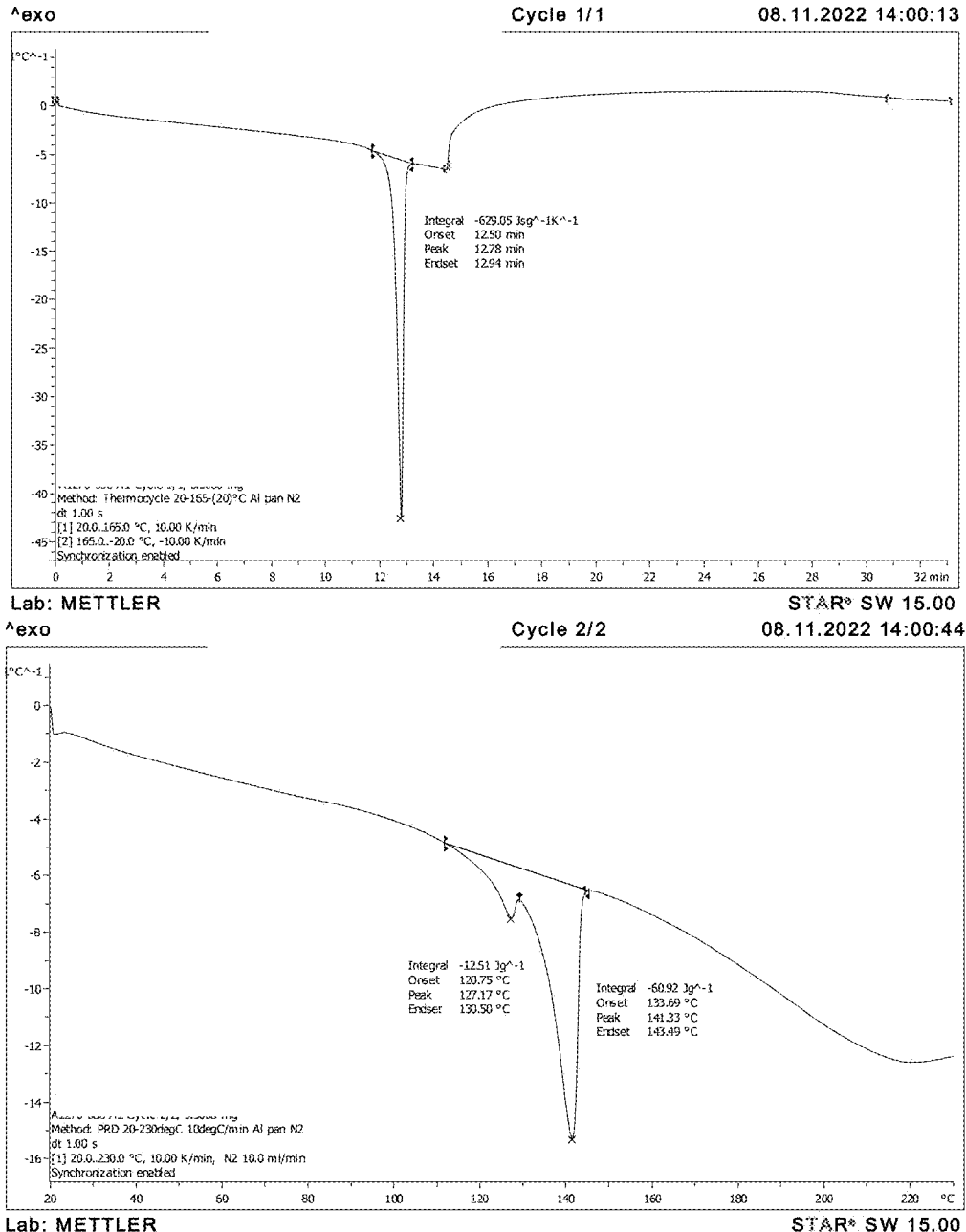

FIG. 850 depicts extracted DSC profiles of Experiment 1-Sample A1 (Tabernanthalog·Sorbate) cycle 1 and cycle 2.

Figure 851:
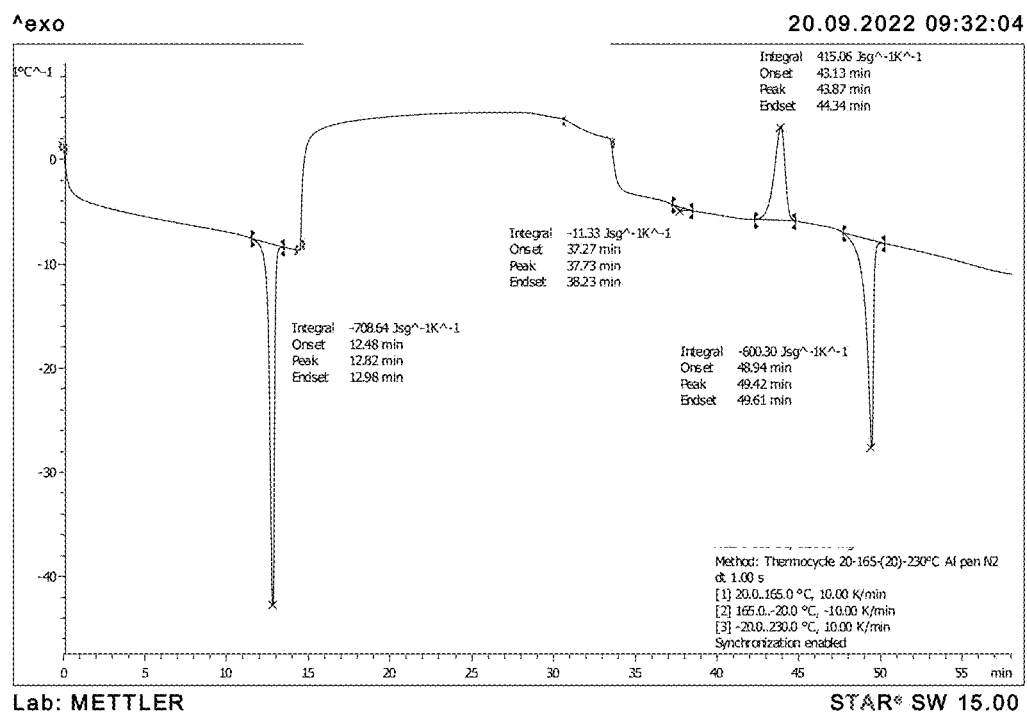

FIG. 851 depicts the complete thermocycle DSC profile of Experiment 1-Sample B1 (Tabernanthalog·Sorbate) (heat flow vs time).

FIG. 852 depicts the extracted DSC profiles of Experiment 2-Sample A1 (Tabernanthalog·Monofumarate, cycle 1 top, cycle 2 bottom).

Figure 853:
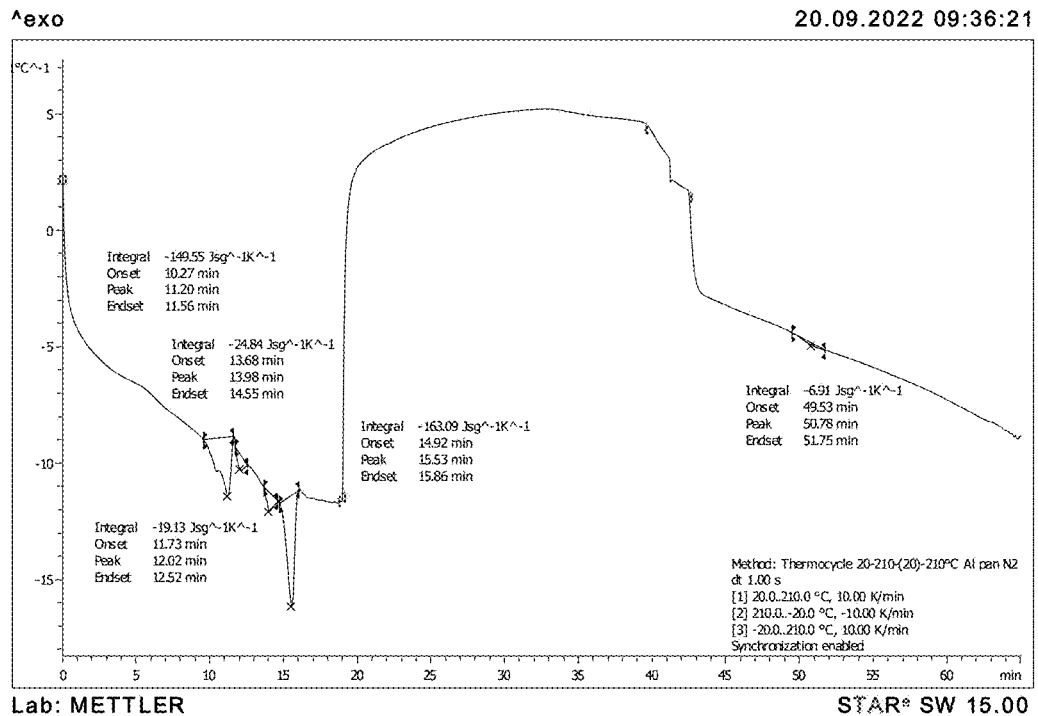

FIG. 853 depicts the thermocycle DSC profile of Experiment 2-Sample B1 (Tabernanthalog·Monofumarate, heat flow vs time).

Figure 854:
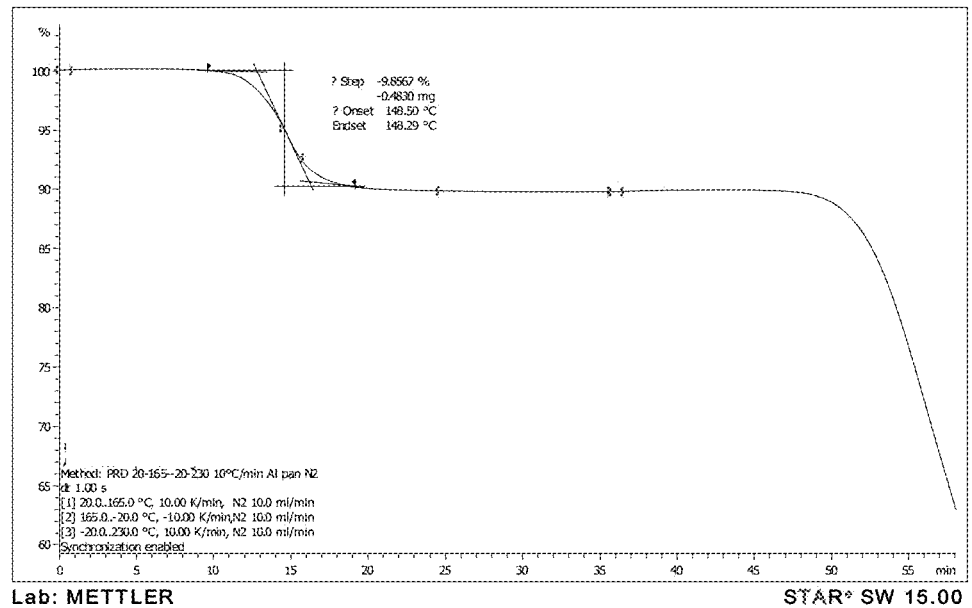

FIG. 854 depicts the thermocycle TGA profile of Experiment 1-Sample C1 (Tabernanthalog·Sorbate, mass loss vs time).

Figure 855:
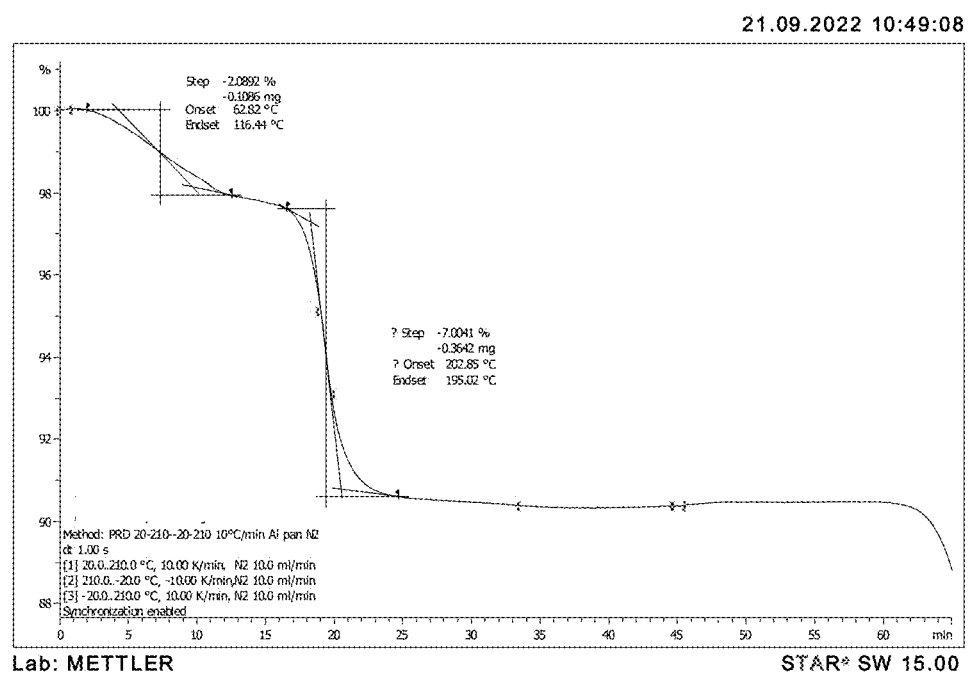

FIG. 855 depicts the thermocycle TGA profile of Experiment 2-Sample C1 (Tabernanthalog·Monofumarate, mass loss vs time).

Figure 856:
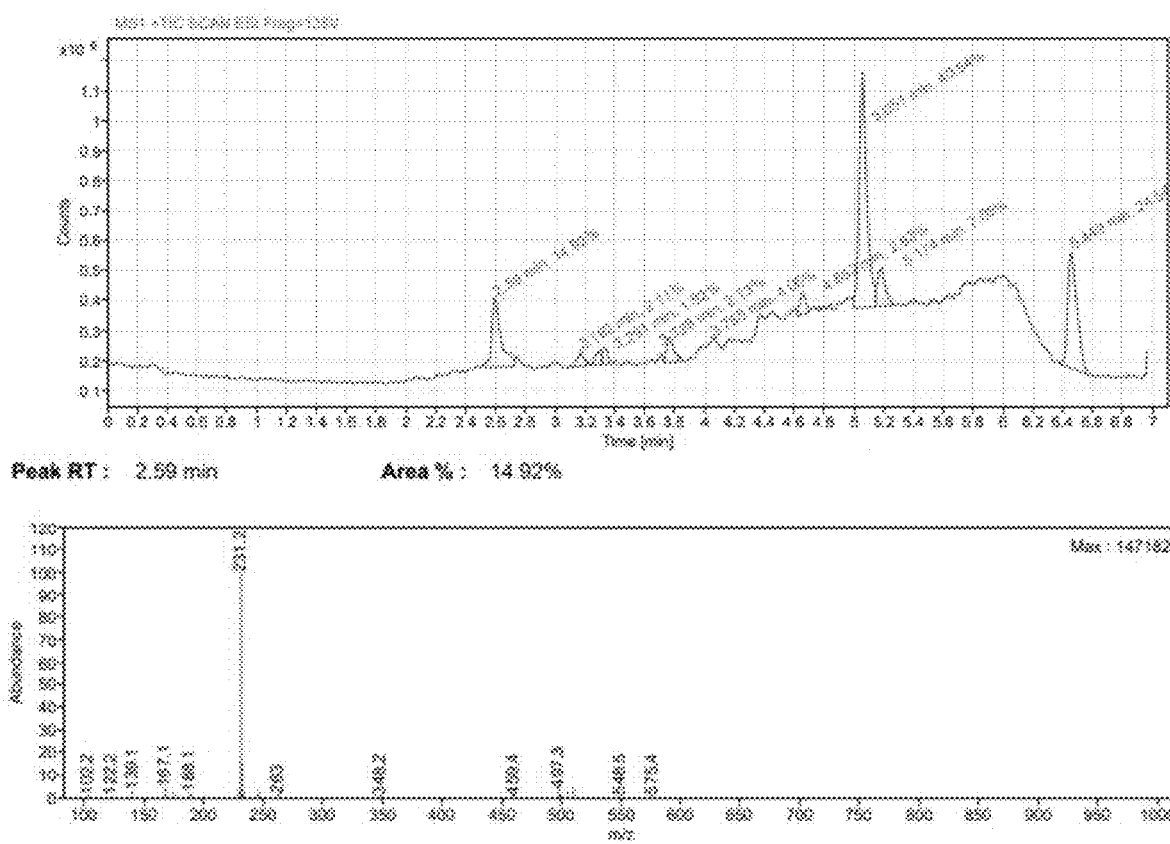

FIG. 856 depicts the LC-MS profile of Experiment 1-Sample E1 (Tabernanthalog·Sorbate, Amorphous), Spectra (top) m/z (bottom).

FIG. 857 depicts the LC-MS profile of Experiment 2-Sample E1 (Tabernanthalog·Monofumarate, amorphous), spectrum (top) m/z (bottom).

Figure 858:
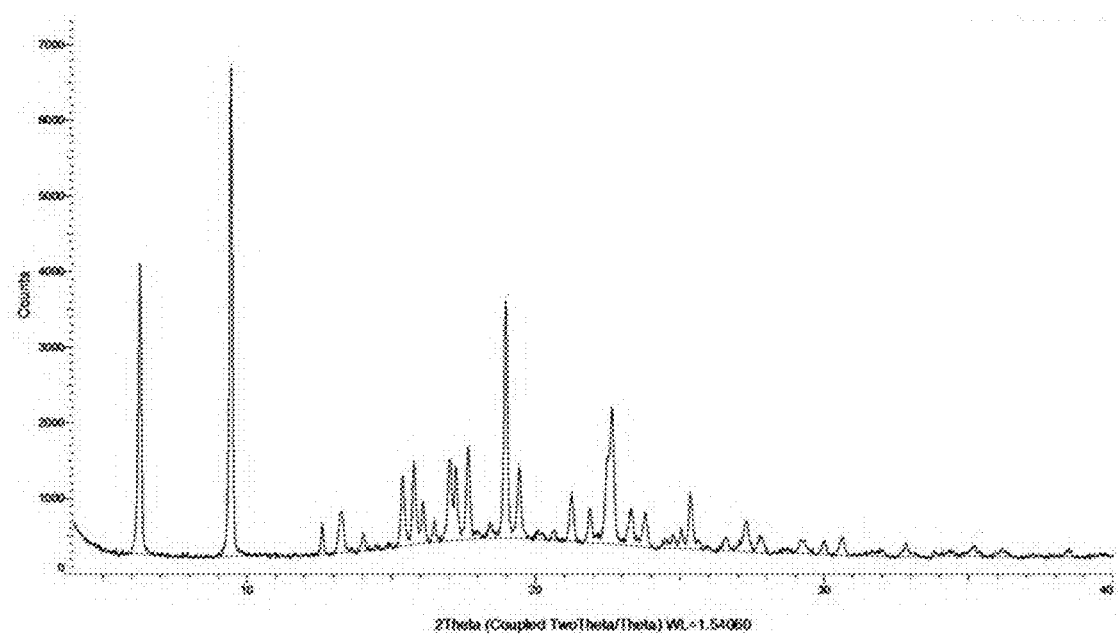

FIG. 858 depicts the XRPD profile of Experiment 3-Sample A1 (Tabernanthalog·Sorbate, Pattern #7).

Figure 859:
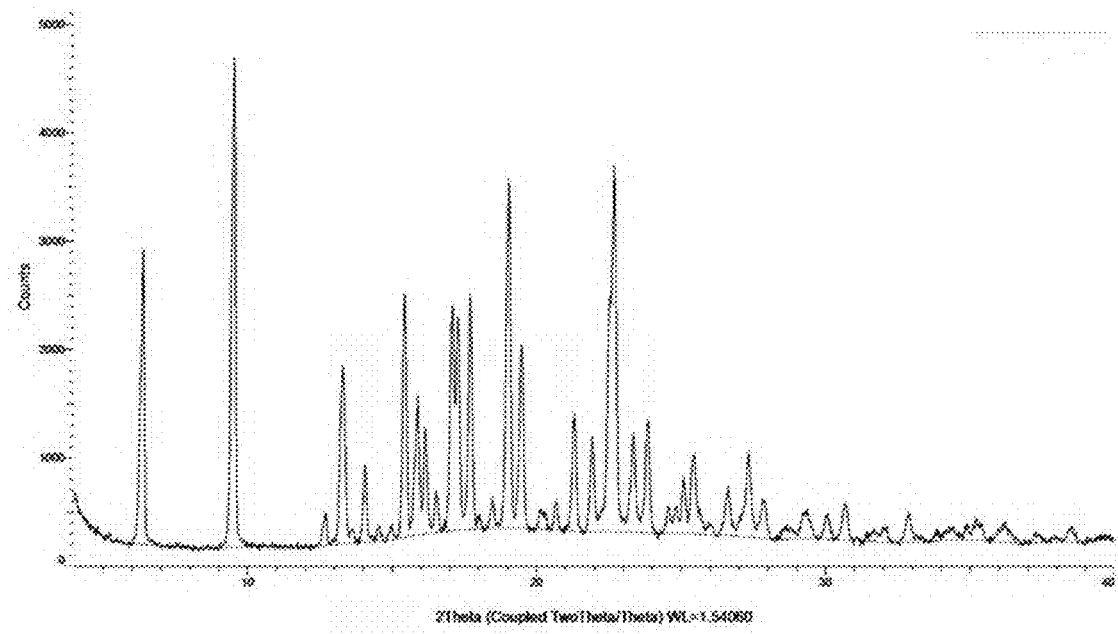

FIG. 859 depicts the XRPD profile of Experiment 3-Sample B1 (Tabernanthalog·Sorbate, Pattern #7) 20° C., 75% RH, 5d.

Figure 860:
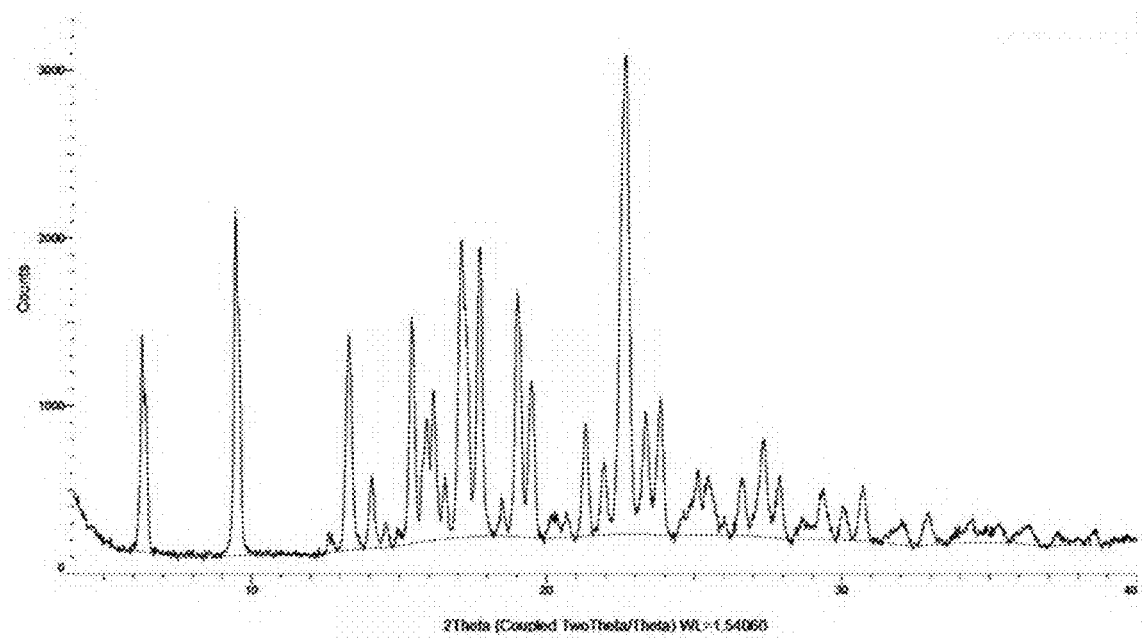

FIG. 860 depicts the XRPD profile of Experiment 3-Sample C1 (Tabernanthalog·Sorbate, Pattern #7). 40° C., 75% RH, 5d.

Figure 861:
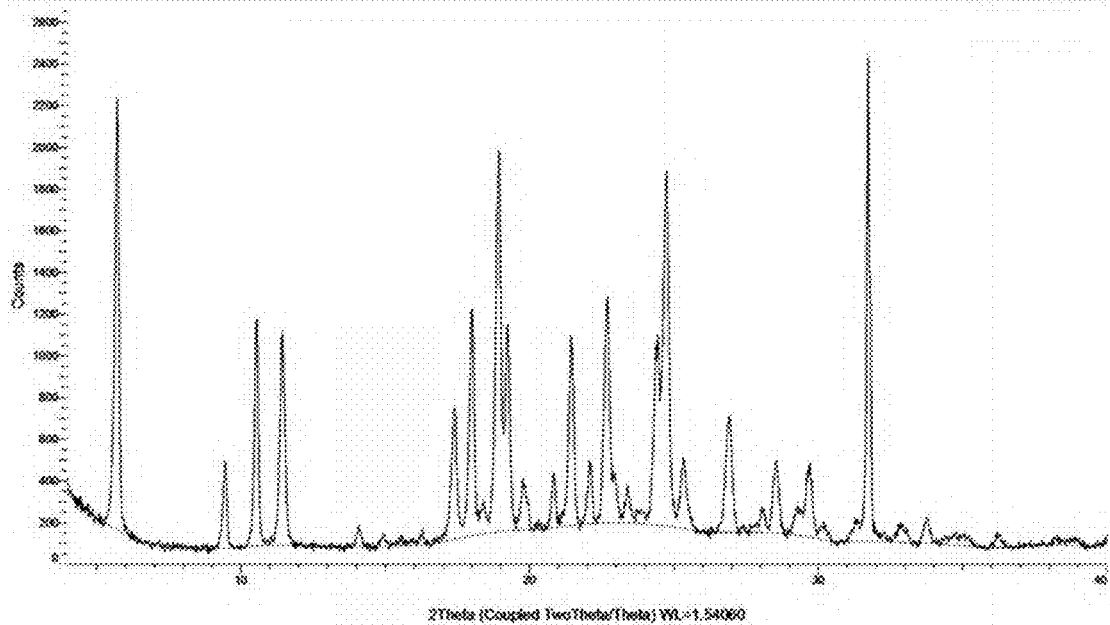

FIG. 861 depicts the XRPD profile of Experiment 3-Sample C2 (Tabernanthalog·Sorbate, Form A), Heated to 100° C. prior to XRPD.

Figure 862:
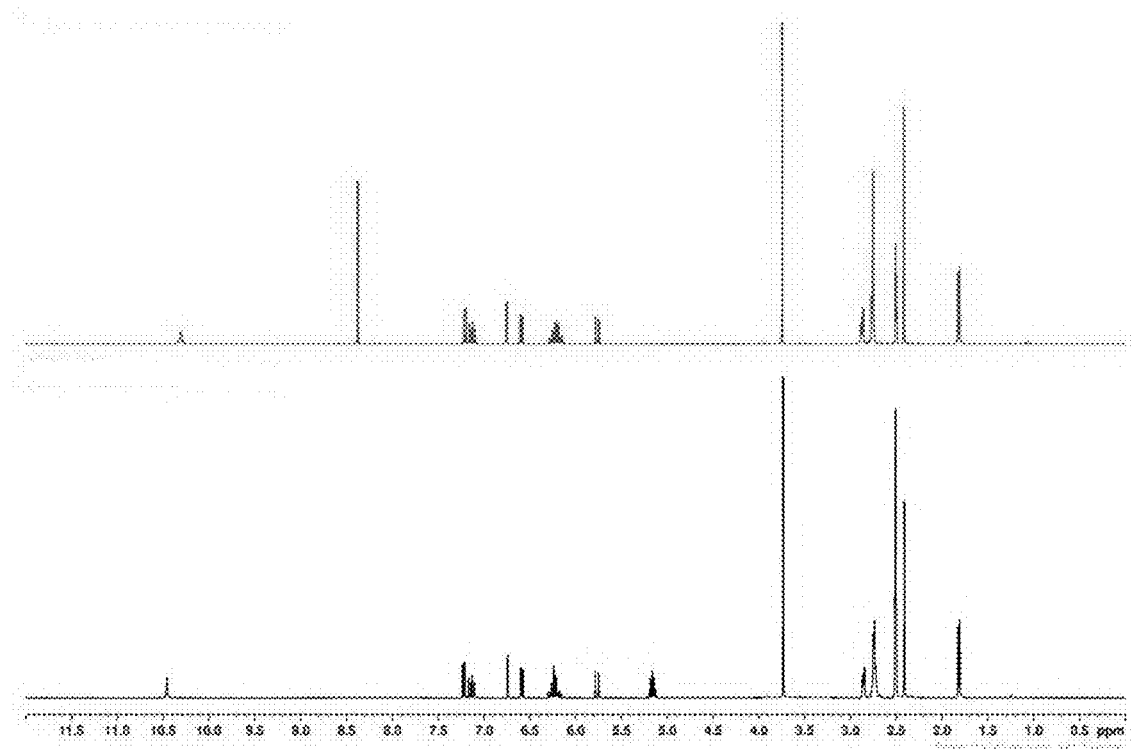

FIG. 862 depicts the overlay of ¹H NMR spectra of A1270-076-A1 (Tabernanthalog·Sorbate, Form A, Internal standard: TCNB DMSO-d6, upper spectrum, top) and Experiment 3-Sample A2 (Tabernanthalog·Sorbate·hemiHFIPA, Pattern #7, DMSO-$d_6$ bottom, lower spectrum).

Figure 863:
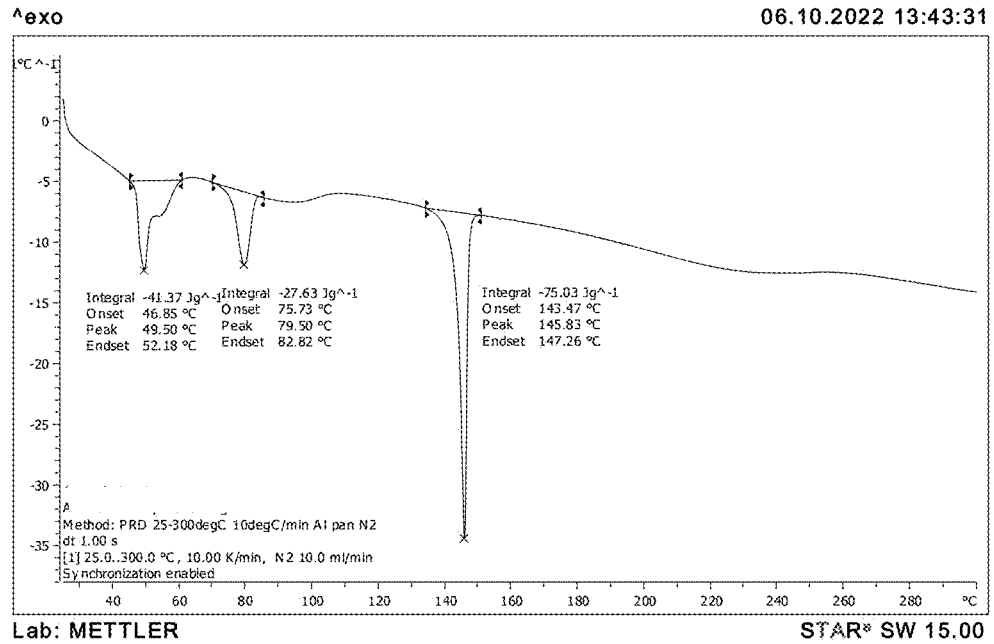

FIG. 863 depicts the DSC profile of Experiment 3-Sample B1 (Tabernanthalog·Sorbate·hemiHFIPA, Pattern #7).

Figure 864:
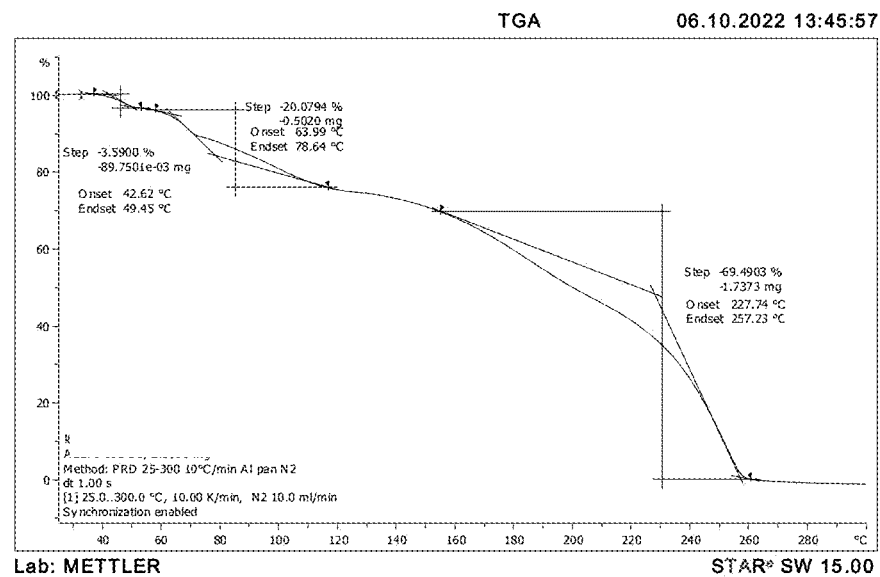

FIG. 864 depicts the TGA profile of Experiment 3-Sample B1 (Tabernanthalog·Sorbate·hemiHFIPA, Pattern #7).

Figure 865:
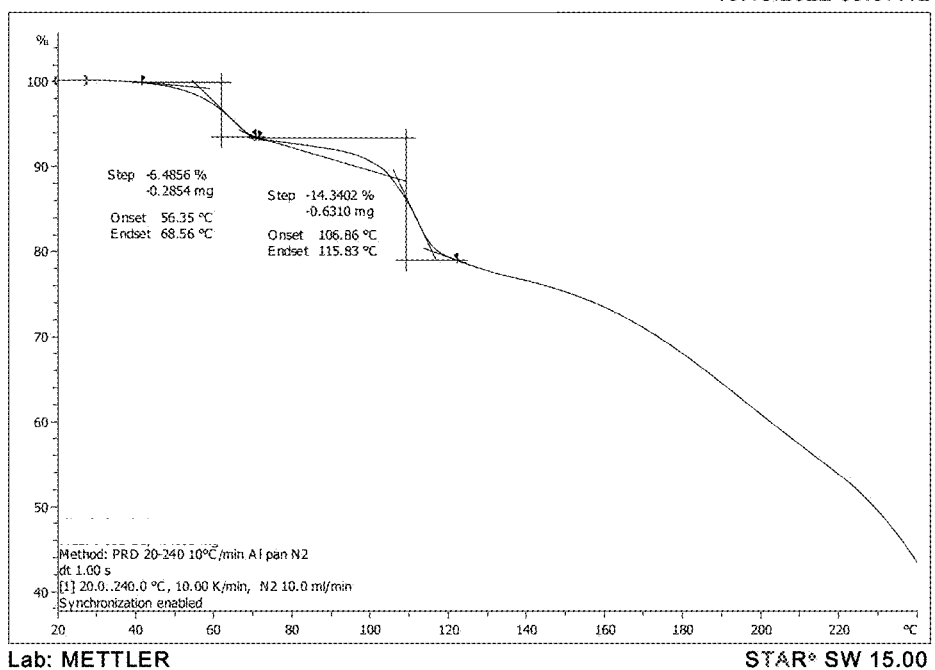

FIG. 865 depicts the TGA profile of Experiment 3-Sample C1 (Tabernanthalog·Sorbate·HemiHFIPA, Pattern #7).

Figure 866:
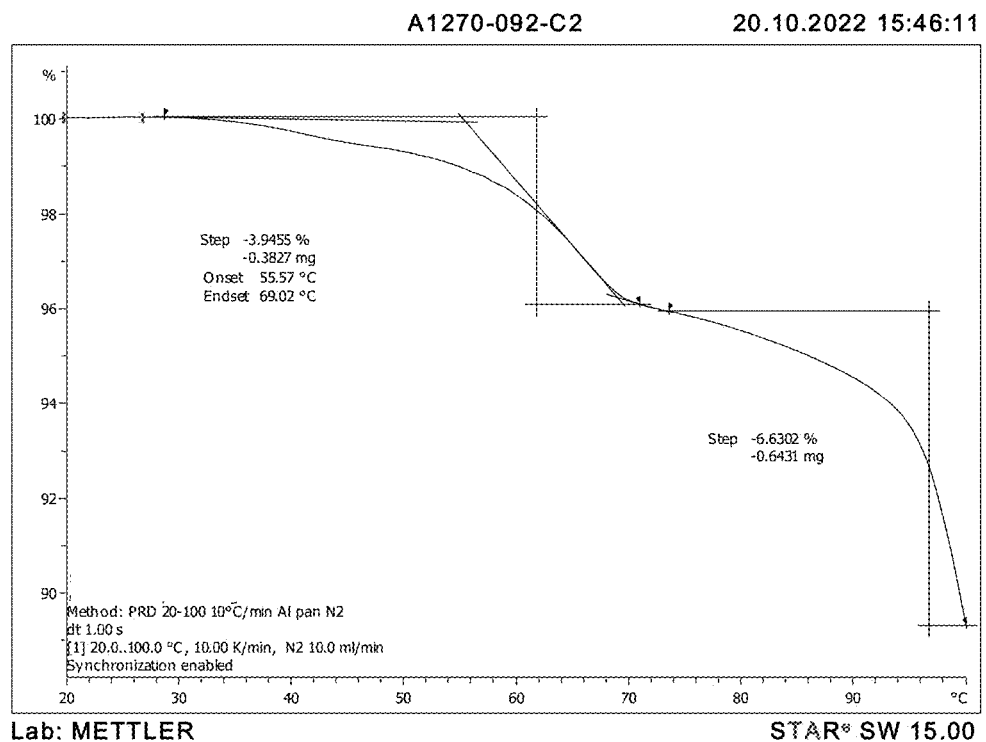

FIG. 866 depicts the TGA Profile of Experiment 3-Sample C2 (Tabernanthalog·Sorbate·HemiHFIPA, Pattern #7).

Figure 867:
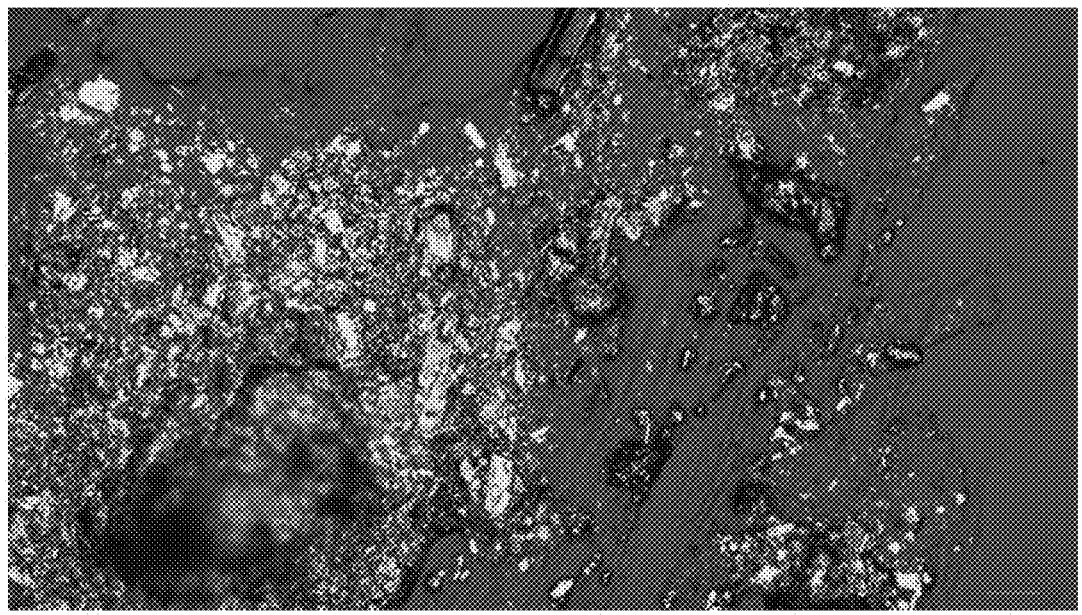

FIG. 867 depicts the microscope image of Experiment 3-Sample A1 (Tabernanthalog·Sorbate·HemiHFIPA, Pattern #7) (10× lens).

Figure 868:
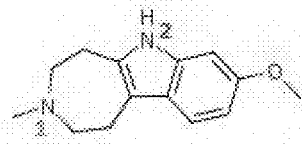

FIG. 868 depicts the molecular representation of Tabernanthalog·Native.

Figure 869:
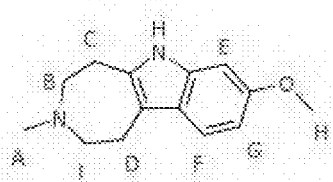

FIG. 869 depicts the molecular representation of Tabernanthalog·Native with protons annotated.

Figure 870:
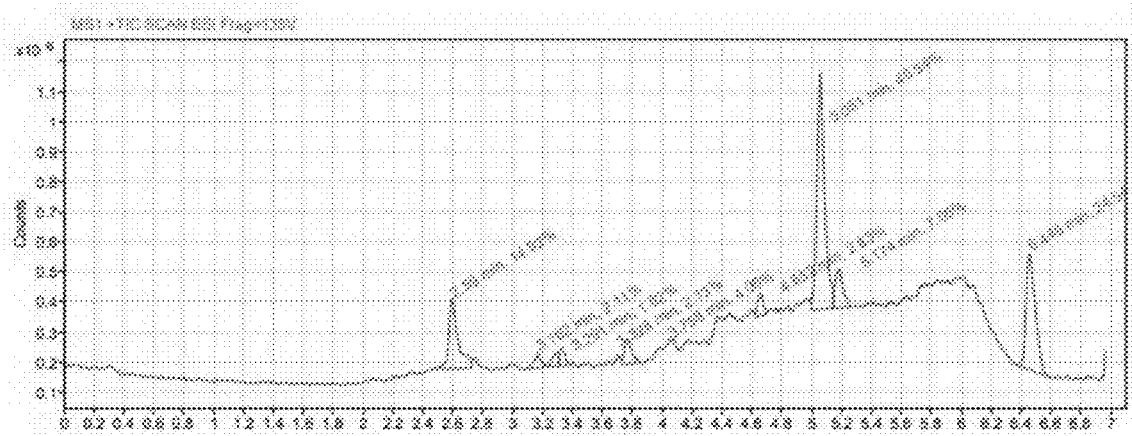

FIG. 870 depicts the LC-MS details for Experiment 1-Sample E1 (Tabernanthalog·Sorbate, amorphous).

Figure 871:
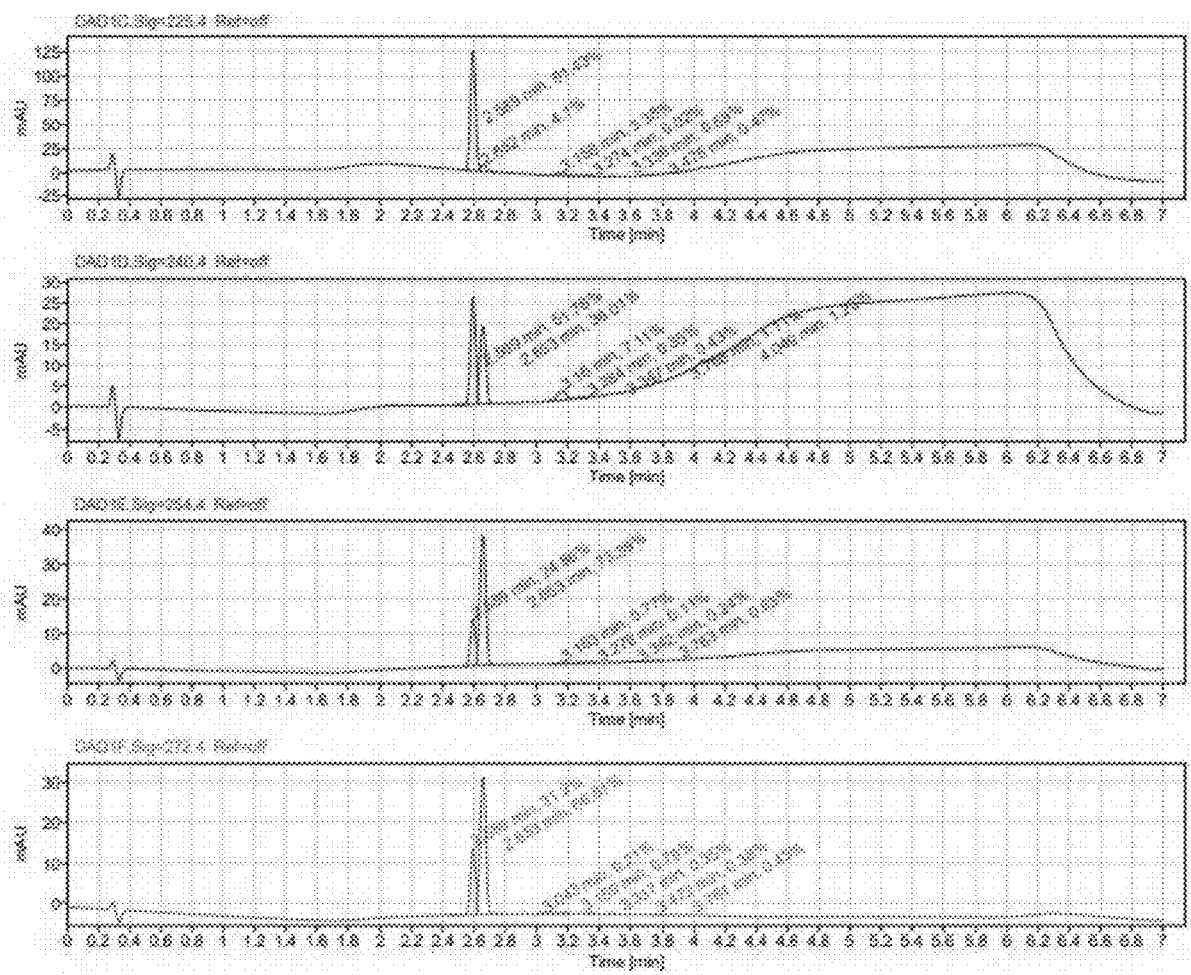

FIG. 871 depicts the LC-MS profile of Experiment 1-Sample E1 (Tabernanthalog·Sorbate, amorphous, API=2.589 min, Sorbic acid=2.653 min).

Figure 872:
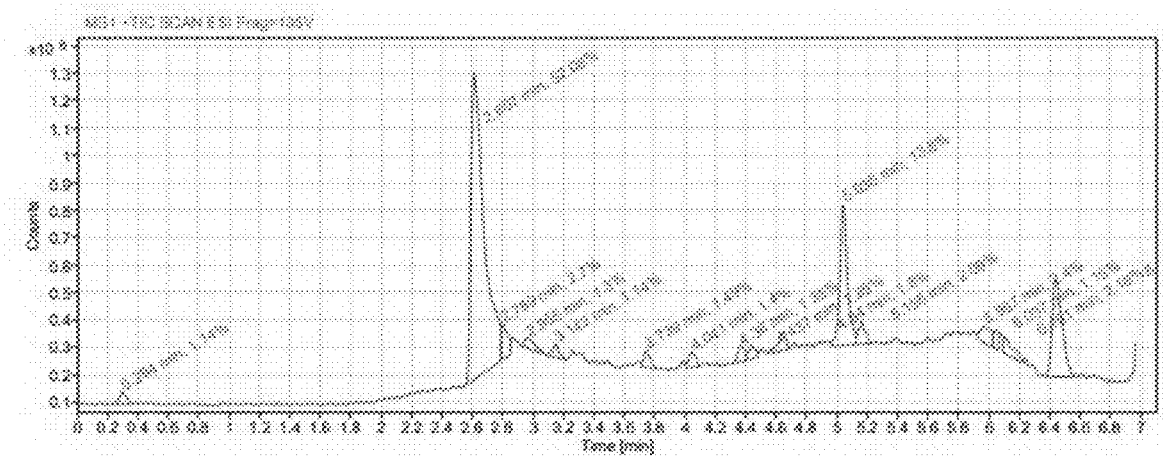

FIG. 872 depicts the LC-MS details for Sorbic Acid.

Figure 873:
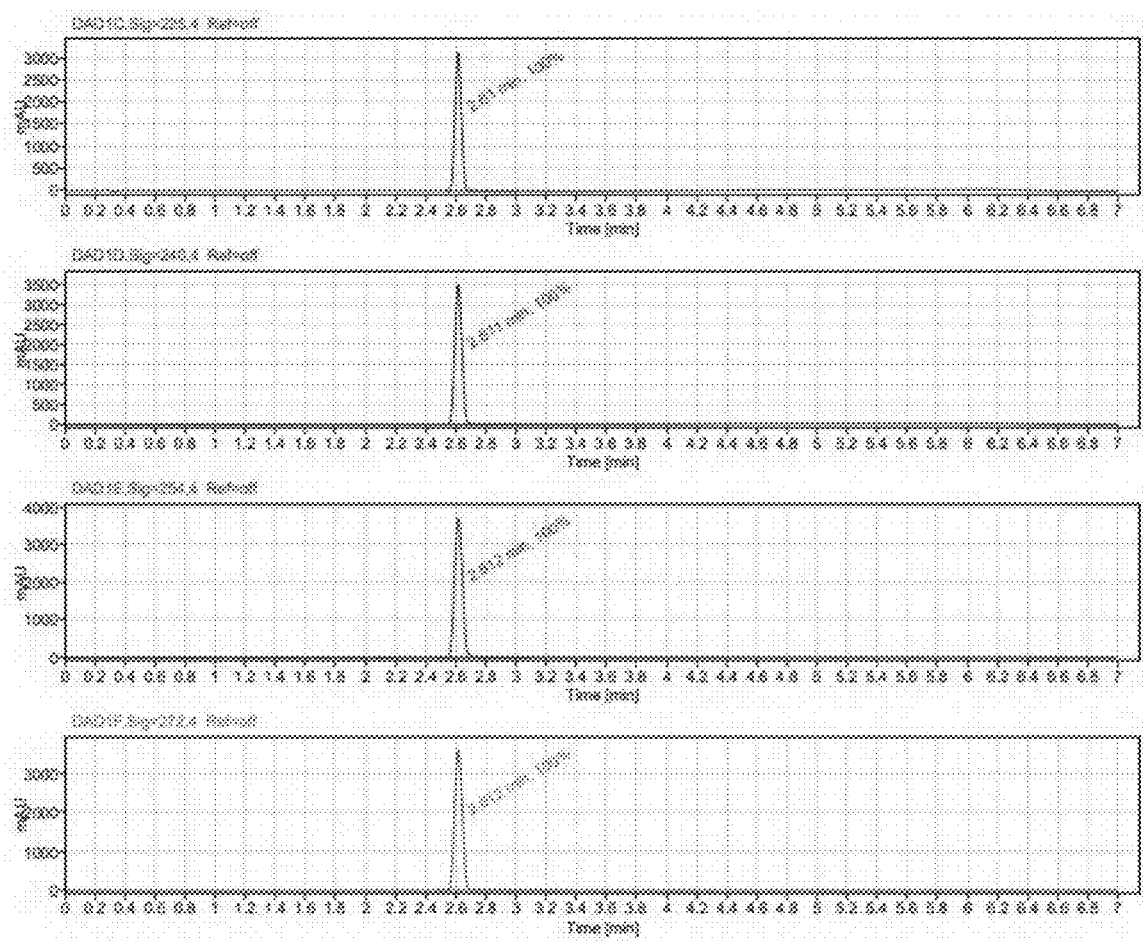

FIG. 873 depicts the LC-MS profile of Sorbic acid=2.61 min.

Figure 874:
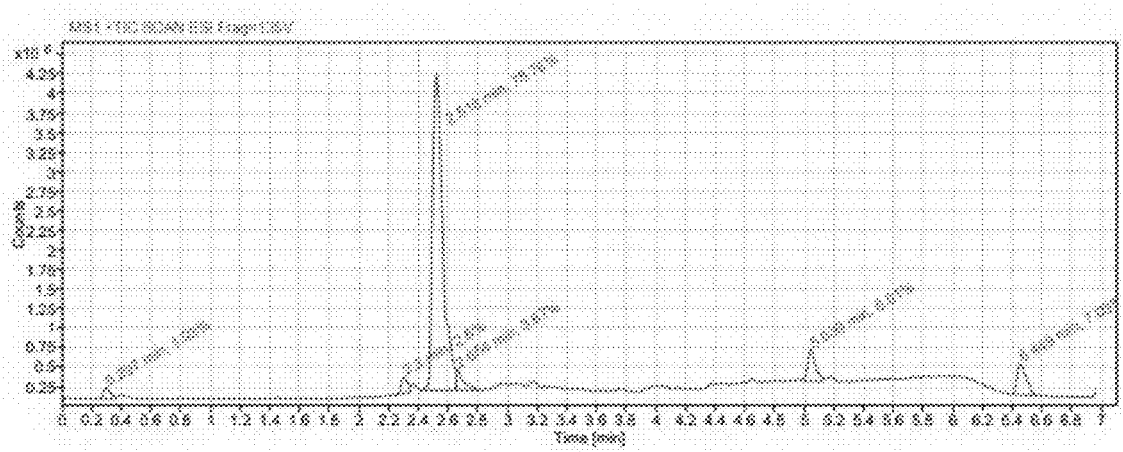

FIG. 874 depicts the LC-MS profile of Experiment 2-Sample E1 (Tabernanthalog·Monofumarate, amorphous).

Figure 875:
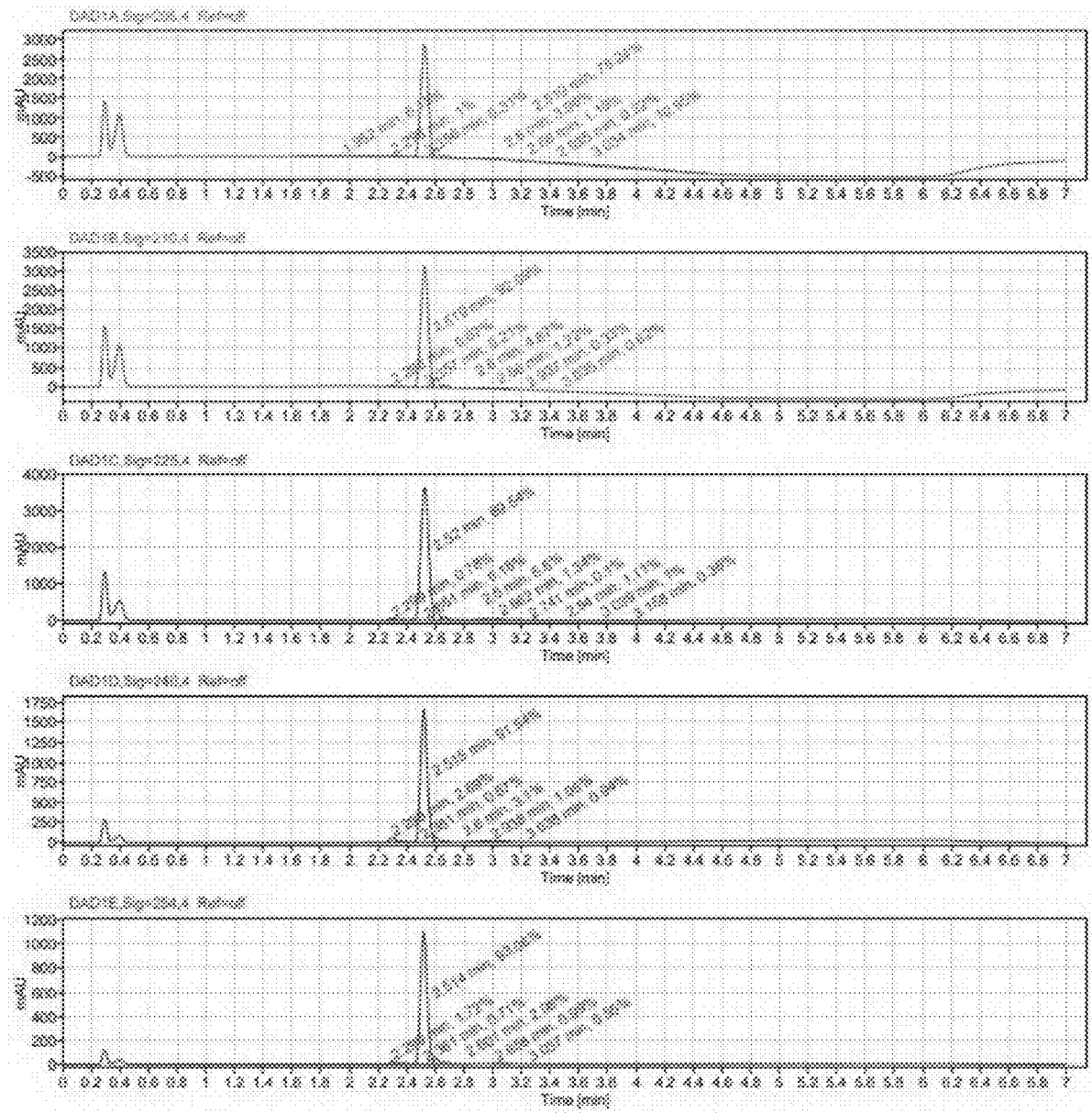

FIG. 875 depicts the LC-MS profile of Experiment 2-Sample E1 (Fumaric acid=~0.3 min, API=2.52 min).

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

When used in the context of XRPD signal values, the term "about" can indicate a peak value ±0.20, ±0.15, ±0.10, ±0.05, or ±0.01 °2θ. In some embodiments, when used in the context of XRPD signal values "about" can indicate a peak value at substantially exactly the disclosed peak value.

The terms "XRPD peak", "XRPD signal" and "XRPD peak/signal" are used interchangeably.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

"Administering" refers to any suitable mode of administration, including, oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Tabernanthalog" refers to the compound

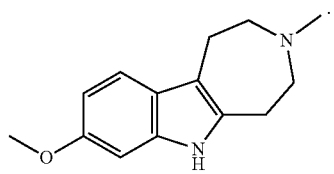

"Tabernanthalog fumarate" or "Tabernanthalog monofumarate" refers to the fumaric acid salt of tabernanthalog

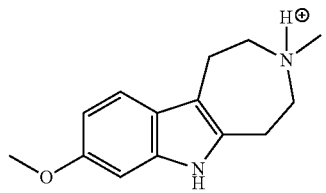

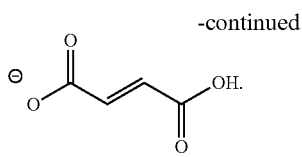

"Tabernanthalog hemifumarate" refers to the hemifumaric acid salt of tabernanthalog

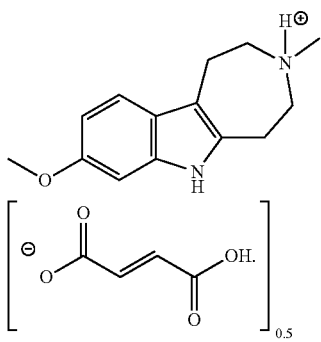

"Subject" refers to an animal, such as a mammal, including, but not limited to, primates (e.g., humans), cows, sheep, goats, horses, dogs, cats, rabbits, rats, mice and the like. In certain embodiments, the subject is a human subject.

"Therapeutically effective amount" or "therapeutically sufficient amount" or "effective or sufficient amount" refers to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

"Neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

"Brain disorder" refers to a neurological disorder which affects the brain's structure and function. Brain disorders can include, but are not limited to, Alzheimer's, Parkinson's disease, psychological disorder, depression, treatment resistant depression, addiction, anxiety, post-traumatic stress disorder, suicidal ideation, major depressive disorder, bipolar disorder, schizophrenia, stroke, traumatic brain injury, and substance use disorder.

"Combination therapy" refers to a method of treating a disease or disorder, wherein two or more different pharmaceutical agents are administered in overlapping regimens so that the subject is simultaneously exposed to both agents. For example, the compounds of the invention can be used in combination with other pharmaceutically active compounds. The compounds of the invention can be administered simultaneously (as a single preparation or separate preparation) or sequentially to the other drug therapy. In general, a combination therapy envisions administration of two or more drugs during a single cycle or course of therapy.

"Neurotrophic factors" refers to a family of soluble peptides or proteins which support the survival, growth, and differentiation of developing and mature neurons.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$) are modulators of the receptor.

"Agonism" refers to the activation of a receptor or enzyme by a modulator, or agonist, to produce a biological response.

"Agonist" refers to a modulator that binds to a receptor or enzyme and activates the receptor to produce a biological response. By way of example only, "$5HT_{2A}$ agonist" can be used to refer to a compound that exhibits an $EC_{50}$ with respect to $5HT_{2A}$ activity of no more than about 100 mM. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

"Positive allosteric modulator" refers to a modulator that binds to a site distinct from the orthosteric binding site and enhances or amplifies the effect of an agonist.

"Antagonism" refers to the inactivation of a receptor or enzyme by a modulator, or antagonist. Antagonism of a receptor, for example, is when a molecule binds to the receptor and does not allow activity to occur.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

"Composition" refers to a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

The terms "powder X-ray diffraction pattern", "PXRD pattern", "X-ray powder diffraction pattern", and "XRPD pattern" are used interchangeably and refer to the experimentally observed diffractogram or parameters derived therefrom. Powder X-ray diffraction patterns are typically characterized by peak position (abscissa) and peak intensities (ordinate). The term "peak intensities" refers to relative signal intensities within a given X-ray diffraction pattern. Factors which can affect the relative peak intensities are sample thickness and preferred orientation (i.e., the crystalline particles are not distributed randomly). The term "peak positions" as used herein refers to X-ray reflection positions as measured and observed in powder X-ray diffraction experiments. Peak positions are directly related to the dimensions of the unit cell. The peaks, identified by their respective peak positions, are extracted from the diffraction patterns for the various polymorphic forms of salts of tabernanthalog.

The term "2 theta value", "2θ" or "2 θ" refers to the peak position in degrees based on the experimental setup of the X-ray diffraction experiment and is a common abscissa unit in diffraction patterns. In general, the experimental setup requires that if a reflection is diffracted when the incoming beam forms an angle theta (θ) with a certain lattice plane, the reflected beam is recorded at an angle 2 theta (2 θ). It should be understood that reference herein to specific 2θ values for a specific polymorphic form is intended to mean the 2θ values (in degrees) as measured using the X-ray diffraction experimental conditions as described herein.

"Preferred orientation effects" refer to variable peak intensities or relative intensity differences between different PXRD measurements of the same samples that can be due to the orientation of the particles. Without wishing to be bound by theory, in PXRD it can be desirable to have a sample in which particles are oriented randomly (e.g., a powder). However, it can be difficult or in some cases impossible to achieve truly random particle orientations in practice. As particle size increases, the randomness of particle orientation can decrease, leading to increased challenges with achieving a preferred orientation. Without wishing to be bound by theory, a smaller particle size can reduce technical challenges associated with preferred orientation and allow for more accurate representation of peaks. However, one of skill in the art will understand how to reduce or mitigate preferred orientation effects and will recognize preferred orientation effects that can exist even between two different measurements of the same sample. For instance, in some embodiments, differences in resolution or relative peak intensities can be attributed to preferred orientation effects.

As used herein, the term "substantially pure" with reference to a particular salt or solid form (or to a mixture of two or more salts) of a compound indicates the salt or solid form (or a mixture) includes less than 10%, less than 5%, less than 3%, less than 1%, less than 0.5%, less than 0.2%, or less than 0.1% by weight of impurities, including other salt or solid forms of the compound. Such purity may be determined, for example, by powder X-ray diffraction.

As used herein, the term "polymorph" or "salt form" refers to different crystalline forms of the same compound and other solid state molecular forms including pseudo-polymorphs, such as hydrates (e.g., bound water present in the crystalline structure) and solvates (e.g., bound solvents other than water) of the same compound. Different crystalline polymorphs have different crystal structures due to a different packing of the molecules in the lattice. This results in a different crystal symmetry and/or unit cell parameters which directly influences its physical properties such as the X-ray diffraction characteristics of crystals or powders. A different polymorph, for example, will in general diffract at a different set of angles and will give different values for the intensities. Therefore, X-ray powder diffraction can be used to identify different polymorphs, or a solid form that comprises more than one polymorph, in a reproducible and reliable way (S. Byrn et al, Pharmaceutical Solids: A Strategic Approach to Regulatory Considerations, Pharmaceutical research, Vol. 12, No. 7, p. 945-954, 1995; J. K. Haleblian and W. McCrone, Pharmacetical Applications of Polymorphism, Journal of Pharmaceutical Sciences, Vol. 58, No. 8, p. 911-929, 1969).

The term "tabernanthalog·salt" refer to the salt of tabernanthalog. The salt is selected from the group consisting of galactarate (mucate), naphthalene-1,5-disulfonate, citrate, sulfate, d-glucuronate, ethane-1,2-disulfonate, lactobionate, p-toluenesulfonate, D-glucoheptonate, thiocyanate, (−)-L-pyroglutamate, methanesulfonate, L-malate, dodecylsulfate, hippurate, naphthalene-2-sulfonate, D-gluconate, benzenesulfonate, D,L-lactate, oxalate, oleate, glycerophosphate, succinate, ethanesulfonate, glutarate, L-aspartate, cinnamate, maleate, adipate, phosphate, sebacate, isethionate, (+)-camphorate, glutamate, acetate, sorbate, tartrate, benzoate, maleate, fumarate, and combinations thereof.

Crystalline polymorphic forms are of interest to the pharmaceutical industry and especially to those involved in the development of suitable dosage forms. If the polymorphic form is not held constant during clinical or stability studies, the exact dosage form used or studied may not be comparable from one lot to another. It is also desirable to have processes for producing a compound with the selected polymorphic form in high purity when the compound is used in clinical studies or commercial products since impurities present may produce undesired toxicological effects. Certain polymorphic forms may exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies.

The term "amorphous" refers to any solid substance which (i) lacks order in three dimensions, or (ii) exhibits order in less than three dimensions, order only over short distances (e.g., less than 10 A), or both. Thus, amorphous substances include partially crystalline materials and crystalline mesophases with, e.g., one- or two-dimensional translational order (liquid crystals), orientational disorder (orientationally disordered crystals), or conformational disorder (conformationally disordered crystals). Amorphous solids may be characterized by known techniques, including powder X-ray diffraction (PXRD) crystallography, solid state nuclear magnet resonance (ssNMR) spectroscopy, differential scanning calorimetry (DSC), or some combination of these techniques. Amorphous solids give diffuse PXRD patterns, typically comprised of one or two broad peaks (i.e., peaks having base widths of about 5 °2θ or greater).

The term "crystalline" refers to any solid substance exhibiting three-dimensional order, which in contrast to an amorphous solid substance, gives a distinctive PXRD pattern with sharply defined peaks.

The term "ambient temperature" refers to a temperature condition typically encountered in a laboratory setting. This includes the approximate temperature range of about 20 to about 30° C.

The term "detectable amount" refers to an amount or amount per unit volume that can be detected using conventional techniques, such as X-ray powder diffraction, differential scanning calorimetry, HPLC, Fourier Transform Infrared Spectroscopy (FT-IR), Raman spectroscopy, and the like.

The term "solvate" describes a molecular complex comprising the drug substance and a stoichiometric or non-stoichiometric amount of one or more solvent molecules (e.g., ethanol). When the solvent is tightly bound to the drug the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex may be non-stoichiometric.

The term "hydrate" describes a solvate comprising the drug substance and a stoichiometric or non-stoichiometric amount of water.

The term "relative humidity" refers to the ratio of the amount of water vapor in air at a given temperature to the maximum amount of water vapor that can be held at that temperature and pressure, expressed as a percentage.

The term "relative intensity" refers to an intensity value derived from a sample X-ray diffraction pattern. The complete ordinate range scale for a diffraction pattern is assigned a value of 100. A peak having intensity falling between about 50% to about 100% on this scale intensity is termed very strong (vs); a peak having intensity falling between about 50% to about 25% is termed strong (s). Additional weaker peaks are present in typical diffraction patterns and are also characteristic of a given polymorph, wherein the additional peaks are termed medium (m), weak (w) and very weak (vw).

The term "slurry" refers to a solid substance suspended in a liquid medium, typically water or an organic solvent.

The term "under vacuum" refers to typical pressures obtainable by a laboratory oil or oil-free diaphragm vacuum pump.

The term "treating", as used herein, unless otherwise indicated, means reversing, alleviating, or inhibiting the progress of the disorder or condition to which such term applies, or one or more symptoms of such disorder or condition. The term "treatment", as used herein, unless otherwise indicated, refers to the act of "treating" as defined immediately above. For example, the terms "treat", "treating" and "treatment" can refer to a method of alleviating or abrogating a particular disorder and/or one or more of its attendant symptoms.

The term "pharmaceutical composition" refers to a composition comprising one or more of the salt or solid forms of tabernanthalog described herein, and other chemical components, such as physiologically/pharmaceutically acceptable carriers, diluents, vehicles and/or excipients. The purpose of a pharmaceutical composition is to facilitate administration of a compound to an organism, such as a human or other mammals.

The term "pharmaceutically acceptable" "carrier", "diluent", "vehicle", or "excipient" refers to a material (or materials) that may be included with a particular pharmaceutical agent to form a pharmaceutical composition, and may be solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropyl methylcellulose, methylmethacrylate and the like.

The term "compound of the present disclosure", "compounds of the present disclosure", "presently disclosed compound", "presently disclosed compounds", "compound disclosed herein", or "compounds disclosed herein" means the salt and solid form(s) of the tabernanthalog or the free base tabernanthalog.

II. Compounds

Recently, researchers reported some progress in developing compounds that maintain the potential therapeutic efficacy of the natural product, ibogaine, but lack ibogaine's toxicity and hallucinogenic effects. For example, the compound tabernanthalog (TBG), a simplified analog of ibogaine (or the iboga alkaloid tabernanthine),

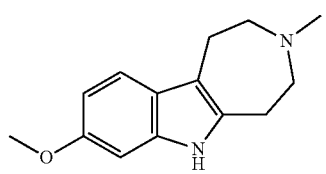

was reported to be non-hallucinogenic, but have 5-HT2A activity.

(See, Dong et al. Cell, 184, 2779-2792; Olson et al. WO 2020/176599; Cameron, et al., *Nature*. 2021; 589(7842): 474-479).

Olson et al. reported isolating tabernanthalog as a fumarate salt. The present inventors observed that the properties of tabernanthalog and the disclosed tabernanthalog fumarate could be improved upon to support its use in the clinical treatment of brain disorders. Accordingly, disclosed herein are novel forms of tabernanthalog, including salts and solid forms of tabernanthalog with improved properties. The disclosed forms are useful to treat various disorders, such as brain disorders. Also disclosed are methods for making salt and solid forms of tabernanthalog and method of administering the salt and solid forms of tabernanthalog to a subject in need thereof.

In some embodiments, the solid form of the compound (tabernanthalog) is a crystalline form of the tabernanthalog. In some embodiments, the solid form of tabernanthalog is a polymorph of tabernanthalog, such as a polymorph of the free base compound or a polymorph of a salt form. In some embodiments, the solid form of the compound is a salt of the compound. In some embodiments, the solid form of the compound is a crystalline salt form of the compound, such as an acid addition salt form. In one embodiment, the solid form of tabernanthalog is the free base of tabernanthalog.

In one embodiment, a solid form of a tabernanthalog salt is made by a method described in the Examples. The solid form of a tabernanthalog salt made by the disclosed method may have at least one improved property compared to another form of the tabernanthalog salt. In one embodiment, the tabernanthalog salt solid form disclosed herein is a crystalline form that has an improved property relative to amorphous tabernanthalog salt. In one embodiment a crystalline form disclosed herein is a polymorph of tabernanthalog salt. In certain embodiments, a disclosed polymorph of tabernanthalog salt has an improved property over one or more other solid forms of tabernanthalog salt.

Also disclosed herein is a solid form of tabernanthalog fumarate that is made by the method described in Example 1.

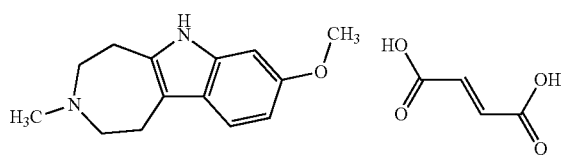

Name: (2E)-but-2-enedioic acid; 8-methoxy-3-methyl-
1H,2H,3H,4H,5H,6H-azepino[4,5-b]indole
Molecular weight: 346.38
Formula: C₁₈H₂₂N₂O₅

The solid form of tabernanthalog fumarate made by the disclosed method may have at least one improved property compared to another form of tabernanthalog fumarate. In one embodiment, the tabernanthalog fumarate solid form disclosed herein is a crystalline form that has an improved property relative to amorphous tabernanthalog fumarate. In one embodiment a crystalline form disclosed herein is a polymorph of tabernanthalog fumarate. In certain embodiments, a disclosed polymorph of tabernanthalog fumarate has an improved property over one or more other solid forms of tabernanthalog fumarate.

Salts

In some embodiments, tabernanthalog is prepared in the form of a salt of tabernanthalog. Suitable salts include pharmaceutically acceptable salts of tabernanthalog. In some embodiments, the salt is provided as a solid form of tabernanthalog that is not, and does not comprise, tabernanthalog fumarate.

In some embodiments, the salt of tabernanthalog is formed from a suitable pharmaceutically acceptable acid, including, without limitation, inorganic acids such as hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like.

In other embodiments, the salt of tabernanthalog may be formed from a suitable pharmaceutically acceptable base, including, without limitation, inorganic bases such as sodium, potassium, lithium, ammonium, calcium, magnesium, iron, zinc, copper, manganese, aluminum salts and the like. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris (hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Additional information concerning pharmaceutically acceptable salts can be found in, for example, S. M. Berge, et al., "Pharmaceutical Salts," J. Pharm. Sci., 1977; 66:1-19 which is incorporated herein by reference.

In some embodiments, the salt is formed using an acid from Table 1.

TABLE 1

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| fumaric acid | carbonic acid |
| galactaric (mucic) acid | |

The acid salts of tabernanthalog disclosed herein can have any suitable stoichiometric ratio of acid to tabernanthalog. In one embodiment, the molar ratio of acid is from about 0.4 to about 2.2 acid to tabernanthalog, such as forms wherein the salt has a stoichiometric ratio of from about 0.5 to about 2, such as about 0.5, about 1 or about 2 moles of the acid for each mole of amine. In some embodiments, the tabernanthalog salt is a tabernanthalog sorbate salt, a tabernanthalog tartrate salt, a tabernanthalog maleate salt, or a tabernanthalog benzoate salt.

In some embodiments, the tabernanthalog salt has at least one of the following characteristics: (a) a unique powder diffraction pattern by XRPD, (b) a flat baseline leading to single melt event by DSC, (c) a flat baseline up to the melt by TGA, (d) a significantly reduced impurity burden and absence of trace solvents by ¹H NMR, and (e) an optically crystalline and reasonably equant morphology under cross-polarized filter.

In some embodiments, the tabernanthalog salt is tabernanthalog sorbate salt. In specific embodiments, the tabernanthalog sorbate salt exhibits higher crystallographic quality than the tabernanthalog fumarate salt. In other specific embodiments, the tabernanthalog sorbate salt provides greater solvent and impurity rejection and give overall better performance in advanced physicochemical screening compared to other tabernanthalog salts. In yet other embodiments, the tabernanthalog sorbate salt is highly soluble in the SIF buffers with no observed disproportionation.

In yet other embodiments, the tabernanthalog salt is at least about 95% pure as measured by HPLC.

In yet other embodiments, the tabernanthalog salt is at least about 96% pure as measured by HPLC.

In yet other embodiments, the tabernanthalog salt is at least about 97% pure as measured by HPLC.

In yet other embodiments, the tabernanthalog salt is at least about 98% pure as measured by HPLC.

In yet other embodiments, the tabernanthalog salt is at least about 99% pure as measured by HPLC.

In yet other embodiments, the tabernanthalog salt is at least about 99.5% pure as measured by HPLC.

In yet other embodiments, the tabernanthalog sorbate salt is at least about 95% pure as measured by HPLC.

In yet other embodiments, the tabernanthalog sorbate salt is at least about 96% pure as measured by HPLC.

In yet other embodiments, the tabernanthalog sorbate salt is at least about 97% pure as measured by HPLC.

In yet other embodiments, the tabernanthalog sorbate salt is at least about 98% pure as measured by HPLC.

In yet other embodiments, the tabernanthalog sorbate salt is at least about 99% pure as measured by HPLC.

In yet other embodiments, the tabernanthalog sorbate salt is at least about 99.5% pure as measured by HPLC.

In yet other embodiments, the tabernanthalog salt is at least about 95% pure as measured by UV chromatographic method.

In yet other embodiments, the tabernanthalog salt is at least about 96% pure as measured by UV chromatographic method.

In yet other embodiments, the tabernanthalog salt is at least about 97% pure as measured by UV chromatographic method.

In yet other embodiments, the tabernanthalog salt is at least about 98% pure as measured by UV chromatographic method.

In yet other embodiments, the tabernanthalog salt is at least about 99% pure as measured by UV chromatographic method.

In yet other embodiments, the tabernanthalog salt is at least about 99.5% pure as measured by UV chromatographic method.

In yet other embodiments, the tabernanthalog sorbate salt is at least about 95% pure as measured by UV chromatographic method.

In yet other embodiments, the tabernanthalog sorbate salt is at least about 96% pure as measured by UV chromatographic method.

In yet other embodiments, the tabernanthalog sorbate salt is at least about 97% pure as measured by UV chromatographic method.

In yet other embodiments, the tabernanthalog sorbate salt is at least about 98% pure as measured by UV chromatographic method.

In yet other embodiments, the tabernanthalog sorbate salt is at least about 99% pure as measured by UV chromatographic method.

In yet other embodiments, the tabernanthalog sorbate salt is at least about 99.5% pure as measured by UV chromatographic method.

In yet other embodiments, the tabernanthalog sorbate salt is at least about 99.64% pure as measured by UV chromatographic method.

Solid Forms

Embodiments of tabernanthalog of the present disclosure are in a solid form. The solid form may be a crystalline form or an amorphous form. In some embodiments, the solid form is a crystalline form. In some embodiments, the solid form of tabernanthalog is a salt. And in certain embodiments, the solid form is a crystalline salt form of the compound. A person of ordinary skill in the art understands that solid forms of tabernanthalog, such as crystalline forms including salt and non-salt crystalline forms of tabernanthalog, may exist in more than one crystal form. Such different forms are referred to as polymorphs. In some embodiments, the disclosed compounds are particular polymorphs of tabernanthalog or tabernanthalog salts.

In some embodiments, the solid form of tabernanthalog disclosed herein is selected to be a crystalline form, such as a particular polymorph of a crystalline form of tabernanthalog, that provides one or more desired properties. In one embodiment, the crystalline form offers advantages over the amorphous form of the molecule. In another embodiment, the disclosed polymorph offers improved properties as compared to another polymorph of tabernanthalog. The tabernanthalog may be a salt or free base compound. The one or more desired properties may include, but are not limited to, physical properties, including but not limited to, hygroscopic properties, solubility in water and/or organic solvents, melting point, glass transition temperature, flowability, and/or stability, such as thermal stability, mechanical stability, shelf life, stability against polymorphic transition, etc.; chemical properties, such as, but not limited to, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph may be produced by techniques known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

Techniques to identify a particular solid form of tabernanthalog are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

It will be understood that characterization data present in the Examples is considered to be part of the present invention. In some embodiments, each of the XRPD tables located in the Examples which contain XRPD signals/peaks are considered as inventive entities individually and separately from the methods of producing the particular XPRD characterization. These tables are referred to by embodiments in the detailed description and are considered part of the detailed description.

Tabernanthalog Fumarate Salt

In some embodiments, the tabernanthalog fumarate salt is crystalline polymorphic unary fumarate salt of Tabernanthalog.

In some embodiments, the tabernanthalog fumarate salt is crystalline polymorphic hemi-fumarate salt of Tabernanthalog.

In some embodiments, the tabernanthalog fumarate salt is crystalline polymorphic salt of Tabernanthalog of Form A, Form B, Form I, or a mixture thereof.

In some embodiments, the tabernanthalog fumarate salt is crystalline polymorphic salt of tabernanthalog with Pattern #1, Pattern #2a, Pattern #2b, Pattern #2c, Pattern #2d, Pattern #3, Pattern #4a, Pattern #4b, Pattern #5, Pattern #6a, Pattern #6b, Pattern #7, Pattern #8, Pattern #9, Pattern #10, Pattern #11, Pattern #12, Pattern #13, Pattern #14, Pattern #15, Pattern #16, Pattern #17, Pattern #18, Pattern #19, Pattern #°2θ, Pattern #21, Pattern #22, or a mixture thereof.

In some embodiments, the solid form of tabernanthalog monofumarate is crystalline tabernanthalog monofumarate (Pattern #12) characterized by two or more, or three or more XRPD signals selected from the group consisting of 16.3 °2θ, 20.2 °2θ, and 25.5 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate (Pattern #12) characterized by XRPD signals at 16.3 °2θ, 20.2 °2θ, and 25.5 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate (Pattern #12) characterized by two or more, or three or more XRPD signals selected from the group consisting of 25.5 °2θ, 16.3 °2θ, 20.2 °2θ, 21.4 °2θ, and 18.1 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate (Pattern #12) characterized by XRPD signals at 25.5 °2θ, 16.3 °2θ, 20.2 °2θ, 21.4 °2θ, and 18.1 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate (Pattern #12) characterized by two or more, or three or more XRPD signals selected from the group consisting of 25.5 °2θ, 16.3 °2θ, 20.2 °2θ, 21.4 °2θ, 18.1 °2θ, 26.8 °2θ, and 8.2 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate (Pattern #12) characterized by XRPD signals at 25.5 °2θ, 16.3 °2θ, 20.2 °2θ, 21.4 °2θ, 18.1 °2θ, 26.8 °2θ, and 8.2°2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate (Pattern #12) characterized by two or more, or three or more XRPD signals selected from the group consisting of 25.5 °2θ, 16.3 °2θ, 20.2 °2θ, 21.4 °2θ, 18.1 °2θ, 26.8 °2θ, 8.2 °2θ, 22.9 °2θ, 9.0 °2θ, and 16.6°2θ (±0.2 °2θ; ±0.1 °2θ; or 0.0 °2θ; Cu Kα1 radiation). In some embodiments, the solid form of tabernanthalog monofumarate is crystalline tabernanthalog monofumarate (Pattern #12) characterized by XRPD signals at 25.5 °2θ, 16.3 °2θ, 20.2 °2θ, 21.4 °2θ, 18.1 °2θ, 26.8 °2θ, 8.2 °2θ, 22.9 °2θ, 9.0 °2θ, and 16.6 °2θ (±0.2 °2θ; ±0.1 °2θ; or ±0.0 °2θ; Cu Kα1 radiation).

In some embodiments, the crystalline tabernanthalog monofumarate (Pattern #12) is characterized by one, two, three, four, five, six, seven, eight, nine, ten, eleven, twelve, thirteen, fourteen, fifteen, sixteen, seventeen, or eighteen XRPD signals selected from those set forth in Table 6.

In some embodiments, the solid form of tabernanthalog monofumarate is crystalline tabernanthalog monofumarate (Pattern #2a) characterized by two or more, or three or more XRPD signals selected from the group consisting of 25.6 °2θ, 16.3 °2θ, and 17.1 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate (Pattern #2a) characterized by XRPD signals at 25.6 °2θ, 16.3 °2θ, and 17.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate (Pattern #2a) characterized by two or more, or three or more XRPD signals selected from the group consisting of 25.6 °2θ, 16.3 °2θ, 17.1 °2θ, 9.1 °2θ, and 27.3 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate (Pattern #2a) characterized by XRPD signals at 25.6 °2θ, 16.3 °2θ, 17.1 °2θ, 9.1 °2θ, and 27.3 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate (Pattern #2a) characterized by two or more, or three or more XRPD signals selected from the group consisting of 25.6 °2θ, 16.3 °2θ, 17.1 °2θ, 9.1 °2θ, 27.3 °2θ, 18.1 °2θ, and 22.9°2θ (±0.2 °2θ; ±0.1 °2θ; or 0.0 °2θ; Cu Kα1 radiation). In some embodiments, the solid form of tabernanthalog monofumarate is crystalline tabernanthalog monofumarate (Pattern #2a) characterized by XRPD signals at 25.6 °2θ, 16.3°2θ, 17.1 °2θ, 9.1 °2θ, 27.3 °2θ, 18.1 °2θ, and 22.9 °2θ (±0.2 °2θ; ±0.1°2θ; or ±0.0 °2θ; Cu Kα1 radiation).

In some embodiments, the solid form of tabernanthalog monofumarate is crystalline tabernanthalog monofumarate (Pattern #2a) characterized by two or more, or three or more XRPD signals selected from the group consisting of 25.6 °2θ, 16.3°2θ, 17.1 °2θ, 9.1 °2θ, 27.3 °2θ, 18.1 °2θ, 22.9 °2θ, 26.8 °2θ, 15.6°2θ, and 12.2°2θ (±0.2°2θ; ±0.1°2θ; or 0.0 °2θ; Cu Kα1 radiation).

In some embodiments, the solid form of tabernanthalog monofumarate is crystalline tabernanthalog monofumarate (Pattern #2a) characterized by XRPD signals at 25.6 °2θ, 16.3°2θ, 17.1 °2θ, 9.1 °2θ, 27.3 °2θ, 18.1 °2θ, 22.9 °2θ, 26.8 °2θ, 15.6°2θ, and 12.2°2θ (±0.2°2θ; ±0.1°2θ; or 0.0 °2θ; Cu Kα1 radiation).

In some embodiments, the crystalline tabernanthalog monofumarate (Pattern #2a) is characterized by one, two, three, four, five, six, seven, eight, nine, ten, eleven, twelve, thirteen, fourteen, fifteen, sixteen, seventeen, or eighteen XRPD signals selected from those set forth in Table 7.

In some embodiments, the solid form of tabernanthalog monofumarate is crystalline tabernanthalog monofumarate (Pattern #15) characterized by two or more, or three or more XRPD signals selected from the group consisting of 16.3°2θ, 16.9°2θ, and 24.5 °2θ (±0.2 °2θ; ±0.1°2θ; or 0.0 °2θ; Cu Kα1 radiation). In some embodiments, the solid form of tabernanthalog monofumarate is crystalline tabernanthalog monofumarate (Pattern #15) characterized by XRPD signals at 16.3°2θ, 16.9°2θ, and 24.5°2θ (±0.2°2θ; ±0.1°2θ; or 0.0 °2θ; Cu Kα1 radiation).

In some embodiments, the solid form of tabernanthalog monofumarate is crystalline tabernanthalog monofumarate (Pattern #15) characterized by two or more, or three or more XRPD signals selected from the group consisting of 16.3°2θ, 16.9 °2θ, 24.5 °2θ, 25.6°2θ, and 23.4°2θ (±0.2°2θ; ±0.1 °2θ; or 0.0 °2θ; Cu Kα1 radiation). In some embodiments, the solid form of tabernanthalog monofumarate is crystalline tabernanthalog monofumarate (Pattern #15) characterized by XRPD signals at 16.3 °2θ, 16.9 °2θ, 24.5 °2θ, 25.6 °2θ, and 23.4°2θ (±0.2°2θ; ±0.1 °2θ; or ±0.0 °2θ; Cu Kα1 radiation).

In some embodiments, the solid form of tabernanthalog monofumarate is crystalline tabernanthalog monofumarate (Pattern #15) characterized by two or more, or three or more XRPD signals selected from the group consisting of 16.3°2θ, 16.9°2θ, 24.5°2θ, 25.6°2θ, 23.4°2θ, 8.5 °2θ, and 17.0°2θ (±0.2°2θ; ±0.1°2θ; or 0.0°2θ; Cu Kα1 radiation). In some embodiments, the solid form of tabernanthalog monofumarate is crystalline tabernanthalog monofumarate (Pattern #15) characterized by XRPD signals at 16.3°2θ, 16.9°2θ, 24.5°2θ, 25.6°2θ, 23.4°2θ, 8.5°2θ, and 17.0°2θ (±0.2°2θ; ±0.1°2θ; or ±0.0°2θ; Cu Kα1 radiation).

In some embodiments, the solid form of tabernanthalog monofumarate is crystalline tabernanthalog monofumarate (Pattern #15) characterized by two or more, or three or more XRPD signals selected from the group consisting of 16.3°2θ, 16.9°2θ, 24.5°2θ, 25.6°2θ, 23.4°2θ, 8.5 °2θ, 17.0°2θ, 17.7°2θ, 19.3°2θ, and 9.5°2θ (±0.2°2θ; ±0.1°2θ; or ±0.0°2θ; Cu Kα1 radiation). In some embodiments, the solid form of tabernanthalog monofumarate is crystalline tabernanthalog monofumarate (Pattern #15) characterized by XRPD signals at 16.3°2θ, 16.9°2θ, 24.5°2θ, 25.6 °2θ, 23.4°2θ, 8.5°2θ, 17.0°2θ, 17.7°2θ, 19.3°2θ, and 9.5°2θ (±0.2°2θ; ±0.1°2θ; or ±0.0°2θ; Cu Kα1 radiation).

In some embodiments, the crystalline tabernanthalog monofumarate (Pattern #15) is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five XRPD signals selected from those set forth in Table 8.

In some embodiments, the solid form of tabernanthalog monofumarate is crystalline tabernanthalog monofumarate (Pattern #1) characterized by two or more, or three or more XRPD signals selected from the group consisting of 25.5°2θ, 16.3°2θ, and 19.3°2θ (±0.2°2θ; ±0.1°2θ; or 0.0°2θ; Cu Kα1 radiation). In some embodiments, the solid form of tabernanthalog monofumarate is crystalline tabernanthalog monofumarate (Pattern #1) characterized by XRPD signals at 25.5°2θ, 16.3°2θ, and 19.3°2θ (±0.2°2θ; ±0.1°2θ; or 0.0°2θ; Cu Kα1 radiation).

In some embodiments, the solid form of tabernanthalog monofumarate is crystalline tabernanthalog monofumarate (Pattern #1) characterized by two or more, or three or more XRPD signals selected from the group consisting of 25.5°2θ, 16.3°2θ, 19.3°2θ, 16.7°2θ, and 9.0°2θ (±0.2°2θ; ±0.1°2θ; or 0.0°2θ; Cu Kα1 radiation). In some embodiments, the solid form of tabernanthalog monofumarate is crystalline tabernanthalog monofumarate (Pattern #1) characterized by XRPD signals at 25.5°2θ, 16.3°2θ, 19.3°2θ, 16.7°2θ, and 9.0°2θ (±0.2°2θ; ±0.1°2θ; or ±0.0°2θ; Cu Kα1 radiation).

In some embodiments, the solid form of tabernanthalog monofumarate is crystalline tabernanthalog monofumarate (Pattern #1) characterized by two or more, or three or more XRPD signals selected from the group consisting of 25.5°2θ, 16.3°2θ, 19.3°2θ, 16.7°2θ, 9.0°2θ, 26.8 °2θ, and 18.1°2θ (±0.2°2θ; ±0.1°2θ; or 0.0°2θ; Cu Kα1 radiation). In some embodiments, the solid form of tabernanthalog monofumarate is crystalline tabernanthalog monofumarate (Pattern #1) characterized by XRPD signals at 25.5°2θ, 16.3°2θ, 19.3°2θ, 16.7°2θ, 9.0°2θ, 26.8°2θ, and 18.1 °2θ (±0.2°2θ; ±0.1°2θ; or 0.0°2θ; Cu Kα1 radiation).

In some embodiments, the solid form of tabernanthalog monofumarate is crystalline tabernanthalog monofumarate (Pattern #1) characterized by two or more, or three or more XRPD signals selected from the group consisting of 25.5°2θ, 16.3°2θ, 19.3°2θ, 16.7°2θ, 9.0°2θ, 26.8 °2θ, 18.1°2θ, 17.7°2θ, 27.2°2θ, and 21.1°2θ (±0.2°2θ; ±0.1°2θ; or 0.0°2θ; Cu Kα1 radiation).

In some embodiments, the solid form of tabernanthalog monofumarate is crystalline tabernanthalog monofumarate (Pattern #1) characterized by XRPD signals at 25.5°2θ, 16.3°2θ, 19.3°2θ, 16.7°2θ, 9.0°2θ, 26.8°2θ, 18.1°2θ, 17.7°2θ, 27.2°2θ, and 21.1°2θ (±0.2°2θ; ±0.1°2θ; or ±0.0°2θ; Cu Kα1 radiation).

In some embodiments, the crystalline tabernanthalog monofumarate (Pattern #1) is characterized by one, two, three, four, five, six, seven, eight, nine, ten, eleven, twelve, thirteen, fourteen, fifteen, sixteen, seventeen, or eighteen XRPD signals selected from those set forth in Table 9.

In some embodiments, the solid form of tabernanthalog monofumarate is crystalline tabernanthalog monofumarate (Pattern #1) characterized by two or more, or three or more XRPD signals selected from the group consisting of 25.5°2θ, 16.3°2θ, and 19.3°2θ (±0.2°2θ; ±0.1°2θ; or 0.0°2θ; Cu Kα1 radiation). In some embodiments, the solid form of tabernanthalog monofumarate is crystalline tabernanthalog monofumarate (Pattern #1) characterized by XRPD signals at 25.5°2θ, 16.3°2θ, and 19.3°2θ (±0.2°2θ; ±0.1°2θ; or 0.0°2θ; Cu Kα1 radiation).

In some embodiments, the solid form of tabernanthalog monofumarate is crystalline tabernanthalog monofumarate (Pattern #1) characterized by two or more, or three or more XRPD signals selected from the group consisting of 25.5°2θ, 16.3°2θ, 19.3°2θ, 16.7°2θ, and 26.1°2θ (±0.2°2θ; ±0.1°2θ; or 0.0°2θ; Cu Kα1 radiation). In some embodiments, the solid form of tabernanthalog monofumarate is crystalline tabernanthalog monofumarate (Pattern #1) characterized by XRPD signals at 25.5°2θ, 16.3°2θ, 19.3°2θ, 16.7°2θ, and 26.1°2θ (±0.2°2θ; ±0.1°2θ; or ±0.0°2θ; Cu Kα1 radiation).

In some embodiments, the solid form of tabernanthalog monofumarate is crystalline tabernanthalog monofumarate (Pattern #1) characterized by two or more, or three or more XRPD signals selected from the group consisting of 25.5 °2θ, 16.3 °2θ, 19.3 °2θ, 16.7 °2θ, 26.1 °2θ, 18.1 °2θ, and 26.8 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate (Pattern #1) characterized by XRPD signals at 25.5 °2θ, 16.3 °2θ, 19.3 °2θ, 16.7 °2θ, 26.1 °2θ, 18.1 °2θ, and 26.8 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate (Pattern #1) characterized by two or more, or three or more XRPD signals selected from the group consisting of 25.5 °2θ, 16.3 °2θ, 19.3 °2θ, 16.7 °2θ, 26.1 °2θ, 18.1 °2θ, 21.8 °2θ, 9.1 °2θ, 21.3 °2θ, and 26.8 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate (Pattern #1) characterized by XRPD signals at 25.5 °2θ, 16.3 °2θ, 19.3 °2θ, 16.7 °2θ, 26.1 °2θ, 18.1 °2θ, 21.8 °2θ, 9.1 °2θ, 21.3 °2θ, and 26.8 °2θ (±0.2 °2θ; ±0.1 °2θ; or 0.0 °2θ; Cu Kα1 radiation).

In some embodiments, the crystalline tabernanthalog monofumarate (Pattern #1) is characterized by one, two, three, four, five, six, seven, eight, nine, ten, eleven, twelve, thirteen, fourteen, fifteen, sixteen, or seventeen XRPD signals selected from those set forth in Table 10.

In some embodiments, the solid form of tabernanthalog hemifumarate is crystalline tabernanthalog hemifumarate (Pattern #5) characterized by two or more, or three or more XRPD signals selected from the group consisting of 8.3 °2θ, 17.0 °2θ, and 11.1 °2θ (±0.2 °2θ; ±0.1 °2θ; or ±0.0 °2θ; Cu Kα1 radiation). In some embodiments, the solid form of tabernanthalog hemifumarate is crystalline tabernanthalog hemifumarate (Pattern #5) characterized by XRPD signals at 8.3 °2θ, 17.0 °2θ, and 11.1 °2θ (±0.2 °2θ; ±0.1 °2θ; or 0.0 °2θ; Cu Kα1 radiation).

In some embodiments, the solid form of tabernanthalog hemifumarate is crystalline tabernanthalog hemifumarate (Pattern #5) characterized by two or more, or three or more XRPD signals selected from the group consisting of 8.3 °2θ, 17.0 °2θ, 11.1 °2θ, 15.4 °2θ, and 21.5 °2θ(±0.2 °2θ; ±0.1 °2θ; or 0.0 °2θ; Cu Kα1 radiation). In some embodiments, the solid form of tabernanthalog hemifumarate is crystalline tabernanthalog hemifumarate (Pattern #5) characterized by XRPD signals at 8.3 °2θ, 17.0 °2θ, 11.1 °2θ, 15.4 °2θ, and 21.5 °2θ (±0.2 °2θ; ±0.1 °2θ; or 0.0 °2θ; Cu Kα1 radiation).

In some embodiments, the crystalline tabernanthalog hemifumarate (Pattern #5) is characterized by one, two, three, four, five, or six XRPD signals selected from those set forth in Table 11.

In some embodiments, the solid form of tabernanthalog monofumarate (Pattern #9) is crystalline tabernanthalog monofumarate (Pattern #9) characterized by two or more, or three or more XRPD signals selected from the group consisting of 25.6 °2θ, 16.4 °2θ, and 15.9 °2θ (±0.2 °2θ; ±0.1 °2θ; or ±0.0 °2θ; Cu Kα1 radiation). In some embodiments, the solid form of tabernanthalog monofumarate (Pattern #9) is crystalline tabernanthalog monofumarate (Pattern #9) characterized by XRPD signals at 25.6 °2θ, 16.4 °2θ, and 15.9 °2θ (±0.2 °2θ; ±0.1 °2θ; or ±0.0 °2θ; Cu Kα1 radiation).

In some embodiments, the solid form of tabernanthalog monofumarate (Pattern #9) is crystalline tabernanthalog monofumarate (Pattern #9) characterized by two or more, or three or more XRPD signals selected from the group consisting of 25.6 °2θ, 16.4 °2θ, 15.9 °2θ, 24.6 °2θ, and 25.3 °2θ (±0.2 °2θ; ±0.1 °2θ; or 0.0 °2θ; Cu Kα1 radiation). In some embodiments, the solid form of tabernanthalog monofumarate (Pattern #9) is crystalline tabernanthalog monofumarate (Pattern #9) characterized by XRPD signals at 25.6 °2θ, 16.4 °2θ, 15.9 °2θ, 24.6 °2θ, and 25.3 °2θ (±0.2 °2θ; ±0.1 °2θ; or ±0.0 °2θ; Cu Kα1 radiation).

In some embodiments, the solid form of tabernanthalog monofumarate (Pattern #9) is crystalline tabernanthalog monofumarate (Pattern #9) characterized by two or more, or three or more XRPD signals selected from the group consisting of 25.6 °2θ, 16.4 °2θ, 15.9 °2θ, 24.6 °2θ, 25.3 °2θ, 19.4 °2θ, and 9.1 °2θ (±0.2 °2θ; ±0.1 °2θ; or 0.0 °2θ; Cu Kα1 radiation). In some embodiments, the solid form of tabernanthalog monofumarate (Pattern #9) is crystalline tabernanthalog monofumarate (Pattern #9) characterized by XRPD signals at 25.6 °2θ, 16.4 °2θ, 15.9 °2θ, 24.6 °2θ, 25.3 °2θ, 19.4 °2θ, and 9.1 °2θ (±0.2 °2θ; ±0.1 °2θ; or 0.0 °2θ; Cu Kα1 radiation).

In some embodiments, the solid form of tabernanthalog monofumarate (Pattern #9) is crystalline tabernanthalog monofumarate (Pattern #9) characterized by two or more, or three or more XRPD signals selected from the group consisting of 25.6 °2θ, 16.4 °2θ, 15.9 °2θ, 24.6 °2θ, 25.3 °2θ, 19.4 °2θ, 9.1 °2θ, 18.1 °2θ, 26.9 °2θ, and 7.9 °2θ (±0.2 °2θ; ±0.1 °2θ; or 0.0 °2θ; Cu Kα1 radiation). In some embodiments, the solid form of tabernanthalog monofumarate (Pattern #9) is crystalline tabernanthalog monofumarate (Pattern #9) characterized by XRPD signals at 25.6 °2θ, 16.4 °2θ, 15.9 °2θ, 24.6 °2θ, 25.3 °2θ, 19.4 °2θ, 9.1 °2θ, 18.1 °2θ, 26.9 °2θ, and 7.9 °2θ (±0.2 °2θ; ±0.1 °2θ; or 0.0 °2θ; Cu Kα1 radiation).

In some embodiments, the crystalline tabernanthalog monofumarate (Pattern #9) is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 12.

In some embodiments, the solid form of tabernanthalog monofumarate (Pattern #10) is crystalline tabernanthalog monofumarate (Pattern #10) characterized by two or more, or three or more XRPD signals selected from the group consisting of 16.9 °2θ, 25.6 °2θ, and 16.4 °2θ (±0.2 °2θ; ±0.1 °2θ; or 0.0 °2θ; Cu Kα1 radiation). In some embodiments, the solid form of tabernanthalog monofumarate (Pattern #10) is crystalline tabernanthalog monofumarate (Pattern #10) characterized by XRPD signals at 16.9 °2θ, 25.6 °2θ, and 16.4 °2θ (±0.2 °2θ; ±0.1 °2θ; or 0.0 °2θ; Cu Kα1 radiation).

In some embodiments, the solid form of tabernanthalog monofumarate (Pattern #10) is crystalline tabernanthalog monofumarate (Pattern #10) characterized by two or more, or three or more XRPD signals selected from the group consisting of 16.9 °2θ, 25.6 °2θ, 16.4 °2θ, 21.4 °2θ, and 23.5 °2θ (±0.2 °2θ; ±0.1 °2θ; or ±0.0 °2θ; Cu Kα1 radiation). In some embodiments, the solid form of tabernanthalog monofumarate (Pattern #10) is crystalline tabernanthalog monofumarate (Pattern #10) characterized by XRPD signals at 16.9 °2θ, 25.6 °2θ, 16.4 °2θ, 21.4 °2θ, and 23.5 °2θ (±0.2 °2θ; ±0.1 °2θ; or 0.0 °2θ; Cu Kα1 radiation).

In some embodiments, the solid form of tabernanthalog monofumarate (Pattern #10) is crystalline tabernanthalog monofumarate (Pattern #10) characterized by two or more, or three or more XRPD signals selected from the group consisting of 16.9 °2θ, 25.6 °2θ, 16.4 °2θ, 21.4 °2θ, 23.5 °2θ, 8.2 °2θ, and 15.2 °2θ (±0.2 °2θ; ±0.1 °2θ; or ±0.0 °2θ; Cu Kα1 radiation). In some embodiments, the solid form of tabernanthalog monofumarate (Pattern #10) is crystalline tabernanthalog monofumarate (Pattern #10) characterized by XRPD signals at 16.9 °2θ, 25.6 °2θ, 16.4 °2θ, 21.4 °2θ, 23.5 °2θ, 8.2 °2θ, and 15.2 °2θ (±0.2 °2θ; ±0.1 °2θ; or ±0.0 °2θ; Cu Kα1 radiation).

In some embodiments, the solid form of tabernanthalog monofumarate (Pattern #10) is crystalline tabernanthalog monofumarate (Pattern #10) characterized by two or more, or three or more XRPD signals selected from the group consisting of 16.9 °2θ, 25.6 °2θ, 16.4 °2θ, 21.4 °2θ, 23.5 °2θ, 8.2 °2θ, 15.2 °2θ, 19.8 °2θ, 9.1 °2θ, and 10.8 °2θ (±0.2 °2θ; 0.1 °2θ; or 0.0 °2θ; Cu Kα1 radiation). In some embodiments, the solid form of tabernanthalog monofumarate (Pattern #10) is crystalline tabernanthalog monofumarate (Pattern #10) characterized by XRPD signals at 16.9 °2θ, 25.6 °2θ, 16.4 °2θ, 21.4 °2θ, 23.5 °2θ, 8.2 °2θ, 15.2 °2θ, 19.8 °2θ, 9.1 °2θ, and 10.8 °2θ (±0.2 °2θ; ±0.1 °2θ; or ±0.0 °2θ; Cu Kα1 radiation).

In some embodiments, the crystalline tabernanthalog monofumarate (Pattern #10) is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 13.

In some embodiments, the solid form of tabernanthalog monofumarate (Pattern #8) is crystalline tabernanthalog monofumarate (Pattern #8) characterized by two or more, or three or more XRPD signals selected from the group consisting of 16.3 °2θ, 25.5 °2θ, and 15.8 °2θ (±0.2 °2θ; ±0.1 °2θ; or 0.0 °2θ; Cu Kα1 radiation). In some embodiments, the solid form of tabernanthalog monofumarate (Pattern #8) is crystalline tabernanthalog monofumarate (Pattern #8) characterized by XRPD signals at 16.3 °2θ, 25.5 °2θ, and 15.8 °2θ (±0.2 °2θ; ±0.1 °2θ; or 0.0 °2θ; Cu Kα1 radiation).

In some embodiments, the solid form of tabernanthalog monofumarate (Pattern #8) is crystalline tabernanthalog monofumarate (Pattern #8) characterized by two or more, or three or more XRPD signals selected from the group consisting of 16.3 °2θ, 25.5 °2θ, 15.8 °2θ, 24.3 °2θ, and 7.6 °2θ (±0.2 °2θ; ±0.1 °2θ; or 0.0 °2θ; Cu Kα1 radiation). In some embodiments, the solid form of tabernanthalog monofumarate (Pattern #8) is crystalline tabernanthalog monofumarate (Pattern #8) characterized by XRPD signals at 16.3 °2θ, 25.5 °2θ, 15.8 °2θ, 24.3 °2θ, and 7.6 °2θ (±0.2 °2θ; ±0.1 °2θ; or ±0.0 °2θ; Cu Kα1 radiation).

In some embodiments, the solid form of tabernanthalog monofumarate (Pattern #8) is crystalline tabernanthalog monofumarate (Pattern #8) characterized by two or more, or three or more XRPD signals selected from the group consisting of 16.3 °2θ, 25.5 °2θ, 15.8 °2θ, 24.3 °2θ, 7.6 °2θ, 19.1 °2θ, and 20.6 °2θ (±0.2 °2θ; ±0.1 °2θ; or 0.0 °2θ; Cu Kα1 radiation). In some embodiments, the solid form of tabernanthalog monofumarate (Pattern #8) is crystalline tabernanthalog monofumarate (Pattern #8) characterized by XRPD signals at 16.3 °2θ, 25.5 °2θ, 15.8 °2θ, 24.3 °2θ, 7.6 °2θ, 19.1 °2θ, and 20.6 °2θ (±0.2 °2θ; ±0.1 °2θ; or 0.0 °2θ; Cu Kα1 radiation).

In some embodiments, the solid form of tabernanthalog monofumarate (Pattern #8) is crystalline tabernanthalog monofumarate (Pattern #8) characterized by two or more, or three or more XRPD signals selected from the group consisting of 16.3 °2θ, 25.5 °2θ, 15.8 °2θ, 24.3 °2θ, 7.6 °2θ, 19.1 °2θ, and 20.6 °2θ, 18.1 °2θ, 9.0 °2θ, and 26.8 °2θ (±0.2 °2θ; ±0.1 °2θ; or ±0.0 °2θ; Cu Kα1 radiation). In some embodiments, the solid form of tabernanthalog monofumarate (Pattern #8) is crystalline tabernanthalog monofumarate (Pattern #8) characterized by XRPD signals at 16.3 °2θ, 25.5 °2θ, 15.8 °2θ, 24.3 °2θ, 7.6 °2θ, 19.1 °2θ, and 20.6 °2θ, 18.1 °2θ, 9.0 °2θ, and 26.8 °2θ (±0.2 °2θ; ±0.1 °2θ; or 0.0 °2θ; Cu Kα1 radiation).

In some embodiments, the crystalline tabernanthalog monofumarate (Pattern #8) is characterized by one, two, three, four, five, six, seven, eight, nine, ten, eleven, twelve, thirteen, fourteen, fifteen, sixteen, seventeen, eighteen, nineteen, twenty, twenty-one, or twenty-two XRPD signals selected from those set forth in Table 14.

In some embodiments, the solid form of tabernanthalog monofumarate (Pattern #6b) is crystalline tabernanthalog monofumarate (Pattern #6b) characterized by two or more, or three or more XRPD signals selected from the group consisting of 19.5 °2θ, 26.1 °2θ, and 8.2 °2θ (±0.2 °2θ; ±0.1 °2θ; or ±0.0 °2θ; Cu Kα1 radiation). In some embodiments, the solid form of tabernanthalog monofumarate (Pattern #6b) is crystalline tabernanthalog monofumarate (Pattern #6b) characterized by XRPD signals at 19.5 °2θ, 26.1 °2θ, and 8.2 °2θ (±0.2 °2θ; ±0.1 °2θ; or 0.0 °2θ; Cu Kα1 radiation).

In some embodiments, the solid form of tabernanthalog monofumarate (Pattern #6b) is crystalline tabernanthalog monofumarate (Pattern #6b) characterized by two or more, or three or more XRPD signals selected from the group consisting of 19.5 °2θ, 26.1 °2θ, 8.2 °2θ, 13.0 °2θ, and 16.5 °2θ (±0.2 °2θ; ±0.1 °2θ; or ±0.0 °2θ; Cu Kα1 radiation). In some embodiments, the solid form of tabernanthalog monofumarate (Pattern #6b) is crystalline tabernanthalog monofumarate (Pattern #6b) characterized by XRPD signals at 19.5 °2θ, 26.1 °2θ, 8.2 °2θ, 13.0 °2θ, and 16.5 °2θ (±0.2 °2θ; ±0.1 °2θ; or 0.0 °2θ; Cu Kα1 radiation).

In some embodiments, the solid form of tabernanthalog monofumarate (Pattern #6b) is crystalline tabernanthalog monofumarate (Pattern #6b) characterized by two or more, or three or more XRPD signals selected from the group consisting of 19.5 °2θ, 26.1 °2θ, 8.2 °2θ, 13.0 °2θ, 16.5 °2θ, 19.6 °2θ, and 20.6 °2θ (±0.2 °2θ; ±0.1 °2θ; or 0.0 °2θ; Cu Kα1 radiation). In some embodiments, the solid form of tabernanthalog monofumarate (Pattern #6b) is crystalline tabernanthalog monofumarate (Pattern #6b) characterized by XRPD signals at 19.5 °2θ, 26.1 °2θ, 8.2 °2θ, 13.0 °2θ, 16.5 °2θ, 19.6 °2θ, and 20.6 °2θ (±0.2 °2θ; ±0.1 °2θ; or ±0.0 °2θ; Cu Kα1 radiation).

In some embodiments, the solid form of tabernanthalog monofumarate (Pattern #6b) is crystalline tabernanthalog monofumarate (Pattern #6b) characterized by two or more, or three or more XRPD signals selected from the group consisting of 25.3 °2θ, 19.5 °2θ, 26.1 °2θ, 8.2 °2θ, 13.0 °2θ, 16.5 °2θ, 19.6 °2θ, and 20.6 °2θ (±0.2 °2θ; ±0.1 °2θ; or 0.0 °2θ; Cu Kα1 radiation). In some embodiments, the solid form of tabernanthalog monofumarate (Pattern #6b) is crystalline tabernanthalog monofumarate (Pattern #6b) characterized by XRPD signals at 25.3 °2θ, 19.5 °2θ, 26.1 °2θ, 8.2 °2θ, 13.0 °2θ, 16.5 °2θ, 19.6 °2θ, and 20.6 °2θ (±0.2 °2θ; ±0.1 °2θ; or ±0.0 °2θ; Cu Kα1 radiation).

In some embodiments, the crystalline tabernanthalog monofumarate (Pattern #6b) is characterized by one, two, three, four, five, six, seven, or eight XRPD signals selected from those set forth in Table 15.

In some embodiments, the solid form of tabernanthalog monofumarate (Pattern #2c) is crystalline tabernanthalog monofumarate (Pattern #2c) characterized by two or more, or three or more XRPD signals selected from the group consisting of 25.7 °2θ, 16.4 °2θ, and 16.1 °2θ (±0.2 °2θ; ±0.1 °2θ; or 0.0 °2θ; Cu Kα1 radiation). In some embodiments, the solid form of tabernanthalog monofumarate (Pattern #2c) is crystalline tabernanthalog monofumarate (Pattern #2c) characterized by XRPD signals at 25.7 °2θ, 16.4 °2θ, and 16.1 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by two or more, or three or more XRPD signals selected from the group consisting of 25.7 °2θ, 16.4 °2θ, 16.1 °2θ, 9.2 °2θ, and 18.2 °2θ (±0.2 °2θ; ±0.1 °2θ; or 0.0 °2θ; Cu Kα1 radiation). In some embodiments, the solid form of tabernanthalog monofumarate (Pattern #2c) is crystalline tabernanthalog monofumarate (Pattern #2c) characterized by XRPD signals at 25.7 °2θ, 16.4 °2θ, 16.1 °2θ, 9.2 °2θ, and 18.2 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by two or more, or three or more XRPD signals selected from the group consisting of 25.7 °2θ, 16.4 °2θ, 16.1 °2θ, 9.2 °2θ, 18.2 °2θ, 7.9 °2θ, and 24.8 °2θ (±0.2 °2θ; ±0.1 °2θ; or 0.0 °2θ; Cu Kα1 radiation). In some embodiments, the solid form of tabernanthalog monofumarate (Pattern #2c) is crystalline tabernanthalog monofumarate (Pattern #2c) characterized by XRPD signals at 25.7 °2θ, 16.4 °2θ, 16.1 °2θ, 9.2 °2θ, 18.2 °2θ, 7.9 °2θ, and 24.8 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by two or more, or three or more XRPD signals selected from the group consisting of 25.7 °2θ, 16.4 °2θ, 16.1 °2θ, 9.2 °2θ, 18.2 °2θ, 7.9 °2θ, 24.8 °2θ, 26.9 °2θ, 19.5 °2θ, and 7.6 °2θ (±0.2 °2θ; ±0.1 °2θ; or 0.0 °2θ; Cu Kα1 radiation). In some embodiments, the solid form of tabernanthalog monofumarate (Pattern #2c) is crystalline tabernanthalog monofumarate (Pattern #2c) characterized by XRPD signals at 25.7 °2θ, 16.4 °2θ, 16.1 °2θ, 9.2 °2θ, 18.2 °2θ, 7.9 °2θ, 24.8 °2θ, 26.9 °2θ, 19.5 °2θ, and 7.6 °2θ (±0.2 °2θ; ±0.1 °2θ; or ±0.0 °2θ; Cu Kα1 radiation).

In some embodiments, the crystalline tabernanthalog monofumarate (Pattern #2c) is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 16.

In some embodiments, the solid form of tabernanthalog monofumarate (Pattern #7) is crystalline tabernanthalog monofumarate (Pattern #7) characterized by two or more, or three or more XRPD signals selected from the group consisting of 25.7 °2θ, 16.4 °2θ, and 16.0 °2θ (±0.2 °2θ; ±0.1 °2θ, or 0.0 °2θ; Cu Kα1 radiation). In some embodiments, the solid form of tabernanthalog monofumarate (Pattern #7)

is crystalline tabernanthalog monofumarate (Pattern #7) characterized by XRPD signals at 25.7 °2θ, 16.4 °2θ, and 16.0 °2θ (±0.2 °2θ; ±0.1 °2θ; or 0.0 °2θ; Cu Kα1 radiation).

In some embodiments, the solid form of tabernanthalog monofumarate (Pattern #7) is crystalline tabernanthalog monofumarate (Pattern #7) characterized by two or more, or three or more XRPD signals selected from the group consisting of 25.7 °2θ, 16.4 °2θ, 16.0 °2θ, 19.5 °2θ, and 21.4 °2θ (±0.2 °2θ; ±0.1 °2θ; or ±0.0 °2θ; Cu Kα1 radiation). In some embodiments, the solid form of tabernanthalog monofumarate (Pattern #7) is crystalline tabernanthalog monofumarate (Pattern #7) characterized by XRPD signals at 25.7 °2θ, 16.4 °2θ, 16.0 °2θ, 19.5 °2θ, and 21.4 °2θ (±0.2 °2θ; ±0.1 °2θ; or 0.0 °2θ; Cu Kα1 radiation).

In some embodiments, the solid form of tabernanthalog monofumarate (Pattern #7) is crystalline tabernanthalog monofumarate (Pattern #7) characterized by two or more, or three or more XRPD signals selected from the group consisting of 25.7 °2θ, 16.4 °2θ, 16.0 °2θ, 19.5 °2θ, 21.4 °2θ, 7.3 °2θ, and 25.0 °2θ (±0.2 °2θ; ±0.1 °2θ; or ±0.0 °2θ; Cu Kα1 radiation). In some embodiments, the solid form of tabernanthalog monofumarate (Pattern #7) is crystalline tabernanthalog monofumarate (Pattern #7) characterized by XRPD signals at 25.7 °2θ, 16.4 °2θ, 16.0 °2θ, 19.5 °2θ, 21.4 °2θ, 7.3 °2θ, and 25.0 °2θ (±0.2 °2θ; ±0.1 °2θ; or 0.0 °2θ; Cu Kα1 radiation).

In some embodiments, the solid form of tabernanthalog monofumarate (Pattern #7) is crystalline tabernanthalog monofumarate (Pattern #7) characterized by two or more, or three or more XRPD signals selected from the group consisting of 25.7 °2θ, 16.4 °2θ, 16.0 °2θ, 19.5 °2θ, 21.4 °2θ, 7.3 °2θ, 25.0 °2θ, 9.2 °2θ, 18.2 °2θ, and 16.8 °2θ (±0.2 °2θ; ±0.1 °2θ; or 0.0 °2θ; Cu Kα1 radiation). In some embodiments, the solid form of tabernanthalog monofumarate (Pattern #7) is crystalline tabernanthalog monofumarate (Pattern #7) characterized by XRPD signals at 25.7 °2θ, 16.4 °2θ, 16.0 °2θ, 19.5 °2θ, 21.4 °2θ, 7.3 °2θ, 25.0 °2θ, 9.2 °2θ, 18.2 °2θ, and 16.8 °2θ (±0.2 °2θ; ±0.1 °2θ; or ±0.0 °2θ; Cu Kα1 radiation).

In some embodiments, the crystalline tabernanthalog monofumarate (Pattern #7) is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 17. In some embodiments, the solid form of tabernanthalog monofumarate (Pattern #11) is crystalline tabernanthalog monofumarate (Pattern #11) characterized by two or more, or three or more XRPD signals selected from the group consisting of 25.6 °2θ, 16.0 °2θ, and 21.5 °2θ (±0.2 °2θ; ±0.1 °2θ; or ±0.0 °2θ; Cu Kα1 radiation). In some embodiments, the solid form of tabernanthalog monofumarate (Pattern #11) is crystalline tabernanthalog monofumarate (Pattern #11) characterized by XRPD signals at 25.6 °2θ, 16.0 °2θ, and 21.5 °2θ (±0.2 °2θ; ±0.1 °2θ; or 0.0 °2θ; Cu Kα1 radiation).

In some embodiments, the solid form of tabernanthalog monofumarate (Pattern #11) is crystalline tabernanthalog monofumarate (Pattern #11) characterized by two or more, or three or more XRPD signals selected from the group consisting of 25.6 °2θ, 16.0 °2θ, 21.5 °2θ, 20.2 °2θ, and 16.3 °2θ (±0.2 °2θ; ±0.1 °2θ; or ±0.0 °2θ; Cu Kα1 radiation). In some embodiments, the solid form of tabernanthalog monofumarate (Pattern #11) is crystalline tabernanthalog monofumarate (Pattern #11) characterized by XRPD signals at 25.6 °2θ, 16.0 °2θ, 21.5 °2θ, 20.2 °2θ, and 16.3 °2θ (±0.2 °2θ; ±0.1 °2θ; or ±0.0 °2θ; Cu Kα1 radiation).

In some embodiments, the solid form of tabernanthalog monofumarate (Pattern #11) is crystalline tabernanthalog monofumarate (Pattern #11) characterized by two or more, or three or more XRPD signals selected from the group consisting of 25.6 °2θ, 16.0 °2θ, 21.5 °2θ, 20.2 °2θ, and 16.3 °2θ, 7.4 °2θ, and 17.2 °2θ (±0.2 °2θ; ±0.1 °2θ; or 0.0 °2θ; Cu Kα1 radiation). In some embodiments, the solid form of tabernanthalog monofumarate (Pattern #11) is crystalline tabernanthalog monofumarate (Pattern #11) characterized by XRPD signals at 25.6 °2θ, 16.0 °2θ, 21.5 °2θ, 20.2 °2θ, and 16.3 °2θ, 7.4 °2θ, and 17.2 °2θ (±0.2 °2θ; ±0.1 °2θ; or ±0.0 °2θ; Cu Kα1 radiation).

In some embodiments, the solid form of tabernanthalog monofumarate (Pattern #11) is crystalline tabernanthalog monofumarate (Pattern #11) characterized by two or more, or three or more XRPD signals selected from the group consisting of 25.6 °2θ, 16.0 °2θ, 21.5 °2θ, 20.2 °2θ, and 16.3 °2θ, 7.4 °2θ, 17.2 °2θ, 20.7 °2θ, 23.7 °2θ, and 26.8 °2θ (±0.2 °2θ; ±0.1 °2θ; or ±0.0 °2θ; Cu Kα1 radiation). In some embodiments, the solid form of tabernanthalog monofumarate (Pattern #11) is crystalline tabernanthalog monofumarate (Pattern #11) characterized by XRPD signals at 25.6 °2θ, 16.0 °2θ, 21.5 °2θ, 20.2 °2θ, and 16.3 °2θ, 7.4 °2θ, 17.2 °2θ, 20.7 °2θ, 23.7 °2θ, and 26.8 °2θ (±0.2 °2θ; ±0.1 °2θ; or ±0.0 °2θ; Cu Kα1 radiation).

In some embodiments, the crystalline tabernanthalog monofumarate (Pattern #11) is characterized by one, two, three, four, five, six, seven, eight, nine, ten, eleven, twelve, thirteen, fourteen, fifteen, sixteen, seventeen, eighteen, or nineteen XRPD signals selected from those set forth in Table 18.

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, and 16.8 °2θ (±0.2 °2θ; ±0.1 °2θ; or 0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, and 16.8 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, 16.8 °2θ, 22.4 °2θ, and 9.2 °2θ (±0.2 °2θ; ±0.1 °2θ; or 0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, 16.8 °2θ, 22.4 °2θ, and 9.2 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, 16.8 °2θ, 22.4 °2θ, 9.2 °2θ, 26.9 °2θ, and 19.4 °2θ (±0.2 °2θ; ±0.1 °2θ; or 0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, 16.8 °2θ, 22.4 °2θ, 9.2 °2θ, 26.9 °2θ, and 19.4 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, 16.8 °2θ, 22.4 °2θ, 9.2 °2θ, 26.9 °2θ, 19.4 °2θ, 18.2 °2θ, 26.2 °2θ, and 20.3 °2θ (±0.2 °2θ; ±0.1 °2θ; or 0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, 16.8 °2θ, 22.4 °2θ, 9.2 °2θ, 26.9 °2θ, 19.4 °2θ, 18.2 °2θ, 26.2 °2θ, and 20.3 °2θ (±0.2 °2θ; ±0.1 °2θ; or 0.0 °2θ; Cu Kα1 radiation).

In some embodiments, the crystalline tabernanthalog monofumarate (Pattern #1) is characterized by one, two, three, four, five, six, seven, eight, nine, ten, eleven, twelve, thirteen, fourteen, fifteen, sixteen, or seventeen XRPD signals selected from those set forth in Table 19.

In some embodiments, the solid form of tabernanthalog monofumarate (Pattern #2c) is crystalline tabernanthalog monofumarate (Pattern #2c) characterized by two or more, or three or more XRPD signals selected from the group consisting of 25.5 °2θ, 9.1 °2θ, and 16.3 °2θ (±0.2 °2θ; ±0.1 °2θ; or ±0.0 °2θ; Cu Kα1 radiation). In some embodiments, the solid form of tabernanthalog monofumarate (Pattern #2c) is crystalline tabernanthalog monofumarate (Pattern #2c) characterized by XRPD signals at 25.5 °2θ, 9.1 °2θ, and 16.3 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by two or more, or three or more XRPD signals selected from the group consisting of 25.5 °2θ, 9.1 °2θ, 16.3 °2θ, 25.1 °2θ, and 18.0 °2θ (±0.2 °2θ; ±0.1 °2θ; or ±0.0 °2θ; Cu Kα1 radiation). In some embodiments, the solid form of tabernanthalog monofumarate (Pattern #2c) is crystalline tabernanthalog monofumarate (Pattern #2c) characterized by XRPD signals at 25.5 °2θ, 9.1 °2θ, 16.3 °2θ, 25.1 °2θ, and 18.0 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by two or more, or three or more XRPD signals selected from the group consisting of 25.5 °2θ, 9.1 °2θ, 16.3 °2θ, 25.1 °2θ, 18.0 °2θ, 21.9 °2θ, and 14.2 °2θ (±0.2 °2θ; ±0.1 °2θ; or 0.0 °2θ; Cu Kα1 radiation). In some embodiments, the solid form of tabernanthalog monofumarate (Pattern #2c) is crystalline tabernanthalog monofumarate (Pattern #2c) characterized by XRPD signals at 25.5 °2θ, 9.1 °2θ, 16.3 °2θ, 25.1 °2θ, 18.0 °2θ, 21.9 °2θ, and 14.2 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by two or more, or three or more XRPD signals selected from the group consisting of 25.5 °2θ, 9.1 °2θ, 16.3 °2θ, 25.1 °2θ, 18.0 °2θ, 21.9 °2θ, 14.2 °2θ, 17.4 °2θ, 26.7 °2θ, and 27.2 °2θ (±0.2 °2θ; ±0.1 °2θ; or 0.0 °2θ; Cu Kα1 radiation). In some embodiments, the solid form of tabernanthalog monofumarate (Pattern #2c) is crystalline tabernanthalog monofumarate (Pattern #2c) characterized by XRPD signals at 25.5 °2θ, 9.1 °2θ, 16.3 °2θ, 25.1 °2θ, 18.0 °2θ, 21.9 °2θ, 14.2 °2θ, 17.4 °2θ, 26.7 °2θ, and 27.2 °2θ (±0.2 °2θ; ±0.1 °2θ; or 0.0 °2θ; Cu Kα1 radiation).

In some embodiments, the crystalline tabernanthalog monofumarate (Pattern #2c) is characterized by one, two, three, four, five, six, seven, eight, nine, ten, eleven, or twelve XRPD signals selected from those set forth in Table 20.

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, and 19.5 °2θ (±0.2 °2θ; ±0.1 °2θ; or ±0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, and 19.5 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, 19.5 °2θ, 16.8 °2θ, and 18.3 °2θ (±0.2 °2θ; ±0.1 °2θ; or ±0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, 19.5 °2θ, 16.8 °2θ, and 18.3 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, 19.5 °2θ, 16.8 °2θ, 18.3 °2θ, 22.4 °2θ, and 27.4 °2θ (±0.2 °2θ; ±0.1 °2θ; or ±0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, 19.5 °2θ, 16.8 °2θ, 18.3 °2θ, 22.4 °2θ, and 27.4 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, 19.5 °2θ, 16.8 °2θ, 18.3 °2θ, 22.4 °2θ, 27.4 °2θ, 9.2 °2θ, 27.0 °2θ, and 26.3 °2θ (±0.2 °2θ; ±0.1 °2θ; or ±0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, 19.5 °2θ, 16.8 °2θ, 18.3 °2θ, 22.4 °2θ, 27.4 °2θ, 9.2 °2θ, 27.0 °2θ, and 26.3 °2θ (±0.2 °2θ; ±0.1 °2θ; or 0.0 °2θ; Cu Kα1 radiation).

In some embodiments, the crystalline tabernanthalog monofumarate (Pattern #1) is characterized by one, two, three, four, five, six, seven, eight, nine, ten, eleven, twelve, thirteen, fourteen, fifteen, sixteen, seventeen, eighteen, or nineteen XRPD signals selected from those set forth in Table 21.

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, and 19.4 °2θ (±0.2 °2θ; ±0.1 °2θ; or ±0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, and 19.4 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, 19.4 °2θ, 16.8 °2θ, and 18.2 °2θ (±0.2 °2θ; ±0.1 °2θ; or 0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, 19.4 °2θ, 16.8 °2θ, and 18.2 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, 19.4 °2θ, 16.8 °2θ, 18.2 °2θ, 27.0 °2θ, and 27.4 °2θ (±0.2 °2θ; ±0.1 °2θ; or 0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, 19.4 °2θ, 16.8 °2θ, 18.2 °2θ, 27.0 °2θ, and 27.4 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 25.7 °2θ, 16.5 °2θ, 19.4 °2θ, 16.8 °2θ, 18.2 °2θ, 27.0 °2θ, 27.4 °2θ, 22.4 °2θ, 9.2 °2θ, and 26.3 °2θ (±0.2 °2θ; ±0.1 °2θ; or 0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.7 °2θ, 16.5 °2θ, 19.4 °2θ, 16.8 °2θ, 18.2 °2θ, 27.0 °2θ, 27.4 °2θ, 22.4 °2θ, 9.2 °2θ, and 26.3 °2θ (±0.2 °2θ; ±0.1 °2θ; or 0.0 °2θ; Cu Kα1 radiation).

In some embodiments, the crystalline tabernanthalog monofumarate (Pattern #1) is characterized by one, two, three, four, five, six, seven, eight, nine, ten, eleven, twelve, thirteen, fourteen, fifteen, sixteen, or seventeen XRPD signals selected from those set forth in Table 22.

In some embodiments, the solid form of tabernanthalog monofumarate (Pattern #1) is crystalline tabernanthalog monofumarate (Pattern #1) characterized by two or more, or three or more XRPD signals selected from the group consisting of 16.4 °2θ, 25.7 °2θ, and 22.4 °2θ (±0.2 °2θ; ±0.1 °2θ; or 0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 16.4 °2θ, 25.7 °2θ, and 22.4 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 16.4 °2θ, 25.7 °2θ, 22.4 °2θ, 16.9 °2θ, and 19.4 °2θ (±0.2 °2θ; ±0.1 °2θ; or ±0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 16.4 °2θ, 25.7 °2θ, 22.4 °2θ, 16.9 °2θ, and 19.4 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 16.4 °2θ, 25.7 °2θ, 22.4 °2θ, 16.9 °2θ, 19.4 °2θ, 18.2 °2θ, and 27.0 °2θ (±0.2 °2θ; ±0.1 °2θ; or ±0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 16.4 °2θ, 25.7 °2θ, 22.4 °2θ, 16.9 °2θ, 19.4 °2θ, 18.2 °2θ, and 27.0 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by two or more, or three or more XRPD signals selected from the group consisting of 16.4 °2θ, 25.7 °2θ, 22.4 °2θ, 16.9 °2θ, 19.4 °2θ, 18.2 °2θ, 27.0 °2θ, 20.4 °2θ, 25.4 °2θ, and 9.2 °2θ (±0.2 °2θ; ±0.1 °2θ; or ±0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 16.4 °2θ, 25.7 °2θ, 22.4 °2θ, 16.9 °2θ, 19.4 °2θ, 18.2 °2θ, 27.0 °2θ, 20.4 °2θ, 25.4 °2θ, and 9.2 °2θ (±0.2 °2θ; ±0.1 °2θ; or ±0.0 °2θ; Cu Kα1 radiation).

In some embodiments, the crystalline tabernanthalog monofumarate (Pattern #1) is characterized by one, two, three, four, five, six, seven, eight, nine, ten, eleven, twelve, thirteen, fourteen, fifteen, sixteen, or seventeen XRPD signals selected from those set forth in Table 23.

In some embodiments, the solid form of tabernanthalog fumarate salt is crystalline tabernanthalog fumarate salt characterized by two or more, or three or more XRPD signals selected from the group consisting of 25.6 °2θ, 16.3 °2θ, and 19.3 °2θ (±0.2 °2θ; ±0.1 °2θ; or ±0.0 °2θ; Cu Kα1 radiation). In some embodiments, the solid form of tabernanthalog fumarate salt is crystalline tabernanthalog fumarate salt characterized by XRPD signals at 25.6 °2θ, 16.3 °2θ, and 19.3 °2θ (±0.2 °2θ; ±0.1 °2θ; or 0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting of 25.6 °2θ, 16.3 °2θ, 19.3 °2θ, 16.7 °2θ, and 18.1 °2θ (±0.2 °2θ; ±0.1 °2θ; or 0.0 °2θ; Cu Kα1 radiation). In some embodiments, the solid form of tabernanthalog fumarate salt is crystalline tabernanthalog fumarate salt characterized by XRPD signals at 25.6 °2θ, 16.3 °2θ, 19.3 °2θ, 16.7 °2θ, and 18.1 °2θ (±0.2 °2θ; ±0.1 °2θ; or 0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting 25.6 °2θ, 16.3 °2θ, 19.3 °2θ, 16.7 °2θ, 18.1 °2θ, 9.1 °2θ, and 22.3 °2θ (±0.2 °2θ; ±0.1 °2θ; or 0.0 °2θ; Cu Kα1 radiation). In some embodiments, the solid form of tabernanthalog fumarate salt is crystalline tabernanthalog fumarate salt characterized by XRPD signals at 25.6 °2θ, 16.3 °2θ, 19.3 °2θ, 16.7 °2θ, 18.1 °2θ, 9.1 °2θ, and 22.3 °2θ (±0.2 °2θ; ±0.1 °2θ; or 0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting of 25.6 °2θ, 16.3 °2θ, 19.3 °2θ, 16.7 °2θ, 18.1 °2θ, 9.1 °2θ, 22.3 °2θ, 27.3 °2θ, 26.8 °2θ, and 26.2 °2θ (±0.2 °2θ; ±0.1 °2θ; or 0.0 °2θ; Cu Kα1 radiation). In some embodiments, the solid form of tabernanthalog fumarate salt is crystalline tabernanthalog fumarate salt characterized by XRPD signals at 25.6 °2θ, 16.3 °2θ, 19.3 °2θ, 16.7 °2θ, 18.1 °2θ, 9.1 °2θ, 22.3 °2θ, 27.3 °2θ, 26.8 °2θ, and 26.2 °2θ (±0.2 °2θ; ±0.1 °2θ; or ±0.0 °2θ; Cu Kα1 radiation).

In some embodiments, the crystalline tabernanthalog fumarate salt is characterized by one, two, three, four, five, six, seven, eight, nine, ten, eleven, twelve, thirteen, fourteen, fifteen, sixteen, seventeen, or eighteen XRPD signals selected from those set forth in Table 24.

In some embodiments, the solid form of tabernanthalog fumarate salt is crystalline tabernanthalog fumarate salt characterized by two or more, or three or more XRPD signals selected from the group consisting of 25.5 °2θ, 16.3 °2θ, and 19.3 °2θ (±0.2 °2θ; ±0.1 °2θ; or 0.0 °2θ; Cu Kα1 radiation). In some embodiments, the solid form of tabernanthalog fumarate salt is crystalline tabernanthalog fumarate salt characterized by XRPD signals at 25.5 °2θ, 16.3 °2θ, and 19.3 °2θ (±0.2 °2θ; ±0.1 °2θ; or 0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting 25.5 °2θ, 16.3 °2θ, 19.3 °2θ, 16.6 °2θ, and 22.3 °2θ (±0.2 °2θ; ±0.1 °2θ; or 0.0 °2θ; Cu Kα1 radiation). In some embodiments, the solid form of tabernanthalog fumarate salt is crystalline tabernanthalog fumarate salt characterized by XRPD signals at 25.5 °2θ, 16.3 °2θ, 19.3 °2θ, 16.6 °2θ, and 22.3 °2θ (±0.2 °2θ; ±0.1 °2θ; or 0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting 25.5 °2θ, 16.3 °2θ, 19.3 °2θ, 16.6 °2θ, 22.3 °2θ, 27.2 °2θ, and 18.1 °2θ(±0.2 °2θ; ±0.1 °2θ; or 0.0 °2θ; Cu Kα1 radiation). In some embodiments, the solid form of tabernanthalog fumarate salt is crystalline tabernanthalog fumarate salt characterized by XRPD signals at 25.5 °2θ, 16.3 °2θ, 19.3 °2θ, 16.6 °2θ, 22.3 °2θ, 27.2 °2θ, and 18.1 °2θ (±0.2 °2θ; ±0.1 °2θ; or ±0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting of 25.5 °2θ, 16.3 °2θ, 19.3 °2θ, 16.6 °2θ, 22.3 °2θ, 27.2 °2θ, and 18.1 °2θ, 26.8 °2θ, 25.1 °2θ, and 26.1 °2θ (±0.2 °2θ; ±0.1 °2θ; or 0.0 °2θ; Cu Kα1 radiation). In some embodiments, the solid form of tabernanthalog fumarate salt is crystalline tabernanthalog fumarate salt characterized by XRPD signals at 25.5 °2θ, 16.3 °2θ, 19.3 °2θ, 16.6 °2θ, 22.3 °2θ, 27.2 °2θ, and 18.1 °2θ, 26.8 °2θ, 25.1 °2θ, and 26.1 °2θ (±0.2 °2θ; ±0.1 °2θ; or 0.0 °2θ; Cu Kα1 radiation).

In some embodiments, the crystalline tabernanthalog fumarate salt is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 25.

In some embodiments, the solid form of tabernanthalog fumarate salt is crystalline tabernanthalog fumarate salt characterized by two or more, or three or more XRPD signals selected from the group consisting of 25.6 °2θ, 16.4 °2θ, and 19.4 °2θ (±0.2 °2θ; ±0.1 °2θ; or 0.0 °2θ; Cu Kα1 radiation). In some embodiments, the solid form of tabernanthalog fumarate salt is crystalline tabernanthalog fumarate salt characterized by XRPD signals at 25.6 °2θ, 16.4 °2θ, and 19.4 °2θ (±0.2 °2θ; ±0.1 °2θ; or 0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting of 25.6 °2θ, 16.4 °2θ, 19.4 °2θ, 16.8 °2θ, and 9.1 °2θ (±0.2 °2θ; ±0.1 °2θ; or ±0.0 °2θ; Cu Kα1 radiation). In some embodiments, the solid form of tabernanthalog fumarate salt is crystalline tabernanthalog fumarate salt characterized by XRPD signals at 25.6 °2θ, 16.4 °2θ, 19.4 °2θ, 16.8 °2θ, and 9.1 °2θ (±0.2 °2θ; ±0.1 °2θ; or 0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting of 25.6 °2θ, 16.4 °2θ, 19.4 °2θ, 16.8 °2θ, 9.1 °2θ, 18.2 °2θ, and 22.4 °2θ (±0.2 °2θ; ±0.1 °2θ; or ±0.0 °2θ; Cu Kα1 radiation). In some embodiments, the solid form of tabernanthalog fumarate salt is crystalline tabernanthalog fumarate salt characterized by XRPD signals at 25.6 °2θ, 16.4 °2θ, 19.4 °2θ, 16.8 °2θ, 9.1 °2θ, 18.2 °2θ, and 22.4 °2θ (±0.2 °2θ; ±0.1 °2θ; or ±0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting of 25.6 °2θ, 16.4 °2θ, 19.4 °2θ, 16.8 °2θ, 9.1 °2θ, 18.2 °2θ, 22.4 °2θ, 27.3 °2θ, 26.9 °2θ, and 25.3 °2θ (±0.2 °2θ; ±0.1 °2θ; or ±0.0 °2θ; Cu Kα1 radiation). In some embodiments, the solid form of tabernanthalog fumarate salt is crystalline tabernanthalog fumarate salt characterized by XRPD signals at 25.6 °2θ, 16.4 °2θ, 19.4 °2θ, 16.8 °2θ, 9.1 °2θ, 18.2 °2θ, 22.4 °2θ, 27.3 °2θ, 26.9 °2θ, and 25.3 °2θ (±0.2 °2θ; ±0.1 °2θ; or 0.0 °2θ; Cu Kα1 radiation).

In some embodiments, the crystalline tabernanthalog fumarate salt is characterized by one, two, three, four, five, six, seven, eight, nine, ten, eleven, twelve, thirteen, fourteen, fifteen, sixteen, seventeen, eighteen, nineteen, twenty, twenty-one, or twenty-two XRPD signals selected from those set forth in Table 26.

In some embodiments, the solid form of tabernanthalog fumarate salt is crystalline tabernanthalog fumarate salt characterized by two or more, or three or more XRPD signals selected from the group consisting of 25.5 °2θ, 16.3 °2θ, and 19.3 °2θ (±0.2 °2θ; ±0.1 °2θ; or ±0.0 °2θ; Cu Kα1 radiation). In some embodiments, the solid form of tabernanthalog fumarate salt is crystalline tabernanthalog fumarate salt characterized by XRPD signals at 25.5 °2θ, 16.3 °2θ, and 19.3 °2θ (±0.2 °2θ; ±0.1 °2θ; or 0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting of 25.5 °2θ, 16.3 °2θ, 19.3 °2θ, 16.7 °2θ, and 22.3 °2θ (±0.2 °2θ; ±0.1 °2θ; or ±0.0 °2θ; Cu Kα1 radiation). In some embodiments, the solid form of tabernanthalog fumarate salt is crystalline tabernanthalog fumarate salt characterized by XRPD signals at 25.5 °2θ, 16.3 °2θ, 19.3 °2θ, 16.7 °2θ, and 22.3 °2θ (±0.2 °2θ; ±0.1 °2θ; or 0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting of 25.5 °2θ, 16.3 °2θ, 19.3 °2θ, 16.7 °2θ, 22.3 °2θ, 27.2 °2θ, and 9.1 °2θ (±0.2 °2θ; ±0.1 °2θ; or 0.0 °2θ; Cu Kα1 radiation). In some embodiments, the solid form of tabernanthalog fumarate salt is crystalline tabernanthalog fumarate salt characterized by XRPD signals at 25.5 °2θ, 16.3 °2θ, 19.3 °2θ, 16.7 °2θ, 22.3 °2θ, 27.2 °2θ, and 9.1 °2θ (±0.2 °2θ; ±0.1 °2θ; or 0.0 °2θ; Cu Kα1 radiation).

In some embodiments, the solid form of tabernanthalog fumarate salt is crystalline tabernanthalog fumarate salt characterized by two or more, or three or more XRPD signals selected from the group consisting 25.5 °2θ, 16.3 °2θ, 19.3 °2θ, 16.7 °2θ, 22.3 °2θ, 27.2 °2θ, 9.1 °2θ, 18.1 °2θ, 26.8 °2θ, and 25.2 °2θ (±0.2 °2θ; ±0.1 °2θ; or 0.0 °2θ; Cu Kα1 radiation). In some embodiments, the solid form of tabernanthalog fumarate salt is crystalline tabernanthalog fumarate salt characterized by XRPD signals at 25.5 °2θ, 16.3 °2θ, 19.3 °2θ, 16.7 °2θ, 22.3 °2θ, 27.2 °2θ, 9.1 °2θ, 18.1 °2θ, 26.8 °2θ, and 25.2 °2θ (±0.2 °2θ; ±0.1 °2θ; or ±0.0 °2θ; Cu Kα1 radiation).

In some embodiments, the crystalline tabernanthalog fumarate salt is characterized by one, two, three, four, five, six, seven, eight, nine, ten, eleven, twelve, thirteen, fourteen, fifteen, sixteen, seventeen, eighteen, or nineteen XRPD signals selected from those set forth in Table 27.

In some embodiments, the solid form of tabernanthalog monofumarate salt is crystalline tabernanthalog monofumarate salt (Pattern #1) characterized by two or more, or three or more XRPD signals selected from the group consisting of 25.6 °2θ, 16.0 °2θ, and 18.0 °2θ (±0.2 °2θ; ±0.1 °2θ; or 0.0 °2θ; Cu Kα1 radiation). In some embodiments, the solid form of tabernanthalog monofumarate salt is crystalline tabernanthalog monofumarate salt (Pattern #1) characterized by XRPD signals at 25.6 °2θ, 16.0 °2θ, and 18.0 °2θ (±0.2 °2θ; ±0.1 °2θ; or 0.0 °2θ; Cu Kα1 radiation).

In some embodiments, the solid form of tabernanthalog monofumarate salt is crystalline tabernanthalog monofumarate salt (Pattern #1) characterized by two or more, or three or more XRPD signals selected from the group consisting of 25.6 °2θ, 16.0 °2θ, 18.0 °2θ, 16.3 °2θ, and 21.4 °2θ (±0.2 °2θ; ±0.1 °2θ; or ±0.0 °2θ; Cu Kα1 radiation). In some embodiments, the solid form of tabernanthalog monofumarate salt is crystalline tabernanthalog monofumarate salt (Pattern #1) characterized by XRPD signals at 25.6 °2θ, 16.0 °2θ, 18.0 °2θ, 16.3 °2θ, and 21.4 °2θ (±0.2 °2θ; ±0.1 °2θ; or 0.0 °2θ; Cu Kα1 radiation).

In some embodiments, the solid form of tabernanthalog monofumarate salt is crystalline tabernanthalog monofumarate salt (Pattern #1) characterized by two or more, or three or more XRPD signals selected from the group consisting of 25.6 °2θ, 16.0 °2θ, 18.0 °2θ, 16.3 °2θ, 21.4 °2θ, 26.8 °2θ, and 23.0 °2θ (±0.2 °2θ; ±0.1 °2θ; or 0.0 °2θ; Cu Kα1 radiation). In some embodiments, the solid form of tabernanthalog monofumarate salt is crystalline tabernanthalog monofumarate salt (Pattern #1) characterized by XRPD signals at 25.6 °2θ, 16.0 °2θ, 18.0 °2θ, 16.3 °2θ, 21.4 °2θ, 26.8 °2θ, and 23.0 °2θ (±0.2 °2θ; ±0.1 °2θ; or 0.0 °2θ; Cu Kα1 radiation).

In some embodiments, the solid form of tabernanthalog monofumarate salt is crystalline tabernanthalog monofumarate salt (Pattern #1) characterized by two or more, or three or more XRPD signals selected from the group consisting of 25.6 °2θ, 16.0 °2θ, 18.0 °2θ, 16.3 °2θ, 21.4 °2θ, 26.8 °2θ, 23.0 °2θ, 25.9 °2θ, 15.5 °2θ, and 11.0 °2θ (±0.2 °2θ; ±0.1 °2θ; or 0.0 °2θ; Cu Kα1 radiation). In some embodiments, the solid form of tabernanthalog monofumarate salt is crystalline tabernanthalog monofumarate salt (Pattern #1) characterized by XRPD signals at 25.6 °2θ, 16.0 °2θ, 18.0 °2θ, 16.3 °2θ, 21.4 °2θ, 26.8 °2θ, 23.0 °2θ, 25.9 °2θ, 15.5 °2θ, and 11.0 °2θ (±0.2 °2θ; ±0.1 °2θ; or 0.0 °2θ; Cu Kα1 radiation).

In some embodiments, the crystalline tabernanthalog monofumarate salt (Pattern #1) is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 29.

In some embodiments, the solid form of tabernanthalog fumarate is crystalline tabernanthalog fumarate characterized by two or more, or three or more XRPD signals selected from the group consisting of 25.6 °2θ, 16.4 °2θ, and 19.3 °2θ (±0.2 °2θ; ±0.1 °2θ; or ±0.0 °2θ; Cu Kα1 radiation). In some embodiments, the solid form of tabernanthalog fumarate is crystalline tabernanthalog fumarate characterized by XRPD signals 25.6 °2θ, 16.4 °2θ, and 19.3 °2θ (±0.2 °2θ; ±0.1 °2θ; or ±0.0 °2θ; Cu Kα1 radiation).

In some embodiments, the solid form of tabernanthalog fumarate is crystalline tabernanthalog fumarate characterized by two or more, or three or more XRPD signals selected from the group consisting of 25.6 °2θ, 16.4 °2θ, 19.3 °2θ, 16.7 °2θ, and 9.1 °2θ (±0.2 °2θ; ±0.1 °2θ; or 0.0 °2θ; Cu Kα1 radiation). In some embodiments, the solid form of tabernanthalog fumarate is crystalline tabernanthalog fumarate characterized by XRPD signals at 25.6 °2θ, 16.4 °2θ, 19.3 °2θ, 16.7 °2θ, and 9.1 °2θ (±0.2 °2θ; ±0.1 °2θ; or ±0.0 °2θ; Cu Kα1 radiation).

In some embodiments, the solid form of tabernanthalog fumarate is crystalline tabernanthalog fumarate characterized by two or more, or three or more XRPD signals selected from the group consisting of 25.6 °2θ, 16.4 °2θ, 19.3 °2θ, 16.7 °2θ, 9.1 °2θ, 18.1 °2θ, and 22.4 °2θ (±0.2 °2θ; ±0.1 °2θ; or 0.0 °2θ; Cu Kα1 radiation). In some embodiments, the solid form of tabernanthalog fumarate is crystalline tabernanthalog fumarate characterized by XRPD signals at 25.6 °2θ, 16.4 °2θ, 19.3 °2θ, 16.7 °2θ, 9.1 °2θ, 18.1 °2θ, and 22.4 °2θ (±0.2 °2θ; ±0.1 °2θ; or 0.0 °2θ; Cu Kα1 radiation).

In some embodiments, the solid form of tabernanthalog fumarate is crystalline tabernanthalog fumarate characterized by two or more, or three or more XRPD signals selected from the group consisting of 25.6 °2θ, 16.4 °2θ, 19.3 °2θ, 16.7 °2θ, 9.1 °2θ, 18.1 °2θ, 22.4 °2θ, 27.3 °2θ, 26.8 °2θ, and 25.2 °2θ (±0.2 °2θ; ±0.1 °2θ; or 0.0 °2θ; Cu Kα1 radiation). In some embodiments, the solid form of tabernanthalog fumarate is crystalline tabernanthalog fumarate characterized by XRPD signals at 25.6 °2θ, 16.4 °2θ, 19.3 °2θ, 16.7 °2θ, 9.1 °2θ, 18.1 °2θ, 22.4 °2θ, 27.3 °2θ, 26.8 °2θ, and 25.2 °2θ (±0.2 °2θ; ±0.1 °2θ; or ±0.0 °2θ; Cu Kα1 radiation).

In some embodiments, the crystalline tabernanthalog fumarate is characterized by one, two, three, four, five, six, seven, eight, nine, ten, eleven, twelve, thirteen, fourteen, fifteen, sixteen, seventeen, eighteen, nineteen, twenty, twenty-one, or twenty-two XRPD signals selected from those set forth in Table 30.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 16.5 °2θ, and 20.6 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #6a characterized by XRPD signals at 19.5 °2θ, 16.5 °2θ, and 20.6 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #6a characterized by two or more, or three or more XRPD signals selected from the group consisting of 19.5 °2θ, 16.5 °2θ, 20.6 °2θ, 25.3 °2θ, and 26.1 °2θ (±0.2 °2θ; ±0.1 °2θ; or 0.0 °2θ; Cu Kα1 radiation). In some embodiments, the solid form of tabernanthalog monofumarate (Pattern #6a) is crystalline tabernanthalog monofumarate pattern #6a characterized by XRPD signals at 19.5 °2θ, 16.5 °2θ, 20.6 °2θ, 25.3 °2θ, and 26.1 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate pattern #6a characterized by two or more, or three or more XRPD signals selected from the group consisting of 19.5 °2θ, 16.5 °2θ, 20.6 °2θ, 25.3 °2θ, 26.1 °2θ, 22.0 °2θ, and 33.5 °2θ (±0.2 °2θ; ±0.1 °2θ; or ±0.0 °2θ; Cu Kα1 radiation). In some embodiments, the solid form of tabernanthalog monofumarate (Pattern #6a) is crystalline tabernanthalog monofumarate pattern #6a characterized by XRPD signals at 19.5 °2θ, 16.5 °2θ, 20.6 °2θ, 25.3 °2θ, 26.1 °2θ, 22.0 °2θ, and 33.5 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate pattern #6a characterized by two or more, or three or more XRPD signals selected from the group consisting of 19.5 °2θ, 16.5 °2θ, 20.6 °2θ, 25.3 °2θ, 26.1 °2θ, 22.0 °2θ, 33.5 °2θ, 12.9 °2θ, and 37.8 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, 20.6 °2θ, 25.3 °2θ, 26.1 °2θ, 22.0 °2θ, 33.5 °2θ, 12.9 °2θ, and 37.8 °2θ (±0.2 °2θ; ±0.1 °2θ; or ±0.0 °2θ; Cu Kα1 radiation).

In some embodiments, the crystalline tabernanthalog monofumarate pattern #6a is characterized by one, two, three, four, five, six, seven, eight, or nine XRPD signals selected from those set forth in Table 31.

In some embodiments, the solid form of Tabernanthalog·0.5Fumarate is crystalline Tabernanthalog·0.5Fumarate characterized by two or more, or three or more XRPD signals selected from the group consisting of 17.0 °2θ, 11.3 °2θ, and 20.2 (±0.2 °2θ; ±0.1 °2θ; or ±0.0 °2θ; Cu Kα1 radiation). In some embodiments, the solid form of Tabernanthalog·0.5Fumarate is crystalline Tabernanthalog·0.5Fumarate characterized by XRPD signals at 17.0 °2θ, 11.3 °2θ, and 20.2 °2θ (±0.2 °2θ; 0.1 °2θ; or ±0.0 °2θ; Cu Kα1 radiation).

In some embodiments, the solid form of Tabernanthalog·0.5Fumarate is crystalline Tabernanthalog·0.5Fumarate characterized by two or more, or three or more XRPD signals selected from the group consisting of 17.0 °2θ, 11.3 °2θ, 20.2 °2θ, 23.6 °2θ, and 21.4 °2θ (±0.2 °2θ; ±0.1 °2θ; or 0.0 °2θ; Cu Kα1 radiation). In some embodiments, the solid form of Tabernanthalog·0.5Fumarate is crystalline Tabernanthalog·0.5Fumarate characterized by XRPD signals at 17.0 °2θ, 11.3 °2θ, 20.2 °2θ, 23.6 °2θ, and 21.4 °2θ (±0.2 °2θ; ±0.1 °2θ; or ±0.0 °2θ; Cu Kα1 radiation).

In some embodiments, the solid form of Tabernanthalog·0.5Fumarate is crystalline Tabernanthalog·0.5Fumarate characterized by two or more, or three or more XRPD signals selected from the group consisting of 17.0 °2θ, 11.3 °2θ, 20.2 °2θ, 23.6 °2θ, 21.4 °2θ, 15.5 °2θ, and 22.6 °2θ (±0.2 °2θ; ±0.1 °2θ; or ±0.0 °2θ; Cu Kα1 radiation). In some embodiments, the solid form of Tabernanthalog·0.5Fumarate is crystalline Tabernanthalog·0.5Fumarate characterized by XRPD signals at 17.0 °2θ, 11.3 °2θ, 20.2 °2θ, 23.6 °2θ, 21.4 °2θ, 15.5 °2θ, and 22.6 °2θ (±0.2 °2θ; ±0.1 °2θ; or 0.0 °2θ; Cu Kα1 radiation).

In some embodiments, the solid form of Tabernanthalog·0.5Fumarate is crystalline Tabernanthalog·0.5Fumarate characterized by two or more, or three or more XRPD signals selected from the group consisting of 17.0 °2θ, 11.3 °2θ, 20.2 °2θ, 23.6 °2θ, 21.4 °2θ, 15.5 °2θ, 22.6 °2θ, 8.2 °2θ, 24.2 °2θ, and 24.7 °2θ (±0.2 °2θ; ±0.1 °2θ; or ±0.0 °2θ; Cu Kα1 radiation). In some embodiments, the solid form of Tabernanthalog·0.5Fumarate is crystalline Tabernanthalog·0.5Fumarate characterized by XRPD signals at 17.0 °2θ, 11.3 °2θ, 20.2 °2θ, 23.6 °2θ, 21.4 °2θ, 15.5 °2θ, 22.6 °2θ, 8.2 °2θ, 24.2 °2θ, and 24.7 °2θ (±0.2 °2θ; ±0.1 °2θ; or 0.0 °2θ; Cu Kα1 radiation).

In some embodiments, the crystalline Tabernanthalog·0.5Fumarate is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 32.

In some embodiments, the solid form of Tabernanthalog·0.5Fumarate is crystalline Tabernanthalog·0.5Fumarate Pattern #14 characterized by two or more, or three or more XRPD signals selected from the group consisting of 8.2 °2θ, 15.5 °2θ, and 17.0 °2θ (±0.2 °2θ; ±0.1 °2θ; or ±0.0 °2θ; Cu Kα1 radiation). In some embodiments, the solid form of Tabernanthalog·0.5Fumarate is crystalline Tabernanthalog·0.5Fumarate Pattern #14 characterized by XRPD signals at 8.2 °2θ, 15.5 °2θ, and 17.0 °2θ (±0.2 °2θ; ±0.1 °2θ; or 0.0 °2θ; Cu Kα1 radiation).

In some embodiments, the solid form of Tabernanthalog·0.5Fumarate is crystalline Tabernanthalog·0.5Fumarate Pattern #14 characterized by two or more, or three or more XRPD signals selected from the group consisting of 8.2 °2θ, 15.5 °2θ, 17.0 °2θ, 22.6 °2θ, and 20.2 °2θ (±0.2 °2θ; ±0.1 °2θ; or 0.0 °2θ; Cu Kα1 radiation). In some embodiments, the solid form of Tabernanthalog·0.5Fumarate is crystalline Tabernanthalog·0.5Fumarate Pattern #14 characterized by XRPD signals at 8.2 °2θ, 15.5 °2θ, 17.0 °2θ, 22.6 °2θ, and 20.2 °2θ (±0.2 °2θ; ±0.1 °2θ; or ±0.0 °2θ; Cu Kα1 radiation).

In some embodiments, the solid form of Tabernanthalog·0.5Fumarate is crystalline Tabernanthalog·0.5Fumarate Pattern #14 characterized by two or more, or three or more XRPD signals selected from the group consisting of 8.2 °2θ, 15.5 °2θ, 17.0 °2θ, 22.6 °2θ, 20.2 °2θ, 11.2 °2θ, and 23.7 °2θ (±0.2 °2θ; ±0.1 °2θ; or ±0.0 °2θ; Cu Kα1 radiation). In some embodiments, the solid form of Tabernanthalog·0.5Fumarate is crystalline Tabernanthalog·0.5Fumarate Pattern #14 characterized by XRPD signals at 8.2 °2θ, 15.5 °2θ, 17.0 °2θ, 22.6 °2θ, 20.2 °2θ, 11.2 °2θ, and 23.7 °2θ (±0.2 °2θ; ±0.1 °2θ; or 0.0 °2θ; Cu Kα1 radiation).

In some embodiments, the solid form of Tabernanthalog·0.5Fumarate is crystalline Tabernanthalog·0.5Fumarate Pattern #14 characterized by two or more, or three or more XRPD signals selected from the group consisting of 8.2 °2θ, 15.5 °2θ, 17.0 °2θ, 22.6 °2θ, 20.2 °2θ, 11.2 °2θ, 23.7 °2θ, 24.8 °2θ, 21.5 °2θ, and 18.1 °2θ (±0.2 °2θ; ±0.1 °2θ; or ±0.0 °2θ; Cu Kα1 radiation). In some embodiments, the solid form of Tabernanthalog·0.5Fumarate is crystalline Tabernanthalog·0.5Fumarate Pattern #14 characterized by XRPD signals at 8.2 °2θ, 15.5 °2θ, 17.0 °2θ, 22.6 °2θ, 20.2 °2θ, 11.2 °2θ, 23.7 °2θ, 24.8 °2θ, 21.5 °2θ, and 18.1 °2θ (±0.2 °2θ; ±0.1 °2θ; or ±0.0 °2θ; Cu Kα1 radiation).

In some embodiments, the crystalline Tabernanthalog·0.5Fumarate Pattern #14 is characterized by one, two, three, four, five, six, seven, eight, nine, ten, eleven, twelve, thirteen, fourteen, fifteen, or sixteen XRPD signals selected from those set forth in Table 32A.

In some embodiments, the solid form of tabernanthalog hemifumarate (Pattern #14) is crystalline tabernanthalog hemifumarate (Pattern #5) characterized by two or more, or three or more XRPD signals selected from the group consisting of 11.3 °2θ, 8.2 °2θ, and 17.1 °2θ (±0.2 °2θ; ±0.1 °2θ; or ±0.0 °2θ; Cu Kα1 radiation).

In some embodiments, the solid form of tabernanthalog hemifumarate (Pattern #14) is crystalline tabernanthalog hemifumarate (Pattern #5) characterized by XRPD signals at 11.3 °2θ, 8.2 °2θ, and 17.1 °2θ (±0.2 °2θ; ±0.1 °2θ; or ±0.0 °2θ; Cu Kα1 radiation).

In some embodiments, the solid form of tabernanthalog hemifumarate (Pattern #14) is crystalline tabernanthalog hemifumarate (Pattern #5) characterized by XRPD signals at 11.3 °2θ, 8.2 °2θ, 17.1 °2θ, 21.5 °2θ, and 23.7 °2θ (±0.2 °2θ; ±0.1 °2θ; or 0.0 °2θ; Cu Kα1 radiation).

In some embodiments, the solid form of tabernanthalog hemifumarate (Pattern #14) is crystalline tabernanthalog hemifumarate (Pattern #5) characterized by XRPD signals at 11.3 °2θ, 8.2 °2θ, 17.1 °2θ, 21.5 °2θ, 23.7 °2θ, 22.7 °2θ, and 20.3 °2θ (±0.2 °2θ; ±0.1 °2θ; or 0.0 °2θ; Cu Kα1 radiation).

In some embodiments, the solid form of tabernanthalog hemifumarate (Pattern #14) is crystalline tabernanthalog hemifumarate (Pattern #5) characterized by XRPD signals at 11.3 °2θ, 8.2 °2θ, 17.1 °2θ, 21.5 °2θ, 23.7 °2θ, 22.7 °2θ, 20.3 °2θ, 25.5 °2θ, 15.6 °2θ, and 16.3 °2θ (±0.2 °2θ; ±0.1 °2θ; or ±0.0 °2θ; Cu Kα1 radiation).

In some embodiments, the crystalline tabernanthalog hemifumarate (Pattern #14) is characterized by one, two, three, four, five, six, seven, eight, nine, ten, eleven, twelve, thirteen, fourteen, or fifteen XRPD signals selected from those set forth in Table 123.

In some embodiments, the solid form of tabernanthalog fumarate is crystalline tabernanthalog fumarate characterized by two or more, or three or more XRPD signals selected from the group consisting of 4.3 °2θ, 17.5 °2θ, and 19.3 °2θ (±0.2 °2θ; ±0.1 °2θ; or ±0.0 °2θ; Cu Kα1 radiation). In some embodiments, the solid form of tabernanthalog fumarate is crystalline tabernanthalog fumarate characterized by XRPD signals at 4.3 °2θ, 17.5 °2θ, and 19.3 °2θ (±0.2 °2θ; ±0.1 °2θ; or 0.0 °2θ; Cu Kα1 radiation).

In some embodiments, the solid form of tabernanthalog fumarate is crystalline tabernanthalog fumarate characterized by two or more, or three or more XRPD signals selected from the group consisting of 4.3 °2θ, 17.5 °2θ, 19.3 °2θ, 20.1 °2θ, and 14.5 °2θ (±0.2 °2θ; ±0.1 °2θ; or ±0.0 °2θ; Cu Kα1 radiation). In some embodiments, the solid form of tabernanthalog fumarate is crystalline tabernanthalog fumarate characterized by XRPD signals 4.3 °2θ, 17.5 °2θ, 19.3 °2θ, 20.1 °2θ, and 14.5 °2θ (±0.2 °2θ; ±0.1 °2θ; or 0.0 °2θ; Cu Kα1 radiation).

In some embodiments, the solid form of tabernanthalog fumarate is crystalline tabernanthalog fumarate characterized by two or more, or three or more XRPD signals selected from the group consisting of 4.3 °2θ, 17.5 °2θ, 19.3 °2θ, 20.1 °2θ, 14.5 °2θ, 21.0 °2θ, and 23.7 °2θ (±0.2 °2θ; ±0.1 °2θ; or 0.0 °2θ; Cu Kα1 radiation). In some embodiments, the solid form of tabernanthalog fumarate is crystalline tabernanthalog fumarate characterized by XRPD signals at 4.3 °2θ, 17.5 °2θ, 19.3 °2θ, 20.1 °2θ, 14.5 °2θ, 21.0 °2θ, and 23.7 °2θ (±0.2 °2θ; ±0.1 °2θ; or 0.0 °2θ; Cu Kα1 radiation).

In some embodiments, the solid form of tabernanthalog fumarate is crystalline tabernanthalog fumarate characterized by two or more, or three or more XRPD signals selected from the group consisting of 4.3 °2θ, 17.5 °2θ, 19.3 °2θ, 20.1 °2θ, 14.5 °2θ, 21.0 °2θ, 23.7 °2θ, 18.7 °2θ, 23.3 °2θ, and 31.8 °2θ (±0.2 °2θ; ±0.1 °2θ; or 0.0 °2θ; Cu Kα1 radiation). In some embodiments, the solid form of tabernanthalog fumarate is crystalline tabernanthalog fumarate characterized by XRPD signals at 4.3 °2θ, 17.5 °2θ, 19.3 °2θ, 20.1 °2θ, 14.5 °2θ, 21.0 °2θ, 23.7 °2θ, 18.7 °2θ, 23.3 °2θ, and 31.8 °2θ (±0.2 °2θ; ±0.1 °2θ; or 0.0 °2θ; Cu Kα1 radiation).

In some embodiments, the crystalline tabernanthalog fumarate is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, or twenty-eight XRPD signals selected from those set forth in Table 33.

In some embodiments, the solid form of Tabernanthalog·0.5Fumarate is crystalline Tabernanthalog·0.5Fumarate characterized by two or more, or three or more XRPD signals selected from the group consisting of 16.9 °2θ, 25.4 °2θ, and 22.7 °2θ (±0.2 °2θ; ±0.1 °2θ; or 0.0 °2θ; Cu Kα1 radiation). In some embodiments, the solid form of Tabernanthalog·0.5Fumarate is crystalline Tabernanthalog·0.5Fumarate characterized by XRPD signals at 16.9 °2θ, 25.4 °2θ, and 22.7 °2θ (±0.2 °2θ; ±0.1 °2θ; or 0.0 °2θ; Cu Kα1 radiation).

In some embodiments, the solid form of Tabernanthalog·0.5Fumarate is crystalline Tabernanthalog·0.5Fumarate characterized by two or more, or three or more XRPD signals selected from the group consisting of 16.9 °2θ, 25.4 °2θ, 22.7 °2θ, 27.2 °2θ, and 20.5 °2θ (±0.2 °2θ; ±0.1 °2θ; or 0.0 °2θ; Cu Kα1 radiation). In some embodiments, the solid form of Tabernanthalog·0.5Fumarate is crystalline Tabernanthalog·0.5Fumarate characterized by XRPD signals 16.9 °2θ, 25.4 °2θ, 22.7 °2θ, 27.2 °2θ, and 20.5 °2θ (±0.2 °2θ; ±0.1 °2θ; or ±0.0 °2θ; Cu Kα1 radiation).

In some embodiments, the solid form of Tabernanthalog·0.5Fumarate is crystalline Tabernanthalog·0.5Fumarate characterized by two or more, or three or more XRPD signals selected from the group consisting of 16.9 °2θ, 25.4 °2θ, 22.7 °2θ, 27.2 °2θ, 20.5 °2θ, 16.2 °2θ, and 15.5 °2θ (±0.2 °2θ; ±0.1 °2θ; or 0.0 °2θ; Cu Kα1 radiation). In some embodiments, the solid form of E Tabernanthalog·0.5Fumarate is crystalline Tabernanthalog·0.5Fumarate characterized by XRPD signals 16.9 °2θ, 25.4 °2θ, 22.7 °2θ, 27.2 °2θ, 20.5 °2θ, 16.2 °2θ, and 15.5 °2θ (±0.2 °2θ; ±0.1 °2θ; or ±0.0 °2θ; Cu Kα1 radiation).

In some embodiments, the solid form of Tabernanthalog·0.5Fumarate is crystalline Tabernanthalog·0.5Fumarate characterized by two or more, or three or more XRPD signals selected from the group consisting of 16.9 °2θ, 25.4 °2θ, 22.7 °2θ, 27.2 °2θ, 20.5 °2θ, 16.2 °2θ, 15.5 °2θ, 24.7 °2θ, 20.8 °2θ, and 21.4 °2θ (±0.2 °2θ; ±0.1 °2θ; or ±0.0 °2θ; Cu Kα1 radiation). In some embodiments, the solid form of Tabernanthalog·0.5Fumarate is crystalline Tabernanthalog·0.5Fumarate characterized by XRPD signals at 16.9 °2θ, 25.4 °2θ, 22.7 °2θ, 27.2 °2θ, 20.5 °2θ, 16.2 °2θ, 15.5 °2θ, 24.7 °2θ, 20.8 °2θ, and 21.4 °2θ (±0.2 °2θ; ±0.1 °2θ; or ±0.0 °2θ; Cu Kα1 radiation).

In some embodiments, the crystalline Tabernanthalog·0.5Fumarate is characterized by one, two, three, four, five, six, seven, eight, nine, ten, eleven, twelve, thirteen, fourteen, fifteen, sixteen, or seventeen XRPD signals selected from those set forth in Table 34.

In some embodiments, the solid form of tabernanthalog monofumarate is crystalline tabernanthalog monofumarate pattern #2b characterized by two or more, or three or more XRPD signals selected from the group consisting of 25.5 °2θ, 16.3 °2θ, and 18.0 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #2b characterized by XRPD signals at 25.5 °2θ, 16.3 °2θ, and 18.0 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #2b characterized by two or more, or three or more XRPD signals selected from the group consisting of 25.5 °2θ, 16.3 °2θ, 18.0 °2θ, 9.0 °2θ, and 26.8 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #2b characterized by XRPD signals 25.5 °2θ, 16.3 °2θ, 18.0 °2θ, 9.0 °2θ, and 26.8 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #2b characterized by two or more, or three or more XRPD signals selected from the group consisting of 25.5 °2θ, 16.3 °2θ, 18.0 °2θ, 9.0 °2θ, 26.8 °2θ, 22.5 °2θ, and 22.3 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #2b characterized by XRPD signals 25.5 °2θ, 16.3 °2θ, 18.0 °2θ, 9.0 °2θ, 26.8 °2θ, 22.5 °2θ, and 22.3 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #2b characterized by two or more, or three or more XRPD signals selected from the group consisting of 25.5 °2θ, 16.3 °2θ, 18.0 °2θ, 9.0 °2θ, 26.8 °2θ, 22.5 °2θ, 22.3 °2θ, 25.0 °2θ, 17.4 °2θ, and 24.7 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #2b characterized by XRPD signals at 25.5 °2θ, 16.3 °2θ, 18.0 °2θ, 9.0 °2θ, 26.8 °2θ, 22.5 °2θ, 22.3 °2θ, 25.0 °2θ, 17.4 °2θ, and 24.7 °2θ (±0.2 °2θ; ±0.1 °2θ; or 0.0 °2θ; Cu Kα1 radiation).

In some embodiments, the crystalline tabernanthalog monofumarate pattern #2b is characterized by one, two, three, four, five, six, seven, eight, nine, ten, eleven, twelve, or thirteen XRPD signals selected from those set forth in Table 37.

In some embodiments, the solid form of tabernanthalog monofumarate is crystalline tabernanthalog monofumarate pattern #1 characterized by two or more, or three or more XRPD signals selected from the group consisting of 25.6 °2θ, 16.4 °2θ, and 19.4 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals at 25.6 °2θ, 16.4 °2θ, and 19.4 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.6 °2θ, 16.4 °2θ, 19.4 °2θ, 16.8 °2θ, and 9.1 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #1 characterized by XRPD signals 25.6 °2θ, 16.4 °2θ, 19.4 °2θ, 16.8 °2θ, and 9.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.6 °2θ, 16.4 °2θ, 19.4 °2θ, 16.8 °2θ, 9.1 °2θ, 18.2 °2θ, and 22.4 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals of 25.6 °2θ, 16.4 °2θ, 19.4 °2θ, 16.8 °2θ, 9.1 °2θ, 18.2 °2θ, and 22.4 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.6 °2θ, 16.4 °2θ, 19.4 °2θ, 16.8 °2θ, 9.1 °2θ, 18.2 °2θ, 22.4 °2θ, 27.3 °2θ, 25.3 °2θ, and 6.8 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by XRPD signals at 25.6 °2θ, 16.4 °2θ, 19.4 °2θ, 16.8 °2θ, 9.1 °2θ, 18.2 °2θ, 22.4 °2θ, 27.3 °2θ, 25.3 °2θ, and 6.8 °2θ (±0.2 °2θ; ±0.1 °2θ; or 0.0 °2θ; Cu Kα1 radiation).

In some embodiments, the crystalline tabernanthalog monofumarate pattern #1 is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 38.

In some embodiments, the solid form of tabernanthalog monofumarate is crystalline tabernanthalog monofumarate pattern #1 characterized by two or more, or three or more XRPD signals selected from the group consisting of 25.5 °2θ, 16.3 °2θ, and 19.3 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals at 25.5 °2θ, 16.3 °2θ, and 19.3 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.5 °2θ, 16.3 °2θ, 19.3 °2θ, 16.7 °2θ, and 18.1 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals 25.5 °2θ, 16.3 °2θ, 19.3 °2θ, 16.7 °2θ, and 18.1 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.5 °2θ, 16.3 °2θ, 19.3 °2θ, 16.7 °2θ, 18.1 °2θ, 22.3 °2θ, and 27.2 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals of 25.5 °2θ, 16.3 °2θ, 19.3 °2θ, 16.7 °2θ, 18.1 °2θ, 22.3 °2θ, and 27.2 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.5 °2θ, 16.3 °2θ, 19.3 °2θ, 16.7 °2θ, 18.1 °2θ, 22.3 °2θ, 27.2 °2θ, 9.1 °2θ, 17.8 °2θ, and 26.8 °2θ (±0.2 °2θ; 0.1 °2θ; or 0.0 °2θ; Cu Kα1 radiation).

In some embodiments, the solid form of tabernanthalog monofumarate is crystalline tabernanthalog monofumarate pattern #1 characterized by XRPD signals at 25.5 °2θ, 16.3 °2θ, 19.3 °2θ, 16.7 °2θ, 18.1 °2θ, 22.3 °2θ, 27.2 °2θ, 9.1 °2θ, 17.8 °2θ, and 26.8 °2θ (±0.2 °2θ; ±0.1 °2θ; or 0.0 °2θ; Cu Kα1 radiation).

In some embodiments, the crystalline tabernanthalog monofumarate pattern #1 is characterized by one, two, three, four, five, six, seven, eight, nine, ten, eleven, twelve, thirteen, fourteen, fifteen, sixteen, seventeen, or eighteen XRPD signals selected from those set forth in Table 39.

In some embodiments, the solid form of tabernanthalog monofumarate is crystalline tabernanthalog monofumarate pattern #1 characterized by two or more, or three or more XRPD signals selected from the group consisting of 25.7 °2θ, 16.4 °2θ, and 19.4 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals at 25.7 °2θ, 16.4 °2θ, and 19.4 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.7 °2θ, 16.4 °2θ, 19.4 °2θ, 16.9 °2θ, and 18.2 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals 25.7 °2θ, 16.4 °2θ, 19.4 °2θ, 16.9 °2θ, and 18.2 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.7 °2θ, 16.4 °2θ, 19.4 °2θ, 16.9 °2θ, 18.2 °2θ, 22.5 °2θ, and 27.3 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals of 25.7 °2θ, 16.4 °2θ, 19.4 °2θ, 16.9 °2θ, 18.2 °2θ, 22.5 °2θ, and 27.3 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.7 °2θ, 16.4 °2θ, 19.4 °2θ, 16.9 °2θ, 18.2 °2θ, 22.5 °2θ, 27.3 °2θ, 27.0 °2θ, 9.2 °2θ, and 17.9 °2θ (±0.2 °2θ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals at 25.7 °2θ, 16.4 °2θ, 19.4 °2θ, 16.9 °2θ, 18.2 °2θ, 22.5 °2θ, 27.3 °2θ, 27.0 °2θ, 9.2 °2θ, and 17.9 °2θ (±0.2 °2θ; ±0.1 °2θ; or ±0.0 °2θ; Cu Kα1 radiation).

In some embodiments, the crystalline tabernanthalog monofumarate pattern #1 is characterized by one, two, three, four, five, six, seven, eight, nine, ten, eleven, twelve, thirteen, fourteen, fifteen, sixteen, seventeen, or eighteen XRPD signals selected from those set forth in Table 40.

In some embodiments, the solid form of tabernanthalog monofumarate is crystalline tabernanthalog monofumarate pattern #1 characterized by two or more, or three or more XRPD signals selected from the group consisting of 25.6 °2θ, 16.3 °2θ, and 19.3 °2θ (±0.2 °2θ; ±0.1 °2θ; or 0.0 °2θ; Cu Kα1 radiation). In some embodiments, the solid form of tabernanthalog monofumarate pattern #1 is crystalline tabernanthalog monofumarate pattern #1 characterized by XRPD signals at 25.6 °2θ, 16.3 °2θ, and 19.3 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.6 °2θ, 16.3 °2θ, 19.3 °2θ, 16.8 °2θ, and 25.4 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals 25.6 °2θ, 16.3 °2θ, 19.3 °2θ, 16.8 °2θ, and 25.4 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.6 °2θ, 16.3 °2θ, 19.3 °2θ, 16.8 °2θ, 25.4 °2θ, 18.2 °2θ, and 9.1 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #1 characterized by XRPD signals of 25.6 °2θ, 16.3 °2θ, 19.3 °2θ, 16.8 °2θ, 25.4 °2θ, 18.2 °2θ, and 9.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.6 °2θ, 16.3 °2θ, 19.3 °2θ, 16.8 °2θ, 25.4 °2θ, 18.2 °2θ, 9.1 °2θ, 22.3 °2θ, 27.3 °2θ, and 17.8 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by XRPD signals at 25.6 °2θ, 16.3 °2θ, 19.3 °2θ, 16.8 °2θ, 25.4 °2θ, 18.2 °2θ, 9.1 °2θ, 22.3 °2θ, 27.3 °2θ, and 17.8 °2θ (±0.2 °2θ; ±0.1 °2θ; or ±0.0 °2θ; Cu Kα1 radiation).

In some embodiments, the crystalline tabernanthalog monofumarate pattern #1 is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 41.

In some embodiments, the solid form of tabernanthalog monofumarate is crystalline tabernanthalog monofumarate pattern #3 characterized by two or more, or three or more XRPD signals selected from the group consisting of 16.7 °2θ, 16.4 °2θ, and 25.5 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #3 characterized by XRPD signals at 16.7 °2θ, 16.4 °2θ, and 25.5 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #3 characterized by two or more, or three or more XRPD signals selected from the group consisting of 16.7 °2θ, 16.4 °2θ, 25.5 °2θ, 9.1 °2θ, and 20.1 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #3 characterized by XRPD signals 16.7 °2θ, 16.4 °2θ, 25.5 °2θ, 9.1 °2θ, and 20.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #3 characterized by two or more, or three or more XRPD signals selected from the group consisting of 16.7 °2θ, 16.4 °2θ, 25.5 °2θ, 9.1 °2θ, 20.1 °2θ, 17.0 °2θ, and 26.1 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #3 characterized by XRPD signals of 16.7 °2θ, 16.4 °2θ, 25.5 °2θ, 9.1 °2θ, 20.1 °2θ, 17.0 °2θ, and 26.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #3 characterized by two or more, or three or more XRPD signals selected from the group consisting of 16.7 °2θ, 16.4 °2θ, 25.5 °2θ, 9.1 °2θ, 20.1 °2θ, 17.0 °2θ, 26.1 °2θ, 22.4 °2θ, 18.8 °2θ, and 26.8 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #3 characterized by XRPD signals at 16.7 °2θ, 16.4 °2θ, 25.5 °2θ, 9.1 °2θ, 20.1 °2θ, 17.0 °2θ, 26.1 °2θ, 22.4 °2θ, 18.8 °2θ, and 26.8 °2θ (±0.2 °2θ; ±0.1 °2θ; or ±0.0 °2θ; Cu Kα1 radiation).

In some embodiments, the crystalline tabernanthalog monofumarate pattern #3 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four XRPD signals selected from those set forth in Table 42.

In some embodiments, the solid form of tabernanthalog monofumarate is crystalline tabernanthalog monofumarate pattern #3 characterized by two or more, or three or more XRPD signals selected from the group consisting of 25.5 °2θ, 16.3 °2θ, and 16.6 °2θ (±0.2 °2θ; ±0.1 °2θ; or 0.0 °2θ; Cu Kα1 radiation). In some embodiments, the solid form tabernanthalog monofumarate is crystalline tabernanthalog monofumarate pattern #3 characterized by XRPD signals at 25.5 °2θ, 16.3 °2θ, and 16.6 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #3 characterized by two or more, or three or more XRPD signals selected from the group consisting of 25.5 °2θ, 16.3 °2θ, 16.6 °2θ, 20.1 °2θ, and 22.3 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #3 characterized by XRPD signals 25.5 °2θ, 16.3 °2θ, 16.6 °2θ, 20.1 °2θ, and 22.3 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #3 characterized by two or more, or three or more XRPD signals selected from the group consisting of 25.5 °2θ, 16.3 °2θ, 16.6 °2θ, 20.1 °2θ, 22.3 °2θ, 26.1 °2θ, and 26.8 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #3 characterized by XRPD signals of 25.5 °2θ, 16.3 °2θ, 16.6 °2θ, 20.1 °2θ, 22.3 °2θ, 26.1 °2θ, and 26.8 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #3 characterized by two or more, or three or more XRPD signals selected from the group consisting of 25.5 °2θ, 16.3 °2θ, 16.6 °2θ, 20.1 °2θ, 22.3 °2θ, 26.1 °2θ, 26.8 °2θ, 18.8 °2θ, 22.5 °2θ, and 9.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #3 characterized by XRPD signals at 25.5 °2θ, 16.3 °2θ, 16.6 °2θ, 20.1 °2θ, 22.3 °2θ, 26.1 °2θ, 26.8 °2θ, 18.8 °2θ, 22.5 °2θ, and 9.1 °2θ (±0.2 °2θ; ±0.1 °2θ; or 0.0 °2θ; Cu Kα1 radiation).

In some embodiments, the crystalline tabernanthalog monofumarate pattern #3 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four XRPD signals selected from those set forth in Table 43.

In some embodiments, the solid form of tabernanthalog monofumarate is crystalline tabernanthalog monofumarate pattern #4b characterized by two or more, or three or more XRPD signals selected from the group consisting of 25.8 °2θ, 16.6 °2θ, and 19.5 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #4b is crystalline tabernanthalog monofumarate is crystalline tabernanthalog monofumarate pattern #4b characterized by XRPD signals at 25.8 °2θ, 16.6 °2θ, and 19.5 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #4b characterized by two or more, or three or more XRPD signals selected from the group consisting of 25.8 °2θ, 16.6 °2θ, 19.5 °2θ, 9.3 °2θ, and 18.3 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #4b characterized by XRPD signals 25.8 °2θ, 16.6 °2θ, 19.5 °2θ, 9.3 °2θ, and 18.3 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #4b characterized by two or more, or three or more XRPD signals selected from the group consisting of 25.8 °2θ, 16.6 °2θ, 19.5 °2θ, 9.3 °2θ, 18.3 °2θ, 27.1 °2θ, and 17.0 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #4b characterized by XRPD signals of 25.8 °2θ, 16.6 °2θ, 19.5 °2θ, 9.3 °2θ, 18.3 °2θ, 27.1 °2θ, and 17.0 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #4b characterized by two or more, or three or more XRPD signals selected from the group consisting of 25.8 °2θ, 16.6 °2θ, 19.5 °2θ, 9.3 °2θ, 18.3 °2θ, 27.1 °2θ, 17.0 °2θ, 22.6 °2θ, 27.5 °2θ, and 21.5 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #4b characterized by XRPD signals at 25.8 °2θ, 16.6

°2θ, 19.5 °2θ, 9.3 °2θ, 18.3 °2θ, 27.1 °2θ, 17.0 °2θ, 22.6 °2θ, 27.5 °2θ, and 21.5 °2θ (±0.2 °2θ; ±0.1 °2θ; or 0.0 °2θ; Cu Kα1 radiation).

In some embodiments, the crystalline tabernanthalog monofumarate pattern #4b is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 44.

In some embodiments, the solid form of tabernanthalog monofumarate is crystalline tabernanthalog monofumarate pattern #4b characterized by two or more, or three or more XRPD signals selected from the group consisting of 25.5 °2θ, 16.3 °2θ, and 8.3 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #4b characterized by XRPD signals at 25.5 °2θ, 16.3 °2θ, and 8.3 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #4b characterized by two or more, or three or more XRPD signals selected from the group consisting of 25.5 °2θ, 16.3 °2θ, 8.3 °2θ, 9.1 °2θ, and 19.3 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #4b characterized by XRPD signals 25.5 °2θ, 16.3 °2θ, 8.3 °2θ, 9.1 °2θ, and 19.3 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #4b characterized by two or more, or three or more XRPD signals selected from the group consisting of 25.5 °2θ, 16.3 °2θ, 8.3 °2θ, 9.1 °2θ, 19.3 °2θ, 18.1 °2θ, and 17.2 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #4b characterized by XRPD signals of 25.5 °2θ, 16.3 °2θ, 8.3 °2θ, 9.1 °2θ, 19.3 °2θ, 18.1 °2θ, and 17.2 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #4b characterized by two or more, or three or more XRPD signals selected from the group consisting of 25.5 °2θ, 16.3 °2θ, 8.3 °2θ, 9.1 °2θ, 19.3 °2θ, 18.1 °2θ, 17.2 °2θ, 16.7 °2θ, 26.8 °2θ, and 11.2 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #4b characterized by XRPD signals at 25.5 °2θ, 16.3 °2θ, 8.3 °2θ, 9.1 °2θ, 19.3 °2θ, 18.1 °2θ, 17.2 °2θ, 16.7 °2θ, 26.8 °2θ, and 11.2 °2θ (±0.2 °2θ; ±0.1 °2θ; or 0.0 °2θ; Cu Kα1 radiation).

In some embodiments, the crystalline tabernanthalog monofumarate pattern #4b is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 45.

In some embodiments, the solid form of tabernanthalog hemifumarate is crystalline tabernanthalog hemifumarate pattern #5 characterized by two or more, or three or more XRPD signals selected from the group consisting of 25.5 °2θ, 16.3 °2θ, and 16.9 °2θ (±0.2 °2θ; ±0.1 °2θ; or ±0.0 °2θ; Cu Kα1 radiation). In some embodiments, the solid form of tabernanthalog hemifumarate is crystalline tabernanthalog hemifumarate pattern #5 characterized by XRPD signals at 25.5 °2θ, 16.3 °2θ, and 16.9 °2θ (±0.2 °2θ; ±0.1 °2θ; or ±0.0 °2θ; Cu Kα1 radiation).

In some embodiments, the solid form of tabernanthalog hemifumarate is crystalline tabernanthalog hemifumarate pattern #5 characterized by two or more, or three or more XRPD signals selected from the group consisting of 25.5 °2θ, 16.3 °2θ, 16.9 °2θ, 21.4 °2θ, and 8.3 °2θ (±0.2 °2θ; ±0.1 °2θ; or 0.0 °2θ; Cu Kα1 radiation). In some embodiments, the solid form of tabernanthalog hemifumarate is crystalline tabernanthalog hemifumarate pattern #5 characterized by XRPD signals of 25.5 °2θ, 16.3 °2θ, 16.9 °2θ, 21.4 °2θ, and 8.3 °2θ (±0.2 °2θ; 0.1 °2θ; or ±0.0 °2θ; Cu Kα1 radiation).

In some embodiments, the solid form of tabernanthalog hemifumarate is crystalline tabernanthalog hemifumarate pattern #5 characterized by two or more, or three or more XRPD signals selected from the group consisting of 25.5 °2θ, 16.3 °2θ, 16.9 °2θ, 21.4 °2θ, 8.3 °2θ, 11.1 °2θ, and 23.6 °2θ (±0.2 °2θ; ±0.1 °2θ; or 0.0 °2θ; Cu Kα1 radiation). In some embodiments, the solid form of tabernanthalog hemifumarate is crystalline tabernanthalog hemifumarate pattern #5 characterized by XRPD signals of 25.5 °2θ, 16.3 °2θ, 16.9 °2θ, 21.4 °2θ, 8.3 °2θ, 11.1 °2θ, and 23.6 °2θ (±0.2 °2θ; ±0.1 °2θ; or 0.0 °2θ; Cu Kα1 radiation).

In some embodiments, the solid form tabernanthalog hemifumarate is crystalline tabernanthalog hemifumarate pattern #5 characterized by two or more, or three or more XRPD signals selected from the group consisting of 25.5 °2θ, 16.3 °2θ, 16.9 °2θ, 21.4 °2θ, 8.3 °2θ, 11.1 °2θ, 23.6 °2θ, 20.0 °2θ, 15.4 °2θ, and 9.1 °2θ (±0.2 °2θ; ±0.1 °2θ; or 0.0 °2θ; Cu Kα1 radiation).

In some embodiments, the solid form tabernanthalog hemifumarate is crystalline tabernanthalog hemifumarate pattern #5 characterized by XRPD signals at 25.5 °2θ, 16.3 °2θ, 16.9 °2θ, 21.4 °2θ, 8.3 °2θ, 11.1 °2θ, 23.6 °2θ, 20.0 °2θ, 15.4 °2θ, and 9.1 °2θ (±0.2 °2θ; ±0.1 °2θ; or 0.0 °2θ; Cu Kα1 radiation).

In some embodiments, the crystalline tabernanthalog hemifumarate pattern #5 is characterized by one, two, three, four, five, six, seven, eight, nine, ten, eleven, twelve, thirteen, fourteen, fifteen, sixteen, seventeen, eighteen, or nineteen XRPD signals selected from those set forth in Table 46.

In some embodiments, the solid form of tabernanthalog monofumarate is crystalline tabernanthalog monofumarate pattern #4a characterized by two or more, or three or more XRPD signals selected from the group consisting of 25.6 °2θ, 8.2 °2θ, and 16.3 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #4a characterized by XRPD signals at 25.6 °2θ, 8.2 °2θ, and 16.3 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #4a characterized by two or more, or three or more XRPD signals selected from the group consisting of 25.6 °2θ, 8.2 °2θ, 16.3 °2θ, 11.3 °2θ, and 17.2 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #4a characterized by XRPD signals of 25.6 °2θ, 8.2 °2θ, 16.3 °2θ, 11.3 °2θ, and 17.2 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #4a characterized by two or more, or three or more XRPD signals selected from the group consisting of 25.6 °2θ, 8.2 °2θ, 16.3 °2θ, 11.3 °2θ, 17.2 °2θ, 21.6 °2θ, and 23.9 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #4a characterized by XRPD signals of 25.6 °2θ, 8.2 °2θ, 16.3 °2θ, 11.3 °2θ, 17.2 °2θ, 21.6 °2θ, and 23.9 °2θ (±0.2 °2θ; ±0.1 °2θ; or 0.0 °2θ; Cu Kα1 radiation).

In some embodiments, the solid form tabernanthalog monofumarate is crystalline tabernanthalog monofumarate pattern #4a characterized by two or more, or three or more XRPD signals selected from the group consisting of 25.6 °2θ, 8.2 °2θ, 16.3 °2θ, 11.3 °2θ, 17.2 °2θ, 21.6 °2θ, 23.9 °2θ, 9.1 °2θ, 20.4 °2θ, and 15.7 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #4a characterized by XRPD signals at 25.6 °2θ, 8.2 °2θ, 16.3 °2θ, 11.3 °2θ, 17.2 °2θ, 21.6 °2θ, 23.9 °2θ, 9.1 °2θ, 20.4 °2θ, and 15.7 °2θ (±0.2 °2θ; ±0.1 °2θ; or 0.0 °2θ; Cu Kα1 radiation).

In some embodiments, the crystalline tabernanthalog monofumarate pattern #4a is characterized by one, two, three, four, five, six, seven, eight, nine, ten, eleven, twelve, thirteen, fourteen, fifteen, sixteen, seventeen, eighteen, nineteen, twenty, twenty-one, or twenty-two XRPD signals selected from those set forth in Table 47.

In some embodiments, the solid form of tabernanthalog monofumarate is crystalline tabernanthalog monofumarate pattern #2d characterized by two or more, or three or more XRPD signals selected from the group consisting of 25.6 °2θ, 16.3 °2θ, and 22.2 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #2d characterized by XRPD signals at 25.6 °2θ, 16.3 °2θ, and 22.2 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #2d characterized by two or more, or three or more XRPD signals selected from the group consisting of 25.6 °2θ, 16.3 °2θ, 22.2 °2θ, 26.0 °2θ, and 25.3 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #2d characterized by XRPD signals of 25.6 °2θ, 16.3 °2θ, 22.2 °2θ, 26.0 °2θ, and 25.3 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #2d characterized by two or more, or three or more XRPD signals selected from the group consisting of 25.6 °2θ, 16.3 °2θ, 22.2 °2θ, 26.0 °2θ, 25.3 °2θ, 20.0 °2θ, and 9.1 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #2d characterized by XRPD signals of 25.6 °2θ, 16.3 °2θ, 22.2 °2θ, 26.0 °2θ, 25.3 °2θ, 20.0 °2θ, and 9.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #2d characterized by two or more, or three or more XRPD signals selected from the group consisting of 25.6 °2θ, 16.3 °2θ, 22.2 °2θ, 26.0 °2θ, 25.3 °2θ, 20.0 °2θ, 9.1 °2θ, 26.9 °2θ, 21.2 °2θ, and 17.6 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #2d characterized by XRPD signals at 25.6 °2θ, 16.3 °2θ, 22.2 °2θ, 26.0 °2θ, 25.3 °2θ, 20.0 °2θ, 9.1 °2θ, 26.9 °2θ, 21.2 °2θ, and 17.6 °2θ (±0.2 °2θ; ±0.1 °2θ; or 0.0 °2θ; Cu Kα1 radiation).

In some embodiments, the crystalline tabernanthalog monofumarate pattern #2d is characterized by one, two, three, four, five, six, seven, eight, nine, ten, eleven, twelve, thirteen, fourteen, or fifteen XRPD signals selected from those set forth in Table 48.

In some embodiments, the solid form of tabernanthalog monofumarate pattern #2b is crystalline tabernanthalog monofumarate pattern #2b characterized by two or more, or three or more XRPD signals selected from the group consisting of 25.5 °2θ, 16.3 °2θ, and 26.8 °2θ (±0.2 °2θ; ±0.1 °2θ; or 0.0 °2θ; Cu Kα1 radiation). In some embodiments, the solid form of tabernanthalog monofumarate pattern #2b is crystalline tabernanthalog monofumarate pattern #2b characterized by XRPD signals at 25.5 °2θ, 16.3 °2θ, and 26.8 (±0.2 °2θ; ±0.1 °2θ; or 0.0 °2θ; Cu Kα1 radiation).

In some embodiments, the solid form of tabernanthalog monofumarate pattern #2b is crystalline tabernanthalog monofumarate pattern #2b characterized by two or more, or three or more XRPD signals selected from the group consisting of 25.5 °2θ, 16.3 °2θ, 26.8 °2θ, 18.0 °2θ, and 9.0 °2θ°2θ (±0.2 °2θ; ±0.1 °2θ; or 0.0 °2θ; Cu Kα1 radiation). In some embodiments, the solid form of tabernanthalog monofumarate pattern #2b is crystalline tabernanthalog monofumarate pattern #2b characterized by XRPD signals of 25.5 °2θ, 16.3 °2θ, 26.8 °2θ, 18.0 °2θ, and 9.0 °2θ (±0.2 °2θ; ±0.1 °2θ; or ±0.0 °2θ; Cu Kα1 radiation).

In some embodiments, the solid form of tabernanthalog monofumarate pattern #2b is crystalline tabernanthalog monofumarate pattern #2b characterized by two or more, or three or more XRPD signals selected from the group consisting of 25.5 °2θ, 16.3 °2θ, 26.8 °2θ, 18.0 °2θ, 9.0 °2θ, 25.1 °2θ, and 22.1 °2θ (±0.2 °2θ; ±0.1 °2θ; or 0.0 °2θ; Cu Kα1 radiation). In some embodiments, the solid form of tabernanthalog monofumarate pattern #2b is crystalline tabernanthalog monofumarate pattern #2b characterized by XRPD signals of 25.5 °2θ, 16.3 °2θ, 26.8 °2θ, 18.0 °2θ, 9.0 °2θ, 25.1 °2θ, and 22.1 (±0.2 °2θ; ±0.1 °2θ; or ±0.0 °2θ; Cu Kα1 radiation).

In some embodiments, the solid form of tabernanthalog monofumarate pattern #2b is crystalline tabernanthalog monofumarate pattern #2b characterized by two or more, or three or more XRPD signals selected from the group consisting of 25.5 °2θ, 16.3 °2θ, 26.8 °2θ, 18.0 °2θ, 9.0 °2θ, 25.1 °2θ, 22.1 °2θ, 22.5 °2θ, 17.4 °2θ, and 27.2 °2θ (±0.2 °2θ; ±0.1 °2θ; or ±0.0 °2θ; Cu Kα1 radiation). In some embodiments, the solid form of tabernanthalog monofumarate pattern #2b is crystalline tabernanthalog monofumarate pattern #2b characterized by XRPD signals at 25.5 °2θ, 16.3 °2θ, 26.8 °2θ, 18.0 °2θ, 9.0 °2θ, 25.1 °2θ, 22.1 °2θ, 22.5 °2θ, 17.4 °2θ, and 27.2 °2θ (±0.2 °2θ; ±0.1 °2θ; or ±0.0 °2θ; Cu Kα1 radiation).

In some embodiments, the crystalline tabernanthalog monofumarate pattern #2b is characterized by one, two, three, four, five, six, seven, eight, nine, ten, eleven, twelve, or thirteen XRPD signals selected from those set forth in Table 49.

In some embodiments, the solid form of tabernanthalog monofumarate is crystalline tabernanthalog monofumarate pattern #1 characterized by two or more, or three or more XRPD signals selected from the group consisting of 25.6 °2θ, 16.4 °2θ, and 19.4 °2θ (±0.2 °2θ; ±0.1 °2θ; or 0.0 °2θ;

Cu Kα1 radiation). In some embodiments, the solid form of tabernanthalog monofumarate is crystalline tabernanthalog monofumarate pattern #1 characterized by XRPD signals at 25.6 °2θ, 16.4 °2θ, and 19.4 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.6 °2θ, 16.4 °2θ, 19.4 °2θ, 16.8 °2θ, and 18.2 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals of 25.6 °2θ, 16.4 °2θ, 19.4 °2θ, 16.8 °2θ, and 18.2 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.6 °2θ, 16.4 °2θ, 19.4 °2θ, 16.8 °2θ, 18.2 °2θ, 22.4 °2θ, and 26.9 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals of 25.6 °2θ, 16.4 °2θ, 19.4 °2θ, 16.8 °2θ, 18.2 °2θ, 22.4 °2θ, and 26.9 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.6 °2θ, 16.4 °2θ, 19.4 °2θ, 16.8 °2θ, 18.2 °2θ, 22.4 °2θ, 26.9 °2θ, 27.3 °2θ, 26.9 °2θ, and 9.1 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by XRPD signals at 25.6 °2θ, 16.4 °2θ, 19.4 °2θ, 16.8 °2θ, 18.2 °2θ, 22.4 °2θ, 26.9 °2θ, 27.3 °2θ, 26.9 °2θ, and 9.1 °2θ (±0.2 °2θ; ±0.1 °2θ; or 0.0 °2θ; Cu Kα1 radiation).

In some embodiments, the crystalline tabernanthalog monofumarate pattern #1 is characterized by one, two, three, four, five, six, seven, eight, nine, ten, eleven, twelve, thirteen, fourteen, fifteen, sixteen, or seventeen XRPD signals selected from those set forth in Table 50.

In some embodiments, the solid form of tabernanthalog monofumarate is crystalline tabernanthalog monofumarate pattern #1 characterized by two or more, or three or more XRPD signals selected from the group consisting of 25.5 °2θ, 16.3 °2θ, and 19.3 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals at 25.5 °2θ, 16.3 °2θ, and 19.3 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.5 °2θ, 16.3 °2θ, 19.3 °2θ, 16.7 °2θ, and 18.1 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals of 25.5 °2θ, 16.3 °2θ, 19.3 °2θ, 16.7 °2θ, and 18.1 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.5 °2θ, 16.3 °2θ, 19.3 °2θ, 16.7 °2θ, 18.1 °2θ, 9.1 °2θ, and 27.2 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #1 characterized by XRPD signals 25.5 °2θ, 16.3 °2θ, 19.3 °2θ, 16.7 °2θ, 18.1 °2θ, 9.1 °2θ, and 27.2 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by two or more, or three or more XRPD signals selected from the group consisting of 25.5 °2θ, 16.3 °2θ, 19.3 °2θ, 16.7 °2θ, 18.1 °2θ, 9.1 °2θ, 27.2 °2θ, 22.3 °2θ, 26.8 °2θ, and 6.7 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #1 characterized by XRPD signals at 25.5 °2θ, 16.3 °2θ, 19.3 °2θ, 16.7 °2θ, 18.1 °2θ, 9.1 °2θ, 27.2 °2θ, 22.3 °2θ, 26.8 °2θ, and 6.7 °2θ (±0.2 °2θ; ±0.1 °2θ; or 0.0 °2θ; Cu Kα1 radiation).

In some embodiments, the crystalline tabernanthalog monofumarate pattern #1 is characterized by one, two, three, four, five, six, seven, eight, nine, ten, eleven, twelve, thirteen, fourteen, fifteen, sixteen, or seventeen XRPD signals selected from those set forth in Table 51.

In some embodiments, the solid form of tabernanthalog monofumarate is crystalline tabernanthalog monofumarate pattern #8 characterized by two or more, or three or more XRPD signals selected from the group consisting of 15.9 °2θ, 16.4 °2θ, and 25.6 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #8 characterized by XRPD signals at 15.9 °2θ, 16.4 °2θ, and 25.6 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #8 characterized by two or more, or three or more XRPD signals selected from the group consisting of 15.9 °2θ, 16.4 °2θ, 25.6 °2θ, 24.3 °2θ, and 20.6 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #8 characterized by XRPD signals of 15.9 °2θ, 16.4 °2θ, 25.6 °2θ, 24.3 °2θ, and 20.6 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #8 characterized by two or more, or three or more XRPD signals selected from the group consisting of 15.9 °2θ, 16.4 °2θ, 25.6 °2θ, 24.3 °2θ, 20.6 °2θ, 7.6 °2θ, and 19.1 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #8 characterized by XRPD signals 15.9 °2θ, 16.4 °2θ, 25.6 °2θ, 24.3 °2θ, 20.6 °2θ, 7.6 °2θ, and 19.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #8 characterized by two or more, or three or more XRPD signals selected from the group consisting of 15.9

°2θ, 16.4 °2θ, 25.6 °2θ, 24.3 °2θ, 20.6 °2θ, 7.6 °2θ, 19.1 °2θ, 20.8 °2θ, 9.1 °2θ, and 18.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #8 characterized by XRPD signals at 15.9 °2θ, 16.4 °2θ, 25.6 °2θ, 24.3 °2θ, 20.6 °2θ, 7.6 °2θ, 19.1 °2θ, 20.8 °2θ, 9.1 °2θ, and 18.1 °2θ (±0.2 °2θ; ±0.1 °2θ; or 0.0 °2θ; Cu Kα1 radiation).

In some embodiments, the crystalline tabernanthalog monofumarate pattern #8 is characterized by one, two, three, four, five, six, seven, eight, nine, ten, eleven, twelve, thirteen, fourteen, fifteen, sixteen, or seventeen XRPD signals selected from those set forth in Table 52.

In some embodiments, the solid form of tabernanthalog monofumarate is crystalline tabernanthalog monofumarate pattern #4a characterized by two or more, or three or more XRPD signals selected from the group consisting of 25.5 °2θ, 16.3 °2θ, and 11.3 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #4a characterized by XRPD signals at 25.5 °2θ, 16.3 °2θ, and 11.3 °2θ (±0.2 °2θ; ±0.1 °2θ; or ±0.0 °2θ; Cu Kα1 radiation).

In some embodiments, the solid form tabernanthalog monofumarate is crystalline tabernanthalog monofumarate pattern #4a characterized by two or more, or three or more XRPD signals selected from the group consisting of 25.5 °2θ, 16.3 °2θ, 11.3 °2θ, 8.2 °2θ, and 17.0 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #4a characterized by XRPD signals 25.5 °2θ, 16.3 °2θ, 11.3 °2θ, 8.2 °2θ, and 17.0 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #4a characterized by two or more, or three or more XRPD signals selected from the group consisting 25.5 °2θ, 16.3 °2θ, 11.3 °2θ, 8.2 °2θ, 17.0 °2θ, 21.5 °2θ, and 23.7 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #4a characterized by XRPD signals 25.5 °2θ, 16.3 °2θ, 11.3 °2θ, 8.2 °2θ, 17.0 °2θ, 21.5 °2θ, and 23.7 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #4a characterized by two or more, or three or more XRPD signals selected from the group consisting of 25.5 °2θ, 16.3 °2θ, 11.3 °2θ, 8.2 °2θ, 17.0 °2θ, 21.5 °2θ, 23.7 °2θ, 20.2 °2θ, 15.6 °2θ, and 9.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #4a characterized by XRPD signals at 25.5 °2θ, 16.3 °2θ, 11.3 °2θ, 8.2 °2θ, 17.0 °2θ, 21.5 °2θ, 23.7 °2θ, 20.2 °2θ, 15.6 °2θ, and 9.1 °2θ (±0.2 °2θ; ±0.1 °2θ; or 0.0 °2θ; Cu Kα1 radiation).

In some embodiments, the crystalline tabernanthalog monofumarate is crystalline tabernanthalog monofumarate pattern #4a is characterized by one, two, three, four, five, six, seven, eight, nine, ten, eleven, twelve, thirteen, fourteen, fifteen, sixteen, seventeen, eighteen, nineteen, twenty, twenty-one, or twenty-two XRPD signals selected from those set forth in Table 53.

In some embodiments, the solid form of tabernanthalog monofumarate is crystalline tabernanthalog monofumarate pattern #13 characterized by two or more, or three or more XRPD signals selected from the group consisting of 25.6 °2θ, 16.0 °2θ, and 16.4 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #13 characterized by XRPD signals at 25.6 °2θ, 16.0 °2θ, and 16.4 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #13 characterized by two or more, or three or more XRPD signals selected from the group consisting of 25.6 °2θ, 16.0 °2θ, 16.4 °2θ, 25.0 °2θ, and 19.7 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #13 characterized by XRPD signals 25.6 °2θ, 16.0 °2θ, 16.4 °2θ, 25.0 °2θ, and 19.7 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate pattern #13 characterized by two or more, or three or more XRPD signals selected from the group consisting of 25.6 °2θ, 16.0 °2θ, 16.4 °2θ, 25.0 °2θ, 19.7 °2θ, 17.5 °2θ, and 8.1 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #13 characterized by XRPD signals 25.6 °2θ, 16.0 °2θ, 16.4 °2θ, 25.0 °2θ, 19.7 °2θ, 17.5 °2θ, and 8.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #13 characterized by two or more, or three or more XRPD signals selected from the group consisting of 25.6 °2θ, 16.0 °2θ, 16.4 °2θ, 25.0 °2θ, 19.7 °2θ, 17.5 °2θ, 8.1 °2θ, 21.9 °2θ, 9.1 °2θ, and 20.9 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #13 characterized by XRPD signals at 25.6 °2θ, 16.0 °2θ, 16.4 °2θ, 25.0 °2θ, 19.7 °2θ, 17.5 °2θ, 8.1 °2θ, 21.9 °2θ, 9.1 °2θ, and 20.9 °2θ (±0.2 °2θ; ±0.1 °2θ; or 0.0 °2θ; Cu Kα1 radiation).

In some embodiments, the crystalline tabernanthalog monofumarate pattern #13 is characterized by one, two, three, four, five, six, seven, eight, nine, ten, eleven, twelve, thirteen, fourteen, fifteen, sixteen, seventeen, eighteen, or nineteen XRPD signals selected from those set forth in Table 54.

In some embodiments, the solid form of tabernanthalog monofumarate is crystalline tabernanthalog monofumarate pattern #2b characterized by two or more, or three or more XRPD signals selected from the group consisting of 25.6 °2θ, 16.3 °2θ, and 9.1 °2θ (±0.2 °2θ; ±0.1 °2θ; or ±0.0 °2θ; Cu Kα1 radiation). In some embodiments, the solid form of tabernanthalog monofumarate is crystalline tabernanthalog monofumarate pattern #2b characterized by XRPD signals at 25.6 °2θ, 16.3 °2θ, and 9.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #2b characterized by two or more, or three or more XRPD signals selected from the group consisting of 25.6 °2θ, 16.3 °2θ, 9.1 °2θ, 24.7 °2θ, and 18.1 °2θ(±0.2 °2θ; ±0.1 °2θ; or 0.0 °2θ; Cu Kα1 radiation). In some embodiments, the solid form of tabernanthalog monofumarate is crystalline tabernanthalog monofumarate pattern #2b characterized by XRPD signals 25.6 °2θ, 16.3 °2θ, 9.1 °2θ, 24.7 °2θ, and 18.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #2b characterized by two or more, or three or more XRPD signals selected from the group consisting of 25.6 °2θ, 16.3 °2θ, 9.1 °2θ, 24.7 °2θ, 18.1 °2θ, 26.8 °2θ, and 17.1 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate pattern #2b characterized by XRPD signals 25.6 °2θ, 16.3 °2θ, 9.1 °2θ, 24.7 °2θ, 18.1 °2θ, 26.8 °2θ, and 17.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #2b characterized by two or more, or three or more XRPD signals selected from the group consisting of 25.6 °2θ, 16.3 °2θ, 9.1 °2θ, 24.7 °2θ, 18.1 °2θ, 26.8 °2θ, 17.1 °2θ, 17.4 °2θ, 15.6 °2θ, and 22.4 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate pattern #2b characterized by XRPD signals at 25.6 °2θ, 16.3 °2θ, 9.1 °2θ, 24.7 °2θ, 18.1 °2θ, 26.8 °2θ, 17.1 °2θ, 17.4 °2θ, 15.6 °2θ, and 22.4 °2θ (±0.2 °2θ; ±0.1 °2θ; or 0.0 °2θ; Cu Kα1 radiation).

In some embodiments, the crystalline tabernanthalog monofumarate pattern #2b is characterized by one, two, three, four, five, six, seven, eight, nine, ten, eleven, twelve, thirteen, fourteen, fifteen, sixteen, seventeen, or eighteen XRPD signals selected from those set forth in Table 55.

In some embodiments, the solid form of tabernanthalog monofumarate (Pattern #1) is crystalline tabernanthalog monofumarate (Pattern #1) characterized by two or more, or three or more XRPD signals selected from the group consisting of 25.6 °2θ, 16.0 °2θ, and 16.4 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.0 °2θ, and 16.4 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.0 °2θ, 16.4 °2θ, 25 °2θ, and 19.7 °2θ (±0.2 °2θ; ±0.1 °2θ; or 0.0 °2θ, Cu Kα1 radiation). In some embodiments, the solid form of tabernanthalog monofumarate (Pattern #1) is crystalline tabernanthalog monofumarate (Pattern #1) characterized by XRPD signals at 25.6 °2θ, 16.0 °2θ, 16.4 °2θ, 25 °2θ, 19.7 °2θ, 17.5 °2θ, and 8.1 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.0 °2θ, 16.4 °2θ, 25 °2θ, 19.7 °2θ, 17.5 °2θ, 8.1 °2θ, 21.9 °2θ, and 9.1 °2θ (±0.2 °2θ; ±0.1 °2θ; or ±0.0 °2θ; Cu Kα1 radiation).

In some embodiments, the crystalline tabernanthalog monofumarate is characterized by one, two, three, four, five, six, seven, eight, or nine XRPD signals selected from those set forth in Table 56.

In some embodiments, the solid form of tabernanthalog monofumarate (Pattern #1) is crystalline tabernanthalog monofumarate (Pattern #1) characterized by two or more, or three or more XRPD signals selected from the group consisting of 25.5 °2θ, 16.3 °2θ, and 16.8 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, and 16.8 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 16.8 °2θ, 19.3 °2θ, and 9.0 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 16.8 °2θ, 19.3 °2θ, 9.0 °2θ, 18.1 °2θ, and 22.3 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 16.8 °2θ, 19.3 °2θ, 9.0 °2θ, 18.1 °2θ, 22.3 °2θ, 24.6 °2θ, and 26.8 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 57.

In some embodiments, the solid form of tabernanthalog monofumarate (Pattern #1) is crystalline tabernanthalog monofumarate (Pattern #1) characterized by two or more, or three or more XRPD signals selected from the group consisting of 25.5 °2θ, 16.3 °2θ, and 19.3 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, and 19.3 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 16.7 °2θ, and 22.3 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 16.7 °2θ, 22.3 °2θ, 22.4 °2θ, and 26.8 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 16.7 °2θ, 22.3 °2θ, 22.4 °2θ, 26.8 °2θ, 9.0 °2θ, and 18.1 °2θ (±0.2 °2θ; ±0.1 °2θ; or ±0.0 °2θ; Cu Kα1 radiation).

In some embodiments, the crystalline tabernanthalog monofumarate is characterized by one, two, three, four, five, six, seven, eight, or nine XRPD signals selected from those set forth in Table 58.

In some embodiments, the solid form of tabernanthalog monofumarate (Pattern #1) is crystalline tabernanthalog monofumarate (Pattern #1) characterized by two or more, or three or more XRPD signals selected from the group consisting of 16.4 °2θ, 25.5 °2θ, and 19.4 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.4 °2θ, 25.5 °2θ, and 19.4 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.4 °2θ, 25.5 °2θ, 19.4 °2θ, 16.8 °2θ, and 9.1 °2θ (±0.2 °2θ; ±0.1 °2θ; or ±0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 16.4 °2θ, 25.5 °2θ, 19.4 °2θ, 16.8 °2θ, 9.1 °2θ, 25.2 °2θ, and 18.2 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.4 °2θ, 25.5 °2θ, 19.4 °2θ, 16.8 °2θ, 9.1 °2θ, 25.2 °2θ, 18.2 °2θ, 26.8 °2θ, and 22.4 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 59.

In some embodiments, the solid form of tabernanthalog monofumarate (Pattern #4a) is crystalline tabernanthalog monofumarate (Pattern #4a) characterized by two or more, or three or more XRPD signals selected from the group consisting of 25.5 °2θ, 16.3 °2θ, and 8.2 °2θ (±0.2 °2θ; ±0.1 °2θ; or 0.0 °2θ; Cu Kα1 radiation).

In some embodiments, the solid form of tabernanthalog monofumarate (Pattern #4a) is crystalline tabernanthalog monofumarate (Pattern #4a) characterized by XRPD signals at 25.5 °2θ, 16.3 °2θ, and 8.2 °2θ (±0.2 °2θ; ±0.1 °2θ; or ±0.0 °2θ; Cu Kα1 radiation).

In some embodiments, the solid form of tabernanthalog monofumarate (Pattern #4a) is crystalline tabernanthalog monofumarate (Pattern #4a) characterized by XRPD signals at 25.5 °2θ, 16.3 °2θ, 8.2 °2θ, 9.0 °2θ, and 17.1 °2θ (±0.2 °2θ; ±0.1 °2θ; or ±0.0 °2θ; Cu Kα1 radiation).

In some embodiments, the solid form of tabernanthalog monofumarate (Pattern #4a) is crystalline tabernanthalog monofumarate (Pattern #4a) characterized by XRPD signals at 25.5 °2θ, 16.3 °2θ, 8.2 °2θ, 9.0 °2θ, 17.1 °2θ, 21.5 °2θ, and 23.8 °2θ (±0.2 °2θ; ±0.1 °2θ; or 0.0 °2θ; Cu Kα1 radiation).

In some embodiments, the solid form of tabernanthalog monofumarate (Pattern #4a) is crystalline tabernanthalog monofumarate (Pattern #4a) characterized by XRPD signals at 25.5 °2θ, 16.3 °2θ, 8.2 °2θ, 9.0 °2θ, 17.1 °2θ, 21.5 °2θ, 23.8 °2θ, 11.2 °2θ, and 26.8 °2θ (±0.2 °2θ; ±0.1 °2θ; or ±0.0 °2θ; Cu Kα1 radiation).

In some embodiments, the crystalline tabernanthalog monofumarate is characterized by one, two, three, four, five, six, seven, eight, or nine XRPD signals selected from those set forth in Table 60.

In some embodiments, the solid form of tabernanthalog monofumarate (Pattern #2b) is crystalline tabernanthalog monofumarate (Pattern #2b) characterized by two or more, or three or more XRPD signals selected from the group consisting of 25.6 °2θ, 16.3 °2θ, and 9.1 °2θ (±0.2 °2θ; ±0.1 °2θ; or 0.0 °2θ; Cu Kα1 radiation).

In some embodiments, the solid form of tabernanthalog monofumarate (Pattern #2b) is crystalline tabernanthalog monofumarate (Pattern #2b) characterized by XRPD signals at 25.6 °2θ, 16.3 °2θ, and 9.1 °2θ (±0.2 °2θ; ±0.1 °2θ; or ±0.0 °2θ; Cu Kα1 radiation).

In some embodiments, the solid form of tabernanthalog monofumarate (Pattern #2b) is crystalline tabernanthalog monofumarate (Pattern #2b) characterized by XRPD signals at 25.6 °2θ, 16.3 °2θ, 9.1 °2θ, 18.1 °2θ, and 24.8 °2θ (±0.2 °2θ; ±0.1 °2θ; or ±0.0 °2θ; Cu Kα1 radiation).

In some embodiments, the solid form of tabernanthalog monofumarate (Pattern #2b) is crystalline tabernanthalog monofumarate (Pattern #2b) characterized by XRPD signals at 25.6 °2θ, 16.3 °2θ, 9.1 °2θ, 18.1 °2θ, 24.8 °2θ, 26.8 °2θ, and 15.5 °2θ (±0.2 °2θ; ±0.1 °2θ; or 0.0 °2θ; Cu Kα1 radiation).

In some embodiments, the solid form of tabernanthalog monofumarate (Pattern #2b) is crystalline tabernanthalog monofumarate (Pattern #2b) characterized by XRPD signals at 25.6 °2θ, 16.3 °2θ, 9.1 °2θ, 18.1 °2θ, 24.8 °2θ, 26.8 °2θ, 15.5 °2θ, 22.6 °2θ, and 17.0 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 61.

In some embodiments, the solid form of tabernanthalog monofumarate (Pattern #3) is crystalline tabernanthalog monofumarate (Pattern #3) characterized by two or more, or three or more XRPD signals selected from the group consisting of 25.5 °2θ, 16.4 °2θ, and 16.6 °2θ (±0.2 °2θ; ±0.1 °2θ; or 0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 25.5 °2θ, 16.4 °2θ, and 16.6 °2θ (±0.2 °2θ; ±0.1 °2θ; or ±0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 25.5 °2θ, 16.4 °2θ, 16.6 °2θ, 22.3 °2θ, and 22.4 °2θ (±0.2 °2θ; ±0.1 °2θ; or ±0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 25.5 °2θ, 16.4 °2θ, 16.6 °2θ, 22.3 °2θ, 22.4 °2θ, 26.0 °2θ, and 20.1 °2θ (±0.2 °2θ; ±0.1 °2θ; or ±0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 25.5 °2θ, 16.4 °2θ, 16.6 °2θ, 22.3 °2θ, 22.4 °2θ, 26.0 °2θ, 20.1 °2θ, 26.7 °2θ, and 16.8 °2θ (±0.2 °2θ; ±0.1 °2θ; or ±0.0 °2θ; Cu Kα1 radiation).

In some embodiments, the crystalline tabernanthalog monofumarate is characterized by one, two, three, four, five, six, seven, eight, or nine XRPD signals selected from those set forth in Table 62.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 26.0 °2θ, and 16.5 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 26.0 °2θ, and 16.5 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 26.0 °2θ, 16.5 °2θ, 20.6 °2θ, and 25.3 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 26.0 °2θ, 16.5 °2θ, 20.6 °2θ, 25.3 °2θ, 22 °2θ, and 19.3 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 26.0 °2θ, 16.5 °2θ, 20.6 °2θ, 25.3 °2θ, 22 °2θ, 19.3 °2θ, 12.9 °2θ, and 33.4 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 63.

In some embodiments, the solid form of tabernanthalog monofumarate (Pattern #19) is crystalline tabernanthalog monofumarate (Pattern #19) characterized by two or more, or three or more XRPD signals selected from the group consisting of 25.3 °2θ, 22.7 °2θ, and 20.5 °2θ (±0.2 °2θ; ±0.1 °2θ; or 0.0 °2θ; Cu Kα1 radiation).

In some embodiments, the solid form of tabernanthalog monofumarate (Pattern #19) is crystalline tabernanthalog monofumarate (Pattern #19) characterized by XRPD signals at 25.3 °2θ, 22.7 °2θ, and 20.5 °2θ (±0.2 °2θ; ±0.1 °2θ; or ±0.0 °2θ; Cu Kα1 radiation).

In some embodiments, the solid form of tabernanthalog monofumarate (Pattern #19) is crystalline tabernanthalog monofumarate (Pattern #19) characterized by XRPD signals at 25.3 °2θ, 22.7 °2θ, 20.5 °2θ, 27.1 °2θ, and 16.5 °2θ (±0.2 °2θ; ±0.1 °2θ; or ±0.0 °2θ; Cu Kα1 radiation).

In some embodiments, the solid form of tabernanthalog monofumarate (Pattern #19) is crystalline tabernanthalog monofumarate (Pattern #19) characterized by XRPD signals at 25.3 °2θ, 22.7 °2θ, 20.5 °2θ, 27.1 °2θ, 16.5 °2θ, 19.3 °2θ, and 26.6 °2θ (±0.2 °2θ; ±0.1 °2θ; or ±0.0 °2θ; Cu Kα1 radiation).

In some embodiments, the solid form of tabernanthalog monofumarate (Pattern #19) is crystalline tabernanthalog monofumarate (Pattern #19) characterized by XRPD signals at 25.3 °2θ, 22.7 °2θ, 20.5 °2θ, 27.1 °2θ, 16.5 °2θ, 19.3 °2θ, 26.6 °2θ, 9.1 °2θ, and 16.9 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 64.

In some embodiments, the solid form of tabernanthalog monofumarate (Pattern #2a) is crystalline tabernanthalog monofumarate (Pattern #2a) characterized by two or more, or three or more XRPD signals selected from the group consisting of 25.7 °2θ, 16.4 °2θ, and 17.2 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.7 °2θ, 16.4 °2θ, and 17.2 °2θ (±0.2 °2θ; ±0.1 °2θ; or 0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.7 °2θ, 16.4 °2θ, 17.2 °2θ, 9.2 °2θ, and 23.0 °2θ (±0.2 °2θ; ±0.1 °2θ; or 0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.7 °2θ, 16.4 °2θ, 17.2 °2θ, 9.2 °2θ, 23.0 °2θ, 27.4 °2θ, and 15.8 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.7 °2θ, 16.4 °2θ, 17.2 °2θ, 9.2 °2θ, 23.0 °2θ, 27.4 °2θ, 15.8 °2θ, 12.4 °2θ, and 22.9 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 65.

In some embodiments, the solid form of tabernanthalog monofumarate (Pattern #1) is crystalline tabernanthalog monofumarate (Pattern #1) characterized by two or more, or three or more XRPD signals selected from the group consisting of 25.6 °2θ, 16.5 °2θ, and 19.4 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.5 °2θ, and 19.4 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.5 °2θ, 19.4 °2θ, 16.7 °2θ, and 18.2 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.5 °2θ, 19.4 °2θ, 16.7 °2θ, 18.2 °2θ, 27 °2θ, and 27.2 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.5 °2θ, 19.4 °2θ, 16.7 °2θ, 18.2 °2θ, 27 °2θ, 27.2 °2θ, 9.2 °2θ, and 22.5 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 66.

In some embodiments, the solid form of tabernanthalog monofumarate (Pattern #1) is crystalline tabernanthalog monofumarate (Pattern #1) characterized by two or more, or three or more XRPD signals selected from the group consisting of 25.6 °2θ, 16.3 °2θ, and 19.3 °2θ (±0.2 °2θ; ±0.1 °2θ; or ±0.0 °2θ; Cu Kα1 radiation).

In some embodiments, the solid form of tabernanthalog monofumarate (Pattern #l) is crystalline tabernanthalog monofumarate (Pattern #1) characterized by XRPD signals at 25.6 °2θ, 16.3 °2θ, and 19.3 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.3 °2θ, 19.3 °2θ, 16.7 °2θ, and 18.1 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.3 °2θ, 19.3 °2θ, 16.7 °2θ, 18.1 °2θ, 27.3 °2θ, and 9.1 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.3 °2θ, 19.3 °2θ, 16.7 °2θ, 18.1 °2θ, 27.3 °2θ, 9.1 °2θ, 22.3 °2θ, and 26.8 °2θ (±0.2 °2θ; ±0.1 °2θ; or ±0.0 °2θ; Cu Kα1 radiation).

In some embodiments, the crystalline tabernanthalog monofumarate is characterized by one, two, three, four, five, six, seven, eight, or nine XRPD signals selected from those set forth in Table 67.

In some embodiments, the solid form of tabernanthalog monofumarate (Pattern #3) is crystalline tabernanthalog monofumarate (Pattern #3) characterized by two or more, or three or more XRPD signals selected from the group consisting of 16.7 °2θ, 25.6 °2θ, and 16.5 °2θ (±0.2 °2θ; ±0.1 °2θ; or ±0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 16.7 °2θ, 25.6 °2θ, and 16.5 °2θ (±0.2 °2θ; ±0.1 °2θ; or ±0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 16.7 °2θ, 25.6 °2θ, 16.5 °2θ, 16.9 °2θ, and 22.4 °2θ (±0.2 °2θ; ±0.1 °2θ; or 0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 16.7 °2θ, 25.6 °2θ, 16.5 °2θ, 16.9 °2θ, 22.4 °2θ, 20.2 °2θ, and 26.2 °2θ (±0.2 °2θ; ±0.1 °2θ; or ±0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 16.7 °2θ, 25.6 °2θ, 16.5 °2θ, 16.9 °2θ, 22.4 °2θ, 20.2 °2θ, 26.2 °2θ, 18.9 °2θ, and 26.9 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 68.

In some embodiments, the solid form of tabernanthalog monofumarate (Pattern #1) is crystalline tabernanthalog monofumarate (Pattern #1) characterized by two or more, or three or more XRPD signals selected from the group consisting of 25.5 °2θ, 16.3 °2θ, and 19.3 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, and 19.3 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 16.7 °2θ, and 18.1 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 16.7 °2θ, 18.1 °2θ, 22.3 °2θ, and 27.2 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 16.7 °2θ, 18.1 °2θ, 22.3 °2θ, 27.2 °2θ, 26.1 °2θ, and 26.8 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 69.

In some embodiments, the solid form of tabernanthalog monofumarate (Pattern #1) is crystalline tabernanthalog monofumarate (Pattern #1) characterized by two or more, or three or more XRPD signals selected from the group consisting of 25.5 °2θ, 25.4 °2θ, and 16.3 °20 (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 25.4 °2θ, and 16.3 °20 (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 25.4 °2θ, 16.3 °2θ, 19.3 °2θ, and 16.1 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 25.4 °2θ, 16.3 °2θ, 19.3 °2θ, 16.1 °2θ, 21.2 °2θ, and 16.7 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 25.4 °2θ, 16.3 °2θ, 19.3 °2θ, 16.1 °2θ, 21.2 °2θ, 16.7 °2θ, 18.1 °2θ, and 9.0 °2θ (±0.2 °2θ; ±0.1 °2θ; or ±0.0 °2θ; Cu Kα1 radiation).

In some embodiments, the crystalline tabernanthalog monofumarate is characterized by one, two, three, four, five, six, seven, eight, or nine XRPD signals selected from those set forth in Table 70.

In some embodiments, the solid form of tabernanthalog monofumarate (Pattern #5) is crystalline tabernanthalog monofumarate (Pattern #5) characterized by two or more, or three or more XRPD signals selected from the group consisting of 17.0 °2θ, 21.4 °2θ, and 15.4 °2θ (±0.2 °2θ; ±0.1 °2θ; or ±0.0 °2θ; Cu Kα1 radiation).

In some embodiments, the solid form of tabernanthalog monofumarate (Pattern #5) is crystalline tabernanthalog monofumarate (Pattern #5) characterized by XRPD signals at 17.0 °2θ, 21.4 °2θ, and 15.4 °2θ (±0.2 °2θ; ±0.1 °2θ; or ±0.0 °2θ; Cu Kα1 radiation).

In some embodiments, the solid form of tabernanthalog monofumarate (Pattern #5) is crystalline tabernanthalog monofumarate (Pattern #5) characterized by XRPD signals at 17.0 °2θ, 21.4 °2θ, 15.4 °2θ, 8.2 °2θ, and 23.6 °2θ (±0.2 °2θ; ±0.1 °2θ; or 0.0 °2θ; Cu Kα1 radiation).

In some embodiments, the solid form of tabernanthalog monofumarate (Pattern #5) is crystalline tabernanthalog monofumarate (Pattern #5) characterized by XRPD signals at 17.0 °2θ, 21.4 °2θ, 15.4020, 8.2 °2θ, 23.6 °2θ, 11.1 °2θ, and 20.0 °2θ (±0.2 °2θ; ±0.1 °2θ; or 0.0 °2θ; Cu Kα1 radiation).

In some embodiments, the solid form of tabernanthalog monofumarate (Pattern #5) is crystalline tabernanthalog monofumarate (Pattern #5) characterized by XRPD signals at 17.0 °2θ, 21.4 °2θ, 15.4 °2θ, 8.2 °2θ, 23.6 °2θ, 11.1 °2θ, 20.0 °2θ, 25.5 °2θ, and 22.5 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 71.

In some embodiments, the solid form of tabernanthalog monofumarate (Pattern #9) is crystalline tabernanthalog monofumarate (Pattern #9) characterized by two or more, or three or more XRPD signals selected from the group consisting of 25.4 °2θ, 24.5 °2θ, and 15.7 °2θ (±0.2 °2θ; ±0.1 °2θ; or ±0.0 °2θ; Cu Kα1 radiation).

In some embodiments, the solid form of tabernanthalog monofumarate (Pattern #9) is crystalline tabernanthalog monofumarate (Pattern #9) characterized by XRPD signals at 25.4 °2θ, 24.5 °2θ, and 15.7 °2θ (±0.2 °2θ; ±0.1 °2θ; or 0.0 °2θ; Cu Kα1 radiation).

In some embodiments, the solid form of tabernanthalog monofumarate (Pattern #9) is crystalline tabernanthalog monofumarate (Pattern #9) characterized by XRPD signals at 25.4 °2θ, 24.5 °2θ, 15.7 °2θ, 16.3 °2θ, and 25.1 °2θ (±0.2 °2θ; ±0.1 °2θ; or 0.0 °2θ; Cu Kα1 radiation).

In some embodiments, the solid form of tabernanthalog monofumarate (Pattern #9) is crystalline tabernanthalog monofumarate (Pattern #9) characterized by XRPD signals at 25.4 °2θ, 24.5 °2θ, 15.7 °2θ, 16.3 °2θ, 25.1 °2θ, 19.3 °2θ, and 16.9 °2θ (±0.2 °2θ; ±0.1 °2θ; or ±0.0 °2θ; Cu Kα1 radiation).

In some embodiments, the solid form of tabernanthalog monofumarate (Pattern #9) is crystalline tabernanthalog monofumarate (Pattern #9) characterized by XRPD signals at 25.4 °2θ, 24.5 °2θ, 15.7 °2θ, 16.3 °2θ, 25.1 °2θ, 19.3 °2θ, 16.9 °2θ, 21.6 °2θ, and 20.6 °2θ (±0.2 °2θ; ±0.1 °2θ; or ±0.0 °2θ; Cu Kα1 radiation).

In some embodiments, the crystalline tabernanthalog monofumarate is characterized by one, two, three, four, five, six, seven, eight, or nine XRPD signals selected from those set forth in Table 72.

In some embodiments, the solid form of tabernanthalog monofumarate (Pattern #1) is crystalline tabernanthalog monofumarate (Pattern #1) characterized by two or more, or three or more XRPD signals selected from the group consisting of 25.5 °2θ, 16.3 °2θ, and 19.3 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, and 19.3 °2θ (±0.2 °2θ; ±0.1 °2θ; or ±0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 16.7 °2θ, and 22.3 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 16.7 °2θ, 22.3 °2θ, 9.0 °2θ, and 27.2 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 16.7 °2θ, 22.3 °2θ, 9.0 °2θ, 27.2 °2θ, 18.1 °2θ, and 26.8 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 73.

In some embodiments, the solid form of tabernanthalog monofumarate (Pattern #2b) is crystalline tabernanthalog monofumarate (Pattern #2b) characterized by two or more, or three or more XRPD signals selected from the group consisting of 25.5 °2θ, 16.1 °2θ, and 26.8 °2θ (±0.2 °2θ; ±0.1 °2θ; or ±0.0 °2θ; Cu Kα1 radiation).

In some embodiments, the solid form of tabernanthalog monofumarate (Pattern #2b) is crystalline tabernanthalog monofumarate (Pattern #2b) characterized by XRPD signals at 25.5 °2θ, 16.1 °2θ, and 26.8 °2θ (±0.2 °2θ; ±0.1 °2θ; or 0.0 °2θ; Cu Kα1 radiation).

In some embodiments, the solid form of tabernanthalog monofumarate (Pattern #2b) is crystalline tabernanthalog monofumarate (Pattern #2b) characterized by XRPD signals at 25.5 °2θ, 16.1 °2θ, 26.8 °2θ, 9.0 °2θ, and 25.2 °2θ (±0.2 °2θ; ±0.1 °2θ; or 0.0 °2θ; Cu Kα1 radiation).

In some embodiments, the solid form of tabernanthalog monofumarate (Pattern #2b) is crystalline tabernanthalog monofumarate (Pattern #2b) characterized by XRPD signals at 25.5 °2θ, 16.1 °2θ, 26.8 °2θ, 9.0 °2θ, 25.2 °2θ, 18.0 °2θ, and 21.2 °2θ (±0.2 °2θ; ±0.1 °2θ; or ±0.0 °2θ; Cu Kα1 radiation).

In some embodiments, the solid form of tabernanthalog monofumarate (Pattern #2b) is crystalline tabernanthalog monofumarate (Pattern #2b) characterized by XRPD signals at 25.5 °2θ, 16.1 °2θ, 26.8 °2θ, 9.0 °2θ, 25.2 °2θ, 18.0 °2θ, 21.2 °2θ, 17.4 °2θ, and 22.6 °2θ (±0.2 °2θ; ±0.1 °2θ; or ±0.0 °2θ; Cu Kα1 radiation).

In some embodiments, the crystalline tabernanthalog monofumarate is characterized by one, two, three, four, five, six, seven, eight, or nine XRPD signals selected from those set forth in Table 74.

In some embodiments, the solid form of tabernanthalog monofumarate (Pattern #1) is crystalline tabernanthalog monofumarate (Pattern #1) characterized by two or more, or three or more XRPD signals selected from the group consisting of 25.6 °2θ, 16.4 °2θ, and 19.4 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.4 °2θ, and 19.4 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.4 °2θ, 19.4 °2θ, 16.8 °2θ, and 22.4 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.4 °2θ, 19.4 °2θ, 16.8 °2θ, 22.4 °2θ, 18.2 °2θ, and 9.1 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.4 °2θ, 19.4 °2θ, 16.8 °2θ, 22.4 °2θ, 18.2 °2θ, 9.1 °2θ, 26.9 °2θ, and 27.3 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 75.

In some embodiments, the solid form of tabernanthalog monofumarate (Pattern #1) is crystalline tabernanthalog monofumarate (Pattern #1) characterized by two or more, or three or more XRPD signals selected from the group consisting of 25.6 °2θ, 16.4 °2θ, and 19.4 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.4 °2θ, and 19.4 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.4 °2θ, 19.4 °2θ, 16.8 °2θ, and 18.2 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.4 °2θ, 19.4 °2θ, 16.8 °2θ, 18.2 °2θ, 9.1 °2θ, and 22.4 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 16.4 °2θ, 19.4 °2θ, 16.8 °2θ, 18.2 °2θ, 9.1 °2θ, 22.4 °2θ, 27.3 °2θ, and 26.9 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 76.

In some embodiments, the solid form of tabernanthalog monofumarate (Pattern #2a) is crystalline tabernanthalog monofumarate (Pattern #2a) characterized by two or more, or three or more XRPD signals selected from the group consisting of 25.5 °2θ, 16.3 °2θ, and 26.7 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.5 °2θ, 16.3 °2θ, and 26.7 °2θ (±0.2 °2θ; ±0.1 °2θ; or 0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.5 °2θ, 16.3 °2θ, 26.7 °2θ, 16.9 °2θ, and 27.1 °2θ (±0.2 °2θ; ±0.1 °2θ; or 0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.5 °2θ, 16.3 °2θ, 26.7 °2θ, 16.9 °2θ, 27.1 °2θ, 18.0 °2θ, and 9.0 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.5 °2θ, 16.3 °2θ, 26.7 °2θ, 16.9 °2θ, 27.1 °2θ, 18.0 °2θ, 9.0 °2θ, 25.0 °2θ, and 29.9 °2θ (±0.2 °2θ; ±0.1 °2θ; or ±0.0 °2θ; Cu Kα1 radiation).

In some embodiments, the crystalline tabernanthalog monofumarate is characterized by one, two, three, four, five, six, seven, eight, or nine XRPD signals selected from those set forth in Table 77.

In some embodiments, the solid form of tabernanthalog monofumarate (Pattern #2a) is crystalline tabernanthalog monofumarate (Pattern #2a) characterized by two or more, or three or more XRPD signals selected from the group consisting of 25.5 °2θ, 16.3 °2θ, and 17.0 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.5 °2θ, 16.3 °2θ, and 17.0 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.5 °2θ, 16.3 °2θ, 17.0 °2θ, 26.7 °2θ, and 27.2 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.5 °2θ, 16.3 °2θ, 17.0 °2θ, 26.7 °2θ, 27.2 °2θ, 9.0 °2θ, and 18.0 °2θ (±0.2 °2θ; ±0.1 °2θ; or 0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.5 °2θ, 16.3 °2θ, 17.0 °2θ, 26.7 °2θ, 27.2 °2θ, 9.0 °2θ, 18.0 °2θ, 22.9 °2θ, and 25.1 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 78.

In some embodiments, the solid form of tabernanthalog monofumarate (Pattern #1) is crystalline tabernanthalog monofumarate (Pattern #1) characterized by two or more, or three or more XRPD signals selected from the group consisting of 25.5 °2θ, 16.3 °2θ, and 19.3 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, and 19.3 °2θ (±0.2 °2θ; ±0.1 °2θ; or 0.0 °2θ; Cu Kα1 radiation). In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 9.0 °2θ, and 16.7 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 9.0 °2θ, 16.7 °2θ, 18.1 °2θ, and 26.8 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.5 °2θ, 16.3 °2θ, 19.3 °2θ, 9.0 °2θ, 16.7 °2θ, 18.1 °2θ, 26.8 °2θ, 27.2 °2θ, and 22.3 °2θ (±0.2 °2θ; ±0.1 °2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 79.

In some embodiments, the solid form of tabernanthalog monofumarate (Pattern #2a) is crystalline tabernanthalog monofumarate (Pattern #2a) characterized by two or more, or three or more XRPD signals selected from the group consisting of 25.6 °2θ, 16.3 °2θ, and 26.8 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.6 °2θ, 16.3 °2θ, and 26.8 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.6 °2θ, 16.3 °2θ, 26.8 °2θ, 9.1 °2θ, and 27.2 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.6 °2θ, 16.3 °2θ, 26.8 °2θ, 9.1 °2θ, 27.2 °2θ, 17.0 °2θ, and 18.1 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 25.6 °2θ, 16.3 °2θ, 26.8 °2θ, 9.1 °2θ, 27.2 °2θ, 17.0 °2θ, 18.1 °2θ, 14.2 °2θ, and 22.3 °2θ (±0.2 °2θ; ±0.1 °2θ; or ±0.0 °2θ; Cu Kα1 radiation).

In some embodiments, the crystalline tabernanthalog monofumarate is characterized by one, two, three, four, five, six, seven, eight, or nine XRPD signals selected from those set forth in Table 80.

In some embodiments, the solid form of tabernanthalog monofumarate (Pattern #2a) is crystalline tabernanthalog monofumarate (Pattern #2a) characterized by two or more, or three or more XRPD signals selected from the group consisting of 16.3 °2θ, 17.0 °2θ, and 25.5 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 16.3 °2θ, 17.0 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 16.3 °2θ, 17.0 °2θ, 22.9 °2θ, 25.5 °2θ, and 27.3 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 15.6 °2θ, 16.3 °2θ, 17.0 °2θ, 22.9 °2θ, 24.8 °2θ, 25.5 °2θ, and 27.3 °2θ (±0.2 °2θ; ±0.1 °2θ; or 0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 9.1 °2θ, 15.6 °2θ, 16.3 °2θ, 17.0 °2θ, 18.1 °2θ, 20.6 °2θ, 22.9 °2θ, 24.8 °2θ, 25.5 °2θ, and 27.3 °2θ (±0.2 °2θ; ±0.1 °2θ; or ±0.0 °2θ; Cu Kα1 radiation).

In some embodiments, the crystalline tabernanthalog monofumarate (Pattern #2a) is characterized by one, two, three, four, five, six, seven, eight, nine, or ten XRPD signals selected from those set forth in Table 81.

In some embodiments, the solid form of tabernanthalog monofumarate (Pattern #7) is crystalline tabernanthalog monofumarate (Pattern #7) characterized by two or more, or three or more XRPD signals selected from the group consisting of 16.3 °2θ, 24.8 °2θ, and 25.5 °2θ (±0.2 °2θ; ±0.1 °2θ; or ±0.0 °2θ; Cu Kα1 radiation).

In some embodiments, the solid form of tabernanthalog monofumarate (Pattern #7) is crystalline tabernanthalog monofumarate salt (Pattern #7) characterized by XRPD signals at 16.3 °2θ, 24.8 °2θ, and 25.5 °2θ (±0.2 °2θ; ±0.1 °2θ; or ±0.0 °2θ; Cu Kα1 radiation).

In some embodiments, the solid form of tabernanthalog monofumarate (Pattern #7) is crystalline tabernanthalog monofumarate (Pattern #7) characterized by XRPD signals at 9.1 °2θ, 15.9 °2θ, 16.3 °2θ, 24.8 °2θ, and 25.5 °2θ (±0.2 °2θ; ±0.1 °2θ; or ±0.0 °2θ; Cu Kα1 radiation).

In some embodiments, the solid form of tabernanthalog monofumarate (Pattern #7) is crystalline tabernanthalog monofumarate (Pattern #7) characterized by XRPD signals at 9.1 °2θ, 15.9 °2θ, 16.3 °2θ, 18.1 °2θ, 19.3 °2θ, 24.8 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #7) is crystalline tabernanthalog monofumarate (Pattern #7) characterized by XRPD signals at 9.1 °2θ, 15.9 °2θ, 16.3 °2θ, 18.1 °2θ, 19.3 °2θ, 19.7 °2θ, 21.2 °2θ, 24.8 °2θ, 25.5 °2θ, and 26.8 °2θ (±0.2 °2θ; ±0.1 °2θ; or 0.0 °2θ; Cu Kα1 radiation).

In some embodiments, the crystalline tabernanthalog monofumarate (Pattern #7) is characterized by one, two, three, four, five, six, seven, eight, nine, or ten XRPD signals selected from those set forth in Table 82.

In some embodiments, the solid form of tabernanthalog monofumarate (Pattern #2a) is crystalline tabernanthalog monofumarate (Pattern #2a) characterized by two or more, or three or more XRPD signals selected from the group consisting of 16.3 °2θ, 17.0 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 16.3 °2θ, 17.0 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 16.3 °2θ, 17.0 °2θ, 22.9 °2θ, 25.5 °2θ, and 27.3 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 9.0 °2θ, 15.6 °2θ, 16.3 °2θ, 17.0 °2θ, 22.9 °2θ, 25.5 °2θ, and 27.3 °2θ (±0.2 °2θ; ±0.1 °2θ; or ±0.0 °2θ; Cu Kα1 radiation).

In some embodiments, the solid form of tabernanthalog monofumarate (Pattern #2a) is crystalline tabernanthalog monofumarate (Pattern #2a) characterized by XRPD signals at 9.0 °2θ, 15.6 °2θ, 16.3 °2θ, 17.0 °2θ, 18.0 °2θ, 20.6 °2θ, 22.9 °2θ, 25.5 °2θ, 26.8 °2θ, and 27.3 °2θ (±0.2 °2θ; ±0.1 °2θ; or 0.0 °2θ; Cu Kα1 radiation).

In some embodiments, the crystalline tabernanthalog monofumarate (Pattern #2a) is characterized by one, two, three, four, five, six, seven, eight, nine, or ten XRPD signals selected from those set forth in Table 83.

In some embodiments, the solid form of tabernanthalog monofumarate (Pattern #10) is crystalline tabernanthalog monofumarate (Pattern #10) characterized by two or more, or three or more XRPD signals selected from the group consisting of 16.8 °2θ, 21.3. °2θ, and 23.4 °2θ (±0.2 °2θ; ±0.1 °2θ; or 0.0 °2θ; Cu Kα1 radiation).

In some embodiments, the solid form of tabernanthalog monofumarate (Pattern #10) is crystalline tabernanthalog monofumarate (Pattern #10) characterized by XRPD signals at 16.8 °2θ, 21.3. °2θ, and 23.4 °2θ (±0.2 °2θ; ±0.1 °2θ; or ±0.0 °2θ; Cu Kα1 radiation).

In some embodiments, the solid form of tabernanthalog monofumarate (Pattern #10) is crystalline tabernanthalog monofumarate (Pattern #10) characterized by XRPD signals at 16.8 °2θ, 19.8 °2θ, 21.3 °2θ, 23.4 °2θ, and 25.3 °2θ (±0.2 °2θ; ±0.1 °2θ; or 0.0 °2θ; Cu Kα1 radiation).

In some embodiments, the solid form of tabernanthalog monofumarate (Pattern #10) is crystalline tabernanthalog monofumarate (Pattern #10) characterized by XRPD signals at 15.2 °2θ, 16.8 °2θ, 19.8 °2θ, 21.3 °2θ, 23.4 °2θ, 23.6 °2θ, and 25.3 °2θ (±0.2 °2θ; ±0.1 °2θ; or 0.0 °2θ; Cu Kα1 radiation).

In some embodiments, the solid form of tabernanthalog monofumarate (Pattern #10) is crystalline tabernanthalog monofumarate (Pattern #10) characterized by XRPD signals at 8.2 °2θ, 10.9 °2θ, 15.2 °2θ, 16.8 °2θ, 19.8 °2θ, 21.3 °2θ, 21.8 °2θ, 23.4 °2θ, 23.6 °2θ, and 25.3 °2θ (±0.2 °2θ; ±0.1 °2θ; or 0.0 °2θ; Cu Kα1 radiation).

In some embodiments, the crystalline tabernanthalog monofumarate (Pattern #10) is characterized by one, two, three, four, five, six, seven, eight, nine, ten, eleven, twelve, thirteen, fourteen, fifteen, sixteen, seventeen, eighteen, or nineteen XRPD signals selected from those set forth in Table 84.

In some embodiments, the solid form of tabernanthalog monofumarate (Pattern #11) is crystalline tabernanthalog monofumarate (Pattern #11) characterized by two or more, or three or more XRPD signals selected from the group consisting of 7.4 °2θ, 16.1 °2θ, and 20.2 °2θ (±0.2 °2θ; ±0.1 °2θ; or 0.0 °2θ; Cu Kα1 radiation).

In some embodiments, the solid form of tabernanthalog monofumarate (Pattern #11) is crystalline tabernanthalog monofumarate (Pattern #11) characterized by XRPD signals at 7.4 °2θ, 16.1 °2θ, and 20.2 °2θ (±0.2 °2θ; ±0.1 °2θ; or 0.0 °2θ; Cu Kα1 radiation).

In some embodiments, the solid form of tabernanthalog monofumarate (Pattern #11) is crystalline tabernanthalog monofumarate (Pattern #11) characterized by XRPD signals at 7.4 °2θ, 16.1 °2θ, 20.2 °2θ, 21.5 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #11) is crystalline tabernanthalog monofumarate (Pattern #11) characterized by XRPD signals at 7.4 °2θ, 16.1 °2θ, 20.2 °2θ, 21.5 °2θ, 25.1 °2θ, 25.5 °2θ, and 25.7 °2θ (±0.2 °2θ; ±0.1 °2θ; or 0.0 °2θ; Cu Kα1 radiation).

In some embodiments, the solid form of tabernanthalog monofumarate (Pattern #11) is crystalline tabernanthalog monofumarate (Pattern #11) characterized by XRPD signals at 7.4 °2θ, 16.1 °2θ, 17.2 °2θ, 20.2 °2θ, 20.7 °2θ, 21.5 °2θ, 22.6 °2θ, 25.1 °2θ, 25.5 °2θ, and 25.7 °2θ (±0.2 °2θ; ±0.1 °2θ; or 0.0 °2θ; Cu Kα1 radiation).

In some embodiments, the crystalline tabernanthalog monofumarate (Pattern #11) is characterized by one, two, three, four, five, six, seven, eight, nine, ten, eleven, thirteen, fourteen, fifteen, or sixteen XRPD signals selected from those set forth in Table 85.

In some embodiments, the solid form of tabernanthalog monofumarate (Pattern #1) is crystalline tabernanthalog monofumarate (Pattern #1) characterized by two or more, or three or more XRPD signals selected from the group consisting of 16.2 °2θ, 19.2 °2θ, and 25.4 °2θ (±0.2 °2θ; ±0.1 °2θ, or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.2 °2θ, 19.2 °2θ, and 25.4 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.2 °2θ, 19.2 °2θ, 22.1 °2θ, 25.4 °2θ, and 27.1 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.2 °2θ, 19.2 °2θ, 22.1 °2θ, 25.4 °2θ, 25.9 °2θ, 26.7 °2θ, and 27.1 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.2 °2θ, 18.0 °2θ, 19.2 °2θ, 20.0 °2θ, 22.1 °2θ, 22.3 °2θ, 25.4 °2θ, 25.9 °2θ, 26.7 °2θ, and 27.1 °2θ (±0.2 °2θ; ±0.1 °2θ; or 0.0 °2θ; Cu Kα1 radiation).

In some embodiments, the crystalline tabernanthalog monofumarate (Pattern #1) is characterized by one, two, three, four, five, six, seven, eight, nine, or ten XRPD signals selected from those set forth in Table 86.

In some embodiments, the solid form of tabernanthalog monofumarate (Pattern #8) is crystalline tabernanthalog monofumarate (Pattern #8) characterized by two or more, or three or more XRPD signals selected from the group consisting of 19.5 °2θ, 25.9 °2θ, and 25.2 °2θ (±0.2 °2θ; ±0.1 °2θ; or 0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 19.5 °2θ, 25.9 °2θ, and 25.2 °2θ (±0.2 °2θ; ±0.1 °2θ; or 0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 19.5 °2θ, 25.2 °2θ, 25.9 °2θ, 26.1 °2θ, and 28.3 °2θ (±0.2 °2θ; ±0.1 °2θ; or 0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 13.0 °2θ, 19.3 °2θ, 19.5 °2θ, 25.2 °2θ, 25.9 °2θ, 26.1 °2θ, and 28.3 °2θ (±0.2 °2θ; ±0.1 °2θ; or ±0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 13.0 °2θ, 16.6 °2θ, 19.3 °2θ, 19.5 °2θ, 25.2 °2θ, 25.9 °2θ, 26.1 °2θ, 28.3 °2θ, 33.7 °2θ, and 37.7 °2θ (±0.2 °2θ; ±0.1 °2θ; or 0.0 °2θ; Cu Kα1 radiation).

In some embodiments, the crystalline tabernanthalog monofumarate (Pattern #8) is characterized by one, two, three, four, five, six, seven, eight, nine, or ten XRPD signals selected from those set forth in Table 87.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 20.6 °2θ, and 25.2 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6 °2θ, and 25.2 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 16.5 °2θ, 19.5 °2θ, 20.6 °2θ, 25.2 °2θ, and 26.0 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 16.5 °2θ, 19.2 °2θ, 19.5 °2θ, 20.6 °2θ, 22.0 °2θ, 25.2 °2θ, and 26.0 °2θ (±0.2 °2θ; ±0.1 °2θ; or 0.0 °2θ; Cu Kai radiation).

In some embodiments, the solid form of tabernanthalog monofumarate (Pattern #6a) is crystalline tabernanthalog monofumarate (Pattern #6a) characterized by XRPD signals at 12.9 °2θ, 16.5 °2θ, 19.2 °2θ, 19.5 °2θ, 20.6 °2θ, 22.0 °2θ, 25.2 °2θ, 26.0 °2θ, 28.0 °2θ, and 33.4 °2θ (±0.2 °2θ; ±0.1 °2θ; or 0.0 °2θ; Cu Kα1 radiation).

In some embodiments, the crystalline tabernanthalog monofumarate (Pattern #6a) is characterized by one, two, three, four, five, six, seven, eight, nine, or ten XRPD signals selected from those set forth in Table 88.

In some embodiments, the solid form of tabernanthalog fumarate salt is crystalline tabernanthalog fumarate salt characterized by two or more, or three or more XRPD signals selected from the group consisting of 9.1 °2θ, 16.3 °2θ, and 25.1 °2θ (±0.2 °2θ; ±0.1 °2θ; or ±0.0 °2θ; Cu Kα1 radiation).

In some embodiments, the solid form of tabernanthalog fumarate salt is crystalline tabernanthalog fumarate salt characterized by XRPD signals at 9.1 °2θ, 16.3 °2θ, and 25.1 °2θ (±0.2 °2θ; ±0.1 °2θ; or ±0.0 °2θ; Cu Kα1 radiation).

In some embodiments, the solid form of tabernanthalog fumarate salt is crystalline tabernanthalog fumarate salt characterized by XRPD signals at 9.1 °2θ, 16.3 °2θ, 25.1 °2θ, and 25.5 °2θ (±0.2 °2θ; ±0.1 °2θ; or 0.0 °2θ; Cu Kα1 radiation).

In some embodiments, the crystalline tabernanthalog fumarate salt is characterized by one, two, three, or four XRPD signals selected from those set forth in Table 90.

In some embodiments, the solid form of tabernanthalog monofumarate (Pattern #2c) is crystalline tabernanthalog monofumarate (Pattern #2c) characterized by two or more, or three or more XRPD signals selected from the group consisting of 9.1 °2θ, 16.3 °2θ, and 25.6 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 16.3 °2θ, and 25.6 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 16.3 °2θ, 19.5 °2θ, 25.1 °2θ, and 25.6 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 14.2 °2θ, 16.3 °2θ, 18.1 °2θ, 19.5 °2θ, 25.1 °2θ, and 25.6 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 14.2 °2θ, 16.3 °2θ, 17.5 °2θ, 18.1 °2θ, 19.5 °2θ, 25.1 °2θ, 25.6 °2θ, 26.1 °2θ, and 26.8 °2θ (±0.2 °2θ; ±0.1 °2θ; or 0.0 °2θ; Cu Kα1 radiation).

In some embodiments, the crystalline tabernanthalog monofumarate (Pattern #2c) is characterized by one, two, three, four, five, six, seven, eight, nine, or ten XRPD signals selected from those set forth in Table 91.

In some embodiments, the solid form of tabernanthalog monofumarate (Pattern #1) is crystalline tabernanthalog monofumarate (Pattern #1) characterized by two or more, or three or more XRPD signals selected from the group consisting of 16.4 °2θ, 19.4 °2θ, and 25.6 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.4 °2θ, 19.4 °2θ, and 25.6 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.4 °2θ, 16.8 °2θ, 18.2 °2θ, 19.4 °2θ, and 25.6 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.4 °2θ, 16.8 °2θ, 18.2 °2θ, 19.4 °2θ, 22.4 °2θ, 25.6 °2θ, and 27.3 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 9.1 °2θ, 16.4 °2θ, 16.8 °2θ, 17.8 °2θ, 18.2 °2θ, 19.4 °2θ, 22.4 °2θ, 25.6 °2θ, 26.9 °2θ, and 27.3 °2θ (±0.2 °2θ; ±0.1 °2θ; or 0.0 °2θ; Cu Kα1 radiation).

In some embodiments, the crystalline tabernanthalog monofumarate (Pattern #1) is characterized by one, two, three, four, five, six, seven, eight, nine, or ten XRPD signals selected from those set forth in Table 92.

In some embodiments, the solid form of tabernanthalog monofumarate (Pattern #1) is crystalline tabernanthalog monofumarate (Pattern #1) characterized by two or more, or three or more XRPD signals selected from the group consisting of 16.3 °2θ, 19.3 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.3 °2θ, 19.3 °2θ, and 25.5 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.3 °2θ, 16.7 °2θ, 19.3 °2θ, 25.5 °2θ, and 27.2 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 16.3 °2θ, 16.7 °2θ, 18.1 °2θ, 19.3 °2θ, 22.3 °2θ, 25.5 °2θ, and 27.2 °2θ (±0.2 °2θ; ±0.1 °2θ; or ±0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 9.0 °2θ, 16.3 °2θ, 16.7 °2θ, 18.1 °2θ, 19.3 °2θ, 22.3 °2θ, 23.1 °2θ, 25.5 °2θ, 26.8 °2θ, and 27.2 °2θ (±0.2 °2θ; ±0.1 °2θ; or 0.0 °2θ; Cu Kα1 radiation).

In some embodiments, the crystalline tabernanthalog monofumarate (Pattern #1) is characterized by one, two, three, four, five, six, seven, eight, nine, or ten XRPD signals selected from those set forth in Table 93.

In some embodiments, the solid form of tabernanthalog monofumarate (Pattern #8) is crystalline tabernanthalog monofumarate (Pattern #8) characterized by two or more, or three or more XRPD signals selected from the group consisting of 15.8 °2θ, 24.2 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 15.8 °2θ, 24.2 °2θ, and 25.5 °2θ (±0.2 °2θ; ±0.1 °2θ; or 0.0 °2θ; Cu Kα1 radiation). In some embodiments, the solid form of tabernanthalog monofumarate (Pattern #8) is crystalline tabernanthalog monofumarate (Pattern #8) characterized by XRPD signals at 15.8 °2θ, 16.3 °2θ, 20.6 °2θ, 24.2 °2θ, and 25.5 °2θ (±0.2 °2θ; ±0.1 °2θ; or ±0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 7.6 °2θ, 15.8 °2θ, 16.3 °2θ, 19.1 °2θ, 20.6 °2θ, 24.2 °2θ, and 25.5 °2θ (±0.2 °2θ; ±0.1 °2θ; or ±0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 7.6 °2θ, 9.1 °2θ, 15.8 °2θ, 16.3 °2θ, 19.1 °2θ, 20.6 °2θ, 21.9 °2θ, 23.8 °2θ, 24.2 °2θ, and 25.5 °2θ (±0.2 °2θ; ±0.1 °2θ; or 0.0 °2θ; Cu Kα1 radiation).

In some embodiments, the crystalline tabernanthalog monofumarate (Pattern #8) is characterized by one, two, three, four, five, six, seven, eight, nine, ten, eleven, twelve, thirteen, fourteen, fifteen or sixteen XRPD signals selected from those set forth in Table 94.

In some embodiments, the solid form of tabernanthalog monofumarate (Pattern #8) is crystalline tabernanthalog monofumarate (Pattern #8) characterized by two or more, or three or more XRPD signals selected from the group consisting of 15.9 °2θ, 24.3 °2θ, and 25.6 °2θ (±0.2 °2θ; ±0.1 °2θ; or 0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 15.9 °2θ, 24.3 °2θ, and 25.6 °2θ (±0.2 °2θ; ±0.1 °2θ; or ±0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 15.9 °2θ, 16.3 °2θ, 20.6 °2θ, 24.3 °2θ, and 25.6 °2θ (±0.2 °2θ; ±0.1 °2θ; or ±0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 7.6 °2θ, 15.9 °2θ, 16.3 °2θ, 19.1 °2θ, 20.6 °2θ, 24.3 °2θ, and 25.6 °2θ (±0.2 °2θ; ±0.1 °2θ; or ±0.0 °2θ; Cu Kα1 radiation).

In some embodiments, the solid form of tabernanthalog monofumarate (Pattern #8) is crystalline tabernanthalog monofumarate (Pattern #8) characterized by XRPD signals at 7.6 °2θ, 9.0 °2θ, 15.9 °2θ, 16.3 °2θ, 18.0 °2θ, 19.1 °2θ, 20.6 °2θ, 24.3 °2θ, 25.6 °2θ, and 26.8 °2θ (±0.2 °2θ; ±0.1 °2θ; or 0.0 °2θ; Cu Kα1 radiation).

In some embodiments, the crystalline tabernanthalog monofumarate (Pattern #8) is characterized by one, two, three, four, five, six, seven, eight, nine, ten eleven, twelve, thirteen, fourteen, fifteen, sixteen, seventeen, eighteen or nineteen XRPD signals selected from those set forth in Table 95.

In some embodiments, the solid form of tabernanthalog monofumarate (Pattern #3) is crystalline tabernanthalog monofumarate (Pattern #3) characterized by two or more, or three or more XRPD signals selected from the group consisting of 16.3 °2θ, 16.6 °2θ, and 25.5 °2θ (±0.2 °2θ; ±0.1 °2θ, or 0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 16.3 °2θ, 16.6 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 16.3 °2θ, 16.6 °2θ, 20.1 °2θ, 25.5 °2θ, and 26.0 °2θ (±0.2 °2θ; ±0.1 °2θ; or 0.0 °2θ: Cu Kα1 radiation).

In some embodiments, the solid form of tabernanthalog monofumarate (Pattern #3) is crystalline tabernanthalog monofumarate (Pattern #3) characterized by XRPD signals at 16.3 °2θ, 16.6 °2θ, 18.7 °2θ, 20.1 °2θ, 22.2 °2θ, 25.5 °2θ, and 26.0 °2θ (±0.2 °2θ; ±0.1 °2θ; or 0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 9.0 °2θ, 16.3 °2θ, 16.6 °2θ, 16.8 °2θ, 18.7 °2θ, 20.1 °2θ, 22.2 °2θ, 25.5 °2θ, 26.0 °2θ, and 26.7 °2θ (±0.2 °2θ; ±0.1 °2θ; or 0.0 °2θ; Cu Kα1 radiation).

In some embodiments, the crystalline tabernanthalog monofumarate (Pattern #3) is characterized by one, two, three, four, five, six, seven, eight, nine, or ten XRPD signals selected from those set forth in Table 96.

In some embodiments, the solid form of tabernanthalog monofumarate (Pattern #3) is crystalline tabernanthalog monofumarate (Pattern #3) characterized by two or more, or three or more XRPD signals selected from the group consisting of 16.3 °2θ, 16.6 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 16.3 °2θ, 16.6 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 16.3 °2θ, 16.6 °2θ, 20.1 °2θ, 25.5 °2θ, and 26.0 °2θ (±0.2 °2θ; ±0.1 °2θ; or ±0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 16.3 °2θ, 16.6 °2θ, 18.8 °2θ, 20.1 °2θ, 22.2 °2θ, 25.5 °2θ, and 26.0 °2θ (±0.2 °2θ; ±0.1 °2θ; or ±0.0 °2θ; Cu Kα1 radiation).

In some embodiments, the solid form of tabernanthalog monofumarate (Pattern #3) is crystalline tabernanthalog monofumarate (Pattern #3) characterized by XRPD signals at 11.1 °2θ, 16.3 °2θ, 16.6 °2θ, 16.9 °2θ, 18.8 °2θ, 20.1 °2θ, 22.2 °2θ, 25.5 °2θ, 26.0 °2θ, and 26.7 °2θ (±0.2 °2θ; ±0.1 °2θ; or 0.0 °2θ; Cu Kα1 radiation).

In some embodiments, the crystalline monofumarate (Pattern #3) is characterized by one, two, three, four, five, six, seven, eight, nine, or ten XRPD signals selected from those set forth in Table 97.

In some embodiments, the solid form of tabernanthalog monofumarate (Pattern #2c) is crystalline tabernanthalog monofumarate (Pattern #2c) characterized by two or more, or three or more XRPD signals selected from the group consisting of 9.1 °2θ, 16.3 °2θ, and 25.5 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 16.3 °2θ, and 25.5 °2θ (±0.2 °2θ; ±0.1 °2θ; or 0.0 °2θ; Cu Kα1 radiation). In some embodiments, the solid form of tabernanthalog monofumarate (Pattern #2c) is crystalline tabernanthalog monofumarate (Pattern #2c) characterized by XRPD signals at 9.1 °2θ, 16.3 °2θ, 20.6 °2θ, 25.1 °2θ, and 25.5 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 16.3 °2θ, 19.4 °2θ, 20.6 °2θ, 25.1 °2θ, 25.5 °2θ, and 26.0 °2θ (±0.2 °2θ; 0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 14.2 °2θ, 16.3 °2θ, 19.4 °2θ, 20.6 °2θ, 21.9 °2θ, 22.2 °2θ, 25.1 °2θ, 25.5 °2θ, and 26.0 °2θ (±0.2 °2θ; ±0.1 °2θ; or 0.0 °2θ; Cu Kα1 radiation).

In some embodiments, the crystalline tabernanthalog monofumarate (Pattern #2c) is characterized by one, two, three, four, five, six, seven, eight, nine, or ten XRPD signals selected from those set forth in Table 98.

In some embodiments, the solid form of tabernanthalog monofumarate (Pattern #2c) is crystalline tabernanthalog monofumarate (Pattern #2c) characterized by two or more, or three or more XRPD signals selected from the group consisting of 9.1 °2θ, 16.3 °2θ, and 19.5 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 16.3 °2θ, and 19.5 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 16.3 °2θ, 19.5 °2θ, 25.6 °2θ, and 26.1 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 16.3 °2θ, 16.4 °2θ, 19.5 °2θ, 25.2 °2θ, 25.6 °2θ, and 26.1 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 12.9 °2θ, 14.2 °2θ, 16.3 °2θ, 16.4 °2θ, 19.5 °2θ, 22.0 °2θ, 25.2 °2θ, 25.6 °2θ, and 26.1 °2θ (±0.2 °2θ; ±0.1 °2θ; or 0.0 °2θ; Cu Kα1 radiation).

In some embodiments, the crystalline tabernanthalog monofumarate (Pattern #2c) is characterized by one, two, three, four, five, six, seven, eight, nine, or ten XRPD signals selected from those set forth in Table 99.

In some embodiments, the solid form of tabernanthalog monofumarate (Pattern #2c) is crystalline tabernanthalog monofumarate (Pattern #2c) characterized by two or more, or three or more XRPD signals selected from the group consisting of 9.1 °2θ, 19.4 °2θ, and 26.0 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 19.4 °2θ, and 26.0 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 16.3 °2θ, 19.4 °2θ, 25.5 °2θ, and 26.0 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 12.9 °2θ, 16.3 °2θ, 19.4 °2θ, 20.6 °2θ, 25.5 °2θ, and 26.0 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 12.9 °2θ, 14.2 °2θ, 16.3 °2θ, 19.4 °2θ, 20.6 °2θ, 21.9 °2θ, 25.1 °2θ, 25.5 °2θ, and 26.0 °2θ (±0.2 °2θ; ±0.1 °2θ; or 0.0 °2θ; Cu Kα1 radiation).

In some embodiments, the crystalline tabernanthalog monofumarate (Pattern #2c) is characterized by one, two, three, four, five, six, seven, eight, nine, or ten XRPD signals selected from those set forth in Table 100.

In some embodiments, the solid form of tabernanthalog monofumarate (Pattern #2c) is crystalline tabernanthalog monofumarate (Pattern #2c) characterized by two or more, or three or more XRPD signals selected from the group consisting of 19.4 °2θ, 25.6 °2θ, and 26.0 °2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 19.4 °2θ, 25.6 °2θ, and 26.0 °2θ (±0.2°2θ; ±0.1°2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 12.9 °2θ, 16.3°2θ, 19.4 °2θ, 25.6 °2θ, and 26.0 °2θ (±0.2°2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 12.9 °2θ, 16.3°2θ, 17.4 °2θ, 19.4 °2θ, 25.6 °2θ, and 26.0°2θ (±0.2 °2θ; ±0.1°2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 12.9 °2θ, 16.3°2θ, 17.4 °2θ, 19.4 °2θ, 25.6 °2θ, 26.0 °2θ, 26.8 °2θ, and 31.2 °2θ (±0.2°2θ; ±0.1 °2θ; or ±0.0 °2θ; Cu Kα1 radiation).

In some embodiments, the crystalline tabernanthalog monofumarate (Pattern #2c) is characterized by one, two, three, four, five, six, seven, eight, or nine XRPD signals selected from those set forth in Table 101.

In some embodiments, the solid form of tabernanthalog monofumarate (Pattern #2c) is crystalline tabernanthalog monofumarate (Pattern #2c) characterized by two or more, or three or more XRPD signals selected from the group consisting of 9.1 °2θ, 16.3 °2θ, and 25.5°20 (±0.2°2θ; ±0.1°2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 16.3 °2θ, and 25.5°20 (±0.2°2θ; ±0.1°2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 14.2 °2θ, 16.3 °2θ, 25.0 °2θ, and 25.5 °2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 14.2 °2θ, 16.3 °2θ, 22.2 °2θ, 25.0 °2θ, 25.5 °2θ, and 26.7°2θ (±0.2 °2θ; ±0.1 °2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.1 °2θ, 14.2 °2θ, 16.3 °2θ, 19.5 °2θ, 21.9 °2θ, 22.2 °2θ, 25.0 °2θ, 25.5 °2θ, 26.1 °2θ, and 26.7 °2θ (±0.2 °2θ; ±0.1 °2θ; or 0.0 °2θ; Cu Kα1 radiation).

In some embodiments, the crystalline tabernanthalog monofumarate (Pattern #2c) is characterized by one, two, three, four, five, six, seven, eight, nine, or ten XRPD signals selected from those set forth in Table 102.

In some embodiments, the solid form of tabernanthalog monofumarate (Pattern #2c) is crystalline tabernanthalog monofumarate (Pattern #2c) characterized by two or more, or three or more XRPD signals selected from the group consisting of 9.2 °2θ, 16.5 °2θ, and 25.7°2θ (±0.2 °2θ; ±0.1 °2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.2 °2θ, 16.5 °2θ, and 25.7 °2θ (±0.2 °2θ; ±0.1°2θ; or 0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.2 °2θ, 16.5 °2θ, 18.3 °2θ, 25.4 °2θ, and 25.7 °2θ (±0.2°2θ; ±0.1°2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.2 °2θ, 14.4 °2θ, 16.5 °2θ, 18.3 °2θ, 25.4 °2θ, 25.7 °2θ, and 27.0 °2θ (±0.2°2θ; ±0.1°2θ; or ±0.0 °2θ; Cu Kα1 radiation).

In some embodiments, the solid form of tabernanthalog monofumarate (Pattern #2c) is crystalline tabernanthalog monofumarate (Pattern #2c) characterized by XRPD signals at 9.2 °2θ, 14.4 °2θ, 16.5 °2θ, 18.3 °2θ, 22.3 °2θ, 22.4 °2θ, 22.5 °2θ, 25.4 °2θ, 25.7 °2θ, and 27.0 °2θ (±0.2 °2θ; ±0.1 °2θ; or 0.0 °2θ; Cu Kα1 radiation).

In some embodiments, the crystalline tabernanthalog monofumarate (Pattern #2c) is characterized by one, two, three, four, five, six, seven, eight, nine, or ten XRPD signals selected from those set forth in Table 103.

In some embodiments, the solid form of tabernanthalog hemifumarate (Pattern #22) is crystalline tabernanthalog hemifumarate (Pattern #22) characterized by two or more, or three or more XRPD signals selected from the group consisting of 10.5 °2θ, 18.9 °2θ, and 27.4 °2θ (±0.2 °2θ; ±0.1 °2θ; or 0.0 °2θ; Cu Kα1 radiation).

In some embodiments, the solid form of tabernanthalog hemifumarate (Pattern #22) is crystalline tabernanthalog hemifumarate (Pattern #22) characterized by XRPD signals at 10.5 °2θ, 18.9 °2θ, and 27.4 °2θ (±0.2 °2θ; ±0.1°2θ; or 0.0 °2θ; Cu Kα1 radiation).

In some embodiments, the solid form of tabernanthalog hemifumarate (Pattern #22) is crystalline tabernanthalog hemifumarate (Pattern #22) characterized by XRPD signals at 10.5 °2θ, 15.1 °2θ, 18.9 °2θ, and 27.4 °2θ (±0.2 °2θ; ±0.1°2θ; or ±0.0 °2θ; Cu Kα1 radiation).

In some embodiments, the crystalline tabernanthalog hemifumarate (Pattern #22) is characterized by one, two, three, or four XRPD signals selected from those set forth in Table 105.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 25.3 °2θ, and 16.5 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 25.3 °2θ, and 16.5 °2θ (±0.2 °2θ; ±0.1 °2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 25.3°2θ, 16.5 °2θ, 20.6 °2θ, and 19.4 °2θ (±0.2 °2θ; ±0.1 °2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 25.3 °2θ, 16.5 °2θ, 20.6 °2θ, 19.4 °2θ, 26 °2θ, and 22.0°2θ (±0.2°2θ; ±0.1 °2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 25.3 °2θ, 16.5 °2θ, 20.6 °2θ, 19.4 °2θ, 26 °2θ, 22.0°2θ, 33.4 °2θ, and 12.9 °2θ (±0.2 °2θ; ±0.1°2θ; or 0.0 °2θ; Cu Kα1 radiation).

In some embodiments, the crystalline tabernanthalog monofumarate (Pattern #6a) is characterized by one, two, three, four, five, six, seven, eight, or nine XRPD signals selected from those set forth in Table 107.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 20.6 °2θ, and 16.5 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6 °2θ, and 16.5°2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6 °2θ, 16.5 °2θ, 25.3 °2θ, and 19.4°2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6°2θ, 16.5 °2θ, 25.3 °2θ, 19.4 °2θ, 26.0 °2θ, and 22.0 °2θ (±0.2°2θ; ±0.1 °2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6°2θ, 16.5 °2θ, 25.3 °2θ, 19.4 °2θ, 26.0 °2θ, 22.0 °2θ, 33.5 °2θ, and 12.9 °2θ (±0.2 °2θ; ±0.1 °2θ; or ±0.0 °2θ; Cu Kα1 radiation).

In some embodiments, the crystalline tabernanthalog monofumarate (Pattern #6a) is characterized by one, two, three, four, five, six, seven, eight, or nine XRPD signals selected from those set forth in Table 108.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 20.6 °2θ, and 16.5 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6 °2θ, and 16.5°2θ (±0.2°2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6 °2θ, 16.5 °2θ, 25.2°2θ, and 26.0 °2θ (±0.2 °2θ; ±0.1 °2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6°2θ, 16.5 °2θ, 25.2 °2θ, 26.0 (±0.2 °2θ; ±0.1 °2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.1 °2θ, 19.5 °2θ, 20.6 °2θ, 16.5 °2θ, 25.2 °2θ, 26.0 °2θ, 22.0 °2θ, and 33.4°2θ (±0.2 °2θ; ±0.1 °2θ; or ±0.0 °2θ; Cu Kul radiation).

In some embodiments, the crystalline tabernanthalog monofumarate (Pattern #6a) is characterized by one, two, three, four, five, six, seven, eight, nine, ten or eleven XRPD signals selected from those set forth in Table 109.

In some embodiments, the solid form of tabernanthalog hemifumarate (Pattern #5) is crystalline tabernanthalog hemifumarate (Pattern #5) characterized by two or more, or three or more XRPD signals selected from the group consisting of 8.2 °2θ, 25.5°2θ, and 17.0°2θ (±0.2 °2θ; ±0.1°2θ; or ±0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 25.5°2θ, and 17.0°2θ (±0.2 °2θ; ±0.1 °2θ; or 0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 25.5°2θ, 17.0 °2θ, 16.2 °2θ, and 21.4°2θ (±0.2°2θ; ±0.1°2θ; or 0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 25.5 °2θ, 17.0 °2θ, 16.2 °2θ, 21.4 °2θ, 11.2 °2θ, and 23.6 °2θ (±0.2°2θ; ±0.1 °2θ; or ±0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 25.5 °2θ, 17.0 °2θ, 16.2 °2θ, 21.4 °2θ, 11.2 °2θ, 23.6 °2θ, 20.2°2θ, 19.2 °2θ, and 15.5°2θ (±0.2 °2θ; ±0.1°2θ; or ±0.0 °2θ; Cu Kα1 radiation).

In some embodiments, the crystalline tabernanthalog hemifumarate (Pattern #5) is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, or twenty-eight XRPD signals selected from those set forth in Table 110.

In some embodiments, the solid form of tabernanthalog monofumarate (Pattern #6b) is crystalline tabernanthalog monofumarate (Pattern #6b) characterized by two or more, or three or more XRPD signals selected from the group consisting of 19.5 °2θ, 26.1 °2θ, and 20.6 °2θ (±0.2 °2θ; ±0.1 °2θ; or 0.0 °2θ; Cu Kα1 radiation).

In some embodiments, the solid form of tabernanthalog monofumarate (Pattern #6b) is crystalline tabernanthalog monofumarate (Pattern #6b) characterized by XRPD signals at 19.5 °2θ, 26.1 °2θ, and 20.6 °2θ (±0.2 °2θ; ±0.1 °2θ; or ±0.0 °2θ; Cu Kα1 radiation).

In some embodiments, the solid form of tabernanthalog monofumarate (Pattern #6b) is crystalline tabernanthalog monofumarate (Pattern #6b) characterized by XRPD signals at 19.5 °2θ, 26.1°2θ, 20.6 °2θ, 16.5 °2θ, and 25.3 °2θ (±0.2 °2θ; ±0.1 °2θ; or ±0.0 °2θ; Cu Kα1 radiation).

In some embodiments, the solid form of tabernanthalog monofumarate (Pattern #6b) is crystalline tabernanthalog monofumarate (Pattern #6b) characterized by XRPD signals at 19.5 °2θ, 26.1 °2θ, 20.6 °2θ, 16.5 °2θ, 25.3 °2θ, 13.0 °2θ, and 22.1°2θ (±0.2°2θ; ±0.1 °2θ; or 0.0 °2θ; Cu Kα1 radiation).

In some embodiments, the solid form of tabernanthalog monofumarate (Pattern #6b) is crystalline tabernanthalog monofumarate (Pattern #6b) characterized by XRPD signals at 19.5 °2θ, 26.1 °2θ, 20.6 °2θ, 16.5 °2θ, 25.3 °2θ, 13.0 °2θ, 22.1 °2θ, and 8.3 °2θ (±0.2°2θ; ±0.1°2θ; or ±0.0 °2θ; Cu Kα1 radiation).

In some embodiments, the crystalline tabernanthalog monofumarate (Pattern #6b) is characterized by one, two, three, four, five, six, seven, or eight XRPD signals selected from those set forth in Table 111.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 16.5 °2θ, and 25.2°2θ (±0.2°2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, and 25.2°2θ (±0.2°2θ; ±0.1°2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, 25.2 °2θ, 20.6 °2θ, and 26.0°2θ (±0.2°2θ; ±0.1°2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, 25.2 °2θ, 20.6 °2θ, 26.0 °2θ, 22.0 °2θ, and 33.4 °2θ (±0.2°2θ; ±0.1 °2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, 25.2 °2θ, 20.6 °2θ, 26.0 °2θ, 22.0 °2θ, 33.4 °2θ, 37.7 °2θ, and 12.9 °2θ (±0.2 °2θ; ±0.1 °2θ; or ±0.0 °2θ; Cu Kα1 radiation).

In some embodiments, the crystalline tabernanthalog monofumarate (Pattern #6a) is characterized by one, two, three, four, five, six, seven, eight, or nine XRPD signals selected from those set forth in Table 112.

In some embodiments, the solid form of tabernanthalog monofumarate (Pattern #1) is crystalline tabernanthalog monofumarate (Pattern #1) characterized by two or more, or three or more XRPD signals selected from the group consisting of 25.6 °2θ, 25.5 °2θ, and 16.4°2θ (±0.2°2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 25.5 °2θ, and 16.4°2θ (±0.2°2θ; ±0.1°2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 25.5 °2θ, 16.4 °2θ, 16.5 °2θ, and 9.1°2θ (±0.2°2θ; ±0.1°2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 25.5°2θ, 16.4 °2θ, 16.5 °2θ, 9.1 °2θ, 19.4 °2θ, and 17.4°2θ (±0.2°2θ; ±0.1 °2θ; or 0.0 °2θ; Cu Kα1 radiation).

In some embodiments, the solid form of tabernanthalog monofumarate (Pattern #1) is crystalline tabernanthalog monofumarate (Pattern #1) characterized by XRPD signals at 25.6 °2θ, 25.5 °2θ, 16.4 °2θ, 16.5 °2θ, 9.1 °2θ, 19.4 °2θ, 17.4 °2θ, 22.6 °2θ, 14.3°2θ, and 18.1 °2θ (±0.2 °2θ; ±0.1 °2θ; or 0.0 °2θ; Cu Kα1 radiation).

In some embodiments, the crystalline tabernanthalog monofumarate (Pattern #1) is characterized by one, two, three, four, five, six, seven, eight, nine, ten, eleven, twelve, thirteen, fourteen, fifteen, sixteen, seventeen, eighteen, and nineteen XRPD signals selected from those set forth in Table 113.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 25.3 °2θ, and 16.5°2θ (±0.2 °2θ; ±0.1°2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 25.3 °2θ, and 16.5°2θ (±0.2°2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 25.3 °2θ, 16.5°2θ, 20.6 °2θ, and 26.0 °2θ (±0.2°2θ; ±0.1°2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 25.3 °2θ, 16.5 °2θ, 20.6 °2θ, 26.0 °2θ, 12.9 °2θ, and 22.0°2θ (±0.2°2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 25.3 °2θ, 16.5 °2θ, 20.6°2θ, 26.0 °2θ, 12.9 °2θ, 22.0 °2θ, and 31.2°2θ (±0.2 °2θ; ±0.1 °2θ; or 0.0 °2θ; Cu Kα1 radiation).

In some embodiments, the crystalline tabernanthalog monofumarate (Pattern #6a) is characterized by one, two, three, four, five, six, seven, or eight XRPD signals selected from those set forth in Table 114.

In some embodiments, the solid form of tabernanthalog monofumarate (Pattern #6b) is crystalline tabernanthalog monofumarate (Pattern #6b) characterized by two or more, or three or more XRPD signals selected from the group consisting of 19.5 °2θ, 8.2 °2θ, and 20.6°2θ (±0.2°2θ; ±0.1°2θ; or ±0.0 °2θ; Cu Kα1 radiation).

In some embodiments, the solid form of tabernanthalog monofumarate (Pattern #6b) is crystalline tabernanthalog monofumarate (Pattern #6b) characterized by XRPD signals at 19.5 °2θ, 8.2 °2θ, and 20.6 °2θ (±0.2 °2θ; ±0.1 °2θ; or 0.0 °2θ; Cu Kα1 radiation).

In some embodiments, the solid form of tabernanthalog monofumarate (Pattern #6b) is crystalline tabernanthalog monofumarate (Pattern #6b) characterized by XRPD signals at 19.5 °2θ, 8.2 °2θ, 20.6°2θ, 16.5 °2θ, and 25.3 °2θ (±0.2 °2θ; ±0.1 °2θ; or ±0.0 °2θ; Cu Kα1 radiation).

In some embodiments, the solid form of tabernanthalog monofumarate (Pattern #6b) is crystalline tabernanthalog monofumarate (Pattern #6b) characterized by XRPD signals at 19.5 °2θ, 8.2 °2θ, 20.6 °2θ, 16.5 °2θ, 25.3 °2θ, 26.0 °2θ, and 12.9°2θ (±0.2°2θ; ±0.1°2θ; or 0.0 °2θ; Cu Kα1 radiation).

In some embodiments, the solid form of tabernanthalog monofumarate (Pattern #6b) is crystalline tabernanthalog monofumarate (Pattern #6b) characterized by XRPD signals at 19.5 °2θ, 8.2 °2θ, 20.6 °2θ, 16.5°2θ, 25.3 °2θ, 26.0 °2θ, 12.9 °2θ, 22.0 °2θ, and 17.1°2θ (±0.2 °2θ; ±0.1°2θ; or ±0.0 °2θ; Cu Kα1 radiation).

In some embodiments, the crystalline tabernanthalog monofumarate (Pattern #6b) is characterized by one, two, three, four, five, six, seven, eight, or nine XRPD signals selected from those set forth in Table 115.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 16.5 °2θ, and 20.6°2θ (±0.2°2θ; ±0.1°2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, and 20.6°2θ (±0.2 °2θ; ±0.1°2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, 20.6°2θ, 25.3 °2θ, and 26.0 °2θ (±0.2°2θ; ±0.1°2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, 20.6 °2θ, 25.3 °2θ, 26.0 °2θ, 22.0 °2θ, and 12.9°2θ (±0.2°2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, 20.6 °2θ, 25.3 °2θ, 26.0 °2θ, 22.0 °2θ, 12.9 °2θ, 33.5 °2θ, and 28.1 °2θ (±0.2 °2θ; ±0.1 °2θ; or ±0.0 °2θ; Cu Kα1 radiation).

In some embodiments, the crystalline tabernanthalog monofumarate (Pattern #6a) is characterized by one, two, three, four, five, six, seven, eight, nine or ten XRPD signals selected from those set forth in Table 116.

In some embodiments, the solid form of tabernanthalog hemifumarate (Pattern #5) is crystalline tabernanthalog hemifumarate (Pattern #5) characterized by two or more, or three or more XRPD signals selected from the group consisting of 8.2 °2θ, 11.3 °2θ, and 17.0°2θ (±0.2°2θ; ±0.1°2θ; or ±0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 11.3 °2θ, and 17.0 °2θ (±0.2 °2θ; ±0.1°2θ; or 0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 11.3 °2θ, 17.0 °2θ, 21.5 °2θ, and 20.2°20 (±0.2 °2θ; ±0.1°2θ; or 0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 11.3 °2θ, 17.0 °2θ, 21.5 °2θ, 20.2 °2θ, 23.7 °2θ, and 15.5°2θ (±0.2 °2θ; ±0.1°2θ; or 0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 11.3 °2θ, 17.0 °2θ, 21.5 °2θ, 20.2 °2θ, 23.7 °2θ, 15.5 °2θ, 22.6 °2θ, 24.4 °2θ, and 19.1 °2θ (±0.2 °2θ; ±0.1 °2θ; or ±0.0 °2θ; Cu Kα1 radiation).

In some embodiments, the crystalline tabernanthalog hemifumarate (Pattern #5) is characterized by one, two, three, four, five, six, seven, eight, nine, ten, eleven, twelve, thirteen, fourteen, and fifteen XRPD signals selected from those set forth in Table 117.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 20.6 °2θ, and 25.3°2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6 °2θ, and 25.3°2θ (±0.2°2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6 °2θ, 25.3 °2θ, 16.5 °2θ, and 19.4°2θ (±0.2 °2θ; ±0.1°2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6 °2θ, 25.3 °2θ, 16.5°2θ, 19.4 °2θ, 26.0 °2θ, and 22.0°2θ (±0.2 °2θ; ±0.1 °2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 20.6 °2θ, 25.3 °2θ, 16.5 °2θ, 19.4 °2θ, 26.0 °2θ, 22.0 °2θ, 39.6 °2θ, 33.4 °2θ, and 28.0°2θ (±0.2 °2θ; ±0.1 °2θ; or ±0.0 °2θ; Cu Kα1 radiation).

In some embodiments, the crystalline tabernanthalog monofumarate (Pattern #6a) is characterized by one, two, three, four, five, six, seven, eight, nine, ten, eleven or twelve XRPD signals selected from those set forth in Table 118.

In some embodiments, the solid form of tabernanthalog monofumarate (Pattern #6a) is crystalline tabernanthalog monofumarate (Pattern #6a) characterized by two or more, or three or more XRPD signals selected from the group consisting of 16.5 °2θ, 19.5 °2θ, and 20.6°2θ (±0.2°2θ; ±0.1°2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 16.5 °2θ, 19.5 °2θ, and 20.6 °2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 16.5 °2θ, 19.5 °2θ, 20.6 °2θ, 25.3 °2θ, and 26.1°2θ (±0.2°2θ; ±0.1°2θ; or 0.0 °2θ; Cu Kα1 radiation). In some embodiments, the solid form of tabernanthalog monofumarate (Pattern #6a) is crystalline tabernanthalog monofumarate (Pattern #6a) characterized by XRPD signals at 16.5 °2θ, 19.5 °2θ, 20.6 °2θ, 25.3 °2θ, 26.1 °2θ, 20.1°2θ, and 16.9 °2θ (±0.2°2θ; ±0.1°2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 16.5 °2θ, 19.5 °2θ, 20.6 °2θ, 25.3 °2θ, 26.1 °2θ, 20.1°2θ, 16.9 °2θ, 19.2 °2θ, 22.2 °2θ, and 22.1°2θ (±0.2 °2θ; ±0.1 °2θ; or ±0.0 °2θ; Cu Kα1 radiation).

In some embodiments, the crystalline tabernanthalog monofumarate (Pattern #6a) is characterized by one, two, three, four, five, six, seven, eight, nine, ten, eleven, twelve, thirteen, fourteen, fifteen, sixteen, seventeen, eighteen, or nineteen XRPD signals selected from those set forth in Table 119.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.6 °2θ, 16.6 °2θ, and 20.7°2θ (±0.2°2θ; ±0.1°2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.6 °2θ, 16.6 °2θ, and 20.7 °2θ (±0.2 °2θ; ±0.1°2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.6 °2θ, 16.6 °2θ, 20.7 °2θ, 25.4 °2θ, and 26.1°2θ (±0.2°2θ; ±0.1°2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.6 °2θ, 16.6 °2θ, 20.7 °2θ, 25.4 °2θ, 26.1 °2θ, 22.1 °2θ, and 13.0 °2θ (±0.2°2θ; ±0.1°2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.6 °2θ, 16.6 °2θ, 20.7 °2θ, 25.4°2θ, 26.1 °2θ, 22.1 °2θ, 13.0 °2θ, and 33.6°2θ (±0.2 °2θ; ±0.1°2θ; or 0.0 °2θ; Cu Kα1 radiation).

In some embodiments, the crystalline tabernanthalog monofumarate (Pattern #6a) is characterized by one, two, three, four, five, six, seven, or eight XRPD signals selected from those set forth in Table 120.

In some embodiments, the solid form of tabernanthalog monofumarate (Pattern #6a) is crystalline tabernanthalog monofumarate (Pattern #6a) characterized by two or more, or three or more XRPD signals selected from the group consisting of 19.5 °2θ, 16.5 °2θ, and 20.6°2θ (±0.2 °2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, and 20.6°2θ (±0.2°2θ; ±0.1 °2θ; or 0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, 20.6 °2θ, 25.3 °2θ, and 26.0 °2θ (±0.2 °2θ; ±0.1 °2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, 20.6 °2θ, 25.3 °2θ, 26.0 °2θ, 22.0 °2θ, and 7.5°2θ (±0.2°2θ; ±0.1 °2θ; or ±0.0 °2θ; Cu Kα1 radiation).

In some embodiments, the solid form of tabernanthalog monofumarate (Pattern #6a) is crystalline tabernanthalog monofumarate (Pattern #6a) characterized by XRPD signals at 19.5 °2θ, 16.5 °2θ, 20.6 °2θ, 25.3 °2θ, 26.0 °2θ, 22.0 °2θ, 7.5 °2θ, 15.9 °2θ, 33.4 °2θ, and 12.9°2θ (±0.2°2θ; ±0.1°2θ; or 0.0 °2θ; Cu Kα1 radiation).

In some embodiments, the crystalline tabernanthalog monofumarate (Pattern #6a) is characterized by one, two, three, four, five, six, seven, eight, nine or ten XRPD signals selected from those set forth in Table 121.

In some embodiments, the solid form of tabernanthalog hemifumarate (Pattern #5) is crystalline tabernanthalog hemifumarate (Pattern #5) characterized by two or more, or three or more XRPD signals selected from the group consisting of 8.2 °2θ, 21.5 °2θ, and 17.0°2θ (±0.2 °2θ; ±0.1°2θ; or ±0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 21.5 °2θ, and 17.0 °2θ (±0.2 °2θ; ±0.1 °2θ; or 0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 21.5 °2θ, 17.0 °2θ, 23.7 °2θ, and 11.3 °2θ (±0.2 °2θ; ±0.1°2θ; or ±0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 21.5 °2θ, 17.0 °2θ, 23.7 °2θ, 11.3 °2θ, 20.2°2θ, and 15.5 °2θ (±0.2°2θ; ±0.1 °2θ; or 0.0 °2θ; Cu Kα1 radiation).

In some embodiments, the solid form of tabernanthalog hemifumarate (Pattern #5) is crystalline tabernanthalog hemifumarate (Pattern #5) characterized by XRPD signals at 8.2 °2θ, 21.5 °2θ, 17.0 °2θ, 23.7 °2θ, 11.3 °2θ, 20.2 °2θ, 15.5 °2θ, 21.3 °2θ, 19.1 °2θ, and 25.5 °2θ (±0.2°2θ; ±0.1°2θ; or ±0.0 °2θ; Cu Kα1 radiation).

In some embodiments, the crystalline tabernanthalog hemifumarate (Pattern #5) is characterized by one, two, three, four, five, six, seven, eight, nine, ten, eleven, twelve, thirteen, fourteen, fifteen, sixteen, seventeen, or eighteen XRPD signals selected from those set forth in Table 122.

In some embodiments, the solid form of tabernanthalog fumarate salt is crystalline tabernanthalog fumarate salt characterized by two or more, or three or more XRPD signals selected from the group consisting of 25.6 °2θ, 16.4 °2θ, and 19.4°2θ (±0.2 °2θ; ±0.1°2θ; or ±0.0 °2θ; Cu Kα1 radiation).

In some embodiments, the solid form of tabernanthalog fumarate salt is crystalline tabernanthalog fumarate salt characterized by XRPD signals at 25.6 °2θ, 16.4 °2θ, and 19.4 °2θ (±0.2°2θ; ±0.1 °2θ; or ±0.0 °2θ; Cu Kα1 radiation).

In some embodiments, the solid form of tabernanthalog fumarate salt is crystalline tabernanthalog fumarate salt characterized by XRPD signals at 25.6 °2θ, 16.4 °2θ, 19.4 °2θ, 16.8 °2θ, and 18.2°2θ (±0.2°2θ; ±0.1°2θ; or 0.0 °2θ; Cu Kα1 radiation).

In some embodiments, the solid form of tabernanthalog fumarate salt is crystalline tabernanthalog fumarate salt characterized by XRPD signals at 25.6 °2θ, 16.4 °2θ, 19.4 °2θ, 16.8 °2θ, 18.2 °2θ, 9.2 °2θ, and 26.9 °2θ (±0.2°2θ; ±0.1°2θ; or 0.0 °2θ; Cu Kα1 radiation).

In some embodiments, the solid form of tabernanthalog fumarate salt is crystalline tabernanthalog fumarate salt characterized by XRPD signals at 25.6 °2θ, 16.4 °2θ, 19.4 °2θ, 16.8 °2θ, 18.2 °2θ, 9.2 °2θ, 26.9 °2θ, 27.3 °2θ, 22.4 °2θ, and 17.9 °2θ (±0.2 °2θ; ±0.1 °2θ; or ±0.0 °2θ; Cu Kα1 radiation).

In some embodiments, the crystalline tabernanthalog fumarate salt is characterized by one, two, three, four, five, six, seven, eight, nine, ten, eleven, twelve, thirteen, fourteen, fifteen, sixteen, or seventeen XRPD signals selected from those set forth in Table 125.

In some embodiments, the solid form of tabernanthalog fumarate salt is crystalline tabernanthalog fumarate salt characterized by two or more, or three or more XRPD signals selected from the group consisting of 25.6 °2θ, 16.3 °2θ, and 8.2°2θ (±0.2 °2θ; ±0.1°2θ; or 0.0 °2θ; Cu Kα1 radiation).

In some embodiments, the solid form of tabernanthalog fumarate salt is crystalline tabernanthalog fumarate salt characterized by XRPD signals at 25.6 °2θ, 16.3 °2θ, and 8.2°2θ (±0.2°2θ; ±0.1°2θ; or 0.0 °2θ; Cu Kα1 radiation).

In some embodiments, the solid form of tabernanthalog fumarate salt is crystalline tabernanthalog fumarate salt characterized by XRPD signals at 25.6 °2θ, 16.3°2θ, 8.2 °2θ, 17.0 °2θ, and 21.5°2θ (±0.2°2θ; ±0.1°2θ; or 0.0 °2θ; Cu Kα1 radiation).

In some embodiments, the solid form of tabernanthalog fumarate salt is crystalline tabernanthalog fumarate salt characterized by XRPD signals at 25.6 °2θ, 16.3 °2θ, 8.2 °2θ, 17.0 °2θ, 21.5 °2θ, 23.7 °2θ, and 11.2 °2θ (±0.2 °2θ; ±0.1 °2θ; or ±0.0 °2θ; Cu Kα1 radiation).

In some embodiments, the solid form of tabernanthalog fumarate salt is crystalline tabernanthalog fumarate salt characterized by XRPD signals at 25.6 °2θ, 16.3 °2θ, 8.2 °2θ, 17.0 °2θ, 21.5 °2θ, 23.7 °2θ, 11.2 °2θ, 21.5 °2θ, 19.5 °2θ, and 20.2°2θ (±0.2 °2θ; ±0.1 °2θ; or ±0.0 °2θ; Cu Kα1 radiation).

In some embodiments, the crystalline tabernanthalog fumarate salt is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four XRPD signals selected from those set forth in Table 126.

In some embodiments, the solid form of tabernanthalog monofumarate (Pattern #24) is crystalline tabernanthalog monofumarate (Pattern #24) characterized by two or more, or three or more XRPD signals selected from the group consisting of 17.2 °2θ, 27.4 °2θ, and 23.0°2θ (±0.2°2θ; ±0.1 °2θ; or 0.0 °2θ; Cu Kα1 radiation).

In some embodiments, the solid form of tabernanthalog monofumarate (Pattern #24) is crystalline tabernanthalog monofumarate (Pattern #24) characterized by XRPD signals at 17.2 °2θ, 27.4 °2θ, and 23.0°2θ (±0.2 °2θ; ±0.1 °2θ; or ±0.0 °2θ; Cu Kα1 radiation).

In some embodiments, the solid form of tabernanthalog monofumarate (Pattern #24) is crystalline tabernanthalog monofumarate (Pattern #24) characterized by XRPD signals at 17.2 °2θ, 27.4 °2θ, 23.0 °2θ, 20.8 °2θ, and 15.7°2θ (±0.2 °2θ; ±0.1 °2θ; or ±0.0 °2θ; Cu Kα1 radiation).

In some embodiments, the solid form of tabernanthalog monofumarate (Pattern #24) is crystalline tabernanthalog monofumarate (Pattern #24) characterized by XRPD signals at 17.2 °2θ, 27.4 °2θ, 23.0 °2θ, 20.8 °2θ, 15.7 °2θ, 22.3 °2θ, and 16.1°2θ (±0.2°2θ; ±0.1°2θ; or 0.0 °2θ; Cu Kα1 radiation).

In some embodiments, the solid form of tabernanthalog monofumarate (Pattern #24) is crystalline tabernanthalog monofumarate (Pattern #24) characterized by XRPD signals at 17.2 °2θ, 27.4 °2θ, 23.0 °2θ, 20.8 °2θ, 15.7 °2θ, 22.3 °2θ, 16.1 °2θ, 21.1 °2θ, 24.9 °2θ, and 12.4°2θ (±0.2°2θ; ±0.1 °2θ; or 0.0 °2θ; Cu Kα1 radiation).

In some embodiments, the crystalline tabernanthalog monofumarate (Pattern #24) is characterized by one, two, three, four, five, six, seven, eight, nine, ten, eleven, twelve, or thirteen XRPD signals selected from those set forth in Table 127.

In some embodiments, the solid form of tabernanthalog monofumarate (Pattern #24) is crystalline tabernanthalog monofumarate (Pattern #24) characterized by two or more, or three or more XRPD signals selected from the group consisting of 17.0 °2θ, 15.6 °2θ, and 22.9°2θ (±0.2°2θ; ±0.1°2θ; or 0.0 °2θ; Cu Kα1 radiation).

In some embodiments, the solid form of tabernanthalog monofumarate (Pattern #24) is crystalline tabernanthalog monofumarate (Pattern #24) characterized by XRPD signals at 17.0 °2θ, 15.6°2θ, and 22.9 °2θ (±0.2°2θ; ±0.1 °2θ; or 0.0 °2θ; Cu Kα1 radiation).

In some embodiments, the solid form of tabernanthalog monofumarate (Pattern #24) is crystalline tabernanthalog monofumarate (Pattern #24) characterized by XRPD signals at 17.0 °2θ, 15.6 °2θ, 22.9 °2θ, 20.7 °2θ, and 27.3°2θ (±0.2°2θ; ±0.1°2θ; or 0.0 °2θ; Cu Kα1 radiation).

In some embodiments, the solid form of tabernanthalog monofumarate (Pattern #24) is crystalline tabernanthalog monofumarate (Pattern #24) characterized by XRPD signals at 17.0 °2θ, 15.6 °2θ, 22.9°2θ, 20.7 °2θ, 27.3 °2θ, 15.9 °2θ, and 21.0 °2θ (±0.2 °2θ; ±0.1 °2θ; or ±0.0 °2θ; Cu Kα1 radiation).

In some embodiments, the solid form of tabernanthalog monofumarate (Pattern #24) is crystalline tabernanthalog monofumarate (Pattern #24) characterized by XRPD signals at 17.0 °2θ, 15.6°2θ, 22.9 °2θ, 20.7 °2θ, 27.3 °2θ, 15.9 °2θ, 21.0 °2θ, 12.2 °2θ, 24.8 °2θ, and 21.5°2θ (±0.2 °2θ; ±0.1 °2θ; or ±0.0 °2θ; Cu Kα1 radiation).

In some embodiments, the crystalline tabernanthalog monofumarate (Pattern #24) is characterized by one, two, three, four, five, six, seven, eight, nine, or ten XRPD signals selected from those set forth in Table 128.

In some embodiments, the solid form of tabernanthalog monofumarate (Pattern #23) is crystalline tabernanthalog monofumarate (Pattern #23) characterized by two or more, or three or more XRPD signals selected from the group consisting of 17.8 °2θ, 23.0 °2θ, and 12.9°2θ (±0.2°2θ; ±0.1°2θ; or ±0.0 °2θ; Cu Kα1 radiation).

In some embodiments, the solid form of tabernanthalog monofumarate (Pattern #23) is crystalline tabernanthalog monofumarate (Pattern #23) characterized by XRPD signals at 17.8 °2θ, 23.0 °2θ, and 12.9°2θ (±0.2 °2θ; ±0.1 °2θ; or ±0.0 °2θ; Cu Kα1 radiation).

In some embodiments, the solid form of tabernanthalog monofumarate (Pattern #23) is crystalline tabernanthalog monofumarate (Pattern #23) characterized by XRPD signals at 17.8 °2θ, 23.0 °2θ, 12.9 °2θ, 27.4 °2θ, and 25.7°2θ (±0.2°2θ; ±0.1 °2θ; or ±0.0 °2θ; Cu Kα1 radiation).

In some embodiments, the solid form of tabernanthalog monofumarate (Pattern #23) is crystalline tabernanthalog monofumarate (Pattern #23) characterized by XRPD signals at 17.8 °2θ, 23.0 °2θ, 12.9 °2θ, 27.4 °2θ, 25.7 °2θ, 16.1 °2θ, and 21.6°2θ (±0.2°2θ; ±0.1°2θ; or 0.0 °2θ; Cu Kα1 radiation).

In some embodiments, the solid form of tabernanthalog monofumarate (Pattern #23) is crystalline tabernanthalog monofumarate (Pattern #23) characterized by XRPD signals at 17.8 °2θ, 23.0 °2θ, 12.9 °2θ, 27.4 °2θ, 25.7 °2θ, 16.1 °2θ, 21.6 °2θ, 17.1 °2θ, 20.9 °2θ, and 26.8°2θ (±0.2°2θ; ±0.1 °2θ; or 0.0 °2θ; Cu Kα1 radiation).

In some embodiments, the crystalline tabernanthalog monofumarate (Pattern #23) is characterized by one, two, three, four, five, six, seven, eight, nine, ten, eleven, twelve, thirteen, fourteen, fifteen, sixteen, seventeen, or eighteen XRPD signals selected from those set forth in Table 129.

In some embodiments, the solid form of tabernanthalog monofumarate (Pattern #23) is crystalline tabernanthalog monofumarate (Pattern #23) characterized by two or more, or three or more XRPD signals selected from the group consisting of 17.6 °2θ, 22.9 °2θ, and 12.8°2θ (±0.2 °2θ; ±0.1 °2θ; or 0.0 °2θ; Cu Kα1 radiation).

In some embodiments, the solid form of tabernanthalog monofumarate (Pattern #23) is crystalline tabernanthalog monofumarate (Pattern #23) characterized by XRPD signals at 17.6 °2θ, 22.9 °2θ, and 12.8°2θ (±0.2°2θ; ±0.1 °2θ; or 0.0 °2θ; Cu Kα1 radiation).

In some embodiments, the solid form of tabernanthalog monofumarate (Pattern #23) is crystalline tabernanthalog monofumarate (Pattern #23) characterized by XRPD signals at 17.6 °2θ, 22.9 °2θ, 12.8 °2θ, 16.0 °2θ, and 27.3°2θ (±0.2°2θ; ±0.1°2θ; or ±0.0 °2θ; Cu Kα1 radiation).

In some embodiments, the solid form of tabernanthalog monofumarate (Pattern #23) is crystalline tabernanthalog monofumarate (Pattern #23) characterized by XRPD signals at 17.6 °2θ, 22.9 °2θ, 12.8°2θ, 16.0 °2θ, 27.3 °2θ, 25.6 °2θ, and 21.4°2θ (±0.2 °2θ; ±0.1 °2θ; or ±0.0 °2θ; Cu Kα1 radiation).

In some embodiments, the solid form of tabernanthalog monofumarate (Pattern #23) is crystalline tabernanthalog monofumarate (Pattern #23) characterized by XRPD signals at 17.6 °2θ, 22.9 °2θ, 12.8 °2θ, 16.0 °2θ, 27.3 °2θ, 25.6 °2θ, 21.4 °2θ, 16.9 °2θ, 16.2 °2θ, and 20.8°2θ (±0.2 °2θ; ±0.1 °2θ; or 0.0 °2θ; Cu Kα1 radiation).

In some embodiments, the crystalline tabernanthalog monofumarate (Pattern #23) is characterized by one, two, three, four, five, six, seven, eight, nine, ten, eleven, twelve, thirteen, fourteen, or fifteen XRPD signals selected from those set forth in Table 130.

In some embodiments, the solid form of tabernanthalog monofumarate salt Pattern #23 is crystalline tabernanthalog monofumarate salt Pattern #23 characterized by two or more, or three or more XRPD signals selected from the group consisting of 19.7 °2θ, 17.8 °2θ, and 23.0°2θ (±0.2 °2θ; ±0.1°2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 19.7 °2θ, 17.8 °2θ, and 23.0°2θ (±0.2 °2θ; ±0.1 °2θ; or 0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 19.7 °2θ, 17.8 °2θ, 23.0 °2θ, 26.3 °2θ, and 13.0°2θ (±0.2 °2θ; ±0.1 °2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 19.7 °2θ, 17.8 °2θ, 23.0 °2θ, 26.3 °2θ, and 13.0 °2θ (±0.2 °2θ; ±0.1°2θ; or 0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 19.7 °2θ, 17.8 °2θ, 23.0 °2θ, 26.3 °2θ, 13.0 °2θ, 20.9 °2θ, and 19.6°2θ (±0.2 °2θ; ±0.1 °2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 19.7 °2θ, 17.8 °2θ, 23.0 °2θ, 26.3 °2θ, 13.0 °2θ, 20.9 °2θ, and 19.6°2θ (±0.2 °2θ; ±0.1 °2θ; or ±0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 19.7 °2θ, 17.8 °2θ, 23.0 °2θ, 26.3 °2θ, 13.0°2θ, 20.9 °2θ, 19.6 °2θ, 16.1 °2θ, 27.5 °2θ, and 21.6°2θ (±0.2 °2θ; ±0.1°2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 19.7 °2θ, 17.8 °2θ, 23.0 °2θ, 26.3 °2θ, 13.0 °2θ, 20.9 °2θ, 19.6 °2θ, 16.1 °2θ, 27.5 °2θ, and 21.6°2θ (±0.2°2θ; ±0.1 °2θ; or 0.0 °2θ; Cu Kα1 radiation).

In some embodiments, the crystalline tabernanthalog monofumarate salt Pattern #23 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 133.

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.6 °2θ, 22.8 °2θ, and 27.2 °2θ (±0.2 °2θ; ±0.1°2θ; or ±0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.6 °2θ, 22.8 °2θ, and 27.2 °2θ (±0.2 °2θ; ±0.1°2θ; or ±0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.6 °2θ, 22.8 °2θ, 27.2 °2θ, 15.9 °2θ, and 21.4 °2θ (±0.2 °2θ; ±0.1 °2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.6 °2θ, 22.8 °2θ, 27.2 °2θ, 15.9 °2θ, and 21.4 °2θ (±0.2 °2θ; ±0.1 °2θ; or ±0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.6 °2θ, 22.8 °2θ, 27.2 °2θ, 15.9 °2θ, 21.4 °2θ, 19.4 °2θ, and 16.2 °2θ (±0.2 °2θ; ±0.1°2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.6 °2θ, 22.8°2θ, 27.2 °2θ, 15.9 °2θ, 21.4 °2θ, 19.4 °2θ, and 16.2°2θ (±0.2°2θ; ±0.1 °2θ; or 0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.6 °2θ, 22.8 °2θ, 27.2 °2θ, 15.9°2θ, 21.4 °2θ, 19.4 °2θ, 16.2, 25.5°2θ, 12.8°2θ, and 20.7°2θ (±0.2°2θ; ±0.1 °2θ; or ±0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.6 °2θ, 22.8 °2θ, 27.2 °2θ, 15.9 °2θ, 21.4 °2θ, 19.4°2θ, 16.2, 25.5 °2θ, 12.8°2θ, and 20.7 °2θ (±0.2 °2θ; ±0.1°2θ; or 0.0 °2θ; Cu Kα1 radiation).

In some embodiments, the crystalline tabernanthalog monofumarate salt Pattern #23 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 134.

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.6 °2θ, 25.5 °2θ, and 22.9°2θ (±0.2 °2θ; ±0.1 °2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.6 °2θ, 25.5 °2θ, and 22.9 °2θ (±0.2 °2θ; ±0.1°2θ; or 0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.6 °2θ, 25.5°2θ, 22.9 °2θ, 17.0 °2θ, and 24.9°2θ (±0.2°2θ; ±0.1 °2θ; or ±0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.6 °2θ, 25.5 °2θ, 22.9 °2θ, 17.0 °2θ, and 24.9 °2θ (±0.2°2θ; ±0.1°2θ; or 0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.6 °2θ, 25.5°2θ, 22.9 °2θ, 17.0 °2θ, 24.9 °2θ, 12.8 °2θ, and 21.0°2θ (±0.2°2θ; ±0.1°2θ; or ±0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.6 °2θ, 25.5 °2θ, 22.9 °2θ, 17.0 °2θ, 24.9 °2θ, 12.8 °2θ, and 21.0°2θ (±0.2°2θ; ±0.1°2θ; or 0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.6 °2θ, 25.5 °2θ, 22.9 °2θ, 17.0 °2θ, 24.9 °2θ, 12.8°2θ, 21.0 °2θ, 27.3 °2θ, 21.5 °2θ and 26.7°2θ (±0.2 °2θ; ±0.1 °2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.6 °2θ, 25.5°2θ, 22.9 °2θ, 17.0 °2θ, 24.9 °2θ, 12.8 °2θ, 21.0°2θ, 27.3 °2θ, 21.5 °2θ, and 26.7°2θ (±0.2°2θ; ±0.1°2θ; or 0.0 °2θ; Cu Kα1 radiation).

In some embodiments, the crystalline tabernanthalog monofumarate salt Pattern #23 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 135.

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.7 °2θ, 22.9 °2θ, and 16.3 °2θ (±0.2 °2θ; ±0.1 °2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.7 °2θ, 22.9 °2θ, and 16.3°2θ (±0.2°2θ; ±0.1 °2θ; or 0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.7 °2θ, 22.9 °2θ, 16.3°2θ, 16.0 °2θ, and 25.6 °2θ (±0.2°2θ; ±0.1 °2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.7 °2θ, 22.9 °2θ, 16.3 °2θ, 16.0 °2θ, and 25.6 °2θ (±0.2°2θ; ±0.1 °2θ; or 0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.7 °2θ, 22.9 °2θ, 16.3 °2θ, 16.0 °2θ, 25.6 °2θ, 12.9 °2θ, and 27.3 °2θ (±0.2 °2θ; ±0.1 °2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at 17.7 °2θ, 22.9 °2θ, 16.3°2θ, 16.0 °2θ, 25.6 °2θ, 12.9 °2θ, and 27.3°2θ (±0.2°2θ; ±0.1 °2θ; or ±0.0 °2θ; Cu Kα1 radiation).

In some embodiments, the solid form of tabernanthalog monofumarate salt Pattern #23 is crystalline tabernanthalog monofumarate salt Pattern #23 characterized by two or more, or three or more XRPD signals selected from the group consisting of 17.7 °2θ, 22.9 °2θ, 16.3°2θ, 16.0 °2θ, 25.6 °2θ, 12.9 °2θ, 27.3 °2θ, 21.5 °2θ, 16.9 °2θ, and 20.8°2θ (±0.2°2θ; ±0.1°2θ; or 0.0 °2θ; Cu Kα1 radiation). In some embodiments, the solid form of tabernanthalog monofumarate salt Pattern #23 is crystalline tabernanthalog monofumarate salt Pattern #23 characterized by XRPD signals at of 17.7 °2θ, 22.9 °2θ, 16.3°2θ, 16.0 °2θ, 25.6 °2θ, 12.9 °2θ, 27.3 °2θ, 21.5 °2θ, 16.9 °2θ, and 20.8 °2θ (±0.2 °2θ; ±0.1 °2θ; or ±0.0 °2θ; Cu Kα1 radiation).

In some embodiments, the crystalline tabernanthalog monofumarate salt Pattern #23 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 136.

In some embodiments, the solid form of tabernanthalog monofumarate salt Pattern #6a is crystalline tabernanthalog monofumarate salt Pattern #6a characterized by two or more, or three or more XRPD signals selected from the group consisting of 19.6 °2θ, 26.2 °2θ, and 20.8°2θ (±0.2 °2θ; ±0.1°2θ; or ±0.0 °2θ; Cu Kα1 radiation). In some embodiments, the solid form of tabernanthalog monofumarate salt Pattern #6a is crystalline tabernanthalog monofumarate salt Pattern #6a characterized by XRPD signals at 19.6 °2θ, 26.2 °2θ, and 20.8°2θ (±0.2°2θ; ±0.1°2θ; or ±0.0 °2θ; Cu Kα1 radiation).

In some embodiments, the solid form of tabernanthalog monofumarate salt Pattern #6a is crystalline tabernanthalog monofumarate salt Pattern #6a characterized by two or more, or three or more XRPD signals selected from the group consisting of 19.6 °2θ, 26.2 °2θ, 20.8 °2θ, 17.1 °2θ, and 16.6°2θ (±0.2 °2θ; ±0.1 °2θ; or 0.0 °2θ; Cu Kα1 radiation). In some embodiments, the solid form of tabernanthalog monofumarate salt Pattern #6a is crystalline tabernanthalog monofumarate salt Pattern #6a characterized by XRPD signals at 19.6 °2θ, 26.2 °2θ, 20.8 °2θ, 17.1 °2θ, and 16.6 °2θ (±0.2 °2θ; ±0.1 °2θ; or ±0.0 °2θ; Cu Kα1 radiation).

In some embodiments, the solid form of tabernanthalog monofumarate salt Pattern #6a is crystalline tabernanthalog monofumarate salt Pattern #6a characterized by two or more, or three or more XRPD signals selected from the group consisting of 19.6 °2θ, 26.2 °2θ, 20.8 °2θ, 17.1°2θ, 16.6 °2θ, 25.4 °2θ, and 13.0°2θ (±0.2°2θ; ±0.1°2θ; or 0.0 °2θ; Cu Kα1 radiation). In some embodiments, the solid form of tabernanthalog monofumarate salt Pattern #6a is crystalline tabernanthalog monofumarate salt Pattern #6a characterized by XRPD signals at 19.6 °2θ, 26.2 °2θ, 20.8 °2θ, 17.1 °2θ, 16.6 °2θ, 25.4 °2θ, and 13.0°2θ (±0.2°2θ; ±0.1°2θ; or 0.0 °2θ; Cu Kα1 radiation).

In some embodiments, the solid form of tabernanthalog monofumarate salt Pattern #6a is crystalline tabernanthalog monofumarate salt Pattern #6a characterized by two or more, or three or more XRPD signals selected from the group consisting of 19.6 °2θ, 26.2 °2θ, 20.8 °2θ, 17.1 °2θ, 16.6 °2θ, 25.4 °2θ, 13.0 °2θ, 23.0°2θ, 27.5 °2θ, and 22.2 °2θ (±0.2°2θ; ±0.1 °2θ; or ±0.0 °2θ; Cu Kα1 radiation). In some embodiments, the solid form of tabernanthalog monofumarate salt Pattern #6a is crystalline tabernanthalog monofumarate salt Pattern #6a characterized by XRPD signals at of 19.6 °2θ, 26.2 °2θ, 20.8 °2θ, 17.1 °2θ, 16.6 °2θ, 25.4 °2θ, 13.0 °2θ, 23.0 °2θ, 27.5 °2θ, and 22.2 °2θ (±0.2°2θ; ±0.1°2θ; or 0.0 °2θ; Cu Kα1 radiation).

In some embodiments, the crystalline tabernanthalog monofumarate salt Pattern #6a is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 137.

In some embodiments, the solid form of tabernanthalog monofumarate salt Pattern #6a is crystalline tabernanthalog monofumarate salt Pattern #6a characterized by two or more, or three or more XRPD signals selected from the group consisting of 19.5 °2θ, 26.1 °2θ, and 16.5 °2θ (±0.2 °2θ; ±0.1 °2θ; or 0.0 °2θ; Cu Kα1 radiation). In some embodiments, the solid form of tabernanthalog monofumarate salt Pattern #6a is crystalline tabernanthalog monofumarate salt Pattern #6a characterized by XRPD signals at 19.5 °2θ, 26.1 °2θ, and 16.5°2θ (±0.2°2θ; ±0.1°2θ; or 0.0 °2θ; Cu Kα1 radiation).

In some embodiments, the solid form of tabernanthalog monofumarate salt Pattern #6a is crystalline tabernanthalog monofumarate salt Pattern #6a characterized by two or more, or three or more XRPD signals selected from the group consisting of 19.5 °2θ, 26.1 °2θ, 16.5 °2θ, 20.7 °2θ, and 25.3 °2θ (±0.2 °2θ; ±0.1°2θ; or 0.0 °2θ; Cu Kα1 radiation). In some embodiments, the solid form of tabernanthalog monofumarate salt Pattern #6a is crystalline tabernanthalog monofumarate salt Pattern #6a characterized by XRPD signals at 19.5 °2θ, 26.1 °2θ, 16.5 °2θ, 20.7 °2θ, and 25.3 °2θ (±0.2°2θ; ±0.1°2θ; or 0.0 °2θ; Cu Kα1 radiation).

In some embodiments, the solid form of tabernanthalog monofumarate salt Pattern #6a is crystalline tabernanthalog monofumarate salt Pattern #6a characterized by two or more, or three or more XRPD signals selected from the group consisting of 19.5 °2θ, 26.1 °2θ, 16.5 °2θ, 20.7 °2θ, 25.3 °2θ, 13.0, and 22.1 °2θ (±0.2°2θ; ±0.1°2θ; or 0.0 °2θ; Cu Kα1 radiation). In some embodiments, the solid form of tabernanthalog monofumarate salt Pattern #6a is crystalline tabernanthalog monofumarate salt Pattern #6a characterized by XRPD signals at 19.5 °2θ, 26.1 °2θ, 16.5 °2θ, 20.7 °2θ, 25.3 °2θ, 13.0 °2θ, and 22.1°2θ (±0.2°2θ; ±0.1 °2θ; or ±0.0 °2θ; Cu Kα1 radiation).

In some embodiments, the solid form of tabernanthalog monofumarate salt Pattern #6a is crystalline tabernanthalog monofumarate salt Pattern #6a characterized by two or more, or three or more XRPD signals selected from the group consisting of 19.5 °2θ, 26.1 °2θ, 16.5 °2θ, 20.7 °2θ, 25.3 °2θ, 13.0°2θ, 22.1 °2θ, 19.4 °2θ, and 17.0°2θ (±0.2 °2θ; ±0.1°2θ; or ±0.0 °2θ; Cu Kα1 radiation). In some embodiments, the solid form of tabernanthalog monofumarate salt Pattern #6a is crystalline tabernanthalog monofumarate salt Pattern #26a characterized by XRPD signals at of 19.5 °2θ, 26.1 °2θ, 16.5 °2θ, 20.7 °2θ, 25.3 °2θ, 13.0 °2θ, 22.1 °2θ, 19.4 °2θ, and 17.0°2θ (±0.2 °2θ; ±0.1 °2θ; or ±0.0 °2θ; Cu Kα1 radiation).

In some embodiments, the crystalline tabernanthalog monofumarate salt Pattern #6a is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 138.

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, and 19.3°2θ (±0.2 °2θ; ±0.1°2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, and 19.3°2θ (±0.2 °2θ; ±0.1 °2θ; or ±0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, 19.3 °2θ, 16.7 °2θ, and 18.1°2θ (±0.2 °2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, 19.3 °2θ, 16.7 °2θ, and 18.1 °2θ (±0.2 °2θ; ±0.1 °2θ; or ±0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, 19.3 °2θ, 16.7 °2θ, 18.1 °2θ, 9.1 °2θ, and 26.8°2θ (±0.2°2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, 19.3 °2θ, 16.7 °2θ, 18.1 °2θ, 9.1 °2θ, and 26.8°2θ (±0.2°2θ; ±0.1°2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, 19.3 °2θ, 16.7 °2θ, 18.1 °2θ, 9.1 °2θ, 26.8 °2θ, 22.3 °2θ, 27.3°2θ and 25.2°2θ (±0.2°2θ; ±0.1°2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, 19.3 °2θ, 16.7 °2θ, 18.1 °2θ, 9.1 °2θ, 26.8 °2θ, 22.3 °2θ, 27.3°2θ and 25.2 °2θ (±0.2°2θ; ±0.1 °2θ; or 0.0 °2θ; Cu Kα1 radiation).

In some embodiments, the crystalline tabernanthalog monofumarate salt Pattern #1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 140.

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, and 26.8 °2θ (±0.2 °2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, and 26.8°2θ (±0.2°2θ; ±0.1°2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, 26.8 °2θ, 18.1 °2θ, and 27.2°2θ (±0.2 °2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, 26.8 °2θ, 18.1 °2θ, and 27.2 °2θ (±0.2°2θ; ±0.1 °2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, 26.8 °2θ, 18.1 °2θ, 27.2 °2θ, 25.1 °2θ, and 22.3°2θ (±0.2°2θ; ±0.1°2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, 26.8 °2θ, 18.1 °2θ, 27.2 °2θ, 25.1 °2θ, and 22.3°2θ (±0.2 °2θ; ±0.1°2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, 26.8 °2θ, 18.1 °2θ, 27.2 °2θ, 25.1 °2θ, 22.3 °2θ, 29.9 °2θ, 9.1°2θ and 17.5°2θ (±0.2°2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, 26.8 °2θ, 18.1 °2θ, 27.2 °2θ, 25.1 °2θ, 22.3 °2θ, 29.9 °2θ, 9.1°2θ and 17.5°2θ (±0.2 °2θ; ±0.1 °2θ; or 0.0 °2θ; Cu Kα1 radiation).

In some embodiments, the crystalline tabernanthalog monofumarate salt Pattern #1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 141.

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, and 9.1°2θ (±0.2°2θ; ±0.1 °2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, and 9.1°2θ (±0.2°2θ; ±0.1°2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, 9.1 °2θ, 25.2 °2θ, and 26.8°2θ (±0.2°2θ; ±0.1°2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, 9.1 °2θ, 25.2 °2θ, and 26.8°2θ (±0.2 °2θ; ±0.1 °2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, 9.1 °2θ, 25.2 °2θ, 26.8 °2θ, 16.7 °2θ, and 18.1°2θ (±0.2°2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, 9.1 °2θ, 25.2 °2θ, 26.8 °2θ, 16.7 °2θ, and 18.1°2θ (±0.2°2θ; ±0.1°2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.6 °2θ, 16.4 °2θ, 9.1 °2θ, 25.2 °2θ, 26.8 °2θ, 16.7 °2θ, 18.1 °2θ, 22.4 °2θ, 30.0°2θ and 27.2°2θ (±0.2 °2θ; ±0.1 °2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.6 °2θ, 16.4 °2θ, 9.1 °2θ, 25.2 °2θ, 26.8 °2θ, 16.7 °2θ, 18.1 °2θ, 22.4 °2θ, 30.0 °2θ and 27.2°2θ (±0.2°2θ; ±0.1 °2θ; or ±0.0 °2θ; Cu Kα1 radiation).

In some embodiments, the crystalline tabernanthalog monofumarate salt Pattern #1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 142.

In some embodiments, the solid form of tabernanthalog monofumarate salt Pattern #1 is crystalline tabernanthalog monofumarate salt Pattern #1 characterized by two or more, or three or more XRPD signals selected from the group consisting of 16.4 °2θ, 25.4 °2θ, and 25.7°2θ (±0.2 °2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 16.4 °2θ, 25.4 °2θ, and 25.7°2θ (±0.2°2θ; ±0.1°2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 16.4 °2θ, 25.4 °2θ, 25.7 °2θ, 9.1 °2θ, and 16.8°2θ (±0.2°2θ; ±0.1 °2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 16.4 °2θ, 25.4 °2θ, 25.7 °2θ, 9.1 °2θ, and 16.8°2θ (±0.2°2θ; ±0.1°2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 16.4 °2θ, 25.4 °2θ, 25.7 °2θ, 9.1 °2θ, 16.8 °2θ, 19.4 °2θ, and 18.2°2θ (±0.2°2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 16.4 °2θ, 25.4 °2θ, 25.7 °2θ, 9.1 °2θ, 16.8 °2θ, 19.4 °2θ, and 18.2 °2θ (±0.2°2θ; ±0.1°2θ; or ±0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 16.4 °2θ, 25.4 °2θ, 25.7 °2θ, 9.1 °2θ, 16.8 °2θ, 19.4 °2θ, 18.2 °2θ, 17.5 °2θ, 26.6°2θ and 14.3°2θ (±0.2 °2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 16.4 °2θ, 25.4 °2θ, 25.7°2θ, 9.1°2θ, 16.8 °2θ, 19.4 °2θ, 18.2 °2θ, 17.5°2θ, 26.6°2θ and 14.3 °2θ (±0.2 °2θ; ±0.1°2θ; or ±0.0 °2θ; Cu Kα1 radiation).

In some embodiments, the crystalline tabernanthalog monofumarate salt Pattern #1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 143.

In some embodiments, the solid form of a mixture of two salts provided herein is a mixture of two crystalline salts provided herein characterized by two or more, or three or more XRPD signals selected from the group consisting of 25.6 °2θ, 16.4 °2θ, and 20.7 °2θ (±0.2 °2θ; ±0.1 °2θ; or 0.0 °2θ; Cu Kα1 radiation). In some embodiments, the mixture of two salts provided herein is a mixture of two crystalline salts provided herein characterized by XRPD signals at 25.6 °2θ, 16.4 °2θ, and 20.7°2θ (±0.2°2θ; ±0.1 °2θ; or 0.0 °2θ; Cu Kα1 radiation).

In some embodiments, the solid form of a mixture of two salts provided herein is a mixture of two crystalline salts provided herein characterized by two or more, or three or more XRPD signals selected from the group consisting of 25.6 °2θ, 16.4 °2θ, 20.7 °2θ, 17.0 °2θ, and 19.5°2θ (±0.2°2θ; ±0.1 °2θ; or 0.0 °2θ; Cu Kα1 radiation). In some embodiments, the mixture of two salts provided herein is a mixture of two crystalline salts provided herein characterized by XRPD signals at 25.6 °2θ, 16.4 °2θ, 20.7 °2θ, 17.0 °2θ, and 19.5°2θ (±0.2°2θ; ±0.1 °2θ; or 0.0 °2θ; Cu Kα1 radiation).

In some embodiments, the solid form of a mixture of two salts provided herein is a mixture of two crystalline salts provided herein characterized by two or more, or three or more XRPD signals selected from the group consisting of 25.6 °2θ, 16.4 °2θ, 20.7 °2θ, 17.0 °2θ, 19.5 °2θ, 16.5 °2θ, and 15.7°2θ (±0.2°2θ; ±0.1°2θ; or 0.0 °2θ; Cu Kα1 radiation). In some embodiments, the mixture of two salts provided herein is a mixture of two crystalline salts provided herein characterized by XRPD signals at 25.6 °2θ, 16.4 °2θ, 20.7 °2θ, 17.0 °2θ, 19.5 °2θ, 16.5 °2θ, and 15.7°2θ (±0.2 °2θ; 0.1°2θ; or ±0.0 °2θ; Cu Kα1 radiation).

In some embodiments, the solid form of a mixture of two salts provided herein is a mixture of two crystalline salts provided herein by two or more, or three or more XRPD signals selected from the group consisting of 25.6 °2θ, 16.4 °2θ, 20.7 °2θ, 17.0 °2θ, 19.5 °2θ, 16.5 °2θ, 15.7 °2θ, 22.9 °2θ, 27.3 °2θ and 9.1 °2θ (±0.2 °2θ; ±0.1 °2θ; or 0.0 °2θ; Cu Kα1 radiation). In some embodiments, the mixture of two salts provided herein is a mixture of two crystalline salts provided herein characterized by XRPD signals at 25.6 °2θ, 16.4 °2θ, 20.7 °2θ, 17.0 °2θ, 19.5 °2θ, 16.5 °2θ, 15.7 °2θ, 22.9 °2θ, 27.3°2θ and 9.1 °2θ (±0.2 °2θ; ±0.1 °2θ; or ±0.0 °2θ; Cu Kα1 radiation).

In some embodiments, the a mixture of two salts provided herein is a mixture of two crystalline salts provided herein is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 144.

In some embodiments, the solid form of a mixture of two salts provided herein is a mixture of two crystalline salts provided herein characterized by two or more, or three or more XRPD signals selected from the group consisting of 19.5 °2θ, 20.6 °2θ, and 16.5°2θ (±0.2 °2θ; ±0.1 °2θ; or 0.0 °2θ; Cu Kα1 radiation). In some embodiments, the mixture of two salts provided herein is a mixture of two crystalline salts provided herein characterized by XRPD signals at 19.5 °2θ, 20.6 °2θ, and 16.5 °2θ (±0.2°2θ; ±0.1 °2θ; or ±0.0 °2θ; Cu Kα1 radiation).

In some embodiments, the solid form of a mixture of two salts provided herein is a mixture of two crystalline salts provided herein characterized by two or more, or three or more XRPD signals selected from the group consisting of 19.5 °2θ, 20.6 °2θ, 16.5 °2θ, 16.4 °2θ, and 25.4 °2θ (±0.2°2θ; ±0.1 °2θ; or ±0.0 °2θ; Cu Kα1 radiation). In some embodiments, the mixture of two salts provided herein is a mixture of two crystalline salts provided herein characterized by XRPD signals at 19.5 °2θ, 20.6 °2θ, 16.5 °2θ, 16.4 °2θ, and 25.4 °2θ (±0.2 °2θ; ±0.1°2θ; or ±0.0 °2θ; Cu Kα1 radiation).

In some embodiments, the solid form of a mixture of two salts provided herein is a mixture of two crystalline salts provided herein characterized by two or more, or three or more XRPD signals selected from the group consisting of 19.5 °2θ, 20.6 °2θ, 16.5 °2θ, 16.4 °2θ, 25.4 °2θ, 25.5 °2θ, and 17.0°2θ (±0.2 °2θ; ±0.1°2θ; or 0.0 °2θ; Cu Kα1 radiation). In some embodiments, the mixture of two salts provided herein is a mixture of two crystalline salts provided herein characterized by XRPD signals at 19.5 °2θ, 20.6 °2θ, 16.5 °2θ, 16.4 °2θ, 25.4 °2θ, 25.5 °2θ, and 17.0°2θ (±0.2°2θ; ±0.1°2θ; or ±0.0 °2θ; Cu Kα1 radiation).

In some embodiments, the solid form of a mixture of two salts provided herein is a mixture of two crystalline salts provided herein by two or more, or three or more XRPD signals selected from the group consisting of 19.5 °2θ, 20.6 °2θ, 16.5 °2θ, 16.4 °2θ, 25.4 °2θ, 25.5°2θ, 17.0 °2θ, 26.0 °2θ, 15.7 °2θ and 22.0°2θ (±0.2°2θ; ±0.1 °2θ; or 0.0 °2θ; Cu Kα1 radiation). In some embodiments, the mixture of two salts provided herein is a mixture of two crystalline salts provided herein characterized by XRPD signals at 19.5 °2θ, 20.6 °2θ, 16.5 °2θ, 16.4 °2θ, 25.4 °2θ, 25.5°2θ, 17.0 °2θ, 26.0 °2θ, 15.7 °2θ and 22.0°2θ (±0.2 °2θ; ±0.1 °2θ; or 0.0 °2θ; Cu Kα1 radiation).

In some embodiments, the a mixture of two salts provided herein is a mixture of two crystalline salts provided herein is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 145.

In some embodiments, the solid form of a mixture of two salts provided herein is a mixture of two crystalline salts provided herein by two or more, or three or more XRPD signals selected from the group consisting of 19.5 °2θ, 20.6 °2θ, 16.5 °2θ, 16.4 °2θ, 25.4 °2θ, 25.5°2θ, 17.0 °2θ, 26.1 °2θ, 15.7°2θ and 22.0°2θ (±0.2°2θ; ±0.1°2θ; or ±0.0 °2θ; Cu Kα1 radiation). In some embodiments, the mixture of two salts provided herein is a mixture of two crystalline salts provided herein characterized by XRPD signals at 19.5 °2θ, 20.6 °2θ, 16.5 °2θ, 16.4 °2θ, 25.4 °2θ, 25.5°2θ, 17.0 °2θ, 26.1 °2θ, 15.7 °2θ, 22.0 °2θ and 9.1°2θ (±0.2 °2θ; ±0.1 °2θ; or ±0.0 °2θ; Cu Kα1 radiation).

In some embodiments, the mixture of two salts provided herein is a mixture of two crystalline salts provided herein is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 146.

In some embodiments, the solid form of a mixture of two salts provided herein is a mixture of two crystalline salts provided herein characterized by two or more, or three or more XRPD signals selected from the group consisting of 19.5 °2θ, 16.5 °2θ, and 20.7°2θ (±0.2°2θ; ±0.1°2θ; or ±0.0 °2θ; Cu Kα1 radiation). In some embodiments, the mixture of two salts provided herein is a mixture of two crystalline salts provided herein characterized by XRPD signals at 19.5 °2θ, 16.5 °2θ, and 20.7 °2θ (±0.2 °2θ; ±0.1 °2θ; or ±0.0 °2θ; Cu Kα1 radiation).

In some embodiments, the solid form of a mixture of two salts provided herein is a mixture of two crystalline salts provided herein characterized by two or more, or three or more XRPD signals selected from the group consisting of 19.5 °2θ, 16.5 °2θ, 20.7 °2θ, 25.5°2θ, and 25.4°2θ (±0.2°2θ; ±0.1°2θ; or ±0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.7 °2θ, 25.5°2θ, and 25.4 °2θ (±0.2°2θ; ±0.1°2θ; or 0.0 °2θ; Cu Kα1 radiation).

In some embodiments, the solid form of a mixture of two salts provided herein is a mixture of two crystalline salts provided herein characterized by two or more, or three or more XRPD signals selected from the group consisting 19.5 °2θ, 16.5 °2θ, 20.7 °2θ, 25.5°2θ, 25.4 °2θ, 17.1 °2θ, and 26.1 °2θ (±0.2 °2θ; ±0.1°2θ; or 0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.7 °2θ, 25.5°2θ, 25.4 °2θ, 17.1 °2θ, and 26.1 °2θ (±0.2 °2θ; ±0.1°2θ; or 0.0 °2θ; Cu Kα1 radiation).

In some embodiments, the solid form of a mixture of two salts provided herein is a mixture of two crystalline salts provided herein by two or more, or three or more XRPD signals selected from the group consisting of 19.5 °2θ, 16.5 °2θ, 20.7 °2θ, 25.5°2θ, 25.4 °2θ, 17.1 °2θ, 26.1 °2θ, 15.7 °2θ, 18.1°2θ and 22.1°2θ (±0.2°2θ; ±0.1°2θ; or ±0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.7 °2θ, 25.5°2θ, 25.4 °2θ, 17.1 °2θ, 26.1 °2θ, 15.7 °2θ, 18.1°2θ and 22.1 (±0.2°2θ; ±0.1 °2θ; or 0.0 °2θ; Cu Kα1 radiation).

In some embodiments, the a mixture of two salts provided herein is a mixture of two crystalline salts provided herein is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 147.

In some embodiments, the solid form of a mixture of two salts provided herein is a mixture of two crystalline salts provided herein characterized by two or more, or three or more XRPD signals selected from the group consisting of 19.5 °2θ, 16.6 °2θ, and 16.5°2θ (±0.2°2θ; ±0.1 °2θ; or ±0.0 °2θ; Cu Kα1 radiation). In some embodiments, the mixture of two salts provided herein is a mixture of two crystalline salts provided herein characterized by XRPD signals at 19.5 °2θ, 16.6 °2θ, and 16.5°2θ (±0.2 °2θ; ±0.1°2θ; or ±0.0 °2θ; Cu Kα1 radiation).

In some embodiments, the solid form of a mixture of two salts provided herein is a mixture of two crystalline salts provided herein characterized by two or more, or three or more XRPD signals selected from the group consisting of 19.5 °2θ, 16.6 °2θ, 16.5 °2θ, 20.7 °2θ, and 25.4°2θ (±0.2 °2θ; ±0.1 °2θ; or 0.0 °2θ; Cu Kα1 radiation). In some embodiments, the mixture of two salts provided herein is a mixture of two crystalline salts provided herein characterized by XRPD signals at 19.5 °2θ, 16.6 °2θ, 16.5 °2θ, 20.7 °2θ, and 25.4°2θ (±0.2°2θ; ±0.1°2θ; or 0.0 °2θ; Cu Kα1 radiation).

In some embodiments, the solid form of a mixture of two salts provided herein is a mixture of two crystalline salts provided herein characterized by two or more, or three or more XRPD signals selected from the group consisting 19.5 °2θ, 16.6 °2θ, 16.5 °2θ, 20.7 °2θ, 25.4 °2θ, 25.5 °2θ, and 18.1°2θ (±0.2°2θ; ±0.1°2θ; or 0.0 °2θ; Cu Kα1 radiation). In some embodiments, the mixture of two salts provided herein is a mixture of two crystalline salts provided herein characterized by XRPD signals at 19.5 °2θ, 16.6 °2θ, 16.50 °2θ, 20.7 °2θ, 25.4°2θ, 25.5°2θ, and 18.1°2θ (±0.2°2θ; ±0.1 °2θ; or ±0.0 °2θ; Cu Kα1 radiation).

In some embodiments, the solid form of a mixture of two salts provided herein is a mixture of two crystalline salts provided herein by two or more, or three or more XRPD signals selected from the group consisting 19.5 °2θ, 16.6 °2θ, 16.50 °2θ, 20.7 °2θ, 25.4 °2θ, 25.5°2θ, 18.1 °2θ, 26.1 °2θ, 17.1 °2θ, and 17.8°2θ (±0.2°2θ; ±0.1°2θ; or 0.0 °2θ; Cu Kα1 radiation). In some embodiments, the mixture of two salts provided herein is a mixture of two crystalline salts provided herein characterized by XRPD signals at 19.5 °2θ, 16.6 °2θ, 16.5 °2θ, 20.7 °2θ, 25.4 °2θ, 25.5°2θ, 18.1 °2θ, 26.1 °2θ, 17.1 °2θ, and 17.8°2θ (±0.2°2θ; ±0.1°2θ; or 0.0 °2θ; Cu Kα1 radiation).

In some embodiments, the a mixture of two salts provided herein is a mixture of two crystalline salts provided herein is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 148.

In some embodiments, the solid form of a mixture of two salts provided herein is a mixture of two crystalline salts provided herein characterized by two or more, or three or more XRPD signals selected from the group consisting of 19.5 °2θ, 16.5 °2θ, and 20.7°2θ (±0.2°2θ; ±0.1 °2θ; or 0.0 °2θ; Cu Kα1 radiation). In some embodiments, the mixture of two salts provided herein is a mixture of two crystalline salts provided herein characterized by XRPD signals at 19.5 °2θ, 16.5 °2θ, and 20.7°2θ (±0.2 °2θ; ±0.1 °2θ; or 0.0 °2θ; Cu Kα1 radiation).

In some embodiments, the solid form of a mixture of two salts provided herein is a mixture of two crystalline salts provided herein characterized by two or more, or three or more XRPD signals selected from the group consisting of 19.5 °2θ, 16.5 °2θ, 20.7 °2θ, 25.4 °2θ, and 25.5 °2θ (±0.2 °2θ; ±0.1°2θ; or 0.0 °2θ; Cu Kα1 radiation). In some embodiments, the mixture of two salts provided herein is a mixture of two crystalline salts provided herein characterized by XRPD signals 19.5 °2θ, 16.5 °2θ, 20.7 °2θ, 25.4 °2θ, and 25.5 °2θ (±0.2°2θ; ±0.1°2θ; or ±0.0 °2θ; Cu Kα1 radiation).

In some embodiments, the solid form of a mixture of two salts provided herein is a mixture of two crystalline salts provided herein characterized by two or more, or three or more XRPD signals selected from the group consisting 19.5 °2θ, 16.5 °2θ, 20.7 °2θ, 25.4 °2θ, 25.5°2θ, 17.1 °2θ, and 26.1°2θ (±0.2°2θ; ±0.1°2θ; or 0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.7 °2θ, 25.4 °2θ, 25.5°2θ, 17.1 °2θ, and 26.1°2θ (±0.2°2θ; ±0.1°2θ; or 0.0 °2θ; Cu Kα1 radiation).

In some embodiments, the solid form of a mixture of two salts provided herein is a mixture of two crystalline salts provided herein by two or more, or three or more XRPD signals selected from the group consisting of 19.5 °2θ, 16.5 °2θ, 20.7 °2θ, 25.4 °2θ, 25.5 °2θ, 17.1 °2θ, 26.1 °2θ, 15.7 °2θ, 22.1°2θ and 22.9°2θ (±0.2°2θ; ±0.1°2θ; or 0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.7 °2θ, 25.4 °2θ, 25.5°2θ, 17.1 °2θ, 26.1 °2θ, 15.7 °2θ, 22.1°2θ and 22.9°2θ (±0.2°2θ; ±0.1°2θ; or ±0.0 °2θ; Cu Kα1 radiation). In some embodiments, the a mixture of two salts provided herein is a mixture of two crystalline salts provided herein is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 149.

In some embodiments, the solid form of a mixture of two salts provided herein is a mixture of two crystalline salts provided herein characterized by two or more, or three or more XRPD signals selected from the group consisting of 19.5 °2θ, 16.5 °2θ, and 20.6°2θ (±0.2°2θ; ±0.1 °2θ; or ±0.0

°2θ; Cu Kα1 radiation). In some embodiments, the mixture of two salts provided herein is a mixture of two crystalline salts provided herein characterized by XRPD signals at 19.5 °2θ, 16.5 °2θ, and 20.6°2θ (±0.2 °2θ; ±0.1 °2θ; or ±0.0 °2θ; Cu Kα1 radiation).

In some embodiments, the solid form of a mixture of two salts provided herein is a mixture of two crystalline salts provided herein characterized by two or more, or three or more XRPD signals selected from the group consisting of 19.5 °2θ, 16.5 °2θ, 20.6 °2θ, 25.4 °2θ, and 26.1°2θ (±0.2 °2θ; ±0.1 °2θ; or 0.0 °2θ; Cu Kα1 radiation). In some embodiments, the mixture of two salts provided herein is a mixture of two crystalline salts provided herein characterized by XRPD signals 19.5 °2θ, 16.5 °2θ, 20.6 °2θ, 25.4 °2θ, and 26.1°2θ (±0.2°2θ; ±0.1°2θ; or 0.0 °2θ; Cu Kα1 radiation).

In some embodiments, the solid form of a mixture of two salts provided herein is a mixture of two crystalline salts provided herein characterized by two or more, or three or more XRPD signals selected from the group consisting 19.5 °2θ, 16.5 °2θ, 20.6 °2θ, 25.4 °2θ, 26.1 °2θ, 17.0 °2θ, and 15.7°2θ (±0.2°2θ; ±0.1°2θ; or 0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.6 °2θ, 25.4 °2θ, 26.1 °2θ, 17.0 °2θ, and 15.7°2θ (±0.2°2θ; ±0.1°2θ; or 0.0 °2θ; Cu Kα1 radiation).

In some embodiments, the solid form of a mixture of two salts provided herein is a mixture of two crystalline salts provided herein by two or more, or three or more XRPD signals selected from the group consisting of 19.5 °2θ, 16.5 °2θ, 20.6 °2θ, 25.4 °2θ, 26.1 °2θ, 17.0 °2θ, 15.7 °2θ, 22.1 °2θ, 9.1°2θ and 12.9°2θ (±0.2 °2θ; ±0.1 °2θ; or 0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.6 °2θ, 25.4 °2θ, 26.1 °2θ, 17.0 °2θ, 15.7 °2θ, 22.1 °2θ, 9.1°2θ and 12.9 °2θ (±0.2 °2θ; ±0.1°2θ; or 0.0 °2θ; Cu Kα1 radiation).

In some embodiments, the a mixture of two salts provided herein is a mixture of two crystalline salts provided herein is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 150.

In some embodiments, the solid form of a mixture of two salts provided herein is a mixture of two crystalline salts provided herein characterized by two or more, or three or more XRPD signals selected from the group consisting of 19.5 °2θ, 16.5 °2θ, 20.6 °2θ, 16.4 °2θ, and 25.3°2θ (±0.2 °2θ; ±0.1°2θ; or 0.0 °2θ; Cu Kα1 radiation). In some embodiments, the mixture of two salts provided herein is a mixture of two crystalline salts provided herein characterized by XRPD signals 19.5 °2θ, 16.5 °2θ, 20.6 °2θ, 16.4 °2θ, and 25.3°2θ (±0.2°2θ; ±0.1°2θ; or ±0.0 °2θ; Cu Kα1 radiation).

In some embodiments, the solid form of a mixture of two salts provided herein is a mixture of two crystalline salts provided herein characterized by two or more, or three or more XRPD signals selected from the group 19.5 °2θ, 16.5 °2θ, 20.6 °2θ, 16.4 °2θ, 25.3 °2θ, 25.5°2θ, and 26.0 °2θ (±0.2°2θ; ±0.1°2θ; or ±0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.6 °2θ, 16.4 °2θ, 25.3 °2θ, 25.5°2θ, and 26.0°2θ (±0.2°2θ; ±0.1 °2θ; or ±0.0 °2θ; Cu Kα1 radiation).

In some embodiments, the solid form of a mixture of two salts provided herein is a mixture of two crystalline salts provided herein by two or more, or three or more XRPD signals selected from the group consisting of 19.5 °2θ, 16.5 °2θ, 20.6 °2θ, 16.4 °2θ, 25.3 °2θ, 25.5 °2θ, 26.0 °2θ, 17.0 °2θ, 22.0°2θ and 18.0°2θ (±0.2°2θ; ±0.1°2θ; or 0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.6 °2θ, 16.4 °2θ, 25.3 °2θ, 25.5 °2θ, 26.0 °2θ, 17.0 °2θ, 22.0 °2θ and 18.0°2θ (±0.2 °2θ; ±0.1 °2θ; or 0.0 °2θ; Cu Kα1 radiation).

In some embodiments, the a mixture of two salts provided herein is a mixture of two crystalline salts provided herein is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 151.

In some embodiments, the solid form of a mixture of two salts provided herein is a mixture of two crystalline salts provided herein characterized by two or more, or three or more XRPD signals selected from the group consisting of 19.6 °2θ, 16.6 °2θ, and 20.7 °2θ (±0.2 °2θ; ±0.1°2θ; or 0.0 °2θ; Cu Kα1 radiation). In some embodiments, the mixture of two salts provided herein is a mixture of two crystalline salts provided herein characterized by XRPD signals at 19.6 °2θ, 16.6 °2θ, and 20.7 °2θ (±0.2°2θ; ±0.1°2θ; or 0.0 °2θ; Cu Kα1 radiation).

In some embodiments, the solid form of a mixture of two salts provided herein is a mixture of two crystalline salts provided herein characterized by two or more, or three or more XRPD signals selected from the group consisting of 19.6 °2θ, 16.6 °2θ, 20.7 °2θ, 25.4 °2θ, and 26.2 °2θ (±0.2°2θ; ±0.1 °2θ; or 0.0 °2θ; Cu Kα1 radiation). In some embodiments, the mixture of two salts provided herein is a mixture of two crystalline salts provided herein characterized by XRPD signals at 9.6 °2θ, 16.6 °2θ, 20.7 °2θ, 25.4 °2θ, and 26.2°2θ (±0.2°2θ; ±0.1°2θ; or 0.0 °2θ; Cu Kα1 radiation).

In some embodiments, the solid form of a mixture of two salts provided herein is a mixture of two crystalline salts provided herein characterized by two or more, or three or more XRPD signals selected from the group consisting of 19.6 °2θ, 16.6 °2θ, 20.7 °2θ, 25.4 °2θ, 26.2 °2θ, 18.1 °2θ, and 22.1°2θ (±0.2 °2θ; ±0.1°2θ; or 0.0 °2θ; Cu Kα1 radiation). In some embodiments, the mixture of two salts provided herein is a mixture of two crystalline salts provided herein characterized by XRPD signals at 19.6 °2θ, 16.6 °2θ, 20.7 °2θ, 25.4 °2θ, 26.2 °2θ, 18.1 °2θ, and 22.1°2θ (±0.2°2θ; ±0.1°2θ; or ±0.0 °2θ; Cu Kα1 radiation).

In some embodiments, the solid form of a mixture of two salts provided herein is a mixture of two crystalline salts provided herein by two or more, or three or more XRPD signals selected from the group consisting of 19.6 °2θ, 16.6 °2θ, 20.7 °2θ, 25.4 °2θ, 26.2 °2θ, 18.1 °2θ, 22.1 °2θ, 17.1 °2θ, 17.8 °2θ, and 15.8 °2θ (±0.2 °2θ; ±0.1 °2θ; or 0.0 °2θ; Cu Kα1 radiation). In some embodiments, the mixture of two salts provided herein is a mixture of two crystalline salts provided herein characterized by XRPD signals at 19.6 °2θ, 16.6 °2θ, 20.7 °2θ, 25.4 °2θ, 26.2 °2θ, 18.1 °2θ, 22.1 °2θ, 17.1 °2θ, 17.8 °2θ, and 15.8 °2θ (±0.2 °2θ; ±0.1°2θ; or ±0.0 °2θ; Cu Kα1 radiation).

In some embodiments, the a mixture of two salts provided herein is a mixture of two crystalline salts provided herein is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 152.

In some embodiments, the solid form of a mixture of two salts provided herein is a mixture of two crystalline salts provided herein characterized by two or more, or three or more XRPD signals selected from the group consisting of 19.5 °2θ, 16.5 °2θ, 20.7 °2θ, 25.4 °2θ, and 18.0°2θ (±0.2 °2θ; ±0.1°2θ; or ±0.0 °2θ; Cu Kα1 radiation). In some embodiments, the mixture of two salts provided herein is a mixture of two crystalline salts provided herein characterized by XRPD signals 19.5 °2θ, 16.5 °2θ, 20.7 °2θ, 25.4 °2θ, and 18.0°2θ (±0.2°2θ; ±0.1°2θ; or 0.0 °2θ; Cu Kα1 radiation).

In some embodiments, the solid form of a mixture of two salts provided herein is a mixture of two crystalline salts provided herein characterized by two or more, or three or more XRPD signals selected from the group consisting 19.5 °2θ, 16.5 °2θ, 20.7 °2θ, 25.4 °2θ, 18.0 °2θ, 17.7 °2θ, and 26.1 °2θ (±0.2 °2θ; ±0.1°2θ; or ±0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.7 °2θ, 25.4 °2θ, 18.0 °2θ, 17.7 °2θ, and 26.1°2θ (±0.2°2θ; ±0.1°2θ; or 0.0 °2θ; Cu Kα1 radiation).

In some embodiments, the solid form of a mixture of two salts provided herein is a mixture of two crystalline salts provided herein by two or more, or three or more XRPD signals selected from the group consisting of 19.5 °2θ, 16.5 °2θ, 20.7 °2θ, 25.4 °2θ, 18.0 °2θ, 17.7 °2θ, 26.1 °2θ, 22.1 °2θ, 22.9 °2θ and 12.9 °2θ (±0.2 °2θ; ±0.1 °2θ; or 0.0 °2θ; Cu Kα1 radiation). In some embodiments, the mixture of two salts provided herein is a mixture of two crystalline salts provided herein characterized by XRPD signals at 19.5 °2θ, 16.5 °2θ, 20.7 °2θ, 25.4 °2θ, 18.0 °2θ, 17.7 °2θ, 26.1 °2θ, 22.1 °2θ, 22.9 °2θ and 12.9 °2θ (±0.2 °2θ; 0.1 °2θ; or ±0.0 °2θ; Cu Kα1 radiation).

In some embodiments, the a mixture of two salts provided herein is a mixture of two crystalline salts provided herein is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 153.

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.5 °2θ, 16.3 °2θ, and 19.3 °2θ (±0.2 °2θ; ±0.1 °2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.5 °2θ, 16.3 °2θ, and 19.3 °2θ (±0.2 °2θ; ±0.1 °2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.5 °2θ, 16.3 °2θ, 19.3 °2θ, 16.7 °2θ, and 18.1 °2θ (±0.2 °2θ; ±0.1 °2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.5 °2θ, 16.3 °2θ, 19.3 °2θ, 16.7 °2θ, and 18.1 °2θ (±0.2 °2θ; ±0.1 °2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.5 °2θ, 16.3 °2θ, 19.3 °2θ, 16.7 °2θ, 18.1 °2θ, 26.8 °2θ, and 27.2 °2θ (±0.2 °2θ; ±0.1 °2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.5 °2θ, 16.3°2θ, 19.3 °2θ, 16.7 °2θ, 18.1 °2θ, 26.8 °2θ, and 27.2°2θ (±0.2 °2θ; ±0.1°2θ; or ±0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.5°2θ, 16.3°2θ, 19.3 °2θ, 16.7 °2θ, 18.1 °2θ, 26.8 °2θ, 27.2 °2θ, 9.0 °2θ, 22.3°2θ and 25.1 °2θ (±0.2°2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.5°2θ, 16.3°2θ, 19.3 °2θ, 16.7 °2θ, 18.1 °2θ, 26.8 °2θ, 27.2 °2θ, 9.0 °2θ, 22.3°2θ and 25.1 °2θ (±0.2 °2θ; ±0.1 °2θ; or ±0.0 °2θ; Cu Kα1 radiation).

In some embodiments, the crystalline tabernanthalog monofumarate salt Pattern #1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 155.

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.5 °2θ, 16.3°2θ, 19.3 °2θ, 16.7 °2θ, 18.1 °2θ, 26.8 °2θ, and 9.0°2θ (±0.2°2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.5°2θ, 16.3°2θ, 19.3 °2θ, 16.7 °2θ, 18.1 °2θ, 26.8 °2θ, and 9.0 °2θ (±0.2°2θ; ±0.1°2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.5 °2θ, 16.3 °2θ, 19.3 °2θ, 16.7 °2θ, 18.1 °2θ, 26.8°2θ, 9.0 °2θ, 22.3 °2θ, 27.2 °2θ and 24.6 °2θ (±0.2 °2θ; ±0.1 °2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at of 25.5°2θ, 16.3°2θ, 19.3 °2θ, 16.7 °2θ, 18.1 °2θ, 26.8 °2θ, 9.0 °2θ, 22.3 °2θ, 27.2 °2θ and 24.6°2θ (±0.2°2θ; ±0.1 °2θ; or 0.0 °2θ; Cu Kα1 radiation).

In some embodiments, the crystalline tabernanthalog monofumarate salt Pattern #1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 156.

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.5°2θ, 16.3°2θ, and 19.3°2θ (±0.2 °2θ; ±0.1 °2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.5°2θ, 16.3°2θ, and 19.3°2θ (±0.2°2θ; ±0.1°2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.5°2θ, 16.3°2θ, 19.3 °2θ, 16.7 °2θ, and 5.1 °2θ (±0.2 °2θ; ±0.1 °2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.5°2θ, 16.3 °2θ, 19.3 °2θ, 16.7 °2θ, and 5.1 °2θ (±0.2 °2θ; ±0.1°2θ; or 0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.5°2θ, 16.3°2θ, 19.3 °2θ, 16.7 °2θ, 5.1 °2θ, 10.2 °2θ, and 27.2 °2θ (±0.2 °2θ; ±0.1°2θ; or ±0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.5°2θ, 16.3°2θ, 19.3 °2θ, 16.7 °2θ, 5.1 °2θ, 10.2 °2θ, and 27.2°2θ (±0.2°2θ; ±0.1 °2θ; or ±0.0 °2θ; Cu Kα1 radiation).

In some embodiments, the solid form of tabernanthalog monofumarate salt Pattern #1 is crystalline tabernanthalog monofumarate salt Pattern #1 characterized by two or more, or three or more XRPD signals selected from the group consisting of 25.5°2θ, 16.3°2θ, 19.3 °2θ, 16.7 °2θ, 5.1 °2θ, 10.2°2θ, 27.2 °2θ, 18.1 °2θ, 9.0°2θ and 26.8°2θ (±0.2°2θ; ±0.1°2θ; or 0.0 °2θ; Cu Kα1 radiation). In some embodiments, the solid form of tabernanthalog monofumarate salt Pattern #1 is crystalline tabernanthalog monofumarate salt Pattern #1 characterized by XRPD signals at 25.5 °2θ, 16.3°2θ, 19.3 °2θ, 16.7 °2θ, 5.1 °2θ, 10.2°2θ, 27.2 °2θ, 18.1 °2θ, 9.0°2θ and 26.8°2θ (±0.2°2θ; ±0.1 °2θ; or ±0.0 °2θ; Cu Kα1 radiation).

In some embodiments, the crystalline tabernanthalog monofumarate salt Pattern #1 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 157.

In some embodiments, the solid form of tabernanthalog monofumarate Pattern #2a is crystalline tabernanthalog monofumarate Pattern #2a characterized by two or more, or three or more XRPD signals selected from the group consisting of 25.6 °2θ, 16.4 °2θ, and 17.1°2θ (±0.2°2θ; ±0.1°2θ; or 0.0 °2θ; Cu Kα1 radiation). In some embodiments, the solid form of tabernanthalog monofumarate Pattern #2a is tabernanthalog monofumarate Pattern #2a characterized by XRPD signals at 25.6 °2θ, 16.4 °2θ, and 17.1°2θ (±0.2°2θ; ±0.1°2θ; or 0.0 °2θ; Cu Kα1 radiation).

In some embodiments, the solid form of tabernanthalog monofumarate Pattern #2a is crystalline tabernanthalog monofumarate Pattern #2a characterized by two or more, or three or more XRPD signals selected from the group consisting of 25.6 °2θ, 16.4 °2θ, 17.1 °2θ, 9.1 °2θ, and 23.0 °2θ (±0.2 °2θ; ±0.1°2θ; or 0.0 °2θ; Cu Kα1 radiation). In some embodiments, the solid form of tabernanthalog monofumarate Pattern #2a is crystalline tabernanthalog monofumarate Pattern #2a characterized by XRPD signals at 25.6 °2θ, 16.4 °2θ, 17.1 °2θ, 9.1 °2θ, and 23.0°2θ (±0.2 °2θ; ±0.1 °2θ; or ±0.0 °2θ; Cu Kα1 radiation).

In some embodiments, the solid form of tabernanthalog monofumarate Pattern #2a is crystalline tabernanthalog monofumarate Pattern #2a characterized by two or more, or three or more XRPD signals selected from the group consisting of 25.6 °2θ, 16.4 °2θ, 17.1 °2θ, 9.1 °2θ, 23.0 °2θ, 27.3 °2θ, and 15.7 °2θ (±0.2°2θ; ±0.1°2θ; or 0.0 °2θ; Cu Kα1 radiation). In some embodiments, the solid form of tabernanthalog monofumarate Pattern #2a is crystalline tabernanthalog monofumarate Pattern #2a characterized by XRPD signals at of 25.6 °2θ, 16.4 °2θ, 17.1 °2θ, 9.1 °2θ, 23.0 °2θ, 27.3 °2θ, and 15.7 °2θ (±0.2°2θ; ±0.1 °2θ; or ±0.0 °2θ; Cu Kα1 radiation).

In some embodiments, the solid form of tabernanthalog monofumarate Pattern #2a is crystalline tabernanthalog monofumarate Pattern #2a characterized by two or more, or three or more XRPD signals selected from the group consisting of 25.6 °2θ, 16.4 °2θ, 17.1 °2θ, 9.1 °2θ, 23.0 °2θ, 27.3 °2θ, 15.7 °2θ, 26.8 °2θ, 18.1 °2θ, and 20.7°2θ (±0.2 °2θ; ±0.1°2θ; or 0.0 °2θ; Cu Kα1 radiation). In some embodiments, the solid form of tabernanthalog monofumarate Pattern #2a is crystalline tabernanthalog monofumarate Pattern #2a characterized by XRPD signals at 25.6 °2θ, 16.4 °2θ, 17.1 °2θ, 9.1 °2θ, 23.0 °2θ, 27.3 °2θ, 15.7 °2θ, 26.8 °2θ, 18.1 °2θ, and 20.7°2θ (±0.2 °2θ; ±0.1 °2θ; or 0.0 °2θ; Cu Kα1 radiation).

In some embodiments, the crystalline tabernanthalog monofumarate Pattern #2a is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 158.

In some embodiments, the solid form of tabernanthalog monofumarate Pattern #2b is crystalline tabernanthalog monofumarate Pattern #2b characterized by two or more, or three or more XRPD signals selected from the group consisting of 25.5 °2θ, 16.3 °2θ, and 24.6°2θ (±0.2 °2θ; ±0.1 °2θ; or 0.0 °2θ; Cu Kα1 radiation). In some embodiments, the solid form of tabernanthalog monofumarate Pattern #2b is crystalline tabernanthalog monofumarate Pattern #2b characterized by XRPD signals at 25.5°2θ, 16.3 °2θ, and 24.6°2θ (±0.2 °2θ; ±0.1 °2θ; or 0.0 °2θ; Cu Kα1 radiation).

In some embodiments, the solid form of tabernanthalog monofumarate Pattern #2b is crystalline tabernanthalog monofumarate Pattern #2b characterized by two or more, or three or more XRPD signals selected from the group consisting of 25.5°2θ, 16.3°2θ, 24.6 °2θ, 18.1 °2θ, and 9.0°2θ (±0.2°2θ; ±0.1 °2θ; or ±0.0 °2θ; Cu Kα1 radiation). In some embodiments, the solid form of tabernanthalog monofumarate Pattern #2b is crystalline tabernanthalog monofumarate Pattern #2b characterized by XRPD signals at 25.5°2θ, 16.3°2θ, 24.6 °2θ, 18.1 °2θ, and 9.0°2θ (±0.2°2θ; ±0.1 °2θ; or 0.0 °2θ; Cu Kα1 radiation).

In some embodiments, the solid form of tabernanthalog monofumarate Pattern #2b is crystalline tabernanthalog monofumarate Pattern #2b characterized by two or more, or three or more XRPD signals selected from the group consisting of 25.5°2θ, 16.3°2θ, 24.6 °2θ, 18.1 °2θ, 9.0 °2θ, 25.1 °2θ, and 15.8 °2θ (±0.2 °2θ; ±0.1°2θ; or ±0.0 °2θ; Cu Kα1 radiation). In some embodiments, the solid form of tabernanthalog monofumarate Pattern #2b is crystalline tabernanthalog monofumarate Pattern #2b characterized by XRPD signals at 25.5°2θ, 16.3 °2θ, 24.6°2θ, 18.1 °2θ, 9.0 °2θ, 25.1 °2θ, and 15.8 °2θ (±0.2°2θ; ±0.1 °2θ; or ±0.0 °2θ; Cu Kα1 radiation).

In some embodiments, the solid form of tabernanthalog monofumarate Pattern #2b is crystalline tabernanthalog monofumarate Pattern #2b characterized by two or more, or three or more XRPD signals selected from the group consisting of 25.5°2θ, 16.3 °2θ, 24.6°2θ, 18.1 °2θ, 9.0 °2θ, 25.1 °2θ, 15.8 °2θ, 26.8 °2θ, 15.5 °2θ, and 17.0°2θ (±0.2 °2θ; ±0.1°2θ; or ±0.0 °2θ; Cu Kα1 radiation). In some embodiments, the solid form of tabernanthalog monofumarate Pattern #2b is crystalline tabernanthalog monofumarate Pattern #2b characterized by XRPD signals at 25.5 °2θ, 16.3°2θ, 24.6 °2θ, 18.1 °2θ, 9.0 °2θ, 25.1 °2θ, 15.8 °2θ, 26.8 °2θ, 15.5 °2θ, and 17.0°2θ (±0.2 °2θ; ±0.1 °2θ; or ±0.0 °2θ; Cu Kα1 radiation).

In some embodiments, the crystalline tabernanthalog monofumarate Pattern #2b is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 159.

In some embodiments, the solid form of tabernanthalog monofumarate Pattern #2c is crystalline tabernanthalog monofumarate Pattern #2c characterized by two or more, or three or more XRPD signals selected from the group consisting of 25.5 °2θ, 16.3 °2θ, and 19.3 °2θ (±0.2 °2θ; ±0.1°2θ; or ±0.0 °2θ; Cu Kα1 radiation). In some embodiments, the solid form of tabernanthalog monofumarate Pattern #2c is crystalline tabernanthalog monofumarate Pattern #2c characterized by XRPD signals at 25.5 °2θ, 16.3°2θ, and 19.3 °2θ (±0.2 °2θ; ±0.1 °2θ; or ±0.0 °2θ; Cu Kα1 radiation).

In some embodiments, the solid form of tabernanthalog monofumarate Pattern #2c is crystalline tabernanthalog monofumarate Pattern #2c characterized by two or more, or three or more XRPD signals selected from the group consisting of 25.5 °2θ, 16.3 °2θ, 19.3 °2θ, 16.7 °2θ, and 22.3 °2θ (±0.2 °2θ; ±0.1°2θ; or 0.0 °2θ; Cu Kα1 radiation). In some embodiments, the solid form of tabernanthalog monofumarate Pattern #2c is crystalline tabernanthalog monofumarate Pattern #2c characterized by XRPD signals at 25.5 °2θ, 16.3 °2θ, 19.3 °2θ, 16.7 °2θ, and 22.3 °2θ (±0.2°2θ; ±0.1 °2θ; or ±0.0 °2θ; Cu Kα1 radiation).

In some embodiments, the solid form of tabernanthalog monofumarate Pattern #2c is crystalline tabernanthalog monofumarate Pattern #2c characterized by two or more, or three or more XRPD signals selected from the group consisting of 25.5 °2θ, 16.3 °2θ, 19.3 °2θ, 16.7 °2θ, 22.3 °2θ, 9.0 °2θ, and 27.2°2θ (±0.2 °2θ; ±0.1 °2θ; or 0.0 °2θ; Cu Kα1 radiation). In some embodiments, the solid form of tabernanthalog monofumarate Pattern #2c is crystalline tabernanthalog monofumarate Pattern #2c characterized by XRPD signals at 25.5 °2θ, 16.3 °2θ, 19.3 °2θ, 16.7 °2θ, 22.3 °2θ, 9.0 °2θ, and 27.2°2θ (±0.2°2θ; ±0.1°2θ; or 0.0 °2θ; Cu Kα1 radiation).

In some embodiments, the solid form of tabernanthalog monofumarate Pattern #2c is crystalline tabernanthalog monofumarate Pattern #2c characterized by two or more, or three or more XRPD signals selected from the group consisting of 25.5 °2θ, 16.3°2θ, 19.3 °2θ, 16.7°2θ, 22.3 °2θ, 9.0 °2θ, 27.2 °2θ, 18.1 °2θ, 26.8 °2θ, and 17.7°2θ (±0.2°2θ; ±0.1°2θ; or ±0.0 °2θ; Cu Kα1 radiation). In some embodiments, the solid form of tabernanthalog monofumarate Pattern #2c is crystalline tabernanthalog monofumarate Pattern #2c characterized by XRPD signals at 25.5 °2θ, 16.3°2θ, 19.3 °2θ, 16.7 °2θ, 22.3 °2θ, 9.0 °2θ, 27.2 °2θ, 18.1 °2θ, 26.8 °2θ, and 17.7 °2θ (±0.2°2θ; ±0.1°2θ; or 0.0 °2θ; Cu Kα1 radiation).

In some embodiments, the crystalline tabernanthalog monofumarate Pattern #2c is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 160.

In some embodiments, the solid form of tabernanthalog monofumarate Pattern #2d is crystalline tabernanthalog monofumarate Pattern #2d characterized by two or more, or three or more XRPD signals selected from the group consisting of 25.6 °2θ, 16.3 °2θ, and 16.2°2θ (±0.2 °2θ; ±0.1°2θ; or 0.0 °2θ; Cu Kα1 radiation). In some embodiments, the solid form of tabernanthalog monofumarate Pattern #2d is crystalline tabernanthalog monofumarate Pattern #2d characterized by XRPD signals at 25.6 °2θ, 16.3 °2θ, and 16.2 °2θ (±0.2 °2θ; ±0.1 °2θ; or ±0.0 °2θ; Cu Kα1 radiation).

In some embodiments, the solid form of tabernanthalog monofumarate Pattern #2d is crystalline tabernanthalog monofumarate Pattern #2d characterized by two or more, or three or more XRPD signals selected from the group consisting of 25.6 °2θ, 16.3°2θ, 16.2 °2θ, 25.2 °2θ, and 9.1°2θ (±0.2°2θ; ±0.1°2θ; or ±0.0 °2θ; Cu Kα1 radiation). In some embodiments, the solid form of tabernanthalog monofumarate Pattern #2d is crystalline tabernanthalog monofumarate Pattern #2d characterized by XRPD signals at 25.6 °2θ, 16.3 °2θ, 16.2 °2θ, 25.2 °2θ, and 9.1°2θ (±0.2 °2θ; ±0.1°2θ; or 0.0 °2θ; Cu Kα1 radiation).

In some embodiments, the solid form of tabernanthalog monofumarate Pattern #2d is crystalline tabernanthalog monofumarate Pattern #2d characterized by two or more, or three or more XRPD signals selected from the group consisting of 25.6 °2θ, 16.3°2θ, 16.2 °2θ, 25.2 °2θ, 9.1 °2θ, 22.1 °2θ, and 26.0 °2θ (±0.2 °2θ; ±0.1 °2θ; or ±0.0 °2θ; Cu Kα1 radiation). In some embodiments, the solid form of tabernanthalog monofumarate Pattern #2d is crystalline tabernanthalog monofumarate Pattern #2d characterized by XRPD signals at 25.6 °2θ, 16.3°2θ, 16.2 °2θ, 25.2 °2θ, 9.1 °2θ, 22.1 °2θ, and 26.0°2θ (±0.2°2θ; ±0.1 °2θ; or ±0.0 °2θ; Cu Kα1 radiation).

In some embodiments, the solid form of tabernanthalog monofumarate Pattern #2d is crystalline tabernanthalog monofumarate Pattern #2d characterized by two or more, or three or more XRPD signals selected from the group consisting of 25.6 °2θ, 16.3 °2θ, 16.2 °2θ, 25.2 °2θ, 9.1 °2θ, 22.1 °2θ, 26.0 °2θ, 26.8 °2θ, 18.1 °2θ, and 19.9°2θ (±0.2 °2θ; ±0.1 °2θ; or 0.0 °2θ; Cu Kα1 radiation). In some embodiments, the solid form of tabernanthalog monofumarate Pattern #2d is crystalline tabernanthalog monofumarate Pattern #2d characterized by XRPD signals at 25.6 °2θ, 16.3°2θ, 16.2 °2θ, 25.2 °2θ, 9.1 °2θ, 22.1 °2θ, 26.0 °2θ, 26.8 °2θ, 18.1 °2θ, and 19.9°2θ (±0.2°2θ; ±0.1 °2θ; or ±0.0 °2θ; Cu Kα1 radiation).

In some embodiments, the crystalline tabernanthalog monofumarate Pattern #2d is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 161.

In some embodiments, the solid form of tabernanthalog monofumarate salt Pattern #3 is crystalline tabernanthalog monofumarate salt Pattern #3 characterized by two or more, or three or more XRPD signals selected from the group consisting of 25.5°2θ, 16.3 °2θ, and 16.6 °2θ (±0.2 °2θ; ±0.1 °2θ; or 0.0 °2θ; Cu Kα1 radiation). In some embodiments, the solid form of tabernanthalog monofumarate salt Pattern #3 is crystalline tabernanthalog monofumarate salt Pattern #3 characterized by XRPD signals at 25.5°2θ, 16.3°2θ, and 16.6°2θ (±0.2°2θ; ±0.1°2θ; or 0.0 °2θ; Cu Kα1 radiation).

In some embodiments, the solid form of tabernanthalog monofumarate salt Pattern #3 is crystalline tabernanthalog monofumarate salt Pattern #3 characterized by two or more, or three or more XRPD signals selected from the group consisting of 25.5 °2θ, 16.3°2θ, 16.6 °2θ, 20.1 °2θ, and 26.0°2θ (±0.2°2θ; ±0.1 °2θ; or 0.0 °2θ; Cu Kα1 radiation). In some embodiments, the solid form of tabernanthalog monofumarate salt Pattern #3 is crystalline tabernanthalog monofumarate salt Pattern #3 characterized by XRPD signals at 25.5 °2θ, 16.3°2θ, 16.6 °2θ, 20.1°2θ, and 26.0 °2θ (±0.2°2θ; ±0.1 °2θ; or 0.0 °2θ; Cu Kα1 radiation).

In some embodiments, the solid form of tabernanthalog monofumarate salt Pattern #3 is crystalline tabernanthalog monofumarate salt Pattern #3 characterized by two or more, or three or more XRPD signals selected from the group consisting of 25.5 °2θ, 16.3 °2θ, 16.6 °2θ, 20.1 °2θ, 26.0 °2θ, 22.2 °2θ, and 26.8 °2θ (±0.2 °2θ; ±0.1 °2θ; or 0.0 °2θ; Cu Kα1 radiation). In some embodiments, the solid form of tabernanthalog monofumarate salt Pattern #3 is crystalline tabernanthalog monofumarate salt Pattern #3 characterized by XRPD signals at 25.5 °2θ, 16.3 °2θ, 16.6 °2θ, 20.1 °2θ, 26.0 °2θ, 22.2 °2θ, and 26.8°2θ (±0.2 °2θ; ±0.1 °2θ; or ±0.0 °2θ; Cu Kα1 radiation).

In some embodiments, the solid form of tabernanthalog monofumarate salt Pattern #3 is crystalline tabernanthalog monofumarate salt Pattern #3 characterized by two or more, or three or more XRPD signals selected from the group consisting of 25.5 °2θ, 16.3 °2θ, 16.6 °2θ, 20.1 °2θ, 26.0 °2θ, 22.2 °2θ, 26.8 °2θ, 16.8 °2θ, 18.8 °2θ, and 9.0°2θ (±0.2 °2θ; ±0.1 °2θ; or ±0.0 °2θ; Cu Kα1 radiation). In some embodiments, the solid form of tabernanthalog monofumarate salt Pattern #3 is crystalline tabernanthalog monofumarate salt Pattern #3 characterized by XRPD signals at 25.5 °2θ, 16.3 °2θ, 16.6 °2θ, 20.1 °2θ, 26.0 °2θ, 22.2 °2θ, 26.8 °2θ, 16.8 °2θ, 18.8 °2θ, and 9.0°2θ (±0.2 °2θ; 0.1°2θ; or ±0.0 °2θ; Cu Kα1 radiation).

In some embodiments, the crystalline tabernanthalog monofumarate salt Pattern #3 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 162.

In some embodiments, the solid form of tabernanthalog monofumarate salt Pattern #4a is crystalline tabernanthalog monofumarate salt Pattern #4a characterized by two or more, or three or more XRPD signals selected from the group consisting of 25.5 °2θ, 16.3°2θ, and 8.2°2θ (±0.2 °2θ; ±0.1°2θ; or ±0.0 °2θ; Cu Kα1 radiation). In some embodiments, the solid form of tabernanthalog monofumarate salt Pattern #4a is crystalline tabernanthalog monofumarate salt Pattern #4a characterized by XRPD signals at 25.5 °2θ, 16.3°2θ, and 8.2°2θ (±0.2 °2θ; ±0.1 °2θ; or ±0.0 °2θ; Cu Kα1 radiation).

In some embodiments, the solid form of tabernanthalog monofumarate salt Pattern #4a is crystalline tabernanthalog monofumarate salt Pattern #4a characterized by two or more, or three or more XRPD signals selected from the group consisting of 25.5 °2θ, 16.3 °2θ, 8.2 °2θ, 11.3 °2θ, and 9.0 °2θ (±0.2 °2θ; ±0.1 °2θ; or ±0.0 °2θ; Cu Kα1 radiation). In some embodiments, the solid form of tabernanthalog monofumarate salt Pattern #4a is crystalline tabernanthalog monofumarate salt Pattern #4a characterized by XRPD signals at 25.5 °2θ, 16.3°2θ, 8.2 °2θ, 11.3 °2θ, and 9.0°2θ (±0.2 °2θ; ±0.1°2θ; or ±0.0 °2θ; Cu Kα1 radiation).

In some embodiments, the solid form of tabernanthalog monofumarate salt Pattern #4a is crystalline tabernanthalog monofumarate salt Pattern #4a characterized by two or more, or three or more XRPD signals selected from the group consisting of 25.5°2θ, 16.3°2θ, 8.2 °2θ, 11.3 °2θ, 9.0 °2θ, 23.8 °2θ, and 17.1°2θ (±0.2°2θ; ±0.1 °2θ; or 0.0 °2θ; Cu Kα1 radiation). In some embodiments, the solid form of tabernanthalog monofumarate salt Pattern #4a is crystalline tabernanthalog monofumarate salt Pattern #4a characterized by XRPD signals at 25.5°2θ, 16.3°2θ, 8.2 °2θ, 11.3 °2θ, 9.0°2θ, 23.8 °2θ, and 17.1 °2θ (±0.2 °2θ; ±0.1 °2θ; or 0.0 °2θ; Cu Kα1 radiation).

In some embodiments, the solid form of tabernanthalog monofumarate salt Pattern #4a is crystalline tabernanthalog monofumarate salt Pattern #4a characterized by two or more, or three or more XRPD signals selected from the group consisting of 25.5 °2θ, 16.3°2θ, 8.2 °2θ, 11.3 °2θ, 9.0 °2θ, 23.8 °2θ, 17.1 °2θ, 19.3°2θ, 19.4 °2θ, and 26.8 °2θ (±0.2 °2θ; ±0.1 °2θ; or ±0.0 °2θ; Cu Kα1 radiation). In some embodiments, the solid form of tabernanthalog monofumarate salt Pattern #4a is crystalline tabernanthalog monofumarate salt Pattern #4a characterized by XRPD signals at 25.5 °2θ, 16.3°2θ, 8.2 °2θ, 11.3 °2θ, 9.0 °2θ, 23.8 °2θ, 17.1 °2θ, 19.3 °2θ, 19.4 °2θ, and 26.8 °2θ (±0.2 °2θ; ±0.1°2θ; or 0.0 °2θ; Cu Kα1 radiation).

In some embodiments, the crystalline tabernanthalog monofumarate salt Pattern #4a is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 163.

In some embodiments, the solid form of tabernanthalog monofumarate salt Pattern #4b is crystalline tabernanthalog monofumarate salt Pattern #4b characterized by two or more, or three or more XRPD signals selected from the group consisting of 25.6 °2θ, 16.3 °2θ, and 8.2°2θ (±0.2 °2θ; ±0.1 °2θ; or 0.0 °2θ; Cu Kα1 radiation). In some embodiments, the solid form of tabernanthalog monofumarate salt Pattern #4b is crystalline tabernanthalog monofumarate salt Pattern #4b characterized by XRPD signals at 25.6 °2θ, 16.3 °2θ, and 8.2°2θ (±0.2°2θ; ±0.1°2θ; or 0.0 °2θ; Cu Kα1 radiation).

In some embodiments, the solid form of tabernanthalog monofumarate salt Pattern #4b is crystalline tabernanthalog monofumarate salt Pattern #4b characterized by two or more, or three or more XRPD signals selected from the group consisting of 25.6 °2θ, 16.3°2θ, 8.2 °2θ, 9.1 °2θ, and 17.2°2θ (±0.2°2θ; ±0.1°2θ; or 0.0 °2θ; Cu Kα1 radiation). In some embodiments, the solid form of tabernanthalog monofumarate salt Pattern #4b is crystalline tabernanthalog monofumarate salt Pattern #4b characterized by XRPD signals at 25.6 °2θ, 16.3°2θ, 8.2 °2θ, 9.1 °2θ, and 17.2°2θ (±0.2°2θ; ±0.1°2θ; or 0.0 °2θ; Cu Kα1 radiation).

In some embodiments, the solid form of tabernanthalog monofumarate salt Pattern #4b is crystalline tabernanthalog monofumarate salt Pattern #4b characterized by two or more, or three or more XRPD signals selected from the group consisting of 25.6 °2θ, 16.3 °2θ, 8.2°2θ, 9.1 °2θ, 17.2 °2θ, 18.1 °2θ, and 26.8°2θ (±0.2°2θ; ±0.1°2θ; or 0.0 °2θ; Cu Kα1 radiation). In some embodiments, the solid form of tabernanthalog monofumarate salt Pattern #4b is crystalline tabernanthalog monofumarate salt Pattern #4b characterized by XRPD signals at 25.6 °2θ, 16.3 °2θ, 8.2 °2θ, 9.1 °2θ, 17.2 °2θ, 18.1 °2θ, and 26.8°2θ (±0.2 °2θ; ±0.1°2θ; or ±0.0 °2θ; Cu Kα1 radiation).

In some embodiments, the solid form of tabernanthalog monofumarate salt Pattern #4b is crystalline tabernanthalog monofumarate salt Pattern #4b characterized by two or more, or three or more XRPD signals selected from the group consisting of 25.6 °2θ, 16.3 °2θ, 8.2°2θ, 9.1 °2θ, 17.2 °2θ, 18.1 °2θ, 26.8 °2θ, 15.7 °2θ, 21.5 °2θ, and 27.3 °2θ (±0.2°2θ; ±0.1 °2θ; or ±0.0 °2θ; Cu Kα1 radiation). In some embodiments, the solid form of tabernanthalog monofumarate salt Pattern #4b is crystalline tabernanthalog monofumarate salt Pattern #4b characterized by XRPD signals at 25.6 °2θ, 16.3°2θ, 8.2 °2θ, 9.1 °2θ, 17.2 °2θ, 18.1 °2θ, 26.8 °2θ, 15.7 °2θ, 21.5 °2θ, and 27.3°2θ (±0.2 °2θ; ±0.1 °2θ; or ±0.0 °2θ; Cu Kα1 radiation).

In some embodiments, the crystalline tabernanthalog monofumarate salt Pattern #4b is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 164.

In some embodiments, the solid form of tabernanthalog unary fumarate salt Pattern #6a is crystalline tabernanthalog unary fumarate salt Pattern #6a characterized by two or more, or three or more XRPD signals selected from the group consisting of 19.6 °2θ, 16.6 °2θ, and 20.7 °2θ (±0.2 °2θ; ±0 1 °2θ; or ±0.0 °2θ; Cu Kα1 radiation). In some embodiments, the solid form of tabernanthalog unary fumarate salt Pattern #6a is crystalline tabernanthalog unary fumarate salt Pattern #6a characterized by XRPD signals at 19.6 °2θ, 16.6 °2θ, and 20.7 °2θ (±0.2 °2θ; ±0.1 °2θ; or ±0.0 °2θ; Cu Kα1 radiation).

In some embodiments, the solid form of tabernanthalog unary fumarate salt Pattern #6a is crystalline tabernanthalog unary fumarate salt Pattern #6a characterized by two or more, or three or more XRPD signals selected from the group consisting of 19.6 °2θ, 16.6 °2θ, 20.7 °2θ, 25.4 °2θ, and 19.3 °2θ (±0.2 °2θ; ±0.1 °2θ; or ±0.0 °2θ; Cu Kα1 radiation). In some embodiments, the solid form of tabernanthalog unary fumarate salt Pattern #6a is crystalline tabernanthalog unary fumarate salt Pattern #6a characterized by XRPD signals at 19.6 °2θ, 16.6 °2θ, 20.7 °2θ, 25.4 °2θ, and 19.3 °2θ (±0.2°2θ; ±0.1 °2θ; or 0.0 °2θ; Cu Kα1 radiation).

In some embodiments, the solid form of tabernanthalog unary fumarate salt Pattern #6a is crystalline tabernanthalog unary fumarate salt Pattern #6a characterized by two or more, or three or more XRPD signals selected from the group consisting 19.6 °2θ, 16.6 °2θ, 20.7 °2θ, 25.4 °2θ, 19.3 °2θ, 26.2 °2θ, and 22.1°2θ (±0.2°2θ; ±0.1°2θ; or ±0.0 °2θ; Cu Kα1 radiation). In some embodiments, the solid form of tabernanthalog unary fumarate salt Pattern #6a is crystalline tabernanthalog unary fumarate salt Pattern #6a characterized by XRPD signals at 19.6 °2θ, 16.6 °2θ, 20.7 °2θ, 25.4 °2θ, 19.3 °2θ, 26.2 °2θ, and 22.1°2θ (±0.2°2θ; ±0.1°2θ; or 0.0 °2θ; Cu Kα1 radiation).

In some embodiments, the solid form of tabernanthalog unary fumarate salt Pattern #6a is crystalline tabernanthalog unary fumarate salt Pattern #6a characterized by two or more, or three or more XRPD signals selected from the group consisting of 19.6 °2θ, 16.6 °2θ, 20.7 °2θ, 25.4 °2θ, 19.3 °2θ, 26.2 °2θ, 22.1 °2θ, 33.6 °2θ, and 13.0 °2θ (±0.2 °2θ; ±0.1 °2θ; or ±0.0 °2θ; Cu Kα1 radiation). In some embodiments, the solid form of tabernanthalog unary fumarate salt Pattern #6a is crystalline tabernanthalog unary fumarate salt Pattern #6a characterized by XRPD signals at 19.6 °2θ, 16.6 °2θ, 20.7 °2θ, 25.4 °2θ, 19.3 °2θ, 26.2 °2θ, 22.1 °2θ, 33.6 °2θ, and 13.0°2θ (±0.2 °2θ; ±0.1 °2θ; or 0.0 °2θ; Cu Kα1 radiation).

In some embodiments, the crystalline tabernanthalog unary fumarate salt Pattern #6a is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 166.

In some embodiments, the solid form of tabernanthalog monofumarate Pattern #6b is crystalline tabernanthalog monofumarate Pattern #6b characterized by two or more, or three or more XRPD signals selected from the group consisting of 19.4 °2θ, 16.5 °2θ, and 20.5°2θ (±0.2 °2θ; ±0.1 °2θ; or 0.0 °2θ; Cu Kα1 radiation). In some embodiments, the solid form of tabernanthalog monofumarate Pattern #6b is crystalline tabernanthalog monofumarate Pattern #6b characterized by XRPD signals at 19.4 °2θ, 16.5 °2θ, and 20.5 °2θ (±0.2 °2θ; ±0.1 °2θ; or 0.0 °2θ; Cu Kα1 radiation).

In some embodiments, the solid form of tabernanthalog monofumarate Pattern #6b is crystalline tabernanthalog monofumarate Pattern #6b characterized by two or more, or three or more XRPD signals selected from the group consisting of 19.4 °2θ, 16.5 °2θ, 20.5 °2θ, 25.3 °2θ, and 26.0°2θ (±0.2 °2θ; ±0.1°2θ; or ±0.0 °2θ; Cu Kα1 radiation). In some embodiments, the solid form of tabernanthalog monofumarate Pattern #6b is crystalline tabernanthalog monofumarate Pattern #6b characterized by XRPD signals at 19.4 °2θ, 16.5 °2θ, 20.5 °2θ, 25.3 °2θ, and 26.0°2θ (±0.2 °2θ; ±0.1°2θ; or 0.0 °2θ; Cu Kα1 radiation).

In some embodiments, the solid form of tabernanthalog monofumarate Pattern #6b is crystalline tabernanthalog monofumarate Pattern #6b characterized by two or more, or three or more XRPD signals selected from the group consisting of 19.4 °2θ, 16.5 °2θ, 20.5 °2θ, 25.3 °2θ, 26.0 °2θ, 22.0 °2θ, and 12.9°2θ (±0.2°2θ; ±0.1°2θ; or ±0.0 °2θ; Cu Kα1 radiation). In some embodiments, the solid form of tabernanthalog monofumarate Pattern #6b is crystalline tabernanthalog monofumarate Pattern #6b characterized by XRPD signals at 19.4 °2θ, 16.5 °2θ, 20.5 °2θ, 25.3 °2θ, 26.0 °2θ, 22.0 °2θ, and 12.9°2θ (±0.2°2θ; ±0.1°2θ; or ±0.0 °2θ; Cu Kα1 radiation).

In some embodiments, the solid form of tabernanthalog monofumarate Pattern #6b is crystalline tabernanthalog monofumarate Pattern #6b characterized by two or more, or three or more XRPD signals selected from the group consisting of 19.4 °2θ, 16.5 °2θ, 20.5 °2θ, 25.3 °2θ, 26.0 °2θ, 22.0 °2θ, 12.9 °2θ, 8.2 °2θ, 33.4 °2θ, and 37.7 °2θ (±0.2 °2θ; ±0.1 °2θ; or 0.0 °2θ; Cu Kα1 radiation). In some embodiments, the solid form of tabernanthalog monofumarate Pattern #6b is crystalline tabernanthalog monofumarate Pattern #6b characterized by XRPD signals at 19.4 °2θ, 16.5 °2θ, 20.5 °2θ, 25.3 °2θ, 26.0 °2θ, 22.0 °2θ, 12.9 °2θ, 8.2 °2θ, 33.4 °2θ, and 37.7 °2θ (±0.2°2θ; ±0.1 °2θ; or ±0.0 °2θ; Cu Kα1 radiation).

In some embodiments, the crystalline tabernanthalog monofumarate Pattern #6b is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 167.

In some embodiments, the solid form of tabernanthalog monofumarate salt Pattern #7 is crystalline tabernanthalog monofumarate salt Pattern #7 characterized by two or more, or three or more XRPD signals selected from the group consisting of 16.4 °2θ, 25.6 °2θ, and 15.9°2θ (±0.2 °2θ; ±0.1 °2θ; or ±0.0 °2θ; Cu Kα1 radiation). In some embodiments, the solid form of tabernanthalog monofumarate salt Pattern #7 is crystalline tabernanthalog monofumarate salt Pattern #7 characterized by XRPD signals at 16.4 °2θ, 25.6 °2θ, and 15.9°2θ (±0.2°2θ; ±0.1°2θ; or ±0.0 °2θ; Cu Kα1 radiation).

In some embodiments, the solid form of tabernanthalog monofumarate salt Pattern #7 is crystalline tabernanthalog monofumarate salt Pattern #7 characterized by two or more, or three or more XRPD signals selected from the group consisting of 16.4 °2θ, 25.6 °2θ, 15.9 °2θ, 7.2 °2θ, and 24.9°2θ (±0.2°2θ; ±0.1 °2θ; or ±0.0 °2θ; Cu Kα1 radiation). In some embodiments, the solid form of tabernanthalog monofumarate salt Pattern #7 is crystalline tabernanthalog monofumarate salt Pattern #7 characterized by XRPD signals at 16.4 °2θ, 25.6 °2θ, 15.9 °2θ, 7.2 °2θ, and 24.9°2θ (±0.2°2θ; ±0.1 °2θ; or ±0.0 °2θ; Cu Kα1 radiation).

In some embodiments, the solid form of tabernanthalog monofumarate salt Pattern #7 is crystalline tabernanthalog monofumarate salt Pattern #7 characterized by two or more, or three or more XRPD signals selected from the group consisting 16.4 °2θ, 25.6 °2θ, 15.9 °2θ, 7.2 °2θ, 24.9 °2θ, 19.4 °2θ, and 9.1 °2θ (±0.2 °2θ; ±0.1°2θ; or ±0.0 °2θ; Cu Kα1 radiation). In some embodiments, the solid form of tabernanthalog monofumarate salt Pattern #7 is crystalline tabernanthalog monofumarate salt Pattern #7 characterized by XRPD signals at 16.4 °2θ, 25.6 °2θ, 15.9 °2θ, 7.2 °2θ, 24.9°2θ, 19.4 °2θ, and 9.1°2θ (±0.2°2θ; ±0.1 °2θ; or ±0.0 °2θ; Cu Kα1 radiation).

In some embodiments, the solid form of tabernanthalog monofumarate salt Pattern #7 is crystalline tabernanthalog monofumarate salt Pattern #7 characterized by two or more, or three or more XRPD signals selected from the group consisting of 16.4 °2θ, 25.6 °2θ, 15.9 °2θ, 7.2 °2θ, 24.9 °2θ, 19.4 °2θ, 9.1 °2θ, 19.8 °2θ, 21.3°2θ, and 16.8°2θ (±0.2°2θ; ±0.1°2θ; or 0.0 °2θ; Cu Kα1 radiation). In some embodiments, the solid form of tabernanthalog monofumarate salt Pattern #7 is crystalline tabernanthalog monofumarate salt Pattern #7 characterized by XRPD signals at 16.4 °2θ, 25.6 °2θ, 15.9 °2θ, 7.2 °2θ, 24.9 °2θ, 19.4 °2θ, 9.1 °2θ, 19.8 °2θ, 21.3 °2θ, and 16.8°2θ (±0.2°2θ; ±0.1°2θ; or 0.0 °2θ; Cu Kα1 radiation).

In some embodiments, the crystalline tabernanthalog monofumarate salt Pattern #7 is characterized by one, two, three, four, five, six, seven, eight, nine, ten, eleven, twelve, thirteen, fourteen, fifteen, sixteen, or seventeen, XRPD signals selected from those set forth in Table 168.

In some embodiments, the solid form of tabernanthalog monofumarate salt Pattern #8 is crystalline tabernanthalog monofumarate salt Pattern #8 characterized by two or more, or three or more XRPD signals selected from the group consisting of 25.5°2θ, 16.3 °2θ, and 15.8 °2θ (±0.2 °2θ; ±0.1°2θ; or 0.0 °2θ; Cu Kα1 radiation). In some embodiments, the solid form of tabernanthalog monofumarate salt Pattern #8 is crystalline tabernanthalog monofumarate salt Pattern #8 characterized by XRPD signals at 25.5°2θ, 16.3°2θ, and 15.8°2θ (±0.2°2θ; ±0.1 °2θ; or 0.0 °2θ; Cu Kα1 radiation).

In some embodiments, the solid form of tabernanthalog monofumarate salt Pattern #8 is crystalline tabernanthalog monofumarate salt Pattern #8 characterized by two or more, or three or more XRPD signals selected from the group consisting of 25.5 °2θ, 16.3°2θ, 15.8 °2θ, 24.2°2θ, and 20.5 °2θ (±0.2 °2θ; ±0.1 °2θ; or ±0.0 °2θ; Cu Kα1 radiation). In some embodiments, the solid form of tabernanthalog monofumarate salt Pattern #8 is crystalline tabernanthalog monofumarate salt Pattern #8 characterized by XRPD signals at 25.5 °2θ, 16.3°2θ, 15.8 °2θ, 24.2 °2θ, and 20.5 °2θ (±0.2°2θ; ±0.1 °2θ; or 0.0 °2θ; Cu Kα1 radiation).

In some embodiments, the solid form of tabernanthalog monofumarate salt Pattern #8 is crystalline tabernanthalog monofumarate salt Pattern #8 characterized by two or more, or three or more XRPD signals selected from the group consisting 25.5°2θ, 16.3°2θ, 15.8 °2θ, 24.2 °2θ, 20.5 °2θ, 24.8 °2θ, and 18.0°2θ (±0.2°2θ; ±0.1°2θ; or 0.0 °2θ; Cu Kα1 radiation). In some embodiments, the solid form of tabernanthalog monofumarate salt Pattern #8 is crystalline tabernanthalog monofumarate salt Pattern #8 characterized by XRPD signals at 25.5 °2θ, 16.3°2θ, 15.8 °2θ, 24.2 °2θ, 20.5 °2θ, 24.8 °2θ, and 18.0°2θ (±0.2°2θ; ±0.1°2θ; or 0.0 °2θ; Cu Kα1 radiation).

In some embodiments, the solid form of tabernanthalog monofumarate salt Pattern #8 is crystalline tabernanthalog monofumarate salt Pattern #8 characterized by two or more, or three or more XRPD signals selected from the group consisting of 25.5°2θ, 16.3°2θ, 15.8 °2θ, 24.2 °2θ, 20.5 °2θ, 24.8 °2θ, 18.0 °2θ, 7.6 °2θ, 9.0 °2θ, and 19.0°2θ (±0.2°2θ; ±0.1 °2θ; or ±0.0 °2θ; Cu Kα1 radiation). In some embodiments, the solid form of tabernanthalog monofumarate salt Pattern #8 is crystalline tabernanthalog monofumarate salt Pattern #8 characterized by XRPD signals at 25.5°2θ, 16.3°2θ, 15.8 °2θ, 24.2°2θ, 20.5 °2θ, 24.8 °2θ, 18.0 °2θ, 7.6°2θ, 9.0 °2θ, and 19.0°2θ (±0.2°2θ; ±0.1°2θ; or 0.0 °2θ; Cu Kα1 radiation).

In some embodiments, the crystalline tabernanthalog monofumarate salt Pattern #8 is characterized by one, two, three, four, five, six, seven, eight, nine, ten, eleven, twelve, thirteen, fourteen, fifteen, sixteen, seventeen, eighteen, or nineteen, XRPD signals selected from those set forth in Table 169.

In some embodiments, the solid form of tabernanthalog monofumarate salt Pattern #9 is crystalline tabernanthalog monofumarate salt Pattern #9 characterized by two or more, or three or more XRPD signals selected from the group consisting of 15.9 °2θ, 25.6 °2θ, and 24.7°2θ (±0.2 °2θ; ±0.1°2θ; or 0.0 °2θ; Cu Kα1 radiation). In some embodiments, the solid form of tabernanthalog monofumarate salt Pattern #9 is crystalline tabernanthalog monofumarate salt Pattern #9 characterized by XRPD signals at 15.9 °2θ, 25.6 °2θ, and 24.7°2θ (±0.2°2θ; ±0.1 °2θ; or ±0.0 °2θ; Cu Kα1 radiation).

In some embodiments, the solid form of tabernanthalog monofumarate salt Pattern #9 is crystalline tabernanthalog monofumarate salt Pattern #9 characterized by two or more, or three or more XRPD signals selected from the group consisting of 15.9 °2θ, 25.6 °2θ, 24.7 °2θ, 16.4 °2θ, and 19.5°2θ (±0.2 °2θ; ±0.1 °2θ; or 0.0 °2θ; Cu Kα1 radiation). In some embodiments, the solid form of tabernanthalog monofumarate salt Pattern #9 is crystalline tabernanthalog monofumarate salt Pattern #9 characterized by XRPD signals at 15.9 °2θ, 25.6 °2θ, 24.7 °2θ, 16.4 °2θ, and 19.5 °2θ (±0.2 °2θ; ±0.1 °2θ; or ±0.0 °2θ; Cu Kα1 radiation).

In some embodiments, the solid form of tabernanthalog monofumarate salt Pattern #9 is crystalline tabernanthalog monofumarate salt Pattern #9 characterized by two or more, or three or more XRPD signals selected from the group consisting 15.9 °2θ, 25.6 °2θ, 24.7 °2θ, 16.4 °2θ, 19.5 °2θ, 21.9 °2θ, and 17.1°2θ (±0.2°2θ; ±0.1°2θ; or 0.0 °2θ; Cu Kα1 radiation). In some embodiments, the solid form of tabernanthalog monofumarate salt Pattern #9 is crystalline tabernanthalog monofumarate salt Pattern #9 characterized by XRPD signals at 15.9 °2θ, 25.6 °2θ, 24.7 °2θ, 16.4 °2θ, 19.5 °2θ, 21.9 °2θ, and 17.1°2θ (±0.2°2θ; ±0.1°2θ; or 0.0 °2θ; Cu Kα1 radiation).

In some embodiments, the solid form of tabernanthalog monofumarate salt Pattern #9 is crystalline tabernanthalog monofumarate salt Pattern #9 characterized by two or more, or three or more XRPD signals selected from the group consisting of 15.9 °2θ, 25.6 °2θ, 24.7 °2θ, 16.4 °2θ, 19.5°2θ, 21.9 °2θ, 17.1 °2θ, 8.0 °2θ, 9.2 °2θ, and 20.8°2θ (±0.2 °2θ; ±0.1°2θ; or ±0.0 °2θ; Cu Kα1 radiation). In some embodiments, the solid form of tabernanthalog monofumarate salt Pattern #9 is crystalline tabernanthalog monofumarate salt Pattern #9 characterized by XRPD signals at 15.9 °2θ, 25.6 °2θ, 24.7 °2θ, 16.4 °2θ, 19.5 °2θ, 21.9 °2θ, 17.1 °2θ, 8.0 °2θ, 9.2 °2θ, and 20.8°2θ (±0.2°2θ; ±0.1 °2θ; or 0.0 °2θ; Cu Kα1 radiation).

In some embodiments, the crystalline tabernanthalog monofumarate salt Pattern #9 is characterized by one, two, three, four, five, six, seven, eight, nine, ten, eleven, twelve, thirteen, fourteen, fifteen, sixteen, seventeen, eighteen, or nineteen, XRPD signals selected from those set forth in Table 170.

In some embodiments, the solid form of tabernanthalog monofumarate salt Pattern #10 is crystalline tabernanthalog monofumarate salt Pattern #10 characterized by two or more, or three or more XRPD signals selected from the group consisting of 25.5 °2θ, 16.9 °2θ, and 16.3 °2θ (±0.2 °2θ; ±0.1 °2θ; or 0.0 °2θ; Cu Kα1 radiation). In some embodiments, the solid form of tabernanthalog monofumarate salt Pattern #10 is crystalline tabernanthalog monofumarate salt Pattern #10 characterized by XRPD signals at 25.5 °2θ, 16.9 °2θ, and 16.3 °2θ (±0.2 °2θ; ±0.1 °2θ; or 0.0 °2θ; Cu Kα1 radiation).

In some embodiments, the solid form of tabernanthalog monofumarate salt Pattern #10 is crystalline tabernanthalog monofumarate salt Pattern #10 characterized by two or more, or three or more XRPD signals selected from the group consisting of 25.5°2θ, 16.9 °2θ, 16.3°2θ, 21.3 °2θ, and 23.5°2θ (±0.2 °2θ; ±0.1 °2θ; or 0.0 °2θ; Cu Kα1 radiation). In some embodiments, the solid form of tabernanthalog monofumarate salt Pattern #10 is crystalline tabernanthalog monofumarate salt Pattern #10 characterized by XRPD signals at 25.5 °2θ, 16.9 °2θ, 16.3 °2θ, 21.3 °2θ, and 23.5 °2θ (±0.2 °2θ; ±0.1°2θ; or 0.0 °2θ; Cu Kα1 radiation).

In some embodiments, the solid form of tabernanthalog monofumarate salt Pattern #10 is crystalline tabernanthalog monofumarate salt Pattern #10 characterized by two or more, or three or more XRPD signals selected from the group consisting 25.5 °2θ, 16.9 °2θ, 16.3°2θ, 21.3 °2θ, 23.5 °2θ, 8.2 °2θ, and 10.8 °2θ (±0.2°2θ; ±0.1°2θ; or ±0.0 °2θ; Cu Kα1 radiation). In some embodiments, the solid form of tabernanthalog monofumarate salt Pattern #10 is crystalline tabernanthalog monofumarate salt Pattern #10 characterized by XRPD signals at 25.5°2θ, 16.9 °2θ, 16.3°2θ, 21.3 °2θ, 23.5 °2θ, 8.2 °2θ, and 10.8 °2θ (±0.2°2θ; ±0.1°2θ; or ±0.0 °2θ; Cu Kα1 radiation).

In some embodiments, the solid form of tabernanthalog monofumarate salt Pattern #10 is crystalline tabernanthalog monofumarate salt Pattern #10 characterized by two or more, or three or more XRPD signals selected from the group consisting of 25.5 °2θ, 16.9 °2θ, 16.3°2θ, 21.3 °2θ, 23.5 °2θ, 8.2 °2θ, 10.8°2θ, 9.1 °2θ, 23.4 °2θ, and 19.8°2θ (±0.2°2θ; ±0.1 °2θ; or ±0.0 °2θ; Cu Kα1 radiation). In some embodiments, the solid form of tabernanthalog monofumarate salt Pattern #10 is crystalline tabernanthalog monofumarate salt Pattern #10 characterized by XRPD signals at 25.5°2θ, 16.9 °2θ, 16.3°2θ, 21.3 °2θ, 23.5 °2θ, 8.2 °2θ, 10.8 °2θ, 9.1 °2θ, 23.4 °2θ, and 19.8°2θ (±0.2°2θ; ±0.1 °2θ; or 0.0 °2θ; Cu Kα1 radiation).

In some embodiments, the crystalline tabernanthalog monofumarate salt Pattern #10 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 171.

In some embodiments, the solid form of tabernanthalog monofumarate salt Pattern #11 is crystalline tabernanthalog monofumarate salt Pattern #11 characterized by two or more, or three or more XRPD signals selected from the group consisting of 16.1 °2θ, 25.7 °2θ, and 16.4 °2θ (±0.2 °2θ; ±0.1°2θ; or ±0.0 °2θ; Cu Kα1 radiation). In some embodiments, the solid form of tabernanthalog monofumarate salt Pattern #11 is crystalline tabernanthalog monofumarate salt Pattern #11 characterized by XRPD signals at 16.1 °2θ, 25.7 °2θ, and 16.4°2θ (±0.2 °2θ; ±0.1°2θ; or ±0.0 °2θ; Cu Kα1 radiation).

In some embodiments, the solid form of tabernanthalog monofumarate salt Pattern #11 is crystalline tabernanthalog monofumarate salt Pattern #11 characterized by two or more, or three or more XRPD signals selected from the group consisting of 16.1020, 25.7 °2θ, 16.4 °2θ, 21.6 °2θ, and 20.4°2θ (±0.2°2θ; ±0.1°2θ; or ±0.0 °2θ; Cu Kα1 radiation). In some embodiments, the solid form of tabernanthalog monofumarate salt Pattern #11 is crystalline tabernanthalog monofumarate salt Pattern #11 characterized by XRPD signals at 16.1 °2θ, 25.7 °2θ, 16.4 °2θ, 21.6 °2θ, and 20.4°2θ (±0.2 °2θ; ±0.1 °2θ; or ±0.0 °2θ; Cu Kα1 radiation).

In some embodiments, the solid form of tabernanthalog monofumarate salt Pattern #11 is crystalline tabernanthalog monofumarate salt Pattern #11 characterized by two or more, or three or more XRPD signals selected from the group consisting 16.1 °2θ, 25.7 °2θ, 16.4 °2θ, 21.6 °2θ, 20.4 °2θ, 7.5 °2θ, and 9.2 °2θ (±0.2 °2θ; ±0.1°2θ; or ±0.0 °2θ; Cu Kα1 radiation). In some embodiments, the solid form of tabernanthalog monofumarate salt Pattern #11 is crystalline tabernanthalog monofumarate salt Pattern #11 characterized by XRPD signals at 16.1 °2θ, 25.7 °2θ, 16.4 °2θ, 21.6 °2θ, 20.4 °2θ, 7.5 °2θ, and 9.2°2θ (±0.2 °2θ; ±0.1°2θ; or 0.0 °2θ; Cu Kα1 radiation). In some embodiments, the crystalline tabernanthalog monofumarate salt Pattern #10tabernanthalog monofumarate salt Pattern #11 is crystalline tabernanthalog monofumarate salt Pattern #11 characterized by two or more, or three or more XRPD signals selected from the group consisting of 16.1 °2θ, 25.7 °2θ, 16.4 °2θ, 21.6 °2θ, 20.4 °2θ, 7.5 °2θ, 9.2 °2θ, 23.9 °2θ, 17.4 °2θ, and 20.9°2θ (±0.2°2θ; ±0.1 °2θ; or 0.0 °2θ; Cu Kα1 radiation). In some embodiments, the solid form of tabernanthalog monofumarate salt Pattern #11 is crystalline tabernanthalog monofumarate salt Pattern #11 characterized by XRPD signals at 16.1 °2θ, 25.7 °2θ, 16.4 °2θ, 21.6 °2θ, 20.4 °2θ, 7.5 °2θ, 9.2 °2θ, 23.9 °2θ, 17.4 °2θ, and 20.9 °2θ (±0.2°2θ; ±0.1°2θ; or 0.0 °2θ; Cu Kα1 radiation).

In some embodiments, the crystalline tabernanthalog monofumarate salt Pattern #11 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or twenty-five XRPD signals selected from those set forth in Table 171.

In some embodiments, the solid form of monofumarate salt Pattern #11 is crystalline tabernanthalog monofumarate salt Pattern #11 characterized by two or more, or three or more XRPD signals selected from the group consisting of 16.1 °2θ, 25.7 °2θ, and 16.4 °2θ (±0.2 °2θ; ±0.1 °2θ; or 0.0 °2θ; Cu Kα1 radiation). In some embodiments, the solid form of tabernanthalog monofumarate salt Pattern #11 is crystalline tabernanthalog monofumarate salt Pattern #11 characterized by XRPD signals at 16.1 °2θ, 25.7 °2θ, and 16.4 °2θ (±0.2 °2θ; ±0.1°2θ; or 0.0 °2θ; Cu Kα1 radiation).

In some embodiments, the solid form of tabernanthalog monofumarate salt Pattern #11 is crystalline tabernanthalog monofumarate salt Pattern #11 characterized by two or more, or three or more XRPD signals selected from the group consisting of 16.1020, 25.7 °2θ, 16.4 °2θ, 21.6 °2θ, and 20.4°2θ (±0.2°2θ; ±0.1 °2θ; or 0.0 °2θ; Cu Kα1 radiation). In some embodiments, the solid form of tabernanthalog monofumarate salt Pattern #11 is crystalline tabernanthalog monofumarate salt Pattern #11 characterized by XRPD signals at 16.1 °2θ, 25.7 °2θ, 16.4 °2θ, 21.6 °2θ, and 20.4°2θ (±0.2 °2θ; ±0.1 °2θ; or 0.0 °2θ; Cu Kα1 radiation).

In some embodiments, the solid form of tabernanthalog monofumarate salt Pattern #11 is crystalline tabernanthalog monofumarate salt Pattern #11 characterized by two or more, or three or more XRPD signals selected from the group consisting 16.1 °2θ, 25.7 °2θ, 16.4 °2θ, 21.6 °2θ, 20.4 °2θ, 7.5 °2θ, and 9.2 °2θ (±0.2 °2θ; ±0.1°2θ; or 0.0 °2θ; Cu Kα1 radiation). In some embodiments, the solid form of tabernanthalog monofumarate salt Pattern #11 is crystalline tabernanthalog monofumarate salt Pattern #11 characterized by XRPD signals at 16.1 °2θ, 25.7 °2θ, 16.4 °2θ, 21.6 °2θ, 20.4 °2θ, 7.5 °2θ, and 9.2 °2θ (±0.2°2θ; ±0.1°2θ; or ±0.0 °2θ; Cu Kα1 radiation).

In some embodiments, the solid form of tabernanthalog monofumarate salt Pattern #11 is crystalline tabernanthalog monofumarate salt Pattern #11 characterized by two or more, or three or more XRPD signals selected from the group consisting of 16.1 °2θ, 25.7 °2θ, 16.4 °2θ, 21.6 °2θ, 20.4 °2θ, 7.5 °2θ, 9.2 °2θ, 23.9 °2θ, 17.4 °2θ, and 20.9°2θ (±0.2 °2θ; ±0.1°2θ; or 0.0 °2θ; Cu Kα1 radiation). In some embodiments, the solid form of tabernanthalog monofumarate salt Pattern #11 is crystalline tabernanthalog monofumarate salt Pattern #11 characterized by XRPD signals at 16.1 °2θ, 25.7 °2θ, 16.4 °2θ, 21.6 °2θ, 20.4 °2θ, 7.5 °2θ, 9.2 °2θ, 23.9 °2θ, 17.4 °2θ, and 20.9 °2θ (±0.2 °2θ; ±0.1 °2θ; or 0.0 °2θ; Cu Kα1 radiation).

In some embodiments, the crystalline tabernanthalog monofumarate salt Pattern #11 is characterized by one, two, three, four, five, six, seven, eight, nine, ten, eleven, twelve, thirteen, fourteen, fifteen, or sixteen XRPD signals selected from those set forth in Table 172.

In some embodiments, the solid form of tabernanthalog monofumarate salt Pattern #12 is crystalline tabernanthalog monofumarate salt Pattern #12 characterized by two or more, or three or more XRPD signals selected from the group consisting of 16.3°2θ, 25.6 °2θ, and 21.6°2θ (±0.2 °2θ; ±0.1 °2θ; or 0.0 °2θ; Cu Kα1 radiation). In some embodiments, the solid form of tabernanthalog monofumarate salt Pattern #12 is crystalline tabernanthalog monofumarate salt Pattern #12 characterized by XRPD signals at 16.3 °2θ, 25.6 °2θ, and 21.6 °2θ (±0.2 °2θ; ±0.1°2θ; or 0.0 °2θ; Cu Kα1 radiation).

In some embodiments, the solid form of tabernanthalog monofumarate salt Pattern #12 is crystalline tabernanthalog monofumarate salt Pattern #12 characterized by two or more, or three or more XRPD signals selected from the group consisting of 16.3°2θ, 25.6 °2θ, 21.6 °2θ, 20.3 °2θ, and 8.3°2θ (±0.2°2θ; ±0.1 °2θ; or ±0.0 °2θ; Cu Kα1 radiation). In some embodiments, the solid form of tabernanthalog monofumarate salt Pattern #12 is crystalline tabernanthalog monofumarate salt Pattern #12 characterized by XRPD signals at 16.3°2θ, 25.6 °2θ, 21.6 °2θ, 20.3 °2θ, and 8.3 °2θ (±0.2°2θ; ±0.1 °2θ; or ±0.0 °2θ; Cu Kα1 radiation).

In some embodiments, the solid form of tabernanthalog monofumarate salt Pattern #12 is crystalline tabernanthalog monofumarate salt Pattern #12 characterized by two or more, or three or more XRPD signals selected from the group consisting 16.3°2θ, 25.6 °2θ, 21.6 °2θ, 20.3 °2θ, 8.3 °2θ, 9.1 °2θ, and 18.2°2θ (±0.2°2θ; ±0.1°2θ; or 0.0 °2θ; Cu Kα1 radiation). In some embodiments, the solid form of tabernanthalog monofumarate salt Pattern #12 is crystalline tabernanthalog monofumarate salt Pattern #12 characterized by XRPD signals at 16.3 °2θ, 25.6°2θ, 21.6 °2θ, 20.3 °2θ, 8.3 °2θ, 9.1 °2θ, and 18.2°2θ (±0.2°2θ; ±0.1°2θ; or 0.0 °2θ; Cu Kα1 radiation).

In some embodiments, the solid form of tabernanthalog monofumarate salt Pattern #12 is crystalline tabernanthalog monofumarate salt Pattern #12 characterized by two or more, or three or more XRPD signals selected from the group consisting of 16.3°2θ, 25.6 °2θ, 21.6 °2θ, 20.3 °2θ, 8.3 °2θ, 9.1 °2θ, 18.2 °2θ, 23.0 °2θ, 10.8 °2θ, and 14.3°2θ (±0.2°2θ; ±0.1°2θ; or ±0.0 °2θ; Cu Kα1 radiation). In some embodiments, the solid form of tabernanthalog monofumarate salt Pattern #12 is crystalline tabernanthalog monofumarate salt Pattern #12 characterized by XRPD signals at 16.3 °2θ, 25.6 °2θ, 21.6 °2θ, 20.3 °2θ, 8.3 °2θ, 9.1 °2θ, 18.2 °2θ, 23.0 °2θ, 10.8 °2θ, and 14.3°2θ (±0.2 °2θ; ±0.1 °2θ; or ±0.0 °2θ; Cu Kα1 radiation).

In some embodiments, the crystalline tabernanthalog monofumarate salt Pattern #12 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 173.

In some embodiments, the solid form of tabernanthalog monofumarate salt Pattern #13 is crystalline tabernanthalog monofumarate salt Pattern #13 characterized by two or more, or three or more XRPD signals selected from the group consisting of 25.6 °2θ, 16.0 °2θ, and 16.4°2θ (±0.2 °2θ; ±0.1 °2θ; or ±0.0 °2θ; Cu Kα1 radiation). In some embodiments, the solid form of tabernanthalog monofumarate salt Pattern #13 is crystalline tabernanthalog monofumarate salt Pattern #13 characterized by XRPD signals at 25.6 °2θ, 16.0 °2θ, and 16.4°2θ (±0.2 °2θ; ±0.1 °2θ; or 0.0 °2θ; Cu Kα1 radiation).

In some embodiments, the solid form of tabernanthalog monofumarate salt Pattern #13 is crystalline tabernanthalog monofumarate salt Pattern #13 characterized by two or more, or three or more XRPD signals selected from the group consisting of 25.6 °2θ, 16.0 °2θ, 16.4 °2θ, 25.0 °2θ, and 19.7°2θ (±0.2 °2θ; ±0.1 °2θ; or 0.0 °2θ; Cu Kα1 radiation). In some embodiments, the solid form of tabernanthalog monofumarate salt Pattern #13 is crystalline tabernanthalog monofumarate salt Pattern #13 characterized by XRPD signals at of 25.6 °2θ, 16.0 °2θ, 16.4 °2θ, 25.0 °2θ, and 19.7°2θ (±0.2°2θ; ±0.1 °2θ; or ±0.0 °2θ; Cu Kα1 radiation).

In some embodiments, the solid form of tabernanthalog monofumarate salt Pattern #13 is crystalline tabernanthalog monofumarate salt Pattern #13 characterized by two or more, or three or more XRPD signals selected from the group consisting of 25.6 °2θ, 16.0 °2θ, 16.4 °2θ, 25.0 °2θ, 19.7 °2θ, 17.5 °2θ, and 8.1 °2θ (±0.2 °2θ; ±0.1°2θ; or ±0.0 °2θ; Cu Kα1 radiation). In some embodiments, the solid form of tabernanthalog monofumarate salt Pattern #13 is crystalline tabernanthalog monofumarate salt Pattern #13 characterized by XRPD signals at 25.6 °2θ, 16.0 °2θ, 16.4 °2θ, 25.0 °2θ, 19.7°2θ, 17.5 °2θ, and 8.1°2θ (±0.2 °2θ; ±0.1 °2θ; or 0.0 °2θ; Cu Kα1 radiation).

In some embodiments, the solid form of tabernanthalog monofumarate salt Pattern #13 is crystalline tabernanthalog monofumarate salt Pattern #13 characterized by two or more, or three or more XRPD signals selected from the group consisting of 25.6 °2θ, 16.0 °2θ, 16.4 °2θ, 25.0 °2θ, 19.7 °2θ, 17.5 °2θ, 8.1 °2θ, 21.9 °2θ, 9.1 °2θ, and 20.9°2θ (±0.2°2θ; ±0.1 °2θ; or 0.0 °2θ; Cu Kα1 radiation). In some embodiments, the solid form of tabernanthalog monofumarate salt Pattern #13 is crystalline tabernanthalog monofumarate salt Pattern #13 characterized by XRPD signals at 25.6 °2θ, 16.0 °2θ, 16.4 °2θ, 25.0 °2θ, 19.7 °2θ, 17.5 °2θ, 8.1 °2θ, 21.9 °2θ, 9.1 °2θ, and 20.9°2θ (±0.2°2θ; ±0.1°2θ; or 0.0 °2θ; Cu Kα1 radiation).

In some embodiments, the crystalline tabernanthalog monofumarate salt Pattern #13 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 174.

In some embodiments, the solid form of tabernanthalog monofumarate salt Pattern #15 is crystalline tabernanthalog monofumarate salt Pattern #15 characterized by two or more, or three or more XRPD signals selected from the group consisting of 16.2 °2θ, 17.0 °2θ, and 25.5°20 (±0.2 °2θ; ±0.1°2θ; or ±0.0 °2θ; Cu Kα1 radiation). In some embodiments, the solid form of tabernanthalog monofumarate salt Pattern #15 is crystalline tabernanthalog monofumarate salt Pattern #15 characterized by XRPD signals 16.2 °2θ, 17.0 °2θ, and 25.5°20 (±0.2°2θ; ±0.1°2θ; or ±0.0 °2θ; Cu Kα1 radiation).

In some embodiments, the solid form of tabernanthalog monofumarate salt Pattern #15 is crystalline tabernanthalog monofumarate salt Pattern #15 characterized by two or more, or three or more XRPD signals selected from the group consisting of 16.2 °2θ, 17.0 °2θ, 25.5°2θ, 23.3 °2θ, and 21.0 °2θ (±0.2 °2θ; ±0.1°2θ; or 0.0 °2θ; Cu Kα1 radiation). In some embodiments, the solid form of tabernanthalog monofumarate salt Pattern #15 is crystalline tabernanthalog monofumarate salt Pattern #15 characterized by XRPD signals at of 16.2 °2θ, 17.0 °2θ, 25.5°2θ, 23.3 °2θ, and 21.0 °2θ (±0.2 °2θ; ±0.1 °2θ; or 0.0 °2θ; Cu Kα1 radiation).

In some embodiments, the solid form of tabernanthalog monofumarate salt Pattern #15 is crystalline tabernanthalog monofumarate salt Pattern #15 characterized by two or more, or three or more XRPD signals selected from the group consisting of 16.2 °2θ, 17.0 °2θ, 25.5°2θ, 23.3 °2θ, 21.0 °2θ, 16.9 °2θ, and 19.9°2θ (±0.2°2θ; 0.1°2θ; or 0.0 °2θ; Cu Kα1 radiation). In some embodiments, the solid form of tabernanthalog monofumarate salt Pattern #15 is crystalline tabernanthalog monofumarate salt Pattern #15 characterized by XRPD signals at 16.2 °2θ, 17.0 °2θ, 25.5 °2θ, 23.3 °2θ, 21.0 °2θ, 16.9 °2θ, and 19.9 °2θ (±0.2 °2θ; ±0.1°2θ; or 0.0 °2θ; Cu Kα1 radiation).

In some embodiments, the solid form of tabernanthalog monofumarate salt Pattern #15 is crystalline tabernanthalog monofumarate salt Pattern #15 characterized by two or more, or three or more XRPD signals selected from the group consisting of 16.2 °2θ, 17.0 °2θ, 25.5 °2θ, 23.3 °2θ, 21.0 °2θ, 16.9 °2θ, 19.9 °2θ, 24.4 °2θ, 8.4°2θ, and 25.1 °2θ (±0.2 °2θ; ±0.1°2θ; or ±0.0 °2θ; Cu Kα1 radiation). In some embodiments, the solid form of tabernanthalog monofumarate salt Pattern #15 is crystalline tabernanthalog monofumarate salt Pattern #15 characterized by XRPD signals at 16.2 °2θ, 17.0 °2θ, 25.5°2θ, 23.3 °2θ, 21.0 °2θ, 16.9 °2θ, 19.9 °2θ, 24.4 °2θ, 8.4 °2θ, and 25.1 °2θ (±0.2°2θ; ±0.1 °2θ; or 0.0 °2θ; Cu Kα1 radiation).

In some embodiments, the crystalline tabernanthalog monofumarate salt Pattern #15 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 176.

In some embodiments, the solid form of tabernanthalog monofumarate salt Pattern #16 is crystalline tabernanthalog monofumarate salt Pattern #16 characterized by two or more, or three or more XRPD signals selected from the group consisting of 25.6 °2θ, 16.4°2θ, and 17.0°2θ (±0.2 °2θ; ±0.1°2θ; or 0.0 °2θ; Cu Kα1 radiation). In some embodiments, the solid form of tabernanthalog monofumarate salt Pattern #16 is crystalline tabernanthalog monofumarate salt Pattern #16 characterized by XRPD signals 25.6 °2θ, 16.4 °2θ, and 17.0°2θ (±0.2°2θ; ±0.1 °2θ; or ±0.0 °2θ; Cu Kα1 radiation).

In some embodiments, the solid form of tabernanthalog monofumarate salt Pattern #16 is crystalline tabernanthalog monofumarate salt Pattern #16 characterized by two or more, or three or more XRPD signals selected from the group consisting of 25.6 °2θ, 16.4 °2θ, 17.0 °2θ, 24.4 °2θ, and 19.3°2θ (±0.2°2θ; ±0.1°2θ; or 0.0 °2θ; Cu Kα1 radiation). In some embodiments, the solid form of tabernanthalog monofumarate salt Pattern #16 is crystalline tabernanthalog monofumarate salt Pattern #16 characterized by XRPD signals at 25.6 °2θ, 16.4 °2θ, 17.0 °2θ, 24.4 °2θ, and 19.3 °2θ (±0.2°2θ; ±0.1 °2θ; or 0.0 °2θ; Cu Kα1 radiation).

In some embodiments, the solid form of tabernanthalog monofumarate salt Pattern #16 is crystalline tabernanthalog monofumarate salt Pattern #16 characterized by two or more, or three or more XRPD signals selected from the group consisting of 25.6 °2θ, 16.4 °2θ, 17.0 °2θ, 24.4 °2θ, 19.3 °2θ, 9.1 °2θ, and 16.8°2θ (±0.2 °2θ; ±0.1°2θ; or 0.0 °2θ; Cu Kα1 radiation). In some embodiments, the solid form of tabernanthalog monofumarate salt Pattern #16 is crystalline tabernanthalog monofumarate salt Pattern #16 characterized by XRPD signals at 25.6 °2θ, 16.4 °2θ, 17.0 °2θ, 24.4 °2θ, 19.3 °2θ, 9.1 °2θ, and 16.8 °2θ (±0.2°2θ; ±0.1°2θ; or ±0.0 °2θ; Cu Kα1 radiation).

In some embodiments, the solid form of tabernanthalog monofumarate salt Pattern #16 is crystalline tabernanthalog monofumarate salt Pattern #16 characterized by two or more, or three or more XRPD signals selected from the group consisting of 25.6 °2θ, 16.4 °2θ, 17.0 °2θ, 24.4 °2θ, 19.3 °2θ, 9.1 °2θ, 16.8 °2θ, 9.6 °2θ, 18.1 °2θ, and 22.4°2θ (±0.2°2θ; ±0.1 °2θ; or ±0.0 °2θ; Cu Kα1 radiation). In some embodiments, the solid form of tabernanthalog monofumarate salt Pattern #16 is crystalline tabernanthalog monofumarate salt Pattern #16 characterized by XRPD signals at 25.6 °2θ, 16.4 °2θ, 17.0 °2θ, 24.4 °2θ, 19.3 °2θ, 9.1 °2θ, 16.8 °2θ, 9.6 °2θ, 18.1 °2θ, and 22.4°2θ (±0.2 °2θ; ±0.1 °2θ; or 0.0 °2θ; Cu Kα1 radiation).

In some embodiments, the crystalline tabernanthalog monofumarate salt Pattern #16 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 177.

In some embodiments, the solid form of tabernanthalog monofumarate salt Pattern #17 is crystalline tabernanthalog monofumarate salt Pattern #17 characterized by two or more, or three or more XRPD signals selected from the group consisting of 25.6 °2θ, 16.4 °2θ, and 16.6 °2θ (±0.2 °2θ; ±0.1°2θ; or ±0.0 °2θ; Cu Kα1 radiation). In some embodiments, the solid form of tabernanthalog monofumarate salt Pattern #17 is crystalline tabernanthalog monofumarate salt Pattern #17 characterized by XRPD signals 25.6 °2θ, 16.4 °2θ, and 16.6°2θ (±0.2 °2θ; ±0.1 °2θ; or ±0.0 °2θ; Cu Kα1 radiation).

In some embodiments, the solid form of tabernanthalog monofumarate salt Pattern #17 is crystalline tabernanthalog monofumarate salt Pattern #17 characterized by two or more, or three or more XRPD signals selected from the group consisting of 25.6 °2θ, 16.4 °2θ, 16.6 °2θ, 23.6 °2θ, and 21.7 °2θ (±0.2 °2θ; ±0.1°2θ; or 0.0 °2θ; Cu Kα1 radiation). In some embodiments, the solid form of tabernanthalog monofumarate salt Pattern #17 is crystalline tabernanthalog monofumarate salt Pattern #17 characterized by XRPD signals at 25.6 °2θ, 16.4 °2θ, 16.6 °2θ, 23.6 °2θ, and 21.7 °2θ (±0.2 °2θ; ±0.1 °2θ; or ±0.0 °2θ; Cu Kα1 radiation).

In some embodiments, the solid form of tabernanthalog monofumarate salt Pattern #17 is crystalline tabernanthalog monofumarate salt Pattern #17 characterized by two or more, or three or more XRPD signals selected from the group consisting of 25.6 °2θ, 16.4 °2θ, 16.6 °2θ, 23.6 °2θ, 21.7 °2θ, 19.6 °2θ, and 26.9 °2θ (±0.2°2θ; ±0.1°2θ; or 0.0 °2θ; Cu Kα1 radiation). In some embodiments, the solid form of tabernanthalog monofumarate salt Pattern #17 is crystalline tabernanthalog monofumarate salt Pattern #17 characterized by XRPD signals at 25.6 °2θ, 16.4 °2θ, 16.6 °2θ, 23.6 °2θ, 21.7 °2θ, 19.6 °2θ, and 26.9°2θ (±0.2°2θ; ±0.1°2θ; or 0.0 °2θ; Cu Kα1 radiation).

In some embodiments, the solid form of tabernanthalog monofumarate salt Pattern #17 is crystalline tabernanthalog monofumarate salt Pattern #17 characterized by two or more, or three or more XRPD signals selected from the group consisting of 25.6 °2θ, 16.4 °2θ, 16.6 °2θ, 23.6°2θ, 21.7°2θ, 19.6 °2θ, 26.9 °2θ, 9.1 °2θ, 22.4 °2θ, and 23.2°2θ (±0.2°2θ; ±0.1°2θ; or ±0.0 °2θ; Cu Kα1 radiation). In some embodiments, the solid form of tabernanthalog monofumarate salt Pattern #17 is crystalline tabernanthalog monofumarate salt Pattern #17 characterized by XRPD signals at 25.6 °2θ, 16.4 °2θ, 16.6 °2θ, 23.6 °2θ, 21.7 °2θ, 19.6 °2θ, 26.9 °2θ, 9.1 °2θ, 22.4 °2θ, and 23.2°2θ (±0.2°2θ; ±0.1 °2θ; or 0.0 °2θ; Cu Kα1 radiation).

In some embodiments, the crystalline tabernanthalog monofumarate salt Pattern #17 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 178.

In some embodiments, the solid form of tabernanthalog monofumarate salt Pattern #18 is crystalline tabernanthalog monofumarate salt Pattern #18 characterized by two or more, or three or more XRPD signals selected from the group consisting of 25.6 °2θ, 16.0 °2θ, and 18.0°2θ (±0.2 °2θ; ±0.1°2θ; or 0.0 °2θ; Cu Kα1 radiation). In some embodiments, the solid form of tabernanthalog monofumarate salt Pattern #18 is crystalline tabernanthalog monofumarate salt Pattern #18 characterized by XRPD signals 25.6 °2θ, 16.0 °2θ, and 18.0 °2θ (±0.2 °2θ; ±0.1 °2θ; or ±0.0 °2θ; Cu Kα1 radiation).

In some embodiments, the solid form of tabernanthalog monofumarate salt Pattern #18 is crystalline tabernanthalog monofumarate salt Pattern #18 characterized by two or more, or three or more XRPD signals selected from the group consisting 25.6 °2θ, 16.0 °2θ, 18.0 °2θ, 16.3 °2θ, and 21.4°2θ (±0.2°2θ; ±0.1 °2θ; or 0.0 °2θ; Cu Kα1 radiation). In some embodiments, the solid form of tabernanthalog monofumarate salt Pattern #18 is crystalline tabernanthalog monofumarate salt Pattern #18 characterized by XRPD signals at 25.6 °2θ, 16.0 °2θ, 18.0°2θ, 16.3°2θ, and 21.4 °2θ (±0.2 °2θ; ±0.1 °2θ; or 0.0 °2θ; Cu Kα1 radiation).

In some embodiments, the solid form of tabernanthalog monofumarate salt Pattern #18 is crystalline tabernanthalog monofumarate salt Pattern #18 characterized by two or more, or three or more XRPD signals selected from the group consisting of 25.6 °2θ, 16.0 °2θ, 18.0 °2θ, 16.3°2θ, 21.4 °2θ, 26.8 °2θ, and 23.0°2θ (±0.2°2θ; ±0.1°2θ; or ±0.0 °2θ; Cu Kα1 radiation). In some embodiments, the solid form of tabernanthalog monofumarate salt Pattern #18 is crystalline tabernanthalog monofumarate salt Pattern #18 characterized by XRPD signals at 25.6 °2θ, 16.0 °2θ, 18.0 °2θ, 16.3°2θ, 21.4 °2θ, 26.8 °2θ, and 23.0°2θ (±0.2 °2θ; ±0.1°2θ; or ±0.0 °2θ; Cu Kα1 radiation).

In some embodiments, the solid form of tabernanthalog monofumarate salt Pattern #18 is crystalline tabernanthalog monofumarate salt Pattern #18 characterized by two or more, or three or more XRPD signals selected from the group consisting of 25.6 °2θ, 16.0 °2θ, 18.0 °2θ, 16.3°2θ, 21.4 °2θ, 26.8 °2θ, 23.0 °2θ, 25.9 °2θ, 15.5 °2θ, and 11.0 °2θ (±0.2 °2θ; ±0.1 °2θ; or 0.0 °2θ; Cu Kα1 radiation). In some embodiments, the solid form of tabernanthalog monofumarate salt Pattern #18 is crystalline tabernanthalog monofumarate salt Pattern #18 characterized by XRPD signals at 25.6 °2θ, 16.0 °2θ, 18.0 °2θ, 16.3°2θ, 21.4 °2θ, 26.8 °2θ, 23.0 °2θ, 25.9 °2θ, 15.5 °2θ, and 11.0°2θ (±0.2°2θ; ±0.1°2θ; or 0.0 °2θ; Cu Kα1 radiation).

In some embodiments, the crystalline tabernanthalog monofumarate salt Pattern #18 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 179.

In some embodiments, the solid form of tabernanthalog monofumarate salt Pattern #19 is crystalline tabernanthalog monofumarate salt Pattern #19 characterized by two or more, or three or more XRPD signals selected from the group consisting of 25.6 °2θ, 25.5°2θ, and 16.4°2θ (±0.2 °2θ; ±0.1°2θ; or 0.0 °2θ; Cu Kα1 radiation). In some embodiments, the solid form of tabernanthalog monofumarate salt Pattern #19 is crystalline tabernanthalog monofumarate salt Pattern #19 characterized by XRPD signals 25.6 °2θ, 25.5 °2θ, and 16.4°2θ (±0.2 °2θ; ±0.1°2θ; or ±0.0 °2θ; Cu Kα1 radiation).

In some embodiments, the solid form of tabernanthalog monofumarate salt Pattern #19 is crystalline tabernanthalog monofumarate salt Pattern #19 characterized by two or more, or three or more XRPD signals selected from the group consisting 25.6 °2θ, 25.5°2θ, 16.4 °2θ, 20.5 °2θ, and 16.3°2θ (±0.2°2θ; ±0.1°2θ; or ±0.0 °2θ; Cu Kα1 radiation). In some embodiments, the solid form of tabernanthalog monofumarate salt Pattern #19 is crystalline tabernanthalog monofumarate salt Pattern #19 characterized by XRPD signals at 25.6 °2θ, 25.5°2θ, 16.4 °2θ, 20.5 °2θ, and 16.3°2θ (±0.2°2θ; ±0.1°2θ; or 0.0 °2θ; Cu Kα1 radiation).

In some embodiments, the solid form of tabernanthalog monofumarate salt Pattern #19 is crystalline tabernanthalog monofumarate salt Pattern #19 characterized by two or more, or three or more XRPD signals selected from the group consisting of 25.6 °2θ, 25.5 °2θ, 16.4 °2θ, 20.5 °2θ, 16.3 °2θ, 26.7 °2θ, and 22.8 °2θ (±0.2 °2θ; ±0.1 °2θ; or 0.0 °2θ; Cu Kα1 radiation). In some embodiments, the solid form of tabernanthalog monofumarate salt Pattern #19 is crystalline tabernanthalog monofumarate salt Pattern #19 characterized by XRPD signals at 25.6 °2θ, 25.5°2θ, 16.4 °2θ, 20.5 °2θ, 16.3°2θ, 26.7 °2θ, and 22.8°2θ (±0.2°2θ; ±0.1 °2θ; or ±0.0 °2θ; Cu Kα1 radiation).

In some embodiments, the solid form of tabernanthalog monofumarate salt Pattern #19 is crystalline tabernanthalog monofumarate salt Pattern #19 characterized by two or more, or three or more XRPD signals selected from the group consisting of 25.6 °2θ, 25.5°2θ, 16.4 °2θ, 20.5 °2θ, 16.3°2θ, 26.7 °2θ, 22.8 °2θ, 19.5 °2θ, 19.4 °2θ, and 17.0°2θ (±0.2 °2θ; ±0.1°2θ; or ±0.0 °2θ; Cu Kα1 radiation). In some embodiments, the solid form of tabernanthalog monofumarate salt Pattern #19 is crystalline tabernanthalog monofumarate salt Pattern #19 characterized by XRPD signals at 25.6 °2θ, 25.5°2θ, 16.4 °2θ, 20.5 °2θ, 16.3°2θ, 26.7 °2θ, 22.8 °2θ, 19.5 °2θ, 19.4 °2θ, and 17.0°2θ (±0.2 °2θ; ±0.1°2θ; or ±0.0 °2θ; Cu Kα1 radiation).

In some embodiments, the crystalline tabernanthalog monofumarate salt Pattern #19 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 180.

In some embodiments, the solid form of tabernanthalog monofumarate salt Pattern #20 is crystalline tabernanthalog monofumarate salt Pattern #20 characterized by two or more, or three or more XRPD signals selected from the group consisting of 6.1 °2θ, 25.5°2θ, and 16.3°2θ (±0.2°2θ; ±0.1°2θ; or ±0.0 °2θ; Cu Kα1 radiation). In some embodiments, the solid form of tabernanthalog monofumarate salt Pattern #20 is crystalline tabernanthalog monofumarate salt Pattern #20 characterized by XRPD signals 6.1 °2θ, 25.5°2θ, and 16.3°2θ (±0.2°2θ; ±0.1°2θ; or ±0.0 °2θ; Cu Kα1 radiation).

In some embodiments, the solid form of tabernanthalog monofumarate salt Pattern #20 is crystalline tabernanthalog monofumarate salt Pattern #20 characterized by two or more, or three or more XRPD signals selected from the group consisting 6.1 °2θ, 25.5°2θ, 16.3°2θ, 19.0 °2θ, and 18.2°2θ (±0.2°2θ; ±0.1 °2θ; or ±0.0 °2θ; Cu Kα1 radiation). In some embodiments, the solid form of tabernanthalog monofumarate salt Pattern #20 is crystalline tabernanthalog monofumarate salt Pattern #20 characterized by XRPD signals at 6.1 °2θ, 25.5°2θ, 16.3°2θ, 19.0 °2θ, and 18.2°2θ (±0.2 °2θ; ±0.1°2θ; or ±0.0 °2θ; Cu Kα1 radiation).

In some embodiments, the solid form of tabernanthalog monofumarate salt Pattern #20 is crystalline tabernanthalog monofumarate salt Pattern #20 characterized by two or more, or three or more XRPD signals selected from the group consisting 6.1 °2θ, 25.5°2θ, 16.3°2θ, 19.0 °2θ, 18.2 °2θ, 15.9 °2θ, and 16.7°2θ (±0.2°2θ; ±0.1°2θ; or 0.0 °2θ; Cu Kα1 radiation). In some embodiments, the solid form of tabernanthalog monofumarate salt Pattern #20 is crystalline tabernanthalog monofumarate salt Pattern #20 characterized by XRPD signals at 6.1 °2θ, 25.5 °2θ, 16.3°2θ, 19.0 °2θ, 18.2 °2θ, 15.9 °2θ, and 16.7°2θ (±0.2°2θ; ±0.1 °2θ; or 0.0 °2θ; Cu Kα1 radiation).

In some embodiments, the crystalline tabernanthalog monofumarate salt Pattern #20 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 181.

In some embodiments, the solid form of tabernanthalog hemifumarate salt Pattern #5 is crystalline tabernanthalog hemifumarate salt Pattern #5 characterized by two or more, or three or more XRPD signals selected from the group consisting of 8.2 °2θ, 16.9 °2θ, and 21.4 °2θ (±0.2 °2θ; ±0.1 °2θ; or 0.0 °2θ; Cu Kα1 radiation). In some embodiments, the solid form of tabernanthalog hemifumarate salt Pattern #5 is crystalline tabernanthalog hemifumarate salt Pattern #5 characterized by XRPD signals at 8.2 °2θ, 16.9 °2θ, and 21.4 °2θ (±0.2 °2θ; ±0.1°2θ; or 0.0 °2θ; Cu Kα1 radiation).

In some embodiments, the solid form of tabernanthalog hemifumarate salt Pattern #5 is crystalline tabernanthalog hemifumarate salt Pattern #5 characterized by two or more, or three or more XRPD signals selected from the group consisting of 8.2 °2θ, 16.9 °2θ, 21.4 °2θ, 23.6 °2θ, and 20.0°2θ (±0.2°2θ; ±0.1°2θ; or ±0.0 °2θ; Cu Kα1 radiation). In some embodiments, the solid form of tabernanthalog hemifumarate salt Pattern #5 is crystalline tabernanthalog hemifumarate salt Pattern #5 characterized by XRPD signals at 8.2 °2θ, 16.9 °2θ, 21.4 °2θ, 23.6 °2θ, and 20.0 °2θ (±0.2 °2θ; ±0.1 °2θ; or ±0.0 °2θ; Cu Kα1 radiation).

In some embodiments, the solid form of tabernanthalog hemifumarate salt Pattern #5 is crystalline tabernanthalog hemifumarate salt Pattern #5 characterized by two or more, or three or more XRPD signals selected from the group consisting of 8.2 °2θ, 16.9 °2θ, 21.4 °2θ, 23.6 °2θ, 20.0 °2θ, 11.1 °2θ, and 15.4 °2θ (±0.2°2θ; ±0.1 °2θ; or 0.0 °2θ; Cu Kα1 radiation). In some embodiments, the solid form of tabernanthalog hemifumarate salt Pattern #5 is crystalline tabernanthalog hemifumarate salt Pattern #5 characterized by XRPD signals at 8.2 °2θ, 16.9 °2θ, 21.4 °2θ, 23.6 °2θ, 20.0 °2θ, 11.1 °2θ, and 15.4°2θ (±0.2°2θ; ±0.1°2θ; or 0.0 °2θ; Cu Kα1 radiation).

In some embodiments, the solid form of tabernanthalog hemifumarate salt Pattern #5 is crystalline tabernanthalog hemifumarate salt Pattern #5 characterized by two or more, or three or more XRPD signals selected from the group consisting of 8.2 °2θ, 16.9 °2θ, 21.4 °2θ, 23.6 °2θ, 20.0 °2θ, 11.1 °2θ, 15.4 °2θ, 25.5°2θ, 22.5 °2θ, and 23.9°2θ (±0.2 °2θ; ±0.1°2θ; or 0.0 °2θ; Cu Kα1 radiation). In some embodiments, the solid form of tabernanthalog hemifumarate salt Pattern #5 is crystalline tabernanthalog hemifumarate salt Pattern #5 characterized by XRPD signals at 8.2 °2θ, 16.9 °2θ, 21.4 °2θ, 23.6 °2θ, 20.0 °2θ, 11.1 °2θ, 15.4 °2θ, 25.5 °2θ, 22.5 °2θ, and 23.9 °2θ (±0.2 °2θ; ±0.1°2θ; or 0.0 °2θ; Cu Kα1 radiation).

In some embodiments, the crystalline tabernanthalog hemifumarate salt Pattern #5 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 181B.

In some embodiments, the solid form of tabernanthalog hemifumarate salt Pattern #14 is crystalline tabernanthalog hemifumarate salt Pattern #14 characterized by two or more, or three or more XRPD signals selected from the group consisting of 8.2 °2θ, 15.5 °2θ, and 17.0 °2θ (±0.2 °2θ; ±0.1 °2θ; or 0.0 °2θ; Cu Kα1 radiation). In some embodiments, the solid form of tabernanthalog hemifumarate salt Pattern #14 is crystalline tabernanthalog hemifumarate salt Pattern #14 characterized by XRPD signals at 8.2 °2θ, 15.5 °2θ, and 17.0°2θ (±0.2°2θ; ±0.1°2θ; or 0.0 °2θ; Cu Kα1 radiation).

In some embodiments, the solid form of tabernanthalog hemifumarate salt Pattern #14 is crystalline tabernanthalog hemifumarate salt Pattern #14 characterized by two or more, or three or more XRPD signals selected from the group consisting of 8.2 °2θ, 15.5 °2θ, 17.0 °2θ, 22.6 °2θ, and 20.2°2θ (±0.2°2θ; ±0.1°2θ; or 0.0 °2θ; Cu Kα1 radiation). In some embodiments, the solid form of tabernanthalog hemifumarate salt Pattern #14 is crystalline tabernanthalog hemifumarate salt Pattern #14 characterized by XRPD signals at 8.2 °2θ, 15.5 °2θ, 17.0 °2θ, 22.6 °2θ, and 20.2°2θ (±0.2°2θ; ±0.1°2θ; or 0.0 °2θ; Cu Kα1 radiation).

In some embodiments, the solid form of tabernanthalog hemifumarate salt Pattern #14 is crystalline tabernanthalog hemifumarate salt Pattern #14 characterized by two or more, or three or more XRPD signals selected from the group consisting of 8.2 °2θ, 15.5 °2θ, 17.0 °2θ, 22.6 °2θ, 20.2 °2θ, 11.2 °2θ, and 23.7°2θ (±0.2°2θ; ±0.1°2θ; or 0.0 °2θ; Cu Kα1 radiation). In some embodiments, the solid form of tabernanthalog hemifumarate salt Pattern #14 is crystalline tabernanthalog hemifumarate salt Pattern #14 characterized by XRPD signals at 8.2 °2θ, 15.5 °2θ, 17.0 °2θ, 22.6 °2θ, 20.2°2θ, 11.2 °2θ, and 23.7°2θ (±0.2°2θ; ±0.1°2θ; or ±0.0 °2θ; Cu Kα1 radiation).

In some embodiments, the solid form of tabernanthalog hemifumarate salt Pattern #14 is crystalline tabernanthalog hemifumarate salt Pattern #14 characterized by two or more, or three or more XRPD signals selected from the group consisting of 8.2 °2θ, 15.5 °2θ, 17.0 °2θ, 22.6 °2θ, 20.2 °2θ, 11.2 °2θ, 23.7 °2θ, 24.8°2θ, 21.5 °2θ, and 18.1 °2θ (±0.2°2θ; ±0.1°2θ; or ±0.0 °2θ; Cu Kα1 radiation). In some embodiments, the solid form of tabernanthalog hemifumarate salt Pattern #14 is crystalline tabernanthalog hemifumarate salt Pattern #14 characterized by XRPD signals at 8.2 °2θ, 15.5 °2θ, 17.0 °2θ, 22.6 °2θ, 20.2°2θ, 11.2 °2θ, 23.7 °2θ, 24.8 °2θ, 21.5 °2θ, and 18.1 °2θ (±0.2°2θ; ±0.1°2θ; or ±0.0 °2θ; Cu Kα1 radiation).

In some embodiments, the crystalline tabernanthalog hemifumarate salt Pattern #14 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 181D.

In some embodiments, the solid form of tabernanthalog hemifumarate salt Pattern #14 is crystalline tabernanthalog hemifumarate salt Pattern #14 characterized by two or more, or three or more XRPD signals selected from the group consisting of 8.2 °2θ, 11.3 °2θ, and 17.1°2θ (±0.2°2θ; ±0.1 °2θ; or ±0.0 °2θ; Cu Kα1 radiation). In some embodiments, the solid form of tabernanthalog hemifumarate salt Pattern #14 is crystalline tabernanthalog hemifumarate salt Pattern #14 characterized by XRPD signals at 8.2 °2θ, 11.3 °2θ, and 17.1 °2θ (±0.2 °2θ; ±0.1 °2θ; or 0.0 °2θ; Cu Kα1 radiation).

In some embodiments, the solid form of tabernanthalog hemifumarate salt Pattern #14 is crystalline tabernanthalog hemifumarate salt Pattern #14 characterized by two or more, or three or more XRPD signals selected from the group consisting of 8.2 °2θ, 11.3 °2θ, 17.1 °2θ, 21.5 °2θ, and 20.3°2θ (±0.2°2θ; ±0.1°2θ; or ±0.0 °2θ; Cu Kα1 radiation). In some embodiments, the solid form of tabernanthalog hemifumarate salt Pattern #14 is crystalline tabernanthalog hemifumarate salt Pattern #14 characterized by XRPD signals at 8.2 °2θ, 11.3 °2θ, 17.1 °2θ, 21.5 °2θ, and 20.3°2θ (±0.2 °2θ; ±0.1°2θ; or ±0.0 °2θ; Cu Kα1 radiation).

In some embodiments, the solid form of tabernanthalog hemifumarate salt Pattern #14 is crystalline tabernanthalog hemifumarate salt Pattern #14 characterized by two or more, or three or more XRPD signals selected from the group consisting of 8.2 °2θ, 11.3 °2θ, 17.1 °2θ, 21.5 °2θ, 20.3 °2θ, 15.6 °2θ, and 12.9°2θ (±0.2 °2θ; ±0.1°2θ; or 0.0 °2θ; Cu Kα1 radiation). In some embodiments, the solid form of tabernanthalog hemifumarate salt Pattern #14 is crystalline tabernanthalog hemifumarate salt Pattern #14 characterized by XRPD signals at 8.2 °2θ, 11.3 °2θ, 17.1 °2θ, 21.5 °2θ, 20.3 °2θ, 15.6°2θ, and 12.9 °2θ (±0.2°2θ; ±0.1°2θ; or ±0.0 °2θ; Cu Kα1 radiation).

In some embodiments, the solid form of tabernanthalog hemifumarate salt Pattern #14 is crystalline tabernanthalog hemifumarate salt Pattern #14 characterized by two or more, or three or more XRPD signals selected from the group consisting of 8.2 °2θ, 11.3 °2θ, 17.1 °2θ, 21.5 °2θ, 20.3 °2θ, 15.6°2θ, 12.9 °2θ, 19.1 °2θ, 21.2 °2θ, and 22.7°2θ (±0.2°2θ; ±0.1°2θ; or 0.0 °2θ; Cu Kα1 radiation). In some embodiments, the solid form of tabernanthalog hemifumarate salt Pattern #14 is crystalline tabernanthalog hemifumarate salt Pattern #14 characterized by XRPD signals at 8.2 °2θ, 11.3 °2θ, 17.1 °2θ, 21.5 °2θ, 20.3 °2θ, 15.6 °2θ, 12.9 °2θ, 19.1 °2θ, 21.2 °2θ, and 22.7°2θ (±0.2 °2θ; ±0.1 °2θ; or 0.0 °2θ; Cu Kα1 radiation).

In some embodiments, the crystalline tabernanthalog hemifumarate salt Pattern #14 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 181E.

In some embodiments, the solid form of tabernanthalog hemifumarate salt Pattern #21 is crystalline tabernanthalog hemifumarate salt Pattern #21 characterized by two or more, or three or more XRPD signals selected from the group consisting of 19.2 °2θ, 16.7 °2θ, and 25.4 °2θ (±0.2 °2θ; ±0.1°2θ; or 0.0 °2θ; Cu Kα1 radiation). In some embodiments, the solid form of tabernanthalog hemifumarate salt Pattern #21 is crystalline tabernanthalog hemifumarate salt Pattern #21 characterized by XRPD signals at 19.2 °2θ, 16.7 °2θ, and 25.4°2θ (±0.2°2θ; ±0.1°2θ; or 0.0 °2θ; Cu Kα1 radiation).

In some embodiments, the solid form of tabernanthalog hemifumarate salt Pattern #21 is crystalline tabernanthalog hemifumarate salt Pattern #21 characterized by two or more, or three or more XRPD signals selected from the group consisting of 19.2 °2θ, 16.7 °2θ, 25.4 °2θ, 22.2 °2θ, and 27.2 °2θ (±0.2 °2θ; ±0.1 °2θ; or 0.0 °2θ; Cu Kα1 radiation). In some embodiments, the solid form of tabernanthalog hemifumarate salt Pattern #21 is crystalline tabernanthalog hemifumarate salt Pattern #21 characterized by XRPD signals at 19.2 °2θ, 16.7 °2θ, 25.4 °2θ, 22.2 °2θ, and 27.2 °2θ (±0.2 °2θ; ±0.1 °2θ; or 0.0 °2θ; Cu Kα1 radiation).

In some embodiments, the solid form of tabernanthalog hemifumarate salt Pattern #21 is crystalline tabernanthalog hemifumarate salt Pattern #21 characterized by two or more, or three or more XRPD signals selected from the group consisting of 19.2 °2θ, 16.7 °2θ, 25.4 °2θ, 22.2 °2θ, 27.2 °2θ, 18.1 °2θ, and 17.7°2θ (±0.2°2θ; ±0.1 °2θ; or ±0.0 °2θ; Cu Kα1 radiation). In some embodiments, the solid form of tabernanthalog hemifumarate salt Pattern #21 is crystalline tabernanthalog hemifumarate salt Pattern #21 characterized by XRPD signals at 19.2 °2θ, 16.7 °2θ, 25.4 °2θ, 22.2 °2θ, 27.2 °2θ, 18.1 °2θ, and 17.7°2θ (±0.2°2θ; ±0.1°2θ; or 0.0 °2θ; Cu Kα1 radiation).

In some embodiments, the solid form of tabernanthalog hemifumarate salt Pattern #21 is crystalline tabernanthalog hemifumarate salt Pattern #21 characterized by two or more, or three or more XRPD signals selected from the group consisting of 19.2 °2θ, 16.7 °2θ, 25.4 °2θ, 22.2 °2θ, 27.2 °2θ, 18.1 °2θ, 17.7 °2θ, 21.2 °2θ, 26.1 °2θ, and 6.7°2θ (±0.2°2θ; ±0.1°2θ; or ±0.0 °2θ; Cu Kα1 radiation). In some embodiments, the solid form of tabernanthalog hemifumarate salt Pattern #21 is crystalline tabernanthalog hemifumarate salt Pattern #21 characterized by XRPD signals at 19.2 °2θ, 16.7 °2θ, 25.4 °2θ, 22.2 °2θ, 27.2 °2θ, 18.1 °2θ, 17.7 °2θ, 21.2 °2θ, 26.1 °2θ, and 6.7 °2θ; Cu Kα1 radiation).

In some embodiments, the crystalline tabernanthalog hemifumarate salt Pattern #21 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 182.

In some embodiments, the solid form of tabernanthalog hemifumarate salt Pattern #22 is crystalline tabernanthalog hemifumarate salt Pattern #22 characterized by two or more, or three or more XRPD signals selected from the group consisting of 18.9 °2θ, 19.3 °2θ, and 16.7°2θ (±0.2 °2θ; ±0.1 °2θ; or ±0.0 °2θ; Cu Kα1 radiation). In some embodiments, the solid form of tabernanthalog hemifumarate salt Pattern #22 is crystalline tabernanthalog hemifumarate salt Pattern #22 characterized by XRPD signals at 18.9 °2θ, 19.3 °2θ, and 16.7 °2θ (±0.2 °2θ; ±0.1 °2θ; or ±0.0 °2θ; Cu Kα1 radiation).

In some embodiments, the solid form of tabernanthalog hemifumarate salt Pattern #22 is crystalline tabernanthalog hemifumarate salt Pattern #22 characterized by two or more, or three or more XRPD signals selected from the group consisting of 18.9 °2θ, 19.3 °2θ, 16.7 °2θ, 27.3 °2θ, and 18.2 °2θ (±0.2 °2θ; ±0.1°2θ; or 0.0 °2θ; Cu Kα1 radiation). In some embodiments, the solid form of tabernanthalog hemifumarate salt Pattern #22 is crystalline tabernanthalog hemifumarate salt Pattern #22 characterized by XRPD signals at 18.9 °2θ, 19.3 °2θ, 16.7 °2θ, 27.3 °2θ, and 18.2 °2θ (±0.2 °2θ; ±0.1 °2θ; or ±0.0 °2θ; Cu Kα1 radiation).

In some embodiments, the solid form of tabernanthalog hemifumarate salt Pattern #22 is crystalline tabernanthalog hemifumarate salt Pattern #22 characterized by two or more, or three or more XRPD signals selected from the group consisting of 18.9 °2θ, 19.3 °2θ, 16.7 °2θ, 27.3 °2θ, 18.2 °2θ, 6.7 °2θ, and 25.5 °2θ (±0.2 °2θ; ±0.1 °2θ; or ±0.0 °2θ; Cu Kα1 radiation). In some embodiments, the solid form of tabernanthalog hemifumarate salt Pattern #22 is crystalline tabernanthalog hemifumarate salt Pattern #22 characterized by XRPD signals at 18.9 °2θ, 19.3 °2θ, 16.7 °2θ, 27.3 °2θ, 18.2 °2θ, 6.7 °2θ, and 25.5 °2θ (±0.2 °2θ; ±0.1 °2θ; or 0.0 °2θ; Cu Kα1 radiation).

In some embodiments, the solid form of tabernanthalog hemifumarate salt Pattern #22 is crystalline tabernanthalog hemifumarate salt Pattern #22 characterized by two or more, or three or more XRPD signals selected from the group consisting of 18.9 °2θ, 19.3 °2θ, 16.7 °2θ, 27.3 °2θ, 18.2 °2θ, 6.7 °2θ, 25.5 °2θ, 17.7 °2θ, 20.2 °2θ, and 22.3 °2θ (±0.2 °2θ; ±0.1 °2θ; or ±0.0 °2θ; Cu Kα1 radiation). In some embodiments, the solid form of tabernanthalog hemifumarate salt Pattern #22 is crystalline tabernanthalog hemifumarate salt Pattern #22 characterized by XRPD signals at 18.9 °2θ, 19.3 °2θ, 16.7 °2θ, 27.3 °2θ, 18.2 °2θ, 6.7 °2θ, 25.5 °2θ, 17.7 °2θ, 20.2 °2θ, and 22.3 °2θ; Cu Kα1 radiation).

In some embodiments, the crystalline tabernanthalog hemifumarate salt Pattern #22 is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-one, fifty-two, fifty-three, fifty-four, fifty-five, fifty-six, fifty-seven, fifty-eight, fifty-nine, sixty, sixty-one, sixty-two, sixty-three, sixty-four, sixty-five, or sixty-six XRPD signals selected from those set forth in Table 183.

In some embodiments, the solid form of tabernanthalog monofumarate (Form A) is crystalline tabernanthalog monofumarate (Form A) characterized by two or more, or three or more XRPD signals selected from the group consisting of 16.2 °2θ, 18.9 °2θ, and 24.9 °2θ (±0.2 °2θ; ±0.1 °2θ; or ±0.0 °2θ; Cu Kα1 radiation).

In some embodiments, the solid form of tabernanthalog monofumarate (Form A) is crystalline tabernanthalog monofumarate (Form A) characterized by XRPD signals at 16.2 °2θ, 18.9 °2θ, and 24.9 °2θ (±0.2 °2θ; ±0.1 °2θ; or 0.0 °2θ; Cu Kα1 radiation).

In some embodiments, the solid form of tabernanthalog monofumarate (Form A) is crystalline tabernanthalog monofumarate (Form A) characterized by XRPD signals at 16.2 °2θ, 18.9 °2θ, 19.2 °2θ, 20.2 °2θ, and 24.9°2θ (±0.2°2θ; ±0.1 °2θ; or 0.0 °2θ; Cu Kα1 radiation).

In some embodiments, the solid form of tabernanthalog monofumarate (Form A) is crystalline tabernanthalog monofumarate (Form A) characterized by XRPD signals at 16.2 °2θ, 18.9 °2θ, 19.2 °2θ, 20.2 °2θ, 21.6 °2θ, 24.9 °2θ, and 25.8 °2θ (±0.2°2θ; ±0.1°2θ; or 0.0 °2θ; Cu Kα1 radiation).

In some embodiments, the solid form of tabernanthalog monofumarate (Form A) is crystalline tabernanthalog monofumarate (Form A) characterized by XRPD signals at 15.7 °2θ, 16.2 °2θ, 18.9 °2θ, 19.2 °2θ, 20.2 °2θ, 21.6 °2θ, 24.9 °2θ, 25.8 °2θ, 27.8 °2θ, and 37.4°2θ (±0.2°2θ; ±0.1 °2θ; or ±0.0 °2θ; Cu Kα1 radiation).

In some embodiments, the crystalline tabernanthalog monofumarate is characterized by one, two, three, four, five, six, seven, eight, nine, or ten XRPD signals selected from those set forth in Table 258.

In some embodiments, the solid form of tabernanthalog monofumarate is crystalline tabernanthalog monofumarate characterized by two or more, or three or more XRPD signals selected from the group consisting of 19.4 °2θ, 26.0 °2θ, and 17.0°2θ (±0.2°2θ; ±0.1 °2θ; or 0.0 °2θ; Cu Kα1 radiation). In some embodiments, the solid form of tabernanthalog monofumarate is crystalline tabernanthalog monofumarate characterized by XRPD signals at 19.4 °2θ, 26.0 °2θ, and 17.0°2θ (±0.2°2θ; ±0.1°2θ; or 0.0 °2θ; Cu Kα1 radiation).

In some embodiments, the solid form of tabernanthalog monofumarate is crystalline tabernanthalog monofumarate characterized by two or more, or three or more XRPD signals selected from the group consisting of 19.4 °2θ, 26.0 °2θ, 17.0 °2θ, 12.9 °2θ, and 24.5°2θ (±0.2°2θ; ±0.1 °2θ; or ±0.0 °2θ; Cu Kα1 radiation). In some embodiments, the solid form of tabernanthalog monofumarate is crystalline tabernanthalog monofumarate characterized by XRPD signals at 19.4 °2θ, 26.0 °2θ, 17.0 °2θ, 12.9 °2θ, and 24.5 °2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate characterized by two or more, or three or more XRPD signals selected from the group consisting of 19.4 °2θ, 26.0 °2θ, 17.0 °2θ, 12.9 °2θ, 24.5 °2θ, 20.6 °2θ, and 18.0 °2θ (±0.2 °2θ; ±0.1°2θ; or ±0.0 °2θ; Cu Kα1 radiation). In some embodiments, the solid form of tabernanthalog monofumarate is crystalline tabernanthalog monofumarate characterized by XRPD signals at 19.4 °2θ, 26.0 °2θ, 17.0 °2θ, 12.9 °2θ, 24.5 °2θ, 20.6 °2θ, and 18.0°2θ (±0.2 °2θ; ±0.1 °2θ; or ±0.0 °2θ; Cu Kα1 radiation).

In some embodiments, the solid form of tabernanthalog monofumarate is crystalline tabernanthalog monofumarate characterized by two or more, or three or more XRPD signals selected from the group consisting of 15.6 °2θ, 19.4 °2θ, 26.0 °2θ, 17.0 °2θ, 12.9 °2θ, 24.5 °2θ, 20.6 °2θ, and 18.0 °2θ (±0.2 °2θ; ±0.1 °2θ; or 0.0 °2θ; Cu Kα1 radiation). In some embodiments, the solid form of tabernanthalog monofumarate is crystalline tabernanthalog monofumarate characterized by XRPD signals at 15.6 °2θ, 19.4 °2θ, 26.0 °2θ, 17.0 °2θ, 12.9 °2θ, 24.5 °2θ, 20.6 °2θ, and 18.0°2θ (±0.2°2θ; ±0.1°2θ; or 0.0 °2θ; Cu Kα1 radiation).

In some embodiments, the crystalline tabernanthalog monofumarate is characterized by one, two, three, four, five, six, seven, or eight XRPD signals selected from those set forth in Table 321.

In some embodiments, the tabernanthalog monofumarate salt is crystalline polymorphic Pattern #1 characterized by two or more, or three XRPD signals selected from the group consisting of 25.5°2θ, 16.3°2θ, 19.3 °2θ, 16.7 °2θ, 18.1 °2θ, 27.2 °2θ, 26.8 °2θ, 9 °2θ, 22.3 °2θ, 25.1 °2θ, 26.1 °2θ, 17.4 °2θ, 23.1 °2θ, 14.2 °2θ, 30020, and 17.7°2θ (±0.2°2θ; ±0.1°2θ; or 0.0 °2θ; Cu Kα1 radiation).

In some embodiments, the tabernanthalog monofumarate salt is crystalline polymorphic Pattern #1 characterized by two or more, or three XRPD signals selected from the group consisting of 25.5°2θ, 16.3°2θ, and 19.3°2θ (±0.2 °2θ; ±0.1°2θ; or 0.0 °2θ; Cu Kα1 radiation).

In some embodiments, the tabernanthalog monofumarate salt is crystalline polymorphic Pattern #1 characterized by XRPD signals at 25.5°2θ, 16.3°2θ, 19.3 °2θ, 16.7 °2θ, 18.1 °2θ, 27.2 °2θ, 26.8 °2θ, 9 °2θ, 22.3 °2θ, 25.1 °2θ, 26.1 °2θ, 17.4 °2θ, 23.1 °2θ, 14.2 °2θ, 30 °2θ, and 17.7°2θ (±0.2°2θ; ±0.1°2θ; or ±0.0 °2θ; Cu Kα1 radiation).

In some embodiments, the tabernanthalog monofumarate salt is crystalline polymorphic Pattern #1 characterized by XRPD signals at 25.5°2θ, 16.3°2θ, and 19.3°2θ (±0.2°2θ; ±0.1°2θ; or ±0.0 °2θ; Cu Kα1 radiation).

In some embodiments, the tabernanthalog monofumarate salt is crystalline polymorphic Pattern #1 characterized by two or more, or three XRPD signals as shown in Table 155.

In some embodiments, the tabernanthalog monofumarate salt is crystalline polymorphic Pattern #1 characterized by two or more, or three XRPD signals selected from the group consisting of 25.5 °2θ, 16.3 °2θ, 19.3 °2θ, 16.7 °2θ, 18.1 °2θ, 26.8 °2θ, 9 °2θ, 22.3 °2θ, 27.2 °2θ, 24.6 °2θ, 17.4 °2θ, 17.8 °2θ, 15.6 °2θ, 23.1 °2θ, 25.1 °2θ, 26.2 °2θ, and 18.8°2θ (±0.2 °2θ; ±0.1 °2θ; or 0.0 °2θ; Cu Kα1 radiation).

In some embodiments, the tabernanthalog monofumarate salt is crystalline polymorphic Pattern #1 characterized by two or more, or three XRPD signals selected from the group consisting of 25.5°2θ, 16.3°2θ, and 19.3°2θ (±0.2°2θ; ±0.1°2θ; or 0.0 °2θ; Cu Kα1 radiation).

In some embodiments, the tabernanthalog monofumarate salt is crystalline polymorphic Pattern #1 characterized by XRPD signals at 25.5°2θ, 16.3°2θ, 19.3 °2θ, 16.7 °2θ, 18.1 °2θ, 26.8 °2θ, 9 °2θ, 22.3 °2θ, 27.2 °2θ, 24.6 °2θ, 17.4 °2θ, 17.8 °2θ, 15.6 °2θ, 23.1 °2θ, 25.1 °2θ, 26.2 °2θ, and 18.8 °2θ (±0.2 °2θ; ±0.1°2θ; or ±0.0 °2θ; Cu Kα1 radiation).

In some embodiments, the tabernanthalog monofumarate salt is crystalline polymorphic Pattern #1 characterized by XRPD signals at 25.5 °2θ, 16.3°2θ, and 19.3 °2θ (±0.2°2θ; ±0.1°2θ; or 0.0 °2θ; Cu Kα1 radiation).

In some embodiments, the tabernanthalog monofumarate salt is crystalline polymorphic Pattern #1 characterized by two or more, or three XRPD signals as shown in Table 156.

In some embodiments, the tabernanthalog fumarate salt has an ¹H NMR spectra as provided in FIGS. 295 and 296.

In some embodiments, the tabernanthalog fumarate salt has a TGA profile as provided in FIG. 299.

In some embodiments, the TGA profile of the tabernanthalog fumarate salt shows a first TG event (−2.1% w/w).

In some embodiments, the tabernanthalog fumarate salt has a DSC profile as provided in FIG. 300.

In some embodiments, the DSC profile of the tabernanthalog fumarate salt exhibits a bimodal transition corresponding to the melting of two different crystal forms.

In some embodiments, the tabernanthalog fumarate salt has a DVS profile as provided in FIG. 301.

In some embodiments, the tabernanthalog monofumarate salt is crystalline polymorphic Pattern #1 characterized by two or more, or three XRPD signals selected from the group consisting of 25.5°2θ, 16.3°2θ, 19.3 °2θ, 16.7 °2θ, 5.1 °2θ, 10.2°2θ, 27.2 °2θ, 18.1 °2θ, 9 °2θ, 26.8 °2θ, 22.3 °2θ, 25.2 °2θ, 17.4 °2θ, 26.1 °2θ, 17.7 °2θ, 23 °2θ, 29.9 °2θ, and 6.7°2θ (±0.2°2θ; ±0.1°2θ; or ±0.0 °2θ; Cu Kα1 radiation).

In some embodiments, the tabernanthalog monofumarate salt is crystalline polymorphic Pattern #1 characterized by two or more, or three XRPD signals selected from the group consisting of 25.5°2θ, 16.3 °2θ, 19.3 °2θ, 16.7 °2θ, 5.1 °2θ, 10.2°2θ, 27.2 °2θ, 18.1 °2θ, 9 °2θ, and 26.8°2θ (±0.2°2θ; ±0.1°2θ; or 0.0 °2θ; Cu Kα1 radiation).

In some embodiments, the tabernanthalog monofumarate salt is crystalline polymorphic Pattern #1 characterized by XRPD signals at 25.5°2θ, 16.3°2θ, 19.3 °2θ, 16.7 °2θ, 5.1 °2θ, 10.2 °2θ, 27.2 °2θ, 18.1 °2θ, 9 °2θ, 26.8 °2θ, 22.3 °2θ, 25.2 °2θ, 17.4 °2θ, 26.1 °2θ, 17.7 °2θ, 23 °2θ, 29.9 °2θ, and 6.7°2θ (±0.2°2θ; ±0.1°2θ; or 0.0 °2θ; Cu Kα1 radiation).

In some embodiments, the tabernanthalog monofumarate salt is crystalline polymorphic Pattern #1 characterized by XRPD signals at 25.5 °2θ, 16.3°2θ, 19.3 °2θ, 16.7 °2θ, 5.1 °2θ, 10.2 °2θ, 27.2 °2θ, 18.1 °2θ, 9 °2θ, and 26.8°2θ (±0.2°2θ; ±0.1°2θ; or ±0.0 °2θ; Cu Kα1 radiation).

In some embodiments, the tabernanthalog monofumarate salt is crystalline polymorphic Pattern #1 characterized by two or more, or three XRPD signals as shown in Table 157.

In some embodiments, the tabernanthalog monofumarate salt is crystalline polymorphic Pattern #2a characterized by two or more, or three XRPD signals selected from the group consisting of 25.6 °2θ, 16.4 °2θ, 17.1 °2θ, 23 °2θ, 9.1 °2θ, 27.3 °2θ, 15.7 °2θ, 26.8 °2θ, 18.1 °2θ, 20.7 °2θ, 12.3 °2θ, 25 °2θ, 22.8 °2θ, 21 °2θ, 14.2 °2θ, 24.7 °2θ, 17.4 °2θ, 18.8 °2θ, and 22.3 °2θ (±0.2 °2θ; ±0.1°2θ; or 0.0 °2θ; Cu Kα1 radiation).

In some embodiments, the tabernanthalog monofumarate salt is crystalline polymorphic Pattern #2a characterized by XRPD signals at 25.6 °2θ, 16.4 °2θ, 17.1 °2θ, 23 °2θ, 9.1 °2θ, 27.3 °2θ, 15.7 °2θ, 26.8 °2θ, 18.1 °2θ, 20.7 °2θ, 12.3 °2θ, 25 °2θ, 22.8 °2θ, 21 °2θ, 14.2 °2θ, 24.7 °2θ, 17.4 °2θ, 18.8 °2θ, and 22.3°2θ (±0.2°2θ; ±0.1 °2θ; or 0.0 °2θ; Cu Kα1 radiation).

In some embodiments, the tabernanthalog monofumarate salt is crystalline polymorphic Pattern #2a characterized by two or more, or three XRPD signals selected from the group consisting of 25.6 °2θ, 16.4 °2θ, and 17.1°2θ (±0.2°2θ; ±0.1°2θ; or 0.0 °2θ; Cu Kα1 radiation).

In some embodiments, the tabernanthalog monofumarate salt is crystalline polymorphic Pattern #2a characterized by XRPD signals at 25.6 °2θ, 16.4 °2θ, and 17.1 °2θ (±0.2 °2θ; ±0.1°2θ; or ±0.0 °2θ; Cu Kα1 radiation).

In some embodiments, the tabernanthalog monofumarate salt is crystalline polymorphic Pattern #2a characterized by two or more, or three XRPD signals as shown in Table 158.

In some embodiments, the tabernanthalog monofumarate salt is crystalline polymorphic Pattern #2a characterized by an ¹H NMR spectrum as depicted in FIG. 313.

Figure 3:
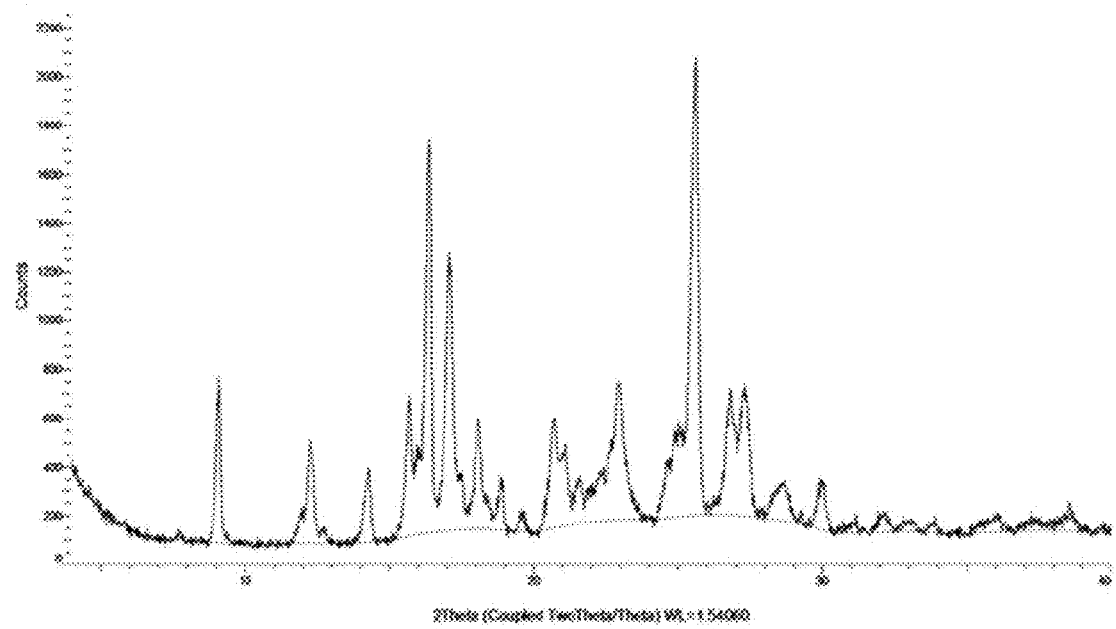
FIG. 3 depicts an XRPD diffractogram of a sample isolated from acetonitrile/heptanes (10 vol acetonitrile/5 vol heptanes stirred at 40° C.) comprising crystalline tabernanthalog fumarate of Pattern #2a. The XRPD signals observed in this diffractogram are characterized in Table 158.

In some embodiments, the tabernanthalog monofumarate salt is crystalline polymorphic Pattern #2a characterized by an XRPD profile as depicted in FIG. 3.

In some embodiments, the tabernanthalog monofumarate salt is crystalline polymorphic Pattern #2a characterized by a TGA profile as depicted in FIG. 315.

In some embodiments, the tabernanthalog monofumarate salt is crystalline polymorphic Pattern #2a characterized by a DSC profile as depicted in FIG. 316. In some embodiments, the tabernanthalog monofumarate salt is crystalline polymorphic Pattern #2b characterized by two or more, or three XRPD signals selected from the group consisting of 25.5 °2θ, 16.3°2θ, 24.6 °2θ, 18.1 °2θ, 9 °2θ, 25.1 °2θ, 15.8 °2θ, 26.8 °2θ, 15.5 °2θ, 17 °2θ, 22.6 °2θ, 17.4 °2θ, 19.4 °2θ, 22.3 °2θ, 14.2 °2θ, 18.8 °2θ, and 21°2θ (±0.2 °2θ; ±0.1 °2θ; or ±0.0 °2θ; Cu Kα1 radiation).

In some embodiments, the tabernanthalog monofumarate salt is crystalline polymorphic Pattern #2b characterized by two or more, or three XRPD signals selected from the group consisting of 25.5 °2θ, 16.3°2θ, 24.6 °2θ, 18.1 °2θ, 9 °2θ, 25.1 °2θ, 15.8 °2θ, 26.8 °2θ, 15.5 °2θ, and 17°2θ (±0.2°2θ; ±0.1 °2θ; or 0.0 °2θ; Cu Kα1 radiation).

In some embodiments, the tabernanthalog monofumarate salt is crystalline polymorphic Pattern #2b characterized by XRPD signals at 25.5°2θ, 16.3 °2θ, 24.6 °2θ, 18.1 °2θ, 9 °2θ, 25.1 °2θ, 15.8 °2θ, 26.8 °2θ, 15.5 °2θ, 17 °2θ, 22.6 °2θ, 17.4 °2θ, 19.4 °2θ, 22.3 °2θ, 14.2 °2θ, 18.8 °2θ, and 21°2θ (±0.2°2θ; ±0.1°2θ; or 0.0 °2θ; Cu Kα1 radiation).

In some embodiments, the tabernanthalog monofumarate salt is crystalline polymorphic Pattern #2b characterized by XRPD signals at 25.5 °2θ, 16.3°2θ, 24.6 °2θ, 18.1 °2θ, 9 °2θ, 25.1 °2θ, 15.8 °2θ, 26.8 °2θ, 15.5 °2θ, and 17 °2θ (±0.2 °2θ; ±0.1°2θ; or ±0.0 °2θ; Cu Kα1 radiation).

In some embodiments, the tabernanthalog monofumarate salt is crystalline polymorphic Pattern #2b characterized by two or more, or three XRPD signals as shown in Table 159.

In some embodiments, the tabernanthalog monofumarate salt is crystalline polymorphic Pattern #2c characterized by two or more, or three XRPD signals selected from the group consisting of 25.5°2θ, 16.3°2θ, 19.3 °2θ, 16.7 °2θ, 22.3 °2θ, 27.2 °2θ, 9 °2θ, 18.1 °2θ, 26.8 °2θ, 17.7 °2θ, 26.1 °2θ, 23 °2θ, 25.1 °2θ, 17.4 °2θ, 21.2 °2θ, and 20.2°2θ (±0.2°2θ; ±0.1°2θ; or 0.0 °2θ; Cu Kα1 radiation).

In some embodiments, the tabernanthalog monofumarate salt is crystalline polymorphic Pattern #2c characterized by two or more, or three XRPD signals selected from the group consisting of 25.5°2θ, 16.3°2θ, 19.3 °2θ, 16.7 °2θ, 22.3 °2θ, 27.2 °2θ, 9 °2θ, 18.1 °2θ, 26.8 °2θ, and 17.7°2θ (±0.2°2θ; ±0.1 °2θ; or 0.0 °2θ; Cu Kα1 radiation).

In some embodiments, the tabernanthalog monofumarate salt is crystalline polymorphic Pattern #2c characterized by XRPD signals at 25.5°2θ, 16.3°2θ, 19.3 °2θ, 16.7 °2θ, 22.3

°2θ, 27.2 °2θ, 9 °2θ, 18.1 °2θ, 26.8 °2θ, 17.7 °2θ, 26.1 °2θ, 23 °2θ, 25.1 °2θ, 17.4 °2θ, 21.2 °2θ, and 20.2 °2θ (±0.2 °2θ; ±0.1 °2θ; or 0.0 °2θ; Cu Kα1 radiation).

In some embodiments, the tabernanthalog monofumarate salt is crystalline polymorphic Pattern #2c characterized by XRPD signals at 25.5 °2θ, 16.3 °2θ, 19.3 °2θ, 16.7 °2θ, 22.3 °2θ, 27.2 °2θ, 9 °2θ, 18.1 °2θ, 26.8 °2θ, and 17.7 °2θ (±0.2 °2θ; ±0.1 °2θ; or ±0.0 °2θ; Cu Kα1 radiation).

In some embodiments, the tabernanthalog monofumarate salt is crystalline polymorphic Pattern #2c characterized by two or more, or three XRPD signals as shown in Table 160.

In some embodiments, the tabernanthalog monofumarate salt is crystalline polymorphic Pattern #2d characterized by two or more, or three XRPD signals selected from the group consisting of 25.6 °2θ, 16.3 °2θ, 16.2 °2θ, 25.2 °2θ, 9.1 °2θ, 22.1 °2θ, 26 °2θ, 26.8 °2θ, 18.1 °2θ, 19.9 °2θ, 21.1 °2θ, 17.5 °2θ, 14.2 °2θ, 30 °2θ, 27.2 °2θ, and 28.6 °2θ (±0.2 °2θ; ±0.1 °2θ; or ±0.0 °2θ; Cu Kα1 radiation).

In some embodiments, the tabernanthalog monofumarate salt is crystalline polymorphic Pattern #2d characterized by two or more, or three XRPD signals selected from the group consisting of 25.6 °2θ, 16.3 °2θ, 16.2 °2θ, 25.2 °2θ, 9.1 °2θ, 22.1 °2θ, 26 °2θ, 26.8 °2θ, 18.1 °2θ, and 19.9 °2θ (±0.2 °2θ; ±0.1 °2θ; or 0.0 °2θ; Cu Kα1 radiation).

In some embodiments, the tabernanthalog monofumarate salt is crystalline polymorphic Pattern #2d characterized by XRPD signals at 25.6 °2θ, 16.3 °2θ, 16.2 °2θ, 25.2 °2θ, 9.1 °2θ, 22.1 °2θ, 26 °2θ, 26.8 °2θ, 18.1 °2θ, 19.9 °2θ, 21.1 °2θ, 17.5 °2θ, 14.2020, 30 °2θ, 27.2 °2θ, and 28.6 °2θ (±0.2 °2θ; ±0.1 °2θ; or 0.0 °2θ; Cu Kα1 radiation).

In some embodiments, the tabernanthalog monofumarate salt is crystalline polymorphic Pattern #2d characterized by XRPD signals at 25.6 °2θ, 16.3 °2θ, 16.2 °2θ, 25.2 °2θ, 9.1 °2θ, 22.1 °2θ, 26 °2θ, 26.8 °2θ, 18.1 °2θ, and 19.9 °2θ (±0.2 °2θ; ±0.1 °2θ; or ±0.0 °2θ; Cu Kα1 radiation).

In some embodiments, the tabernanthalog monofumarate salt is crystalline polymorphic Pattern #2d characterized by two or more, or three XRPD signals as shown in Table 161.

In some embodiments, the tabernanthalog monofumarate salt is crystalline polymorphic Pattern #3 characterized by two or more, or three XRPD signals selected from the group consisting of 25.5 °2θ, 16.3 °2θ, 16.6 °2θ, 20.1 °2θ, 26.0 °2θ, 22.2 °2θ, 26.8 °2θ, 16.8 °2θ, 18.8 °2θ, 9.0 °2θ, 22.5 °2θ, 18 °2θ, 25 °2θ, 11.1 °2θ, 24.7 °2θ, 12.5 °2θ, 14.4 °2θ, 14.3 °2θ, 8.4 °2θ, 19.3 °2θ, 27.2 °2θ, 17.4 °2θ, 29.9 °2θ, and 9.8 °2θ (±0.2 °2θ; ±0.1 °2θ; or ±0.0 °2θ; Cu Kα1 radiation).

In some embodiments, the tabernanthalog monofumarate salt is crystalline polymorphic Pattern #3 characterized by two or more, or three XRPD signals selected from the group consisting of 25.5 °2θ, 16.3 °2θ, 16.6 °2θ, 20.1 °2θ, 26.0 °2θ, 22.2 °2θ, 26.8 °2θ, 16.8 °2θ, 18.8 °2θ, and 9.0 °2θ (±0.2 °2θ; ±0.1 °2θ; or 0.0 °2θ; Cu Kα1 radiation).

In some embodiments, the tabernanthalog monofumarate salt is crystalline polymorphic Pattern #3 characterized by XRPD signals at 25.5 °2θ, 16.3 °2θ, 16.6 °2θ, 20.1 °2θ, 26.0 °2θ, 22.2 °2θ, 26.8 °2θ, 16.8 °2θ, 18.8 °2θ, 9.0 °2θ, 22.5 °2θ, 18 °2θ, 25 °2θ, 11.1 °2θ, 24.7 °2θ, 12.5 °2θ, 14.4 °2θ, 14.3 °2θ, 8.4 °2θ, 19.3 °2θ, 27.2 °2θ, 17.4 °2θ, 29.9 °2θ, and 9.8°2θ (±0.2°2θ; ±0.1 °2θ; or 0.0 °2θ; Cu Kα1 radiation).

In some embodiments, the tabernanthalog monofumarate salt is crystalline polymorphic Pattern #3 characterized by XRPD signals at 25.5 °2θ, 16.3 °2θ, 16.6 °2θ, 20.1 °2θ, 26.0 °2θ, 22.2 °2θ, 26.8 °2θ, 16.8 °2θ, 18.8 °2θ, and 9.0°2θ (±0.2°2θ; ±0.1°2θ; or 0.0 °2θ; Cu Kα1 radiation).

In some embodiments, the tabernanthalog monofumarate salt is crystalline polymorphic Pattern #3 characterized by two or more, or three XRPD signals as shown in Table 162.

In some embodiments, the tabernanthalog monofumarate salt is crystalline polymorphic Pattern #4a characterized by two or more, or three XRPD signals selected from the group consisting of 25.5 °2θ, 16.3 °2θ, 8.2 °2θ, 11.3 °2θ, 9.0 °2θ, 23.8 °2θ, 19.3 °2θ, 17.1 °2θ, 19.4 °2θ, 26.8 °2θ, 21.5 °2θ, 18 °2θ, 20.5 °2θ, 20.4 °2θ, 15.6 °2θ, 25.2 °2θ, 22.6 °2θ, 18.9 °2θ, 14.2 °2θ, 12.7 °2θ, and 30020 (±0.2 °2θ; ±0.1°2θ; or 0.0 °2θ; Cu Kα1 radiation).

In some embodiments, the tabernanthalog monofumarate salt is crystalline polymorphic Pattern #4a characterized by two or more, or three XRPD signals selected from the group consisting of 25.5 °2θ, 16.3 °2θ, 8.2 °2θ, 11.3 °2θ, 9.0 °2θ, 23.8 °2θ, 19.3 °2θ, 17.1 °2θ, 19.4 °2θ, and 26.8°2θ (±0.2°2θ; ±0.1°2θ; or 0.0 °2θ; Cu Kα1 radiation).

In some embodiments, the tabernanthalog monofumarate salt is crystalline polymorphic Pattern #4a characterized by XRPD signals at 25.5 °2θ, 16.3 °2θ, 8.2 °2θ, 11.3 °2θ, 9.0 °2θ, 23.8 °2θ, 19.3 °2θ, 17.1 °2θ, 19.4 °2θ, 26.8 °2θ, 21.5 °2θ, 18 °2θ, 20.5 °2θ, 20.4 °2θ, 15.6 °2θ, 25.2 °2θ, 22.6 °2θ, 18.9 °2θ, 14.2 °2θ, 12.7 °2θ, and 30°2θ (±0.2°2θ; ±0.1°2θ; or 0.0 °2θ; Cu Kα1 radiation).

In some embodiments, the tabernanthalog monofumarate salt is crystalline polymorphic Pattern #4a characterized by XRPD signals at 25.5 °2θ, 16.3°2θ, 8.2 °2θ, 11.3 °2θ, 9.0°2θ, 23.8 °2θ, 19.3 °2θ, 17.1 °2θ, 19.4 °2θ, and 26.8°2θ (±0.2°2θ; ±0.1 °2θ; or 0.0 °2θ; Cu Kα1 radiation).

In some embodiments, the tabernanthalog monofumarate salt is crystalline polymorphic Pattern #4a characterized by two or more, or three XRPD signals as shown in Table 163.

In some embodiments, the tabernanthalog monofumarate salt is crystalline polymorphic Pattern #4b characterized by two or more, or three XRPD signals selected from the group consisting of 25.6 °2θ, 16.3°2θ, 8.2 °2θ, 9.1 °2θ, 17.2 °2θ, 18.1 °2θ, 26.8 °2θ, 15.7 °2θ, 27.3 °2θ, 21.5 °2θ, 11.3 °2θ, 22.6 °2θ, 23.9 °2θ, 25.2 °2θ, 20.4 °2θ, 21.4 °2θ, 19.3 °2θ, 17.4 °2θ, 14.2 °2θ, 16.8 °2θ, 18.8 °2θ, and 22.4°2θ (±0.2 °2θ, 0.1°2θ; or ±0.0 °2θ; Cu Kα1 radiation).

In some embodiments, the tabernanthalog monofumarate salt is crystalline polymorphic Pattern #4b characterized by two or more, or three XRPD signals selected from the group consisting of 25.6 °2θ, 16.3 °2θ, 8.2 °2θ, 9.1 °2θ, 17.2 °2θ, 18.1 °2θ, 26.8 °2θ, 15.7 °2θ, 27.3 °2θ, and 21.5°2θ (±0.2°2θ; ±0.1°2θ; or 0.0 °2θ; Cu Kα1 radiation).

In some embodiments, the tabernanthalog monofumarate salt is crystalline polymorphic Pattern #4b characterized by XRPD signals at 25.6 °2θ, 16.3 °2θ, 8.2 °2θ, 9.1 °2θ, 17.2 °2θ, 18.1 °2θ, 26.8 °2θ, 15.7 °2θ, 27.3 °2θ, 21.5 °2θ, 11.3 °2θ, 22.6 °2θ, 23.9 °2θ, 25.2 °2θ, 20.4 °2θ, 21.4 °2θ, 19.3 °2θ, 17.4 °2θ, 14.2 °2θ, 16.8 °2θ, 18.8 °2θ, and 22.4°2θ (±0.2°2θ; ±0.1°2θ; or 0.0 °2θ; Cu Kα1 radiation).

In some embodiments, the tabernanthalog monofumarate salt is crystalline polymorphic Pattern #4b characterized by XRPD signals at 25.6 °2θ, 16.3°2θ, 8.2 °2θ, 9.1 °2θ, 17.2 °2θ, 18.1 °2θ, 26.8 °2θ, 15.7 °2θ, 27.3 °2θ, and 21.5 °2θ (±0.2 °2θ; ±0.1°2θ; or ±0.0 °2θ; Cu Kα1 radiation).

In some embodiments, the tabernanthalog monofumarate salt is crystalline polymorphic Pattern #4b characterized by two or more, or three XRPD signals as shown in Table 164.

In some embodiments, the tabernanthalog hemifumarate salt is crystalline polymorphic Pattern #5 characterized by two or more, or three XRPD signals selected from the group consisting of 8.2 °2θ, 16.9 °2θ, 21.4 °2θ, 23.6 °2θ, 20.0 °2θ, 11.1 °2θ, 15.4 °2θ, 25.5 °2θ, 22.5 °2θ, 23.9 °2θ, 30.2 °2θ, 22.2 °2θ, 19.1 °2θ, 16.3 °2θ, 12.8 °2θ, and 26.8°2θ (±0.2°2θ; ±0.1°2θ; or ±0.0 °2θ; Cu Kα1 radiation).

In some embodiments, the tabernanthalog hemifumarate salt is crystalline polymorphic Pattern #5 characterized by two or more, or three XRPD signals selected from the group consisting of 8.2 °2θ, 16.9 °2θ, 21.4 °2θ, 23.6 °2θ, 20.0 °2θ, 11.1 °2θ, 15.4 °2θ, 25.5 °2θ, 22.5 °2θ, and 23.9 °2θ (±0.2°2θ; ±0.1°2θ; or ±0.0 °2θ; Cu Kα1 radiation).

In some embodiments, the tabernanthalog hemifumarate salt is crystalline polymorphic Pattern #5 characterized by XRPD signals at 8.2 °2θ, 16.9 °2θ, 21.4 °2θ, 23.6 °2θ, 20.0 °2θ, 11.1 °2θ, 15.4 °2θ, 25.5 °2θ, 22.5 °2θ, 23.9 °2θ, 30.2 °2θ, 22.2 °2θ, 19.1 °2θ, 16.3°2θ, 12.8 °2θ, and 26.8°2θ (±0.2 °2θ; 0.1°2θ; or ±0.0 °2θ; Cu Kα1 radiation).

In some embodiments, the tabernanthalog hemifumarate salt is crystalline polymorphic Pattern #5 characterized by XRPD signals at 8.2 °2θ, 16.9 °2θ, 21.4 °2θ, 23.6 °2θ, 20.0 °2θ, 11.1 °2θ, 15.4 °2θ, 25.5°2θ, 22.5 °2θ, and 23.9 °2θ (±0.2 °2θ; ±0.1 °2θ; or ±0.0 °2θ; Cu Kα1 radiation).

In some embodiments, the tabernanthalog hemifumarate salt is crystalline polymorphic Pattern #5 characterized by two or more, or three XRPD signals as shown in Table 181B.

In some embodiments, the tabernanthalog monofumarate salt is crystalline polymorphic Pattern #6a characterized by two or more, or three XRPD signals selected from the group consisting of 19.6 °2θ, 16.6 °2θ, 20.7 °2θ, 25.4 °2θ, 19.3 °2θ, 26.2 °2θ, 22.1 °2θ, 33.6 °2θ, and 13°2θ (±0.2 °2θ; ±0.1°2θ; or 0.0 °2θ; Cu Kα1 radiation).

In some embodiments, the tabernanthalog monofumarate salt is crystalline polymorphic Pattern #6a characterized by two or more, or three XRPD signals selected from the group consisting of 19.6 °2θ, 16.6 °2θ, 20.7 °2θ, 25.4 °2θ, 19.3 °2θ, 26.2 °2θ, 22.1 °2θ, and 33.6°2θ (±0.2°2θ; ±0.1 °2θ; or 0.0 °2θ; Cu Kα1 radiation).

In some embodiments, the tabernanthalog monofumarate salt is crystalline polymorphic Pattern #6a characterized by two or more, or three XRPD signals selected from the group consisting of 19.6 °2θ, 16.6 °2θ, 20.7 °2θ, 25.4 °2θ, 19.3 °2θ, 26.2 °2θ, and 22.1°2θ (±0.2°2θ; ±0.1°2θ; or ±0.0 °2θ; Cu Kα1 radiation).

In some embodiments, the tabernanthalog monofumarate salt is crystalline polymorphic Pattern #6a characterized by two or more, or three XRPD signals selected from the group consisting of 19.6 °2θ, 16.6 °2θ, 20.7 °2θ, 25.4 °2θ, 19.3 °2θ, and 26.2°2θ (±0.2°2θ; ±0.1°2θ; or 0.0 °2θ; Cu Kα1 radiation).

In some embodiments, the tabernanthalog monofumarate salt is crystalline polymorphic Pattern #6a characterized by two or more, or three XRPD signals selected from the group consisting of 19.6 °2θ, 16.6 °2θ, 20.7 °2θ, 25.4 °2θ, 19.3 °2θ, and 26.2°2θ (±0.2°2θ; ±0.1 °2θ; or 0.0 °2θ; Cu Kα1 radiation).

In some embodiments, the tabernanthalog monofumarate salt is crystalline polymorphic Pattern #6a characterized by two or more, or three XRPD signals selected from the group consisting of 19.6 °2θ, 16.6 °2θ, 20.7 °2θ, 25.4 °2θ, and 19.3°2θ (±0.2 °2θ; ±0.1°2θ; or 0.0 °2θ; Cu Kα1 radiation).

In some embodiments, the tabernanthalog monofumarate salt is crystalline polymorphic Pattern #6a characterized by two or more, or three XRPD signals selected from the group consisting of 19.6 °2θ, 16.6 °2θ, 20.7 °2θ, and 25.4°2θ (±0.2°2θ; ±0.1 °2θ; or ±0.0 °2θ; Cu Kα1 radiation). In some embodiments, the tabernanthalog monofumarate salt is crystalline polymorphic Pattern #6a characterized by two or more, or three XRPD signals selected from the group consisting of 19.6 °2θ, 16.6 °2θ, and 20.7 °2θ (±0.2 °2θ; ±0.1 °2θ; or ±0.0 °2θ; Cu Kα1 radiation).

In some embodiments, the tabernanthalog monofumarate salt is crystalline polymorphic Pattern #6a characterized by XRPD signals at 19.6 °2θ, 16.6 °2θ, 20.7 °2θ, 25.4 °2θ, 19.3 °2θ, 26.2 °2θ, 22.1 °2θ, 33.6 °2θ, and 13°2θ (±0.2°2θ; ±0.1°2θ; or 0.0 °2θ; Cu Kα1 radiation).

In some embodiments, the tabernanthalog monofumarate salt is crystalline polymorphic Pattern #6a characterized by XRPD signals at 19.6 °2θ, 16.6 °2θ, 20.7 °2θ, 25.4 °2θ, 19.3 °2θ, 26.2 °2θ, 22.1 °2θ, and 33.6 °2θ (±0.2 °2θ; ±0.1°2θ; or 0.0 °2θ; Cu Kα1 radiation).

In some embodiments, the tabernanthalog monofumarate salt is crystalline polymorphic Pattern #6a characterized by XRPD signals at 19.6 °2θ, 16.6 °2θ, 20.7 °2θ, 25.4 °2θ, 19.3 °2θ, 26.2 °2θ, and 22.1 °2θ (±0.2°2θ; ±0.1 °2θ; or ±0.0 °2θ; Cu Kα1 radiation).

In some embodiments, the tabernanthalog monofumarate salt is crystalline polymorphic Pattern #6a characterized by XRPD signals at 19.6 °2θ, 16.6 °2θ, 20.7 °2θ, 25.4 °2θ, 19.3 °2θ, and 26.2°2θ (±0.2°2θ; ±0.1 °2θ; or ±0.0 °2θ; Cu Kα1 radiation).

In some embodiments, the tabernanthalog monofumarate salt is crystalline polymorphic Pattern #6a characterized by XRPD signals at 19.6 °2θ, 16.6 °2θ, 20.7 °2θ, 25.4 °2θ, and 19.3°2θ (±0.2°2θ; ±0.1°2θ; or 0.0 °2θ; Cu Kα1 radiation).

In some embodiments, the tabernanthalog monofumarate salt is crystalline polymorphic Pattern #6a characterized by XRPD signals at 19.6 °2θ, 16.6 °2θ, 20.7 °2θ, and 25.4 °2θ (±0.2 °2θ; ±0.1°2θ; or ±0.0 °2θ; Cu Kα1 radiation).

In some embodiments, the tabernanthalog monofumarate salt is crystalline polymorphic Pattern #6a characterized by XRPD signals at 19.6 °2θ, 16.6 °2θ, 20.7 °2θ, and 25.4°2θ (±0.2°2θ; ±0.1°2θ; or 0.0 °2θ; Cu Kα1 radiation).

In some embodiments, the tabernanthalog monofumarate salt is crystalline polymorphic Pattern #6a characterized by XRPD signals at 19.6 °2θ, 16.6 °2θ, and 20.7°2θ (±0.2°2θ; ±0.1 °2θ; or 0.0 °2θ; Cu Kα1 radiation).

In some embodiments, the tabernanthalog monofumarate salt is crystalline polymorphic Pattern #6a characterized by two or more, or three XRPD signals as shown in Table 166.

In some embodiments, the tabernanthalog monofumarate salt is crystalline polymorphic Pattern #6a characterized by an $^1$H NMR spectrum as depicts in FIG. 344.

Figure 13:
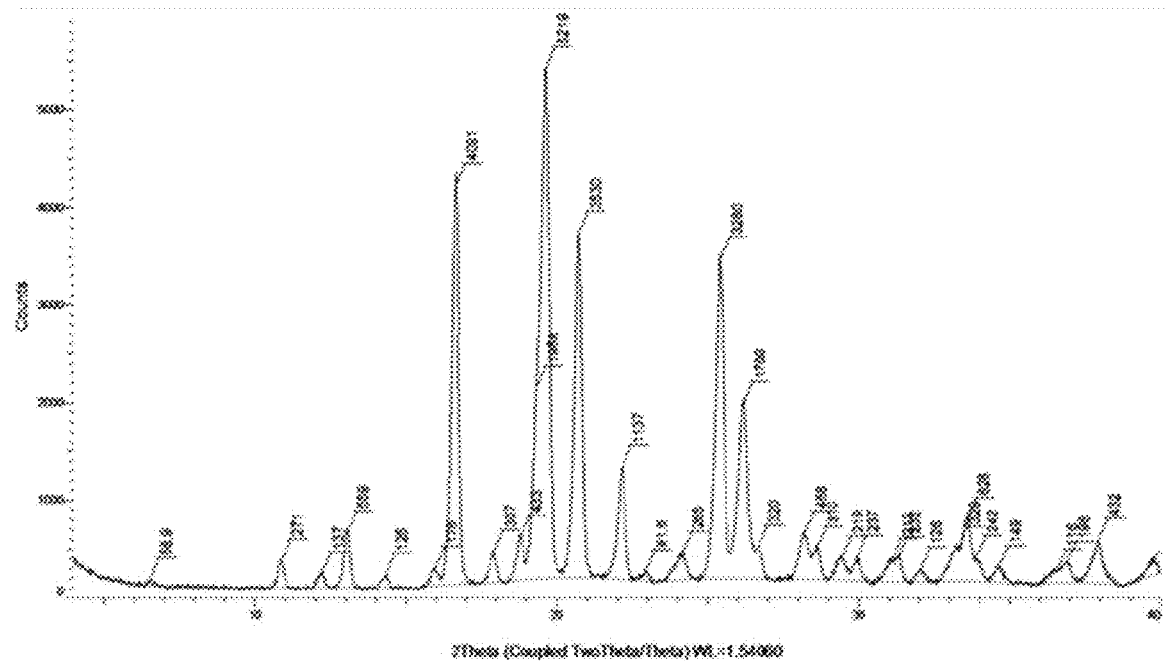
FIG. 13 depicts an XRPD diffractogram of a sample comprising crystalline tabernanthalog fumarate of Pattern #6a. The XRPD signals observed in this diffractogram are characterized in Table 166.

In some embodiments, the tabernanthalog monofumarate salt is crystalline polymorphic Pattern #6a characterized by an XRPD profile as depicts in FIG. 13.

In some embodiments, the tabernanthalog monofumarate salt is crystalline polymorphic Pattern #6a characterized by TGA profile as depicted in FIG. 347.

In some embodiments, the tabernanthalog monofumarate salt is crystalline polymorphic Pattern #6a characterized by a DSC profile as depicted in FIG. 348.

In some embodiments, the tabernanthalog monofumarate salt is crystalline polymorphic Pattern #6b characterized by two or more, or three XRPD signals selected from the group consisting of 19.4 °2θ, 16.5 °2θ, 20.5 °2θ, 25.3 °2θ, 26 °2θ, 22 °2θ, 12.9 °2θ, 8.2 °2θ, 33.4 °2θ, and 37.7°2θ (±0.2 °2θ; ±0.1 °2θ; or 0.0 °2θ; Cu Kα1 radiation).

In some embodiments, the tabernanthalog monofumarate salt is crystalline polymorphic Pattern #6b characterized by XRPD signals at 19.4 °2θ, 16.5 °2θ, 20.5 °2θ, 25.3 °2θ, 26 °2θ, 22 °2θ, 12.9 °2θ, 8.2 °2θ, 33.4 °2θ, and 37.7°2θ (±0.2 °2θ; ±0.1°2θ; or ±0.0 °2θ; Cu Kα1 radiation).

In some embodiments, the tabernanthalog monofumarate salt is crystalline polymorphic Pattern #6b characterized by two or more, or three XRPD signals as shown in Table 167.

In some embodiments, the tabernanthalog monofumarate salt is crystalline polymorphic Pattern #7 characterized by two or more, or three XRPD signals selected from the group consisting of 16.4 °2θ, 25.6 °2θ, 15.9 °2θ, 7.2 °2θ, 24.9 °2θ, 19.4 °2θ, 9.1 °2θ, 21.3 °2θ, 19.8 °2θ, 16.8 °2θ, 27.3 °2θ, 22.5 °2θ, 18.2 °2θ, 26.9 °2θ, 14.3 °2θ, 20.8 °2θ, and 17.5°2θ (±0.2 °2θ; ±0.1°2θ; or ±0.0 °2θ; Cu Kα1 radiation).

In some embodiments, the tabernanthalog monofumarate salt is crystalline polymorphic Pattern #7 characterized by two or more, or three XRPD signals selected from the group consisting of 16.4 °2θ, 25.6 °2θ, 15.9 °2θ, 7.2 °2θ, 24.9 °2θ, 19.4 °2θ, 9.1 °2θ, 21.3 °2θ, 19.8 °2θ, and 16.8°2θ (±0.2°2θ; ±0.1°2θ; or 0.0 °2θ; Cu Kα1 radiation).

In some embodiments, the tabernanthalog monofumarate salt is crystalline polymorphic Pattern #7 characterized by XRPD signals at 16.4 °2θ, 25.6 °2θ, 15.9 °2θ, 7.2 °2θ, 24.9 °2θ, 19.4 °2θ, 9.1 °2θ, 21.3 °2θ, 19.8 °2θ, 16.8 °2θ, 27.3 °2θ, 22.5 °2θ, 18.2 °2θ, 26.9 °2θ, 14.3 °2θ, 20.8 °2θ, and 17.5°2θ (±0.2 °2θ; ±0.1°2θ; or 0.0 °2θ; Cu Kα1 radiation).

In some embodiments, the tabernanthalog monofumarate salt is crystalline polymorphic Pattern #7 characterized by XRPD signals at 16.4 °2θ, 25.6 °2θ, 15.9 °2θ, 7.2 °2θ, 24.9 °2θ, 19.4 °2θ, 9.1 °2θ, 21.3 °2θ, 19.8 °2θ, and 16.8°2θ (±0.2°2θ; ±0.1°2θ; or 0.0 °2θ; Cu Kα1 radiation).

In some embodiments, the tabernanthalog monofumarate salt is crystalline polymorphic Pattern #7 characterized by two or more, or three XRPD signals as shown in Table 168.

In some embodiments, the tabernanthalog monofumarate salt is crystalline polymorphic Pattern #8 characterized by two or more, or three XRPD signals selected from the group consisting of 25.5 °2θ, 16.3 °2θ, 15.8 °2θ, 24.2 °2θ, 20.5 °2θ, 24.8 °2θ, 18 °2θ, 19 °2θ, 7.6 °2θ, 9 °2θ, 26.7 °2θ, 22.5 °2θ, 27.2 °2θ, 17.4 °2θ, 18.9 °2θ, 19.5 °2θ, 22.3 °2θ, 21.9 °2θ, and 14.2°2θ (±0.2 °2θ; ±0.1 °2θ; or ±0.0 °2θ; Cu Kα1 radiation).

In some embodiments, the tabernanthalog monofumarate salt is crystalline polymorphic Pattern #8 characterized by two or more, or three XRPD signals selected from the group consisting of 25.5 °2θ, 16.3°2θ, 15.8 °2θ, 24.2 °2θ, 20.5 °2θ, 24.8 °2θ, 18 °2θ, 19 °2θ, 7.6 °2θ, and 9°2θ (±0.2 °2θ, ±0.1°2θ; or ±0.0 °2θ; Cu Kα1 radiation).

In some embodiments, the tabernanthalog monofumarate salt is crystalline polymorphic Pattern #8 characterized by XRPD signals at 25.5°2θ, 16.3°2θ, 15.8 °2θ, 24.2 °2θ, 20.5 °2θ, 24.8 °2θ, 18 °2θ, 19 °2θ, 7.6 °2θ, 9 °2θ, 26.7 °2θ, 22.5 °2θ, 27.2 °2θ, 17.4 °2θ, 18.9 °2θ, 19.5 °2θ, 22.3 °2θ, 21.9 °2θ, and 14.2°2θ (±0.2°2θ; ±0.1°2θ; or ±0.0 °2θ; Cu Kα1 radiation).

In some embodiments, the tabernanthalog monofumaratefmonoumarate salt is crystalline polymorphic Pattern #8 characterized by XRPD signals at 25.5°2θ, 16.3°2θ, 15.8 °2θ, 24.2 °2θ, 20.5 °2θ, 24.8 °2θ, 18 °2θ, 19 °2θ, 7.6 °2θ, and 9°2θ (±0.2°2θ; ±0.1°2θ; or ±0.0 °2θ; Cu Kα1 radiation).

In some embodiments, the tabernanthalog monofumarate salt is crystalline polymorphic Pattern #8 characterized by two or more, or three XRPD signals as shown in Table 169.

In some embodiments, the tabernanthalog monofumarate salt is crystalline polymorphic Pattern #9 characterized by two or more, or three XRPD signals selected from the group consisting of 15.9 °2θ, 25.6 °2θ, 24.7 °2θ, 16.4 °2θ, 19.5 °2θ, 21.9 °2θ, 17.1 °2θ, 8 °2θ, 9.2 °2θ, 20.8 °2θ, 27 °2θ, 18.2 °2θ, 28.8 °2θ, 19.2 °2θ, 22.4 °2θ, 14.3 °2θ, 10.5 °2θ, 12.2 °2θ, and 27.3°2θ (±0.2°2θ; ±0.1°2θ; or ±0.0 °2θ; Cu Kα1 radiation).

In some embodiments, the tabernanthalog monofumarate salt is crystalline polymorphic Pattern #9 characterized by two or more, or three XRPD signals selected from the group consisting of 15.9 °2θ, 25.6 °2θ, 24.7 °2θ, 16.4 °2θ, 19.5 °2θ, 21.9 °2θ, 17.1 °2θ, 8 °2θ, 9.2 °2θ, and 20.8°2θ (±0.2°2θ; ±0.1°2θ; or ±0.0 °2θ; Cu Kα1 radiation).

In some embodiments, the tabernanthalog monofumarate salt is crystalline polymorphic Pattern #9 characterized by XRPD signals at 15.9 °2θ, 25.6 °2θ, 24.7 °2θ, 16.4 °2θ, 19.5 °2θ, 21.9 °2θ, 17.1 °2θ, 8 °2θ, 9.2020, 20.8 °2θ, 27 °2θ, 18.2 °2θ, 28.8 °2θ, 19.2 °2θ, 22.4 °2θ, 14.3 °2θ, 10.5 °2θ, 12.2 °2θ, and 27.3°2θ (±0.2°2θ; ±0.1 °2θ; or ±0.0 °2θ; Cu Kα1 radiation).

In some embodiments, the tabernanthalog monofumarate salt is crystalline polymorphic Pattern #9 characterized by XRPD signals at 15.9 °2θ, 25.6 °2θ, 24.7 °2θ, 16.4 °2θ, 19.5 °2θ, 21.9 °2θ, 17.1 °2θ, 8020, 9.2020, and 20.8°2θ (±0.2 °2θ; ±0.1°2θ; or ±0.0 °2θ; Cu Kα1 radiation). In some embodiments, the tabernanthalog monofumarate salt is crystalline polymorphic Pattern #9 characterized by two or more, or three XRPD signals as shown in Table 170.

In some embodiments, the tabernanthalog monofumarate salt is crystalline polymorphic Pattern #10 characterized by two or more, or three XRPD signals selected from the group consisting of 25.5°2θ, 16.9 °2θ, 16.3°2θ, 21.3 °2θ, 23.5 °2θ, 8.2 °2θ, 10.8 °2θ, 23.4 °2θ, 9.1 °2θ, 19.8 °2θ, 15.2 °2θ, 23.6 °2θ, 26.8 °2θ, 21.8 °2θ, 22.2 °2θ, 18 °2θ, 25.2 °2θ, 19.6 °2θ, 14.2 °2θ, 19.1 °2θ, 29.8 °2θ, 22.6 °2θ, 17.4 °2θ, 26.1 °2θ, and 18.8 °2θ (±0.2 °2θ; ±0.1°2θ; or ±0.0 °2θ; Cu Kα1 radiation).

In some embodiments, the tabernanthalog monofumarate salt is crystalline polymorphic Pattern #10 characterized by two or more, or three XRPD signals selected from the group consisting of 25.5 °2θ, 16.9 °2θ, 16.3°2θ, 21.3 °2θ, 23.5 °2θ, 8.2 °2θ, 10.8 °2θ, 23.4 °2θ, 9.1 °2θ, and 19.8°2θ (±0.2°2θ; ±0.1 °2θ; or ±0.0 °2θ; Cu Kα1 radiation).

In some embodiments, the tabernanthalog monofumarate salt is crystalline polymorphic Pattern #10 characterized by XRPD signals at 25.5°2θ, 16.9 °2θ, 16.3°2θ, 21.3 °2θ, 23.5 °2θ, 8.2 °2θ, 10.8 °2θ, 23.4 °2θ, 9.1 °2θ, 19.8 °2θ, 15.2 °2θ, 23.6 °2θ, 26.8 °2θ, 21.8 °2θ, 22.2 °2θ, 18 °2θ, 25.2 °2θ, 19.6 °2θ, 14.2 °2θ, 19.1 °2θ, 29.8 °2θ, 22.6 °2θ, 17.4 °2θ, 26.1 °2θ, and 18.8°2θ (±0.2 °2θ; ±0.1°2θ; or ±0.0 °2θ; Cu Kα1 radiation).

In some embodiments, the tabernanthalog monofumarate salt is crystalline polymorphic Pattern #10 characterized by XRPD signals at 25.5°2θ, 16.9 °2θ, 16.3°2θ, 21.3 °2θ, 23.5 °2θ, 8.2 °2θ, 10.8 °2θ, 23.4 °2θ, 9.1 °2θ, and 19.8°2θ (±0.2 °2θ; ±0.1 °2θ; or ±0.0 °2θ; Cu Kα1 radiation).

In some embodiments, the tabernanthalog monofumarate salt is crystalline polymorphic Pattern #10 characterized by two or more, or three XRPD signals as shown in Table 171.

In some embodiments, the tabernanthalog monofumarate salt is crystalline polymorphic Pattern #11 characterized by two or more, or three XRPD signals selected from the group consisting of 16.1 °2θ, 25.7 °2θ, 16.4 °2θ, 21.6 °2θ, 20.4 °2θ, 7.5 °2θ, 9.2 °2θ, 23.9 °2θ, 20.9 °2θ, 17.4 °2θ, 22.8 °2θ, 11.2 °2θ, 27 °2θ, 24 °2θ, 18.2 °2θ, 10.8 °2θ, 25.3 °2θ, 22.5 °2θ, and 14.3°2θ (±0.2°2θ; ±0.1 °2θ; or ±0.0 °2θ; Cu Kα1 radiation).

In some embodiments, the tabernanthalog monofumarate salt is crystalline polymorphic Pattern #11 characterized by two or more, or three XRPD signals selected from the group consisting of 16.1 °2θ, 25.7 °2θ, 16.4 °2θ, 21.6 °2θ, 20.4 °2θ, 7.5 °2θ, 9.2 °2θ, 23.9 °2θ, 20.9 °2θ, and 17.4°2θ (±0.2 °2θ; ±0.1°2θ; or ±0.0 °2θ; Cu Kα1 radiation).

In some embodiments, the tabernanthalog monofumarate salt is crystalline polymorphic Pattern #11 characterized by XRPD signals at 16.1 °2θ, 25.7 °2θ, 16.4 °2θ, 21.6°2θ, 20.4 °2θ, 7.5 °2θ, 9.2 °2θ, 23.9 °2θ, 20.9 °2θ, 17.4 °2θ, 22.8 °2θ, 11.2 °2θ, 27 °2θ, 24 °2θ, 18.2 °2θ, 10.8 °2θ, 25.3 °2θ, 22.5 °2θ, and 14.3°2θ (±0.2 °2θ; ±0.1°2θ; or 0.0 °2θ; Cu Kα1 radiation).

In some embodiments, the tabernanthalog monofumarate salt is crystalline polymorphic Pattern #11 characterized by XRPD signals at 16.1 °2θ, 25.7 °2θ, 16.4 °2θ, 21.6 °2θ, 20.4 °2θ, 7.5 °2θ, 9.2 °2θ, 23.9 °2θ, 20.9 °2θ, and 17.4 °2θ (±0.2 °2θ; ±0.1°2θ; or ±0.0 °2θ; Cu Kα1 radiation).

In some embodiments, the tabernanthalog monofumarate salt is crystalline polymorphic Pattern #11 characterized by two or more, or three XRPD signals as shown in Table 172.

In some embodiments, the tabernanthalog monofumarate salt is crystalline polymorphic Pattern #12 characterized by two or more, or three XRPD signals selected from the group consisting of 16.3 °2θ, 25.6 °2θ, 21.6 °2θ, 20.3 °2θ, 8.3 °2θ, 9.1 °2θ, 18.2 °2θ, 23 °2θ, 10.8 °2θ, and 14.3 °2θ (±0.2°2θ; ±0.1 °2θ; or 0.0 °2θ; Cu Kα1 radiation).

In some embodiments, the tabernanthalog monofumarate salt is crystalline polymorphic Pattern #12 characterized by XRPD signals at 16.3°2θ, 25.6 °2θ, 21.6 °2θ, 20.3 °2θ, 8.3 °2θ, 9.1 °2θ, 18.2 °2θ, 23 °2θ, 10.8 °2θ, and 14.3°2θ (±0.2°2θ; ±0.1 °2θ; or ±0.0 °2θ; Cu Kα1 radiation).

In some embodiments, the tabernanthalog monofumarate salt is crystalline polymorphic Pattern #12 characterized by two or more, or three XRPD signals as shown in Table 173.

In some embodiments, the tabernanthalog monofumarate salt is crystalline polymorphic Pattern #13 characterized by two or more, or three XRPD signals selected from the group consisting of 25.6 °2θ, 16 °2θ, 16.4 °2θ, 25.0 °2θ, 19.7 °2θ, 17.5 °2θ, 8.1 °2θ, 21.9 °2θ, 9.1 °2θ, 10.5 °2θ, 26.9 °2θ, 20.9 °2θ, 18.1 °2θ, 22.7 °2θ, 23.4 °2θ, 24.5 °2θ, 28.7 °2θ, 14.3 °2θ, and 18.9°2θ (±0.2°2θ; ±0.1°2θ; or ±0.0 °2θ; Cu Kα1 radiation).

In some embodiments, the tabernanthalog monofumarate salt is crystalline polymorphic Pattern #13 characterized by two or more, or three XRPD signals selected from the group consisting of 25.6 °2θ, 16 °2θ, 16.4 °2θ, 25.0 °2θ, 19.7 °2θ, 17.5 °2θ, 8.1 °2θ, 21.9 °2θ, 9.1 °2θ, and 10.5°2θ (±0.2°2θ; ±0.1°2θ; or 0.0 °2θ; Cu Kα1 radiation).

In some embodiments, the tabernanthalog monofumarate salt is crystalline polymorphic Pattern #13 characterized by XRPD signals at 25.6 °2θ, 16 °2θ, 16.4 °2θ, 25.0 °2θ, 19.7 °2θ, 17.5 °2θ, 8.1 °2θ, 21.9 °2θ, 9.1 °2θ, 10.5 °2θ, 26.9 °2θ, 20.9 °2θ, 18.1 °2θ, 22.7 °2θ, 23.4 °2θ, 24.5 °2θ, 28.7 °2θ, 14.3 °2θ, and 18.9°2θ (±0.2 °2θ; ±0.1 °2θ; or 0.0 °2θ; Cu Kα1 radiation).

In some embodiments, the tabernanthalog monofumarate salt is crystalline polymorphic Pattern #13 characterized by XRPD signals at 25.6 °2θ, 16 °2θ, 16.4°2θ, 25.0 °2θ, 19.7 °2θ, 17.5 °2θ, 8.1 °2θ, 21.9 °2θ, 9.1 °2θ, and 10.5°2θ (±0.2 °2θ; ±0.1°2θ; or ±0.0 °2θ; Cu Kα1 radiation). In some embodiments, the tabernanthalog monofumarate salt is crystalline polymorphic Pattern #13 characterized by two or more, or three XRPD signals as shown in Table 174.

In some embodiments, the tabernanthalog hemifumarate salt is crystalline polymorphic Pattern #14 characterized by two or more, or three XRPD signals selected from the group consisting of 8.2 °2θ, 15.5 °2θ, 17 °2θ, 22.6 °2θ, 20.2 °2θ, 11.2 °2θ, 23.7 °2θ, 24.8 °2θ, 21.5 °2θ, 18.1 °2θ, 19.2 °2θ, 24.3 °2θ, 19.4 °2θ, 18.4 °2θ, 21.3 °2θ, and 12.8°2θ (±0.2°2θ; ±0.1°2θ; or 0.0 °2θ; Cu Kai radiation).

In some embodiments, the tabernanthalog hemifumarate salt is crystalline polymorphic Pattern #14 characterized by two or more, or three XRPD signals selected from the group consisting of 8.2 °2θ, 15.5 °2θ, 17 °2θ, 22.6 °2θ, 20.2 °2θ, 11.2 °2θ, 23.7 °2θ, 24.8 °2θ, 21.5 °2θ, and 18.1 °2θ (±0.2°2θ; ±0.1°2θ; or ±0.0 °2θ; Cu Kα1 radiation).

In some embodiments, the tabernanthalog hemifumarate salt is crystalline polymorphic Pattern #14 characterized by two or more, or three XRPD signals selected from the group consisting of 8.2 °2θ, 15.5 °2θ, 17 °2θ, 22.6 °2θ, 20.2°2θ, 11.2 °2θ, 23.7 °2θ, 24.8 °2θ, and 21.5°2θ (±0.2 °2θ; ±0.1°2θ; or 0.0 °2θ; Cu Kα1 radiation).

In some embodiments, the tabernanthalog hemifumarate salt is crystalline polymorphic Pattern #14 characterized by two or more, or three XRPD signals selected from the group consisting of 8.2 °2θ, 15.5 °2θ, 17 °2θ, 22.6 °2θ, 20.2°2θ, 11.2 °2θ, 23.7 °2θ, and 24.8°2θ (±0.2°2θ; ±0.1 °2θ; or ±0.0 °2θ; Cu Kα1 radiation).

In some embodiments, the tabernanthalog hemifumarate salt is crystalline polymorphic Pattern #14 characterized by two or more, or three XRPD signals selected from the group consisting of 8.2 °2θ, 15.5 °2θ, 17 °2θ, 22.6 °2θ, 20.2°2θ, 11.2 °2θ, and 23.7°2θ (±0.2°2θ; ±0.1°2θ; or 0.0 °2θ; Cu Kα1 radiation).

In some embodiments, the tabernanthalog hemifumarate salt is crystalline polymorphic Pattern #14 characterized by two or more, or three XRPD signals selected from the group consisting of 8.2 °2θ, 15.5 °2θ, 17 °2θ, 22.6 °2θ, 20.2°2θ, and 11.2°2θ (±0.2°2θ; ±0.1°2θ; or ±0.0 °2θ; Cu Kα1 radiation).

In some embodiments, the tabernanthalog hemifumarate salt is crystalline polymorphic Pattern #14 characterized by two or more, or three XRPD signals selected from the group consisting of 8.2 °2θ, 15.5 °2θ, 17 °2θ, 22.6 °2θ, and 20.2°2θ (±0.2°2θ; ±0.1°2θ; or ±0.0 °2θ; Cu Kα1 radiation).

In some embodiments, the tabernanthalog hemifumarate salt is crystalline polymorphic Pattern #14 characterized by two or more, or three XRPD signals selected from the group consisting of 8.2 °2θ, 15.5 °2θ, 17020, and 22.6 °2θ (±0.2 °2θ; ±0.1 °2θ; or ±0.0 °2θ; Cu Kα1 radiation).

In some embodiments, the tabernanthalog hemifumarate salt is crystalline polymorphic Pattern #14 characterized by two or more, or three XRPD signals selected from the group consisting of 8.2 °2θ, 15.5 °2θ, and 17°2θ (±0.2 °2θ; ±0.1 °2θ; or 0.0 °2θ; Cu Kα1 radiation).

In some embodiments, the tabernanthalog hemifumarate salt is crystalline polymorphic Pattern #14 characterized by XRPD signals at 8.2 °2θ, 15.5 °2θ, 17 °2θ, 22.6 °2θ, 20.2°2θ, 11.2 °2θ, 23.7 °2θ, 24.8 °2θ, 21.5 °2θ, 18.1 °2θ, 19.2 °2θ, 24.3 °2θ, 19.4 °2θ, 18.4 °2θ, 21.3 °2θ, and 12.8°2θ (±0.2°2θ; ±0.1 °2θ; or ±0.0 °2θ; Cu Kα1 radiation).

In some embodiments, the tabernanthalog hemifumarate salt is crystalline polymorphic Pattern #14 characterized by XRPD signals at 8.2 °2θ, 15.5 °2θ, 17020, 22.6 °2θ, 20.2 °2θ, 11.2 °2θ, 23.7 °2θ, 24.8 °2θ, 21.5 °2θ, and 18.1°2θ (±0.2°2θ; ±0.1°2θ; or ±0.0 °2θ; Cu Kα1 radiation).

In some embodiments, the tabernanthalog hemifumarate salt is crystalline polymorphic Pattern #14 characterized by XRPD signals at 8.2 °2θ, 15.5 °2θ, 17 °2θ, 22.6 °2θ, 20.2°2θ, 11.2 °2θ, 23.7 °2θ, 24.8 °2θ, and 21.5°2θ (±0.2°2θ; ±0.1 °2θ; or 0.0 °2θ; Cu Kα1 radiation).

In some embodiments, the tabernanthalog hemifumarate salt is crystalline polymorphic Pattern #14 characterized by XRPD signals at 8.2 °2θ, 15.5 °2θ, 17 °2θ, 22.6 °2θ, 20.2 °2θ, 11.2 °2θ, 23.7 °2θ, and 24.8 °2θ (±0.2 °2θ; ±0.1°2θ; or ±0.0 °2θ; Cu Kα1 radiation).

In some embodiments, the tabernanthalog hemifumarate salt is crystalline polymorphic Pattern #14 characterized by XRPD signals at 8.2 °2θ, 15.5 °2θ, 17 °2θ, 22.6 °2θ, 20.2°2θ, 11.2 °2θ, and 23.7 °2θ (±0.2 °2θ; ±0.1°2θ; or ±0.0 °2θ; Cu Kα1 radiation).

In some embodiments, the tabernanthalog hemifumarate salt is crystalline polymorphic Pattern #14 characterized by XRPD signals at 8.2 °2θ, 15.5 °2θ, 17 °2θ, 22.6 °2θ, 20.2°2θ, and 11.2 °2θ (±0.2 °2θ; ±0.1 °2θ; or 0.0 °2θ; Cu Kα1 radiation).

In some embodiments, the tabernanthalog hemifumarate salt is crystalline polymorphic Pattern #14 characterized by XRPD signals at 8.2 °2θ, 15.5 °2θ, 17 °2θ, 22.6 °2θ, and 20.2°2θ (±0.2°2θ; ±0.1°2θ; or 0.0 °2θ; Cu Kα1 radiation).

In some embodiments, the tabernanthalog hemifumarate salt is crystalline polymorphic Pattern #14 characterized by XRPD signals at 8.2 °2θ, 15.5 °2θ, 17 °2θ, and 22.6 °2θ (±0.2 °2θ; ±0.1 °2θ; or ±0.0 °2θ; Cu Kα1 radiation).

In some embodiments, the tabernanthalog hemifumarate salt is crystalline polymorphic Pattern #14 characterized by XRPD signals at 8.2 °2θ, 15.5 °2θ, and 17 °2θ (±0.2 °2θ; ±0.1 °2θ; or ±0.0 °2θ; Cu Kα1 radiation).

In some embodiments, the tabernanthalog hemifumarate salt is crystalline polymorphic Pattern #14 characterized by two or more, or three XRPD signals as shown in Table 181D.

In some embodiments, the tabernanthalog hemifumarate salt is crystalline polymorphic Pattern #14 characterized by an $^1$H NMR spectrum as depicted in FIG. 377E.

In some embodiments, the tabernanthalog hemifumarate salt is crystalline polymorphic Pattern #14 characterized by an XRPD profile as depicted in FIG. 377F.

In some embodiments, the tabernanthalog hemifumarate salt is crystalline polymorphic Pattern #14 characterized by a TGA profile as depicted in FIG. 377I.

In some embodiments, the tabernanthalog hemifumarate salt is crystalline polymorphic Pattern #14 characterized by a DSC profile as depicted in FIG. 377J.

In some embodiments, the tabernanthalog monofumarate salt is crystalline polymorphic Pattern #15 characterized by two or more, or three XRPD signals selected from the group consisting of 16.2 °2θ, 17 °2θ, 25.5 °2θ, 23.3 °2θ, 21 °2θ, 16.9 °2θ, 19.9 °2θ, 24.4 °2θ, 8.4 °2θ, 25.1 °2θ, 18 °2θ, 15 °2θ, 26 °2θ, 17.7°2θ, 9 °2θ, 10.5 °2θ, 18.9 °2θ, 23.6 °2θ, 26.7°2θ, 22.5 °2θ, 24.8 °2θ, and 19.2°2θ (±0.2°2θ; ±0.1°2θ; or ±0.0 °2θ; Cu Kα1 radiation).

In some embodiments, the tabernanthalog monofumarate salt is crystalline polymorphic Pattern #15 characterized by two or more, or three XRPD signals selected from the group consisting of 16.2 °2θ, 17 °2θ, 25.5 °2θ, 23.3 °2θ, 21 °2θ, 16.9 °2θ, 19.9 °2θ, 24.4 °2θ, 8.4 °2θ, and 25.1 °2θ (±0.2 °2θ; ±0.1°2θ; or 0.0 °2θ; Cu Kα1 radiation).

In some embodiments, the tabernanthalog monofumarate salt is crystalline polymorphic Pattern #15 characterized by XRPD signals at 16.2 °2θ, 17 °2θ, 25.5 °2θ, 23.3 °2θ, 21 °2θ, 16.9 °2θ, 19.9 °2θ, 24.4 °2θ, 8.4 °2θ, 25.1 °2θ, 18 °2θ, 15 °2θ, 26 °2θ, 17.7 °2θ, 9 °2θ, 10.5 °2θ, 18.9 °2θ, 23.6 °2θ, 26.7 °2θ, 22.5 °2θ, 24.8 °2θ, and 19.2 °2θ (±0.2 °2θ; ±0.1 °2θ; or ±0.0 °2θ; Cu Kα1 radiation).

In some embodiments, the tabernanthalog monofumarate salt is crystalline polymorphic Pattern #15 characterized by XRPD signals at 16.2 °2θ, 17 °2θ, 25.5 °2θ, 23.3 °2θ, 21 °2θ, 16.9 °2θ, 19.9 °2θ, 24.4 °2θ, 8.4 °2θ, and 25.1 °2θ (±0.2 °2θ; ±0.1°2θ; or ±0.0 °2θ; Cu Kα1 radiation).

In some embodiments, the tabernanthalog monofumarate salt is crystalline polymorphic Pattern #15 characterized by two or more, or three XRPD signals as shown in Table 176.

In some embodiments, the tabernanthalog monofumarate salt is crystalline polymorphic Pattern #16 characterized by two or more, or three XRPD signals selected from the group consisting of 25.6 °2θ, 16.4 °2θ, 17 °2θ, 24.4 °2θ, 19.3 °2θ, 9.1 °2θ, 16.8 °2θ, 9.6 °2θ, 18.1 °2θ, 22.4 °2θ, 17.8 °2θ, 27.3 °2θ, 26.8 °2θ, 20.3 °2θ, 25.2 °2θ, 19 °2θ, 17.5 °2θ, 9 °2θ, 26.2 °2θ, 14.2 °2θ, 23.8 °2θ, and 23.2°2θ (±0.2 °2θ; ±0.1°2θ; or ±0.0 °2θ; Cu Kα1 radiation).

In some embodiments, the tabernanthalog monofumarate salt is crystalline polymorphic Pattern #16 characterized by two or more, or three XRPD signals selected from the group consisting of 25.6 °2θ, 16.4 °2θ, 17 °2θ, 24.4 °2θ, 19.3 °2θ, 9.1 °2θ, 16.8 °2θ, 9.6 °2θ, 18.1 °2θ, and 22.4°2θ (±0.2°2θ; ±0.1°2θ; or 0.0 °2θ; Cu Kα1 radiation).

In some embodiments, the tabernanthalog monofumarate salt is crystalline polymorphic Pattern #16 characterized by XRPD signals at 25.6 °2θ, 16.4 °2θ, 17 °2θ, 24.4 °2θ, 19.3 °2θ, 9.1 °2θ, 16.8 °2θ, 9.6 °2θ, 18.1 °2θ, 22.4 °2θ, 17.8 °2θ, 27.3 °2θ, 26.8 °2θ, 20.3 °2θ, 25.2 °2θ, 19 °2θ, 17.5 °2θ, 9 °2θ, 26.2 °2θ, 14.2 °2θ, 23.8 °2θ, and 23.2°2θ (±0.2°2θ; ±0.1°2θ; or ±0.0 °2θ; Cu Kα1 radiation).

In some embodiments, the tabernanthalog monofumarate salt is crystalline polymorphic Pattern #16 characterized by XRPD signals at 25.6 °2θ, 16.4 °2θ, 17 °2θ, 24.4 °2θ, 19.3 °2θ, 9.1 °2θ, 16.8 °2θ, 9.6 °2θ, 18.1 °2θ, and 22.4°2θ (±0.2°2θ; ±0.1°2θ; or ±0.0 °2θ; Cu Kα1 radiation).

In some embodiments, the tabernanthalog monofumarate salt is crystalline polymorphic Pattern #16 characterized by two or more, or three XRPD signals as shown in Table 177.

In some embodiments, the tabernanthalog monofumarate salt is crystalline polymorphic Pattern #17 characterized by two or more, or three XRPD signals selected from the group consisting of 25.6 °2θ, 16.4 °2θ, 16.6 °2θ, 23.6 °2θ, 21.7 °2θ, 19.6 °2θ, 26.9 °2θ, 9.1 °2θ, 22.4 °2θ, 23.2 °2θ, 18.1 °2θ, 27.1 °2θ, 8.1 °2θ, 11.2 °2θ, 25.2 °2θ, 15.4 °2θ, 30.3 °2θ, 14.3 °2θ, and 21.2°2θ (±0.2°2θ; ±0.1°2θ; or 0.0 °2θ; Cu Kα1 radiation).

In some embodiments, the tabernanthalog monofumarate salt is crystalline polymorphic Pattern #17 characterized by two or more, or three XRPD signals selected from the group consisting of 25.6 °2θ, 16.4 °2θ, 16.6 °2θ, 23.6 °2θ, 21.7 °2θ, 19.6 °2θ, 26.9 °2θ, 9.1 °2θ, 22.4 °2θ, and 23.2 °2θ (±0.2°2θ; ±0.1°2θ; or ±0.0 °2θ; Cu Kα1 radiation).

In some embodiments, the tabernanthalog monofumarate salt is crystalline polymorphic Pattern #17 characterized by XRPD signals at 25.6 °2θ, 16.4 °2θ, 16.6 °2θ, 23.6 °2θ, 21.7 °2θ, 19.6 °2θ, 26.9 °2θ, 9.1 °2θ, 22.4 °2θ, 23.2 °2θ, 18.1 °2θ, 27.1 °2θ, 8.1 °2θ, 11.2 °2θ, 25.2 °2θ, 15.4 °2θ, 30.3 °2θ, 14.3 °2θ, and 21.2°2θ (±0.2°2θ; ±0.1°2θ; or ±0.0 °2θ; Cu Kα1 radiation). In some embodiments, the tabernanthalog monofumarate salt is crystalline polymorphic Pattern #17 characterized by XRPD signals at 25.6 °2θ, 16.4 °2θ, 16.6 °2θ, 23.6 °2θ, 21.7 °2θ, 19.6 °2θ, 26.9 °2θ, 9.1 °2θ, 22.4 °2θ, and 23.2°2θ (±0.2 °2θ; ±0.1 °2θ; or ±0.0 °2θ; Cu Kα1 radiation).

In some embodiments, the tabernanthalog monofumarate salt is crystalline polymorphic Pattern #17 characterized by two or more, or three XRPD signals as shown in Table 178.

In some embodiments, the tabernanthalog monofumarate salt is crystalline polymorphic Pattern #18 characterized by two or more, or three XRPD signals selected from the group consisting of 25.6 °2θ, 16 °2θ, 18 °2θ, 16.3 °2θ, 21.4 °2θ, 26.8 °2θ, 23 °2θ, 25.9 °2θ, 15.5 °2θ, 11.0 °2θ, 18.9 °2θ, 20.9 °2θ, 22.4 °2θ, 14.1 °2θ, 19.3 °2θ, 12.6 °2θ, 16.8 °2θ, 24.9 °2θ, 9.1 °2θ, 12.1 °2θ, and 8.7 °2θ (±0.2°2θ; ±0.1°2θ; or ±0.0 °2θ; Cu Kα1 radiation).

In some embodiments, the tabernanthalog monofumarate salt is crystalline polymorphic Pattern #18 characterized by two or more, or three XRPD signals selected from the group consisting of 25.6 °2θ, 16 °2θ, 18 °2θ, 16.3 °2θ, 21.4 °2θ, 26.8 °2θ, 23 °2θ, 25.9 °2θ, 15.5 °2θ, and 11.0°2θ (±0.2°2θ; ±0.1°2θ; or 0.0 °2θ; Cu Kα1 radiation).

In some embodiments, the tabernanthalog monofumarate salt is crystalline polymorphic Pattern #18 characterized by XRPD signals at 25.6 °2θ, 16 °2θ, 18 °2θ, 16.3 °2θ, 21.4 °2θ, 26.8 °2θ, 23 °2θ, 25.9 °2θ, 15.5 °2θ, 11.0 °2θ, 18.9 °2θ, 20.9 °2θ, 22.4 °2θ, 14.1 °2θ, 19.3 °2θ, 12.6 °2θ, 16.8 °2θ, 24.9 °2θ, 9.1 °2θ, 12.1 °2θ, and 8.7 °2θ (±0.2 °2θ; ±0.1°2θ; or ±0.0 °2θ; Cu Kα1 radiation).

In some embodiments, the tabernanthalog monofumarate salt is crystalline polymorphic Pattern #18 characterized by XRPD signals at 25.6 °2θ, 16 °2θ, 18 °2θ, 16.3 °2θ, 21.4 °2θ, 26.8 °2θ, 23 °2θ, 25.9 °2θ, 15.5 °2θ, and 11.0°2θ (±0.2 °2θ; ±0.1 °2θ; or ±0.0 °2θ; Cu Kα1 radiation).

In some embodiments, the tabernanthalog monofumarate salt is crystalline polymorphic Pattern #18 characterized by two or more, or three XRPD signals as shown in Table 179.

In some embodiments, the tabernanthalog monofumarate salt is crystalline polymorphic Pattern #19 characterized by two or more, or three XRPD signals selected from the group consisting of 25.6 °2θ, 25.5 °2θ, 16.4 °2θ, 20.5 °2θ, 16.3 °2θ, 26.7 °2θ, 22.8 °2θ, 19.5 °2θ, 19.4 °2θ, 17.0 °2θ, 33.3 °2θ, 9.1 °2θ, 21.5 °2θ, 27.1 °2θ, 21.9 °2θ, 24.7 °2θ, 18.6 °2θ, 15.7 °2θ, 12.2 °2θ, and 29.8°2θ (±0.2°2θ; ±0.1°2θ; or 0.0 °2θ; Cu Kα1 radiation).

In some embodiments, the tabernanthalog monofumarate salt is crystalline polymorphic Pattern #19 characterized by two or more, or three XRPD signals selected from the group consisting of 25.6 °2θ, 25.5 °2θ, 16.4 °2θ, 20.5 °2θ, 16.3 °2θ, 26.7 °2θ, 22.8 °2θ, 19.5 °2θ, 19.4 °2θ, and 17 °2θ (±0.2°2θ; ±0.1°2θ; or ±0.0 °2θ; Cu Kα1 radiation).

In some embodiments, the tabernanthalog monofumarate salt is crystalline polymorphic Pattern #19 characterized by XRPD signals at 25.6 °2θ, 25.5 °2θ, 16.4 °2θ, 20.5 °2θ, 16.3 °2θ, 26.7 °2θ, 22.8 °2θ, 19.5 °2θ, 19.4 °2θ, 17 °2θ, 33.3 °2θ, 9.1 °2θ, 21.5 °2θ, 27.1 °2θ, 21.9 °2θ, 24.7 °2θ, 18.6 °2θ, 15.7 °2θ, 12.2 °2θ, and 29.8°2θ (±0.2°2θ; ±0.1 °2θ; or 0.0 °2θ; Cu Kα1 radiation).

In some embodiments, the tabernanthalog monofumarate salt is crystalline polymorphic Pattern #19 characterized by XRPD signals at 25.6 °2θ, 25.5 °2θ, 16.4 °2θ, 20.5 °2θ, 16.3 °2θ, 26.7 °2θ, 22.8 °2θ, 19.5 °2θ, 19.4 °2θ, and 17°2θ (±0.2°2θ; ±0.1 °2θ; or ±0.0 °2θ; Cu Kα1 radiation).

In some embodiments, the tabernanthalog monofumarate salt is crystalline polymorphic Pattern #19 characterized by two or more, or three XRPD signals as shown in Table 180.

In some embodiments, the tabernanthalog monofumarate salt is crystalline polymorphic Pattern #20 characterized by two or more, or three XRPD signals selected from the group consisting of 6.1 °2θ, 25.5 °2θ, 16.3 °2θ, 19 °2θ, 18.2 °2θ, 15.9 °2θ, and 16.7°2θ (±0.2°2θ; ±0.1°2θ; or 0.0 °2θ; Cu Kα1 radiation).

In some embodiments, the tabernanthalog monofumarate salt is crystalline polymorphic Pattern #20 characterized by XRPD signals at 6.1 °2θ, 25.5°2θ, 16.3 °2θ, 19020, 18.2 °2θ, 15.9 °2θ, and 16.7°2θ (±0.2°2θ; ±0.1°2θ; or 0.0 °2θ; Cu Kα1 radiation).

In some embodiments, the tabernanthalog monofumarate salt is crystalline polymorphic Pattern #20 characterized by two or more, or three XRPD signals as shown in Table 181.

In some embodiments, the tabernanthalog hemifumarate salt is crystalline polymorphic Pattern #21 characterized by two or more, or three XRPD signals selected from the group consisting of 19.2 °2θ, 16.7 °2θ, 25.4 °2θ, 22.2 °2θ, 27.2 °2θ, 18.1 °2θ, 17.7 °2θ, 21.2 °2θ, 26.1 °2θ, 6.7 °2θ, 20.1 °2θ, 17.6 °2θ, 12.8 °2θ, 23 °2θ, 23.6 °2θ, 28.7 °2θ, 14.9 °2θ, 30.1 °2θ, 8.2 °2θ, and 16.3°20 (±0.2°2θ; ±0.1°2θ; or 0.0 °2θ; Cu Kα1 radiation).

In some embodiments, the tabernanthalog hemifumarate salt is crystalline polymorphic Pattern #21 characterized by two or more, or three XRPD signals selected from the group consisting of 19.2 °2θ, 16.7 °2θ, 25.4 °2θ, 22.2 °2θ, 27.2 °2θ, 18.1 °2θ, 17.7 °2θ, 21.2 °2θ, 26.1 °2θ, and 6.7°2θ (±0.2 °2θ; ±0.1 °2θ; or 0.0 °2θ; Cu Kα1 radiation).

In some embodiments, the tabernanthalog hemifumarate salt is crystalline polymorphic Pattern #21 characterized by XRPD signals at 19.2 °2θ, 16.7 °2θ, 25.4 °2θ, 22.2 °2θ, 27.2 °2θ, 18.1 °2θ, 17.7 °2θ, 21.2 °2θ, 26.1 °2θ, 6.7 °2θ, 20.1°2θ, 17.6 °2θ, 12.8 °2θ, 23 °2θ, 23.6 °2θ, 28.7 °2θ, 14.9 °2θ, 30.1 °2θ, 8.2 °2θ, and 16.3°20 (±0.2°2θ; ±0.1°2θ; or ±0.0 °2θ; Cu Kα1 radiation). In some embodiments, the tabernanthalog hemifumarate salt is crystalline polymorphic Pattern #21 characterized by XRPD signals at 19.2 °2θ, 16.7 °2θ, 25.4 °2θ, 22.2 °2θ, 27.2 °2θ, 18.1 °2θ, 17.7 °2θ, 21.2 °2θ, 26.1 °2θ, and 6.7°2θ (±0.2 °2θ; ±0.1 °2θ; or 0.0 °2θ; Cu Kα1 radiation).

In some embodiments, the tabernanthalog hemifumarate salt is crystalline polymorphic Pattern #21 characterized by two or more, or three XRPD signals as shown in Table 182.

In some embodiments, the tabernanthalog hemifumarate salt is crystalline polymorphic Pattern #22 characterized by two or more, or three XRPD signals selected from the group consisting of 18.9 °2θ, 19.3 °2θ, 16.7 °2θ, 27.3 °2θ, 18.2 °2θ, 25.5 °2θ, 6.7 °2θ, 17.7 °2θ, 20.2 °2θ, 22.3 °2θ, 26.2 °2θ, 15.0 °2θ, 23.7 °2θ, 10.4 °2θ, 21.3 °2θ, 12.9 °2θ, 25.4 °2θ, and 23.1°2θ (±0.2 °2θ; ±0.1 °2θ; or ±0.0 °2θ; Cu Kα1 radiation).

In some embodiments, the tabernanthalog hemifumarate salt is crystalline polymorphic Pattern #22 characterized by two or more, or three XRPD signals selected from the group consisting of 18.9 °2θ, 19.3 °2θ, 16.7 °2θ, 27.3 °2θ, 18.2 °2θ, 25.5 °2θ, 6.7 °2θ, 17.7 °2θ, 20.2 °2θ, and 22.3 °2θ (±0.2°2θ; ±0.1°2θ; or 0.0 °2θ; Cu Kα1 radiation).

In some embodiments, the tabernanthalog hemifumarate salt is crystalline polymorphic Pattern #22 characterized by XRPD signals at 18.9 °2θ, 19.3 °2θ, 16.7 °2θ, 27.3 °2θ, 18.2 °2θ, 25.5 °2θ, 6.7 °2θ, 17.7 °2θ, 20.2 °2θ, 22.3 °2θ, 26.2 °2θ, 15 °2θ, 23.7 °2θ, 10.4 °2θ, 21.3 °2θ, 12.9 °2θ, 25.4 °2θ, and 23.1 °2θ (±0.2 °2θ; ±0.1°2θ; or 0.0 °2θ; Cu Kα1 radiation).

In some embodiments, the tabernanthalog hemifumarate salt is crystalline polymorphic Pattern #22 characterized by XRPD signals at 18.9 °2θ, 19.3 °2θ, 16.7 °2θ, 27.3 °2θ, 18.2 °2θ, 25.5 °2θ, 6.7 °2θ, 17.7 °2θ, 20.2 °2θ, and 22.3°2θ (±0.2°2θ; ±0.1°2θ; or 0.0 °2θ; Cu Kα1 radiation).

In some embodiments, the tabernanthalog hemifumarate salt is crystalline polymorphic Pattern #22 characterized by two or more, or three XRPD signals as shown in Table 183.

Figure 78:
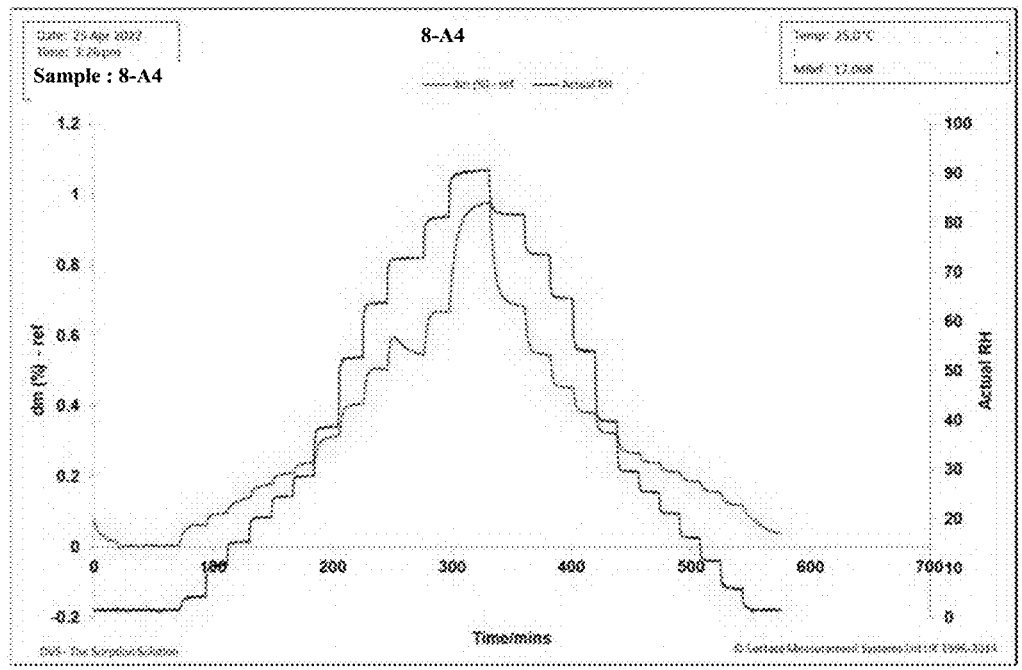
FIG. 78 depicts the mass equilibrated DVS data of 4-A4 (Experiment Reference 4-Sample Reference A4) (Form A, Pattern #6a).

In some embodiments, the tabernanthalog monofumarate salt has Pattern #6a (Form A) and is characterized by at least one of the following properties:

(a) 33.5% w/w th. of fumaric acid;
(b) a hydrogen bonding network wherein the fumaric acid adopted a 1,4-orientated linear configuration, exhibiting head to tail hydrogen bonding between oxygen atoms O3-O4 (2.48 Å), while oxygen atom O2 was hydrogen bonded to nitrogen atom N1, located on the azepine ring (O2-N1, 2.70 Å), assumed to be salified;
(c) monoclinic crystal system 300(2) with $P2_1/c$ space group 300(2);
(d) a unit cell 300(2) K: a=7.43280(10) Å, b=8.59740(10) Å, c=27.5143(3) Å, a=g 90°, b=96.6990(10)°, V=1746.24(4) Å$^3$;
(e) an asymmetric unit which contained one molecule of API and one molecule of fumaric acid (crystal bonded);
(f) one or more, or two or more, or three or more XRPD signals selected from the group consisting of 12.9°, 14.1°, 15.8°, 16.5°, 19.2°, 19.4°, 20.6°, 22.0°, 25.2°, 26.0°, 28.0°, 33.4°, °(2θ, 1 d.p);
(g) a DSC profile exhibiting an onset at 187.0° C. (−117.9 Jg$^{-1}$, endotherm, melt) as shown in FIG. 149;

(h) a TGA profile exhibiting onsets at 220.8° C. (−16.0% w/w, ablation), 289.5° C. (−1.2% w/w, ablation), 315.3° C. (−1.5% w/w, ablation), 325.9° C. (−3.8% w/w, ablation), 373.7° C. (−14.0% w/w, ablation) as shown in FIG. 148;

(i) DVS 0 to 90 to 0% RH (dm/dt<0.002%): 0.0 (0.0004%), 5.0 (0.0627%), 10.0 (0.0957%), 15.0 (0.1397%), 20.0 (0.1778%), 25.0 (0.2093%), 30.0 (0.2401%), 40.0 (0.3145%), 50.0 (0.4051%), 60.0 (0.5029%), 70.0 (0.5451%), 80.0 (0.6660%), 90.0 (0.9766%), 90.0 (0.9766%), 80.0 (0.6827%), 70.0 (0.5442%), 60.0 (0.4515%), 50.0 (0.3797%), 40.0 (0.3210%), 30.0 (0.2656%), 25.0 (0.2387%), 20.0 (0.2126%), 15.0 (0.1857%), 10.0 (0.1551%), 5.0 (0.1179%), 0.0 (0.0381%) (8-A4) as shown in FIG. 78;

(j) a UV chromatographic purity of 99.04% area (212 nm) as shown in FIG. 151;

(k) an $^1$H NMR: (DMSO-d6, 400 MHz); δ 10.6 (s, 1H), 7.3 (d, J=8.6 Hz, 1H), 6.8 (s, 1 H), 6.6 (dd, J=8.6, 2.2 Hz, 1H), 6.5 (s, 2H), 3.7 (s, 3H), 3.1-3.0 (m, 6H), 2.9 (t, J=9.9, 5.6 Hz, 2H), 2.6 (s, 3H) conforms to the molecular structure (Σ20H) as shown in FIG. 146;

(l) an appearance as shown in FIG. 152-FIG. 155;

(m) a crystal data as shown in FIG. 285 when collected using Single Crystal XRD; and (n) soluble in FaSSIF, FeSSIF and FaSSGF at 37° C. up to 24 h.

In some embodiments, the tabernanthalog monofumarate salt has Pattern #6a (Form A) and has a crystal data as shown in FIG. 285 when collected using Single Crystal XRD.

In some embodiments, the tabernanthalog monofumarate salt has Pattern #6a (Form A) and has a crystal data when collected using Single Crystal XRD as follows: $C_{18}H_{22}N_2O_5$, $M_r$=346.37, monoclinic, P2$_1$/c (No. 14), a=7.43280(10) Å, b=8.59740(10) Å, c=27.5143(3) Å, β=96.6990(10)°, α=γ=90°, V=1746.24(4) Å$^3$, T=300(2) K, Z=4, Z'=1, μ(Cu K$_α$)=0.801 mm$^{-1}$, 32845 reflections measured, 3622 unique (R$_{int}$=0.0333) which were used in all calculations. The final wR$_2$ was 0.1071 (all data) and R$_1$ was 0.0409 (I≥2 σ(I)).

In some embodiments, Form A of the tabernanthalog monofumarate salt is obtained from suspension equilibration of the tabernanthalog fumarate salt in water (5 vol) at 90° C., and the product is isolated by filtration and dried under sustained nitrogen flux (<1 bar) over 20 h at 20° C.

In some embodiments, Form A of the tabernanthalog monofumarate salt is obtained from suspension equilibration of the tabernanthalog fumarate salt in water (5 vol) at 20° C., and the product is isolated by filtration and dried under sustained nitrogen flux (<1 bar) over 20 h at 20° C.

In some embodiments, the tabernanthalog monofumarate salt has Pattern #2a (Form B) and is characterized by at least one of the following properties:

(a) 33.5% w/w th. of fumaric acid;

(b) one or more, or two or more, or three or more XRPD signals selected from the group consisting of 9.1°, 12.3°, 14.2°, 15.7°, 16.4°, 17.1°, 17.4°, 18.1°, 18.8°, 20.7°, 21.0°, 22.3°, 22.8°, 23.0°, 24.7°, 25.0°, 25.6°, 26.8°, 27.3°, 2θ, 1 d.p), (A1272-022-B2) as shown in FIG. 3;

(c) a DSC profile exhibiting onsets at 100.6° C. (−0.74 Jg$^{-1}$, endotherm), 125.7° C. (−1.57 Jg$^{-1}$, endotherm), and 174.1° C. (−31.27 Jg$^{-1}$, endotherm, melt) as shown in FIG. 316;

(d) a TGA profile exhibiting onsets at 219.0° C. (−10.3% w/w, ablation), 286.8° C. (−1.9% w/w, ablation), and 324.6° C. (−2.5% w/w, ablation) as shown in FIG. 315;

(e) an $^1$H NMR: (DMSO-d6, 400 MHz); δ 10.6 (s, 1H), 7.3 (d, J=8.6 Hz, 1H), 6.8 (s, 1H), 6.6 (dd, J=8.6, 2.2 Hz, 1H), 6.5 (s, 2H), 3.7 (s, 3H), 3.1-3.0 (m, 6H), 2.9 (t, J=9.9, 5.6 Hz, 2 H), 2.6 (s, 3H) conforms to the molecular structure (Σ20H) as shown in FIG. 313); and (f) Residual solvents ICH Q2C (R8): acetonitrile (0.1% w/w (0.03% w/w, ICH listed 10 ppm).

In some embodiments, Form B of the tabernanthalog monofumarate salt is obtained from suspension equilibration of the tabernanthalog fumarate salt in acetonitrile (5 vol) at 40° C., and the product is isolated by centrifugation and oven-dried under vacuum over 20 h at 40° C.

In some embodiments, the tabernanthalog hemifumarate salt has Pattern #14 (Form I) and is characterized by at least one of the following properties:

(a) 20.1% w/w th. of fumaric acid;

(b) a hydrogen bonding network wherein the fumaric acid is situated in-between two molecules of Tabernanthalog via hydrogen bonds to the azepine (N1-O2, 2.70 Å) and indole nitrogen atoms (N2-O3, 2.81 Å) as shown in FIG. 292;

(c) monoclinic crystal system 300(2) with C2/c space group 300(2);

(d) a unit cell 300(2) K: a=21.7386(8) Å, b=9.7033(5) Å, c=15.8640(8) Å, a=g=90°, b=99.182(4)°, V=3303.4(3) Å$^3$;

(e) an asymmetric unit which contained one molecule of API and half molecule of fumaric acid (crystal bonded);

(f) one or more, or two or more, or three or more XRPD signals selected from the group consisting of 8.2°, 11.2°, 12.8°, 15.5°, 17.0°, 18.1°, 18.3°, 19.2°, 19.4°, 20.2°, 21.3°, 21.5°, 22.6°, 23.7°, 24.3°, 24.8°, (2θ, 1 d.p) as shown in FIG. 377F;

(g) a DSC profile exhibiting onsets at 50.1° C. (−22.64 Jg$^{-1}$, endotherm), 115.1° C. (−22.28 Jg$^{-1}$, endotherm), 183° C. (−14.73 Jg$^{-1}$, endotherm), and 210.7 (−111.8 Jg$^{-1}$, endotherm, melt) as shown in FIG. 377J;

(h) a TGA profile exhibiting onsets at 75.9° C. (−1.2% w/w, solvent release), 141.5° C. (−1.3% w/w, solvent release), and 224.0° C. (−23.6% w/w, ablation) as shown in FIG. 377I;

(i) an $^1$H NMR: (DMSO-d6, 400 MHz); δ 10.6 (s, I H), 7.3 (d, J=8.6 Hz, 1H), 6.8 (s, 1H), 6.6 (dd, J=8.6, 2.2 Hz, 1H), 6.5 (s, 2H), 3.7 (s, 3H), 3.1-3.0 (m, 6H), 2.9 (t, J=9.9, 5.6 Hz, 2 H), 2.6 (s, 3H) conforms to the molecular structure (Σ20H*) as shown in FIG. 377E (*The molecular formula ($C_{18}H_{22}N_2O_5$) includes the carboxylic acid protons; however, they co-resonate with water.);

(j) Residual solvents: 5-B3 (acetonitrile 0.3% w/w, ICH listed 410 ppm, acetone 0.2% w/w, ICH listed 5000 ppm and methanol, 2.4% w/w, ICH listed 3000 ppm). and (k) a crystal data as shown in FIG. 286 when collected using single Crystal XRD.

In some embodiments, the tabernanthalog hemifumarate salt has Pattern #14 (Form I) and has a crystal data as shown in FIG. 286 when collected using single Crystal XRD.

In some embodiments, the tabernanthalog hemifumarate salt has Pattern #14 (Form I) and has a crystal data when collected using Single Crystal XRD as follows: $C_{8.12}H_{10.5}NO_{1.62}$, $M_r$=148.17, monoclinic, C2/c (No. 15), a=21.7386(8) Å, b=9.7033(5) Å, c=15.8640(8) Å, β=99.182(4)°, α=γ=90°, V=3303.4(3) Å$^3$, T=300(2) K, Z=16, Z'=2, μ(Cu K$_α$)=0.680 mm$^{-1}$, 11278 reflections measured, 3227 unique ($R_{int}$=0.0472) which were used in all calculations. The final $wR_2$ was 0.2751 (all data) and $R_1$ was 0.0857 (I≥2 σ(I)).

In some embodiments, Form I of the tabernanthalog hemifumarate salt is obtained from dissolution of Tabernanthalog (native); TBG Native and fumaric acid (0.5 equiv) in methanol (20 vol).

In some embodiments, the tabernanthalog fumarate salt Form A (unary fumarate, Pattern #6a), is prepared from water (anhydrous form, generated via suspension equilibration in water at 20° C.).

In some embodiments, in the presence of Form A, Form B slowly evolves into Form A under competitive suspension equilibration conditions.

In some embodiments, metastable forms obtained via suspension equilibration and wet pellets, readily undergo conversion into Form A during drying.

In some embodiments, Form A exhibits greatest relative stability amongst other forms of the tabernanthalog fumarate salt.

In some embodiments, the hemi-fumarate salt of the tabernanthalog fumarate salt is prepared and re-proportionated into the fumarate salt during an ageing cycle.

In some embodiments, stability assessment of the supplied material (Pattern #1) at 40° C./75% RH executed over a 4-to-5-week period shows no evidence for hydrate formation, chemical degradation or disproportionation of the API.

Tabernanthalog Sorbate Salt

In some embodiments, the solid form of tabernanthalog sorbate salt (Form A) is crystalline tabernanthalog sorbate salt (Form A) characterized by two or more, or three or more XRPD signals selected from the group consisting of 5.7 °2θ, 11.4 °2θ, and 22.8 °2θ (±0.2 °2θ; ±0.1 °2θ; or ±0.0 °2θ; Cu Kα1 radiation).

In some embodiments, the solid form of tabernanthalog sorbate salt (Form A) is crystalline tabernanthalog sorbate salt (Form A) characterized by XRPD signals at 5.7 °2θ, 11.4 °2θ, and 22.8 °2θ (±0.2 °2θ; ±0.1 °2θ; or ±0.0 °2θ; Cu Kα1 radiation).

In some embodiments, the crystalline tabernanthalog sorbate salt (Form A) is characterized by one, two, or three XRPD signals selected from those set forth in Table 273.

In some embodiments, the solid form of tabernanthalog sorbate salt is crystalline tabernanthalog sorbate salt characterized by two or more, or three or more XRPD signals selected from the group consisting of 5.7 °2θ, 11.5 °2θ, and 24.7 °2θ (±0.2°2θ; ±0.1 °2θ; or 0.0 °2θ; Cu Kα1 radiation).

In some embodiments, the solid form of tabernanthalog sorbate salt is crystalline tabernanthalog sorbate salt characterized by XRPD signals at 5.7 °2θ, 11.5 °2θ, and 24.7°2θ (±0.2 °2θ; ±0.1 °2θ; or ±0.0 °2θ; Cu Kα1 radiation).

In some embodiments, the solid form of tabernanthalog sorbate salt is crystalline tabernanthalog sorbate salt characterized by XRPD signals at 5.7 °2θ, 11.5 °2θ, 18.9 °2θ, 22.8 °2θ, and 24.7°2θ (±0.2°2θ; ±0.1 °2θ; or 0.0 °2θ; Cu Kα1 radiation).

In some embodiments, the solid form of tabernanthalog sorbate salt is crystalline tabernanthalog sorbate salt characterized by XRPD signals at 5.7 °2θ, 10.6 °2θ, 11.5 °2θ, 18.9 °2θ, 22.8 °2θ, 24.5 °2θ, and 24.7 °2θ (±0.2°2θ; ±0.1°2θ; or 0.0 °2θ; Cu Kα1 radiation).

In some embodiments, the crystalline tabernanthalog sorbate salt is characterized by one, two, three, four, five, six, or seven XRPD signals selected from those set forth in Table 274.

In some embodiments, the solid form of tabernanthalog sorbate salt (Pattern #1) is crystalline tabernanthalog sorbate (Pattern #1) characterized by one or more XRPD signals selected from the group consisting of 7.5°2θ and 15.1 °2θ (±0.2°2θ; ±0.1 °2θ; or 0.0 °2θ; Cu Kα1 radiation).

In some embodiments, the solid form of tabernanthalog sorbate salt (Pattern #1) is crystalline tabernanthalog sorbate (Pattern #1) characterized by XRPD signals at 7.5°2θ and 15.1 °2θ (±0.2 °2θ; ±0.1°2θ; or 0.0 °2θ; Cu Kα1 radiation).

In some embodiments, the crystalline tabernanthalog sorbate salt is characterized by one or two XRPD signals selected from those set forth in Table 276.

In some embodiments, the solid form of tabernanthalog sorbate salt (Pattern #1) is crystalline tabernanthalog sorbate (Pattern #1) characterized by one or more XRPD signals selected from the group consisting of 7.6°2θ and 15.1 °2θ (±0.2 °2θ; ±0.1 °2θ; or ±0.0 °2θ; Cu Kα1 radiation).

In some embodiments, the solid form of tabernanthalog sorbate salt (Pattern #1) is crystalline tabernanthalog sorbate (Pattern #1) characterized by XRPD signals at 7.6 °2θ and 15.1 °2θ (±0.2°2θ; ±0.1°2θ; or 0.0 °2θ; Cu Kα1 radiation).

In some embodiments, the crystalline tabernanthalog sorbate salt is characterized by one or two XRPD signals selected from those set forth in Table 277.

In some embodiments, the solid form of tabernanthalog sorbate salt (Pattern #2) is crystalline tabernanthalog sorbate (Pattern #2) characterized by one or more XRPD signals selected from the group consisting of 5.7°2θ and 11.5 °2θ (±0.2 °2θ; ±0.1°2θ; or ±0.0 °2θ; Cu Kα1 radiation).

In some embodiments, the solid form of tabernanthalog sorbate salt (Pattern #2) is crystalline tabernanthalog sorbate (Pattern #2) characterized by XRPD signals at 5.7°2θ and 11.5 °2θ (±0.2°2θ; ±0.1 °2θ; or 0.0 °2θ; Cu Kα1 radiation).

In some embodiments, the crystalline tabernanthalog sorbate salt is characterized by one or two XRPD signals selected from those set forth in Table 279.

In some embodiments, the solid form of tabernanthalog sorbate salt (Pattern #2) is crystalline tabernanthalog sorbate salt (Pattern #2) characterized by two or more, or three or more XRPD signals selected from the group consisting of 5.7 °2θ, 16.7 °2θ, and 22.4°2θ (±0.2°2θ; ±0.1 °2θ; or ±0.0 °2θ; Cu Kα1 radiation).

In some embodiments, the solid form of tabernanthalog sorbate salt (Pattern #2) is crystalline tabernanthalog sorbate salt (Pattern #2) characterized by XRPD signals at 5.7 °2θ, 16.7 °2θ, and 22.4°2θ (±0.2°2θ; ±0.1 °2θ; or 0.0 °2θ; Cu Kα1 radiation).

In some embodiments, the solid form of tabernanthalog sorbate salt (Pattern #2) is crystalline tabernanthalog sorbate salt (Pattern #2) characterized by XRPD signals at 5.7 °2θ, 11.5 °2θ, 16.7 °2θ, 17.3°2θ, and 22.4 °2θ (±0.2°2θ; ±0.1 °2θ; or 0.0 °2θ; Cu Kα1 radiation).

In some embodiments, the solid form of tabernanthalog sorbate salt (Pattern #2) is crystalline tabernanthalog sorbate salt (Pattern #2) characterized by XRPD signals at 5.7 °2θ, 11.5 °2θ, 16.7°2θ, 17.3 °2θ, 18.5 °2θ, 18.7 °2θ, and 22.4°2θ (±0.2 °2θ; ±0.1°2θ; or ±0.0 °2θ; Cu Kα1 radiation).

In some embodiments, the solid form of tabernanthalog sorbate salt (Pattern #2) is crystalline tabernanthalog sorbate salt (Pattern #2) characterized by XRPD signals at 5.7 °2θ, 11.2 °2θ, 11.5 °2θ, 16.7 °2θ, 17.3 °2θ, 17.8 °2θ, 18.5 °2θ, 18.7 °2θ, 20.1°2θ, and 22.4 °2θ (±0.2 °2θ; ±0.1 °2θ; or ±0.0 °2θ; Cu Kα1 radiation).

In some embodiments, the crystalline tabernanthalog sorbate salt is characterized by one, two, three, four, five, six, seven, eight, nine, or ten XRPD signals selected from those set forth in Table 280.

In some embodiments, the solid form of tabernanthalog sorbate salt (Pattern #3) is crystalline tabernanthalog sorbate salt (Pattern #3) characterized by two or more, or three or more XRPD signals selected from the group consisting of 5.7 °2θ, 7.3 °2θ, and 11.5°2θ (±0.2 °2θ; ±0.1 °2θ; or ±0.0 °2θ; Cu Kα1 radiation).

In some embodiments, the solid form of tabernanthalog sorbate salt (Pattern #3) is crystalline tabernanthalog sorbate salt (Pattern #3) characterized by XRPD signals at 5.7 °2θ, 7.3 °2θ, and 11.5 °2θ (±0.2 °2θ; ±0.1°2θ; or ±0.0 °2θ; Cu Kα1 radiation).

In some embodiments, the solid form of tabernanthalog sorbate salt (Pattern #3) is crystalline tabernanthalog sorbate salt (Pattern #3) characterized by XRPD signals at 5.7 °2θ, 7.3 °2θ, 7.4 °2θ, 11.5°2θ, and 18.9 °2θ (±0.2 °2θ; ±0.1°2θ; or ±0.0 °2θ; Cu Kα1 radiation).

In some embodiments, the solid form of tabernanthalog sorbate salt (Pattern #3) is crystalline tabernanthalog sorbate salt (Pattern #3) characterized by XRPD signals at 5.7 °2θ, 7.3 °2θ, 7.4 °2θ, 11.5 °2θ, 18.9 °2θ, 24.7°2θ, and 24.8 °2θ (±0.2°2θ; ±0.1 °2θ; or ±0.0 °2θ; Cu Kα1 radiation).

In some embodiments, the solid form of tabernanthalog sorbate salt (Pattern #3) is crystalline tabernanthalog sorbate salt (Pattern #3) characterized by XRPD signals at 5.7 °2θ, 7.3 °2θ, 7.4 °2θ, 10.6 °2θ, 11.5 °2θ, 18.9°2θ, 23.0 °2θ, 24.7 °2θ, 24.8 °2θ, and 29.7 °2θ (±0.2°2θ; ±0.1 °2θ; or 0.0 °2θ; Cu Kα1 radiation).

In some embodiments, the crystalline tabernanthalog sorbate salt is characterized by one, two, three, four, five, six, seven, eight, nine, or ten XRPD signals selected from those set forth in Table 282.

In some embodiments, the solid form of tabernanthalog sorbate salt (Pattern #4) is crystalline tabernanthalog sorbate salt (Pattern #4) characterized by two or more, or three or more XRPD signals selected from the group consisting of 5.8 °2θ, 5.9 °2θ, and 22.5 °2θ (±0.2 °2θ; ±0.1 °2θ; or 0.0 °2θ; Cu Kα1 radiation).

In some embodiments, the solid form of tabernanthalog sorbate salt (Pattern #4) is crystalline tabernanthalog sorbate salt (Pattern #4) characterized by XRPD signals at 5.8 °2θ, 5.9 °2θ, and 22.5 °2θ (±0.2 °2θ; ±0.1 °2θ; or ±0.0 °2θ; Cu Kα1 radiation).

In some embodiments, the solid form of tabernanthalog sorbate salt (Pattern #4) is crystalline tabernanthalog sorbate salt (Pattern #4) characterized by XRPD signals at 5.8 °2θ, 5.9 °2θ, 16.8 °2θ, 18.6 °2θ, and 22.5°2θ (±0.2°2θ; ±0.1°2θ; or ±0.0 °2θ; Cu Kα1 radiation).

In some embodiments, the solid form of tabernanthalog sorbate salt (Pattern #4) is crystalline tabernanthalog sorbate salt (Pattern #4) characterized by XRPD signals at 5.8 °2θ, 5.9 °2θ, 11.6 °2θ, 16.8 °2θ, 17.5 °2θ, 18.6 °2θ, and 22.5°2θ (±0.2°2θ; ±0.1°2θ; or 0.0 °2θ; Cu Kα1 radiation).

In some embodiments, the solid form of tabernanthalog sorbate salt (Pattern #4) is crystalline tabernanthalog sorbate salt (Pattern #4) characterized by XRPD signals at 5.8 °2θ, 5.9 °2θ, 11.3 °2θ, 11.6 °2θ, 16.8 °2θ, 17.5 °2θ, 17.9 °2θ, 18.6 °2θ, 18.8 °2θ, and 22.5°2θ (±0.2 °2θ; ±0.1 °2θ; or 0.0 °2θ; Cu Kα1 radiation).

In some embodiments, the crystalline tabernanthalog sorbate salt is characterized by one, two, three, four, five, six, seven, eight, nine, or ten XRPD signals selected from those set forth in Table 284.

In some embodiments, the solid form of tabernanthalog sorbate salt (Pattern #5) is crystalline tabernanthalog sorbate salt (Pattern #5) characterized by two or more, or three or more XRPD signals selected from the group consisting of 14.1 °2θ, 16.5 °2θ, and 20.5 °2θ (±0.2 °2θ; ±0.1°2θ; or ±0.0 °2θ; Cu Kα1 radiation).

In some embodiments, the solid form of tabernanthalog sorbate salt (Pattern #5) is crystalline tabernanthalog sorbate salt (Pattern #5) characterized by XRPD signals at 14.1 °2θ, 16.5 °2θ, and 20.5 °2θ (±0.2 °2θ; ±0.1°2θ; or 0.0 °2θ; Cu Kα1 radiation).

In some embodiments, the solid form of tabernanthalog sorbate salt (Pattern #5) is crystalline tabernanthalog sorbate salt (Pattern #5) characterized by XRPD signals at 14.1 °2θ, 16.5 °2θ, 20.5 °2θ, 20.8 °2θ, and 21.2 °2θ (±0.2°2θ; ±0.1 °2θ; or ±0.0 °2θ; Cu Kα1 radiation).

In some embodiments, the solid form of tabernanthalog sorbate salt (Pattern #5) is crystalline tabernanthalog sorbate salt (Pattern #5) characterized by XRPD signals at 14.1 °2θ, 16.5 °2θ, 18.3 °2θ, 20.5 °2θ, 20.8 °2θ, 21.2 °2θ, and 27.4°2θ (±0.2°2θ; ±0.1°2θ; or ±0.0 °2θ; Cu Kα1 radiation).

In some embodiments, the solid form of tabernanthalog sorbate salt (Pattern #5) is crystalline tabernanthalog sorbate salt (Pattern #5) characterized by XRPD signals at 7.7 °2θ, 14.1 °2θ, 16.5 °2θ, 18.3 °2θ, 19.2 °2θ, 20.5 °2θ, 20.8 °2θ, 21.2 °2θ, 23.2 °2θ, and 27.4 °2θ (±0.2 °2θ; ±0.1 °2θ; or 0.0 °2θ; Cu Kα1 radiation).

In some embodiments, the crystalline tabernanthalog sorbate salt is characterized by one, two, three, four, five, six, seven, eight, nine, or ten XRPD signals selected from those set forth in Table 286.

In some embodiments, the solid form of tabernanthalog sorbate salt (Pattern #6) is crystalline tabernanthalog sorbate (Pattern #6) characterized by one or more XRPD signals selected from the group consisting of 7.2°2θ and 5.7 °2θ (±0.2°2θ; ±0.1°2θ; or 0.0 °2θ; Cu Kα1 radiation).

In some embodiments, the solid form of tabernanthalog sorbate salt (Pattern #6) is crystalline tabernanthalog sorbate (Pattern #6) characterized by XRPD signals at 7.2°2θ and 5.7 °2θ (±0.2°2θ; ±0.1 °2θ; or 0.0 °2θ; Cu Kα1 radiation).

In some embodiments, the crystalline tabernanthalog sorbate salt is characterized by one or two XRPD signals selected from those set forth in Table 288.

In some embodiments, the solid form of tabernanthalog sorbate salt (Form A) is crystalline tabernanthalog sorbate salt (Form A) characterized by two or more, or three or more XRPD signals selected from the group consisting of 5.7 °2θ, 11.4 °2θ, and 24.7°2θ (±0.2°2θ; ±0.1°2θ; or 0.0 °2θ; Cu Kα1 radiation).

In some embodiments, the solid form of tabernanthalog sorbate salt (Form A) is crystalline tabernanthalog sorbate salt (Form A) characterized by XRPD signals at 5.7 °2θ, 11.4 °2θ, and 24.7 °2θ (±0.2°2θ; ±0.1 °2θ; or 0.0 °2θ; Cu Kα1 radiation).

In some embodiments, the solid form of tabernanthalog sorbate salt (Form A) is crystalline tabernanthalog sorbate salt (Form A) characterized by XRPD signals at 5.7 °2θ, 11.4 °2θ, 22.6 °2θ, and 24.7°2θ (±0.2 °2θ; ±0.1°2θ; or 0.0 °2θ; Cu Kα1 radiation).

In some embodiments, the crystalline tabernanthalog sorbate salt is characterized by one, two, three, or four XRPD signals selected from those set forth in Table 289.

In some embodiments, the solid form of tabernanthalog sorbate salt is crystalline tabernanthalog sorbate salt characterized by two or more, or three or more XRPD signals selected from the group consisting of 18.1 °2θ, 21.8 °2θ, and 25.0°2θ (±0.2 °2θ; ±0.1°2θ; or ±0.0 °2θ; Cu Kα1 radiation).

In some embodiments, the solid form of tabernanthalog sorbate salt is crystalline tabernanthalog sorbate salt characterized by XRPD signals at 18.1 °2θ, 21.8 °2θ, and 25.0°2θ (±0.2 °2θ; ±0.1 °2θ; or ±0.0 °2θ; Cu Kα1 radiation).

In some embodiments, the solid form of tabernanthalog sorbate salt is crystalline tabernanthalog sorbate salt (characterized by XRPD signals at 17.9 °2θ, 18.1 °2θ, 20.1°2θ, 21.8 °2θ, and 25.0°2θ (±0.2 °2θ; ±0.1°2θ; or 0.0 °2θ; Cu Kα1 radiation).

In some embodiments, the solid form of tabernanthalog sorbate salt is crystalline tabernanthalog sorbate salt characterized by XRPD signals at 17.9 °2θ, 18.1 °2θ, 18.7 °2θ, 20.1 °2θ, 21.8 °2θ, 25.0 °2θ, and 29.1 °2θ (±0.2°2θ; ±0.1°2θ; or 0.0 °2θ; Cu Kα1 radiation).

In some embodiments, the solid form of tabernanthalog sorbate salt is crystalline tabernanthalog sorbate salt characterized by XRPD signals at 12.5 °2θ, 17.9 °2θ, 18.1 °2θ, 18.7 °2θ, 20.1°2θ, 21.8 °2θ, 25.0 °2θ, 26.0 °2θ, 27.5 °2θ, and 29.1°2θ (±0.2°2θ; ±0.1 °2θ; or ±0.0 °2θ; Cu Kα1 radiation).

In some embodiments, the crystalline tabernanthalog sorbate salt is characterized by one, two, three, four, five, six, seven, eight, nine, or ten XRPD signals selected from those set forth in Table 290.

In some embodiments, the solid form of tabernanthalog sorbate salt (Form A) is crystalline tabernanthalog sorbate salt (Form A) characterized by two or more, or three or more XRPD signals selected from the group consisting of 5.7 °2θ, 11.5 °2θ, and 23.0°2θ (±0.2°2θ; ±0.1°2θ; or 0.0 °2θ; Cu Kα1 radiation).

In some embodiments, the solid form of tabernanthalog sorbate salt (Form A) is crystalline tabernanthalog sorbate salt (Form A) characterized by XRPD signals at 5.7 °2θ, 11.5 °2θ, and 23.0 °2θ (±0.2°2θ; ±0.1°2θ; or 0.0 °2θ; Cu Kα1 radiation).

In some embodiments, the solid form of tabernanthalog sorbate salt (Form A) is crystalline tabernanthalog sorbate salt (Form A) characterized by XRPD signals at 5.7 °2θ, 11.5 °2θ, 18.8 °2θ, and 23.0°2θ (±0.2 °2θ; ±0.1°2θ; or ±0.0 °2θ; Cu Kα1 radiation).

In some embodiments, the crystalline tabernanthalog sorbate salt (Form A) is characterized by one, two, three, or four XRPD signals selected from those set forth in Table 291.

In some embodiments, the solid form of tabernanthalog sorbate Form A is crystalline tabernanthalog sorbate Form A characterized by two or more, or three or more XRPD signals selected from the group consisting of 18.9 °2θ, 24.5 °2θ, and 17.9°2θ (±0.2°2θ; ±0.1°2θ; or 0.0 °2θ; Cu Kα1 radiation). In some embodiments, the solid form of tabernanthalog sorbate Form A is crystalline tabernanthalog sorbate Form A characterized by XRPD signals at 18.9 °2θ, 24.5 °2θ, and 17.9°2θ (±0.2°2θ; ±0.1 °2θ; or 0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 18.9 °2θ, 24.5 °2θ, 17.9 °2θ, 22.6 °2θ, and 5.6°2θ (±0.2 °2θ; ±0.1 °2θ; or 0.0 °2θ; Cu Kα1 radiation). In some embodiments, the solid form of tabernanthalog sorbate Form A is crystalline tabernanthalog sorbate Form A characterized by XRPD signals at 18.9 °2θ, 24.5 °2θ, 17.9 °2θ, 22.6 °2θ, and 5.6°2θ (±0.2°2θ; ±0.1°2θ; or 0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 18.9 °2θ, 24.5 °2θ, 17.9 °2θ, 22.6 °2θ, 5.6 °2θ, 17.4 °2θ, and 11.3°2θ (±0.2°2θ; ±0.1°2θ; or 0.0 °2θ; Cu Kα1 radiation). In some embodiments, the solid form of tabernanthalog sorbate Form A is crystalline tabernanthalog sorbate Form A characterized by XRPD signals at 18.9 °2θ, 24.5 °2θ, 17.9 °2θ, 22.6 °2θ, 5.6 °2θ, 17.4 °2θ, and 11.3°2θ (±0.2°2θ; ±0.1°2θ; or 0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 18.9 °2θ, 24.5 °2θ, 17.9 °2θ, 22.6 °2θ, 5.6 °2θ, 17.4 °2θ, 11.3 °2θ, 10.5 °2θ, 21.4 °2θ, and 26.7 °2θ (±0.2°2θ; ±0.1°2θ; or ±0.0 °2θ; Cu Kα1 radiation). In some embodiments, the solid form of tabernanthalog sorbate Form A is crystalline tabernanthalog sorbate Form A characterized by XRPD signals at 18.9 °2θ, 24.5 °2θ, 17.9 °2θ, 22.6 °2θ, 5.6 °2θ, 17.4 °2θ, 11.3 °2θ, 10.5 °2θ, 21.4 °2θ, and 26.7°2θ (±0.2°2θ; ±0.1°2θ; or ±0.0 °2θ; Cu Kα1 radiation).

In some embodiments, the crystalline tabernanthalog sorbate Form A is characterized by one, two, three, four, five, six, seven, eight, nine, ten, eleven, twelve, thirteen, fourteen, fifteen, or sixteen XRPD signals selected from those set forth in Table 317.

In some embodiments, the solid form of tabernanthalog sorbate Form A is crystalline tabernanthalog sorbate Form A characterized by two or more, or three or more XRPD signals selected from the group consisting of 18.9 °2θ, 24.6 °2θ, and 24.5°2θ (±0.2°2θ; ±0.1°2θ; or 0.0 °2θ; Cu Kα1 radiation). In some embodiments, the solid form of tabernanthalog sorbate Form A is crystalline tabernanthalog sorbate Form A characterized by XRPD signals at 18.9 °2θ, 24.6 °2θ, and 24.5°2θ (±0.2°2θ; ±0.1°2θ; or 0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 18.9 °2θ, 24.6 °2θ, 24.5 °2θ, 19.1 °2θ, and 17.9°2θ (±0.2°2θ; ±0.1 °2θ; or ±0.0 °2θ; Cu Kα1 radiation). In some embodiments, the solid form of tabernanthalog sorbate Form A is crystalline tabernanthalog sorbate Form A characterized by XRPD signals at 18.9 °2θ, 24.6 °2θ, 24.5 °2θ, 19.1 °2θ, and 17.9°2θ (±0.2 °2θ; ±0.1 °2θ; or 0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 18.9 °2θ, 24.6 °2θ, 24.5 °2θ, 19.1 °2θ, 17.9 °2θ, 22.6 °2θ, and 5.6°2θ (±0.2°2θ; ±0.1°2θ; or 0.0 °2θ; Cu Kα1 radiation). In some embodiments, the solid form of tabernanthalog sorbate Form A is crystalline tabernanthalog sorbate Form A characterized by XRPD signals at 18.9 °2θ, 24.6 °2θ, 24.5 °2θ, 19.1 °2θ, 17.9 °2θ, 22.6 °2θ, and 5.6°2θ (±0.2°2θ; ±0.1°2θ; or ±0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 18.9 °2θ, 24.6 °2θ, 24.5 °2θ, 19.1 °2θ, 17.9 °2θ, 22.6 °2θ, 5.6 °2θ, 21.4 °2θ, 10.5 °2θ, and 11.4°2θ (±0.2°2θ; ±0.1°2θ; or ±0.0 °2θ; Cu Kα1 radiation). In some embodiments, the solid form of tabernanthalog sorbate Form A is crystalline tabernanthalog sorbate Form A characterized by XRPD signals at 18.9 °2θ, 24.6 °2θ, 24.5 °2θ, 19.1 °2θ, 17.9 °2θ, 22.6 °2θ, 5.6 °2θ, 21.4 °2θ, 10.5 °2θ, and 11.4020 (±0.2°2θ; ±0.1°2θ; or 0.0 °2θ; Cu Kα1 radiation).

In some embodiments, the crystalline tabernanthalog sorbate Form A is characterized by one, two, three, four, five, six, seven, eight, nine, ten, eleven, twelve, thirteen, fourteen, fifteen, sixteen, seventeen, or eighteen XRPD signals selected from those set forth in Table 318.

In some embodiments, the solid form of tabernanthalog sorbate Form A is crystalline tabernanthalog sorbate Form A characterized by two or more, or three or more XRPD signals selected from the group consisting of 18.9 °2θ, 5.7 °2θ, and 24.7°2θ (±0.2°2θ; ±0.1°2θ; or 0.0 °2θ; Cu Kα1 radiation). In some embodiments, the solid form of tabernanthalog sorbate Form A is crystalline tabernanthalog sorbate Form A characterized by XRPD signals at 18.9 °2θ, 5.7 °2θ, and 24.7°2θ (±0.2°2θ; ±0.1°2θ; or ±0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 18.9 °2θ, 5.7 °2θ, 24.7 °2θ, 24.5 °2θ, and 10.5°2θ (±0.2°2θ; ±0.1°2θ; or ±0.0 °2θ; Cu Kα1 radiation). In some embodiments, the solid form of tabernanthalog sorbate Form A is crystalline tabernanthalog sorbate Form A characterized by XRPD signals at 18.9 °2θ, 5.7 °2θ, 24.7 °2θ, 24.5 °2θ, and 10.5°2θ (±0.2°2θ; ±0.1 °2θ; or ±0.0 °2θ; Cu Kα1 radiation). In some embodiments, the solid form of tabernanthalog sorbate Form A is crystalline tabernanthalog sorbate Form A characterized by two or more, or three or more XRPD signals selected from the group consisting of 18.9 °2θ, 5.7 °2θ, 24.7 °2θ, 24.5 °2θ, 10.5 °2θ, 11.4 °2θ, and 22.6°2θ (±0.2°2θ; ±0.1 °2θ; or ±0.0 °2θ; Cu Kα1 radiation). In some embodiments, the solid form of tabernanthalog sorbate Form A is crystalline tabernanthalog sorbate Form A characterized by XRPD signals at 18.9 °2θ, 5.7 °2θ, 24.7 °2θ, 24.5 °2θ, 10.5 °2θ, 11.4 °2θ, and 22.6 °2θ (±0.2°2θ; ±0.1°2θ; or ±0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 18.9 °2θ, 5.7 °2θ, 24.7 °2θ, 24.5 °2θ, 10.5 °2θ, 11.4 °2θ, 22.6 °2θ, 17.9 °2θ, 19.1 °2θ, and 21.4°2θ (±0.2°2θ; ±0.1°2θ; or 0.0°2θ; Cu Kα1 radiation). In some embodiments, the solid form of tabernanthalog sorbate Form A is crystalline tabernanthalog sorbate Form A characterized by XRPD signals at 18.9 °2θ, 5.7 °2θ, 24.7 °2θ, 24.5 °2θ, 10.5 °2θ, 11.4 °2θ, 22.6 °2θ, 17.9 °2θ, 19.1 °2θ, and 21.4 °2θ (±0.2 °2θ; ±0.1°2θ; or 0.0 °2θ; Cu Kα1 radiation).

In some embodiments, the crystalline tabernanthalog sorbate Form A is characterized by one, two, three, four, five, six, seven, eight, nine, ten, eleven, twelve, thirteen, fourteen, fifteen, sixteen, seventeen, eighteen, or nineteen XRPD signals selected from those set forth in Table 319.

In some embodiments, the solid form of tabernanthalog sorbate is crystalline tabernanthalog sorbate characterized by two or more, or three or more XRPD signals selected from the group consisting of 18.7 °2θ, 24.5 °2θ, and 22.5°2θ (±0.2 °2θ; ±0.1 °2θ; or 0.0 °2θ; Cu Kα1 radiation).

In some embodiments, the solid form of tabernanthalog sorbate is crystalline tabernanthalog sorbate characterized by XRPD signals at 18.7 °2θ, 24.5 °2θ, and 22.5°2θ (±0.2°2θ; ±0.1°2θ; or ±0.0 °2θ; Cu Kα1 radiation).

In some embodiments, the solid form of tabernanthalog sorbate is crystalline tabernanthalog sorbate characterized by two or more, or three or more XRPD signals selected from the group consisting of 18.7 °2θ, 24.5 °2θ, 22.5 °2θ, 11.2 °2θ, and 24.2 °2θ (±0.2 °2θ; ±0.1°2θ; or ±0.0 °2θ; Cu Kα1 radiation). In some embodiments, the solid form of tabernanthalog sorbate is crystalline tabernanthalog sorbate characterized by XRPD signals at 18.7 °2θ, 24.5 °2θ, 22.5 °2θ, 11.2 °2θ, and 24.2°2θ (±0.2°2θ; ±0.1 °2θ; or ±0.0 °2θ; Cu Kα1 radiation).

In some embodiments, the solid form of tabernanthalog sorbate is crystalline tabernanthalog sorbate characterized by two or more, or three or more XRPD signals selected from the group consisting of 18.7 °2θ, 24.5 °2θ, 22.5 °2θ, 11.2020, 24.2 °2θ, 22.8 °2θ, and 19.0 °2θ (±0.2 °2θ; ±0.1 °2θ; or ±0.0 °2θ; Cu Kα1 radiation). In some embodiments, the solid form of tabernanthalog sorbate is crystalline tabernanthalog sorbate characterized by XRPD signals at 18.7 °2θ, 24.5 °2θ, 22.5 °2θ, 11.2 °2θ, 24.2 °2θ, 22.8 °2θ, and 19.0°2θ (±0.2 °2θ; ±0.1 °2θ; or 0.0 °2θ; Cu Kα1 radiation).

In some embodiments, the solid form of tabernanthalog sorbate is crystalline tabernanthalog sorbate characterized by two or more, or three or more XRPD signals selected from the group consisting of 18.7 °2θ, 24.5 °2θ, 22.5 °2θ, 11.2 °2θ, 24.2 °2θ, 22.8 °2θ, 19.0 °2θ, 21.3 °2θ, 17.9 °2θ, and 26.7°2θ (±0.2°2θ; ±0.1 °2θ; or 0.0 °2θ; Cu Kα1 radiation). In some embodiments, the solid form of tabernanthalog sorbate is crystalline tabernanthalog sorbate characterized by XRPD signals at 18.7 °2θ, 24.5 °2θ, 22.5 °2θ, 11.2 °2θ, 24.2 °2θ, 22.8 °2θ, 19.0 °2θ, 21.3 °2θ, 17.9 °2θ, and 26.7 °2θ (±0.2 °2θ; ±0.1°2θ; or 0.0 °2θ; Cu Kα1 radiation).

In some embodiments, the crystalline tabernanthalog sorbate is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 320.

In some embodiments, the solid form of Tabernanthalog·Sorbate·Pattern #7 is crystalline Tabernanthalog·Sorbate·Pattern #7 characterized by two or more, or three or more XRPD signals selected from the group consisting of 9.4 °2θ, 6.3 °2θ, and 19.0 °2θ (±0.2 °2θ; ±0.1°2θ; or ±0.0 °2θ; Cu Kα1 radiation). In some embodiments, the solid form of Tabernanthalog·Sorbate·Pattern #7 is crystalline Tabernanthalog·Sorbate·Pattern #7 characterized by XRPD signals at 9.4 °2θ, 6.3 °2θ, and 19.0 °2θ (±0.2 °2θ; ±0.1°2θ; or ±0.0 °2θ; Cu Kα1 radiation).

In some embodiments, the solid form of Tabernanthalog·Sorbate·Pattern #7 is crystalline Tabernanthalog·Sorbate·Pattern #7 characterized by two or more, or three or more XRPD signals selected from the group consisting of 9.4 °2θ, 6.3 °2θ, 19.0 °2θ, 22.6 °2θ, and 17.7°2θ (±0.2 °2θ; ±0.1°2θ; or 0.0 °2θ; Cu Kα1 radiation). In some embodiments, the solid form of Tabernanthalog·Sorbate·Pattern #7 is crystalline Tabernanthalog·Sorbate·Pattern #7 characterized by XRPD signals at 9.4 °2θ, 6.3 °2θ, 19.0 °2θ, 22.6 °2θ, and 17.7°2θ (±0.2°2θ; ±0.1°2θ; or 0.0 °2θ; Cu Kα1 radiation).

In some embodiments, the solid form of Tabernanthalog·Sorbate·Pattern #7 is crystalline Tabernanthalog·Sorbate·Pattern #7 characterized by two or more, or three or more XRPD signals selected from the group consisting of 9.4 °2θ, 6.3 °2θ, 19.0 °2θ, 22.6 °2θ, 17.7 °2θ, 17.1 °2θ, and 15.8°2θ (±0.2°2θ; ±0.1°2θ; or 0.0 °2θ; Cu Kα1 radiation). In some embodiments, the solid form of Tabernanthalog·Sorbate-Pattern #7 is crystalline Tabernanthalog·Sorbate·Pattern #7 characterized by XRPD signals at 9.4 °2θ, 6.3 °2θ, 19.0 °2θ, 22.6 °2θ, 17.7 °2θ, 17.1 °2θ, and 15.8 °2θ (±0.2 °2θ; ±0.1°2θ; or 0.0 °2θ; Cu Kα1 radiation).

In some embodiments, the solid form of Tabernanthalog·Sorbate-Pattern #7 is crystalline Tabernanthalog·Sorbate·Pattern #7 characterized by two or more, or three or more XRPD signals selected from the group consisting of 9.4 °2θ, 6.3 °2θ, 19.0 °2θ, 22.6 °2θ, 17.7 °2θ, 17.1 °2θ, 15.8 °2θ, 19.4 °2θ, 15.4 °2θ, and 17.2°2θ (±0.2 °2θ; ±0.1 °2θ; or 0.0 °2θ; Cu Kα1 radiation). In some embodiments, the solid form of Tabernanthalog·Sorbate·Pattern #7 is crystalline Tabernanthalog·Sorbate·Pattern #7 characterized by XRPD signals at 9.4 °2θ, 6.3 °2θ, 19.0 °2θ, 22.6 °2θ, 17.7 °2θ, 17.1 °2θ, 15.8 °2θ, 19.4 °2θ, 15.4 °2θ, and 17.2°2θ (±0.2°2θ; ±0.1°2θ; or 0.0 °2θ; Cu Kα1 radiation).

In some embodiments, the crystalline Tabernanthalog·Sorbate·Pattern #7 is characterized by one, two, three, four, five, six, seven, eight, nine, ten, or eleven XRPD signals selected from those set forth in Table 322.

In some embodiments, the solid form of Tabernanthalog·Sorbate·Pattern #7 is crystalline Tabernanthalog·Sorbate-Pattern #7 characterized by two or more, or three or more XRPD signals selected from the group consisting of 9.5 °2θ, 19.0 °2θ, and 22.6°2θ (±0.2°2θ; ±0.1°2θ; or 0.0 °2θ; Cu Kα1 radiation). In some embodiments, the solid form of Tabernanthalog·Sorbate-Pattern #7 is crystalline Tabernanthalog·Sorbate·Pattern #7 characterized by XRPD signals at 9.5 °2θ, 19.0 °2θ, and 22.6 °2θ (±0.2°2θ; ±0.1°2θ; or ±0.0 °2θ; Cu Kα1 radiation).

In some embodiments, the solid form of Tabernanthalog·Sorbate·Pattern #7 is crystalline Tabernanthalog·Sorbate·Pattern #7 characterized by two or more, or three or more XRPD signals selected from the group consisting of 9.5 °2θ, 19.0 °2θ, 22.6 °2θ, 6.4 °2θ, and 15.4°2θ (±0.2°2θ; ±0.1°2θ; or ±0.0 °2θ; Cu Kα1 radiation). In some embodiments, the solid form of Tabernanthalog·Sorbate-Pattern #7 is crystalline Tabernanthalog·Sorbate·Pattern #7 characterized by XRPD signals at 9.5 °2θ, 19.0 °2θ, 22.6 °2θ, 6.4 °2θ, and 15.4°2θ (±0.2°2θ; ±0.1°2θ; or 0.0 °2θ; Cu Kα1 radiation).

In some embodiments, the solid form of Tabernanthalog·Sorbate·Pattern #7 is crystalline Tabernanthalog·Sorbate·Pattern #7 characterized by two or more, or three or more XRPD signals selected from the group consisting of 9.5 °2θ, 19.0 °2θ, 22.6 °2θ, 6.4 °2θ, 15.4 °2θ, 17.7 °2θ, and 17.1°2θ (±0.2 °2θ; ±0.1 °2θ; or ±0.0 °2θ; Cu Kα1 radiation). In some embodiments, the solid form of Tabernanthalog·Sorbate·Pattern #7 is crystalline Tabernanthalog·Sorbate·Pattern #7 characterized by XRPD signals at 9.5 °2θ, 19.0 °2θ, 22.6 °2θ, 6.4 °2θ, 15.4 °2θ, 17.7 °2θ, and 17.1 °2θ (±0.2°2θ; ±0.1°2θ; or 0.0 °2θ; Cu Kα1 radiation).

In some embodiments, the solid form of Tabernanthalog·Sorbate·Pattern #7 is crystalline Tabernanthalog·Sorbate·Pattern #7 characterized by two or more, or three or more XRPD signals selected from the group consisting of 9.5 °2θ, 19.0 °2θ, 22.6 °2θ, 6.4 °2θ, 15.4 °2θ, 17.7 °2θ, 17.1 °2θ, 17.2 °2θ, 19.5 °2θ, and 13.3°2θ (±0.2 °2θ; ±0.1 °2θ; or 0.0 °2θ; Cu Kα1 radiation). In some embodiments, the solid form of Tabernanthalog·Sorbate·Pattern #7 is crystalline Tabernanthalog·Sorbate·Pattern #7 characterized by XRPD signals at 9.5 °2θ, 19.0 °2θ, 22.6 °2θ, 6.4 °2θ, 15.4 °2θ, 17.7°2θ, 17.1 °2θ, 17.2 °2θ, 19.5°2θ, and 13.3 °2θ (±0.2°2θ; ±0.1 °2θ; or ±0.0 °2θ; Cu Kα1 radiation).

In some embodiments, the crystalline Tabernanthalog·Sorbate·Pattern #7 is characterized by one, two, three, four, five, six, seven, eight, nine, ten, eleven, twelve, thirteen, fourteen, fifteen, sixteen, seventeen, eighteen, nineteen, twenty, or twenty-one XRPD signals selected from those set forth in Table 323.

In some embodiments, the solid form of Tabernanthalog·Sorbate·Pattern #7 is crystalline Tabernanthalog·Sorbate·Pattern #7 characterized by two or more, or three or more XRPD signals selected from the group consisting of 22.7 °2θ, 17.7 °2θ, and 17.2 °2θ (±0.2 °2θ; ±0.1 °2θ; or 0.0 °2θ; Cu Kα1 radiation). In some embodiments, the solid form of Tabernanthalog·Sorbate·Pattern #7 is crystalline Tabernanthalog·Sorbate-Pattern #7 characterized by XRPD signals at 22.7 °2θ, 17.7 °2θ, and 17.2°2θ (±0.2 °2θ; ±0.1 °2θ; or ±0.0 °2θ; Cu Kα1 radiation).

In some embodiments, the solid form of Tabernanthalog·Sorbate·Pattern #7 is crystalline Tabernanthalog·Sorbate·Pattern #7 characterized by two or more, or three or more XRPD signals selected from the group consisting of 22.7 °2θ, 17.7 °2θ, 17.2 °2θ, 9.5 °2θ, and 19.0 °2θ (±0.2 °2θ; ±0.1 °2θ; or ±0.0 °2θ; Cu Kα1 radiation). In some embodiments, the solid form of Tabernanthalog·Sorbate·Pattern #7 is crystalline Tabernanthalog·Sorbate·Pattern #7 characterized by XRPD signals at 22.7 °2θ, 17.7 °2θ, 17.2 °2θ, 9.5 °2θ, and 19.0°2θ (±0.2°2θ; ±0.1 °2θ; or ±0.0 °2θ; Cu Kα1 radiation).

In some embodiments, the solid form of Tabernanthalog·Sorbate-Pattern #7 is crystalline Tabernanthalog·Sorbate·Pattern #7 characterized by two or more, or three or more XRPD signals selected from the group consisting of 22.7 °2θ, 17.7 °2θ, 17.2 °2θ, 9.5 °2θ, 19.0 °2θ, 15.4 °2θ, and 13.3 °2θ (±0.2 °2θ; ±0.1 °2θ; or ±0.0 °2θ; Cu Kα1 radiation). In some embodiments, the solid form of Tabernanthalog·Sorbate·Pattern #7 is crystalline Tabernanthalog·Sorbate·Pattern #7 characterized by XRPD signals at 22.7 °2θ, 17.7 °2θ, 17.2 °2θ, 9.5 °2θ, 19.0 °2θ, 15.4 °2θ, and 13.3 °2θ (±0.2 °2θ; ±0.1°2θ; or ±0.0 °2θ; Cu Kα1 radiation).

In some embodiments, the solid form of Tabernanthalog·Sorbate·Pattern #7 is crystalline Tabernanthalog·Sorbate·Pattern #7 characterized by two or more, or three or more XRPD signals selected from the group consisting of 22.7 °2θ, 17.7 °2θ, 17.2 °2θ, 9.5 °2θ, 19.0 °2θ, 15.4 °2θ, 13.3 °2θ, 6.3 °2θ, 19.5 °2θ, and 16.2 °2θ (±0.2 °2θ; ±0.1 °2θ; or ±0.0 °2θ; Cu Kα1 radiation). In some embodiments, the solid form of Tabernanthalog·Sorbate-Pattern #7 is crystalline Tabernanthalog·Sorbate·Pattern #7 characterized by XRPD signals at 22.7 °2θ, 17.7 °2θ, 17.2 °2θ, 9.5 °2θ, 19.0 °2θ, 15.4 °2θ, 13.3°2θ, 6.3 °2θ, 19.5 °2θ, and 16.2 °2θ (±0.2 °2θ; ±0.1 °2θ; or 0.0 °2θ; Cu Kα1 radiation).

In some embodiments, the crystalline Tabernanthalog·Sorbate·Pattern #7 is characterized by one, two, three, four, five, six, seven, eight, nine, ten, eleven, twelve, thirteen, fourteen, fifteen, sixteen, seventeen, eighteen, nineteen, twenty, twenty-one, twenty-two, or twenty-three XRPD signals selected from those set forth in Table 324.

In some embodiments, the solid form of tabernanthalog sorbate Form A is crystalline tabernanthalog sorbate Form A characterized by two or more, or three or more XRPD signals selected from the group consisting of 5.7 °2θ, 18.9 °2θ, and 31.7 °2θ (±0.2°2θ; ±0.1 °2θ; or ±0.0 °2θ; Cu Kα1 radiation). In some embodiments, the solid form of tabernanthalog sorbate Form A is crystalline tabernanthalog sorbate Form A characterized by XRPD signals at 5.7 °2θ, 18.9 °2θ, and 31.7°2θ (±0.2°2θ; ±0.1 °2θ; or ±0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 5.7 °2θ, 18.9 °2θ, 31.7 °2θ, 24.7 °2θ, and 10.5 °2θ (±0.2 °2θ; ±0.1 °2θ;

or 0.0 °2θ; Cu Kα1 radiation). In some embodiments, the solid form of tabernanthalog sorbate Form A is crystalline tabernanthalog sorbate Form A characterized by XRPD signals at 5.7 °2θ, 18.9 °2θ, 31.7 °2θ, 24.7 °2θ, and 10.5 °2θ (±0.2 °2θ; ±0.1°2θ; or 0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 5.7 °2θ, 18.9 °2θ, 31.7 °2θ, 24.7 °2θ, 10.5 °2θ, 18.0 °2θ, and 22.7°2θ (±0.2°2θ; ±0.1°2θ; or 0.0 °2θ; Cu Kα1 radiation). In some embodiments, the solid form of tabernanthalog sorbate Form A is crystalline tabernanthalog sorbate Form A characterized by XRPD signals at 5.7 °2θ, 18.9 °2θ, 31.7 °2θ, 24.7 °2θ, 10.5 °2θ, 18.0 °2θ, and 22.7°2θ (±0.2 °2θ; ±0.1 °2θ; or 0.0 °2θ; Cu Kα1 radiation).

In some embodiments, the solid form of tabernanthalog sorbate Form A is crystalline tabernanthalog sorbate Form A characterized by two or more, or three or more XRPD signals selected from the group consisting of 5.7 °2θ, 18.9 °2θ, 31.7 °2θ, 24.7 °2θ, 10.5 °2θ, 18.0 °2θ, 22.7 °2θ, 11.4 °2θ, 19.2 °2θ, and 21.4°2θ (±0.2 °2θ; 0.1°2θ; or ±0.0 °2θ; Cu Kα1 radiation). In some embodiments, the solid form of tabernanthalog sorbate Form A is crystalline tabernanthalog sorbate Form A characterized by XRPD signals at 5.7 °2θ, 18.9 °2θ, 31.7 °2θ, 24.7 °2θ, 10.5 °2θ, 18.0 °2θ, 22.7 °2θ, 11.4 °2θ, 19.2 °2θ, and 21.4°2θ (±0.2 °2θ; ±0.1 °2θ; or 0.0 °2θ; Cu Kα1 radiation).

In some embodiments, the crystalline tabernanthalog sorbate Form A is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 325.

In some embodiments, the solid form of Tabernanthalog·Sorbate HemiHFIPA (pattern #7) is crystalline Tabernanthalog·Sorbate HemiHFIPA (pattern #7) characterized by two or more, or three or more XRPD signals selected from the group consisting of 22.6 °2θ, 9.4 °2θ, and 17.7°2θ (±0.2°2θ; ±0.1 °2θ, or 0.0 °2θ; Cu Kα1 radiation). In some embodiments, the solid form Tabernanthalog·Sorbate HemiHFIPA (pattern #7) is crystalline Tabernanthalog·Sorbate HemiHFIPA (pattern #7) characterized by XRPD signals at 22.6 °2θ, 9.4 °2θ, and 17.7°2θ (±0.2 °2θ; ±0.1 °2θ; or ±0.0 °2θ; Cu Kα1 radiation).

In some embodiments, the solid form of Tabernanthalog·Sorbate HemiHFIPA (pattern #7) is crystalline Tabernanthalog·Sorbate HemiHFIPA (pattern #7) characterized by two or more, or three or more XRPD signals selected from the group consisting of 22.6 °2θ, 9.4 °2θ, 17.7 °2θ, 17.1 °2θ, and 19.0 °2θ (±0.2 °2θ; ±0.1°2θ; or 0.0 °2θ; Cu Kα1 radiation). In some embodiments, the solid form of Tabernanthalog·Sorbate HemiHFIPA (pattern #7) is crystalline Tabernanthalog·Sorbate HemiHFIPA (pattern #7) characterized by XRPD signals at 22.6 °2θ, 9.4 °2θ, 17.7 °2θ, 17.1 °2θ, and 19.0°2θ (±0.2°2θ; ±0.1 °2θ; or 0.0 °2θ; Cu Kα1 radiation).

In some embodiments, the solid form of Tabernanthalog·Sorbate HemiHFIPA (pattern #7) salt is crystalline Tabernanthalog·Sorbate HemiHFIPA (pattern #7) characterized by two or more, or three or more XRPD signals selected from the group consisting of 22.6 °2θ, 9.4 °2θ, 17.7 °2θ, 17.1 °2θ, 19.0 °2θ, 6.3 °2θ, and 15.4 °2θ, (±0.2 °2θ; ±0.1°2θ; or 0.0 °2θ; Cu Kα1 radiation). In some embodiments, the solid form of Tabernanthalog·Sorbate HemiHFIPA (pattern #7) is crystalline Tabernanthalog·Sorbate HemiHFIPA (pattern #7) characterized by XRPD signals at 22.6 °2θ, 9.4 °2θ, 17.7 °2θ, 17.1 °2θ, 19.0 °2θ, 6.3 °2θ, and 15.4°2θ (±0.2°2θ; ±0.1°2θ; or 0.0 °2θ; Cu Kα1 radiation).

In some embodiments, the solid form of Tabernanthalog·Sorbate HemiHFIPA (pattern #7) is crystalline Tabernanthalog·Sorbate HemiHFIPA (pattern #7) characterized by two or more, or three or more XRPD signals selected from the group consisting of 22.6 °2θ, 9.4 °2θ, 17.7 °2θ, 17.1 °2θ, 19.0 °2θ, 6.3 °2θ, 15.4 °2θ, 17.1 °2θ, 19.4 °2θ, 13.3 °2θ, and 23.8 °2θ (±0.2°2θ; ±0.1°2θ; or ±0.0 °2θ; Cu Kα1 radiation). In some embodiments, the solid form of Tabernanthalog·Sorbate HemiHFIPA (pattern #7) is Tabernanthalog·Sorbate HemiHFIPA (pattern #7) characterized by XRPD signals at 22.6 °2θ, 9.4 °2θ, 17.7 °2θ, 17.1 °2θ, 19.0 °2θ, 6.3 °2θ, 15.4 °2θ, 17.1 °2θ, 19.4 °2θ, 13.3 °2θ, and 23.8 °2θ (±0.2 °2θ; ±0.1 °2θ; or 0.0 °2θ; Cu Kα1 radiation).

In some embodiments, the crystalline Tabernanthalog·Sorbate HemiHFIPA (pattern #7) is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four XRPD signals selected from those set forth in Table 303.

In some embodiments, the solid form of tabernanthalog sorbate salt is crystalline Tabernanthalog sorbate salt characterized by two or more XRPD signals selected from the group consisting of 5.7 °2θ, 11.4 °2θ, and 24.6 °2θ (±0.2 °2θ; ±0.1°2θ; or ±0.0 °2θ; Cu Kα1 radiation). In some embodiments, the solid form of Tabernanthalog sorbate salt is crystalline Tabernanthalog sorbate salt characterized by XRPD signals 5.7 °2θ, 11.4 °2θ, and 24.6°2θ (±0.2 °2θ; ±0.1°2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 5.7 °2θ, 11.4 °2θ, 24.6 °2θ, 24.5 °2θ, and 18.9°2θ (±0.2°2θ; ±0.1°2θ; or 0.0 °2θ; Cu Kα1 radiation). In some embodiments, the solid form of Tabernanthalog sorbate salt is crystalline Tabernanthalog sorbate salt characterized by XRPD signals at 5.7 °2θ, 11.4 °2θ, 24.6 °2θ, 24.5 °2θ, and 18.9°2θ (±0.2°2θ; ±0.1°2θ; or ±0.0 °2θ; Cu Kα1 radiation).

In some embodiments, the crystalline Tabernanthalog sorbate salt is characterized by one, two, three, four, five, or six XRPD signals selected from those set forth in Table 304.

In some embodiments, the solid form of Tabernanthalog sorbate salt is crystalline Tabernanthalog sorbate salt characterized by two or more, or three or more XRPD signals selected from the group consisting of 5.6 °2θ, 11.3 °2θ, and 18.9°2θ (±0.2°2θ; ±0.1 °2θ; or ±0.0 °2θ; Cu Kα1 radiation). In some embodiments, the solid form of Tabernanthalog sorbate salt is crystalline Tabernanthalog sorbate salt characterized by XRPD signals at 5.6 °2θ, 11.3 °2θ, and 18.9°2θ (±0.2 °2θ; ±0.1°2θ; or 0.0 °2θ; Cu Kα1 radiation).

In some embodiments, the crystalline Tabernanthalog sorbate salt is characterized by one, two, or three XRPD signals selected from those set forth in Table 305.

In some embodiments, the solid form of Tabernanthalog sorbate salt is crystalline Tabernanthalog sorbate salt characterized by two or more, or three or more XRPD signals selected from the group consisting of 5.7 °2θ, 11.4 °2θ, and 18.9°2θ (±0.2°2θ; ±0.1°2θ; or ±0.0 °2θ; Cu Kα1 radiation). In some embodiments, the solid form Tabernanthalog sorbate salt is crystalline Tabernanthalog sorbate salt characterized by XRPD signals at 5.7 °2θ, 11.4 °2θ, and 18.9 °2θ (±0.2 °2θ; ±0.1 °2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 5.7 °2θ, 11.4 °2θ, 18.9 °2θ, 24.7 °2θ, and 10.5°2θ (±0.2°2θ; ±0.1 °2θ; or ±0.0 °2θ; Cu Kα1 radiation). In some embodiments, the solid form of Tabernanthalog sorbate salt is crystalline Tabernanthalog sorbate salt characterized by XRPD signals at 5.7 °2θ, 11.4 °2θ, 18.9 °2θ, 24.7 °2θ, and 10.5°2θ (±0.2°2θ; ±0.1 °2θ; or 0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 5.7 °2θ, 11.4 °2θ, 18.9 °2θ, 24.7 °2θ, 10.5 °2θ, 22.7 °2θ, and 18.0°2θ (±0.2 °2θ; ±0.1 °2θ; or ±0.0 °2θ; Cu Kα1 radiation). In some embodiments, the solid form of Tabernanthalog sorbate salt is crystalline Tabernanthalog sorbate salt characterized by XRPD signals at 5.7 °2θ, 11.4 °2θ, 18.9 °2θ, 24.7 °2θ, 10.5 °2θ, 22.7 °2θ, and 18.0 °2θ (±0.2 °2θ; ±0.1 °2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 5.7 °2θ, 11.4 °2θ, 18.9 °2θ, 24.7 °2θ, 10.5 °2θ, 22.7 °2θ, 18.0 °2θ, 24.4 °2θ, 19.2 °2θ, and 21.4 °2θ (±0.2°2θ; ±0.1 °2θ; or ±0.0 °2θ; Cu Kα1 radiation). In some embodiments, the solid form of Tabernanthalog sorbate salt is crystalline Tabernanthalog sorbate salt characterized by XRPD signals at 5.7 °2θ, 11.4 °2θ, 18.9 °2θ, 24.7 °2θ, 10.5 °2θ, 22.7°2θ, 18.0 °2θ, 24.4 °2θ, 19.2 °2θ, and 21.4°2θ (±0.2°2θ; ±0.1°2θ; or 0.0 °2θ; Cu Kα1 radiation).

In some embodiments, the crystalline Tabernanthalog sorbate salt is characterized by one, two, three, four, five, six, seven, eight, nine, or ten, XRPD signals selected from those set forth in Table 306.

In some embodiments, the solid form of Tabernanthalog sorbate salt is crystalline Tabernanthalog sorbate salt characterized by two or more, or three or more XRPD signals selected from the group consisting of 5.7 °2θ, 11.4 °2θ, 18.9°2θ, 22.8°2θ (±0.2°2θ; ±0.1 °2θ; or 0.0 °2θ; Cu Kα1 radiation). In some embodiments, the solid form of Tabernanthalog sorbate salt is crystalline Tabernanthalog sorbate salt characterized by XRPD signals at 5.7 °2θ, 11.4 °2θ, 18.9 °2θ, 22.8°2θ (±0.2°2θ; ±0.1 °2θ; or 0.0 °2θ; Cu Kα1 radiation).

In some embodiments, the crystalline Tabernanthalog sorbate salt is characterized by one, two, three, or four XRPD signals selected from those set forth in Table 307.

In some embodiments, the solid form of Tabernanthalog sorbate salt is crystalline Tabernanthalog sorbate salt characterized by one or two XRPD signals selected from the group consisting of 5.7 °2θ, and 11.4 °2θ (±0.2°2θ; ±0.1 °2θ; or 0.0 °2θ; Cu Kα1 radiation). In some embodiments, the solid form of Tabernanthalog sorbate salt is crystalline Tabernanthalog sorbate salt characterized by XRPD signals at 5.7 °2θ, and 11.4 °2θ (±0.2 °2θ; ±0.1 °2θ; or 0.0 °2θ; Cu Kα1 radiation).

In some embodiments, the crystalline Tabernanthalog sorbate salt is characterized by one or two XRPD signals selected from those set forth in Table 308.

In some embodiments, the solid form of Tabernanthalog sorbate salt is crystalline Tabernanthalog sorbate salt characterized by two or more, or three or more XRPD signals selected from the group consisting of 22.5 °2θ, 22.7 °2θ, and 7.6 °2θ (±0.2°2θ; ±0.1 °2θ; or ±0.0 °2θ; Cu Kα1 radiation).

In some embodiments, the solid form Tabernanthalog sorbate salt is crystalline Tabernanthalog sorbate salt characterized by XRPD signals at 22.5 °2θ, 22.7 °2θ, and 7.6 °2θ (±0.2 °2θ; ±0.1 °2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 22.5 °2θ, 22.7 °2θ, 7.6°2θ, 5.7 °2θ, and 22.6 °2θ (±0.2 °2θ; ±0.1°2θ; or 0.0 °2θ; Cu Kα1 radiation). In some embodiments, the solid form of Tabernanthalog sorbate salt is crystalline Tabernanthalog sorbate salt characterized by XRPD signals at 22.5 °2θ, 22.7 °2θ, 7.6 °2θ, 5.7 °2θ, and 22.6°2θ (±0.2 °2θ; ±0.1 °2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 22.5 °2θ, 22.7 °2θ, 7.6 °2θ, 5.7 °2θ, 22.6 °2θ, 17.1°2θ, and 13.3 °2θ(±0.2°2θ; ±0.1 °2θ; or 0.0 °2θ; Cu Kα1 radiation). In some embodiments, the solid form of Tabernanthalog sorbate salt is crystalline Tabernanthalog sorbate salt characterized by XRPD signals at 22.5 °2θ, 22.7 °2θ, 7.6 °2θ, 5.7 °2θ, 22.6 °2θ, 17.1 °2θ, and 13.3 °2θ (±0.2 °2θ; ±0.1 °2θ; or 0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 22.5 °2θ, 22.7 °2θ, 7.6 °2θ, 5.7 °2θ, 22.6 °2θ, 17.1 °2θ, 13.3 °2θ, 15.4 °2θ, 9.5 °2θ, and 11.5°2θ (±0.2 °2θ; ±0.1 °2θ; or ±0.0 °2θ; Cu Kα1 radiation). In some embodiments, the solid form of Tabernanthalog sorbate salt is crystalline Tabernanthalog sorbate salt characterized by XRPD signals at 22.5 °2θ, 22.7 °2θ, 7.6 °2θ, 5.7 °2θ, 22.6 °2θ, 17.1 °2θ, 13.3 °2θ, 15.4 °2θ, 9.5 °2θ, and 11.5 °2θ (±0.2 °2θ; 0.1 °2θ; or ±0.0 °2θ; Cu Kα1 radiation).

In some embodiments, the crystalline Tabernanthalog sorbate salt is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four XRPD signals selected from those set forth in Table 309.

In some embodiments, the solid form of Tabernanthalog sorbate salt is crystalline Tabernanthalog sorbate salt characterized by two or more, or three or more XRPD signals selected from the group consisting of 5.7 °2θ, 18.9 °2θ, and 24.7 °2θ (±0.2 °2θ; ±0.1 °2θ; or ±0.0 °2θ; Cu Kα1 radiation). In some embodiments, the solid form Tabernanthalog sorbate salt is crystalline Tabernanthalog sorbate salt characterized by XRPD signals 5.7 °2θ, 18.9 °2θ, and 24.7 °2θ (±0.2 °2θ; 0.1 °2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 5.7 °2θ, 18.9 °2θ, 24.7 °2θ, 11.4 °2θ, and 24.5 °2θ (±0.2 °2θ; ±0.1 °2θ; or 0.0 °2θ; Cu Kα1 radiation). In some embodiments, the solid form of Tabernanthalog sorbate salt is crystalline Tabernanthalog sorbate salt characterized by XRPD signals at 5.7 °2θ, 18.9 °2θ, 24.7 °2θ, 11.4 °2θ, and 24.5 °2θ (±0.2 °2θ; ±0.1 °2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 5.7 °2θ, 18.9 °2θ, 24.7 °2θ, 11.4 °2θ, 24.5 °2θ, 10.5 °2θ, and 22.6 °2θ (±0.2 °2θ;

±0.1 °2θ; or 0.0 °2θ; Cu Kα1 radiation). In some embodiments, the solid form of Tabernanthalog sorbate salt is crystalline Tabernanthalog sorbate salt characterized by XRPD signals at 5.7 °2θ, 18.9 °2θ, 24.7 °2θ, 11.4 °2θ, 24.5 °2θ, 10.5 °2θ, and 22.6 °2θ (±0.2 °2θ; ±0.1 °2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 5.7 °2θ, 18.9 °2θ, 24.7 °2θ, 11.4 °2θ, 24.5 °2θ, 10.5 °2θ, 22.6 °2θ, 19.1 °2θ, 17.9 °2θ, and 21.4 °2θ (±0.2 °2θ; ±0.1 °2θ; or ±0.0 °2θ; Cu Kα1 radiation). In some embodiments, the solid form of Tabernanthalog sorbate salt is crystalline Tabernanthalog sorbate salt characterized by XRPD signals at 5.7 °2θ, 18.9 °2θ, 24.7 °2θ, 11.4 °2θ, 24.5 °2θ, 10.5 °2θ, 22.6 °2θ, 19.1 °2θ, 17.9 °2θ, and 21.4°2θ (±0.2 °2θ; ±0.1 °2θ; or ±0.0 °2θ; Cu Kα1 radiation).

In some embodiments, the crystalline Tabernanthalog sorbate salt is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four XRPD signals selected from those set forth in Table 310.

In some embodiments, the solid form of Tabernanthalog sorbate salt is crystalline Tabernanthalog sorbate salt characterized by two or more, or three or more XRPD signals selected from the group consisting of 18.9 °2θ, 5.7 °2θ, and 10.5°2θ (±0.2°2θ; ±0.1°2θ; or 0.0 °2θ; Cu Kα1 radiation). In some embodiments, the solid form of Tabernanthalog sorbate salt is crystalline Tabernanthalog sorbate salt characterized by XRPD signals at 18.9 °2θ, 5.7 °2θ, and 10.5°2θ (±0.2°2θ; ±0.1 °2θ; or 0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 18.9 °2θ, 5.7 °2θ, 10.5 °2θ, 15.1 °2θ, and 27.4°2θ (±0.2°2θ; ±0.1 °2θ; or ±0.0 °2θ; Cu Kα1 radiation). In some embodiments, the solid form of Tabernanthalog sorbate salt is crystalline Tabernanthalog sorbate salt characterized by XRPD signals at 18.9 °2θ, 5.7 °2θ, 10.5 °2θ, 15.1 °2θ, and 27.4°2θ (±0.2°2θ; ±0.1°2θ; or 0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 18.9 °2θ, 5.7 °2θ, 10.5 °2θ, 15.1 °2θ, 27.4 °2θ, 18.0 °2θ, and 24.7°2θ (±0.2°2θ; ±0.1°2θ; or ±0.0 °2θ; Cu Kα1 radiation). In some embodiments, the solid form of Tabernanthalog sorbate salt is crystalline Tabernanthalog sorbate salt characterized by XRPD signals at 18.9 °2θ, 5.7 °2θ, 10.5 °2θ, 15.1 °2θ, 27.4 °2θ, 18.0 °2θ, and 24.7 °2θ (±0.2°2θ; ±0.1 °2θ; or ±0.0 °2θ; Cu Kα1 radiation).

In some embodiments, the crystalline Tabernanthalog sorbate salt is characterized by one, two, three, four, five, six, or seven XRPD signals selected from those set forth in Table 311.

In some embodiments, the solid form of Tabernanthalog sorbate salt is crystalline Tabernanthalog sorbate salt characterized by two or more, or three or more XRPD signals selected from the group consisting of 5.7 °2θ, 18.9 °2θ, and 10.5°2θ (±0.2°2θ; ±0.1°2θ; or ±0.0 °2θ; Cu Kα1 radiation). In some embodiments, the solid form Tabernanthalog sorbate salt is crystalline Tabernanthalog sorbate salt characterized by XRPD signals 5.7 °2θ, 18.9 °2θ, and 10.5 °2θ°2θ (±0.2°2θ; ±0.1 °2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 5.7 °2θ, 18.9 °2θ, 10.5 °2θ, 11.5 °2θ, and 24.7°2θ (±0.2 °2θ; ±0.1 °2θ; or 0.0 °2θ; Cu Kα1 radiation). In some embodiments, the solid form of Tabernanthalog sorbate salt is crystalline Tabernanthalog sorbate salt characterized by XRPD signals at 5.7 °2θ, 18.9 °2θ, 10.5 °2θ, 11.5 °2θ, and 24.7°2θ (±0.2°2θ; ±0.1°2θ; or 0.0 °2θ; Cu Kα1 radiation).

In some embodiments, the solid form of Tabernanthalog sorbate salt s crystalline Tabernanthalog sorbate salt characterized by two or more, or three or more XRPD signals selected from the group consisting of 5.7 °2θ, 18.9 °2θ, 10.5 °2θ, 11.5 °2θ, 24.7 °2θ, 18.0 °2θ, 24.6 °2θ (±0.2°2θ; ±0.1°2θ; or 0.0 °2θ; Cu Kα1 radiation). In some embodiments, the solid form of Tabernanthalog sorbate salt is crystalline Tabernanthalog sorbate salt characterized by XRPD signals at 5.7 °2θ, 18.9 °2θ, 10.5 °2θ, 11.5 °2θ, 24.7 °2θ, 18.0 °2θ, 24.6 °2θ (±0.2 °2θ; ±0.1°2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 5.7 °2θ, 18.9 °2θ, 10.5 °2θ, 11.5 °2θ, 24.7 °2θ, 18.0 °2θ, 24.6 °2θ, 19.2 °2θ, 18.4 °2θ, and 22.7°2θ (±0.2 °2θ; ±0.1 °2θ; or 0.0 °2θ; Cu Kα1 radiation). In some embodiments, the solid form of Tabernanthalog sorbate salt is crystalline Tabernanthalog sorbate salt characterized by XRPD signals at 5.7 °2θ, 18.9°2θ, 10.5 °2θ, 11.5 °2θ, 24.7 °2θ, 18.0 °2θ, 24.6 °2θ, 19.2 °2θ, 18.4 °2θ, and 22.7 °2θ (±0.2 °2θ; ±0.1 °2θ; or ±0.0 °2θ; Cu Kα1 radiation).

In some embodiments, the crystalline Tabernanthalog sorbate salt is characterized by one, two, three, four, five, six, seven, eight, nine, ten, eleven, twelve, thirteen, fourteen, or fifteen XRPD signals selected from those set forth in Table 312.

In some embodiments, the solid form of Tabernanthalog sorbate salt is crystalline Tabernanthalog sorbate salt characterized by two or more, or three or more XRPD signals selected from the group consisting of 18.9 °2θ, 5.7 °2θ, and 24.7 °2θ (±0.2 °2θ; ±0.1 °2θ; or ±0.0 °2θ; Cu Kα1 radiation). In some embodiments, the solid form Tabernanthalog sorbate salt is crystalline Tabernanthalog sorbate salt characterized by XRPD signals 18.9 °2θ, 5.7 °2θ, and 24.7 °2θ (±0.2 °2θ; ±0.1 °2θ; or 0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 18.9 °2θ, 5.7 °2θ, 24.7 °2θ, 19.1 °2θ, and 10 5 °2θ (±0.2 °2θ; ±0.1 °2θ; or ±0.0 °2θ; Cu Kα1 radiation). In some embodiments, the solid form of Tabernanthalog sorbate salt is crystalline Tabernanthalog sorbate salt characterized by XRPD signals at 18.9 °2θ, 5.7 θ2θ, 24.7 °2θ, 19.1 °2θ, and 10.5 °2θ (±0.2 °2θ; ±0.1 °2θ; or ±0.0 °2θ; Cu Kα1 radiation).

In some embodiments, the solid form of Tabernanthalog sorbate salt s crystalline Tabernanthalog sorbate salt characterized by two or more, or three or more XRPD signals selected from the group consisting of 18.9 °2θ, 5.7 °2θ, 24.7 °2θ, 19.1 °2θ, 10.5 °2θ, 18.4 °2θ, and 18 °2θ (±0.2 °2θ; ±0.1 °2θ; or 0.0 °2θ; Cu Kα1 radiation). In some embodiments, the solid form of Tabernanthalog sorbate salt is crystalline Tabernanthalog sorbate salt characterized by XRPD signals at 18.9 °2θ, 5.7 °2°, 24.7 °2θ, 19.1 °2θ, 10.5 °2θ, 18.4 °2θ, and 18 °2θ (±0.2 °2θ; ±0.1 °2θ; or ±0.0 °2θ; Cu Kα1 radiation).

In some embodiments, the solid form of Tabernanthalog sorbate salt is crystalline Tabernanthalog sorbate salt characterized by two or more, or three or more XRPD signals selected from the group consisting of 18.9 °2θ, 5.7 °2θ, 24.7 °2θ, 19.1 °2θ, 10.5 °2θ, 18.4 °2θ, 18 °2θ, 11.4 °2θ, 24.5 °2θ, and 22.6 °2θ (±0.2 °2θ; ±0.1 °2θ; or ±0.0 °2θ; Cu Kα1 radiation). In some embodiments, the solid form of Tabernanthalog sorbate salt is crystalline Tabernanthalog sorbate salt characterized by XRPD signals at 18.9 °2θ, 5.7 °2θ, 24.7 °2θ, 19.1 °2θ, 10.5 °2θ, 18.4 °2θ, 18 °2θ, 11.4 °2θ, 24.5 °2θ, and 22.6 °2θ (±0.2 °2θ; ±0.1 °2θ; or ±0.0 °2θ; Cu Kα1 radiation).

In some embodiments, the crystalline Tabernanthalog sorbate salt is characterized by one, two, three, four, five, six, seven, eight, nine, ten, eleven, twelve, thirteen, fourteen, fifteen, sixteen, or seventeen XRPD signals selected from those set forth in Table 313.

In some embodiments, the solid form of Tabernanthalog monofumarate salt is crystalline Tabernanthalog monofumarate salt characterized by two or more, or three or more XRPD signals selected from the group consisting of 16.3 °2θ, 9.1 °2θ, and 25.6 °2θ (±0.2 °2θ; ±0.1°2θ; or ±0.0 °2θ; Cu Kα1 radiation). In some embodiments, the solid form Tabernanthalog monofumarate salt is crystalline Tabernanthalog monofumarate salt characterized by XRPD signals 16.3 °2θ, 9.1 °2θ, and 25.6 °2θ (±0.2 °2θ; ±0.1 °2θ; or ±0.0 °2θ; Cu Kα1 radiation).

In some embodiments, the solid form of Tabernanthalog monofumarate salt is crystalline Tabernanthalog monofumarate salt characterized by two or more, or three or more XRPD signals selected from the group consisting of 16.3 °2θ, 9.1°2θ, 25.6 °2θ, 19.3 °2θ, and 26.8 °2θ (±0.2 °2θ; ±0.1 °2θ; or ±0.0 °2θ; Cu Kα1 radiation). In some embodiments, the solid form of Tabernanthalog monofumarate salt is crystalline Tabernanthalog monofumarate salt characterized by XRPD signals at 16.3 θ2θ, 9.1 °2θ, 25.6 °2θ, 19.3 °2θ, and 26.8 °2θ (±0.2 °2θ; ±0.1 °2θ; or 0.0 °2θ; Cu Kα1 radiation).

In some embodiments, the solid form of Tabernanthalog monofumarate salt s crystalline Tabernanthalog monofumarate salt characterized by two or more, or three or more XRPD signals selected from the group consisting of 16.3 °2θ, 9.1 °2θ, 25.6 °2θ, 19.3 °2θ, 26.8 °2θ, 25.1 °2θ, and 16.7 °2θ(±0.2 °2θ; ±0.1 °2θ; or 0.0 °2θ; Cu Kα1 radiation). In some embodiments, the solid form of Tabernanthalog monofumarate salt is crystalline Tabernanthalog monofumarate salt characterized by XRPD signals at 16.3 °2θ, 9.1 °2θ, 25.6 °2θ, 19.3 °2θ, 26.8 °2θ, 25.1 °2θ, and 16.7 °2θ (±0.2 °2θ; ±0.1 °2θ; or 0.0 °2θ; Cu Kα1 radiation).

In some embodiments, the solid form of Tabernanthalog monofumarate salt is crystalline Tabernanthalog monofumarate salt characterized by two or more, or three or more XRPD signals selected from the group consisting of 16.3 °2θ, 9.1 °2θ, 25.6 °2θ, 19.3 °2θ, 26.8 °2θ, 25.1 °2θ, 16.7 °2θ, 18.1 °2θ, 22.3 °2θ, and 27.2 °2θ (±0.2 °2θ; ±0.1 °2θ; or 0.0 °2θ; Cu Kα1 radiation). In some embodiments, the solid form of Tabernanthalog monofumarate salt is crystalline Tabernanthalog monofumarate salt characterized by XRPD signals at 16.3 °2θ, 9.1 °2θ, 25.6 °2θ, 19.3 °2θ, 26.8 °2θ, 25.1 °2θ, 16.7 °2θ, 18.1 °2θ, 22.3 °2θ, and 27.2 °2θ (±0.2 °2θ; ±0.1 °2θ; or ±0.0 °2θ; Cu Kα1 radiation).

In some embodiments, the crystalline Tabernanthalog monofumarate salt is characterized by one, two, three, four, five, six, seven, eight, nine, ten, eleven, or twelve XRPD signals selected from those set forth in Table 314.

In some embodiments, the solid form of Tabernanthalog monofumarate salt is crystalline Tabernanthalog monofumarate salt characterized by two or more, or three or more XRPD signals selected from the group consisting of 7.4 °2θ, 21.5 °2θ, and 16.0 °2θ (±0.2 °2θ; ±0.1 °2θ; or 0.0 °2θ; Cu Kα1 radiation). In some embodiments, the solid form Tabernanthalog monofumarate salt is crystalline Tabernanthalog monofumarate salt characterized by XRPD signals 7.4 °2θ, 21.5 °2θ, and 16.0 °2θ (±0.2 °2θ; ±0.1 °2θ; or ±0.0 °2θ; Cu Kα1 radiation).

In some embodiments, the solid form of Tabernanthalog monofumarate salt is crystalline Tabernanthalog monofumarate salt characterized by two or more, or three or more XRPD signals selected from the group consisting of 7.4 °2θ, 21.5 °2θ, 16.0 °2θ, 20.3 °2θ, and 25.7 °2θ (±0.2 °2θ; ±0.1 °2θ; or ±0.0 °2θ; Cu Kα1 radiation). In some embodiments, the solid form of Tabernanthalog monofumarate salt is crystalline Tabernanthalog monofumarate salt characterized by XRPD signals at 7.4 °2θ, 21.5 °2θ, 16.0 °2θ, 20 3°2θ, and 25.7 °2θ (±0.2 °2θ; ±0.1°2θ; or 0.0 °2θ; Cu Kα1 radiation).

In some embodiments, the solid form of Tabernanthalog monofumarate salt s crystalline Tabernanthalog monofumarate salt characterized by two or more, or three or more XRPD signals selected from the group consisting of 7.4 °2θ, 21.5 °2θ, 16.0°2θ, 20.3°2θ, 257 °2θ, and 20.8 °2θ (±0.2 °2θ; ±0.1°2θ; or 0.0 °2θ; Cu Kα1 radiation). In some embodiments, the solid form of Tabernanthalog monofumarate salt is crystalline Tabernanthalog monofumarate salt characterized by XRPD signals at 7.4 °2θ, 21.5 °2θ, 16.0 °2θ, 20.3 °2θ, 25.7 °2θ, and 20.8 °2θ (±0.2 °2θ; ±0.1 °2θ; or 0.0 °2θ; Cu Kα1 radiation).

In some embodiments, the crystalline Tabernanthalog monofumarate salt is characterized by one, two, three, four, five, or six XRPD signals selected from those set forth in Table 315.

In some embodiments, the solid form of Tabernanthalog monofumarate salt is crystalline Tabernanthalog monofumarate salt characterized by two or more, or three or more XRPD signals selected from the group consisting of 8.2°2θ, 11.2°2θ, and 17.1 °2θ (±0.2 °2θ; ±0.1°2θ; or ±0.0 °2θ; Cu Kα1 radiation). In some embodiments, the solid form Tabernanthalog monofumarate salt is crystalline Tabernanthalog monofumarate salt characterized by XRPD signals 8.2 °2θ, 11.2°2θ, and 17.1 °2θ (±0.2 °2θ; ±0.1 °2θ; or ±0.0 °2θ; Cu Kα1 radiation).

In some embodiments, the solid form of Tabernanthalog monofumarate salt is crystalline Tabernanthalog monofumarate salt characterized by two or more, or three or more XRPD signals selected from the group consisting of 8.2 °2θ, 11.2 °2θ, 17.1 °2θ, 24.4°2θ, and 23.8 °2θ (±0.2 °2θ; ±0.1 °2θ; or ±0.0 °2θ; Cu Kα1 radiation). In some embodiments, the solid form of Tabernanthalog monofumarate salt is crystalline Tabernanthalog monofumarate salt characterized by XRPD signals at 8.2 °2θ, 11.2°2θ, 17.1 °2θ, 24.4 °2θ, and 23.8 °2θ (±0.2 °2θ; ±0.1 °2θ; or 0.0 °2θ; Cu Kα1 radiation).

In some embodiments, the solid form of Tabernanthalog monofumarate salt s crystalline Tabernanthalog monofumarate salt characterized by two or more, or three or more XRPD signals selected from the group consisting of 8.2 °2θ, 11.2 °2θ, 17.1°2θ, 24.4 °2θ, 23.8 °2θ, 21.5 °2θ, and 20.2 °2θ (±0.2 °2θ; ±0.1°2θ; or 0.0 °2θ; Cu Kα1 radiation). In some embodiments, the solid form of Tabernanthalog monofumarate salt is crystalline Tabernanthalog monofumarate salt characterized by XRPD signals at 8.2 °2θ, 11.2°2θ, 17.1

°2θ, 24.4 °2θ, 23.8°2θ, 21.5 °2θ, and 20.2 °2θ(±0.2 °2θ; ±0.1 °2θ; or 0.0 °2θ; Cu Kα1 radiation).

In some embodiments, the solid form of Tabernanthalog monofumarate salt is crystalline Tabernanthalog monofumarate salt characterized by two or more, or three or more XRPD signals selected from the group consisting of 8.2 °2θ, 11.2 °2θ, 17.1°2θ, 24.4 °2θ, 23.8° 2θ, 21.5 °2θ, 20.2 °2θ, and 8.9°2θ (±0.2 °2θ; ±0.1 °2θ; or ±0.0 °2θ; Cu Kα1 radiation). In some embodiments, the solid form of Tabernanthalog monofumarate salt is crystalline Tabernanthalog monofumarate salt characterized by XRPD signals at 8.2 °2θ, 11.2 °2θ, 17.1 °2θ, 24.4°2θ, 23.8 °2θ, 21.5 °2θ, 20.2 °2θ, and 8.9 °2θ (±0.2 °2θ; ±0.1°2θ; or 0.0 °2θ; Cu Kα1 radiation).

In some embodiments, the crystalline Tabernanthalog monofumarate salt is characterized by one, two, three, four, five, six, seven, or eight XRPD signals selected from those set forth in Table 316.

In some embodiments, Form A of the tabernanthalog sorbate salt is obtained from heat-up/cool-down crystallization of tabernanthalog (native) with sorbic acid in ethanol (5.0 vol) at 85° C.

The product was isolated by centrifugation and was oven-dried under reduced pressure over 20 h at 40° C.

In yet other embodiments, Form A of the tabernanthalog sorbate salt is obtained heat-up/cool-down crystallization of tabernanthalog (native) with sorbic acid in ethanol (3.0 vol) and the salt is isolated by filtration and dried under sustained nitrogen flux (<1 bar) over 20 h at 20° C.

In one embodiment, Form A of the tabernanthalog sorbate salt is a unary sorbate with 24.7% w/w th., sorbic acid (i.e., 1.0 mol of API to 1.0 mol sorbic acid).

In one embodiment, Form A of the tabernanthalog sorbate salt is crystalline characterized by two or more, or three XRPD signals selected from the group consisting of 5.7 °2θ, 11.4 °2θ, 24.7 °2θ, 18.8 °2θ, 10.5 °2θ, 22.6 °2θ, 24.4 °2θ, 26.9 °2θ, 19.1 °2θ, 21.4 °2θ, 17.9 °2θ, and 22.9 °2θ (±0.2 °2θ; ±0.1 °2θ; or ±0.0 °2θ; Cu Kα1 radiation).

In one embodiment, Form A of the tabernanthalog sorbate salt is crystalline characterized by two or more, or three XRPD signals selected from the group consisting of 5.7 °2θ, 11.4 °2θ, 24.7 °2θ, 18.8 °2θ, 10.5 °2θ, 22.6 °2θ, 24.4 °2θ, 26.9 °2θ, 19.1°2θ, 21.4 °2θ, and 17.9 °2θ (±0.2 °2θ; ±0.1 °2θ; or 0.0 °2θ: Cu Kα1 radiation).

In one embodiment, Form A of the tabernanthalog sorbate salt is crystalline characterized by two or more, or three XRPD signals selected from the group consisting of 5.7 °2θ, 11.4 °2θ, 24.7 °2θ, 18.8 °2θ, 10.5 °2θ, 22.6 °2θ, 24.4 °2θ, 26.9 °2θ, 19.1 °2θ, and 21.4 °2θ (±0.2 °2θ; ±0.1 °2θ; or ±0.0 °2θ; Cu Kα1 radiation).

In one embodiment, Form A of the tabernanthalog sorbate salt is crystalline characterized by two or more, or three XRPD signals selected from the group consisting of 5.7 °2θ, 11.4 °2θ, 24.7 °2θ, 18.8 °2θ, 10.5 °2θ, 22.6 °2θ, 24.4 °2θ, 26.9 °2θ, and 19.1 °2θ (±0.2 °2θ; ±0.1°2θ; or ±0.0 °2θ; Cu Kα1 radiation).

In one embodiment, Form A of the tabernanthalog sorbate salt is crystalline characterized by two or more, or three XRPD signals selected from the group consisting of 5.7 °2θ, 11.4 °2θ, 24.7 °2θ, 18.8 °2θ, 10.5 °2θ, 22.6 °2θ, 24.4 °2θ, and 26.9 °2θ (±0.2 °2θ; ±0.1 °2θ; or ±0.0 °2θ; Cu Kα1 radiation).

In one embodiment, Form A of the tabernanthalog sorbate salt is crystalline characterized by two or more, or three XRPD signals selected from the group consisting of 5.7 °2θ, 11.4 °2θ, 24.7 °2θ, 18.8 °2θ, 10.5 °2θ, and 22.6 °2θ (±0.2 °2θ; ±0.1°2θ; or ±0.0 °2θ; Cu Kα1 radiation).

In one embodiment, Form A of the tabernanthalog sorbate salt is crystalline characterized by two or more, or three XRPD signals selected from the group consisting of 5.7 °2θ, 11.4 °2θ, 24.7 °2θ, 18.8 °2θ, and 10.5°2θ (±0.2°2θ; ±0.1 °2θ; or 0.0 °2θ; Cu Kα1 radiation).

In one embodiment, Form A of the tabernanthalog sorbate salt is crystalline characterized by two or more, or three XRPD signals selected from the group consisting of 5.7 °2θ, 11.4 °2θ, 24.7 °2θ, and 18.8°2θ (±0.2 °2θ; ±0.1 °2θ; or 0.0 °2θ; Cu Kα1 radiation).

In one embodiment, Form A of the tabernanthalog sorbate salt is crystalline characterized by two or more, or three XRPD signals selected from the group consisting of 5.7 °2θ, 11.4 °2θ, and 24.7°2θ (±0.2°2θ; ±0.1°2θ; or ±0.0 °2θ; Cu Kα1 radiation).

In one embodiment, Form A of the tabernanthalog sorbate salt is crystalline characterized XRPD signals at 5.7 °2θ, 11.4°2θ, 24.7 °2θ, 18.8 °2θ, 10.5 °2θ, 22.6 °2θ, 24.4 °2θ, 26.9 °2θ, 19.1 °2θ, 21.4 °2θ, 17.9 °2θ, and 22.9 °2θ (±0.2 °2θ; ±0.1°2θ; or 0.0 °2θ; Cu Kα1 radiation).

In one embodiment, Form A of the tabernanthalog sorbate salt is crystalline characterized by XRPD signals at 5.7 °2θ, 11.4 °2θ, 24.7 °2θ, 18.8 °2θ, 10.5 °2θ, 22.6 °2θ, 24.4 °2θ, 26.9 °2θ, 19.1 °2θ, 21.4 °2θ, and 17.9 °2θ (0.2 °2θ; ±0.1 °2θ; or 0.0 °2θ; Cu Kα1 radiation).

In one embodiment, Form A of the tabernanthalog sorbate salt is crystalline characterized by XRPD signals at 5.7 °2θ, 11.4 °2θ, 24.7 °2θ, 18.8 °2θ, 10.5 °2θ, 22.6 °2θ, 24.4 °2θ, 26.9 °2θ, 19.1 °2θ, and 21.4 °2θ (±0.2 °2θ; ±0.1°2θ; or ±0.0 °2θ; Cu Kα1 radiation).

In one embodiment, Form A of the tabernanthalog sorbate salt is crystalline characterized by XRPD signals at 5.7 °2θ, 11.4°2θ, 24.7 °2θ, 18.8 °2θ, 10.5 °2θ, 22.6 °2θ, 24.4 °2θ, 26.9 °2θ, and 19.1°2θ (±0.2°2θ; ±0.1 °2θ; or 0.0 °2θ; Cu Kα1 radiation).

In one embodiment, Form A of the tabernanthalog sorbate salt is crystalline characterized by XRPD signals at 5.7 °2θ, 11.4 °2θ, 24.7 °2θ, 18.8 °2θ, 10.5 °2θ, 22.6 °2θ, 24.4 °2θ, and 26.9 °2θ (±0.2°2θ; ±0.1 °2θ; or ±0.0 °2θ; Cu Kα1 radiation).

In one embodiment, Form A of the tabernanthalog sorbate salt is crystalline characterized by XRPD signals at 5.7 °2θ, 11.4 °2θ, 24.7 °2θ, 18.8 °2θ, 10.5 °2θ, 22.6 °2θ, and 24.4 °2θ (±0.2°2θ; ±0.1°2θ; or 0.0 °2θ; Cu Kα1 radiation).

In one embodiment, Form A of the tabernanthalog sorbate salt is crystalline characterized by XRPD signals at 5.7 °2θ, 11.4 °2θ, 24.7 °2θ, 18.8 °2θ, 10.5 °2θ, and 22.6°2θ (±0.2°2θ; ±0.1°2θ; or ±0.0 °2θ; Cu Kα1 radiation).

In one embodiment, Form A of the tabernanthalog sorbate salt is crystalline characterized by XRPD signals at 5.7 °2θ, 11.4 °2θ, 24.7 °2θ, 18.8 °2θ, and 10.5 °2θ (±0.2 °2θ; ±0.1°2θ; or 0.0 °2θ; Cu Kα1 radiation).

In one embodiment, Form A of the tabernanthalog sorbate salt is crystalline characterized by XRPD signals at 5.7 °2θ, 11.4 °2θ, 24.7 °2θ, and 18.8 °2θ (±0.2°2θ; ±0.1°2θ; or 0.0 °2θ; Cu Kα1 radiation).

In one embodiment, Form A of the tabernanthalog sorbate salt is crystalline characterized by XRPD signals at 5.7 °2θ, 11.4 °2θ, and 24.7 °2θ (±0.2°2θ; ±0.1°2θ; or ±0.0 °2θ; Cu Kα1 radiation).

In some embodiments, Form A of the tabernanthalog sorbate salt is crystalline characterized two or more, or three XRPD signals as shown in Table 216.

In some embodiments, Form A of the tabernanthalog sorbate salt is crystalline characterized two or more, or three XRPD signals as shown in FIG. 384.

In some embodiments, Form A of the tabernanthalog sorbate salt exhibits an $^1$H NMR spectrum as depicted in FIG. 451, FIG. 561, or FIG. 562.

In some embodiments, Form A of the tabernanthalog sorbate salt exhibits a DSC profile as depicted in FIG. 453.

In some embodiments, Form A of the tabernanthalog sorbate salt exhibits a TGA profile as depicted in FIG. 454.

In some embodiments, Form A of the tabernanthalog sorbate salt exhibits a DVS profile as depicted in FIG. 455 or FIG. 456.

In some embodiments, Form A of the tabernanthalog sorbate salt exhibits an XRPD pattern as depicted in FIG. 384.

In some embodiments, Form A of the tabernanthalog sorbate salt exhibits an XRPD pattern post DVS as depicted in FIG. 458.

In some embodiments, Form A of the tabernanthalog sorbate salt exhibits an HPLC spectrum as depicted in FIG. 460 or FIG. 566.

In some embodiments, Form A of the tabernanthalog sorbate salt exhibits at least one property as listed in Table 192.

In some embodiments, the solid form of Tabernanthalog·Sorbate (Form A) is crystalline Tabernanthalog·Sorbate (Form A) characterized by two or more, or three or more XRPD signals selected from the group consisting of 19.1 °2θ, 25.0 °2θ, and 5.8 °2θ (±0.2 °2θ; ±0.1 °2θ; or 0.0 °2θ; Cu Kα1 radiation). In some embodiments, the solid form of Tabernanthalog·Sorbate (Form A) is crystalline Tabernanthalog·Sorbate (Form A) characterized by XRPD signals at 19.1 °2θ, 25.0 °2θ, and 5.8 °2θ (±0.2 °2θ; ±0.1 °2θ; or ±0.0 °2θ; Cu Kα1 radiation).

In some embodiments, the solid form of Tabernanthalog·Sorbate (Form A) is crystalline Tabernanthalog·Sorbate (Form A) characterized by two or more, or three or more XRPD signals selected from the group consisting of 19.1 °2θ, 25.0 °2θ, 5.8 °2θ, 10.7 °2θ, and 22.9 °2θ (±0.2 °2θ; ±0.1 °2θ; or 0.0 °2θ; Cu Kα1 radiation). In some embodiments, the solid form of Tabernanthalog·Sorbate (Form A) is crystalline Tabernanthalog·Sorbate (Form A) characterized by XRPD signals at 19.1 °2θ, 25.0 °2θ, 5.8 °2θ, 10.7 °2θ, and 22.9 °2θ (±0.2 °2θ; ±0.1 °2θ; or 0.0 °2θ; Cu Kα1 radiation).

In some embodiments, the solid form of Tabernanthalog·Sorbate (Form A) is crystalline Tabernanthalog·Sorbate (Form A) characterized by two or more, or three or more XRPD signals selected from the group consisting of 19.1 °2θ, 25.0 °2θ, 5.8 °2θ, 10.7 °2θ, 22.9 °2θ, 18.1 °2θ, and 24.7 °2θ (±0.2 °2θ; ±0.1 °2θ; or 0.0 °2θ; Cu Kα1 radiation). In some embodiments, the solid form of Tabernanthalog·Sorbate (Form A) is crystalline Tabernanthalog·Sorbate (Form A) characterized by XRPD signals at 19.1 °2θ, 25.0 °2θ, 5.8 °2θ, 10.7 °2θ, 22.9 °2θ, 18.1 °2θ, and 24.7°2θ (±0.2 °2θ; ±0.1°2θ; or 0.0 °2θ; Cu Kα1 radiation).

In some embodiments, the solid form of Tabernanthalog·Sorbate (Form A) is crystalline Tabernanthalog·Sorbate (Form A) characterized by two or more, or three or more XRPD signals selected from the group consisting of 19.1 °2θ, 25.0 °2θ, 5.8 °2θ, 10.7 °2θ, 22.9 °2θ, 18.1 °2θ, 24.7 °2θ, 11.6 °2θ, 21.7 °2θ, and 27.3°2θ (±0.2°2θ; ±0.1°2θ; or ±0.0 °2θ; Cu Kα1 radiation). In some embodiments, the solid form of Tabernanthalog·Sorbate (Form A) is crystalline Tabernanthalog·Sorbate (Form A) characterized by XRPD signals at 19.1 °2θ, 25.0 °2θ, 5.8 °2θ, 10.7 °2θ, 22.9 °2θ, 18.1 °2θ, 24.7 °2θ, 11.6 °2θ, 21.7 °2θ, and 27.3°2θ (±0.2°2θ; ±0.1°2θ; or ±0.0 °2θ; Cu Kα1 radiation).

In some embodiments, the crystalline Tabernanthalog·Sorbate (Form A) is characterized by one, two, three, four, five, six, seven, eight, nine, ten, eleven, twelve, thirteen, fourteen, fifteen, sixteen, seventeen, eighteen, or nineteen XRPD signals selected from those as set forth in Table 293B.

In some embodiments, the solid form of Tabernanthalog·Sorbate·H$_2$O is crystalline Tabernanthalog·Sorbate·H$_2$O characterized by two or more, or three or more XRPD signals selected from the group consisting of 22.7 °2θ, 5.8 °2θ, and 17.0°2θ (±0.2 °2θ; ±0.1 °2θ; or 0.0 °2θ; Cu Kα1 radiation). In some embodiments, the solid form of Tabernanthalog·Sorbate·H$_2$O is crystalline Tabernanthalog·Sorbate·H$_2$O characterized by XRPD signals at 22.7 °2θ, 5.8 °2θ, and 17.0°2θ (±0.2°2θ; ±0.1 °2θ; or ±0.0 °2θ; Cu Kα1 radiation).

In some embodiments, the solid form of Tabernanthalog·Sorbate·H$_2$O is crystalline Tabernanthalog·Sorbate·H$_2$O characterized by two or more, or three or more XRPD signals selected from the group consisting of 22.7 °2θ, 5.8 °2θ, 17.0 °2θ, 18.7 °2θ, and 17.9°2θ (±0.2 °2θ; ±0.1 °2θ; or 0.0 °2θ; Cu Kα1 radiation). In some embodiments, the solid form of Tabernanthalog·Sorbate·H$_2$O is crystalline Tabernanthalog·Sorbate·H$_2$O characterized by XRPD signals at 22.7 °2θ, 5.8 °2θ, 17.0 °2θ, 18.7 °2θ, and 17.9°2θ (±0.2°2θ; ±0.1°2θ; or 0.0 °2θ; Cu Kα1 radiation).

In some embodiments, the solid form of Tabernanthalog·Sorbate·H$_2$O is crystalline Tabernanthalog·Sorbate·H$_2$O characterized by two or more, or three or more XRPD signals selected from the group consisting of 22.7 °2θ, 5.8 °2θ, 17.0 °2θ, 18.7 °2θ, 17.9 °2θ, 30.0 °2θ, and 11.3 °2θ (±0.2°2θ; ±0.1°2θ; or ±0.0 °2θ; Cu Kα1 radiation). In some embodiments, the solid form of Tabernanthalog·Sorbate·H$_2$O is crystalline Tabernanthalog·Sorbate·H$_2$O characterized by XRPD signals at 22.7 °2θ, 5.8 °2θ, 17.0 °2θ, 18.7 °2θ, 17.9 °2θ, 30.0 °2θ, and 11.3°2θ (±0.2°2θ; ±0.1°2θ; or ±0.0 °2θ; Cu Kα1 radiation).

In some embodiments, the solid form of Tabernanthalog·Sorbate·H$_2$O is crystalline Tabernanthalog·Sorbate·H$_2$O characterized by two or more, or three or more XRPD signals selected from the group consisting of 22.7 °2θ, 5.8 °2θ, 17.0 °2θ, 18.7 °2θ, 17.9 °2θ, 30.0 °2θ, 11.3 °2θ, 17.4 °2θ, 18.9 °2θ, and 11.7°2θ (±0.2°2θ; ±0.1°2θ; or ±0.0 °2θ; Cu Kα1 radiation). In some embodiments, the solid form of Tabernanthalog·Sorbate·H$_2$O is crystalline Tabernanthalog·Sorbate·H$_2$O characterized by XRPD signals at 22.7 °2θ, 5.8 °2θ, 17.0 °2θ, 18.7 °2θ, 17.9 °2θ, 30.0 °2θ, 11.3 °2θ, 17.4 °2θ, 18.9 °2θ, and 11.7020 (±0.2°2θ; ±0.1 °2θ; or ±0.0 °2θ; Cu Kα1 radiation).

In some embodiments, the crystalline Tabernanthalog·Sorbate·H$_2$O is characterized by one, two, three, four, five, six, seven, eight, nine, ten, eleven, twelve, thirteen, fourteen, fifteen, sixteen, or seventeen XRPD signals selected from those as set forth in Table 294B.

In one embodiment, the tabernanthalog sorbate salt is characterized by one of the following properties: (1) show minimal reduction in CP (from 99.76% area to 99.70% area), (2) is highly soluble in the SIF buffers (apart from FaSSGF), (3) exhibits higher crystallographic quality than the tabernanthalog fumarate salt, (4) has better solvent and impurity rejection on scale-up.

In some embodiments, the tabernanthalog sorbate salt (Form I) is characterized by at least one of the following properties:
- (a) 24.7% w/w th., sorbic acid (i.e., 1.0 mol of API to 1.0 mol sorbic acid);
- (b) hydrogen bonding between both oxygen molecules on the sorbate ion. One to N1 (tryptamine nitrogen atom) of one API molecules, the other to N2 (hydro-azepine nitrogen atom) of a separate API molecule. Due to hydrogen bonding present in the structure builds up chains between API and salt molecule. Causing stacking of API and sorbate molecules closely packed to one another. This leads to less free space in the crystal structure and void radius of only ~0.9 A, much smaller than the 1.4 required for a water molecule to occupy. Bond between Sorbates and API, N1-O3, 2.857 Å (hydrogen bond), N2-O2, 2.7015 Å (salification hydrogen bond) N1=Indole, N2=Hydroazepine. Sorbate molecule is disordered and bond lengths stated are an average of the two mapped positions;
- (c) Crystal system 100(2) K: monoclinic
  Space group 100(2) K: P2$_1$/c
  Unit cell 100(2) K: a=9.3410(3) Å, b=6.4173(2) Å, c=30.5108(12) Å. A=γ=90° β=95.374(3)°, V=1820.90(11) Å3
  Asymmetric unit: contains one API molecule one sorbate ion;
- (d) XRPD: 5.7°, 10.5θ, 11.4°, 17.9°, 18.8°, 19.1°, 21.4°, 22.6°, 22.9θ, 24.4θ, 24.7°, 26.8° (2θ, 1 d.p) as shown in FIG. 384 and Table 216;
- (e) DSC: onset 143.9° C. (−84.1 Jg$^{-1}$, endotherm, melt) as shown in FIG. 453;
- (f) TGA: onset 171.8° C. (−26.0% w/w, ablation) 250.0° C. (−19.9% w/w, ablation) as shown in FIG. 454;
- (g) DVS 0 to 90 to 0% RH (dm/dt<0.002%): 0.0 (0.00%), 5.0 (0.0%), 10.0 (0.01%), 15.0 (0.01%), 20.0 (0.02%), 25.0 (0.03%), 30.0 (0.03%), 40.0 (0.05%), 50.0 (0.07%), 60.0 (0.10%), 70.0 (0.14%), 80.0 (0.21%), 90.0 (0.98%), 90.0 (0.98%), 80.0 (0.48%), 70.0 (0.30%), 60.0 (0.18%), 50.0 (0.06%), 40.0 (0.03%), 30.0 (0.00%), 25.0 (−0.007%), 20.0 (−0.02%), 15.0 (−0.03%), 10.0 (−0.04%), 5.0 (−0.05%), 0.0 (−0.06%) as shown in FIGS. 455 and 456;
- (h) UV chromatographic purity: 99.64% area (212 nm) as shown in FIG. 566.
- (i) $^1$H NMR: (DMSO-d6, 400 MHz); δ 10.4 (s, 1H), 7.2 (d, J=9.4 Hz, 1H), 7.1 (dd, J=15.4, 9.6 Hz 1H), 6.7 (d, 1=2.3 Hz, 1H), 6.6 (dd, J=8.5, 2.2 Hz, 1H), 6.3-6.2 (m, 2H), 5.8 (d, J=15.4 Hz, 1H), 3.7 (s, 3H), 2.9-2.7 (m, 8H) 2.4 (s, 3H), 1.8 (d, J=5.9 Hz, 3H) conforms to the molecular structure (225H*) as shown in FIG. 562;
- (j) Residual solvents ICH Q3C (R8): 4-A2 (ethanol 0.1% w/w); 3-C1 (ethanol 0.3% w/w); 2-V2 (ethanol 0.1% w/w, ICH listed 5000 ppm);
- (k) Appearance: columnar, prismatic crystals, [(4-A2), FIGS. 567-572]; and
- (l) Solubility in SIF buffers: Insoluble in FeSSIF at 37° C. up to 1 h. Insoluble in FaSSGF at 37° C. up to 24 h.

In some embodiments, the tabernanthalog sorbate salt (Form A) is characterized by at least one of the following properties:
- (a) 24.7% w/w th., sorbic acid (i.e., 1.0 mol of API to 1.0 mol sorbic acid);
- (b) hydrogen bonding between both oxygen molecules on the sorbate ion. One to N1 (tryptamine nitrogen atom) of one API molecules, the other to N2 (hydro-azepine nitrogen atom) of a separate API molecule. Due to hydrogen bonding present in the structure builds up chains between API and salt molecule. Causing stacking of API and sorbate molecules closely packed to one another. This leads to less free space in the crystal structure and void radius of only −0.9 A, much smaller than the 1.4 required for a water molecule to occupy. Bond between Sorbates and API, N1-O3, 2.857 Å (hydrogen bond), N2-O2, 2.7015 Å (salification hydrogen bond) N1=Indole, N2=Hydroazepine. Sorbate molecule is disordered and bond lengths stated are an average of the two mapped positions;
- (c) Crystal system 100(2) K: monoclinic
  Space group 100(2) K: P2$_1$/c
  Unit cell 100(2) K: a=9.3410(3) Å, b=6.4173(2) Å, c=30.5108(12) Å. A=γ=90° β=95.374(3)°, V=1820.90(11) Å3.
  Asymmetric unit: contains one API molecule one sorbate ion;
- (d) XRPD: 5.7°, 11.4°, 22.8° as shown in FIG. 564 and Table 273;
- (e) DSC: onset 140.03° C. (−106.66 Jg$^{-1}$, endotherm, melt);
- (f) TGA: onset 177.6° C. (−36.4% w/w, ablation) 263.5° C. (−59% w/w, ablation);
- (g) DVS 0 to 90 to 0% RH (dm/dt<0.002%): 0.0 (0.00%), 5.0 (0.0%), 10.0 (0.01%), 15.0 (0.01%), 20.0 (0.02%), 25.0 (0.03%), 30.0 (0.03%), 40.0 (0.05%), 50.0 (0.07%), 60.0 (0.10%), 70.0 (0.14%), 80.0 (0.21%), 90.0 (0.98%), 90.0 (0.98%), 80.0 (0.48%), 70.0 (0.30%), 60.0 (0.18%), 50.0 (0.06%), 40.0 (0.03%), 30.0 (0.00%), 25.0 (0.00%), 20.0 (0.02%), 15.0 (0.03%), 10.0 (0.04%), 5.0 (0.05%), 0.0 (0.06%);
- (h) UV chromatographic purity: 99.64% area (212 nm);
- (i) $^1$H NMR: (DMSO-d$_6$, 400 MHz); δ 10.5 (s, 1H), 7.2 (d, J=8.56 Hz, 1H), 7.1 (dd, J=15.2, 15.3 Hz, 1H), 6.7 (d, J=1.9 Hz, 1H), 6.6 (dd, J=8.56, 2.2 Hz, 1H), 6.2 (d, m, 2H), 5.8 (d, J=15.0 Hz, 1H), 3.7 (s, 3H), 2.8 (m, 2H), 2.7 (m, 6H), 2.4 (s, 3H), 1.8 (d, J=5.8 Hz, 3H) ppm; conforms to the molecular structure (725H) as shown FIG. 564;
- (j) Residual solvents ICH Q3C (R8): ethanol 0.1% w/w, ICH listed 5000 ppm; and
- (k) Q $^1$H NMR: 99.9% w/w.

In some embodiments, the tabernanthalog sorbate salt (Form A) has a crystal data when collected using Single Crystal XRD as follows: $C_{20}H_{26}N_2O_3$, $M_r$=342.43, monoclinic, P2$_1$/c (No. 14), a=9.3410(3) Å, b=6.4173(2) Å, c=30.5108(12) Å, b=95.374(3)°, a=g=90°, V=1820.90(11) Å$^3$, T=100(2) K, Z=4, Z'=1, m(Cu K$_a$)=0.675 mm$^{-1}$, 13832 reflections measured, 3694 unique ($R_{int}$=0.0462) which were used in all calculations. The final wR$_2$ was 0.2098 (all data) and R$_1$ was 0.0826 (I≥2 s(I)).

In some embodiments, the tabernanthalog sorbate salt is crystalline polymorphic (Form A) and characterized by XRPD signals at 5.7 °2θ, 11.4 °2θ, and 22.8°2θ (±0.2 °2θ; ±0.1 °2θ; or ±0.0 °2θ; Cu Kα1 radiation).

In some embodiments, the tabernanthalog sorbate salt is crystalline polymorphic (Form A) and characterized by two or more, or three XRPD signals selected from the group consisting of 5.7 °2θ, 11.4 °2θ, and 22.8°2θ (±0.2 °2θ; ±0.1 °2θ; or ±0.0 °2θ; Cu Kα1 radiation).

In some embodiments, the tabernanthalog sorbate salt is crystalline polymorphic (Form A) and characterized by XRPD signals at 5.7 °2θ, 11.4 °2θ, 22.6°2θ and 24.7 °2θ (±0.2 °2θ; ±0.1°2θ; or 0.0 °2θ; Cu Kα1 radiation).

In some embodiments, the tabernanthalog sorbate salt is crystalline polymorphic (Form A) and characterized by two or more, or three XRPD signals selected from the group consisting of 5.7 °2θ, 11.4 °2θ, 22.6 °2θ and 24.7 °2θ (±0.2 °2θ; ±0.1 °2θ; or ±0.0 °2θ; Cu Kα1 radiation).

In some embodiments, the tabernanthalog sorbate salt (Form B, Pattern #1) is characterized by at least one of the following properties:
(a) XRPD: 7.5°, 15.10;
(b) DSC: onset 48.4° C. ($-231.36$ Jg$^{-1}$, endotherm, dehydration), 69.9° C. ($-160.38$ Jg$^{-1}$, endotherm, dehydration), 144.6° C. ($-102.24$ Jg$^{-1}$, endotherm, melt);
(c) TGA: onset 54.8° C. ($-1.37\%$ w/w, dehydration; this event was observed when sample was re-prepared for TGA analysis after 7 days (refer to FIG. 564) 164.37° C. ($-29.24\%$ w/w, ablation); and
(d) $^1$H NMR: (DMSO-d$_6$, 400 MHz); δ 10.3 (s, 1H), 7.2 (d, J=8.56 Hz, 1H), 7.1 (ddd, J=15.2, 15.3, 0.56 Hz, 1H), 6.7 (d, J=2.24 Hz, 1H), 6.6 (dd, J=8.54, 2.33 Hz, 1H), 6.2 (d, m, 2H), 5.8 (d, J=15.32 Hz, 1H), 3.7 (s, 3H), 2.8 (m, 2H), 2.7 (m, 6H), 2.4 (s, 3H), 1.8 (d, J=5.96 Hz, 3H) ppm; conforms to the molecular structure (225H).

In some embodiments, the tabernanthalog sorbate salt is crystalline polymorphic (Form B; Pattern #1) and characterized by XRPD signals at 7.5 °2θ, and 15.1 °2θ (±0.2°2θ; ±0.1°2θ; or 0.0 °2θ; Cu Kα1 radiation).

In some embodiments, the tabernanthalog sorbate salt (Form C, Pattern #2) is characterized by at least one of the following properties:
(a) XRPD: 5.7°, 11.1°, 11.5°, 13.9°, 16.70, 17.3°, 17.8°, 18.5°, 18.7°, 20.1°, 22.4°, 29.7°;
(b) DSC: onset 76.6° C. ($-99.32$ Jg$^{-1}$, endotherm), 145.1° C. ($-95.88$ Jg$^{-1}$, endotherm);
(c) TGA: onset 71.6° C. ($-4.4\%$ w/w, dehydration), 168.7° C. ($-27.9\%$ w/w, ablation);
(d) UV chromatographic purity: 99.69% area (212 nm); and
(e) $^1$H NMR: (DMSO-d$_6$, 400 MHz); δ 10.3 (s, 1H), 7.2 (d, J=8.6 Hz, 1H), 7.1 (ddd, J=15.3, 14.8, 0.56 Hz, 1H), 6.7 (d, J=2.2 Hz, 1H), 6.6 (dd, J=10.8, 6.2 Hz, 1H), 6.2 (m, 2H), 5.8 (d, 0.1=15.3 Hz, 1H), 3.7 (s, 3H), 2.9 (m, 2H), 2.7 (m, 6H), 2.4 (s, 3H), 1.8 (d, J=5.9 Hz, 3H) ppm; conforms to the molecular structure (Σ25H).

In some embodiments, the tabernanthalog sorbate salt is crystalline polymorphic (Form C; Pattern #2) and characterized by XRPD signals at 5.7 °2θ, and 11.5 °2θ (±0.2°2θ; ±0.1°2θ; or ±0.0 °2θ; Cu Kα1 radiation).

In some embodiments, the tabernanthalog sorbate salt is crystalline polymorphic (Form C; Pattern #2) and characterized by XRPD signals at 5.7 °2θ, 22.4 °2θ, 11.5 °2θ, 16.7 °2θ, 17.3 °2θ, 18.5 °2θ, 18.7 °2θ, 17.8 °2θ, 11.2 °2θ, 20.1 °2θ, 13.9 °2θ, and 29.7°2θ (±0.2 °2θ; ±0.1 °2θ; or ±0.0 °2θ; Cu Kα1 radiation).

In some embodiments, the tabernanthalog sorbate salt is crystalline polymorphic (Form C; Pattern #2) and characterized by two or more, or three XRPD signals selected from the group consisting of 5.7 °2θ, 22.4 °2θ, 11.5 °2θ, 16.7 °2θ, 17.3 °2θ, 18.5 °2θ, 18.7 °2θ, 17.8 °2θ, 11.2 °2θ, 20.1 °2θ, 13.9 °2θ, and 29.7°2θ (±0.2°2θ; ±0.1°2θ; or ±0.0 °2θ; Cu Kα1 radiation).

In some embodiments, the tabernanthalog sorbate salt·H$_2$O (hydrate) has a crystal data when collected using Single Crystal XRD as follows: C$_{20}$H$_{28}$N$_2$O$_4$, M$_r$=360.44, monoclinic, P2$_1$/c (No. 14), a=16.07470(10) Å, b=12.14150 (10) Å, c=10.85080(10) Å, b=109.2390(10)°, a=g=90°, V=1999.49(3) Å$^3$, T=100(2) K, Z=4, Z'=1, m(Cu K$_a$)=0.676 mm$^{-1}$, 51305 reflections measured, 3786 unique (R$_{int}$=0.0483) which were used in all calculations. The final wR$_2$ was 0.0874 (all data) and R$_1$ was 0.0347 (I≥2 s(I)).

Tabernanthalog Tartrate Salt

In yet other embodiments, the tabernanthalog tartrate salt is obtained from heat-up/cool-down crystallization of tabernanthalog (native) with L-tartaric acid in ethanol (11.2 vol) and water (7.2 vol) at 85° C. The product was isolated by centrifugation and was oven-dried under reduced pressure over 20 h at 40° C.

In yet other embodiments, the tabernanthalog tartrate salt is obtained from heat-up/cool-down crystallization of tabernanthalog (native) with L-tartaric acid in ethanol (5.0 vol) and water (5.75 vol) at 85° C. Product was isolated by filtration and dried under sustained nitrogen flux (<1 bar) over 20 h at 20° C.

In one embodiment, the tabernanthalog tartrate salt is crystalline characterized by two or more, or three XRPD signals selected from the group consisting of 17.3 °2θ, 20.4 °2θ, 21.3 °2θ, 22.4 °2θ, 16.4 °2θ, 28.3 °2θ, 19.9 °2θ, and 24 °2θ, 26.1 °2θ, 16.1 °2θ, 37.8 °2θ, 24.3 °2θ, 34.3 °2θ, 32.9 °2θ, 38.1 °2θ, 26.8 °2θ, 32.6 °2θ, and 18.2 °2θ (±0.2 °2θ; ±0.1°2θ; or ±0.0 °2θ; Cu Kα1 radiation).

In one embodiment, the tabernanthalog tartrate salt is crystalline characterized by two or more, or three XRPD signals selected from the group consisting of 17.3 °2θ, 20.4 °2θ, and 21.3 °2θ (±0.2°2θ; ±0.1°2θ; or 0.0 °2θ; Cu Kα1 radiation).

In one embodiment, the tabernanthalog tartrate salt is crystalline characterized by XRPD signals at 17.3 °2θ, 20.4 °2θ, 21.3 °2θ, 22.4 °2θ, 16.4 °2θ, 28.3 °2θ, 19.9 °2θ, and 24 °2θ, 26.1 °2θ, 16.1 °2θ, 37.8 °2θ, 24.3 °2θ, 34.3 °2θ, 32.9 °2θ, 38.1 °2θ, 26.8 °2θ, 32.6 °2θ, and 18.2°2θ (±0.2°2θ; ±0.1 °2θ; or 0.0 °2θ; Cu Kα1 radiation).

In one embodiment, the tabernanthalog tartrate salt is crystalline characterized by XRPD signals at 17.3 °2θ, 20.4 °2θ, and 21.3°2θ (±0.2°2θ; ±0.1°2θ; or ±0.0 °2θ; Cu Kα1 radiation).

In some embodiments, the tabernanthalog tartrate salt is crystalline characterized two or more, or three XRPD signals as shown in Table 217.

In some embodiments, the tabernanthalog tartrate salt is crystalline characterized two or more, or three XRPD signals as shown in FIG. 385.

In some embodiments, Form A of the tabernanthalog tartrate salt exhibits an XRPD pattern post DVS as depicted in FIG. 474.

In some embodiments the tabernanthalog tartrate salt exhibits an $^1$H NMR spectrum as depicted in FIG. 467, FIG. 545, or FIG. 546.

In some embodiments the tabernanthalog tartrate salt is a unary tartrate with 39.5% w/w th., L-tartaric acid (i.e., 1.0 mol of API to 1.0 mol fumaric acid).

In some embodiments, the tabernanthalog tartrate salt exhibits a DSC profile as depicted in FIG. 469.

In some embodiments, the tabernanthalog tartrate salt exhibits a TGA profile as depicted in FIG. 470.

In some embodiments, the tabernanthalog tartrate salt exhibits a DVS profile as depicted in FIG. 471 or FIG. 472.

In some embodiments, the tabernanthalog tartrate salt exhibits an HPLC spectrum as depicted in FIG. 476.

In some embodiments, the tabernanthalog tartrate salt exhibits at least one property as listed in Table 193.

Tabernanthalog Benzoate Salt

In yet other embodiments, the tabernanthalog benzoate salt is obtained from heat-up/cool-down crystallization of tabernanthalog (native) with benzoic acid in ethanol (8.4 vol) and water (1.4 vol) at 85° C. The product was isolated by centrifugation and was oven-dried under reduced pressure over 20 h at 40° C.

In yet other embodiments, the tabernanthalog benzoate salt is obtained from heat-up/cool-down crystallization of tabernanthalog (native) with benzoic acid in ethanol (5.0 vol) and water (0.85 vol) at 85° C. Product was isolated by filtration and dried under sustained nitrogen flux (<1 bar) over 20 h at 20° C.

In one embodiment, the tabernanthalog benzoate salt is crystalline characterized by two or more, or three XRPD signals selected from the group consisting of ±9 °2θ, 18.1 °2θ, 23.7 °2θ, 26.3 °2θ, 16.7 °2θ, 28.9 °2θ, 15.6 °2θ, and 17.7 °2θ, 19.6 °2θ, 22.9 °2θ, 24.4 °2θ, 21.3 °2θ, and 14.1 °2θ (±0.2°2θ; ±0.1°2θ; or 0.0 °2θ; Cu Kα1 radiation).

In one embodiment, the tabernanthalog benzoate salt is crystalline characterized by two or more, or three XRPD signals selected from the group consisting of ±9 °2θ, 18.1 °2θ, and 23.7 °2θ (±0.2 °2θ; ±0.1°2θ; or 0.0 °2θ; Cu Kα1 radiation).

In one embodiment, the tabernanthalog benzoate salt is crystalline characterized by signals at 9020, 18.1 °2θ, and 23.7 °2θ (±0.2°2θ; ±0.1°2θ; or 0.0 °2θ; Cu Kα1 radiation).

In one embodiment, the tabernanthalog benzoate salt is crystalline characterized by XRPD signals at 9 °2θ, 18.1 °2θ, 23.7 °2θ, 26.3 °2θ, 16.7 °2θ, 28.9 °2θ, 15.6 °2θ, 17.7 °2θ, 19.6 °2θ, and 22.9°2θ (±0.2°2θ; ±0.1°2θ; or 0.0 °2θ; Cu Kα1 radiation).

In one embodiment, the tabernanthalog benzoate salt is crystalline characterized by XRPD signals at 9 °2θ, 18.1 °2θ, and 23.7°2θ (±0.2°2θ; ±0.1°2θ; or 0.0 °2θ; Cu Kα1 radiation).

In some embodiments, the tabernanthalog benzoate salt is crystalline characterized two or more, or three XRPD signals as shown in Table 218.

In some embodiments, the tabernanthalog benzoate salt is crystalline characterized two or more, or three XRPD signals as shown in FIG. 388.

In some embodiments, Form A of the tabernanthalog benzoate salt exhibits an XRPD pattern post DVS as depicted in FIG. 486(C).

In some embodiments the tabernanthalog benzoate salt exhibits an $^1$H NMR spectrum as depicted in FIG. 493, FIG. 547, or FIG. 548.

In some embodiments the tabernanthalog benzoate salt is a unary benzoate with 34.6% w/w th., benzoic acid (i.e., 1.0 mol of API to 1.0 mol benzoic acid).

In some embodiments, the tabernanthalog benzoate salt exhibits a DSC profile as depicted in FIG. 495 or FIG. 552.

In some embodiments, the tabernanthalog benzoate salt exhibits a TGA profile as depicted in FIG. 496 or FIG. 556.

In some embodiments, the tabernanthalog benzoate salt exhibits a DVS profile as depicted in FIG. 486(A) or FIG. 486(B).

In some embodiments, the tabernanthalog benzoate salt exhibits an HPLC spectrum as depicted in FIG. 486(E).

In some embodiments, the tabernanthalog benzoate salt exhibits at least one property as listed in Table 194.

Other Tabernanthalog Salts and Other Embodiments

In some embodiments, the tabernanthalog malate salt is crystalline characterized two or more, or three XRPD signals as shown in Table 219.

In some embodiments, the tabernanthalog tosylate salt is crystalline characterized two or more, or three XRPD signals as shown in Table 220.

In some embodiments, the tabernanthalog adipate salt is crystalline characterized two or more, or three XRPD signals as shown in Table 221.

In some embodiments, the tabernanthalog glucuronate salt is crystalline characterized two or more, or three XRPD signals as shown in Table 222.

In some embodiments, the tabernanthalog phosphate salt is crystalline characterized two or more, or three XRPD signals as shown in Table 223.

In some embodiments, the tabernanthalog edisylate salt is crystalline characterized two or more, or three XRPD signals as shown in Table 224.

In some embodiments, the solid form of native tabernanthalog is crystalline native tabernanthalog characterized by two or more, or three or more XRPD signals selected from the group consisting of 18.9 °2θ, 27.3 °2θ, and 27.4°2θ (±0.2°2θ; ±0.1 °2θ; or 0.0 °2θ; Cu Kα1 radiation). In some embodiments, the solid form of native tabernanthalog is crystalline native tabernanthalog characterized by XRPD signals 18.9 °2θ, 27.3 °2θ, and 27.4°2θ (±0.2 °2θ; ±0.1 °2θ; or ±0.0 °2θ; Cu Kα1 radiation).

In some embodiments, the solid form of native tabernanthalog is crystalline native tabernanthalog characterized by two or more, or three or more XRPD signals selected from the group consisting of 18.9 °2θ, 27.3 °2θ, 27.4 °2θ, 15.1 °2θ, and 10.4°2θ (±0.2°2θ; ±0.1°2θ; or 0.0 °2θ; Cu Kα1 radiation). In some embodiments, the solid form of native tabernanthalog is crystalline native tabernanthalog characterized by XRPD signals at 18.9 °2θ, 27.3 °2θ, 27.4 °2θ, 15.1 °2θ, and 10.4°2θ (±0.2 °2θ; ±0.1°2θ; or 0.0 °2θ; Cu Kα1 radiation).

In some embodiments, the crystalline native tabernanthalog is characterized by one, two, three, four, or five XRPD signals selected from those set forth in Table 215.

In some embodiments, the solid form of tabernanthalog sorbate salt is crystalline tabernanthalog sorbate characterized by two or more, or three or more XRPD signals selected from the group consisting of 5.7 °2θ, 11.4 °2θ, and 24.7 °2θ (±0.2°2θ; ±0.1 °2θ; or ±0.0 °2θ; Cu Kα1 radiation). In some embodiments, the solid form tabernanthalog sorbate salt is crystalline tabernanthalog sorbate characterized by XRPD signals at 5.7 °2θ, 11.4 °2θ, and 24.7 °2θ (±0.2 °2θ; ±0.1 °2θ; or ±0.0 °2θ; Cu Kα1 radiation).

In some embodiments, the solid form of tabernanthalog sorbate salt is crystalline tabernanthalog sorbate characterized by two or more, or three or more XRPD signals selected from the group consisting of at 5.7 °2θ, 11.4 °2θ, 24.7 °2θ, 18.8 °2θ, and 10.5 °2θ (±0.2°2θ; ±0.1 °2θ; or ±0.0 °2θ; Cu Kα1 radiation). In some embodiments, the solid form of tabernanthalog sorbate salt is crystalline tabernanthalog sorbate characterized by XRPD signals at 5.7 °2θ, 11.4 °2θ, 24.7 °2θ, 18.8 °2θ, and 10.5°2θ (±0.2 °2θ; ±0.1°2θ; or 0.0 °2θ; Cu Kα1 radiation).

In some embodiments, the solid form of tabernanthalog sorbate salt is crystalline tabernanthalog sorbate characterized by two or more, or three or more XRPD signals selected from the group consisting of 5.7 °2θ, 11.4 °2θ, 24.7 °2θ, 18.8 °2θ, 10.5 °2θ, 22.6 °2θ, and 24.4°2θ (±0.2 °2θ; ±0.1 °2θ; or ±0.0 °2θ; Cu Kα1 radiation). In some embodiments, the solid form of tabernanthalog sorbate salt is crystalline tabernanthalog sorbate characterized by XRPD signals at 5.7 °2θ, 11.4 °2θ, 24.7 °2θ, 18.8 °2θ, 10.5 °2θ, 22.6 °2θ, and 24.4 °2θ (±0.2°2θ; ±0.1°2θ; or ±0.0 °2θ; Cu Kα1 radiation).

In some embodiments, the solid form of tabernanthalog sorbate salt is crystalline tabernanthalog sorbate characterized by two or more, or three or more XRPD signals selected from the group consisting of 5.7 °2θ, 11.4 °2θ, 24.7 °2θ, 18.8°2θ, 10.5 °2θ, 22.6 °2θ, 24.4 °2θ, 26.9 °2θ, 19.1 °2θ, and 21.4 °2θ (±0.2 °2θ; ±0.1°2θ; or 0.0 °2θ; Cu Kα1 radiation). In some embodiments, the solid form of tabernanthalog sorbate salt is crystalline tabernanthalog sorbate characterized by XRPD signals at 5.7 °2θ, 11.4 °2θ, 24.7 °2θ, 18.8 °2θ, 10.5 °2θ, 22.6 °2θ, 24.4 °2θ, 26.9 °2θ, 19.1 °2θ, and 21.4 °2θ (±0.2 °2θ; ±0.1°2θ; or ±0.0 °2θ; Cu Kα1 radiation).

In some embodiments, the crystalline tabernanthalog sorbate salt is characterized by one, two, three, four, five, six, seven, eight, nine, ten, eleven, or twelve XRPD signals selected from those set forth in Table 216.

In some embodiments, the solid form of tabernanthalog tartrate salt is crystalline tabernanthalog tartrate characterized by two or more, or three or more XRPD signals selected from the group consisting of 17.3 °2θ, 20.4 °2θ, and 21.3 °2θ (±0.2 °2θ; ±0.1°2θ; or ±0.0 °2θ; Cu Kα1 radiation). In some embodiments, the solid form tabernanthalog tartrate salt is crystalline tabernanthalog tartrate characterized by XRPD signals at 17.3 °2θ, 20.4°2θ, and 21.3 °2θ (±0.2 °2θ; ±0.1°2θ; or ±0.0 °2θ; Cu Kα1 radiation).

In some embodiments, the solid form of tabernanthalog tartrate salt is crystalline tabernanthalog tartrate characterized by two or more, or three or more XRPD signals selected from the group consisting of at 17.3 °2θ, 20.4 °2θ, 21.3 °2θ, 22.4 °2θ, and 16.4 °2θ (±0.2°2θ; ±0.1 °2θ; or 0.0 °2θ; Cu Kα1 radiation). In some embodiments, the solid form of tabernanthalog tartrate salt is crystalline tabernanthalog tartrate characterized by XRPD signals at 17.3 °2θ, 20.4 °2θ, 21.3 °2θ, 22.4 °2θ, and 16.4°2θ (±0.2 °2θ; ±0.1°2θ; or ±0.0 °2θ; Cu Kα1 radiation).

In some embodiments, the solid form of tabernanthalog tartrate salt is crystalline tabernanthalog tartrate characterized by two or more, or three or more XRPD signals selected from the group consisting of 17.3 °2θ, 20.4 °2θ, 21.3 °2θ, 22.4 °2θ, 16.4 °2θ, 28.3 °2θ, and 19.9°2θ (±0.2°2θ; ±0.1°2θ; or 0.0 °2θ; Cu Kα1 radiation). In some embodiments, the solid form of tabernanthalog tartrate salt is crystalline tabernanthalog tartrate characterized by XRPD signals at 17.3 °2θ, 20.4 °2θ, 21.3 °2θ, 22.4 °2θ, 16.4 °2θ, 28.3 °2θ, and 19.9°2θ (±0.2 °2θ; ±0.1 °2θ; or ±0.0°2θ; Cu Kα1 radiation).

In some embodiments, the solid form of tabernanthalog tartrate salt is crystalline tabernanthalog tartrate characterized by two or more, or three or more XRPD signals selected from the group consisting of 17.3 °2θ, 20.4 °2θ, 21.3 °2θ, 22.4 °2θ, 16.4°2θ, 28.3 °2θ, 19.9 °2θ, 24.0 °2θ, 26.1 °2θ, and 16.1 °2θ (±0.2 °2θ; ±0.1 °2θ; or ±0.0 °2θ; Cu Kα1 radiation). In some embodiments, the solid form of tabernanthalog tartrate salt is crystalline tabernanthalog tartrate characterized by XRPD signals at 17.3 °2θ, 20.4 °2θ, 21.3 °2θ, 22.4 °2θ, 16.4 °2θ, 28.3 °2θ, 19.9 °2θ, 24.0 °2θ, 26.1 °2θ, and 16.1°2θ (±0.2 °2θ; ±0.1°2θ; or 0.0 °2θ; Cu Kα1 radiation).

In some embodiments, the crystalline tabernanthalog tartrate salt is characterized by one, two, three, four, five, six, seven, eight, nine, ten, eleven, twelve, thirteen, fourteen, fifteen, sixteen, seventeen, or eighteen XRPD signals selected from those set forth in Table 217.

In some embodiments, the solid form of tabernanthalog benzoate salt is crystalline tabernanthalog benzoate characterized by two or more, or three or more XRPD signals selected from the group consisting of 9.0 °2θ, 18.1 °2θ, and 23.7 °2θ (±0.2 °2θ; ±0.1°2θ; or ±0.0 °2θ; Cu Kα1 radiation).

In some embodiments, the solid form tabernanthalog benzoate salt is crystalline tabernanthalog benzoate characterized by XRPD signals at 9.0 °2θ, 18.1 °2θ, and 23.7°2θ (±0.2 °2θ; ±0.1 °2θ; or 0.0 °2θ; Cu Kα1 radiation).

In some embodiments, the solid form of tabernanthalog benzoate salt is crystalline tabernanthalog benzoate characterized by two or more, or three or more XRPD signals selected from the group consisting of at 9.0 °2θ, 18.1 °2θ, 23.7 °2θ, 26.3 °2θ, and 16.7°2θ (±0.2 °2θ; ±0.1 °2θ; or ±0.0 °2θ; Cu Kα1 radiation). In some embodiments, the solid form of tabernanthalog benzoate salt is crystalline tabernanthalog benzoate characterized by XRPD signals at 9.0 °2θ, 18.1 °2θ, 23.7 °2θ, 26.3 °2θ, and 16.7°2θ (±0.2°2θ; ±0.1°2θ; or ±0.0 °2θ; Cu Kα1 radiation).

In some embodiments, the solid form of tabernanthalog benzoate salt is crystalline tabernanthalog benzoate characterized by two or more, or three or more XRPD signals selected from the group consisting of 9.0 °2θ, 18.1 °2θ, 23.7 °2θ, 26.3 °2θ, 16.7 °2θ, 28.9 °2θ, and 15.6°2θ (±0.2°2θ; ±0.1°2θ; or 0.0 °2θ; Cu Kα1 radiation). In some embodiments, the solid form of tabernanthalog benzoate salt is crystalline tabernanthalog benzoate characterized by XRPD signals at 9.0 °2θ, 18.1 °2θ, 23.7 °2θ, 26.3°2θ, 16.7 °2θ, 28.9 °2θ, and 15.6 °2θ (±0.2 °2θ; 0.1 °2θ; or ±0.0 °2θ; Cu Kα1 radiation).

In some embodiments, the solid form of tabernanthalog benzoate salt is crystalline tabernanthalog benzoate characterized by two or more, or three or more XRPD signals selected from the group consisting of 9.0 °2θ, 18.1 °2θ, 23.7°2θ, 26.3 °2θ, 16.7 °2θ, 28.9 °2θ, 15.6°2θ, 17.7 °2θ, 19.6 °2θ, and 22.9 °2θ (±0.2 °2θ; ±0.1°2θ; or ±0.0 °2θ; Cu Kα1 radiation). In some embodiments, the solid form of tabernanthalog benzoate salt is crystalline tabernanthalog benzoate characterized by XRPD signals at 9.0 °2θ, 18.1 °2θ, 23.7 °2θ, 26.3 °2θ, 16.7 °2θ, 28.9 °2θ, 15.6 °2θ, 17.7 °2θ, 19.6 °2θ, and 22.9°2θ (±0.2°2θ; ±0.1 °2θ; or 0.0 °2θ; Cu Kα1 radiation).

In some embodiments, the crystalline tabernanthalog benzoate salt is characterized by one, two, three, four, five, six, seven, eight, nine, ten, eleven, twelve, or thirteen XRPD signals selected from those set forth in Table 218.

In some embodiments, the solid form of tabernanthalog malate salt is crystalline tabernanthalog malate characterized by two or more, or three or more XRPD signals selected from the group consisting of 19.5 °2θ, 21.4 °2θ, and 16.7 °2θ (±0.2 °2θ; ±0.1°2θ; or ±0.0 °2θ; Cu Kα1 radiation). In some embodiments, the solid form tabernanthalog malate salt is crystalline tabernanthalog malate characterized by XRPD signals at 19.5 °2θ, 21.4°2θ, and 16.7 °2θ, (±0.2 °2θ; ±0.1 °2θ; or 0.0 °2θ; Cu Kα1 radiation).

In some embodiments, the solid form of tabernanthalog malate salt is crystalline tabernanthalog malate characterized by two or more, or three or more XRPD signals selected from the group consisting of at 19.5 °2θ, 21.4 °2θ, 16.7 °2θ, 14.0 °2θ, and 27.0 °2θ (±0.2 °2θ; ±0.1 °2θ; or 0.0 °2θ; Cu Kα1 radiation). In some embodiments, the solid form of tabernanthalog malate salt is crystalline tabernanthalog malate characterized by XRPD signals at 19.5 °2θ, 21.4 °2θ, 16.7 °2θ, 14.0 °2θ, and 27.0°2θ (±0.2°2θ; ±0.1°2θ; or ±0.0 °2θ; Cu Kα1 radiation).

In some embodiments, the solid form of tabernanthalog malate salt is crystalline tabernanthalog malate characterized by two or more, or three or more XRPD signals selected from the group consisting of 19.5 °2θ, 21.4 °2θ, 16.7 °2θ, 14.0 °2θ, 27.0 °2θ, 18.3 °2θ, and 25.1 °2θ (±0.2°2θ; ±0.1°2θ; or 0.0 °2θ; Cu Kα1 radiation). In some embodiments, the solid form of tabernanthalog malate salt is crystalline tabernanthalog malate characterized by XRPD signals at 19.5 °2θ, 21.4 °2θ, 16.7 °2θ, 14.0°2θ, 27.0 °2θ, 18.3 °2θ, and 25.1 °2θ (±0.2 °2θ; ±0.1 °2θ; or ±0.0 °2θ; Cu Kα1 radiation).

In some embodiments, the solid form of tabernanthalog malate salt is crystalline tabernanthalog malate characterized by two or more, or three or more XRPD signals selected from the group consisting of 19.5 °2θ, 21.4 °2θ, 16.7 °2θ, 14.0 °2θ, 27.0°2θ, 18.3 °2θ, 25.1 °2θ, 23.9 °2θ, 31.2 °2θ and 6.1 °2θ (±0.2 °2θ; ±0.1 °2θ; or ±0.0 °2θ; Cu Kα1 radiation). In some embodiments, the solid form of tabernanthalog malate salt is crystalline tabernanthalog malate characterized by XRPD signals at 19.5 °2θ, 21.4 °2θ, 16.7 °2θ, 14.0 °2θ, 27.0 °2θ, 18.3°2θ, 25.1 °2θ, 23.9 °2θ, 31.2°2θ and 6.1°2θ (±0.2°2θ; ±0.1°2θ; or 0.0 °2θ; Cu Kα1 radiation).

In some embodiments, the crystalline tabernanthalog malate salt is characterized by one, two, three, four, five, six, seven, eight, nine, ten, eleven, twelve, or thirteen XRPD signals selected from those set forth in Table 219.

In some embodiments, the solid form of tabernanthalog tosylate salt is crystalline tabernanthalog tosylate characterized by one or two XRPD signals selected from the group consisting of 5.5 °2θ and 11.0 °2θ (±0.2°2θ; ±0.1 °2θ; or ±0.0 °2θ; Cu Kα1 radiation). In some embodiments, the solid form tabernanthalog tosylate salt is crystalline tabernanthalog tosylate characterized by XRPD signals at 5.5°2θ and 11.0 °2θ (±0.2 °2θ; ±0.1 °2θ; or ±0.0 °2θ; Cu Kα1 radiation).

In some embodiments, the crystalline tabernanthalog tosylate salt is characterized by one, or two XRPD signals selected from those set forth in Table 220.

In some embodiments, the solid form of tabernanthalog adipate salt is crystalline tabernanthalog adipate characterized by two or more, or three or more XRPD signals selected from the group consisting of 17.8 °2θ, 20.6 °2θ, and 19.4°2θ (±0.2°2θ; ±0.1 °2θ; or ±0.0 °2θ; Cu Kα1 radiation). In some embodiments, the solid form tabernanthalog adipate salt is crystalline tabernanthalog adipate characterized by XRPD signals at 17.8 °2θ, 20.6 °2θ, and 19.4°2θ (±0.2 °2θ; ±0.1 °2θ; or 0.0 °2θ; Cu Kα1 radiation).

In some embodiments, the solid form of tabernanthalog adipate salt is crystalline tabernanthalog adipate characterized by two or more, or three or more XRPD signals selected from the group consisting of at 17.8 °2θ, 20.6 °2θ, 19.4 °2θ, 15.7 °2θ, and 21.0 °2θ (±0.2°2θ; ±0.1 °2θ; or ±0.0 °2θ; Cu Kα1 radiation). In some embodiments, the solid form of tabernanthalog adipate salt is crystalline tabernanthalog adipate characterized by XRPD signals at 17.8 °2θ, 20.6 °2θ, 19.4 °2θ, 15.7 °2θ, and 21.0 °2θ (±0.2 °2θ; ±0.1°2θ; or 0.0 °2θ; Cu Kα1 radiation).

In some embodiments, the solid form of tabernanthalog adipate salt is crystalline tabernanthalog adipate characterized by two or more, or three or more XRPD signals selected from the group consisting of 17.8 °2θ, 20.6 °2θ, 19.4 °2θ, 15.7 °2θ, 21.0 °2θ, 16.5 °2θ, and 24.0°2θ (±0.2 °2θ; ±0.1 °2θ; or 0.0 °2θ; Cu Kα1 radiation). In some embodiments, the solid form of tabernanthalog adipate salt is crystalline tabernanthalog adipate characterized by XRPD signals at 17.8 °2θ, 20.6 °2θ, 19.4 °2θ, 15.7 °2θ, 21.0 °2θ, 16.5 °2θ, and 24.0°2θ (±0.2°2θ; ±0.1 °2θ; or ±0.0 °2θ; Cu Kα1 radiation).

In some embodiments, the solid form of tabernanthalog adipate salt is crystalline tabernanthalog adipate characterized by two or more, or three or more XRPD signals selected from the group consisting of 17.8 °2θ, 20.6 °2θ, 19.4 °2θ, 15.7 °2θ, 21.0 °2θ, 16.5 °2θ, 24.0 °2θ, 25.5 °2θ, 21.8 °2θ, and 18.6°2θ (±0.2 °2θ; ±0.1 °2θ; or ±0.0 °2θ; Cu Kα1 radiation). In some embodiments, the solid form of tabernanthalog adipate salt is crystalline tabernanthalog adipate characterized by XRPD signals at 17.8 °2θ, 20.6 °2θ, 19.4 °2θ, 15.7 °2θ, 21.0 °2θ, 16.5 °2θ, 24.0 °2θ, 25.5°2θ, 21.8 °2θ, and 18.6°2θ (±0.2 °2θ; ±0.1 °2θ; or ±0.0 °2θ; Cu Kα1 radiation).

In some embodiments, the crystalline tabernanthalog adipate salt is characterized by one, two, three, four, five, six, seven, eight, nine, ten, eleven, twelve, thirteen, fourteen, fifteen, sixteen, or seventeen XRPD signals selected from those set forth in Table 221.

In some embodiments, the solid form of tabernanthalog glucoronate salt is crystalline tabernanthalog glucoronate characterized by two or more, or three or more XRPD signals selected from the group consisting of 20.7 °2θ, 20.1°2θ, and 6.6 °2θ (±0.2 °2θ; ±0.1 °2θ; or ±0.0 °2θ; Cu Kα1 radiation). In some embodiments, the solid form tabernanthalog glucoronate salt is crystalline tabernanthalog glucoronate characterized by XRPD signals at 20.7 °2θ, 20.1 °2θ, and 6.6°2θ (±0.2 °2θ; ±0.1°2θ; or 0.0 °2θ; Cu Kα1 radiation).

In some embodiments, the solid form of tabernanthalog glucoronate salt is crystalline tabernanthalog glucoronate characterized by two or more, or three or more XRPD signals selected from the group consisting of at 20.7 °2θ, 20.1 °2θ, 6.6 °2θ, 12.5°2θ, and 18.1 °2θ (±0.2 °2θ; ±0.1 °2θ; or ±0.0 °2θ; Cu Kα1 radiation). In some embodiments, the solid form of tabernanthalog glucoronate salt is crystalline tabernanthalog glucoronate characterized by XRPD signals at 20.7 °2θ, 20.1°2θ, 6.6 °2θ, 12.5 °2θ, and 18.1 °2θ (±0.2 °2θ; ±0.1°2θ; or ±0.0 °2θ; Cu Kα1 radiation).

In some embodiments, the solid form of tabernanthalog glucoronate salt is crystalline tabernanthalog glucoronate characterized by two or more, or three or more XRPD signals selected from the group consisting of 20.7 °2θ, 20.1°2θ, 6.6 °2θ, 12.5 °2θ, 18.1 °2θ, 24.5 °2θ, and 22.9 °2θ(±0.2 °2θ; ±0.1°2θ; or 0.0 °2θ; Cu Kα1 radiation). In some embodiments, the solid form of tabernanthalog glucoronate salt is crystalline tabernanthalog glucoronate characterized by XRPD signals at 20.7 °2θ, 20.1°2θ, 6.6 °2θ, 12.5°2θ, 18.1 °2θ, 24.5 °2θ, and 22.9 °2θ (±0.2 °2θ; ±0.1 °2θ; or 0.0 °2θ; Cu Kα1 radiation).

In some embodiments, the solid form of tabernanthalog glucoronate salt is crystalline tabernanthalog glucoronate characterized by two or more, or three or more XRPD signals selected from the group consisting of 20.7 °2θ, 20.1 °2θ, 6.6 °2θ, 12.5 °2θ, 18.1 °2θ, 24.5 °2θ, 22.9 °2θ, 18.7 °2θ, 15.1 °2θ, and 29.9 °2θ (±0.2 °2θ; ±0.1°2θ; or ±0.0 °2θ; Cu Kα1 radiation). In some embodiments, the solid form of tabernanthalog glucoronate salt is crystalline tabernanthalog glucoronate characterized by XRPD signals at 20.7 °2θ, 20.1 °2θ, 6.6 °2θ, 12.5 °2θ, 18.1 °2θ, 24.5 °2θ, 22.9 °2θ, 18.7 °2θ, 15.1 °2θ, and 29.9 °2θ (±0.2 °2θ; ±0.1 °2θ; or 0.0 °2θ; Cu Kα1 radiation).

In some embodiments, the crystalline tabernanthalog glucoronate salt is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven XRPD signals selected from those set forth in Table 222.

In some embodiments, the solid form of tabernanthalog phosphate salt is crystalline tabernanthalog phosphate characterized by two or more, or three or more XRPD signals selected from the group consisting of 5.3 °2θ, 14.4 °2θ, and 14.7 °2θ (±0.2 °2θ; ±0.1°2θ; or ±0.0 °2θ; Cu Kα1 radiation). In some embodiments, the solid form tabernanthalog phosphate salt is crystalline tabernanthalog phosphate characterized by XRPD signals at 5.3 °2θ, 14.4 °2θ, and 14.7 °2θ (±0.2 °2θ; ±0.1°2θ; or ±0.0 °2θ; Cu Kα1 radiation).

In some embodiments, the solid form of tabernanthalog phosphate salt is crystalline tabernanthalog phosphate characterized by two or more, or three or more XRPD signals selected from the group consisting of at 5.3 °2θ, 14.4 °2θ, 14.7 °2θ, 20.2°2θ, and 22.9 °2θ (±0.2°2θ; ±0.1 °2θ; or ±0.0 °2θ; Cu Kα1 radiation). In some embodiments, the solid form of tabernanthalog phosphate salt is crystalline tabernanthalog phosphate characterized by XRPD signals at 5.3 °2θ, 14.4 °2θ, 14.7 °2θ, 20.2 °2θ, and 22.9°2θ (±0.2 °2θ; ±0.1°2θ; or ±0.0 °2θ; Cu Kα1 radiation).

In some embodiments, the solid form of tabernanthalog phosphate salt is crystalline tabernanthalog phosphate characterized by two or more, or three or more XRPD signals selected from the group consisting of 5.3 °2θ, 14.4 °2θ, 14.7 °2θ, 20.2 °2θ, 22.9 °2θ, 24.0 °2θ, and 22.7°2θ (±0.2 °2θ; ±0.1 °2θ; or 0.0 °2θ; Cu Kα1 radiation). In some embodiments, the solid form of tabernanthalog phosphate salt is crystalline tabernanthalog phosphate characterized by XRPD signals at 5.3 °2θ, 14.4 °2θ, 14.7 °2θ, 20.2°2θ, 22.9 °2θ, 24.0 °2θ, and 22.7 °2θ (±0.2°2θ; ±0.1°2θ; or 0.0 °2θ; Cu Kα1 radiation).

In some embodiments, the solid form of tabernanthalog phosphate salt is crystalline tabernanthalog phosphate characterized by two or more, or three or more XRPD signals selected from the group consisting of 5.3 °2θ, 14.4 °2θ, 14.7 °2θ, 20.2°2θ, 22.9 °2θ, 24.0 °2θ, 22.7 °2θ, 25.5 °2θ, 19.7 °2θ, and 24.3 °2θ (±0.2 °2θ; ±0.1 °2θ; or ±0.0 °2θ; Cu Kα1 radiation). In some embodiments, the solid form of tabernanthalog phosphate salt is crystalline tabernanthalog phosphate characterized by XRPD signals at 5.3 °2θ, 14.4 °2θ, 14.7 °2θ, 20.2 °2θ, 22.9 °2θ, 24.0 °2θ, 22.7 °2θ, 25.5 °2θ, 19.7 °2θ, and 24.3 °2θ (±0.2 °2θ; ±0.1°2θ; or 0.0 °2θ; Cu Kα1 radiation).

In some embodiments, the crystalline tabernanthalog phosphate salt is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 223.

In some embodiments, the solid form of tabernanthalog edisylate salt is crystalline tabernanthalog edisylate characterized by two or more, or three or more XRPD signals selected from the group consisting of 17.4 °2θ, 19.9 °2θ, and 20.8°2θ (±0.2 °2θ; ±0.1 °2θ; or 0.0 °2θ; Cu Kα1 radiation). In some embodiments, the solid form tabernanthalog edisylate salt is crystalline tabernanthalog edisylate characterized by XRPD signals at 17.4 °2θ, 19.9 °2θ, and 20.8°2θ (±0.2 °2θ; ±0.1 °2θ; or 0.0 °2θ; Cu Kα1 radiation).

In some embodiments, the solid form of tabernanthalog edisylate salt is crystalline tabernanthalog edisylate characterized by two or more, or three or more XRPD signals selected from the group consisting of at 17.4 °2θ, 19.9 °2θ, 20.8 °2θ, 21.8 °2θ, and 12.6°2θ (±0.2 °2θ; ±0.1 °2θ; or 0.0 °2θ; Cu Kα1 radiation). In some embodiments, the solid form of tabernanthalog edisylate salt is crystalline tabernanthalog edisylate characterized by XRPD signals at 17.4 °2θ, 19.9 °2θ, 20.8 °2θ, 21.8 °2θ, and 12.6 °2θ (±0.2°2θ; ±0.1°2θ; or ±0.0 °2θ; Cu Kα1 radiation).

In some embodiments, the solid form of tabernanthalog edisylate salt is crystalline tabernanthalog edisylate characterized by two or more, or three or more XRPD signals selected from the group consisting of 17.4 °2θ, 19.9 °2θ, 20.8 °2θ, 21.8 °2θ, 12.6 °2θ, 20.4 °2θ, and 12.8°2θ (±0.2 °2θ; ±0.1°2θ; or 0.0 °2θ; Cu Kα1 radiation). In some embodiments, the solid form of tabernanthalog edisylate salt is crystalline tabernanthalog edisylate characterized by XRPD signals at 17.4 °2θ, 19.9 °2θ, 20.8 °2θ, 21.8 °2θ, 12.6 °2θ, 20.4 °2θ, and 12.8°2θ (±0.2 °2θ; ±0.1 °2θ; or ±0.0 °2θ; Cu Kα1 radiation).

In some embodiments, the solid form of tabernanthalog edisylate salt is crystalline tabernanthalog edisylate characterized by two or more, or three or more XRPD signals selected from the group consisting of 17.4 °2θ, 19.9 °2θ, 20.8 °2θ, 21.8 °2θ, 12.6°2θ, 20.4 °2θ, 12.8 °2θ, 18.4 °2θ, 4.5 °2θ, and 19.6 °2θ (±0.2 °2θ; ±0.1 °2θ; or 0.0 °2θ; Cu Kα1 radiation). In some embodiments, the solid form of tabernanthalog edisylate salt is crystalline tabernanthalog edisylate characterized by XRPD signals at 17.4 °2θ, 19.9 °2θ, 20.8 °2θ, 21.8 °2θ, 12.6°2θ, 20.4 °2θ, 12.8 °2θ, 18.4 °2θ, 4.5 °2θ, and 19.6 °2θ (±0.2 °2θ; ±0.1°2θ; or ±0.0 °2θ; Cu Kα1 radiation).

In some embodiments, the crystalline tabernanthalog edisylate salt is characterized by one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two XRPD signals selected from those set forth in Table 224.

In some embodiments, the solid form of tabernanthalog maleate salt is crystalline tabernanthalog maleate characterized by two or more, or three or more XRPD signals selected from the group consisting of 20.7 °2θ, 26.8 °2θ, and 19.4 °2θ (±0.2 °2θ; ±0.1 °2θ; or ±0.0 °2θ; Cu Kα1 radiation). In some embodiments, the solid form tabernanthalog maleate salt is crystalline tabernanthalog maleate characterized by XRPD signals at 20.7 °2θ, 26.8 °2θ, and 19.4°2θ (±0.2 °2θ; ±0.1 °2θ; or 0.0 °2θ; Cu Kα1 radiation).

In some embodiments, the solid form of tabernanthalog maleate salt is crystalline tabernanthalog maleate characterized by two or more, or three or more XRPD signals selected from the group consisting of at 20.7 °2θ, 26.8 °2θ, 19.4 °2θ, 25.3 °2θ, and 12.6 °2θ (±0.2°2θ; ±0.1 °2θ; or ±0.0 °2θ; Cu Kα1 radiation). In some embodiments, the solid form of tabernanthalog maleate salt is crystalline tabernanthalog maleate characterized by XRPD signals at 20.7 °2θ, 26.8 °2θ, 19.4 °2θ, 25.3 °2θ, and 12.6 °2θ (±0.2 °2θ; 0.1°2θ; or 0.0 °2θ; Cu Kα1 radiation).

In some embodiments, the solid form of tabernanthalog maleate salt is crystalline tabernanthalog maleate characterized by two or more, or three or more XRPD signals selected from the group consisting of 20.7 °2θ, 26.8 °2θ, 19.4 °2θ, 25.3 °2θ, 12.6 °2θ, 22.2 °2θ, and 10.4 °2θ(±0.2°2θ; ±0.1 °2θ; or 0.0 °2θ; Cu Kα1 radiation). In some embodiments, the solid form of tabernanthalog maleate salt is crystalline tabernanthalog maleate characterized by XRPD signals at 20.7 °2θ, 26.8 °2θ, 19.4 °2θ, 25.3 °2θ, 12.6 °2θ, 22.2°2θ, and 10.4°2θ (±0.2 °2θ; ±0.1°2θ; or ±0.0 °2θ; Cu Kα1 radiation).

In some embodiments, the solid form of tabernanthalog maleate salt is crystalline tabernanthalog maleate characterized by two or more, or three or more XRPD signals selected from the group consisting of 20.7 °2θ, 26.8 °2θ, 19.4 °2θ, 25.3 °2θ, 12.6 °2θ, 22.2 °2θ, 10.4 °2θ, 18.9 °2θ, 25.3 °2θ, and 21.0 °2θ (±0.2 °2θ; ±0.1 °2θ; or ±0.0 °2θ; Cu Kα1 radiation). In some embodiments, the solid form of tabernanthalog maleate salt is crystalline tabernanthalog maleate characterized by XRPD signals at 20.7 °2θ, 26.8 °2θ, 19.4 °2θ, 25.3 °2θ, 12.6 °2θ, 22.2 °2θ, 10.4 °2θ, 18.9 °2θ, 25.3 °2θ, and 21.0°2θ (±0.2 °2θ; ±0.1 °2θ; or ±0.0 °2θ; Cu Kα1 radiation).

In some embodiments, the crystalline tabernanthalog maleate salt is characterized by one, two, three, four, five, six, seven, eight, nine, ten, eleven, twelve, thirteen, fourteen, or fifteen XRPD signals selected from those set forth in Table 225.

In some embodiments, the solid form of tabernanthalog galactarate salt is crystalline tabernanthalog galactarate characterized by two or more, or three or more XRPD signals selected from the group consisting of 19.6 °2θ, 30.7 °2θ, and 37.7 °2θ (±0.2°2θ; ±0.1 °2θ; or ±0.0 °2θ; Cu Kα1 radiation). In some embodiments, the solid form tabernanthalog galactarate salt is crystalline tabernanthalog galactarate characterized by XRPD signals at 19.6 °2θ, 30.7 °2θ, and 37.7 °2θ (±0.2 °2θ; 0.1°2θ; or 0.0 °2θ; Cu Kα1 radiation).

In some embodiments, the solid form of tabernanthalog galactarate salt is crystalline tabernanthalog galactarate characterized by two or more, or three or more XRPD signals selected from the group consisting of at 19.6 °2θ, 30.7 °2θ, 37.7 °2θ, 18.1 °2θ, and 37.6°2θ (±0.2 °2θ; ±0.1 °2θ; or ±0.0 °2θ; Cu Kα1 radiation). In some embodiments, the solid form of tabernanthalog galactarate salt is crystalline tabernanthalog galactarate characterized by XRPD signals at 19.6 °2θ, 30.7 °2θ, 37.7 °2θ, 18.1 °2θ, and 37.6°2θ (±0.2°2θ; ±0.1°2θ; or 0.0 °2θ; Cu Kα1 radiation).

In some embodiments, the solid form of tabernanthalog galactarate salt is crystalline tabernanthalog galactarate characterized by two or more, or three or more XRPD signals selected from the group consisting of 19.6 °2θ, 30.7 °2θ, 37.7 °2θ, 18.1 °2θ, 37.6 °2θ, 5.7 °2θ, and 34.5°2θ (±0.2°2θ; ±0.1°2θ; or 0.0 °2θ; Cu Kα1 radiation). In some embodiments, the solid form of tabernanthalog galactarate salt is crystalline tabernanthalog galactarate characterized by XRPD signals at 19.6 °2θ, 30.7 °2θ, 37.7 °2θ, 18.1 °2θ, 37.6 °2θ, 5.7 °2θ, and 34.5 °2θ (±0.2 °2θ; ±0.1 °2θ; or 0.0 °2θ; Cu Kα1 radiation).

In some embodiments, the solid form of tabernanthalog galactarate salt is crystalline tabernanthalog galactarate characterized by two or more, or three or more XRPD signals selected from the group consisting of 19.6 °2θ, 30.7 °2θ, 37.7 °2θ, 18.1 °2θ, 37.6 °2θ, 5.7 °2θ, 34.5 °2θ, 21.5 °2θ, 26.8 °2θ, and 36.8 °2θ (±0.2°2θ; ±0.1°2θ; or ±0.0 °2θ; Cu Kα1 radiation). In some embodiments, the solid form of tabernanthalog galactarate salt is crystalline tabernanthalog galactarate characterized by XRPD signals at 19.6 °2θ, 30.7 °2θ, 37.7 °2θ, 18.1°2θ, 37.6 °2θ, 5.7 °2θ, 34.5 °2θ, 21.5 °2θ, 26.8 °2θ, and 36.8°2θ (±0.2°2θ; ±0.1 °2θ; or 0.0 °2θ; Cu Kα1 radiation).

In some embodiments, the crystalline tabernanthalog galactarate salt is characterized by one, two, three, four, five, six, seven, eight, nine, ten, eleven, twelve, thirteen, fourteen, fifteen, sixteen, seventeen, eighteen, nineteen, or twenty XRPD signals selected from those set forth in Table 226.

In some embodiments, the solid form of tabernanthalog citrate salt is crystalline tabernanthalog citrate characterized by two or more, or three or more XRPD signals selected from the group consisting of 16.6 °2θ, 12.5 °2θ, and 20.9°2θ (±0.2°2θ; ±0.1 °2θ; or ±0.0 °2θ; Cu Kα1 radiation). In some embodiments, the solid form tabernanthalog citrate salt is crystalline tabernanthalog citrate characterized by XRPD signals at 16.6 °2θ, 12.5 °2θ, and 20.9°2θ (±0.2 °2θ; ±0.1 °2θ; or ±0.0 °2θ; Cu Kα1 radiation).

In some embodiments, the solid form of tabernanthalog citrate salt is crystalline tabernanthalog citrate characterized by two or more, or three or more XRPD signals selected from the group consisting of at 16.6 °2θ, 12.5 °2θ, 20.9 °2θ, 13.0 °2θ, and 21.9 °2θ (±0.2 °2θ; ±0.1 °2θ; or 0.0 °2θ; Cu Kα1 radiation). In some embodiments, the solid form of tabernanthalog citrate salt is crystalline tabernanthalog citrate characterized by XRPD signals at 16.6 °2θ, 12.5 °2θ, 20.9 °2θ, 13.0 °2θ, and 21.9°2θ (±0.2°2θ; ±0.1°2θ; or ±0.0 °2θ; Cu Kα1 radiation).

In some embodiments, the solid form of tabernanthalog citrate salt is crystalline tabernanthalog citrate characterized by two or more, or three or more XRPD signals selected from the group consisting of 16.6 °2θ, 12.5 °2θ, 20.9 °2θ, 13.0 °2θ, 21.9 °2θ, 23.7 °2θ, and 17.6°2θ (±0.2°2θ; ±0.1°2θ; or 0.0 °2θ; Cu Kα1 radiation). In some embodiments, the solid form of tabernanthalog citrate salt is crystalline tabernanthalog citrate characterized by XRPD signals at 16.6 °2θ, 12.5 °2θ, 20.9 °2θ, 13.0 °2θ, 21.9 °2θ, 23.7 °2θ, and 17.6°2θ (±0.2 °2θ; ±0.1 °2θ; or ±0.0 °2θ; Cu Kα1 radiation).

In some embodiments, the solid form of tabernanthalog citrate salt is crystalline tabernanthalog citrate characterized by two or more, or three or more XRPD signals selected from the group consisting of 16.6 °2θ, 12.5 °2θ, 20.9 °2θ, 13.0 °2θ, 21.9 °2θ, 23.7 °2θ, 17.6 °2θ, 17.7 °2θ, 26.0 °2θ, and 19.1 °2θ (±0.2 °2θ; ±0.1 °2θ; or ±0.0 °2θ; Cu Kα1 radiation). In some embodiments, the solid form of tabernanthalog citrate salt is crystalline tabernanthalog citrate characterized by XRPD signals at 16.6 °2θ, 12.5 °2θ, 20.9 °2θ, 13.0 °2θ, 21.9 °2θ, 23.7 °2θ, 17.6 °2θ, 17.7 °2θ, 26.0 °2θ, and 19.1°2θ (±0.2 °2θ; ±0.1°2θ; or 0.0 °2θ; Cu Kα1 radiation).

In some embodiments, the crystalline tabernanthalog citrate salt is characterized by one, two, three, four, five, six, seven, eight, nine, ten, eleven, twelve, or thirteen XRPD signals selected from those set forth in Table 227.

In some embodiments, the solid form of tabernanthalog glycolate salt is crystalline tabernanthalog glycolate characterized by two or more, or three or more XRPD signals selected from the group consisting of 23.5 °2θ, 18.0 °2θ, and 23.4 °2θ (±0.2°2θ; ±0.1°2θ; or ±0.0 °2θ; Cu Kα1 radiation). In some embodiments, the solid form tabernanthalog glycolate salt is crystalline tabernanthalog glycolate characterized by XRPD signals at 23.5 °2θ, 18.0 °2θ, and 23.4 °2θ (±0.2 °2θ; 0.1°2θ; or 0.0 °2θ; Cu Kα1 radiation).

In some embodiments, the solid form of tabernanthalog glycolate salt is crystalline tabernanthalog glycolate characterized by two or more, or three or more XRPD signals selected from the group consisting of at 23.5 °2θ, 18.0 °2θ, 23.4 °2θ, 9.1 °2θ, and 9.7°2θ (±0.2 °2θ; ±0.1 °2θ; or ±0.0 °2θ; Cu Kα1 radiation). In some embodiments, the solid form of tabernanthalog glycolate salt is crystalline tabernanthalog glycolate characterized by XRPD signals at 23.5 °2θ, 18.0 °2θ, 23.4 °2θ, 9.1 °2θ, and 9.7°2θ (±0.2°2θ; ±0.1°2θ; or ±0.0 °2θ; Cu Kα1 radiation).

In some embodiments, the solid form of tabernanthalog glycolate salt is crystalline tabernanthalog glycolate characterized by two or more, or three or more XRPD signals selected from the group consisting of 23.5 °2θ, 18.0 °2θ, 23.4 °2θ, 9.1 °2θ, 9.7 °2θ, 19.0 °2θ, and 18.3°2θ (±0.2°2θ; ±0.1°2θ; or 0.0 °2θ; Cu Kα1 radiation). In some embodiments, the solid form of tabernanthalog glycolate salt is crystalline tabernanthalog glycolate characterized by XRPD signals at 23.5 °2θ, 18.0 °2θ, 23.4 °2θ, 9.1 °2θ, 9.7°2θ, 19.0 °2θ, and 18.3 °2θ (±0.2 °2θ; ±0.1 °2θ; or ±0.0 °2θ; Cu Kα1 radiation).

In some embodiments, the solid form of tabernanthalog glycolate salt is crystalline tabernanthalog glycolate characterized by two or more, or three or more XRPD signals selected from the group consisting of 23.5 °2θ, 18.0 °2θ, 23.4 °2θ, 9.1 °2θ, 9.7 °2θ, 19.0 °2θ, 18.3 °2θ, 19.6 °2θ, 19.8 °2θ, and 29.5 °2θ (±0.2 °2θ; ±0.1°2θ; or 0.0 °2θ; Cu Kα1 radiation). In some embodiments, the solid form of tabernanthalog glycolate salt is crystalline tabernanthalog glycolate characterized by XRPD signals at 23.5 °2θ, 18.0 °2θ, 23.4 °2θ, 9.1 °2θ, 9.7 °2θ, 19.0 °2θ, 18.3 °2θ, 19.6 °2θ, 19.8 °2θ, and 29.5°2θ (±0.2°2θ; ±0.1 °2θ; or 0.0 °2θ; Cu Kα1 radiation).

In some embodiments, the crystalline tabernanthalog glycolate salt is characterized by one, two, three, four, five, six, seven, eight, nine, ten, eleven, twelve, thirteen, fourteen, fifteen, or sixteen XRPD signals selected from those set forth in Table 228.

In some embodiments, the solid form of tabernanthalog succinate salt is crystalline tabernanthalog succinate characterized by two or more, or three or more XRPD signals selected from the group consisting of 8.3 °2θ, 17.2 °2θ, and 24.7 °2θ (±0.2 °2θ; ±0.1 °2θ; or ±0.0 °2θ; Cu Kα1 radiation). In some embodiments, the solid form tabernanthalog succinate salt is crystalline tabernanthalog succinate characterized by XRPD signals at 8.3 °2θ, 17.2 °2θ, and 24.7 °2θ (±0.2 °2θ; ±0.1 °2θ; or 0.0 °2θ; Cu Kα1 radiation).

In some embodiments, the solid form of tabernanthalog succinate salt is crystalline tabernanthalog succinate characterized by two or more, or three or more XRPD signals selected from the group consisting of at 8.3 °2θ, 17.2 °2θ, 24.7 °2θ, 22.2 °2θ, and 15.4°2θ (±0.2 °2θ; ±0.1 °2θ; or ±0.0 °2θ; Cu Kα1 radiation). In some embodiments, the solid form of tabernanthalog succinate salt is crystalline tabernanthalog succinate characterized by XRPD signals 8.3 °2θ, 17.2 °2θ, 24.7 °2θ, 22.2 °2θ, and 15.4 (±0.2°2θ; ±0.1°2θ; or ±0.0 °2θ; Cu Kα1 radiation).

In some embodiments, the solid form of tabernanthalog succinate salt is crystalline tabernanthalog succinate characterized by two or more, or three or more XRPD signals selected from the group consisting of 8.3 °2θ, 17.2 °2θ, 24.7 °2θ, 22.2 °2θ, 15.4 °2θ, 24.1 °2θ, and 16.1°2θ (±0.2°2θ; ±0.1 °2θ; or 0.0 °2θ; Cu Kα1 radiation). In some embodiments, the solid form of tabernanthalog succinate salt is crystalline tabernanthalog succinate characterized by XRPD signals at 8.3 °2θ, 17.2 °2θ, 24.7 °2θ, 22.2°2θ, 15.4 °2θ, 24.1 °2θ, and 16.1 (±0.2°2θ; ±0.1°2θ; or 0.0 °2θ; Cu Kα1 radiation).

In some embodiments, the solid form of tabernanthalog succinate salt is crystalline tabernanthalog succinate characterized by two or more, or three or more XRPD signals selected from the group consisting of 8.3 °2θ, 17.2 °2θ, 24.7°2θ, 22.2 °2θ, 15.4 °2θ, 24.1 °2θ, 16.1 °2θ, 11.0 °2θ, 21.3 °2θ, and 20.1 °2θ (±0.2 °2θ; ±0.1 °2θ; or ±0.0 °2θ; Cu Kα1 radiation). In some embodiments, the solid form of tabernanthalog succinate salt is crystalline tabernanthalog succinate characterized by XRPD signals at 8.3 °2θ, 17.2 °2θ, 24.7°2θ, 22.2 °2θ, 15.4 °2θ, 24.1 °2θ, 16.1 °2θ, 11.0 °2θ, 21.3 °2θ, and 20.1 °2θ (±0.2°2θ; ±0.1°2θ; or 0.0 °2θ; Cu Kα1 radiation).

In some embodiments, the crystalline tabernanthalog succinate salt is characterized by one, two, three, four, five, six, seven, eight, nine, ten, eleven, twelve, thirteen, fourteen, fifteen, sixteen, or seventeen XRPD signals selected from those set forth in Table 229.

In some embodiments, the solid form of tabernanthalog tartrate salt is crystalline tabernanthalog tartrate characterized by two or more, or three or more XRPD signals selected from the group consisting of 17.3 °2θ, 20.4 °2θ, and 22.3 °2θ (±0.2 °2θ; ±0.1°2θ; or ±0.0 °2θ; Cu Kα1 radiation). In some embodiments, the solid form tabernanthalog tartrate salt is crystalline tabernanthalog tartrate characterized by XRPD signals at 17.3 °2θ, 20.4°2θ, and 22.3 °2θ (±0.2 °2θ; ±0.1°2θ; or ±0.0 °2θ; Cu Kα1 radiation).

In some embodiments, the solid form of tabernanthalog tartrate salt is crystalline tabernanthalog tartrate characterized by two or more, or three or more XRPD signals selected from the group consisting of at 17.3 °2θ, 20.4 °2θ, 22.3 °2θ, 21.3 °2θ, and 16.4 °2θ (±0.2°2θ; ±0.1 °2θ; or 0.0 °2θ; Cu Kα1 radiation). In some embodiments, the solid form of tabernanthalog tartrate salt is crystalline tabernanthalog tartrate characterized by XRPD signals 17.3 °2θ, 20.4 °2θ, 22.3°2θ, 21.3 °2θ, and 16.4°2θ (±0.2 °2θ; ±0.1°2θ; or ±0.0 °2θ; Cu Kα1 radiation).

In some embodiments, the solid form of tabernanthalog tartrate salt is crystalline tabernanthalog tartrate characterized by two or more, or three or more XRPD signals selected from the group consisting of 17.3 °2θ, 20.4 °2θ, 22.3 °2θ, 21.3 °2θ, 16.4 °2θ, 28.3 °2θ, and 19.9°2θ (±0.2°2θ; ±0.1 °2θ; or 0.0 °2θ; Cu Kα1 radiation). In some embodiments, the solid form of tabernanthalog tartrate salt is crystalline tabernanthalog tartrate characterized by XRPD signals at 17.3 °2θ, 20.4 °2θ, 22.3 °2θ, 21.3 °2θ, 16.4 °2θ, 28.3 °2θ, and 19.9°2θ (±0.2 °2θ; ±0.1 °2θ; or ±0.0 °2θ; Cu Kα1 radiation).

In some embodiments, the solid form of tabernanthalog tartrate salt is crystalline tabernanthalog tartrate characterized by two or more, or three or more XRPD signals selected from the group consisting of 17.3 °2θ, 20.4 °2θ, 22.3 °2θ, 21.3 °2θ, 16.4°2θ, 28.3 °2θ, 19.9 °2θ, 26.1 °2θ, 24.0 °2θ, and 16.1 °2θ (±0.2 °2θ; ±0.1 °2θ; or ±0.0 °2θ; Cu Kα1 radiation). In some embodiments, the solid form of tabernanthalog tartrate salt is crystalline tabernanthalog tartrate characterized by XRPD signals at 17.3 °2θ, 20.4 °2θ, 22.3 °2θ, 21.3 °2θ, 16.4 °2θ, 28.3 °2θ, 19.9 °2θ, 26.1 °2θ, 24.0 °2θ, and 16.1°2θ (±0.2 °2θ; ±0.1°2θ; or 0.0 °2θ; Cu Kα1 radiation).

In some embodiments, the crystalline tabernanthalog tartrate salt is characterized by one, two, three, four, five, six, seven, eight, nine, ten, eleven, twelve, thirteen, fourteen, or fifteen XRPD signals selected from those set forth in Table 230.

In some embodiments, the solid form of tabernanthalog benzoate salt is crystalline tabernanthalog benzoate characterized by two or more XRPD signals selected from the group consisting of 9.0 °2θ, 18.0 °2θ, and 23.8 °2θ (±0.2 °2θ; ±0.1 °2θ; or ±0.0 °2θ; Cu Kα1 radiation). In some embodiments, the solid form tabernanthalog benzoate salt is crystalline tabernanthalog benzoate characterized by XRPD signals at 9.0 °2θ, 18.0 °2θ, and 23.8°2θ (±0.2 °2θ; ±0.1 °2θ; or ±0.0 °2θ; Cu Kα1 radiation).

In some embodiments, the crystalline tabernanthalog benzoate salt is characterized by one, two, or three XRPD signals selected from those set forth in Table 231.

In some embodiments, the solid form of tabernanthalog sorbate salt is crystalline tabernanthalog sorbate characterized by two or more XRPD signals selected from the group consisting of 5.7 °2θ, 11.4 °2θ, and 24.7°2θ (±0.2 °2θ; ±0.1°2θ; or ±0.0 °2θ; Cu Kα1 radiation). In some embodiments, the solid form tabernanthalog sorbate salt is crystalline tabernanthalog sorbate characterized by XRPD signals at 5.7 °2θ, 11.4 °2θ, and 24.7 °2θ (±0.2 °2θ; ±0.1 °2θ; or ±0.0 °2θ; Cu Kα1 radiation).

In some embodiments, the solid form of tabernanthalog sorbate salt is crystalline tabernanthalog sorbate characterized by two, three, or more XRPD signals selected from the group consisting of 5.7 °2θ, 11.4 °2θ, 24.7°2θ, and 22.6°2θ (±0.2°2θ; ±0.1 °2θ; or 0.0 °2θ; Cu Kα1 radiation). In some embodiments, the solid form tabernanthalog sorbate salt is crystalline tabernanthalog sorbate characterized by XRPD signals at 5.7 °2θ, 11.4 °2θ, 24.7 °2θ, and 22.6 °2θ (±0.2°2θ; ±0.1 °2θ; or ±0.0 °2θ; Cu Kα1 radiation).

In some embodiments, the crystalline tabernanthalog sorbate salt is characterized by one, two, three, or four XRPD signals selected from those set forth in Table 232.

In some embodiments, the solid form of tabernanthalog sorbate salt is crystalline tabernanthalog sorbate characterized by two or more XRPD signals selected from the group consisting of 5.7 °2θ, 11.4 °2θ, and 22.8 °2θ (±0.2 °2θ; ±0.1°2θ; or 0.0 °2θ; Cu Kα1 radiation). In some embodiments, the solid form tabernanthalog sorbate salt is crystalline tabernanthalog sorbate characterized by XRPD signals at 5.7 °2θ, 11.4 °2θ, and 22.8 °2θ (±0.2 °2θ; ±0.1°2θ; or 0.0 °2θ; Cu Kα1 radiation).

In some embodiments, the crystalline tabernanthalog sorbate salt is characterized by one, two, or three XRPD signals selected from those set forth in Table 233.

In some embodiments, the solid form of tabernanthalog benzoate salt is crystalline tabernanthalog benzoate characterized by two or more, or three or more XRPD signals selected from the group consisting of 23.7 °2θ, 18.1 °2θ, and 16.7°2θ (±0.2 °2θ; ±0.1 °2θ; or 0.0 °2θ; Cu Kα1 radiation). In some embodiments, the solid form tabernanthalog benzoate salt is crystalline tabernanthalog benzoate characterized by XRPD signals at 23.7 °2θ, 18.1 °2θ, and 16.7°2θ (±0.2 °2θ; ±0.1 °2θ; or ±0.0 °2θ; Cu Kα1 radiation).

In some embodiments, the solid form of tabernanthalog benzoate salt is crystalline tabernanthalog benzoate characterized by two or more, or three or more XRPD signals selected from the group consisting of 23.7 °2θ, 18.1 °2θ, 16.7 °2θ, 9.0 °2θ, and 15.7°2θ (±0.2°2θ; ±0.1 °2θ; or 0.0 °2θ; Cu Kα1 radiation). In some embodiments, the solid form of tabernanthalog benzoate salt is crystalline tabernanthalog benzoate characterized by XRPD signals at 23.7 °2θ, 18.1 °2θ, 16.7 °2θ, 9.0 °2θ, and 15.7 °2θ (±0.2 °2θ; ±0.1°2θ; or 0.0 °2θ; Cu Kα1 radiation).

In some embodiments, the solid form of tabernanthalog benzoate salt is crystalline tabernanthalog benzoate characterized by two or more, or three or more XRPD signals selected from the group consisting of 23.7 °2θ, 18.1 °2θ, 16.7 °2θ, 9.0 °2θ, 15.7 °2θ, 26.4 °2θ, and 14.2°2θ (±0.2 °2θ; 0.1°2θ; or ±0.0 °2θ; Cu Kα1 radiation). In some embodiments, the solid form of tabernanthalog benzoate salt is crystalline tabernanthalog benzoate characterized by XRPD signals at 23.7 °2θ, 18.1 °2θ, 16.7 °2θ, 9.0 °2θ, 15.7 °2θ, 26.4°2θ, and 14.2 °2θ (±0.2 °2θ; ±0.1°2θ; or ±0.0 °2θ; Cu Kα1 radiation).

In some embodiments, the solid form of tabernanthalog benzoate salt is crystalline tabernanthalog benzoate characterized by two or more, or three or more XRPD signals selected from the group consisting of 23.7 °2θ, 18.1 °2θ, 16.7 °2θ, 9.0 °2θ, 15.7 °2θ, 26.4 °2θ, 14.2 °2θ, 23.0 °2θ, 21.4 °2θ and 17.7 °2θ (±0.2 °2θ; ±0.1 °2θ; or 0.0 °2θ; Cu Kα1 radiation). In some embodiments, the solid form of tabernanthalog benzoate salt is crystalline tabernanthalog benzoate characterized by XRPD signals at 23.7 °2θ, 18.1 °2θ, 16.7 °2θ, 9.0 °2θ, 15.7 °2θ, 26.4 °2θ, 14.2 °2θ, 23.0 °2θ, 21.4 °2θ and 17.7 °2θ (±0.2 °2θ; ±0.1 °2θ; or ±0.0 °2θ; Cu Kα1 radiation).

In some embodiments, the crystalline tabernanthalog benzoate salt is characterized by one, two, three, four, five, six, seven, eight, nine, ten, eleven, twelve, thirteen, fourteen, fifteen, or sixteen XRPD signals selected from those set forth in Table 234.

In some embodiments, the solid form of tabernanthalog benzoate salt is crystalline tabernanthalog benzoate characterized by two or more, or three or more XRPD signals selected from the group consisting of 23.7 °2θ, 18.1 °2θ, and 16.8°2θ (±0.2 °2θ; ±0.1 °2θ; or 0.0 °2θ; Cu Kα1 radiation). In some embodiments, the solid form tabernanthalog benzoate salt is crystalline tabernanthalog benzoate characterized by XRPD signals at 23.7 °2θ, 18.1 °2θ, and 16.8 °2θ (±0.2 °2θ; ±0.1°2θ; or 0.0 °2θ; Cu Kα1 radiation).

In some embodiments, the solid form of tabernanthalog benzoate salt is crystalline tabernanthalog benzoate characterized by two or more, or three or more XRPD signals selected from the group consisting of 23.7 °2θ, 18.1 °2θ, 16.8 °2θ, 9.0 °2θ, and 15.7°2θ (±0.2°2θ; ±0.1°2θ; or ±0.0 °2θ; Cu Kα1 radiation). In some embodiments, the solid form of tabernanthalog benzoate salt is crystalline tabernanthalog benzoate characterized by XRPD signals at 23.7 °2θ, 18.1 °2θ, 16.8 °2θ, 9.0 °2θ, and 15.7°2θ (±0.2 °2θ; ±0.1°2θ; or 0.0 °2θ; Cu Kα1 radiation).

In some embodiments, the solid form of tabernanthalog benzoate salt is crystalline tabernanthalog benzoate characterized by two or more, or three or more XRPD signals selected from the group consisting of 23.7 °2θ, 18.1 °2θ, 16.8 °2θ, 9.0 °2θ, 15.7 °2θ, 26.4 °2θ, and 14.2°2θ (±0.2 °2θ; ±0.1°2θ; or 0.0 °2θ; Cu Kα1 radiation). In some embodiments, the solid form of tabernanthalog benzoate salt is crystalline tabernanthalog benzoate characterized by XRPD signals at 23.7 °2θ, 18.1 °2θ, 16.8 °2θ, 9.0 °2θ, 15.7 °2θ, 26.4 °2θ, and 14.2°2θ (±0.2°2θ; ±0.1°2θ; or ±0.0 °2θ; Cu Kα1 radiation).

In some embodiments, the solid form of tabernanthalog benzoate salt is crystalline tabernanthalog benzoate characterized by two or more, or three or more XRPD signals selected from the group consisting of 23.7 °2θ, 18.1 °2θ, 16.8 °2θ, 9.0 °2θ, 15.7 °2θ, 26.4 °2θ, 14.2 °2θ, 17.7 °2θ, 21.4 °2θ, and 23.0 °2θ (±0.2°2θ; ±0.1°2θ; or ±0.0 °2θ; Cu Kα1 radiation). In some embodiments, the solid form of tabernanthalog benzoate salt is crystalline tabernanthalog benzoate characterized by XRPD signals at 23.7 °2θ, 18.1 °2θ, 16.8 °2θ, 9.0 °2θ, 15.7 °2θ, 26.4 °2θ, 14.2 °2θ, 17.7 °2θ, 21.4 °2θ, and 23.0°2θ (±0.2 °2θ; ±0.1°2θ; or 0.0 °2θ; Cu Kα1 radiation).

In some embodiments, the crystalline tabernanthalog benzoate salt is characterized by one, two, three, four, five, six, seven, eight, nine, ten, eleven, or twelve XRPD signals selected from those set forth in Table 235.

In some embodiments, the solid form of tabernanthalog benzoate is crystalline tabernanthalog benzoate characterized by two or more, or three or more XRPD signals selected from the group consisting of 8.1 °2θ, 16.2 °2θ, and 17.1 °2θ (±0.2°2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 8.1 °2θ, 16.2 °2θ, and 17.1 °2θ (±0.2 °2θ; ±0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 8.1 °2θ, 16.2 °2θ, 17.1 °2θ, 23.7 °2θ, and 25.8°2θ (±0.2 °2θ; ±0.1 °2θ; or 0.0 °2θ; Cu Kα1 radiation). In some embodiments, the solid form of tabernanthalog benzoate is crystalline tabernanthalog benzoate characterized by XRPD signals at 8.1 °2θ, 16.2 °2θ, 17.1 °2θ, 23.7 °2θ, and 25.8 °2θ (±0.2 °2θ; ±0.1 °2θ; or ±0.0 °2θ; Cu Kα1 radiation).

In some embodiments, the solid form of tabernanthalog benzoate is crystalline tabernanthalog benzoate characterized by two or more, or three or more XRPD signals selected from the group consisting of 8.1 °2θ, 16.2 °2θ, 17.1 °2θ, 23.7°2θ, 25.8 °2θ, 27.7 °2θ, and 30.1°2θ (±0.2 °2θ; ±0.1°2θ;

or 0.0 °2θ; Cu Kα1 radiation). In some embodiments, the solid form of tabernanthalog benzoate is crystalline tabernanthalog benzoate characterized by XRPD signals 8.1 °2θ, 16.2 °2θ, 17.1 °2θ, 23.7 °2θ, 25.8 °2θ, 27.7 °2θ, and 30.1°2θ (±0.2°2θ; ±0.1 °2θ; or ±0.0 °2θ; Cu Kα1 radiation).

In some embodiments, the crystalline tabernanthalog benzoate is characterized by one, two, three, four, five, six, or seven XRPD signals selected from those set forth in Table 236.

In some embodiments, the solid form of tabernanthalog sorbate is crystalline tabernanthalog sorbate characterized by two or more, or three or more XRPD signals selected from the group consisting of 22.8 °2θ, 11.4 °2θ, and 27.7 °2θ (±0.2 °2θ; ±0.1°2θ; or ±0.0 °2θ; Cu Kα1 radiation).

In some embodiments, the solid form of tabernanthalog sorbate is crystalline tabernanthalog sorbate characterized by XRPD signals at 22.8 °2θ, 11.4 °2θ, and 27.7 °2θ (±0.2 °2θ; ±0.1°2θ; or 0.0 °2θ; Cu Kα1 radiation).

In some embodiments, the solid form of tabernanthalog sorbate is crystalline tabernanthalog sorbate characterized by two or more, or three or more XRPD signals selected from the group consisting of 22.8 °2θ, 11.4 °2θ, 27.7 °2θ, 24.7 °2θ, and 12.9°2θ (±0.2°2θ; ±0.1°2θ; or 0.0 °2θ; Cu Kα1 radiation). In some embodiments, the solid form of tabernanthalog sorbate is crystalline tabernanthalog sorbate characterized by XRPD signals at 22.8 °2θ, 11.4 °2θ, 27.7 °2θ, 24.7 °2θ, and 12.9°2θ (±0.2°2θ; ±0.1°2θ; or 0.0 °2θ; Cu Kα1 radiation).

In some embodiments, the solid form of tabernanthalog sorbate is crystalline tabernanthalog sorbate characterized by two or more, or three or more XRPD signals selected from the group consisting of 22.8 °2θ, 11.4 °2θ, 27.7 °2θ, 24.7 °2θ, 12.9 °2θ, and 23.4°2θ (±0.2 °2θ; ±0.1 °2θ; or ±0.0 °2θ; Cu Kα1 radiation). In some embodiments, the solid form of tabernanthalog sorbate is crystalline tabernanthalog sorbate characterized by XRPD signals at 22.8 °2θ, 11.4 °2θ, 27.7 °2θ, 24.7 °2θ, 12.9 °2θ, and 23.4 °2θ (±0.2 °2θ; ±0.1 °2θ; or 0.0 °2θ; Cu Kα1 radiation).

In some embodiments, the crystalline tabernanthalog sorbate is characterized by one, two, three, four, five, or six XRPD signals selected from those set forth in Table 237.

In some embodiments, the solid form of tabernanthalog benzoate is crystalline tabernanthalog benzoate characterized by two or more, or three or more XRPD signals selected from the group consisting of 23.7 °2θ, 18.1 °2θ, and 16.7°2θ (±0.2 °2θ; ±0.1 °2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, and 16.7 °2θ (±0.2 °2θ; ±0.1 °2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 15.6 °2θ, and 26.3°2θ (±0.2°2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 15.6 °2θ, and 26.3°2θ (±0.2 °2θ; ±0.1 °2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 15.6°2θ, 26.3 °2θ, 22.9 °2θ, and 8.9°2θ (±0.2 °2θ; ±0.1 °2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 15.6 °2θ, 26.3 °2θ, 22.9 °2θ, and 8.9°2θ (±0.2 °2θ; 0.1°2θ; or ±0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 15.6 °2θ, 26.3 °2θ, 22.9°2θ, 8.9 °2θ, 21.3 °2θ, 14.1 °2θ, and 17.6 °2θ (±0.2°2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 15.6 °2θ, 26.3 °2θ, 22.9 °2θ, 8.9 °2θ, 21.3 °2θ, 14.1 °2θ, and 17.6°2θ (±0.2 °2θ; ±0.1 °2θ; or ±0.0 °2θ; Cu Kα1 radiation).

In some embodiments, the crystalline tabernanthalog benzoate is characterized by one, two, three, four, five, six, seven, eight, nine, ten, eleven, twelve, or thirteen XRPD signals selected from those set forth in Table 238.

In some embodiments, the solid form of tabernanthalog benzoate is crystalline tabernanthalog benzoate characterized by two or more, or three or more XRPD signals selected from the group consisting of 23.7 °2θ, 18.1 °2θ, and 16.7°2θ (±0.2°2θ; ±0.1 °2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, and 16.7°2θ (±0.2 °2θ; ±0.1 °2θ; or ±0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 15.6 °2θ, and 22.9 °2θ (±0.2°2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 15.6 °2θ, and 22.9°2θ (±0.2°2θ; ±0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 15.6 °2θ, 22.9 °2θ, 26.3 °2θ, and 8.9°2θ (±0.2°2θ; ±0.1°2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 15.6 °2θ, 22.9 °2θ, 26.3 °2θ, and 8.9°2θ (±0.2°2θ, 0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 15.6 °2θ, 22.9 °2θ, 26.3 °2θ, 8.9 °2θ, 14.1 °2θ, 17.7 °2θ, and 19.6°2θ (±0.2°2θ; ±0.1°2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 15.6 °2θ, 22.9 °2θ, 26.3 °2θ, 8.9 °2θ, 14.1 °2θ, 17.7 °2θ, and 19.6°2θ (±0.2 °2θ 0.1 °2θ; or ±0.0 °2θ; Cu Kα1 radiation).

In some embodiments, the crystalline tabernanthalog benzoate is characterized by one, two, three, four, five, six, seven, eight, nine, ten, eleven, twelve, thirteen, fourteen, or fifteen XRPD signals selected from those set forth in Table 239.

In some embodiments, the solid form of tabernanthalog benzoate is crystalline tabernanthalog benzoate characterized by two or more, or three or more XRPD signals selected from the group consisting of 8.1 °2θ, 17.1 °2θ, and 16.2 °2θ

(±0.2 °2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 8.1 °2θ, 17.1 °2θ, and 16.2°2θ (±0.2 °2θ; ±0.1 °2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 8.1 °2θ, 17.1 °2θ, 16.2 °2θ, 23.7 °2θ, and 25.8°2θ (±0.2°2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 8.1 °2θ, 17.1 °2θ, 16.2 °2θ, 23.7 °2θ, and 25.8°2θ (±0.2°2θ; ±0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 8.1 °2θ, 17.1 °2θ, 16.2 °2θ, 23.7 °2θ, 25.8 °2θ, 27.7 °2θ, and 30.0 °2θ (±0.2 °2θ; ±0.1 °2θ; or 0.0 °2θ; Cu Kα1 radiation). In some embodiments, the solid form of tabernanthalog benzoate is crystalline tabernanthalog benzoate characterized by XRPD signals at 8.1 °2θ, 17.1 °2θ, 16.2 °2θ, 23.7 °2θ, 25.8 °2θ, 27.7 °2θ, and 30.0°2θ (±0.2°2θ; ±0.1°2θ; or 0.0 °2θ; Cu Kα1 radiation).

In some embodiments, the crystalline tabernanthalog benzoate is characterized by one, two, three, four, five, six, or seven XRPD signals selected from those set forth in Table 240.

In some embodiments, the solid form of tabernanthalog sorbate is crystalline tabernanthalog sorbate characterized by two or more, or three or more XRPD signals selected from the group consisting of 22.8 °2θ, 11.4 °2θ, and 12.9°2θ (±0.2°2θ; ±0.1°2θ; or ±0.0 °2θ; Cu Kα1 radiation).

In some embodiments, the solid form of tabernanthalog sorbate is crystalline tabernanthalog sorbate characterized by XRPD signals at 22.8 °2θ, 11.4 °2θ, and 12.9°2θ (±0.2°2θ; ±0.1°2θ; or 0.0 °2θ; Cu Kα1 radiation).

In some embodiments, the solid form of tabernanthalog sorbate is crystalline tabernanthalog sorbate characterized by two or more, or three or more XRPD signals selected from the group consisting of 22.8 °2θ, 11.4 °2θ, 12.9 °2θ, 27.7 °2θ, and 24.8 °2θ (±0.2 °2θ; ±0.1 °2θ; or ±0.0 °2θ; Cu Kα1 radiation). In some embodiments, the solid form of tabernanthalog sorbate is crystalline tabernanthalog sorbate characterized by XRPD signals at 22.8 °2θ, 11.4 °2θ, 12.9 °2θ, 27.7 °2θ, and 24.8°2θ (±0.2°2θ; ±0.1°2θ; or ±0.0 °2θ; Cu Kα1 radiation).

In some embodiments, the crystalline tabernanthalog sorbate is characterized by one, two, three, four, or five XRPD signals selected from those set forth in Table 241.

In some embodiments, the solid form of tabernanthalog benzoate is crystalline tabernanthalog benzoate characterized by two or more, or three or more XRPD signals selected from the group consisting of 23.6 °2θ, 18.0 °2θ, and 15.6°2θ (±0.2 °2θ; ±0.1°2θ; or 0.0 °2θ; Cu Kα1 radiation). In some embodiments, the solid form of tabernanthalog benzoate is crystalline tabernanthalog benzoate characterized by XRPD signals at 23.6 °2θ, 18.0 °2θ, and 15.6°2θ (±0.2 °2θ; ±0.1 °2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.6 °2θ, 18.0 °2θ, 15.6 °2θ, 16.7 °2θ, and 26.3°2θ (±0.2°2θ; ±0.1 °2θ; or ±0.0 °2θ; Cu Kα1 radiation). In some embodiments, the solid form of tabernanthalog benzoate is crystalline tabernanthalog ben-zoate characterized by XRPD signals at 23.6 °2θ, 18.0 °2θ, 15.6 °2θ, 16.7 °2θ, and 26.3°2θ (±0.2°2θ; ±0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.6 °2θ, 18.0 °2θ, 15.6 °2θ, 16.7 °2θ, 26.3 °2θ, 22.9 °2θ, and 8.9°2θ (±0.2°2θ; ±0.1 °2θ; or 0.0 °2θ; Cu Kα1 radiation). In some embodiments, the solid form of tabernanthalog benzoate is crystalline tabernanthalog benzoate characterized by XRPD signals at 23.6 °2θ, 18.0 °2θ, 15.6 °2θ, 16.7 °2θ, 26.3 °2θ, 22.9 °2θ, and 8.9°2θ (±0.2°2θ; ±0.1°2θ; or ±0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.6 °2θ, 18.0 °2θ, 15.6 °2θ, 16.7 °2θ, 26.3 °2θ, 22.9 °2θ, 8.9 °2θ, 21.3 °2θ, 17.6 °2θ, and 28.8 °2θ (±0.2 °2θ; ±0.1°2θ; or ±0.0 °2θ; Cu Kα1 radiation). In some embodiments, the solid form of tabernanthalog benzoate is crystalline tabernanthalog benzoate characterized by XRPD signals at 23.6 °2θ, 18.0 °2θ, 15.6 °2θ, 16.7 °2θ, 26.3 °2θ, 22.9 °2θ, 8.9 °2θ, 21.3 °2θ, 17.6 °2θ, and 28.8°2θ (±0.2 °2θ; ±0.1°2θ; or ±0.0 °2θ; Cu Kα1 radiation).

In some embodiments, the crystalline tabernanthalog benzoate is characterized by one, two, three, four, five, six, seven, eight, nine, ten, eleven, twelve, thirteen, or fourteen XRPD signals selected from those set forth in Table 242.

In some embodiments, the solid form of tabernanthalog benzoate is crystalline tabernanthalog benzoate characterized by two or more, or three or more XRPD signals selected from the group consisting of 23.7 °2θ, 18.1 °2θ, and 16.7°2θ (±0.2°2θ; ±0.1 °2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, and 16.7°2θ (±0.2 °2θ; ±0.1 °2θ; or ±0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 15.7 °2θ, and 26.4°2θ (±0.2°2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 15.7 °2θ, and 26.4°2θ (±0.2°2θ; ±0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 15.7 °2θ, 26.4 °2θ, 9.0 °2θ, and 23.0°2θ (±0.2°2θ; ±0.1°2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 15.7 °2θ, 26.4 °2θ, 9.0 °2θ, and 23.0°2θ (±0.2°2θ; ±0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 15.7 °2θ, 26.4 °2θ, 9.0 °2θ, 23.0 °2θ, 21.4 °2θ, 14.2 °2θ, and 17.7°2θ (±0.2°2θ; ±0.1°2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 15.7

°2θ, 26.4 °2θ, 9.0 °2θ, 23.0 °2θ, 21.4 °2θ, 14.2 °2θ, and 17.7°2θ (±0.2°2θ; ±0.1 °2θ; or ±0.0 °2θ; Cu Kα1 radiation).

In some embodiments, the crystalline tabernanthalog benzoate is characterized by one, two, three, four, five, six, seven, eight, nine, ten, eleven, twelve, thirteen, fourteen, or fifteen XRPD signals selected from those set forth in Table 243.

In some embodiments, the solid form of tabernanthalog benzoate is crystalline tabernanthalog benzoate characterized by two or more, or three or more XRPD signals selected from the group consisting of 8.1 °2θ, 17.1 °2θ, and 23.7°2θ (±0.2 °2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 8.1 °2θ, 17.1 °2θ, and 23.7°2θ (±0.2 °2θ; ±0.1 °2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 8.1 °2θ, 17.1 °2θ, 23.7 °2θ, 25.8 °2θ, and 16.2°2θ (±0.2°2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 8.1 °2θ, 17.1 °2θ, 23.7 °2θ, 25.8 °2θ, and 16.2°2θ (±0.2°2θ; ±0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 8.1 °2θ, 17.1 °2θ, 23.7 °2θ, 25.8 °2θ, 16.2 °2θ, 27.7 °2θ, and 30.0 °2θ (±0.2 °2θ; ±0.1 °2θ; or 0.0 °2θ; Cu Kα1 radiation). In some embodiments, the solid form of tabernanthalog benzoate is crystalline tabernanthalog benzoate characterized by XRPD signals at 8.1 °2θ, 17.1 °2θ, 23.7 °2θ, 25.8°2θ, 16.2 °2θ, 27.7 °2θ, and 30.0°2θ (±0.2°2θ; ±0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 8.1 °2θ, 17.1 °2θ, 23.7 °2θ, 25.8 °2θ, 16.2 °2θ, 27.7 °2θ, 30.0°2θ and 19.0°2θ (±0.2°2θ; ±0.1°2θ; or ±0.0 °2θ; Cu Kα1 radiation). In some embodiments, the solid form of tabernanthalog benzoate is crystalline tabernanthalog benzoate characterized by XRPD signals at 8.1 °2θ, 17.1 °2θ, 23.7 °2θ, 25.8 °2θ, 16.2 °2θ, 27.7 °2θ, 30.0°2θ and 19.0°2θ (±0.2°2θ; ±0.1°2θ; or 0.0 °2θ; Cu Kα1 radiation).

In some embodiments, the crystalline tabernanthalog benzoate is characterized by one, two, three, four, five, six, seven, or eight XRPD signals selected from those set forth in Table 244.

In some embodiments, the solid form of tabernanthalog sorbate is crystalline tabernanthalog sorbate characterized by two or more, or three or more XRPD signals selected from the group consisting of 22.8 °2θ, 11.4 °2θ, and 12.9°2θ (±0.2 °2θ; ±0.1 °2θ; or ±0.0 °2θ; Cu Kα1 radiation).

In some embodiments, the solid form of tabernanthalog sorbate is crystalline tabernanthalog sorbate characterized by XRPD signals at 22.8 °2θ, 11.4 °2θ, and 12.9°2θ (±0.2°2θ; ±0.1°2θ; or ±0.0 °2θ; Cu Kα1 radiation).

In some embodiments, the solid form of tabernanthalog sorbate is crystalline tabernanthalog sorbate characterized by two or more, or three or more XRPD signals selected from the group consisting of 22.8 °2θ, 11.4 °2θ, 12.9 °2θ, 27.7 °2θ, and 24.7 °2θ (±0.2 °2θ; ±0.1°2θ; or 0.0 °2θ; Cu Kα1 radiation). In some embodiments, the solid form of tabernanthalog sorbate is crystalline tabernanthalog sorbate characterized by XRPD signals at 22.8 °2θ, 11.4 °2θ, 12.9 °2θ, 27.7 °2θ, and 24.7°2θ (±0.2°2θ; ±0.1°2θ; or 0.0 °2θ; Cu Kα1 radiation).

In some embodiments, the crystalline tabernanthalog sorbate is characterized by one, two, three, four, or five XRPD signals selected from those set forth in Table 245.

In some embodiments, the solid form of tabernanthalog benzoate is crystalline tabernanthalog benzoate characterized by two or more, or three or more XRPD signals selected from the group consisting of 23.7 °2θ, 18.1 °2θ, and 15.7 °2θ (±0.2 °2θ; ±0.1 °2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, and 15.7 °2θ (±0.2 °2θ; ±0.1 °2θ; or ±0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 15.7 °2θ, 16.8 °2θ, and 26.4°2θ (±0.2°2θ; ±0.1 °2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 15.7 °2θ, 16.8 °2θ, and 26.4 °2θ (±0.2 °2θ; ±0.1 °2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 15.7 °2θ, 16.8 °2θ, 26.4 °2θ, 9.0 °2θ, and 23.0°2θ (±0.2°2θ; ±0.1°2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 15.7 °2θ, 16.8 °2θ, 26.4 °2θ, 9.0 °2θ, and 23.0 °2θ (±0.2°2θ; ±0.1 °2θ; or ±0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 15.7 °2θ, 16.8 °2θ, 26.4 °2θ, 9.0 °2θ, 23.0 °2θ, 14.2 °2θ, 17.7 °2θ, and 21.4°2θ (±0.2°2θ; ±0.1 °2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 15.7 °2θ, 16.8°2θ, 26.4 °2θ, 9.0 °2θ, 23.0 °2θ, 14.2 °2θ, 17.7 °2θ, and 21.4 °2θ (±0.2°2θ; ±0.1°2θ; or 0.0 °2θ; Cu Kα1 radiation).

In some embodiments, the crystalline tabernanthalog benzoate is characterized by one, two, three, four, five, six, seven, eight, nine, ten, eleven, twelve, thirteen, fourteen, or fifteen XRPD signals selected from those set forth in Table 246.

In some embodiments, the solid form of tabernanthalog benzoate is crystalline tabernanthalog benzoate characterized by two or more, or three or more XRPD signals selected from the group consisting of 23.7 °2θ, 18.1 °2θ, and 16.7°2θ (±0.2°2θ; ±0.1°2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, and 16.7°2θ (±0.2 °2θ; ±0.1 °2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 26.3 °2θ, and 15.6°2θ (±0.2°2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 26.3 °2θ, and 15.6°2θ (±0.2 °2θ; ±0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 26.3 °2θ, 15.6 °2θ, 22.9 °2θ, and 21.3 °2θ (±0.2 °2θ; ±0.1 °2θ; or 0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 26.3 °2θ, 15.6 °2θ, 22.9 °2θ, and 21.3°2θ (±0.2°2θ; ±0.1 °2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 18.1 °2θ, 16.7 °2θ, 26.3 °2θ, 15.6 °2θ, 22.9 °2θ, 21.3 °2θ, 14.1 °2θ, 8.9 °2θ, and 17.7°2θ (±0.2 °2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 23.7 °2θ, 18.1 °2θ, 16.7 °2θ, 26.3 °2θ, 15.6 °2θ, 22.9 °2θ, 21.3 °2θ, 14.1 °2θ, 8.9 °2θ, and 17.7°2θ (±0.2 °2θ; ±0.1°2θ; or ±0.0 °2θ; Cu Kα1 radiation).

In some embodiments, the crystalline tabernanthalog benzoate is characterized by one, two, three, four, five, six, seven, eight, nine, ten, eleven, twelve, or thirteen XRPD signals selected from those set forth in Table 247.

In some embodiments, the solid form of tabernanthalog benzoate is crystalline tabernanthalog benzoate characterized by two or more, or three or more XRPD signals selected from the group consisting of 8.1 °2θ, 23.7 °2θ, and 17.1 °2θ (±0.2°2θ; ±0.1 °2θ; or ±0.0 °2θ; Cu Kai radiation). In some embodiments, the solid form of tabernanthalog benzoate is crystalline tabernanthalog benzoate characterized by XRPD signals at 8.1 °2θ, 23.7 °2θ, and 17.1 °2θ (±0.2 °2θ; ±0.1 °2θ; or ±0.0 °2θ; Cu Kα1 radiation).

In some embodiments, the solid form of tabernanthalog benzoate is crystalline tabernanthalog benzoate characterized by two or more, or three or more XRPD signals selected from the group consisting of 8.1 °2θ, 23.7 °2θ, 17.1 °2θ, 25.7 °2θ, and 16.2°2θ (±0.2°2θ; ±0.1°2θ; or 0.0 °2θ; Cu Kα1 radiation). In some embodiments, the solid form of tabernanthalog benzoate is crystalline tabernanthalog benzoate characterized by XRPD signals at 8.1 °2θ, 23.7 °2θ, 17.1 °2θ, 25.7 °2θ, and 16.2°2θ (±0.2 °2θ; 0.1 °2θ; or ±0.0 °2θ; Cu Kα1 radiation).

In some embodiments, the solid form of tabernanthalog benzoate is crystalline tabernanthalog benzoate characterized by two or more, or three or more XRPD signals selected from the group consisting of 8.1 °2θ, 23.7 °2θ, 17.1 °2θ, 25.7 °2θ, 16.2 °2θ, 27.6 °2θ, and 30.0°2θ (±0.2°2θ; ±0.1°2θ; or 0.0 °2θ; Cu Kα1 radiation). In some embodiments, the solid form of tabernanthalog benzoate is crystalline tabernanthalog benzoate characterized by XRPD signals at 8.1 °2θ, 23.7 °2θ, 17.1 °2θ, 25.7 °2θ, 16.2 °2θ, 27.6 °2θ, and 30.0°2θ (±0.2°2θ; ±0.1°2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 8.1 °2θ, 23.7 °2θ, 17.1 °2θ, 25.7 °2θ, 16.2 °2θ, 27.6 °2θ, 30.0 °2θ and 19.0°2θ (±0.2°2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 8.1 °2θ, 23.7 °2θ, 17.1 °2θ, 25.7 °2θ, 16.2 °2θ, 27.6 °2θ, 30.0°2θ and 19.0°2θ (±0.2 °2θ; ±0.1 °2θ; or 0.0 °2θ; Cu Kα1 radiation).

In some embodiments, the crystalline tabernanthalog benzoate is characterized by one, two, three, four, five, six, seven, or eight XRPD signals selected from those set forth in Table 248.

In some embodiments, the solid form of tabernanthalog sorbate is crystalline tabernanthalog sorbate characterized by two or more, or three or more XRPD signals selected from the group consisting of 22.7 °2θ, 11.4 °2θ, and 12.9 °2θ (±0.2 °2θ; ±0.1°2θ; or ±0.0 °2θ; Cu Kα1 radiation).

In some embodiments, the solid form of tabernanthalog sorbate is crystalline tabernanthalog sorbate characterized by XRPD signals at 22.7 °2θ, 11.4 °2θ, and 12.9°2θ (±0.2 °2θ; ±0.1 °2θ; or 0.0 °2θ; Cu Kα1 radiation).

In some embodiments, the solid form of tabernanthalog sorbate is crystalline tabernanthalog sorbate characterized by two or more, or three or more XRPD signals selected from the group consisting of 22.7 °2θ, 11.4 °2θ, 12.9 °2θ, 27.7 °2θ, and 24.7°2θ (±0.2°2θ; ±0.1°2θ; or ±0.0 °2θ; Cu Kα1 radiation). In some embodiments, the solid form of tabernanthalog sorbate is crystalline tabernanthalog sorbate characterized by XRPD signals at 22.7 °2θ, 11.4 °2θ, 12.9 °2θ, 27.7 °2θ, and 24.7°2θ (±0.2°2θ; ±0.1 °2θ; or ±0.0 °2θ; Cu Kα1 radiation).

In some embodiments, the crystalline tabernanthalog sorbate is characterized by one, two, three, four, or five XRPD signals selected from those set forth in Table 249.

In some embodiments, the solid form of tabernanthalog monofumarate is crystalline tabernanthalog monofumarate characterized by two or more, or three or more XRPD signals selected from the group consisting of 19.5 °2θ, 16.5 °2θ, and 20.6 °2θ (±0.2 °2θ; ±0.1°2θ; or ±0.0 °2θ; Cu Kα1 radiation). In some embodiments, the solid form of tabernanthalog monofumarate is crystalline tabernanthalog monofumarate characterized by XRPD signals at 19.5 °2θ, 16.5 °2θ, and 20.6°2θ (±0.2°2θ; ±0.1 °2θ; or ±0.0 °2θ; Cu Kα1 radiation).

In some embodiments, the solid form of tabernanthalog monofumarate is crystalline tabernanthalog monofumarate characterized by two or more, or three or more XRPD signals selected from the group consisting of 19.5 °2θ, 16.5 °2θ, 20.6 °2θ, 25.3 °2θ, and 26.1 °2θ (±0.2°2θ; ±0.1 °2θ; or 0.0 °2θ; Cu Kα1 radiation). In some embodiments, the solid form of tabernanthalog monofumarate is crystalline tabernanthalog monofumarate characterized by XRPD signals at 19.5 °2θ, 16.5 °2θ, 20.6 °2θ, 25.3 °2θ, and 26.1 °2θ (±0.2 °2θ; ±0.1 °2θ; or 0.0 °2θ; Cu Kα1 radiation).

In some embodiments, the solid form of tabernanthalog monofumarate is crystalline tabernanthalog monofumarate characterized by two or more, or three or more XRPD signals selected from the group consisting of 19.5 °2θ, 16.5 °2θ, 20.6 °2θ, 25.3 °2θ, 26.1 °2θ, 22.1 °2θ, and 33.5°2θ (±0.2°2θ; ±0.1 °2θ; or ±0.0 °2θ; Cu Kα1 radiation). In some embodiments, the solid form of tabernanthalog monofumarate is crystalline tabernanthalog monofumarate characterized by XRPD signals at 19.5 °2θ, 16.5 °2θ, 20.6 °2θ, 25.3 °2θ, 26.1 °2θ, 22.1 °2θ, and 33.5 °2θ (±0.2 °2θ; ±0.1°2θ; or 0.0 °2θ; Cu Kα1 radiation).

In some embodiments, the solid form of tabernanthalog monofumarate is crystalline tabernanthalog monofumarate characterized by two or more, or three or more XRPD signals selected from the group consisting of 19.5 °2θ, 16.5 °2θ, 20.6 °2θ, 25.3 °2θ, 26.1 °2θ, 22.1 °2θ, 33.5 °2θ and 12.9°2θ (±0.2 °2θ; ±0.1°2θ; or 0.0 °2θ; Cu Kα1 radiation). In some embodiments, the solid form of tabernanthalog monofumarate is crystalline tabernanthalog monofumarate characterized by XRPD signals at 19.5 °2θ, 16.5 °2θ, 20.6 °2θ, 25.3 °2θ, 26.1 °2θ, 22.1 °2θ, 33.5 °2θ and 12.9°2θ (±0.2 °2θ; ±0.1°2θ; or 0.0 °2θ; Cu Kα1 radiation).

In some embodiments, the crystalline tabernanthalog monofumarate is characterized by one, two, three, four, five, six, seven, eight, or nine XRPD signals selected from those set forth in Table 250.

In some embodiments, the solid form of tabernanthalog monofumarate is crystalline tabernanthalog monofumarate characterized by two or more, or three or more XRPD signals selected from the group consisting of 19.6 °2θ, 16.6 °2θ, and 20.7°2θ (±0.2 °2θ; ±0.1°2θ; or 0.0 °2θ; Cu Kα1 radiation). In some embodiments, the solid form of tabernanthalog monofumarate is crystalline tabernanthalog monofumarate characterized by XRPD signals at 19.6 °2θ, 16.6°2θ, and 20.7°2θ (±0.2°2θ; ±0.1°2θ; or 0.0 °2θ; Cu Kα1 radiation).

In some embodiments, the solid form of tabernanthalog monofumarate is crystalline tabernanthalog monofumarate characterized by two or more, or three or more XRPD signals selected from the group consisting of 19.6 °2θ, 16.6 °2θ, 20.7 °2θ, 25.3 °2θ, and 26.1°2θ (±0.2°2θ; ±0.1 °2θ; or ±0.0 °2θ; Cu Kα1 radiation). In some embodiments, the solid form of tabernanthalog monofumarate is crystalline tabernanthalog monofumarate characterized by XRPD signals at 19.6 °2θ, 16.6 °2θ, 20.7 °2θ, 25.3 °2θ, and 26.1°2θ (±0.2°2θ; ±0.1 °2θ; or ±0.0 °2θ; Cu Kα1 radiation).

In some embodiments, the solid form of tabernanthalog monofumarate is crystalline tabernanthalog monofumarate characterized by two or more, or three or more XRPD signals selected from the group consisting of 19.6 °2θ, 16.6 °2θ, 20.7 °2θ, 25.3 °2θ, 26.1 °2θ, 22.1 °2θ, and 33.5 °2θ (±0.2°2θ; ±0.1 °2θ; or ±0.0 °2θ; Cu Kα1 radiation). In some embodiments, the solid form of tabernanthalog monofumarate is crystalline tabernanthalog monofumarate characterized by XRPD signals at 19.6 °2θ, 16.6 °2θ, 20.7 °2θ, 25.3 °2θ, 26.1 °2θ, 22.1 °2θ, and 33.5°2θ (±0.2 °2θ; ±0.1°2θ; or ±0.0 °2θ; Cu Kα1 radiation).

In some embodiments, the solid form of tabernanthalog monofumarate is crystalline tabernanthalog monofumarate characterized by two or more, or three or more XRPD signals selected from the group consisting of 19.6 °2θ, 16.6 °2θ, 20.7 °2θ, 25.3 °2θ, 26.1 °2θ, 22.1 °2θ, 33.5 °2θ, and 13.0°2θ (±0.2°2θ; ±0.1°2θ; or 0.0 °2θ; Cu Kα1 radiation). In some embodiments, the solid form of tabernanthalog monofumarate is crystalline tabernanthalog monofumarate characterized by XRPD signals at 19.6 °2θ, 16.6 °2θ, 20.7 °2θ, 25.3 °2θ, 26.1 °2θ, 22.1 °2θ, 33.5 °2θ, and 13.0°2θ (±0.2°2θ; ±0.1°2θ; or 0.0 °2θ; Cu Kα1 radiation).

In some embodiments, the crystalline tabernanthalog monofumarate is characterized by one, two, three, four, five, six, seven, or eight XRPD signals selected from those set forth in Table 251.

In some embodiments, the solid form of tabernanthalog tartrate is crystalline tabernanthalog tartrate characterized by two or more, or three or more XRPD signals selected from the group consisting of 17.3 °2θ, 20.4 °2θ, and 22.4°2θ (±0.2°2θ; ±0.1°2θ; or 0.0 °2θ; Cu Kα1 radiation).

In some embodiments, the solid form of tabernanthalog tartrate is crystalline tabernanthalog tartrate characterized by XRPD signals at 17.3 °2θ, 20.4 °2θ, and 22.4°2θ (±0.2°2θ; ±0.1°2θ; or 0.0 °2θ; Cu Kα1 radiation).

In some embodiments, the solid form of tabernanthalog tartrate is crystalline tabernanthalog tartrate characterized by two or more, or three or more XRPD signals selected from the group consisting of 17.3 °2θ, 20.4 °2θ, 22.4 °2θ, 21.3 °2θ, and 16.4 °2θ (±0.2 °2θ; ±0.1 °2θ; or ±0.0 °2θ; Cu Kα1 radiation). In some embodiments, the solid form of tabernanthalog tartrate is crystalline tabernanthalog tartrate characterized by XRPD signals at 17.3 °2θ, 20.4 °2θ, 22.4 °2θ, 21.3 °2θ, and 16.4°2θ (±0.2°2θ; ±0.1°2θ; or ±0.0 °2θ; Cu Kα1 radiation).

In some embodiments, the solid form of tabernanthalog tartrate is crystalline tabernanthalog tartrate characterized by two or more, or three or more XRPD signals selected from the group consisting of 17.3 °2θ, 20.4 °2θ, 22.4 °2θ, 21.3 °2θ, 16.4 °2θ, 28.3 °2θ, and 19.9 °2θ (±0.2°2θ; ±0.1 °2θ; or ±0.0 °2θ; Cu Kα1 radiation). In some embodiments, the solid form of tabernanthalog tartrate is crystalline tabernanthalog tartrate characterized by XRPD signals at 17.3 °2θ, 20.4 °2θ, 22.4 °2θ, 21.3 °2θ, 16.4 °2θ, 28.3 °2θ, and 19.9°2θ (±0.2°2θ; ±0.1 °2θ; or 0.0 °2θ; Cu Kα1 radiation).

In some embodiments, the solid form of tabernanthalog tartrate is crystalline tabernanthalog tartrate characterized by two or more, or three or more XRPD signals selected from the group consisting of 17.3 °2θ, 20.4 °2θ, 22.4 °2θ, 21.3 °2θ, 16.4 °2θ, 28.3 °2θ, 19.9 °2θ, 26.1 °2θ, 24.0 °2θ, and 16.1°2θ (±0.2 °2θ; ±0.1 °2θ; or 0.0 °2θ; Cu Kα1 radiation). In some embodiments, the solid form of tabernanthalog tartrate is crystalline tabernanthalog tartrate characterized by XRPD signals at 17.3 °2θ, 20.4 °2θ, 22.4 °2θ, 21.3 °2θ, 16.4 °2θ, 28.3 °2θ, 19.9 °2θ, 26.1 °2θ, 24.0 °2θ, and 16.1 °2θ (±0.2 °2θ; ±0.1°2θ; or 0.0 °2θ; Cu Kα1 radiation).

In some embodiments, the crystalline tabernanthalog tartrate is characterized by one, two, three, four, five, six, seven, eight, nine, ten, eleven, twelve, thirteen, or fourteen XRPD signals selected from those set forth in Table 252.

In some embodiments, the solid form of tabernanthalog tartrate is crystalline tabernanthalog tartrate characterized by two or more, or three or more XRPD signals selected from the group consisting of 17.4 °2θ, 20.5 °2θ, and 22.5°2θ (±0.2 °2θ; ±0.1°2θ; or ±0.0 °2θ; Cu Kα1 radiation).

In some embodiments, the solid form of tabernanthalog tartrate is crystalline tabernanthalog tartrate characterized by XRPD signals at 17.4 °2θ, 20.5 °2θ, and 22.5°2θ (±0.2 °2θ; 0.1°2θ; or ±0.0 °2θ; Cu Kα1 radiation).

In some embodiments, the solid form of tabernanthalog tartrate is crystalline tabernanthalog tartrate characterized by two or more, or three or more XRPD signals selected from the group consisting of 17.4 °2θ, 20.5 °2θ, 22.5 °2θ, 21.4 °2θ, and 16.5°2θ (±0.2°2θ; ±0.1 °2θ; or ±0.0 °2θ; Cu Kα1 radiation). In some embodiments, the solid form of tabernanthalog tartrate is crystalline tabernanthalog tartrate characterized by XRPD signals at 17.4 °2θ, 20.5 °2θ, 22.5 °2θ, 21.4 °2θ, and 16.5°2θ (±0.2°2θ; ±0.1°2θ; or 0.0 °2θ; Cu Kα1 radiation).

In some embodiments, the solid form of tabernanthalog tartrate is crystalline tabernanthalog tartrate characterized by two or more, or three or more XRPD signals selected from the group consisting of 17.4 °2θ, 20.5 °2θ, 22.5 °2θ, 21.4 °2θ, 16.5 °2θ, 28.4 °2θ, and 20.0 °2θ (±0.2 °2θ; ±0.1 °2θ; or 0.0 °2θ; Cu Kα1 radiation). In some embodiments, the solid form of tabernanthalog tartrate is crystalline tabernanthalog tartrate characterized by XRPD signals at 17.4 °2θ, 20.5 °2θ, 22.5 °2θ, 21.4 °2θ, 16.5 °2θ, 28.4 °2θ, and 20.0°2θ (±0.2°2θ; ±0.1°2θ; or ±0.0 °2θ; Cu Kα1 radiation).

In some embodiments, the solid form of tabernanthalog tartrate is crystalline tabernanthalog tartrate characterized by two or more, or three or more XRPD signals selected from the group consisting of 17.4 °2θ, 20.5 °2θ, 22.5 °2θ, 21.4 °2θ, 16.5 °2θ, 28.4 °2θ, 20.0 °2θ, 16.2 °2θ, 24.1 °2θ, and 26.2 °2θ (±0.2 °2θ; ±0.1 °2θ; or 0.0 °2θ; Cu Kα1 radiation). In some embodiments, the solid form of tabernanthalog tartrate is crystalline tabernanthalog tartrate characterized by XRPD signals at 17.4 °2θ, 20.5 °2θ, 22.5 °2θ, 21.4 °2θ, 16.5 °2θ, 28.4 °2θ, 20.0 °2θ, 16.2 °2θ, 24.1 °2θ, and 26.2 °2θ (±0.2 °2θ; ±0.1 °2θ; or 0.0 °2θ; Cu Kα1 radiation).

In some embodiments, the crystalline tabernanthalog tartrate is characterized by one, two, three, four, five, six, seven, eight, nine, ten, or eleven XRPD signals selected from those set forth in Table 253.

In some embodiments, the solid form of tabernanthalog benzoate is crystalline tabernanthalog benzoate characterized by two or more, or three or more XRPD signals selected from the group consisting of 9.0 °2θ, 18.0 °2θ, and 23.7 °2θ (±0.2 °2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 9.0 °2θ, 18.0 °2θ, and 23.7 °2θ (±0.2 °2θ; ±0.1 °2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 9.0 °2θ, 18.0 °2θ, 23.7 °2θ, 9.1 °2θ, and 27.1 °2θ (±0.2 °2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 9.0 °2θ, 18.0 °2θ, 23.7 °2θ, 9.1 °2θ, and 27.1 °2θ (±0.2 °2θ; ±0.1 °2θ; or 0.0 °2θ; Cu Kα1 radiation).

In some embodiments, the crystalline tabernanthalog benzoate is characterized by one, two, three, four, or five XRPD signals selected from those set forth in Table 254.

In some embodiments, the solid form of tabernanthalog benzoate is crystalline tabernanthalog benzoate characterized by two or more, or three or more XRPD signals selected from the group consisting of 23.7 °2θ, 9.0 °2θ, and 26.4 °2θ (±0.2 °2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 23.7 °2θ, 9.0 °2θ, and 26.4 °2θ (±0.2 °2θ; ±0.1 °2θ; or ±0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 9.0 °2θ, 26.4 °2θ, 18.1 °2θ, and 24.4 °2θ (±0.2 °2θ; ±0.1 °2θ; or ±0.0 °2θ; Cu Kα1 radiation). In some embodiments, the solid form of tabernanthalog benzoate is crystalline tabernanthalog benzoate characterized by XRPD signals at 23.7 °2θ, 9.0 °2θ, 26.4 °2θ, 18.1 °2θ, and 24.4°2θ (±0.2 °2θ; ±0.1 °2θ; or 0.0 °2θ; Cu Kα1 radiation).

In some embodiments, the solid form of tabernanthalog benzoate is crystalline tabernanthalog benzoate characterized by two or more, or three or more XRPD signals selected from the group consisting of 23.7 °2θ, 9.0 °2θ, 26.4 °2θ, 18.1 °2θ, 24.4 °2θ, 19.7 °2θ, and 16.8°2θ (±0.2 °2θ, ±0.1 °2θ; or ±0.0 °2θ; Cu Kα1 radiation). In some embodiments, the solid form of tabernanthalog benzoate is crystalline tabernanthalog benzoate characterized by XRPD signals at 23.7 °2θ, 9.0 °2θ, 26.4 °2θ, 18.1 °2θ, 24.4 °2θ, 19.7 °2θ, and 16.8°2θ (±0.2°2θ; ±0.1°2θ; or ±0.0 °2θ; Cu Kα1 radiation).

In some embodiments, the crystalline tabernanthalog benzoate is characterized by one, two, three, four, five, six, seven, or eight XRPD signals selected from those set forth in Table 255.

In some embodiments, the solid form of tabernanthalog sorbate is crystalline tabernanthalog sorbate characterized by two or more, or three or more XRPD signals selected from the group consisting of 5.7 °2θ, 11.5 °2θ, and 18.9 °2θ (±0.2 °2θ; ±0.1 °2θ; or ±0.0 °2θ; Cu Kα1 radiation). In some embodiments, the solid form of tabernanthalog sorbate is crystalline tabernanthalog sorbate characterized by XRPD signals at 5.7 °2θ, 11.5 °2θ, and 18.9°2θ (±0.2°2θ; ±0.1°2θ; or 0.0 °2θ; Cu Kα1 radiation).

In some embodiments, the solid form of tabernanthalog sorbate is crystalline tabernanthalog sorbate characterized by two or more, or three or more XRPD signals selected from the group consisting of 5.7 °2θ, 11.5 °2θ, 18.9 °2θ, and 23.0°2θ (±0.2°2θ; ±0.1°2θ; or 0.0 °2θ; Cu Kα1 radiation). In some embodiments, the solid form of tabernanthalog sorbate is crystalline tabernanthalog sorbate characterized by XRPD signals at 5.7 °2θ, 11.5 °2θ, 18.9 °2θ, and 23.0°2θ (±0.2°2θ; ±0.1 °2θ; or 0.0 °2θ; Cu Kα1 radiation).

In some embodiments, the crystalline tabernanthalog sorbate is characterized by one, two, three, or four XRPD signals selected from those set forth in Table 256.

In some embodiments, the solid form of tabernanthalog sorbate is crystalline tabernanthalog sorbate characterized by two or more, or three or more XRPD signals selected from the group consisting of 5.7 °2θ, 11.4 °2θ, and 18.9°2θ (±0.2 °2θ; ±0.1°2θ; or 0.0 °2θ; Cu Kα1 radiation). In some embodiments, the solid form of tabernanthalog sorbate is crystalline tabernanthalog sorbate characterized by XRPD signals at 5.7 °2θ, 11.4 °2θ, and 18.9 °2θ (±0.2 °2θ; ±0.1 °2θ; or ±0.0 °2θ; Cu Kα1 radiation).

In some embodiments, the solid form of tabernanthalog sorbate is crystalline tabernanthalog sorbate characterized by two or more, or three or more XRPD signals selected from the group consisting of 5.7 °2θ, 11.4 °2θ, 18.9 °2θ, 18.8 °2θ, and 24.6 °2θ (±0.2 °2θ; ±0.1 °2θ; or ±0.0 °2θ; Cu Kα1 radiation). In some embodiments, the solid form of tabernanthalog sorbate is crystalline tabernanthalog sorbate characterized by XRPD signals at 5.7 °2θ, 11.4 °2θ, 18.9 °2θ, 18.8 °2θ, and 24.6 °2θ (±0.2°2θ; ±0.1 °2θ; or 0.0 °2θ; Cu Kα1 radiation).

In some embodiments, the crystalline tabernanthalog sorbate is characterized by one, two, three, four, or five XRPD signals selected from those set forth in Table 257.

Pharmaceutical Compositions and Formulations

In some embodiments, the present disclosure provides a pharmaceutical composition comprising one or more of the salt or solid forms of tabernanthalog, illustrated above, and a pharmaceutically acceptable excipient. Such compositions are suitable for administration to a subject, such as a human subject.

The presently disclosed pharmaceutical compositions can be prepared in a wide variety of oral, parenteral, such as intravenous, and topical dosage forms. Oral preparations include tablets, pills, powder, capsules, lozenges, cachets, slurries, suspensions, etc., suitable for ingestion by the patient. The compositions of the present invention can also be administered as solutions, orally or parenterally, such as by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present disclosure also provides pharmaceutical compositions including a pharmaceutically acceptable carrier or excipient and the salt or solid form of tabernanthalog of the present disclosure.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from about 5% to about 70% or from about 10% to about 70% of the compounds of the present disclosure.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen.

If desired, disintegrating or solubilizing agents may be added, such as the cross-linked polyvinyl pyrrolidone, agar, alginic acid, or a salt thereof, such as sodium alginate.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions and suspensions, for example, water or water/propylene glycol suspensions.

Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include suspensions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present disclosure can also be delivered as microspheres for slow release in the body. For example, microspheres can be formulated for administration via intradermal injection of drug-containing microspheres, which slowly release subcutaneously (see Rao, J. Biomaler Sci. Polyn. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In some embodiments, the pharmaceutical compositions of the present disclosure can be formulated for parenteral administration, such as intravenous (IV) administration or administration into a body cavity or lumen of an organ. The formulations for administration will commonly comprise a solution or suspension of the compositions of the present disclosure dissolved or suspended in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions or suspensions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present disclosure in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the present disclosure can be delivered using liposomes which fuse with the cellular membrane or are endocytosed, for example, by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

In one embodiment, the compositions disclosed herein can also contain other compatible therapeutic agents. The compounds described herein can be used in combination with at least one other active agent.

In another embodiment, the compositions disclosed herein can also contain other compatible therapeutic agents. The compounds described herein can be used in combination with at least one other active agent known to be useful in modulating a glucocorticoid receptor, or with adjunctive agents that may not be effective alone, but may contribute to the efficacy of the active agent.

Administration:

The compositions of the present disclosure can be administered by any suitable means, including oral, parenteral and topical methods. Transdermal administration methods, by a topical route, can be formulated as applicator sticks, suspensions, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The salt and solid forms of tabernanthalog of the present invention can be present in any suitable amount, and can depend on various factors including, but not limited to, weight and age of the subject, state of the disease, and the like as is known to those of ordinary skill in the art.

The compound forms (salt and solid forms of tabernanthalog) disclosed herein also can be administered at any suitable frequency, interval and duration.

The compound forms of the present invention can be co-administered with a second active agent. In some embodiments, co-administration can be accomplished by co-formulation, such as by preparing a single pharmaceutical composition including both the compound form of the present disclosure (salt or solid form of tabernanthalog) and a second active agent. In other embodiments, the compound of the present disclosure and the second active agent can be formulated separately.

Methods of Treatment

In some embodiments, the salt and solid forms of the tabernanthalog of the present disclosure can be used to increase neuronal plasticity. In other embodiments, the salt and solid forms of the tabernanthalog of the present disclosure can also be used to treat any brain disease. The salt and solid forms of the tabernanthalog of the present disclosure can also be used to increase at least one of translation, transcription or secretion of neurotrophic factors.

In some embodiments, a compound of the present disclosure is used to treat neurological diseases. In some embodiments, the compound of the present disclosure has, for example, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder). In some embodiments, the neurological disease is a migraine or cluster headache. In some embodiments, the neurological disease is a neurodegenerative disorder, Alzheimer's disease, or Parkinson's disease. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, a compound of the present disclosure is used to increase neuronal plasticity. In some embodiments, the compounds of the present disclosure are used to treat a brain disorder. In some embodiments, the compounds of the present disclosure are used to increase at least one of translation, transcription, or secretion of neurotrophic factors.

In some embodiments, the present disclosure provides a method of treating a disease, including administering to a subject in need thereof, a therapeutically effective amount of a compound of the present disclosure. In some embodiments, the disease is a musculoskeletal pain disorder including fibromyalgia, muscle pain, joint stiffness, osteoarthritis, rheumatoid arthritis, muscle cramps. In some embodiments, the present invention provides a method of treating a disease of women's reproductive health including premenstrual dysphoric disorder (PMDD), premenstrual syndrome (PMS), post-partum depression, and menopause.

In some embodiments, the salt and solid forms of tabernanthalog of the present disclosure have activity as 5-HT$_{2A}$ modulators. In some embodiments, the compounds of the present disclosure elicit a biological response by activating the 5-HT$_{2A}$ receptor (e.g., allosteric modulation or modulation of a biological target that activates the 5-HT$_{2A}$ receptor). 5-HT$_{2A}$ agonism has been correlated with the promotion of neural plasticity (Ly et al., Cell Rep. 2018 Jun. 12; 23(11): 3170-3182). 5-HT$_{2A}$ antagonists abrogate the neuritogenesis and spinogenesis effects of hallucinogenic compounds with 5-HT$_{2A}$ agonist activity, for example, DMT, LSD, and DOI. In some embodiments, the compounds of the present disclosure are 5-HT$_{2A}$ modulators and promote neural plasticity (e.g., cortical structural plasticity). In some embodiments, the compounds of the present disclosure are selective 5-HT$_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, the 5-HT$_{2A}$ modulators (e.g., 5-HT$_{2A}$ agonists) are non-hallucinogenic.

In some embodiments, non-hallucinogenic 5-HT$_{2A}$ modulators (e.g., 5-HT$_{2A}$ agonists) are used to treat neurological diseases, which modulators do not elicit dissociative side-effects. In some embodiments, the hallucinogenic potential of the compounds of the present disclosure described herein is assessed in vitro. In some embodiments, the hallucinogenic potential assessed in vitro of the compounds of the present disclosure is compared to the hallucinogenic potential assessed in vitro of hallucinogenic homologs. In some embodiments, the compounds of the present disclosure elicit less hallucinogenic potential in vitro than the hallucinogenic homologs.

In some embodiments, serotonin receptor modulators, such as modulators of serotonin receptor 2A (5-HT$_{2A}$ modulators, e.g., 5-HT$_{2A}$ agonists), are used to treat a brain disorder. The presently disclosed compounds (salt and solid forms of tabernanthalog) can function as 5-HT$_{2A}$ agonists alone, or in combination with a second therapeutic agent that also is a 5-HT$_{2A}$ modulator. In such cases the second therapeutic agent can be an agonist or an antagonist. In some instances, it may be helpful administer a 5-HT$_{2A}$ antagonist in combination with a compound of the present disclosure to mitigate undesirable effects of 5-HT$_{2A}$ agonism, such as potential hallucinogenic effects. Serotonin receptor modulators useful as second therapeutic agents for combination therapy as described herein are known to those of skill in the art and include, without limitation, ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperidone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methiothepin, methysergide, trazodone, cinitapride, cyproheptadine, brexpiprazole, cariprazine, agomelatine, setoperone, 1-(1-Naphthyl)piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-I-R91150, 5-MeO-NBpBrT, 9-Aminomethyl-9,10-dihydroanthracene, niaprazine, SB-215505, SB-204741, SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, and an extended-release form of aripiprazole including Abilify Maintena, or a pharmaceutically acceptable salt, solvate, metabolite, derivative, or prodrug thereof. In some embodiments, the serotonin receptor modulator used as a second therapeutic is pimavanserin or a pharmaceutically acceptable salt, solvate, metabolite, derivative, or prodrug thereof.

In some embodiments, the serotonin receptor modulator is administered prior to a compound of the present disclosure, such as about three or about one hours prior to the administration of a compound of the present disclosure. In some embodiments, the serotonin receptor modulator is administered at most about one hour prior to the presently disclosed compound. Thus, in some embodiments of combination therapy with the presently disclosed compounds, the second therapeutic agent is a serotonin receptor modulator.

In some embodiments, the salt and solid forms of the tabernanthalog act as non-hallucinogenic 5-HT2$_A$ modulators (e.g., 5-HT2$_A$ agonists) that are used to treat neurological diseases. In some embodiments, the neurological diseases comprise decreased neural plasticity, decreased cortical structural plasticity, decreased 5-HT$_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, the salt and solid forms of the tabernanthalog act as non-hallucinogenic 5-HT$_{2A}$ modulators (e.g., 5-HT$_{2A}$ agonists) are used for increasing neuronal plasticity. In some embodiments, non-hallucinogenic 5-HT$_{2A}$ modulators (e.g., 5-HT$_{2A}$ agonists) are used for treating a brain disorder. In some embodiments, non-hallucinogenic 5-HT$_{2A}$ modulators (e.g., 5-FIT$_{2A}$ agonists) are used for increasing at least one of translation, transcription, or secretion of neurotrophic factors.

Methods for Increasing Neuronal Plasticity

Neuronal plasticity refers to the ability of the brain to change structure and/or function throughout a subject's life. New neurons can be produced and integrated into the central nervous system throughout the subject's life. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity by treating a subject with a salt or solid form of tabernanthalog can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the present disclosure provides methods for increasing neuronal plasticity, comprising contacting a neuronal cell with a compound of the present disclosure. In some embodiments, increasing neuronal plasticity improves a brain disorder described herein.

In some embodiments, a compound of the present disclosure is used to increase neuronal plasticity. In some embodiments, the compounds used to increase neuronal plasticity have, for example, anti-addictive properties, antidepressant properties, anxiolytic properties, or a combination thereof. In some embodiments, decreased neuronal plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). In some embodiments, brain disorders include, for example, migraines, addiction (e.g., substance use disorder), depression, and anxiety.

In some embodiments, the experiment or assay to determine increased neuronal plasticity of any compound of the present disclosure is a phenotypic assay, a dendritogenesis assay, a spinogenesis assay, a synaptogenesis assay, a Sholl analysis, a concentration-response experiment, a $5\text{-HT}_{2A}$ agonist assay, a $5\text{-HT}_{2A}$ antagonist assay, a $5\text{-HT}_{2A}$ binding assay, or a $5\text{-HT}_{2A}$ blocking experiment (e.g., ketanserin blocking experiments). In some embodiments, the experiment or assay to determine the hallucinogenic potential of any compound of the present invention is a mouse head-twitch response (HTR) assay.

In some embodiments, the present disclosure provides a method for increasing neuronal plasticity, comprising contacting a neuronal cell with a compound disclosed herein.

Methods of Treating a Brain Disorder

In some embodiments, the present disclosure provides a method of treating a disease, including administering to a subject in need thereof, a therapeutically effective amount of a salt or solid form of tabernanthalog of the present disclosure. In some embodiments, the disease is a musculoskeletal pain disorder including fibromyalgia, muscle pain, joint stiffness, osteoarthritis, rheumatoid arthritis, muscle cramps. In some embodiments, the present disclosure provides a method of treating a disease of women's reproductive health including premenstrual dysphoric disorder (PMDD), premenstrual syndrome (PMS), post-partum depression, and menopause. In some embodiments, the present disclosure provides a method of treating a brain disorder, including administering to a subject in need thereof, a therapeutically effective amount of a compound of the present disclosure. In some embodiments, the present disclosure provides a method of treating a brain disorder with combination therapy, including administering to a subject in need thereof, a therapeutically effective amount of a compound of the present disclosure and at least one additional therapeutic agent.

In some embodiments, $5\text{-HT}_{2A}$ modulators (e.g., $5\text{-HT}_{2A}$ agonists) are used to treat a brain disorder. In some embodiments, the brain disorders comprise decreased neural plasticity, decreased cortical structural plasticity, decreased $5\text{-HT}_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, a compound of the present disclosure is used to treat brain disorders. In some embodiments, the compounds have, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, panic disorder, suicidality, schizophrenia, and addiction (e.g., substance abuse disorder). In some embodiments, brain disorders include, for example, migraines, addiction (e.g., substance use disorder), depression, and anxiety.

In some embodiments, the present disclosure provides a method of treating a brain disorder, comprising administering to a subject in need thereof a therapeutically effective amount of a compound disclosed herein.

In some embodiments, the brain disorder is a neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the brain disorder is a neurodegenerative disorder, Alzheimer's, or Parkinson's disease. In some embodiments, the brain disorder is a psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury or substance use disorder. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the method further comprises administering one or more additional therapeutic agent that is lithium, olanzapine (Zyprexa), quetiapine (Seroquel), risperidone (Risperdal), aripiprazole (Abilify), ziprasidone (Geodon), clozapine (Clozaril), divalproex sodium (Depakote), lamotrigine (Lamictal), valproic acid (Depakene), carbamazepine (Equetro), topiramate (Topamax), levomilnacipran (Fetzima), duloxetine (Cymbalta, Yentreve), venlafaxine (Effexor), citalopram (Celexa), fluvoxamine (Luvox), escitalopram (Lexapro), fluoxetine (Prozac), paroxetine (Paxil), sertraline (Zoloft), clomipramine (Anafranil), amitriptyline (Elavil), desipramine (Norpramin), imipramine (Tofranil), nortriptyline (Pamelor), phenelzine (Nardil), tranylcypromine (Parnate), diazepam (Valium), alprazolam (Xanax), or clonazepam (Klonopin).

In certain embodiments of the method for treating a brain disorder with a solid form disclosed herein, a second therapeutic agent that is an empathogenic agent is administered. Examples of suitable empathogenic agents for use in combination with the present solid forms include phenethylamines, such as 3,4-methylene-dioxymethamphetamine (MDMA), and analogs thereof.

Other suitable empathogenic agents for use in combination with the presently disclosed salts and solid forms include, without limitation,
N-Allyl-3,4-methylenedioxy-amphetamine (MDAL)
N-Butyl-3,4-methylenedioxyamphetamine (MDBU)
N-Benzyl-3,4-methylenedioxyamphetamine (MDBZ)
N-Cyclopropylmethyl-3,4-methylenedioxyamphetamine (MDCPM)
N,N-Dimethyl-3,4-methylenedioxyamphetamine (MDDM)
N-Ethyl-3,4-methylenedioxyamphetamine (MDE; MDEA)
N-(2-Hydroxyethyl)-3,4-methylenedioxy amphetamine (MDHOET)
N-Isopropyl-3,4-methylenedioxyamphetamine (MDIP)
N-Methyl-3,4-ethylenedioxyamphetamine (MDMC)
N-Methoxy-3,4-methylenedioxyamphetamine (MDMEO)
N-(2-Methoxyethyl)-3,4-methylenedioxyamphetamine (MDMEOET)
alpha,alpha,N-Trimethyl-3,4-methylenedioxyphenethylamine (MDMP;
3,4-Methylenedioxy-N-methylphentermine)
N-Hydroxy-3,4-methylenedioxyamphetamine (MDOH)
3,4-Methylenedioxyphenethylamine (MDPEA)
alpha,alpha-Dimethyl-3,4-methylenedioxyphenethylamine (MDPH; 3,4-methylenedioxyphentermine)
N-Propargyl-3,4-methylenedioxyamphetamine (MDPL)
Methylenedioxy-2-aminoindane (MDAL)
1,3-Benzodioxolyl-N-methylbutanamine MBDB
3,4-methylenedioxy-N-methyl-α-ethylphenylethylamine
3,4-Methylenedioxyamphetamine MDA
Methylone (also known as "3,4-methylenedioxy-N-methylcathinone
Ethylone, also known as 3,4-methylenedioxy-N-ethylcathinone
GHB or Gamma Hydroxybutyrate or sodium oxybate
N-Propyl-3,4-methylenedioxyamphetamine (MDPR), and the like.

In some embodiments, the compounds of the present disclosure are used in combination with the standard of care therapy for a neurological disease described herein. Non-limiting examples of the standard of care therapies, may include, for example, lithium, olanzapine, quetiapine, risperidone, aripiprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Nonlimiting examples of standard of care therapy for depression are sertraline, fluoxetine, escitalopram, venlafaxine, or aripiprazole. Non-limiting examples of standard of care therapy for depression are citalopram, escitalopram, fluoxetine, paroxetine, diazepam, or sertraline. Additional examples of standard of care therapeutics are known to those of ordinary skill in the art.

Methods of Increasing at Least One of Translation, Transcription, or Secretion of Neurotrophic Factors Neurotrophic factors refer to a family of soluble peptides or proteins which support the survival, growth, and differentiation of developing and mature neurons. Increasing at least one of translation, transcription, or secretion of neurotrophic factors can be useful for, but not limited to, increasing neuronal plasticity, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing at least one of translation, transcription, or secretion of neurotrophic factors can increasing neuronal plasticity. In some embodiments, increasing at least one of translation, transcription, or secretion of neurotrophic factors can promoting neuronal growth, promoting neuritogenesis, promoting synaptogenesis, promoting dendritogenesis, increasing dendritic arbor complexity, and/or increasing dendritic spine density.

In some embodiments, 5-$HT_{2A}$ modulators (e.g., 5-$HT_{2A}$ agonists) are used to increase at least one of translation, transcription, or secretion of neurotrophic factors. In some embodiments, a compound of the present disclosure is used to increase at least one of translation, transcription, or secretion of neurotrophic factors. In some embodiments, increasing at least one of translation, transcription or secretion of neurotrophic factors treats a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder).

In some embodiments, the experiment or assay used to determine increase translation of neurotrophic factors includes ELISA, western blot, immunofluorescence assays, proteomic experiments, and mass spectrometry. In some embodiments, the experiment or assay used to determine increase transcription of neurotrophic factors includes gene expression assays, PCR, and microarrays. In some embodiments, the experiment or assay used to determine increase secretion of neurotrophic factors includes ELISA, western blot, immunofluorescence assays, proteomic experiments, and mass spectrometry.

In some embodiments, the present disclosure provides a method for increasing at least one of translation, transcription or secretion of neurotrophic factors, comprising contacting a neuronal cell with a compound disclosed herein.

EXAMPLES

In the following Examples, the relative intensity values in peak tables were calculated using the Net. intensity values.

Example 1: Polymorph Production of Tabernanthalog Fumarate

The active pharmaceutical ingredient (API), tabernanthalog fumarate, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data is used to assess crystallinity.

PLM data is used to evaluate crystallinity and particle size/morphology. DSC data is used to evaluate melting point, thermal stability, and crystalline form conversion. TG data is used to evaluate if the API is a solvate or hydrate, and to evaluate thermal stability. DVS data is used to evaluate hygroscopicity of the API and if hydrates can be formed at high relative humidity. About 10 to 15 solvents may be selected from Table 2, based on their properties (polarity, dielectric constant, and dipole moment).

TABLE 2

List of Solvents

Solvents

| | |
|---|---|
| acetic acid | n-heptane |
| acetone | n-hexane |
| acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | methanol |
| chlorobenzene | methoxy benzene (anisole) |
| chloroform | methyl acetate |
| di(ethylene glycol) | methyl ethyl ketone (2-butanone) |
| dichloromethane | methyl isobutyl ketone |
| diethyl ether | nitromethane |
| diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | perfluorohexane |
| 1,4-dioxane | propyl acetate |
| 1,2-ethanediol (ethylene glycol) | 1,1,2,2-tetrachloroethane |
| ethanol | tetrahydrofuran |
| ethanolamine | toluene |
| 2-ethoxyethanol (Cellosolve) | 1,1,1-trichloroethane |
| ethyl acetate | 2,2,2-trifluoroethanol |
| ethyl formate | water |
| formic acid | o-xylene (1,2-dimethylbenzene) |
| glycerol | p-xylene (1,4-dimethylbenzene) |

The information obtained is used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

API is dissolved in a solvent or mixture of solvents, and the solvents are evaporated at different rates (slow evaporation or fast evaporation) and at different temperatures (ambient or elevated).

API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).

API is dissolved in a solvent or mixture of solvents, and an antisolvent is added to precipitate the salt. The solids formed will be recovered by filtration and dried (air dried or vacuum dried).

API is added to a solvent or mixture of solvents, where the API is not fully dissolved. The slurry will be agitated at different temperatures for a number of days. The solids formed will be recovered by filtration and (air dried or vacuum dried).

API is milled (by mechanical milling or by mortar and pestle), with a drop of solvent, or without any solvent.

API is melted and cooled (at different cooling rates, fast and slow, and cooled to different temperatures) to obtain solids.

API is suspended in a solvent or mixture of solvents, and the slurry is placed in a heating/cooling cycle for multiple cycles. The remaining solids after the final cooling cycle will be filtered and (air dried or vacuum dried).

API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.

API is exposed to elevated humidity (or elevated temperature, or combination thereof), or to solvent vapors for extended period of days.

Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).

API is heated to a specific temperature and cooled (at ambient conditions or in a dry box).

The solids obtained are analyzed by XRPD to determine if they are crystalline and, if so, by DSC to see the melting point and by TG to see if they are hydrated/solvated, and by $^1$H NMR spectroscopy to ensure chemical integrity. Karl Fischer water titration is performed on forms that are hydrated. DVS analysis is performed to evaluate hygroscopicity of the form and if hydrated form is present. In particular, variable temperature analyses, including variable temperature XRPD, are performed to assess the stability of each physical form as well as its crystallinity.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C., and heated to 250-300° C. at a heating rate of 10° C./min under continuous nitrogen flow. TG analysis of the samples is performed with a Q 50 (TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45 °2θ with steps of 0.10, and the measuring time is 1.0 second/step. All samples are ground to similar size before exposure to radiation. The powder samples are illuminated using CuKα radiation (λ=1.54056 Å) at 30 kV and 15 mA.

Variable temperature XRPD data are collected using a Huber Imaging Plate Guinier Camera 670 employing Ni-filtered CuKα$_1$ radiation (λ=1.5405981 Å) produced at 40 kV and 20 mA by a Philips PW1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmin$^{-1}$ using a Huber High Temperature Controller HTC 9634 unit with the capillary rotation device 670.2. The temperature is held constant at selected intervals for 10 min while the sample is exposed to X-rays and multiple scans are recorded. A 2θ-range of 4.00-100.0° is used with a step size of 0.005 °2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fisher titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

Example 2: Preparation of Tabernanthalog Fumarate

Tabernanthalog fumarate was prepared according to WO 2020/176599. Analysis of the fumarate salt using thermal techniques suggest a propensity to form solvates and to disproportionate into the hemi-fumarate salt and/or the free base and non-associated fumaric acid. Accordingly improved forms of the molecule were sought.

Solubility assessment of tabernanthalog fumarate revealed only sparing solubility in a variety of solvents. Consistent with Example 1, samples were dissolved in various solvents/solvent systems and cooled to isolate solid material.

Tabernanthalog fumarate dissolved at 5 vol (200 mg/mL) only at reflux in two solvents, water and methanol. At 15 vol the product dissolved in both refluxing butanol and ethanol. Consistent with Example 1, the dissolved samples were cooled. On cooling, each of the four effective solvents yielded solid material. The solids thus obtained were analyzed by XRPD yielding diffractograms with novel peaks from products isolated from each of the four protic solvents.

Figure 1:
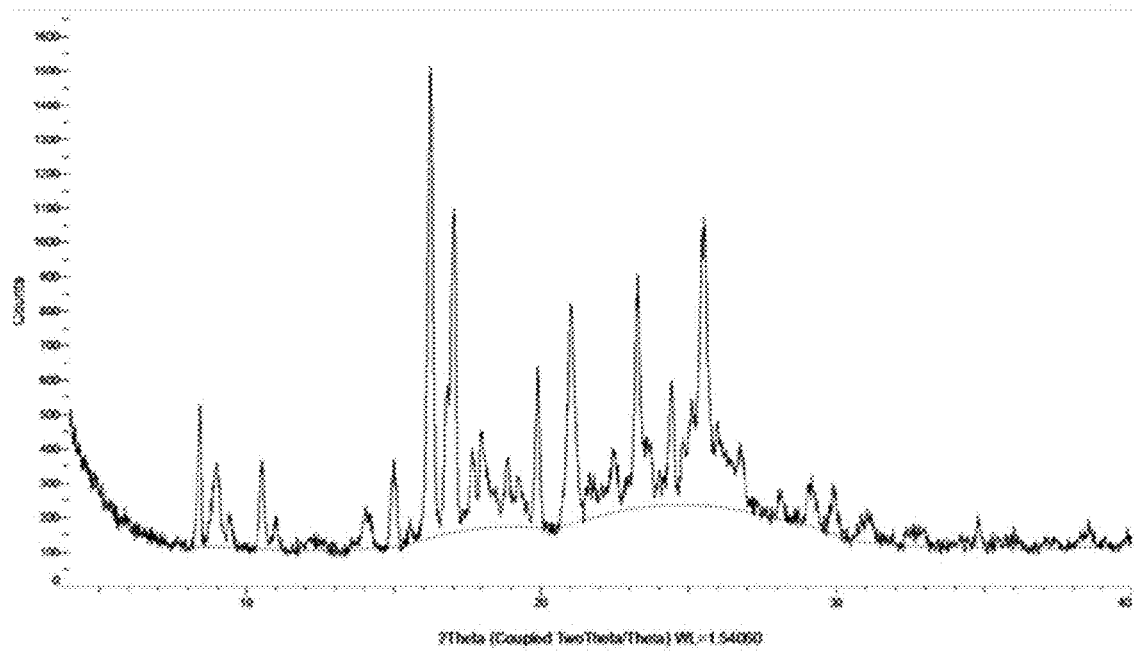
FIG. 1 depicts an XRPD diffractogram of a sample comprising crystalline tabernanthalog fumarate of Pattern #15. The XRPD signals observed in this diffractogram are characterized in Table 176.

The sample isolated from butanol comprised crystalline material responsible for the XRPD diffractogram of FIG. 1. Such material is referred to as Pattern #15 herein.

Figure 2:
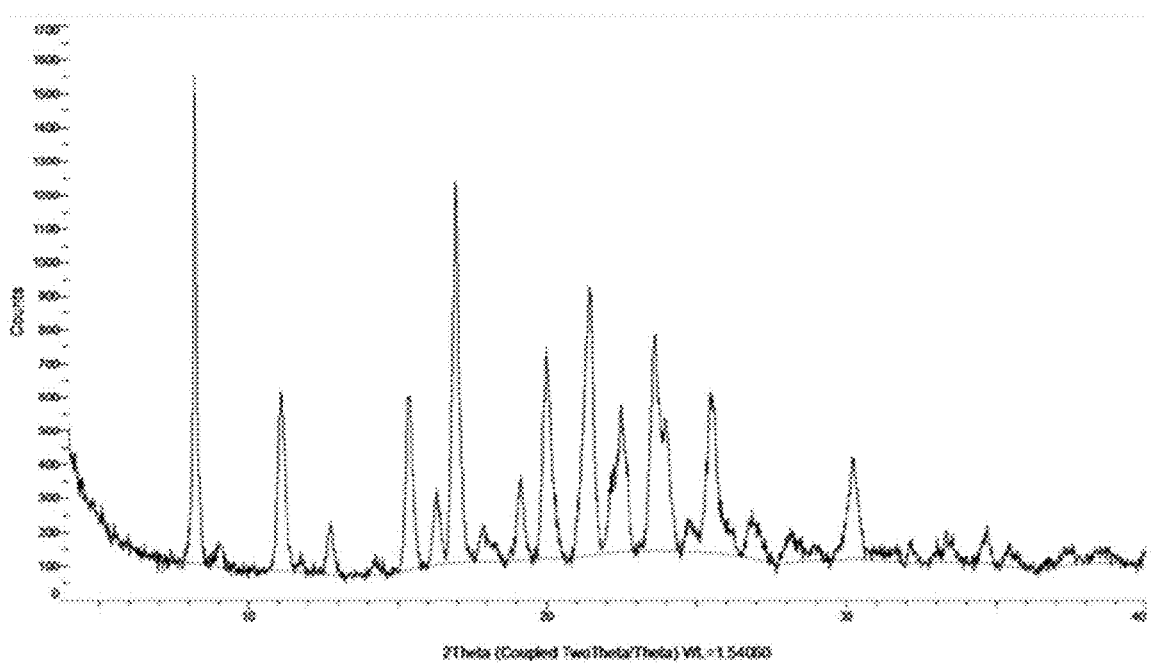
FIG. 2 depicts an XRPD diffractogram of a sample comprising crystalline tabernanthalog fumarate of Pattern #5. The XRPD signals observed in this diffractogram are characterized in Table 181B.

A sample isolated from ethanol (reflux 20 vol followed by cooling) yielded solid crystalline material having Pattern #5, as illustrated by FIG. 2.

Figure 5:
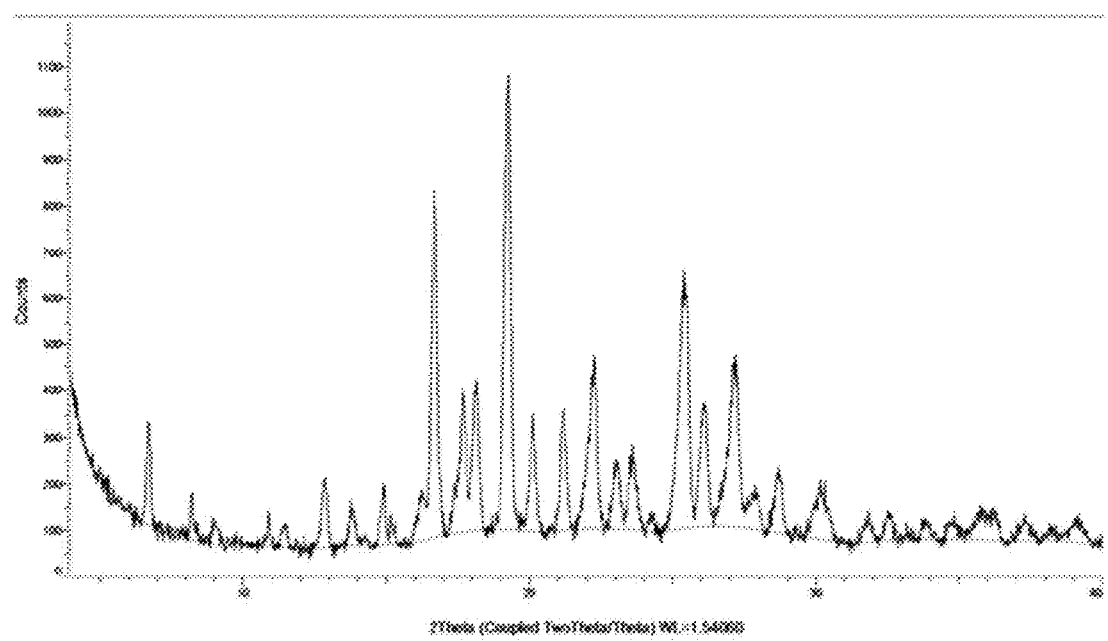
FIG. 5 depicts an XRPD diffractogram of a sample comprising crystalline tabernanthalog hemifumarate salt having XRPD Pattern #21. The XRPD signals observed in this diffractogram are characterized in Table 182.

A sample was isolated from IPA (isopropanol)/heptanes (10 vol IPA/5 vol heptanes stirred at 40° C.), yielding material comprising crystalline tabernanthalog hemifumarate salt having XRPD Pattern #21, as illustrated in FIG. 5.

Figure 14:
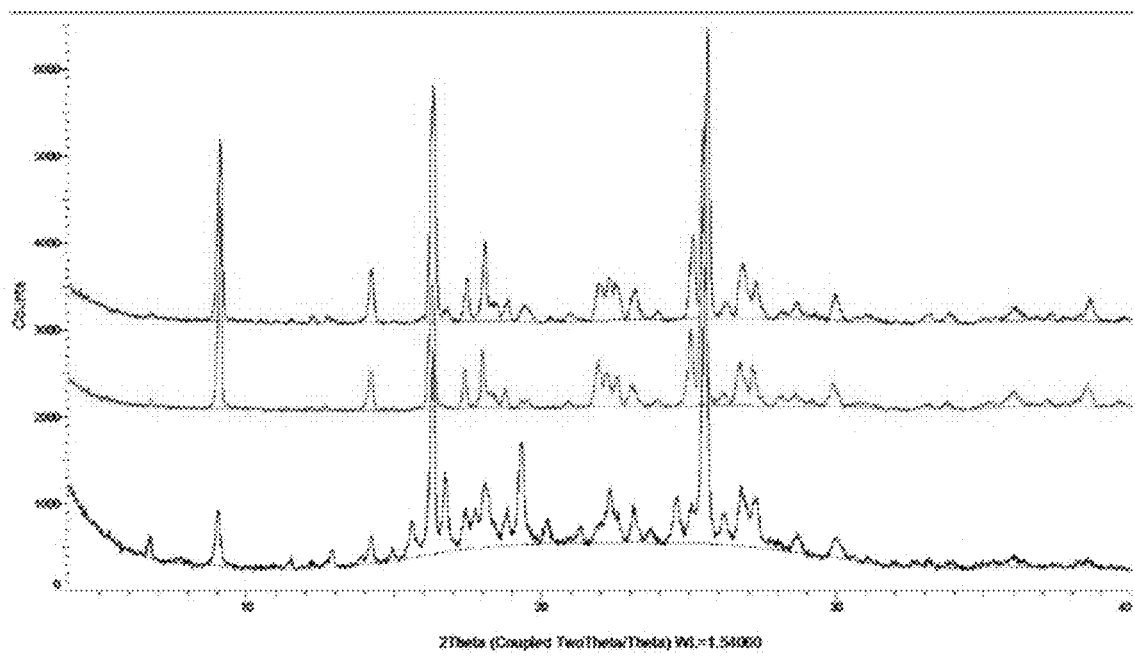
FIG. 14 depicts XRPD diffractograms of a sample comprising crystalline tabernanthalog fumarate crystallized from water (top two traces) compared to an alternate crystalline form of tabernanthalog fumarate (bottom trace). The XRPD signals observed in the top two traces in the diffractogram are characterized in Table 160.

A sample was crystallized from purified water, yielding crystalline tabernanthalog fumarate characterized by the XRPD diffractogram provided as FIG. 14, with the top trace produced from an oven-dried crystalline sample, the middle trace produced from the sample prior to drying. The bottom trace of FIG. 14 was obtained from an alternate crystalline form of tabernanthalog fumarate.

Figure 15:
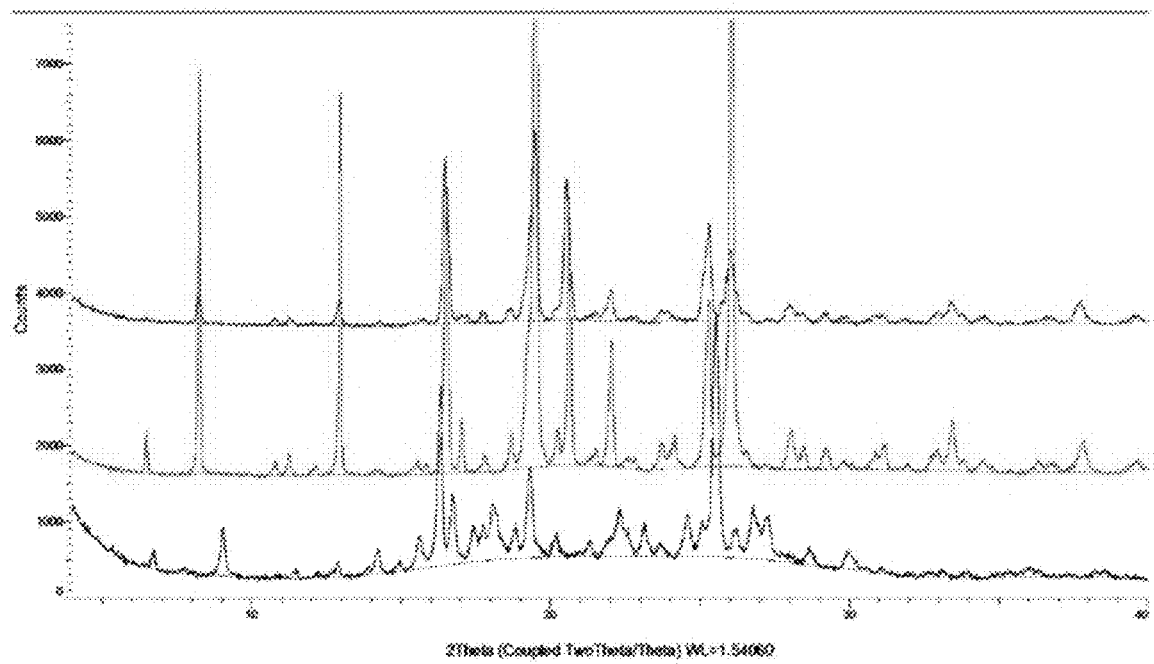
FIG. 15 depicts XRPD diffractograms of a sample comprising crystalline tabernanthalog fumarate crystallized from methanol (top two traces) compared to an alternate crystalline form of tabernanthalog fumarate (bottom trace). The XRPD signals observed in the top two traces in the diffractogram are characterized in Table 167.
Figure 16:
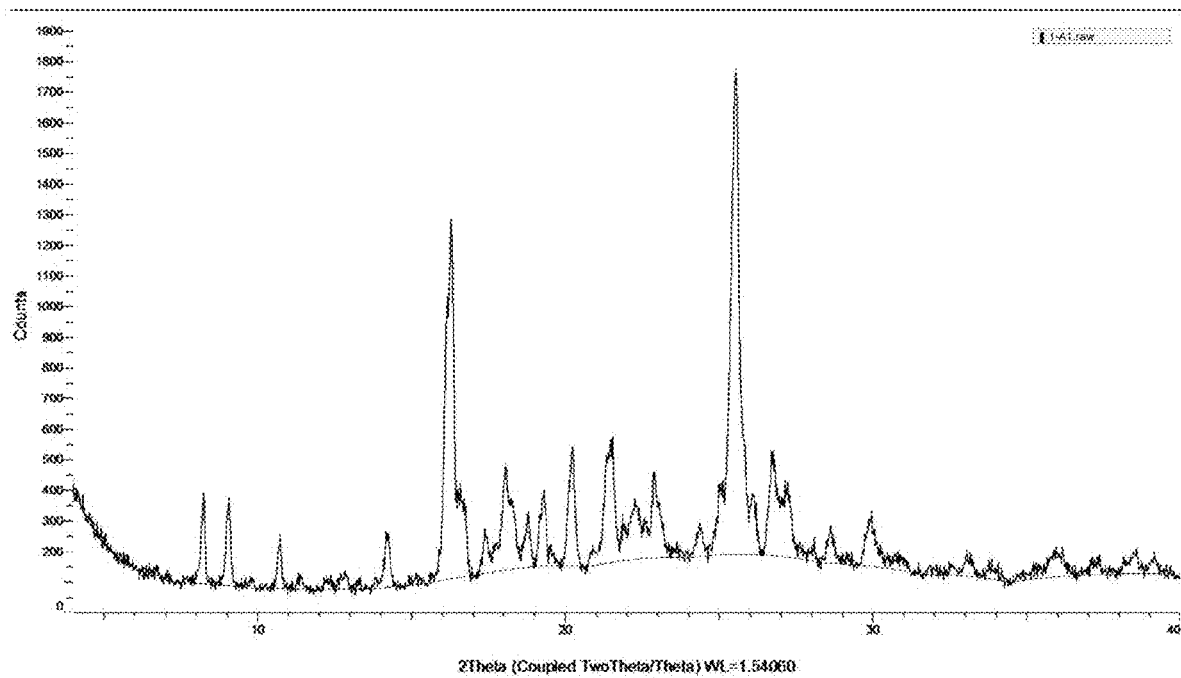
FIG. 16 depicts the XRPD profile of 1-A1 (Experiment Reference 1-Sample Reference A1) (wet pellet, Pattern #12).
Figure 17:
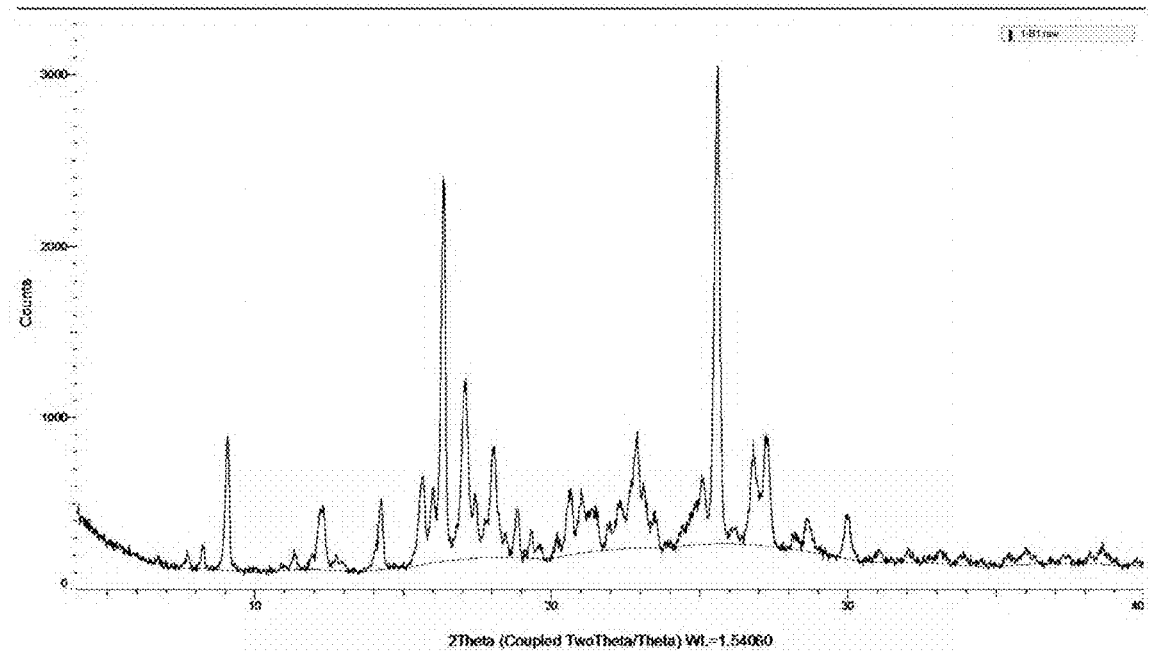
FIG. 17 depicts the XRPD profile of 1-B1 (Experiment Reference 1-Sample Reference B1) (wet pellet, Pattern #2a, Form B).
Figure 18:
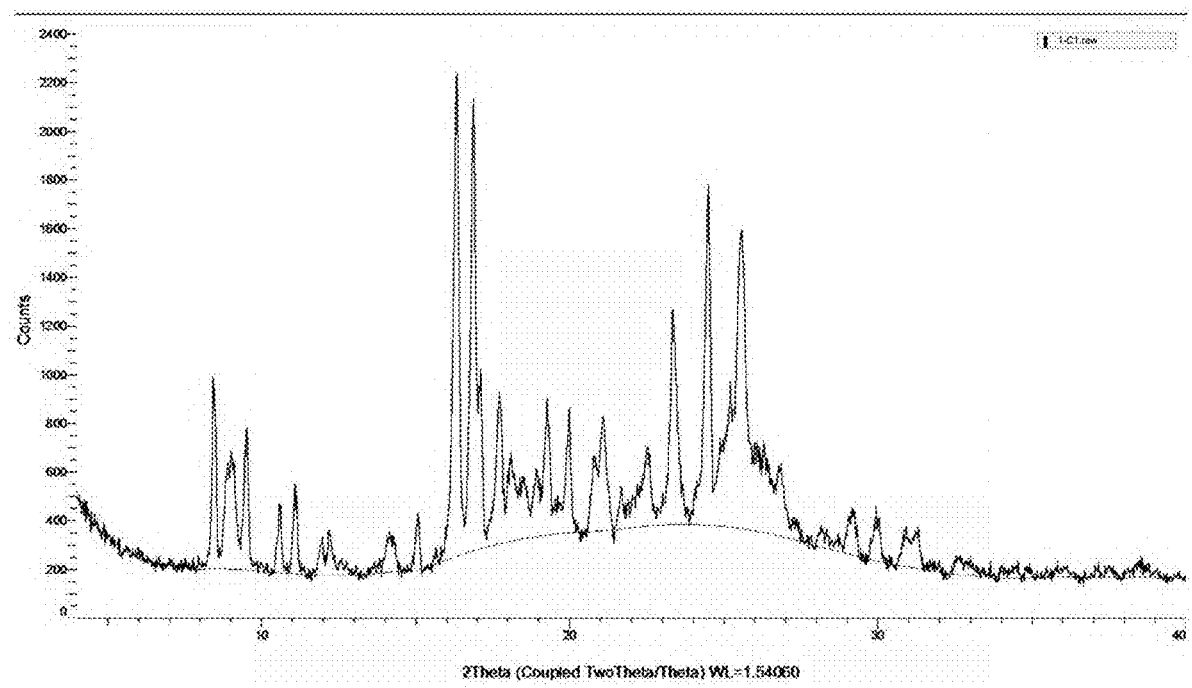
FIG. 18 depicts the XRPD profile of 1-C1 (Experiment Reference 1-Sample Reference C1) (wet pellet, Pattern #15).
Figure 19:
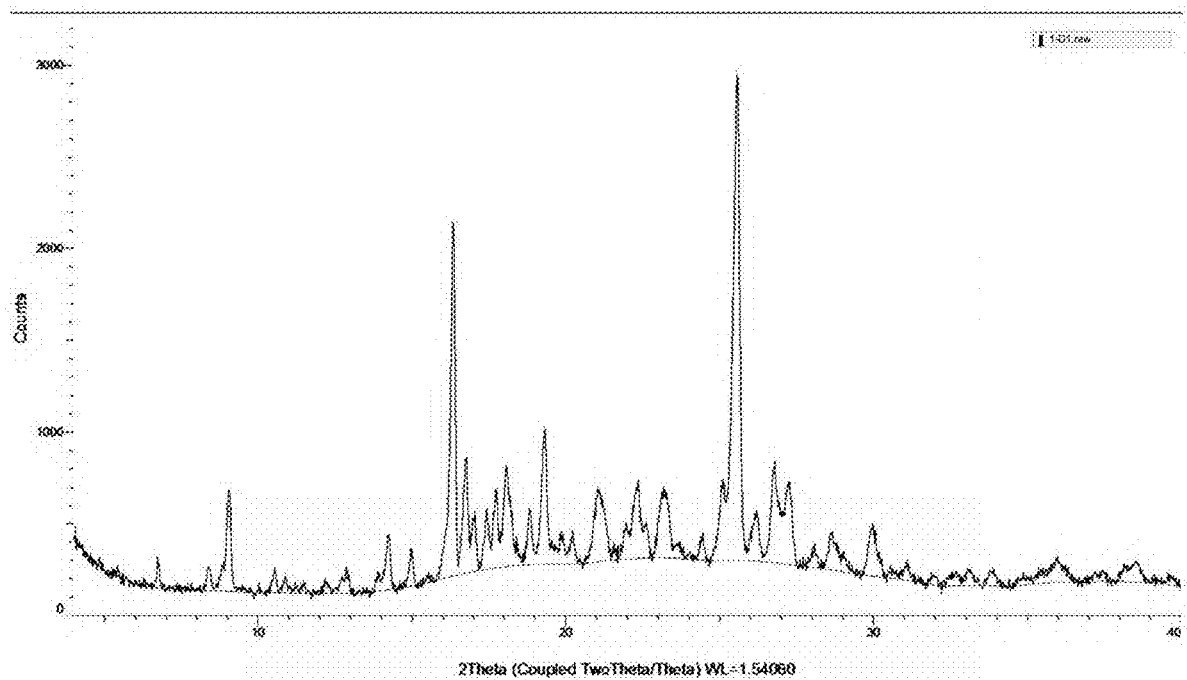
FIG. 19 depicts the XRPD profile of 1-D1 (Experiment Reference 1-Sample Reference D1) (wet pellet, Pattern #1).
Figure 20:
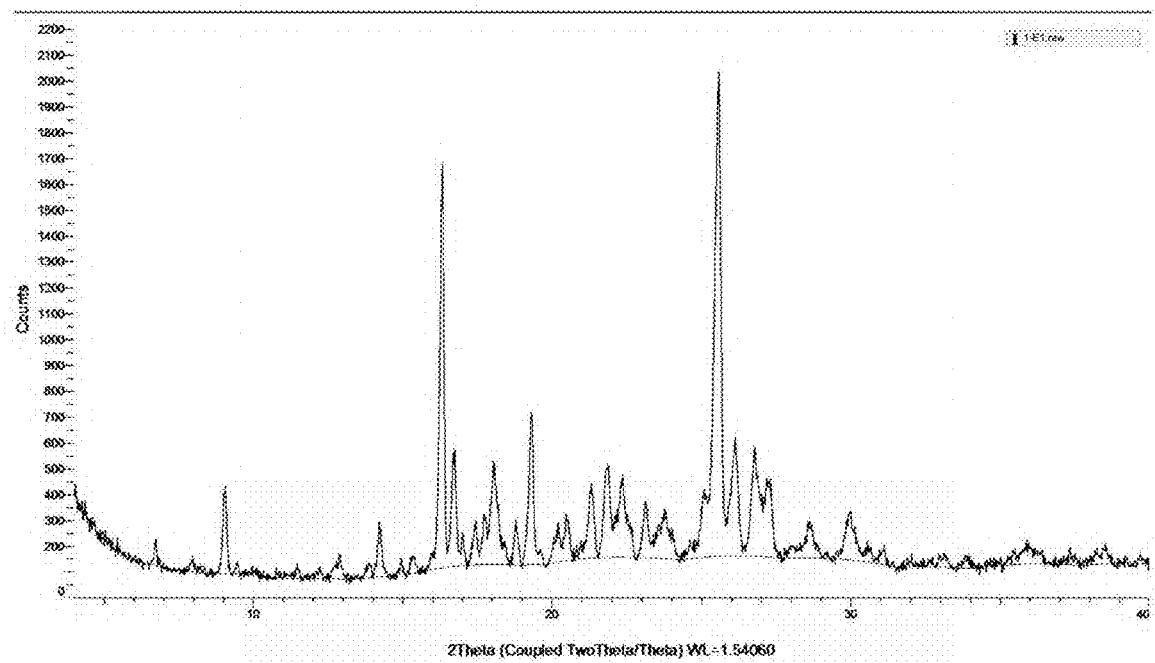
FIG. 20 depicts the XRPD profile of 1-E1 (Experiment Reference 1-Sample Reference E1) (wet pellet, Pattern #1).
Figure 21:
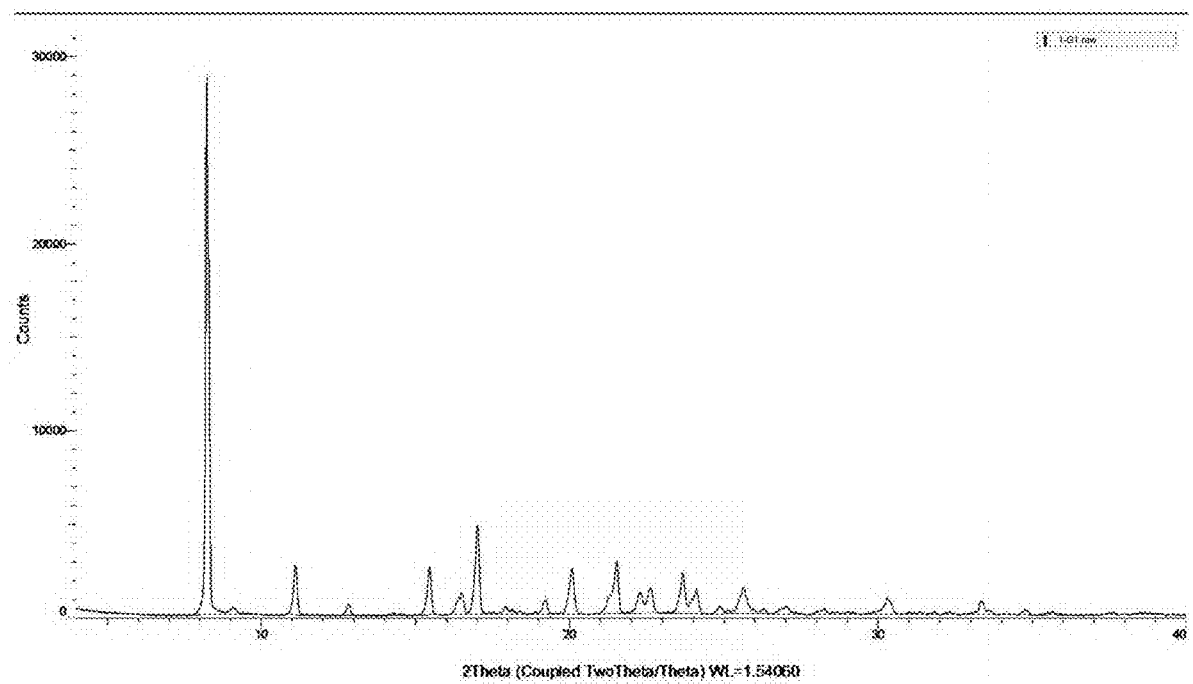
FIG. 21 depicts the XRPD profile of 1-G1 (Experiment Reference 1-Sample Reference G1) (wet pellet, Pattern #5).
Figure 22:
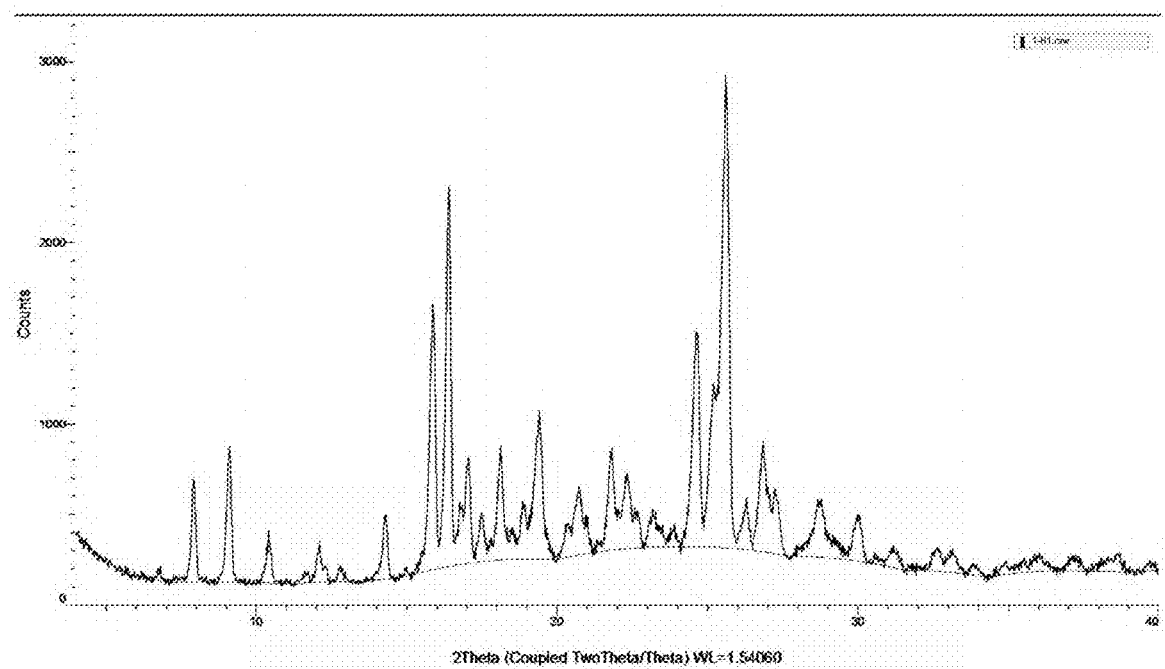
FIG. 22 depicts the XRPD profile of 1-H1 (Experiment Reference 1-Sample Reference H1) (wet pellet, Pattern #9).
Figure 23:
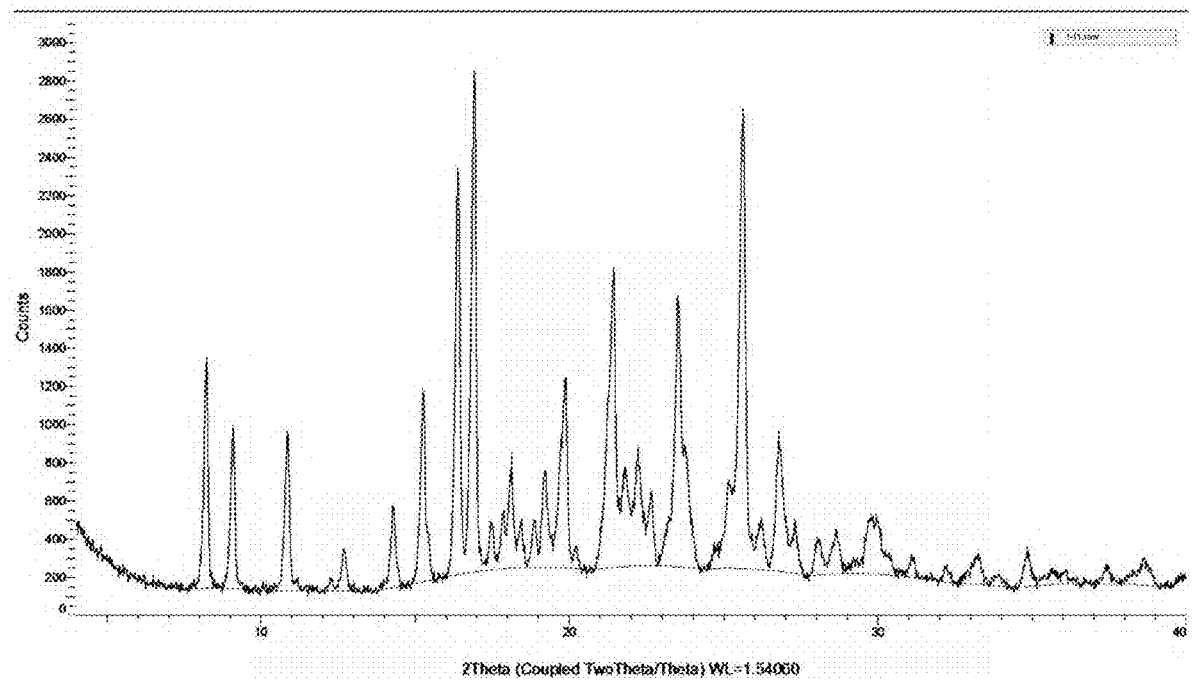
FIG. 23 depicts the XRPD profile of 1-I1 (Experiment Reference 1-Sample Reference I1) (wet pellet, Pattern #10).
Figure 24:
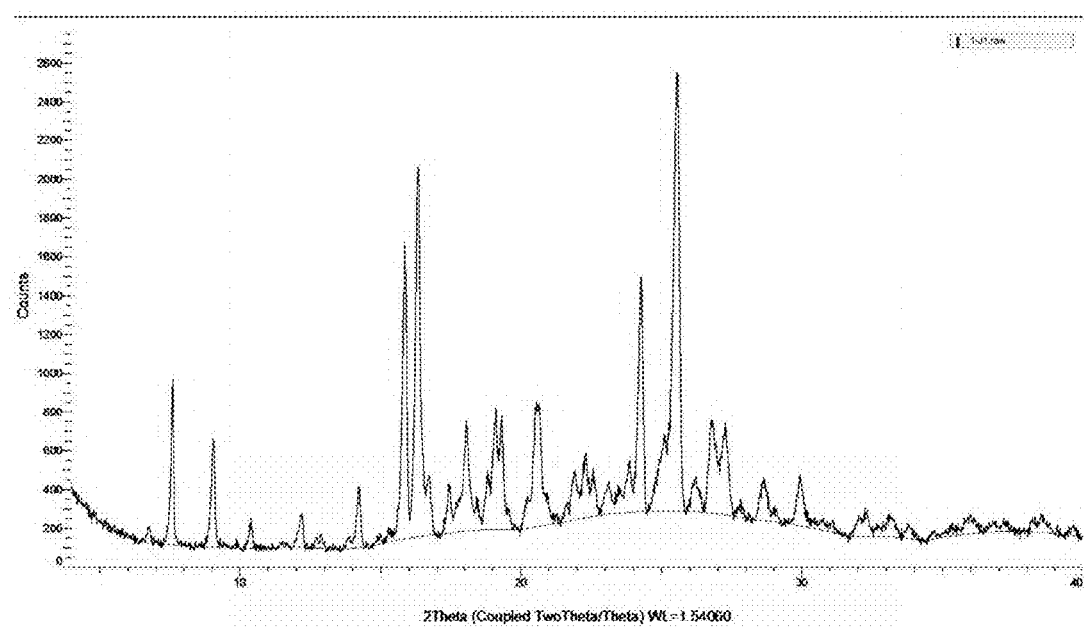
FIG. 24 depicts the XRPD profile of 1-J1 (Experiment Reference 1-Sample Reference J1) (wet pellet, Pattern #8).
Figure 25:
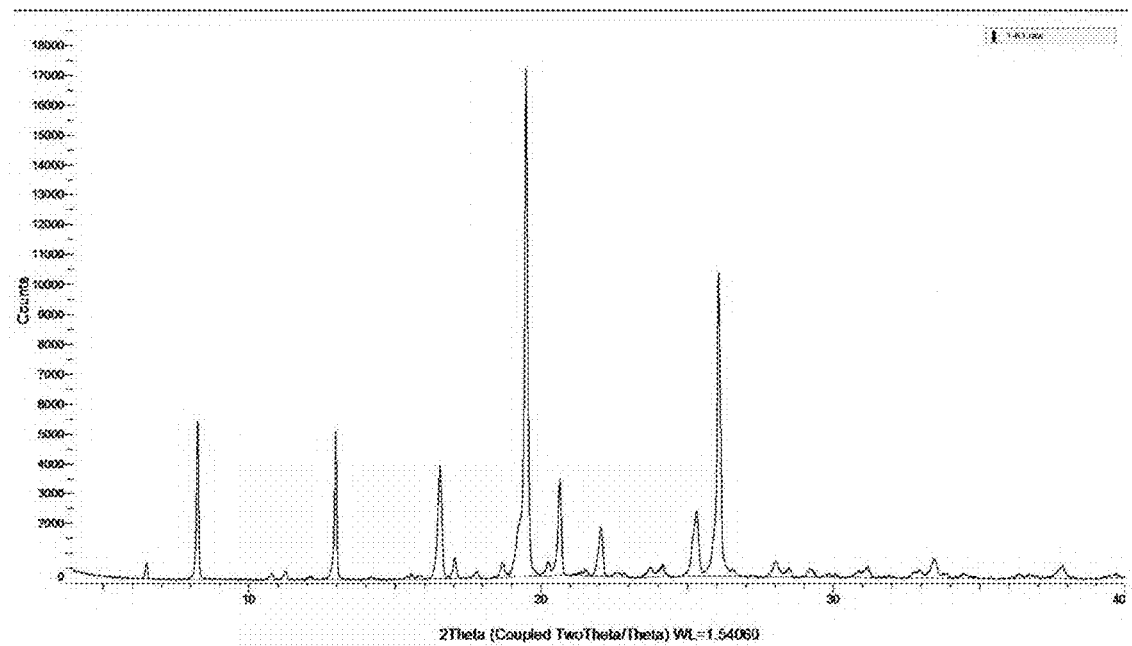
FIG. 25 depicts the XRPD profile of 1-K1 (Experiment Reference 1-Sample Reference K1) (wet pellet, Pattern #6b).
Figure 26:
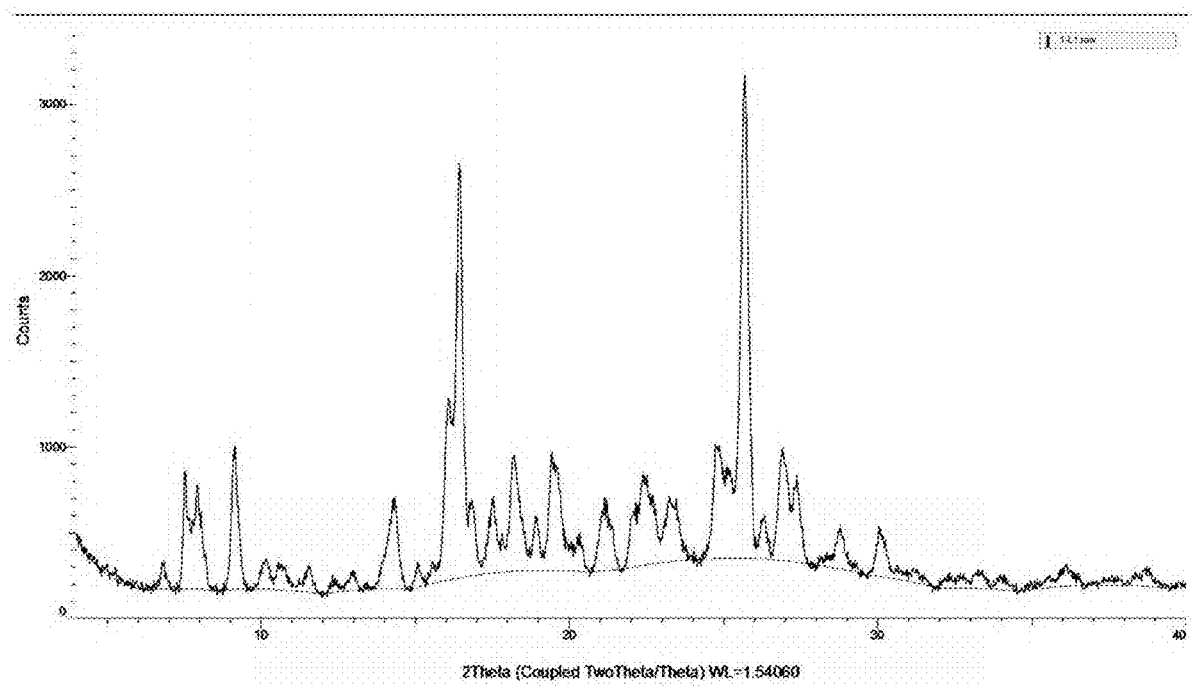
FIG. 26 depicts the XRPD profile of 1-L1 (Experiment Reference 1-Sample Reference L1) (wet pellet, not assigned).
Figure 27:
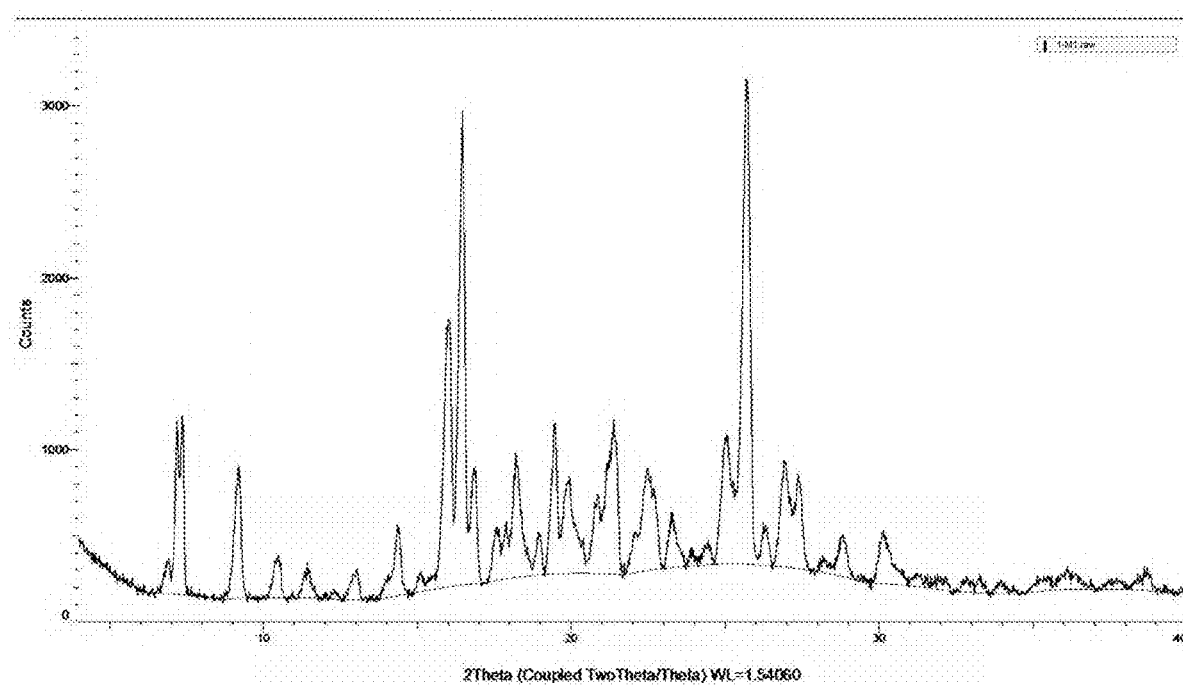
FIG. 27 depicts the XRPD profile of 1-M1 (Experiment Reference 1-Sample Reference M1) (wet pellet, Pattern #7).
Figure 28:
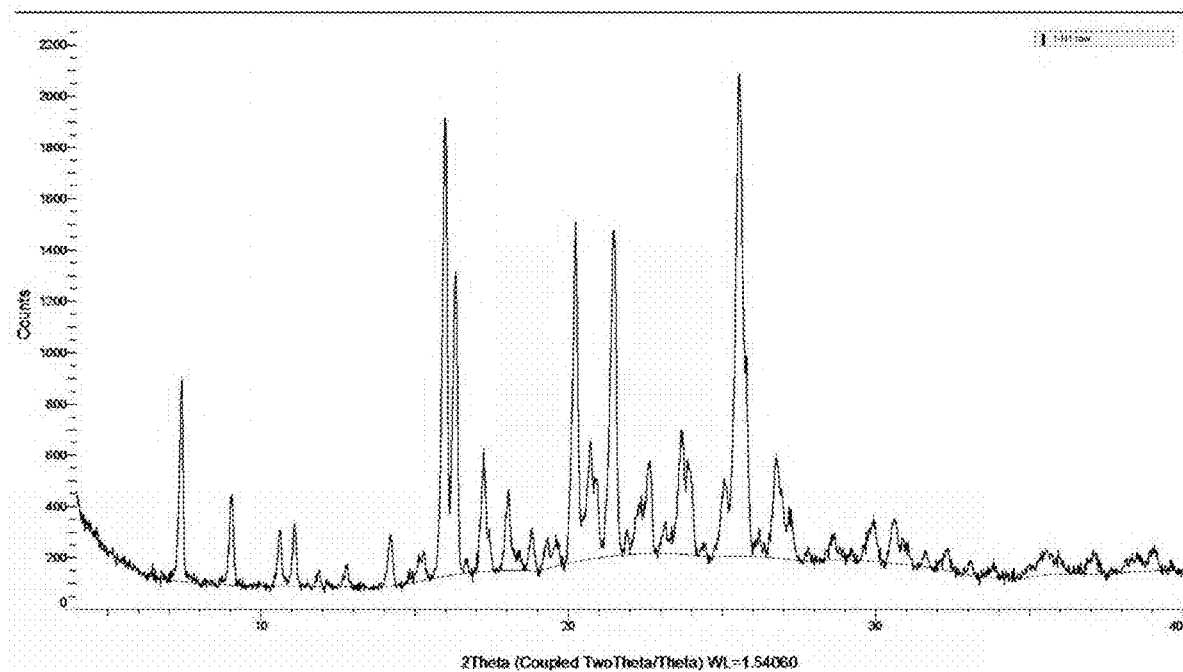
FIG. 28 depicts the XRPD profile of 1-N1 (Experiment Reference 1-Sample Reference N1) (wet pellet, Pattern #11).
Figure 29:
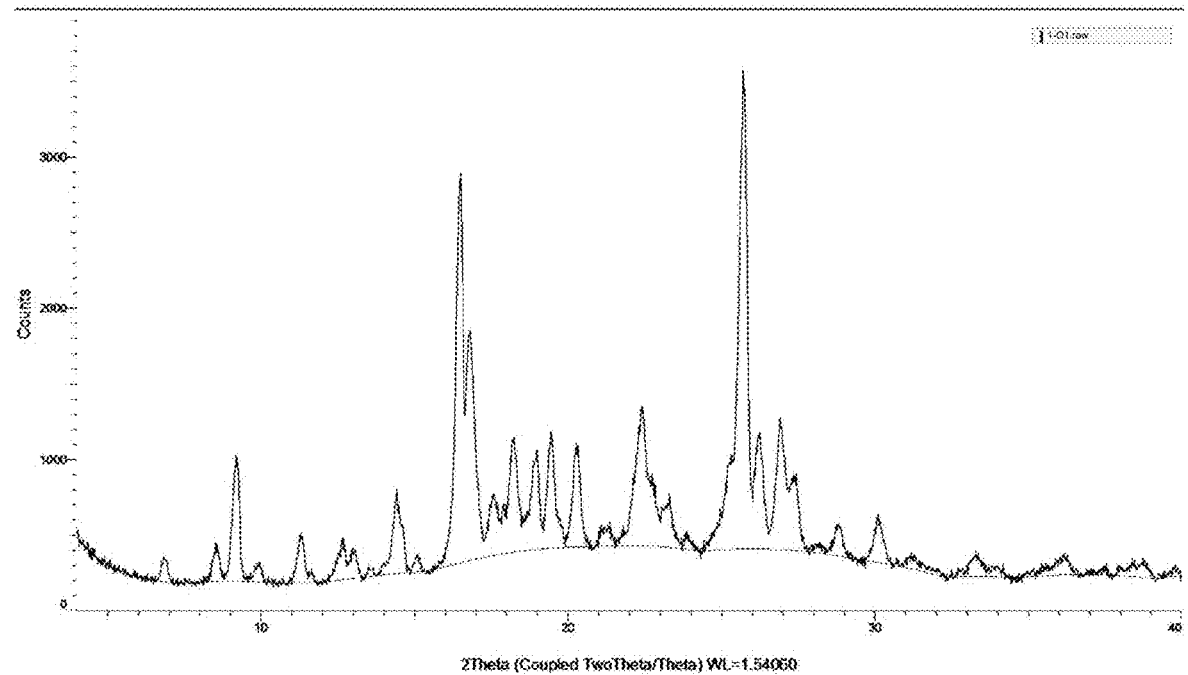
FIG. 29 depicts the XRPD profile of 1-O1 (Experiment Reference 1-Sample Reference O1) (wet pellet, Pattern #1).

A sample was crystallized from methanol yielding tabernanthalog fumarate characterized by the XRPD diffractogram provided as FIG. 15, with the top trace produced from an oven-dried crystalline sample, the middle trace produced from the sample prior to drying. The bottom trace of FIG. 15 was obtained from an alternate crystalline form of tabernanthalog fumarate.

Example 3: Polymorph Production of Tabernanthalog Fumarate Via Suspension Equilibration Consistent with Example 1, tabernanthalog fumarate also was subjected to suspension equilibration in various solvents. According to this example crystalline materials were observed from suspension stirring in various solvents. The materials were analyzed by proton NMR to confirm identity, stoichiometry and solvent content. Table 3 summarizes the crystalline forms identified using suspension equilibration.

TABLE 3

List of crystalline forms of tabernanthalog fumarate identified using suspension equilibration.

Figure 4:
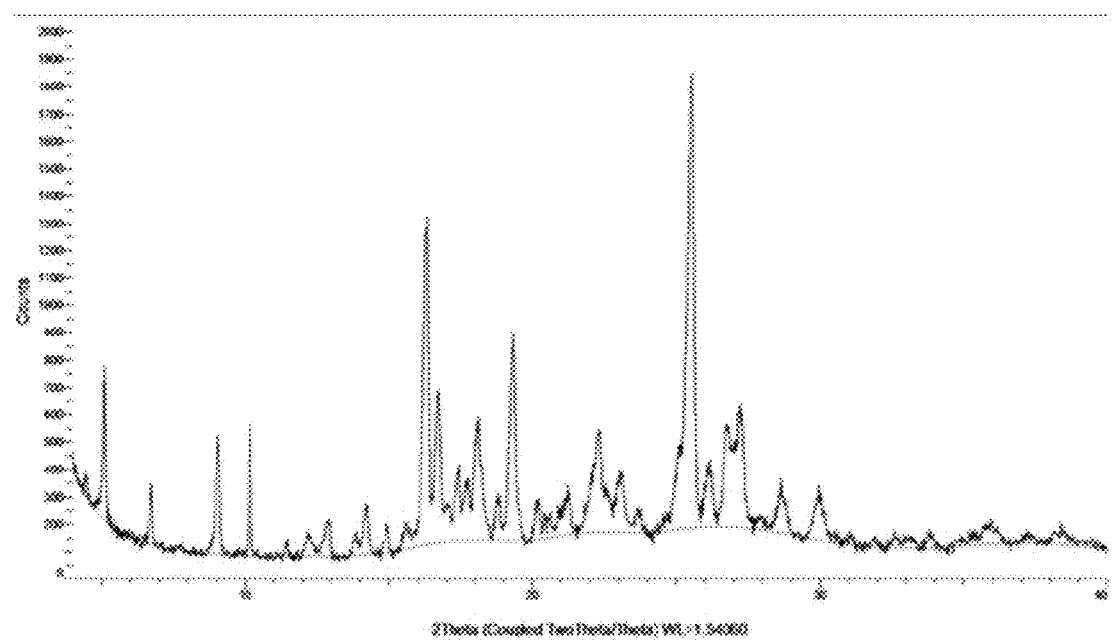
FIG. 4 depicts an XRPD diffractogram of a sample comprising crystalline tabernanthalog fumarate of Pattern #1 isolated from 2-MeTHF/heptanes (10 vol 2-MeTHF/5 vol heptanes stirred at 40° C.). The XRPD signals observed in this diffractogram are characterized in Table 157.
Figure 8:
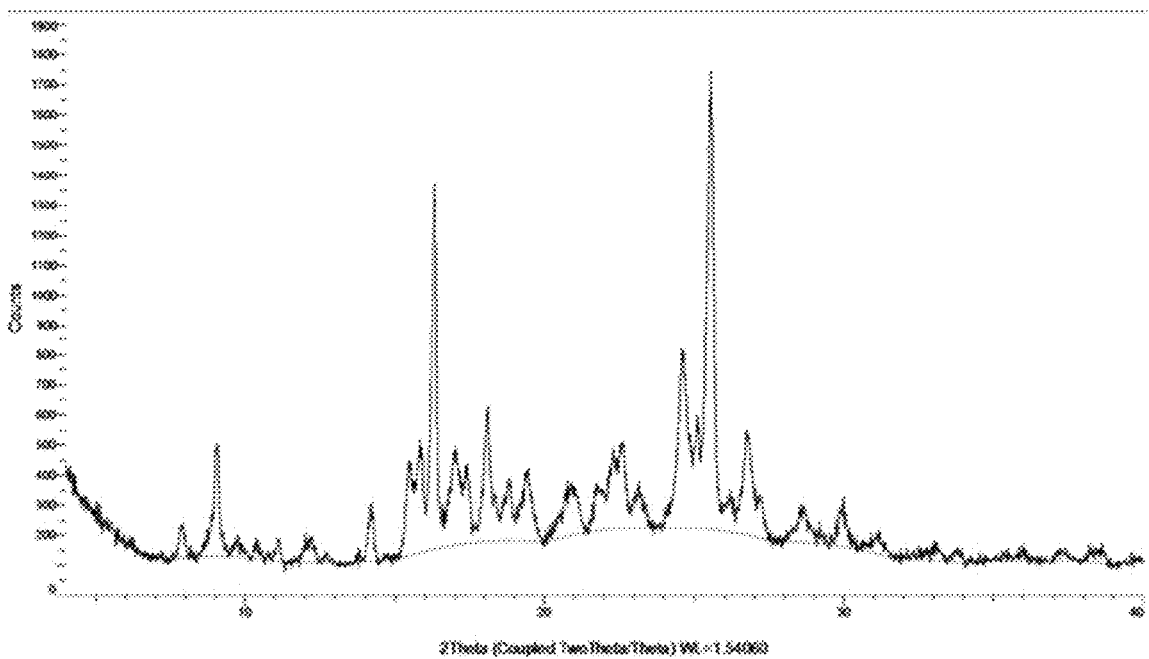
FIG. 8 depicts an XRPD diffractogram of a sample comprising crystalline tabernanthalog fumarate of Pattern #2b. The XRPD signals observed in this diffractogram are characterized in Table 159.
Figure 9:
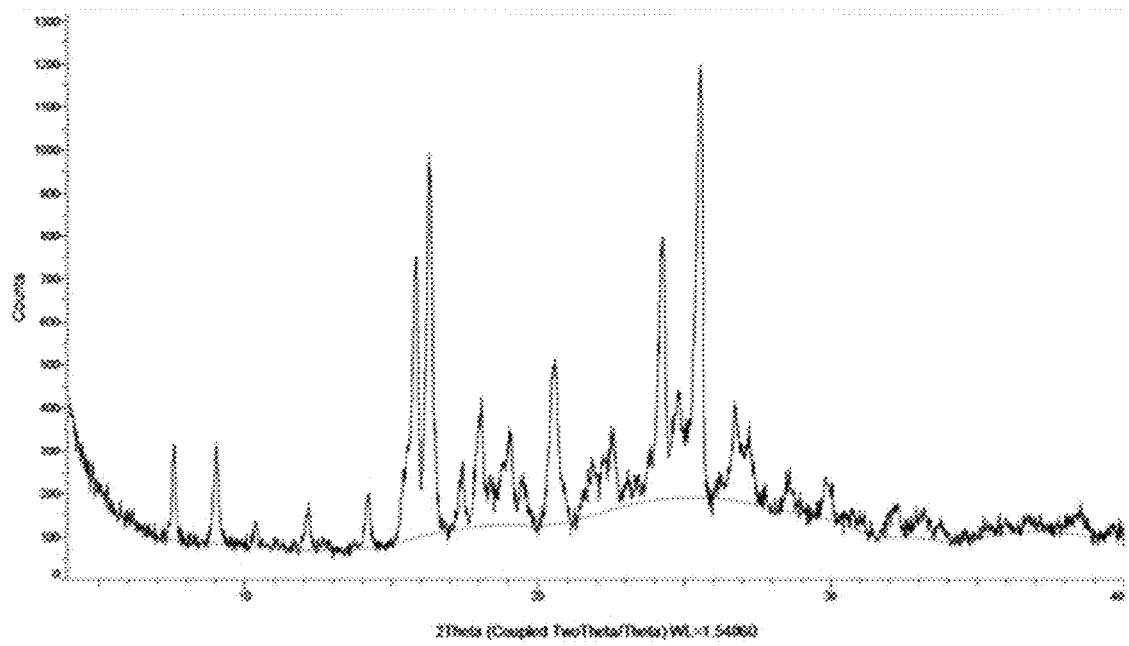
FIG. 9 depicts an XRPD diffractogram of a sample comprising crystalline tabernanthalog monofumarate of Pattern #8. The XRPD signals observed in this diffractogram are characterized in Table 169.
Figure 10:
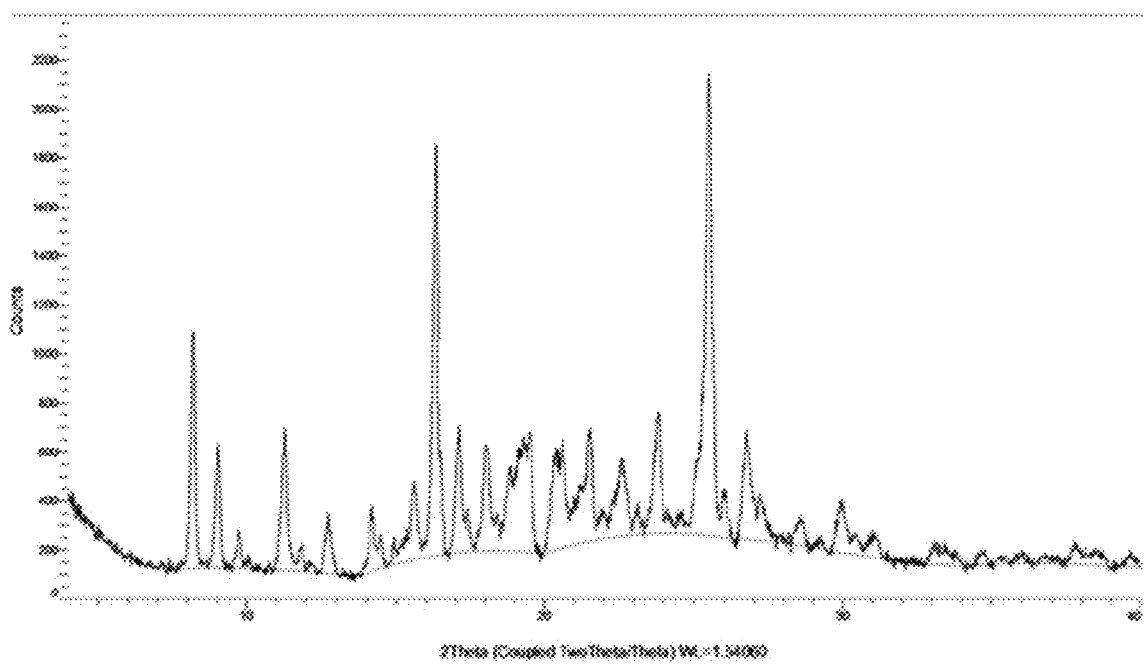
FIG. 10 depicts an XRPD diffractogram of a sample comprising crystalline tabernanthalog fumarate of Pattern #4a. The XRPD signals observed in this diffractogram are characterized in Table 163.
Figure 11:
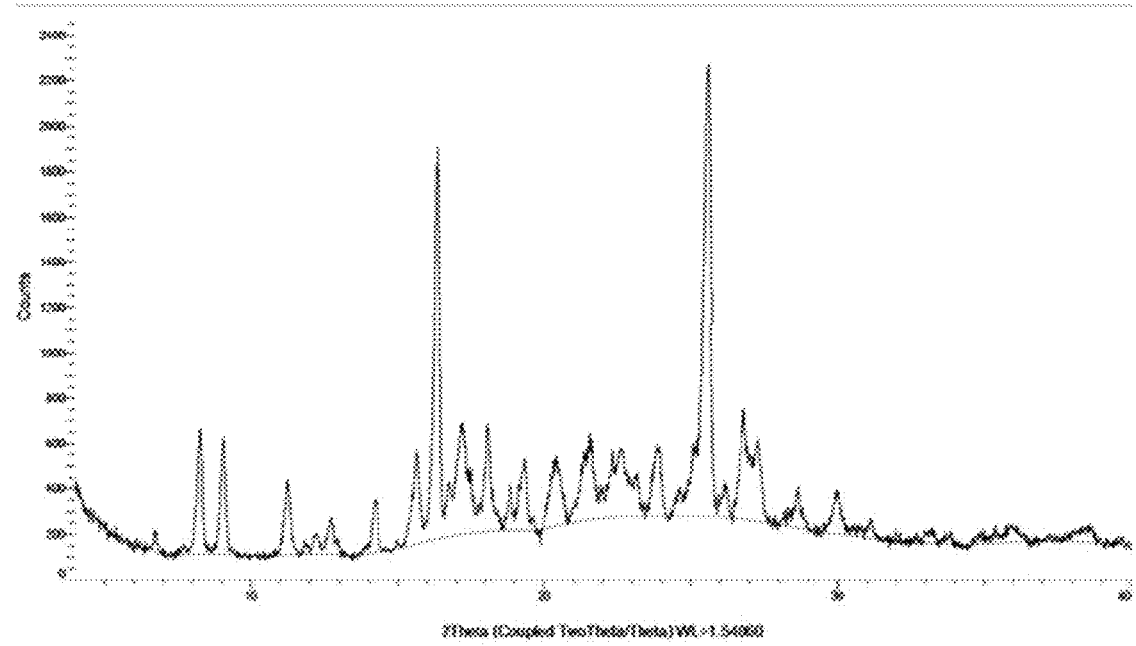
FIG. 11 depicts an XRPD diffractogram of a sample comprising crystalline tabernanthalog fumarate of Pattern #4b. The XRPD signals observed in this diffractogram are characterized in Table 164.
Figure 12:
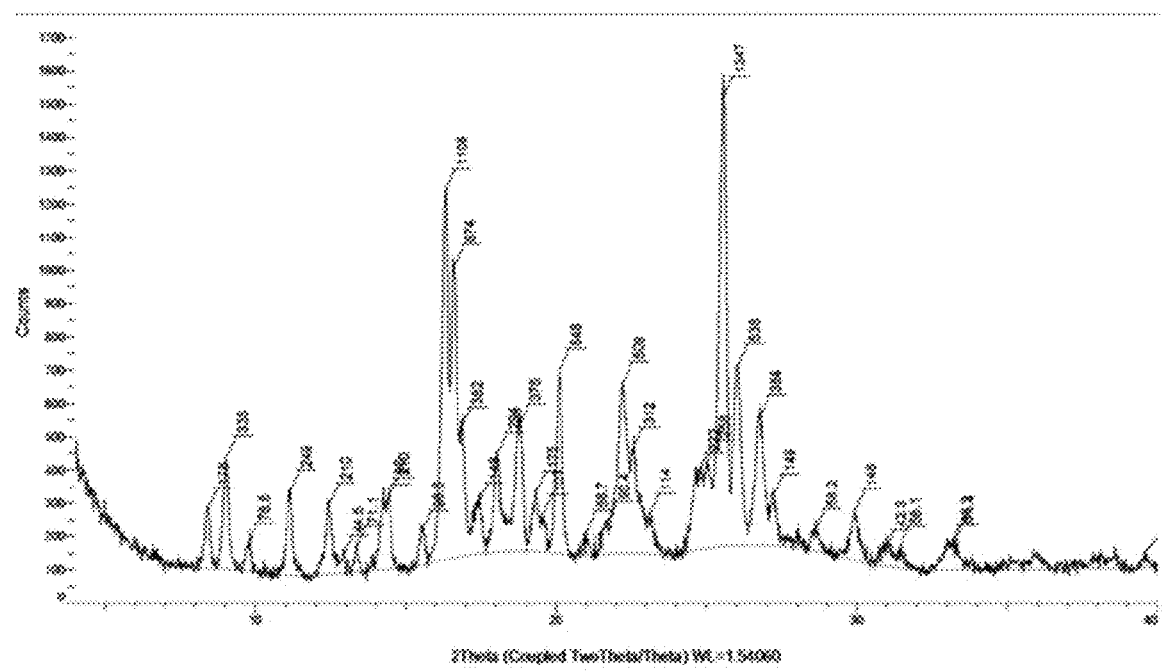
FIG. 12 depicts an XRPD diffractogram of a sample comprising crystalline tabernanthalog fumarate of Pattern #3. The XRPD signals observed in this diffractogram are characterized in Table 162.

| Conditions | XRPD | FIG. | Solvent Content (via $^1$H NMR) |
|---|---|---|---|
| Stirred at 40° C. in 10 vol MeCN and 5 vol heptanes | Pattern #2a | FIG. 3 | 0.1% MeCN |
| Stirred at 40° C. in 10 vol 2-MeTHF and 5 vol heptanes | Pattern #1 | FIG. 4 | N.D MeTHF |
| Stirred at 40° C. in 10 vol IPA and 5 vol heptanes | Hemifumarate Pattern #21 | FIG. 5 | 0.9% IPA |
| Stirred at 20° C. in 10 vol EtOAc and 5 vol heptanes | Pattern #2b | FIG. 8 | 4.0% EtOAc |
| Stirred at 20° C. in 10 vol IPAc and 5 vol heptanes | Pattern #8 | FIG. 9 | 10% IPAc (isopropyl acetate) |
| Stirred at 20° C. in 10 vol MeOH and 5 vol heptanes | Pattern #4a | FIG. 10 | 0.2% MeOH |
| Stirred at 20° C. in 10 vol MeNO$_2$ and 5 vol heptanes | Pattern #4b | FIG. 11 | 0.2% MeNO$_2$ |
| Stirred at 20° C. in 10 vol Toluene and 5 vol heptanes | Pattern #3 | FIG. 12 | 5% Toluene |
| Stirred at 20° C. in 10 vol Water and 5 vol heptanes | Pattern #6a | FIG. 13 | N.D. Water |

Example 4: Production of the Tabernanthalog Hemifumarate Salt

Figure 6:
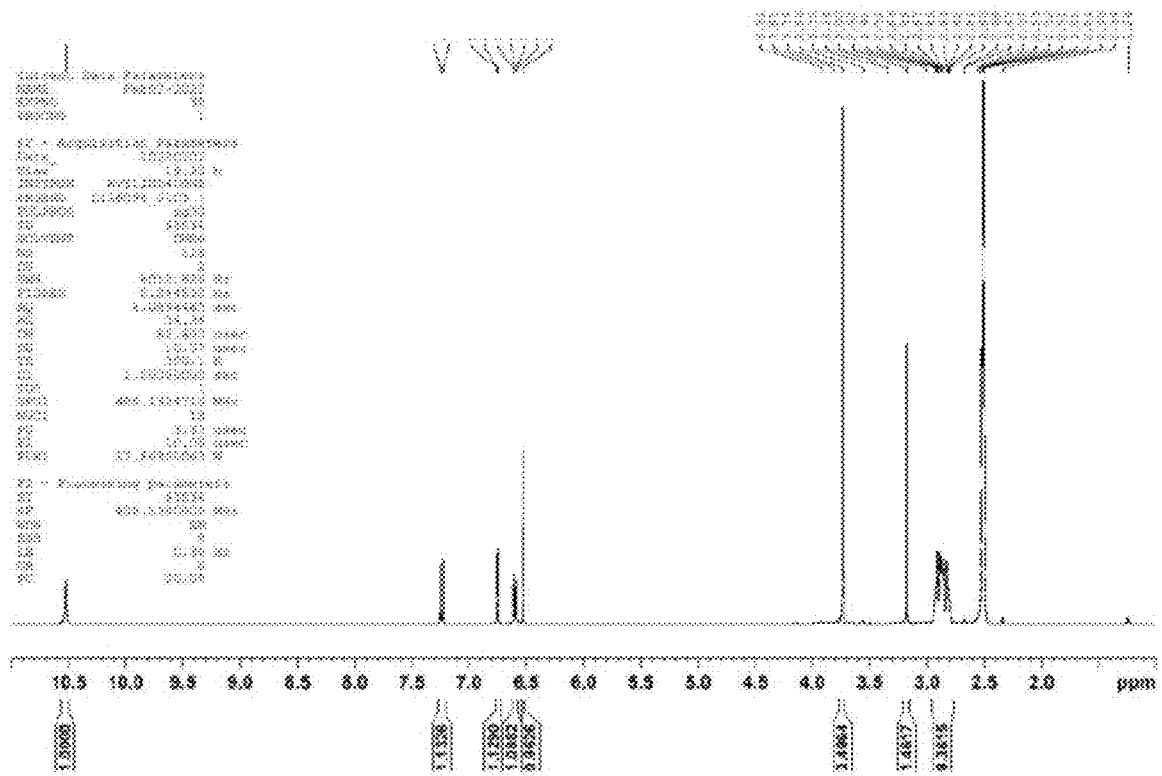
FIG. 6 depicts a proton NMR spectrum of tabernanthalog hemifumarate salt.
Figure 7:
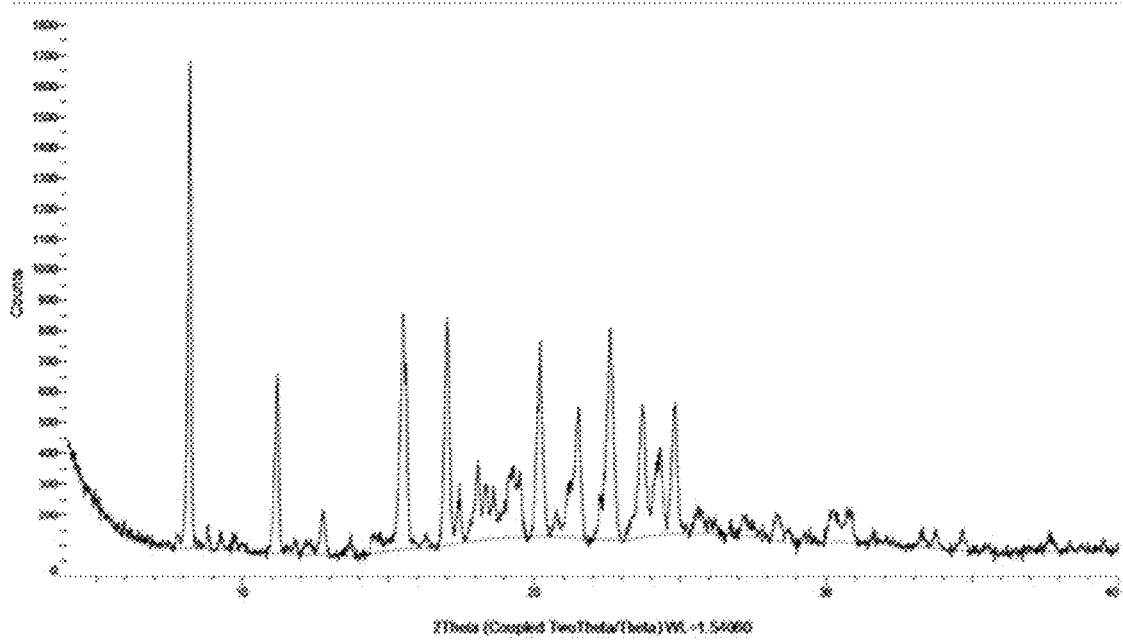
FIG. 7 depicts an XRPD diffractogram of a sample comprising crystalline tabernanthalog hemifumarate salt having Pattern #14. The XRPD signals observed in this diffractogram are characterized in Table 181D.

This example describes the production of tabernanthalog hemifumarate. Tabernanthalog free base and fumaric acid in equimolar amounts were dissolved methanol (10 vol) with heating, and the resultant solution was concentrated to dryness and the solid residue was analyzed by $^1$H NMR, XRPD and DSC. The $^1$H NMR spectrum for the hemifumarate product is provided as FIG. 6. This sample was subjected to equilibration in 20 vol acetonitrile, dried and reanalyzed with XRPD, to provide crystalline tabernanthalog hemifumarate yielding the diffractogram provided in FIG. 7.

Example 5: Polymorph Screen of the Tabernanthalog Fumarate Salt

| Abbreviations | |
|---|---|
| $a_w$ | Water activity |
| AWS | Analytical Working Standard |
| ca. | circa, approximately |
| cf. | to confer, to compare |
| ° C. | degree Celsius |
| CP | Chemical Purity |
| Da | Dalton |
| DSC | Differential Scanning Calorimetry |
| DTA | Differential Thermal Analyses |
| DVS | Dynamic Vapour Sorption |
| e.g. | for example |
| etc. | etcetera |
| FaSSIF | Fasted State Simulated Intestinal Fluid |
| FaSSGF | Fasted State Simulated Gastric Fluid |
| FeSSIF | Fed State Simulated Intestinal Fluid |
| g | gram |
| GRAS | Generally Recognized As Safe |
| h | hour |
| HPLC | High Performance Liquid Chromatography |
| HSM | Hot Stage Microscopy |
| i.e. | that is |
| IR | Infrared Spectroscopy |
| IPC | In Process Check |
| J | Joule |
| KF | Karl Fischer (determination of the water content by coulometric titration) |
| kg | kilogram |
| LOD | Loss On Drying |
| mAu | milli-Absorption units (chromatographic unit of peak height) |
| mAu*s | milli-Absorption units multiplied by second (chromatographic unit of peak area) |
| MET/CR | Aptuit chromatography method reference |
| min. | minute |
| mg | milligram |
| ml | milliliter |
| mol | mole, amount of substance |
| M.L | Mother Liquors |
| N/A | Not Applicable |
| n.a. | not analyzed |
| n.d. | not detected |
| nm | nanometre |
| NMR | Nuclear Magnetic Resonance |
| oab | on anhydrous basis |
| osfb | on solvent free basis |
| oasfb | on anhydrous solvent free basis |
| pH | $-\log [H^+]$ or pH = $-\log a_{H}^+$ |
| $pK_a$ | $-\log (K_a)$, acid dissociation constant |
| PLM | Polarized Light Microscopy |
| REP | Aptuit report reference |
| RFA | Request for analysis (unique reference number) |
| RB | Round bottom (referring to glassware) |
| RH | Relative Humidity ($a_w$ * 100) |
| RP | Reverse Phase |
| RT | Room Temperature (ambient, typically: 18 to 23° C.) |
| s | second |
| T | Temperature (° C.) |
| TCNB | 2,3,5,6-Tetrachloronitrobenzene ($C_6HCl_4NO_2$, F.W. 260.89 gmol$^{-1}$) |
| TGA | Thermogravimetric Analysis |
| th. | theoretical yield |
| UV | Ultra Violet |
| vol. | volume |
| vs. | versus |
| v/v | volume/volume |
| W | Watt |
| w/w | weight/weight |
| XRPD | X-Ray Powder Diffraction |

Definitions

| | |
|---|---|
| Amorphous | Exhibits no long-range crystal order and displays a diffuse noise halo x-ray diffraction pattern |
| Cross polarized light | Light passed through two polaroid filters orientated at ninety degrees to one another |
| Disordered | The API lacks long range order and tends towards the amorphous phase. Crystalline substances are characterized by well-defined XRPD reflections that occur because atoms are periodically arranged in space. When the API exhibits a reduction in long range periodicity the X-rays are scattered in a greater number of directions leading to less resolved and lowered intensity peaks. When the scattering occurs in many directions the structure is said to be disordered or amorphous |
| Habit (crystal) | Different crystal size or shape |
| Isostructural | Contains many similarities to the crystal lattice of the related single form |
| Isomorphic | Retains the structural characteristics of the original lattice after dehydration or de-solvation and is usually metastable, e.g. a dehydrated non-stoichiometric hydrate; i.e. exhibits homomorphism usually generated via loss of solvent or water. The dehydrated lattice is usually disordered and physically unstable and can readily absorb molecules of similar size and affinities to generate isomorphic solvates. |
| Normal light | Vibrates in all directions perpendicular to the axis to which the light travels |
| Particle size | Normally expressed as a volume distribution, (semi-qualitative measurements may be performed by SEM. |
| Plane polarized light | Light passed through a polaroid filter which allows light vibrating in one plane to be transmitted. |
| Photomicrograph | Image captured of a small object under magnification through an optical microscope. |
| Polymorphism | Crystalline solid able to exhibit different crystalline phases. |
| Pseudopolymorphism | Different crystal structure attributed to the incorporation of molecular water or solvent |

| | |
|---|---|
| Stoichiometric solvate | Contains a fixed ratio of solvent that is integral to the crystal structure |
| Non-stoichiometric solvate | Contains a non-fixed ratio of solvent that occupies various structural voids. The crystal structure is retained even as the solvent ratio varies |
| Thermogram | Differential scanning calorimetry trace: heat flow on y-ordinate (mW), time (minutes)/temperature (° C.) on x-ordinate. |

A. Study Overview

This study summarizes the data collected from the polymorph screen that was performed on the tabernanthalog monofumarate salt.

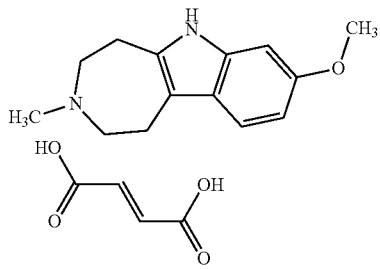

Name: (2E)-but-2-enedioic acid;
8-methoxy-3-methyl-
1H,2H,3H,4H,5H,6H-
azepino[4,5-b]indole
Molecular weight: 346.38
Formula: $C_{18}H_{22}N_2O_5$

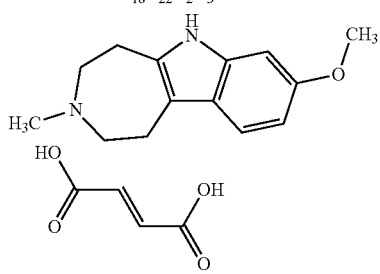

Name: (2E)-but-2-enedioic acid;
8-methoxy-3-methyl-
1H,2H,3H,4H,5H,6H-
azepino[4,5-b]indole
Molecular weight: 346.38
Formula: $C_{18}H_{22}N_2O_5$ Tabernanthalog Monofumarate Salt Tabernanthalog monofumarate was supplied as crystalline solid (supplied batch, Pattern #1) and stoichiometry in the supplied batch, is 1.0 to 1.0 by $^1$H NMR. Fumaric acid is a 1,4-dicarboxylic acid and is mono-salified; hence, the tabernanthalog monofumarate salt as supplied, is a hydrogen fumarate acid salt. There was a risk that the tabernanthalog monofumarate salt may reproportionate into Tabernanthalog hemifumarate salt+0.5 fumaric acid; or disproportionate into discrete non-ionized entities, i.e., Tabernanthalog (native) and fumaric acid. Any manufacturing crystallization must involve complete dissolution of each precursor, otherwise there is a risk that regions of the tabernanthalog monofumarate salt, Tabernanthalog hemifumarate salt, non-ionized Tabernanthalog and non-ionized fumaric acid may occur in the solid phase. Chemically, the azepine ring system of Tabernanthalog, is incapable of Michael addition to the fumaric acid counter ion. Esterification of the fumaric acid counterion by several alcohols is possible (this was monitored by $^1$H NMR).

B. Objectives

The objectives of this study were (a) to survey the experimental polymorph space of the tabernanthalog monofumarate salt, (b) identify and characterize single anhydrous forms, and (c) determine the succession of these forms and nominate a preferred form that is suitable for manufacturing scale-up.

C. Experimental

Instrumentation i. DSC

A Mettler Toledo DSC 3 instrument was used for the thermal analysis operating with STARe™ software. The analysis was conducted in 40 µl open aluminum pans, under nitrogen and sample sizes ranged from 1 to 10 mg. Typical analysis method was 20 to 250° C. at 10° C./minute.

Alternatively, a Mettler Toledo DSC 821 instrument was used for the thermal analysis operating with STARe™ software. The analysis was conducted in 40 µl open aluminum pans, under nitrogen and sample sizes ranged from 1 to 10 mg. Typical analysis method was 20 to 250° C. at 10° C./minute.

ii. FT-IR

FT-IR Spectra were acquired using a PerkinElmer Frontier FT-IR spectrometer. Samples were analyzed directly using a universal ATR attachment in the Mid and Far frequency ranges; 4000 to 30 cm$^{-1}$. Spectra were processed using Spectrum software. Standard KBr windows are used for mid-IR applications; polyethylene and polyethylene/diamond windows are used for operation in the far-IR. Further capabilities of the instrument include a liquid flow cell with ZnSe windows used for rapid monitoring of reactions. This couples with timebase software which allows time-resolved measurements to be taken.

iii. LC-MS

Routine Liquid Chromatography-Mass Spectrometry (LC-MS) data were collected using the Agilent 1260 Infinity II interfaced with 1260 Infinity II DAD HS and Agilent series 1260 Infinity II binary pump.

The instrument used a single quadrupole InfinityLab MSD. The instrument was calibrated up to 2000 Da.

iv. $^1$H NMR $^1$H NMR Spectra were acquired using a Bruker 400 MHz spectrometer and data was processed using Topspin. Samples were prepared in DMSO-d$_6$ at typical concentrations of 10 to 20 mg/mL and up to 50 mg/mL for $^1$H NMR w/w assay and calibrated to the corresponding non-deuterated solvent residual at 2.50 ppm.

v. $^1$H NMR w/w Assay

Assays (w/w) of API by $^1$H NMR spectroscopy were measured by the project chemist.

Internal standard 2,3,5,6-terachloronitrobenzene (TCNB), (ca. 20 mg, F.W. 260.89) were dissolved in DMSO-$d_6$ (2.0 mL) and the $^1$H NMR spectrum was acquired using an extended relaxation method.

vi. Thermal Gravimetric Analysis

A Mettler Toledo TGA 2 instrument was used to measure the weight loss as a function of temperature from 25 to 500° C. The scan rate was typically 5 or 10° C. per minute. Experiments and analysis were carried out using the STARe™ software. The analysis was conducted in 100 µL open aluminum pans, under nitrogen and sample sizes ranged from 1 to 10 mg.

vii. XRPD Analysis

X-Ray powder diffraction (XRPD) analysis was carried out using a Bruker D2 Phaser powder diffractometer equipped with a LynxEye detector. The specimens underwent minimum preparation but, if necessary, they were lightly milled in a pestle and mortar before acquisition. The specimens were located at the center of a silicon sample holder within a 5 mm pocket (ca. 5 to 10 mg).

The samples were continuously spun during data collection and scanned using a step size of 0.02° 2-theta (2θ) between the range of 4° to 40° 2-theta. Data was acquired using either 3- or 20-minutes acquisition methods. Data was processed using Bruker Diffrac.Suite.

Peak tables report only peaks >10%.

Relative intensity values in peak tables were calculated using the Net. intensity values.

Background curvature is automatically calculated over 4 to 40° 2-theta by the Brucker EVA software.

viii. HPLC (MET/CR/2616)

HPLC data was acquired using an Agilent HPLC instrument. Samples were diluted to 1 mg/mL concentration in $H_2O$/DMSO (1/1, v/v).

Method Parameters:
Column: Halo C18, 150×4.6 mm, 2.7 µm
Inj. volume: 5 µL
Detection: UV @ 212 nm
Mobile Phase A: 0.1% TFA in water/acetonitrile 95/5 v/v
Mobile Phase B: 0.05% TFA in water/acetonitrile 5/95 v/v

| Time | % A | % B |
|---|---|---|
| 0.0 | 100 | 0 |
| 2.0 | 100 | 0 |
| 25.0 | 50 | 50 |
| 30.0 | 0 | 100 |
| 32.0 | 0 | 100 |
| 32.1 | 100 | 0 |
| 37.0 | 100 | 0 |

Flow rate: 1 mL/min
Column temperature: 30° C.
Run time: 37 minutes
Integration time: 32 minutes
Wash vial or syringe wash: Sample diluent ix. DVS The moisture sorption properties of the feed API were analyzed by DVS Intrinsic instrument (Surface Measurement System). Approximately 20 to 50 mg of API was weighed onto an aluminum pan and loaded into the instrument equilibrated at 25° C. The sample was equilibrated under a dry atmosphere (0% relative humidity) for 60 minutes, before increasing the humidity from 0% to 30% at 5% step increment and from 30% to 90% at 10% step increment. A desorption cycle was also applied from 90% to 30% (10% step decrement) and from 30% to 0% (5% step decrement). A rate of change in mass per time unit (dm/dt) of 0.002%/min was set as the equilibrium parameter. Kinetic and isotherm graphs were calculated.

x. Solvents

Twenty-one solvents were selected for the polymorph screen and included the majority of ICH listed Class 3 (Table 4).

TABLE 4

Solvents used in the solubility screen

| Solvents | b.p. (° C.) | ICH Classes |
|---|---|---|
| Acetone | 56 | 3 |
| Acetonitrile | 82 | 2 |
| tert-Butylmethyl ether | 55 | 3 |
| Dichloromethane | 40 | 2 |
| DMSO | | |
| Ethanol | 78 | 3 |
| Ethyl acetate | 75 | 3 |
| 2-Propanol | 83 | 3 |
| iPrOAc | 87 | 3 |
| Methanol | 65 | 2 |
| Methylethyl ketone | 80 | 3 |
| 2-Methyl THF | 80 | # |
| Tetrahydrofuran | 66 | 2 |
| Toluene | 111 | 2 |
| Water | 100 | # |

D. Polymorph Screen i. Qualitative Solubility Screen (Experiment Reference 1)

a. Experimental Procedure

The tabernanthalog monofumarate salt (Pattern #1, Sample Reference 1, 25 mg, 1 wt) was weighed out in 20 separate vials to qualitatively examine the solubility in an array of diverse solvents. The solubility was tested initially at 5 vol at 20° C., 40° C., and reflux. If insoluble at 5 vol, the solvent quantity was increased to 10 vol, 15 vol and 20 vol of the respective solvent. The suspensions that occurred upon cooling down (vials that did not show precipitation at 20° C., were subjected to sub-ambient temperatures) were centrifuged and the solvent wet pellets were analyzed by XRPD. The insoluble suspensions were additionally worked up for XRPD analysis. The resultant powder patterns were subsequently cross-referenced against the input supplied material.

A summary of the experimental conditions and the findings is provided in Table 5.

TABLE 5

Summary of findings from solubility assessment*

| Experiment Reference-Sample Reference | Solvent | ICH Class | 5 vol Solution at 20° C. | 5 vol Solution at 40° C. | 5 vol re-flux | 5 vol Solid on cool-ing | 10 vol Solution at 20° C. | 10 vol Solution at 40° C. | 10 vol re-flux | 10 vol Solid on cool-ing | 15 vol Solution at 20° C. | 15 vol Solution at 40° C. | 15 vol re-flux | 15 vol Solid on cool-ing | 20 vol Solution at 20° C. | 20 vol Solution at 40° C. | 20 vol re-flux | 20 vol Solid on cool-ing |
|---|---|---|---|---|---|---|---|---|---|---|---|---|---|---|---|---|---|---|
| 1-A1 | Acetone | 3 | X | X | X | — | X | X | X | — | X | X | X | — | X | X | X | — |
| 1-B1 | MeCN | 2 | X | X | X | — | X | X | X | — | X | X | X | — | X | X | X | — |
| 1-C1 | Butanol | 3 | X | X | X | — | X | X | Partial | Yes | X | X | ✓ | Yes | | | | |
| 1-D1 | tBME | 3 | X | X | X | — | X | X | X | — | X | X | X | — | X | X | X | — |
| 1-E1 | DCM | 2 | X | X | X | — | X | X | — | — | X | X | — | — | X | X | — | — |
| 1-F1 | Et$_2$O | 3 | X | X | X | — | X | X | — | — | X | X | — | — | X | X | — | — |
| 1-G1 | Ethanol | 3 | X | X | X | — | X | X | X | — | X | Partial | ✓ | Yes | X | Partial | ✓ | Yes |
| 1-H1 | EtOAc | 3 | X | X | X | — | X | X | X | — | X | X | X | — | X | X | X | — |
| 1-I1 | IPA | 3 | X | X | X | — | X | X | X | — | X | X | X | — | X | X | X | — |
| 1-J1 | iPrOAc | 3 | X | X | X | — | X | X | X | — | X | X | X | — | X | X | X | — |
| 1-K1 | Methanol | 2 | X | X | ✓ | Yes | | | | | | | | | | | | |
| 1-L1 | MEK | 3 | X | X | X | — | X | X | X | — | X | X | X | — | X | X | X | — |
| 1-M1 | 2-MeTHF | 3 | X | X | X | — | X | X | X | — | X | X | X | — | X | X | X | — |
| 1-N1 | THF | 2 | X | X | X | — | X | X | X | — | X | X | X | — | X | X | X | — |
| 1-O1 | Toluene | 2 | X | X | X | — | X | X | X | — | X | X | X | — | X | X | X | — |
| 1-P1 | Water | # | X | X | ✓ | Yes | X | Partial | ✓ | Yes | | | | | | | | |
| 1-Q1 | Dioxane | 3 | X | X | X | — | X | X | X | — | X | X | X | — | X | X | X | — |
| 1-R1 | CPME | 3 | X | X | X | — | X | X | X | — | X | X | X | — | X | X | X | — |
| 1-S1 | Heptane | 3 | X | X | X | — | X | X | X | — | X | X | X | — | X | X | X | — |
| 1-T1 | MIBK | 3 | X | X | X | — | X | X | X | — | X | X | X | — | X | X | X | — |
| 1-A1 | Acetone | 3 | X | X | X | — | X | X | X | — | X | X | X | — | X | X | X | — |
| 1-B1 | MeCN | 2 | X | X | X | — | X | X | X | — | X | X | X | — | X | X | X | — |
| 1-C1 | Butanol | 3 | X | X | X | — | X | X | Partial | Yes | X | X | ✓ | Yes | | | | |
| 1-D1 | tBME | 3 | X | X | X | — | X | X | X | — | X | X | X | — | X | X | X | — |
| 1-E1 | DCM | 2 | X | X | — | — | X | X | — | — | X | X | — | — | X | X | — | — |
| 1-F1 | Et$_2$O | 3 | X | X | — | — | X | X | — | — | X | X | — | — | X | X | — | — |
| 1-G1 | Ethanol | 3 | X | X | X | — | X | X | X | — | X | Partial | ✓ | Yes | X | Partial | ✓ | Yes |
| 1-H1 | EtOAc | 3 | X | X | X | — | X | X | X | — | X | X | X | — | X | X | X | — |
| 1-I1 | IPA | 3 | X | X | X | — | X | X | X | — | X | X | X | — | X | X | X | — |
| 1-J1 | iPrOAc | 3 | X | X | X | — | X | X | X | — | X | X | X | — | X | X | X | — |
| 1-K1 | Methanol | 2 | X | X | ✓ | Yes | | | | | | | | | | | | |
| 1-L1 | MEK | 3 | X | X | X | — | X | X | X | — | X | X | X | — | X | X | X | — |
| 1-M1 | 2-MeTHF | 3 | X | X | X | — | X | X | X | — | X | X | X | — | X | X | X | — |
| 1-N1 | THF | 2 | X | X | X | — | X | X | X | — | X | X | X | — | X | X | X | — |
| 1-O1 | Toluene | 2 | X | X | X | — | X | X | X | — | X | X | X | — | X | X | X | — |
| 1-P1 | Water | # | X | X | ✓ | Yes | X | Partial | ✓ | Yes | | | | | | | | |
| 1-Q1 | Dioxane | 3 | X | X | X | — | X | X | X | — | X | X | X | — | X | X | X | — |
| 1-R1 | CPME | 3 | X | X | X | — | X | X | X | — | X | X | X | — | X | X | X | — |
| 1-S1 | Heptane | 3 | X | X | X | — | X | X | X | — | X | X | X | — | X | X | X | — |
| 1-T1 | MIBK | 3 | X | X | X | — | X | X | X | — | X | X | X | — | X | X | X | — |

*The tabernanthalog fumarate salt was soluble in refluxing methanol and water at 5 vol (200 mg/ml) and butanol at 15 vol (67 mg/ml).

b. Analytical Characterization Data

XRPD

The analytical characterization data of this study are provided in FIGS. 16-33 and Tables 6-23.

TABLE 6

Peak angle data of 1-A1 (Experiment Reference 1-Sample Reference A1) (wet pellet, Pattern #12)

| 2-θ (°) | d Value | Rel. Intensity (%) |
|---|---|---|
| 8.2 | 10.75 | 17 |
| 9.0 | 9.78 | 16 |
| 14.2 | 6.23 | 11 |
| 16.3 | 5.45 | 66 |
| 16.6 | 5.35 | 15 |
| 18.1 | 4.90 | 22 |
| 18.2 | 4.86 | 14 |
| 18.8 | 4.73 | 11 |
| 19.3 | 4.60 | 14 |
| 20.2 | 4.39 | 24 |
| 21.4 | 4.14 | 24 |

TABLE 6-continued

Peak angle data of 1-A1 (Experiment Reference 1-Sample Reference A1) (wet pellet, Pattern #12)

| 2-θ (°) | d Value | Rel. Intensity (%) |
|---|---|---|
| 22.3 | 3.99 | 12 |
| 22.9 | 3.88 | 17 |
| 25.1 | 3.55 | 13 |
| 25.5 | 3.49 | 100 |
| 26.1 | 3.41 | 13 |
| 26.8 | 3.33 | 22 |
| 27.2 | 3.28 | 14 |

TABLE 7

Peak angle data of 1-B1 (Experiment Reference 1-Sample Reference B1) (wet pellet, Pattern #2a, Form B)

| 2-θ (°) | d Value | Rel. Intensity (%) |
|---|---|---|
| 9.1 | 9.74 | 28 |
| 12.2 | 7.22 | 13 |

TABLE 7-continued

Peak angle data of 1-B1 (Experiment Reference 1-Sample Reference B1) (wet pellet, Pattern #2a, Form B)

| 2-θ (°) | d Value | Rel. Intensity (%) |
| --- | --- | --- |
| 14.2 | 6.22 | 13 |
| 15.6 | 5.67 | 19 |
| 16.0 | 5.52 | 13 |
| 16.3 | 5.42 | 82 |
| 17.1 | 5.19 | 38 |
| 17.4 | 5.09 | 12 |
| 18.1 | 4.91 | 22 |
| 18.8 | 4.71 | 10 |
| 20.6 | 4.30 | 12 |
| 21.0 | 4.22 | 12 |
| 22.9 | 3.89 | 22 |
| 23.1 | 3.85 | 13 |
| 25.1 | 3.55 | 13 |
| 25.6 | 3.48 | 100 |
| 26.8 | 3.32 | 20 |
| 27.3 | 3.27 | 24 |

TABLE 8

Peak angle data of 1-C1 (Experiment Reference 1-Sample Reference C1) (wet pellet, Pattern #15)

| 2-θ (°) | d Value | Rel. Intensity (%) |
| --- | --- | --- |
| 8.5 | 10.44 | 36 |
| 9.0 | 9.82 | 23 |
| 9.5 | 9.31 | 28 |
| 10.6 | 8.36 | 14 |
| 11.1 | 7.98 | 19 |
| 16.3 | 5.43 | 100 |
| 16.9 | 5.25 | 92 |
| 17.0 | 5.21 | 33 |
| 17.7 | 5.00 | 32 |
| 18.1 | 4.90 | 19 |
| 18.5 | 4.80 | 12 |
| 18.9 | 4.68 | 13 |
| 19.3 | 4.60 | 29 |
| 20.0 | 4.45 | 22 |
| 20.9 | 4.26 | 14 |
| 21.1 | 4.21 | 23 |
| 22.5 | 3.95 | 17 |
| 23.4 | 3.80 | 44 |
| 24.2 | 3.67 | 10 |
| 24.5 | 3.63 | 68 |
| 25.0 | 3.56 | 16 |
| 25.2 | 3.53 | 25 |
| 25.6 | 3.48 | 63 |
| 26.3 | 3.38 | 18 |
| 26.8 | 3.32 | 14 |

TABLE 9

Peak angle data of 1-D1 (Experiment Reference 1-Sample Reference D1) (wet pellet, Pattern #1)

| 2-θ (°) | d Value | Rel. Intensity (%) |
| --- | --- | --- |
| 9.0 | 9.76 | 22 |
| 14.2 | 6.23 | 12 |
| 16.3 | 5.43 | 73 |
| 16.7 | 5.29 | 24 |
| 17.0 | 5.21 | 11 |
| 17.4 | 5.08 | 12 |
| 17.7 | 5.00 | 17 |
| 18.1 | 4.90 | 20 |
| 18.8 | 4.71 | 12 |
| 19.3 | 4.59 | 27 |
| 21.1 | 4.21 | 15 |
| 22.3 | 3.98 | 15 |
| 23.2 | 3.83 | 15 |
| 25.1 | 3.54 | 14 |
| 25.5 | 3.49 | 100 |
| 26.8 | 3.32 | 21 |
| 27.2 | 3.27 | 17 |
| 30.0 | 2.98 | 10 |

TABLE 10

Peak angle data of 1-E1 (Experiment Reference 1-Sample Reference E1) (wet pellet, Pattern #1)

| 2-θ (°) | d Value | Rel. Intensity (%) |
| --- | --- | --- |
| 9.1 | 9.76 | 18 |
| 14.2 | 6.22 | 11 |
| 16.3 | 5.43 | 84 |
| 16.7 | 5.30 | 23 |
| 18.1 | 4.91 | 19 |
| 19.3 | 4.60 | 32 |
| 21.3 | 4.17 | 16 |
| 21.8 | 4.07 | 19 |
| 22.3 | 3.98 | 16 |
| 23.1 | 3.84 | 12 |
| 23.8 | 3.74 | 10 |
| 25.1 | 3.54 | 13 |
| 25.5 | 3.49 | 100 |
| 26.1 | 3.41 | 23 |
| 26.8 | 3.32 | 23 |
| 27.2 | 3.27 | 16 |
| 30.0 | 2.98 | 10 |

TABLE 11

Peak angle data of 1-G1 (Experiment Reference 1-Sample Reference G1) (wet pellet, Pattern #5)

| 2-θ (°) | d Value | Rel. Intensity (%) |
| --- | --- | --- |
| 8.3 | 10.70 | 100 |
| 11.1 | 7.97 | 11 |
| 15.4 | 5.74 | 11 |
| 17.0 | 5.21 | 19 |
| 21.5 | 4.13 | 11 |
| 21.5 | 4.13 | 11 |

TABLE 12

Peak angle data of 1-H1 (Experiment Reference 1-Sample Reference H1) (wet pellet, Pattern #9)

| 2-θ (°) | d Value | Rel. Intensity (%) |
| --- | --- | --- |
| 7.9 | 11.15 | 22 |
| 9.1 | 9.71 | 28 |
| 10.4 | 8.48 | 11 |
| 14.3 | 6.20 | 14 |
| 15.9 | 5.59 | 57 |
| 16.4 | 5.41 | 79 |
| 16.8 | 5.27 | 12 |
| 17.0 | 5.20 | 21 |
| 17.5 | 5.06 | 10 |
| 18.1 | 4.89 | 24 |
| 18.9 | 4.69 | 11 |
| 19.4 | 4.57 | 29 |
| 20.7 | 4.29 | 14 |
| 21.8 | 4.07 | 20 |
| 22.3 | 3.98 | 16 |
| 24.6 | 3.61 | 47 |

TABLE 12-continued

Peak angle data of 1-H1 (Experiment Reference 1-Sample Reference H1) (wet pellet, Pattern #9)

| 2-θ (°) | d Value | Rel. Intensity (%) |
|---|---|---|
| 25.3 | 3.52 | 32 |
| 25.6 | 3.48 | 100 |
| 26.9 | 3.32 | 24 |
| 27.3 | 3.27 | 13 |
| 28.7 | 3.11 | 12 |

TABLE 13

Peak angle data of 1-I1 (Experiment Reference 1-Sample Reference I1) (wet pellet, Pattern #10)

| 2-θ (°) | d Value | Rel. Intensity (%) |
|---|---|---|
| 8.2 | 10.75 | 43 |
| 9.1 | 9.72 | 33 |
| 10.8 | 8.15 | 32 |
| 14.3 | 6.20 | 17 |
| 15.2 | 5.81 | 40 |
| 16.4 | 5.41 | 84 |
| 16.9 | 5.24 | 100 |
| 18.1 | 4.90 | 18 |
| 19.2 | 4.62 | 20 |
| 19.8 | 4.47 | 34 |
| 21.4 | 4.15 | 57 |
| 21.8 | 4.07 | 19 |
| 22.2 | 4.00 | 24 |
| 22.6 | 3.93 | 14 |
| 23.5 | 3.78 | 55 |
| 23.7 | 3.75 | 23 |
| 25.2 | 3.53 | 17 |
| 25.6 | 3.48 | 91 |
| 26.8 | 3.32 | 25 |
| 29.8 | 3.00 | 12 |
| 30.0 | 2.98 | 11 |

TABLE 14

Peak angle data of 1-J1 (Experiment Reference 1-Sample Reference J1) (wet pellet, Pattern #8)

| 2-θ (°) | d Value | Rel. Intensity (%) |
|---|---|---|
| 7.6 | 11.66 | 34 |
| 9.0 | 9.78 | 22 |
| 14.2 | 6.23 | 14 |
| 15.8 | 5.59 | 67 |
| 16.3 | 5.43 | 85 |
| 16.7 | 5.32 | 12 |
| 17.4 | 5.08 | 10 |
| 18.1 | 4.91 | 26 |
| 18.8 | 4.71 | 11 |
| 19.1 | 4.64 | 28 |
| 19.3 | 4.61 | 19 |
| 20.6 | 4.31 | 28 |
| 21.9 | 4.05 | 11 |
| 22.3 | 3.98 | 15 |
| 23.8 | 3.73 | 11 |
| 24.3 | 3.67 | 53 |
| 25.0 | 3.56 | 12 |
| 25.1 | 3.54 | 17 |
| 25.5 | 3.49 | 100 |
| 26.8 | 3.32 | 21 |
| 27.2 | 3.27 | 18 |
| 29.9 | 2.98 | 12 |

TABLE 15

Peak angle data of 1-K1 (Experiment Reference 1-Sample Reference K1) (wet pellet, Pattern #6b)

| 2-θ (°) | d Value | Rel. Intensity (%) |
|---|---|---|
| 8.2 | 10.71 | 29 |
| 13.0 | 6.83 | 26 |
| 16.5 | 5.36 | 22 |
| 19.6 | 4.53 | 18 |
| 19.5 | 4.55 | 100 |
| 20.6 | 4.30 | 17 |
| 25.3 | 3.52 | 12 |
| 26.1 | 3.42 | 59 |

TABLE 16

Peak angle data of 1-L1 (Experiment Reference 1-Sample Reference L1) (wet pellet, not assigned)

| 2-θ (°) | d Value | Rel. Intensity (%) |
|---|---|---|
| 7.6 | 11.66 | 19 |
| 7.9 | 11.12 | 22 |
| 9.2 | 9.66 | 30 |
| 14.3 | 6.19 | 18 |
| 16.1 | 5.49 | 33 |
| 16.4 | 5.39 | 86 |
| 16.8 | 5.27 | 15 |
| 17.5 | 5.06 | 14 |
| 18.2 | 4.87 | 24 |
| 19.5 | 4.55 | 21 |
| 21.2 | 4.20 | 13 |
| 22.1 | 4.02 | 11 |
| 22.4 | 3.96 | 19 |
| 22.6 | 3.93 | 12 |
| 23.3 | 3.82 | 13 |
| 23.4 | 3.80 | 11 |
| 24.8 | 3.59 | 22 |
| 25.1 | 3.54 | 18 |
| 25.7 | 3.47 | 100 |
| 26.9 | 3.31 | 22 |
| 27.4 | 3.26 | 16 |

TABLE 17

Peak angle data of 1-M1 (Experiment Reference 1-Sample Reference M1) (wet pellet, Pattern #7)

| 2-θ (°) | d Value | Rel. Intensity (%) |
|---|---|---|
| 7.3 | 12.06 | 29 |
| 9.2 | 9.63 | 26 |
| 14.4 | 6.16 | 14 |
| 16.0 | 5.54 | 54 |
| 16.4 | 5.39 | 92 |
| 16.8 | 5.26 | 23 |
| 17.6 | 5.04 | 11 |
| 18.2 | 4.86 | 24 |
| 19.5 | 4.56 | 31 |
| 19.9 | 4.46 | 19 |
| 20.9 | 4.26 | 15 |
| 21.4 | 4.15 | 30 |
| 21.4 | 4.16 | 31 |
| 22.5 | 3.95 | 21 |
| 23.3 | 3.82 | 11 |
| 25.0 | 3.56 | 27 |
| 25.7 | 3.47 | 100 |
| 27.0 | 3.31 | 21 |
| 27.4 | 3.25 | 19 |
| 30.1 | 2.96 | 10 |

TABLE 18

Peak angle data of 1-N1 (Experiment Reference 1-Sample Reference N1) (wet pellet, Pattern #11)

| 2-θ (°) | d Value | Rel. Intensity (%) |
|---|---|---|
| 7.4 | 11.93 | 39 |
| 9.0 | 9.78 | 17 |
| 10.6 | 8.34 | 11 |
| 11.1 | 7.98 | 13 |
| 14.2 | 6.23 | 11 |
| 16.0 | 5.55 | 94 |
| 16.3 | 5.44 | 61 |
| 17.2 | 5.14 | 24 |
| 18.0 | 4.91 | 16 |
| 20.2 | 4.39 | 66 |
| 20.7 | 4.28 | 24 |
| 20.8 | 4.26 | 16 |
| 21.5 | 4.14 | 67 |
| 22.6 | 3.93 | 19 |
| 23.7 | 3.75 | 22 |
| 23.9 | 3.72 | 17 |
| 25.1 | 3.55 | 15 |
| 25.6 | 3.48 | 100 |
| 26.8 | 3.32 | 20 |

TABLE 19

Peak angle data of 1-O1 (Experiment Reference 1-Sample Reference O1) (wet pellet, Pattern #1)

| 2-θ (°) | d Value | Rel. Intensity (%) |
|---|---|---|
| 9.2 | 9.61 | 26 |
| 14.4 | 6.14 | 17 |
| 14.4 | 6.14 | 18 |
| 16.5 | 5.38 | 80 |
| 16.8 | 5.27 | 48 |
| 17.6 | 5.04 | 12 |
| 18.2 | 4.86 | 24 |
| 18.9 | 4.68 | 19 |
| 19.4 | 4.56 | 25 |
| 20.3 | 4.38 | 21 |
| 22.4 | 3.97 | 29 |
| 22.7 | 3.92 | 14 |
| 25.3 | 3.51 | 19 |
| 25.7 | 3.46 | 100 |
| 26.2 | 3.40 | 24 |
| 26.9 | 3.31 | 26 |
| 27.4 | 3.26 | 16 |

TABLE 20

Peak angle data of 1-P1 (Experiment Reference 1-Sample Reference P1) (wet pellet, Pattern #2c)

| 2-θ (°) | d Value | Rel. Intensity (%) |
|---|---|---|
| 9.1 | 9.73 | 62 |
| 14.2 | 6.23 | 14 |
| 16.3 | 5.44 | 44 |
| 17.4 | 5.09 | 14 |
| 18.0 | 4.92 | 18 |
| 21.9 | 4.05 | 16 |
| 22.2 | 4.00 | 11 |
| 22.5 | 3.94 | 11 |
| 25.1 | 3.55 | 27 |
| 25.5 | 3.49 | 100 |
| 26.7 | 3.33 | 13 |
| 27.2 | 3.28 | 12 |

TABLE 21

Peak angle data of 1-R1 (Experiment Reference 1-Sample Reference R1) (wet pellet, Pattern #1)

| 2-θ (°) | d Value | Rel. Intensity (%) |
|---|---|---|
| 9.2 | 9.61 | 24 |
| 14.4 | 6.16 | 12 |
| 15.1 | 5.87 | 5 |
| 16.5 | 5.38 | 77 |
| 16.8 | 5.26 | 38 |
| 17.7 | 5.02 | 16 |
| 17.9 | 4.96 | 17 |
| 18.3 | 4.85 | 35 |
| 19.0 | 4.67 | 11 |
| 19.5 | 4.56 | 47 |
| 20.3 | 4.37 | 13 |
| 21.4 | 4.16 | 10 |
| 22.4 | 3.96 | 30 |
| 23.3 | 3.82 | 15 |
| 25.7 | 3.47 | 100 |
| 26.3 | 3.39 | 18 |
| 27.0 | 3.30 | 24 |
| 27.4 | 3.25 | 27 |
| 30.1 | 2.96 | 12 |

TABLE 22

Peak angle data of 1-S1 (Experiment Reference 1-Sample Reference S1) (wet pellet, Pattern #1)

| 2-θ (°) | d Value | Rel. Intensity (%) |
|---|---|---|
| 9.2 | 9.63 | 24 |
| 14.4 | 6.16 | 10 |
| 16.5 | 5.38 | 76 |
| 16.8 | 5.27 | 36 |
| 17.6 | 5.03 | 16 |
| 17.8 | 4.97 | 14 |
| 18.2 | 4.86 | 30 |
| 19.0 | 4.67 | 11 |
| 19.4 | 4.57 | 47 |
| 22.2 | 4.00 | 14 |
| 22.4 | 3.96 | 26 |
| 23.2 | 3.82 | 12 |
| 25.7 | 3.47 | 100 |
| 26.3 | 3.39 | 17 |
| 27.0 | 3.30 | 27 |
| 27.4 | 3.26 | 27 |
| 30.1 | 2.97 | 10 |

TABLE 23

Peak angle data of 1-T1 (Experiment Reference 1-Sample Reference T1) (wet pellet, Pattern #1)

| 2-θ (°) | d Value | Rel. Intensity (%) |
|---|---|---|
| 9.2 | 9.61 | 22 |
| 14.4 | 6.16 | 14 |
| 14.3 | 6.19 | 13 |
| 16.4 | 5.39 | 100 |
| 16.9 | 5.25 | 28 |
| 17.6 | 5.04 | 12 |
| 18.2 | 4.86 | 27 |
| 19.0 | 4.67 | 16 |
| 19.4 | 4.56 | 28 |
| 20.4 | 4.35 | 23 |
| 22.4 | 3.97 | 35 |
| 23.2 | 3.84 | 13 |
| 25.4 | 3.51 | 23 |
| 25.7 | 3.47 | 94 |
| 26.4 | 3.38 | 22 |
| 27.0 | 3.30 | 27 |
| 27.4 | 3.26 | 17 | c. Conclusion

Figure 30:
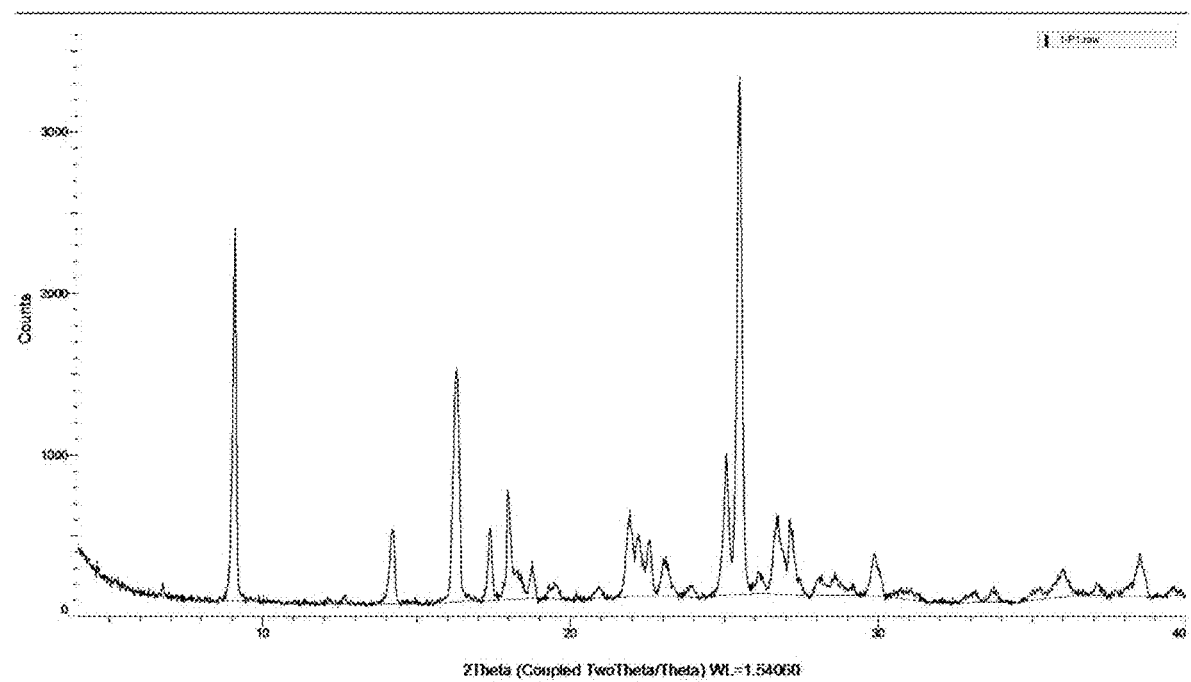
FIG. 30 depicts the XRPD profile of 1-P1 (Experiment Reference 1-Sample Reference P1) (wet pellet, Pattern #2c).
Figure 31:
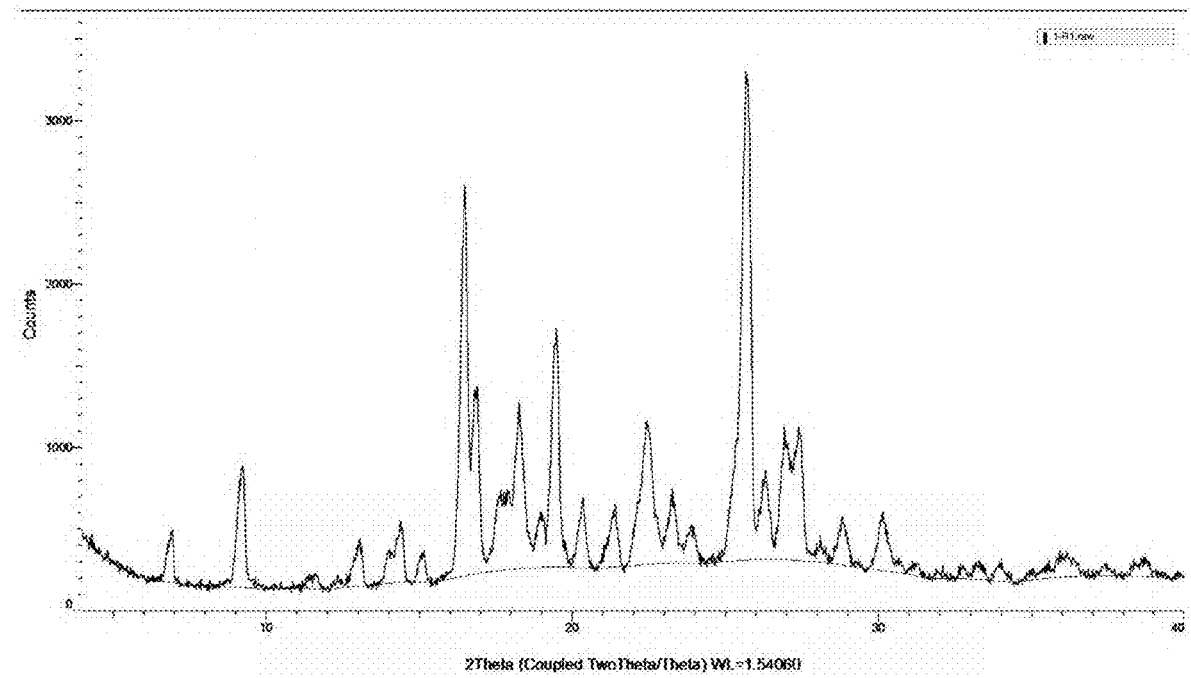
FIG. 31 depicts the XRPD profile of 1-R1 (Experiment Reference 1-Sample Reference R1) (wet pellet, Pattern #1).
Figure 32:
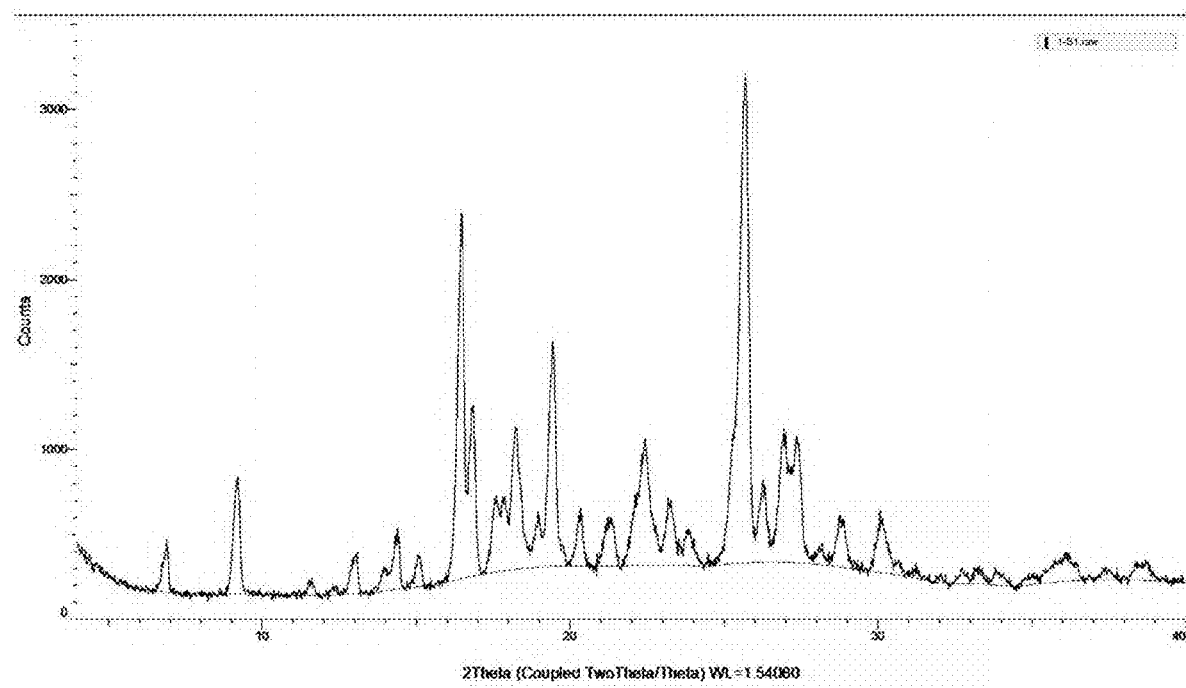
FIG. 32 depicts the XRPD profile of 1-S1 (Experiment Reference 1-Sample Reference S1) (wet pellet, Pattern #1).
Figure 33:
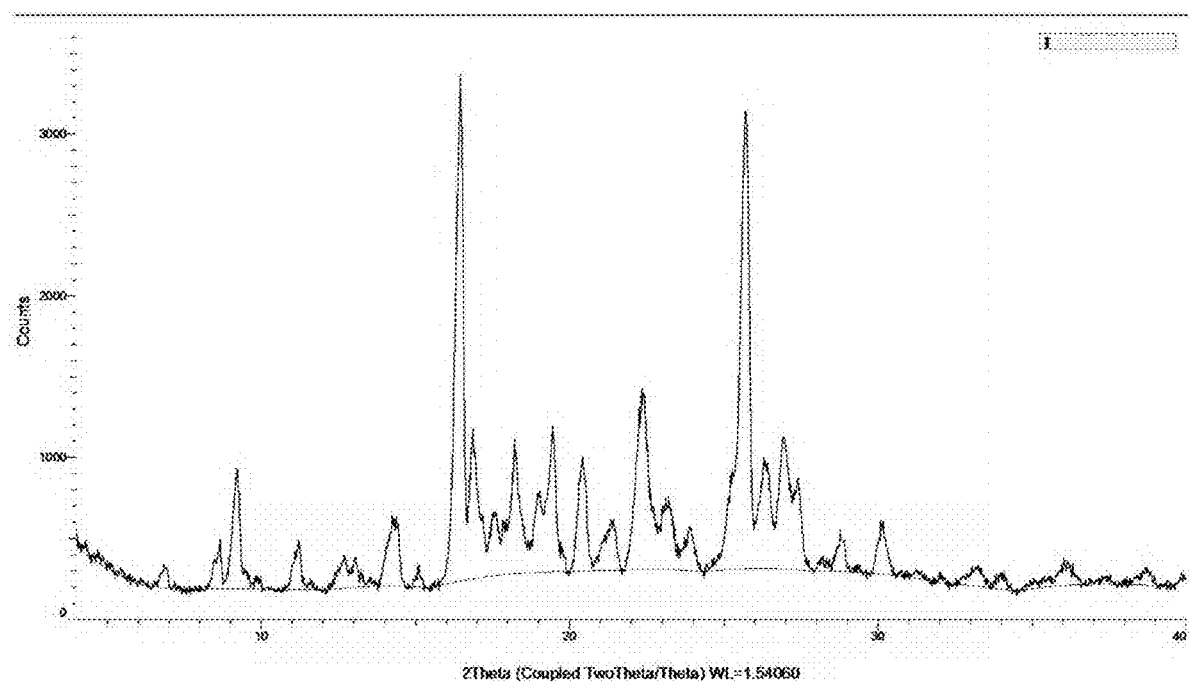
FIG. 33 depicts the XRPD profile of 1-T1 (Experiment Reference 1-Sample Reference T1) (wet pellet, Pattern #1).
Figure 34:
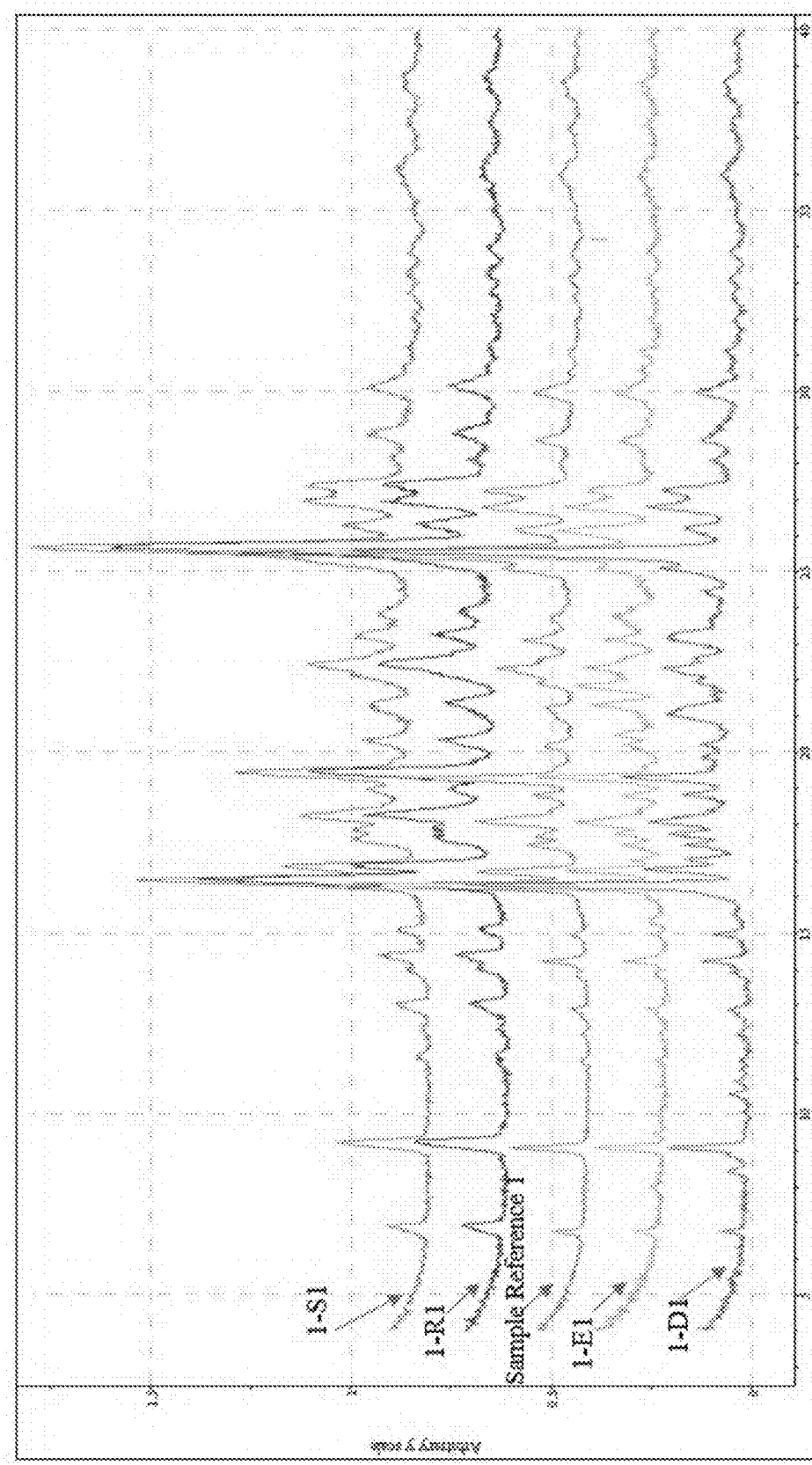
FIG. 34 depicts the XRPD patterns that matched the tabernanthalog monofumarate salt (Sample Reference 1, Pattern #1).
Figure 35:
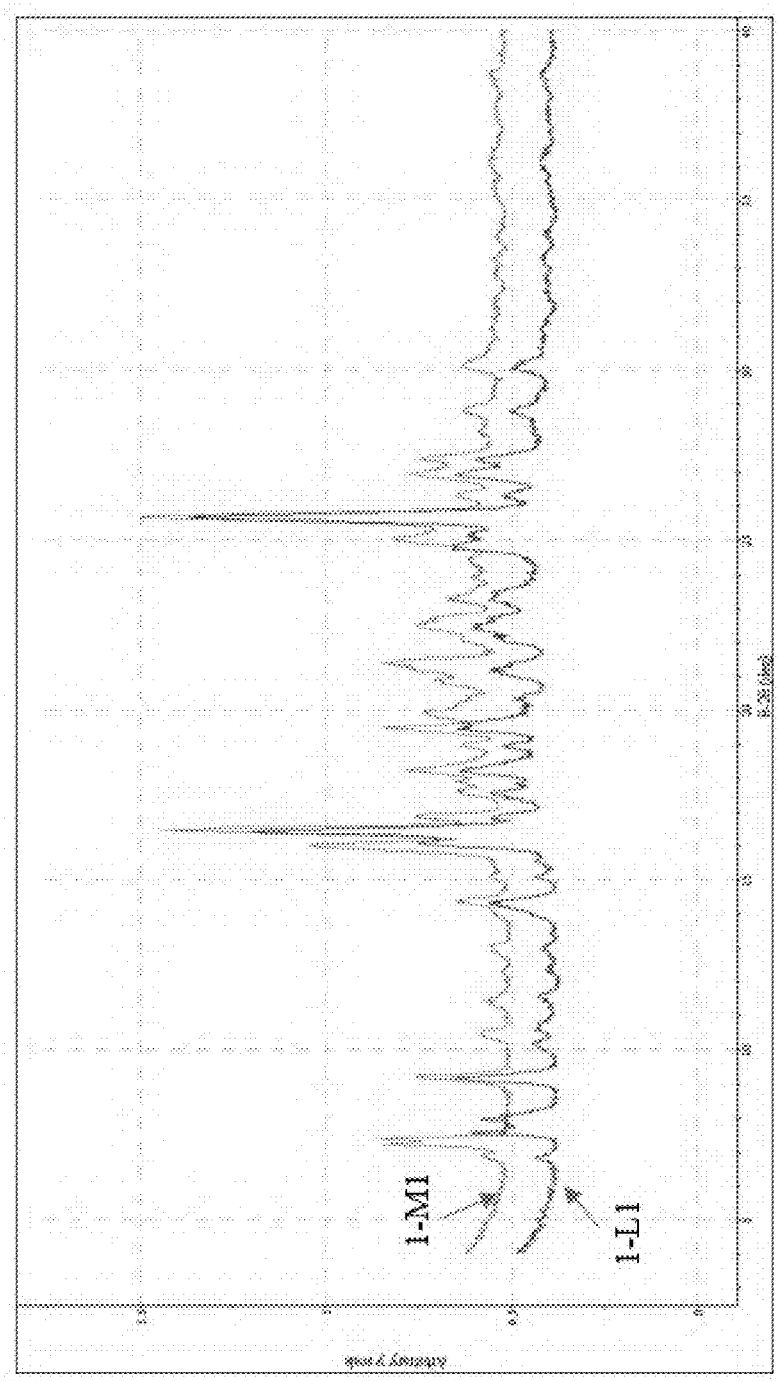
FIG. 35 depicts the XRPD patterns that are approximate match with the tabernanthalog monofumarate salt (Sample Reference 1, Pattern #1).
Figure 36:
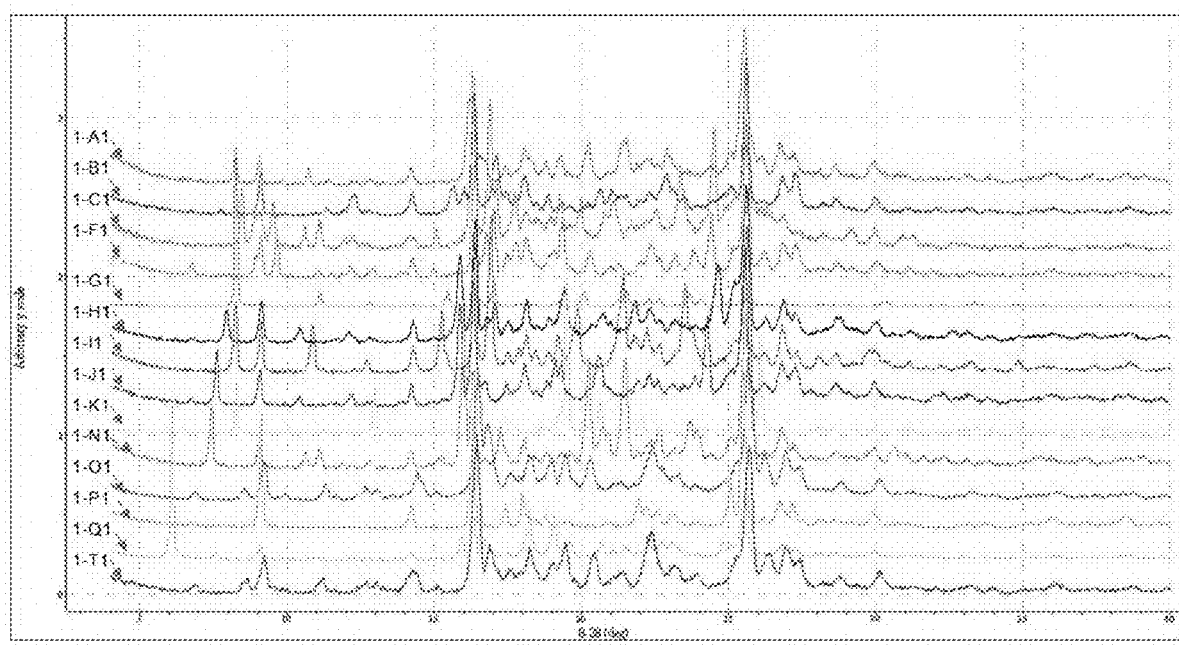
FIG. 36 depicts the XRPD patterns that exhibit differences compared to the tabernanthalog monofumarate salt (Sample Reference 1, Pattern #1).

From the initial findings, the tabernanthalog monofumarate salt appeared to be a strong solvator. Samples 1-C1 (crystallized from butanol), 1-G1 (crystallized from ethanol), 1-K1 (crystallized from methanol) and 1-P1 (crystallized from water), were reanalyzed after drying, to include XRPD, TGA and $^1$H NMR, and confirm that the forms are true anhydrous polymorphs or solvated forms. The XRPD data collected are summarized below:

- Powder patterns of 1-E1 (different 21.8 °2θ), 1-D1, 1-O1, 1-R1, 1-S1, 1-T1 closely resembled the tabernanthalog monofumarate salt (Sample Reference 1, refer to FIG. 34).
- Powder patterns 1-L1 and 1-M1 were paired and resembled Sample Reference 1, except many of the reflections were offset by 0.1 to 0.2 °2θ (refer to FIG. 35).
- Powder pattern 1-A1, closely resembled Sample Reference 1, except additional reflections were present at 8.30, 10.7° and 21.5 °2θ (refer to FIG. 36 and FIG. 16).
- Powder pattern 1-F1, closely resembled Sample Reference 1, except additional reflections were present at 9.7°, 17.1° and 24.4 °2θ (refer to FIG. 36 and FIG. 373).
- Reflections of powder pattern 1-P1 were closely aligned with those of Sample Reference 1, except key reflections at 16.7°, 19.3° were absent (refer to FIG. 36 and FIG. 30). It is worth mentioning that 100% water is often a poor crystallization solvent because it exerts weak control on lipophilic impurities; although water can serve as a polarity modifier in certain binary compositions.
- Powder pattern 1-B1, exhibited key reflection differences at 12.3°, 15.7°, 16.0°, 17.2°, 19.3°, 20.7° and 22.9°2θ (refer to FIG. 36 and FIG. 17).
- Powder pattern 1-C1, appeared to be a mixture of Sample Reference 1 and potentially a new form, that exhibited key reflection differences 8.5°, 9.6°, 10.6°, 11.1°, 16.9°, 17.8°, 20.0°, 20.9, 23.8° and 24.5° (refer to FIG. 36 and FIG. 18).
- Powder pattern 1-G1, exhibited significant preferred orientation effects, with v. strong reflection at 8.3°, this made comparison more difficult, the phase appeared to be a new form that contained remanets of Sample Reference 1 (refer to FIG. 36 and FIG. 21).
- Powder pattern 1-K1, appeared to be a new stable form (refer to FIG. 36 and FIG. 25). Methanol 5 vol, may be a suitable crystallization solvent.

The remainder of the patterns exhibited differences.

ii. Stability Examination of Supplied Material at 40° C./75% RH (Experiment Reference 2)

a. Experimental Procedure

The tabernanthalog monofumarate salt (Pattern #1, Sample Reference 1, 100 mg) was placed inside a wide-necked, open vial (suffix-A) The tabernanthalog monofumarate salt (Pattern #1, Sample Reference 1, 100 mg) was placed inside a wide-necked, open vial and then inside double polyethene bags (SPC/PK/0052), tied tightly with cable ties (suffix-B). Both samples were maintained under equilibrium humidity of 75% RH at 40° C. (chamber placed in a pre-heated oven) and monitored, initially at hourly and then weekly time points.

b. Analytical Characterization Data $^1$H NMR

Figure 37:
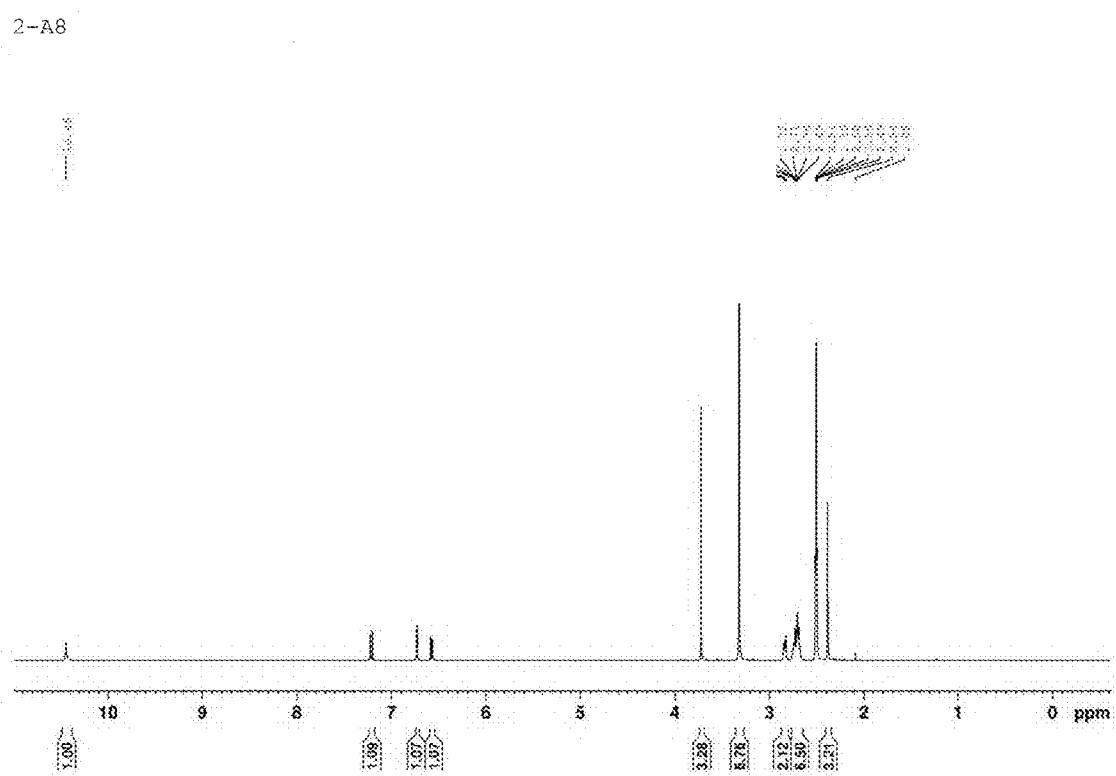
FIG. 37 depicts the $^1$H NMR spectrum of 2-A8 (Experiment Reference 2-Sample Reference A8) (t=5 w, open vial), spectrum was acquired in DMSO-$d_6$ and calibrated to the non-deuterated solvent residual at 2.50 ppm.
Figure 38:
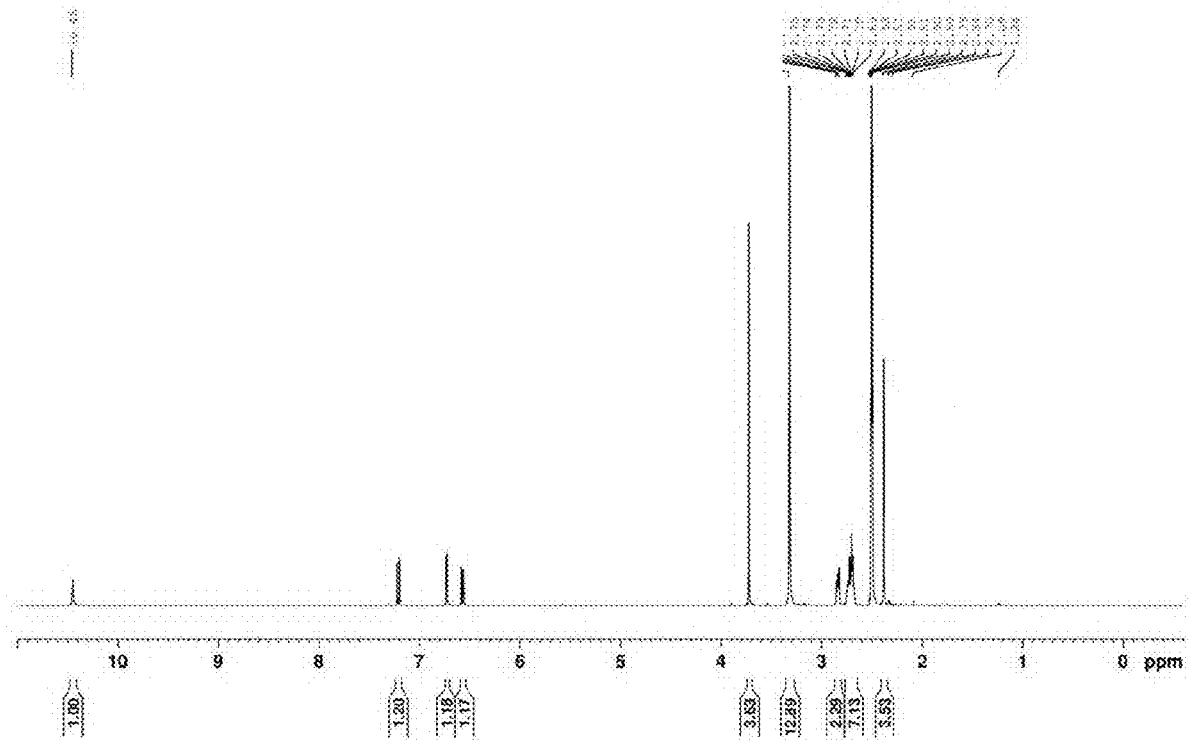
FIG. 38 depicts the $^1$H NMR spectrum of 2-B8 (Experiment Reference 2-Sample Reference B8) (t=5 w, double bagged open vial), spectrum was acquired in DMSO-$d_6$ and calibrated to the non-deuterated solvent residual at 2.50 ppm.

The $^1$H NMR spectrum of 2-A8 (Experiment Reference 2-Sample Reference A8) (t=5 w, open vial), spectrum was acquired in DMSO-$d_6$ and calibrated to the non-deuterated solvent residual at 2.50 ppm (FIG. 37). The $^1$H NMR spectrum of 2-B8 (Experiment Reference 2-Sample Reference B8) (t=5 w, double bagged open vial), spectrum was acquired in DMSO-$d_6$ and calibrated to the non-deuterated solvent residual at 2.50 ppm (FIG. 38).

TGA

Figure 39:
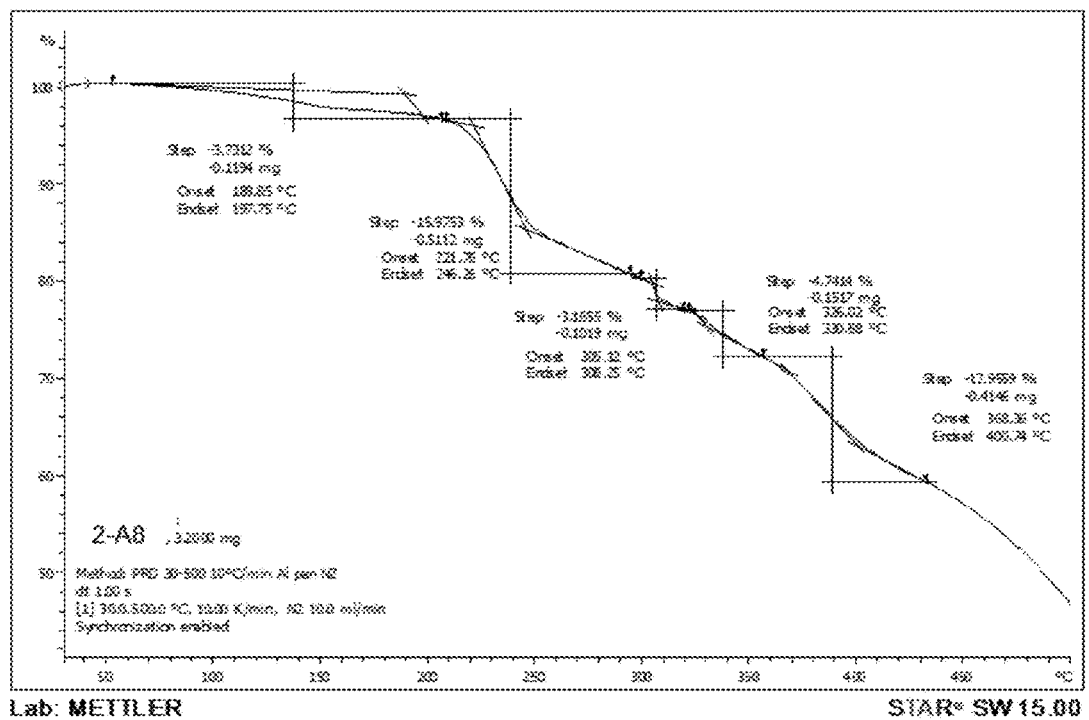
FIG. 39 depicts the TGA profile of 2-A8 (Experiment Reference 2-Sample Reference A8) (t=5 weeks), analysis was acquired at a ramp rate of +10° C./minute.
Figure 40:
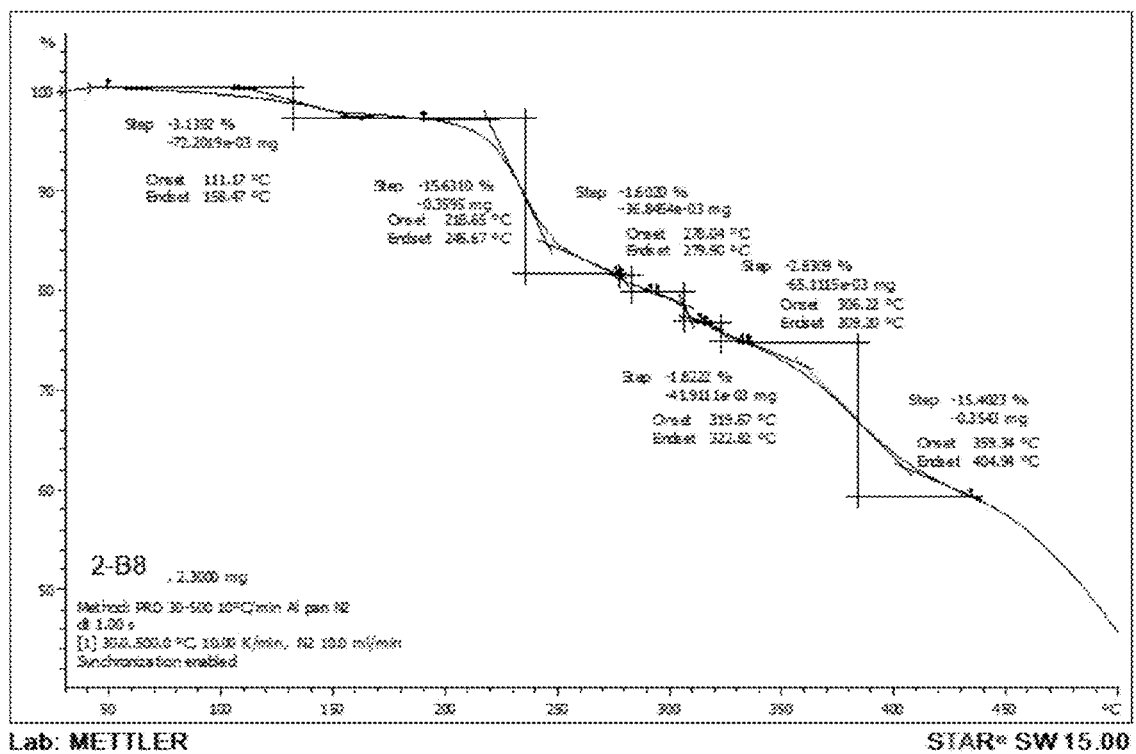
FIG. 40 depicts the TGA profile of 2-B8 (Experiment Reference 2-Sample Reference B8) (t=5 weeks), analysis was acquired at a ramp rate of +10° C./minute.

TGA profile of 2-A8 (Experiment Reference 2-Sample Reference A8) (t=5 weeks), analysis was acquired at a ramp rate of +10° C./minute (FIG. 39). TGA profile of 2-B8 (Experiment Reference 2-Sample Reference B8) (t=5 weeks), analysis was acquired at a ramp rate of +10° C./minute (FIG. 40).

DSC

Figure 41:
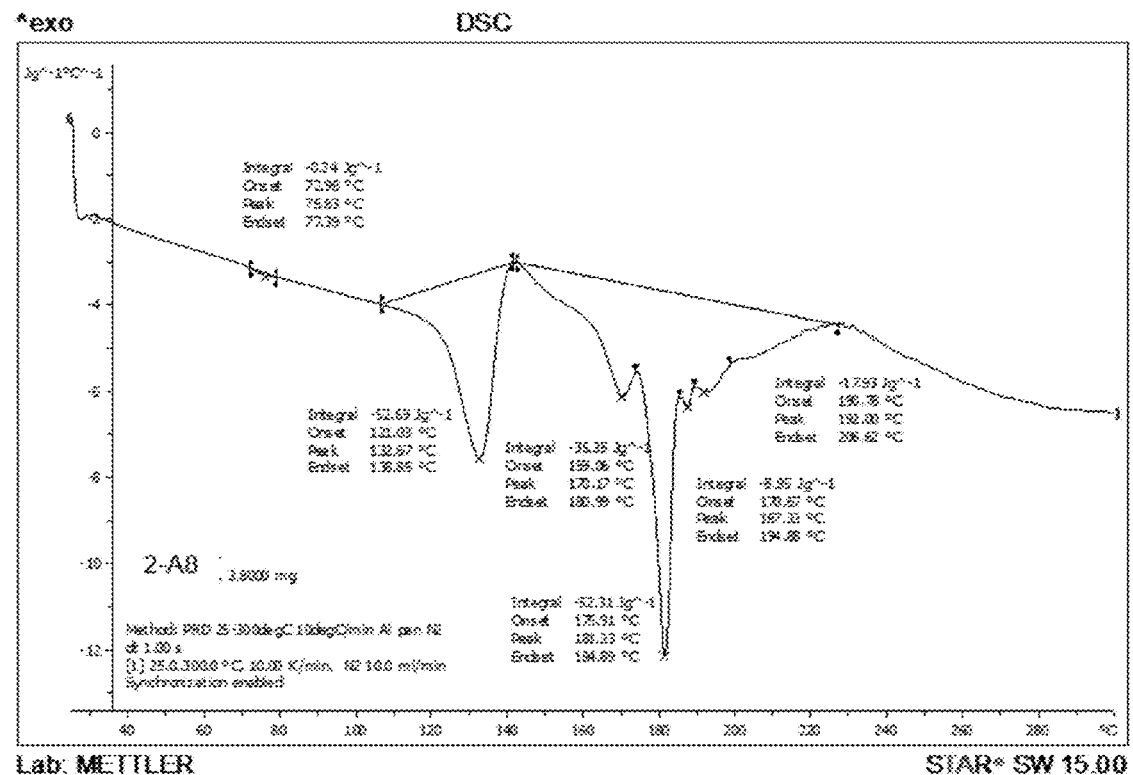
FIG. 41 depicts the DSC profile of 2-A8 (Experiment Reference 2-Sample Reference A8) (t=5 weeks), analysis was acquired at a ramp rate of +10° C./minute.
Figure 42:
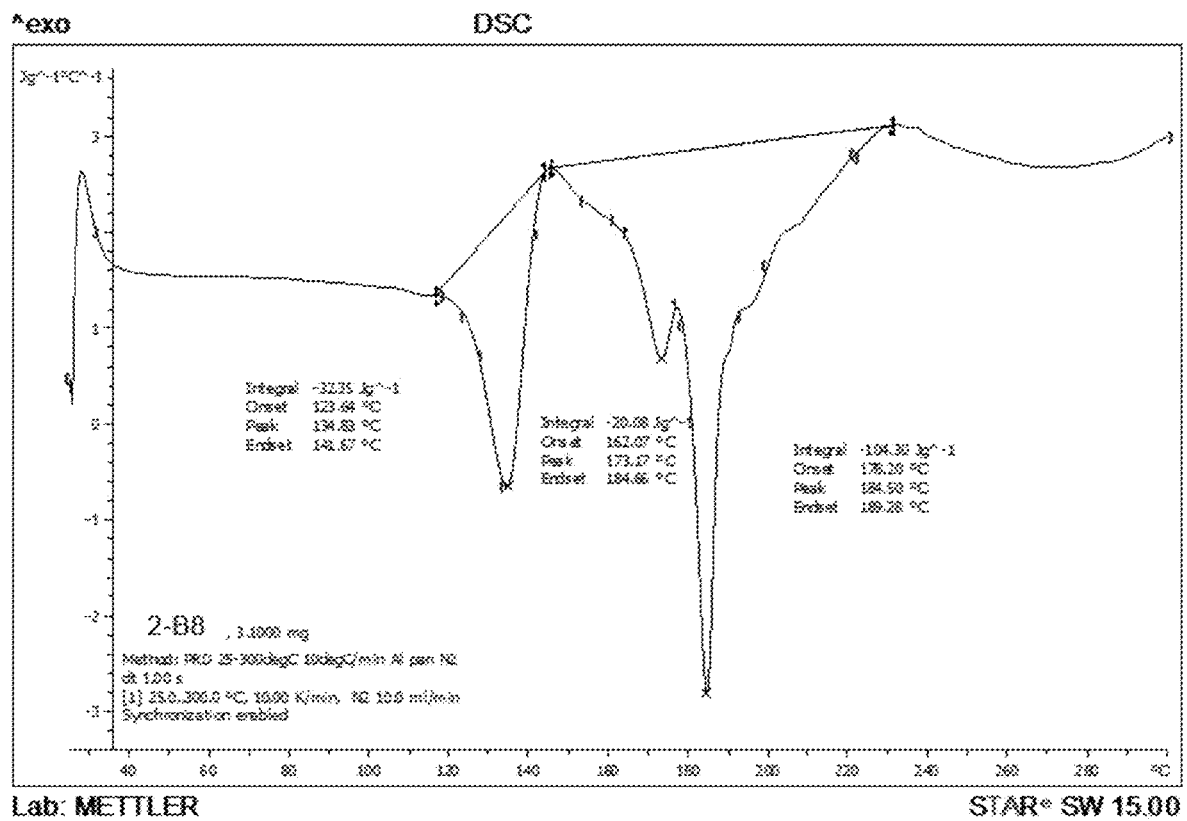
FIG. 42 depicts the DSC profile of 2-B8 (Experiment Reference 2-Sample Reference B8) (t=5 weeks), analysis was acquired at a ramp rate of +10° C./minute.

DSC profile of 2-A8 (Experiment Reference 2-Sample Reference A8) (t=5 weeks), analysis was acquired at a ramp rate of +10° C./minute (FIG. 41). DSC profile of 2-B8 (Experiment Reference 2-Sample Reference B8) (t=5 weeks), analysis was acquired at a ramp rate of +10° C./minute (FIG. 42).

XRPD

Figure 43:
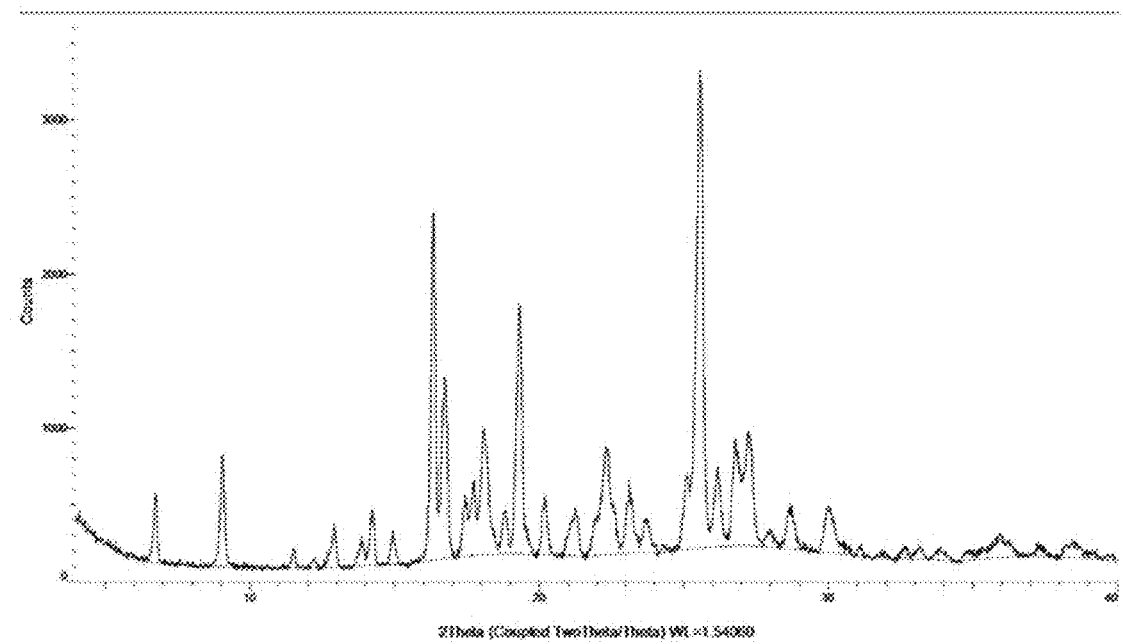
FIG. 43 depicts the XRPD profile of 2-A7 (Experiment Reference 2-Sample Reference A7).
Figure 44:
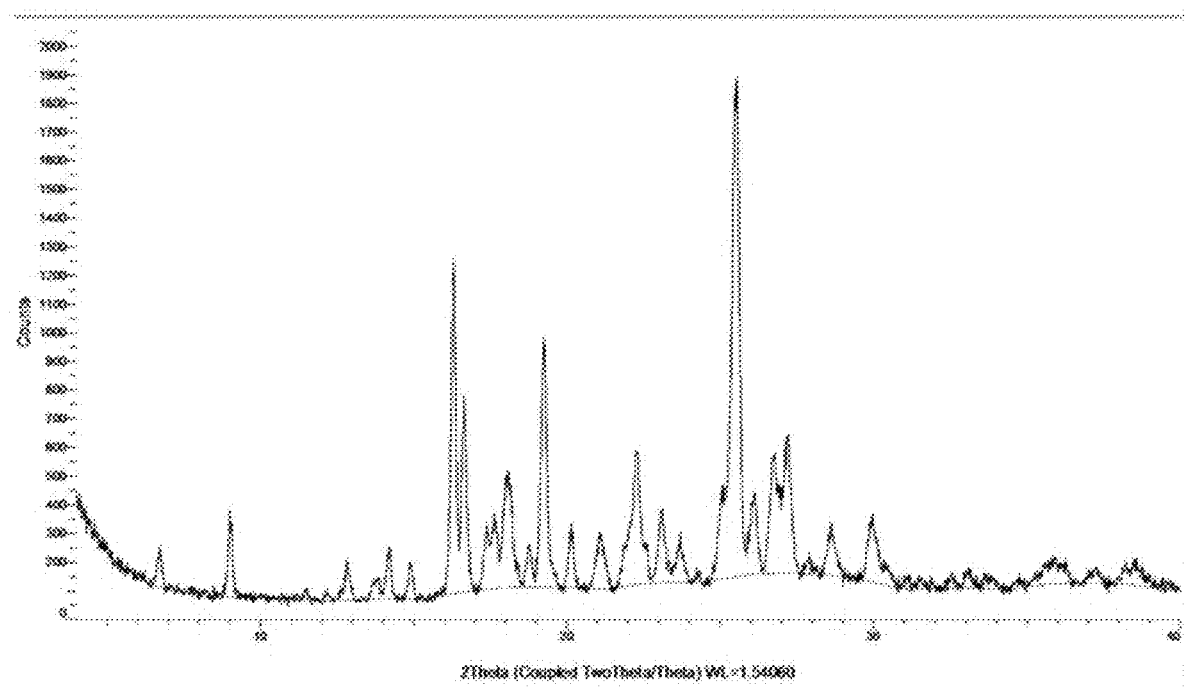
FIG. 44 depicts the XRPD profile of 2-A8 (Experiment Reference 2-Sample Reference A8).
Figure 45:
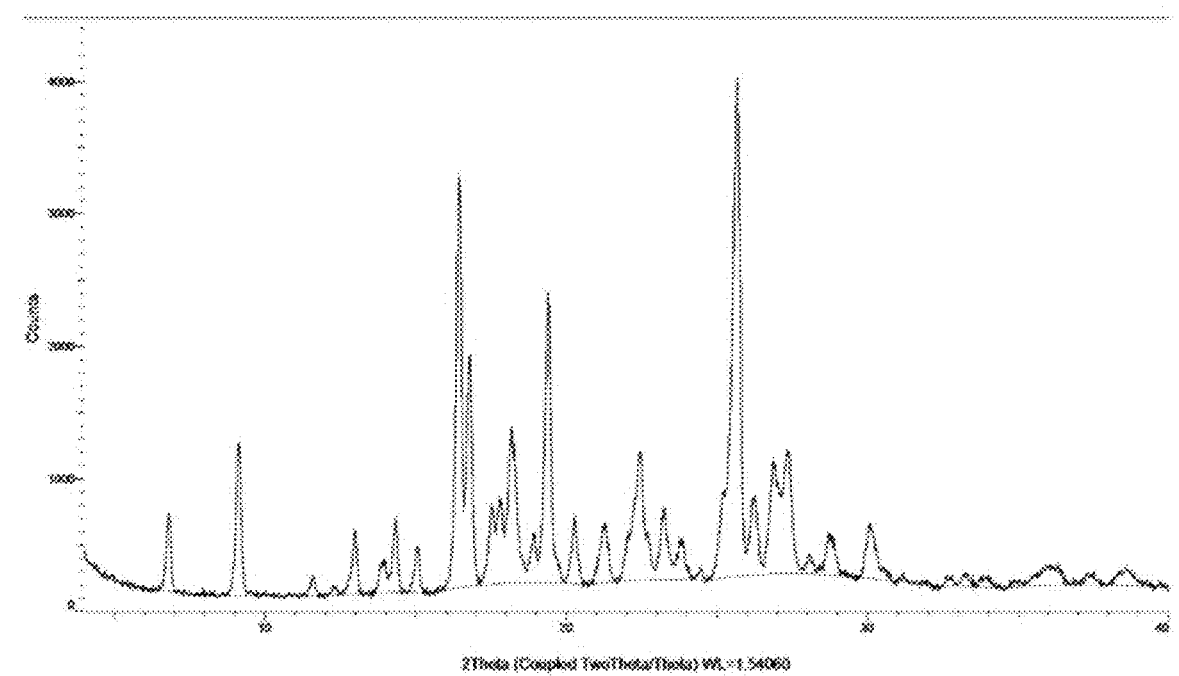
FIG. 45 depicts the XRPD profile of 2-B7 (Experiment Reference 2-Sample Reference B7).
Figure 46:
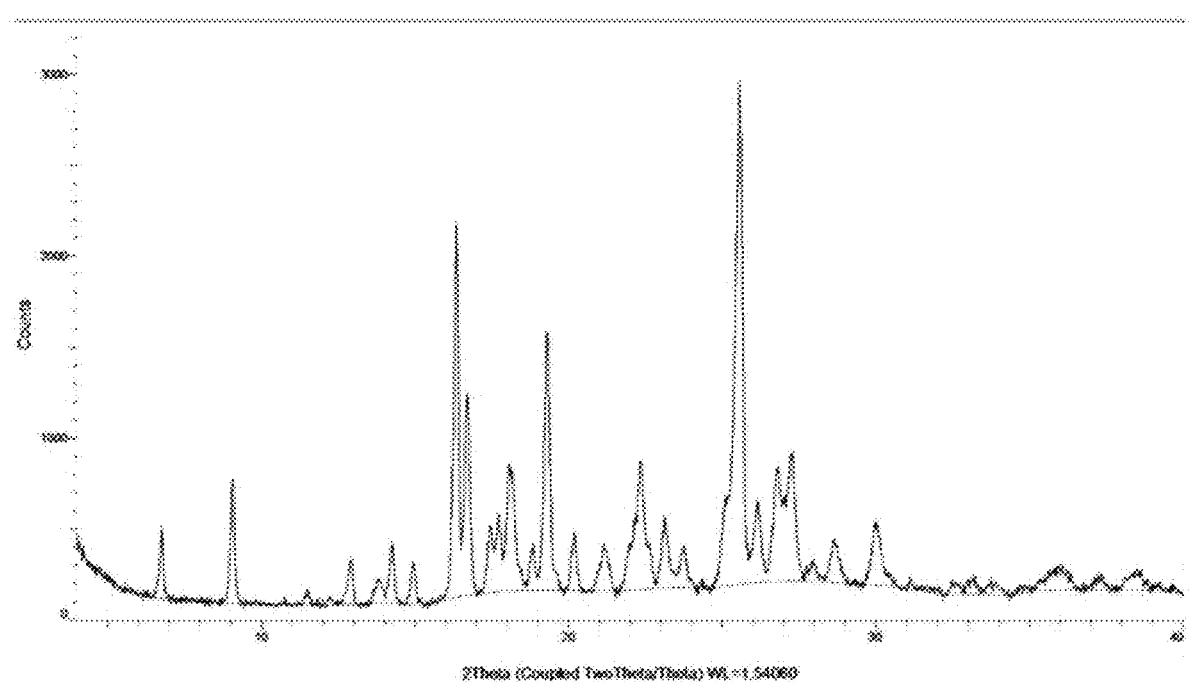
FIG. 46 depicts the XRPD profile of 2-B8 (Experiment Reference 2-Sample Reference B8).

XRPD diffractograms reported herein are for t=4 w and 5 w as no form change was observed during the 5-week period. The XRPD profile of 2-A7 (Experiment Reference 2-Sample Reference A7) (t=4 w) is presented in FIG. 43 and the peaks are listed in Table 24. The XRPD profile of 2-A8 (Experiment Reference 2-Sample Reference A8) (t=5 w) is presented in FIG. 44 and the peaks are listed in Table 25. The XRPD profile of 2-B7 (Experiment Reference 2-Sample Reference B7) (t=4 w) is presented in FIG. 45 and the peaks are listed in Table 26. The XRPD profile of 2-B8 (Experiment Reference 2-Sample Reference B8) (t=5 w) is presented in FIG. 46 and the peaks are listed in Table 27.

TABLE 24

Peak angle data of 2-A7 (Experiment Reference 2-Sample Reference A7) (t = 4 w)

| 2-θ (°) | d Value | Rel. Intensity (%) |
|---|---|---|
| 6.7 | 13.15 | 13 |
| 9.1 | 9.76 | 24 |
| 14.2 | 6.22 | 12 |
| 16.3 | 5.42 | 73 |
| 16.7 | 5.30 | 39 |
| 17.5 | 5.07 | 10 |
| 17.7 | 5.00 | 15 |
| 18.1 | 4.89 | 26 |
| 19.3 | 4.59 | 52 |
| 20.2 | 4.39 | 12 |
| 22.3 | 3.98 | 23 |
| 22.5 | 3.95 | 13 |
| 23.1 | 3.84 | 13 |
| 25.1 | 3.54 | 16 |
| 25.6 | 3.48 | 100 |
| 26.2 | 3.40 | 17 |
| 26.8 | 3.32 | 21 |
| 27.3 | 3.27 | 23 |

TABLE 25

Peak angle data of 2-A8 (Experiment Reference 2-Sample Reference A8) (t = 5 w)

| 2-θ (°) | d Value | Rel. Intensity (%) |
|---|---|---|
| 9.0 | 9.79 | 15 |
| 14.2 | 6.24 | 10 |

TABLE 25-continued

Peak angle data of 2-A8 (Experiment Reference 2-Sample Reference A8) (t = 5 w)

| 2-θ (°) | d Value | Rel. Intensity (%) |
|---|---|---|
| 16.3 | 5.44 | 68 |
| 16.6 | 5.32 | 41 |
| 17.4 | 5.08 | 12 |
| 17.6 | 5.02 | 16 |
| 18.1 | 4.90 | 24 |
| 19.3 | 4.61 | 52 |
| 20.1 | 4.41 | 11 |
| 21.1 | 4.21 | 11 |
| 22.3 | 3.99 | 28 |
| 23.1 | 3.85 | 15 |
| 23.7 | 3.75 | 10 |
| 25.1 | 3.55 | 19 |
| 25.5 | 3.49 | 100 |
| 26.1 | 3.41 | 17 |
| 26.8 | 3.33 | 24 |
| 27.2 | 3.28 | 28 |
| 28.6 | 3.12 | 11 |
| 30.0 | 2.98 | 13 |

TABLE 26

Peak angle data of 2-B7 (Experiment Reference 2-Sample Reference B7) (t = 4 w)

| 2-θ (°) | d Value | Rel. Intensity (%) |
|---|---|---|
| 6.8 | 13.01 | 16 |
| 9.1 | 9.67 | 31 |
| 13.0 | 6.82 | 13 |
| 14.3 | 6.18 | 14 |
| 16.4 | 5.39 | 83 |
| 16.8 | 5.28 | 46 |
| 17.6 | 5.04 | 15 |
| 17.8 | 4.98 | 16 |
| 18.2 | 4.87 | 31 |
| 19.4 | 4.57 | 57 |
| 20.3 | 4.38 | 14 |
| 21.3 | 4.17 | 11 |
| 22.2 | 4.01 | 10 |
| 22.4 | 3.96 | 25 |
| 22.6 | 3.93 | 12 |
| 23.2 | 3.82 | 15 |
| 25.3 | 3.52 | 18 |
| 25.6 | 3.47 | 100 |
| 26.2 | 3.39 | 16 |
| 26.9 | 3.31 | 22 |
| 27.3 | 3.26 | 25 |
| 30.1 | 2.97 | 11 |

TABLE 27

Peak angle data of 2-B8 (Experiment Reference 2-Sample Reference B8) (t = 5 w)

| 2-θ (°) | d Value | Rel. Intensity (%) |
|---|---|---|
| 6.7 | 13.13 | 12 |
| 9.1 | 9.75 | 25 |
| 11.5 | 7.69 | 3 |
| 14.2 | 6.22 | 11 |
| 16.3 | 5.42 | 75 |
| 16.7 | 5.31 | 41 |
| 17.5 | 5.07 | 13 |
| 17.7 | 5.00 | 16 |
| 18.1 | 4.89 | 24 |
| 19.3 | 4.59 | 53 |
| 20.2 | 4.40 | 10 |
| 22.3 | 3.98 | 26 |
| 23.1 | 3.84 | 14 |
| 25.2 | 3.53 | 18 |
| 25.5 | 3.48 | 100 |
| 26.1 | 3.41 | 17 |
| 26.8 | 3.32 | 22 |
| 27.2 | 3.27 | 26 |
| 30.0 | 2.97 | 13 |

HPLC

Figure 47:
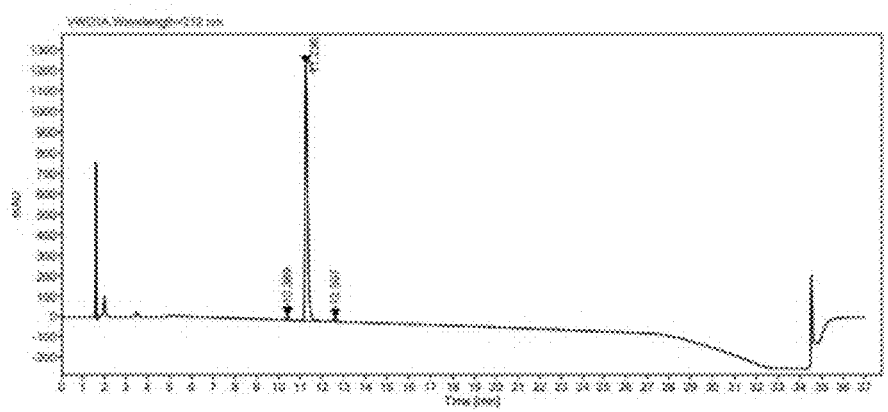
FIG. 47 depicts the HPLC profile of 2-A5 (Experiment Reference 2-Sample Reference A5) (t=2 w).
Figure 48:
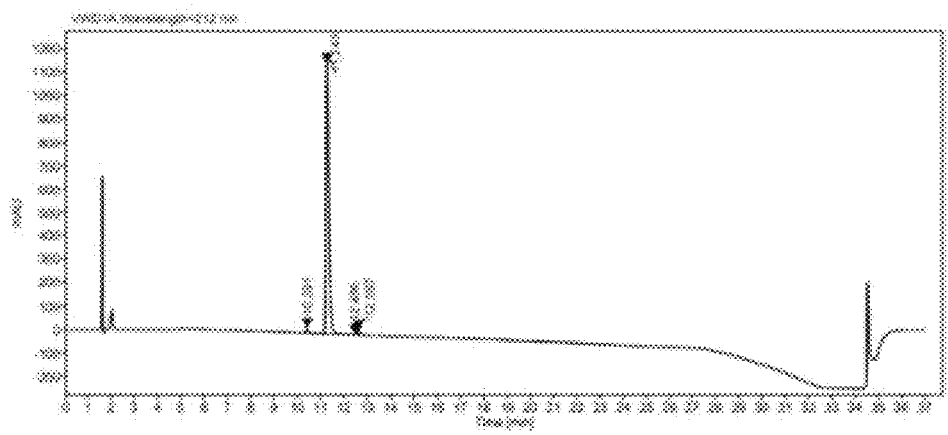
FIG. 48 depicts the HPLC profile of 2-A6 (Experiment Reference 2-Sample Reference A6) (t=3 w).
Figure 49:
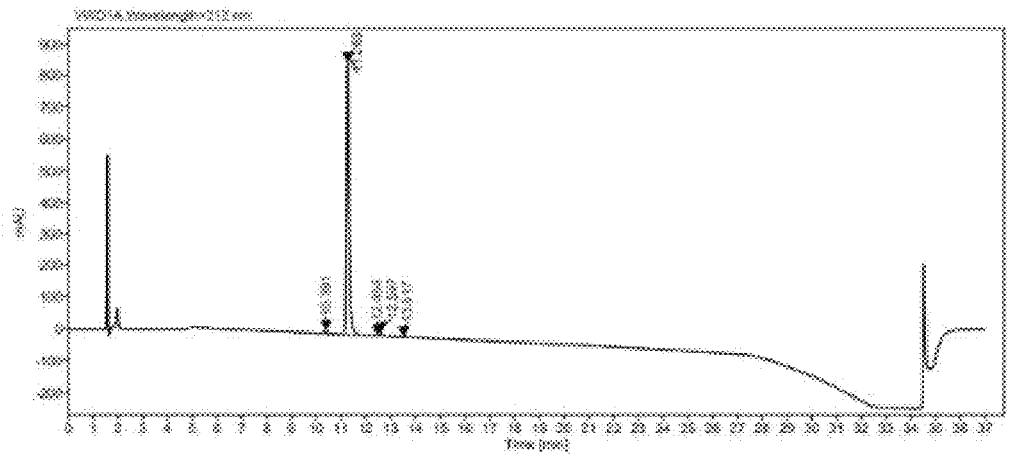
FIG. 49 depicts the HPLC profile of 2-A7 (Experiment Reference 2-Sample Reference A7) (t=4 w).
Figure 50:
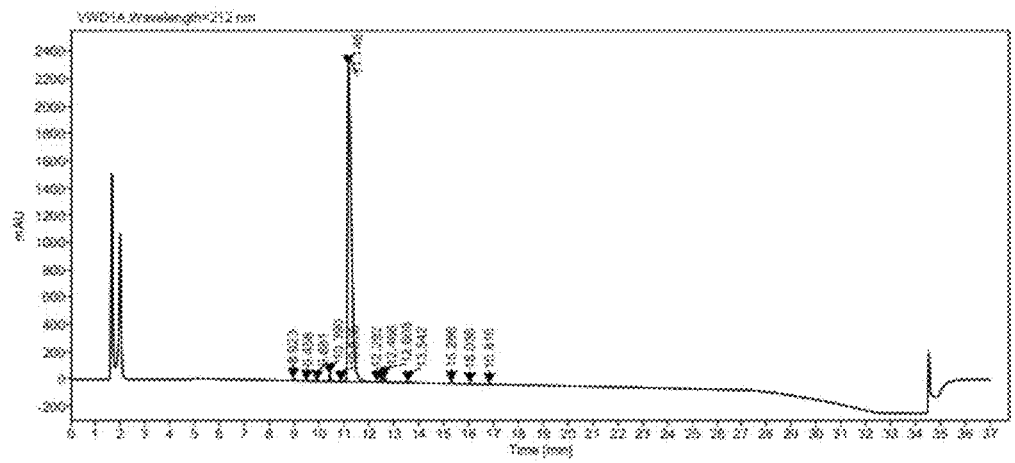
FIG. 50 depicts the HPLC profile of 2-A8 (Experiment Reference 2-Sample Reference A8) (t=5 w).
Figure 51:
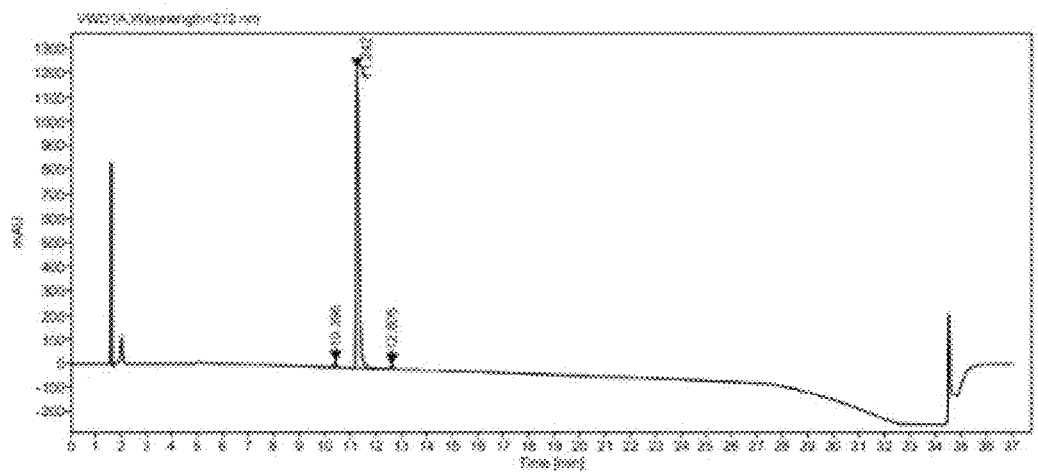
FIG. 51 depicts the HPLC profile of 2-B5 (Experiment Reference 2-Sample Reference B5) (t=2 w).
Figure 52:
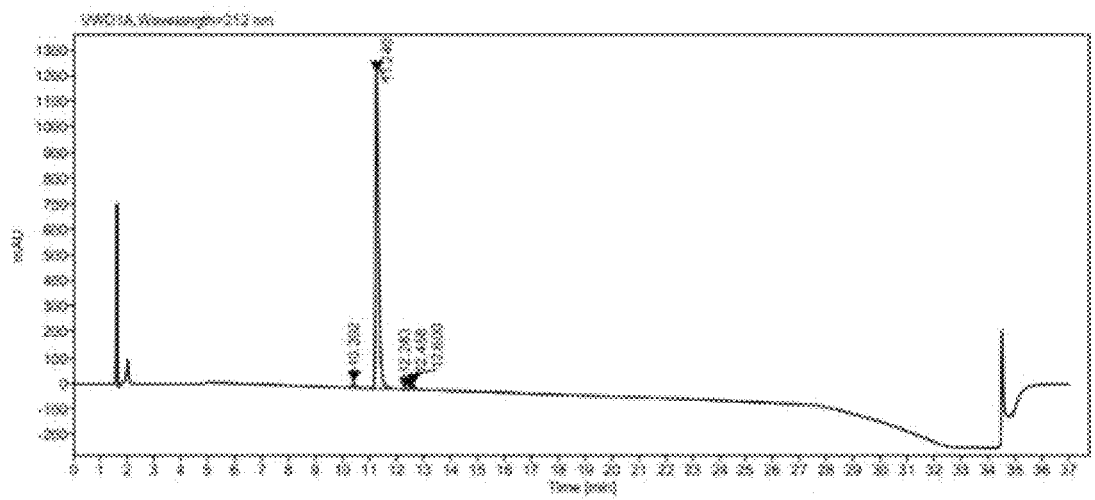
FIG. 52 depicts the HPLC profile of 2-B6 (Experiment Reference 2-Sample Reference B6) (t=3 w).
Figure 53:
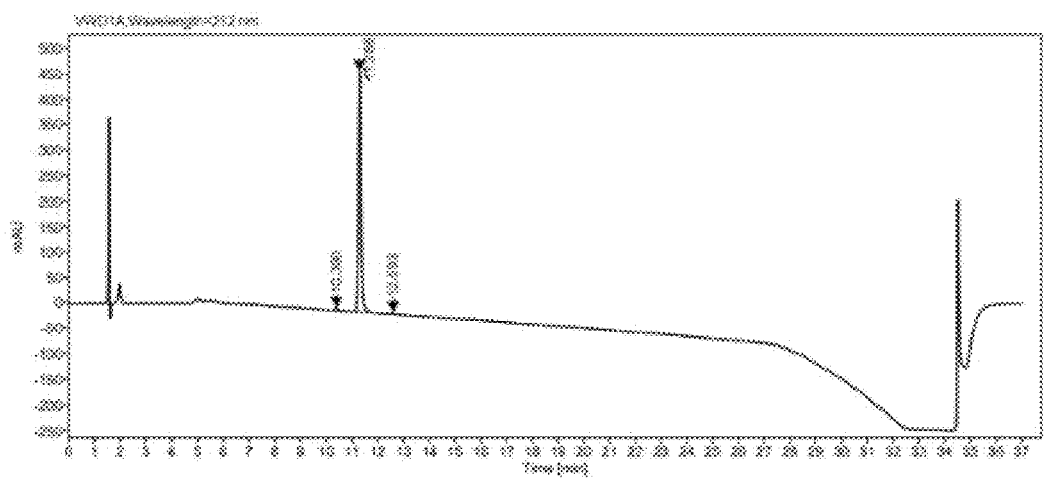
FIG. 53 depicts the HPLC profile of 2-B7 (Experiment Reference 2-Sample Reference B7) (t=4 w).
Figure 54:
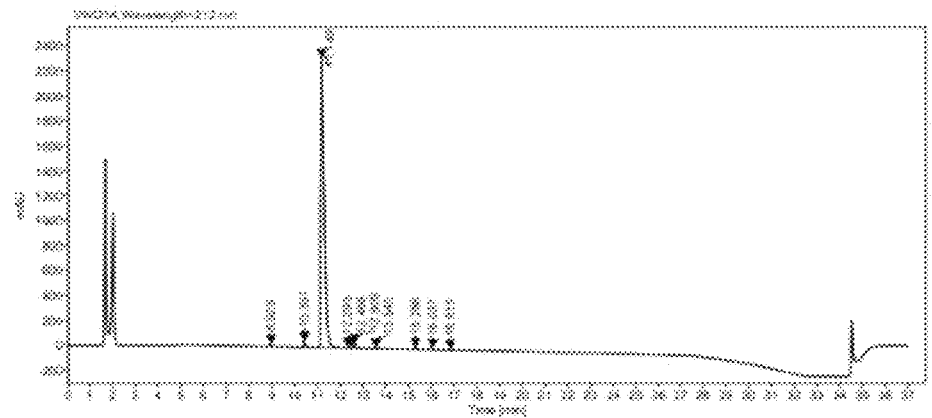
FIG. 54 depicts the HPLC profile of 2-B8 (Experiment Reference 2-Sample Reference B8) (t=5 w).
Figure 55:
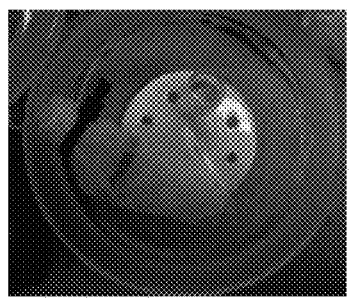
FIG. 55 depicts the 2-A (Experiment Reference 2-Sample Reference A) and 2-B (Experiment Reference 2-Sample Reference B) (t=0 h). Input for both is Pattern #1, Sample Reference 1 (ca. 100 mg). The photograph shows the vials right before being subjected to 75% RH.
Figure 56:
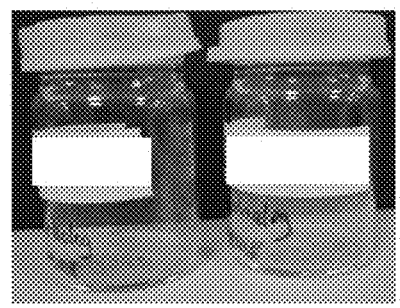
FIG. 56 depicts the 2-A1 (Experiment Reference 2-Sample Reference A1) and 2-B1 (Experiment Reference 2-Sample Reference B1) (t=3 h).
Figure 57:
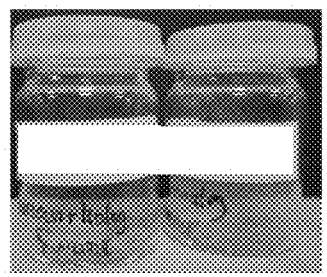
FIG. 57 depicts the 2-A2 (Experiment Reference 2-Sample Reference A2) and 2-B2 (Experiment Reference 2-Sample Reference B2) (t=24 h).
Figure 58:
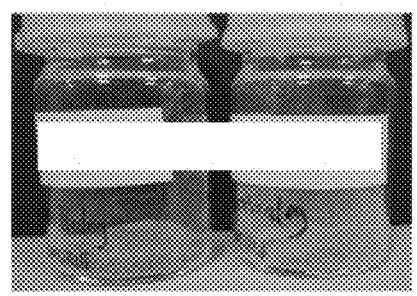
FIG. 58 depicts the 2-A3 (Experiment Reference 2-Sample Reference A3) and 2-B3 (Experiment Reference 2-Sample Reference B3) (t=4 d).
Figure 59:
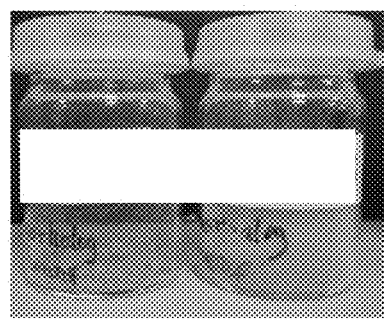
FIG. 59 depicts the 2-A4 (Experiment Reference 2-Sample Reference A4) and 2-B4 (Experiment Reference 2-Sample Reference B4) (t=7 d).
Figure 60:
FIG. 60 depicts the 2-A6 (Experiment Reference 2-Sample Reference A6) and 2-B6 (Experiment Reference 2-Sample Reference B6) (t=3 w).
Figure 61:
FIG. 61 depicts the 2-A8 (Experiment Reference 2-Sample Reference A8) and 2-B8 (Experiment Reference 2-Sample Reference B8) (t=5 w).

The HPLC profile of 2-A5 (Experiment Reference 2-Sample Reference A5) (t=2w) FIG. 47. The HPLC profile of 2-A6 (Experiment Reference 2-Sample Reference A6) (t=3 w) is presented in FIG. 48. The HPLC profile of 2-A7 (Experiment Reference 2-Sample Reference A7) (t=4 w) is presented in FIG. 49. The HPLC profile of 2-A8 (Experiment Reference 2-Sample Reference A8) (t=5 w) is presented in FIG. 50. The HPLC profile of 2-B5 (Experiment Reference 2-Sample Reference B5) (t=2 w) is presented in FIG. 51. The HPLC profile of 2-B6 (Experiment Reference 2-Sample Reference B6) (t=3 w) is presented in FIG. 52. The HPLC profile of 2-B7 (Experiment Reference 2-Sample Reference B7) (t=4 w) is presented in FIG. 53. The HPLC profile of 2-B8 (Experiment Reference 2-Sample Reference B8) (t=5 w) is presented in FIG. 54.

Photography

The results of these experiments are provided in FIGS. 55-61.

c. Conclusion

Two equal portions of the tabernanthalog monofumarate salt (Pattern #1, Sample Reference 1, 100 mg, CP 97.64% area) were weighed out; one of which was placed inside an open vial, while the other was double polyethene bagged, each bag was tied tightly with cable ties. The area of finely divided solid, exposed to the condition was the same across both experiments. The experiment is performed to mimic a typical packaging configuration and monitor the stability of the material directly exposed to the conditions, and the stability of the same amount when double-bagged. Both samples were maintained at 75% RH at 40° C., and monitored by XRPD at time points t=1 h, 3 h, 24 h, 48 h, 7 d, 2 w, 3 w, 4 w and 5 w.

Figure 62:
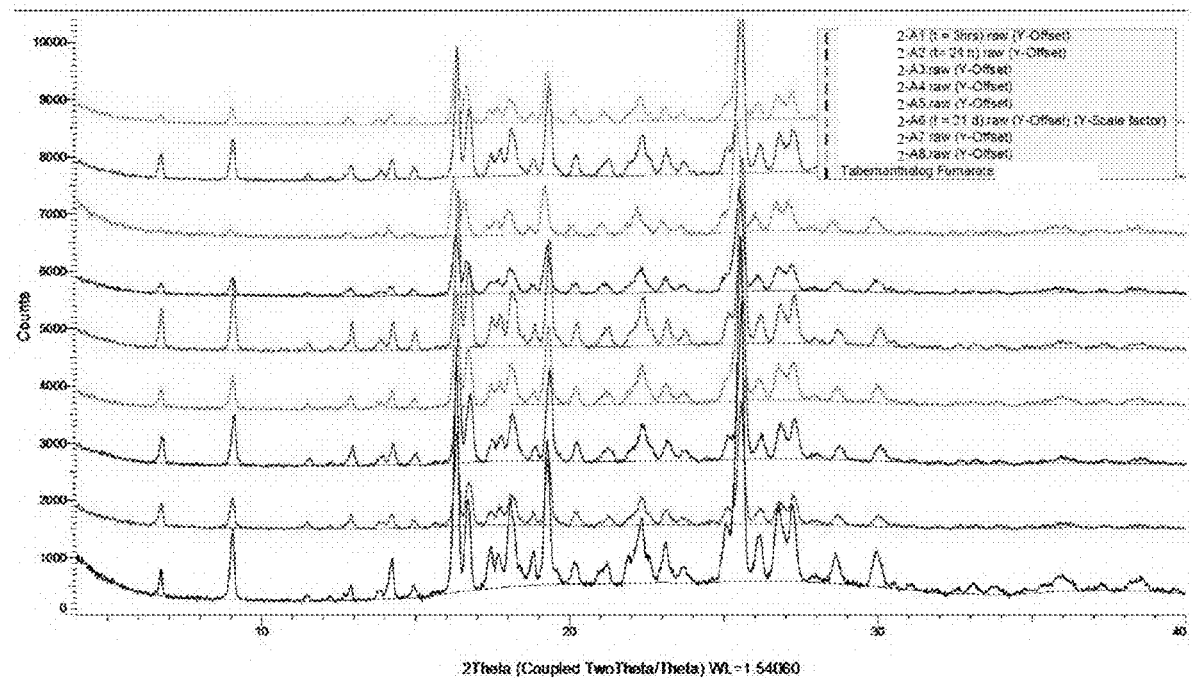
FIG. 62 depicts the XRPD diffractogram overlay of the time point monitoring of 2-A (open vial) at 75% RH at 40° C. Overlay of, from bottom to top, the tabernanthalog monofumarate (Sample Reference 1, t=0), 2-A1 (t=3 h), 2-A2 (t=24 h), 2-A3 (t=48 h), 2-A4 (t=7 days), 2-A5 (t=2 weeks), 2-A6 (t=3 weeks), 2-A7 (t=4 weeks), 2-A8 (t=5 weeks).
Figure 63:
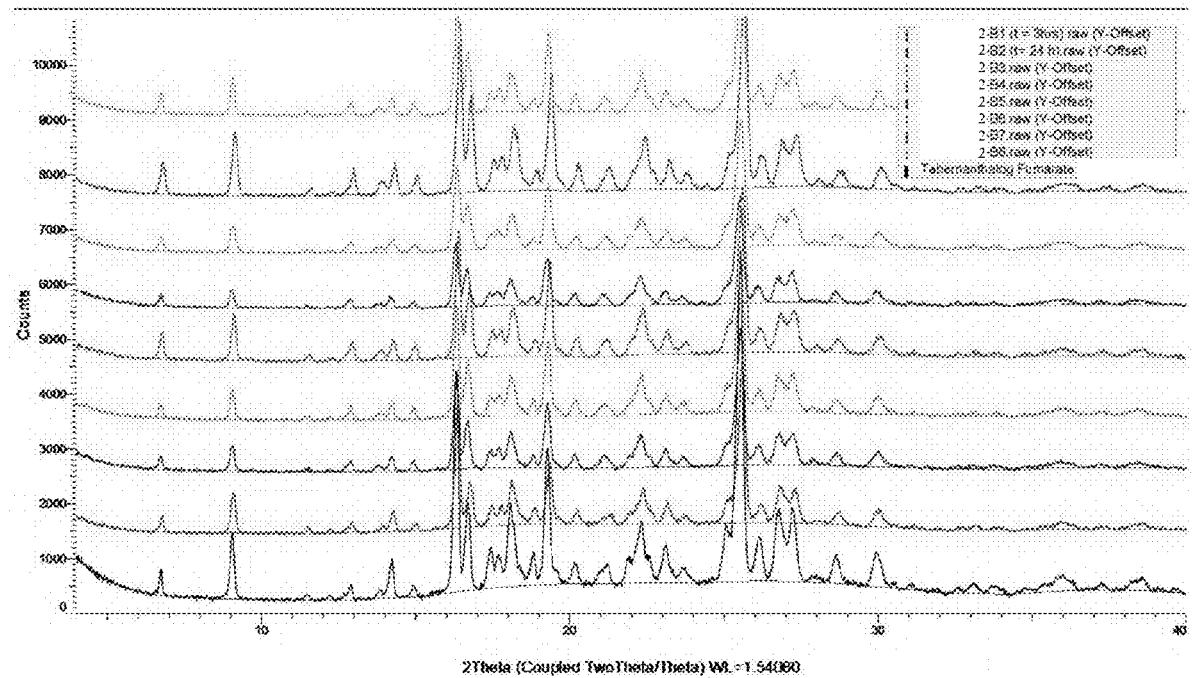
FIG. 63 depicts the XRPD diffractogram overlay of the time point monitoring of 2-B (double bagged open vial) at 75% RH at 40° C. Overlay of, from bottom to top, the tabernanthalog monofumarate salt (Sample Reference 1, t=0), 2-B1 (t=3 h), 2-B2 (t=24 h), 2-B3 (t=48 h), 2-B4 (t=7 days), 2-B5 (t=2 weeks), 2-B6 (t=3 weeks), 2-B7 (t=4 weeks), 2-B8 (t=5 weeks).

Under the conditions evaluated during this study, all analyses were consistent with Pattern #1 of Reference Sample 1 (refer to FIG. 62 and FIG. 63), indicating that the tabernanthalog monofumarate salt is physically and chemically stable under these conditions. HPLC (chromatography was performed using generic method) data collected did not show significant changes in chemical purity, indicating good stability of the phase under the conditions examined. Photographs were also taken to observe any differences in appearance. 2-A became darker during its exposure to the humidity conditions.

Figure 64:
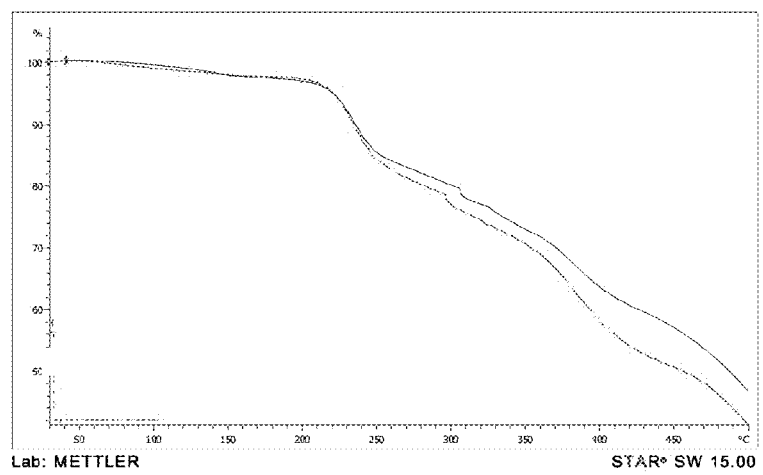
FIG. 64 depicts the TGA overlay of 2-A8 (Experiment Reference 2-Sample Reference A8) (t=5 weeks, open vial) and the tabernanthalog monofumarate salt (Sample Reference 1, Pattern #1, t=0).
Figure 65:
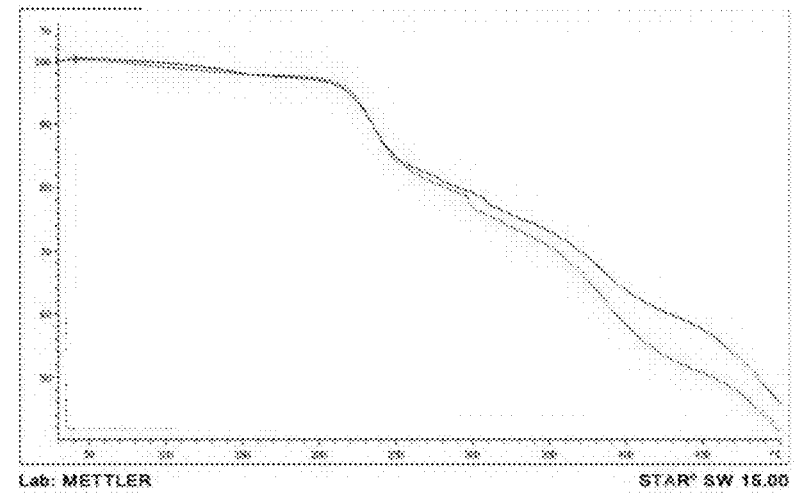
FIG. 65 depicts the TGA overlay of 2-B8 (Experiment Reference 2-Sample Reference B8) (t=5 weeks, double-bagged vial) and the tabernanthalog monofumarate salt (Sample Reference 1, Pattern #1, t=0).
Figure 66:
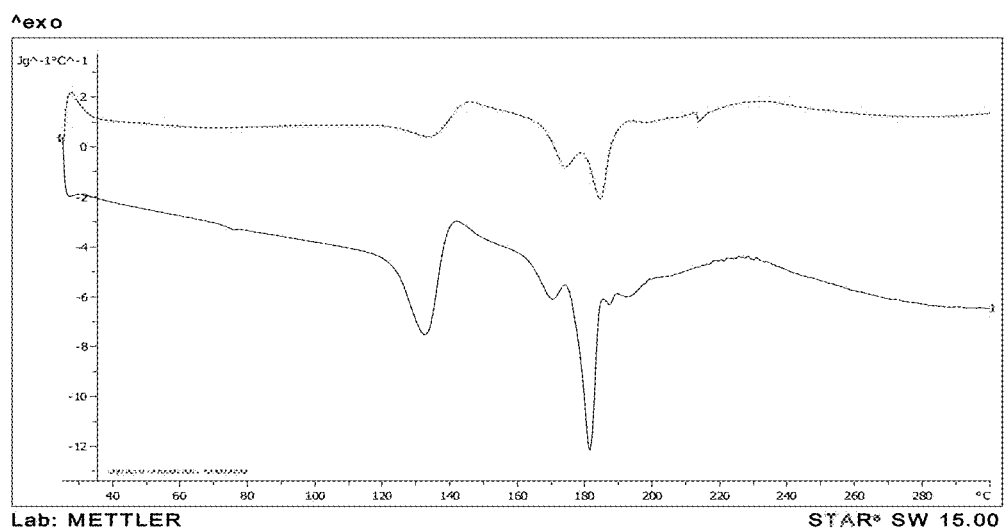
FIG. 66 depicts the DSC overlay of 2-A8 (Experiment Reference 2-Sample Reference A8) (bottom, t=5 weeks, open vial) and the tabernanthalog monofumarate salt (Sample Reference 1, Pattern #1, top t=0).
Figure 67:
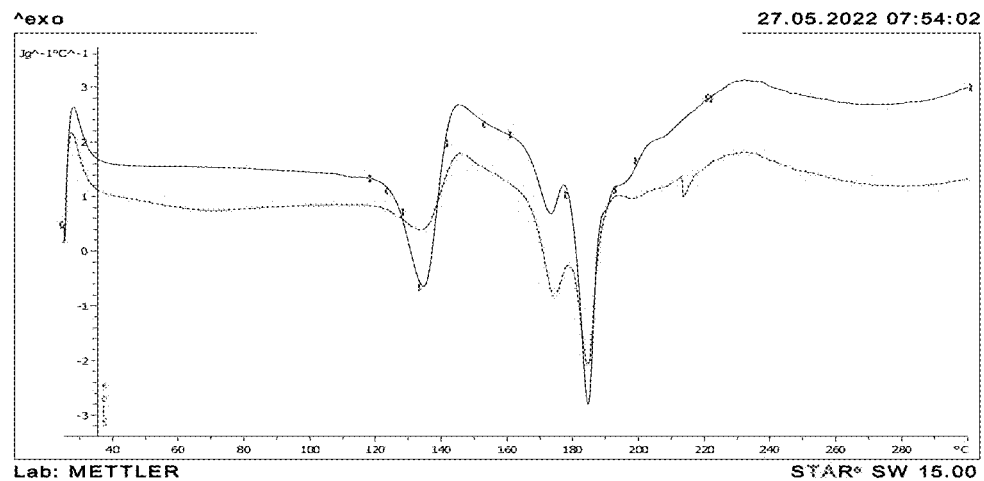
FIG. 67 depicts the DSC overlay of 2-B8 (Experiment Reference 2-Sample Reference B8) (t=5 weeks, double-bagged vial) and the tabernanthalog monofumarate salt (Sample Reference 1, Pattern #1, t=0).

TG analyses of the last timepoint collected from both experiments were consistent with the input with no significant water absorption (refer to FIG. 64 and FIG. 65). DSC analyses of the two absorbents were comparable with the input. 2-A8 and 2-B8 exhibited a slightly larger endotherm event with onset 121° C. compared to Sample Reference 1 (Pattern #1, refer to FIG. 66 and FIG. 67). The summary of HPLC data collected during Experiment Reference 2 is provided in Table 28.

TABLE 28

Summary of HPLC data collected during Experiment Reference 2

| Reference | Input Conditions | Batch | HPLC (% area) | XRPD t = 3 h (-A1, -B1) | XRPD t = 24 h (-A2, -B2) | XRPD t = 48 h (-A3, -B3) | XRPD t = 7 days (-A4, -B4) | XRPD t = 2 w (-A5, -B5) |
|---|---|---|---|---|---|---|---|---|
| 2-A1 to 2-A8 | Open-necked, wide vial at 75% RH/40° C. for 5 weeks | Tabernanthalog fumarate (CAT8931) | 97.64 | Consistent with input batch of tabernanthalog fumarate | Consistent with input batch of tabernanthalog fumarate | Consistent with input batch of tabernanthalog fumarate | Consistent with input batch of tabernanthalog fumarate | Consistent with input batch of tabernanthalog fumarate |
| 2-B1 to 2-B8 | Sealed PK0056 electrostatic bags at 75% RH/40° C. 5 weeks | Tabernanthalog fumarate (CAT8931) | | Consistent with input batch of tabernanthalog fumarate | Consistent with input batch of tabernanthalog fumarate | Consistent with input batch of tabernanthalog fumarate | Consistent with input batch of tabernanthalog fumarate | Consistent with input batch of tabernanthalog fumarate |

| Reference | HPLC (% area) | XRPD t = 3 w (-A6, -B6) | HPLC (% area) | XRPD t = 4 w (-A7, -B7) | HPLC (% area) | XRPD t = 5 w (-A8, -B8) | HPLC (% area) |
|---|---|---|---|---|---|---|---|
| 2-A1 to 2-A8 | 97.26 | Consistent with input batch of tabernanthalog fumarate | 97.01 | Consistent with input batch of tabernanthalog fumarate | 97.98 | Consistent with input batch of tabernanthalog fumarate | 97.34 |
| 2-B1 to 2-B8 | 97.44 | Consistent with input batch of tabernanthalog fumarate | 97.02 | Consistent with input batch of tabernanthalog fumarate | 98.38 | Consistent with input batch of tabernanthalog fumarate | 97.54 | iii. Thermal Examinations a. Experimental Procedure

Figure 72:
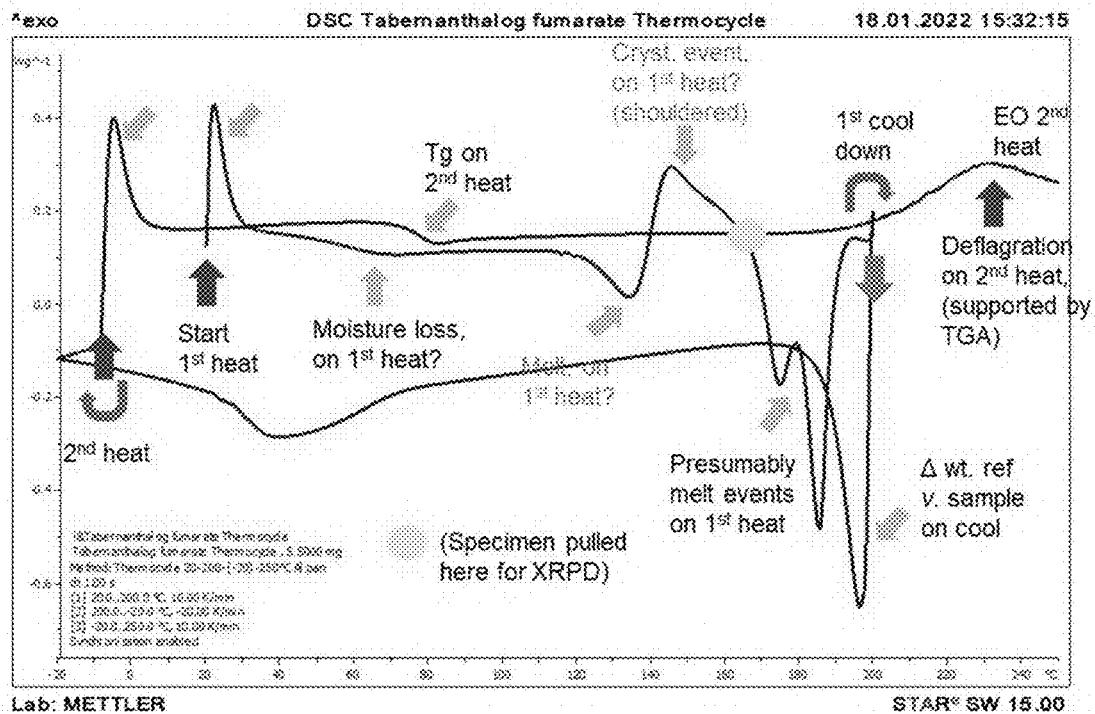
FIG. 72 depicts the DSC thermocycle of the tabernanthalog monofumarate salt (Sample Reference 1, Pattern #1).
Figure 75:
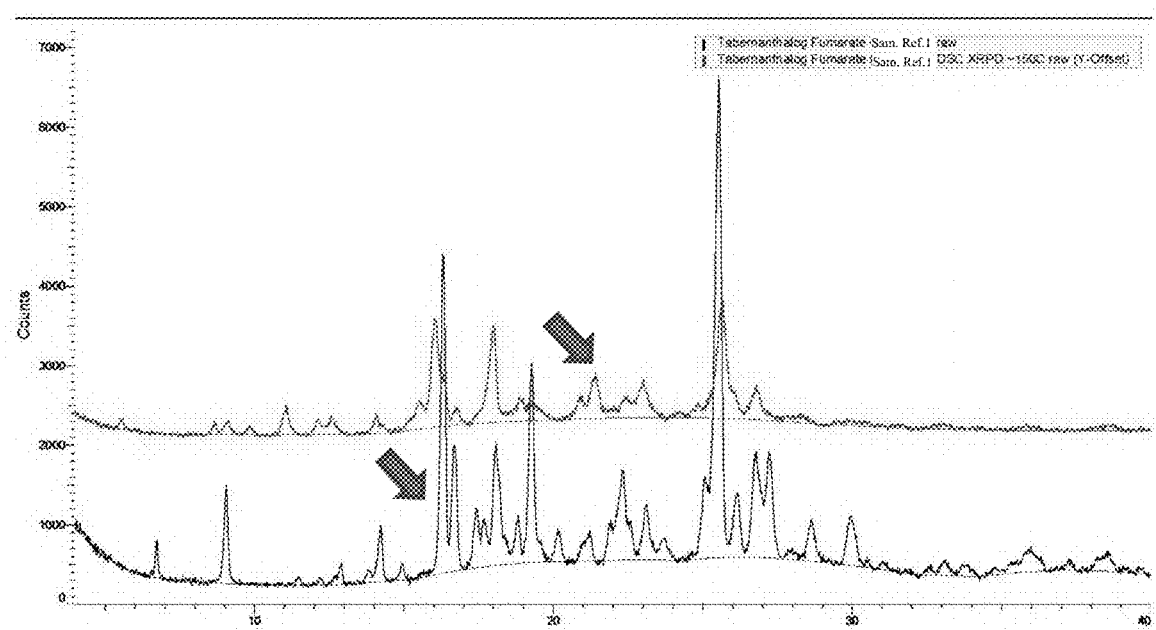
FIG. 75 depicts the XRPD overlay of the tabernanthalog monofumarate salt (Sample Reference 1, Pattern #1, input, bottom) and specimen heated at ca. 150° C. (top).

Described for the supplied (Sample Reference 1): The tabernanthalog monofumarate salt (ca 10.0 mg, Pattern #1) was placed in an aluminum crucible (40 µl) and heated at a rate of +10° C./min from 20 to 155° C. to capture the exothermic event that occurred ca 135 to 155° C. (FIG. 72). The crucible was removed from the instrument and allowed to cool to 20° C. (<1 s), the specimen was expressed from the spent crucible and analyzed by XRPD and compared with the starting material (refer to FIG. 75).

b. Analytical Characterization Data

Figure 68:
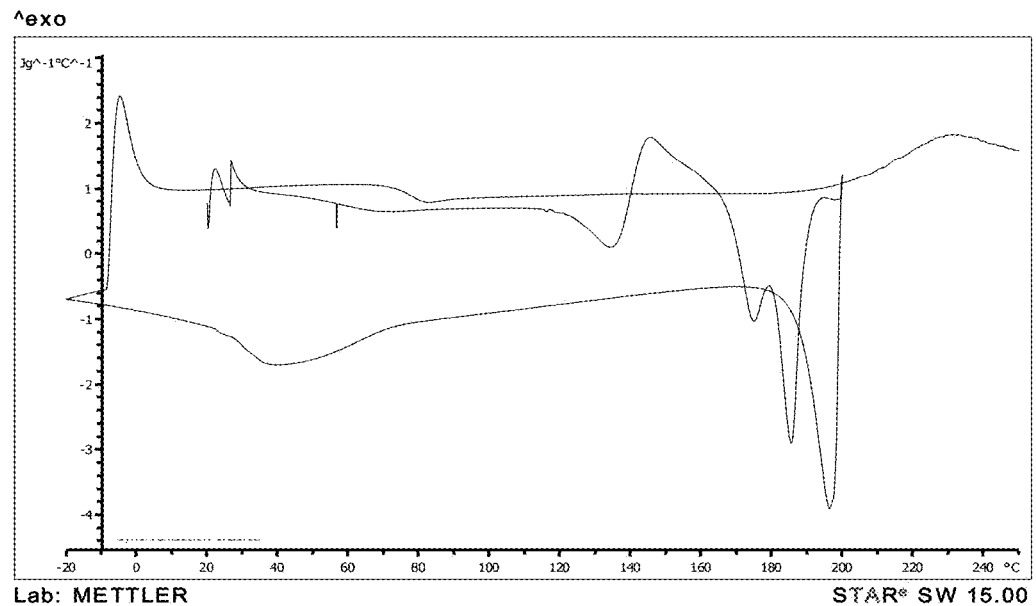
FIG. 68 depicts the DSC thermocycle of the tabernanthalog monofumarate salt (Sample Reference 1, Pattern #1). Coordinate system: Normalized to sample size (Y-Axis), Reference temperature (X-Axis).
Figure 69:
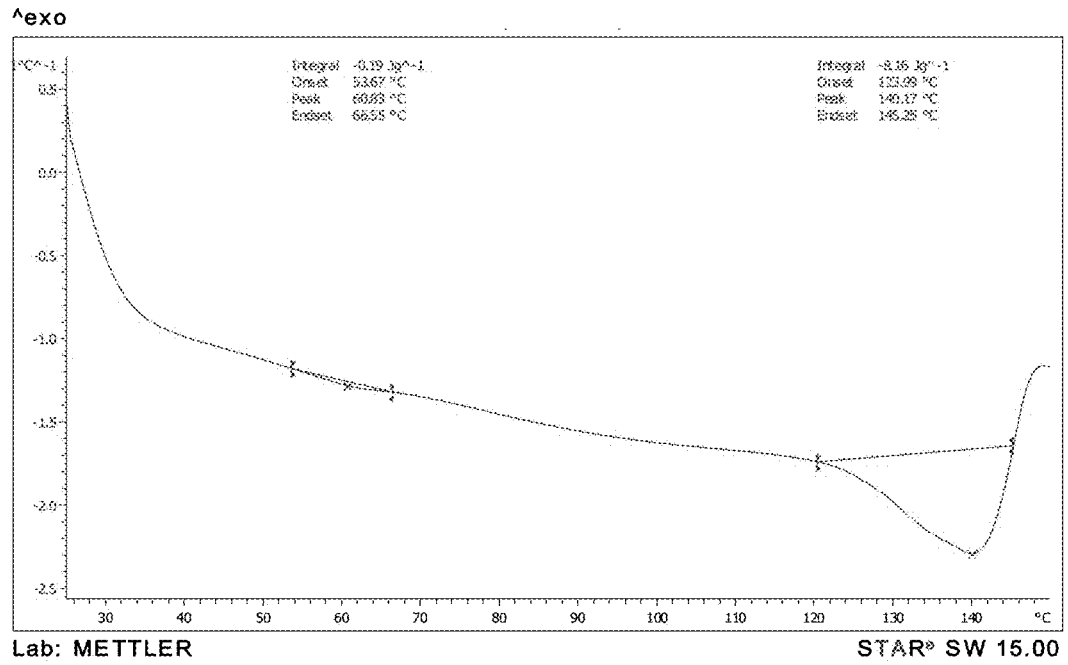
FIG. 69 depicts the DSC thermocycle of the tabernanthalog monofumarate salt (Sample Reference 1, Pattern #1). Coordinate system: Normalized to sample size (Y-Axis), time (X-Axis).
Figure 70:
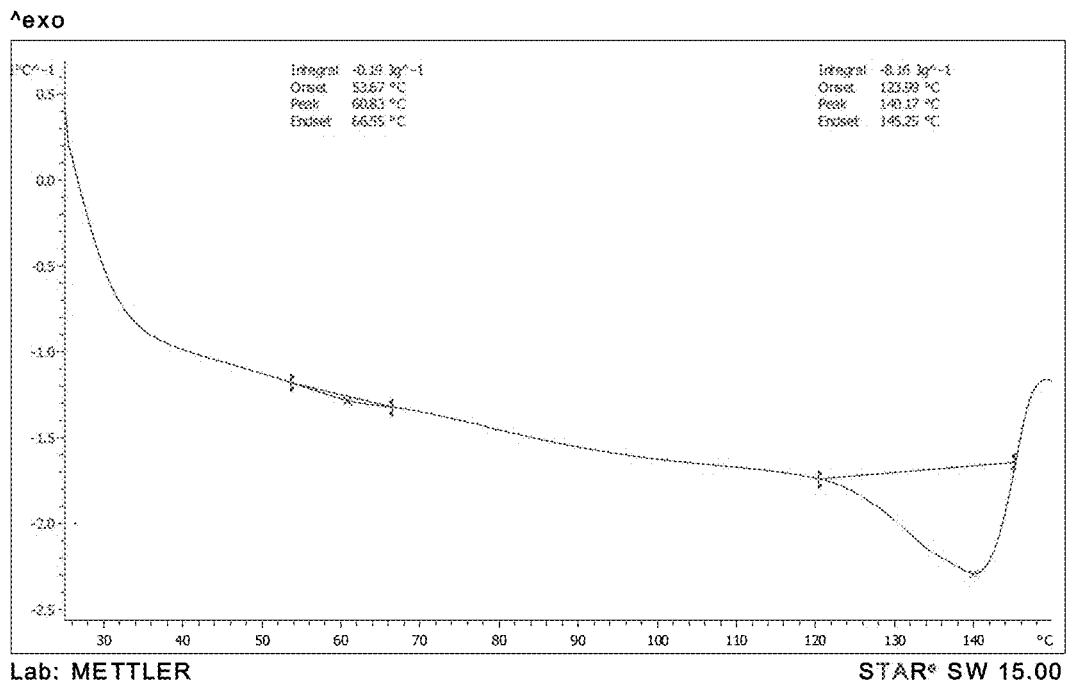
FIG. 70 depicts the DSC of the tabernanthalog monofumarate salt (Sample Reference 1, Pattern #1) that was acquired from 25° C. to 155° C. at a ramp rate of +10° C./min.
Figure 71:
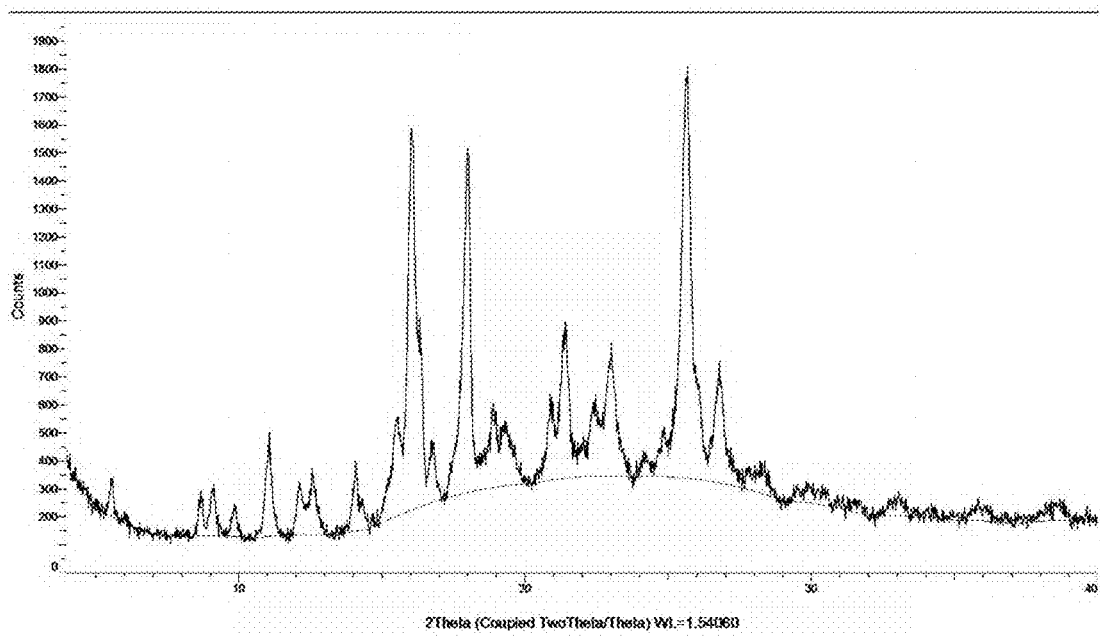
FIG. 71 depicts the XRPD profile of the tabernanthalog monofumarate salt (Sample Reference 1, Pattern #1) specimen from DSC crucible at ca. 150° C.

DSC
The DSC results are provided in FIGS. 68-70.
XRPD
The XRD results are provided in FIG. 71 and Table 29.

TABLE 29

Peak angle data of the tabernanthalog monofumarate salt (Sample Reference 1, Pattern #1) specimen from DSC crucible at ca. 150° C.

| 2-θ (°) | d Value | Rel. Intensity (%) |
|---|---|---|
| 8.7 | 10.19 | 11 |
| 9.1 | 9.72 | 12 |

TABLE 29-continued

Peak angle data of the tabernanthalog monofumarate salt (Sample Reference 1, Pattern #1) specimen from DSC crucible at ca. 150° C.

| 2-θ (°) | d Value | Rel. Intensity (%) |
|---|---|---|
| 11.0 | 8.00 | 23 |
| 12.1 | 7.28 | 12 |
| 12.6 | 7.03 | 15 |
| 14.1 | 6.28 | 17 |
| 15.5 | 5.70 | 25 |
| 16.0 | 5.52 | 96 |
| 16.3 | 5.45 | 45 |
| 16.8 | 5.29 | 14 |
| 18.0 | 4.93 | 86 |
| 18.9 | 4.69 | 20 |
| 19.3 | 4.60 | 16 |
| 20.9 | 4.24 | 19 |
| 21.4 | 4.15 | 35 |
| 22.4 | 3.96 | 17 |
| 23.0 | 3.87 | 29 |
| 24.9 | 3.58 | 12 |
| 25.6 | 3.47 | 100 |
| 25.9 | 3.43 | 27 |
| 26.8 | 3.33 | 30 | c. Conclusion

Figure 73:
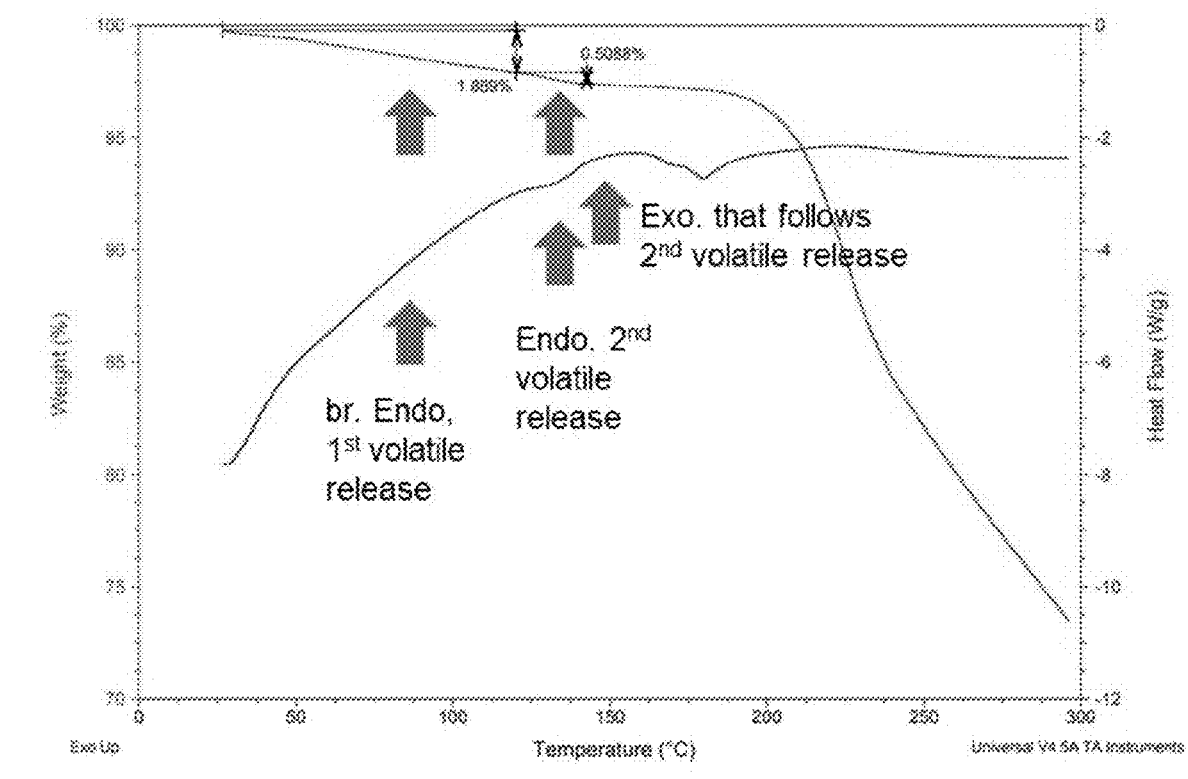
FIG. 73 depicts the simultaneous DSC and TGA analyses of the tabernanthalog monofumarate salt (Sample Reference 1, Pattern #1).

An initial thermocycle experiment was performed to identify the events during a cycle from 20° C. to 200° C. at +10° C./min, from 200° C. to −20° C. at −20° C./min and −20° C. to 25° C. at +10° C./min (refer to FIG. 72). The abrupt change in $c_p$, at the beginning of each thermal segment was attributed to the weight difference between the reference and sample pans. The shallow endotherm (36 to 101° C.) is ambiguous and may be drying of surface moisture/release of weakly bound water, the transition approximately coincided with TG $-\Delta$ wt. $-2.1\%$ w/w, (72 to 122° C., refer to FIG. 299). This was confirmed via simultaneous TGA/DSC (FIG. 73).

At first glance, the $2^{nd}$ endotherm (onset 121° C.), appeared to be a melt, followed by shouldered exotherm (onset 140° C.), which may correspond to crystallization; whether these events extend across the entire bulk phase are not known.

The molten specimen did not recrystallize into the same form on cooling. Unlikely that disproportionation occurred on heating (m.p. non-ionized Fu ac 287° C.).

At higher resolution, the shallow endotherm (36 to 101° C.) would seem to be associated with non-crystal-bonded volatile release, presumably water [$-\Delta$ wt. $-1.9\%$ w/w, (up to 120° C.)]. The $2^{nd}$ endotherm (onset 121° C.) is also associated with volatile release, presumably water (–0.5% w/w), or perhaps water and acetonitrile (–0.3+–0.2% w/w), FIG. 73. We can surmise that these volatiles (–0.5% w/w) are probably crystal-bonded, since the exotherm that followed at ca 140° C., most likely corresponded to significant structural re-organization (modulated DSC to impart better granularity to this event is reported (FIG. 74).

Figure 74:
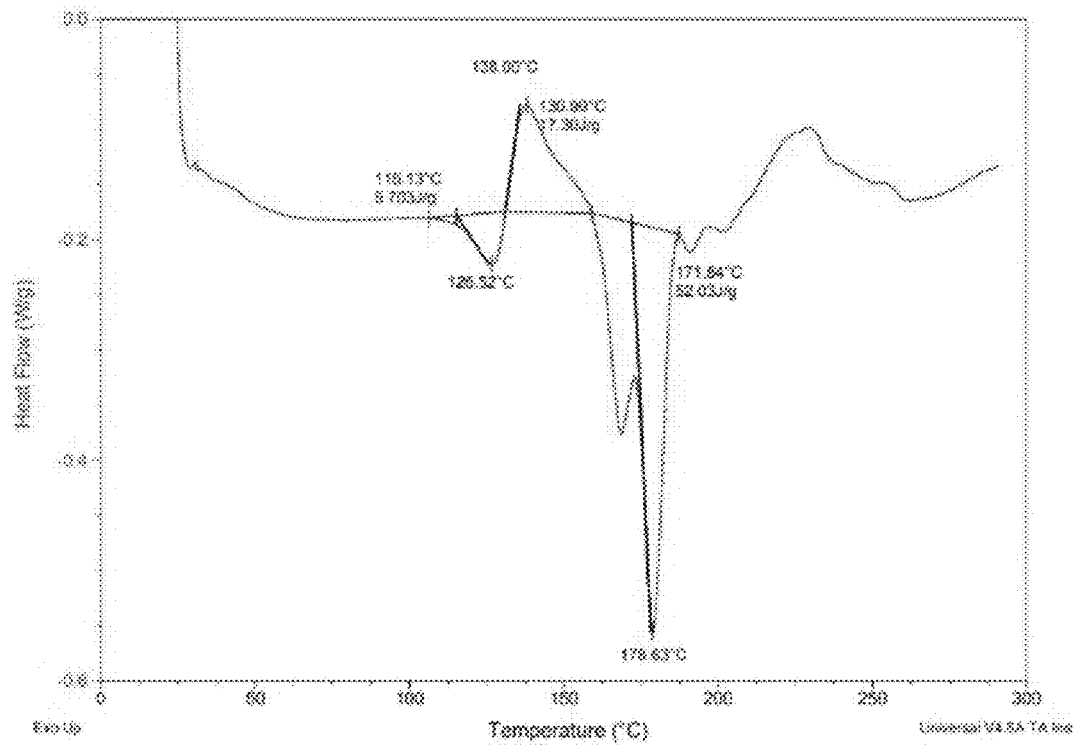
FIG. 74 depicts the modulated DSC of the tabernanthalog monofumarate salt (Sample Reference 1, Pattern #1).

With modulated DSC, the proposed crystallization events (138° C.) were slightly better resolved; however, it was still shouldered (refer to FIG. 74). Therefore, the simple melt-crystallization explanation (120 to 160° C.) given on FIG. 73 is not quite true and now appears to consist of volatile release and endothermic transition (melt), followed by exothermic transition (crystallization, refer to FIG. 74) and bimodal endotherm.

Following the data collected above, XRPD analysis was performed on the specimen that was heated at ca. 155° C. (refer to yellow circle in FIG. 72) in an aluminum DSC crucible (FIG. 70). The specimen was withdrawn slightly prematurely, nevertheless, based on XRPD diffractogram overlay with the input (FIG. 75), we can conclude that the exo. event ca 135 to 155° C., corresponded to structural re-organization (crystallization).

iv. DVS Analyses (Experiment Reference 4)

a. Experimental Procedure

The moisture sorption properties of the feed API (active pharmaceutical ingredient) were analyzed by DVS Intrinsic instrument (Surface Measurement System). Approximately 20 to 50 mg of API was weighed onto an aluminum pan and loaded into the instrument equilibrated at 25° C. The sample was equilibrated under a dry atmosphere (0% relative humidity) for 60 minutes, before increasing the humidity from 0% to 30% at 5% step increment and from 30% to 90% at 10% step increment. A desorption cycle was also applied from 90% to 30% (10% step decrement) and from 30% to 0% (5% step decrement). A rate of change in mass per time unit (dm/dt) of 0.002%/min was set as the equilibrium parameter. Kinetic and isotherm graphs were calculated.

It is noted that 4-A4 (Experiment Reference 4-Sample Reference A4) and 8-A4 (Experiment Reference 8-Sample Reference A4) are identical. Furthermore, 4-A2 (Experiment Reference 4-Sample Reference A2) and 8-A2 (Experiment Reference 8-Sample Reference A2) are identical.

b. Analytical Characterization Data

DVS

Figure 76:
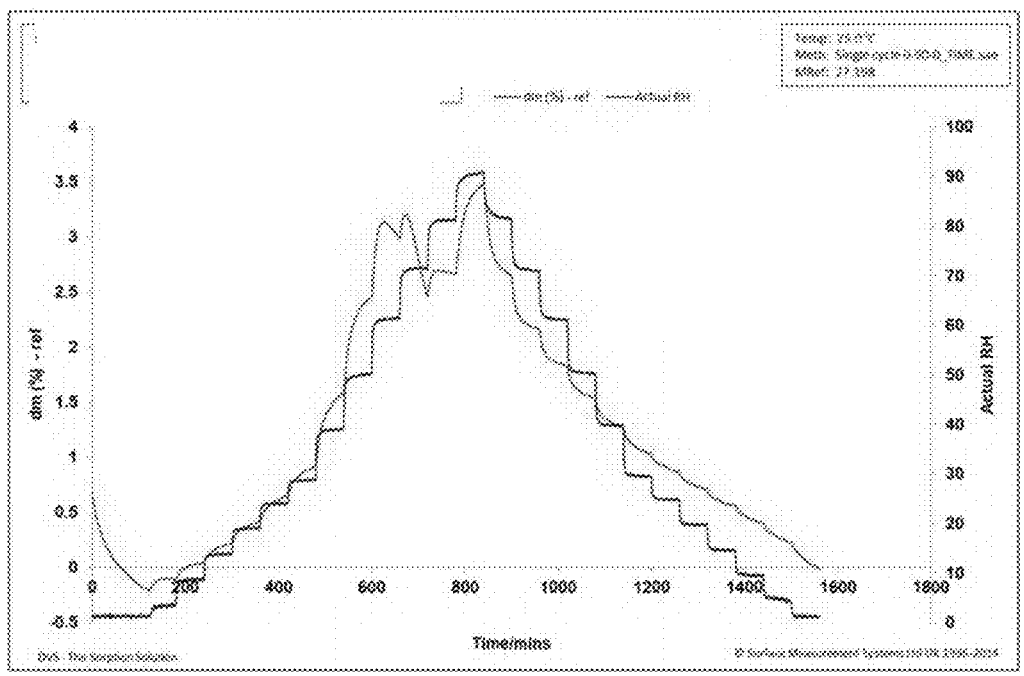
FIG. 76 depicts the DVS data of the tabernanthalog monofumarate salt (Sample Reference 1, Pattern #1).
Figure 77:
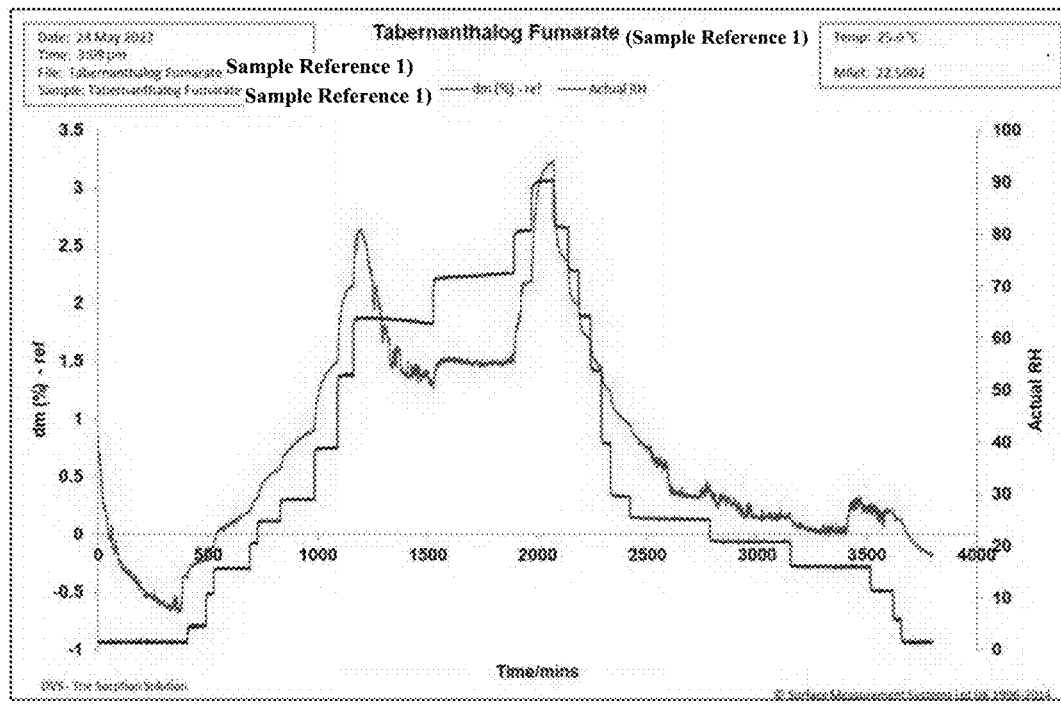
FIG. 77 depicts the mass equilibrated DVS Data of the tabernanthalog monofumarate salt (Sample Reference 1, Pattern #1). This is the mass equilibrated DVS of the supplied material.

DVS data of Sample Reference 1 is provided in FIG. 76. The mass equilibrated DVS data of Sample Reference 1 is provided in FIG. 77. Mass equilibrated DVS data of tabernanthalog monofumarate salt (Pattern #1, supplied material 4-A4 (Experiment Reference 4-Sample Reference A4) (Form A) is provided in FIG. 78.

XRPD

Figure 79:
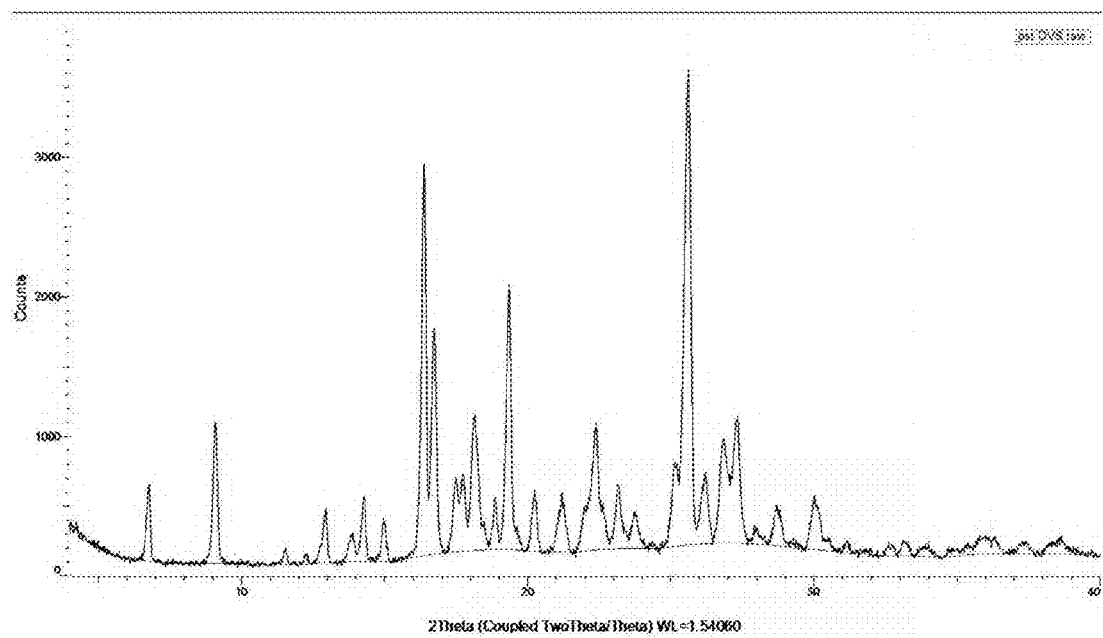
FIG. 79 depicts the XRPD profile of Sample Reference 1 post DVS (Pattern #1, Mass equilibrated DVS) of the supplied material.

The XRPD profile of Sample Reference 1 post DVS (Mass equilibrated DVS) is provided in FIG. 79 and the list of peaks are provided in Table 30.

Figure 80:
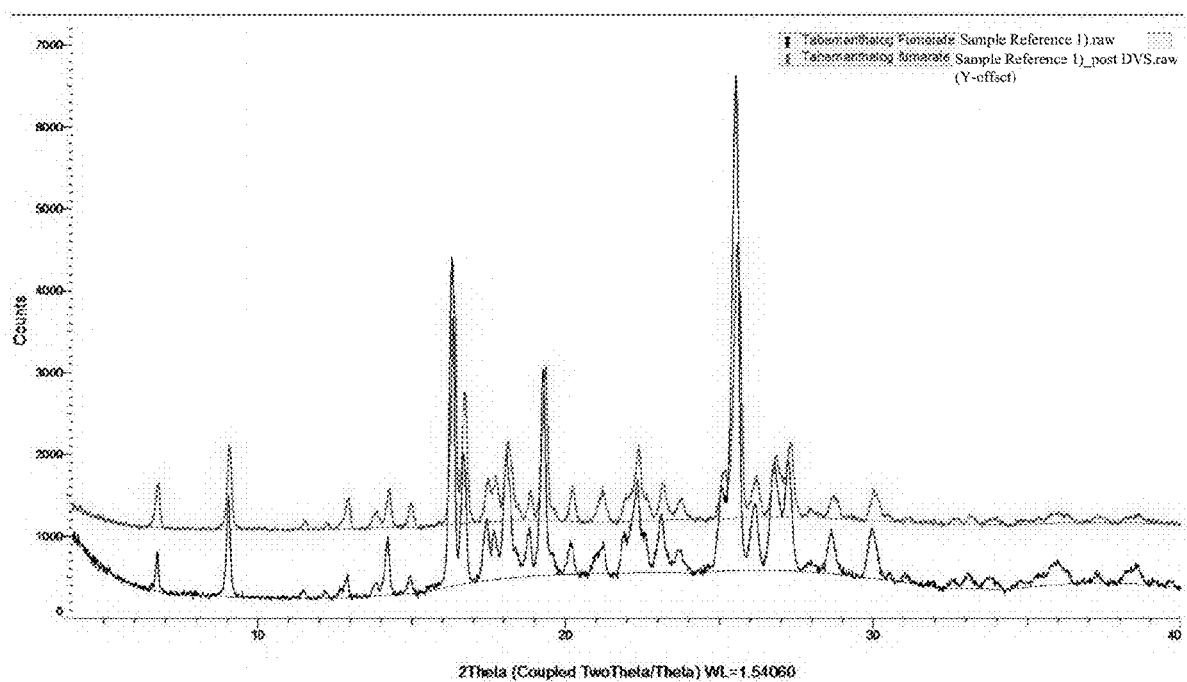
FIG. 80 depicts the XRPD overlay of the tabernanthalog monofumarate salt (Sample Reference 1, pattern #1, bottom) and post DVS (top, Pattern #1).
Figure 81:
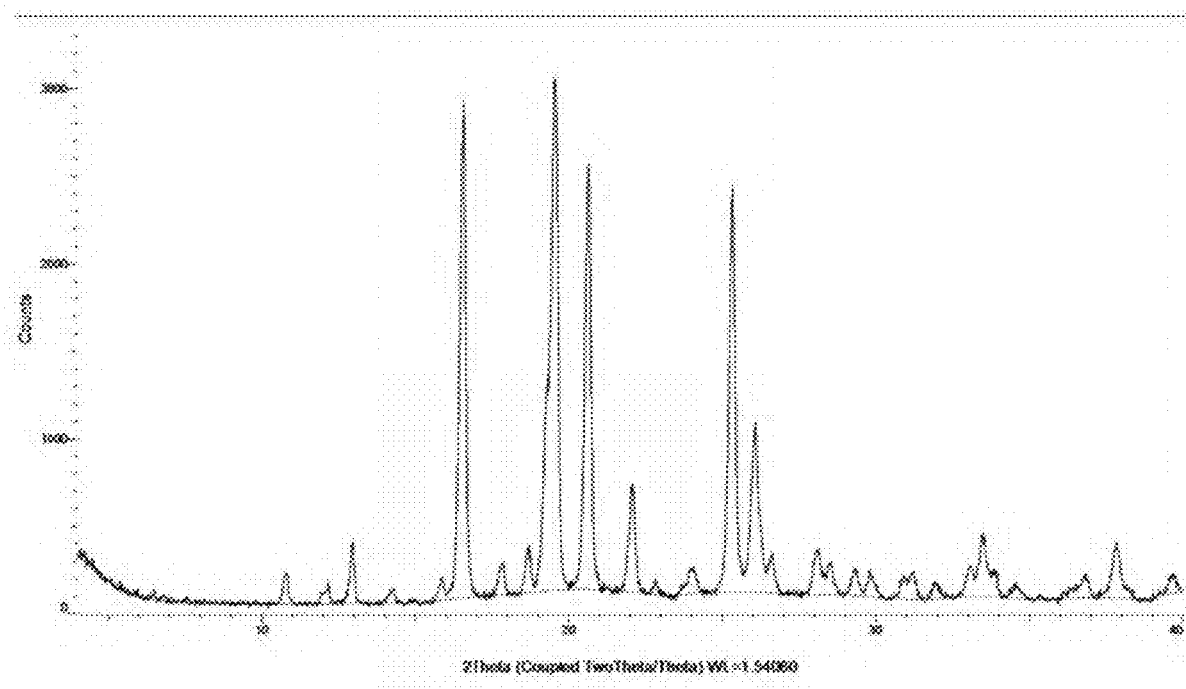
FIG. 81 depicts the XRPD profile of 4-A4 (Experiment Reference 4-Sample Reference A4) post DVS (Pattern #6a) (Mass equilibrated DVS).

The XRPD overlay of the tabernanthalog monofumarate salt (Sample Reference 1, pattern #1, black) post DVS (red, Pattern #1) is provided in FIG. 80. The XRPD profile of 4-A4 (Experiment Reference 4-Sample Reference A4) post DVS (Mass equilibrated DVS, Pattern #6a) is provided in FIG. 81 and the peak listing is provided in Table 31.

TABLE 30

Peak angle data of Sample Reference 1 post DVS (Pattern #1)

| 2-θ (°) | d Value | Rel. Intensity (%) |
|---|---|---|
| 6.7 | 13.10 | 15 |
| 9.1 | 9.73 | 30 |
| 12.9 | 6.85 | 10 |
| 14.3 | 6.21 | 14 |
| 16.4 | 5.41 | 80 |
| 16.7 | 5.30 | 48 |
| 17.5 | 5.06 | 14 |
| 17.7 | 5.00 | 16 |
| 18.1 | 4.88 | 29 |
| 18.9 | 4.70 | 11 |
| 19.3 | 4.59 | 54 |
| 20.2 | 4.39 | 13 |
| 21.2 | 4.19 | 13 |
| 22.4 | 3.97 | 26 |
| 22.5 | 3.94 | 10 |
| 23.2 | 3.84 | 14 |
| 25.2 | 3.53 | 17 |
| 25.6 | 3.48 | 100 |
| 26.2 | 3.40 | 14 |
| 26.8 | 3.32 | 22 |
| 27.3 | 3.27 | 26 |
| 30.0 | 2.97 | 10 |

TABLE 31

Peak angle data of 4-A4 (Experiment Reference 4-Sample Reference A4) post DVS (Pattern #6a)

| 2-θ (°) | d Value | Rel. Intensity (%) |
|---|---|---|
| 12.9 | 6.84 | 11 |
| 16.5 | 5.36 | 89 |
| 19.5 | 4.54 | 100 |
| 20.6 | 4.30 | 80 |
| 22.0 | 4.03 | 20 |
| 25.3 | 3.52 | 77 |
| 26.1 | 3.42 | 32 |
| 33.5 | 2.67 | 12 |
| 37.8 | 2.38 | 11 | c. Conclusion

There are two main methods, one is by time where the equilibration is given by a fixed time, i.e., 1 hour per step.

The second one is by mass per time unit (dm/dt) of 0.002%/min, that is when the difference in weight is less than 0.002% the instrument moves onto the next step. For unknown hygroscopicity, the method by time is indicated because it gives an idea of water affinity. Ideally the analysis is repeated using the mass equilibration method to confirm. By experience for hygroscopic samples, the analysis can continue for days. For non-hygroscopic samples the difference between the two methods may not be significant.

Figure 82:
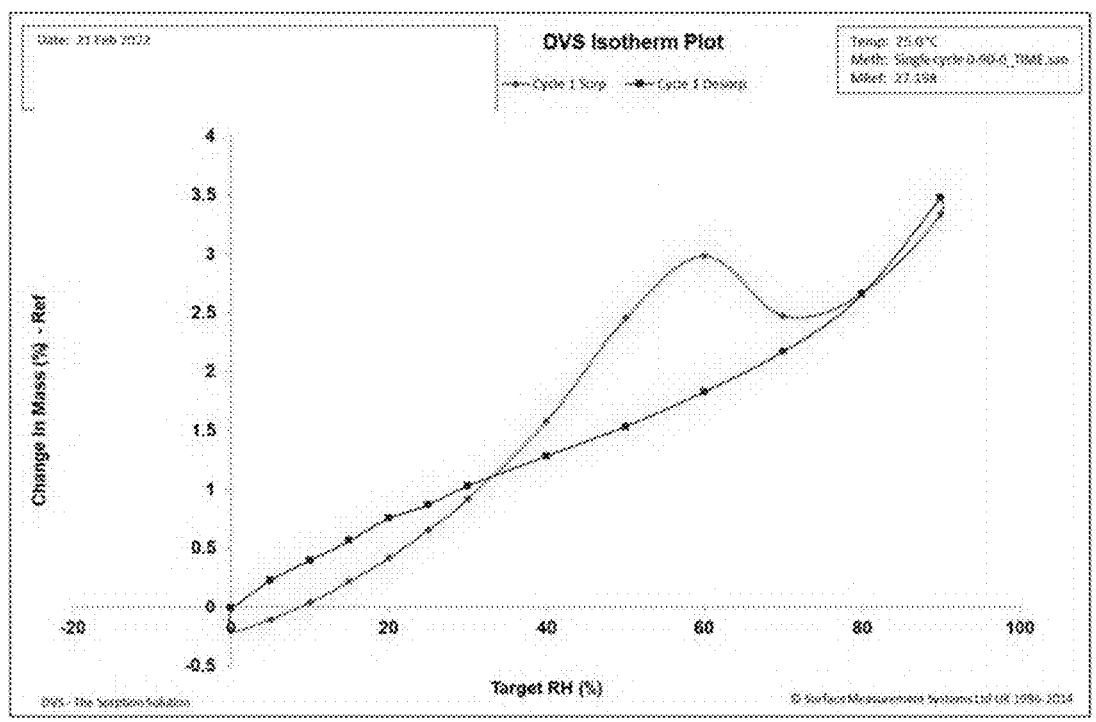
FIG. 82 depicts the DVS isotherm plot of the tabernanthalog monofumarate salt (Sample Reference 1, pattern #1) obtained with 0% to 90% to 0% RH vs time.

DVS Isotherm plot of the tabernanthalog monofumarate salt (Sample Reference 1, Pattern #1) obtained with 0 to 90% to 0% RH vs time is provided in FIG. 82. Mass equilibrated DVS Isotherm plot of The tabernanthalog fumarate salt (Sample Reference 1) obtained with 0 to 90%/to 0%/RH is provided in FIG. 83. Mass equilibrated DVS Isotherm plot of The tabernanthalog fumarate salt (4-A4) obtained with 0 to 90% to 00% RH is provided in FIG. 84.

Figure 83:
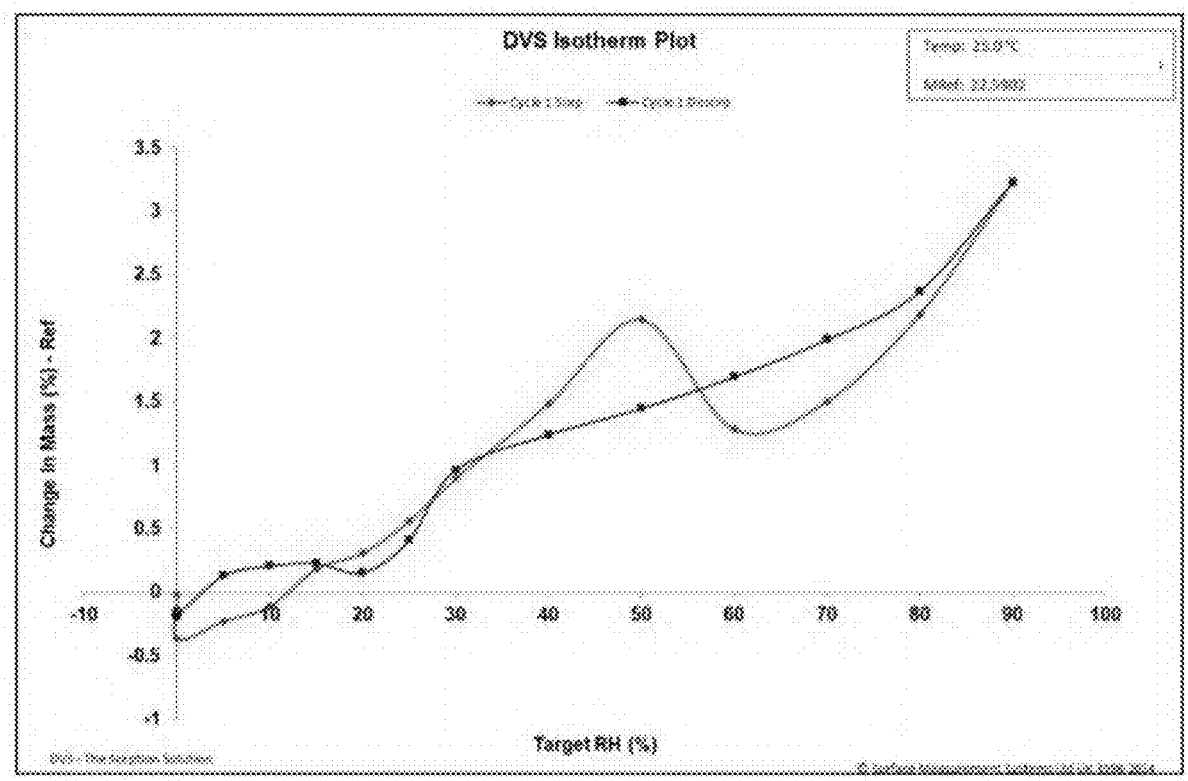
FIG. 83 depicts the mass equilibrated DVS isotherm plot of the tabernanthalog monofumarate salt (Sample Reference 1, pattern #1) obtained with 0% to 90% to 0% RH.
Figure 84:
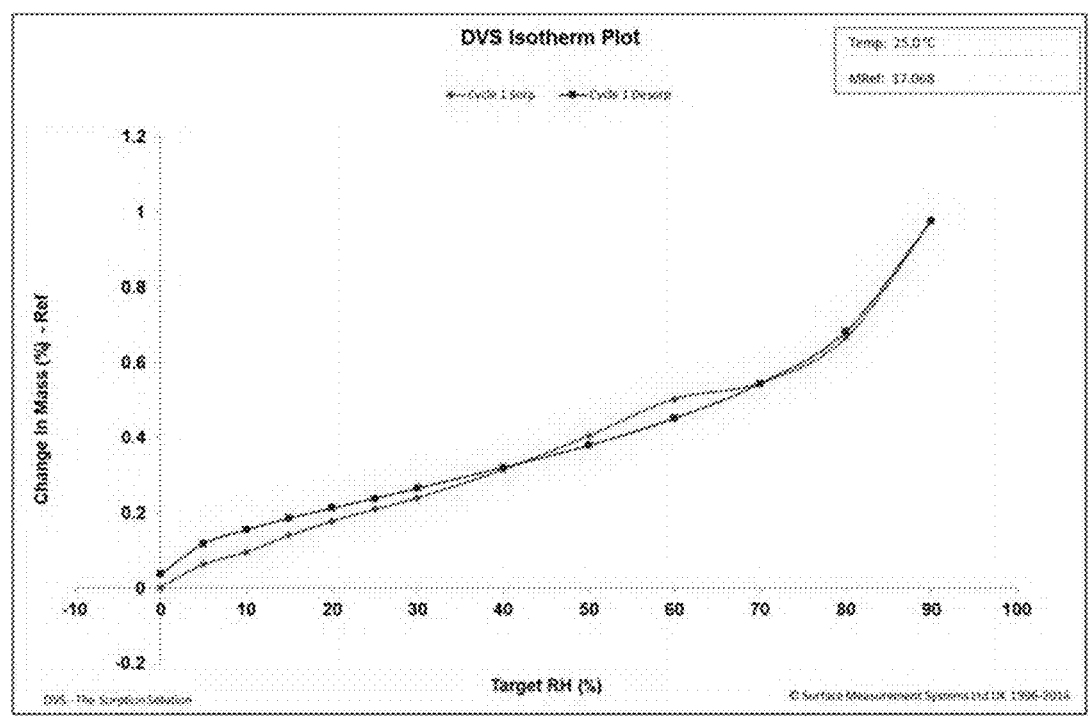
FIG. 84 depicts the mass equilibrated DVS isotherm plot of the tabernanthalog monofumarate salt (4-A4, Pattern #6a, Form A) obtained with 0% to 90%/c to 0% RH.

Consequently, supplied batch Sample Reference 1 was initially analyzed by the fixed time method (FIG. 82) and subsequently by mass per time unit (dm/dt) of 0.002%/min (FIG. 83) and once the stable form was generated (4-A2) (Experiment Reference 4-Sample Reference A2, Pattern #6a, Form A) the analysis was repeated is by mass per time unit (dm/dt) of 0.002%/min (FIG. 84). The sample exhibited hygroscopic isotherm with negligible hysteresis.

v. Re-Proportionation Examination (Experiment Reference 5)

a. Experimental Procedure

Equimolar quantities Tabernanthalog (native) (TBG Native, 25.6 mg) and the tabernanthalog monofumarate salt (Pattern #1, Sample Reference 1, 37.9 mg) were dissolved in methanol (1 ml, 20 vol) at reflux and the resultant solution was dried to a residue (5-O1) (Experiment Reference 5-Sample Reference O1) under nitrogen flow. $^1$H NMR spectroscopy (FIG. 85), to confirm the formation of the tabernanthalog hemifumarate.

Expt. #1: Tabernanthalog hemifumarate (5-O1) (Experiment Reference 5-Sample Reference O1) was equilibrated in acetonitrile at 20° C., and sampled at time points 20 h to determine if the hemi-salt (Experiment 2-03) is metastable with respect to the unary salt and reverts to the tabernanthalog monofumarate salt under suspension equilibration conditions (i.e. 2Tabernanthalog hemifumarate→Tabernanthalog monofumarate salt+Tabernanthalog (native)).

Figure 94:
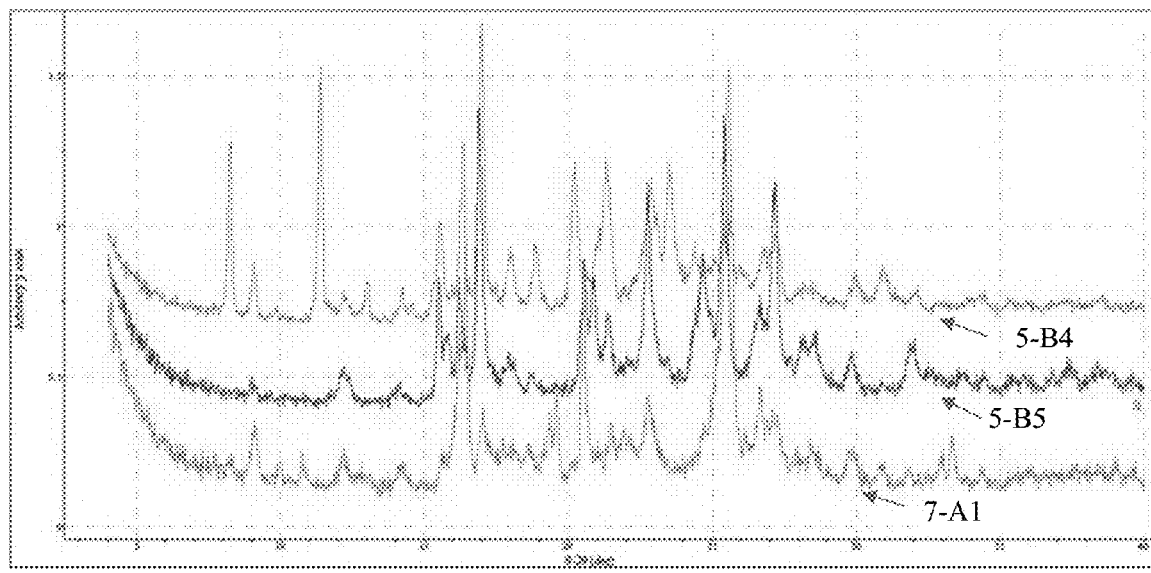
FIG. 94 depicts the XRPD overlay of, form top to bottom, a mixture of Tabernanthalog·0.5Fumarate and Tabernanthalog·Fumarate equilibrated in acetonitrile at 20° C., a mixture of Tabernanthalog·0.5Fumarate and Tabernanthalog·Fumarate equilibrated in acetonitrile at 40° C., and Tabernanthalog fumarate Pattern 19.
Figure 95:
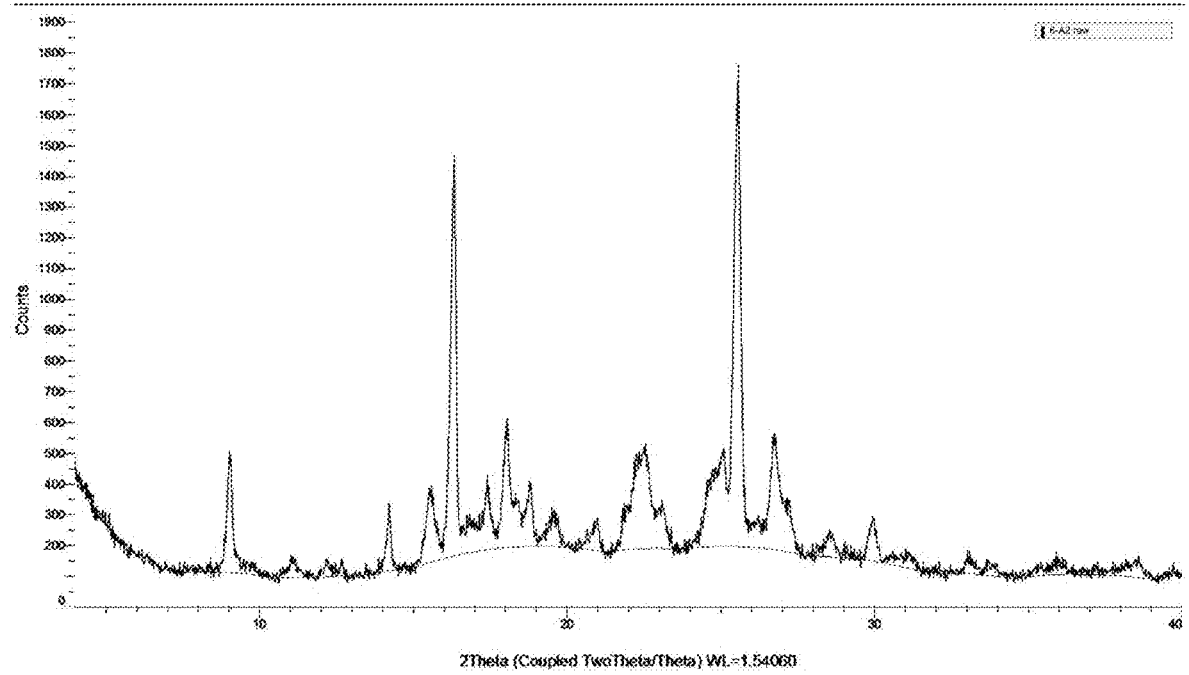
FIG. 95 depicts the XRPD profile of 6-A2 (Experiment Reference 6-Sample Reference A2) (Pattern #2b).
Figure 96:
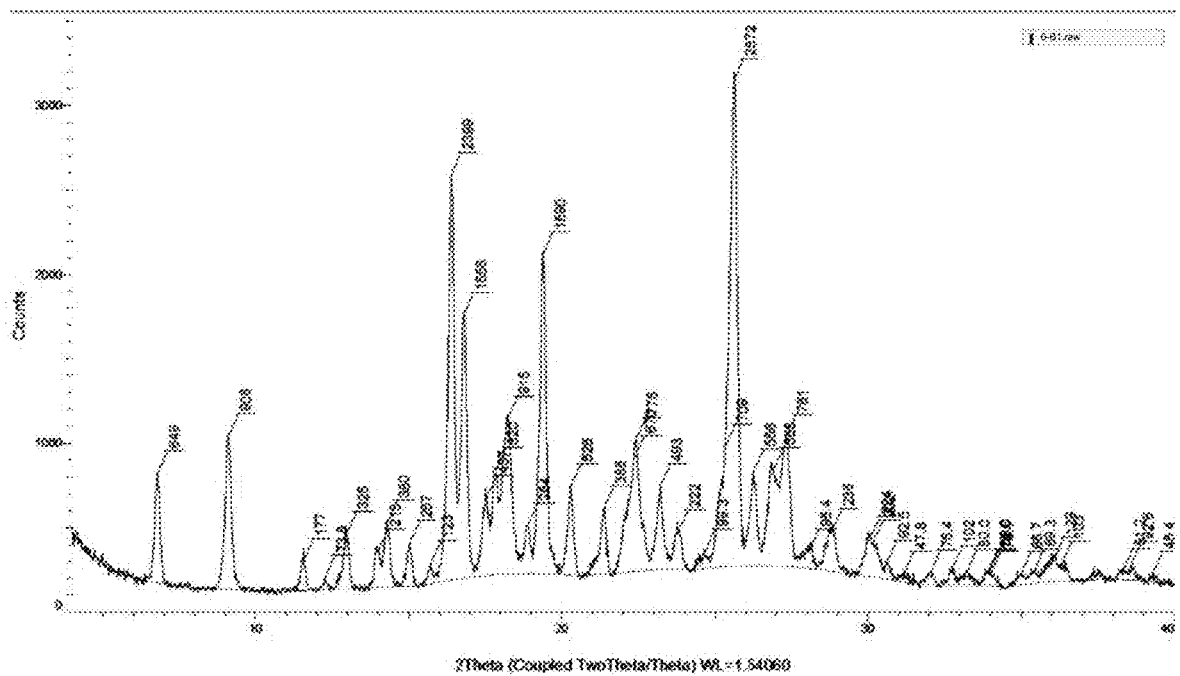
FIG. 96 depicts the XRPD profile of 6-B1 (Experiment Reference 6-Sample Reference B1) (Pattern #1).
Figure 97:
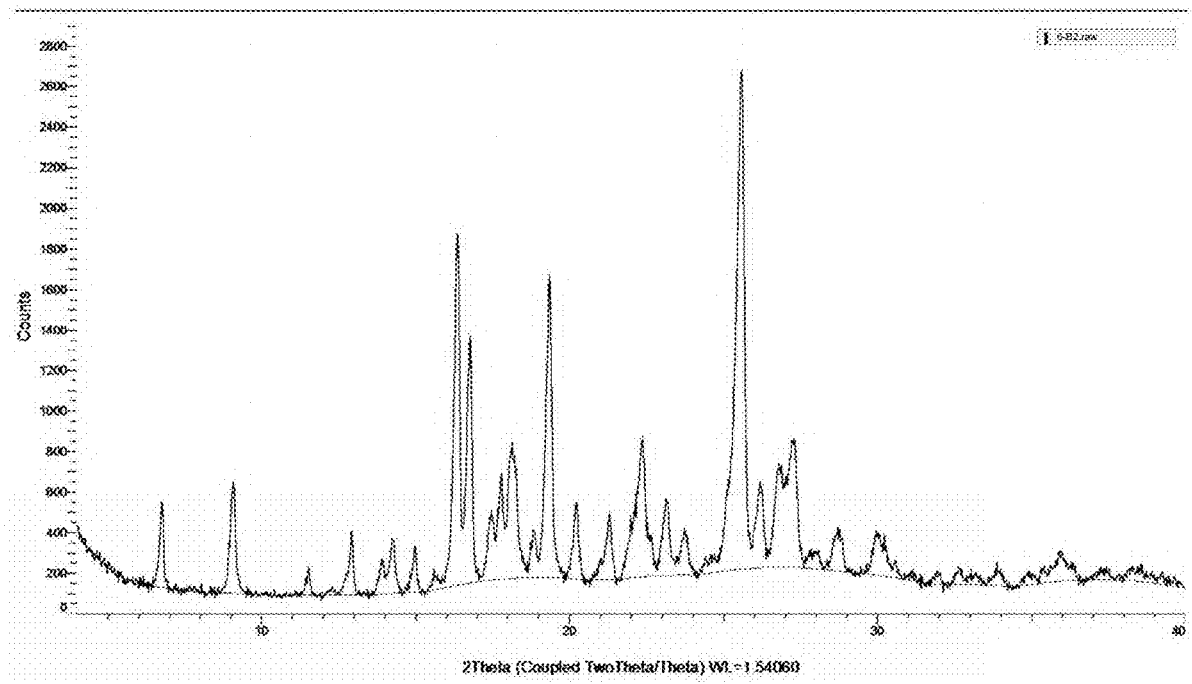
FIG. 97 depicts the XRPD profile of 6-B2 (Experiment Reference 6-Sample Reference B2) (Pattern #1).
Figure 98:
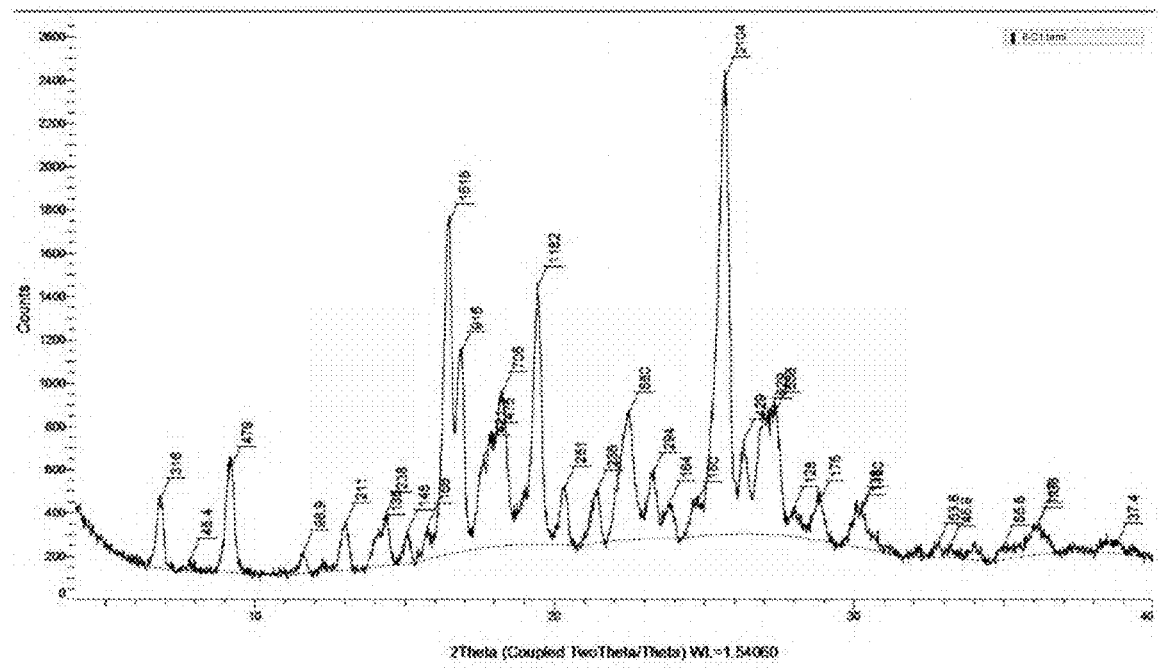
FIG. 98 depicts the XRPD profile of 6-C1 (Experiment Reference 6-Sample Reference C1) (Pattern #1).
Figure 99:
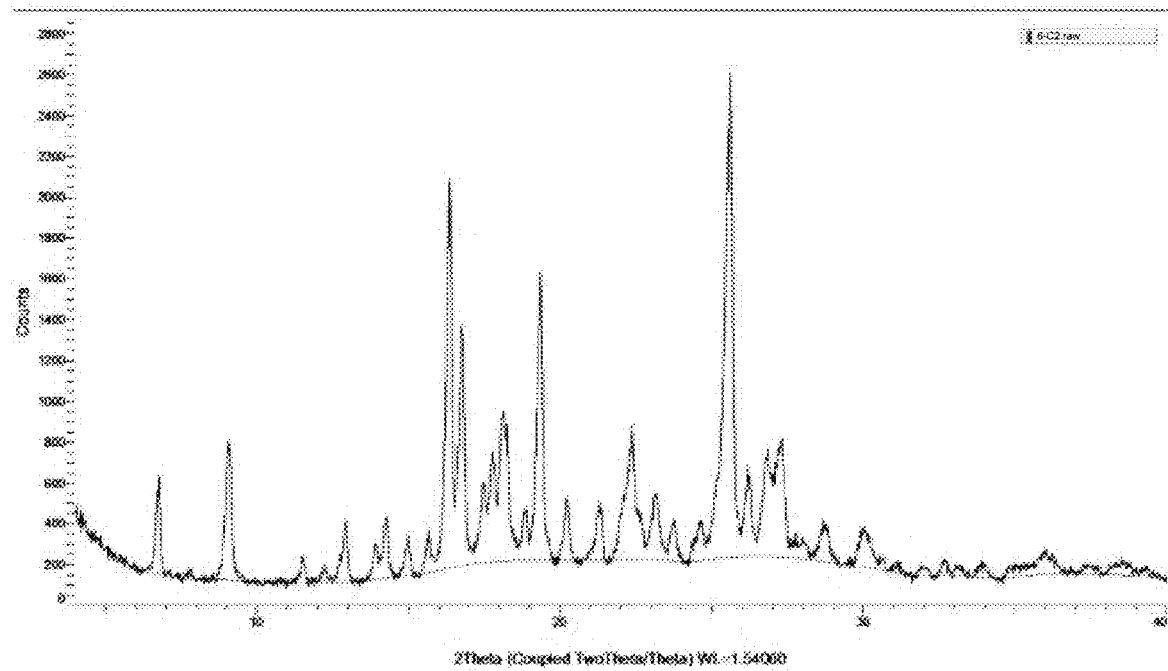
FIG. 99 depicts the XRPD profile of 6-C2 (Experiment Reference 6-Sample Reference C2) (Pattern #1).
Figure 100:
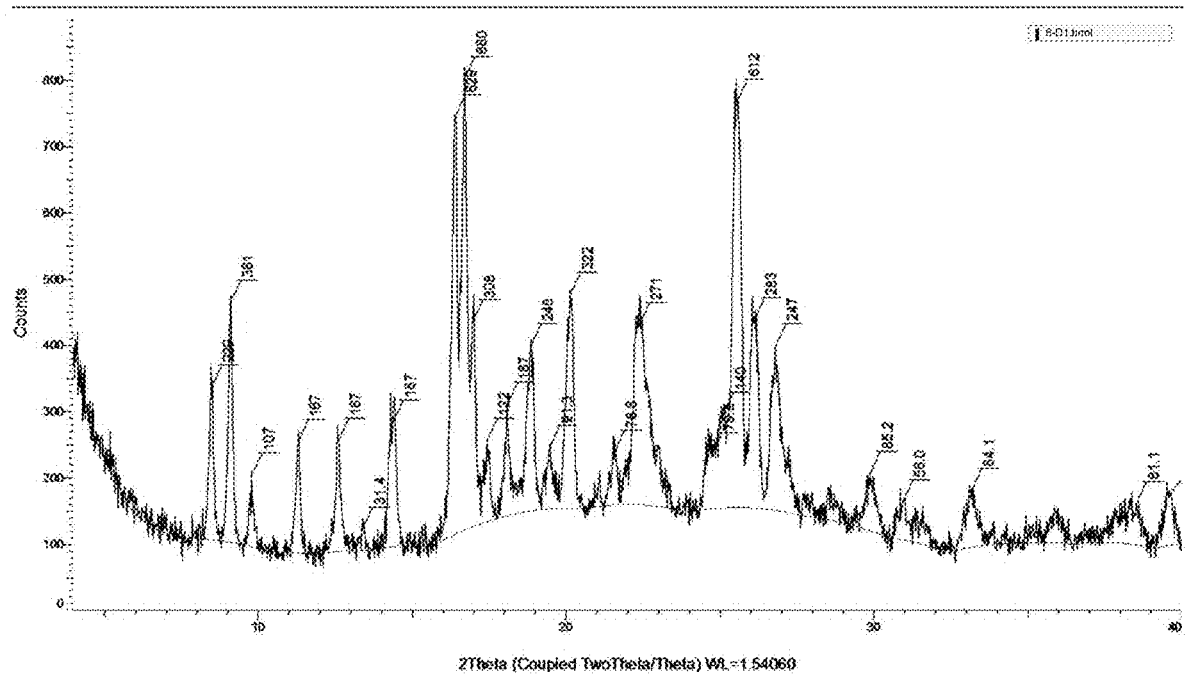
FIG. 100 depicts the XRPD profile of 6-D1 (Experiment Reference 6-Sample Reference D1) (Pattern #3).
Figure 101:
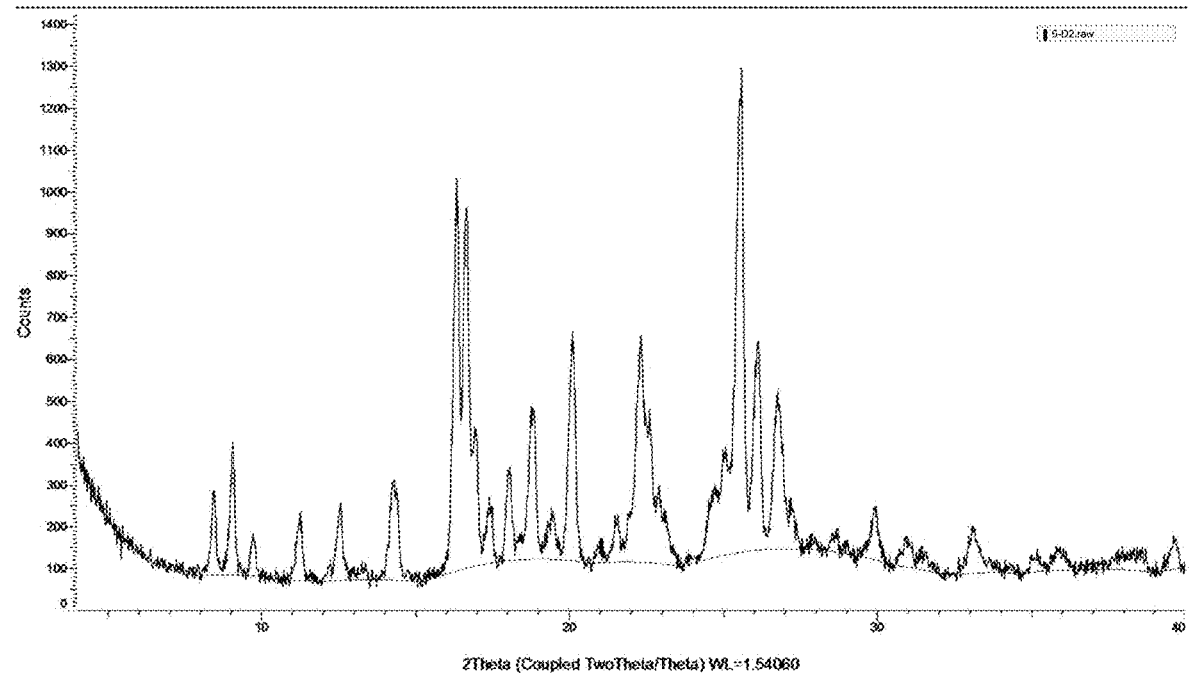
FIG. 101 depicts the XRPD profile of 6-D2 (Experiment Reference 6-Sample Reference D2) (Pattern #3).
Figure 102:
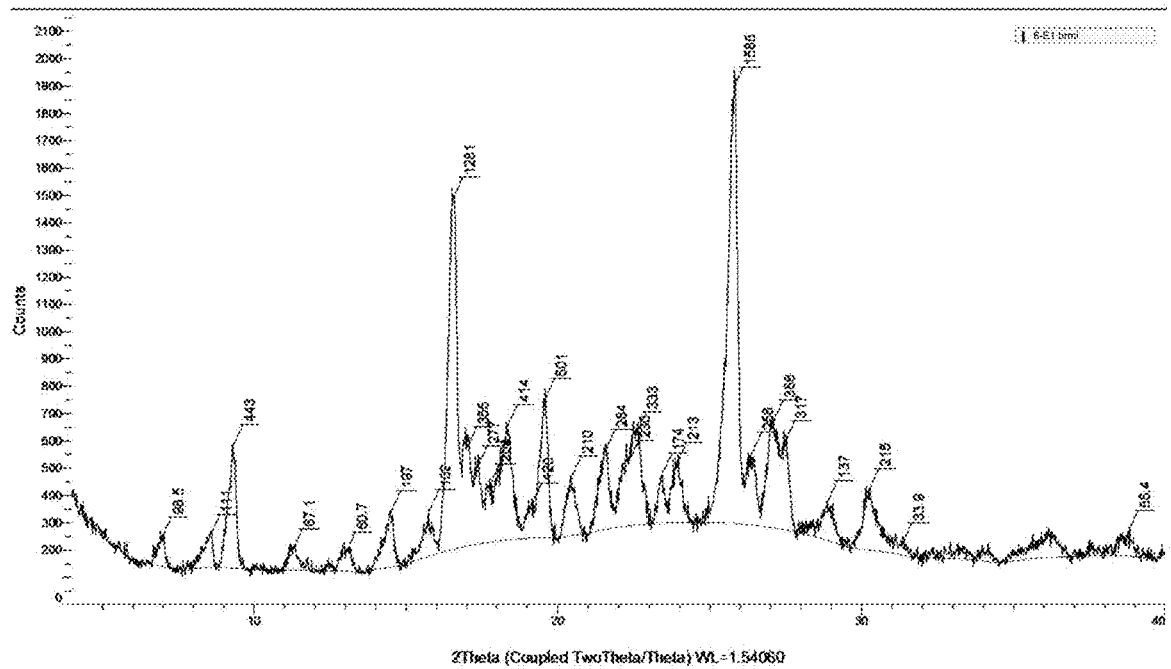
FIG. 102 depicts the XRPD profile of 6-E1 (Experiment Reference 6-Sample Reference E1) (Pattern #4b).
Figure 103:
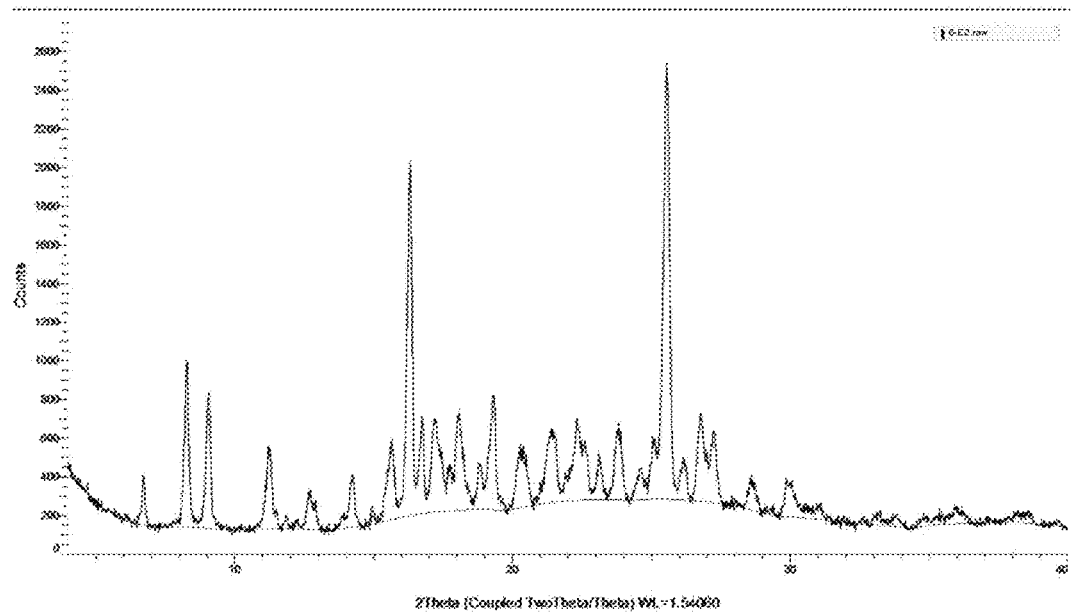
FIG. 103 depicts the XRPD profile of 6-E2 (Experiment Reference 6-Sample Reference E2) (Pattern #4b).
Figure 104:
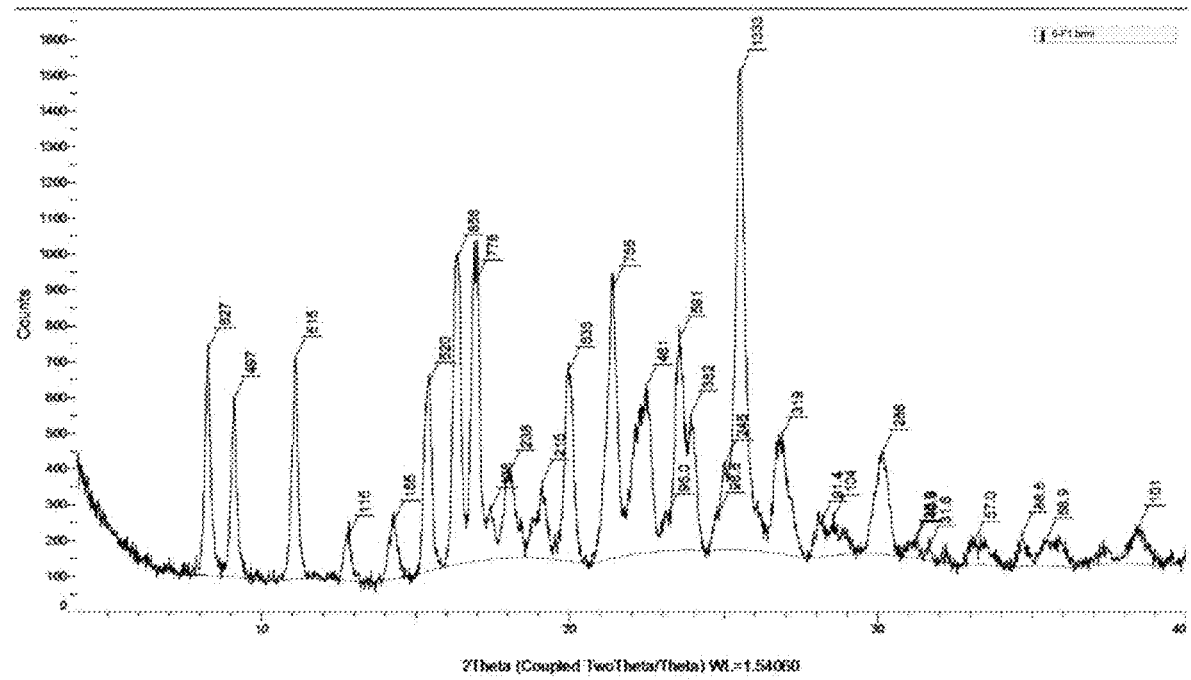
FIG. 104 depicts the XRPD profile of 6-F1 (Experiment Reference 6-Sample Reference F1) (Pattern #5).
Figure 105:
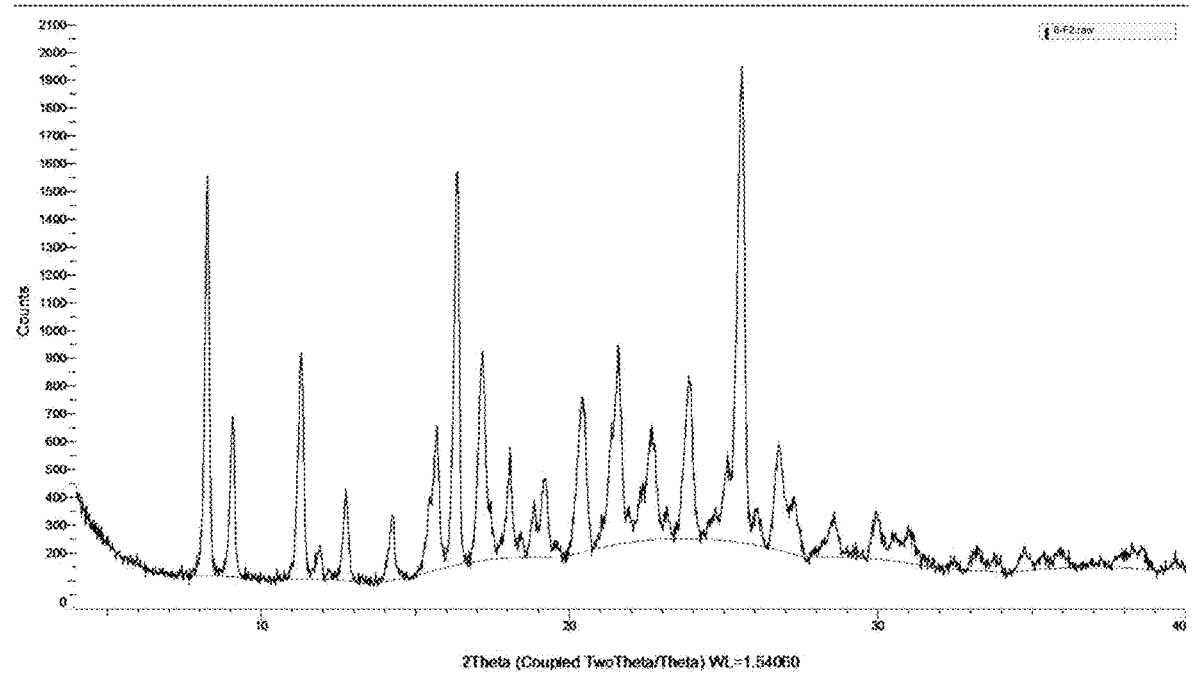
FIG. 105 depicts the XRPD profile of 6-F2 (Experiment Reference 6-Sample Reference F2) (Pattern #4a).
Figure 106:
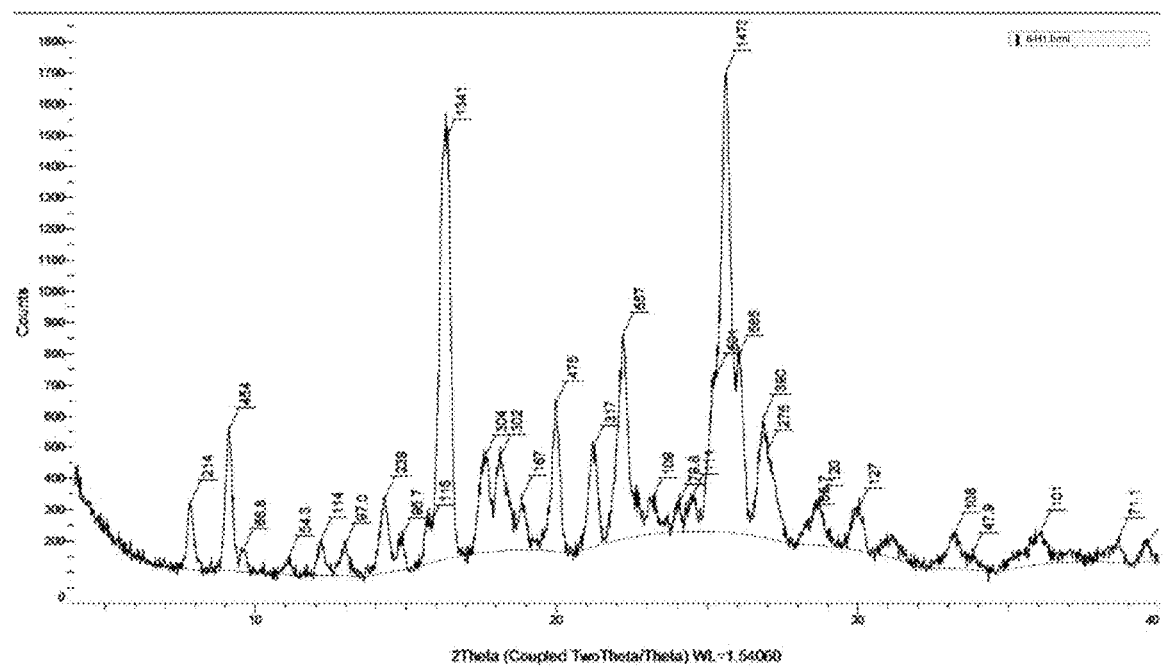
FIG. 106 depicts the XRPD profile of 6-H1 (Experiment Reference 6-Sample Reference H1) (Pattern #2d).
Figure 107:
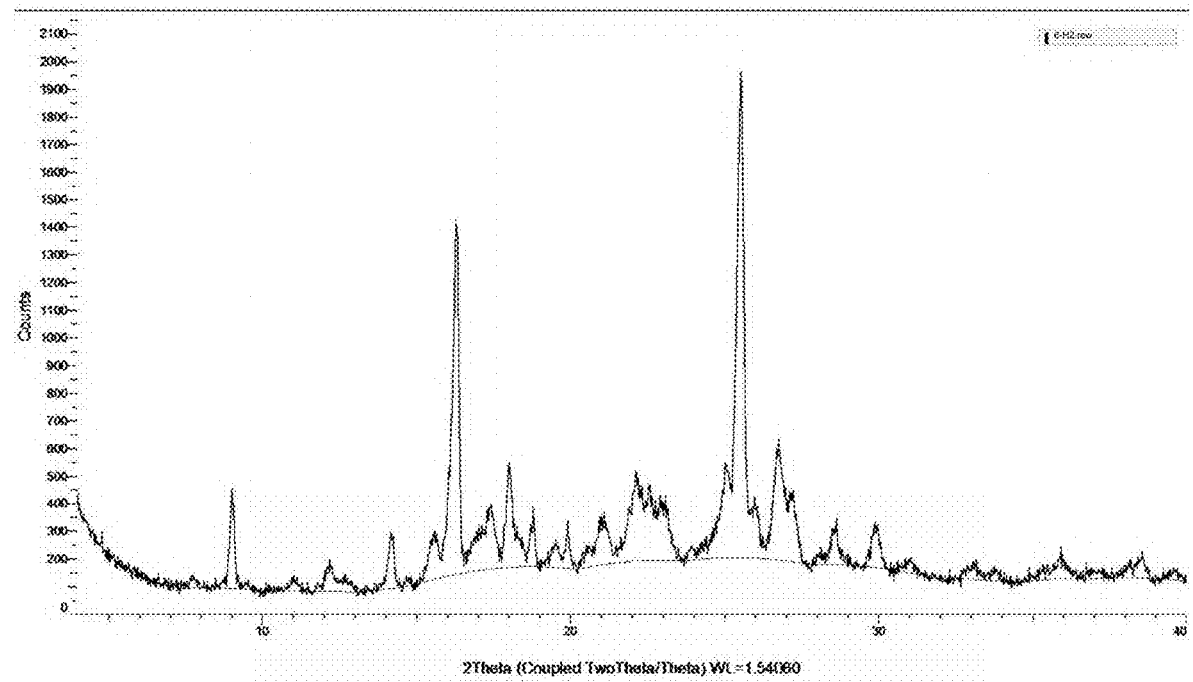
FIG. 107 depicts the XRPD profile of 6-H2 (Experiment Reference 6-Sample Reference H2) (Pattern #2b).
Figure 108:
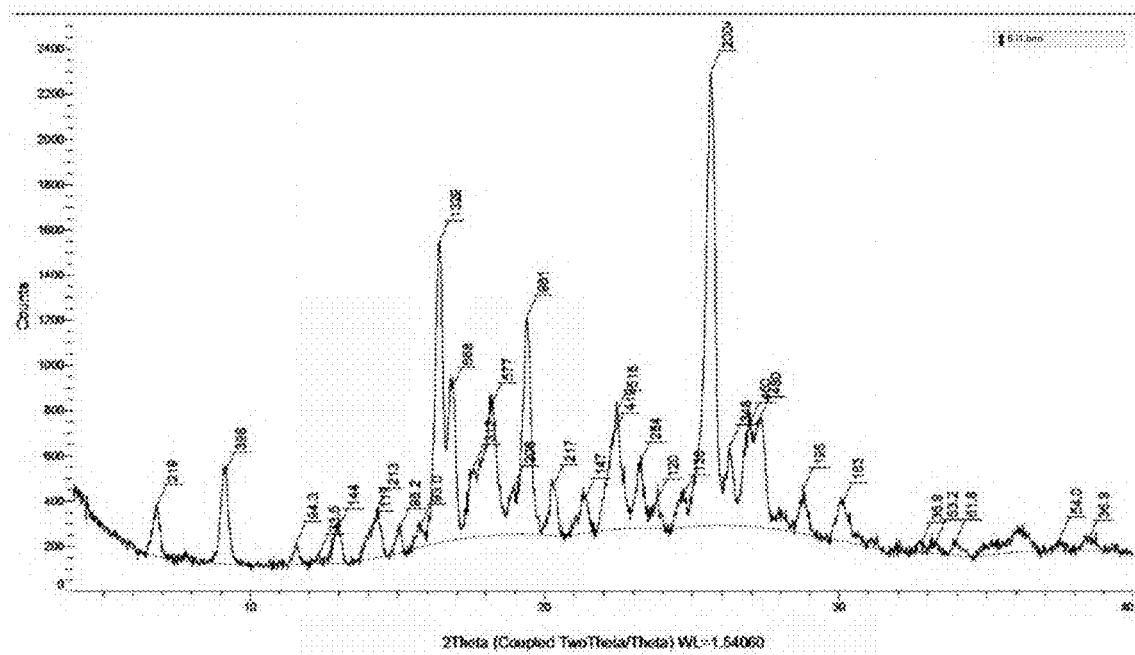
FIG. 108 depicts the XRPD profile of 6-I1 (Experiment Reference 6-Sample Reference I1) (Pattern #1).
Figure 109:
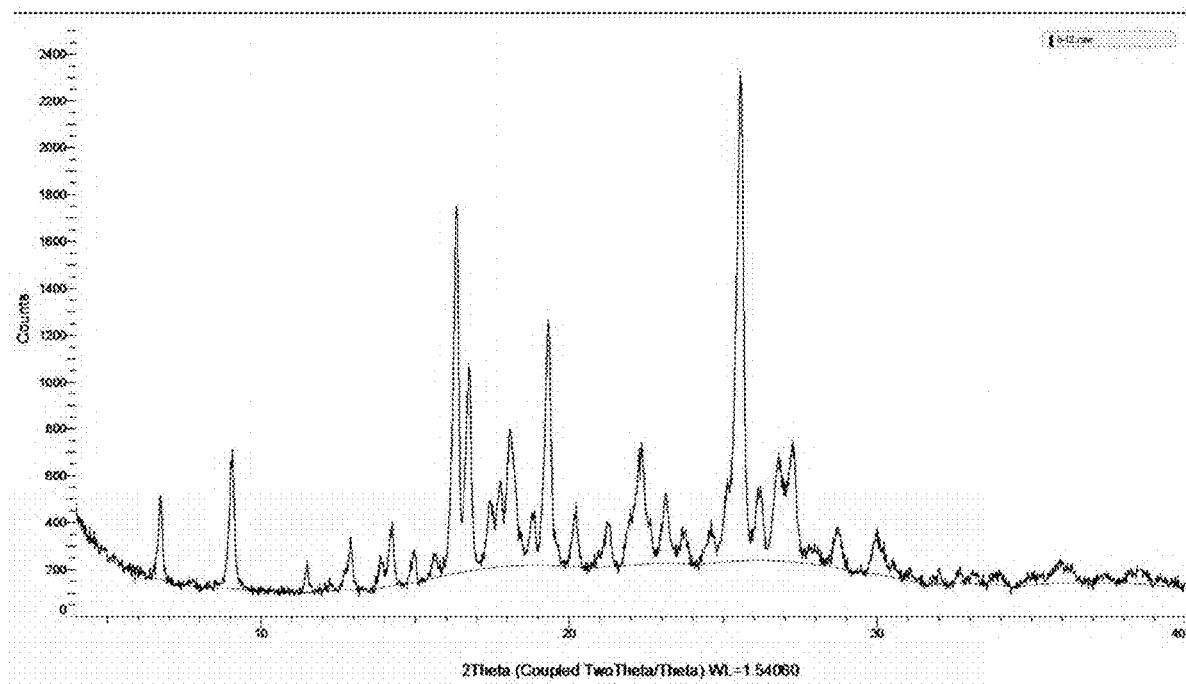
FIG. 109 depicts the XRPD profile of 6-I2 (Experiment Reference 6-Sample Reference I2) (Pattern #1).
Figure 110:
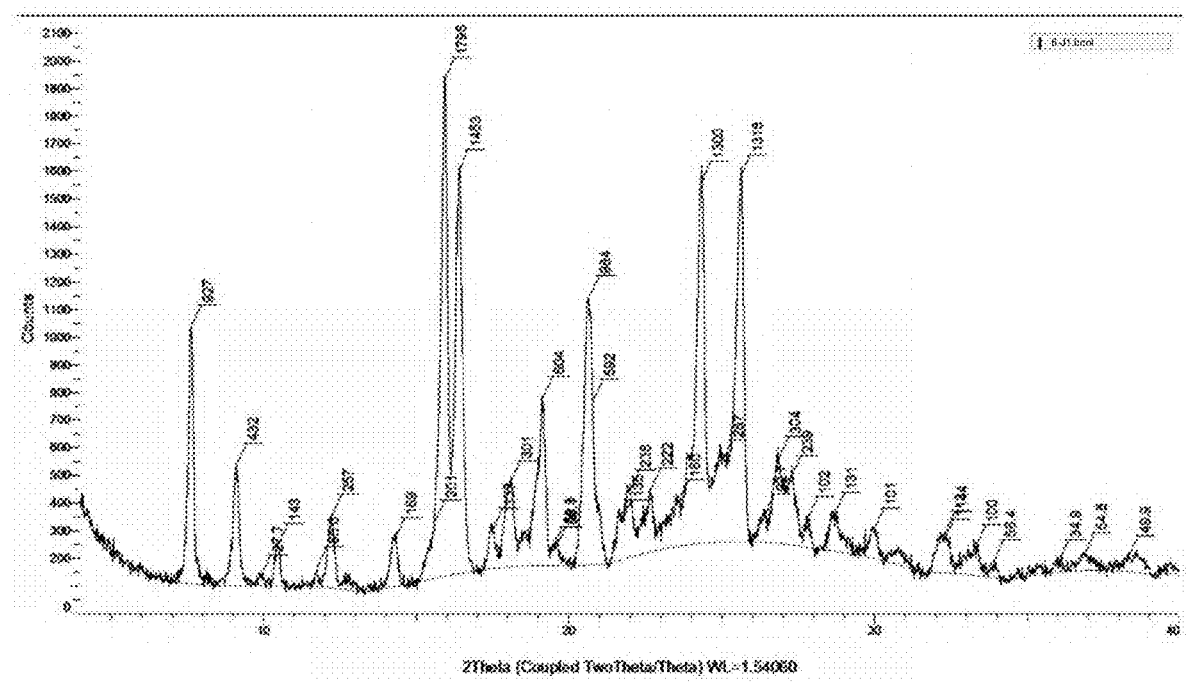
FIG. 110 depicts the XRPD profile of 6-J1 (Experiment Reference 6-Sample Reference J1) (Pattern #8).
Figure 111:
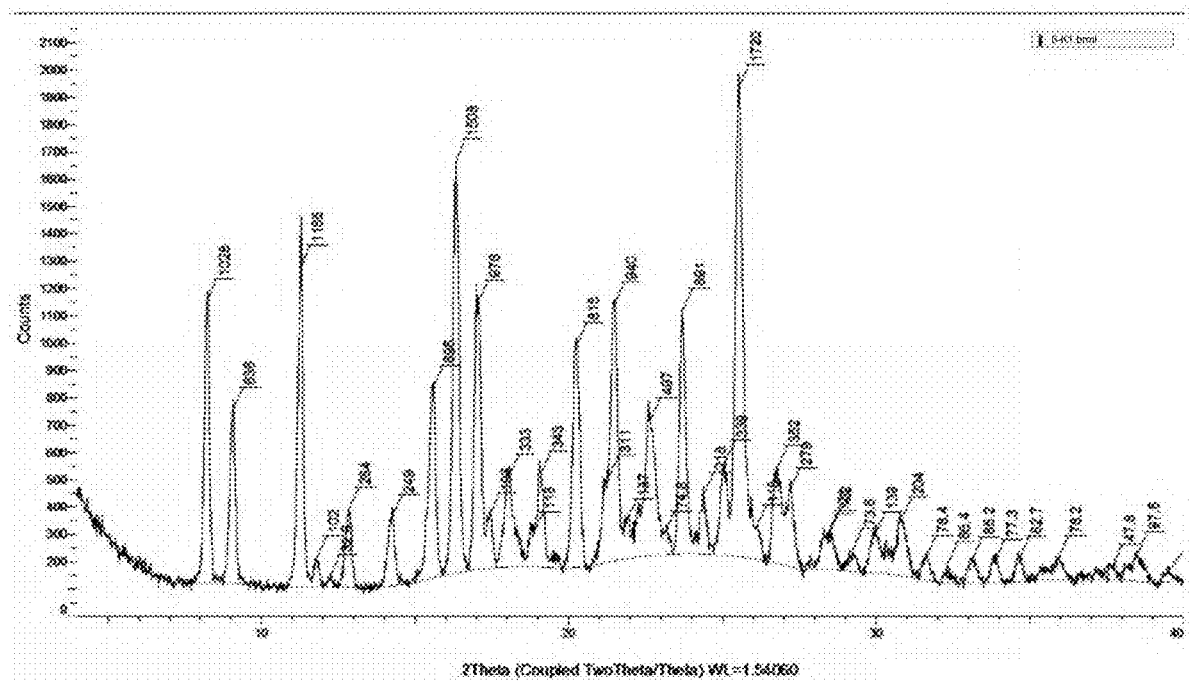
FIG. 111 depicts the XRPD profile of 6-K1 (Experiment Reference 6-Sample Reference K1) (Pattern #4a).
Figure 112:
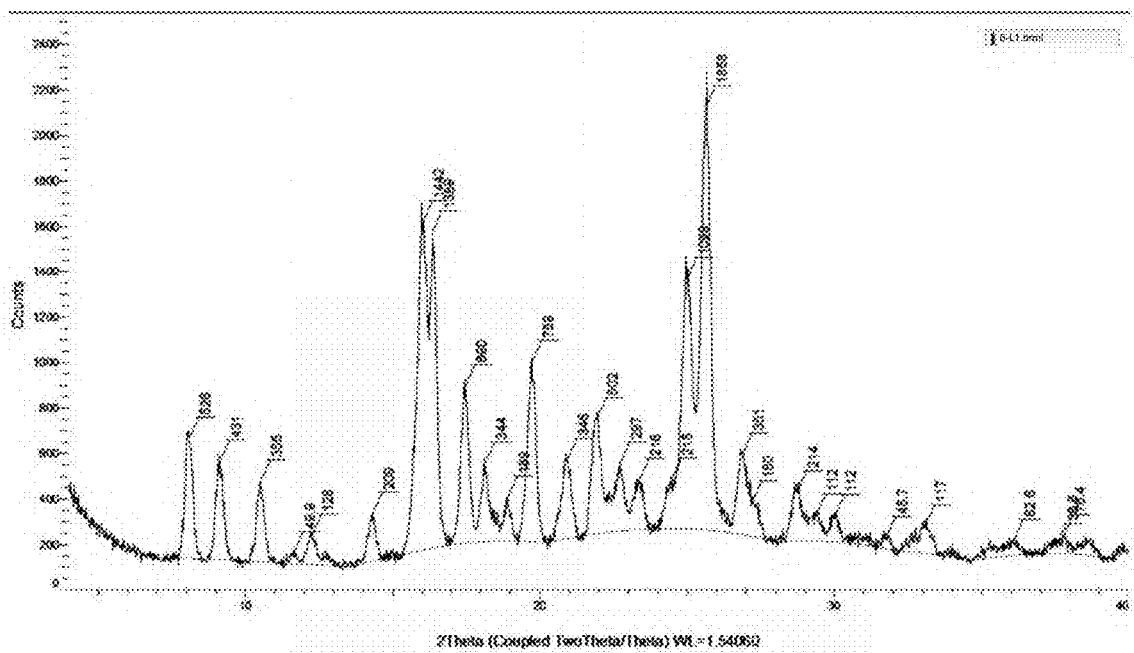
FIG. 112 depicts the XRPD profile of 6-L1 (Experiment Reference 6-Sample Reference L1) (Pattern #13).
Figure 113:
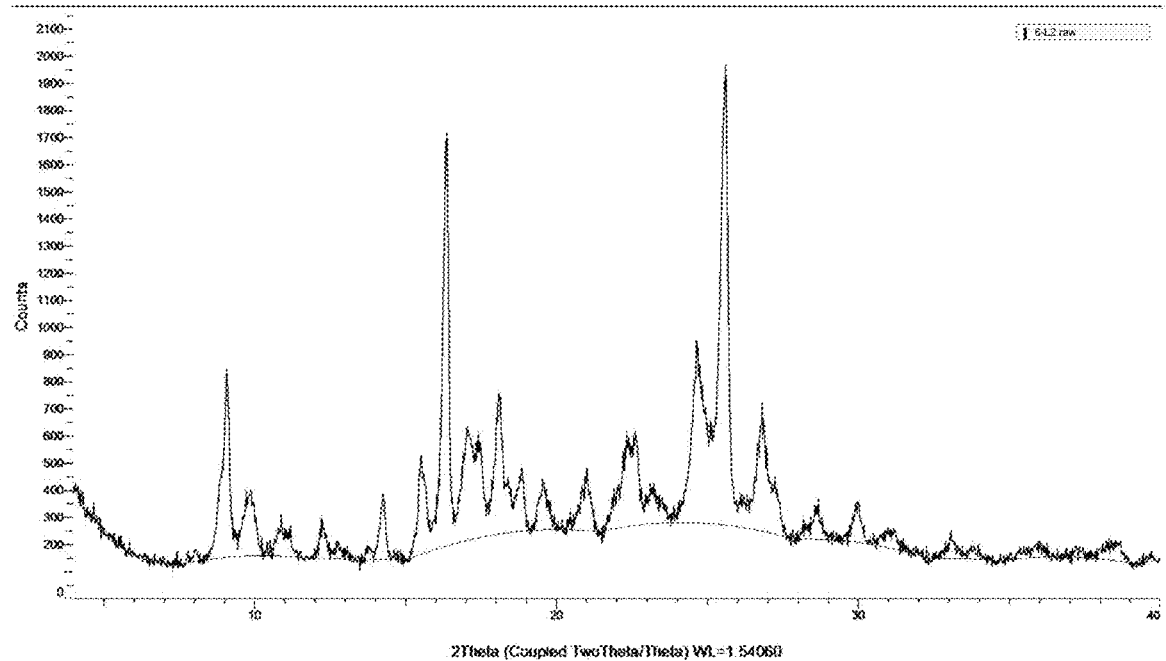
FIG. 113 depicts the XRPD profile of 6-L2 (Experiment Reference 6-Sample Reference L2) (Pattern #2b).
Figure 114:
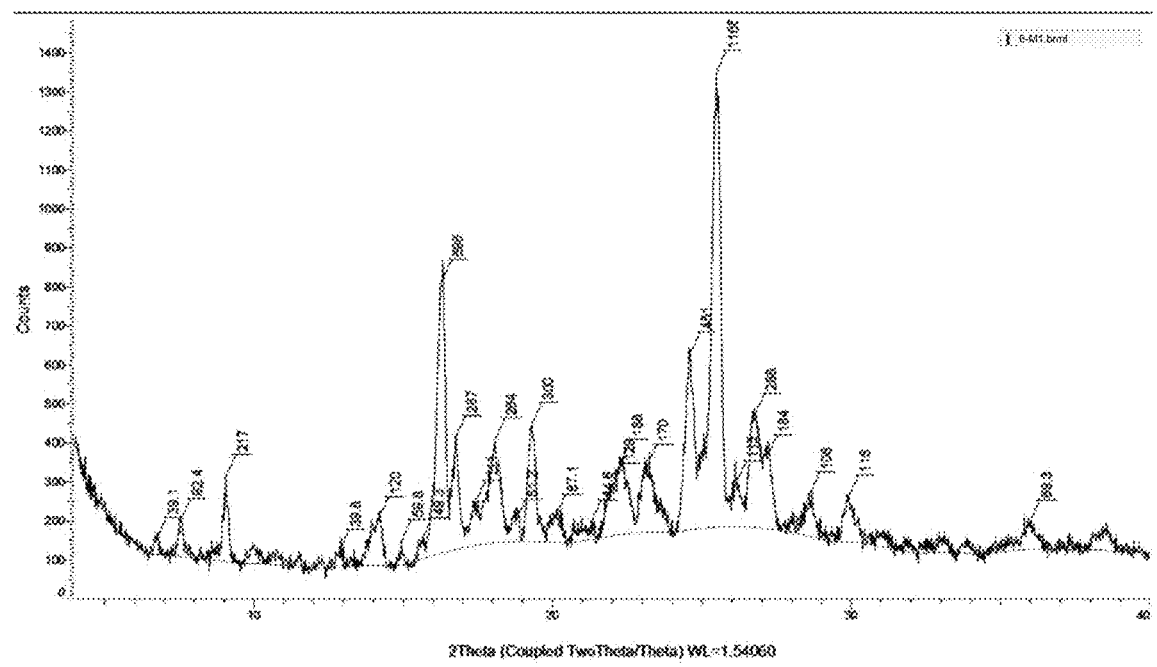
FIG. 114 depicts the XRPD profile of 6-M1 (Experiment Reference 6-Sample Reference M1) (Pattern #1).
Figure 115:
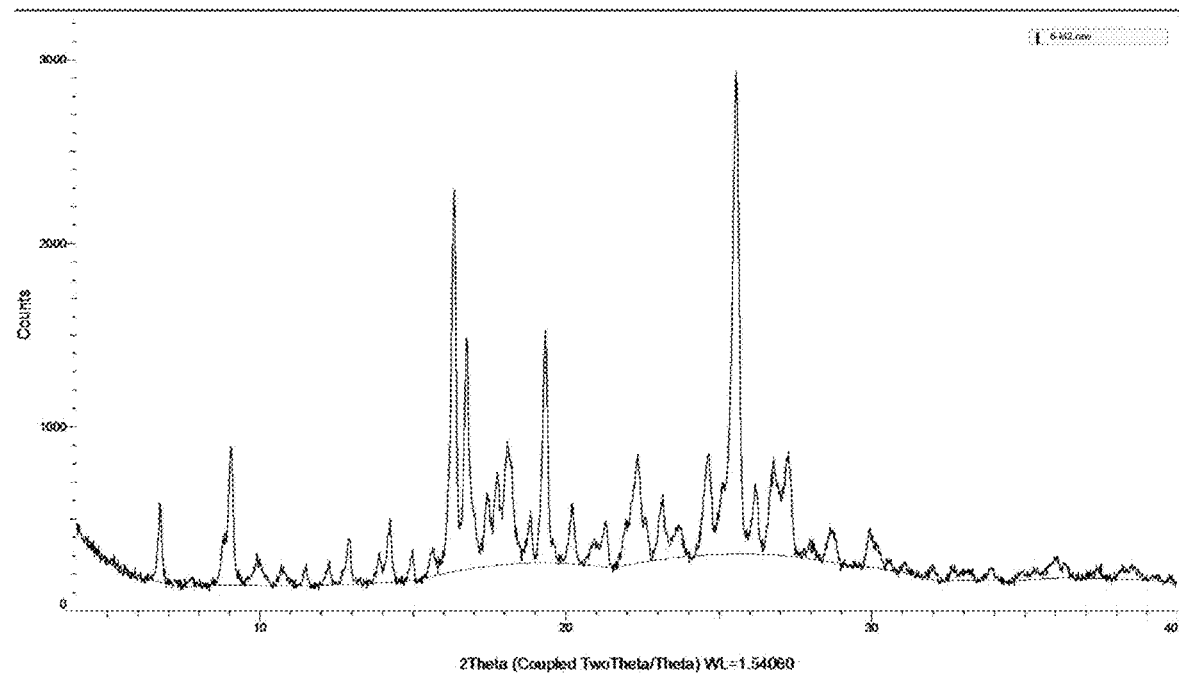
FIG. 115 depicts the XRPD profile of 6-M2 (Experiment Reference 6-Sample Reference M2) (Pattern #1).
Figure 116:
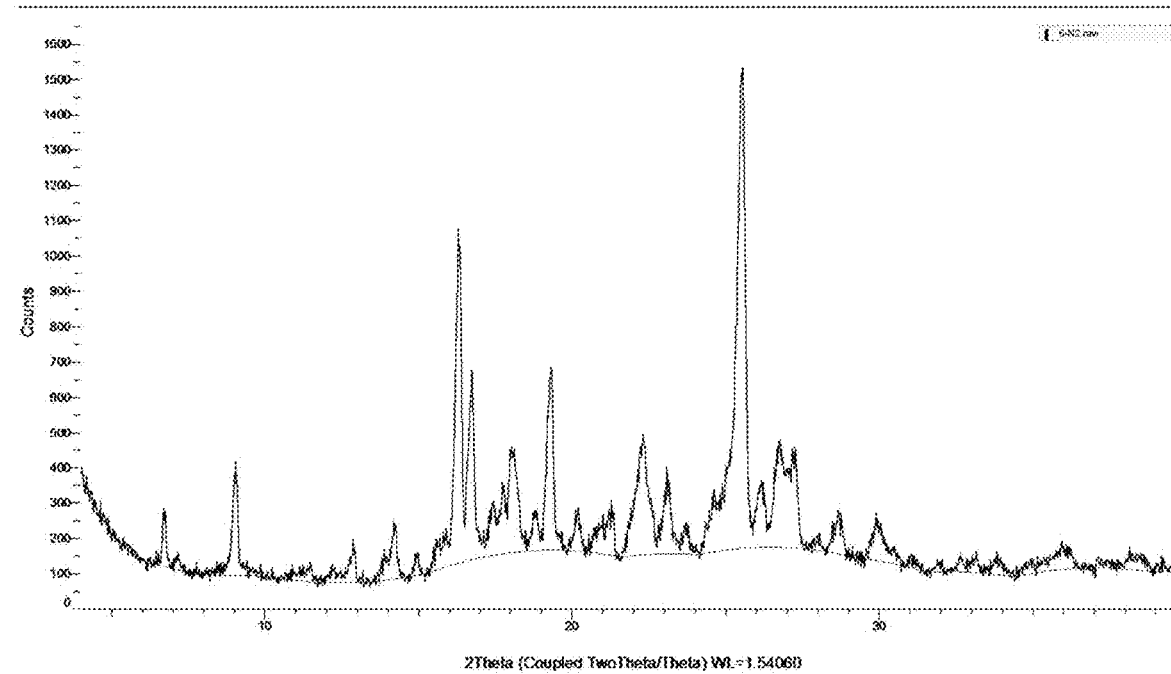
Figure 117:
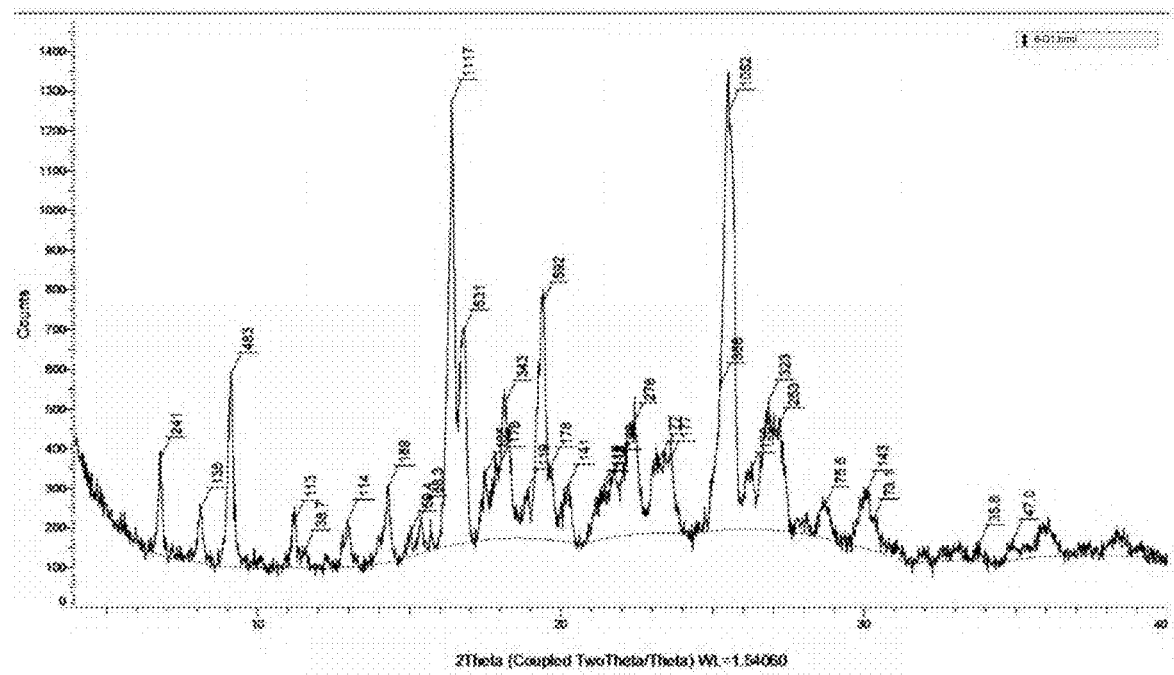
Figure 118:
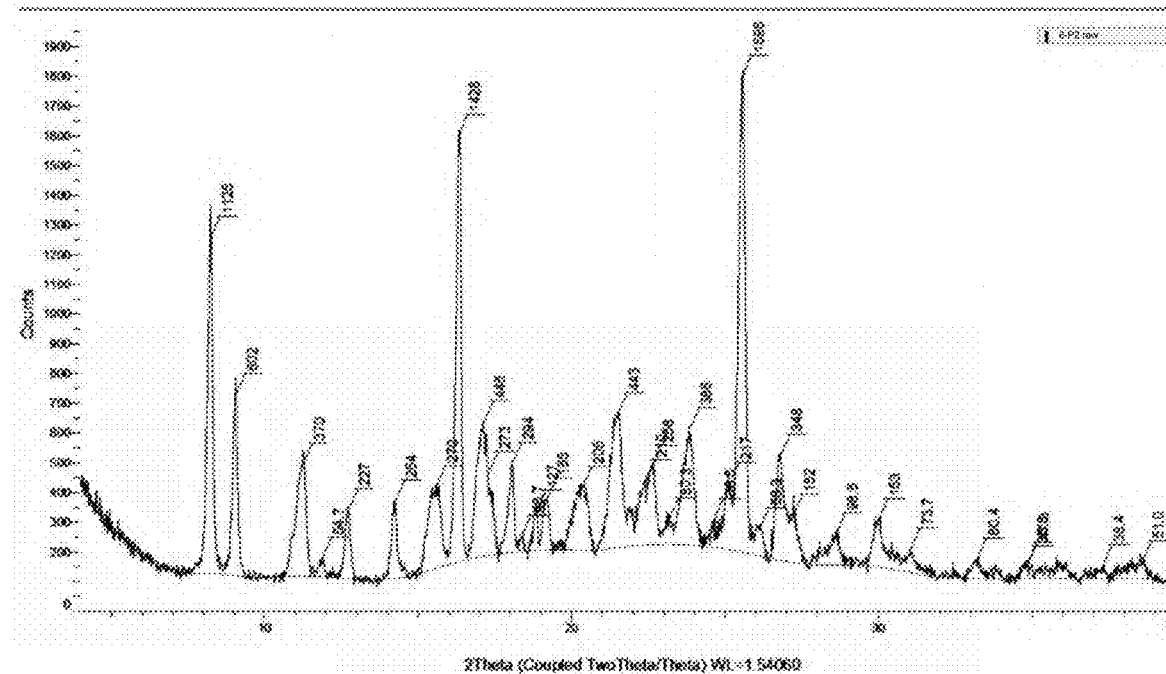
Figure 119:
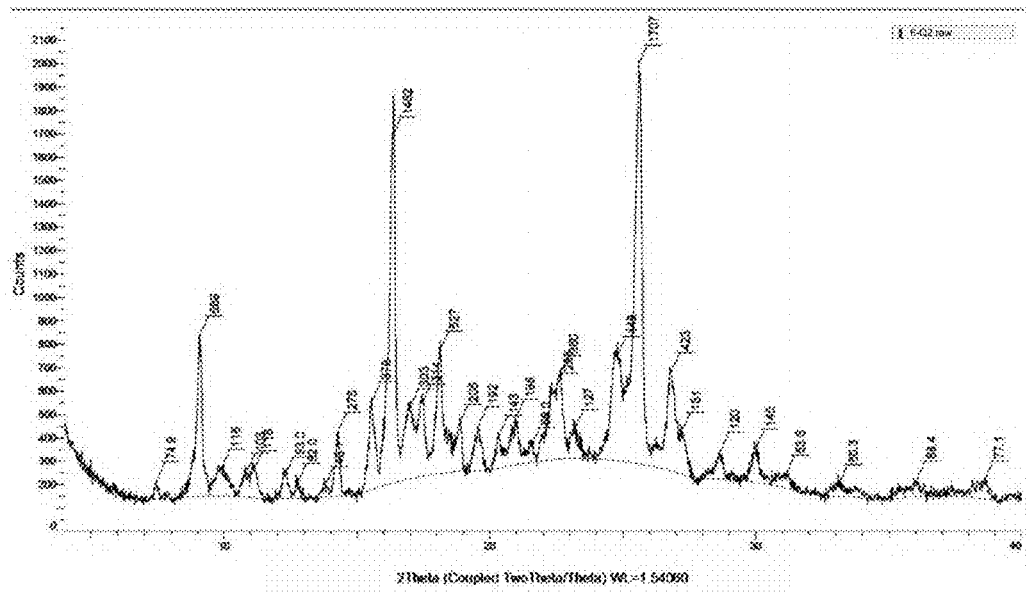
Figure 120:
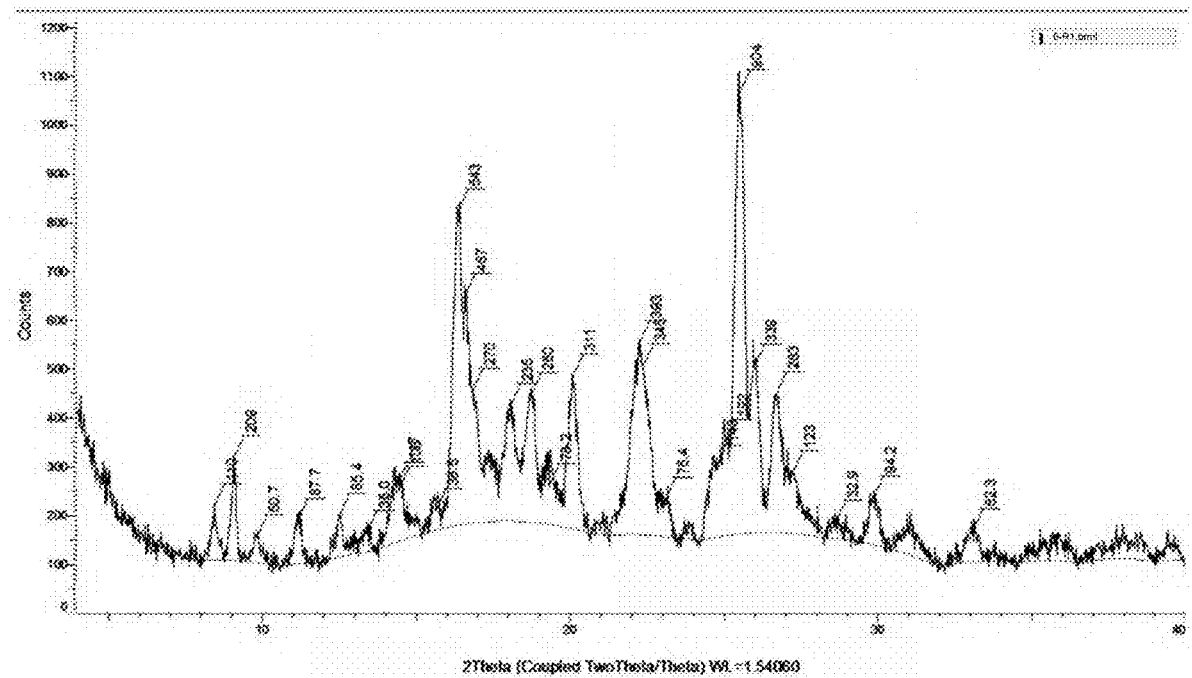
Figure 121:
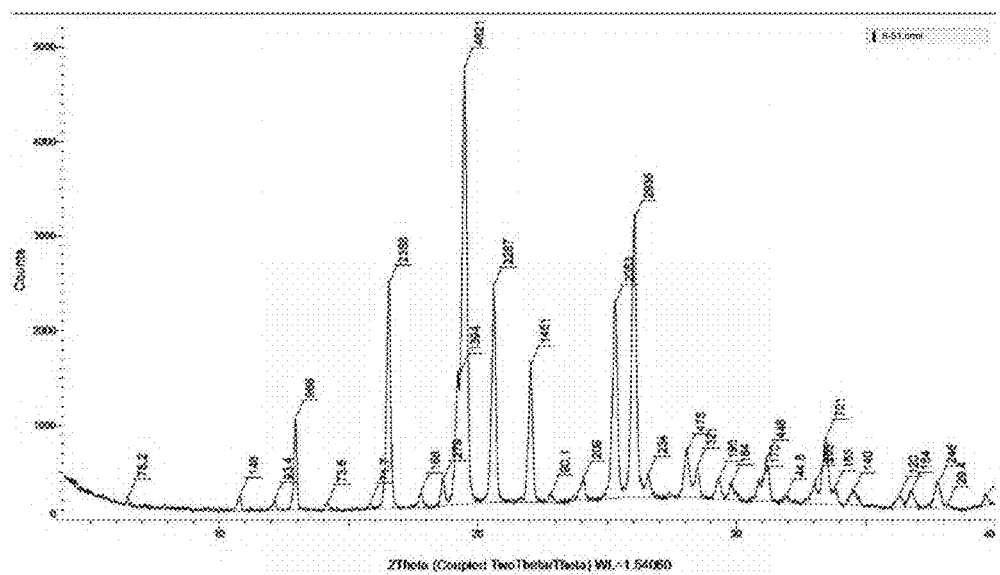
Figure 122:
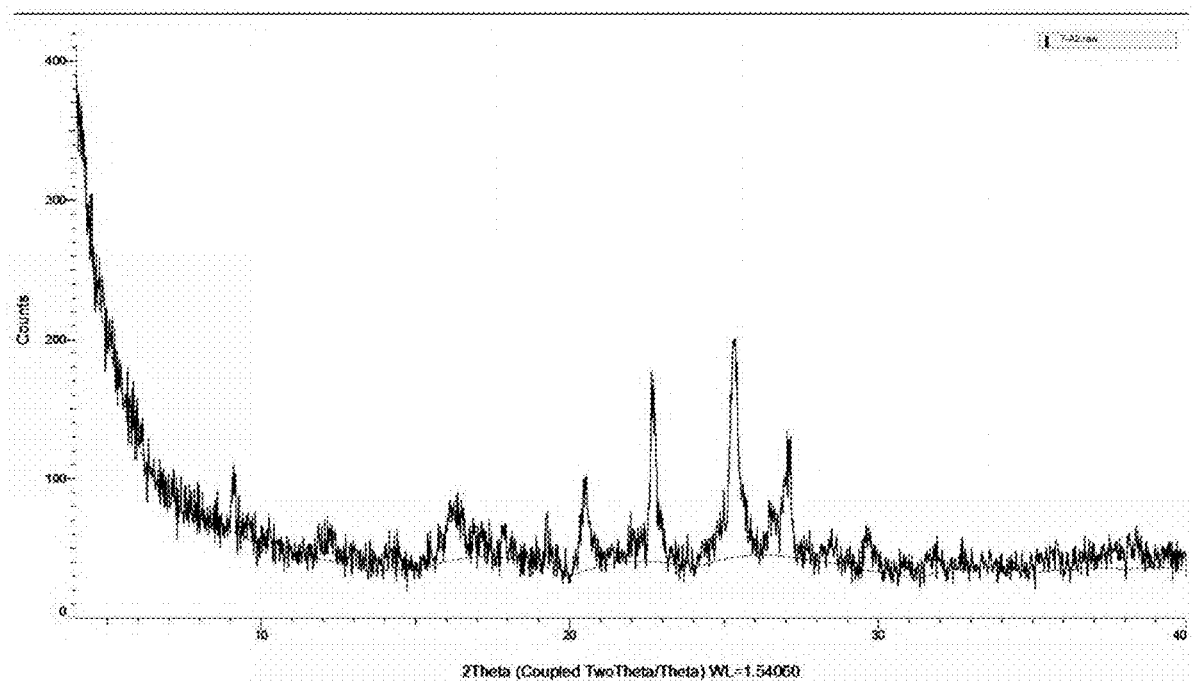
Figure 123:
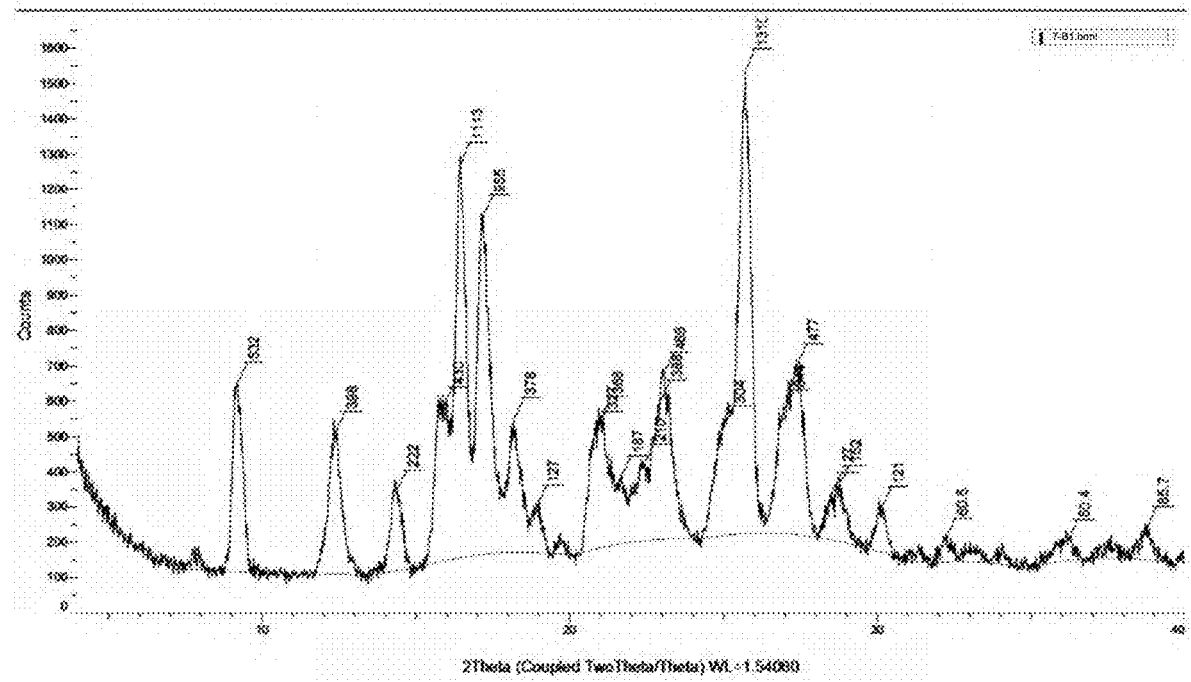
Figure 124:
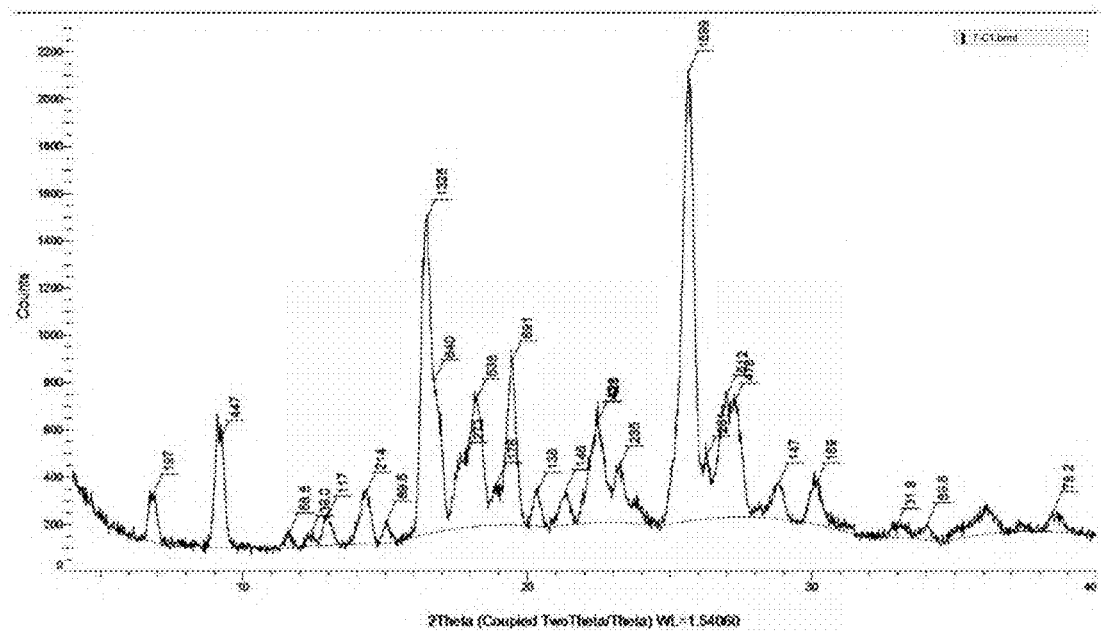
Figure 125:
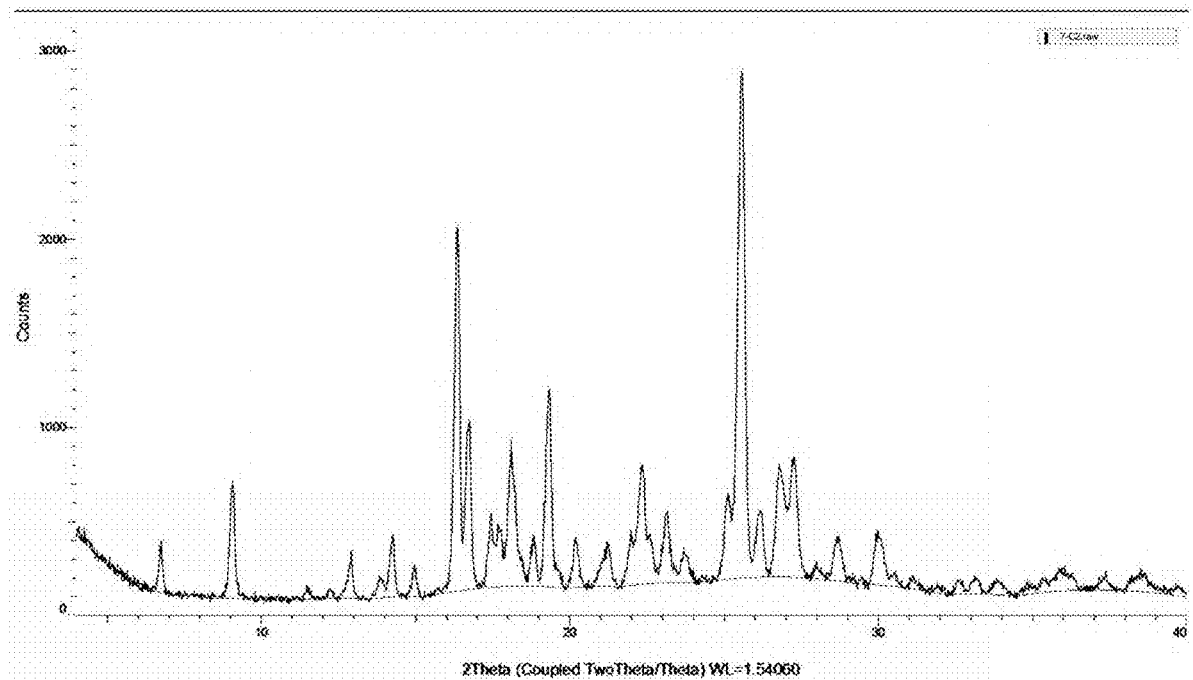
Figure 126:
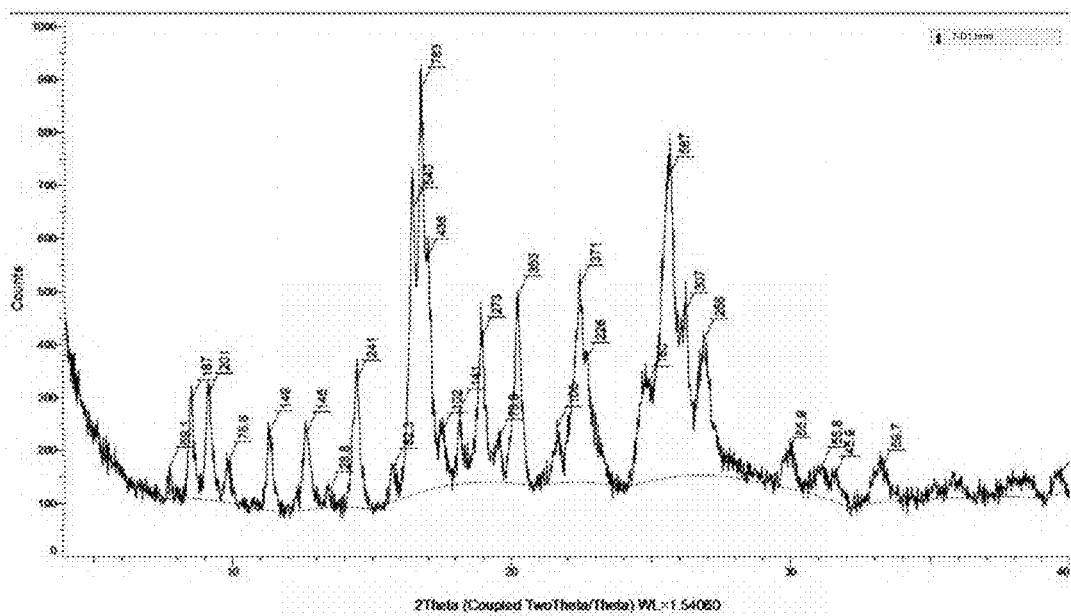
Figure 127:
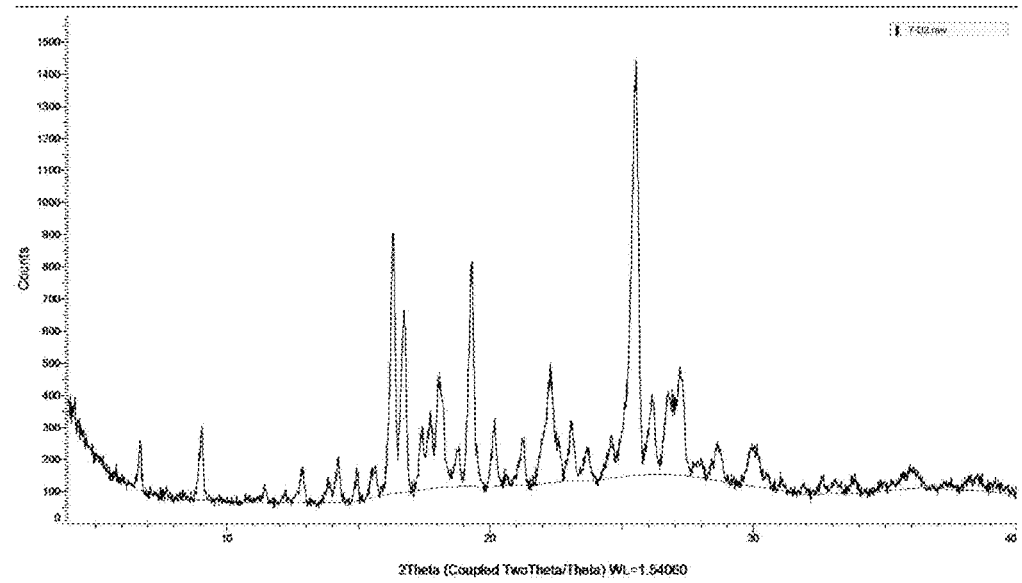

Expt. #2: an equi-weight mixture of tabernanthalog hemifumarate (Pattern #14, 5-B3) (Expt. #2 of Experiment Reference 5-Sample Reference B3) and the tabernanthalog monofumarate salt (Pattern 1, Reference Number 1, 23.6 mg) were competitively equilibrated in acetonitrile at 20° C. (5-B4; Experiment Reference 5-Sample Reference B4) and 40° C. (5-B5; Experiment Reference 5-Sample Reference B5). The output was analyzed by XRPD (FIG. 94).

Figure 85:
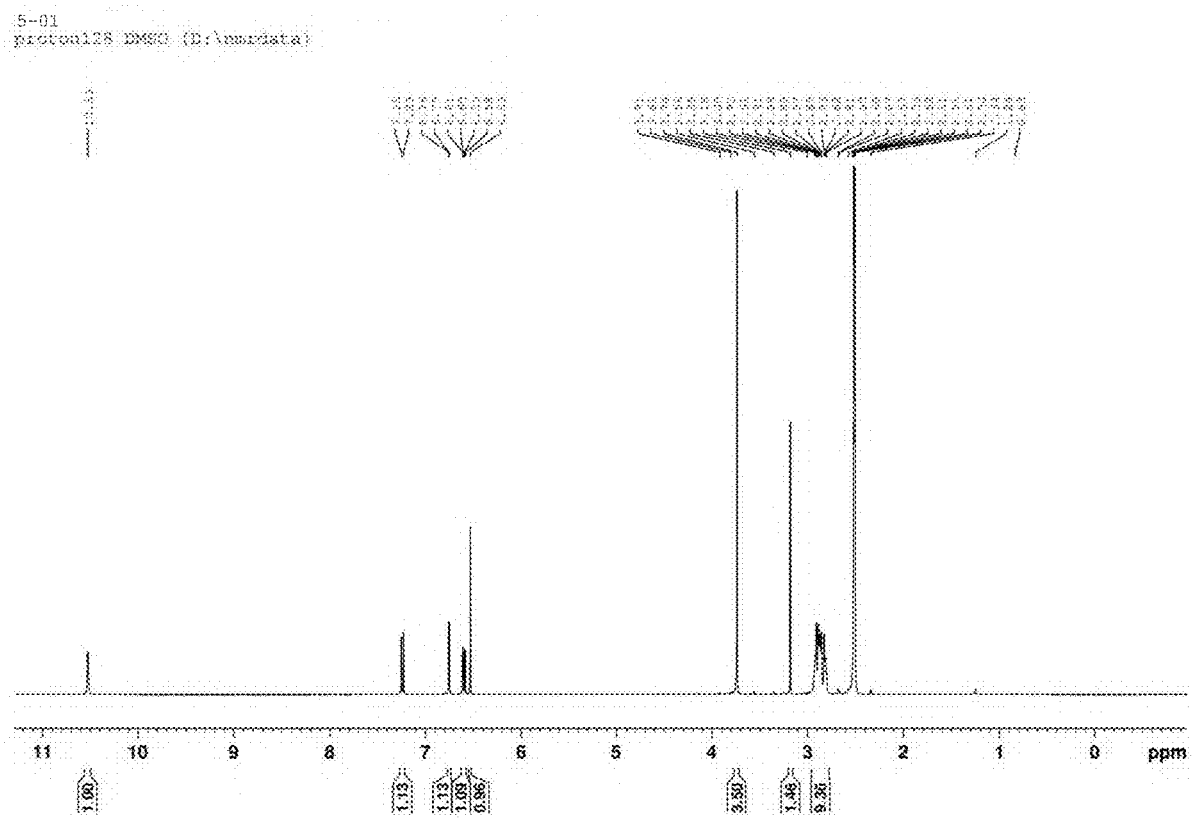
FIG. 85 depicts the $^1$H NMR spectrum of (5-O1) (Experiment Reference 5-Sample Reference O1) that was acquired in DMSO-d6 and calibrated to the non-deuterated solvent residual at 2.50 ppm API to Fumaric acid, 1.0 to 0.5.
Figure 86:
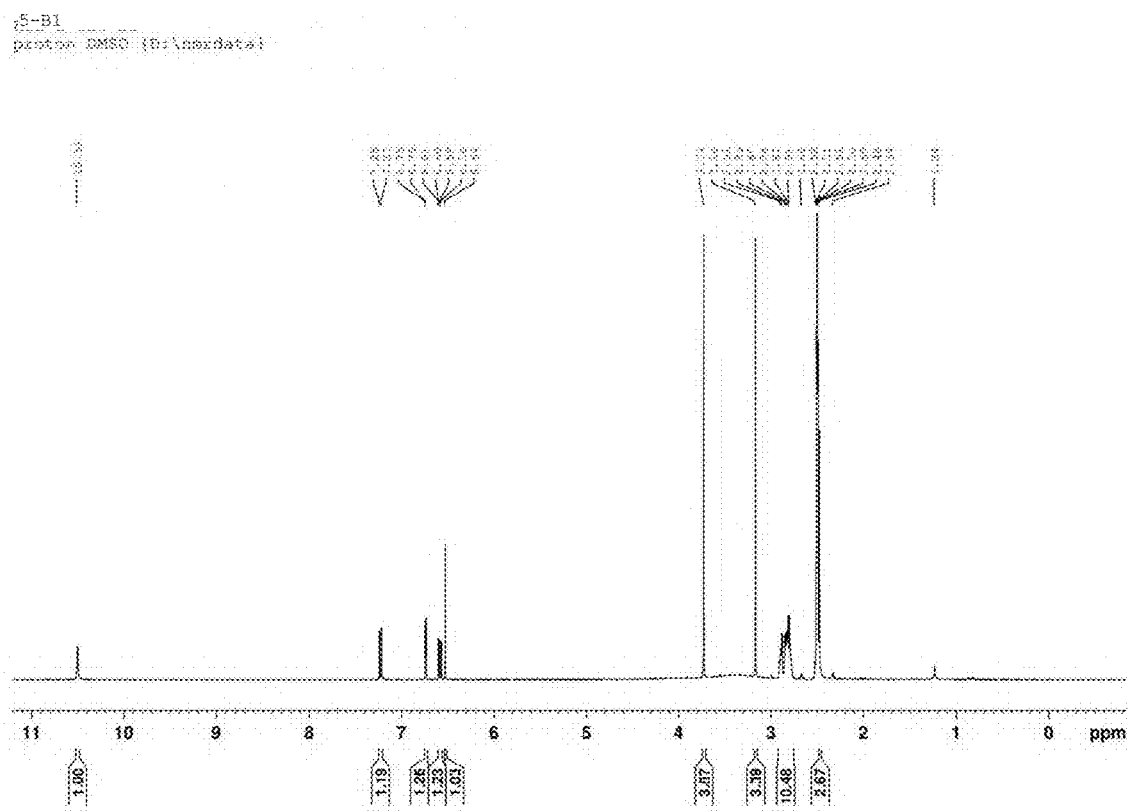
FIG. 86 depicts the $^1$H NMR spectrum of 5-B1 (Experiment Reference 5-Sample Reference B1) that was acquired in DMSO-d6 and calibrated to the non-deuterated solvent residual at 2.50 ppm API to Fumaric acid, 1.0 to 0.5.
Figure 86A:
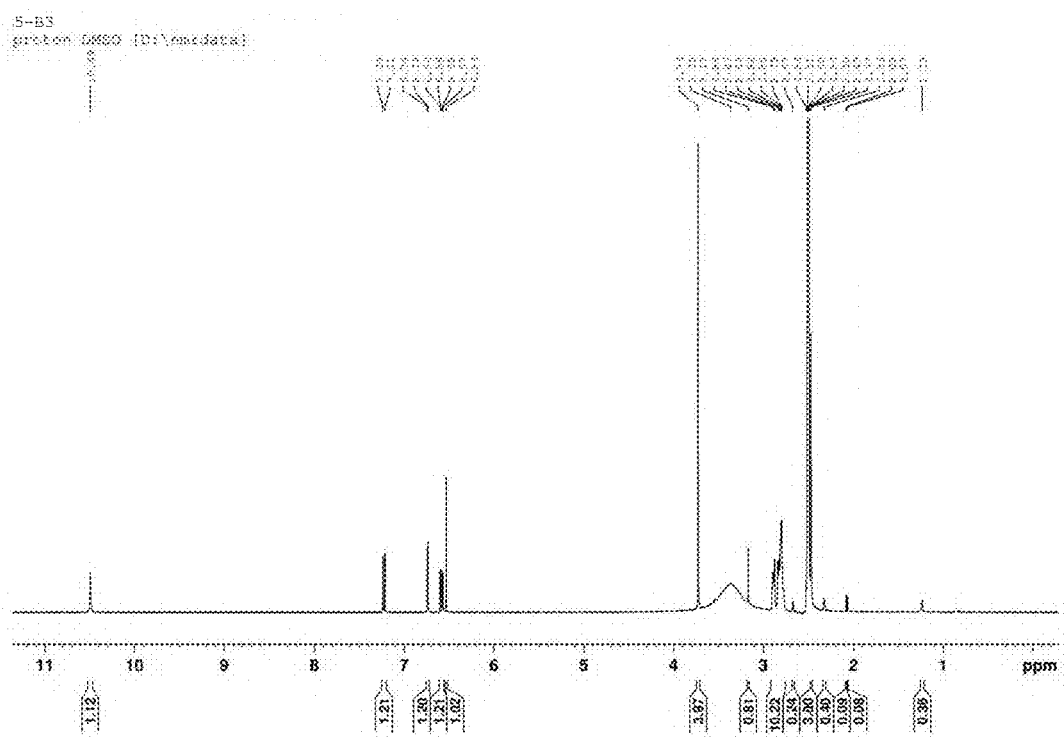
FIG. 86A depicts the $^1$H NMR spectrum of 5-B3 was acquired in DMSO-d, and calibrated to the non-deuterated solvent residual at 2.50 ppm API to Fumaric acid, 1.0 to 0.5. Residual solvents: MeOH: 2.4% w/w, MeCN: 0.3% w/w (acetone detected derived from NMR tube, as it was not used in the process: 0.2% w/w).
Figure 87:
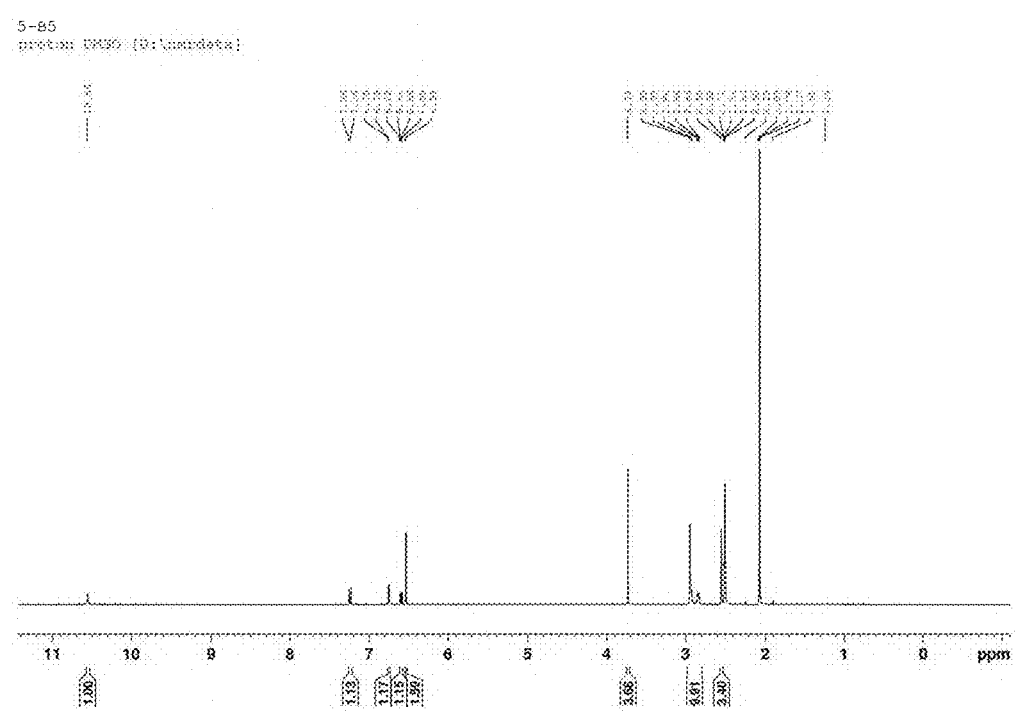
FIG. 87 depicts the $^1$H NMR spectrum of 5-B5 (Experiment Reference 5-Sample Reference B5) that was acquired in DMSO-d6 and calibrated to the non-deuterated solvent residual at 2.50 ppm API to Fumaric acid, 1.0 to 0.5.

On a separate note, the hemi-salt preparation was repeated by dissolving Tabernanthalog (native) (TBG Native, 50.6 mg) and fumaric acid (10.3 mg, 0.5 equiv) in methanol (1 ml, 20 vol), as more material was required for 5-B4 (Experiment Reference 5-Sample Reference B4).

b. Analytical Characterization Data $^1$H NMR $^1$H NMR spectrum of (5-O1) (Experiment Reference 5-Sample Reference O1) was acquired in DMSO-$d_6$ and calibrated to the non-deuterated solvent residual at 2.50 ppm API to Fumaric acid, 1.0 to 0.5 (FIG. 85). $^1$H NMR spectrum of 5-B1 (Experiment Reference 5-Sample Reference B1) was acquired in DMSO-$d_6$ and calibrated to the non-deuterated solvent residual at 2.50 ppm API to Fumaric acid, 1.0 to 0.5 (FIG. 86). 1H NMR spectrum of 5-B3 was acquired in DMSO-4 and calibrated to the non-deuterated solvent residual at 2.50 ppm API to Fumaric acid, 1.0 to 0.5. Residual solvents: MeOH: 2.4% w/w, MeCN: 0.3% w/w (acetone detected derived from NMR tube, as it was not used in the process: 0.2% w/w) (FIG. 86A). $^1$H NMR spectrum of 5-B5 (Experiment Reference 5-Sample Reference B5) was acquired in DMSO-d6 and calibrated to the non-deuterated solvent residual at 2.50 ppm API to Fumaric acid, 1.0 to 0.5 (FIG. 87).

DSC

Figure 87A:
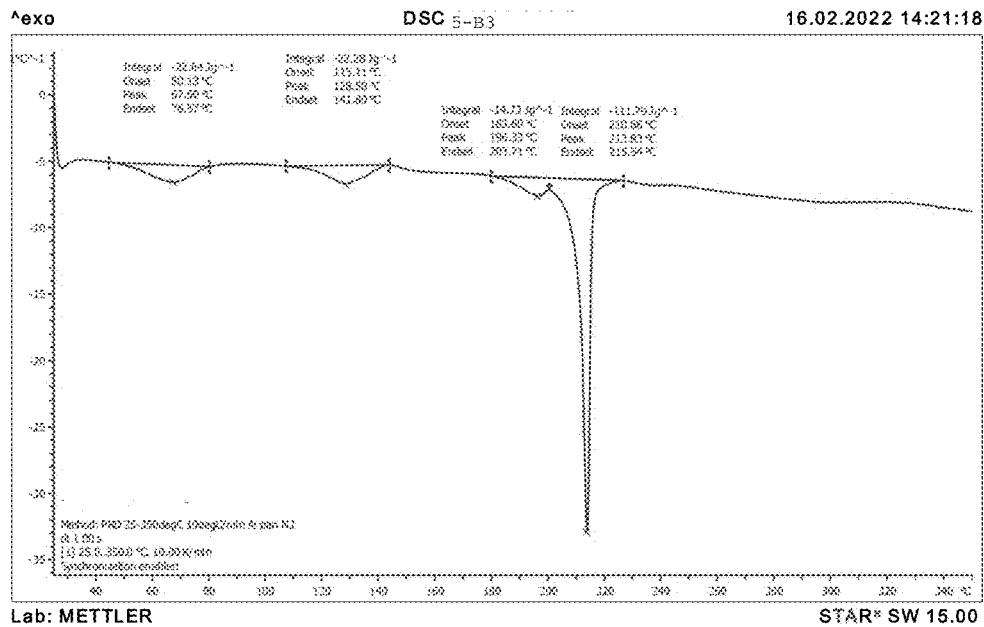
FIG. 87A depicts the DSC profile of 5-B3 (Experiment Reference 5-Sample Reference B3), analysis was acquired at a ramp rate of +10° C./minute.

DSC profile of 5-B3 (Experiment Reference 5-Sample Reference B3), analysis was acquired at a ramp rate of +10° C./minute (FIG. 87A).

Figure 88:
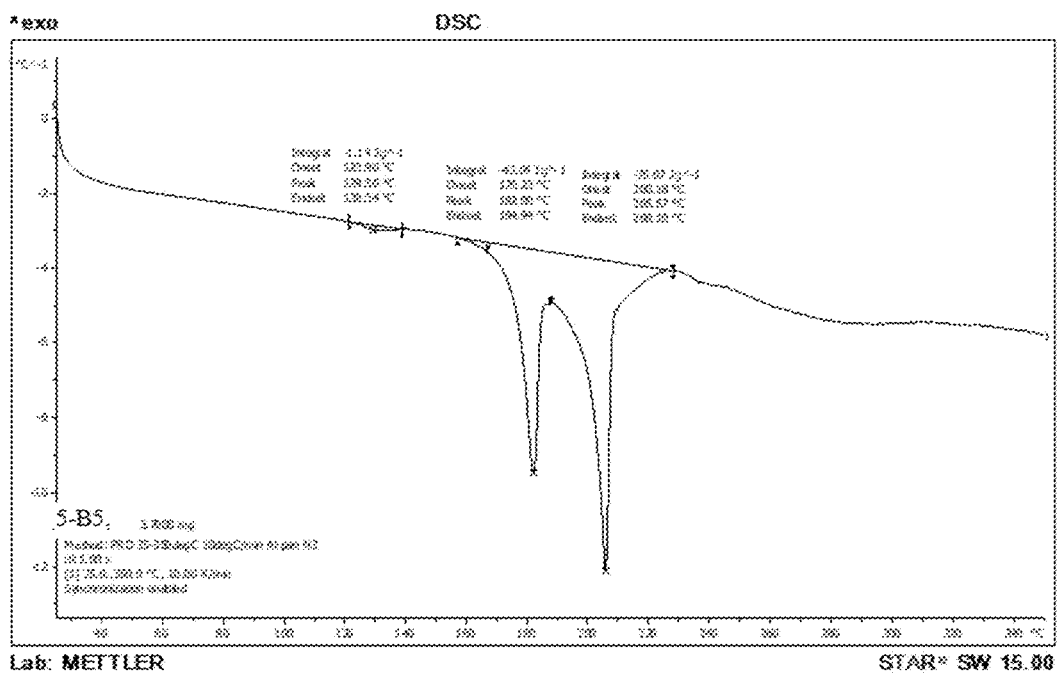
FIG. 88 depicts the DSC profile of 5-B5 (Experiment Reference 5-Sample Reference B5), analysis was acquired at a ramp rate of +10° C./minute.

DSC profile of 5-B5 (Experiment Reference 5-Sample Reference B5), analysis was acquired at a ramp rate of +10° C./minute (FIG. 88).

XRPD

Figure 89:
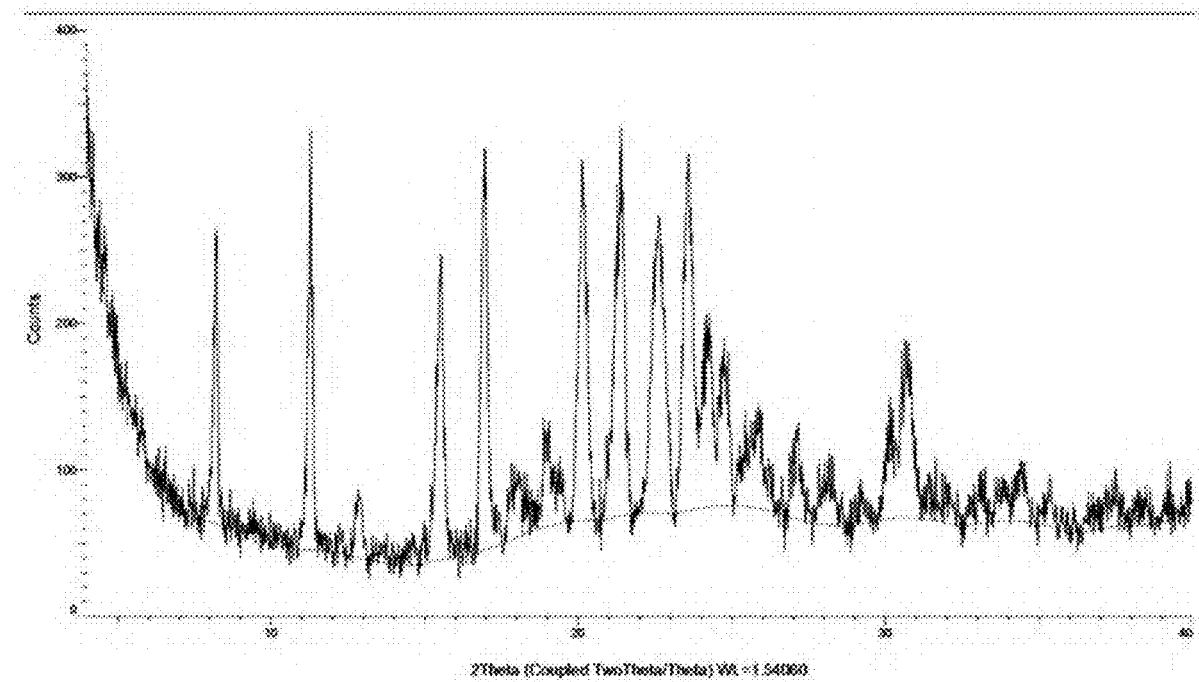
FIG. 89 depicts the XRPD profile of 5-B2 (Tabernanthalog·0.5Fumarate; Experiment Reference 5-Sample Reference B2).
Figure 89A:
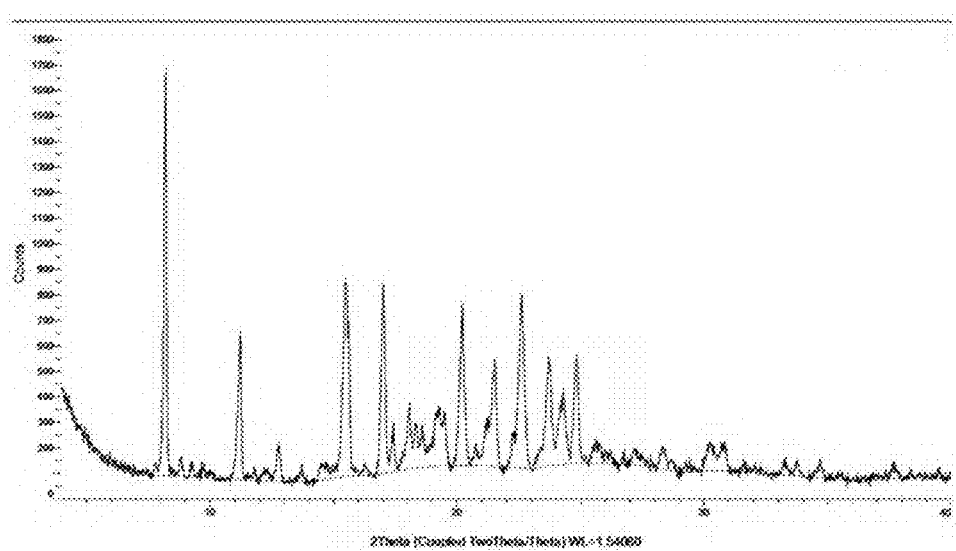
FIG. 89A depicts the XRPD profile of 5-B3 (Experiment Reference 5-Sample Reference B3).

XRPD profile of 5-B2 (Tabernanthalog·0.5Fumarate; Experiment Reference 5-Sample Reference B2) is presented in FIG. 89 and the peak angle data is provided in Table 32. XRPD profile of 5-B3 (Experiment Reference 5-Sample Reference B3) is presented in FIG. 89A and the peak angle data is provided in Table 32A.

Figure 90:
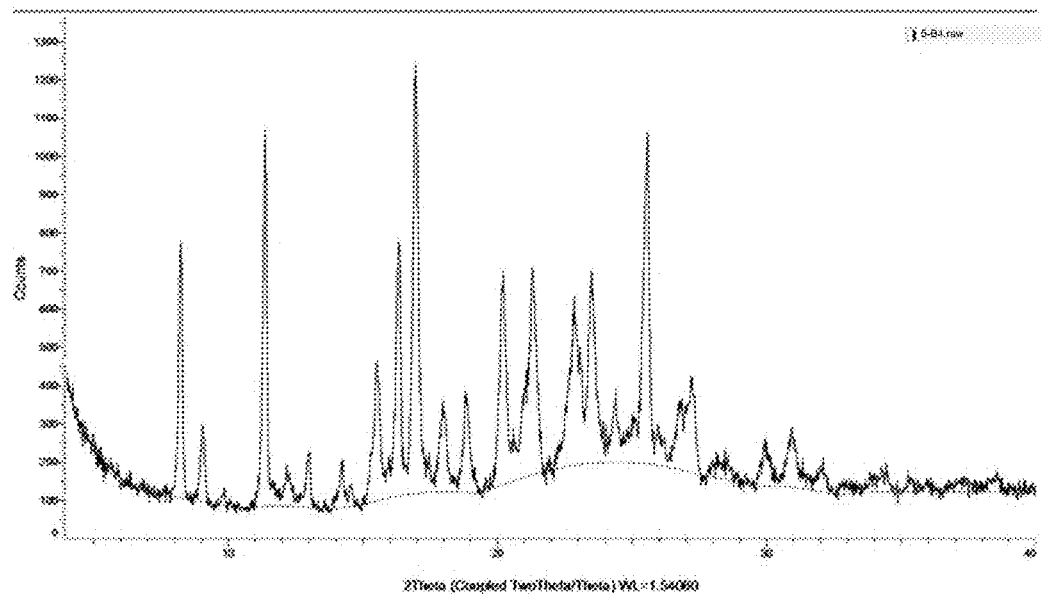
FIG. 90 depicts the XRPD profile of 5-B4 (Experiment Reference 5-Sample Reference B4).
Figure 91:
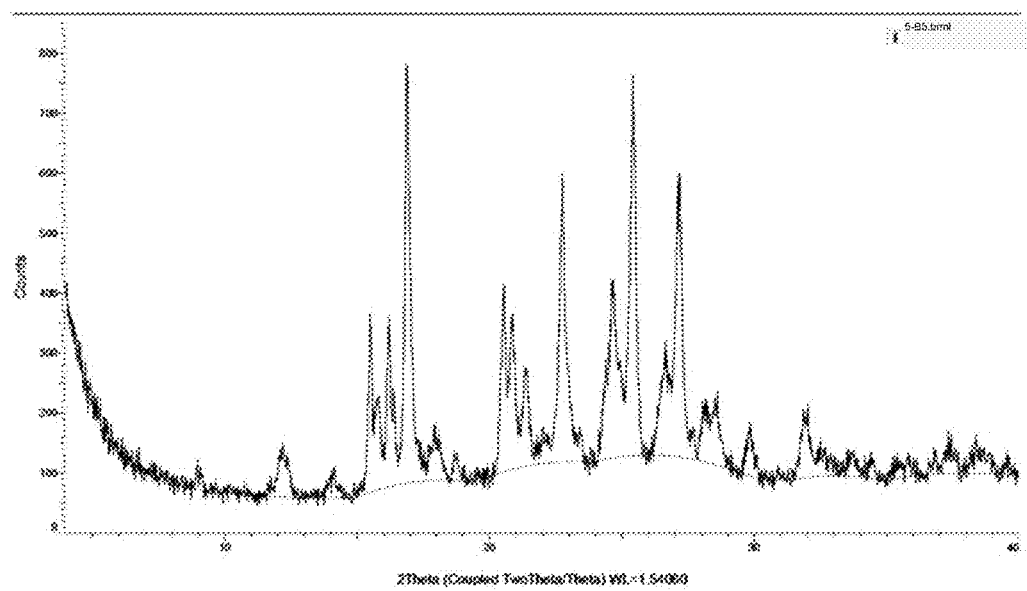
FIG. 91 depicts the XRPD profile of 5-B5 (Experiment Reference 5-Sample Reference B5).

XRPD profile of 5-B4 (Experiment Reference 5-Sample Reference B4) is presented in FIG. 90 and the peak angle data is provided in Table 33. XRPD profile of 5-B5 (Experiment Reference 5-Sample Reference B5) is presented in FIG. 91 and the peak angle data is provided in Table 34.

TABLE 32

Peak angle data of 5-B2 (Tabernanthalog·0.5Fumarate; Experiment Reference 5-Sample Reference B2)

| 2-θ (°) | d Value | Rel. Intensity (%) |
| --- | --- | --- |
| 8.2 | 10.78 | 66 |
| 11.3 | 7.84 | 91 |
| 12.8 | 6.89 | 16 |
| 15.5 | 5.71 | 74 |
| 17.0 | 5.23 | 100 |
| 17.8 | 4.97 | 15 |
| 18.0 | 4.91 | 15 |
| 19.0 | 4.67 | 17 |
| 18.9 | 4.70 | 18 |
| 19.4 | 4.57 | 16 |
| 20.2 | 4.40 | 90 |
| 21.4 | 4.15 | 89 |
| 22.6 | 3.93 | 74 |
| 23.6 | 3.77 | 90 |
| 24.2 | 3.67 | 43 |
| 24.7 | 3.60 | 40 |
| 25.9 | 3.44 | 20 |
| 27.1 | 3.29 | 20 |
| 30.2 | 2.96 | 21 |
| 30.7 | 2.91 | 37 |
| 34.4 | 2.61 | 12 |

TABLE 32A

Peak angle data of 5-B3 (Experiment Reference 5-Sample Reference B3)

| 8.2 | 10.79 | 100 |
| --- | --- | --- |
| 11.2 | 7.902 | 36 |
| 12.8 | 6.93 | 10 |

TABLE 32A-continued

Peak angle data of 5-B3 (Experiment Reference 5-Sample Reference B3)

| | | |
|---|---|---|
| 15.5 | 5.70 | 56 |
| 17.0 | 5.21 | 54 |
| 18.1 | 4.91 | 18 |
| 18.4 | 4.83 | 13 |
| 19.2 | 4.61 | 17 |
| 19.4 | 4.56 | 13 |
| 20.2 | 4.39 | 44 |
| 21.3 | 4.17 | 13 |
| 21.5 | 4.13 | 29 |
| 22.6 | 3.93 | 51 |
| 23.7 | 3.75 | 32 |
| 24.3 | 3.67 | 17 |
| 24.8 | 3.59 | 31 |

TABLE 33

Peak angle data of 5-B4 (Experiment Reference 5-Sample Reference B4)

| 2-θ (°) | d Value | Rel. Intensity (%) |
|---|---|---|
| 4.3 | 20.31 | 100 |
| 8.7 | 10.15 | 12 |
| 13.1 | 6.77 | 29 |
| 14.5 | 6.12 | 68 |
| 16.2 | 5.46 | 10 |
| 16.9 | 5.25 | 22 |
| 17.5 | 5.08 | 94 |
| 18.7 | 4.74 | 55 |
| 19.3 | 4.59 | 81 |
| 20.1 | 4.42 | 71 |
| 21.0 | 4.23 | 64 |
| 21.8 | 4.07 | 17 |
| 23.3 | 3.81 | 43 |
| 23.7 | 3.75 | 62 |
| 24.8 | 3.59 | 16 |
| 26.8 | 3.33 | 14 |
| 27.5 | 3.24 | 34 |
| 28.0 | 3.18 | 23 |
| 29.1 | 3.07 | 13 |
| 29.2 | 3.06 | 11 |
| 29.7 | 3.01 | 27 |
| 30.8 | 2.90 | 13 |
| 31.8 | 2.81 | 36 |
| 33.3 | 2.69 | 11 |
| 35.0 | 2.56 | 13 |
| 36.1 | 2.48 | 13 |
| 37.6 | 2.39 | 12 |
| 38.9 | 2.31 | 31 |

TABLE 34

Peak angle data of 5-B5 (Experiment Reference 5-Sample Reference B5)

| 2-θ (°) | d Value | Rel. Intensity (%) |
|---|---|---|
| 12.2 | 7.27 | 11 |
| 15.5 | 5.71 | 41 |
| 15.8 | 5.62 | 21 |
| 16.2 | 5.47 | 42 |
| 16.9 | 5.24 | 100 |
| 20.5 | 4.32 | 46 |
| 20.8 | 4.26 | 38 |
| 21.4 | 4.16 | 24 |
| 22.7 | 3.91 | 69 |
| 24.7 | 3.61 | 40 |
| 25.4 | 3.50 | 93 |
| 26.6 | 3.34 | 22 |
| 27.2 | 3.28 | 66 |
| 28.2 | 3.17 | 15 |
| 28.5 | 3.13 | 16 |
| 29.8 | 2.99 | 11 |
| 31.9 | 2.80 | 13 |

LC-MS

LC-MS report of (5-01) (Experiment Reference 5-Sample Reference O1) is provided in FIG. 92.

c. Conclusion

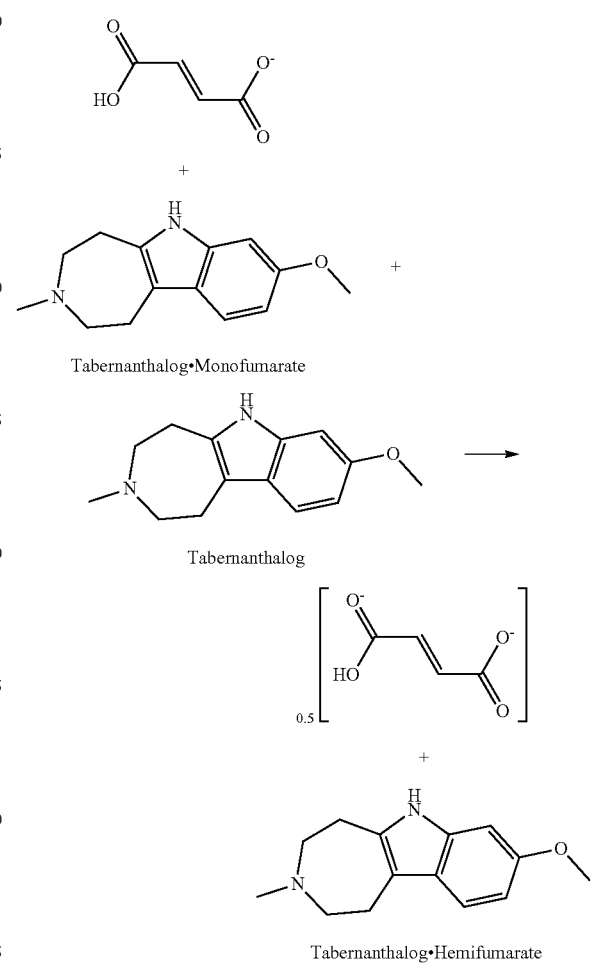

Reproportionation of Tabernanthalog Hemifumarate

Figure 93:
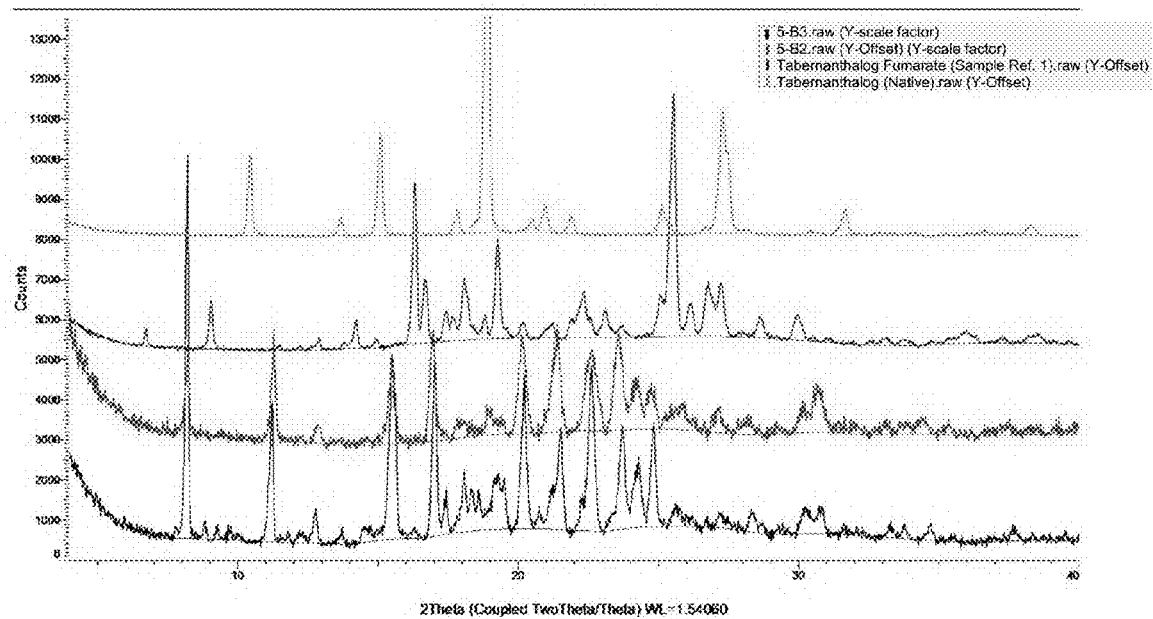
FIG. 93 relates to Experiment #1. It depicts the XRPD overlay of, from top to bottom, tabernanthalog (Native) (non-ionized,), tabernanthalog monofumarate (Sample Reference 1, Pattern #1) and tabernanthalog hemifumarate (Pattern #14, 5-B2, and 5-B3,). Y-scale factor was increased for 5-B2 and -B3, as the intensity of their diffractograms was low and difficult to compare with the reference powder diffraction patterns.

Expt. #1: at the 20 h time point, tabernanthalog hemifumarate, did not re-proportionate into the tabernanthalog monofumarate salt and fumaric acid; the output was consistent with tabernanthalog hemifumarate (FIG. 93).

Expt. #2: stirred for 48 h at 20° C., and 18 h at 40° C.; during this time the powder diffraction pattern of the product began to resemble Pattern #19 (a unary fumarate; 7-A1; Experiment Reference 7-Sample Reference A1); hence re-proportionation into the unary-fumarate appeared to be favored over the hemi-fumarate, under competitive suspension equilibration conditions (FIG. 94). Therefore, if regions of tabernanthalog hemifumarate are generated during the production of the tabernanthalog monofumarate salt, the former would be expected to revert to the latter during the ageing cycle.

vi. Suspension Equilibration at 20° C. (Experiment Reference 6) and 40° C. (Experiment Reference 7)

a. Experimental Procedure

Separate portions of the tabernanthalog monofumarate salt (Sample Reference 1, Pattern #1, ca 50 mg, 1.0 wt.) were charged to separate vessels. The appropriate solvents (e.g. 250 µl, 5.0 vol), were charged to the vessels and the mixtures were stirred for several days at their relevant temperatures e.g. 20 and 40° C. After this time the products were cooled, isolated by centrifugation, analyzed as wet pellet (suffix-1) by XRPD and dried under reduced pressure at 40° C. (suffix-2) and re-analyzed by XRPD and companion analyses for evidence of alternative crystalline forms.

b. Analytical Characterization Data

Suspension equilibration is a thermodynamic dwelling technique, designed to promote the evolution of the API into a more stable phase. The tabernanthalog monofumarate salt (Sample Reference 1, Pattern #1) was subjected to this technique at ambient temperature (20° C., Table 35) and at elevated temperature (40° C., Table 36), in a diverse range of solvents. The primary aim is to identify a stable, anhydrous monotropic form that is suitable for future development.

The products were isolated by centrifugation and analyzed wet by XRPD. After drying, the samples were reanalyzed.

TABLE 35

Summary table of suspension equilibration at 20° C.

| Experiment Reference-Sample Reference | Input reference | Input weight (mg) | Solvent | Key chemical functional groups | b.p. (° C.) | ICH Classes | Observations (t = 0 @ 20° C.) | Observations (t = 1 d @ 20° C.) | Observations (t = 7 d @ 20° C.) | XRPD (IPC, 6 d, wet) | XRPD (post oven dried) |
|---|---|---|---|---|---|---|---|---|---|---|---|
| 6-A | Tabernanthalog•Monofumarate (CAT8931) | 50.0 | Acetone | Symmetrical ketone | 56 | 3 | Suspension | Suspension | Suspension | Pattern #12 | Pattern #2b |
| 6-B | | 50.2 | Acetonitrile | Simple dipolar-aprotic nitrile | 82 | 2 | Suspension | Suspension | Suspension | Pattern #1 | Pattern #1 |
| 6-C | | 50.0 | tert-Butyl-methyl ether | Branched aliphatic methoxy ether | 55 | 3 | Suspension | Suspension | Suspension | Pattern #1 | Pattern #1 |
| 6-D | | 50.7 | Chlorobenzene | Aromatic halide | 131 | 2 | Suspension | Suspension | Suspension | Pattern #3 | Pattern #3 |
| 6-E | | 50.1 | Dichloromethane | Chlorinated hydrocarbon | 40 | 2 | Suspension | Suspension | Suspension | Pattern #4b | Pattern #4b |
| 6-F | | 50.8 | Ethanol | Linear aliphatic alcohol | 78 | 3 | Suspension | Suspension | Suspension | Pattern #5 | Pattern #4a |
| 6-G | | 50.4 | Ethyl acetate | Aliphatic ester | 75 | 3 | Suspension | Suspension | Suspension | Pattern #9 | Pattern #2b |
| 6-H | | 50.1 | Ethyl formate | Aldehyde aliphatic ester | 54 | 3 | Suspension | Suspension | Suspension | Pattern #2d | Pattern #2b |
| 6-I | | 50.4 | Heptane | Linear alkane | 98 | 3 | Suspension | Suspension | Suspension | Pattern #1 | Pattern #1 |
| 6-J | | 50.0 | Isopropyl acetate | Branched aliphatic ester | 87 | 3 | Suspension | Suspension | Suspension | Pattern #8 | Pattern #8 |
| 6-K | | 50.1 | Methanol | Simple aliphatic alcohol | 65 | 2 | Suspension | Suspension | Suspension | Pattern #4a | Pattern #4a |
| 6-L | | 50.8 | Methyl acetate | Simple aliphatic ester | 57 | 3 | Suspension | Suspension | Suspension | Pattern #13 | Pattern #2b |
| 6-M | | 50.0 | Methylethyl ketone | Asymmetric dialkyl ketone | 80 | 3 | Suspension | Suspension | Suspension | Pattern #1 | Pattern #1 |
| 6-N | | 50.4 | 2-Methyl THF | Asymmetric cyclic ether | 80 | # | Suspension | Suspension | Suspension | Pattern #7 | Pattern #1 |
| 6-O | | 50.1 | Nitromethane | Dipolar aprotic nitro | 100 | 2 | Suspension | Suspension | Suspension | Pattern #1 | Pattern #4b |
| 6-P | | 50.4 | 2-Propanol | Branched aliphatic alcohol | 83 | 3 | Suspension | Suspension | Suspension | Pattern #10 | Pattern #4a |
| 6-Q | | 50.3 | Tetrahydrofuran | Symmetric cyclic ether | 66 | 2 | Suspension | Suspension | Suspension | Pattern #11 | Pattern #2b |
| 6-R | | 50.2 | Toluene | Alkyl aromatic hydrocarbon | 111 | 2 | Suspension | Suspension | Suspension | Pattern #3 | Pattern #3 |
| 6-S | | 50.7 | Water | Dihydrogen oxide | 100 | # | Suspension | Suspension | Suspension | Pattern #6a | Pattern #6a |

TABLE 36

Summary table of suspension equilibration at 40° C.

| Experiment Reference-Sample Reference | Input reference | Input weight (mg) | Solvent | Key chemical functional groups | b.p. (° C.) | ICH Classes | Observations (t = 0 @ 40° C.) | Observations (t= 1 d @ 40° C.) | Observations t = 7 d @ 40° C.) | XRPD (6 d, wet) | XRPD (post oven dried) |
|---|---|---|---|---|---|---|---|---|---|---|---|
| 7-A | Tabernanthalog.fumarate (CAT8931) | 50.0 | Acetone | Symmetrical ketone | 56 | 3 | Suspension | Suspension | Suspension | Pattern #19 | Pattern #19 |
| 7-B | | 50.2 | Acetonitrile | Simple dipolar-aprotic nitrile | 82 | 2 | Suspension | Suspension | Suspension | Pattern #2a | Pattern #2a |
| 7-C | | 50.0 | tert-Butyl methyl ether | Branched aliphatic methoxy ether | 55 | 3 | Suspension | Feint suspension | Suspension | Pattern #1 | Pattern #1 |
| 7-D | | 50.7 | Chlorobenzene | Aromatic halide | 131 | 2 | Suspension | Suspension | Suspension | Pattern #3 | Pattern #1 |
| 7-E | | 50.1 | Dichloromethane | Chlorinated hydrocarbon | 40 | 2 | Suspension | Suspension | Suspension | Not analysed | Pattern #1 |
| 7-F | | 50.8 | Ethanol | Linear aliphatic alcohol | 78 | 3 | Suspension | Suspension | Suspension | Pattern #5 | Insufficient material |
| 7-G | | 50.4 | Ethyl acetate | Aliphatic ester | 75 | 3 | Suspension | Suspension | Suspension | Pattern #9 | Pattern #1 |
| 7-H | | 50.1 | Ethyl formate | Aldehyde aliphatic ester | 54 | 3 | Suspension | Suspension | Suspension | Pattern #2d | Pattern #2b |
| 7-I | | 50.4 | Heptane | Linear alkane | 98 | 3 | Suspension | Suspension | Suspension | Pattern #1 | Pattern #1 |
| 7-J | | 50.0 | Isopropyl acetate | Branched aliphatic ester | 87 | 3 | Suspension | Suspension | Suspension | Pattern #2a | Pattern #2a |
| 7-K | | 50.1 | Methanol | Simple aliphatic alcohol | 65 | 2 | Suspension | Partial dissolution | Suspension | Insufficient material | Insufficient material |
| 7-L | | 50.8 | Methyl acetate | Simple aliphatic ester | 57 | 3 | Suspension | Suspension | Suspension | Pattern #13 | Pattern #1 |
| 7-M | | 50.0 | Methylethyl ketone | Asymmetric dialkyl ketone | 80 | 3 | Suspension | Suspension | Suspension | Pattern #2a | Pattern #2a |
| 7-N | | 50.4 | 2-Methyl THF | Asymmetric cyclic ether | 80 | # | Suspension | Suspension | Suspension | Pattern #7 | Pattern #1 |
| 7-O | | 50.1 | Nitromethane | Dipolar aprotic nitro | 100 | 2 | Suspension | Suspension | Suspension | Pattern #17 | Pattern #2a |
| 7-P | | 50.4 | 2-Propanol | Branched aliphatic alcohol | 83 | 3 | Suspension | Suspension | Suspension | Pattern #10 | Pattern #21 |
| 7-Q | | 50.3 | Tetrahydrofuran | Symmetric cyclic ether | 66 | 2 | Suspension | Sticky Solid | Suspension | Pattern #11 | Insufficient material |
| 7-R | | 50.2 | Toluene | Alkyl aromatic hydrocarbon | 111 | 2 | Suspension | Suspension | Suspension | Pattern #1 | Insufficient material |
| 7-S | | 50.7 | Water | Dihydrogen oxide | 100 | # | Suspension | Partial dissolution | Suspension | Pattern #8 (amorphised) | Insufficient material |

XRPD

The XRPD data is provided in FIGS. 95-145 and Tables 37-87. XRPD diffractograms not shown are reported on the characterization data section.

TABLE 37

Peak angle data of 6-A2 (Experiment Reference 6-Sample Reference A2) (Pattern #2b)

| 2-θ (°) | d Value | Rel. Intensity (%) |
|---|---|---|
| 9.0 | 9.78 | 27 |
| 14.2 | 6.24 | 12 |
| 15.5 | 5.69 | 16 |
| 16.3 | 5.44 | 82 |
| 17.4 | 5.09 | 17 |
| 18.0 | 4.91 | 28 |
| 18.8 | 4.72 | 14 |
| 22.3 | 3.98 | 21 |
| 22.5 | 3.95 | 23 |
| 24.7 | 3.60 | 17 |
| 25.0 | 3.56 | 21 |

TABLE 37-continued

Peak angle data of 6-A2 (Experiment Reference 6-Sample Reference A2) (Pattern #2b)

| 2-θ (°) | d Value | Rel. Intensity (%) |
|---|---|---|
| 25.5 | 3.49 | 100 |
| 26.8 | 3.33 | 26 |

TABLE 38

Peak angle data of 6-B1 (Experiment Reference 6-Sample Reference B1) (Pattern #1)

| 2-θ (°) | d Value | Rel. Intensity (%) |
|---|---|---|
| 6.8 | 13.03 | 23 |
| 9.1 | 9.70 | 32 |
| 13.0 | 6.83 | 11 |
| 14.3 | 6.20 | 13 |
| 16.4 | 5.41 | 84 |
| 16.8 | 5.27 | 54 |
| 17.5 | 5.05 | 16 |

TABLE 38-continued

Peak angle data of 6-B1 (Experiment Reference 6-Sample Reference B1) (Pattern #1)

| 2-θ (°) | d Value | Rel. Intensity (%) |
|---|---|---|
| 17.8 | 4.97 | 22 |
| 18.2 | 4.87 | 32 |
| 19.4 | 4.57 | 66 |
| 20.3 | 4.37 | 18 |
| 21.4 | 4.16 | 14 |
| 22.3 | 3.97 | 23 |
| 22.4 | 3.97 | 27 |
| 23.2 | 3.83 | 17 |
| 25.3 | 3.51 | 25 |
| 25.6 | 3.48 | 100 |
| 26.3 | 3.39 | 19 |
| 26.9 | 3.31 | 20 |
| 27.3 | 3.26 | 27 |

TABLE 39

Peak angle data of 6-B2 (Experiment Reference 6-Sample Reference B2) (Pattern #1)

| 2-θ (°) | d Value | Rel. Intensity (%) |
|---|---|---|
| 6.7 | 13.14 | 16 |
| 9.1 | 9.75 | 22 |
| 12.9 | 6.86 | 10 |
| 14.2 | 6.22 | 11 |
| 16.3 | 5.43 | 69 |
| 16.7 | 5.29 | 45 |
| 17.5 | 5.07 | 14 |
| 17.8 | 4.99 | 20 |
| 18.1 | 4.89 | 27 |
| 19.3 | 4.59 | 58 |
| 20.2 | 4.39 | 15 |
| 21.3 | 4.17 | 12 |
| 22.3 | 3.98 | 27 |
| 23.1 | 3.84 | 16 |
| 25.5 | 3.48 | 100 |
| 26.2 | 3.40 | 17 |
| 26.8 | 3.32 | 20 |
| 27.2 | 3.27 | 26 |

TABLE 40

Peak angle data of 6-C1 (Experiment Reference 6-Sample Reference C1) (Pattern #1)

| 2-θ (°) | d Value | Rel. Intensity (%) |
|---|---|---|
| 6.8 | 12.93 | 15 |
| 9.2 | 9.63 | 23 |
| 13.0 | 6.81 | 10 |
| 14.3 | 6.17 | 11 |
| 16.4 | 5.39 | 72 |
| 16.9 | 5.25 | 44 |
| 17.6 | 5.02 | 20 |
| 17.9 | 4.94 | 23 |
| 18.2 | 4.86 | 34 |
| 19.4 | 4.56 | 56 |
| 20.3 | 4.37 | 12 |
| 21.4 | 4.15 | 11 |
| 22.5 | 3.96 | 28 |
| 23.3 | 3.82 | 14 |
| 25.7 | 3.47 | 100 |
| 26.3 | 3.38 | 20 |
| 27.0 | 3.29 | 25 |
| 27.3 | 3.26 | 27 |

TABLE 41

Peak angle data of 6-C2 (Experiment Reference 6-Sample ReferenceC2) (Pattern #1)

| 2-θ (°) | d Value | Rel. Intensity (%) |
|---|---|---|
| 6.7 | 13.11 | 17 |
| 9.1 | 9.74 | 30 |
| 12.9 | 6.85 | 12 |
| 14.3 | 6.21 | 13 |
| 16.3 | 5.42 | 84 |
| 16.8 | 5.28 | 52 |
| 17.5 | 5.06 | 16 |
| 17.8 | 4.98 | 24 |
| 18.2 | 4.88 | 32 |
| 18.9 | 4.70 | 10 |
| 19.3 | 4.59 | 59 |
| 20.2 | 4.39 | 14 |
| 21.3 | 4.17 | 13 |
| 22.3 | 3.98 | 28 |
| 22.5 | 3.94 | 11 |
| 23.1 | 3.84 | 14 |
| 25.4 | 3.51 | 39 |
| 25.6 | 3.48 | 100 |
| 26.2 | 3.40 | 19 |
| 26.9 | 3.32 | 23 |
| 27.3 | 3.27 | 25 |

TABLE 42

Peak angle data of 6-D1 (Experiment Reference 6-Sample Reference D1) (Pattern #3)

| 2-θ (°) | d Value | Rel. Intensity (%) |
|---|---|---|
| 8.5 | 10.42 | 34 |
| 9.1 | 9.71 | 53 |
| 9.8 | 9.03 | 16 |
| 11.3 | 7.83 | 25 |
| 12.6 | 7.02 | 24 |
| 14.4 | 6.16 | 27 |
| 16.4 | 5.41 | 92 |
| 16.7 | 5.30 | 100 |
| 17.0 | 5.22 | 45 |
| 17.4 | 5.08 | 18 |
| 18.1 | 4.90 | 25 |
| 18.8 | 4.70 | 36 |
| 19.5 | 4.56 | 13 |
| 20.1 | 4.41 | 47 |
| 21.6 | 4.12 | 12 |
| 22.4 | 3.97 | 40 |
| 24.7 | 3.60 | 12 |
| 25.1 | 3.55 | 21 |
| 25.5 | 3.49 | 90 |
| 26.1 | 3.41 | 42 |
| 26.8 | 3.32 | 36 |
| 29.9 | 2.99 | 13 |
| 33.2 | 2.70 | 12 |
| 39.6 | 2.27 | 11 |

TABLE 43

Peak angle data of 6-D2 (Experiment Reference 6-Sample Reference D2) (Pattern #3)

| 2-θ (°) | d Value | Rel. Intensity (%) |
|---|---|---|
| 8.4 | 10.47 | 19 |
| 9.1 | 9.76 | 28 |
| 11.2 | 7.88 | 14 |
| 12.5 | 7.06 | 16 |
| 14.3 | 6.19 | 22 |
| 16.3 | 5.43 | 86 |
| 16.6 | 5.32 | 79 |
| 16.9 | 5.24 | 27 |
| 17.4 | 5.09 | 14 |

TABLE 43-continued

Peak angle data of 6-D2 (Experiment Reference 6-Sample Reference D2)
(Pattern #3)

| 2-θ (°) | d Value | Rel. Intensity (%) |
|---|---|---|
| 18.0 | 4.91 | 19 |
| 18.8 | 4.72 | 33 |
| 19.4 | 4.57 | 11 |
| 20.1 | 4.42 | 49 |
| 22.3 | 3.98 | 49 |
| 22.5 | 3.95 | 30 |
| 22.9 | 3.89 | 14 |
| 23.1 | 3.85 | 10 |
| 24.8 | 3.59 | 15 |
| 25.1 | 3.55 | 23 |
| 25.5 | 3.49 | 100 |
| 26.1 | 3.41 | 44 |
| 26.8 | 3.33 | 34 |
| 27.2 | 3.28 | 11 |
| 29.9 | 2.99 | 12 |

TABLE 44

Peak angle data of 6-E1 (Experiment Reference 6-Sample Reference E1)
(Pattern #4b)

| 2-θ (°) | d Value | Rel. Intensity (%) |
|---|---|---|
| 9.3 | 9.51 | 28 |
| 14.5 | 6.12 | 12 |
| 15.7 | 5.63 | 10 |
| 16.6 | 5.35 | 81 |
| 17.0 | 5.21 | 22 |
| 17.3 | 5.11 | 17 |
| 17.7 | 5.00 | 13 |
| 18.3 | 4.84 | 26 |
| 19.5 | 4.54 | 32 |
| 20.4 | 4.34 | 13 |
| 21.5 | 4.12 | 18 |
| 22.3 | 3.98 | 14 |
| 22.6 | 3.94 | 21 |
| 23.4 | 3.80 | 11 |
| 23.9 | 3.72 | 13 |
| 25.8 | 3.45 | 100 |
| 26.4 | 3.38 | 16 |
| 27.1 | 3.29 | 24 |
| 27.5 | 3.25 | 20 |
| 30.2 | 2.95 | 14 |

TABLE 45

Peak angle data of 6-E2 (Experiment Reference 6-Sample Reference E2)
(Pattern #4b)

| 2-θ (°) | d Value | Rel. Intensity (%) |
|---|---|---|
| 6.7 | 13.14 | 11 |
| 8.3 | 10.69 | 37 |
| 9.1 | 9.76 | 30 |
| 11.2 | 7.87 | 17 |
| 14.2 | 6.23 | 12 |
| 15.6 | 5.67 | 17 |
| 16.3 | 5.43 | 78 |
| 16.7 | 5.29 | 20 |
| 17.2 | 5.14 | 21 |
| 18.1 | 4.90 | 22 |
| 18.8 | 4.71 | 11 |
| 19.3 | 4.60 | 26 |
| 20.3 | 4.37 | 13 |
| 21.4 | 4.14 | 16 |
| 22.3 | 3.98 | 17 |
| 22.6 | 3.93 | 13 |

TABLE 45-continued

Peak angle data of 6-E2 (Experiment Reference 6-Sample Reference E2)
(Pattern #4b)

| 2-θ (°) | d Value | Rel. Intensity (%) |
|---|---|---|
| 23.8 | 3.74 | 17 |
| 25.1 | 3.54 | 13 |
| 25.5 | 3.49 | 100 |
| 26.8 | 3.33 | 20 |
| 27.2 | 3.27 | 16 |

TABLE 46

Peak angle data of 6-F1 (Experiment Reference 6-Sample Reference F1)
(Pattern #5)

| 2-θ (°) | d Value | Rel. Intensity (%) |
|---|---|---|
| 8.3 | 10.70 | 47 |
| 9.1 | 9.71 | 37 |
| 11.1 | 7.98 | 46 |
| 14.3 | 6.21 | 12 |
| 15.4 | 5.75 | 39 |
| 16.3 | 5.42 | 64 |
| 16.9 | 5.23 | 58 |
| 17.4 | 5.09 | 10 |
| 18.0 | 4.91 | 18 |
| 19.1 | 4.64 | 16 |
| 20.0 | 4.44 | 40 |
| 21.4 | 4.15 | 57 |
| 22.5 | 3.95 | 35 |
| 23.6 | 3.77 | 44 |
| 23.9 | 3.72 | 29 |
| 25.0 | 3.55 | 18 |
| 25.5 | 3.49 | 100 |
| 26.8 | 3.32 | 24 |
| 30.1 | 2.96 | 21 |

TABLE 47

Peak angle data of 6-F2 (Experiment Reference 6-Sample Reference F2)
(Pattern #4a)

| 2-θ (°) | d Value | Rel. Intensity (%) |
|---|---|---|
| 8.2 | 10.72 | 90 |
| 9.1 | 9.75 | 34 |
| 11.3 | 7.84 | 50 |
| 12.7 | 6.95 | 20 |
| 14.2 | 6.22 | 14 |
| 15.7 | 5.65 | 31 |
| 15.7 | 5.66 | 27 |
| 16.3 | 5.43 | 88 |
| 17.2 | 5.16 | 46 |
| 18.1 | 4.91 | 23 |
| 18.9 | 4.70 | 12 |
| 19.2 | 4.62 | 17 |
| 20.4 | 4.35 | 34 |
| 21.6 | 4.12 | 40 |
| 22.4 | 3.97 | 13 |
| 22.7 | 3.92 | 25 |
| 23.9 | 3.73 | 35 |
| 25.1 | 3.54 | 15 |
| 25.6 | 3.48 | 100 |
| 26.8 | 3.32 | 24 |
| 27.2 | 3.27 | 12 |
| 29.9 | 2.98 | 11 |

TABLE 48

Peak angle data of 6-H1 (Experiment Reference 6-Sample Reference H1) (Pattern #2d)

| 2-θ (°) | d Value | Rel. Intensity (%) |
|---|---|---|
| 7.9 | 11.24 | 15 |
| 9.1 | 9.68 | 31 |
| 14.3 | 6.20 | 16 |
| 16.3 | 5.43 | 91 |
| 17.6 | 5.03 | 21 |
| 18.1 | 4.89 | 20 |
| 18.9 | 4.70 | 11 |
| 20.0 | 4.44 | 32 |
| 21.2 | 4.18 | 22 |
| 22.2 | 4.00 | 45 |
| 25.3 | 3.52 | 34 |
| 25.6 | 3.48 | 100 |
| 26.0 | 3.42 | 38 |
| 26.9 | 3.31 | 26 |
| 27.0 | 3.30 | 19 |

TABLE 49

Peak angle data of 6-H2 (Experiment Reference 6-Sample Reference H2) (Pattern #2b)

| 2-θ (°) | d Value | Rel. Intensity (%) |
|---|---|---|
| 9.0 | 9.80 | 20 |
| 14.2 | 6.24 | 12 |
| 15.6 | 5.69 | 10 |
| 16.3 | 5.45 | 74 |
| 17.4 | 5.09 | 13 |
| 18.0 | 4.92 | 22 |
| 22.1 | 4.01 | 17 |
| 22.5 | 3.94 | 16 |
| 25.1 | 3.55 | 18 |
| 25.5 | 3.49 | 100 |
| 26.0 | 3.43 | 10 |
| 26.8 | 3.33 | 24 |
| 27.2 | 3.28 | 13 |

TABLE 50

Peak angle data of 6-I1 (Experiment Reference 6-Sample Reference I1) (Pattern #1)

| 2-θ (°) | d Value | Rel. Intensity (%) |
|---|---|---|
| 6.8 | 12.97 | 11 |
| 9.1 | 9.68 | 20 |
| 14.3 | 6.19 | 11 |
| 16.4 | 5.40 | 66 |
| 16.8 | 5.26 | 33 |
| 17.6 | 5.03 | 16 |
| 18.2 | 4.87 | 29 |
| 18.9 | 4.68 | 10 |
| 19.4 | 4.57 | 48 |
| 20.3 | 4.37 | 11 |
| 22.3 | 3.98 | 21 |
| 22.4 | 3.96 | 26 |
| 23.2 | 3.83 | 14 |
| 25.6 | 3.47 | 100 |
| 26.3 | 3.39 | 17 |
| 26.9 | 3.31 | 22 |
| 27.3 | 3.26 | 24 |

TABLE 51

Peak angle data of 6-I2 (Experiment Reference 6-Sample Reference I2) (Pattern #1)

| 2-θ (°) | d Value | Rel. Intensity (%) |
|---|---|---|
| 6.7 | 13.17 | 17 |
| 9.1 | 9.76 | 25 |
| 14.2 | 6.23 | 11 |
| 16.3 | 5.43 | 74 |
| 16.7 | 5.29 | 38 |
| 17.5 | 5.07 | 13 |
| 17.8 | 4.99 | 17 |
| 18.1 | 4.89 | 28 |
| 19.3 | 4.59 | 49 |
| 22.3 | 3.98 | 22 |
| 22.5 | 3.95 | 12 |
| 23.1 | 3.84 | 14 |
| 25.2 | 3.53 | 15 |
| 25.5 | 3.49 | 100 |
| 26.2 | 3.40 | 13 |
| 26.8 | 3.32 | 21 |
| 27.2 | 3.27 | 23 |

TABLE 52

Peak angle data of 6-J1 (Experiment Reference 6-Sample Reference J1) (Pattern #8)

| 2-θ (°) | d Value | Rel. Intensity (%) |
|---|---|---|
| 7.6 | 11.59 | 52 |
| 9.1 | 9.70 | 24 |
| 12.2 | 7.24 | 14 |
| 15.6 | 5.68 | 11 |
| 15.9 | 5.57 | 100 |
| 16.4 | 5.41 | 81 |
| 18.1 | 4.91 | 17 |
| 19.1 | 4.64 | 34 |
| 20.6 | 4.30 | 54 |
| 20.8 | 4.27 | 33 |
| 21.9 | 4.05 | 13 |
| 22.6 | 3.92 | 12 |
| 24.3 | 3.66 | 72 |
| 25.0 | 3.56 | 16 |
| 25.6 | 3.48 | 73 |
| 26.9 | 3.32 | 17 |
| 27.3 | 3.27 | 13 |

TABLE 53

Peak angle data of 6-K1 (Experiment Reference 6-Sample Reference K1) (Pattern #4a)

| 2-θ (°) | d Value | Rel. Intensity (%) |
|---|---|---|
| 8.2 | 10.74 | 60 |
| 9.1 | 9.74 | 37 |
| 11.3 | 7.85 | 68 |
| 12.8 | 6.90 | 17 |
| 14.2 | 6.22 | 14 |
| 15.6 | 5.69 | 40 |
| 16.3 | 5.43 | 88 |
| 17.0 | 5.20 | 57 |
| 17.4 | 5.09 | 11 |
| 18.0 | 4.91 | 19 |
| 19.1 | 4.65 | 20 |
| 20.2 | 4.38 | 47 |
| 21.3 | 4.17 | 18 |
| 21.5 | 4.14 | 55 |
| 22.6 | 3.93 | 29 |
| 23.7 | 3.75 | 52 |
| 24.4 | 3.65 | 13 |
| 25.0 | 3.55 | 20 |
| 25.5 | 3.49 | 100 |
| 26.8 | 3.33 | 20 |

TABLE 53-continued

Peak angle data of 6-K1 (Experiment Reference 6-Sample Reference K1)
(Pattern #4a)

| 2-θ (°) | d Value | Rel. Intensity (%) |
|---|---|---|
| 27.2 | 3.28 | 16 |
| 30.8 | 2.90 | 12 |

TABLE 54

Peak angle data of 6-L1 (Experiment Reference 6-Sample Reference L1)
(Pattern #13)

| 2-θ (°) | d Value | Rel. Intensity (%) |
|---|---|---|
| 8.1 | 10.91 | 28 |
| 18.1 | 4.89 | 18 |
| 18.9 | 4.69 | 10 |
| 19.7 | 4.50 | 42 |
| 20.9 | 4.24 | 19 |
| 21.9 | 4.05 | 27 |
| 22.7 | 3.91 | 16 |
| 23.4 | 3.81 | 12 |
| 24.5 | 3.64 | 12 |
| 25.0 | 3.56 | 59 |
| 25.6 | 3.47 | 100 |
| 9.1 | 9.68 | 23 |
| 26.9 | 3.31 | 19 |
| 28.7 | 3.11 | 12 |
| 10.5 | 8.41 | 19 |
| 14.3 | 6.19 | 11 |
| 16.0 | 5.53 | 78 |
| 16.4 | 5.41 | 75 |
| 17.5 | 5.07 | 37 |

TABLE 55

Peak angle data of 6-L2 (Experiment Reference 6-Sample Reference L2)
(Pattern #2b)

| 2-θ (°) | d Value | Rel. Intensity (%) |
|---|---|---|
| 9.1 | 9.75 | 41 |
| 9.8 | 8.98 | 14 |
| 14.2 | 6.21 | 15 |
| 15.6 | 5.69 | 20 |
| 16.3 | 5.42 | 92 |
| 17.1 | 5.18 | 24 |
| 17.4 | 5.09 | 22 |
| 18.1 | 4.90 | 32 |
| 18.4 | 4.83 | 11 |
| 18.8 | 4.71 | 12 |
| 19.5 | 4.54 | 11 |
| 21.0 | 4.23 | 11 |
| 22.4 | 3.97 | 20 |
| 22.6 | 3.94 | 19 |
| 24.7 | 3.60 | 40 |
| 25.6 | 3.48 | 100 |
| 26.8 | 3.32 | 25 |
| 27.2 | 3.27 | 10 |

TABLE 56

Peak angle data of 6-M1 (Experiment Reference 6-Sample Reference M1)
(Pattern #1)

| 2-θ (°) | d Value | Rel. Intensity (%) |
|---|---|---|
| 8.1 | 10.91 | 28 |
| 9.1 | 9.68 | 23 |
| 10.5 | 8.41 | 19 |
| 14.3 | 6.19 | 11 |
| 16.0 | 5.53 | 78 |

TABLE 56-continued

Peak angle data of 6-M1 (Experiment Reference 6-Sample Reference M1)
(Pattern #1)

| 2-θ (°) | d Value | Rel. Intensity (%) |
|---|---|---|
| 16.4 | 5.41 | 75 |
| 17.5 | 5.07 | 37 |
| 18.1 | 4.89 | 18 |
| 18.9 | 4.69 | 10 |
| 19.7 | 4.50 | 42 |
| 20.9 | 4.24 | 19 |
| 21.9 | 4.05 | 27 |
| 22.7 | 3.91 | 16 |
| 23.4 | 3.81 | 12 |
| 24.5 | 3.64 | 12 |
| 25.0 | 3.56 | 59 |
| 25.6 | 3.47 | 100 |
| 26.9 | 3.31 | 19 |
| 28.7 | 3.11 | 12 |

TABLE 57

Peak angle data of 6-M2 (Experiment Reference 6-Sample Reference M2)
(Pattern #1)

| 2-θ (°) | d Value | Rel. Intensity (%) |
|---|---|---|
| 6.7 | 13.15 | 16 |
| 9.0 | 9.77 | 28 |
| 14.2 | 6.23 | 10 |
| 16.3 | 5.43 | 77 |
| 16.8 | 5.28 | 49 |
| 17.5 | 5.07 | 14 |
| 17.8 | 4.99 | 19 |
| 18.1 | 4.89 | 25 |
| 19.3 | 4.59 | 48 |
| 20.2 | 4.39 | 13 |
| 22.3 | 3.98 | 22 |
| 23.1 | 3.84 | 12 |
| 24.6 | 3.61 | 20 |
| 25.2 | 3.53 | 14 |
| 25.5 | 3.48 | 100 |
| 26.2 | 3.40 | 14 |
| 26.8 | 3.32 | 20 |
| 27.3 | 3.27 | 20 |

TABLE 58

Peak angle data of 6-N2 (Experiment Reference 6-Sample Reference N2)
(Pattern #1)

| 2-θ (°) | d Value | Rel. Intensity (%) |
|---|---|---|
| 9.0 | 9.78 | 21 |
| 14.2 | 6.23 | 12 |
| 16.3 | 5.44 | 69 |
| 16.7 | 5.30 | 35 |
| 17.4 | 5.08 | 11 |
| 17.8 | 4.98 | 14 |
| 18.1 | 4.90 | 20 |
| 19.3 | 4.60 | 37 |
| 22.3 | 3.99 | 24 |
| 22.4 | 3.97 | 23 |
| 23.1 | 3.85 | 16 |
| 24.6 | 3.61 | 12 |
| 25.5 | 3.49 | 100 |
| 26.2 | 3.40 | 13 |
| 26.8 | 3.33 | 23 |
| 27.2 | 3.28 | 19 |

TABLE 59

Peak angle data of 6-O1 (Experiment Reference 6-Sample Reference O1) (Pattern #1)

| 2-θ (°) | d Value | Rel. Intensity (%) |
|---|---|---|
| 6.8 | 13.06 | 22 |
| 8.1 | 10.88 | 12 |
| 9.1 | 9.70 | 43 |
| 11.2 | 7.90 | 10 |
| 13.0 | 6.83 | 10 |
| 14.3 | 6.20 | 17 |
| 16.4 | 5.41 | 100 |
| 16.8 | 5.28 | 48 |
| 17.5 | 5.06 | 15 |
| 17.9 | 4.95 | 16 |
| 18.2 | 4.88 | 31 |
| 18.9 | 4.70 | 11 |
| 19.4 | 4.58 | 53 |
| 19.6 | 4.52 | 16 |
| 20.2 | 4.39 | 13 |
| 21.3 | 4.17 | 11 |
| 21.4 | 4.15 | 10 |
| 21.8 | 4.08 | 15 |
| 22.4 | 3.97 | 25 |
| 23.2 | 3.83 | 16 |
| 23.5 | 3.78 | 16 |
| 25.2 | 3.53 | 33 |
| 25.5 | 3.49 | 94 |
| 26.2 | 3.40 | 12 |
| 26.8 | 3.32 | 29 |
| 27.1 | 3.29 | 23 |
| 30.1 | 2.97 | 13 |

TABLE 60

Peak angle data of 6-P2 (Experiment Reference 6-Sample Reference P2) (Pattern #4a)

| 2-θ (°) | d Value | Rel. Intensity (%) |
|---|---|---|
| 8.2 | 10.74 | 71 |
| 9.0 | 9.78 | 38 |
| 11.2 | 7.88 | 23 |
| 12.7 | 6.96 | 14 |
| 14.2 | 6.23 | 16 |
| 15.6 | 5.69 | 17 |
| 16.3 | 5.43 | 90 |
| 17.1 | 5.18 | 28 |
| 17.3 | 5.13 | 17 |
| 18.0 | 4.91 | 18 |
| 19.2 | 4.63 | 10 |
| 20.3 | 4.37 | 13 |
| 21.5 | 4.14 | 28 |
| 22.4 | 3.97 | 13 |
| 22.6 | 3.93 | 16 |
| 23.8 | 3.73 | 24 |
| 25.1 | 3.54 | 14 |
| 25.5 | 3.49 | 100 |
| 26.8 | 3.33 | 22 |

TABLE 61

Peak angle data of 6-Q2 (Experiment Reference 6-Sample Reference Q2) (Pattern #2b)

| 2-θ (°) | d Value | Rel. Intensity (%) |
|---|---|---|
| 9.1 | 9.73 | 40 |
| 14.3 | 6.21 | 16 |
| 15.5 | 5.70 | 22 |
| 16.3 | 5.42 | 87 |
| 17.0 | 5.22 | 18 |
| 17.4 | 5.08 | 18 |
| 18.1 | 4.89 | 31 |
| 18.8 | 4.71 | 12 |

TABLE 61-continued

Peak angle data of 6-Q2 (Experiment Reference 6-Sample Reference Q2) (Pattern #2b)

| 2-θ (°) | d Value | Rel. Intensity (%) |
|---|---|---|
| 19.5 | 4.54 | 11 |
| 20.9 | 4.24 | 12 |
| 21.5 | 4.12 | 4 |
| 22.4 | 3.97 | 17 |
| 22.6 | 3.93 | 21 |
| 24.8 | 3.59 | 26 |
| 25.6 | 3.48 | 100 |
| 26.8 | 3.32 | 25 |
| 27.2 | 3.28 | 11 |

TABLE 62

Peak angle data of 6-R1 (Experiment Reference 6-Sample Reference R1) (Pattern #3)

| 2-θ (°) | d Value | Rel. Intensity (%) |
|---|---|---|
| 8.4 | 10.46 | 12 |
| 9.1 | 9.74 | 23 |
| 14.4 | 6.16 | 13 |
| 14.4 | 6.13 | 12 |
| 16.4 | 5.42 | 71 |
| 16.6 | 5.34 | 52 |
| 16.8 | 5.26 | 30 |
| 18.1 | 4.91 | 26 |
| 18.7 | 4.73 | 29 |
| 20.1 | 4.42 | 34 |
| 22.3 | 3.99 | 44 |
| 22.4 | 3.97 | 38 |
| 24.7 | 3.60 | 16 |
| 25.1 | 3.55 | 21 |
| 25.5 | 3.49 | 100 |
| 26.0 | 3.43 | 38 |
| 26.7 | 3.34 | 31 |
| 27.2 | 3.27 | 14 |
| 29.8 | 2.99 | 10 |

TABLE 63

Peak angle data of 6-S1 (Experiment Reference 6-Sample Reference S1) (Pattern #6a)

| 2-θ (°) | d Value | Rel. Intensity (%) |
|---|---|---|
| 12.9 | 6.84 | 21 |
| 16.5 | 5.36 | 51 |
| 19.3 | 4.59 | 30 |
| 19.5 | 4.55 | 100 |
| 20.6 | 4.31 | 49 |
| 22.0 | 4.03 | 31 |
| 25.3 | 3.52 | 44 |
| 26.0 | 3.42 | 64 |
| 28.1 | 3.18 | 10 |
| 33.4 | 2.68 | 15 |

TABLE 64

Peak angle data of 7-A2 (Experiment Reference 7-Sample Reference A2) (Pattern #19)

| 2-θ (°) | d Value | Rel. Intensity (%) |
|---|---|---|
| 9.1 | 9.72 | 18 |
| 16.5 | 5.37 | 26 |
| 16.9 | 5.25 | 18 |
| 17.9 | 4.96 | 13 |
| 19.3 | 4.60 | 25 |
| 20.5 | 4.33 | 43 |

TABLE 64-continued

Peak angle data of 7-A2 (Experiment Reference 7-Sample Reference A2) (Pattern #19)

| 2-θ (°) | d Value | Rel. Intensity (%) |
|---|---|---|
| 22.7 | 3.91 | 77 |
| 25.3 | 3.51 | 100 |
| 26.6 | 3.35 | 21 |
| 27.1 | 3.29 | 43 |
| 29.7 | 3.01 | 13 |

TABLE 65

Peak angle data of 7-B1 (Experiment Reference 7-Sample Reference B1) (Pattern #2a)

| 2-θ (°) | d Value | Rel. Intensity (%) |
|---|---|---|
| 9.2 | 9.62 | 41 |
| 12.4 | 7.15 | 30 |
| 14.3 | 6.17 | 17 |
| 15.8 | 5.60 | 33 |
| 16.4 | 5.39 | 85 |
| 17.2 | 5.16 | 73 |
| 18.2 | 4.87 | 29 |
| 20.8 | 4.26 | 25 |
| 21.0 | 4.23 | 28 |
| 21.6 | 4.10 | 14 |
| 22.4 | 3.97 | 16 |
| 22.9 | 3.88 | 30 |
| 23.0 | 3.86 | 36 |
| 25.0 | 3.56 | 23 |
| 25.7 | 3.46 | 100 |
| 26.9 | 3.31 | 26 |
| 27.4 | 3.26 | 36 |
| 28.7 | 3.10 | 12 |

TABLE 66

Peak angle data of 7-C1 (Experiment Reference 7-Sample Reference C1) (Pattern #1)

| 2-θ (°) | d Value | Rel. Intensity (%) |
|---|---|---|
| 6.8 | 12.91 | 10 |
| 9.2 | 9.63 | 24 |
| 14.3 | 6.19 | 11 |
| 16.5 | 5.38 | 70 |
| 16.7 | 5.29 | 34 |
| 17.7 | 5.00 | 14 |
| 18.2 | 4.87 | 28 |
| 19.4 | 4.56 | 36 |
| 22.5 | 3.96 | 22 |
| 22.4 | 3.96 | 22 |
| 23.2 | 3.83 | 12 |
| 25.6 | 3.47 | 100 |
| 26.3 | 3.39 | 14 |
| 27.0 | 3.30 | 27 |
| 27.2 | 3.27 | 25 |

TABLE 67

Peak angle data of 7-C2 (Experiment Reference 7-Sample Reference C2) (Pattern #1)

| 2-θ (°) | d Value | Rel. Intensity (%) |
|---|---|---|
| 9.1 | 9.75 | 23 |
| 14.2 | 6.22 | 11 |
| 16.3 | 5.42 | 72 |
| 16.7 | 5.30 | 31 |
| 17.5 | 5.07 | 14 |
| 17.7 | 5.01 | 12 |

TABLE 67-continued

Peak angle data of 7-C2 (Experiment Reference 7-Sample Reference C2) (Pattern #1)

| 2-θ (°) | d Value | Rel. Intensity (%) |
|---|---|---|
| 18.1 | 4.89 | 26 |
| 19.3 | 4.59 | 37 |
| 22.3 | 3.98 | 22 |
| 23.1 | 3.84 | 14 |
| 23.7 | 3.75 | 6 |
| 25.1 | 3.54 | 16 |
| 25.6 | 3.48 | 100 |
| 26.2 | 3.40 | 13 |
| 26.8 | 3.32 | 21 |
| 27.3 | 3.27 | 24 |

TABLE 68

Peak angle data of 7-D1 (Experiment Reference 7-Sample Reference D1) (Pattern #3)

| 2-θ (°) | d Value | Rel. Intensity (%) |
|---|---|---|
| 8.5 | 10.39 | 25 |
| 9.1 | 9.67 | 26 |
| 11.3 | 7.81 | 20 |
| 12.6 | 7.00 | 19 |
| 14.4 | 6.14 | 32 |
| 16.5 | 5.38 | 71 |
| 16.7 | 5.29 | 100 |
| 16.9 | 5.23 | 57 |
| 17.5 | 5.07 | 13 |
| 18.1 | 4.88 | 19 |
| 18.9 | 4.69 | 36 |
| 19.5 | 4.54 | 10 |
| 20.2 | 4.39 | 46 |
| 21.7 | 4.10 | 14 |
| 22.4 | 3.96 | 49 |
| 22.6 | 3.93 | 30 |
| 24.8 | 3.59 | 24 |
| 25.6 | 3.47 | 74 |
| 26.2 | 3.40 | 40 |
| 26.9 | 3.31 | 34 |

TABLE 69

Peak angle data of 7-D2 (Experiment Reference 7-Sample Reference D2) (Pattern #1)

| 2-θ (°) | d Value | Rel. Intensity (%) |
|---|---|---|
| 6.7 | 13.18 | 11 |
| 9.0 | 9.78 | 17 |
| 14.2 | 6.23 | 11 |
| 16.3 | 5.44 | 67 |
| 16.7 | 5.30 | 43 |
| 17.4 | 5.09 | 15 |
| 17.7 | 5.00 | 18 |
| 18.1 | 4.90 | 30 |
| 19.3 | 4.60 | 57 |
| 20.2 | 4.40 | 14 |
| 21.2 | 4.18 | 12 |
| 22.3 | 3.99 | 30 |
| 22.5 | 3.95 | 11 |
| 23.1 | 3.85 | 14 |
| 24.6 | 3.62 | 11 |
| 25.5 | 3.49 | 100 |
| 26.1 | 3.41 | 21 |
| 26.8 | 3.32 | 20 |
| 27.2 | 3.27 | 27 |

TABLE 70

Peak angle data of 7-E2 (Experiment Reference 7-Sample Reference E2)
(Pattern #1)

| 2-θ (°) | d Value | Rel. Intensity (%) |
|---|---|---|
| 6.7 | 13.14 | 11 |
| 9.0 | 9.77 | 24 |
| 10.9 | 8.14 | 11 |
| 12.2 | 7.26 | 15 |
| 12.8 | 6.90 | 12 |
| 14.2 | 6.24 | 10 |
| 15.5 | 5.73 | 14 |
| 16.1 | 5.50 | 43 |
| 16.3 | 5.44 | 68 |
| 16.7 | 5.30 | 37 |
| 17.4 | 5.08 | 19 |
| 17.7 | 5.01 | 23 |
| 18.1 | 4.90 | 26 |
| 19.3 | 4.60 | 52 |
| 20.2 | 4.40 | 14 |
| 21.2 | 4.19 | 42 |
| 22.0 | 4.04 | 10 |
| 22.3 | 3.99 | 23 |
| 23.1 | 3.85 | 16 |
| 25.4 | 3.51 | 79 |
| 25.5 | 3.49 | 100 |
| 26.1 | 3.41 | 12 |
| 26.8 | 3.33 | 17 |
| 27.2 | 3.27 | 23 |
| 30.0 | 2.98 | 10 |

TABLE 71

Peak angle data of 7-F1 (Experiment Reference 7-Sample Reference F1)
(Pattern #5)

| 2-θ (°) | d Value | Rel. Intensity (%) |
|---|---|---|
| 8.2 | 10.74 | 58 |
| 9.1 | 9.74 | 10 |
| 11.1 | 7.99 | 57 |
| 12.8 | 6.92 | 12 |
| 15.4 | 5.75 | 65 |
| 16.2 | 5.45 | 24 |
| 17.0 | 5.22 | 100 |
| 17.9 | 4.95 | 10 |
| 19.1 | 4.64 | 22 |
| 20.0 | 4.43 | 55 |
| 21.4 | 4.15 | 84 |
| 22.2 | 4.01 | 25 |
| 22.5 | 3.95 | 31 |
| 23.6 | 3.77 | 58 |
| 24.0 | 3.70 | 28 |
| 25.5 | 3.50 | 50 |
| 30.3 | 2.95 | 24 |

TABLE 72

Peak angle data of 7-G1 (Experiment Reference 7-Sample Reference G1)
(Pattern #9)

| 2-θ (°) | d Value | Rel. Intensity (%) |
|---|---|---|
| 7.9 | 11.21 | 20 |
| 9.1 | 9.76 | 15 |
| 14.2 | 6.24 | 10 |
| 15.7 | 5.62 | 70 |
| 16.3 | 5.44 | 47 |
| 16.9 | 5.24 | 32 |
| 18.0 | 4.92 | 12 |
| 19.3 | 4.60 | 40 |
| 20.6 | 4.31 | 22 |
| 21.6 | 4.10 | 29 |
| 22.2 | 4.00 | 12 |
| 24.5 | 3.64 | 88 |
| 25.1 | 3.54 | 46 |
| 25.4 | 3.50 | 100 |
| 26.1 | 3.41 | 13 |
| 26.7 | 3.33 | 22 |
| 28.6 | 3.12 | 22 |
| 29.9 | 2.99 | 11 |

TABLE 73

Peak angle data of 7-G2 (Experiment Reference 7-Sample Reference G2)
(Pattern #1)

| 2-θ (°) | d Value | Rel. Intensity (%) |
|---|---|---|
| 9.0 | 9.80 | 20 |
| 16.3 | 5.44 | 64 |
| 16.7 | 5.30 | 34 |
| 17.4 | 5.09 | 12 |
| 17.7 | 5.00 | 15 |
| 18.1 | 4.90 | 19 |
| 19.3 | 4.60 | 49 |
| 20.2 | 4.40 | 10 |
| 21.2 | 4.18 | 11 |
| 22.3 | 3.99 | 25 |
| 23.0 | 3.86 | 13 |
| 25.1 | 3.54 | 13 |
| 25.5 | 3.49 | 100 |
| 26.1 | 3.41 | 14 |
| 26.8 | 3.33 | 17 |
| 27.2 | 3.27 | 20 |

TABLE 74

Peak angle data of 7-H2 (Experiment Reference 7-Sample Reference H2)
(Pattern #2b)

| 2-θ (°) | d Value | Rel. Intensity (%) |
|---|---|---|
| 9.0 | 9.80 | 18 |
| 14.2 | 6.24 | 10 |
| 16.1 | 5.49 | 25 |
| 17.4 | 5.09 | 11 |
| 18.0 | 4.92 | 17 |
| 21.2 | 4.19 | 15 |
| 22.6 | 3.93 | 11 |
| 23.1 | 3.85 | 11 |
| 25.2 | 3.53 | 18 |
| 25.5 | 3.49 | 100 |
| 26.8 | 3.33 | 21 |

TABLE 75

Peak angle data of 7-11 (Experiment Reference 7-Sample Reference I1)
(Pattern #1)

| 2-θ (°) | d Value | Rel. Intensity (%) |
|---|---|---|
| 9.1 | 9.69 | 23 |
| 16.4 | 5.41 | 70 |
| 16.8 | 5.28 | 29 |
| 17.5 | 5.06 | 11 |
| 18.2 | 4.88 | 25 |
| 19.4 | 4.58 | 32 |
| 22.4 | 3.97 | 26 |
| 23.2 | 3.84 | 11 |
| 25.3 | 3.52 | 14 |
| 25.6 | 3.48 | 100 |
| 26.2 | 3.39 | 11 |

TABLE 75-continued

Peak angle data of 7-I1 (Experiment Reference 7-Sample Reference I1) (Pattern #1)

| 2-θ (°) | d Value | Rel. Intensity (%) |
|---|---|---|
| 26.9 | 3.31 | 21 |
| 27.3 | 3.26 | 21 |
| 30.0 | 2.97 | 11 |

TABLE 76

Peak angle data of 7-I2 (Experiment Reference 7-Sample Reference I2) (Pattern #1)

| 2-θ (°) | d Value | Rel. Intensity (%) |
|---|---|---|
| 6.8 | 13.07 | 12 |
| 9.1 | 9.72 | 27 |
| 14.3 | 6.20 | 13 |
| 16.4 | 5.41 | 78 |
| 16.8 | 5.29 | 43 |
| 17.5 | 5.06 | 13 |
| 17.8 | 4.98 | 17 |
| 18.2 | 4.88 | 28 |
| 18.9 | 4.70 | 11 |
| 19.4 | 4.58 | 48 |
| 20.3 | 4.38 | 11 |
| 21.3 | 4.17 | 13 |
| 22.1 | 4.01 | 10 |
| 22.4 | 3.97 | 23 |
| 23.2 | 3.84 | 16 |
| 25.2 | 3.53 | 15 |
| 25.6 | 3.48 | 100 |
| 26.2 | 3.40 | 15 |
| 26.9 | 3.31 | 21 |
| 27.3 | 3.26 | 23 |

TABLE 77

Peak angle data of 7-J1 (Experiment Reference 7-Sample Reference J1) (Pattern #2a)

| 2-θ (°) | d Value | Rel. Intensity (%) |
|---|---|---|
| 9.0 | 9.79 | 16 |
| 16.3 | 5.45 | 65 |
| 16.9 | 5.23 | 19 |
| 18.0 | 4.93 | 18 |
| 25.0 | 3.56 | 16 |
| 25.5 | 3.49 | 100 |
| 26.7 | 3.33 | 26 |
| 27.1 | 3.28 | 19 |
| 29.9 | 2.99 | 12 |

TABLE 78

Peak angle data of 7-J2 (Experiment Reference 7-Sample Reference J2) (Pattern #2a)

| 2-θ (°) | d Value | Rel. Intensity (%) |
|---|---|---|
| 9.0 | 9.79 | 20 |
| 12.2 | 7.24 | 10 |
| 14.2 | 6.24 | 12 |
| 15.6 | 5.67 | 12 |
| 16.3 | 5.44 | 70 |
| 17.0 | 5.22 | 29 |
| 18.0 | 4.92 | 20 |
| 20.6 | 4.30 | 15 |
| 22.2 | 3.99 | 11 |
| 22.9 | 3.89 | 20 |
| 25.1 | 3.55 | 17 |
| 25.5 | 3.49 | 100 |

TABLE 78-continued

Peak angle data of 7-J2 (Experiment Reference 7-Sample Reference J2) (Pattern #2a)

| 2-θ (°) | d Value | Rel. Intensity (%) |
|---|---|---|
| 26.7 | 3.33 | 25 |
| 27.2 | 3.28 | 22 |
| 29.9 | 2.99 | 12 |

TABLE 79

Peak angle data of 7-L2 (Experiment Reference 7-Sample Reference L2) (Pattern #1)

| 2-θ (°) | d Value | Rel. Intensity (%) |
|---|---|---|
| 9.0 | 9.80 | 24 |
| 14.2 | 6.24 | 10 |
| 16.0 | 5.52 | 11 |
| 16.3 | 5.44 | 59 |
| 16.7 | 5.30 | 24 |
| 17.4 | 5.10 | 11 |
| 17.7 | 5.00 | 11 |
| 18.1 | 4.91 | 23 |
| 19.3 | 4.60 | 36 |
| 22.3 | 3.99 | 19 |
| 23.1 | 3.85 | 12 |
| 25.1 | 3.54 | 10 |
| 25.5 | 3.49 | 100 |
| 26.1 | 3.41 | 11 |
| 26.8 | 3.33 | 23 |
| 27.2 | 3.27 | 20 |

TABLE 80

Peak angle data of 7-M1 (Experiment Reference 7-Sample Reference M1) (Pattern #2a)

| 2-θ (°) | d Value | Rel. Intensity (%) |
|---|---|---|
| 9.1 | 9.73 | 25 |
| 14.2 | 6.22 | 13 |
| 15.6 | 5.67 | 11 |
| 16.3 | 5.42 | 75 |
| 17.0 | 5.21 | 20 |
| 18.1 | 4.90 | 20 |
| 18.8 | 4.71 | 11 |
| 22.3 | 3.98 | 12 |
| 25.6 | 3.48 | 100 |
| 26.8 | 3.32 | 26 |
| 27.2 | 3.27 | 21 |
| 29.9 | 2.98 | 10 |

TABLE 81

Peak angle data of 7-M2 (Experiment Reference 7-Sample Reference M2) (Pattern #2a)

| 2-θ (°) | d Value | Rel. Intensity (%) |
|---|---|---|
| 9.1 | 9.76 | 27 |
| 12.2 | 7.22 | 24 |
| 14.2 | 6.22 | 14 |
| 15.6 | 5.67 | 36 |
| 15.9 | 5.56 | 18 |
| 16.3 | 5.43 | 78 |
| 17.0 | 5.21 | 64 |
| 17.4 | 5.09 | 11 |
| 18.1 | 4.90 | 26 |
| 18.8 | 4.71 | 11 |
| 19.3 | 4.59 | 15 |
| 20.6 | 4.30 | 28 |
| 21.0 | 4.23 | 22 |

TABLE 81-continued

Peak angle data of 7-M2 (Experiment Reference 7-Sample Reference M2) (Pattern #2a)

| 2-θ (°) | d Value | Rel. Intensity (%) |
|---|---|---|
| 21.5 | 4.13 | 16 |
| 22.3 | 3.98 | 14 |
| 22.9 | 3.89 | 39 |
| 24.8 | 3.59 | 34 |
| 25.5 | 3.48 | 100 |
| 26.8 | 3.32 | 26 |
| 27.3 | 3.27 | 45 |
| 28.6 | 3.11 | 11 |
| 29.9 | 2.98 | 11 |

TABLE 82

Peak ang0le data of 7-N1 (Experiment Reference 7-Sample Reference N1) (Pattern #7)

| 2-θ (°) | d Value | Rel. Intensity (%) |
|---|---|---|
| 7.2 | 12.27 | 17 |
| 9.1 | 9.72 | 27 |
| 14.2 | 6.22 | 12 |
| 15.9 | 5.58 | 62 |
| 16.3 | 5.43 | 86 |
| 16.7 | 5.32 | 19 |
| 17.5 | 5.06 | 11 |
| 18.1 | 4.89 | 25 |
| 19.3 | 4.59 | 26 |
| 19.7 | 4.50 | 25 |
| 20.8 | 4.27 | 14 |
| 21.2 | 4.18 | 22 |
| 22.4 | 3.97 | 18 |
| 24.8 | 3.58 | 83 |
| 25.5 | 3.48 | 100 |
| 26.8 | 3.32 | 23 |
| 27.2 | 3.28 | 19 |
| 30.0 | 2.98 | 10 |

TABLE 83

Peak angle data of 7-O2 (Experiment Reference 7-Sample Reference O2) (Pattern #2a)

| 2-θ (°) | d Value | Rel. Intensity (%) |
|---|---|---|
| 9.0 | 9.79 | 23 |
| 12.2 | 7.24 | 20 |
| 14.2 | 6.24 | 13 |
| 15.6 | 5.67 | 26 |
| 15.9 | 5.56 | 14 |
| 16.3 | 5.43 | 78 |
| 17.0 | 5.21 | 49 |
| 17.4 | 5.10 | 13 |
| 18.0 | 4.92 | 21 |
| 20.6 | 4.30 | 22 |
| 21.0 | 4.23 | 15 |
| 22.9 | 3.89 | 30 |
| 25.0 | 3.56 | 15 |
| 25.5 | 3.49 | 100 |
| 26.8 | 3.33 | 22 |
| 27.3 | 3.27 | 28 |

TABLE 84

Peak angle data of 7-P1 (Experiment Reference 7-Sample Reference P1) (Pattern #10)

| 2-θ (°) | d Value | Rel. Intensity (%) |
|---|---|---|
| 8.2 | 10.77 | 32 |
| 10.9 | 8.14 | 30 |

TABLE 84-continued

Peak angle data of 7-P1 (Experiment Reference 7-Sample Reference P1) (Pattern #10)

| 2-θ (°) | d Value | Rel. Intensity (%) |
|---|---|---|
| 15.2 | 5.82 | 32 |
| 16.2 | 5.47 | 20 |
| 16.8 | 5.26 | 100 |
| 17.8 | 4.98 | 12 |
| 19.1 | 4.65 | 17 |
| 19.8 | 4.49 | 47 |
| 21.3 | 4.17 | 68 |
| 21.8 | 4.08 | 32 |
| 22.1 | 4.01 | 29 |
| 22.5 | 3.95 | 10 |
| 23.4 | 3.79 | 66 |
| 23.6 | 3.76 | 41 |
| 25.3 | 3.51 | 62 |
| 26.1 | 3.41 | 14 |
| 26.7 | 3.34 | 21 |
| 29.7 | 3.00 | 27 |
| 34.7 | 2.58 | 11 |

TABLE 85

Peak angle data of 7-Q1 (Experiment Reference 7-Sample Reference Q1) (Pattern #11)

| 2-θ (°) | d Value | Rel. Intensity (%) |
|---|---|---|
| 7.4 | 11.88 | 53 |
| 10.6 | 8.32 | 13 |
| 11.1 | 7.96 | 12 |
| 16.1 | 5.52 | 91 |
| 17.2 | 5.14 | 17 |
| 18.0 | 4.92 | 12 |
| 20.2 | 4.39 | 100 |
| 20.7 | 4.28 | 15 |
| 21.5 | 4.13 | 48 |
| 22.6 | 3.93 | 18 |
| 23.8 | 3.73 | 13 |
| 23.9 | 3.72 | 13 |
| 25.1 | 3.54 | 19 |
| 25.5 | 3.49 | 32 |
| 25.7 | 3.46 | 20 |
| 26.7 | 3.34 | 12 |

TABLE 86

Peak angle data of 7-R1 (Experiment Reference 7-Sample Reference R1) (Pattern #1)

| 2-θ (°) | d Value | Rel. Intensity (%) |
|---|---|---|
| 16.2 | 5.45 | 48 |
| 18.0 | 4.92 | 17 |
| 18.7 | 4.75 | 15 |
| 19.2 | 4.62 | 29 |
| 20.0 | 4.43 | 16 |
| 22.1 | 4.01 | 26 |
| 22.3 | 3.98 | 22 |
| 22.9 | 3.87 | 12 |
| 25.4 | 3.50 | 100 |
| 25.9 | 3.44 | 23 |
| 26.7 | 3.34 | 26 |
| 27.1 | 3.28 | 29 |
| 29.9 | 2.99 | 13 |

TABLE 87

Peak angle data of 7-S1 (Experiment Reference
7-Sample Reference S1) (Pattern #8, amorphized)

| 2-θ (°) | d Value | Rel. Intensity (%) |
| --- | --- | --- |
| 13.0 | 6.83 | 28 |
| 16.6 | 5.33 | 20 |
| 19.3 | 4.59 | 44 |
| 19.5 | 4.56 | 80 |
| 25.2 | 3.54 | 67 |
| 25.9 | 3.43 | 100 |
| 26.1 | 3.41 | 67 |
| 28.3 | 3.15 | 52 |
| 33.7 | 2.66 | 25 |
| 37.7 | 2.38 | 20 | c. Conclusion

Powder diffraction patterns of wetted pellets tended to exhibit greater incoherence and higher background. During drying the solvent wet specimens resembling Pattern #1 frequently underwent form change. Patterns #3 and #6a were identified as single melt event forms (both melt events approximately coincided) and Pattern #6b was determined as higher melt forms from water (Patterns #6a and #6b were approximately isostructural by XRPD).

Pattern #3 contained toluene (th., 0.25% w/w toluene solvate), released as a discrete transition before melting (FIG. 330). TG analysis of Pattern #3 specimen exhibited a weight loss transition consistent with toluene release (th., 0.25% w/w toluene solvate), prior to melting and may result in re-organization when released (FIG. 329).

Pattern #6a, was anhydrous and TGA −Δ wt. Transition was absent pre-melt and ablative post melt, which is consistent with decomposition (FIG. 347).

Pattern #6b specimen may contain crystal bonded acetonitrile and methanol and cannot be oven dried (FIG. 353) TG analyses performed on the specimen corresponding to Pattern #6b exhibited a weight loss transition in the vicinity of melting and was attributed to crystal bonded acetonitrile and methanol (FIG. 352);

Patterns #3, #6a, and #6b require further investigation as they may provide access to polymorphic forms with desirable physical properties:

Pattern #6a specimen was placed in vacuum oven for an additional 72 h at 40° C., and the solvent content was quantified by $^1$H NMR spectroscopy after this treatment (methanol 0.6% w/w, acetonitrile n.d.), supporting our belief that methanol is strongly bonded;

potentially, maturation of Patterns #3 and #6b specimens, in an aqueous solvent, such as ethanol at moderate water activity may be applied to break the solvates; judging the two powder patterns, Pattern #6a/b is preferred over Pattern #3 and #6 appears to belong to a more symmetrical, crystallographic space group;

Pattern #6a (m.p.>189° C.) is now the desired form.

vii. Form Control: Suspension Equilibration in Water at 20° C. (Experiment Reference 8)

a. Experimental Procedure

The tabernanthalog monofumarate salt (Sample Reference 1, Pattern #1, 1.0 g, 1 wt) was suspended in water (5 ml, 5 vol) at 20° C. for 10 days (the suspension was sub-sampled to monitor the conversion to Pattern #6a by XRPD). The suspension was filtered through a sintered funnel and the filter cake was dried under nitrogen flow for ca. 24 h. Sample 8-A4 (Experiment Reference 8-Sample Reference A4) was collected as a brown solid (560.6 mg, 56% yield uncorr.). Yield was not corrected for impurities, solvents, etc.

b. Analytical Characterization Data $^1$H NMR $^1$H NMR spectrum of 8-A4 (Experiment Reference 8-Sample Reference A4) was acquired in DMSO-$d_6$ and calibrated to the non-deuterated solvent residual at 2.50 ppm API to Fumaric acid, 1.0 to 1.0 is provided in FIG. 146. $^1$H NMR spectra overlay of 8-A4 (Experiment Reference 8-Sample Reference A4) and input (Sample Reference 1) is presented in FIG. 147.

TGA

TGA profile of 8-A4 (Experiment Reference 8-Sample Reference A4), analysis was acquired at a ramp rate of +10° C./minute, is presented in FIG. 148.

DSC

DSC profile of 8-A4 (Experiment Reference 8-Sample Reference A4), analysis was acquired at a ramp rate of +10° C./minute, is provided in FIG. 149.

XRPD

The XRPD profile of 8-A4 (Experiment Reference 8-Sample Reference A4) (Form A) is presented in FIG. 150 and the peaks are provided in Table 88.

TABLE 88

Peak angle data of 8-A4 (Experiment Reference
8-Sample Reference A4) (Form A, Pattern #6a)

| 2-θ (°) | d Value | Rel. Intensity (%) |
| --- | --- | --- |
| 12.9 | 6.85 | 12 |
| 16.5 | 5.37 | 74 |
| 19.2 | 4.61 | 27 |
| 19.5 | 4.56 | 100 |
| 20.6 | 4.32 | 90 |
| 22.0 | 4.04 | 32 |
| 25.2 | 3.52 | 81 |
| 26.0 | 3.43 | 56 |
| 28.0 | 3.18 | 12 |
| 33.4 | 2.68 | 17 |

HPLC

The HPLC profile of 8-A4 (Experiment Reference 8-Sample Reference A4) is presented in FIG. 151.

PLM

PLM results are shown in FIGS. 152-155.

c. Conclusion

The suspension was sub-sampled, and the wet pellet was analyzed by XRPD until complete conversion was achieved (FIG. 156). The tabernanthalog monofumarate salt (Sample Reference 1, Pattern #1) was successfully converted to the desired form (Pattern #6a, Form A, FIG. 157). Optically, the crystallographic quality of the batch was not judged suitable for SC-XRD.

viii. Thermocycling (Experiment Reference 9)

a. Experimental Procedure

The tabernanthalog monofumarate salt (Pattern #1, 75 mg, 1 wt) was weighed out in to 4 separate vials and the corresponding solvents (750 µl, 10 vol) from Table 89 were charged.

The suspensions underwent constant amplitude thermocycling at +0.5° C./min up to 75% of the relevant solvent b.p, and −0.5° C./min down to 20° C. The thermocycle was repeated 5 times for 9-A (Experiment Reference 9-Sample Reference A) to 9-D (Experiment Reference 9-Sample Reference D) prior to working up the samples, analyzed by XRPD (wet and dry). 9-E (Experiment Reference 9-Sample Reference E) and 9-F (Experiment Reference 9-Sample Reference F) were subjected to 10 cycles and 9-G (Experiment Reference 9-Sample Reference G) to 35 cycles.

TABLE 89

Thermocycle experiment setup description

| References | Input reference | Input weights (mg) | Solvent | b.p. (° C.) | Thermocycle peak T (° C.) | Number of cycles |
|---|---|---|---|---|---|---|
| 9-A | Sample Reference 1 | 75.5 | Water | 100 | 75 | 5 |
| 9-B |  | 75.7 | TBME | 55 | 41 | 5 |
| 9-C |  | 75.1 | iPAC | 89 | 69 | 5 |
| 9-D |  | 75.5 | Toluene | 110 | 83 | 5 |
| 9-E |  | 75.3 | Water | 100 | 75 | 10 |
| 9-F | 8-A4 (Experiment Reference 8-Sample Reference A4) | 75.2 | Water | 100 | 75 | 10 |
| 9-G | Sample Reference 1 | 75.4 | Water | 100 | 75 | 35 | b. Analytical Characterization Data

Thermocycling in different solvents can promote the formation of alternative polymorphic forms. The tabernanthalog monofumarate salt (Pattern #1), was heated and cooled between 20° C. and 75% of the relevant solvent b.p. at 0.5° C./minute, for 5 consecutive cycles; a 10-minute dwell was incorporated at each inflection. Thermocycling is ripening technique, that encourages particle size enlargement and promotes the evolution of the API into a stable phase. Smaller, less stable particles dissolve as the upper temperature boundary is approached, leaving larger stable particles behind; during cooling the concentrated supernatant de-supersaturates resulting in growth in the presence of the larger particles; after thermocycling, the particles should be larger and fewer in number. The products were analyzed both wet and dry to determine if form changes had occurred, all products were consistent with previously encountered patterns, and by DSC none of the products were single phase.

For samples that contain wet pellets, suffix 1 is used. For oven-dried samples, suffix 2 is used.

$^1$H NMR

The relevant NMR spectra are provided in FIGS. 158-163.

TGA

The relevant TGA profiles are provided in FIGS. 164-169.

DSC

The relevant DSC profiles are provided in FIGS. 170-176.

XRPD

The relevant XRD data is provided in FIGS. 177-190 and Tables 90-103.

TABLE 90

Peak angle data of 9-A1 (Experiment Reference 9-Sample Reference A1)

| 2-θ (°) | d Value | Rel. Intensity (%) |
|---|---|---|
| 9.1 | 9.71 | 100 |
| 16.3 | 5.45 | 20 |
| 25.1 | 3.55 | 23 |
| 25.5 | 3.49 | 18 |

TABLE 91

Peak angle data of 9-A2 (Experiment Reference 9-Sample Reference A2) (Pattern #2c)

| 2-θ (°) | d Value | Rel. Intensity (%) |
|---|---|---|
| 9.1 | 9.74 | 62 |
| 14.2 | 6.21 | 23 |
| 16.3 | 5.42 | 91 |
| 17.5 | 5.08 | 14 |
| 18.1 | 4.90 | 21 |
| 19.5 | 4.55 | 29 |
| 22.0 | 4.03 | 13 |
| 22.2 | 4.00 | 13 |
| 25.1 | 3.54 | 29 |
| 25.6 | 3.48 | 100 |
| 26.1 | 3.42 | 19 |
| 26.8 | 3.32 | 20 |

TABLE 92

Peak angle data of 9-B1 (Experiment Reference 9-Sample Reference B1) (Pattern #1)

| 2-θ (°) | d Value | Rel. Intensity (%) |
|---|---|---|
| 6.8 | 13.04 | 12 |
| 9.1 | 9.69 | 23 |
| 14.3 | 6.21 | 11 |
| 16.4 | 5.41 | 69 |
| 16.8 | 5.28 | 39 |
| 17.6 | 5.04 | 17 |
| 17.8 | 4.98 | 19 |
| 18.2 | 4.88 | 29 |
| 19.4 | 4.58 | 50 |
| 20.2 | 4.38 | 12 |
| 22.1 | 4.01 | 11 |
| 22.4 | 3.97 | 25 |
| 23.2 | 3.83 | 13 |
| 25.3 | 3.52 | 18 |
| 25.6 | 3.48 | 100 |
| 26.2 | 3.39 | 16 |
| 26.9 | 3.31 | 21 |
| 27.3 | 3.27 | 28 |

TABLE 93

Peak angle data of 9-B2 (Experiment Reference 9-Sample Reference B2) (Pattern #1)

| 2-θ (°) | d Value | Rel. Intensity (%) |
|---|---|---|
| 9.0 | 9.78 | 15 |
| 14.2 | 6.23 | 10 |
| 16.3 | 5.43 | 58 |
| 16.7 | 5.29 | 38 |
| 17.4 | 5.08 | 11 |
| 17.8 | 4.98 | 12 |
| 18.1 | 4.90 | 24 |
| 19.3 | 4.60 | 51 |
| 20.2 | 4.40 | 13 |
| 22.3 | 3.98 | 24 |

TABLE 93-continued

Peak angle data of 9-B2 (Experiment Reference 9-Sample Reference B2) (Pattern #1)

| 2-θ (°) | d Value | Rel. Intensity (%) |
|---|---|---|
| 23.1 | 3.85 | 15 |
| 25.5 | 3.49 | 100 |
| 26.2 | 3.40 | 15 |
| 26.8 | 3.32 | 20 |
| 27.2 | 3.28 | 27 |

TABLE 94

Peak angle data of 9-C1 (Experiment Reference 9-Sample Reference C1) (Pattern #8)

| 2-θ (°) | d Value | Rel. Intensity (%) |
|---|---|---|
| 7.6 | 11.66 | 40 |
| 9.1 | 9.76 | 21 |
| 12.2 | 7.27 | 13 |
| 15.5 | 5.69 | 10 |
| 15.8 | 5.59 | 100 |
| 16.3 | 5.43 | 71 |
| 18.0 | 4.92 | 17 |
| 19.1 | 4.65 | 45 |
| 20.6 | 4.31 | 56 |
| 21.9 | 4.06 | 20 |
| 23.8 | 3.73 | 19 |
| 24.2 | 3.67 | 90 |
| 24.9 | 3.57 | 19 |
| 25.5 | 3.49 | 78 |
| 26.8 | 3.33 | 18 |
| 27.2 | 3.27 | 17 |

TABLE 95

Peak angle data of 9-C2 (Experiment Reference 9-Sample Reference C2) (Pattern #8)

| 2-θ (°) | d Value | Rel. Intensity (%) |
|---|---|---|
| 7.6 | 11.67 | 39 |
| 9.0 | 9.78 | 21 |
| 12.2 | 7.27 | 12 |
| 14.2 | 6.23 | 11 |
| 15.9 | 5.58 | 100 |
| 16.3 | 5.42 | 78 |
| 17.4 | 5.08 | 11 |
| 18.0 | 4.92 | 16 |
| 18.9 | 4.69 | 11 |
| 19.1 | 4.65 | 37 |
| 20.6 | 4.31 | 52 |
| 21.9 | 4.05 | 15 |
| 23.8 | 3.73 | 14 |
| 24.3 | 3.66 | 84 |
| 25.0 | 3.56 | 14 |
| 25.6 | 3.48 | 81 |
| 26.3 | 3.38 | 6 |
| 26.8 | 3.33 | 16 |
| 27.3 | 3.27 | 15 |

TABLE 96

Peak angle data of 9-D1 (Experiment Reference 9-Sample Reference D1) (Pattern #3)

| 2-θ (°) | d Value | Rel. Intensity (%) |
|---|---|---|
| 8.4 | 10.54 | 24 |
| 9.0 | 9.80 | 29 |
| 9.7 | 9.08 | 10 |
| 11.1 | 7.95 | 28 |

TABLE 96-continued

Peak angle data of 9-D1 (Experiment Reference 9-Sample Reference D1) (Pattern #3)

| 2-θ (°) | d Value | Rel. Intensity (%) |
|---|---|---|
| 12.4 | 7.12 | 23 |
| 14.4 | 6.16 | 23 |
| 16.3 | 5.43 | 83 |
| 16.6 | 5.35 | 94 |
| 16.8 | 5.26 | 42 |
| 17.3 | 5.11 | 10 |
| 18.0 | 4.92 | 19 |
| 18.7 | 4.73 | 42 |
| 20.1 | 4.42 | 59 |
| 21.6 | 4.11 | 10 |
| 22.2 | 4.00 | 47 |
| 22.5 | 3.94 | 25 |
| 22.8 | 3.90 | 13 |
| 24.6 | 3.61 | 20 |
| 25.0 | 3.56 | 25 |
| 25.5 | 3.49 | 100 |
| 26.0 | 3.42 | 62 |
| 26.7 | 3.33 | 31 |

TABLE 97

Peak angle data of 9-D2 (Experiment Reference 9-Sample Reference D2) (Pattern #3)

| 2-θ (°) | d Value | Rel. Intensity (%) |
|---|---|---|
| 8.4 | 10.50 | 14 |
| 9.0 | 9.78 | 18 |
| 11.1 | 7.93 | 24 |
| 12.4 | 7.10 | 16 |
| 14.4 | 6.15 | 18 |
| 16.3 | 5.43 | 75 |
| 16.6 | 5.34 | 76 |
| 16.9 | 5.26 | 32 |
| 17.4 | 5.10 | 10 |
| 18.0 | 4.91 | 18 |
| 18.8 | 4.73 | 33 |
| 20.1 | 4.41 | 52 |
| 21.6 | 4.11 | 11 |
| 22.2 | 4.00 | 43 |
| 22.5 | 3.95 | 23 |
| 22.8 | 3.90 | 11 |
| 24.7 | 3.61 | 21 |
| 25.0 | 3.56 | 20 |
| 25.5 | 3.49 | 100 |
| 26.0 | 3.42 | 53 |
| 26.7 | 3.33 | 32 |
| 29.9 | 2.98 | 11 |

TABLE 98

Peak angle data of 9-E1 (Experiment Reference 9-Sample Reference E1) (Pattern# 2c)

| 2-θ (°) | d Value | Rel. Intensity (%) |
|---|---|---|
| 9.1 | 9.73 | 100 |
| 14.2 | 6.23 | 20 |
| 16.3 | 5.44 | 69 |
| 17.4 | 5.09 | 15 |
| 18.0 | 4.92 | 12 |
| 19.4 | 4.56 | 32 |
| 20.6 | 4.31 | 35 |
| 21.9 | 4.05 | 18 |
| 22.2 | 4.01 | 17 |
| 25.1 | 3.55 | 50 |
| 25.5 | 3.49 | 66 |
| 26.0 | 3.42 | 32 |
| 26.8 | 3.33 | 13 |
| 38.5 | 2.34 | 10 |

TABLE 99

Peak angle data of 9-E2 (Experiment Reference 9-Sample Reference E2) (Pattern #2c)

| 2-θ (°) | d Value | Rel. Intensity (%) |
|---|---|---|
| 9.1 | 9.73 | 79 |
| 12.9 | 6.84 | 23 |
| 14.2 | 6.22 | 21 |
| 16.3 | 5.42 | 69 |
| 16.4 | 5.42 | 64 |
| 17.5 | 5.08 | 13 |
| 18.1 | 4.90 | 15 |
| 19.5 | 4.55 | 100 |
| 20.6 | 4.30 | 17 |
| 22.0 | 4.03 | 24 |
| 22.2 | 4.00 | 17 |
| 25.2 | 3.54 | 35 |
| 25.6 | 3.48 | 68 |
| 26.1 | 3.42 | 65 |
| 26.8 | 3.32 | 17 |
| 27.2 | 3.27 | 10 |

TABLE 100

Peak angle data of 9-F1 (Experiment Reference 9-Sample Reference F1) (Pattern #2c)

| 2-θ (°) | d Value | Rel. Intensity (%) |
|---|---|---|
| 9.1 | 9.73 | 93 |
| 12.9 | 6.85 | 49 |
| 14.2 | 6.23 | 16 |
| 16.3 | 5.42 | 60 |
| 17.4 | 5.09 | 10 |
| 18.0 | 4.92 | 13 |
| 19.4 | 4.57 | 100 |
| 20.6 | 4.30 | 33 |
| 21.9 | 4.05 | 19 |
| 22.2 | 4.00 | 10 |
| 25.1 | 3.55 | 22 |
| 25.5 | 3.49 | 75 |
| 26.0 | 3.42 | 81 |
| 26.7 | 3.33 | 15 |
| 29.3 | 3.05 | 12 |

TABLE 101

Peak angle data of 9-F2 (Experiment Reference 9-Sample Reference F2) (Pattern #2c)

| 2-θ (°) | d Value | Rel. Intensity (%) |
|---|---|---|
| 9.1 | 9.74 | 17 |
| 12.9 | 6.85 | 19 |
| 16.3 | 5.42 | 38 |
| 17.4 | 5.09 | 14 |
| 19.4 | 4.56 | 100 |
| 25.6 | 3.48 | 40 |
| 26.0 | 3.42 | 86 |
| 26.8 | 3.32 | 10 |
| 31.2 | 2.87 | 13 |

TABLE 102

Peak angle data of 9-G1 (Experiment Reference 9-Sample Reference G1) (Pattern #2c)

| 2-θ (°) | d Value | Rel. Intensity (%) |
|---|---|---|
| 9.1 | 9.73 | 100 |
| 14.2 | 6.24 | 18 |
| 16.3 | 5.45 | 54 |
| 18.0 | 4.92 | 11 |
| 19.5 | 4.56 | 13 |
| 21.9 | 4.06 | 13 |
| 22.2 | 4.01 | 15 |
| 25.0 | 3.55 | 38 |
| 25.5 | 3.49 | 66 |
| 26.1 | 3.42 | 13 |
| 26.7 | 3.33 | 14 |
| 38.5 | 2.34 | 12 |

TABLE 103

Peak angle data of 9-G2 (Experiment Reference 9-Sample Reference G2) (Pattern #2c)

| 2-θ (°) | d Value | Rel. Intensity (%) |
|---|---|---|
| 9.2 | 9.59 | 76 |
| 14.4 | 6.16 | 21 |
| 16.5 | 5.37 | 100 |
| 17.6 | 5.03 | 13 |
| 18.3 | 4.85 | 28 |
| 19.0 | 4.67 | 12 |
| 19.7 | 4.51 | 11 |
| 22.4 | 3.97 | 16 |
| 22.3 | 3.98 | 16 |
| 22.5 | 3.94 | 17 |
| 25.4 | 3.50 | 45 |
| 25.7 | 3.46 | 100 |
| 27.0 | 3.30 | 27 |
| 27.4 | 3.26 | 12 |

PLM

PLM data is provided in FIGS. 191-198.

c. Conclusion

9-A2 (Experiment Reference 9-Sample Reference A2) was a mixed phase by DSC; however, the highest melt event observed was ca 10° C. higher than the melt of Pattern #6a (onset 199° C., peak 203° C. Therefore, two follow-up experiments were performed which involved subjecting Sample Reference 1 and 8-A (Experiment Reference 8-Sample Reference A; single melt form) to prolonged thermocycling in purified water (9-E (Experiment Reference 9-Sample Reference E) and 9-F (Experiment Reference 9-Sample Reference F), respectively). The collected data are summarized in Table 104

TABLE 104

Summary for thermocycling experiment

| References | Input reference | Input weights (mg) | Solvent | b.p. (° C.) | Thermo-cycle peak T (° C.) | XRPD crystal-linity (oven dried) | crystal form change following dry | Yield % | XRPD (moist pellet) | XRPD (dried pellet) | TGA (dried pellet) | $^1$H NMR (solvent content, % w/w) |
|---|---|---|---|---|---|---|---|---|---|---|---|---|
| 9-A | Sample Reference 1 | 75.5 | Water | 100 | 75 | 82.1% | ✓ | 31.0% | Incoherent | Pattern #2c | Flat baseline | — |
| 9-B | | 75.7 | TBME | 55 | 41 | 73.6% | x | 75.4% | Pattern #1 | Pattern #1 | −2.8% w/w (102.9° C.) | 0.3% |
| 9-C | | 75.1 | iPAC | 89 | 69 | 72.8% | x | 84.8% | Pattern #8 | Pattern #8 | −21.0% w/w (114.1° C.) | 13.2% |
| 9-D | | 75.5 | Toluene | 110 | 83 | 74.5% | x | 56.2% | Pattern #3 | Pattern #3 | −9.1% w/w (126.0° C.) | 6.0% |
| 9-E | | 75.3 | Water | 100 | 75 | 77.1% | x | 42.1% | Pattern #2c | Pattern #20 | −3.4% w/w (155.1° C.) | N/A |
| 9-F | 8-A4 (Experiment Reference 8-Sample Reference A4) | 75.2 | Water | 100 | 75 | 82.3% | ✓ | 25.5% | Pattern #2c | Pattern #2c | −2.0% w/w (146.3° C.) | N/A |
| 9-G | Sample Reference 1 | 75.4 | Water | 100 | 75 | 81.1% | x | 21.5% | Pattern #2c | Pattern #2c | N/A | N/A |

Comparative XRPD data is provided in FIGS. 199-206.

9-E (Experiment Reference 9-Sample Reference E) and 9-F (Experiment Reference 9-Sample Reference F) formed consistent crystal structures throughout oven drying (FIG. 203 and FIG. 204). The same crystal structure was formed for 9-A (Experiment Reference 9-Sample Reference A), (9-E (Experiment Reference 9-Sample Reference E) and 9-F (Experiment Reference 9-Sample Reference F) (FIG. 205). However, form change was observed in 9-F (Experiment Reference 9-Sample Reference F), when compared to the input material of 8-A2 (Experiment Reference 8-Sample Reference A2) which suggested that the crystal form evolved from the thermocycle could be more stable than the previous form following water equilibration (FIG. 206). Therefore, 9-G (Experiment Reference 9-Sample Reference G) was performed in purified water, applying 35 cycles to enforce the conversion to a single higher melt event material. The DSC profile of the product obtained showed the same 3 melting point events (FIG. 176). The product from the thermocycle then underwent equilibration in purified water at 90° C. to attempt to evolve the phase solely into the higher melt form, however, were not able to isolate the higher melt event material (insufficient quantity for analysis, material appeared as a film around the vial). Based on the above observations, a new form investigation was performed by preparing the hemi-fumarate salt in purified water in order to rule out the presence of tabernanthalog hemifumarate, or related metastable polymorphs (refer to re-proportionation investigation).

ix. Re-Proportionation Investigation (Experiment Reference 10)

a. Experimental Procedure

10-A: Tabernanthalog (native) (50.8 mg, 1 wt) and fumaric acid (6.8 mg, 0.5 equiv) were charged into a vial. Purified water (250 ml, 5 vol) was subsequently added, and the suspension was stirred at 50° C. for ca. 24 h. The brown suspension was filtered through a sintered funnel and was dried under nitrogen flow.

10-B: Tabernanthalog (native) (50.6 mg, 1 wt) and fumaric acid (8.9 mg, 0.5 equiv) were charged into a vial. Purified water (250 ml, 5 vol) was subsequently added, and the suspension was stirred at 20° C. for ca. 24 h. The brown suspension was filtered through a sintered funnel and was dried under nitrogen flow.

b. Analytical Characterization Data

DSC

DSC profiles are provided in FIGS. 207 and 208.

XRPD

XRPD data is provided in FIG. 209 and Table 105.

TABLE 105

Peak angle data of 10-A1 (Experiment Reference 10-Sample Reference A1) (Pattern #22)

| 2-θ (°) | d Value | Rel. Intensity (%) |
|---|---|---|
| 10.5 | 8.44 | 25 |
| 15.1 | 5.86 | 18 |
| 18.9 | 4.68 | 100 |
| 27.4 | 3.26 | 24 | c. Conclusion

DSC analysis of this specimen (FIG. 210, black thermogram 10-B1 (Experiment Reference 10-Sample Reference B1)) exhibited 3 endothermic events, one of which coincided with the new peak that was observed during the thermocycling study (Experiment Reference 9). This phase then underwent crystallization into the stable hemi-fumarate at ca. 208° C.

Based on these results, the new higher melting form observed is most likely a disproportionated by-product (Tabernanthalog hemifumarate) and not a supraordinate version of the tabernanthalog fumarate salt. Therefore, Form A is still the progressable stable form (8-A4) (Experiment Reference 8-Sample Reference A4).

x. Heat-Up/Cool Down (HUCD) Crystallization in Different Solvents (Experiment Reference 11)

a. Experimental Procedure

Separate portions of the tabernanthalog monofumarate salt (Pattern #1, Sample Reference 1, ca 75 mg, 1.0 wt.) were charged to separate vessels. The appropriate solvents (750 µl, 10.0 vol, refer to Table 106) were charged to the relevant vessels and subsequent charges of the appropriate co-solvent were made to accomplish dissolution at reflux. The solutions were cooled to 18 to 23° C. and allowed to stand undisturbed, until crystallization was judged complete. After this time the products were isolated by centrifugation, washed with recycled maturation solvent, dried under reduced pressure at 40° C., and analyzed by XRPD for evidence of alternative crystalline forms.

b. Analytical Characterization Data

XRPD

Related XRPD data is provided in FIGS. 211-227 and Tables 107-123.

TABLE 107

Peak angle data of 11-A2 (Experiment Reference 11-Sample Reference A2) (Pattern #6a)

| 2-θ (°) | d Value | Rel. Intensity (%) |
|---|---|---|
| 12.9 | 6.86 | 11 |
| 16.5 | 5.37 | 71 |
| 19.4 | 4.58 | 45 |
| 19.5 | 4.56 | 100 |
| 20.6 | 4.32 | 67 |
| 22.0 | 4.04 | 22 |
| 25.3 | 3.52 | 72 |
| 26.0 | 3.42 | 39 |
| 33.4 | 2.68 | 14 |

TABLE 106

HUCD screen setup description

| Experiment Reference-Sample Reference | Input reference | Input weights (mg) | Solvent A | Solvent B | Co-solvents (volumes added, µl) | Key chemical functional groups | b.p. (° C.) | ICH Classes |
|---|---|---|---|---|---|---|---|---|
| 11-A | Tabernanthalog fumarate Sample Reference 1 | 74.7 | Acetone | water | 80 | Symmetrical ketone | 56 | 3 |
| 11-B | | 76.9 | Acetonitrile | water | 120 | Simple dipolar-aprotic nitrile | 82 | 2 |
| 11-C | | 77.6 | Butanol | water | 60 | Linear aliphatic alcohol | 118 | 3 |
| 11-D | | 76.7 | tert-Butyl-methyl ether | methanol | 2800 | Branched aliphatic methoxy ether | 55 | 3 |
| 11-E | | 75.7 | Dichloromethane | methanol | 880 | Chlorinated hydrocarbon | 40 | 2 |
| 11-F | | 77.2 | Ethanol | water | 60 | Linear aliphatic alcohol | 78 | 3 |
| 11-G | | 76.0 | methyl acetate | water/methanol | 80 | Aliphatic ester | 57 | 3 |
| 11-H | | 76.3 | 2-Propanol | water | 80 | Branched aliphatic alcohol | 83 | 3 |
| 11-I | | 77.4 | methanol | None | N/A | Linear aliphatic alcohol | 65 | 3 |
| 11-J | | 76.2 | Methylethyl ketone | water | 60 | Asymmetric dialkyl ketone | 80 | 3 |
| 11-K | | 75.5 | 2-Methyl THF | methanol | 1560 | Asymmetric cyclic ether | 80 | 3 |
| 11-L | | 74.8 | Tetrahydrofuran | water | 60 | Symmetric cyclic ether | 80 | # |
| 11-M | | 75.2 | Toluene | methanol | 980 | Alkyl aromatic hydrocarbon | 111 | 3 |
| 11-N | | 76.8 | Water | None | N/A | water | 100 | # |
| 11-O | | 74.6 | Dioxane | water | 60 | Symmetric cyclic ether | 101 | 2 |
| 11-P | | 76.4 | CPME | methanol | 1320 | Symmetric cyclic ether | 106 | 2 |
| 11-Q | | 75.6 | MIBK | methanol | 1300 | Asymmetric dialkyl ketone | 116 | 3 |

TABLE 108

Peak angle data of 11-B2 (Experiment Reference 11-Sample Reference B2) (Pattern #6a)

| 2-θ (°) | d Value | Rel. Intensity (%) |
|---|---|---|
| 12.9 | 6.85 | 10 |
| 16.5 | 5.36 | 88 |
| 19.4 | 4.58 | 39 |
| 19.5 | 4.54 | 100 |
| 20.6 | 4.30 | 94 |
| 22.0 | 4.03 | 22 |
| 25.3 | 3.52 | 76 |
| 26.0 | 3.42 | 35 |
| 33.5 | 2.67 | 13 |

TABLE 109

Peak angle data of 11-C2 (Experiment Reference 11-Sample Reference C2) (Pattern #6a)

| 2-θ (°) | d Value | Rel. Intensity (%) |
|---|---|---|
| 12.9 | 6.85 | 13 |
| 16.5 | 5.38 | 68 |
| 19.1 | 4.64 | 23 |
| 19.5 | 4.56 | 100 |
| 20.6 | 4.32 | 69 |
| 22.0 | 4.04 | 21 |
| 25.2 | 3.53 | 61 |
| 26.0 | 3.42 | 37 |
| 28.0 | 3.18 | 10 |
| 33.4 | 2.68 | 14 |
| 37.7 | 2.38 | 12 |

TABLE 110

Peak angle data of 11-D2 (Experiment Reference 11-Sample Reference D2) (Pattern #5)

| 2-θ (°) | d Value | Rel. Intensity (%) |
|---|---|---|
| 8.2 | 10.77 | 100 |
| 9.0 | 9.78 | 26 |
| 9.7 | 9.09 | 20 |
| 11.2 | 7.87 | 46 |
| 12.8 | 6.92 | 15 |
| 14.2 | 6.21 | 11 |
| 14.5 | 6.12 | 17 |
| 15.0 | 5.90 | 12 |
| 15.1 | 5.87 | 11 |
| 15.5 | 5.71 | 34 |
| 16.2 | 5.45 | 51 |
| 17.0 | 5.20 | 64 |
| 18.0 | 4.92 | 24 |
| 18.3 | 4.84 | 15 |
| 19.0 | 4.66 | 32 |
| 19.2 | 4.61 | 38 |
| 20.2 | 4.39 | 44 |
| 20.8 | 4.26 | 16 |
| 21.2 | 4.19 | 31 |
| 21.4 | 4.14 | 47 |
| 22.6 | 3.93 | 23 |
| 22.5 | 3.94 | 23 |
| 23.6 | 3.76 | 46 |
| 24.3 | 3.66 | 25 |
| 25.1 | 3.55 | 13 |
| 25.5 | 3.49 | 71 |
| 26.8 | 3.33 | 18 |
| 29.9 | 2.98 | 10 |

TABLE 111

Peak angle data of 11-E2 (Experiment Reference 11-Sample Reference E2) (Pattern #6b)

| 2-θ (°) | d Value | Rel. Intensity (%) |
|---|---|---|
| 8.3 | 10.70 | 10 |
| 13.0 | 6.82 | 20 |
| 16.5 | 5.35 | 29 |
| 19.5 | 4.55 | 100 |
| 20.6 | 4.30 | 30 |
| 22.1 | 4.03 | 15 |
| 25.3 | 3.51 | 21 |
| 26.1 | 3.41 | 57 |

TABLE 112

Peak angle data of 11-F2 (Experiment Reference 11-Sample Reference F2) (Pattern #6a)

| 2-θ (°) | d Value | Rel. Intensity (%) |
|---|---|---|
| 12.9 | 6.84 | 12 |
| 16.5 | 5.38 | 85 |
| 19.5 | 4.56 | 100 |
| 20.6 | 4.32 | 78 |
| 22.0 | 4.04 | 20 |
| 25.2 | 3.53 | 83 |
| 26.0 | 3.42 | 37 |
| 33.4 | 2.68 | 15 |
| 37.7 | 2.38 | 13 |

TABLE 113

Peak angle data of 11-G2 (Experiment Reference 11-Sample Reference G2) (Pattern #1)

| 2-θ (°) | d Value | Rel. Intensity (%) |
|---|---|---|
| 9.1 | 9.71 | 40 |
| 10.6 | 8.31 | 14 |
| 14.3 | 6.19 | 20 |
| 15.9 | 5.58 | 15 |
| 16.4 | 5.41 | 58 |
| 16.5 | 5.37 | 44 |
| 17.4 | 5.08 | 23 |
| 18.1 | 4.88 | 20 |
| 19.4 | 4.56 | 38 |

TABLE 113-continued

Peak angle data of 11-G2
(Experiment Reference
11-Sample Reference G2)
(Pattern #1)

| 2-θ (°) | d Value | Rel. Intensity (%) |
|---|---|---|
| 20.6 | 4.30 | 15 |
| 22.0 | 4.03 | 13 |
| 22.3 | 3.98 | 17 |
| 22.6 | 3.94 | 21 |
| 25.5 | 3.49 | 64 |
| 25.6 | 3.48 | 100 |
| 26.1 | 3.41 | 14 |
| 26.8 | 3.32 | 16 |
| 27.3 | 3.27 | 15 |
| 30.0 | 2.98 | 16 |

TABLE 114

Peak angle data of 11-H2
(Experiment Reference
11-Sample Reference H2)
(Pattern #6a)

| 2-θ (°) | d Value | Rel. Intensity (%) |
|---|---|---|
| 12.9 | 6.85 | 14 |
| 16.5 | 5.37 | 58 |
| 19.5 | 4.56 | 100 |
| 20.6 | 4.31 | 49 |
| 22.0 | 4.04 | 14 |
| 25.3 | 3.52 | 59 |
| 26.0 | 3.42 | 38 |
| 31.2 | 2.87 | 12 |

TABLE 115

Peak angle data of 11-I2
(Experiment Reference
11-Sample Reference I2)
(Pattern #6b)

| 2-θ (°) | d Value | Rel. Intensity (%) |
|---|---|---|
| 8.2 | 10.71 | 55 |
| 12.9 | 6.83 | 18 |
| 16.5 | 5.36 | 48 |
| 17.1 | 5.19 | 10 |
| 19.5 | 4.55 | 100 |
| 20.6 | 4.30 | 49 |
| 22.0 | 4.03 | 12 |
| 25.3 | 3.52 | 46 |
| 26.0 | 3.42 | 41 |

TABLE 116

Peak angle data of 11-J2
(Experiment Reference
11-Sample Reference J2)
(Pattern #6a)

| 2-θ (°) | d Value | Rel. Intensity (%) |
|---|---|---|
| 12.9 | 6.84 | 15 |
| 16.5 | 5.36 | 89 |

TABLE 116-continued

Peak angle data of 11-J2
(Experiment Reference
11-Sample Reference J2)
(Pattern #6a)

| 2-θ (°) | d Value | Rel. Intensity (%) |
|---|---|---|
| 19.5 | 4.55 | 99 |
| 19.5 | 4.55 | 100 |
| 20.6 | 4.30 | 84 |
| 22.0 | 4.03 | 20 |
| 25.3 | 3.52 | 75 |
| 26.0 | 3.42 | 37 |
| 28.1 | 3.18 | 10 |
| 33.5 | 2.68 | 12 |

TABLE 117

Peak angle data of 11-K2
(Experiment Reference
11-Sample Reference K2)
(Pattern #5)

| 2-θ (°) | d Value | Rel. Intensity (%) |
|---|---|---|
| 8.2 | 10.76 | 100 |
| 11.3 | 7.86 | 77 |
| 12.8 | 6.89 | 15 |
| 15.5 | 5.70 | 33 |
| 17.0 | 5.20 | 59 |
| 19.1 | 4.64 | 21 |
| 19.5 | 4.55 | 16 |
| 20.2 | 4.39 | 39 |
| 21.2 | 4.18 | 13 |
| 21.5 | 4.13 | 45 |
| 22.6 | 3.92 | 26 |
| 23.7 | 3.75 | 38 |
| 24.4 | 3.65 | 26 |
| 25.5 | 3.49 | 12 |
| 30.8 | 2.90 | 11 |

TABLE 118

Peak angle data of 11-L2
(Experiment Reference
11-Sample Reference L2)
(Pattern #6a)

| 2-θ (°) | d Value | Rel. Intensity (%) |
|---|---|---|
| 12.9 | 6.85 | 12 |
| 16.5 | 5.37 | 66 |
| 17.8 | 4.98 | 11 |
| 19.4 | 4.58 | 61 |
| 19.5 | 4.56 | 100 |
| 20.6 | 4.31 | 95 |
| 22.0 | 4.04 | 15 |
| 25.3 | 3.52 | 71 |
| 26.0 | 3.42 | 55 |
| 28.0 | 3.18 | 13 |
| 33.4 | 2.68 | 14 |
| 39.6 | 2.28 | 15 |

TABLE 119

Peak angle data of 11-M2
(Experiment Reference
11-Sample Reference M2)
(Pattern #6a)

| 2-θ (°) | d Value | Rel. Intensity (%) |
|---|---|---|
| 8.4 | 10.49 | 11 |
| 11.2 | 7.91 | 13 |
| 12.5 | 7.09 | 11 |
| 12.9 | 6.85 | 12 |
| 14.4 | 6.14 | 11 |
| 16.5 | 5.36 | 100 |
| 16.9 | 5.24 | 22 |
| 18.8 | 4.73 | 16 |
| 19.2 | 4.62 | 22 |
| 19.5 | 4.55 | 81 |
| 20.1 | 4.41 | 27 |
| 20.6 | 4.31 | 60 |
| 22.1 | 4.02 | 18 |
| 22.2 | 4.00 | 21 |
| 25.3 | 3.52 | 53 |
| 25.6 | 3.47 | 18 |
| 26.1 | 3.42 | 53 |
| 26.7 | 3.34 | 12 |
| 33.4 | 2.68 | 12 |

TABLE 120

Peak angle data of 11-N2
(Experiment Reference
11-Sample Reference N2)
(Pattern #6a)

| 2-θ (°) | d Value | Rel. Intensity (%) |
|---|---|---|
| 13.0 | 6.80 | 15 |
| 16.6 | 5.33 | 71 |
| 19.6 | 4.53 | 100 |
| 20.7 | 4.29 | 50 |
| 22.1 | 4.01 | 22 |
| 25.4 | 3.51 | 50 |
| 26.1 | 3.41 | 38 |
| 33.6 | 2.67 | 11 |

TABLE 121

Peak angle data of 11-O2
(Experiment Reference
11-Sample Reference O2)
(Pattern #6a)

| 2-θ (°) | d Value | Rel. Intensity (%) |
|---|---|---|
| 7.5 | 11.80 | 14 |
| 12.9 | 6.86 | 11 |
| 15.9 | 5.58 | 13 |
| 16.5 | 5.37 | 63 |
| 19.5 | 4.56 | 100 |
| 20.6 | 4.31 | 51 |
| 22.0 | 4.04 | 21 |
| 25.3 | 3.52 | 51 |
| 26.0 | 3.42 | 42 |
| 33.4 | 2.68 | 13 |

TABLE 122

Peak angle data of 11-P2
(Experiment Reference
11-Sample Reference P2)
(Pattern #5)

| 2-θ (°) | d Value | Rel. Intensity (%) |
|---|---|---|
| 8.2 | 10.77 | 100 |
| 11.3 | 7.85 | 51 |
| 12.8 | 6.90 | 15 |
| 15.5 | 5.70 | 43 |
| 16.3 | 5.43 | 15 |
| 17.0 | 5.20 | 64 |
| 19.1 | 4.64 | 31 |
| 19.4 | 4.56 | 16 |
| 20.2 | 4.39 | 47 |
| 20.6 | 4.32 | 12 |
| 21.3 | 4.16 | 33 |
| 21.5 | 4.13 | 77 |
| 22.7 | 3.92 | 26 |
| 23.7 | 3.75 | 53 |
| 24.3 | 3.65 | 15 |
| 25.5 | 3.49 | 29 |
| 26.0 | 3.42 | 11 |
| 30.8 | 2.90 | 11 |

TABLE 123

Peak angle data of 11-Q2
(Experiment Reference
11-Sample Reference Q2)
(Pattern #14)

| 2-θ (°) | d Value | Rel. Intensity (%) |
|---|---|---|
| 8.2 | 10.71 | 89 |
| 11.3 | 7.82 | 100 |
| 12.9 | 6.88 | 14 |
| 15.6 | 5.69 | 25 |
| 16.3 | 5.43 | 16 |
| 17.1 | 5.19 | 56 |
| 19.1 | 4.63 | 13 |
| 20.3 | 4.38 | 35 |
| 21.3 | 4.17 | 13 |
| 21.5 | 4.12 | 37 |
| 22.7 | 3.91 | 36 |
| 23.7 | 3.75 | 37 |
| 24.4 | 3.65 | 10 |
| 25.5 | 3.48 | 27 |
| 30.8 | 2.90 | 11 | c. Conclusion

Crystallization from different solvents can be a useful method to investigate alternative polymorphic forms. This crystallization screen of the tabernanthalog monofumarate salt could also be used to identify potential conditions for scale-up crystallizations to control the form outcome. XRPD analysis of the final products showed Patterns #1, #5, #6a and #6b. Evidently, in the presence of water, Patterns #6a and #6b were delivered (refer to Table 124). Apart from 11-E (Experiment Reference 11-Sample Reference E) were DCM and methanol were used.

TABLE 124

Summary for HUCD crystallization experiment

| Experiment Reference-Sample Reference | Input reference | Input weights (mg) | Solvent A | Solvent B | Co-solvents (volumes added, μl) | Key chemical functional groups | b.p. (° C.) | ICH Classes | Observations (t = 0 @ T = 20° C.) | XRPD (oven dried) | Tare | Gross | Net | Yield % |
|---|---|---|---|---|---|---|---|---|---|---|---|---|---|---|
| 11-A | Tabernanthalog fumarate Sample Reference 1 | 74.7 | Acetone | water | 80 | Symmetrical ketone | 56 | 3 | suspension | Pattern #6a | 1.0071 | 1.028 | 0.0209 | 28.0% |
| 11-B | | 76.9 | Acetonitrile | water | 120 | Simple dipolar-aprotic nitrile | 82 | 2 | cloudy | Pattern #6a | 1.0039 | 1.0394 | 0.0355 | 46.2% |
| 11-C | | 77.6 | Butanol | water | 60 | Linear aliphatic alcohol | 118 | 3 | suspension | Pattern #6a | 1.0024 | 1.0457 | 0.0433 | 55.8% |
| 11-D | | 76.7 | tert-Butylmethyl ether | methanol | 2800 | Branched aliphatic methoxyether | 55 | 3 | cloudy | Pattern #5 | 1.0007 | 1.0271 | 0.0264 | 34.4% |
| 11-E | | 75.7 | Dichloromethane | methanol | 880 | Chlorinated hydrocarbon | 40 | 2 | suspension | Pattern #6b | 1.0027 | 1.0508 | 0.048 | 63.5% |
| 11-F | | 77.2 | Ethanol | water | 60 | Linear aliphatic alcohol | 78 | 3 | suspension | Pattern #6a | 1.0035 | 1.0401 | 0.0366 | 47.4% |
| 11-G | | 76.0 | methyl acetate | water / methanol | 80 | Aliphatic ester | 57 | 3 | suspension | Pattern #1 | 1.0008 | 1.0289 | 0.0281 | 37.0% |
| 11-H | | 76.3 | 2-Propanol | water | 80 | Branched aliphatic alcohol | 83 | 3 | cloudy | Pattern #6a | 1.0026 | 1.0404 | 0.0378 | 49.5% |
| 11-I | | 77.4 | methanol | None | N/A | Linear aliphatic alcohol | 65 | 3 | suspension | Pattern #6b | 1.0051 | 1.0633 | 0.0582 | 75.2% |
| 11-J | | 76.2 | Methylethyl ketone | water | 60 | Asymmetric dialkyl ketone | 80 | 3 | suspension | Pattern #6a | 1.0043 | 1.0436 | 0.0393 | 51.6% |
| 11-K | | 75.5 | 2-Methyl THF | methanol | 1560 | Asymmetric cyclic ether | 80 | 3 | suspension | Pattern #5 | 0.9988 | 1.0312 | 0.0324 | 42.9% |
| 11-L | | 74.8 | Tetrahydrofuran | water | 60 | Symmetric cyclic ether | 80 | # | solution | Pattern #6a | 1.0119 | 1.0287 | 0.0168 | 22.5% |
| 11-M | | 75.2 | Toluene | methanol | 980 | Alkyl aromatic hydrocarbon | 111 | 3 | suspension | Pattern #6b | 1.0171 | 1.0568 | 0.0397 | 52.8% |
| 11-N | | 76.8 | Water | None | N/A | water | 100 | # | suspension | Pattern #6a | 1.0032 | 1.0542 | 0.051 | 66.4% |
| 11-O | | 74.6 | Dioxane | water | 60 | Symmetric cyclic ether | 101 | 2 | suspension | Pattern #6a | 1.0052 | 1.0253 | 0.0201 | 26.9% |
| 11-P | | 76.4 | CPME | methanol | 1320 | Symmetric cyclic ether | 106 | 2 | suspension | Pattern #5 | 1.0102 | 1.036 | 0.0258 | 33.8% |
| 11-Q | | 75.6 | MIBK | methanol | 1300 | Asymmetric dialkyl ketone | 116 | 3 | solution | Pattern #5 | 1.0079 | 1.0457 | 0.0378 | 50.0% | x. Mechanochemistry (LAG) (Experiment Reference 12)

a. Experimental Procedure

The tabernanthalog monofumarate salt (Pattern #1, Sample Reference 1, 75 mg) and one ball-bearing (7.0 mm, 1.4 g) were placed inside a steel vessel (1.5 ml), and attached to a Retsch MM 500, VARIO mixer-mill.

The vessel was oscillated at 500 rpm for 30 minutes, under neat grinding condition (NG, suffix-A) and liquid assisted grinding condition (LAG, methanol $\eta$=0.5, suffix-B).

b. Analytical Characterization Data

DSC
DSC results are provided in FIGS. 228 and 229.
XRPD
XRPD results are provided in FIGS. 230 and 231 and Tables 125 and 126.

TABLE 125

Peak angle data of 12-A1 (Experiment Reference 12-Sample Reference A1)

| 2-θ (°) | d Value | Rel. Intensity (%) |
|---|---|---|
| 6.8 | 12.98 | 13 |
| 9.2 | 9.65 | 30 |
| 14.3 | 6.18 | 15 |
| 16.4 | 5.39 | 90 |
| 16.8 | 5.27 | 35 |
| 17.6 | 5.05 | 15 |
| 17.9 | 4.95 | 16 |
| 18.2 | 4.87 | 32 |
| 18.9 | 4.69 | 14 |
| 19.4 | 4.57 | 41 |
| 22.2 | 4.00 | 11 |
| 22.4 | 3.96 | 21 |
| 23.2 | 3.83 | 13 |
| 25.6 | 3.47 | 100 |
| 26.3 | 3.39 | 12 |
| 26.9 | 3.31 | 26 |
| 27.3 | 3.27 | 22 |

TABLE 126

Peak angle data of 12-B1 (Experiment Reference 12-Sample Reference B1)

| 2-θ (°) | d Value | Rel. Intensity (%) |
|---|---|---|
| 8.2 | 10.74 | 44 |
| 9.1 | 9.76 | 25 |
| 11.2 | 7.88 | 27 |
| 12.8 | 6.90 | 12 |
| 14.2 | 6.22 | 13 |
| 15.5 | 5.71 | 21 |
| 16.3 | 5.42 | 82 |
| 17.0 | 5.20 | 39 |
| 18.1 | 4.91 | 16 |
| 19.3 | 4.60 | 18 |
| 19.5 | 4.55 | 26 |
| 20.2 | 4.39 | 26 |
| 20.6 | 4.30 | 17 |
| 21.5 | 4.14 | 27 |
| 21.5 | 4.13 | 29 |
| 22.0 | 4.04 | 10 |
| 22.6 | 3.94 | 22 |
| 22.6 | 3.93 | 23 |
| 23.7 | 3.75 | 28 |
| 25.6 | 3.48 | 100 |

TABLE 126-continued

Peak angle data of 12-B1 (Experiment Reference 12-Sample Reference B1)

| 2-θ (°) | d Value | Rel. Intensity (%) |
|---|---|---|
| 26.0 | 3.43 | 15 |
| 26.8 | 3.32 | 22 |
| 27.2 | 3.28 | 14 |
| 30.0 | 2.98 | 11 | c. Conclusion

Both pulverization conditions, appeared to promote incomplete conversion into the stable form identified as 6-S2 (Experiment Reference 6-Sample Reference S2), Pattern #6a (provided below). DSC thermograms under neat grinding (NG, 12-A1 (Experiment Reference 12-Sample Reference A1)) and under liquid assisted grinding conditions (LAG, 12-B1 (Experiment Reference 12-Sample Reference B1)) are presented in FIG. 232. XRPD diffractograms under neat grinding (NG, black. 12-A1 (Experiment Reference 12-Sample Reference A1), Pattern #6a, top right) and under liquid assisted grinding conditions (LAG, black, 12-B1 (Experiment Reference 12-Sample Reference B1), Pattern #6a, bottom, right) are presented in FIG. 233.

xi. Vapour Diffusion (Experiment Reference 13)

a. Experimental Procedure

The tabernanthalog monofumarate salt (Sample Reference 1, Pattern #1, 3×75 mg, 1 wt) was weighed out in to 3 separate snap-top vials and DMSO (375 ul, 5 vol) was charged to each vial. Gentle warning was applied to ensure full dissolution and the vials (open) were placed inside amber jars that contained 6 ml of DCM (13-A) (Experiment Reference 13-Sample Reference A), tBME (13-B) (Experiment Reference 13-Sample Reference B) and water (13-C) (Experiment Reference 13-Sample Reference C).

The 3 jars that contained the vials were left standing at 20° C., to allow slow movement of the diffusant solvent from the outer jar into the solvent inside the smaller, open wide-necked vessel and promote crystallization by altering the solvent composition.

b. Analytical Characterization Data $^1$H NMR
Relevant NMR spectra are provided in FIGS. 234 and 235.
TGA
Relevant TGA profiles are provided in FIGS. 236 and 237.
DSC
Relevant DSC profiles are provided in FIGS. 238 and 239.
XRPD
XRPD results are provided in FIG. 240-243 and Table 127-130.

TABLE 127

Peak angle data of 13-B1 (Experiment Reference 13-Sample Reference B1) (Pattern #24)

| 2-θ (°) | d Value | Rel. Intensity (%) |
|---|---|---|
| 12.4 | 7.16 | 19 |
| 15.7 | 5.63 | 31 |

TABLE 127-continued

Peak angle data of 13-B1 (Experiment Reference 13-Sample Reference B1) (Pattern #24)

| 2-θ (°) | d Value | Rel. Intensity (%) |
|---|---|---|
| 16.1 | 5.50 | 25 |
| 16.7 | 5.29 | 14 |
| 17.2 | 5.16 | 100 |
| 20.1 | 4.41 | 13 |
| 20.8 | 4.27 | 37 |
| 21.1 | 4.20 | 22 |
| 21.6 | 4.11 | 19 |
| 22.3 | 3.99 | 28 |
| 23.0 | 3.86 | 39 |
| 24.9 | 3.57 | 20 |
| 27.4 | 3.25 | 40 |

TABLE 128

Peak angle data of 13-B2 (Experiment Reference 13-Sample Reference B2) (Pattern #24)

| 2-θ (°) | d Value | Rel. Intensity (%) |
|---|---|---|
| 12.2 | 7.22 | 20 |
| 15.6 | 5.66 | 39 |
| 15.9 | 5.56 | 25 |
| 17.0 | 5.20 | 100 |
| 20.7 | 4.29 | 32 |
| 21.0 | 4.23 | 22 |
| 21.5 | 4.13 | 15 |
| 22.9 | 3.88 | 38 |
| 24.8 | 3.59 | 19 |
| 27.3 | 3.26 | 30 |

TABLE 129

Peak angle data of 13-C1 (Experiment Reference 13-Sample Reference C1) (Pattern #23)

| 2-θ (°) | d Value | Rel. Intensity (%) |
|---|---|---|
| 12.9 | 6.85 | 72 |
| 15.0 | 5.90 | 11 |
| 16.1 | 5.51 | 47 |
| 17.1 | 5.19 | 33 |
| 17.8 | 4.99 | 100 |
| 18.8 | 4.72 | 12 |
| 20.5 | 4.32 | 26 |
| 20.9 | 4.24 | 29 |
| 21.6 | 4.12 | 44 |
| 22.3 | 3.99 | 15 |
| 23.0 | 3.87 | 98 |
| 23.2 | 3.83 | 20 |
| 25.0 | 3.56 | 20 |
| 25.7 | 3.47 | 61 |
| 26.8 | 3.32 | 28 |
| 27.4 | 3.25 | 69 |
| 28.1 | 3.18 | 14 |
| 38.9 | 2.31 | 12 |

TABLE 130

Peak angle data of 13-C2 (Experiment Reference 13-Sample Reference C2) (Pattern #23)

| 2-θ (°) | d Value | Rel. Intensity (%) |
|---|---|---|
| 12.2 | 7.25 | 12 |
| 12.8 | 6.90 | 40 |
| 14.9 | 5.94 | 11 |
| 16.0 | 5.54 | 39 |
| 16.2 | 5.45 | 23 |
| 16.9 | 5.24 | 24 |
| 17.6 | 5.02 | 100 |
| 20.4 | 4.35 | 19 |
| 20.8 | 4.27 | 22 |
| 21.4 | 4.14 | 30 |
| 22.9 | 3.89 | 76 |
| 23.1 | 3.85 | 16 |
| 25.6 | 3.48 | 36 |
| 26.7 | 3.33 | 19 |
| 27.3 | 3.27 | 39 |

PLM

PLM results are provided in FIGS. 244-247.

c. Conclusion

Vapour diffusion is a slower thermodynamic crystallization technique and good for generating single crystals suitable for SCXRD. It involved a solution of the tabernanthalog monofumarate salt in the relevant non-diffusant solvent (DMSO was used due to the inherent low solubility of the tabernanthalog monofumarate salt), being placed inside a small, wide-necked vessel. The wide-necked vessel was then placed inside a larger jar, and the appropriate diffusant solvent (DCM, tBME and water were used. Water was included as one of the diffusant solvents, to try and generate crystals suitable for SCXRD) was added to the jar, to form a moat of diffusant around the smaller vessel (FIG. 248).

As the diffusant solvent gradually evaporated, the composition of the non-diffusant solvent changed and in doing so, promoted de-supersaturation and crystallization of the tabernanthalog monofumarate salt. (13-A) (Experiment Reference 13-Sample Reference A) remained in full solution, and (13-A) (Experiment Reference 13-Sample Reference A) and (13-B) (Experiment Reference 13-Sample Reference B) did not appear to give suitable crystals for SCXRD (refer to Table 131). Microscopy showed that (13-B) (Experiment Reference 13-Sample Reference B) had much larger single crystals than (13-C) (Experiment Reference 13-Sample Reference C). Both samples showed large amounts of aggregation.

TABLE 131

Summary of vapour diffusion experiment

| Experiment Reference-Sample Reference | Input reference | Input weights (mg) | Solvent A (5 vol) | Solvent B | Co-solvents (volumes added, mL) | XRPD crystallinity (wet pellet) | XRPD crystallinity (oven dried) | crystal form change following dry | Tare (mg) | Gross (mg) | Net (mg) | Yield % | $^1$H NMR (solvent content, % w/w) |
|---|---|---|---|---|---|---|---|---|---|---|---|---|---|
| 13-A | Sample | 75.1 | DMSO | DCM | 6.0 | | | OP | 1019.2 | | | | |
| 13-B | Refer- | 75.1 | DMSO | TBME | 6.0 | Pattern #24 | Pattern #24 | O | 1000.7 | 1017.7 | 17.0 | 22 | DMSO = |

TABLE 131-continued

Summary of vapour diffusion experiment

| Experiment Reference-Sample Reference | Input reference | Input weights (mg) | Solvent A (5 vol) | Solvent B | Co-solvents (volumes added, mL) | XRPD crystallinity (wet pellet) | XRPD crystallinity (oven dried) | crystal form change following dry | Tare (mg) | Gross (mg) | Net (mg) | Yield % | 1H NMR (solvent content, % w/w) |
|---|---|---|---|---|---|---|---|---|---|---|---|---|---|
| 13-C | ence 1 | 75.5 | DMSO | Water | 6.0 | (v disordered) Pattern #23 (v. disordered) | (v. disordered) Pattern #23 (v. disordered) | O | 999.8 | 1019.5 | 19.7 | 26 | 1.14 DMSO = 0.78 | xii. Evaporation Screen (Experiment Reference 14)

a. Experimental Procedure

Crystallization of the API was examined by changing the composition of the crystallization solvent by evaporation of a volatile diluent. This technique is useful for generating kinetic forms and solvates. Separate portions of the tabernanthalog monofumarate salt (Pattern #1, Sample Reference 1, ca 50 mg, 1.0 wt.) were charged to separate vessels. DMSO (100 µl, 2.0 vol, refer to Table 132) was charged to the relevant vessels and subsequent charges of the appropriate co-solvent (900 µl, 18.0 vol) were made to accomplish dissolution. The vials were covered with an aluminum foil cap and pierced with a single hole, then left to stand at 20° C. After 6 days, gentle nitrogen flux was applied to dryness. The products were analyzed by XRPD and companion analyses, for evidence of alternative crystalline forms.

TABLE 132

Evaporation screen setup description

| Experiment Reference-Sample Reference | Input reference | Input weights (mg) | Solvent A (1 vol) | Solvent volume added (mL) | Solvent B (19 vol) | Co-solvents volumes added (mL) |
|---|---|---|---|---|---|---|
| 14-A | Sample | 51.0 | DMSO | 0.1 | EtOH | 0.9 |
| 14-B | Reference | 49.2 | DMSO | 0.1 | nBuOH | 0.9 |
| 14-C | 1 | 50.2 | DMSO | 0.1 | Water | 0.9 | b. Analytical Characterization Data

1H NMR
Relevant NMR spectra are provided in FIGS. 249-251.
TGA
Relevant TGA profiles are provided in FIGS. 252-254.
XRPD
Relevant XRPD profiles are provided in FIGS. 255-260 and Tables 133-138.

TABLE 133

Peak angle data of 14-A1 (Experiment Reference 14-Sample Reference A1) (wet sample, disordered Pattern #23)

| 2-θ (°) | d Value | Rel. Intensity (%) |
|---|---|---|
| 7.8 | 11.34 | 11 |
| 12.4 | 7.14 | 15 |
| 13.0 | 6.82 | 44 |
| 13.0 | 6.78 | 31 |
| 15.0 | 5.89 | 12 |
| 16.1 | 5.49 | 35 |
| 16.4 | 5.39 | 18 |
| 16.7 | 5.30 | 24 |
| 17.2 | 5.16 | 23 |
| 17.8 | 4.98 | 78 |
| 18.4 | 4.82 | 13 |
| 19.6 | 4.53 | 38 |
| 19.7 | 4.51 | 100 |
| 20.9 | 4.25 | 41 |
| 21.6 | 4.11 | 33 |
| 22.3 | 3.98 | 31 |
| 23.0 | 3.86 | 66 |
| 23.3 | 3.82 | 18 |
| 25.6 | 3.48 | 30 |
| 26.1 | 3.41 | 22 |
| 26.3 | 3.39 | 49 |
| 26.9 | 3.32 | 18 |
| 27.5 | 3.24 | 33 |
| 28.1 | 3.17 | 11 |

TABLE 134

Peak angle data of 14-A2 (Experiment Reference 14-Sample Reference A2) (oven dried sample, Pattern #23)

| 2-θ (°) | d Value | Rel. Intensity (%) |
|---|---|---|
| 7.7 | 11.50 | 11 |
| 12.2 | 7.28 | 12 |
| 12.8 | 6.93 | 24 |

TABLE 134-continued

Peak angle data of 14-A2 (Experiment Reference 14-Sample Reference A2) (oven dried sample, Pattern #23)

| 2-θ (°) | d Value | Rel. Intensity (%) |
| --- | --- | --- |
| 14.9 | 5.96 | 12 |
| 15.9 | 5.56 | 32 |
| 16.2 | 5.46 | 26 |
| 16.5 | 5.38 | 22 |
| 16.8 | 5.26 | 21 |
| 17.6 | 5.04 | 100 |
| 19.4 | 4.56 | 27 |
| 20.4 | 4.35 | 17 |
| 20.7 | 4.30 | 23 |
| 21.4 | 4.15 | 28 |
| 22.1 | 4.02 | 12 |
| 22.8 | 3.89 | 64 |
| 23.1 | 3.85 | 13 |
| 25.4 | 3.50 | 22 |
| 25.5 | 3.49 | 26 |
| 26.7 | 3.34 | 16 |
| 27.2 | 3.27 | 34 |
| 27.9 | 3.20 | 11 |

TABLE 135

Peak angle data of 14-B1 (Experiment Reference 14-Sample Reference B1) (wet sample, disordered Pattern #23)

| 2-θ (°) | d Value | Rel. Intensity (%) |
| --- | --- | --- |
| 7.7 | 11.45 | 27 |
| 12.3 | 7.19 | 15 |
| 12.8 | 6.92 | 48 |
| 15.7 | 5.64 | 31 |
| 16.0 | 5.55 | 32 |
| 16.3 | 5.45 | 20 |
| 17.0 | 5.20 | 60 |
| 17.6 | 5.02 | 100 |
| 20.7 | 4.28 | 39 |
| 21.0 | 4.22 | 48 |
| 21.5 | 4.14 | 45 |
| 22.9 | 3.88 | 71 |
| 24.9 | 3.57 | 56 |
| 25.5 | 3.49 | 91 |
| 26.7 | 3.33 | 42 |
| 27.3 | 3.26 | 46 |

TABLE 136

Peak angle data of 14-B2 (Experiment Reference 14-Sample Reference B2) (oven dried sample, Pattern #23)

| 2-θ (°) | d Value | Rel. Intensity (%) |
| --- | --- | --- |
| 12.2 | 7.22 | 12 |
| 12.9 | 6.88 | 32 |
| 16.0 | 5.52 | 37 |
| 16.3 | 5.43 | 39 |
| 16.9 | 5.23 | 20 |
| 17.7 | 5.01 | 100 |
| 20.4 | 4.34 | 17 |
| 20.8 | 4.26 | 18 |
| 21.5 | 4.13 | 23 |
| 22.2 | 4.00 | 11 |

TABLE 136-continued

Peak angle data of 14-B2 (Experiment Reference 14-Sample Reference B2) (oven dried sample, Pattern #23)

| 2-θ (°) | d Value | Rel. Intensity (%) |
| --- | --- | --- |
| 22.9 | 3.88 | 61 |
| 23.1 | 3.84 | 13 |
| 25.6 | 3.48 | 34 |
| 26.8 | 3.33 | 17 |
| 27.3 | 3.26 | 29 |

TABLE 137

Peak angle data of 14-C1 (Experiment Reference 14-Sample Reference C1) (wet sample, high background Pattern #6a)

| 2-θ (°) | d Value | Rel. Intensity (%) |
| --- | --- | --- |
| 13.0 | 6.79 | 14 |
| 16.6 | 5.33 | 17 |
| 17.1 | 5.17 | 20 |
| 19.6 | 4.53 | 100 |
| 20.8 | 4.27 | 31 |
| 22.2 | 4.01 | 10 |
| 23.0 | 3.86 | 13 |
| 25.4 | 3.50 | 17 |
| 26.2 | 3.40 | 58 |
| 27.5 | 3.25 | 11 |

TABLE 138

Peak angle data of 14-C2 (Experiment Reference 14-Sample Reference C2) (oven dried sample, Pattern #6a)

| 2-θ (°) | d Value | Rel. Intensity (%) |
| --- | --- | --- |
| 13.0 | 6.83 | 24 |
| 16.5 | 5.35 | 44 |
| 17.0 | 5.20 | 10 |
| 19.4 | 4.58 | 18 |
| 19.5 | 4.55 | 100 |
| 20.7 | 4.30 | 44 |
| 22.1 | 4.02 | 21 |
| 25.3 | 3.51 | 37 |
| 26.1 | 3.41 | 61 |

Photography

Photography results are shown in FIGS. 261-263.

c. Conclusion

An evaporation screen of the tabernanthalog monofumarate salt was performed to determine if alternative polymorphic forms were generated by evaporative crystallization from different solvents. XRPD results showed much higher crystallinity following oven dry (FIGS. 264-266) and TGA showed no solvent release. Table 139 presents a summary of evaporation screen experiment.

TABLE 139

Summary of evaporation screen experiment

| Experiment Reference-Sample Reference | Input reference | Input weights (mg) | Solvent A (1 vol) | Solvent volume added (mL) | Solvent B (19 vol) | Co-solvents volumes added (mL) | XRPD crystallinity (wet pellet) | XRPD crystallinity (oven dried) | Yield % | $^1$H NMR (solvent content, % w/w) |
|---|---|---|---|---|---|---|---|---|---|---|
| 14-A | Sample Reference 1 | 51.0 | DMSO | 0.1 | EtOH | 0.9 | Disordered (Pattern #23) | Pattern 23 | 37.5 | DMSO = 0.75 Ethanol ND |
| 14-B | | 49.2 | DMSO | 0.1 | nBuOH | 0.9 | Disordered (Pattern #23) | Pattern 23 | 64.2 | DMSO = 0.91 Butanol ND |
| 14-C | | 50.2 | DMSO | 0.1 | Water | 0.9 | High background (Pattern #6a) | Pattern 6a | 91.2 | DMSO = 2.21 | xiii. In-Situ Hydration Evaluation (Experiment Reference 15)

a. Experimental Procedure

An XRPD plate was made up with a small amount of the tabernanthalog monofumarate salt (Pattern #1, Sample Reference 1, 5 mg, 1.0 wt) and analyzed by XRPD on the 9-minute method and labelled as T=0. After the run, the sample was charged with purified water (10 µL, 2.0 vol) and analyzed again by XRPD, labelled as T=9. This was repeated twice more for T=18 and T=27. The sample was left to stand under ambient conditions (15-25° C., ambient humidity, and pressure) in the fume hood for 33 h and then analyzed by XRPD.

b. Analytical Characterization Data

XRPD

XRPD results are shown in FIGS. 267-271 and Tables 140-143.

TABLE 140

Peak angle data of 15-T0 (Experiment Reference 15-Sample Reference T0) (Pattern #1, Sample Reference 1)

| 2-θ (°) | d Value | Rel. Intensity (%) |
|---|---|---|
| 9.1 | 9.72 | 27 |
| 14.2 | 6.21 | 13 |
| 16.4 | 5.42 | 74 |
| 16.7 | 5.30 | 29 |
| 17.5 | 5.07 | 12 |
| 17.7 | 5.00 | 10 |
| 18.1 | 4.89 | 29 |
| 19.3 | 4.59 | 34 |
| 22.3 | 3.98 | 24 |
| 22.5 | 3.95 | 11 |
| 23.1 | 3.84 | 11 |
| 25.2 | 3.53 | 18 |
| 25.6 | 3.48 | 100 |
| 26.2 | 3.40 | 13 |
| 26.8 | 3.32 | 25 |
| 27.3 | 3.27 | 24 |
| 28.7 | 3.11 | 11 |
| 30.0 | 2.98 | 11 |

TABLE 141

Peak angle data of 15-T9 (Experiment Reference 15-Sample Reference T9) (amorphousised Pattern #1)

| 2-θ (°) | d Value | Rel. Intensity (%) |
|---|---|---|
| 9.1 | 9.70 | 13 |
| 14.3 | 6.20 | 11 |
| 16.4 | 5.41 | 65 |
| 17.5 | 5.07 | 13 |
| 18.1 | 4.90 | 17 |
| 22.3 | 3.98 | 14 |
| 25.1 | 3.54 | 15 |
| 25.6 | 3.48 | 100 |
| 26.8 | 3.33 | 24 |
| 27.2 | 3.28 | 16 |
| 29.9 | 2.98 | 14 |

TABLE 142

Peak angle data of 15-T27 (Experiment Reference 15-Sample Reference T27) (amorphousised Pattern #1)

| 2-θ (°) | d Value | Rel. Intensity (%) |
|---|---|---|
| 6.8 | 13.06 | 11 |
| 9.1 | 9.68 | 31 |
| 14.3 | 6.20 | 15 |
| 16.4 | 5.41 | 80 |
| 16.7 | 5.31 | 24 |
| 18.1 | 4.89 | 19 |
| 19.4 | 4.58 | 16 |
| 22.4 | 3.96 | 19 |
| 25.2 | 3.53 | 25 |
| 25.6 | 3.48 | 100 |
| 26.8 | 3.32 | 25 |
| 27.2 | 3.27 | 17 |
| 28.1 | 3.17 | 11 |
| 28.6 | 3.12 | 16 |
| 30.0 | 2.98 | 19 |

TABLE 143

Peak angle data of 15-T33 (Experiment Reference 15-Sample Reference T33) (amorphized Pattern #1)

| 2-θ (°) | d Value | Rel. Intensity (%) |
|---|---|---|
| 6.8 | 13.03 | 16 |
| 9.1 | 9.68 | 43 |
| 14.3 | 6.19 | 18 |
| 15.1 | 5.88 | 6 |
| 16.2 | 5.46 | 18 |
| 16.4 | 5.39 | 100 |
| 16.8 | 5.26 | 34 |
| 17.5 | 5.06 | 19 |
| 17.9 | 4.96 | 15 |
| 18.2 | 4.87 | 21 |
| 18.9 | 4.69 | 13 |

TABLE 143-continued

Peak angle data of 15-T33 (Experiment Reference 15-Sample Reference T33) (amorphized Pattern #1)

| 2-θ (°) | d Value | Rel. Intensity (%) |
|---|---|---|
| 19.4 | 4.57 | 33 |
| 22.4 | 3.96 | 17 |
| 24.9 | 3.57 | 12 |
| 25.4 | 3.51 | 84 |
| 25.7 | 3.47 | 61 |
| 26.6 | 3.34 | 19 |
| 26.8 | 3.32 | 16 | c. Conclusion

The overlaid XRPD results indicate that the same crystal form is recovered following hydration and subsequent drying (FIG. 272).

xiv. Competitive Suspension Equilibration (Form A and Form B) (Experiment Reference 16)

a. Experimental Procedure

Equimolar quantities of Form A (Pattern #6a, 25.4 mg, 1 wt, 8-A4, (Experiment Reference 8-Sample Reference A4)) and Form B (Pattern #2a, 25.0 mg, 1 wt, Sample B-A2) were suspended in tBME (250 μl, 5.0 vol). The first experiment was agitated at 20° C., (16-A) (Experiment Reference 16-Sample Reference A), while the other was agitated at 40° C. (16-B) (Experiment Reference 16-Sample Reference B). The suspension was monitored by XRPD analysis.

b. Analytical Characterization Data

XRPD

XRPD results are provided in FIGS. 273-282 and Tables 144-153.

TABLE 144

Peak angle data of 16-A1 (Experiment Reference 16-Sample Reference A1) (wet sample, t = 24 h)

| 2-θ (°) | d Value | Rel. Intensity (%) |
|---|---|---|
| 9.1 | 9.74 | 24 |
| 12.2 | 7.22 | 24 |
| 14.2 | 6.22 | 12 |
| 15.7 | 5.65 | 32 |
| 15.9 | 5.57 | 17 |
| 16.4 | 5.41 | 92 |
| 16.5 | 5.36 | 49 |
| 17.0 | 5.20 | 63 |
| 18.1 | 4.91 | 23 |
| 19.5 | 4.54 | 56 |
| 20.7 | 4.30 | 64 |
| 21.0 | 4.23 | 18 |
| 22.1 | 4.02 | 15 |
| 22.9 | 3.88 | 28 |
| 24.9 | 3.57 | 13 |
| 25.6 | 3.48 | 100 |
| 26.1 | 3.41 | 19 |
| 26.8 | 3.33 | 22 |
| 27.3 | 3.26 | 27 |

TABLE 145

Peak angle data of 16-A2 (Experiment Reference 16-Sample Reference A2) (wet sample, t = 48 h)

| 2-θ (°) | d Value | Rel. Intensity (%) |
|---|---|---|
| 9.0 | 9.77 | 19 |
| 12.2 | 7.24 | 18 |
| 12.9 | 6.85 | 12 |
| 14.2 | 6.23 | 12 |
| 15.7 | 5.66 | 26 |
| 15.9 | 5.58 | 17 |
| 16.4 | 5.41 | 75 |
| 16.5 | 5.38 | 82 |
| 17.0 | 5.20 | 41 |
| 17.9 | 4.94 | 12 |
| 18.0 | 4.92 | 14 |
| 18.7 | 4.74 | 10 |
| 19.5 | 4.55 | 100 |
| 20.6 | 4.30 | 88 |
| 20.9 | 4.25 | 13 |
| 22.0 | 4.03 | 21 |
| 22.9 | 3.88 | 18 |
| 24.8 | 3.58 | 11 |
| 25.4 | 3.51 | 73 |
| 25.5 | 3.49 | 66 |
| 26.0 | 3.42 | 29 |
| 26.7 | 3.33 | 14 |
| 27.3 | 3.27 | 16 |
| 33.5 | 2.68 | 10 |

TABLE 146

Peak angle data of 16-A3 (Experiment Reference 16-Sample Reference A3) (wet sample, t = 108 h)

| 2-θ (°) | d Value | Rel. Intensity (%) |
|---|---|---|
| 9.1 | 9.76 | 21 |
| 12.2 | 7.23 | 19 |
| 12.9 | 6.84 | 12 |
| 14.2 | 6.23 | 12 |
| 15.7 | 5.65 | 23 |
| 16.4 | 5.39 | 75 |
| 16.5 | 5.37 | 82 |
| 17.0 | 5.20 | 41 |
| 18.0 | 4.92 | 16 |
| 19.5 | 4.55 | 100 |
| 20.6 | 4.30 | 87 |
| 21.0 | 4.24 | 11 |
| 22.0 | 4.03 | 21 |
| 22.9 | 3.88 | 17 |
| 25.4 | 3.51 | 68 |
| 25.5 | 3.49 | 59 |
| 26.1 | 3.42 | 32 |
| 26.8 | 3.33 | 16 |
| 27.3 | 3.26 | 14 |
| 33.5 | 2.68 | 11 |

TABLE 147

Peak angle data of 16-A4 (Experiment Reference 16-Sample Reference A4) (wet sample, t = 192 h)

| 2-θ (°) | d Value | Rel. Intensity (%) |
|---|---|---|
| 9.1 | 9.71 | 17 |
| 12.3 | 7.20 | 16 |
| 13.0 | 6.82 | 14 |
| 15.7 | 5.63 | 21 |
| 16.5 | 5.36 | 87 |
| 17.1 | 5.19 | 30 |
| 18.1 | 4.90 | 21 |
| 19.5 | 4.54 | 100 |
| 20.7 | 4.29 | 77 |
| 22.1 | 4.02 | 21 |

TABLE 147-continued

Peak angle data of 16-A4 (Experiment Reference 16-Sample Reference A4) (wet sample, t = 192 h)

| 2-θ (°) | d Value | Rel. Intensity (%) |
|---|---|---|
| 23.0 | 3.87 | 17 |
| 25.4 | 3.50 | 67 |
| 25.5 | 3.48 | 55 |
| 26.1 | 3.41 | 30 |
| 26.8 | 3.32 | 13 |
| 26.8 | 3.32 | 11 |
| 27.4 | 3.26 | 13 |
| 33.5 | 2.67 | 10 |

TABLE 148

Peak angle data of 16-A8 (Experiment Reference 16-Sample Reference A8) (wet sample, t = 4 weeks)

| 2-θ (°) | d Value | Rel. Intensity (%) |
|---|---|---|
| 12.2 | 7.23 | 11 |
| 12.9 | 6.83 | 14 |
| 16.6 | 5.34 | 96 |
| 16.5 | 5.36 | 96 |
| 17.1 | 5.19 | 20 |
| 17.8 | 4.97 | 19 |
| 18.1 | 4.91 | 30 |
| 18.8 | 4.73 | 12 |
| 19.5 | 4.54 | 100 |
| 20.7 | 4.30 | 76 |
| 22.1 | 4.03 | 18 |
| 22.9 | 3.88 | 11 |
| 25.4 | 3.51 | 66 |
| 25.5 | 3.49 | 46 |
| 26.1 | 3.41 | 28 |

TABLE 149

Peak angle data of 16-B1 (Experiment Reference 16-Sample Reference B1) (wet sample, t = 24 h)

| 2-θ (°) | d Value | Rel. Intensity (%) |
|---|---|---|
| 9.1 | 9.73 | 16 |
| 12.2 | 7.22 | 14 |
| 13.0 | 6.83 | 14 |
| 15.7 | 5.65 | 25 |
| 15.9 | 5.56 | 12 |
| 16.5 | 5.36 | 76 |
| 17.1 | 5.19 | 38 |
| 18.0 | 4.91 | 16 |
| 18.8 | 4.72 | 10 |
| 19.5 | 4.55 | 100 |
| 20.7 | 4.30 | 75 |
| 21.0 | 4.24 | 11 |
| 22.1 | 4.03 | 23 |
| 22.9 | 3.88 | 18 |
| 25.4 | 3.50 | 57 |
| 25.5 | 3.49 | 53 |
| 26.1 | 3.42 | 36 |
| 26.8 | 3.33 | 13 |
| 27.3 | 3.26 | 14 |

TABLE 150

Peak angle data 16-B2 (Experiment Reference 16-Sample Reference B2) (wet sample, t = 48 h)

| 2-θ (°) | d Value | Rel. Intensity (%) |
|---|---|---|
| 9.1 | 9.75 | 15 |
| 12.2 | 7.22 | 14 |
| 12.9 | 6.84 | 15 |
| 15.7 | 5.65 | 22 |
| 16.5 | 5.37 | 63 |
| 17.0 | 5.20 | 31 |
| 18.0 | 4.91 | 15 |
| 19.5 | 4.55 | 100 |
| 20.6 | 4.30 | 56 |
| 20.9 | 4.24 | 13 |
| 22.1 | 4.03 | 21 |
| 22.9 | 3.88 | 14 |
| 25.4 | 3.50 | 50 |
| 26.1 | 3.42 | 44 |
| 27.3 | 3.26 | 12 |
| 33.5 | 2.68 | 11 |

TABLE 151

Peak angle data of 16-B3 (Experiment Reference 16-Sample Reference B3) (wet sample, t = 108 h)

| 2-θ (°) | d Value | Rel. Intensity (%) |
|---|---|---|
| 9.0 | 9.76 | 13 |
| 12.2 | 7.24 | 13 |
| 12.9 | 6.85 | 12 |
| 14.2 | 6.23 | 10 |
| 15.7 | 5.66 | 19 |
| 16.4 | 5.41 | 55 |
| 16.5 | 5.38 | 72 |
| 17.0 | 5.20 | 29 |
| 18.0 | 4.92 | 20 |
| 19.5 | 4.56 | 100 |
| 20.6 | 4.31 | 70 |
| 20.8 | 4.26 | 14 |
| 22.0 | 4.03 | 22 |
| 22.9 | 3.88 | 19 |
| 25.3 | 3.51 | 54 |
| 25.5 | 3.49 | 46 |
| 26.0 | 3.42 | 36 |
| 26.7 | 3.33 | 13 |
| 27.3 | 3.27 | 11 |
| 33.4 | 2.68 | 10 |

TABLE 152

Peak angle data of 16-B4 (Experiment Reference 16-Sample Reference B4) (wet sample, t = 192 h)

| 2-θ (°) | d Value | Rel. Intensity (%) |
|---|---|---|
| 12.3 | 7.18 | 10 |
| 13.0 | 6.78 | 12 |
| 15.8 | 5.59 | 15 |
| 16.6 | 5.33 | 68 |
| 17.1 | 5.17 | 21 |
| 17.8 | 4.98 | 19 |
| 18.1 | 4.91 | 35 |
| 18.8 | 4.71 | 10 |
| 19.6 | 4.53 | 100 |
| 20.7 | 4.28 | 54 |
| 22.1 | 4.01 | 24 |
| 23.0 | 3.86 | 13 |
| 25.4 | 3.50 | 53 |
| 26.2 | 3.40 | 41 |

TABLE 153

Peak angle data of 16-B8 (Experiment Reference 16-Sample Reference B8) (wet sample, t = 4 weeks)

| 2-θ (°) | d Value | Rel. Intensity (%) |
|---|---|---|
| 13.0 | 6.78 | 10 |
| 12.9 | 6.84 | 16 |
| 16.1 | 5.52 | 12 |
| 16.5 | 5.35 | 85 |
| 17.0 | 5.22 | 11 |
| 17.7 | 5.01 | 32 |
| 18.0 | 4.91 | 44 |
| 19.5 | 4.55 | 100 |
| 20.7 | 4.29 | 62 |
| 22.1 | 4.02 | 21 |
| 22.9 | 3.88 | 18 |
| 25.4 | 3.51 | 61 |
| 26.1 | 3.41 | 32 |
| 26.7 | 3.34 | 11 |
| 33.5 | 2.67 | 10 | c. Conclusion

Competitive suspension equilibration of Form A (8-A4) (Experiment Reference 8-Sample Reference A4) versus Form B (Sample B-A2) was performed at 20° C. ((16-A; Experiment Reference 16-Sample Reference A) and 40° C. ((16-B; Experiment Reference 16-Sample Reference B) in tBME (5.0 vol) to verify that Form A (Pattern #6a) is more stable. The output of the suspension was monitored by XRPD analysis and overlaid with the two inputs to confirm the conversion towards Form A. The stacked XRPD timepoints were consistent with gradual transformation of Form B (Pattern #2a) into Form A (Pattern #6a) in both experiments, supporting the relative stability of succession Form A>Form B ((FIG. 283 and FIG. 284). At the end of the experiment, Form A was the dominant form, therefore the stable one. Summary of competitive suspension equilibration between Form A and Form B (16-A (Experiment Reference 16-Sample Reference A) and 16-B (Experiment Reference 16-Sample Reference B)) is provided in Table 153A.

block-shaped crystal with dimensions 0.13×0.05×0.03 mm$^3$ was selected. This crystal was mounted on a MITIGEN holder in perfluoro ether oil on a Rigaku 007HF diffractometer with HF Varimax confocal mirrors, an UG2 goniometer and HyPix 6000HE detector. The crystal was kept at a steady T=300(2) K during data collection. The structure was solved with the ShelXT 2014/5 (Sheldrick, 2014) solution program using dual methods and by using Olex2 1.5 (Dolomanov et al., 2009) as the graphical interface. The model was refined with ShelXL 2014/7 (Sheldrick, 2015) using full matrix least squares minimisation on F$^2$.

11-M2 (Experiment Reference 11-Sample Reference M2): X-ray data were collected upon a colorless block-shaped crystal with dimensions 0.13×0.05×0.03 mm$^3$, which was mounted on a MITIGEN holder in perfluoro ether oil. X-ray diffraction data were collected using a Rigaku 007HF diffractometer with HF Varimax confocal mirrors, an UG2 goniometer and HyPix 6000HE detector equipped with an Oxford Cryosystems low-temperature device, operating at T=300(2) K.

Data were measured using profile data from ω-scans of 0.5° per frame for 3.0/12.0 s using Cu K α radiation (Rotating anode, 40.0 kV, 30.0 mA). The total number of runs and images was based on the strategy calculation from the program CrysAlisPro 1.171.42.51a (Rigaku OD, 2022). The maximum resolution achieved was Θ=76.907°.

Cell parameters were retrieved using the CrysAlisPro 1.171.42.51a (Rigaku OD, 2022) software and refined using CrysAlisPro 1.171.42.51a (Rigaku OD, 2022) on 14613 reflections, 44% of the observed reflections. Data reduction was performed using the CrysAlisPro 1.171.42.51a (Rigaku OD, 2022) software which corrects for Lorentz polarisation. The final completeness is 100.00% (IUCr) out to 76.907° in Θ

A multi-scan absorption correction was performed using CrysAlisPro 1.171.42.51a (Rigaku Oxford Diffraction, 2022) Empirical absorption correction using spherical harmonics, implemented in SCALE3 ABSPACK scaling algorithm. The absorption coefficient m of this material is 0.801 mm$^{-1}$ at this wavelength (λ=1.54184 Å) and the minimum and maximum transmissions are 0.696 and 1.000.

TABLE 153A

Summary of competitive suspension equilibration between Form A and Form B (16-A and 16-B). More time points were examined between 192 h and 4 weeks; however, they were very similar with 16-A4 (Experiment Reference 16-Sample Reference A4) an 16-B4 (Experiment Reference 16-Sample Reference B4), respectively.

| References | Input reference | Input weights (mg) | Solvent | T (° C.) | XRPD (24 h, -A1) | XRPD (48 h, -A2) | XRPD (108 h, -A3) | XRPD (192 h, -A4) | XRPD (4 weeks, -A8) |
|---|---|---|---|---|---|---|---|---|---|
| 16-A | 8-A4 (Form A) and Sample B-A2 (Form B) | 25.4 (Form A) and 25.0 (Form B) | TBME (5.0 vol) | 20 | Form A > Form B | Form A > Form B | Form A > Form B | Form A >> Form B | Form A >> Form B |
| 16-B | | | | 40 | Form A > Form B | Form A > Form B | Form A > Form B | Form A >> Form B | Form A >> Form B | xiv. SCXRD (Single Crystal (SC) Experiments)

a. Experimental Procedure

A crystalline sample of 11-M2 (Experiment Reference 11-Sample Reference M2) and 11-Q2 (Experiment Reference 11-Sample Reference Q2), which were used as supplied, was isolated. A small portion of this sample was suspended in perfluoro ether oil and a suitable colorless The structure was solved in the space group P2$_1$/c (#14) by using dual methods using the ShelXT 2014/5 (Sheldrick, 2014) structure solution program and refined by full matrix least squares minimisation on F$^2$ using version 2014/7 of ShelXL 2014/7 (Sheldrick, 2015). All non-hydrogen atoms were refined anisotropically. The positions of the N—H atoms H1 and H2 and the O—H atom H4 were located from the electron difference map and refined with their thermal parameters linked to their parent atoms. The positions of the remaining H atoms were calculated geometrically and refined using the riding model.

There is a single molecule in the asymmetric unit, which is represented by the reported sum formula. In other words: Z is 4 and Z' is 1.

11-Q2 (Experiment Reference 11-Sample Reference Q2): X-ray data were collected upon a yellow rod-shaped crystal with dimensions 0.10×0.03×0.01 mm$^3$, which was mounted on a MITIGEN holder in perfluoro ether oil. X-ray diffraction data were collected using a Rigaku 007HF diffractometer with HF Varimax confocal mirrors, an UG2 goniometer and HyPix 6000HE detector equipped with an Oxford Cryosystems low-temperature device, operating at T=300(2) K.

Data were measured using profile data from ω-scans of 0.5° per frame for 9.0/36.0 s using Cu K α radiation (Rotating anode, 40.0 kV, 30.0 mA). The total number of runs and images was based on the strategy calculation from the program CrysAlisPro 1.171.42.51a (Rigaku OD, 2022). The maximum resolution achieved was Θ=77.152°.

Cell parameters were retrieved using the CrysAlisPro 1.171.42.51a (Rigaku OD, 2022) software and refined using CrysAlisPro 1.171.42.51a (Rigaku OD, 2022) on 2649 reflections, 23% of the observed reflections. Data reduction was performed using the CrysAlisPro 1.171.42.51a (Rigaku OD, 2022) software which corrects for Lorentz polarisation. The final completeness is 98.10% (IUCr) out to 77.152° in Θ.

A multi-scan absorption correction was performed using CrysAlisPro 1.171.42.51a (Rigaku Oxford Diffraction, 2022) Empirical absorption correction using spherical harmonics, implemented in SCALE3 ABSPACK scaling algorithm. The absorption coefficient m of this material is 0.680 mm$^{-1}$ at this wavelength (λ=1.54184 Å) and the minimum and maximum transmissions are 0.733 and 1.000.

The structure was solved in the space group C2/c (#15) by using dual methods using the ShelXT 2014/5 (Sheldrick, 2014) structure solution program and refined by full matrix least squares minimisation on F$^2$ using version 2014/7 of ShelXL 2014/7 (Sheldrick, 2015). All non-hydrogen atoms were refined anisotropically. The positions of the N—H atoms H1 and H2 and the O—H atom H4 were located from the electron difference map and refined with their thermal parameters linked to their parent atoms. The positions of the remaining H atoms were calculated geometrically and refined using the riding model.

The value of Z' is 2. This means that there are two independent molecules in the asymmetric unit.

b. Analytical Characterization Data

Crystal data for 11-M2 (Experiment Reference 11-Sample Reference M2) and Crystal data for 11-Q2 (Experiment Reference 1 I-Sample Reference Q2) are provided in FIGS. 285 and 286, respectively.

c. Conclusion (i) SCXRD Form A (Pattern #6a)

The crystalline tabernanthalog monofumarate (Pattern #6a) is characterized by XRPD signals as forth in Table 119.

Crystal Data for 11-M2 (Experiment Reference 11-Sample Reference M2) (FIG. 287). $C_{18}H_{22}N_2O_5$, M$_r$=346.37, monoclinic, P2$_1$/c (No. 14), a=7.43280(10) Å, b=8.59740(10) Å, c=27.5143(3) Å, b=96.6990(10)°, a=g=90°, V=1746.24(4) Å$^3$, T=300(2) K, Z=4, Z'=1, m(Cu K$_a$)=0.801 mm$^{-1}$, 32845 reflections measured, 3622 unique (R$_{int}$=0.0333) which were used in all calculations. The final wR$_2$ was 0.1071 (all data) and R$_1$ was 0.0409 (I≥2 s(I)).

One molecule of Tabernanthalog and one molecule of fumaric acid were present in the unit cell. The hydrogen bonding network is shown (FIG. 288), thus, fumaric acid adopted a 1,4-orientated linear configuration, exhibiting head to tail hydrogen bonding between oxygen atoms O3-O4 (2.48 Å), while oxygen atom O2 was hydrogen bonded to nitrogen atom N1, located on the azepine ring (O2-N1, 2.70 Å), assumed to be salified.

Form A (Pattern #6a) is now definitely characterized. Cameron et al. (Nature, 2021 January; 589(7842):474-479) did not contain a crystallographic information file and a search of the Cambridge Crystallographic Data base, did not reveal a hit set for Tabernanthalog or its salts, only originator Ibogaine. Accordingly, this phase is a novel and stable polymorph.

The simulated powder pattern obtained from the single crystal diffraction data at 300° K, adequately explained the experimentally observed powder diffraction pattern of Form A (11-M2 (Experiment Reference 11-Sample Reference M2)), at the same temperature.

Comparison of simulated powder pattern (11-M2 (Experiment Reference 11-Sample Reference M2)) and experimentally obtained powder diffraction pattern for 6-S2 (Experiment Reference 6-Sample Reference S2) (Form A, Pattern #6a, reference) is provided in FIG. 289. XRPD diffractogram overlay of simulated powder diffraction pattern of (11-M2 (Experiment Reference 11-Sample Reference M2); Form A) and 6-S2 ((Experiment Reference 6-Sample Reference S2), red, Form A reference) is provided in FIG. 289A.

Void space was calculated for solvent accessible surface (FIG. 290). For illustration, the void space was arbitrarily calculated for minimum probe radii of 0.6 and 0.9 A (for example, well beneath that of water at 1.4 Å). No regular voids in the crystal structure were large enough to accommodate non-crystal-bonded, molecular water.

(ii) SCXRD Form I (Pattern #14)

The crystalline tabernanthalog hemifumarate (Pattern #14) is characterized by XRPD signals as forth in Table 123.

Crystal Data for 11-Q2 (Experiment Reference 11-Sample Reference Q2) (Form I, refer to FIG. 291). $C_{8.12}H_{10.5}NO_{1.62}$, M$_r$=148.17, monoclinic, C2/c (No. 15), a=21.7386(8) Å, b=9.7033(5) Å, c=15.8640(8) Å, b=99.182 (4)°, a=g=90°, V=3303.4(3) Å$^3$, T=300(2) K, Z=16, Z'=2, m(Cu K$_a$)=0.680 mm$^{-1}$, 11278 reflections measured, 3227 unique (R$_R$A=0.0472) which were used in all calculations. The final wR$_2$ was 0.2751 (all data) and R$_1$ was 0.0857 (I≥2 s(I)).

One molecule of Tabernanthalog and one-half molecule of fumaric acid were present in the unit cell; in addition, non-crystal bonded methanol (disordered) was present in a structural pocket.

The hydrogen bonding network is shown; thus, fumaric acid was situated in-between two molecules of Tabernanthalog via hydrogen bonds to the azepine (N1-O2, 2.70 Å) and indole nitrogen atoms (N2-O3, 2.81 Å). The methanol molecule is not crystal-bonded to the API, i.e., it is located in a structural pocket and will tumble, within this pocket, contributing to its disorder; this mode of solvent occupancy would be classified as a channel, or non-stoichiometric solvate. Because the precise location of the methanol within the pocket is not known, due to non-crystal bonding and tumbling, there is uncertainty regarding the stoichiometry; however, methanol is estimated to be 0.25 molecule occupancy in the unit cell. Expungement of methanol from the crystal at low pressure and/or relative humidity, is expected to be facile and should not result in major re-organization of the crystal structure. Form I, hemi-fumarate is definitively characterized. Hydrogen bonding network of Tabernanthalog hemifumarate (Pattern #14, Form I) is provided in FIG. 292.

The simulated powder pattern obtained from the single crystal diffraction data at 300° K (11-Q2 (Experiment Reference 11-Sample Reference Q2)), explained the experimentally observed powder diffraction pattern at the same temperature, of previously assigned Form I (Pattern #14), tabernanthalog hemifumarate (reference 5-B3 (Experiment Reference 5-Sample Reference B3), FIG. 293).

XRPD diffractogram overlay of simulated powder diffraction pattern (11-Q2 (Experiment Reference 11-Sample Reference Q2), Form I) and 5-B3 ((Experiment Reference 5-Sample Reference B3), Form I reference) is provided in FIG. 293A.

Unit cell volume of tabernanthalog hemifumarate, Pattern #14, Form I (3303 Å) was almost double that of the tabernanthalog monofumarate salt, Pattern #6a, Form A (1746 Å), consistent with greater vacancy in the structure (FIG. 294). The pocket in which the methanol molecule resides is shown (refer to green atom label 04 and the methanol molecule appeared to be 'doubled-up', because of uncertainty regarding its position due to tumbling, i.e. contributed to disordering). Void space was calculated for solvent accessible surface and contingent on local solvent activities, it may be possible to exchange the methanol molecule by small molecules such as water, acetone etc.

E. Characterisation Data

The Tabernanthalog Monofumarate Salt (Sample Reference 1, Pattern #1)

IUPAC name is 8-methoxy-3-methyl-1H,2H,3H,4H,5H,6H-azepino[4,5-b]indole fumarate [Mass: 346.383; Exact mass: 346.152871816: Formula: $C_{18}H_{22}N_2O_5$; and Composition: C (62.42%), H (6.40%), N (8.09%), O (23.09%)].

Table 154 lists a summary of the characterization data of the batch used to for the polymorph screen experiments.

TABLE 154

Batch used to for the polymorph screen experiments

| Batch reference | HPLC (% area) | Q $^1$H NMR (% w/w) | MeCN content (% w/w) | KF titre (% w/w water) | XRPD assignment |
|---|---|---|---|---|---|
| Sample Reference 1 | 97.64 | 93.13 | 0.16 | 2.6* | Pattern #1 |

* Theoretical hemihydrate = 2.5% w/w, 355.4 molg$^{-1}$ $^1$H NMR spectra are provided in FIGS. 295 and 296. XRPD results are provided in FIGS. 297 and 298 and Tables 155 and 156.

TABLE 155

Peak angle data of the tabernanthalog monofumarate salt (Pattern #1, Sample Reference 1)

| 2-θ (°) | d Value | Rel. Intensity (%) |
|---|---|---|
| 9.0 | 9.77 | 21 |
| 14.2 | 6.23 | 11 |
| 16.3 | 5.43 | 70 |
| 16.7 | 5.31 | 28 |
| 17.4 | 5.08 | 13 |
| 17.7 | 5.01 | 10 |

TABLE 155-continued

Peak angle data of the tabernanthalog monofumarate salt (Pattern #1, Sample Reference 1)

| 2-θ (°) | d Value | Rel. Intensity (%) |
|---|---|---|
| 18.1 | 4.90 | 26 |
| 19.3 | 4.60 | 43 |
| 22.3 | 3.98 | 19 |
| 23.1 | 3.85 | 12 |
| 25.1 | 3.54 | 16 |
| 25.5 | 3.49 | 100 |
| 26.1 | 3.41 | 13 |
| 26.8 | 3.33 | 23 |
| 27.2 | 3.27 | 23 |
| 30.0 | 2.98 | 11 |

TABLE 156

Peak angle data of the tabernanthalog monofumarate salt ground (Pattern #1, Sample Reference 1)

| 2-θ (°) | d Value | Rel. Intensity (%) |
|---|---|---|
| 9.0 | 9.79 | 20 |
| 15.6 | 5.67 | 14 |
| 16.3 | 5.43 | 69 |
| 16.7 | 5.29 | 28 |
| 17.4 | 5.08 | 15 |
| 17.8 | 4.99 | 14 |
| 18.1 | 4.90 | 23 |
| 18.8 | 4.72 | 11 |
| 19.3 | 4.59 | 37 |
| 22.3 | 3.98 | 18 |
| 23.1 | 3.84 | 11 |
| 24.6 | 3.62 | 17 |
| 25.1 | 3.54 | 11 |
| 25.5 | 3.48 | 100 |
| 26.2 | 3.40 | 11 |
| 26.8 | 3.32 | 22 |
| 27.2 | 3.27 | 18 |

The TGA profile of the tabernanthalog fumarate salt (Sample Reference 1) was acquired at a ramp rate of +10° C./minute (FIG. 299). The first TG event (−2.1% w/w) was consistent with the release of volatiles, potentially water and solvent (water −2.6% w/w+acetonitrile −0.2% w/w). Significant weight loss was observed at higher temperature (>200° C.), attributed to chemical degradation and ablation of the sample.

The DSC profile of the tabernanthalog fumarate salt (Sample Reference 1) was acquired at a ramp rate of +10° C./minute (FIG. 300). The DSC profile exhibited a bimodal transition that corresponds to the melting of two different crystal forms.

The DVS profiles of the tabernanthalog fumarate salt (Sample Reference 1) is provided in FIG. 301 and the PLM data is provided in FIGS. 302 and 303. The SEM data is provided in FIGS. 304-307. As can be seen in FIG. 307 (resolution at 2500×), large irregular particles were observed. SEM surface topography appeared to consist of tightly compacted foliated plates. Bright particles at wide field were associated with electrical discharge effects. HPLC profile is provided in FIG. 308.

Summary of Forms
i. Monofumarate Salts

1Pattern #1 (7-N2, Example 2) (Experiment Reference 7-Sample Reference N2)

The list of representative experiments that resulted in Pattern #1 is provided in Table 156A.

TABLE 156A

List of representative experiments that resulted in Pattern #1.
PATTERN #1

| | |
|---|---|
| 1-S1; shifted +0.2° 2θ | 6-B1 |
| 1-R1; shifted +0.2° 2θ | 6-B2 |
| 2-A1 (t = 3 h) | 6-C2 |
| 2-A2 (t = 24 h); shifted +0.1° 2θ | 6-C1 (strained) |
| 2-A3 (t = 4 d); shifted +0.1° 2θ | 1-E1 (20.6°, 21.9°, 24.6° 2θ) |
| | 7-G2 |
| 2-A5 (t = 14 d) | 7-D2 |
| 2-A6 (t = 21 d) | 6-N2 |
| 2-B1 (t = 3 h); shifted +0.1° 2θ | 6-M2 |
| 2-B2 (t = 24 h) | 6-M1 |
| 2-B3 | 7-E2 |
| 2-B5 | 1-D1 |
| 2-B6 | 6-O1 |
| 6-I1 | 7-N2 |
| 6-I2 | 1-T1 |
| 7-C1 | 1-O1 |
| 7-C2 | 7-R1 |
| 7-I1; shifted +0.1° 2θ | |
| 7-I2 | 9-B1 |
| 7-L2 | 15-T0 (CAT8931) |
| 2-B4; shifted +0.1° 2θ | 9-B2 |
| 2-A4; shifted +0.1° 2θ | 11-G2 |

Preparation

Pattern #1 was prepared in acetonitrile/water or in 2Me-THF.

The characterization data of 7-N2 (Experiment Reference 7-Sample Reference N2) is provided in FIG. 4, FIG. 309, FIG. 311, and FIG. 312 and Table 157.

TABLE 157

Peak angle data of 7-N2 (Experiment Reference 7-Sample Reference N2) (oven dried)

| 2-θ (°) | d Value | Rel. Intensity (%) |
|---|---|---|
| 5.1 | 17.41 | 31 |
| 6.7 | 13.15 | 11 |
| 9.0 | 9.78 | 24 |
| 10.2 | 8.69 | 29 |
| 16.3 | 5.43 | 70 |
| 16.7 | 5.30 | 33 |
| 17.4 | 5.09 | 16 |
| 17.7 | 5.00 | 13 |
| 18.1 | 4.90 | 26 |
| 19.3 | 4.60 | 43 |
| 22.3 | 3.99 | 22 |
| 23.0 | 3.86 | 12 |
| 25.2 | 3.54 | 18 |
| 25.5 | 3.49 | 100 |
| 26.1 | 3.41 | 14 |
| 26.8 | 3.32 | 23 |
| 27.2 | 3.27 | 27 |
| 29.9 | 2.98 | 12 |

2. Pattern #2a (Form B, Unary Fumarate, 7-B2 (Experiment Reference 7-Sample Reference 1B2))

The list of representative experiments that resulted in Pattern #2a is provided in Table 157A.

TABLE 157A

List of representative experiments that resulted in Pattern #2a.
PATTERN #2a

7-J1
7-J2
7-M1
7-B1 (v. br., high background)
7-B2
7-O2 (little strained)
1-B1
7-M2

Preparation

Pattern #2a was prepared in acetonitrile.

The characterization data of 7-1B2 (Experiment Reference 7-Sample Reference B2) is provided in FIG. 3, FIG. 313, FIG. 315 and FIG. 316 and Table 158.

TABLE 158

XRPD Signal angle data of 7-B2 (Experiment Reference 7-Sample Reference B2) (oven dried)

| 2-θ (°) | d Value | Rel. Intensity (%) |
|---|---|---|
| 9.1 | 9.73 | 31 |
| 12.3 | 7.20 | 22 |
| 14.2 | 6.21 | 15 |
| 15.7 | 5.64 | 28 |
| 16.4 | 5.42 | 86 |
| 17.1 | 5.18 | 62 |
| 17.4 | 5.09 | 13 |
| 18.1 | 4.90 | 24 |
| 18.8 | 4.71 | 11 |
| 20.7 | 4.29 | 24 |
| 21.0 | 4.22 | 16 |
| 22.3 | 3.98 | 11 |
| 22.8 | 3.90 | 19 |
| 23.0 | 3.87 | 31 |
| 24.7 | 3.60 | 13 |
| 25.0 | 3.55 | 21 |
| 25.6 | 3.48 | 100 |
| 26.8 | 3.32 | 28 |
| 27.3 | 3.26 | 29 |

3. Pattern #2b (6-G2 (Experiment Reference 6-Sample Reference G2))

The list of representative experiments that resulted in Pattern #2b is provided in Table 158A.

TABLE 158A

List of representative experiments that resulted in Pattern #2b
PATTERN #2b

6-H2
6-A2
6-Q2
6-G2
6-L2
7-H2

Preparation

Pattern #2b was prepared in ethyl acetate.

The characterization data of 6-G2 (Experiment Reference 6-Sample Reference G2) is provided in FIG. 8, FIG. 317, FIG. 319 and FIG. 320 and Table 159.

TABLE 159

XRPD Signal angle data of 6-G2-(Experiment Reference 6-Sample Reference G2) (oven dried)

| 2-θ (°) | d Value | Rel. Intensity (%) |
|---|---|---|
| 9.0 | 9.76 | 26 |
| 14.2 | 6.23 | 13 |
| 15.5 | 5.70 | 21 |
| 15.8 | 5.59 | 25 |
| 16.3 | 5.43 | 80 |
| 17.0 | 5.21 | 20 |
| 17.4 | 5.10 | 17 |
| 18.1 | 4.90 | 30 |
| 18.8 | 4.72 | 13 |
| 19.4 | 4.57 | 17 |
| 21.0 | 4.24 | 10 |
| 22.3 | 3.98 | 16 |
| 22.6 | 3.94 | 18 |
| 24.6 | 3.61 | 39 |
| 25.1 | 3.54 | 26 |
| 25.5 | 3.48 | 100 |
| 26.8 | 3.33 | 23 |

4. Pattern #2c (1-P2 (Experiment Reference 1-Sample Reference P2))

The list of representative experiments that resulted in Pattern #2c is provided in Table 159A.

TABLE 159A

List of representative experiments that resulted in Pattern #2c.
PATTERN #2c

| |
|---|
| 1-P2 |
| 1-P1 |
| 1-L1 |
| 9-A2 |
| 9-G1 |
| 9-G2 |
| 9-E1 |
| 9-E2 |
| 9-F1 |
| 9-F2 |

Preparation

Pattern #2c was prepared in water.

The characterization data of 1-P2 (Experiment Reference 1-Sample Reference P2) is provided in FIGS. 321-325 and Table 160.

TABLE 160

XRPD Signal angle data of 1-P2 (Experiment Reference 1-Sample Reference P2) (oven dried)

| 2-θ (°) | d Value | Rel. Intensity (%) |
|---|---|---|
| 9.0 | 9.80 | 20 |
| 16.3 | 5.44 | 64 |
| 16.7 | 5.30 | 34 |
| 17.4 | 5.09 | 12 |
| 17.7 | 5.00 | 15 |
| 18.1 | 4.90 | 19 |
| 19.3 | 4.60 | 49 |
| 20.2 | 4.40 | 10 |
| 21.2 | 4.18 | 11 |
| 22.3 | 3.99 | 25 |
| 23.0 | 3.86 | 13 |
| 25.1 | 3.54 | 13 |
| 25.5 | 3.49 | 100 |
| 26.1 | 3.41 | 14 |
| 26.8 | 3.33 | 17 |
| 27.2 | 3.27 | 20 |

5. Pattern #2d (7-H1 (Experiment Reference 7-Sample Reference H1))

The list of representative experiments that resulted in Pattern #2d is provided in Table 160A.

TABLE 160A

List of representative experiments that resulted in Pattern #2d.
PATTERN #2d

| |
|---|
| 7-H1 |
| 6-H1 |

Preparation

Pattern #2d was prepared in ethyl formate.

XRPD data of 7-H1 (Experiment Reference 7-Sample Reference H1) is provided in FIG. 326 and Table 161. 7-H1 (Experiment Reference 7-Sample Reference H1) converted to Pattern #2b upon oven-drying (7-H2) (Experiment Reference 7-Sample Reference H-2).

TABLE 161

XRPD Signal angle data of 7-H1 (Experiment Reference 7-Sample Reference H1) (wet pellet).

| 2-θ (°) | d Value | Rel. Intensity (%) |
|---|---|---|
| 9.1 | 9.72 | 29 |
| 14.2 | 6.21 | 15 |
| 16.2 | 5.46 | 57 |
| 16.3 | 5.43 | 81 |
| 17.5 | 5.05 | 15 |
| 18.1 | 4.90 | 21 |
| 19.9 | 4.46 | 17 |
| 21.1 | 4.20 | 17 |
| 22.1 | 4.02 | 28 |
| 25.2 | 3.54 | 37 |
| 25.6 | 3.48 | 100 |
| 26.0 | 3.43 | 27 |
| 26.8 | 3.32 | 25 |
| 27.2 | 3.28 | 11 |
| 28.6 | 3.12 | 10 |
| 30.0 | 2.98 | 11 |

6. Pattern #3 (6-R2 (Experiment Reference 6-Sample Reference R2))

The list of representative experiments that resulted in Pattern #3 is provided in Table 161A.

TABLE 161A

List of representative experiments that resulted in Pattern #3.

PATTERN #3

| |
|---|
| 6-D2 |
| 6-D1 |
| 6-R1 (disordered) |
| 6-R2 |
| 7-D1 |

TABLE 161A-continued

List of representative experiments that resulted in Pattern #3.

| PATTERN #3 |
|---|
| 9-D1 |
| 9-D2 |

Preparation

Pattern #3 was prepared in toluene.

The characterization data of 6-R2 (Experiment Reference 6-Sample Reference R2) is provided in FIG. 12, FIG. 327, FIG. 329 and FIG. 330 and Table 162.

TABLE 162

XRPD Signal angle data of 6-R2
(Experiment Reference 6-Sample Reference R2) (oven dried)

| 2-θ (°) | d Value | Rel. Intensity (%) |
|---|---|---|
| 8.4 | 10.51 | 13.2011 |
| 9.0 | 9.78 | 24.8928 |
| 9.8 | 9.06 | 5.6975 |
| 11.1 | 7.94 | 18.5193 |
| 12.5 | 7.10 | 15.6155 |
| 14.3 | 6.20 | 14.1395 |
| 14.4 | 6.15 | 15.5720 |
| 16.3 | 5.43 | 82.2143 |
| 16.6 | 5.34 | 64.8774 |
| 16.8 | 5.26 | 28.3532 |
| 17.4 | 5.09 | 11.0713 |
| 18.0 | 4.91 | 21.7920 |
| 18.8 | 4.73 | 27.8544 |
| 19.3 | 4.59 | 12.9813 |
| 20.1 | 4.41 | 40.6675 |
| 22.2 | 4.00 | 37.7836 |
| 22.5 | 3.94 | 23.1797 |
| 24.7 | 3.60 | 16.5107 |
| 25.0 | 3.55 | 19.1800 |
| 25.5 | 3.49 | 100.0000 |
| 26.0 | 3.42 | 39.9175 |
| 26.8 | 3.33 | 28.4983 |
| 27.2 | 3.27 | 11.0895 |
| 29.9 | 2.98 | 10.9865 |

7. Pattern #4a (6-K2 (Experiment Reference 6-Sample Reference K2))

The list of representative experiments that resulted in Pattern #±4a is provided in Table 162A.

TABLE 162A

List of representative experiments that resulted in Pattern #4a.

| PATTERN #4a |
|---|
| 6-P2 |
| 6-F2 |
| 6-K1 |
| 6-K2 |

Preparation

Pattern #4a was prepared in methanol.

The characterization data of 6-K2 (Experiment Reference 6-Sample Reference K2) is provided in FIG. 10, FIG. 331, FIG. 333 and FIG. 334 and Table 163.

TABLE 163

XRPD Signal angle data of 6-K2
(Experiment Reference 6-Sample Reference K2) (oven dried)

| 2-θ (°) | d Value | Rel. Intensity (%) |
|---|---|---|
| 8.2 | 10.79 | 52 |
| 9.0 | 9.78 | 27 |
| 11.3 | 7.85 | 31 |
| 12.7 | 6.95 | 12 |
| 14.2 | 6.23 | 14 |
| 15.6 | 5.67 | 17 |
| 16.3 | 5.43 | 89 |
| 17.1 | 5.18 | 25 |
| 18.0 | 4.91 | 22 |
| 18.9 | 4.69 | 16 |
| 19.3 | 4.60 | 25 |
| 19.4 | 4.57 | 24 |
| 20.4 | 4.35 | 18 |
| 20.5 | 4.32 | 21 |
| 21.5 | 4.13 | 23 |
| 22.6 | 3.93 | 16 |
| 23.8 | 3.74 | 26 |
| 25.2 | 3.53 | 17 |
| 25.5 | 3.49 | 100 |
| 26.8 | 3.33 | 24 |
| 30.0 | 2.98 | 10 |

9. Pattern #4b (6-O2 (Experiment Reference 6-Sample Reference O2))

The list of representative experiments that resulted in Pattern #4b is provided in Table 163A.

TABLE 163A

List of representative experiments that resulted in Pattern #4b.

| PATTERN #4b |
|---|
| 6-E2 |
| 6-E1 |
| 6-O2 |

Preparation

Pattern #4b was prepared in nitromethane.

The characterization data of 6-O2 (Experiment Reference 6-Sample Reference O2) is provided in FIG. 11, FIG. 335, FIG. 337 and FIG. 338 and Table 164.

TABLE 164

XRPD Signal angle data of 6-O2
(Experiment Reference 6-Sample Reference O2) (oven dried)

| 2-θ (°) | d Value | Rel. Intensity (%) |
|---|---|---|
| 8.2 | 10.71 | 25 |
| 9.1 | 9.76 | 25 |
| 11.3 | 7.86 | 16 |
| 14.2 | 6.22 | 12 |
| 15.7 | 5.66 | 19 |
| 16.3 | 5.43 | 84 |
| 16.8 | 5.27 | 11 |
| 17.2 | 5.15 | 23 |
| 17.4 | 5.10 | 13 |
| 18.1 | 4.90 | 23 |
| 18.8 | 4.71 | 10 |
| 19.3 | 4.60 | 13 |
| 20.4 | 4.35 | 14 |
| 21.4 | 4.14 | 13 |
| 21.5 | 4.12 | 17 |
| 22.4 | 3.97 | 10 |
| 22.6 | 3.93 | 16 |
| 23.9 | 3.73 | 15 |

TABLE 164-continued

XRPD Signal angle data of 6-O2
(Experiment Reference 6-Sample Reference O2) (oven dried)

| 2-θ (°) | d Value | Rel. Intensity (%) |
|---|---|---|
| 25.2 | 3.54 | 14 |
| 25.6 | 3.48 | 100 |
| 26.8 | 3.32 | 22 |
| 27.3 | 3.27 | 17 |

9. Pattern #6a (Form A, Unary Fumarate, 6-S2 (Experiment Reference 6-Sample Reference S2))

The list of representative experiments that resulted in Pattern #6a is provided in Table 164A.

TABLE 164A

List of representative experiments that resulted in Pattern #6a.

| PATTERN #6a | |
|---|---|
| 6-S2 (strain) | 11-O2 |
| 6-S1 | 11-N2 |
| 11-A2 | 8-A1 |
| 11-B2 | 8-A2 |
| 11-F2 | 8-A3 |
| 11-H2 | 8-A4 |
| 11-J2 | 14-C1 |
| 11-L2 | 14-C2 |
| 11-M2 | |

* Strain refers to change across unit cell axis and leads to change in d-spacing that causes small shift in peak angle reflection (ca. 0.1 to 0.3° 2-θ).

Preparation

Pattern #6a was prepared in water.

The characterization data of 6-S2 (Experiment Reference 6-Sample Reference S2) is provided in FIG. 13, FIG. 344, FIG. 345, FIG. 347 and FIG. 348 and Table 166 and Table 166-A. DVS analyses of Form A is provided in FIG. 78.

TABLE 166

XRPD Signal angle data of 6-S2
(Experiment Reference 6-Sample Reference S2) (oven dried)

| 2-θ (°) | d Value | Rel. Intensity (%) |
|---|---|---|
| 13.0 | 6.79 | 11 |
| 16.6 | 5.33 | 78 |
| 19.3 | 4.59 | 38 |
| 19.6 | 4.52 | 100 |
| 20.7 | 4.29 | 68 |
| 22.1 | 4.01 | 22 |
| 25.4 | 3.50 | 63 |
| 26.2 | 3.40 | 34 |
| 33.6 | 2.67 | 12 |

TABLE 166A

Peak table of a calculated powder pattern for tabernanthalog monofumarate, Pattern #6a, Form A.

| Peak number | 2-θ (°) | Rel Intensity % |
|---|---|---|
| Peak #1 | 12.9 | 10 |
| Peak #2 | 16.6 | 100 |
| Peak #3 | 18.7 | 10 |
| Peak #4 | 19.3 | 25 |
| Peak #5 | 19.6 | 95 |
| Peak #6 | 20.6 | 94 |
| Peak #7 | 22.1 | 22 |
| Peak #8 | 25.3 | 90 |
| Peak #9 | 26.1 | 31 |
| Peak #10 | 26.3 | 11 |
| Peak #11 | 33.5 | 14 |
| Peak #12 | 37.8 | 12 |

10. Pattern #6b (Form A, 1-K2 (Experiment Reference 1-Sample Reference K2))

The list of representative experiments that resulted in Pattern #6b is provided in Table 166B.

TABLE 166B

List of representative experiments that resulted in Pattern #6b.

| PATTERN #6b |
|---|
| 1-K2 |
| 1-K1 |
| 11-E2 |
| 11-I2 |

Preparation

Pattern #6b was prepared in methanol.

The characterization data of 1-K2 (Experiment Reference 1-Sample Reference K2) is provided in FIGS. 349-353 and Table 167.

TABLE 167

XRPD Signal angle data of 1-K2
(Experiment Reference 1-Sample Reference K2) (oven dried)

| 2-θ (°) | d Value | Rel. Intensity (%) |
|---|---|---|
| 8.2 | 10.72 | 12 |
| 12.9 | 6.84 | 14 |
| 16.5 | 5.37 | 79 |
| 19.4 | 4.56 | 100 |
| 20.5 | 4.32 | 72 |
| 22.0 | 4.04 | 16 |
| 25.3 | 3.52 | 44 |
| 26.0 | 3.42 | 37 |
| 33.4 | 2.68 | 12 |
| 37.7 | 2.38 | 11 |

11. Pattern #7 (6-N1) (Experiment Reference 6-Sample Reference N1)

The list of representative experiments that resulted in Pattern #7 is provided in Table 167A.

TABLE 167A

List of representative experiments that resulted in Pattern #7.

| PATTERN #7 |
|---|
| 6-N1 |
| 1-M1 |
| 7-N1 |

Preparation

Pattern #7 was prepared in 2-MeTHF.

The characterization data of (6-N1) (Experiment Reference 6-Sample Reference N1) is provided in FIG. 354 and Table 168. It is worth noting that 7-N1 (Experiment Reference 7-Sample Reference N1) converted to Pattern #2b upon oven-drying (7-N2) (Experiment Reference 7-Sample Reference N2).

TABLE 168

XRPD Signal angle data of 6-N1 (wet pellet)
(Experiment Reference 6-Sample Reference N1)

| 2-θ (°) | d Value | Rel. Intensity (%) |
|---|---|---|
| 7.2 | 12.25 | 36 |
| 9.1 | 9.71 | 26 |
| 14.3 | 6.20 | 15 |
| 15.9 | 5.56 | 59 |
| 16.4 | 5.42 | 100 |
| 16.8 | 5.27 | 23 |
| 17.5 | 5.06 | 11 |
| 18.2 | 4.88 | 20 |
| 19.4 | 4.58 | 28 |
| 19.8 | 4.48 | 25 |
| 20.8 | 4.26 | 13 |
| 21.3 | 4.17 | 25 |
| 22.5 | 3.95 | 20 |
| 24.9 | 3.57 | 34 |
| 25.6 | 3.48 | 99 |
| 26.9 | 3.32 | 20 |
| 27.3 | 3.27 | 22 |

12. Pattern #8 (6-J2) (Experiment Reference 6-Sample Reference J2)

The list of representative experiments that resulted in Pattern #8 is provided in Table 168A.

TABLE 168A

List of representative experiments that resulted in Pattern #8.

| PATTERN #8 |
|---|
| 6-J1 |
| 6-J2 |
| 1-J1 |
| 7-S1 (Predom. amorph.) |
| 9-C1 |
| 9-C2 |

Preparation

Pattern #8 was prepared in isopropyl acetate.

The characterization data of (6-J2) (Experiment Reference 6-Sample Reference J2) is provided in FIG. 9, FIG. 355, FIG. 357, and FIG. 358 and Table 169.

TABLE 169

XRPD Signal angle data of 6-J2 (oven dried)
(Experiment Reference 6-Sample Reference J2)

| 2-θ (°) | d Value | Rel. Intensity (%) |
|---|---|---|
| 7.6 | 11.69 | 23 |
| 9.0 | 9.79 | 23 |
| 14.2 | 6.24 | 11 |
| 15.8 | 5.59 | 64 |
| 16.3 | 5.44 | 90 |
| 17.4 | 5.10 | 14 |
| 18.0 | 4.92 | 24 |
| 18.9 | 4.70 | 14 |
| 19.0 | 4.66 | 23 |
| 19.5 | 4.55 | 11 |
| 20.5 | 4.32 | 37 |
| 21.9 | 4.05 | 11 |
| 22.3 | 3.99 | 11 |
| 22.5 | 3.94 | 15 |
| 24.2 | 3.67 | 60 |
| 24.8 | 3.59 | 26 |
| 25.5 | 3.49 | 100 |
| 26.7 | 3.33 | 20 |
| 27.2 | 3.28 | 15 |

13. Pattern #9 (6-G1) (Experiment Reference 6-Sample Reference G1)

The list of representative experiments that resulted in Pattern #9 is provided in Table 669A.

TABLE 169A

List of representative experiments that resulted in Pattern #9.

| PATTERN #9 |
|---|
| 6-G1 |
| 1-H1 |
| 7-G1 |

Preparation

Pattern #9 was prepared in ethyl acetate.

The characterization data of 6-G1 is provided in FIG. 359 and Table 170. It is noted that 7-G1 (Experiment Reference 7-Sample Reference G1) converted to Pattern #2b upon oven-drying 7-G2 (Experiment Reference 7-Sample Reference G2).

TABLE 170

XRPD Signal angle data of 6-G1 (wet pellet)
(Experiment Reference 6-Sample Reference G1)

| 2-θ (°) | d Value | Rel. Intensity (%) |
|---|---|---|
| 8.0 | 11.05 | 32 |
| 9.2 | 9.63 | 27 |
| 10.5 | 8.43 | 13 |
| 12.2 | 7.27 | 13 |
| 14.3 | 6.17 | 14 |
| 15.9 | 5.56 | 100 |
| 16.4 | 5.39 | 78 |
| 17.1 | 5.18 | 35 |
| 18.2 | 4.87 | 18 |
| 19.2 | 4.63 | 15 |
| 19.5 | 4.56 | 41 |
| 20.8 | 4.27 | 25 |
| 21.9 | 4.06 | 39 |
| 22.4 | 3.96 | 15 |
| 24.7 | 3.60 | 84 |
| 25.6 | 3.47 | 96 |
| 27.0 | 3.30 | 21 |
| 27.3 | 3.27 | 10 |
| 28.8 | 3.09 | 18 |

14. Pattern #10 (6-P1) (Experiment Reference 6-Sample Reference P1)

The list of representative experiments that resulted in Pattern #10 is provided in Table 170A.

TABLE 170A

List of representative experiments that resulted in Pattern #10.

| PATTERN #10 |
| --- |
| 6-P1 |
| 1-I1 |
| 7-P1 |

Preparation
Pattern #10 was prepared in 2-propanol.

The characterization data of 6-P1 is provided in FIG. 360 and Table 171. It is noted that 7-P1 (Experiment Reference 7-Sample Reference P1) converted to Pattern #4a upon oven-drying (7-P2) (Experiment Reference 7-Sample Reference P2).

TABLE 171

XRPD Signal angle data of 6-P1 (wet pellet)
(Experiment Reference 6-Sample Reference P1)

| 2-θ (°) | d Value | Rel. Intensity (%) |
| --- | --- | --- |
| 8.2 | 10.78 | 47 |
| 9.1 | 9.75 | 41 |
| 10.8 | 8.17 | 42 |
| 14.2 | 6.21 | 20 |
| 15.2 | 5.82 | 37 |
| 16.3 | 5.43 | 94 |
| 16.9 | 5.25 | 96 |
| 17.4 | 5.08 | 12 |
| 18.0 | 4.91 | 23 |
| 18.8 | 4.71 | 12 |
| 19.1 | 4.63 | 17 |
| 19.6 | 4.51 | 21 |
| 19.8 | 4.48 | 39 |
| 21.3 | 4.16 | 56 |
| 21.8 | 4.07 | 29 |
| 22.2 | 4.00 | 27 |
| 22.6 | 3.94 | 15 |
| 23.4 | 3.80 | 41 |
| 23.5 | 3.79 | 53 |
| 23.6 | 3.76 | 32 |
| 25.2 | 3.53 | 22 |
| 25.5 | 3.48 | 100 |
| 26.1 | 3.41 | 12 |
| 26.8 | 3.33 | 31 |
| 29.8 | 3.00 | 15 |

15. Pattern #11 (6-Q1) (Experiment Reference 6-Sample Reference Q1)

The list of representative experiments that resulted in Pattern #11 is provided in Table 171A.

TABLE 171A

List of representative experiments that resulted in Pattern #11.

| PATTERN #11 |
| --- |
| 6-Q1 |
| 1-N1 |
| 7-Q1 |

Preparation
Pattern #11 was prepared in THF.

The characterization data of 6-Q1 is provided in FIG. 361 and Table 172.

TABLE 172

XRPD Signal angle data of 6-Q1 (wet pellet)
(Experiment Reference 6-Sample Reference Q1)

| 2-θ (°) | d Value | Rel. Intensity (%) |
| --- | --- | --- |
| 7.5 | 11.76 | 39 |
| 9.2 | 9.64 | 27 |
| 10.8 | 8.22 | 14 |
| 11.2 | 7.88 | 16 |
| 14.3 | 6.17 | 11 |
| 16.1 | 5.49 | 100 |
| 16.4 | 5.40 | 66 |
| 17.4 | 5.09 | 22 |
| 18.2 | 4.87 | 15 |
| 20.4 | 4.36 | 51 |
| 20.9 | 4.25 | 22 |
| 21.6 | 4.11 | 59 |
| 22.5 | 3.94 | 13 |
| 22.8 | 3.90 | 19 |
| 23.9 | 3.72 | 24 |
| 24.0 | 3.70 | 16 |
| 25.3 | 3.52 | 14 |
| 25.7 | 3.46 | 80 |
| 27.0 | 3.30 | 16 |

16. Pattern #12 (6-A1) (Experiment Reference 6-Sample Reference A1)

The list of representative experiments that resulted in Pattern #12 is provided in Table 172A.

TABLE 172A

List of representative experiments that resulted in Pattern #12

| PATTERN #12 |
| --- |
| 6-A1 |
| 1-A1 |

Preparation
Pattern #12 was prepared in acetone.

The characterization data of 6-A1 is provided in FIG. 362 and Table 173. It is noted that 7-A1 (Experiment Reference 7-Sample Reference A1) converted to Pattern #2b upon oven-drying (7-A2) (Experiment Reference 7-Sample Reference A2).

TABLE 173

XRPD Signal angle data of (6-A1) (wet pellet)
(Experiment Reference 6-Sample Reference A1)

| 2-θ (°) | d Value | Rel. Intensity (%) |
| --- | --- | --- |
| 8.3 | 10.64 | 25 |
| 9.1 | 9.67 | 24 |
| 10.8 | 8.17 | 14 |
| 14.3 | 6.18 | 14 |
| 16.3 | 5.42 | 100 |
| 18.2 | 4.86 | 21 |
| 20.3 | 4.37 | 26 |
| 21.6 | 4.11 | 30 |
| 23.0 | 3.87 | 18 |
| 25.6 | 3.47 | 96 |

17. Pattern #13 (7-L1) (Experiment Reference 7-Sample Reference L1)

The list of representative experiments that resulted in Pattern #13 is provided in Table 173A.

TABLE 173A

List of representative experiments that resulted in Pattern #13.

| PATTERN #13 |
|---|
| 7-L1 |
| 6-L1 |

Preparation
Pattern #13 was prepared in methyl acetate.

TABLE 174

XRPD Signal angle data of 7-L1 (wet pellet)
(Experiment Reference 7-Sample Reference L1)

| 2-θ (°) | d Value | Rel. Intensity (%) |
|---|---|---|
| 8.1 | 10.91 | 28 |
| 18.1 | 4.89 | 18 |
| 18.9 | 4.69 | 10 |
| 19.7 | 4.50 | 42 |
| 20.9 | 4.24 | 19 |
| 21.9 | 4.05 | 27 |
| 22.7 | 3.91 | 16 |
| 23.4 | 3.81 | 12 |
| 24.5 | 3.64 | 12 |
| 25.0 | 3.56 | 59 |
| 25.6 | 3.47 | 100 |
| 9.1 | 9.68 | 23 |
| 26.9 | 3.31 | 19 |
| 28.7 | 3.11 | 12 |
| 10.5 | 8.41 | 19 |
| 14.3 | 6.19 | 11 |
| 16.0 | 5.53 | 78 |
| 16.4 | 5.41 | 75 |
| 17.5 | 5.07 | 37 |

18. Pattern #15 ((1-C2) (Experiment Reference 1-Sample Reference C2))

The list of representative experiments that resulted in Pattern #15 is provided in Table 174A.

TABLE 174A

List of representative experiments that resulted in Pattern #15.

| PATTERN #15 |
|---|
| 1-C2 |
| 1-C1 |

Preparation
Pattern #15 was prepared in butanol.
The characterization data of 1-C2 is provided in FIG. 1, FIG. 368, FIG. 370, FIG. 371 and FIG. 372 and Table 176.

TABLE 176

XRPD Signal angle data of 1-C2 (oven dried)
(Experiment Reference 1-Sample Reference C2)

| 2-θ (°) | d Value | Rel. Intensity (%) |
|---|---|---|
| 8.4 | 10.51 | 24.0824 |
| 9.0 | 9.84 | 17.0488 |

TABLE 176-continued

XRPD Signal angle data of 1-C2 (oven dried)
(Experiment Reference 1-Sample Reference C2)

| 2-θ (°) | d Value | Rel. Intensity (%) |
|---|---|---|
| 10.5 | 8.39 | 16.7679 |
| 15.0 | 5.90 | 18.8008 |
| 16.2 | 5.46 | 100.0000 |
| 16.9 | 5.24 | 33.2111 |
| 17.0 | 5.21 | 66.3567 |
| 17.7 | 5.01 | 17.5463 |
| 18.0 | 4.92 | 19.8925 |
| 18.9 | 4.70 | 14.2790 |
| 19.2 | 4.61 | 10.7662 |
| 19.9 | 4.46 | 30.8267 |
| 21.0 | 4.22 | 46.5241 |
| 22.5 | 3.96 | 12.6072 |
| 23.3 | 3.82 | 49.3726 |
| 23.6 | 3.77 | 13.7509 |
| 24.4 | 3.64 | 25.9068 |
| 24.8 | 3.58 | 12.4289 |
| 25.1 | 3.54 | 21.2087 |
| 25.5 | 3.49 | 61.0403 |
| 26.0 | 3.42 | 18.0249 |
| 26.7 | 3.33 | 13.4083 |

19. Pattern #16 (1-F1) (Experiment Reference 1-Sample Reference F1)

The list of representative experiments that resulted in Pattern #16 is provided in Table 176A.

TABLE 176A

List of representative experiments that resulted in Pattern #16.

| PATTERN #16 |
|---|
| 1-F1 |

Preparation
Pattern #16 was prepared in diethyl ether.

TABLE 177

XRPD Signal angle data of 1-F1 (wet pellet)
(Experiment Reference 1-Sample Reference F1)

| 2-θ (°) | d Value | Rel. Intensity (%) |
|---|---|---|
| 9.0 | 9.81 | 13 |
| 9.1 | 9.75 | 25 |
| 9.6 | 9.18 | 24 |
| 14.2 | 6.21 | 12 |
| 16.4 | 5.42 | 76 |
| 16.8 | 5.27 | 25 |
| 17.0 | 5.21 | 38 |
| 17.5 | 5.06 | 13 |
| 17.8 | 4.99 | 19 |
| 18.1 | 4.89 | 23 |
| 19.0 | 4.66 | 14 |
| 19.3 | 4.59 | 35 |
| 20.3 | 4.38 | 15 |
| 22.4 | 3.97 | 20 |
| 23.2 | 3.84 | 11 |
| 23.8 | 3.73 | 12 |
| 24.4 | 3.65 | 36 |
| 25.2 | 3.53 | 15 |
| 25.6 | 3.48 | 100 |
| 26.2 | 3.40 | 12 |
| 26.8 | 3.32 | 17 |
| 27.3 | 3.27 | 19 |

20. Pattern #17 (7-O1) (Experiment Reference 7-Sample Reference O1)

The list of representative experiments that resulted in Pattern #17 is provided in Table 177A.

TABLE 177A

| List of representative experiments that resulted in Pattern #17. PATTERN #17 |
|---|
| 7-O1 |

Preparation
Pattern #17 was prepared in nitromethane.
The characterization data of 7-O1 is provided in FIG. 374 and Table 178.

TABLE 178

XRPD Signal angle data of 7-O1 (wet pellet) (Experiment Reference 7-Sample Reference O1)

| 2-θ (°) | d Value | Rel. Intensity (%) |
|---|---|---|
| 8.1 | 10.87 | 18 |
| 9.1 | 9.69 | 27 |
| 11.2 | 7.89 | 18 |
| 14.3 | 6.19 | 12 |
| 15.4 | 5.76 | 17 |
| 16.4 | 5.39 | 85 |
| 16.6 | 5.33 | 78 |
| 18.1 | 4.89 | 21 |
| 19.6 | 4.52 | 42 |
| 21.2 | 4.18 | 11 |
| 21.7 | 4.08 | 45 |
| 22.4 | 3.96 | 26 |
| 23.2 | 3.83 | 26 |
| 23.6 | 3.77 | 56 |
| 25.2 | 3.53 | 17 |
| 25.6 | 3.47 | 100 |
| 26.9 | 3.31 | 38 |
| 27.1 | 3.28 | 20 |
| 30.3 | 2.95 | 13 |

21. Pattern #18 (Sample Reference 1, Cold Cryst., 150° C.)

The list of representative experiments that resulted in Pattern #18 is provided in Table 178A

TABLE 178A

| List of representative experiments that resulted in Pattern #18. PATTERN #18 |
|---|
| Tabernanthalog monofumarate, Sample Reference 1, cold cryst., 150 ° C. |

Preparation
N/A
The characterization data of Sample Reference 1 is provided in FIG. 375 and Table 179.

TABLE 179

XRPD Signal angle data of tabernanthalog DSC XRPD 150C (Sample Reference 1), cold cryst., 150 ° C.

| 2-θ (°) | d Value | Rel. Intensity (%) |
|---|---|---|
| 8.7 | 10.19 | 11 |
| 9.1 | 9.72 | 12 |

TABLE 179-continued

XRPD Signal angle data of tabernanthalog DSC XRPD 150C (Sample Reference 1), cold cryst., 150 ° C.

| 2-θ (°) | d Value | Rel. Intensity (%) |
|---|---|---|
| 11.0 | 8.00 | 23 |
| 12.1 | 7.28 | 12 |
| 12.6 | 7.03 | 15 |
| 14.1 | 6.28 | 17 |
| 15.5 | 5.70 | 25 |
| 16.0 | 5.52 | 96 |
| 16.3 | 5.45 | 45 |
| 16.8 | 5.29 | 14 |
| 18.0 | 4.93 | 86 |
| 18.9 | 4.69 | 20 |
| 19.3 | 4.60 | 16 |
| 20.9 | 4.24 | 19 |
| 21.4 | 4.15 | 35 |
| 22.4 | 3.96 | 17 |
| 23.0 | 3.87 | 29 |
| 24.9 | 3.58 | 12 |
| 25.6 | 3.47 | 100 |
| 25.9 | 3.43 | 27 |
| 26.8 | 3.33 | 30 |

22. Pattern #19 (7-A1; Experiment Reference 7-Sample Reference A1)

The list of representative experiments that resulted in Pattern #19 is provided in Table 179A

TABLE 179A

| List of representative experiments that resulted in Pattern #19. PATTERN #19 |
|---|
| 7-A1 |
| 7-A2 |

Preparation
Pattern #19 was prepared in acetone.
The characterization data of 7-A1 is provided in FIG. 376 and Table 180.

TABLE 180

XRPD Signal angle data of 7-A1 (wet pellet) (Experiment Reference 7-Sample Reference A1)

| 2-θ (°) | d Value | Rel. Intensity (%) |
|---|---|---|
| 9.1 | 9.74 | 18 |
| 12.2 | 7.27 | 11 |
| 15.7 | 5.66 | 12 |
| 16.3 | 5.43 | 55 |
| 16.4 | 5.41 | 78 |
| 17.0 | 5.21 | 24 |
| 18.6 | 4.77 | 13 |
| 19.4 | 4.58 | 25 |
| 19.5 | 4.54 | 27 |
| 20.5 | 4.33 | 73 |
| 21.5 | 4.13 | 17 |
| 21.9 | 4.05 | 16 |
| 22.8 | 3.90 | 30 |
| 24.7 | 3.60 | 14 |
| 25.5 | 3.49 | 90 |
| 25.6 | 3.48 | 100 |
| 26.7 | 3.34 | 31 |
| 27.1 | 3.28 | 17 |
| 29.8 | 2.99 | 11 |
| 33.3 | 2.69 | 18 |

23. Pattern #20 (1-Q1; Experiment Reference 1-Sample Reference Q1)

The list of representative experiments that resulted in Pattern #20 is provided in Table 180A.

TABLE 180A

| List of representative experiments that resulted in Pattern #20. PATTERN #20 |
| --- |
| 1-Q1 |

Preparation

Pattern #20 was prepared in 1,4-dioxane.

The characterization data of 1-Q1 is provided in FIG. 377 and Table 181.

TABLE 181

XRPD Signal angle data of 1-Q1 (wet pellet; Pattern #20)

| 2-θ (°) | d Value | Rel. Intensity (%) |
| --- | --- | --- |
| 6.1 | 14.54 | 100 |
| 15.9 | 5.57 | 13 |
| 16.3 | 5.43 | 27 |
| 16.7 | 5.32 | 12 |
| 18.2 | 4.87 | 25 |
| 19.0 | 4.66 | 27 |
| 25.5 | 3.49 | 37 | ii. Hemifumarate Salts

1. Pattern #5 (1-G2 (Experiment Reference 1-Sample Reference G2))

The list of representative experiments that resulted in Pattern #5 is provided in Table 181A.

TABLE 181A

| List of representative experiments that resulted in Pattern #5. PATTERN #5 |
| --- |
| 1-G2 |
| 1-G1 |
| 7-F1 |
| 6-F1 |
| 11-P2 |
| 11-K2 |
| 11-D2 |

Preparation

Pattern #5 was prepared in ethanol.

The characterization data of 1-G2 (Experiment Reference 1-Sample Reference G2) is provided in FIG. 2, FIGS. 377A-337D and Table 181B. In the TGA profile, the weight loss transition (−5.8% w/w) attributed to ethanol release (probable ethanol, hemi-solvate).

TABLE 181B

XRPD Signal angle data of 1-G2 (Experiment Reference 1-Sample Reference G2) (oven dried)

| 2-θ (°) | d Value | Rel. Intensity (%) |
| --- | --- | --- |
| 8.2 | 10.75 | 100 |
| 11.1 | 7.97 | 38 |
| 12.8 | 6.94 | 10 |
| 15.4 | 5.76 | 37 |

TABLE 181B-continued

XRPD Signal angle data of 1-G2 (Experiment Reference 1-Sample Reference G2) (oven dried)

| 2-θ (°) | d Value | Rel. Intensity (%) |
| --- | --- | --- |
| 16.3 | 5.43 | 15 |
| 16.9 | 5.23 | 82 |
| 19.1 | 4.64 | 16 |
| 20.0 | 4.44 | 42 |
| 21.4 | 4.15 | 56 |
| 22.2 | 4.00 | 18 |
| 22.5 | 3.95 | 31 |
| 23.6 | 3.77 | 46 |
| 23.9 | 3.72 | 28 |
| 25.5 | 3.49 | 33 |
| 26.8 | 3.32 | 10 |
| 30.2 | 2.95 | 21 |

2. Pattern #14 (Form 1, Hemi-Fumarate, 5-B3) (Experiment Reference 5-Sample Reference 1B3)

The list of representative experiments that resulted in Pattern #14 is provided in Table 181C.

TABLE 181C

| List of representative experiments that resulted in Pattern #14. PATTERN #14 |
| --- |
| 5-03 (re-proportionation) |
| 5-02 (re-proportionation) |
| 5-B2 |
| 5-B3 |
| 11-Q2 |

Preparation

Pattern #14 was prepared in isopropyl acetate.

The characterization data of 5-B3 (Form I, hemi-fumarate) is provided in FIGS. 377E-377J and Table 181D and Table 181E.

TABLE 181D

XRPD Signal angle data of (5-B3) (Experiment Reference 5-Sample Reference B3)

| 2-θ (°) | d Value | Rel. Intensity (%) |
| --- | --- | --- |
| 8.2 | 10.79 | 100 |
| 11.2 | 7.90 | 36 |
| 12.8 | 6.93 | 10 |
| 15.5 | 5.70 | 56 |
| 17.0 | 5.21 | 54 |
| 18.1 | 4.91 | 18 |
| 18.4 | 4.83 | 13 |
| 19.2 | 4.61 | 17 |
| 19.4 | 4.56 | 13 |
| 20.2 | 4.39 | 44 |
| 21.3 | 4.17 | 13 |
| 21.5 | 4.13 | 29 |
| 22.6 | 3.93 | 51 |
| 23.7 | 3.75 | 32 |
| 24.3 | 3.67 | 17 |
| 24.8 | 3.59 | 31 |

TABLE 181E

Peak table of a calculated powder pattern for tabernanthalog hemifumarate, Pattern #14, Form I (11-Q2).

| 2-θ (°) | Rel Intensity % |
|---|---|
| 8.2 | 100 |
| 11.3 | 62 |
| 12.9 | 18 |
| 15.4 | 11 |
| 15.6 | 38 |
| 17.1 | 51 |
| 19.1 | 18 |
| 20.3 | 40 |
| 21.2 | 14 |
| 21.5 | 45 |
| 22.7 | 14 |
| 22.9 | 11 |

3. Pattern #21 (7-P2; Experiment Reference 7-Sample Reference P2)

The list of representative experiments that resulted in Pattern #21 is provided in Table 181F.

TABLE 181F

List of representative experiments that resulted in Pattern #21.
PATTERN #21

7-P2

Preparation
Pattern #21 was prepared in isopropanol.

The characterization data of 7-P2 is provided in FIG. 5, FIG. 378, FIG. 380 and FIG. 381 and Table 182.

TABLE 182

XRPD Signal angle data of 7-P2 (oven dried) (Experiment Reference 7-Sample Reference P2)

| 2-θ (°) | d Value | Rel. Intensity (%) |
|---|---|---|
| 6.7 | 13.15 | 23 |
| 8.2 | 10.74 | 11 |
| 12.8 | 6.89 | 16 |
| 14.9 | 5.94 | 13 |
| 16.3 | 5.45 | 10 |
| 16.7 | 5.31 | 80 |
| 17.6 | 5.04 | 16 |
| 17.7 | 5.01 | 30 |
| 18.1 | 4.89 | 31 |
| 19.2 | 4.61 | 100 |
| 20.1 | 4.41 | 23 |
| 21.2 | 4.19 | 27 |
| 22.2 | 3.99 | 38 |
| 23.0 | 3.86 | 16 |
| 23.6 | 3.77 | 16 |
| 25.4 | 3.50 | 55 |
| 26.1 | 3.41 | 26 |
| 27.2 | 3.28 | 36 |
| 28.7 | 3.11 | 15 |
| 30.1 | 2.96 | 13 |

4. Pattern #22 (10-B1; Experiment Reference 10-Sample Reference B1)

The list of representative experiments that resulted in Pattern #22 is provided in Table 182A.

TABLE 182A

List of representative experiments that resulted in Pattern #22.
PATTERN #22

10-B1

Preparation
Pattern #22 was prepared in water.

The characterization data of 10-B1 is provided in FIGS. 382-383 and Table 183.

TABLE 183

XRPD Signal angle data of 10-B1 (Experiment Reference 10-Sample Reference B1)

| 2-θ (°) | d Value | Rel. Intensity (%) |
|---|---|---|
| 6.7 | 13.18 | 24 |
| 10.4 | 8.50 | 14 |
| 12.9 | 6.87 | 12 |
| 15.0 | 5.90 | 18 |
| 16.7 | 5.29 | 48 |
| 17.7 | 4.99 | 22 |
| 18.2 | 4.87 | 32 |
| 18.9 | 4.70 | 100 |
| 19.3 | 4.59 | 83 |
| 20.2 | 4.39 | 21 |
| 21.3 | 4.17 | 13 |
| 22.3 | 3.98 | 21 |
| 23.1 | 3.84 | 11 |
| 23.7 | 3.75 | 15 |
| 25.4 | 3.51 | 11 |
| 25.5 | 3.49 | 24 |
| 26.2 | 3.40 | 19 |
| 27.3 | 3.27 | 47 |

F. Overall Summary

A summary of important findings based on this study is provided below:
Supplied batch (Sample Reference 1, Pattern #1) exhibited two potential melt events were evident by DSC (FIG. 300).
Qualitative solubility:
The tabernanthalog monofumarate salt was sparingly soluble in most of the common solvents investigated and was soluble in methanol/water (200 mg/ml) at reflux (Experiment Reference 1)
crystallized samples from the qualitative solubility pane, included those from butanol, ethanol methanol and water, these were dried and analysed further and supported the formation of butanol hemi-solvate, ethanol hemi-fumarate/solvate and anhydrous forms from methanol and water.
Re-proportionation:
the hemi-fumarate salt exhibited a propensity to re-proportionate to the fumarate salt during an ageing cycle
Stability evaluation at 40° C./75% RH:
executed over a 4 to 5 week period
no evidence for hydration was observed
Suspension equilibrations:
against 20 solvents at two temperature set-points, various patterns were identified (84)
many of these were identified via XRPD analyses of wet pellets and when dried, often converted into Form A; therefore, thermal analyses were not possible on the metastable forms.

Single forms identified from the screen included:
The tabernanthalog monofumarate salt Form A (Pattern #6a) was identified as the stable polymorphic form
The tabernanthalog monofumarate salt Form B (Pattern #2a), identified as the metastable polymorphic form
Tabernanthalog hemifumarate was also isolated as an enriched phase and assigned Form I (Pattern #14).

Single crystal structures were determined for Form A (Pattern #6a, 11-M2; Experiment Reference 11-Sample Reference M2) and Form I (tabernanthalog hemifumarate (Pattern #14); 11-Q2; Experiment Reference 11-Sample Reference Q2) (FIGS. 285 and 286, respectively).

Mass equilibrated DVS of Form A (Pattern #6a) was performed (FIG. 83 and FIG. 84). The analysis showed hygroscopic isotherm with negligible hysteresis.

Competitive suspension equilibration studies of equimolar mixtures of Form A (Pattern #6a) and Form B (Pattern #14) at temperature set points 20 and 40° C. After stirring at both temperatures for 4 weeks, Form A (Pattern #6a) was dominant in the isolated wet pellets indicating that it is more stable compared to Form B (Pattern #14).

Table 184: Summary of the powder patterns identified during polymorph screen and accompanied by their analytical data (1/5).

| Designation | Experimental reference | Solvent | Profile | DSC Event | DSC Thermal measurements | | TGA % Δwt. | TGA Comment | 1H NMR (stoichiometry) | 1H NMR (solvent) | Assignment | S CX RD (single anhydrous forms) |
|---|---|---|---|---|---|---|---|---|---|---|---|---|
| PATTERN #1 | Supplied Sample Reference 1 | Acetonitrile and water | | Multiple events; main endotherm quoted | Integral / Onset / Peak / Endset | -20.53 Jg^-1 / 177.95 °C / 184.50 °C / 188.41 °C | -2.1% w/w, onset 72.4 °C | Stepped baseline (broad transition) | 1 to 1 (API to fumarate) | KF (~2.6 % w/w) + acetonitrile (~0.2 % w/w) | Pattern #1 | — |
| PATTERN #1 (example 2) | 7-N2 (oven dried) | 2Me-THF | | Multiple events; main endotherm quoted | Integral / Onset / Peak / Endset | -38.78 Jg^-1 / 206.07 °C / 212.67 °C / 216.10 °C | -1.2% w/w, onset 115.6 °C | Stepped baseline (sharper transition) | 1 to 1 (API to fumarate) | 2Me-THF (n.d.) | Pattern #1 | — |
| PATTERN #2a | 7-B2 (oven dried) | Acetonitrile | | Multiple events; main endotherm quoted (shouldered, br.) | Integral / Onset / Peak / Endset | -31.27 Jg^-1 / 174.06 °C / 183.50 °C / 187.40 °C | -10.3% w/w, onset 219.1 °C | Flat baseline (anhydrous) | 1 to 1 (API to fumarate) | MeCN (0.1% w/w) | Form B (unary fumarate) | — |
| PATTERN #2b | 6-G2 (oven dried) | Ethyl acetate | | Multiple events; main endotherm quoted | Integral / Onset / Peak / Endset | -3.1% Jg^-1 / 191.15 °C / 195.50 °C / 199.25 °C | -3.1% w/w, onset 114.0 °C, -13.5% w/w, onset 220 °C | Stepped baseline | 1 to 1 (API to fumarate) | EtOAc (4.0% w/w) | Pattern #2b | — |
| PATTERN #2c | 1-P2 | Water | | Multiple events; main endotherm quoted | Integral / Onset / Peak / Endset | -120.94 Jg^-1 / 196.55 °C / 200.33 °C / 202.48 °C | -26.5% w/w, onset 213 °C | Flat baseline (anhydrous) | Co-resonated | — | Pattern #2c | — |
| PATTERN #2d | 7-H1 (moist pellet) | Ethyl formate | — | — | — | — | — | — | — | — | Pattern #2d | — |
| ▽ | 7-H2 (oven dried) | Ethyl formate | — | — | — | — | — | — | — | — | Pattern #2b | — |

Table 184: (continued) Summary of the powder patterns identified during polymorph screen and accompanied by their analytical data (2/5).

| Designation | Experimental reference | Solvent | Profile | DSC Event | DSC Thermal measurements | | TGA % Δwt. | TGA Comment | ¹H NMR (stoichiometry) | ¹H NMR (solvent) | Assignment | S CX RD (single anhydrous forms) |
|---|---|---|---|---|---|---|---|---|---|---|---|---|
| PATTERN #3 | 6-R2 (oven dried) | Toluene | 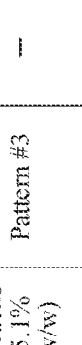 | Multiple events; main endotherm quoted | Integral<br>Onset<br>Peak<br>Endset | -28.78 Jg^-1<br>181.12 °C<br>185.17 °C<br>188.72 °C | -4.0% w/w, onset 122.8 °C; -13.4% w/w, onset 219.6 °C | Stepped baseline | 1 to 1 (API to fumarate) | Toluene (5.1% w/w) | Pattern #3 | — |
| PATTERN #4a | 6-K2 (oven dried) | Methanol |  | Two melt events; main endotherm quoted | Integral<br>Onset<br>Peak<br>Endset | -62.00 Jg^-1<br>188.55 °C<br>192.00 °C<br>194.93 °C | -0.8% w/w, onset 65.0 °C; -17.6% w/w, onset 220.0 °C | Stepped baseline | 1 to 1 (API to fumarate) | MeOH (0.2% w/w) | Pattern #4a | — |
| PATTERN #4b | 6-O2 (oven dried) | Nitromethane |  | Two melt events; main endotherm quoted | Integral<br>Onset<br>Peak<br>Endset | -5.06 Jg^-1<br>188.41 °C<br>188.41 °C<br>195.40 °C | -14.2% w/w, onset 219.9 °C | Stepped baseline | 1 to 1 (API to fumarate) | MeNO₂ (0.2% w/w) | Pattern #4b | — |
| PATTERN #5 | 1-G2 (oven dried) | Ethanol | 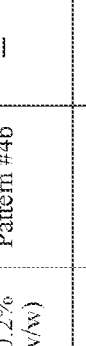 | Multiple events; main endotherm quoted | Integral<br>Onset<br>Peak<br>Endset | -51.50 Jg^-1<br>208.70 °C<br>214.33 °C<br>217.38 °C | -5.8% w/w, onset 143.8 °C; -26.9% w/w, onset 223.6 °C | Stepped baseline | 2 to 1 (API to fumarate) | EtOH (4.9% w/w) | Pattern #5 | — |
| PATTERN #6a | 6-S2 (oven dried) | Water | 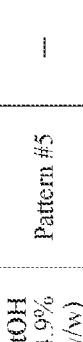 | Single melt event | Integral<br>Onset<br>Peak<br>Endset | -76.81 Jg^-1<br>189.18 °C<br>193.83 °C<br>196.56 °C | -15.1% w/w, onset 143.8 °C | Flat baseline (anhydrous) | 1 to 1 (API to fumarate) | n.d. | Form A (unary fumarate) | Crystals not suitable, attempting to regrow |
| PATTERN #6b | 1-K2 (oven dried) | Methanol |  | Mixed phase | Integral<br>Onset<br>Peak<br>Endset | -72.13 Jg^-1<br>188.24 °C<br>192.67 °C<br>195.48 °C | -1.2% w/w, onset 192.0 °C; -17.4% w/w, onset 223.9 °C | Flat baseline (anhydrous) | 1 to 1 (API to fumarate) | MeOH (0.7% w/w) | Form A (isostructural + reflections) | — |

Table 184: (continued) Summary of the powder patterns identified during polymorph screen and accompanied by their analytical data (3/5).

| Designation | Experimental reference | Solvent | DSC | | | | TGA | | ¹H NMR | | Assignment |
| --- | --- | --- | --- | --- | --- | --- | --- | --- | --- | --- | --- |
| | | | Profile | Event | Thermal measurements | | % Δwt. | Comment | ¹H NMR (stoichiometry) | ¹H NMR (solvent) | |
| PATTERN #7 | 6-N1 (moist pellet) | 2Me-THF | — | — | — | — | — | — | — | — | Pattern #7 |
| ▽ | 6-N2 (oven dried) | 2Me-THF | — | — | — | — | — | — | — | — | Pattern #2b |
| PATTERN #8 | 6-J2 (oven dried) | Isopropyl acetate | | Multiple events, main endotherm quoted | Integral -43.79 Jg^-1 | | -6.6% w/w, onset 109.8 °C | Stepped baseline | 1 to 1 (API to fumarate) | Isopropyl acetate (10.0% w/w) | Pattern #8 |
| | | | | | Onset | 180.65 °C | | | | | |
| | | | | | Peak | 185.50 °C | | | | | |
| | | | | | Endset | 188.42 °C | | | | | |
| PATTERN #9 | 6-G1 (moist pellet) | Ethyl acetate | — | — | — | — | — | — | — | — | Pattern #9 |
| ▽ | 6-G2 (oven dried) | Ethyl acetate | — | — | — | — | — | — | — | — | Pattern #2b |
| PATTERN #10 | 6-P1 (moist pellet) | 2-Propanol | — | — | — | — | — | — | — | — | Pattern #10 |
| ▽ | 6-P2 (oven dried) | 2-Propanol | — | — | — | — | — | — | — | — | Pattern #4a |
| PATTERN #11 | 6-Q1 (moist pellet) | THF | — | — | — | — | — | — | — | — | Pattern #11 |

Table 184: (continued) Summary of the powder patterns identified during polymorph screen and accompanied by their analytical data (4/5).

| Designation | Experimental reference | Solvent | DSC Profile | DSC Event | DSC Thermal measurements | | TGA % Δwt. | TGA Comment | ¹H NMR (stoichiometry) | ¹H NMR (solvent) | Assignment |
|---|---|---|---|---|---|---|---|---|---|---|---|
| PATTERN #12 | 6-A1 (moist pellet) | Acetone | — | — | — | — | — | — | — | — | Pattern #12 |
| | 6-A2 (oven dried) | Methyl acetate | — | — | — | — | — | — | — | — | Pattern #2b |
| PATTERN #13 | 7-L1 (moist pellet) | | — | — | — | — | — | — | — | — | Pattern #13 |
| PATTERN #14 | 5-B3 | Isopropyl acetate | | Multiple small solvent release events; main endotherm quoted | Integral -111.79 Jg^-1 | | -1.2% w/w, onset 75.9 °C; -1.3% w/w, onset 141.5 °C | Stepped baseline | 2 to 1 (API to fumarate) | Acetone (0.2% w/w), acetonitrile (0.3% w/w), methanol (2.4% w/w) | Form 1 (hemi-fumarate) |
| | | | | | Onset 210.66 °C | | | | | | |
| | | | | | Peak 213.83 °C | | | | | | |
| | | | | | Endset 215.54 °C | | | | | | |
| PATTERN #15 | 1-C2 (oven dried) | Butanol | | Multiple solvent release events; main endotherm quoted | Integral -42.54 Jg^-1 | | -8.6% w/w, onset 127 °C; -20.2% w/w, onset 221.1 °C | Stepped baseline | 1 to 1 (API to fumarate) | Butanol (6.3% w/w) | Pattern #15 |
| | | | | | Onset 179.26 °C | | | | | | |
| | | | | | Peak 187.50 °C | | | | | | |
| | | | | | Endset 194.22 °C | | | | | | |
| PATTERN #16 | 1-F1 (moist pellet) | Diethyl ether | — | — | — | — | — | — | — | — | Pattern #16 |
| PATTERN #17 | 7-O1 (moist pellet) | Nitromethane | — | — | — | — | — | — | — | — | Pattern #17 |

Table 184: (continued) Summary of the powder patterns identified during polymorph screen and accompanied by their analytical data (5/5).

| Designation | Experimental reference | Solvent | DSC Profile | DSC Event | DSC Thermal Measurements | | | TGA % Δwt. | TGA Comment | 1H NMR (stoichiometry) | 1H NMR (solvent) | Assignment |
|---|---|---|---|---|---|---|---|---|---|---|---|---|
| PATTERN #18 | Sample Reference 1 (Cold cryst. 150° C) | N/A | --- | --- | --- | --- | --- | --- | --- | --- | --- | Pattern #18 (high disorder) |
| PATTERN #19 | 7-A1 (moist pellet) | Acetone | --- | --- | --- | --- | --- | --- | --- | --- | --- | Pattern #19 (high disorder) |
| PATTERN #19 | 7-A1 (oven dried) | Acetone | Insufficient sample for analyses | --- | --- | --- | --- | --- | --- | --- | --- | Pattern #19 (v. high disorder; insufficient sample for full analyses) |
| PATTERN #20 | 1-Q1 (moist pellet) | 1,4 Dioxane | --- | --- | --- | --- | --- | --- | --- | --- | --- | Pattern #19 (high disorder) |
| PATTERN #21 | 7-P2 (oven dried) | Isopropanol | | De-solvation, cold crystallisation and melt; main endotherm quoted | Integral | -84.97 Jg^-1 | | -2.3% w/w, onset 154.7 °C | Stepped baseline | 2 to 1 (API to fumarate) | Isopropanol (0.9% w/w) | Pattern #21 |
| | | | | | Onset | 177.25 °C | | | | | | |
| | | | | | Peak | 185.00 °C | | | | | | |
| | | | | | Endset | 190.14 °C | | | | | | |
| PATTERN #22 | 10-B2 (suction dried) | Water | | Multiple events; main event quoted | Integral | -43.56 Jg^-1 | | --- | --- | 2 to 1 (API to fumarate); metastable and stable forms | --- | --- |
| | | | | | Onset | 206.73 °C | | | | | | |
| | | | | | Peak | 210.67 °C | | | | | | |
| | | | | | Endset | 213.11 °C | | | | | | |

Tables 185-187 summarizes the characterization data of Forms A, B and I, respectively.

TABLE 185

| The tabernanthalog Monofumarate salt (Form A, Pattern #6a) | |
| --- | --- |
| Provenances of reference batches | The tabernanthalog monofumarate salt (Form A, Pattern #6a, unary fumarate) |
| 8-A4 (Experiment Reference 8-Sample Reference A4): obtained from suspension equilibration of tabernanthalog monofumarate (Sample Reference 1; Pattern #1) in water (5 vol) at 90° C. The product was isolated by filtration and dried under sustained nitrogen flux (<1 bar) over 20 h at 20° C. 6-S2 (Experiment Reference 6-Sample Reference S2): (obtained from suspension equilibration of Sample Reference 1 in water (5 vol) at 20° C. and isolated as above. [6-S1 (Experiment Reference 6-Sample Reference S1) and 6-S2 (Experiment Reference 6-Sample Reference S2) gave the same powder diffraction pattern. The thermal data were collected from the dried material.] | Reference batches: 6-S1 (Experiment Reference 6-Sample Reference S1), 6-S2 (Experiment Reference 6-Sample Reference S2), 11-A2 (Experiment Reference 11-Sample Reference A2), 11-B2 (Experiment Reference 11-Sample Reference B2), 11-F2 (Experiment Reference 11-Sample Reference F2), 11-H2 (Experiment Reference 11-Sample Reference H2), 11-J2 (Experiment Reference 11-Sample Reference J2), 11-L2 (Experiment Reference 11-Sample Reference L2), 11-M2 (Experiment Reference 11-Sample Reference M2), 11-N2 (Experiment Reference 11-Sample Reference N2), 11-O2 (Experiment Reference 11-Sample Reference O2), 8-A1 (Experiment Reference 8-Sample Reference A1), 8-A2 (Experiment Reference 8-Sample Reference A2), 8-A3 (Experiment Reference 8-Sample Reference A3), 8-A4 (Experiment Reference 8-Sample Reference A4), 14-C1 (Experiment Reference 14-Sample Reference C1), and 14-C2 (Experiment Reference 14-Sample Reference C2). Molecular weight: 346.383 gmol$^{-1}$ Exact molecular weight: 346.153 Molecular formula: $C_{18}H_{22}N_2O_5$ Unary fumarate: 33.5% w/w th., fumaric acid (i.e., 1.0 mol of API to 1.0 mol fumaric acid) Nature of hydrogen bonding: fumaric acid adopted a 1,4-orientated linear configuration, exhibiting head to tail hydrogen bonding between oxygen atoms O3-O4 (2.48 Å), while oxygen atom O2 was hydrogen bonded to nitrogen atom N1, located on the azepine ring (O2-N1, 2.70 Å), assumed to be salified. Crystal system 300(2): monoclinic (FIG. 285) Space group 300(2): P2$_1$/$_C$ Unit cell 300(2) K: a = 7.43280(10) Å, b = 8.59740(10) Å, c = 27.5143(3) Å, a = g = 90°, b = 96.6990(10)°, V = 1746.24(4) Å$^3$ Asymmetric unit: contained one molecule of API and one molecule of fumaric acid (crystal bonded). XRPD: 12.9°, 14.1°, 15.8°, 16.5°, 19.2°, 19.4°, 20.6°, 22.0°, 25.2°, 26.0°, 28.0°, 33.4°, ° (2θ, 1 d.p), (8-A4). [Only peaks with >10% rel. intensity are provided.] DSC: onset 187.0° C. (−117.9 Jg$^{-1}$, endotherm, melt). TGA (only ablation events): onset 220.8° C. (−16.0% w/w, ablation) 289.5° C. (−1.2% w/w, ablation), 315.3° C. (−1.5% w/w, ablation), 325.9° C. (−3.8% w/w, ablation), 373.7° C. (−14.0% w/w, ablation), (8-A4). This is shown in FIG. 148. DVS 0 to 90 to 0% RH (dm/dt <0.002%): 0.0 (0.0004%), 5.0 (0.0627%), 10.0 (0.0957%), 15.0 (0.1397%), 20.0 (0.1778%), 25.0 (0.2093%), 30.0 (0.2401%), 40.0 (0.3145%), 50.0 (0.4051%), 60.0 (0.5029%), 70.0 (0.5451%), 80.0 (0.6660%), 90.0 (0.9766%), 90.0 (0.9766%), 80.0 (0.6827%), 70.0 (0.5442%), 60.0 (0.4515%), 50.0 (0.3797%), 40.0 (0.3210%), 30.0 (0.2656%), 25.0 (0.2387%), 20.0 (0.2126%), 15.0 (0.1857%), 10.0 (0.1551%), 5.0 (0.1179%), 0.0 (0.0381%) (8-A4)as shown in FIG. 78. UV chromatographic purity: 99.04% area (212 nm), (8-A4; Experiment Reference 8-Sample Reference A4 as shown in FIG. 151. $^1$H NMR: (DMSO-d6, 400 MHz); δ 10.6 (s, 1 H), 7.3 (d, J = 8.6 Hz, 1 H), 6.8 (s, 1 H), 6.6 (dd, J = 8.6, 2.2 Hz, 1 H), 6.5 (s, 2 H), 3.7 (s, 3 H), 3.1-3.0 (m, 6 H), 2.9 (t, J = 9.9, 5.6 Hz, 2 H), 2.6 (s, 3 H) conforms to the molecular structure (Σ20H*), (8-A4; Experiment Reference 8-Sample Reference A4), as shown in FIG. 146. Appearance: refer to FIG. 152 to FIG. 155 of 8-A4; Experiment Reference 8-Sample Reference A4. Solubility in SIF buffers: Soluble in FaSSIF, FeSSIF and FaSSGF at 37° C. up to 24 h. |

*The molecular formula ($C_{18}H_{22}N_2O_5$) includes the carboxylic acid protons; however, they co-resonate with water..

TABLE 186

The tabernanthalog monofumarate salt (Form B, Pattern #2a)

| Provenances of reference batches | The tabernanthalog Monofumarate salt (Form B, Pattern #2a, unary fumarate) |
|---|---|
| 7-B2 (Experiment Reference 7-Sample Reference B2): obtained from suspension equilibration of tabernanthalog monofumarate (Sample Reference 1, Pattern #1) in acetonitrile (5 vol) at 40° C. The product was isolated by centrifugation and was oven-dried under vacuum over 20 h at 40° C. | Reference batches:<br>7-J1 (Experiment Reference 7-Sample Reference J1),<br>7-J2 (Experiment Reference 7-Sample Reference J2),<br>7-M1 (Experiment Reference 7-Sample Reference M1),<br>7-B1 (Experiment Reference 7-Sample Reference B1),<br>7-B2 (Experiment Reference 7-Sample Reference B2),<br>7-O2 (Experiment Reference 7-Sample Reference O2),<br>1-B1 (Experiment Reference 1-Sample Reference B1), and<br>7-M2 (Experiment Reference 7-Sample Reference M2).<br>Molecular weight: 346.383 gmol$^{-1}$<br>Exact molecular weight: 346.153<br>Molecular formula: $C_{18}H_{22}N_2O_5$<br>Unary fumarate: 33.5% w/w th., fumaric acid (i.e., 1.0 mol of API to 1.0 mol fumaric acid).<br>XRPD: 9.1°, 12.3°, 14.2°, 15.7°, 16.4°, 17.1°, 17.4°, 18.1°, 18.8°, 20.7°, 21.0°, 22.3°, 22.8°, 23.0°, 24.7°, 25.0°, 25.6°, 26.8°, 27.3°, 2θ, 1 d.p), (A1272-022-B2, refer To FIG. 3, [Only peaks with >10% rel. intensity are provided.]<br>DSC: onset 100.6° C. (−0.74 Jg$^{-1}$, endotherm), 125.7° C. (−1.57 Jg$^{-1}$, endotherm) 174.1° C. (−31.27 Jg$^{-1}$, endotherm, melt); refer to FIG. 316.<br>TGA (only ablations events): onset 219.0° C. (−10.3% w/w, ablation) 286.8° C. (−1.9% w/w, ablation), 324.6° C. (−2.5% w/w, ablation); refer to FIG. 315.<br>$^1$H NMR: (DMSO-d6, 400 MHz); δ 10.6 (s, 1 H), 7.3 (d, J = 8.6 Hz, 1 H), 6.8 (s, 1 H), 6.6 (dd, J = 8.6, 2.2 Hz, 1 H), 6.5 (s, 2 H), 3.7 (s, 3 H), 3.1-3.0 (m, 6 H), 2.9 (t, J = 9.9, 5.6 Hz, 2 H), 2.6 (s, 3 H) conforms to the molecular structure (Σ20H*) as shown in FIG. 313).<br>Residual solvents ICH Q2C (R8): 7-B2 [acetonitrile (0.1% w/w (0.03% w/w, ICH listed 10 ppm)]. |

*The molecular formula ($C_{18}H_{22}N_2O_5$) includes the carboxylic acid protons; however, they co-resonate with water.

TABLE 187

Tabernanthalog hemifumarate (Form I, Pattern #14)

| Provenances of reference batches | Tabernanthalog hemifumarate (Form I, Pattern #14, hemi-fumarate) |
|---|---|
| (5-B3) (Experiment Reference 5-Sample Reference B3): obtained from dissolution of tabernanthalog (native); TBG Native) and fumaric acid (0.5 equiv) in methanol (20 vol). | Reference batches:<br>5-03,<br>5-02,<br>5-B2 (Experiment Reference 5-Sample Reference B2)<br>5-B3 (Experiment Reference 5-Sample Reference B3), and<br>11-Q2 (Experiment Reference 11-Sample Reference Q2)<br>Molecular weight: 576.694 gmol$^{-1}$<br>Exact molecular weight: 576.2947<br>Molecular formula: $C_{32}H_{40}N_4O_6$<br>Hemi-fumarate: 20.1% w/w th., fumaric acid (i.e., 2.0 mol of API to 1.0 mol fumaric acid).<br>Nature of hydrogen bonding: fumaric acid was situated in-between two molecules of Tabernanthalog via hydrogen bonds to the azepine (N1-O2, 2.70 Å) and indole nitrogen atoms (N2-O3, 2.81 Å).<br>Crystal system 300(2): monoclinic (refer to Section 9.16.2, page 375)<br>Space group 300(2): C2/c<br>Unit cell 300(2) K: a = 21.7386(8) Å, b = 9.7033(5) Å, c = 15.8640(8) Å, a = g = 90°, b = 99.182(4)°, V = 3303.4(3) Å$^3$<br>Asymmetric unit: contained one molecule of API and half molecule of fumaric acid (crystal bonded).<br>XRPD: 8.2°, 11.2°, 12.8°, 15.5°, 17.0°, , 18.1°, 18.3°, 19.2°, 19.4°, 20.2°, 21.3°, 21.5°, 22.6°, 23.7°, 24.3°, 24.8°, (2θ, 1 d.p), (refer to FIG. 377F) [Only peaks with >10% rel. intensity are provided.]<br>DSC: onset 50.1° C. (−22.64 Jg$^{-1}$, endotherm), 115.1° C. (−22.28 Jg$^{-1}$, endotherm) 183° C. (−14.73 Jg$^{-1}$, endotherm) 210.7 (−111.8 Jg$^{-1}$, endotherm, melt) (5-B3, FIG. 377J).<br>TGA (only ablations events): onset 75.9° C. (−1.2% w/w, solvent release) 141.5° C. (−1.3% w/w, solvent release), 224.0° C. (−23.6% w/w, ablation) (FIG. 377I).<br>$^1$H NMR: (DMSO-d6, 400 MHZ); δ 10.6 (s, 1 H), 7.3 (d, J = 8.6 Hz, 1 H), 6.8 (s, 1 H), 6.6 (dd, J = 8.6, 2.2 Hz, 1 H), 6.5 (s, 1 H), 3.7 (s, 3 H), 3.1-3.0 (m, 6 H), 2.9 (t, J = 9.9, 5.6 Hz, 2 H), 2.6 (s, 3 H) conforms to |

TABLE 187-continued

Tabernanthalog hemifumarate (Form I, Pattern #14)

| | |
|---|---|
| Provenances of reference batches | Tabernanthalog hemifumarate (Form I, Pattern #14, hemi-fumarate) |
| | the molecular structure (Σ19H*) (FIG. 377E).<br>Residual solvents: 5-B3 (acetonitrile 0.3% w/w, ICH listed 410 ppm, acetone 0.2% w/w, ICH listed 5000 ppm and methanol, 2.4% w/w, ICH listed 3000 ppm). |

*The molecular formula ($C_{18}H_{22}N_2O_5$) includes the carboxylic acid protons; however, they co-resonate with water.

G. Overall Conclusion

The tabernanthalog monofumarate salt Form A (unary fumarate, Pattern #6a), was prepared from water (anhydrous form, generated via suspension equilibration in water at 20° C.). Form A was subsequently scaled up to afford batch 8-A4 (Experiment Reference 8-Sample Reference A4) (560 mg, 56% th., yield uncorr.), to provide the control input for the salt screen stability and solubility panels. Form B was also identified, from acetonitrile; however, we were not able to obtain SC-XRD on this form.

In the presence of Form A, Form B slowly evolved into Form A under competitive suspension equilibration conditions. Metastable forms obtained via suspension equilibration and analyzed wet pellet, readily underwent conversion into Form A during drying. This supported the conclusion that Form A exhibited greatest relative stability amongst the forms identified. The hemi-fumarate salt was prepared and re-proportionated into the fumarate salt during an ageing cycle. Stability assessment of the supplied material (Pattern #1) at 40° C./75% RH executed over a 4-to-5-week period showed no evidence for hydrate formation, chemical degradation or disproportionation of the API.

Example 6: Salt Screen

Tabernanthalog is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data are used to assess crystallinity. PLM data are used to evaluate crystallinity and particle size/morphology. DSC data are used to evaluate melting point, thermal stability, and crystalline form conversion. TG data are used to evaluate if the free base is a solvate or hydrate, and to evaluate thermal stability. DVS data are used to evaluate hygroscopicity of the free base and if hydrates can be formed at high relative humidity. About 10 to 15 solvents are selected from Table 188, based on their properties (polarity, dielectric constant and dipole moment).

TABLE 188

List of Solvents Used in Salt Screening
Solvents

| | |
|---|---|
| acetic acid | n-heptane |
| Acetone | n-hexane |
| Acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | Methanol |
| Chlorobenzene | methoxybenzene (anisole) |
| Chloroform | methyl acetate |
| di(ethylene glycol) | methyl ethyl ketone (2-butanone) |
| Dichloromethane | methyl isobutyl ketone |
| diethyl ether | Nitromethane |
| Diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | Perfluorohexane |
| 1,4-dioxane | propyl acetate |
| 1,2-ethanediol (ethylene glycol) | 1,1,2,2-tetrachloroethane |
| Ethanol | Tetrahydrofuran |
| Ethanolamine | Toluene |
| 2-ethoxyethanol (Cellosolve) | 1,1,1-trichloroethane |
| ethyl acetate | 2,2,2-trifluoroethanol |
| ethyl formate | Water |
| formic acid | o-xylene (1,2-dimethylbenzene) |
| Glycerol | p-xylene (1,4-dimethylbenzene) |

The information obtained is used for designing the subsequent salt screen. The salt screen is performed by reacting the free base with pharmaceutically acceptable acids under various conditions in attempts to generate crystalline salts. Pharmaceutically acceptable acids that may be used are listed in Table 189 below. Specific acids are selected based on the pKa of the free base, and typically 15 to 20 acids are selected. Experiments are performed using 0.5 molar equivalent, 1 molar equivalent and/or 2 molar equivalents of the acid.

TABLE 189

Exemplary Acids

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |

TABLE 189-continued

Exemplary Acids

| | |
|---|---|
| gentisic acid | stearic acid |
| L-tartaric acid | orotic acid |
| fumaric acid | carbonic acid |
| galactaric (mucic) acid | |

Solvent systems for the salt crystallization experiments are selected based on the solubility of the free base and the selected acid. Solvents are used as a single solvent or as solvent mixtures, some containing water. The techniques that are used for salt crystallization are chosen based on the solvent selected and properties of the free base. The following techniques (or combination of techniques) may be used for salt crystallization:

- Free base and acid are dissolved in a solvent or mixture of solvents, and the solvents are evaporated at different rates (slow evaporation or fast evaporation) and at different temperatures (ambient or elevated).
- Free base and acid are dissolved in a solvent or mixture of solvents (at ambient temperature or an elevated temperature), and the final solution is cooled to a sub-ambient temperature (between −78° C. to 15° C.). The cooling method can be a fast cooling (by plunging the sample into an ice bath or a dry ice/acetone bath), or slow cooling. The solids formed will be recovered by filtration and dried (air dried or vacuum dried).
- Free base and acid are dissolved in a solvent or mixture of solvents, and an antisolvent is added to precipitate the salt. The solids formed will be recovered by filtration and dried (air dried or vacuum dried).
- Free base and acid are added to a solvent or mixture of solvents, where one or both components are not fully dissolved. The slurry is agitated at different temperatures for a number of days. The solids formed will be recovered by filtration and dried (air dried or vacuum dried). The same experiment can be also performed in solvent systems where the solvents are not miscible.
- Free base and acid are milled together (by mechanical milling or by mortar and pestle), with a drop of solvent, or without any solvent.
- Free base and acid are melted together and cooled to various temperatures using various cooling rates.
- If an amorphous form of a salt is obtained, the amorphous salt will be exposed to elevated humidity, or elevated temperature (or combination of both), or solvent vapors at various temperatures to form crystalline salts.

The stoichiometric ratio of acid to tabernanthalog, is confirmed by $^1$H NMR, HPLC, or both as is known to those of ordinary skill in the art.

The salts obtained are analyzed by XRPD to determine if they are crystalline and, if so, by DSC to see the melting point and by TG to see if they are hydrated/solvated, and by 1H NMR spectroscopy to ensure chemical integrity. KF water titration is performed on salts that are hydrated. DVS analysis is performed to evaluate hygroscopicity of the salt and if hydrated form is present.

Consistent with the methods above, the tabernanthalog salts listed in Table 190 were prepared and characterized.

TABLE 190

List of Prepared and Characterized Tabernanthalog Salts

| Salt | XRPD | Stoichiometry | Melting Point | $^1$H NMR Consistent with Structure? |
|---|---|---|---|---|
| Sorbate | FIG. 384 | 1.0 to 1.0 | 144° C. | Yes |
| Tartrate | FIG. 385 | 1.0 to 1.0 | 208° C. | Yes |
| Malate | FIG. 386 | 1.0 to 1.0 | 131° C. | Yes |
| Tosylate | FIG. 387 | 1.0 to 1.0 | 189° C. | Yes |
| Benzoate | FIG. 388 | 1.0 to 1.0 | 183° C. | Yes |
| Adipate | FIG. 389 | 1.0 to 1.0 | 149° C. | Yes |
| Glucoronate | FIG. 390 | 1.0 to 0.7 | 174° C. | Yes |
| Phosphate | FIG. 391 | — | 207° C. | Yes |
| Edisylate | FIG. 392 | 1.0 to 1 | — | Yes |
| Free Base | FIG. 393 | — | 149° C. | Yes |
| Sulfate | — | — | — | Yes |
| Maleate | FIG. 394 | 1.0 to 1.0 | — | Yes |
| Galactarate | FIG. 395 | 1.0 to 1.0 | — | Yes |
| Citrate | FIG. 396 | 1.0 to 0.9 | — | Yes |
| Glycolate | FIG. 397 | 1.0 to 1.0 | — | Yes |
| Succinate | FIG. 398 | 1.0 to 0.4 | — | Yes |

Example 7: Polymorph Screen of Tabernanthalog Salts

The active pharmaceutical ingredient (API), tabernanthalog, which may be a free base or a salt, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data are used to assess crystallinity. PLM data are used to evaluate crystallinity and particle size/morphology. DSC data are used to evaluate melting point, thermal stability, and crystalline form conversion. TG data are used to evaluate if the API is a solvate or hydrate, and to evaluate thermal stability. DX'S data are used to evaluate hygroscopicity of the API and if hydrates can be formed at high relative humidity. About 10 to 15 solvents may be selected from the list provided in Table 191 below, based on their properties (polarity, dielectric constant, and dipole moment).

TABLE 191

List of Solvents

| Solvents | |
|---|---|
| acetic acid | n-heptane |
| acetone | n-hexane |
| acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | methanol |
| chlorobenzene | methoxybenzene (anisole) |
| chloroform | methyl acetate |
| di(ethylene glycol) | methyl ethyl ketone (2-butanone) |
| dichloromethane | methyl isobutyl ketone |
| diethyl ether | nitromethane |
| diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | perfluorohexane |
| 1,4-dioxane | propyl acetate |
| 1,2-ethanediol (ethylene glycol) | 1,1,2,2-tetrachloroethane |
| ethanol | tetrahydrofuran |
| ethanolamine | toluene |

TABLE 191-continued

List of Solvents

| Solvents | |
|---|---|
| 2-ethoxyethanol (Cellosolve) | 1,1,1-trichloroethane |
| ethyl acetate | 2,2,2-trifluoroethanol |
| ethyl formate | water |
| formic acid | o-xylene (1,2-dimethylbenzene) |
| glycerol | p-xylene (1,4-dimethylbenzene) |

The information obtained is used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

- API is dissolved in a solvent or mixture of solvents, and the solvents are evaporated at different rates (slow evaporation or fast evaporation) and at different temperatures (ambient or elevated).
- API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).
- API is dissolved in a solvent or mixture of solvents, and an antisolvent is added to precipitate the salt. The solids formed will be recovered by filtration and dried (air dried or vacuum dried).
- API is added to a solvent or mixture of solvents, where the API is not fully dissolved. The slurry will be agitated at different temperatures for a number of days. The solids formed will be recovered by filtration and (air dried or vacuum dried).
- API is milled (by mechanical milling or by mortar and pestle), with a drop of solvent, or without any solvent.
- API is melted and cooled (at different cooling rates, fast and slow, and cooled to different temperatures) to obtain solids.
- API is suspended in a solvent or mixture of solvents, and the slurry is placed in a heating/cooling cycle for multiple cycles. The remaining solids after the final cooling cycle will be filtered and (air dried or vacuum dried).
- API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.
- API is exposed to elevated humidity (or elevated temperature, or combination thereof), or to solvent vapors for extended period of days.
- Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).
- API is heated to a specific temperature and cooled (at ambient conditions or in a dry box).

The solids obtained are analyzed by XRPD to determine if they are crystalline and, if so, by DSC to see the melting point and by TG to see if they are hydrated/solvated, and by $^1$H NMR spectroscopy to ensure chemical integrity. KF water titration is performed on forms that are hydrated. DVS analysis is performed to evaluate hygroscopicity of the form and if hydrated form is present. In particular, variable temperature analyses, including variable temperature XRPD, are performed to assess the stability of each physical form as well as its crystallinity.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C., and heated to 250-300° C. at a heating rate of 10° C./min under continuous nitrogen flow. TG analysis of the samples is performed with a Q 50 (TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45 °2θ with steps of 0.1°, and the measuring time is 1.0 second/step. All samples are ground to similar size before exposure to radiation. The powder samples are illuminated using CuKα radiation (λ=1.54056 Å) at 30 kV and 15 mA.

Variable temperature XRPD data are collected using a Huber Imaging Plate Guinier Camera 670 employing Ni-filtered CuKα$_1$ radiation (λ=1.5405981 Å) produced at 40 kV and 20 mA by a Philips PW1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 Kmin$^{-1}$ using a Huber High Temperature Controller HTC 9634 unit with the capillary rotation device 670.2. The temperature is held constant at selected intervals for 10 min while the sample is exposed to X-rays and multiple scans were recorded. A 2θ-range of 4.00-100.00 is used with a step size of 0.005 °2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fisher titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

Example 8: Salt Screen of Tabernanthalog

List of Abbreviations $a_w$ Water activity
ASD Amorphous solid dispersion
ca. circa, approximately
cf. to confer, to compare
° C. degree Celsius, absolute temperature
CP Chemical Purity
CP Cross-polarized light
CP-MAS Cross Polarized Magic Angle Spinning ($^{13}$C NMR solid state technique)
CPME Cyclopentyl methyl ether
Da Dalton
DCM Dichloromethane
DF Dilution factor
DiPE Diisopropyl ether
DMSO Dimethyl Sulfoxide
DSC Differential Scanning Calorimetry (measures changes in heat capacity)
DTA Differential Thermal Analysis (measures changes in temperature)
DVS Dynamic Vapour Sorption (used interchangeably with GVS)
e.g. for example
etc. etcetera
FaSSIF Fasted State Simulated Intestinal Fluid
FeSSIF Fed State Simulated Intestinal Fluid
FaSSGF Fasted State Simulated Gastric Fluid
FT-IR InfraRed spectroscopy (prefixed mid and far)
g gram(me)
GRAS Generally Recognised As Safe
GVS Gravimetric Vapour Sorption
h hour
HPLC High Performance Liquid Chromatography
HSM Hot Stage Microscopy
i.e. that is
IPA Isopropyl alcohol
IPrOAc Isopropyl acetate; sometimes abbreviated to IPAc
J Joule
K Degrees Kelvin. Si unit of temperature, used interchangeably with ° C. to express increment/decrement rate of change of temperature set point (e.g. ramp rate on DSC thermogram 10 K/min); note K sign not prefixed by °
KF Karl Fischer (aquametry, determination of the water content by coulometric titration)
kg kilogram(me)
l litre
LOD Loss On Drying
mag magnification
mAu milli Absorption units (chromatographic unit of peak height)
mAu*s milli Absorption units multiplied by second (chromatographic unit of peak area)
MEK Methyl ethyl ketone (butanone)
MET/CR Aptuit QC chromatography method reference
Me-THF 2-Methyltetrahydrofuran
min. minute
mg milligram(me)
ml millilitre
mol mole, amount of substance
N/A Not Applicable
n.a. not analysed
n.d. not detected
nm nanometre
NMP N-Methyl-2-Pyrrolidone
NMR Nuclear Magnetic Resonance (heteronuclear, prefixed by the stable isotope under analysis: $^{13}$C, $^{19}$F, $^1$H and $^{31}$P)
NP non-polarized
oab on anhydrous basis
oasfb on anhydrous solvent free basis
osfb on solvent free basis
PGI Potential genotoxic impurity
pH −log [H$^+$] or pH=−log $a_H^+$
$pK_a$ −log ($K_a$), acid dissociation constant
pI isoelectric point, quoted in unit pH
PLM Polarized Light Microscopy
Rel RT Relative Retention Time (not be confused RT)
REP/Aptuit report (REP) reference
RFA Request For Analysis (unique reference number)
RH Relative Humidity ($a_w$*100)
RT Room Temperature (ambient, typically: 18 to 23° C.)
s second
SCXD Single Crystal X-Ray Determination
SIF Simulated Intestinal Fluid
STA Simulated Thermal Analysis (STA=TGA+DTA)
t time in seconds, minutes, hour, days etc. (interval specified in parentheses); alias is in common use metric tonne (t)
t Tonne, metric unit of mass (1000 kg; 1 mg), (compaction force in kg, suffixed in parentheses)
T Temperature recorded in degrees Celsius (° C.); alias is in common use, SI unit of magnetic flux density, also denoted T
tBME tert-Butyl methyl ether
TCNB 2,3,5,6-Tetrachloronitrobenzene ($C_6HCl_4NO_2$, F.W. 260.89 gmol$^{-1}$); used as an internal stand for Q $^1$H NMR assay
TFE Trifluoroethanol
TGA Thermogravimetric Analysis
th. theoretical
UV Ultra Violet
vol volume
W Watt
w/w weight/weight
vs. versus
v/v volume/volume
XRPD X-Ray Powder Diffraction Counter Ion Abbreviations EDS Ethanesulfonic acid
MSA Methanesulfonic acid
TSA 4-Toluenesulfonic acid List of Definitions Amorphous Exhibits no long-range crystal order and displays a diffuse noise halo X-ray diffraction pattern.
Cross polarized light Light passed through two polaroid filters orientated at ninety degrees to one another.
Habit (crystal) Different crystal size or shape.
Native Refers to an API in its native or non-ionised form.

Normal light Vibrates in all directions perpendicular to the axis to which the light travels.

Particle size Expressed as probability distribution, i.e., the range D10>PSD<D90 captures the sizes of 80% of the particles.

Plane polarized light Light passed through a polaroid filter which allows light vibrating in one plane to be transmitted.

Polymorphism Crystalline solid able to exhibit different crystalline phases.

Photomicrograph Imaged captured of a small object under magnification through an optical microscope.

Pseudopolymorphism Different crystal structure attributed to the incorporation of molecular water or solvent.

Solvates Contains a molecule of solvent in the crystal lattice.

Thermogram Differential scanning calorimetry trace: heat flow on y-ordinate (mW), time (minutes)/temperature (° C.) on x-ordinate.

A. Study Overview

This study describes the salt screen performed on the API (tabernanthalog, native, non-ionized form). It covers the accompanying physicochemical evaluations that enabled nomination of a preferred salt form, i.e., The tabernanthalog sorbate salt (API to counter-ion ratio, 1 to 1).

B. Objectives

The objectives of this study of the salt screen are (a) to identify and characterize a fit for purpose salt form of Tabernanthalog, that is stable, crystalline, and exhibit improved physicochemical properties, compared to the native form, and (b) to demonstrate that the selected salt form is suitable for development scale-up.

C. Summary

Tabernanthalog (native) (non-ionized form, free base) was supplied as a crystalline solid (FIG. 393 and Table 215) and exhibited a single melt event evident by DSC (m.p 149° C., FIG. 439). The non-ionized form was freely soluble in most common solvents investigated at 20° C., apart from tBME, heptane and water (Experiment 1 and Table 198).

The non-ionized form of Tabernanthalog was screened against 23 common, Classes 1, 2 and 3 acidic counter-ions in selected solvents. The API delivered multiple hits (Experiment 2). Those salt forms that exhibited multiple thermal events by DSC and TGA, prior to deflagration were deprioritized (these activities often indicate that solvatomorphism or polymorphism complications may be present).

Salt selection was driven by the following desirable characteristics: (a) unique powder diffraction pattern by XRPD (this also confirms salification as the powder diffraction pattern should not match the free base API or the acid used), (b) flat baseline leading to single melt event by DSC, (c) flat baseline up to the melt by TGA, (d) significantly reduced impurity burden and absence of trace solvents by $^1$H NMR (stoichiometry should also be 1 to 1 ratio API to acid), and (e) optically crystalline and reasonably equant morphology under cross-polarized filter.

Based on the above criteria, the front-runner salt forms were the tabernanthalog sorbate salt, the tabernanthalog tartrate salt, the tabernanthalog malate salt, and the tabernanthalog benzoate salt.

This set of API salts were obtained as 1 to 1 ratio and were subsequently subjected to physicochemical studies that included: (a) solubility determination in FaSSIF, FeSSIF and FaSSGF buffers and the pH adjusted after each time point (Experiment 5), (b) stability evaluation at 40° C./75% RH for 10 days (the Equilibrium Humidity Evaluation Experiment) (no hydrate formation observed), and (c) DVS analyses (mass equilibrated, the Dynamic Vapour Sorption (DVS) Study).

The above studies concluded that the tabernanthalog sorbate salt was the preferred candidate as it exhibited much higher crystallographic quality than the tabernanthalog monofumarate salt. The is a key physical attribute required in later screening. Because the tabernanthalog sorbate salt exhibited a higher crystallographic quality, it is expected to provide greater solvent and impurity rejection and give overall better performance in advanced physicochemical screening. Furthermore, the chemical purity did not reduce significantly during stability, the salt was highly soluble in the SIF buffers examined and disproportionation was not observed. It is noted that sorbic acid is GRAS and is used as a food additive.

The tables of characterization are provided in Tables 192-194.

TABLE 192

| The Tabernanthalog Sorbate Salt | |
|---|---|
| Provenances of reference batches | The tabernanthalog sorbate salt (Form A) |
| 2-V2 (Experiment Reference 2-Sample Reference V2): obtained from heat-up / cool-down crystallization of Tabernanthalog (native) with sorbic acid in ethanol (5.0 vol) at 85° C. The product was isolated by centrifugation and was oven-dried under reduced pressure over 20 h at 40° C.<br>3-C1 (Experiment | Reference batches: 2-V2 (Experiment Reference 2-Sample Reference V2), 3-C1 (Experiment Reference 3-Sample Reference C1), 4-A2 (Experiment Reference 4-Sample Reference A2)<br>Molecular weight: 342.439 g · mol$^{-1}$<br>Exact molecular weight: 342.1943<br>Molecular formula: $C_{20}H_{26}N_2O_3$<br>Unary sorbate: 24.7% w/w th., sorbic acid (i.e., 1.0 mol of API to 1.0 mol sorbic acid)<br>SCXRD: Unary / mono sorbate. The simulated powder pattern, predicted from single crystal structure at 100K agreed with the experimentally observed Form A powder pattern obtained at 298K.<br>Nature of hydrogen bonding: Hydrogen bonding between both oxygen molecules on the sorbate ion. One to N1 (tryptamine nitrogen atom) of one API molecules, the other to N2 (hydro-azepine nitrogen atom) of a separate API molecule. Due to hydrogen bonding present in the structure builds up chains between API and salt molecule. Causing stacking of API and sorbate molecules closely packed to one another. This leads to less free space in the crystal structure and void radius of only ~0.9 A, much smaller than the 1.4 required for a water molecule to occupy. Bond between Sorbates and API, |

TABLE 192-continued

The Tabernanthalog Sorbate Salt

| Provenances of reference batches | The tabernanthalog sorbate salt (Form A) |
|---|---|
| Reference 3-Sample Reference C1): same as above. However, dissolution was achieved in ethanol (3.0 vol) and was isolated by filtration and dried under sustained nitrogen flux (<1 bar) over 20 h at 20° C. 4-A2 (Experiment Reference 4-Sample Reference A2): same as 3-C1 (Experiment Reference 3-Sample Reference C1). | N1-O3, 2.857 Å (hydrogen bond), N2-O2, 2.7015 Å (salification hydrogen bond) N1 = Indole, N2 = Hydroazepine. Sorbate molecule is disordered and bond lengths stated are an average of the two mapped positions. Crystal system 100(2)K: monoclinic Space group 100(2)K: $P2_1/_C$ Unit cell 100(2)K: a = 9.3410(3) Å, b = 6.4173(2) Å, c = 30.5108(12) Å. A = γ = 90° β = 95.374(3)°, V = 1820.90(11) Å3. Asymmetric unit: contains one API molecule one sorbate ion. XRPD: 5.7°, 10.5°, 11.4°, 17.9°, 18.8°, 19.1°, 21.4°, 22.6°, 22.9°, 24.4°, 24.7°, 26.8° (2θ, 1 d.p) [(2-V2), FIG. 384 and Table 216]. DSC: onset 143.9° C. (−84.1 Jg$^{-1}$, endotherm, melt) [(2-V2), FIG. 453]. TGA: onset 171.8° C. (−26.0% w/w, ablation) 250.0° C. (−19.9% w/w, ablation) [(2-V2), FIG. 454]. DVS 0 to 90 to 0% RH (dm/dt <0.002%): 0.0 (0.00%), 5.0 (0.0%), 10.0 (0.01%), 15.0 (0.01%), 20.0 (0.02%), 25.0 (0.03%), 30.0 (0.03%), 40.0 (0.05%), 50.0 (0.07%), 60.0 (0.10%), 70.0 (0.14%), 80.0 (0.21%), 90.0 (0.98%), 90.0 (0.98%), 80.0 (0.48%), 70.0 (0.30%), 60.0 (0.18%), 50.0 (0.06%), 40.0 (0.03%), 30.0 (0.00%), 25.0 (−0.007%), 20.0 (−0.02%), 15.0 (−0.03%), 10.0 (−0.04%), 5.0 (−0.05%), 0.0 (−0.06%) [(4-A2), FIGS. 455 and 456]. UV chromatographic purity: 99.64% area (212 nm), [(4-A2), FIG. 566]. $^1$H NMR: (DMSO-d6, 400 MHz); δ 10.4 (s, 1 H), 7.2 (d, J = 9.4 Hz, 1 H), 7.1 (dd, J = 15.4, 9.6 Hz 1 H), 6.7 (d, J = 2.3 Hz, 1 H), 6.6 (dd, J = 8.5, 2.2 Hz, 1 H), 6.3-6.2 (m, 2 H), 5.8 (d, J = 15.4 Hz, 1 H), 3.7 (s, 3 H), 2.9-2.7 (m, 8 H) 2.4 (s, 3 H), 1.8 (d, J = 5.9 Hz, 3 H) conforms to the molecular structure (Σ25H*), (Experiment 4-A2, FIG. 562). Residual solvents ICH Q3C (R8): 4-A2 (ethanol 0.1% w/w); 3-C1 (ethanol 0.3% w/w); 2-V2 (ethanol 0.1% w/w, ICH listed 5000 ppm). Appearance: columnar, prismatic crystals, [(4-A2), FIGS. 567-572]. Solubility in SIF buffers: Insoluble in FeSSIF at 37° C. up to 1 h. Insoluble in FaSSGF at 37° C. up to 24 h. |

*The molecular formula ($C_{20}H_{26}N_2O_3$) includes the carboxylic acid proton that is not detected by $^1$H NMR

TABLE 193

The Tabernanthalog Tartrate Salt

| Provenances of reference batches | The tabernanthalog tartrate salt |
|---|---|
| 2-I2 (Experiment Reference 2-Sample Reference I2): obtained from heat-up / cool-down crystallization of Tabernanthalog (native) with L-tartaric acid in ethanol (11.2 vol) and water (7.2 vol) at 85° C. The product was isolated by centrifugation and was oven-dried under reduced pressure over 20 h at 40° C. 3-A1 (Experiment Reference 3-Sample Reference A1): same as above, however, dissolution was achieved in ethanol (5.0 vol) and water (5.75 vol) at 85° C. Product was isolated by filtration and dried under | Reference batches: 2-I2 (Experiment Reference 2-Sample Reference I2), 3-A1 (Experiment Reference 3-Sample Reference A1) Molecular weight: 380.397 g · mol$^{-1}$ Exact molecular weight: 380.1583 Molecular formula: $C_{18}H_{24}N_2O_7$ Unary tartrate: 39.5% w/w th., L-tartaric acid (i.e., 1.0 mol of API to 1.0 mol tartaric acid) XRPD: 16.1°, 16.4°, 17.3°, 18.2°, 19.9°, 20.4°, 21.3°, 22.4°, 24.0°, 24.3°, 26.1°, 26.8°, 28.3°, 32.6°, 32.9°, 34.3°, 37.8°, 38.1° (2θ, 1 d.p) [(2-I2), FIG. 385 and Table 217]. DSC: onset 208.2° C. (−137.2 Jg$^{-1}$, endotherm, melt) [(2-I2), FIG. 469]. TGA: onset 219.3° C. (−56.1% w/w, ablation) 322.1° C. (−9.5% w/w, ablation) [(2-I2), FIG. 470]. DVS 0 to 90 to 0% RH (dm/dt <0.002%): 0.0 (0.00%), 5.0 (0.01%), 10.0 (0.02%), 15.0 (0.04%), 20.0 (0.05%), 25.0 (0.07%), 30.0 (0.10%), 40.0 (0.16%), 50.0 (0.24%), 60.0 (0.34%), 70.0 (0.48%), 80.0 (0.72%), 90.0 (1.34%), 90.0 (1.34%), 80.0 (0.75%), 70.0 (0.51%), 60.0 (0.37%), 50.0 (0.27%), 40.0 (0.20%), 30.0 (0.13%), 25.0 (0.11%), 20.0 (0.08%), 15.0 (0.07%), 10.0 (0.04%), 5.0 (0.03%), 0.0 (0.02%) [(3-A1) FIGS. 471 and 472]. UV chromatographic purity: 99.58% area (212 nm) [(3-A1) FIG. 476]. $^1$H NMR: (DMSO-d6, 400 MHz); δ 10.6 (s, 1 H), 7.3 (d, J = 8.2 Hz, 1 H), 6.8 (d, J = 2.3 Hz, 1 H), 6.6 (dd, J = 8.7, 2.2 Hz, 1 H), 4.0 (s, 2H), 3.7 (s, 3 H), 3.1-3.0 (m, 6 H), 2.9 (t, J = 10.6, 5.6 Hz, 2 H), 2.6 (s, 3 H) conforms to the molecular structure (Σ20H*), [(3-A1) FIGS. 545 and 546]. Residual solvents ICH Q3C (R8): 3-A1 (ethanol 0.05% w/w); 2-I2 (ethanol 0.1% w/w, ICH listed 5000 ppm). Appearance: non-homogeneous plates, [(3-A1) FIGS. 477-482]. Solubility in SIF buffers: Soluble in all SIF buffers at 37° C. during 24 h. |

TABLE 193-continued

The Tabernanthalog Tartrate Salt

| Provenances of reference batches | The tabernanthalog tartrate salt |
|---|---|
| sustained nitrogen flux (<1 bar) over 20 h at 20° C. | |

*The molecular formula ($C_{18}H_{24}N_2O_7$) includes the hydroxyl and carboxylic acid protons that are not detected by $^1H$ NMR.

TABLE 194

The Tabernanthalog Benzoate Salt

| Provenances of reference batches | Tabernanthalog•Benzoate |
|---|---|
| 2-R2 (Experiment Reference 2-Sample Reference R2): obtained from heat-up / cool-down crystallization of Tabernanthalog (native) with benzoic acid in ethanol (8.4 vol) and water (1.4 vol) at 85° C. The product was isolated by centrifugation and was oven-dried under reduced pressure over 20 h at 40° C. 3-B1 (Experiment Reference 3-Sample Reference B1): same as above, however, dissolution was achieved in ethanol (5.0 vol) and water (0.85 vol) at 85° C. Product was isolated by filtration and dried under sustained nitrogen flux (<1 bar) over 20 h at 20° C. | Reference batches: 2-R2 (Experiment Reference 2-Sample Reference R2), 3-B1 (Experiment Reference 3-Sample Reference B1) Molecular weight: 352.43 g · mol$^{-1}$ Exact molecular weight: 352.1786 Molecular formula: $C_{21}H_{24}N_2O_3$ Unary benzoate: 34.6% w/w th., benzoic acid (i.e., 1.0 mol of API to 1.0 mol benzoic acid) XRPD: 9.0°, 14.1°, 15.6°, 16.7°, 17.7°, 18.1°, 19.6°, 21.3°, 22.9°, 23.7°, 24.4°, 26.3°, 28.9° (2θ, 1 d.p), [(2-R2) FIG. 388 and Table 218]. DSC: onset 186.0° C. (−107.1 Jg$^{-1}$, endotherm, melt) [(3-B1) FIG. 552]. TGA: onset 205.3° C. (−54.5% w/w, ablation) [(3-B1) FIG. 556]. DVS 0 to 90 to 0% RH (dm/dt <0.002%): 0.0 (0.00%), 5.0 (−0.001%), 10.0 (0.002%), 15.0 (−0.002%), 20.0 (−0.003%), 25.0 (−0.002%), 30.0 (0.002%), 40.0 (0.002%), 50.0 (0.006%), 60.0 (0.009%), 70.0 (0.009%), 80.0 (0.046%), 90.0 (0.118%), 90.0 (0.118%), 80.0 (0.063%), 70.0 (0.034%), 60.0 (−0.001%), 50.0 (−0.014%), 40.0 (−0.018%), 30.0 (−0.023%), 25.0 (−0.028%), 20.0 (−0.029%), 15.0 (−0.032%), 10.0 (−0.032%), 5.0 (−0.034%), 0.0 (−0.037%) [(3-B1) FIGS. 486(A) and 486(B)]. UV chromatographic purity: 99.23% area (212 nm), (3-B1) FIG. 486(E)]. $^1H$ NMR: (DMSO-d6, 400 MHz); δ 10.0 (s, 1 H), 7.9 (dd, J = 8.0, 1.0 Hz, 2 H), 7.6 (td, J = 14.7, 7.2, 2.6, 1.1 Hz, 1 H), 7.5 (t, J = 15.1, 7.8 Hz, 1 H), 7.2 (d, J = 8.6 Hz, 1 H), 6.7 (d, J = 8.6, 2.2 Hz, 1 H), 3.7 (s, 3 H), 2.9-2.8 (m, 2 H), 2.8-2.7 (m, 6 H), 2.4 (s, 3 H) conforms to the molecular structure (Σ23H*) [(3-B1) FIGS. 547 and 548]. Residual solvents ICH Q3C (R8): 3-B1 (ethanol 0.3% w/w); 2-R2 (ethanol 0.1% w/w, ICH listed 5000 ppm). Appearance: [(3-B1) FIGS. 486(F)-486(K)]. Solubility in SIF buffers: Soluble in all SIF buffers at 37° C. during 24 h. |

*The molecular formula ($C_{21}H_{24}N_2O_3$) includes the carboxylic acid proton that is not detected by $^1H$ NMR

D. Salt Screen

The objective of the salt screen was to identify a pharmaceutically acceptable crystalline salt form of the API. In addition, the elected salt form should exhibit appropriate physicochemical properties and should possess relevant toxicological considerations that are judged suitable for development scale-up. Additionally, a preliminary process to access the elected salt form was evaluated.

The pKa of Tabernanthalog was calculated (cpKa) using MarvinSketch 20.21.0 from ChemAxon Ltd. Compounds most suited to salification contain an ionizable functional group at least 3 pKa units removed from the counter-ions being screened. Non-ionized Tabernanthalog has cpKa of 8.0 on the azepine nitrogen, while the indole nitrogen is assumed to be non-ionizable in both compounds (FIG. 399).

The counterions for the salt screened were selected based on their theoretical pKa values. The initial screen was carried out against ca. 22 acids (refer to Table 195, Table 196, Table 197).

TABLE 195

Class 1 counter ions proposed for salt screen on Tabernanthalog.

| REAGENT | pK$_a$ Value | | | EXAMPLE USE |
| | pK$_a$ 1 | pK$_a$ 2 | pK$_a$ 3 | |
|---|---|---|---|---|
| Hydrochloric acid | −6.0 | — | — | Nearly half of all salts of basic drug substances |
| Sulfuric acid | −3.0 | 1.9 | — | Amphetamine sulfate |
| Maleic acid | 1.9 | 6.2 | — | Bromophenir-amine maleate, |

TABLE 195-continued

Class 1 counter ions proposed for salt screen on Tabernanthalog.

| REAGENT | pK$_a$ 1 | pK$_a$ 2 | pK$_a$ 3 | EXAMPLE USE |
|---|---|---|---|---|
| Phosphoric acid | 1.9 | 7.1 | 12.3 | chlorpheniramine maleate (OTC) Codeine Phosphate, clindamycin phosphate |
| (+)-L-Tartaric acid | 3 | 4.4 | — | Zolpidem tartrate, Brimonidine tartrate, Revastigmine tartrate |
| Fumaric acid | 3 | 4.4 | — | Ketotifen fumarate (OTC), Clemastine fumarate (OTC) |
| Galactaric acid | 3.1 | 3.6 | — | Quinidine polygalacturonate |
| Citric acid | 3.1 | 4.8 | 6.4 | Sildenafil citrate, Tamoxifen citrate, Azithromycin citrate |
| D-Glucuronic acid | 3.2 | — | — | Trimetrexate glucuronate, Neutrexin |
| Glycolic acid | 3.3 | — | — | |
| (−)-L-Malic acid | 3.5 | 5.1 | — | Acetophenazine maleate, Pheniramine maleate, Chlorheniramine maleate |
| D-Gluconic acid | 3.8 | — | — | Chlorhexidine gluconate, Quinidine gluconate |
| L-Lactic | 3.9 | — | — | Haloperidol lactate |
| L-Ascorbic acid | 4.2 | — | — | Vascor |
| Succinic acid | 4.2 | — | — | Desvenlafaxine succinate, Loxapine succinate, Sumatriptan succinate |
| Acetic acid | 4.8 | — | — | Hydrocortisone acetate, Desmopressin |
| Adipic acid | 4.4 | 5.4 | | fatty acid metabolite |
| Sorbic acid | 4.7 | | | food-grade preservative |

TABLE 196

Class 2 counter ions proposed for salt screen on Tabernanthalog

| REAGENT | pKa 1 | pKa 2 | pKa 3 | EXAMPLE USE |
|---|---|---|---|---|
| p-Toluenesulfonic acid* | −1.3 | — | — | — |
| Methanesulfonic acid* | 2.1 | — | — | Almitrine, anatzoline |
| Ethane sulfonic acid* | 2.05 | — | — | Ergotoxine, dihydroergocornine |
| Benzoic acid | 4.2 | | | Rizatriptan benzoate, Betamethasone benzoate |

*PGI risk, in conjunction with alcohols.

TABLE 197

Class 3 counter ions proposed for salt screen on Tabernanthalog.

| REAGENT | pK$_a$ 1 | pK$_a$ 2 | pK$_a$ 3 | EXAMPLE USE |
|---|---|---|---|---|
| Hydrobromic acid | −9.0 | — | — | Citalopram, lithium | i. Targeted Solubility of Tabernanthalog in Common Solvents (Experiment 1)

The approximate solubility of Tabernanthalog (native) was determined in various solvents at room temperature, 40° C., and at reflux. The solutions were observed after cooling to determine if crystallization occurred on standing at room temperature.

This study provided essential solubility information, necessary to select appropriate solvents to undertake the salt screen. The solubility of Tabernanthalog (native) was assessed against 19 common solvents. The API, Tabernanthalog (native) was soluble in 16 solvents at reflux (various volumes) and solid was observed upon cooling (Table 198). Exceptions were tBME, heptane and water.

By analogy with the solubility properties of the tabernanthalog monofumarate salt, ethanol was selected as the initial solvent to use in the salt screen [1-F1 (Experiment Reference 1-Sample Reference F1), Table 198].

ii. Heat-Up Cool-Down Crystallization Salt Screen (Experiment 2)

Evidence of salt formation in the solid state was provided by the following analyses (a) presentation of a unique powder diffraction pattern, that exhibited significant differences from the powder patterns of Tabernanthalog (native), the native acid counterion (also assumed non-ionized) and importantly, was non-congruent with the sum of their reflections, (b) presence of integer stoichiometry of the counterion with respect to tabernanthalog (native) and a measurable change in the chemical shift (δ values), of the relevant ionizable proton resonances, by solution $^1$H NMR, and (c) change in the temperature of fusion and ΔH fusion by DSC, compared to the values exhibited by Tabernanthalog (native) and the acid counterion.

TABLE 198

Targeted solubility screen of Tabernanthalog (native) in common solvents.

| Experiment Reference-Sample Reference | Solvent | ICH Class | 5 vol Solution at 20° C. | 5 vol Solution at 40° C. | 5 vol Reflux | 5 vol Solid on cooling | 10 vol Solution at 20° C. | 10 vol Solution at 40° C. | 10 vol reflux | 10 vol Solid on cooling |
|---|---|---|---|---|---|---|---|---|---|---|
| 1-A | Acetone | 3 | x | x | ✓ | Yes | | | | |
| 1-B | Acetonitrile | 2 | x | x | x | — | x | x | ✓ | Yes |

TABLE 198-continued

Targeted solubility screen of Tabernanthalog (native) in common solvents.

| | | | | | | | | | | |
|---|---|---|---|---|---|---|---|---|---|---|
| 1-C | terl-Butylmethyl ether | 3 | x | x | x | — | x | x | x | — |
| 1-D | Chlorobenzene | 2 | x | x | ✓ | Yes | | | | |
| 1-E | Dichloromethane | 2 | x | x | ✓ | Yes | | | | |
| 1-F | Ethanol | 3 | x | x | ✓ | Yes | | | | |
| 1-G | Ethyl acetate | 3 | x | x | x | — | x | x | ✓ | Yes |
| 1-H | Ethyl formate | 3 | x | x | x | — | x | x | ✓ | Yes |
| 1-I | Heptane | 3 | x | x | x | — | x | x | x | — |
| 1-J | Isopropyl acetate | 3 | x | x | x | — | x | x | x | — |
| 1-K | Methanol | 2 | x | x | ✓ | Yes | | | | |
| 1-L | Methyl acetate | 3 | x | x | x | — | x | x | ✓ | Yes |
| 1-M | Methylethyl ketone | 3 | x | x | ✓ | Yes | | | | |
| 1-N | 2-Methyl THF | # | x | x | ✓ | Yes | | | | |
| 1-O | Nitromethane | 2 | x | x | ✓ | Yes | | | | |
| 1-P | 2-Propanol | 3 | x | x | ✓ | Yes | | | | |
| 1-Q | Tetrahydrofuran | 2 | x | x | ✓ | Yes | | | | |
| 1-R | Toluene | 2 | x | x | x | — | x | x | x | — |
| 1-S | Water | # | x | x | x | — | x | x | x | — |

| Experiment | 15 vol | | | | 20 vol | | | |
|---|---|---|---|---|---|---|---|---|
| Reference-Sample | Solution at | | | Solid on | Solution at | | | Solid on |
| Reference | 20° C. | 40° C. | reflux | cooling | 20° C. | 40° C. | reflux | cooling |
| 1-A | | | | | | | | |
| 1-B | | | | | | | | |
| 1-C | x | x | x | — | x | x | x | — |
| 1-D | | | | | | | | |
| 1-E | | | | | | | | |
| 1-F | | | | | | | | |
| 1-G | | | | | | | | |
| 1-H | | | | | | | | |
| 1-I | x | x | x | — | x | x | x | — |
| 1-J | x | x | ✓ | Yes | | | | |
| 1-K | | | | | | | | |
| 1-L | | | | | | | | |
| 1-M | | | | | | | | |
| 1-N | | | | | | | | |
| 1-O | | | | | | | | |
| 1-P | | | | | | | | |
| 1-Q | | | | | | | | |
| 1-R | x | x | ✓ | Yes | | | | |
| 1-S | x | x | x | | x | x | x | — |

Priority was given to those salts that exhibited good crystallinity and little obvious disordering by XRPD, a flat DSC baseline in conjunction with a single sharp melt event and negligible weight loss, prior to deflagration by TGA, were also considered to be desirable characteristics. The analytical data of the rejected salt forms are reported in FIGS. 529, 394-398, and 535-544 and Tables 225-229.

Five anhydrous, solvent free, single melt, stable forms of salified Tabernanthalog were identified (i.e. 1.0 mol of API to 1.0 mol stoichiometry salts (green shaded entries in Table 199), in conjunction with a suitable stable form of the tabernanthalog monofumarate salt (Pattern #6a (Form A), for example, Table 185 of Example 5). More specifically, the tabernanthalog sorbate salt (2-V2 or Experiment Reference 2-Sample Reference V2), The tabernanthalog tartrate salt (2-I2 or Experiment Reference 2-Sample Reference I2), The tabernanthalog malate salt (2-O2 or Experiment Reference 2-Sample Reference O2) and The tabernanthalog benzoate salt (2-R2 or Experiment Reference 2-Sample Reference R2) were selected and progressed through into the physicochemical evaluation, using the tabernanthalog monofumarate salt (Pattern #6a, Form A, 8-A4 (Experiment Reference 8-Sample Reference A4) of Example 5 above), as the control. The entries not reported in Table 199 did not crystallize and remained as solutions at sub-ambient temperature.

The tabernanthalog sorbate salt (2-V2 (Experiment Reference 2-Sample Reference V2), FIGS. 451-466 and Table 216) was highly crystalline by XRPD analysis and exhibited unique powder diffraction pattern (FIG. 400). Negligible change in the impurity burden was observed in aryl and aliphatic regions (FIG. 451). Sharp melt (onset 144° C.) was observed as shown in FIG. 453 (non-ionized Tabernanthalog (m.p. 149° C.) and sorbic acid (m.p. 135° C.), as well as a flat TG baseline (FIG. 454).

The tabernanthalog tartrate salt (2-I2 (Experiment Reference 2-Sample Reference I2), FIGS. 467-482 and Table 217) showed a highly crystalline powder diffraction pattern that was different from Tabernanthalog (native) and L-tartaric acid (FIG. 401). $^1$H NMR analysis exhibited a decrease in the impurity burden was observed in aryl and aliphatic regions (FIG. 467). The specimen exhibited sharp, single melt event (208° C.) as shown in FIG. 469 (non-ionized Tabernanthalog (m.p. 149° C.) and L-tartaric acid (m.p. 169° C.)), and a flat TG baseline prior ablation (FIG. 470).

The tabernanthalog malate salt (2-O2 (Experiment Reference 2-Sample Reference O2), FIGS. 488-492 and Table 219) was highly crystalline with sharp, well resolved reflections and a unique powder diffraction pattern (FIG. 402). A small increase in the impurity burden in aryl and aliphatic regions was observed in the $^1$H NMR spectrum of 2-O2 (FIG. 488). The thermogram exhibited a sharp melt event (131° C.) as shown in FIG. 490 (non-ionized Tabernanthalog (m.p. 149° C., and malic acid (m.p. 130° C.)), and TGA showed a flat baseline (FIG. 491).

The tabernanthalog benzoate salt (2-R2 (Experiment Reference 2-Sample Reference R2), FIGS. 388, 483-486(B) and 486(C)-486(K) and Table 218) was unique by XRPD (FIG. 404) and highly crystalline with low background. Negligible change in the impurity burden was observed in aryl and aliphatic regions (FIG. 484). Sharp melt event (onset 183° C., as shown in FIG. 485 was observed by DSC (non-ionized

TABLE 199

Experiment 2 Results from salt screen on Tabernanthalog. The five salt forms highlighted in dark green were nominated for scale-up

| Experiment Reference-Sample Reference | Salt | Flat baseline (DSC)? | Discrete melt (DSC)? | Flat baseline pre-melt (TGA)? | $^1$H NMR concordant with structure? | $^1$H NMR (impurity burden)? |
|---|---|---|---|---|---|---|
| 2-V2 | Tabernanthalog•Sorbate | ✓ | ✓ | ✓ | ✓ | Reduced |
| 2-I2 | Tabernanthalog•Tartrate | ✓ | ✓ | ✓ | ✓ | Reduce |
| 2-O2 | Tabernanthalog•Malate | ✓ | ✓ | ✓ | ✓ | Maintained |
| 2-E2 | Tabernanthalog•Tosylate | ✓ | ✓ | ✓ | ✓ | Reduced |
| 2-R2 | Tabernanthalog•Benzoate | ✓ | ✓ | ✓ | ✓ | Reduced |
| 2-U2 | Tabernanthalog•Adipate | ✓ | ✓ | x | ✓ | Reduced |
| 2-M2 | Tabernanthalog•Glucuronate | ✓ | ✓ | ✓ | ✓ | Elevated |
| 2-H2 | Tabernanthalog•Phosphate | ✓ | ✓ | x | ✓ | Elevated |
| 2-J2 | Tabernanthalog•Edisylate | x | x | x | ✓ | Reduced |
| 2-C2 | Tabernanthalog•Sulfate | x | x | — | ✓ | Not acquired |
| 2-G2 | Tabernanthalog•Maleate | x | x | x | ✓ | Reduced |
| 2-K2 | Tabernanthalog•Galactarate | x | x | ✓ | ✓ | Reduced |
| 2-L2 | Tabernanthalog•Citrate | x | x | x | ✓ | Reduced |
| 2-N2 | Tabernanthalog•Glycolate | x | x | x | ✓ | Reduced |
| 2-S2 | Tabernanthalog•Succinate | x | x | x | ✓ | Reduced |

Experiment 2 Results from salt screen on Tabernanthalog. The five salt forms highlighted in dark green were nominated for scale-up

| Experiment Reference-Sample Reference | Unique XRPD? | Solvent (ICH listed < 5000 ppm) | Salt stoichiometry | Acceptable pharmaceutical sale form? | Salt class |
|---|---|---|---|---|---|
| 2-V2 | ✓ | 0.1% | 1.0 to 1.0 | ✓ | 1 |
| 2-I2 | ✓ | 0.1% | 1.0 to 1.0 | ✓ | 1 |
| 2-O2 | ✓ | 0.2% | 1.0 to 1.0 | ✓ | 1 |
| 2-E2 | ✓ | 0.1% | 1.0 to 1.0 | ✓ | 2 |
| 2-R2 | ✓ | 0.1% | 1.0 to 1.0 | ✓ | 2 |
| 2-U2 | ✓ | 0.3% | 1.0 to 1.0 | ✓ | 1 |
| 2-M2 | ✓ | 0.2% | 1.0 to 0.7 | ✓ | 1 |
| 2-H2 | Disordered | 0.3% | Not determined | ✓ | 1 |
| 2-J2 | Disordered | 0.4% | 1.0 to 1.1 | ✓ | 2 |
| 2-C2 | Amorphous | — | — | ✓ | 1 |
| 2-G2 | Disordered | 3.7% | 1.0 to 1.0 | ✓ | 1 |
| 2-K2 | v. Disordered | 0.1% | 1.0 to 1.0 | ✓ | 1 |
| 2-L2 | v. Disordered | 2.2% | 1.0 to 0.9 | ✓ | 1 |
| 2-N2 | Glucuronic acid | 8.5% | 1.0 to 1.0 | ✓ | 1 |
| 2-S2 | ✓ | 2.3% | 1.0 to 0.4 | ✓ | 1 |

Front-runner salt forms
Back-up salt forms
Undesirable characteristic
Deprioritised salt forms The tabernanthalog tosylate salt's (2-E2 (Experiment Reference 2-Sample Reference E2), FIGS. 493-496A and Table 220) diffractogram was also unique (FIG. 403) and highly crystalline by XRPD, with low angle reflection dominated, probably due to particle effects. It is noted that diffraction pattern should improve with increased powder averaging. $^1$H NMR analysis showed a small decrease in the impurity burden in aryl and aliphatic regions (FIG. 493). DSC thermogram contained a single melt event (189° C.) as shown in FIG. 495 (non-ionized Tabernanthalog (m.p. 149° C.) and toluene sulfonic acid (m.p. 105 to 107° C.)), and TGA thermogram exhibited a small weight-loss transition, attributed to water from hydrated tosic acid (FIG. 496).

Tabernanthalog (m.p. 149° C.) and benzoic acid (m.p. 122° C.)), and a flat baseline by TGA analysis (FIG. 486).

The salt forms selected for the 1 g scale-up and physicochemical evaluation (Experiment 3 and the Physicochemical Evaluation study) were the tabernanthalog tartrate salt, the tabernanthalog benzoate salt and the tabernanthalog sorbate salt.

iii. Scale-Up Preparation of Nominated Salt Forms
(Experiment 3)

The experimental procedure is provided in Section G.ii, and the analytical characterization data are provided in I.ii.

Tabernanthalog (native) was used for the selected salts scale-up.

The tabernanthalog tartrate salt (3-A1; Experiment Reference 3-Sample Reference A1), was delivered as a beige solid at 95% uncorr. yield and the form matched the form, from the previous batch (2-I2; Experiment Reference 2-Sample Reference I2) as shown in FIG. 405).

The tabernanthalog benzoate salt (3-B1; Experiment Reference 3-Sample Reference B1), was provided as a light brown solid at 87% uncorr. yield and was the same form as the previous batch (2-R2; Experiment Reference 2-Sample Reference R2) as shown in FIG. 406).

The tabernanthalog sorbate salt (3-C1; Experiment Reference 3-Sample Reference C1), was obtained as a light brown solid at 87% uncorr. yield and the form matched the form, from the previous batch (2-V2 (Experiment Reference 2-Sample Reference V2) shown in FIG. 407.

Comparison of m.p. onset and melt enthalpies is summarized in Table 200. Discrepancies in m.p. were evident on the scaled-up samples. A DSC specimen of 3-BJ (Experiment Reference 3-Sample Reference B1) was further examined because decomposition and ablative activity appeared to occur well after melting (arrow in FIG. 408), the DSC was programmed as follows: 20° C. to 220° C., 220° C. to 20° C., and 20° C. to 300° C. The aim was to melt, crystallize and re-melt and assess the new onset temperature.

The thermocycle applied did not show a crystallization event and a melt was not observed, therefore this was not repeated on the rest of the specimens as shown in FIG. 554.

TABLE 200

Comparison of m.p. onset and melt enthalpies

| Experiment Reference-Sample Reference | Counter ion | $pK_a 1$ $pK_a 1$ | $pK_a 2$ $pK_a 2$ | DSC (m.p. onset and enthalpy data) |
|---|---|---|---|---|
| 2-I2 3-A1 | (+)-L-Tartaric acid | 3.00 | 4.40 | 208.22° C. (−137.23 Jg^−1) 202.62° C. (−161.53 Jg^−1) |
| 2-R2 3-B1 | Benzoic acid | 4.20 | N/A | 183.18° C. (−157.08 Jg^−1) 186.01° C. (−107.08 Jg^−1) |
| 2-V2 3-C1 | Sorbic acid | 4.75 | N/A | 143.89° C. (−84.09 Jg^−1) 146.48° C. (−65.05 Jg^−1) |

Scale Up of the Tabernanthalog Sorbate Salt to 5 g (Experiment 4)

The experimental procedure is provided in Section G.ii, and the analytical characterization data is provided in FIGS. 561-572 and Table 233.

The salification was performed via heat-up cool-down crystallization of tabernanthalog (native) with sorbic acid from ethanol and afforded light brown crystals, (5.1 g, 87% th.) The product was analyzed by XRPD, $^1$H NMR, TGA, DSC, HPLC, KF (0.12% w/w water content) and PLM.

In summary, the scale-up of the tabernanthalog sorbate salt (4-A2; Experiment Reference 4-Sample Reference A2), performed as expected as shown in the overlays with 3-C1 ((Experiment Reference 3-Sample Reference C1) which corresponds to the initial scale up of nominated salts for physicochemical evaluation) depicted in FIGS. 409-412.

E. Physicochemical Evaluation

An informal physicochemical evaluation of the tabernanthalog monofumarate salt (Pattern #6a, Form A, 8-A4 of Example 5 [Experiment Reference 8-Sample Reference A4 of Example 5]), the tabernanthalog tartrate salt (3-A1 [Experiment Reference 3-Sample Reference A1]), the tabernanthalog benzoate salt (3-B1 [Experiment Reference 3-Sample Reference B1]), and the tabernanthalog sorbate salt (3-C1 [Experiment Reference 3-Sample Reference C1]) was performed to enable selection of the preferred salt form Once the salt is selected, physicochemical properties are further evaluated as part of the DS (drug substance) activities.

i. Solubility Determinations in SIF Buffers (Experiment 5)

The experimental procedure is provided in Section G.ii, and the analytical characterization data are provided in I.iv The solubility of the tabernanthalog monofumarate salt (Pattern #6a, Form A, 8-A4 of Example 5 [Experiment Reference 8-Sample Reference A4 of Example 5]), the tabernanthalog tartrate salt (3-A1 [Experiment Reference 3-Sample Reference A 1]), the tabernanthalog benzoate salt (3-B1 [Experiment Reference 3-Sample Reference B1]), and the tabernanthalog sorbate salt (3-C1 [Experiment Reference 3-Sample Reference C1]) were determined in FaSSIF, FeSSIF and FaSSGF by reference to the calibration curve of Tabernanthalog (native) (Section G.ii) in conjunction with monitoring the suspended phase for evidence of form change, hydrate formation or possible disproportionation.

The four salt forms (150 mg) were suspended in the relevant SIF buffer (5.0 ml) to give a concentration of 30 mg/ml (Table 214). The temperature was maintained at 37° C. for 24 h. At this concentration (30 mg/ml), solutions were formed in all apart from the tabernanthalog benzoate salt (5-C [Experiment Reference 5-Sample Reference C], 5-G [Experiment Reference 5-Sample Reference G], 5-K [Experiment Reference 5-Sample Reference K]) which precipitated in all three SIF buffers as shown in FIG. 413. The tabernanthalog sorbate salt (5-L [Experiment Reference 5-Sample Reference L]) only remained suspended in FaSSGF. The suspensions were sampled at the relevant time points and centrifuged. The centrifuged pellets, obtained at the time points were analysed by XRPD as a wet pellet and dried, for evidence of form change.

Chromatography was performed. The tabernanthalog monofumarate salt (Pattern #6a, Form A, 8-A4 of Example 5 [Experiment Reference 8-Sample Reference A4 of Example 5]) and the tabernanthalog tartrate salt (3-A1 [Experiment Reference 3-Sample Reference A1]) exhibited solubilities >30 mg/ml in all three buffers for the duration of the study. The tabernanthalog sorbate salt (3-C1 [Experiment Reference 3-Sample Reference C1]) exhibited a solubility >30 mg/ml in FaSSIF and FeSSIF (Tables 203 and 204).

FaSSIF Buffer

XRPD analysis of the solid from the benzoate salt (5-C [Experiment Reference 5-Sample Reference C]) at each timepoint (as a wet and dry pellet) in FaSSIF, confirmed that the phase was consistent with the tabernanthalog benzoate salt (3-B1 [Experiment Reference 3-Sample Reference B1]), indicating that the salt was stable and did not disproportionate in FaSSIF (FIG. 414). Chemical purity of the wet pellets obtained from the various time points (5-C: Experiment Reference 5-Sample Reference C) is exhibited in Table 201, where the decrease in chemical purity is noticeable (ca. 1.22% area decrease).

TABLE 201

Trended HPLC data of the tabernanthalog benzoate salt in FaSSIF

| Experiment Reference-Sample Reference | Comments | Area (mAu*) for reference RRT = 1.00 | 9.80 0.86 | 10.15 0.89 | 10.60 0.93 | 11.40 1.00 | Tabernanthalog 12.31 1.08 | 12.54 1.10 | 12.65 1.11 |
|---|---|---|---|---|---|---|---|---|---|
| 3-B1 | Tabernanthalog• Benzoate | 21551.15 | 0.02 | 0.04 | 0.61 | 99.23 | | 0.08 | 0.02 |
| 5-C1 | t = 1 h in FaSSIF | 3193.23 | | | 0.92 | 98.67 | 0.13 | | 0.28 |
| 5-C4 | t = 3 h in FaSSIF | 2243.96 | | | 1.04 | 98.77 | 0.20 | | |
| 5-C7 | t = 6 h in FaSSIF | 3242.56 | | | 1.26 | 98.58 | 0.16 | | |
| 5-C10 | t = 24 h in FaSSIF | 3292.94 | | | 1.51 | 98.01 | 0.24 | 0.11 | 0.13 |

FeSSIF Buffer

Analogous to the FaSSIF experiment, solid from the benzoate salt (5-G [Experiment Reference 5-Sample Reference G]), was isolated by centrifugation, analysed at each timepoint as a wet and dry pellet. The phase was consistent with the tabernanthalog benzoate salt (3-B1 [Experiment Reference 3-Sample Reference B1]), indicating that the salt was stable and did not disproportionate in FeSSIF (FIG. 415). Trended HPLC data of 5-G (Experiment Reference 5-Sample Reference G) showed a decrease in chemical purity like the one observed for 5-C (Experiment Reference 5-Sample Reference C) as shown in Table 202.

TABLE 202

Trended HPLC data of The tabernanthalog benzoate salt in FeSSIF

| Experiment Reference-Sample Reference | Comments | Area (mAu*) for reference RRT = 1.00 | 9.84 0.86 | 10.18 0.89 | 10.64 0.93 | 11.44 1.00 | Tabernanthalog 12.35 1.08 | 12.58 1.10 | 12.70 1.11 |
|---|---|---|---|---|---|---|---|---|---|
| 3-B1 | Tabernanthalog• Benzoate | 21551.15 | 0.02 | 0.04 | 0.61 | 99.23 | | 0.08 | 0.02 |
| 5-G1 | t = 1 h in FeSSIF | 3714.33 | | | 0.84 | 99.05 | 0.11 | | |
| 5-G4 | t = 3 h in FeSSIF | 3930.69 | | | 0.81 | 99.03 | 0.10 | | 0.06 |
| 5-G7 | t = 6 h in FeSSIF | 4473.57 | | | 1.00 | 98.69 | 0.15 | 0.07 | 0.09 |
| 5-G10 | t = 24 h in FeSSIF | 3610.91 | | 0.15 | 1.36 | 98.17 | 0.19 | 0.13 | |

TABLE 203

Summary of HPLC and XRPD data of the selected Tabernanthalog salts in SIF buffers at t = 1 h and t = 3 h.

| Experiment Reference-Sample Reference | SIF Buffer | Input | Weights input (mg) | t = 1 h @ 37° C. Solubility (mg/ml) | XRPD (wet) | XRPD (dried) | pH | t = 3 h @ 37° C. Solubility (mg/ml) | XRPD (wet) | XRPD (dried) | pH |
|---|---|---|---|---|---|---|---|---|---|---|---|
| 5-A | FaSSIF (pH 6.5) | Tabernanthalog• Fumarate | 119.4 | Solution, >30 mg/ml | N/A | N/A | 6.37 | Solution, >30 mg/ml | N/A | N/A | 6.55 |
| 5-B | FaSSIF (pH 6.5) | Tabernanthalog• Tartrate | 149.8 | Solution, >30 mg/ml | N/A | N/A | 6.74 | Solution, >30 mg/ml | N/A | N/A | 6.46 |
| 5-C | FaSSIF (pH 6.5) | Tabernanthalog• Benzoate | 149.6 | 8.85 | Consistent with input | Consistent with input | 6.63 | 6.22 | Consistent with input | Consistent with input | 6.32 |
| 5-D | FaSSIF (pH 6.5) | Tabernanthalog• Sorbate | 150.6 | Solution, >30 mg/ml | N/A | N/A | 6.55 | Solution, >30 mg/ml | N/A | N/A | 6.54 |
| 5-E | FeSSIF (pH 5.0) | Tabernanthalog• Fumarate | 120.2 | Solution, >30 mg/ml | N/A | N/A | 5.08 | Solution, >30 mg/ml | N/A | N/A | 5.07 |
| 5-F | FeSSIF (pH 5.0) | Tabernanthalog• Tartrate | 150.1 | Solution, >30 mg/ml | N/A | N/A | 5.01 | Solution, >30 mg/ml | N/A | N/A | 5.03 |
| 5-G | FeSSIF (pH 5.0) | Tabernanthalog• Benzoate | 150.2 | 10.29 | Consistent with input | Consistent with input | 5.07 | 10.89 | Consistent with input | Consistent with input | 5.00 |
| 5-H | FeSSIF (pH 5.0) | Tabernanthalog• Sorbate | 149.6 | 27.15 | Insufficient for analysis | Insufficient for analysis | 5.19 | Solution, >30 mg/ml | N/A | N/A | 5.18 |
| 5-I | FaSSGF (pH 1.6) | Tabernanthalog• Fumarate | 119.4 | Solution, >30 mg/ml | N/A | N/A | 1.68 | Solution, >30 mg/ml | N/A | N/A | 1.61 |
| 5-J | FaSSGF (pH 1.6) | Tabernanthalog• Tartrate | 149.8 | Solution, >30 mg/ml | N/A | N/A | 1.63 | Solution, >30 mg/ml | N/A | N/A | 1.64 |

TABLE 203-continued

Summary of HPLC and XRPD data of the selected Tabernanthalog salts in SIF buffers at t = 1 h and t = 3 h.

| Experiment Reference- Sample Reference | SIF Buffer | Input | Weights input (mg) | t = 1 h @ 37° C. | | | | t = 3 h @ 37° C. | | | |
|---|---|---|---|---|---|---|---|---|---|---|---|
| | | | | Solubility (mg/ml) | XRPD (wet) | XRPD (dried) | pH | Solulibility (mg/ml) | XRPD (wet) | XRPD (dried) | pH |
| 5-K | FaSSGF (pH 1.6) | Tabernanthalog• Benzoate | 150.2 | 29.91 | Benzoic acid | Benzoic acid | 1.63 | 26.21 | Benzoic acid | Benzoic acid | 1.63 |
| 5-L | FaSSGF (pH 1.6) | Tabernanthalog• Sorbate | 150.4 | 21.88 | Sorbic acid | Sorbic acid | 1.73 | 29.84 | Sorbic acid | Sorbic acid | 1.62 |

TABLE 204

Summary of HPLC and XRPD data of the selected Tabernanthalog salts in SIF buffers at t = 6 h and t = 24 h.

| Experiment Reference- Sample Reference | SIF Buffer | Input | Weights input (mg) | t = 6 h @ 37° C. | | | | t = 24 h @ 37° C. | | | |
|---|---|---|---|---|---|---|---|---|---|---|---|
| | | | | Solubility (mg/ml) | XRPD (wet) | XRPD (dried) | pH | Solubility (mg/ml) | XRPD (wet) | XRPD (dried) | pH |
| 5-A | FaSSIF (pH 6.5) | Tabernanthalog• Fumarate | 119.4 | Solution, >30 mg/ml | N/A | N/A | 6.54 | Solution, >30 mg/ml | N/A | N/A | 6.41 |
| 5-B | FaSSIF (pH 6.5) | Tabernanthalog• Tartrate | 149.8 | Solution, >30 mg/ml | N/A | N/A | 6.37 | Solution, >30 mg/ml | N/A | N/A | 6.47 |
| 5-C | FaSSIF (pH 6.5) | Tabernanthalog• Benzoate | 149.6 | 8.98 | Consistent with input | Consistent with input | 6.40 | 9.12 | Consistent with input | Consistent with input | 6.50 |
| 5-D | FaSSIF (pH 6.5) | Tabernanthalog• Sorbate | 150.6 | Solution, >30 mg/ml | N/A | N/A | 6.51 | Solution, >30 mg/ml | N/A | N/A | 6.36 |
| 5-E | FeSSIF (pH 5.0) | Tabernanthalog• Fumarate | 120.2 | Solution, >30 mg/ml | N/A | N/A | 5.05 | Solution, >30 mg/ml | N/A | N/A | 5.01 |
| 5-F | FeSSIF (pH 5.0) | Tabernanthalog• Tartrate | 150.1 | Solution, >30 mg/ml | N/A | N/A | 5.01 | Solution, >30 mg/ml | N/A | N/A | 4.93 |
| 5-G | FeSSIF (pH 5.0) | Tabernanthalog• Benzoate | 150.2 | 12.39 | Consistent with input | Consistent with input | 5.03 | 10.00 | Consistent with input | Consistent with input | 4.97 |
| 5-H | FeSSIF (pH 5.0) | Tabernanthalog• Sorbate | 149.6 | Solution, >30 mg/ml | N/A | N/A | 5.07 | Solution, >30 mg/ml | N/A | N/A | 5.05 |
| 5-I | FaSSGF (pH 1.6) | Tabernanthalog• Fumarate | 119.4 | Solution, >30 mg/ml | N/A | N/A | 1.62 | Solution, >30 mg/ml | N/A | N/A | 1.79 |
| 5-J | FaSSGF (pH 1.6) | Tabernanthalog• Tartrate | 149.8 | Solution, >30 mg/ml | N/A | N/A | 1.56 | Solution, >30 mg/ml | N/A | N/A | 1.74 |
| 5-K | FaSSGF (pH 1.6) | Tabernanthalog• Benzoate | 150.2 | 30.86 | Benzoic acid | Benzoic acid | 1.54 | 30.69 | Benzoic acid | Benzoic acid | 1.70 |
| 5-L | FaSSGF (pH 1.6) | Tabernanthalog• Sorbate | 150.4 | 30.27 | Sorbic acid | Sorbic acid | 1.58 | 29.90 | Sorbic acid | Sorbic acid | 1.78 |

FaSSGF Buffer

The powder pattern of the solid residue (5-K12; Experiment Reference 5-Sample Reference K12) obtained at all timepoints did not match the tabernanthalog benzoate salt (3-B1 [Experiment Reference 3-Sample Reference B1]), or tabernanthalog (native) (FIG. 416).

The reference pattern for benzoic acid was highly preferred and gave poor agreement with the isolated solid residue, (5-K12; Experiment Reference 5-Sample Reference K12) (FIG. 417). However, by $^1$H NMR analysis (FIG. 418) of the dry pellet (5-K12; Experiment Reference 5-Sample Reference K12) was consistent with benzoic acid; therefore, at lower pH, a different form of benzoic acid was isolated. The chemical purity of 5-K (Experiment Reference 5-Sample Reference K) did not decrease as significantly during the 24 h in FaSSGF (Table 205), when compared to the tabernanthalog benzoate salt (3-B1 [Experiment Reference 3-Sample Reference B1]) in FaSSIF and FeSSIF.

TABLE 205

Trended HPLC data of the tabernanthalog benzoate salt in FaSSGF

| Experiment Reference-Sample Reference | Comments | Area (mAu*) for reference RRT = 1.00 | Tabernanthalog | | | | | | |
|---|---|---|---|---|---|---|---|---|---|
| | | | 9.83 0.86 | 10.17 0.89 | 10.63 0.93 | 11.43 1.00 | 12.45 1.09 | 12.57 1.10 | 12.68 1.11 |
| 3-B1 | Tabernanthalog•Benzoate | 21551.15 | 0.02 | 0.04 | 0.61 | 99.23 | 0.08 | 0.02 | |
| 5-K1 | t = 1 h in FaSSGF | 5398.87 | | | 0.55 | 99.33 | 0.07 | 0.02 | 0.03 |
| 5-K4 | t = 3 h in FaSSGF | 4731.19 | | | 0.58 | 99.34 | 0.07 | | |
| 5-K7 | t = 6 h in FaSSGF | 5569.91 | | | 0.59 | 99.33 | 0.08 | | |
| 5-K10 | t = 24 h in FaSSGF | 5538.89 | | | 0.63 | 99.29 | 0.08 | | |

The powder diffraction patterns of the tabernanthalog sorbate salt solid residue (5-L; Experiment Reference 5-Sample Reference L) in FaSSGF, were consistent with that of sorbic acid (FIG. 419 and FIG. 420), while the mass balance of tabernanthalog (native) remained in solution. $^1$H NMR analysis of (5-L12; Experiment Reference 5-Sample Reference L12) supported disproportionation when overlaid with tabernanthalog sorbate salt (3-C1; [Experiment Reference 3-Sample Reference C1]) (FIG. 421).

Trended HPLC data of the tabernanthalog sorbate salt in FaSSGF is provided in Table 206.

TABLE 206

Trended HPLC data of the tabernanthalog sorbate salt in FaSSGF

| Experiment Reference-Sample Reference | Comments | Area (mAu*) for reference RRT = 1.00 | Tabernanthalog | | | | | |
|---|---|---|---|---|---|---|---|---|
| | | | 10.16 0.89 | 10.62 0.93 | 11.42 1.00 | 12.45 1.09 | 12.67 1.11 | 12.79 1.12 |
| 3-C1 | Tabernanthalog•Sorbate | 25461.25 | 0.05 | 0.41 | 99.41 | 0.06 | 0.02 | 0.05 |
| 5-L1 | t = 1 h in FaSSGF | 4064.06 | | 0.48 | 99.52 | | | |
| 5-L4 | t = 3 h in FaSSGF | 5542.85 | | 0.49 | 99.36 | 0.07 | 0.08 | |
| 5-L7 | t = 6 h in FaSSGF | 5626.46 | | 0.55 | 99.30 | 0.08 | 0.07 | |
| 5-L10 | t = 24 h in FaSSGF | 5554.20 | | 0.50 | 99.33 | 0.09 | 0.08 | | ii. Equilibrium Humidity Evaluation

The experimental procedure that accompany this experiment is provided in Section G.ii. Photographs of the vials taken during the study are exhibited in FIGS. 430-432. The fates of the tabernanthalog monofumarate salt (Pattern #6a, Form A, 8-A4 of Example 5 [Experiment Reference 8-Sample Reference A4 of Example 5]), the tabernanthalog tartrate salt (3-A1 [Experiment Reference 3-Sample Reference A1]), the tabernanthalog benzoate salt (3-B1 [Experiment Reference 3-Sample Reference B1]) and the tabernanthalog sorbate salt (3-C1 [Experiment Reference 3-Sample Reference C1]) absorbents, were determined under constant equilibrium condition at 75% RH/40° C. for 10 days.

All forms were maintained under constant equilibrium humidity (75% RH). XRPD, DSC, TGA, PLM and $^1$H NMR analyses were performed on the absorbents at t=5 d and t=10 d, to confirm their physical fates and to determine the extent of residual solvent exchange or sequestration.

The Tabernanthalog Monofumarate Salt (40° C., 75% RH)

The characterization data that accompany this experiment is provided in FIGS. 605-620 and Tables 250-251. The absorbent tabernanthalog monofumarate salt (Pattern #6a, Form A, 8-A4 of Example 5 [Experiment Reference 8-Sample Reference A4 of Example 5]) was included in the panel as the control. The powder diffraction patterns (6-A1 [Experiment Reference 6-Sample Reference A1], t=5 days and 6-A2 [Experiment Reference 6-Sample Reference A2], t=10 days) resembled the input phase (Pattern #6a, Form A, 8-A4 of Example 5 [Experiment Reference 8-Sample Reference A4 of Example 5]), confirming that significant structural reorganization had not occurred (FIG. 422). The NMR spectrum overlay confirmed that the molecular structure of the API was concordant with the input (FIG. 426). No weight loss transitions were detected at typical water release temperatures by TG analyses (FIGS. 609 and 610) and the flat baseline, observed by DSC at both time points, was consistent with no significant water uptake, under this condition (FIGS. 607 and 608). HPLC data showed a slight decrease in chemical purity after 10 days [6-A2 (Experiment Reference 6-Sample Reference A2)] as shown in Table 207.

The Tabernanthalog Tartrate Salt (40° C., 75% RH)

The characterization data that accompany this experiment is provided in FIGS. 621-636 and Tables 252-253.

The tabernanthalog tartrate salt at t=5 days (6-B1 [Experiment Reference 6-Sample Reference B1]) and t=10 days (6-B2 [Experiment Reference 6-Sample Reference B2]) showed no significant changes to the powder diffraction pattern by XRPD when compared with the input (3-A1 [Experiment Reference 3-Sample Reference A1]) as no peak shift to lower angle, was observed which sometimes is indicative of moisture absorption was observed (FIG. 423). The absorbent was concordant with the API molecular structure and ethanol was not detected by $^1$H NMR spectroscopy (FIG. 427). The TGA profile of 6-B1 (Experiment Reference 6-Sample Reference B1) and 6-B2 (Experiment Reference 6-Sample Reference B2) was consistent with the input (3-A1 [Experiment Reference 3-Sample Reference A1]) with no significant water absorption (FIGS. 625 and 626). DSC analyses exhibited a flat baseline, as no water release endotherms were evident (FIGS. 623 and 624). HPLC data showed the largest decrease in chemical purity after 10 days compared to the rest of the salts (Table 208).

The Tabernanthalog Benzoate Salt (40° C. 75% RH)

The characterization data that accompany this experiment is provided in FIGS. 637-652 and Tables 254-255.

By XRPD, tabernanthalog benzoate salt at t=5 days (6-C1 [Experiment Reference 6-Sample Reference C1]) and t=10 days (6-C2 [Experiment Reference 6-Sample Reference C2]) were consistent with the input 3-B1 [Experiment Reference 3-Sample Reference B1]) (FIG. 424).

$^1$H NMR spectroscopy confirmed the molecular structure of the input material, with a small decrease in ethanol content from 0.3% w/w to 0.2% w/w (FIG. 428). TG analyses did not show any weight loss events attributed to water absorbance (FIGS. 641 and 642). The DSC thermograms at the two time points were also consistent with no significant water uptake (FIGS. 639 and 640). The chemical purity did not decrease significantly at the cessation of the experiment (Table 209).

The Tabernanthalog Sorbate Salt (40° C. 75% RH)

The characterization data that accompany this experiment is provided in FIGS. 653-668 and Tables 256-257.

The powder diffraction pattern of tabernanthalog sorbate at t=5 days (6-D1 [Experiment Reference 6-Sample Reference D1]) and t=10 days (6-D2 [Experiment Reference 6-Sample Reference D2]) matched the diffractogram of the input material 3-C1 [Experiment Reference 3-Sample Reference C1]) (FIG. 425). The $^1$H NMR spectrum obtained showed an ethanol content decrease from 0.3% w/w to 0.1% w/w and confirmed that the molecular structure of the API at both time points was concordant with the input (3-C1 [Experiment Reference 3-Sample Reference C1]) (FIG. 429). The TGA profiles from the two time points did not exhibit any water absorption events (FIGS. 657 and 658). DSC analysis showed a flat baseline, consistent with the input material (FIGS. 655 and 656). Trended HPLC data confirmed the lowest decrease in chemical purity compared to the rest of the salts (Table 210).

TABLE 207

Trended HPLC data of 6-A (Experiment Reference 6-Sample Reference A)

| Experiment Reference-Sample Reference | Comments | Area (mAu*) for reference RRT = 1.00 | Tabernanthalog | | | | | | | | |
|---|---|---|---|---|---|---|---|---|---|---|---|
| | | | 7.83 0.64 | 8.93 0.73 | 10.04 0.82 | 10.53 0.86 | 11.02 0.90 | 11.63 0.95 | 11.75 0.96 | 11.99 0.98 | 12.24 1.00 |
| 8-A4 of Example 5 | Fumarate salt | 5659.39 | | | | | | | | | 99.04 |
| 6-A1 | t = 5 d at 75% RH at 40° C. | 8764.06 | 0.25 | 0.01 | 0.04 | 0.02 | 0.03 | 0.02 | 0.01 | 0.02 | 99.12 |
| 6-A2 | t = 10 d at 75% RH at 40° C. | 8319.38 | 0.27 | 0.01 | 0.16 | 0.06 | 0.04 | 0.07 | 0.01 | 0.02 | 98.71 |

Trended HPLC data of 6-A (Experiment Reference 6-Sample Reference A)

| Experiment Reference-Sample Reference | Comments | Area (mAu*) for reference RRT = 1.00 | Tabernanthalog | | | | | | | | |
|---|---|---|---|---|---|---|---|---|---|---|---|
| | | | 13.46 1.10 | 13.59 1.11 | 13.71 1.12 | 14.44 1.18 | 14.56 1.19 | 16.16 1.32 | 16.40 1.34 | 16.65 1.36 | 16.89 1.38 |
| 8-A4 of Example 5 | Fumarate salt | 5659.39 | | 0.96 | | | | | | | |
| 6-A1 | t =5 d at 75% RH at 40° C. | 8764.06 | 0.02 | 0.08 | 0.05 | 0.01 | 0.04 | 0.16 | 0.01 | |0.02 | 0.07 |
| 6-A2 | t = 10 d at 75% RH at 40° C. | 8319.38 | 0.02 | 0.13 | 0.10 | 0.01 | 0.05 | 0.18 | 0.01 | 0.02 | 0.09 |

TABLE 208

Trended HPLC data of 6-B (Experiment Reference 6-Sample Reference B)

| Experiment Reference-Sample Reference | Comments | Area for reference RRT = 1.00 (mAu*) | Tabernanthalog | | | | | | | |
|---|---|---|---|---|---|---|---|---|---|---|
| | | | 8.03 0.63 | 10.45 0.82 | 10.96 0.86 | 11.08 0.87 | 11.47 0.90 | 11.98 0.94 | 12.10 0.95 | 12.36 0.97 |
| 3-A1 | Tartrate salt | 8237.15 | | 0.05 | | 0.07 | 0.02 | 0.21 | | 0.01 |
| 6-B1 | t = 5 d at 75% RH at 40° C. | 3831.45 | 0.60 | 0.04 | 0.03 | 0.03 | 0.02 | 0.11 | 0.01 | 0.02 |
| 6-B2 | t = 10 d at 75% RH at 40° C. | 3526.78 | 0.60 | 0.04 | 0.03 | 0.03 | 0.03 | 0.15 | 0.03 | 0.03 |

TABLE 208-continued

Trended HPLC data of 6-B (Experiment Reference 6-Sample Reference B)

| Experiment Reference- Sample Reference | Comments | Area for reference RRT = 1.00 (mAu*) | Tabernanthalog | | | | | | |
|---|---|---|---|---|---|---|---|---|---|
| | | | 12.74 1.00 | 13.89 1.09 | 14.01 1.10 | 14.14 1.11 | 14.91 1.17 | 15.03 1.18 | 17.20 1.35 |
| 3-A1 | Tartrate salt | 8237.15 | 99.39 | 0.11 | 0.02 | 0.04 | 0.01 | 0.04 | 0.05 |
| 6-B1 | t = 5 d at 75% RH at 40° C. | 3831.45 | 98.86 | 0.11 | 0.03 | 0.02 | 0.03 | 0.03 | 0.04 |
| 6-B2 | t = 10 d at 75% RH at 40° C. | 3526.78 | 98.82 | 0.09 | 0.01 | 0.01 | 0.03 | 0.02 | 0.03 |

TABLE 209

Trended HPLC data of 6-C (Experiment Reference 6-Sample Reference C)

| Experiment Reference- Sample Reference | Comments | Area (mAu*) for reference RRT = 1.00 | Tabernanthalog | | | | | | | |
|---|---|---|---|---|---|---|---|---|---|---|
| | | | 8.12 0.64 | 9.26 0.73 | 10.40 0.82 | 10.91 0.86 | 11.03 0.87 | 11.54 0.91 | 12.05 0.95 | 12.43 0.98 | 12.68 1.00 |
| 3-B1 | Benzoate salt | 10224.04 | 0.19 | 0.02 | 0.22 | | 0.26 | 0.02 | 0.51 | 0.01 | 98.56 |
| 6-C1 | t =5 d at 75% RH at 40° C. | 10122.50 | 0.17 | | 0.28 | | 0.10 | 0.01 | 0.54 | 0.01 | 98.36| |
| 6-C2 | t = 10 d at 75% RH at 40° C. | 4243.62 | 0.51 | | 0.25 | 0.09 | 0.21 | 0.03 | 0.47 | 0.02 | 98.17 |

Trended HPLC data of 6-C (Experiment Reference 6-Sample Reference C)

| Experiment Reference- Sample Reference | Comments | Area (mAu*) for reference RRT = 1.00 | Tabernanthalog | | | | | | | |
|---|---|---|---|---|---|---|---|---|---|---|
| | | | 13.95 1.10 | 14.20 1.12 | 14.33 1.13 | 14.96 1.18 | 15.09 1.19 | 15.22 1.20 | 15.85 1.25 | 16.87 1.33 |
| 3-B1 | Benzoate salt | 10224.04 | 0.08 | 0.03 | 0.04 | | 0.02 | 0.05 | | |
| 6-C1 | t =5 d at 75% RH at 40° C. | 10122.50 | 0.08 | 0.04 | 0.03 | 0.01 | 0.04 | 0.05 | 0.01 | 0.01 |
| 6-C2 | t = 10 d at 75% RH at 40° C. | 4243.62 | 0.09 | 0.03 | | 0.03 | 0.03 | 0.05 | | |

TABLE 210

Trended HPLC data of 6-D (Experiment Reference 6-Sample Reference D)

| Experiment Reference- Sample Reference | Comments | Area (mAu*) for reference RRT = 1.00 | Tabernanthalog | | | | | | | | | | | | |
|---|---|---|---|---|---|---|---|---|---|---|---|---|---|---|---|
| | | | 8.11 0.63 | 10.42 0.81 | 10.94 0.85 | 11.07 0.86 | 11.45 0.89 | 11.97 0.93 | 12.48 0.97 | 12.87 1.00 | 13.90 1.08 | 14.28 1.11 | 14.93 1.16 | 15.19 1.18 | 15.57 1.21 |
| 3-C1 | Sorbate salt | 60353.67 | 0.04 | 0.04 | | 0.04 | | 0.07 | | 99.76 | 0.01 | 0.02 | | 0.01 | |
| 6-D1 | t = 5 d at 75% RH at 40° C. | 8531.09 | 0.28 | 0.03 | 0.01 | 0.01 | | 0.05 | 0.01 | 99.52 | 0.02 | | 0.03 | 0.01 | 0.01 |
| 6-D2 | t = 10 d at 75% RH at 40° C. | 15174.05 | 0.15 | 0.02 | 0.01 | 0.01 | 0.01 | 0.04 | 0.01 | 99.70 | 0.01 | 0.01 | 0.01 | 0.01 | | iii. Dynamic Vapour Sorption (DVS)

The tabernanthalog monofumarate salt [Pattern #6a, Form A, 8-A4 of example 5 (Experiment Reference 8-Sample Reference A4) of Example 5)] was included as the control. Tabernanthalog monofumarate salt [Pattern #6a, Form A, 8-A4 of example 5 (Experiment Reference 8-Sample Reference A4) of Example 5)], the tabernanthalog tartrate salt (3-A1 [Experiment Reference 3-Sample Reference A1]), the tabernanthalog benzoate salt (3-B1 [Experiment Reference 3-Sample Reference B1]) and the tabernanthalog sorbate salt (3-C1 [Experiment Reference 3-Sample Reference C1])

were equilibrated at 0% RH for 60 min, prior to DVS analyses (stepped increment % RH up to 90% RH and stepped decrement % RH down to 0% RH).

Sorption/Desorption Isotherms

The sorption/desorption isotherms are provided in FIGS. 433-436.

The Tabernanthalog Monofumarate Salt

The DVS analyses are provided in FIGS. 669 and 670 and the powder diffraction analysis is provided in FIG. 671. The tabernanthalog monofumarate salt [Pattern #6a, Form A, 8-A4 of example 5 (Experiment Reference 8-Sample Reference A4) of Example 5)] exhibited hygroscopic isotherm, with negligible hysteresis (FIG. 433). A small peak shift was evident in the diffraction pattern acquired after 0 to 90 to 0% RH treatment, when compared to the diffraction pattern acquired at the beginning of the cycle; that being said, the diffraction patterns closely resembled each other (FIG. 671), indicating that any structural changes that had occurred to the absorbent during DVS treatment were minimal.

The Tabernanthalog Tartrate Salt

The DVS analyses are provided in FIGS. 471 and 472 and the powder diffraction analyses are provided in FIGS. 474 and 475. The tabernanthalog tartrate salt (3-A1 [Experiment Reference 3-Sample Reference A1]) showed a hygroscopic type of isotherm which suggested reversible water affinity. Negligible hysteresis was observed (FIG. 434). The diffraction patterns pre- and post-treatment (0 to 90 to 0% RH) approximately coincided, indicating that minor structural alterations to the absorbent that occurred under elevated humidity were reversible.

The Tabernanthalog Benzoate Salt

The DVS analyses are provided in FIGS. 486(A) and 486(B), and the powder diffraction analyses are provided in FIGS. 486(C) and 486(D). The tabernanthalog benzoate salt (3-B1 [Experiment Reference 3-Sample Reference B1]) appeared to be slightly hygroscopic (red line) isotherm (FIG. 435). Again, the diffraction pattern acquired after 0 to 90 to 0% RH treatment exhibited a small peak shift when compared to the diffraction pattern of the input, indicating that any structural changes that had occurred to the absorbent during DVS treatment were minimal.

The Tabernanthalog Sorbate Salt

The DVS analyses are provided in FIGS. 455 and 456, and the powder diffraction analyses are provided in FIGS. 458 and 459. The tabernanthalog sorbate salt (4-A2 [Experiment Reference 4-Sample Reference A2]) was slightly hygroscopic up to 80% RH (red isotherm, FIG. 436), hysteresis observed in the 80% to 50% range, during the desorption cycle. The diffraction patterns pre- and post-treatment (0 to 90 to 0% RH) approximately coincided, confirming that minor structural alterations to the absorbent that occurred under elevated humidity were reversible.

The percent mass change numbers and the curve shape of the DVS isotherm, does not seem to result in developability issues associated with the tabernanthalog sorbate salt (4-A2 [Experiment Reference 4-Sample Reference A2]) being hygroscopic.

F. Conclusions

The tabernanthalog sorbate salt was the best candidate amongst the salts that were screened and physiochemically evaluated and was therefore nominated for polymorph screening. Focusing on its performance in the advanced physicochemical screening, the tabernanthalog sorbate salt showed minimal reduction in CP under 75% RH at 40° C. (6-D [Experiment Reference 6-Sample Reference D] from 99.76% area to 99.70% area). It was highly soluble in the SIF buffers used, apart from FaSSGF (5-L [Experiment Reference 5-Sample Reference L]). The tabernanthalog sorbate salt (3-C1 [Experiment Reference 3-Sample Reference C1] and 4-A2 [Experiment Reference 4-Sample Reference A2]) exhibited much higher crystallographic quality than the tabernanthalog monofumarate salt (Pattern #6a, Form A, 4-A4 [Experiment Reference 4-Sample Reference A4]) which is a key physical attribute required in later screening, as it results in better solvent and impurity rejection on scale-up. Furthermore, sorbic acid is GRAS and is in use as a food additive.

G. Experimental i. Instrumentation

DSC: A Mettler Toledo DSC 3 instrument was used for the thermal analysis operating with STARe™ software. The analysis was conducted in 40 μl open aluminum pans, under nitrogen and sample sizes ranged from 1 to 10 mg. Typical analysis method was 20 to 250° C. at 10° C./minute. Alternatively, a Mettler Toledo DSC1 with auto-sampler instrument was used for the thermal analysis operating with STARe™ software. The analysis was conducted in 40 μl open aluminum pans, under nitrogen and sample sizes ranged from 1 to 10 mg. Typical analysis method was 25 to 30 0° C. at 10° C./minute.

DVS: The moisture sorption properties of the feed API were analyzed by DVS Intrinsic instrument (Surface Measurement System). Approximately 20-50 mg of API was weighed on an aluminum pan and loaded into the instrument equilibrated at 25° C. The sample was allowed to equilibrate under dry atmosphere (0% relative humidity) for 60 minutes before increasing the humidity from 0% to 30% at 5% step increment and from 30% to 90% at 10% step increment. A desorption cycle was also applied from 90% to 30% (10% step) and from 30% to 0% (5% decrement). A rate of change in mass per time unit (dm/dt) of 0.002%/min was set as the equilibrium parameter. Kinetic and isotherm graphs were calculated.

LC-MS: Routine Liquid Chromatography-Mass Spectrometry (LC-MS) data were collected using the Agilent 1260 Infinity II interfaced with 1260 Infinity II DAD HS and Agilent series 1260 Infinity II binary pump. The instrument used a single quadrupole InfinityLab MSD. The instrument was calibrated up to 2000 Da.

LC-MS method parameters:
Inj. vol: 5 μl
Detection: UV @c. 254 nm
Mobile Phase A: Acetonitrile+0.1% TFA/H$_2$O 95:5
Mobile Phase B: Acetonitrile±0.05% TFA/H$_2$O 5:95

| Time (mins) | % A | % B |
|---|---|---|
| 0.0 | 100 | 0 |
| 1 | 100 | 0 |
| 10.00 | 0 | 100 |
| 10.01 | 100 | 0 |
| 12.00 | 100 | 0 |

Flow Rate: 1 ml/min
Column temperature: 30° C.
Run time 12 minutes.

$^1$H NMR: $^1$H NMR Spectra were acquired using a Bruker 400 MHz spectrometer and data was processed using Topspin. Samples were prepared in DMSO-D$_6$ at typical concentrations of 10 to 20 mg/ml and up to 50 mg/ml for $^1$H NMR w/w assay and calibrated to the corresponding non-deuterated solvent residual at 2.50 ppm.

$^1$H NMR w/w assay: Assays (w/w) of API by $^1$H NMR spectroscopy were measured using Topspin. Internal standard 2,3,5,6-terachloronitrobenzene (TCNB), (ca. 20 mg, F.W. 260.89) was dissolved in DMSO-D6 (2.0 ml) and the $^1$H NMR spectrum was acquired using an extended relaxation method.

TGA. A Mettler Toledo TGA 2 instrument was used to measure the weight loss as a function of temperature from 25 to 500° C. The scan rate was typically 5 or 10 (C per minute. Experiments and analysis were carried out using the STARe™ software. The analysis was conducted in 100 μl open aluminum pans, under nitrogen and sample sizes ranged from 1 to 10 mg.

XRPD: X-ray powder diffraction (XRPD) analysis was carried out using a Bruker D2 Phaser powder diffractometer equipped with a LynxEye detector. The specimens underwent minimum preparation but, if necessary, they were lightly milled in a pestle and mortar before acquisition. The specimens were located at the center of a silicon sample holder within a 5 mm pocket (ca. 5 to 10 mg). The samples were continuously spun during data collection and scanned using a step size of 0.02°2-theta (2θ) between the range of 4° to 40° 2-theta or 5° to 60°2-theta. Data was acquired using either 3 minute or 10-minute acquisition methods. Data was processed using Bruker Diffrac.Suite. Relative intensity values in peak tables were calculated using the Net. intensity values. FT-IR: FT-IR Spectra were acquired using a PerkinElmer Frontier FT-IR spectrometer. Samples were analyzed directly using a universal ATR attachment in the Mid and Far frequency ranges; 4000 to 30 cm$^{-1}$. Spectrums were processed using Spectrum software. Standard KBr windows are used for mid-IR applications; polyethylene and polyethylene/diamond windows are used for operation in the far-IR. Further capabilities of the instrument include a liquid flow cell with ZnSe windows used for rapid monitoring of reactions. This couples with Timebase software which allows time-resolved measurements to be taken.

HPLC (MET/CR/2616): HPLC data was acquired using an Agilent HPLC instrument. Samples were diluted to 1 mg/mL concentration in H$_2$O/DMSO (1/1, v/v).
Method Parameters:
 Column: Halo C18, 150×4.6 mm, 2.7 μm
 Inj. volume: 5 μL
 Detection: UV @ 212 nm
 Mobile Phase A: 0.1% TFA in water/acetonitrile 95/5 v/v
 Mobile Phase B: 0.05% TFA in water/acetonitrile 5/95 v/v

| Time | % A | % B |
|---|---|---|
| 0.0 | 100 | 0 |
| 2.0 | 100 | 0 |
| 25.0 | 50 | 50 |
| 30.0 | 0 | 100 |
| 32.0 | 0 | 100 |
| 32.1 | 100 | 0 |
| 37.0 | 100 | 0 |

Flow rate: 1 mL/min
Column temperature: 30° C.
Run time: 37 minutes
Integration time; 32 minutes
Wash vial or syringe wash: Sample diluent
ii. Procedures Targeted Solubility Assessment (Experiment Reference 7)

To portions of tabernanthalog (native) (50 mg, 1 wt), were added 5 vol aliquots of the relevant solvent (Table 198). Observations were made at 20° C., 40° C., and reflux and the mixtures were cooled to 20° C. Contingent upon these findings, an additional 5 vol aliquot of the relevant solvent was added and the process was repeated until 20 vol of solvent was added in total.

Heat-Up Cool-Down Crystallization Salt Screen (Experiment 2)

Tabernanthalog (native) (50 mg, 1 wt) was charged to a solution of the relevant counter ion (1.0 mol equivalence of counter ion) in ethanol (5.0 vol, 250 μl). The mixtures were warmed to 85° C., and small aliquots of water were added until dissolution occurred (Table 212 for additional charges of solvent). The solutions were cooled and allowed to stand undisturbed under sub-ambient conditions overnight (Table 211). Solutions were observed in all vials upon cooling at 20° C. Products were isolated via centrifugation. The corresponding pellets were sub-sampled and analyzed wet by XRPD; after which, they were dried at 40° C. under reduced pressure over 20 h and reanalyzed by XRPD. Any product that exhibited a unique diffraction pattern was further analyzed by $^1$H NMR for confirmation of chemical identity, counter-ion stoichiometry and solvent content and DSC and TGA to record their thermal profiles. Once the crystallization experiments were completed, salt formation was confirmed by $^1$H NMR, XRPD, DSC and TGA.

TABLE 211

Vials that showed crystals upon cooling.

| Input reference | Experiment Reference-Sample Reference | Tabernanthalog native | Counter ion | pK$_a$1 | pK$_a$2 | pK$_a$3 | Observations upon cooling to 20° C. | Observations upon sub-ambient cooling to 6 to 8 C. (40 hr) |
|---|---|---|---|---|---|---|---|---|
| Tabernanthalog native | 2-A1 | 50.30 | Hydrobromic acid | −9.00 | | | Solution | Solution |
| | 2-B1 | 50.30 | Hydrochloric acid | −6.00 | | | Solution | Solution |
| | 2-C1 | 50.20 | Sulfuric acid | −3.00 | 1.90 | | Solution | Crystallised |
| | 2-D1 | 50.50 | Ethanesulfonic acid | −2.10 | −1.50 | | Solution | Solution |
| | 2-E1 | 50.10 | p-Toluenesulfonic acid | −1.30 | | | Solution | Crystallised |

TABLE 211-continued

Vials that showed crystals upon cooling.

| Input reference | Experiment Reference-Sample Reference | Tabernanthalog native | Counter ion | pK$_a$1 | pK$_a$2 | pK$_a$3 | Observations upon cooling to 20° C. | Observations upon sub-ambient cooling to 6 to 8 C. (40 hr) |
|---|---|---|---|---|---|---|---|---|
| | 2-F1 | 50.00 | Methanesulfonic acid | 2.10 | | | Solution | Solution |
| | 2-G1 | 50.00 | Maleic acid | 1.90 | 6.20 | | Solution | Crystallised |
| | 2-H1 | 50.60 | Phosphoric acid | 1.90 | 7.10 | 12.30 | Solution | Crystallised |
| | 2-I1 | 50.50 | (+)-L-Tartaric acid | 3.00 | 4.40 | | Solution | Crystallised |
| | 2-J1 | 50.80 | Ethane-1,2-disulfonic acid | −2.10 | −1.50 | | Solution | Crystallised |
| | 2-K1 | 50.30 | Galactaric acid (mucic acid) | 3.10 | 3.60 | | Solution | Crystallised |
| | 2-L1 | 50.20 | Citric acid (monohydrate) | 3.10 | 4.80 | 6.40 | Solid | Crystallised |
| | 2-M1 | 50.30 | D-Glucuronic acid | 3.20 | | | Solution | Crystallised |
| | 2-N1 | 50.20 | Glycolic acid | 3.30 | | | Solution | Crystallised |
| | 2-O1 | 50.00 | (-)-L-Malic acid | 3.50 | 5.10 | | Solution | Crystallised |
| | 2-P1 | 50.80 | D-Gluconic acid | 3.80 | | | Solution | Solution |
| | 2-Q1 | 50.70 | L-Ascorbic acid | 4.20 | | | Solution | Gum |
| | 2-R1 | 50.90 | Benzoic acid | 4.20 | | | Solution | Crystallised |
| | 2-S1 | 50.10 | Succinic acid | 4.20 | | | Solution | Crystallised |
| | 2-T1 | 50.30 | L-Lactic acid | 3.90 | | | Solution | Solution |
| | 2-U1 | 50.70 | Adipic acid | 4.41 | 5.41 | | Solution | Solution |
| | 2-V1 | 50.40 | Sorbic acid | 4.75 | | | Solution | Crystallised |
| | 2-W1 | 50.70 | Acetic acid | 4.75 | | | Solution | Solution |

TABLE 212

Additional volume of solvents charged to achieve full dissolution at temperature

| Experiment Reference-Sample Reference | EtOH charge (5 vol, μl) | Additional EtOH charge 0.25 ml + (μl) | Water charge for dissolution at 70° C. (μl) |
|---|---|---|---|
| 2-A1 | 250.0 | — | — |
| 2-B1 | 250.0 | — | — |
| 2-C1 | 250.0 | — | 20 |
| 2-D1 | 250.0 | — | — |
| 2-E1 | 250.0 | 310.0 | — |
| 2-F1 | 250.0 | — | — |
| 2-G1 | 250.0 | — | — |
| 2-H1 | 250.0 | 310.0 | — |
| 2-I1 | 250.0 | 310.0 | 360 |
| 2-J1 | 250.0 | — | — |
| 2-K1 | 250.0 | 270.0 | 720 |
| 2-L1 | 250.0 | 100.0 | — |
| 2-M1 | 250.0 | 310.0 | 150 |
| 2-N1 | 250.0 | — | — |
| 2-O1 | 250.0 | 170.0 | 30 |
| 2-P1 | 250.0 | — | — |
| 2-Q1 | 250.0 | 240.0 | 20 |
| 2-R1 | 250.0 | 170.0 | 70 |
| 2-S1 | 250.0 | 170.0 | 30 |
| 2-T1 | 250.0 | — | — |
| 2-U1 | 250.0 | — | — |
| 2-V1 | 250.0 | — | — |
| 2-W1 | 250.0 | — | — |

Scale-Up Preparation of Nominated Salt Forms (Experiment 3)

The tabernanthalog tartrate salt: Tabernanthalog (native) (1.0 g, 1.0 wt,) and L-tartaric acid (717.0 mg, 0.72 wt, 1.1 equiv) were dissolved in ethanol (5.0 ml, 5 vol) and water (5.75 ml, 5.75 vol) at 85 to 90° C. The clear brown solution was left to cool down to ambient (solid was observed) before standing undisturbed under 0 to 8° C. conditions for ca 18 h. The product was isolated by filtration, de-liquored and left to pull dry under steady nitrogen flux for ca. 3 h. No wash cycle was applied (to minimize potential losses). The product was off-loaded from the filtration assembly and was oven-dried under vacuum at 40° C. for ca 18 h to afford 3-A1 (Experiment Reference 3-Sample Reference A1) (1.57 g, 95% uncorr. yield). 3-A1 was analyzed by XRPD, $^1$H NMR, TGA, DSC, HPLC.

The tabernanthalog benzoate salt: Tabernanthalog (native) (1.0 g, 1.0 wt) and benzoic acid (587 mg, 0.59 wt, 1.1 equiv) were dissolved in ethanol (5.0 ml, 5.0 vol) and water (850 μl, 0.85 vol) at 85 to 90° C. The clear brown solution was left to cool down to ambient (solid was observed) before standing undisturbed under sub-ambient conditions for ca. 18 h. The product was isolated by filtration, de-liquored and left to pull dry under steady nitrogen flux for ca. 3 h. No wash cycle was applied (to minimize potential losses). The product was off-loaded from the filtration assembly and was oven-dried under vacuum at 40° C. for ca. 18 h to afford 3-B1 (Experiment Reference 3-Sample Reference B1) (1.34 g, 87% uncorr. yield). 3-B1 was analyzed by XRPD, $^1$H NMR, TGA, DSC, HPLC.

The tabernanthalog sorbate salt: Tabernanthalog (native) (1.0 g, 1.0 wt) and sorbic acid (539 mg, 0.54 wt, 1.1 equiv) were dissolved in ethanol (3.0 ml, 3.0 vol) at 85 to 90° C. The clear brown solution was left to cool down to ambient (solid was observed) before standing undisturbed under sub-ambient conditions for ca 18 h. The product was isolated by filtration, de-liquored and left to pull dry under steady nitrogen flux for ca. 3 h. No wash cycle was applied. The product was off-loaded from the filtration assembly and was oven-dried under vacuum at 40° C. for ca 18 h to afford 3-C1 (Experiment Reference 3-Sample Reference C1) (1.57 g, 87% uncorr. yield). 3-C1 was analyzed by XRPD, $^1$H NMR, TGA, DSC, HPLC.

Scale Up of the Tabernanthalog Sorbate Salt to 5 g
(Experiment 4)

Tabernanthalog (native) (3.87 g, 1.0 wt) and sorbic acid (2.07 g, 0.53 wt, 1.1 equiv) were dissolved in ethanol (11 ml, 3.0 vol) at 85 to 90° C. The clear brown solution was left to cool down to ambient (solid was observed) before standing It is noted that tabernanthalog is insoluble in typical HPLC sample diluents, acetonitrile/water. Therefore, DMSO and water were investigated as sample diluents. The ratios trialed were DMSO/water (2/3, v/v) and DMSO/water (1/1, v/v), to verify that Tabernanthalog did not elute in the void, when higher DMSO concentrations were applied. Thus, DMSO/water (1/1, v/v) was selected as the appropriate diluent composition to perform the study and generate the calibration curve, for the SIF panel solubility.

Solubility Determinations in SIF Buffers
(Experiment 5)

The tabernanthalog monofumarate salt (120 mg; Pattern #6a, Form A; 8-A4 of Example 5 [Experiment Reference 8-Sample Reference A4 of Example 5]), the tabernanthalog tartrate salt (150 mg; 3-A1 [Experiment Reference 3-Sample

TABLE 213

Summary of the average peak areas (mAu*s) of the peak areas corresponding to the concentrations used.

| Experiment Reference- Sample Reference | Input weight aims | Tabernanthalog input weights (mg) | Volumes of sample diluent (ml) | Concentration tabernanthalog (mg/ml) | Measured peak areas of calibrants (mAu*s) | x Peak areas (mAu*s) |
|---|---|---|---|---|---|---|
| 8-A1 Inj 1 | 10.00 | 9.80 | 100.00 | 0.10 | 2885.88 | 2882.36 |
| 8-A1 Inj 2 | 10.00 | 9.80 | 100.00 | 0.10 | 2878.84 | |
| | | | | | y = 27622x | |
| 8-B1 Inj 1 | 20.00 | 20.60 | 100.00 | 0.21 | 6010.05 | 6016.22 |
| 8-B1 Inj 2 | 20.00 | 20.60 | 100.00 | 0.21 | 6022.38 | |
| 8-C1 Inj 1 | 30.00 | 29.30 | 100.00 | 0.29 | 8613.78 | 8598.57 |
| 8-C1 Inj 2 | 30.00 | 29.30 | 100.00 | 0.29 | 8583.36 | |
| 8-D1 Inj 1 | 40.00 | 39.90 | 100.00 | 0.40 | 11616.71 | 11597.46 |
| 8-D1 Inj 2 | 40.00 | 39.90 | 100.00 | 0.40 | 11578.21 | |
| 8-E1 Inj 1 | 50.00 | 50.60 | 100.00 | 0.51 | 14592.63 | 14593.09 |
| 8-E1 Inj 2 | 50.00 | 50.60 | 100.00 | 0.51 | 14593.56 | |
| 8-F1 Inj 1 | 60.00 | 60.20 | 100.00 | 0.60 | 17197.63 | 17169.00 |
| 8-F1 Inj 2 | 60.00 | 60.20 | 100.00 | 0.60 | 17140.37 | |
| 8-G1 Inj 1 | 70.00 | 69.00 | 100.00 | 0.69 | 19587.54 | 19565.97 |
| 8-G1 Inj 2 | 70.00 | 69.00 | 100.00 | 0.69 | 19544.40 | |
| 8-H1 Inj 2 | 80.00 | 79.10 | 100.00 | 0.79 | 22049.76 | 22059.65 |
| 8-H1 Inj 2 | 80.00 | 79.10 | 100.00 | 0.79 | 22069.54 | |
| 8-I1 Inj 2 | 90.00 | 86.00 | 100.00 | 0.86 | 26032.60 | 25997.77 |
| 8-I1 Inj 2 | 90.00 | 86.00 | 100.00 | 0.86 | 25962.94 | |
| 8-J1 Inj 2 | 100.00 | 94.10 | 100.00 | 0.94 | 23812.20 | 23828.71 |
| 8-J1 Inj 2 | 100.00 | 94.10 | 100.00 | 0.94 | 23845.21 | | undisturbed under sub-ambient conditions for ca 18 h. The product was isolated by filtration, de-liquored and left to pull dry under steady nitrogen flux for ca. 3 h. No wash cycle was applied. The product was off-loaded from the filtration assembly and was oven-dried under vacuum at 40° C. for ca 18 h to afford 4-A2 (Experiment Reference 4-Sample Reference A2) (5.05 g, 87% uncorr. yield). 4-A2 was analyzed by XRPD, $^1$H NMR, TGA, DSC, HPLC.

Calibration Curve of Non-Ionized Tabernanthalog
(Experiment Reference 8)

Separate portions of Tabernanthalog (native) were weighed out into aluminum boats and were charged to the relevant volumetric flasks. Solutions were made to volume with 1 to 1 (v/v) DMSO/purified water to give calibrants of known API concentrations (Table 213) and analyzed by HPLC, suitable to determine the concentration of Tabernanthalog (native) in the SIF buffer solubility study (Experiment 5 and FIGS. 589-604). Peak areas of the calibrants were plotted against concentration to generate the corresponding calibration curve with slope 27622 and $R^2$ 0.9917 (FIG. 437). At the calculated concentrations the measured value exhibited positive agreement with the predicted value.

Reference A1]), the tabernanthalog benzoate salt (150 mg; 3-B1 [Experiment Reference 3-Sample Reference B1]) and the tabernanthalog sorbate salt (150 mg; 3-C1 [Experiment Reference 3-Sample Reference C1]) were suspended in the relevant SIF buffer (5.0 ml, except for the tabernanthalog fumarate salt in which 4 ml was used to deliver 30 mg/ml concentration) at a concentration of 30 mg/ml (Table 214). The temperature was maintained at 37° C. for 24 h. At this concentration (30 mg/ml), solutions were formed in all but the tabernanthalog benzoate salt (5-C, -G, -K [Experiment Reference 5-Sample Reference C, G, K, respectively]) in all three SIF buffers and the tabernanthalog sorbate salt (5-L [Experiment Reference 5-Sample Reference L]) in FaSSGF.

The suspension was sampled at the relevant time points and centrifuged. The centrifuged supernatant was sub-sampled and analyzed by HPLC and the concentration of Tabernanthalog (native) in solution was determined by comparison with the calibration curve (FIG. 437). The centrifuged pellets, obtained at the time points were analyzed by XRPD as a wet pellet and dried, for evidence of form change. The remainder of the solubility panel remained in solution for the duration of the study.

TABLE 214

Experimental summary of the tabernanthalog salts solubility in SIF buffers

| Experiment Reference-Sample Reference | Input masses (mg) | Input reference | Input details | mw | Buffer | Buffer Charge (ml) |
|---|---|---|---|---|---|---|
| 5-A | 119.4 | 8-A4 of Example 5 | Tabernanthalog•Fumarate | 346.38 | FaSSIF (pH 6.5) | 4 |
| 5-B | 149.8 | 3-A1 | Tabernanthalog•Tartrate | 380.40 | FaSSIF (pH 6.5) | 5 |
| 5-C | 149.6 | 3-B1 | Tabernanthalog•Benzoate | 352.43 | FaSSIF (pH 6.5) | 5 |
| 5-D | 150.6 | 3-C1 | Tabernanthalog•Sorbate | 342.44 | FaSSIF (pH 6.5) | 5 |
| 5-E | 120.2 | 8-A4 of Example 5 | Tabernanthalog•Fumarate | 346.38 | FeSSIF (pH 5.0) | 4 |
| 5-F | 150.1 | 3-A1 | Tabernanthalog•Tartrate | 380.40 | FeSSIF (pH 5.0) | 5 |
| 5-G | 150.2 | 3-B1 | Tabernanthalog•Benzoate | 352.43 | FeSSIF (pH 5.0) | 5 |
| 5-H | 149.6 | 3-C1 | Tabernanthalog•Sorbate | 342.44 | FeSSIF (pH 5.0) | 5 |
| 5-I | 119.4 | 8-A4 of Example 5 | Tabernanthalog•Fumarate | 346.38 | FaSSGF (pH 1.6) | 4 |
| 5-J | 149.8 | 3-A1 | Tabernanthalog•Tartrate | 380.40 | FaSSGF (pH 1.6) | 5 |
| 5-K | 150.2 | 3-B1 | Tabernanthalog•Benzoate | 352.43 | FaSSGF (pH 1.6) | 5 |
| 5-L | 150.4 | 3-C1 | Tabernanthalog•Sorbate | 342.44 | FaSSGF (pH 1.6) | 5 |

5-A to 5-L correspond to "Experiment Reference 5-Sample Reference A" to "Experiment Reference 5-Sample Reference L";
8-A4 of Example 5 is Experiment Reference 8-Sample Reference A4 of Example 5.
3-A1 is Experiment Reference 3-Sample Reference A1;
3-B1 is Experiment Reference 3-Sample Reference B1; and
3-C1 is Experiment Reference 3-Sample Reference C1.

Equilibrium Humidity Evaluation (Experiment 6)

100 mg portions of Tabernanthalog salts (Table 214A) were placed in the relevant open vials. The powders were finely divided and distributed evenly over the base of the vial, such that equal material coverage across the panel was observed. These samples were then maintained 40° C. under 75% RH. The samples were sub-sampled at intervals of 5 and 10 days and analyzed by H NMR, HPLC, XRPD, DSC, TGA and PLM, for evidence of phase change or chemical degradation.

TABLE 214A

Summary of salts.

| Inputs | | |
|---|---|---|
| Experimental reference | Experimental input reference | Input (mg) |
| 6-A1 (Non-ionised) | 8-A4 of Example 5 | 100.5 |
| 6-B1 (tartarate salt) | 3-A1 | 100.3 |
| 6-C1 (benzoate salt) | 3-B1 | 100.3 |
| 6-D1 (sorbate salt) | 3-C1 | 100.4 |

6-A1 is Experiment Reference 6-Sample Reference A1;
6-B1 is Experiment Reference 6-Sample Reference B1;
6-C1 is Experiment Reference 6-Sample Reference C1;
6-D1 is Experiment Reference 6-Sample Reference D1;
3-A1 is Experiment Reference 3-Sample Reference A1;
3-B1 is Experiment Reference 3-Sample Reference B1;
3-C1 is Experiment Reference 3-Sample Reference C1 and 8-A4 of Example 5 is Experiment Reference 8-Sample Reference A4 of Example 5.

H. Characterisation Data i. Tabernanthalog (Native)

The characterization data of tabernanthalog native are provided in FIGS. 393, 438-440, and 442-450 and Table 215.

TABLE 215

XRDP Peak angle data of Tabernanthalog (native). Reported only peaks >10%. Rel. Intensity values calculated based on Net. Intensity values.

| 2-θ (°) | d Value | Rel. Intensity (%) |
|---|---|---|
| 10.4 | 8.47 | 19 |
| 15.1 | 5.87 | 24 |
| 18.9 | 4.69 | 100 |
| 27.3 | 3.26 | 29 |
| 27.4 | 3.26 | 25 | ii. The Tabernanthalog Sorbate Salt (2-V2 (Experiment Reference 2-Sample Reference V2), 3-C1 (Experiment Reference 3-Sample Reference C1), 4-A2 (Experiment Reference 4-Sample Reference A2))

The representative experiments that results in tabernanthalog sorbate salt are (2-V2 (Experiment Reference 2-Sample Reference V2), 3-C1 (Experiment Reference 3-Sample Reference C1), and 4-A2 (Experiment Reference 4-Sample Reference A2)).

The characterization data of the tabernanthalog sorbate salt are provided in FIGS. 451-466 and Table 216.

TABLE 216

XRPD Signal angle data of the tabernanthalog sorbate salt (2-V2 (Experiment Reference 2-Sample Reference V2)). Reported only peaks >10%. Rel. Intensity values calculated based on Net. Intensity values.

| 2-θ (°) | d Value | Rel. Intensity (%) |
|---|---|---|
| 5.7 | 15.59 | 100 |
| 10.5 | 8.44 | 22 |
| 11.4 | 7.76 | 46 |
| 17.9 | 4.95 | 13 |
| 18.8 | 4.71 | 32 |
| 19.1 | 4.64 | 14 |
| 21.4 | 4.16 | 14 |
| 22.6 | 3.93 | 22 |
| 22.9 | 3.89 | 11 |
| 24.4 | 3.65 | 22 | iii. The Tabernanthalog Tartrate Salt (2-I2 (Experiment Reference 2-Sample Reference I2), 3-A1 (Experiment Reference 3-Sample Reference A1))

The representative experiments that results in tabernanthalog tartrate salt are (2-I2 (Experiment Reference 2-Sample Reference I2), and 3-A1 (Experiment Reference 3-Sample Reference A1)). The characterization data of the tabernanthalog tartrate salt are provided in FIGS. 385, 467-472, and 474-482 and Table 217.

TABLE 217

XRPD Signal angle data of the tabernanthalog tartrate salt (2-12 (Experiment Reference 2-Sample Reference I2)). Reported only peaks >10%. Rel. Intensity values calculated based on Net. Intensity values.

| 2-θ (°) | d Value | Rel. Intensity (%) |
|---|---|---|
| 16.1 | 5.51 | 22 |
| 16.4 | 5.39 | 46 |
| 17.3 | 5.11 | 100 |
| 18.2 | 4.87 | 10 |
| 19.9 | 4.46 | 32 |
| 20.4 | 4.34 | 80 |
| 21.3 | 4.16 | 62 |
| 22.4 | 3.97 | 61 |
| 24.0 | 3.70 | 32 |
| 24.3 | 3.66 | 15 |
| 26.1 | 3.41 | 27 |
| 26.8 | 3.32 | 11 |
| 28.3 | 3.15 | 37 |
| 32.6 | 2.74 | 11 |
| 32.9 | 2.72 | 12 |
| 34.3 | 2.61 | 13 |
| 37.8 | 2.38 | 22 |
| 38.1 | 2.36 | 12 | iv. The Tabernanthalog Benzoate Salt (2-R2 (Experiment Reference 2-Sample Reference R2), 3-B1 (Experiment Reference 3-Sample Reference B1))

The representative experiments that results in tabernanthalog benzoate salt are 2-R2 (Experiment Reference 2-Sample Reference R2), and 3-B1 (Experiment Reference 3-Sample Reference B1). The characterization data of the tabernanthalog benzoate salt are provided in FIGS. 483-486 (K) and Table 218.

TABLE 218

XRPD Signal angle data of the tabernanthalog benzoate salt (2-R2; Experiment Reference 2-Sample Reference R2). Reported only peaks >10%. Rel. Intensity values calculated based on Net. Intensity values.

| 2-θ (°) | d Value | Rel. Intensity (%) |
|---|---|---|
| 9.0 | 9.85 | 100 |
| 14.1 | 6.26 | 11 |
| 15.6 | 5.66 | 28 |
| 16.7 | 5.31 | 31 |
| 17.7 | 5.01 | 19 |
| 18.1 | 4.91 | 82 |
| 19.6 | 4.52 | 19 |
| 21.3 | 4.16 | 13 |
| 22.9 | 3.88 | 15 |
| 23.7 | 3.76 | 63 |
| 24.4 | 3.64 | 14 |
| 26.3 | 3.38 | 35 |
| 28.9 | 3.09 | 29 | v. The Tabernanthalog Malate Salt (2-O2 (Experiment Reference 2-Sample Reference O2))

The characterization data of the tabernanthalog malate salt are provided in FIGS. 488-492 and Table 219.

TABLE 219

XRPD Signal angle data of the tabernanthalog malate salt (2-02 (Experiment Reference 2-Sample Reference O2)). Reported only peaks >10%. Rel. Intensity values calculated based on Net. Intensity values.

| 2-θ (°) | d Value | Rel. Intensity (%) |
|---|---|---|
| 6.1 | 14.59 | 11 |
| 14.0 | 6.31 | 43 |
| 16.7 | 5.30 | 44 |
| 18.3 | 4.85 | 29 |
| 19.0 | 4.67 | 11 |
| 19.5 | 4.56 | 100 |
| 21.4 | 4.14 | 55 |
| 21.4 | 4.14 | 55 |
| 23.9 | 3.71 | 12 |
| 25.1 | 3.55 | 17 |
| 25.9 | 3.44 | 11 |
| 27.0 | 3.30 | 39 |
| 31.2 | 2.87 | 12 | vi. The Tabernanthalog Tosylate Salt (2-E2 (Experiment Reference 2-Sample Reference E2))

The characterization data of the tabernanthalog tosylate salt are provided in FIGS. 493-496A and Table 220.

TABLE 220

XRPD Signal angle data of the tabernanthalog tosylate salt (2-E2; Experiment Reference 2-Sample Reference E2). Reported only peaks >10%. Rel. Intensity values calculated based on Net. Intensity values.

| 2-θ (°) | d Value | Rel. Intensity (%) |
|---|---|---|
| 5.5 | 16.11 | 100 |
| 11.0 | 8.05 | 15 | vii. The Tabernanthalog Adipate Salt (2-U2; Experiment Reference 2-Sample Reference U2)

The characterization data of the tabernanthalog adipate salt are provided in FIGS. 389 and 509-512 and Table 221.

---

TABLE 216-continued

XRPD Signal angle data of the tabernanthalog sorbate salt (2-V2 (Experiment Reference 2-Sample Reference V2)). Reported only peaks >10%. Rel. Intensity values calculated based on Net. Intensity values.

| 2-θ (°) | d Value | Rel. Intensity (%) |
|---|---|---|
| 24.7 | 3.61 | 41 |
| 26.9 | 3.32 | 16 |

TABLE 221

XRPD Signal angle data of the tabernanthalog adipate salt (2-U2; Experiment Reference 2-Sample Reference U2). Reported only peaks >10%. Rel. Intensity values calculated based on Net. Intensity values.

| 2-θ (°) | d Value | Rel. Intensity (%) |
|---|---|---|
| 5.9 | 15.05 | 16 |
| 12.0 | 7.39 | 17 |
| 15.7 | 5.62 | 66 |
| 16.5 | 5.37 | 49 |
| 17.8 | 4.99 | 100 |
| 18.6 | 4.76 | 22 |
| 19.4 | 4.57 | 76 |
| 20.6 | 4.30 | 86 |
| 21.0 | 4.24 | 61 |
| 21.4 | 4.15 | 20 |
| 21.8 | 4.08 | 25 |
| 24.0 | 3.71 | 49 |
| 24.6 | 3.62 | 20 |
| 25.5 | 3.49 | 28 |
| 25.9 | 3.44 | 14 |
| 28.2 | 3.16 | 17 |
| 29.9 | 2.99 | 14 | viii. The Tabernanthalog Glucuronate Salt (2-M2; Experiment Reference 2-Sample Reference M2))

The characterization data of the tabernanthalog glucuronate salt are provided in FIGS. 390 and 514-517 and Table 222.

TABLE 222

XRPD Signal angle data of the tabernanthalog glucuronate salt (2-M2; Experiment Reference 2-Sample Reference M2). Reported only peaks >10%. Rel. Intensity values calculated based on Net. Intensity values.

| 2-θ (°) | d Value | Rel. Intensity (%) |
|---|---|---|
| 6.6 | 13.37 | 92 |
| 12.5 | 7.09 | 80 |
| 13.3 | 6.67 | 26 |
| 15.1 | 5.87 | 32 |
| 15.4 | 5.74 | 13 |
| 16.1 | 5.49 | 16 |
| 18.1 | 4.89 | 63 |
| 18.7 | 4.75 | 42 |
| 20.1 | 4.42 | 98 |
| 20.7 | 4.29 | 100 |
| 21.4 | 4.16 | 27 |
| 21.5 | 4.13 | 17 |
| 22.9 | 3.88 | 60 |
| 24.5 | 3.63 | 6. |
| 24.8 | 3.59 | 18 |
| 25.1 | 3.55 | 17 |
| 25.5 | 3.48 | 11 |
| 26.5 | 3.36 | 28 |
| 28.3 | 3.15 | 26 |
| 28.5 | 3.13 | 21 |
| 29.9 | 2.99 | 31 |
| 31.2 | 2.87 | 15 |
| 32.0 | 2.79 | 11 |
| 33.5 | 2.67 | 16 |
| 33.6 | 2.67 | 19 |
| 34.4 | 2.61 | 17 |
| 37.8 | 2.38 | 10 | ix. The Tabernanthalog Phosphate Salt (2-H2; Experiment Reference 2-Sample Reference H2)

The characterization data of the tabernanthalog phosphate salt are provided in FIGS. 391 and 519-522 and Table 223.

TABLE 223

XRPD Signal angle data of the tabernanthalog phosphate salt (2-H2; Experiment Reference 2-Sample Reference H2). Reported only peaks >10%. Rel. Intensity values calculated based on Net. Intensity values.

| 2-θ (°) | d Value | Rel. Intensity (%) |
|---|---|---|
| 5.3 | 16.73 | 100 |
| 10.5 | 8.41 | 16 |
| 14.4 | 6.15 | 60 |
| 14.7 | 6.02 | 54 |
| 15.2 | 5.81 | 16 |
| 15.8 | 5.61 | 15 |
| 17.2 | 5.16 | 14 |
| 19.5 | 4.55 | 19 |
| 19.7 | 4.51 | 25 |
| 20.2 | 4.40 | 50 |
| 22.7 | 3.92 | 33 |
| 22.9 | 3.88 | 37 |
| 23.6 | 3.77 | 13 |
| 24.0 | 3.71 | 37 |
| 24.3 | 3.66 | 20 |
| 25.6 | 3.47 | 20 |
| 25.5 | 3.49 | 31 |
| 26.3 | 3.39 | 12 |
| 29.9 | 2.98 | 13 |
| 30.1 | 2.97 | 10 | x. The Tabernanthalog Edisylate Salt (242; Experiment Reference 2-Sample Reference J2)

The characterization data of the tabernanthalog edisylate salt are provided in FIGS. 392 and 524-527 and Table 224.

TABLE 224

XRPD Signal angle data of the tabernanthalog edisylate salt (2-J2; Experiment Reference 2-Sample Reference J2). Reported only peaks >10%. Rel. Intensity values calculated based on Net. Intensity values.

| 2-θ (°) | d Value | Rel. Intensity (%) |
|---|---|---|
| 4.4 | 20.14 | 21 |
| 4.5 | 19.50 | 25 |
| 8.1 | 10.88 | 22 |
| 8.7 | 10.16 | 11 |
| 12.2 | 7.22 | 16 |
| 12.6 | 7.02 | 32 |
| 12.8 | 6.91 | 27 |
| 14.0 | 6.33 | 20 |
| 14.7 | 6.01 | 24 |
| 15.1 | 5.87 | 2 |
| 16.2 | 5.47 | 19 |
| 16.8 | 5.29 | 21 |
| 17.4 | 5.09 | 100 |
| 18.0 | 4.93 | 16 |
| 18.4 | 4.83 | 27 |
| 18.7 | 4.75 | 10 |
| 19.9 | 4.46 | 80 |
| 19.6 | 4.52 | 25 |
| 19.9 | 4.45 | 91 |
| 20.4 | 4.34 | 30 |
| 20.8 | 4.26 | 42 |
| 21.5 | 4.13 | 22 |
| 21.8 | 4.07 | 38 |
| 22.2 | 4.00 | 18 |
| 23.3 | 3.81 | 2 |
| 24.2 | 3.68 | 17 |
| 24.5 | 3.64 | 23 |
| 25.4 | 3.50 | 14 |
| 26.8 | 3.33 | 17 |
| 27.4 | 3.25 | 15 |
| 28.2 | 3.16 | 11 |
| 29.2 | 3.06 | 15 |

I. Experimental Data i. Heat-Up Cool-Down Crystallization Salt Screen (Experiment 2 Rejected Salt Forms)

The experimental data of the heat-up cool-down crystallization salt screen (Experiment 2 rejected salt forms) are provided in FIGS. 529-544 and tables 225-229.

TABLE 225

XRPD Signal angle data of the tabernanthalog maleate salt (2-G2; Experiment Reference 2-Sample Reference G2). Reported only peaks >10% Rel. Intensity values calculated based on Net. Intensity values.

| 2-θ (°) | d Value | Rel. Intensity (%) |
|---|---|---|
| 9.2 | 9.65 | 18 |
| 10.4 | 8.47 | 26 |
| 12.6 | 7.04 | 28 |
| 16.8 | 5.27 | 11 |
| 18.9 | 4.69 | 26 |
| 19.4 | 4.57 | 46 |
| 20.7 | 4.29 | 100 |
| 21.0 | 4.23 | 19 |
| 22.2 | 4.01 | 27 |
| 25.3 | 3.52 | 25 |
| 25.3 | 3.52 | 29 |
| 26.8 | 3.32 | 58 |
| 27.6 | 3.22 | 18 |
| 27.7 | 3.21 | 13 |
| 28.3 | 3.16 | 15 |

TABLE 226

XRPD Signal angle data of the tabernanthalog galactarate salt (2-K2; Experiment Reference 2-Sample Reference K2). Reported only peaks >10%. Rel. Intensity values calculated based on Net. Intensity values.

| 2-θ (°) | d Value | Rel. Intensity (%) |
|---|---|---|
| 5.7 | 15.49 | 30 |
| 12.0 | 7.40 | 17 |
| 13.0 | 6.81 | 10 |
| 14.3 | 6.20 | 12 |
| 17.1 | 5.17 | 12 |
| 17.6 | 5.04 | 13 |
| 18.1 | 4.88 | 46 |
| 19.6 | 4.53 | 100 |
| 21.5 | 4.13 | 26 |
| 22.0 | 4.03 | 16 |
| 24.0 | 3.71 | 13 |
| 24.5 | 3.63 | 15 |
| 26.1 | 3.41 | 13 |
| 26.8 | 3.33 | 20 |
| 30.7 | 2.91 | 68 |
| 34.5 | 2.60 | 28 |
| 36.8 | 2.44 | 18 |
| 37.0 | 2.43 | 16 |
| 37.6 | 2.39 | 35 |
| 37.7 | 2.39 | 65 |

TABLE 227

XRPD Signal angle data of the tabernanthalog citrate salt (2-L2; Experiment Reference 2-Sample Reference L2). Reported only peaks >10%. Rel. Intensity values calculated based on Net. Intensity values.

| 2-θ (°) | d Value | Rel. Intensity (%) |
|---|---|---|
| 12.5 | 7.09 | 81 |
| 13.0 | 6.79 | 59 |
| 16.6 | 5.35 | 100 |
| 17.7 | 5.00 | 38 |
| 17.6 | 5.02 | 44 |
| 19.1 | 4.64 | 20 |
| 19.7 | 4.51 | 20 |
| 20.9 | 4.25 | 75 |
| 21.9 | 4.05 | 46 |
| 23.7 | 3.75 | 45 |
| 26.0 | 3.42 | 33 |
| 26.9 | 3.32 | 11 |
| 34.7 | 2.58 | 11 |

TABLE 228

XRPD Signal angle data of the tabernanthalog glycolate salt (2-N2; Experiment Reference 2-Sample Reference N2)). Reported only peaks >10%. Rel. Intensity values calculated based on Net. Intensity values.

| 2-θ (°) | d Value | Rel. Intensity (%) |
|---|---|---|
| 9.1 | 9.72 | 62 |
| 9.7 | 9.09 | 56 |
| 11.6 | 7.60 | 13 |
| 18.0 | 4.93 | 97 |
| 18.3 | 4.85 | 27 |
| 19.0 | 4.67 | 37 |
| 19.6 | 4.53 | 25 |
| 19.8 | 4.48 | 25 |
| 20.1 | 4.41 | 19 |
| 23.5 | 3.79 | 100 |
| 23.4 | 3.80 | 84 |
| 24.6 | 3.61 | 13 |
| 25.2 | 3.53 | 11 |
| 26.2 | 3.40 | 16 |
| 26.5 | 3.36 | 10 |
| 29.5 | 3.02 | 23 |

TABLE 229

XRPD Signal angle data of the tabernanthalog succinate salt (2-S2; Experiment Reference 2-Sample Reference S2). Reported only peaks >10%. Rel. Intensity values calculated based on Net. Intensity values.

| 2-θ (°) | d Value | Rel. Intensity (%) |
|---|---|---|
| 7.9 | 11.21 | 14 |
| 8.3 | 10.62 | 100 |
| 11.0 | 8.02 | 17 |
| 15.4 | 5.75 | 27 |
| 15.7 | 5.62 | 15 |
| 16.1 | 5.51 | 19 |
| 17.2 | 5.16 | 69 |
| 20.1 | 4.41 | 16 |
| 21.3 | 4.18 | 16 |
| 21.3 | 4.16 | 17 |
| 22.2 | 4.01 | 43 |
| 23.6 | 3.77 | 14 |
| 24.1 | 3.69 | 23 |
| 24.7 | 3.60 | 57 |
| 28.1 | 3.17 | 11 |

TABLE 229-continued

XRPD Signal angle data of the tabernanthalog succinate salt (2-S2; Experiment Reference 2-Sample Reference S2). Reported only peaks >10%. Rel. Intensity values calculated based on Net. Intensity values.

| 2-θ (°) | d Value | Rel. Intensity (%) |
|---|---|---|
| 28.9 | 3.09 | 13 |
| 29.9 | 2.98 | 11 | ii. Scale Up of Nominated Salt Forms (Experiment 3)

The experimental data of the scale up of nominated salt forms (Experiment 3) are provided in FIGS. 545-560 and Tables 230-232. HPLC, DVS and PLM data for these batches are reported in Sections H.ii, H.iii, and H.iv.

TABLE 230

XRPD Signal angle data of tabernanthalog tartrate salt (3-A1; Experiment Reference 3-Sample Reference A1). Reported only peaks >10%. Rel. Intensity values calculated based on Net. Intensity values.

| 2-θ (°) | d Value | Rel. Intensity (%) |
|---|---|---|
| 6.0 | 14.63 | 13 |
| 16.1 | 5.51 | 21 |
| 16.4 | 5.39 | 37 |
| 17.3 | 5.12 | 100 |
| 18.2 | 4.87 | 11 |
| 19.9 | 4.46 | 27 |
| 20.4 | 4.35 | 63 |
| 21.3 | 4.16 | 46 |
| 22.3 | 3.98 | 59 |
| 24.0 | 3.71 | 23 |
| 24.3 | 3.65 | 12 |
| 26.1 | 3.41 | 27 |
| 28.3 | 3.16 | 31 |
| 32.9 | 2.72 | 11 |
| 37.8 | 2.38 | 21 |

TABLE 231

XRPD Signal angle data of tabernanthalog benzoate salt (3-B1; Experiment Reference 3-Sample Reference B1). Reported only peaks >10%. Rel. Intensity values calculated based on Net. Intensity values.

| 2-θ (°) | d Value | Rel. Intensity (%) |
|---|---|---|
| 9.0 | 9.82 | 100 |
| 18.0 | 4.91 | 78 |
| 23.8 | 3.74 | 45 |

TABLE 232

XRPD Signal angle data of tabernanthalog sorbate salt (3-C1; Experiment Reference 3-Sample Reference C1). Reported only peaks >10%. Rel. Intensity values calculated based on Net. Intensity values.

| 2-θ (°) | d Value | Rel. Intensity (%) |
|---|---|---|
| 5.7 | 15.54 | 100 |
| 11.4 | 7.76 | 42 |

TABLE 232-continued

XRPD Signal angle data of tabernanthalog sorbate salt (3-C1; Experiment Reference 3-Sample Reference C1). Reported only peaks >10%. Rel. Intensity values calculated based on Net. Intensity values.

| 2-θ (°) | d Value | Rel. Intensity (%) |
|---|---|---|
| 22.6 | 3.93 | 10 |
| 24.7 | 3.60 | 22 | iii. Scale Up of the Tabernanthalog Sorbate Salt to 5 g (Experiment 4)

The experimental data of the scale up of the tabernanthalog sorbate salt to 5 g (Experiment 4) are provided in FIGS. 561-572 and Table 233.

TABLE 233

XRPD Signal angle data of tabernanthalog sorbate (4-A2; Experiment Reference 4-Sample Reference A2). Reported only peaks >10%. Rel. Intensity values calculated based on Net. Intensity values.

| 2-θ (°) | d Value | Rel. Intensity (%) |
|---|---|---|
| 5.7 | 15.53 | 100 |
| 11.4 | 7.75 | 40 |
| 22.8 | 3.89 | 11 | iv. Solubility Determinations in SIF Buffers (Experiment 5)

The experimental data of the solubility assessment in SIF buffers (Experiment 5) are provided in FIGS. 573-604 and Tables 234-249. The powder diffraction patterns reported here are obtained from the dry pellets.

TABLE 234

XRPD Signal angle data of tabernanthalog benzoate salt (5-C3; Experiment Reference 5-Sample Reference C3). Reported only peaks >10%. Rel. Intensity values calculated based on Net. Intensity values.

| 2-θ (°) | d Value | Rel. Intensity (%) |
|---|---|---|
| 9.0 | 9.81 | 27 |
| 11.5 | 7.72 | 10 |
| 14.2 | 6.24 | 20 |
| 15.7 | 5.65 | 26 |
| 16.7 | 5.29 | 34 |
| 17.7 | 5.00 | 16 |
| 18.1 | 4.89 | 85 |
| 19.4 | 4.56 | 13 |
| 19.7 | 4.51 | 16 |
| 21.4 | 4.15 | 17 |
| 23.0 | 3.87 | 17 |
| 23.0 | 3.86 | 20 |
| 23.7 | 3.75 | 100 |
| 24.5 | 3.64 | 14 |
| 26.4 | 3.38 | 25 |
| 28.9 | 3.09 | 13 |

TABLE 235

XRPD Signal angle data of tabernanthalog benzoate salt (5-G3; Experiment Reference 5-Sample Reference G3). Reported only peaks >10%. Rel. Intensity values calculated based on Net. Intensity values.

| 2-θ (°) | d Value | Rel. Intensity (%) |
|---|---|---|
| 9.0 | 9.81 | 25 |
| 14.2 | 6.24 | 16 |
| 15.7 | 5.65 | 19 |
| 16.8 | 5.29 | 27 |
| 17.7 | 5.00 | 16 |
| 18.1 | 4.89 | 63 |
| 19.7 | 4.51 | 12 |
| 21.4 | 4.15 | 16 |
| 23.0 | 3.86 | 15 |
| 23.7 | 3.74 | 100 |
| 26.4 | 3.37 | 17 |
| 28.9 | 3.09 | 11 |

TABLE 236

XRPD Signal angle data of tabernanthalog benzoate salt 5-K3 (Experiment Reference 5-Sample Reference K3). Reported only peaks >10%. Rel. Intensity values calculated based on Net. Intensity values.

| 2-θ (°) | d Value | Rel. Intensity (%) |
|---|---|---|
| 8.1 | 10.94 | 100 |
| 16.2 | 5.46 | 31 |
| 17.1 | 5.17 | 25 |
| 23.7 | 3.75 | 23 |
| 25.8 | 3.46 | 14 |
| 27.7 | 3.22 | 10 |
| 30.1 | 2.97 | 10 |

TABLE 237

XRPD Signal angle data of tabernanthalog sorbate salt (5-L3; Experiment Reference 5-Sample Reference L3). Reported only peaks >10%. Rel. Intensity values calculated based on Net. Intensity values.

| 2-θ (°) | d Value | Rel. Intensity (%) |
|---|---|---|
| 11.4 | 7.77 | 36 |
| 12.9 | 6.84 | 29 |
| 22.8 | 3.90 | 100 |
| 23.4 | 3.80 | 11 |
| 24.7 | 3.59 | 31 |
| 27.7 | 3.22 | 32 |

TABLE 238

XRPD Signal angle data of 5-C6 (Experiment Reference 5-Sample Reference C6). Reported only peaks > 10%. Rel. Intensity values calculated based on Net. Intensity values.

| 2-θ (°) | d Value | Rel. Intensity (%) |
|---|---|---|
| 8.9 | 9.89 | 17 |
| 14.1 | 6.27 | 13 |
| 15.6 | 5.67 | 23 |
| 16.7 | 5.31 | 25 |
| 17.6 | 5.02 | 13 |
| 18.1 | 4.91 | 67 |
| 19.6 | 4.53 | 11 |
| 21.3 | 4.16 | 17 |
| 22.9 | 3.88 | 19 |
| 23.7 | 3.76 | 100 |
| 24.4 | 3.65 | 13 |
| 26.3 | 3.38 | 22 |
| 28.8 | 3.09 | 13 |

TABLE 239

XRPD Signal angle data of tabernanthalog benzoate salt (5-G6 (Experiment Reference 5-Sample Reference G6). Reported only peaks > 10%. Rel. Intensity values calculated based on Net. Intensity values.

| 2-θ (°) | d Value | Rel. Intensity (%) |
|---|---|---|
| 8.9 | 9.89 | 16 |
| 14.1 | 6.26 | 15 |
| 15.6 | 5.67 | 25 |
| 16.7 | 5.31 | 31 |
| 17.7 | 5.02 | 15 |
| 18.1 | 4.91 | 70 |
| 19.4 | 4.58 | 11 |
| 19.6 | 4.52 | 15 |
| 21.3 | 4.16 | 14 |
| 22.9 | 3.87 | 23 |
| 23.7 | 3.75 | 100 |
| 24.4 | 3.64 | 13 |
| 26.3 | 3.38 | 22 |
| 28.9 | 3.09 | 15 |
| 31.7 | 2.82 | 12 |

TABLE 240

XRPD Signal angle data of tabernanthalog benzoate salt (5-K6 (Experiment Reference 5-Sample Reference K6). Reported only peaks > 10%. Rel. Intensity values calculated based on Net. Intensity values.

| 2-θ (°) | d Value | Rel. Intensity (%) |
|---|---|---|
| 8.1 | 10.96 | 100 |
| 16.2 | 5.47 | 29 |
| 17.1 | 5.18 | 33 |
| 23.7 | 3.75 | 26 |
| 25.8 | 3.46 | 22 |
| 27.7 | 3.22 | 16 |
| 30.0 | 2.97 | 12 |

TABLE 241

XRPD Signal angle data of tabernanthalog sorbate salt (5-L6; Experiment Reference 5-Sample Reference L6). Reported only peaks > 10%. Rel. Intensity values calculated based on Net. Intensity values.

| 2-θ (°) | d Value | Rel. Intensity (%) |
|---|---|---|
| 11.4 | 7.75 | 50 |
| 12.9 | 6.83 | 29 |
| 22.8 | 3.90 | 100 |
| 24.8 | 3.59 | 20 |
| 27.7 | 3.21 | 23 |

TABLE 242

XRPD Signal angle data of tabernanthalog benzoate salt
(5-C9 (Experiment Reference 5-Sample Reference C9).
Reported only peaks > 10%.
Rel. Intensity values calculated based on Net. Intensity values.

| 2-θ (°) | d Value | Rel. Intensity (%) |
|---|---|---|
| 8.9 | 9.89 | 15 |
| 14.1 | 6.27 | 12 |
| 15.6 | 5.67 | 20 |
| 16.7 | 5.32 | 20 |
| 17.6 | 5.03 | 13 |
| 18.0 | 4.91 | 60 |
| 19.4 | 4.57 | 10 |
| 19.6 | 4.53 | 12 |
| 21.3 | 4.16 | 15 |
| 22.9 | 3.88 | 18 |
| 23.6 | 3.76 | 100 |
| 24.4 | 3.65 | 11 |
| 26.3 | 3.39 | 20 |
| 28.8 | 3.10 | 13 |

TABLE 243

XRPD Signal angle data of tabernanthalog benzoate salt
(5-G9 (Experiment Reference 5-Sample Reference G9).
Reported only peaks > 10%.
Rel. Intensity values calculated based on Net. Intensity values.

| 2-θ (°) | d Value | Rel. Intensity (%) |
|---|---|---|
| 9.0 | 9.84 | 21 |
| 11.4 | 7.73 | 10 |
| 14.2 | 6.25 | 15 |
| 15.7 | 5.66 | 24 |
| 16.7 | 5.30 | 28 |
| 17.7 | 5.01 | 13 |
| 18.1 | 4.90 | 64 |
| 19.4 | 4.57 | 11 |
| 19.6 | 4.52 | 13 |
| 21.4 | 4.15 | 17 |
| 23.0 | 3.87 | 20 |
| 23.7 | 3.75 | 100 |
| 24.4 | 3.64 | 11 |
| 26.4 | 3.38 | 24 |
| 28.9 | 3.09 | 12 |

TABLE 244

XRPD Signal angle data of tabernanthalog benzoate salt
(5-K9 (Experiment Reference 5-Sample Reference K9).
Reported only peaks > 10%.
Rel. Intensity values calculated based on Net. Intensity values.

| 2-θ (°) | d Value | Rel. Intensity (%) |
|---|---|---|
| 8.1 | 10.95 | 100 |
| 16.2 | 5.47 | 36 |
| 17.1 | 5.17 | 57 |
| 19.0 | 4.67 | 13 |
| 23.7 | 3.75 | 57 |
| 25.8 | 3.46 | 48 |
| 27.7 | 3.22 | 30 |
| 30.0 | 2.97 | 25 |

TABLE 245

XRPD Signal angle data of tabernanthalog sorbate salt
(5-L9 (Experiment Reference 5-Sample Reference L9).
Reported only peaks > 10%.
Rel. Intensity values calculated based on Net. Intensity values.

| 2-θ (°) | d Value | Rel. Intensity (%) |
|---|---|---|
| 11.4 | 7.76 | 52 |
| 12.9 | 6.84 | 25 |
| 22.8 | 3.90 | 100 |
| 24.7 | 3.60 | 14 |
| 27.7 | 3.22 | 17 |

TABLE 246

XRPD Signal angle data of tabernanthalog benzoate salt
(5-C12 (Experiment Reference 5-Sample Reference C12).
Reported only peaks > 10%.
Rel. Intensity values calculated based on Net. Intensity values.

| 2-θ (°) | d Value | Rel. Intensity (%) |
|---|---|---|
| 9.0 | 9.81 | 22 |
| 11.5 | 7.71 | 11 |
| 14.2 | 6.24 | 19 |
| 15.7 | 5.64 | 34 |
| 16.8 | 5.29 | 32 |
| 17.7 | 4.99 | 17 |
| 18.1 | 4.89 | 79 |
| 19.5 | 4.55 | 10 |
| 19.7 | 4.51 | 13 |
| 21.4 | 4.15 | 17 |
| 23.0 | 3.86 | 21 |
| 23.7 | 3.75 | 100 |
| 24.5 | 3.64 | 13 |
| 26.4 | 3.38 | 23 |
| 28.9 | 3.08 | 13 |

TABLE 247

XRPD Signal angle data of tabernanthalog benzoate salt
(5-G12 (Experiment Reference 5-Sample Reference G12).
Reported only peaks > 10%.
Rel. Intensity values calculated based on Net. Intensity values.

| 2-θ (°) | d Value | Rel. Intensity (%) |
|---|---|---|
| 8.9 | 9.89 | 14 |
| 14.1 | 6.27 | 15 |
| 15.6 | 5.67 | 24 |
| 16.7 | 5.31 | 28 |
| 17.7 | 5.02 | 14 |
| 18.1 | 4.91 | 73 |
| 19.6 | 4.53 | 14 |
| 21.3 | 4.16 | 17 |
| 22.9 | 3.88 | 20 |
| 23.7 | 3.76 | 100 |
| 24.4 | 3.65 | 13 |
| 26.3 | 3.38 | 26 |
| 28.8 | 3.09 | 14 |

TABLE 248

XRPD Signal angle data of tabernanthalog benzoate salt
(5-K12 (Experiment Reference 5-Sample Reference K12).
Reported only peaks > 10%.
Rel. Intensity values calculated based on Net. Intensity values.

| 2-θ (°) | d Value | Rel. Intensity (%) |
|---|---|---|
| 8.1 | 10.90 | 100 |
| 16.2 | 5.47 | 34 |
| 17.1 | 5.17 | 72 |

TABLE 248-continued

XRPD Signal angle data of tabernanthalog benzoate salt
(5-K12 (Experiment Reference 5-Sample Reference K12).
Reported only peaks > 10%.
Rel. Intensity values calculated based on Net. Intensity values.

| 2-θ (°) | d Value | Rel. Intensity (%) |
|---|---|---|
| 19.0 | 4.67 | 12 |
| 23.7 | 3.75 | 74 |
| 25.7 | 3.46 | 46 |
| 27.6 | 3.22 | 25 |
| 30.0 | 2.98 | 24 |

TABLE 249

XRPD Signal angle data of tabernanthalog sorbate salt
(5-L12 (Experiment Reference 5-Sample Reference L12).
Reported only peaks > 10%.
Rel. Intensity values calculated based on Net. Intensity values.

| 2-θ (°) | d Value | Rel. Intensity (%) |
|---|---|---|
| 11.4 | 7.76 | 34 |
| 12.9 | 6.84 | 29 |
| 22.7 | 3.91 | 100 |
| 24.7 | 3.60 | 17 |
| 27.7 | 3.22 | 19 | v. Equilibrium Humidity Evaluation (75% RH/40° C.), (Experiment 6)

The Tabernanthalog Monofumarate Salt;
The experimental data of the tabernanthalog fumarate salt are provided in FIGS. 605-620 and Tables 250-251.

TABLE 250

XRPD Signal angle data of tabernanthalog monofumarate salt
(6-A1; Experiment Reference 6-Sample Reference A1).
Reported only peaks > 10%.
Rel. Intensity values calculated based on Net. Intensity values.

| 2-θ (°) | d Value | Rel. Intensity (%) |
|---|---|---|
| 12.9 | 6.83 | 10 |
| 16.5 | 5.35 | 94 |
| 19.5 | 4.55 | 89 |
| 19.5 | 4.54 | 100 |
| 20.6 | 4.30 | 86 |
| 22.1 | 4.02 | 21 |
| 25.3 | 3.51 | 74 |
| 26.1 | 3.41 | 32 |
| 33.5 | 2.67 | 11 |

TABLE 251

XRPD Signal angle data of tabernanthalog monofumarate salt
(6-A2 (Experiment Reference 6-Sample Reference A2).
Reported only peaks > 10%.
Rel. Intensity values calculated based on Net. Intensity values.

| 2-θ (°) | d Value | Rel. Intensity (%) |
|---|---|---|
| 13.0 | 6.82 | 10 |
| 16.6 | 5.35 | 93 |
| 19.6 | 4.53 | 100 |
| 20.7 | 4.30 | 83 |
| 22.1 | 4.02 | 21 |
| 25.3 | 3.51 | 75 |
| 26.1 | 3.41 | 33 |
| 33.5 | 2.67 | 12 |

The Tabernanthalog Tartrate Salt

The experimental data of the tabernanthalog tartrate salt are provided in FIGS. 621-636 and Tables 252-253.

TABLE 252

XRPD Signal angle data of tabernanthalog tartrate salt
(6-B1; Experiment Reference 6-Sample Reference B1).
Reported only peaks > 10%.
Rel. Intensity values calculated based on Net. Intensity values.

| 2-θ (°) | d Value | Rel. Intensity (%) |
|---|---|---|
| 16.1 | 5.52 | 21 |
| 16.4 | 5.39 | 38 |
| 17.1 | 5.18 | 15 |
| 17.3 | 5.11 | 100 |
| 19.9 | 4.46 | 30 |
| 20.4 | 4.35 | 70 |
| 21.3 | 4.16 | 47 |
| 22.4 | 3.97 | 64 |
| 24.0 | 3.71 | 27 |
| 24.3 | 3.66 | 12 |
| 26.1 | 3.41 | 28 |
| 28.3 | 3.15 | 35 |
| 32.9 | 2.72 | 11 |
| 37.8 | 2.38 | 19 |

TABLE 253

XRPD Signal angle data of tabernanthalog tartrate salt
(6-B2 (Experiment Reference 6-Sample
Reference B2). Reported only peaks > 10%.
Rel. Intensity values calculated
based on Net. Intensity values.

| 2-θ (°) | d Value | Rel. Intensity (%) |
|---|---|---|
| 16.2 | 5.48 | 25 |
| 16.5 | 5.36 | 40 |
| 17.4 | 5.09 | 100 |
| 20.0 | 4.44 | 29 |
| 20.5 | 4.33 | 63 |
| 21.4 | 4.14 | 48 |
| 22.5 | 3.96 | 56 |
| 24.1 | 3.69 | 23 |
| 26.2 | 3.40 | 23 |
| 28.4 | 3.14 | 30 |
| 37.9 | 2.37 | 18 |

The Tabernanthalog Benzoate Salt

The experimental data of the tabernanthalog benzoate salt are provided in FIGS. 637-652 and Tables 254-255.

TABLE 254

XRPD Signal angle data of tabernanthalog
benzoate salt (6-C1; Experiment
Reference 6-Sample Reference C1).
Reported only peaks > 10%.
Rel. Intensity values calculated
based on Net. Intensity values.

| 2-θ (°) | d Value | Rel. Intensity (%) |
|---|---|---|
| 9.0 | 9.85 | 100 |
| 9.1 | 9.75 | 11 |
| 18.0 | 4.92 | 73 |
| 23.7 | 3.75 | 36 |
| 27.1 | 3.28 | 10 |

TABLE 255

XRPD Signal angle data of tabernanthalog
benzoate salt (6-C2 (Experiment
Reference 6-Sample Reference C2).
Reported only peaks > 10%.
Rel. Intensity values calculated
based on Net. Intensity values.

| 2-θ (°) | d Value | Rel. Intensity (%) |
|---|---|---|
| 9.0 | 9.80 | 46 |
| 16.8 | 5.28 | 12 |
| 18.1 | 4.90 | 22 |
| 19.7 | 4.51 | 15 |
| 19.7 | 4.51 | 15 |
| 23.7 | 3.74 | 100 |
| 24.4 | 3.64 | 21 |
| 26.4 | 3.37 | 40 |

The Tabernanthalog Sorbate Salt

The experimental data of the tabernanthalog sorbate salt are provided in FIGS. 653-668 and Tables 256-257.

TABLE 256

XRPD Signal angle data of tabernanthalog
sorbate salt (6-D1; Experiment
Reference 6-Sample Reference D1).
Reported only peaks > 10%.
Rel. Intensity values calculated
based on Net. Intensity values.

| 2-θ (°) | d Value | Rel. Intensity (%) |
|---|---|---|
| 5.7 | 15.37 | 100 |
| 11.5 | 7.71 | 56 |
| 18.9 | 4.69 | 16 |
| 23.0 | 3.86 | 11 |

TABLE 257

XRPD Signal angle data of tabernanthalog
sorbate salt (6-D2 (Experiment
Reference 6-Sample Reference D2).
Reported only peaks > 10%.
Rel. Intensity values calculated
based on Net. Intensity values.

| 2-θ (°) | d Value | Rel. Intensity (%) |
|---|---|---|
| 5.7 | 15.49 | 100 |
| 11.4 | 7.74 | 40 |
| 18.9 | 4.70 | 15 |
| 18.8 | 4.71 | 13 |
| 24.6 | 3.61 | 11 | vi. Dynamic Vapour Sorption (DVS)

The experimental data are provided in FIGS. 669-671.

Example 9: Synthesis of Tabernanthalog Fumarate

A. Published Literature Method to Synthesize Tabernanthalog Fumarate Results in Crystalline Pattern #1

8-Methoxy-3-methyl-2,4,5,6-tetrahydro-1H-azepino[4,5-b]indole fumarate salt—The methodology detailed in WO 2020/176599 was followed. In this particular example, Fumaric acid (408 mg, 3.5 mmol, 0.8 equiv) was added to a sealed tube containing acetone (20 mL). The solution was carefully heated until all of the fumaric acid dissolved. After cooling the solution to rt, a solution of 8-Methoxy-3-methyl-2,4,5,6-tetrahydro-1H-azepino[4,5-b]indole (1.028 g, 4.4 mmol, 1.0 equiv) in acetone (5 mL) was added dropwise, and the mixture was cooled in the freezer overnight. The solid was filtered, washed with acetone, and dried under reduced pressure to yield the title compound (1.055 g, 69%) as a 1:1 salt.

As-received fumarate material (ref. batch: Sample Reference 1) was characterized as Pattern #1 (FIG. 672).

B. Novel Method to Synthesize Tabernanthalog Fumarate Results in Form A (Pattern #6a)

8-Methoxy-3-methyl-2,4,5,6-tetrahydro-1H-azepino[4,5-b]indole fumarate salt (polymorph Form A) The following is a new synthesis method identified through polymorph screening to prepare stable crystalline fumarate Form A.

Tabernanthalog fumarate salt (1.0 g, 1.0 wt) was charged to the vessel at 20° C. Purified water (5 ml, 5.0 vol) was charged at 20° C., and the contents of the vessel were stirred at 20° C. for ca. 10 days. The suspension was filtered through a sintered funnel. The vessel was rinsed with purified water (0.5 ml, 0.5 vol) at 20° C., and this was used to transfer any remaining solids and to wash the filter cake. The product was dried on the filter at 20° C. under sustained nitrogen flux for ca. 20 to 24 h. The dried material was collected and the yield was recorded (560.6 mg, 56% yield) and analyzed.

The XRPD profile of Pattern #6a, Form A is provided is FIG. 673.

C. Synthesis of Tabernanthalog Fumarate Form A Based on the Novel Method

8-Methoxy-3-methyl-2,4,5,6-tetrahydro-1H-azepino[4,5-b]indole fumarate salt (polymorph Form A)

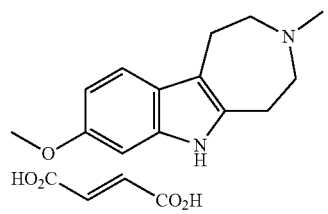

Experimental Description

Samples transferred to a Bruker sample holder.

A preliminary scan in the 2θ range of 5-100° was performed to determine the extent of the crystallinity, and the appropriate settings to use for the full scan.

Incident optics: Divergence Slit=1.0 mm|Diffracted optics: Ni Kβ filter.

2theta range: 5-70°, step size=0.03°, 1.0 s step$^{-1}$.

Synthesis:

To a refluxing suspension of fumaric acid (1.29 g, 11.1 mmol) in acetone (25 mL) was added a suspension of 8-methoxy-3-methyl-2,4,5,6-tetrahydro-1H-azepino[4,5-b]indole (3.20 g, 13.9 mmol) in acetone (25 mL). A yellow precipitate immediately formed. The suspension was heated at reflux for 20 min before cooling overnight. The precipitate was filtered, and the filter cake was washed with acetone (50 mL), and dried on a drying tray at 40° C. for 12 h. The solid was suspended in deionised water (20 mL) and heated to 50° C., where it remained a suspension. The suspension was then cooled to rt and stirred for 12 days. The off-white suspension was isolated by filtration, and the filter cake was washed with deionised water (2×5 mL) and dried overnight on a drying tray at 40° C. to afford the title compound, polymorph Form A (2.80 g, 58%) as a pale yellow solid. Retention time 1.095 min; Calculated for $[C_{14}H_{18}N_2O]^+$ 231.1; found 231.2; $^1$H NMR (400 MHz, DMSO-$d_6$) δ 10.50 (s, 1H), 7.24 (d, J=8.6 Hz, 1H), 6.75 (d, J=2.2 Hz, 1H), 6.66-6.51 (m, 3H), 3.73 (s, 3H), 3.02-2.78 (m, 8H), 2.55 (s, 3H).

XRPD of Tabernanthalog Fumarate Sample Prepared is Provided in FIG. 674, Table 258.

TABLE 258

XRPD Signal angle data of the Tabernanthalog Fumarate (Form A) sample prepared

| Pos. [°2θ] | d-spacing [Å] | Rel. Int. [%] |
|---|---|---|
| 12.6 | 7.02 | 13 |
| 15.7 | 5.63 | 16 |
| 16.2 | 5.48 | 98 |
| 17.3 | 5.11 | 13 |
| 18.9 | 4.68 | 100 |
| 19.2 | 4.61 | 75 |
| 20.2 | 4.39 | 86 |
| 21.6 | 4.11 | 27 |
| 23.6 | 3.77 | 9 |
| 24.9 | 3.57 | 86 |
| 25.8 | 3.45 | 38 |
| 27.8 | 3.21 | 21 |
| 29.2 | 3.06 | 9 |
| 33.0 | 2.71 | 13 |
| 33.0 | 2.71 | 13 |
| 36.2 | 2.48 | 10 |
| 37.4 | 2.40 | 19 |
| 39.3 | 2.29 | 12 |
| 41.2 | 2.19 | 14 |
| 43.7 | 2.07 | 8 |

Example 10: Polymorph Screen of Tabernanthalog Sorbate

| Abbreviations | |
|---|---|
| Å | Unit of atomic measurement (0.1 nm) |
| φ$_i$ | Water activity coefficient |
| a$_w$ | Water activity |
| ASD | Amorphous solid dispersion |
| ca. | circa (Latin: approximately) |
| cf. | Confer/conferatur (Latin: to confer, to compare) |
| ° C. | degree Celsius |
| CP | Chemical Purity |
| CP-MAS | Cross Polarised Magic Angle Spinning ($^{13}$C NMR solid state technique) |
| Da | Dalton |
| DSC | Differential Scanning Calorimetry (measures changes in heat capacity) |
| DTA | Differential Thermal Analyses (measures changes in temperature) |
| DVS | Dynamic Vapour Sorption (used interchangeably with GVS) |
| e.g. | Exempli gratia (Latin: for example) |
| etc. | Et cetera (Latin: 'and others' or 'and so on') |
| FaSSIF | Fasted State Simulated Intestinal Fluid |
| FaSSGF | Fasted State Simulated Gastric Fluid |
| FeSSIF | Fed State Simulated Intestinal Fluid |
| FT-IR | Fourier Transformed, InfraRed spectroscopy (prefixed mid and far) |
| g | Gram (s) |
| GRAS | Generally Recognised As Safe |
| GVS | Gravimetric Vapour Sorption |
| h | Hour (s) |
| HPLC | High Performance Liquid Chromatography |
| HSM | Hot Stage Microscopy (thermal microscopy) |
| HUCD | Heat-up/cool-down crystallisation |
| i.e. | Id Est (Latin: that is) |
| IR | InfraRed Spectroscopy |
| J | Joule |
| Kelvin | Kelvin. SI unit of temperature, used interchangeably with ° C. to express increment/decrement of temperature set point change (e.g., ramp rate on DSC thermogram 10 K/min); note K sign not prefixed by degree sign. |
| KF | Karl Fischer aquametry (determination of the water content by coulometric titration) |
| kg | Kilogram (s) |
| LOD | Loss On Drying |
| mag. | magnification |
| mAu | milli-Absorption units (chromatographic unit of peak height) |
| mAu*s | milli-Absorption units swept across by second (chromatographic unit of peak area) |
| MET/CR | Aptuit chromatography method reference |
| min | Minute (s) |
| mg | Milligram (s) |
| ml | Milliliter (s); liter (l) is not a capital noun; however, it is sometimes denoted as L (mL) |
| mol | mole, amount of substance |
| N/A | Not Applicable |
| n.a. | not analysed |
| n.d. | not detected |
| nm | Nanometre ($10^{-9}$ m, 10 Å) |
| NMR | Nuclear Magnetic Resonance |
| oab | on anhydrous basis |

| Abbreviations | |
|---|---|
| osfb | on solvent free basis |
| oasfb | on anhydrous solvent free basis |
| pH | $-\log [H^+]$ or pH = $-\log a_{H}^+$ (assuming equivalent hydrogen ion activity) |
| $pK_a$ | $-\log (K_a)$, acid dissociation constant |
| pI | isoelectric point, quoted in unit pH |
| PLM | Polarised Light Microscopy |
| RelRT | Relative Retention Time (not be confused RT) |
| REP/ | Aptuit report (REP) reference |
| RFA | Request For Analysis (Aptuit unique reference number) |
| RH | Relative Humidity ($a_w$ * 100) |
| RT | Room Temperature (ambient, typically: 18 to 23° C.) |
| s | Second (s) |
| SC-XRD | Single Crystal X-Ray structure Determination |
| SMPT | Solvent-mediated phase transition |
| STA | Simultaneous Thermal Analysis (STA = TGA + DTA) |
| t | time in seconds, minutes, hour, days etc. (interval specified in parentheses); alias in common use tonne (t) |
| t | Tonne, metric unit of mass (1000 kg; 1 Mg), (compaction force in kg, suffixed in parentheses) |
| T | Temperature recorded in degrees Celsius (° C.); alias in common use, SI unit of magnetic flux density, also denoted T |
| MTBE | Methyl tert-butyl ether |
| TCNB | 2,3,5,6-Tetrachloronitrobenzene ($C_6HCl_4NO_2$, F.W. 260.89 gmol$^{-1}$) |
| TFE | Trifluoroethanol (solvent used for solvent drop grinding) |
| TGA | Thermogravimetric Analysis |
| th. | theoretical |
| UV | Ultraviolet |
| vol. | Volume or relative volume |
| vs. | versus |
| v/v | Volume/volume |
| W | Watt |
| w/w | Weight/weight |
| XRPD | X-Ray Powder Diffraction |

| DEFINITIONS | |
|---|---|
| Isostructural | Crystals are said to be isostructural if they have the same crystal structure but not necessarily the same cell dimensions nor the same chemical composition (Kálmán, A., Párkányi, L. & Argay, G. (1993) Acta Cryst. B49, 1039-1049.) |
| Isomorphic | two crystalline solids are isomorphous if both have the same unit-cell dimensions and space group (source, vide supra). |
| Isomorphic desolvate | via solvent release from an isostructural solvate. |
| Native | Refers to an API in its native or non-ionised form. |
| Normal light | Light oscillating in all directions perpendicular to the axis to which it travels. |
| Particle size | Expressed as a volume distribution, the range x10 > PSD < x90 captures the sizes of 80% of the particles. |
| Plane polarised light | Light passed through a polaroid filter which allows only light oscillating in one plane to be transmitted. |
| Polymorphism | Crystalline solid able to exhibit different crystalline phases. |
| Photomicrograph | Imaged captured of a small object under magnification through an optical microscope. |
| Pseudopolymorphism | Different crystal structure attributed to the incorporation of molecular water or solvent |
| Solvates | Contains a molecule of solvent in the crystal lattice. |
| Thermogram | Differential scanning calorimetry trace: heat flow on y-ordinate (mW), time (minutes)/temperature (° C.) on x-ordinate. |

Summary

Tabernanthalog sorbate salt, Form A crystallised as prisms from ethanol and was identified as the stable single polymorphic form, suitable for advanced phase development. The sorbate salt exhibited modest water affinity (ca. 1% w/w) up to 90% RH. Specimens were retrieved post DVS and analysed by XRPD at 0%, 80% and 90% RH and were consistent with Form A, indicating that the water uptake was predominantly, non-bonded: however, small shifts in d-spacings were evident and minimal hysteresis in the RH range between 70% to 80% RH, was observed.

Tabernanthalog sorbate salt crystal structure (Form A) was determined and the simulated powder pattern at 100 K, fully explained the experimentally observed powder pattern at 298 K. A hydrate form was also identified (refer to the SC-XRD section).

Tabernanthalog sorbate salt (Form A) was subjected to stability studies at 40° C., 75% RH (the experimental data are reported in Experiment 6 of Example 8.) and 20° C., 95% RH and was sampled at t=5 days and t=10 days. The analytical data collected from the experiment performed at 40° C., 75% RH showed that Form A was stable as the powder diffraction patterns matched the diffractogram of the input material, $^1$H NMR analysis confirmed that the molecular structure of the API was concordant with the input and thermal data did not exhibit any water absorption events. More importantly, trended HPLC data confirmed the lowest decrease in chemical purity compared to the rest of the salts. The stability study at 20° C., 95% RH showed that Tabernanthalog sorbate salt (Form A) converted to Form C (Pattern #2) after 5 days in the open vial and after 10 days in the double-bagged vial. Thermal analysis suggested that Form C (Pattern #2) was likely to be a weakly crystal-bonded hydrate and DVS data obtained from 0% to 90% to 0% RH confirmed this statement as Form C (Pattern #2) reverted to Form A on the desorption cycle (0% to 90 RH). The NMR data collected agreed with the molecular structure of the input.

Solubility assessment of Tabernanthalog sorbate salt (Form A) in SIF buffers was, as part of the physicochemical evaluation of the salt, which showed that it was readily soluble in FaSSIF and FeSSIF during 24 h, and only exhibited disproportionation after 24 h in FaSSGF (the experimental data are reported in Experiment 5 of Example 8). Sorbic acid is a monobasic acid counter ion and therefore cannot undergo re-proportionation In conjunction with Form A, Tabernanthalog sorbate salt presented in 3 different forms. Form B (refer to Table 261A). We believe that Form B and Form C are labile, crystal-bonded hydrates; the TG weight loss transitions were under unity and suggested that regions of disorder were present in the bulk phases.

A. Introduction

Tabernanthalog sorbate salt was nominated as the preferred salt version and this section summarises the data collected from the polymorph screen, that was performed on tabernanthalog sorbate salt.

B. Project Design

The polymorph screen included the following activities:

Scale-up of tabernanthalog sorbate salt to ca. 5 g.

Full characterisation of the scaled-up batch, including Q $^1$H NMR, XRPD, TGA, DSC, PLM and SC-XRD.

Qualitative solubility investigation against 22 solvents (selected from Classes 1 and 2 ICH Q3C (R8) Residual solvents, 20/05/21).

Suspension equilibration panels in selected solvents at 20° C., and 40° C.

Heat-up/cool-down crystallisations in selected solvents.

Determination of the relative stability of the identified forms via competitive suspension equilibration; or if not possible, this was inferred from the outcome of superficial drying activities.

Evaluation of chemical and physical stability of the selected form at 20° C./95% RH (for 40° C./95% RH, refer to Example 8)

DVS, investigations of the stable form and phase analyses of residues acquired specific % RH set-points.

The objective of the polymorph screen was to identify a stable, anhydrous monotropic polymorph, that was judged suitable for advanced phase development. The preferred form was tabernanthalog sorbate salt (Form A).

C. Results and Discussion

This section details the work plan that was undertaken to examine the polymorph screen of tabernanthalog sorbate salt.

1. Tables of Characterisation

The characterisation of the tabernanthalog sorbate salt is summarized in Tables 259-261.

TABLE 259

Tabernanthalog sorbate salt (Form A).

| Provenances of reference batches | Tabernanthalog sorbate salt (Form A) |
|---|---|
| Experiment 1-Sample A2: crystallised from ethanol. The product was isolated by suction filtration and dried under steady nitrogen flux for ca 3 h; the filter cake (5.2 g, 0.2% w/w ethanol) was off-loaded from the filtration apparatus, trayed-up and dried under reduced pressure at 40° C. for ca. 18 h. Experiment 13-Sample C1: | Reference batches: Experiment 1-Sample A2, Experiment 13-Sample C1, Experiment 11-Sample A1<br>Molecular weight: 342.44 gmol$^{-1}$<br>Exact molecular weight: 342.1943<br>Molecular formula: $C_{20}H_{26}N_2O_3$<br>Unary/mono sorbate: 24.7% w/w th., sorbic acid (i.e., 1.0 mol of API to 1.0 mol sorbic acid).<br>SCXRD: Unary/mono sorbate. The simulated powder pattern, predicted from single crystal structure at 100K agreed with the experimentally observed Form A powder pattern obtained at 298K (refer to the SC-XRPD section).<br>Nature of hydrogen bonding: Hydrogen bonding between both oxygen molecules on the sorbate ion. One to N1 (tryptamine nitrogen atom) of one API molecules, the other to N2 (hydro-azepine nitrogen atom) of a separate API molecule. Due to hydrogen bonding present in the structure builds up chains between API and salt molecule. Causing stacking of API and sorbate molecules closely packed to one another. This leads to less free space in the crystal structure and void radius of only~0.9 A, much smaller than the 1.4 required for a water molecule to occupy. Bond between Sorbates and API, N1—O3, 2.857 Å (hydrogen bond), N2—O2, 2.7015 Å (salification hydrogen bond)<br>N1 = Indole, N2 = Hydroazepine.<br>Sorbate molecule is disordered and bond lengths stated are an average of the two mapped positions.<br>Crystal system 100(2) K: monoclinic |

TABLE 259-continued

| Tabernanthalog sorbate salt (Form A). | |
|---|---|
| Provenances of reference batches | Tabernanthalog sorbate salt (Form A) |
| | Space group 100(2) K: P2$_1$/c<br>Unit cell 100(2) K: a = 9.3410(3) Å, b = 6.4173(2) Å, c = 30.5108(12) Å.<br>A = γ = 90° β = 95.374(3)°, V = 1820.90(11) Å3.<br>Asymmetric unit: contains one API molecule one sorbate ion.<br>XRPD: 5.7°, 11.4°, 22.8° (Experiment 1-Sample A2, refer to FIG. 564 and Table 273).<br>DSC: onset 140.03° C. (−106.66 Jg$^{-1}$, endotherm, melt) (Experiment 1-Sample A2, refer to Section D.1).<br>TGA: onset 177.6° C. (−36.4% w/w, ablation) 263.5° C. (−59% w/w, ablation) (Experiment 1-Sample A2, refer to Section D.1).<br>DVS 0 to 90 to 0% RH (dm/dt < 0.002%): 0.0 (0.00%), 5.0 (0.0%), 10.0 (0.01%), 15.0 (0.01%), 20.0 (0.02%), 25.0 (0.03%), 30.0 (0.03%), 40.0 (0.05%), 50.0 (0.07%), 60.0 (0.10%), 70.0 (0.14%), 80.0 (0.21%), 90.0 (0.98%), 90.0 (0.98%), 80.0 (0.48%), 70.0 (0.30%), 60.0 (0.18%), 50.0 (0.06%), 40.0 (0.03%), 30.0 (0.00%), 25.0 (0.00%), 20.0 (0.02%), 15.0 (0.03%), 10.0 (0.04%), 5.0 (0.05%), 0.0 (0.06%) (Experiment 1-Sample A2, refer to Section D.1).<br>UV chromatographic purity: 99.64% area (212 nm), (Experiment 1-Sample A2, refer to section D. 1)<br>$^1$H NMR: (DMSO-d$_6$, 400 MHZ); δ 10.5 (s, 1H), 7.2 (d, J = 8.56 Hz, 1H), 7.1 (dd, J = 15.2, 15.3 Hz, 1H), 6.7 (d, J = 1.9 Hz, 1H), 6.6 (dd, J = 8.56, 2.2 Hz, 1H), 6.2 (d, m, 2H), 5.8 (d, J = 15.0 Hz, 1H), 3.7 (s, 3H), 2.8 (m, 2H), 2.7 (m, 6H), 2.4 (s, 3H), 1.8 (d, J = 5.8 Hz, 3H) ppm; conforms to the molecular structure (Σ25H; this event was observed when sample was re-prepared for TGA analysis after 7 days (refer to FIG. 564)), (Experiment 1-Sample A2, refer to D.1)<br>Residual solvents ICH Q3C (R8): Experiment 1-Sample A2 (ethanol 0.1% w/w, ICH listed 5000 ppm)<br>Q $^1$H NMR: 99.9% w/w (Experiment 1-Sample A2, refer to Section D.1)<br>Appearance: refer to section G.1 (Experiment 13-Sample C1). |

TABLE 260

| Tabernanthalog sorbate salt (Form B, Pattern #1). | |
|---|---|
| Provenances of reference batches | Tabernanthalog sorbate salt (Form B, Pattern #1) |
| Experiment 2-Sample S1: crystallised from water<br><br>Experiment 6-Sample A1: crystallised from methanol/water (2/1, v/v) via evaporation<br><br>Experiment 12-Sample A2: | Reference batches: Experiment 2-Sample S1, Experiment 6-Sample A1 and Experiment 12-Sample A2.<br>Molecular weight: 342.44 gmol$^{-1}$<br>Exact molecular weight: 342.1943<br>Molecular formula: C$_{20}$H$_{26}$N$_2$O$_3$<br>Unary/mono salt: (i.e., 1.0 mol of API to 1.0 mol sorbic acid).<br>XRPD: 7.5°, 15.1° (Experiment 2-Sample S1, refer to SectionD.2)<br>DSC: onset 48.4° C. (−231.36 Jg$^{-1}$, endotherm, dehydration), 69.9° C. (−160.38 Jg$^{-1}$, endotherm, dehydration), 144.6° C. (−102.24 Jg$^{-1}$, endotherm, melt) (Experiment 6-Sample A1, refer to sectionD.2).<br>TGA: onset 54.8° C. (−1.37% w/w, dehydration; this event was observed when sample was re-prepared for TGA analysis after 7 days (refer to FIG. 564) 164.37° C. (−29.24% w/w, ablation) (Experiment 6-Sample A1, refer to section D.2)<br>$^1$H NMR: (DMSO-d$_6$, 400 MHZ); δ 10.3 (s, 1H), 7.2 (d, J = 8.56 Hz, 1H), 7.1 (ddd, J = 15.2, 15.3, 0.56 Hz, 1H), 6.7 (d, J = 2.24 Hz, 1H), 6.6 (dd, J = 8.54, 2.33 Hz, 1H), 6.2 (d, m, 2H), 5.8 (d, J = 15.32 Hz, 1H), 3.7 (s, 3H), 2.8 (m, 2H), 2.7 (m, 6H), 2.4 (s, 3H), 1.8 (d, J = 5.96 Hz, 3H) ppm; conforms to the molecular structure (Σ25H; the molecular formula (C$_{20}$H$_{26}$N$_2$O$_3$) includes the |

TABLE 260-continued

Tabernanthalog sorbate salt (Form B, Pattern #1).

| | |
|---|---|
| Provenances of reference batches | Tabernanthalog sorbate salt (Form B, Pattern #1) |
| | carboxylic acid proton however, it co-resonates with water), (Experiment 6-Sample A1, refer to section D.2)<br>Residual solvents ICH Q3C (R8): Experiment 6-Sample A1: Methanol not detected<br>Appearance: refer to Section D.2 (Experiment 12-Sample A2). |

TABLE 261

Tabernanthalog sorbate salt (Form C, Pattern #2).

| | |
|---|---|
| Provenances of reference batches | Tabernanthalog sorbate salt (Form C, Pattern #2) |
| Experiment 3-Sample R1: crystallised from water<br><br>Sample A2: material from stability at 95% RH | Reference batches: Experiment 3-Sample R1 and Experiment 10-Sample A2<br>Molecular weight: 342.44 gmol$^{-1}$<br>Exact molecular weight: 342.1943<br>Molecular formula: $C_{20}H_{26}N_2O_3$<br>Unary/mono salt: (i.e., 1.0 mol of API to 1.0 mol sorbic acid)<br>Experiment 10-<br>XRPD: 5.7°, 11.1°, 11.5°, 13.9°, 16.7°, 17.3°, 17.8°, 18.5°, 18.7°, 20.1°, 22.4°, 29.7° (Experiment 10-Sample A2) (refer to Section D.3)<br>DSC: onset 76.6° C. (−99.32 Jg$^{-1}$, endotherm), 145.1° C. (−95.88 Jg$^{-1}$, endotherm) (Experiment 10-Sample A2), (refer to section D.3).<br>TGA: onset 71.6° C. (−4.4% w/w, dehydration), 168.7° C. (−27.9% w/w, ablation), (Experiment 10-Sample A2), (refer to section D.3)<br>UV chromatographic purity: 99.69% area (212 nm), (Experiment 10-Sample A2), (refer to section D.3)<br>$^1$H NMR: (DMSO-d$_6$, 400 MHz); δ 10.3 (s, 1H), 7.2 (d, J = 8.6 Hz, 1 H), 7.1 (ddd, J = 15.3, 14.8, 0.56 Hz, 1H), 6.7 (d, J = 2.2 Hz, 1H), 6.6 (dd, J = 10.8, 6.2 Hz, 1H), 6.2 (m, 2H), 5.8 (d, J = 15.3 Hz, 1H), 3.7 (s, 3H), 2.9 (m, 2H), 2.7 (m, 6H), 2.4 (s, 3H), 1.8 (d, J = 5.9 Hz, 3H) ppm; conforms to the molecular structure (Σ25H; the molecular formula ($C_{20}H_{26}N_2O_3$) includes the carboxylic acid proton however, it co-resonates with water), (Experiment 10-Sample A2), (refer to section D.3)<br>Residual solvents ICH Q3C (R8): Experiment 10-Sample A2: Methanol not detected<br>Appearance: refer to section D.3 (Experiment 10-Sample A2 and Experiment 3-Sample R1) |

2. Polymorph Screen

The summary of the Forms is provided in Table 261A.

Table 261A. Form Summary Table

| Designation | Solvent | DSC | | | | TGA | | ¹H NMR | | | Assignment | SCXRD | Attempt to re-prepare and result |
|---|---|---|---|---|---|---|---|---|---|---|---|---|---|
| | | Profile | Event | Thermal measurements | | % Δwt. | Comment | ¹H NMR (stoichiometry) | ¹H NMR (solvent) | | | | |
| Form A | Crystallisation from ethanol | [profile] | Single melt event | Integral | -106.66 Jg^-1 | Onset of ablation 178 °C | Flat baseline, pre-melt (anhydrous) | 1 to 1 (API to sorbate) | Q ¹H NMR (99.9% w/w), ethanol (0.1% w/w); HPLC: 99.64% area | Form A | -076-A1 (SC-XRD, collection completed, refinement in progress) | --- |
| | | | | Onset | 140.03 °C | | | | | | | | |
| | | | | Peak | 142.50 °C | | | | | | | | |
| | | | | Endset | 144.06 °C | | | | | | | | |
| PATTERN #1 | S1: water A1: methanol / water 060: methanol / water evaporation | [profile] | Hydrate-multiple events; thermally reverted to Form A | Integral | -102.24 Jg^-1 | -078-A2: -3.0% w/w, onset 58.4 °C (cf. unary hydrate 5.0% w/w) | Flat baseline, pre-melt (anhydrous) | 1 to 1 (API to sorbate) | -064-A1: methanol | Form B (judged to be metastable crystal bonded hydrate) | -078-A2 (unit cell: 10.86 12.2 15.1 90 109 90) | -078-A2: Converted into Form C |
| | | | | Onset | 144.61 °C | | | | | | | | |
| | | | | Peak | 147.33 °C | | | | | | | | |
| | | | | Endset | 149.58 °C | | | | | | | | |
| PATTERN #2 | Water, 95% RH | [profile] | Hydrate, thermally reverted to Form A | Integral | -95.88 Jg^-1 | -4.4% w/w, onset 71.6 °C (cf. unary hydrate 5.0% w/w) | Onset of ablation 169 °C | 1 to 1 (API to sorbate) | -072-A2: ethanol | Form C (crystal bonded hydrate) | -052-R1 (unit cell: 10.85, 12.14, 16.07, 90, 109.24) | SCXRD obtained on sample -78-A2 |
| | | | | Onset | 145.12 °C | | | | | | | | |
| | | | | Peak | 148.17 °C | | | | | | | | |
| | | | | Endset | 149.84 °C | | | | | | | | |
| PATTERN #4 | 056: water, 6 d @ 40 °C 060: HUCD in acetone water | --- | --- | --- | --- | --- | --- | --- | --- | PATTERN #4 | -056-R1 (unit cell: 10.86 12.2 15.1 90 109 90) | Targeted Pattern #4, resulted in Pattern #2 (Form C) |
| PATTERN #5 (partially amorphous, v. disordered) | Dichloromethane, 6 d @ 40 °C | --- | --- | --- | --- | --- | --- | --- | --- | PATTERN #5 | --- | Resulted in v. disordered Pattern #5; too sticky for companion analyses |
| PATTERN #6 | Crystallised from ethyl formate / heptane | --- | --- | --- | --- | --- | --- | --- | --- | PATTERN #6 | Converted into Form A | Targeted Pattern #6, resulted in Form A |
| PATTERN #3 (mixture of Form A, Pattern #1 and Pattern #6) | Ethyl formate, 6 d @ 40 °C | [profile] | --- | --- | --- | --- | --- | --- | --- | Pattern #3 | Converted into Form A | |

Qualitative Solubility Screen (Experiment Reference: 2)

For experimental procedure refer to Section F.2. The characterization data reported here are for Pattern #1 (Form B, Experiment 2-Sample S1, refer to Section D.2), as the rest of the pellets resembled Form A by XRPD (refer to Table 263).

Note: For this experiment a scale up of the Tabernanthalog sorbate salt was performed. For experimental procedure refer to Section F.6 and for experimental characterization data refer to Section D.1. The product (Experiment 1-Sample A2, Form A, 5.05 g, 87% uncorr. yield) was analysed by DSC, TGA, $^1$H NMR, XRPD, KF (0.12% w/w water content) and PLM. All the analysis results were congruent with the reference pattern (Experiment 13-Sample C1, Form A).

The qualitative solubility screen was carried out to determine the range of solvents incorporated into future suspension equilibration panels. Products that crystallised were centrifuged and analysed as wet pellet by XRPD, dried under reduced pressure and re-analysed by XRPD, with selected samples further analysed by TGA and $^1$H NMR spectroscopy.

Apart from minor strain effects, the products were consistent with the input phase (Form A), indicating that the sorbate salt is predominantly monomorphic (the preferred result); however, a metastable phase was detected as wet pellet, from water, this reverted to Form A, when dried (entry-S1), yet contained a low-level transition, by TGA.

Based on the finds from this evaluation, two panels of suspension equilibration of Tabernanthalog sorbate salt were performed at 20 and 40° C. against 22 solvents, including the aqueous systems. The solubility screen of tabernanthalog sorbate is provided in Table 262 and the summary of the results is provided in Table 263.

TABLE 262

Solubility screen of Tabernanthalog sorbate.

| Reference | Solvent | ICH Class | 5 vol Solution at 20° C. | 5 vol Solution at 40° C. | 5 vol reflux | 5 vol Solid on cooling | 10 vol Solution at 20° C. | 10 vol Solution at 40° C. | 10 vol reflux | 10 vol Solid on cooling | 15 vol Solution at 20° C. | 15 vol Solution at 40° C. | 15 vol reflux | 15 vol Solid on cooling | 20 vol Solution at 20° C. | 20 vol Solution at 40° C. | 20 vol reflux | 20 vol Solid on cooling |
|---|---|---|---|---|---|---|---|---|---|---|---|---|---|---|---|---|---|---|
| Experiment 2-Sample -A1 | Acetone | 3 | x | x | x | ✓ | x | x | ✓ | ✓ | x | x | ✓ | ✓ | x | x | ✓ | ✓ |
| Experiment 2-Sample -B1 | MeCN | 2 | x | x | ✓ | ✓ | x | x | ✓ | ✓ | x | x | ✓ | ✓ | x | x | ✓ | ✓ |
| Experiment 2-Sample -C1 | TBME | 3 | x | x | x | ✓ | x | x | ✓ | ✓ | x | x | x | ✓ | x | x | x | ✓ |
| Experiment 2-Sample -D1 | Chlorobenzene | 2 | x | x | ✓ | ✓ | x | x | ✓ | ✓ | x | x | ✓ | ✓ | x | x | ✓ | ✓ |
| Experiment 2-Sample -E1 | DCM | 2 | x | x | ✓ | ✓ | x | ✓ | ✓ | ✓ | x | ✓ | ✓ | ✓ | | | | |
| Experiment 2-Sample -F1 | EtOH | 3 | x | x | ✓ | ✓ | x | ✓ | ✓ | ✓ | x | ✓ | ✓ | ✓ | | | | |
| Experiment 2-Sample -G1 | EtOAc | 3 | x | x | ✓ | ✓ | x | x | ✓ | ✓ | x | x | ✓ | ✓ | x | x | ✓ | ✓ |
| Experiment 2-Sample -H1 | Ethyl formate | 3 | x | x | ✓ | ✓ | x | x | ✓ | ✓ | x | x | ✓ | ✓ | x | x | ✓ | ✓ |
| Experiment 2-Sample -I1 | Heptane | 3 | x | x | x | ✓ | x | x | Oiled | | | | | | | | | |
| Experiment 2-Sample -J1 | Isopropyl acetate | 3 | x | x | ✓ | ✓ | x | x | ✓ | ✓ | x | x | ✓ | ✓ | x | x | ✓ | ✓ |
| Experiment 2-Sample -K1 | MeOH | 2 | ✓ | | x | | | | | | | | | | | | | |
| Experiment 2-Sample -L1 | Methyl acetate | 3 | x | x | ✓ | ✓ | x | x | ✓ | ✓ | x | x | ✓ | ✓ | x | x | ✓ | ✓ |
| Experiment 2-Sample -M1 | MEK | 3 | x | x | ✓ | ✓ | x | x | ✓ | ✓ | x | x | ✓ | ✓ | x | x | ✓ | ✓ |
| Experiment 2-Sample -N1 | MeTHF | # | x | x | ✓ | ✓ | x | x | ✓ | ✓ | x | x | ✓ | ✓ | x | ✓ | ✓ | ✓ |
| Experiment 2-Sample -O1 | Nitromethane | 2 | x | x | ✓ | ✓ | x | x | ✓ | ✓ | x | x | ✓ | ✓ | x | x | ✓ | ✓ |
| Experiment 2-Sample -P1 | 2-Propanol | 3 | x | x | ✓ | ✓ | x | x | ✓ | ✓ | x | x | ✓ | ✓ | | | | |
| Experiment 2-Sample -Q1 | THF | 2 | x | x | ✓ | ✓ | x | x | ✓ | ✓ | x | x | ✓ | ✓ | x | x | ✓ | ✓ |
| Experiment 2-Sample -R1 | Toluene | 2 | x | x | ✓ | ✓ | x | x | ✓ | ✓ | x | x | ✓ | ✓ | x | x | ✓ | ✓ |
| A1270-048-S1 | Water | # | x | x | ✓ | ✓ | | | | | | | | | | | | |
| Experiment 2-Sample -T1 | Acetone/Water (5% v/v, 0.5 aw) | 2 | x | ✓ | ✓ | ✓ | | | | | | | | | | | | |
| Experiment 2-Sample -U1 | Ethanol/Water (15% v/v, 0.5 aw) | 2 | ✓ | | | | | | | | | | | | | | | |
| A Experiment 2-Sample -V1 | Isopropanol / Water (12%, v/v, 0.5 aw) | 2 | x | ✓ | | | | | | | | | | | | | | |

TABLE 262-continued

Solubility screen of Tabernanthalog sorbate.

| Reference | Solvent | ICH Class | 5 vol Solution at 20° C. | 5 vol Solution at 40° C. | 5 vol reflux | 5 vol Solid on cooling | 10 vol Solution at 20° C. | 10 vol Solution at 40° C. | 10 vol reflux | 10 vol Solid on cooling | 15 vol Solution at 20° C. | 15 vol Solution at 40° C. | 15 vol reflux | 15 vol Solid on cooling | 20 vol Solution at 20° C. | 20 vol Solution at 40° C. | 20 vol reflux | 20 vol Solid on cooling |
|---|---|---|---|---|---|---|---|---|---|---|---|---|---|---|---|---|---|---|
| Experiment 2-Sample A1 | Acetone | 3 | × | × | × | ✓ | × | × | ✓ | ✓ | × | × | ✓ | ✓ | × | × | ✓ | ✓ |
| Experiment 2-Sample B1 | MeCN | 2 | × | × | ✓ | ✓ | × | × | ✓ | ✓ | × | × | ✓ | ✓ | × | × | ✓ | ✓ |
| Experiment 2-Sample C1 | TBME | 3 | × | × | × | ✓ | × | × | ✓ | ✓ | × | × | × | ✓ | × | × | × | |
| Experiment 2-Sample D1 | Chlorobenzene | 2 | × | × | ✓ | ✓ | × | × | ✓ | ✓ | × | × | ✓ | ✓ | × | × | ✓ | ✓ |
| Experiment 2-Sample E1 | DCM | 2 | × | × | ✓ | ✓ | × | ✓ | ✓ | ✓ | × | ✓ | ✓ | | | | | |
| Experiment 2-Sample F1 | EtOH | 3 | × | × | ✓ | ✓ | × | ✓ | ✓ | ✓ | × | ✓ | | | | | | |
| Experiment 2-Sample G1 | EtOAc | 3 | × | × | ✓ | ✓ | × | × | ✓ | ✓ | × | × | ✓ | ✓ | × | × | ✓ | ✓ |
| Experiment 2-Sample H1 | Ethyl formate | 3 | × | × | ✓ | ✓ | × | × | ✓ | ✓ | × | × | ✓ | ✓ | × | × | ✓ | ✓ |
| Experiment 2-Sample I1 | Heptane | 3 | × | × | × | ✓ | × | × | Oiled | | | | | | | | | |
| Experiment 2-Sample J1 | Isopropyl acetate | 3 | × | × | ✓ | ✓ | × | × | ✓ | ✓ | × | × | ✓ | ✓ | × | × | ✓ | ✓ |
| Experiment 2-Sample K1 | MeOH | 2 | ✓ | ✓ | ✓ | × | | | | | | | | | | | | |
| Experiment 2-Sample L1 | Methyl acetate | 3 | × | × | ✓ | ✓ | × | × | ✓ | ✓ | × | × | ✓ | ✓ | × | × | ✓ | ✓ |
| Experiment 2-Sample M1 | MEK | 3 | × | × | ✓ | ✓ | × | × | ✓ | ✓ | × | × | ✓ | ✓ | × | × | ✓ | ✓ |
| Experiment 2-Sample N1 | MeTHF | # | × | × | ✓ | ✓ | × | × | ✓ | ✓ | × | × | ✓ | ✓ | × | × | ✓ | ✓ |
| Experiment 2-Sample O1 | Nitromethane | 2 | × | × | ✓ | ✓ | × | × | ✓ | ✓ | × | × | ✓ | ✓ | × | × | ✓ | ✓ |
| Experiment 2-Sample P1 | 2-Propanol | 3 | × | × | ✓ | ✓ | × | × | ✓ | ✓ | | | | | | | | |
| Experiment 2-Sample Q1 | THF | 2 | × | × | ✓ | ✓ | × | × | ✓ | ✓ | × | × | ✓ | ✓ | × | × | ✓ | ✓ |
| Experiment 2-Sample R1 | Toluene | 2 | × | × | ✓ | ✓ | × | × | ✓ | ✓ | × | × | ✓ | ✓ | × | × | ✓ | ✓ |
| Experiment 2-Sample S1 | Water | # | × | × | ✓ | ✓ | × | × | ✓ | ✓ | | | | | | | | |
| Experiment 2-Sample T1 | Acetone/Water (5% v/v, 0.5 aw) | 2 | × | ✓ | ✓ | ✓ | | | | | | | | | | | | |
| Experiment 2-Sample U1 | Ethanol/Water (15% v/v, 0.5 aw) | 2 | ✓ | ✓ | | | | | | | | | | | | | | |
| Experiment 2-Sample V1 | Isopropanol / Water (12%, v/v, 0.5 aw) | 2 | × | ✓ | | | | | | | | | | | | | | |

TABLE 263

Summary of results.

| Reference | Solvent | Assignment (wet pellet XRPD) | Assignment (dry pellet XRPD) | $^1$H NMR |
|---|---|---|---|---|
| Experiment 2-Sample A1 | Acetone | Form A (absent shoulder 22.82° 2θ) | Form A | — |
| Experiment 2-Sample B1 | MeCN | Form A (absent shoulder 18.77°, 22.82° 2θ) | Form A | — |
| Experiment 2-Sample C1 | TBME | Form A | Form A (shoulder 22.60° 2θ) | insufficient material |
| Experiment 2-Sample D1 | Chlorobenzene | Form A (absent shoulder 18.77° 2θ) | Form A (shoulder 22.62° 2θ) | — |
| Experiment 2-Sample E1 | DCM | Form A + split reflections 5.90°, 10.70°, 11.62°, 23.14° 2θ | Form A | — |
| Experiment 2-Sample F1 | EtOH | Insufficient material | — | — |
| Experiment 2-Sample G1 | EtOAc | Form A | Form A | — |
| Experiment 2-Sample H1 | Ethyl formate | Form A + new shoulders 18.72°, 23.01° 2θ | Form A + new shoulders 18.30°, 19.46°, 23.01° 2θ | insufficient material |
| Experiment 2-Sample I1 | Heptane | Oiled | — | — |
| Experiment 2-Sample J1 | Isopropyl acetate | Form A, some shift of d-spacings | Form A | — |
| Experiment 2-Sample K1 | MeOH | — | — | — |
| Experiment 2-Sample L1 | Methyl acetate | Form A | Form A | — |
| Experiment 2-Sample M1 | MEK | Form A + shoulder 22.89° 2 | Form A + new shoulder 11.61° 2θ | MEK n.d. |
| Experiment 2-Sample N1 | MeTHF | Form A + split reflections 5.87°, 11.56°, 2θ | Form A | — |
| Experiment 2-Sample O1 | Nitromethane | Form A + split reflections 17.97°, 2θ | Form A (strain 23.04° 2θ) | nitromethane n.d. |
| Experiment 2-Sample P1 | 2-Propanol | Form A | Form A | — |
| Experiment 2-Sample Q1 | THF | Form A + new shoulders 22.52° 2θ | Form A | — |
| Experiment 2-Sample R1 | Toluene | Form A | Form A (strain 14.63°, 24.62° 2θ) | — |
| Experiment 2-Sample S1 | Water | Pattern #1 | Converted into Form A | insufficient materiall for KF analysis |
| Reference | Solvent | Assignment (wet pellet XRPD) | Assignment (dry pellet XRPD) | 1H NMR |
| Experiment 2-Sample T1 | Acetone/Water (5% v/v, 0.5 aw) | Insufficient material | — | — |
| Experiment 2-Sample U1 | Ethanol/Water (15% v/v, 0.5 aw) | Insufficient material | — | — |
| Experiment 2-Sample V1 | Isopropanol / Water (12%, v/v, 0.5 aw) | Insufficient material | — | — |

$^1$H NMR spectroscopy was performed on selected samples to determine solvent content and confirm the chemical identity of the output (refer to FIG. 676, FIG. 677 and FIG. 678). The structure did not show any alterations/degradation on the selected batches. Solvents were not retained.

Suspension equilibration at 20 and 40° C. Experiment reference: 3 and 4 For experimental procedure refer to Section F.2. Suspension equilibration at 20° C. (A1270-052) delivered Pattern #2 (Form C, Experiment 3-Sample R1) as a new metastable form and the characterization data are reported in Section D.3. Suspension equilibration at 40° C. (A1270-056) gave Pattern #5 (Experiment 4-Sample E1, refer to Section D.6) and Pattern #3 (Experiment 4-Sample H1, refer to Section D.4) as new metastable forms. Pattern #4 is reported as experiment number Experiment 5-Sample R1 (refer to Section D.5).

Suspension equilibration is a thermodynamic dwelling technique, designed to promote the evolution of the API into a more stable phase. The purpose of this panel is to determine if Form A evolves into a supra-ordinate form. The companion panel at 40° C. set-point is in place to detect enantiotropic behaviour via different relative proportions in different solvents.

XRPD data of the moist pellets obtained from the suspension equilibration study at 20° C. (Experiment 3, refer to Table 264) were consistent with Form A, except from water which was different (refer to FIG. 679); however, upon oven drying, the phase reverted to Form A, indicating that Pattern #2 is almost certainly metastable with respect to Form A. Analyses of the rest of the dried pellets were consistent with the stable form (Form A).

TABLE 264

Suspension equilibration at 20° C.

| References | Input weight (mg) | Solvent (1 part, 5 vol total) | Key chemical functional groups | b.p. (° C.) | ICH Classes | Observations (t = 0 @ 20° C.) | Observations (t = 1 d @ 20° C.) | Observations (t = 10 d @ 20° C.) | XRPD (IPC, 6 d, wet) | XRPD (post oven dried) |
|---|---|---|---|---|---|---|---|---|---|---|
| Experiment 3-Sample A | 49.6 | Acetone | Symmetrical ketone | 56 | 3 | Suspension | Suspension | Suspension | Form A | Form A |
| Experiment 3-Sample B | 50.2 | Acetonitrile | Simple dipolar-aprotic nitrile | 82 | 2 | Suspension | Suspension | Suspension | Form A | Form A |

TABLE 264-continued

Suspension equilibration at 20° C.

| References | Input weight (mg) | Solvent (1 part, 5 vol total) | Key chemical functional groups | b.p. (° C.) | ICH Classes | Observations (t = 0 @ 20° C.) | Observations (t = 1 d @ 20° C.) | Observations (t = 10 d @ 20° C.) | XRPD (IPC, 6 d, wet) | XRPD (post oven dried) |
|---|---|---|---|---|---|---|---|---|---|---|
| Experiment 3-Sample C | 49.7 | tBME | Branched aliphatic methoxyether | 55 | 3 | Suspension | Suspension | Suspension | Form A | Form A |
| Experiment 3-Sample D | 49.8 | Chlorobenzene | Aromatic halide | 131 | 2 | Suspension | Suspension | Suspension | Form A | Form A |
| Experiment 3-Sample E | 49.7 | Dichloromethane | Chlorinated hydrocarbon | 40 | 2 | Suspension | Suspension | Suspension | Form A | Form A |
| Experiment 3-Sample F | 50.0 | Ethanol | Linear aliphatic alcohol | 78 | 3 | Suspension | Suspension | Suspension | Form A | Form A |
| Experiment 3-Sample G | 50.1 | Ethyl acetate | Aliphatic ester | 75 | 3 | Suspension | Suspension | Suspension | Form A | Form A |
| Experiment 3-Sample H | 50.4 | Ethyl formate | Aldehyde aliphatic ester | 54 | 3 | Suspension | Suspension | Suspension | Form A | Form A |
| Experiment 3-Sample I | 50.3 | Heptane | Linear alkane | 98 | 3 | Suspension | Suspension | Suspension | Form A | Form A |
| Experiment 3-Sample J | 50.1 | Isopropyl acetate | Branched aliphatic ester | 87 | 3 | Suspension | Suspension | Suspension | Form A | Form A |
| Experiment 3-Sample K | 49.5 | Methyl Acetate | Aliphatic ester | 57 | 3 | Suspension | Suspension | Suspension | Form A | Form A |
| Experiment 3-Sample L | 50.1 | MEK | Asymmetric dialkyl ketone | 80 | 3 | Suspension | Suspension | Suspension | Form A | Form A |
| Experiment 3-Sample M | 50.2 | 2-Methyl THF | Asymmetric cyclic ether | 80 | # | Suspension | Suspension | Suspension | Form A | Form A |
| Experiment 3-Sample N | 49.7 | Nitromethane | Dipolar aprotic nitro | 100 | 2 | Suspension | Suspension | Suspension | Form A | Form A |
| Experiment 3-Sample O | 50.0 | 2-Propanol | Branched aliphatic alcohol | 83 | 3 | Suspension | Suspension | Suspension | Form A | Form A |
| Experiment 3-Sample P | 50.2 | Tetrahydrofuran | Symmetric cyclic ether | 66 | 2 | Suspension | Suspension | Suspension | Form A | Form A |
| Experiment 3-Sample Q | 49.9 | Toluene | Alkyl aromatic hydrocarbon | 111 | 2 | Suspension | Suspension | Suspension | Form A | Form A |
| Experiment 3-Sample R | 50.3 | Water | Dihydrogen oxide | 100 | # | Suspension | Suspension | Suspension | Pattern #2 | Form A |
| Experiment 3-Sample S | 50.0 | Acetone/Water (10% v/v, 0.5 aw) | Symmetrical ketone/ Dihydrogen oxide | 56 | 3 | Solution | Solution | Feint suspension | — | — |
| Experiment 3-Sample T | 50.3 | Isopropanol / Water (12%, v/v, 0.5 aw) | Branched aliphatic alcohol/ Dihydrogen oxide | 83 | 3 | Solution | Solution | Solution | — | — |

TABLE 265

Suspension equilibration at 40° C.

| References | Input weight (mg) | Solvent (1 part, 5 vol total) | Key chemical functional groups | b.p. (° C.) | ICH Classes | Observations (t = 0 @ 40° C.) | Observations (t = 1 d @ 40° C.) | Observations (t = 10 d @ 40° C.) | XRPD (IPC, 6 d, wet) | XRPD (post oven dried) |
|---|---|---|---|---|---|---|---|---|---|---|
| Experiment 4-Sample A | 49.7 | Acetone | Symmetrical ketone | 56 | 3 | Suspension | Suspension | Suspension | Form A | Form A |
| Experiment 4-Sample B | 49.8 | Acetonitrile | Simple dipolar-aprotic nitrile | 82 | 2 | Suspension | Suspension | Suspension | Form A | Form A |
| Experiment 4-Sample C | 49.5 | tert-Butylmethyl ether | Branched aliphatic methoxyether | 55 | 3 | Suspension | Suspension | Suspension | Form A (disordered) | Form A |
| Experiment 4-Sample D | 49.5 | Chlorobenzene | Aromatic halide | 131 | 2 | Suspension | Suspension | Suspension | Form A | Form A |
| Experiment 4-Sample E | 49.8 | Dichloromethane | Chlorinated hydrocarbon | 40 | 2 | Partial | Solution | Beige suspension | Pattern #5 | Insuff. mat. |
| Experiment 4-Sample F | 50.3 | Ethanol | Linear aliphatic alcohol | 78 | 3 | Partial | Partial | Feint suspension | Form A | Form A |
| Experiment 4-Sample G | 50.2 | Ethyl acetate | Aliphatic ester | 75 | 3 | Suspension | Suspension | Suspension | Form A | Form A |
| Experiment 4-Sample H | 50.0 | Ethyl formate | Aldehyde aliphatic ester | 54 | 3 | Suspension | Suspension | Suspension | Pattern #3 | Form A |
| Experiment 4-Sample I | 50.3 | Heptane | Linear alkane | 98 | 3 | Suspension | Suspension | Suspension | Form A | Form A |
| Experiment 4-Sample J | 50.2 | Isopropyl acetate | Branched aliphatic ester | 87 | 3 | Suspension | Suspension | Suspension | Form A | Form A |

TABLE 265-continued

Suspension equilibration at 40° C.

| References | Input weight (mg) | Solvent (1 part, 5 vol total) | Key chemical functional groups | b.p. (° C.) | ICH Classes | Observations (t = 0 @ 40° C.) | Observations (t = 1 d @ 40° C.) | Observations (t = 10 d @ 40° C.) | XRPD (IPC, 6 d, wet) | XRPD (post oven dried) |
|---|---|---|---|---|---|---|---|---|---|---|
| Experiment 4-Sample K | 49.6 | Methyl Acetate | Aliphatic ester | 57 | 3 | Suspension | Suspension | Suspension | Form A | Form A |
| Experiment 4-Sample L | 50.3 | Methylethyl ketone | Asymmetric dialkyl ketone | 80 | 3 | Suspension | Suspension | Suspension | Form A | Form A |
| Experiment 4-Sample M | 5. | 2-Methyl THF | Asymmetric cyclic ether | 80 | # | Suspension | Suspension | Suspension | Form A | Form A |
| Experiment 4-Sample N | 49.9 | Nitromethane | Dipolar aprotic nitro | 100 | 2 | Suspension | Suspension | Suspension | Form A | Form A |
| Experiment 4-Sample O | 50.0 | 2-Propanol | Branched aliphatic alcohol | 83 | 3 | Suspension | Suspension | Suspension | Insuff. mat. | Insuff. mat. |
| Experiment 4-Sample P | 50.0 | Tetrahydrofuran | Symmetric cyclic ether | 66 | 2 | Suspension | Suspension | Suspension | Form A | Form A |
| Experiment 4-Sample Q | 50.3 | Toluene | Alkyl aromatic hydrocarbon | 111 | 2 | Suspension | Suspension | Suspension | Form A | Form A |
| Experiment 4-Sample R | 49.7 | Water | Dihydrogen oxide | 100 | # | Suspension | Suspension | Suspension | Pattern #4 | Form A |

XRPD analysis of several moist pellets obtained from the suspension equilibration experiment were inconsistent with Form A (refer to Table 265 and FIG. 680). Analyses of the dried pellets were consistent with the stable form (Form A).

Heat-Up/Cool-Down Crystallisations (HUCD) (Experiment 5)

For experimental procedure refer to Section F.2. The new metastable forms delivered are reported in Section D.5 (Experiment 5-Sample R1, Pattern #4) and Section D.7 (Experiment 5-Sample G1, Pattern #6).

Crystallisation from different solvents can be a useful method to investigate alternative polymorphic forms. Tabernanthalog sorbate salt (Experiment 1-Sample A2, Form A) was crystallised from the binary solvents tabulated in Table 266.

A number of metastable forms were identified, Pattern #1 (Experiment 5-Sample Q1), Pattern #4 (Experiment 5-Sample R1) and Pattern #6 (Experiment 5-Sample G1), all of which readily reverted to Form A, during oven drying.

TABLE 266

Heat-up/cool-down crystallisations results.

| References | Input referen | Input weights (mg) | Solvent A (3.0 vol) | Solvent B | Co-solvents (volumes added, μl) | Key chemical functional groups | b.p. (° C.) | ICH Classes | Observations (t = 1 @ T = 20° C.) | XRPD (centrifuged, wet) | XRPD (oven dried @ 40° C., 20 h) |
|---|---|---|---|---|---|---|---|---|---|---|---|
| Experiment 5-Sample A | Tabernanthalog sorbate salt | 74.7 | Heptane | Acetone | 1075 | Symmetrical ketone | 56 | 3 | Partial | Form A | Form A |
| Experiment 5-Sample B | | 75.2 | tBME | MeCN | 875 | Simple dipolar-aprotic nitrile | 82 | 2 | Solid | Form A | Form A |
| Experiment 5-Sample C | | 75.8 | Heptane | Chlorobenzene | 1150 | Aromatic halide | 131 | 2 | Solid | Form A | Form A |
| Experiment 5-Sample D | | 75.3 | Heptane | DCM | 1275 | Chlorinated hydrocarbon | 40 | 2 | Liquid | Form A | Form A |
| Experiment 5-Sample E | | 75.5 | Heptane | EtOH | 300 | Linear aliphatic alcohol | 78 | 3 | Partial | Form A | Form A |
| Experiment 5-Sample F | | 74.4 | Heptane | EtOAc | 1150 | Aliphatic ester | 75 | 3 | Partial | Form A | Form A |
| Experiment 5-Sample G | | 74.8 | Heptane | Ethyl formate | 1325 | Aldehyde aliphatic ester | 54 | 3 | Partial | Pattern #6 | Form A |
| Experiment 5-Sample H | | 74.4 | Heptane | Isopropyl acetate | 2150 | Branched aliphatic ester | 87 | 3 | Partial | Form A | Form A |
| Experiment 5-Sample I | | 74.7 | tBME | MeOH | 150 | Simple aliphatic alcohol | 65 | 2 | Liquid | Form A | Form A |
| Experiment 5-Sample J | | 74.8 | Heptane | Methyl acetate | 1475 | Aliphatic ester | 57 | 3 | Partial | Form A | Form A |
| Experiment 5-Sample K | | 75.4 | Heptane | MEK | 775 | Asymmetric dialkyl ketone | 80 | 3 | Partial | Form A | Form A |
| Experiment 5-Sample L | | 75.4 | Heptane | MeTHF | 1250 | Asymmetric cyclic ether | 80 | # | Partial | Form A | Form A |
| Experiment 5-Sample M | | 75.3 | Heptane | Nitromethane | 1000 | Dipolar aprotic nitro | 100 | 2 | Liquid | Form A | Form A |
| Experiment 5-Sample N | | 75.5 | Heptane | 2-Propanol | 575 | Branched aliphatic alcohol | 83 | 3 | Partial | Form A | Form A |
| Experiment 5-Sample O | | 75.4 | Heptane | THF | 650 | Symmetric cyclic ether | 66 | 2 | Liquid | Form A | Form A |
| Experiment 5-Sample P | | 74.5 | Heptane | Toluene | 3200 | Alkyl aromatic hydrocarbon | 111 | 2 | Partial | Form A | Form A |

TABLE 266-continued

Heat-up/cool-down crystallisations results.

| References | Input referen | Input weights (mg) | Solvent A (3.0 vol) | Solvent B | Co-solvents (volumes added, µl) | Key chemical functional groups | b.p. (° C.) | ICH Classes | Observations (t = 1 @ T = 20° C.) | XRPD (centrifuged, wet) | XRPD (oven dried @ 40 ° C., 20 h) |
|---|---|---|---|---|---|---|---|---|---|---|---|
| Experiment 5-Sample Q | | 75.5 | Water | — | | Water | 100 | # | Solid | Pattern #1 | Form A |
| Experiment 5-Sample R | | 74.3 | Acetone | Water | 25 | Water | 100 | # | Liquid | Pattern #4 | Form A |

Liquid Assisted (LAG) and Neat Pulverisation (Experiment 7)

(For experimental procedure refer to Section F.2 and for experimental characterization data that accompany this section refer to Sections H.1 and H.2).

The products from water (Experiment 7-Sample B) and neat (Experiment 7-Sample A) grinding were retrieved (a gum was obtained from TFE) and analysed by XRPD. The phase obtained from neat grinding was consistent with the input (Experiment 1-Sample A2, Form A, refer to FIG. 681), as no polymorphic changes was observed under these conditions. The phase delivered from the pulverisation in the presence of water (Experiment 7-Sample B) matched Pattern #2 (refer to FIG. 684). DSC analyses of both products agreed with the XRPD data.

Considering that the oscillations input a large amount of kinetic and mechanical energy, designed to promote chemical and physical change, the products were additionally analysed by $^1$H NMR spectroscopy (refer to FIG. FIG. 682 and FIG. 685). No significant chemical changes were observed.

The DSC profile of Experiment 7-Sample A neat is provided in FIG. 683 and the DSC profile of Experiment 7-Sample B water is provided in FIG. 686.

Binary Solvent Evaporation Crystallisation (Experiment 6)

(For experimental procedure refer to Section F.2 and for experimental characterization data that accompany this section refer to Section I.1).

Separate portions of Tabernanthalog sorbate salt (Experiment 1-Sample A2, Form A) were dissolved in a binary solvent mixture composed of methanol and water (Experiment 6-Sample A1), acetone (Experiment 6-Sample B1), acetonitrile (Experiment 6-Sample C1), THF (Experiment 6-Sample D1) and DCM (Experiment 6-Sample E1). Each vial was capped with aluminium foil, pierced, and allowed to stand undisturbed until the evaporation was completed.

The products were analysed by XRPD, and several differences were observed; some of which may be attributed to over emphasis of the reflection along a certain aspect, others may arise from different crystal structures. The product from methanol/water (Experiment 6-Sample A) was consistent with Pattern #1. $^1$H NMR spectroscopy was chemically indistinguishable from Tabernanthalog sorbate salt (Experiment 1-Sample A2, Form A) in the initial analysis (t=0). A different powder diffraction pattern is normally associated with crystal bonding; therefore Pattern #1 is assumed to be a hydrate.

Thermally promoted water-release caused facile re-organisation into the stable Form A while the transition enthalpy was not readily detected. A strong crystal bonded hydrate obliterates the crystal when de-hydrated, which is obvious by DSC, while dehydration of a solely channel or pocket hydrate affords an isomorphic de-hydrate, with little structural reorganisation (refer to Appendix #4, Section 1.4). Methanol was not detected by $^1$H NMR spectroscopy.

The binary solvent evaporation panel results are provided in Table 267 and the picture of Experiment 6-Sample A, B, C, D and E after 7 days is provided in FIG. 687.

TABLE 267

Binary solvent evaporation panel results.

| References | Input reference | Input weights (mg) | Solvent A (10 vol) | Solvent B (5 vol) | b.p. (° C.) | ICH Classes | Yield (%) | XRPD (dried under nitrogen) |
|---|---|---|---|---|---|---|---|---|
| Experiment 6-Sample A | Tabernanthalog Sorbate (EXPERIMENT 1-SAMPLE A2) | 49.7 | MeOH | Water | 100 | 3 | 101.0 | Pattern #1 |
| Experiment 6-Sample B | | 50.0 | MeOH | Acetone | 56 | 2 | 98.4 | Pattern #1 > Form A > unk |
| Experiment 6-Sample C | | 50.4 | MeOH | Acetonitrile | 8 | 2 | 96.0 | Form A |
| Experiment 6-Sample D | | 50.1 | MeOH | THF | 65 | 2 | 94.6 | Form A |
| Experiment 6-Sample E | | 50.3 | MeOH | DCM | 40 | 3 | 95.6 | Form A |

Powder pattern changed from Pattern #1 (Form B, refer to t=0, refer to FIG. 688) on standing (refer to t=8 days, refer to FIG. 691), into a form that resembled Form A, yet exhibited a small, sharp DSC endo. (Refer to 692), and coincident, small weight loss transition by TGA (FIG. 693), which is likely to be attributed to the incomplete equilibration of Pattern #1 into Form A.

The DSC profile of Experiment 6-Sample A1 T=0. Dehydration behaviour more consistent with channel or pocket hydration; no transition was evident into Form A is provided in FIG. 689. Overlaid of $^1$H NMR spectra of Tabernanthalog Sorbate at t=0: Experiment 6-Sample A 1 (via evaporation from water and consistent with pattern #1, Form B, blue) and Experiment 1-Sample A2 (Form A, red). DMSO-$d_6$ used as deuterated solvent is provided in FIG. 690.

A DSC sample of Experiment 6-Sample A1 (t=8 days, refer to the red diffraction pattern in FIG. FIG. 694) was heated to 80° C., cooled under nitrogen to 20° C., and the residue was analysed by XRPD (black powder pattern in FIG. FIG. 694) was congruent with Form A.

Experiment 6-Sample A1 (t=8 days) specimen is Form A>Pattern #1 (Form B), because the phase transition was under equilibration, and if left standing for an extended time, the mixed component would have wholly reverted to Form A.

DSC profile of Experiment 6-Sample A1 Rep. is provided in FIG. 695.

The best course of action was to definitively characterise the proposed hydrate (Pattern #1, Form B) via SCXRD, as this will enable us to confidently assign the mode of hydration The crystals from the binary solvent evaporation crystallisation experiment Experiment 6-Sample A1 were not suitable. Examination of previous crystals of Pattern #1 (Form B, Experiment 5-Sample Q2), obtained via heat-up/cool-down from water (refer to Section C.2) were judged to be small to sufficiently diffract; therefore, an attempt to re-grow and maintain the crystals water 'wetted', prior to the structure determination in Section C.2.

The PLM of Experiment 6-Sample A1 (normal polarisation, ×2 magn.) is provided in FIG. 696.

Reproducibility of HUCD Crystallisations

For experimental procedure refer to Section F.2.

Patterns #1 and 6 (Experiment 8)

(For experimental characterisation data that accompany this section refer to Sections H.3) Initial heat-up/cool-down crystallisations (Experiment 5) delivered Patterns #1 (Form B, water) and Pattern #6 (heptane/ethyl formate). The selected experiments were repeated to provide enough of these forms for full characterisation.

Oven-drying of the output was avoided as it previously promoted formation of Form A, therefore, isolation was performed via filtration through a Hirsch funnel. XRPD diffractograms of moist pellets (Experiment 8-Sample A1 and Experiment 8-Sample B1) were obtained 30 min after filtration. Samples were left to dry for ca. 2 h under $N_2$ flux at ambient temperature; however, Pattern #1 (Form B) was altered after drying (Experiment 8-Sample A2) and Pattern #6 Experiment 8-Sample), crystallised as Form A.

Experiment 8-Sample A2 (after drying under gentle nitrogen flux) was different from the target Pattern #1 (Form B) and Form A. Exhibited an only small weight loss of –0.5% w/w by TGA. Designated Pattern #7 (Form D). $^1$H NMR spectroscopy of Experiment 8-Sample A2 (Pattern #7) was a different chemical composition, attributed to reaction with ethyl formate. This occurred during the oven-drying process. Evaluated it for potential SC-XRD by PLM and were not suitable. The results are summarized in Table 268. The overlaid of $^1$H NMR spectra of Tabernanthalog Sorbate samples: Experiment 1-Sample A2 (Form A), Experiment 8-Sample A1 (wet pellet, Pattern #1, Form B), Experiment 8-Sample A2 (dried under $N_2$ purge, different from Pattern #1, Form B and Form A) and Experiment 5-Sample Q1 (Pattern #1, Form B crystallised from water) is provided in FIG. 697. The overlaid of $^1$H NMR spectra of Tabernanthalog Sorbate samples: Experiment 1-Sample A2 (Form A), Experiment 8-Sample B1 (wet pellet, Form A), Experiment 8-Sample B2 (dried under $N_2$ purge, Form A) and Experiment 5-Sample G1 (Pattern '#6, crystallised from EtOAc/heptane) is provided in FIG. 698.

TABLE 268

Summary of results.

| References | Input reference | Input weights (mg) | Solvent A (3.0 vol) | Solvent B | Co-solvents (volumes added, μl) | Yield % | Target form | XRPD (centrifuged, wet) | XRPD (under nitrogen flow) |
|---|---|---|---|---|---|---|---|---|---|
| Experiment 8-Sample A | EXPERIMENT 1-SAMPLE A2| | 74.7 | Water | — | 225 | 53.3 | Pattern #1 | Pattern #1 | Chemical composition altered |
| Experiment 8-Sample B | | 75.2 | Heptane | Ethyl formate | 1325 | 43.6 | Pattern #6 | Form A | Form A |

Patterns #2, #3, #4 and 75 (Experiment 9)

(For companion analytical data refer to Section D.1).

Suspension equilibration at 40° C. for 7 days was repeated, as these were the conditions used previously, aiming to generate #2 (water), #3 (ethyl formate), Pattern #4 (from water) and Pattern #5 (DCM) for TG analyses.

Preparation of Pattern #2 was successful; however, preparations of Pattern #3, Pattern #4 and Pattern #5 were not successful, giving instead Form A, Pattern #2 and a very disordered product, respectively. The summary of the results are provided in Table 269.

TABLE 269

Summary of results.

| References | Input reference | Input weight (mg) | Solvent (1 part, 5 vol total) | Observations (t = 0 @ 20° C.) | Observations (t = 1 d @ 20° C.) | Observations (t = 5 d @ 20° C.) | Target | XRPD (IPC, 5 d, wet) | XRPD (post Filter dried) | DSC (Jg^-1) | TGA (% w/w) | ¹H NMR (solvent content, % w/w) |
|---|---|---|---|---|---|---|---|---|---|---|---|---|
| Experiment 9-Sample A | Form A | 75.1 | Water | Suspension | Suspension | White suspension | Pattern #2 | Pattern #2 | Pattern #2 | Onset: 78.10° C. (−118.50) Onset: 144.81° C. (−113.28) | Onset: 70.18 ° C. (−2.5400) Onset: 88.73 ° C. −1.4218 % | ND |

| References | Input reference | Input weight (mg) | Solvent (1 part, 5 vol total) | Observations (t = 0 @ 40° C.) | Observations (t = 1 d @ 40° C.) | Observations (t = 5 d @ 40° C.) | Target | XRPD (IPC, 5 d, wet) | XRPD (post Filter dried) | DSC (Jg^-1) | TGA (% w/w) | ¹H NMR (solvent content, % w/w) |
|---|---|---|---|---|---|---|---|---|---|---|---|---|
| Experiment 9-Sample C | Form A | 75.2 | EtOAc | Suspension | Suspension | White suspension | Pattern #3 | Form A | Form A | — | — | — |
| Experiment 9-Sample B | | 74.8 | Water | Suspension | Suspension | Brown suspension | Pattern #4 | Pattern #2 | Pattern #2 | Onset: 54.68° C. (−4.68) Onset: 145.44° C. (−94.02) | Onset: 72.90° C. (−2.9321) Onset: 175.16° C. (−23.4734 %) | ND |
| Experiment 9-Sample D | | 75.0 | DCM | Suspension | Suspension | Beige suspension | Pattern #5 | Pattern #5 | v. Disordered Pattern #5 (d-spacings to higher angle) | insufficient material (gummy) | insufficient material (gummy) | insufficient material (gummy) |

Stability at 95% RH (KNO₃) at 20° C. (Experiment 10)

(For experimental data that accompany this section refer to refer to Section F.2 and for characterization data refer to Section 1.2).

Tabernanthalog sorbate salt Experiment 10-Sample A (open vial) and Experiment 10-Sample B (open vial, double-bagged in polyethene bags tied tightly with cable ties) were placed in the humidity chamber (FIG. 698A)

The samples were maintained under equilibrium humidity of 95% RH at 20° C., and monitored at 5 day by XRPD and 10 day time points by ¹H NMR, XRPD, DSC, TGA and PLM.

Form A converted to Pattern #2 after 5 days in the open vial (Experiment 10-Sample A1) and after 10 days in the closed vial (Experiment 10-Sample B2), for companion analytical data refer to Appendix #2 (refer to Section 1.2; absorbent was stable at 40° C./75% RH, 10 days (refer to Experiment 6 of Example 8). DVS is reproduced in Appendix #5 (refer to Section 1.5).

DVS Analyses of Form A (Performed on Batch Reference: Experiment 11-Sample-A1)

To determine whether Form A underwent form change at high % RH, DVS residues of Form A, from 0 to 80% RH and 0 to 90%6 RH, were examined. The specimens were equilibrated to constant mass, at 80% and 90% RH set-points, removed, placed in a capped vial, and analysed by XRPD and DSC. Based on the SC-XRD at 100 K, no regular voids in the crystal structure were large enough to accommodate non-crystal-bonded, molecular water with minimum probe radius of 1.4 Å.

DVS data of Experiment 1-Sample A2 is provided in FIG. 699.

DVS Analyses of Form A to 80% RH

The analytical data of the specimen that was retrieved from the experiment performed from 0 to 80% RH are reported in FIG. 700 (XRPD) and in FIG. 701 (DSC). The powder diffraction pattern post-DVS (black diffractogram) was consistent with Form A (red diffractogram). The m.p. of specimen at 80% RH was also consistent with Form A.

DVS Analyses of Form A to 90% RH

The powder diffraction pattern of the specimen retrieved at 90% RH matched the reference batch of Form A (refer to FIG. 702). Th DSC thermogram of the specimen was consistent with Form A (refer to FIG. 703).

Examination of Variability of Fusion Temperature

The factors that were assessed to explain the observed variability in fusion temperature found amongst Form A samples were sample loading, preferred orientation and particle size/homogeneity (Table 271). A weak relationship between sample loading and melt onset was observed, the remainder of the factors examined, appeared to be unrelated.

Samples from the evaporation panel exhibited over emphasis of reflections at 7.5°, 28.5° and 29.5° 2-theta (refer to FIG. 704, Experiment 6-Sample C1, -D1, E1). This property did not appear to be related to the variance in fusion temperature observed by DSC.

TABLE 271

Fusion temperature of various batches of Form A (25-220° C. at 10° C. min$^{-1}$).*

| Experiment | Sample size (mg) | Melt onset (° C.) | Peak (° C.) | Endset (° C.) | melt enthalpy (Jg$^{-1}$) |
|---|---|---|---|---|---|
| A1270-20-V2 | 4.2 | 143.9 | 148.8 | 152.0 | −84.1 |
| Experiment 13-Sample C1 | 2.5 | 139.9 | 142.5 | 144.5 | −105.8 |
| Experiment 1-Sample A2 | 3.4 | 140.0 | 142.5 | 144.1 | −106.7 |
| Experiment 6-Sample C1 | 5.5 | 144.7 | 148.8 | 151.0 | −100.5 |
| Experiment 6-Sample D1 | 3.5 | 144.0 | 148.0 | 150.2 | −105.7 |
| Experiment 6-Sample E1 | 4.3 | 145.0 | 148.8 | 151.6 | −105.7 |
| Experiment 7-Sample A neat | 2.4 | 144.4 | 146.8 | 148.5 | −122.5 |
| Experiment 7-Sample B water | 3.5 | 144.5 | 146.8 | 148.4 | −115.1 |
| Experiment 8-Sample B2 | 3.5 | 141.8 | 144.3 | 146.0 | −98.0 |
| Experiment 11-Sample A1 | 5.7 | 145.8 | 149.8 | 152.5 | −92.3 |
| Minimum | | 139.9 | 142.5 | 144.1 | −122.5 |
| Maximum | | 145.8 | 149.8 | 152.5 | −84.1 |
| Mean | | 143.4 | 146.7 | 148.9 | −103.4 |
| Standard Deviation | | 2.1 | 2.7 | 3.1 | 11.5 |
| Sample Variance | | 4.4 | 7.3 | 9.7 | 132.1 |

*The DSC data reported in Table 271 derived from samples that DSC analyses were collected for Form A. Table 272 includes all the samples that resembled Form A, for which DSC data were not collected for some of them.

SC-XRD

Form A

For experimental data that accompany this section refer to Section F.2 and for characterization data refer to Section 1.7.

Crystal Data for Experiment 11-Sample A1 (refer to FIG. 705). $C_{20}H_{26}N_2O_3$, $M_r$=342.43, monoclinic, P2$_1$/c (No. 14), a=9.3410(3) Å, b=6.4173(2) Å, c=30.5108(12) Å, b=95.374(3)°, a=g=90°, V=1820.90(11) Å$^3$, T=100(2) K, Z=4, Z'=1, m(Cu K$_a$)=0.675 mm$^{-1}$, 13832 reflections measured, 3694 unique (R$_{int}$=0.0462) which were used in all calculations. The final wR$_2$ was 0.2098 (all data) and R$_1$ was 0.0826 (I≥2 s(I)).

Th asymmetric structure contains one API molecule one sorbate ion. Hydrogen bonding takes place between both oxygen molecules on the sorbate ion (refer to FIG. 720). One to N1 (tryptamine nitrogen atom) of one API molecules, the other to N2 (hydro-azepine nitrogen atom) of a separate API molecule.

The hydrogen bonding network of Tabernanthalog sorbate salt (Experiment 1 I-Sample A1, Form A) is shown in FIG. 706 and FIG. 707.

Due to hydrogen bonding present in the structure builds up chains between API and salt molecule, which causes stacking of API and sorbate molecules closely packed to one another (refer to FIG. 707). This leads to less free space in the crystal structure and void radius of only ~0.9 A, much smaller than the 1.4 required for a water molecule to occupy. Hydrogen bond lengths between Sorbates and API are N1 (indole)-O3, 2.857 Å (hydrogen bond), N2 (hydroazepine)-O2, 2.7015 Å (salification hydrogen bond). Sorbate molecule is disordered, and bond lengths stated are an average of the two mapped positions (refer to FIG. 708).

The calculated powder diffraction pattern is depicted in FIG. 709. The comparison of the simulated and experimental powder diffraction pattern is depicted in FIG. 710.

Hydrate

Crystal Data of Experiment 12-Sample A2 (refer to FIG. 711). $C_{20}H_{28}N_2O_4$, $M_r$=360.44, monoclinic, P2$_1$/c (No. 14), a=16.07470(10) Å, b=12.14150(10) Å, c=10.85080(10) Å, b=109.2390(10)°, a=g=90°, V=1999.49(3) Å$^3$, T=100(2) K, Z=4, Z'=1, m(Cu K$_a$)=0.676 mm$^{-1}$, 51305 reflections measured, 3786 unique (R$_{int}$=0.0483) which were used in all calculations. The final wR$_2$ was 0.0874 (all data) and R1 was 0.0347 (I≥2 s(I)).

Unit cell contains t API, 1 sorbate, 1 water molecule (refer to FIG. 712) with same space group setting P2$_1$/C as Form A. Hydrogen bonding takes place between water molecule, API and sorbates (refer to FIG. 713). Salification of the API occurs at N2 (refer to FIG. 714).

Void space analysis, maximum void radius=0.98 Å, much smaller than 1.4 Å required for another water molecule to be present (refer to FIG. 715). Change in packing compared to Form A due to the hydrogen bonding from the water molecule (refer to FIG. 716). Powder pattern of Experiment 12-Sample A2 contained a mixture of patterns, and overlap is observed between simulated powder pattern (refer to FIG. 717 and FIG. 718).

D. Summary of Forms

1. Tabernanthalog Sorbate Salt Form A (Experiment 1-Sample A2)

TABLE 272

List of experiments that resulted in Form A.
Form A

| | | |
|---|---|---|
| Experiment 1-Sample A2 | Experiment 2-Sample J1 | Experiment 4-Sample F2 |
| Experiment 6-Sample D1 | Experiment 2-Sample H1 | Experiment 4-Sample L2 |
| Experiment 6-Sample A1 | Experiment 2-Sample M2 | Experiment 4-Sample Q1 |
| Experiment 6-Sample E1 | Experiment 2-Sample Q1 | Experiment 5-Sample A1 |
| Experiment 3-Sample I1 | Experiment 3-Sample L1 | Experiment 5-Sample B1 |
| Experiment 4-Sample N1 | Experiment 3-Sample P1 | Experiment 5-Sample B2 |
| Experiment 6-Sample C1 | Experiment 3-Sample N1 | Experiment 5-Sample E2 |
| Experiment 6-Sample B1 | Experiment 3-Sample Q1 | Experiment 5-Sample F2 |
| Experiment 2-Sample A2 | Experiment 4-Sample G1 | Experiment 5-Sample H2 |
| Experiment 2-Sample A2 | Experiment 4-Sample F1 | Experiment 5-Sample J2 |
| Experiment 2-Sample B2 | Experiment 4-Sample M1 | Experiment 5-Sample K2 |
| Experiment 2-Sample C1 | Experiment 4-Sample L1 | Experiment 5-Sample P1 |
| Experiment 2-Sample C2 | Experiment 4-Sample P1 | Experiment 5-Sample J1 |
| Experiment 2-Sample D2 | Experiment 4-Sample J1 | Experiment 5-Sample C1 |
| Experiment 2-Sample G2 | Experiment 4-Sample A1 | Experiment 5-Sample A2 |
| Experiment 2-Sample J2 | Experiment 4-Sample B1 | Experiment 5-Sample C2 |
| Experiment 2-Sample N1 | Experiment 4-Sample K1 | Experiment 5-Sample I2 |
| Experiment 2-Sample N2 | Experiment 4-Sample M2 | Experiment 5-Sample L2 |
| Experiment 2-Sample Q2 | Experiment 4-Sample N2 | Experiment 5-Sample P2 |
| Experiment 2-Sample R1 | Experiment 4-Sample P2 | Experiment 5-Sample D2 |
| Experiment 2-Sample R2 | Experiment 4-Sample Q2 | Experiment 8-Sample B2 |

TABLE 272-continued

List of experiments that resulted in Form A.
Form A

| Experiment 2-Sample S2 | Experiment 4-Sample A2. | Experiment 9-Sample C1 |
|---|---|---|
| Experiment 2-Sample E1 | Experiment 4-Sample B2. | Experiment 10-Sample B1 (5days) |
| Experiment 2-Sample E2 | Experiment 4-Sample J2 | Experiment 11-Sample A1 |
| Experiment 2-Sample D1 | Experiment 4-Sample K2 | Experiment 13-Sample C1 |
| Experiment 2-Sample P1 | Experiment 4-Sample G2 | |
| Experiment 2-Sample P2 | Experiment 4-Sample 02 | |

The $^1$H NMR spectrum of Experiment 1-Sample A2 in DMSO-$d_6$ used as deuterated solvent is provided in FIG. 719, The Q NMR assay of Experiment 1-Sample A2 in DMSO-$d_6$ used as deuterated solvent. 99.9% w/w assay is provided in FIG. 720. The overlay of $^1$H NMR spectra of Experiment 1-Sample A2 (red) and Experiment 13-Sample C1 (reference pattern, black) is provided in FIG. 409, The DSC profile of Experiment 1-Sample A2 is provided in FIG. 563. The overlay of DSC profiles of Experiment 1-Sample A2 (black) and Experiment 13-Sample C1 (reference pattern, red) is provided in FIG. 410.

The TGA profile of Experiment 1-Sample A2 is provided in 564. The overlaid of TGA profiles of Experiment d-Sample A2 (black) and Experiment 13-Sample C (reference pattern, red) is provided in FIG. 411.

The HPLC profile of Experiment 1-Sample A2 is provided in FIG. 566. The polarised light microscopy (PLM) of Experiment 1-Sample A2 is provided in FIGS. 567-570.

The XRPD profile of Experiment 1-Sample A2 is provided in FIG. 564.

TABLE 273

Peak angle data of Experiment 1-Sample A2.
Reported only peaks > 10%.
Rel. Intensity values calculated based on Net. Intensity values.

| 2-θ (°) | d Value | Rel. Intensity (%) |
|---|---|---|
| 5.7 | 15.53 | 100 |
| 11.4 | 7.75 | 40 |
| 22.8 | 3.89 | 11 |

The overlaid of XRPD profiles of Experiment 1-Sample A2 (black) and Experiment 13-Sample C1 (reference pattern, red) is provided in FIG. 412. The DVS Experiment 1-Sample A2, kinetic plot and isotherm analysis report is provided in FIG. 455. The DVS Experiment 1-Sample A2, isothermal plot is provided in FIG. 455.

The XRPD profile of Experiment 1-Sample A2_post DVS is provided in FIG. 458 and Table 274.

TABLE 274

Peak angle data of Experiment 1-Sample A2-post DVS. Reported only peaks >10%. Rel. Intensity values calculated based on Net. Intensity values.

| 2-θ (°) | d Value | Rel. Intensity (%) |
|---|---|---|
| 5.7 | 15.37 | 100 |
| 10.6 | 8.36 | 15 |
| 11.5 | 7.70 | 41 |

TABLE 274-continued

Peak angle data of Experiment 1-Sample A2-post DVS. Reported only peaks >10%. Rel. Intensity values calculated based on Net. Intensity values.

| 2-θ (°) | d Value | Rel. Intensity (%) |
|---|---|---|
| 18.9 | 4.68 | 22 |
| 22.8 | 3.90 | 17 |
| 24.5 | 3.63 | 12 |
| 24.7 | 3.60 | 23 |

2. Tabernanthalog Sorbate Salt Form B (Pattern #1, Experiment 2-Sample S1, A270-060-Q1, Experiment 6-Sample A1, Experiment 8-Sample A1 Experiment 12-Sample A2)

A list of experiments that resulted in Form B (Pattern #1) is provided in Table 275. The characterization is provided in FIGS. 721-728A and Tables 276 and 277.

TABLE 275

List of experiments that resulted in Form B (Pattern #1).
Form B (PATTERN #1)

Experiment 2-Sample S1
Experiment 6-Sample A1
Experiment 8-Sample A1
Experiment 5-Sample Q1
Experiment 12-Sample A2

TABLE 276

Peak angle data of Experiment 2-Sample S1. Reported only peaks >10%. Rel. Intensity values calculated based on Net. Intensity values.

| 2-θ (°) | d Value | Rel. Intensity (%) |
|---|---|---|
| 7.5 | 11.73 | 100 |
| 15.1 | 5.85 | 15 |

TABLE 277

Peak angle data of Experiment 6-Sample A1. Reported only peaks >10%. Rel. Intensity values calculated based on Net. Intensity values.

| 2-θ (°) | d Value | Rel. Intensity (%) |
|---|---|---|
| 7.6 | 11.7 | 100 |
| 15.1 | 5.85 | 13 |

3. Tabernanthalog Sorbate Salt Form C (Pattern #2, Experiment 3-Sample R1 and Experiment 10-Sample A2)

The list of experiments that resulted in Form C (Pattern #2) is provided in Table 278. The characterization is provided in FIGS. 729-736 and Tables 279 and 280.

TABLE 278

List of experiments that resulted in Form C (Pattern #2).
Form C (Pattern #2)

Experiment 3-Sample R1
Experiment 9-Sample A1
Experiment 10-Sample A1 (5 days)

TABLE 278-continued

List of experiments that resulted in Form C (Pattern #2).
Form C (Pattern #2)

Experiment 10-Sample A2
Experiment 10-Sample B2
Experiment 9-Sample A2
Experiment 9-Sample B2
Experiment 7-Sample B (water)
Experiment 9-Sample B1

TABLE 279

Peak angle data of Experiment 3-Sample R1. Reported only peaks >10%.
Rel. Intensity values calculated based on Net. Intensity values.

| 2-θ (°) | d Value | Rel. Intensity (%) |
|---|---|---|
| 5.7 | 15.37 | 100 |
| 11.5 | 7.67 | 24 |

TABLE 280

Peak angle data of Experiment 10-Sample A2. Reported only peaks >10%. Rel. Intensity values calculated based on Net. Intensity values.

| 2-θ (°) | d Value | Rel. Intensity (%) |
|---|---|---|
| 5.7 | 15.41 | 100 |
| 11.2 | 7.90 | 14 |
| 11.5 | 7.68 | 28 |
| 13.9 | 6.35 | 11 |
| 16.7 | 5.30 | 28 |
| 17.3 | 5.11 | 28 |
| 17.8 | 4.99 | 19 |
| 18.5 | 4.80 | 21 |
| 18.7 | 4.74 | 21 |
| 20.1 | 4.41 | 12 |
| 22.4 | 3.96 | 95 |
| 29.7 | 3.01 | 10 |

4. Tabernanthalog Sorbate Salt Pattern #3
(Experiment 4-Sample H1)

The list of experiments that resulted in Pattern #3 (mixture of Form A, Pattern #1 and Pattern #6) is provided in Table 281. The characterization is provided in FIG. 737 and Table 282.

TABLE 281

List of experiments that resulted in Pattern #3 (mixture of Form A, Pattern #1 and Pattern #6).
Pattern #3

Experiment 4-Sample H1

TABLE 282

Peak angle data of Experiment 4-Sample H1. Reported only peaks >10%.
Rel. Intensity values calculated based on Net. Intensity values.

| 2-θ (°) | d Value | Rel. Intensity (%) |
|---|---|---|
| 5.7 | 15.36 | 100 |
| 5.7 | 15.59 | 79 |
| 7.3 | 12.18 | 98 |
| 7.4 | 11.87 | 36 |
| 9.5 | 9.35 | 13 |
| 10.6 | 8.33 | 19 |

TABLE 282-continued

Peak angle data of Experiment 4-Sample H1. Reported only peaks >10%.
Rel. Intensity values calculated based on Net. Intensity values.

| 2-θ (°) | d Value | Rel. Intensity (%) |
|---|---|---|
| 11.5 | 7.70 | 60 |
| 11.5 | 7.71 | 73 |
| 14.5 | 6.10 | 15 |
| 18.9 | 4.68 | 53 |
| 22.8 | 3.89 | 13 |
| 23.0 | 3.86 | 24 |
| 24.7 | 3.60 | 25 |
| 24.8 | 3.59 | 28 |
| 27.0 | 3.30 | 10 |
| 29.3 | 3.04 | 10 |
| 29.7 | 3.00 | 15 |

5. Tabernanthalog Sorbate Salt Pattern #4
(Experiment 5-Sample R1)

The list of experiments that resulted in Pattern #4 is provided in Table 283. The characterization is provided in FIG. 738 and Table 284.

TABLE 283

List of experiments that resulted in Pattern #4.
Pattern #4

Experiment 5-Sample R1

TABLE 284

Peak angle data of Experiment 5-Sample R1. Reported only peaks >10%.
Rel. Intensity values calculated based on Net. Intensity values.

| 2-θ (°) | d Value | Rel. Intensity (%) |
|---|---|---|
| 5.9 | 14.90 | 100 |
| 5.8 | 15.10 | 51 |
| 11.3 | 7.83 | 14 |
| 11.6 | 7.60 | 17 |
| 16.8 | 5.27 | 23 |
| 17.5 | 5.08 | 17 |
| 17.9 | 4.96 | 16 |
| 18.6 | 4.78 | 20 |
| 18.8 | 4.72 | 17 |
| 20.2 | 4.38 | 10 |
| 22.5 | 3.94 | 66 |

6. Tabernanthalog Sorbate Salt Pattern #5
(Experiment 4-Sample E1)

The list of experiments that resulted in Pattern #5 is provided in Table 285. The characterization is provided in FIG. 739 and Table 286.

TABLE 285

List of experiments that resulted in Pattern #5.
Pattern #5

Experiment 4-Sample E1

TABLE 286

Peak angle data of Experiment 4-Sample E1. Reported only peaks >10%.
Rel. Intensity values calculated based on Net. Intensity values.

| 2-θ (°) | d Value | Rel. Intensity (%) |
|---|---|---|
| 7.7 | 11.53 | 34 |
| 8.4 | 10.46 | 12 |
| 10.9 | 8.10 | 11 |
| 12.5 | 7.05 | 13 |
| 14.1 | 6.28 | 100 |
| 14.7 | 6.01 | 13 |
| 15.4 | 5.75 | 30 |
| 15.7 | 5.65 | 12 |
| 16.5 | 5.37 | 78 |
| 17.9 | 4.96 | 13 |
| 18.3 | 4.85 | 39 |
| 18.6 | 4.77 | 13 |
| 19.2 | 4.61 | 33 |
| 19.9 | 4.46 | 14 |
| 20.5 | 4.34 | 62 |
| 20.8 | 4.26 | 51 |
| 21.2 | 4.19 | 42 |
| 21.8 | 4.07 | 12 |
| 22.9 | 3.88 | 21 |
| 23.2 | 3.82 | 37 |
| 24.3 | 3.66 | 25 |
| 25.4 | 3.50 | 16 |
| 26.2 | 3.39 | 15 |
| 27.4 | 3.25 | 40 |
| 28.5 | 3.13 | 14 |
| 28.7 | 3.10 | 18 |
| 29.8 | 3.00 | 13 |
| 31.1 | 2.88 | 18 |
| 31.7 | 2.82 | 11 |
| 32.5 | 2.75 | 11 |
| 32.6 | 2.75 | 13 |

7. Tabernanthalog Sorbate Salt Pattern #6 (Experiment 5-Sample G1)

The list of experiments that resulted in Pattern #6 is provided in Table 287. The characterization is provided in FIG. 740 and Table 288.

TABLE 287

List of experiments that resulted in Pattern #6.
Pattern #6

Experiment 5-Sample G1

TABLE 288

Peak angle data of Experiment 5-Sample G1. Reported only peaks >10%.
Rel. Intensity values calculated based on Net. Intensity values.

| 2-θ (°) | d Value | Rel. Intensity (%) |
|---|---|---|
| 5.7 | 15.46 | 10 |
| 7.2 | 12.19 | 100 |

E. Conclusions

SCXRD data for Tabernanthalog sorbate salt (Experiment 11-Sample A1, Form A, anhydrous) were obtained, as well as for Tabernanthalog sorbate salt·$H_2O$ (Experiment 12-Sample A2, mainly Pattern #1, assigned Form B, metastable hydrate, unique XRPD, evolves into Form C, enriched specimen with the crystallographer.

The metastable forms identified during the polymorph screen were:
  Experiment 10-Sample A2 (Pattern #2, assigned Form C, unary hydrate); assumed to be crystal bonded, unique XRPD, not isomorphic with Form A, specimen.
  Experiment 4-Sample E1 (Pattern #3) converted into Form A.
  Experiment 4-Sample R1 (Pattern #4) converted into Form A and was not suitable for SC-XRD.
  Experiment 4-Sample E1 (Pattern #5) converted into Form A.
  Experiment 5-Sample G1 (Pattern #6) converted into Form A.

The metastable forms were obtained via suspension equilibration or HUCD and the wet pellet, readily underwent conversion into Form A during drying.

Tabernanthalog sorbate salt (Form A) was subjected to 20° C./95% RH, where it was converted to Pattern #2 after 5 days in the open vial (Experiment 10-Sample A1) and after 10 days in the closed vial (Experiment 10-Sample B2).

F. Experimental

1. Instrumentation

DSC

A Mettler Toledo DSC 3 instrument was used for the thermal analysis operating with STARe™ software. The analysis was conducted in open aluminium pans (40 μl), under nitrogen and sample sizes ranged from 1 to 10 mg. Typical analysis method was 20 to 250° C. at 10° C./minute. Alternatively, a Mettler Toledo DSC1 with auto-sampler instrument was used for the thermal analysis operating with STARe™ software. The analysis was conducted in open aluminium pans (40 μl), under nitrogen and sample sizes ranged from 1 to 10 mg. Typical analysis method was 25 to 300° C. at 10° C./minute.

DVS

The moisture sorption properties of the feed API were analysed by DVS Intrinsic instrument (Surface Measurement System). Approximately 20 to 50 mg of API was weighed onto an aluminium pan and loaded into the instrument equilibrated at 25° C. The sample was equilibrated under a dry atmosphere (0% relative humidity) for 60 minutes, before increasing the humidity from 0% to 30% at 5% step increment and from 30% to 90% at 10% step increment. A desorption cycle was also applied from 90% to 30% (10% step decrement) and from 30% to 0% (5% step decrement). A rate of change in mass per time unit (dm/dt) of 0.002%/min was set as the equilibrium parameter. Kinetic and isotherm graphs were calculated.

LC-MS

Routine Liquid Chromatography-Mass Spectrometry (LC-MS) data were collected using the Agilent 1260 Infinity II interfaced with 1260 Infinity II DAD HS and Agilent series 1260 Infinity II binary pump.

The instrument used a single quadrupole InfinityLab MSD. The instrument was calibrated up to 2000 Da.

LC-MS Method Parameters:
  Inj. vol: 5 μl
  Detection: UV @ 254 nm
  Mobile Phase A: Acetonitrile+0.1% TFA/$H_2O$ 95:5
  Mobile Phase B: Acetonitrile±0.05% TFA/$H_2O$ 5:95

| Time (min) | % A | % B |
|---|---|---|
| 0.0 | 100 | 0 |
| 1 | 100 | 0 |
| 10.00 | 0 | 100 |
| 10.01 | 100 | 0 |
| 12.00 | 100 | 0 |

Flow Rate: 1 ml/min
Column temperature: 30° C.
Run time 12 minutes.

FT-IR

FT-IR Spectra were acquired using a PerkinElmer Frontier FT-IR spectrometer. Samples were analysed directly using a universal ATR attachment in the mid and far frequency ranges; 4000 to 30 cm$^{-1}$. Spectra were processed using Spectrum software. Standard KBr windows are used for mid-IR applications; polyethylene and polyethylene/diamond windows are used for operation in the far-IR. Further capabilities of the instrument include a liquid flow cell with ZnSe windows used for rapid monitoring of reactions. This couples with time-based software which allows time-resolved measurements to be taken.

$^1$H NMR $^1$H NMR spectra were acquired using a Bruker 400 MHz spectrometer and data was processed using Topspin. Samples were prepared in DMSO-d$_6$ at typical concentrations of 10 to 20 mg/ml and up to 50 mg/ml for $^1$H NMR w/w assay and calibrated to the corresponding non-deuterated solvent residual at 2.50 ppm.

$^1$H NMR assay

Assays (w/w) of API by $^1$H NMR spectroscopy were measured by the project chemist using Topspin. Internal standard 2,3,5,6-terachloronitrobenzene (TCNB, ca. 20 mg, F.W. 260.89) were dissolved in DMSO-d$_6$ (2.0 ml) and the $^1$H NMR spectrum was acquired using an extended relaxation method.

HPLC (MET/CR/2616)

HPLC data was acquired using an Agilent HPLC instrument. Samples were diluted to 1 mg/mL concentration in H$_2$O/DMSO (1/1, v/v).

Method Parameters:
Column: Halo C18, 150×4.6 mm, 2.77 m
Inj. volume: 5 □L
Detection: UV @ 212 nm
Mobile Phase A: 0.1% TFA in water/acetonitrile 95/5 v/v
Mobile Phase B: 0.05% TFA in water/acetonitrile 5/95 v/v

| Time (min) | % A | % B |
|---|---|---|
| 0.0 | 100 | 0 |
| 2.0 | 100 | 0 |
| 25.0 | 50 | 50 |
| 30.0 | 0 | 100 |
| 32.0 | 0 | 100 |
| 32.1 | 100 | 0 |
| 37.0 | 100 | 0 |

Flow rate: 1 mL/min
Column temperature: 30° C.
Run time: 37 minutes
Integration time: 32 minutes
Wash vial or syringe wash: Sample diluent Crystal 16 Apparatus A Technobis instrument that is used to program heat up and cooled down ramps at specific rates, whilst measuring the transmissivity of the contents of the vials. The response is reported in % and denotes the clear and cloud points at specific concentrations. The instrument offers 4 chambers where 4 vials can be placed.

TGA

A Mettler Toledo TGA-2 instrument was used to measure the weight loss as a function of temperature from 25 to 500° C. The scan rate was typically 5 or 10° C. per minute. Experiments and analysis were carried out using the STARe™ software. The analysis was conducted in 100 μl open aluminium pans, under nitrogen and sample sizes ranged from 1 to 10 mg.

XRPD

X-ray powder diffraction (XRPD) analysis was carried out using a Bruker D2 Phaser powder diffractometer equipped with a LynxEye detector. The specimens underwent minimum preparation but, if necessary, were lightly milled in a pestle and mortar before acquisition. The specimens were located at the centre of a silicon sample holder within a 5 mm pocket (ca. 5 to 10 mg). The samples were continuously spun during data collection and scanned using a step size of 0.02 °2-theta (2θ) between the range of 4° to 40° 2-theta or 5° to 60° 2-theta. Data were acquired using either 3 minute or 10-minute acquisition methods. Bruker Diffrac.Suite was used to process the data.

2. General procedures

Preparation of Form A

Experimental Reference: Experiment 1-Sample A2

Tabernanthalog (native) (3.87 g, 1.0 wt) and sorbic acid (2.07 g, 0.53 wt, 1.1 equiv) were dissolved in ethanol (11 ml, 3.0 vol) at 85 to 90° C. The clear brown solution was left to cool down to ambient (solid was observed) before standing undisturbed under sub-ambient conditions for ca 18 h. The product was isolated by filtration, de-liquored and left to pull dry under steady nitrogen flux for ca. 3 h. No wash cycle was applied. The product was off-loaded from the filtration assembly and was oven-dried under vacuum at 40° C. for ca 18 h to afford Experiment 1-Sample A2 (5.05 g, 87% uncorr. yield, 0.2% w/w ethanol).

Preparation of Form B (Form B (Pattern #1) was initially observed in the qualitatively solubility study (Experiment 2-Sample S1))

Experimental Reference: Experiment 5-Sample Q1 and Experiment 8-Sample A1 (HUCD)

Tabernanthalog sorbate salt (1.0 wt, Experiment 1-Sample A2, Form A) was weighed out in a vial and water (3.0 vol) was charged and warmed to temperature. The clear solution was left to cool down and stand undisturbed under sub-ambient conditions for several days. After crystallisation was judged complete, the product was isolated by centrifugation and the pellet was analysed by XRPD, which matched Form B (Pattern #1, Experiment 5-Sample Q1). The phase of the wet filter cake was consistent with Form B (Pattern #1, Experiment 8-Sample A1)

Experimental Reference: Experiment 6-Sample A1 (Binary Solvent Evaporation Crystallisation)

Tabernanthalog sorbate salt (ca. 50 mg, 1.0 wt, Experiment 1-Sample A2, Form A) was dissolved in a binary solvent mixture composed of methanol (500 μl) and water (250 µl). The vial was capped with aluminium foil, pierced, and allowed to stand undisturbed until the evaporation is completed.

Preparation of Form C

Experimental Reference: Experiment 3-Sample R1 and Experiment 9-Sample A1 and -A2 (Suspension Equilibration at 20° C.)

Tabernanthalog sorbate salt (1.0 wt, Experiment 1-Sample A2, Form A) was charged to a vial and water (5 vol) was subsequently added. The suspension was stirred at 20° C. for 6 days, prior to isolating the product by centrifugation (Experiment 3-Sample R1). XRPD analysis of the wet pellet showed conversion from Form A to Pattern #2. The latter phase did not revert to Form A upon drying on the filter (Experiment 9-Sample A2).

Experimental Reference: Experiment 9-Sample B1 and -B2 (Suspension Equilibration at 40° C.)

Tabernanthalog sorbate salt (1.0 wt, Experiment 1-Sample A2, Form A) was charged to a vial and water (5 vol) was subsequently added. The suspension was stirred at 40° C. for 5 days, prior to isolating the product by filtration. XRPD analysis of the wet and dried filter cake confirmed the conversion of Form A to Pattern #2.

Experimental reference: Experiment 10-Sample A1 (-A2) and Experiment 10-Sample B2 (Stability at 95% RH ($KNO_3$) at 20° C.)

Tabernanthalog sorbate salt (ca. 100 mg, 1.0 wt, Experiment 1-Sample A2, Form A) was weighed out in an open-capped vial and was placed inside a humidity chamber at 95% RH at 20° C. At t=5 d, Form A converted to Pattern #2.

Tabernanthalog sorbate salt (ca. 100 mg, 1.0 wt, Experiment 1-Sample A2, Form A) was weighed out in an open-capped vial, which was subsequently double-bagged in polyethene bags tied tightly with cable ties and was placed inside a humidity chamber at 95% RH at 20° C. At t=10 d, Form A converted to Pattern #2.

Experimental Reference: Experiment 7-Sample B (LAG in Water)

Tabernanthalog sorbate salt (50 mg, Experiment 1-Sample A2, Form A) was pulverised in the presence of water (25 µl, η=0.5), a single 7 mm steel bead was added to the reactor, after which they were sealed, and oscillated for 30 minutes at 8.0 Hz (ca. 500 rpm).

Qualitative Solubility Screen (Experiment 2)

Tabernanthalog sorbate salt (Experiment 1-Sample A2, Form A, 25 mg, 1 wt) was weighed out in 22 separate vials to qualitatively examine the solubility in an array of diverse solvents. The solubility was tested initially at 5 vol at 20° C., 40° C., and reflux. If insoluble at 5 vol, the solvent quantity was increased to 10 vol, 15 vol and 20 vol of the respective solvent. The suspensions that occurred upon cooling down were centrifuged and the solvent wet pellets were analysed by XRPD. The insoluble suspensions were additionally worked up for XRPD analysis. The resultant powder patterns were subsequently cross-referenced against the input supplied material.

Suspension Equilibration (Experiments 3 and 4)

Portions of Tabernanthalog sorbate salt (50 mg, 1.0 wt, Experiment 1-Sample A2, Form A) were charged to separate vials. The relevant solvent (5 vol) was added to the appropriate vial and the suspensions were stirred and warmed to the predetermined temperature with stirring. Once equilibration was completed (10 days at 20° C.), stirring was suspended and the products were isolated by centrifugation, wet and dried (at 40° C. under reduced pressure) pellets were analysed by XRPD.

Heat-Up/Cool-Down Crystallisation Screen (Experiment 5)

Portions of Tabernanthalog sorbate salt (ca 75 mg, 1.0 wt, Experiment 1-Sample A2, Form A) were charged to separate vials. The relevant solvent (0.225 ml, 3.0 vol) was added to the appropriate vial and the suspensions were stirred and warmed to temperature. If dissolution was not observed, further solvent was added until the solute dissolved, or aliquots of a secondary co-solvent were added to complete dissolution. Once dissolved, the solutions were left to cool down and stand undisturbed under sub-ambient conditions for several days. After crystallisation was judged complete, the products were isolated by centrifugation and the pellets were dried at 40° C. under reduced pressure. Products from the crystallisation (wet and dry) were initially analysed by XRPD (9-minute method), further analyses of certain products were performed by $^1$H NMR, DSC and TGA, if the diffraction pattern indicated differences.

Liquid Assisted (LAG) and Neat Pulverisation (Experiment 7)

Separate portions of Tabernanthalog sorbate salt (50 mg, Experiment 1-Sample A2, Form A) were pulverised in the presence of water (25 µl, η=0.5), trifluoroethanol (25 µl, η=0.5) as well as under neat grind conditions.

A single 7 mm steel bead was added to each reactor, after which they were sealed, and oscillated for 30 minutes at 8.0 Hz (ca. 500 rpm).

Binary Solvent Evaporation Crystallisation (Experiment 6)

Separate portions of Tabernanthalog sorbate salt (50 mg, Experiment 1-Sample A2, Form A) were dissolved in a binary solvent mixture composed of methanol (500 µl) and one of either water (250 µl, -A1), acetone (250 µl, -B1), acetonitrile (250 µl, -C1), THF (250 µl, -D1) and DCM (250 µl, -E1).

Each vial was capped with aluminium foil, pierced, and allowed to stand undisturbed until the evaporation is completed.

Equilibrium Humidity Stability (Experiment 10)

100 mg portions of Tabernanthalog sorbate salt (Experiment 1-Sample A2, Form A) were placed in the relevant vials. Experiment 10-Sample A was open-capped, and Experiment 10-Sample B was open-capped inside double, cable-tied, electrostatic polythene bags (to mimic a typical packaging configuration) and both were placed inside the same humidity chamber at 95% RH at 20° C. The powders were finely divided and distributed evenly over the base of the vial, such that equal material coverage across the panel was observed. The samples were sub-sampled at intervals of t=0, 5 d and 10 d and analysed by XRPD, DSC, TGA and $^1$H NMR, for evidence of phase change or chemical degradation SC-XRD (Experiment 11) (Form A)

A crystalline sample of Experiment 11-Sample A1, which had been recrystallised from water, was isolated and submitted by Aptuit. A small portion of this sample was suspended in perfluoroether oil and a suitable colourless block-shaped crystal with dimensions 0.24-0.07×0.03 mm$^3$ was selected. This crystal was mounted on a MITIGEN holder in oil on a Rigaku 007HF diffractometer with HF Varimax confocal mirrors, an UG2 goniometer and HyPix 6000HE detector. The crystal was kept at a steady T=100(2) K during data collection. The structure was solved with the ShelXT 2014/5 (Sheldrick, 2014) solution program using dual methods and by using Olex2 1.5 (Dolomanov et al., 2009) as the graphical interface. The model was refined with ShelXL 2014/7 (Sheldrick, 2015) using full matrix least squares minimisation on F$^2$.

Experimental Reference: Experiment 12-Sample A2 (Hydrate)

To a vial containing Tabernanthalog sorbate salt (50 mg, Experiment 1-Sample A2, Form A) was charged water (1.0 ml, 20.0 vol) and the contents were heated from 20° C. to 70° C. at 0.5° C./min and was held at that temperature for 1 h prior cooling down to 5° C. at 0.1° C./min. This experiment was a repeat of Experiment 12-A 1, which was cooled down to 10° C. instead of 5° C. at the final step of the method. The method was programmed on a C16 apparatus. The contains of the vial remained at that temperature for ca. 18 h before assessing their quality for SC-XRD analysis by PLM.

A crystalline sample of Experiment 12-Sample A2, which had been recrystallised from water, was isolated and submitted by Aptuit. A small portion of this sample was suspended in perfluoroether oil and a suitable colourless block-shaped crystal with dimensions 0.22×0.16×0.02 mm$^3$ was selected. This crystal was mounted on a MITIGEN holder in oil on a Rigaku 007HF diffractometer with HF Varimax confocal mirrors, a UG2 goniometer and HyPix 6000HE detector. The crystal was kept at a steady T=100(2) K during data collection. The structure was solved with the ShelXT 2014/5 (Sheldrick, 2014) solution program using dual methods and by using Olex2 1.5 (Dolomanov et al., 2009) as the graphical interface. The model was refined with ShelXL 2014/7 (Sheldrick, 2015) using full matrix least squares minimisation on F$^2$.

G. Characterisation Data

1. Tabernanthalog Sorbate Salt (Experiment 13-Sample C1, Form A Reference) the Characterization Data are Provided in FIGS. 741-756 and Table 289

TABLE 289

Peak angle data of Experiment 13-Sample C1. Reported only peaks >10%. Rel. Intensity values calculated based on Net. Intensity values.

| 2-θ (°) | d Value | Rel. Intensity (%) |
|---|---|---|
| 5.7 | 15.54 | 100 |
| 11.4 | 7.76 | 42 |
| 22.6 | 3.93 | 10 |
| 24.7 | 3.60 | 22 |

H. Experimental Data

1. Experiment 7-Sample A (Neat)

The characterization data are provided in FIGS. 757 and 758.

2. Experiment 7-Sample B (Water)

The characterization data are provided in FIGS. 759 and 760.

3. Experiment 8-Sample A2

The characterization data are provided in FIGS. 761-765 and Table 290.

TABLE 290

Peak angle data of Experiment 8-Sample A2. Reported only peaks >10%. Rel. Intensity values calculated based on Net. Intensity values.

| 2-θ (°) | d Value | Rel. Intensity (%) |
|---|---|---|
| 6.5 | 13.67 | 20 |
| 12.5 | 7.08 | 38 |
| 12.8 | 6.90 | 20 |
| 13.6 | 6.48 | 23 |
| 15.4 | 5.74 | 12 |
| 17.6 | 5.03 | 18 |
| 17.9 | 4.94 | 53 |
| 18.1 | 4.89 | 100 |
| 18.7 | 4.73 | 52 |
| 20.1 | 4.42 | 61 |
| 20.6 | 4.32 | 22 |
| 21.8 | 4.07 | 81 |
| 25.0 | 3.56 | 70 |
| 25.6 | 3.48 | 12 |
| 26.0 | 3.43 | 49 |
| 27.5 | 3.24 | 35 |
| 28.2 | 3.17 | 18 |
| 28.5 | 3.13 | 14 |
| 29.1 | 3.07 | 52 |

489

TABLE 290-continued

Peak angle data of Experiment 8-Sample A2. Reported only peaks >10%. Rel. Intensity values calculated based on Net. Intensity values.

| 2-θ (°) | d Value | Rel. Intensity (%) |
|---|---|---|
| 30.4 | 2.94 | 15 |
| 34.5 | 2.59 | 12 |

4. Experiment 8-Sample B

The characterization data are provided in FIGS. 766-769 and Table 291.

TABLE 291

Peak angle data of Experiment 8-Sample B2. Reported only peaks >10%. Rel. Intensity values calculated based on Net. Intensity values.

| 2-θ (°) | d Value | Rel. Intensity (%) |
|---|---|---|
| 5.7 | 15.43 | 100 |
| 11.5 | 7.72 | 47 |
| 18.8 | 4.71 | 11 |
| 23.0 | 3.86 | 12 |

5. Experiment 12-Sample A2

The characterization data are provided in FIG. 770.

I. Supplementary Experiments

1. Evaporation Panel

Experiment 6

From methanol/acetone evaporation (Experiment B), the principal component phase was Form A; small quantity of Pattern #1 was evident by powder and small endo. by DSC (FIGS. 771-782). Likely the water ingress took place during open evaporation.

Experiment 9-Sample A (Pattern #2)

Suspension equilibration in water (5 vol) at 20° C. for 7 days was repeated, aiming to obtain Pattern #2. Again, oven-drying was avoided due to risk of conversion of the metastable form to Form A. Analysis and isolation was the same as in Experiment 8.

XRPD diffractogram overlay of both wet (Experiment 9-Sample A1) and dry (Experiment 9-Sample A2) solid matched Pattern #2 (Experiment 3-Sample R1) (FIG. 783). Other characterization data are provided in FIGS. 784 and 785.

Experiment Reference: Experiment 9-Sample B

Characterization data are provided in FIGS. 786-789.

Experiment Reference: Experiment 9-Sample C and D

Characterization data are provided in FIGS. 790 and 791.

2. Stability Panel at 95% RH (Experiment 10)

Characterization data are provided in FIGS. 792-802.

3. Re-Preparation of Tabernanthalog Sorbate Salt (Scale Up to 5 g)

Experiment 11-Sample A1

Characterization data are provided in FIGS. 803-807.

4. Hypothetical Illustration of Hydration Classification

The hypothetical illustration of hydration classification is provided in Scheme I.

Scheme I

1)
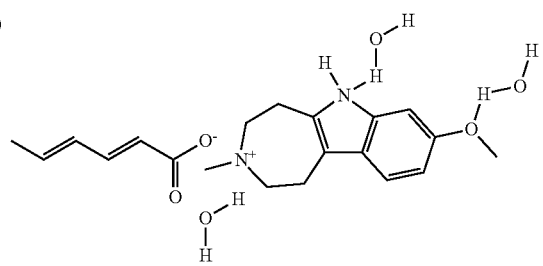
Water is the H-bond donor, API multiple H-bond acceptor sites: Crystal or site bonded, stoichiometric hydrate.

2)
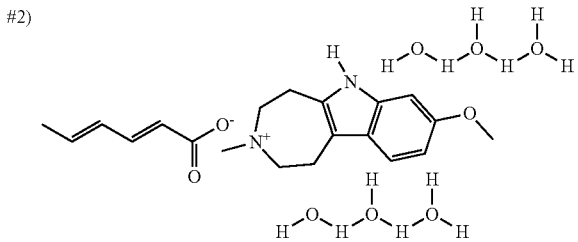
Water is the H-bond donor and acceptor to the other water molecules, API is not involved in H-bond to water: Non-crystal bonded, channel, non-stoichiometric hydrate

3)
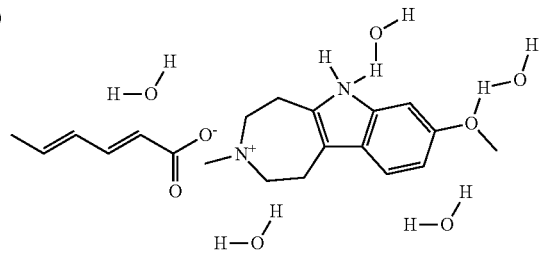
Water molecules tumble in isolated pockets, not H-bonded to water or the API: Non-crystal bonded, pocket hydrate, non-stoichiometric hydrate.

4)

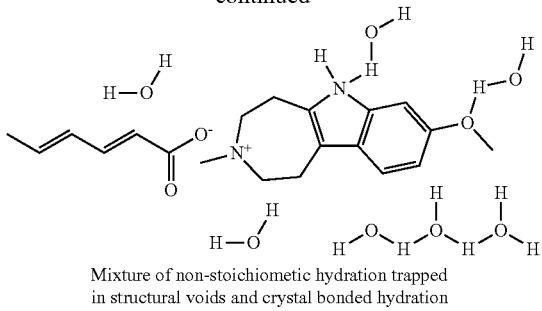

Mixture of non-stoichiometic hydration trapped in structural voids and crystal bonded hydration

5. DVS Analyses: 0% to 90% DVS Mass Per Unit Time Equilibrated at Dm/Dt (0.0002%/Min)

Experiment 1-Sample A2

Tabernanthalog sorbate salt, slightly hygroscopic up to 80% RH (red isotherm), hysteresis observed in the 80% to 50% RH range, held onto water >50% RH, during the desorption cycle. Th., unary hydrate 5.0% w/w (20° C./95% RH, 5 days gave Pattern #2), likely seeing partial conversion into Pattern #2 and reversion back into Form A on the desorption cycle (FIG. 808).

Residue at completion of the run was consistent with Form A (FIG. 809).

6. DSC Analyses, Form A

DSC data were collected from 25 to 220 C at a scan rate of at 10° C. min$^{-1}$ (Table 292).

TABLE 292

Summary of results.

| Experiment | melt onset ° C. | peak ° C. | Endset ° C. | melt enthalpy Jg-1 |
|---|---|---|---|---|
| A1270-20-V2 | 143.89 | 148.83 | 151.95 | −84.09 |
| Experiment 13-Sample C1 | 139.87 | 142.50 | 144.46 | −105.78 |
| Experiment 1-Sample A2 | 140.03 | 142.50 | 144.06 | −106.66 |
| Experiment 6-Sample C1 | 144.66 | 148.83 | 151.02 | −100.48 |
| Experiment 6-Sample D1 | 144.03 | 148.00 | 150.17 | −166.35 |
| Experiment 6-Sample E1 | 145.00 | 148.83 | 151.59 | −105.68 |
| Experiment 7-Sample A neat | 144.39 | 146.83 | 148.53 | −122.47 |
| Experiment 7-Sample B water | 144.54 | 146.83 | 148.41 | −115.11 |
| Experiment 8-Sample B2 | 141.82 | 144.33 | 145.97 | −98.01 |
| Experiment 11-Sample A1 | 145.84 | 149.83 | 152.48 | −92.27 |
| mean | 143.41 | 146.73 | 148.86 | −109.69 |
| variance | 4.37 | 7.34 | 9.73 | 513.74 |

7. SC-XRPD

SC-XRPD Characterization of Tabernanthalog Sorbate Form A

Experimental. A crystalline sample of Experiment 11-Sample A1, which had been recrystallised from water, was isolated and submitted by Aptuit A small portion of this sample was suspended in perfluoroether oil and a suitable colourless block-shaped crystal with dimensions 0.24×0.07× 0.03 mm$^3$ was selected. This crystal was mounted on a MITIGEN holder in oil on a Rigaku 007HF diffractometer with HF Varimax confocal mirrors, an UG2 goniometer and HyPix 6000HE detector. The crystal was kept at a steady T=100(2) K during data collection. The structure was solved with the SheXT 2014/5 (Sheldrick, 2014) solution program using dual methods and by using Olex2 1.5 (Dolomanov et al., 2009) as the graphical interface. The model was refined with SheXL 2014/7 (Sheldrick, 2015) using full matrix least squares minimisation on F.

Crystal Data. $C_{20}H_{26}N_2O_3$, $M_r$=342.43, monoclinic, $P2_1/c$ (No. 14), a=9.3410(3) Å, b=6.4173(2) Å, c=30.5108 (12) Å, β=95.374(3)°, α=γ=90°, V=1820.90(11) Å$^3$, T=100 (2) K, Z=4, Z'=1, μ(Cu K$_a$)=0.675 mm$^{-1}$, 13832 reflections measured, 3694 unique ($R_1$, =0.0462) which were used in all calculations. The final w$R_2$ was 0.2098 (all data) and $R_1$ was 0.0826 (I≥2 σ(I)).

Discussion. A colourless block-shaped crystal with dimensions 0.24×0.07×0.03 mm$^3$ was mounted on a MITIGEN holder in oil. X-ray diffraction data were collected using a Rigaku 007HF diffractometer with HF Varimax confocal mirrors, an UG2 goniometer and HyPix 6000HE detector equipped with an Oxford Cryosystems low-temperature device, operating at T=100(2) K.

Data were measured using profile data from w-scans of 0.5° per frame for 1.5/6.0 s using Cu K$_a$ radiation (Rotating anode, 40.0 kV, 30.0 mA). The total number of runs and images was based on the strategy calculation from the program CrysAlisPro 1.171.42.61a (Rigaku OD, 2022). The maximum resolution achieved was Q=76.705°.

Cell parameters were retrieved using the CrysAlisPro 1.171.42.61a (Rigaku OD, 2022) software and refined using CrysAlisPro 1.171.42.61a (Rigaku OD, 2022) on 5628 reflections, 41% of the observed reflections. Data reduction was performed using the CrysAlisPro 1.171.42.61a (Rigaku OD, 2022) software which corrects for Lorentz polarisation. The final completeness is 99.20% out to 76.705° in Q.

A multi-scan absorption correction was performed using CrysAlisPro 1.171.42.61a (Rigaku Oxford Diffraction, 2022) Empirical absorption correction using spherical harmonics, implemented in SCALE3 ABSPACK scaling algorithm. The absorption coefficient m of this material is 0.675 mm$^{-1}$ at this wavelength (l=1.54184 Å) and the minimum and maximum transmissions are 0.768 and 1.000.

The structure was solved in the space group $P2_1/c$ (#14) by using dual methods using the ShelXT 2014/5 (Sheldrick, 2014) structure solution program and refined by full matrix least squares minimisation on P using version 2014/7 of ShelXL 2014/7 (Sheldrick, 2015). All non-hydrogen atoms were refined anisotropically. The position of the N—H atoms H1 and H2 were located from the electron difference map and refined with their thermal parameters linked to their parent atoms. The positions of the remaining H atoms were calculated geometrically and refined using the riding model (FIG. 810 and Table 293).

TABLE 293

SC-XRPD Characterization of Tabernanthalog Sorbate Form A

| Compound | Experiment 11-Sample A1 |
|---|---|
| Formula | $C_{20}H_{26}N_2O_3$ |
| $D_{calc.}$/g cm$^{-3}$ | 1.249 |
| m/mm$^{-1}$ | 0.675 |
| Formula Weight | 342.43 |
| Colour | colourless |
| Shape | block-shaped |
| Size/mm$^3$ | 0.24 × 0.07 × 0.03 |
| T/K | 100(2) |
| Crystal System | monoclinic |
| Space Group | $P2_1/c$ |

TABLE 293-continued

SC-XRPD Characterization of
Tabernanthalog Sorbate Form A

| Compound | Experiment 11-Sample A1 |
|---|---|
| a/Å | 9.3410(3) |
| b/Å | 6.4173(2) |
| c/Å | 30.5108(12) |
| a/° | 90 |
| b/° | 95.374(3) |
| g/° | 90 |
| V/Å$^3$ | 1820.90(11) |
| Z | 4 |
| Z' | 1 |
| Wavelength/Å | 1.54184 |
| Radiation type | Cu K$_a$ |
| Q$_{min}$/° | 4.755 |
| Q$_{max}$/° | 76.705 |
| Measured Refl's. | 13832 |
| Indep't Refl's | 3694 |
| Refl's I ≥ 2 s(I) | 3203 |
| R$_{int}$ | 0.0462 |
| Parameters | 300 |
| Restraints | 568 |
| Largest Peak | 0.359 |
| Deepest Hole | −0.311 |
| GooF | 1.094 |
| wR$_2$ (all data) | 0.2098 |
| wR$_2$ | 0.2030 |
| R$_1$ (all data) | 0.0931 |
| R$_1$ | 0.0826 |

The simulated powder diffraction pattern of Tabernanthalog·Sorbate (Form A) is provided in Table 293B

TABLE 293B

Simulated powder diffraction pattern of
Tabernanthalog•Sorbate (Form A).

| Peak number | 2-θ (°) | Rel Intensity % |
|---|---|---|
| Peak #1 | 5.8 | 86 |
| Peak #2 | 9.5 | 22 |
| Peak #3 | 10.7 | 61 |
| Peak #4 | 11.6 | 45 |
| Peak #5 | 17.5 | 36 |
| Peak #6 | 18.1 | 50 |
| Peak #7 | 19.1 | 100 |
| Peak #8 | 19.4 | 35 |
| Peak #9 | 21.0 | 11 |
| Peak #10 | 21.7 | 43 |
| Peak #11 | 22.3 | 10 |
| Peak #12 | 22.9 | 53 |
| Peak #13 | 23.4 | 10 |
| Peak #14 | 24.7 | 47 |
| Peak #15 | 25.0 | 96 |
| Peak #16 | 25.6 | 22 |
| Peak #17 | 27.3 | 38 |
| Peak #18 | 28.8 | 22 |
| Peak #19 | 29.9 | 26 |

SC-XRPD Characterization of Tabernanthalog Sorbate Hydrate

Experimental. A crystalline sample of Experiment 12-Sample A2, which had been recrystallised from water, was isolated and submitted by Aptuit. A small portion of this sample was suspended in perfluoroether oil and a suitable colourless block-shaped crystal with dimensions 0.22×0.16× 0.02 mm$^3$ was selected. This crystal was mounted on a MITIGEN holder in oil on a Rigaku 007HF diffractometer with HF Varimax confocal mirrors, a UG2 goniometer and HyPix 6000HE detector. The crystal was kept at a steady T=100(2) K during data collection. The structure was solved with the ShelXT 2014/5 (Sheldrick, 2014) solution program using dual methods and by using Olex2 1.5 (Dolomanov et al., 2009) as the graphical interface. The model was refined with SheXL 2014/7 (Sheldrick, 2015) using full matrix least squares minimisation on F$^1$.

Crystal Data. C$_{20}$H$_{28}$N$_2$O$_4$, M$_r$=360.44, monoclinic, P2$_1$/c (No. 14), a=16.07470(10) Å, b=12.14150(10) Å, c=10.85080(10) Å, =β3109.2390(10γ=α, °)=90°, V=1999.49(3) Å$^3$, T=100(2) K, Z=4, Z'=1, μ(Cu K$_α$)=0.676 mm$^{-1}$, 51305 reflections measured, 3786 unique (R$_{int}$=0.0483) which were used in all calculations. The final wR$_2$ was 0.0874 (all data) and R$_1$ was 0.0347 (I≥2 σ(I)).

Discussion X-ray data were collected upon a colourless block-shaped crystal with dimensions 0.22×0.16×0.02 mm$^{-1}$, which was mounted on a MITIGEN holder in oil. X-ray diffraction data were collected using a Rigaku 007HF diffractometer with HF Varimax confocal mirrors, a UG2 goniometer and HyPix 6000HE detector equipped with an Oxford Cryosystems low-temperature device, operating at T=100(2) K.

Data were measured using profile data from w-scans of 0.5° per frame for 0.5/4.0 s using Cu K$_a$ radiation (Rotating anode, 40.0 kV, 30.0 mA). The total number of runs and images was based on the strategy calculation from the program CrysAlisPro 1.171.42.61a (Rigaku OD. 2022). The maximum resolution achieved was Q=70.074°.

Cell parameters were retrieved using the CrysAlisPro 1.171.42.61a (Rigaku OD, 2022) software and refined using CrysAlisPro 1.171.42.61a (Rigaku OD, 2022) on 35970 reflections, 70% of the observed reflections. Data reduction was performed using the CrysAlisPro 1.171.42.61a (Rigaku OD, 2022) software which corrects for Lorentz polarisation. The final completeness is 100.00% (IUCr) out to 70.074° in Q.

A multi-scan absorption correction was performed using CrysAlisPro 1.171.42.61a (Rigaku Oxford Diffraction. 2022) Empirical absorption correction using spherical harmonics, implemented in SCALE3 ABSPACK scaling algorithm. The absorption coefficient m of this material is 0.676 mm$^{-1}$ at this wavelength (l=1.54184 Å) and the minimum and maximum transmissions are 0.784 and 1.000.

The structure was solved in the space group P2$_1$/c (#14) by using dual methods using the ShelXT 2014/5 (Sheldrick, 2014) structure solution program and refined by full matrix least squares minimisation on F$^2$ using version 2014/7 of ShelXL 2014/7 (Sheldrick, 2015). All non-hydrogen atoms were refined anisotropically. The position of the N—H atoms H1 and H2 and the O—H atoms H4A and H4B were located from the electron difference map and refined with their thermal parameters linked to their parent atoms. The positions of the remaining H atoms were calculated geometrically and refined using the riding model.

There is a single molecule in the asymmetric unit, which is represented by the reported sum formula. In other words: Z is 4 and Z' is 1. SC-XRPD Characterization of Tabernanthalog Sorbate Hydrate is provided in Table 294 and FIG. 811.

TABLE 294

SC-XRPD Characterization of Tabernanthalog Sorbate Hydrate

| Compound | Experiment 12-Sample A2 |
|---|---|
| Formula | C$_{20}$H$_{28}$N$_2$O$_4$ |
| D$_{calc}$/g cm$^{-3}$ | 1.197 |
| m/mm$^{-1}$ | 0.676 |

TABLE 294-continued

SC-XRPD Characterization of Tabernanthalog Sorbate Hydrate

| Compound | Experiment 12-Sample A2 |
|---|---|
| Formula Weight | 360.44 |
| Colour | colourless |
| Shape | block-shaped |
| Size/mm$^3$ | 0.22 × 0.16 × 0.02 |
| T/K | 100(2) |
| Crystal System | monoclinic |
| Space Group | $P2_{1/c}$ |
| a/Å | 16.07470(10) |
| b/Å | 12.14150(10) |
| c/Å | 10.85080(10) |
| a/° | 90 |
| b/° | 109.2390(10) |
| g/° | 90 |
| V/Å$^3$ | 1999.49(3) |
| Z | 4 |
| Z' | 1 |
| Wavelength/Å | 1.54184 |
| Radiation type | Cu K$_\alpha$ |
| $Q_{min}$/° | 2.912 |
| $Q_{max}$/° | 70.074 |
| Measured Refl's. | 51305 |
| Indep't Refl's | 3786 |
| Refl's I ≥ 2 s(I) | 3542 |
| $R_{int}$ | 0.0483 |
| Parameters | 250 |
| Restraints | 0 |
| Largest Peak | 0.233 |
| Deepest Hole | −0.188 |
| GooF | 1.039 |
| wR$_2$ (all data) | 0.0874 |
| wR$_2$ | 0.0861 |
| R$_1$ (all data) | 0.0369 |
| R$_1$ | 0.0347 |

The simulated powder diffraction pattern of Tabernanthalog·Sorbate·H$_2$O is provided in Table 294B

TABLE 294B

Simulated powder diffraction pattern of Tabernanthalog•Sorbate•H$_2$O

| Peak number | 2-θ (°) | Rel Intensity % |
|---|---|---|
| Peak #1 | 5.8 | 62 |
| Peak #2 | 11.3 | 20 |
| Peak #3 | 11.7 | 14 |
| Peak #4 | 13.8 | 11 |
| Peak #5 | 14.0 | 14 |
| Peak #6 | 17.0 | 32 |
| Peak #7 | 17.4 | 18 |
| Peak #8 | 17.9 | 25 |
| Peak #9 | 18.7 | 28 |
| Peak #10 | 18.9 | 18 |
| Peak #11 | 20.2 | 14 |
| Peak #12 | 22.7 | 100 |
| Peak #13 | 25.0 | 13 |
| Peak #14 | 27.7 | 11 |
| Peak #15 | 28.1 | 11 |
| Peak #16 | 30.0 | 22 |
| Peak #17 | 32.3 | 14 |

Example 11: Preparation and Characterisation of Amorphous Forms of Tabernanthalog·Monofumarate and Tabernanthalog·Sorbate

| Abbreviations | |
|---|---|
| $\phi_i$ | Water activity coefficient |
| $a_w$ | Water activity |
| ASD | Amorphous solid dispersion |
| ca. | circa (Latin: approximately) |
| cf. | Confer/conferatur (Latin: to confer, to compare) |
| ° C. | degree Celsius |
| CP | Chemical Purity |
| CP-MAS | Cross Polarised Magic Angle Spinning (13C NMR solid state technique) |
| Da | Dalton |
| DSC | Differential Scanning Calorimetry (measures changes in heat capacity) |
| DTA | Differential Thermal Analyses (measures changes in temperature) |
| DVS | Dynamic Vapour Sorption (used interchangeably with GVS) |
| e.g. | Exempli gratia (Latin: for example) |
| etc. | Et cetera (Latin: 'and others' or 'and so on') |
| FT-IR | Fourier Transformed, InfraRed spectroscopy (prefixed mid and far) |
| g | Gram (s) |
| GRAS | Generally Recognised As Safe |
| GVS | Gravimetric Vapour Sorption |
| h | Hour (s) |
| HFIPA | Hexafluoroisopropanol |
| HPLC | High Performance Liquid Chromatography |
| HSM | Hot Stage Microscopy (thermal microscopy) |
| HUCD | Heat-up / cool-down crystallisation |
| i.e. | Id Est (Latin: that is) |
| IR | InfraRed Spectroscopy |
| J | Joule |
| Kelvin | Kelvin. SI unit of temperature, used interchangeably with ° C. to express increment/decrement of temperature set point (e.g. ramp rate on DSC thermogram 10K/min); note K sign not prefixed by. |
| KF | Karl Fischer (determination of the water content by coulometric titration) |
| kg | Kilogram (s) |
| LOD | Loss On Drying |
| mag | magnification |
| mAu | milli-Absorption units (chromatographic unit of peak height) |
| mAu * s | milli-Absorption units multiplied by second (chromatographic unit of peak area) |
| MET/CR | Aptuit chromatography method reference |

| Abbreviations | |
|---|---|
| min | Minute (s) |
| mg | Milligram (s) |
| ml | Milliliter (s) |
| mol | mole, amount of substance |
| N/A | Not Applicable |
| n.a. | not analysed |
| n.d. | not detected |
| nm | nanometre |
| NMR | Nuclear Magnetic Resonance |
| oab | on anhydrous basis |
| osfb | on solvent free basis |
| oasfb | on anhydrous solvent free basis |
| pH | $-\log [H^+]$ or pH = $-\log a_{H^+}$ |
| $pK_a$ | $-\log (K_a)$, acid dissociation constant |
| pI | isoelectric point, quoted in unit pH |
| PLM | Polarised Light Microscopy |
| RelRT | Relative Retention Time (not be confused RT) |
| REP/ | Aptuit report (REP) reference |
| RFA | Request For Analysis (unique reference number) |
| RH | Relative Humidity ($a_w$ * 100) |
| RT | Room Temperature (ambient, typically: 15 to 25° C.) |
| S | Second (s) |
| SCXD | Single Crystal X-Ray Determination |
| SMPT | Solvent mediated phase transition |
| STA | Simulated Thermal Analysis (STA = TGA + DTA) |
| t | time in seconds, minutes, hour, days etc. (interval specified in parentheses); alias in common use tonne (t) |
| t | Tonne, metric unit of mass (1000 kg; 1 Mg), (compaction force in kg, suffixed in parentheses) |
| T | Temperature recorded in degrees Celsius (° C.); alias in common use, SI unit of magnetic flux density, also denoted T |
| MTBE | Methyl tert-butyl ether |
| TCNB | 2,3,5,6-Tetrachloronitrobenzene ($C_6HCl_4NO_2$, F.W. 260.89 gmol$^{-1}$) |
| TFE | Trifluoroethanol (solvent used for solvent drop grinding) |
| Tg | Glass temperature |
| TGA | Thermogravimetric Analysis |
| th. | theoretical |
| UV | Ultra Violet |
| vol. | Volume or relative volume |
| vs. | versus |
| v/v | volume/volume |
| W | Watt |
| w/w | weight/weight |
| XRPD | X-Ray Powder Diffraction |

| Definitions | |
|---|---|
| Isostructural | Crystals are said to be isostructural if they have the same crystal structure but not necessarily the same cell dimensions nor the same chemical composition (Kálmán, A., Párkányi, L. & Argay, G. (1993) *Acta Cryst.* B49, 1039-1049.) |
| Isomorphic | two crystalline solids are isomorphous if both have the same unit-cell dimensions and space group (source, *vide supra*). |
| Isomorphic desolvate | via solvent release from an isostructural solvate. |
| Native | Refers to an API in its native or non-ionised form. |
| Normal light | Light oscillating in all directions perpendicular to the axis to which it travels. |
| Particle size | Expressed as a volume distribution, the range x10 > PSD < x90 captures the sizes of 80% of the particles. |
| Plane polarised light | Light passed through a polaroid filter which allows only light oscillating in one plane to be transmitted. |
| Polymorphism | Crystalline solid able to exhibit different crystalline phases. |
| Photomicrograph | Imaged captured of a small object under magnification through an optical microscope. |
| Pseudopolymorphism | Different crystal structure attributed to the incorporation of molecular water or solvent. |
| Solvates | Contains a molecule of solvent in the crystal lattice. |
| Thermogram | Differential scanning calorimetry trace: heat flow on y-ordinate (mW), time (minutes)/temperature (° C.) on x-ordinate. |

1. Summary

Characterisation of amorphous Tabernanthalog·Monofumarate and Tabernanthalog·Sorbate:

- Several attempts were made to generate amorphous forms of Tabernanthalog·Monofumarate and Tabernanthalog·Sorbate utilising methods such as lyophilisation/cryodesiccation, spray drying, communition via bead milling and evaporation. None of the methods were successful.
- Thermal methods (TGA and DSC) were used to generate and analyse the amorphous form in situ. The glass temperatures (Tg) were determined for Tabernanthalog·Monofumarate and Tabernanthalog·Sorbate.
- Unable to proceed with large scale generation of amorphous material, therefore, water activity studies were not progressed.
- A unique powder pattern (#7) was observed after treatment of Tabernanthalog·Sorbate with hexafluoroisopropanol (HFIPA).
- Pattern #7 was regenerated by evaporation of a solution of Tabernanthalog·Sorbate in HFIPA. The product was characterised by $^1$H NMR and $^{19}$F NMR spectroscopy, XRPD, DSC, TGA and underwent stability to equilibrium humidity evaluations at 20° C./75% RH and 40° C./75% RH.
- Pattern #7 was determined to be Tabernanthalog·Sorbate·HemiHFIPA, the solvate reverted to the input form (Form A) by heating to 100° C., confirmed by XRPD analysis.

2. Project Design

This report describes the following activities:
- Analysis of the amorphous forms to determine their Tg.
- Approaches taken to generate the amorphous forms, including bead-milling, evaporation, nitrogen streams, and freeze drying/cryodesiccation.
- Amorphous forms were not generated utilising these techniques; therefore, thermal treatments to access the amorphous phase were carried out and in-situ analysis was performed. Employing a thermocycle technique on both TGA and DSC to melt the sample and then reanalyse to determine Tg, was successful for all compounds.
- Specimens of the Tabernanthalog salts were heated in XRPD low background silicon sample holders to generate enough amorphous material for XRPD analysis. Once the specimens were confirmed to be amorphous, solution analyses by $^1$H NMR and LCMS were used to determine if thermal deterioration of the sample had occurred.

3. Results and Discussion

3.1 Tables of Characterisation

TABLE 295

| | Tabernanthalog•Sorbate |
|---|---|
| Provenances of reference batches | Tabernanthalog•Sorbate |
| Experiment 1-Sample D1, Experiment 1-Sample E1 Heated up past the melt event on a hot stage microscope | Reference batches: Experiment 1-Sample D1, Experiment 1-Sample E1<br>Molecular weight: 342.439 gmol$^{-1}$<br>Exact molecular weight: 342.19<br>Molecular formula: $C_{20}H_{26}N_2O_3$<br>XRPD: Amorphous, (Experiment 1-Sample D1 refer to section).<br>$^1$H NMR: (DMSO-d$_6$, 400 MHz); δ 10.5 (s, 1H), 7.2 (d, J = 8.56 Hz, 1H), 7.1 (dd, J = 15.2, 15.3 Hz, 1H), 6.7 (d, J = 1.9 Hz, 1H), 6.6 (d, J = 8.56, 2.2 Hz, 1H), 6.2 (d, m, 2H), 5.8 (d, J = 15.0 Hz, 1H), 3.7 (s, 3H), 2.8 (m, 2H), 2.7 (m, 6H), 2.4 (s, 3H), 1.8 (d, J = 5.8 Hz, 3H) ppm; conforms to the molecular structure (Σ[25H])[1]. (Experiment 1-Sample D1 refer to section). |

[1]The molecular formula ($C_{20}H_{26}N_2O_3$) includes the carboxylic acid proton however, it co-resonates with water.

TABLE 296

| | Tabernanthalog•Sorbate•HemiHFIPA |
|---|---|
| Provenances of reference batches | Tabernanthalog•Sorbate•HemiHFIPA |
| Experiment 3-Sample A2 Crystallisation of Tabernanthalo•Sorbate from a solution of Hexafluoroisopropanol (HFIPA) | Reference batches: Experiment 3-Sample A2<br>Molecular weight: 510.48 gmol$^{-1}$<br>Exact molecular weight: 510.20<br>Molecular formula: $C_{23}H_{28}F_6N_2O_4$<br>XRPD: 6.3°, 0.4°, 13.3°, 14.0°, 15.4°, 15.8°, 16.1°, 16.5°, 17.1°, 17.1v, 17.7°, 19.0°, 19.4°, 21.2°, 21.9°, 22.6°, 23.3°, 23.8°, 25.1°, 26.6°, 27.3°, 27.8°, 29.3°, 30.6° (2θ, 1 d.p), (Experiment 3-Sample A2 refer to section)<br>DSC: onset 74.57° C. (−49.44 Jg$^{-1}$, endotherm, desolvation), 102.81° C. (−41.07 Jg$^{-1}$, endotherm, desolvation), 143.78° C. (−8.17 Jg$^{-1}$, |

TABLE 296-continued

Tabernanthalog•Sorbate•HemiHFIPA

| Provenances of reference batches | Tabernanthalog•Sorbate•HemiHFIPA |
|---|---|
| | endotherm, desolvation), (Experiment 3-Sample A2 refer to section) TGA: onset 70.03° C. (−12.4028% w/w, dehydration), 102.83° C. (−18.6893% w/w, dehydration), 220.77° C. (−55.2875% w/w, ablation) (Experiment 3-Sample A2 refer to section). $^1$H NMR: (DMSO-$d_6$, 400 MHz); δ 10.5 (s, 1H), 7.2 (d, 1H), 7.1 (dd, 1H), 6.7 (d, 1H), 6.6 (dd, 1H), 6.2 (m, 2H), 5.8 (d, 1H), 3.7 (s, 3H), 2.8 (t, 2H), 2.7 (d, 6H), 2.4 (s, 3H), 1.8 (d, 3H) ppm; conforms to the molecular structure (Σ25H). (Experiment 3-Sample A2 refer to section) Q$^{19}$F NMR: 13% w/w HFIPA (Experiment 3-Sample A2 refer to section) |

TABLE 297

Tabernanthalog•Monofumarate

| Provenances of reference batches | Tabernanthalog•Monofumarate |
|---|---|
| Experiment 2-Sample D1, Experiment 2-Sample E1 Heated up past the melt event on a hot stage microscope | Reference batches: Experiment 2-Sample D1, Experiment 2-Sample E1 Molecular weight: 346.383 gmol$^{-1}$ Exact molecular weight: 346.153 Molecular formula: $C_{18}H_{22}N_2O_5$ XRPD: Amorphous (Experiment 2-Sample D1 refer to section) $^1$H NMR: (DMSO-$d_6$, 400 MHz); δ 10.6 (s, 1 H), 7.3 (d, 1 H), 6.8 (s, 1 H), 6.6 (dd, 1 H), 6.5 (s, 2 H), 3.7 (s, 3 H), 3.1 −3.0 (m, 6 H), 2.9 (t, 2 H), 2.6 (s, 3 H) conforms to the molecular structure (Σ20H). (Experiment 2-Sample D1 refer to section) |

[1] The molecular formula ($C_{20}H_{26}N_2O_3$) includes the carboxylic acid proton however, it co-resonates with water.

FIGS. 812-875 provide additional details about the preparation and characterisation of amorphous forms of Tabernanthalog·Monofumarate and Tabernanthalog·Sorbate.

Table 298. Form Summary Table

| Designation | Experimental reference | Solvent | DSC Profile | DSC Event | DSC Thermal measurements | | | TGA % Δwt. | TGA Comment | ¹H NMR (stoich.) | ¹H NMR (solvent) | Form Assignment |
|---|---|---|---|---|---|---|---|---|---|---|---|---|
| Pattern #7 (Tabernanthalog·Sorbate) | Experiment 3-Sample A1 | HFIPA | | Complex thermal profile | Integral | -49.44 Jg^-1 | | -12.4%, 70 °C; -18.6%, 102.83 °C, -55.29%, 220.77 °C | De-solvation | 1 to 1 (API to Sorbate) | ¹⁹F: 13% w/w HFIPA | Pattern #7 (HFIPA solvate) |
| | | | | | Onset | 71.57 °C | | | | | | |
| | | | | | Peak | 79.00 °C | | | | | | |
| | | | | | Endset | 82.25 °C | | | | | | |
| Amorphous (Tabernanthalog·Sorbate) | Experiment 1-Sample D1, Experiment 1-Sample E1 | - | | Tg, Crystallisation, Melt | Integral | -2.46 Jg^-1 | | -9.9%, 148.5 °C | De-solvation | 1 to 1 (API to Sorbate) | - | Amorphous |
| | | | | | Onset | 21.82 °C | | | | | | |
| | | | | | Peak | 27.33 °C | | | | | | |
| | | | | | Endset | 32.62 °C | | | | | | |
| Amorphous (Tabernanthalog·Monofumarate) | Experiment 2-Sample D1, Experiment 2-Sample E1 | - | | Tg | Integral | -1.88 Jg^-1 | | -2.1%, 62.8 °C, -7%, 202.9 °C | De-solvation | 1 to 1 (API to fumarate) | - | Amorphous |
| | | | | | Onset | 57.16 °C | | | | | | |
| | | | | | Peak | 69.83 °C | | | | | | |
| | | | | | Endset | 84.03 °C | | | | | | |

Note: Reaction codes ending in -D1 consumed for NMR analysis and a repeat experiment (reaction codes ending in -E1) for LC-MS data was performed.

A new powder pattern (Pattern #7) was observed from experiments (Experiment 4-Sample B1) involving hexafluoroisopropanol treatments, indicating that a potential solvate was formed.

TABLE 299

Amorphous study of Tabernanthalog•Monofumarate and Tabernanthalog•Sorbate.

| Experiment references | Salt form | Scale investigation | Amorphisation activity | Outcome | Form by XRPD |
|---|---|---|---|---|---|
| Experiment 4-Sample A1 | Tabernanthalog•Sorbate | 50 mg | Freeze dry | Crystalline | Form A |
| Experiment 4-Sample A2 | Tabernanthalog•Sorbate | 50 mg | Rotary Vac (MeOH) | Crystalline | Form A |
| Experiment 4-Sample A3 | Tabernanthalog•Sorbate | 50 mg | THF/$N_2$ | Crystalline | Form A |
| Experiment 4-Sample A4 | Tabernanthalog•Sorbate | 50 mg | Antisolvent/$N_2$ Flow | Crystalline | Form A |
| Experiment 4-Sample B1 | Tabernanthalog•Sorbate | 50 mg | HFIP Evaporation | Crystalline | Pattern #7 |
| Experiment 4-Sample B2 | Tabernanthalog•Sorbate | 50 mg | HFIP Evaporation | Gum | |
| Experiment 4-Sample B3 | Tabernanthalog•Sorbate | 50 mg | HFIP Evaporation | Crystalline | Pattern #7 |
| Experiment 4-Sample C1 | Tabernanthalog•Sorbate | 100 mg | Milling | Crystalline | Form A |
| Experiment 4-Sample D1 | Tabernanthalog•Sorbate | 100 mg | Spray drying (MeOH) | Crystalline | Form A |
| Experiment 4-Sample D2 | Tabernanthalog•Sorbate | 100 mg | Spray drying (MeOH) | Crystalline | Form A |
| Experiment 4-Sample E1 | Tabernanthalog•Sorbate | 100 mg | Spray drying (15% EtOH/Water) | Crystalline | Form A |
| Experiment 5-Sample A1 | Tabernanthalog•Monofumarate | 50 mg | Freeze dry | Crystalline | Pattern #1 |
| Experiment 5-Sample A2 | Tabernanthalog•Monofumarate | 50 mg | THF/$N_2$ | Crystalline | Pattern #11 |
| Experiment 5-Sample A3 | Tabernanthalog•Monofumarate | 50 mg | Crash cool | Crystalline | Pattern #3 |
| Experiment 4-Sample D1 | Tabernanthalog•Sorbate | 250 mg | Hot Melt Extrusion | Black crystalline material | Form A |
| Experiment 4-Sample D2 | Tabernanthalog•Sorbate | 250 mg | Hot Melt Extrusion (Overnight) | Black crystalline material | Form A |
| Experiment 6-Sample A1 | Tabernanthalog•Sorbate | 50 mg | Milling | Crystalline | Form A |
| Experiment 6-Sample A2 | Tabernanthalog•Sorbate | 50 mg | Milling | Crystalline | Form A |
| Experiment 6-Sample A3 | Tabernanthalog•Sorbate | 50 mg | Milling | Crystalline | Form A |

3.2.2 Thermal Study

Initial experiments to produce the amorphous phase were unsuccessful for Tabernanthalog·Sorbate and Tabernanthalog Monofumarate. Therefore, thermal techniques would be used to access the amorphous phase in-situ and complete characterisation of the glass temperature (Tg).

Each salt was analysed by DSC and TGA to determine the Tg of the amorphous form. Amorphous forms were generated by thermocycling the salt past the melt temperature, cooling the sample, and once cooled the samples were reheated. Open pan and sealed pan DSC were utilised, open pan DSC were heated past the melt event, cooled, and left to stand under ambient conditions overnight. Sealed pans were immediately cycled with no time left to stand.

TGA (open pan) samples were analysed by thermocycle, with no time for the sample to stand under ambient conditions.

The amorphous forms were generated in these studies and characterised with their Tg being measured.

A hot stage microscope heating block was used to generate the amorphous phase in-situ, to allow analysis by XRPD. A silicon XRPD sample plate was loaded with the appropriate salt. The plate was heated past the melt event, removed from the hot stage microscope block and cooled to ambient in air and analysed by XRPD to ensure that the amorphous form was generated. The amorphous material was then analysed by $^1$H NMR and LC-MS to ensure there was no change in chemical composition. Each sample was successfully analysed obtaining the amorphous form and thermal characterisation, $^1$H NMR and LC-MS proved there was no change in chemical composition of the samples after treatment.

TABLE 300

Thermal study of Tabernanthalog•Monofumarate and Tabernanthalog•Sorbate.

| Experiment references | Salt form | Experiment | Temperature range (° C.) | Outcome |
|---|---|---|---|---|
| Experiment 1-Sample A1 | Tabernanthalog•Sorbate | Open Pan DSC | 20 to 165 to −20, O/N 20 to 230 | Amorphous |
| Experiment 1-Sample B1 | Tabernanthalog•Sorbate | Sealed DSC | 20 to 165 to −20 to 230 | Amorphous |
| Experiment 1-Sample C1 | Tabernanthalog•Sorbate | TGA | 20 to 165 to −20 to 230 | Amorphous |
| Experiment 1-Sample D1 | Tabernanthalog•Sorbate | Hot plate heat up | 20 to 170 | Amorphous |
| Experiment 1-Sample D2 | Tabernanthalog•Sorbate | Experiment 1-Sample D1 standing overnight | ambient | Crystalline |
| Experiment 1-Sample E1 | Tabernanthalog•Sorbate | Hot stage plate heat up | 20 to 170 | Amorphous |
| Experiment 2-Sample A1 | Tabernanthalog•Monofumarate | Open Pan DSC | 20 to 210 to −20, O/N 20 to 210 | Amorphous |
| Experiment 2-Sample B1 | Tabernanthalog•Monofumarate | Sealed DSC | 20 to 210 to −20 to 210 | Amorphous |
| Experiment 2-Sample C1 | Tabernanthalog•Monofumarate | TGA | 20 to 210 to −20 to 210 | Amorphous |
| Experiment 2-Sample D1 | Tabernanthalog•Monofumarate | Hot plate heat up | 20 to 210 | Amorphous |
| Experiment 2-Sample E1 | Tabernanthalog•Monofumarate | Hot stage plate heat up | 20 to 210 | Almost Amorphous |

TABLE 301

Glass transition temperature (Tg) for Tabernanthalog•Monofumarate and Tabernanthalog•Sorbate.

| Experimental Reference | Salt | Glass temperature (Tgs) |
|---|---|---|
| Experiment 1-Sample B1 | Tabernanthalog•Sorbate | 22° C. |
| Experiment 2-Sample B1 | Tabernanthalog•Monofumarate | 63° C. |

3.2.3 Milling

Bead milling was attempted to generate the amorphous form of Tabernanthalog·Sorbate (Tabernanthalog·Sorbate, Form A). The salt underwent neat milling and separately with the addition of tetradecafluorohexane (TDFH). The following experiments were performed: Experiment 6-Sample A1 (30 Hz, 2 h), Experiment 6-Sample A2 (30 Hz, 5.5 h) and Experiment 6-Sample A3 (30 Hz 1 h, TDFH), the products from each experiment was analysed by XRPD to determine the extent of crystallinity (FIG. 812). None of the experiments provided amorphous material.

3.2.4 Generation of the Hexafluoroisopropanol (HFIPA) Solvate

During the initial amorphous experiments, a new powder pattern was observed attributed to a HFIPA solvate, this form was reprepared and characterised.

The Tabernanthalog·Sorbate·hemiHFIPA solvate was generated by the evaporation of a solution of Tabernanthalog·Sorbate (Tabernanthalog·Sorbate, Form A), dissolved in HFIPA. This was characterised by $^1$H NMR, $^{19}$F NMR, XRPD, TGA, DSC.

Stability of the salt (Table 302) at elevated relative humidity was examined at 20 and 40° C., to determine if the HFIPA solvent can be replaced by water to generate the isomorphic hydrate. A partial loss of HFIPA was observed after 5 days, by $^{19}$F NMR. No change in the powder pattern was observed from this treatment and the powder pattern did not match the powder pattern of the hydrate single crystal structure.

Tabernanthalog·Sorbate·HemiHFIPA was heated to expel any solvent present in the sample. The sample was analysed by XRPD to determine if the loss of solvent changed the form. The analysis demonstrated that upon loss of solvent, the phase reverts to Form A, the same as the input material (Tabernanthalog·Sorbate).

TABLE 302

Generation of Tabernanthalog•Sorbate•hemiHFIPA

| Experiment references | Input | Activity | Outcome |
|---|---|---|---|
| Experiment 3-Sample A1 | Tabernanthalog•Sorbate | HFIPA evaporation | HemiHFIPA |
| Experiment 3-Sample A2 | Experiment 3-Sample A1 | Drying under N2 | HemiHFIPA |
| Experiment 3-Sample B1 | Experiment 3-Sample A2 | 75% RH 20° C. | HemiHFIPA |
| Experiment 3-Sample C1 | Experiment 3-Sample A2 | 75% RH 40° C. | HemiHFIPA |
| Experiment 3-Sample C2 | Experiment 3-Sample C1 | TGA (20-100° C.) | Converted to Form A |

4. Conclusions

The preparation and characterisation of the amorphous phase was carried out and Tg was determined for each compound (refer to Table 301). The residues were analysed by $^1$H NMR spectroscopy and LC-MS, to confirm that the sample had not degraded during the thermal treatment.

Due to the issues associated with the generation of multiple gramme quantities of the amorphous phase, the remainder of the change order could not be completed.

A Tabernanthalog·Sorbate hemiHFIPA solvate was generated from the evaporation of a solution of Tabernanthalog·Sorbate in HFIPA, the product was characterised by XRPD, $^1$H NMR, $^{19}$F NMR, TGA and DSC analyses. Stability of this sample was examined over 5 days at 75% RH at 20 and 40° C. Samples, when reanalysed, exhibited a reduction of HFIPA at the 5 days, time point and probable replacement of HFIPA by water in the crystal structure.

5. Experimental

5.1 Instrumentation

5.1.1 DSC

A Mettler Toledo DSC 3 instrument was used for the thermal analysis operating with STARe™ software. The analysis was conducted in open aluminium pans (40 µl), under nitrogen and sample sizes ranged from 1 to 10 mg. Typical analysis method was 20 to 250° C. at 10° C./minute. Alternatively, a Mettler Toledo DSC1 with auto-sampler instrument was used for the thermal analysis operating with STARe™ software. The analysis was conducted in open aluminium pans (40 µl), under nitrogen and sample sizes ranged from 1 to 10 mg. Typical analysis method was 25 to 300° C. at 10 K/minute.

5.1.2 LC-MS

Routine Liquid Chromatography-Mass Spectrometry (LC-MS) data were collected using the Agilent 1260 Infinity II interfaced with 1260 Infinity II DAD HS and Agilent series 1260 Infinity II binary pump.

The instrument used a single quadrupole InfinityLab MSD. The instrument was calibrated up to 2000 Da.

LC-MS method parameters:
inj. vol: 5 µl
Detection: UV @ 254 nm
Mobile Phase A: Acetonitrile+0.1% TFA/H$_2$O 95:5
Mobile Phase B: Acetonitrile±0.05% TFA/H$_2$O 5:95

| Time (mins) | % A | % B |
|---|---|---|
| 0.0 | 100 | 0 |
| 1 | 100 | 0 |
| 10.00 | 0 | 100 |
| 10.01 | 100 | 0 |
| 12.00 | 100 | 0 |

Flow Rate: 1.0 ml/min
Column temperature: 30° C.
Run time 12 minutes.

5.1.3 1H NMR $^1$H NMR spectra were acquired using a Bruker 400 MHz spectrometer and data was processed using Topspin. Samples were prepared in DMSO-d$_6$ at typical concentrations of 10 to 20 mg/ml and up to 50 mg/ml for quantitative (Q) $^1$H NMR w/w assay and calibrated to the corresponding non-deuterated solvent residual at 2.50 ppm.

5.1.4 $^1$H NMR Assay

Assays (w/w) of the API by $^1$H NMR spectroscopy were measured by the project chemist using Topspin. Internal standard 2,3,5,6-terachloronitrobenzene (TCNB, ca. 20 mg, F.W. 260.89) were dissolved in DMSO-d& (1.0 ml) and the $^1$H NMR spectrum was acquired using an extended relaxation method.

5.1.5 TGA

A Mettler Toledo TGA-2 instrument was used to measure the weight loss as a function of temperature from 25 to 500° C. The scan rate was typically 5 or 10° C. per minute. Experiments and analysis were carried out using the STARe™ software. The analysis was conducted in 100 µl open aluminium pans, under nitrogen and sample sizes ranged from 1 to 10 mg.

5.1.6 XRPD

X-ray powder diffraction (XRPD) analysis was carried out using a Bruker D2 Phaser powder diffractometer equipped with a LynxEye detector. The specimens underwent minimum preparation but, if necessary, were lightly milled in a pestle and mortar before acquisition. The specimens were located at the centre of a silicon sample holder within a 5 mm pocket (ca. 5 to 10 mg). The samples were continuously spun during data collection and scanned using a step size of 0.02° 2-theta (2θ) between the range of 4° to 40° 2-theta or 5° to 60° 2-theta. Data were acquired using either 9 minute or 20-minute acquisition methods. Bruker Diffrac.Suite was used to process the data

5.1.7 Bead Milling

Comminution was carried out by a MM500 Vario Mixing Mill, inside 1.5 and 5 ml stainless steel jars with 5 mm ball bearings. Milling was performed at 30 Hz between 2-16 hours, sample sizes ranged from 50-100 mg. The extent of pulverisation was determined by the nature of the API, the number of ball bearings employed and the frequency of oscillation of the vessel.

5.1.8 Spray Drying

Spray drying was performed on a ProCept 4M8-Trix closed loop nitrogen system, Nozzle size 1.0 mm. Parameters:
Inlet Gas Flow—0.3 ml/min
Inlet Temperature—130° C.
Column out temp—69° C.
Cyclone In Temperature—59° C.
Underpressure Column—5.5 mBar
Cyclone Differential Pressure—58 mBar
Nozzle Gas Flow—10.6/min
Chiller temp—−15° C.
Oxygen level—1.6%

5.2 General Procedures

5.2.1 Cryodesiccation/Freeze Drying

Experimental Reference: Experiment 4-Sample A1, Experiment 5-Sample A1

Each salt was charged to a 7 ml vial (50 mg, 1.0 wt). To the vial containing Tabernanthalog·Monofumarate (Tabernanthalog·Monofumarate), was charged water (10.0 vol), to fully dissolve the sample. Tabernanthalog·Sorbate (A1270-076-A1) was taken-up in ethanol/water (15% v/v, 10 vol), a further charge of water (1.0 ml), was added to ensure that the sample dissolved. Vials containing the salt solutions were placed on the freeze drier apparatus overnight, and the cryo-desiccated products were recovered the following morning and analysed by XRPD each product remained crystalline.

5.2.2 Evaporation

Experimental Reference: Experiment 5-Sample A2

Tabernanthalog·Monofumarate (A1272-082-A2, 51.1 mg, 1.0 wt) was charged to a 7 ml scintillation vial followed by THF (2 ml, 60 vol), the suspension was heated to 50° C., until full dissolution was observed. The vial was stoppered by foil and a pin hole was pierced in the top. The vial was located under a steady $N_2$ stream. The solvent evaporated to dryness overnight, and the product was analysed by XRPD yielding crystalline material

5.2.3 HFIPA Evaporation

Experimental Reference: Experiment 3-Sample A1, Experiment 3-Sample A2

Tabernanthalog·Sorbate (A1270-076-A1, 99.4 mg, 1.0 wt) was charged to a 7 ml scintillation vial, followed by hexafluoroisopropanol (HFIPA, 5.0 vol, 0.5 ml), after which, the sample fully dissolved. The cap was replaced by foil and pierced on the top. Solvent was allowed to evaporate, to afford a dry, brown solid that was analysed by XRPD yielding crystalline pattern #7. Sample were dried under $N_2$ stream for 5 h and reanalysed by XRPD, remaining as pattern #7

5.2.4 Rotary Evaporation

Experimental Reference: Experiment 4-Sample B1

Tabernanthalog·Sorbate (A1270-076-A1, 50.0 mg, 1.0 wt) was charged to a 7 ml scintillation vial followed by hexafluoroisopropanol (HFIPA, 0.5 ml, 10 vol), to yield a clear solution. The solution was concentrated to dryness, by rotary evaporation, yielding an oil, that was allowed to stand undisturbed overnight. The product exhibited crystallinity by XRPD.

5.2.5 Binary Solvent

Experimental Reference: Experiment 4-Sample A4

Tabernanthalog·Sorbate (A1270-076-A1, 50.0 mg, 1.0 wt) was charged to a 7 ml scintillation vial, followed by methanol (300 µl, 6.0 vol). The solution was clarified by filtration into a 7 ml scintillation vial, containing diethyl ether (1.0 ml, 20.0 vol). The solution was dried under sustained $N_2$ stream and was analysed by XRPD yielding crystalline material HFIPA desiccator sample Experimental Reference: Experiment 4-Sample B2, Experiment 4-Sample B3

Tabernanthalog·Sorbate (Experiment 4-Sample B1, 50.0 mg, 1.0 wt, Pattern #7) was taken up in HFIPA (50.0 µl, 1 vol) and transferred to a low background, silicon XRPD sample plate, and dried inside a vacuum desiccator for 4 h at 20° C. The sample was removed from the desiccator to yield a clear gum, that was analysed by XRPD yielding partially crystalline material. Sample placed into desiccator and left to dry overnight before reanalysis by XRPD yielding fully crystalline material indicating crystallisation of sample overnight.

5.2.6 Spray Drying

Experimental Reference: Experiment 4-Sample D1

Tabernanthalog·Sorbate (A1270-076-A1, 102 mg, 1 wt) was charged to a 7.0 ml scintillation vial followed by methanol (1.9 ml, 19.0 vol). The solution was loaded into the spray drier apparatus. The procedure yielded a brown powder (30 mg, 30% th.). Crystalline material was evident by XRPD. The specimen was allowed to stand, undisturbed overnight, prior to reanalysis by XRPD; consequently, the specimen exhibited much improved crystallinity, after this time.

5.2.7 Bead Milling

Experimental Reference: A1270-084-A1

Tabernanthalog·Sorbate (A1270-076-A1, Form A) was charged to a 1.5 ml steel milling-vessel with a single 5 mm ball bearing. The sample was milled for 5.5 h at 30 Hz and yielded an off-white powder, that was analysed by XRPD, no change in crystallinity. 5.2.8 DSC Experimental Reference: Experiment 1-Sample A1, Experiment 1-Sample B1, Experiment 2-Sample A1, Experiment 2-Sample B1

Two DSC pans were charge with the appropriate salt (Tabernanthalog·Sorbate, A1270-076-A1 and Tabernanthalog·Monofumarate, Tabernanthalog·Monofumarate), the first DSC pan was not sealed (open pan DSC), the second was sealed (hermetic sealed pan DSC). The open pan DSC was cycled from 20° C. to just after the melt event for each, cooled to −20° C., and left to stand under ambient conditions over night. The open pan DSC was then heated to just before the thermal degradation event (Tabernanthalog·Sorbate ca. 160° C., Tabernanthalog·Monofumarate ca. 210° C.) The hermetic sealed DSC was heated from 20° C. to just after the melt event, cooled to −20° C. then headed to just before the same degradation event.

5.2.9 TGA

Experimental Reference: Experiment 1-Sample C1, Experiment 2-Sample C1

Two TGA crucibles were charged with the appropriate salt (Tabernanthalog·Sorbate, A1270-076-A1, Tabernanthalog·Monofumarate, Tabernanthalog·Monofumarate), both were thermocycled from 20° C. to past the melt event and then cooled to −20° C., each pan was then immediately heated to just before the degradation event to measure the Tg event.

5.2.10 Hot Plate Melt

Experimental Reference: Experiment 1-Sample D1, Experiment 2-Sample E1

A XRPD, low-background silicon sample plate was loaded with the appropriate salt (Tabernanthalog·Sorbate, Tabernanthalog·Monofumarate), and heated on a hot plate mantle until melted, the melt was cooled and analysed by XRPD to ensure amorphous.

5.2.11 Hot Stage Microscope Melt

Experimental Reference: Experiment 1-Sample E1, Experiment 2-Sample E1

A XRPD, low background silicon sample plate was loaded with the appropriate salt (Tabernanthalog·Sorbate, Tabernanthalog·Monofumarate,) and heated on a hot stage microscope block until melted: the specimens were cooled and analysed by XRPD to ensure that the phases were amorphous. Once amorphous material was obtained, both samples were analysed by LC-MS and $^1$H NMR to ensure that no change in chemical composition had occurred.

5.2.12 Stability at 75% RH 20° C., and 40° C.

Experimental Reference: Experiment 3-Sample B1, Experiment 3-Sample C1

Tabernanthalog·Sorbate·HemiHFIPA (Experiment 3-Sample A2, 28.2 mg, 1 wt) was charged into a wide necked solid sample vial, the uncapped vial was placed inside a larger amber jar containing an aqueous NaCl slurry. The amber jar was sealed and left to stand for 5 days. The specimen analysed by XRPD, $^{19}$F NMR, TGA and DSC after 5 days. No change in powder pattern observed and a small decrease in HFIPA content after 5 days,

TABLE 303

Peak angle data of Experiment 3-Sample A2. Reported only peaks >10%. Rel. Intensity values calculated using Net Intensity values.

| 2-θ (°) | d Value | Rel. Intensity (%) |
|---|---|---|
| 22.6 | 3.9 | 100.0 |
| 9.4 | 9.4 | 79.6 |
| 17.7 | 5.0 | 63.4 |
| 17.1 | 5.2 | 59.4 |
| 19.0 | 4.7 | 54.6 |
| 6.3 | 14.0 | 51.4 |
| 15.4 | 5.8 | 44.7 |
| 17.1 | 5.2 | 40.3 |
| 19.4 | 4.6 | 33.5 |
| 13.3 | 6.7 | 30.3 |
| 23.8 | 3.7 | 30.2 |
| 23.3 | 3.8 | 30.1 |
| 21.2 | 4.2 | 29.3 |
| 16.1 | 5.5 | 26.8 |
| 15.8 | 5.6 | 23.1 |
| 27.3 | 3.3 | 22.0 |
| 21.9 | 4.1 | 15.2 |
| 30.6 | 2.9 | 13.5 |
| 27.8 | 3.2 | 12.7 |
| 16.5 | 5.4 | 12.3 |
| 14.0 | 6.3 | 12.2 |
| 25.1 | 3.6 | 12.1 |
| 26.6 | 3.4 | 11.5 |
| 29.3 | 3.0 | 10.8 |

TABLE 304

Peak angle data of Experiment 4-Sample A1. Reported only peaks > 10%. Rel. Intensity values calculated using Net Intensity values.

| 2-θ (°) | d Value | Rel. Intensity (%) |
|---|---|---|
| 5.7 | 15.6 | 100.0 |
| 11.4 | 7.8 | 29.9 |
| 18.9 | 4.7 | 15.9 |
| 22.6 | 3.9 | 11.9 |
| 24.5 | 3.6 | 17.1 |
| 24.6 | 3.6 | 19.9 |

TABLE 305

Peak angle data of Experiment 4-Sample A2. Reported only peaks > 10%. Rel. Intensity values calculated using Net Intensity values.

| 2-θ (°) | d Value | Rel. Intensity (%) |
|---|---|---|
| 5.6 | 15.64 | 100.0 |
| 11.3 | 7.80 | 40.0 |
| 18.9 | 4.69 | 13.6 |

TABLE 306

Peak angle data of Experiment 4-Sample A3. Reported only peaks > 10%. Rel. Intensity values calculated using Net Intensity values.

| 2-θ (°) | d Value | Rel. Intensity (%) |
|---|---|---|
| 5.7 | 15.51 | 100 |
| 10.5 | 8.39 | 18 |
| 11.4 | 7.75 | 45 |
| 18.0 | 4.93 | 13 |
| 18.9 | 4.69 | 27 |
| 19.2 | 4.62 | 11 |
| 21.4 | 4.15 | 11 |
| 22.7 | 3.92 | 14 |
| 24.4 | 3.64 | 11 |
| 24.7 | 3.60 | 23 |

TABLE 307

Peak angle data of Experiment 4-Sample A4. Reported only peaks > 10%. Rel. Intensity values calculated using Net Intensity values.

| 2-θ (°) | d Value | Rel. Intensity (%) |
|---|---|---|
| 5.7 | 15.59 | 100 |
| 11.4 | 7.78 | 48 |
| 18.9 | 4.70 | 19 |
| 22.8 | 3.89 | 11 |

TABLE 308

Peak angle data of Experiment 4-Sample B1. Reported only peaks > 10%. Rel. Intensity values calculated using Net Intensity values.

| 2-θ (°) | d Value | Rel. Intensity (%) |
|---|---|---|
| 5.7 | 15.53 | 100 |
| 11.4 | 7.77 | 23 |

TABLE 309

Peak angle data of Experiment 4-Sample B3. Reported only peaks > 10%. Rel. Intensity values calculated using Net Intensity values.

| 2-θ (°) | d Value | Rel. Intensity (%) |
|---|---|---|
| 22.5 | 3.95 | 100 |
| 22.7 | 3.92 | 99 |
| 7.6 | 11.61 | 98 |
| 5.7 | 15.38 | 67 |
| 22.6 | 3.94 | 58 |
| 17.1 | 5.20 | 48 |
| 13.3 | 6.66 | 38 |

TABLE 309-continued

Peak angle data of Experiment 4-Sample B3. Reported only peaks > 10%. Rel. Intensity values calculated using Net Intensity values.

| 2-θ (°) | d Value | Rel. Intensity (%) |
|---|---|---|
| 15.4 | 5.75 | 38 |
| 9.5 | 9.34 | 33 |
| 11.5 | 7.72 | 30 |
| 23.3 | 3.81 | 27 |
| 19.0 | 4.68 | 25 |
| 17.2 | 5.14 | 19 |
| 23.6 | 3.76 | 19 |
| 14.1 | 6.29 | 18 |
| 23.8 | 3.74 | 18 |
| 15.2 | 5.81 | 16 |
| 17.7 | 5.01 | 14 |
| 6.3 | 14.02 | 14 |
| 15.9 | 5.56 | 13 |
| 23.1 | 3.85 | 12 |
| 16.9 | 5.24 | 12 |
| 21.3 | 4.17 | 12 |
| 17.5 | 5.05 | 11 |

TABLE 310

Peak angle data of Experiment 4-Sample C1. Reported only peaks > 10%. Rel. Intensity values calculated using Net Intensity values.

| 2-θ (°) | d Value | Rel. Intensity (%) |
|---|---|---|
| 5.7 | 15.57 | 100 |
| 18.9 | 4.70 | 87 |
| 24.7 | 3.61 | 76 |
| 11.4 | 7.75 | 56 |
| 24.5 | 3.63 | 52 |
| 10.5 | 8.43 | 50 |
| 22.6 | 3.93 | 45 |
| 19.1 | 4.64 | 44 |
| 17.9 | 4.94 | 36 |
| 21.4 | 4.15 | 30 |
| 26.9 | 3.31 | 22 |
| 17.3 | 5.12 | 22 |
| 9.4 | 9.42 | 18 |
| 29.6 | 3.02 | 16 |
| 28.5 | 3.13 | 16 |
| 25.2 | 3.53 | 13 |

TABLE 311

Peak angle data of Experiment 4-Sample D1. Reported only peaks > 10%. Rel. Intensity values calculated using Net Intensity values.

| 2-θ (°) | d Value | Rel. Intensity (%) |
|---|---|---|
| 18.9 | 4.68 | 100 |
| 5.7 | 15.36 | 27 |
| 10.5 | 8.41 | 24 |
| 15.1 | 5.85 | 22 |
| 27.4 | 3.25 | 22 |
| 18.0 | 4.93 | 17 |
| 24.7 | 3.60 | 12 |

TABLE 312

Peak angle data of Experiment 4-Sample D2. Reported only peaks > 10%. Rel. Intensity values calculated using Net Intensity values.

| 2-θ (°) | d Value | Rel. Intensity (%) |
|---|---|---|
| 5.7 | 15.46 | 100 |
| 18.9 | 4.69 | 55 |
| 10.5 | 8.39 | 47 |
| 11.5 | 7.72 | 38 |
| 24.7 | 3.60 | 35 |
| 18.0 | 4.92 | 27 |
| 24.6 | 3.62 | 24 |
| 19.2 | 4.63 | 24 |
| 18.4 | 4.81 | 23 |
| 22.7 | 3.92 | 20 |
| 10.3 | 8.57 | 18 |
| 9.4 | 9.36 | 18 |
| 21.5 | 4.14 | 15 |
| 17.4 | 5.09 | 14 |
| 26.9 | 3.31 | 10 |

TABLE 313

Peak angle data of Experiment 4-Sample E1. Reported only peaks >10%. Rel. Intensity values calculated using Net Intensity values.

| 2-θ (°) | d Value | Rel. Intensity (%) |
|---|---|---|
| 18.9 | 4.68 | 100 |
| 5.7 | 15.57 | 77 |
| 24.7 | 3.61 | 49 |
| 19.1 | 4.63 | 46 |
| 10.5 | 8.39 | 44 |
| 18.4 | 4.82 | 42 |
| 18.0 | 4.91 | 40 |
| 11.4 | 7.77 | 32 |
| 24.5 | 3.64 | 31 |
| 22.6 | 3.92 | 29 |
| 10.4 | 8.49 | 28 |
| 21.5 | 4.14 | 27 |
| 17.5 | 5.08 | 22 |
| 26.8 | 3.32 | 15 |
| 9.5 | 9.35 | 14 |
| 15.2 | 5.84 | 11 |
| 27.4 | 3.25 | 11 |

TABLE 314

Peak angle data of Experiment 5-Sample A1. Reported only peaks >10%. Rel. Intensity values calculated using Net Intensity values.

| 2-θ (°) | d Value | Rel. Intensity (%) |
|---|---|---|
| 16.3 | 5.43 | 100 |
| 9.1 | 9.76 | 91 |
| 25.6 | 3.48 | 81 |
| 19.3 | 4.60 | 31 |
| 26.8 | 3.33 | 31 |
| 25.1 | 3.54 | 22 |
| 16.7 | 5.31 | 20 |
| 18.1 | 4.89 | 19 |
| 22.3 | 3.99 | 16 |
| 27.2 | 3.27 | 15 |
| 30.0 | 2.98 | 14 |
| 23.1 | 3.85 | 11 |

TABLE 3151

Peak angle data of Experiment 5-Sample A2. Reported only peaks >10%. Rel. Intensity values calculated using Net Intensity values.

| 2-θ (°) | d Value | Rel. Intensity (%) |
|---|---|---|
| 7.4 | 11.89 | 100.0 |
| 21.5 | 4.13 | 36.2 |
| 16.0 | 5.54 | 34.1 |
| 20.3 | 4.38 | 15.9 |
| 25.7 | 3.46 | 11.5 |
| 20.8 | 4.27 | 10.1 |

TABLE 316

Peak angle data of Experiment 5-Sample A3. Reported only peaks >10%. Rel. Intensity values calculated using Net Intensity values.

| 2-θ (°) | d Value | Rel. Intensity (%) |
|---|---|---|
| 8.2 | 10.75 | 100 |
| 11.2 | 7.88 | 31 |
| 17.1 | 5.20 | 29 |
| 24.4 | 3.65 | 13 |
| 23.8 | 3.74 | 13 |
| 21.5 | 4.12 | 13 |
| 20.2 | 4.39 | 12 |
| 8.9 | 9.93 | 11 |

TABLE 3172

Peak angle data of Experiment 6-Sample A1. Reported only peaks >10%. Rel. Intensity values calculated using Net Intensity values.

| 2-θ (°) | d Value | Rel. Intensity (%) |
|---|---|---|
| 18.9 | 4.70 | 100 |
| 24.5 | 3.63 | 67 |
| 17.9 | 4.94 | 45 |
| 22.6 | 3.94 | 37 |
| 5.6 | 15.77 | 35 |
| 17.4 | 5.10 | 32 |
| 11.3 | 7.82 | 29 |
| 10.5 | 8.42 | 28 |
| 21.4 | 4.15 | 27 |
| 26.7 | 3.34 | 20 |
| 25.3 | 3.52 | 18 |
| 26.8 | 3.33 | 16 |
| 29.6 | 3.02 | 14 |
| 9.4 | 9.44 | 14 |
| 19.7 | 4.51 | 13 |
| 28.5 | 3.13 | 13 |

TABLE 318

Peak angle data of Experiment 6-Sample A2. Reported only peaks >10%. Rel. Intensity values calculated using Net Intensity values.

| 2-θ (°) | d Value | Rel. Intensity (%) |
|---|---|---|
| 18.9 | 4.70 | 100 |
| 24.6 | 3.62 | 84 |
| 24.5 | 3.63 | 69 |
| 19.1 | 4.65 | 53 |
| 17.9 | 4.94 | 52 |
| 22.6 | 3.93 | 49 |
| 5.6 | 15.70 | 49 |
| 21.4 | 4.15 | 39 |
| 10.5 | 8.42 | 38 |
| 11.4 | 7.79 | 33 |
| 17.3 | 5.11 | 33 |
| 26.8 | 3.32 | 25 |
| 29.6 | 3.02 | 20 |
| 28.5 | 3.13 | 20 |
| 25.3 | 3.52 | 20 |
| 9.4 | 9.42 | 16 |
| 19.7 | 4.50 | 15 |
| 22.0 | 4.04 | 12 |

TABLE 319

Peak angle data of Experiment 6-Sample A3. Reported only peaks >10%. Rel. Intensity values calculated using Net Intensity values.

| 2-θ (°) | d Value | Rel. Intensity (%) |
|---|---|---|
| 18.9 | 4.70 | 100 |
| 5.7 | 15.54 | 92 |
| 24.7 | 3.61 | 80 |
| 24.5 | 3.62 | 57 |
| 10.5 | 8.42 | 53 |
| 11.4 | 7.75 | in |
| 22.6 | 3.93 | 52 |
| 17.9 | 4.94 | 45 |
| 19.1 | 4.63 | 44 |
| 21.4 | 4.15 | 37 |
| 17.4 | 5.11 | 32 |
| 26.9 | 3.32 | 25 |
| 9.4 | 9.41 | 24 |
| 28.5 | 3.13 | 19 |
| 29.6 | 3.01 | 19 |
| 25.3 | 3.52 | 16 |
| 22.1 | 4.03 | 14 |
| 20.8 | 4.27 | 11 |
| 19.7 | 4.49 | 10 |

TABLE 320

Peak angle data of Experiment 1-Sample D2. Reported only peaks >10%. Rel. Intensity values calculated using Net Intensity values.

| 2-θ (°) | d Value | Rel. Intensity (%) |
|---|---|---|
| 18.7 | 4.73 | 100 |
| 24.5 | 3.62 | 94 |
| 22.5 | 3.95 | 62 |
| 11.2 | 7.86 | 61 |
| 24.2 | 3.67 | 55 |
| 22.8 | 3.90 | 46 |
| 19.0 | 4.66 | 45 |
| 21.3 | 4.17 | 36 |
| 17.9 | 4.96 | 36 |
| 26.7 | 3.33 | 33 |
| 18.2 | 4.86 | 32 |
| 28.4 | 3.14 | 25 |
| 29.5 | 3.02 | 25 |
| 21.9 | 4.05 | 19 |
| 17.2 | 5.14 | 17 |
| 20.6 | 4.30 | 14 |
| 25.2 | 3.53 | 13 |
| 29.1 | 3.06 | 12 |
| 10.3 | 8.57 | 11 |
| 23.4 | 3.80 | 11 |
| 27.3 | 3.27 | 11 |

TABLE 321

Peak angle data of Experiment 2-Sample E1. Reported only peaks >10%. Rel. Intensity values calculated using Net Intensity values.

| 2-θ (°) | d Value | Rel. Intensity (%) |
|---|---|---|
| 19.4 | 4.57 | 100 |
| 26.0 | 3.43 | 75 |
| 17.0 | 5.21 | 29 |
| 12.9 | 6.87 | 28 |
| 24.5 | 3.63 | 18 |
| 20.6 | 4.31 | 16 |
| 18.0 | 4.93 | 16 |
| 15.6 | 5.69 | 15 |

TABLE 322

Peak angle data of Experiment 3-Sample A1. Reported only peaks >10%. Rel. Intensity values calculated using Net Intensity values.

| 2-θ (°) | d Value | Rel. Intensity (%) |
|---|---|---|
| 9.4 | 9.36 | 100 |
| 6.3 | 14.04 | 58 |
| 19.0 | 4.68 | 48 |
| 22.6 | 3.93 | 23 |
| 17.7 | 5.02 | 19 |
| 17.1 | 5.20 | 16 |
| 15.8 | 5.61 | 16 |
| 19.4 | 4.57 | 15 |
| 15.4 | 5.75 | 14 |
| 17.2 | 5.15 | 13 |
| 25.4 | 3.51 | 11 |

TABLE 323

Peak angle data of Experiment 3-Sample B1. Reported only peaks >10%. Rel. Intensity values calculated using Net Intensity values.

| 2-θ (°) | d Value | Rel. Intensity (%) |
|---|---|---|
| 9.5 | 9.30 | 100 |
| 19.0 | 4.66 | 79 |
| 22.6 | 3.92 | 73 |
| 6.4 | 13.90 | 60 |
| 15.4 | 5.74 | 59 |
| 17.7 | 5.01 | 57 |
| 17.1 | 5.18 | 49 |
| 17.2 | 5.14 | 46 |
| 19.5 | 4.56 | 44 |
| 13.3 | 6.66 | 43 |
| 15.9 | 5.58 | 30 |
| 21.3 | 4.17 | 27 |
| 23.8 | 3.73 | 27 |
| 16.1 | 5.49 | 26 |
| 23.3 | 3.81 | 23 |
| 21.9 | 4.05 | 23 |
| 27.3 | 3.26 | 20 |
| 25.4 | 3.50 | 19 |
| 14.1 | 6.29 | 19 |
| 25.1 | 3.54 | 12 |
| 26.6 | 3.35 | 11 |

TABLE 324

Peak angle data of Experiment 3-Sample C1. Reported only peaks >10%. Rel. Intensity values calculated using Net Intensity values.

| 2-θ (°) | d Value | Rel. Intensity (%) |
|---|---|---|
| 22.7 | 3.92 | 100 |
| 17.7 | 5.00 | 59 |
| 17.2 | 5.17 | 57 |
| 9.5 | 9.29 | 56 |
| 19.0 | 4.66 | 49 |
| 15.4 | 5.73 | 46 |
| 13.3 | 6.65 | 44 |
| 6.3 | 13.91 | 35 |
| 19.5 | 4.55 | 33 |
| 16.2 | 5.48 | 31 |
| 23.8 | 3.73 | 28 |
| 23.4 | 3.81 | 26 |
| 21.3 | 4.16 | 24 |
| 16.0 | 5.54 | 22 |
| 27.3 | 3.26 | 20 |
| 21.9 | 4.05 | 16 |
| 14.1 | 6.28 | 15 |
| 25.1 | 3.54 | 13 |
| 16.6 | 5.35 | 13 |
| 27.9 | 3.20 | 12 |
| 26.6 | 3.35 | 12 |
| 25.5 | 3.49 | 12 |
| 30.7 | 2.91 | 11 |

TABLE 325

Peak angle data of Experiment 3-Sample C2. Reported only peaks >10%. Rel. Intensity values calculated using Net Intensity values.

| 2-θ (°) | d Value | Rel. Intensity (%) |
|---|---|---|
| 5.7 | 15.49 | 100 |
| 18.9 | 4.69 | 90 |
| 31.7 | 2.82 | 89 |
| 24.7 | 3.60 | 80 |
| 10.5 | 8.39 | 53 |
| 18.0 | 4.93 | 53 |
| 22.7 | 3.92 | 53 |
| 11.4 | 7.73 | 50 |
| 19.2 | 4.61 | 45 |
| 21.4 | 4.14 | 44 |
| 24.5 | 3.64 | 40 |
| 17.4 | 5.10 | 32 |
| 26.9 | 3.31 | 27 |
| 9.4 | 9.36 | 20 |
| 28.5 | 3.13 | 17 |
| 25.3 | 3.51 | 17 |
| 22.1 | 4.02 | 15 |
| 29.7 | 3.01 | 15 |
| 20.8 | 4.26 | 13 |
| 19.8 | 4.48 | 10 |

SC-XRD Bond Length Comparison

Intermolecular interactions of the single crystal structures obtained were analysed. Bond length of interactions at the salification sites were ~5% shorter on average than hydrogen bonding interactions at other available sites, suggesting these are salts (incorporation of ionised species into the crystal network) being formed and not co-crystals (incorporation of neutral species into the crystal network).

TABLE 326

Intermolecular bonds observed in Crystal structures.

| Experiment references | Salt form | Salification bond length (A) | Hydrogen bond length (A) | Hydrogen bond length (A) |
|---|---|---|---|---|
| A1270-076-A1 | Tabernanthalog • Sorbate | 2.7015 | 2.847 | — |
| A1272-032-M2 | Tabernanthalog • Monofumarate | 2.704 | 2.893 | 2.477 (between Fumarates) |
| A1272-032-M2 | Tabernanthalog • Monofumarate | 2.697 | 2.811 | |

NMR Shift Comparison

Comparison of $^1$H NMR spectrum between the native form of Tabernanthalog compared to Tabernanthalog·Sorbate and Tabernanthalog·Monofumarate, Small shift in ppm between peaks near the ionisation sites, however shifts appear to be driven by $\Delta pK_a$.

$^1$H NMR Spectrum Used:
Tabernanthalog·Native
Tabernanthalog·Sorbate
Tabernanthalog·Monofumarate

TABLE 327

$^1$H NMR peak shift comparison, reported in ppm.

| Proton | Tabernanthalog • Native | Tabernanthalog • Sorbate | Asorbate | Tabernanthalog • Monofumarate | Afumarate |
|---|---|---|---|---|---|
| A | 2.392 | 2.405 | 0.013 | 2.595 | 0.203 |
| BCDI | 2.715 | 2.736 | 0.021 | 2.97 | 0.255 |
| BCDI | 2.858 | 2.856 | -0.002 | 2.996 | 0.138 |
| Average | | | 0.01 | | 0.20 |

LCMS

LC-MS was performed on each salt (Tabernanthalog·Sorbate, Tabernanthalog·Monofumarate,) to ensure there was no change in chemical composition during the heating process, two peaks were observed in A1270-088-E1, switching in intensity with changing UV wavelength. A sample was pure sorbic acid was also analysed to ensure the $2^{nd}$ peak (2.65 min) was sorbic acid. The sample of pure sorbic acid contained a singular peak (2.61 min) suggesting the first peak is in fact API, the second sorbic acid.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A solid form of tabernanthalog monofumarate salt of the following formula:

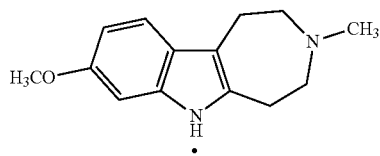

-continued

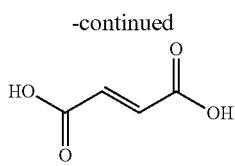

wherein the solid form is crystalline polymorphic Pattern #6a;

(i) wherein crystalline polymorphic Pattern #6a is characterized by an X-ray powder diffraction diffractogram comprising two signals at angles (°2θ) selected from the group consisting of 19.6°±0.2 °2θ, 20.8°±0.2 °2θ, and 26.2°±0.2 °2θ; or (ii) wherein crystalline polymorphic Pattern #6a is characterized by an X-ray powder diffraction diffractogram comprising three signals at angles (°2θ) selected from the group consisting of 16.2°±0.2 °2θ, 18.9°±0.2 °2θ, 20.2°±0.2 °2θ, and 24.9°±0.2 °2θ; and wherein the X-ray powder diffraction diffractogram signals are present when the X-ray powder diffraction is carried out using Cu Kα1 radiation.

2. The solid form of claim 1, wherein the crystalline polymorphic Pattern #6a is characterized by an X-ray powder diffraction diffractogram comprising two signals at angles (°2θ) selected from the group consisting of 19.6°±0.2 °2θ, 20.8°±0.2 °2θ, and 26.2°±0.2 °2θ.

3. The solid form of claim 2, wherein the crystalline polymorphic Pattern #6a is further characterized by an X-ray powder diffraction diffractogram comprising one or two additional signals at angles (°2θ) selected from the group consisting of 16.6°±0.2 °2θ, 17.1°±0.2 °2θ, and 25.4°±0.2 °2θ.

4. The solid form of claim 3, wherein the crystalline polymorphic Pattern #6a is further characterized by an X-ray powder diffraction diffractogram comprising one or two additional signals at angles (°2θ) selected from the group consisting of 13.0°±0.2 °2θ, 22.2°±0.2 °2θ, 23.0°±0.2 °2θ, and 27.5°±0.2 °2θ.

5. The solid form of claim 1, wherein the crystalline polymorphic Pattern #6a is characterized by an X-ray powder diffraction diffractogram comprising three signals at angles (°2θ) selected from the group consisting of 16.2°±0.2 °2θ, 18.9°±0.2 °2θ, 20.2°±0.2 °2θ, and 24.9°±0.2 °2θ.

6. The solid form of claim 5, wherein the crystalline polymorphic Pattern #6a is further characterized by an X-ray powder diffraction diffractogram comprising one or two additional signals at angles (°2θ) selected from the group consisting of 19.2°±0.2 °2θ and 25.8°±0.2 °2θ.

7. The solid form of claim 6, wherein the crystalline polymorphic Pattern #6a is further characterized by an X-ray powder diffraction diffractogram comprising one or two additional signals at angles (°2θ) selected from the group consisting of 12.6°±0.2 °2θ, 15.7°±0.2 °2θ, 17.3°±0.2 °2θ, 21.6°±0.2 °2θ, 23.6°±0.2 °2θ, 27.8°±0.2 °2θ, 29.2°±0.2 °2θ, 33.0°±0.2 °2θ, 36.2°±0.2 °2θ, 37.4°±0.2 °2θ, 39.3°±0.2 °2θ, 41.2°±0.2 °2θ, and 43.7°±0.2 °2θ.

8. A pharmaceutical composition comprising a pharmaceutically acceptable excipient and the solid form of claim 1.

9. A method for modulating 5-hydroxytryptamine$_{2A}$ (5-HT$_{2A}$) receptor activity in a subject, wherein the method comprises administering to the subject in need thereof a therapeutically effective amount of the solid form of claim 1.

10. The method of claim 9, wherein the subject has a disorder selected from the group consisting of a neurological disorder and a psychiatric disorder, or a combination thereof.

11. A solid form of tabernanthalog monofumarate salt of the following formula:

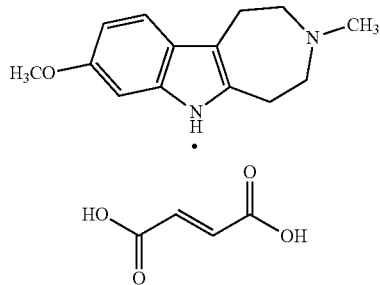 [SMILES: COc1ccc2c3c([nH]c2c1)CCN(C)CC3 ; O=C(O)/C=C/C(=O)O]

wherein the solid form is crystalline polymorphic Pattern #6a;
wherein crystalline polymorphic Pattern #6a is characterized by an X-ray powder diffraction diffractogram comprising two signals at angles (°2θ) selected from the group consisting of 16.2°±0.2 °2θ, 16.6°±0.2 °2θ, 18.9°±0.2 °2θ, 19.6°±0.2 °2θ, 20.2°±0.2 °2θ, 20.7°±0.2 °2θ, 24.9°±0.2 °2θ, and 26.2°±0.2 °2θ; and
wherein the X-ray powder diffraction diffractogram signals are present when the X-ray powder diffraction is carried out using Cu Kα1 radiation.

12. The solid form of claim 11, wherein the crystalline polymorphic Pattern #6a is further characterized by an X-ray powder diffraction diffractogram comprising one, two, three, or four additional signals at angles (°2θ) selected from the group consisting of 17.10°±0.2 °2θ, 19.3°±0.2 °2θ, 25.4°±0.2 °2θ, and 25.8°±0.2 °2θ.

13. The solid form of claim 12, wherein the crystalline polymorphic Pattern #6a is further characterized by an X-ray powder diffraction diffractogram comprising one, two, three, four, five, six, seven, or eight additional signals at angles (°2θ) selected from the group consisting of 12.6°±0.2 °2θ, 12.9°±0.2 °2θ, 13.0°±0.2 °2θ, 15.7°±0.2 °2θ, 17.3°±0.2 °2θ, 18.7°±0.2 °2θ, 19.2°±0.2 °2θ, 20.6°±0.2 °2θ, 21.6°±0.2 °2θ, 22.1°±0.2 °2θ, 22.2°±0.2 °2θ, 23.0°±0.2 °2θ, 23.6°±0.2 °2θ, 25.3°±0.2 °2θ, 26.1°±0.2 °2θ, 26.3°±0.2 °2θ, 27.5°±0.2 °2θ, 27.8°±0.2 °2θ, 29.2°±0.2 °2θ, 33.0°±0.2 °2θ, 33.5°±0.2 °2θ, 33.6°±0.2 °2θ, 36.2°±0.2 °2θ, 37.4°±0.2 °2θ, 37.8°±0.2 °2θ, 39.3°±0.2 °2θ, 41.2°±0.2 °2θ, and 43.7°±0.2 °2θ.

14. A pharmaceutical composition comprising a pharmaceutically acceptable excipient and the solid form of claim 11.

15. A method for modulating 5-hydroxytryptamine$_{2A}$ (5-HT$_{2A}$) receptor activity in a subject, wherein the method comprises administering to the subject in need thereof a therapeutically effective amount of the solid form of claim 11.

16. The method of claim 15, wherein the subject has a disorder selected from the group consisting of a neurological disorder a psychiatric disorder, or a combination thereof.

17. A solid form of tabernanthalog monofumarate salt of the following formula:

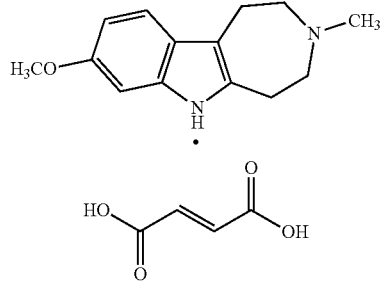 [SMILES: COc1ccc2c3c([nH]c2c1)CCN(C)CC3 ; O=C(O)/C=C/C(=O)O]

wherein the solid form is crystalline polymorphic Pattern #6a;
wherein crystalline polymorphic Pattern #6a is characterized by an X-ray powder diffraction diffractogram comprising two signals at angles (°2θ) selected from the group consisting of 16.6°±0.2 °2θ, 19.6°±0.2 °2θ, and 20.7°±0.2 °2θ; and
wherein the X-ray powder diffraction diffractogram signals are present when the X-ray powder diffraction is carried out using Cu Kα1 radiation.

18. The solid form of claim 17, wherein the crystalline polymorphic Pattern #6a is further characterized by an X-ray powder diffraction diffractogram comprising three signals at angles (°2θ) of 16.6°±0.2 °2θ, 19.6°±0.2 °2θ, and 20.7°±0.2 °2θ.

19. The solid form of claim 17, wherein the crystalline polymorphic Pattern #6a is further characterized by an X-ray powder diffraction diffractogram comprising one or two additional signals at angles (°2θ) selected from the group consisting of 19.3°±0.2 °2θ and 25.4°±0.2 °2θ.

20. The solid form of claim 17, wherein the crystalline polymorphic Pattern #6a is further characterized by an X-ray powder diffraction diffractogram comprising one, two, three, or four additional signals at angles (°2θ) selected from the group consisting of 19.3°±0.2 °2θ, 22.1°±0.2 °2θ, 25.4°±0.2 °2θ, and 26.2°±0.2 °2θ.

21. The solid form of claim 17, wherein the crystalline polymorphic Pattern #6a is further characterized by an X-ray powder diffraction diffractogram comprising one, two, three, four, five, or six additional signals at angles (°2θ) selected from the group consisting of 13.0°±0.2 °2θ, 16.6°±0.2 °2θ, 19.3°±0.2 °2θ, 19.6°±0.2 °2θ, 20.7°±0.2 °2θ, 22.1°±0.2 °2θ, 25.4°±0.2 °2θ, 26.2°±0.2 °2θ, and 33.6°±0.2 °2θ.

22. The solid form of claim 17, wherein the crystalline polymorphic Pattern #6a is further characterized by an X-ray powder diffraction diffractogram comprising one, two, three, four, five, six, seven, or eight additional signals at angles (°2θ) selected from the group consisting of 13.0°±0.2 °2θ, 16.6°±0.2 °2θ, 19.3°±0.2 °2θ, 19.6°±0.2 °2θ, 20.7°±0.2 °2θ, 22.1°±0.2 °2θ, 25.4°±0.2 °2θ, 26.2°±0.2 °2θ, and 33.6°±0.2 °2θ.

23. The solid form of claim 17, wherein the crystalline polymorphic Pattern #6a is further characterized by an X-ray powder diffraction diffractogram as depicted in FIG. 13.

24. The solid form of claim 17, wherein the crystalline polymorphic Pattern #6a is further characterized by an X-ray powder diffraction diffractogram as depicted in FIG. 346(A).

25. The solid form of claim 17, wherein the crystalline polymorphic Pattern #6a is further characterized by two or more properties selected from the group consisting of:
   (i) an X-ray powder diffraction diffractogram as depicted in FIG. 13;
   (ii) a $^1$H nuclear magnetic resonance (NMR) spectrum as depicted in FIG. 344;
   (iii) a thermogravimetric analysis (TGA) thermogram as depicted in FIG. 347; and
   (iv) a differential scanning calorimetry (DSC) thermogram as depicted in FIG. 348.

26. A pharmaceutical composition comprising a pharmaceutically acceptable excipient and the solid form of claim 17.

27. A method for modulating 5-hydroxytryptamine2A (5-HT$_{2A}$) receptor activity in a subject, wherein the method comprises administering to the subject in need thereof a therapeutically effective amount of the solid form of claim 17.

28. The method of claim 27, wherein the subject has a disorder selected from the group consisting of a neurological disorder and a psychiatric disorder, or a combination thereof.

* * * * *